(12) United States Patent
Buckman et al.

(10) Patent No.: US 8,975,235 B2
(45) Date of Patent: Mar. 10, 2015

(54) LYSOPHOSPHATIDIC ACID RECEPTOR ANTAGONISTS

(75) Inventors: Brad O. Buckman, Oakland, CA (US); John B. Nicholas, Redwood City, CA (US); Kumaraswamy Emayan, Berkeley, CA (US); Scott D. Seiwert, Half Moon Bay, CA (US)

(73) Assignee: InterMune, Inc., Brisbane, CA (US)

( * ) Notice: Subject to any disclaimer, the term of this patent is extended or adjusted under 35 U.S.C. 154(b) by 90 days.

(21) Appl. No.: 13/585,716

(22) Filed: Aug. 14, 2012

(65) Prior Publication Data

US 2013/0072449 A1  Mar. 21, 2013

Related U.S. Application Data

(60) Provisional application No. 61/523,776, filed on Aug. 15, 2011, provisional application No. 61/570,739, filed on Dec. 14, 2011, provisional application No. 61/613,395, filed on Mar. 20, 2011, provisional application No. 61/674,214, filed on Jul. 20, 2012.

(51) Int. Cl.

| | |
|---|---|
| C07D 495/04 | (2006.01) |
| C07D 307/66 | (2006.01) |
| C07D 213/75 | (2006.01) |
| C07D 413/10 | (2006.01) |
| C07D 417/12 | (2006.01) |
| C07D 231/40 | (2006.01) |
| C07D 401/10 | (2006.01) |
| C07D 405/12 | (2006.01) |
| C07D 413/04 | (2006.01) |
| C07D 249/06 | (2006.01) |
| C07D 257/06 | (2006.01) |
| C07D 401/04 | (2006.01) |
| A61K 31/381 | (2006.01) |
| A61K 31/426 | (2006.01) |
| C07D 333/20 | (2006.01) |
| A61K 31/4192 | (2006.01) |
| A61K 31/4427 | (2006.01) |
| A61K 31/415 | (2006.01) |
| C07D 275/03 | (2006.01) |
| C07D 261/14 | (2006.01) |
| A61K 31/4155 | (2006.01) |
| C07D 471/04 | (2006.01) |
| C07H 15/26 | (2006.01) |
| C07D 491/04 | (2006.01) |
| A61K 31/425 | (2006.01) |
| A61K 31/421 | (2006.01) |
| C07D 491/048 | (2006.01) |
| C07D 277/46 | (2006.01) |
| C07D 263/48 | (2006.01) |
| C07D 207/34 | (2006.01) |
| A61K 31/42 | (2006.01) |

(52) U.S. Cl.
CPC ............ *C07D 495/04* (2013.01); *C07D 401/04* (2013.01); *A61K 31/381* (2013.01); *C07D 231/40* (2013.01); *C07D 213/75* (2013.01); *C07D 401/10* (2013.01); *A61K 31/426* (2013.01); *C07D 333/20* (2013.01); *A61K 31/4192* (2013.01); *C07D 417/12* (2013.01); *C07D 249/06* (2013.01); *A61K 31/4427* (2013.01); *A61K 31/415* (2013.01); *C07D 257/06* (2013.01); *C07D 275/03* (2013.01); *C07D 261/14* (2013.01); *A61K 31/4155* (2013.01); *C07D 471/04* (2013.01); *C07D 413/10* (2013.01); *C07H 15/26* (2013.01); *C07D 491/04* (2013.01); *A61K 31/425* (2013.01); *C07D 413/04* (2013.01); *A61K 31/421* (2013.01); *C07D 491/048* (2013.01); *C07D 277/46* (2013.01); *C07D 263/48* (2013.01); *C07D 207/34* (2013.01); *C07D 405/12* (2013.01); *A61K 31/42* (2013.01); *C07D 307/66* (2013.01)
USPC .................. 514/25; 514/210.18; 514/255.01; 514/302; 514/342; 514/380; 544/391; 546/114; 546/115; 546/209; 546/271.1; 548/245

(58) Field of Classification Search
None
See application file for complete search history.

(56) References Cited

U.S. PATENT DOCUMENTS

| | | | |
|---|---|---|---|
| 5,455,348 A | 10/1995 | Austel et al. | |
| 6,964,975 B2 | 11/2005 | Ueno et al. | |
| 7,160,887 B1 | 1/2007 | Oi et al. | |
| 8,058,300 B2 * | 11/2011 | Hutchinson et al. | .......... 514/380 |
| 2002/0183324 A1 | 12/2002 | Jacobson et al. | |

(Continued)

FOREIGN PATENT DOCUMENTS

| | | |
|---|---|---|
| EP | 0528369 A2 | 2/1993 |
| JP | 2004182657 | 7/2004 |

(Continued)

OTHER PUBLICATIONS

Beck et al., Discovery of potent LPA₂ (EDG4) antagonists as potential anticancer agents, Bioorg. Med. Chem. Lett. (2008) 18(3): 1037-1041.

Ma et al., Evidence for lysophosphatidic acid 1 receptor signaling in the early phase of neuropathic pain mechanisms in experiments using Ki-16425, a lysophosphatidic acid 1 receptor antagonist, J. Neurochem. (2009) 109(2): 603-610.

(Continued)

*Primary Examiner* — Kamal Saeed
(74) *Attorney, Agent, or Firm* — Knobbe Martens Olson & Bear LLP

(57) ABSTRACT

Compounds, methods of making such compounds, pharmaceutical compositions and medicaments comprising such compounds, and methods of using such compounds to treat, prevent or diagnose diseases, disorders, or conditions associated with one or more of the lysophosphatidic acid receptors are provided.

35 Claims, No Drawings

(56) References Cited

U.S. PATENT DOCUMENTS

| | | |
|---|---|---|
| 2004/0072802 A1 | 4/2004 | Duan et al. |
| 2004/0167132 A1 | 8/2004 | Shankar et al. |
| 2004/0171582 A1 | 9/2004 | Nakade et al. |
| 2004/0192739 A1 | 9/2004 | Solow-Cordero et al. |
| 2004/0214888 A1 | 10/2004 | Matsuura et al. |
| 2005/0014833 A1 | 1/2005 | Clark et al. |
| 2005/0065194 A1 | 3/2005 | Shankar et al. |
| 2005/0107447 A1 | 5/2005 | Lynch et al. |
| 2005/0250798 A1 | 11/2005 | Dollings et al. |
| 2005/0256160 A1 | 11/2005 | Habashita et al. |
| 2006/0009507 A1 | 1/2006 | Miller et al. |
| 2006/0135577 A1 | 6/2006 | Nakade et al. |
| 2006/0135578 A1 | 6/2006 | Momose et al. |
| 2006/0148830 A1 | 7/2006 | Terakado et al. |
| 2006/0194850 A1 | 8/2006 | Yamamoto et al. |
| 2006/0270634 A1 | 11/2006 | Miller et al. |
| 2007/0117803 A1 | 5/2007 | Sundermann et al. |
| 2007/0149595 A1 | 6/2007 | Tanaka et al. |
| 2007/0161604 A1 | 7/2007 | Hayashi et al. |
| 2009/0131403 A1 | 5/2009 | Kusuda et al. |
| 2010/0152257 A1 | 6/2010 | Hutchinson et al. |
| 2010/0311799 A1 | 12/2010 | Hutchinson et al. |
| 2011/0082164 A1 | 4/2011 | Clark et al. |
| 2011/0082181 A1 | 4/2011 | Seiders et al. |
| 2012/0184521 A1 | 7/2012 | Kawaminami et al. |
| 2012/0258987 A1 | 10/2012 | Seiders et al. |

FOREIGN PATENT DOCUMENTS

| | | |
|---|---|---|
| JP | 2006096712 | 4/2006 |
| JP | 2008297278 | 12/2008 |
| WO | WO 93/21182 | 10/1993 |
| WO | WO 95/33750 | 12/1995 |
| WO | WO 98/08845 | 3/1998 |
| WO | WO 00/23420 | 4/2000 |
| WO | WO 00/64876 | 11/2000 |
| WO | WO 01/12838 | 2/2001 |
| WO | WO 01/66098 | 9/2001 |
| WO | WO 01/70734 | 9/2001 |
| WO | WO 01/71022 | 9/2001 |
| WO | WO 02/00651 | 1/2002 |
| WO | WO 02/29001 | 4/2002 |
| WO | WO 03/007955 | 1/2003 |
| WO | WO 03/018536 | 3/2003 |
| WO | WO 2005/012269 | 2/2005 |
| WO | WO 2005/014533 | 2/2005 |
| WO | WO 2005/044797 | 5/2005 |
| WO | WO 2005/077345 | 8/2005 |
| WO | WO 2005/110973 | 11/2005 |
| WO | WO 2006/093823 | 9/2006 |
| WO | WO 2006/123257 | 11/2006 |
| WO | WO 2006/125208 | 11/2006 |
| WO | WO 2006/129199 | 12/2006 |
| WO | WO 2007/011905 | 1/2007 |
| WO | WO 2007/095602 | 8/2007 |
| WO | WO 2007/106525 | 9/2007 |
| WO | WO 2007/122401 | 11/2007 |
| WO | WO 2007/129019 | 11/2007 |
| WO | WO 2007/139946 | 12/2007 |
| WO | WO 2007/143745 | 12/2007 |
| WO | WO 2007/145838 | 12/2007 |
| WO | WO 2008/014286 | 1/2008 |
| WO | WO 2008/079291 | 7/2008 |
| WO | WO 2008/134693 | 11/2008 |
| WO | WO 2008/157361 | 12/2008 |
| WO | WO 2009/096198 | 8/2009 |
| WO | WO 2009/135590 | 11/2009 |
| WO | WO 2009/152356 | 12/2009 |
| WO | WO 2010/051053 | 5/2010 |
| WO | WO 2010/068775 | 6/2010 |
| WO | WO 2010/077882 | 7/2010 |
| WO | WO 2010/093704 | 8/2010 |
| WO | WO 2010/096395 | 8/2010 |
| WO | WO 2010/141761 | 9/2010 |
| WO | WO 2010/141768 | 12/2010 |
| WO | WO 2010/148422 | 12/2010 |
| WO | WO 2011/017350 | 2/2011 |
| WO | WO 2011/031965 | 3/2011 |
| WO | WO 2011/041462 | 4/2011 |
| WO | WO 2011/041694 | 4/2011 |
| WO | WO 2011/053948 | 5/2011 |
| WO | WO 2011/097300 | 8/2011 |
| WO | WO 2011/159550 | 12/2011 |
| WO | WO 2011/159632 | 12/2011 |
| WO | WO 2011/159633 | 12/2011 |
| WO | WO 2011/159635 | 12/2011 |
| WO | WO 2012/024620 | 2/2012 |
| WO | WO 2012/028243 | 3/2012 |
| WO | 2012/078593 A2 † | 6/2012 |
| WO | WO 2012/078593 | 6/2012 |
| WO | WO 2012/078805 | 6/2012 |
| WO | WO 2012/100436 | 8/2012 |
| WO | WO 2012/138648 | 10/2012 |
| WO | WO 2012/138797 | 10/2012 |
| WO | WO 2013/025733 | 2/2013 |
| WO | WO 2013/070879 | 5/2013 |
| WO | WO 2013/085824 | 6/2013 |
| WO | WO 2013/189862 | 12/2013 |
| WO | WO 2013/189864 | 12/2013 |
| WO | WO 2013/189865 | 12/2013 |

OTHER PUBLICATIONS

Matsuzaki et al., Lysophosphatidic Acid Inhibits CC Chemokine Ligand 5/RANTES Production by Blocking IRF-1-Mediated Gene Transcription in Human Bronchial Epithelial Cells, J. Immunol. (2010) 185(8): 4863-4872.

Ohta et al., Ki16425, a Subtype-Selective Antagonist for EDG-Family Lysophosphatidic Acid Receptors, Mol. Pharmacol. (2003) 64(4): 994-1005.

Qian et al. Discovery of Highly Selective and Orally Active Lysophosphatidic Acid Receptor-1 Antagonists with Potent Activity on Human Lung Fibroblasts. J Med Chem. (Epub: Aug. 2012) 55(17): 7920-7939.

Reiter et al., Synthesis of 4(5)-acyl-, 1-substituted 5-acyl and 1-substituted 4 acyl-1H imidazoles from 4-aminoisoxazoles, J. Org. Chem. (1987) 52(13): 2714-2726.

Swaney et al., A novel, orally active LPA(1) receptor antagonist inhibits lung fibrosis in the mouse bleomycin model. Br. J. Pharmacol. (2010) 160(7): 1699-1713.

Yamada et al., Lysophosphatidic Acid (LPA) in Malignant Ascites Stimulates Motility of Human Pancreatic Cancer Cells through LPA1, J. Biol. Chem. (2004) 279(8): 6595-6605.

Yamamoto et al., Synthesis and evaluation of isoxazole derivatives as lysophosphatidic acid (LPA) antagonists, Bioorg Med Chem Lett. (2007) 17(13): 3736-3740.

International Preliminary Report on Patentability dated Nov. 7, 2013 in Application No. PCT/US2012/050824, filed Aug. 14, 2012.

International Search Report and Written Opinion dated Dec. 21, 2012 in PCT/US2012/050824, filed Aug. 14, 2012.

International Written Opinion [Rule 66] dated Jul. 26, 2013 in PCT/US2012/050824, filed Aug. 14, 2012.

\* cited by examiner
† cited by third party

LYSOPHOSPHATIDIC ACID RECEPTOR ANTAGONISTS

CROSS-REFERENCE TO RELATED APPLICATIONS

The present application claims the benefit of priority to U.S. Appl. No. 61/523,776, filed Aug. 15, 2011, U.S. Appl. No. 61/570,739, filed Dec. 14, 2011, U.S. Appl. No. 61/613,395, filed Mar. 20, 2012, and U.S. Appl. No. 61/674,214, filed Jul. 20, 2012, all of which are hereby incorporated by references in their entireties.

FIELD OF THE INVENTION

Compounds, methods of making such compounds, pharmaceutical compositions and medicaments comprising such compounds, and methods of using such compounds to treat, prevent or diagnose diseases, disorders, or conditions associated with one or more of the lysophosphatidic acid receptors are provided.

BACKGROUND OF THE INVENTION

Lysophospholipids are membrane-derived bioactive lipid mediators that affect fundamental cellular functions. These cellular functions include, but are not limited to, proliferation, differentiation, survival, migration, adhesion, invasion, and morphogensis. These cellular functions influence biological processes that include, but are not limited to, neurogensis, angiogenesis, wound healing, fibrosis, immunity, and carcinogenesis.

Lysophosphatidic acid (LPA) is a lysophospholipid that has been demonstrated to act through sets of specific G protein-coupled receptors (GPCRs) in an autocrine and paracrine fashion. LPA binding to its cognate GPCRs (LPA$_1$, LPA$_2$, LPA$_3$, LPA$_4$, LPA$_5$, and LPA$_6$) activates intracellular signaling pathways to produce a variety of biological responses. Antagonists of the LPA receptors can be employed in the treatment of diseases, disorders, or conditions in which LPA plays a role.

SUMMARY OF THE INVENTION

In a first aspect, a compound of Formula (I) is provided:

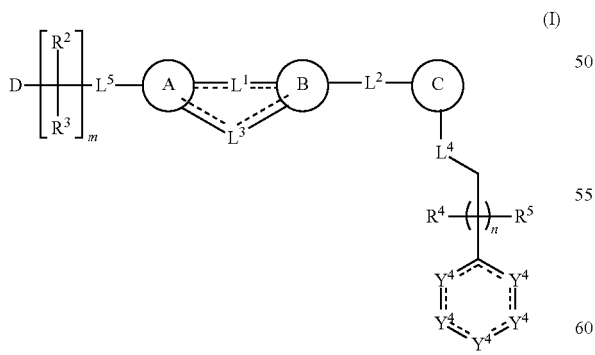

or a pharmaceutically acceptable salt thereof, wherein:
A is an acetylene or a ring system selected from 4-7 membered heterocycle, 4-7 membered cyclic hydrocarbyl, 8-11 membered bicyclic heterocycle, or 8-11 membered bicyclic hydrocarbyl, wherein the ring system is non-aromatic, aromatic, or partially aromatic, and wherein the ring system is unsubstituted or substituted with one or more substituents selected from alkyl, halo, cyano or oxo;

For example. A can be selected from:

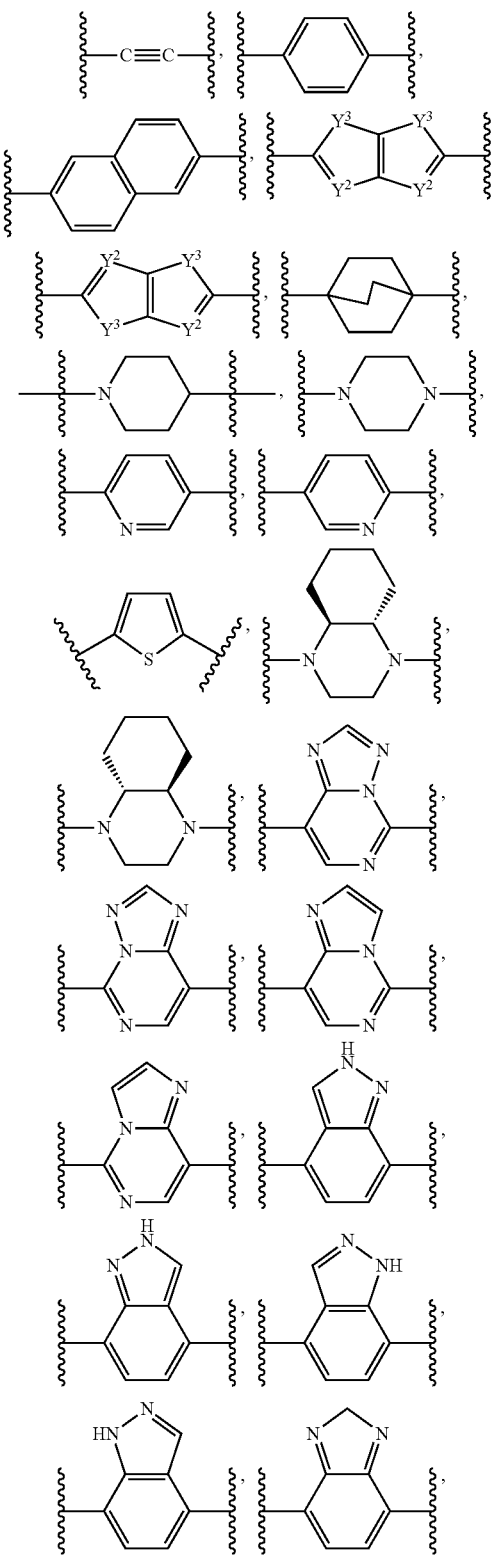

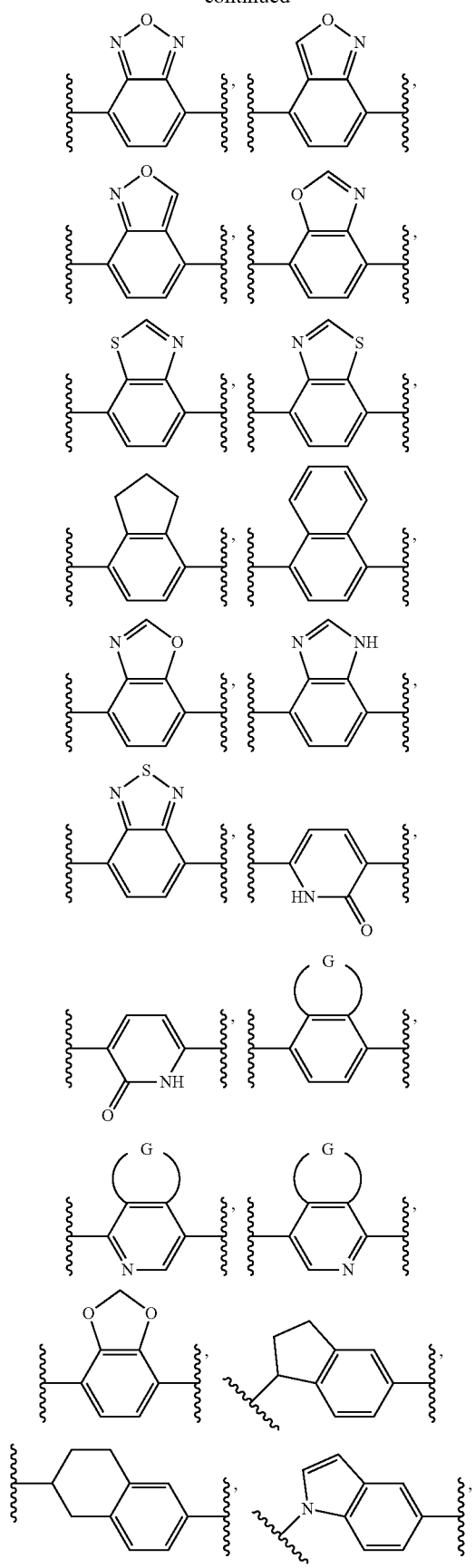

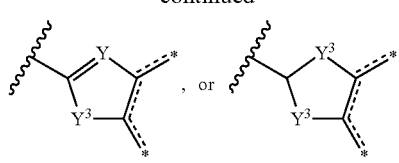

wherein each * is a point of attachment of A to $L^1$ or $L^3$, and wherein the rings in A are unsubstituted or substituted with one or more substituents selected from alkyl, halo, cyano, or oxo;

B is an acetylene or a ring system selected from 4-7 membered heterocycle, 4-7 membered cyclic hydrocarbyl, 8-11 membered bicyclic heterocycle, or 8-11 membered bicyclic hydrocarbyl, wherein the ring system is non-aromatic, aromatic, or partially aromatic, and wherein the ring system is unsubstituted or substituted with one or more substituents selected from alkyl, halo, cyano, or oxo;

For example, B can be selected from

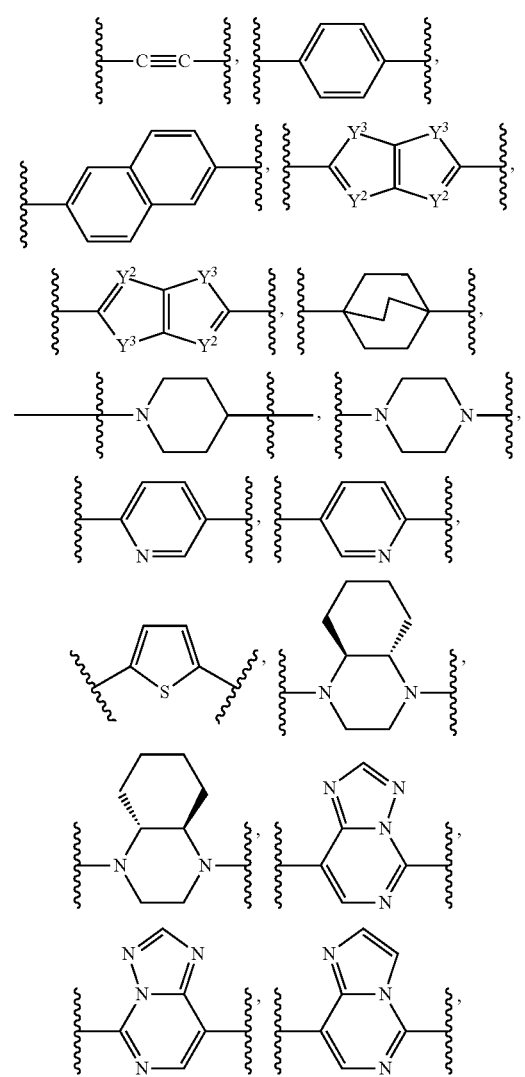

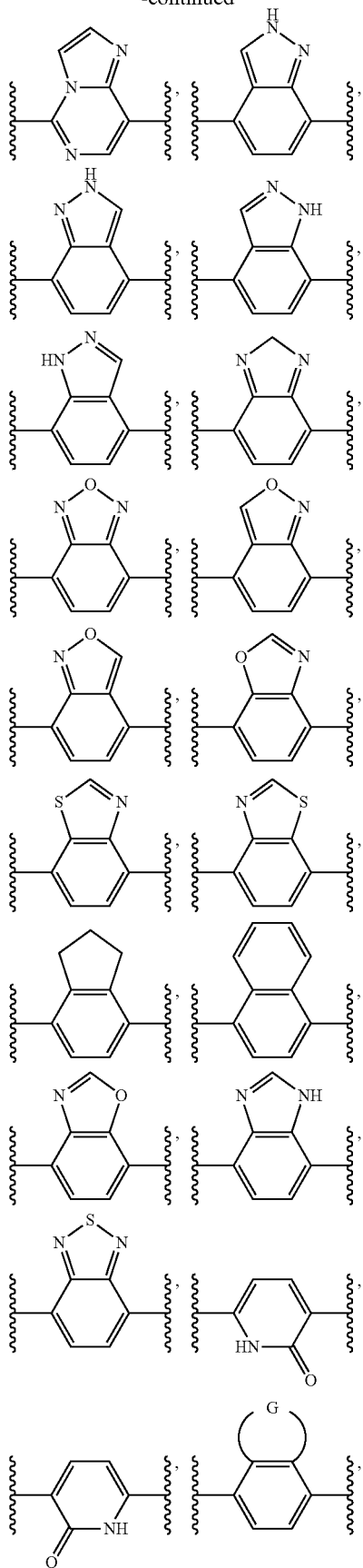

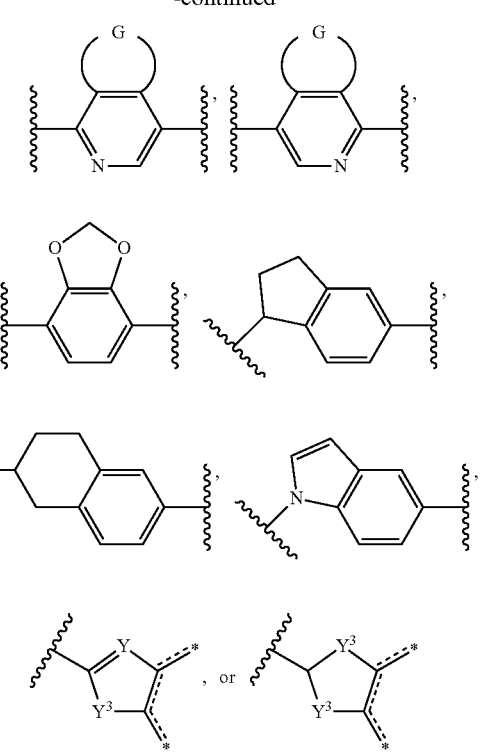

wherein each * is a point of attachment of B to $L^1$ or $L^3$, and wherein the rings in B are unsubstituted or substituted with one or more substituents selected from alkyl, halo, cyano, or oxo;

or B is optionally absent when

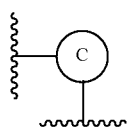

is

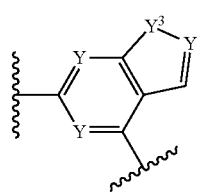

or an optionally substituted variant thereof;

G together with the atoms to which it is attached forms a ring system selected from 4-7 membered heterocycle, 4-7 membered cyclic hydrocarbyl, 8-11 membered bicyclic heterocycle, 8-11 membered bicyclic hydrocarbyl, wherein the ring system is non-aromatic, aromatic, or partially aromatic, and wherein the ring system is unsubstituted or substituted with one or more substituents selected from alkyl, halo, or oxo;

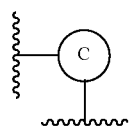
is a ring system selected from 5-7 membered heterocycle, 5-7 membered cyclic hydrocarbyl, 8-11 membered bicyclic heterocycle and 8-11 membered bicyclic hydrocarbyl, wherein the ring system is non-aromatic, aromatic or partially aromatic, and wherein the ring system can be optionally substituted;
For example,
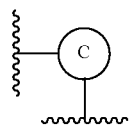
can be selected from:
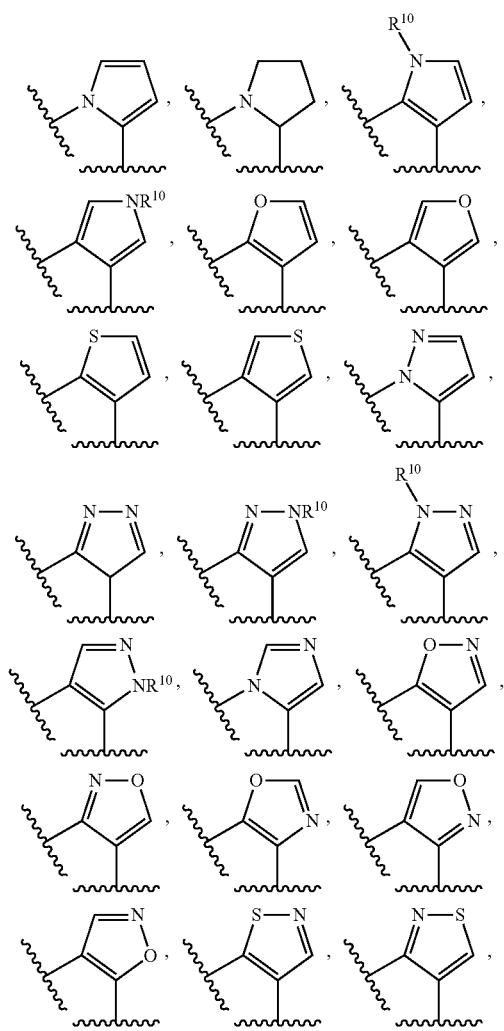
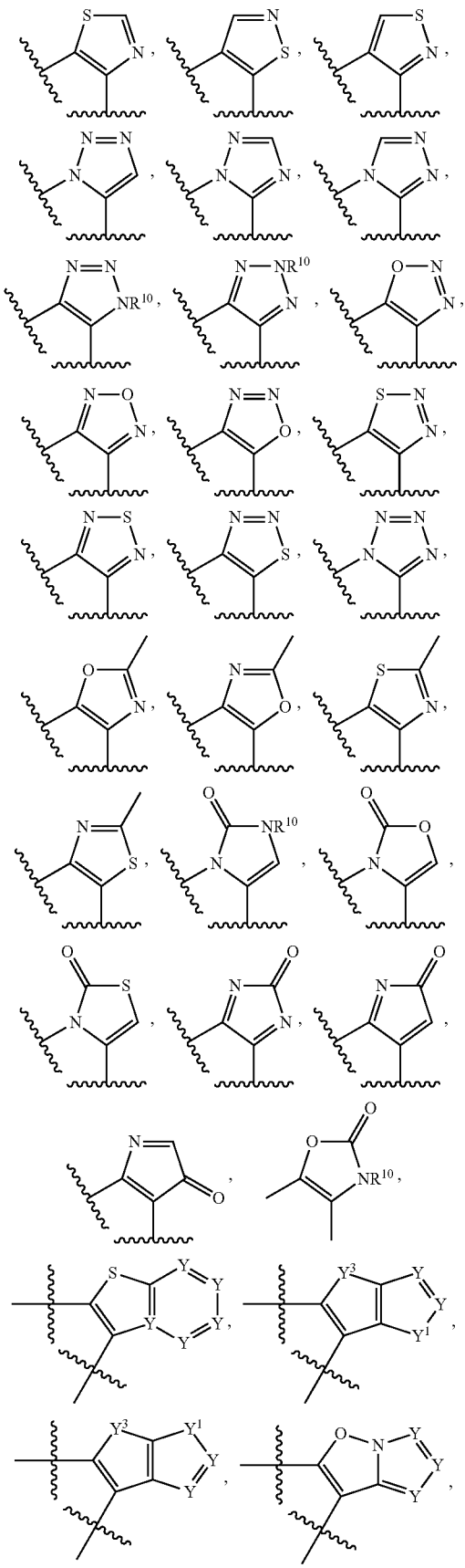

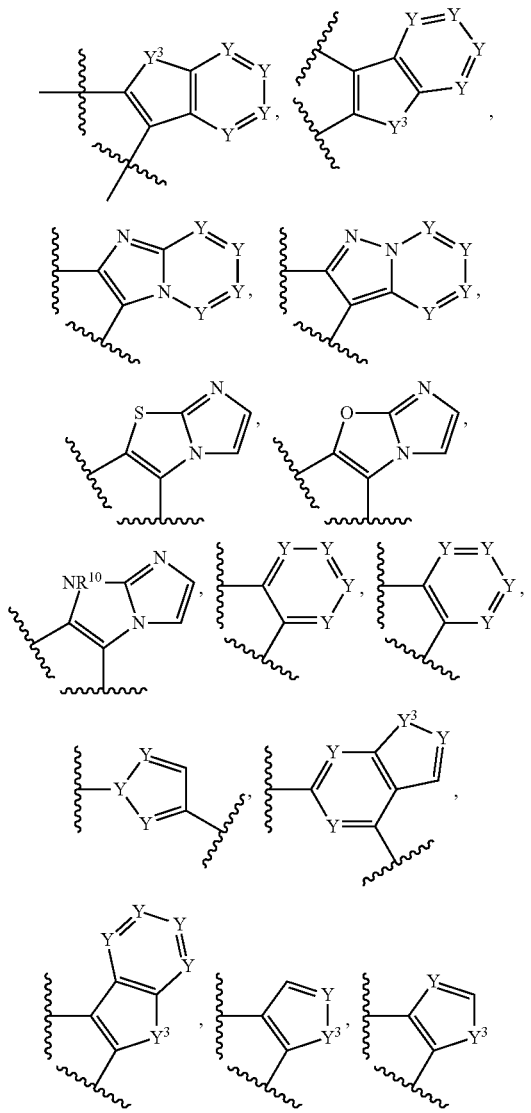
or optionally substituted variants thereof, and $L^4$ is
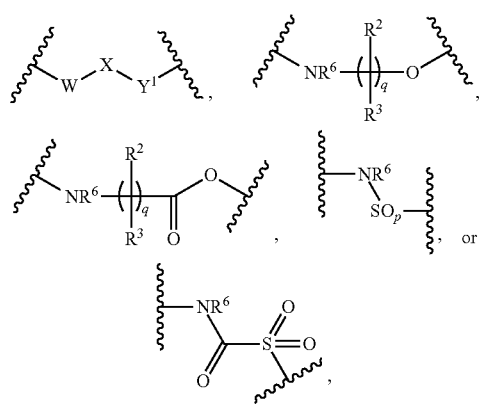
or alternatively,
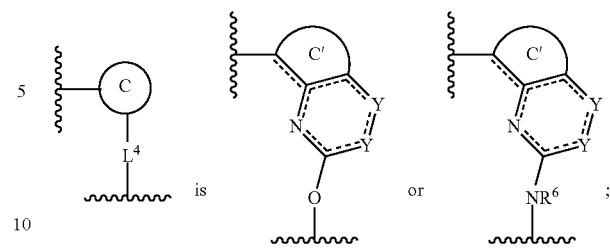
is selected from:
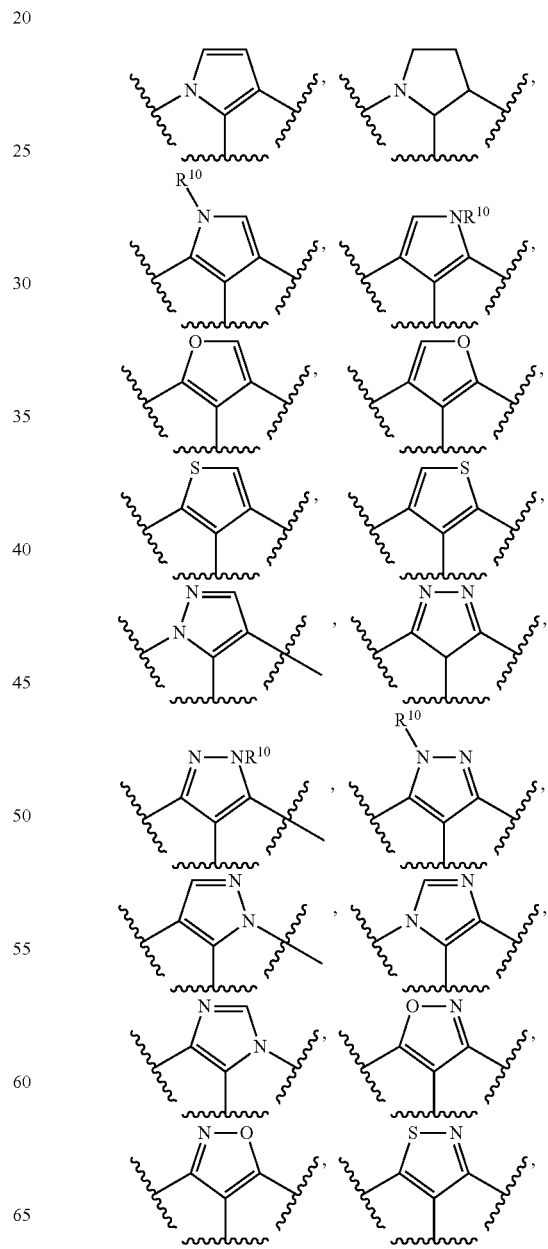

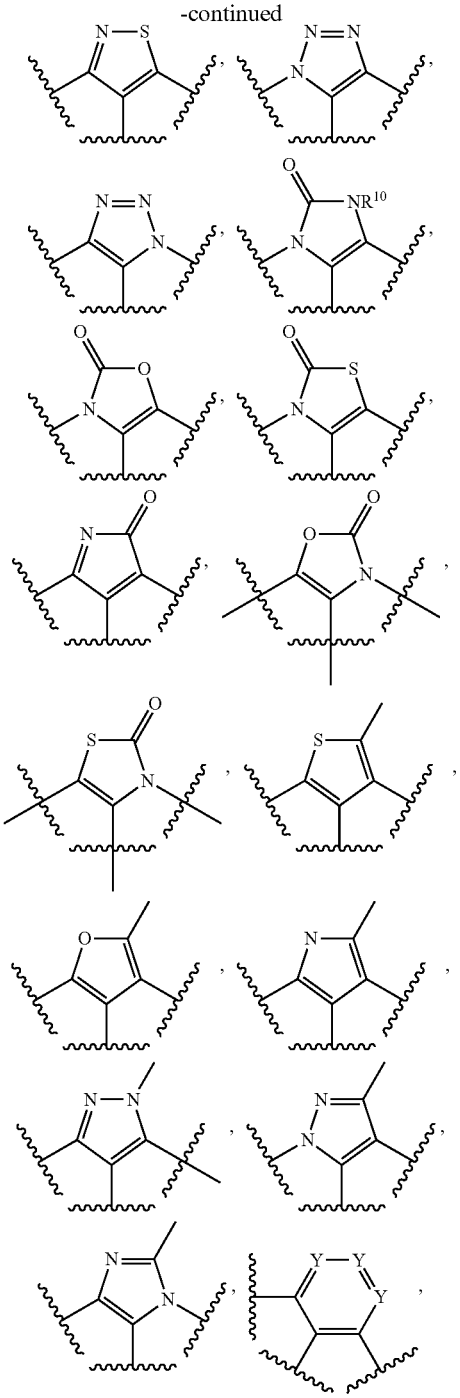

or optionally substituted variants thereof;

L¹ is selected from a bond, a —O— linker, a —NH— linker, a —C(O)— linker, a —CH₂— linker, a —CH₂O— linker, a —OCH₂— linker, a —C≡C— linker, a —CH=CH— linker, a =C(R¹⁵)— linker, or a —C(R¹⁵)= linker;

L² is selected from a bond, a —O— linker, a —NH— linker, a —C(O)— linker, a —CH₂— linker, a —CH₂O— linker, a —OCH₂— linker, a —C≡C— linker, or a —CH=CH— linker;

L³ is absent,

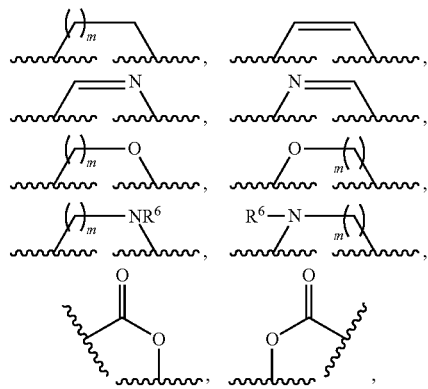

a =C(R¹⁵)— linker, or a —C(R¹⁵)= linker;
W is C(R⁶)₂, NR⁶, or O; X is

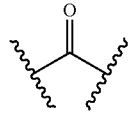 [SMILES: *C(*)=O]

or S(O)$_p$;

each Y is independently selected from CR⁶ or N;
Y¹ is C(R⁶)₂, NR⁶, or O; Y² is —CH=, =CH—, or N; Y³ is C(R⁶)₂, NR⁶, O, or S; each Y⁴ is independently absent, CR⁹, C(R⁹)₂, N or NH, provided that only one Y⁴ can be absent;

L⁵ is selected from a bond, a —CH₂O— linker, a —OCH₂— linker, a —CH=CH— linker or a 4-7 membered heterocycle;

D is selected from

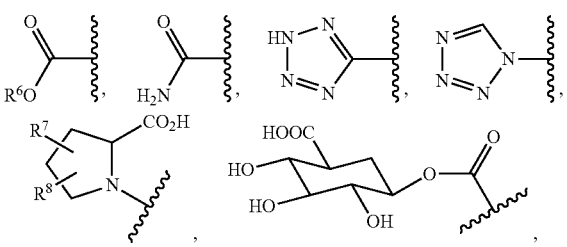

or carboxylic acid isosteres;

R² and R³ are each independently selected from H, alkyl, aryl, or heteroaryl; or R² and R³ are joined together with the atom to which they are attached to form an optionally substituted cycloalkyl or an optionally substituted heterocycle; or R² is selected from H, alkyl, aryl, or heteroaryl, and R³ is joined to an atom alpha to a point of attachment of L⁵ to A to form an optionally substituted cycloalkyl or an optionally substituted heterocycle; or R³ is selected from H, alkyl, aryl, or heteroaryl, and R² is joined to an atom alpha to a point of attachment of L⁵ to A to form an optionally substituted cycloalkyl or an optionally substituted heterocycle;

each R⁴ and R⁵ is independently selected from H and alkyl; or R⁴ and R⁵ are joined together with the atom to which they are attached to form an optionally substituted cycloalkyl or optionally substituted heterocycle;

each $R^6$ is independently selected from H, alkyl, halo, aryl, or $C_{3-6}$ cycloalkyl;

each $R^{10}$ is independently selected from H, alkyl, halo, aryl, $C_{3-6}$ cycloalkyl, or cyano;

each $R^9$ is independently selected from H, alkyl or halogen or two $R^9$ are joined together with the atoms to which they are attached to form an optionally substituted carbocycle or an optionally substituted heterocycle;

each $R^7$ and $R^8$ is independently H or $C_{1-6}$ alkyl, or $R^7$ and $R^8$ are joined together with the atom or atoms to which they are attached to form a spirocyclic heterocycle, a spirocyclic carbocycle, a fused heterocycle, or a fused carbocycle;

each $R^{15}$ is independently selected from H, alkyl, halo, or cyano;

m is independently an integer from 0-3; n is an integer from 0-3; p is an integer from 1-2; q is an integer from 1-6; and ===== represents a single or double bond; provided that at least one of the following conditions is met in the compound of Formula (I):

(1) if A and B are each independently selected from phenyl, cyclohexyl, indolyl, 5-membered heteroaryl, 6-membered heteroaryl, and variants thereof substituted with halo or methyl;

if

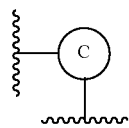

is

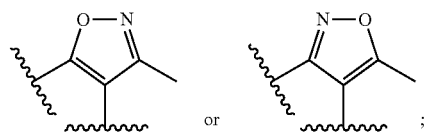

if $L^3$ is absent; if $L^5$ is a bond; if D is —COOR$^6$ and m is 0 or 1; and if $R^2$ and $R^3$ are both H, or $R^2$ is H and $R^3$ is alkyl, or $R^2$ and $R^3$ are joined together with the atom to which they are attached to form an optionally substituted cycloalkyl;

if $R^9$ is selected from H, alkyl or halogen; then

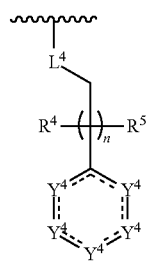

is not

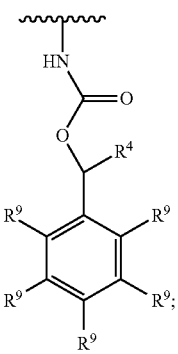

(2) if A and B are both phenyl;
if $L^1$ is a —CH$_2$O— linker, a —OCH$_2$— linker, or a —C≡C— linker;
if

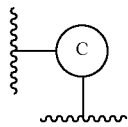

is

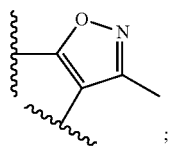 [SMILES: *c1onc(C)c1*]

if $L^3$ is absent; if $L^5$ is a bond; and if D is —COOH and m is 1;
then

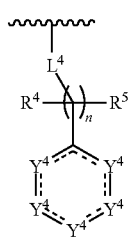

is not

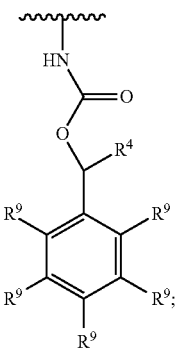

(3) if A and B are both phenyl;
if

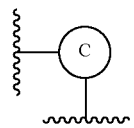

is

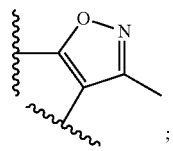 [SMILES: *c1onc(C)c1*]

if $L^1$, $L^2$, and $L^5$ are all a bond; if $L^3$ is absent; if D is
—COOH and m is 1; if $R^2$ and $R^3$ are both H, or $R^2$ is
H and $R^3$ is alkyl, or $R^2$ and $R^3$ are joined together with
the atom to which they are attached to form an optionally substituted cycloalkyl; if $R^4$ and $R^5$ are H or alkyl;
if

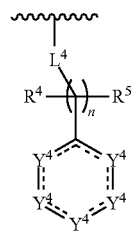

is

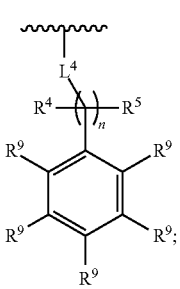

then $L^4$ is not an amide linkage, a carbamate linkage,
a urea linkage, a methyl urea linkage, a —CH$_2$S(=O)
CH$_2$— linkage, or a —CH$_2$C(=O)CH$_2$— linkage;
(4) if A and B are both phenyl;
if

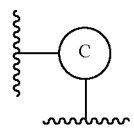

is

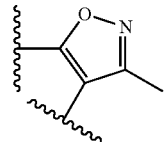

if $L^1$, $L^2$, and $L^5$ are all a bond; if $L^3$ is absent; if D is
—COOH and m is 1; if n is 1; if one $R^9$ is chloro; and
if $R^4$ and $R^5$ are both H;
if

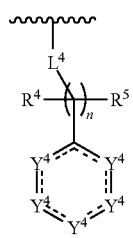

is

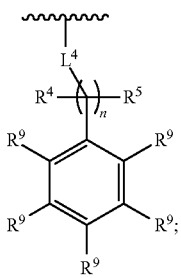

then $L^4$ is not a —NH—SO$_2$— linkage; and
(5) if A is

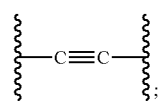

if B is phenyl;
if

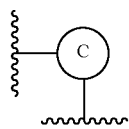

is

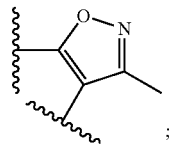 [SMILES: *c1onc(C)c1*]

if n is 1;
if one $R^9$ is chloro;
if $R^4$ is methyl; and
if $R^5$ is hydrogen;
if

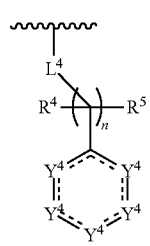

is

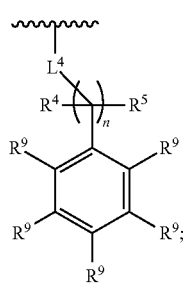

then $L^4$ is not —NHC(O)O—;
and provided that the compound of Formula (I) cannot have the structure selected from the group consisting of:

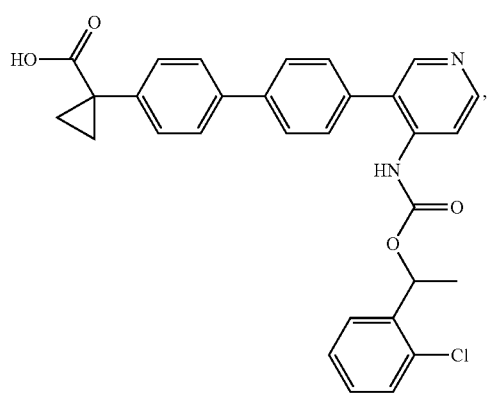

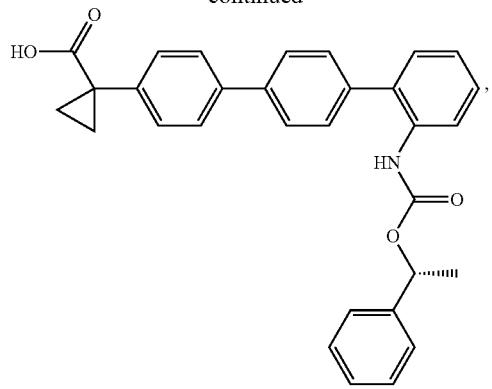

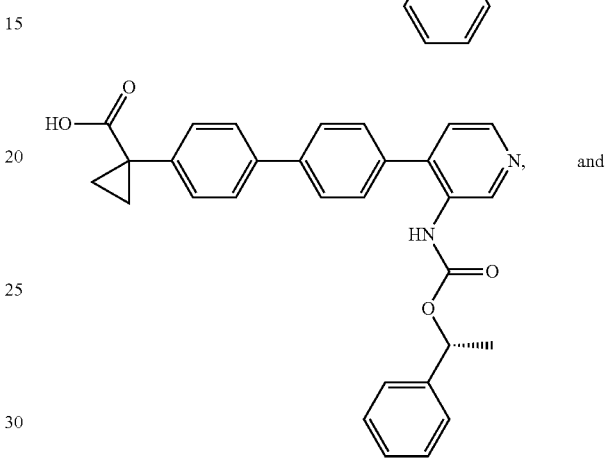

and

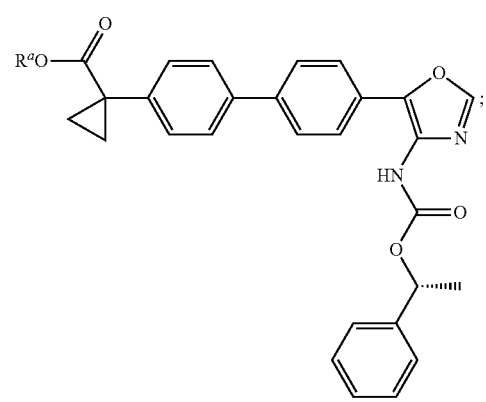

wherein $R^a$ is H or ethyl.

In an embodiment of the first aspect, the compound of formula (I) or pharmaceutical salts thereof further includes at least one of the following conditions:

(1) if $L^1$, $L^2$, and $L^5$ are all a bond; if $L^3$ is absent; and if D is —COOH and m is 1; then $L^4$ is not an amide linkage, a carbamate linkage, a urea linkage, a methyl urea linkage, a —CH$_2$S(=O)CH$_2$— linkage, or a —CH$_2$C(=O)CH$_2$— linkage; and (2) if A and B are both phenyl; if $L^1$, $L^2$, and $L^5$ are all a bond; if $L^3$ is absent; if D is —COOH and m is 1; if n is 1; if one $R^9$ is chloro; and if $R^4$ and $R^5$ are both H; then $L^4$ is not a —NH—SO$_2$— linkage.

In an embodiment of the first aspect, the compound is selected from the compounds of Table 1, and pharmaceutically acceptable salts thereof.

In an embodiment of the first aspect, the compound is selected from the compounds of Table 2, and pharmaceutically acceptable salts thereof.

In an embodiment of the first aspect, the compound is selected from the compounds of Table 3, and pharmaceutically acceptable salts thereof.

In an embodiment of the first aspect, the compound is selected from the compounds of Table 4, and pharmaceutically acceptable salts thereof.

In an embodiment of the first aspect, the compound is selected from the compounds of Table 5, and pharmaceutically acceptable salts thereof.

In an embodiment of the first aspect, the compound is selected from the compounds of Table 6, and pharmaceutically acceptable salts thereof.

In an embodiment of the first aspect, the compound is selected from the compounds of Table 7, and pharmaceutically acceptable salts thereof.

In an embodiment of the first aspect, the compound is selected from the compounds of Table 8, and pharmaceutically acceptable salts thereof.

In an embodiment of the first aspect, the compound is selected from the compounds of Table 9, and pharmaceutically acceptable salts thereof.

In an embodiment of the first aspect, the compound is selected from the compounds of Table 10, and pharmaceutically acceptable salts thereof.

In an embodiment of the first aspect, the compound is selected from the compounds of Table 11, and pharmaceutically acceptable salts thereof.

In an embodiment of the first aspect, the compound is selected from the compounds of Table 12, and pharmaceutically acceptable salts thereof.

In an embodiment of the first aspect, the compound is selected from the compounds of Table 13, and pharmaceutically acceptable salts thereof.

In an embodiment of the first aspect, the compound is selected from the compounds of Table 14, and pharmaceutically acceptable salts thereof.

In an embodiment of the first aspect, the compound is selected from the compounds of Table 15, and pharmaceutically acceptable salts thereof.

In an embodiment of the first aspect, the compound is selected from the compounds of Table 16, and pharmaceutically acceptable salts thereof.

In an embodiment of the first aspect, the compound is selected from the compounds of Table 17, and pharmaceutically acceptable salts thereof.

In an embodiment of the first aspect, the compound is selected from the compounds of Table 18, and pharmaceutically acceptable salts thereof.

In an embodiment of the first aspect, the compound is selected from the compounds of Table 19, and pharmaceutically acceptable salts thereof.

In an embodiment of the first aspect, the compound is selected from the compounds 5-8, 14-21, 23, 24, 26, 27, 29, 31-34, 37-42, 44-46, 51-53, 56, 60-94, 96-255, and 274 as described in the specification, and pharmaceutically acceptable salts thereof.

In an embodiment of the first aspect, the compound of Formula (I) is an (R)-isomer represented by Formula (Ig):

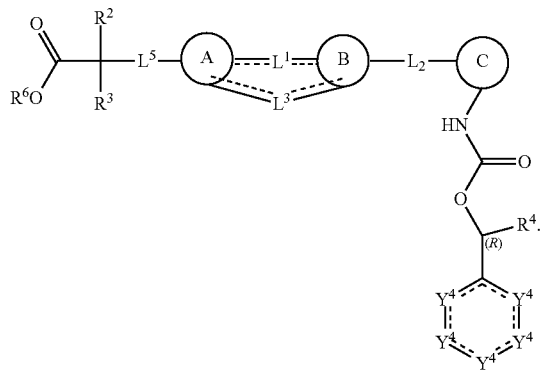

In an embodiment of the first aspect, the compound of Formula (I) is an (S)-isomer represented by Formula (Ih):

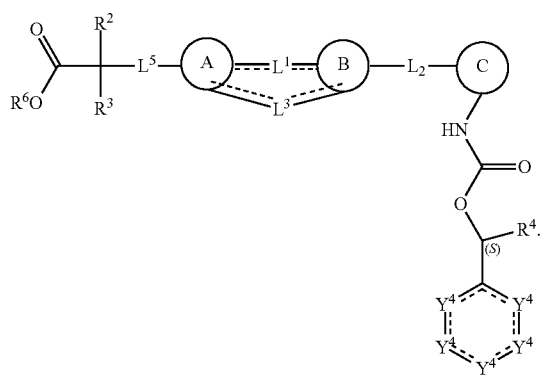

In an embodiment of the first aspect, at least one of the following conditions is met in the compound of Formula (I):

(1) if $L^1$, $L^2$, and $L^5$ are all a bond; if $L^3$ is absent; and if D is —COOH and m is 1; then $L^4$ is not an amide linkage, a carbamate linkage, a urea linkage, a methyl urea linkage, a —CH$_2$S(=O)CH$_2$-linkage, or a —CH$_2$C(=O)CH$_2$— linkage; and (2) if A and B are both phenyl; if $L^1$, $L^2$, and $L^5$ are all a bond; if $L^3$ is absent; if D is —COOH and m is 1; if n is 1; if one $R^9$ is chloro; and if $R^4$ and $R^5$ are both H; then $L^4$ is not a —NH—SO$_2$— linkage.

In an embodiment of the first aspect, at least the following conditions is met in the compound of Formula (I):

if A and B are each independently selected from phenyl, cyclohexyl, indolyl, 5-membered heteroaryl, 6-membered heteroaryl, and variants thereof substituted with halo or methyl;

if

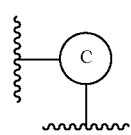

is

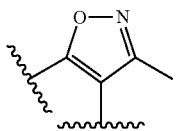 or 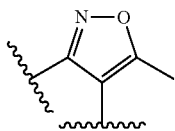 ;

if L³ is absent;
if L⁵ is a bond;
if D is —COOR⁶ and m is 0 or 1; and
if R² and R³ are both H, or R² is H and R³ is alkyl, or R² and R³ are joined together with the atom to which they are attached to form an optionally substituted cycloalkyl;
then

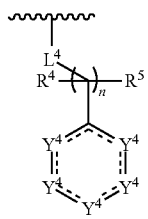

is not

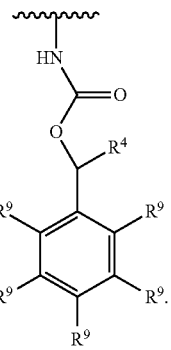

In a second aspect, the compound or pharmaceutically acceptable salt thereof of the first aspect is also represented by Formula (Ia):

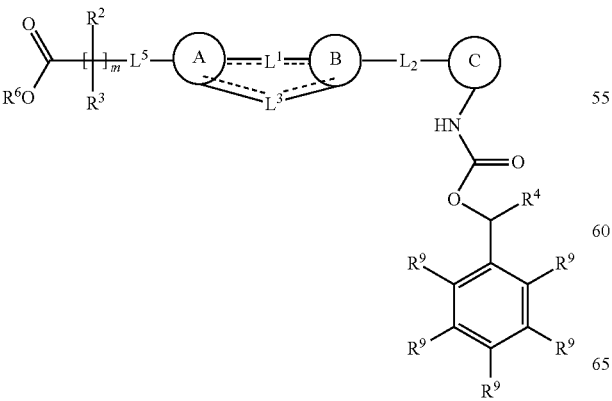

(Ia)

A is selected from:

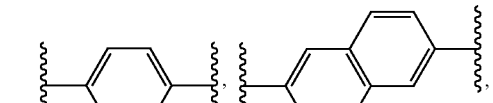

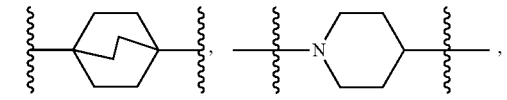

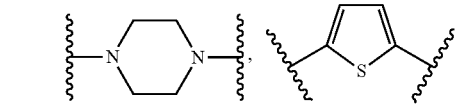

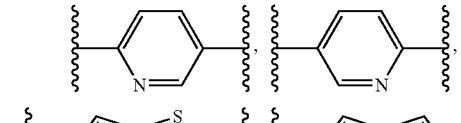

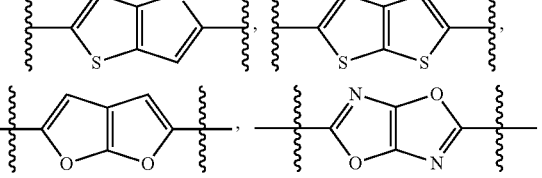

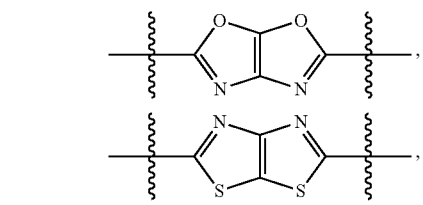

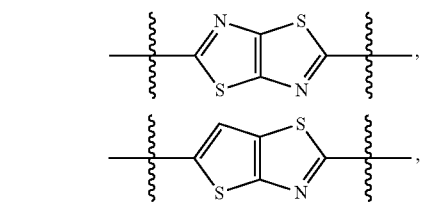

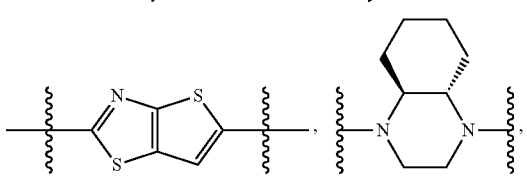

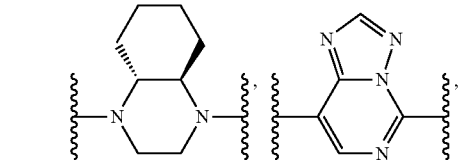

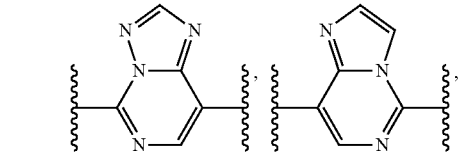

-continued
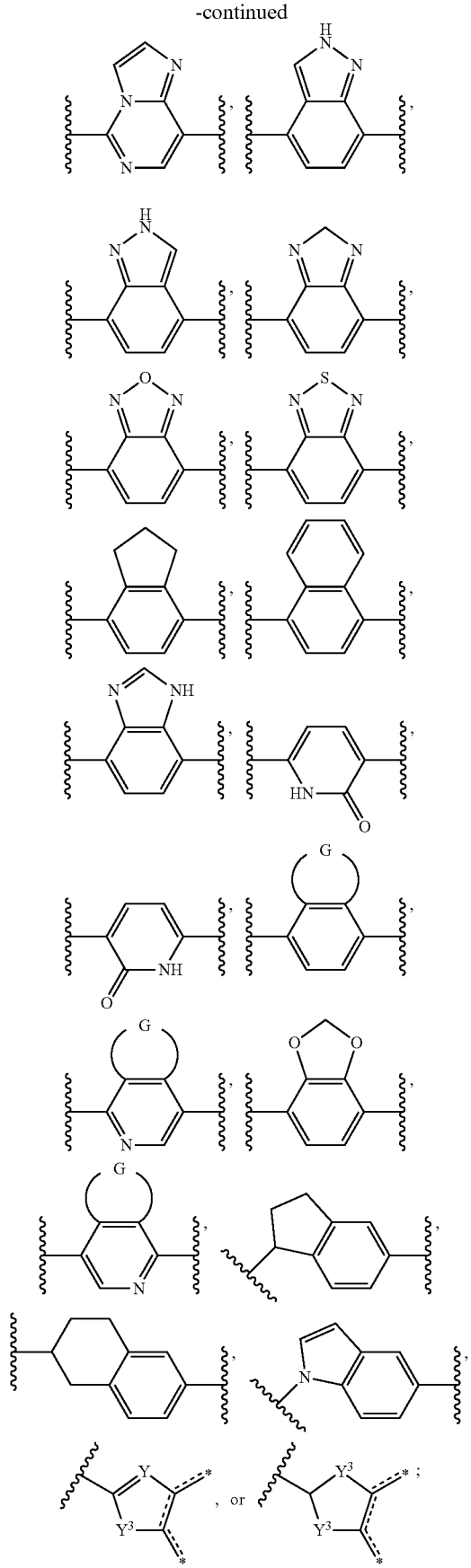
wherein the rings in A is unsubstituted or substituted with one or more substituents selected from alkyl, halo, cyano, or oxo;
B is selected from:
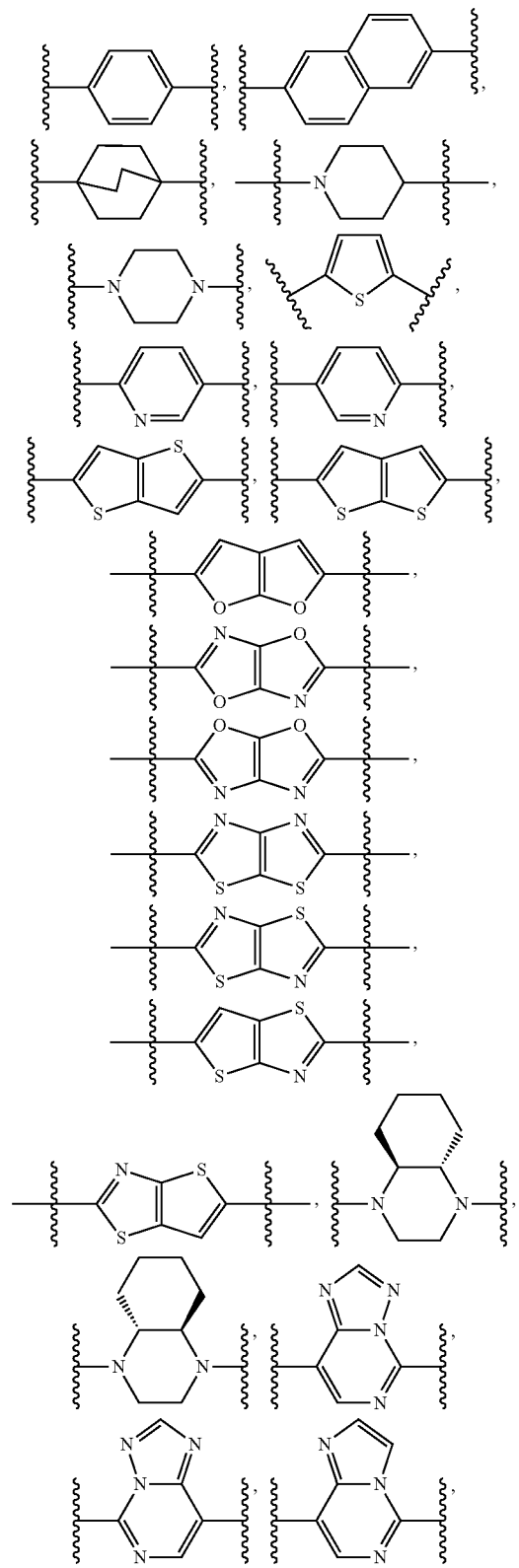

-continued

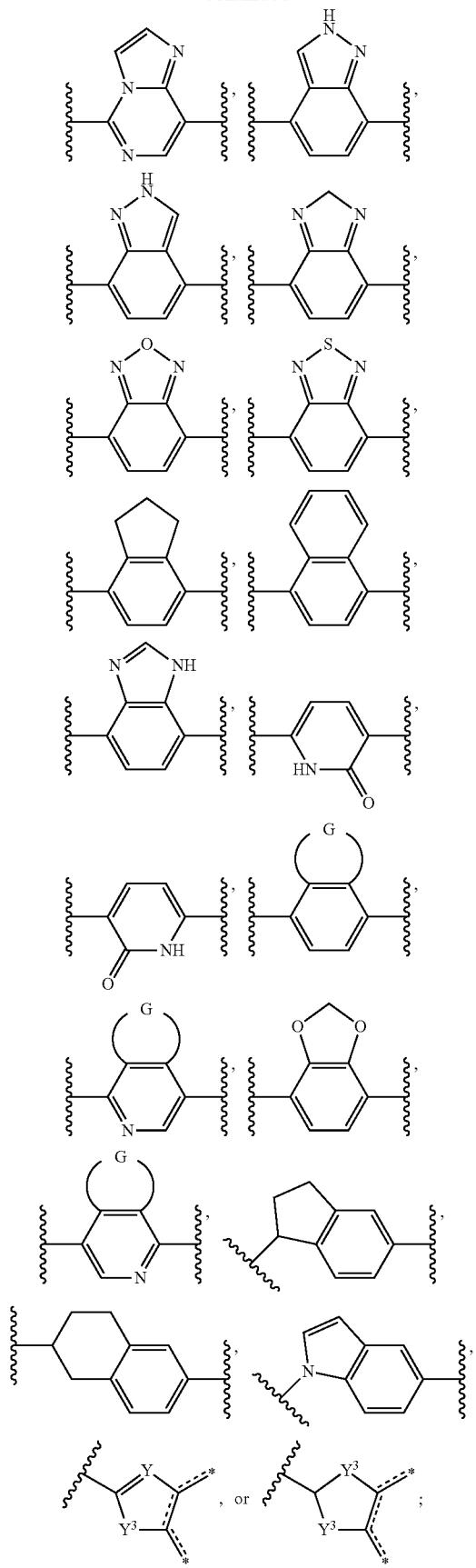

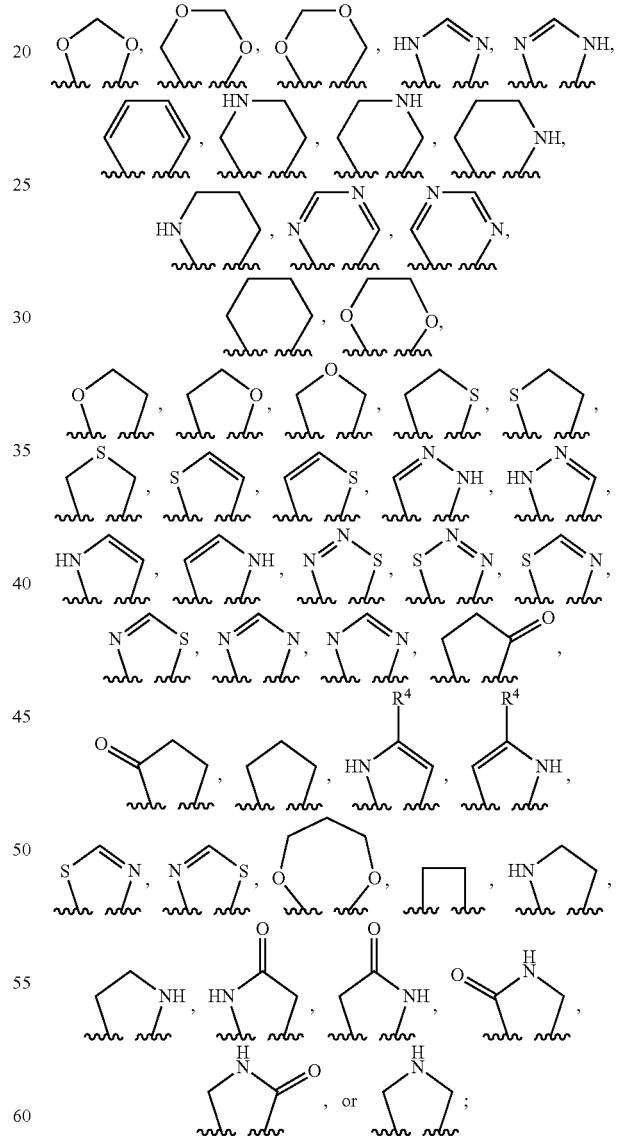

wherein the rings in B are unsubstituted or substituted with one or more substituents selected from alkyl, halo, cyano, or oxo;

C is selected from optionally substituted oxazole, optionally substituted isoxazole, optionally substituted thiazole, and optionally substituted isothiazole;

$L^1$ is selected from a bond, a —CH$_2$O— linker, a —OCH$_2$— linker, a —CH=CH— linker, a —NH- linker, a =C(R$^{15}$)— linker, or a —C(R$^{15}$)= linker;

$L^2$ is selected from a bond, a —CH$_2$O— linker, a —OCH$_2$— linker, a —CH=CH— linker, or a —NH- linker; and $L^5$ are each independently selected from a bond, a —CH$_2$O— linker, a —OCH$_2$— linker, a —CH=CH— linker, or a 4-7 membered heterocycle.

In an embodiment of the second aspect, G is selected from:

wherein each $R^4$ is independently selected from H or alkyl.

In an embodiment of the second aspect, $R^6$ is H.

In an embodiment of the second aspect, m=1; $R^2$ is hydrogen and $R^3$ is selected from phenyl, imidazole, pyridine, thiazole, or oxazole.

In an embodiment of the second aspect, m=1; $R^2$ and $R^3$ are joined together with the atom to which they are attached to form an optionally substituted azetidine, an optionally substituted oxetane, an optionally substituted beta-lactam, an optionally substituted tetrahydropyran, an optionally substituted cyclopropyl, an optionally substituted cyclobutyl, an optionally substituted cyclopentyl, or an optionally substituted cyclohexyl.

In an embodiment of the second aspect, $R^2$ and $R^3$ are joined together with the atom to which they are attached to form a cyclopropyl.

In an embodiment of the second aspect, $R^2$ and $R^3$ are joined together with the atom to which they are attached to form a 1-optionally substituted azetidine, and wherein the substituent is selected from the group consisting of alkyl, aryl, benzyl, ester, sulfonyl and amido.

In an embodiment of the second aspect, $R^2$ and $R^3$ are joined together with the atom to which they are attached to form a cyclobutyl.

In an embodiment of the second aspect, $R^2$ and $R^3$ are joined together with the atom to which they are attached to form a cyclopentyl.

In an embodiment of the second aspect, $R^2$ and $R^3$ are joined together with the atom to which they are attached to form a cyclohexyl.

In an embodiment of the second aspect, wherein A is phenyl, B is phenyl, L is a bond, and $L^3$ selected from:

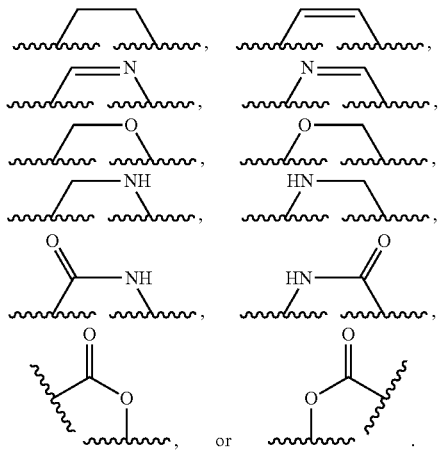

In an embodiment of the second aspect, $L^3$ is

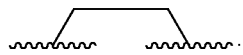

In an embodiment of the second aspect, L is a bond and wherein R is selected from:

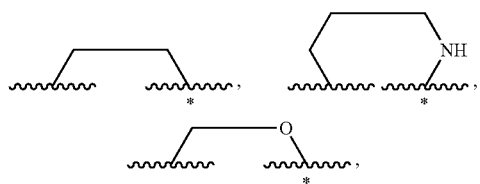

wherein * is a point of attachment of $R^3$ to A.

In an embodiment of the second aspect, A is phenyl and wherein B is selected from:

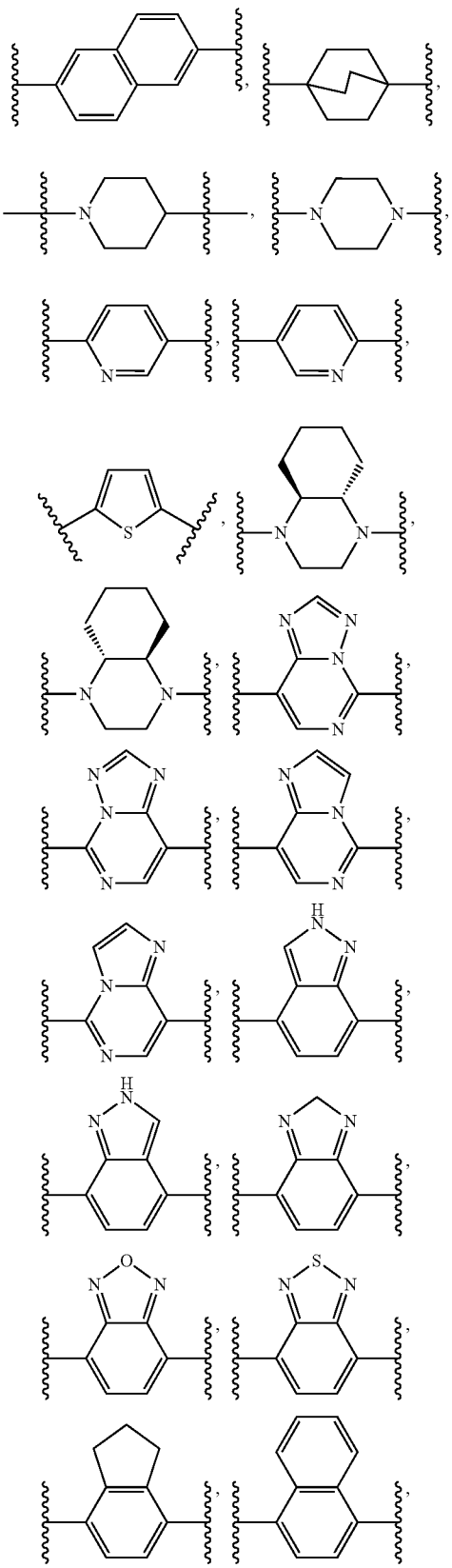

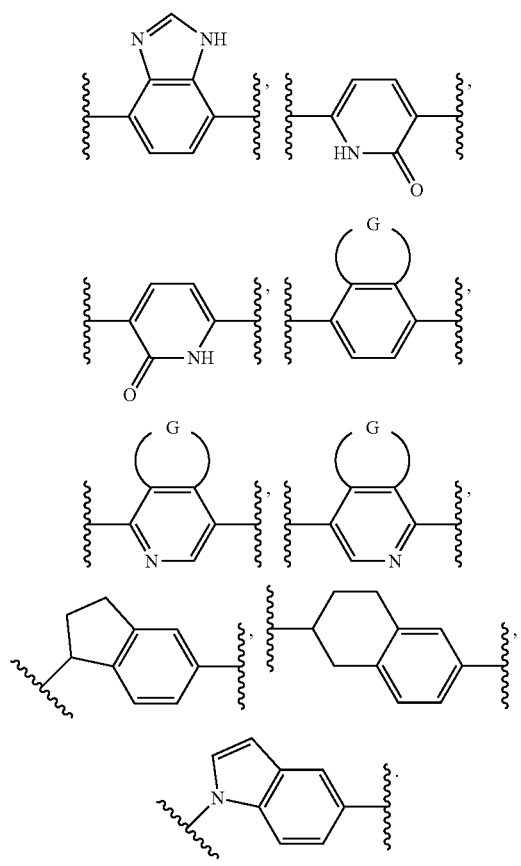
In an embodiment of the second aspect, B is phenyl and wherein A is selected from:
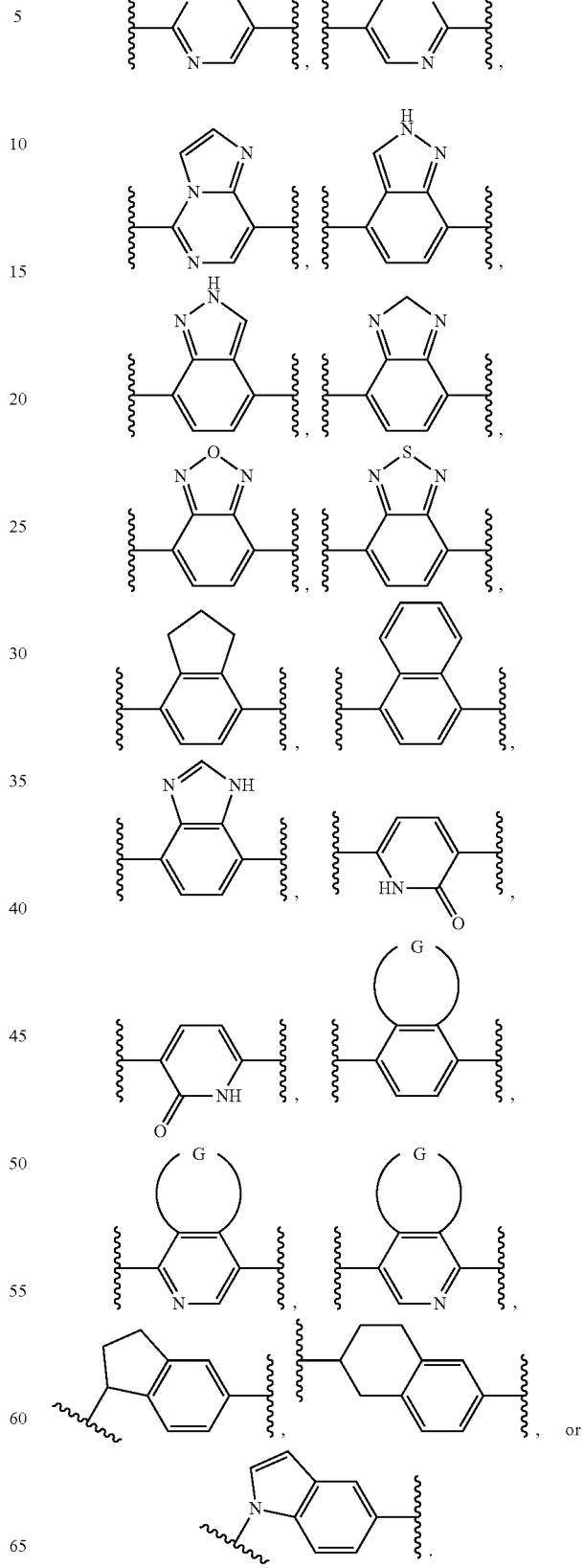

In an embodiment of the second aspect, A is phenyl and B is

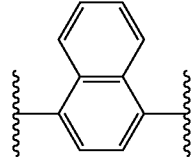 [SMILES: *c1ccc(*)c2ccccc12]

or wherein B is phenyl and A is

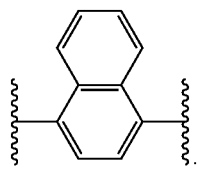 [SMILES: *c1ccc(*)c2ccccc12]

In an embodiment of the second aspect, A is phenyl and B is

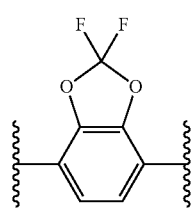 [SMILES: *c1ccc(*)c2c1OC(F)(F)O2]

or wherein B is phenyl and A is

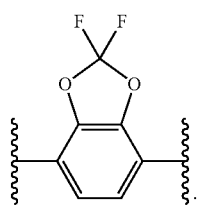 [SMILES: *c1ccc(*)c2c1OC(F)(F)O2]

In an embodiment of the second aspect, A is phenyl and B is

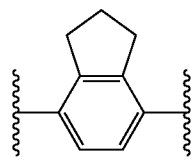 [SMILES: *c1ccc(*)c2c1CCC2]

or wherein B is phenyl and A is

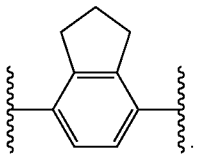 [SMILES: *c1ccc(*)c2c1CCC2]

In an embodiment of the second aspect, A is phenyl and B is

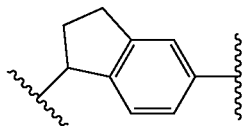 [SMILES: *c1ccc2c(c1)CCC2*]

or B is phenyl and A is

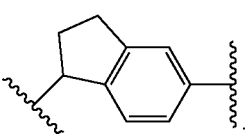 [SMILES: *c1ccc2c(c1)CCC2*]

In an embodiment of the second aspect, A is phenyl and B is

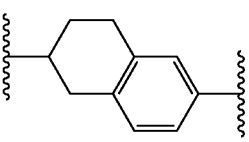 [SMILES: *c1ccc2c(c1)CCC(*)C2]

or B is phenyl and A is

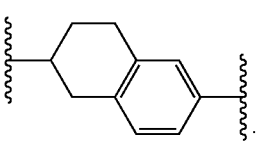 [SMILES: *c1ccc2c(c1)CCC(*)C2]

In an embodiment of the second aspect, A is phenyl and B is

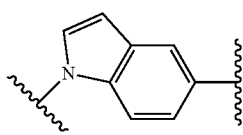 [SMILES: *c1ccc2c(ccn2*)c1]

or B is phenyl and A is

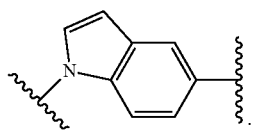 [SMILES: *c1ccc2c(ccn2*)c1]

In an embodiment of the second aspect, A is phenyl and B is

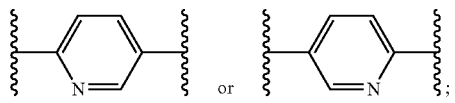 [SMILES: *c1ccc(*)nc1 ; "or" ; *c1ccc(*)nc1 ; ";"]

or wherein B is phenyl and A is

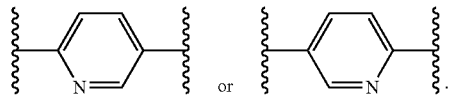

In a third aspect, the compound or pharmaceutically acceptable salt thereof of the first aspect is also represented by Formula (Ib):

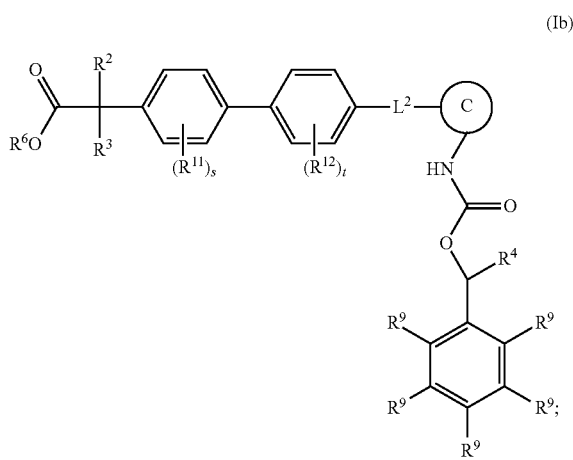

each $R^2$ and $R^3$ is independently selected from H, alkyl, and aryl; or $R^2$ and $R^3$ are joined together with the atom to which they are attached to form an optionally substituted cycloalkyl or an optionally substituted heterocycle; each $R^4$ is independently selected from H and alkyl; and $L^2$ is a bond, —O—, —C(O)—, or —CH$_2$—; each $R^{11}$ and $R^{12}$ is independently selected from alkyl, halogen, or cyano; s is an integer of 0-4; and t is an integer of 0-4.

In an embodiment of the third aspect, wherein $R^2$ and $R^3$ are joined together with the atom to which they are attached to form an optionally substituted azetidine, an optionally substituted oxetane, an optionally substituted beta-lactam, an optionally substituted tetrahydropyran, or an optionally substituted cyclopropyl, an optionally substituted cyclobutyl, an optionally substituted cyclopentyl, or an optionally substituted cyclohexyl.

In an embodiment of the third aspect, $R^2$ and $R^3$ are joined together with the atom to which they are attached to form an optionally substituted cyclopropyl.

In an embodiment of the third aspect, $R^2$ and $R^3$ are joined together with the atom to which they are attached to form an optionally substituted cyclobutyl.

In an embodiment of the third aspect, $R^2$ and $R^3$ are joined together with the atom to which they are attached to form an optionally substituted cyclopentyl.

In an embodiment of the third aspect, $R^2$ and $R^3$ are joined together with the atom to which they are attached to form an optionally substituted cyclohexyl.

In an embodiment of the third aspect, $R^2$ and $R^3$ are joined together with the atom to which they are attached to form an optionally substituted oxetane.

In an embodiment of the third aspect, $R^2$ and $R^3$ are joined together with the atom to which they are attached to form an optionally substituted tetrahydropyran.

In an embodiment of the third aspect, $R^2$ and $R^3$ are joined together with the atom to which they are attached to form an 1-optionally substituted azetidine, and wherein the substituent is selected from the group consisting of alkyl, aryl, benzyl, ester, sulfonyl and amido.

In an embodiment of the third aspect, $R^2$ and $R^3$ are joined together with the atom to which they are attached to form an optionally substituted beta-lactam.

In an embodiment of the third aspect, $R^6$ is H.

In an embodiment of the third aspect, $R^2$ and $R^3$ are both H.

In an embodiment of the third aspect, $R^4$ is $C_{1-3}$ alkyl.

In an embodiment of the third aspect, at least one $R^9$ is halogen or alkyl.

In an embodiment of the third aspect, all $R^9$ are hydrogen.

In an embodiment of the third aspect, at least one $R^{11}$ is halogen, alkyl or cyano.

In a further embodiment, at least one $R^{11}$ is halogen.

In an embodiment of the third aspect, at least one $R^{12}$ is halogen, alkyl, or cyano. In a further embodiment, at least one $R^{12}$ is halogen.

In an embodiment of the third aspect, both s and t are zero.

In an embodiment of the third aspect,

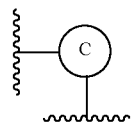

is optionally substituted

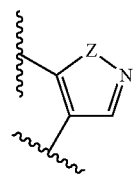

wherein Z is selected from $NR^{10}$, or S.

In an embodiment of the third aspect,

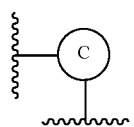

is

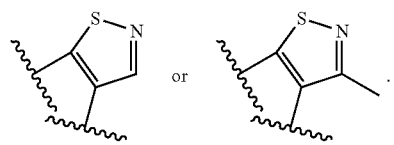

In an embodiment of the third aspect,

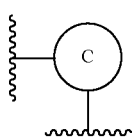

is

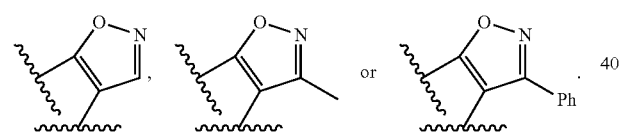

In an embodiment of the third aspect,

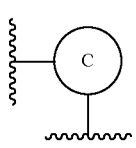

is optionally substituted

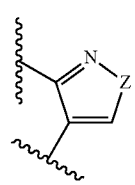

wherein Z is selected from NR[10], O, or S.

In an embodiment of the third aspect,

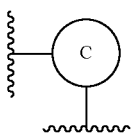

is optionally substituted

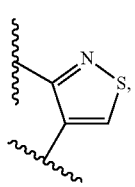

optionally substituted

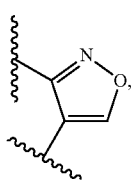 [SMILES: *c1conc1*]

or optionally substituted

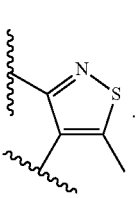

In an embodiment of the third aspect,

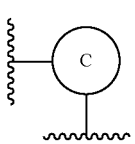

is optionally substituted

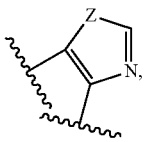

wherein Z is selected from O and S.

In an embodiment of the third aspect,

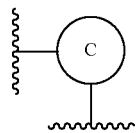

is

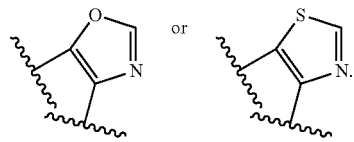 [SMILES: *c1ncoc1* ; "or" ; *c1ncsc1*]

In an embodiment of the third aspect,

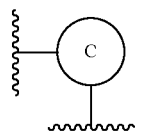

is optionally substituted

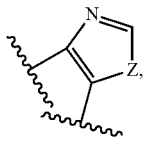

wherein Z is selected from O and S.

In an embodiment of the third aspect,

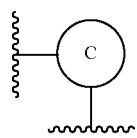

is

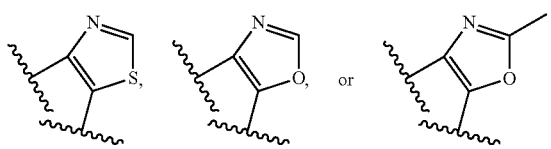

In an embodiment of the third aspect,

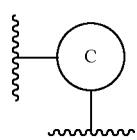

is selected from optionally substituted:

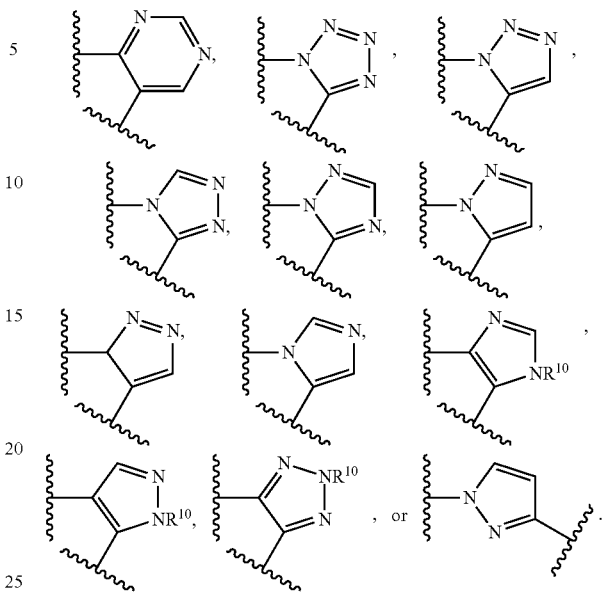

In an embodiment of the third aspect,

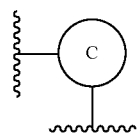

is

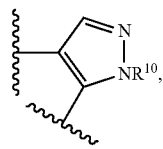

and wherein $R^{10}$ is $C_{1-3}$ alkyl or $C_{3-6}$ cycloalkyl.

In an embodiment of the third aspect,


is

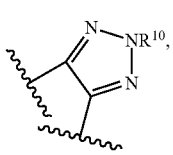

and wherein $R^{10}$ is hydrogen or $C_{1-3}$ alkyl.

In an embodiment of the third aspect,
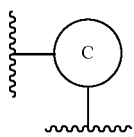
is
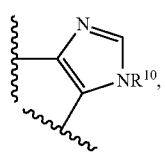
wherein R¹⁰ is hydrogen or $C_{1-3}$ alkyl.
In an embodiment of the third aspect,
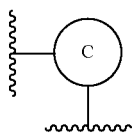
is
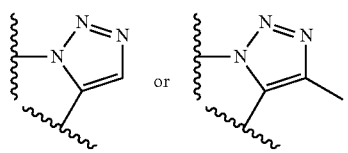
In an embodiment of the third aspect,
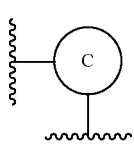
is
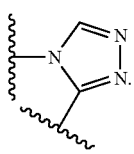 [SMILES: *c1nncn1*]
In an embodiment of the third aspect,
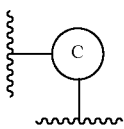
is
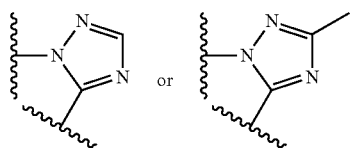
In an embodiment of the third aspect,
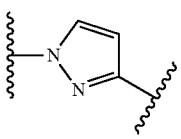
is
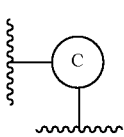
In an embodiment of the third aspect,
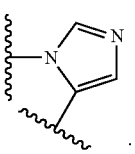
is
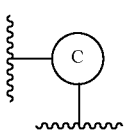
In an embodiment of the third aspect, is optionally substituted

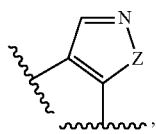

wherein Z is O or S. In a particular embodiment,

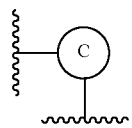

is optionally substituted

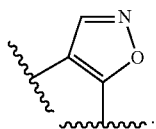

In an embodiment of the third aspect,

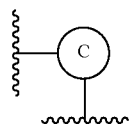

is optionally substituted

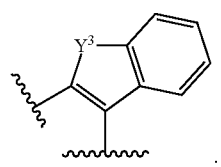

In an embodiment of the third aspect,

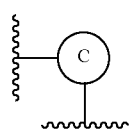

is optionally substituted

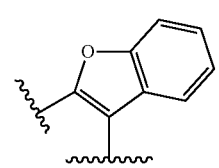 [SMILES: *c1oc2ccccc2c1*]

or optionally substituted

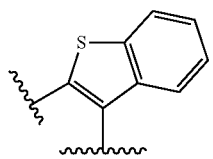

and wherein the phenyl moiety in C is optionally substituted with one or more alkyl or halogen.

In an embodiment of the third aspect,

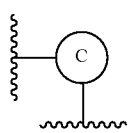

is

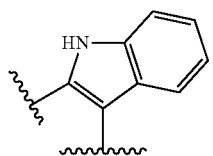

and wherein the phenyl moiety in C is optionally substituted with one or more alkyl or halogen group.

In an embodiment of the third aspect,

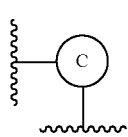

is optionally substituted

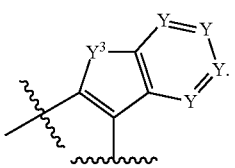

In an embodiment of the third aspect,

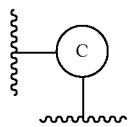

is optionally substituted

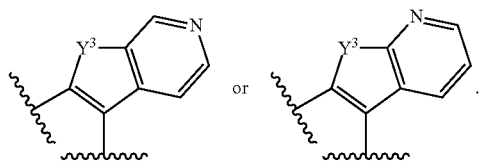

In an embodiment of the third aspect,

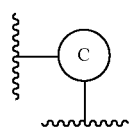

is optionally substituted

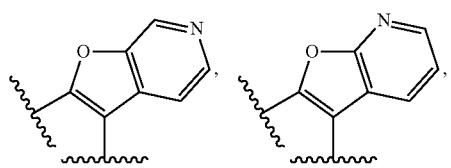 [SMILES: *c1oc2cnccc2c1* ; *c1oc2ncccc2c1*]

or optionally substituted

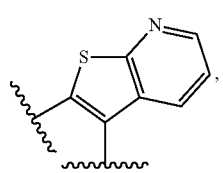 [SMILES: *c1sc2ncccc2c1*]

wherein optionally substituent in ring C is $C_{1-3}$ alkyl or $C_{1-3}$ haloalkyl.

In an embodiment of the third aspect,

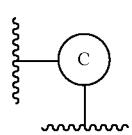

is selected from

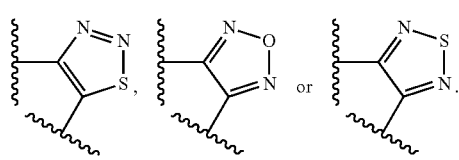

In an embodiment of the third aspect,

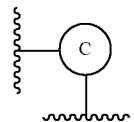

is optionally substituted

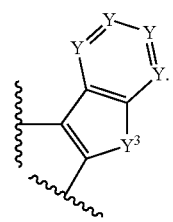

In an embodiment of the third aspect,

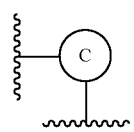

is optionally substituted

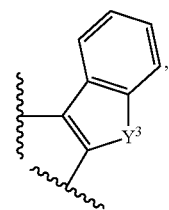

wherein $Y^3$ is O or S.

In an embodiment of the third aspect,

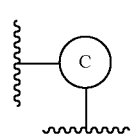

is optionally substituted

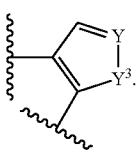

In a further embodiment,
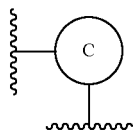
is
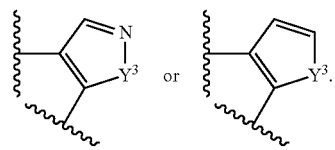
In an embodiment of the third aspect,
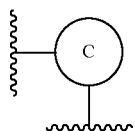
is optionally substituted
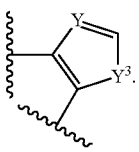
In a further embodiment,
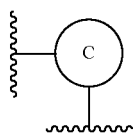
is optionally substituted
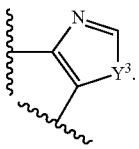
In an embodiment of the third aspect,
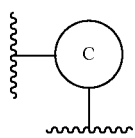
is selected from optionally substituted
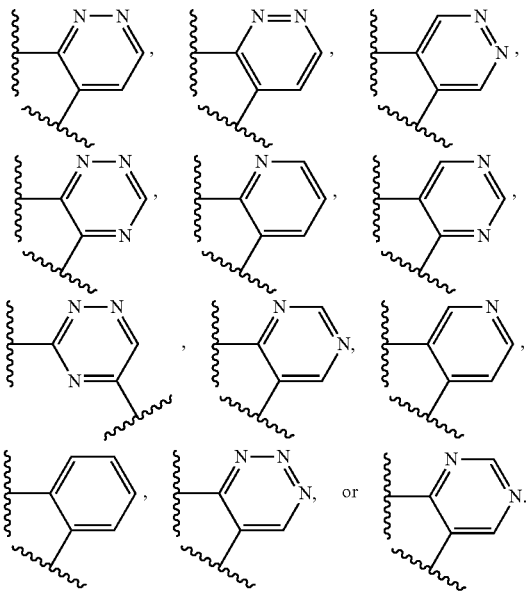
In an embodiment of the third aspect,
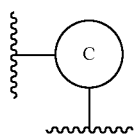
is optionally substituted
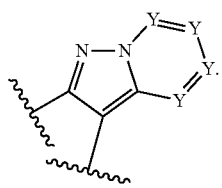
In a further embodiment,
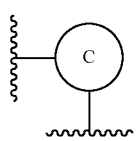
is selected from optionally substituted:
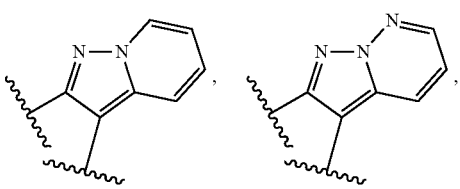

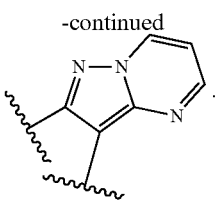

In an embodiment of the third aspect,

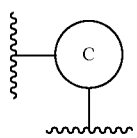

is optionally substituted

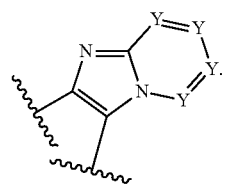

In a further embodiment,

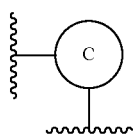

is selected from optionally substituted:

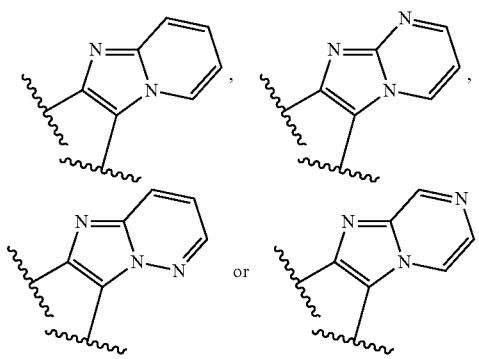

In an embodiment of the third aspect, the optionally substituted group in ring C is selected from $C_{1-3}$ alkyl, halogen, $C_{3-6}$ cycloalkyl, $C_{1-3}$ haloalkyl, or cyano.

In an embodiment of the third aspect, $R^6$ is hydrogen.

In an embodiment of the third aspect, $R^6$ is $C_{1-3}$ alkyl.

In a fourth aspect, the compound or pharmaceutically acceptable salt thereof of the first aspect is also represented by Formula (Ic):

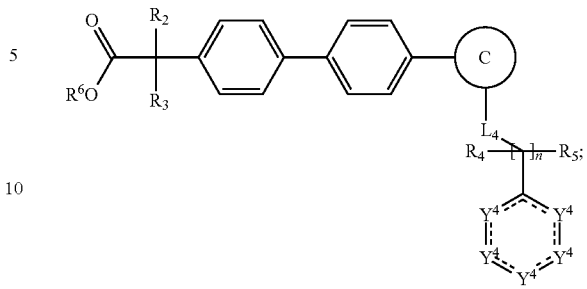

(Ic)

each $R^2$ and $R^3$ is independently selected from H, alkyl, and aryl; or $R^2$ and $R^3$ are joined together with the atom to which they are attached to form an optionally substituted cycloalkyl or an optionally substituted heterocycle; and

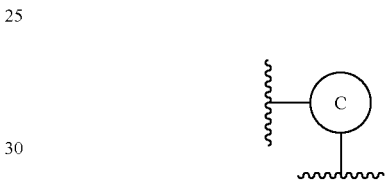

is selected from optionally substituted oxazole, optionally substituted isoxazole, optionally substituted isothiazole, and optionally substituted thiazole.

In one embodiment of the fourth aspect, $R^6$ is H.

In one embodiment of the fourth aspect, $R^6$ is $C_{1-3}$ alkyl.

In an embodiment of the fourth aspect, at least one of $R^2$ and $R^3$ is a $C_{1-3}$ alkyl.

In an embodiment of the fourth aspect, $R^2$ and $R^3$ are joined together with the atom to which they are attached to form a cyclopropyl.

In an embodiment of the fourth aspect, $R^2$ and $R^3$ are both H.

In an embodiment of the fourth aspect, n is 1 and $R^4$ and $R^5$ are both H.

In an embodiment of the fourth aspect, n is 0.

In an embodiment of the fourth aspect, $R^4$ and $R^5$ are joined together with the atom to which they are attached to form an optionally substituted cycloalkyl.

In an embodiment of the fourth aspect, n is 1, 2 or 3, and $R^4$ and $R^5$ are each independently selected from H and $C_{1-3}$ alkyl.

In an embodiment of the fourth aspect, at least one $Y^4$ is $CR^9$.

In an embodiment of the fourth aspect, at least one $R^9$ is halogen.

In an embodiment of the fourth aspect, at least one $Y^4$ is N.

In an embodiment of the fourth aspect, all $R^9$ are hydrogen.

In an embodiment of the fourth aspect, Formula (Ic) is also represented by Formula (Im):

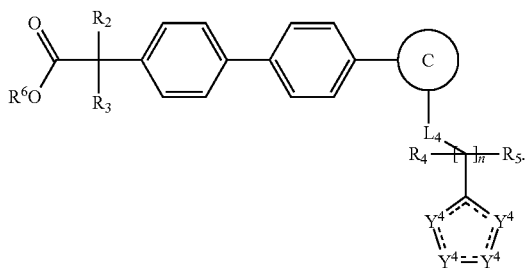
(Im)

In an embodiment of the fourth aspect, at least one ------ between two $Y^4$ atoms is a double bond. In a further embodiment,

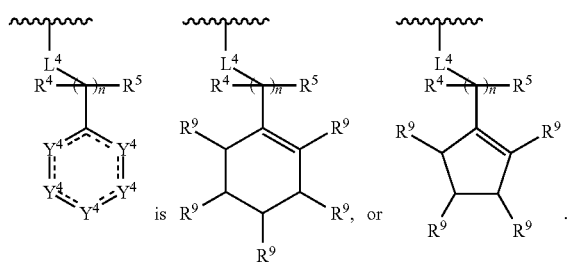 is

In an embodiment of the fourth aspect,

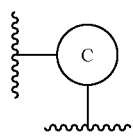 is

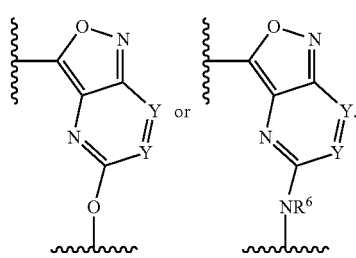

In an embodiment of the fourth aspect, each Y is CH.

In an embodiment of the fourth aspect, $L^4$ is a —NH—SO$_2$— linkage.

In an embodiment of the fourth aspect, $L^4$ is

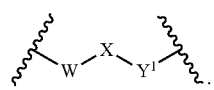

In an embodiment of the fourth aspect, $L^4$ is

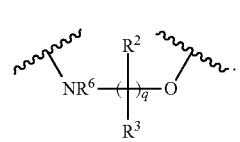

In an embodiment of the fourth aspect, $L^4$ is

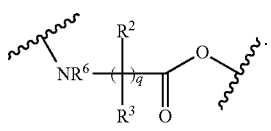

In an embodiment of the fourth aspect, $L^4$ is

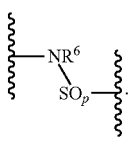

In an embodiment of the fourth aspect, $L^4$ is

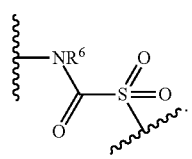

In an embodiment of the fourth aspect, each $R^6$ is independently selected from H or alkyl.

In an embodiment of the fourth aspect, q is 1 or 2 and, in the definition of $L^4$, $R^2$ and $R^3$ are each independently selected from H or $C_{1-3}$ alkyl.

In an embodiment of the fourth aspect, $L^4$ comprises a —NH—SO$_2$—NH— linkage.

In an embodiment of the fourth aspect, $L^4$ comprises a —NH—C(=O)—SO$_2$— linkage.

In an embodiment of the fourth aspect, $L^4$ comprises a —NH—(CH$_2$)$_2$—O— linkage.

In an embodiment of the fourth aspect, $L^4$ comprises a —NH—CH$_2$—C(=O)—O— linkage.

In a fifth aspect, the compound or pharmaceutically acceptable salt thereof of the first aspect is also represented by Formula (Id) or (Ie):

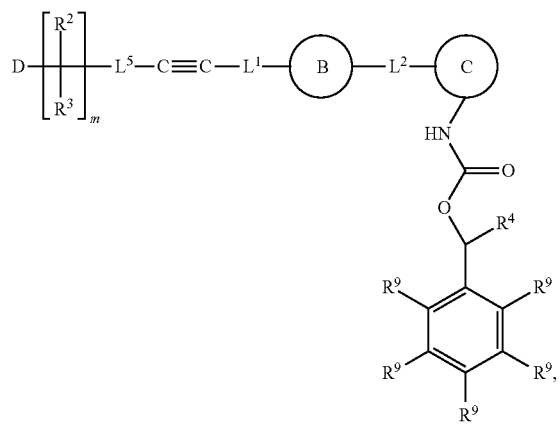

(Id)

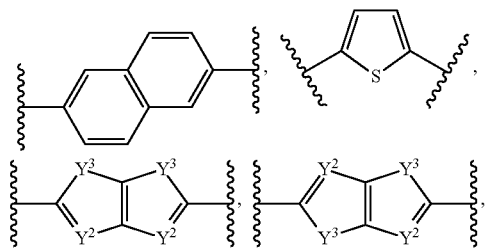

wherein each ring in B is unsubstituted or substituted with one or more substituents selected from alkyl, halogen, or oxo.

In an embodiment of the fifth aspect, each A or B is independently selected from:

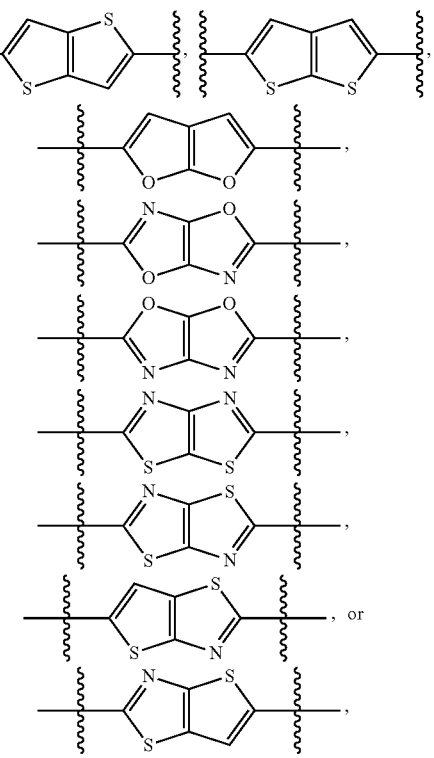

(Ie)

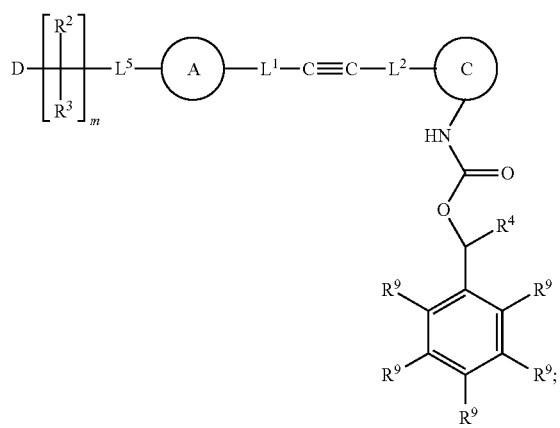

$L^1$, $L^2$ and $L^5$ are each independently selected from a bond, a —CH$_2$O— linker, a —OCH$_2$— linker, and a —CH═CH— linker; and $R^4$ is selected from H and alkyl.

In an embodiment of the fifth aspect, D is COOH.

In one embodiment of the fifth aspect, A is selected from phenyl,

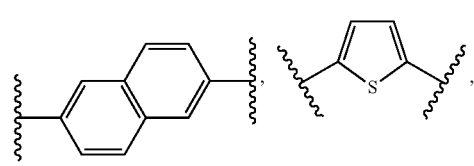

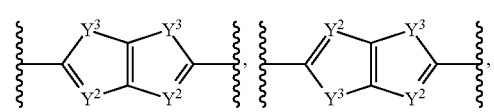

wherein each ring in A is unsubstituted or substituted with one or more substituents selected from alkyl, halogen, or oxo.

In one embodiment of the fifth aspect, B is selected from phenyl, each is unsubstituted or substituted with one or more substituents selected from alkyl, halo or oxo.

In an embodiment of the fifth aspect, $R^4$ is selected from H and $C_{1-3}$ alkyl.

In an embodiment of the fifth aspect, at least one $R^9$ is $C_{1-3}$ alkyl or halogen.

In an embodiment of the fifth aspect, A or B is

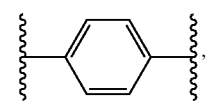 [SMILES: *c1ccc(*)cc1]

unsubstituted or substituted with one or more substituents selected from alkyl, halo or oxo.

In an embodiment of the fifth aspect, D is —C(═O)OH and $R^2$ and $R^3$ are joined together with the atom to which they are attached to form a cyclopropyl.

In an embodiment of the fifth aspect, D is —C(=O)OH, and both R² and R³ are hydrogen.

In an embodiment of the fifth aspect, A or B is

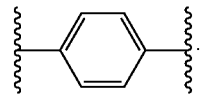 [SMILES: *c1ccc(*)cc1]

In an embodiment of the fifth aspect, A or B is

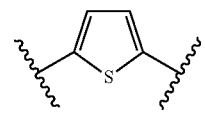 [SMILES: *c1ccc(*)s1]

unsubstituted or substituted with one or more substituents selected from alkyl, halo or oxo.

In an embodiment of the fifth aspect, A or B is

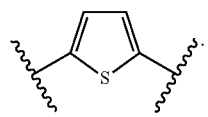

In an embodiment of the fifth aspect, A or B is

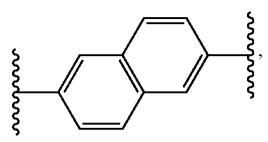 [SMILES: *c1ccc2cc(*)ccc2c1]

unsubstituted or substituted with one or more substituents selected from alkyl, halo or oxo. In a further embodiment, A or B is

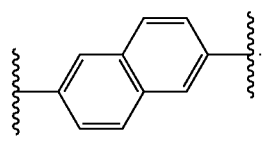 [SMILES: *c1ccc2cc(*)ccc2c1]

In an embodiment of the fifth aspect,

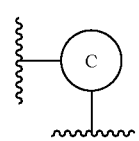

is selected from an optionally substituted oxazole, an optionally substituted isoxazole, an optionally substituted thiazole, an optionally substituted isothiazole, an optionally substituted

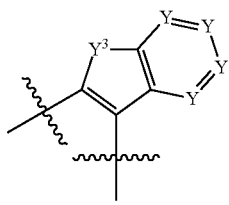

or an optionally substituted

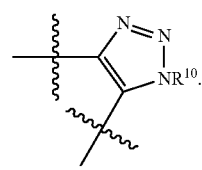

In an embodiment of the fifth aspect,

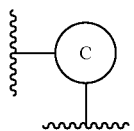

is selected from

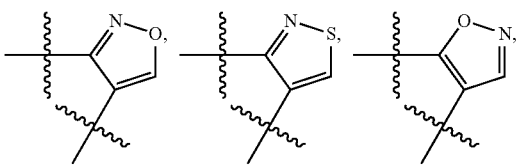

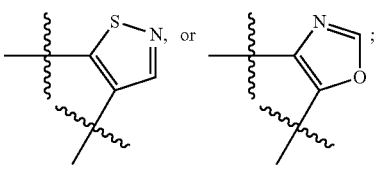

and wherein each ring C is unsubstituted or substituted with one or more substituents selected from $C_{1-3}$ alkyl, $C_{3-6}$ cycloalkyl, halogen or cyano.

In an embodiment of the fifth aspect,

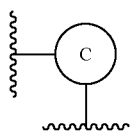

is selected from

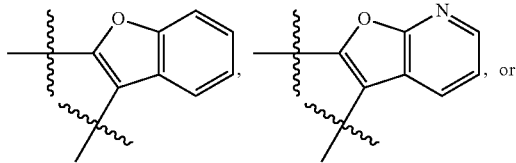

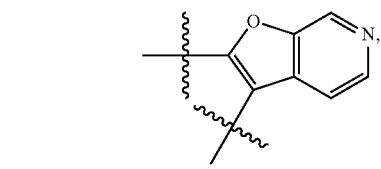

wherein each ring C is unsubstituted or substituted with one or more substituents selected from $C_{1-3}$ alkyl, $C_{3-6}$ cycloalkyl, halogen or cyano.

In an embodiment of the fifth aspect,

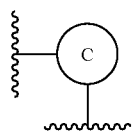

is

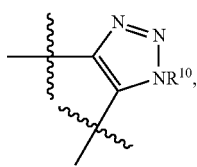

and wherein $R^{10}$ is selected from hydrogen, $C_{1-3}$ alkyl, $C_{3-6}$ cycloalkyl, or cyano.

In an embodiment of the fifth aspect, each ring C is unsubstituted or substituted with one or more substituents selected from $C_{1-6}$ alkyl, $C_{3-6}$ cycloalkyl, halogen or cyano.

In an embodiment of the fifth aspect, both $L^1$ and $L^2$ are a bond.

In an embodiment of the fifth aspect, one of $L^1$ and $L^2$ is a bond and the other is independently selected from a bond, a —$CH_2O$— linker, a —$OCH_2$— linker, and a —CH=CH— linker.

In an embodiment of the fifth aspect, one of $L^1$ and $L^2$ is a bond and the other is a —$CH_2O$— linker.

In an embodiment of the fifth aspect, one of $L^1$ and $L^2$ is a bond and the other is a —$OCH_2$— linker.

In an embodiment of the fifth aspect, one of $L^1$ and $L^2$ is a bond and the other is a —CH=CH— linker.

In a sixth aspect, the compound or pharmaceutically acceptable salt thereof of the first aspect is also represented by Formula (If):

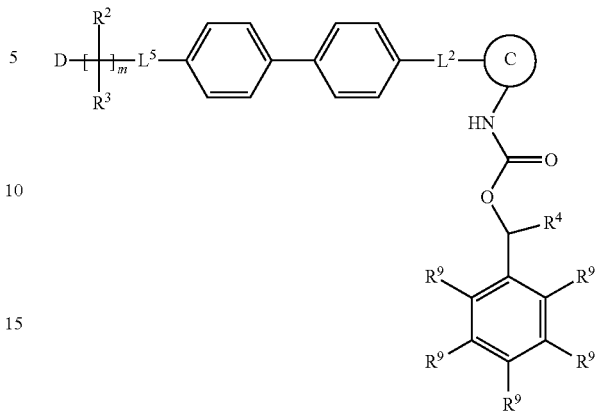

wherein each $R^2$ and $R^3$ is independently selected from H, alkyl, and aryl; or $R^2$ and $R^3$ are joined together with the atom to which they are attached to form an optionally substituted cycloalkyl or an optionally substituted heterocycle; $L^5$ is selected from a bond, or a 4-7 membered heterocycle, $L^2$ is selected from a bond, a —O— linker, a —NH— linker, a —C(O)— linker, a —$CH_2$— linker, a —$CH_2O$— linker, a —$OCH_2$— linker, a —C≡C— linker, or a —CH=CH— linker, and wherein C is selected from optionally substituted oxazole, optionally substituted isoxazole, optionally substituted thiazole and optionally substituted isothiazole.

In one embodiment of the sixth aspect, m is 0.

In one embodiment of the sixth aspect, m is 1.

In one embodiment of the sixth aspect, $L^5$ is a bond.

In one embodiment of the sixth aspect, $L^2$ is a bond.

In one embodiment of the sixth aspect, wherein m=1, $R^2$ and $R^3$ are joined together with the atom to which they are attached to form a cyclopropyl, and D is

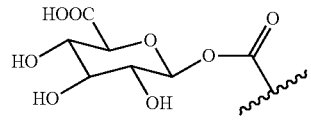

In one embodiment of the sixth aspect, D is C(=O)$OR^6$.

In one embodiment of the sixth aspect, $R^6$ is H.

In one embodiment of the sixth aspect, $L^5$ is selected from optionally substituted pyrrolidine or optionally substituted piperidine.

In one embodiment of the sixth aspect, $L^5$ is

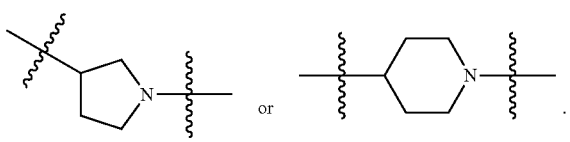 [SMILES: *C1CCN(*)C1 ; *C1CCN(*)CC1]

In a seventh aspect, the compound or pharmaceutically acceptable salt thereof of the first aspect is also represented by Formula (Ii):

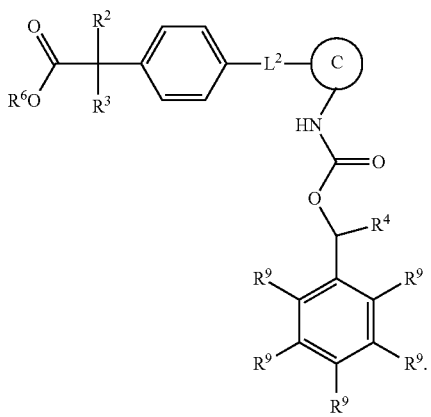

(Ii)

In an embodiment of the seventh aspect, $L^2$ is a bond and C is optionally substituted

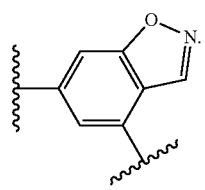 [SMILES: *c1cc(*)c2cnoc2c1]

In an embodiment of the seventh aspect, each $R^2$ and $R^3$ is independently selected from H, alkyl, and aryl; or $R^2$ and $R^3$ are joined together with the atom to which they are attached to form a cyclopropyl.

In an embodiment of the seventh aspect, wherein $R^4$ is H or alkyl.

In an embodiment of the seventh aspect, both $R^6$ and $R^9$ are H.

In an eighth aspect, the compound or pharmaceutically acceptable salt thereof of the first aspect is also represented by Formula (Ij):

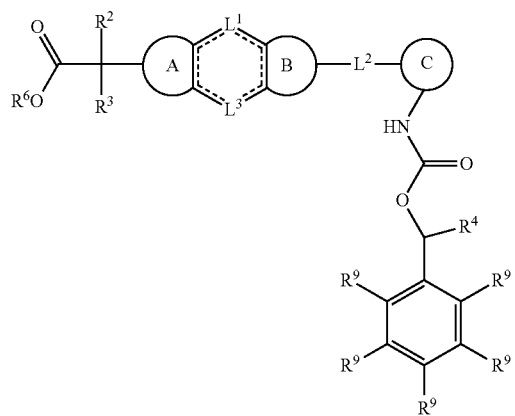

(Ij)

wherein:

A is selected from

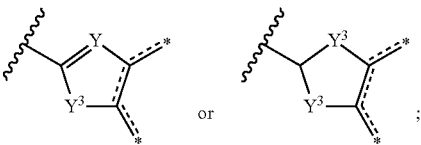

B is selected from

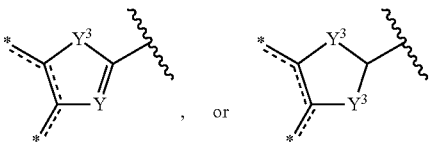

wherein each * is a point of attachment of $L^1$ or $L^3$; and
wherein $L^1$ and $L^3$ are independently a $=C(R^{15})-$ linker, or a $-C(R^{15})=$ linker.

In an embodiment of the eighth aspect, A is

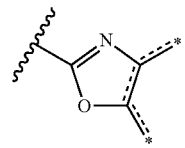

and B is

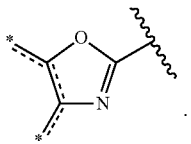

In an embodiment of the eighth aspect, wherein C is optionally substituted isoxazole. In a further embodiment, C is

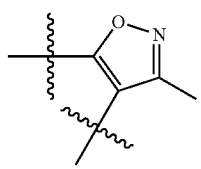

In an embodiment of the eighth aspect, wherein $R^2$ and $R^3$ are joined together with the atom to which they are attached to form a cyclopropyl.

In an embodiment of the eighth aspect, $R^4$ is hydrogen or $C_{1-3}$ alkyl.

In an embodiment of the eighth aspect, wherein Formula (Ij) is selected from:

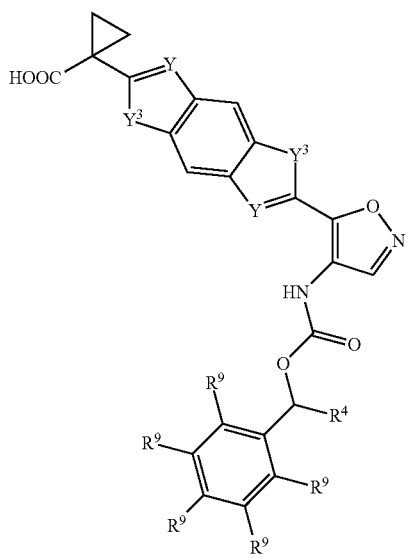
or
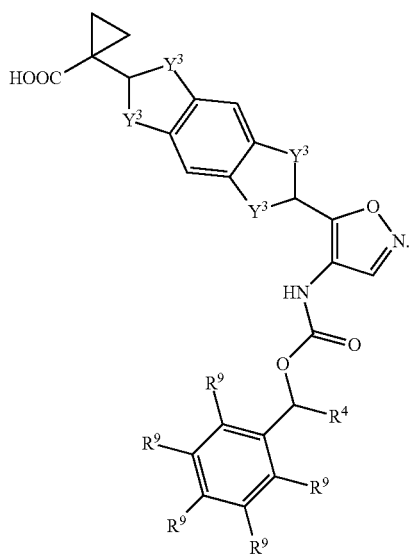
In an nineth aspect; the compound or pharmaceutically acceptable salt thereof of the first aspect is also represented by Formula (Ik):
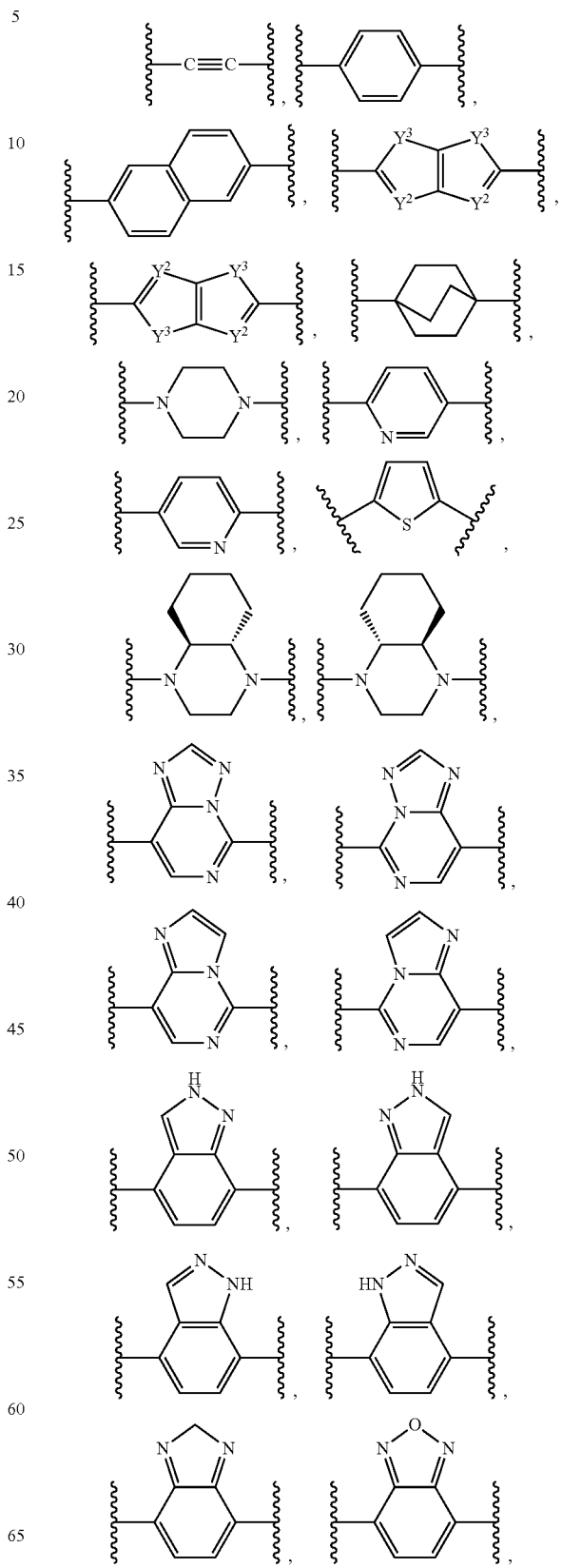
wherein:
A is selected from:

-continued

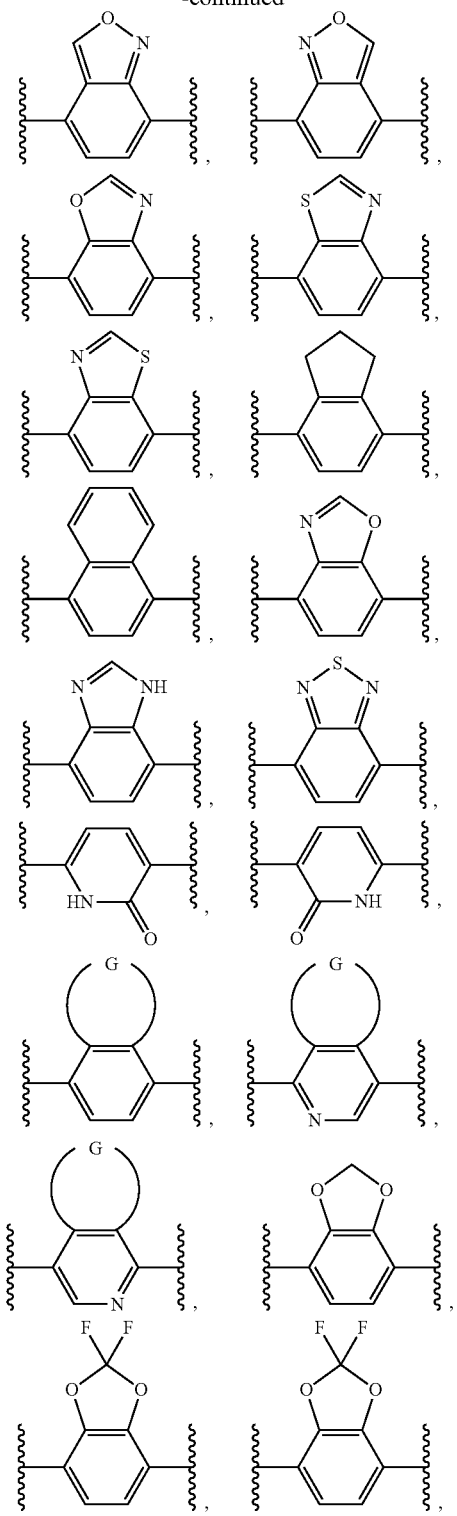

or a ring system selected from 4-7 membered heterocycle, 4-7 membered cyclic hydrocarbyl, 8-11 membered bicyclic heterocycle, or 8-11 membered bicyclic hydrocarbyl, wherein the ring system is non-aromatic, aromatic, or partially aromatic, and wherein the ring system is unsubstituted or substituted with one or more substituents selected from alkyl, halo, or oxo; and B is selected from:

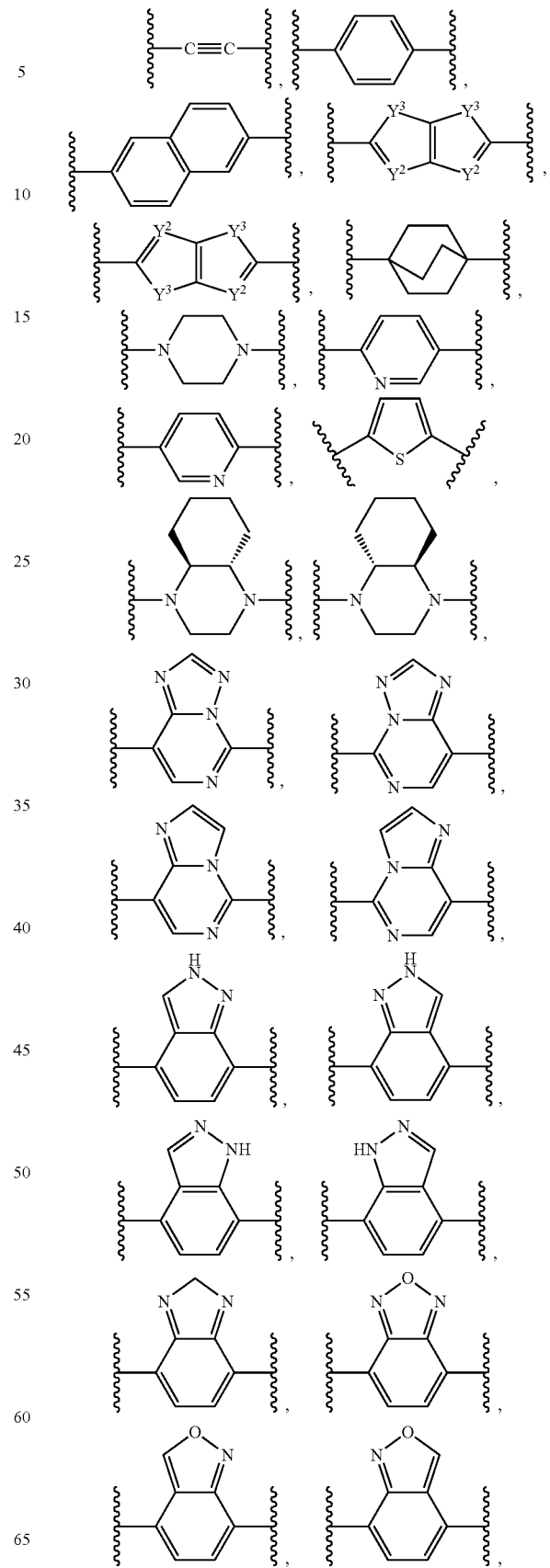

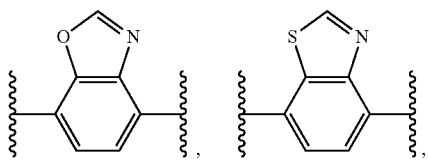
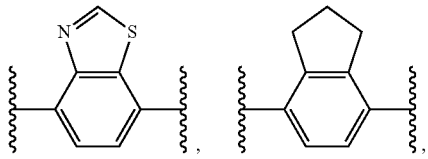
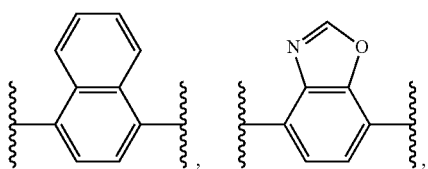
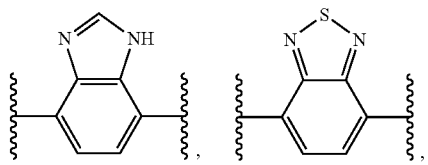
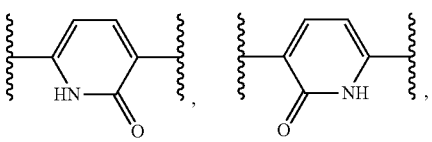
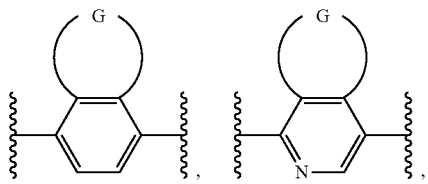
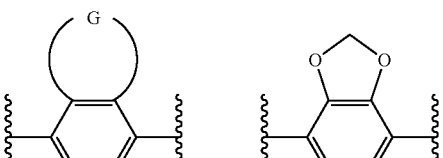
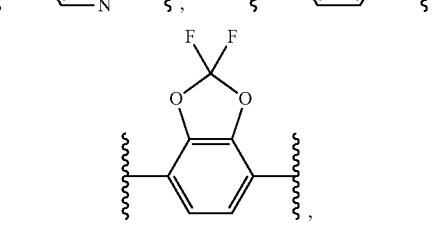

or a ring system selected from 4-7 membered heterocycle, 4-7 membered cyclic hydrocarbyl, 8-11 membered bicyclic heterocycle, or 8-11 membered bicyclic hydrocarbyl, wherein the ring system is non-aromatic, aromatic, or partially aromatic, and wherein the ring system is unsubstituted or substituted with one or more substituents selected from alkyl, halo, or oxo; and

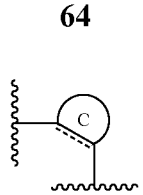

is selected from:

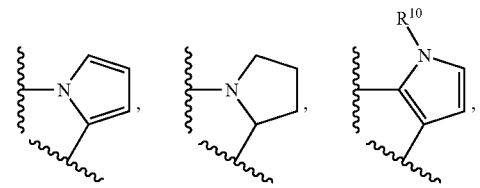
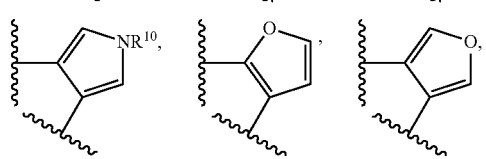
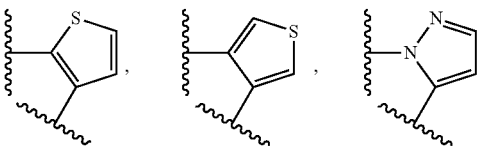
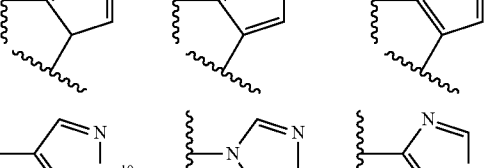
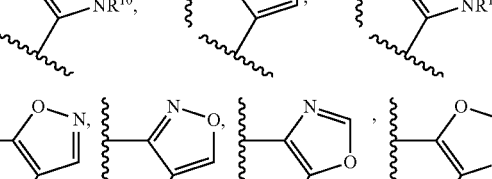
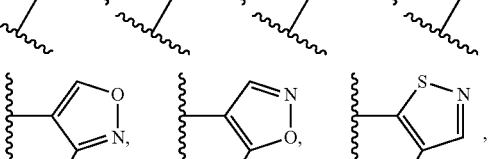
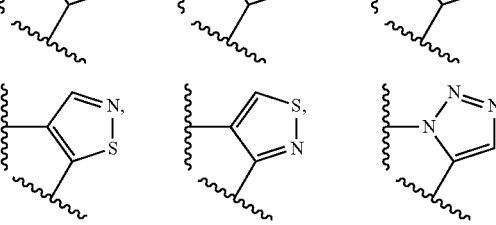

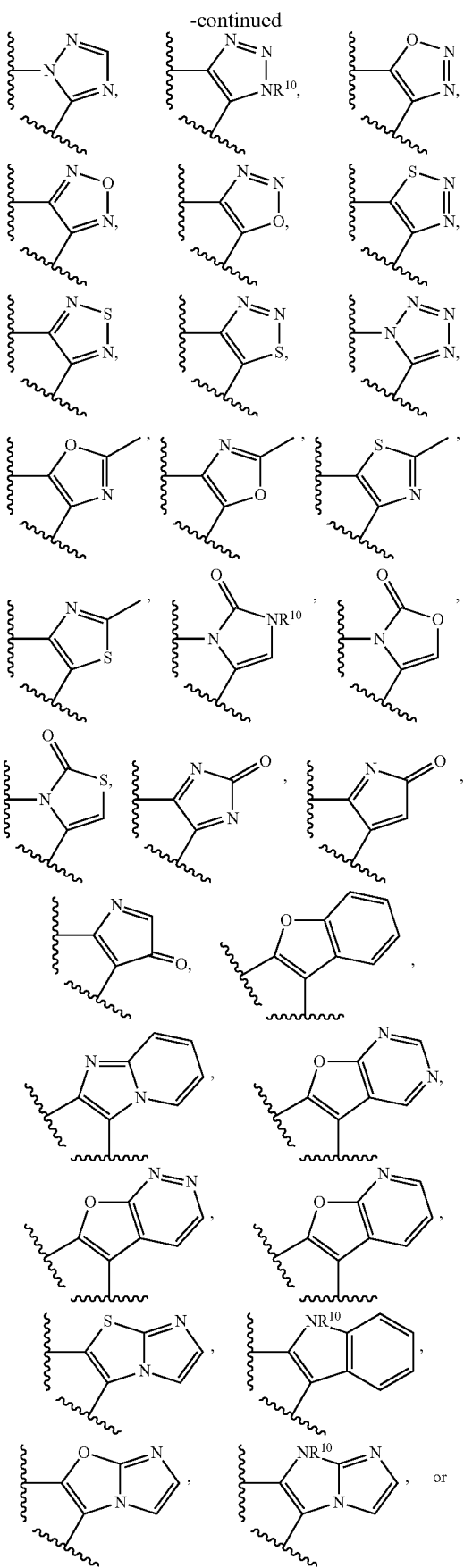
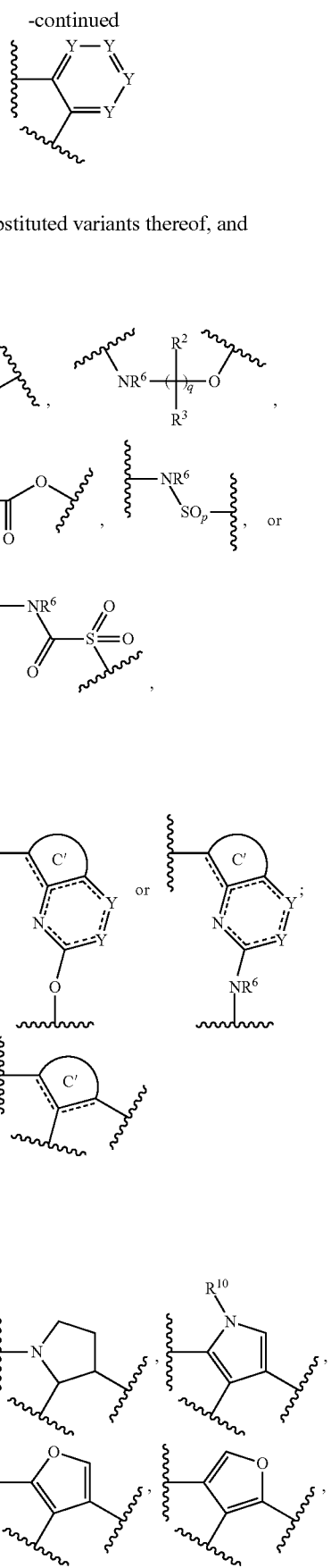
-continued
or optionally substituted variants thereof, and $L^4$ is
or alternatively,
is selected from:

-continued

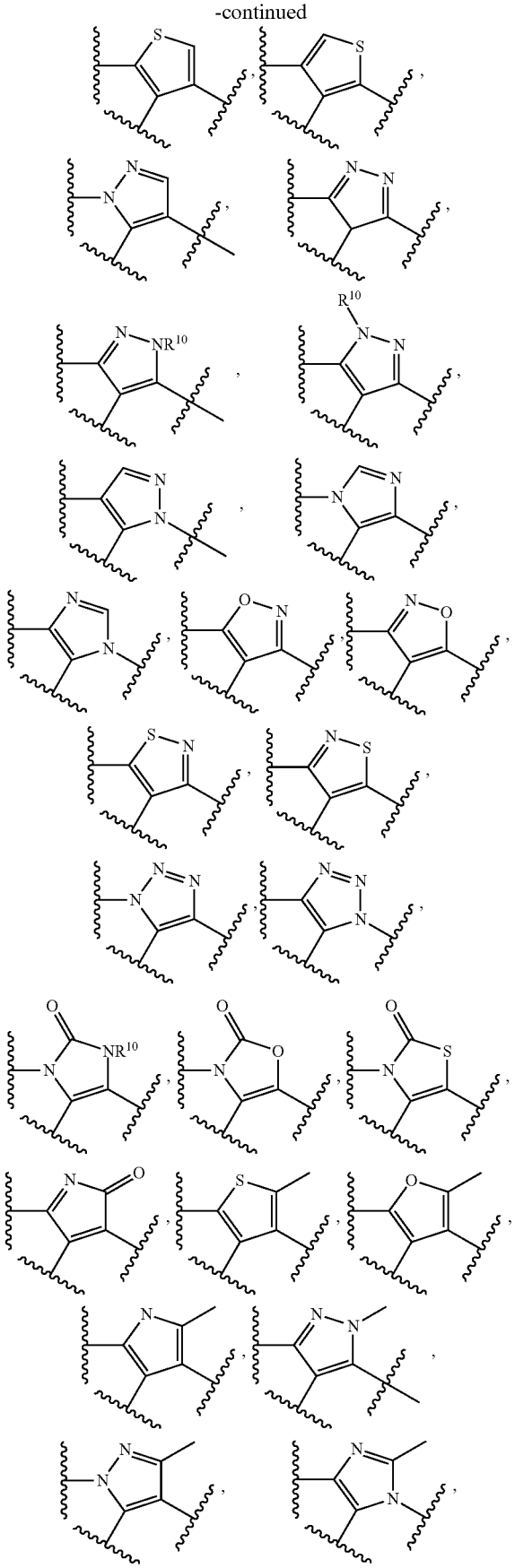

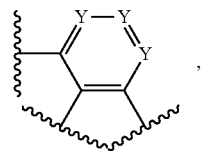

or optionally substituted variants thereof;

$L^1$ and $L^2$ are each independently selected from a bond, a —O— linker, a —C(O)— linker, a —CH$_2$— linker, a —CH$_2$O— linker, a —OCH$_2$— linker, a —C≡C— linker, or a —CH=CH— linker;

$L^3$ is absent,

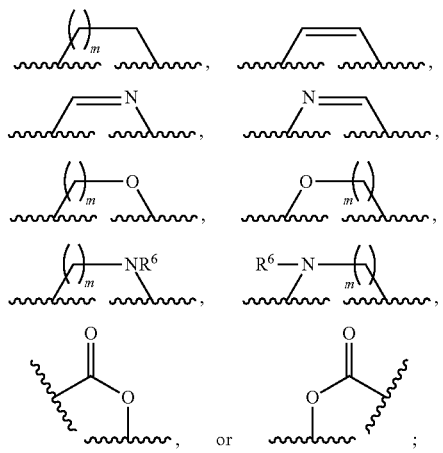

D is selected from

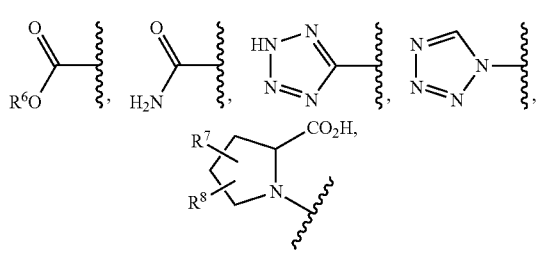

or carboxylic acid isosteres;

$L^5$ is selected from a bond, a —CH$_2$O— linker, a —OCH$_2$— linker, or a —CH=CH— linker;

$R^9$ is selected from H, alkyl or halogen;

each $R^6$ and $R^{10}$ is independently selected from H or alkyl;

$Y^2$ is —CH=, =CH—, or N; and $Y^3$ is $C(R^6)_2$, $NR^6$, O, or S; and provided that at least one of the following conditions is met in the compound of Formula (Ik):

(1) if A and B are each independently selected from phenyl, cyclohexyl, indolyl, 5-membered heteroaryl, 6-membered heteroaryl, and variants thereof substituted with fluoro, trifluoromethyl or methoxy;

if

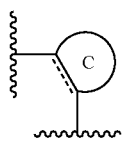

is

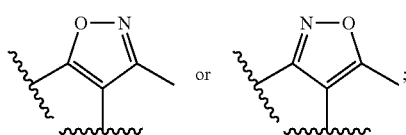

if $L^3$ is absent; if $L^5$ is a bond; and if D is —COOH and m is 1;
then

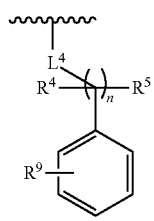

is not

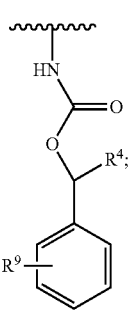

(2) if A and B are both phenyl;
if $L^1$ is a —CH$_2$O— linker, a —OCH$_2$— linker, or a —C≡C— linker;
if

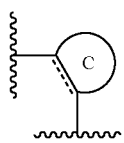

is

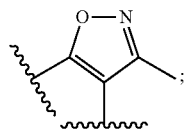 [SMILES: *c1onc(C)c1*]

if $L^3$ is absent; if $L^5$ is a bond; and if D is —COOH and m is 1;
then

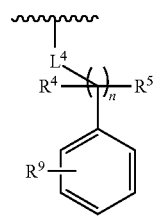

is not

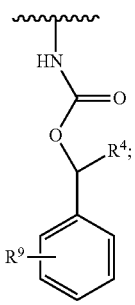

(3) if A and B are both phenyl;
if

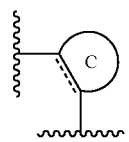

is

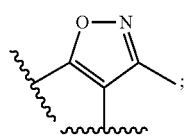 [SMILES: *c1onc(C)c1*]

if $L^1$, $L^2$, and $L^5$ are all a bond; if $L^3$ is absent; and if D is —COOH and m is 1; then $L^4$ is not an amide linkage, a carbamate linkage, a urea linkage, a methyl urea linkage, a —CH$_2$S(═O)CH$_2$— linkage, or a —CH$_2$C(═O)CH$_2$— linkage; and (4) if A and B are both phenyl;
if

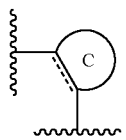

is

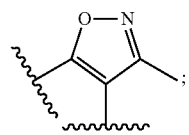 [SMILES: *c1onc(C)c1*]

if $L^1$, $L^2$, and $L^5$ are all a bond; if $L^3$ is absent; if D is —COOH and m is 1; if n is 1; if $R^9$ is chloro; and if $R^4$ and $R^5$ are both H; then $L^4$ is not a —NH—$SO_2$— linkage.

In a tenth aspect, a compound of Formula (II) is provided:

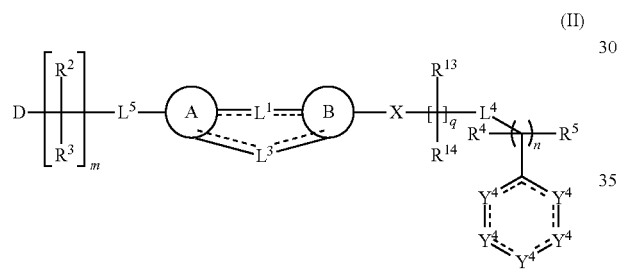

or a pharmaceutically acceptable salt thereof, wherein

A is an acetylene or a ring system selected from 4-7 membered heterocycle, 4-7 membered cyclic hydrocarbyl, 8-11 membered bicyclic heterocycle, or 8-11 membered bicyclic hydrocarbyl, wherein the ring system is non-aromatic, aromatic, or partially aromatic, and wherein the ring system is unsubstituted or substituted with one or more substituents selected from alkyl, halo, cyano, or oxo;

for example, A can be selected from the group consisting of:

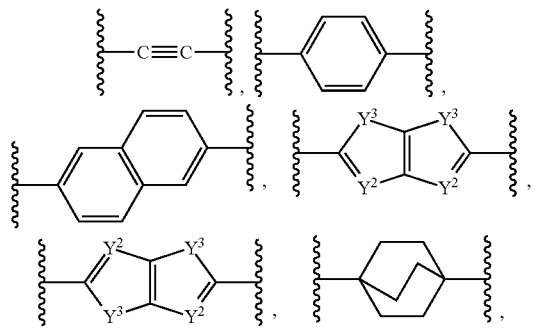

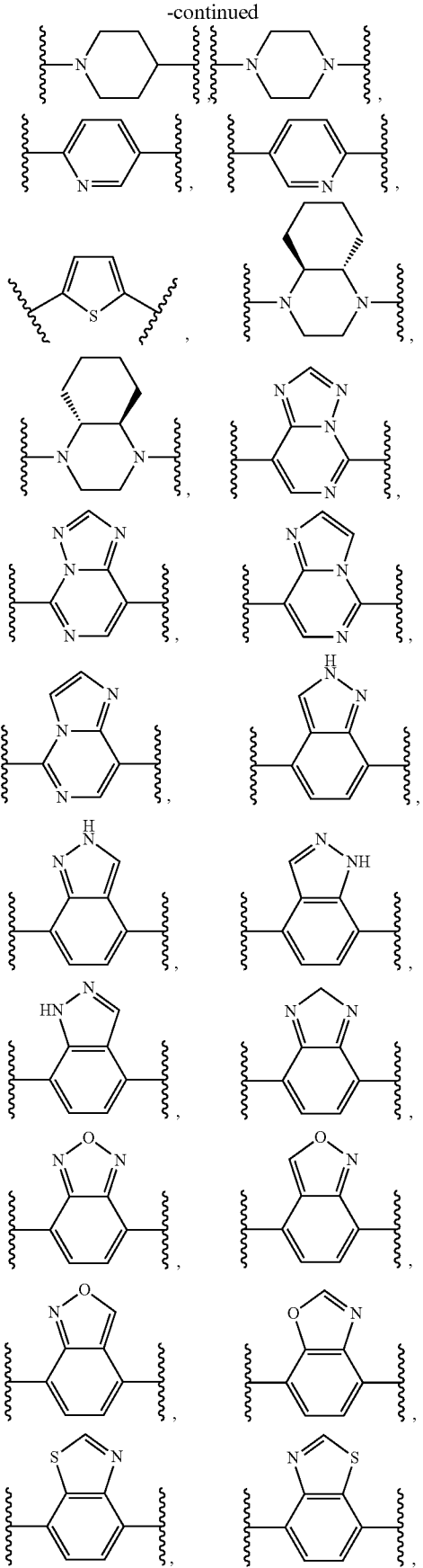

-continued

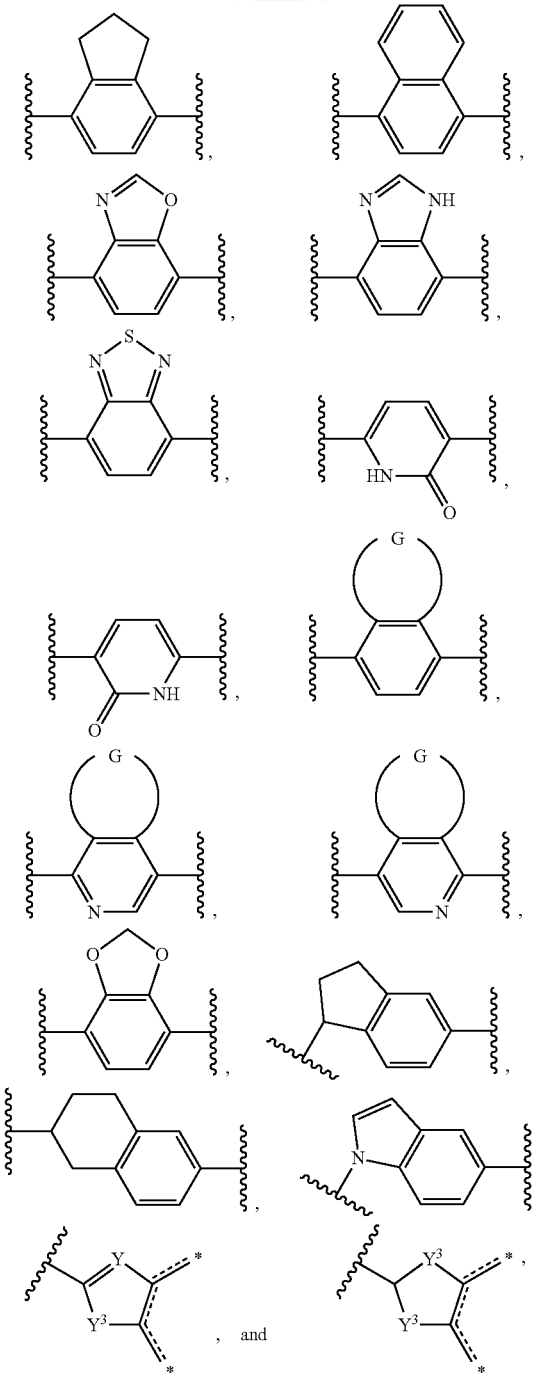

wherein each * is a point of attachment of A to L¹ or L³, and wherein the rings in A are unsubstituted or substituted with one or more substituents selected from alkyl, halo, cyano, or oxo;

B is an acetylene or a ring system selected from 4-7 membered heterocycle, 4-7 membered cyclic hydrocarbyl, 8-11 membered bicyclic heterocycle, or 8-11 membered bicyclic hydrocarbyl, wherein the ring system is non-aromatic, aromatic, or partially aromatic, and wherein the ring system is unsubstituted or substituted with one or more substituents selected from alkyl, halo, cyano, or oxo;

for example, B can be selected from the group consisting of:

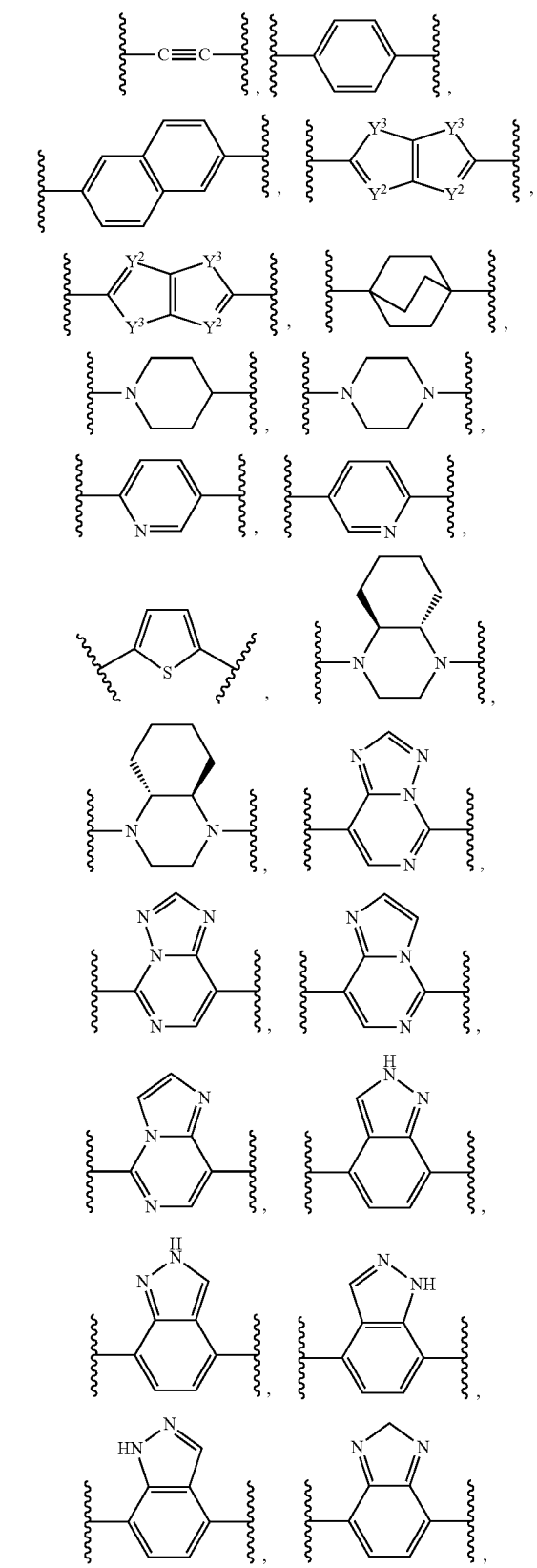

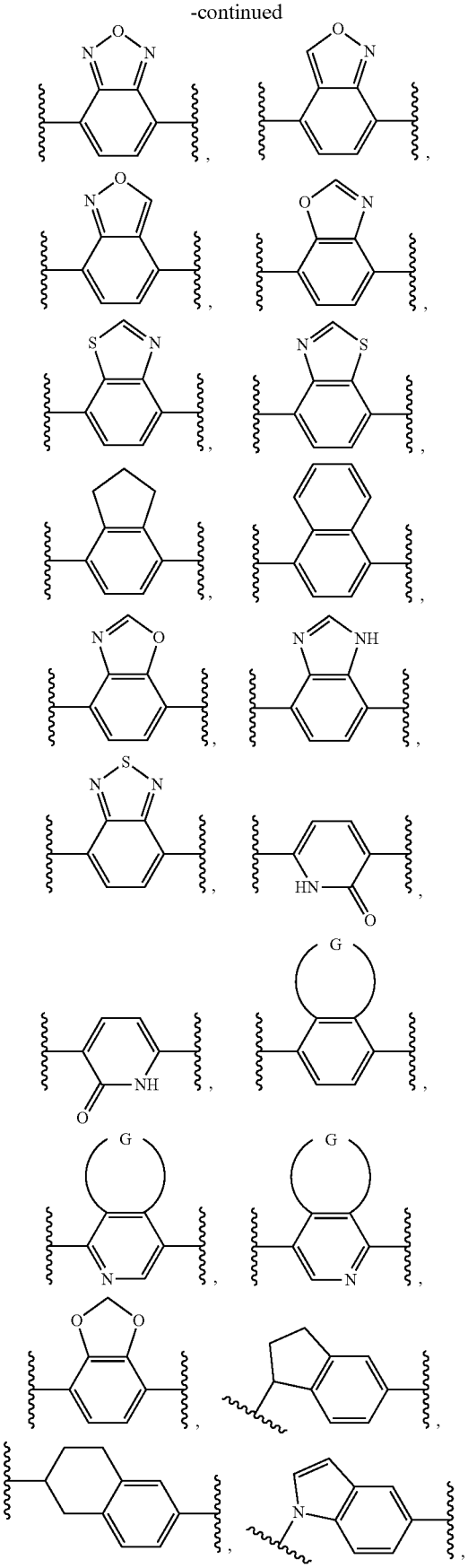

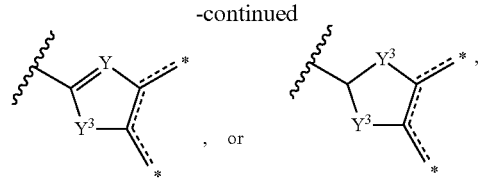

wherein each * is a point of attachment of B to $L^1$ or $L^3$, and wherein the rings in B are unsubstituted or substituted with one or more substituents selected from alkyl, halo, cyano, or oxo;

G together with the atoms to which it is attached forms a ring system selected from 4-7 membered heterocycle, 4-7 membered cyclic hydrocarbyl, 8-11 membered bicyclic heterocycle, 8-11 membered bicyclic hydrocarbyl, wherein the ring system is non-aromatic, aromatic, or partially aromatic, and wherein the ring system is unsubstituted or substituted with one or more substituents selected from alkyl, halo, or oxo;

$L^1$ is selected from a bond, a —O— linker, a —NH— linker, a —C(O)— linker, a —CH$_2$— linker, a —CH$_2$O— linker, a —OCH$_2$— linker, a —C≡C— linker, a —CH=CH— linker, a =C(R$^{15}$)— linker, or a —C(R$^{15}$)= linker;

$L^3$ is absent,

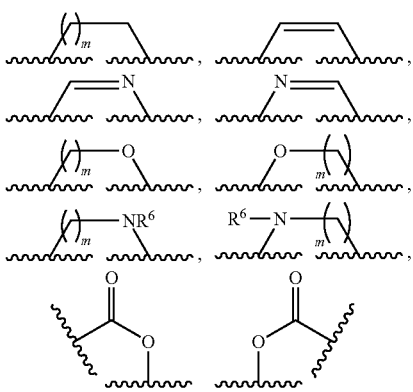

a =C(R$^{15}$)— linker, or a —C(R$^{15}$)= linker;

$L^4$ is

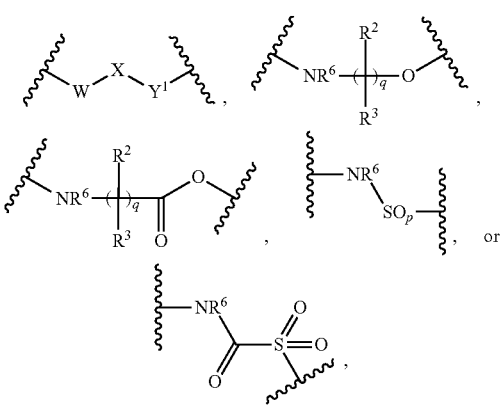

W is C(R$^6$)$_2$, NR$^6$, or O;

each X is independently

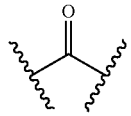 [SMILES: *C(*)=O]

or S(O)$_p$;
each Y is independently selected from CR$^6$ or N;
each Y$^1$ is independently C(R$^6$)$_2$, NR$^6$, or O;
each Y$^4$ is independently CR$^9$ or N, wherein one Y$^4$ can be absent;
Y$^2$ is —CH=, =CH—, or N;
Y$^3$ is C(R$^6$)$_2$, NR$^6$, O, or S;
L$^5$ is selected from a bond, a —CH$_2$O— linker, a —OCH$_2$— linker, a —CH=CH— linker, a —NH— linker, or a 4-7 membered heterocycle;
D is selected from

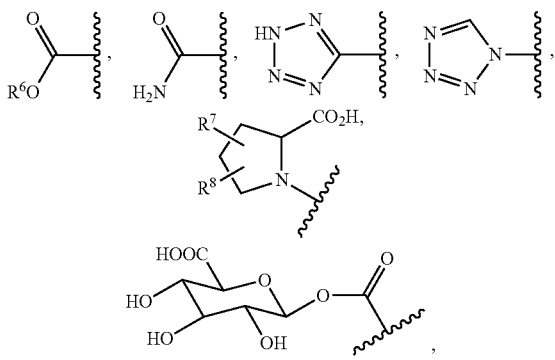

or carboxylic acid isosteres;
R$^2$ and R$^3$ are each independently selected from H, alkyl, aryl, or heteroaryl; or R$^2$ and R$^3$ are joined together with the atom to which they are attached to form an optionally substituted cycloalkyl or an optionally substituted heterocycle; or R$^2$ is selected from H, alkyl, or aryl and R$^3$ is joined to an atom alpha to a point of attachment of L$^5$ to A to form an optionally substituted cycloalkyl or an optionally substituted heterocycle; or R$^3$ is selected from H, alkyl, and aryl and R$^2$ is joined to an atom alpha to a point of attachment of L$^5$ to A to form an optionally substituted cycloalkyl or an optionally substituted heterocycle;
each R$^4$ and R$^5$ is independently selected from H and alkyl; or R$^4$ and R$^5$ are joined together with the atom to which they are attached to form an optionally substituted cycloalkyl or optionally substituted heterocycle;
each R$^6$ is independently selected from H, alkyl, halo, aryl, or cycloalkyl;
each R$^7$ and R$^8$ is independently H or C$_{1-6}$ alkyl, or R$^7$ and R$^8$ are joined together with the atom or atoms to which they are attached to form a spirocyclic heterocycle, a spirocyclic carbocycle, a fused heterocycle, or a fused carbocycle;
each R$^9$ is independently selected from H, alkyl or halogen or two R$^9$ are joined together with the atoms to which they are attached to form an optionally substituted carbocycle or an optionally substituted heterocycle;
each R$^{15}$ is independently selected from H, alkyl, halo or cyano;
each R$^{13}$ and R$^{14}$ is independently selected from H, optionally substituted alkyl, optionally substituted aryl, or optionally substituted arylalkyl; or R$^{13}$ and R$^{14}$ are joined together with the atom to which they are attached to form an optionally substituted cycloalkyl or an optionally substituted heterocycle;
m is independently an integer from 0-3;
n is an integer from 0-3;
p is an integer from 1-2;
q is an integer from 1-6; and
═══ represents a single or double bond.

In an embodiment of the tenth aspect, the compound of Formula (II) is an (R)-isomer represented by Formula (IIc):

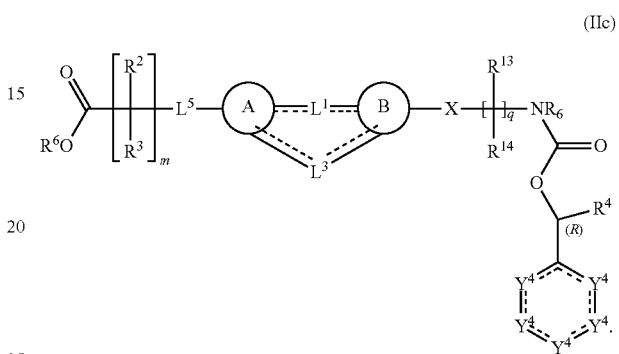

(IIc)

In an embodiment of the tenth aspect, the compound of Formula (II) is an (S)-isomer represented by Formula (IId):

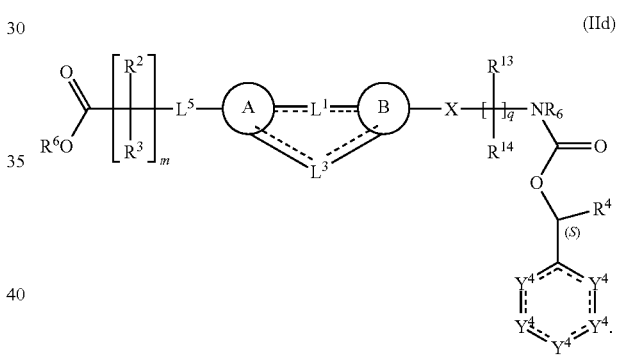

(IId)

In an embodiment of the tenth aspect, the compound of Formula (II) is selected from the compounds of Table 21, and pharmaceutically acceptable salts thereof.

In an eleventh aspect, the compound or pharmaceutically acceptable salt thereof of the tenth aspect is also represented by Formula (IIa):

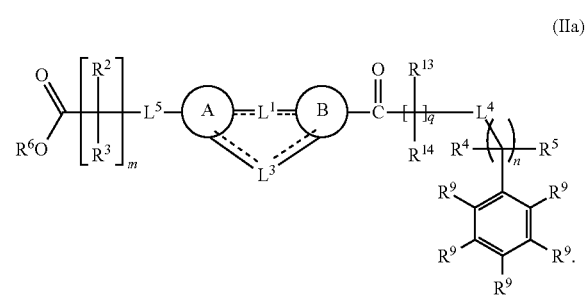

(IIa)

In an embodiment of the eleventh aspect, L$^5$ is selected from a bond, a —CH$_2$O— linker, a —OCH$_2$— linker, a —CH=CH— linker, a 4-7 membered heterocycle.

In an embodiment of the eleventh aspect, $L^1$ is selected from a bond, a —$CH_2O$— linker, a —$OCH_2$— linker, a —CH=CH— linker, a —NH-linker, a =$C(R^{15})$— linker, or a —$C(R^{15})$= linker.

In an embodiment of the eleventh aspect, m is 1, $R^2$ is hydrogen, and $R^3$ is hydrogen.

In an embodiment of the eleventh aspect, m is 1, and wherein $R^2$ and $R^3$ are joined together with the atom to which they are attached to form an optionally substituted azetidine, an optionally substituted oxetane, an optionally substituted beta-lactam, an optionally substituted tetrahydropyran, an optionally substituted cyclopropyl, an optionally substituted cyclobutyl, an optionally substituted cyclopentyl, or an optionally substituted cyclohexyl.

In an embodiment of the eleventh aspect, $R^2$ and $R^3$ are joined together with the atom to which they are attached to form a cyclopropyl.

In an embodiment of the eleventh aspect, wherein A is

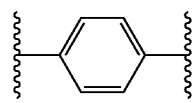

and wherein B is

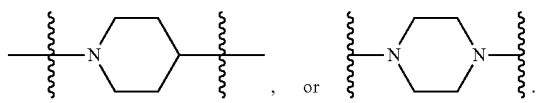

In an embodiment of the eleventh aspect, wherein B is

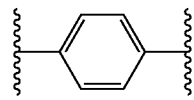

and wherein A is

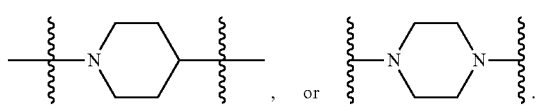

In an embodiment of the eleventh aspect, q is 1.
In an embodiment of the eleventh aspect, q is 2.
In an embodiment of the eleventh aspect, q is 3.
In an embodiment of the eleventh aspect, $L^4$ is

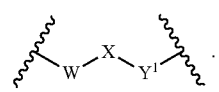

In an embodiment of the eleventh aspect, W is $NR^6$, X of $L^4$ is

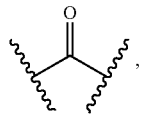 [SMILES: *C(*)=O]

and $Y^1$ is O.

In an embodiment of the eleventh aspect, wherein n is 1, and wherein one of $R^4$ and $R^5$ is hydrogen.

In a twelfth aspect, the compound or pharmaceutically acceptable salt thereof of the tenth aspect is also represented by Formula (IIb):

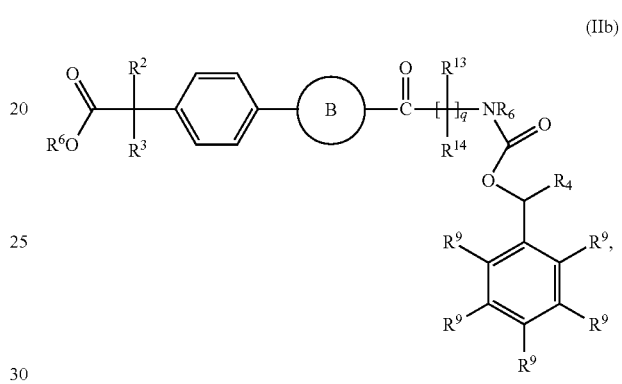

(IIb)

wherein
B is

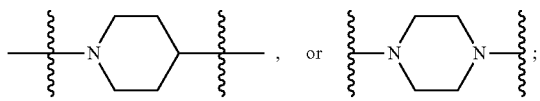

each $R^2$ and $R^3$ is independently selected from H, alkyl, and aryl; or $R^2$ and $R^3$ are joined together with the atom to which they are attached to form an optionally substituted cycloalkyl or an optionally substituted heterocycle; and
each $R^4$ and $R^6$ is independently selected from H and alkyl.

In an embodiment of the twelfth aspect, both $R^2$ and $R^3$ are hydrogen.

In an embodiment of the twelfth aspect, $R^2$ and $R^3$ are joined together with the atom to which they are attached to form an optionally substituted cyclopropyl.

In an embodiment of the twelfth aspect, both $R^{13}$ and $R^{14}$ are hydrogen.

In an embodiment of the twelfth aspect, q is 1, $R^{13}$ is hydrogen, and $R^{14}$ is selected from alkyl, optionally substituted phenyl or optionally substituted benzyl group.

In an embodiment of the twelfth aspect, $R^4$ is hydrogen.
In an embodiment of the twelfth aspect, $R^4$ is alkyl.
In an embodiment of the twelfth aspect, $R^6$ is alkyl.
In an embodiment of the twelfth aspect, all $R^9$ are hydrogen.

These and other embodiments are described in greater detail below.

DETAILED DESCRIPTION OF THE PREFERRED EMBODIMENTS

Lysophosphatidic Acid (LPA) Activity

Lysophospholipids (such as lysophosphatidic acid (LPA)) affect fundamental cellular functions that include cellular proliferation, differentiation, survival, migration, adhesion, invasion, and morphogensis. These functions influence many biological processes that include neurogensis, angiogenesis, wound healing, immunity, and carcinogenesis. LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, and $LPA_6$) activates intracellular signaling pathways to produce a variety of biological responses. LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated. Activation of the LPA receptors ($LPA_1$, $LPA_2$, $LPA_3$, $LPA_4$, $LPA_5$, and $LPA_6$) with LPA mediates a range of downstream signaling cascades. The actual pathway and realized end point are dependent on a range of variables that include receptor usage, cell type, expression level of a receptor or signaling protein, and LPA concentration. Nearly all mammalian cells, tissues, and organs co-express several LPA-receptor subtypes, which indicates that LPA receptors signal in a cooperative manner. $LPA_1$, $LPA_2$, and $LPA_3$ share high amino acid sequence similarity.

A method of treatment of a preferred embodiment comprises inhibiting the physiological activity of LPA in a mammal by administering a therapeutically effective amount of a compound of a preferred embodiment or a pharmaceutically acceptable salt thereof to the mammal in need thereof.

Medicaments for treating a LPA-dependent or LPA-mediated disease or condition in a mammal are provided comprising a therapeutically effective amount of a compound of a preferred embodiment. A compound of a preferred embodiment can also be employed in the manufacture of a medicament for the treatment of a LPA-dependent or LPA-mediated disease or condition. Use of a compound of a preferred embodiment in the treatment or prevention is also provided.

In any of the methods of treatment described herein involving the treatment of LPA dependent diseases or conditions by administration of a compound of a preferred embodiment are also contemplated methods comprising administering at least one additional agent in addition to the compound of preferred embodiments. In various embodiments, each agent is administered in any order, including simultaneously. The compounds of preferred embodiments are useful as antagonists of at least one LPA receptor, or for inhibiting the activity of at least one LPA receptor, or for the treatment of a disease or condition that would benefit from inhibition of the activity of at least one LPA receptor.

The compounds of preferred embodiments, pharmaceutically acceptable salts, pharmaceutically acceptable prodrugs, and pharmaceutically acceptable solvates thereof, which are antagonists of at least one LPA receptor (e.g., $LPA_1$, $LPA_2$, $LPA_3$) can be used to treat patients suffering from one or more LPA-dependent or LPA-mediated conditions or diseases, including, but not limited to, ideopathic pulmonary fibrosis. In some embodiments, LPA-dependent conditions or diseases include those wherein an absolute or relative excess of LPA is present and/or observed.

One or more of the compounds of preferred embodiments can be provided in the form of pharmaceutically acceptable salts, solvates, active metabolites, tautomers, or prodrugs thereof. The compounds of preferred embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, inhalation, nasal administration, topical administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The pharmaceutical compositions of preferred embodiments can further comprise one or more additional therapeutically active agents other than a compound of the preferred embodiments. Such agents can include, but are not limited to, corticosteroids, immunosuppresants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines, mucolytics, anticholinergics, antitussives, expectorants, and β13-2 agonists.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description Definitions Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
Ac Acetyl
Ac$_2$O Acetic anhydride
aq. Aqueous
Bn Benzyl
Bz Benzoyl
BOC or Boc tert-Butoxycarbonyl
Bu n-Butyl
cat. Catalytic
Cbz Carbobenzyloxy
CDI 1,1'-carbonyldiimidazole
° C. Temperature in degrees Centigrade
DBU 1,8-Diazabicyclo[5.4.0]undec-7-ene
DCE 1,2-Dichloroethane
DCM Methylene chloride
DIEA Diisopropylethylamine
DMA Dimethylacetamide
DME Dimethoxyethane
DMF N,N'-Dimethylformamide
DMSO Dimethylsulfoxide
DPPA Diphenylphosphoryl azide
ee % Enantiomeric excess
Et Ethyl
EtOAc Ethyl acetate
g Gram(s)
h or hr Hour(s)
HATU 2-(1H-7-azabenzotriazol-1-yl)-1,1,3,3-tetramethyl uronium hexafluorophosphate
HOBT N-Hydroxybenzotriazole
iPr Isopropyl
LCMS Liquid chromatography-mass spectrometry
LDA Lithium diisopropylamide
m Minute(s)
mCPBA meta-Chloroperoxybenzoic Acid
MeOH Methanol
MeCN Acetonitrile
mL Milliliter(s)
MTBE Methyl tertiary-butyl ether
NH$_4$OAc Ammonium acetate
PG Protecting group
Pd/C Palladium on activated carbon
Pd(dppf)Cl$_2$ 1,1'-Bis(diphenylphosphino)ferrocene-palladium(II)dichloride
Ph Phenyl
ppt Precipitate
RCM Ring closing metathesis
rt Room temperature
sBuLi sec-Butyllithium
SFC Supercritical fluid chromatography
TEA Triethylamine
TCDI 1,1'-Thiocarbonyl diimidazole
Tert, t tertiary
TFA Trifluoracetic acid
THF Tetrahydrofuran
TLC Thin-layer chromatography
TMEDA Tetramethylethylenediamine
□L Microliter(s)

The terms "individual," "host," "subject," and "patient" are broad terms, and are to be given their ordinary and customary meaning to a person of ordinary skill in the art (and are not to be limited to a special or customized meaning), and refer without limitation to a mammal, including, but not limited to, primates, including simians (chimpanzees, apes, monkeys) and humans, cattle, horses, sheep, goats, swine, rabbits, dogs, cats, rodents, rats, mice guinea pigs, or the like.

As used herein, the terms "treatment," "treating," and the like are broad terms, and are to be given their ordinary and customary meaning to a person of ordinary skill in the art (and are not to be limited to a special or customized meaning), and refer without limitation to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The term "modulate" as used herein is a broad term, and is to be given its ordinary and customary meaning to a person of ordinary skill in the art (and is not to be limited to a special or customized meaning), and refers without limitation to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein is a broad term, and is to be given its ordinary and customary meaning to a person of ordinary skill in the art (and is not to be limited to a special or customized meaning), and refers without limitation to a molecule that interacts with a target either directly or indirectly. The interactions include, but are not limited to, the interactions of an agonist, partial agonist, an inverse agonist, and antagonist. In one embodiment, a modulator is an antagonist.

The term "agonist" as used herein is a broad term, and is to be given its ordinary and customary meaning to a person of ordinary skill in the art (and is not to be limited to a special or customized meaning), and refers without limitation to a molecule such as a compound, a drug, an enzyme activator or a hormone modulator that binds to a specific receptor and triggers a response in the cell. An agonist mimics the action of an endogenous ligand (such as LPA, prostaglandin, hormone, or neurotransmitter) that binds to the same receptor.

The term "antagonist" as used herein is a broad term, and is to be given its ordinary and customary meaning to a person of ordinary skill in the art (and is not to be limited to a special or customized meaning), and refers without limitation to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists, and inverse agonists.

The term "LPA-dependent" as used herein is a broad term, and is to be given its ordinary and customary meaning to a person of ordinary skill in the art (and is not to be limited to a special or customized meaning), and refers without limitation to conditions or disorders that would not occur, or would not occur to the same extent, in the absence of LPA.

The term "LPA-mediated" as used herein is a broad term, and is to be given its ordinary and customary meaning to a person of ordinary skill in the art (and is not to be limited to a special or customized meaning), and refers without limitation to conditions or disorders that might occur in the absence of LPA but can occur in the presence of LPA.

The term "selectivity," as applied to one LPA receptor versus other LPA receptors, as used herein is a broad term, and is to be given its ordinary and customary meaning to a person of ordinary skill in the art (and is not to be limited to a special or customized meaning), and refers without limitation to a compound that has an $IC_{50}$ (Ca Flux assay) for the indicated LPA receptor that is at least 10-fold less than the $IC_{50}$ for other LPA receptors. In some embodiments, selectivity for one LPA receptor versus other LPA receptor means that the compound has an $IC_{50}$ for the indicated LPA receptor that is at least 10-fold, at least 20-fold, at least 40-fold, at least 50-fold, at least 100-fold, at least 200-fold, at least 500-fold, or at least 1000-fold, less than the $IC_{50}$ for other LPA receptors. For example, a selective $LPA_1$ receptor antagonist has an $IC_{50}$ that is at least 10-fold, at least 20-fold, at least 40-fold, at least 50-fold, at least 100-fold, at least 200-fold, at least 500-fold, or at least 1000-fold, less than the $IC_{50}$ for other LPA receptors (e.g., LPA2, $LPA_3$).

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R^2$, $R^3$, $R^4$, $R^5$, $R^6$, $R^9$, and $R^{10}$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

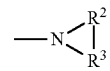

Whenever a group is described as being "optionally substituted" that group may be unsubstituted or substituted with one or more of the indicated substituents Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, 0-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "carbocyclyl" or "cyclic hydrocarbyl" refers to all carbon ring systems. Such systems can be unsaturated, can include some unsaturation, or can contain some aromatic portion, or be all aromatic. A carbocyclyl group may be unsubstituted or substituted.

As used herein, "aryl" refers to a carbocyclic (all carbon) monocyclic or multicyclic aromatic ring system (including, e.g., fused, bridged, or spiroring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to ring systems including at least one heteroatom (e.g., O, N, S). Such systems can be unsaturated, can include some unsaturation, or can contain some aromatic portion, or be all aromatic. A heterocyclyl group may be unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" is a heterocyclic or a heteroalicyclylic group connected, as a substituent, via a lower alkylene group. The lower alkylene and heterocyclic or a heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "aryloxy" and "arylthio" refers to RO— and RS—, in which R is an aryl, such as but not limited to phenyl. Both an aryloxy and arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —$NH_2$ group.
As used herein, the term "hydroxy" refers to a —OH group.
A "cyano" group refers to a "—CN" group.
The term "azido" as used herein refers to a —$N_3$ group.
An "isocyanato" group refers to a "—NCO" group.
A "thiocyanato" group refers to a "—CNS" group.
An "isothiocyanato" group refers to an "—NCS" group.
A "mercapto" group refers to an "—SH" group.
A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine, and iodine.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "—N-linked amino acid" refers to an amino acid that is attached to the indicated moiety via one of its main-chain amino or mono-substituted amino groups. When the amino acid is attached in an —N-linked amino acid, one of the hydrogens that is part of the main-chain amino or mono-substituted amino group is not present and the amino acid is attached via the nitrogen. As used herein, the term "amino acid" refers to any amino acid (both standard and non-standard amino acids), including, but limited to, □-amino acids, □-amino acids, □-amino acids and □-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine. Additional examples of suitable amino acids include, but are not limited to, selenocysteine, ornithine, taurine, hydroxyproline, selenomethionine, hypusine, lanthionine, 2-aminoisobutyric acid, dehydroalanine, gamma-aminobutyric acid, citrulline, beta-alanine, alpha-ethyl-glycine, alpha-propyl-glycine, homo-alanine, and norleucine. N-linked amino acids can be substituted or unsubstituted.

The term "—N-linked amino acid ester derivative" refers to an amino acid in which one of its main-chain carboxylic acid groups has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include, methyl-O—C(=O)—, ethyl-O—C(=O)—, n-propyl-O—C(=O)—, isopropyl-O—C(=O)—, n-butyl-O—C(=O)—, isobutyl-β—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, and benzyl-O—C(=O)—. N-linked amino acid ester derivatives can be substituted or unsubstituted.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, $5^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

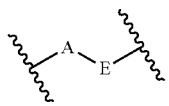

includes the substituent being oriented such that the A is attached at the leftmost attachment point of the molecule as well as the case in which A is attached at the rightmost attachment point of the molecule.

It is to be understood that certain radical naming conventions can include either a mono-radical or a di-radical, depending on the context. For example, where a substituent requires two points of attachment to the rest of the molecule, it is understood that the substituent is a di-radical. A substituent identified as alkyl, that requires two points of attachment, includes di-radicals such as —$CH_2$—, —$CH_2CH_2$—, —$CH_2CH(CH_3)CH_2$—, and the like; a substituent depicted as alkoxy that requires two points of attachment, includes di-radicals such as —$OCH_2$—, —$OCH_2CH_2$—, —$OCH_2CH(CH_3)CH_2$—, and the like: and a substituent depicted as arylC(=O)— that requires two points of attachment, includes di-radicals such as

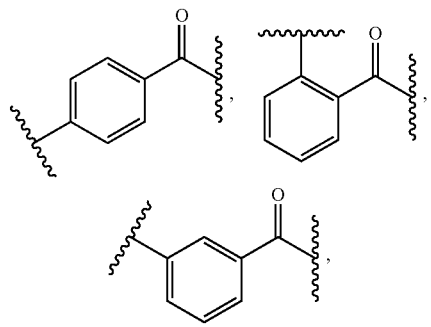

and the like.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and formulations described herein include the use of N-oxides (if appropriate), crystalline forms (also known as polymorphs, which include the different crystal packing arrangements of the same elemental composition of a compound), amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, prodrugs, crystalline forms, amorphous form, solvated forms, enantiomeric forms, tautomeric forms, and the like).

Diseases, Disorders and Conditions Associated with LPA Activity

The compounds of preferred embodiments inhibit the physiological activity of LPA. As such the compounds of preferred embodiments are useful as agents for the treatment or prevention of diseases in which inhibition of the physiological activity of LPA is desirable, such as in the treatment of diseases in which an LPA receptor participates, or is involved in the etiology or pathology of the disease, or is otherwise associated with at least one symptom of the disease. The compounds of preferred embodiments can be employed for the treatment or prevention of side effects, complications, or adverse events associated with the use of a conventional therapeutic agent or therapeutic action (e.g., surgery, etc.) used in treating a disease or condition in which inhibition of LPA physiological activity is desirable. The compounds of preferred embodiments are antagonists of at least one of the LPA receptors, e.g., $LPA_1$, $LPA_2$, $LPA_3$, $LPA_4$, $LPA_5$, and/or $LPA_6$. Certain of the compounds of preferred embodiments are selective antagonists for one or more of the LPA receptors relative to the other LPA receptors.

The compounds of preferred embodiments are used in the treatment of diseases, disorders, or conditions in which activation of at least one LPA receptor by LPA contributes to the symptomology or progression of the disease, disorder, or condition. The compounds of preferred embodiments are antagonists of LPA receptor(s). Diseases, disorders, or conditions that the compounds of preferred embodiments can be used to treat include, but are not limited to, fibrosis, cancer, or respiratory disorders. For examples, the fibrosis can include pulmonary fibrosis, dermal fibrosis, kidney fibrosis, or liver fibrosis. In one embodiment, the fibrosis is idiopathic pulmonary fibrosis.

The terms "fibrosis" or "fibrosing disorder," as used herein, are broad terms and refer without limitation to conditions that are associated with the abnormal accumulation of cells and/or fibronectin and/or collagen and/or increased fibroblast recruitment and include but are not limited to fibrosis of individual organs or tissues such as the lung. Exemplary diseases, disorders, or conditions that involve fibrosis include, but are not limited to, idiopathic pulmonary fibrosis.

LPA and $LPA_1$ play key pathogenic roles in pulmonary fibrosis. Fibroblast chemoattractant activity plays a role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterizes this fibrotic condition. The LPA-$LPA_2$ pathway contributes to the activation of the TGF-β pathway in pulmonary fibrosis. Compounds that inhibit $LPA_2$ may show efficacy in the treatment of lung fibrosis. Compounds that inhibit both $LPA_1$ and $LPA_2$ may show improved efficacy in the treatment of lung fibrosis compared to compounds which inhibit only $LPA_1$ or $LPA_2$.

Compounds

Provided herein are compounds having the Formula (I):

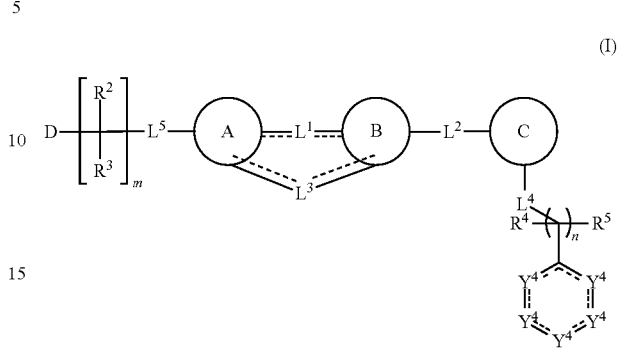

(I)

wherein the groups A, B, C, D, $L^1$, $L^2$, $L^3$, $L^4$, $L^5$, $R^2$, $R^3$, $R^4$, $R^5$, and $Y^4$, and any subgroups contained therein are as defined elsewhere herein.

Provided herein are compounds having the Formula (II):

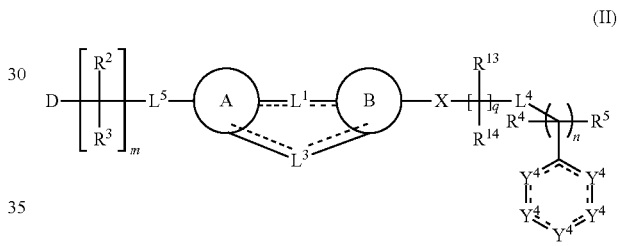

(II)

wherein the groups A, B, D, $L^1$, $L^3$, $L^4$, $L^5$, $R^2$, $R^3$, $R^4$, $R^5$, $R^{13}$, $R^{14}$, and $Y^4$, and any subgroups contained therein are as defined elsewhere herein.

Any compounds specifically disclosed in the following references and falling within the scope of compounds defined by Formula (I) are expressly excluded from the compounds and methods encompassed by or claimed within the present application or any application claiming prioity thereto: PCT Intl. Publ. No. WO/2011017350-A1; PCT Intl. Publ. No. WO/2010141768-A1; PCT Intl. Publ. No. WO/2010077883-A1; PCT Intl. Publ. No. WO/2010077882-A1; PCT Intl. Publ. No. WO/2010068775-A1; U.S. Pat. Publ. No. US-20110098352-A1; U.S. Pat. Publ. No. US-20110098302-A1; U.S. Pat. Publ. No. US-20110082181-A1; U.S. Pat. Publ. No. US-20110082164-A1; U.S. Pat. Publ. No. US-20100311799-A1; U.S. Pat. Publ. No. US-20100152257-A1; PCT Intl. Publ. No. WO/2010141761-A1; PCT Intl. Publ. No. WO/2011041729-A1; PCT Intl. Publ. No. WO/2011041694-A1; PCT Intl. Publ. No. WO/2011041462-A1; and PCT Intl. Publ. No. WO/2011041461-A1.

Exemplary Reaction Schemes

The following reaction schemes can be employed in the preparation of selected compounds of preferred embodiments. Unless otherwise specifically defined with respect to a particular reaction scheme, the groups and subgroups included in compounds in the reaction schemes are as defined elsewhere herein.

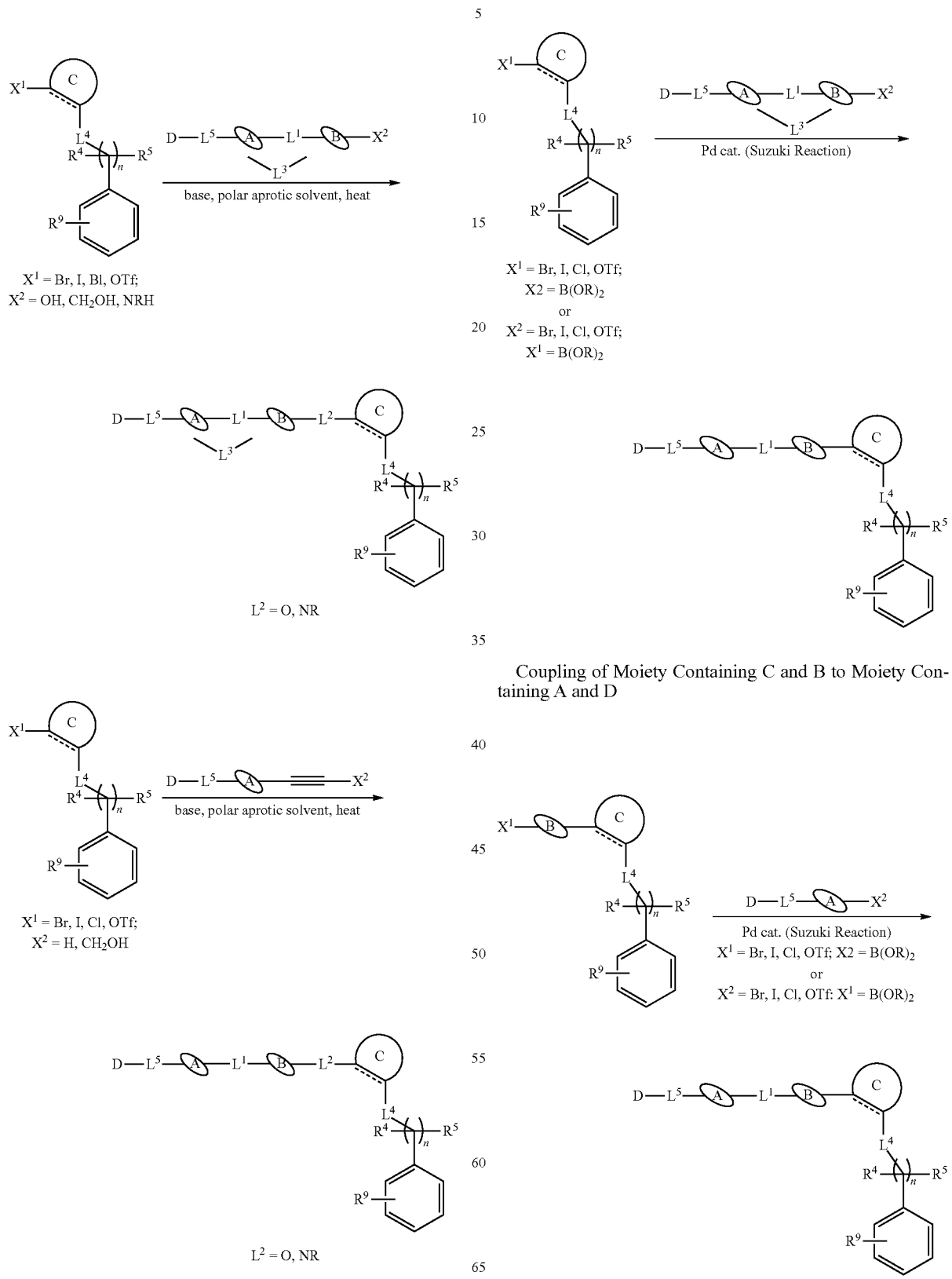

99
Carbamate C or Carbamate B, C Synthesis
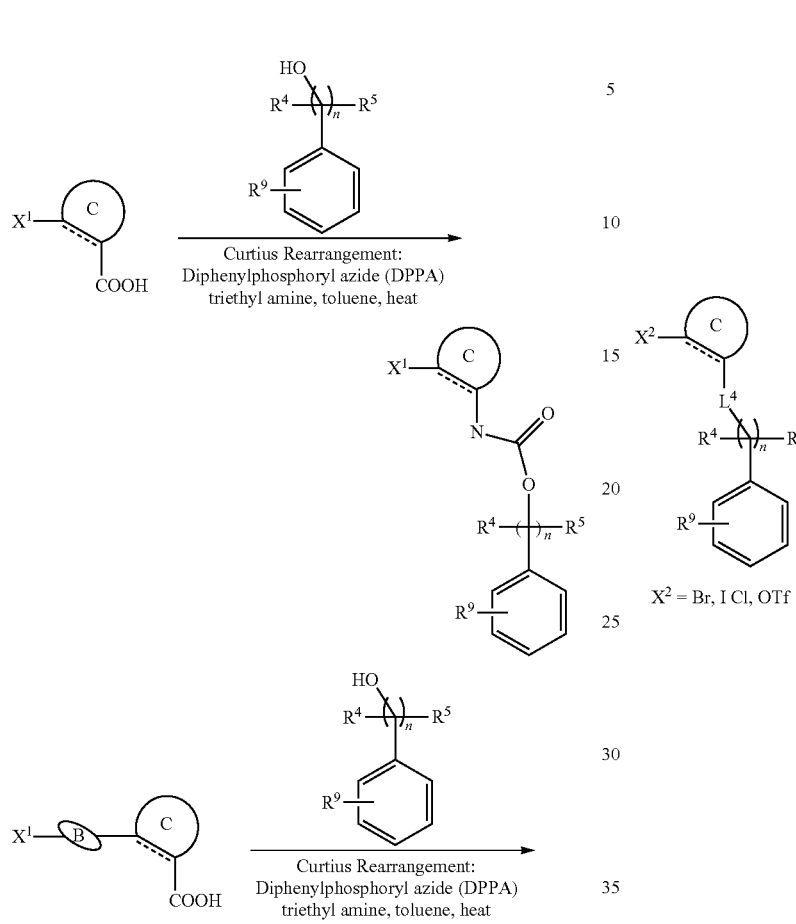
Coupling of Acetylene Linker
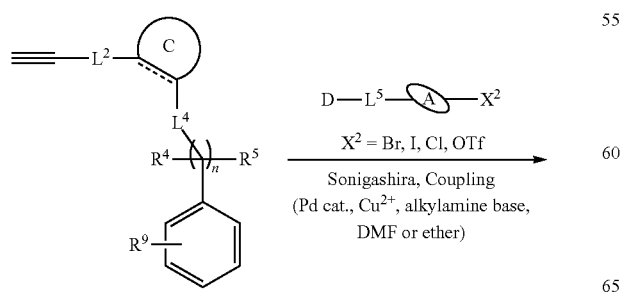
100
-continued
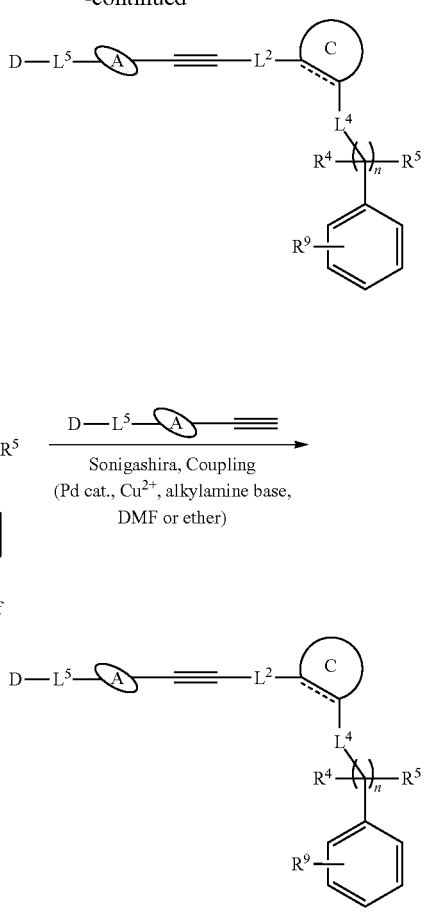
Synthesis of Substituted Benzofuran and Azo-Benzofuran
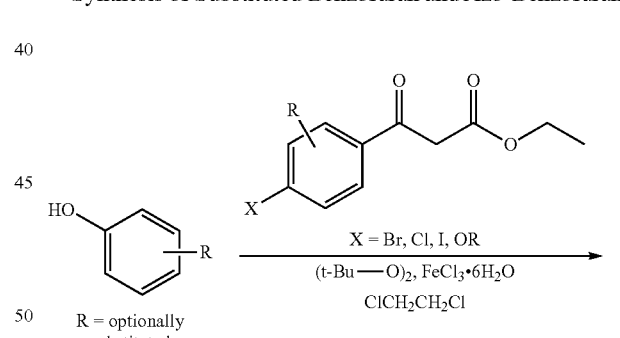
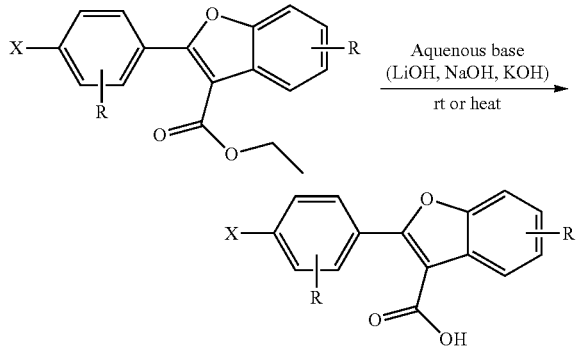

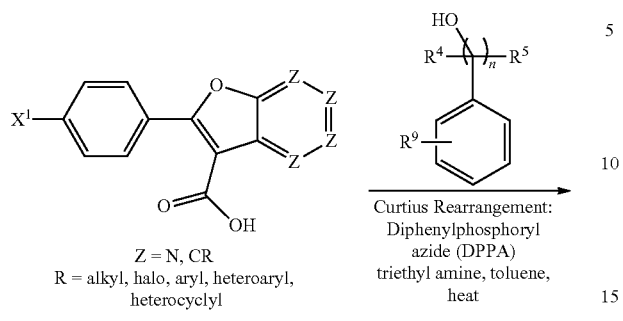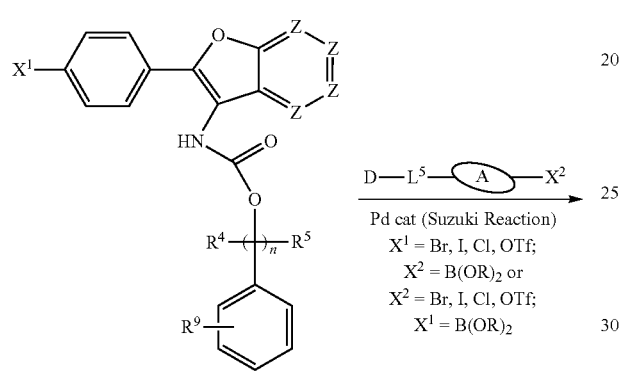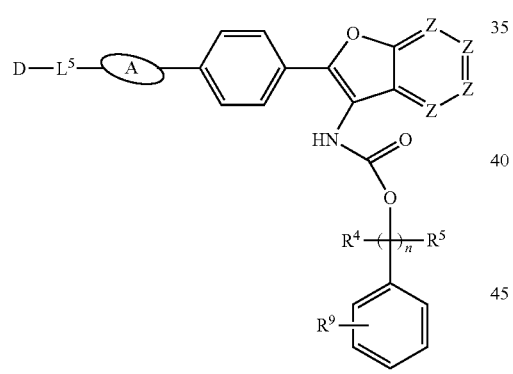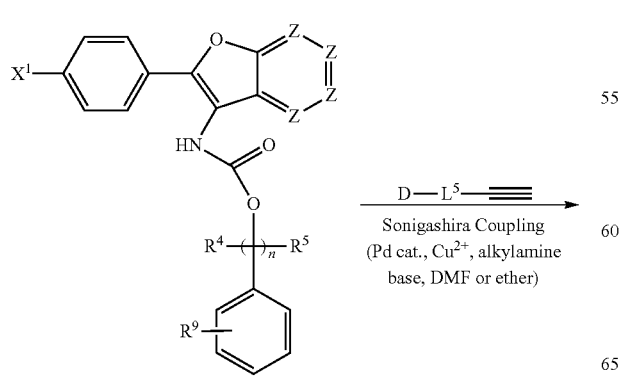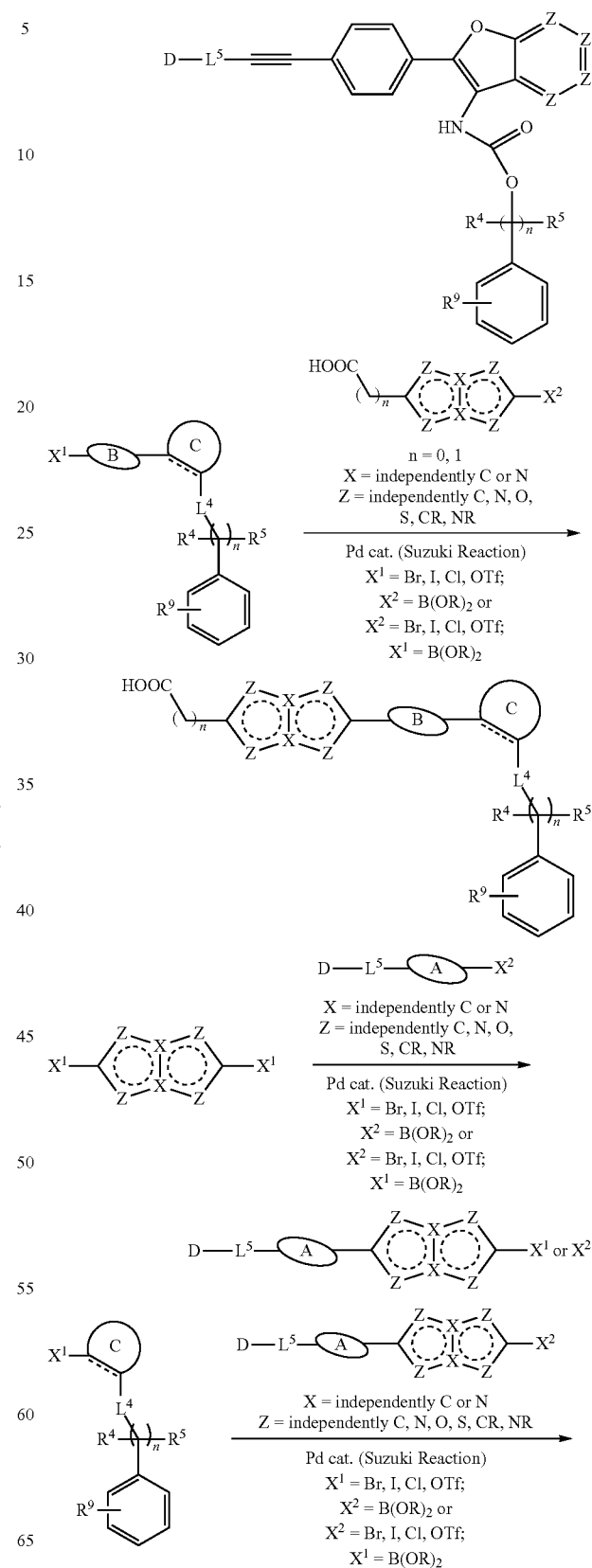

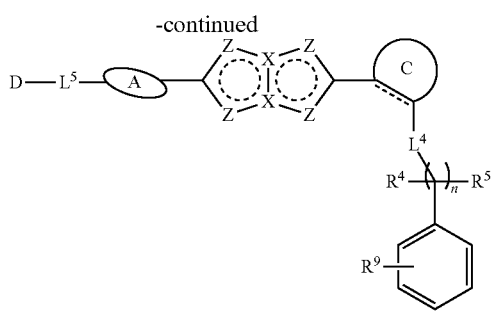

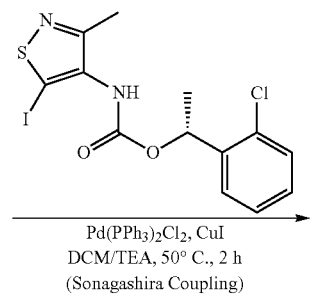

Synthesis of Acetylene Compounds

The following reaction schemes can be employed in the preparation of selected acetylene compounds of preferred embodiments. Unless otherwise specifically defined with respect to a particular reaction scheme, the groups and subgroups included in compounds in the reaction schemes are as defined elsewhere herein.

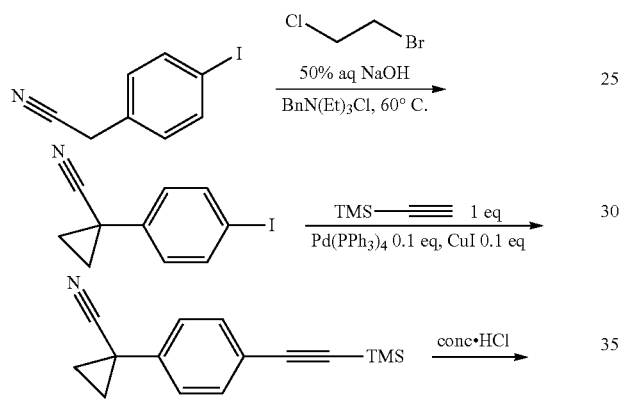

Synthesis of Tetrahydropyran Compounds

The following reaction schemes can be employed in the preparation of selected tetrahydropyran compounds of preferred embodiments. Unless otherwise specifically defined with respect to a particular reaction scheme, the groups and subgroups included in compounds in the reaction schemes are as defined elsewhere herein.

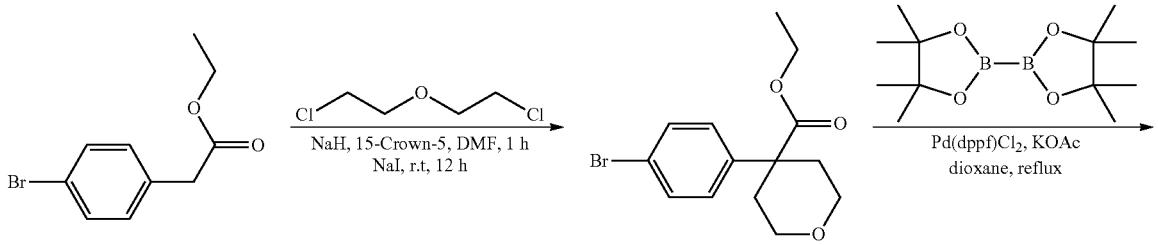

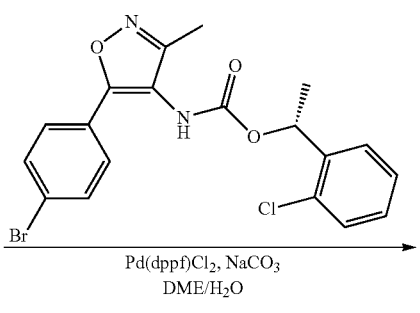

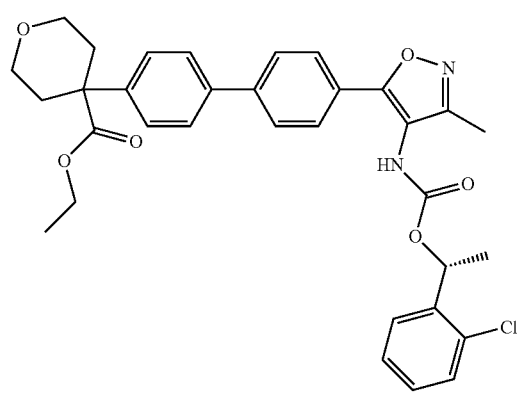
105

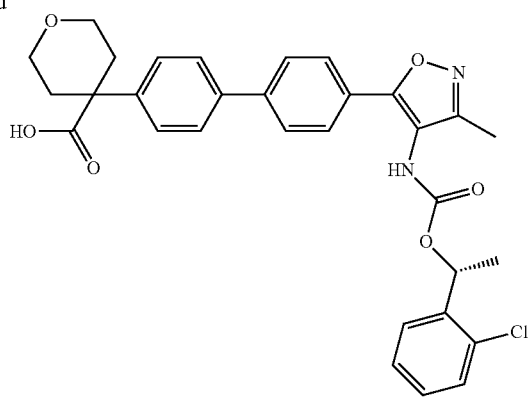
106

-continued

Synthesis of Oxetane Compounds

The following reaction schemes can be employed in the preparation of selected oxetane compounds of preferred embodiments. Unless otherwise specifically defined with respect to a particular reaction scheme, the groups and subgroups included in compounds in the reaction schemes are as defined elsewhere herein.

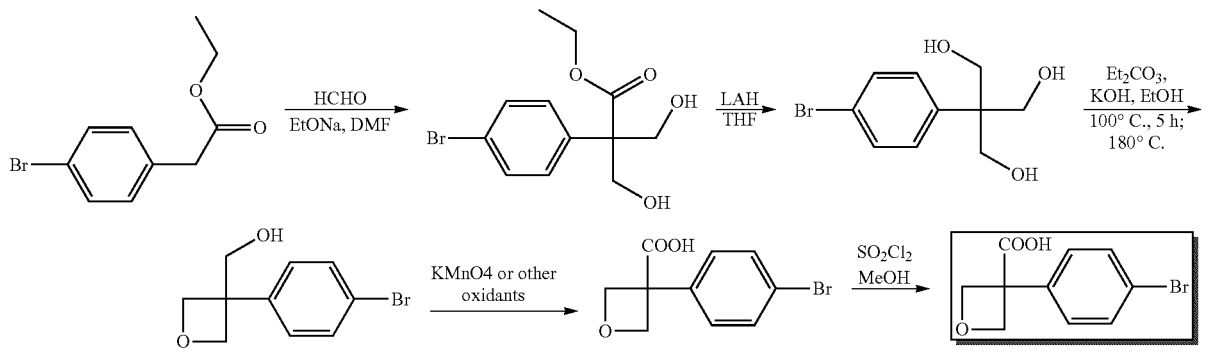

or alternate route:

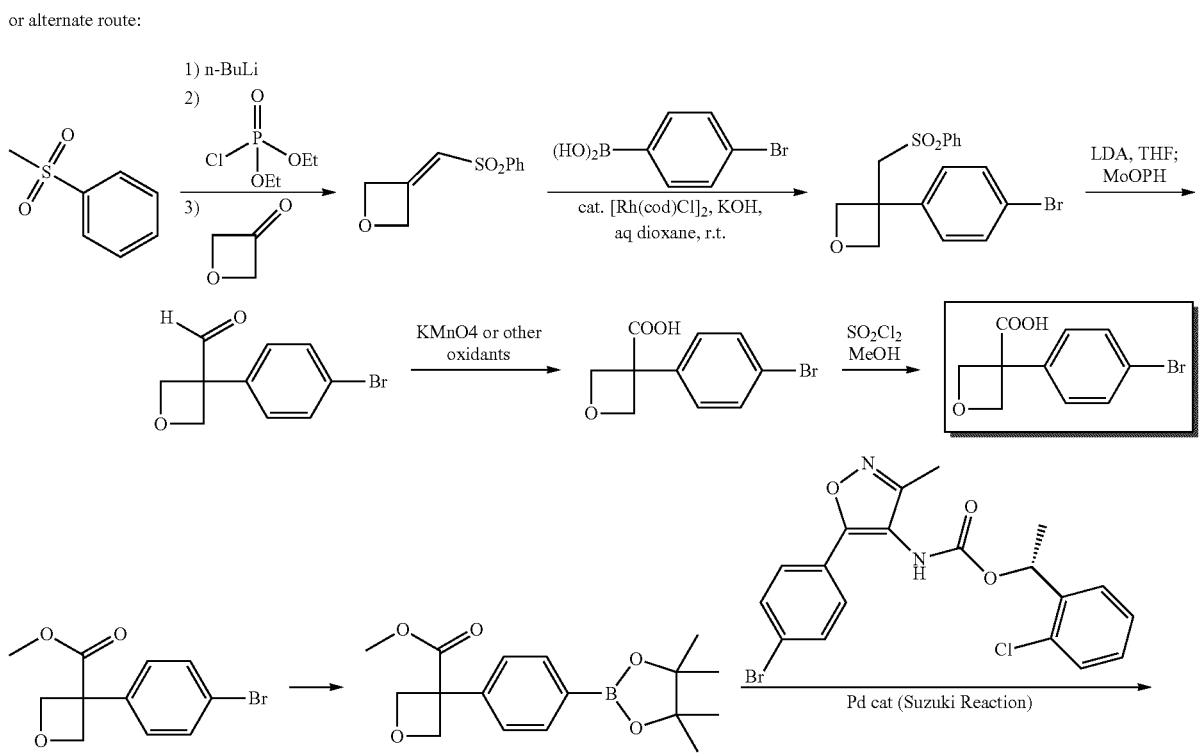

-continued

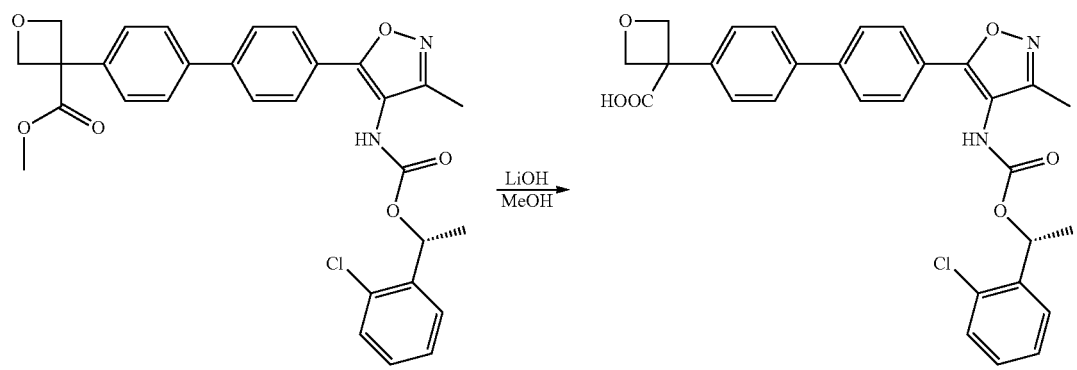

Synthesis of Azetidine Compounds

The following reaction schemes can be employed in the preparation of selected azetidine compounds of preferred embodiments. Unless otherwise specifically defined with respect to a particular reaction scheme, the groups and sub-groups included in compounds in the reaction schemes are as defined elsewhere herein.

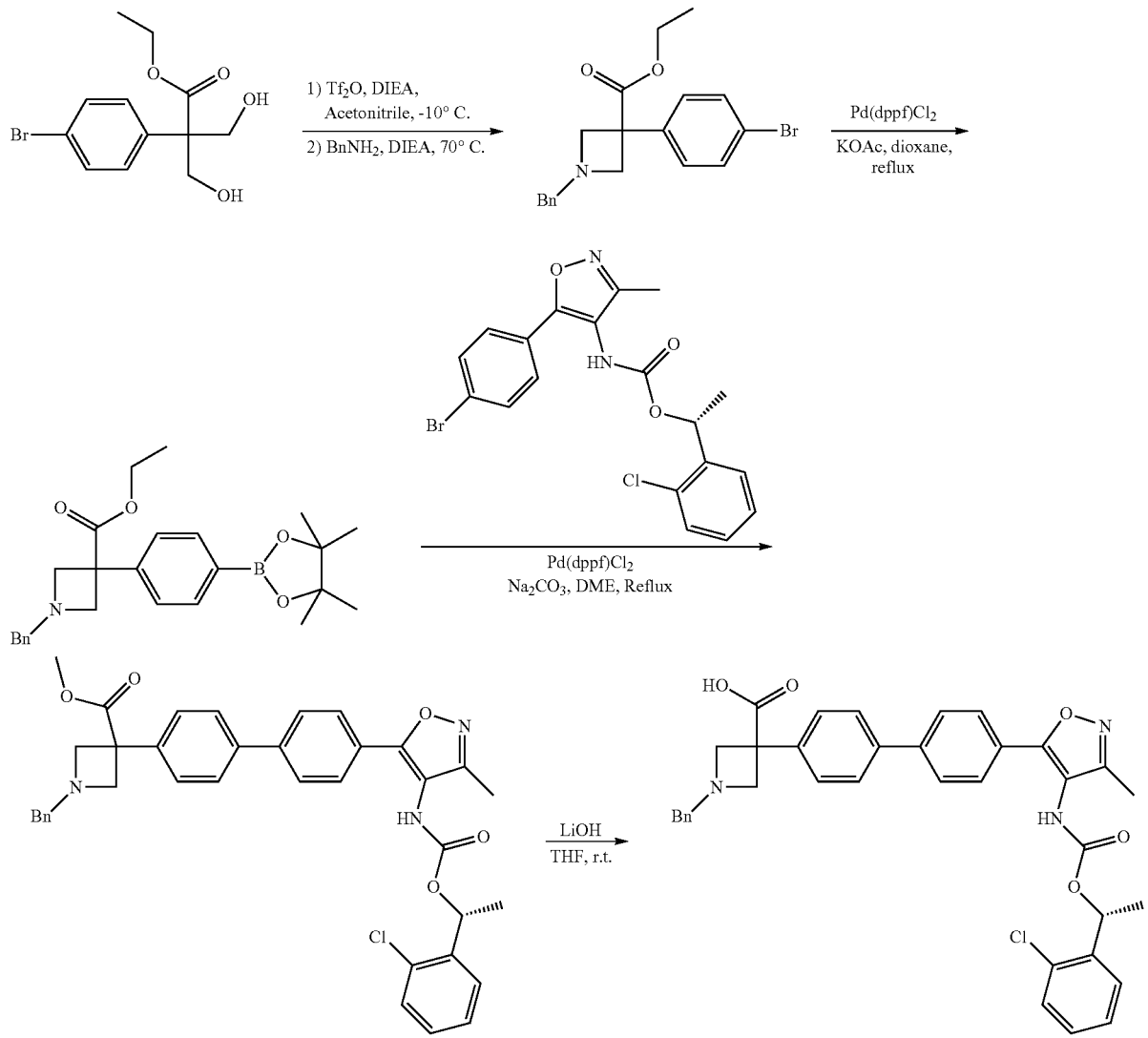

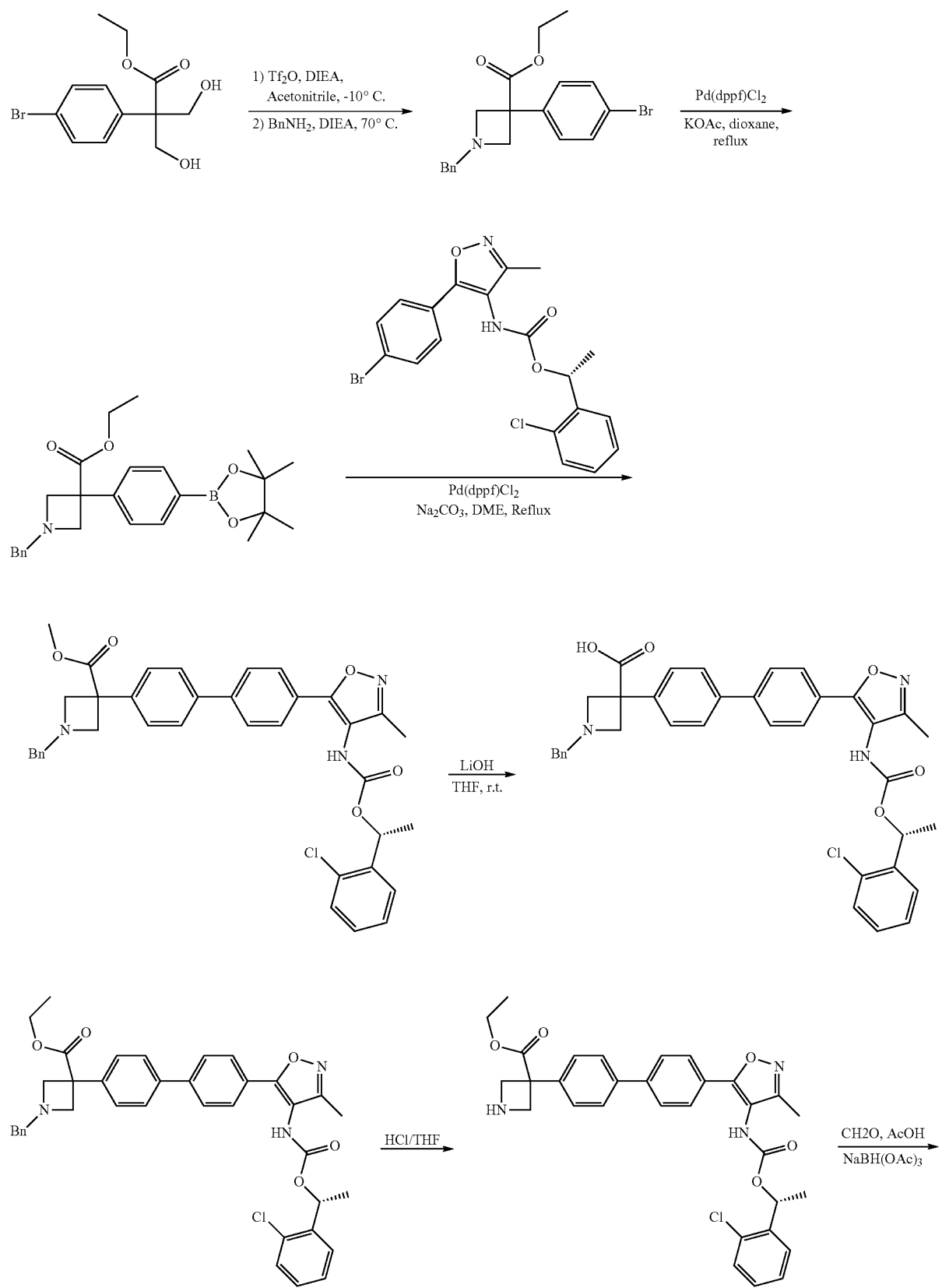
-continued

-continued
111
112
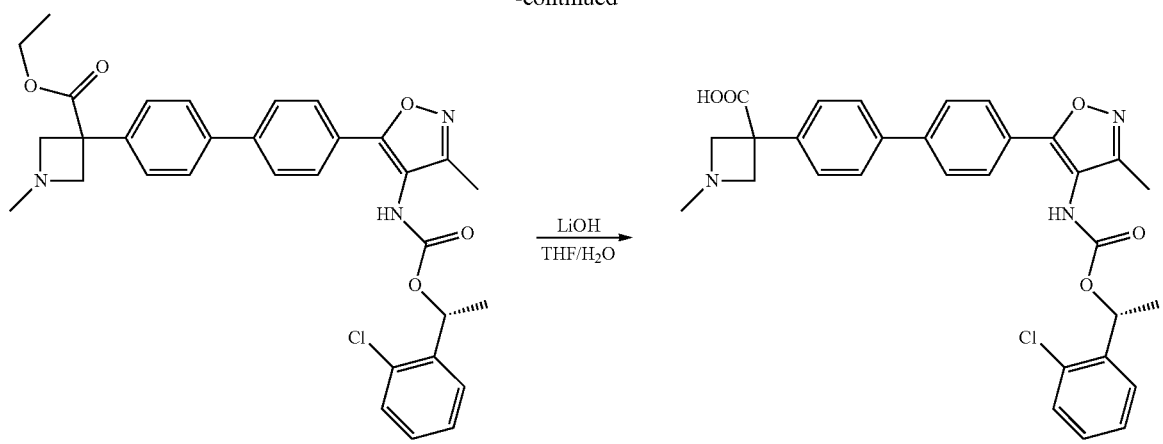
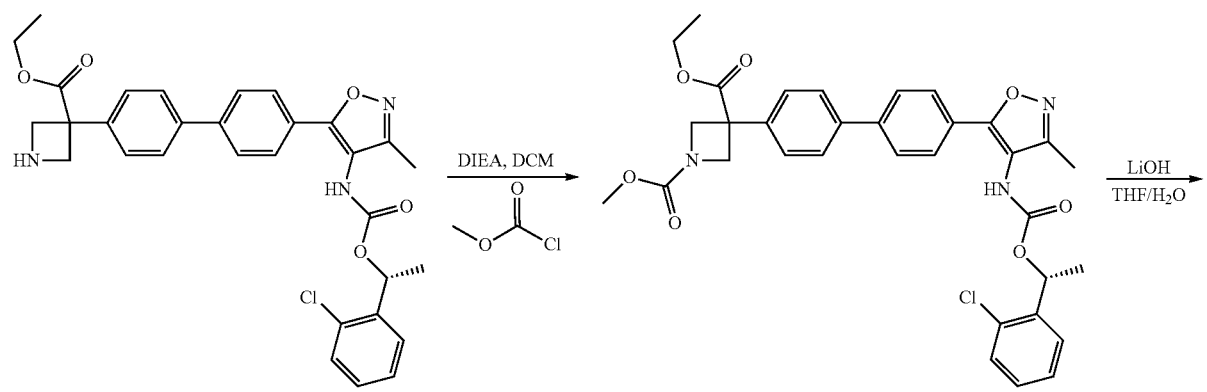
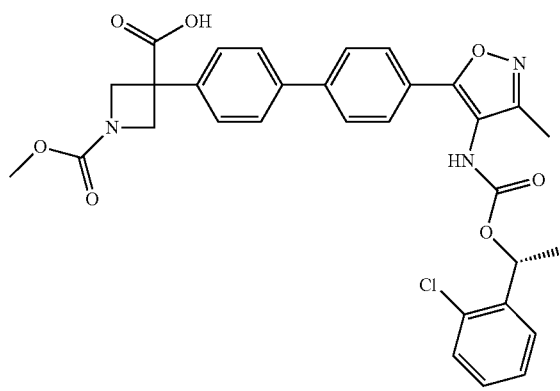
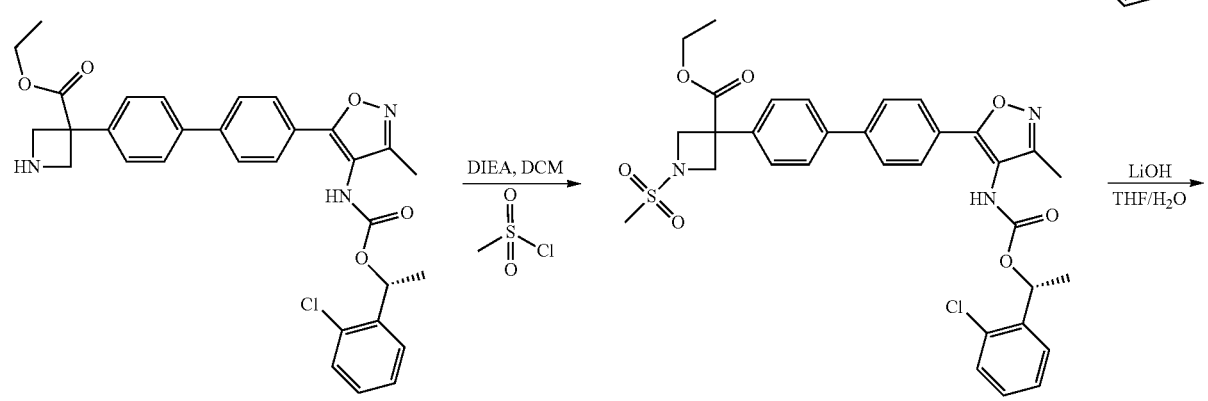

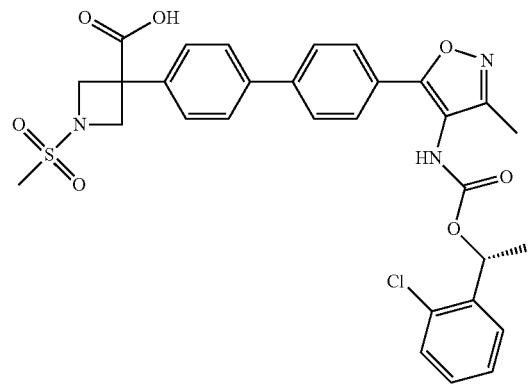
Synthesis of Beta-Lactam Compounds
The following reaction schemes can be employed in the preparation of selected beta-lactam compounds of preferred embodiments. Unless otherwise specifically defined with respect to a particular reaction scheme, the groups and subgroups included in compounds in the reaction schemes are as defined elsewhere herein.
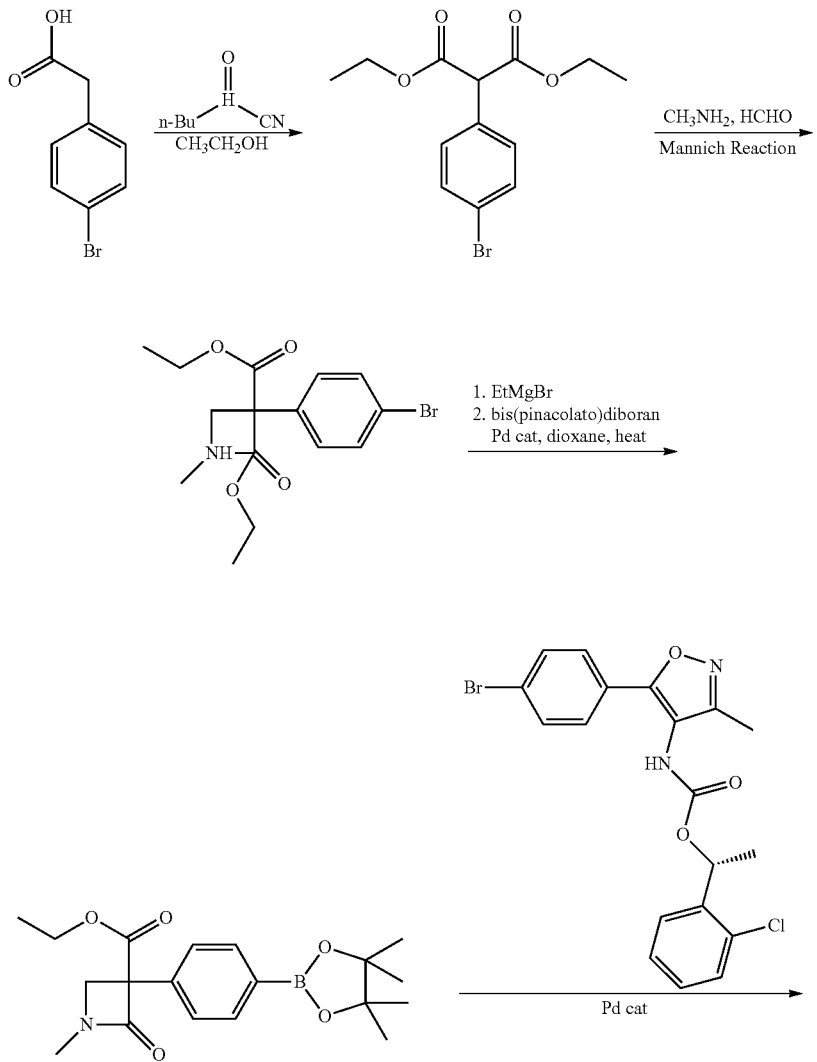

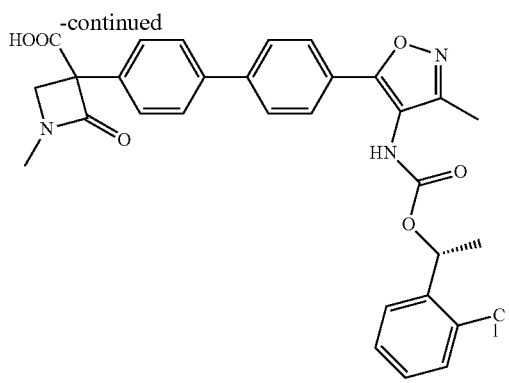

Chemische Berichte, 90, 1357-63; 1975
Justus Liebigs Annalen der Chemie, 661, 181-7; 1963
Bioorganic & Medicinal Chemistry Letters, 20(16), 4757-4761; 2010

Synthesis of Benzofuran Compounds

The following reaction schemes can be employed in the preparation of selected benzofuran compounds of preferred embodiments. Unless otherwise specifically defined with respect to a particular reaction scheme, the groups and subgroups included in compounds in the reaction schemes are as defined elsewhere herein.

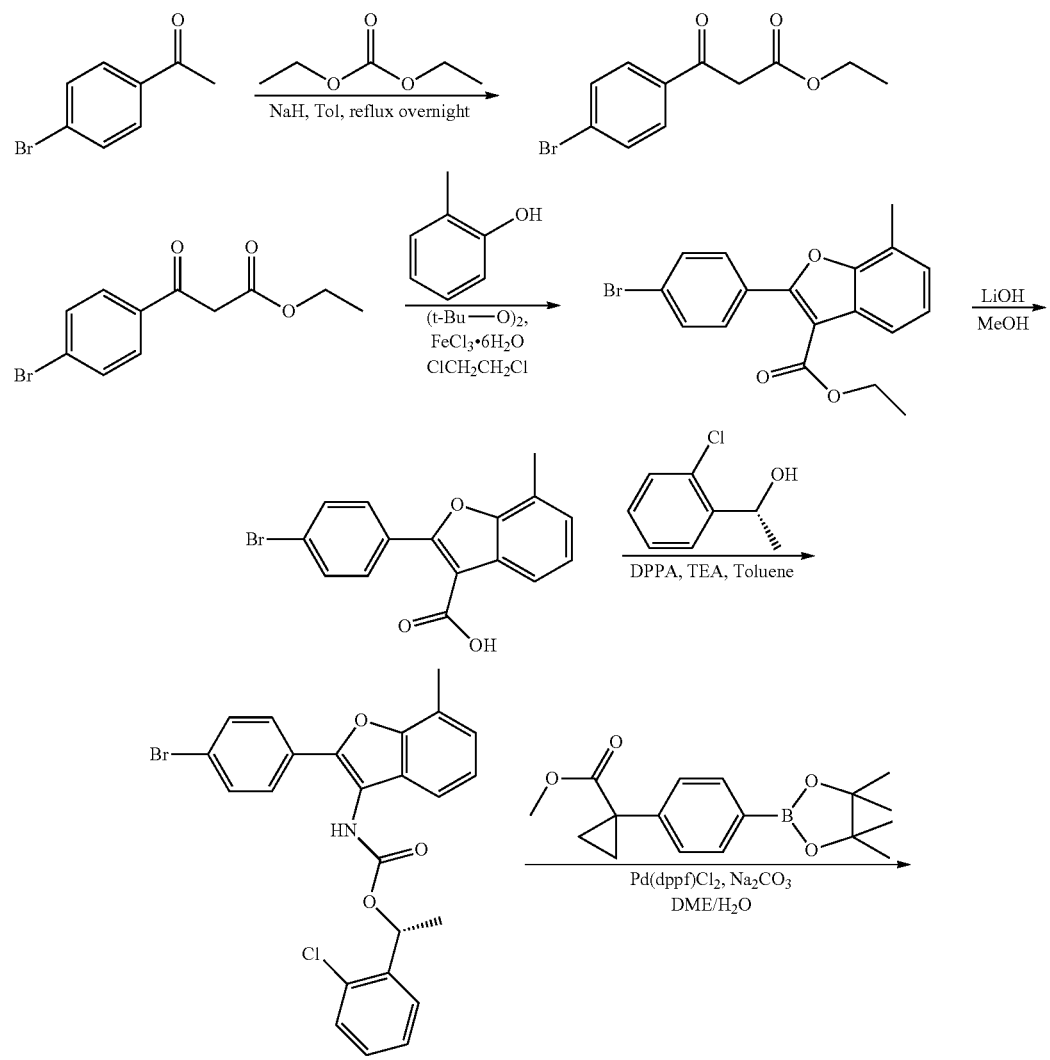

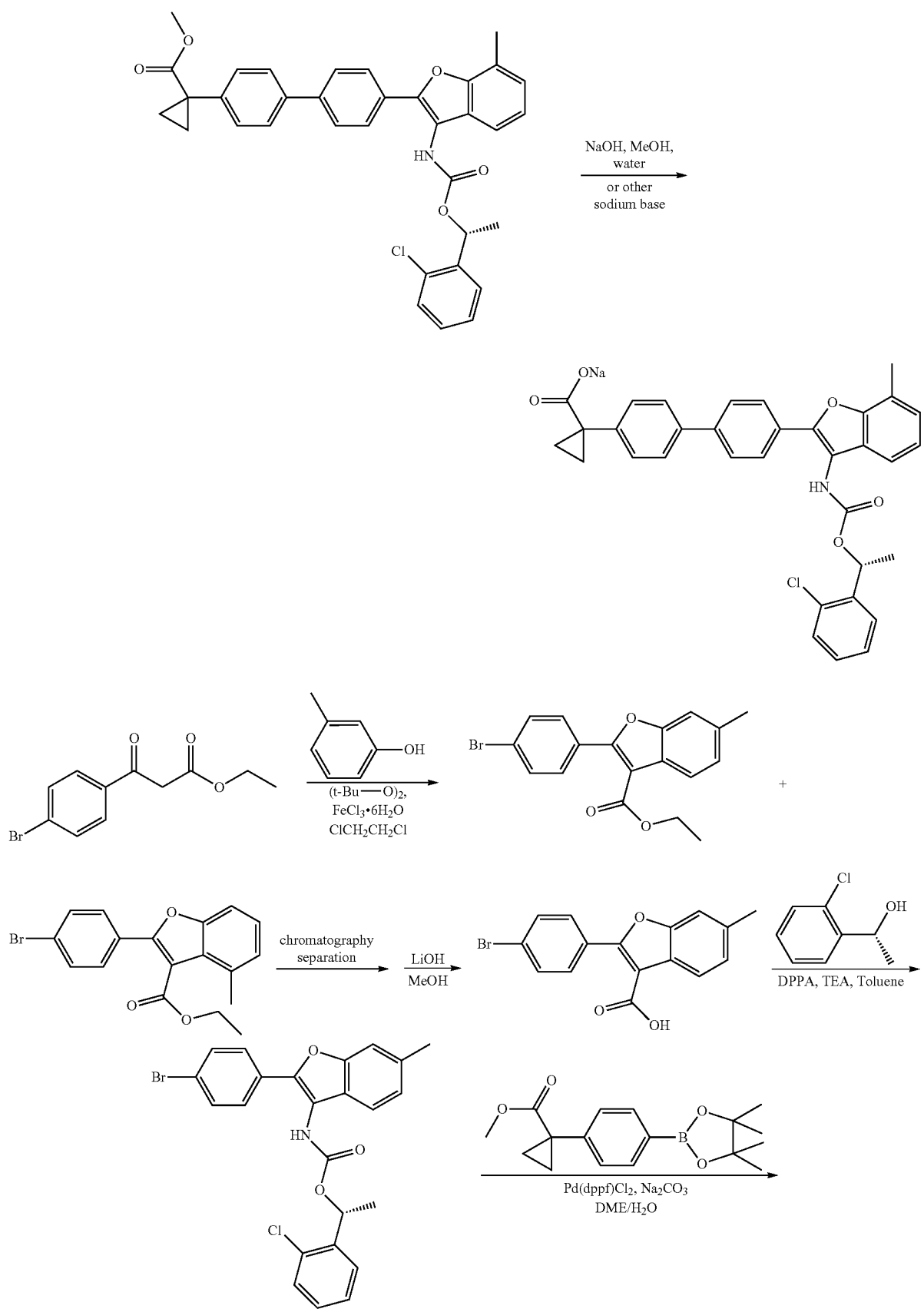

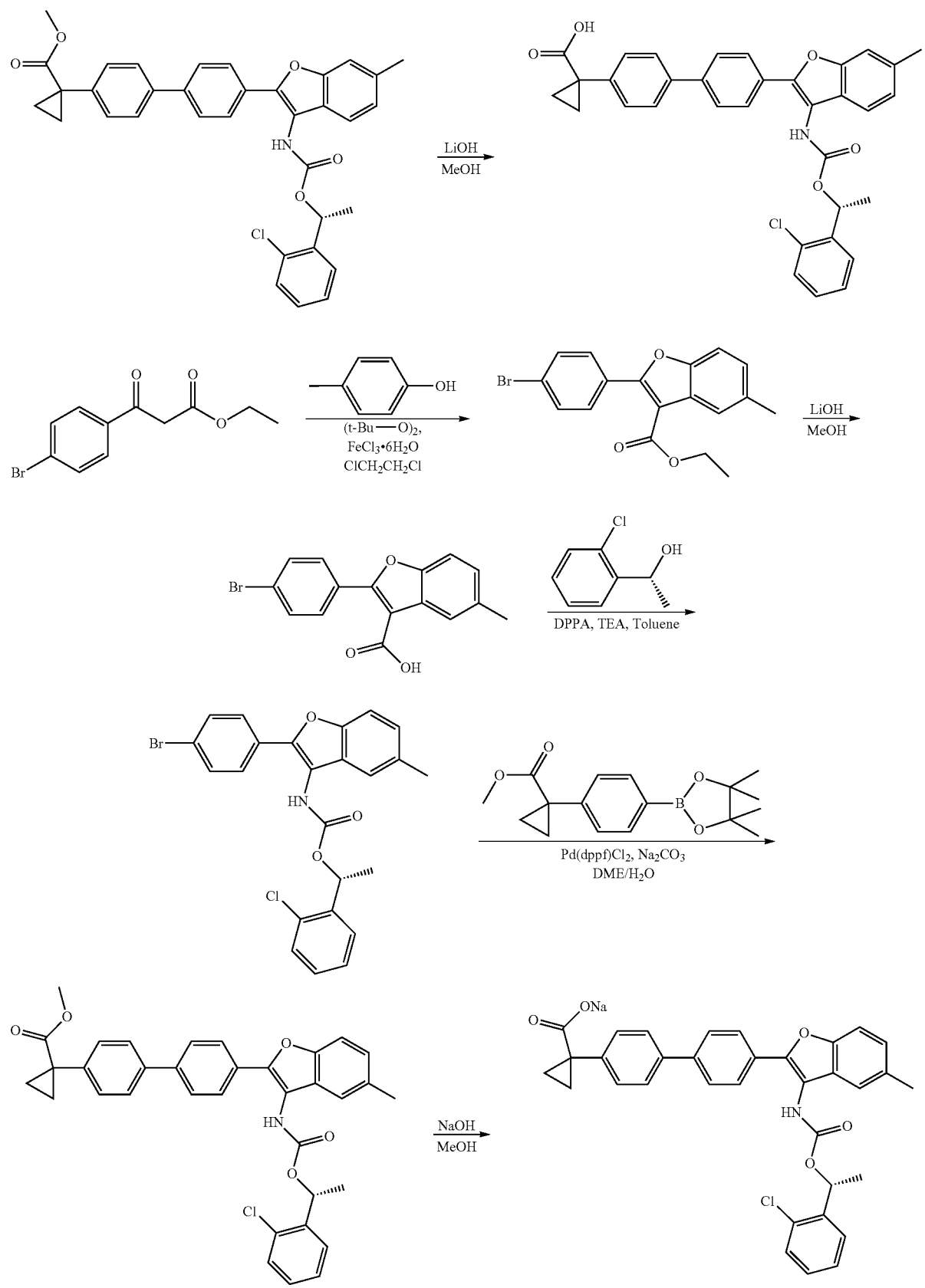

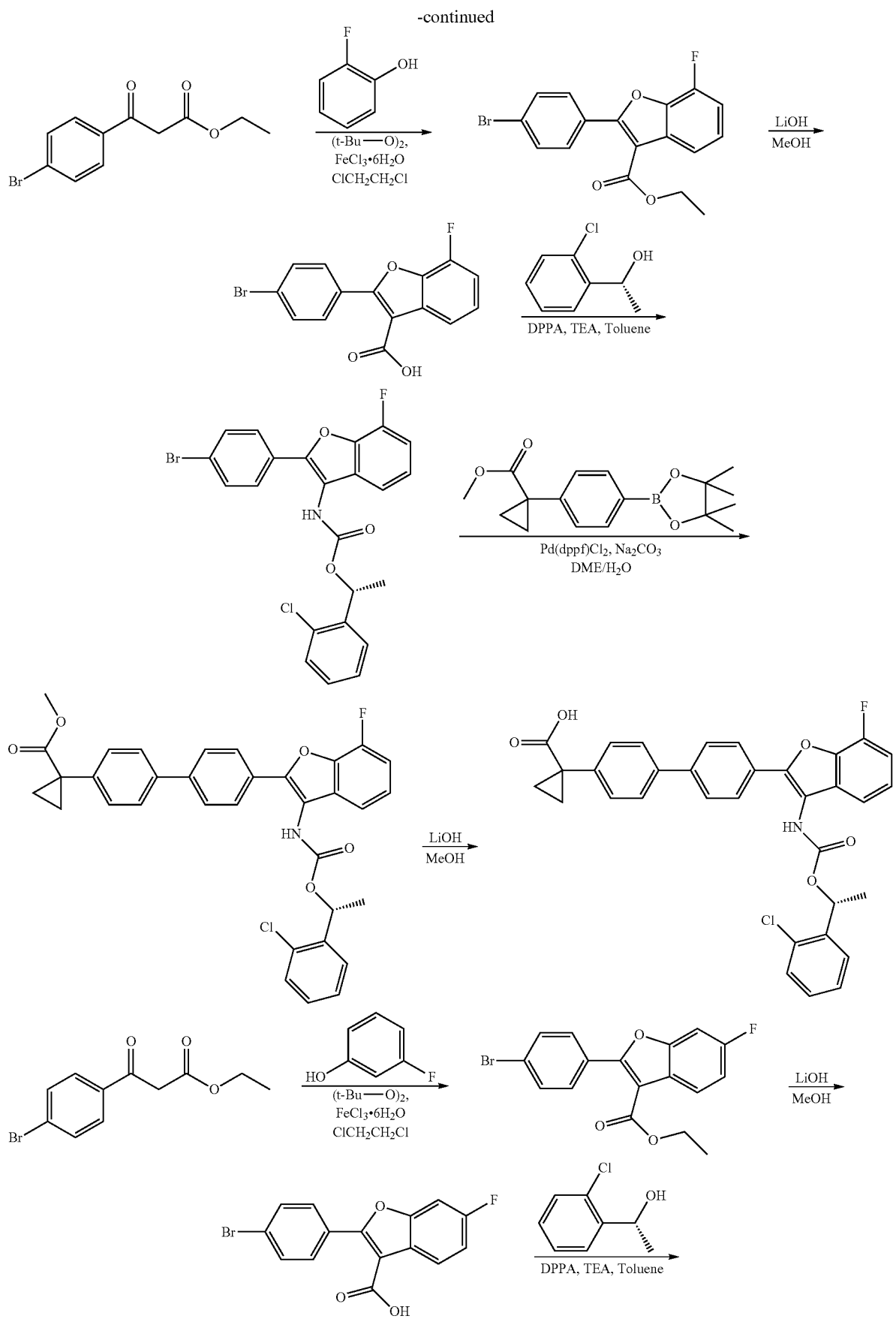

-continued
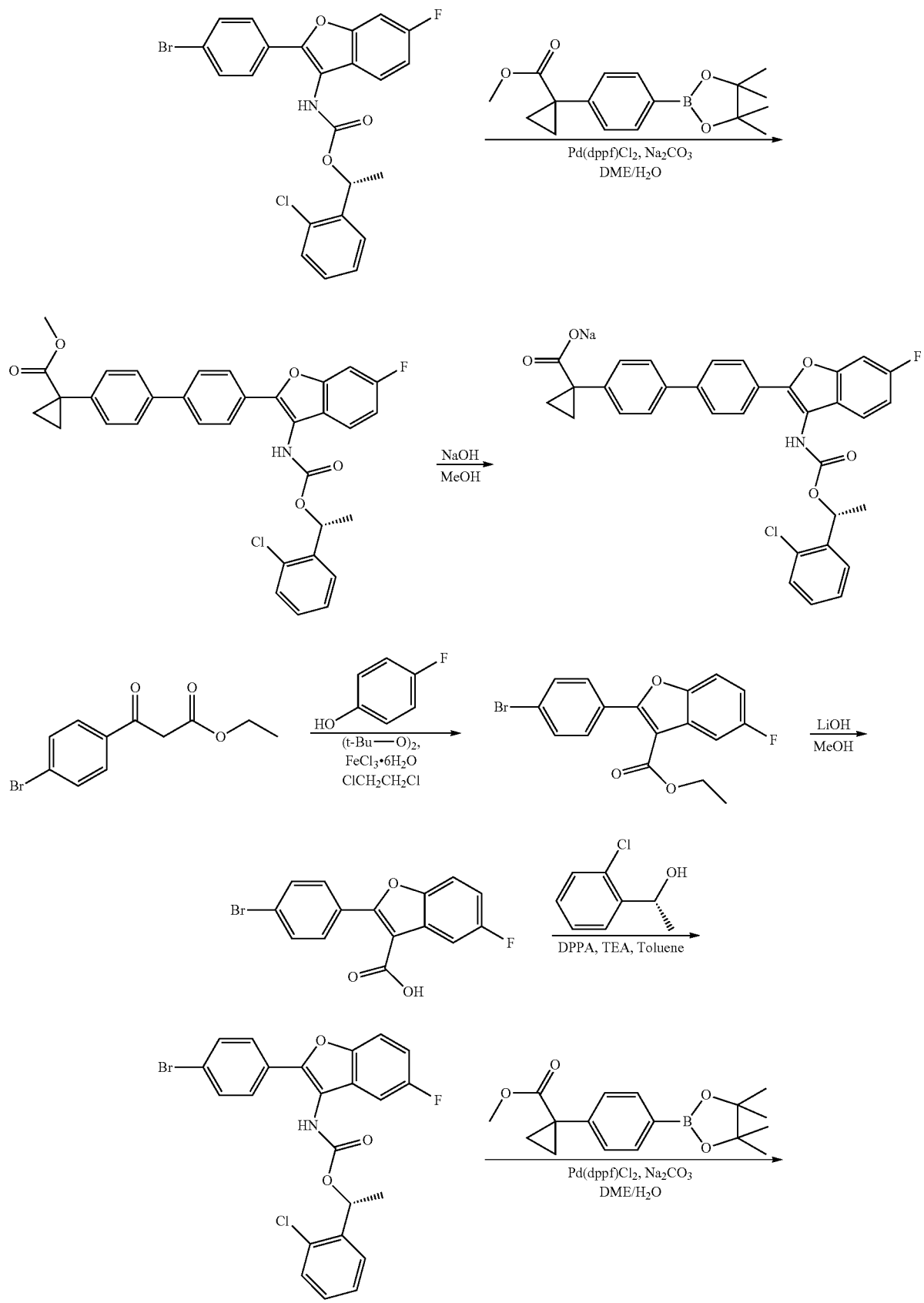

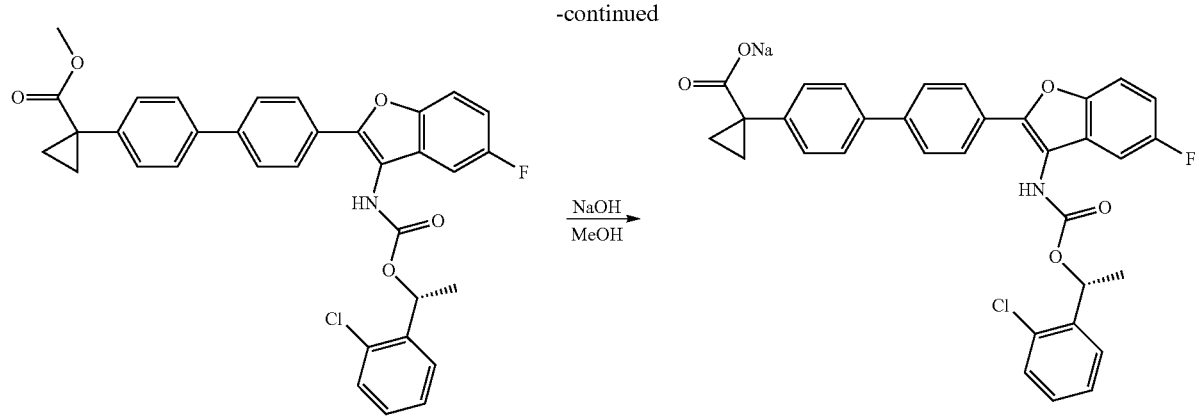
Synthesis of Indole Compounds
The following reaction schemes can be employed in the preparation of selected indole compounds of preferred embodiments. Unless otherwise specifically defined with respect to a particular reaction scheme, the groups and subgroups included in compounds in the reaction schemes are as defined elsewhere herein.
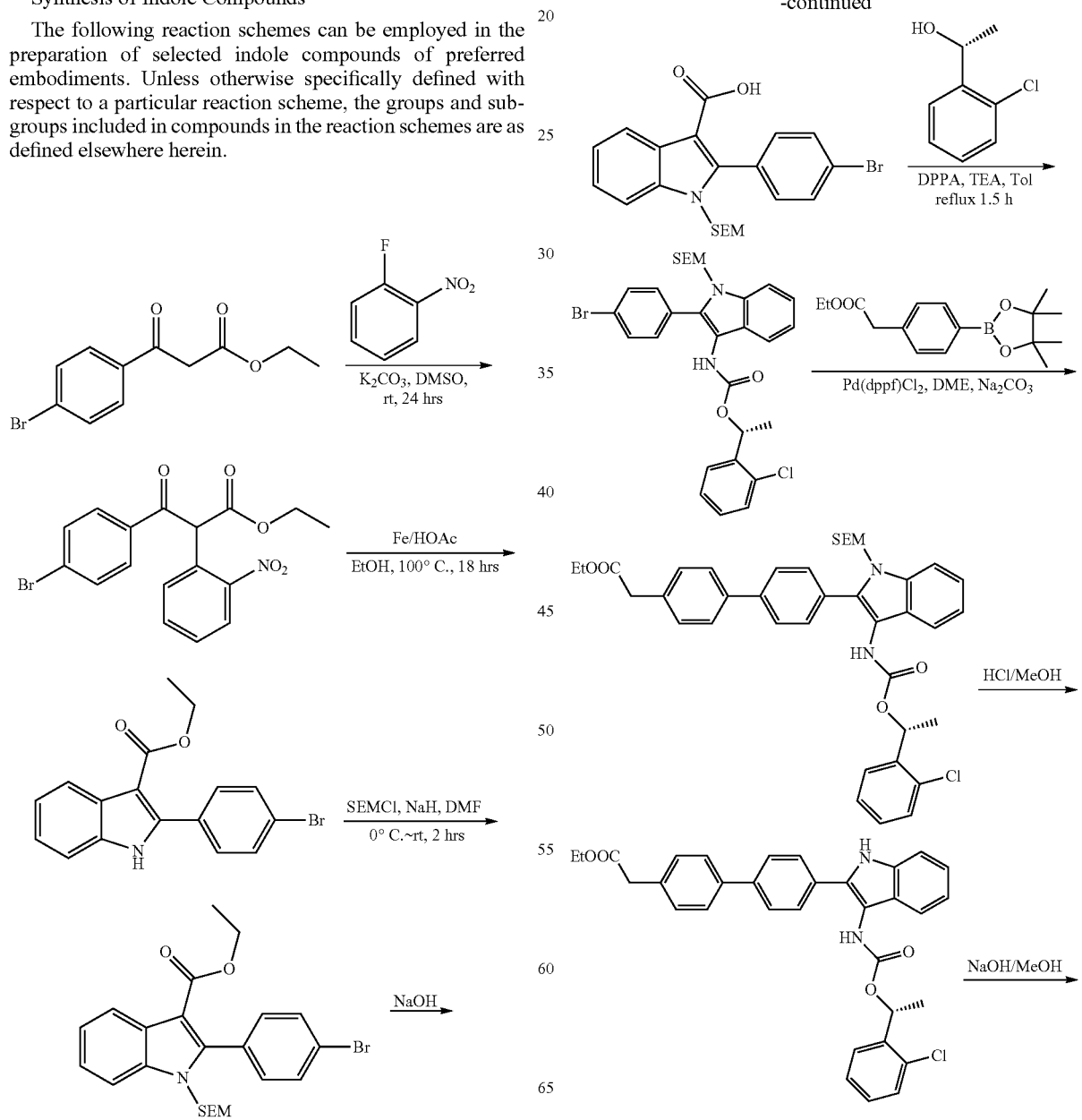

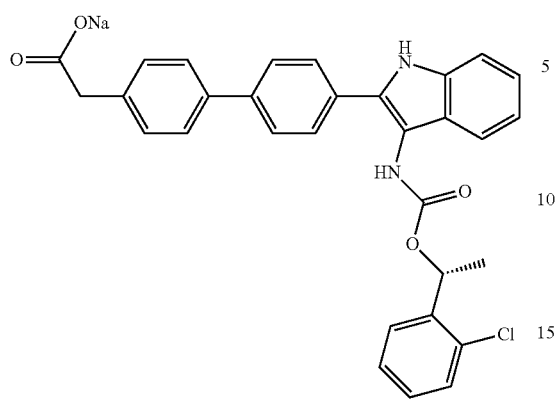
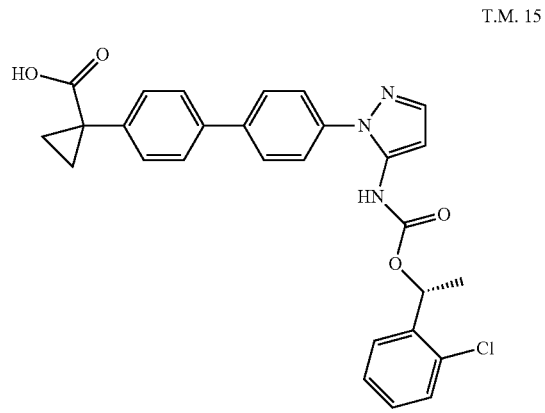
T.M. 15
T.M. 24
Exemplary Heteroaryl Compounds
The following exemplary compounds of Formula (I) were prepared according to the various reaction schemes presented below.
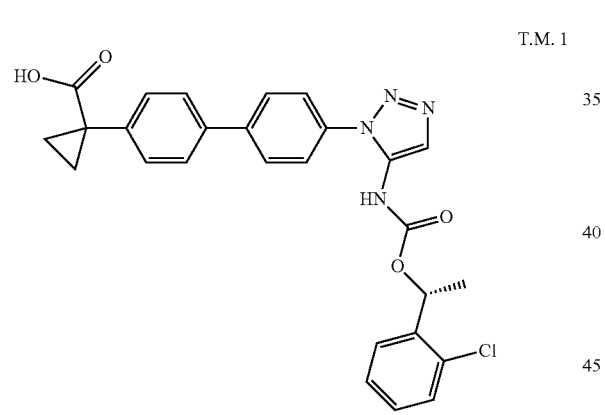
T.M. 1
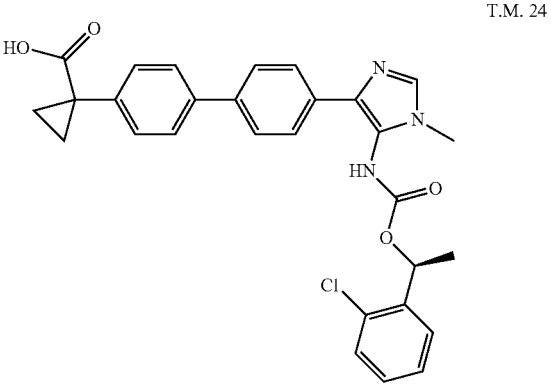
T.M. 30
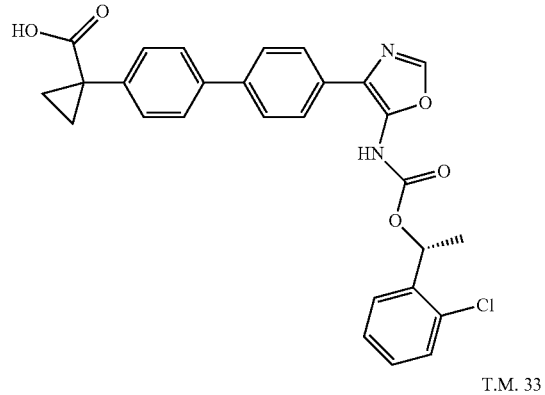
T.M. 33
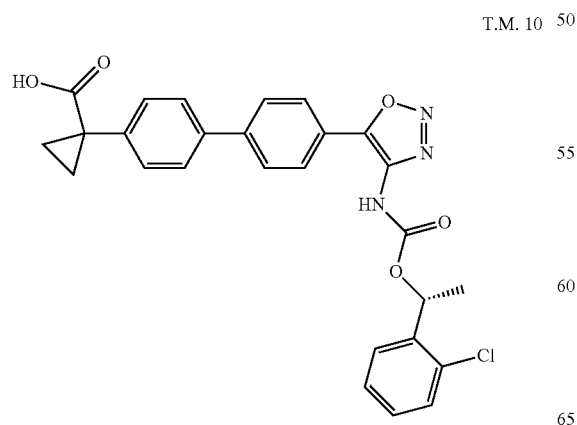
T.M. 10
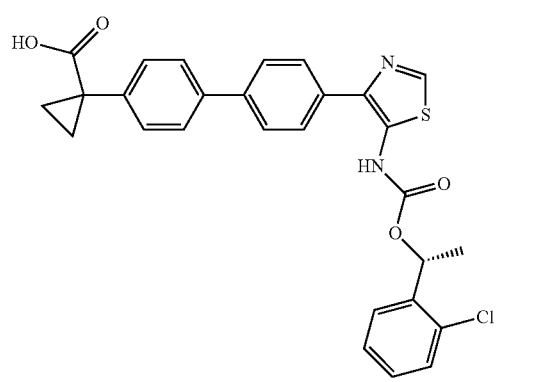
The 1,2,3-triazole compound T.M.1 was prepared according to the following route:

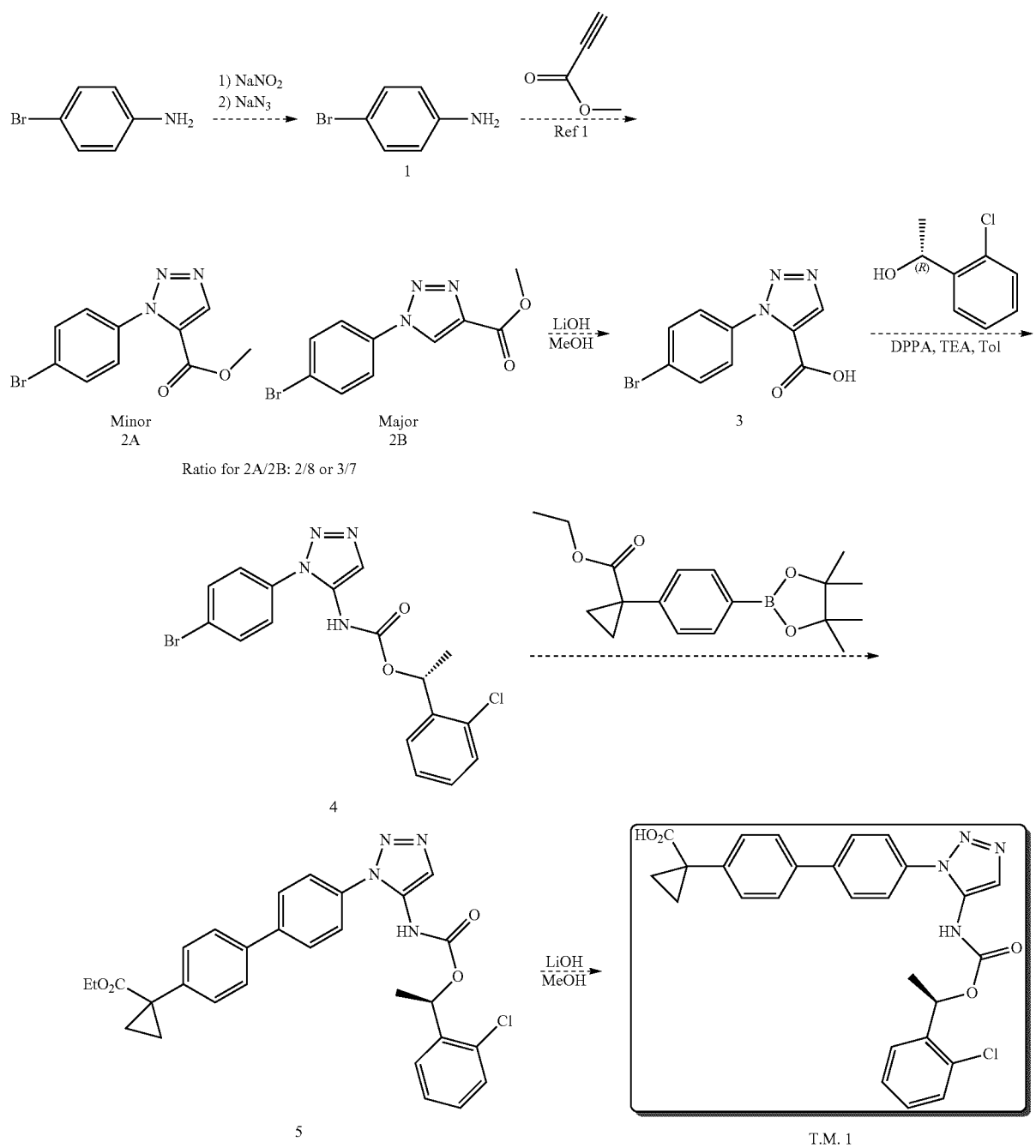
Ref 1: *Chemistry-A European Journal*, 9(12), 2770-2774; 2003
A first alternative route to preparing the 1,2,3-triazole compound T.M.1 was as follows:
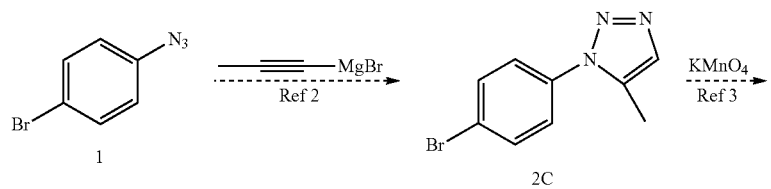

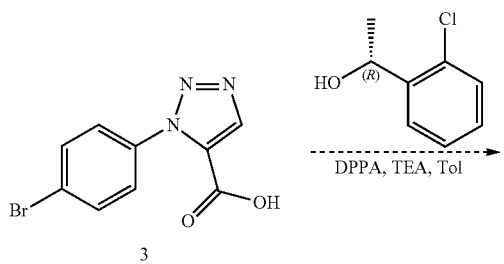
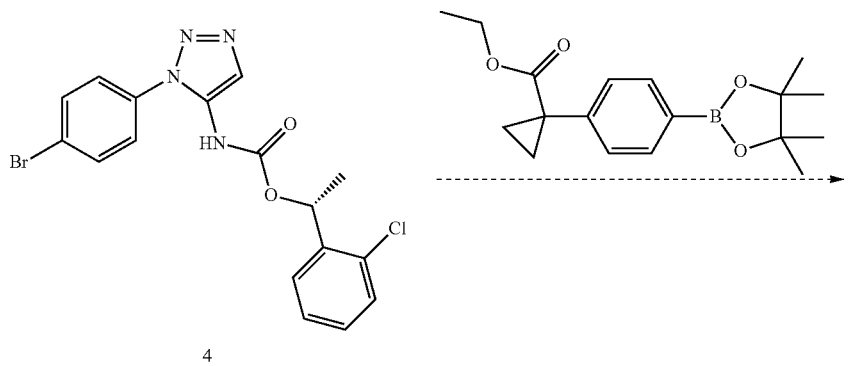
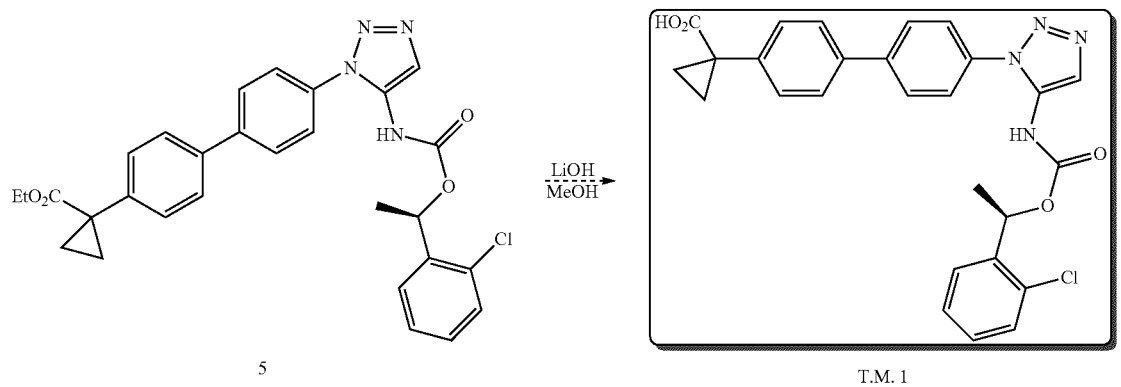
Ref 2: *Organic Process Research & Development*, 13(6), 1407-1412; 2009
Ref 3: *Journal of Heterocyclic Chemistry*, 24(5), 1275-9; 1987
A second alternative route to preparing the 1,2,3-triazole compound T.M.1 was as follows:
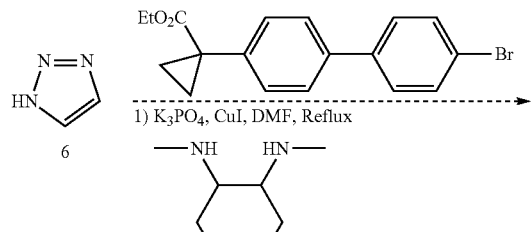
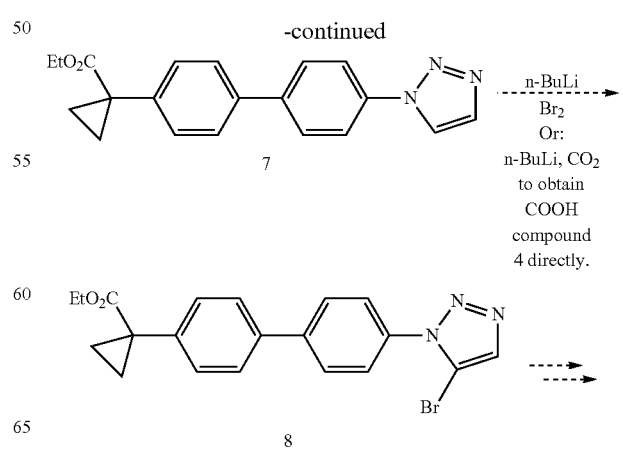

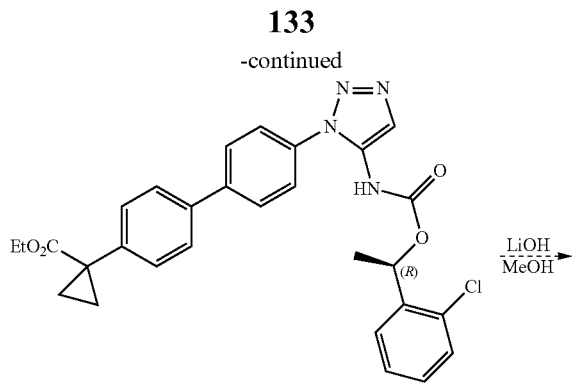

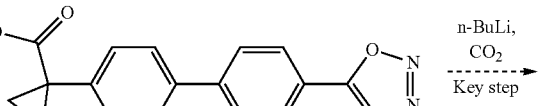

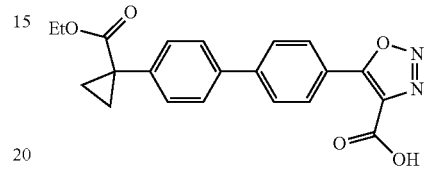

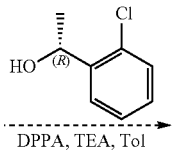

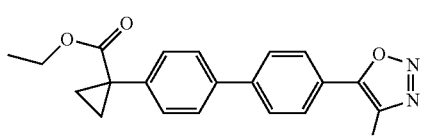

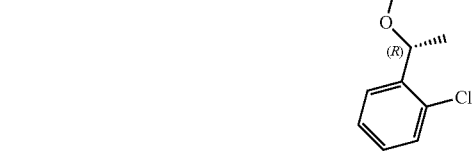

Selected methods described in U.S. Pat. Publ. No. 2008/0139572, the contents of which are hereby incorporated herein by reference in their entirety, were employed in synthesizing the 1,2,3-triazole compound T.M.1:

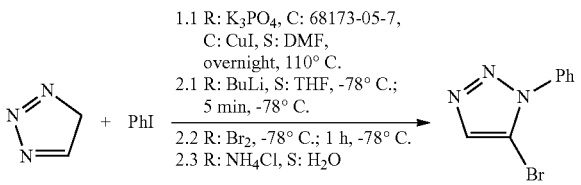

1.1 R: $K_3PO_4$, C: 68173-05-7, C: CuI, S: DMF, overnight, 110° C.
2.1 R: BuLi, S: THF, -78° C.; 5 min, -78° C.
2.2 R: $Br_2$, -78° C.; 1 h, -78° C.
2.3 R: $NH_4Cl$, S: $H_2O$ The 1,2,3-triazole compound T.M.10 was prepared as follows:

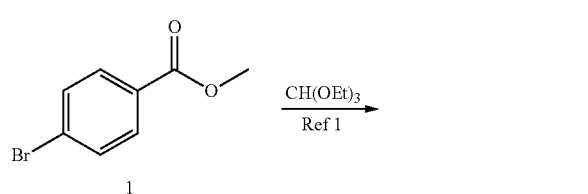

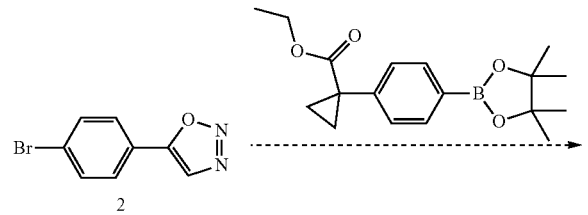

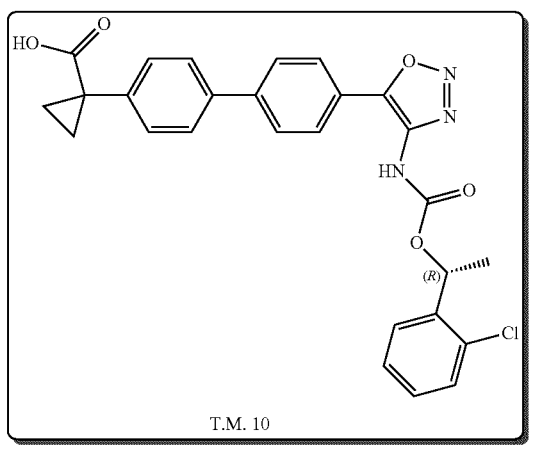

Ref 1: PCT Int. Appl., 2005084296, 15 Sep. 2005

The 1,2-pyrazole compound T.M.15 was prepared as follows:

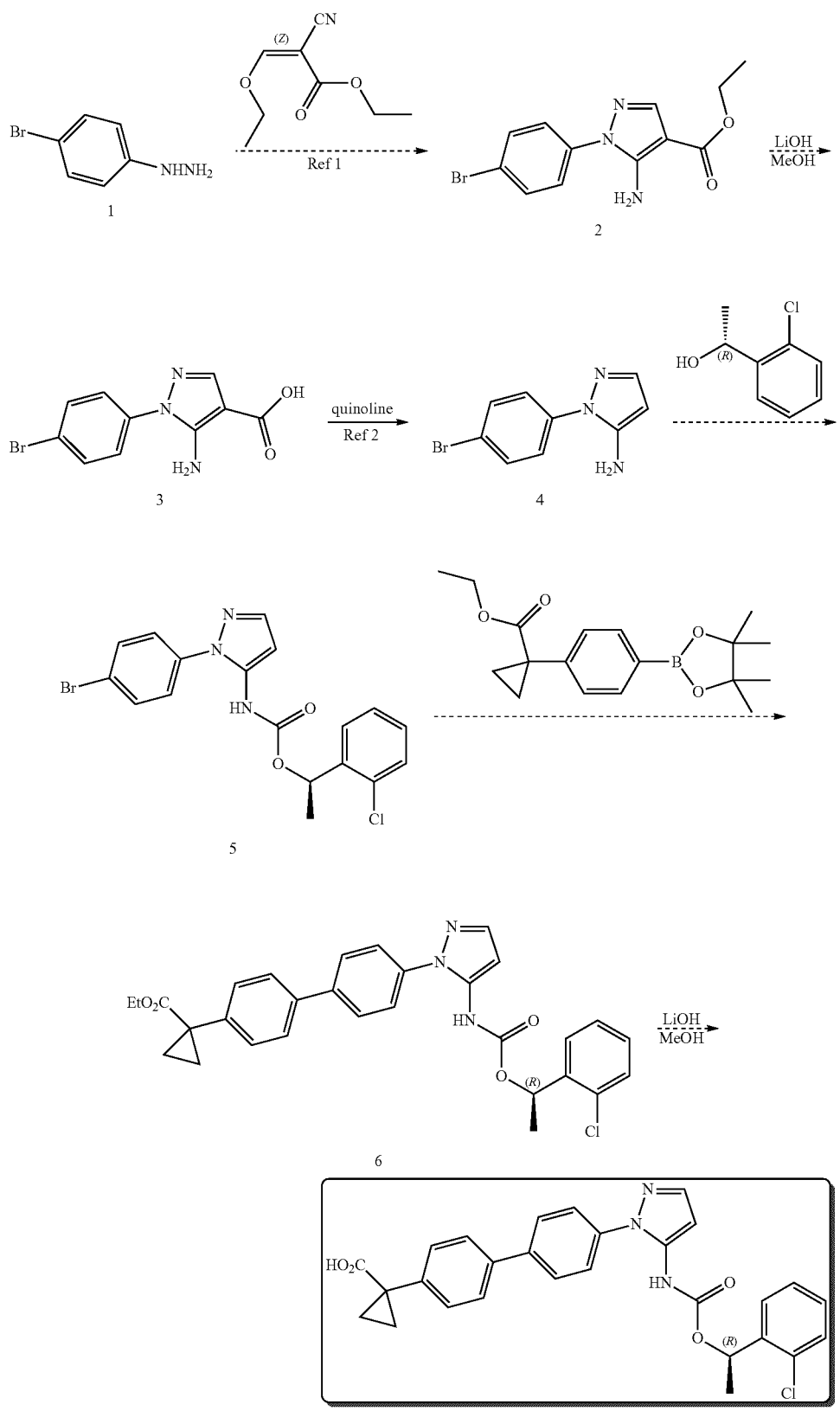
T.M 15
Ref 1: *Heterocyclic Communications*, 11(5), 385-388, 2005
Ref 2: PCT Int. Appl., 2006132811, 14 Dec. 2006

An alternative route for the preparation of the 1,2-pyrazole compound T.M.15 was as follows:

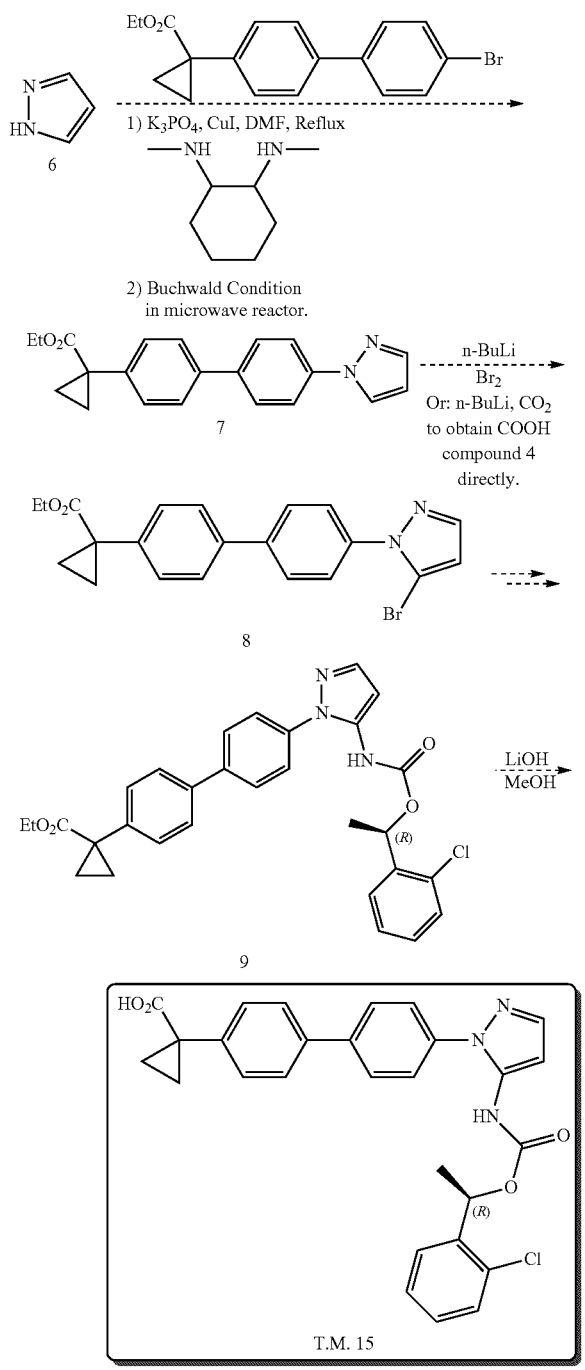

Selected methods described in Journal of Organic Chemistry, 73(1), 177-183 (2008), the contents of which are hereby incorporated herein by reference in their entirety, were employed in synthesizing the 1,2-pyrazole compound T.M.15:

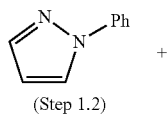

(Step 1.2)

-continued

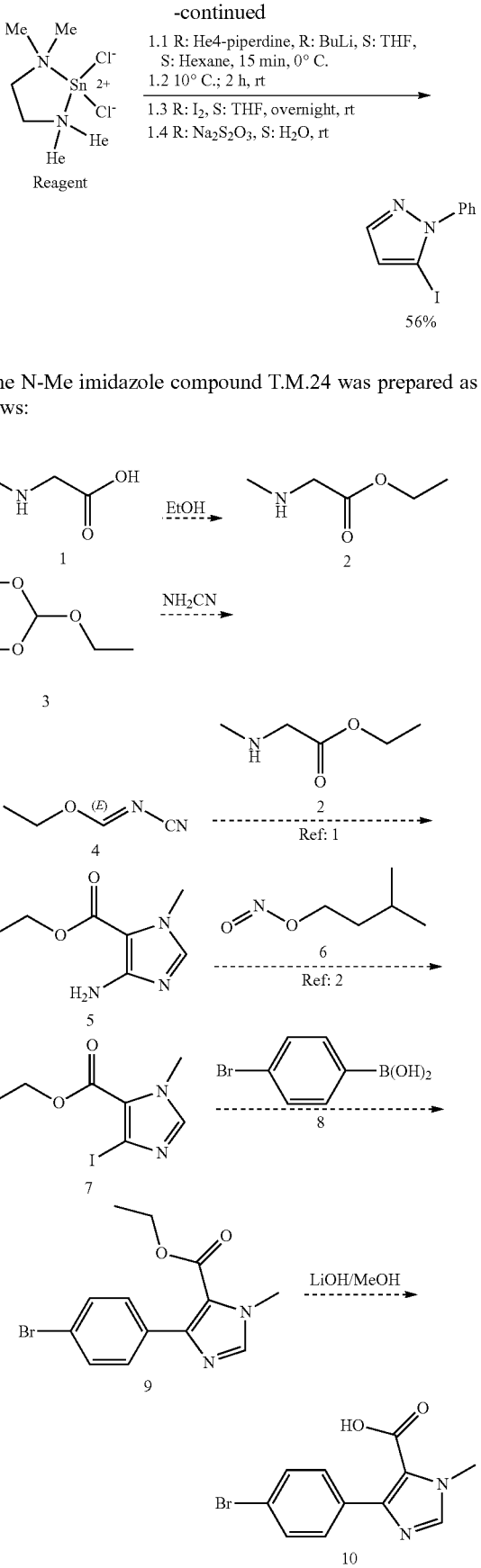

1.1 R: He4-piperdine, R: BuLi, S: THF, S: Hexane, 15 min, 0° C.
1.2 10° C.; 2 h, rt
1.3 R: I$_2$, S: THF, overnight, rt
1.4 R: Na$_2$S$_2$O$_3$, S: H$_2$O, rt The N-Me imidazole compound T.M.24 was prepared as follows:

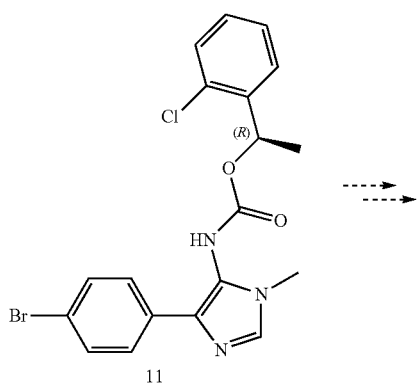
11
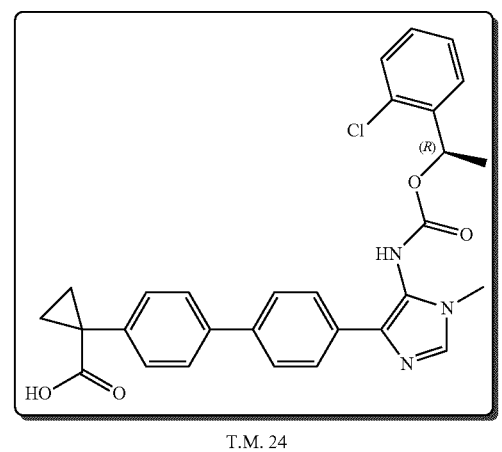
T.M. 24
Ref 1: US 20090275561
Ref 2: WO2009137454
An alternative route for preparation of the N-Me imidazole compound T.M.24 was as follows:
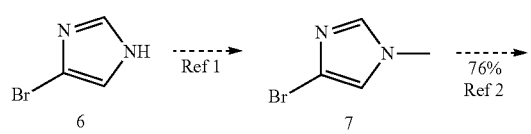
Also commercially available
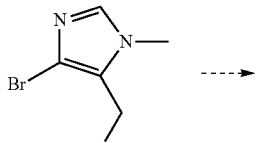
8
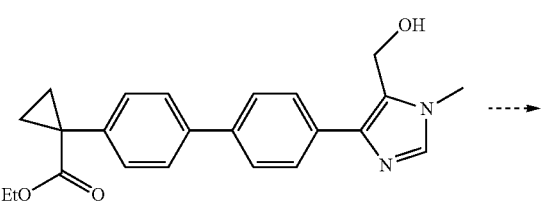
9
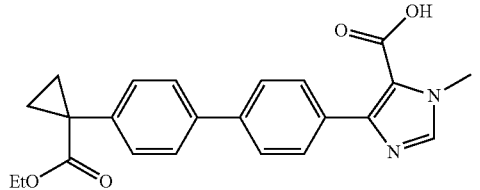
10
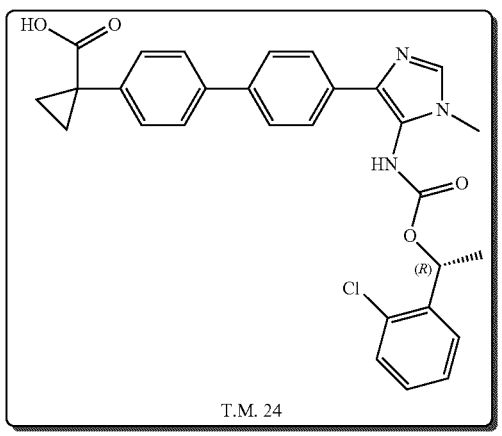
T.M. 24
Ref 1: Synthesis, (10), 767-71; 1988
Ref 2: Chemical & Pharmaceutical Bulletin, 42(9), 1784-90; 1994
The 1,3-oxazole compound T.M.30 was prepared as follows:
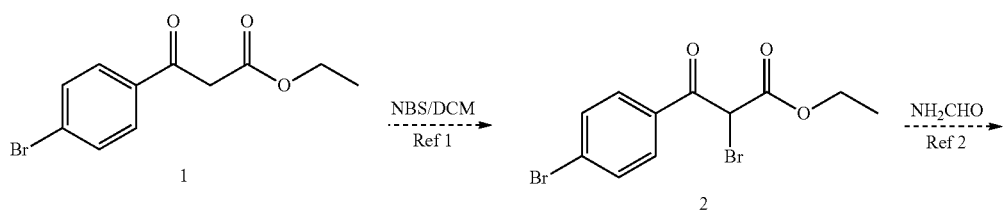

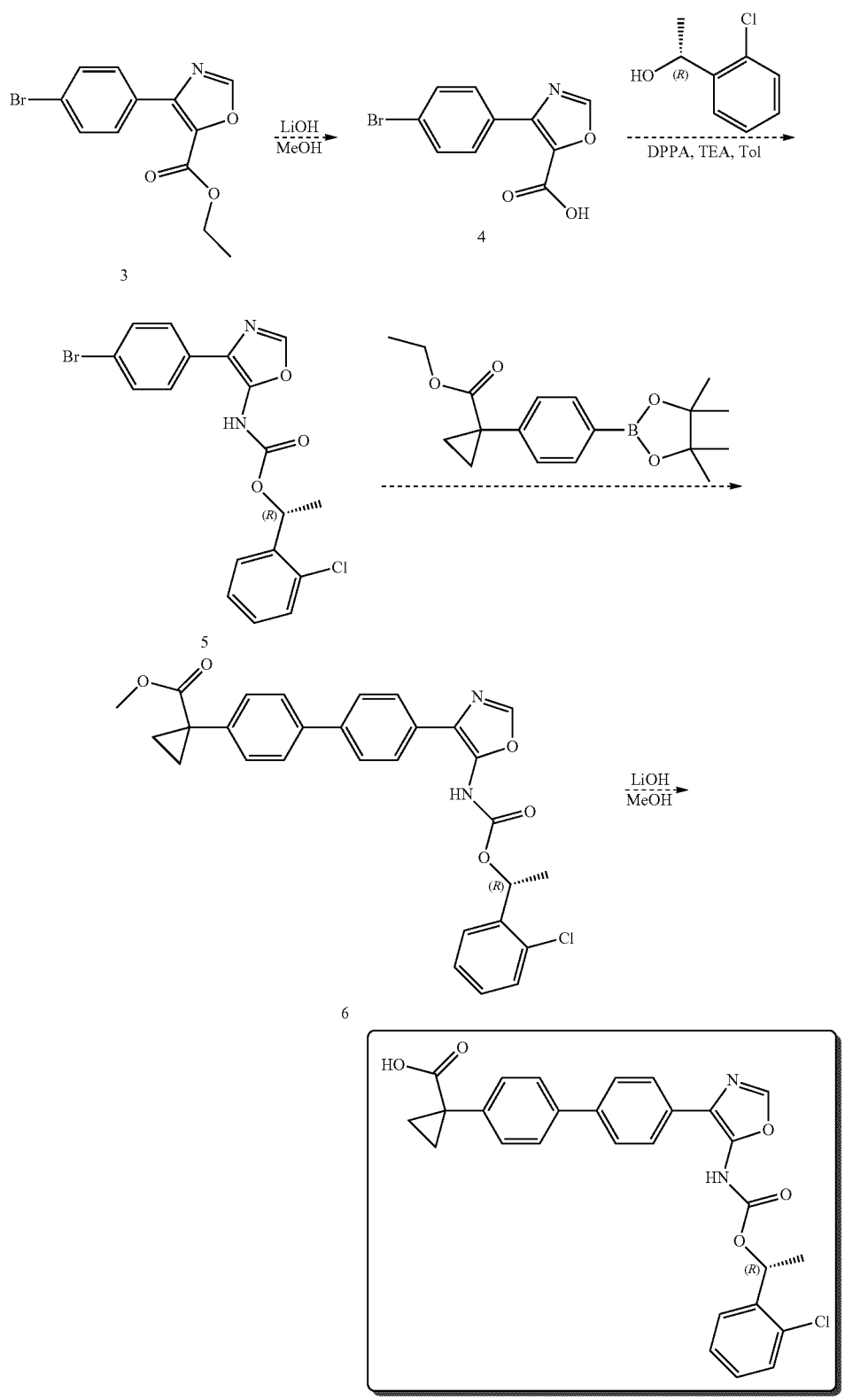
T.M. 30
Ref 1: WO 2009102318
Ref 2: Tetrahefron, 66(7), 1465-1471; 2010

The 1,3-thiazole compound T.M.33 was prepared as follows:
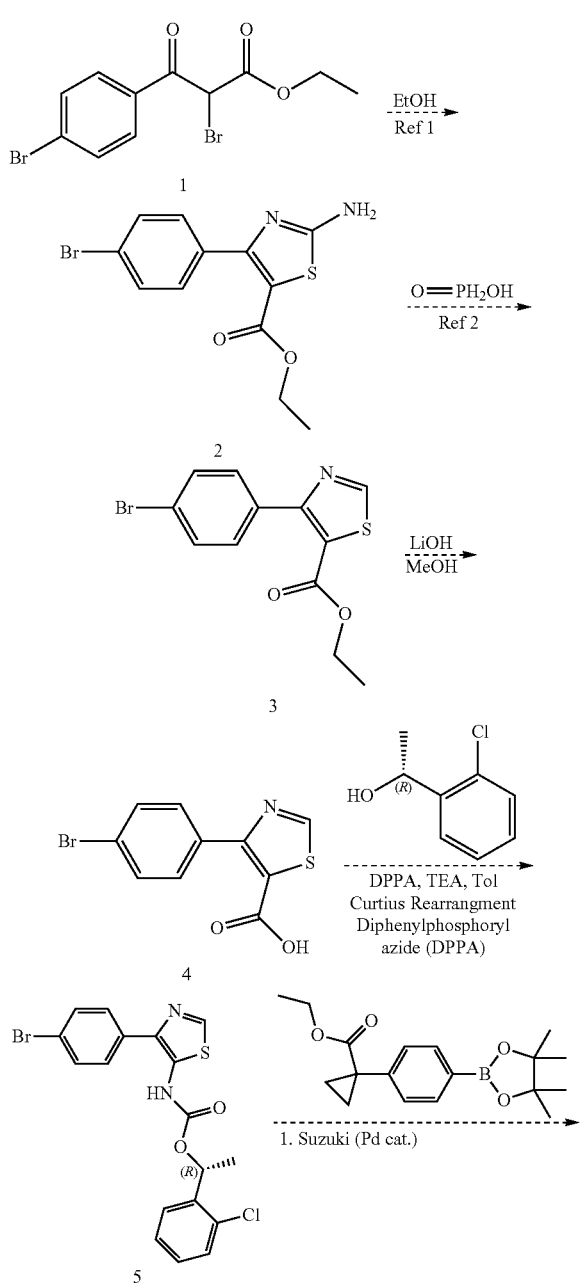
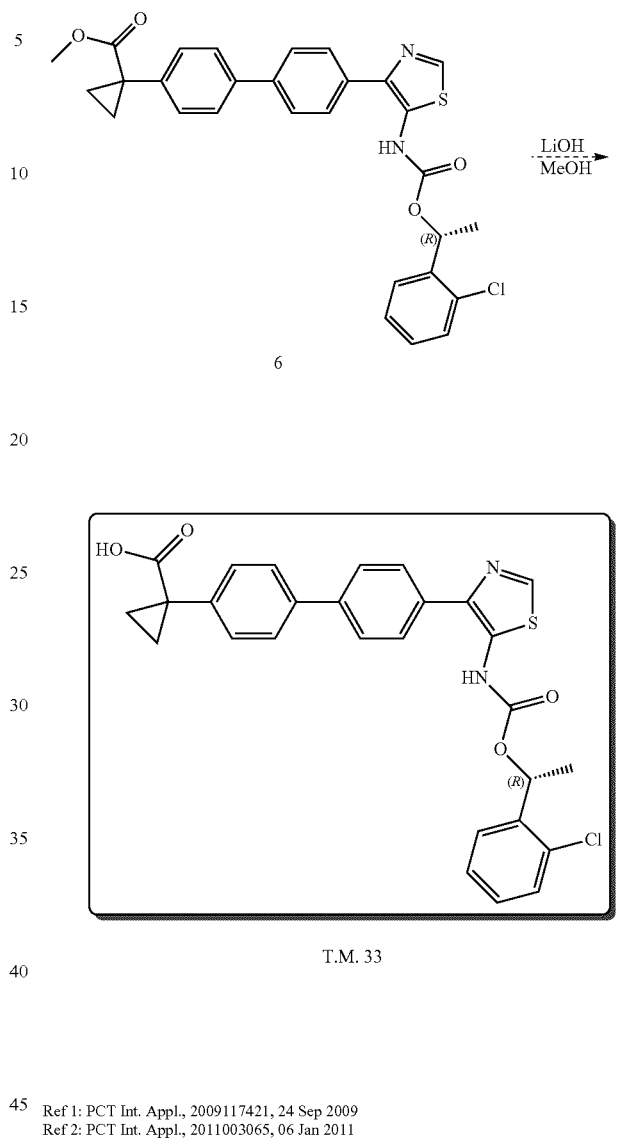
Ref 1: PCT Int. Appl., 2009117421, 24 Sep 2009
Ref 2: PCT Int. Appl., 2011003065, 06 Jan 2011
The thiadiazole compound T.M.12 was prepared as follows:
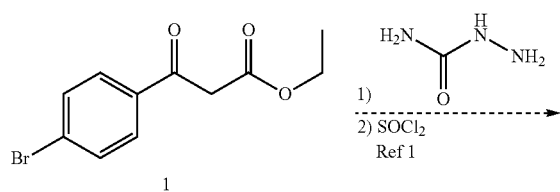

-continued
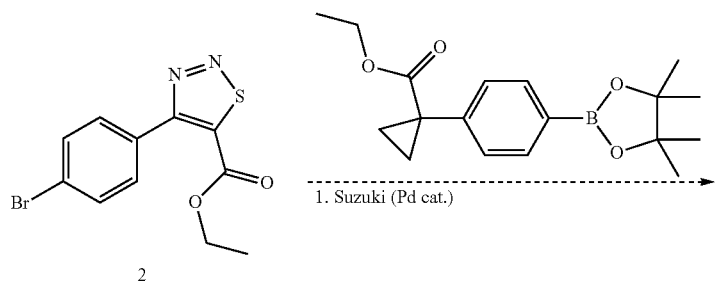
2
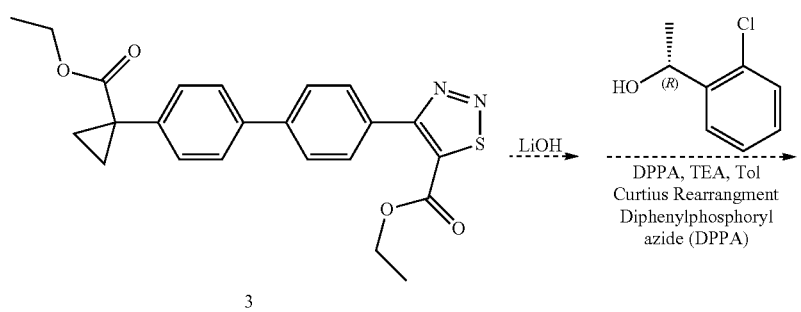
3
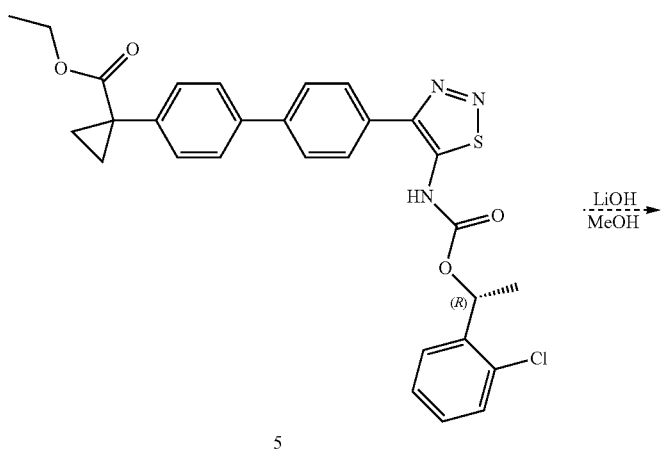
5
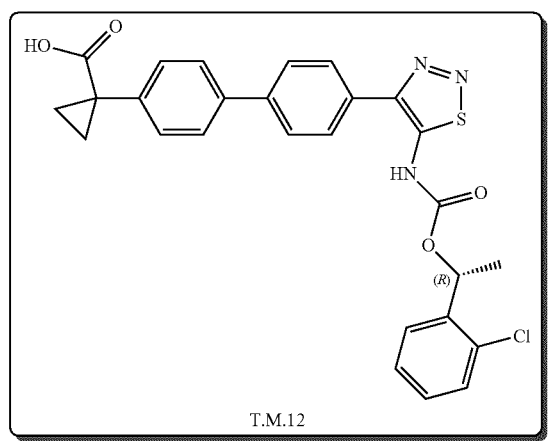
T.M.12
Ref 1: *Asian Journal of Chemistry*, 19(6), 4679-4683; 2007

147
Exemplary Aromatic Oxazole Carbamates
The following exemplary compounds of Formula (I) were prepared according to the various reaction schemes presented below.
T.M.101
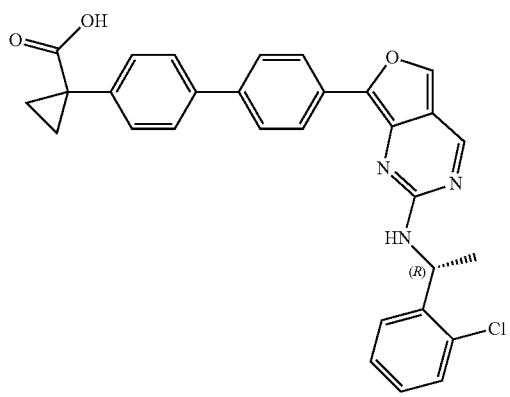
T.M.102
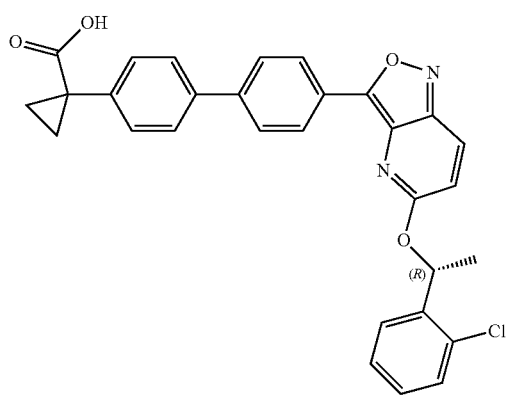
The carbamate T.M.101 was prepared as follows:
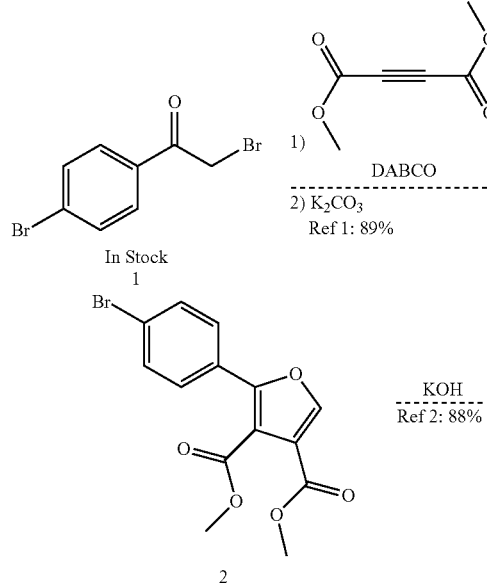
148
-continued
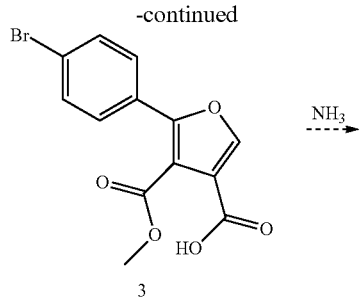
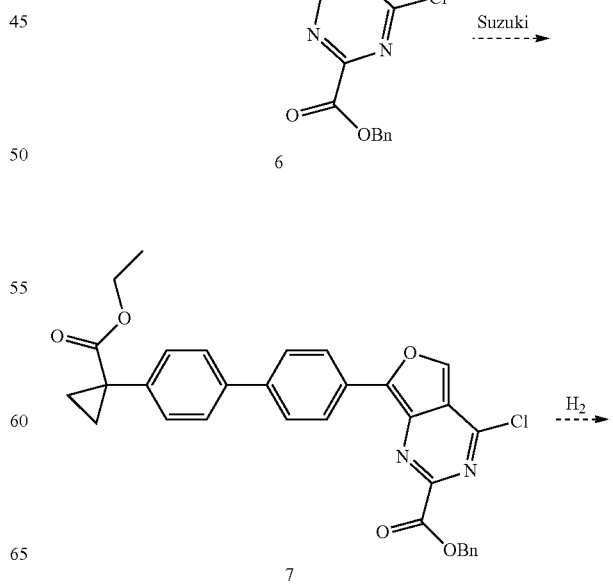

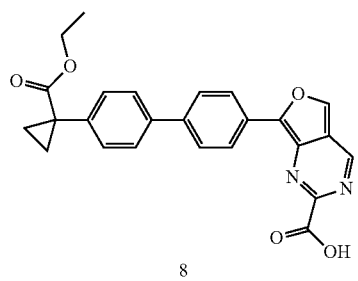

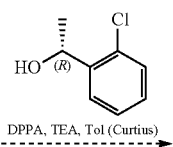

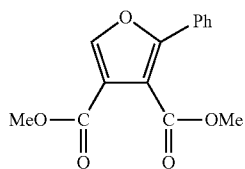

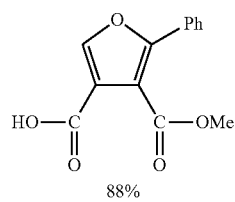

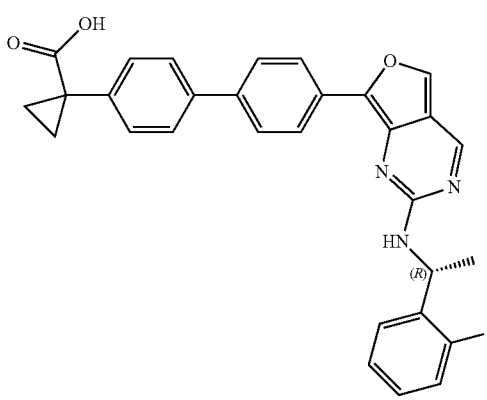

T.M. 101

Selected methods described in Journal of Organic Chemistry, 70(20), 8204-8207 (2005), the contents of which are hereby incorporated herein by reference in their entirety, were employed in synthesizing the carbamate compound T.M.101:

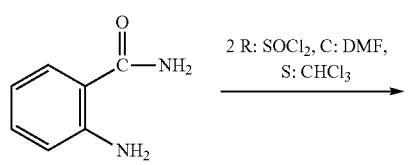

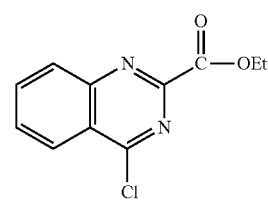

Selected methods described in Heterocycles, 55(2), 265-277 (2001), the contents of which are hereby incorporated herein by reference in their entirety, were employed in synthesizing the carbamate compound T.M.101:

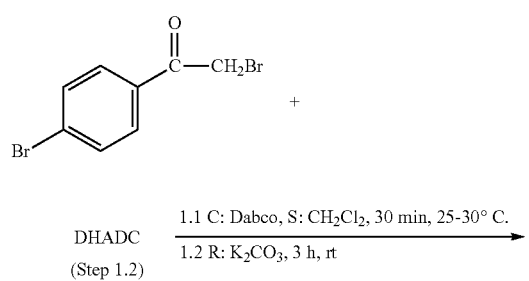

Selected methods described in PCT Int. Publ. No. 2002/076976, 3 Oct. 2002, the contents of which are hereby incorporated herein by reference in their entirety, were employed in synthesizing the carbamate compound T.M.101:

An alternative route for the preparation of carbamate T.M.101 was as follows:

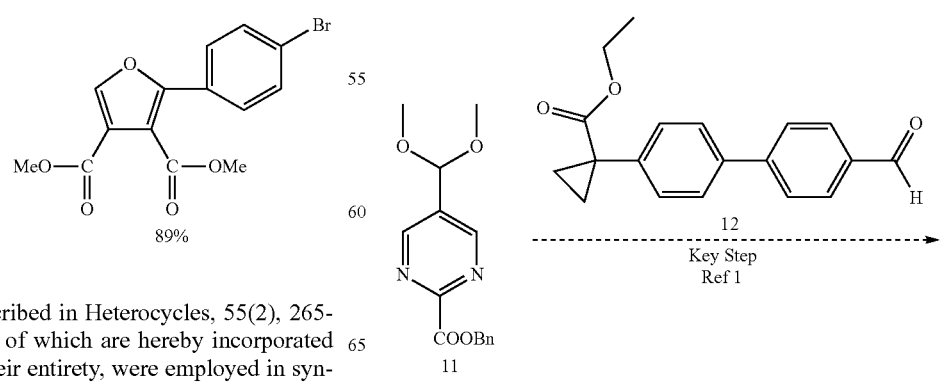

-continued
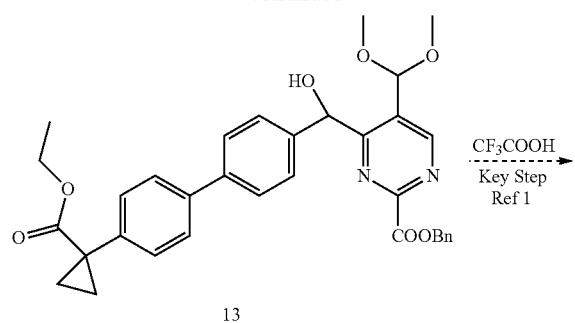
13
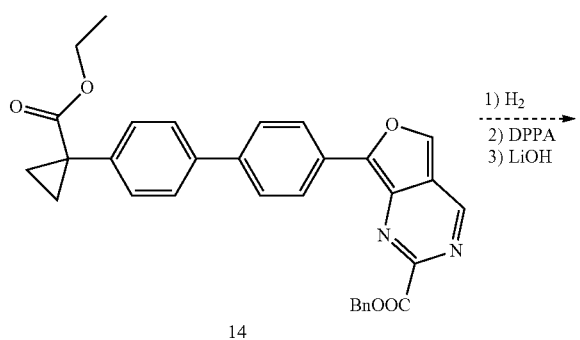
14
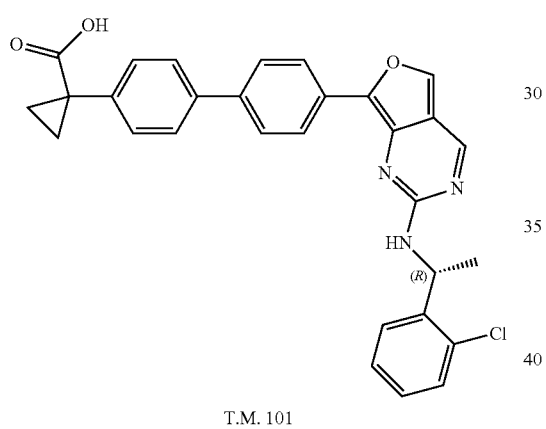
T.M. 101
Ref 1: Journal of Organic Chemistry, 67(3), 1001-1003; 2002
Selected methods described in Journal of Organic Chemistry, 67(3), 1001-1003; 2002, the contents of which are hereby incorporated herein by reference in their entirety, were employed in synthesizing the carbamate compound T.M.101.
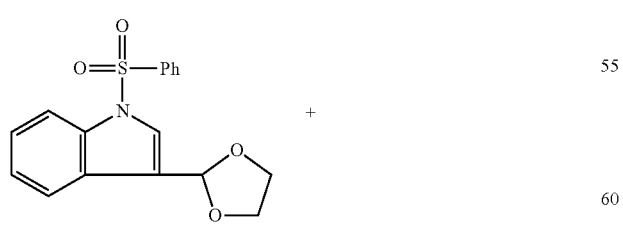
-continued
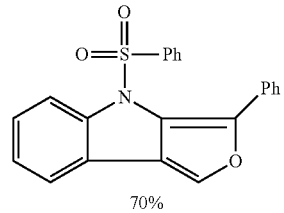
70%
The carbamate T.M.102 was prepared as follows:
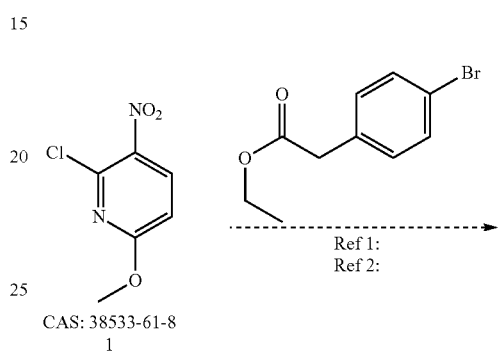
CAS: 38533-61-8
1
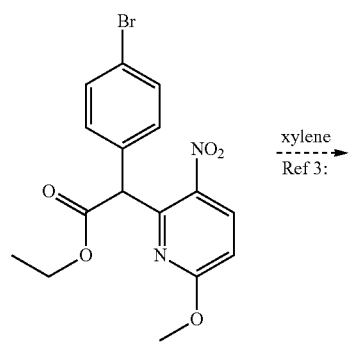
2
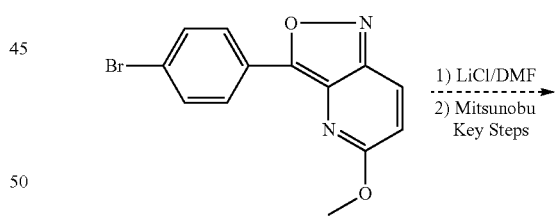
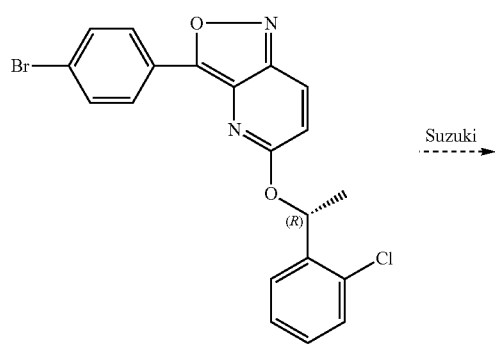
4

153
-continued

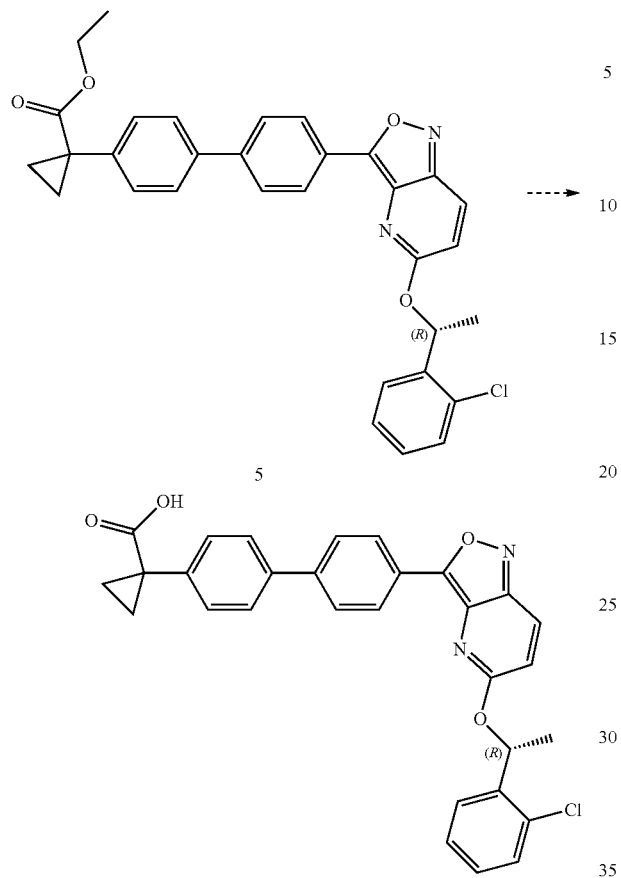

T.M. 102

Ref 1: *Zhurnal Organicheskoi Khimii*, 24(9), 1806-16; 1988
Ref 2: *PCT Int. Appl.*, 2010088177, 05 Aug 2010
Ref 3: *Journal of the Chemical Society, Chemical Communications*, (23), 2457-9; 1995

154

Selected methods described in Zhurnal Organicheskoi Khimii, 24(9), 1806-16; 1988, the contents of which are hereby incorporated herein by reference in their entirety, were employed in synthesizing the carbamate compound T.M.102.

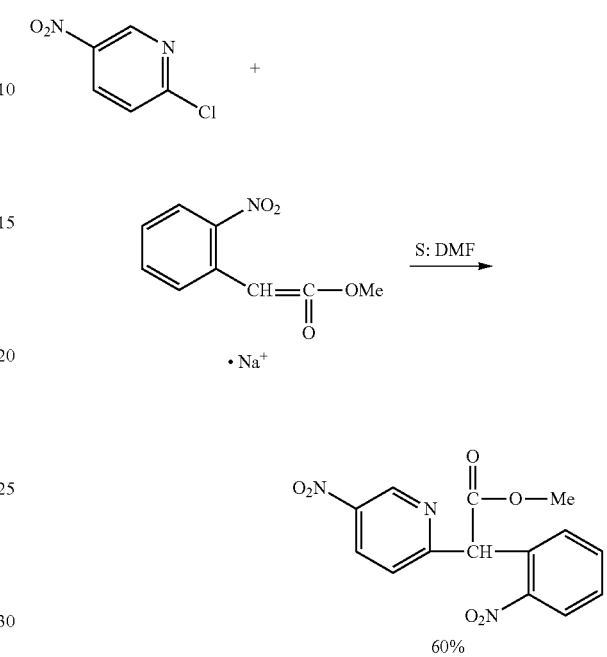

Selected methods described in PCT Int. Publ., 2010088177, 5 Aug. 2010, the contents of which are hereby incorporated herein by reference in their entirety, were employed in synthesizing the carbamate compound T.M.102:

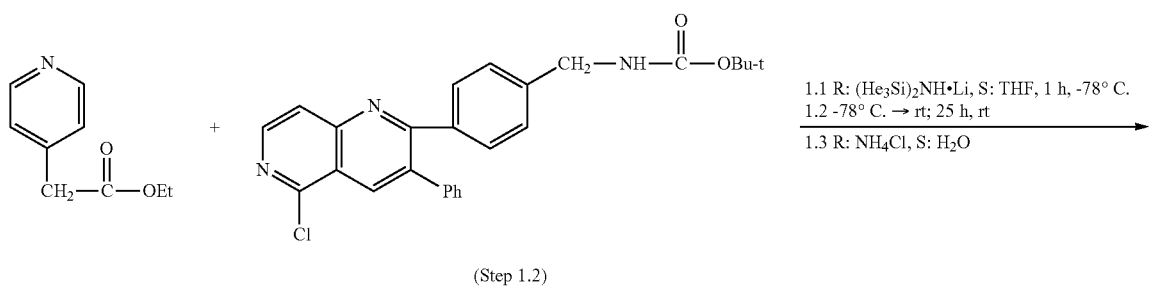

(Step 1.2)

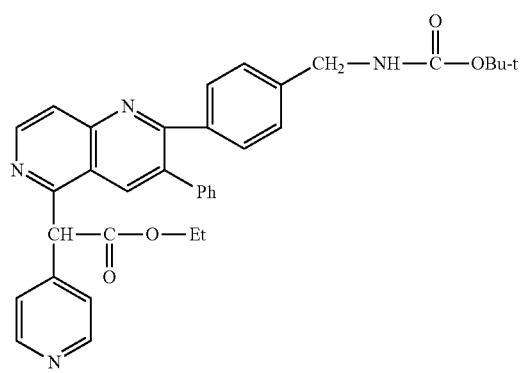

Selected methods described in Journal of the Chemical Society, Chemical Communications, (23), 2457-9; 1995, the contents of which are hereby incorporated herein by reference in their entirety, were employed in synthesizing the carbamate compound T.M.102:

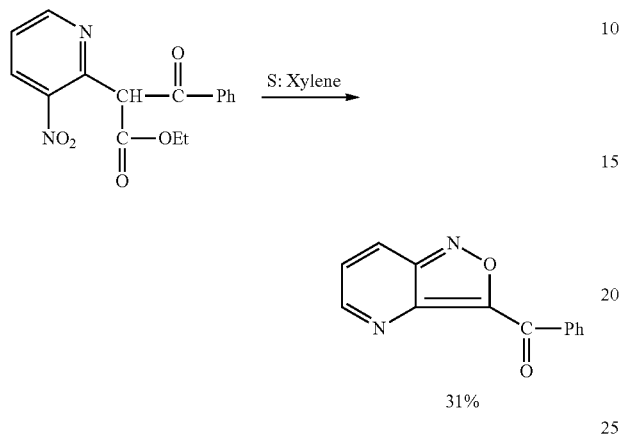

An alternative route for the synthesis of carbamate T.M.102 was as follows:

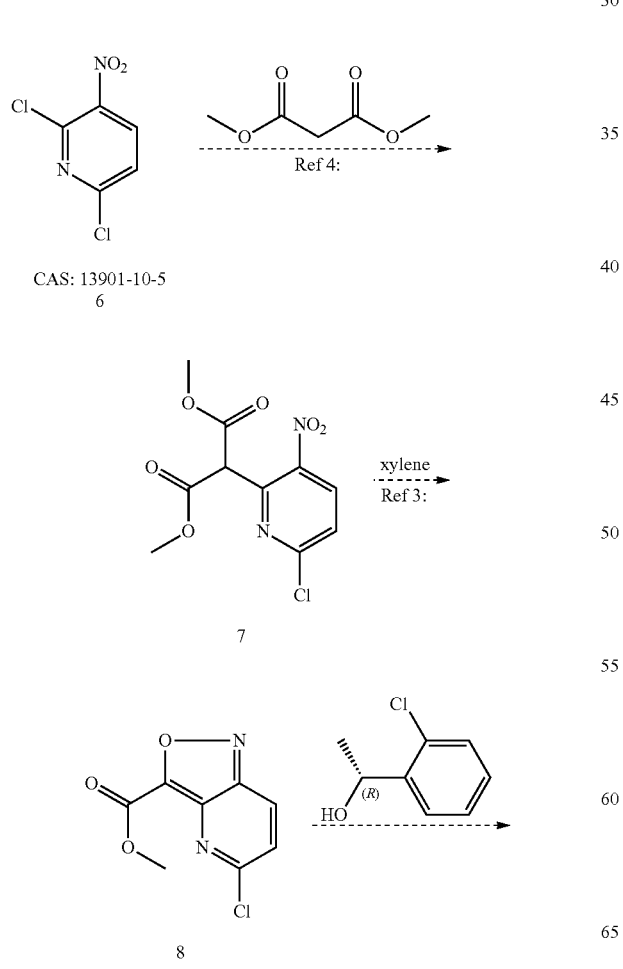

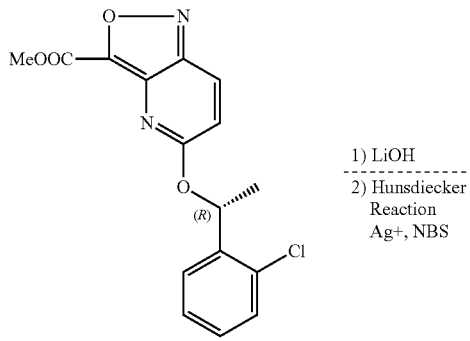

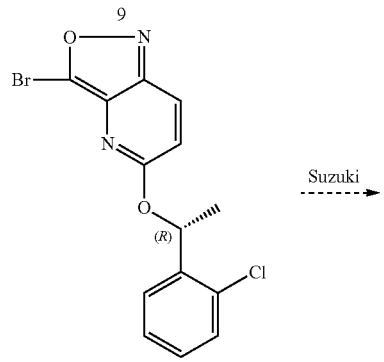

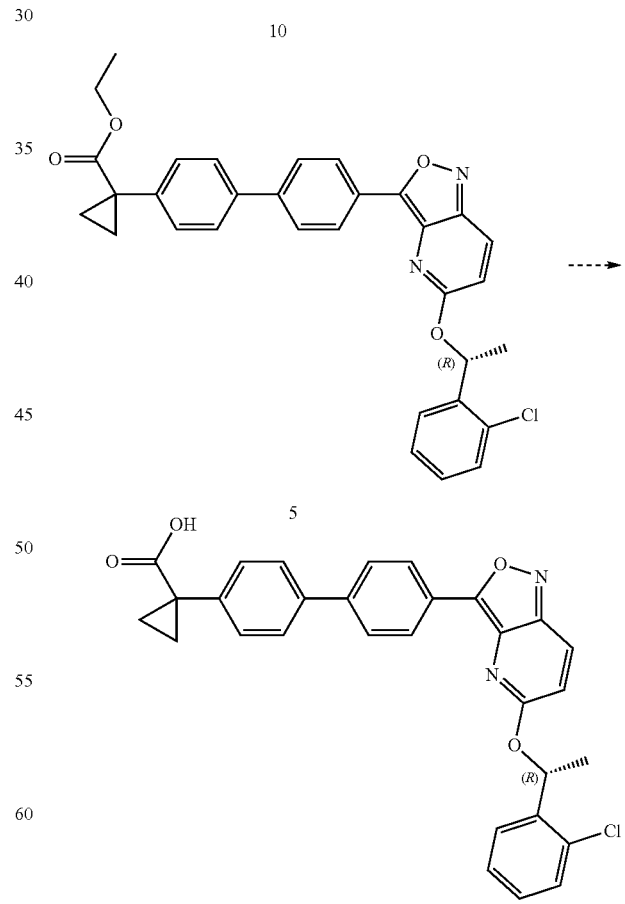

T.M. 102

Ref 3: *Journal of the Chemical Society, Chemical Communication*, (23), 2457-9; 1995
Ref 4: *Faming Zhuanli Shenqing Gongkai Shuomingshu*, 101704815, 12 May 2010

Selected methods described in Faming Zhuanli Shenqing Gongkai Shuomingshu, 101704815, 12 May 2010, the contents of which are hereby incorporated herein by reference in their entirety, were employed in synthesizing the carbamate compound T.M.102.

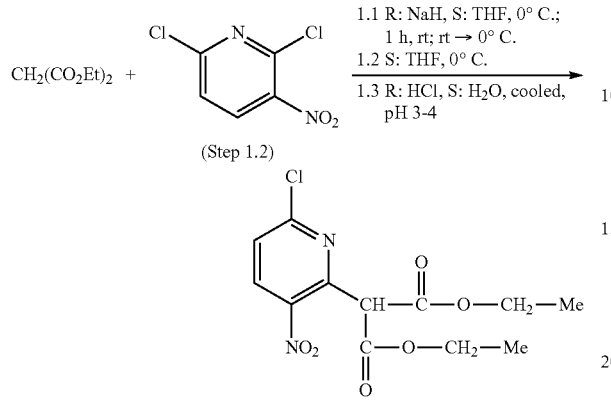

(Step 1.2)

Selected methods described in Journal of the Chemical Society, Chemical Communications, (23), 2457-9; 1995, the contents of which are hereby incorporated herein by reference in their entirety, were employed in synthesizing the carbamate compound T.M.102.

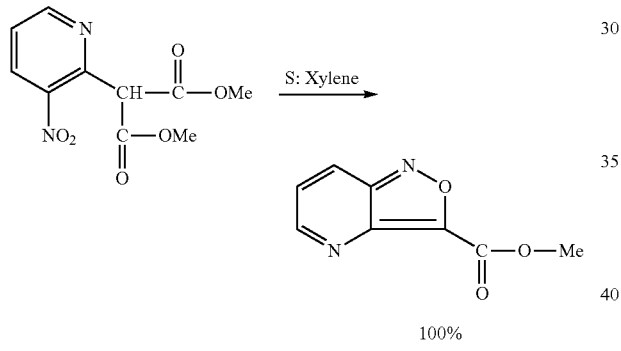

Exemplary Phenyl Substituted Thiazoles

The following exemplary compound of Formula (I) was prepared according to the various reaction schemes presented below.

T.M.201

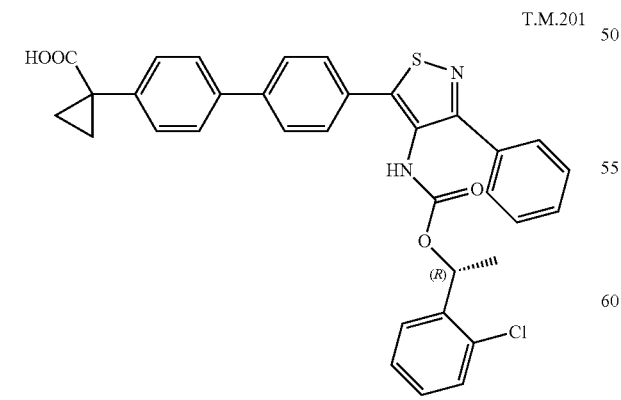

The phenyl substituted thiazole T.M.201 was prepared as follows:

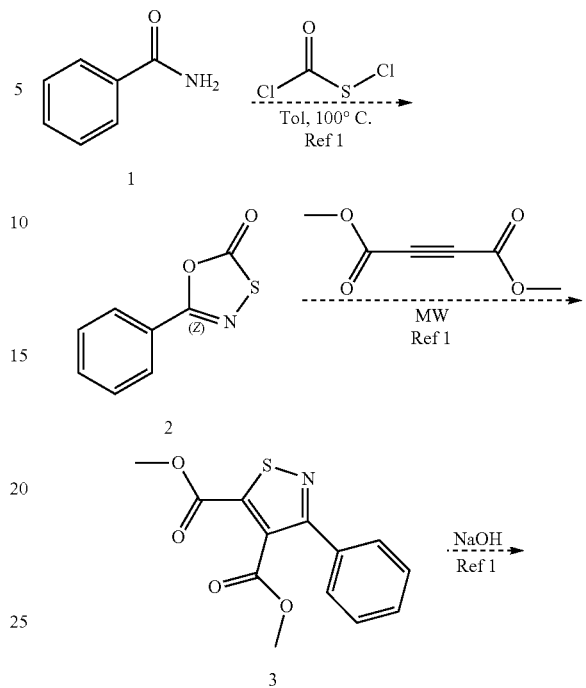

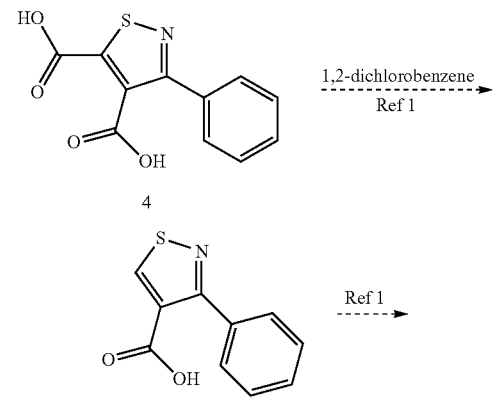

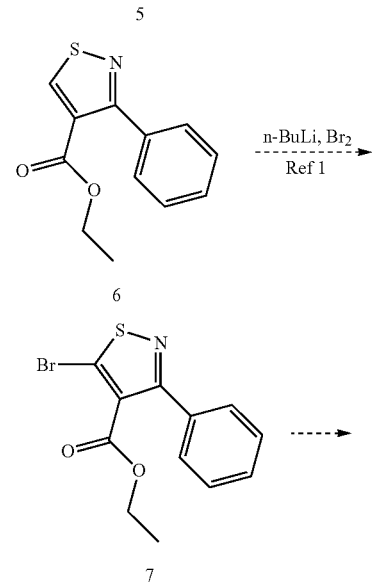

-continued
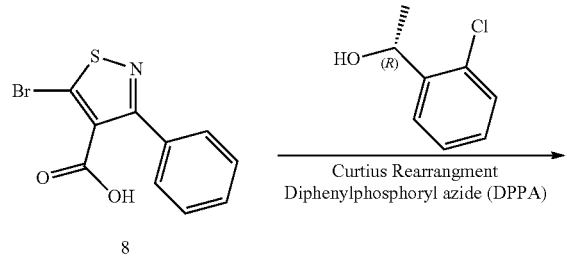
8
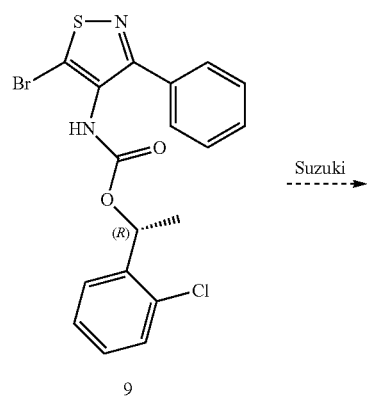
9
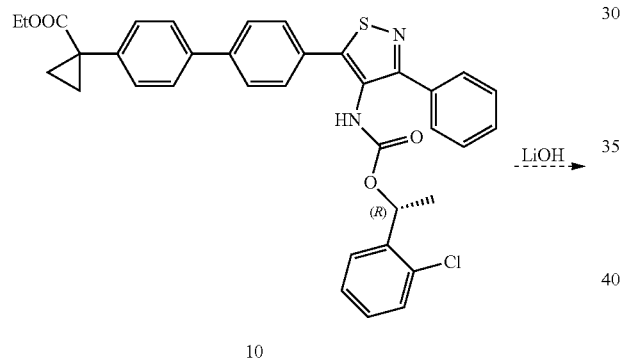
10
-continued
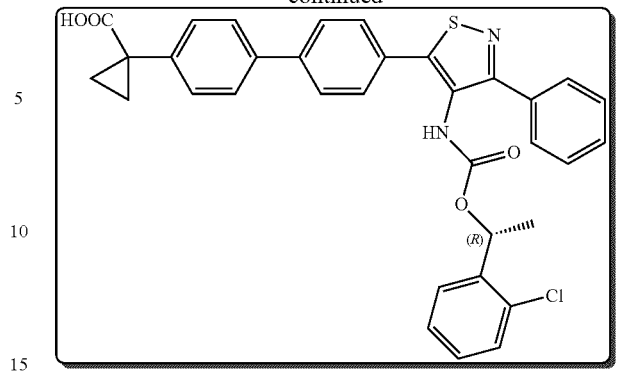
T.M. 201
Ref 1: PCT Int. Appl., 2009007098, 15 Jan 2009
Exemplary Terminal Proline Carboxylic Acids
The following exemplary compound of Formula (I) was prepared according to the various reaction schemes presented below.
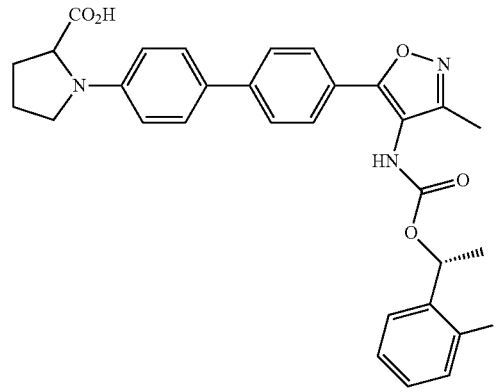
T.M.202
The terminal proline carboxylic acid T.M.202 was prepared as follows:
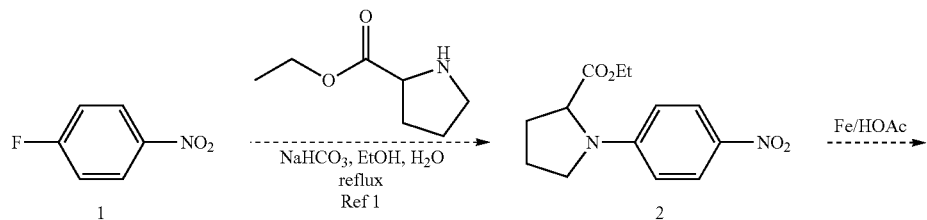
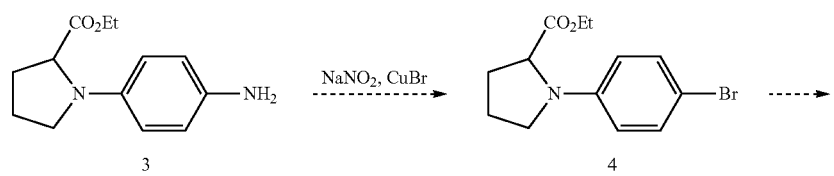

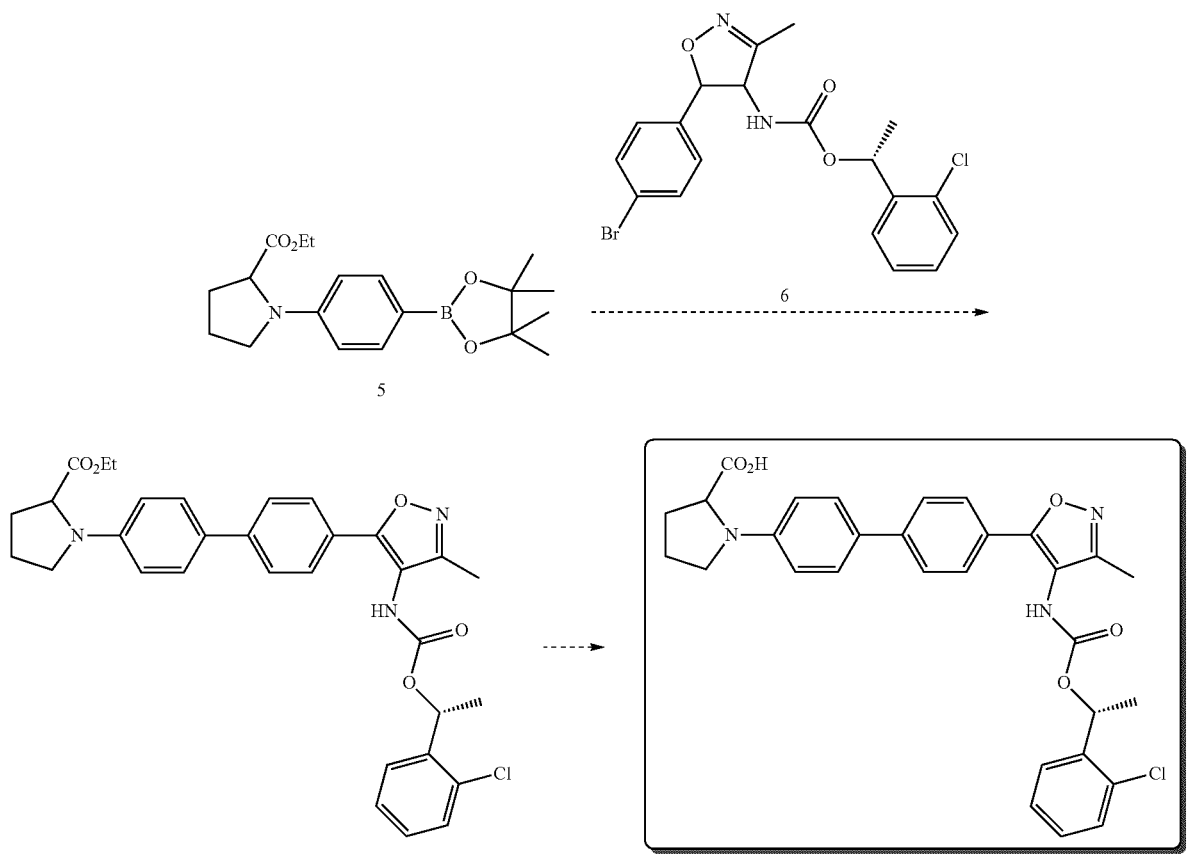

Ref 1: *Organic Letters*, 9(19), 3853-3855; 2007

Note: route will obtain a mixture of 2 diastereomers that will be separated.
Can start from pure chiral proline, also.

Exemplary Naphthyl-Acetylene Linker Compound

The following exemplary compounds of Formula (I) were prepared according to the various reaction schemes presented below.

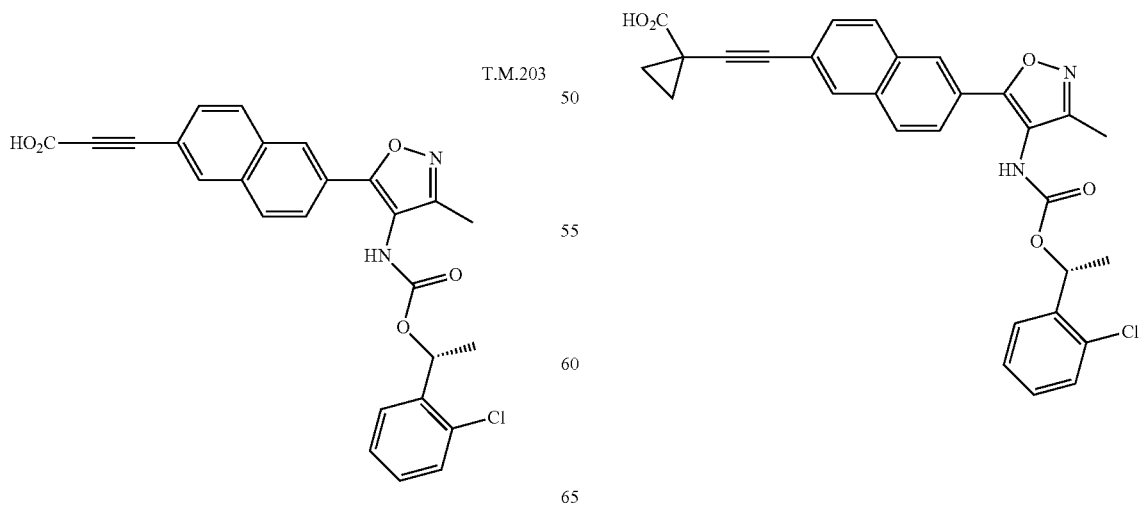

The naphthyl-acetylene linker compound T.M.203 was prepared as follows:

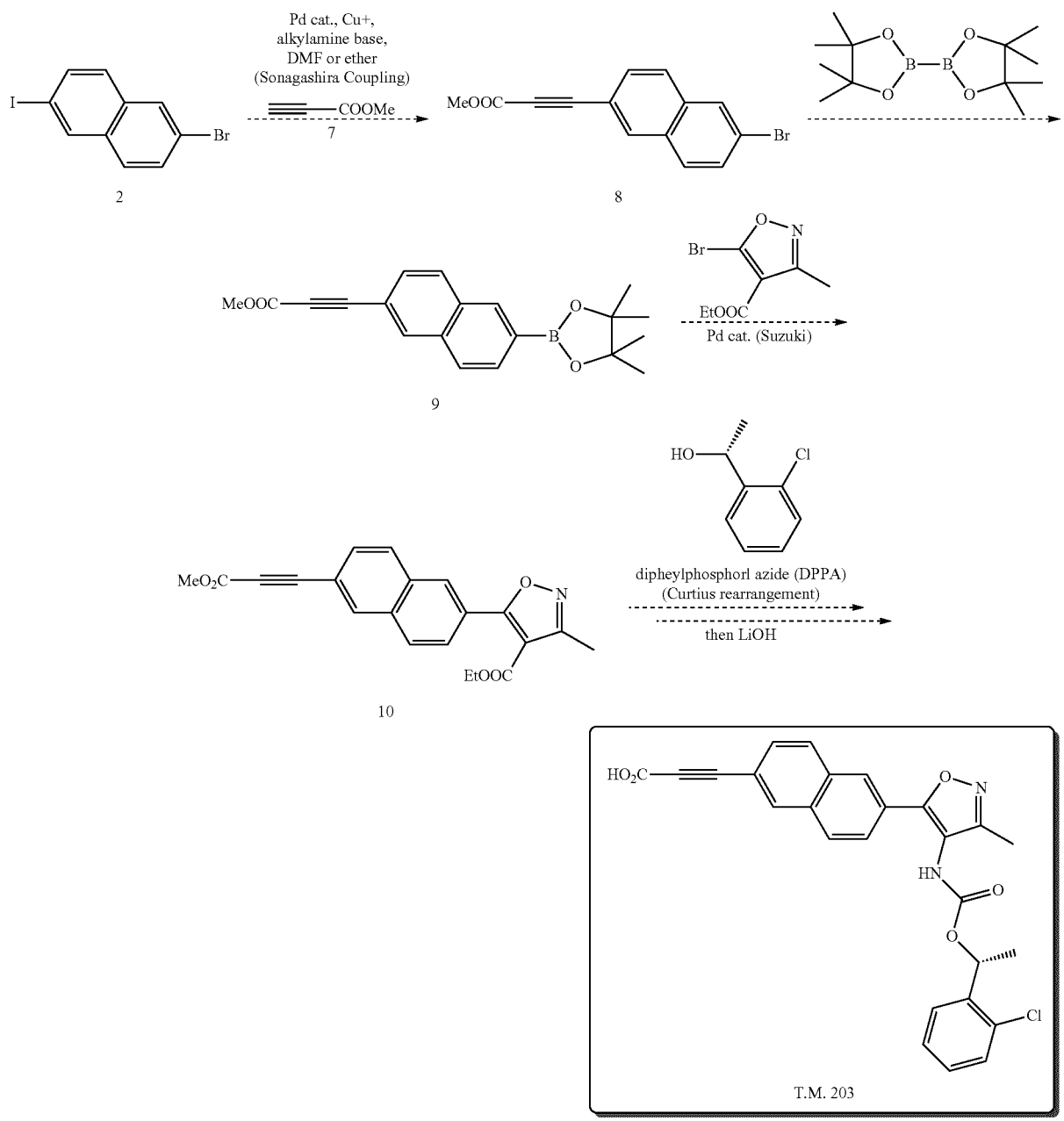
The naphthyl-acetylene linker compound T.M.204 was prepared as follows:
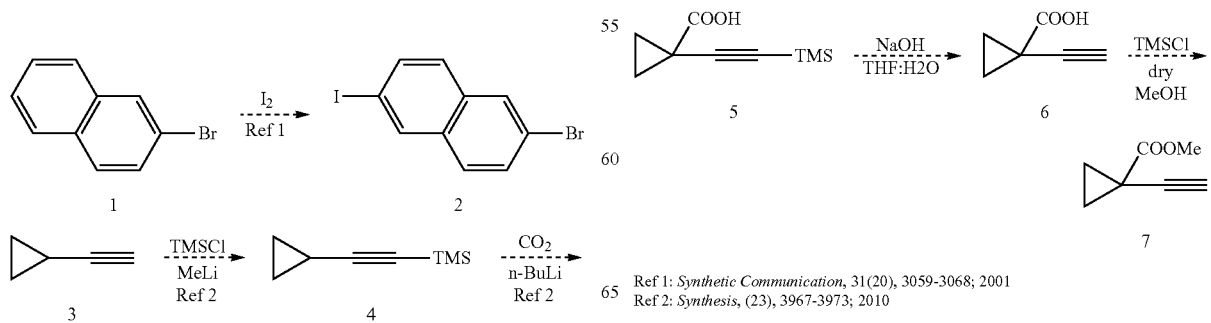
Ref 1: *Synthetic Communication*, 31(20), 3059-3068; 2001
Ref 2: *Synthesis*, (23), 3967-3973; 2010

Exemplary Benzoxazole Compound
The benzoxazole compound T.MB was prepared as follows:
Route 1:
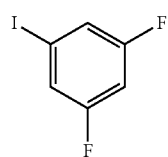
1
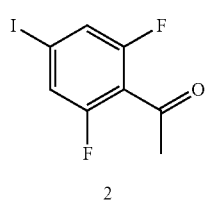
2
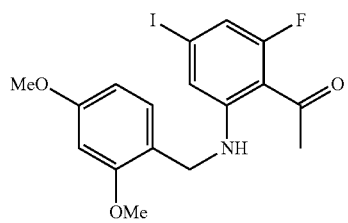
3
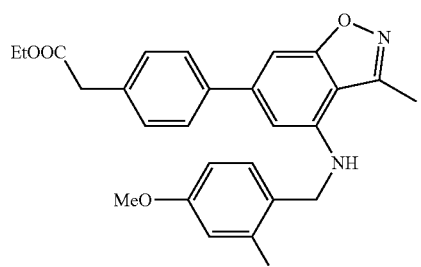
4
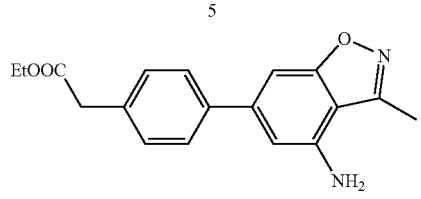
5
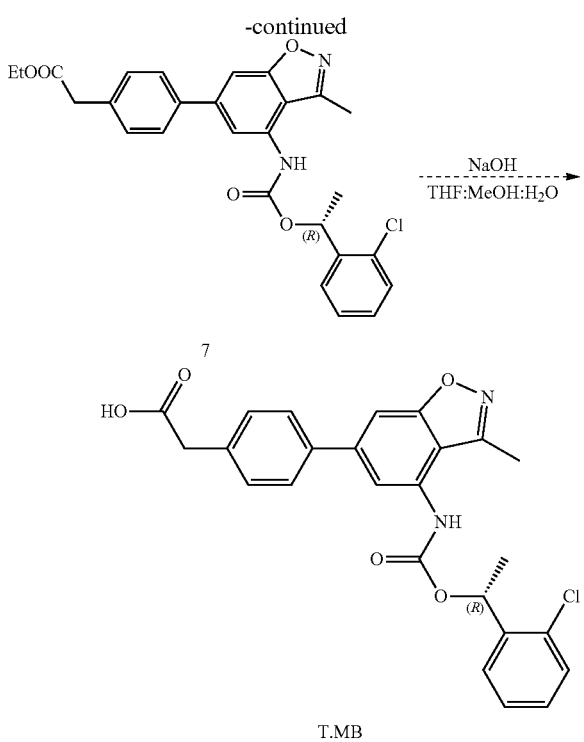
T.MB
An alternative synthesis of the benzoxazole compound T.MB was as follows:
Route 2:
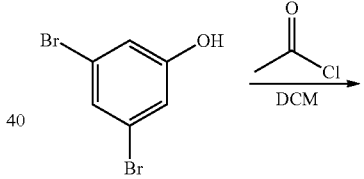
1
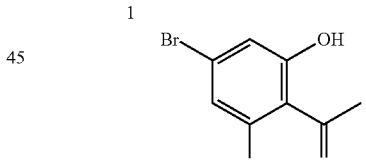
2
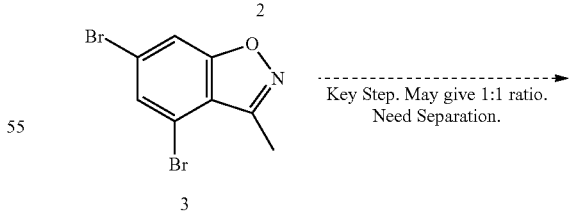

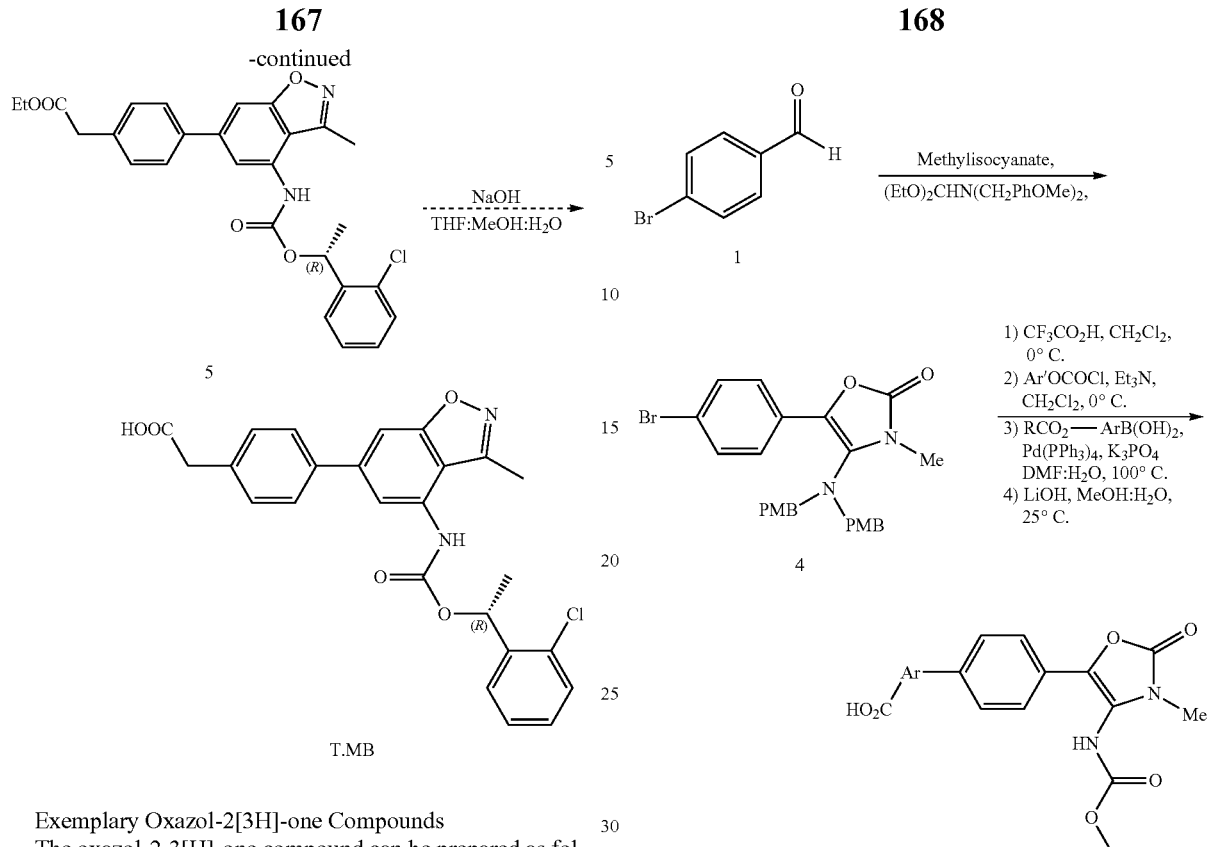
Exemplary Oxazol-2[3H]-one Compounds
The oxazol-2-3[H]-one compound can be prepared as follows:
Ref.: *Chemische Berichte*, 1970, vol. 103, p. 236-244.
The 3-methoxyoxazole-2-3[H]-one compound can be prepared as follows:
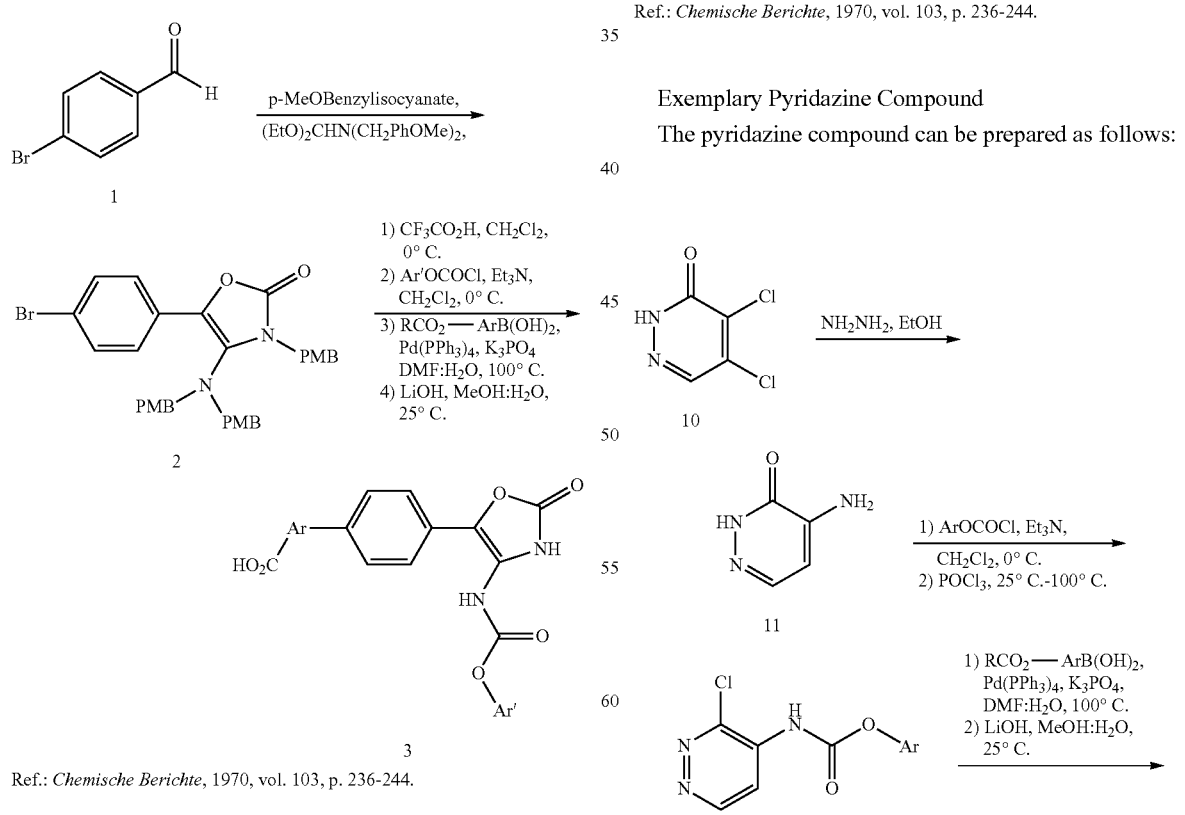
Ref.: *Chemische Berichte*, 1970, vol. 103, p. 236-244.
Exemplary Pyridazine Compound
The pyridazine compound can be prepared as follows:

-continued
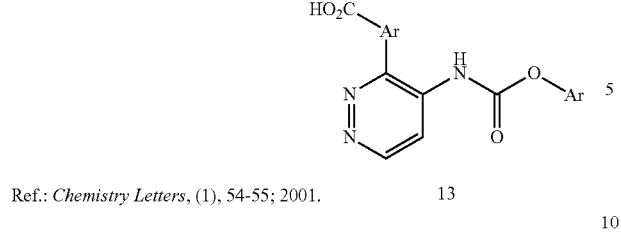
Ref.: *Chemistry Letters*, (1), 54-55; 2001.    13
Exemplary Heterobicyclic-Acetylene Compounds
The following exemplary compounds of Formula (I) can be prepared according to the various reaction schemes presented below:
T.M. 301
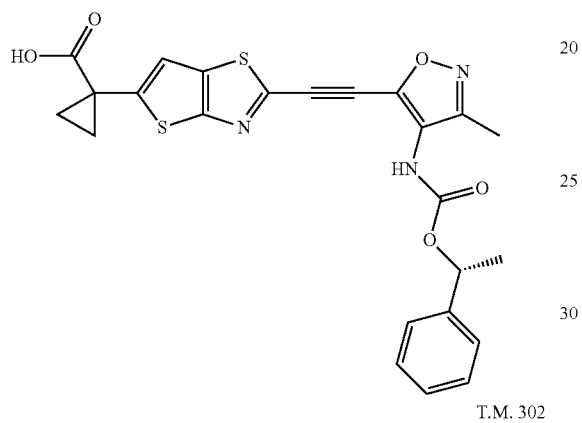
T.M. 302
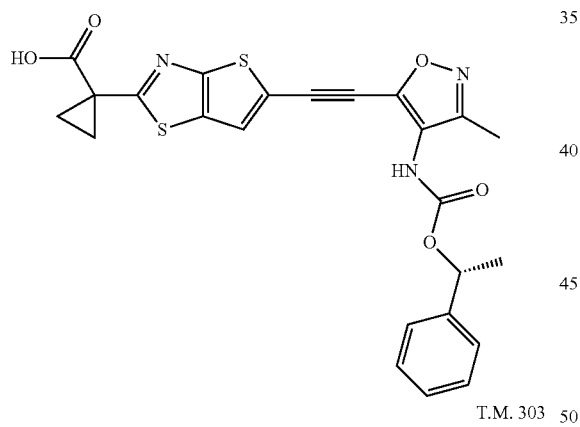
T.M. 303
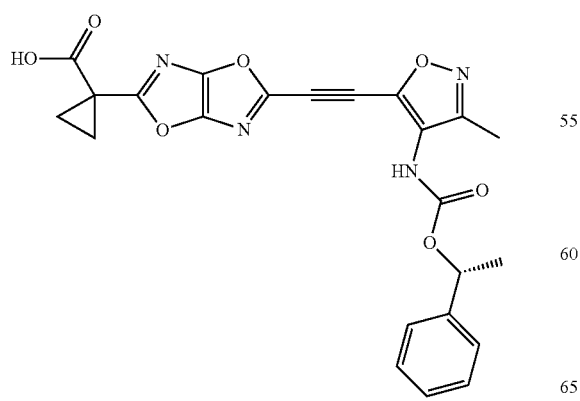
Compound T.M. 301 can be prepared using the synthetic scheme as follows:
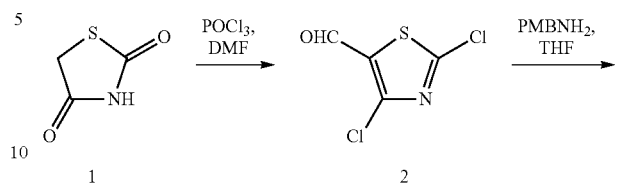
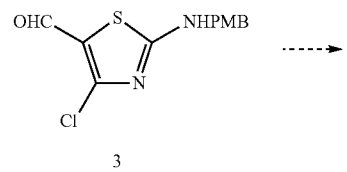
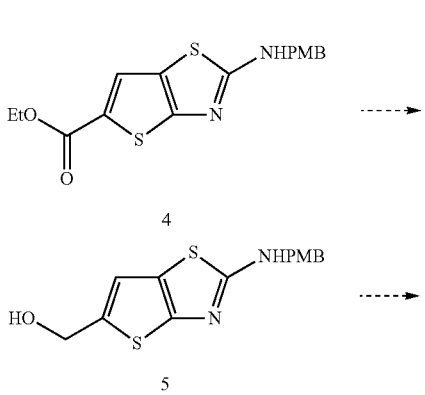
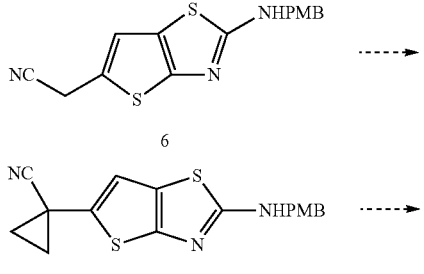
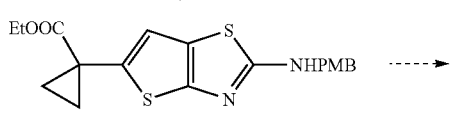
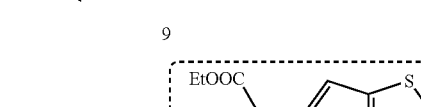
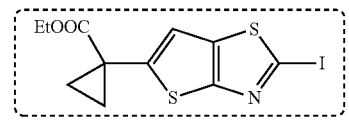
T.M. 301-10
Compound T.M. 302 can be prepared using the synthetic scheme as follows:

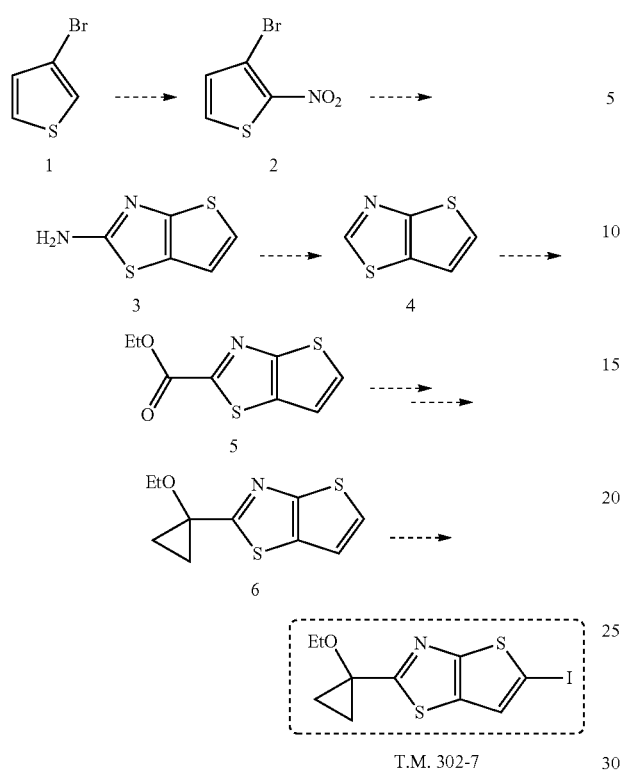
Compound T.M. 303 can be prepared using the synthetic scheme as follows:
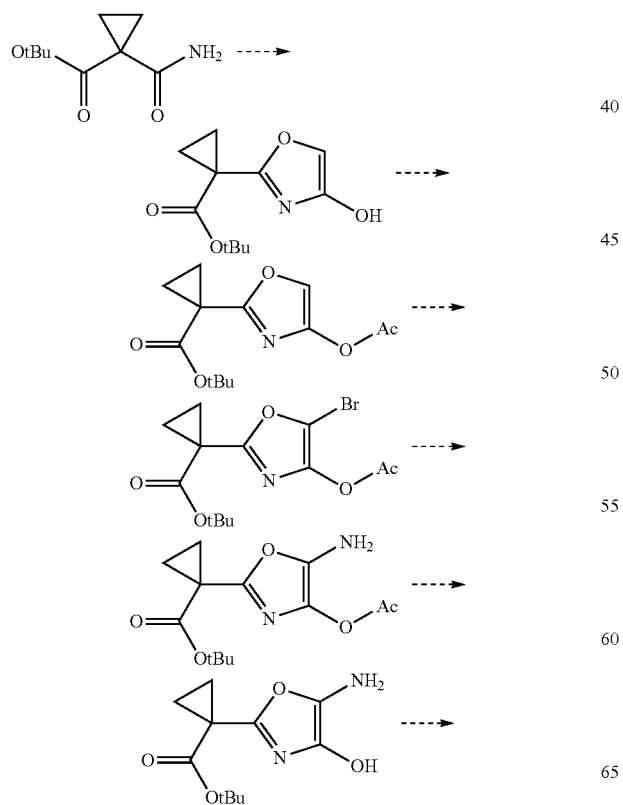
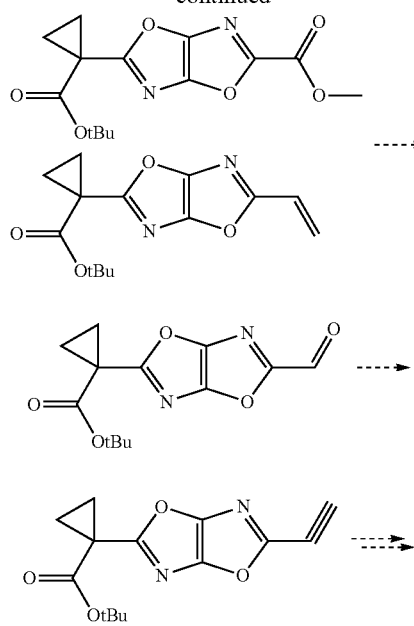
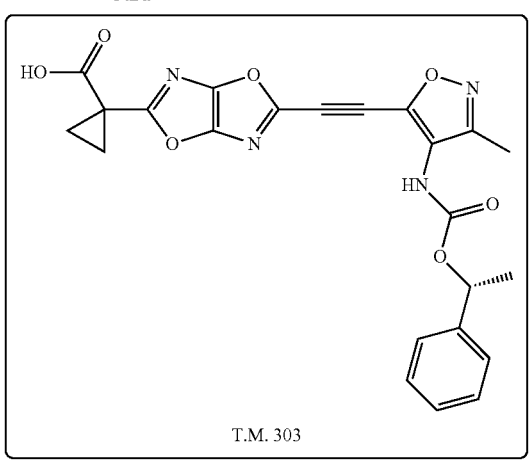
T.M. 303
Exemplary 5,6-Fused Heterobicyclic Compounds
The following exemplary compounds of Formula (I) can be prepared according to the various reaction schemes presented below:
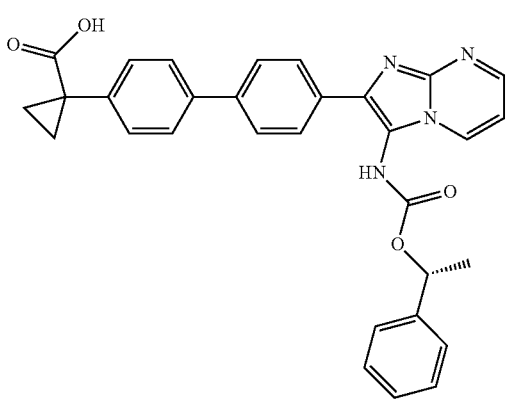
T.M. 401

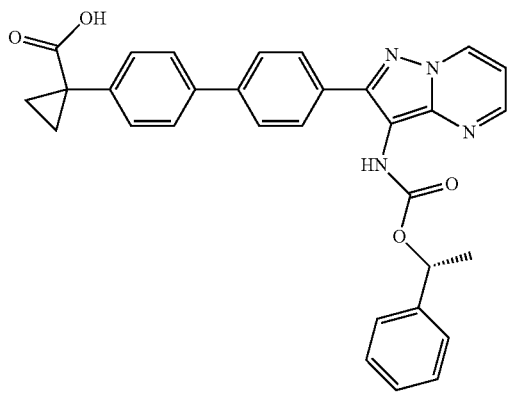
T.M. 402
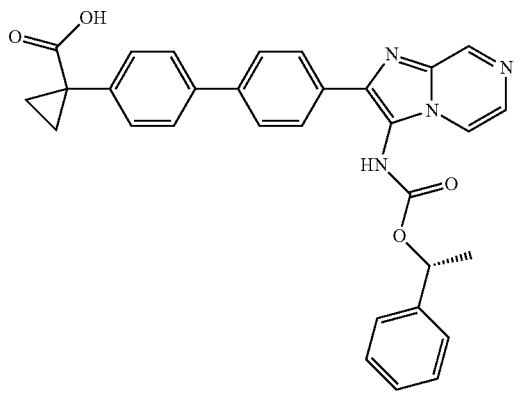
T.M. 405
The imidazo-pyrimidine compound T.M. 401 can be prepared by the synthetic scheme as follows:
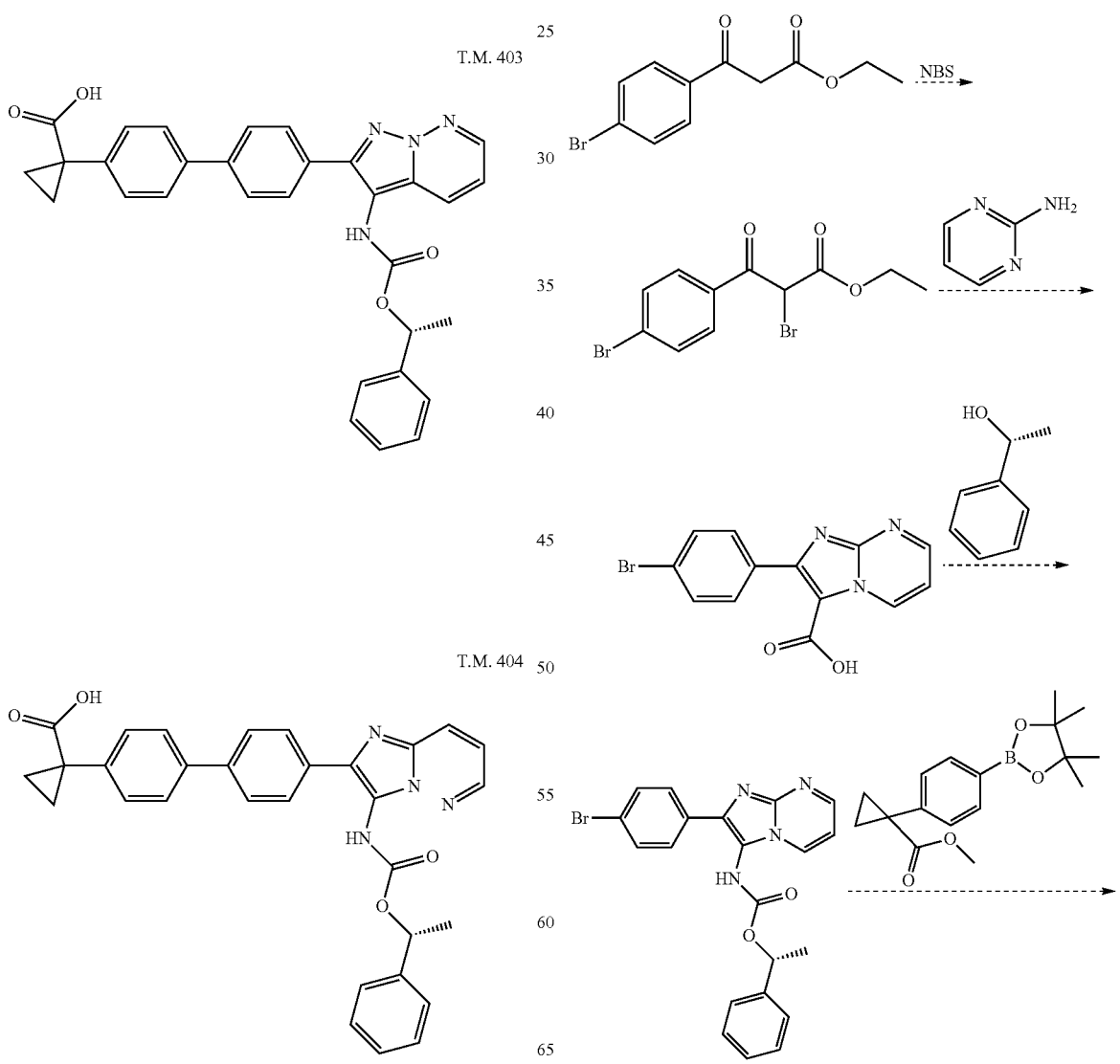

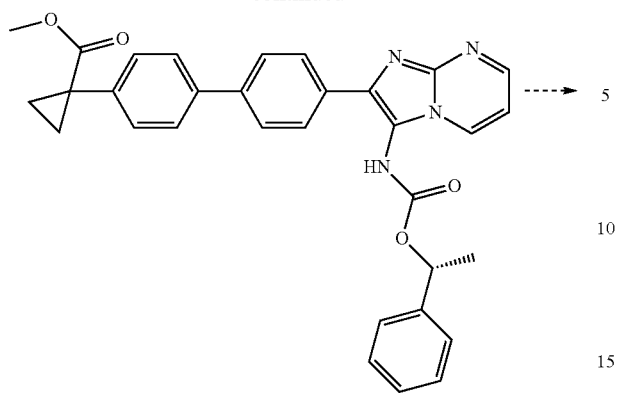
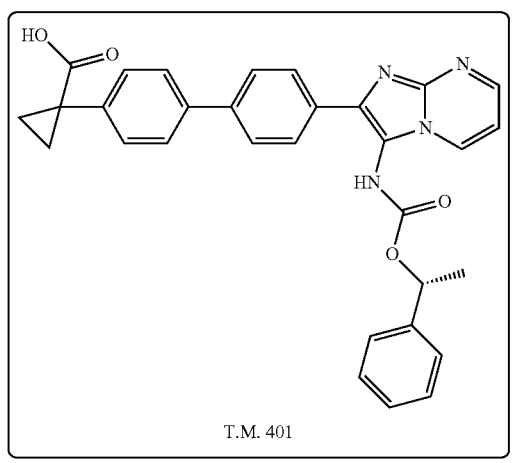 [SMILES: C[C@@H](OC(=O)Nc1c(-c2ccc(-c3ccc(C4(C(=O)O)CC4)cc3)cc2)nc2ncccn12)c1ccccc1]
T.M. 401
The substituted pyrimidine analogs that can be used in the synthesis comprises:
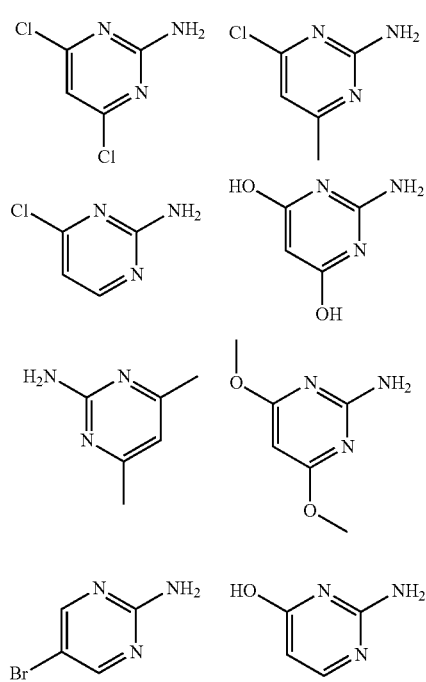
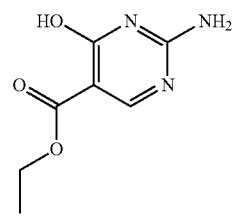
The pyrazolo-pyrimidine compound T.M. 402 can be prepared by the synthetic scheme as follows:
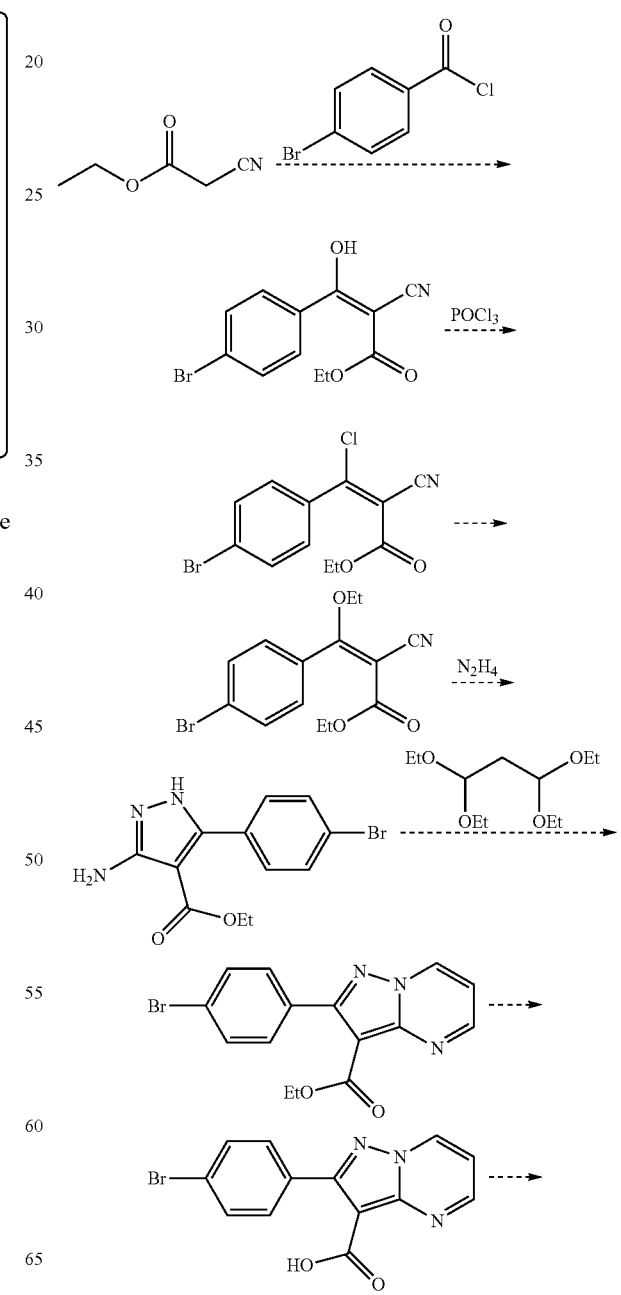

177
-continued
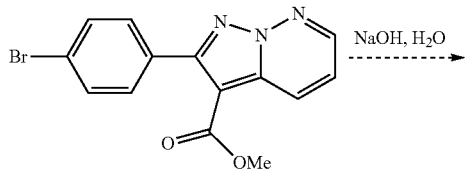
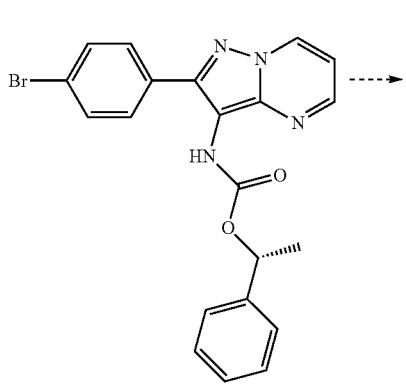
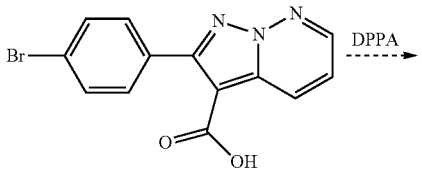
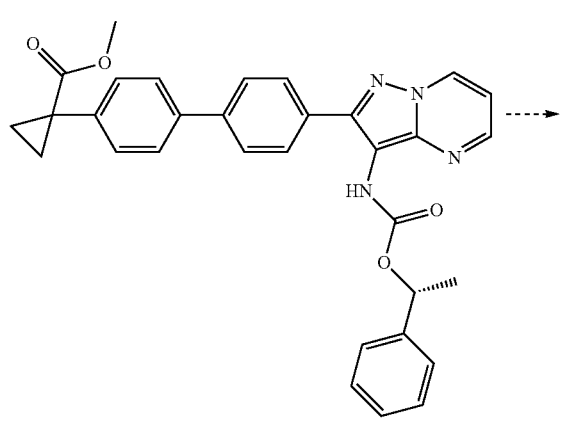
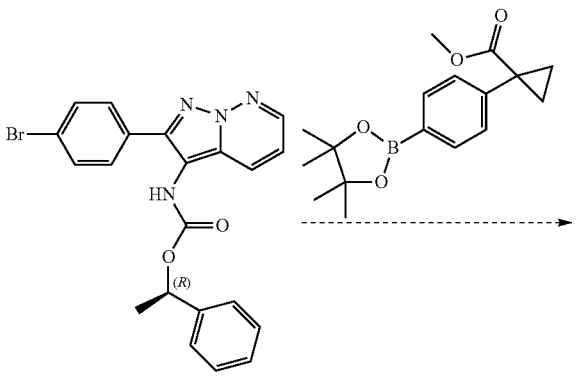
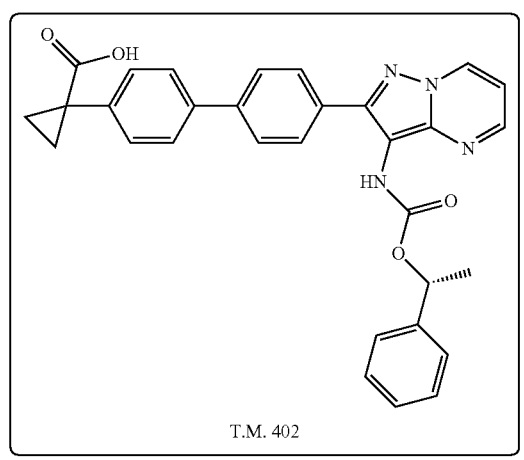
T.M. 402
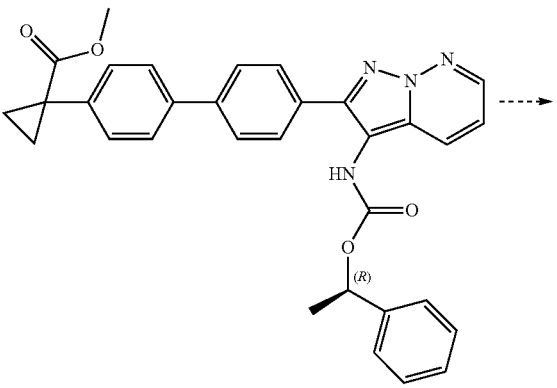
The pyrazolo-pyridazine compound T.M. 403 can be prepared by the synthetic scheme as follows:
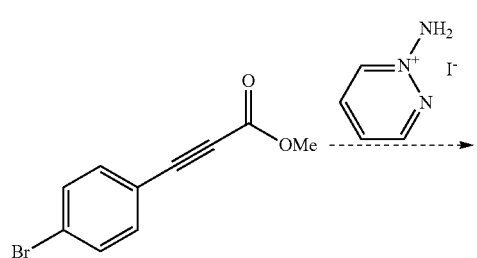
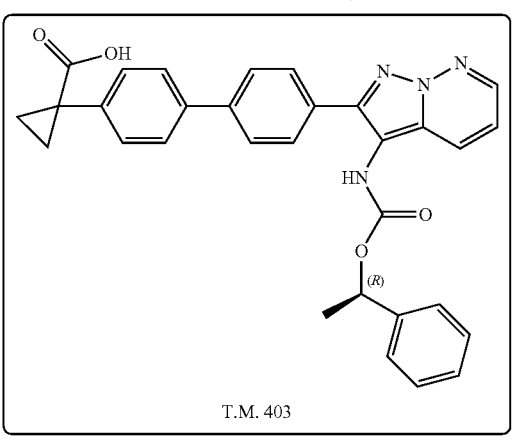
T.M. 403
The imidazo-pyridazine compound T.M. 404 can be prepared by the synthetic scheme as follows:

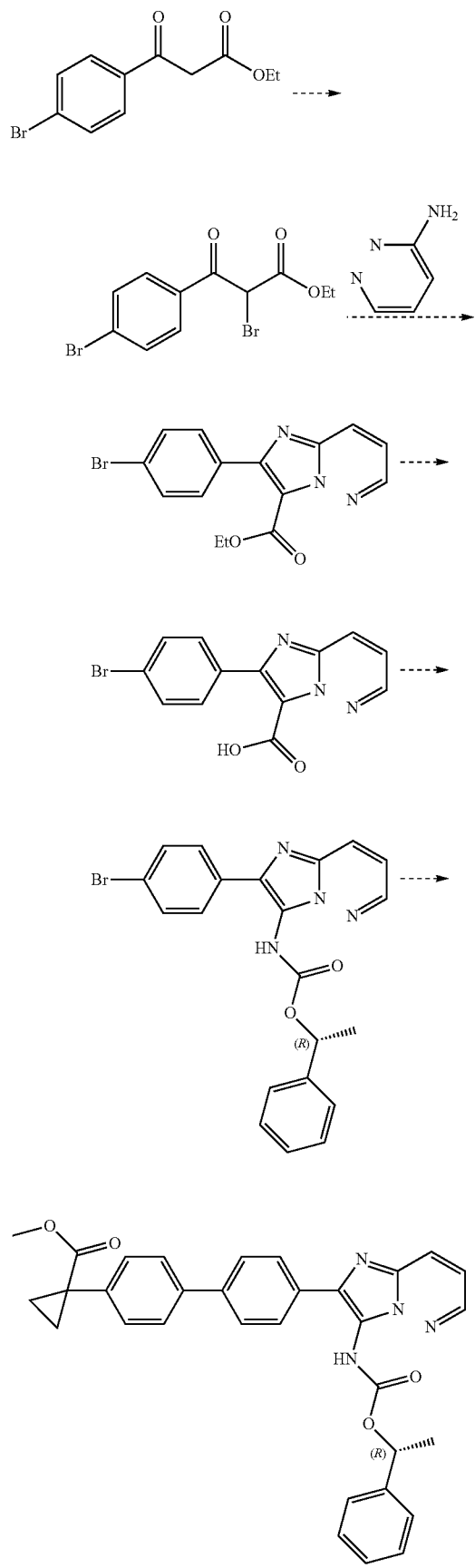
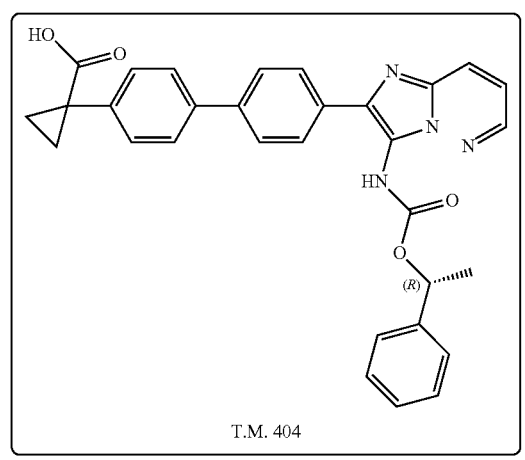
T.M. 404
The substituted aminopyridazines that can be used in the synthesis comprise:
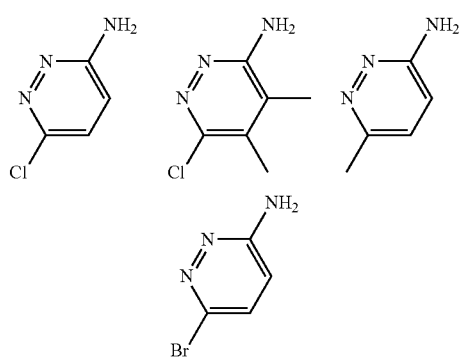
The imidazo-pyrazine compound T.M. 405 can be prepared by the synthetic scheme as follows:
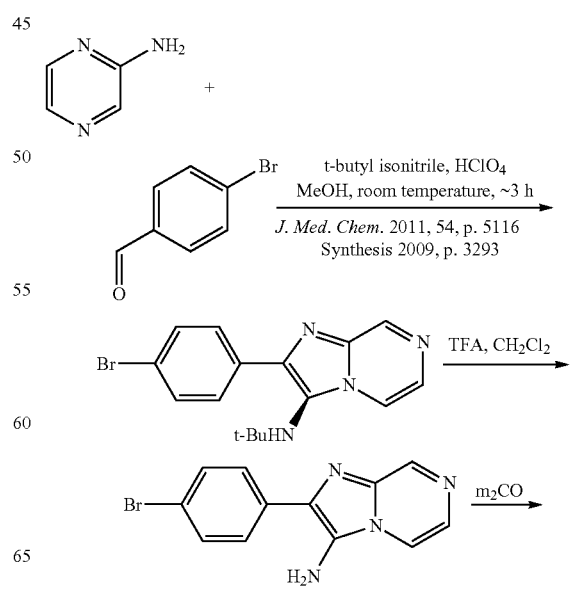

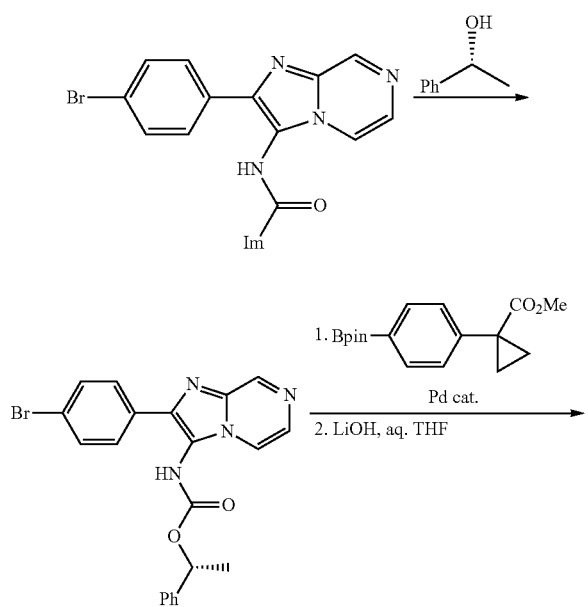
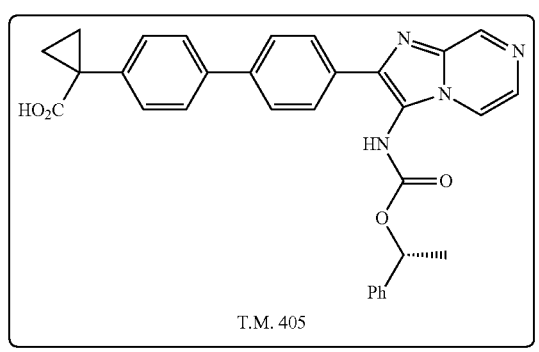
T.M. 405
The following exemplary thieno-pyridine compounds of Formula (I) can be prepared according to the various reaction schemes presented below:
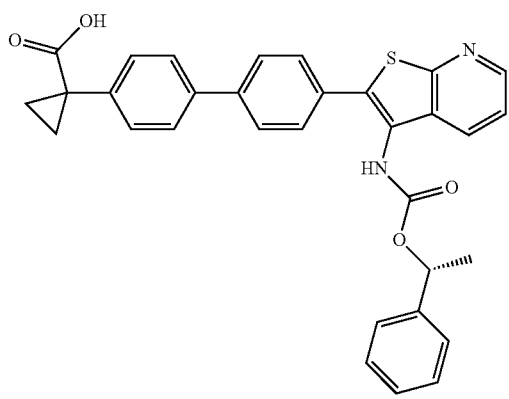
T.M. 501
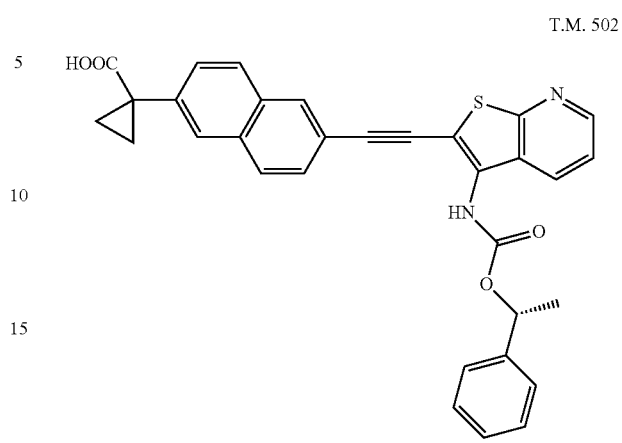
T.M. 502
An alternative synthetic scheme for the synthesis of T.M. 501 is as follows:
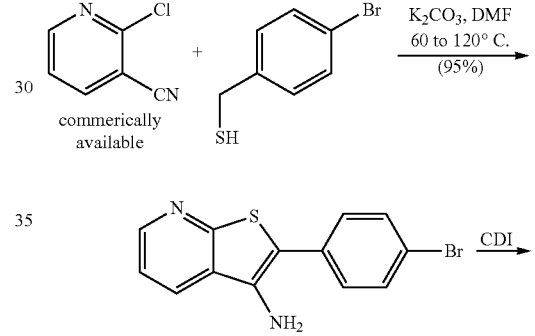
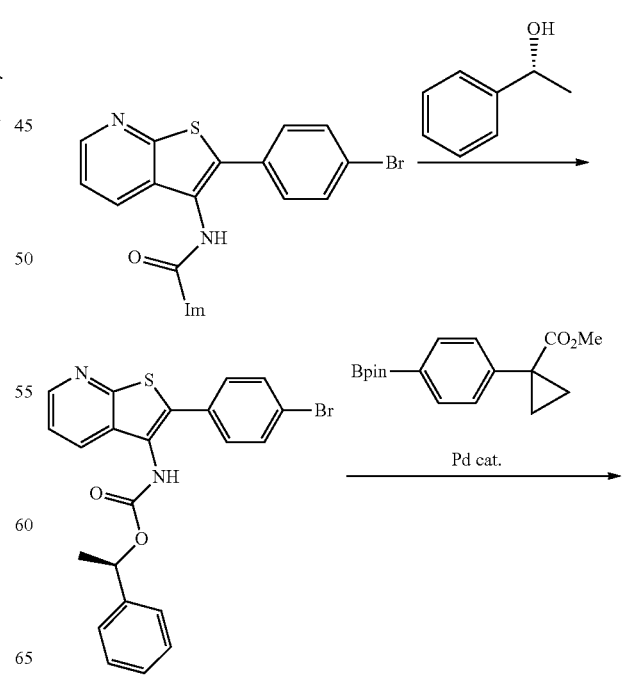

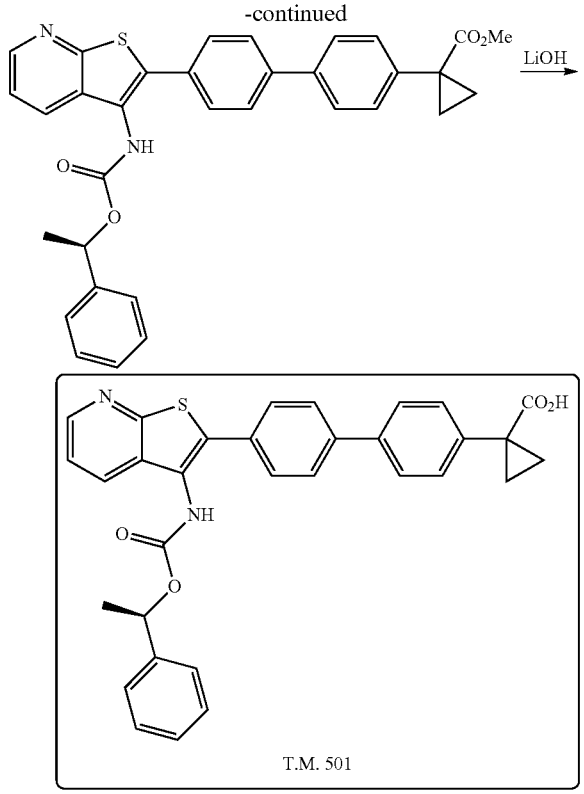
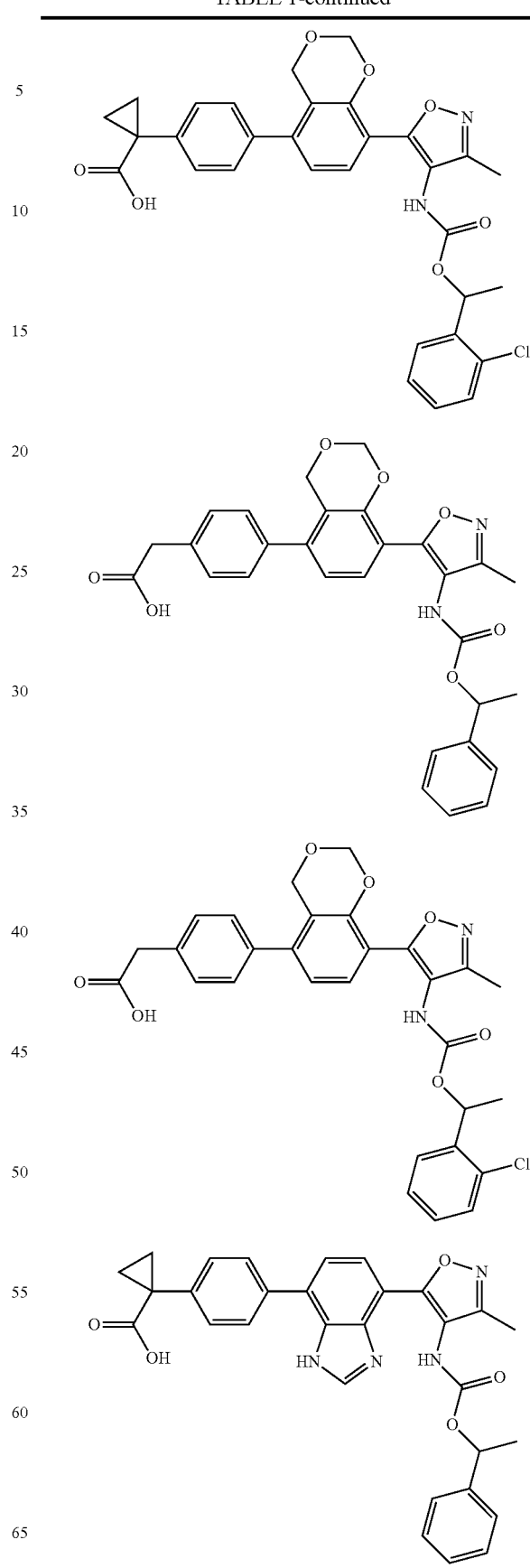
TABLE 1-continued
An alternative synthetic scheme for the synthesis of T.M. 502 is as follows:
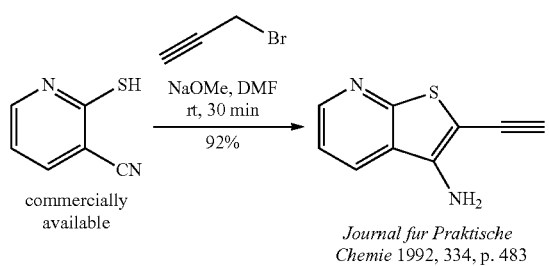
In some embodiments, compounds of Formula (I) are selected from the following compounds as listed in Table 1.
TABLE 1
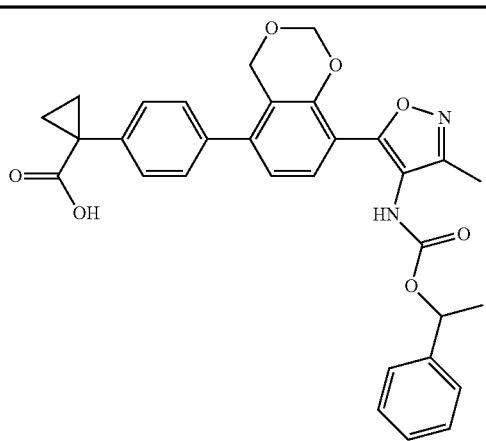

TABLE 1-continued
185
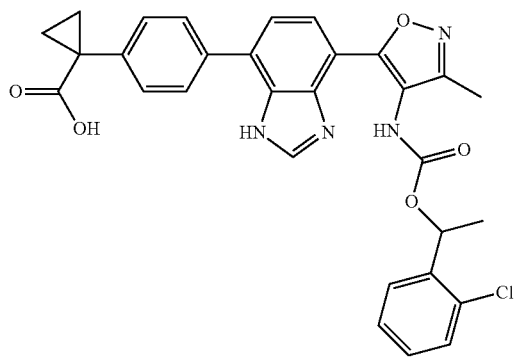 [SMILES: Cc1noc(-c2ccc(-c3ccc(C4(C(=O)O)CC4)cc3)c3[nH]cnc23)c1NC(=O)OC(C)c1ccccc1Cl]
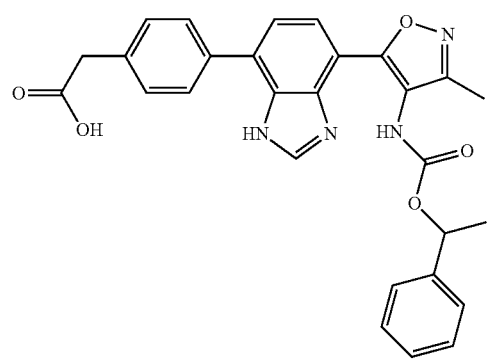 [SMILES: Cc1noc(-c2ccc(-c3ccc(CC(=O)O)cc3)c3[nH]cnc23)c1NC(=O)OC(C)c1ccccc1]
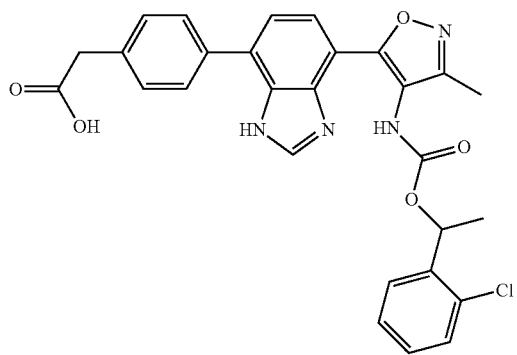 [SMILES: Cc1noc(-c2ccc(-c3ccc(CC(=O)O)cc3)c3[nH]cnc23)c1NC(=O)OC(C)c1ccccc1Cl]
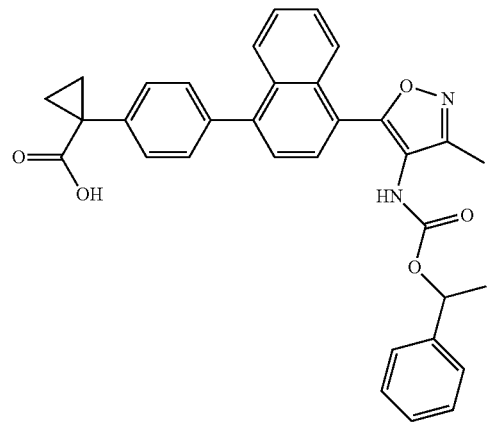 [SMILES: Cc1noc(-c2ccc(-c3ccc(C4(C(=O)O)CC4)cc3)c3ccccc23)c1NC(=O)OC(C)c1ccccc1]
TABLE 1-continued
186
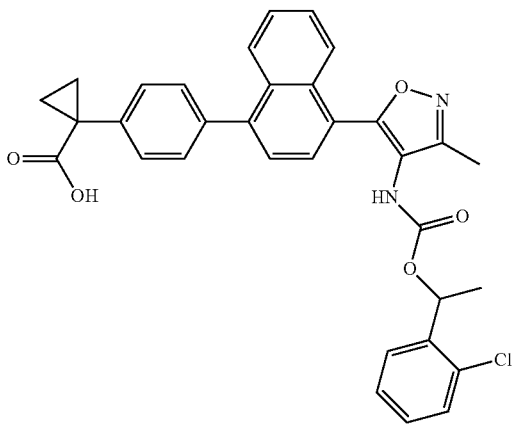 [SMILES: Cc1noc(-c2ccc(-c3ccc(C4(C(=O)O)CC4)cc3)c3ccccc23)c1NC(=O)OC(C)c1ccccc1Cl]
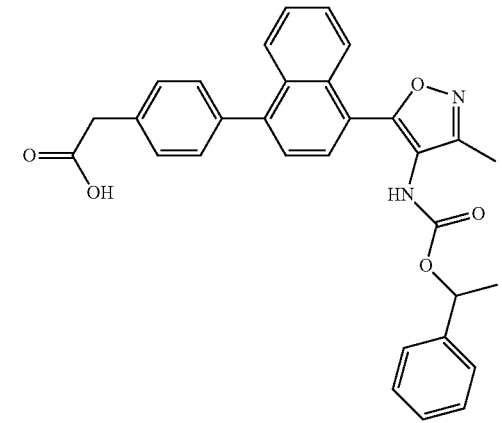 [SMILES: Cc1noc(-c2ccc(-c3ccc(CC(=O)O)cc3)c3ccccc23)c1NC(=O)OC(C)c1ccccc1]
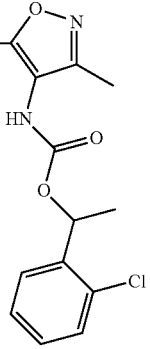

187
TABLE 1-continued
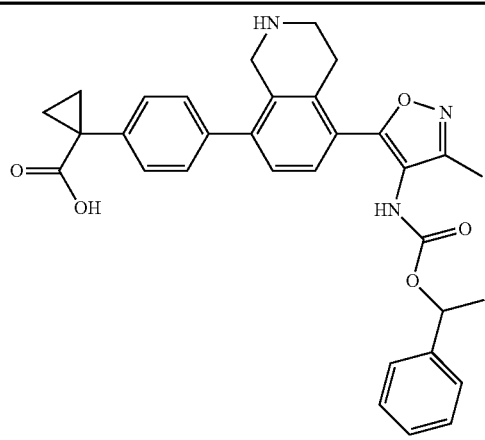
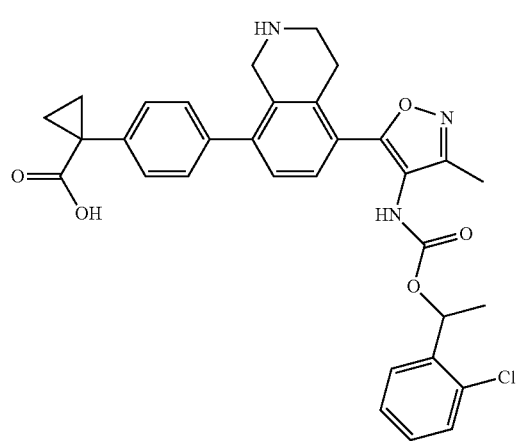 [SMILES: Cc1noc(-c2ccc(-c3ccc(C4(C(=O)O)CC4)cc3)c3c2CCNC3)c1NC(=O)OC(C)c1ccccc1Cl]
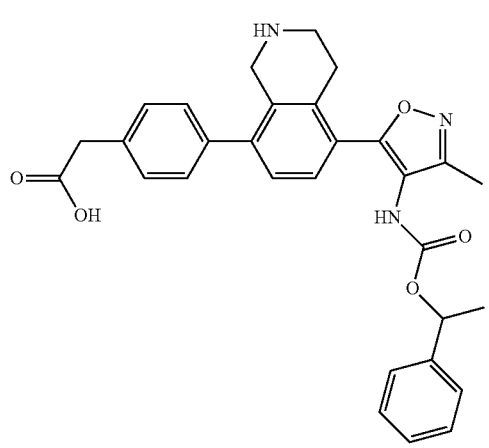 [SMILES: Cc1noc(-c2ccc(-c3ccc(CC(=O)O)cc3)c3c2CCNC3)c1NC(=O)OC(C)c1ccccc1]
188
TABLE 1-continued
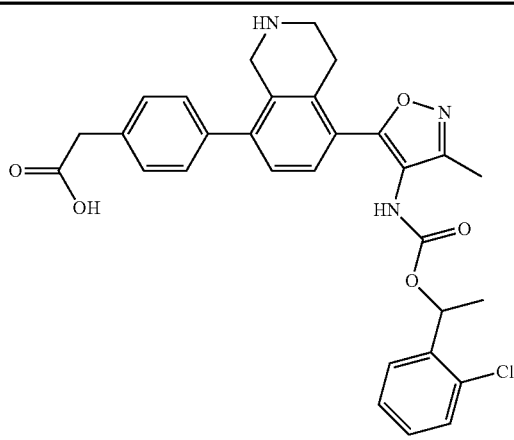
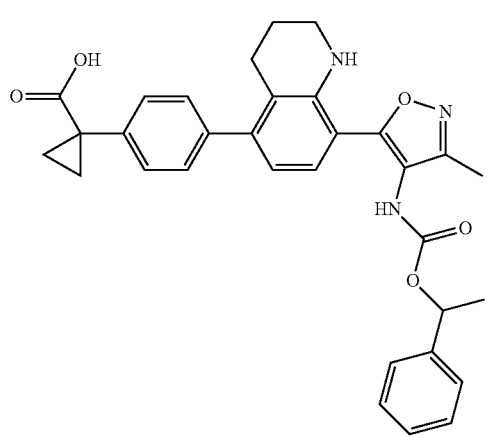 [SMILES: Cc1noc(-c2ccc(-c3ccc(C4(C(=O)O)CC4)cc3)c3c2NCCC3)c1NC(=O)OC(C)c1ccccc1]
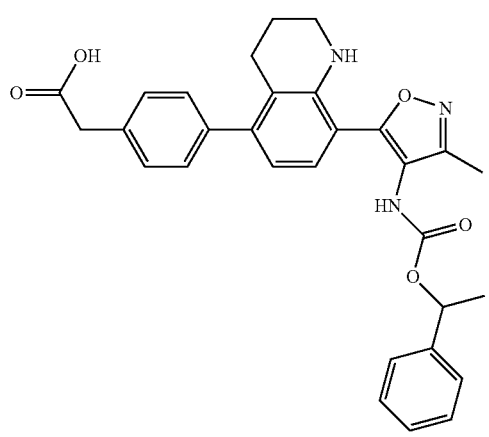 [SMILES: Cc1noc(-c2ccc(-c3ccc(CC(=O)O)cc3)c3c2NCCC3)c1NC(=O)OC(C)c1ccccc1]

189
TABLE 1-continued
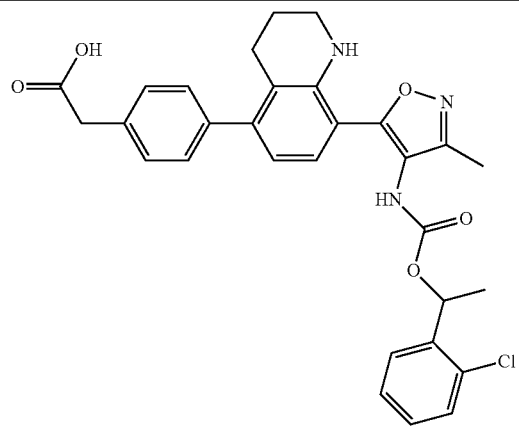
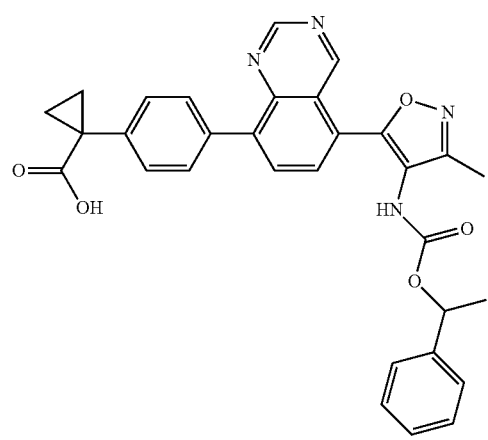 [SMILES: Cc1noc(-c2ccc(-c3ccc(C4(C(=O)O)CC4)cc3)c3ncncc23)c1NC(=O)OC(C)c1ccccc1]
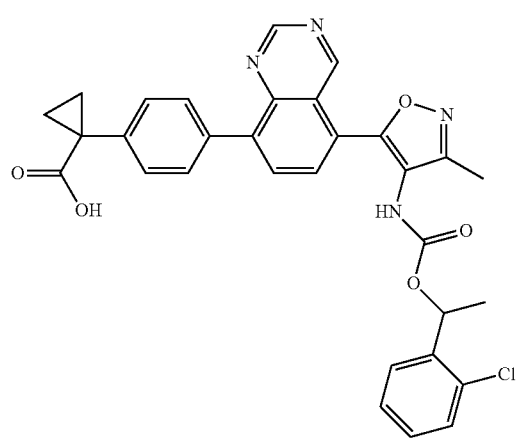 [SMILES: Cc1noc(-c2ccc(-c3ccc(C4(C(=O)O)CC4)cc3)c3ncncc23)c1NC(=O)OC(C)c1ccccc1Cl]
190
TABLE 1-continued
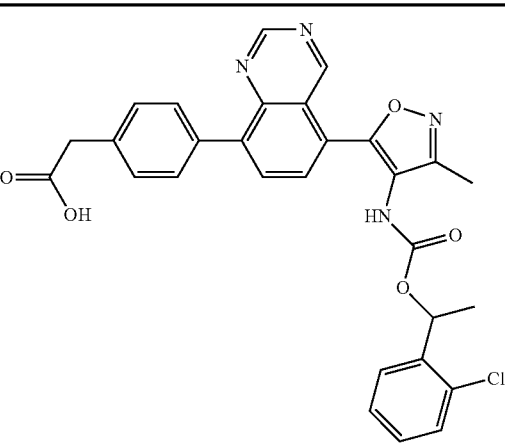
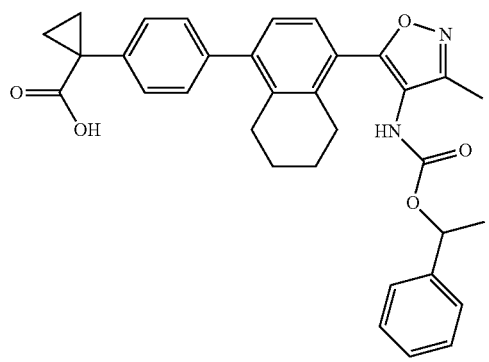 [SMILES: Cc1noc(-c2ccc(-c3ccc(C4(C(=O)O)CC4)cc3)c3c2CCCC3)c1NC(=O)OC(C)c1ccccc1]
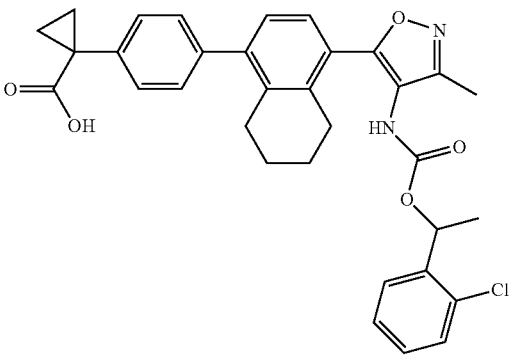 [SMILES: Cc1noc(-c2ccc(-c3ccc(C4(C(=O)O)CC4)cc3)c3c2CCCC3)c1NC(=O)OC(C)c1ccccc1Cl]
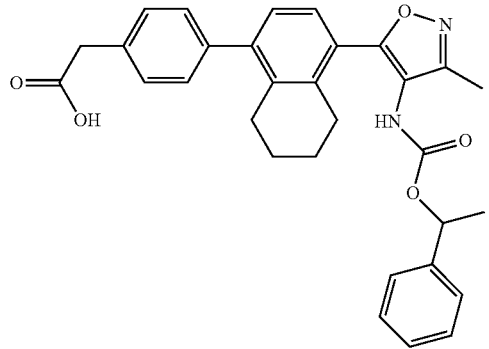 [SMILES: Cc1noc(-c2ccc(-c3ccc(CC(=O)O)cc3)c3c2CCCC3)c1NC(=O)OC(C)c1ccccc1]

| 191 | 192 |
|---|---|
| TABLE 1-continued | TABLE 1-continued |
| 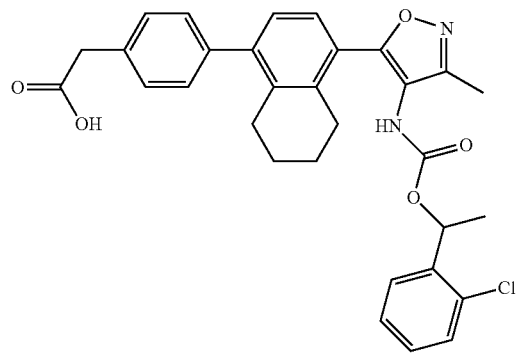 [SMILES: Cc1noc(-c2ccc(-c3ccc(CC(=O)O)cc3)c3c2CCCC3)c1NC(=O)OC(C)c1ccccc1Cl] | 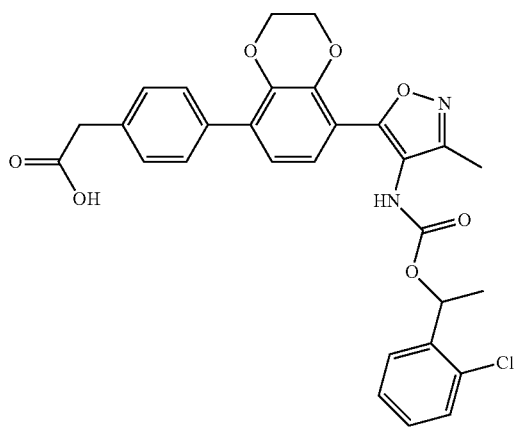 |
| 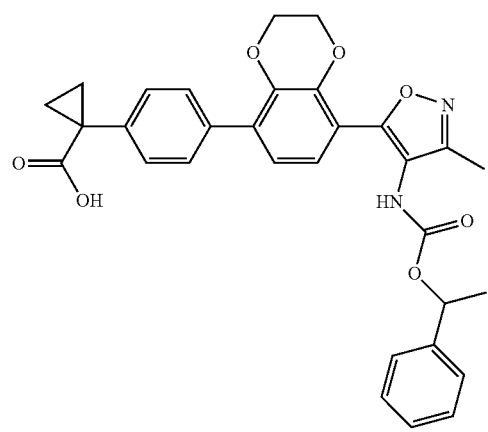 [SMILES: Cc1noc(-c2ccc(-c3ccc(C4(C(=O)O)CC4)cc3)c3c2OCCO3)c1NC(=O)OC(C)c1ccccc1] | |
| 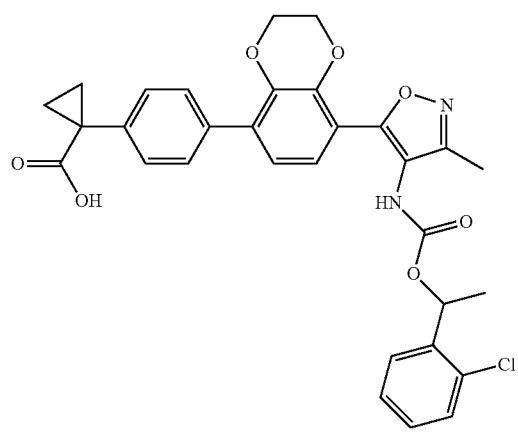 [SMILES: Cc1noc(-c2ccc(-c3ccc(C4(C(=O)O)CC4)cc3)c3c2OCCO3)c1NC(=O)OC(C)c1ccccc1Cl] | 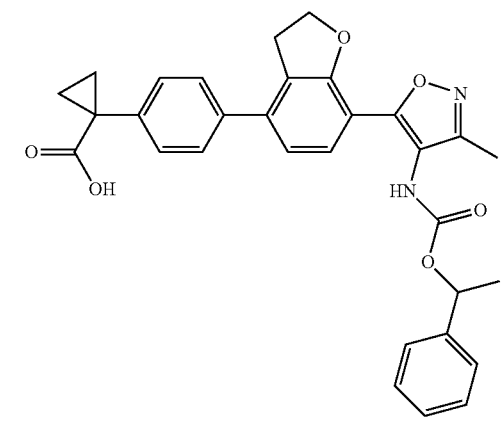 |
| 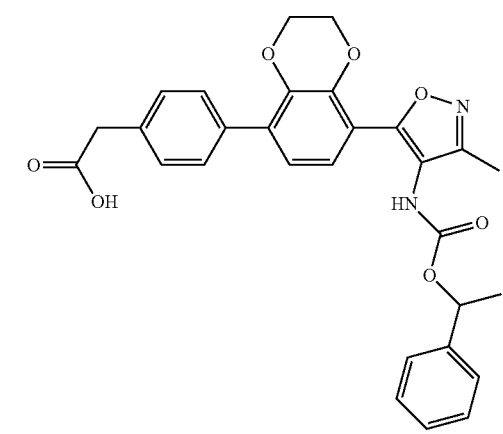 [SMILES: Cc1noc(-c2ccc(-c3ccc(CC(=O)O)cc3)c3c2OCCO3)c1NC(=O)OC(C)c1ccccc1] | 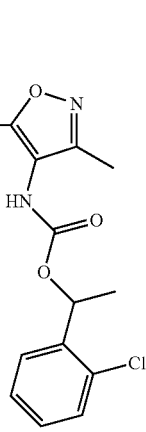 |

TABLE 1-continued
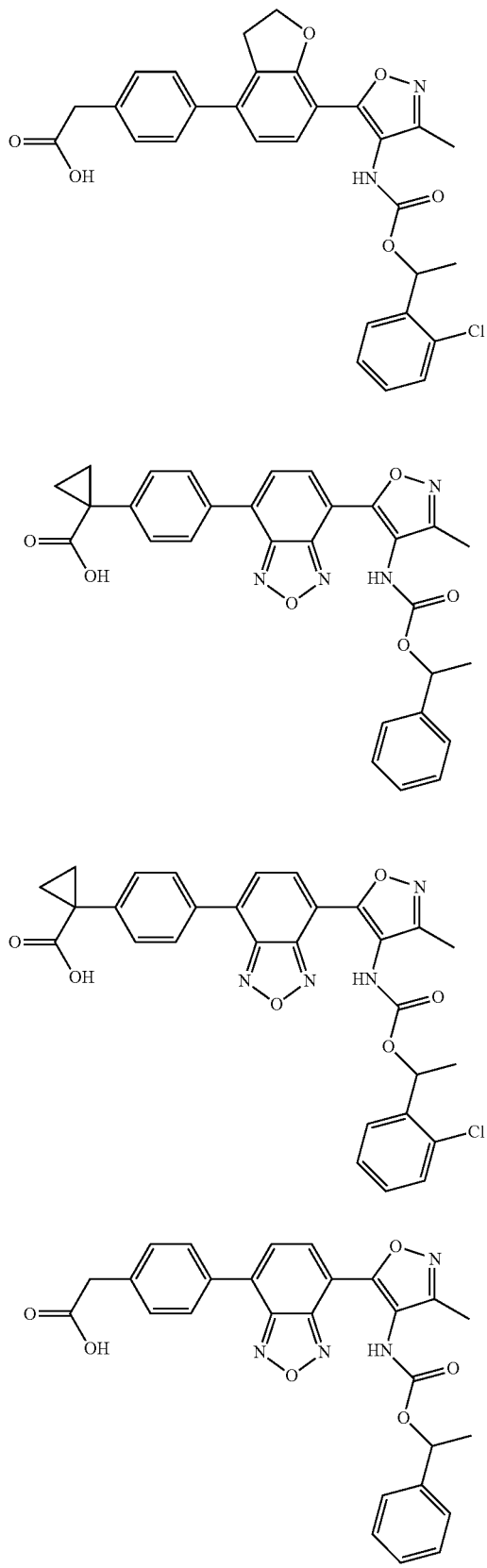
TABLE 1-continued
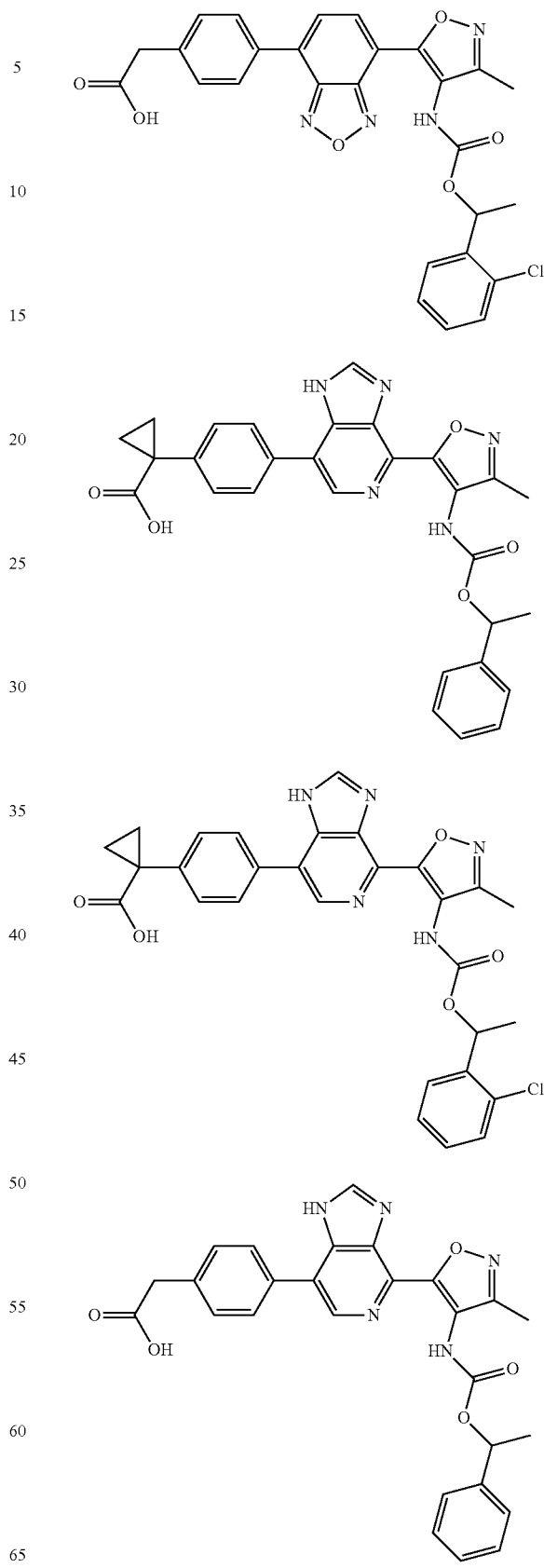

| 195 | 196 |
|---|---|
| TABLE 1-continued | TABLE 1-continued |
| 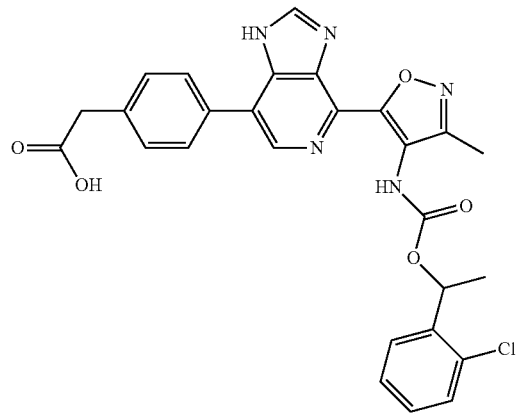 [SMILES: Cc1noc(-c2ncc(-c3ccc(CC(=O)O)cc3)c3[nH]cnc23)c1NC(=O)OC(C)c1ccccc1Cl] | 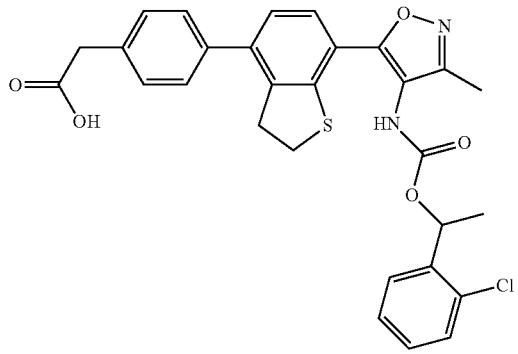 |
| 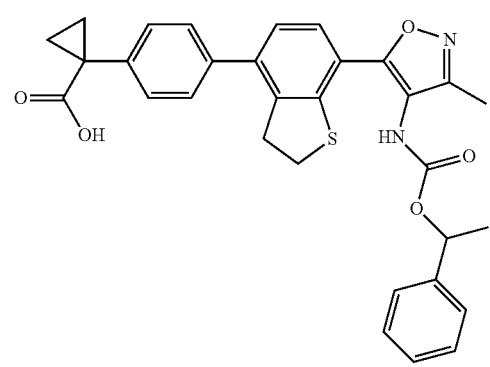 [SMILES: Cc1noc(-c2ccc(-c3ccc(C4(C(=O)O)CC4)cc3)c3c2SCC3)c1NC(=O)OC(C)c1ccccc1] | 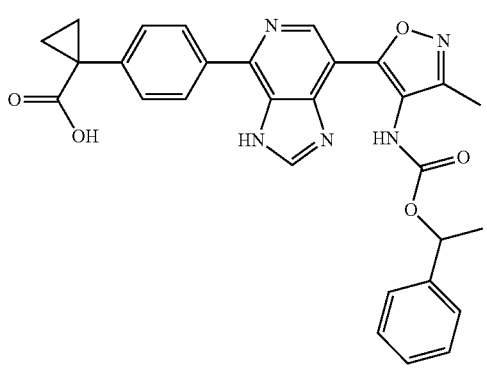 |
| 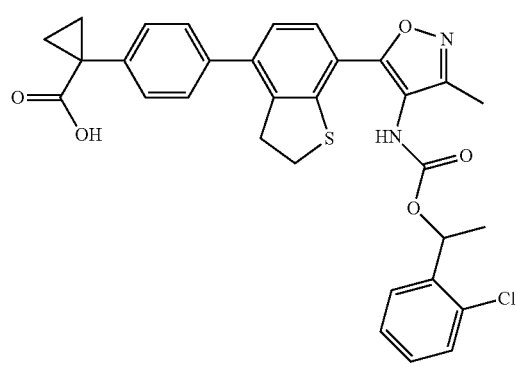 [SMILES: Cc1noc(-c2ccc(-c3ccc(C4(C(=O)O)CC4)cc3)c3c2SCC3)c1NC(=O)OC(C)c1ccccc1Cl] | 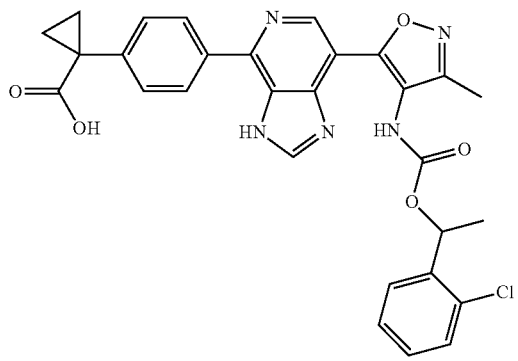 [SMILES: Cc1noc(-c2cnc(-c3ccc(C4(C(=O)O)CC4)cc3)c3[nH]cnc23)c1NC(=O)OC(C)c1ccccc1Cl] |
| 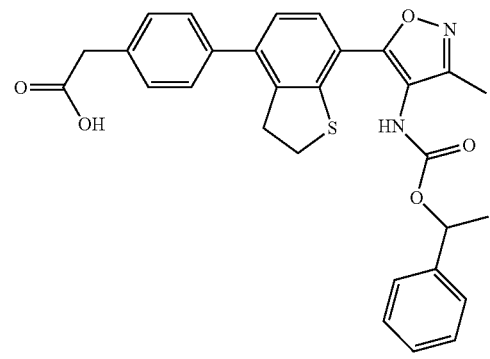 | 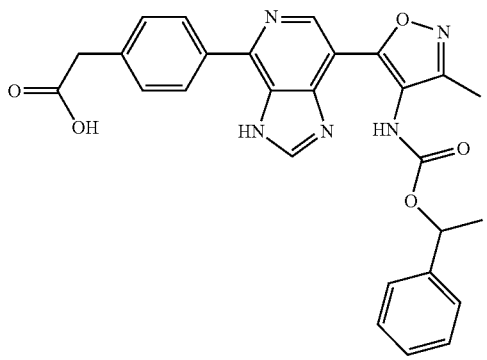 [SMILES: Cc1noc(-c2cnc(-c3ccc(CC(=O)O)cc3)c3[nH]cnc23)c1NC(=O)OC(C)c1ccccc1] |

TABLE 1-continued
197
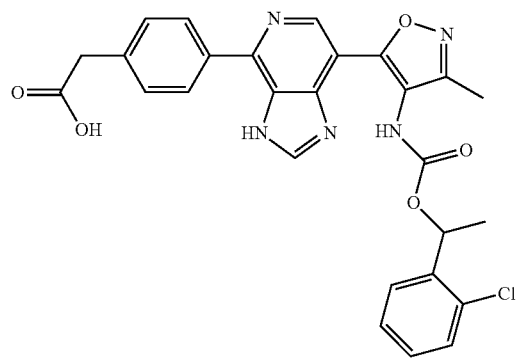 [SMILES: Cc1noc(-c2cnc(-c3ccc(CC(=O)O)cc3)c3[nH]cnc23)c1NC(=O)OC(C)c1ccccc1Cl]
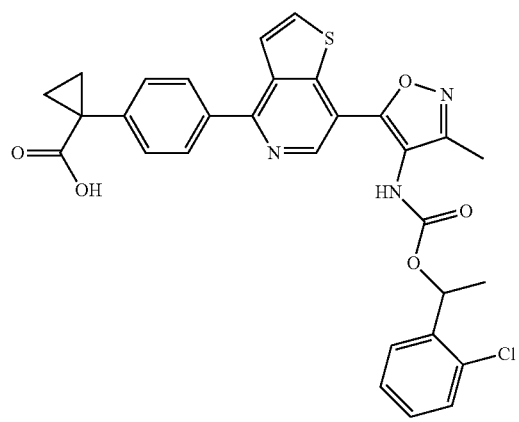 [SMILES: Cc1noc(-c2cnc(-c3ccc(C4(C(=O)O)CC4)cc3)c3ccsc23)c1NC(=O)OC(C)c1ccccc1Cl]
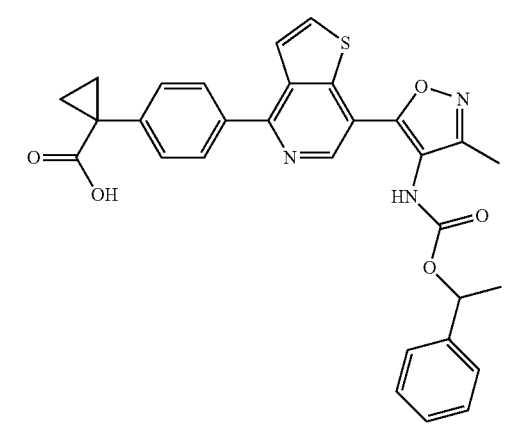 [SMILES: Cc1noc(-c2cnc(-c3ccc(C4(C(=O)O)CC4)cc3)c3ccsc23)c1NC(=O)OC(C)c1ccccc1]
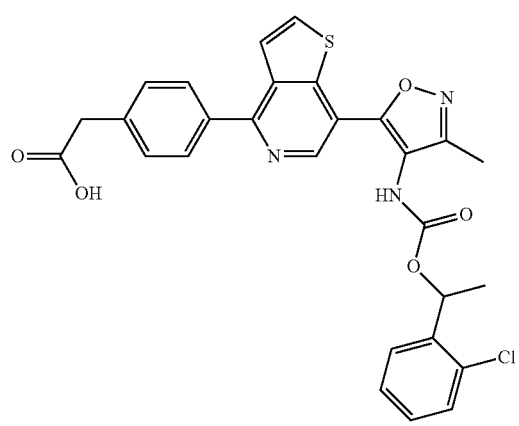 [SMILES: Cc1noc(-c2cnc(-c3ccc(CC(=O)O)cc3)c3ccsc23)c1NC(=O)OC(C)c1ccccc1Cl]
198
TABLE 1-continued
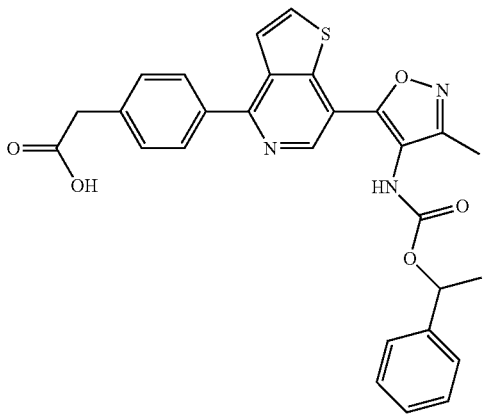 [SMILES: Cc1noc(-c2cnc(-c3ccc(CC(=O)O)cc3)c3ccsc23)c1NC(=O)OC(C)c1ccccc1]
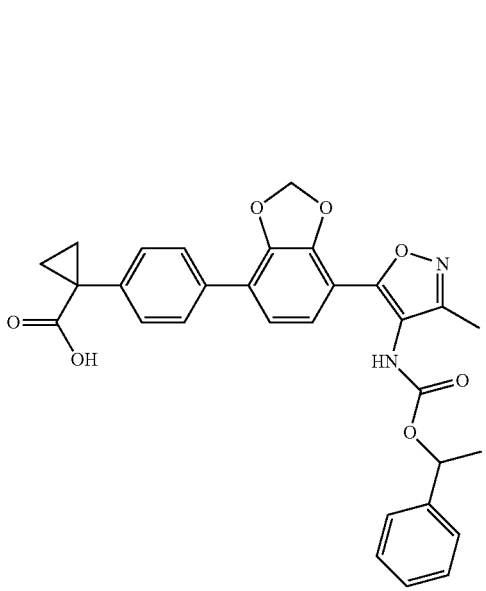 [SMILES: Cc1noc(-c2ccc(-c3ccc(C4(C(=O)O)CC4)cc3)c3c2OCO3)c1NC(=O)OC(C)c1ccccc1]
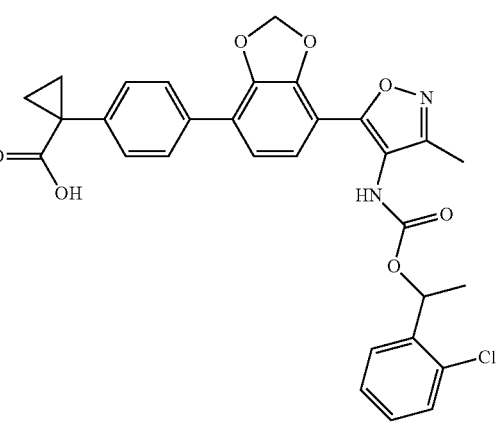

| 199 | 200 |
|---|---|
| TABLE 1-continued | TABLE 1-continued |
| 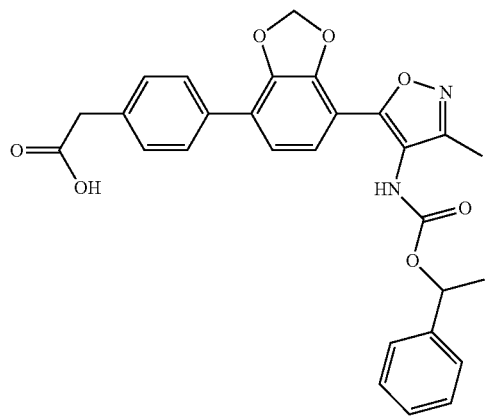 [SMILES: Cc1noc(-c2ccc(-c3ccc(CC(=O)O)cc3)c3c2OCO3)c1NC(=O)OC(C)c1ccccc1] | 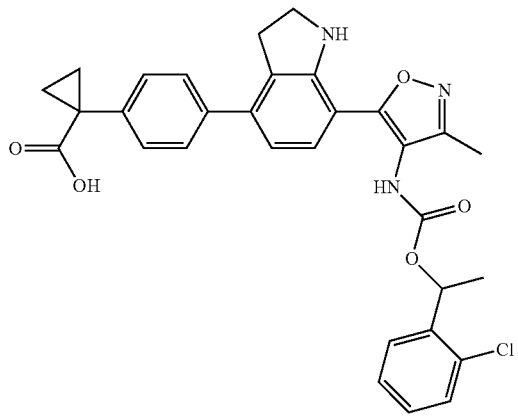 |
| 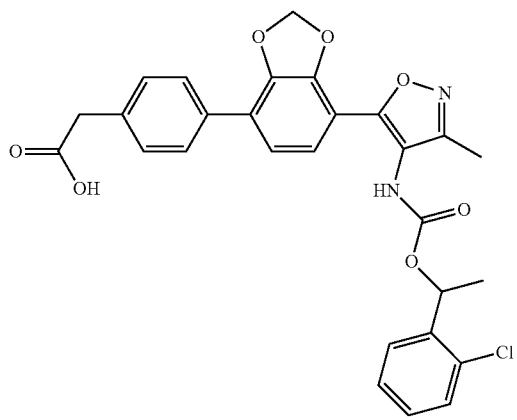 [SMILES: Cc1noc(-c2ccc(-c3ccc(CC(=O)O)cc3)c3c2OCO3)c1NC(=O)OC(C)c1ccccc1Cl] | 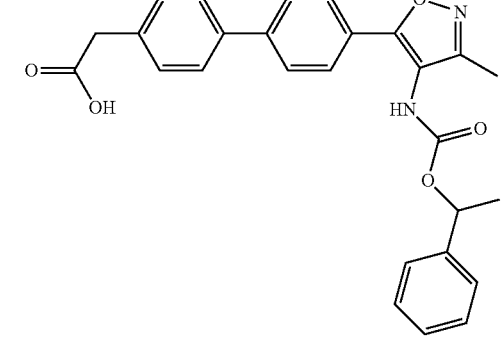 |
| 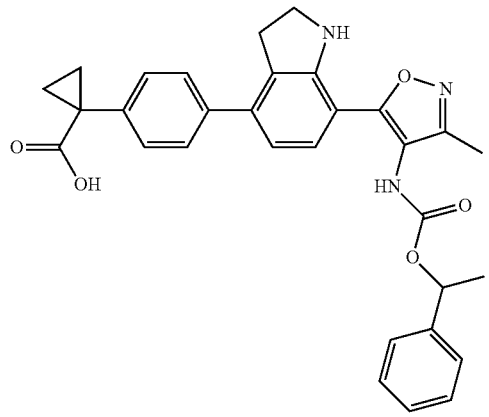 [SMILES: Cc1noc(-c2ccc(-c3ccc(C4(C(=O)O)CC4)cc3)c3c2NCC3)c1NC(=O)OC(C)c1ccccc1] | 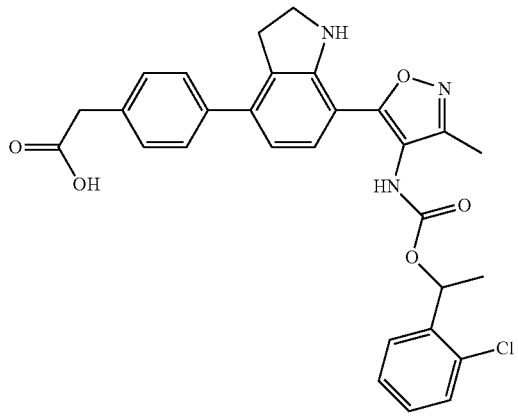 [SMILES: Cc1noc(-c2ccc(-c3ccc(CC(=O)O)cc3)c3c2NCC3)c1NC(=O)OC(C)c1ccccc1Cl] |

201
TABLE 1-continued
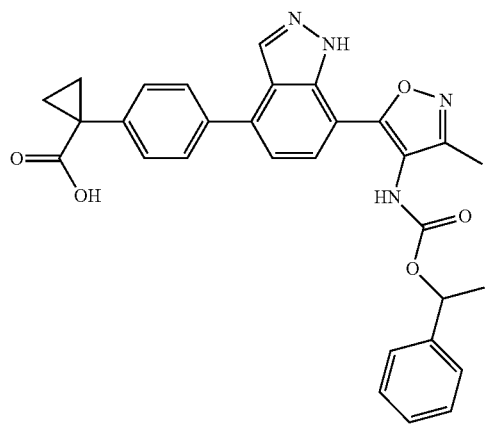 [SMILES: Cc1noc(-c2ccc(-c3ccc(C4(C(=O)O)CC4)cc3)c3cn[nH]c23)c1NC(=O)OC(C)c1ccccc1]
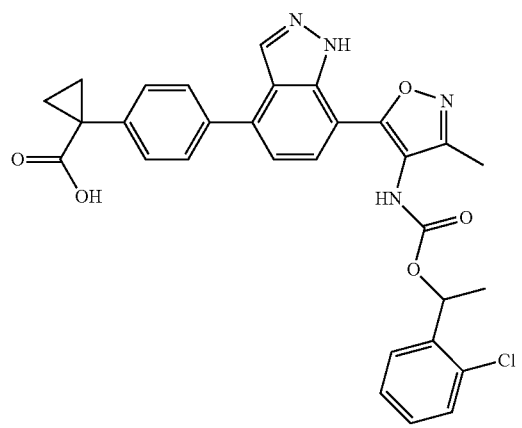 [SMILES: Cc1noc(-c2ccc(-c3ccc(C4(C(=O)O)CC4)cc3)c3cn[nH]c23)c1NC(=O)OC(C)c1ccccc1Cl]
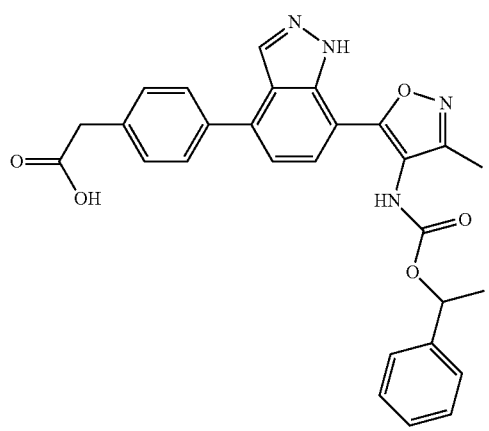 [SMILES: Cc1noc(-c2ccc(-c3ccc(CC(=O)O)cc3)c3cn[nH]c23)c1NC(=O)OC(C)c1ccccc1]
202
TABLE 1-continued
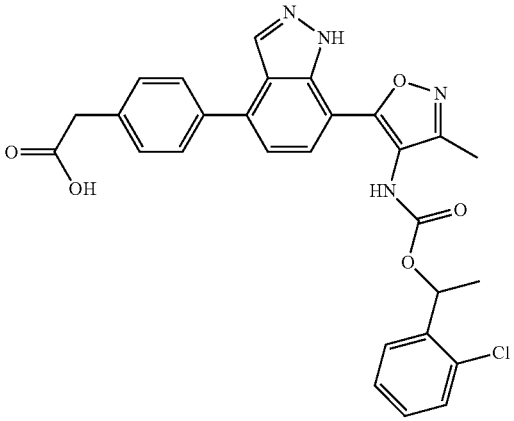 [SMILES: Cc1noc(-c2ccc(-c3ccc(CC(=O)O)cc3)c3cn[nH]c23)c1NC(=O)OC(C)c1ccccc1Cl]
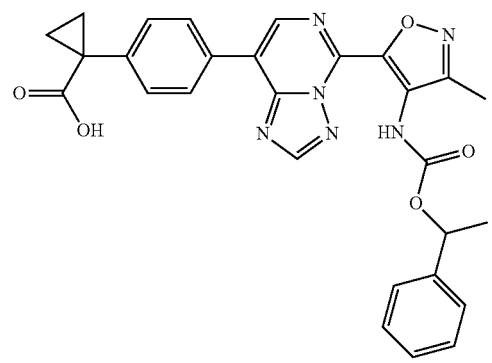 [SMILES: Cc1noc(-c2ncc(-c3ccc(C4(C(=O)O)CC4)cc3)c3ncnn23)c1NC(=O)OC(C)c1ccccc1]
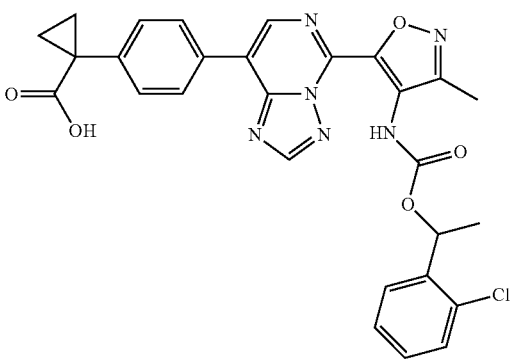 [SMILES: Cc1noc(-c2ncc(-c3ccc(C4(C(=O)O)CC4)cc3)c3ncnn23)c1NC(=O)OC(C)c1ccccc1Cl]
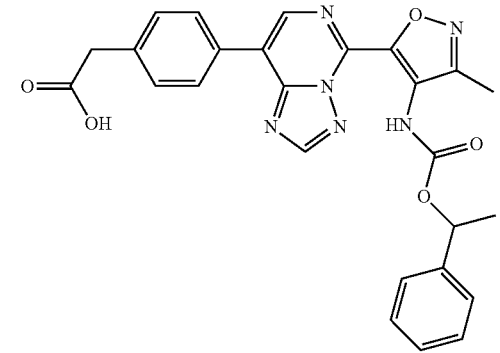 [SMILES: Cc1noc(-c2ncc(-c3ccc(CC(=O)O)cc3)c3ncnn23)c1NC(=O)OC(C)c1ccccc1]

TABLE 1-continued
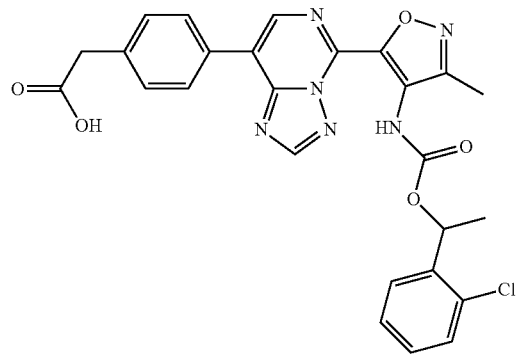 [SMILES: Cc1noc(-c2ncc(-c3ccc(CC(=O)O)cc3)c3ncnn23)c1NC(=O)OC(C)c1ccccc1Cl]
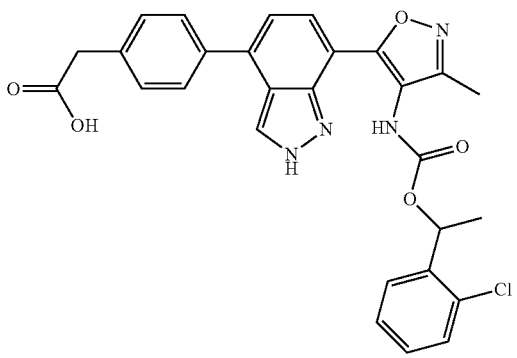
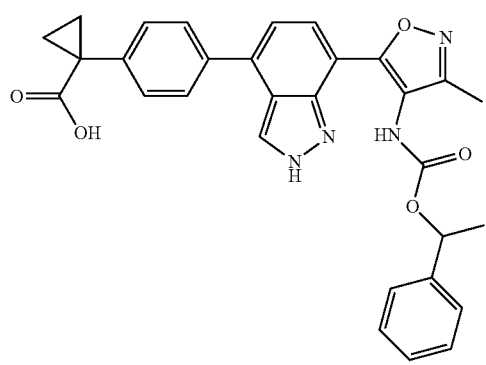 [SMILES: Cc1noc(-c2ccc(-c3ccc(C4(C(=O)O)CC4)cc3)c3c[nH]nc23)c1NC(=O)OC(C)c1ccccc1]
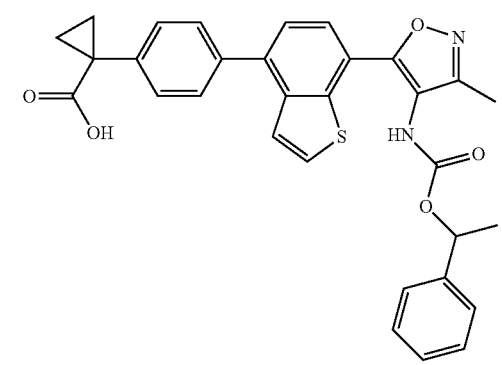
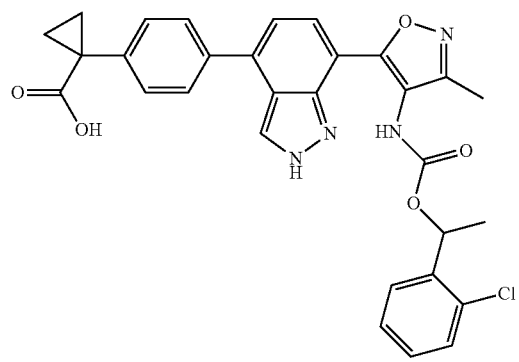 [SMILES: Cc1noc(-c2ccc(-c3ccc(C4(C(=O)O)CC4)cc3)c3c[nH]nc23)c1NC(=O)OC(C)c1ccccc1Cl]
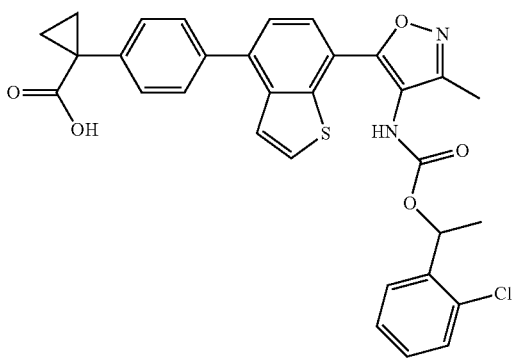
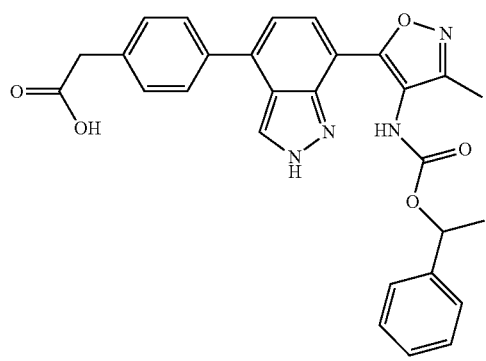 [SMILES: Cc1noc(-c2ccc(-c3ccc(CC(=O)O)cc3)c3c[nH]nc23)c1NC(=O)OC(C)c1ccccc1]
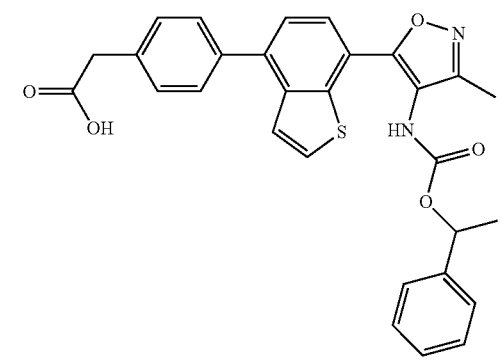 [SMILES: Cc1noc(-c2ccc(-c3ccc(CC(=O)O)cc3)c3ccsc23)c1NC(=O)OC(C)c1ccccc1]

TABLE 1-continued
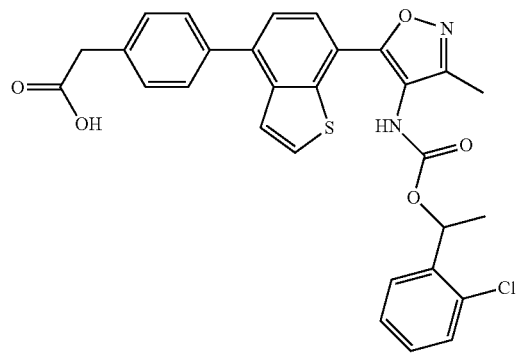 [SMILES: Cc1noc(-c2ccc(-c3ccc(CC(=O)O)cc3)c3ccsc23)c1NC(=O)OC(C)c1ccccc1Cl]
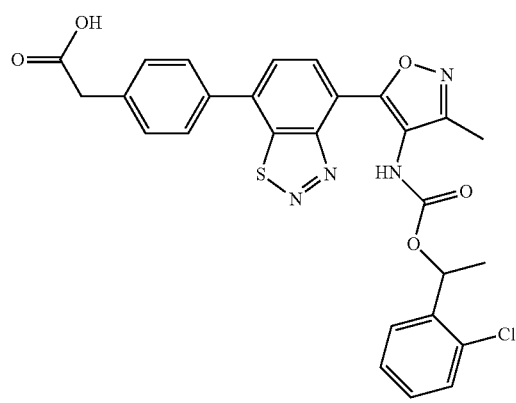 [SMILES: Cc1noc(-c2ccc(-c3ccc(CC(=O)O)cc3)c3snnc23)c1NC(=O)OC(C)c1ccccc1Cl]
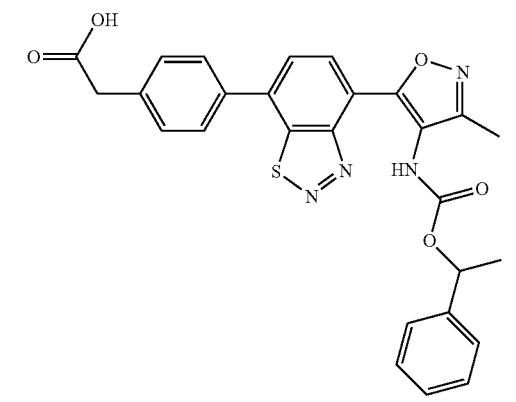 [SMILES: Cc1noc(-c2ccc(-c3ccc(CC(=O)O)cc3)c3snnc23)c1NC(=O)OC(C)c1ccccc1]
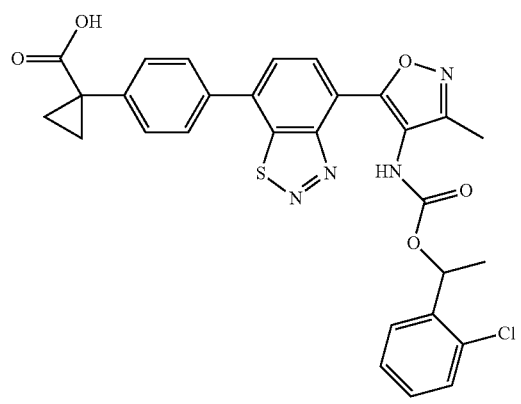 [SMILES: Cc1noc(-c2ccc(-c3ccc(C4(C(=O)O)CC4)cc3)c3snnc23)c1NC(=O)OC(C)c1ccccc1Cl]
TABLE 1-continued
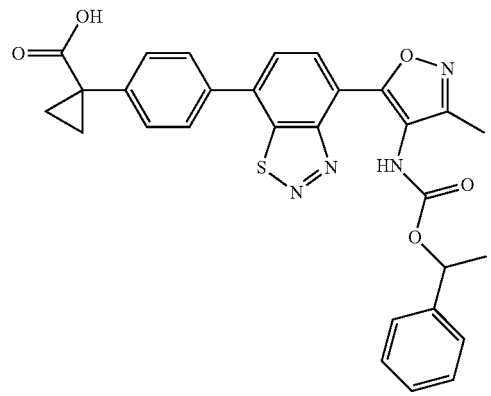 [SMILES: Cc1noc(-c2ccc(-c3ccc(C4(C(=O)O)CC4)cc3)c3snnc23)c1NC(=O)OC(C)c1ccccc1]
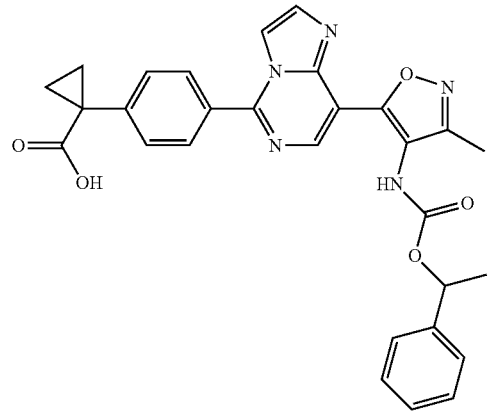 [SMILES: Cc1noc(-c2cnc(-c3ccc(C4(C(=O)O)CC4)cc3)n3ccnc23)c1NC(=O)OC(C)c1ccccc1]
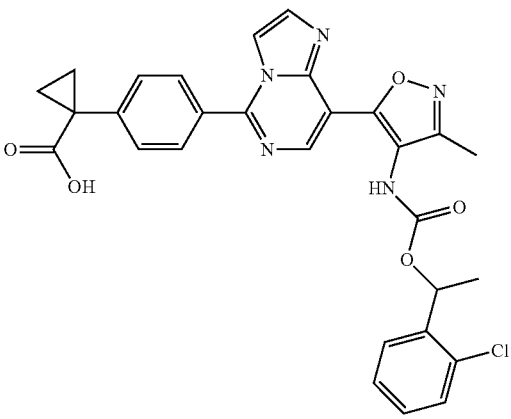 [SMILES: Cc1noc(-c2cnc(-c3ccc(C4(C(=O)O)CC4)cc3)n3ccnc23)c1NC(=O)OC(C)c1ccccc1Cl]
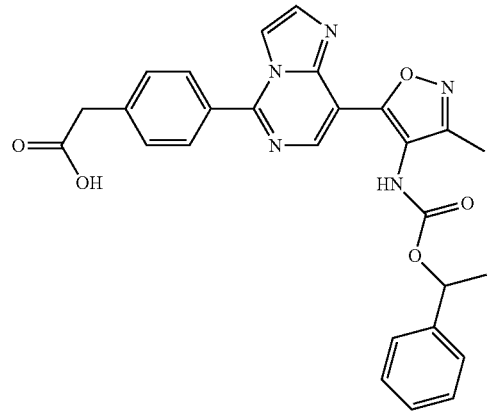 [SMILES: Cc1noc(-c2cnc(-c3ccc(CC(=O)O)cc3)n3ccnc23)c1NC(=O)OC(C)c1ccccc1]

TABLE 1-continued
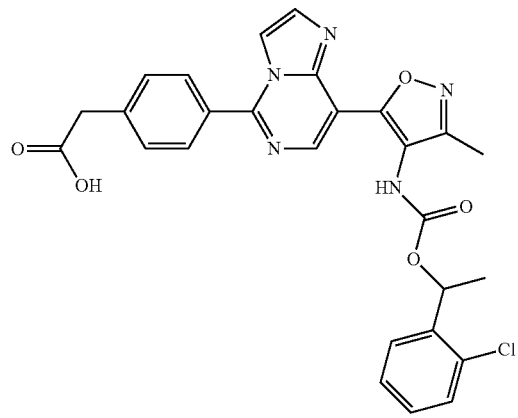 [SMILES: Cc1noc(-c2cnc(-c3ccc(CC(=O)O)cc3)n3ccnc23)c1NC(=O)OC(C)c1ccccc1Cl]
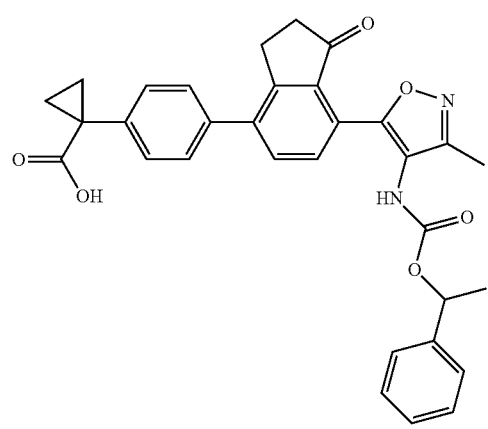 [SMILES: Cc1noc(-c2ccc(-c3ccc(C4(C(=O)O)CC4)cc3)c3c2C(=O)CC3)c1NC(=O)OC(C)c1ccccc1]
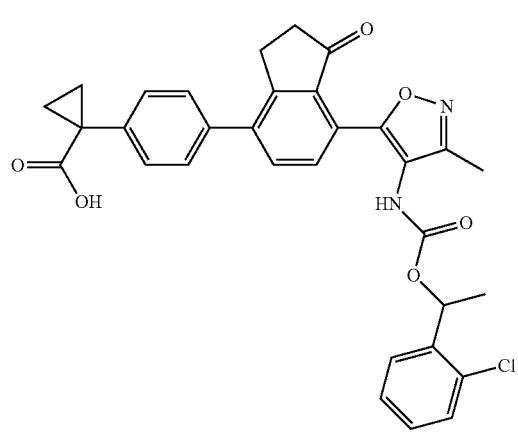 [SMILES: Cc1noc(-c2ccc(-c3ccc(C4(C(=O)O)CC4)cc3)c3c2C(=O)CC3)c1NC(=O)OC(C)c1ccccc1Cl]
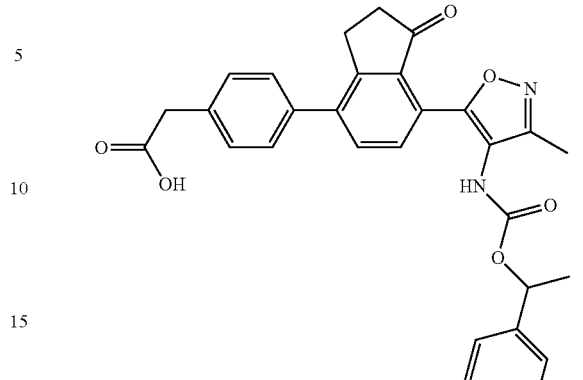
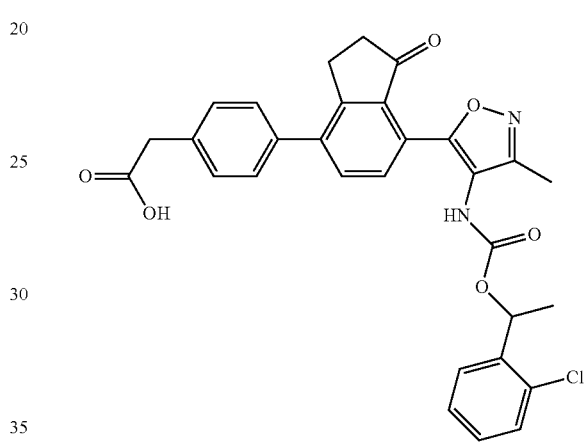
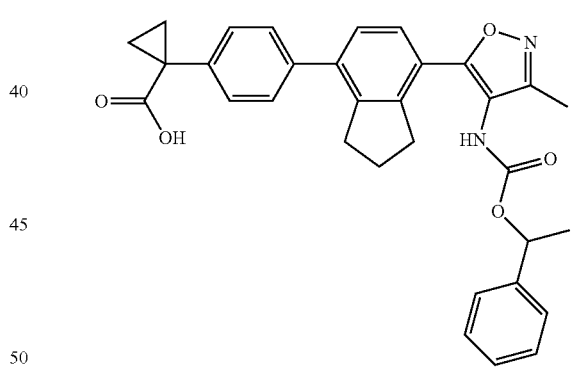
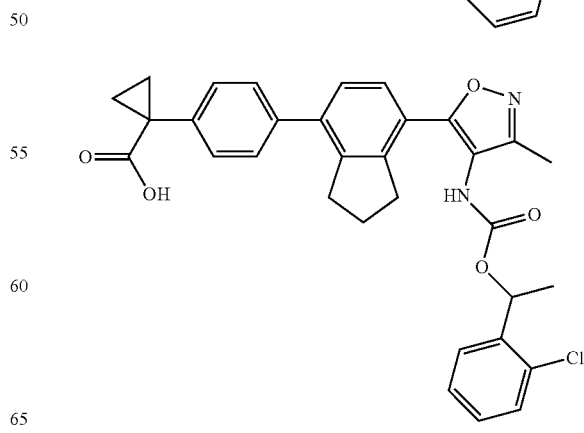

209
TABLE 1-continued
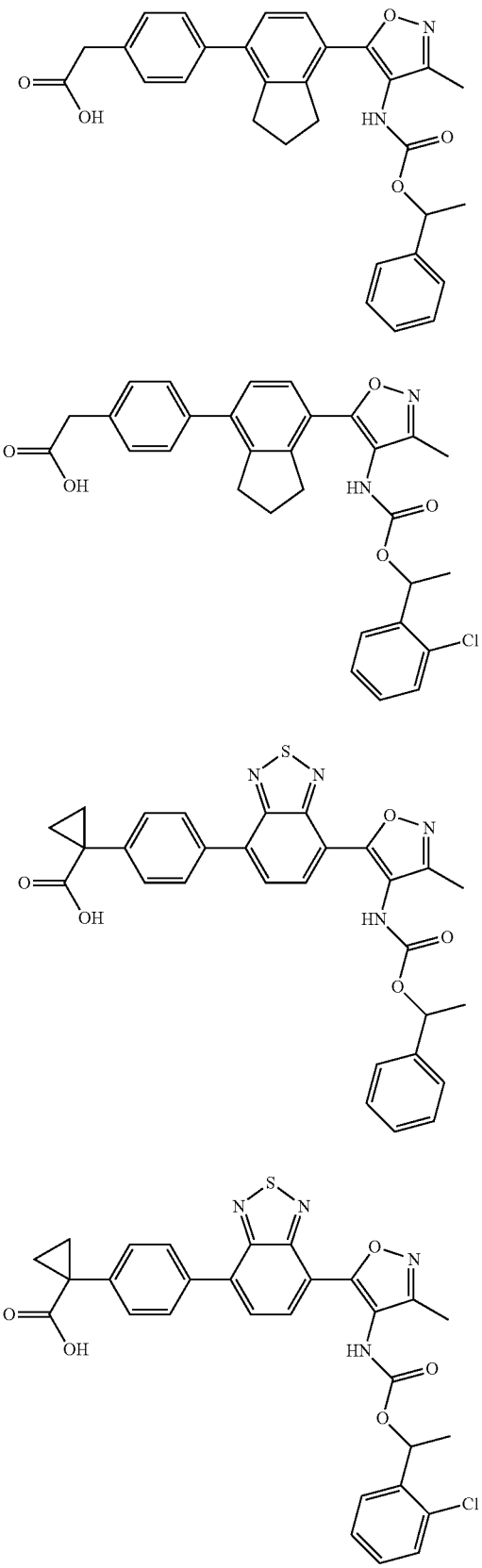
210
TABLE 1-continued
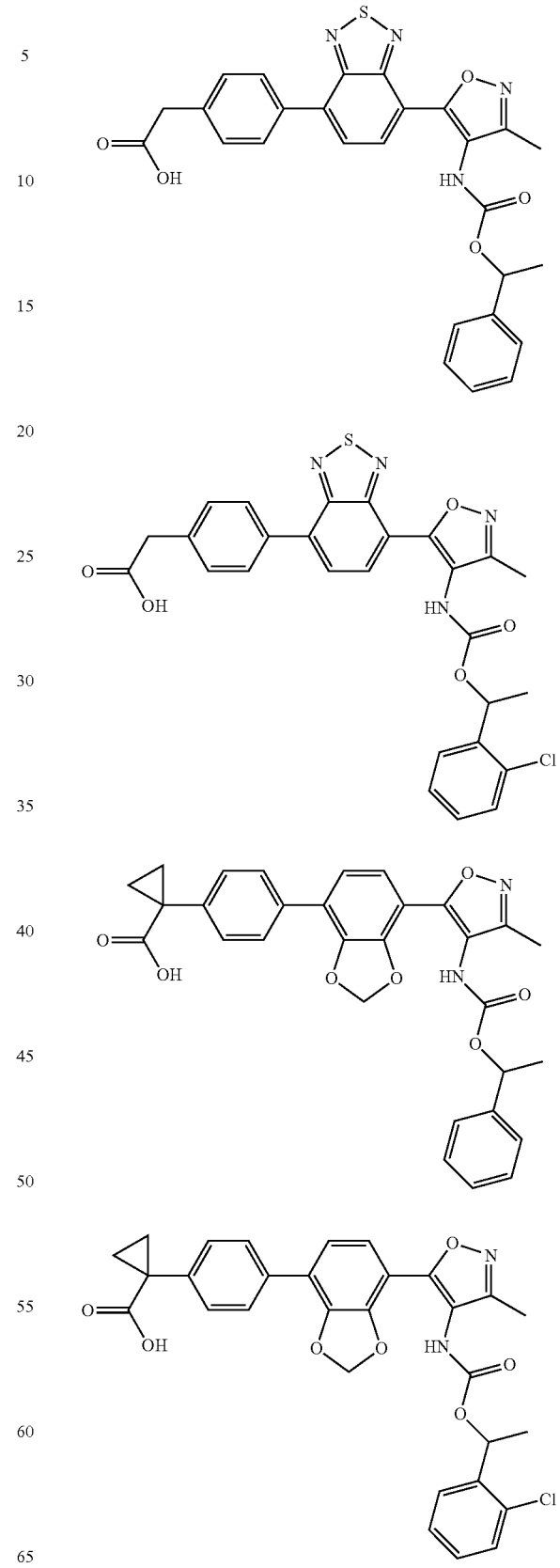

211
TABLE 1-continued
212
TABLE 1-continued
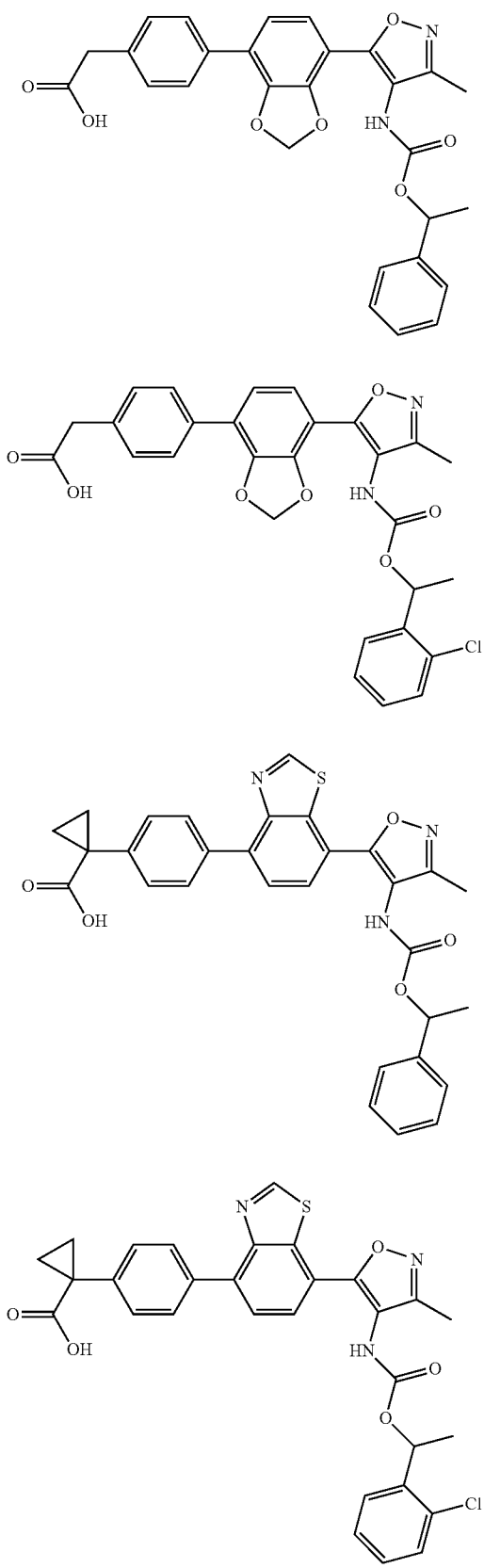
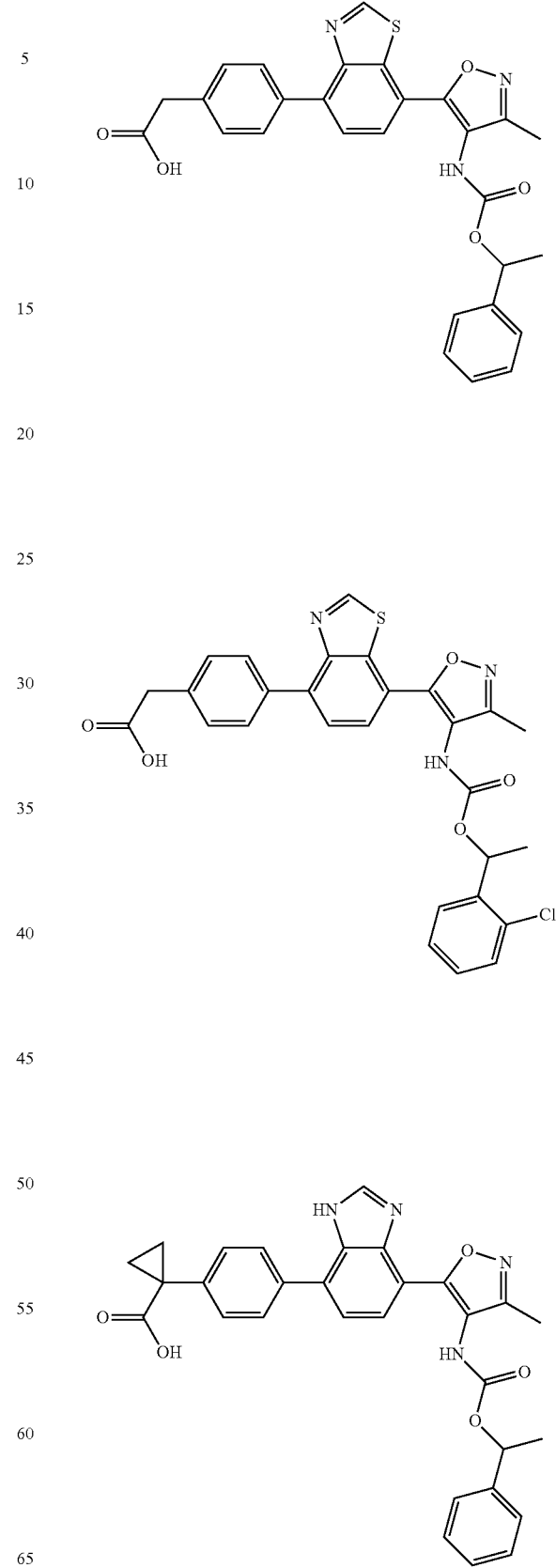

TABLE 1-continued
213
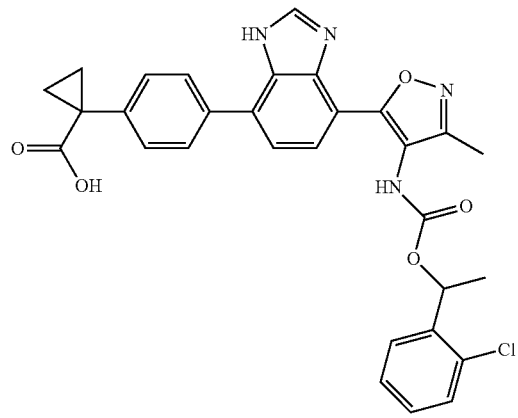 [SMILES: Cc1noc(-c2ccc(-c3ccc(C4(C(=O)O)CC4)cc3)c3[nH]cnc23)c1NC(=O)OC(C)c1ccccc1Cl]
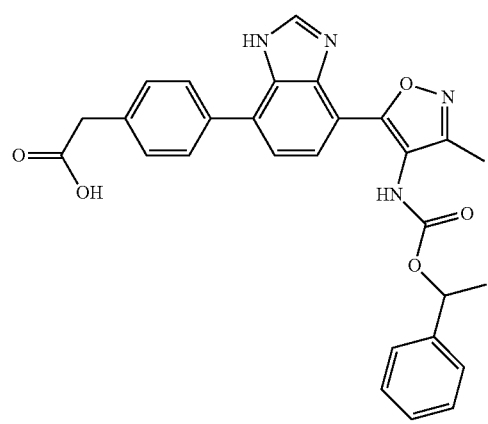 [SMILES: Cc1noc(-c2ccc(-c3ccc(CC(=O)O)cc3)c3[nH]cnc23)c1NC(=O)OC(C)c1ccccc1]
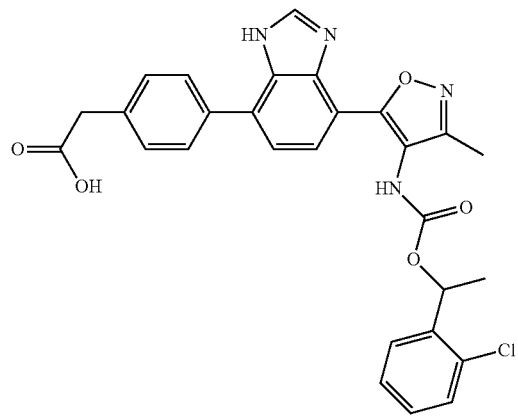 [SMILES: Cc1noc(-c2ccc(-c3ccc(CC(=O)O)cc3)c3[nH]cnc23)c1NC(=O)OC(C)c1ccccc1Cl]
TABLE 1-continued
214
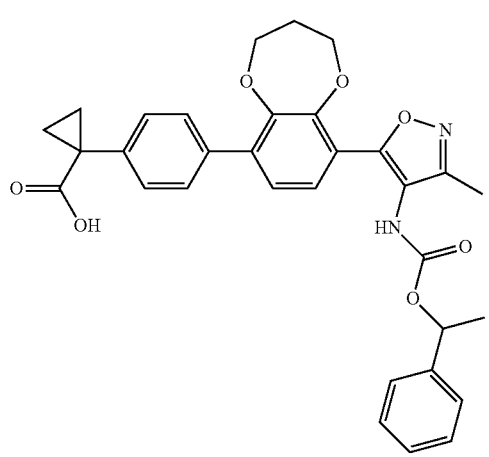 [SMILES: Cc1noc(-c2ccc(-c3ccc(C4(C(=O)O)CC4)cc3)c3c2OCCCO3)c1NC(=O)OC(C)c1ccccc1]
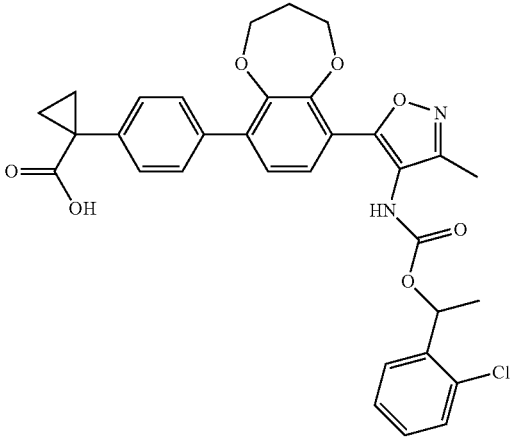 [SMILES: Cc1noc(-c2ccc(-c3ccc(C4(C(=O)O)CC4)cc3)c3c2OCCCO3)c1NC(=O)OC(C)c1ccccc1Cl]
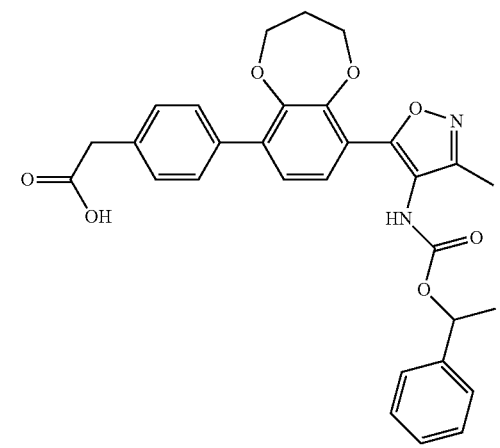 [SMILES: Cc1noc(-c2ccc(-c3ccc(CC(=O)O)cc3)c3c2OCCCO3)c1NC(=O)OC(C)c1ccccc1]

215
TABLE 1-continued
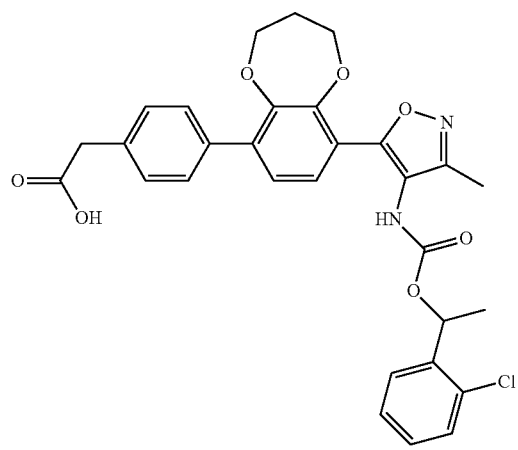 [SMILES: Cc1noc(-c2ccc(-c3ccc(CC(=O)O)cc3)c3c2OCCCO3)c1NC(=O)OC(C)c1ccccc1Cl]
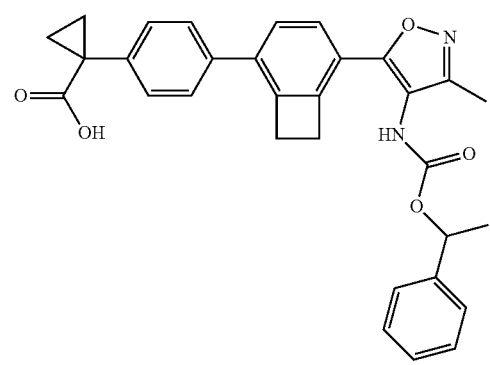 [SMILES: Cc1noc(-c2ccc(-c3ccc(C4(C(=O)O)CC4)cc3)c3c2CC3)c1NC(=O)OC(C)c1ccccc1]
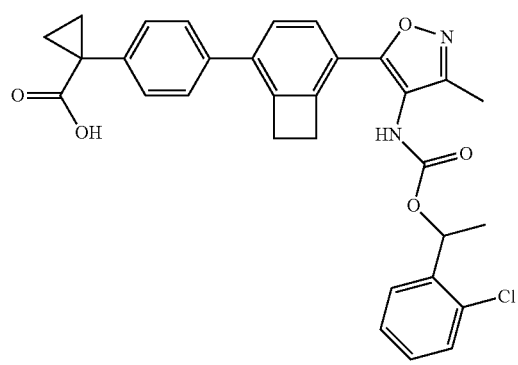 [SMILES: Cc1noc(-c2ccc(-c3ccc(C4(C(=O)O)CC4)cc3)c3c2CC3)c1NC(=O)OC(C)c1ccccc1Cl]
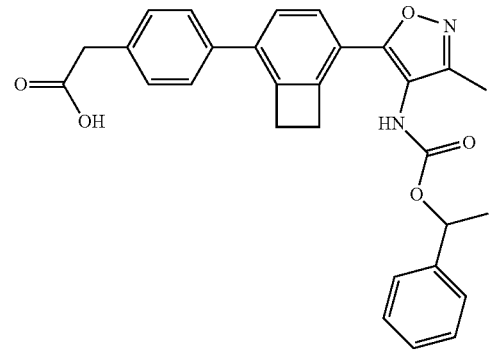 [SMILES: Cc1noc(-c2ccc(-c3ccc(CC(=O)O)cc3)c3c2CC3)c1NC(=O)OC(C)c1ccccc1]
216
TABLE 1-continued
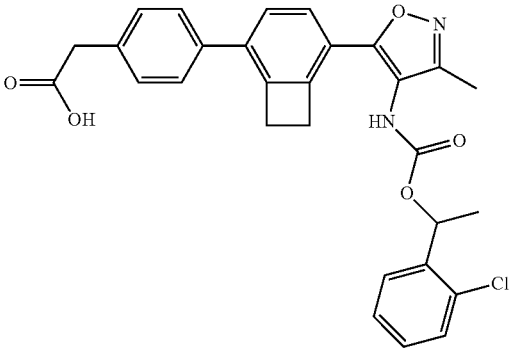 [SMILES: Cc1noc(-c2ccc(-c3ccc(CC(=O)O)cc3)c3c2CC3)c1NC(=O)OC(C)c1ccccc1Cl]
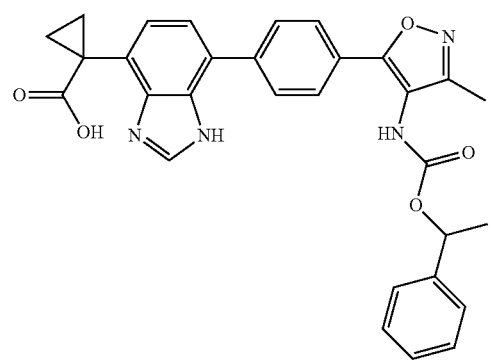 [SMILES: Cc1noc(-c2ccc(-c3ccc(C4(C(=O)O)CC4)c4nc[nH]c34)cc2)c1NC(=O)OC(C)c1ccccc1]
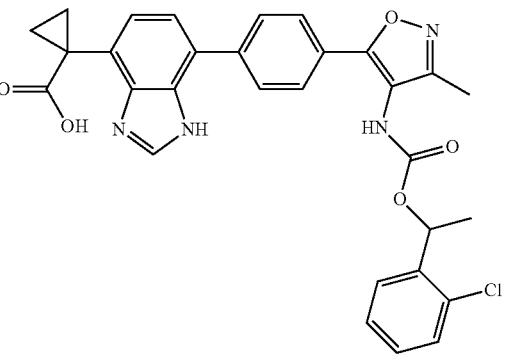 [SMILES: Cc1noc(-c2ccc(-c3ccc(C4(C(=O)O)CC4)c4nc[nH]c34)cc2)c1NC(=O)OC(C)c1ccccc1Cl]
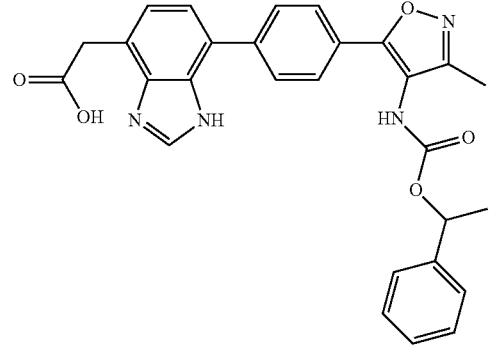

| 217 | 218 |
|---|---|
| TABLE 1-continued | TABLE 1-continued |
| 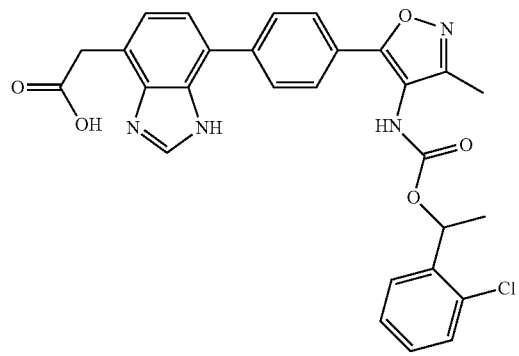 [SMILES: Cc1noc(-c2ccc(-c3ccc(CC(=O)O)c4nc[nH]c34)cc2)c1NC(=O)OC(C)c1ccccc1Cl] | 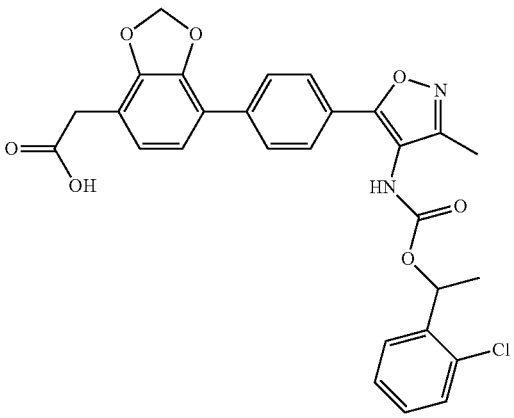 |
| 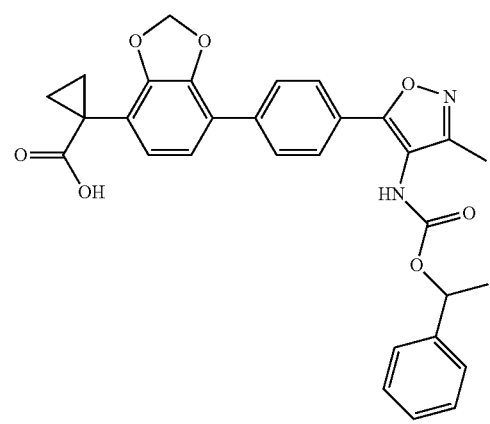 [SMILES: Cc1noc(-c2ccc(-c3ccc(C4(C(=O)O)CC4)c4c3OCO4)cc2)c1NC(=O)OC(C)c1ccccc1] | |
| 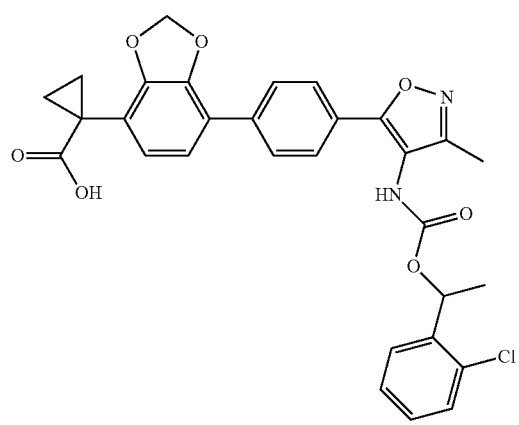 [SMILES: Cc1noc(-c2ccc(-c3ccc(C4(C(=O)O)CC4)c4c3OCO4)cc2)c1NC(=O)OC(C)c1ccccc1Cl] | |
| 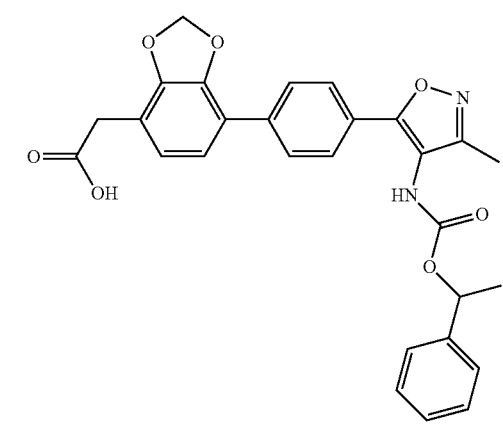 [SMILES: Cc1noc(-c2ccc(-c3ccc(CC(=O)O)c4c3OCO4)cc2)c1NC(=O)OC(C)c1ccccc1] | |

219
TABLE 1-continued
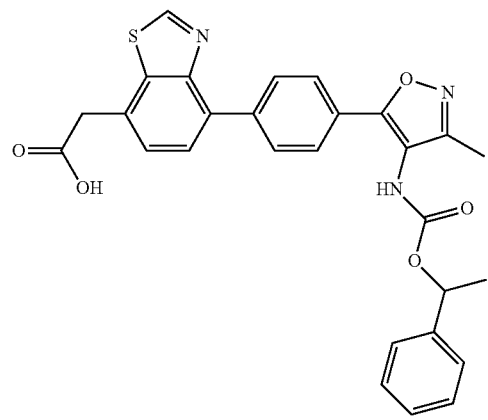 [SMILES: Cc1noc(-c2ccc(-c3ccc(CC(=O)O)c4scnc34)cc2)c1NC(=O)OC(C)c1ccccc1]
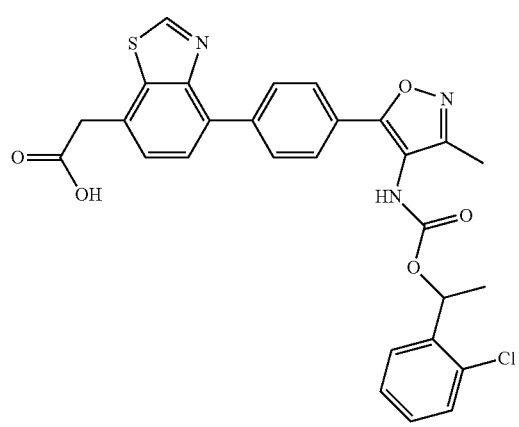 [SMILES: Cc1noc(-c2ccc(-c3ccc(CC(=O)O)c4scnc34)cc2)c1NC(=O)OC(C)c1ccccc1Cl]

220
TABLE 1-continued

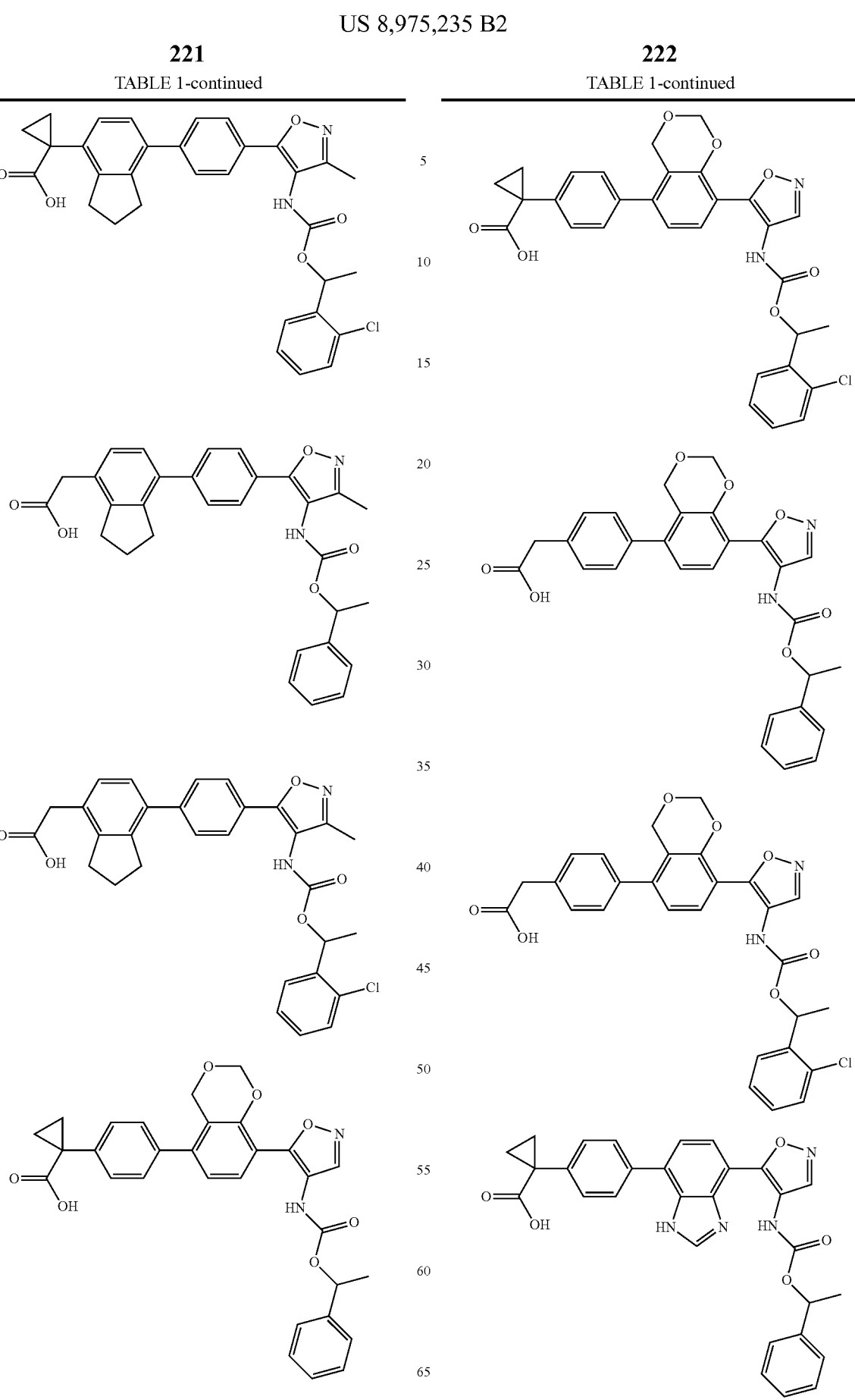

TABLE 1-continued
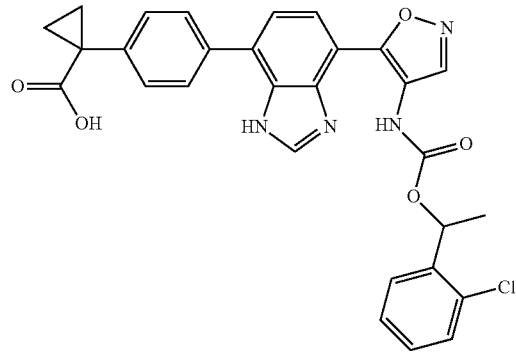 [SMILES: CC(OC(=O)Nc1cnoc1-c1ccc(-c2ccc(C3(C(=O)O)CC3)cc2)c2[nH]cnc12)c1ccccc1Cl]
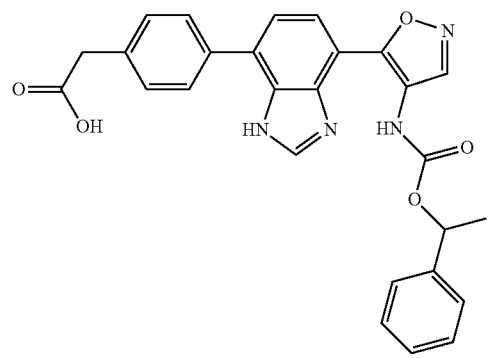 [SMILES: CC(OC(=O)Nc1cnoc1-c1ccc(-c2ccc(CC(=O)O)cc2)c2[nH]cnc12)c1ccccc1]
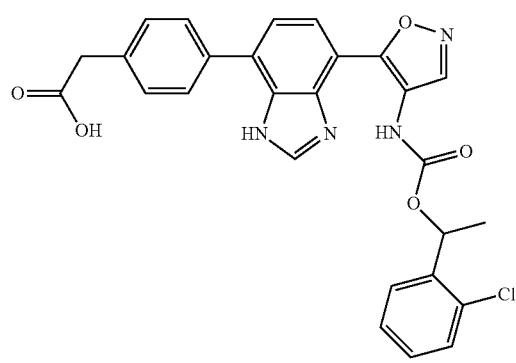 [SMILES: CC(OC(=O)Nc1cnoc1-c1ccc(-c2ccc(CC(=O)O)cc2)c2[nH]cnc12)c1ccccc1Cl]
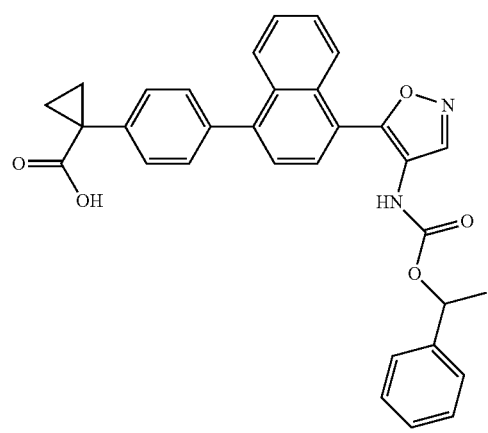 [SMILES: CC(OC(=O)Nc1cnoc1-c1ccc(-c2ccc(C3(C(=O)O)CC3)cc2)c2ccccc12)c1ccccc1]
TABLE 1-continued
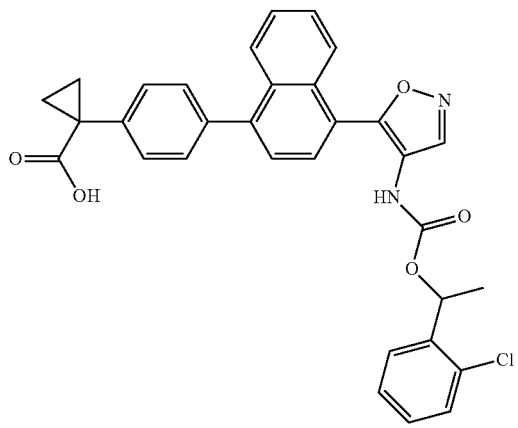 [SMILES: CC(OC(=O)Nc1cnoc1-c1ccc(-c2ccc(C3(C(=O)O)CC3)cc2)c2ccccc12)c1ccccc1Cl]
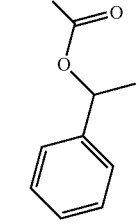
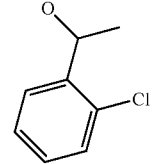

TABLE 1-continued
225
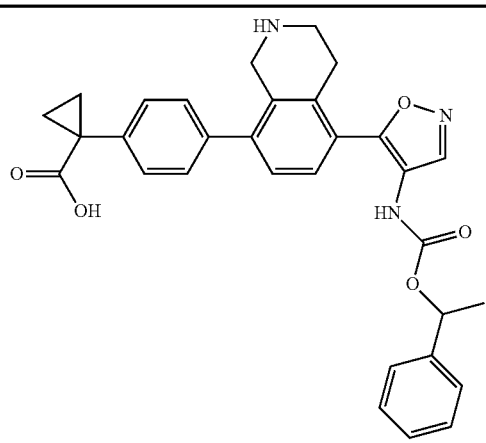
226
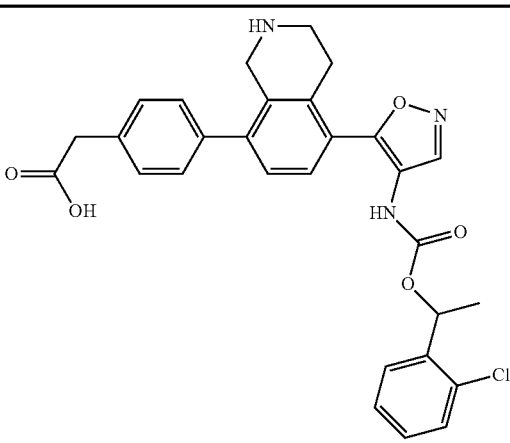
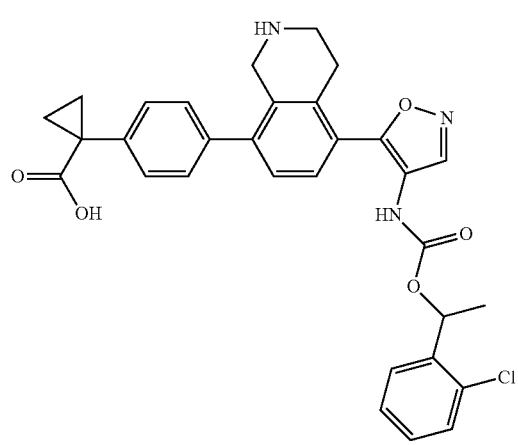 [SMILES: CC(OC(=O)Nc1cnoc1-c1ccc(-c2ccc(C3(C(=O)O)CC3)cc2)c2c1CCNC2)c1ccccc1Cl]
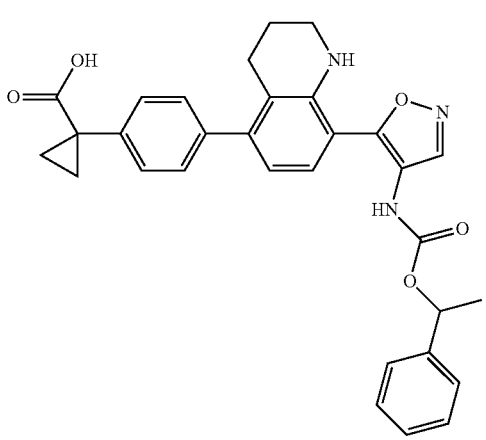
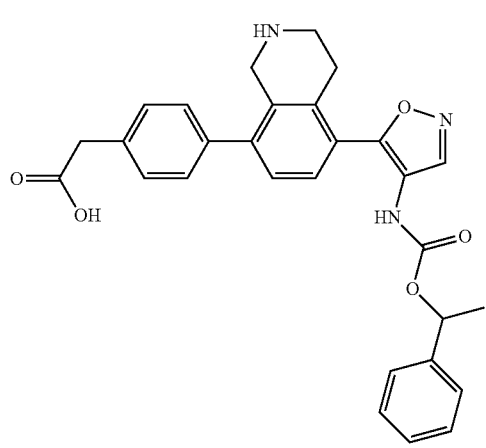 [SMILES: CC(OC(=O)Nc1cnoc1-c1ccc(-c2ccc(CC(=O)O)cc2)c2c1CCNC2)c1ccccc1]
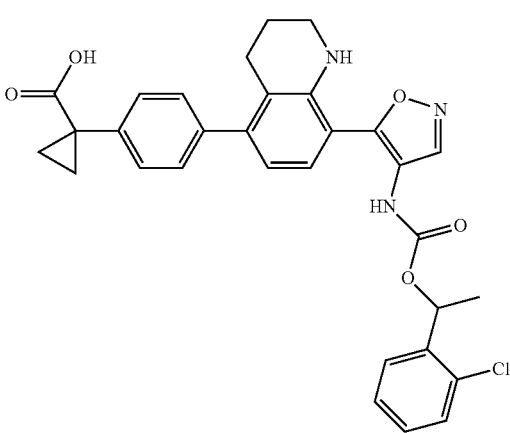 [SMILES: CC(OC(=O)Nc1cnoc1-c1ccc(-c2ccc(C3(C(=O)O)CC3)cc2)c2c1NCCC2)c1ccccc1Cl]

TABLE 1-continued
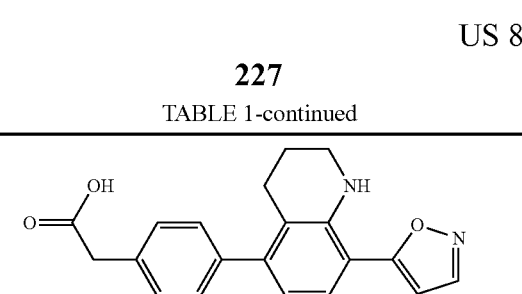
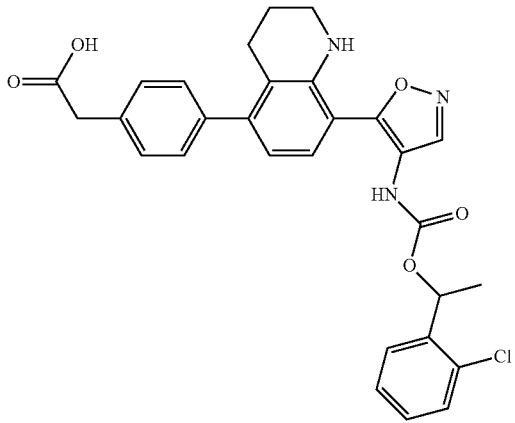 [SMILES: CC(OC(=O)Nc1cnoc1-c1ccc(-c2ccc(CC(=O)O)cc2)c2c1NCCC2)c1ccccc1Cl]
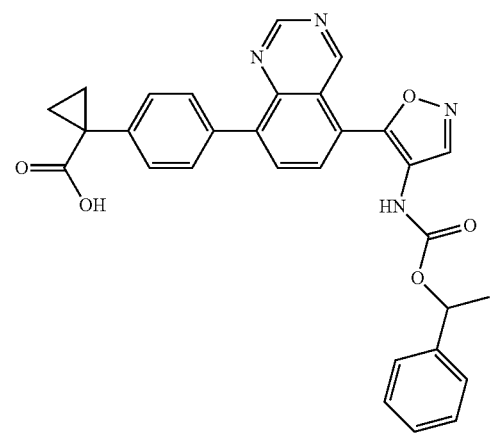 [SMILES: CC(OC(=O)Nc1cnoc1-c1ccc(-c2ccc(C3(C(=O)O)CC3)cc2)c2ncncc12)c1ccccc1]
TABLE 1-continued
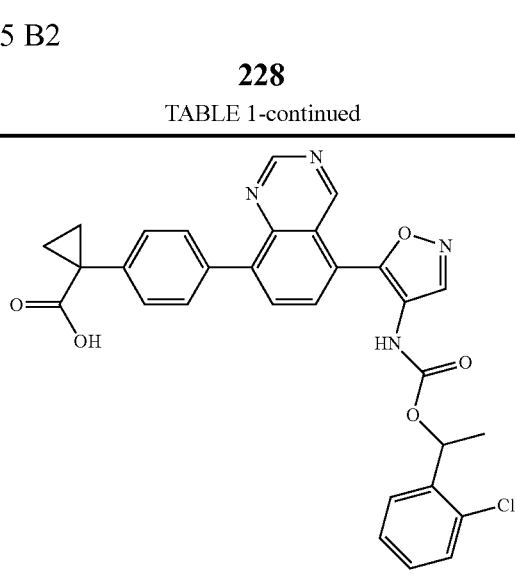
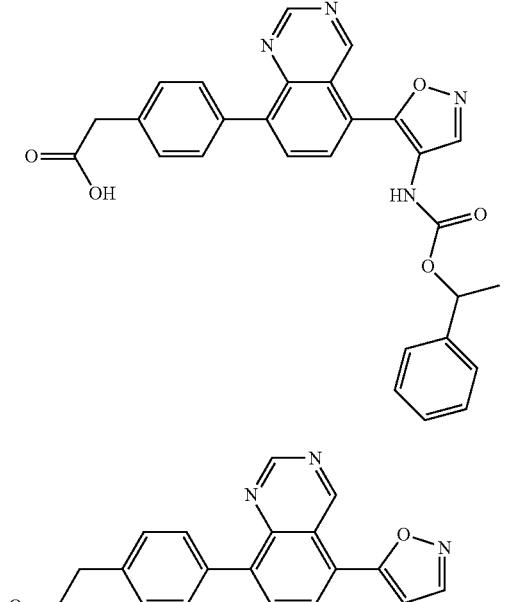
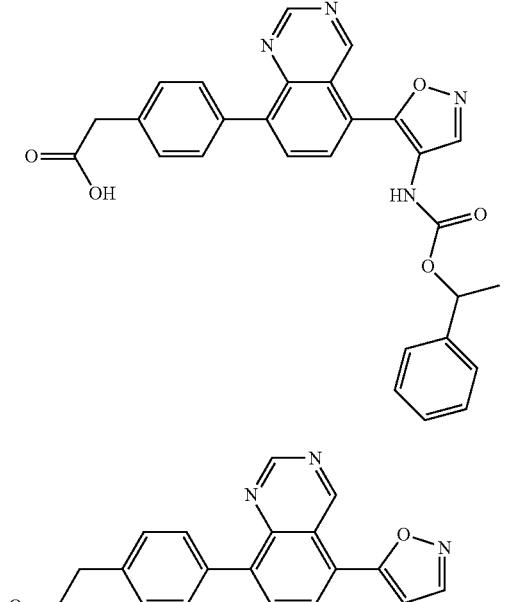
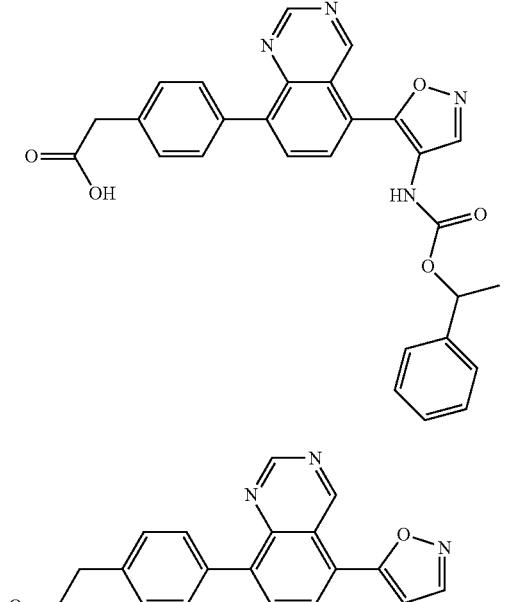

TABLE 1-continued
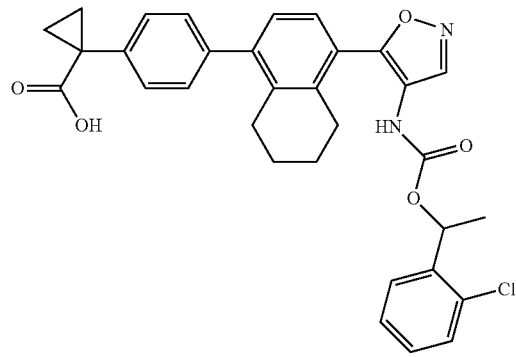 [SMILES: CC(OC(=O)Nc1cnoc1-c1ccc(-c2ccc(C3(C(=O)O)CC3)cc2)c2c1CCCC2)c1ccccc1Cl]
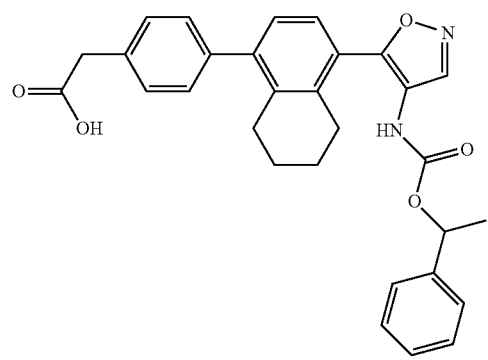 [SMILES: CC(OC(=O)Nc1cnoc1-c1ccc(-c2ccc(CC(=O)O)cc2)c2c1CCCC2)c1ccccc1]
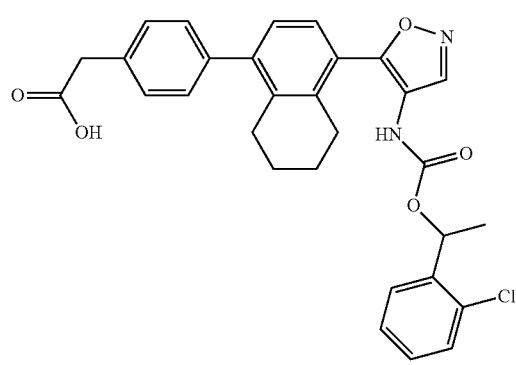 [SMILES: CC(OC(=O)Nc1cnoc1-c1ccc(-c2ccc(CC(=O)O)cc2)c2c1CCCC2)c1ccccc1Cl]
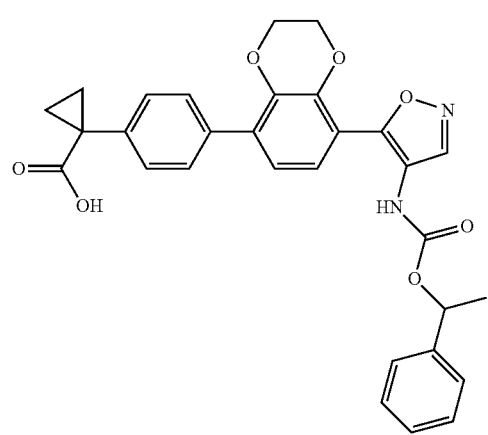 [SMILES: CC(OC(=O)Nc1cnoc1-c1ccc(-c2ccc(C3(C(=O)O)CC3)cc2)c2c1OCCO2)c1ccccc1]
TABLE 1-continued
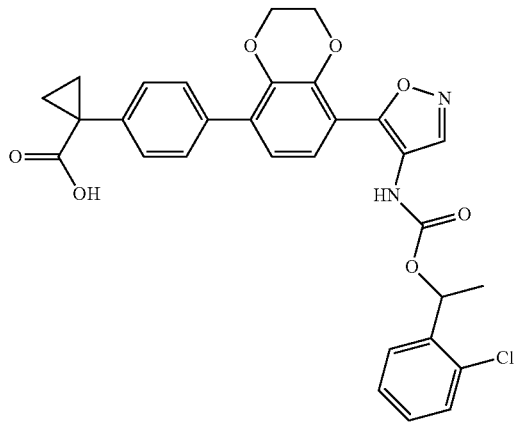 [SMILES: CC(OC(=O)Nc1cnoc1-c1ccc(-c2ccc(C3(C(=O)O)CC3)cc2)c2c1OCCO2)c1ccccc1Cl]
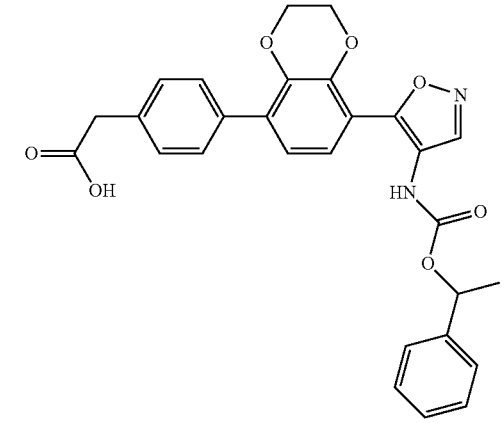 [SMILES: CC(OC(=O)Nc1cnoc1-c1ccc(-c2ccc(CC(=O)O)cc2)c2c1OCCO2)c1ccccc1]
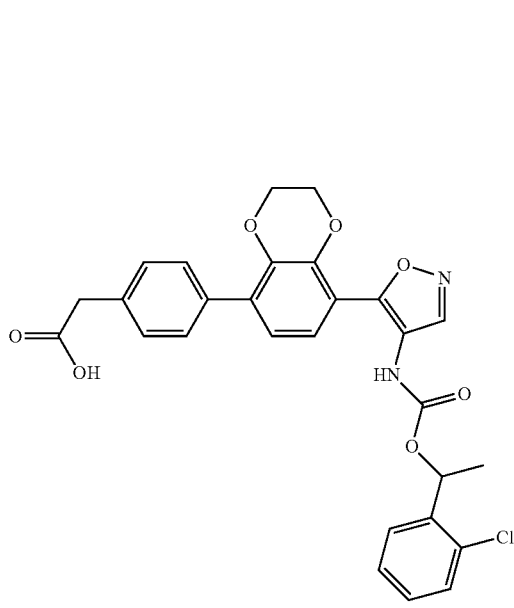 [SMILES: CC(OC(=O)Nc1cnoc1-c1ccc(-c2ccc(CC(=O)O)cc2)c2c1OCCO2)c1ccccc1Cl]

TABLE 1-continued
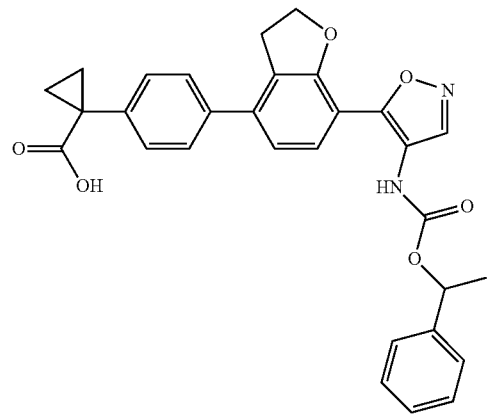 [SMILES: CC(OC(=O)Nc1cnoc1-c1ccc(-c2ccc(C3(C(=O)O)CC3)cc2)c2c1OCC2)c1ccccc1]
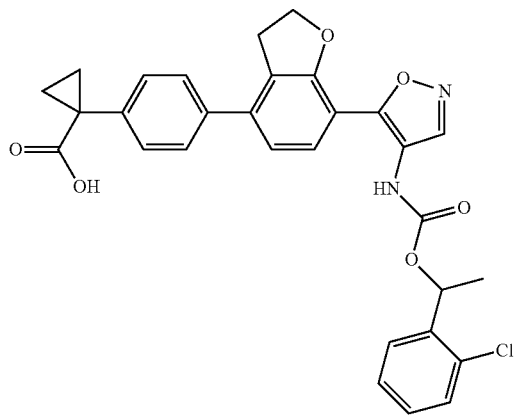 [SMILES: CC(OC(=O)Nc1cnoc1-c1ccc(-c2ccc(C3(C(=O)O)CC3)cc2)c2c1OCC2)c1ccccc1Cl]
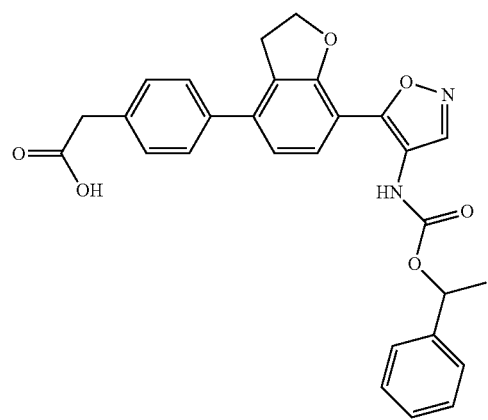 [SMILES: CC(OC(=O)Nc1cnoc1-c1ccc(-c2ccc(CC(=O)O)cc2)c2c1OCC2)c1ccccc1]
TABLE 1-continued
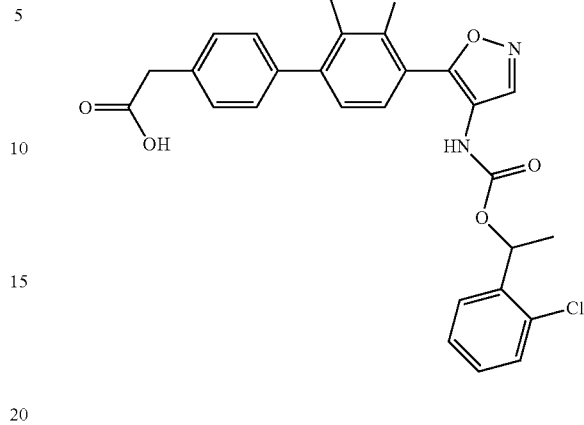
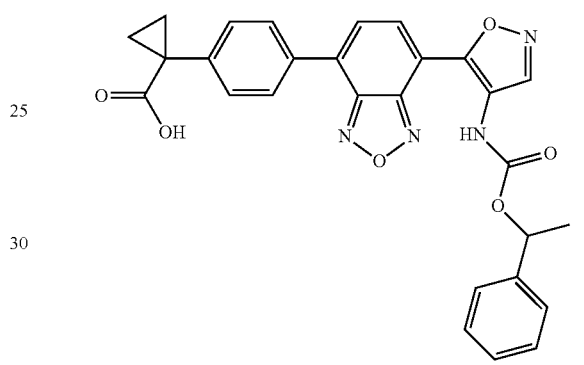
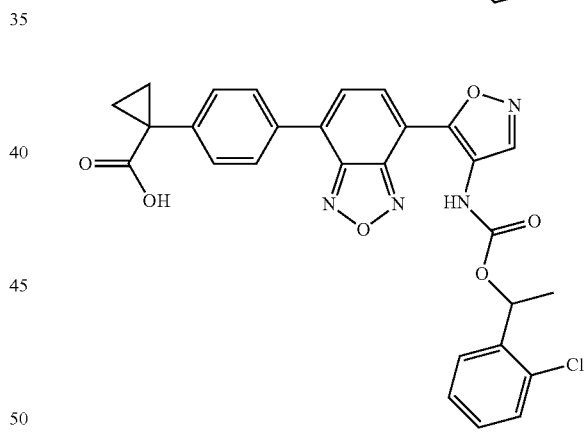
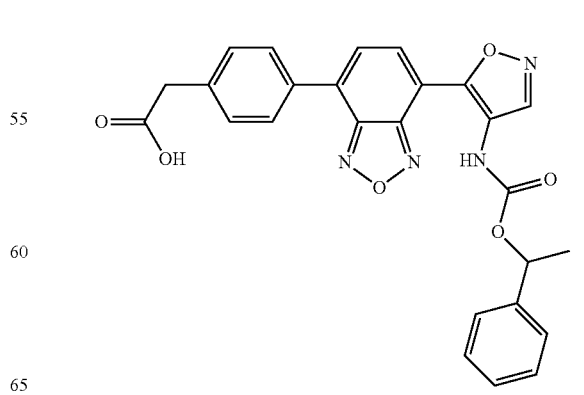

233
TABLE 1-continued
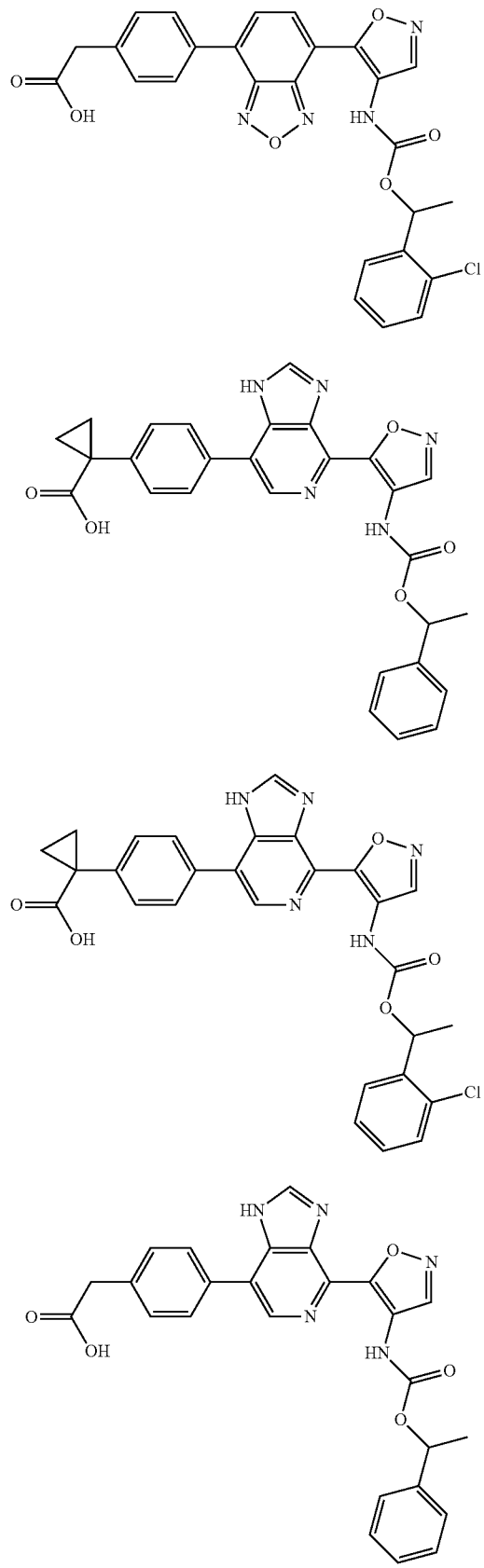
234
TABLE 1-continued
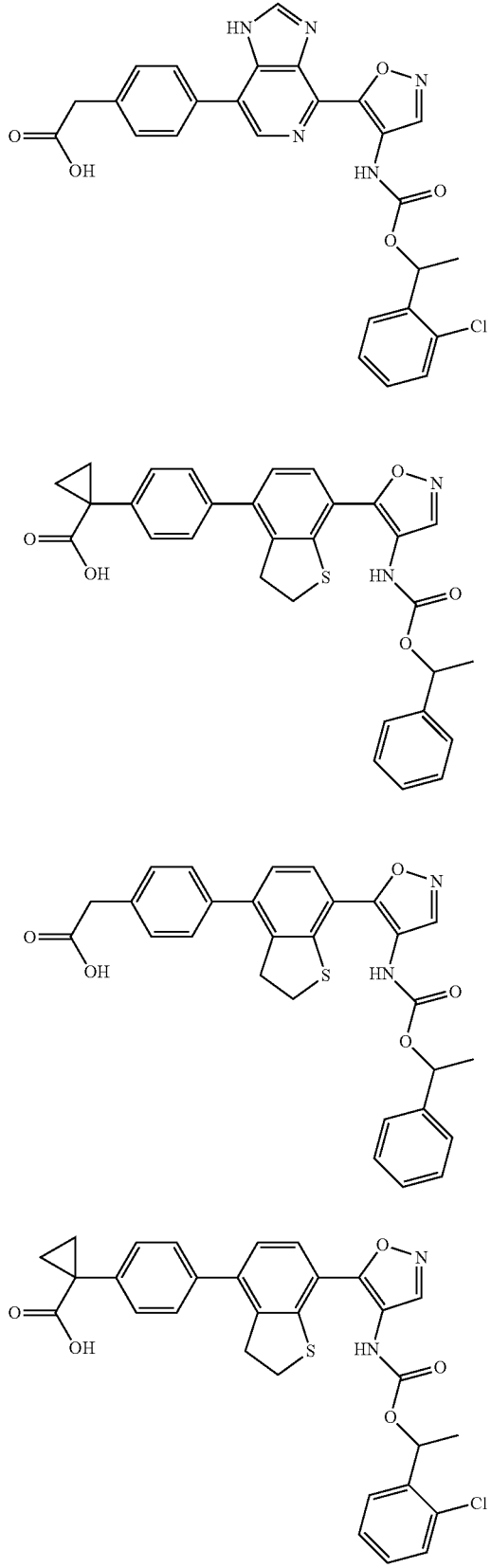

TABLE 1-continued
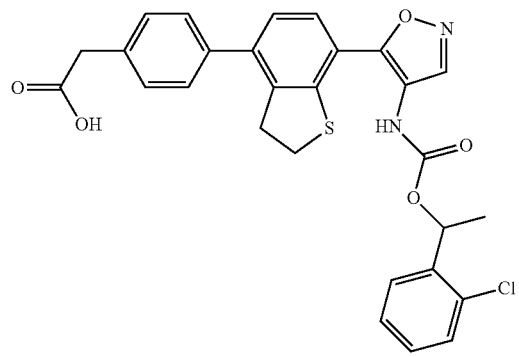
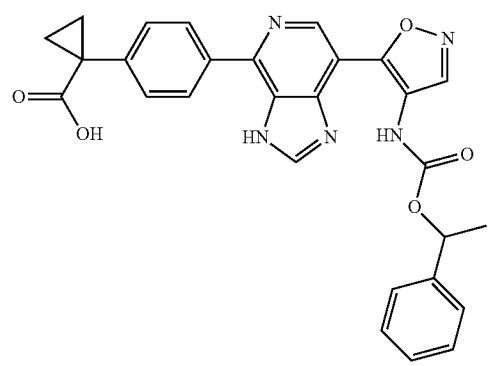 [SMILES: CC(OC(=O)Nc1cnoc1-c1cnc(-c2ccc(C3(C(=O)O)CC3)cc2)c2[nH]cnc12)c1ccccc1]
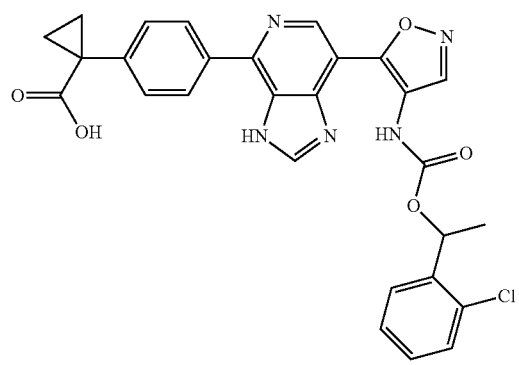 [SMILES: CC(OC(=O)Nc1cnoc1-c1cnc(-c2ccc(C3(C(=O)O)CC3)cc2)c2[nH]cnc12)c1ccccc1Cl]
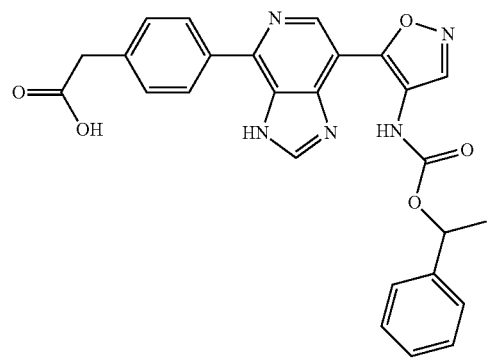 [SMILES: CC(OC(=O)Nc1cnoc1-c1cnc(-c2ccc(CC(=O)O)cc2)c2[nH]cnc12)c1ccccc1]
TABLE 1-continued
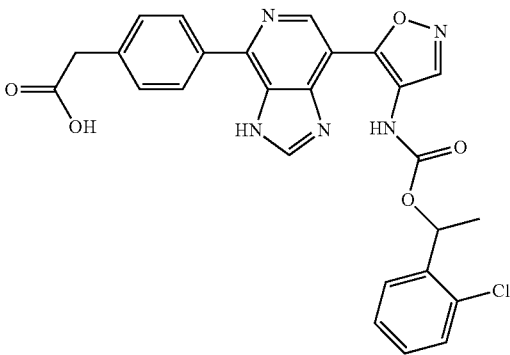 [SMILES: CC(OC(=O)Nc1cnoc1-c1cnc(-c2ccc(CC(=O)O)cc2)c2[nH]cnc12)c1ccccc1Cl]
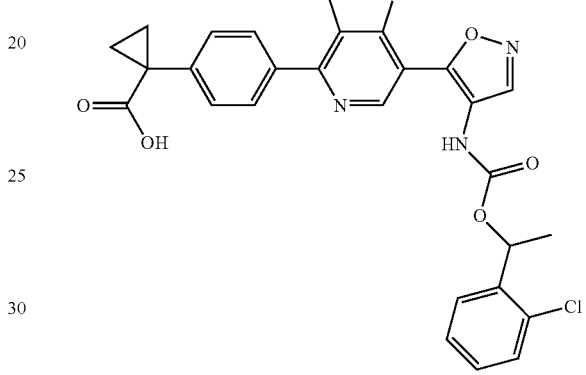
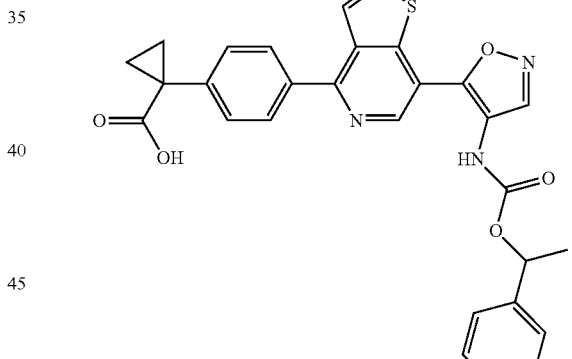
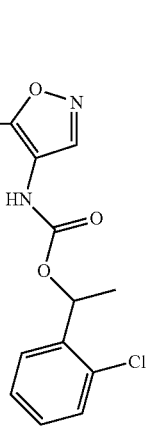

TABLE 1-continued
237
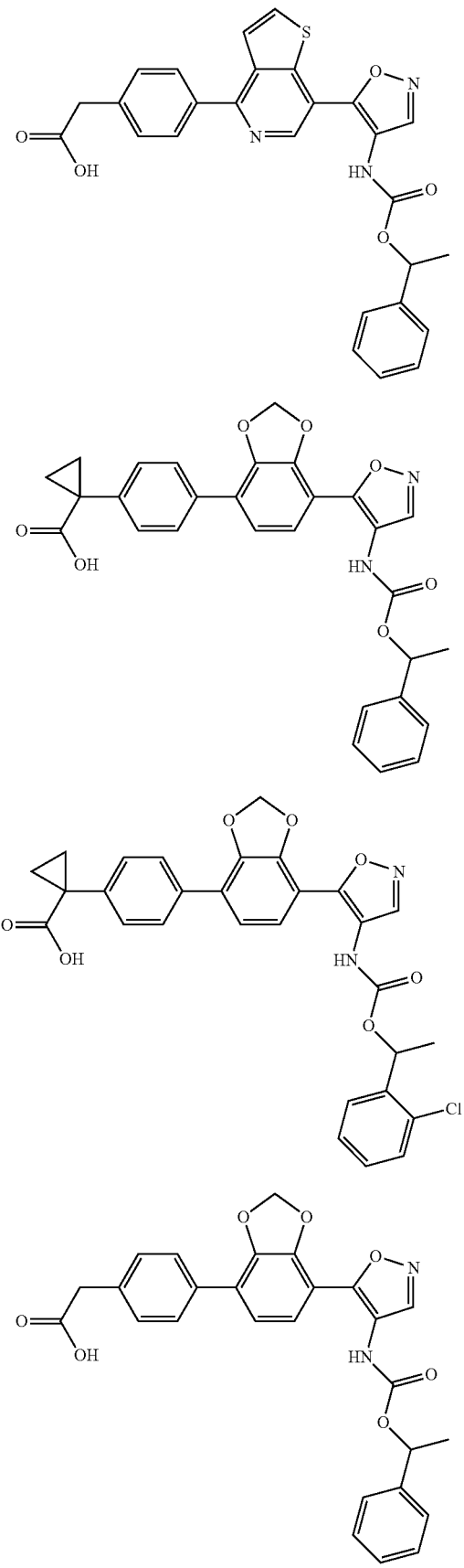
TABLE 1-continued
238
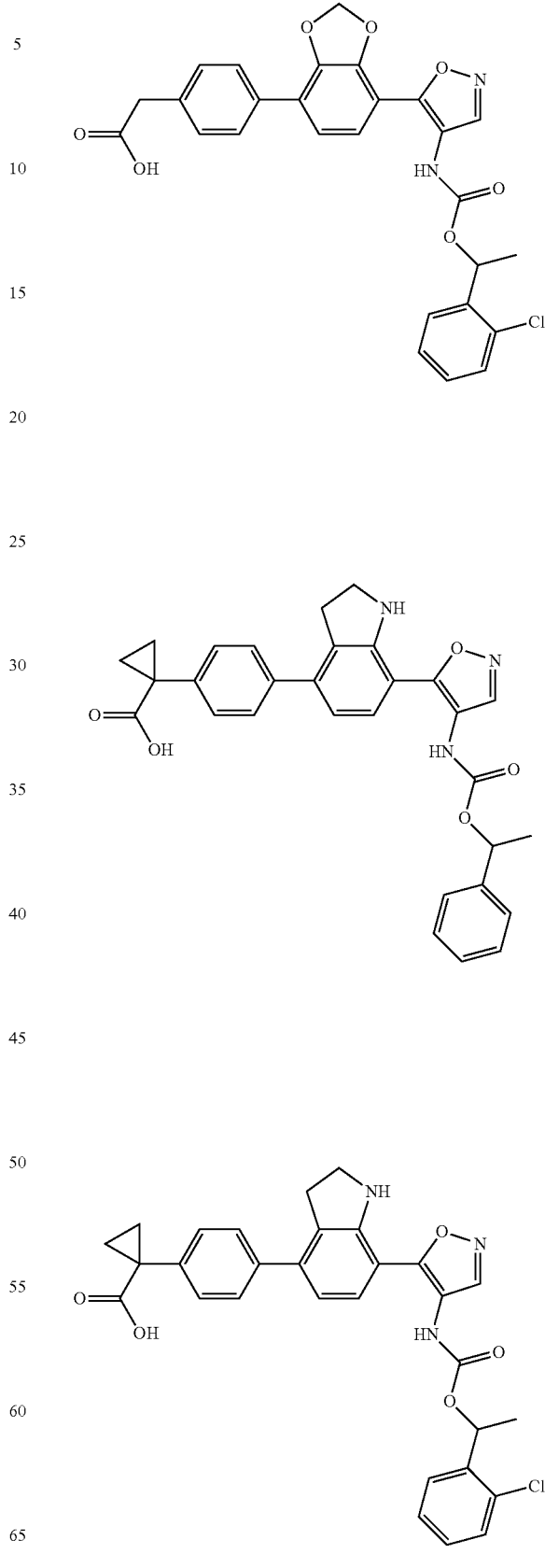

239
TABLE 1-continued
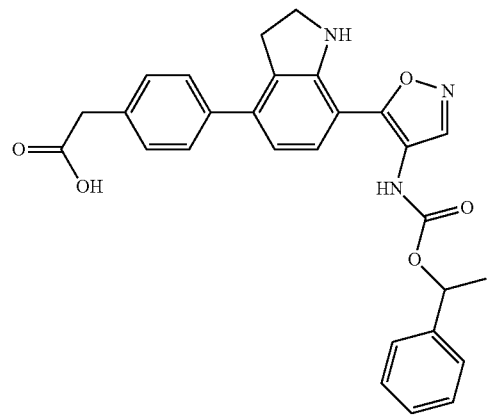 [SMILES: CC(OC(=O)Nc1cnoc1-c1ccc(-c2ccc(CC(=O)O)cc2)c2c1NCC2)c1ccccc1]
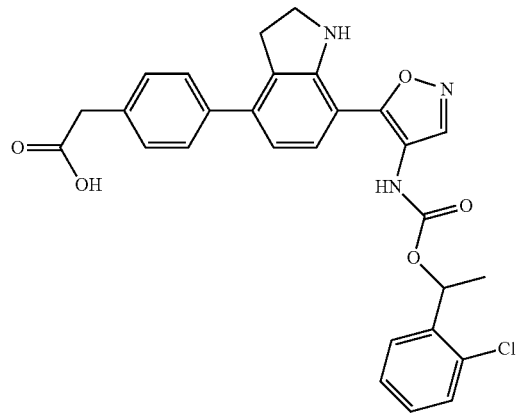 [SMILES: CC(OC(=O)Nc1cnoc1-c1ccc(-c2ccc(CC(=O)O)cc2)c2c1NCC2)c1ccccc1Cl]
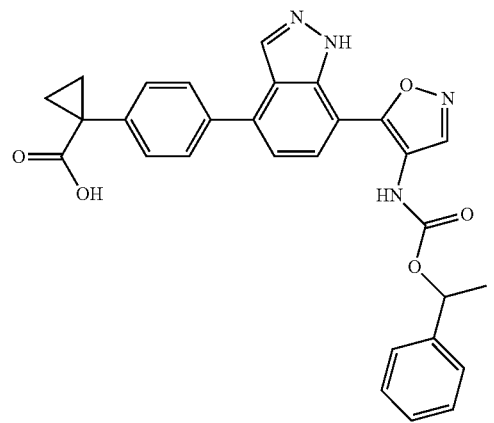 [SMILES: CC(OC(=O)Nc1cnoc1-c1ccc(-c2ccc(C3(C(=O)O)CC3)cc2)c2cn[nH]c12)c1ccccc1]
240
TABLE 1-continued
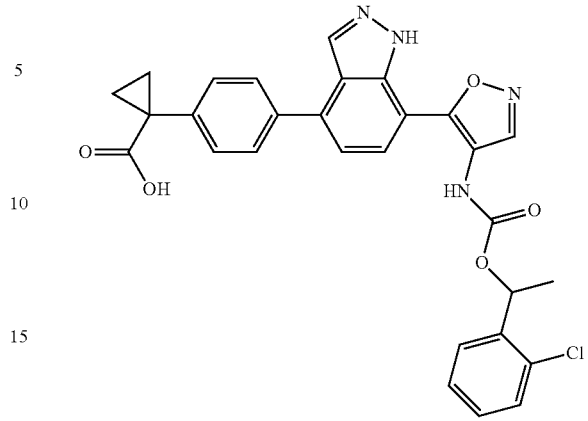
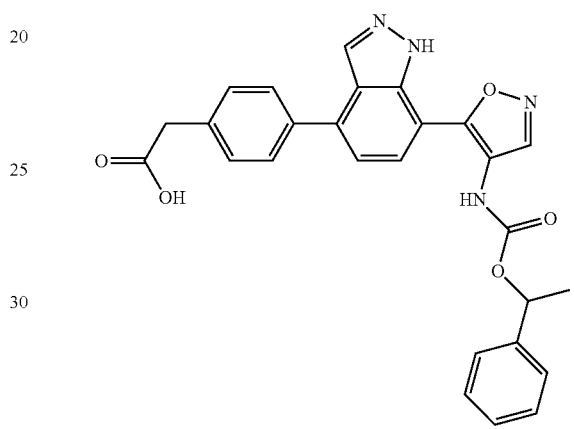
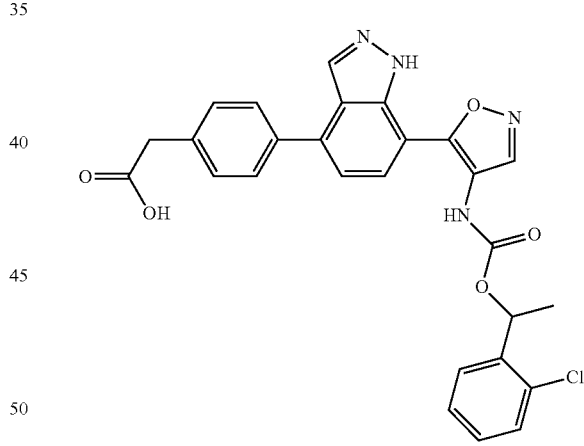

241
TABLE 1-continued
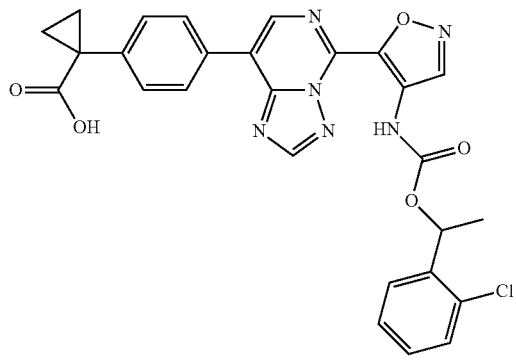 [SMILES: CC(OC(=O)Nc1cnoc1-c1ncc(-c2ccc(C3(C(=O)O)CC3)cc2)c2ncnn12)c1ccccc1Cl]
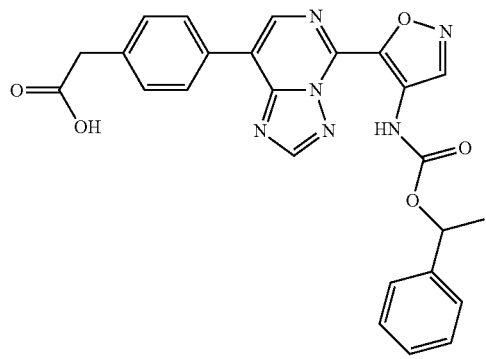 [SMILES: CC(OC(=O)Nc1cnoc1-c1ncc(-c2ccc(CC(=O)O)cc2)c2ncnn12)c1ccccc1]
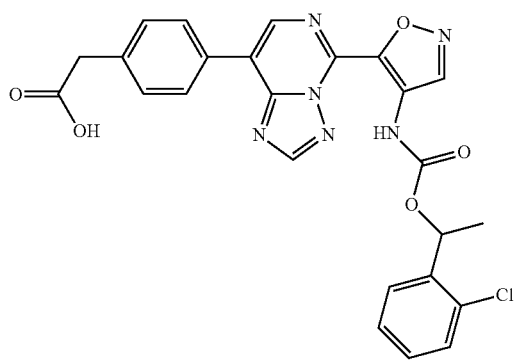 [SMILES: CC(OC(=O)Nc1cnoc1-c1ncc(-c2ccc(CC(=O)O)cc2)c2ncnn12)c1ccccc1Cl]
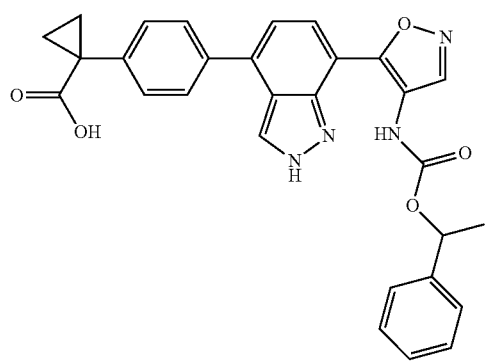 [SMILES: CC(OC(=O)Nc1cnoc1-c1ccc(-c2ccc(C3(C(=O)O)CC3)cc2)c2c[nH]nc12)c1ccccc1]
242
TABLE 1-continued
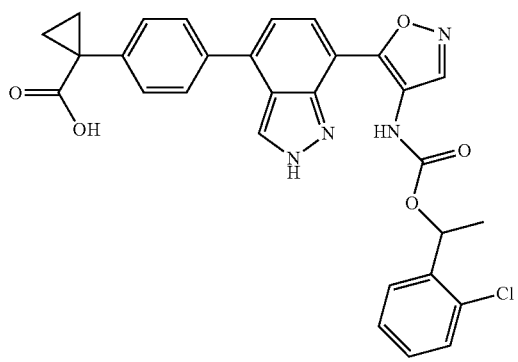 [SMILES: CC(OC(=O)Nc1cnoc1-c1ccc(-c2ccc(C3(C(=O)O)CC3)cc2)c2c[nH]nc12)c1ccccc1Cl]
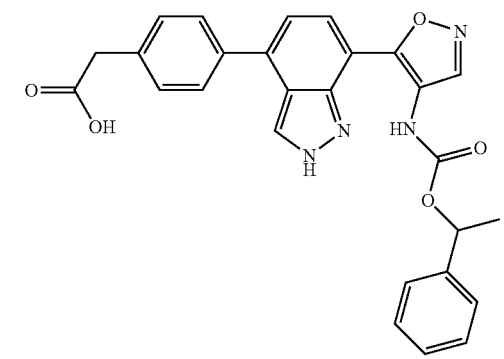 [SMILES: CC(OC(=O)Nc1cnoc1-c1ccc(-c2ccc(CC(=O)O)cc2)c2c[nH]nc12)c1ccccc1]
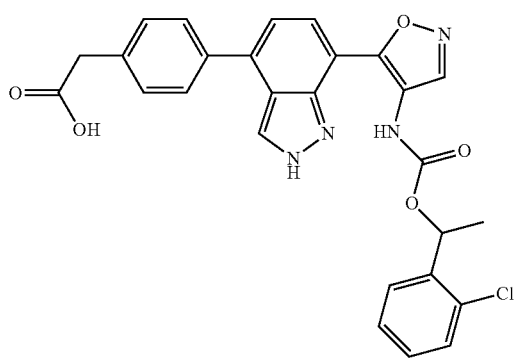 [SMILES: CC(OC(=O)Nc1cnoc1-c1ccc(-c2ccc(CC(=O)O)cc2)c2c[nH]nc12)c1ccccc1Cl]
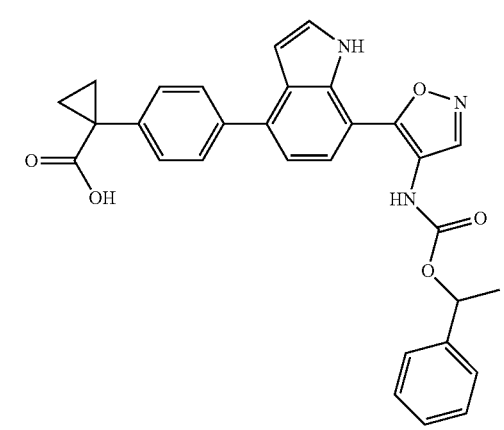 [SMILES: CC(OC(=O)Nc1cnoc1-c1ccc(-c2ccc(C3(C(=O)O)CC3)cc2)c2cc[nH]c12)c1ccccc1]

| 243 | 244 |
|---|---|
| TABLE 1-continued | TABLE 1-continued |
| 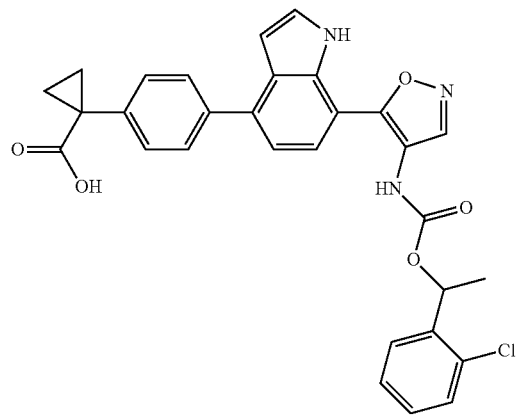 [SMILES: CC(OC(=O)Nc1cnoc1-c1ccc(-c2ccc(C3(C(=O)O)CC3)cc2)c2cc[nH]c12)c1ccccc1Cl] | 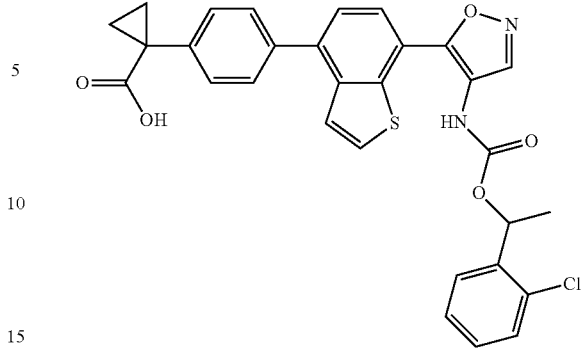 |
| 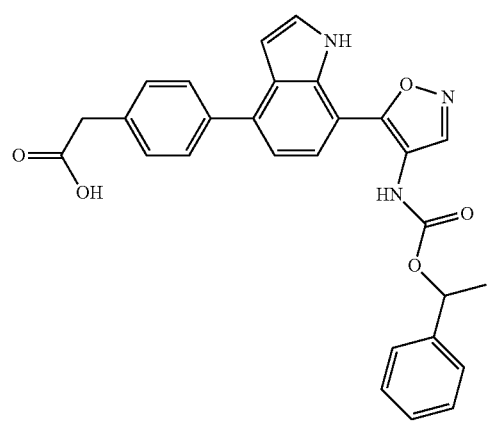 [SMILES: CC(OC(=O)Nc1cnoc1-c1ccc(-c2ccc(CC(=O)O)cc2)c2cc[nH]c12)c1ccccc1] | 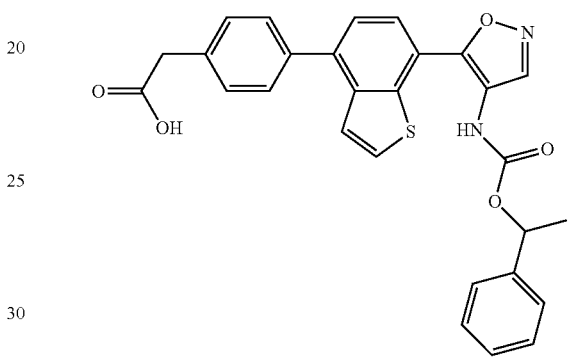 |
| 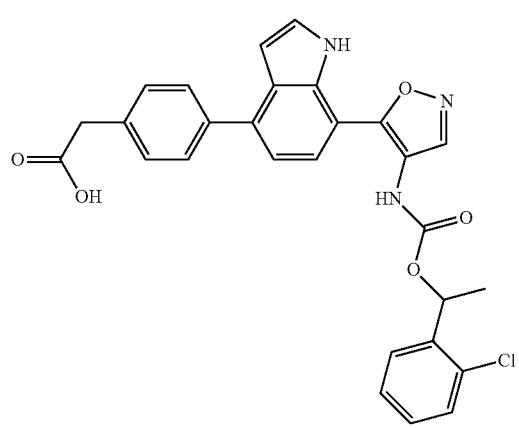 [SMILES: CC(OC(=O)Nc1cnoc1-c1ccc(-c2ccc(CC(=O)O)cc2)c2cc[nH]c12)c1ccccc1Cl] | 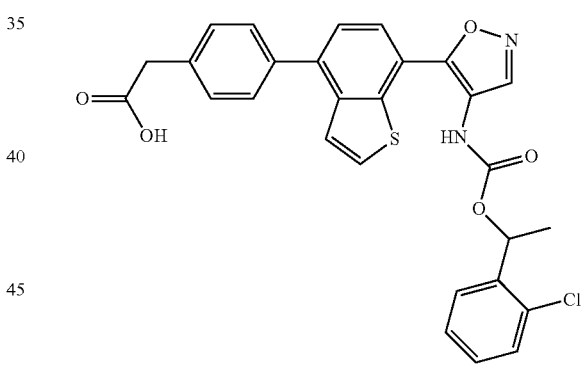 |
| 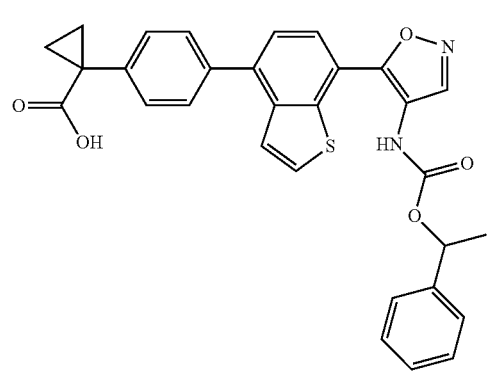 | 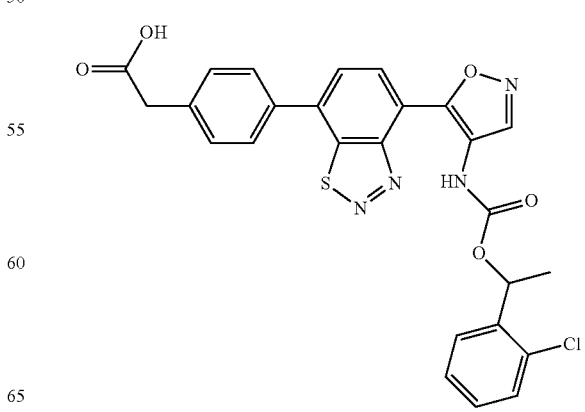 |

245
TABLE 1-continued
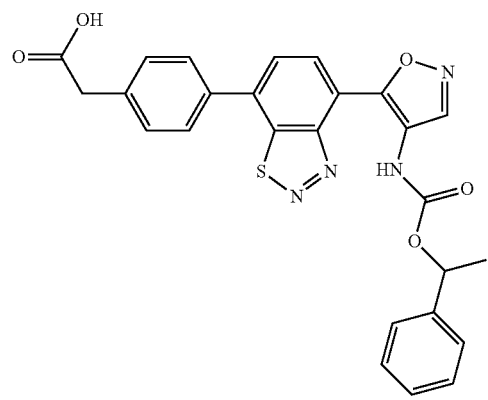 [SMILES: CC(OC(=O)Nc1cnoc1-c1ccc(-c2ccc(CC(=O)O)cc2)c2snnc12)c1ccccc1]
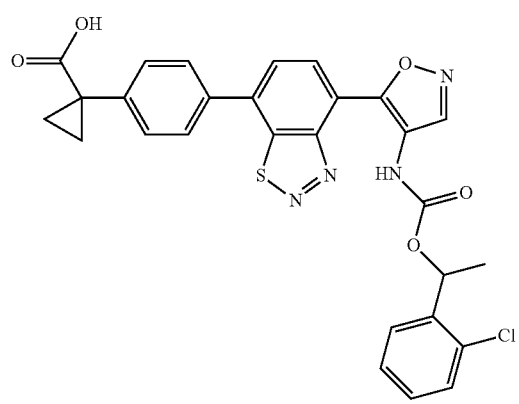 [SMILES: CC(OC(=O)Nc1cnoc1-c1ccc(-c2ccc(C3(C(=O)O)CC3)cc2)c2snnc12)c1ccccc1Cl]
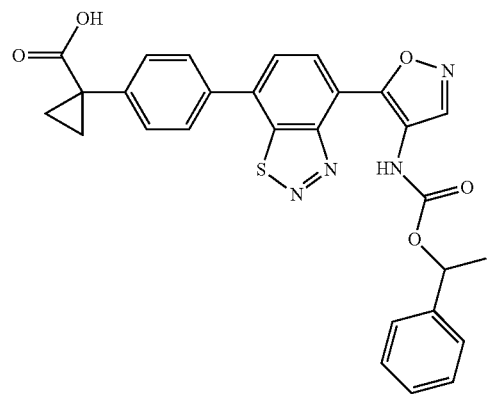 [SMILES: CC(OC(=O)Nc1cnoc1-c1ccc(-c2ccc(C3(C(=O)O)CC3)cc2)c2snnc12)c1ccccc1]
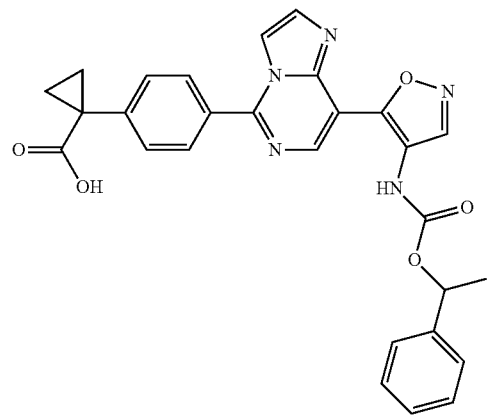 [SMILES: CC(OC(=O)Nc1cnoc1-c1cnc(-c2ccc(C3(C(=O)O)CC3)cc2)n2ccnc12)c1ccccc1]
246
TABLE 1-continued
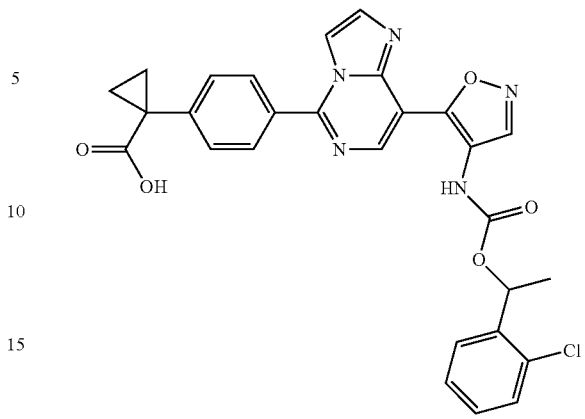
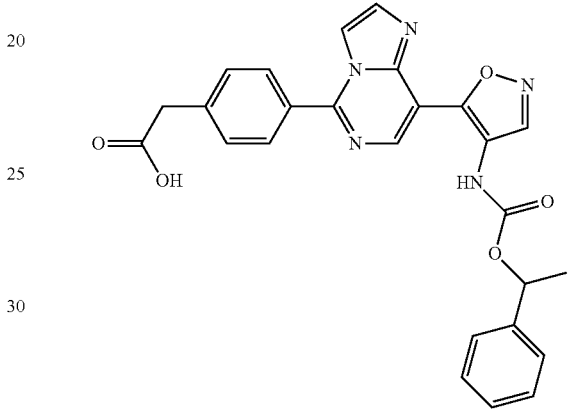
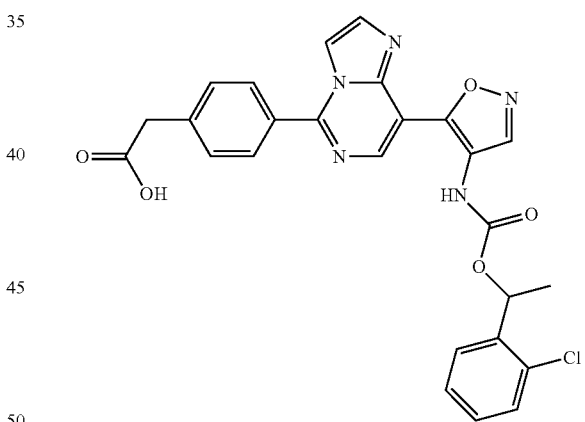
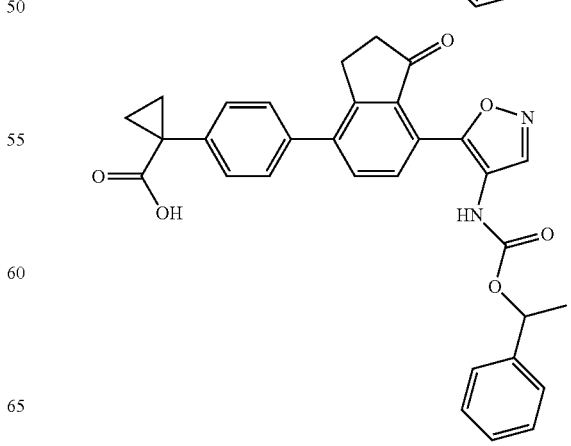

TABLE 1-continued
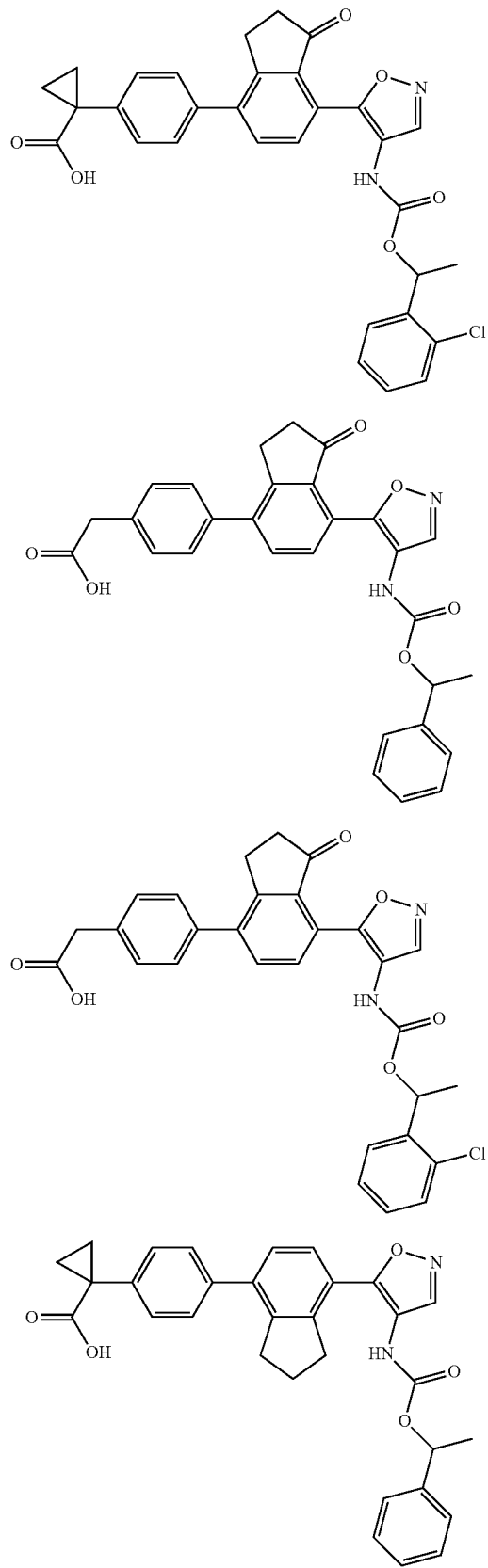
TABLE 1-continued
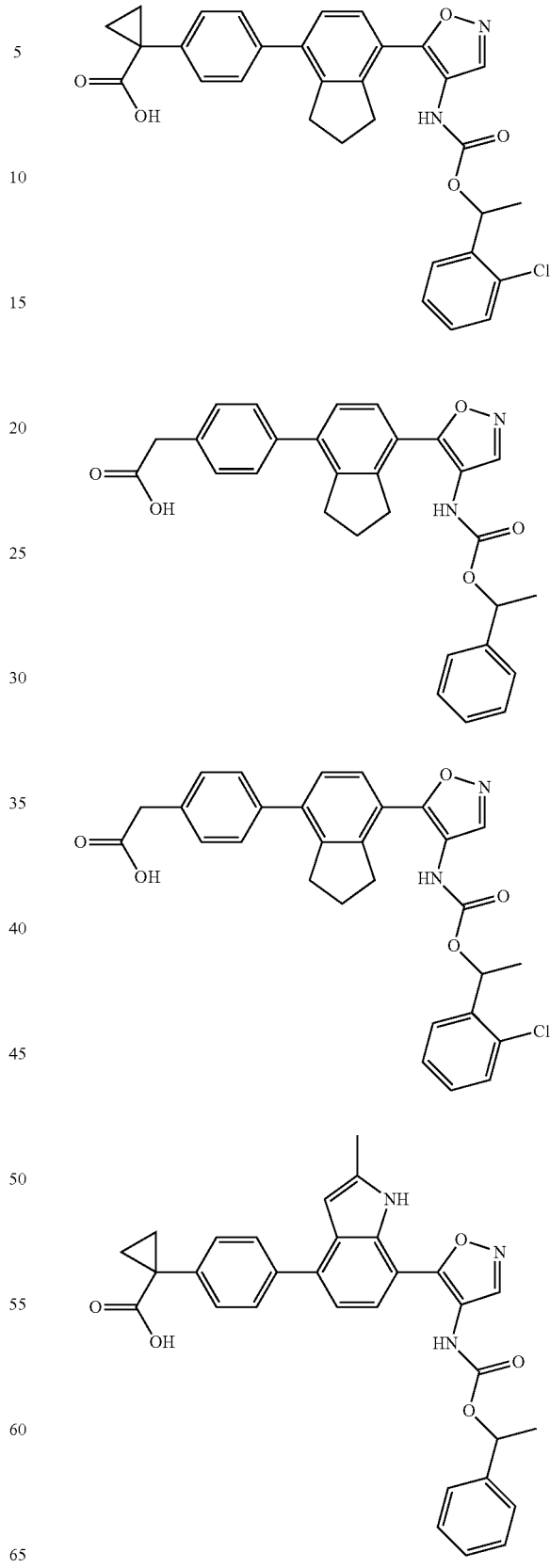

| 249 | 250 |
|---|---|
| TABLE 1-continued | TABLE 1-continued |
| 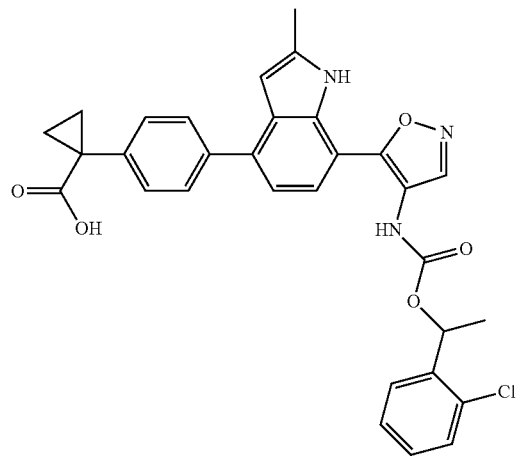 [SMILES: Cc1cc2c(-c3ccc(C4(C(=O)O)CC4)cc3)ccc(-c3oncc3NC(=O)OC(C)c3ccccc3Cl)c2[nH]1] | 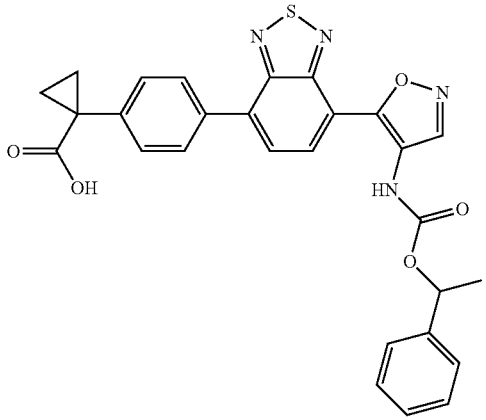 |
| 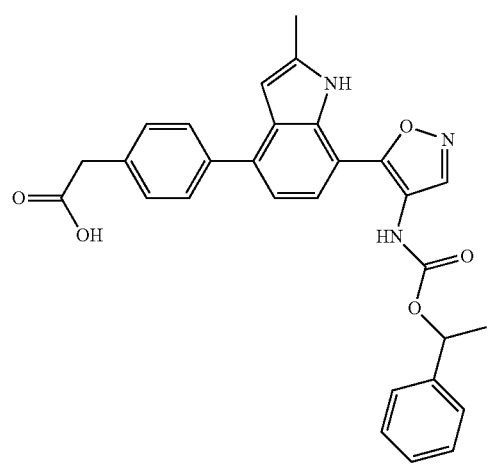 [SMILES: Cc1cc2c(-c3ccc(CC(=O)O)cc3)ccc(-c3oncc3NC(=O)OC(C)c3ccccc3)c2[nH]1] | 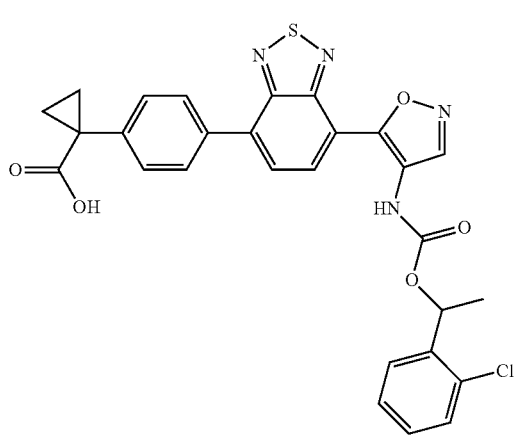 |
| 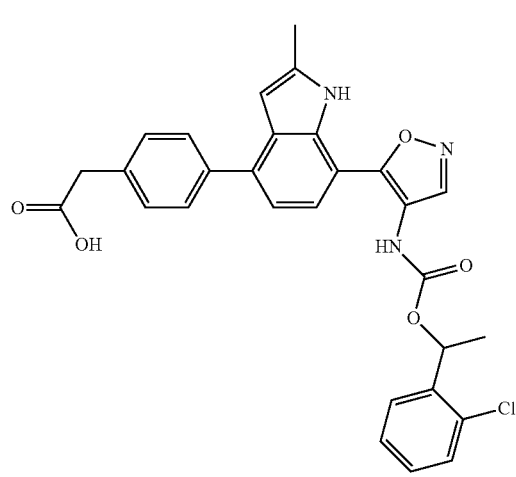 [SMILES: Cc1cc2c(-c3ccc(CC(=O)O)cc3)ccc(-c3oncc3NC(=O)OC(C)c3ccccc3Cl)c2[nH]1] | 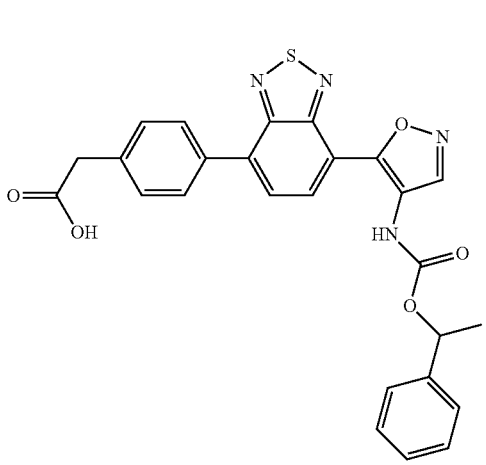 [SMILES: CC(OC(=O)Nc1cnoc1-c1ccc(-c2ccc(CC(=O)O)cc2)c2nsnc12)c1ccccc1] |

| 251 | 252 |
|---|---|
| TABLE 1-continued | TABLE 1-continued |
| 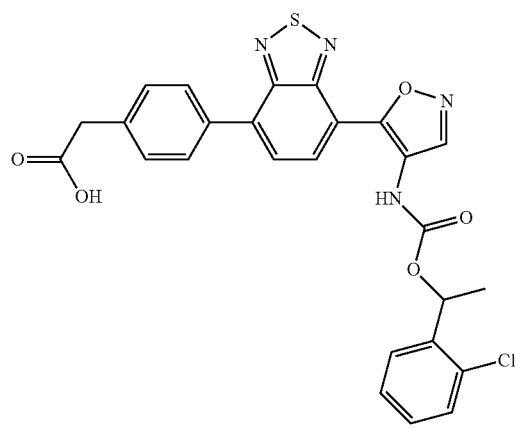 [SMILES: CC(OC(=O)Nc1cnoc1-c1ccc(-c2ccc(CC(=O)O)cc2)c2nsnc12)c1ccccc1Cl] | 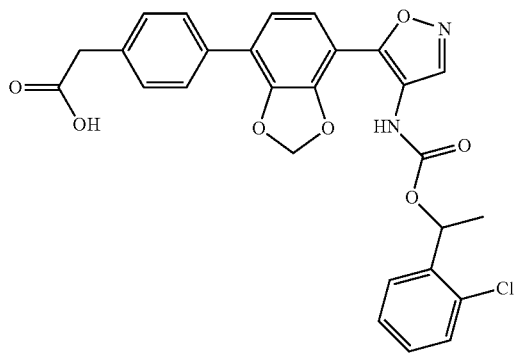 |
| 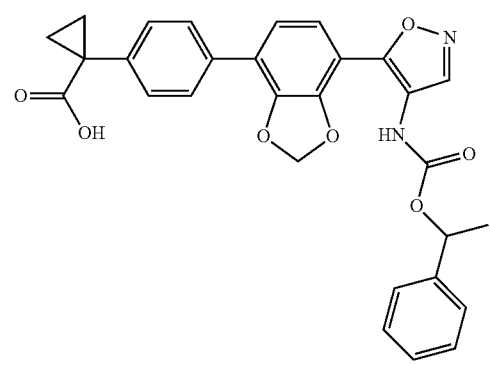 | 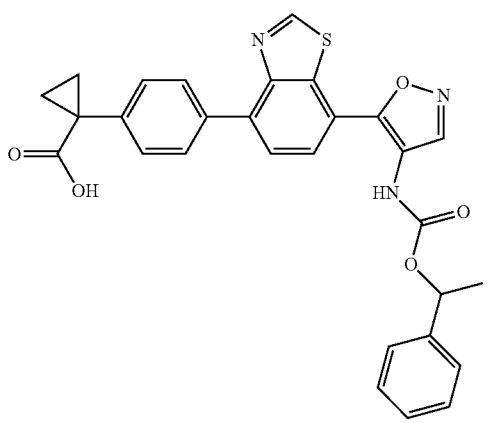 |
| 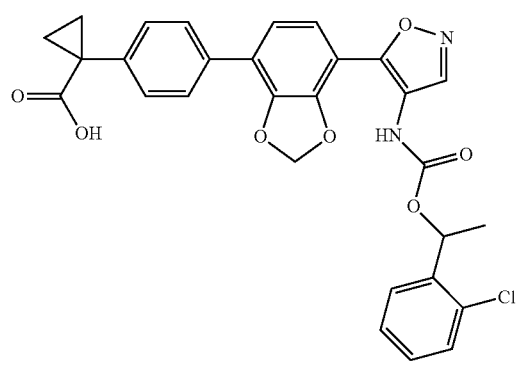 | 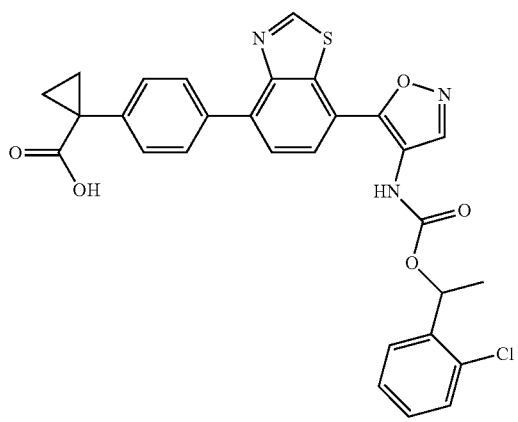 |
| 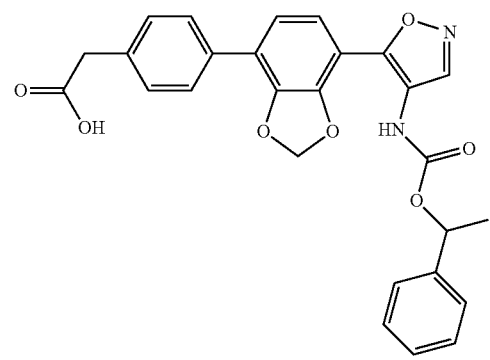 | 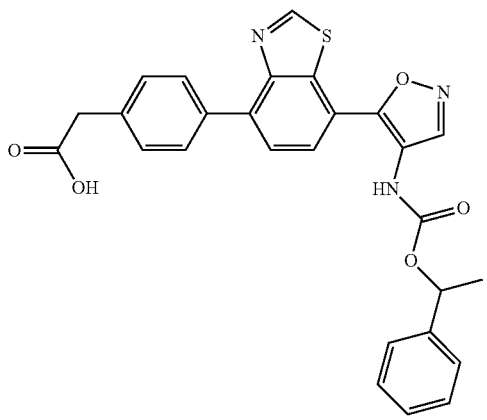 |

253
TABLE 1-continued
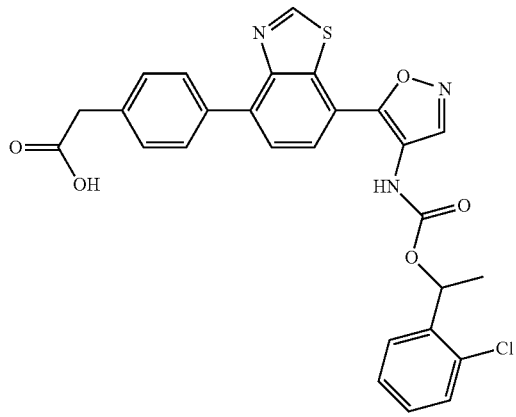
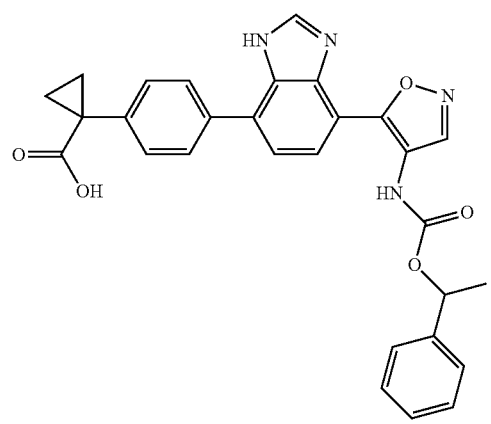 [SMILES: CC(OC(=O)Nc1cnoc1-c1ccc(-c2ccc(C3(C(=O)O)CC3)cc2)c2[nH]cnc12)c1ccccc1]
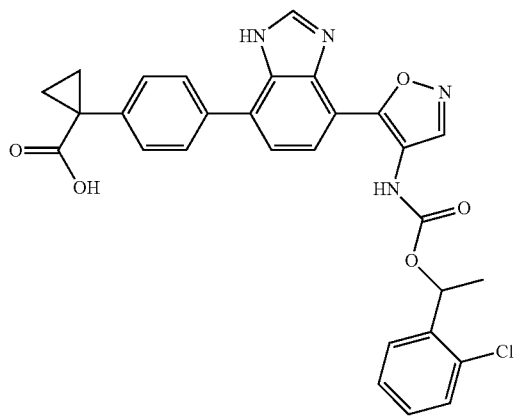 [SMILES: CC(OC(=O)Nc1cnoc1-c1ccc(-c2ccc(C3(C(=O)O)CC3)cc2)c2[nH]cnc12)c1ccccc1Cl]
254
TABLE 1-continued
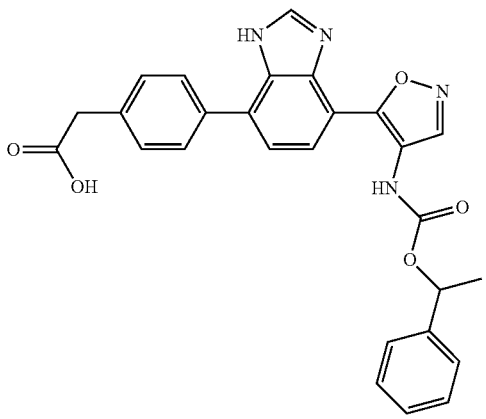
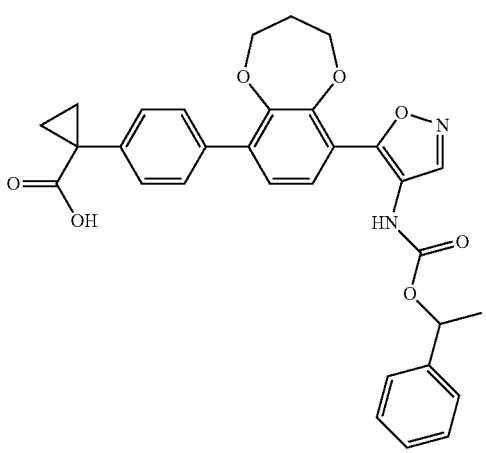

TABLE 1-continued
255
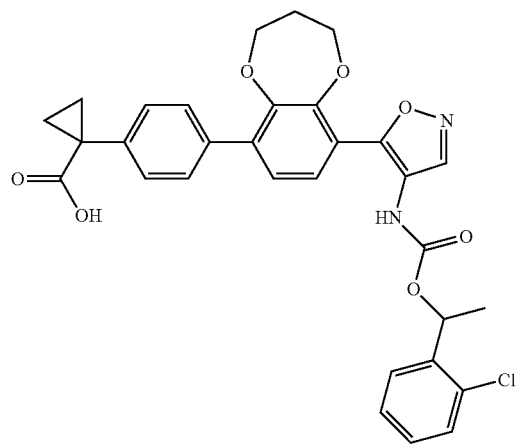 [SMILES: CC(OC(=O)Nc1cnoc1-c1ccc(-c2ccc(C3(C(=O)O)CC3)cc2)c2c1OCCCO2)c1ccccc1Cl]
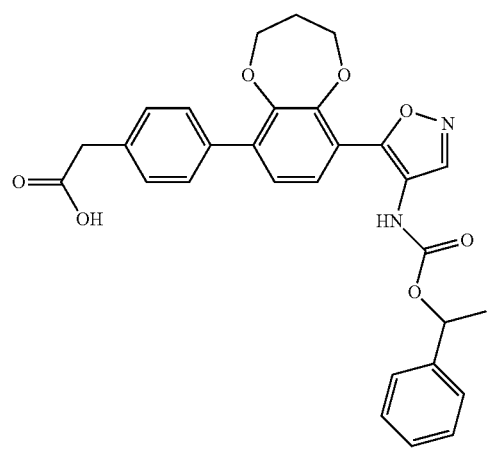
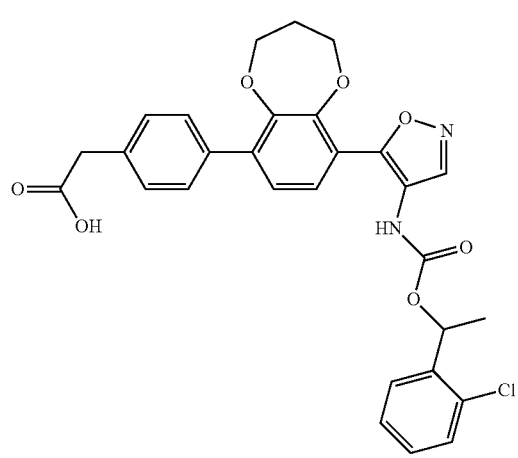
TABLE 1-continued
256
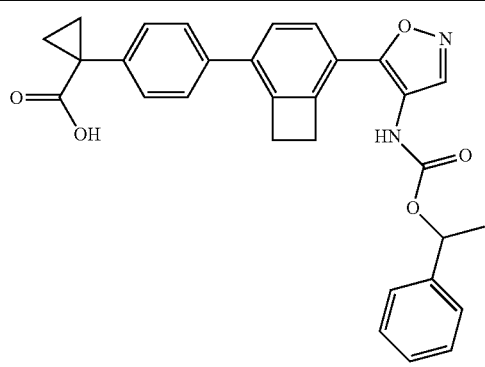
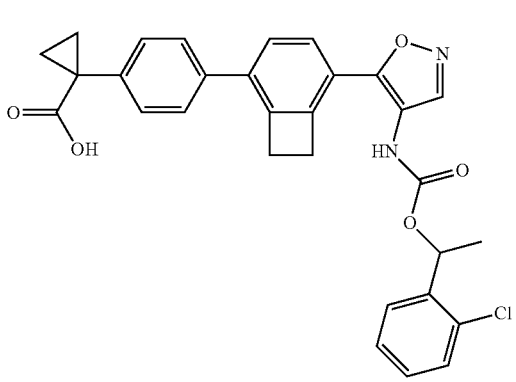 [SMILES: CC(OC(=O)Nc1cnoc1-c1ccc(-c2ccc(C3(C(=O)O)CC3)cc2)c2c1CC2)c1ccccc1Cl]
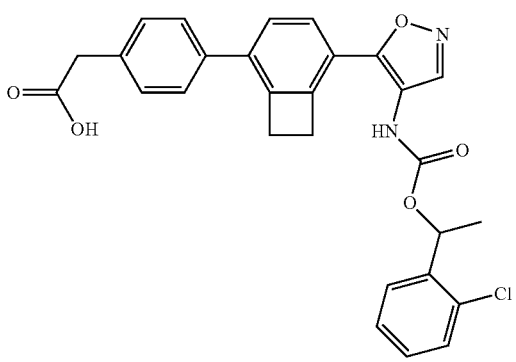 [SMILES: CC(OC(=O)Nc1cnoc1-c1ccc(-c2ccc(CC(=O)O)cc2)c2c1CC2)c1ccccc1Cl]

257
TABLE 1-continued
258
TABLE 1-continued
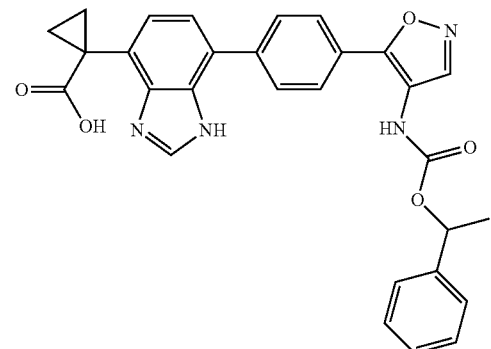
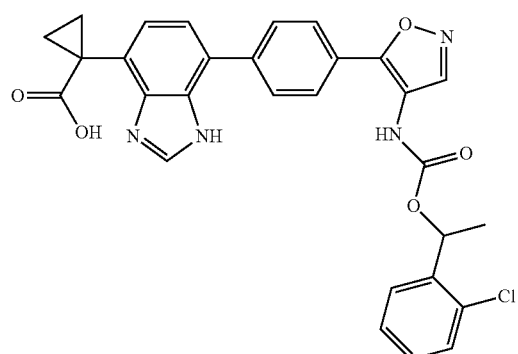
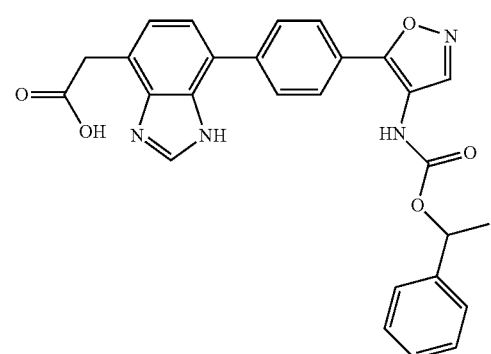
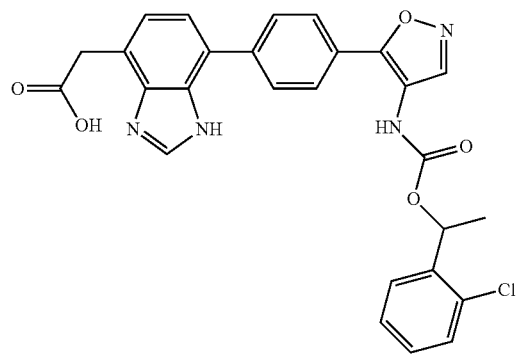 [SMILES: CC(OC(=O)Nc1cnoc1-c1ccc(-c2ccc(CC(=O)O)c3nc[nH]c23)cc1)c1ccccc1Cl]
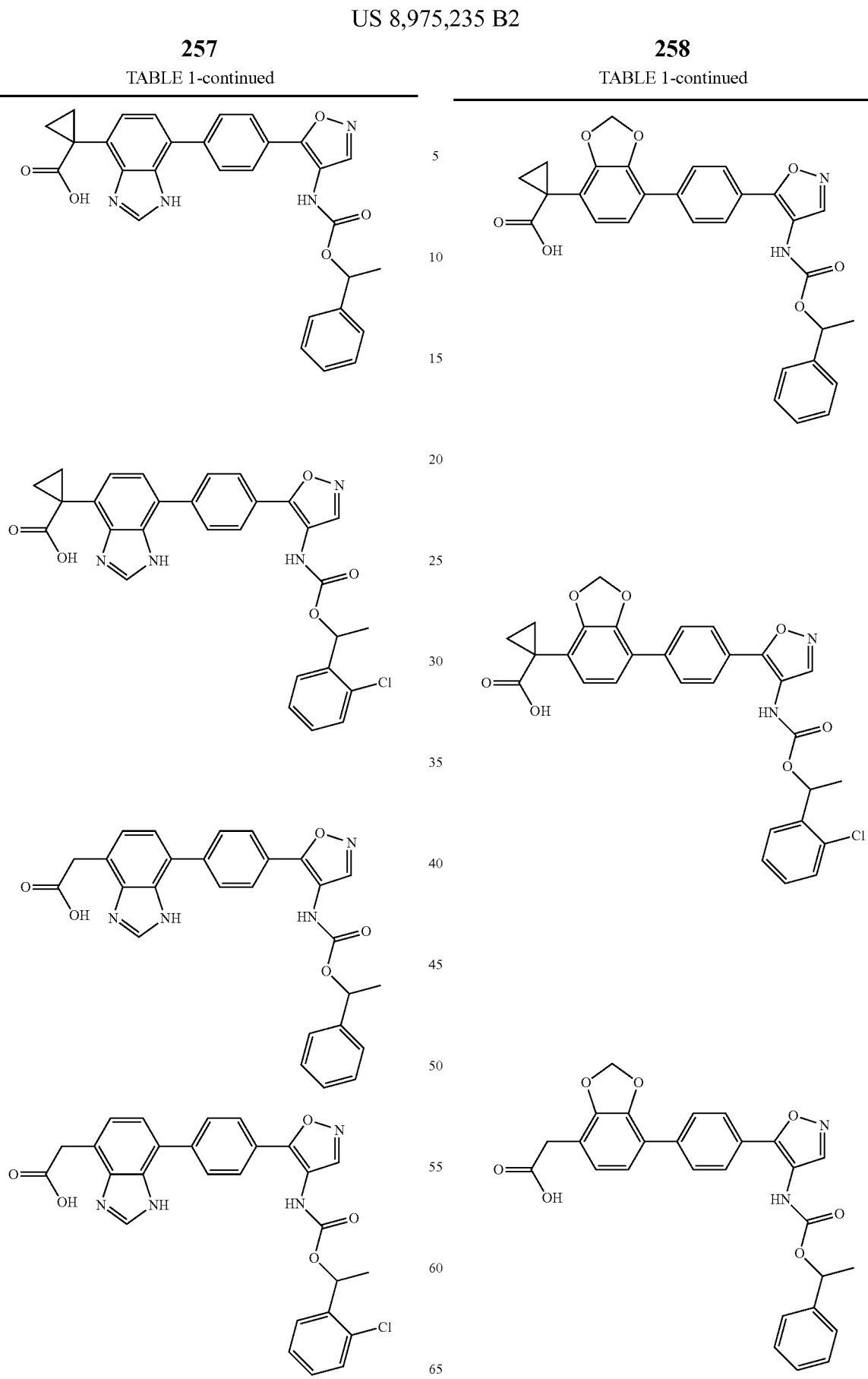

| 259 | 260 |
|---|---|
| TABLE 1-continued | TABLE 1-continued |
| 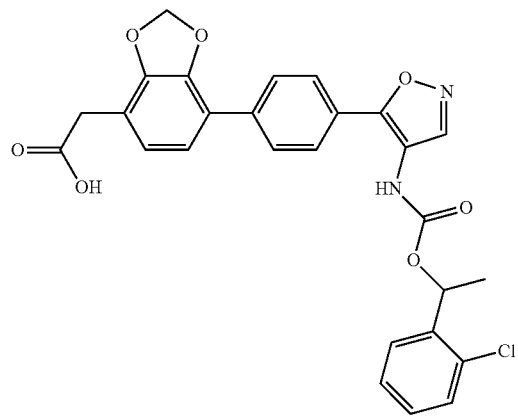 | 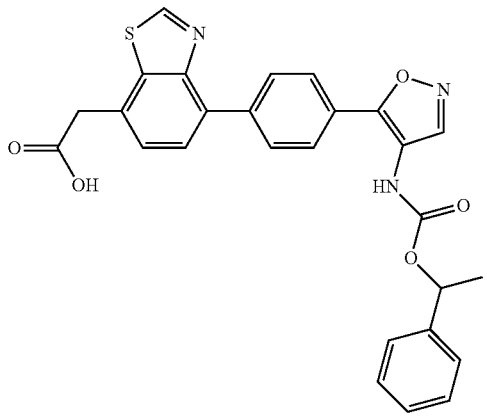 |
| 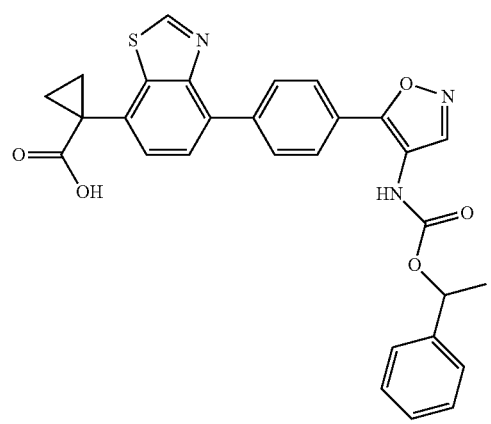 | 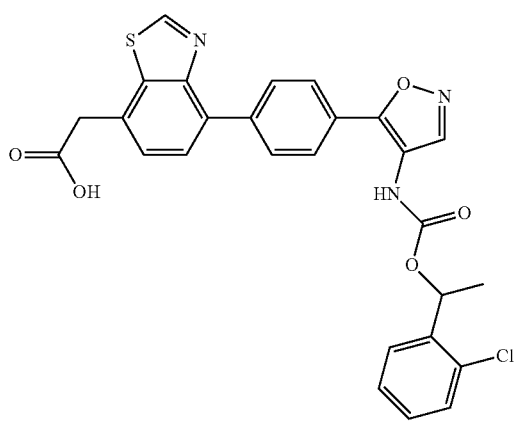 |
| 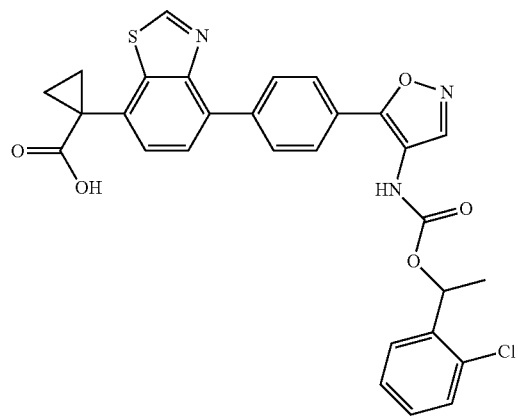 | 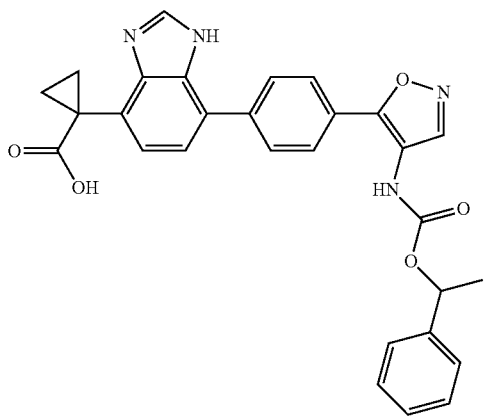 |

261
TABLE 1-continued
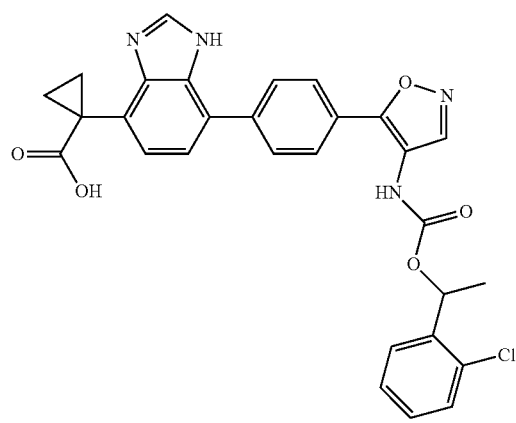
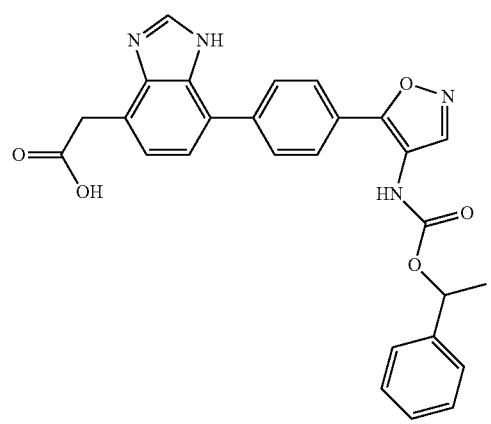
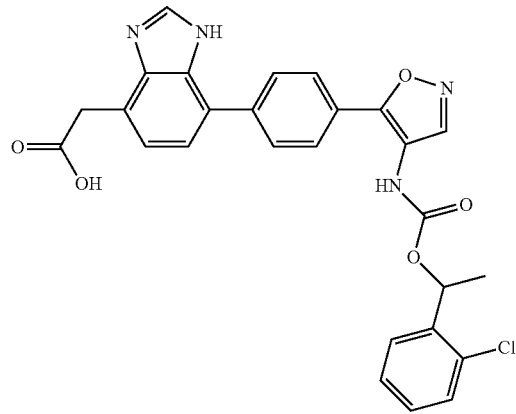
262
TABLE 1-continued
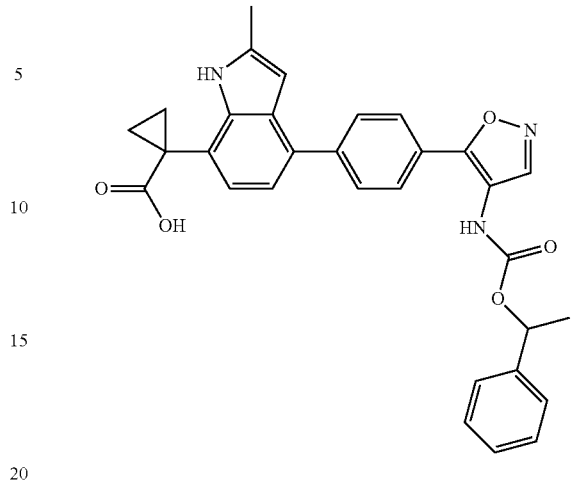
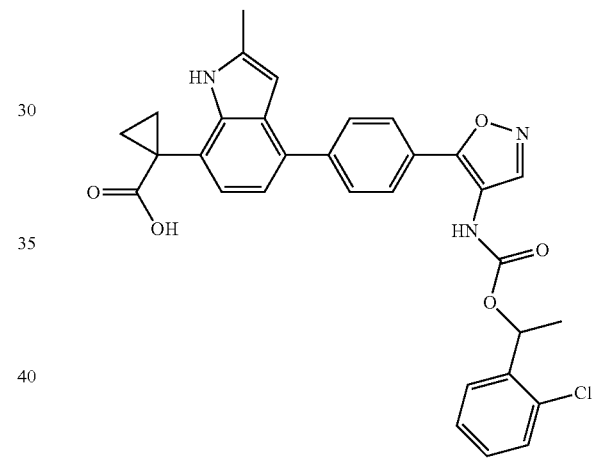

TABLE 1-continued
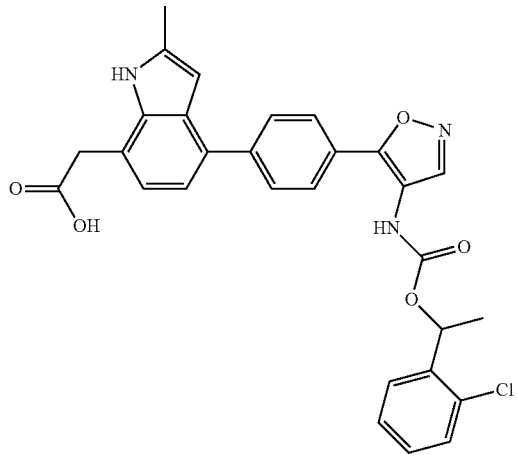 [SMILES: Cc1cc2c(-c3ccc(-c4oncc4NC(=O)OC(C)c4ccccc4Cl)cc3)ccc(CC(=O)O)c2[nH]1]
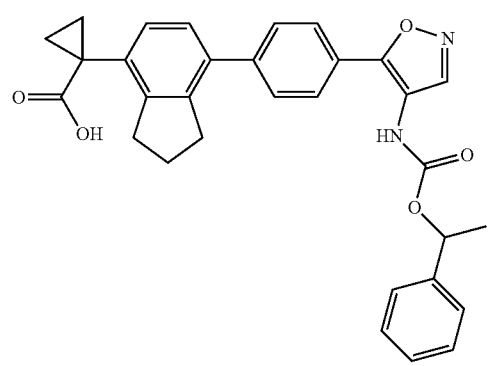
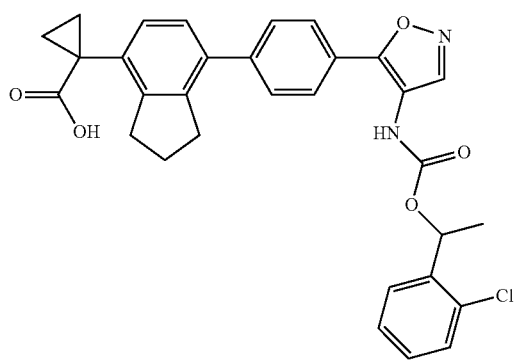
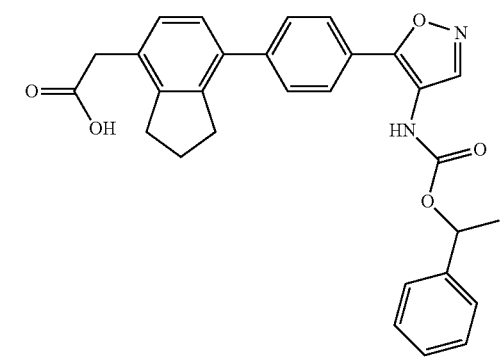 [SMILES: CC(OC(=O)Nc1cnoc1-c1ccc(-c2ccc(CC(=O)O)c3c2CCC3)cc1)c1ccccc1]
TABLE 1-continued
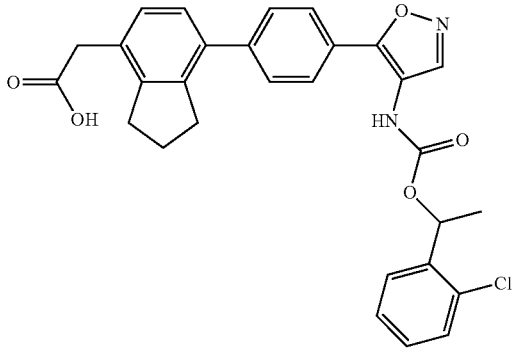 [SMILES: CC(OC(=O)Nc1cnoc1-c1ccc(-c2ccc(CC(=O)O)c3c2CCC3)cc1)c1ccccc1Cl]
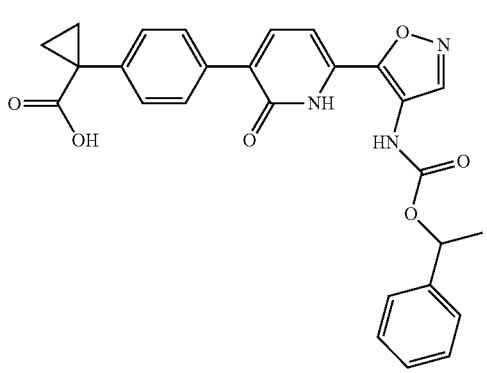 [SMILES: CC(OC(=O)Nc1cnoc1-c1ccc(-c2ccc(C3(C(=O)O)CC3)cc2)c(=O)[nH]1)c1ccccc1]
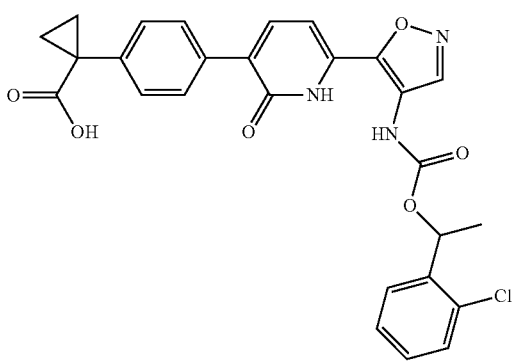 [SMILES: CC(OC(=O)Nc1cnoc1-c1ccc(-c2ccc(C3(C(=O)O)CC3)cc2)c(=O)[nH]1)c1ccccc1Cl]
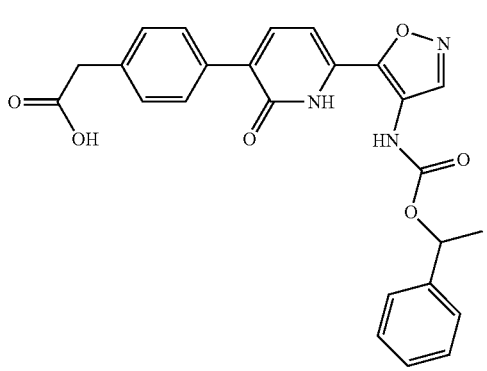 [SMILES: CC(OC(=O)Nc1cnoc1-c1ccc(-c2ccc(CC(=O)O)cc2)c(=O)[nH]1)c1ccccc1]

TABLE 1-continued
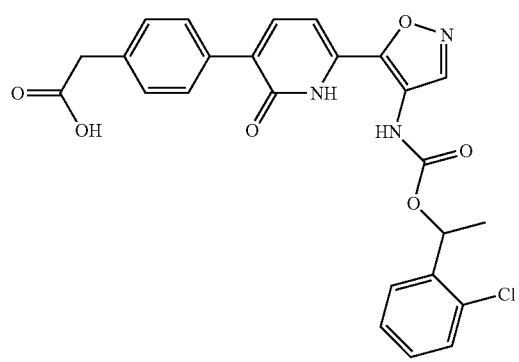 [SMILES: CC(OC(=O)Nc1cnoc1-c1ccc(-c2ccc(CC(=O)O)cc2)c(=O)[nH]1)c1ccccc1Cl]
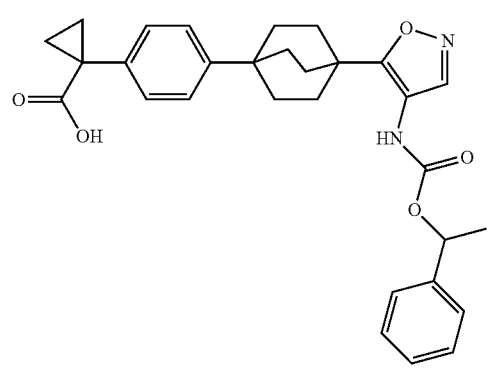 [SMILES: CC(OC(=O)Nc1cnoc1C12CCC(c3ccc(C4(C(=O)O)CC4)cc3)(CC1)CC2)c1ccccc1]
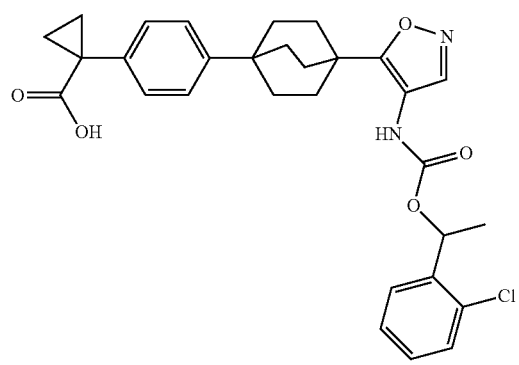 [SMILES: CC(OC(=O)Nc1cnoc1C12CCC(c3ccc(C4(C(=O)O)CC4)cc3)(CC1)CC2)c1ccccc1Cl]
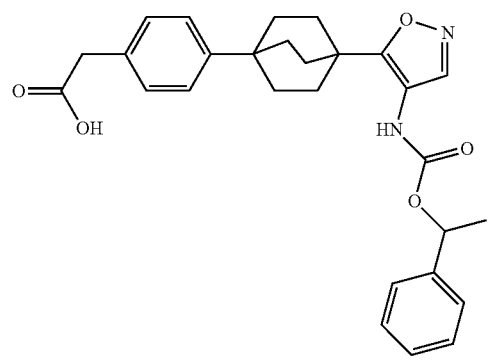 [SMILES: CC(OC(=O)Nc1cnoc1C12CCC(c3ccc(CC(=O)O)cc3)(CC1)CC2)c1ccccc1]
TABLE 1-continued
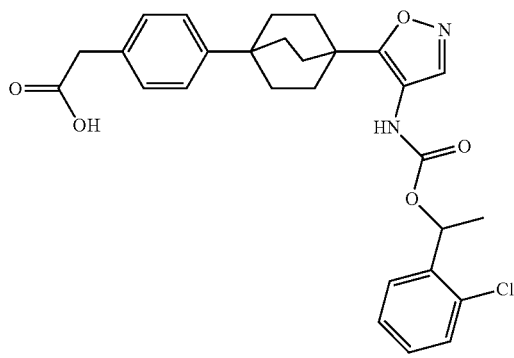 [SMILES: CC(OC(=O)Nc1cnoc1C12CCC(c3ccc(CC(=O)O)cc3)(CC1)CC2)c1ccccc1Cl]
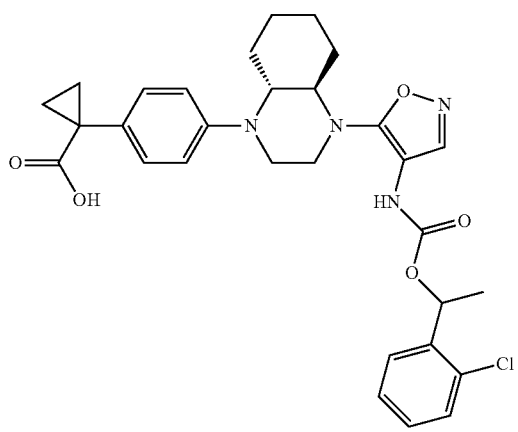 [SMILES: CC(OC(=O)Nc1cnoc1N1CCN(c2ccc(C3(C(=O)O)CC3)cc2)[C@@H]2CCCC[C@H]21)c1ccccc1Cl]
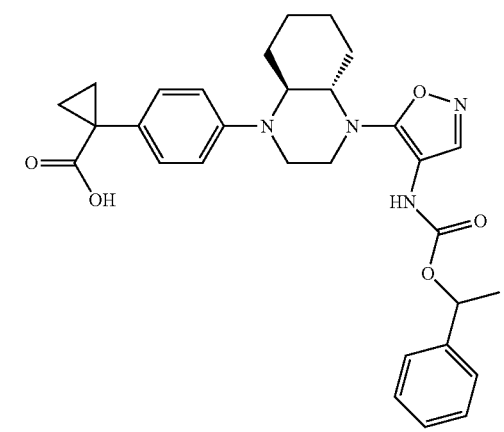 [SMILES: CC(OC(=O)Nc1cnoc1N1CCN(c2ccc(C3(C(=O)O)CC3)cc2)[C@H]2CCCC[C@@H]21)c1ccccc1]
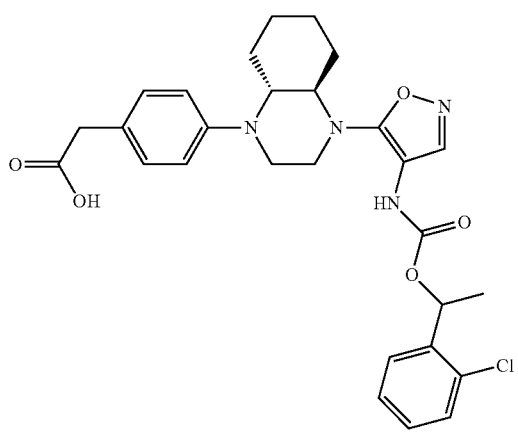 [SMILES: CC(OC(=O)Nc1cnoc1N1CCN(c2ccc(CC(=O)O)cc2)[C@@H]2CCCC[C@H]21)c1ccccc1Cl]

267
TABLE 1-continued
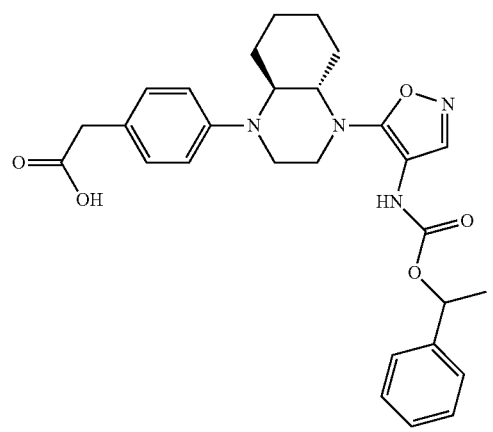 [SMILES: CC(OC(=O)Nc1cnoc1N1CCN(c2ccc(CC(=O)O)cc2)[C@H]2CCCC[C@@H]21)c1ccccc1]
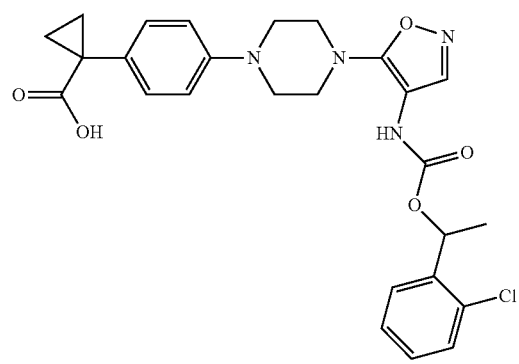 [SMILES: CC(OC(=O)Nc1cnoc1N1CCN(c2ccc(C3(C(=O)O)CC3)cc2)CC1)c1ccccc1Cl]
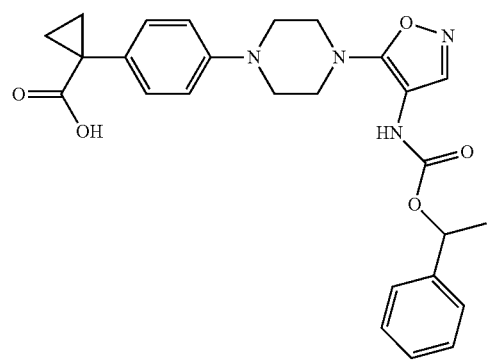 [SMILES: CC(OC(=O)Nc1cnoc1N1CCN(c2ccc(C3(C(=O)O)CC3)cc2)CC1)c1ccccc1]
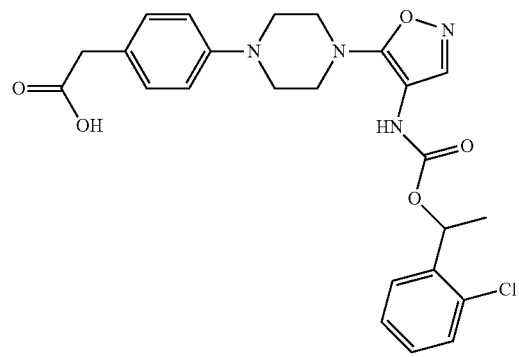 [SMILES: CC(OC(=O)Nc1cnoc1N1CCN(c2ccc(CC(=O)O)cc2)CC1)c1ccccc1Cl]
268
TABLE 1-continued
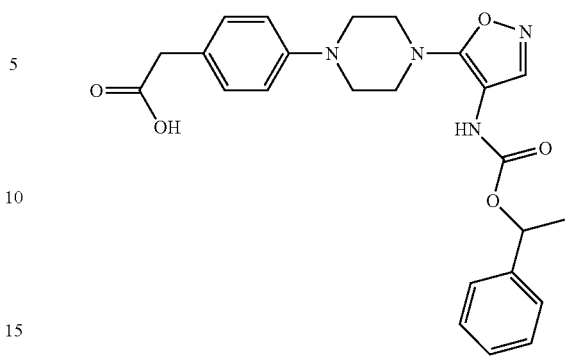
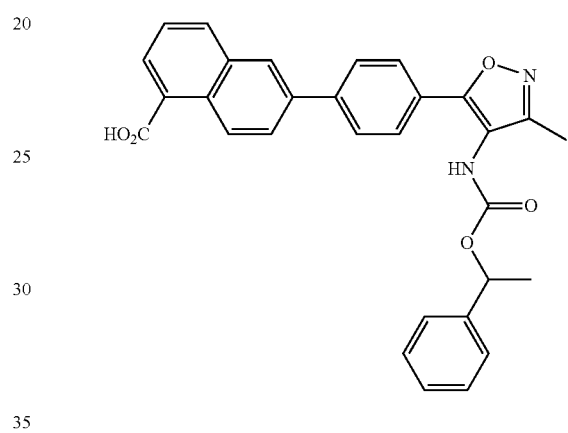
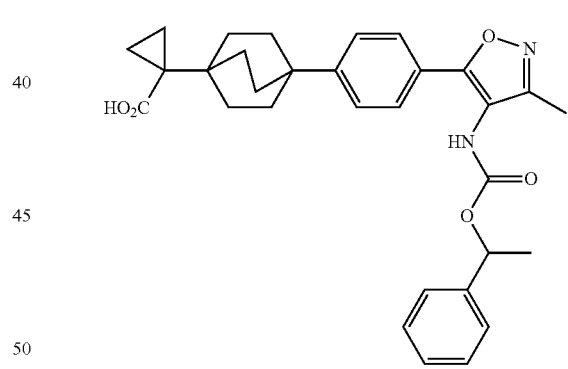
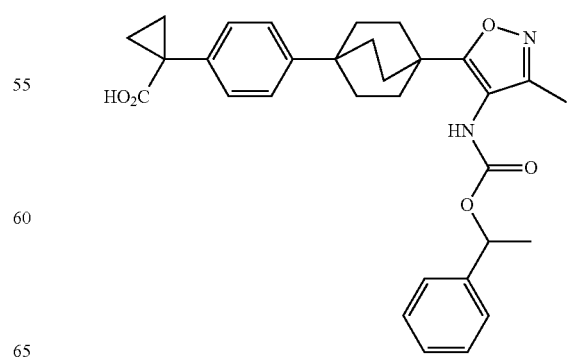

TABLE 1-continued
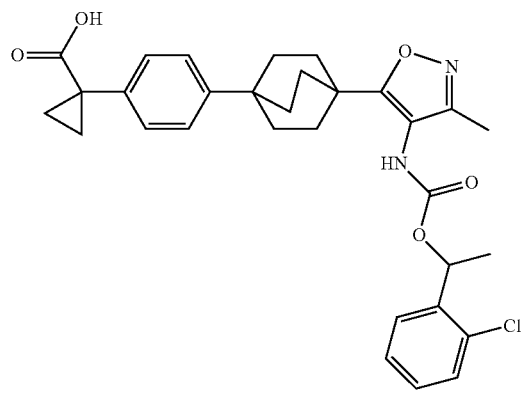 [SMILES: Cc1noc(C23CCC(c4ccc(C5(C(=O)O)CC5)cc4)(CC2)CC3)c1NC(=O)OC(C)c1ccccc1Cl]
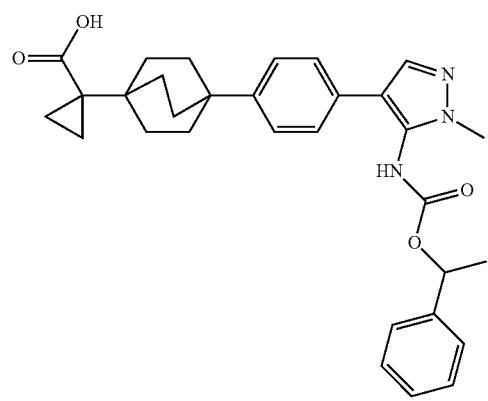 [SMILES: CC(OC(=O)Nc1c(-c2ccc(C34CCC(C5(C(=O)O)CC5)(CC3)CC4)cc2)cnn1C)c1ccccc1]
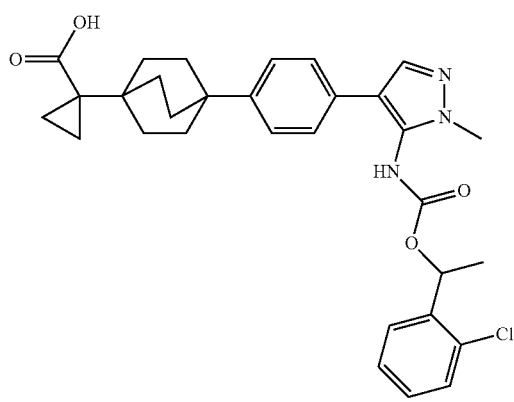 [SMILES: CC(OC(=O)Nc1c(-c2ccc(C34CCC(C5(C(=O)O)CC5)(CC3)CC4)cc2)cnn1C)c1ccccc1Cl]
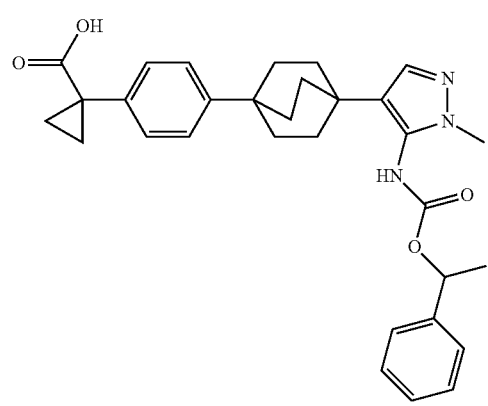
TABLE 1-continued
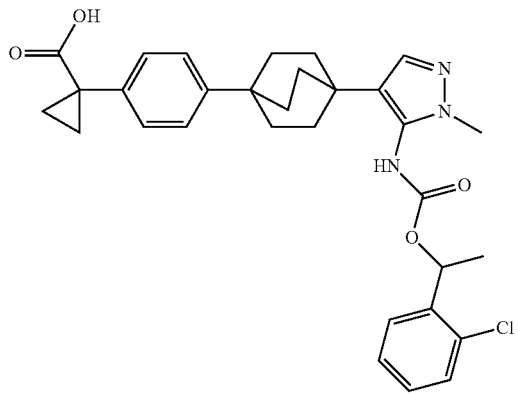 [SMILES: CC(OC(=O)Nc1c(C23CCC(c4ccc(C5(C(=O)O)CC5)cc4)(CC2)CC3)cnn1C)c1ccccc1Cl]
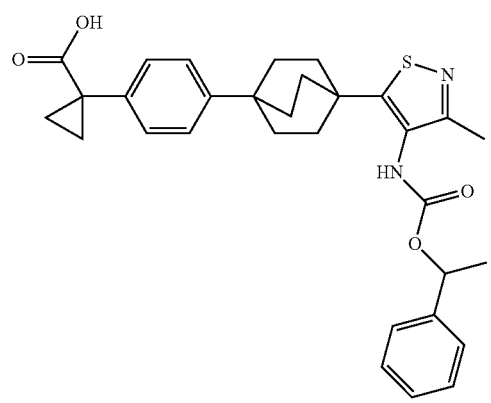 [SMILES: Cc1nsc(C23CCC(c4ccc(C5(C(=O)O)CC5)cc4)(CC2)CC3)c1NC(=O)OC(C)c1ccccc1]
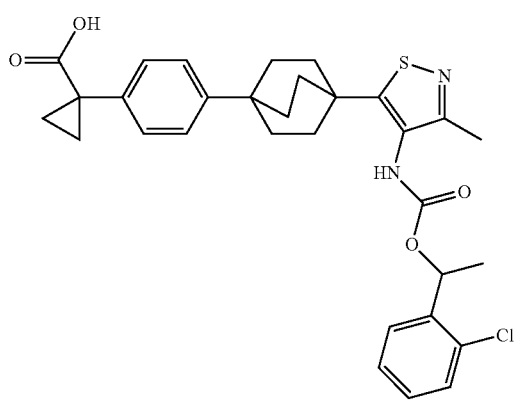 [SMILES: Cc1nsc(C23CCC(c4ccc(C5(C(=O)O)CC5)cc4)(CC2)CC3)c1NC(=O)OC(C)c1ccccc1Cl]
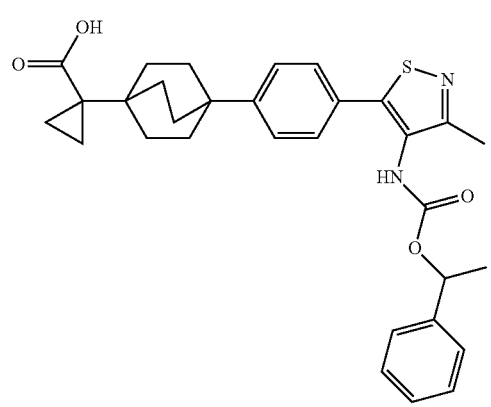 [SMILES: Cc1nsc(-c2ccc(C34CCC(C5(C(=O)O)CC5)(CC3)CC4)cc2)c1NC(=O)OC(C)c1ccccc1]

TABLE 1-continued
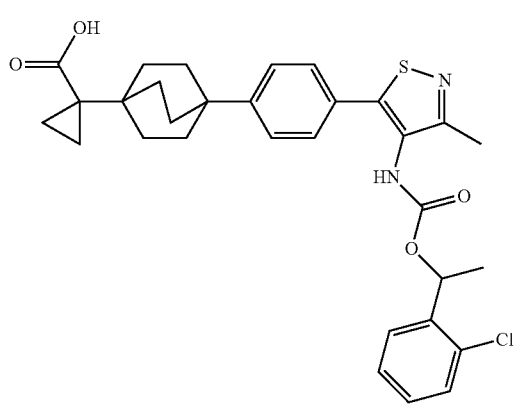 [SMILES: Cc1nsc(-c2ccc(C34CCC(C5(C(=O)O)CC5)(CC3)CC4)cc2)c1NC(=O)OC(C)c1ccccc1Cl]
In some embodiments, compounds of Formula (I) are selected from the following compounds as listed in Table 1A.
TABLE 1A
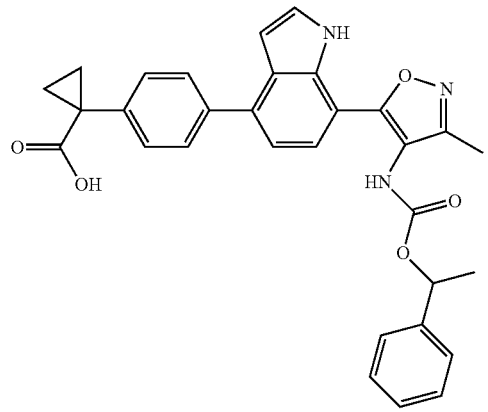 [SMILES: Cc1noc(-c2ccc(-c3ccc(C4(C(=O)O)CC4)cc3)c3cc[nH]c23)c1NC(=O)OC(C)c1ccccc1]
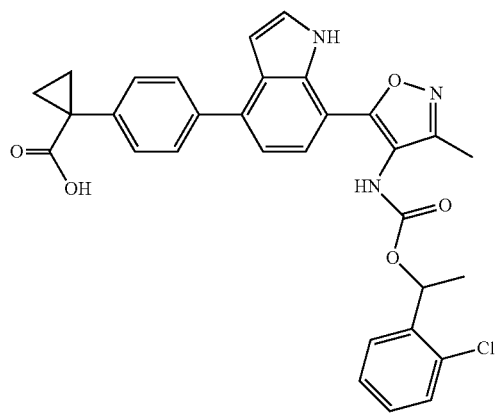 [SMILES: Cc1noc(-c2ccc(-c3ccc(C4(C(=O)O)CC4)cc3)c3cc[nH]c23)c1NC(=O)OC(C)c1ccccc1Cl]
TABLE 1A-continued
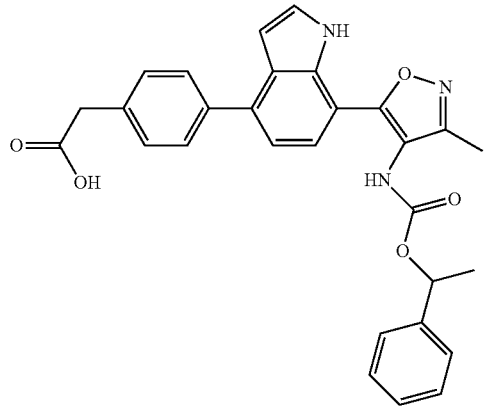 [SMILES: Cc1noc(-c2ccc(-c3ccc(CC(=O)O)cc3)c3cc[nH]c23)c1NC(=O)OC(C)c1ccccc1]
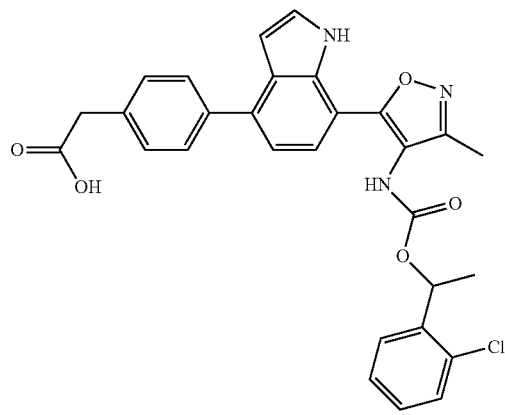 [SMILES: Cc1noc(-c2ccc(-c3ccc(CC(=O)O)cc3)c3cc[nH]c23)c1NC(=O)OC(C)c1ccccc1Cl]
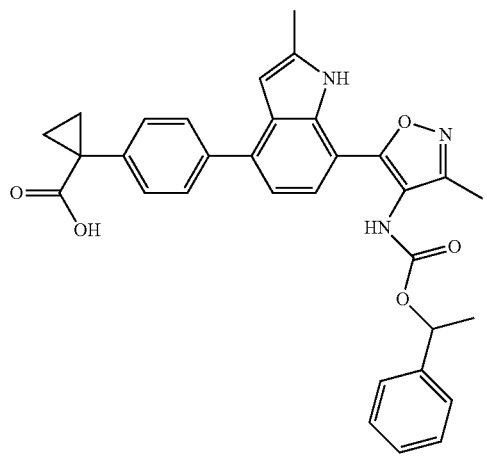 [SMILES: Cc1cc2c(-c3ccc(C4(C(=O)O)CC4)cc3)ccc(-c3onc(C)c3NC(=O)OC(C)c3ccccc3)c2[nH]1]

TABLE 1A-continued
273
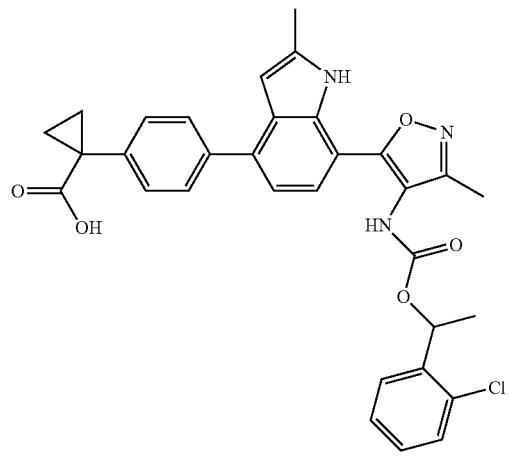 [SMILES: Cc1cc2c(-c3ccc(C4(C(=O)O)CC4)cc3)ccc(-c3onc(C)c3NC(=O)OC(C)c3ccccc3Cl)c2[nH]1]
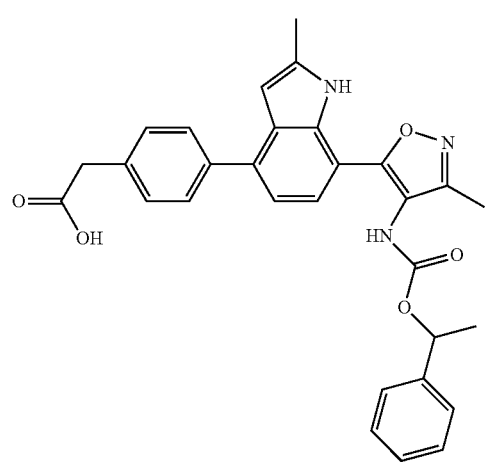 [SMILES: Cc1cc2c(-c3ccc(CC(=O)O)cc3)ccc(-c3onc(C)c3NC(=O)OC(C)c3ccccc3)c2[nH]1]
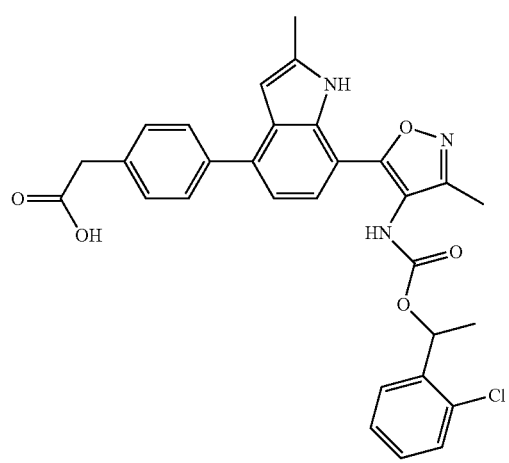 [SMILES: Cc1cc2c(-c3ccc(CC(=O)O)cc3)ccc(-c3onc(C)c3NC(=O)OC(C)c3ccccc3Cl)c2[nH]1]
TABLE 1A-continued
274
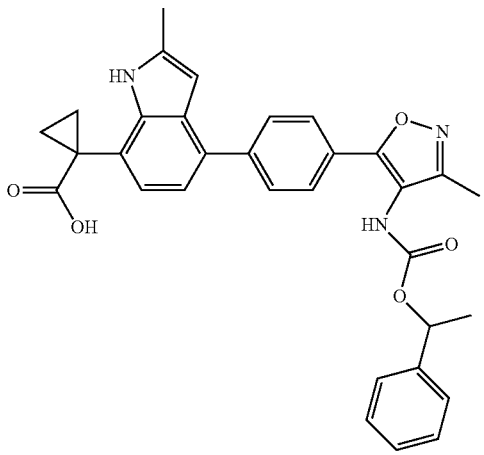 [SMILES: Cc1cc2c(-c3ccc(-c4onc(C)c4NC(=O)OC(C)c4ccccc4)cc3)ccc(C3(C(=O)O)CC3)c2[nH]1]
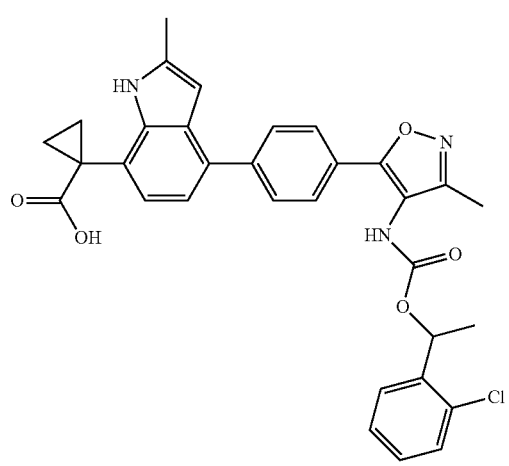 [SMILES: Cc1cc2c(-c3ccc(-c4onc(C)c4NC(=O)OC(C)c4ccccc4Cl)cc3)ccc(C3(C(=O)O)CC3)c2[nH]1]
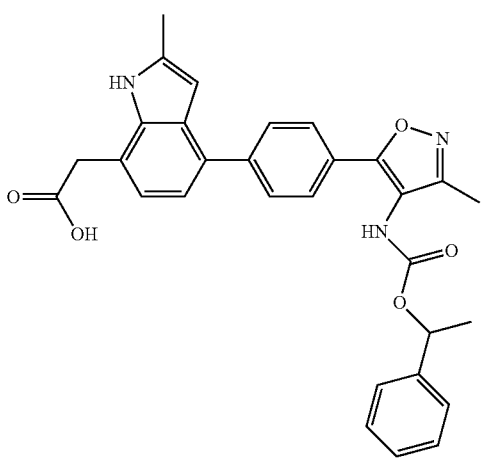 [SMILES: Cc1cc2c(-c3ccc(-c4onc(C)c4NC(=O)OC(C)c4ccccc4)cc3)ccc(CC(=O)O)c2[nH]1]

TABLE 1A-continued
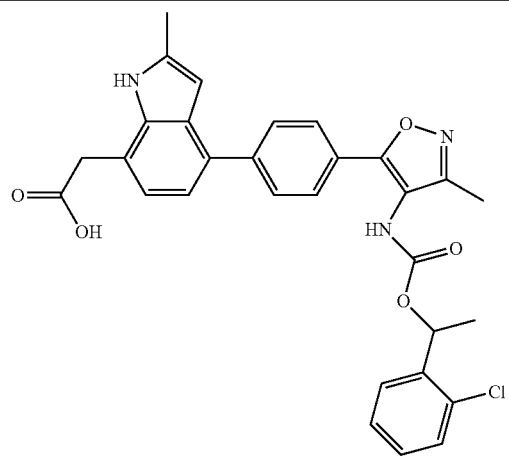
In some embodiments, compounds of Formula (I) are selected from the following compounds as listed in Table 2.
TABLE 2
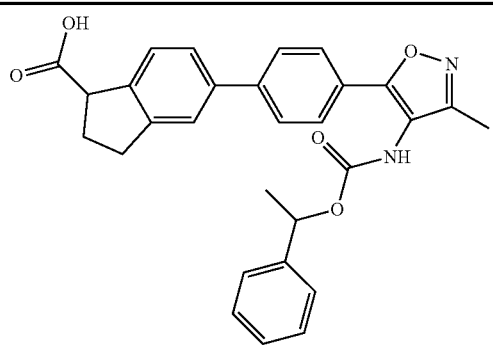
TABLE 2-continued
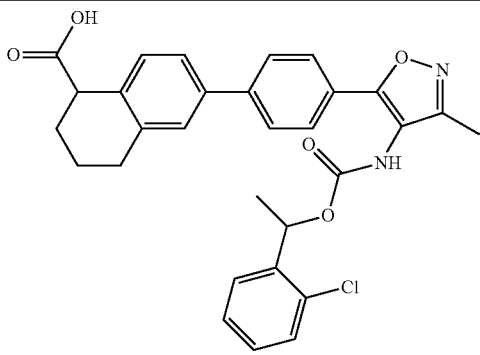
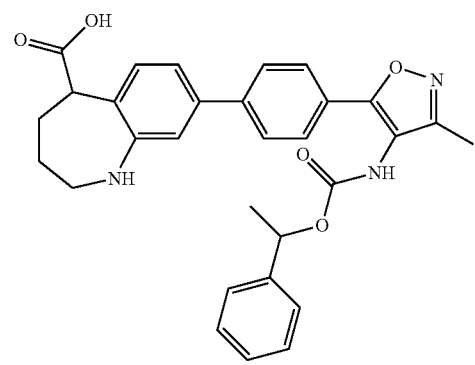 [SMILES: Cc1noc(-c2ccc(-c3ccc4c(c3)NCCCC4C(=O)O)cc2)c1NC(=O)OC(C)c1ccccc1]
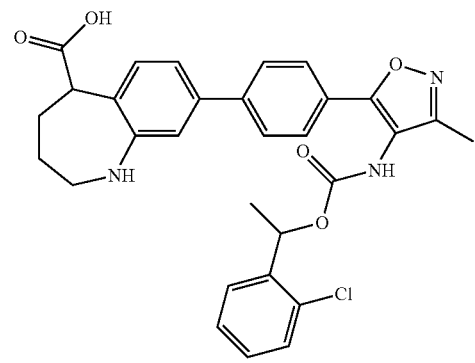 [SMILES: Cc1noc(-c2ccc(-c3ccc4c(c3)NCCCC4C(=O)O)cc2)c1NC(=O)OC(C)c1ccccc1Cl]
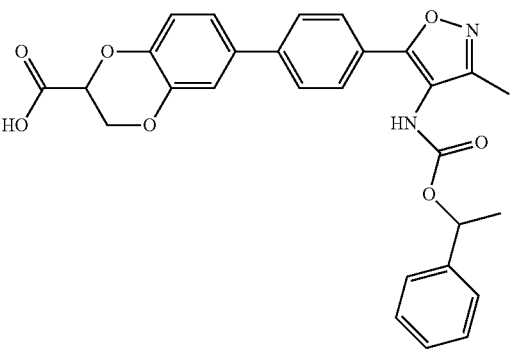 [SMILES: Cc1noc(-c2ccc(-c3ccc4c(c3)OCC(C(=O)O)O4)cc2)c1NC(=O)OC(C)c1ccccc1]

TABLE 2-continued
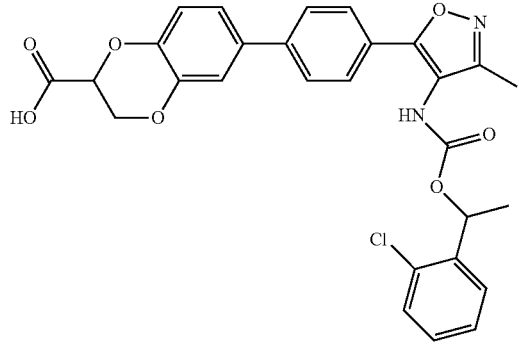 [SMILES: Cc1noc(-c2ccc(-c3ccc4c(c3)OCC(C(=O)O)O4)cc2)c1NC(=O)OC(C)c1ccccc1Cl]
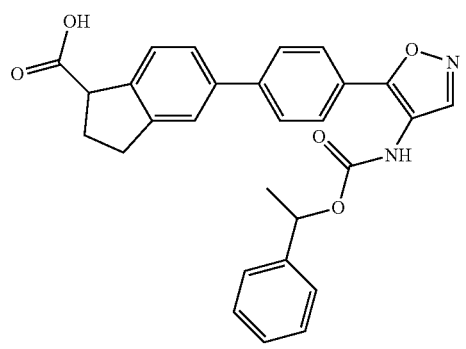 [SMILES: CC(OC(=O)Nc1cnoc1-c1ccc(-c2ccc3c(c2)CCC3C(=O)O)cc1)c1ccccc1]
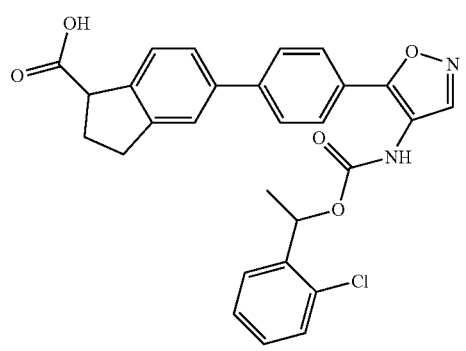 [SMILES: CC(OC(=O)Nc1cnoc1-c1ccc(-c2ccc3c(c2)CCC3C(=O)O)cc1)c1ccccc1Cl]
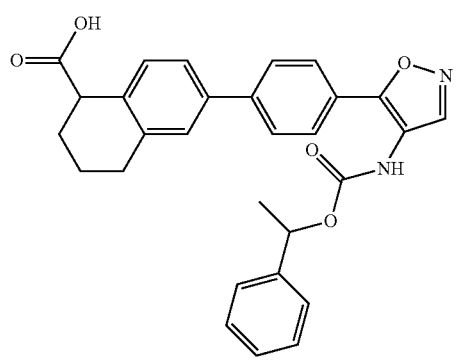 [SMILES: CC(OC(=O)Nc1cnoc1-c1ccc(-c2ccc3c(c2)CCCC3C(=O)O)cc1)c1ccccc1]
TABLE 2-continued
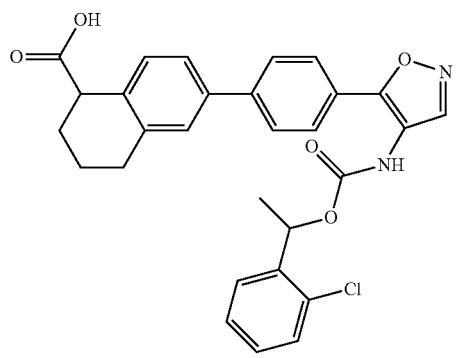 [SMILES: CC(OC(=O)Nc1cnoc1-c1ccc(-c2ccc3c(c2)CCCC3C(=O)O)cc1)c1ccccc1Cl]
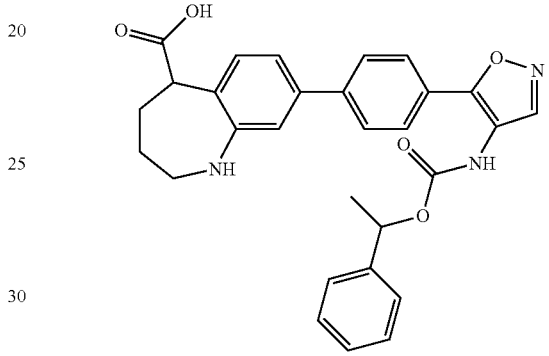
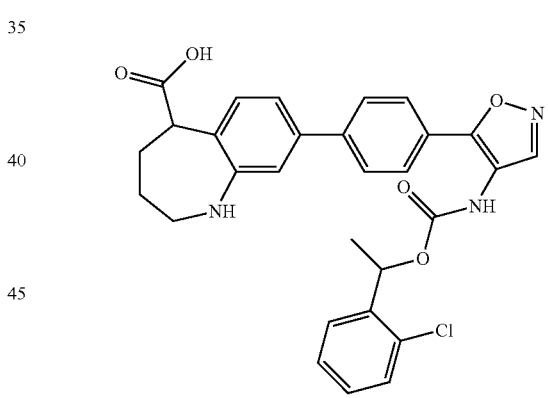
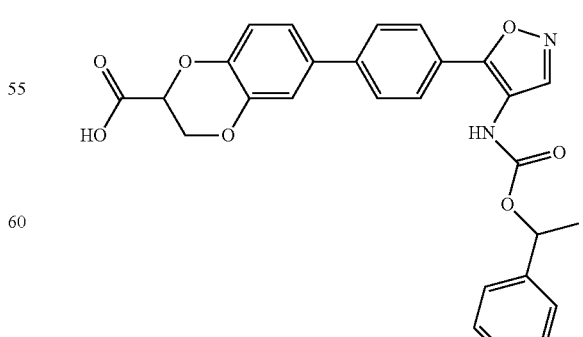

TABLE 2-continued
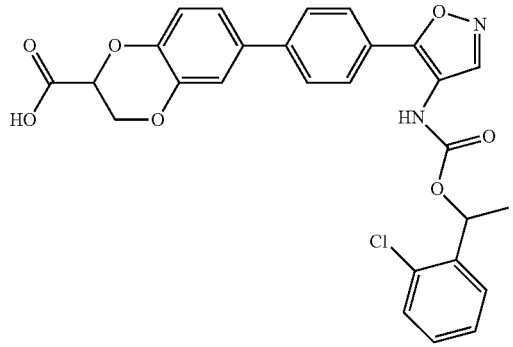 [SMILES: CC(OC(=O)Nc1cnoc1-c1ccc(-c2ccc3c(c2)OCC(C(=O)O)O3)cc1)c1ccccc1Cl]
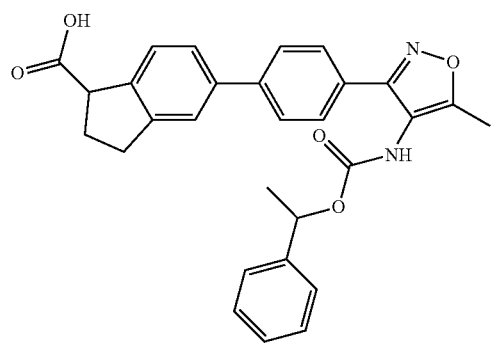 [SMILES: Cc1onc(-c2ccc(-c3ccc4c(c3)CCC4C(=O)O)cc2)c1NC(=O)OC(C)c1ccccc1]
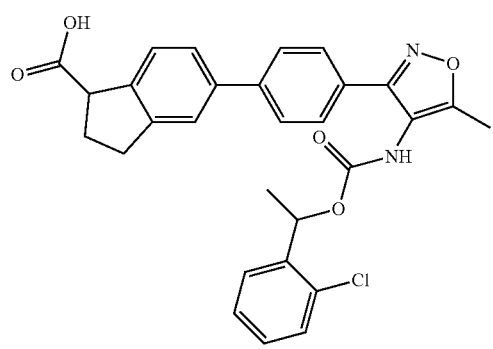
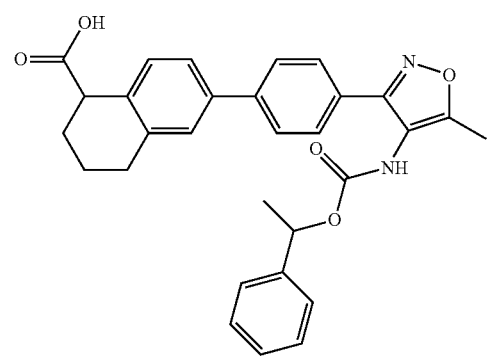 [SMILES: Cc1onc(-c2ccc(-c3ccc4c(c3)CCCC4C(=O)O)cc2)c1NC(=O)OC(C)c1ccccc1]
TABLE 2-continued
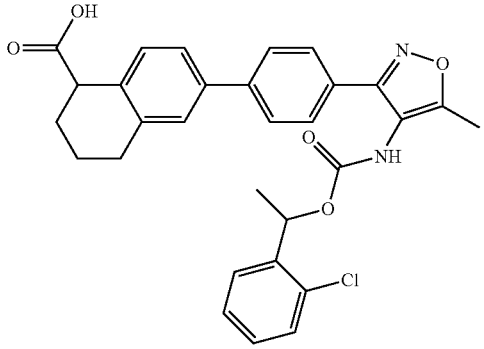 [SMILES: Cc1onc(-c2ccc(-c3ccc4c(c3)CCCC4C(=O)O)cc2)c1NC(=O)OC(C)c1ccccc1Cl]
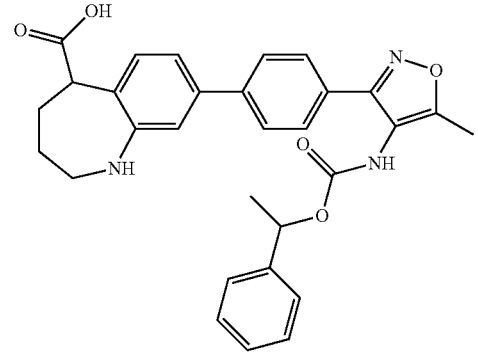 [SMILES: Cc1onc(-c2ccc(-c3ccc4c(c3)NCCCC4C(=O)O)cc2)c1NC(=O)OC(C)c1ccccc1]
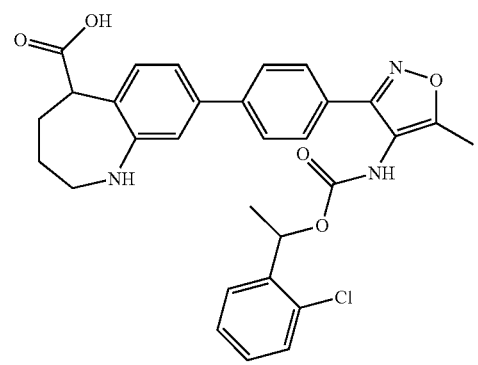 [SMILES: Cc1onc(-c2ccc(-c3ccc4c(c3)NCCCC4C(=O)O)cc2)c1NC(=O)OC(C)c1ccccc1Cl]
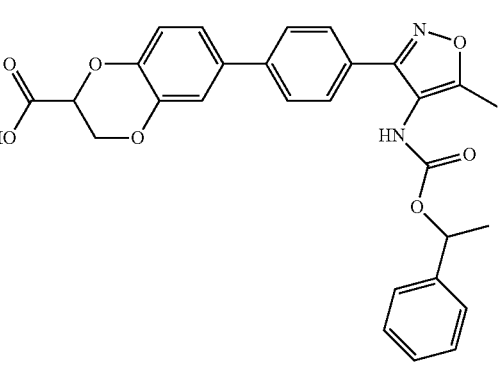

281
TABLE 2-continued
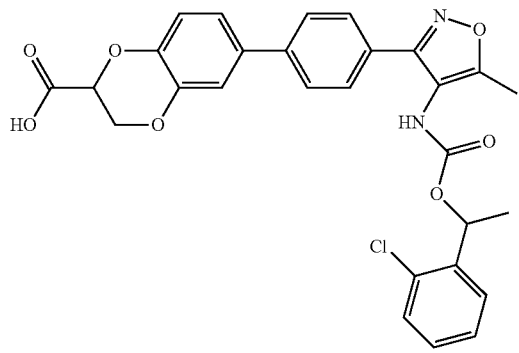 [SMILES: Cc1onc(-c2ccc(-c3ccc4c(c3)OCC(C(=O)O)O4)cc2)c1NC(=O)OC(C)c1ccccc1Cl]
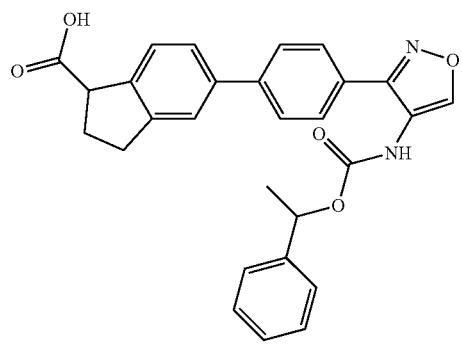 [SMILES: CC(OC(=O)Nc1conc1-c1ccc(-c2ccc3c(c2)CCC3C(=O)O)cc1)c1ccccc1]
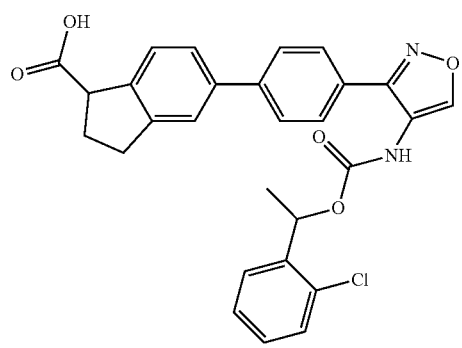 [SMILES: CC(OC(=O)Nc1conc1-c1ccc(-c2ccc3c(c2)CCC3C(=O)O)cc1)c1ccccc1Cl]
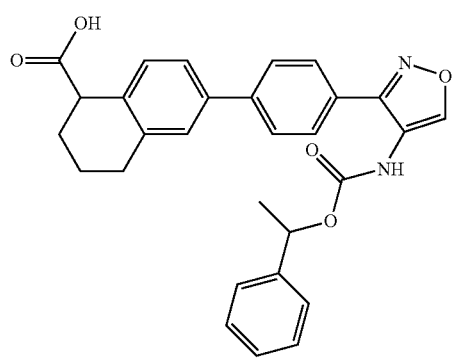 [SMILES: CC(OC(=O)Nc1conc1-c1ccc(-c2ccc3c(c2)CCCC3C(=O)O)cc1)c1ccccc1]
282
TABLE 2-continued
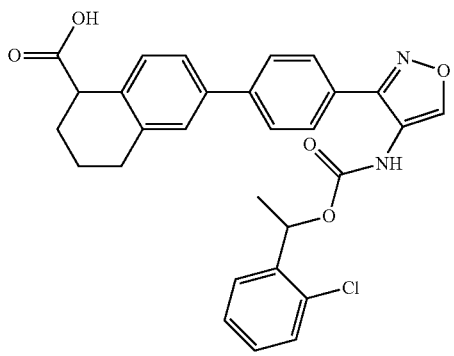 [SMILES: CC(OC(=O)Nc1conc1-c1ccc(-c2ccc3c(c2)CCCC3C(=O)O)cc1)c1ccccc1Cl]
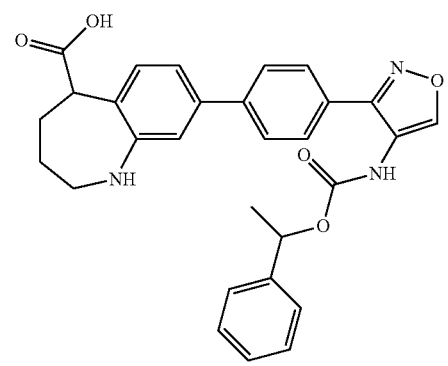
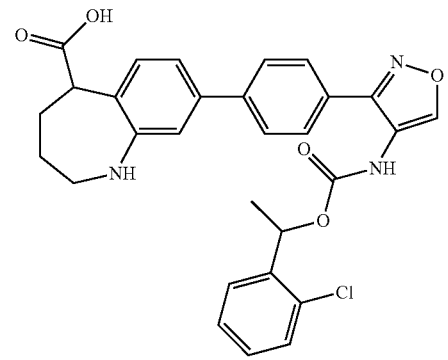 [SMILES: CC(OC(=O)Nc1conc1-c1ccc(-c2ccc3c(c2)NCCCC3C(=O)O)cc1)c1ccccc1Cl]
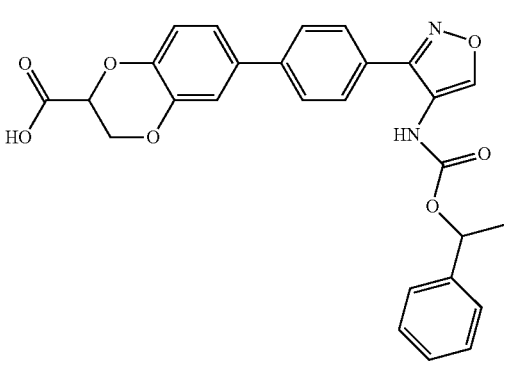 [SMILES: CC(OC(=O)Nc1conc1-c1ccc(-c2ccc3c(c2)OCC(C(=O)O)O3)cc1)c1ccccc1]

TABLE 2-continued
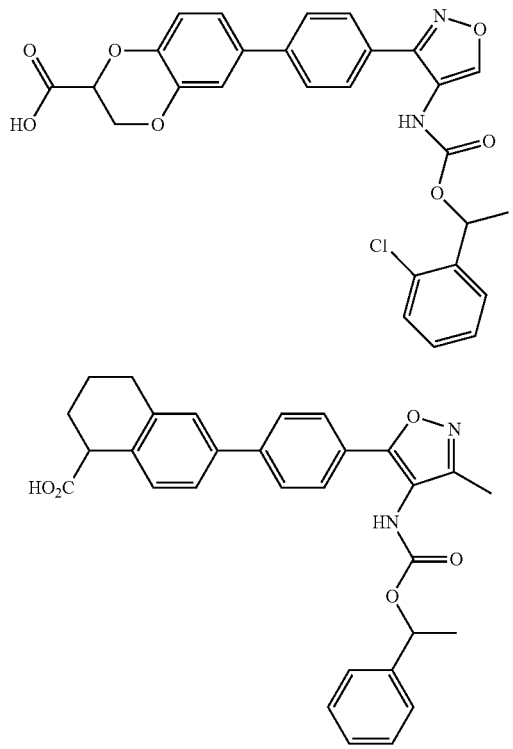
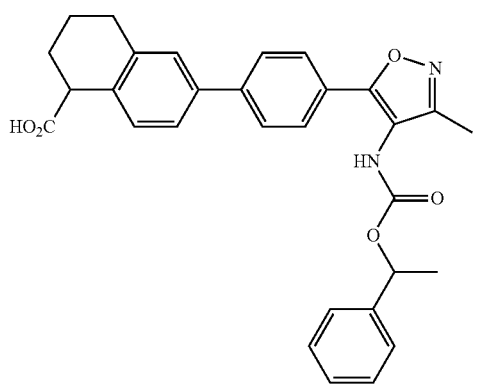 [SMILES: Cc1noc(-c2ccc(-c3ccc4c(c3)CCCC4C(=O)O)cc2)c1NC(=O)OC(C)c1ccccc1]
In some embodiments, compounds of Formula (I) are selected from the following compounds as listed in Table 3.
TABLE 3
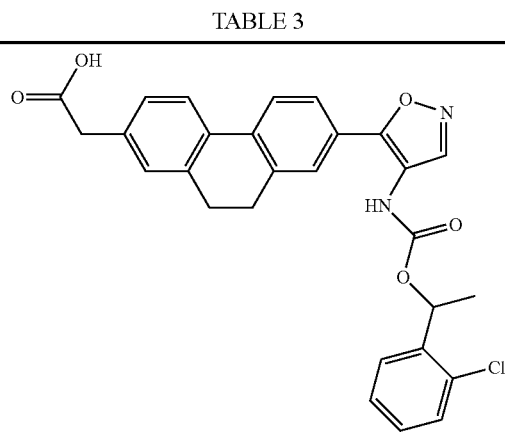
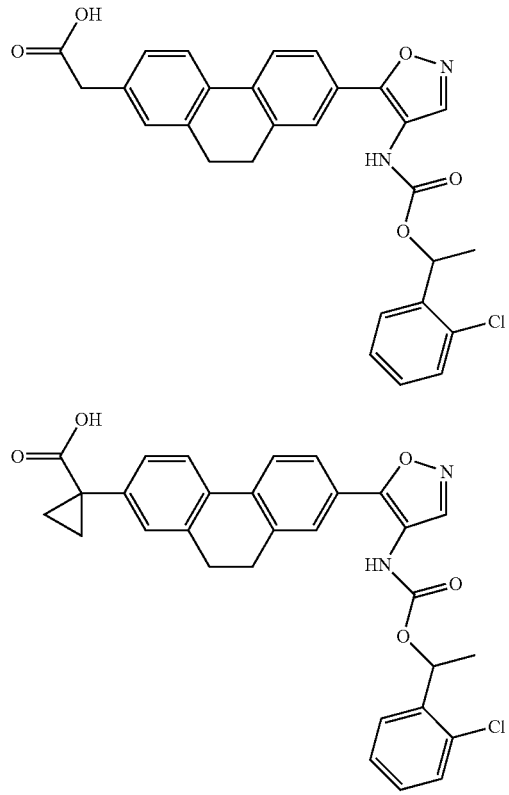
TABLE 3-continued
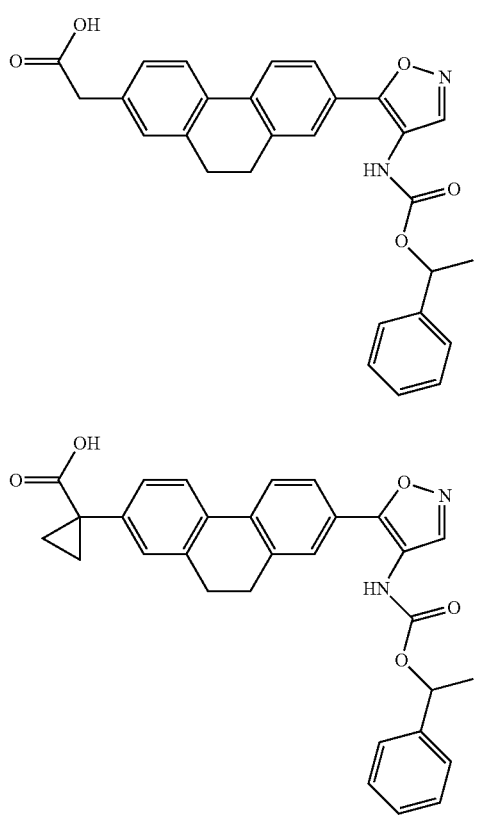
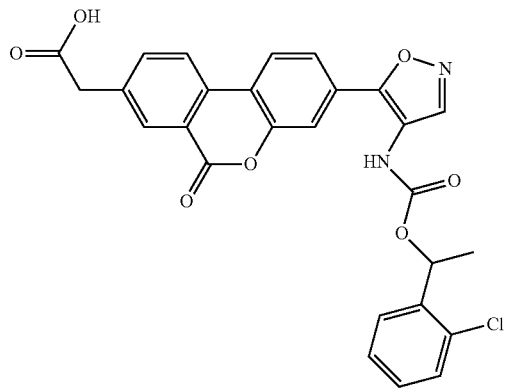
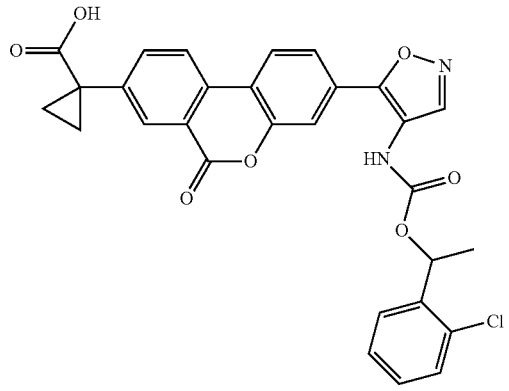 [SMILES: CC(OC(=O)Nc1cnoc1-c1ccc2c(c1)oc(=O)c1cc(C3(C(=O)O)CC3)ccc12)c1ccccc1Cl]

TABLE 3-continued
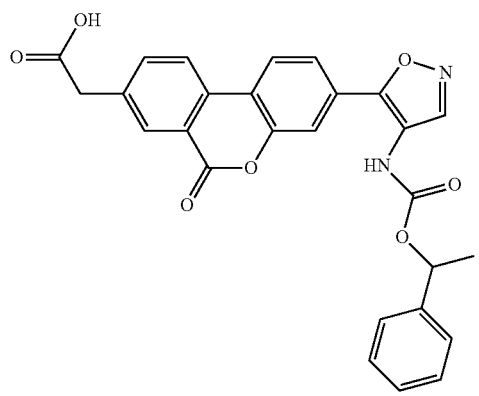 [SMILES: CC(OC(=O)Nc1cnoc1-c1ccc2c(c1)oc(=O)c1cc(CC(=O)O)ccc12)c1ccccc1]
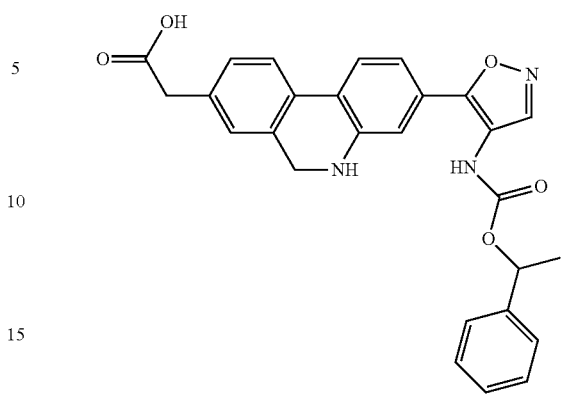
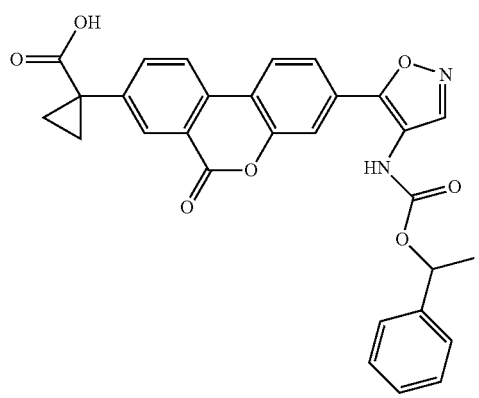 [SMILES: CC(OC(=O)Nc1cnoc1-c1ccc2c(c1)oc(=O)c1cc(C3(C(=O)O)CC3)ccc12)c1ccccc1]
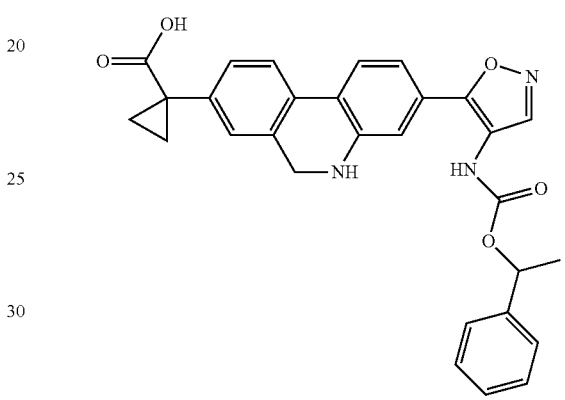
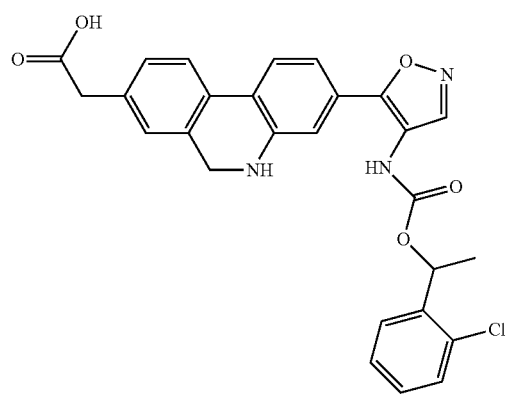 [SMILES: CC(OC(=O)Nc1cnoc1-c1ccc2c(c1)NCc1cc(CC(=O)O)ccc1-2)c1ccccc1Cl]
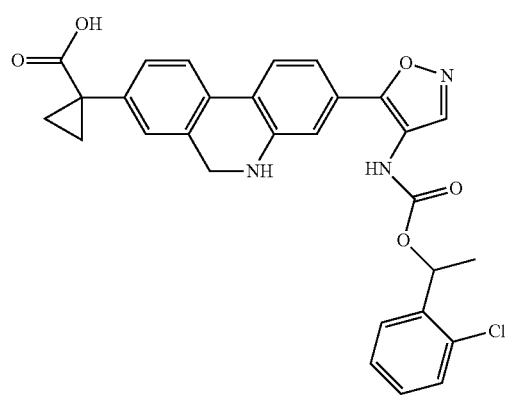 [SMILES: CC(OC(=O)Nc1cnoc1-c1ccc2c(c1)NCc1cc(C3(C(=O)O)CC3)ccc1-2)c1ccccc1Cl]
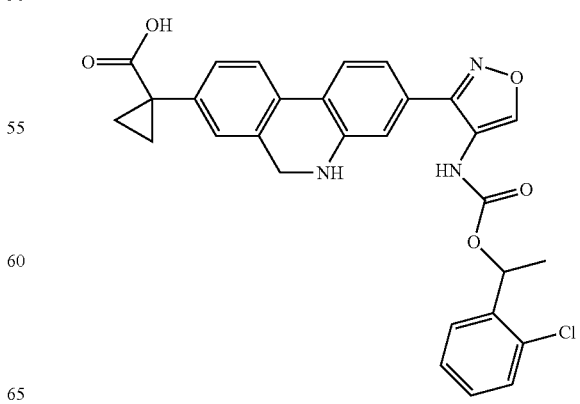

287
TABLE 3-continued
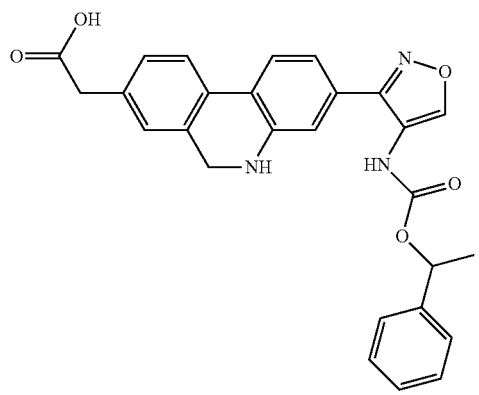 [SMILES: CC(OC(=O)Nc1conc1-c1ccc2c(c1)NCc1cc(CC(=O)O)ccc1-2)c1ccccc1]
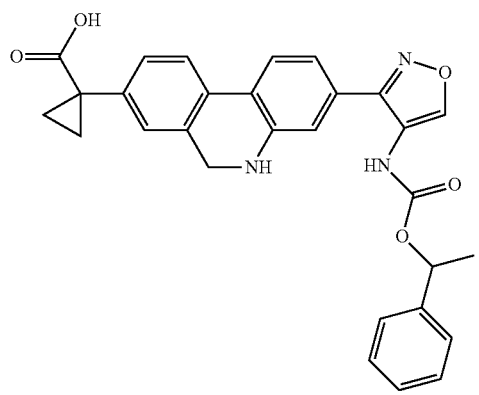 [SMILES: CC(OC(=O)Nc1conc1-c1ccc2c(c1)NCc1cc(C3(C(=O)O)CC3)ccc1-2)c1ccccc1]
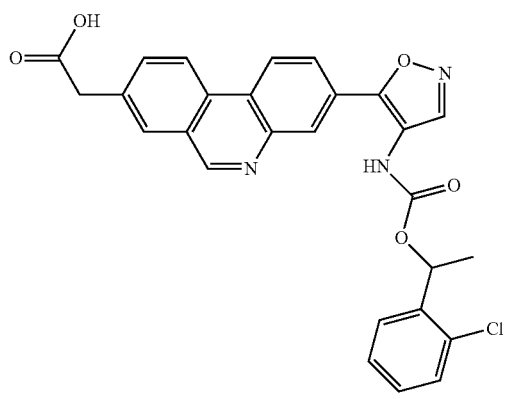 [SMILES: CC(OC(=O)Nc1cnoc1-c1ccc2c(c1)ncc1cc(CC(=O)O)ccc12)c1ccccc1Cl]
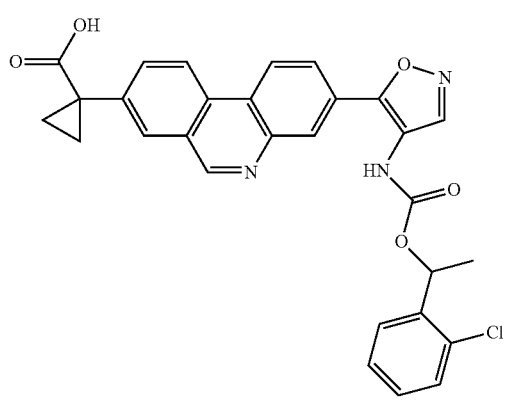 [SMILES: CC(OC(=O)Nc1cnoc1-c1ccc2c(c1)ncc1cc(C3(C(=O)O)CC3)ccc12)c1ccccc1Cl]
288
TABLE 3-continued
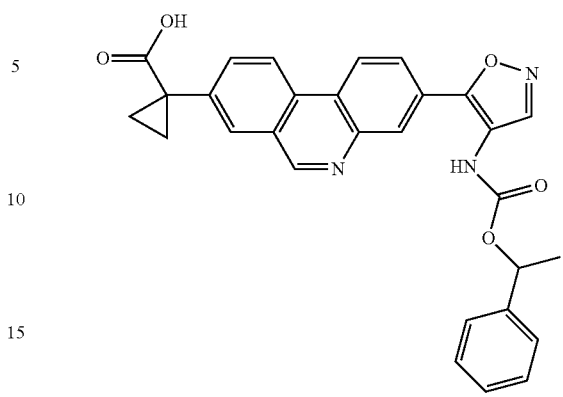
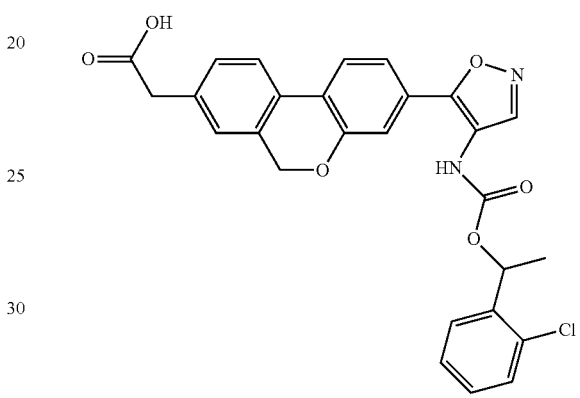
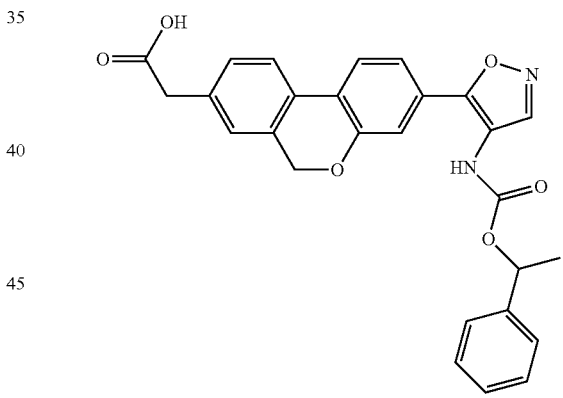
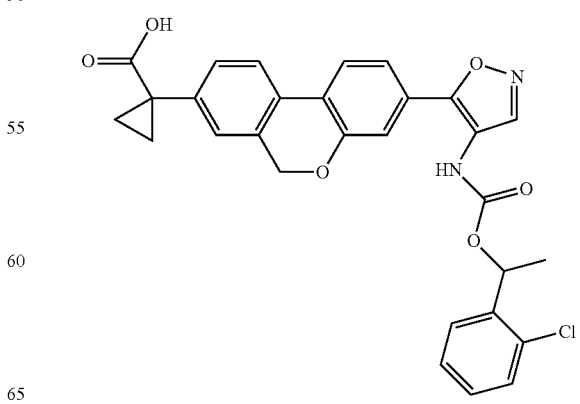

TABLE 3-continued
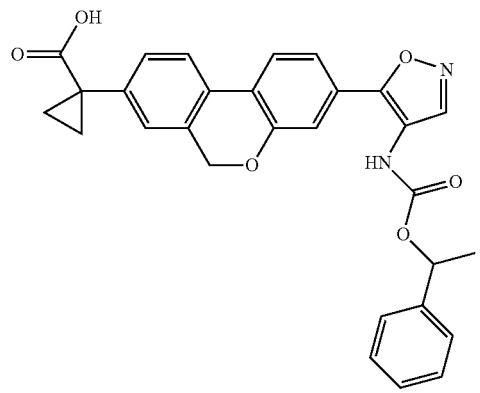 [SMILES: CC(OC(=O)Nc1cnoc1-c1ccc2c(c1)OCc1cc(C3(C(=O)O)CC3)ccc1-2)c1ccccc1]
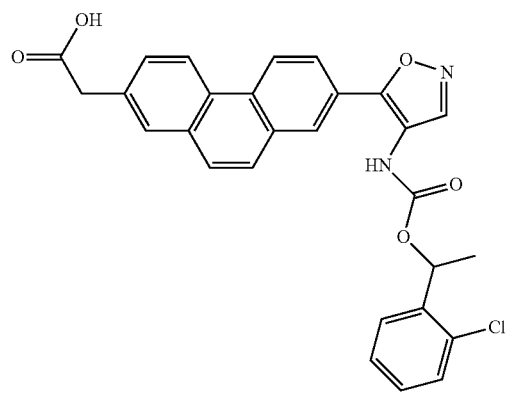 [SMILES: CC(OC(=O)Nc1cnoc1-c1ccc2c(ccc3cc(CC(=O)O)ccc32)c1)c1ccccc1Cl]
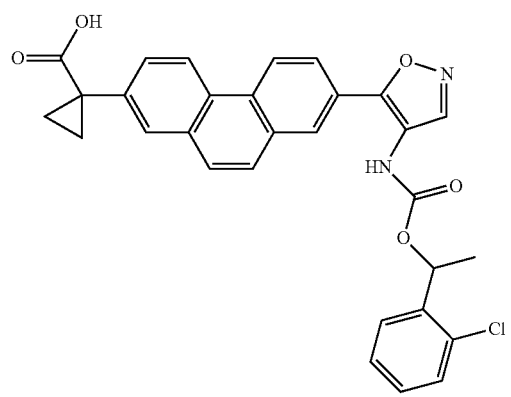 [SMILES: CC(OC(=O)Nc1cnoc1-c1ccc2c(ccc3cc(C4(C(=O)O)CC4)ccc32)c1)c1ccccc1Cl]
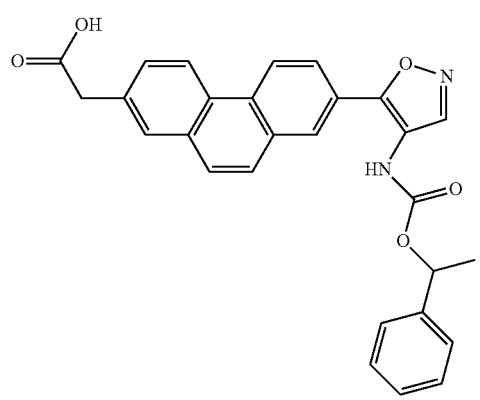 [SMILES: CC(OC(=O)Nc1cnoc1-c1ccc2c(ccc3cc(CC(=O)O)ccc32)c1)c1ccccc1]
TABLE 3-continued
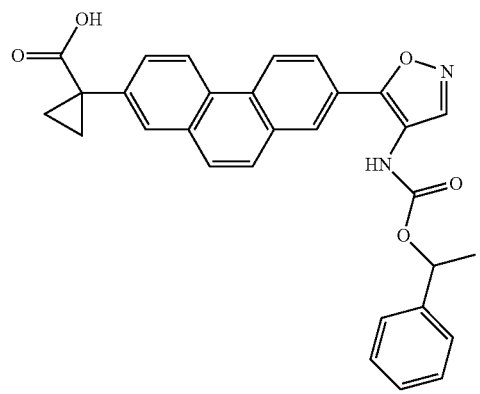
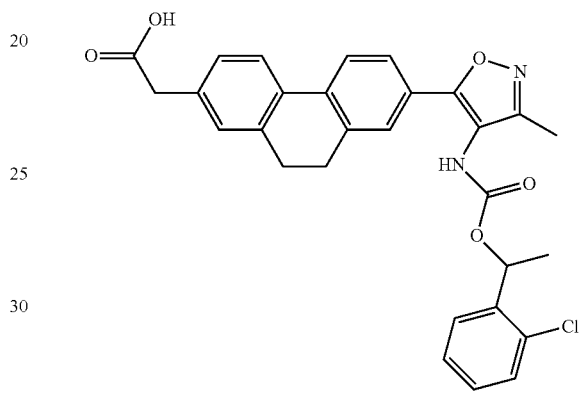
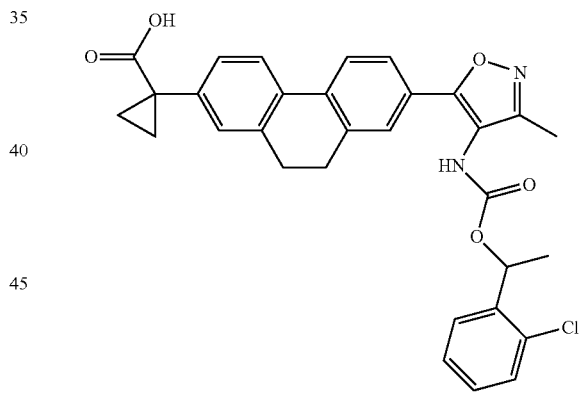
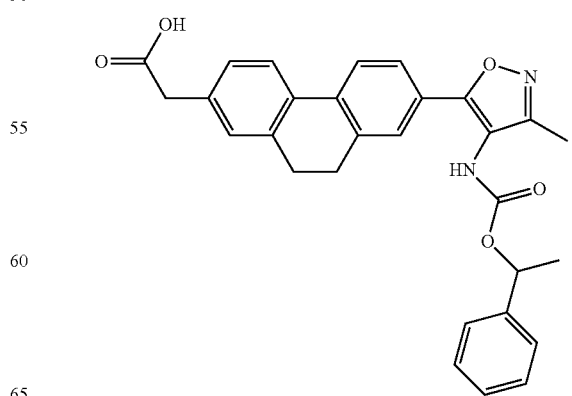

TABLE 3-continued
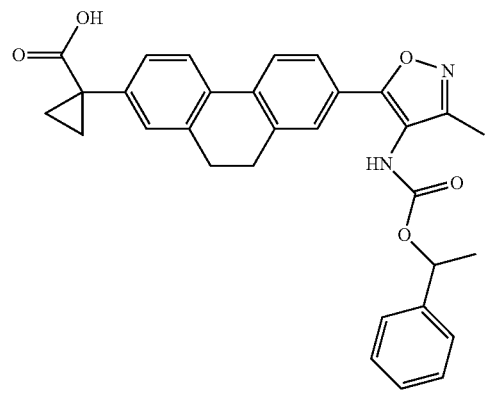
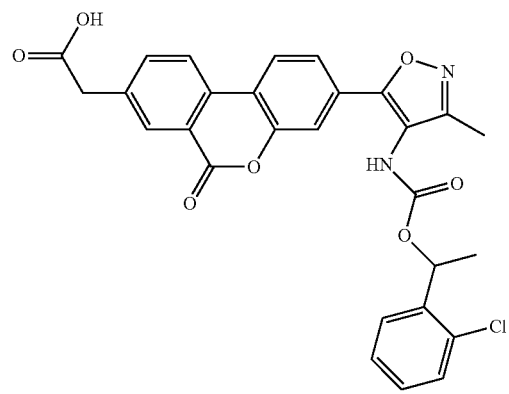 [SMILES: Cc1noc(-c2ccc3c(c2)oc(=O)c2cc(CC(=O)O)ccc23)c1NC(=O)OC(C)c1ccccc1Cl]
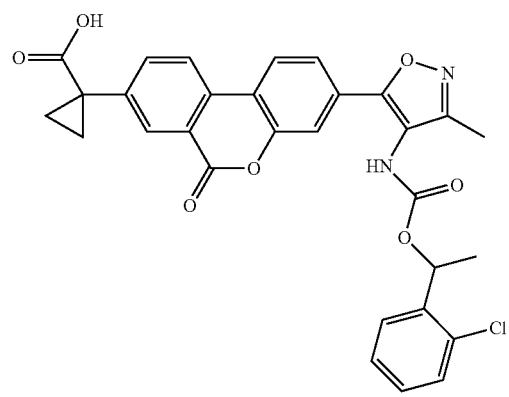 [SMILES: Cc1noc(-c2ccc3c(c2)oc(=O)c2cc(C4(C(=O)O)CC4)ccc23)c1NC(=O)OC(C)c1ccccc1Cl]
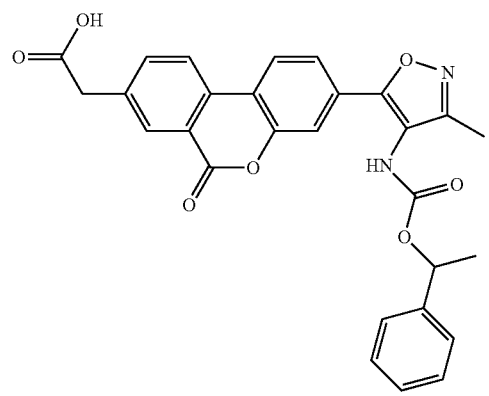 [SMILES: Cc1noc(-c2ccc3c(c2)oc(=O)c2cc(CC(=O)O)ccc23)c1NC(=O)OC(C)c1ccccc1]
TABLE 3-continued
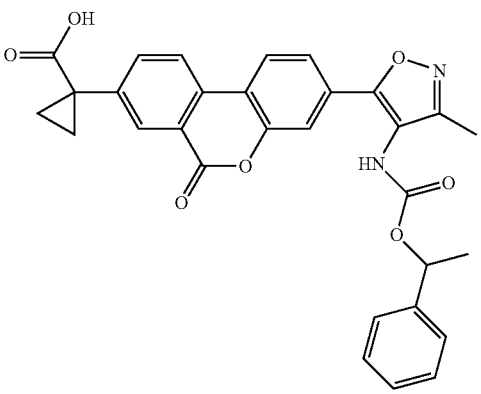 [SMILES: Cc1noc(-c2ccc3c(c2)oc(=O)c2cc(C4(C(=O)O)CC4)ccc23)c1NC(=O)OC(C)c1ccccc1]
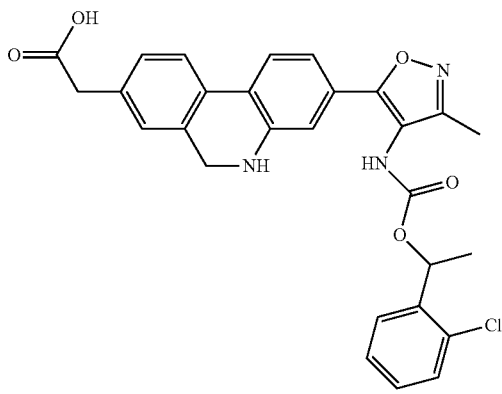 [SMILES: Cc1noc(-c2ccc3c(c2)NCc2cc(CC(=O)O)ccc2-3)c1NC(=O)OC(C)c1ccccc1Cl]
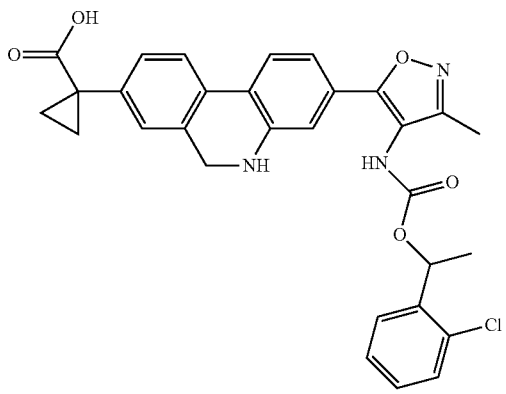 [SMILES: Cc1noc(-c2ccc3c(c2)NCc2cc(C4(C(=O)O)CC4)ccc2-3)c1NC(=O)OC(C)c1ccccc1Cl]
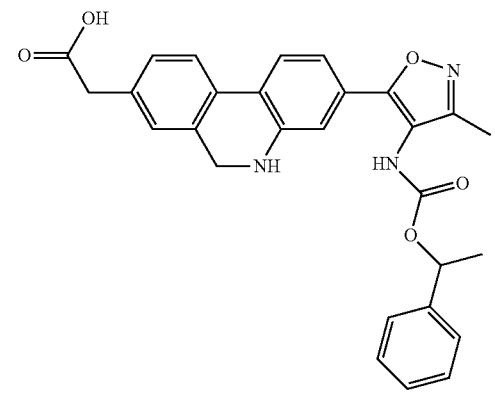 [SMILES: Cc1noc(-c2ccc3c(c2)NCc2cc(CC(=O)O)ccc2-3)c1NC(=O)OC(C)c1ccccc1]

TABLE 3-continued
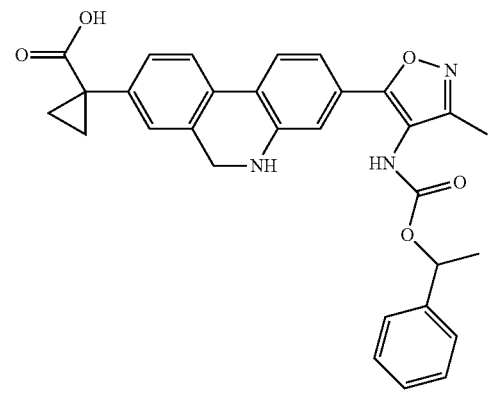
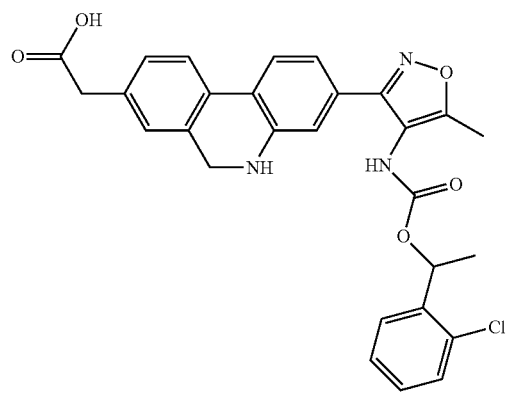 [SMILES: Cc1onc(-c2ccc3c(c2)NCc2cc(CC(=O)O)ccc2-3)c1NC(=O)OC(C)c1ccccc1Cl]
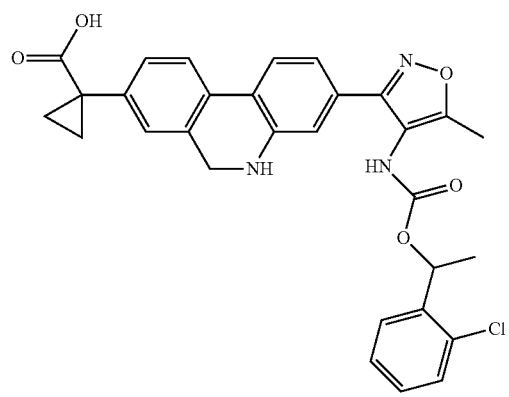
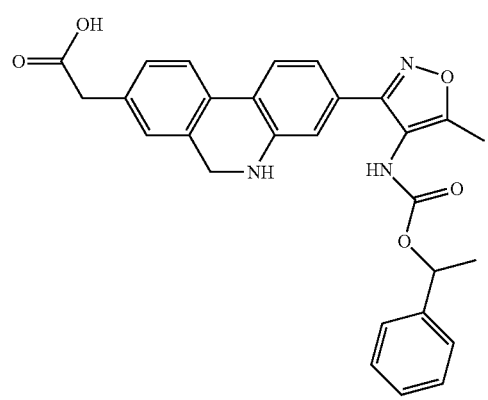 [SMILES: Cc1onc(-c2ccc3c(c2)NCc2cc(CC(=O)O)ccc2-3)c1NC(=O)OC(C)c1ccccc1]
TABLE 3-continued
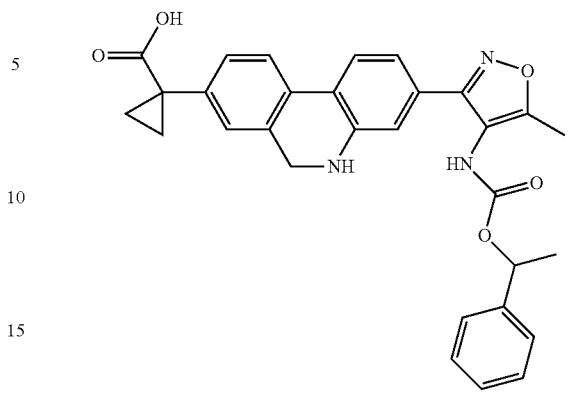
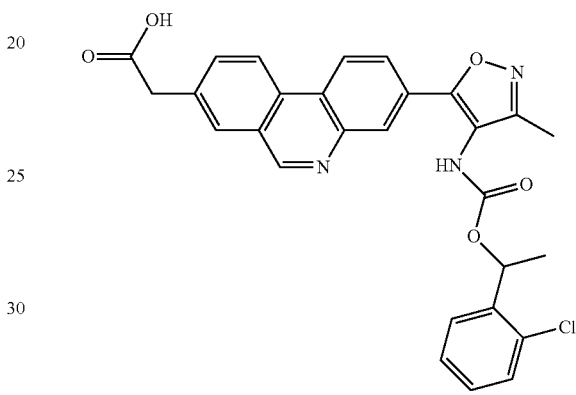
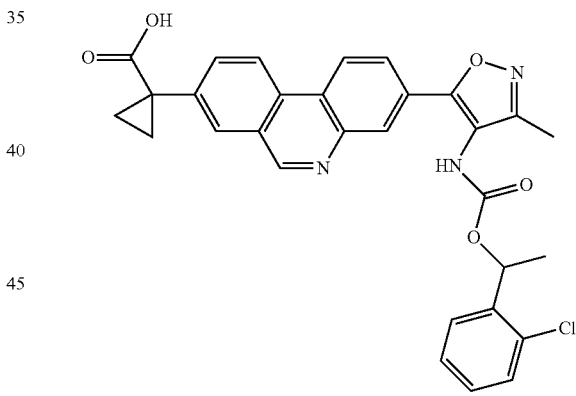
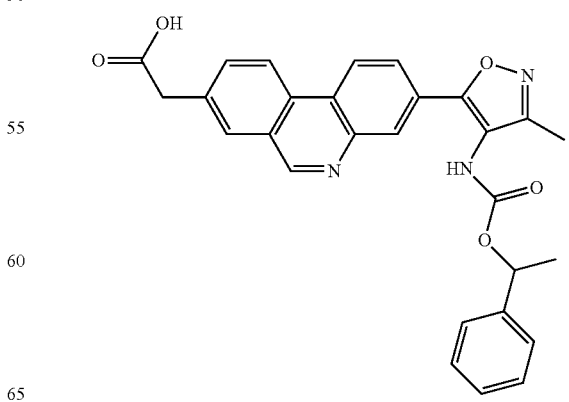

TABLE 3-continued
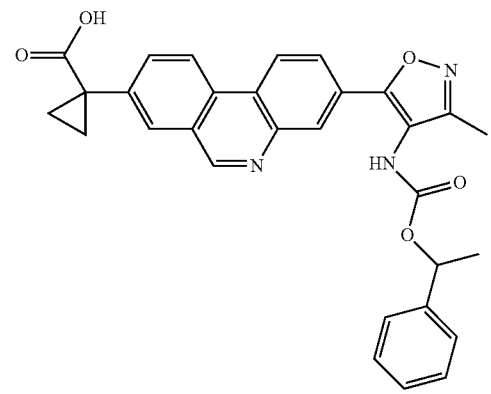 [SMILES: Cc1noc(-c2ccc3c(c2)ncc2cc(C4(C(=O)O)CC4)ccc23)c1NC(=O)OC(C)c1ccccc1]
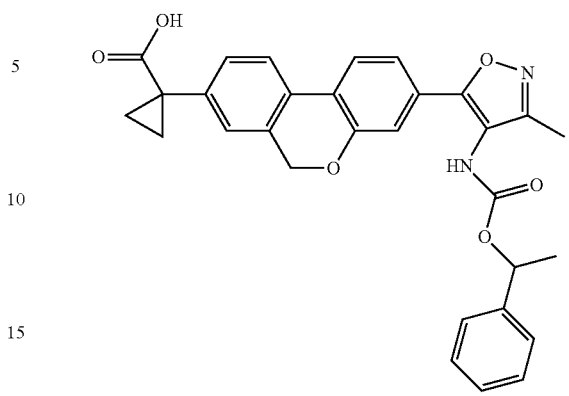
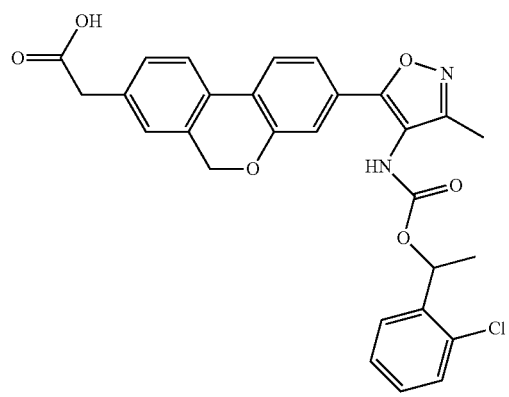 [SMILES: Cc1noc(-c2ccc3c(c2)OCc2cc(CC(=O)O)ccc2-3)c1NC(=O)OC(C)c1ccccc1Cl]

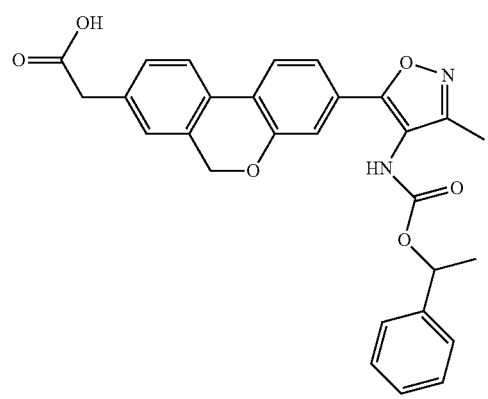 [SMILES: Cc1noc(-c2ccc3c(c2)OCc2cc(CC(=O)O)ccc2-3)c1NC(=O)OC(C)c1ccccc1]

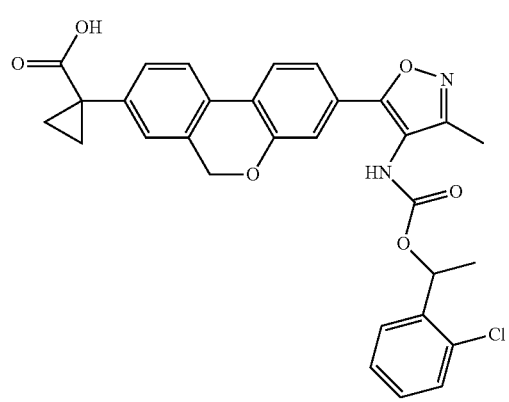 [SMILES: Cc1noc(-c2ccc3c(c2)OCc2cc(C4(C(=O)O)CC4)ccc2-3)c1NC(=O)OC(C)c1ccccc1Cl]
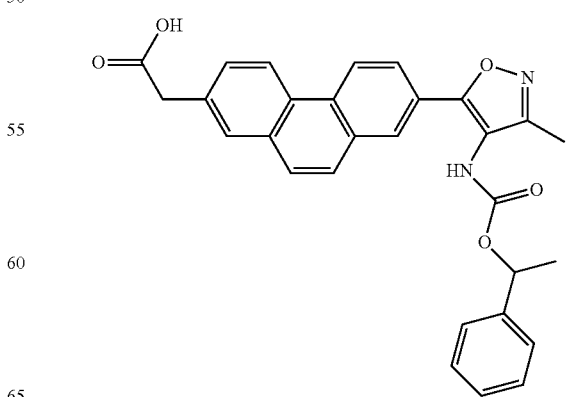

TABLE 3-continued
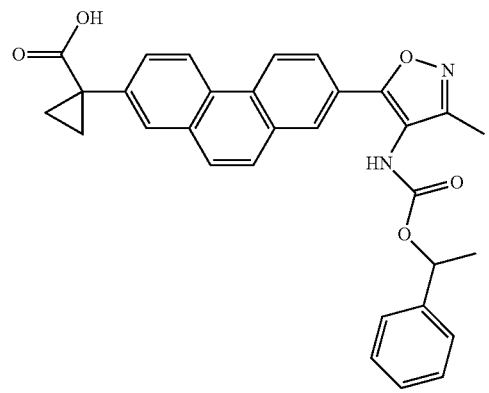
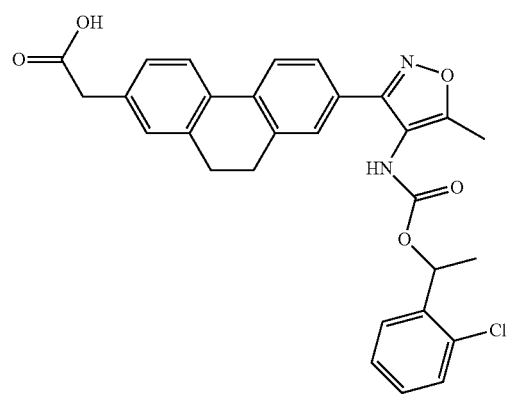 [SMILES: Cc1onc(-c2ccc3c(c2)CCc2cc(CC(=O)O)ccc2-3)c1NC(=O)OC(C)c1ccccc1Cl]
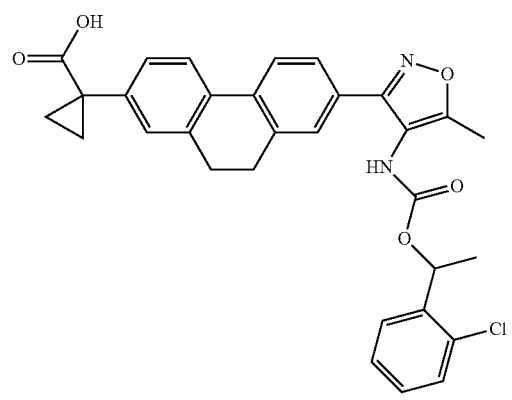 [SMILES: Cc1onc(-c2ccc3c(c2)CCc2cc(C4(C(=O)O)CC4)ccc2-3)c1NC(=O)OC(C)c1ccccc1Cl]
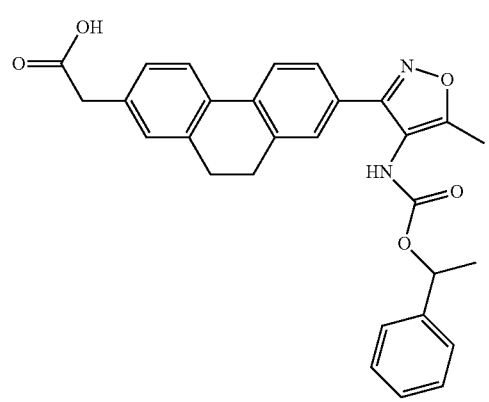 [SMILES: Cc1onc(-c2ccc3c(c2)CCc2cc(CC(=O)O)ccc2-3)c1NC(=O)OC(C)c1ccccc1]
TABLE 3-continued
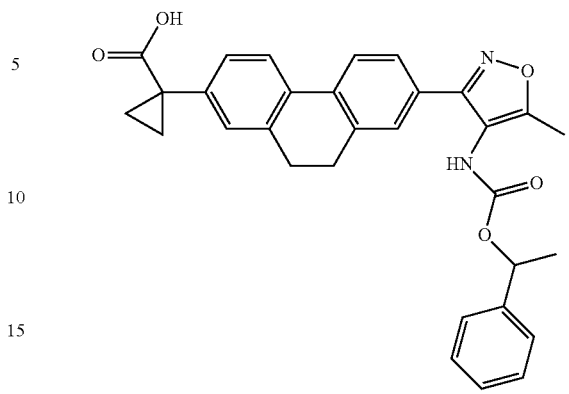
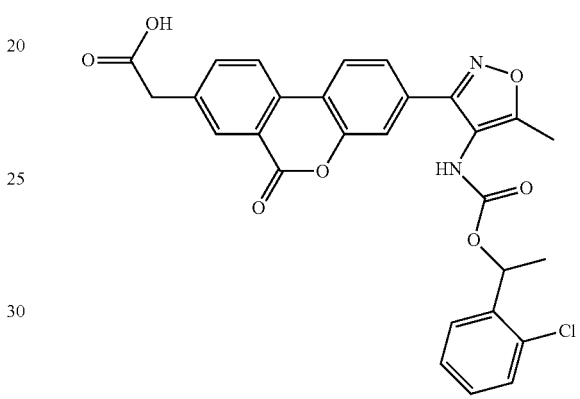

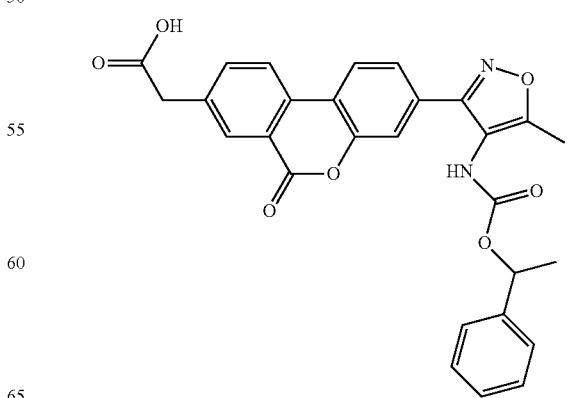

TABLE 3-continued
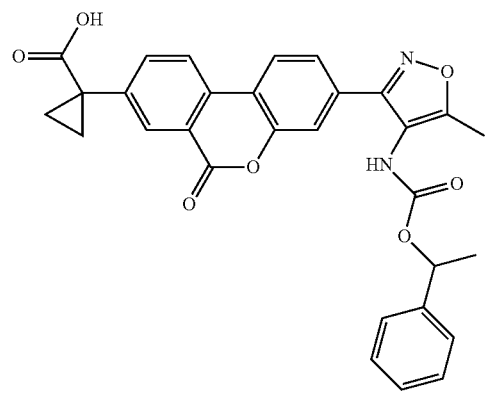 [SMILES: Cc1onc(-c2ccc3c(c2)oc(=O)c2cc(C4(C(=O)O)CC4)ccc23)c1NC(=O)OC(C)c1ccccc1]
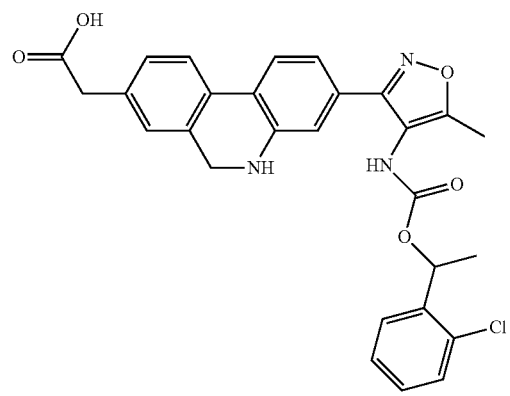 [SMILES: Cc1onc(-c2ccc3c(c2)NCc2cc(CC(=O)O)ccc2-3)c1NC(=O)OC(C)c1ccccc1Cl]
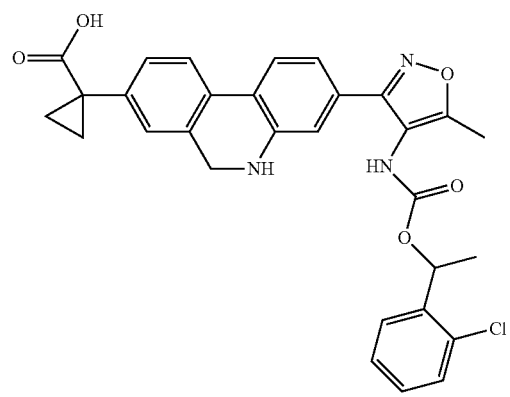
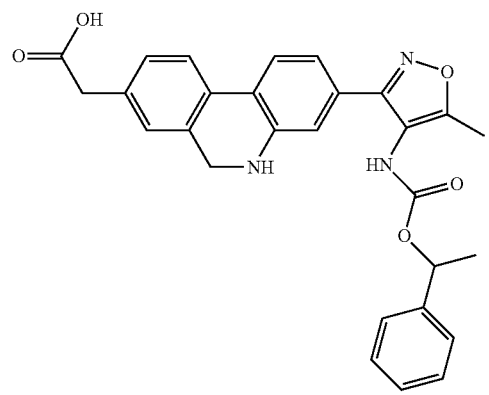 [SMILES: Cc1onc(-c2ccc3c(c2)NCc2cc(CC(=O)O)ccc2-3)c1NC(=O)OC(C)c1ccccc1]
TABLE 3-continued
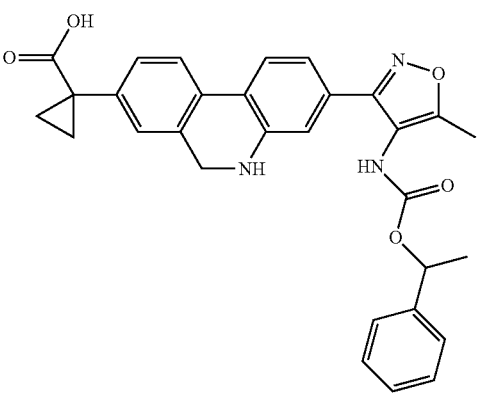 [SMILES: Cc1onc(-c2ccc3c(c2)NCc2cc(C4(C(=O)O)CC4)ccc2-3)c1NC(=O)OC(C)c1ccccc1]
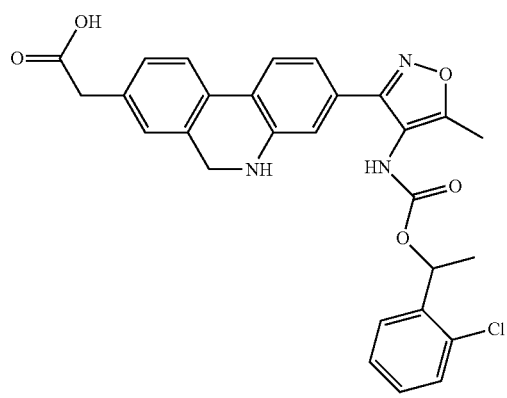 [SMILES: Cc1onc(-c2ccc3c(c2)NCc2cc(CC(=O)O)ccc2-3)c1NC(=O)OC(C)c1ccccc1Cl]
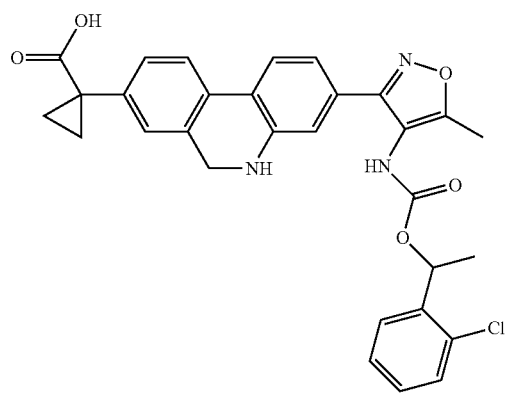 [SMILES: Cc1onc(-c2ccc3c(c2)NCc2cc(C4(C(=O)O)CC4)ccc2-3)c1NC(=O)OC(C)c1ccccc1Cl]
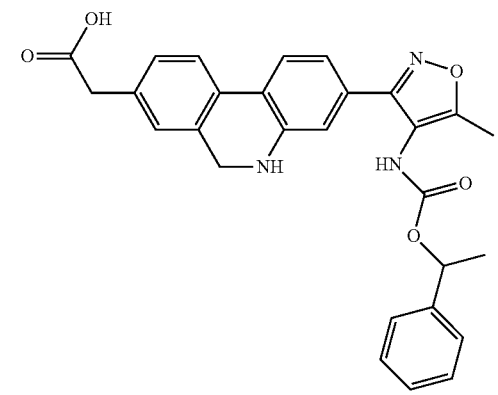

TABLE 3-continued
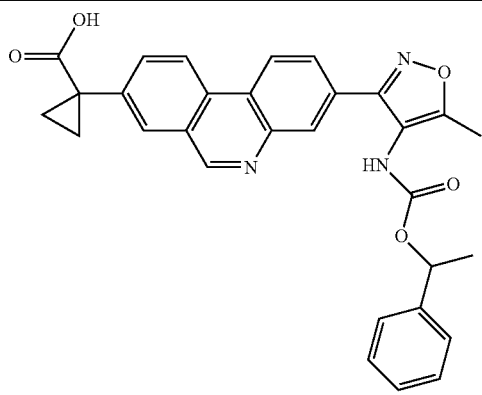
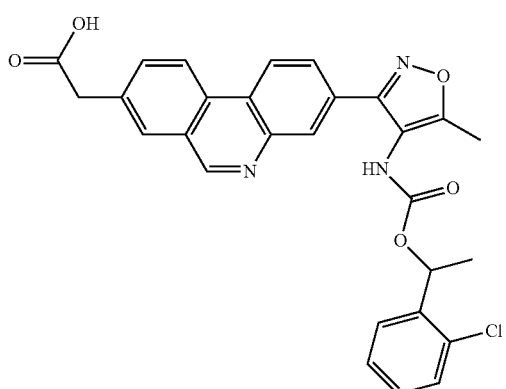
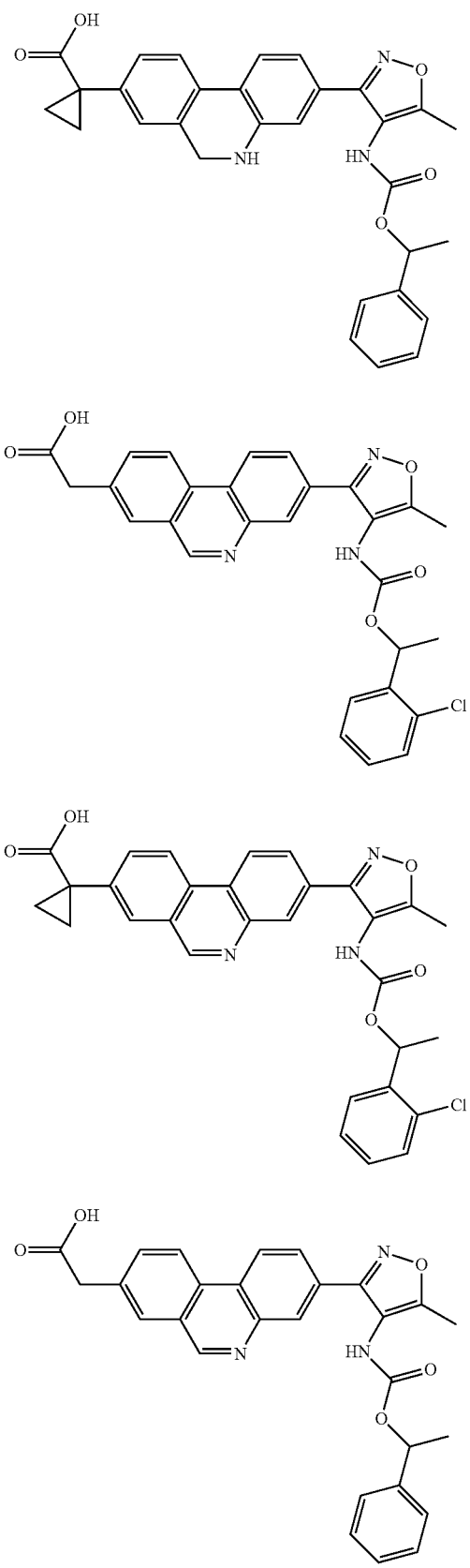
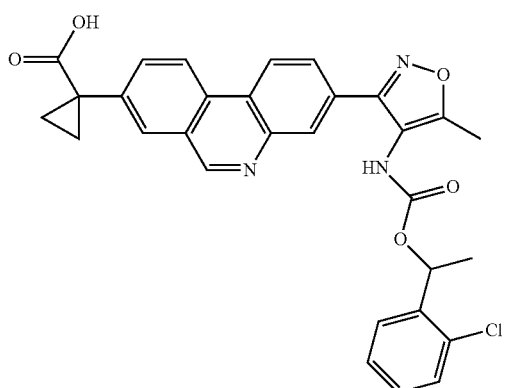
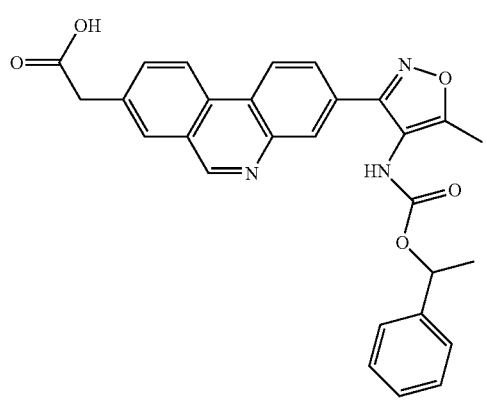 [SMILES: Cc1onc(-c2ccc3c(c2)ncc2cc(CC(=O)O)ccc23)c1NC(=O)OC(C)c1ccccc1]
In some embodiments, compounds of Formula (I) are selected from the following compounds as listed in Table 4.

TABLE 4
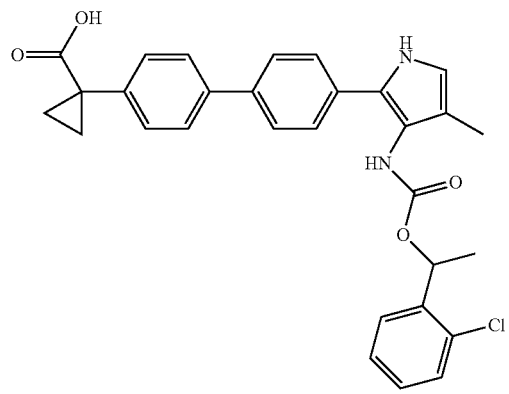
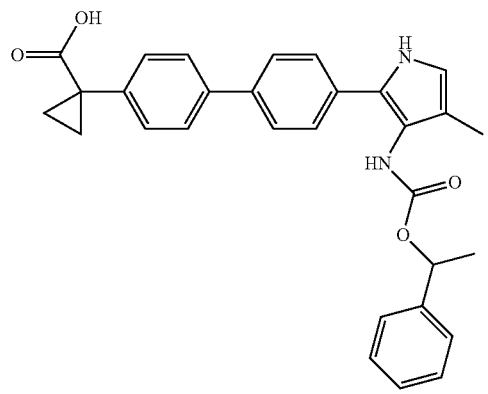
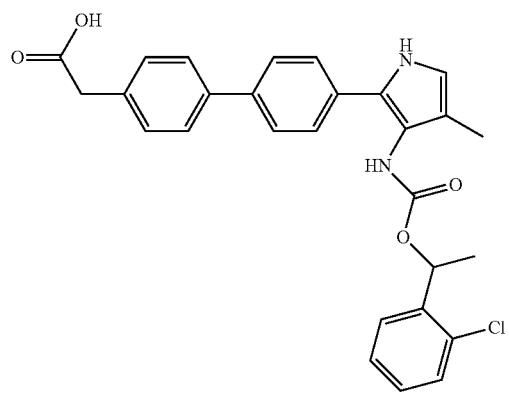
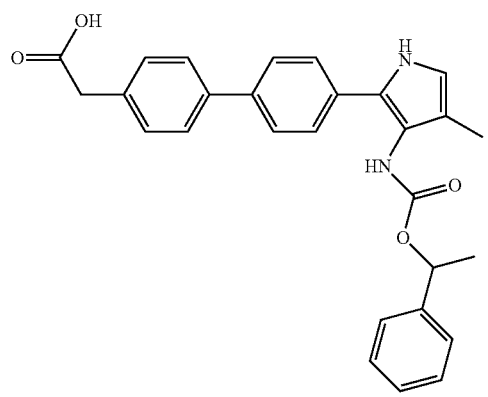
TABLE 4-continued
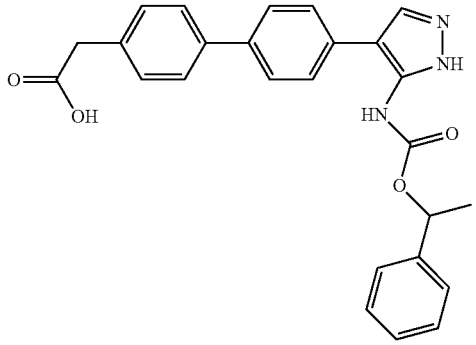 [SMILES: CC(OC(=O)Nc1[nH]ncc1-c1ccc(-c2ccc(CC(=O)O)cc2)cc1)c1ccccc1]
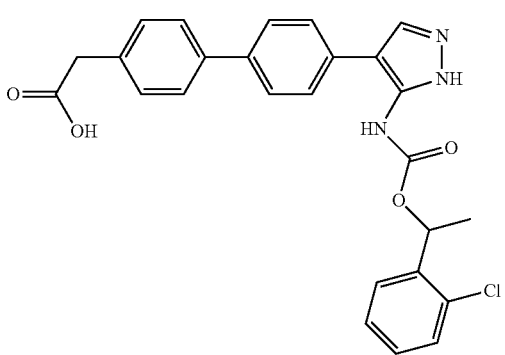 [SMILES: CC(OC(=O)Nc1[nH]ncc1-c1ccc(-c2ccc(CC(=O)O)cc2)cc1)c1ccccc1Cl]
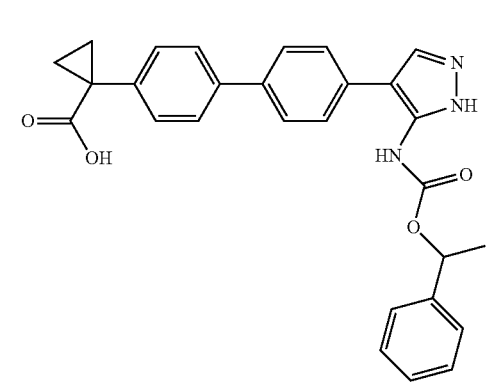
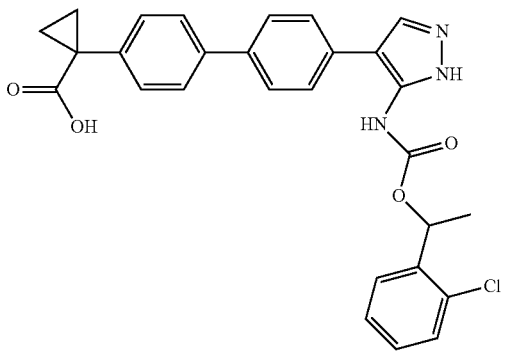 [SMILES: CC(OC(=O)Nc1[nH]ncc1-c1ccc(-c2ccc(C3(C(=O)O)CC3)cc2)cc1)c1ccccc1Cl]

TABLE 4-continued
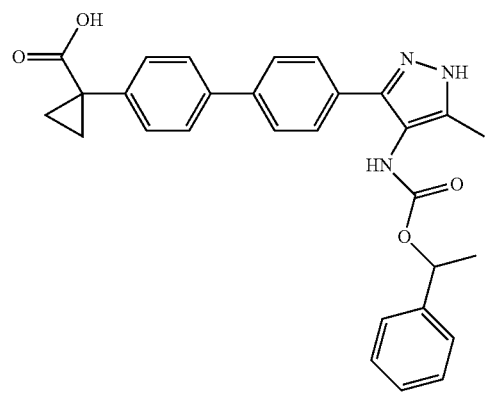 [SMILES: Cc1[nH]nc(-c2ccc(-c3ccc(C4(C(=O)O)CC4)cc3)cc2)c1NC(=O)OC(C)c1ccccc1]
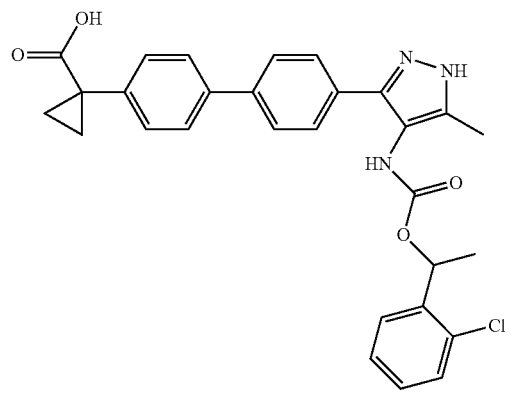 [SMILES: Cc1[nH]nc(-c2ccc(-c3ccc(C4(C(=O)O)CC4)cc3)cc2)c1NC(=O)OC(C)c1ccccc1Cl]
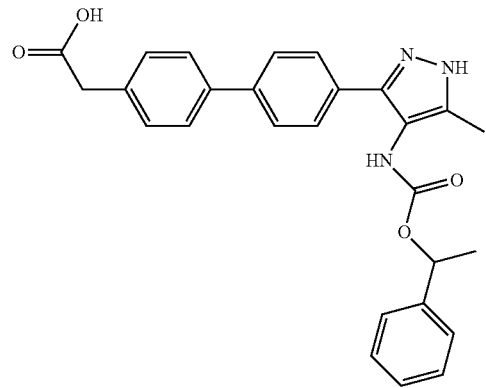 [SMILES: Cc1[nH]nc(-c2ccc(-c3ccc(CC(=O)O)cc3)cc2)c1NC(=O)OC(C)c1ccccc1]
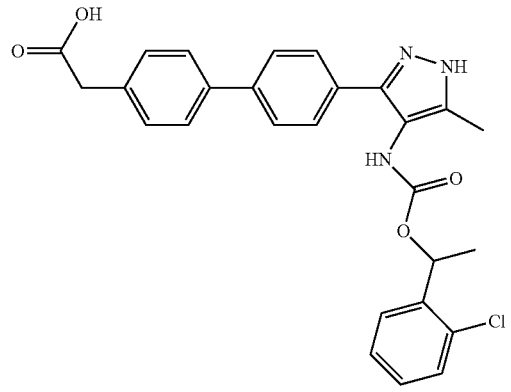
TABLE 4-continued
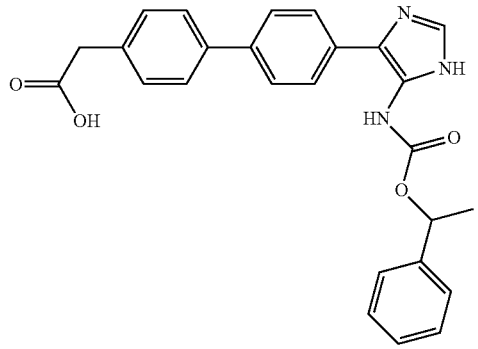 [SMILES: CC(OC(=O)Nc1[nH]cnc1-c1ccc(-c2ccc(CC(=O)O)cc2)cc1)c1ccccc1]
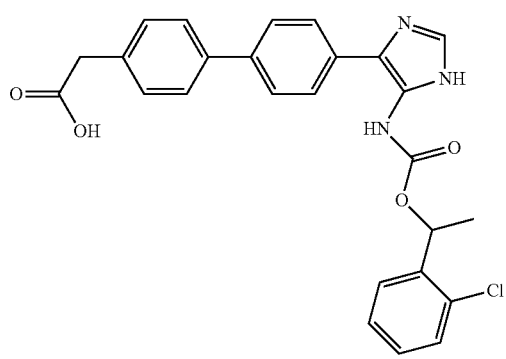 [SMILES: CC(OC(=O)Nc1[nH]cnc1-c1ccc(-c2ccc(CC(=O)O)cc2)cc1)c1ccccc1Cl]
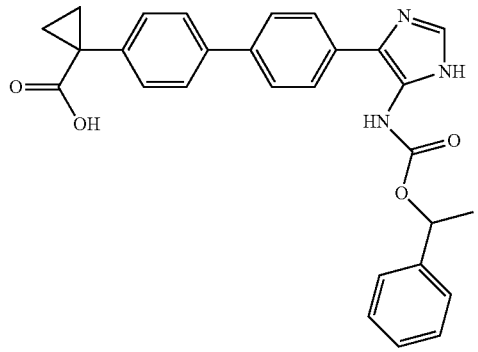
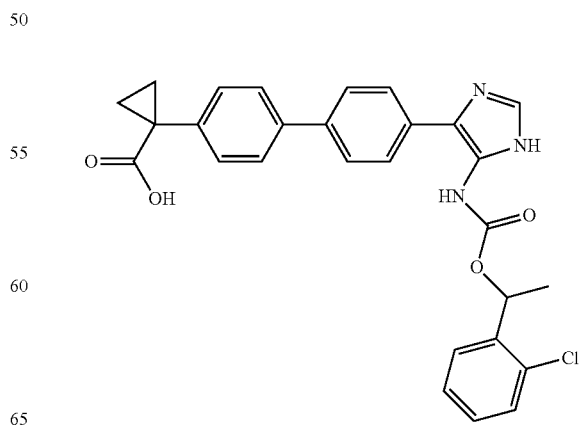

TABLE 4-continued
307
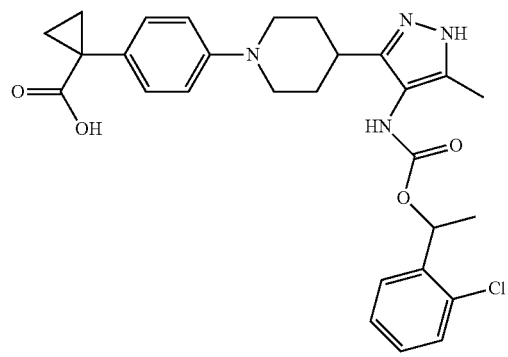 [SMILES: Cc1[nH]nc(C2CCN(c3ccc(C4(C(=O)O)CC4)cc3)CC2)c1NC(=O)OC(C)c1ccccc1Cl]
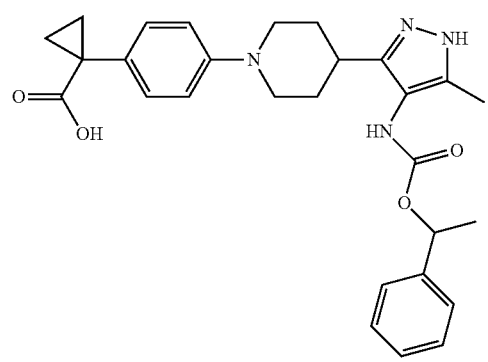 [SMILES: Cc1[nH]nc(C2CCN(c3ccc(C4(C(=O)O)CC4)cc3)CC2)c1NC(=O)OC(C)c1ccccc1]
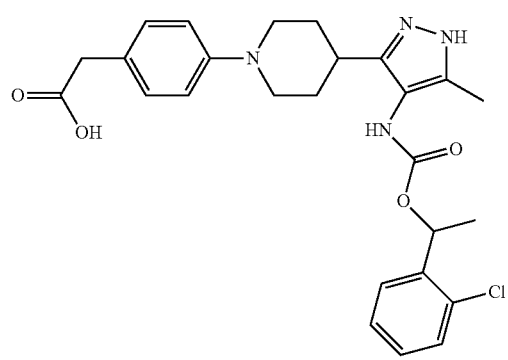 [SMILES: Cc1[nH]nc(C2CCN(c3ccc(CC(=O)O)cc3)CC2)c1NC(=O)OC(C)c1ccccc1Cl]
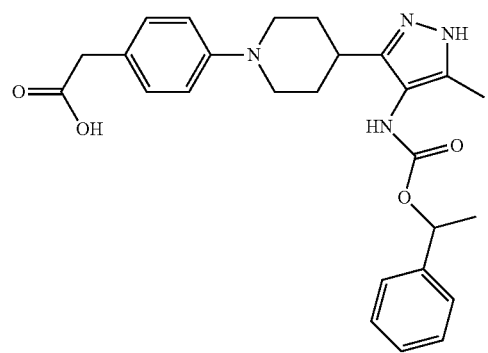 [SMILES: Cc1[nH]nc(C2CCN(c3ccc(CC(=O)O)cc3)CC2)c1NC(=O)OC(C)c1ccccc1]
308
TABLE 4-continued
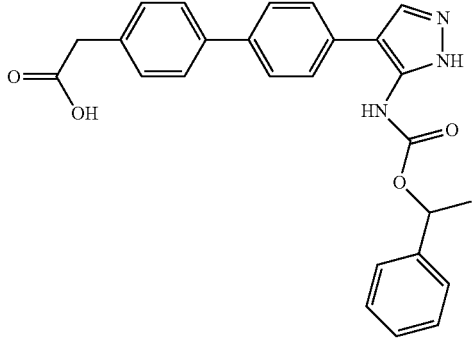 [SMILES: CC(OC(=O)Nc1[nH]ncc1-c1ccc(-c2ccc(CC(=O)O)cc2)cc1)c1ccccc1]
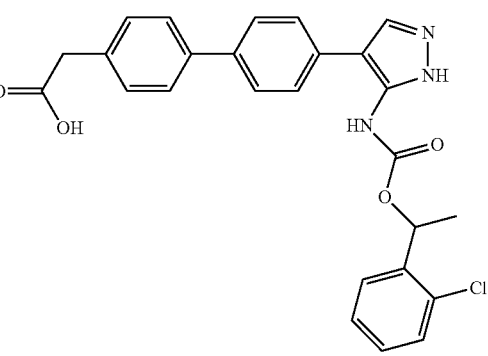
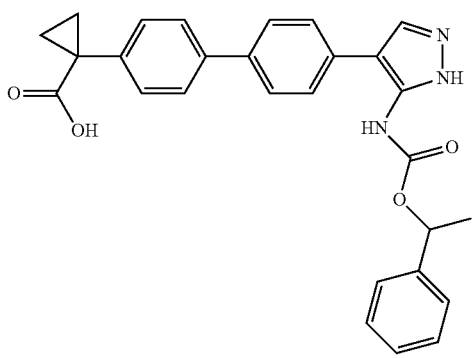
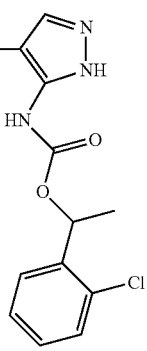

| 309 | 310 |
|---|---|
| TABLE 4-continued | TABLE 4-continued |
| 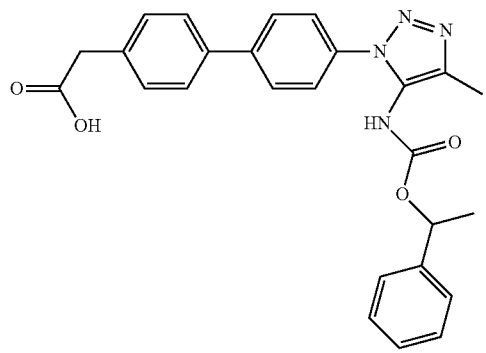 [SMILES: Cc1nnn(-c2ccc(-c3ccc(CC(=O)O)cc3)cc2)c1NC(=O)OC(C)c1ccccc1] | 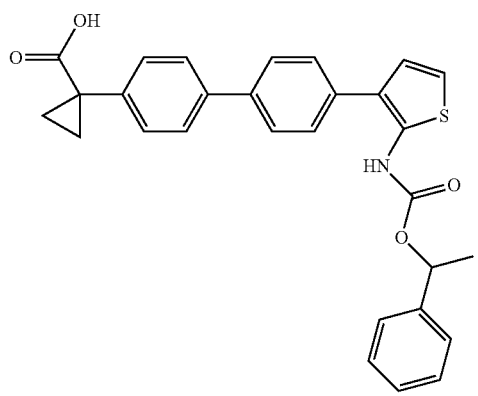 |
| 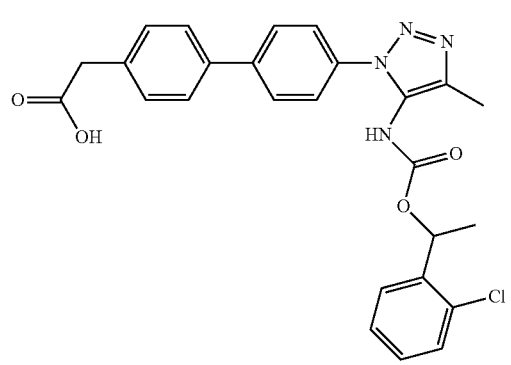 [SMILES: Cc1nnn(-c2ccc(-c3ccc(CC(=O)O)cc3)cc2)c1NC(=O)OC(C)c1ccccc1Cl] | 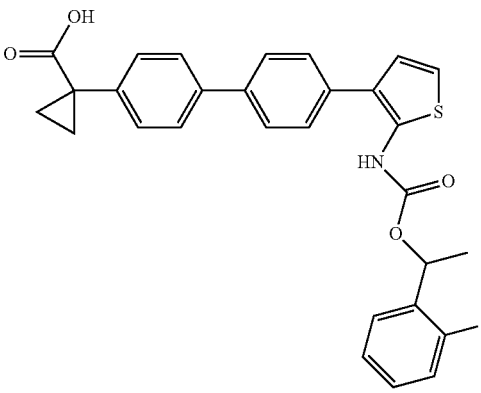 |
| 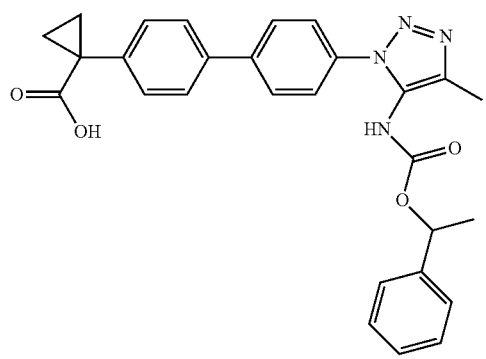 [SMILES: Cc1nnn(-c2ccc(-c3ccc(C4(C(=O)O)CC4)cc3)cc2)c1NC(=O)OC(C)c1ccccc1] | 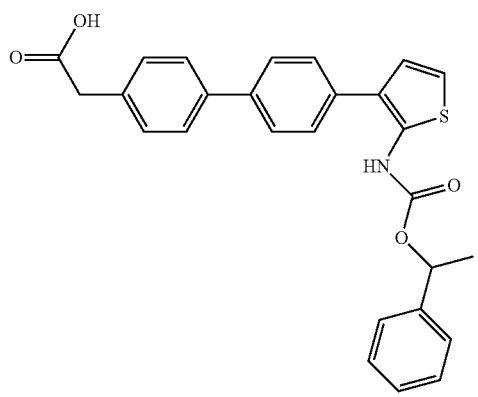 |
| 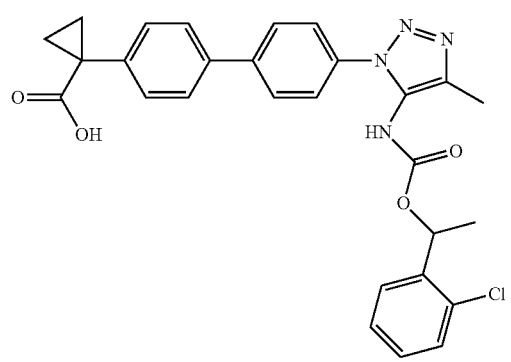 [SMILES: Cc1nnn(-c2ccc(-c3ccc(C4(C(=O)O)CC4)cc3)cc2)c1NC(=O)OC(C)c1ccccc1Cl] | 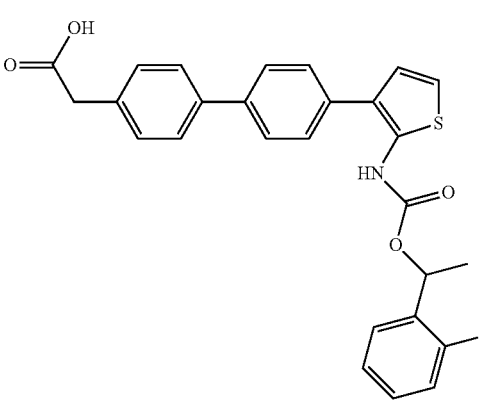 |

TABLE 4-continued
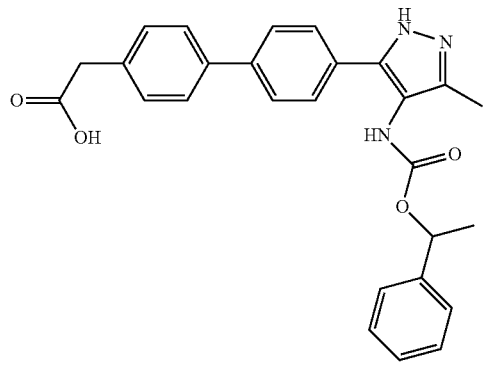 [SMILES: Cc1n[nH]c(-c2ccc(-c3ccc(CC(=O)O)cc3)cc2)c1NC(=O)OC(C)c1ccccc1]
311
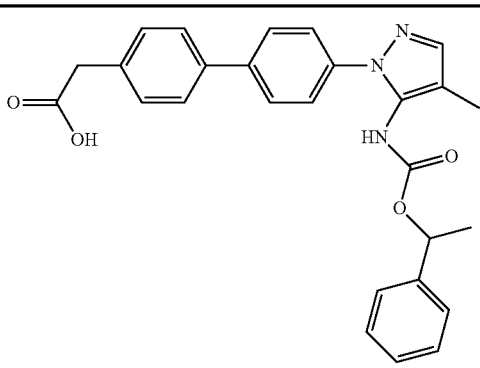
312
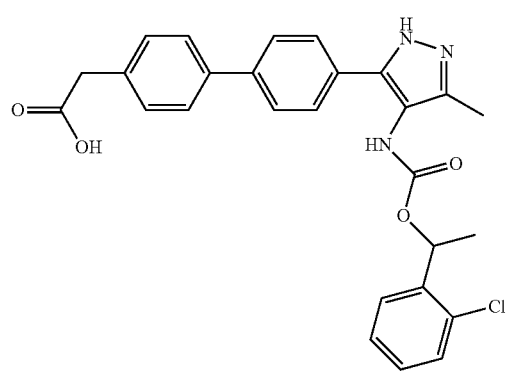 [SMILES: Cc1n[nH]c(-c2ccc(-c3ccc(CC(=O)O)cc3)cc2)c1NC(=O)OC(C)c1ccccc1Cl]
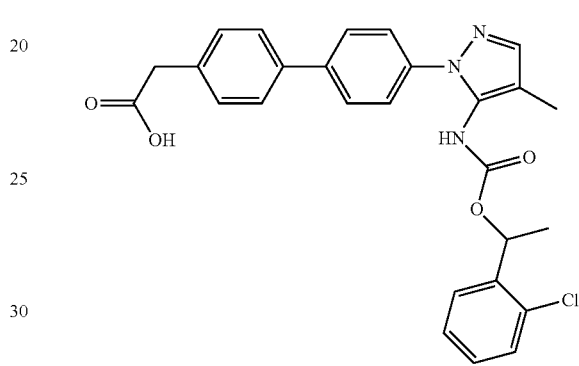
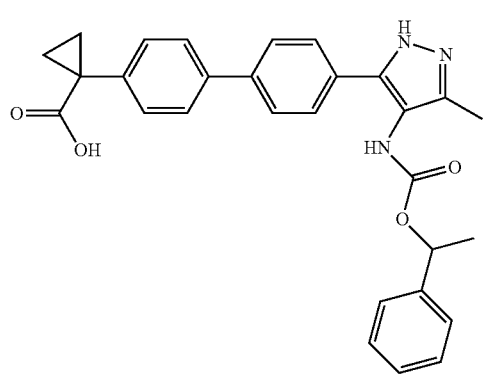 [SMILES: Cc1n[nH]c(-c2ccc(-c3ccc(C4(C(=O)O)CC4)cc3)cc2)c1NC(=O)OC(C)c1ccccc1]
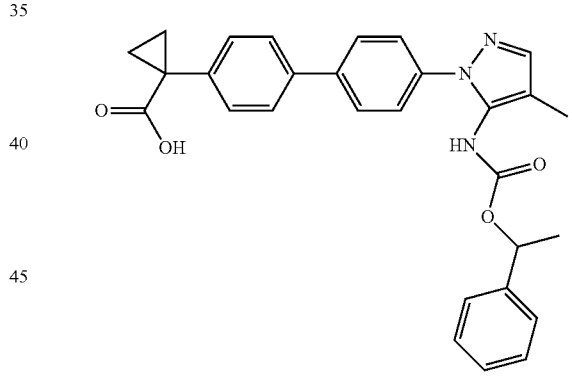
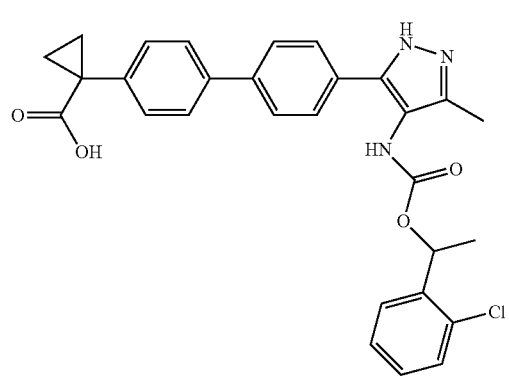 [SMILES: Cc1n[nH]c(-c2ccc(-c3ccc(C4(C(=O)O)CC4)cc3)cc2)c1NC(=O)OC(C)c1ccccc1Cl]
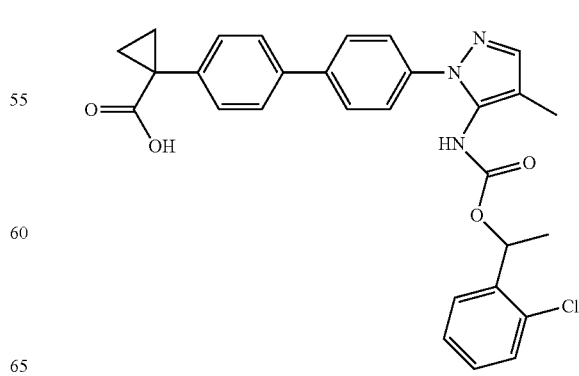

313
TABLE 4-continued
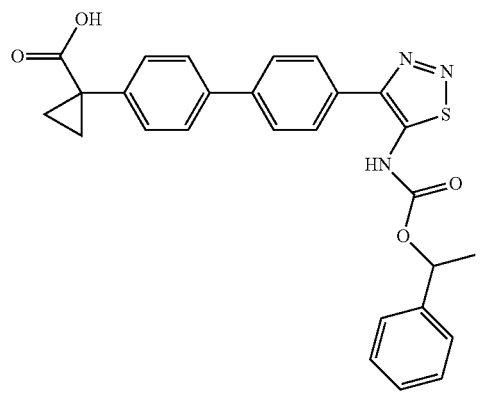
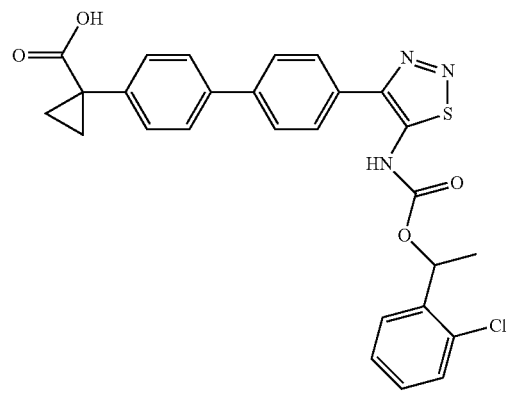 [SMILES: CC(OC(=O)Nc1snnc1-c1ccc(-c2ccc(C3(C(=O)O)CC3)cc2)cc1)c1ccccc1Cl]
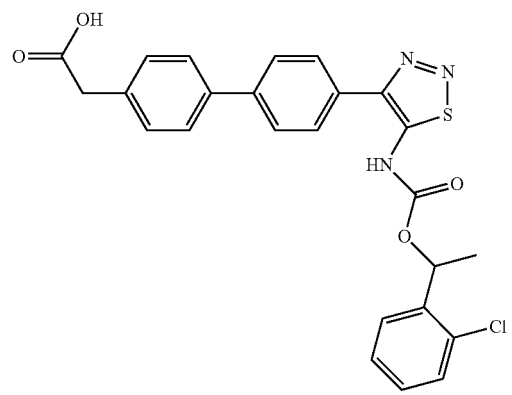 [SMILES: CC(OC(=O)Nc1snnc1-c1ccc(-c2ccc(CC(=O)O)cc2)cc1)c1ccccc1Cl]
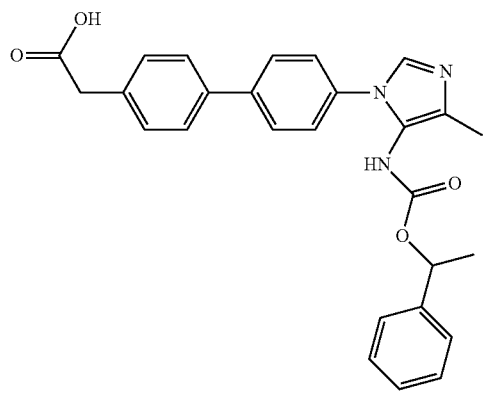 [SMILES: Cc1ncn(-c2ccc(-c3ccc(CC(=O)O)cc3)cc2)c1NC(=O)OC(C)c1ccccc1]
314
TABLE 4-continued
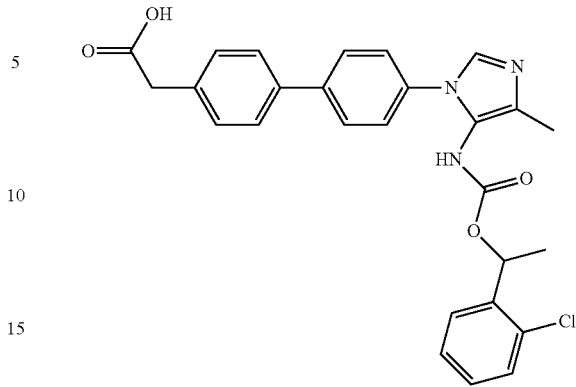
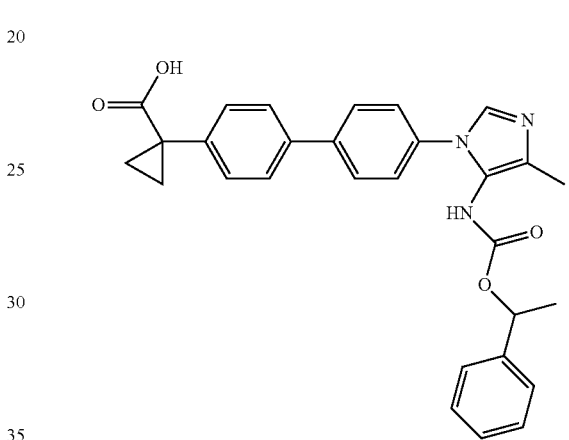
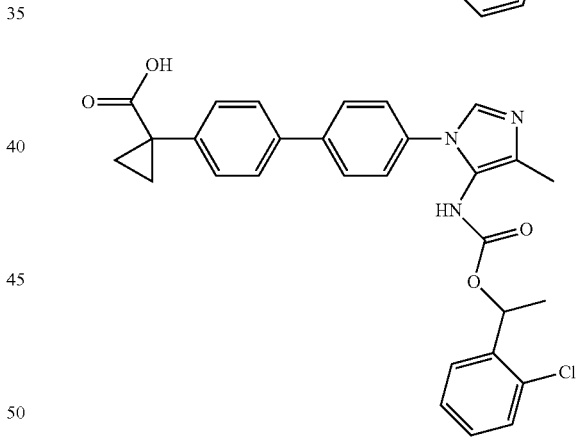
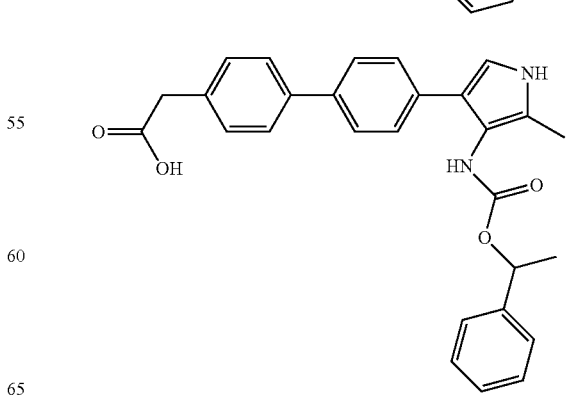

TABLE 4-continued
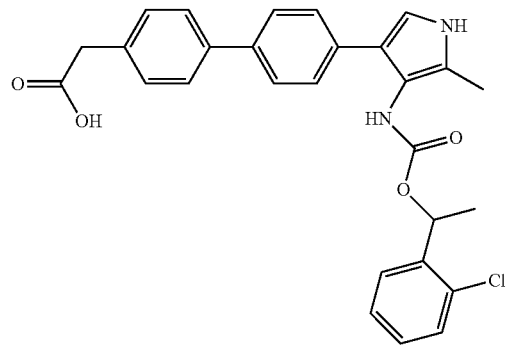 [SMILES: Cc1[nH]cc(-c2ccc(-c3ccc(CC(=O)O)cc3)cc2)c1NC(=O)OC(C)c1ccccc1Cl]
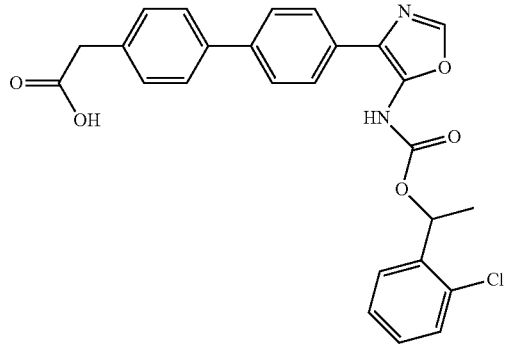
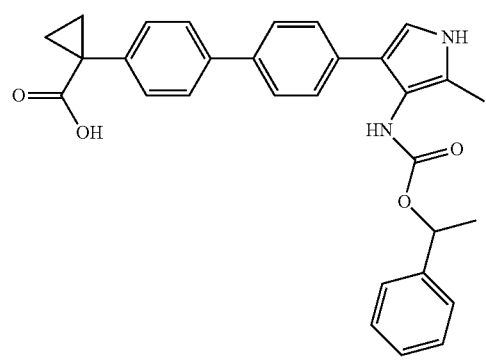 [SMILES: Cc1[nH]cc(-c2ccc(-c3ccc(C4(C(=O)O)CC4)cc3)cc2)c1NC(=O)OC(C)c1ccccc1]
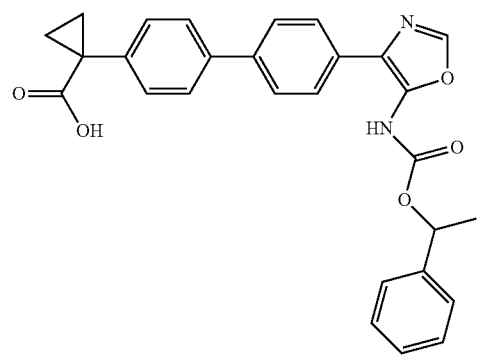
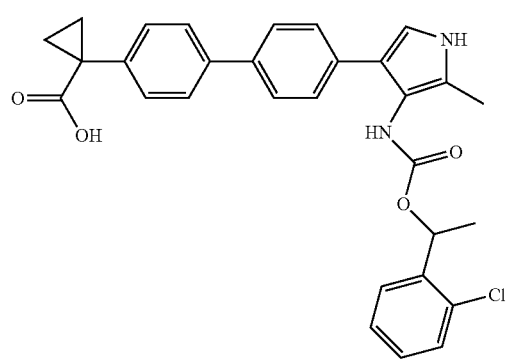 [SMILES: Cc1[nH]cc(-c2ccc(-c3ccc(C4(C(=O)O)CC4)cc3)cc2)c1NC(=O)OC(C)c1ccccc1Cl]
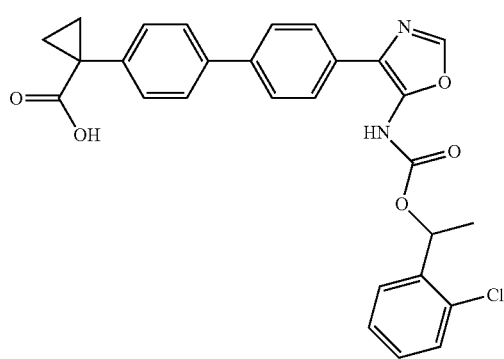
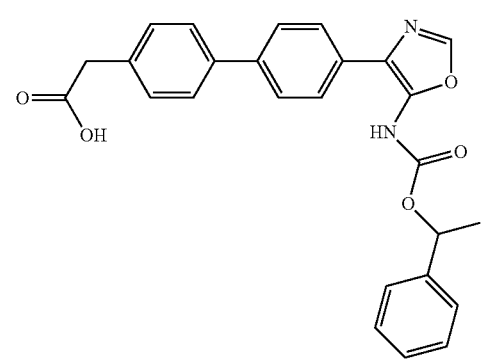 [SMILES: CC(OC(=O)Nc1ocnc1-c1ccc(-c2ccc(CC(=O)O)cc2)cc1)c1ccccc1]
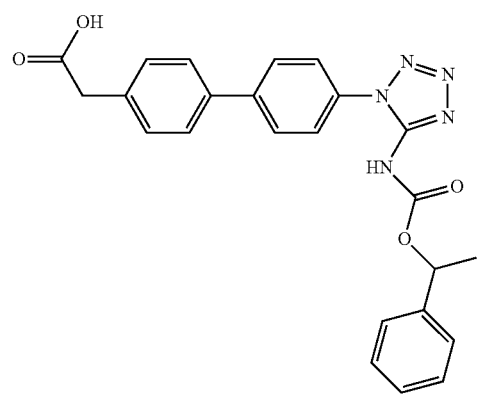 [SMILES: CC(OC(=O)Nc1nnnn1-c1ccc(-c2ccc(CC(=O)O)cc2)cc1)c1ccccc1]

| 317 | 318 |
|---|---|
| TABLE 4-continued | TABLE 4-continued |
| 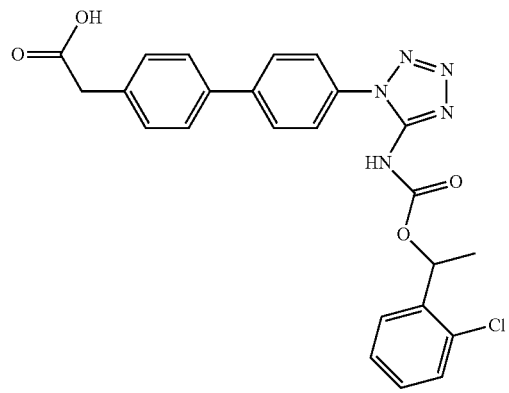 [SMILES: CC(OC(=O)Nc1nnnn1-c1ccc(-c2ccc(CC(=O)O)cc2)cc1)c1ccccc1Cl] | 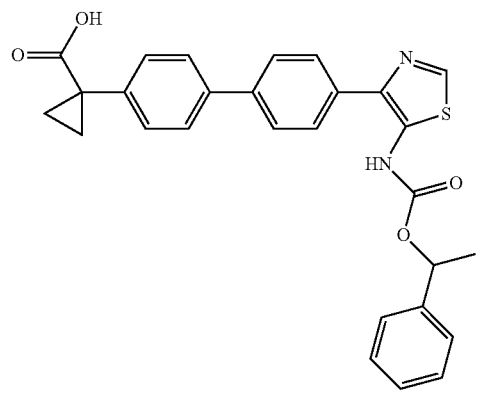 |
| 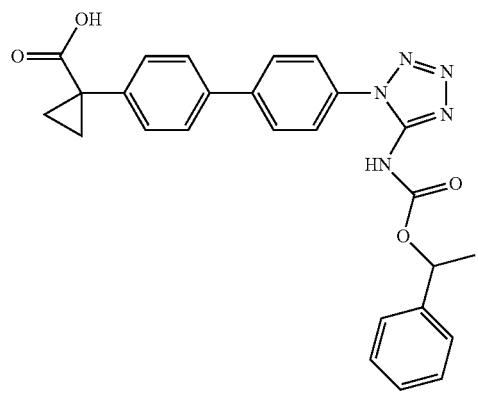 [SMILES: CC(OC(=O)Nc1nnnn1-c1ccc(-c2ccc(C3(C(=O)O)CC3)cc2)cc1)c1ccccc1] | 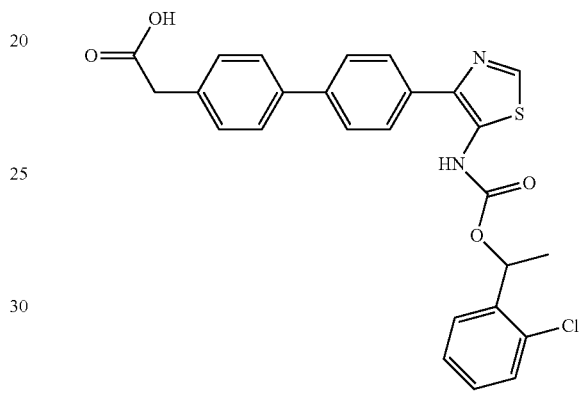 |
| 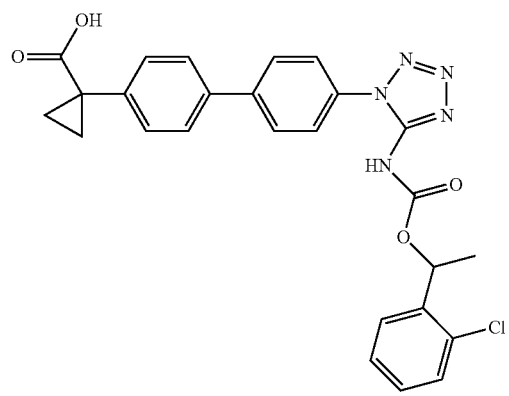 [SMILES: CC(OC(=O)Nc1nnnn1-c1ccc(-c2ccc(C3(C(=O)O)CC3)cc2)cc1)c1ccccc1Cl] | 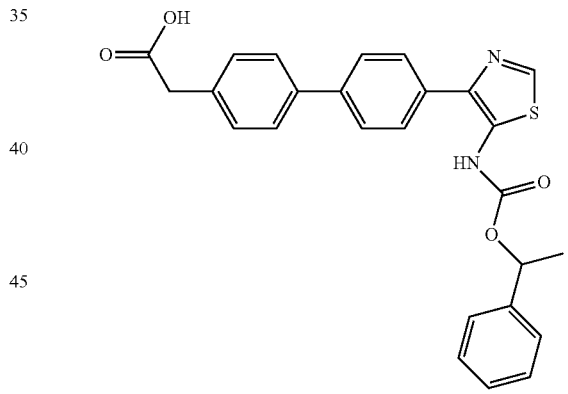 |
| 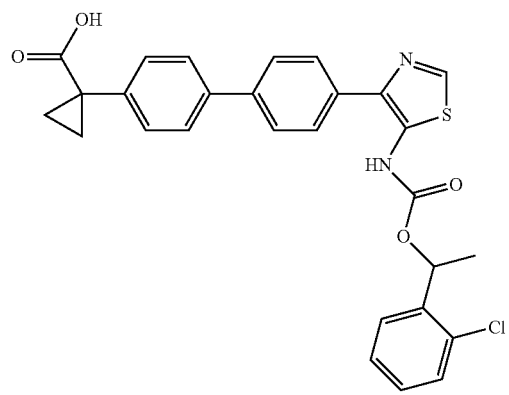 | 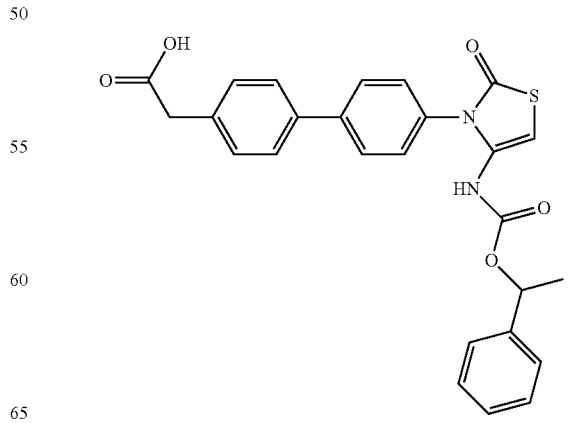 |

TABLE 4-continued
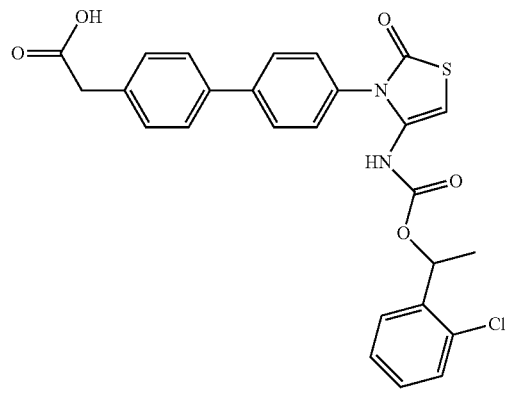 [SMILES: CC(OC(=O)Nc1csc(=O)n1-c1ccc(-c2ccc(CC(=O)O)cc2)cc1)c1ccccc1Cl]
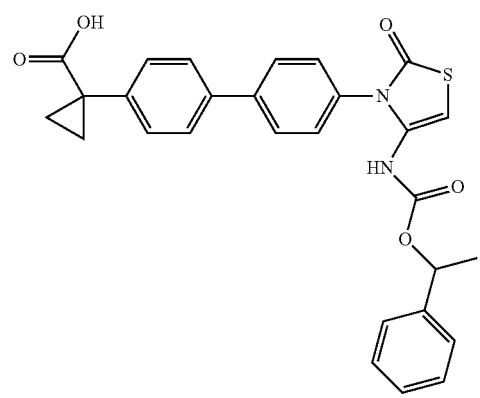 [SMILES: CC(OC(=O)Nc1csc(=O)n1-c1ccc(-c2ccc(C3(C(=O)O)CC3)cc2)cc1)c1ccccc1]
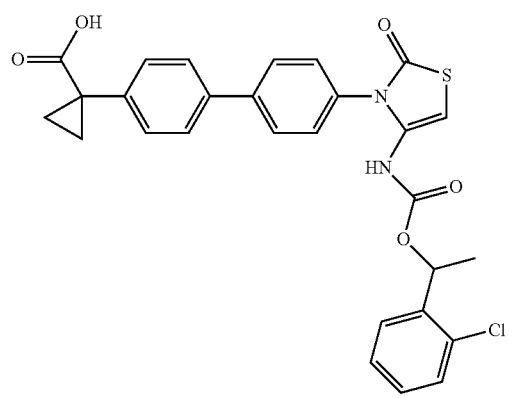 [SMILES: CC(OC(=O)Nc1csc(=O)n1-c1ccc(-c2ccc(C3(C(=O)O)CC3)cc2)cc1)c1ccccc1Cl]
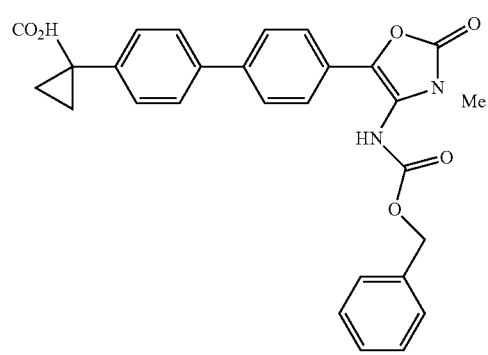 [SMILES: O=C(Nc1[nH]c(=O)oc1-c1ccc(-c2ccc(C3(C(=O)O)CC3)cc2)cc1)OCc1ccccc1]
TABLE 4-continued
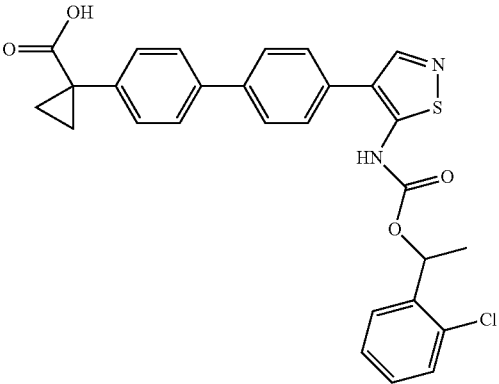 [SMILES: CC(OC(=O)Nc1sncc1-c1ccc(-c2ccc(C3(C(=O)O)CC3)cc2)cc1)c1ccccc1Cl]
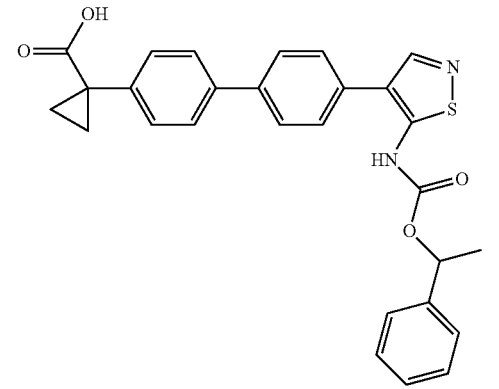
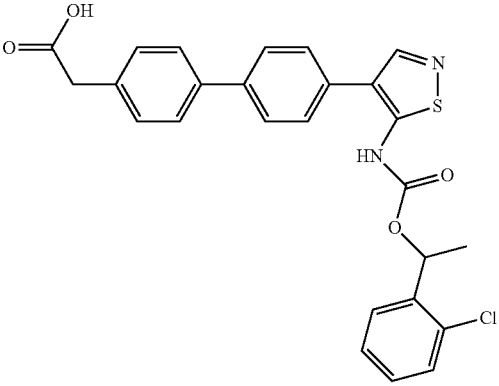 [SMILES: CC(OC(=O)Nc1sncc1-c1ccc(-c2ccc(CC(=O)O)cc2)cc1)c1ccccc1Cl]
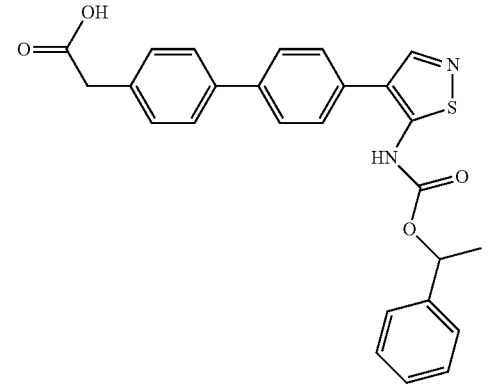

TABLE 4-continued
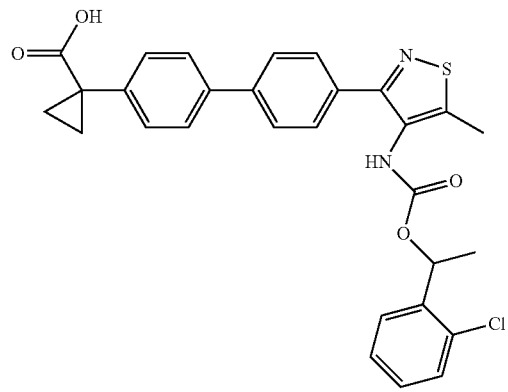 [SMILES: Cc1snc(-c2ccc(-c3ccc(C4(C(=O)O)CC4)cc3)cc2)c1NC(=O)OC(C)c1ccccc1Cl]
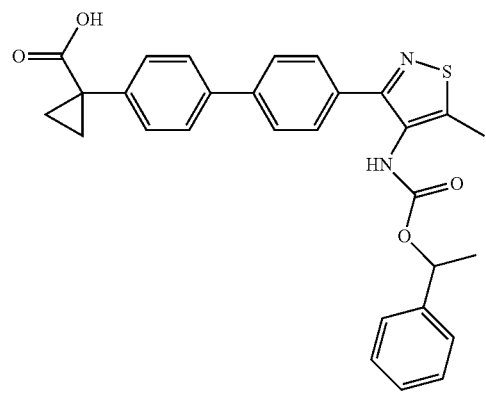 [SMILES: Cc1snc(-c2ccc(-c3ccc(C4(C(=O)O)CC4)cc3)cc2)c1NC(=O)OC(C)c1ccccc1]
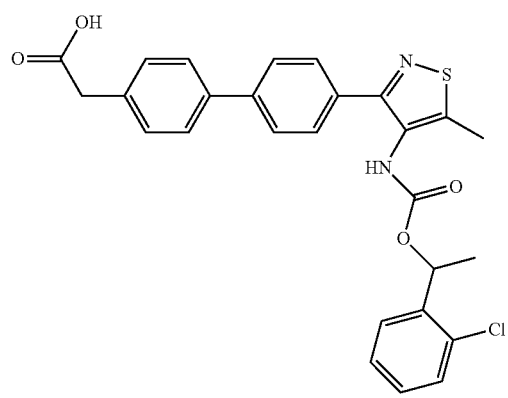 [SMILES: Cc1snc(-c2ccc(-c3ccc(CC(=O)O)cc3)cc2)c1NC(=O)OC(C)c1ccccc1Cl]
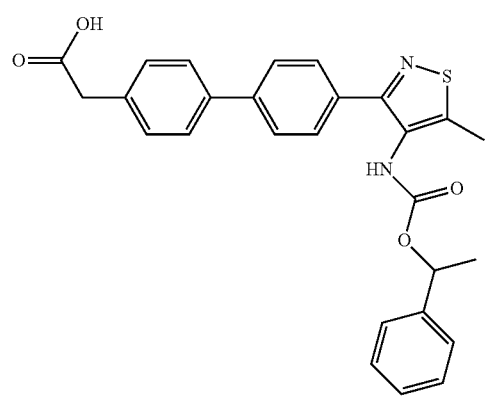
TABLE 4-continued
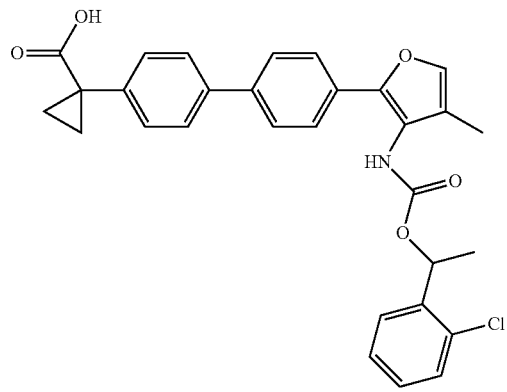 [SMILES: Cc1coc(-c2ccc(-c3ccc(C4(C(=O)O)CC4)cc3)cc2)c1NC(=O)OC(C)c1ccccc1Cl]
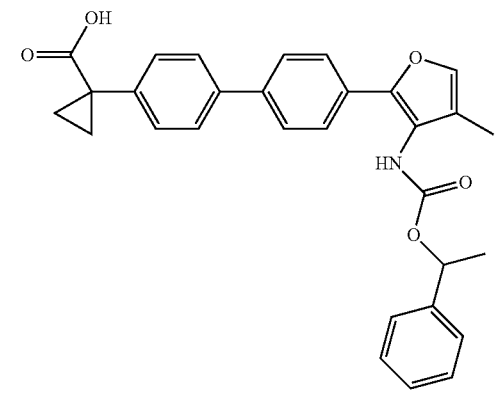
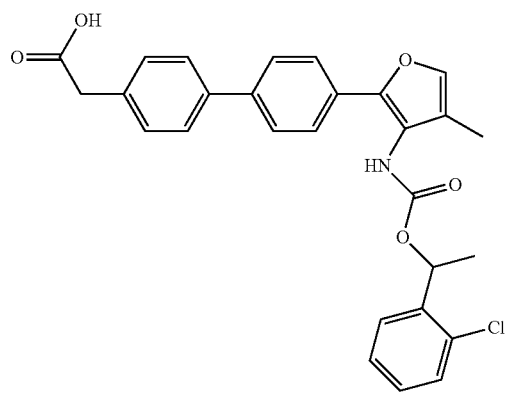 [SMILES: Cc1coc(-c2ccc(-c3ccc(CC(=O)O)cc3)cc2)c1NC(=O)OC(C)c1ccccc1Cl]
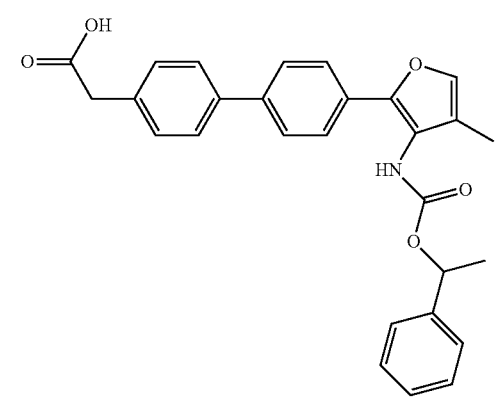 [SMILES: Cc1coc(-c2ccc(-c3ccc(CC(=O)O)cc3)cc2)c1NC(=O)OC(C)c1ccccc1]

TABLE 4-continued
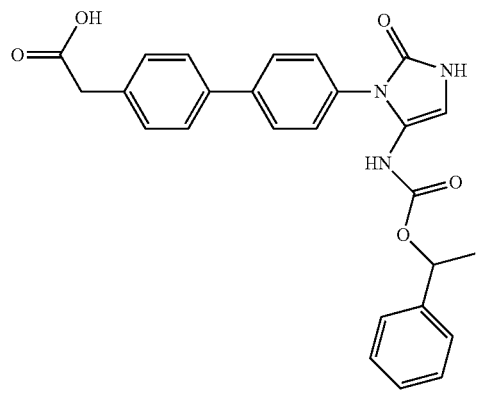 [SMILES: CC(OC(=O)Nc1c[nH]c(=O)n1-c1ccc(-c2ccc(CC(=O)O)cc2)cc1)c1ccccc1]
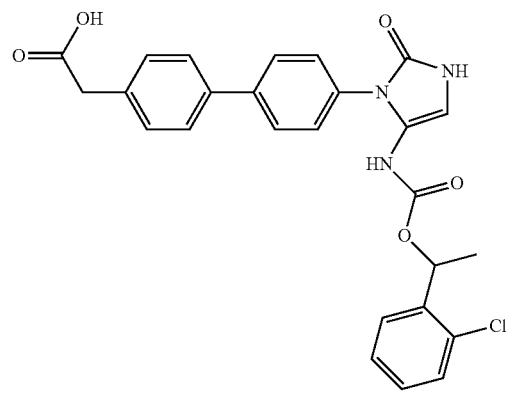
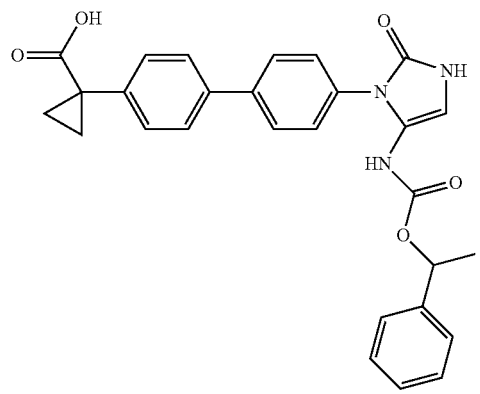 [SMILES: CC(OC(=O)Nc1c[nH]c(=O)n1-c1ccc(-c2ccc(C3(C(=O)O)CC3)cc2)cc1)c1ccccc1]
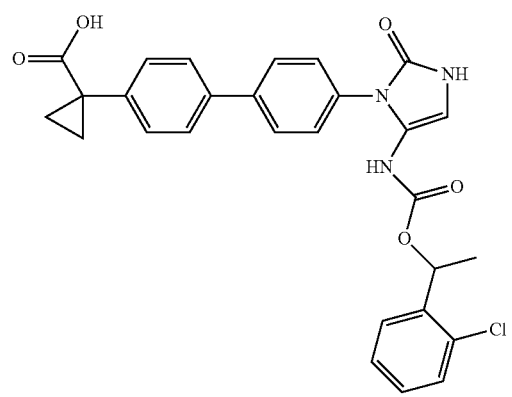 [SMILES: CC(OC(=O)Nc1c[nH]c(=O)n1-c1ccc(-c2ccc(C3(C(=O)O)CC3)cc2)cc1)c1ccccc1Cl]
TABLE 4-continued
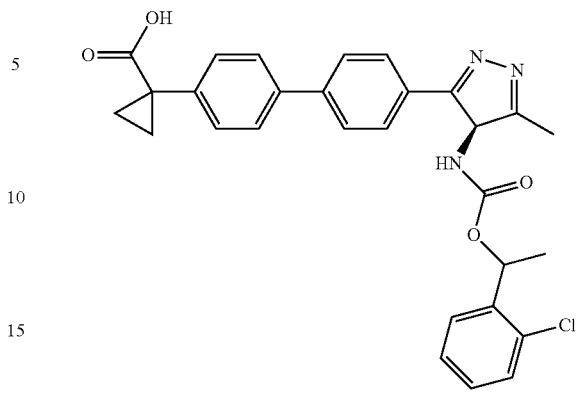
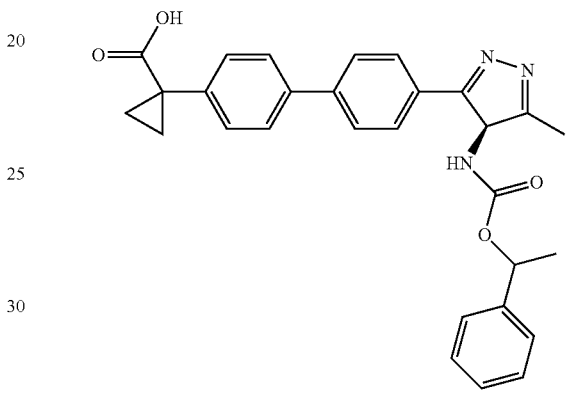
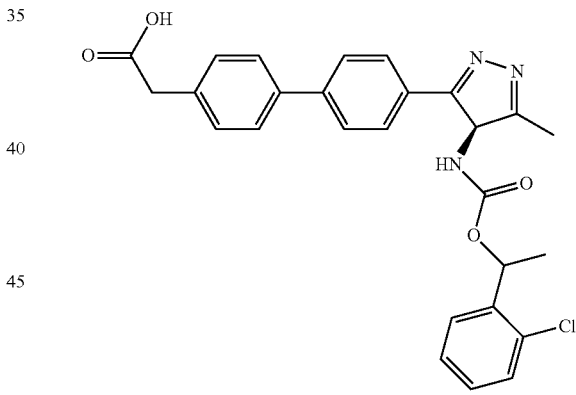
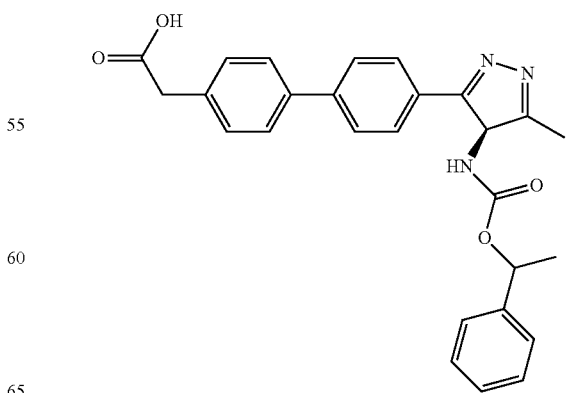

TABLE 4-continued
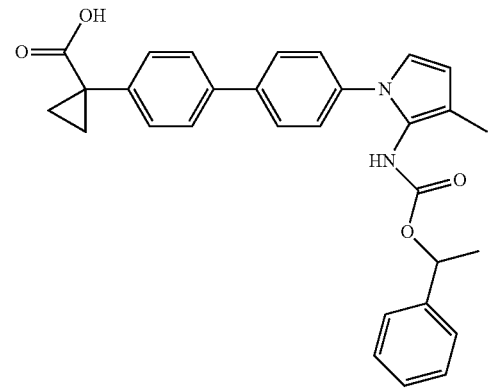
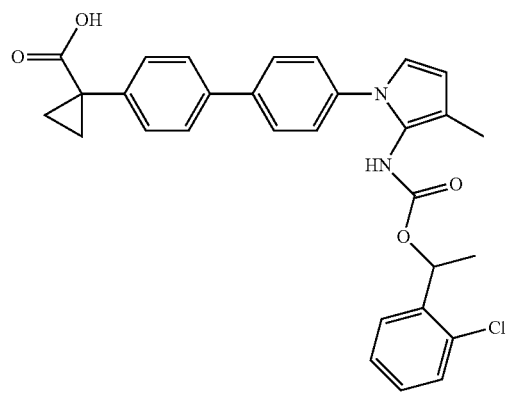 [SMILES: Cc1ccn(-c2ccc(-c3ccc(C4(C(=O)O)CC4)cc3)cc2)c1NC(=O)OC(C)c1ccccc1Cl]
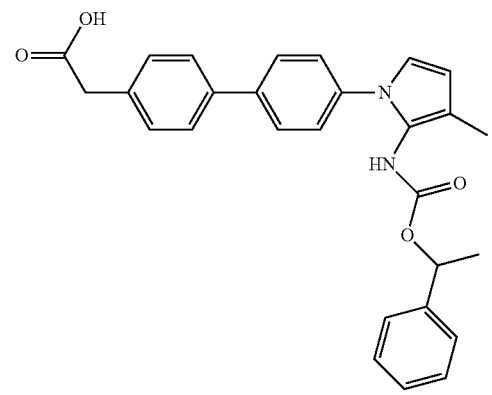 [SMILES: Cc1ccn(-c2ccc(-c3ccc(CC(=O)O)cc3)cc2)c1NC(=O)OC(C)c1ccccc1]
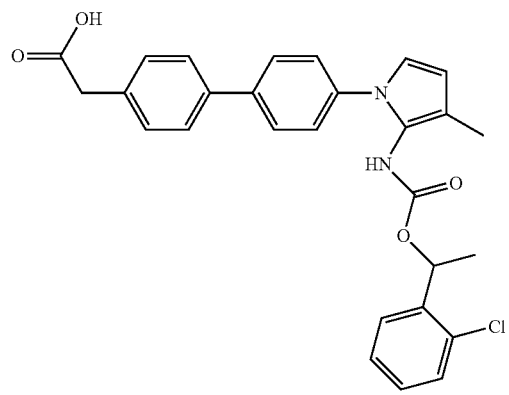
TABLE 4-continued
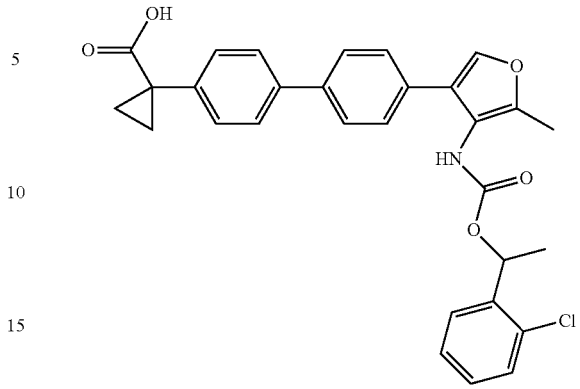
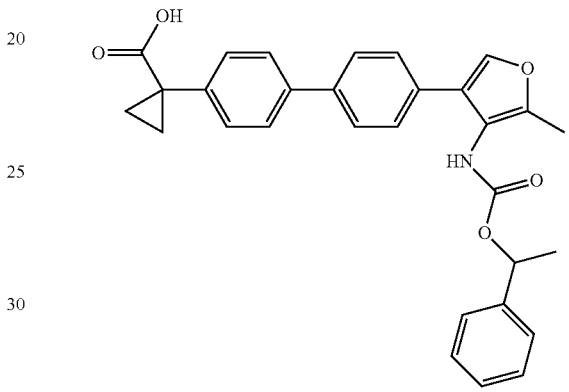
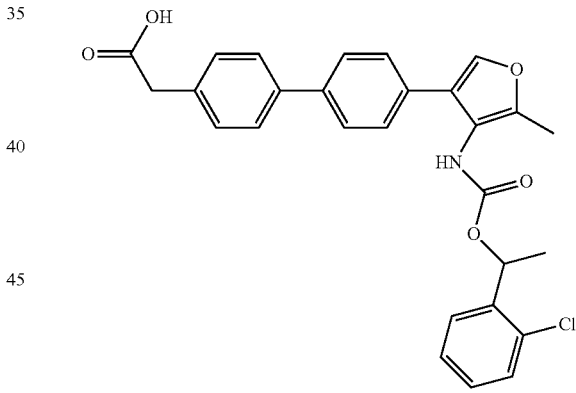
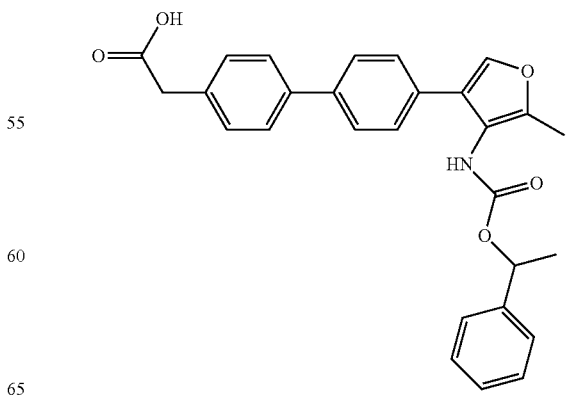

TABLE 4-continued
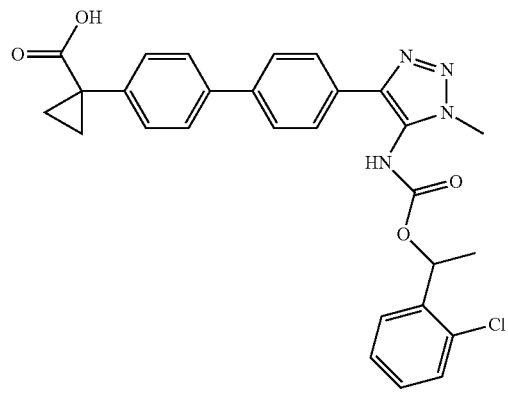 [SMILES: CC(OC(=O)Nc1c(-c2ccc(-c3ccc(C4(C(=O)O)CC4)cc3)cc2)nnn1C)c1ccccc1Cl]
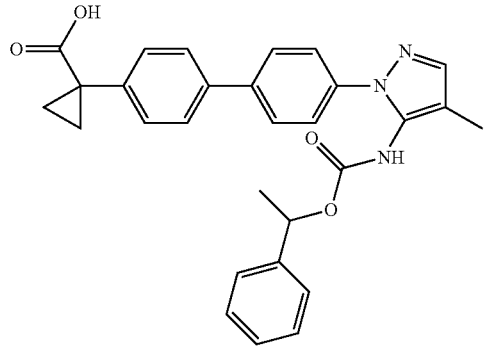
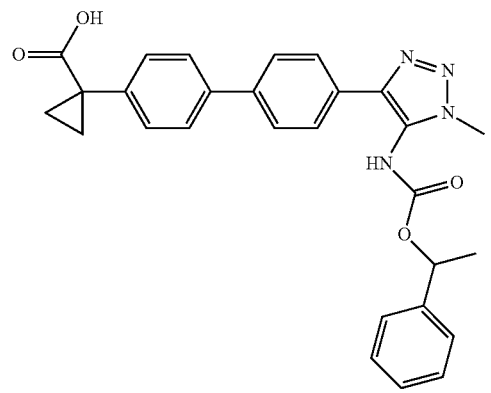 [SMILES: CC(OC(=O)Nc1c(-c2ccc(-c3ccc(C4(C(=O)O)CC4)cc3)cc2)nnn1C)c1ccccc1]
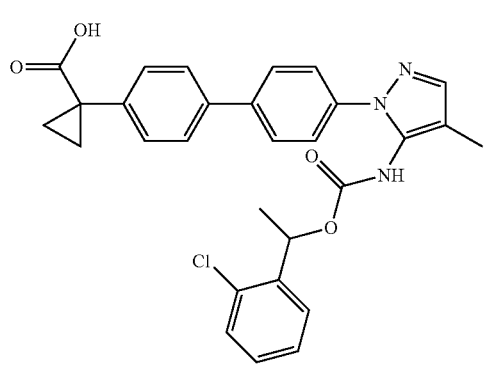
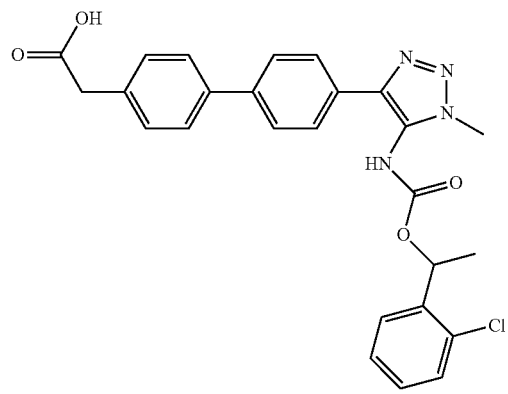 [SMILES: CC(OC(=O)Nc1c(-c2ccc(-c3ccc(CC(=O)O)cc3)cc2)nnn1C)c1ccccc1Cl]
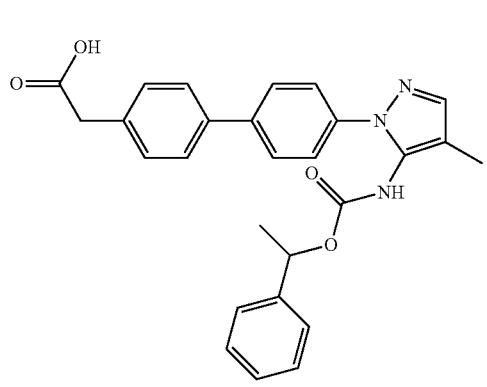
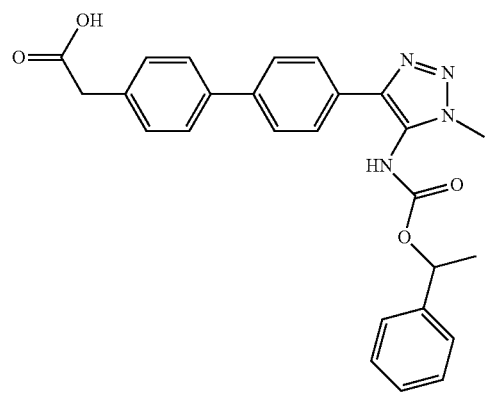 [SMILES: CC(OC(=O)Nc1c(-c2ccc(-c3ccc(CC(=O)O)cc3)cc2)nnn1C)c1ccccc1]
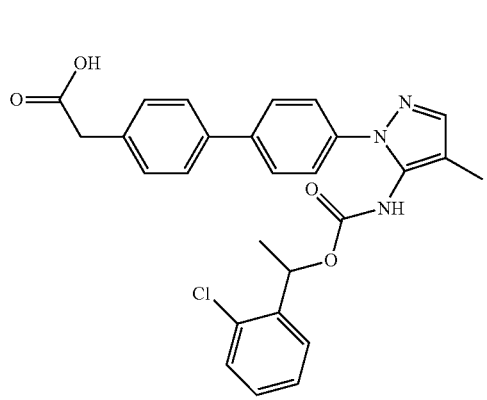 [SMILES: Cc1cnn(-c2ccc(-c3ccc(CC(=O)O)cc3)cc2)c1NC(=O)OC(C)c1ccccc1Cl]

TABLE 4-continued
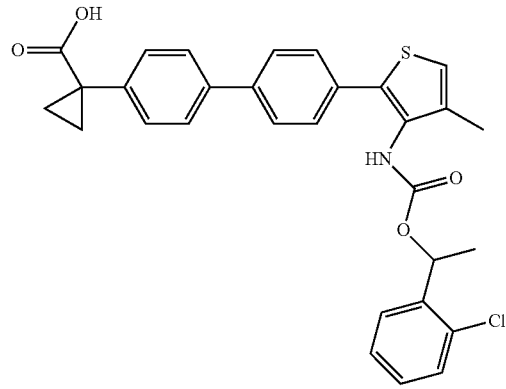
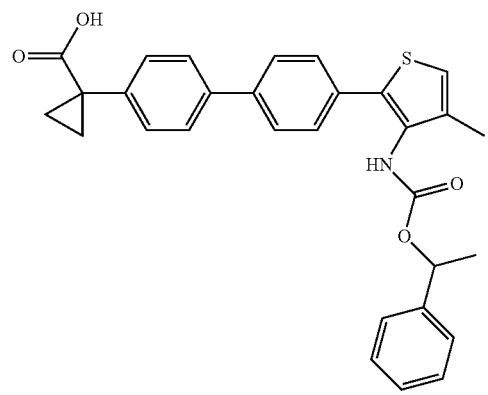 [SMILES: Cc1csc(-c2ccc(-c3ccc(C4(C(=O)O)CC4)cc3)cc2)c1NC(=O)OC(C)c1ccccc1]
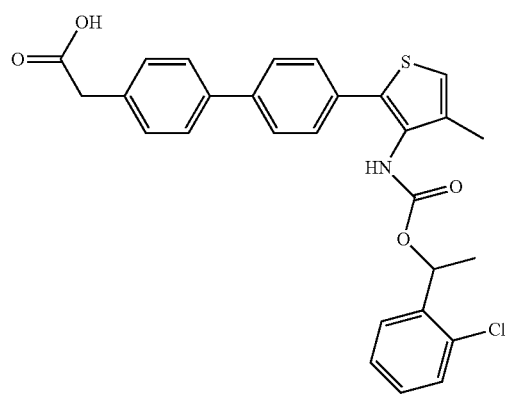
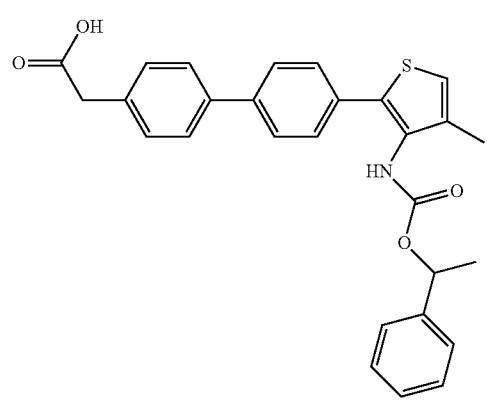 [SMILES: Cc1csc(-c2ccc(-c3ccc(CC(=O)O)cc3)cc2)c1NC(=O)OC(C)c1ccccc1]
TABLE 4-continued
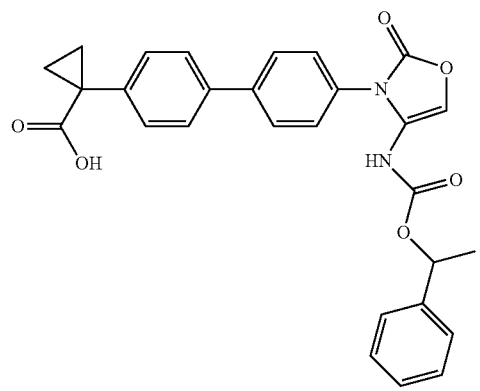 [SMILES: CC(OC(=O)Nc1coc(=O)n1-c1ccc(-c2ccc(C3(C(=O)O)CC3)cc2)cc1)c1ccccc1]
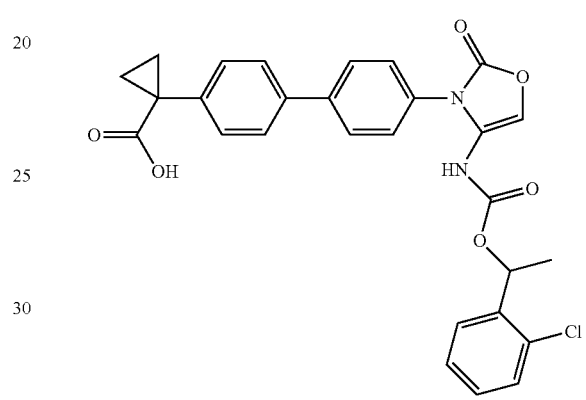
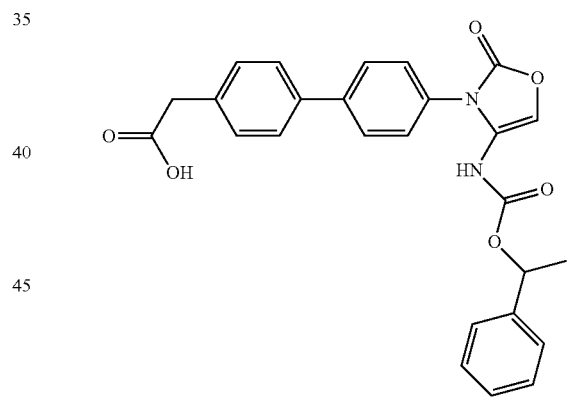

TABLE 4-continued
331
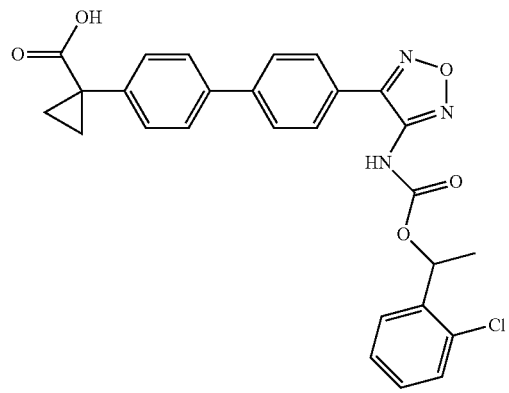
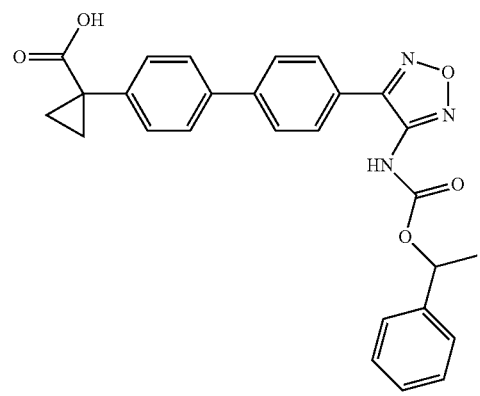 [SMILES: CC(OC(=O)Nc1nonc1-c1ccc(-c2ccc(C3(C(=O)O)CC3)cc2)cc1)c1ccccc1]
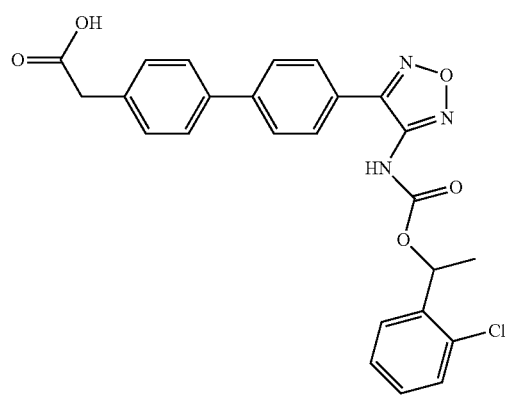 [SMILES: CC(OC(=O)Nc1nonc1-c1ccc(-c2ccc(CC(=O)O)cc2)cc1)c1ccccc1Cl]
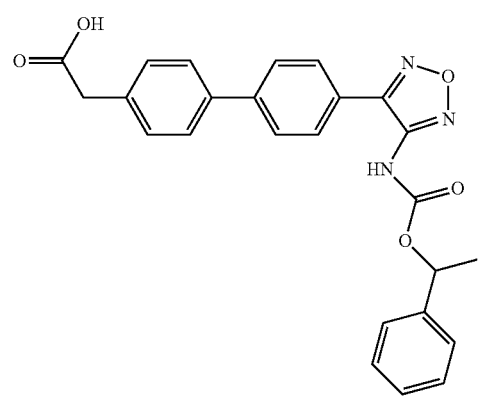 [SMILES: CC(OC(=O)Nc1nonc1-c1ccc(-c2ccc(CC(=O)O)cc2)cc1)c1ccccc1]
TABLE 4-continued
332
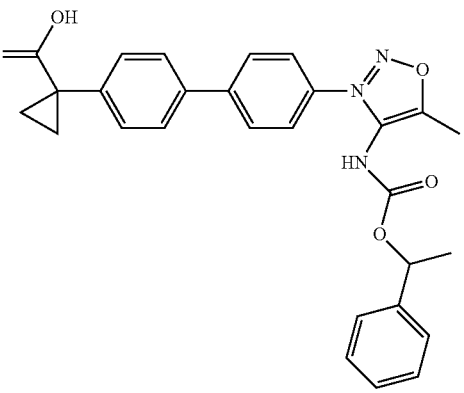
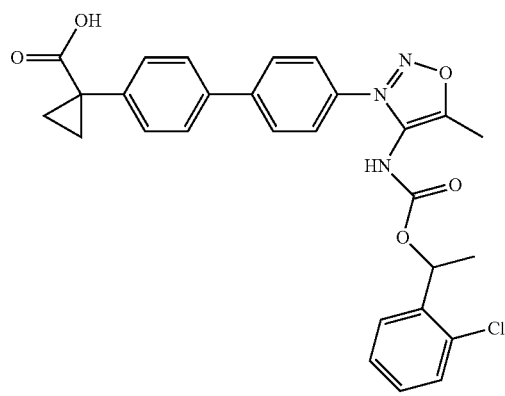

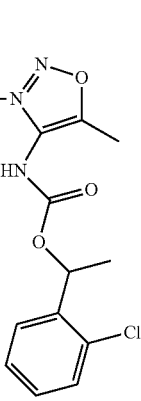

TABLE 4-continued
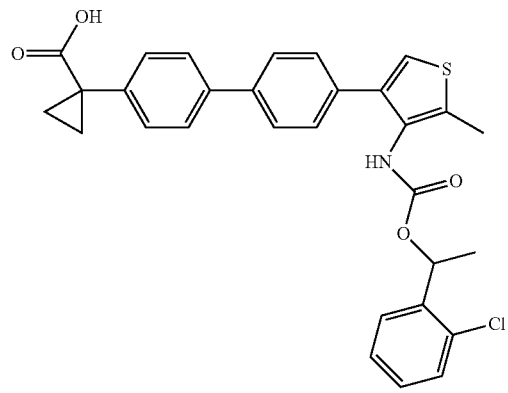 [SMILES: Cc1scc(-c2ccc(-c3ccc(C4(C(=O)O)CC4)cc3)cc2)c1NC(=O)OC(C)c1ccccc1Cl]
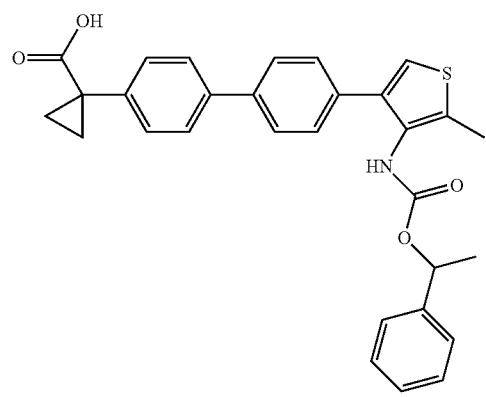 [SMILES: Cc1scc(-c2ccc(-c3ccc(C4(C(=O)O)CC4)cc3)cc2)c1NC(=O)OC(C)c1ccccc1]
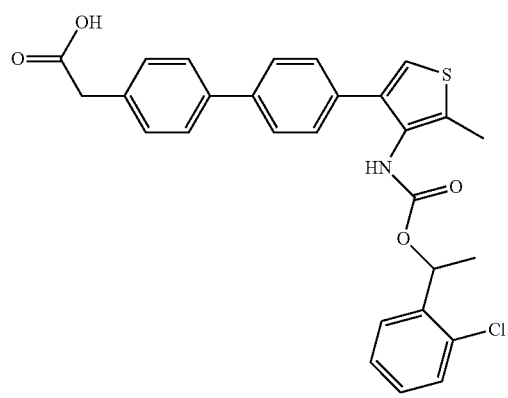
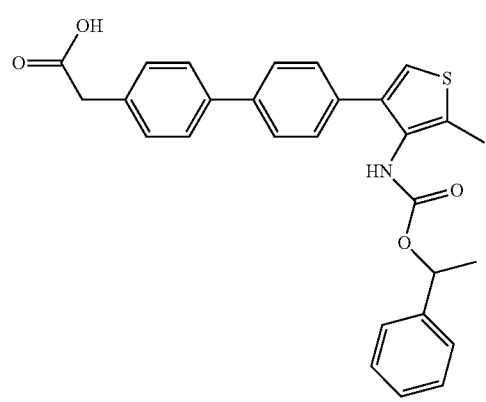 [SMILES: Cc1scc(-c2ccc(-c3ccc(CC(=O)O)cc3)cc2)c1NC(=O)OC(C)c1ccccc1]
TABLE 4-continued
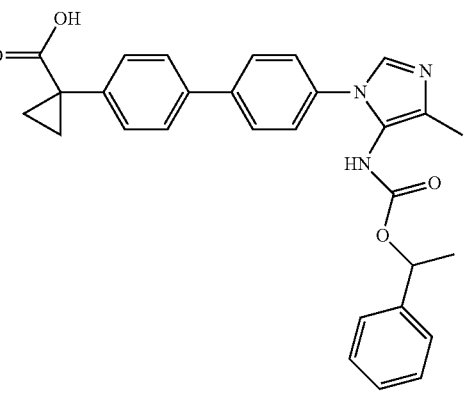
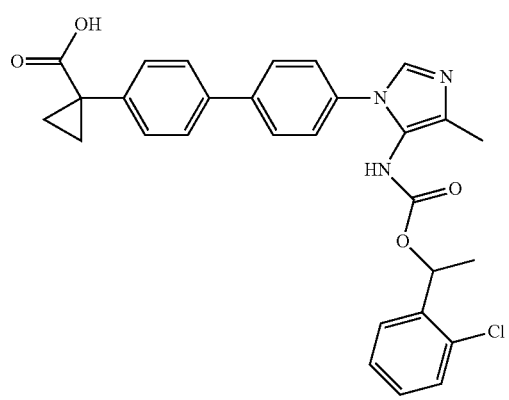 [SMILES: Cc1ncn(-c2ccc(-c3ccc(C4(C(=O)O)CC4)cc3)cc2)c1NC(=O)OC(C)c1ccccc1Cl]
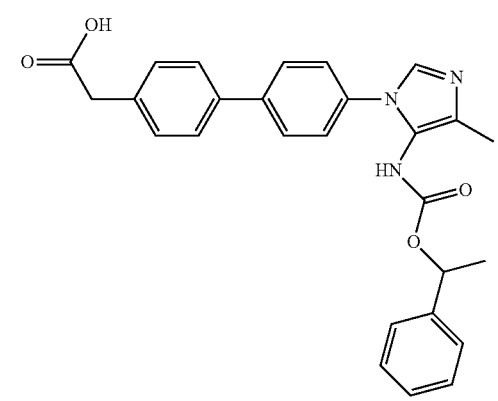
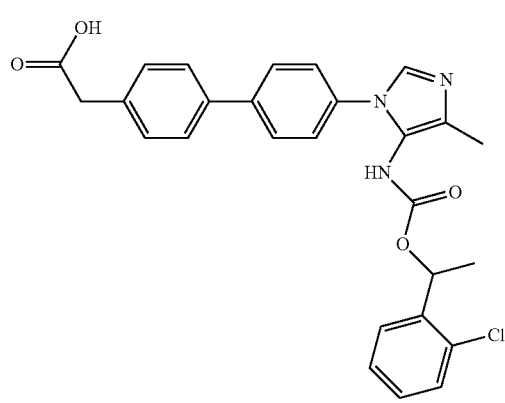 [SMILES: Cc1ncn(-c2ccc(-c3ccc(CC(=O)O)cc3)cc2)c1NC(=O)OC(C)c1ccccc1Cl]

TABLE 4-continued
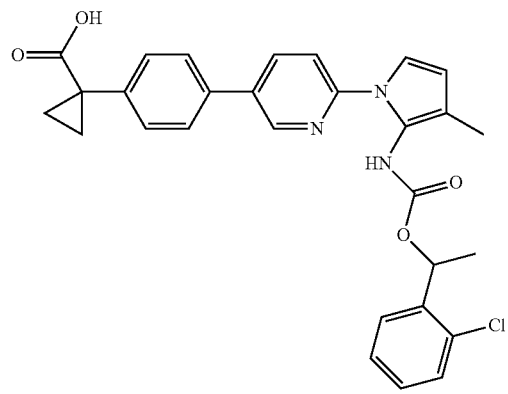 [SMILES: Cc1ccn(-c2ccc(-c3ccc(C4(C(=O)O)CC4)cc3)cn2)c1NC(=O)OC(C)c1ccccc1Cl]
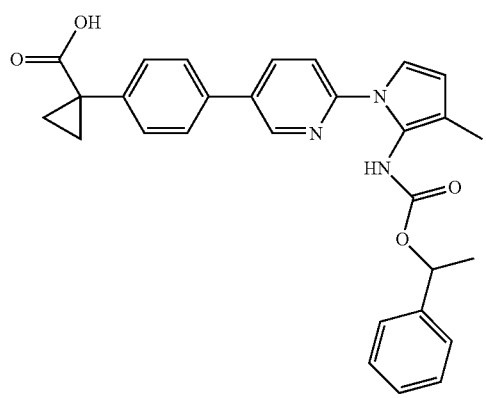 [SMILES: Cc1ccn(-c2ccc(-c3ccc(C4(C(=O)O)CC4)cc3)cn2)c1NC(=O)OC(C)c1ccccc1]
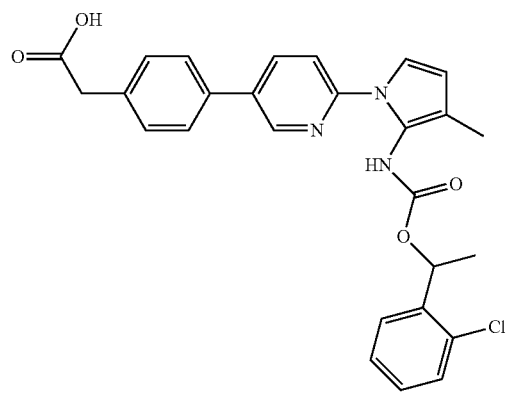 [SMILES: Cc1ccn(-c2ccc(-c3ccc(CC(=O)O)cc3)cn2)c1NC(=O)OC(C)c1ccccc1Cl]
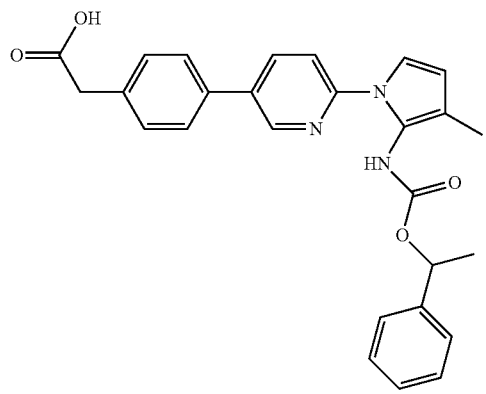 [SMILES: Cc1ccn(-c2ccc(-c3ccc(CC(=O)O)cc3)cn2)c1NC(=O)OC(C)c1ccccc1]
TABLE 4-continued
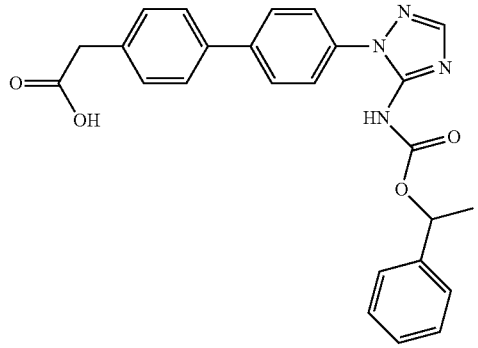 [SMILES: CC(OC(=O)Nc1ncnn1-c1ccc(-c2ccc(CC(=O)O)cc2)cc1)c1ccccc1]
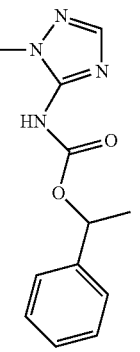
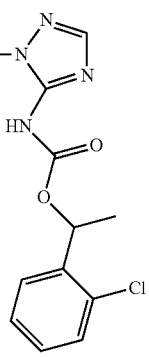

337
TABLE 4-continued
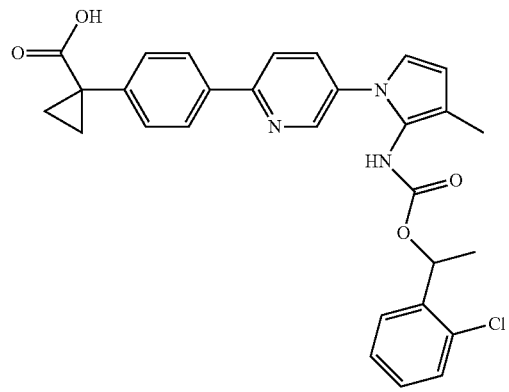 [SMILES: Cc1ccn(-c2ccc(-c3ccc(C4(C(=O)O)CC4)cc3)nc2)c1NC(=O)OC(C)c1ccccc1Cl]
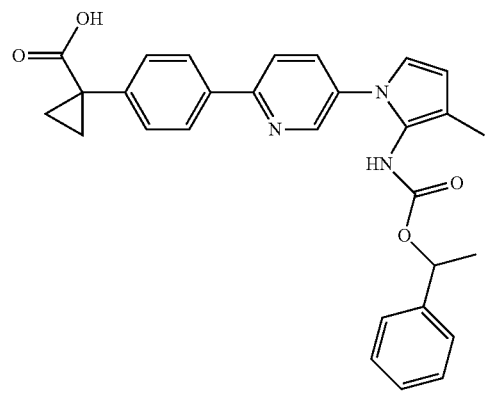 [SMILES: Cc1ccn(-c2ccc(-c3ccc(C4(C(=O)O)CC4)cc3)nc2)c1NC(=O)OC(C)c1ccccc1]
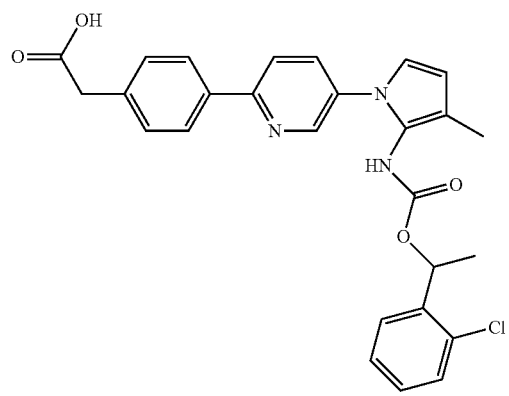 [SMILES: Cc1ccn(-c2ccc(-c3ccc(CC(=O)O)cc3)nc2)c1NC(=O)OC(C)c1ccccc1Cl]
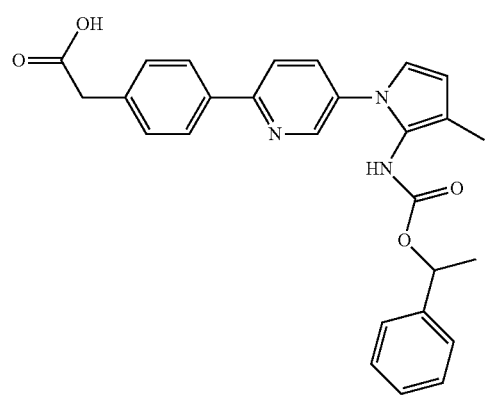
338
TABLE 4-continued
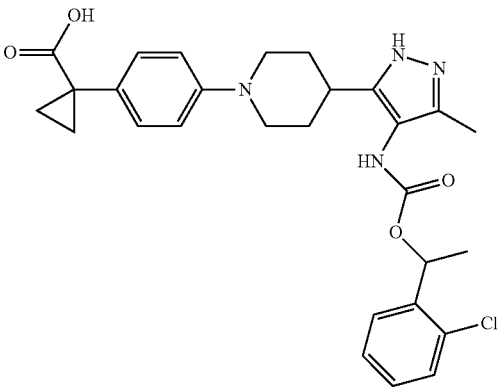 [SMILES: Cc1n[nH]c(C2CCN(c3ccc(C4(C(=O)O)CC4)cc3)CC2)c1NC(=O)OC(C)c1ccccc1Cl]
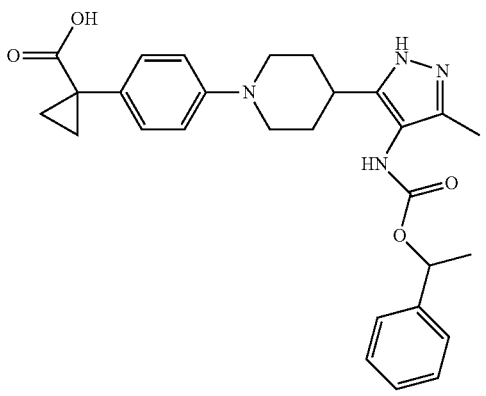 [SMILES: Cc1n[nH]c(C2CCN(c3ccc(C4(C(=O)O)CC4)cc3)CC2)c1NC(=O)OC(C)c1ccccc1]
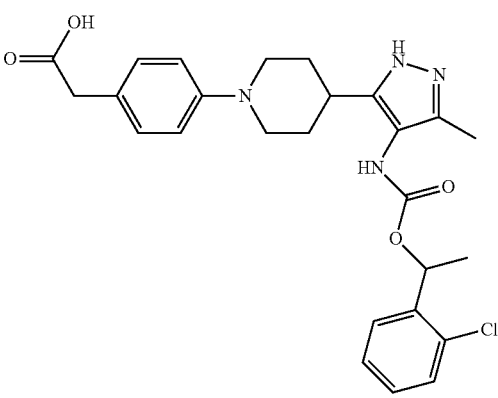 [SMILES: Cc1n[nH]c(C2CCN(c3ccc(CC(=O)O)cc3)CC2)c1NC(=O)OC(C)c1ccccc1Cl]
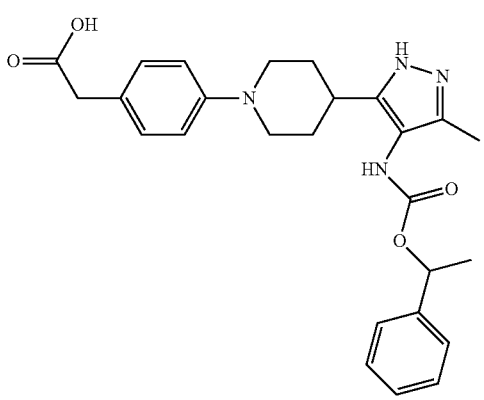 [SMILES: Cc1n[nH]c(C2CCN(c3ccc(CC(=O)O)cc3)CC2)c1NC(=O)OC(C)c1ccccc1]

TABLE 4-continued
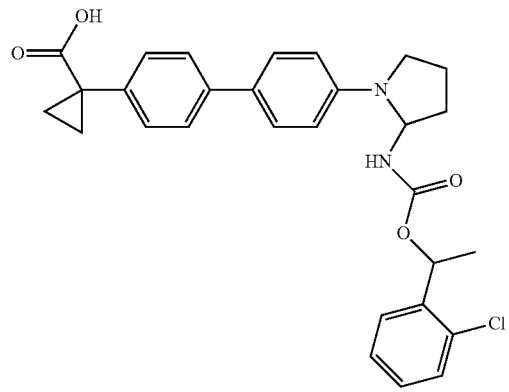 [SMILES: CC(OC(=O)NC1CCCN1c1ccc(-c2ccc(C3(C(=O)O)CC3)cc2)cc1)c1ccccc1Cl]
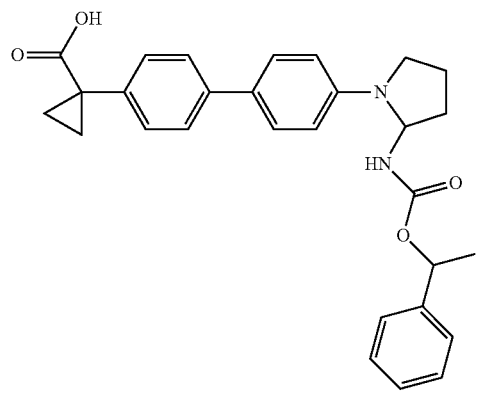 [SMILES: CC(OC(=O)NC1CCCN1c1ccc(-c2ccc(C3(C(=O)O)CC3)cc2)cc1)c1ccccc1]
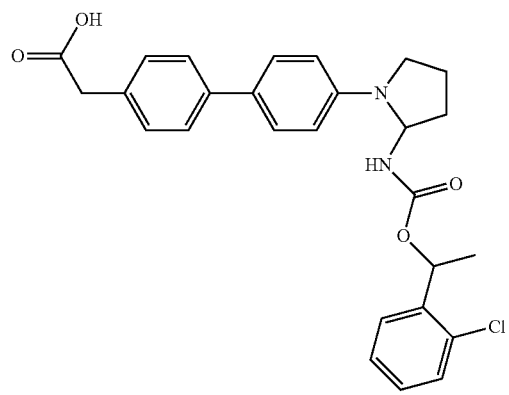 [SMILES: CC(OC(=O)NC1CCCN1c1ccc(-c2ccc(CC(=O)O)cc2)cc1)c1ccccc1Cl]
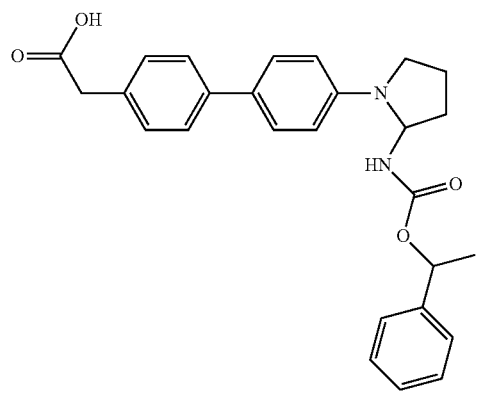 [SMILES: CC(OC(=O)NC1CCCN1c1ccc(-c2ccc(CC(=O)O)cc2)cc1)c1ccccc1]
TABLE 4-continued
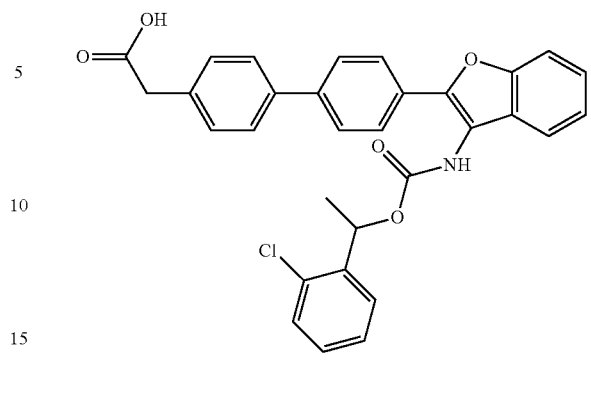
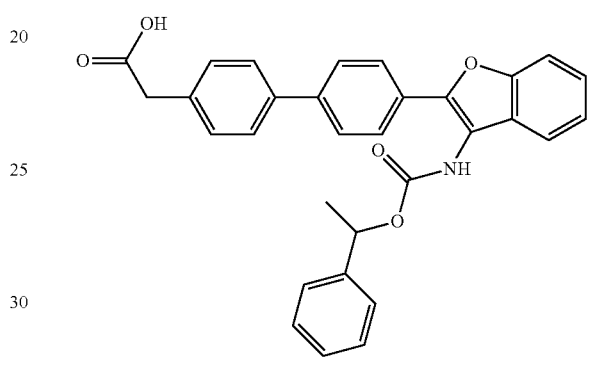
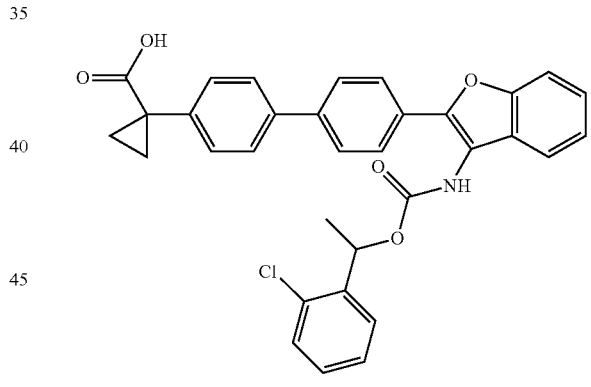
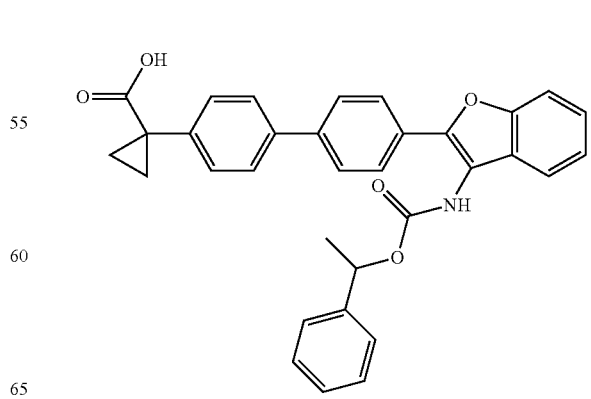

341
TABLE 4-continued
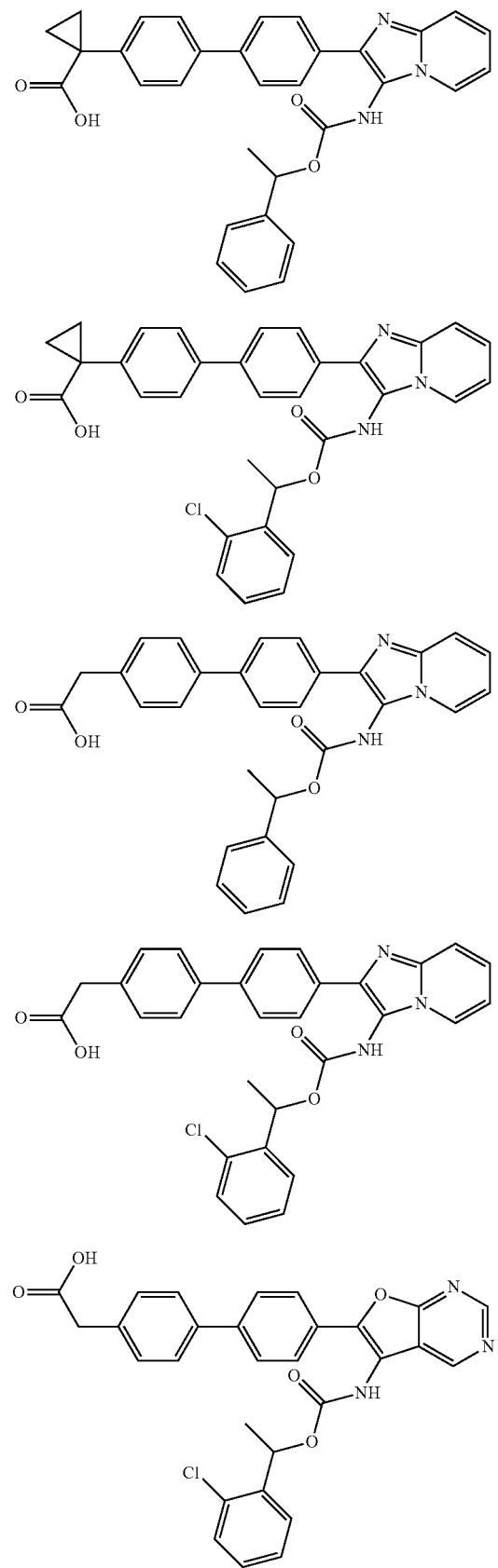
342
TABLE 4-continued
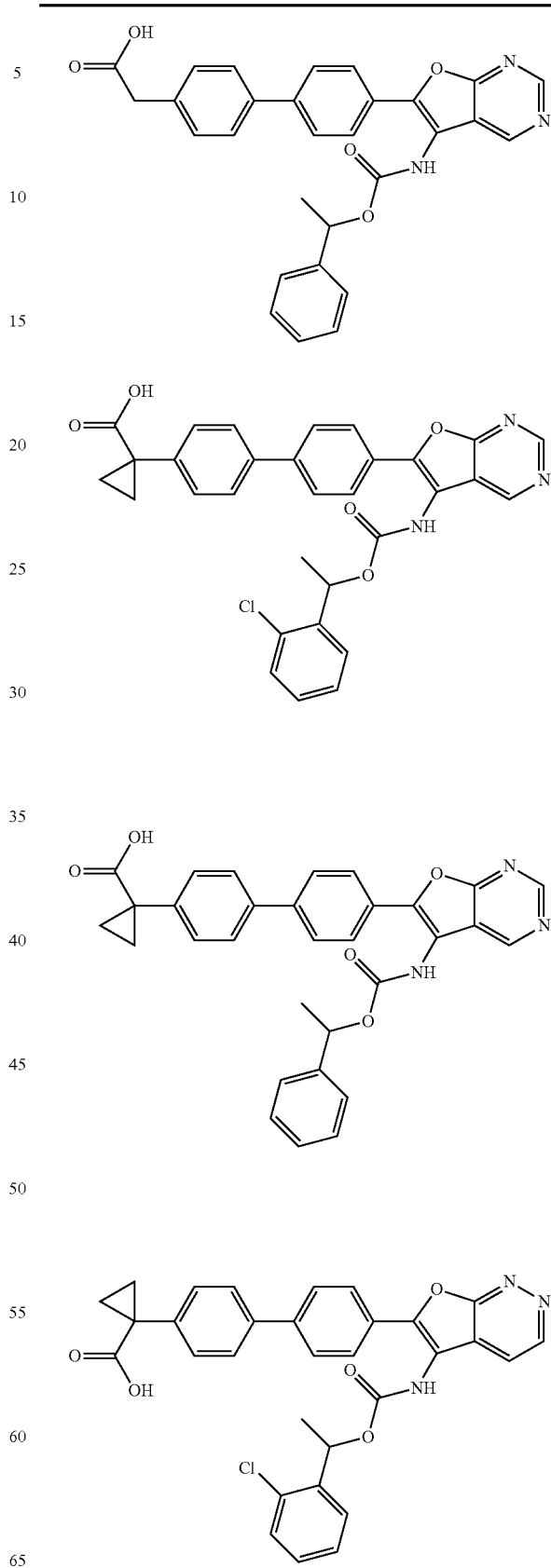

343
TABLE 4-continued
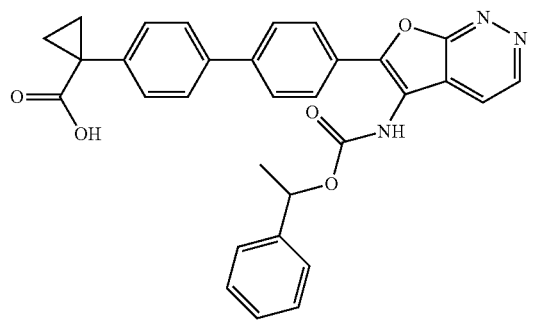 [SMILES: CC(OC(=O)Nc1c(-c2ccc(-c3ccc(C4(C(=O)O)CC4)cc3)cc2)oc2nnccc12)c1ccccc1]
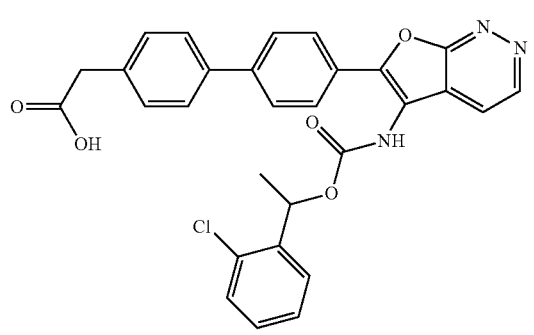 [SMILES: CC(OC(=O)Nc1c(-c2ccc(-c3ccc(CC(=O)O)cc3)cc2)oc2nnccc12)c1ccccc1Cl]
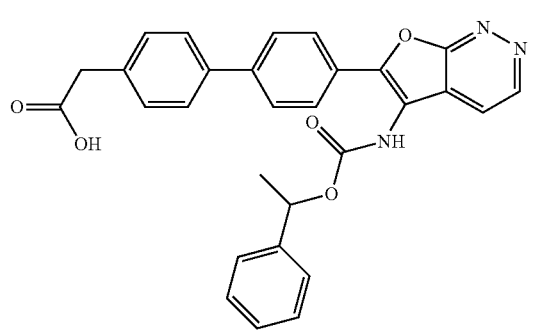 [SMILES: CC(OC(=O)Nc1c(-c2ccc(-c3ccc(CC(=O)O)cc3)cc2)oc2nnccc12)c1ccccc1]
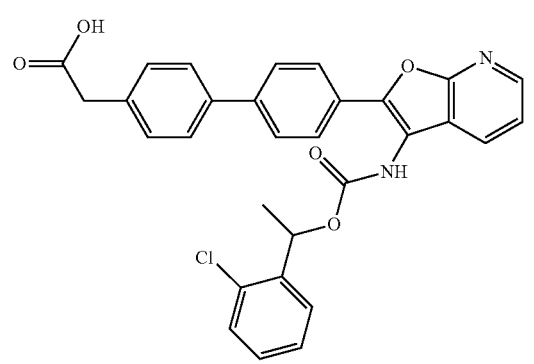 [SMILES: CC(OC(=O)Nc1c(-c2ccc(-c3ccc(CC(=O)O)cc3)cc2)oc2ncccc12)c1ccccc1Cl]
344
TABLE 4-continued
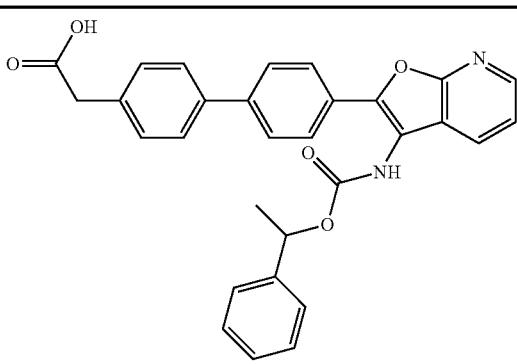
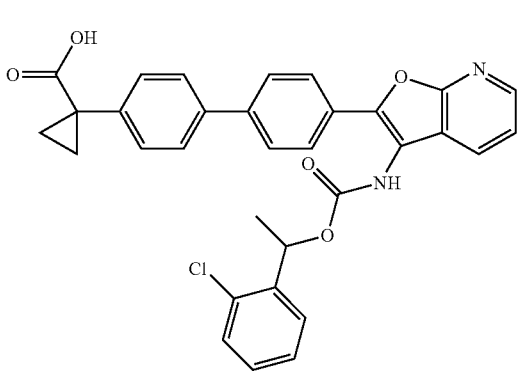 [SMILES: CC(OC(=O)Nc1c(-c2ccc(-c3ccc(C4(C(=O)O)CC4)cc3)cc2)oc2ncccc12)c1ccccc1Cl]
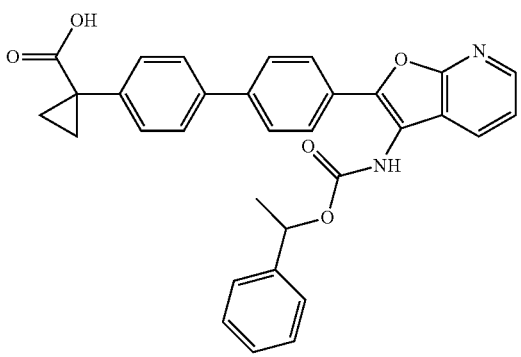 [SMILES: CC(OC(=O)Nc1c(-c2ccc(-c3ccc(C4(C(=O)O)CC4)cc3)cc2)oc2ncccc12)c1ccccc1]
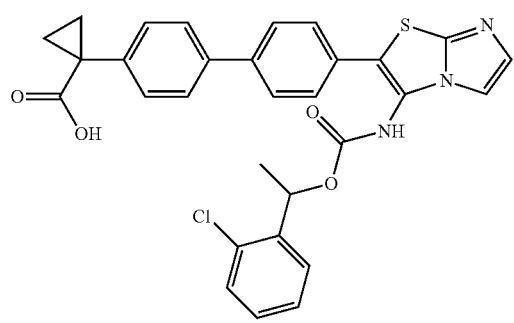 [SMILES: CC(OC(=O)Nc1c(-c2ccc(-c3ccc(C4(C(=O)O)CC4)cc3)cc2)oc2nccn12)c1ccccc1Cl]

TABLE 4-continued
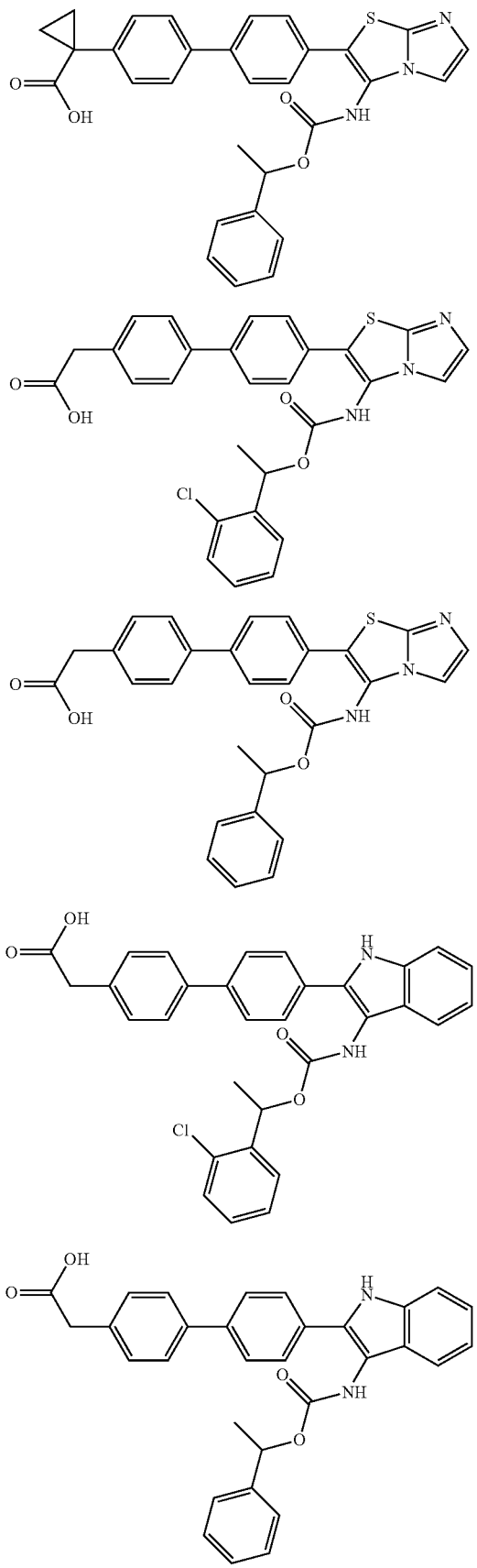
TABLE 4-continued
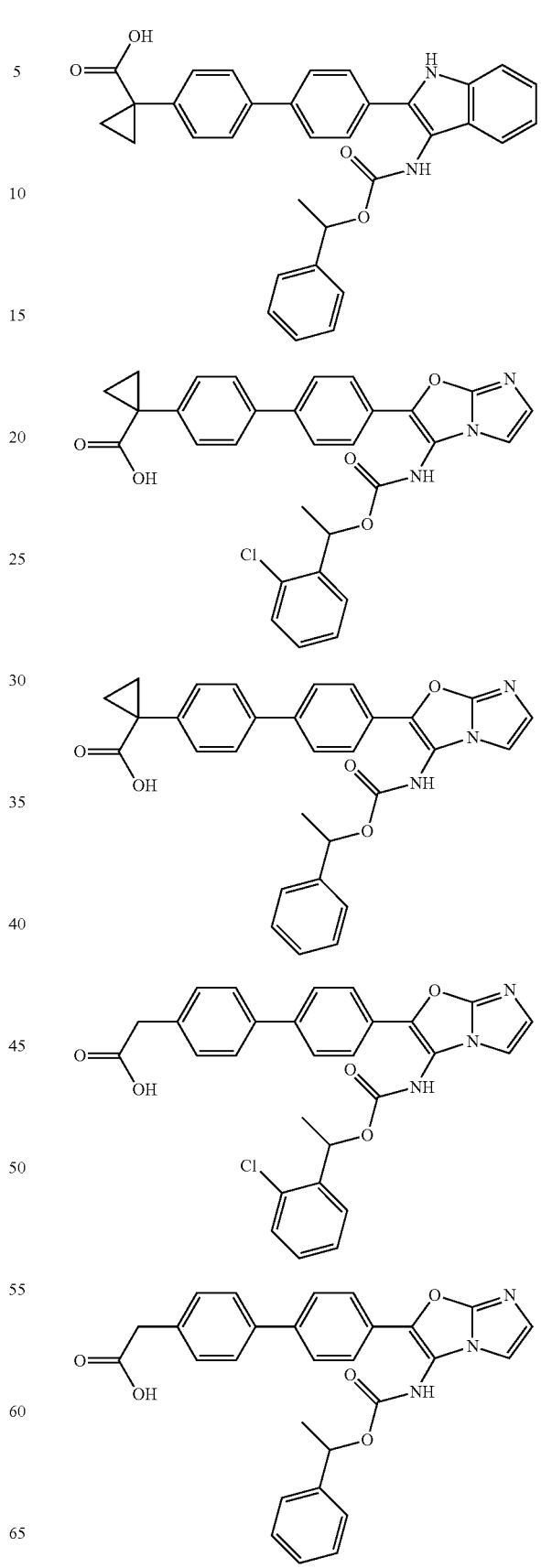

TABLE 4-continued
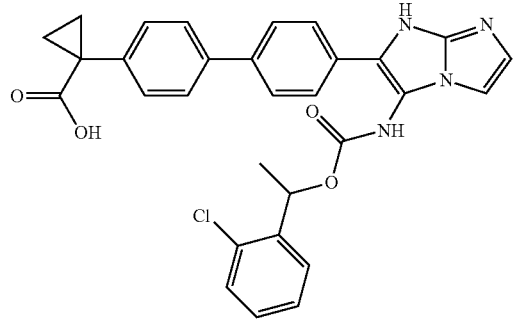 [SMILES: CC(OC(=O)Nc1c(-c2ccc(-c3ccc(C4(C(=O)O)CC4)cc3)cc2)[nH]c2nccn12)c1ccccc1Cl]
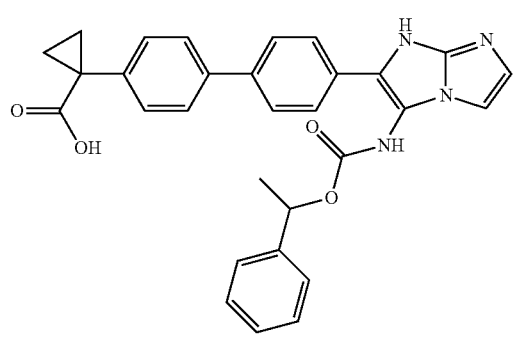 [SMILES: CC(OC(=O)Nc1c(-c2ccc(-c3ccc(C4(C(=O)O)CC4)cc3)cc2)[nH]c2nccn12)c1ccccc1]
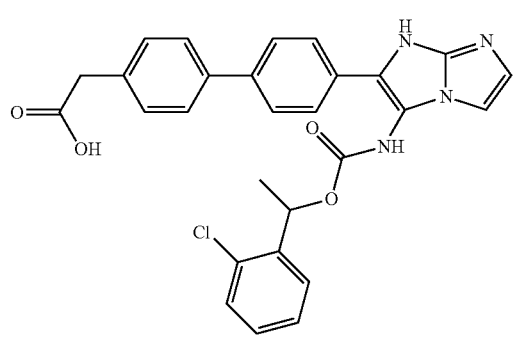 [SMILES: CC(OC(=O)Nc1c(-c2ccc(-c3ccc(CC(=O)O)cc3)cc2)[nH]c2nccn12)c1ccccc1Cl]
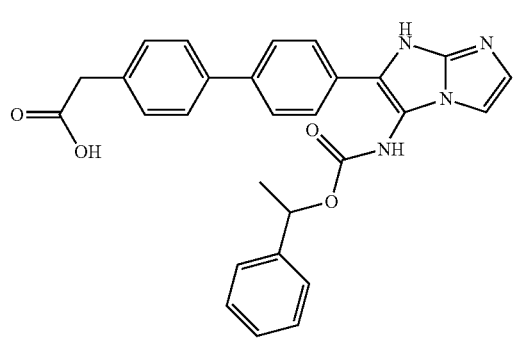 [SMILES: CC(OC(=O)Nc1c(-c2ccc(-c3ccc(CC(=O)O)cc3)cc2)[nH]c2nccn12)c1ccccc1]
TABLE 4-continued
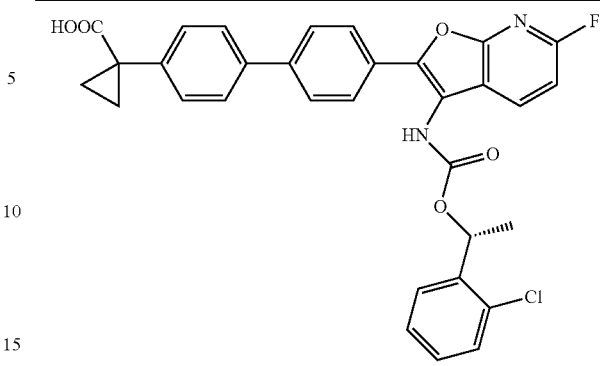
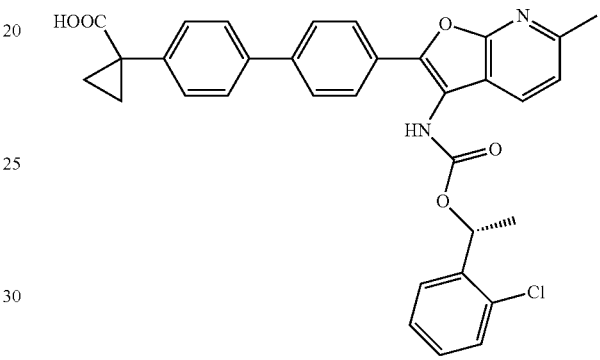
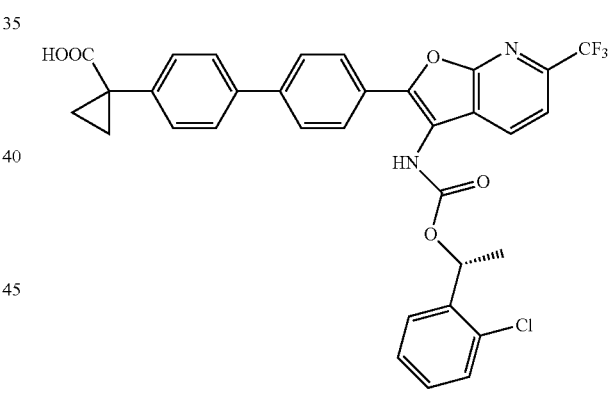
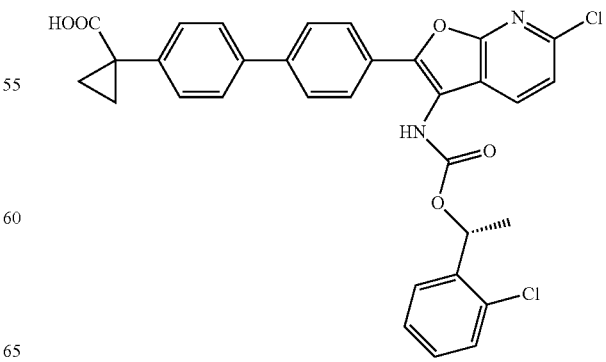

TABLE 4-continued
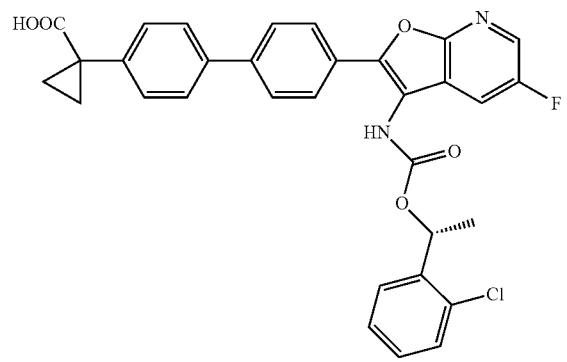 [SMILES: C[C@@H](OC(=O)Nc1c(-c2ccc(-c3ccc(C4(C(=O)O)CC4)cc3)cc2)oc2ncc(F)cc12)c1ccccc1Cl]
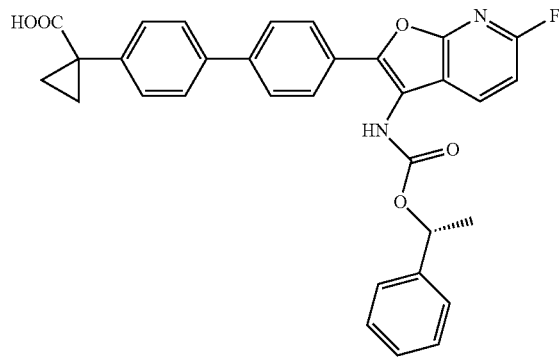
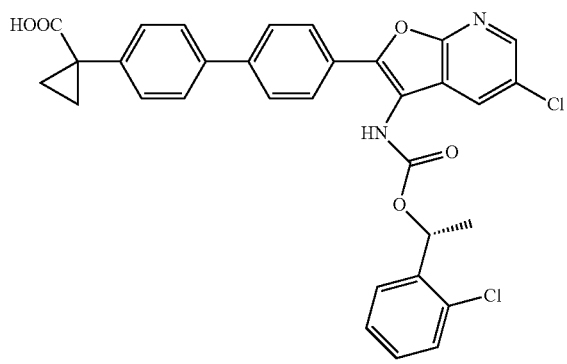 [SMILES: C[C@@H](OC(=O)Nc1c(-c2ccc(-c3ccc(C4(C(=O)O)CC4)cc3)cc2)oc2ncc(Cl)cc12)c1ccccc1Cl]
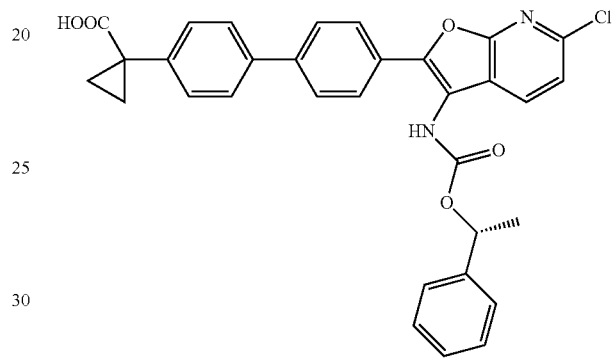
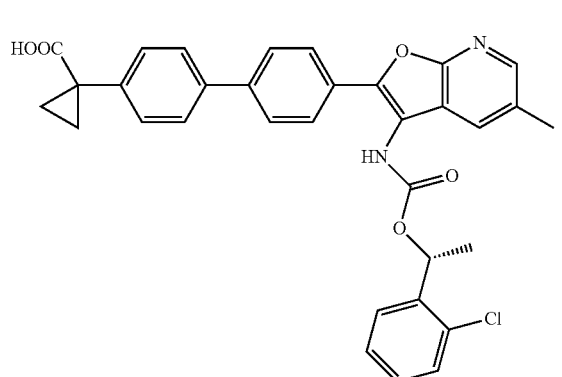
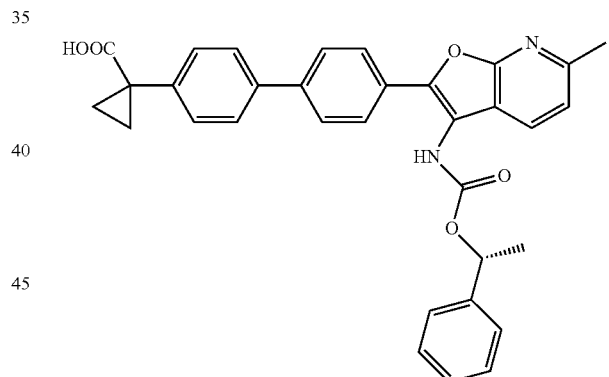
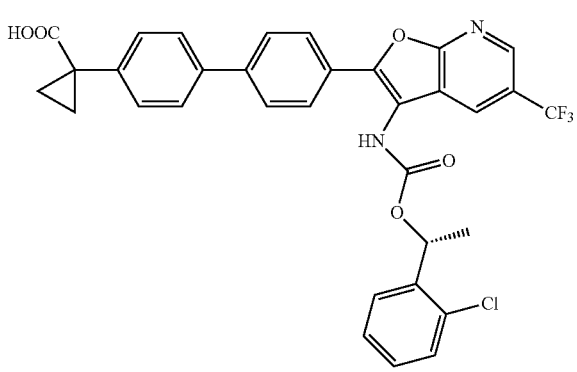
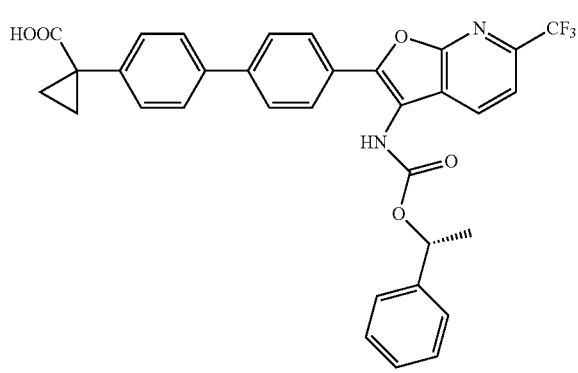 [SMILES: C[C@@H](OC(=O)Nc1c(-c2ccc(-c3ccc(C4(C(=O)O)CC4)cc3)cc2)oc2nc(C(F)(F)F)ccc12)c1ccccc1]

| 351 | 352 |
|---|---|
| TABLE 4-continued | TABLE 4-continued |
| 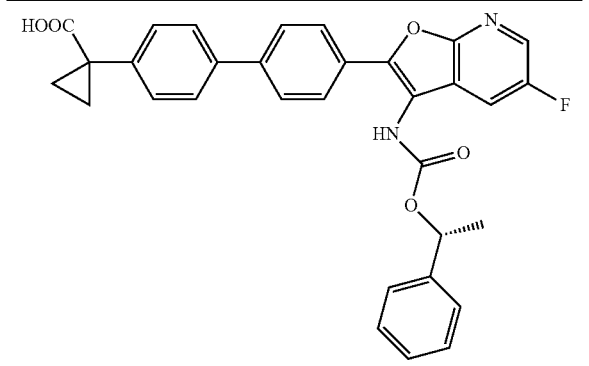 | 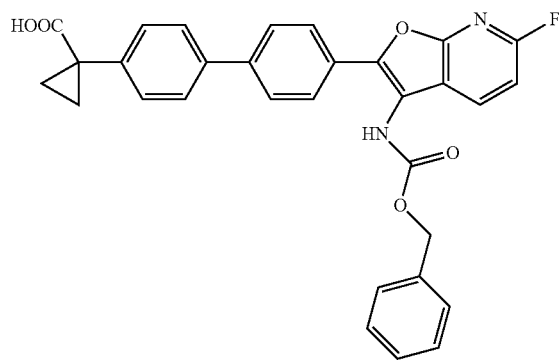 |
| 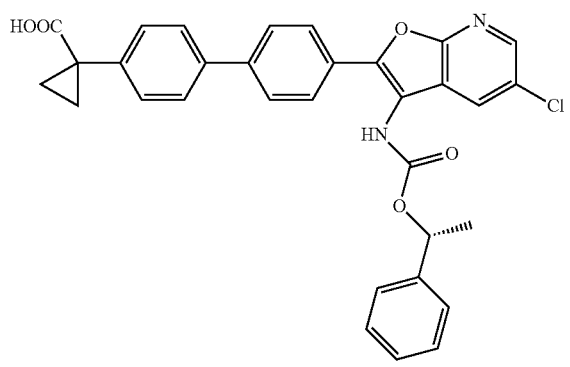 | 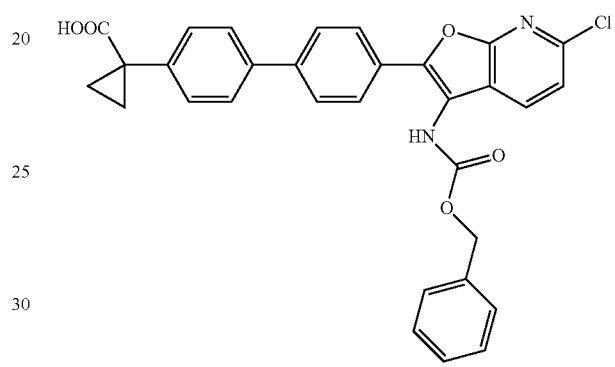 |
| 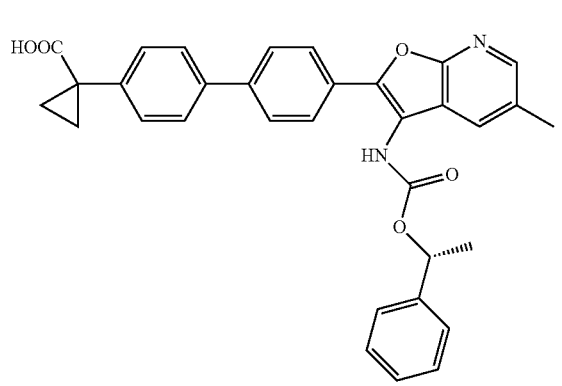 | 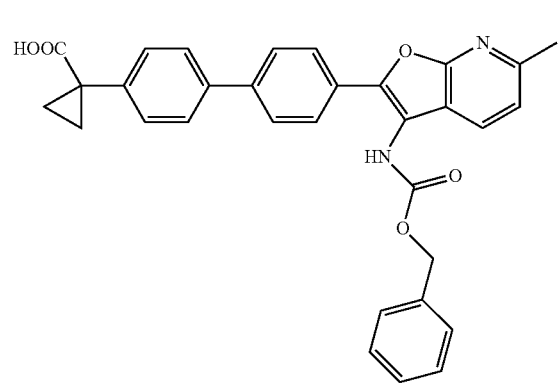 |
| 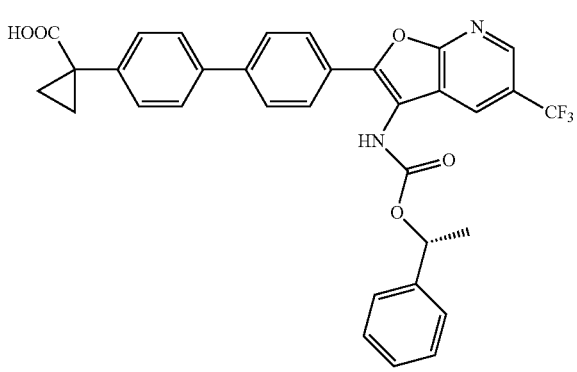 [SMILES: C[C@@H](OC(=O)Nc1c(-c2ccc(-c3ccc(C4(C(=O)O)CC4)cc3)cc2)oc2ncc(C(F)(F)F)cc12)c1ccccc1] | 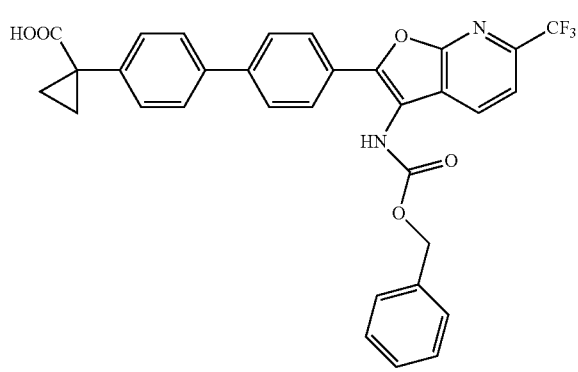 [SMILES: O=C(Nc1c(-c2ccc(-c3ccc(C4(C(=O)O)CC4)cc3)cc2)oc2nc(C(F)(F)F)ccc12)OCc1ccccc1] |

353
TABLE 4-continued
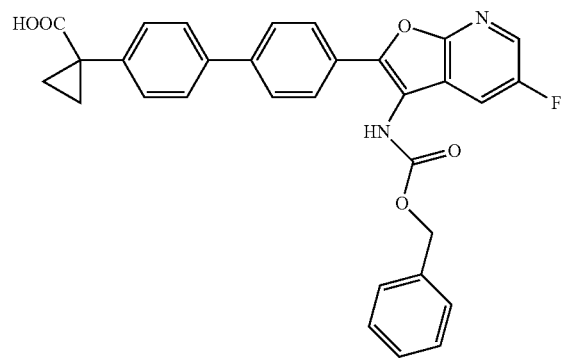 [SMILES: O=C(Nc1c(-c2ccc(-c3ccc(C4(C(=O)O)CC4)cc3)cc2)oc2ncc(F)cc12)OCc1ccccc1]
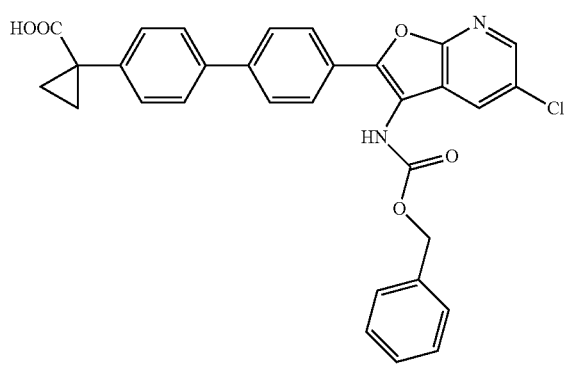 [SMILES: O=C(Nc1c(-c2ccc(-c3ccc(C4(C(=O)O)CC4)cc3)cc2)oc2ncc(Cl)cc12)OCc1ccccc1]
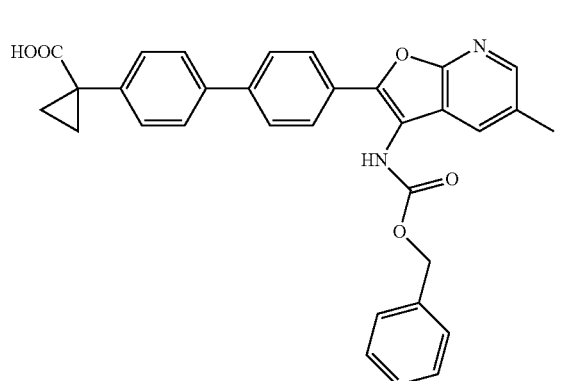
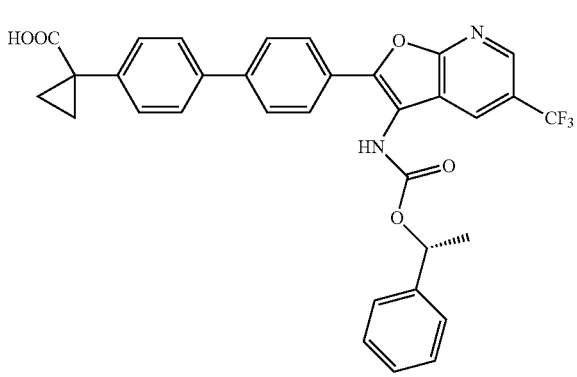 [SMILES: C[C@@H](OC(=O)Nc1c(-c2ccc(-c3ccc(C4(C(=O)O)CC4)cc3)cc2)oc2ncc(C(F)(F)F)cc12)c1ccccc1]
354
TABLE 4-continued
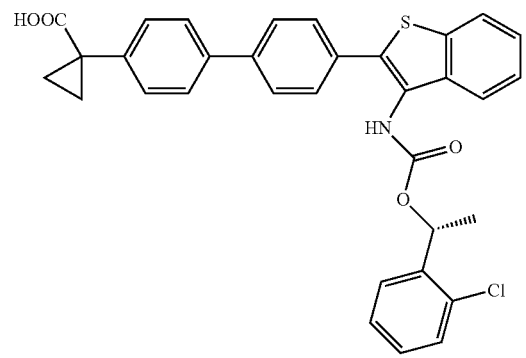 [SMILES: C[C@@H](OC(=O)Nc1c(-c2ccc(-c3ccc(C4(C(=O)O)CC4)cc3)cc2)sc2ccccc12)c1ccccc1Cl]
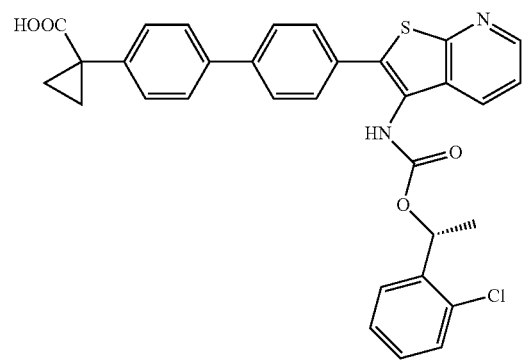 [SMILES: C[C@@H](OC(=O)Nc1c(-c2ccc(-c3ccc(C4(C(=O)O)CC4)cc3)cc2)sc2ncccc12)c1ccccc1Cl]
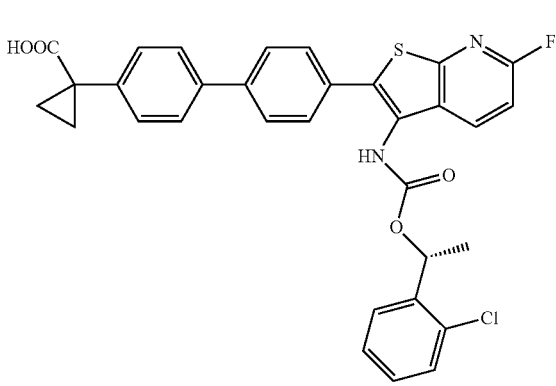 [SMILES: C[C@@H](OC(=O)Nc1c(-c2ccc(-c3ccc(C4(C(=O)O)CC4)cc3)cc2)sc2nc(F)ccc12)c1ccccc1Cl]
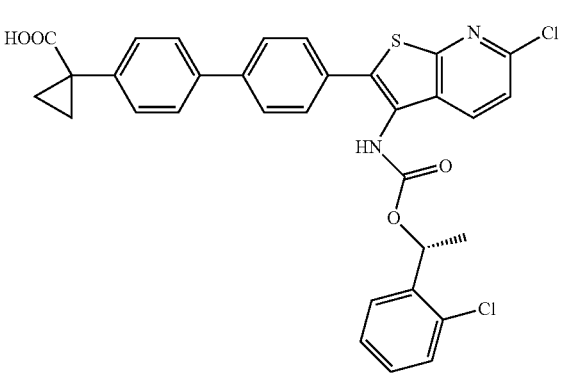 [SMILES: C[C@@H](OC(=O)Nc1c(-c2ccc(-c3ccc(C4(C(=O)O)CC4)cc3)cc2)sc2nc(Cl)ccc12)c1ccccc1Cl]

TABLE 4-continued
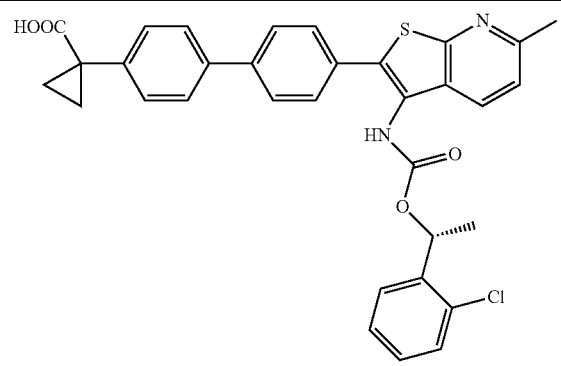
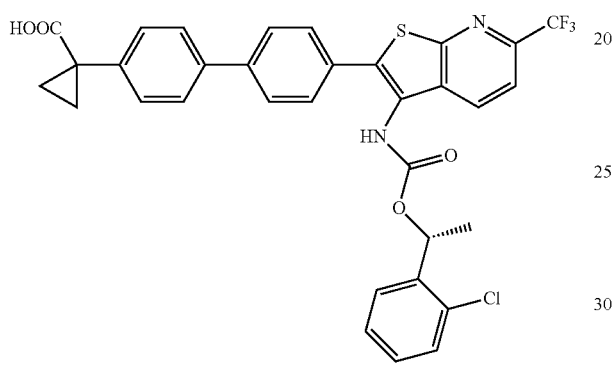
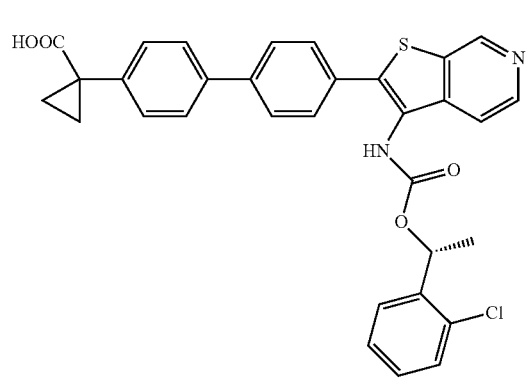 [SMILES: C[C@@H](OC(=O)Nc1c(-c2ccc(-c3ccc(C4(C(=O)O)CC4)cc3)cc2)sc2cnccc12)c1ccccc1Cl]
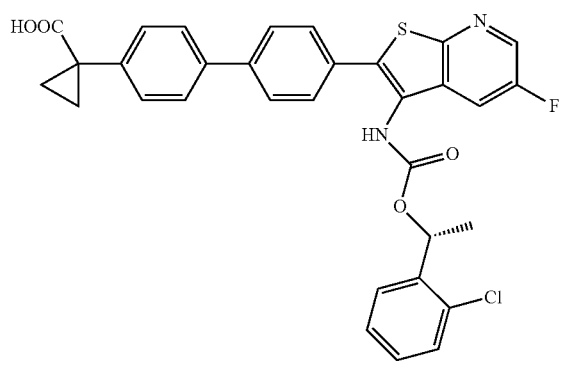
TABLE 4-continued
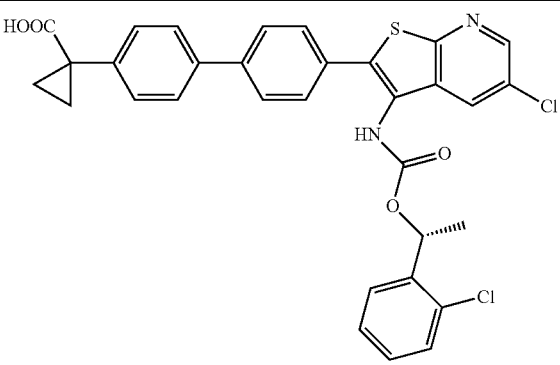
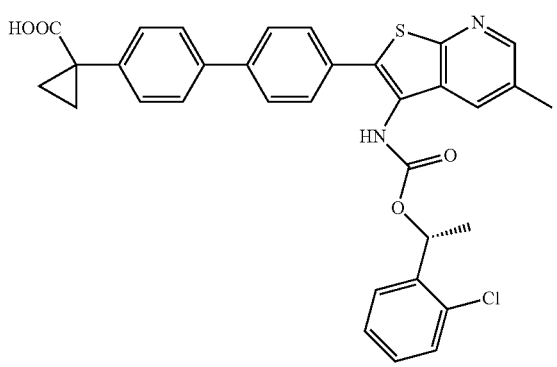
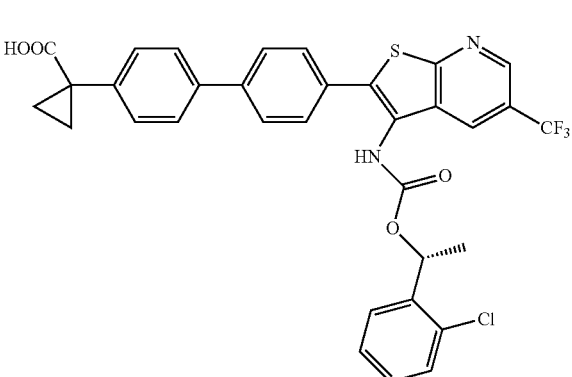
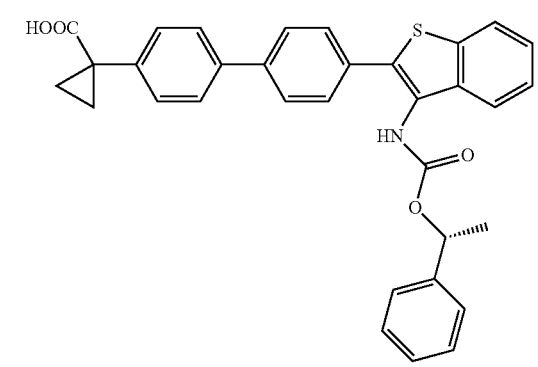 [SMILES: C[C@@H](OC(=O)Nc1c(-c2ccc(-c3ccc(C4(C(=O)O)CC4)cc3)cc2)sc2ccccc12)c1ccccc1]

TABLE 4-continued
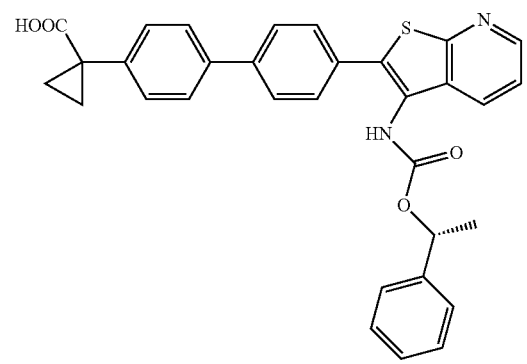 [SMILES: C[C@@H](OC(=O)Nc1c(-c2ccc(-c3ccc(C4(C(=O)O)CC4)cc3)cc2)sc2ncccc12)c1ccccc1]
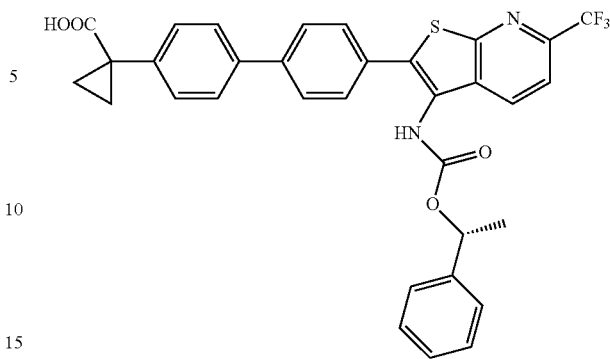
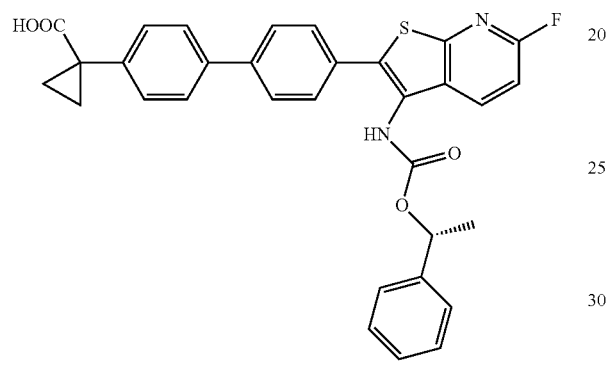
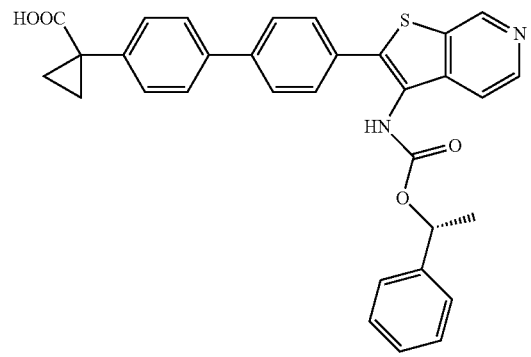 [SMILES: C[C@@H](OC(=O)Nc1c(-c2ccc(-c3ccc(C4(C(=O)O)CC4)cc3)cc2)sc2cnccc12)c1ccccc1]
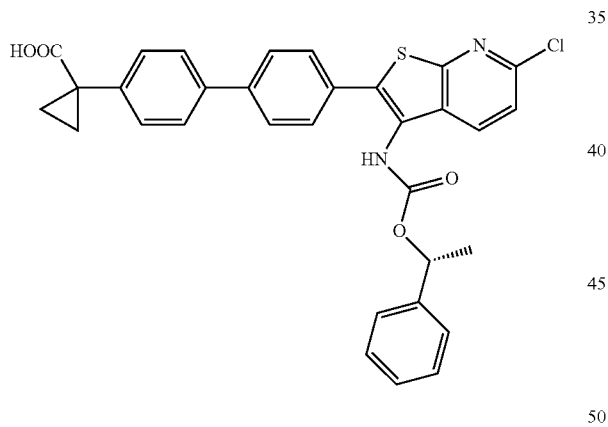
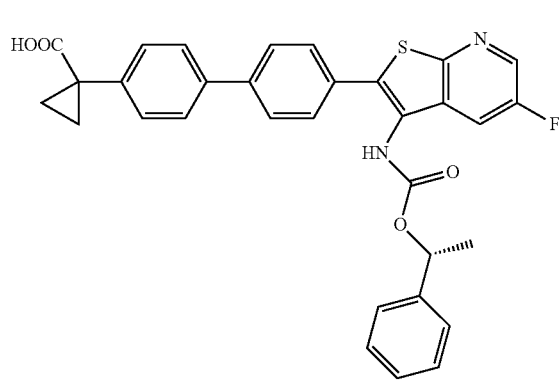 [SMILES: C[C@@H](OC(=O)Nc1c(-c2ccc(-c3ccc(C4(C(=O)O)CC4)cc3)cc2)sc2ncc(F)cc12)c1ccccc1]
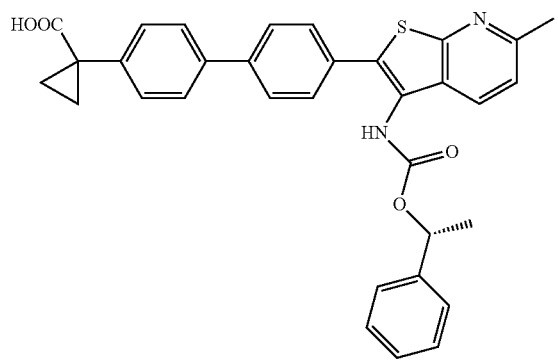
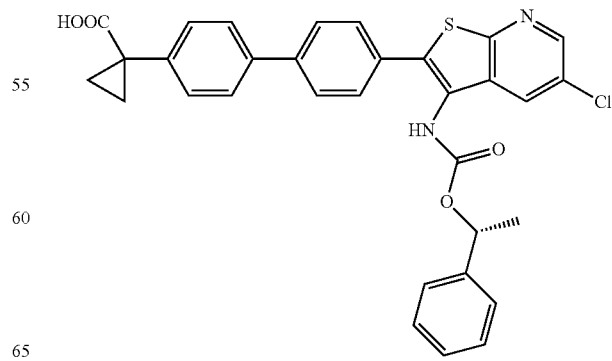

TABLE 4-continued
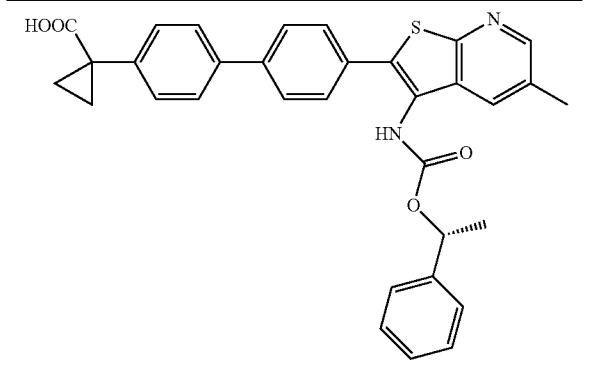
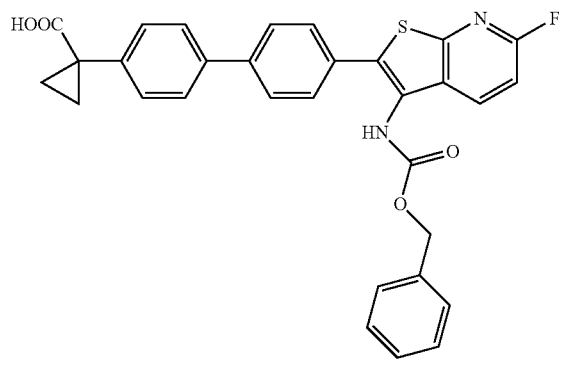
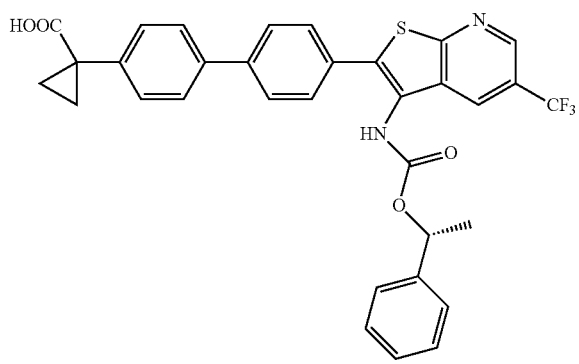
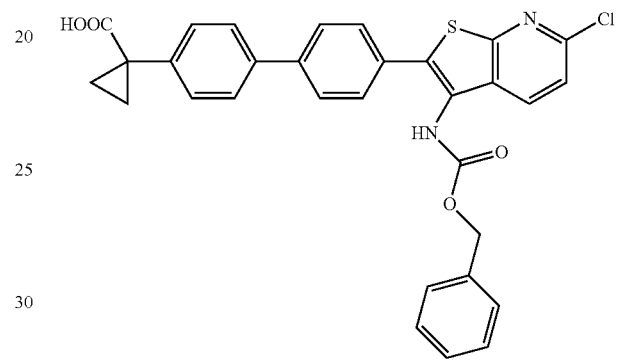
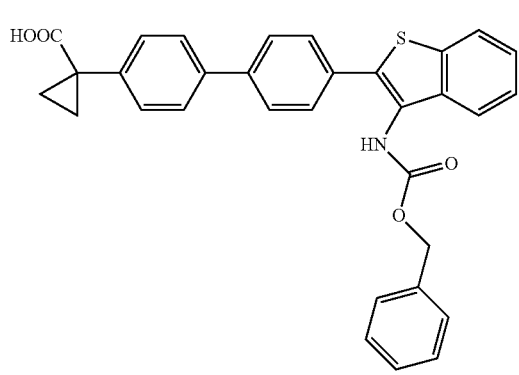 [SMILES: O=C(Nc1c(-c2ccc(-c3ccc(C4(C(=O)O)CC4)cc3)cc2)sc2ccccc12)OCc1ccccc1]
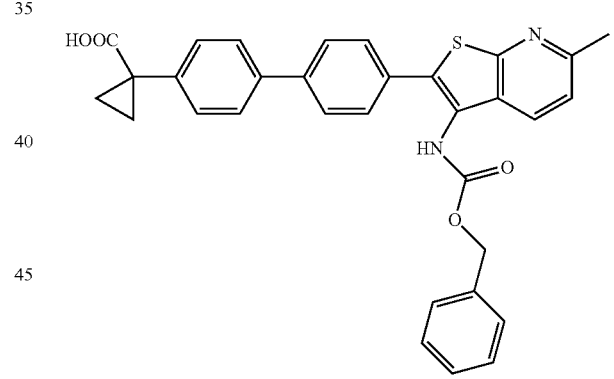
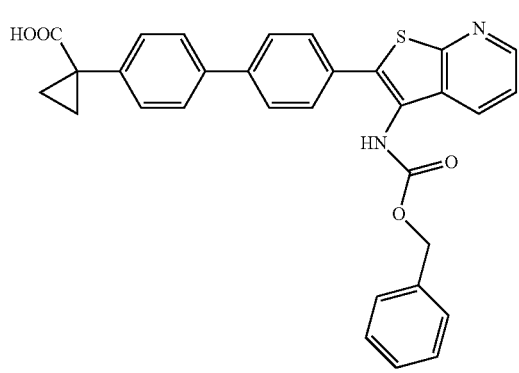 [SMILES: O=C(Nc1c(-c2ccc(-c3ccc(C4(C(=O)O)CC4)cc3)cc2)sc2ncccc12)OCc1ccccc1]
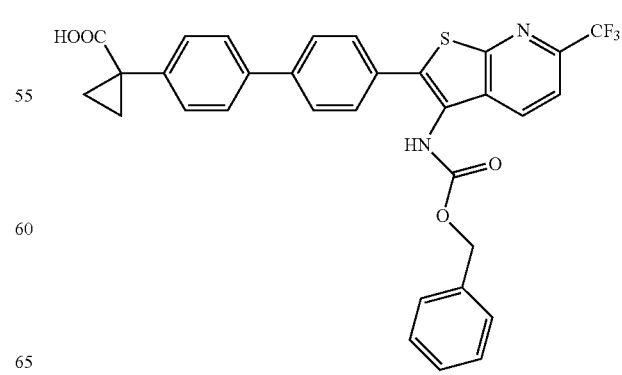

TABLE 4-continued
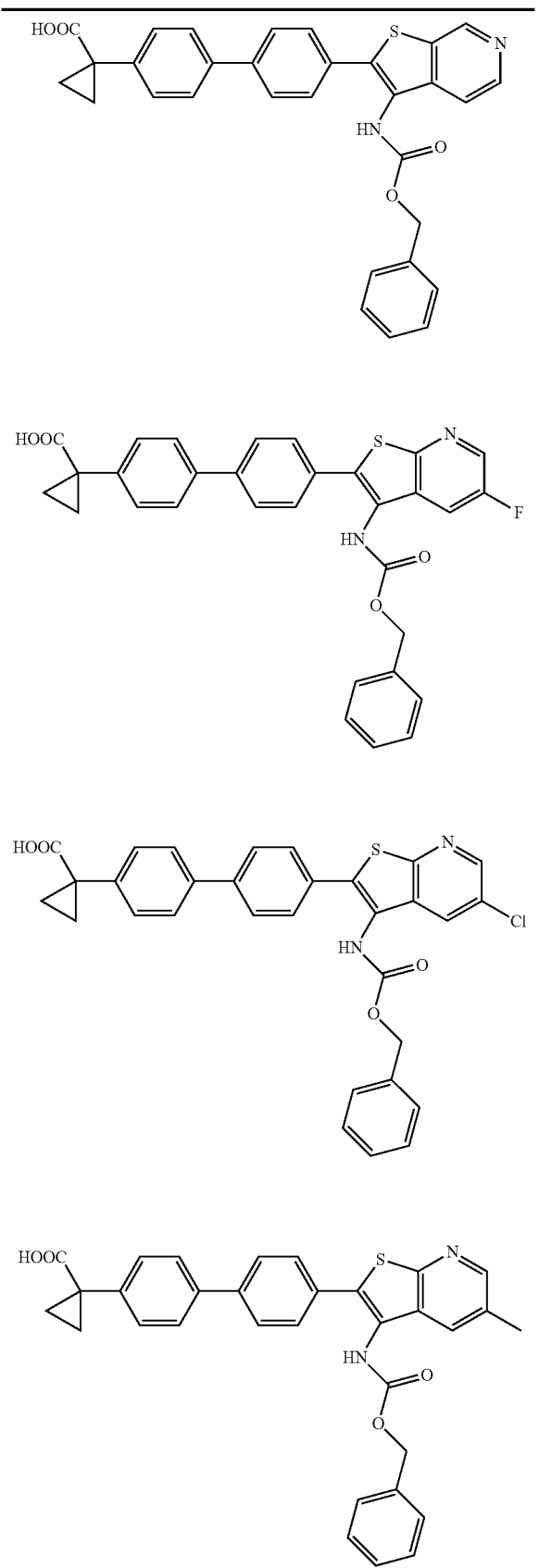
TABLE 4-continued
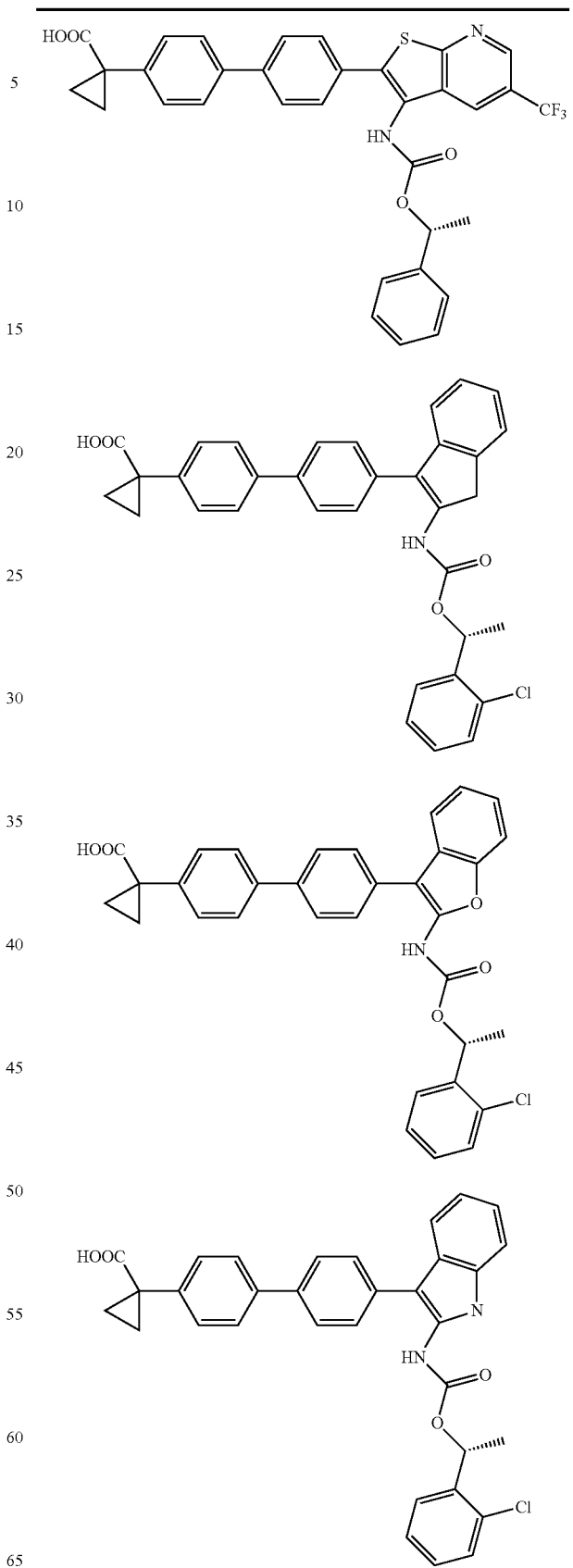

TABLE 4-continued
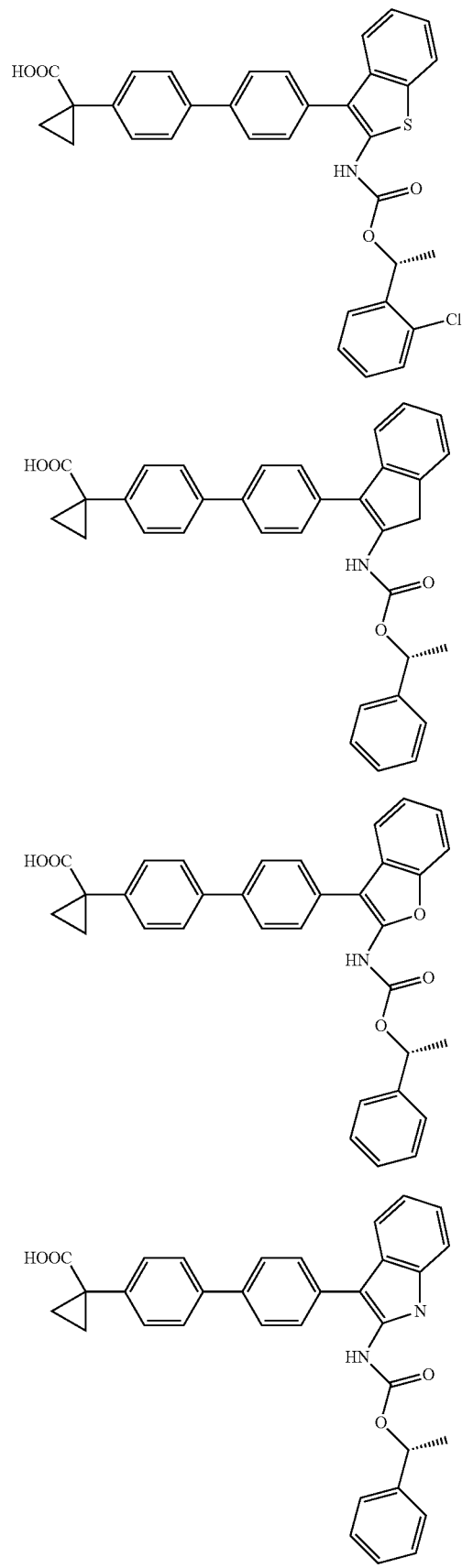
TABLE 4-continued
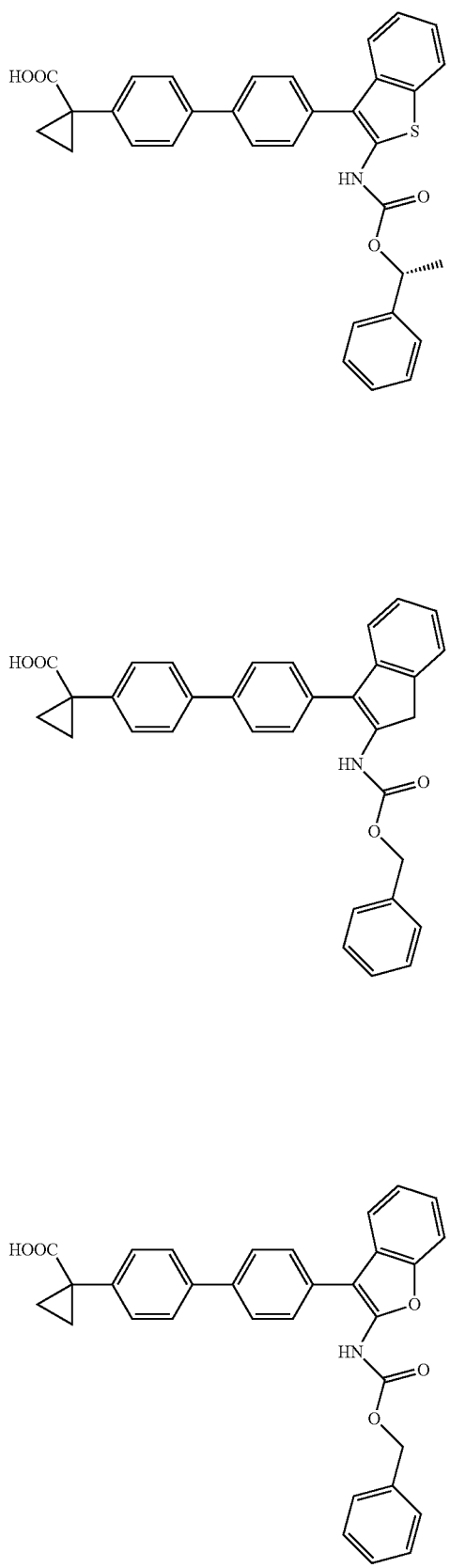

TABLE 4-continued
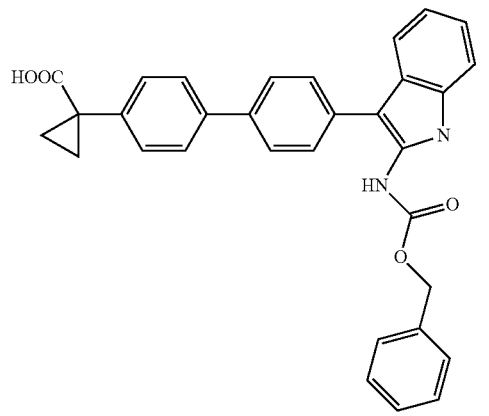 [SMILES: O=C(Nc1sc2ccccc2c1-c1ccc(-c2ccc(C3(C(=O)O)CC3)cc2)cc1)OCc1ccccc1]
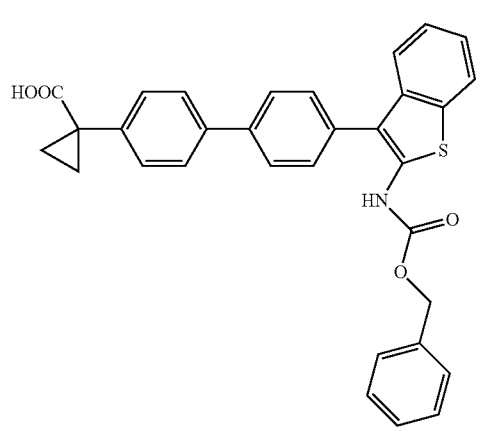
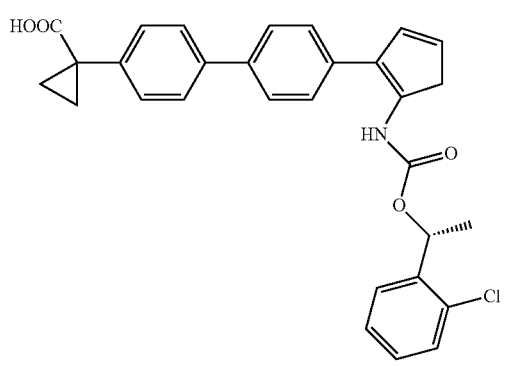 [SMILES: C[C@@H](OC(=O)Nc1[nH]ccc1-c1ccc(-c2ccc(C3(C(=O)O)CC3)cc2)cc1)c1ccccc1Cl]
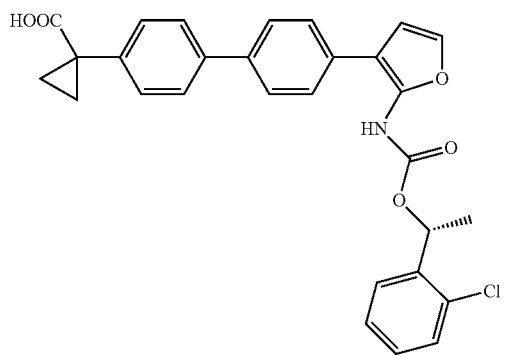 [SMILES: C[C@@H](OC(=O)Nc1sccc1-c1ccc(-c2ccc(C3(C(=O)O)CC3)cc2)cc1)c1ccccc1Cl]
TABLE 4-continued
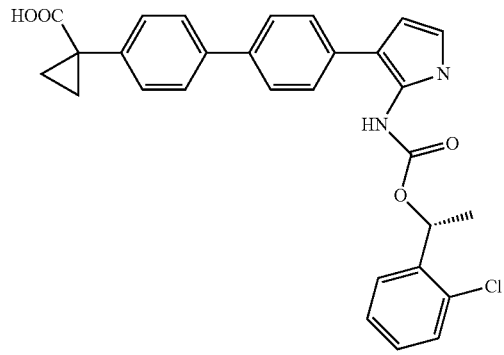
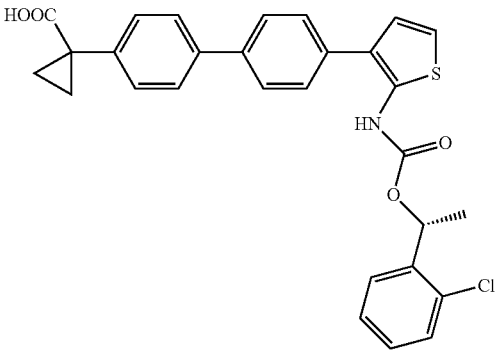
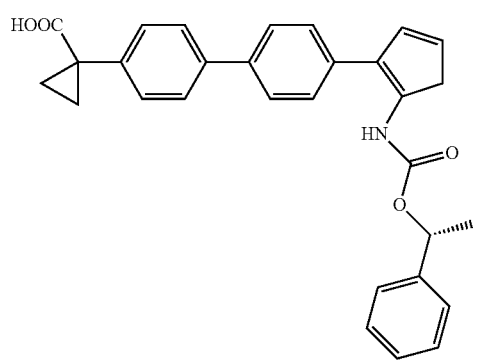 [SMILES: C[C@@H](OC(=O)Nc1occc1-c1ccc(-c2ccc(C3(C(=O)O)CC3)cc2)cc1)c1ccccc1]
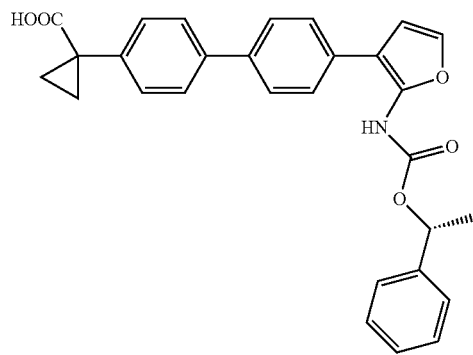

TABLE 4-continued
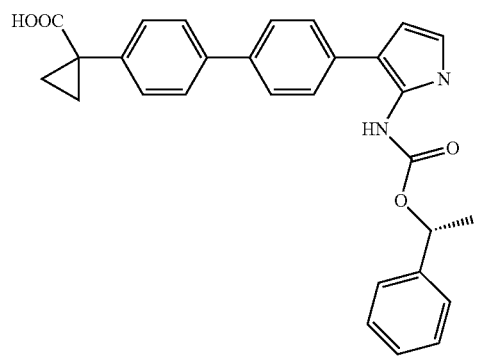 [SMILES: C[C@@H](OC(=O)Nc1[nH]ccc1-c1ccc(-c2ccc(C3(C(=O)O)CC3)cc2)cc1)c1ccccc1]
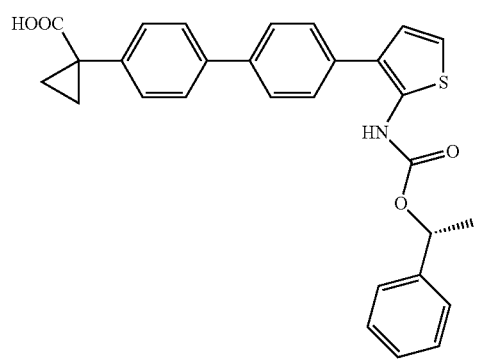
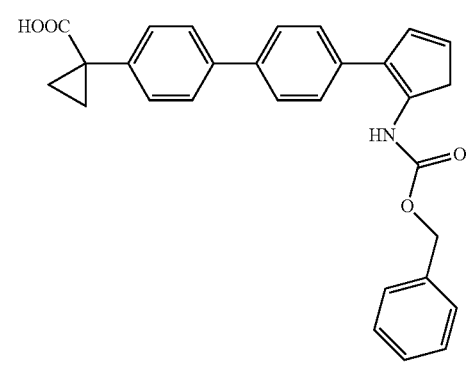
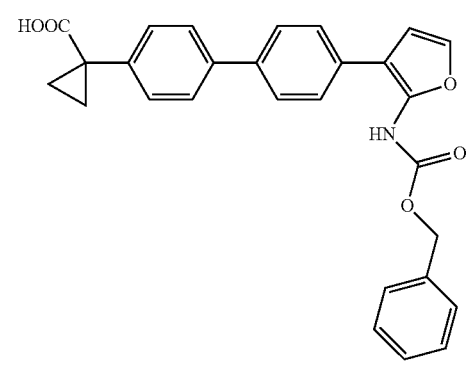
TABLE 4-continued
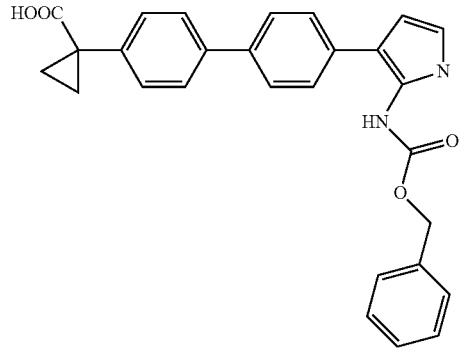
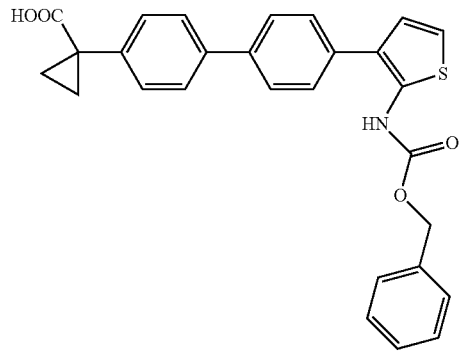 [SMILES: O=C(NC1=C(c2ccc(-c3ccc(C4(C(=O)O)CC4)cc3)cc2)C=CC1)OCc1ccccc1]
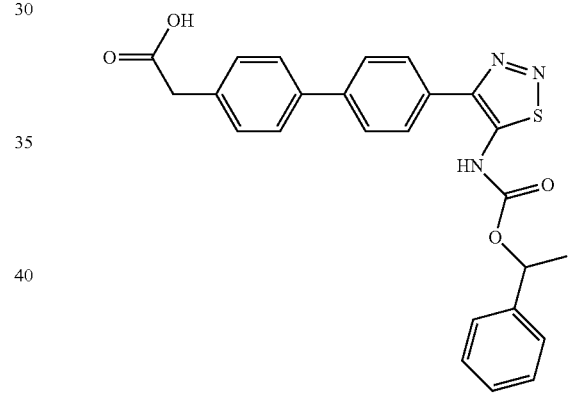
In some embodiments, compounds of Formula (I) are selected from the following compounds as listed in Table 5.
TABLE 5
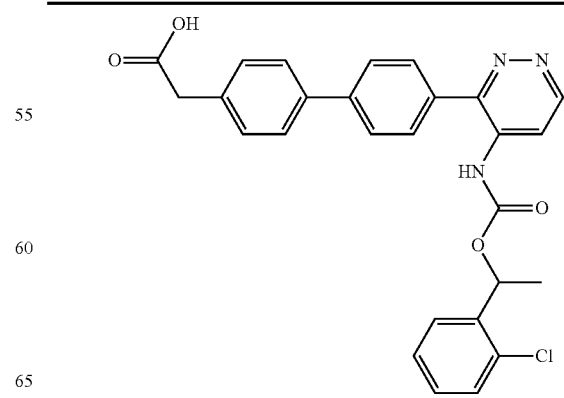

TABLE 5-continued
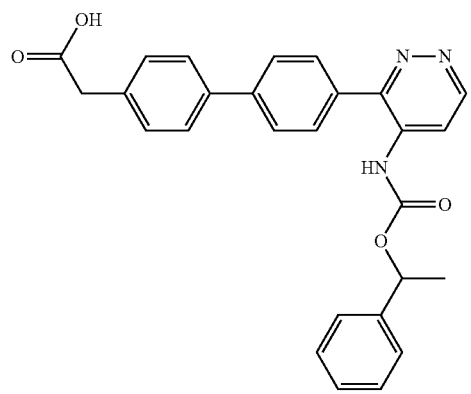 [SMILES: CC(OC(=O)Nc1ccnnc1-c1ccc(-c2ccc(CC(=O)O)cc2)cc1)c1ccccc1]
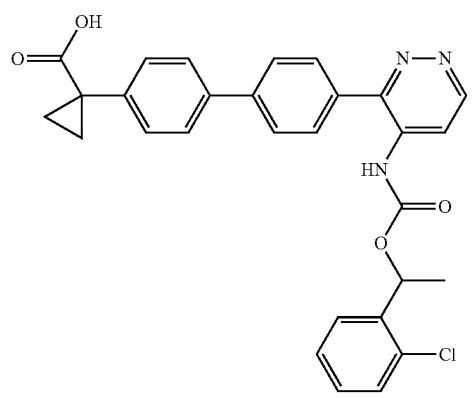
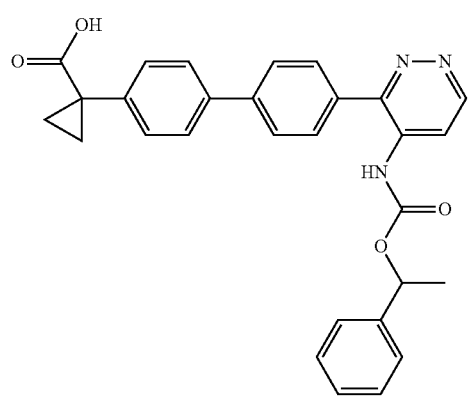 [SMILES: CC(OC(=O)Nc1ccnnc1-c1ccc(-c2ccc(C3(C(=O)O)CC3)cc2)cc1)c1ccccc1]
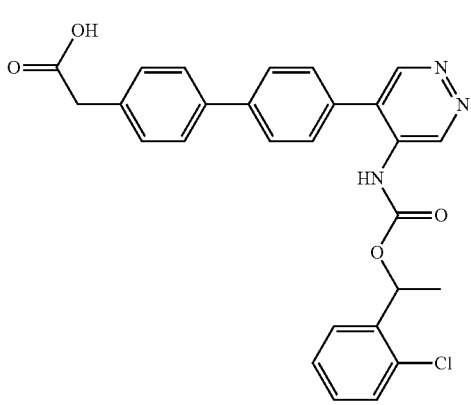 [SMILES: CC(OC(=O)Nc1cnncc1-c1ccc(-c2ccc(CC(=O)O)cc2)cc1)c1ccccc1Cl]
TABLE 5-continued
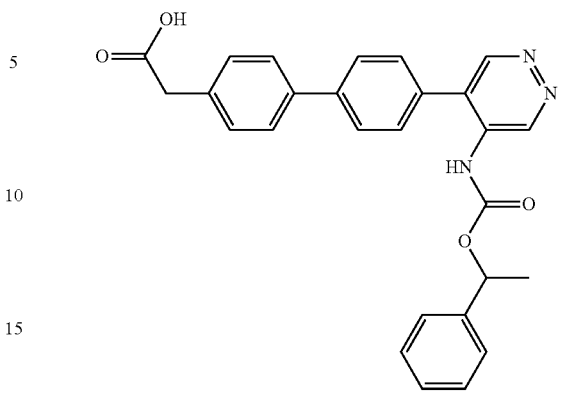

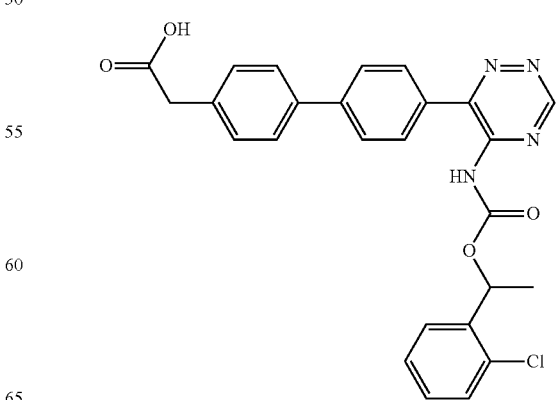

TABLE 5-continued
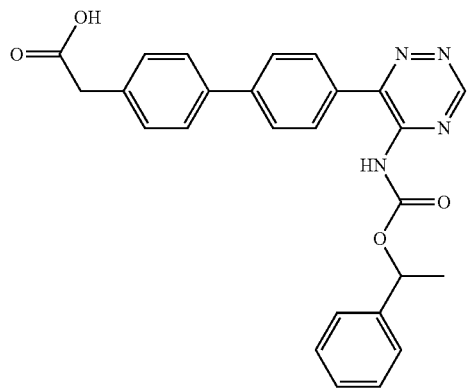 [SMILES: CC(OC(=O)Nc1ncnnc1-c1ccc(-c2ccc(CC(=O)O)cc2)cc1)c1ccccc1]
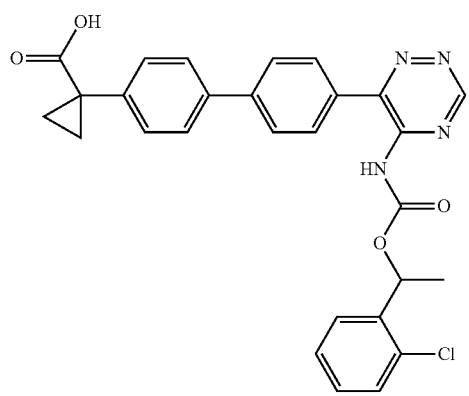
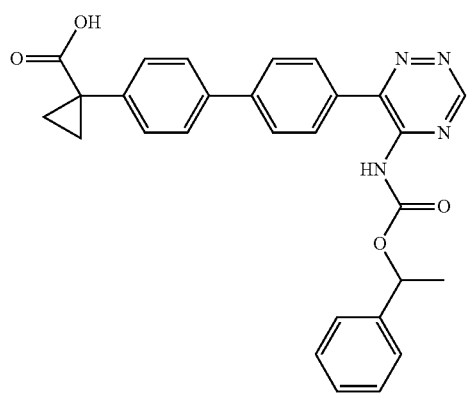 [SMILES: CC(OC(=O)Nc1ncnnc1-c1ccc(-c2ccc(C3(C(=O)O)CC3)cc2)cc1)c1ccccc1]
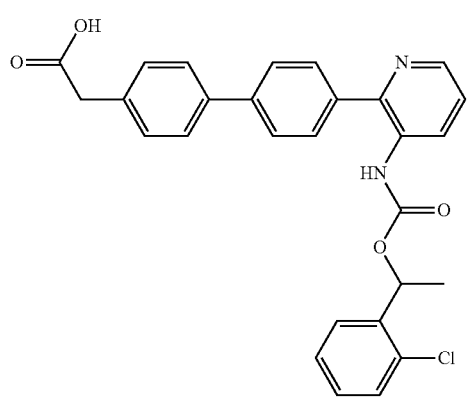 [SMILES: CC(OC(=O)Nc1ncncc1-c1ccc(-c2ccc(CC(=O)O)cc2)cc1)c1ccccc1Cl]
TABLE 5-continued
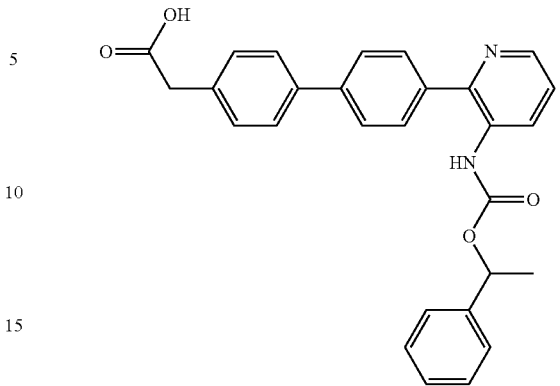
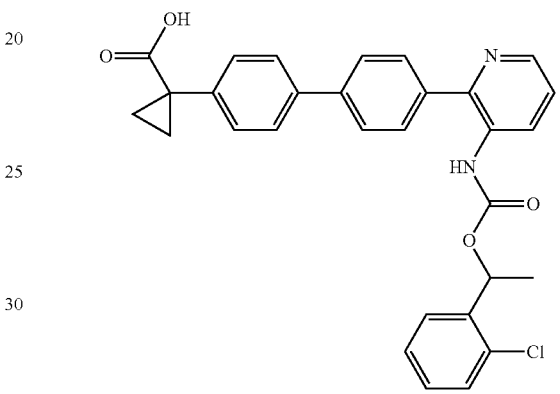

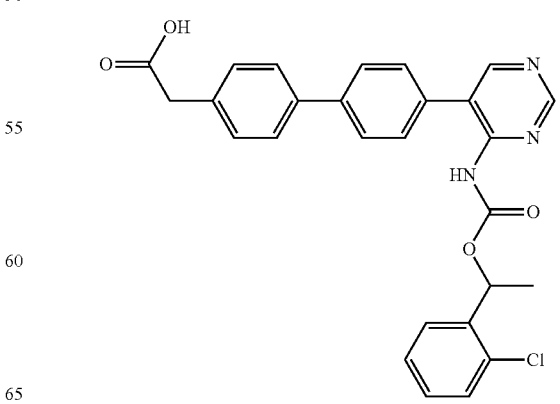

TABLE 5-continued
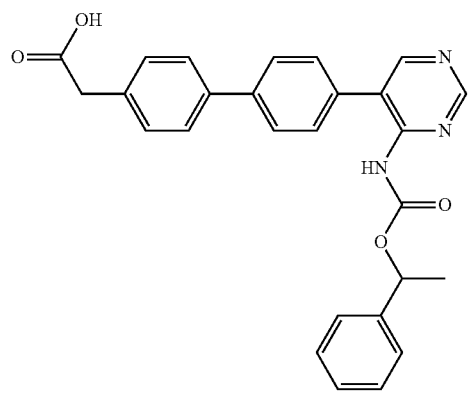 [SMILES: CC(OC(=O)Nc1ncncc1-c1ccc(-c2ccc(CC(=O)O)cc2)cc1)c1ccccc1]
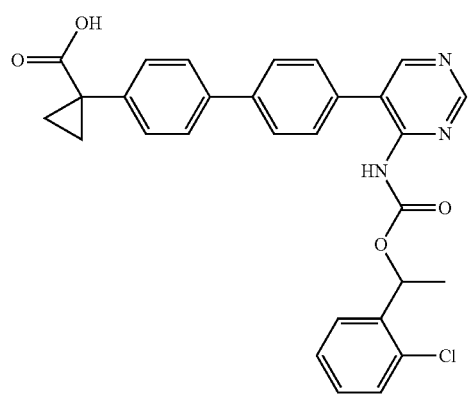 [SMILES: CC(OC(=O)Nc1ncncc1-c1ccc(-c2ccc(C3(C(=O)O)CC3)cc2)cc1)c1ccccc1Cl]
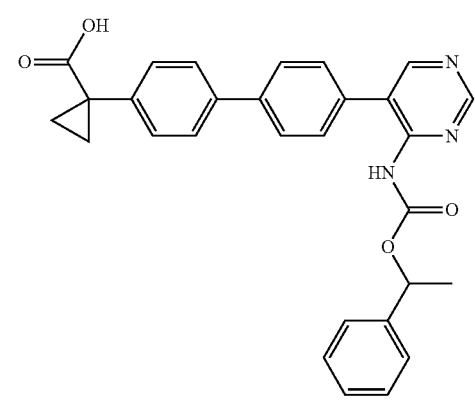
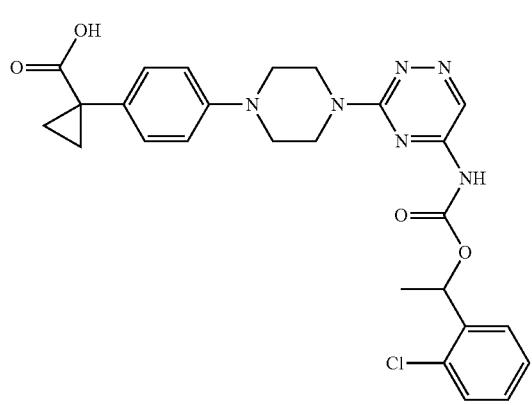 [SMILES: CC(OC(=O)Nc1cnnc(N2CCN(c3ccc(C4(C(=O)O)CC4)cc3)CC2)n1)c1ccccc1Cl]
TABLE 5-continued
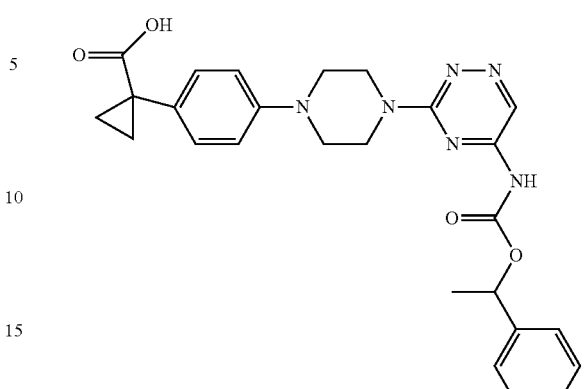
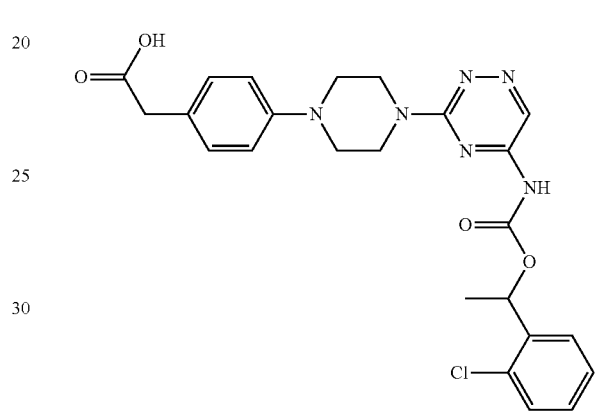
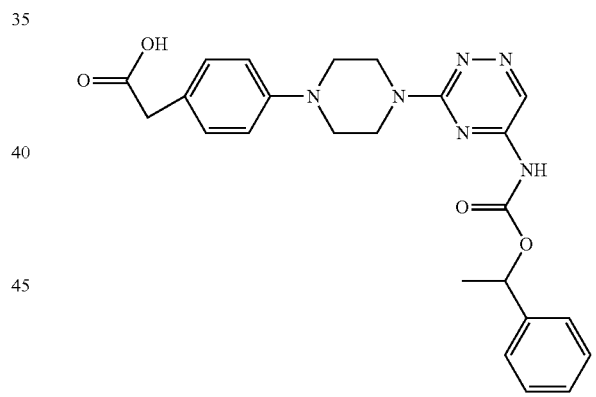
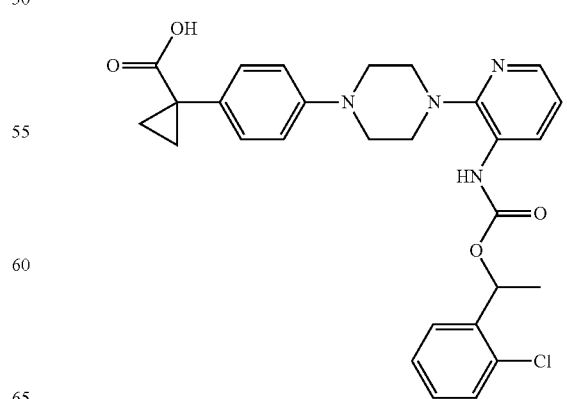

TABLE 5-continued
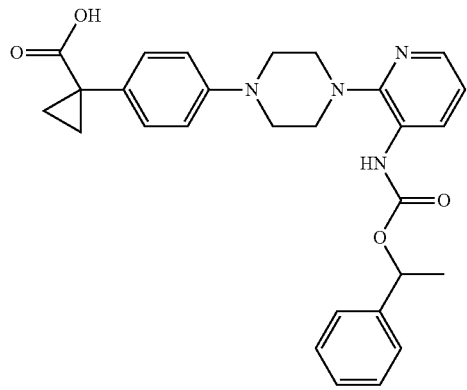 [SMILES: CC(OC(=O)Nc1cccnc1N1CCN(c2ccc(C3(C(=O)O)CC3)cc2)CC1)c1ccccc1]
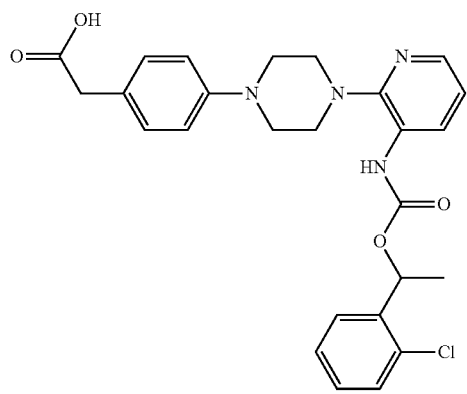 [SMILES: CC(OC(=O)Nc1cccnc1N1CCN(c2ccc(CC(=O)O)cc2)CC1)c1ccccc1Cl]
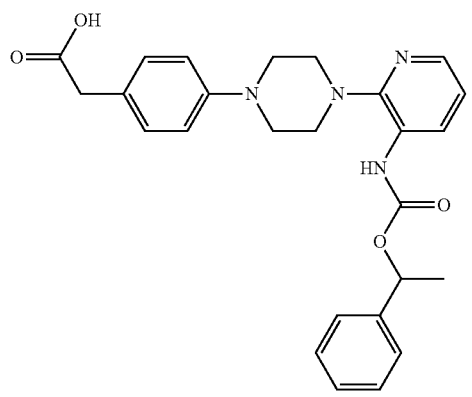 [SMILES: CC(OC(=O)Nc1cccnc1N1CCN(c2ccc(CC(=O)O)cc2)CC1)c1ccccc1]
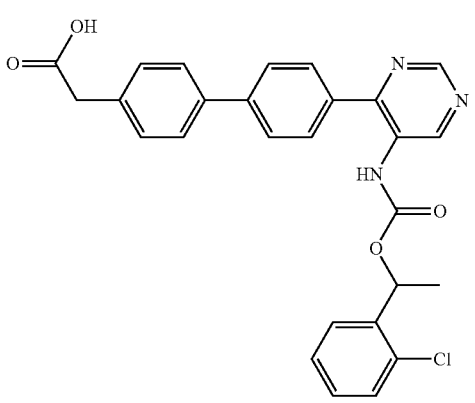 [SMILES: CC(OC(=O)Nc1cncnc1-c1ccc(-c2ccc(CC(=O)O)cc2)cc1)c1ccccc1Cl]
TABLE 5-continued
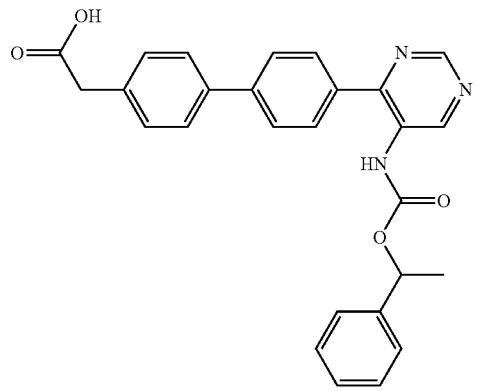 [SMILES: CC(OC(=O)Nc1cncnc1-c1ccc(-c2ccc(CC(=O)O)cc2)cc1)c1ccccc1]
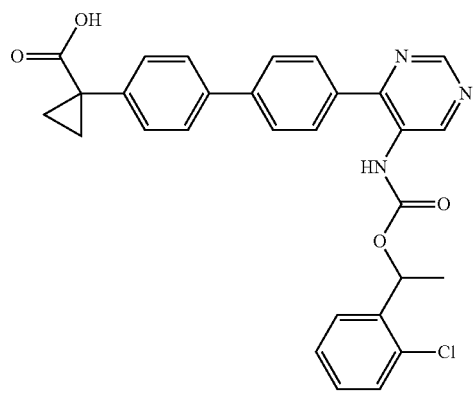 [SMILES: CC(OC(=O)Nc1cncnc1-c1ccc(-c2ccc(C3(C(=O)O)CC3)cc2)cc1)c1ccccc1Cl]
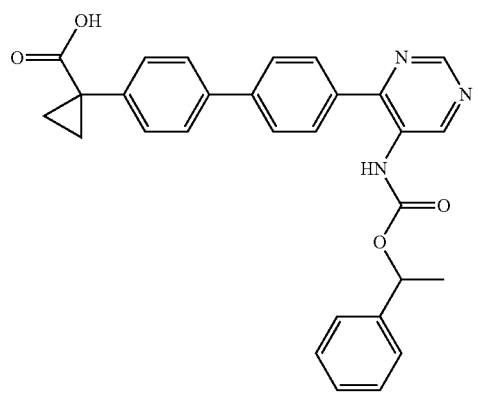 [SMILES: CC(OC(=O)Nc1cncnc1-c1ccc(-c2ccc(C3(C(=O)O)CC3)cc2)cc1)c1ccccc1]
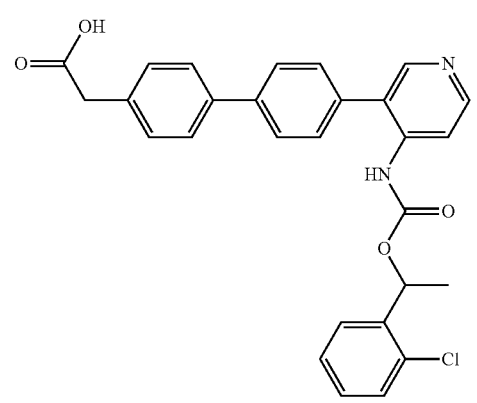

TABLE 5-continued
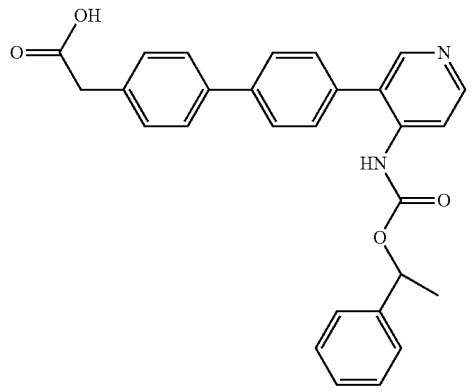 [SMILES: CC(OC(=O)Nc1ccncc1-c1ccc(-c2ccc(CC(=O)O)cc2)cc1)c1ccccc1]
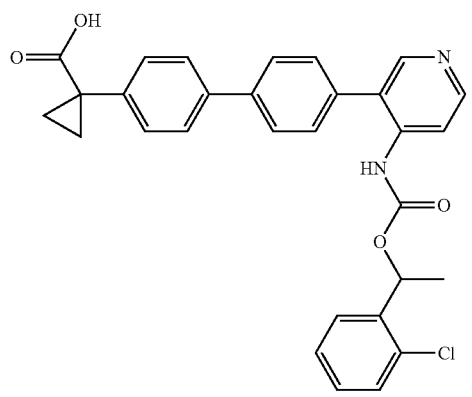 [SMILES: CC(OC(=O)Nc1ccncc1-c1ccc(-c2ccc(C3(C(=O)O)CC3)cc2)cc1)c1ccccc1Cl]
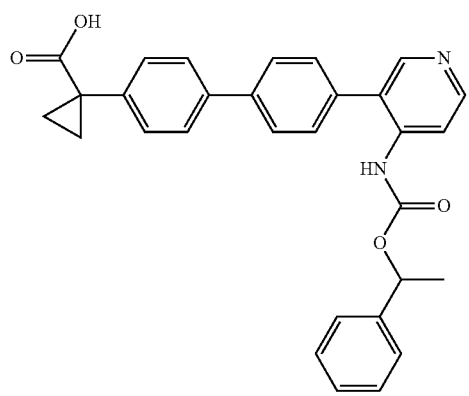 [SMILES: CC(OC(=O)Nc1ccncc1-c1ccc(-c2ccc(C3(C(=O)O)CC3)cc2)cc1)c1ccccc1]
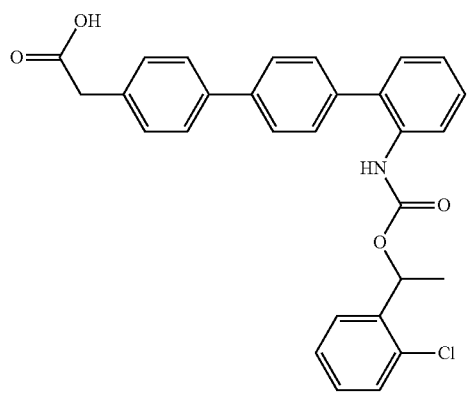
TABLE 5-continued
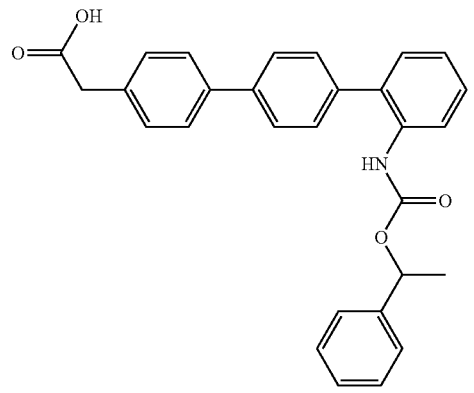 [SMILES: CC(OC(=O)Nc1ccccc1-c1ccc(-c2ccc(CC(=O)O)cc2)cc1)c1ccccc1]
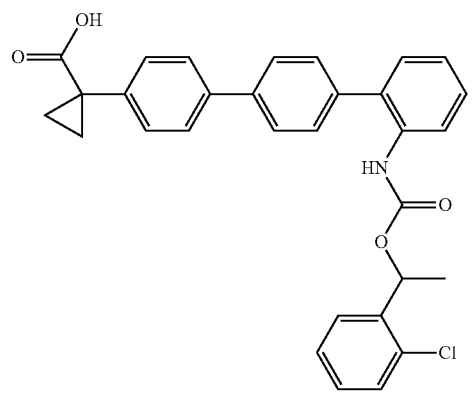 [SMILES: CC(OC(=O)Nc1ccccc1-c1ccc(-c2ccc(C3(C(=O)O)CC3)cc2)cc1)c1ccccc1Cl]
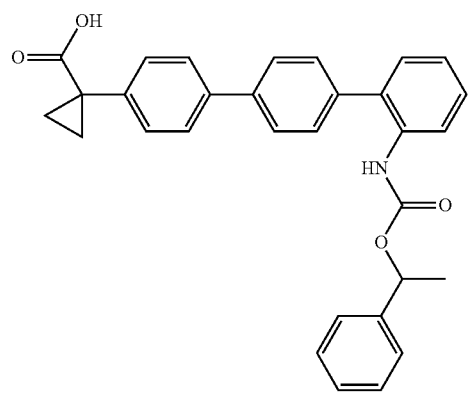
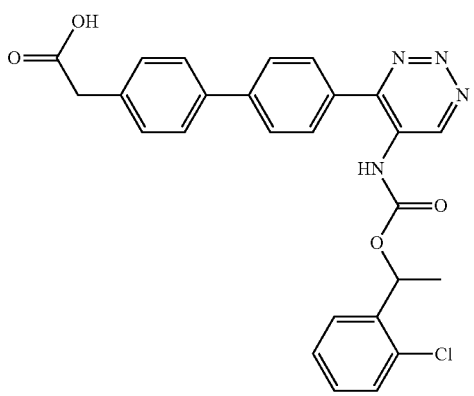 [SMILES: CC(OC(=O)Nc1cnnnc1-c1ccc(-c2ccc(CC(=O)O)cc2)cc1)c1ccccc1Cl]

TABLE 5-continued
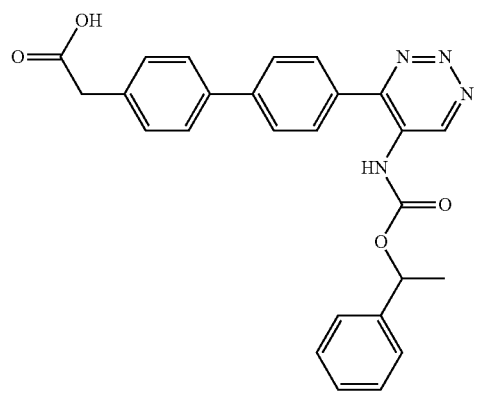 [SMILES: CC(OC(=O)Nc1cnnnc1-c1ccc(-c2ccc(CC(=O)O)cc2)cc1)c1ccccc1]
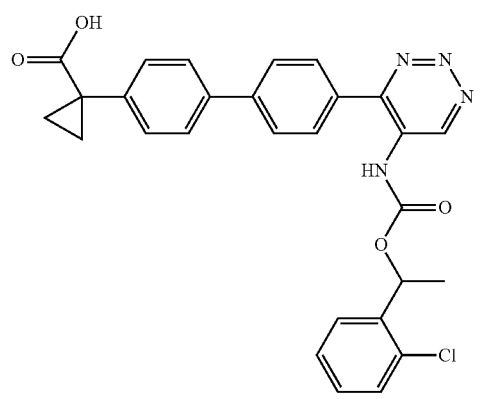
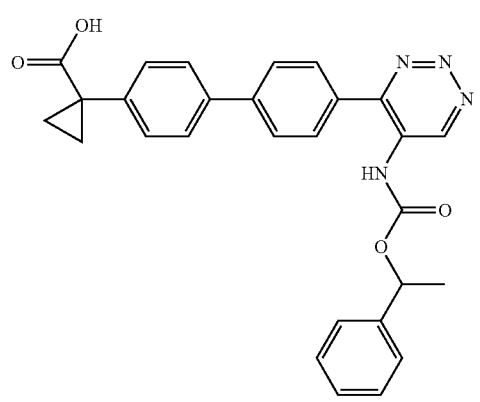 [SMILES: CC(OC(=O)Nc1cnnnc1-c1ccc(-c2ccc(C3(C(=O)O)CC3)cc2)cc1)c1ccccc1]
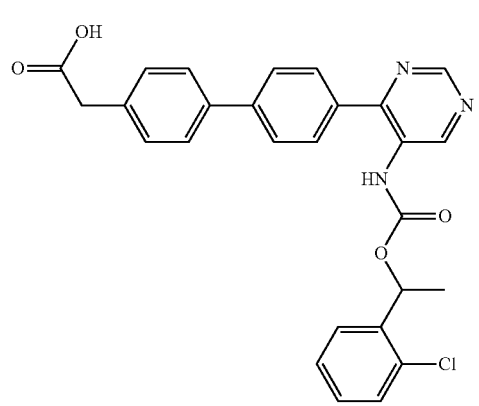
TABLE 5-continued
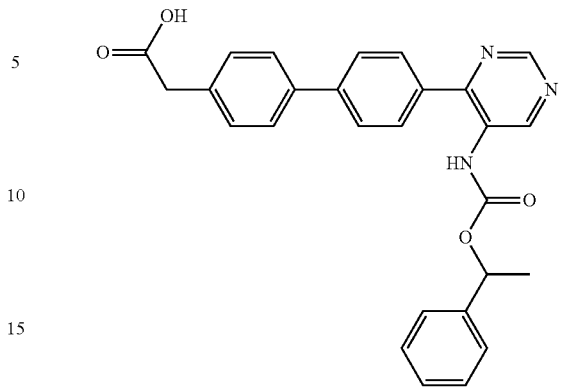

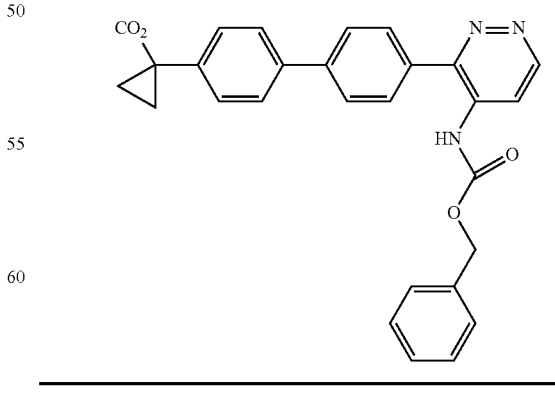
In some embodiments, compounds of Formula (I) are selected from the following compounds as listed in Table 6.

TABLE 6
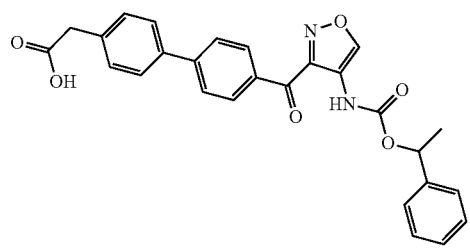 [SMILES: CC(OC(=O)Nc1conc1C(=O)c1ccc(-c2ccc(CC(=O)O)cc2)cc1)c1ccccc1]
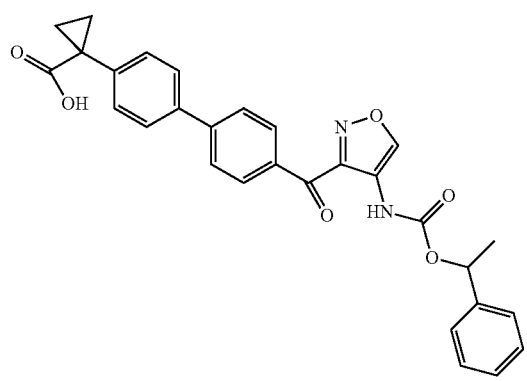 [SMILES: CC(OC(=O)Nc1conc1C(=O)c1ccc(-c2ccc(C3(C(=O)O)CC3)cc2)cc1)c1ccccc1]
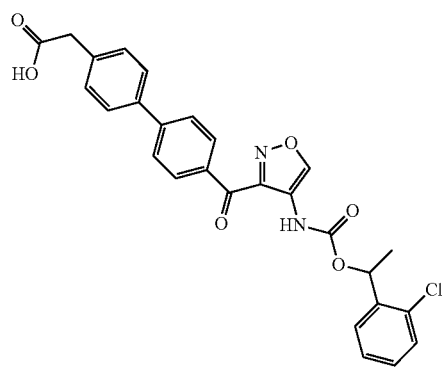 [SMILES: CC(OC(=O)Nc1conc1C(=O)c1ccc(-c2ccc(CC(=O)O)cc2)cc1)c1ccccc1Cl]
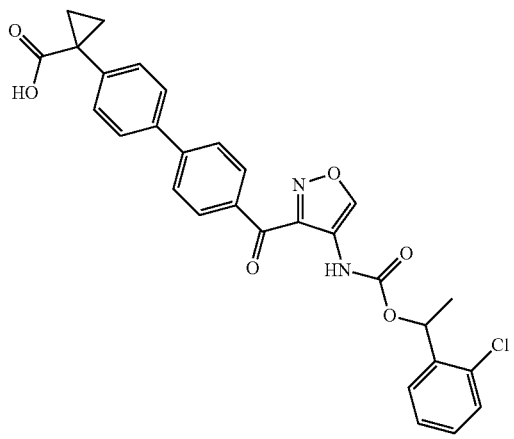 [SMILES: CC(OC(=O)Nc1conc1C(=O)c1ccc(-c2ccc(C3(C(=O)O)CC3)cc2)cc1)c1ccccc1Cl]
TABLE 6-continued
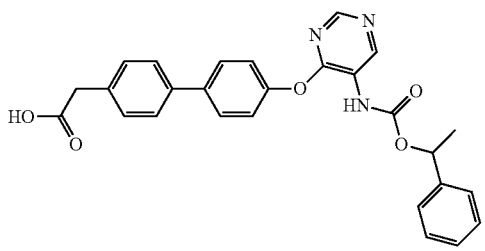 [SMILES: CC(OC(=O)Nc1cncnc1Oc1ccc(-c2ccc(CC(=O)O)cc2)cc1)c1ccccc1]
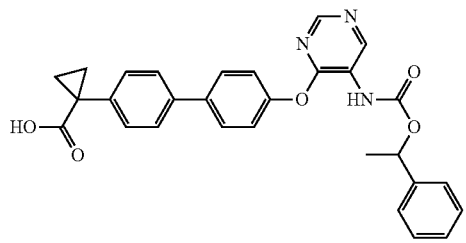 [SMILES: CC(OC(=O)Nc1cncnc1Oc1ccc(-c2ccc(C3(C(=O)O)CC3)cc2)cc1)c1ccccc1]
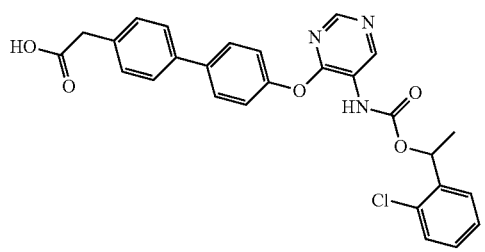 [SMILES: CC(OC(=O)Nc1cncnc1Oc1ccc(-c2ccc(CC(=O)O)cc2)cc1)c1ccccc1Cl]
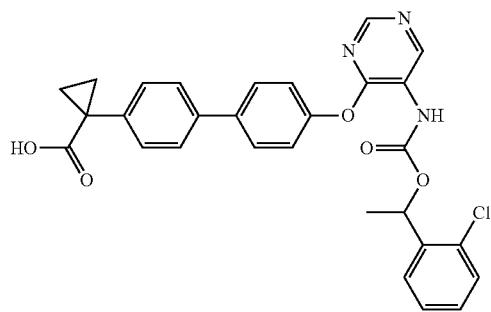 [SMILES: CC(OC(=O)Nc1cncnc1Oc1ccc(-c2ccc(C3(C(=O)O)CC3)cc2)cc1)c1ccccc1Cl]
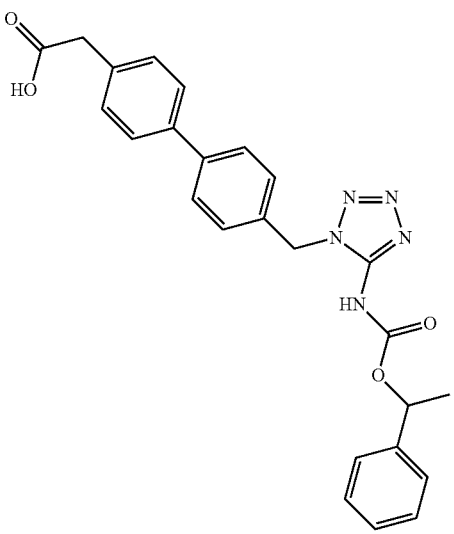 [SMILES: CC(OC(=O)Nc1nnnn1Cc1ccc(-c2ccc(CC(=O)O)cc2)cc1)c1ccccc1]

TABLE 6-continued
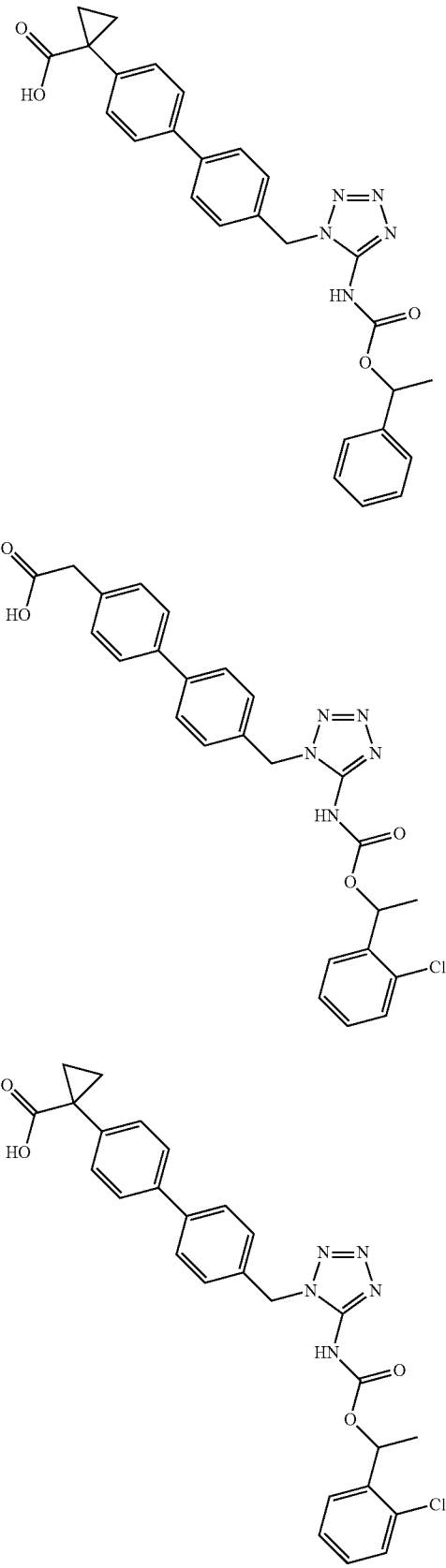
TABLE 6-continued
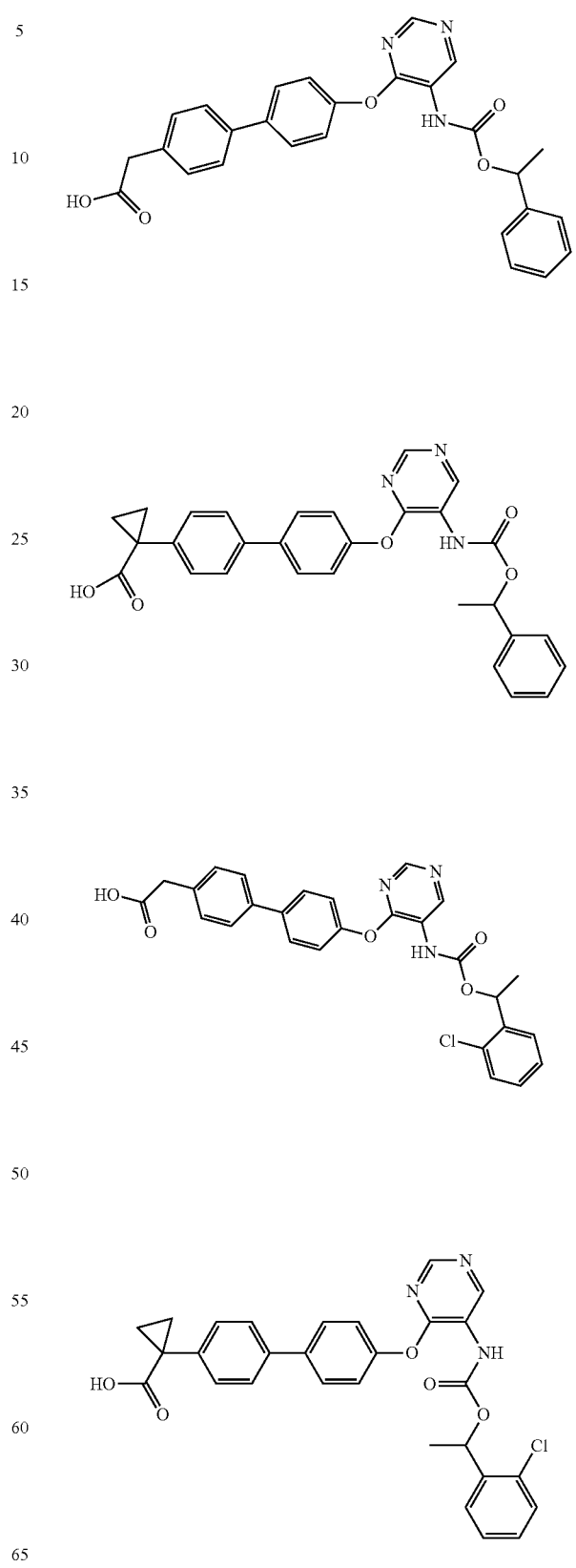

TABLE 6-continued
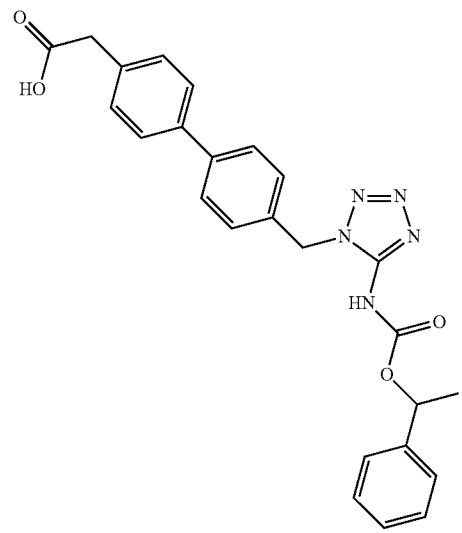 [SMILES: CC(OC(=O)Nc1nnnn1Cc1ccc(-c2ccc(CC(=O)O)cc2)cc1)c1ccccc1]
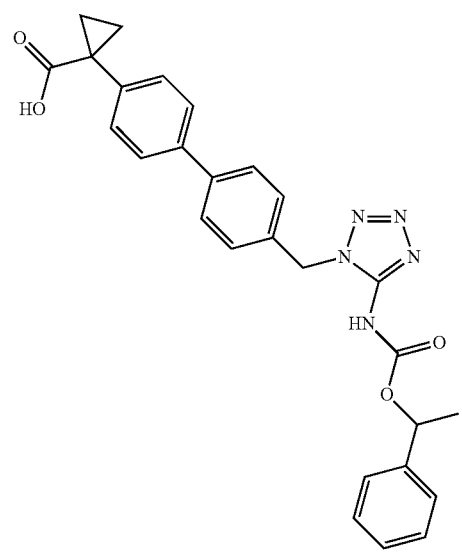 [SMILES: CC(OC(=O)Nc1nnnn1Cc1ccc(-c2ccc(C3(C(=O)O)CC3)cc2)cc1)c1ccccc1]
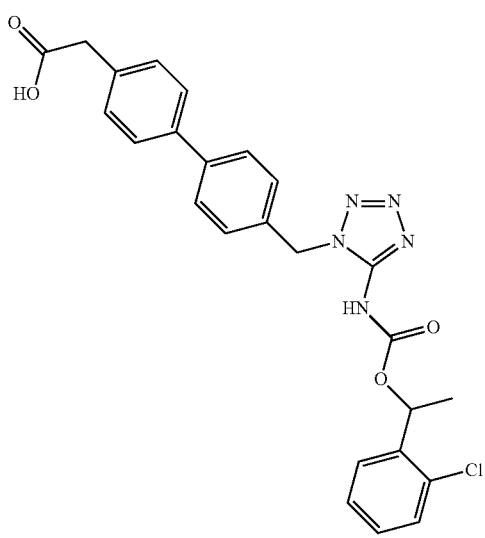 [SMILES: CC(OC(=O)Nc1nnnn1Cc1ccc(-c2ccc(CC(=O)O)cc2)cc1)c1ccccc1Cl]
TABLE 6-continued
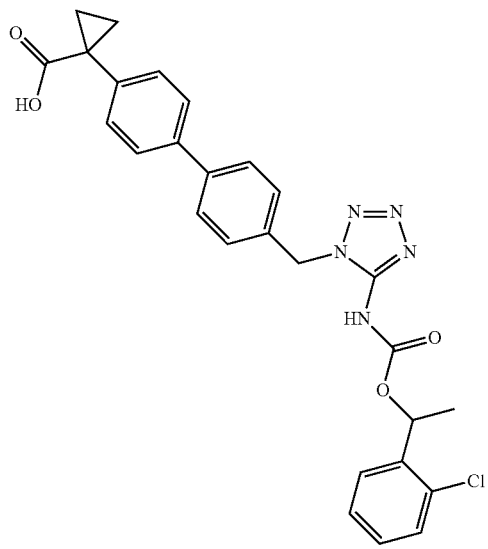 [SMILES: CC(OC(=O)Nc1nnnn1Cc1ccc(-c2ccc(C3(C(=O)O)CC3)cc2)cc1)c1ccccc1Cl]
In some embodiments, compounds of Formula (I) are selected from the following compounds as listed in Table 7.
TABLE 7
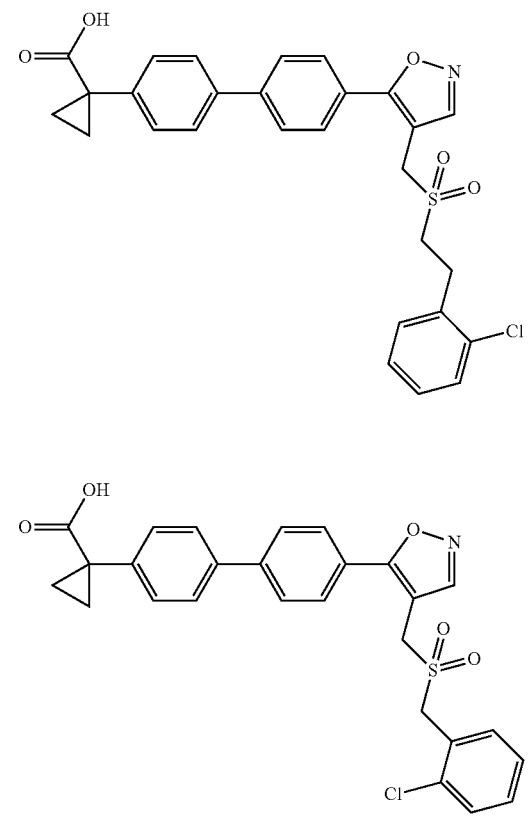

TABLE 7-continued
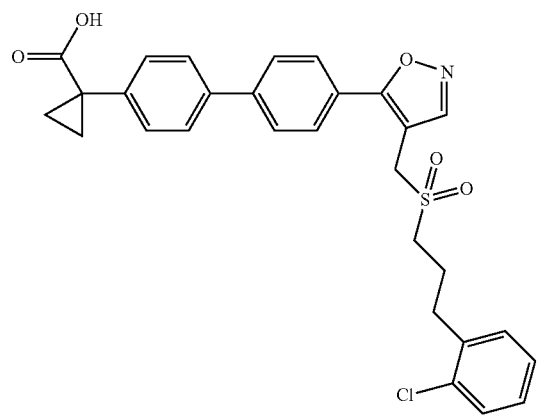 [SMILES: O=C(O)C1(c2ccc(-c3ccc(-c4oncc4CS(=O)(=O)CCCc4ccccc4Cl)cc3)cc2)CC1]
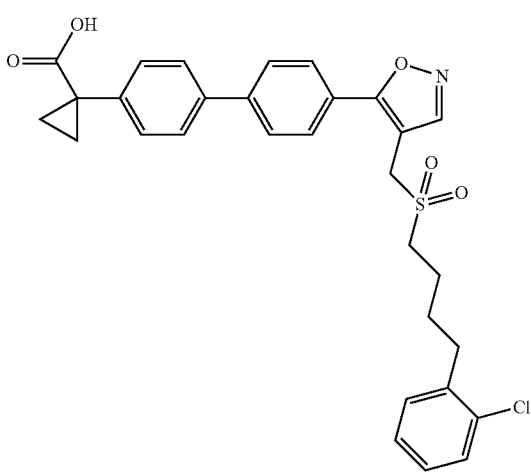 [SMILES: O=C(O)C1(c2ccc(-c3ccc(-c4oncc4CS(=O)(=O)CCCCc4ccccc4Cl)cc3)cc2)CC1]
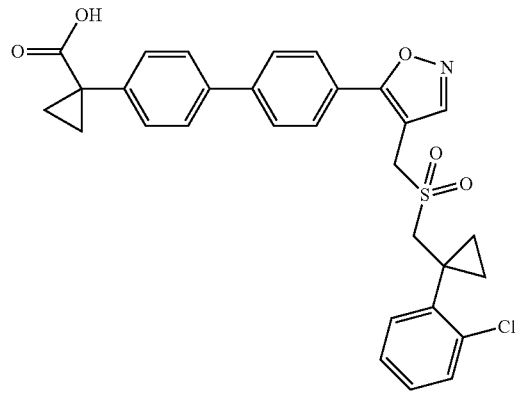 [SMILES: O=C(O)C1(c2ccc(-c3ccc(-c4oncc4CS(=O)(=O)CC4(c5ccccc5Cl)CC4)cc3)cc2)CC1]
TABLE 7-continued
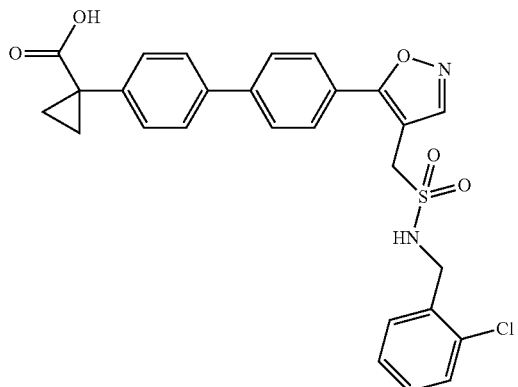
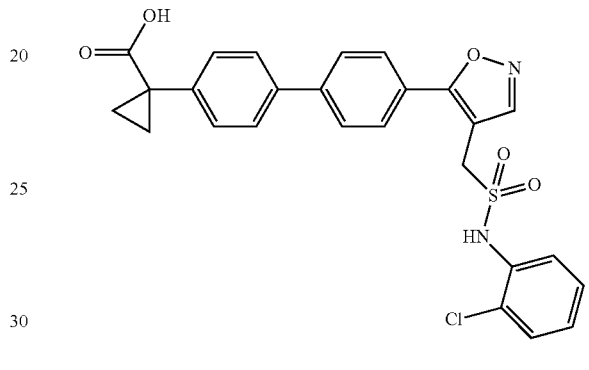
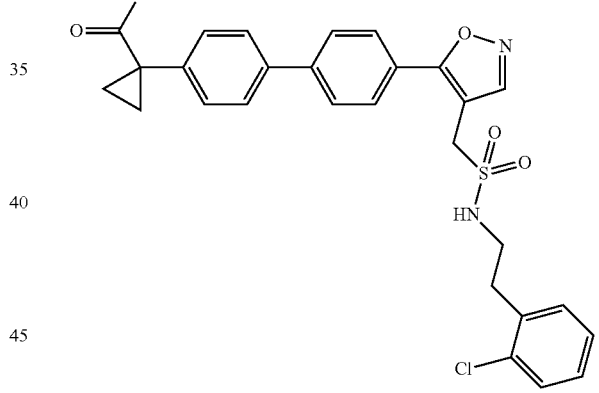

TABLE 7-continued
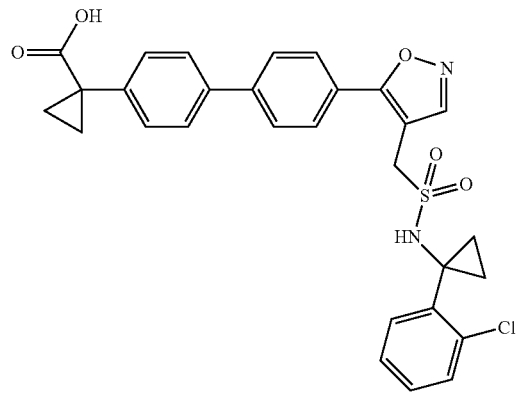 [SMILES: O=C(O)C1(c2ccc(-c3ccc(-c4oncc4CS(=O)(=O)NC4(c5ccccc5Cl)CC4)cc3)cc2)CC1]
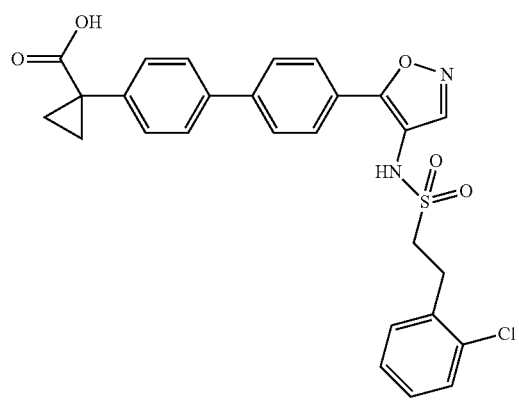 [SMILES: O=C(O)C1(c2ccc(-c3ccc(-c4oncc4NS(=O)(=O)CCc4ccccc4Cl)cc3)cc2)CC1]
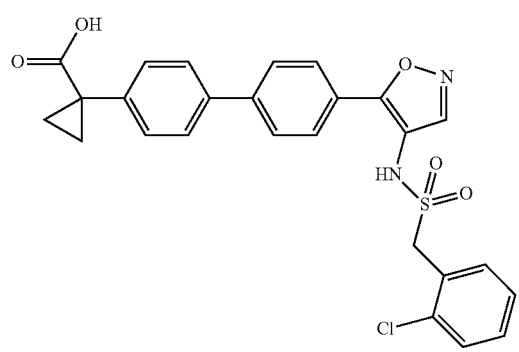 [SMILES: O=C(O)C1(c2ccc(-c3ccc(-c4oncc4NS(=O)(=O)Cc4ccccc4Cl)cc3)cc2)CC1]
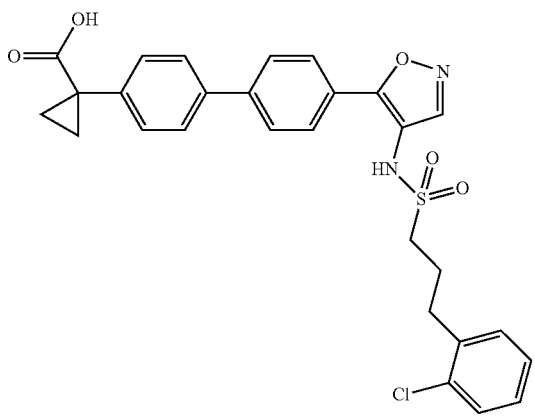 [SMILES: O=C(O)C1(c2ccc(-c3ccc(-c4oncc4NS(=O)(=O)CCCc4ccccc4Cl)cc3)cc2)CC1]
TABLE 7-continued
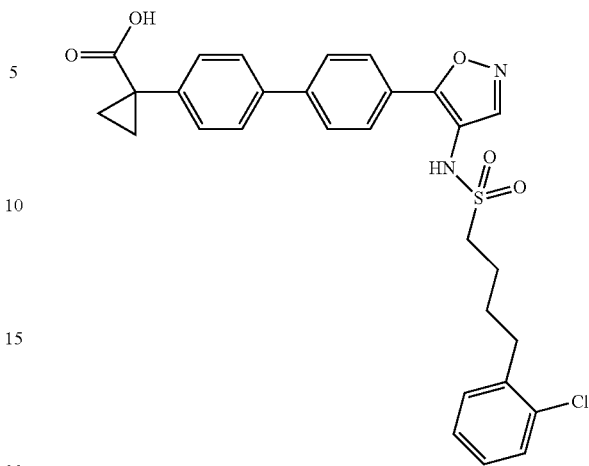
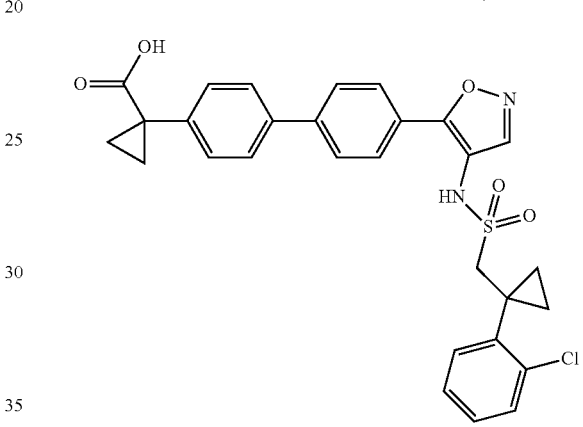
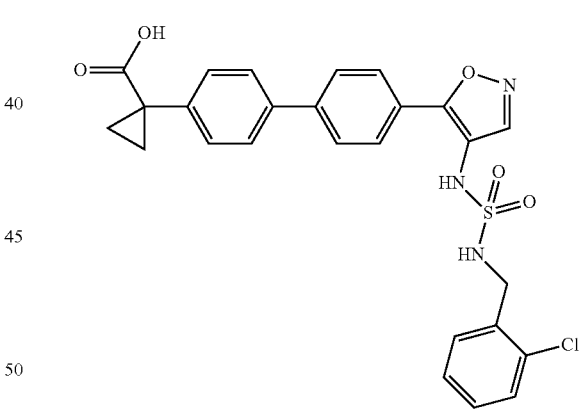
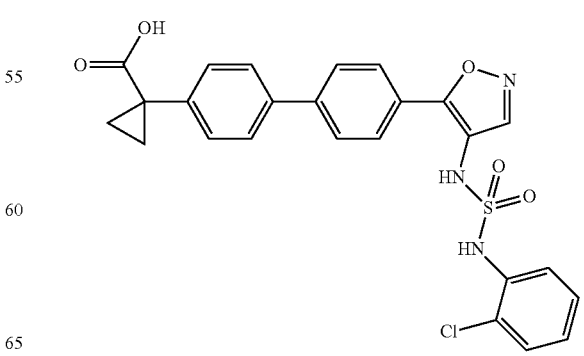

TABLE 7-continued
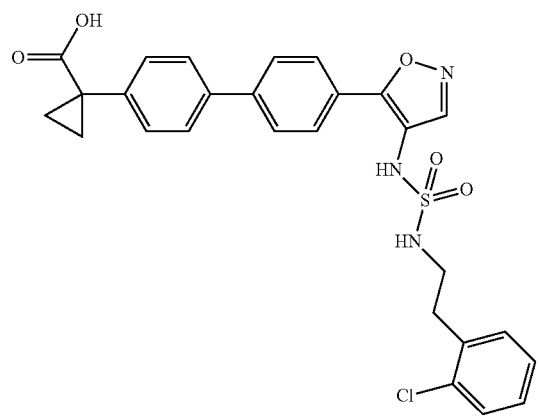 [SMILES: O=C(O)C1(c2ccc(-c3ccc(-c4oncc4NS(=O)(=O)NCCc4ccccc4Cl)cc3)cc2)CC1]
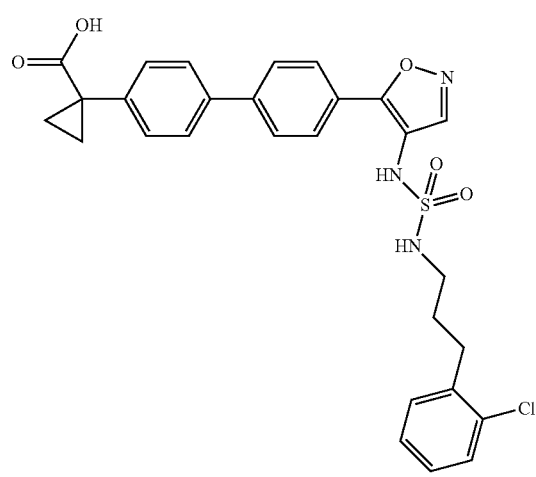 [SMILES: O=C(O)C1(c2ccc(-c3ccc(-c4oncc4NS(=O)(=O)NCCCc4ccccc4Cl)cc3)cc2)CC1]
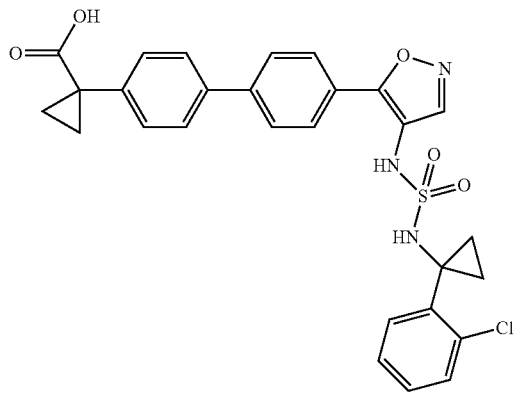
TABLE 7-continued
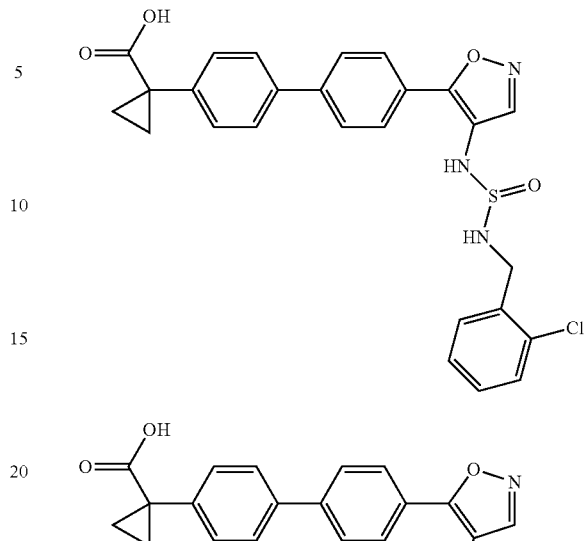
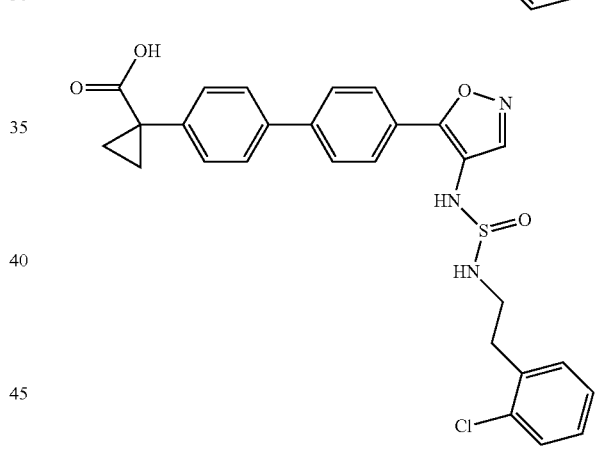
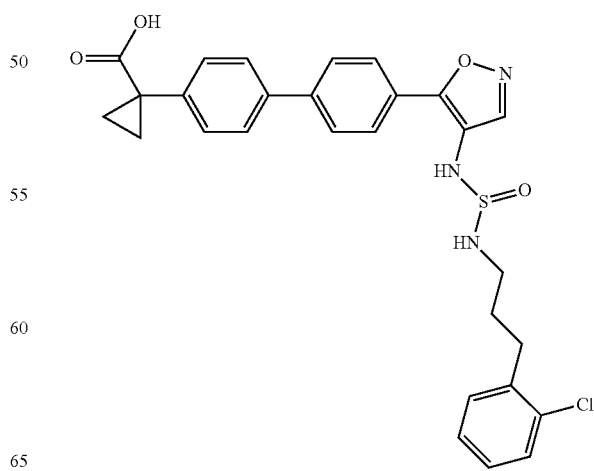

TABLE 7-continued
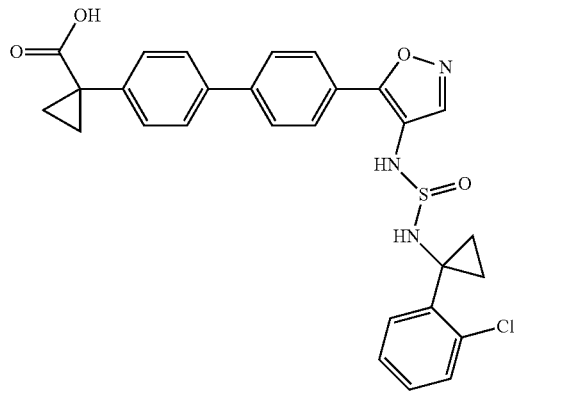 [SMILES: O=C(O)C1(c2ccc(-c3ccc(-c4oncc4NS(=O)NC4(c5ccccc5Cl)CC4)cc3)cc2)CC1]
In some embodiments, compounds of Formula (I) are selected from the following compounds as listed in Table 8.
TABLE 8
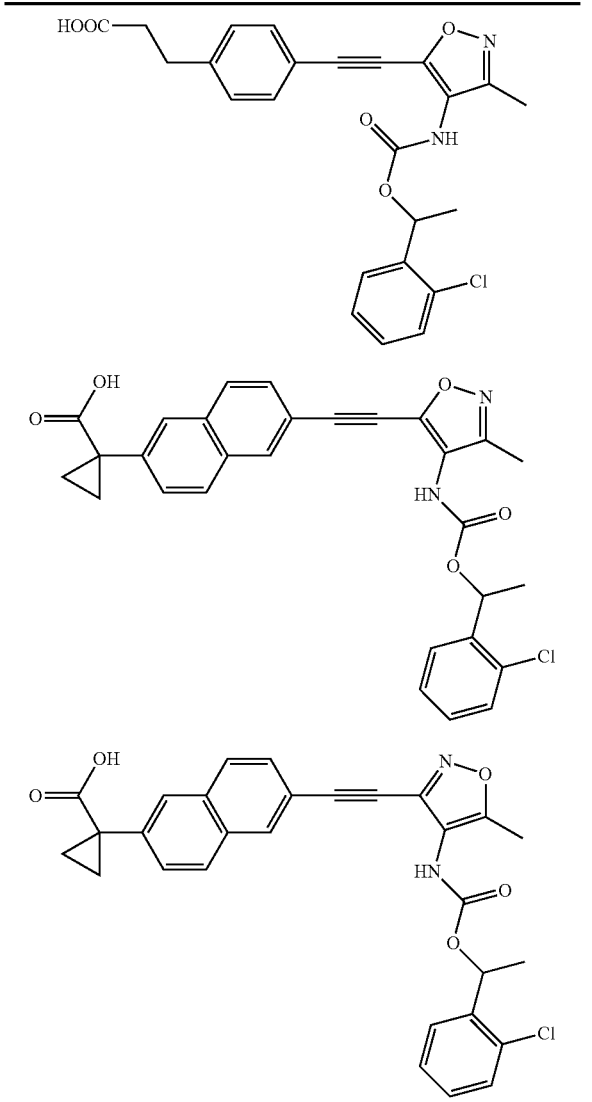
TABLE 8-continued
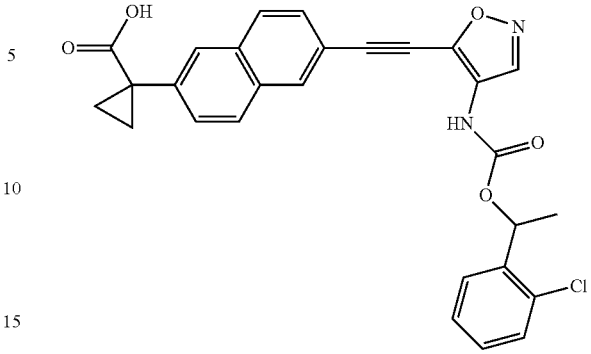
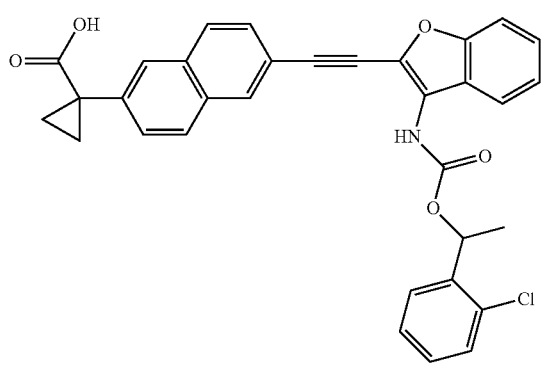 [SMILES: CC(OC(=O)Nc1c(C#Cc2ccc3cc(C4(C(=O)O)CC4)ccc3c2)oc2ccccc12)c1ccccc1Cl]
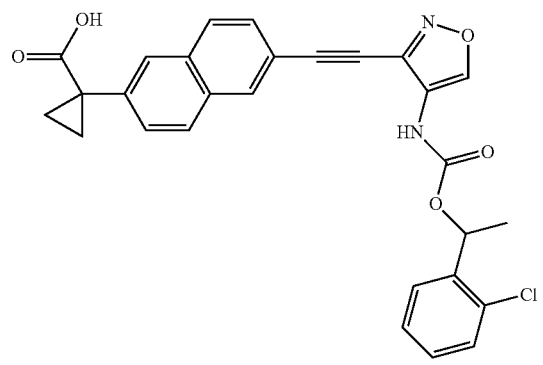 [SMILES: CC(OC(=O)Nc1conc1C#Cc1ccc2cc(C3(C(=O)O)CC3)ccc2c1)c1ccccc1Cl]
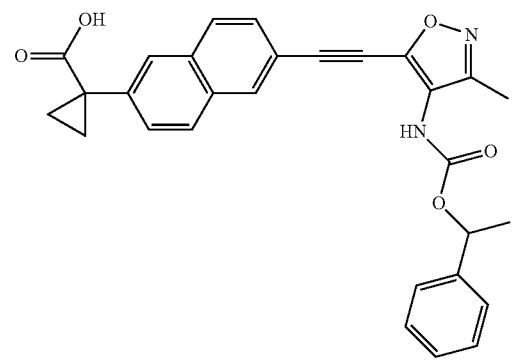 [SMILES: Cc1noc(C#Cc2ccc3cc(C4(C(=O)O)CC4)ccc3c2)c1NC(=O)OC(C)c1ccccc1]

395
TABLE 8-continued
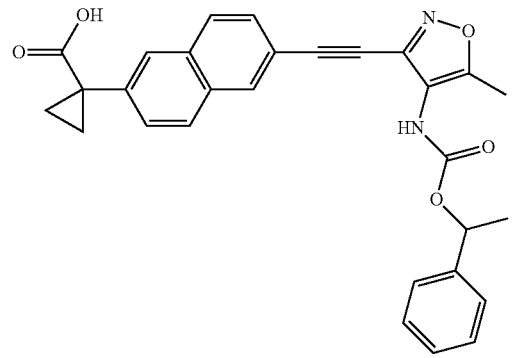 [SMILES: Cc1onc(C#Cc2ccc3cc(C4(C(=O)O)CC4)ccc3c2)c1NC(=O)OC(C)c1ccccc1]
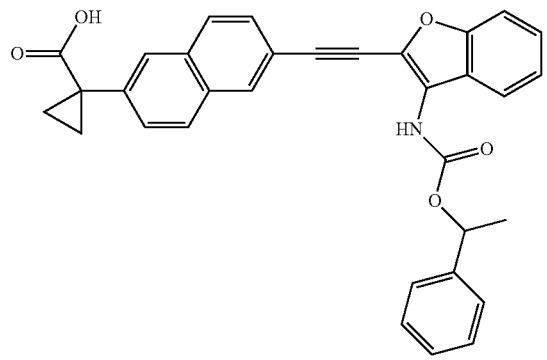 [SMILES: CC(OC(=O)Nc1c(C#Cc2ccc3cc(C4(C(=O)O)CC4)ccc3c2)oc2ccccc12)c1ccccc1]
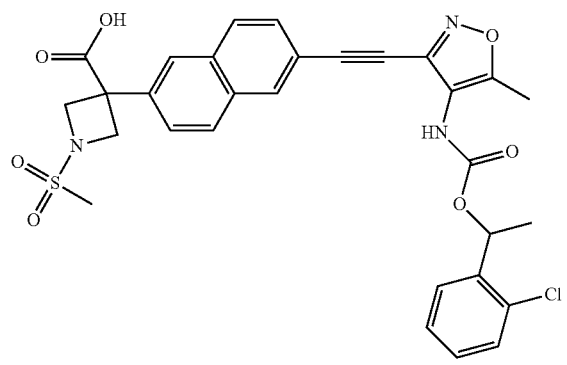 [SMILES: Cc1onc(C#Cc2ccc3cc(C4(C(=O)O)CN(S(C)(=O)=O)C4)ccc3c2)c1NC(=O)OC(C)c1ccccc1Cl]
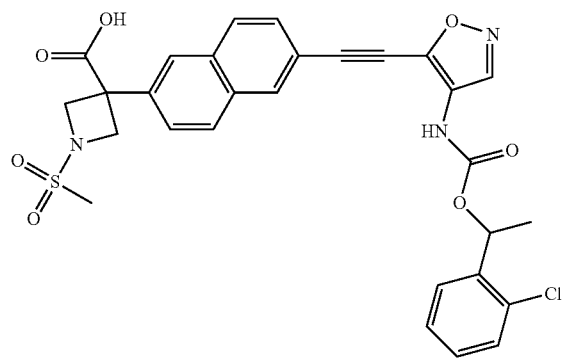 [SMILES: CC(OC(=O)Nc1cnoc1C#Cc1ccc2cc(C3(C(=O)O)CN(S(C)(=O)=O)C3)ccc2c1)c1ccccc1Cl]
396
TABLE 8-continued
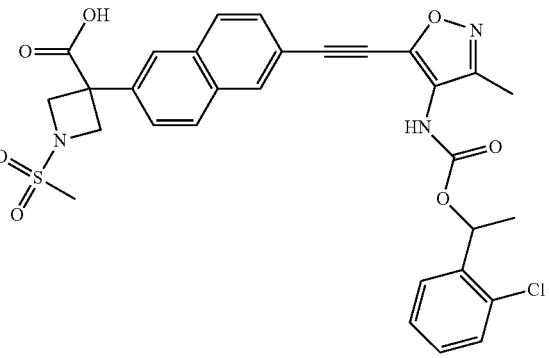

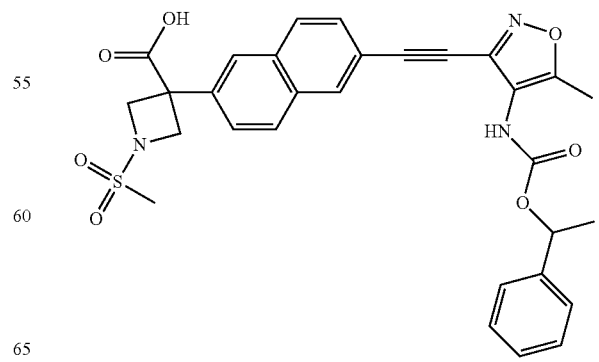

TABLE 8-continued
397
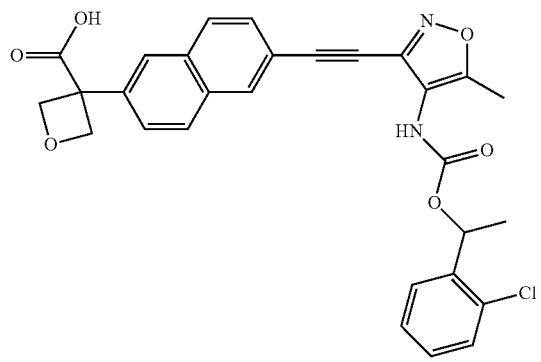 [SMILES: Cc1onc(C#Cc2ccc3cc(C4(C(=O)O)COC4)ccc3c2)c1NC(=O)OC(C)c1ccccc1Cl]
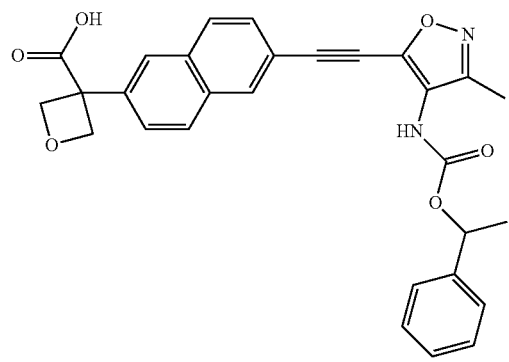 [SMILES: Cc1noc(C#Cc2ccc3cc(C4(C(=O)O)COC4)ccc3c2)c1NC(=O)OC(C)c1ccccc1]
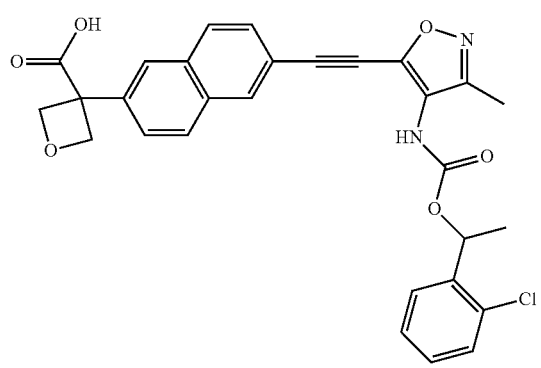 [SMILES: Cc1noc(C#Cc2ccc3cc(C4(C(=O)O)COC4)ccc3c2)c1NC(=O)OC(C)c1ccccc1Cl]
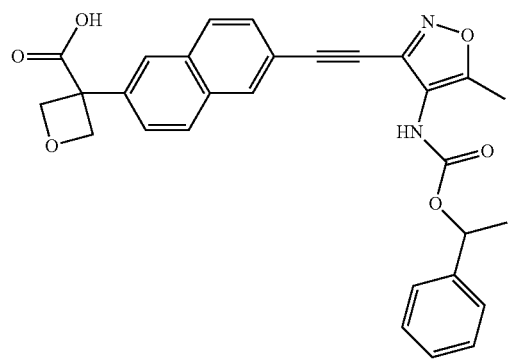 [SMILES: Cc1onc(C#Cc2ccc3cc(C4(C(=O)O)COC4)ccc3c2)c1NC(=O)OC(C)c1ccccc1]
TABLE 8-continued
398
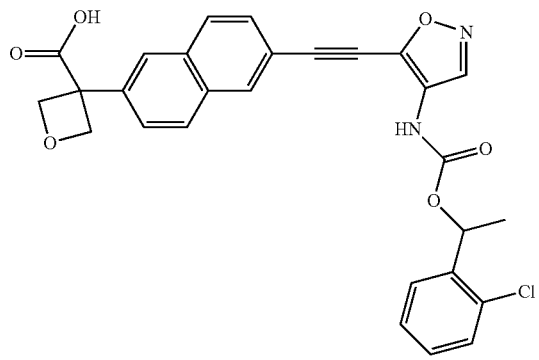 [SMILES: CC(OC(=O)Nc1cnoc1C#Cc1ccc2cc(C3(C(=O)O)COC3)ccc2c1)c1ccccc1Cl]
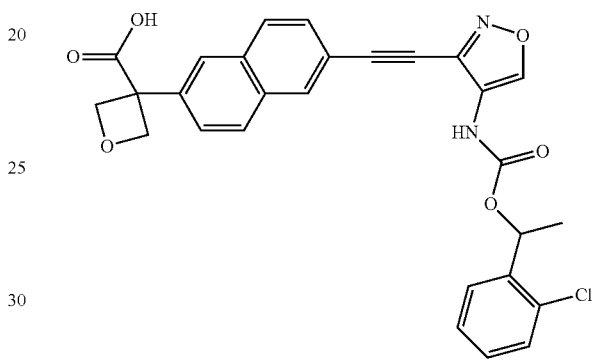
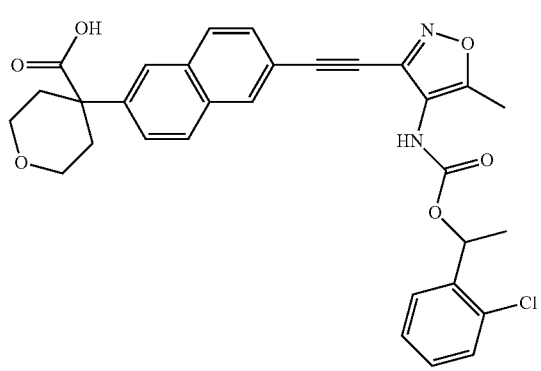 [SMILES: Cc1onc(C#Cc2ccc3cc(C4(C(=O)O)CCOCC4)ccc3c2)c1NC(=O)OC(C)c1ccccc1Cl]
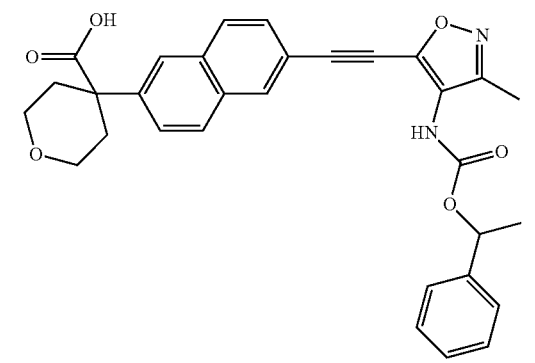 [SMILES: Cc1noc(C#Cc2ccc3cc(C4(C(=O)O)CCOCC4)ccc3c2)c1NC(=O)OC(C)c1ccccc1]

TABLE 8-continued
399
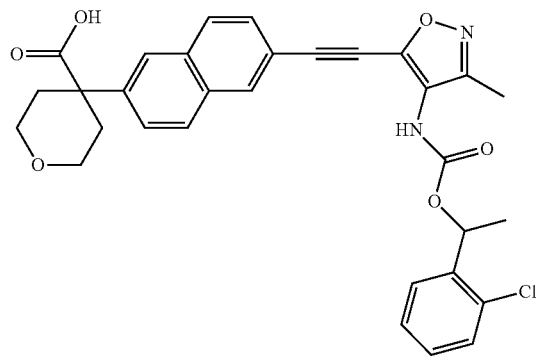 [SMILES: Cc1noc(C#Cc2ccc3cc(C4(C(=O)O)CCOCC4)ccc3c2)c1NC(=O)OC(C)c1ccccc1Cl]
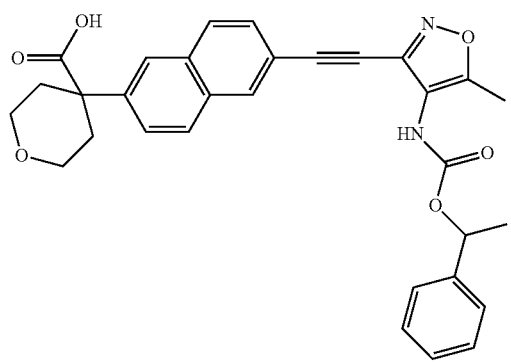 [SMILES: Cc1onc(C#Cc2ccc3cc(C4(C(=O)O)CCOCC4)ccc3c2)c1NC(=O)OC(C)c1ccccc1]
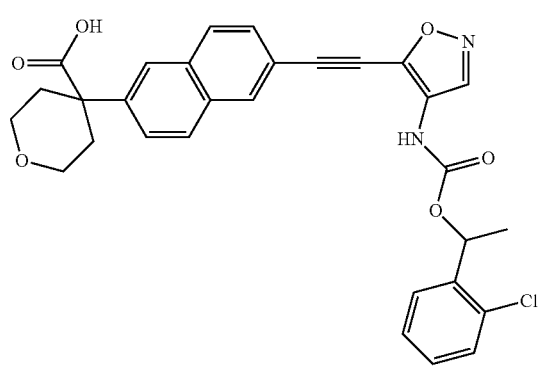 [SMILES: CC(OC(=O)Nc1cnoc1C#Cc1ccc2cc(C3(C(=O)O)CCOCC3)ccc2c1)c1ccccc1Cl]
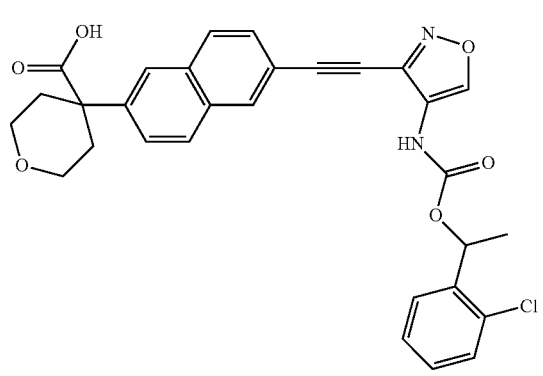 [SMILES: CC(OC(=O)Nc1conc1C#Cc1ccc2cc(C3(C(=O)O)CCOCC3)ccc2c1)c1ccccc1Cl]
TABLE 8-continued
400
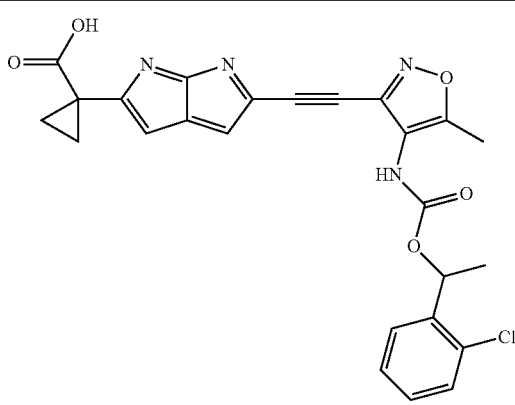
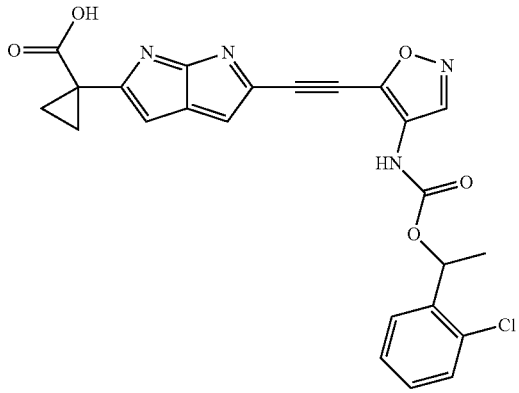 [SMILES: CC(OC(=O)Nc1cnoc1C#CC1=NC2=NC(C3(C(=O)O)CC3)=CC2=C1)c1ccccc1Cl]
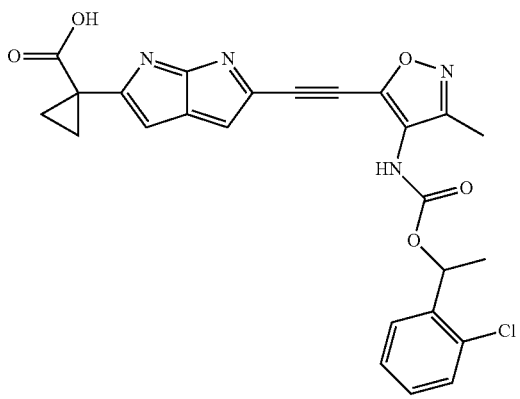 [SMILES: Cc1noc(C#CC2=NC3=NC(C4(C(=O)O)CC4)=CC3=C2)c1NC(=O)OC(C)c1ccccc1Cl]
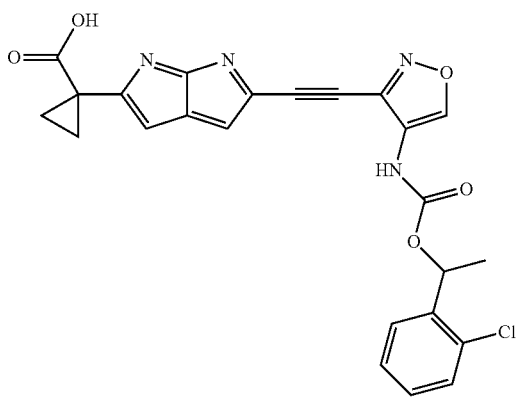 [SMILES: CC(OC(=O)Nc1conc1C#CC1=NC2=NC(C3(C(=O)O)CC3)=CC2=C1)c1ccccc1Cl]

TABLE 8-continued
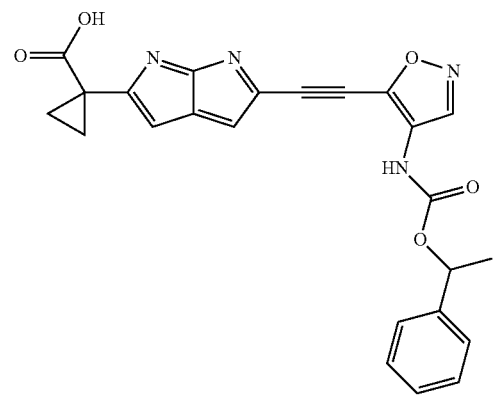 [SMILES: CC(OC(=O)Nc1cnoc1C#CC1=NC2=NC(C3(C(=O)O)CC3)=CC2=C1)c1ccccc1]
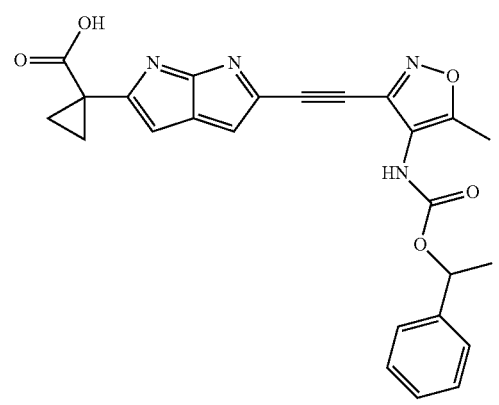 [SMILES: Cc1onc(C#CC2=NC3=NC(C4(C(=O)O)CC4)=CC3=C2)c1NC(=O)OC(C)c1ccccc1]
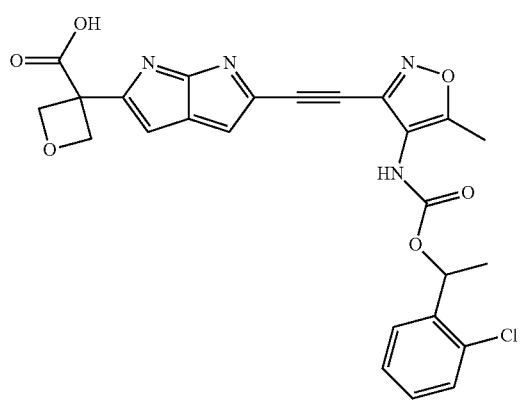 [SMILES: Cc1onc(C#CC2=NC3=NC(C4(C(=O)O)COC4)=CC3=C2)c1NC(=O)OC(C)c1ccccc1Cl]
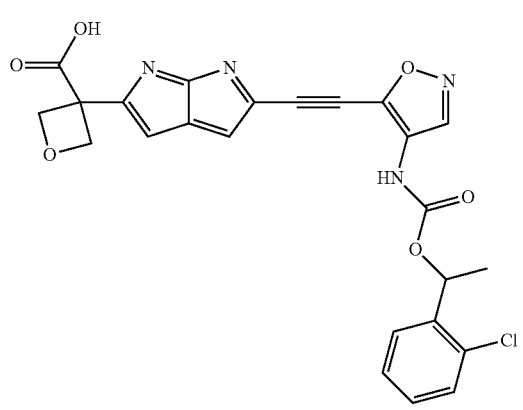 [SMILES: CC(OC(=O)Nc1cnoc1C#CC1=NC2=NC(C3(C(=O)O)COC3)=CC2=C1)c1ccccc1Cl]
TABLE 8-continued
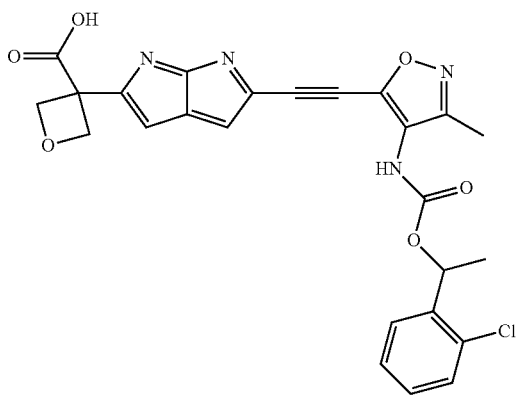 [SMILES: Cc1noc(C#CC2=NC3=NC(C4(C(=O)O)COC4)=CC3=C2)c1NC(=O)OC(C)c1ccccc1Cl]
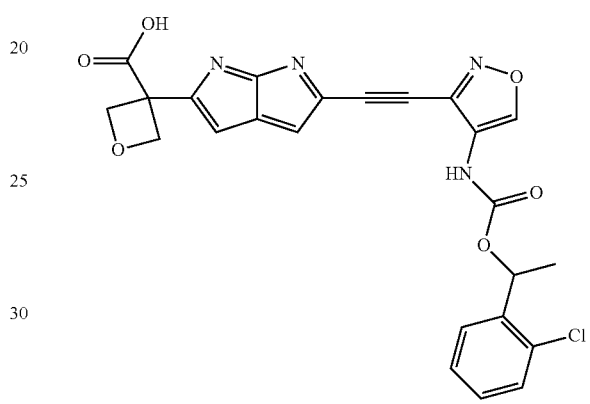
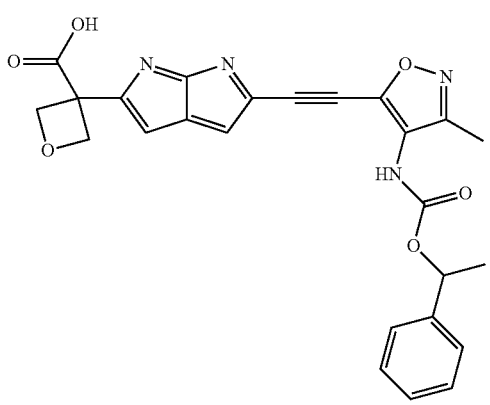
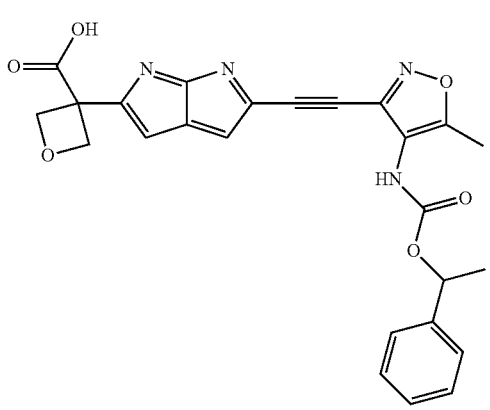 [SMILES: Cc1onc(C#CC2=NC3=NC(C4(C(=O)O)COC4)=CC3=C2)c1NC(=O)OC(C)c1ccccc1]

| 403 | 404 |
|---|---|
| TABLE 8-continued | TABLE 8-continued |
| 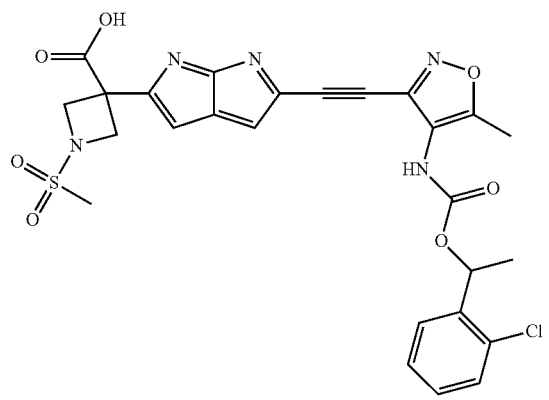 [SMILES: Cc1onc(C#CC2=NC3=NC(C4(C(=O)O)CN(S(C)(=O)=O)C4)=CC3=C2)c1NC(=O)OC(C)c1ccccc1Cl] | 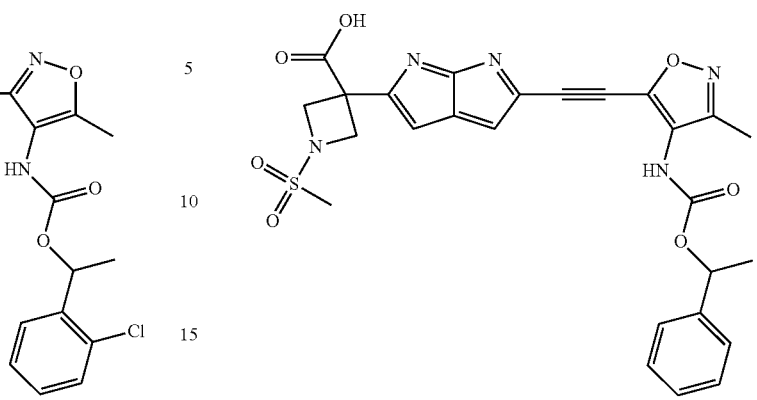 |
| 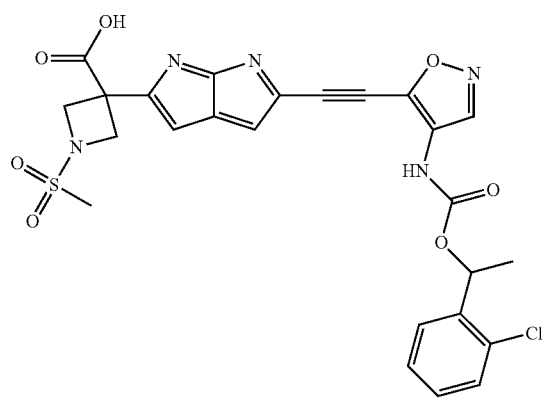 [SMILES: CC(OC(=O)Nc1cnoc1C#CC1=NC2=NC(C3(C(=O)O)CN(S(C)(=O)=O)C3)=CC2=C1)c1ccccc1Cl] | 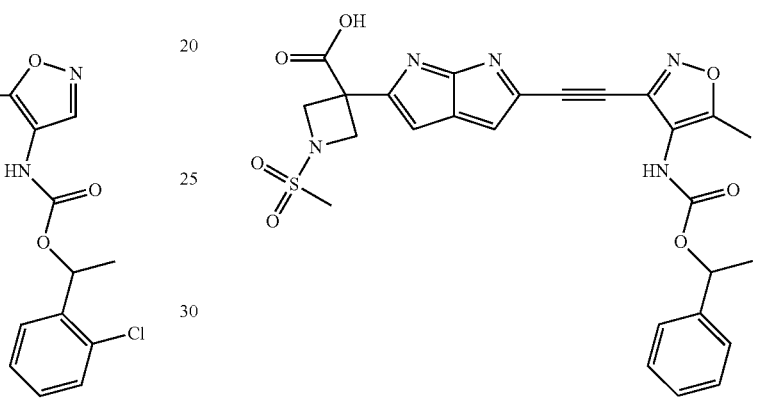 |
| 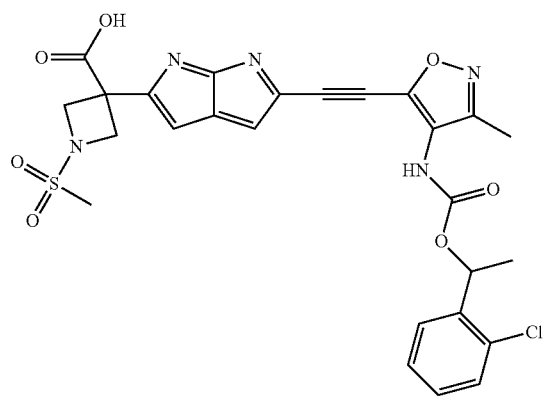 [SMILES: Cc1noc(C#CC2=NC3=NC(C4(C(=O)O)CN(S(C)(=O)=O)C4)=CC3=C2)c1NC(=O)OC(C)c1ccccc1Cl] | 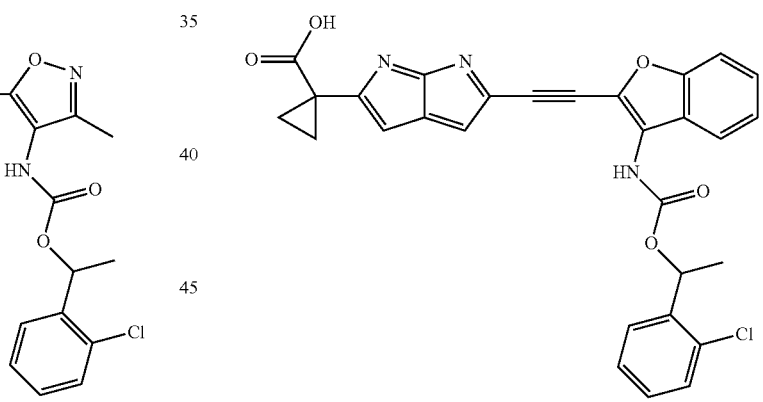 |
| 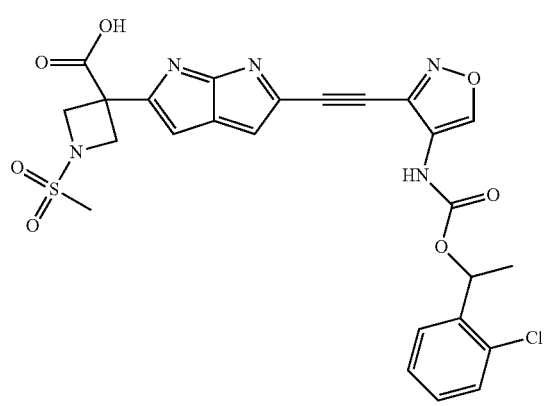 [SMILES: CC(OC(=O)Nc1conc1C#CC1=NC2=NC(C3(C(=O)O)CN(S(C)(=O)=O)C3)=CC2=C1)c1ccccc1Cl] | 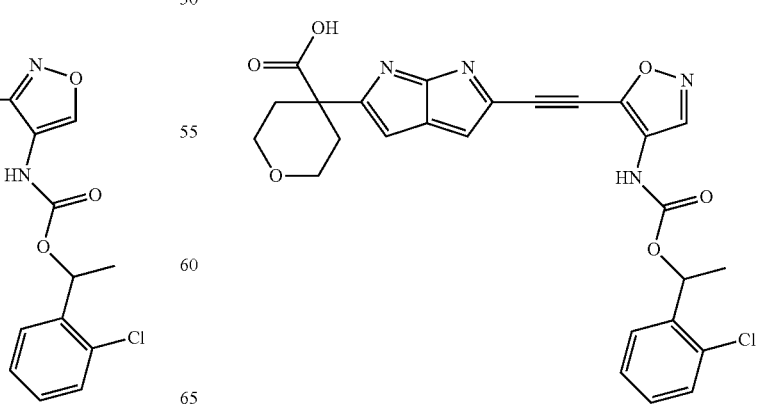 |

TABLE 8-continued
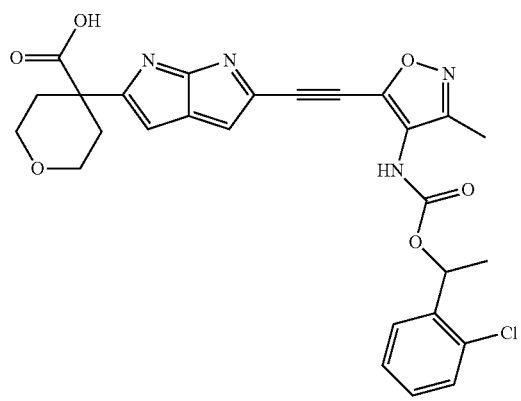 [SMILES: Cc1noc(C#CC2=NC3=NC(C4(C(=O)O)CCOCC4)=CC3=C2)c1NC(=O)OC(C)c1ccccc1Cl]
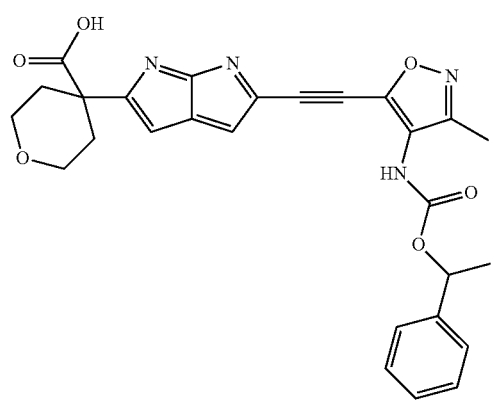 [SMILES: Cc1noc(C#CC2=NC3=NC(C4(C(=O)O)CCOCC4)=CC3=C2)c1NC(=O)OC(C)c1ccccc1]
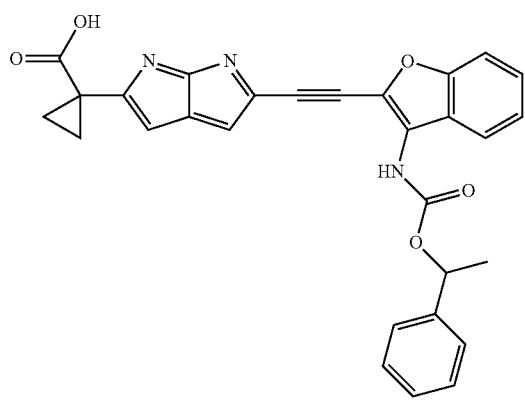 [SMILES: CC(OC(=O)Nc1c(C#CC2=NC3=NC(C4(C(=O)O)CC4)=CC3=C2)oc2ccccc12)c1ccccc1]
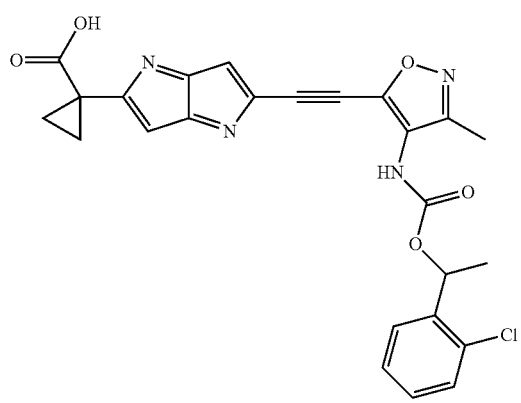 [SMILES: Cc1noc(C#CC2=CC3=NC(C4(C(=O)O)CC4)=CC3=N2)c1NC(=O)OC(C)c1ccccc1Cl]
TABLE 8-continued
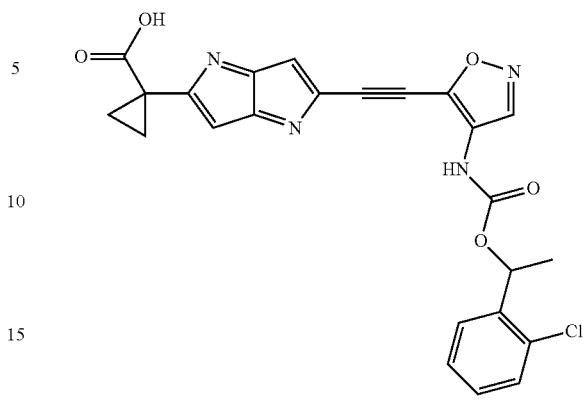
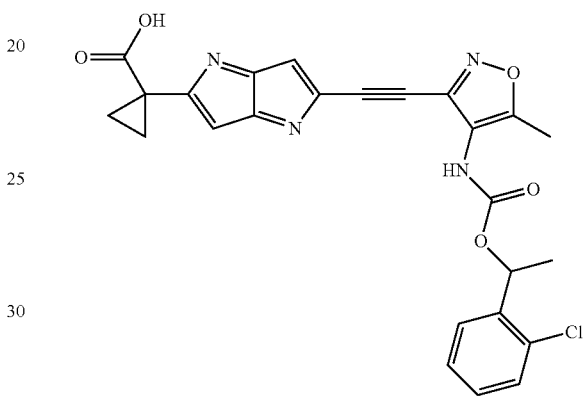
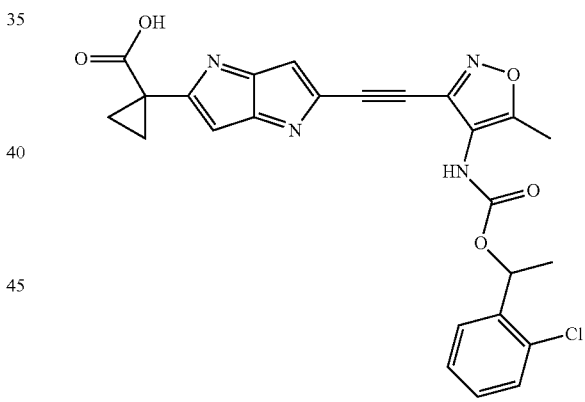
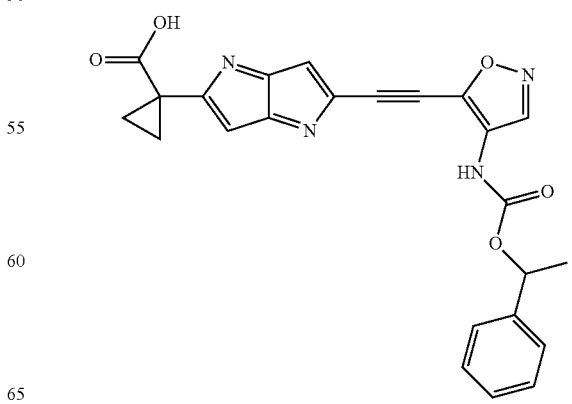

TABLE 8-continued
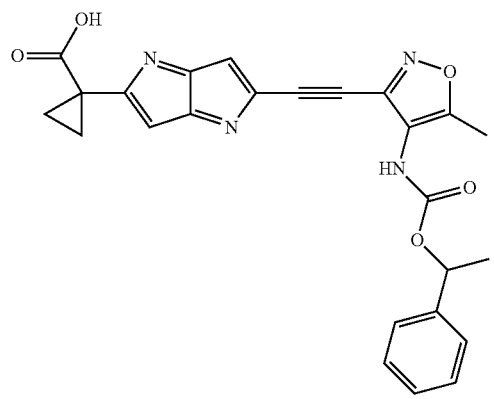 [SMILES: Cc1onc(C#CC2=CC3=NC(C4(C(=O)O)CC4)=CC3=N2)c1NC(=O)OC(C)c1ccccc1]
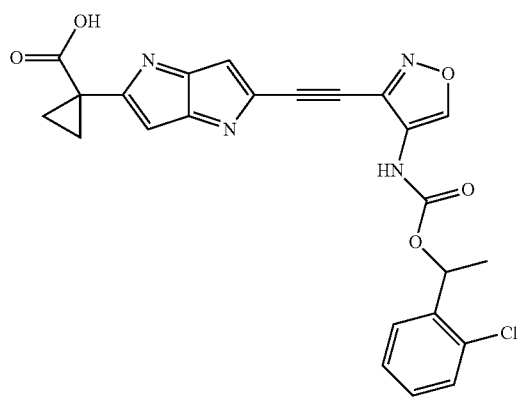 [SMILES: CC(OC(=O)Nc1conc1C#CC1=CC2=NC(C3(C(=O)O)CC3)=CC2=N1)c1ccccc1Cl]
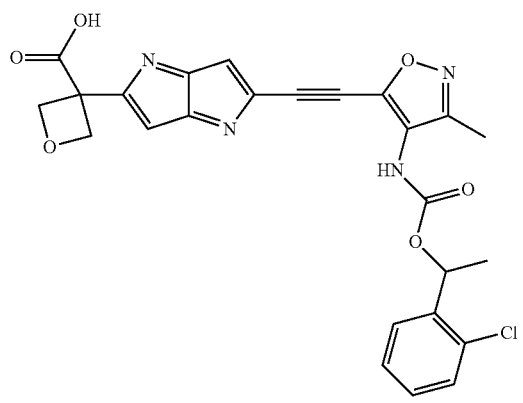 [SMILES: Cc1noc(C#CC2=CC3=NC(C4(C(=O)O)COC4)=CC3=N2)c1NC(=O)OC(C)c1ccccc1Cl]
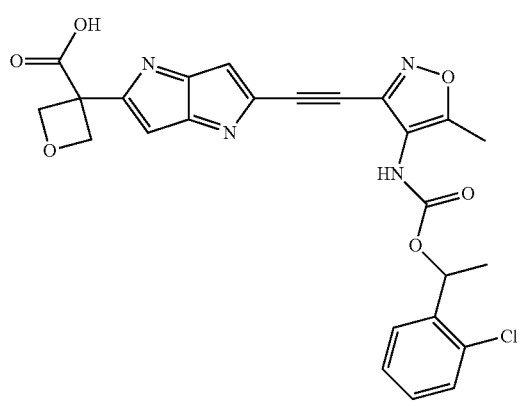 [SMILES: Cc1onc(C#CC2=CC3=NC(C4(C(=O)O)COC4)=CC3=N2)c1NC(=O)OC(C)c1ccccc1Cl]
TABLE 8-continued
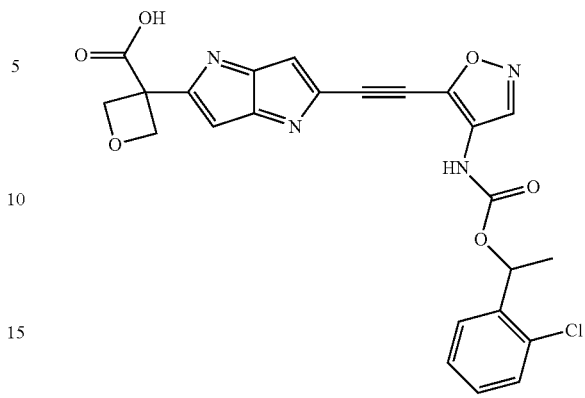
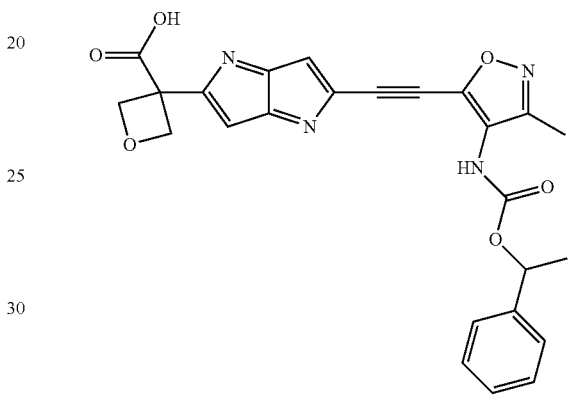
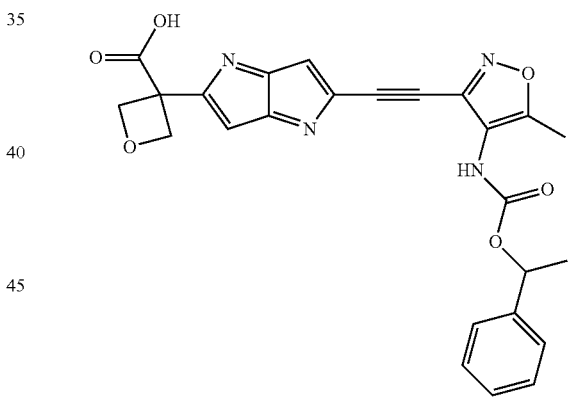
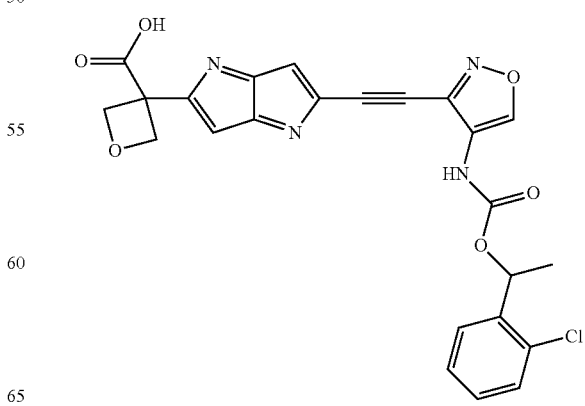

TABLE 8-continued
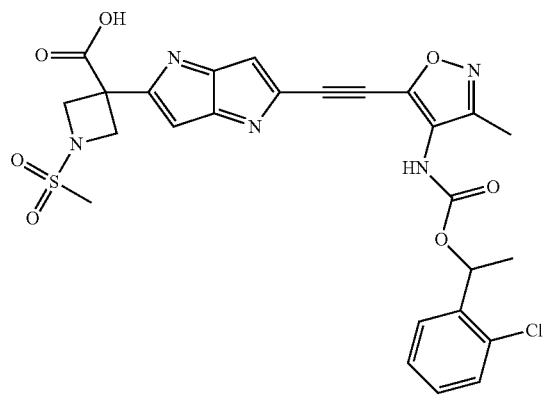 [SMILES: Cc1noc(C#CC2=CC3=NC(C4(C(=O)O)CN(S(C)(=O)=O)C4)=CC3=N2)c1NC(=O)OC(C)c1ccccc1Cl]
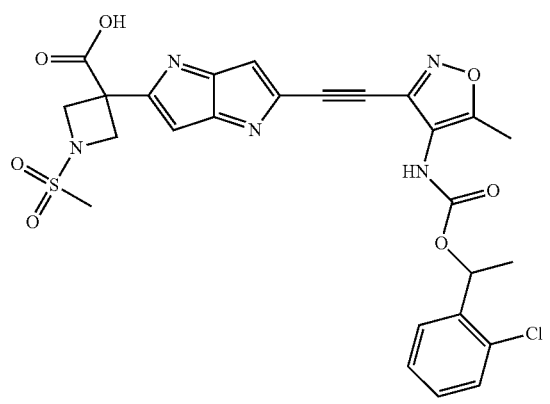 [SMILES: Cc1onc(C#CC2=CC3=NC(C4(C(=O)O)CN(S(C)(=O)=O)C4)=CC3=N2)c1NC(=O)OC(C)c1ccccc1Cl]
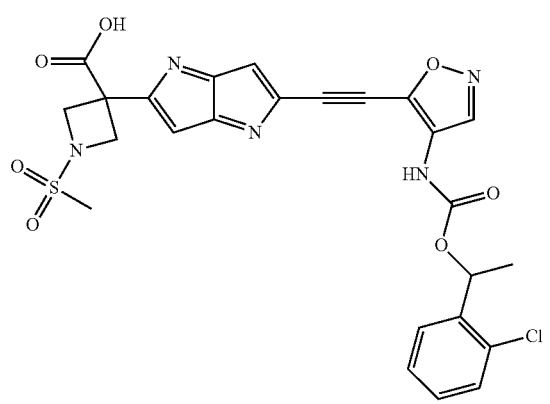
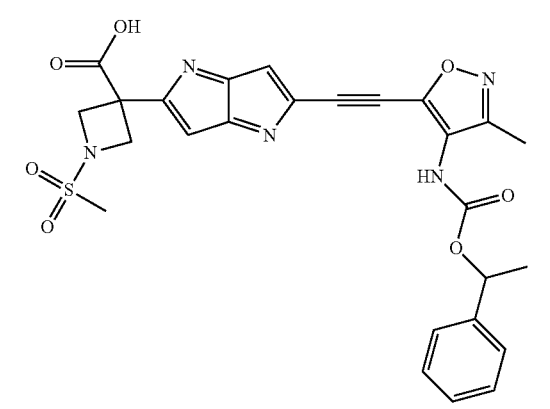 [SMILES: Cc1noc(C#CC2=CC3=NC(C4(C(=O)O)CN(S(C)(=O)=O)C4)=CC3=N2)c1NC(=O)OC(C)c1ccccc1]
TABLE 8-continued
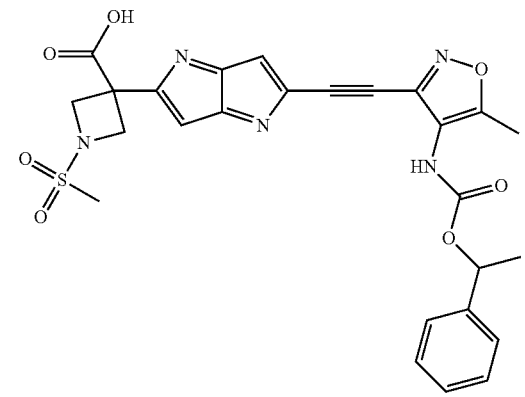 [SMILES: Cc1onc(C#CC2=CC3=NC(C4(C(=O)O)CN(S(C)(=O)=O)C4)=CC3=N2)c1NC(=O)OC(C)c1ccccc1]
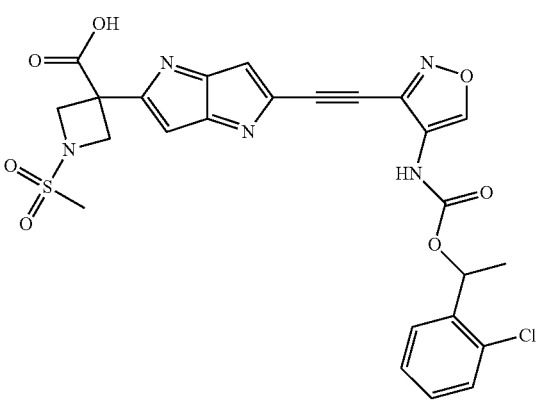 [SMILES: CC(OC(=O)Nc1conc1C#CC1=CC2=NC(C3(C(=O)O)CN(S(C)(=O)=O)C3)=CC2=N1)c1ccccc1Cl]
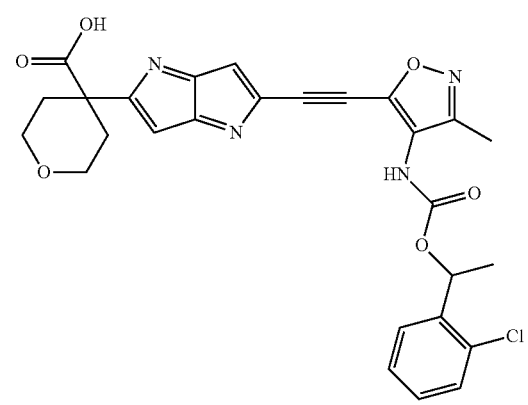
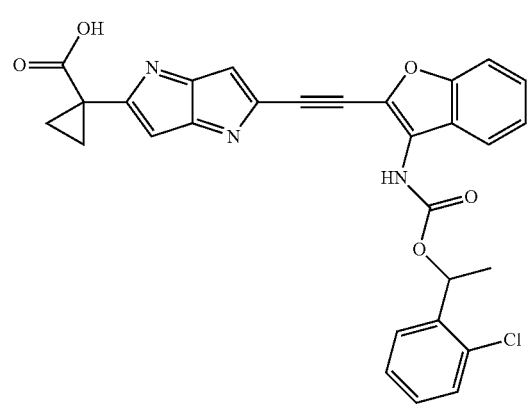 [SMILES: CC(OC(=O)Nc1c(C#CC2=CC3=NC(C4(C(=O)O)CC4)=CC3=N2)oc2ccccc12)c1ccccc1Cl]

TABLE 8-continued
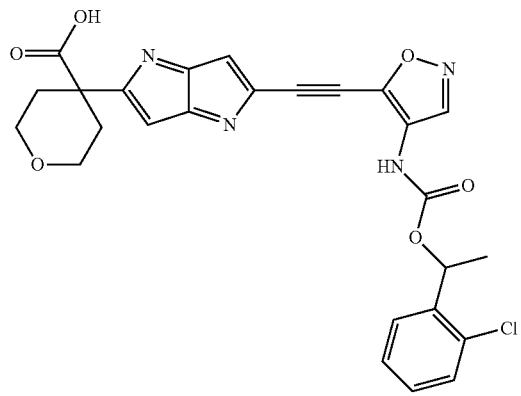 [SMILES: CC(OC(=O)Nc1cnoc1C#CC1=CC2=NC(C3(C(=O)O)CCOCC3)=CC2=N1)c1ccccc1Cl]
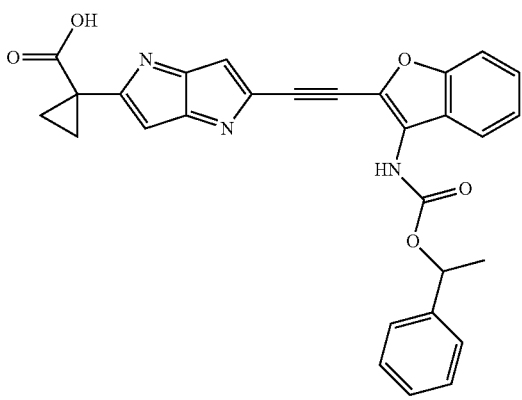 [SMILES: CC(OC(=O)Nc1c(C#CC2=CC3=NC(C4(C(=O)O)CC4)=CC3=N2)oc2ccccc12)c1ccccc1]
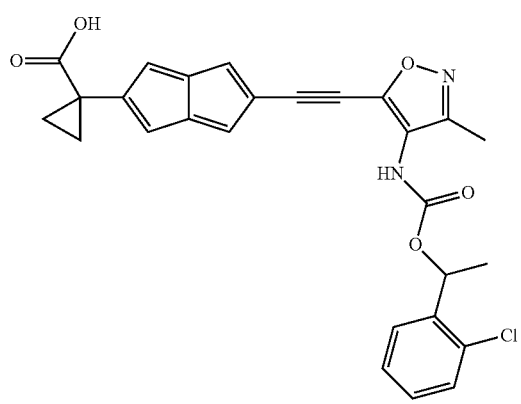 [SMILES: Cc1noc(C#CC2=CC3=CC(C4(C(=O)O)CC4)=CC3=C2)c1NC(=O)OC(C)c1ccccc1Cl]
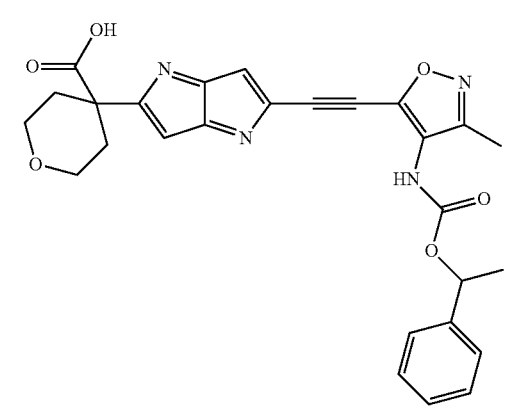 [SMILES: Cc1noc(C#CC2=CC3=NC(C4(C(=O)O)CCOCC4)=CC3=N2)c1NC(=O)OC(C)c1ccccc1]
TABLE 8-continued
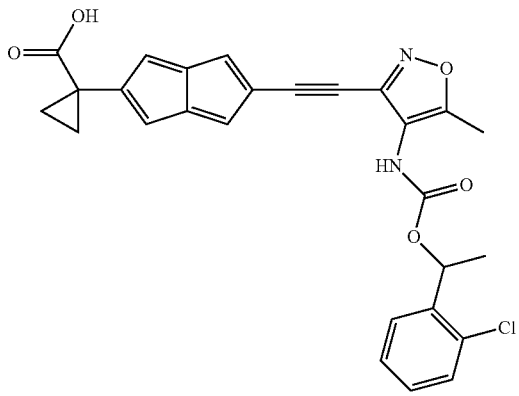

TABLE 8-continued
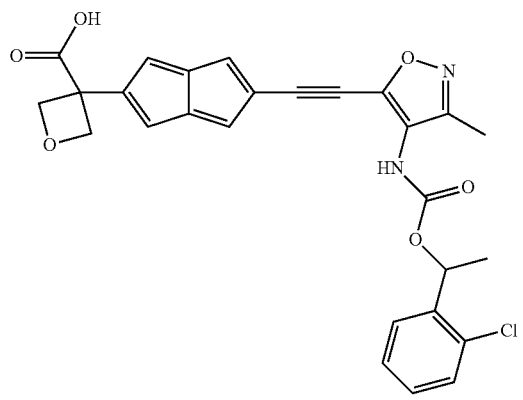 [SMILES: Cc1noc(C#CC2=CC3=CC(C4(C(=O)O)COC4)=CC3=C2)c1NC(=O)OC(C)c1ccccc1Cl]
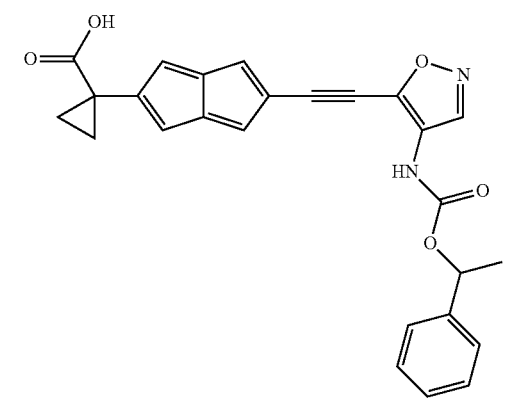 [SMILES: CC(OC(=O)Nc1cnoc1C#CC1=CC2=CC(C3(C(=O)O)CC3)=CC2=C1)c1ccccc1]
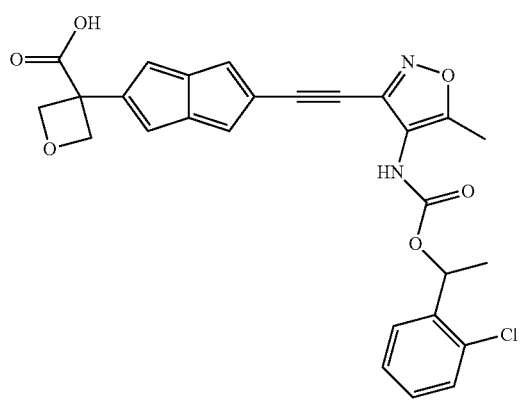 [SMILES: Cc1onc(C#CC2=CC3=CC(C4(C(=O)O)COC4)=CC3=C2)c1NC(=O)OC(C)c1ccccc1Cl]
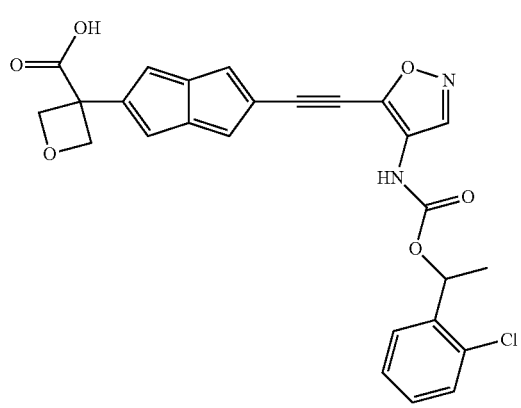 [SMILES: CC(OC(=O)Nc1cnoc1C#CC1=CC2=CC(C3(C(=O)O)COC3)=CC2=C1)c1ccccc1Cl]
TABLE 8-continued
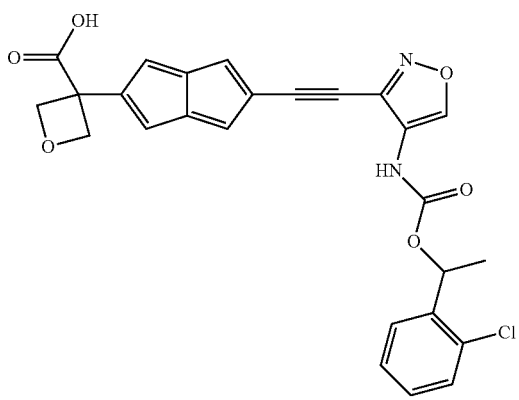 [SMILES: CC(OC(=O)Nc1conc1C#CC1=CC2=CC(C3(C(=O)O)COC3)=CC2=C1)c1ccccc1Cl]
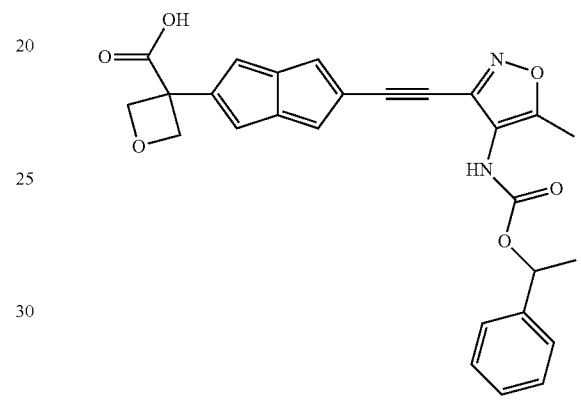
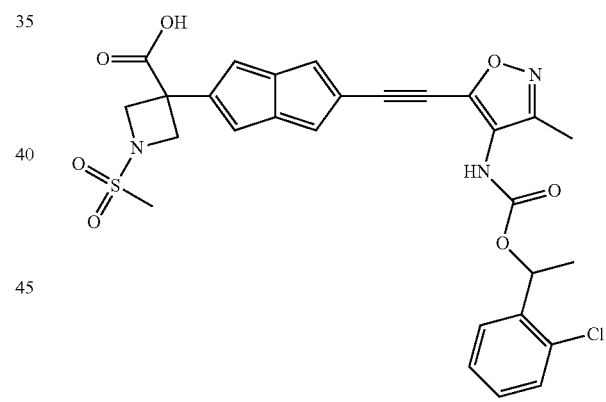
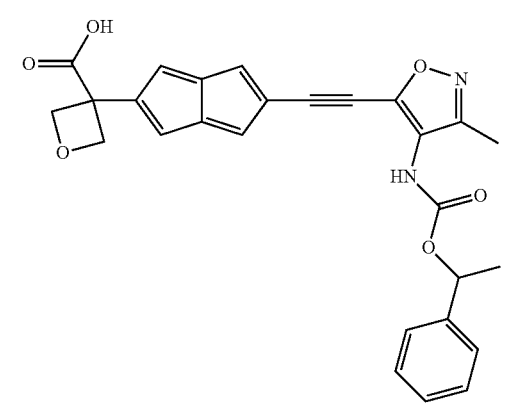 [SMILES: Cc1noc(C#CC2=CC3=CC(C4(C(=O)O)COC4)=CC3=C2)c1NC(=O)OC(C)c1ccccc1]

TABLE 8-continued
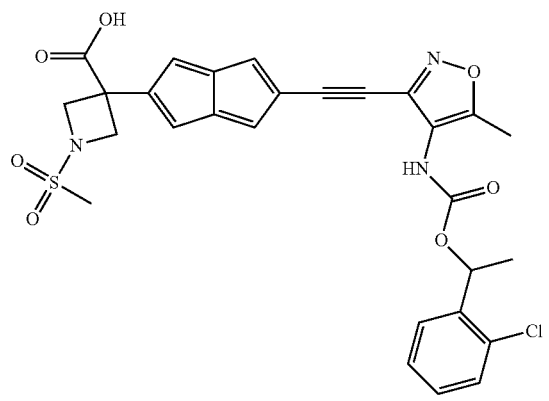 [SMILES: Cc1onc(C#CC2=CC3=CC(C4(C(=O)O)CN(S(C)(=O)=O)C4)=CC3=C2)c1NC(=O)OC(C)c1ccccc1Cl]
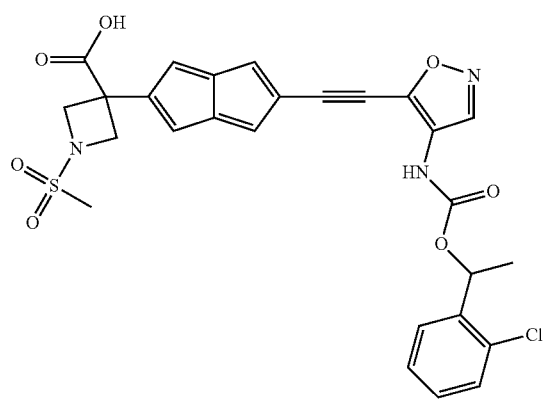 [SMILES: CC(OC(=O)Nc1cnoc1C#CC1=CC2=CC(C3(C(=O)O)CN(S(C)(=O)=O)C3)=CC2=C1)c1ccccc1Cl]
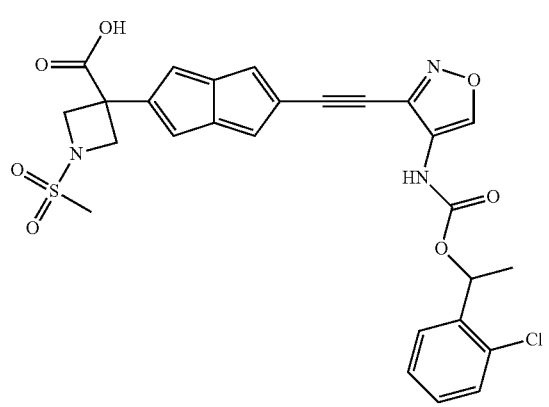 [SMILES: CC(OC(=O)Nc1conc1C#CC1=CC2=CC(C3(C(=O)O)CN(S(C)(=O)=O)C3)=CC2=C1)c1ccccc1Cl]
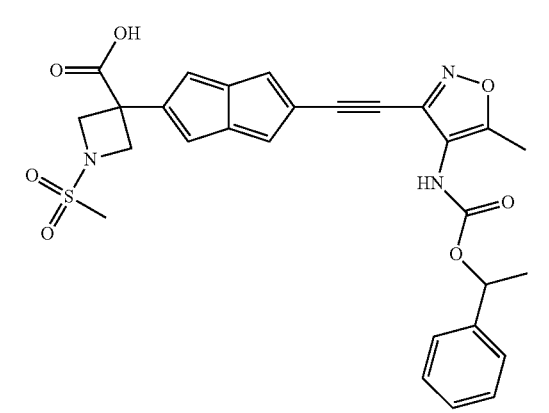 [SMILES: Cc1onc(C#CC2=CC3=CC(C4(C(=O)O)CN(S(C)(=O)=O)C4)=CC3=C2)c1NC(=O)OC(C)c1ccccc1]
TABLE 8-continued
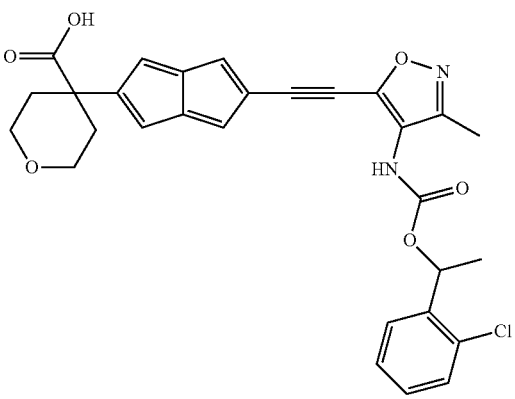 [SMILES: Cc1noc(C#CC2=CC3=CC(C4(C(=O)O)CCOCC4)=CC3=C2)c1NC(=O)OC(C)c1ccccc1Cl]
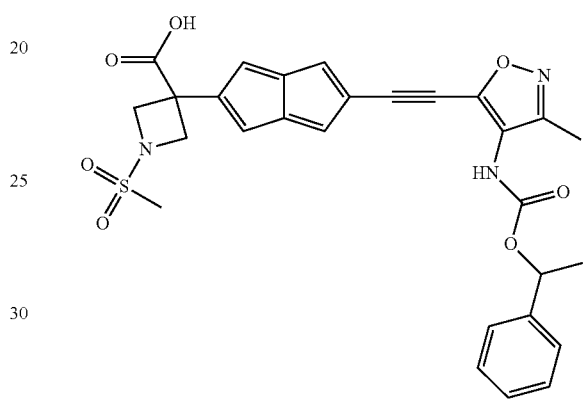
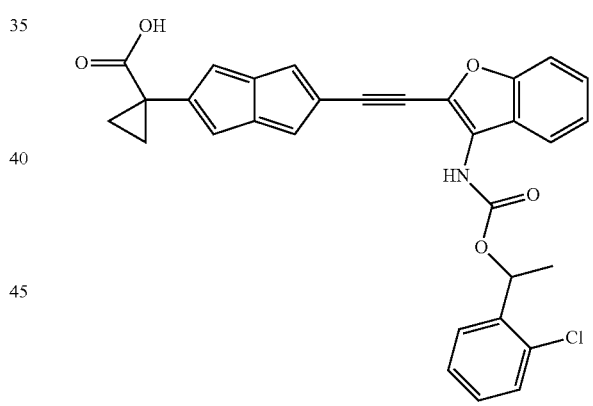
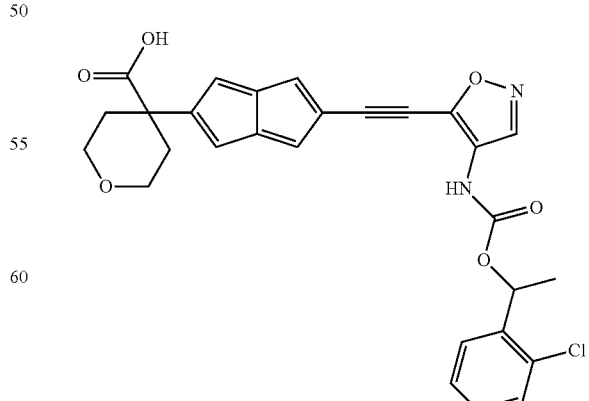

| 417 | 418 |
|---|---|
| TABLE 8-continued | TABLE 8-continued |
| 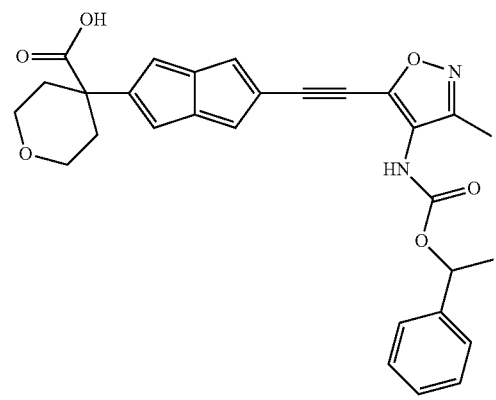 [SMILES: Cc1noc(C#CC2=CC3=CC(C4(C(=O)O)CCOCC4)=CC3=C2)c1NC(=O)OC(C)c1ccccc1] | 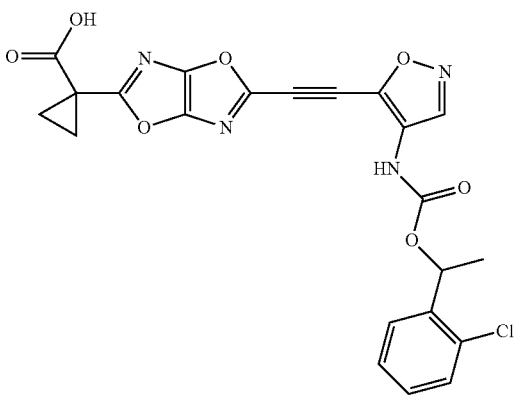 |
| 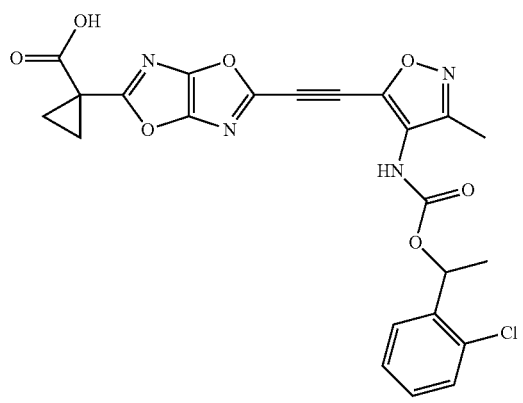 | 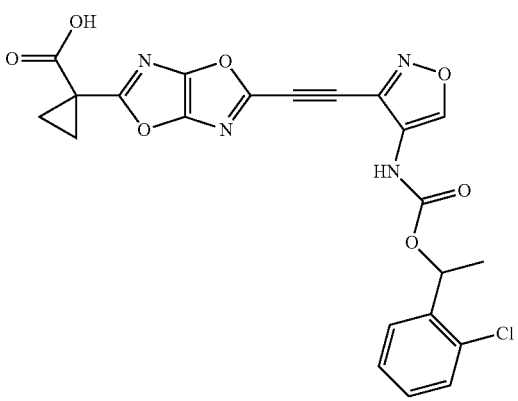 [SMILES: CC(OC(=O)Nc1conc1C#Cc1nc2oc(C3(C(=O)O)CC3)nc2o1)c1ccccc1Cl] |
| 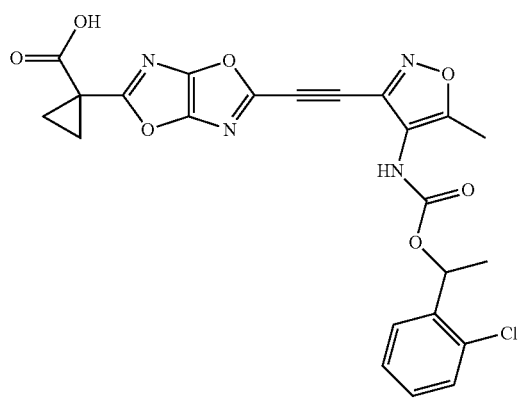 | 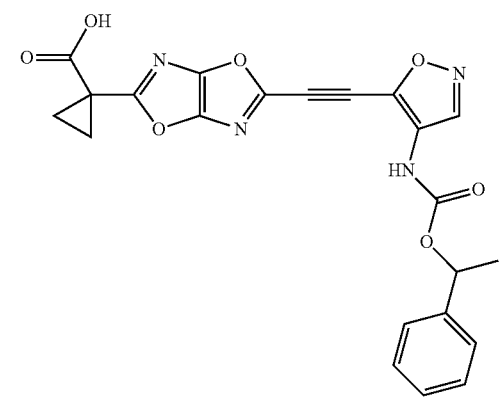 [SMILES: CC(OC(=O)Nc1cnoc1C#Cc1nc2oc(C3(C(=O)O)CC3)nc2o1)c1ccccc1] |
| 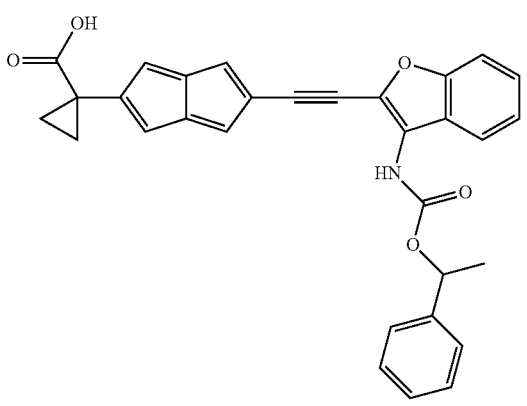 | 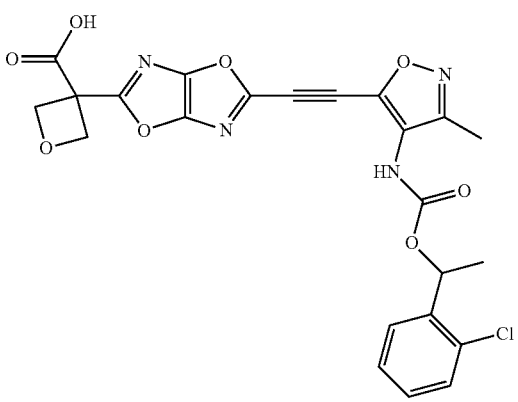 [SMILES: Cc1noc(C#Cc2nc3oc(C4(C(=O)O)COC4)nc3o2)c1NC(=O)OC(C)c1ccccc1Cl] |

TABLE 8-continued
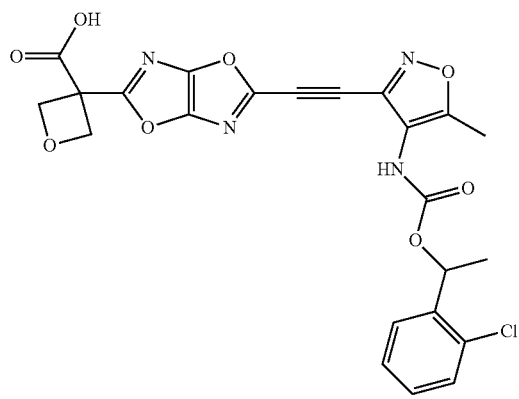
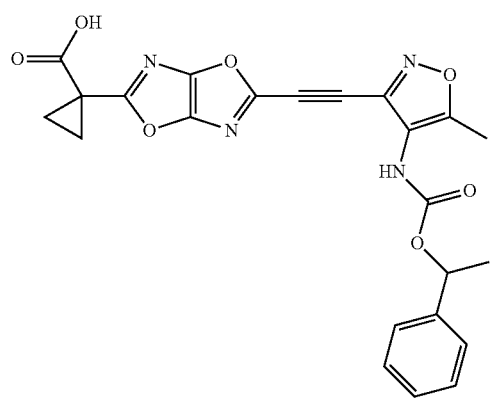 [SMILES: Cc1onc(C#Cc2nc3oc(C4(C(=O)O)CC4)nc3o2)c1NC(=O)OC(C)c1ccccc1]
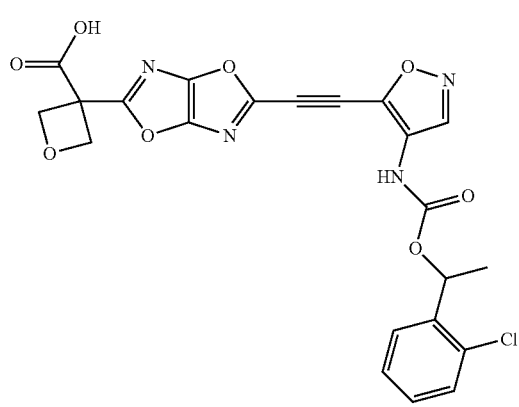 [SMILES: CC(OC(=O)Nc1cnoc1C#Cc1nc2oc(C3(C(=O)O)COC3)nc2o1)c1ccccc1Cl]
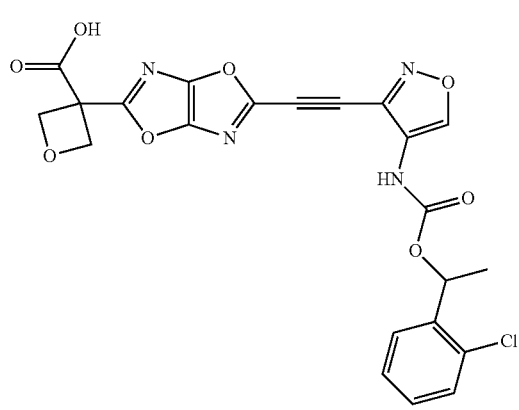
TABLE 8-continued
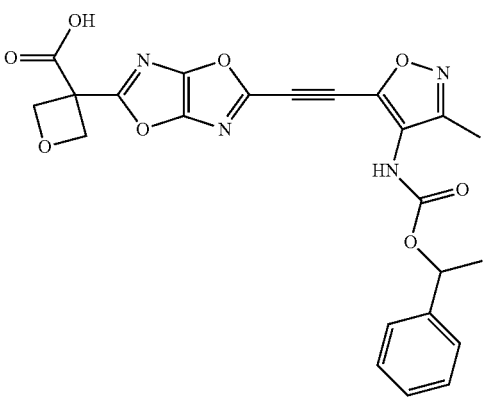 [SMILES: Cc1noc(C#Cc2nc3oc(C4(C(=O)O)COC4)nc3o2)c1NC(=O)OC(C)c1ccccc1]
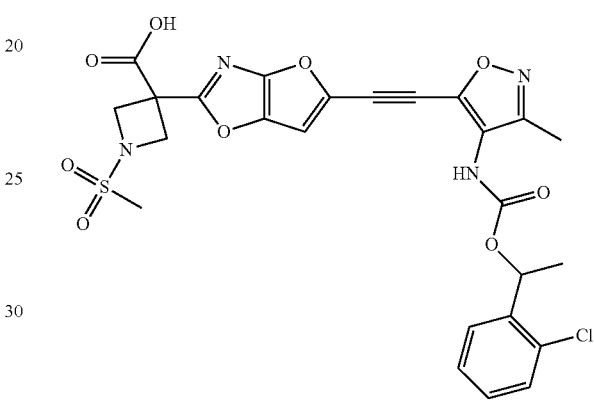
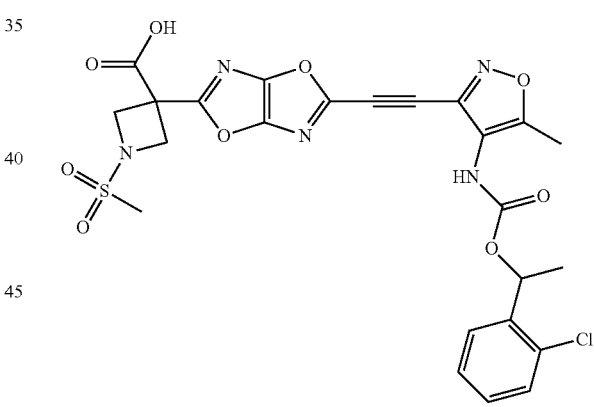
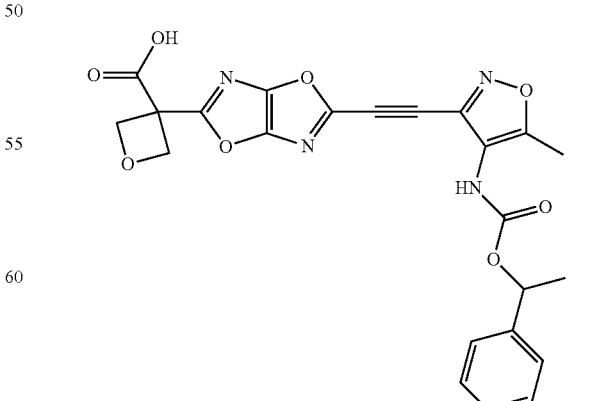

TABLE 8-continued
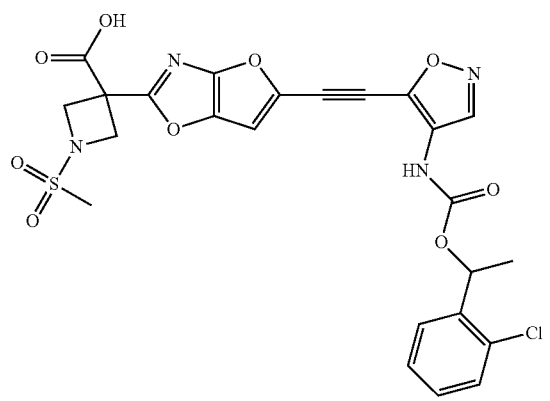 [SMILES: CC(OC(=O)Nc1cnoc1C#Cc1cc2oc(C3(C(=O)O)CN(S(C)(=O)=O)C3)nc2o1)c1ccccc1Cl]
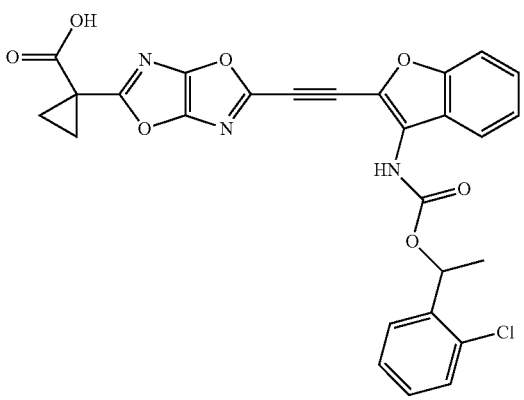 [SMILES: CC(OC(=O)Nc1c(C#Cc2nc3oc(C4(C(=O)O)CC4)nc3o2)oc2ccccc12)c1ccccc1Cl]
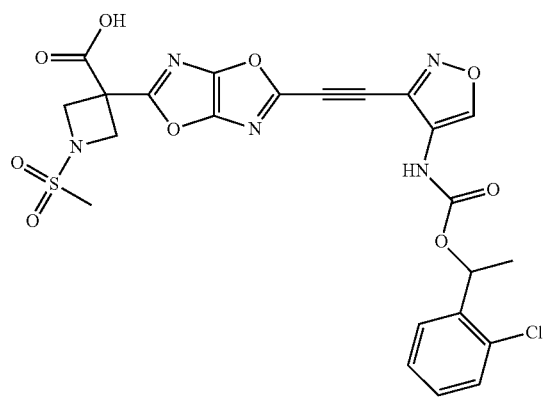
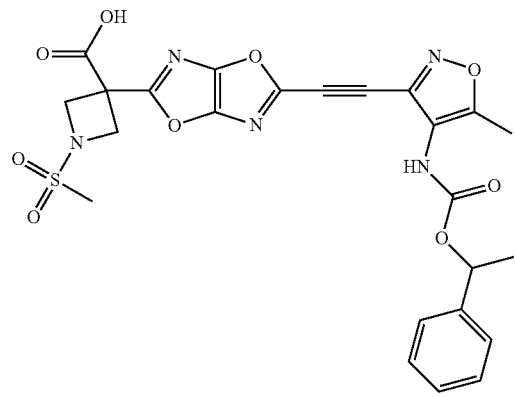 [SMILES: Cc1onc(C#Cc2nc3oc(C4(C(=O)O)CN(S(C)(=O)=O)C4)nc3o2)c1NC(=O)OC(C)c1ccccc1]
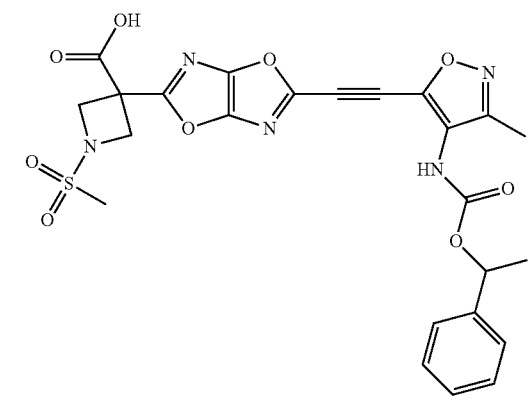
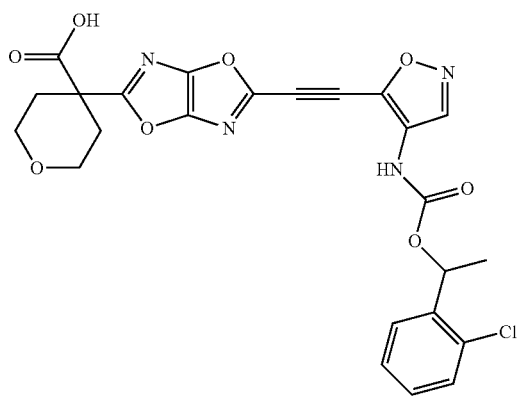 [SMILES: CC(OC(=O)Nc1cnoc1C#Cc1nc2oc(C3(C(=O)O)CCOCC3)nc2o1)c1ccccc1Cl]
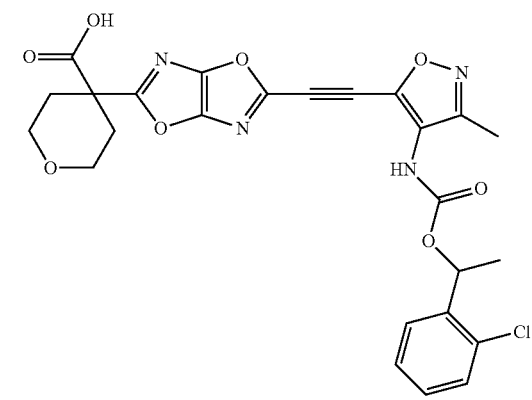
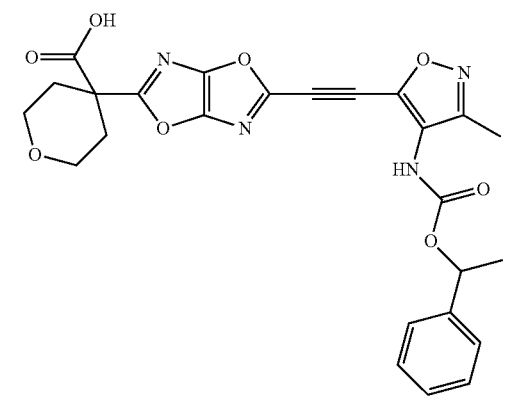 [SMILES: Cc1noc(C#Cc2nc3oc(C4(C(=O)O)CCOCC4)nc3o2)c1NC(=O)OC(C)c1ccccc1]

423
| | |
|---|---|
| 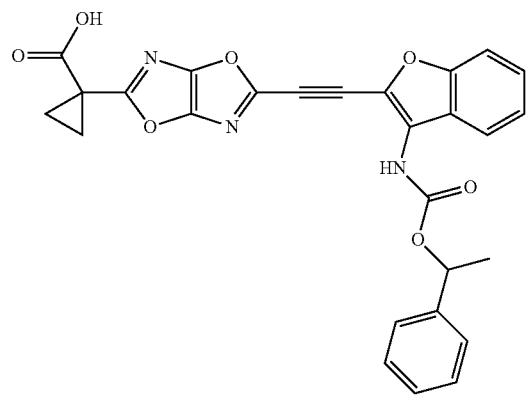 [SMILES: CC(OC(=O)Nc1c(C#Cc2nc3oc(C4(C(=O)O)CC4)nc3o2)oc2ccccc12)c1ccccc1] | 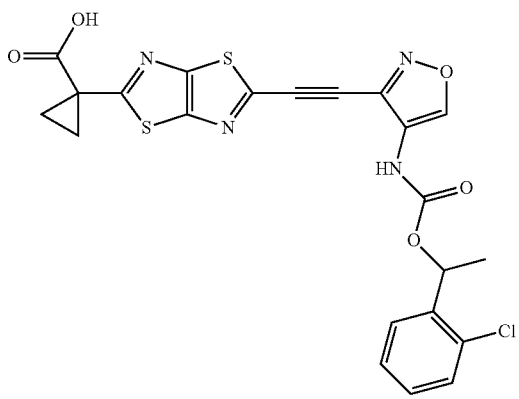 |
|  | 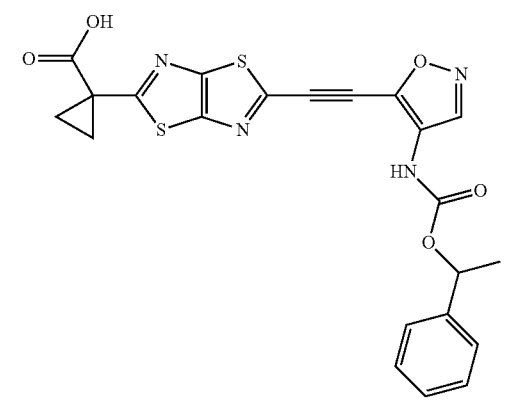 |
|  | 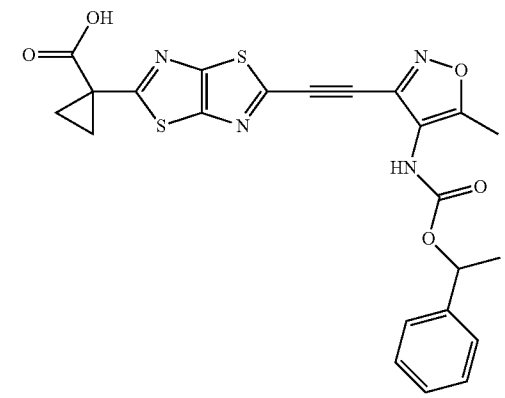 |
|  | 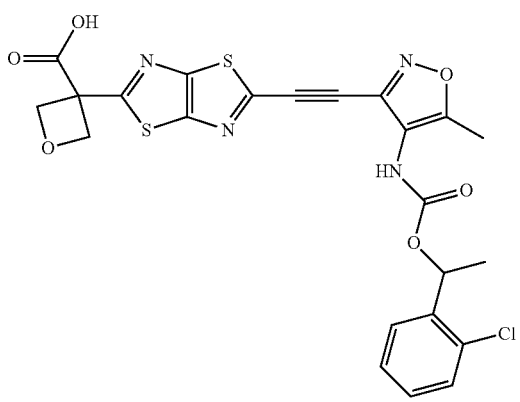 [SMILES: Cc1onc(C#Cc2nc3sc(C4(C(=O)O)COC4)nc3s2)c1NC(=O)OC(C)c1ccccc1Cl] |
424

TABLE 8-continued
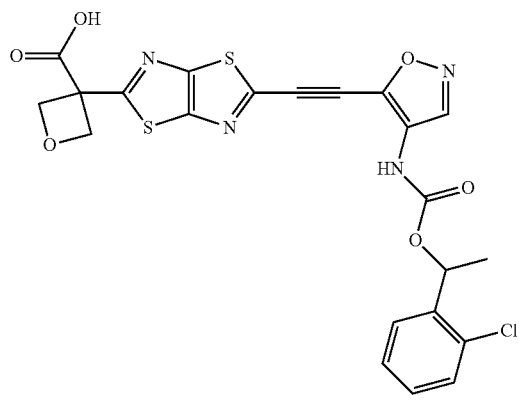 [SMILES: CC(OC(=O)Nc1cnoc1C#Cc1nc2sc(C3(C(=O)O)COC3)nc2s1)c1ccccc1Cl]
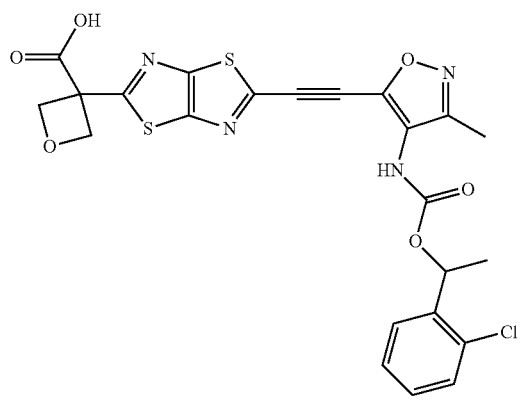
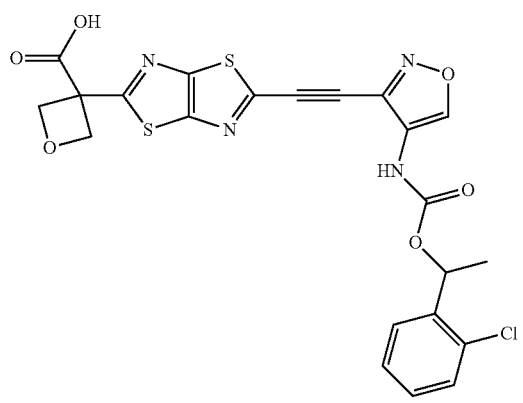 [SMILES: CC(OC(=O)Nc1conc1C#Cc1nc2sc(C3(C(=O)O)COC3)nc2s1)c1ccccc1Cl]
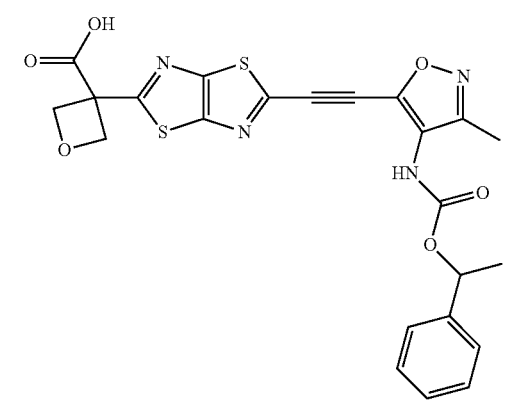 [SMILES: Cc1noc(C#Cc2nc3sc(C4(C(=O)O)COC4)nc3s2)c1NC(=O)OC(C)c1ccccc1]
TABLE 8-continued
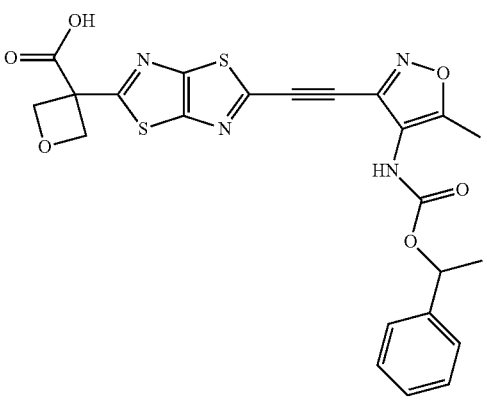
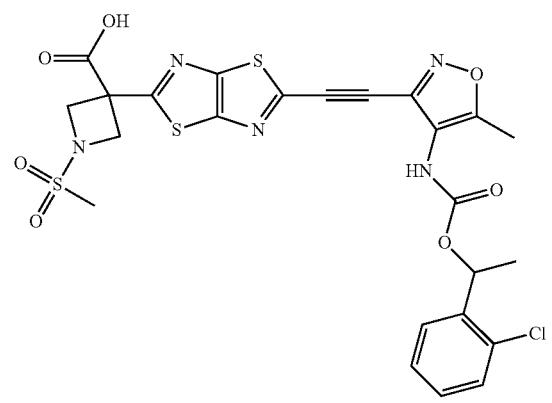 [SMILES: Cc1onc(C#Cc2nc3sc(C4(C(=O)O)CN(S(C)(=O)=O)C4)nc3s2)c1NC(=O)OC(C)c1ccccc1Cl]
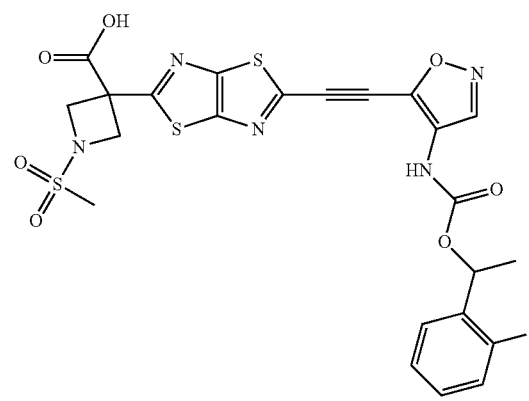
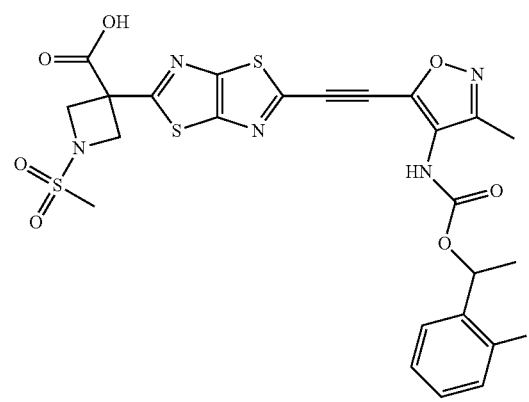

427
TABLE 8-continued
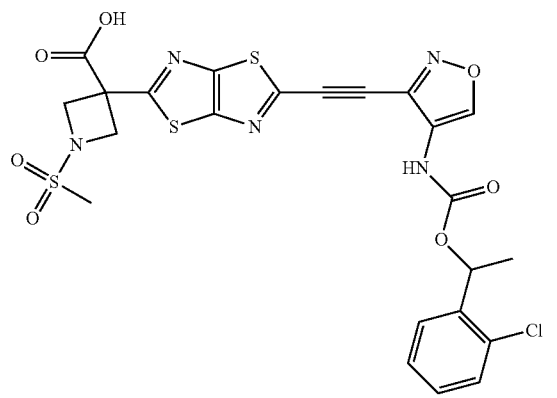 [SMILES: CC(OC(=O)Nc1conc1C#Cc1nc2sc(C3(C(=O)O)CN(S(C)(=O)=O)C3)nc2s1)c1ccccc1Cl]
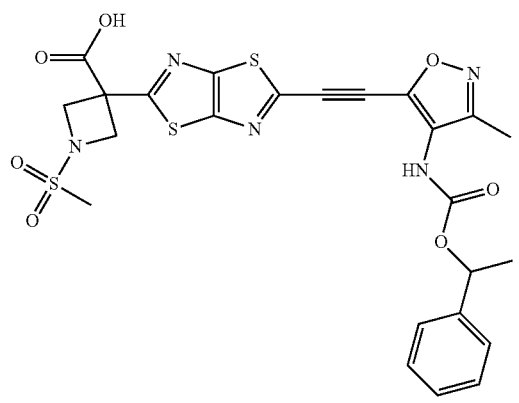
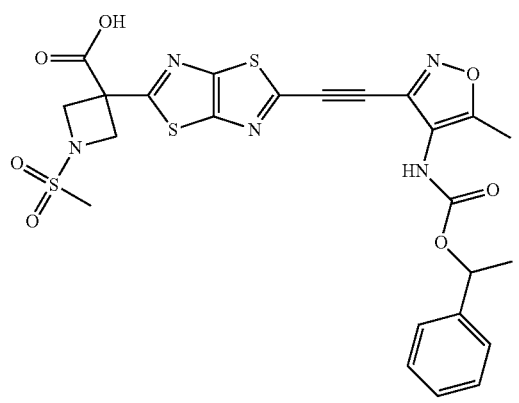 [SMILES: Cc1onc(C#Cc2nc3sc(C4(C(=O)O)CN(S(C)(=O)=O)C4)nc3s2)c1NC(=O)OC(C)c1ccccc1]
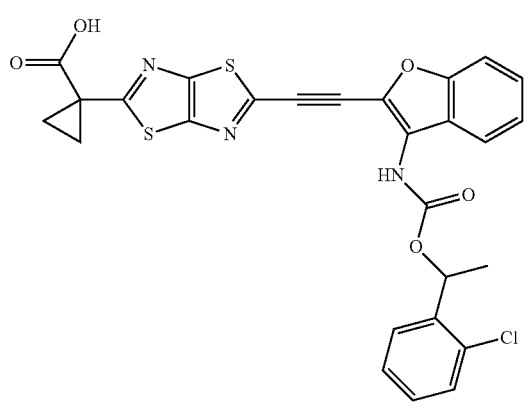
428
TABLE 8-continued

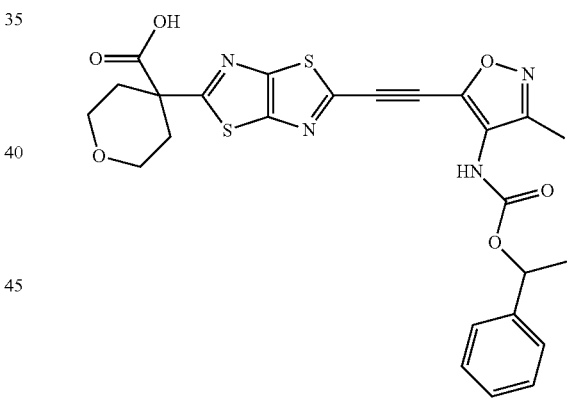
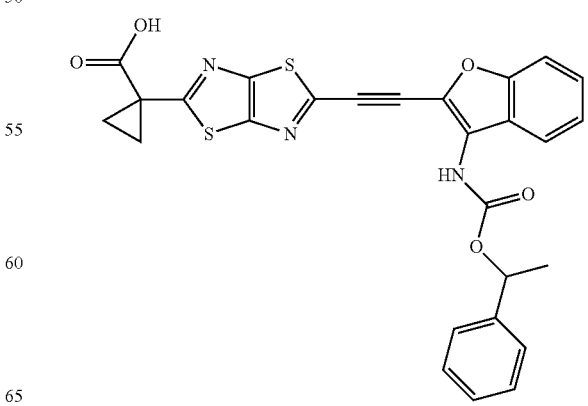

TABLE 8-continued
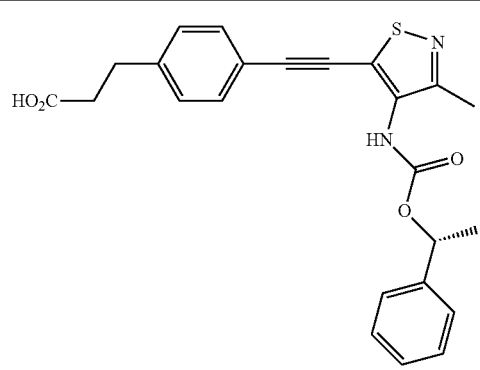
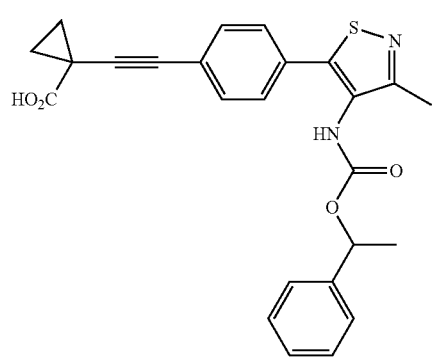 [SMILES: Cc1nsc(-c2ccc(C#CC3(C(=O)O)CC3)cc2)c1NC(=O)OC(C)c1ccccc1]
In some embodiments, compounds of Formula (I) are selected from the following compounds as listed in Table 9.
TABLE 9
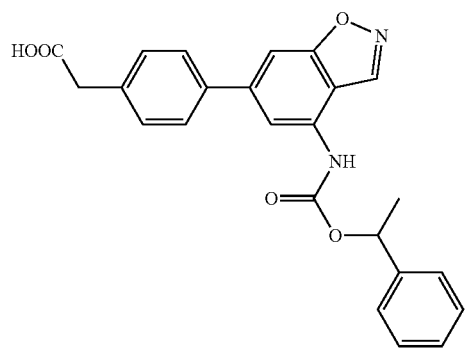 [SMILES: CC(OC(=O)Nc1cc(-c2ccc(CC(=O)O)cc2)cc2oncc12)c1ccccc1]
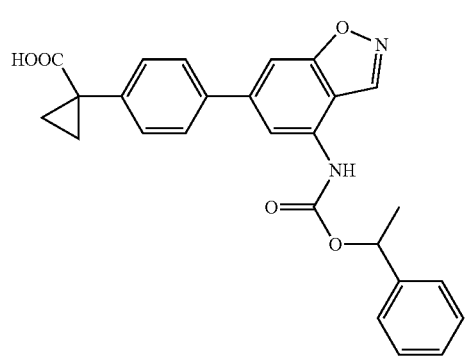 [SMILES: CC(OC(=O)Nc1cc(-c2ccc(C3(C(=O)O)CC3)cc2)cc2oncc12)c1ccccc1]
TABLE 9-continued
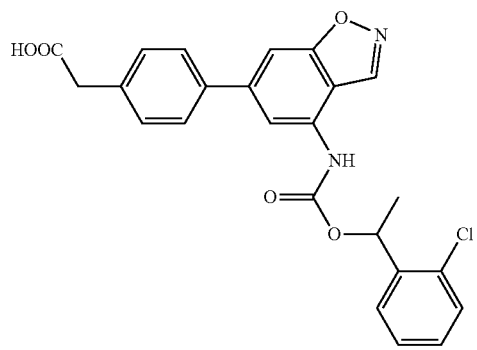 [SMILES: CC(OC(=O)Nc1cc(-c2ccc(CC(=O)O)cc2)cc2oncc12)c1ccccc1Cl]
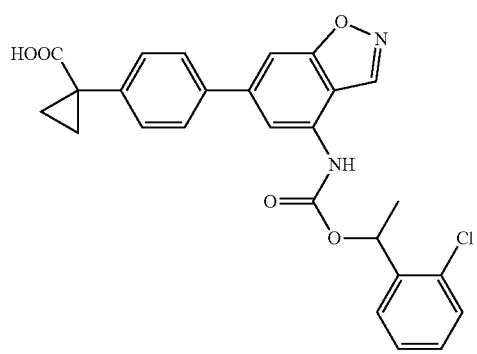 [SMILES: CC(OC(=O)Nc1cc(-c2ccc(C3(C(=O)O)CC3)cc2)cc2sncc12)c1ccccc1Cl]
In some embodiments, compounds of Formula (I) are selected from the following compounds as listed in Table 10.

TABLE 10
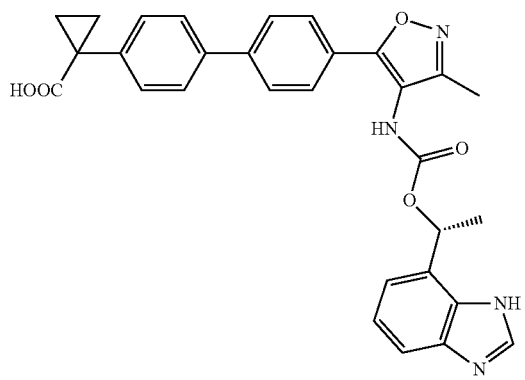 [SMILES: Cc1noc(-c2ccc(-c3ccc(C4(C(=O)O)CC4)cc3)cc2)c1NC(=O)O[C@H](C)c1cccc2nc[nH]c12]
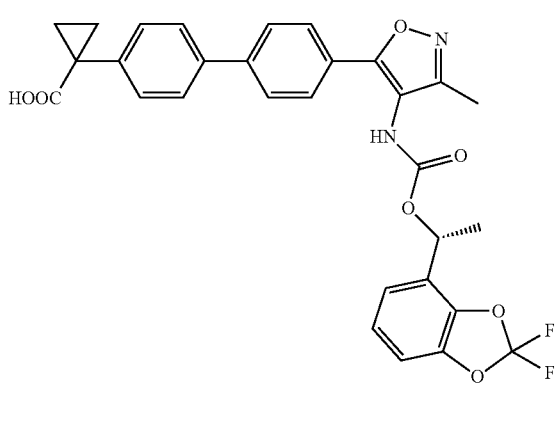 [SMILES: Cc1noc(-c2ccc(-c3ccc(C4(C(=O)O)CC4)cc3)cc2)c1NC(=O)O[C@H](C)c1cccc2c1OC(F)(F)O2]
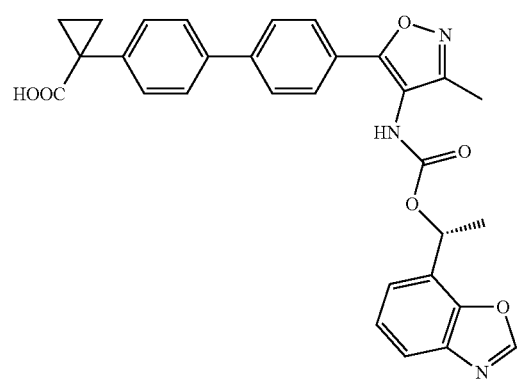 [SMILES: Cc1noc(-c2ccc(-c3ccc(C4(C(=O)O)CC4)cc3)cc2)c1NC(=O)O[C@H](C)c1cccc2ncoc12]
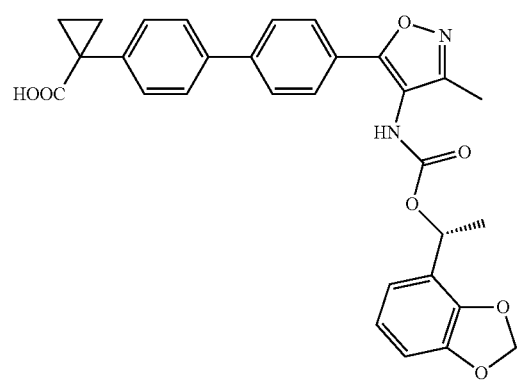 [SMILES: Cc1noc(-c2ccc(-c3ccc(C4(C(=O)O)CC4)cc3)cc2)c1NC(=O)O[C@H](C)c1cccc2c1OCO2]
TABLE 10-continued
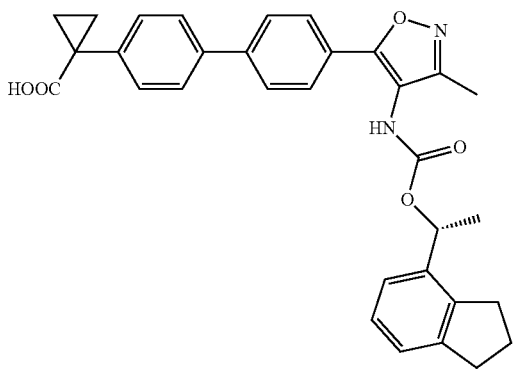 [SMILES: Cc1noc(-c2ccc(-c3ccc(C4(C(=O)O)CC4)cc3)cc2)c1NC(=O)O[C@H](C)c1cccc2c1CCC2]
In some embodiments, compounds of Formula (I) are selected from the following compounds as listed in Table 11.
TABLE 11
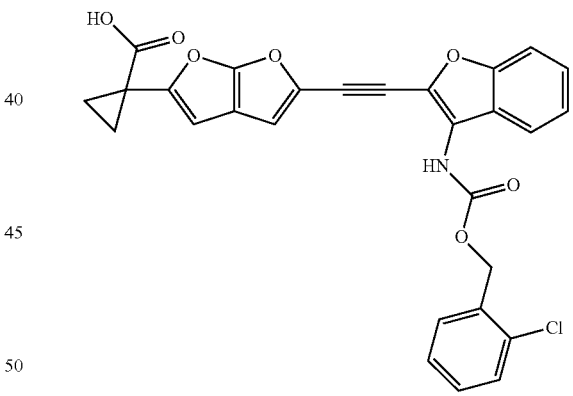
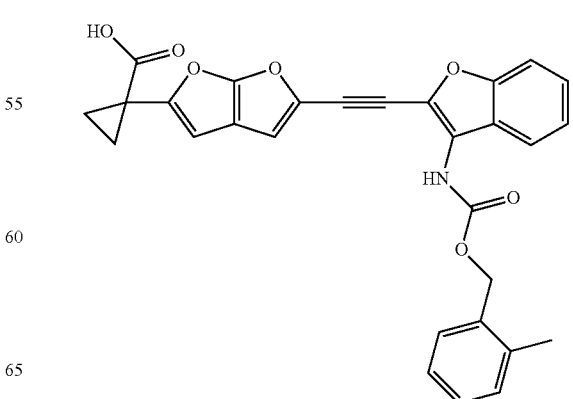

TABLE 11-continued
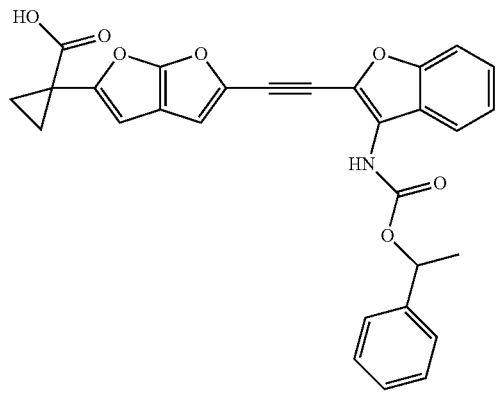 [SMILES: CC(OC(=O)Nc1c(C#Cc2cc3cc(C4(C(=O)O)CC4)oc3o2)oc2ccccc12)c1ccccc1]
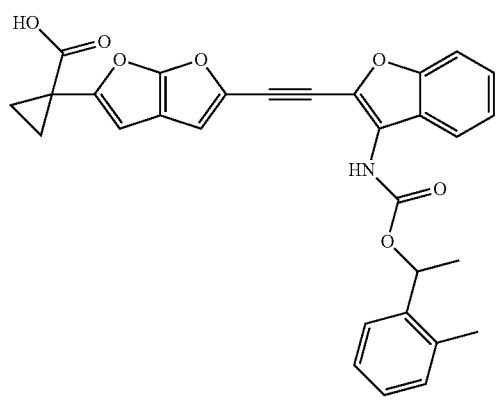 [SMILES: Cc1ccccc1C(C)OC(=O)Nc1c(C#Cc2cc3cc(C4(C(=O)O)CC4)oc3o2)oc2ccccc12]
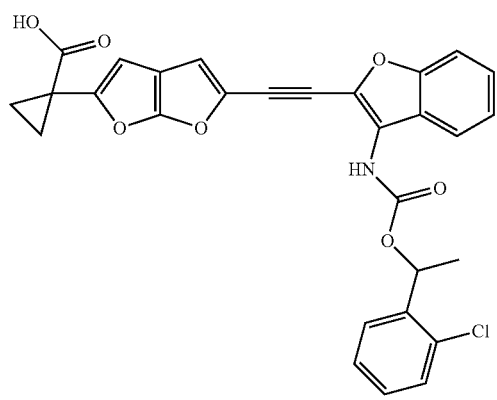 [SMILES: CC(OC(=O)Nc1c(C#Cc2cc3cc(C4(C(=O)O)CC4)oc3o2)oc2ccccc12)c1ccccc1Cl]
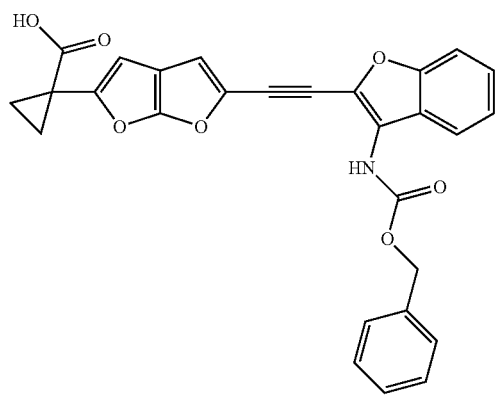
TABLE 11-continued
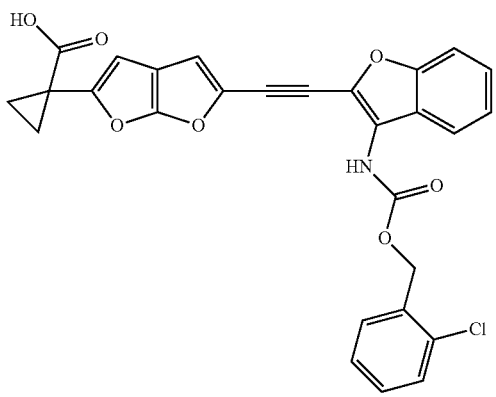 [SMILES: O=C(Nc1c(C#Cc2cc3cc(C4(C(=O)O)CC4)oc3o2)oc2ccccc12)OCc1ccccc1Cl]
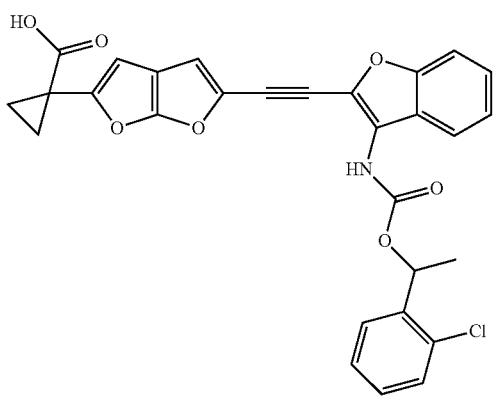 [SMILES: CC(OC(=O)Nc1c(C#Cc2cc3cc(C4(C(=O)O)CC4)oc3o2)oc2ccccc12)c1ccccc1Cl]
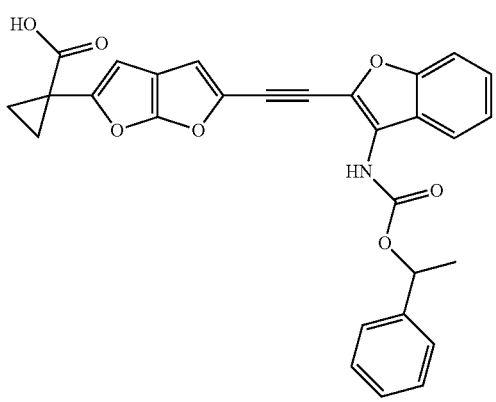 [SMILES: CC(OC(=O)Nc1c(C#Cc2cc3cc(C4(C(=O)O)CC4)oc3o2)oc2ccccc12)c1ccccc1]
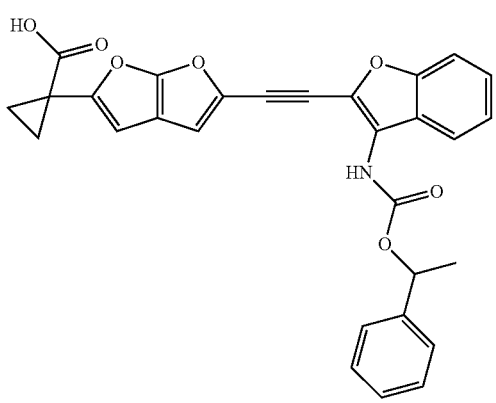 [SMILES: CC(OC(=O)Nc1c(C#Cc2cc3cc(C4(C(=O)O)CC4)oc3o2)oc2ccccc12)c1ccccc1]

TABLE 11-continued
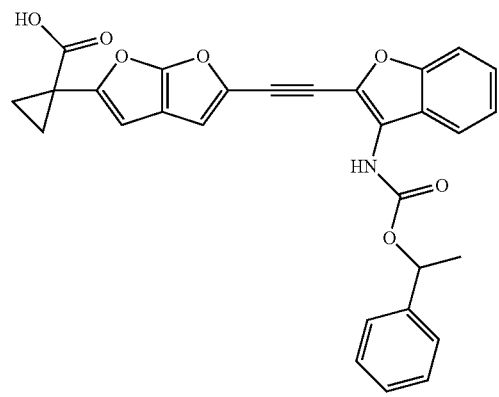
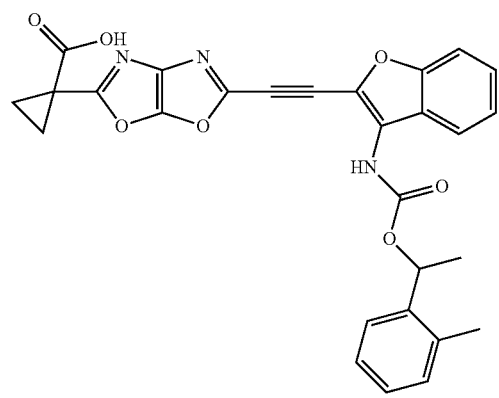 [SMILES: Cc1ccccc1C(C)OC(=O)Nc1c(C#Cc2nc3nc(C4(C(=O)O)CC4)oc3o2)oc2ccccc12]
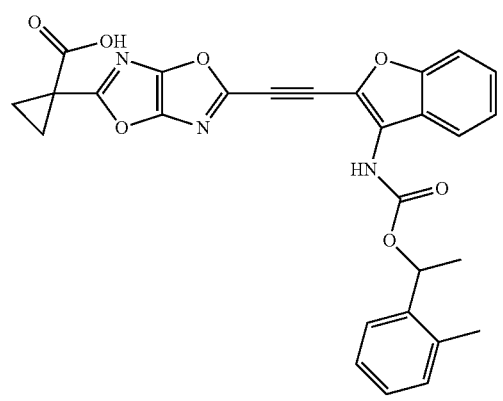 [SMILES: Cc1ccccc1C(C)OC(=O)Nc1c(C#Cc2nc3oc(C4(C(=O)O)CC4)nc3o2)oc2ccccc12]
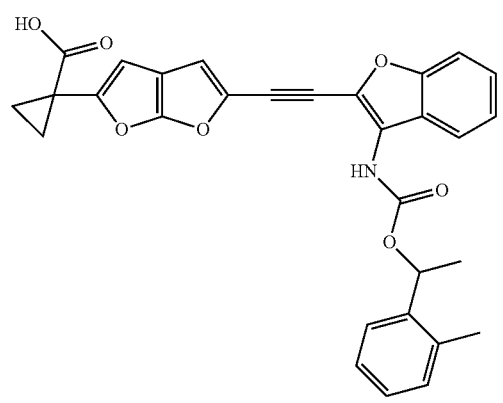
TABLE 11-continued
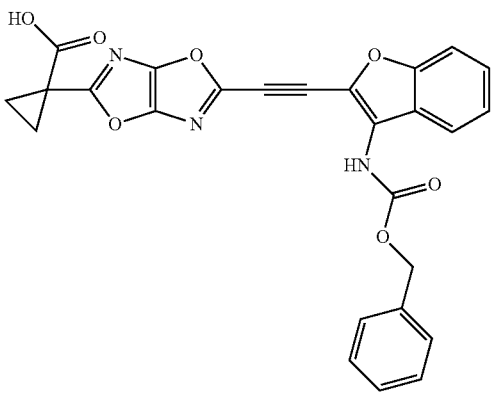 [SMILES: O=C(Nc1c(C#Cc2nc3oc(C4(C(=O)O)CC4)nc3o2)oc2ccccc12)OCc1ccccc1]
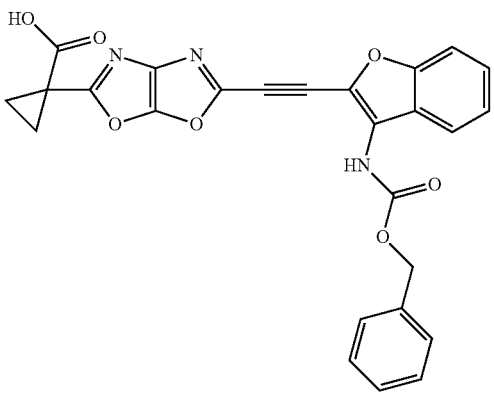 [SMILES: O=C(Nc1c(C#Cc2nc3nc(C4(C(=O)O)CC4)oc3o2)oc2ccccc12)OCc1ccccc1]
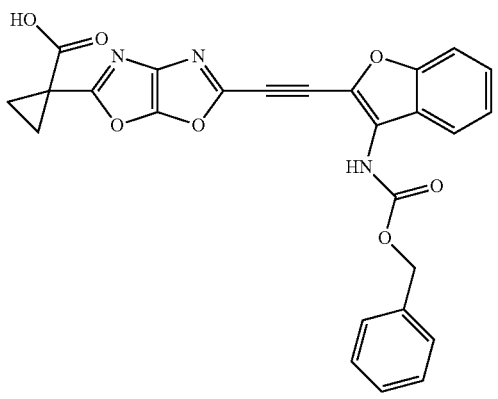
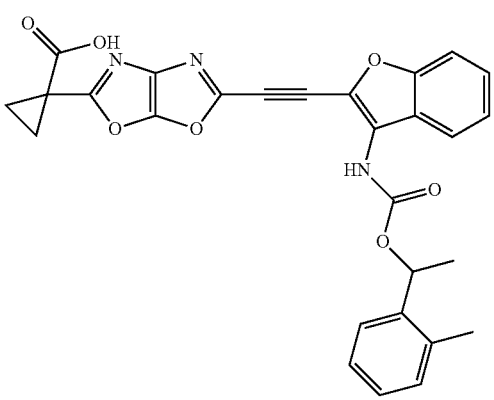 [SMILES: Cc1ccccc1C(C)OC(=O)Nc1c(C#Cc2nc3nc(C4(C(=O)O)CC4)oc3o2)oc2ccccc12]

TABLE 11-continued
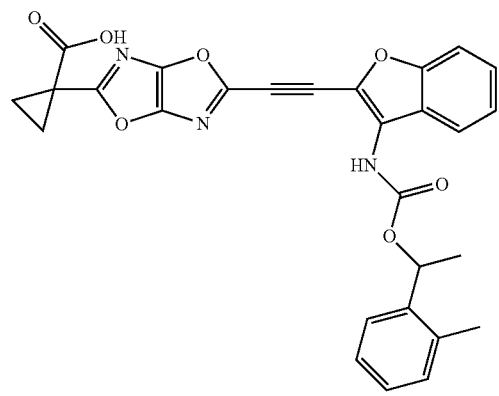 [SMILES: Cc1ccccc1C(C)OC(=O)Nc1c(C#Cc2nc3oc(C4(C(=O)O)CC4)nc3o2)oc2ccccc12]
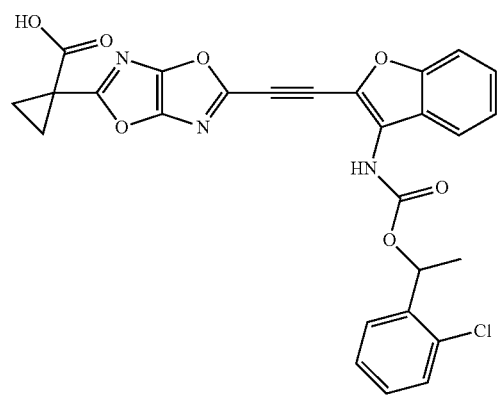
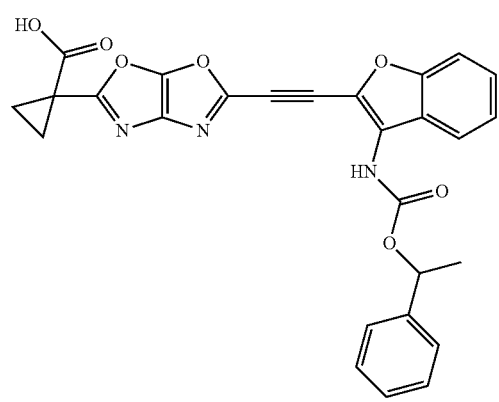 [SMILES: CC(OC(=O)Nc1c(C#Cc2nc3nc(C4(C(=O)O)CC4)oc3o2)oc2ccccc12)c1ccccc1]
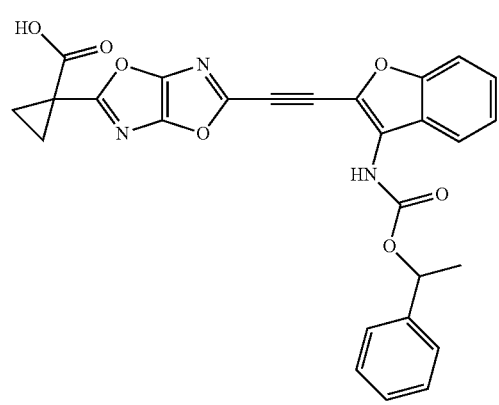 [SMILES: CC(OC(=O)Nc1c(C#Cc2nc3oc(C4(C(=O)O)CC4)nc3o2)oc2ccccc12)c1ccccc1]
TABLE 11-continued
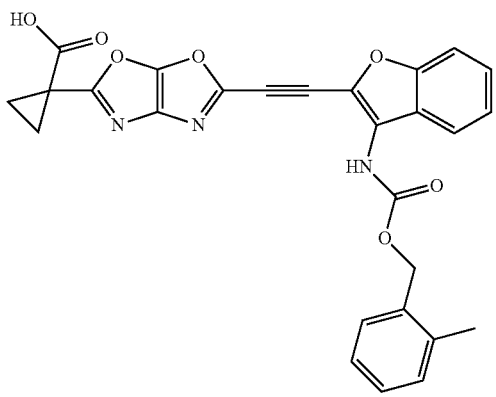 [SMILES: Cc1ccccc1COC(=O)Nc1c(C#Cc2nc3nc(C4(C(=O)O)CC4)oc3o2)oc2ccccc12]
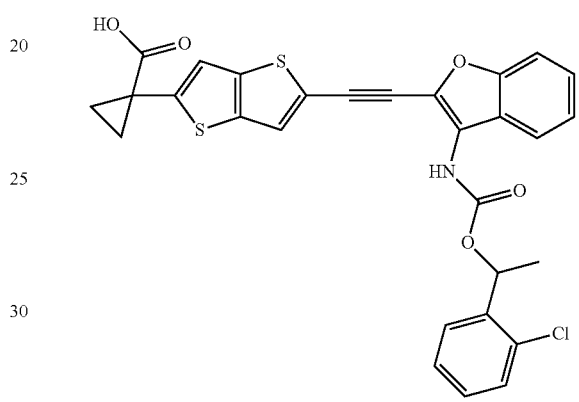
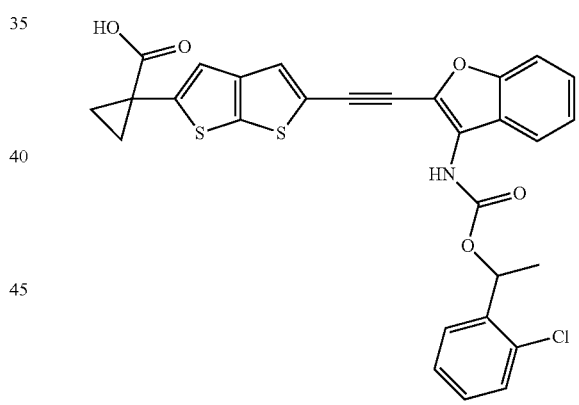
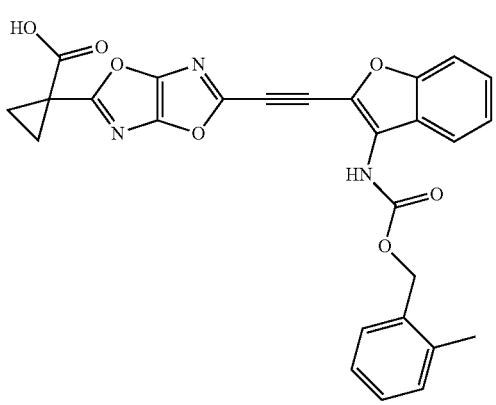 [SMILES: Cc1ccccc1COC(=O)Nc1c(C#Cc2nc3oc(C4(C(=O)O)CC4)nc3o2)oc2ccccc12]

TABLE 11-continued
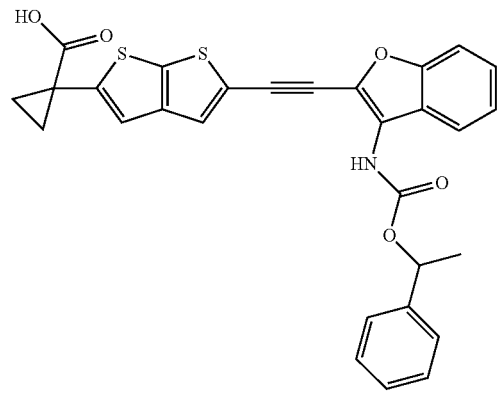 [SMILES: CC(OC(=O)Nc1c(C#Cc2cc3cc(C4(C(=O)O)CC4)sc3s2)oc2ccccc12)c1ccccc1]
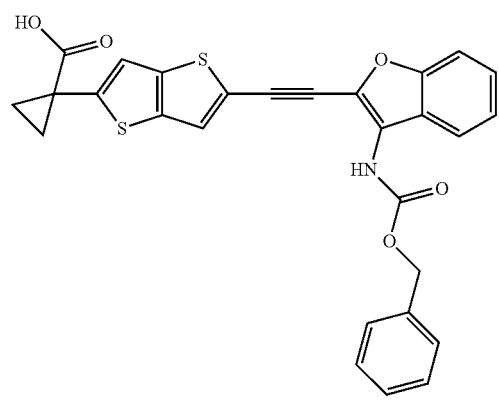 [SMILES: O=C(Nc1c(C#Cc2cc3sc(C4(C(=O)O)CC4)cc3s2)oc2ccccc12)OCc1ccccc1]
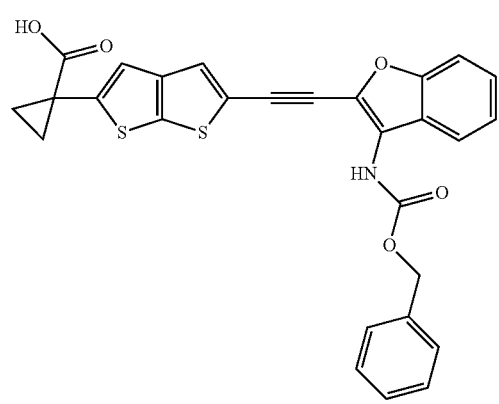 [SMILES: O=C(Nc1c(C#Cc2cc3cc(C4(C(=O)O)CC4)sc3s2)oc2ccccc12)OCc1ccccc1]
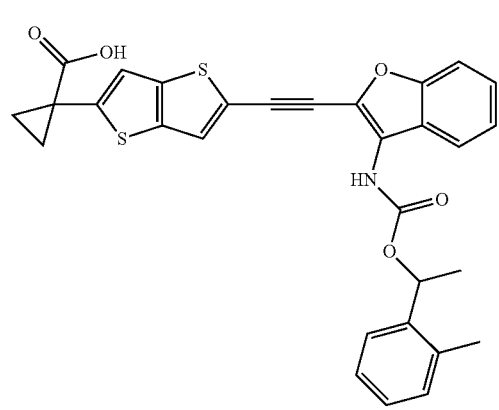 [SMILES: Cc1ccccc1C(C)OC(=O)Nc1c(C#Cc2cc3sc(C4(C(=O)O)CC4)cc3s2)oc2ccccc12]
TABLE 11-continued
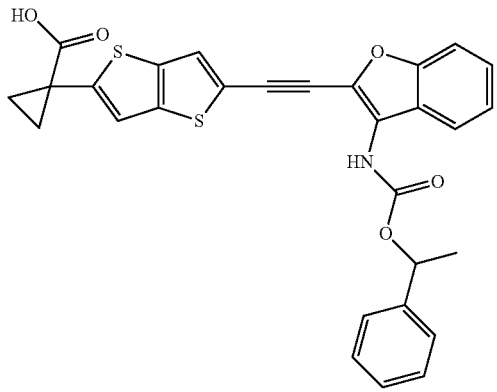 [SMILES: CC(OC(=O)Nc1c(C#Cc2cc3sc(C4(C(=O)O)CC4)cc3s2)oc2ccccc12)c1ccccc1]
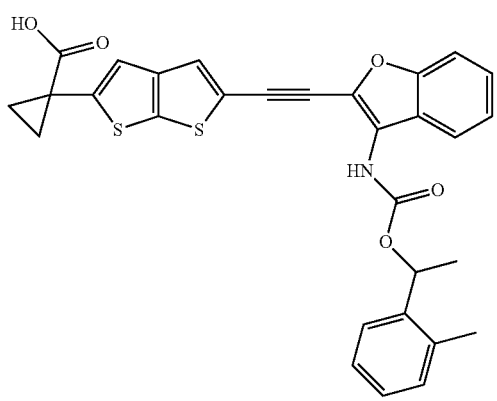 [SMILES: Cc1ccccc1C(C)OC(=O)Nc1c(C#Cc2cc3cc(C4(C(=O)O)CC4)sc3s2)oc2ccccc12]
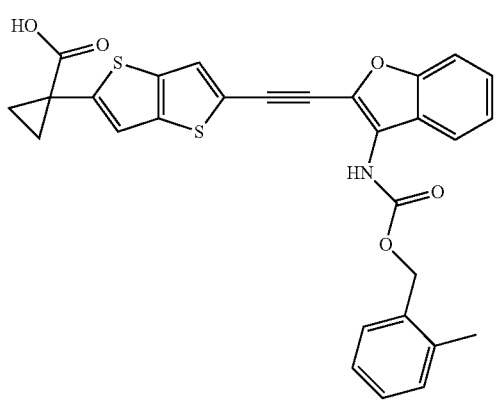 [SMILES: Cc1ccccc1COC(=O)Nc1c(C#Cc2cc3sc(C4(C(=O)O)CC4)cc3s2)oc2ccccc12]
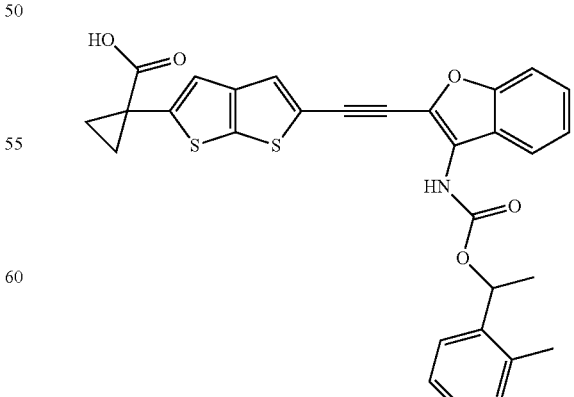

TABLE 11-continued
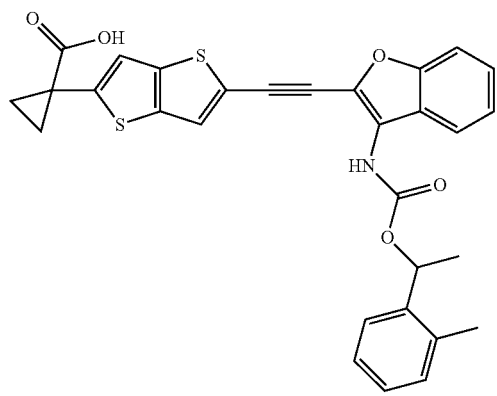 [SMILES: Cc1ccccc1C(C)OC(=O)Nc1c(C#Cc2cc3sc(C4(C(=O)O)CC4)cc3s2)oc2ccccc12]
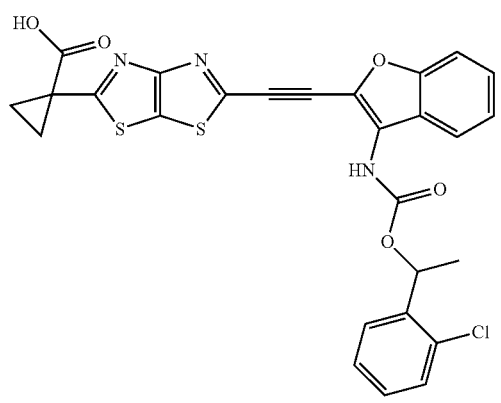 [SMILES: CC(OC(=O)Nc1c(C#Cc2nc3nc(C4(C(=O)O)CC4)sc3s2)oc2ccccc12)c1ccccc1Cl]
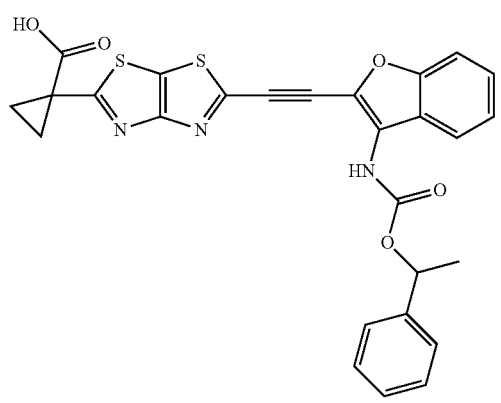
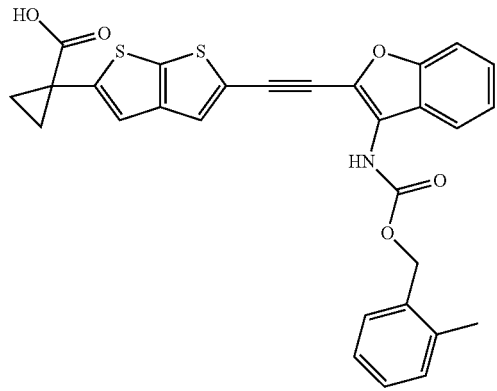
TABLE 11-continued
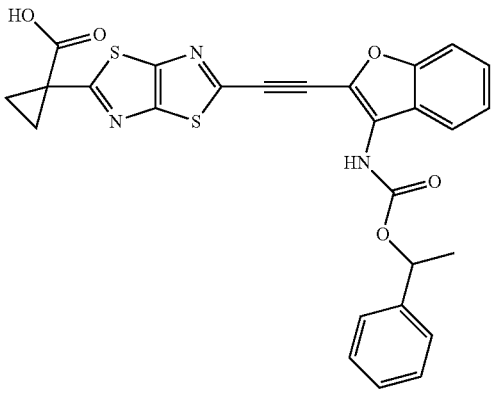 [SMILES: CC(OC(=O)Nc1c(C#Cc2nc3sc(C4(C(=O)O)CC4)nc3s2)oc2ccccc12)c1ccccc1]
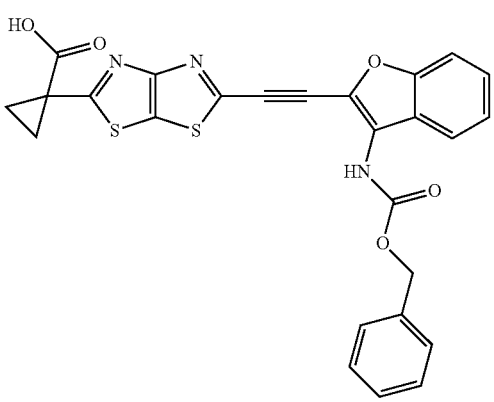
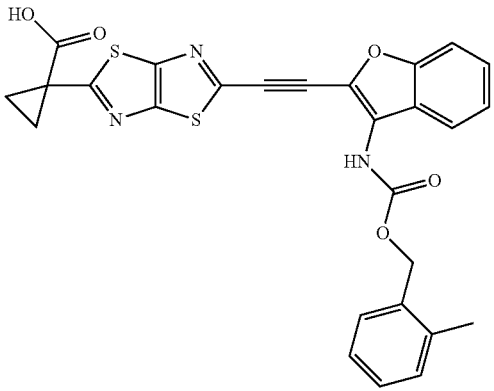

TABLE 11-continued
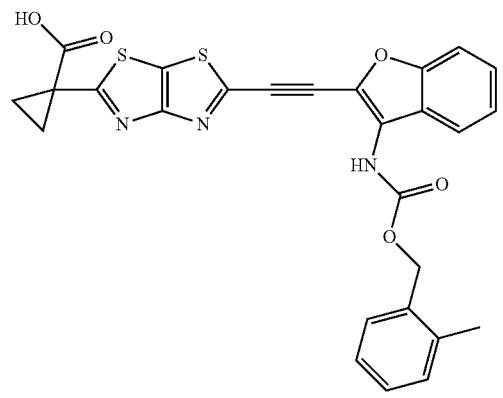
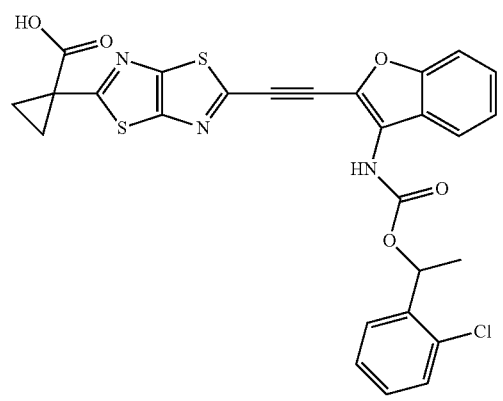 [SMILES: CC(OC(=O)Nc1c(C#Cc2nc3sc(C4(C(=O)O)CC4)nc3s2)oc2ccccc12)c1ccccc1Cl]
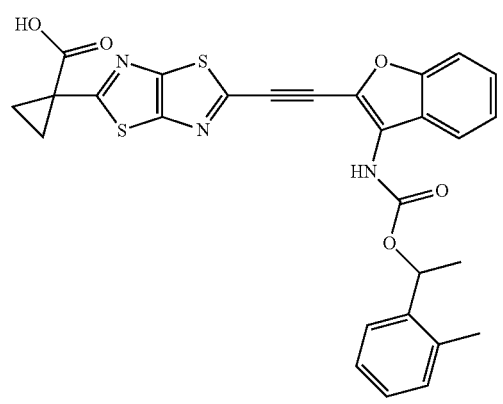 [SMILES: Cc1ccccc1C(C)OC(=O)Nc1c(C#Cc2nc3sc(C4(C(=O)O)CC4)nc3s2)oc2ccccc12]
TABLE 11-continued
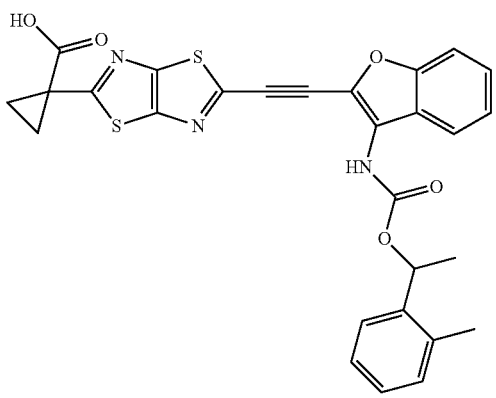 [SMILES: Cc1ccccc1C(C)OC(=O)Nc1c(C#Cc2nc3sc(C4(C(=O)O)CC4)nc3s2)oc2ccccc12]
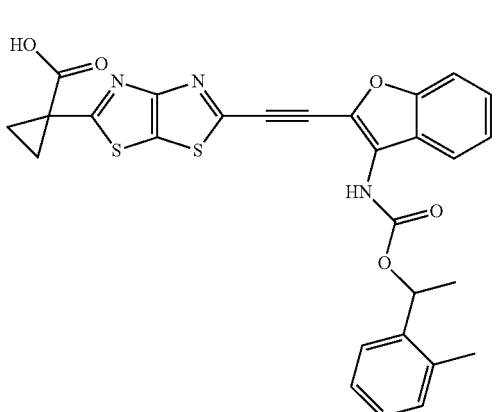
In some embodiments, compounds of Formula (I) are selected from the following compounds as listed in Table 12.
TABLE 12
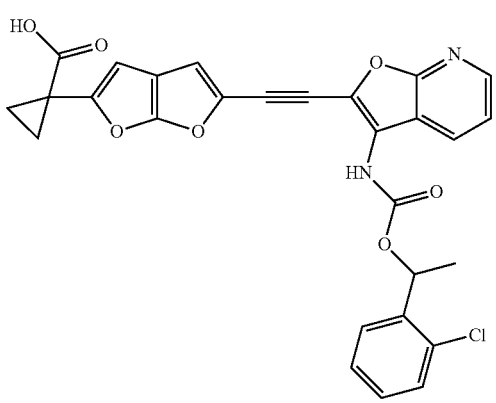 [SMILES: CC(OC(=O)Nc1c(C#Cc2cc3cc(C4(C(=O)O)CC4)oc3o2)oc2ncccc12)c1ccccc1Cl]

| 445 | 446 |
|---|---|
| TABLE 12-continued | TABLE 12-continued |
| 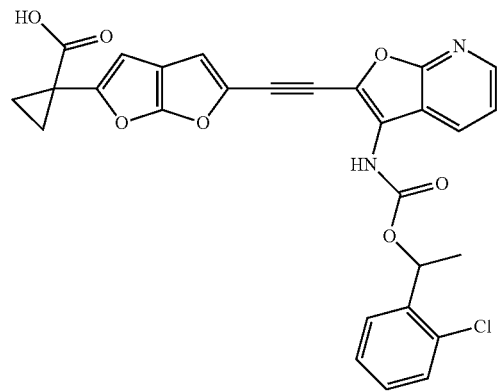 [SMILES: CC(OC(=O)Nc1c(C#Cc2cc3cc(C4(C(=O)O)CC4)oc3o2)oc2ncccc12)c1ccccc1Cl] | 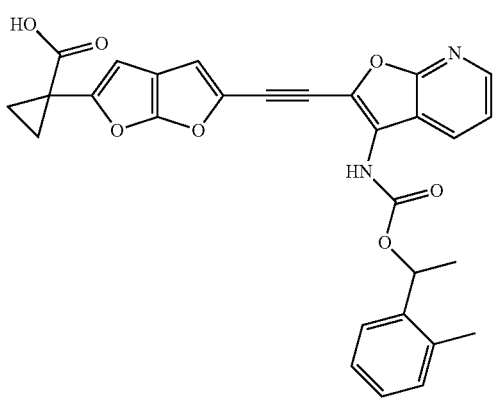 |
| 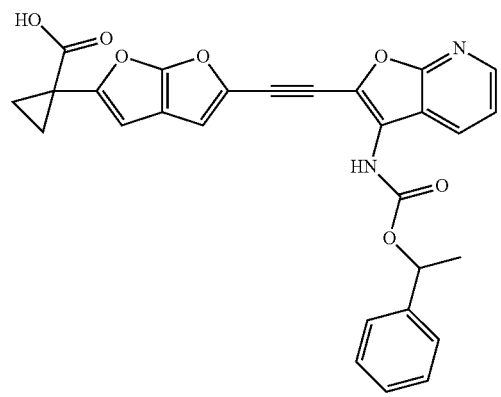 [SMILES: CC(OC(=O)Nc1c(C#Cc2cc3cc(C4(C(=O)O)CC4)oc3o2)oc2ncccc12)c1ccccc1] | |
| 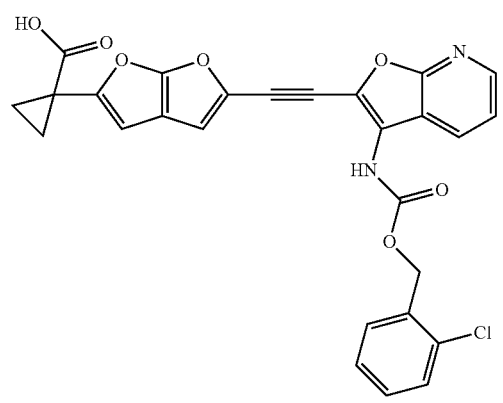 [SMILES: O=C(Nc1c(C#Cc2cc3cc(C4(C(=O)O)CC4)oc3o2)oc2ncccc12)OCc1ccccc1Cl] | 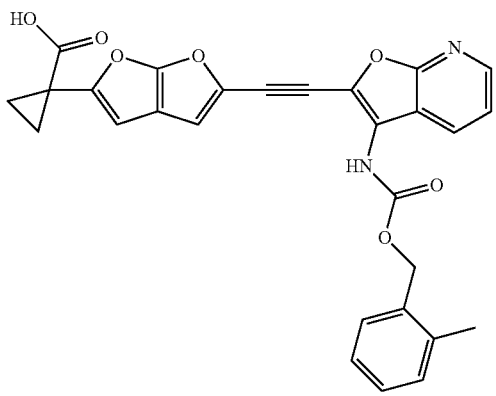 [SMILES: Cc1ccccc1COC(=O)Nc1c(C#Cc2cc3cc(C4(C(=O)O)CC4)oc3o2)oc2ncccc12] |
| 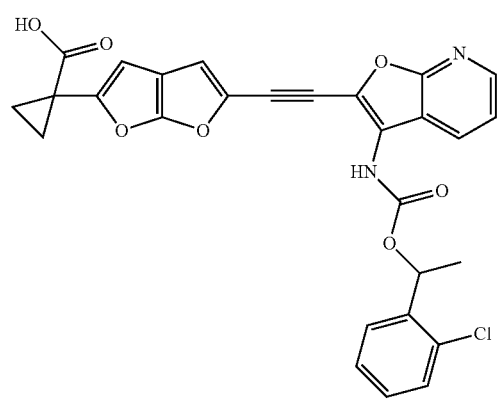 | 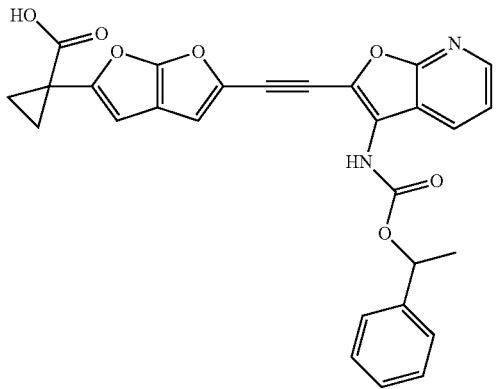 [SMILES: CC(OC(=O)Nc1c(C#Cc2cc3cc(C4(C(=O)O)CC4)oc3o2)oc2ncccc12)c1ccccc1] |

447
TABLE 12-continued
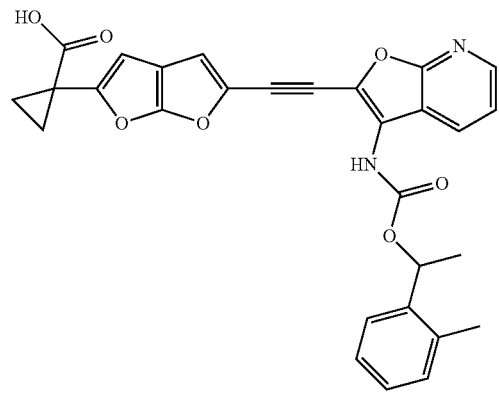
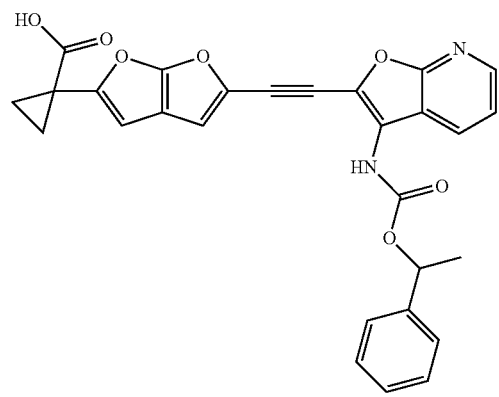 [SMILES: CC(OC(=O)Nc1c(C#Cc2cc3cc(C4(C(=O)O)CC4)oc3o2)oc2ncccc12)c1ccccc1]
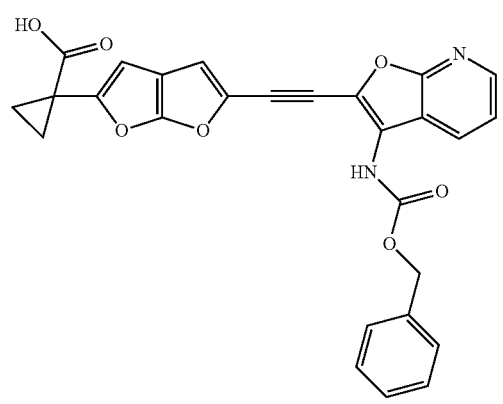
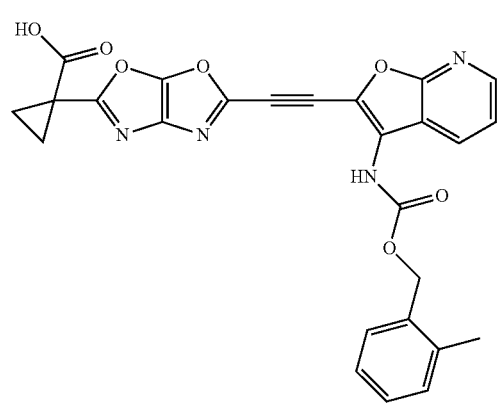 [SMILES: Cc1ccccc1COC(=O)Nc1c(C#Cc2nc3nc(C4(C(=O)O)CC4)oc3o2)oc2ncccc12]
448
TABLE 12-continued
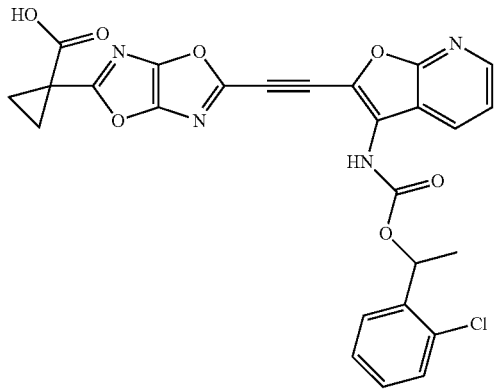
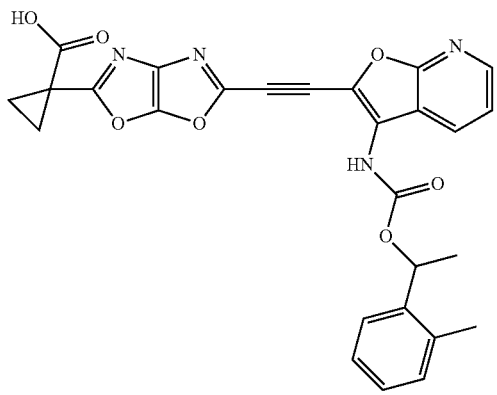
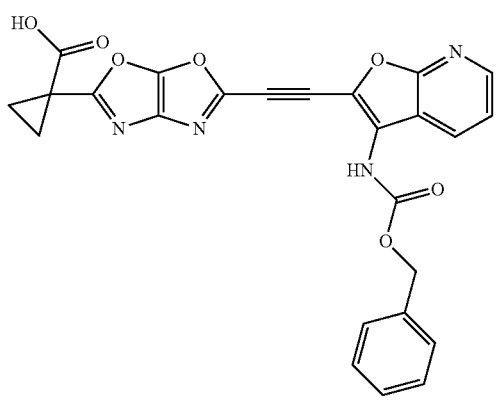 [SMILES: O=C(Nc1c(C#Cc2nc3nc(C4(C(=O)O)CC4)oc3o2)oc2ncccc12)OCc1ccccc1]
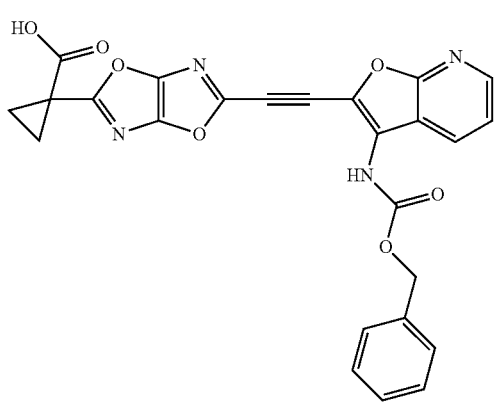 [SMILES: O=C(Nc1c(C#Cc2nc3oc(C4(C(=O)O)CC4)nc3o2)oc2ncccc12)OCc1ccccc1]

449
TABLE 12-continued
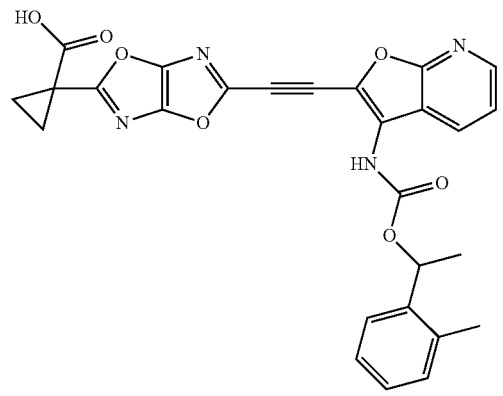 [SMILES: Cc1ccccc1C(C)OC(=O)Nc1c(C#Cc2nc3oc(C4(C(=O)O)CC4)nc3o2)oc2ncccc12]
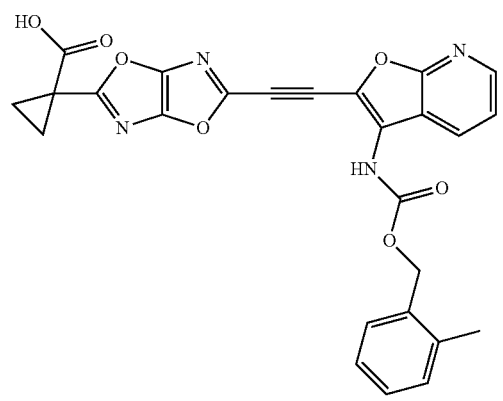
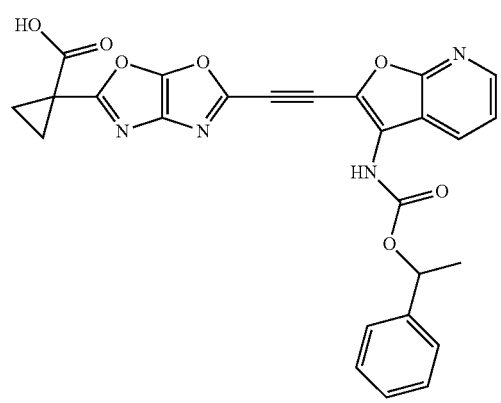
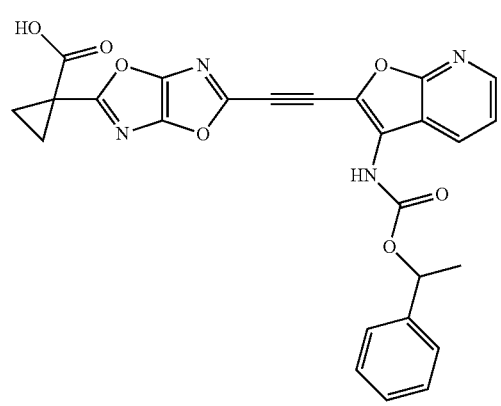
450
TABLE 12-continued
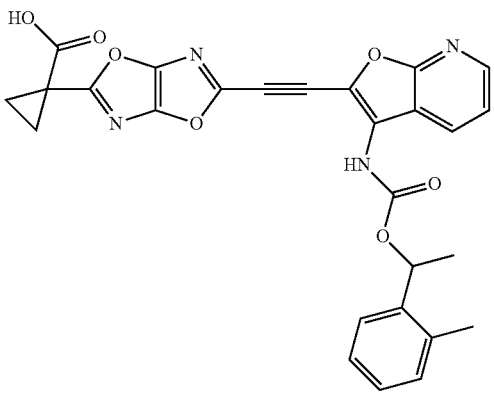 [SMILES: Cc1ccccc1C(C)OC(=O)Nc1c(C#Cc2nc3oc(C4(C(=O)O)CC4)nc3o2)oc2ncccc12]
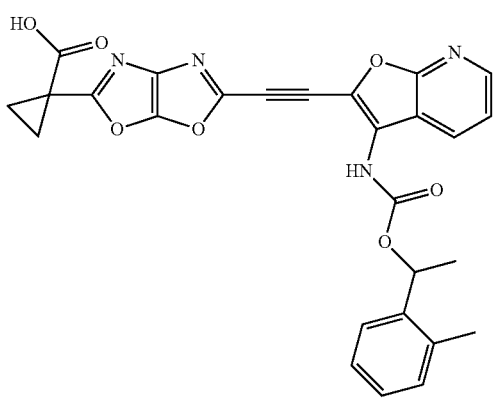 [SMILES: Cc1ccccc1C(C)OC(=O)Nc1c(C#Cc2nc3nc(C4(C(=O)O)CC4)oc3o2)oc2ncccc12]
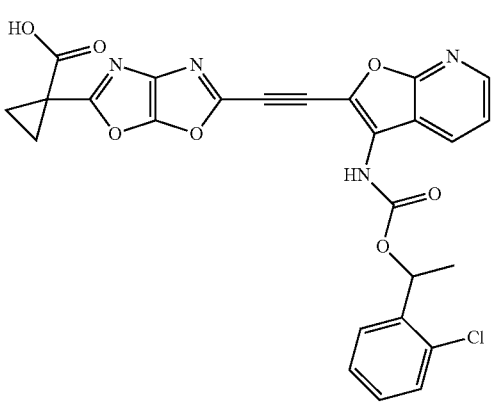 [SMILES: CC(OC(=O)Nc1c(C#Cc2nc3nc(C4(C(=O)O)CC4)oc3o2)oc2ncccc12)c1ccccc1Cl]
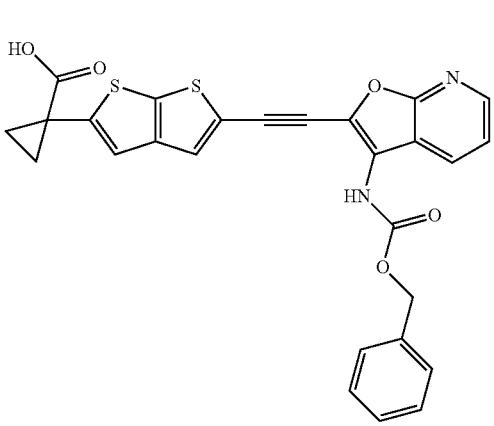 [SMILES: O=C(Nc1c(C#Cc2cc3cc(C4(C(=O)O)CC4)sc3s2)oc2ncccc12)OCc1ccccc1]

TABLE 12-continued
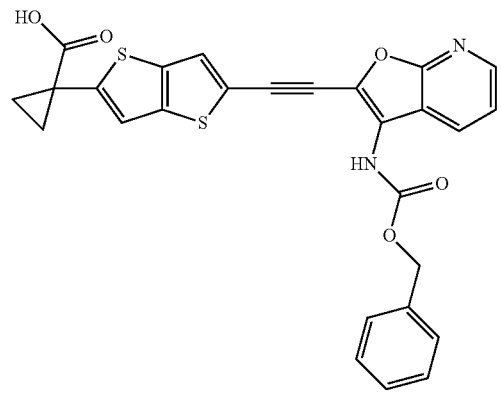 [SMILES: O=C(Nc1c(C#Cc2cc3sc(C4(C(=O)O)CC4)cc3s2)oc2ncccc12)OCc1ccccc1]
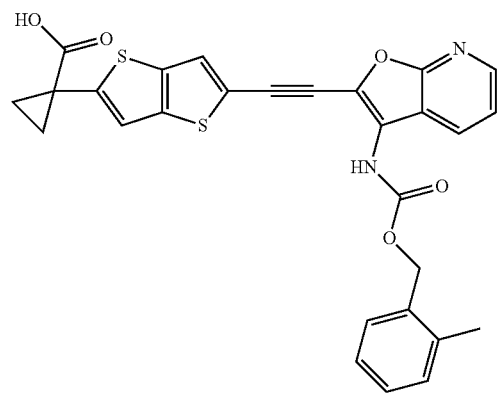 [SMILES: Cc1ccccc1COC(=O)Nc1c(C#Cc2cc3sc(C4(C(=O)O)CC4)cc3s2)oc2ncccc12]
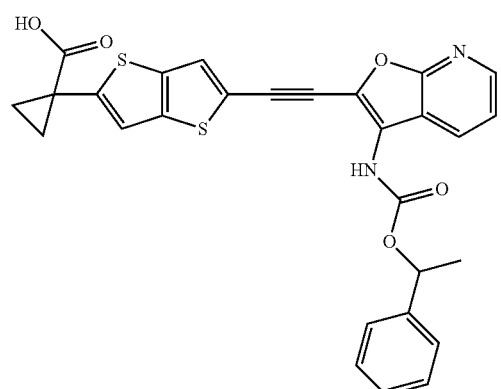
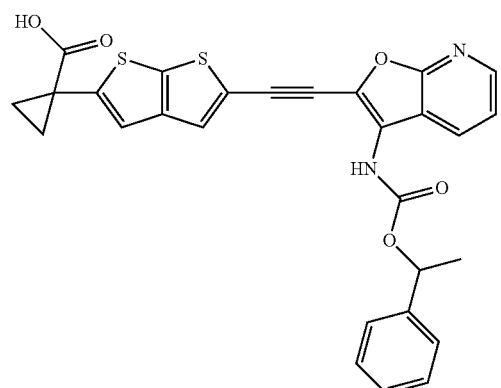
TABLE 12-continued
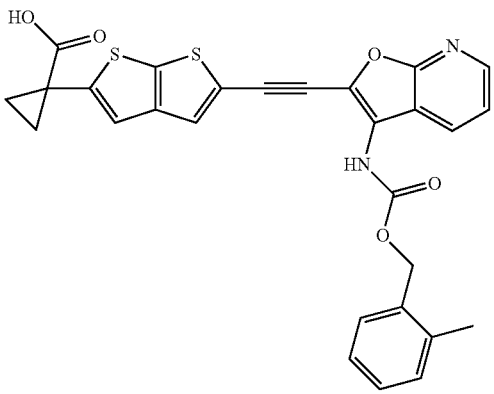
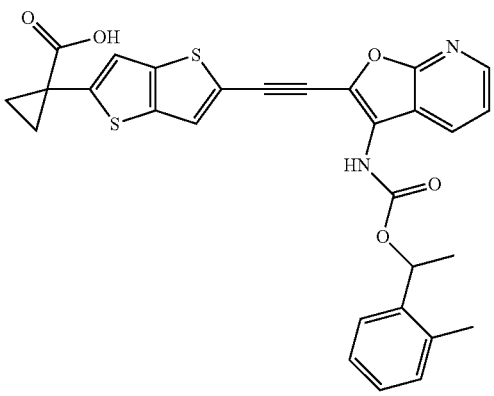
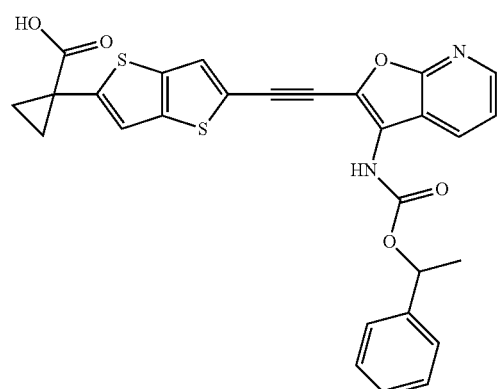
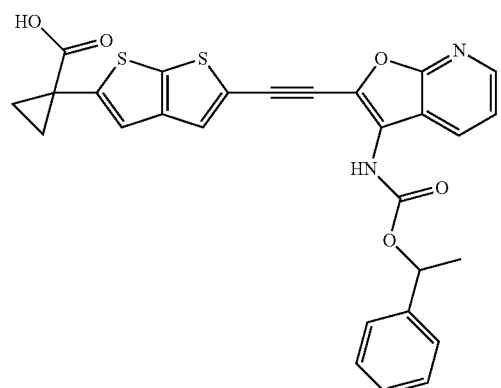

TABLE 12-continued
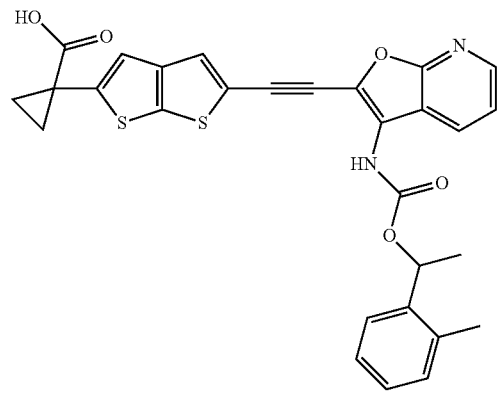
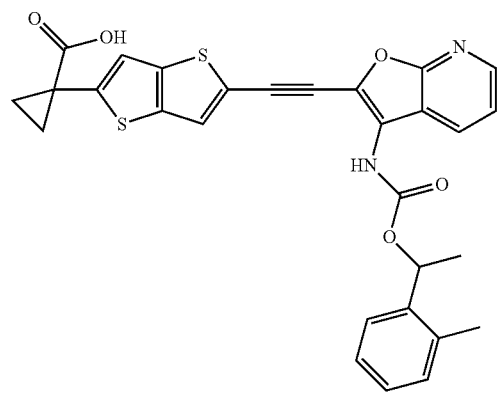
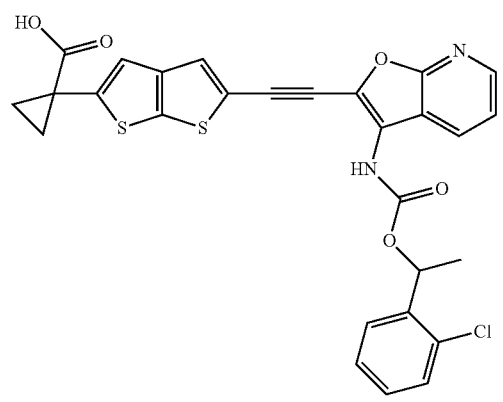 [SMILES: CC(OC(=O)Nc1c(C#Cc2cc3cc(C4(C(=O)O)CC4)sc3s2)oc2ncccc12)c1ccccc1Cl]
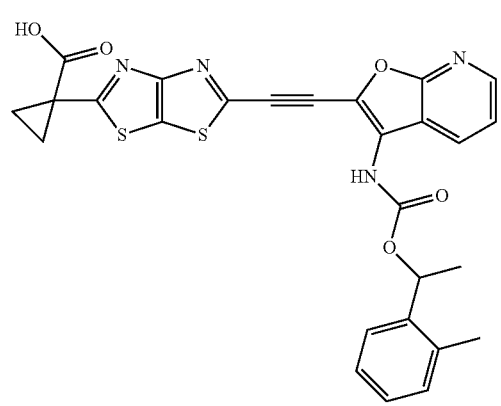
TABLE 12-continued
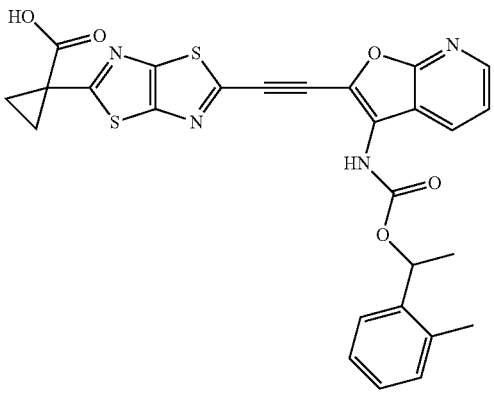 [SMILES: Cc1ccccc1C(C)OC(=O)Nc1c(C#Cc2nc3sc(C4(C(=O)O)CC4)nc3s2)oc2ncccc12]
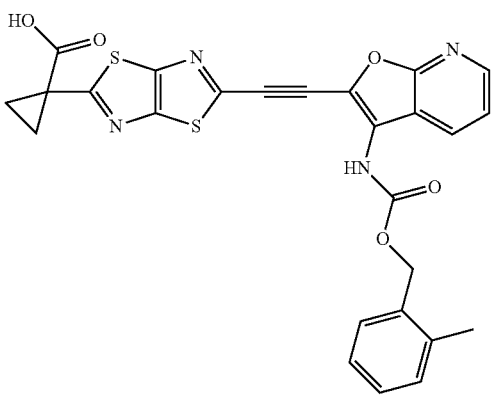 [SMILES: Cc1ccccc1COC(=O)Nc1c(C#Cc2nc3sc(C4(C(=O)O)CC4)nc3s2)oc2ncccc12]
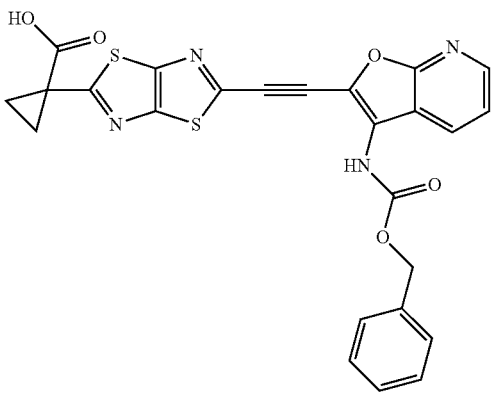 [SMILES: O=C(Nc1c(C#Cc2nc3sc(C4(C(=O)O)CC4)nc3s2)oc2ncccc12)OCc1ccccc1]
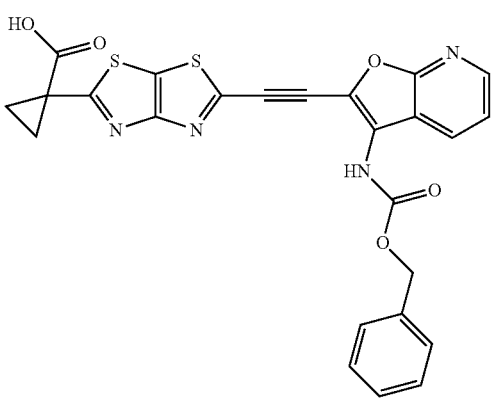 [SMILES: O=C(Nc1c(C#Cc2nc3nc(C4(C(=O)O)CC4)sc3s2)oc2ncccc12)OCc1ccccc1]

455
TABLE 12-continued
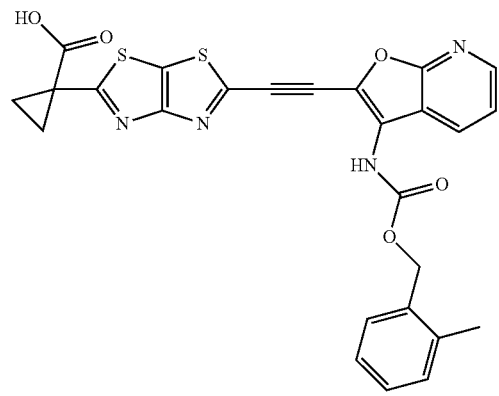 [SMILES: Cc1ccccc1COC(=O)Nc1c(C#Cc2nc3nc(C4(C(=O)O)CC4)sc3s2)oc2ncccc12]
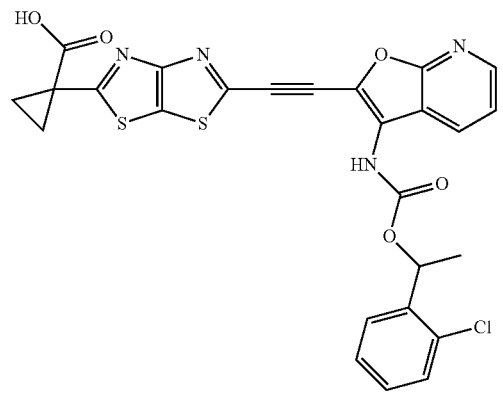 [SMILES: CC(OC(=O)Nc1c(C#Cc2nc3nc(C4(C(=O)O)CC4)sc3s2)oc2ncccc12)c1ccccc1Cl]
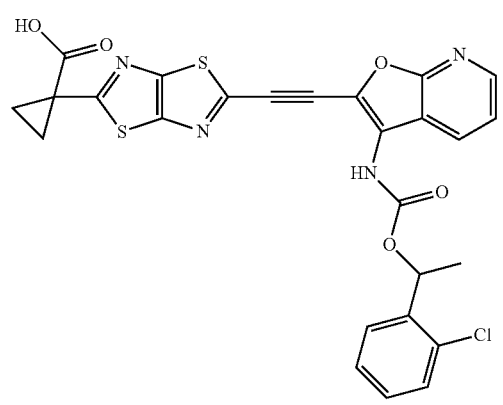
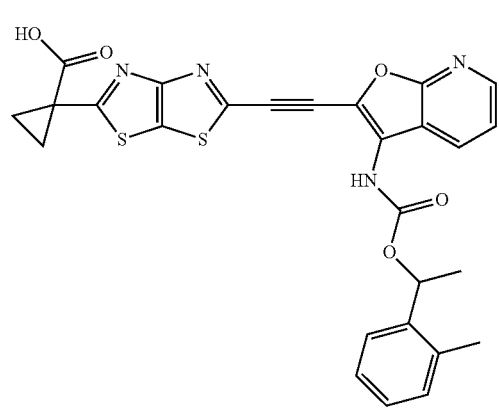
456
TABLE 12-continued
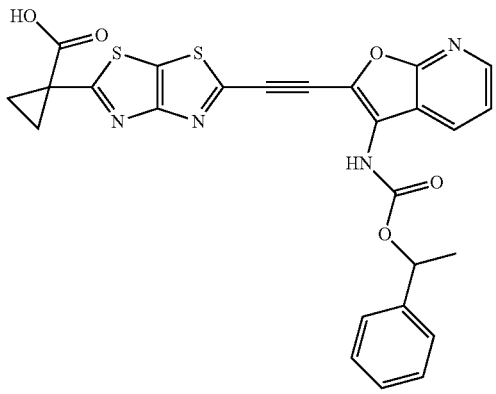 [SMILES: CC(OC(=O)Nc1c(C#Cc2nc3nc(C4(C(=O)O)CC4)sc3s2)oc2ncccc12)c1ccccc1]
In some embodiments, compounds of Formula (I) are selected from the following compounds as listed in Table 13.

TABLE 13
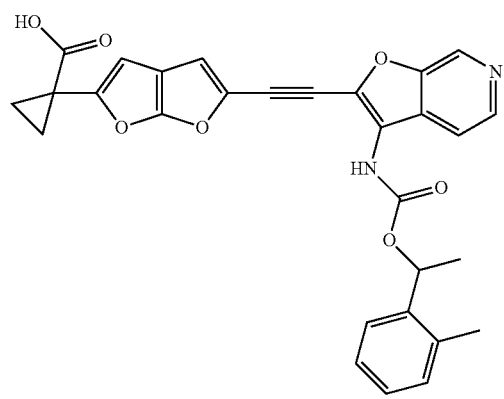 [SMILES: Cc1ccccc1C(C)OC(=O)Nc1c(C#Cc2cc3cc(C4(C(=O)O)CC4)oc3o2)oc2cnccc12]
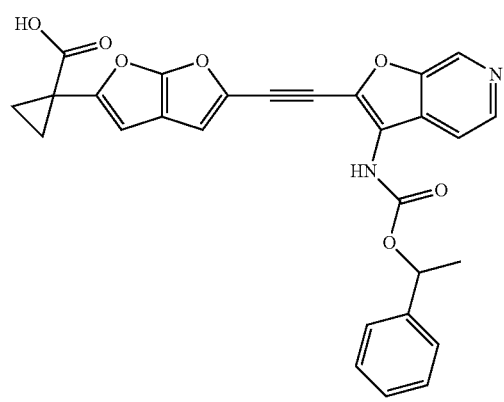 [SMILES: CC(OC(=O)Nc1c(C#Cc2cc3cc(C4(C(=O)O)CC4)oc3o2)oc2cnccc12)c1ccccc1]
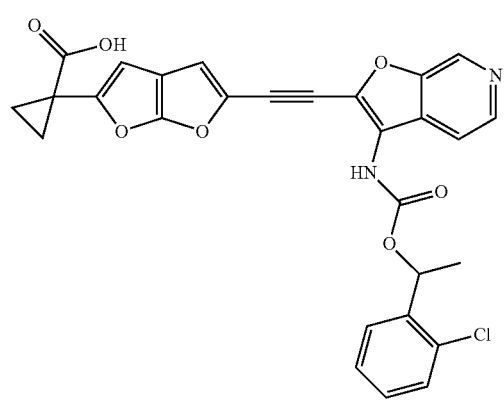 [SMILES: CC(OC(=O)Nc1c(C#Cc2cc3cc(C4(C(=O)O)CC4)oc3o2)oc2cnccc12)c1ccccc1Cl]
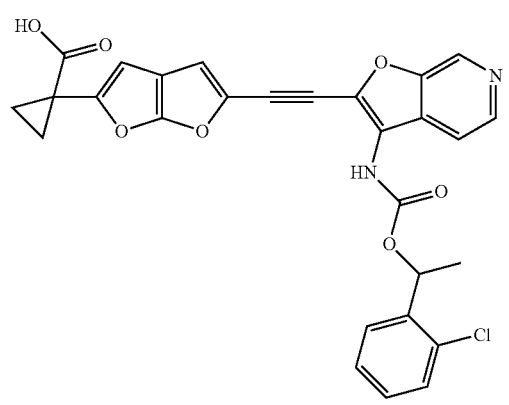 [SMILES: CC(OC(=O)Nc1c(C#Cc2cc3cc(C4(C(=O)O)CC4)oc3o2)oc2cnccc12)c1ccccc1Cl]
TABLE 13-continued
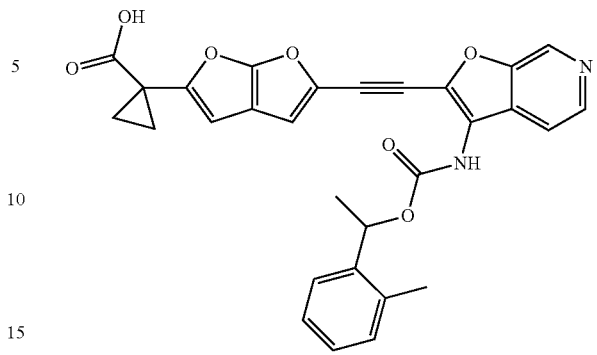

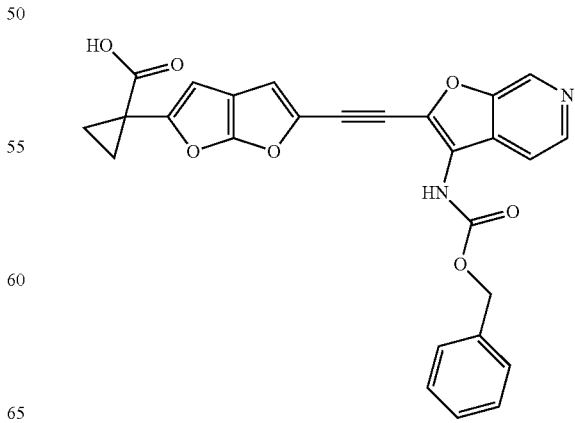

TABLE 13-continued
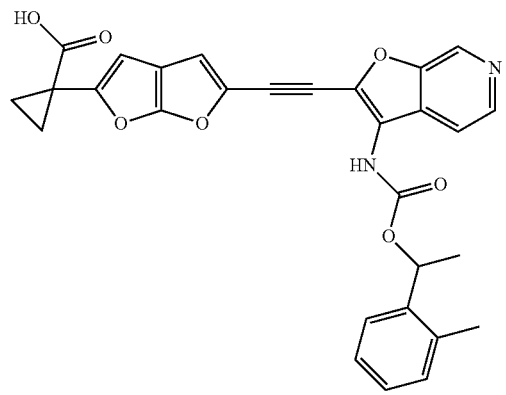
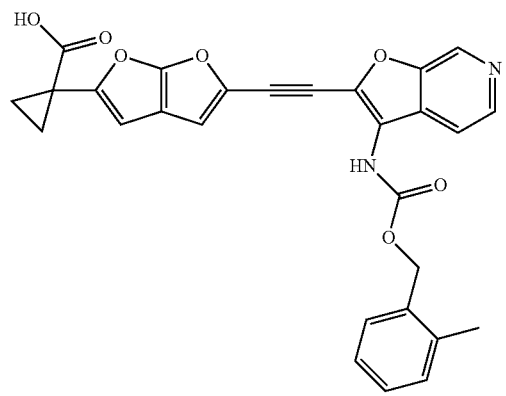 [SMILES: O=C(Nc1c(C#Cc2cc3cc(C4(C(=O)O)CC4)oc3o2)oc2cnccc12)OCc1ccccc1Cl]
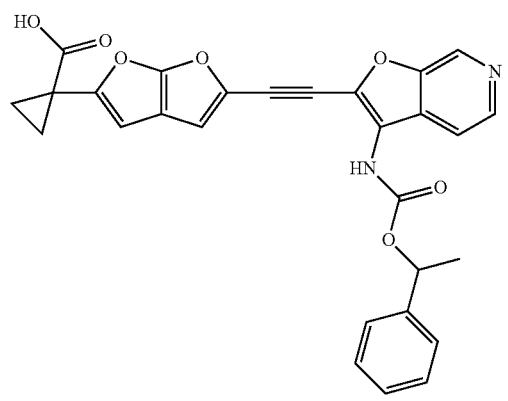
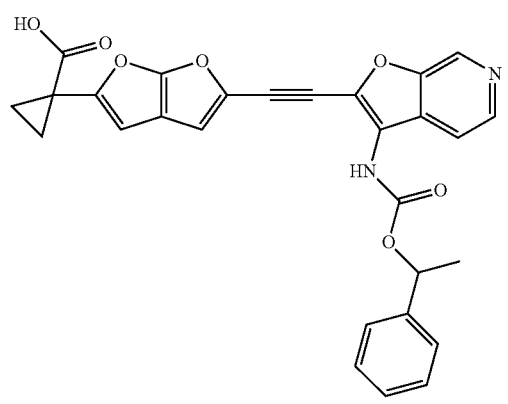
TABLE 13-continued
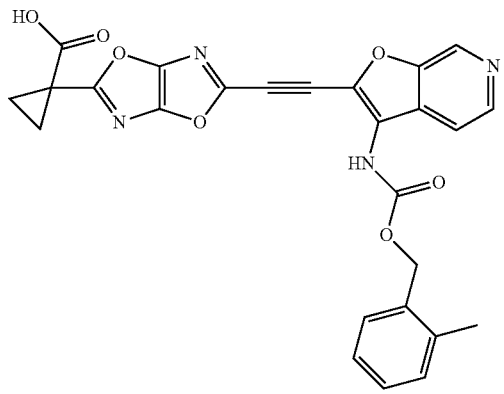 [SMILES: Cc1ccccc1COC(=O)Nc1c(C#Cc2nc3oc(C4(C(=O)O)CC4)nc3o2)oc2cnccc12]
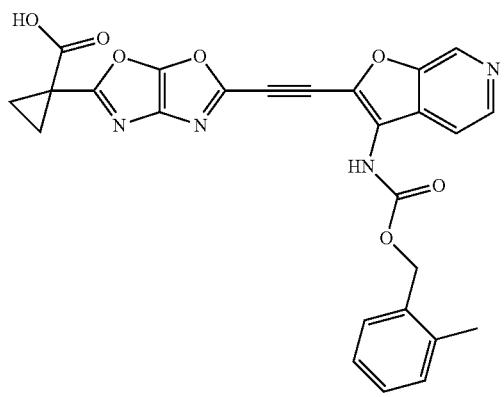
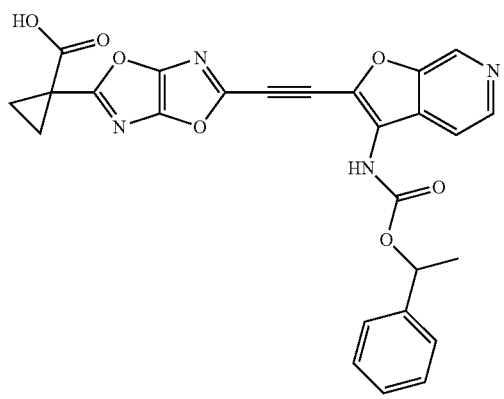 [SMILES: CC(OC(=O)Nc1c(C#Cc2nc3oc(C4(C(=O)O)CC4)nc3o2)oc2cnccc12)c1ccccc1]
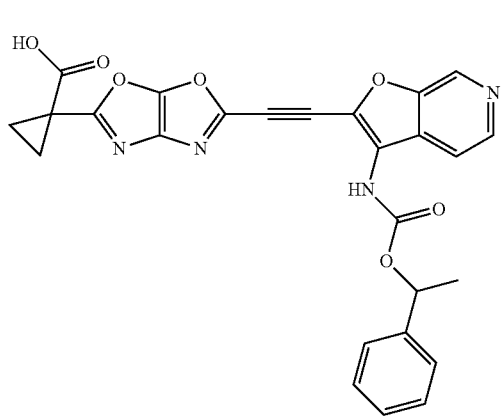 [SMILES: CC(OC(=O)Nc1c(C#Cc2nc3nc(C4(C(=O)O)CC4)oc3o2)oc2cnccc12)c1ccccc1]

TABLE 13-continued
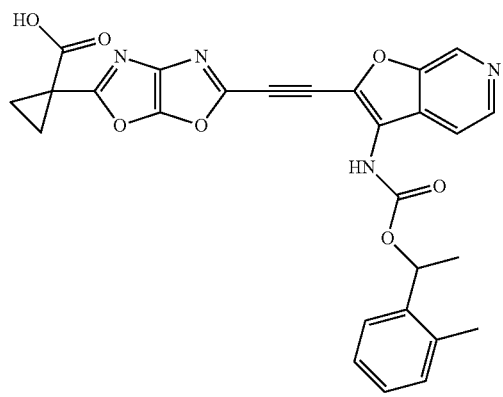 [SMILES: Cc1ccccc1C(C)OC(=O)Nc1c(C#Cc2nc3nc(C4(C(=O)O)CC4)oc3o2)oc2cnccc12]
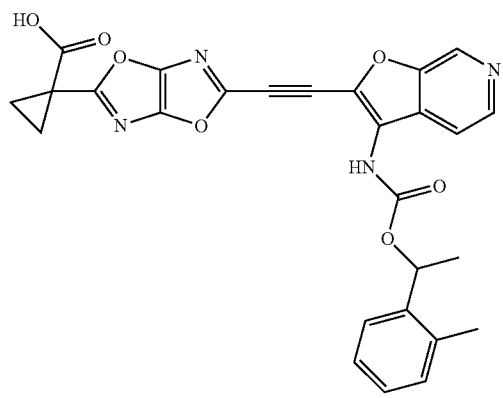 [SMILES: Cc1ccccc1C(C)OC(=O)Nc1c(C#Cc2nc3oc(C4(C(=O)O)CC4)nc3o2)oc2cnccc12]
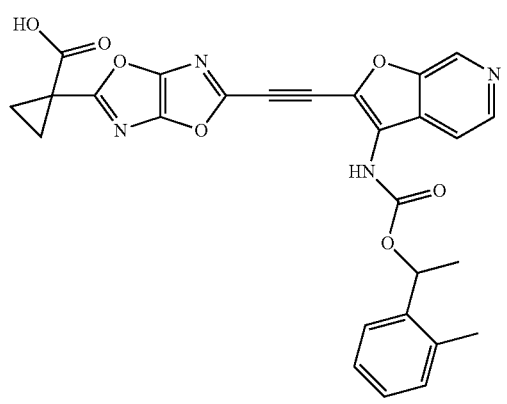 [SMILES: Cc1ccccc1C(C)OC(=O)Nc1c(C#Cc2nc3oc(C4(C(=O)O)CC4)nc3o2)oc2cnccc12]
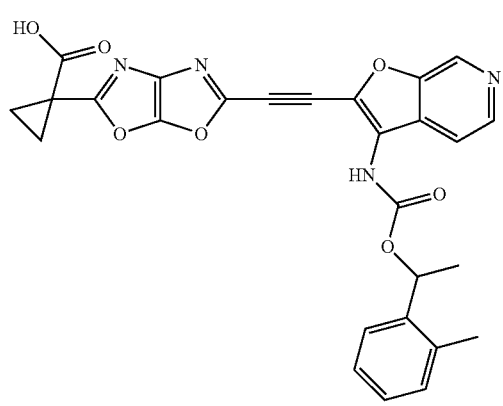 [SMILES: Cc1ccccc1C(C)OC(=O)Nc1c(C#Cc2nc3nc(C4(C(=O)O)CC4)oc3o2)oc2cnccc12]
TABLE 13-continued
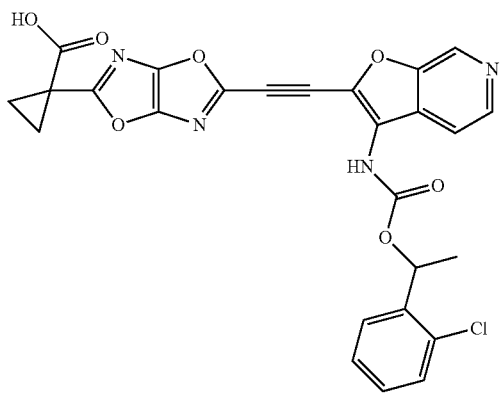 [SMILES: CC(OC(=O)Nc1c(C#Cc2nc3oc(C4(C(=O)O)CC4)nc3o2)oc2cnccc12)c1ccccc1Cl]
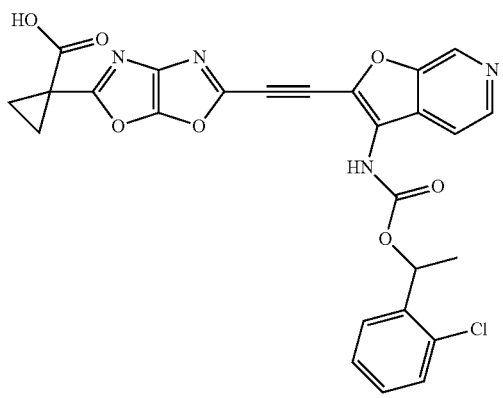
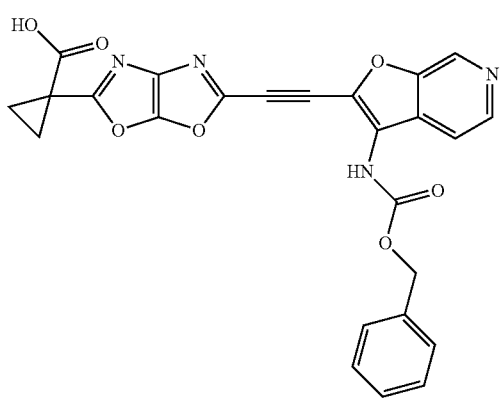
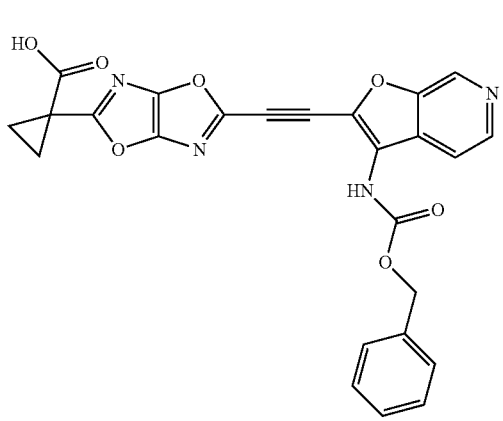 [SMILES: O=C(Nc1c(C#Cc2nc3oc(C4(C(=O)O)CC4)nc3o2)oc2cnccc12)OCc1ccccc1]

TABLE 13-continued
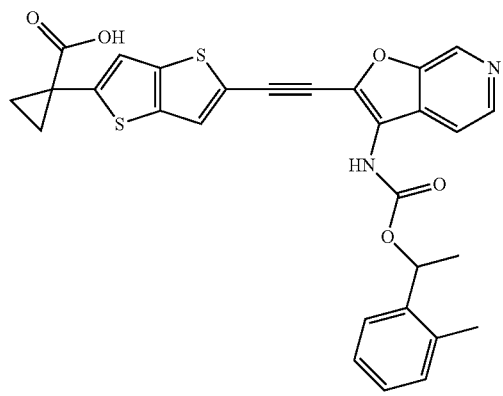 [SMILES: Cc1ccccc1C(C)OC(=O)Nc1c(C#Cc2cc3sc(C4(C(=O)O)CC4)cc3s2)oc2cnccc12]
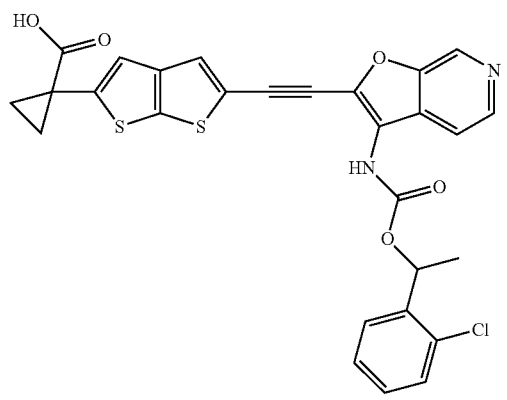
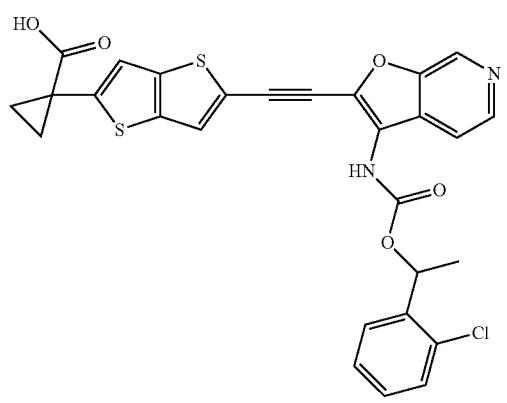
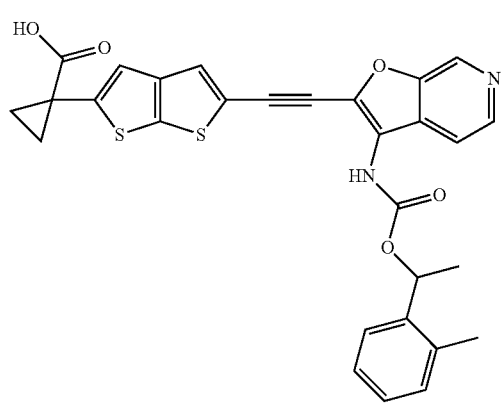
TABLE 13-continued
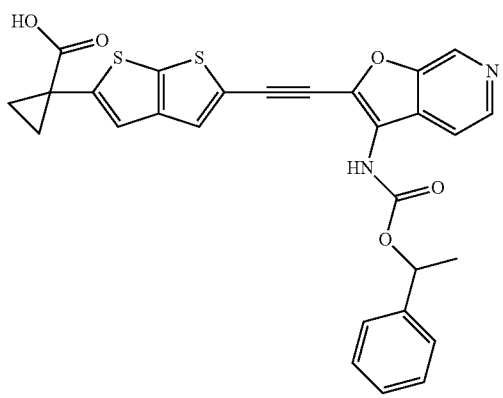
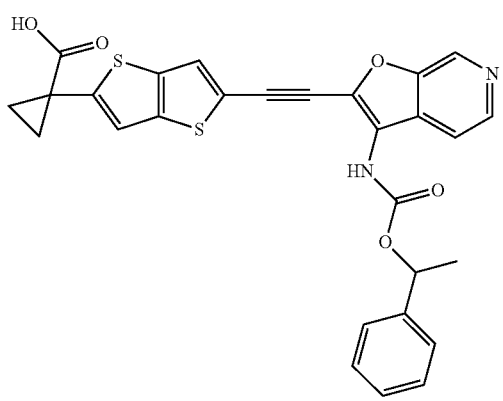 [SMILES: CC(OC(=O)Nc1c(C#Cc2cc3sc(C4(C(=O)O)CC4)cc3s2)oc2cnccc12)c1ccccc1]
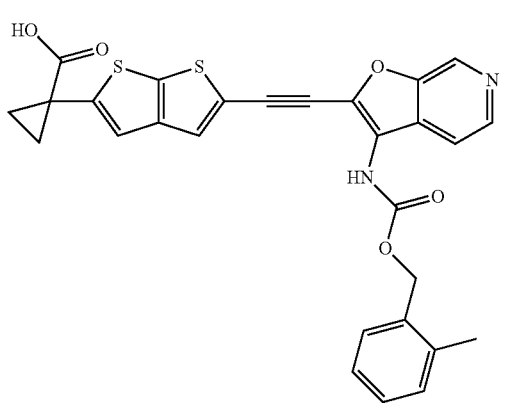
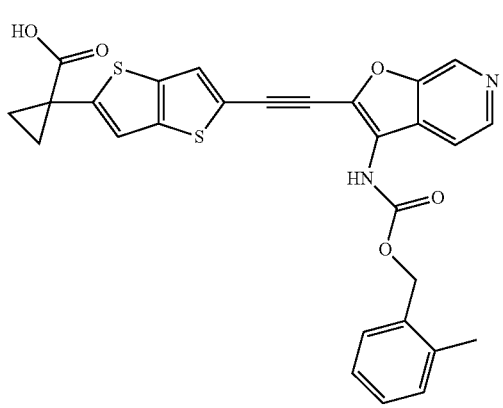

465
TABLE 13-continued
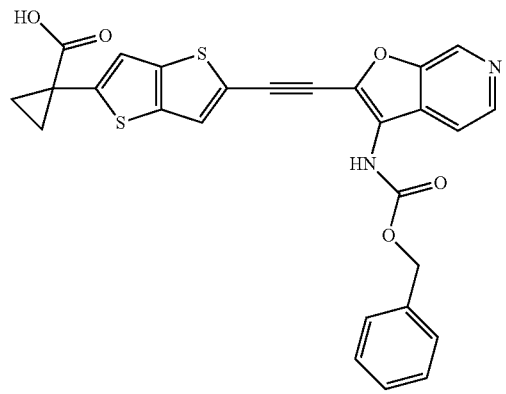 [SMILES: O=C(Nc1c(C#Cc2cc3sc(C4(C(=O)O)CC4)cc3s2)oc2cnccc12)OCc1ccccc1]
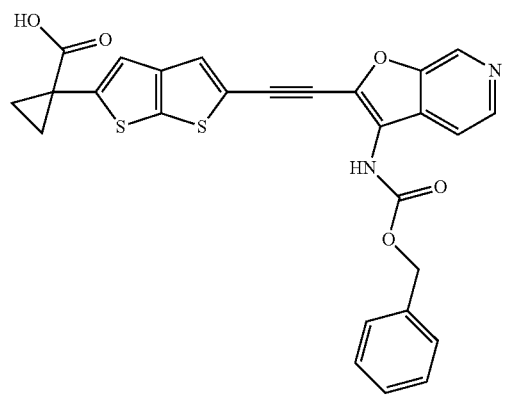 [SMILES: O=C(Nc1c(C#Cc2cc3cc(C4(C(=O)O)CC4)sc3s2)oc2cnccc12)OCc1ccccc1]
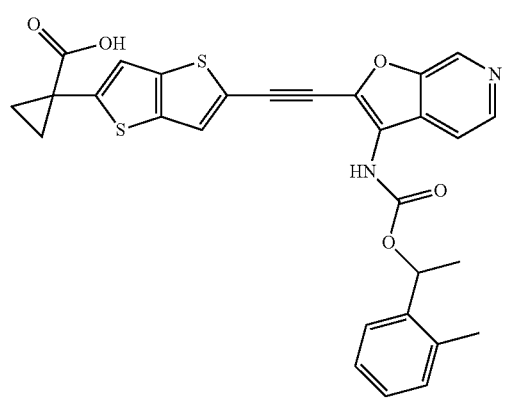 [SMILES: Cc1ccccc1C(C)OC(=O)Nc1c(C#Cc2cc3sc(C4(C(=O)O)CC4)cc3s2)oc2cnccc12]
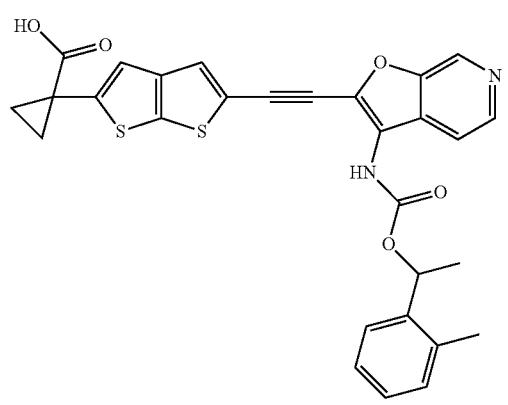 [SMILES: Cc1ccccc1C(C)OC(=O)Nc1c(C#Cc2cc3cc(C4(C(=O)O)CC4)sc3s2)oc2cnccc12]
466
TABLE 13-continued
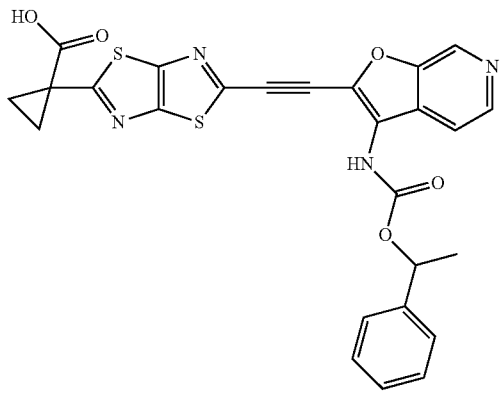 [SMILES: CC(OC(=O)Nc1c(C#Cc2nc3sc(C4(C(=O)O)CC4)nc3s2)oc2cnccc12)c1ccccc1]
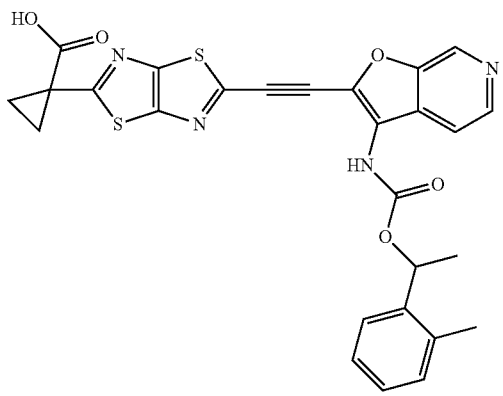 [SMILES: Cc1ccccc1C(C)OC(=O)Nc1c(C#Cc2nc3sc(C4(C(=O)O)CC4)nc3s2)oc2cnccc12]
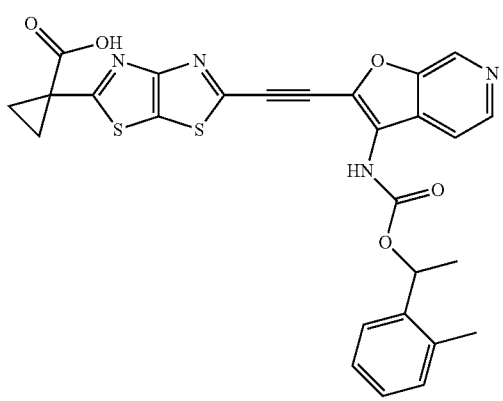 [SMILES: Cc1ccccc1C(C)OC(=O)Nc1c(C#Cc2nc3nc(C4(C(=O)O)CC4)sc3s2)oc2cnccc12]
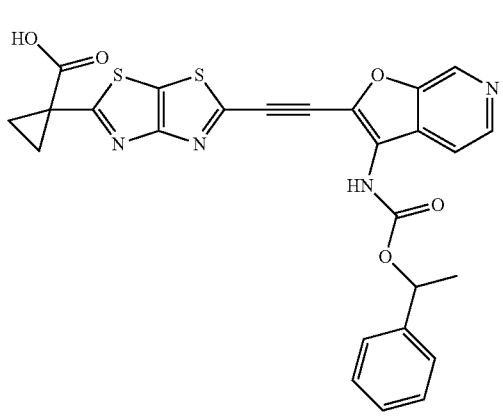

467
TABLE 13-continued
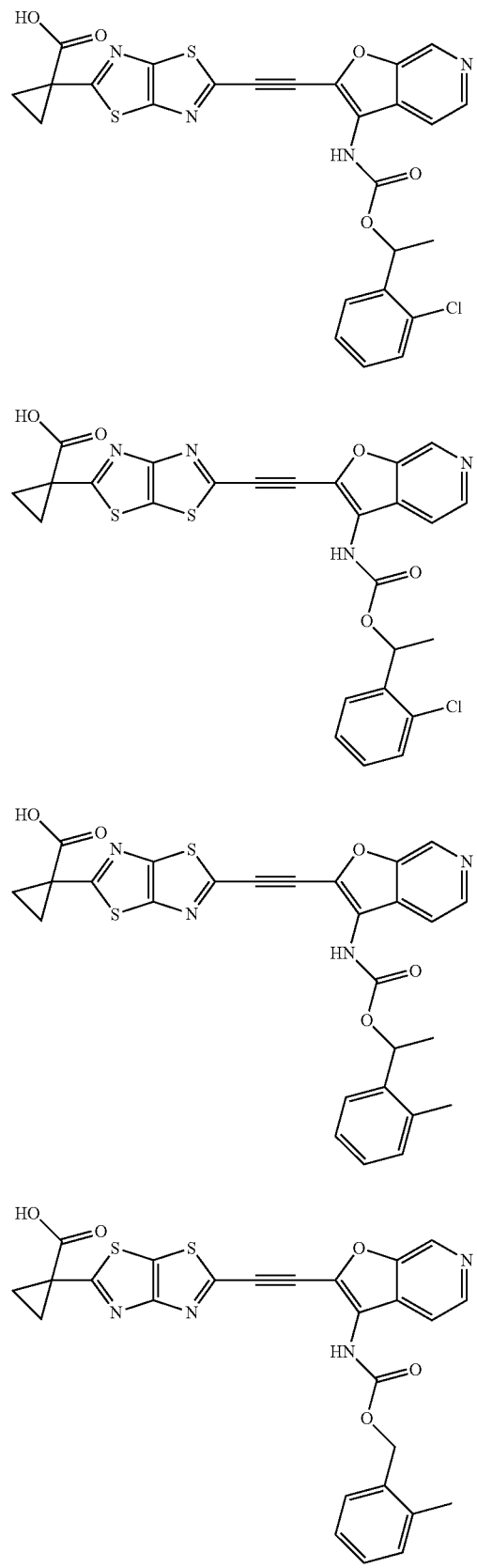
468
TABLE 13-continued
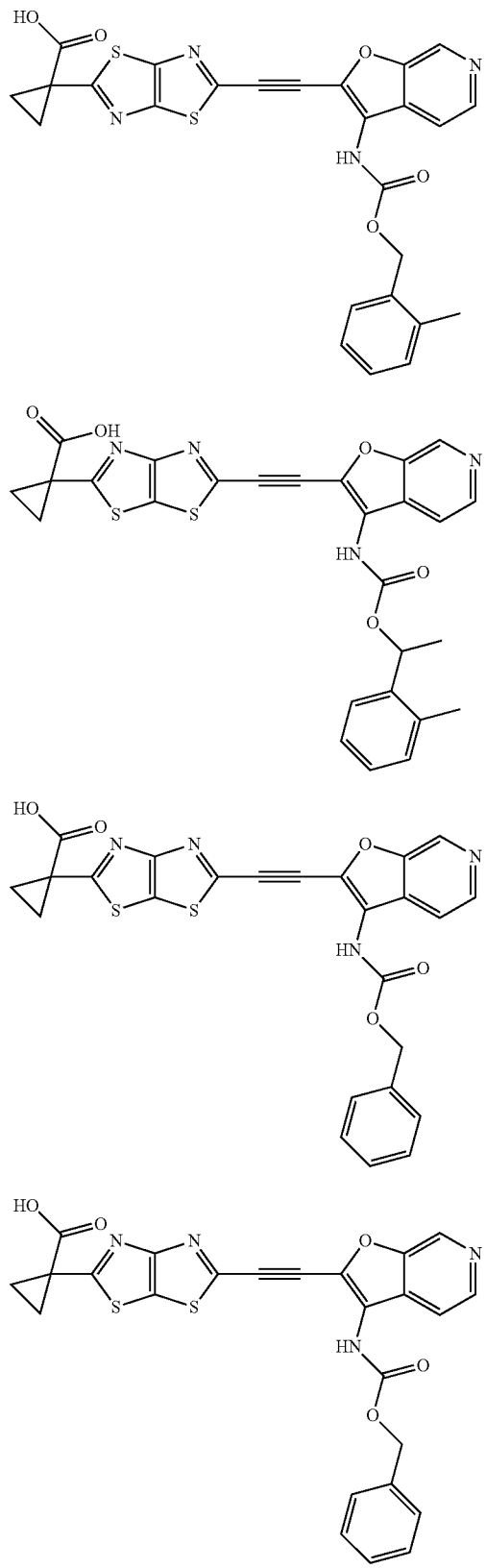
In some embodiments, compounds of Formula (I) are selected from the following compounds as listed in Table 14.

TABLE 14
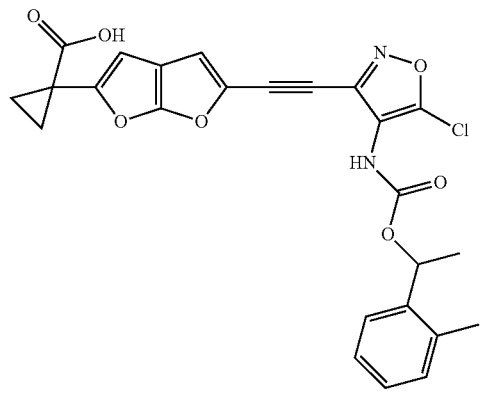
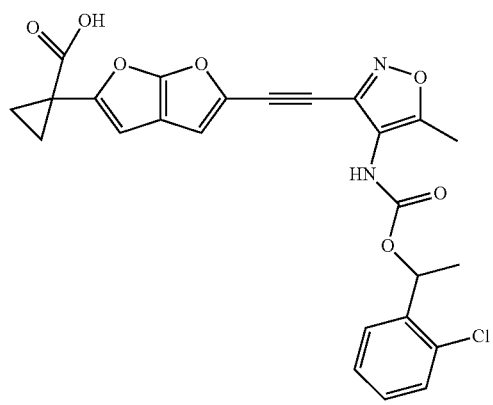 [SMILES: Cc1onc(C#Cc2cc3cc(C4(C(=O)O)CC4)oc3o2)c1NC(=O)OC(C)c1ccccc1Cl]
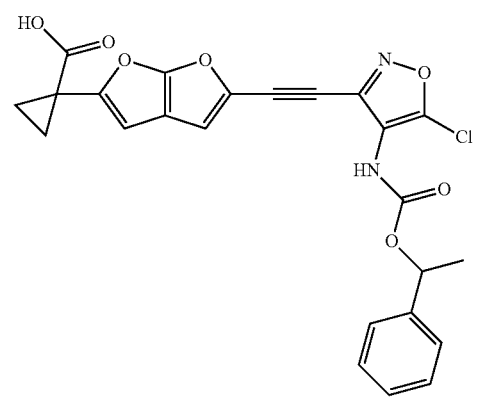
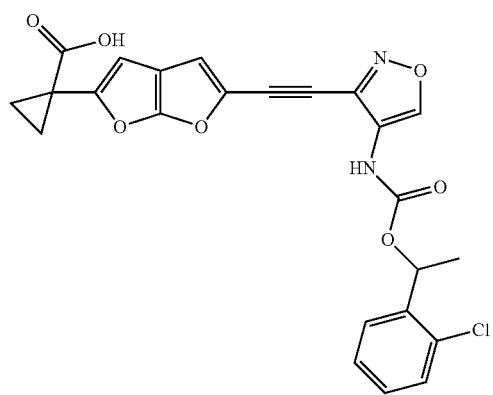 [SMILES: CC(OC(=O)Nc1conc1C#Cc1cc2cc(C3(C(=O)O)CC3)oc2o1)c1ccccc1Cl]
TABLE 14-continued
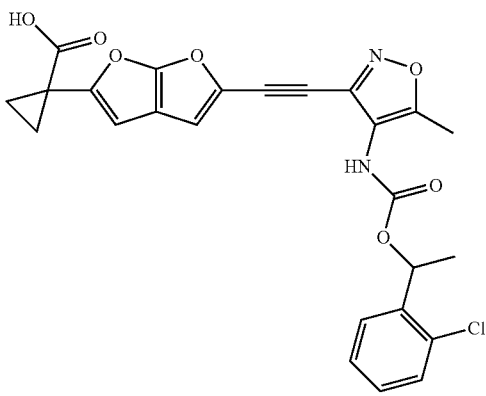
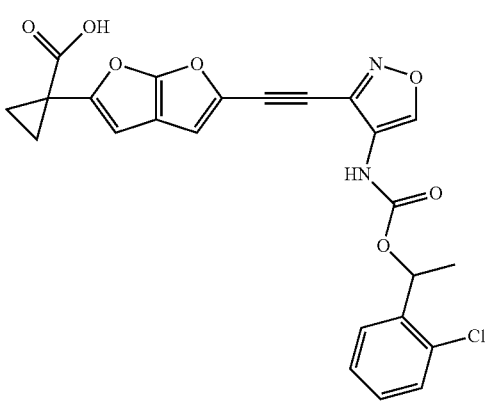 [SMILES: CC(OC(=O)Nc1conc1C#Cc1cc2cc(C3(C(=O)O)CC3)oc2o1)c1ccccc1Cl]
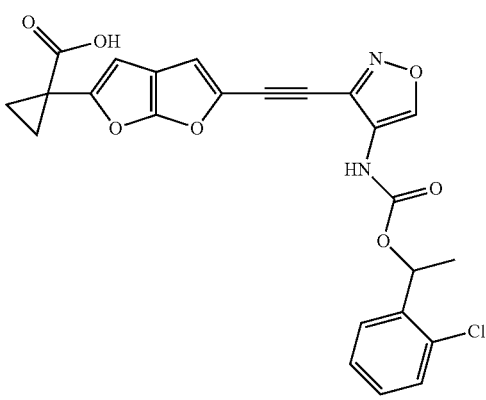 [SMILES: CC(OC(=O)Nc1conc1C#Cc1cc2cc(C3(C(=O)O)CC3)oc2o1)c1ccccc1Cl]
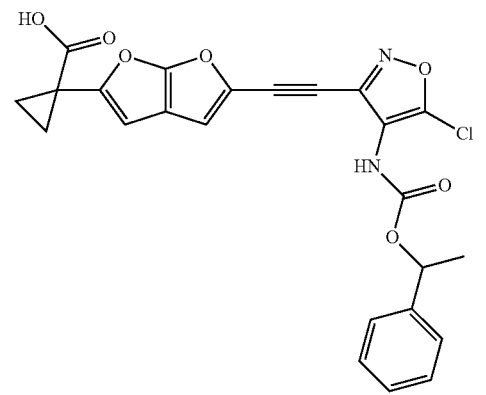

TABLE 14-continued
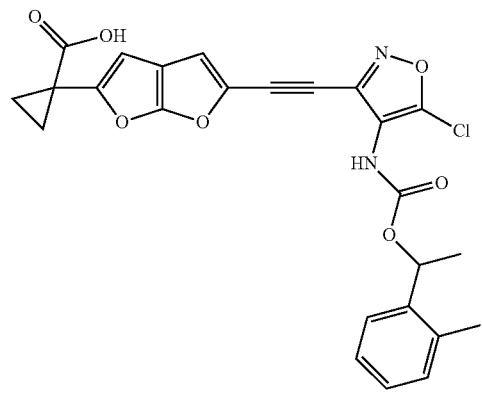
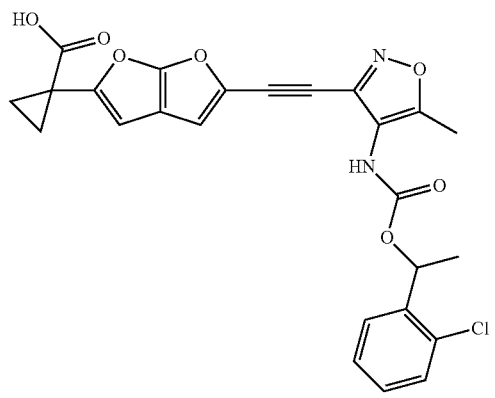 [SMILES: Cc1onc(C#Cc2cc3cc(C4(C(=O)O)CC4)oc3o2)c1NC(=O)OC(C)c1ccccc1Cl]
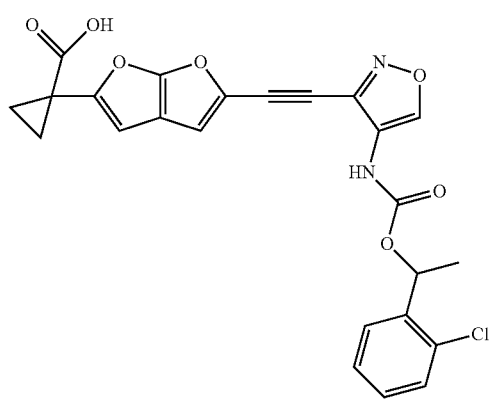 [SMILES: CC(OC(=O)Nc1conc1C#Cc1cc2cc(C3(C(=O)O)CC3)oc2o1)c1ccccc1Cl]
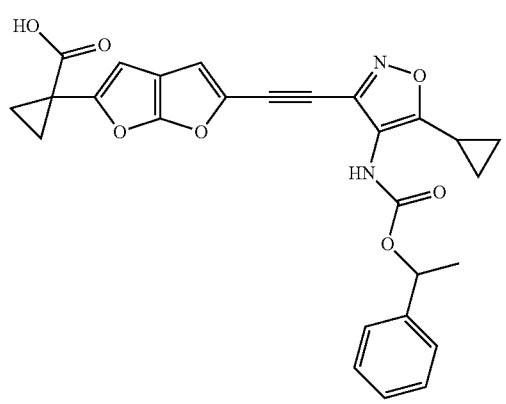 [SMILES: CC(OC(=O)Nc1c(C#Cc2cc3cc(C4(C(=O)O)CC4)oc3o2)noc1C1CC1)c1ccccc1]
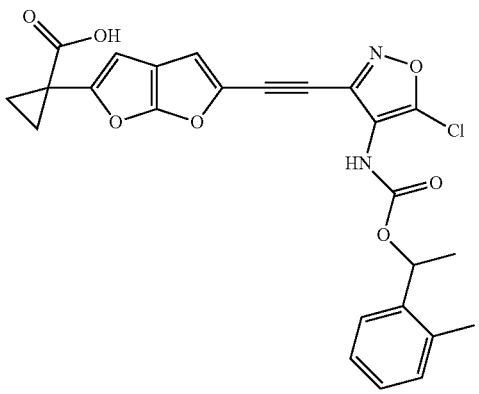
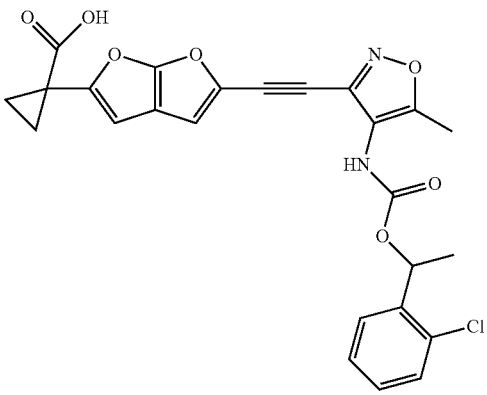 [SMILES: Cc1onc(C#Cc2cc3cc(C4(C(=O)O)CC4)oc3o2)c1NC(=O)OC(C)c1ccccc1Cl]
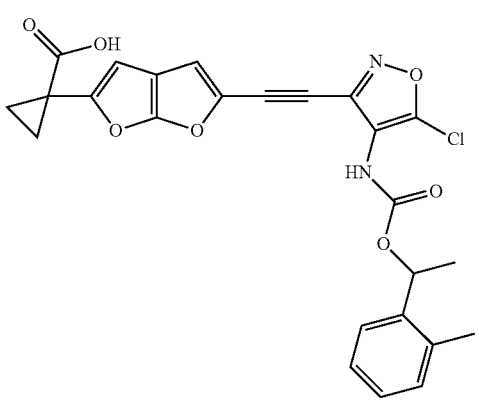 [SMILES: Cc1ccccc1C(C)OC(=O)Nc1c(C#Cc2cc3cc(C4(C(=O)O)CC4)oc3o2)noc1Cl]
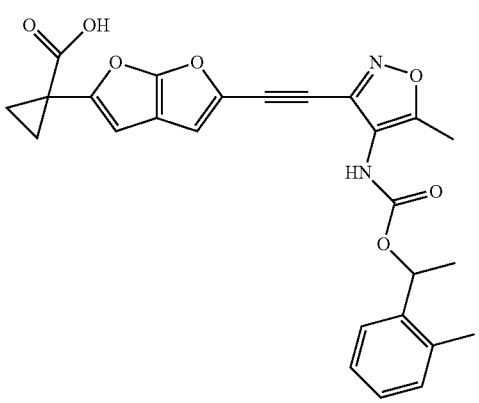 [SMILES: Cc1ccccc1C(C)OC(=O)Nc1c(C#Cc2cc3cc(C4(C(=O)O)CC4)oc3o2)noc1C]

TABLE 14-continued
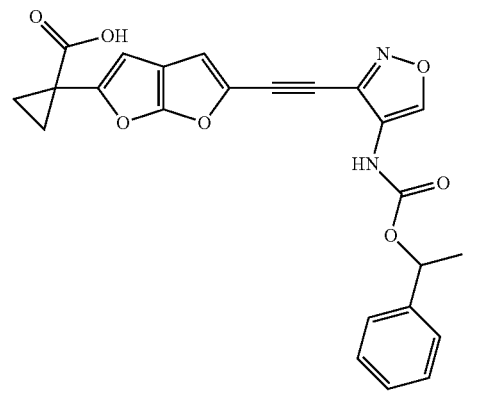 [SMILES: CC(OC(=O)Nc1conc1C#Cc1cc2cc(C3(C(=O)O)CC3)oc2o1)c1ccccc1]
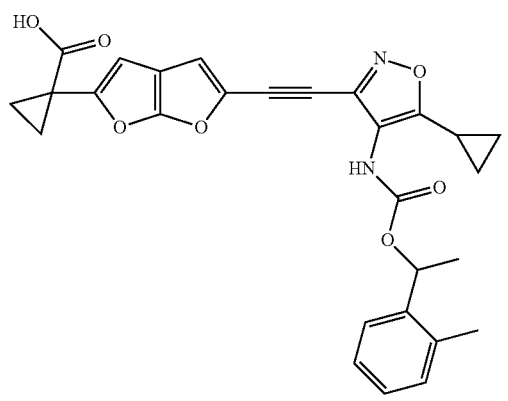 [SMILES: Cc1ccccc1C(C)OC(=O)Nc1c(C#Cc2cc3cc(C4(C(=O)O)CC4)oc3o2)noc1C1CC1]
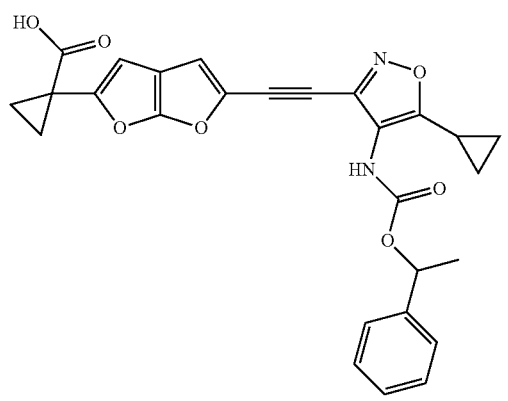 [SMILES: CC(OC(=O)Nc1c(C#Cc2cc3cc(C4(C(=O)O)CC4)oc3o2)noc1C1CC1)c1ccccc1]
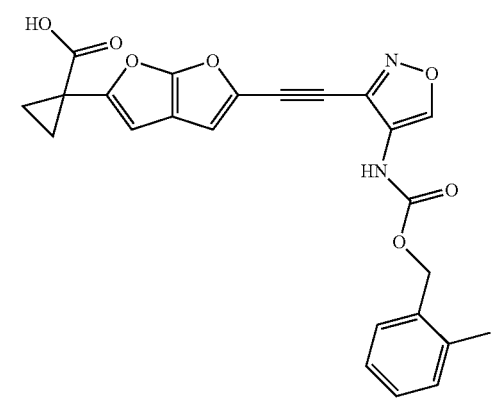 [SMILES: Cc1ccccc1COC(=O)Nc1conc1C#Cc1cc2cc(C3(C(=O)O)CC3)oc2o1]
TABLE 14-continued
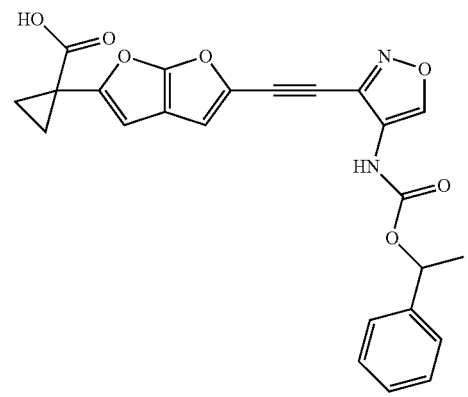
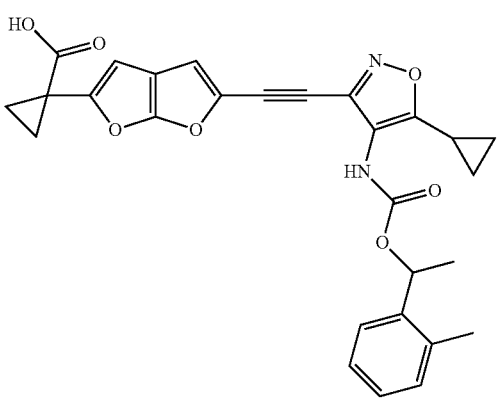 [SMILES: Cc1ccccc1C(C)OC(=O)Nc1c(C#Cc2cc3cc(C4(C(=O)O)CC4)oc3o2)noc1C1CC1]
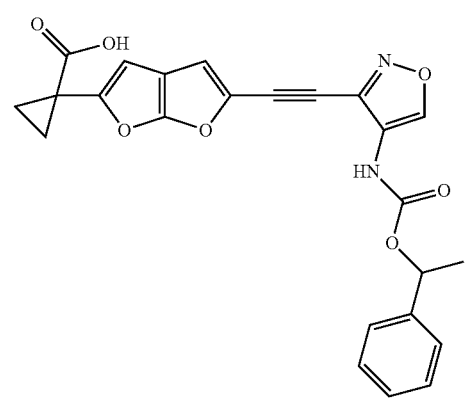 [SMILES: CC(OC(=O)Nc1conc1C#Cc1cc2cc(C3(C(=O)O)CC3)oc2o1)c1ccccc1]
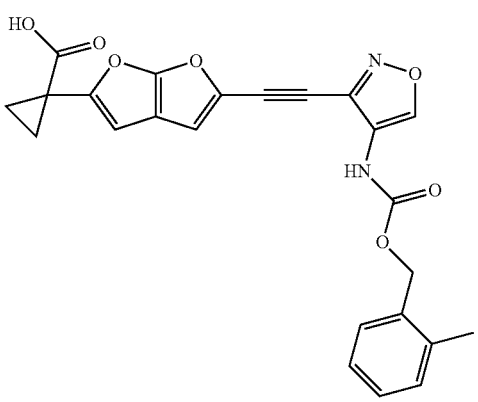 [SMILES: Cc1ccccc1COC(=O)Nc1conc1C#Cc1cc2cc(C3(C(=O)O)CC3)oc2o1]

TABLE 14-continued
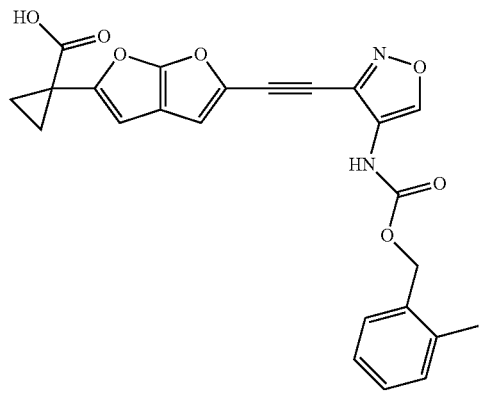 [SMILES: Cc1ccccc1COC(=O)Nc1conc1C#Cc1cc2cc(C3(C(=O)O)CC3)oc2o1]
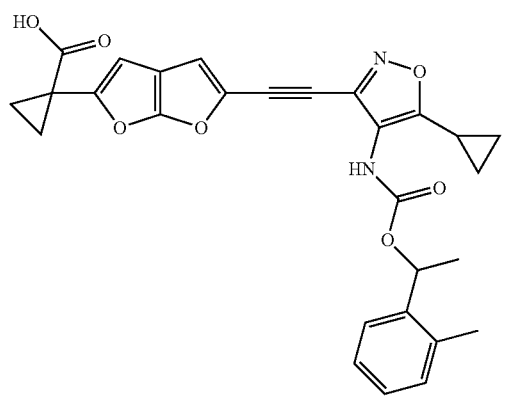 [SMILES: Cc1ccccc1C(C)OC(=O)Nc1c(C#Cc2cc3cc(C4(C(=O)O)CC4)oc3o2)noc1C1CC1]
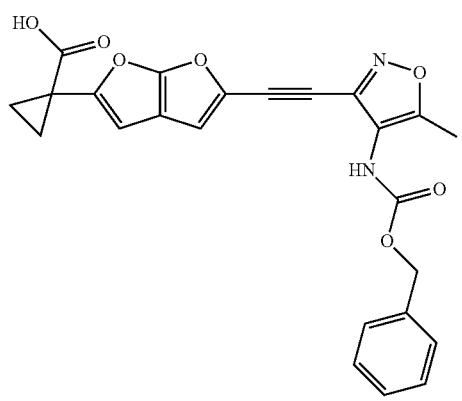 [SMILES: Cc1onc(C#Cc2cc3cc(C4(C(=O)O)CC4)oc3o2)c1NC(=O)OCc1ccccc1]
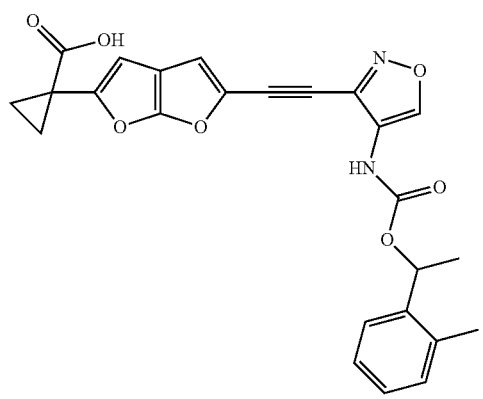 [SMILES: Cc1ccccc1C(C)OC(=O)Nc1conc1C#Cc1cc2cc(C3(C(=O)O)CC3)oc2o1]
TABLE 14-continued
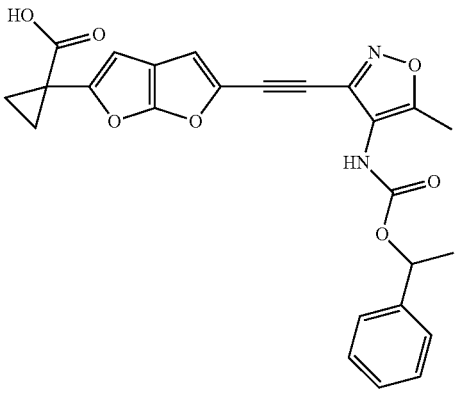 [SMILES: Cc1onc(C#Cc2cc3cc(C4(C(=O)O)CC4)oc3o2)c1NC(=O)OC(C)c1ccccc1]
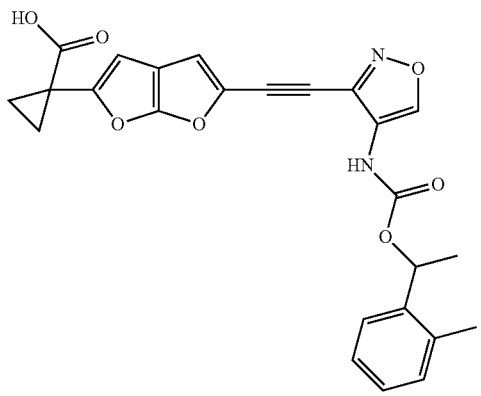 [SMILES: Cc1ccccc1C(C)OC(=O)Nc1conc1C#Cc1cc2cc(C3(C(=O)O)CC3)oc2o1]
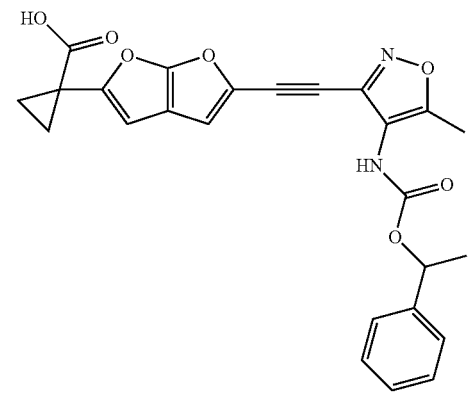
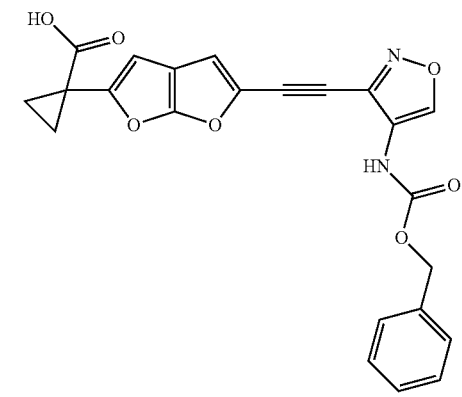 [SMILES: O=C(Nc1conc1C#Cc1cc2cc(C3(C(=O)O)CC3)oc2o1)OCc1ccccc1]

TABLE 14-continued
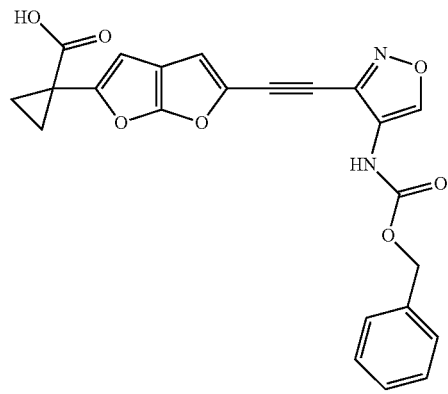 [SMILES: O=C(Nc1conc1C#Cc1cc2cc(C3(C(=O)O)CC3)oc2o1)OCc1ccccc1]
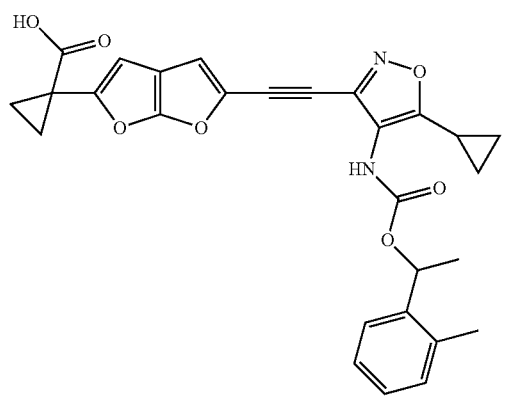 [SMILES: Cc1ccccc1C(C)OC(=O)Nc1c(C#Cc2cc3cc(C4(C(=O)O)CC4)oc3o2)noc1C1CC1]
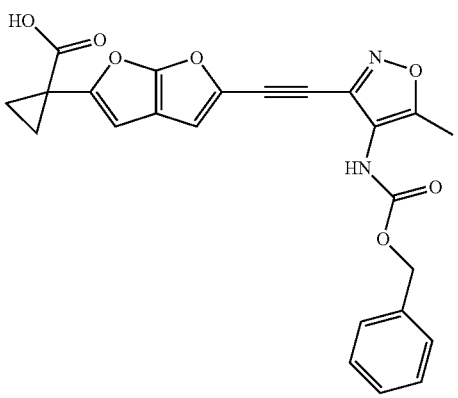 [SMILES: Cc1onc(C#Cc2cc3cc(C4(C(=O)O)CC4)oc3o2)c1NC(=O)OCc1ccccc1]
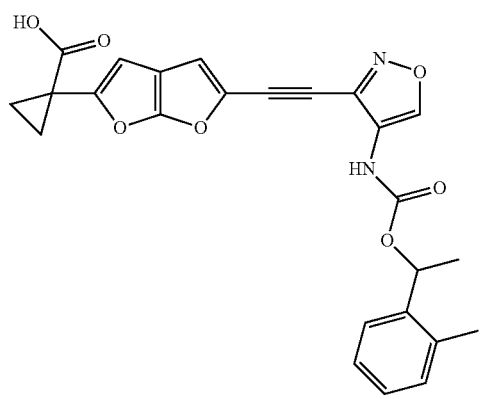 [SMILES: Cc1ccccc1C(C)OC(=O)Nc1conc1C#Cc1cc2cc(C3(C(=O)O)CC3)oc2o1]
TABLE 14-continued
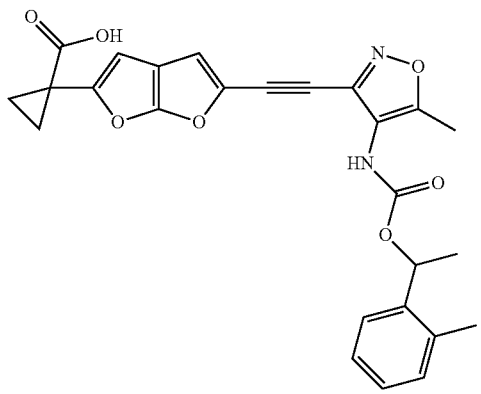
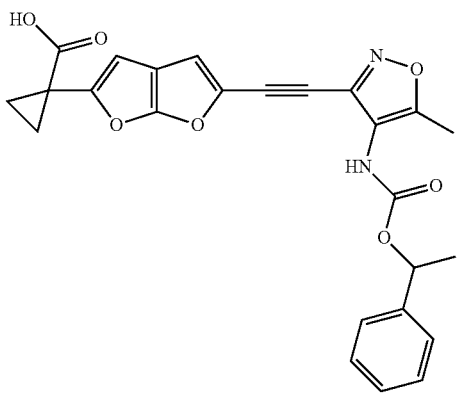 [SMILES: Cc1onc(C#Cc2cc3cc(C4(C(=O)O)CC4)oc3o2)c1NC(=O)OC(C)c1ccccc1]
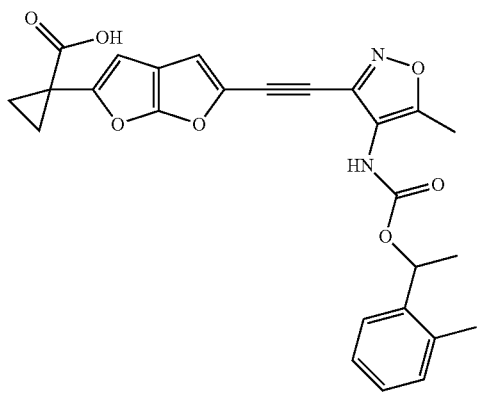 [SMILES: Cc1ccccc1C(C)OC(=O)Nc1c(C#Cc2cc3cc(C4(C(=O)O)CC4)oc3o2)noc1C]
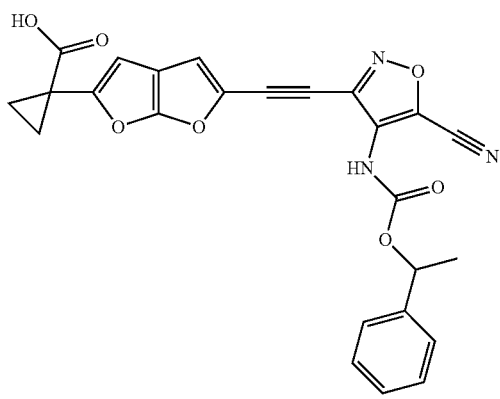

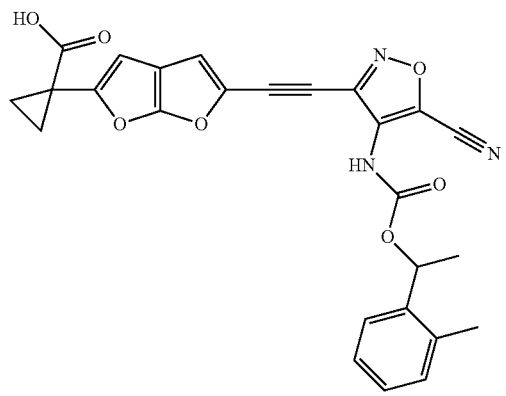 [SMILES: Cc1ccccc1C(C)OC(=O)Nc1c(C#Cc2cc3cc(C4(C(=O)O)CC4)oc3o2)noc1C#N]
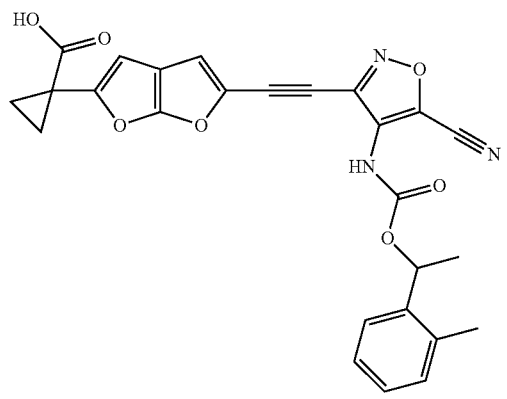 [SMILES: Cc1ccccc1C(C)OC(=O)Nc1c(C#Cc2cc3cc(C4(C(=O)O)CC4)oc3o2)noc1C#N]
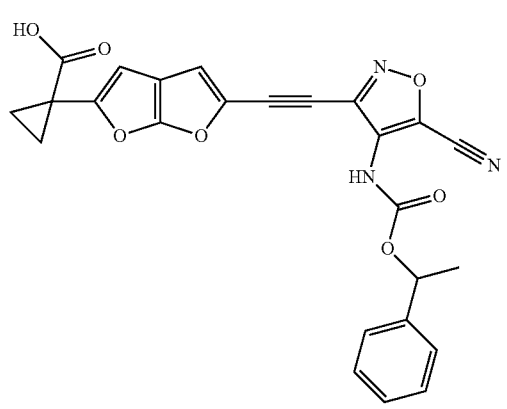 [SMILES: CC(OC(=O)Nc1c(C#Cc2cc3cc(C4(C(=O)O)CC4)oc3o2)noc1C#N)c1ccccc1]
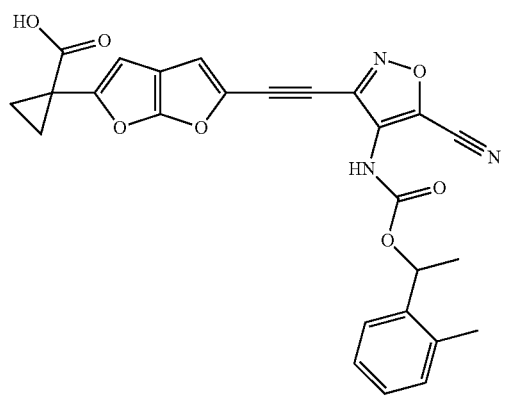 [SMILES: Cc1ccccc1C(C)OC(=O)Nc1c(C#Cc2cc3cc(C4(C(=O)O)CC4)oc3o2)noc1C#N]
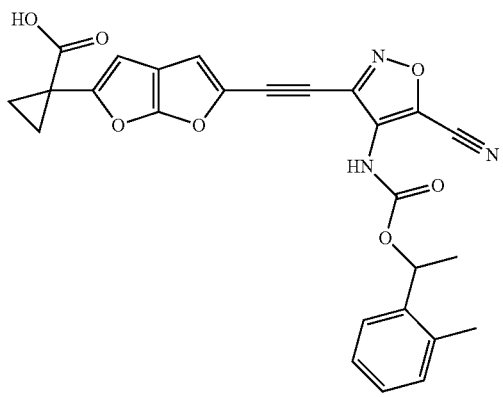 [SMILES: Cc1ccccc1C(C)OC(=O)Nc1c(C#Cc2cc3cc(C4(C(=O)O)CC4)oc3o2)noc1C#N]
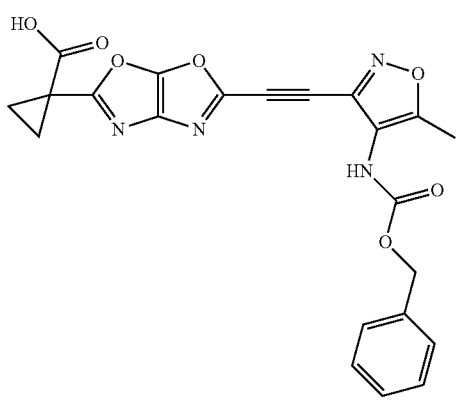 [SMILES: Cc1onc(C#Cc2nc3nc(C4(C(=O)O)CC4)oc3o2)c1NC(=O)OCc1ccccc1]
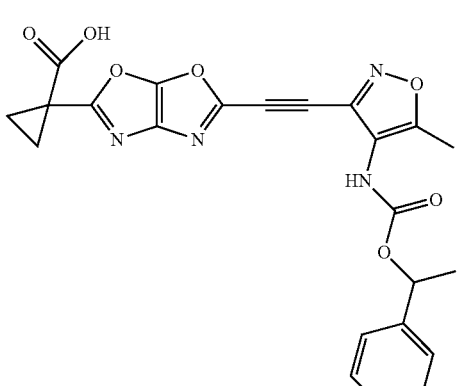
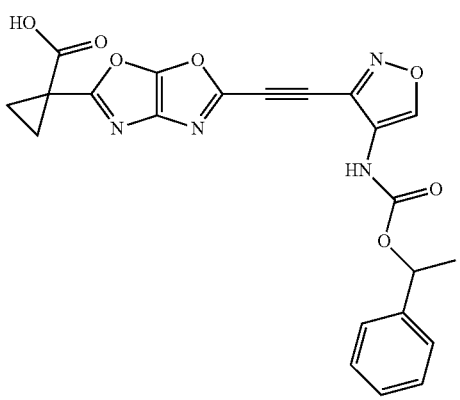

TABLE 14-continued
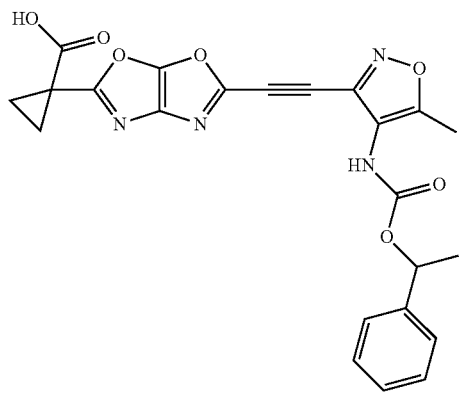
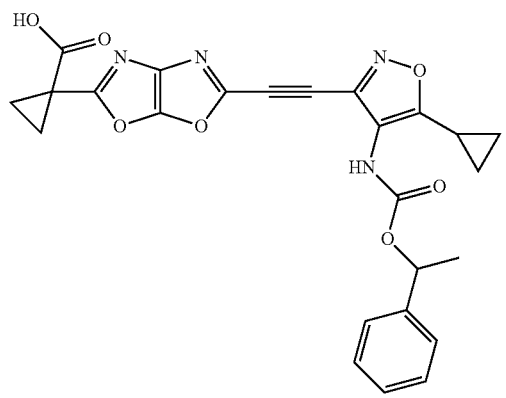 [SMILES: CC(OC(=O)Nc1c(C#Cc2nc3nc(C4(C(=O)O)CC4)oc3o2)noc1C1CC1)c1ccccc1]
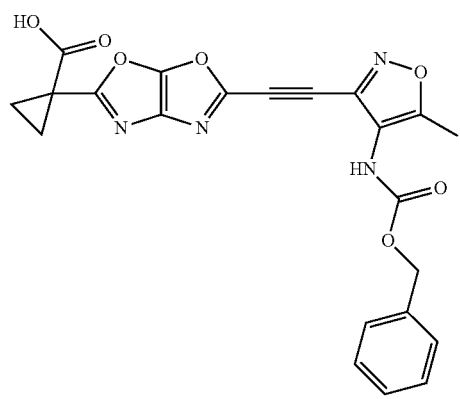 [SMILES: Cc1onc(C#Cc2nc3nc(C4(C(=O)O)CC4)oc3o2)c1NC(=O)OCc1ccccc1]
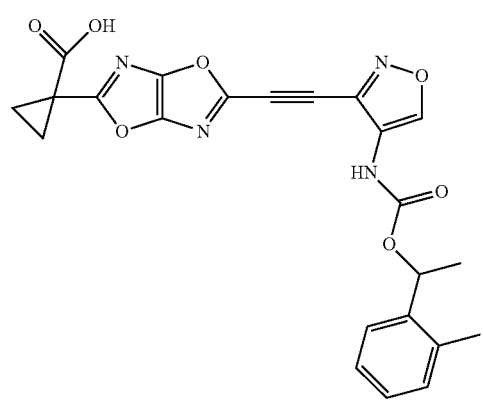
TABLE 14-continued
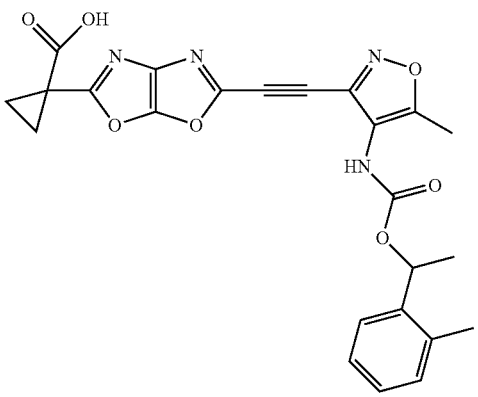
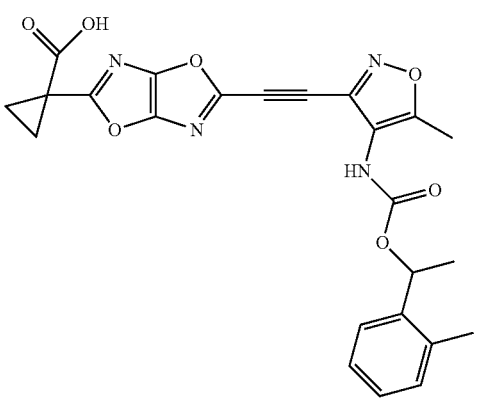
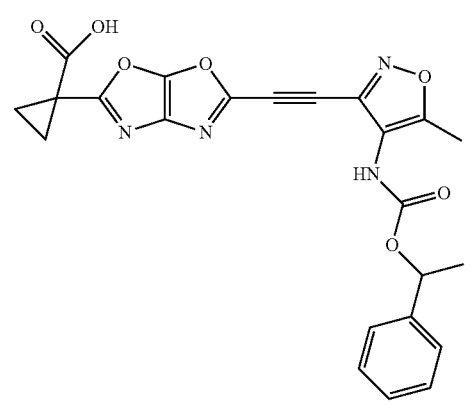 [SMILES: Cc1onc(C#Cc2nc3nc(C4(C(=O)O)CC4)oc3o2)c1NC(=O)OC(C)c1ccccc1]
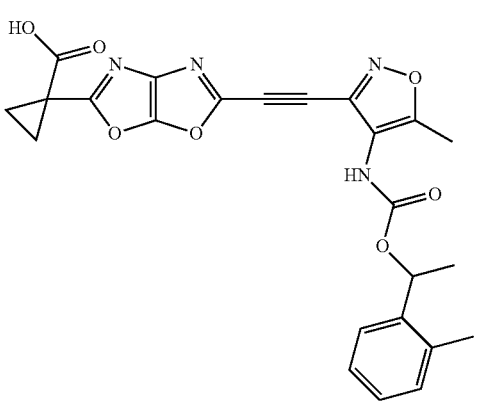 [SMILES: Cc1ccccc1C(C)OC(=O)Nc1c(C#Cc2nc3nc(C4(C(=O)O)CC4)oc3o2)noc1C]

TABLE 14-continued
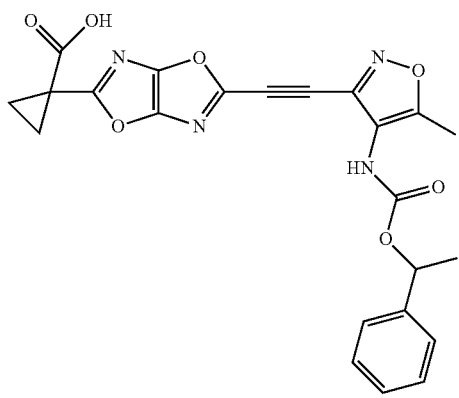 [SMILES: Cc1onc(C#Cc2nc3oc(C4(C(=O)O)CC4)nc3o2)c1NC(=O)OC(C)c1ccccc1]
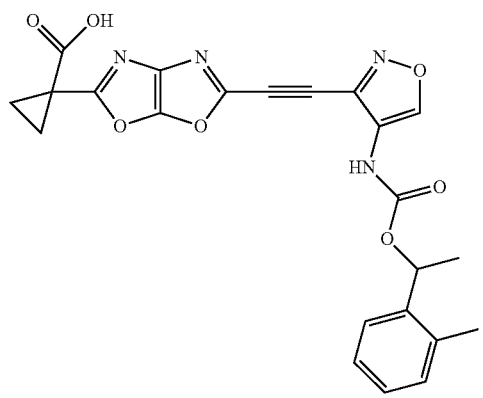 [SMILES: Cc1ccccc1C(C)OC(=O)Nc1conc1C#Cc1nc2nc(C3(C(=O)O)CC3)oc2o1]
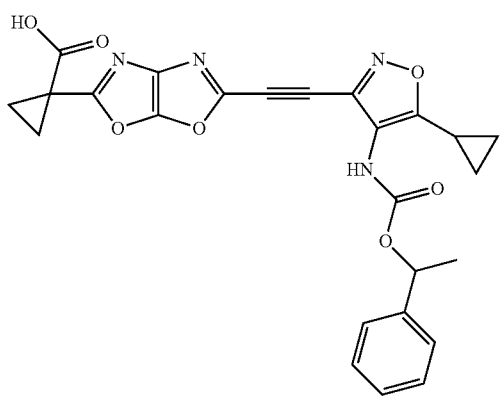 [SMILES: CC(OC(=O)Nc1c(C#Cc2nc3nc(C4(C(=O)O)CC4)oc3o2)noc1C1CC1)c1ccccc1]
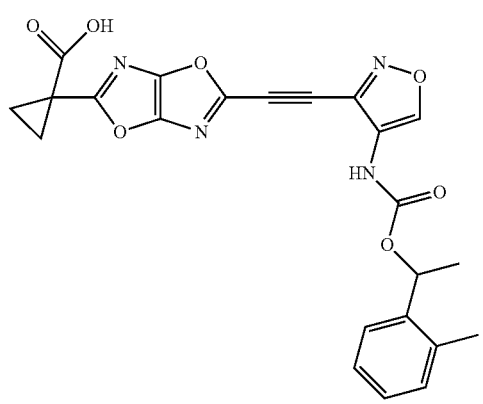
TABLE 14-continued
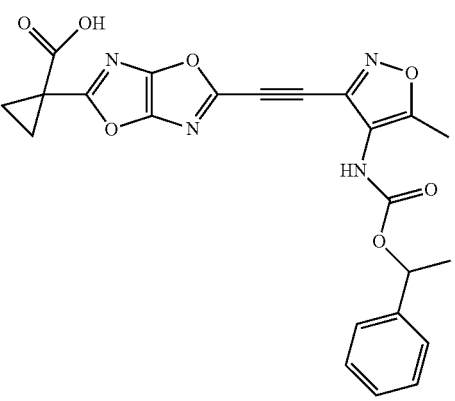 [SMILES: Cc1onc(C#Cc2nc3oc(C4(C(=O)O)CC4)nc3o2)c1NC(=O)OC(C)c1ccccc1]
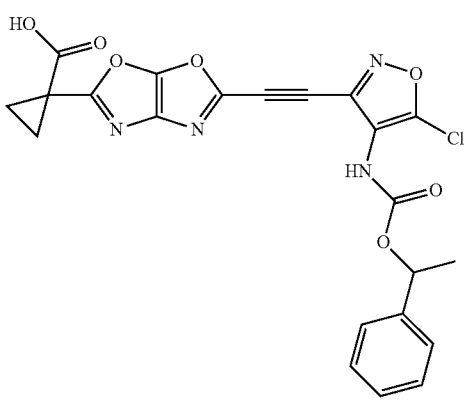
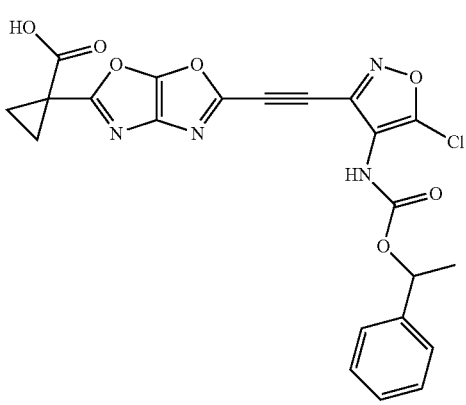
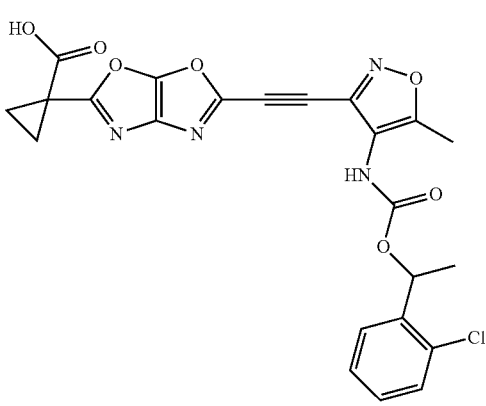 [SMILES: Cc1onc(C#Cc2nc3nc(C4(C(=O)O)CC4)oc3o2)c1NC(=O)OC(C)c1ccccc1Cl]

485
TABLE 14-continued
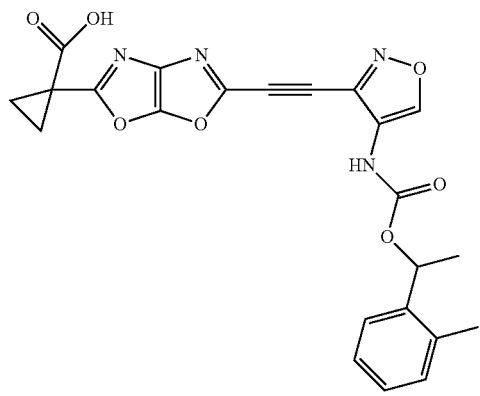
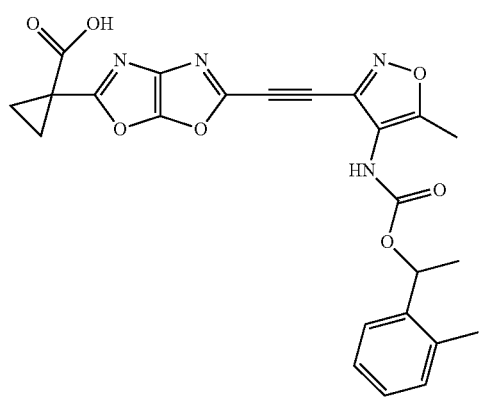 [SMILES: Cc1ccccc1C(C)OC(=O)Nc1c(C#Cc2nc3nc(C4(C(=O)O)CC4)oc3o2)noc1C]
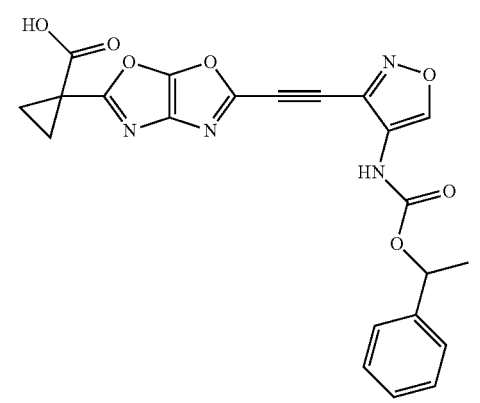 [SMILES: CC(OC(=O)Nc1conc1C#Cc1nc2nc(C3(C(=O)O)CC3)oc2o1)c1ccccc1]
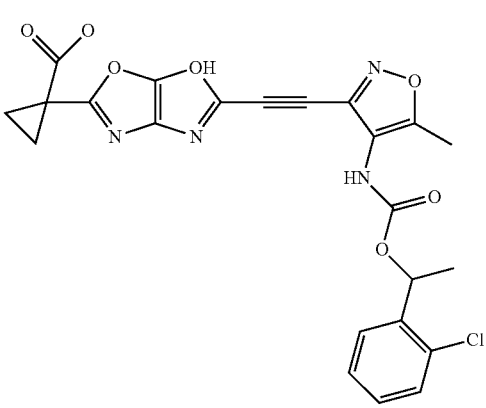 [SMILES: Cc1onc(C#Cc2nc3nc(C4(C(=O)O)CC4)oc3o2)c1NC(=O)OC(C)c1ccccc1Cl]
486
TABLE 14-continued
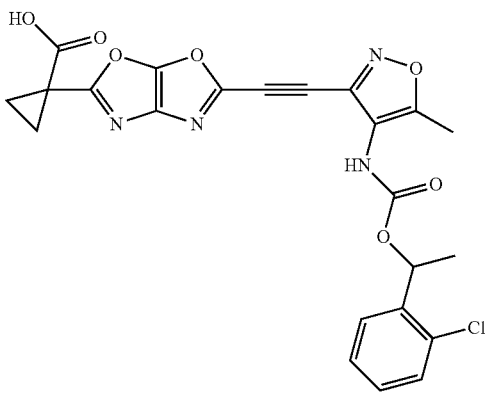 [SMILES: Cc1onc(C#Cc2nc3nc(C4(C(=O)O)CC4)oc3o2)c1NC(=O)OC(C)c1ccccc1Cl]
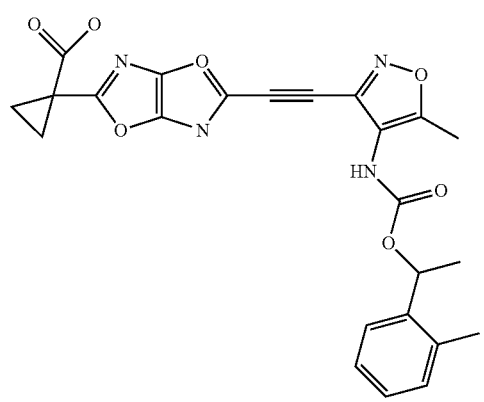
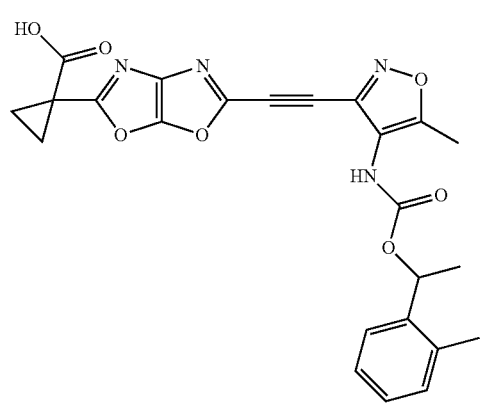 [SMILES: Cc1ccccc1C(C)OC(=O)Nc1c(C#Cc2nc3nc(C4(C(=O)O)CC4)oc3o2)noc1C]
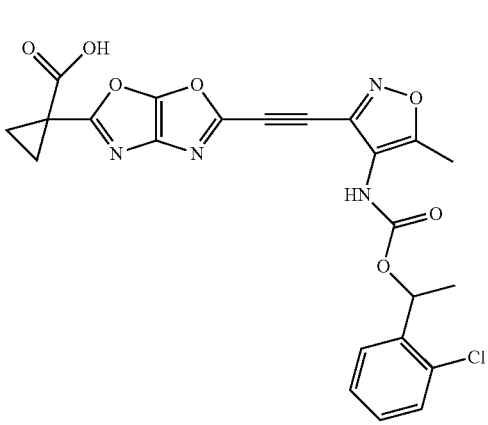 [SMILES: Cc1onc(C#Cc2nc3nc(C4(C(=O)O)CC4)oc3o2)c1NC(=O)OC(C)c1ccccc1Cl]

TABLE 14-continued
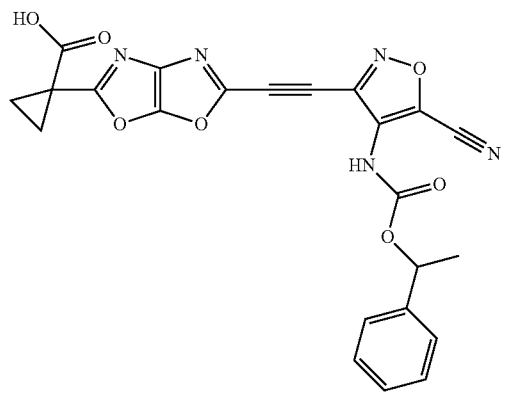 [SMILES: CC(OC(=O)Nc1c(C#Cc2nc3nc(C4(C(=O)O)CC4)oc3o2)noc1C#N)c1ccccc1]
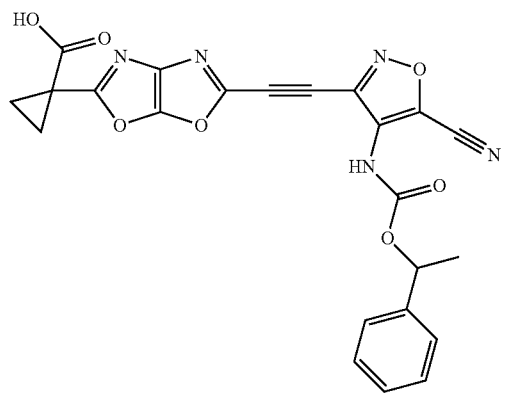 [SMILES: CC(OC(=O)Nc1c(C#Cc2nc3nc(C4(C(=O)O)CC4)oc3o2)noc1C#N)c1ccccc1]
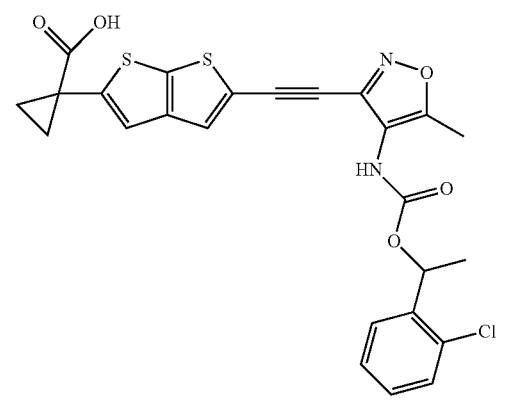 [SMILES: Cc1onc(C#Cc2cc3cc(C4(C(=O)O)CC4)sc3s2)c1NC(=O)OC(C)c1ccccc1Cl]
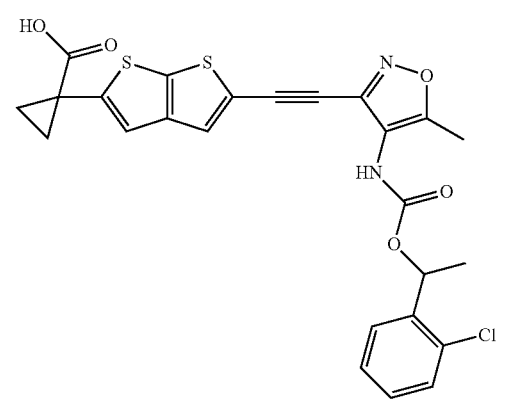
TABLE 14-continued
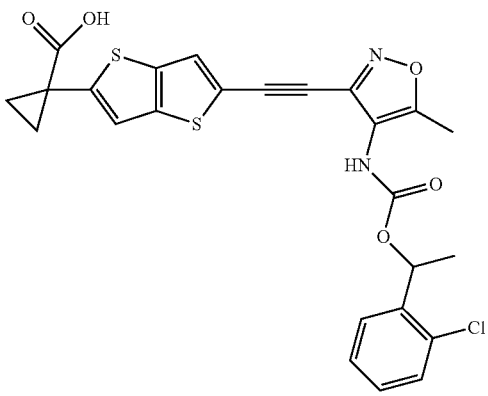 [SMILES: Cc1onc(C#Cc2cc3sc(C4(C(=O)O)CC4)cc3s2)c1NC(=O)OC(C)c1ccccc1Cl]
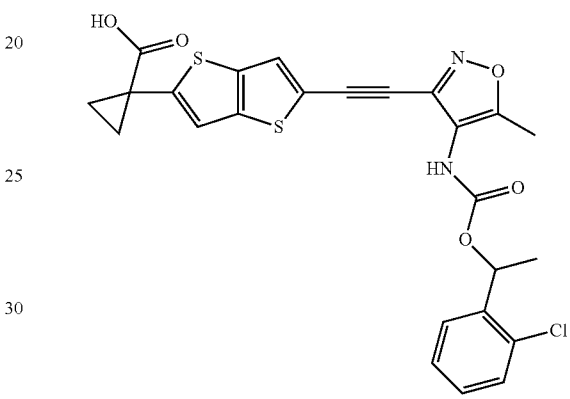
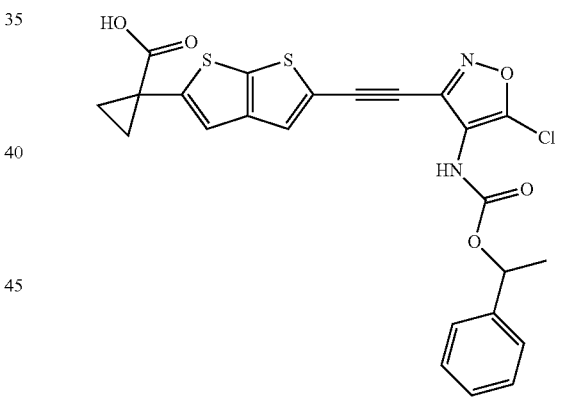
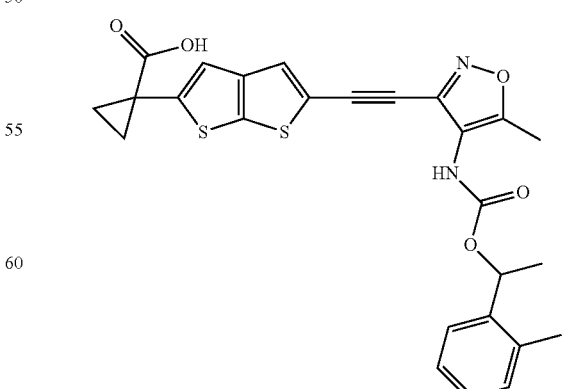

TABLE 14-continued
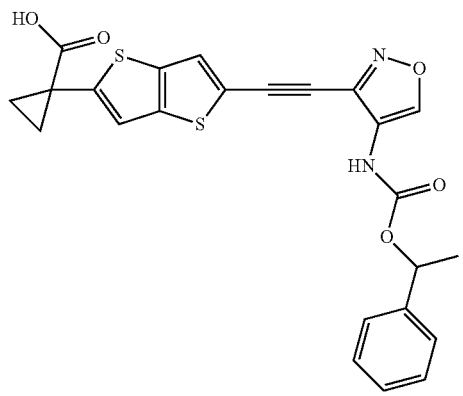
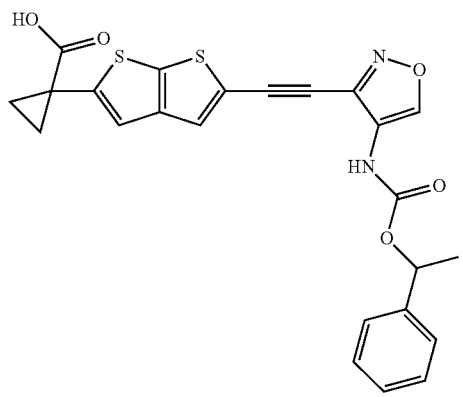 [SMILES: CC(OC(=O)Nc1conc1C#Cc1cc2cc(C3(C(=O)O)CC3)sc2s1)c1ccccc1]
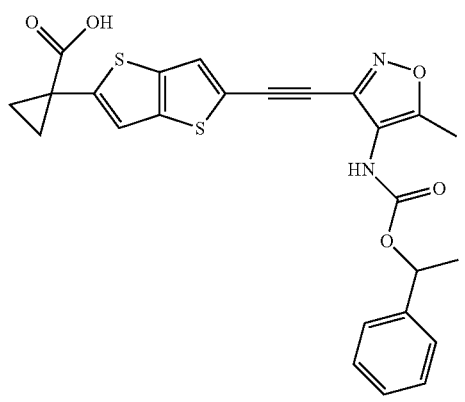 [SMILES: Cc1onc(C#Cc2cc3sc(C4(C(=O)O)CC4)cc3s2)c1NC(=O)OC(C)c1ccccc1]
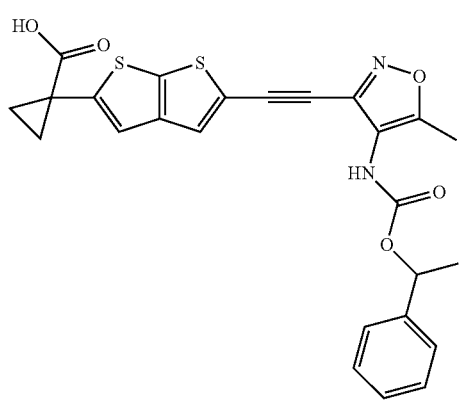
TABLE 14-continued
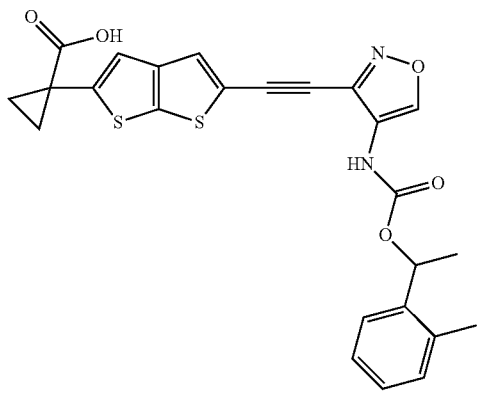
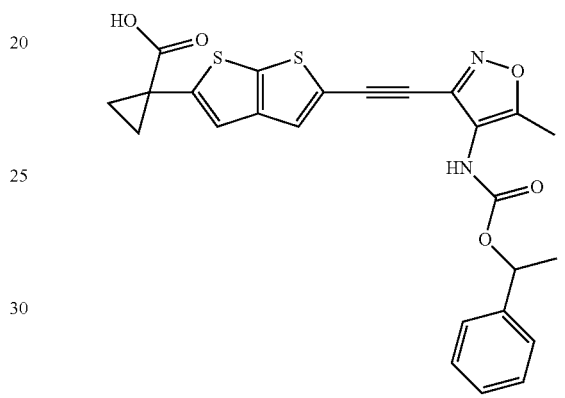

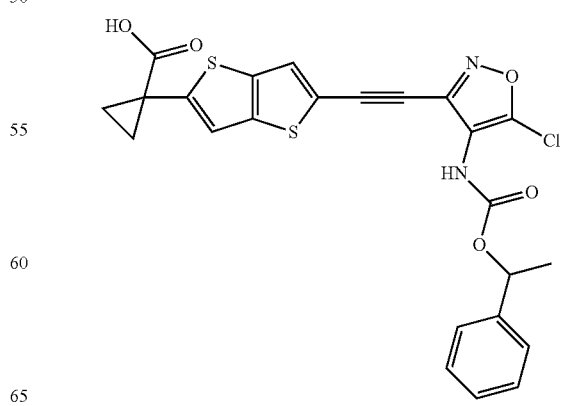

TABLE 14-continued
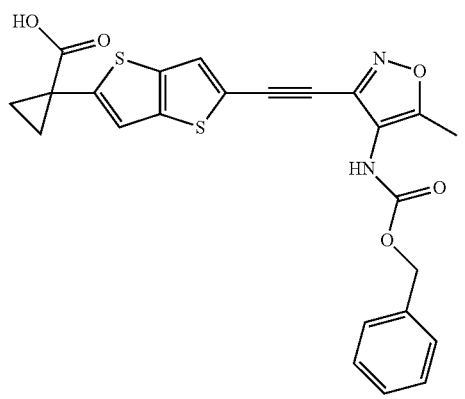 [SMILES: Cc1onc(C#Cc2cc3sc(C4(C(=O)O)CC4)cc3s2)c1NC(=O)OCc1ccccc1]
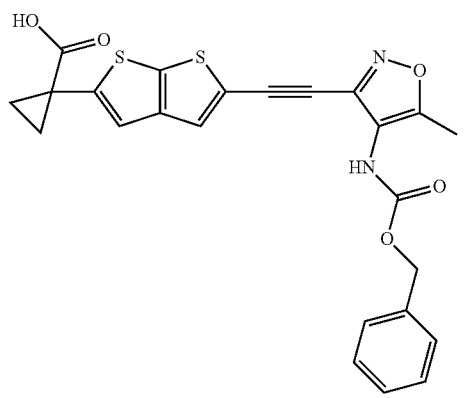
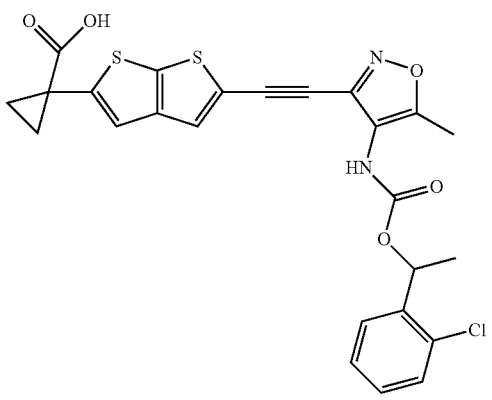
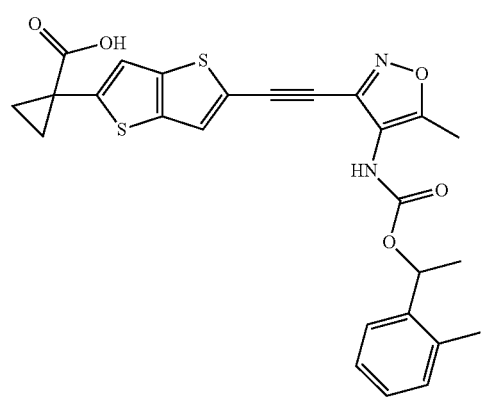
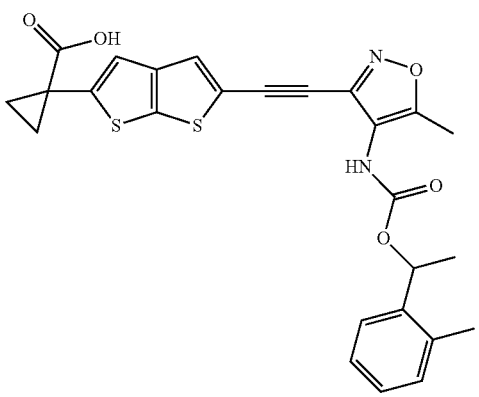
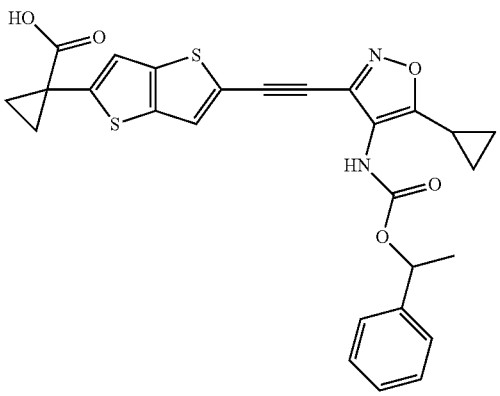 [SMILES: CC(OC(=O)Nc1c(C#Cc2cc3sc(C4(C(=O)O)CC4)cc3s2)noc1C1CC1)c1ccccc1]
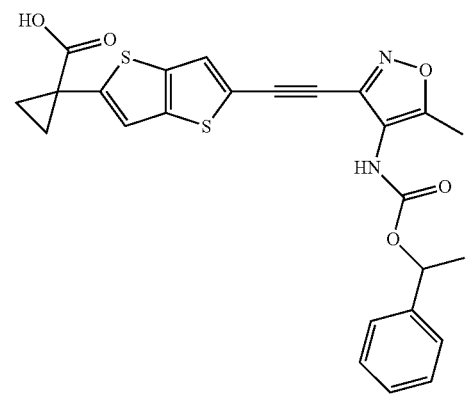 [SMILES: Cc1onc(C#Cc2cc3sc(C4(C(=O)O)CC4)cc3s2)c1NC(=O)OC(C)c1ccccc1]
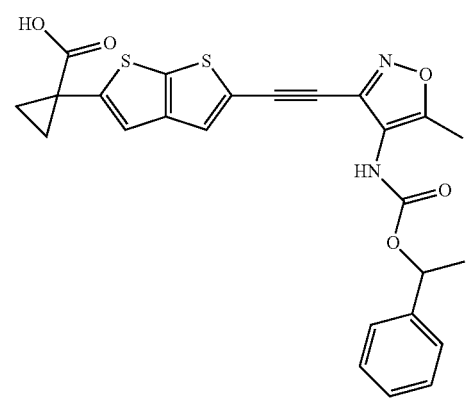 [SMILES: Cc1onc(C#Cc2cc3cc(C4(C(=O)O)CC4)sc3s2)c1NC(=O)OC(C)c1ccccc1]

TABLE 14-continued
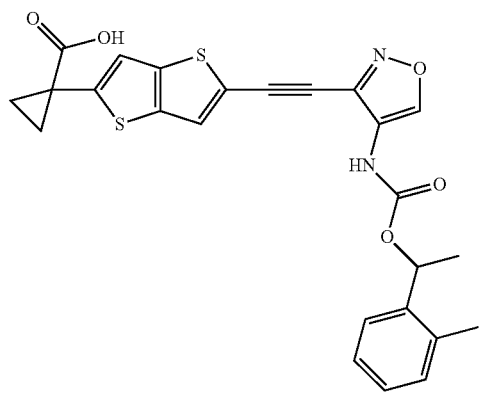 [SMILES: Cc1ccccc1C(C)OC(=O)Nc1conc1C#Cc1cc2sc(C3(C(=O)O)CC3)cc2s1]
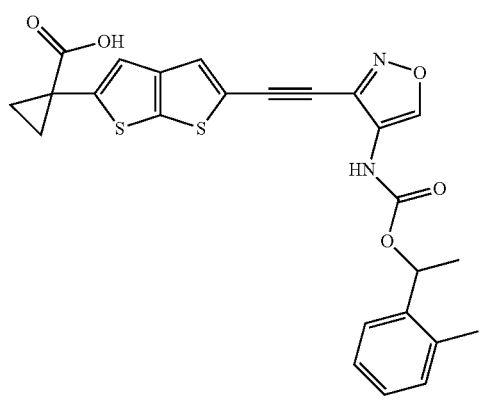 [SMILES: Cc1ccccc1C(C)OC(=O)Nc1conc1C#Cc1cc2cc(C3(C(=O)O)CC3)sc2s1]
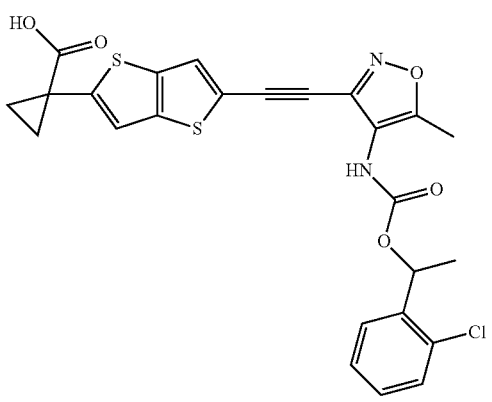 [SMILES: Cc1onc(C#Cc2cc3sc(C4(C(=O)O)CC4)cc3s2)c1NC(=O)OC(C)c1ccccc1Cl]
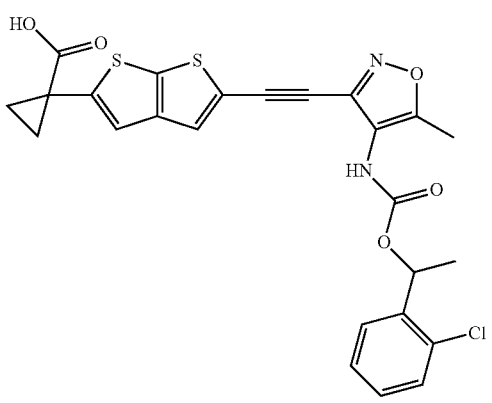 [SMILES: Cc1onc(C#Cc2cc3cc(C4(C(=O)O)CC4)sc3s2)c1NC(=O)OC(C)c1ccccc1Cl]
TABLE 14-continued
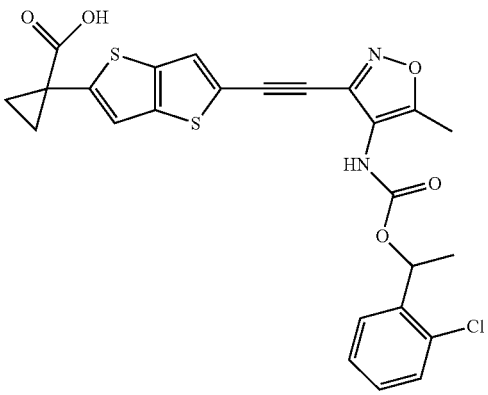 [SMILES: Cc1onc(C#Cc2cc3sc(C4(C(=O)O)CC4)cc3s2)c1NC(=O)OC(C)c1ccccc1Cl]
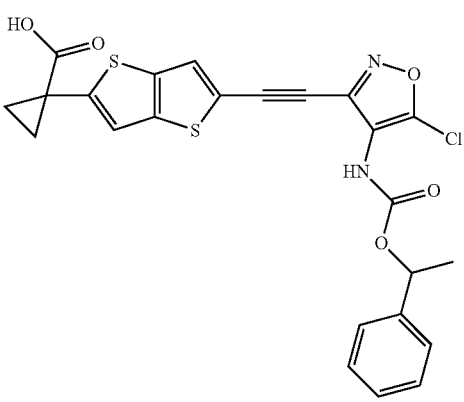 [SMILES: CC(OC(=O)Nc1c(C#Cc2cc3sc(C4(C(=O)O)CC4)cc3s2)noc1Cl)c1ccccc1]
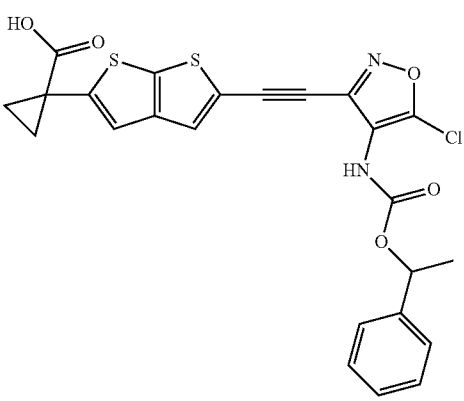 [SMILES: CC(OC(=O)Nc1c(C#Cc2cc3cc(C4(C(=O)O)CC4)sc3s2)noc1Cl)c1ccccc1]
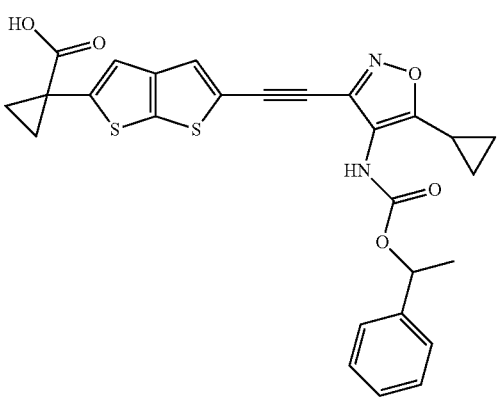

TABLE 14-continued
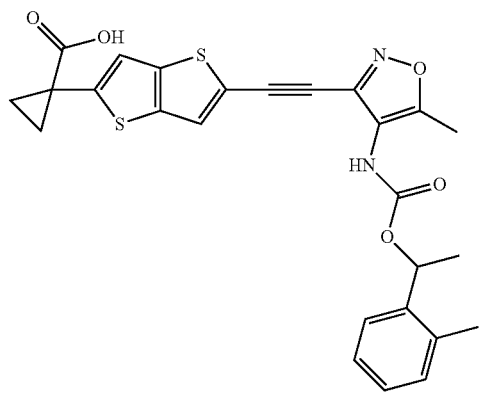 [SMILES: Cc1ccccc1C(C)OC(=O)Nc1c(C#Cc2cc3sc(C4(C(=O)O)CC4)cc3s2)noc1C]
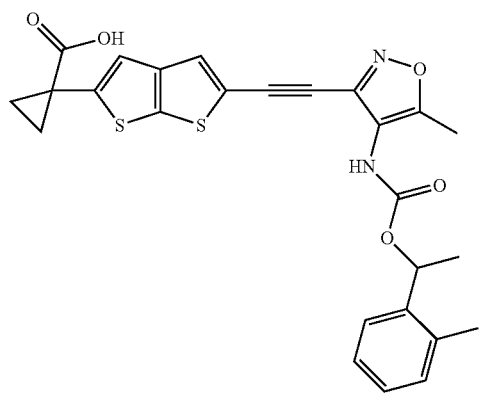
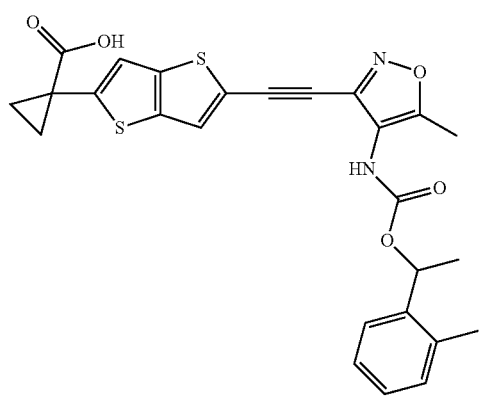 [SMILES: Cc1ccccc1C(C)OC(=O)Nc1c(C#Cc2cc3sc(C4(C(=O)O)CC4)cc3s2)noc1C]
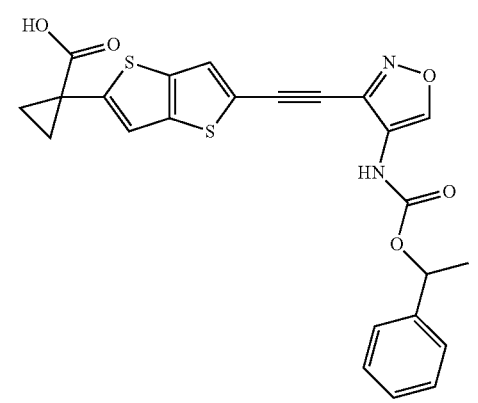 [SMILES: CC(OC(=O)Nc1conc1C#Cc1cc2sc(C3(C(=O)O)CC3)cc2s1)c1ccccc1]
TABLE 14-continued
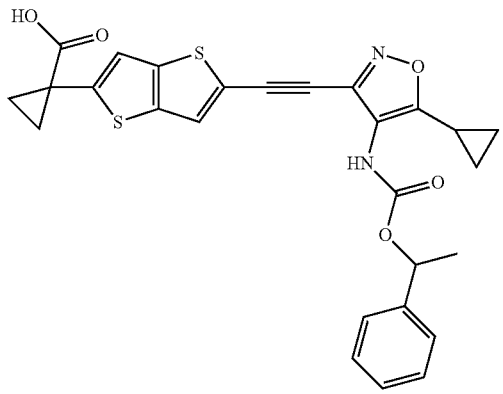 [SMILES: CC(OC(=O)Nc1c(C#Cc2cc3sc(C4(C(=O)O)CC4)cc3s2)noc1C1CC1)c1ccccc1]
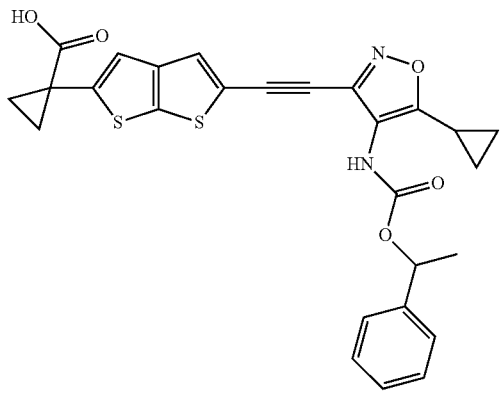
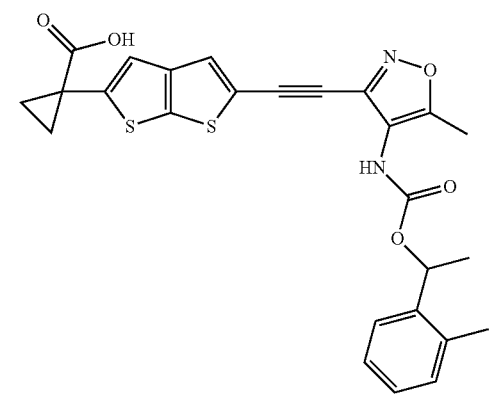
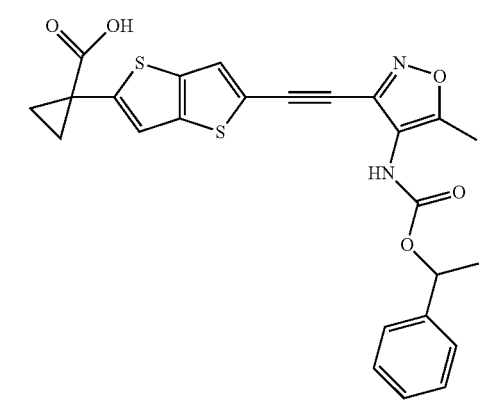 [SMILES: Cc1onc(C#Cc2cc3sc(C4(C(=O)O)CC4)cc3s2)c1NC(=O)OC(C)c1ccccc1]

TABLE 14-continued
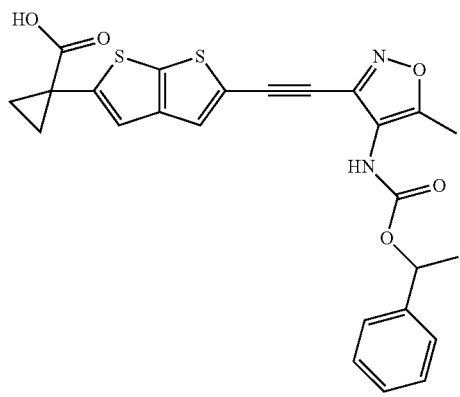 [SMILES: Cc1onc(C#Cc2cc3cc(C4(C(=O)O)CC4)sc3s2)c1NC(=O)OC(C)c1ccccc1]
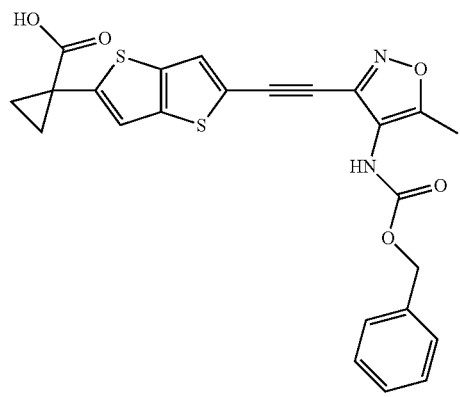 [SMILES: Cc1onc(C#Cc2cc3sc(C4(C(=O)O)CC4)cc3s2)c1NC(=O)OCc1ccccc1]
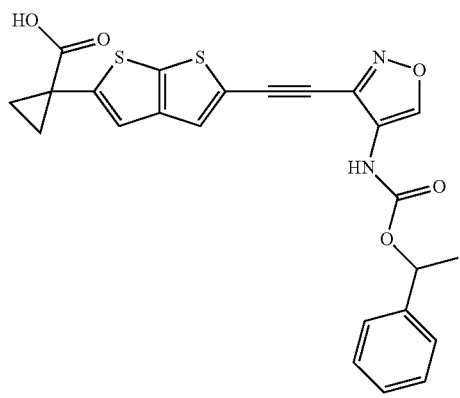 [SMILES: CC(OC(=O)Nc1conc1C#Cc1cc2cc(C3(C(=O)O)CC3)sc2s1)c1ccccc1]
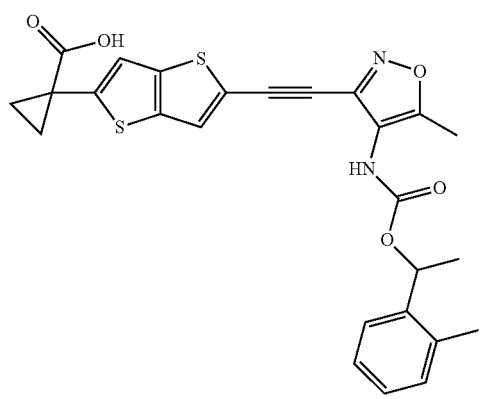 [SMILES: Cc1ccccc1C(C)OC(=O)Nc1c(C#Cc2cc3sc(C4(C(=O)O)CC4)cc3s2)noc1C]
TABLE 14-continued
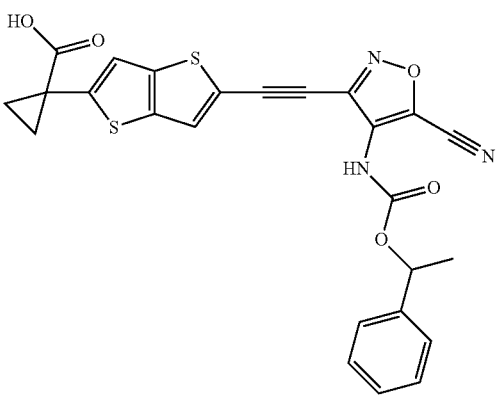 [SMILES: CC(OC(=O)Nc1c(C#Cc2cc3sc(C4(C(=O)O)CC4)cc3s2)noc1C#N)c1ccccc1]
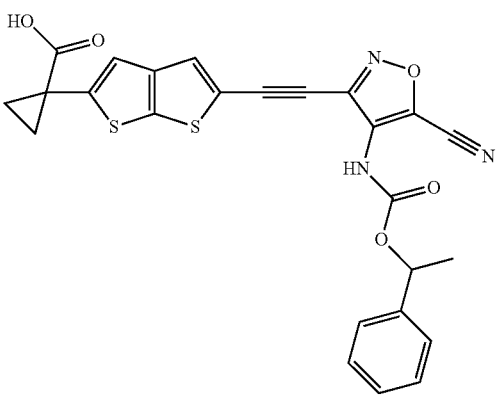
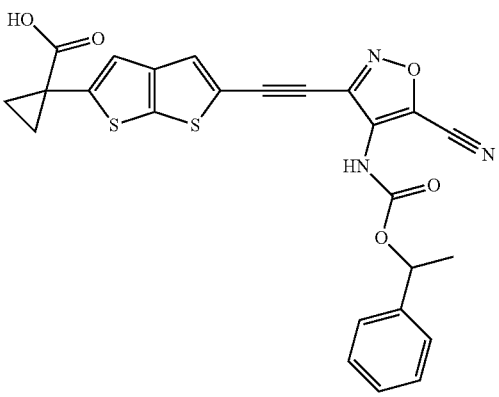
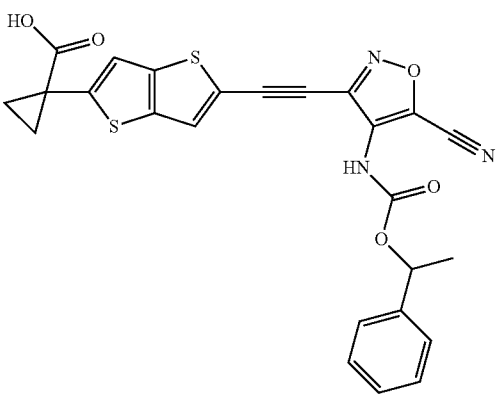 [SMILES: CC(OC(=O)Nc1c(C#Cc2cc3sc(C4(C(=O)O)CC4)cc3s2)noc1C#N)c1ccccc1]

499
TABLE 14-continued
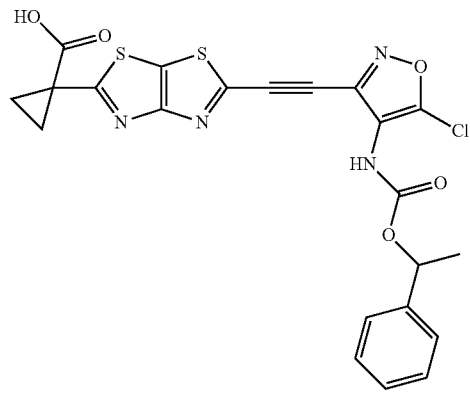 [SMILES: CC(OC(=O)Nc1c(C#Cc2nc3nc(C4(C(=O)O)CC4)sc3s2)noc1Cl)c1ccccc1]
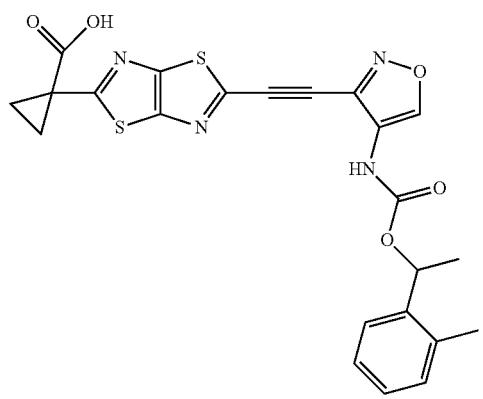 [SMILES: Cc1ccccc1C(C)OC(=O)Nc1conc1C#Cc1nc2sc(C3(C(=O)O)CC3)nc2s1]
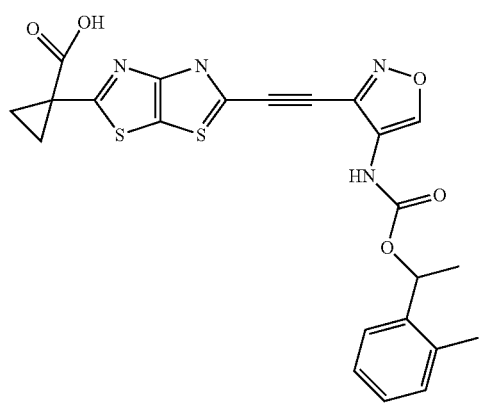
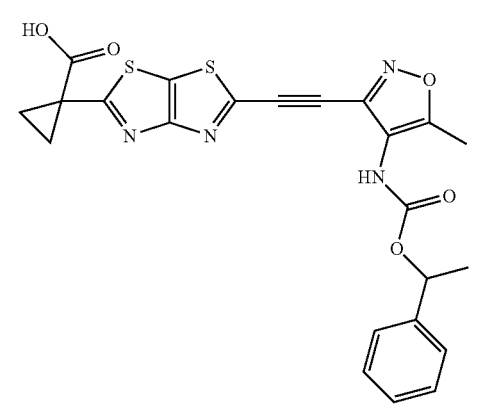 [SMILES: Cc1onc(C#Cc2nc3nc(C4(C(=O)O)CC4)sc3s2)c1NC(=O)OC(C)c1ccccc1]
500
TABLE 14-continued
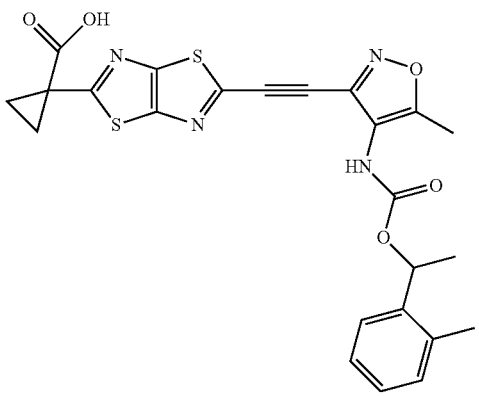 [SMILES: Cc1ccccc1C(C)OC(=O)Nc1c(C#Cc2nc3sc(C4(C(=O)O)CC4)nc3s2)noc1C]
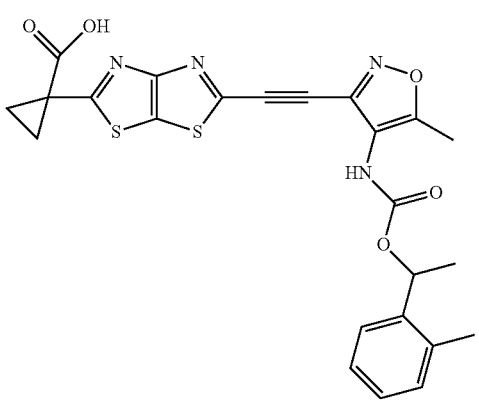
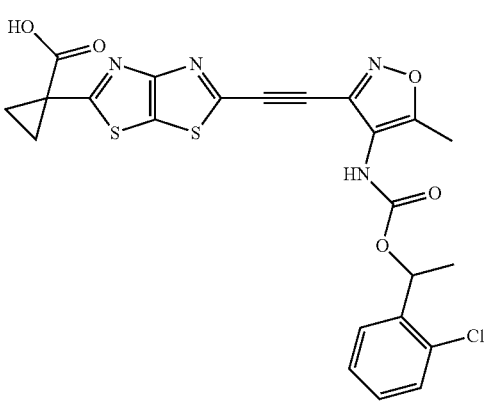 [SMILES: Cc1onc(C#Cc2nc3nc(C4(C(=O)O)CC4)sc3s2)c1NC(=O)OC(C)c1ccccc1Cl]
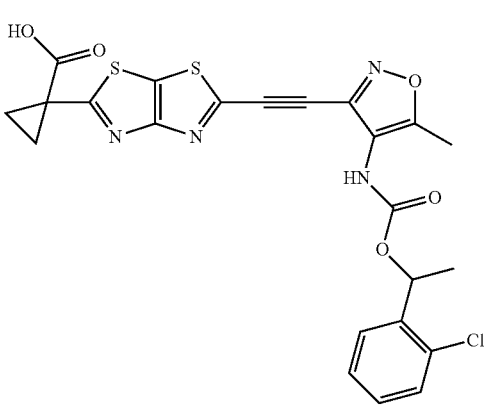

TABLE 14-continued
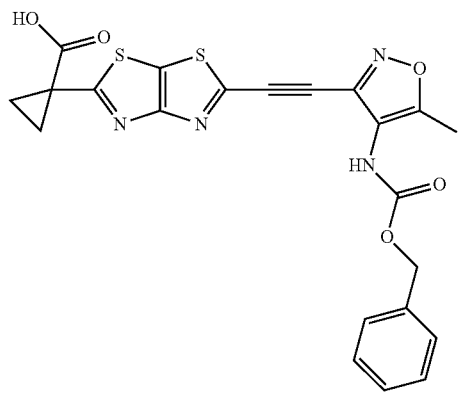
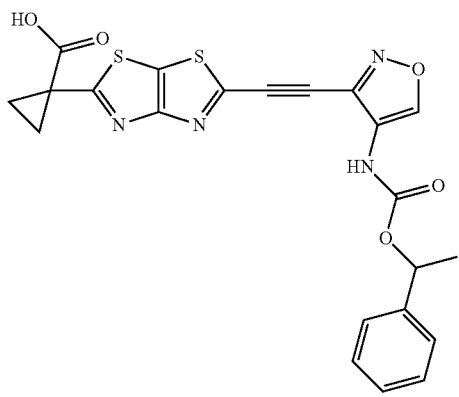
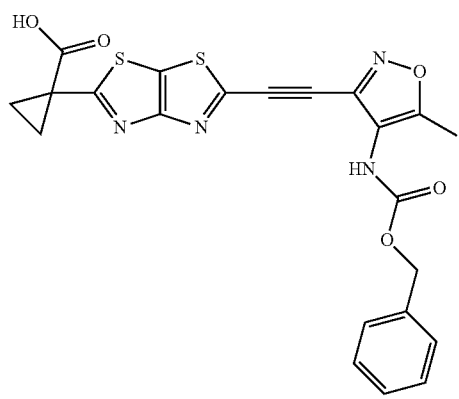
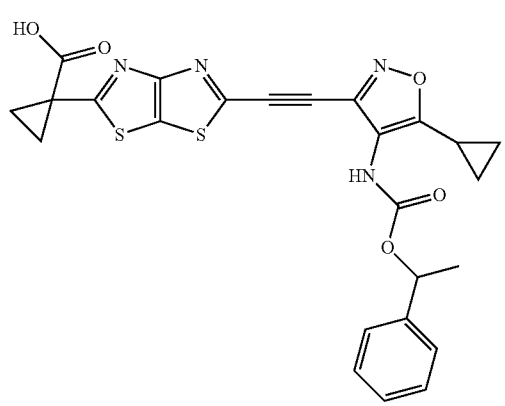 [SMILES: CC(OC(=O)Nc1c(C#Cc2nc3nc(C4(C(=O)O)CC4)sc3s2)noc1C1CC1)c1ccccc1]
TABLE 14-continued
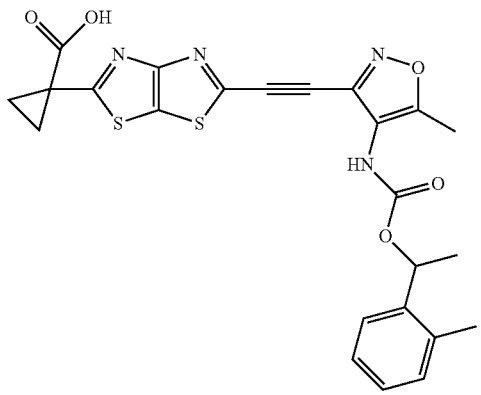
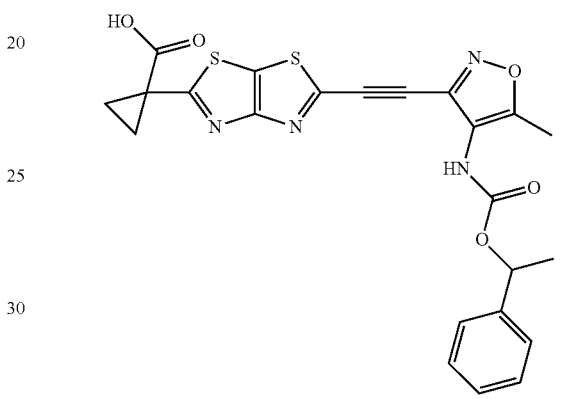
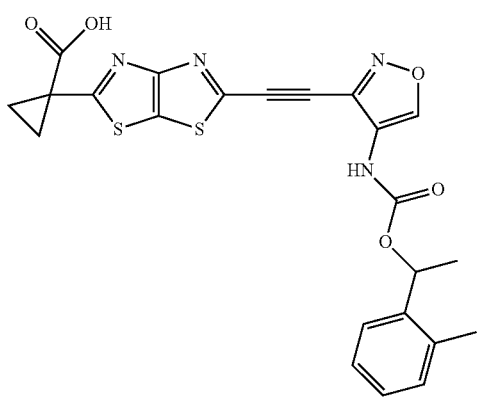 [SMILES: Cc1ccccc1C(C)OC(=O)Nc1conc1C#Cc1nc2nc(C3(C(=O)O)CC3)sc2s1]
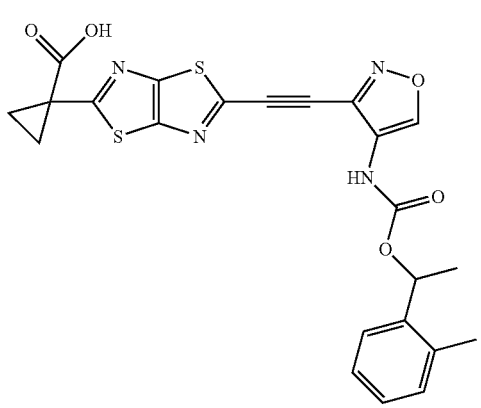

TABLE 14-continued
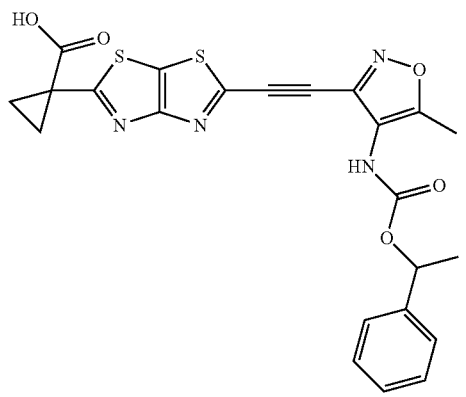
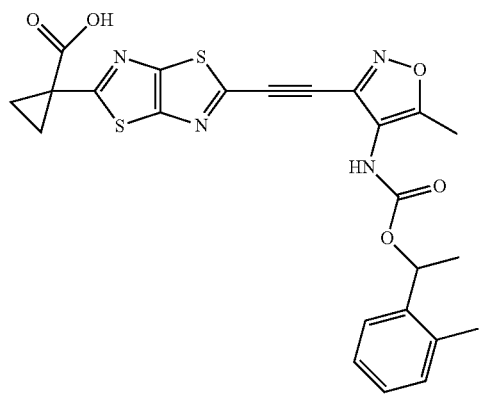 [SMILES: Cc1ccccc1C(C)OC(=O)Nc1c(C#Cc2nc3sc(C4(C(=O)O)CC4)nc3s2)noc1C]
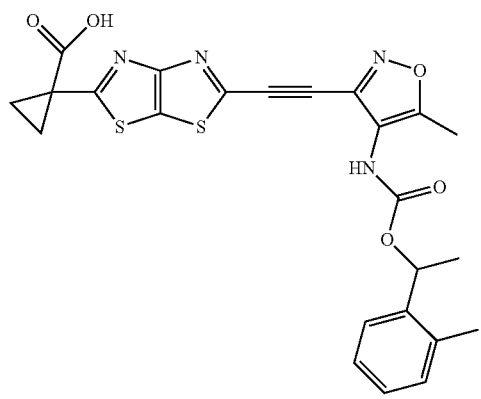 [SMILES: Cc1ccccc1C(C)OC(=O)Nc1c(C#Cc2nc3nc(C4(C(=O)O)CC4)sc3s2)noc1C]
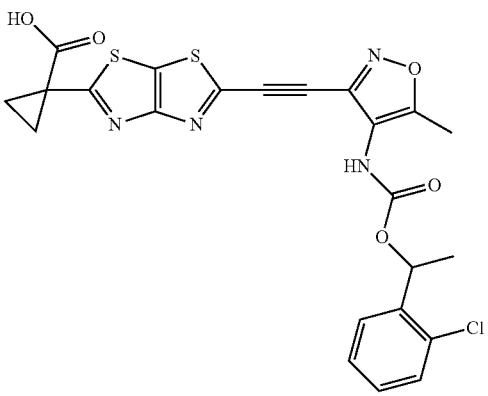
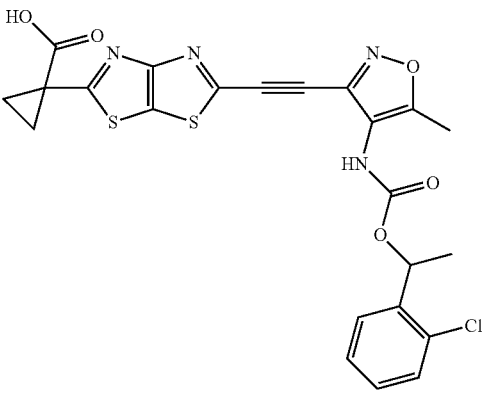
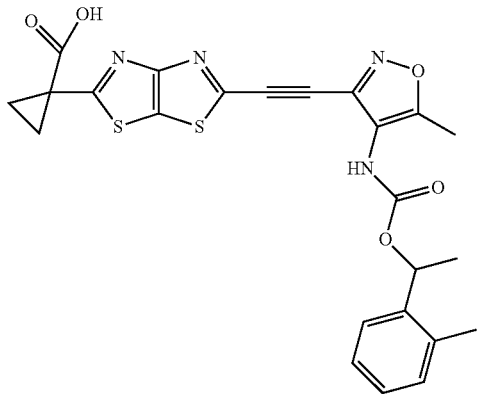 [SMILES: Cc1ccccc1C(C)OC(=O)Nc1c(C#Cc2nc3nc(C4(C(=O)O)CC4)sc3s2)noc1C]
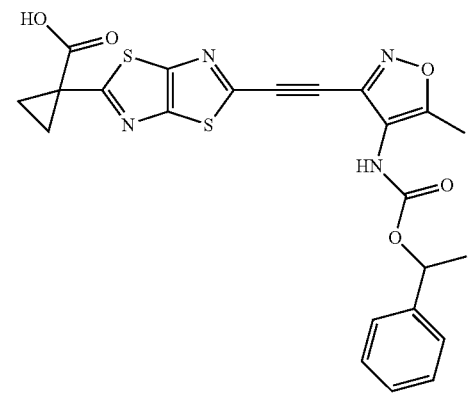 [SMILES: Cc1onc(C#Cc2nc3sc(C4(C(=O)O)CC4)nc3s2)c1NC(=O)OC(C)c1ccccc1]
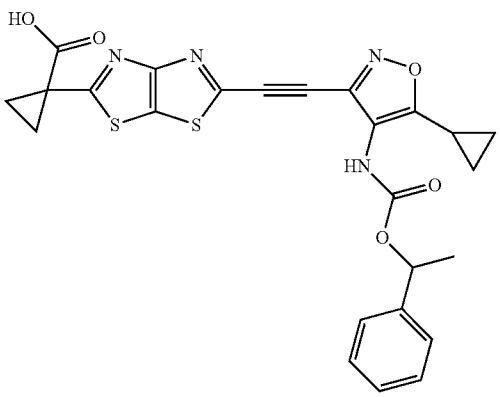 [SMILES: CC(OC(=O)Nc1c(C#Cc2nc3nc(C4(C(=O)O)CC4)sc3s2)noc1C1CC1)c1ccccc1]

TABLE 14-continued
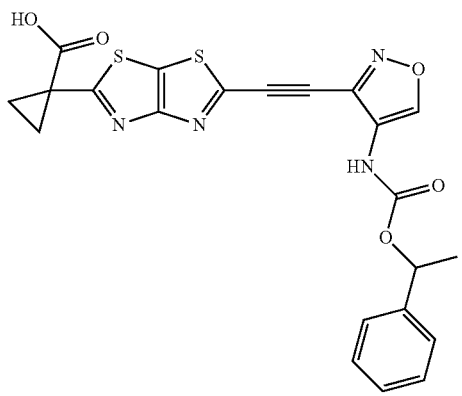
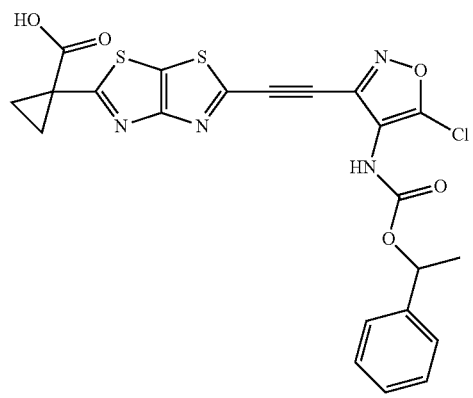
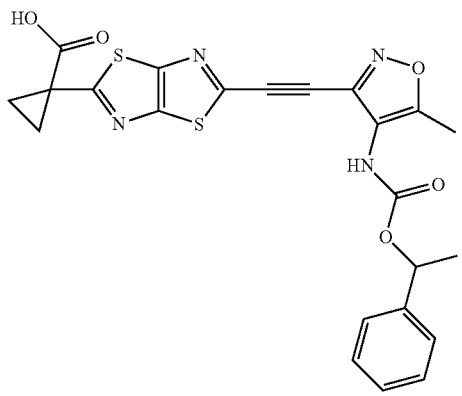
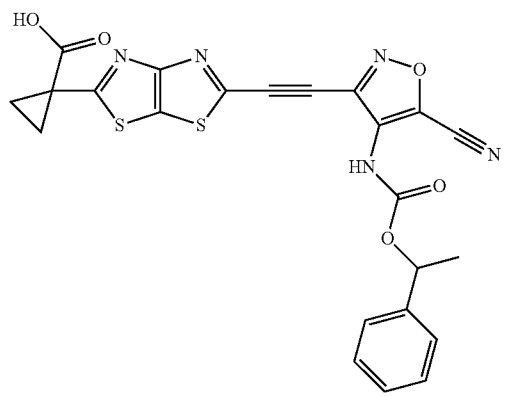 [SMILES: CC(OC(=O)Nc1c(C#Cc2nc3nc(C4(C(=O)O)CC4)sc3s2)noc1C#N)c1ccccc1]
TABLE 14-continued
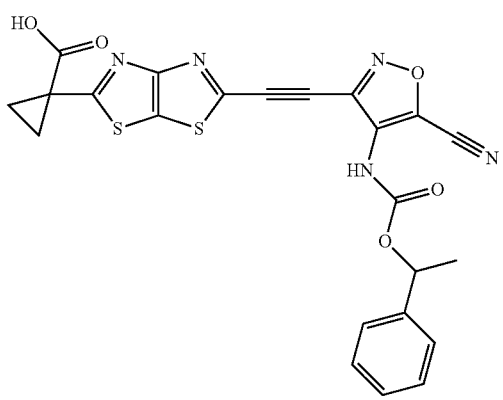
In some embodiments, compounds of Formula (I) are selected from the following compounds as listed in Table 15.
TABLE 15
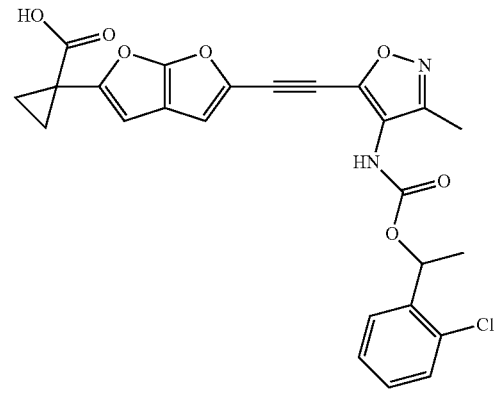 [SMILES: Cc1noc(C#Cc2cc3cc(C4(C(=O)O)CC4)oc3o2)c1NC(=O)OC(C)c1ccccc1Cl]
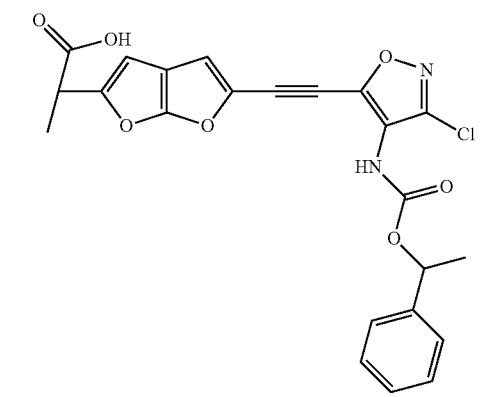 [SMILES: CC(OC(=O)Nc1c(Cl)noc1C#Cc1cc2cc(C(C)C(=O)O)oc2o1)c1ccccc1]

TABLE 15-continued
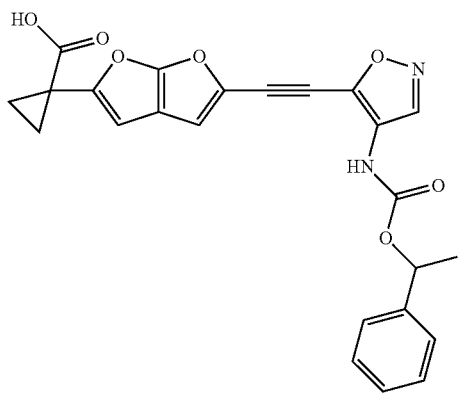 [SMILES: CC(OC(=O)Nc1cnoc1C#Cc1cc2cc(C3(C(=O)O)CC3)oc2o1)c1ccccc1]
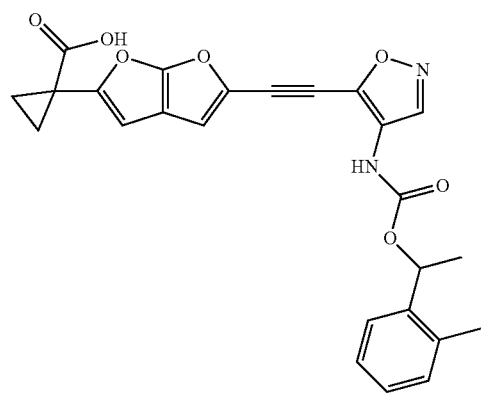
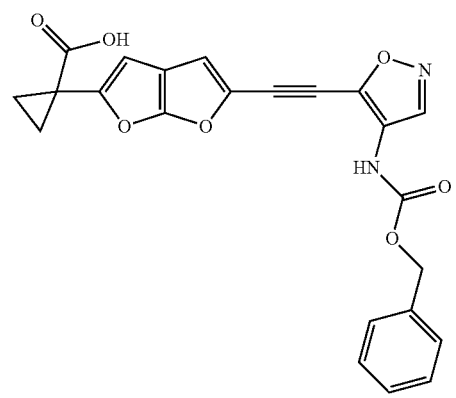 [SMILES: O=C(Nc1cnoc1C#Cc1cc2cc(C3(C(=O)O)CC3)oc2o1)OCc1ccccc1]
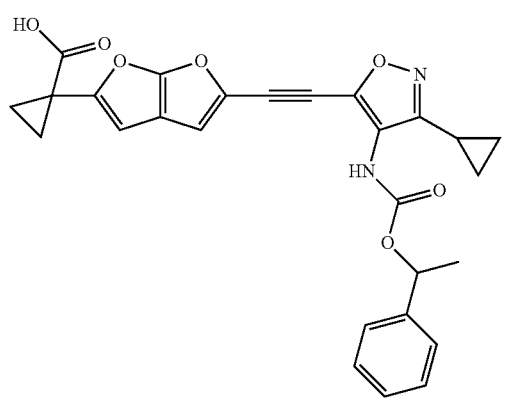
TABLE 15-continued
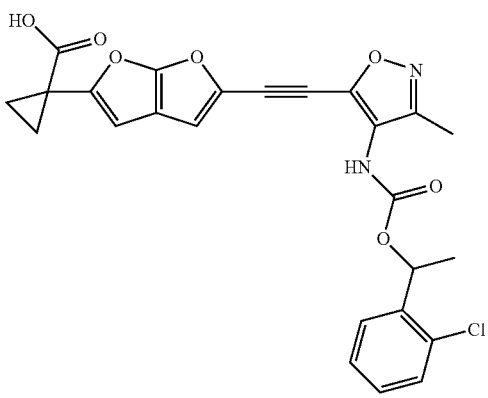 [SMILES: Cc1noc(C#Cc2cc3cc(C4(C(=O)O)CC4)oc3o2)c1NC(=O)OC(C)c1ccccc1Cl]
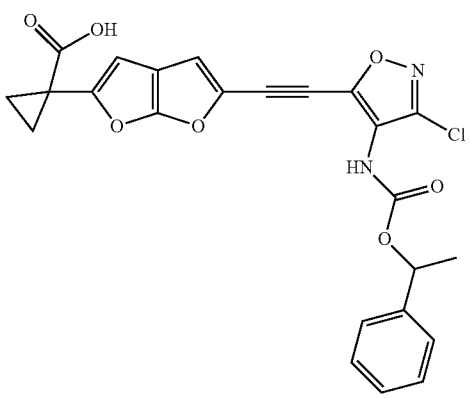 [SMILES: CC(OC(=O)Nc1c(Cl)noc1C#Cc1cc2cc(C3(C(=O)O)CC3)oc2o1)c1ccccc1]
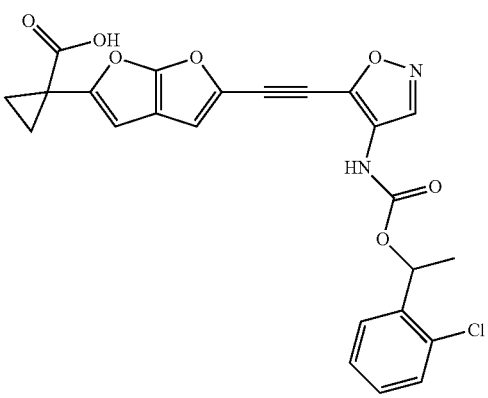 [SMILES: CC(OC(=O)Nc1cnoc1C#Cc1cc2cc(C3(C(=O)O)CC3)oc2o1)c1ccccc1Cl]
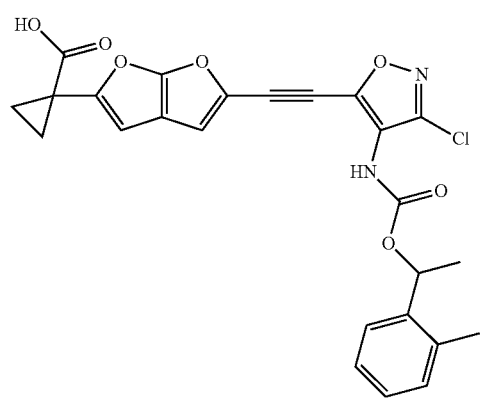 [SMILES: Cc1ccccc1C(C)OC(=O)Nc1c(Cl)noc1C#Cc1cc2cc(C3(C(=O)O)CC3)oc2o1]

TABLE 15-continued
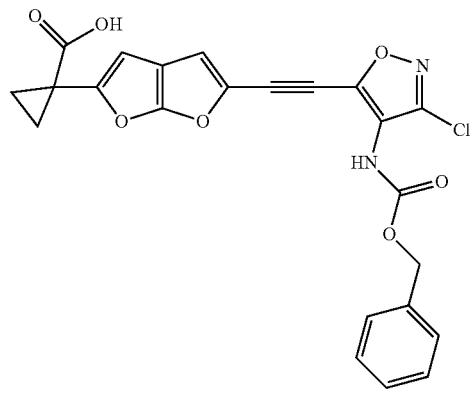 [SMILES: O=C(Nc1c(Cl)noc1C#Cc1cc2cc(C3(C(=O)O)CC3)oc2o1)OCc1ccccc1]
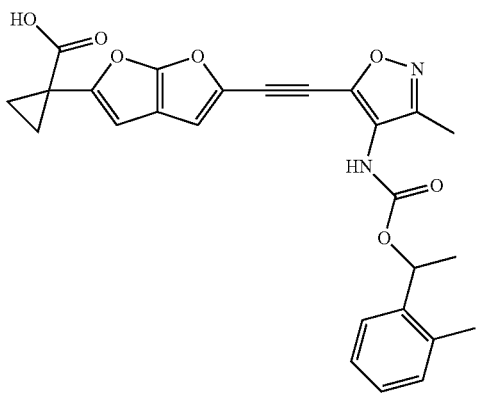 [SMILES: Cc1ccccc1C(C)OC(=O)Nc1c(C)noc1C#Cc1cc2cc(C3(C(=O)O)CC3)oc2o1]
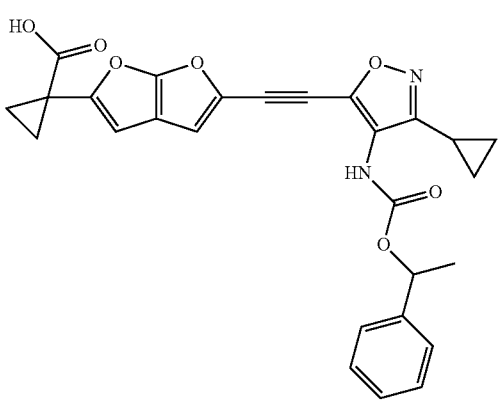
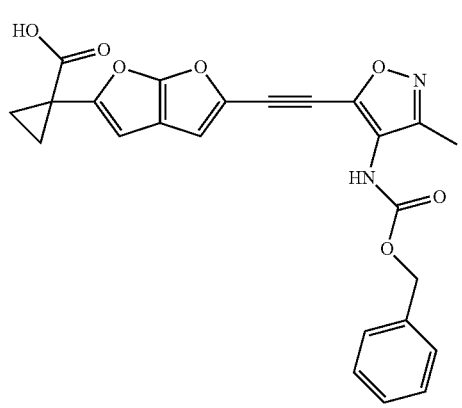 [SMILES: Cc1noc(C#Cc2cc3cc(C4(C(=O)O)CC4)oc3o2)c1NC(=O)OCc1ccccc1]
TABLE 15-continued
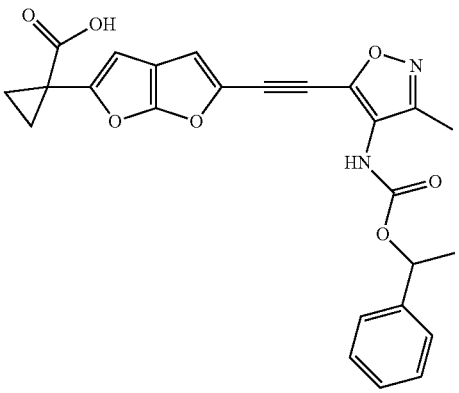 [SMILES: Cc1noc(C#Cc2cc3cc(C4(C(=O)O)CC4)oc3o2)c1NC(=O)OC(C)c1ccccc1]
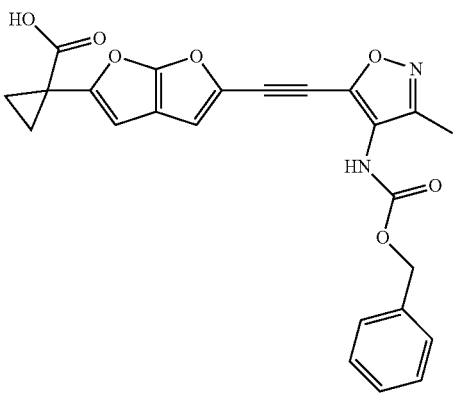 [SMILES: Cc1noc(C#Cc2cc3cc(C4(C(=O)O)CC4)oc3o2)c1NC(=O)OCc1ccccc1]
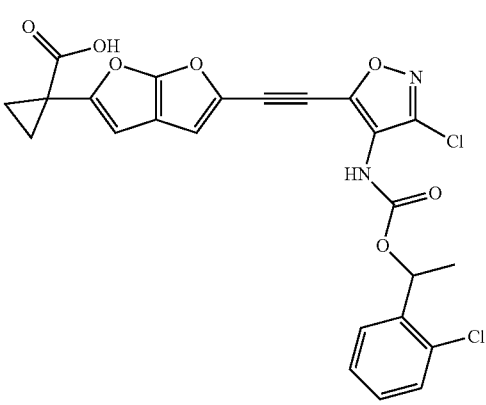
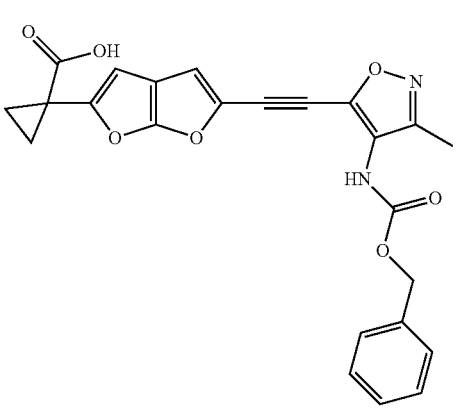 [SMILES: Cc1noc(C#Cc2cc3cc(C4(C(=O)O)CC4)oc3o2)c1NC(=O)OCc1ccccc1]

TABLE 15-continued
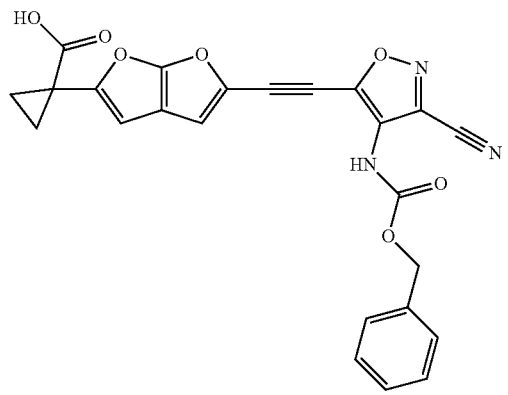 [SMILES: N#Cc1noc(C#Cc2cc3cc(C4(C(=O)O)CC4)oc3o2)c1NC(=O)OCc1ccccc1]
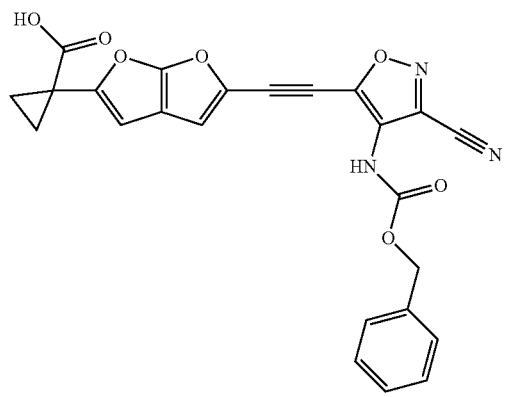 [SMILES: N#Cc1noc(C#Cc2cc3cc(C4(C(=O)O)CC4)oc3o2)c1NC(=O)OCc1ccccc1]
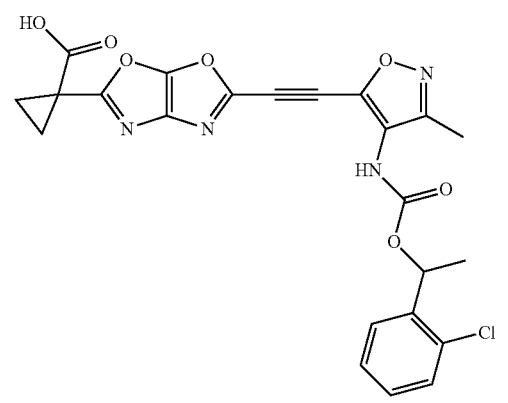
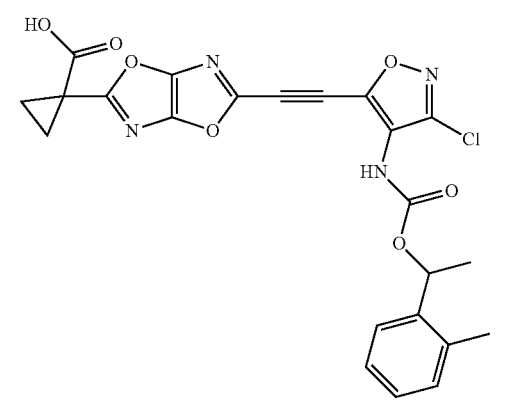 [SMILES: Cc1ccccc1C(C)OC(=O)Nc1c(Cl)noc1C#Cc1nc2oc(C3(C(=O)O)CC3)nc2o1]
TABLE 15-continued
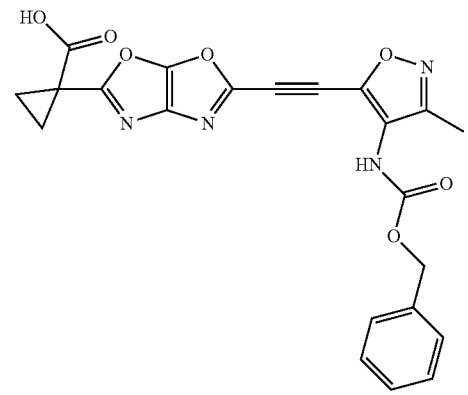
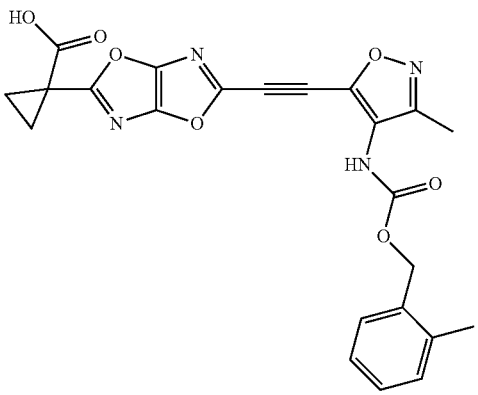 [SMILES: Cc1ccccc1COC(=O)Nc1c(C)noc1C#Cc1nc2oc(C3(C(=O)O)CC3)nc2o1]
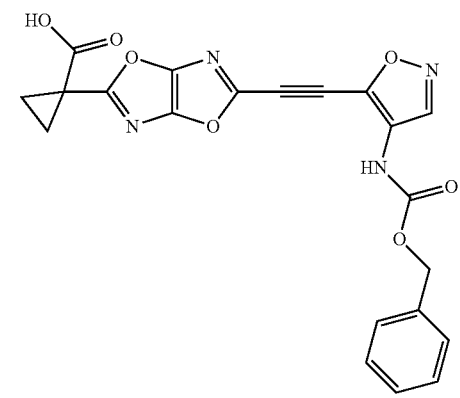
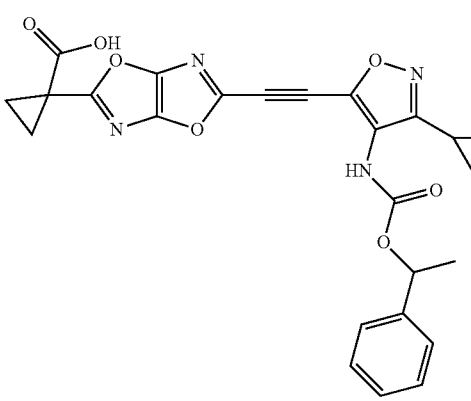

TABLE 15-continued
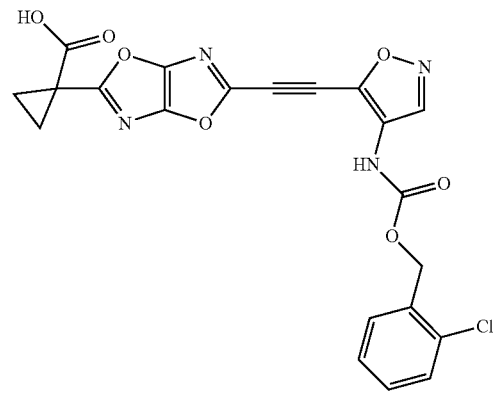 [SMILES: O=C(Nc1cnoc1C#Cc1nc2oc(C3(C(=O)O)CC3)nc2o1)OCc1ccccc1Cl]
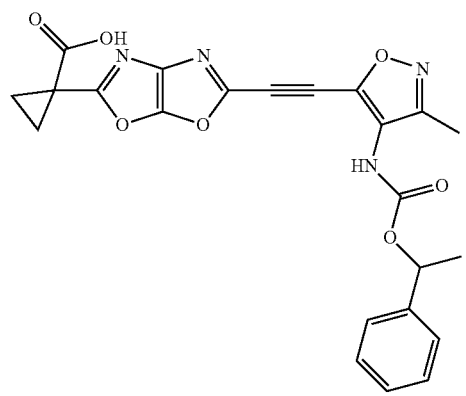 [SMILES: Cc1noc(C#Cc2nc3nc(C4(C(=O)O)CC4)oc3o2)c1NC(=O)OC(C)c1ccccc1]
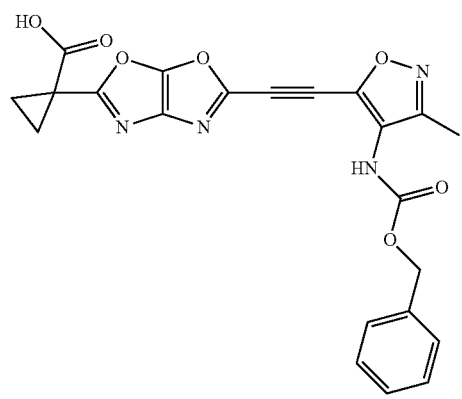 [SMILES: Cc1noc(C#Cc2nc3nc(C4(C(=O)O)CC4)oc3o2)c1NC(=O)OCc1ccccc1]
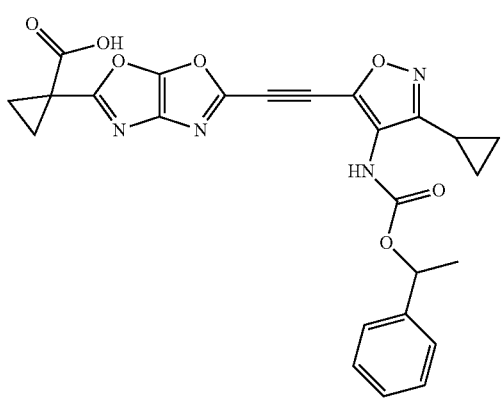 [SMILES: CC(OC(=O)Nc1c(C2CC2)noc1C#Cc1nc2nc(C3(C(=O)O)CC3)oc2o1)c1ccccc1]
TABLE 15-continued
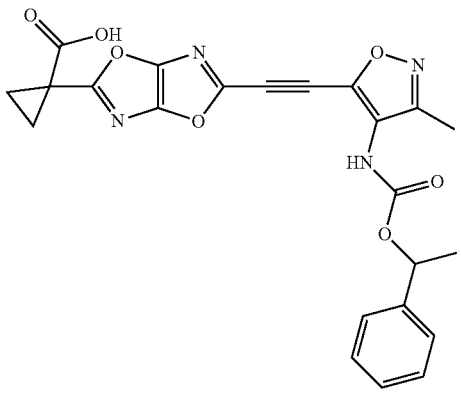 [SMILES: Cc1noc(C#Cc2nc3oc(C4(C(=O)O)CC4)nc3o2)c1NC(=O)OC(C)c1ccccc1]
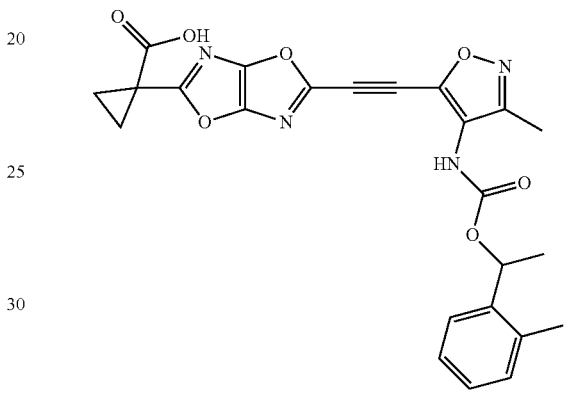
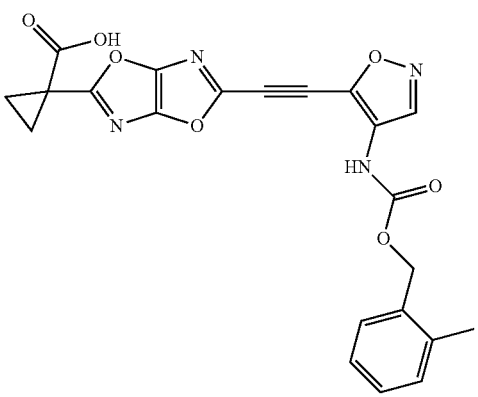 [SMILES: Cc1ccccc1COC(=O)Nc1cnoc1C#Cc1nc2oc(C3(C(=O)O)CC3)nc2o1]
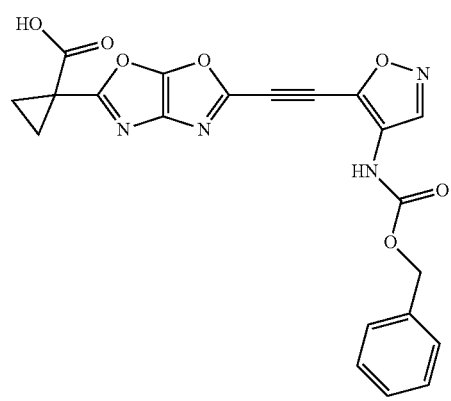 [SMILES: O=C(Nc1cnoc1C#Cc1nc2nc(C3(C(=O)O)CC3)oc2o1)OCc1ccccc1]

TABLE 15-continued
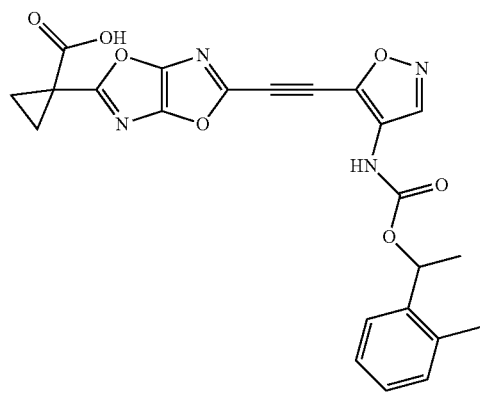 [SMILES: Cc1ccccc1C(C)OC(=O)Nc1cnoc1C#Cc1nc2oc(C3(C(=O)O)CC3)nc2o1]
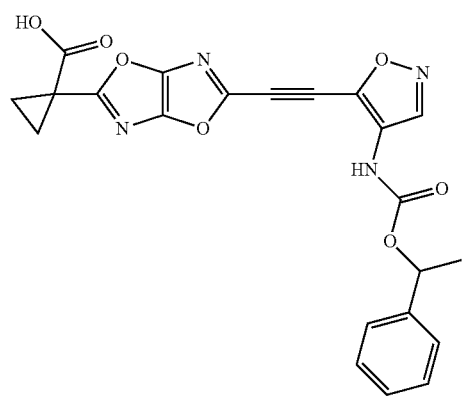 [SMILES: CC(OC(=O)Nc1cnoc1C#Cc1nc2oc(C3(C(=O)O)CC3)nc2o1)c1ccccc1]
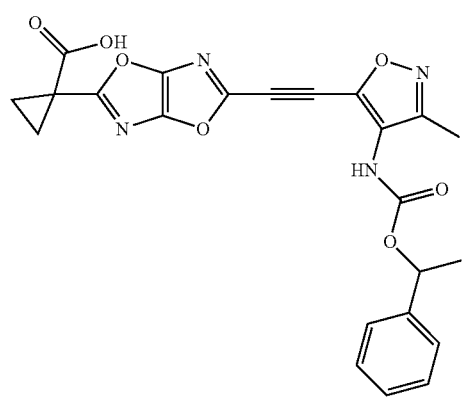 [SMILES: Cc1noc(C#Cc2nc3oc(C4(C(=O)O)CC4)nc3o2)c1NC(=O)OC(C)c1ccccc1]
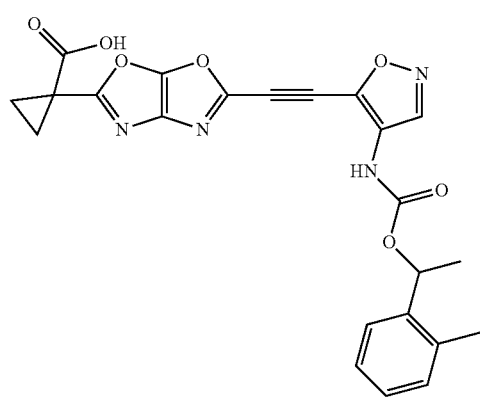 [SMILES: Cc1ccccc1C(C)OC(=O)Nc1cnoc1C#Cc1nc2nc(C3(C(=O)O)CC3)oc2o1]
TABLE 15-continued
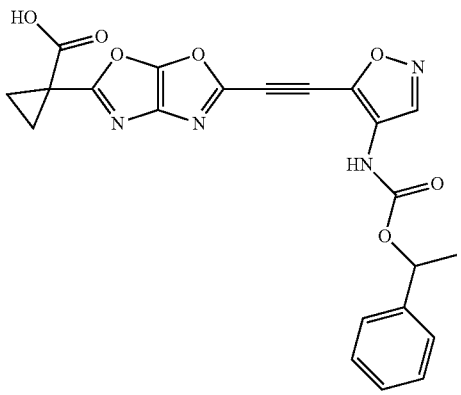 [SMILES: CC(OC(=O)Nc1cnoc1C#Cc1nc2nc(C3(C(=O)O)CC3)oc2o1)c1ccccc1]
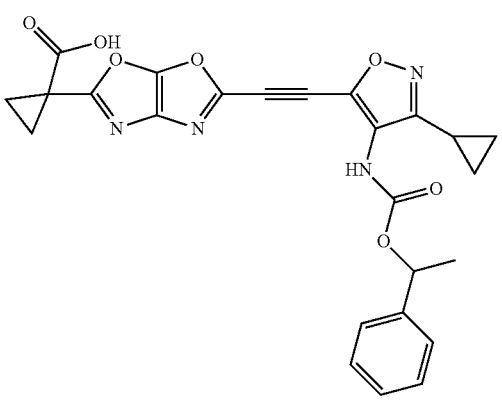 [SMILES: CC(OC(=O)Nc1c(C2CC2)noc1C#Cc1nc2nc(C3(C(=O)O)CC3)oc2o1)c1ccccc1]
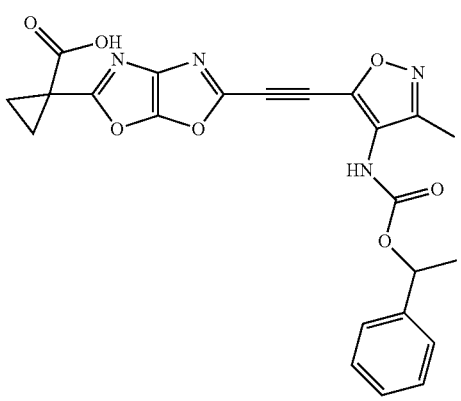 [SMILES: Cc1noc(C#Cc2nc3nc(C4(C(=O)O)CC4)oc3o2)c1NC(=O)OC(C)c1ccccc1]
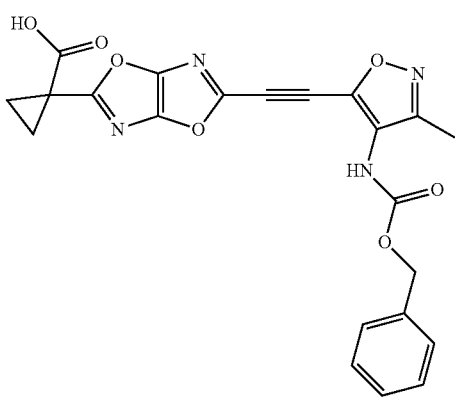 [SMILES: Cc1noc(C#Cc2nc3oc(C4(C(=O)O)CC4)nc3o2)c1NC(=O)OCc1ccccc1]

TABLE 15-continued
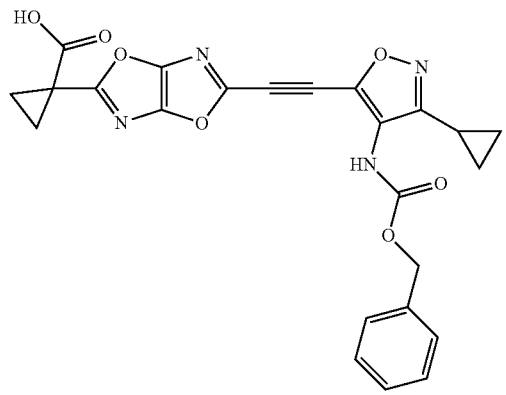 [SMILES: O=C(Nc1c(C2CC2)noc1C#Cc1nc2oc(C3(C(=O)O)CC3)nc2o1)OCc1ccccc1]
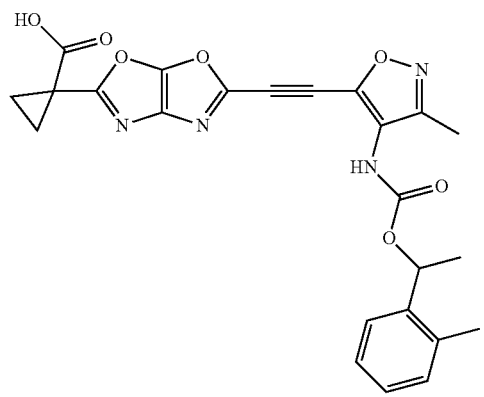 [SMILES: Cc1ccccc1C(C)OC(=O)Nc1c(C)noc1C#Cc1nc2nc(C3(C(=O)O)CC3)oc2o1]
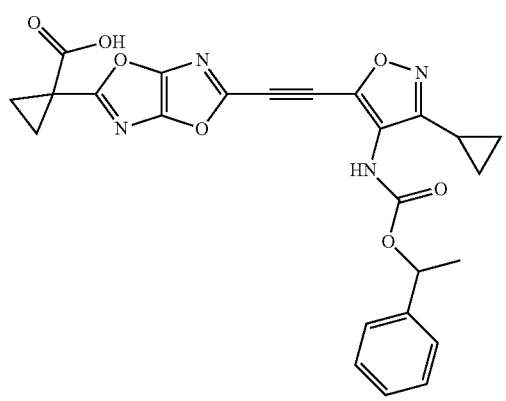 [SMILES: CC(OC(=O)Nc1c(C2CC2)noc1C#Cc1nc2oc(C3(C(=O)O)CC3)nc2o1)c1ccccc1]
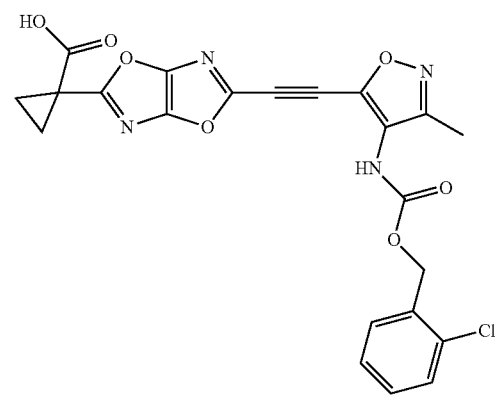 [SMILES: Cc1noc(C#Cc2nc3oc(C4(C(=O)O)CC4)nc3o2)c1NC(=O)OCc1ccccc1Cl]
TABLE 15-continued
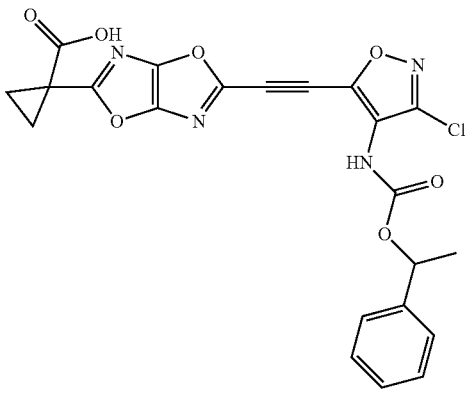 [SMILES: CC(OC(=O)Nc1c(Cl)noc1C#Cc1nc2oc(C3(C(=O)O)CC3)nc2o1)c1ccccc1]
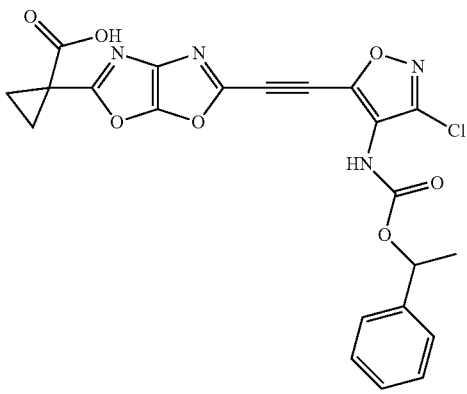 [SMILES: CC(OC(=O)Nc1c(Cl)noc1C#Cc1nc2nc(C3(C(=O)O)CC3)oc2o1)c1ccccc1]
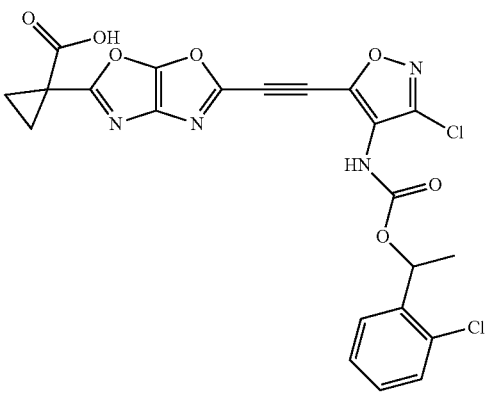 [SMILES: CC(OC(=O)Nc1c(Cl)noc1C#Cc1nc2nc(C3(C(=O)O)CC3)oc2o1)c1ccccc1Cl]
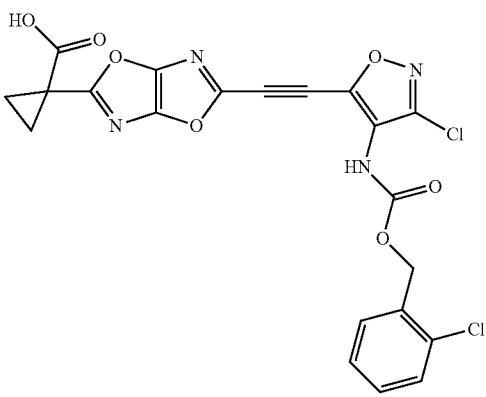 [SMILES: O=C(Nc1c(Cl)noc1C#Cc1nc2oc(C3(C(=O)O)CC3)nc2o1)OCc1ccccc1Cl]

TABLE 15-continued
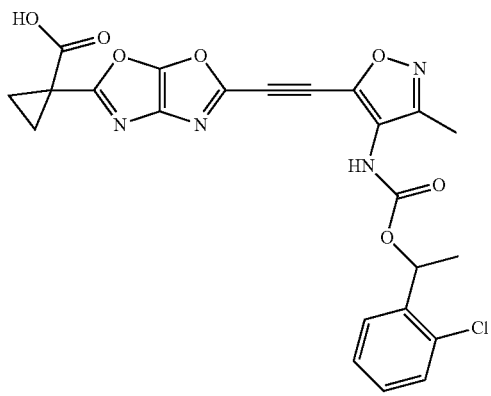 [SMILES: Cc1noc(C#Cc2nc3nc(C4(C(=O)O)CC4)oc3o2)c1NC(=O)OC(C)c1ccccc1Cl]
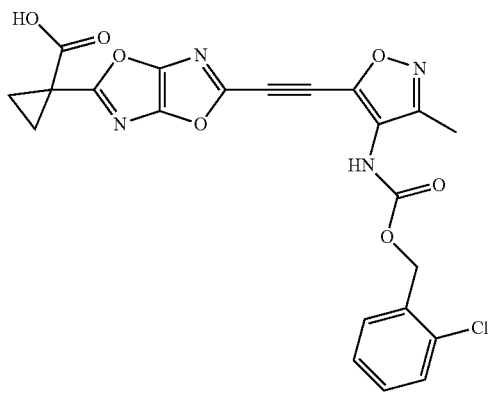 [SMILES: Cc1noc(C#Cc2nc3oc(C4(C(=O)O)CC4)nc3o2)c1NC(=O)OCc1ccccc1Cl]
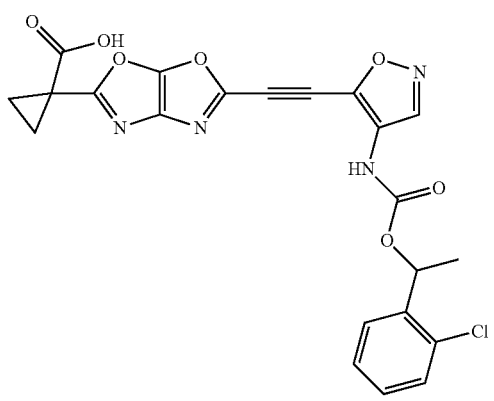 [SMILES: CC(OC(=O)Nc1cnoc1C#Cc1nc2nc(C3(C(=O)O)CC3)oc2o1)c1ccccc1Cl]
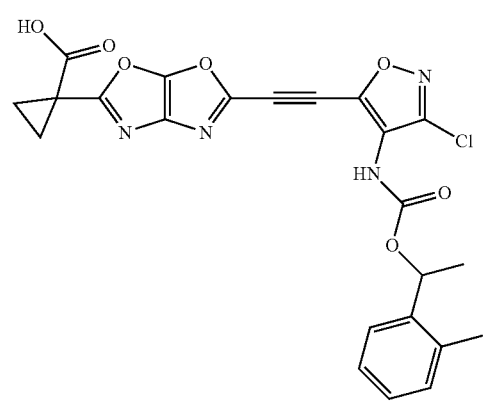 [SMILES: Cc1ccccc1C(C)OC(=O)Nc1c(Cl)noc1C#Cc1nc2nc(C3(C(=O)O)CC3)oc2o1]
TABLE 15-continued
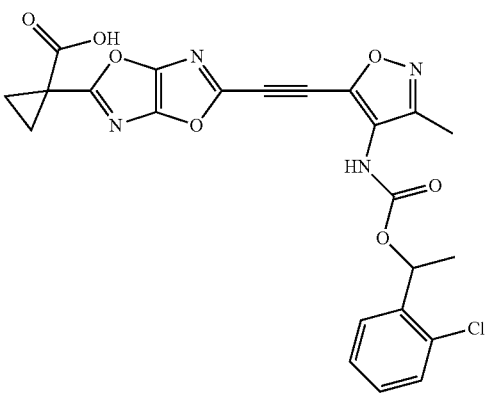 [SMILES: Cc1noc(C#Cc2nc3oc(C4(C(=O)O)CC4)nc3o2)c1NC(=O)OC(C)c1ccccc1Cl]
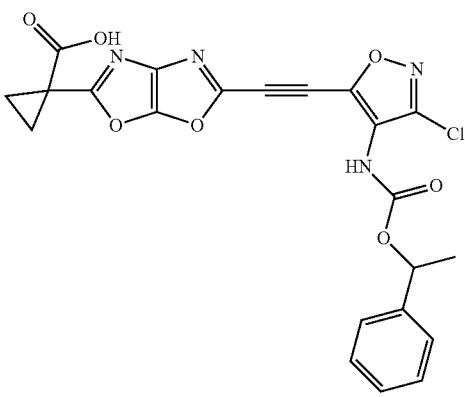 [SMILES: CC(OC(=O)Nc1c(Cl)noc1C#Cc1nc2nc(C3(C(=O)O)CC3)oc2o1)c1ccccc1]
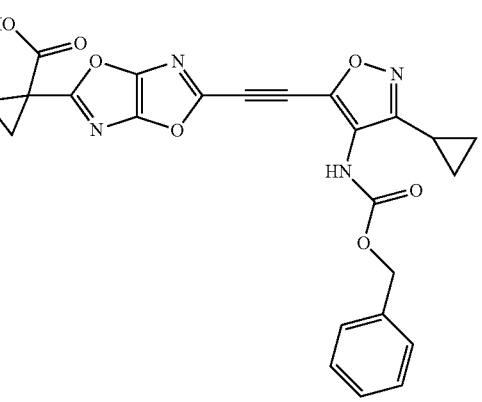
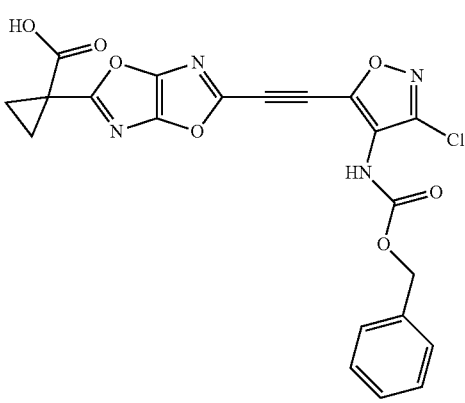

TABLE 15-continued
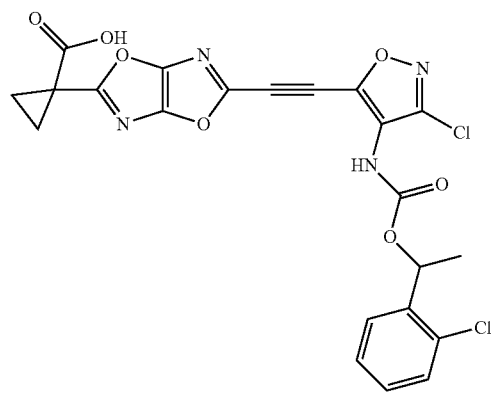 [SMILES: CC(OC(=O)Nc1c(Cl)noc1C#Cc1nc2oc(C3(C(=O)O)CC3)nc2o1)c1ccccc1Cl]
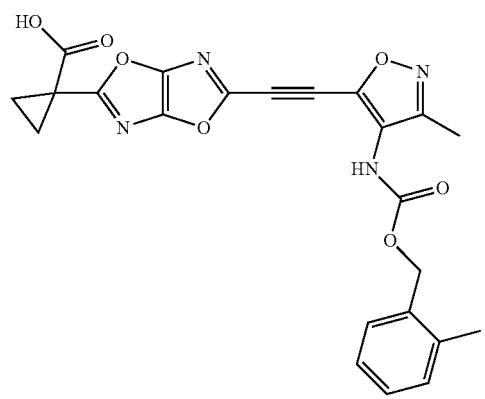 [SMILES: Cc1ccccc1COC(=O)Nc1c(C)noc1C#Cc1nc2oc(C3(C(=O)O)CC3)nc2o1]
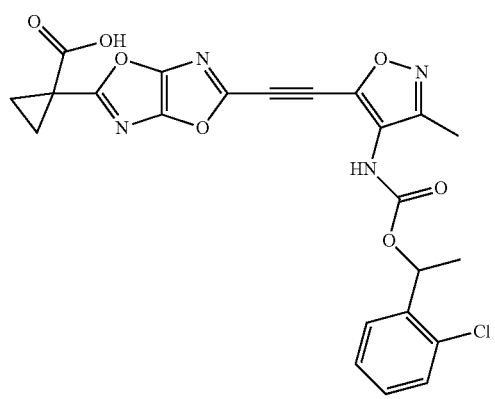 [SMILES: Cc1noc(C#Cc2nc3oc(C4(C(=O)O)CC4)nc3o2)c1NC(=O)OC(C)c1ccccc1Cl]
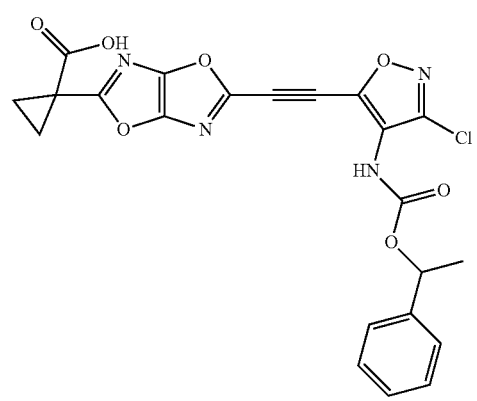 [SMILES: CC(OC(=O)Nc1c(Cl)noc1C#Cc1nc2oc(C3(C(=O)O)CC3)nc2o1)c1ccccc1]
TABLE 15-continued
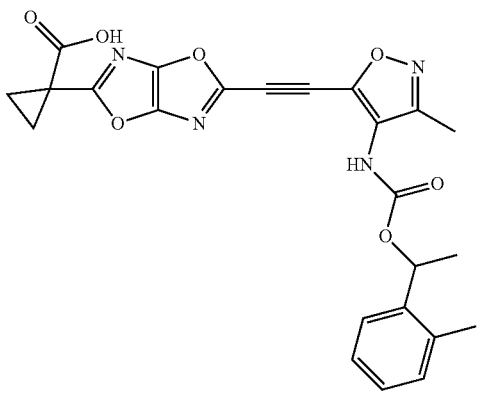 [SMILES: Cc1ccccc1C(C)OC(=O)Nc1c(C)noc1C#Cc1nc2oc(C3(C(=O)O)CC3)nc2o1]
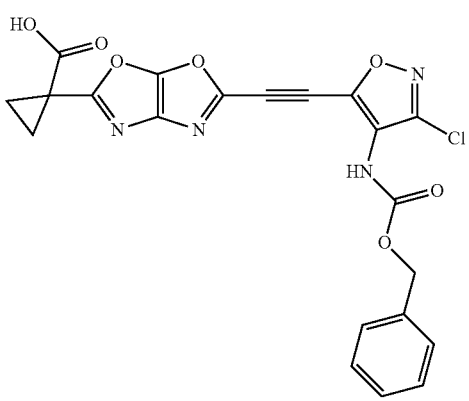
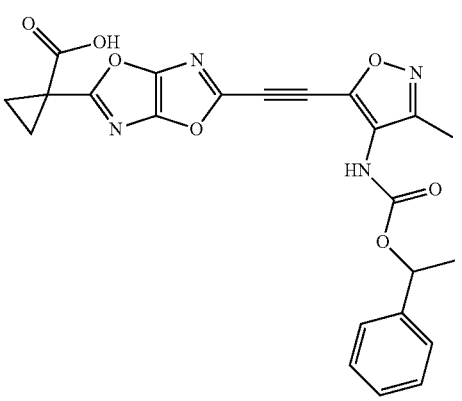 [SMILES: Cc1noc(C#Cc2nc3oc(C4(C(=O)O)CC4)nc3o2)c1NC(=O)OC(C)c1ccccc1]
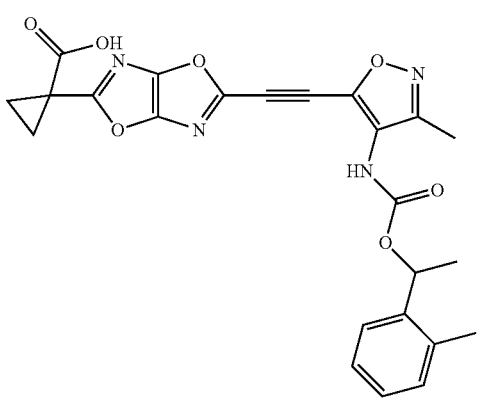

TABLE 15-continued
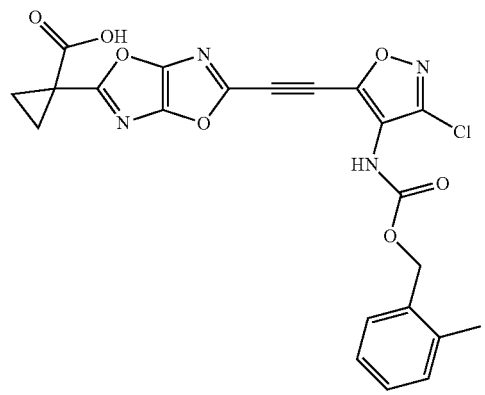 [SMILES: Cc1ccccc1COC(=O)Nc1c(Cl)noc1C#Cc1nc2oc(C3(C(=O)O)CC3)nc2o1]
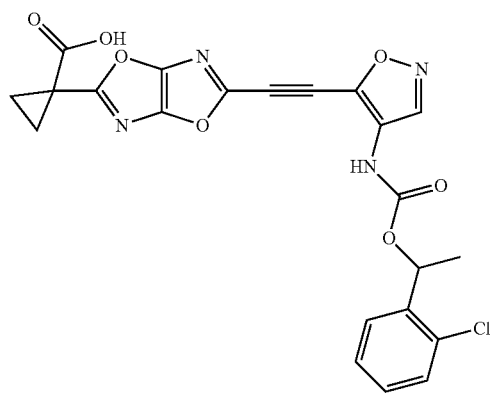 [SMILES: CC(OC(=O)Nc1cnoc1C#Cc1nc2oc(C3(C(=O)O)CC3)nc2o1)c1ccccc1Cl]
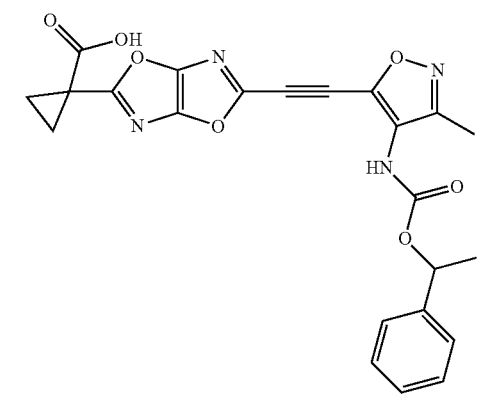 [SMILES: Cc1noc(C#Cc2nc3oc(C4(C(=O)O)CC4)nc3o2)c1NC(=O)OC(C)c1ccccc1]
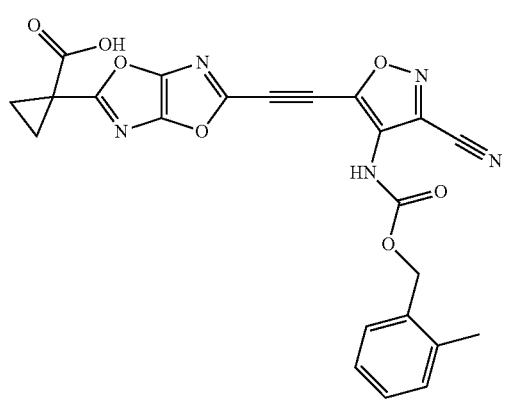 [SMILES: Cc1ccccc1COC(=O)Nc1c(C#N)noc1C#Cc1nc2oc(C3(C(=O)O)CC3)nc2o1]
TABLE 15-continued
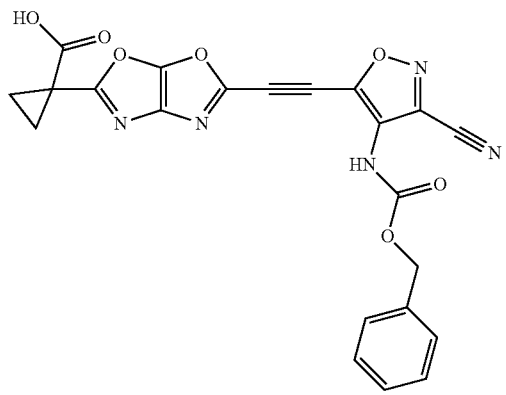 [SMILES: N#Cc1noc(C#Cc2nc3nc(C4(C(=O)O)CC4)oc3o2)c1NC(=O)OCc1ccccc1]
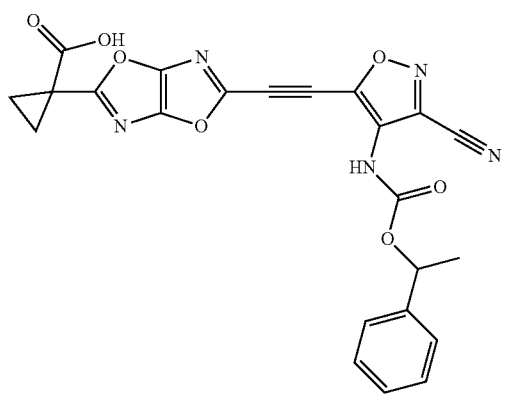 [SMILES: CC(OC(=O)Nc1c(C#N)noc1C#Cc1nc2oc(C3(C(=O)O)CC3)nc2o1)c1ccccc1]
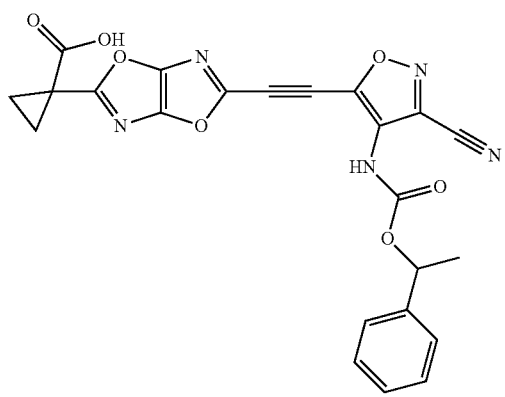 [SMILES: CC(OC(=O)Nc1c(C#N)noc1C#Cc1nc2oc(C3(C(=O)O)CC3)nc2o1)c1ccccc1]
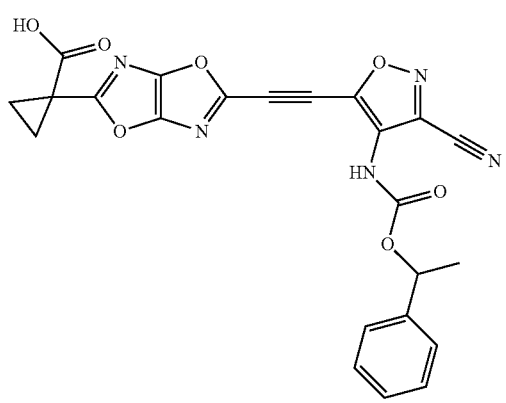 [SMILES: CC(OC(=O)Nc1c(C#N)noc1C#Cc1nc2oc(C3(C(=O)O)CC3)nc2o1)c1ccccc1]

TABLE 15-continued
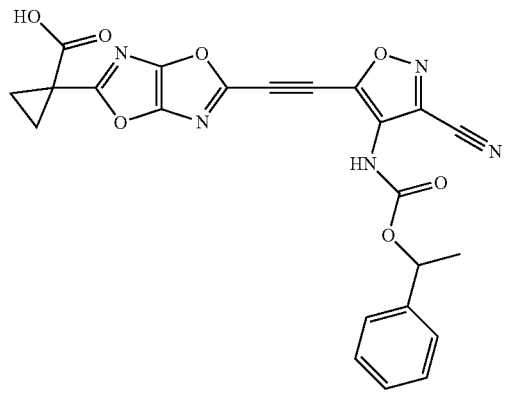 [SMILES: CC(OC(=O)Nc1c(C#N)noc1C#Cc1nc2oc(C3(C(=O)O)CC3)nc2o1)c1ccccc1]
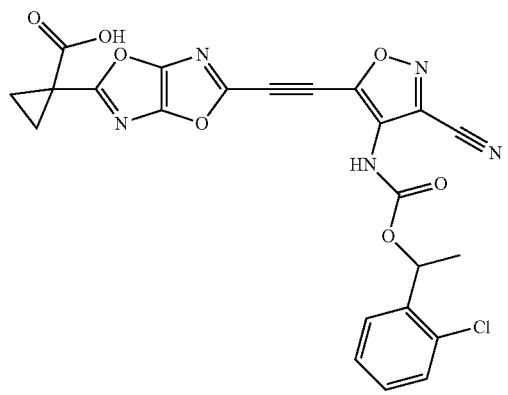 [SMILES: CC(OC(=O)Nc1c(C#N)noc1C#Cc1nc2oc(C3(C(=O)O)CC3)nc2o1)c1ccccc1Cl]
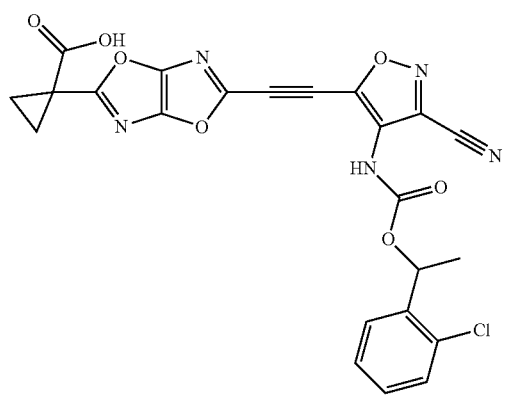 [SMILES: CC(OC(=O)Nc1c(C#N)noc1C#Cc1nc2oc(C3(C(=O)O)CC3)nc2o1)c1ccccc1Cl]
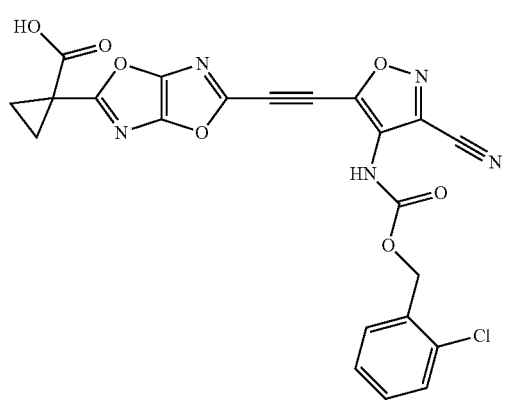 [SMILES: N#Cc1noc(C#Cc2nc3oc(C4(C(=O)O)CC4)nc3o2)c1NC(=O)OCc1ccccc1Cl]
TABLE 15-continued
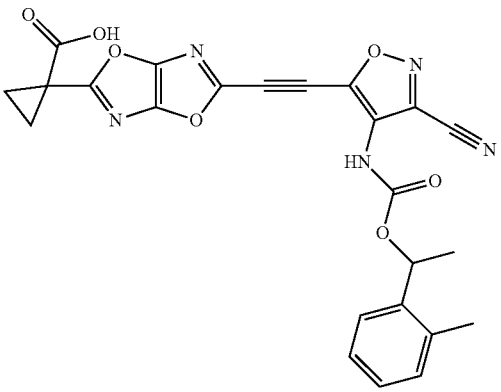 [SMILES: Cc1ccccc1C(C)OC(=O)Nc1c(C#N)noc1C#Cc1nc2oc(C3(C(=O)O)CC3)nc2o1]
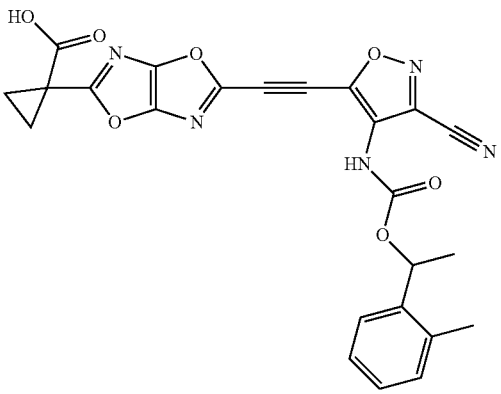 [SMILES: Cc1ccccc1C(C)OC(=O)Nc1c(C#N)noc1C#Cc1nc2oc(C3(C(=O)O)CC3)nc2o1]
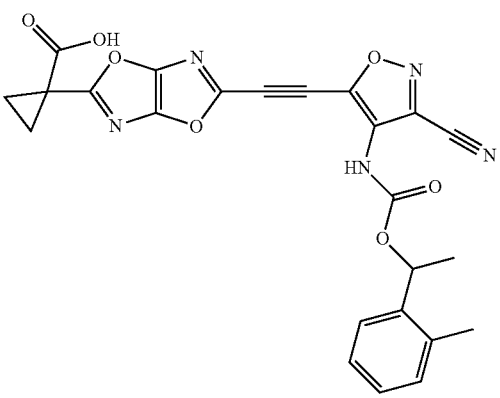 [SMILES: Cc1ccccc1C(C)OC(=O)Nc1c(C#N)noc1C#Cc1nc2oc(C3(C(=O)O)CC3)nc2o1]
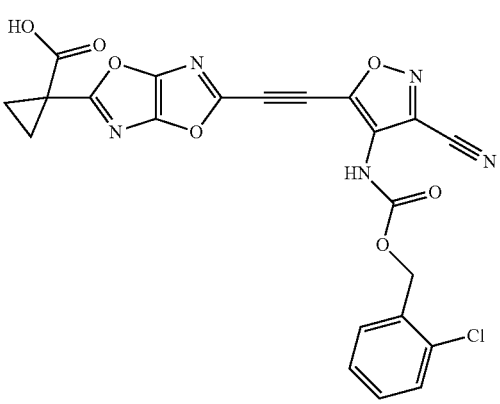 [SMILES: N#Cc1noc(C#Cc2nc3oc(C4(C(=O)O)CC4)nc3o2)c1NC(=O)OCc1ccccc1Cl]

US 8,975,235 B2
TABLE 15-continued
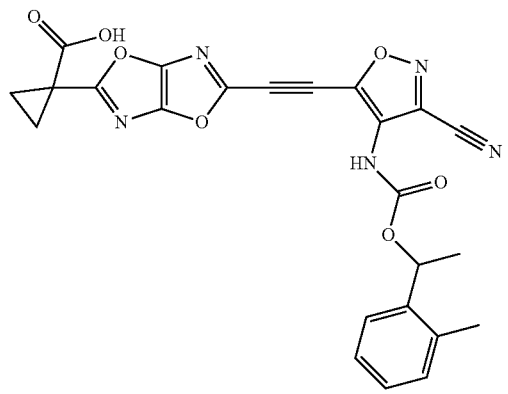
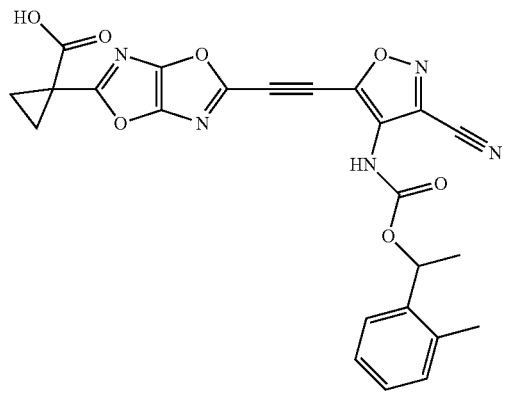 [SMILES: Cc1ccccc1C(C)OC(=O)Nc1c(C#N)noc1C#Cc1nc2oc(C3(C(=O)O)CC3)nc2o1]
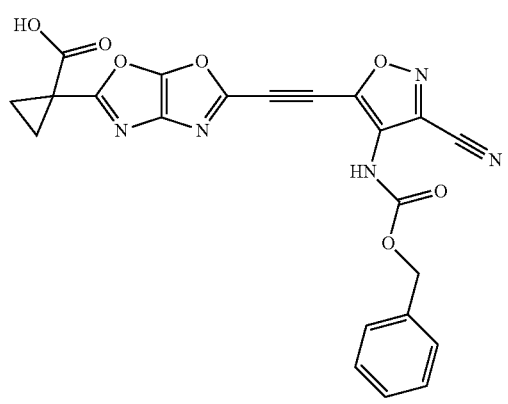 [SMILES: N#Cc1noc(C#Cc2nc3nc(C4(C(=O)O)CC4)oc3o2)c1NC(=O)OCc1ccccc1]
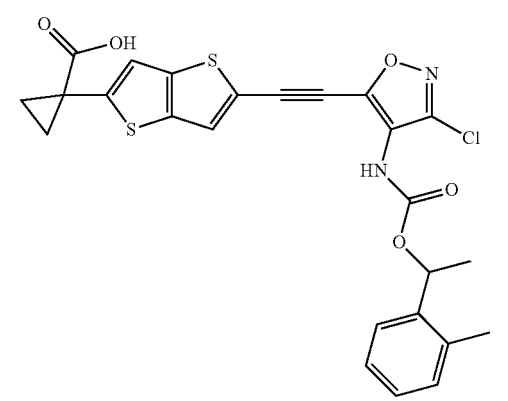
TABLE 15-continued
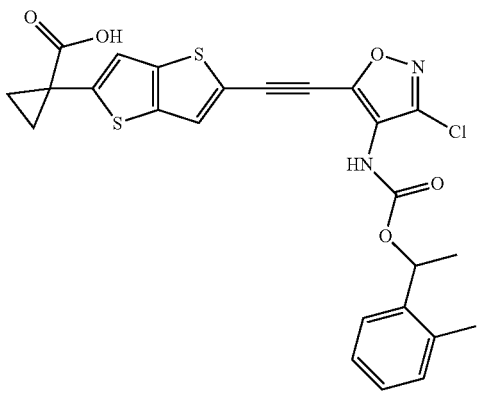
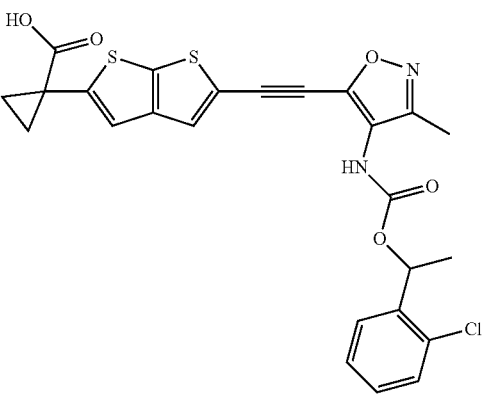 [SMILES: Cc1noc(C#Cc2cc3cc(C4(C(=O)O)CC4)sc3s2)c1NC(=O)OC(C)c1ccccc1Cl]
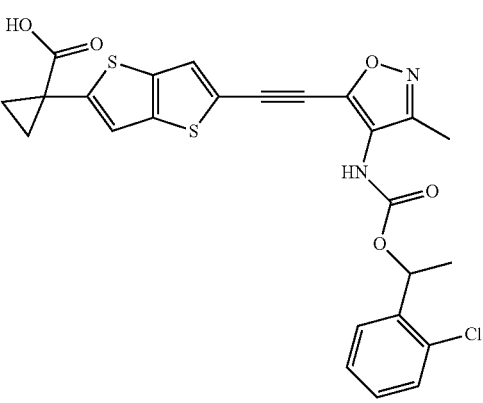
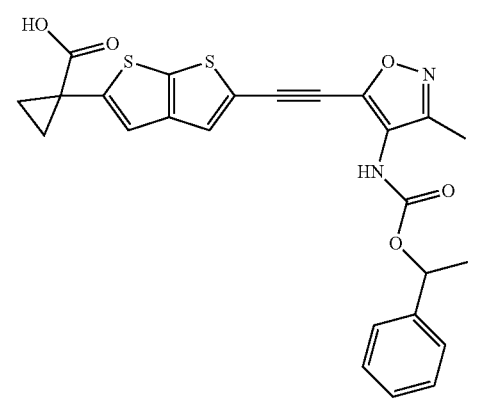 [SMILES: Cc1noc(C#Cc2cc3cc(C4(C(=O)O)CC4)sc3s2)c1NC(=O)OC(C)c1ccccc1]

TABLE 15-continued
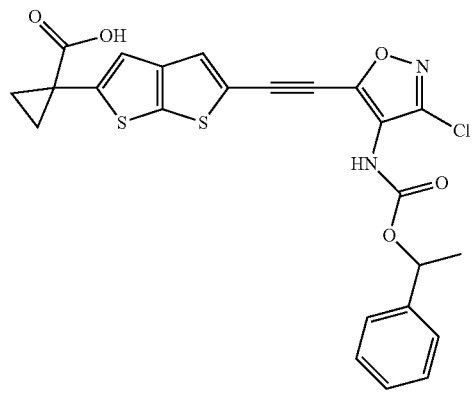 [SMILES: CC(OC(=O)Nc1c(Cl)noc1C#Cc1cc2cc(C3(C(=O)O)CC3)sc2s1)c1ccccc1]
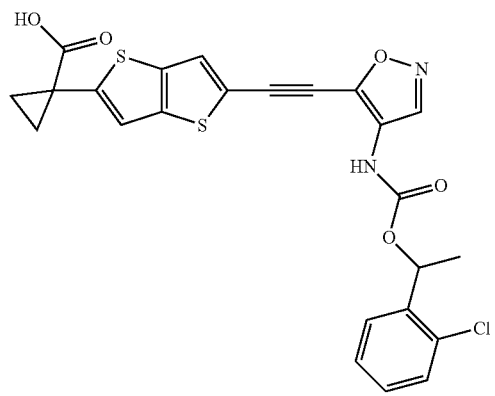 [SMILES: CC(OC(=O)Nc1cnoc1C#Cc1cc2sc(C3(C(=O)O)CC3)cc2s1)c1ccccc1Cl]
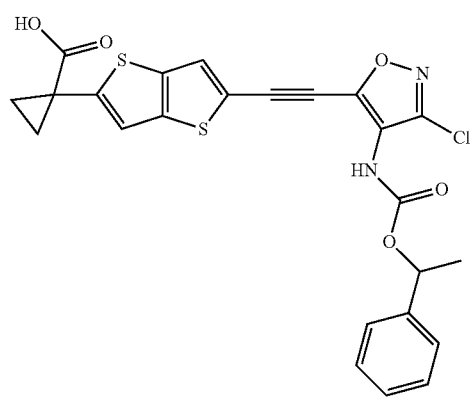 [SMILES: CC(OC(=O)Nc1c(Cl)noc1C#Cc1cc2sc(C3(C(=O)O)CC3)cc2s1)c1ccccc1]
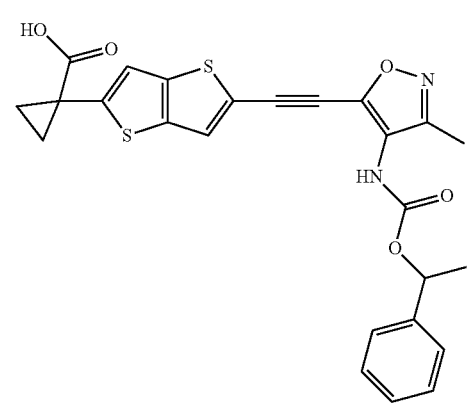 [SMILES: Cc1noc(C#Cc2cc3sc(C4(C(=O)O)CC4)cc3s2)c1NC(=O)OC(C)c1ccccc1]
TABLE 15-continued
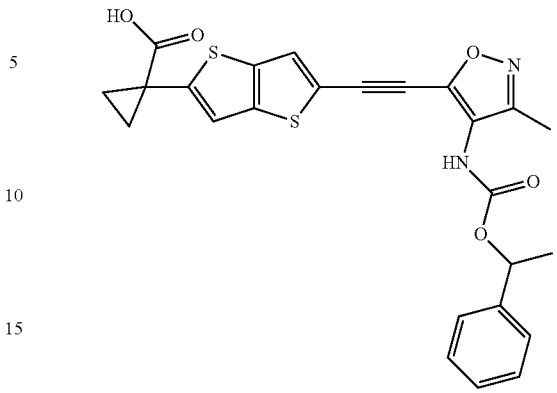
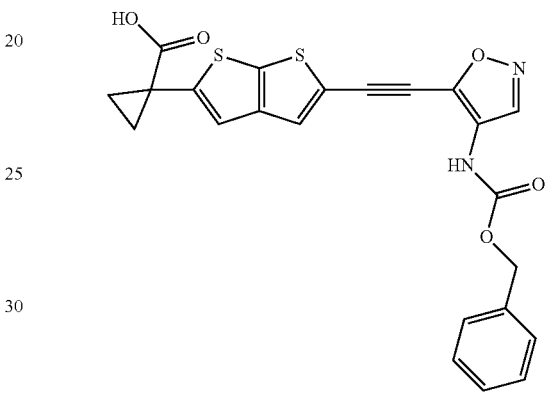
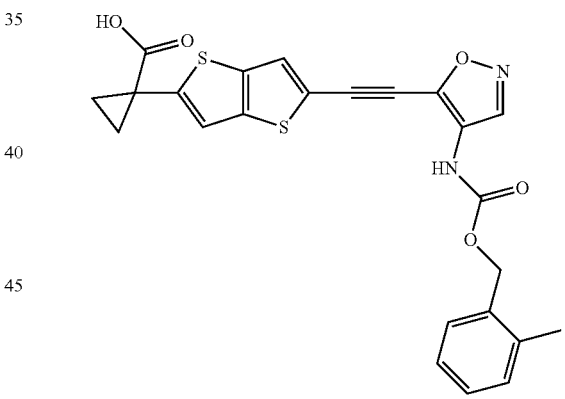
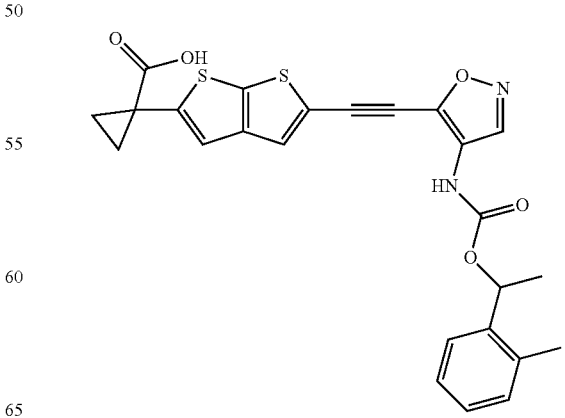

TABLE 15-continued
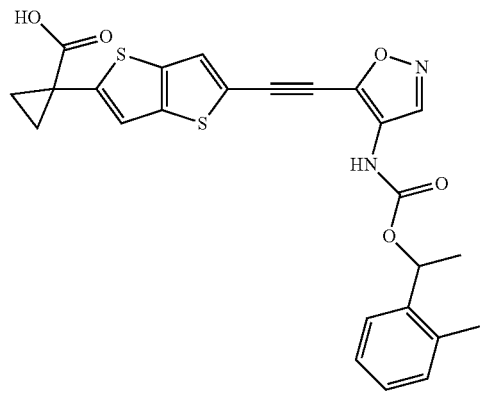 [SMILES: Cc1ccccc1C(C)OC(=O)Nc1cnoc1C#Cc1cc2sc(C3(C(=O)O)CC3)cc2s1]
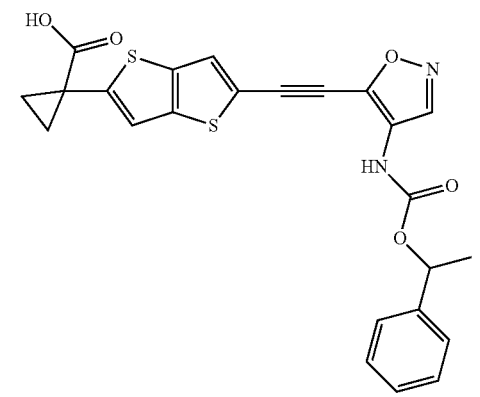 [SMILES: CC(OC(=O)Nc1cnoc1C#Cc1cc2sc(C3(C(=O)O)CC3)cc2s1)c1ccccc1]
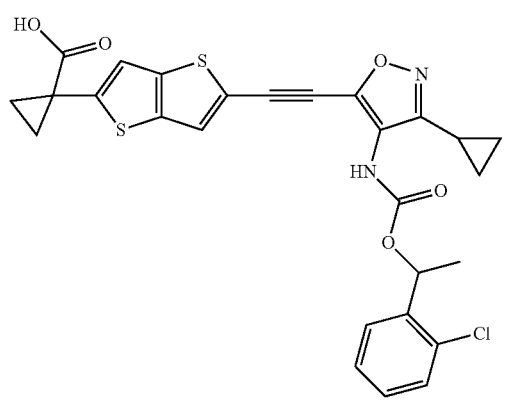 [SMILES: CC(OC(=O)Nc1c(C2CC2)noc1C#Cc1cc2sc(C3(C(=O)O)CC3)cc2s1)c1ccccc1Cl]
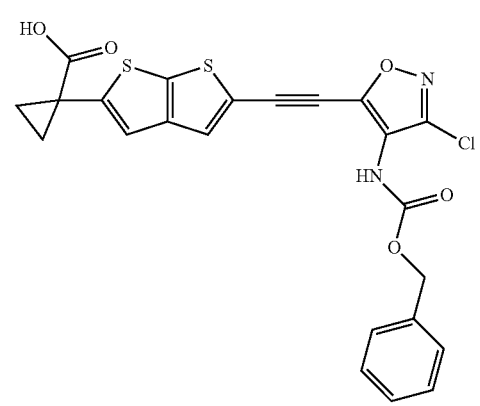
TABLE 15-continued
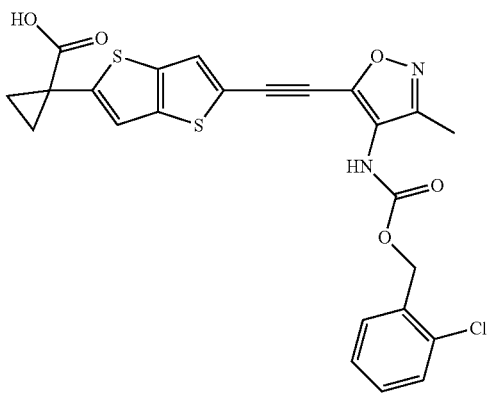 [SMILES: Cc1noc(C#Cc2cc3sc(C4(C(=O)O)CC4)cc3s2)c1NC(=O)OCc1ccccc1Cl]
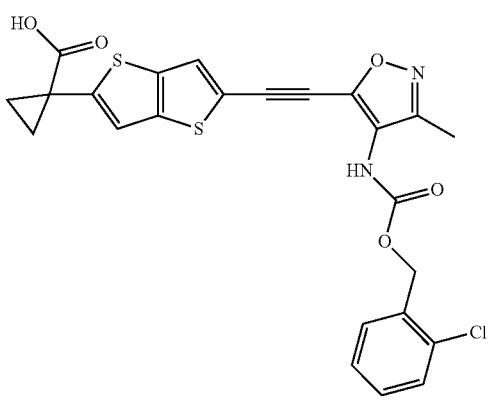 [SMILES: Cc1noc(C#Cc2cc3sc(C4(C(=O)O)CC4)cc3s2)c1NC(=O)OCc1ccccc1Cl]
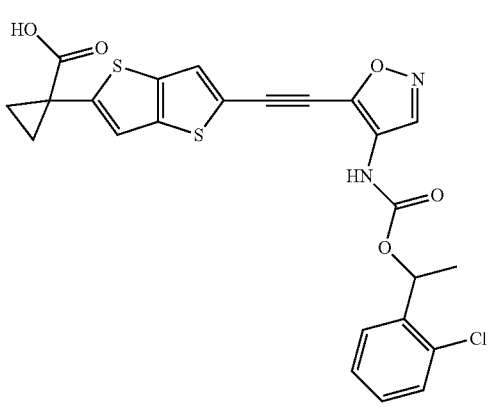 [SMILES: CC(OC(=O)Nc1cnoc1C#Cc1cc2sc(C3(C(=O)O)CC3)cc2s1)c1ccccc1Cl]
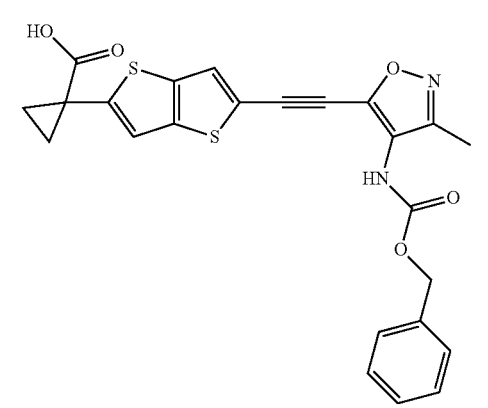 [SMILES: Cc1noc(C#Cc2cc3sc(C4(C(=O)O)CC4)cc3s2)c1NC(=O)OCc1ccccc1]

TABLE 15-continued
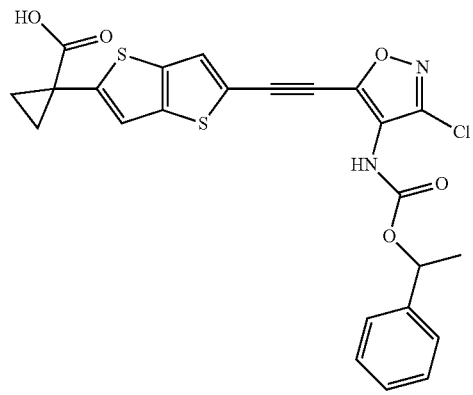 [SMILES: CC(OC(=O)Nc1c(Cl)noc1C#Cc1cc2sc(C3(C(=O)O)CC3)cc2s1)c1ccccc1]
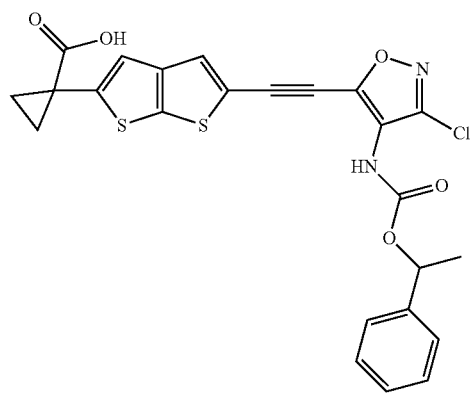 [SMILES: CC(OC(=O)Nc1c(Cl)noc1C#Cc1cc2cc(C3(C(=O)O)CC3)sc2s1)c1ccccc1]
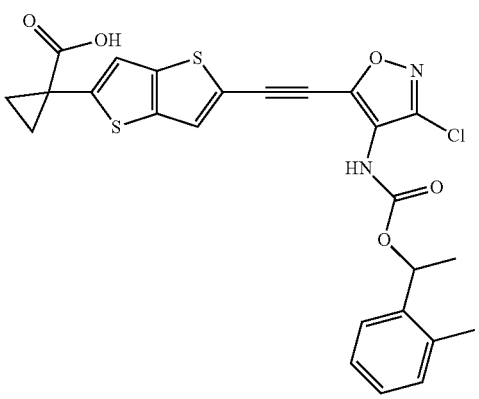
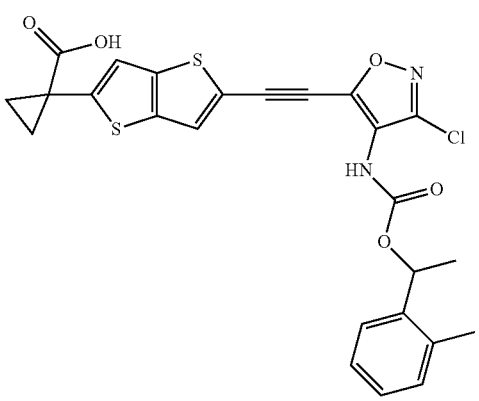 [SMILES: Cc1ccccc1C(C)OC(=O)Nc1c(Cl)noc1C#Cc1cc2sc(C3(C(=O)O)CC3)cc2s1]
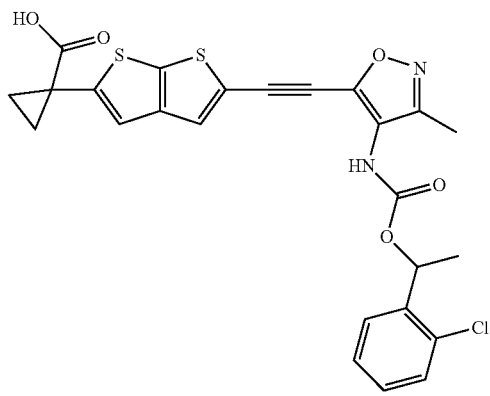 [SMILES: Cc1noc(C#Cc2cc3cc(C4(C(=O)O)CC4)sc3s2)c1NC(=O)OC(C)c1ccccc1Cl]
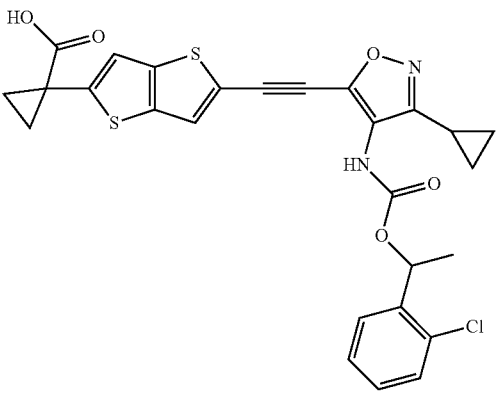 [SMILES: CC(OC(=O)Nc1c(C2CC2)noc1C#Cc1cc2sc(C3(C(=O)O)CC3)cc2s1)c1ccccc1Cl]
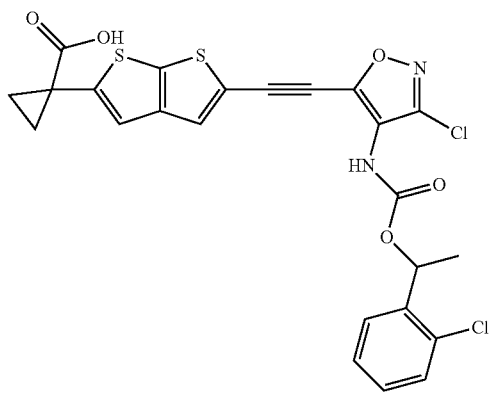 [SMILES: CC(OC(=O)Nc1c(Cl)noc1C#Cc1cc2cc(C3(C(=O)O)CC3)sc2s1)c1ccccc1Cl]
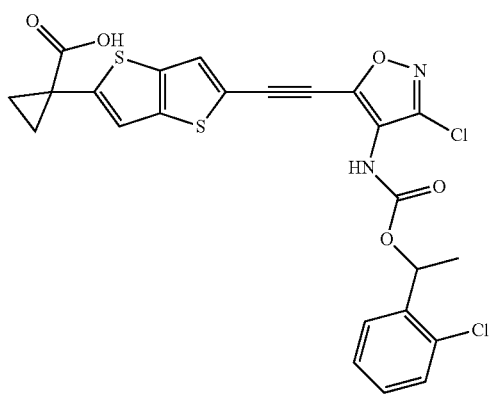 [SMILES: CC(OC(=O)Nc1c(Cl)noc1C#Cc1cc2sc(C3(C(=O)O)CC3)cc2s1)c1ccccc1Cl]

TABLE 15-continued
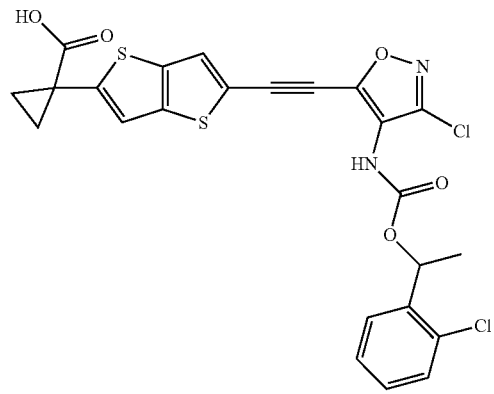 [SMILES: CC(OC(=O)Nc1c(Cl)noc1C#Cc1cc2sc(C3(C(=O)O)CC3)cc2s1)c1ccccc1Cl]
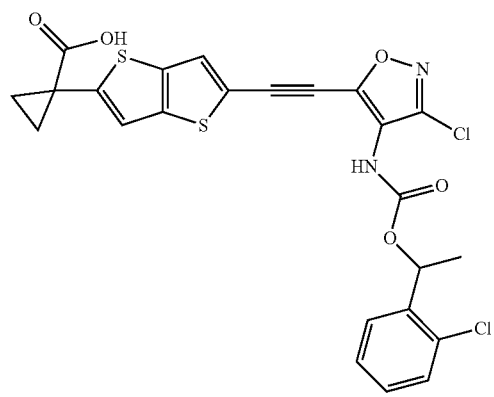 [SMILES: CC(OC(=O)Nc1c(Cl)noc1C#Cc1cc2sc(C3(C(=O)O)CC3)cc2s1)c1ccccc1Cl]
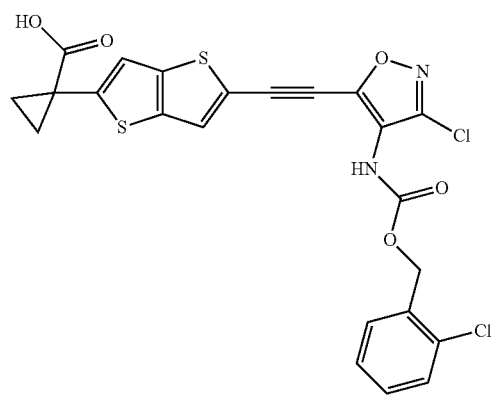 [SMILES: O=C(Nc1c(Cl)noc1C#Cc1cc2sc(C3(C(=O)O)CC3)cc2s1)OCc1ccccc1Cl]
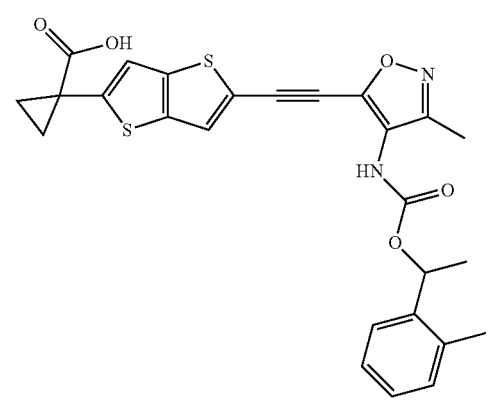 [SMILES: Cc1ccccc1C(C)OC(=O)Nc1c(C)noc1C#Cc1cc2sc(C3(C(=O)O)CC3)cc2s1]
TABLE 15-continued
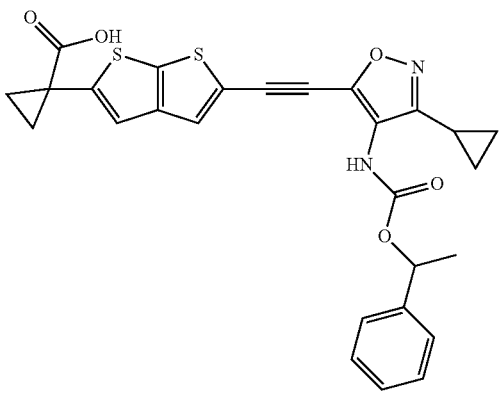 [SMILES: CC(OC(=O)Nc1c(C2CC2)noc1C#Cc1cc2cc(C3(C(=O)O)CC3)sc2s1)c1ccccc1]
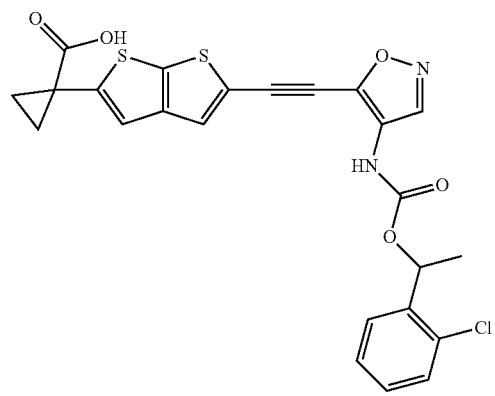 [SMILES: CC(OC(=O)Nc1cnoc1C#Cc1cc2cc(C3(C(=O)O)CC3)sc2s1)c1ccccc1Cl]
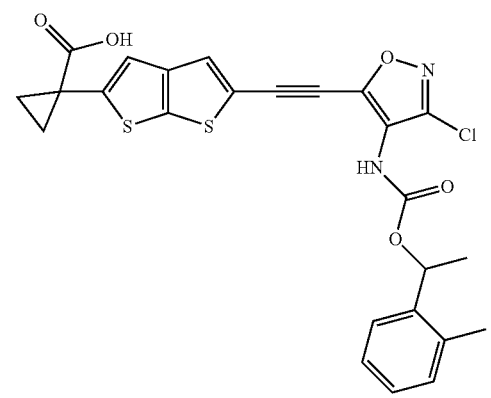 [SMILES: Cc1ccccc1C(C)OC(=O)Nc1c(Cl)noc1C#Cc1cc2cc(C3(C(=O)O)CC3)sc2s1]
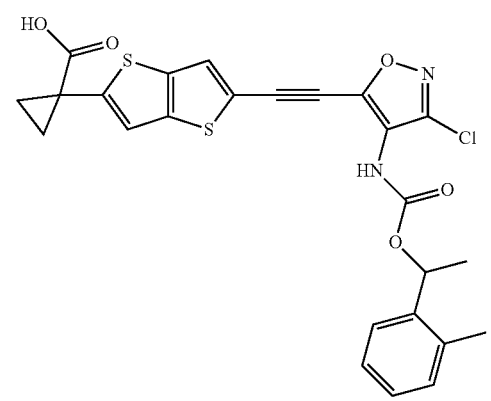 [SMILES: Cc1ccccc1C(C)OC(=O)Nc1c(Cl)noc1C#Cc1cc2sc(C3(C(=O)O)CC3)cc2s1]

TABLE 15-continued
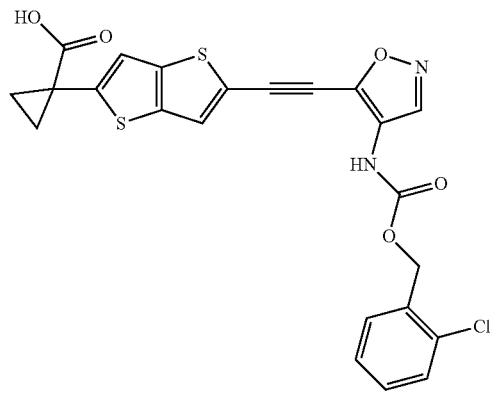 [SMILES: O=C(Nc1cnoc1C#Cc1cc2sc(C3(C(=O)O)CC3)cc2s1)OCc1ccccc1Cl]
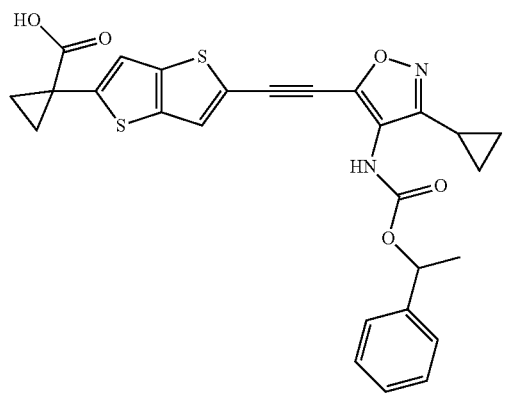
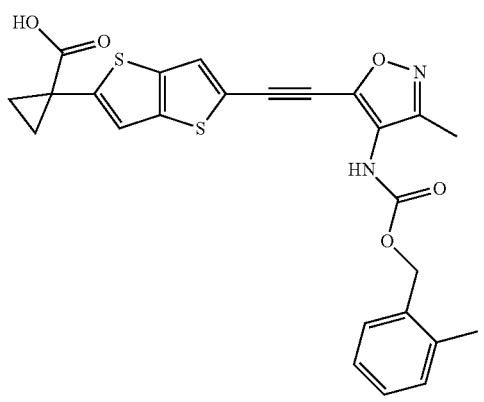 [SMILES: Cc1ccccc1COC(=O)Nc1c(C)noc1C#Cc1cc2sc(C3(C(=O)O)CC3)cc2s1]
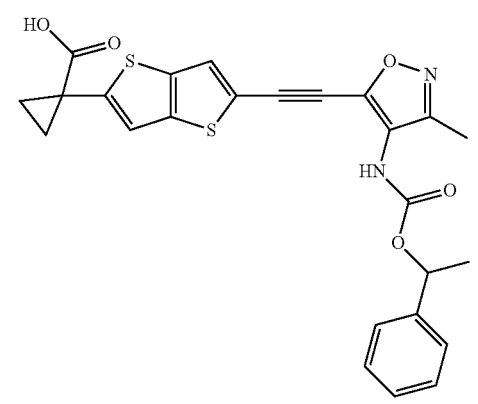 [SMILES: Cc1noc(C#Cc2cc3sc(C4(C(=O)O)CC4)cc3s2)c1NC(=O)OC(C)c1ccccc1]
TABLE 15-continued
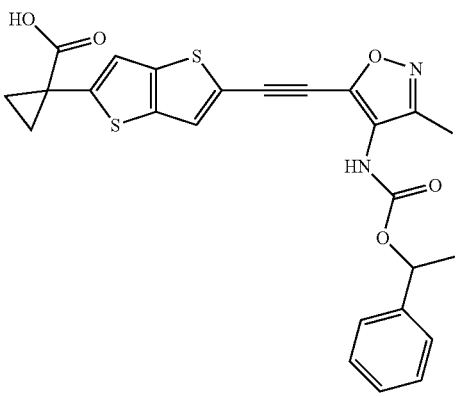 [SMILES: Cc1noc(C#Cc2cc3sc(C4(C(=O)O)CC4)cc3s2)c1NC(=O)OC(C)c1ccccc1]
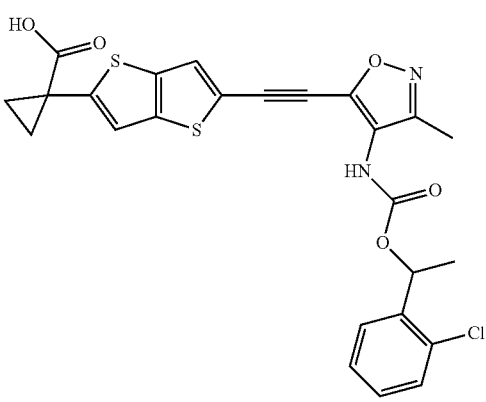 [SMILES: Cc1noc(C#Cc2cc3sc(C4(C(=O)O)CC4)cc3s2)c1NC(=O)OC(C)c1ccccc1Cl]
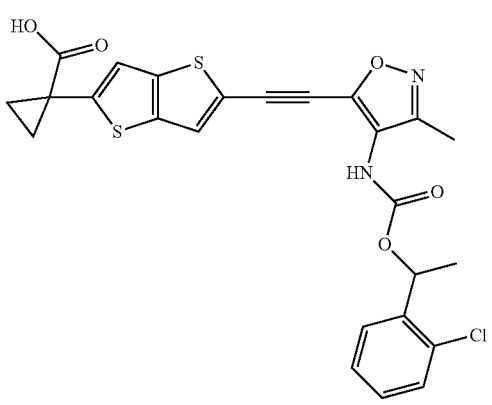 [SMILES: Cc1noc(C#Cc2cc3sc(C4(C(=O)O)CC4)cc3s2)c1NC(=O)OC(C)c1ccccc1Cl]
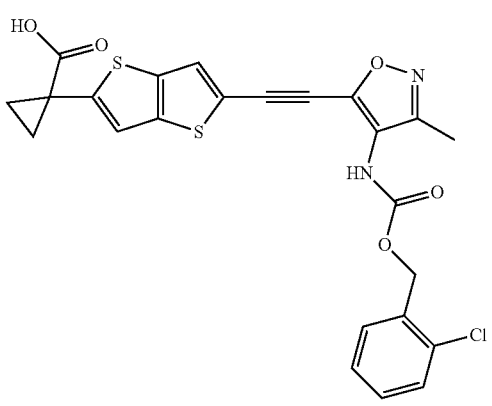 [SMILES: Cc1noc(C#Cc2cc3sc(C4(C(=O)O)CC4)cc3s2)c1NC(=O)OCc1ccccc1Cl]

TABLE 15-continued
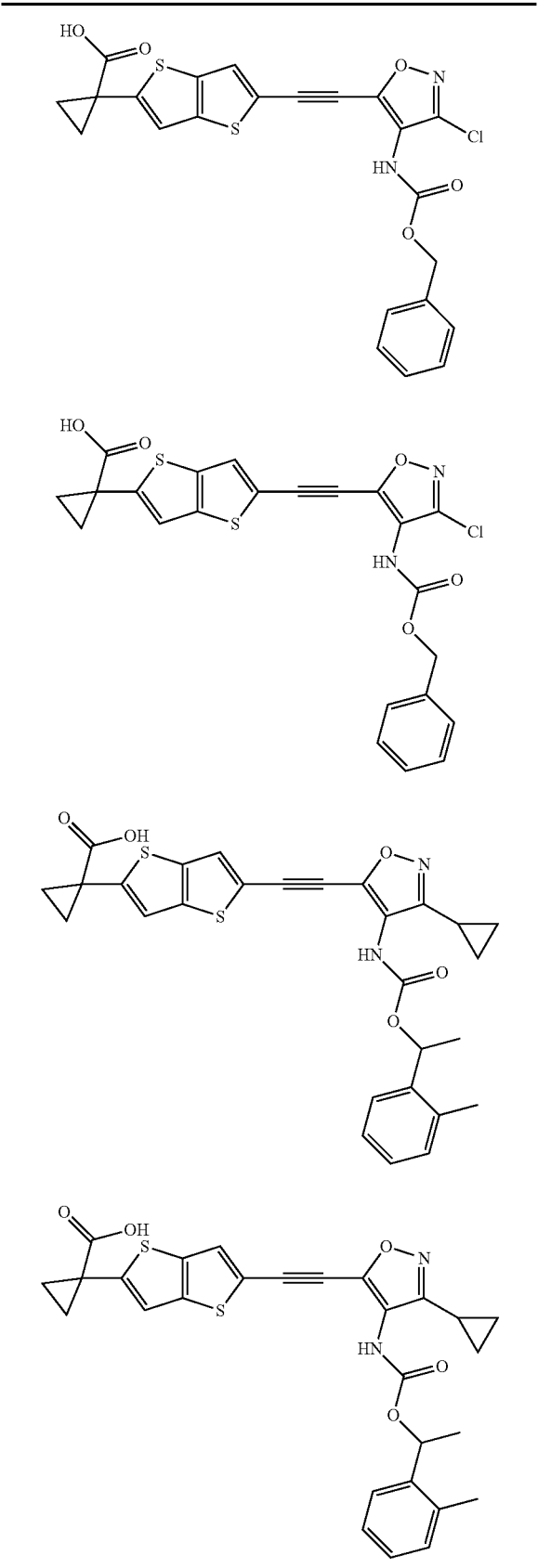
TABLE 15-continued
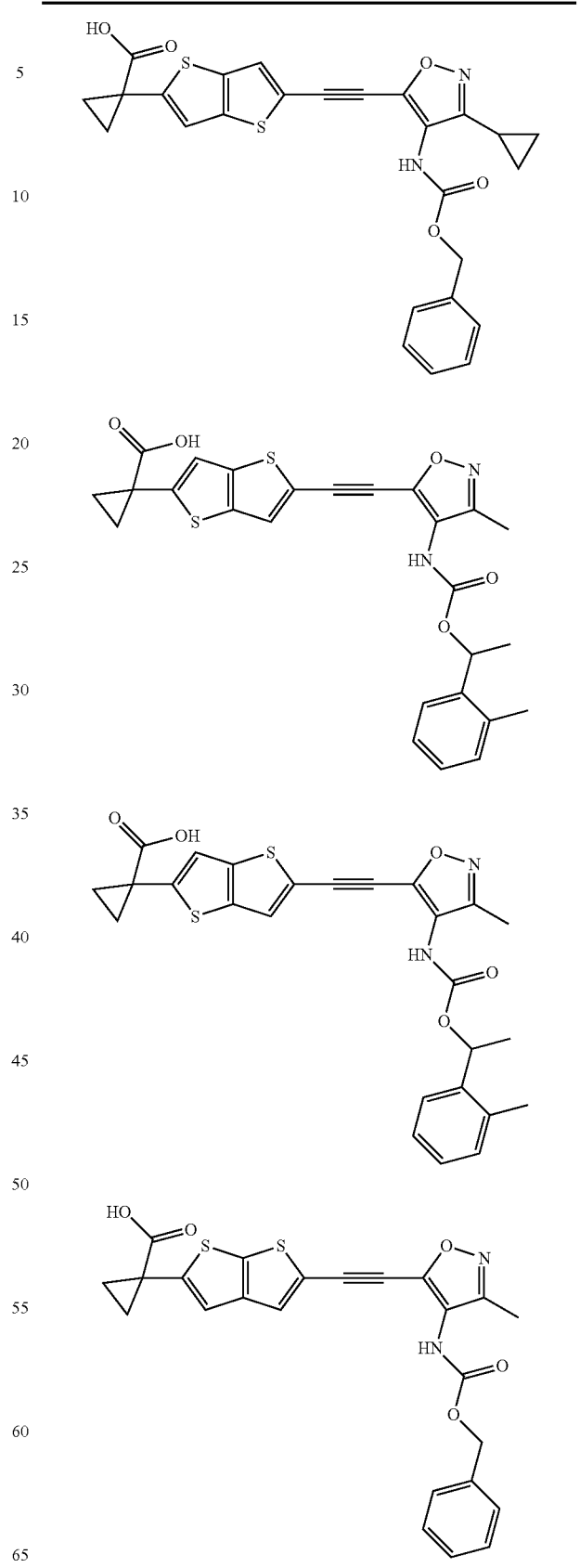

TABLE 15-continued
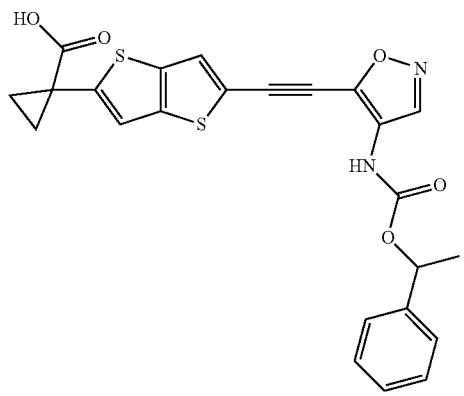
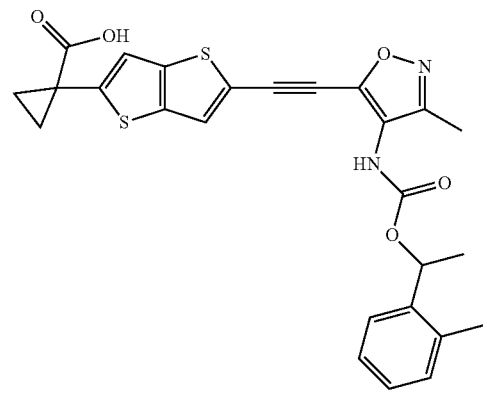 [SMILES: Cc1ccccc1C(C)OC(=O)Nc1c(C)noc1C#Cc1cc2sc(C3(C(=O)O)CC3)cc2s1]
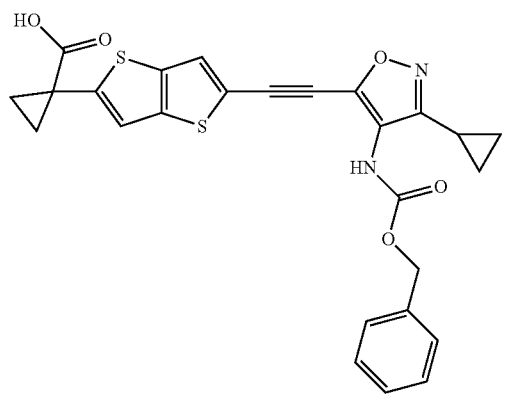 [SMILES: O=C(Nc1c(C2CC2)noc1C#Cc1cc2sc(C3(C(=O)O)CC3)cc2s1)OCc1ccccc1]
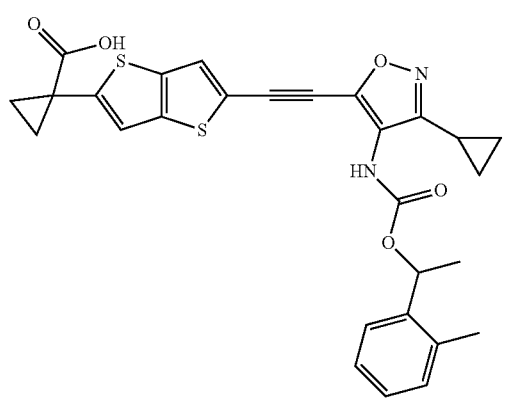 [SMILES: Cc1ccccc1C(C)OC(=O)Nc1c(C2CC2)noc1C#Cc1cc2sc(C3(C(=O)O)CC3)cc2s1]
TABLE 15-continued
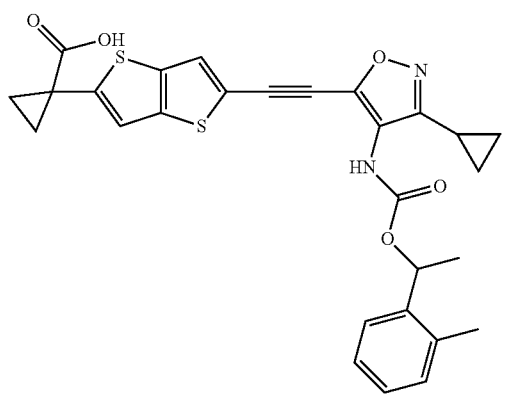 [SMILES: Cc1ccccc1C(C)OC(=O)Nc1c(C2CC2)noc1C#Cc1cc2sc(C3(C(=O)O)CC3)cc2s1]
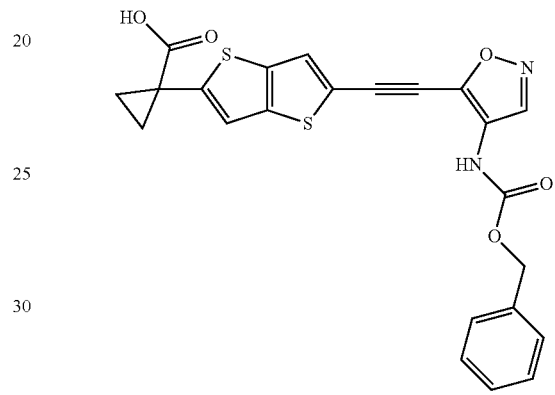
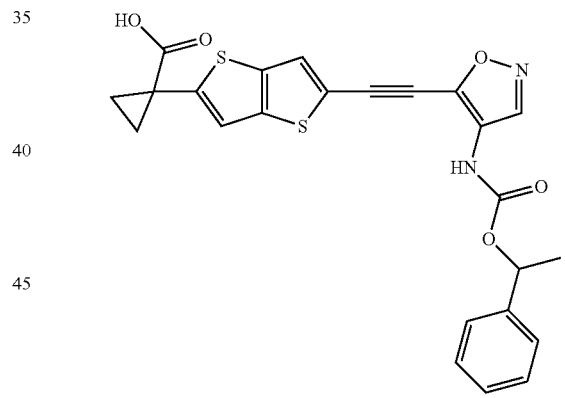
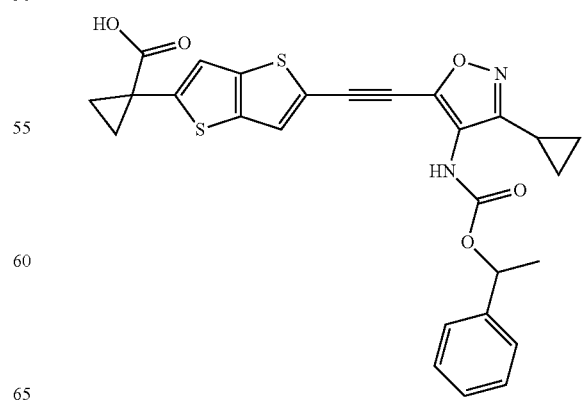

TABLE 15-continued
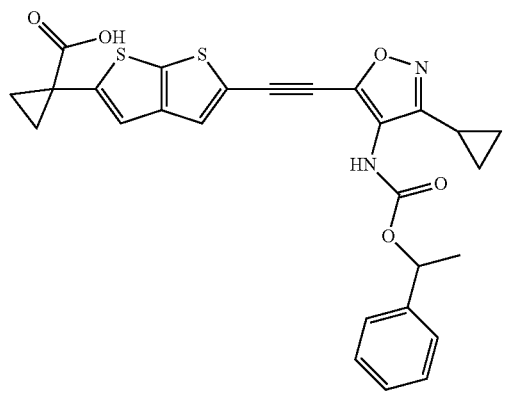 [SMILES: CC(OC(=O)Nc1c(C2CC2)noc1C#Cc1cc2cc(C3(C(=O)O)CC3)sc2s1)c1ccccc1]
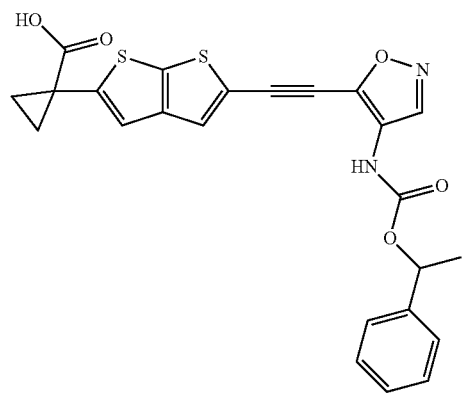 [SMILES: CC(OC(=O)Nc1cnoc1C#Cc1cc2cc(C3(C(=O)O)CC3)sc2s1)c1ccccc1]
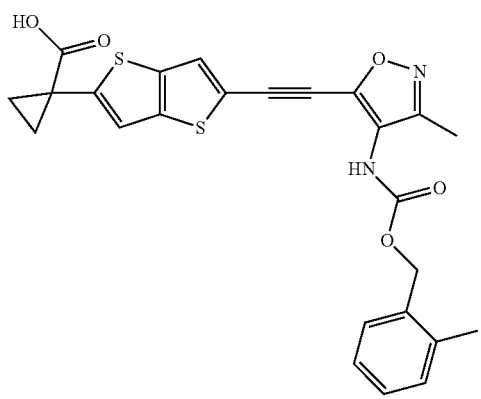 [SMILES: Cc1ccccc1COC(=O)Nc1c(C)noc1C#Cc1cc2sc(C3(C(=O)O)CC3)cc2s1]
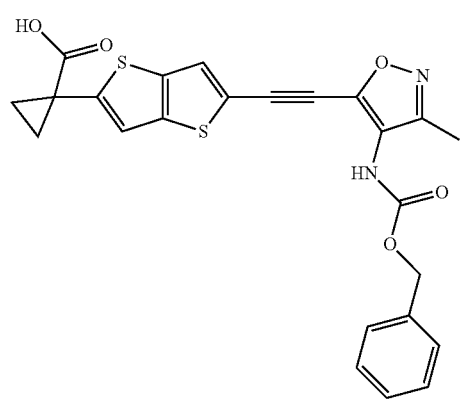 [SMILES: Cc1noc(C#Cc2cc3sc(C4(C(=O)O)CC4)cc3s2)c1NC(=O)OCc1ccccc1]
TABLE 15-continued
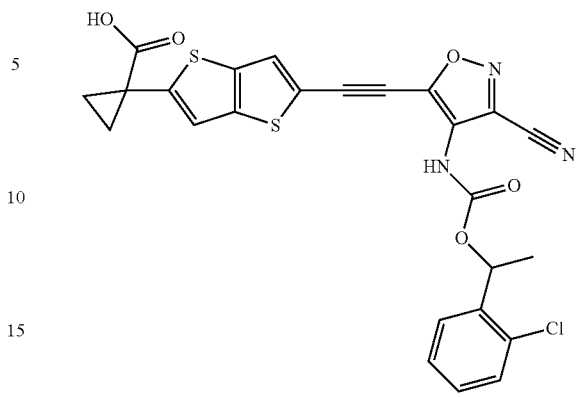

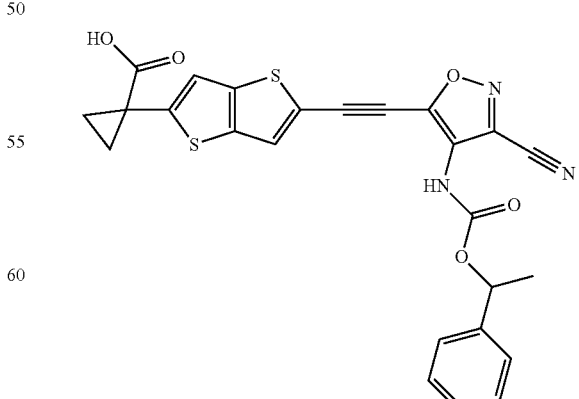

TABLE 15-continued
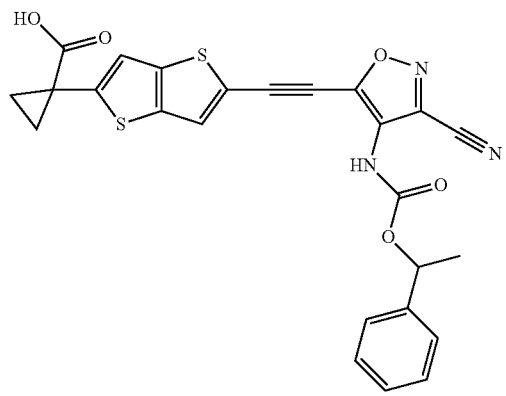
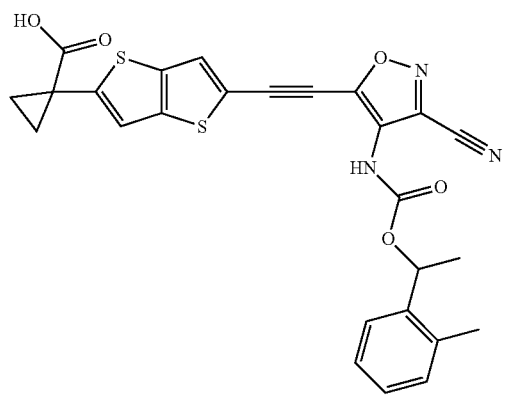 [SMILES: CC(OC(=O)Nc1c(C#N)noc1C#Cc1cc2sc(C3(C(=O)O)CC3)cc2s1)c1ccccc1Cl]
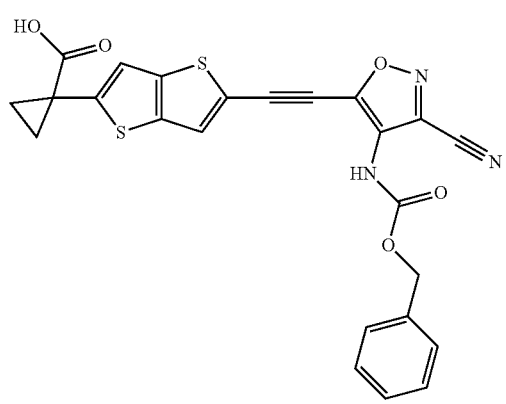 [SMILES: N#Cc1noc(C#Cc2cc3sc(C4(C(=O)O)CC4)cc3s2)c1NC(=O)OCc1ccccc1]
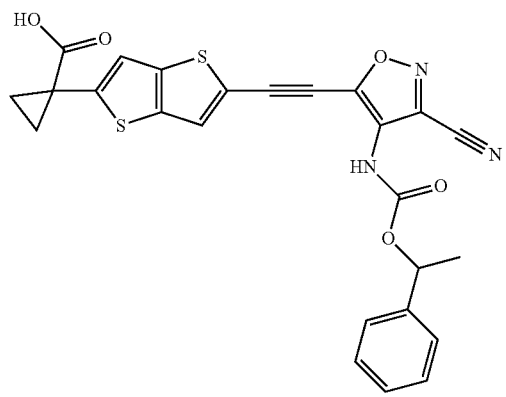 [SMILES: CC(OC(=O)Nc1c(C#N)noc1C#Cc1cc2sc(C3(C(=O)O)CC3)cc2s1)c1ccccc1]
TABLE 15-continued
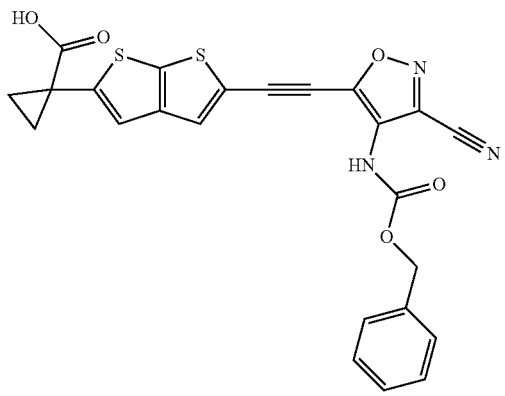
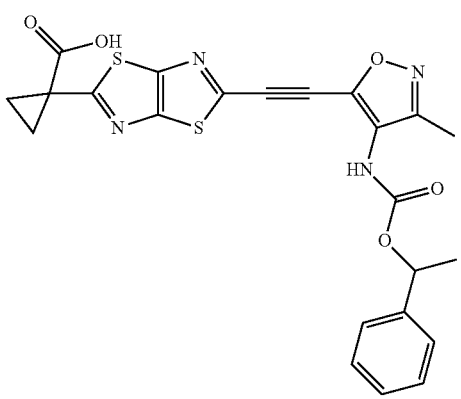 [SMILES: Cc1noc(C#Cc2nc3sc(C4(C(=O)O)CC4)nc3s2)c1NC(=O)OC(C)c1ccccc1]

TABLE 15-continued
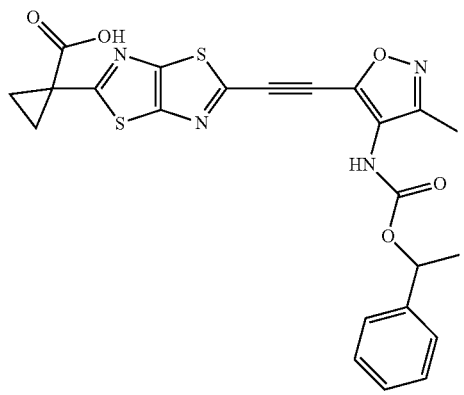 [SMILES: Cc1noc(C#Cc2nc3sc(C4(C(=O)O)CC4)nc3s2)c1NC(=O)OC(C)c1ccccc1]
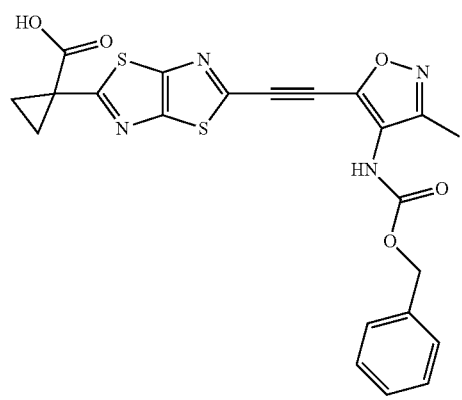
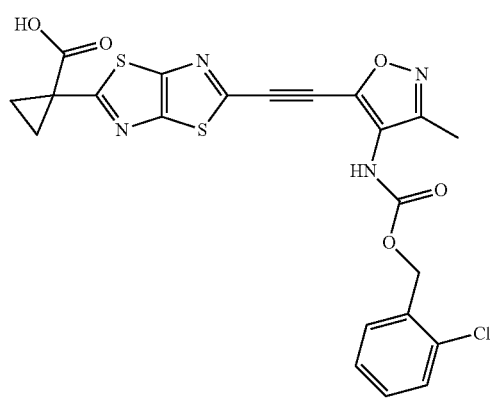
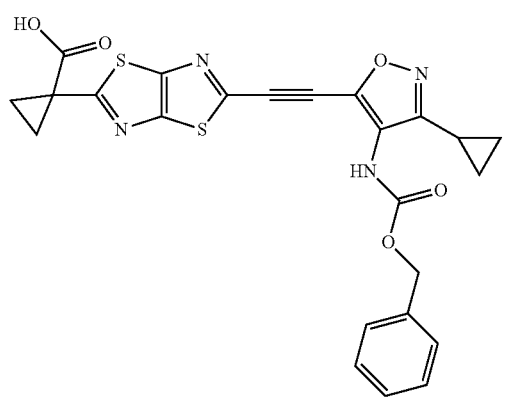
TABLE 15-continued
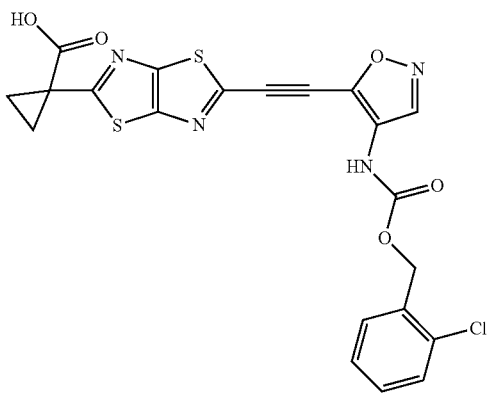 [SMILES: O=C(Nc1cnoc1C#Cc1nc2sc(C3(C(=O)O)CC3)nc2s1)OCc1ccccc1Cl]
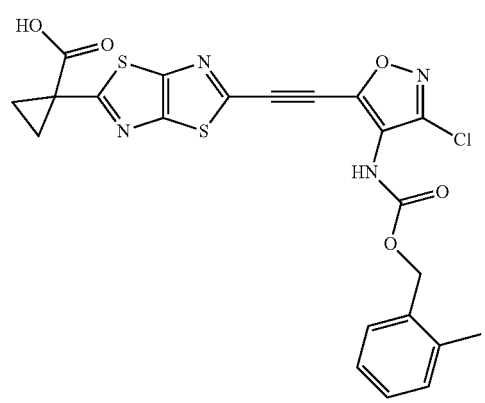
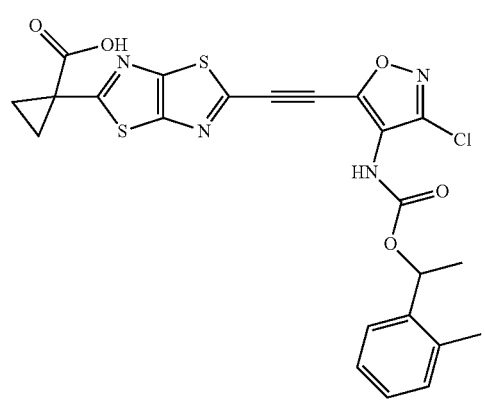
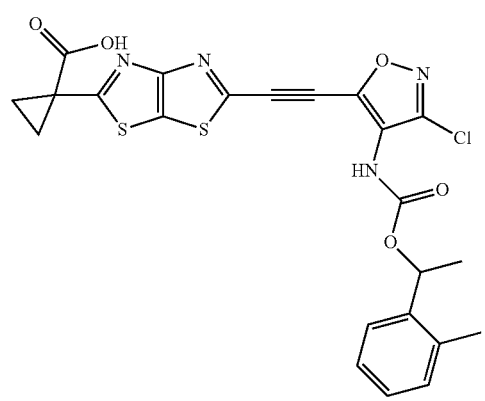 [SMILES: Cc1ccccc1C(C)OC(=O)Nc1c(Cl)noc1C#Cc1nc2nc(C3(C(=O)O)CC3)sc2s1]

TABLE 15-continued
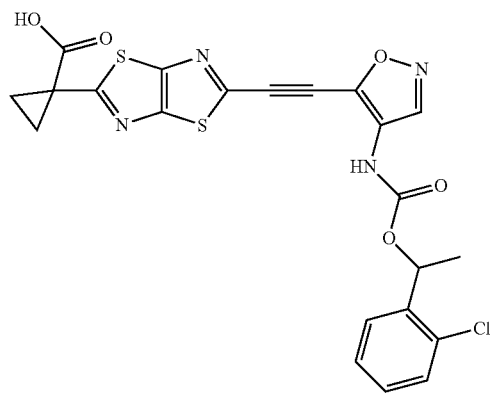 [SMILES: CC(OC(=O)Nc1cnoc1C#Cc1nc2sc(C3(C(=O)O)CC3)nc2s1)c1ccccc1Cl]
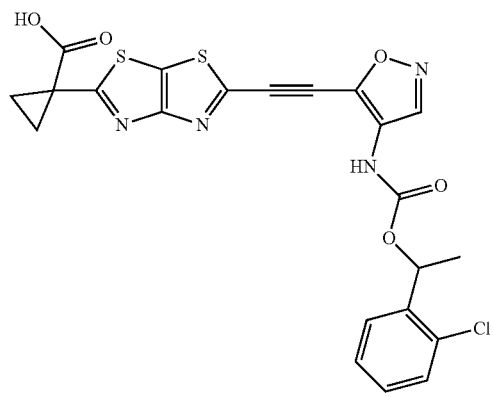 [SMILES: CC(OC(=O)Nc1cnoc1C#Cc1nc2nc(C3(C(=O)O)CC3)sc2s1)c1ccccc1Cl]
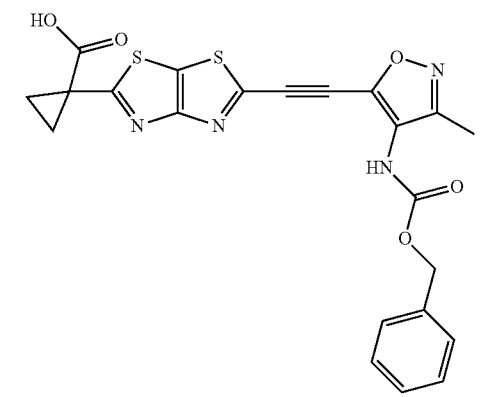
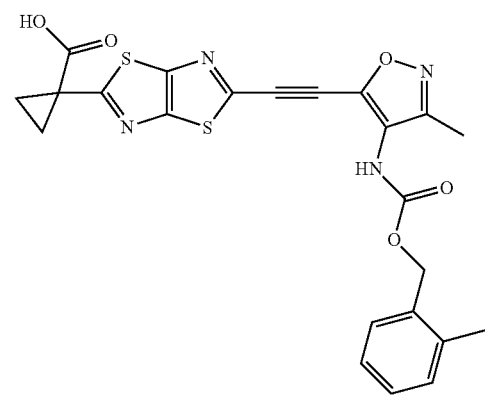 [SMILES: Cc1ccccc1COC(=O)Nc1c(C)noc1C#Cc1nc2sc(C3(C(=O)O)CC3)nc2s1]
TABLE 15-continued
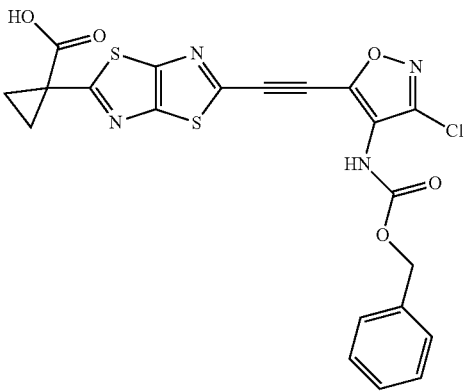 [SMILES: O=C(Nc1c(Cl)noc1C#Cc1nc2sc(C3(C(=O)O)CC3)nc2s1)OCc1ccccc1]
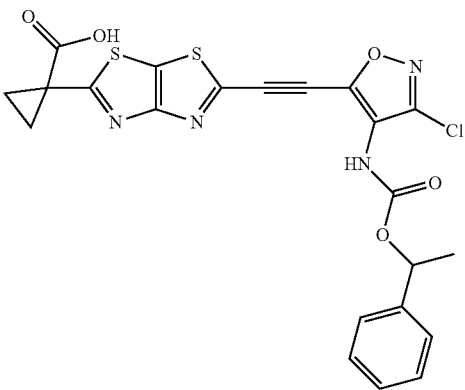 [SMILES: CC(OC(=O)Nc1c(Cl)noc1C#Cc1nc2nc(C3(C(=O)O)CC3)sc2s1)c1ccccc1]
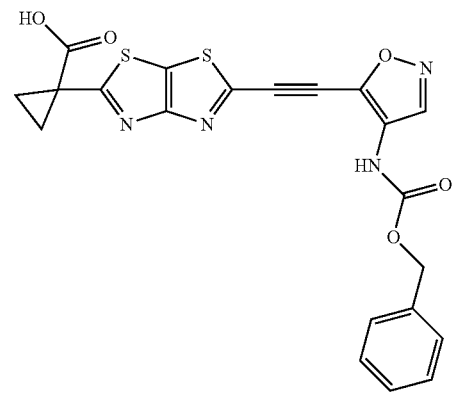 [SMILES: O=C(Nc1cnoc1C#Cc1nc2nc(C3(C(=O)O)CC3)sc2s1)OCc1ccccc1]
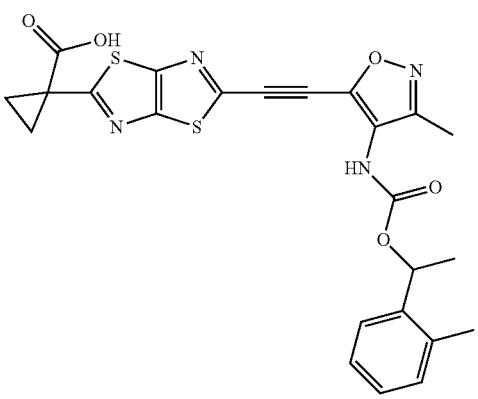 [SMILES: Cc1ccccc1C(C)OC(=O)Nc1c(C)noc1C#Cc1nc2sc(C3(C(=O)O)CC3)nc2s1]

| | |
|---|---|
| 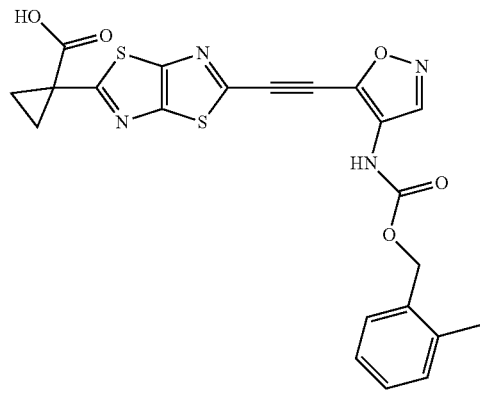 [SMILES: Cc1ccccc1COC(=O)Nc1cnoc1C#Cc1nc2sc(C3(C(=O)O)CC3)nc2s1] | 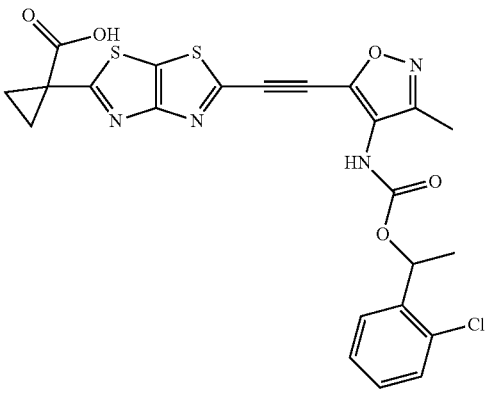 |
| 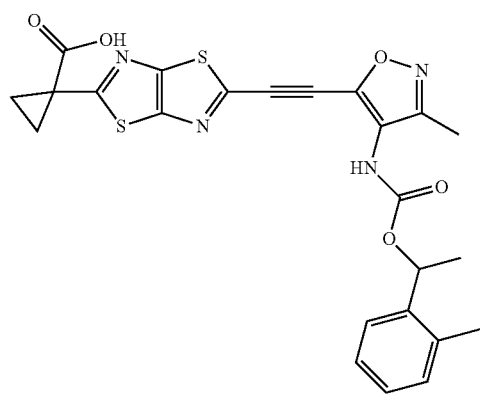 [SMILES: Cc1ccccc1C(C)OC(=O)Nc1c(C)noc1C#Cc1nc2sc(C3(C(=O)O)CC3)nc2s1] | 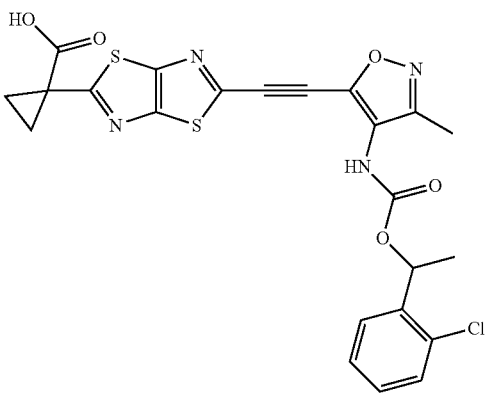 |
| 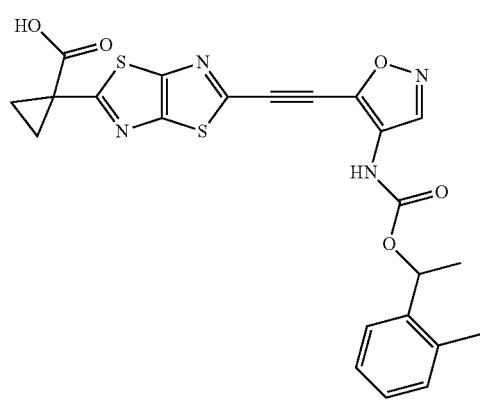 [SMILES: Cc1ccccc1C(C)OC(=O)Nc1cnoc1C#Cc1nc2sc(C3(C(=O)O)CC3)nc2s1] | 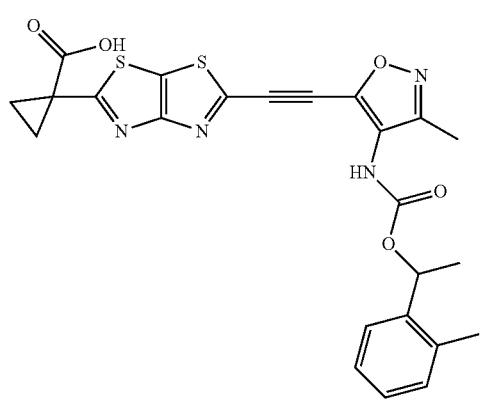 |
| 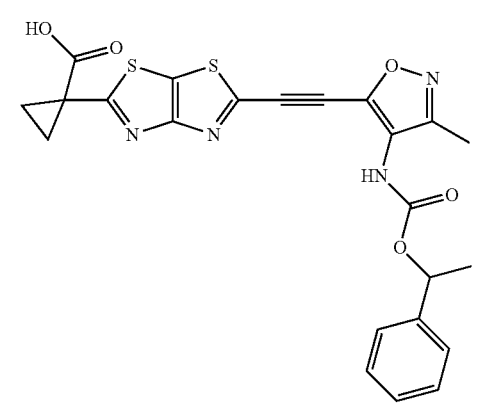 [SMILES: Cc1noc(C#Cc2nc3nc(C4(C(=O)O)CC4)sc3s2)c1NC(=O)OC(C)c1ccccc1] | 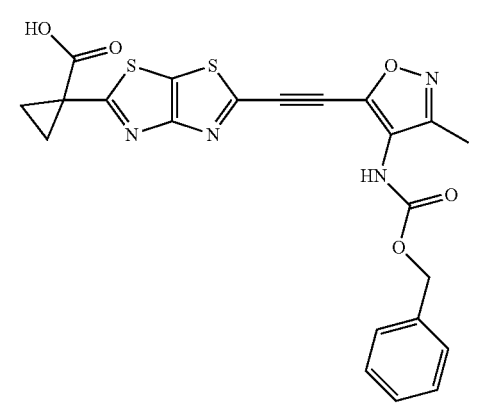 [SMILES: Cc1noc(C#Cc2nc3nc(C4(C(=O)O)CC4)sc3s2)c1NC(=O)OCc1ccccc1] |

TABLE 15-continued
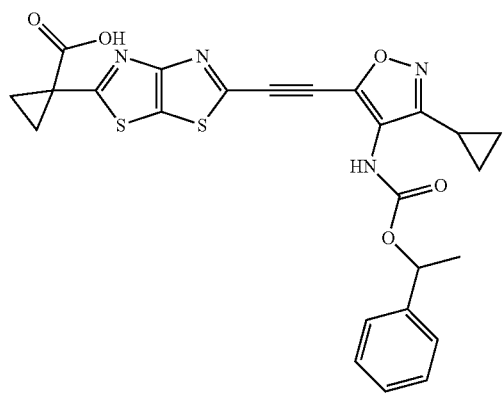 [SMILES: CC(OC(=O)Nc1c(C2CC2)noc1C#Cc1nc2nc(C3(C(=O)O)CC3)sc2s1)c1ccccc1]
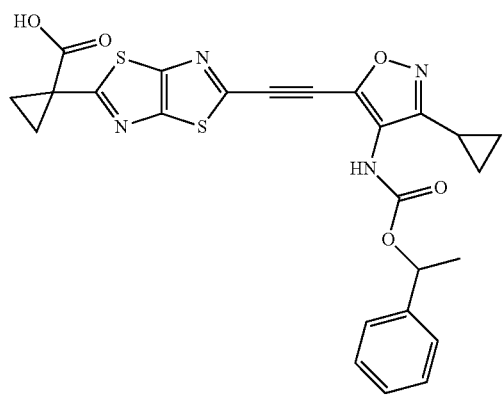 [SMILES: CC(OC(=O)Nc1c(C2CC2)noc1C#Cc1nc2sc(C3(C(=O)O)CC3)nc2s1)c1ccccc1]
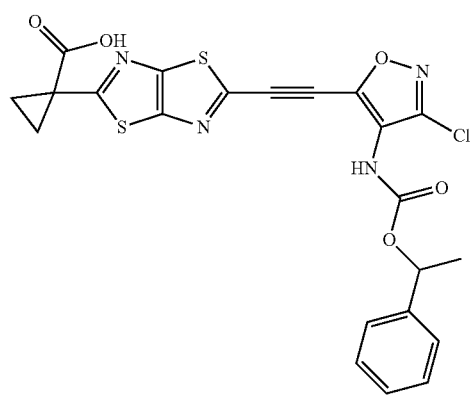
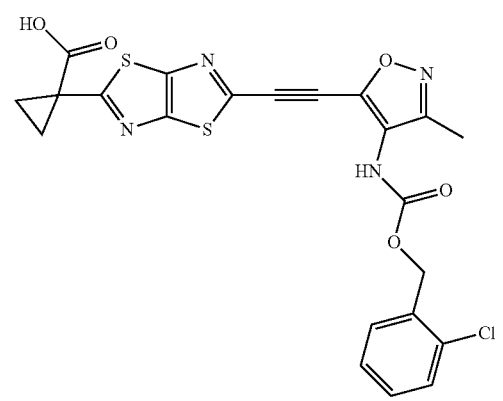
TABLE 15-continued
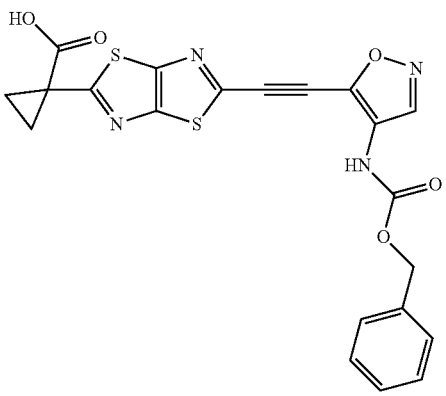 [SMILES: O=C(Nc1cnoc1C#Cc1nc2sc(C3(C(=O)O)CC3)nc2s1)OCc1ccccc1]
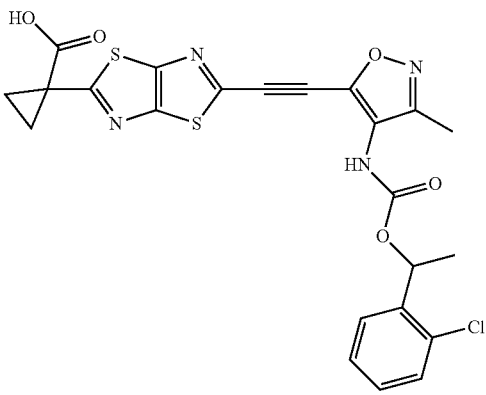 [SMILES: Cc1noc(C#Cc2nc3sc(C4(C(=O)O)CC4)nc3s2)c1NC(=O)OC(C)c1ccccc1Cl]
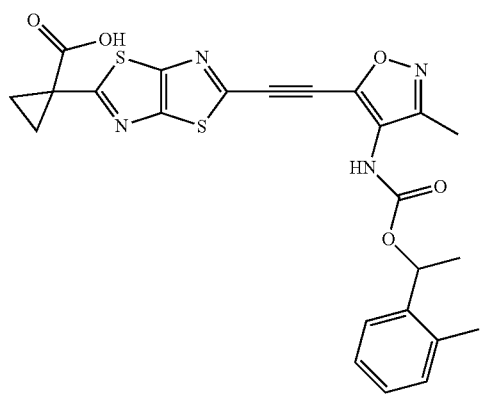 [SMILES: Cc1ccccc1C(C)OC(=O)Nc1c(C)noc1C#Cc1nc2sc(C3(C(=O)O)CC3)nc2s1]
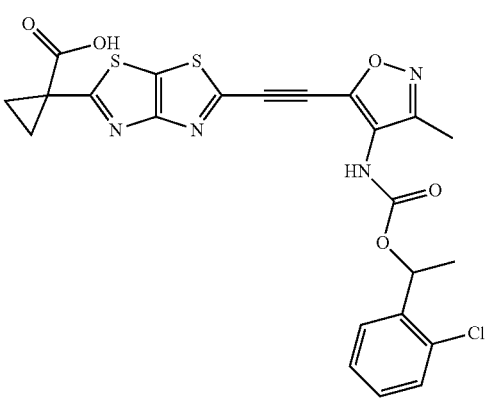 [SMILES: Cc1noc(C#Cc2nc3nc(C4(C(=O)O)CC4)sc3s2)c1NC(=O)OC(C)c1ccccc1Cl]

TABLE 15-continued
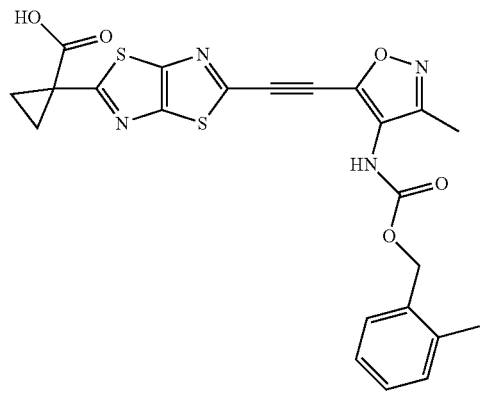
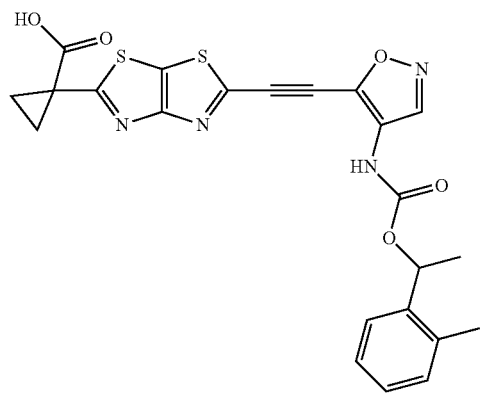 [SMILES: Cc1ccccc1C(C)OC(=O)Nc1cnoc1C#Cc1nc2nc(C3(C(=O)O)CC3)sc2s1]
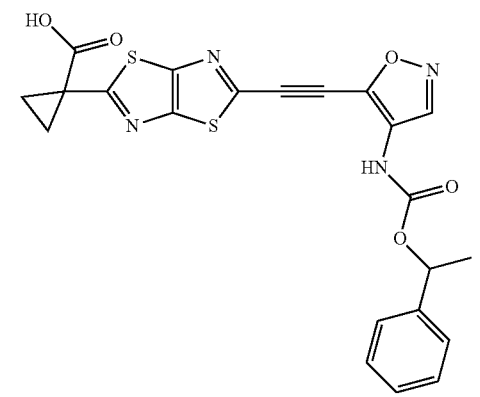 [SMILES: CC(OC(=O)Nc1cnoc1C#Cc1nc2sc(C3(C(=O)O)CC3)nc2s1)c1ccccc1]
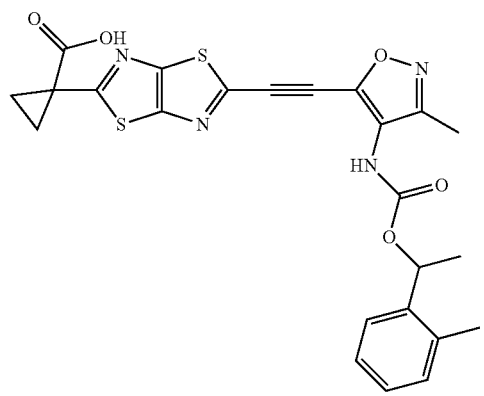
TABLE 15-continued
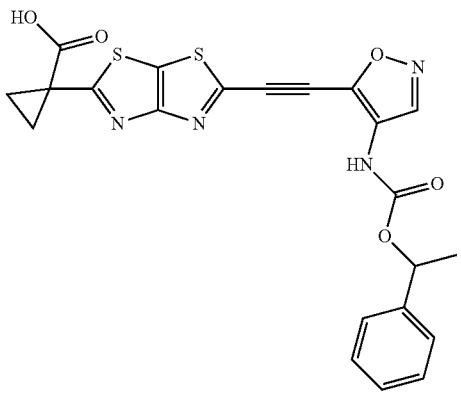 [SMILES: CC(OC(=O)Nc1cnoc1C#Cc1nc2nc(C3(C(=O)O)CC3)sc2s1)c1ccccc1]
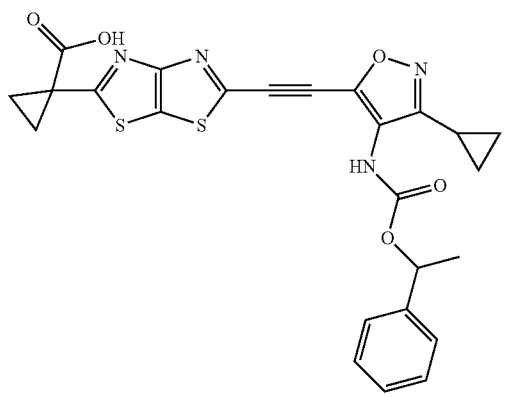 [SMILES: CC(OC(=O)Nc1c(C2CC2)noc1C#Cc1nc2nc(C3(C(=O)O)CC3)sc2s1)c1ccccc1]
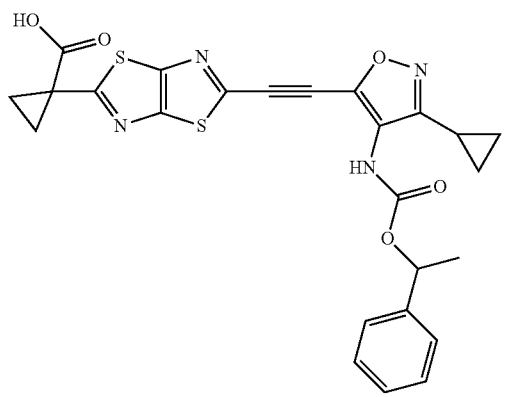 [SMILES: CC(OC(=O)Nc1c(C2CC2)noc1C#Cc1nc2sc(C3(C(=O)O)CC3)nc2s1)c1ccccc1]

TABLE 15-continued
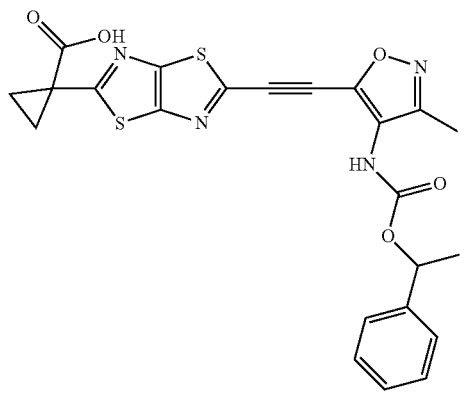 [SMILES: Cc1noc(C#Cc2nc3sc(C4(C(=O)O)CC4)nc3s2)c1NC(=O)OC(C)c1ccccc1]
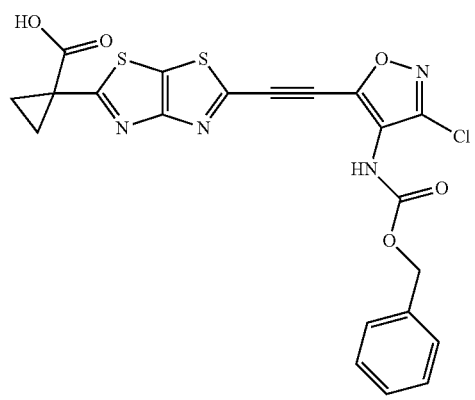
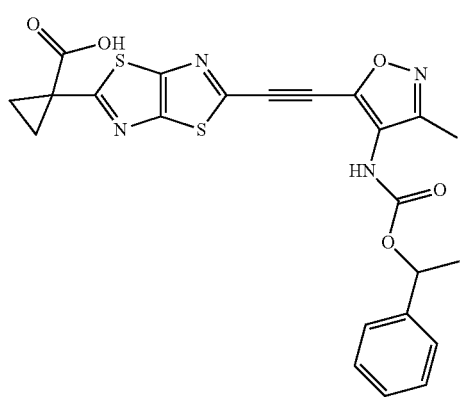 [SMILES: Cc1noc(C#Cc2nc3sc(C4(C(=O)O)CC4)nc3s2)c1NC(=O)OC(C)c1ccccc1]
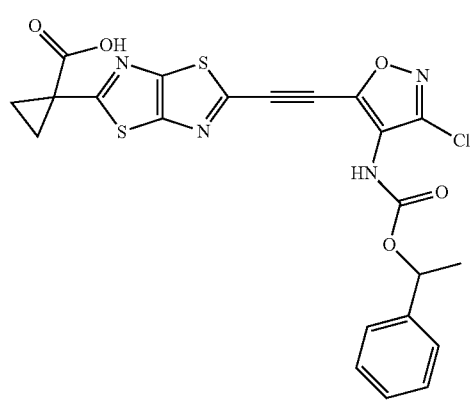
TABLE 15-continued
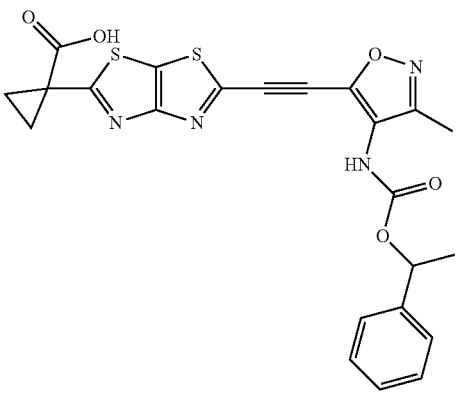 [SMILES: Cc1noc(C#Cc2nc3nc(C4(C(=O)O)CC4)sc3s2)c1NC(=O)OC(C)c1ccccc1]
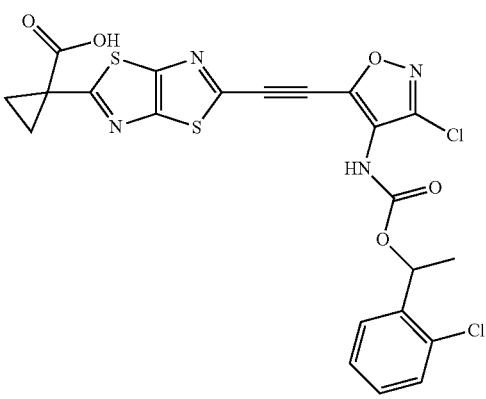
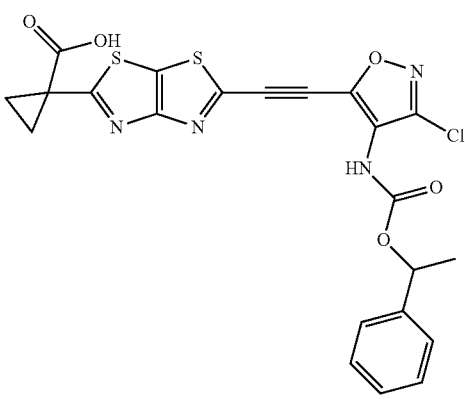 [SMILES: CC(OC(=O)Nc1c(Cl)noc1C#Cc1nc2nc(C3(C(=O)O)CC3)sc2s1)c1ccccc1]
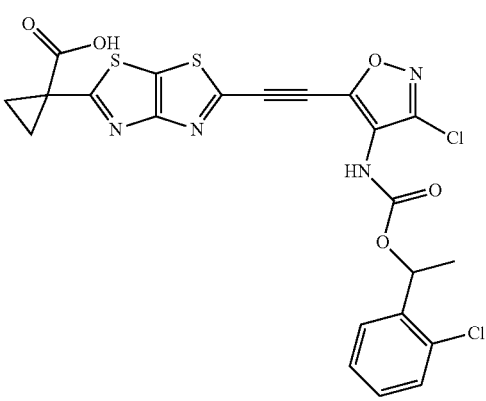 [SMILES: CC(OC(=O)Nc1c(Cl)noc1C#Cc1nc2nc(C3(C(=O)O)CC3)sc2s1)c1ccccc1Cl]

TABLE 15-continued
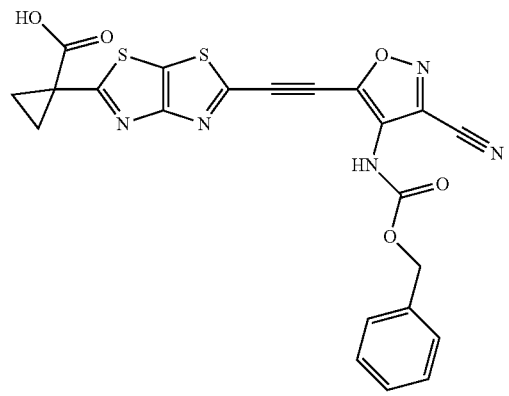
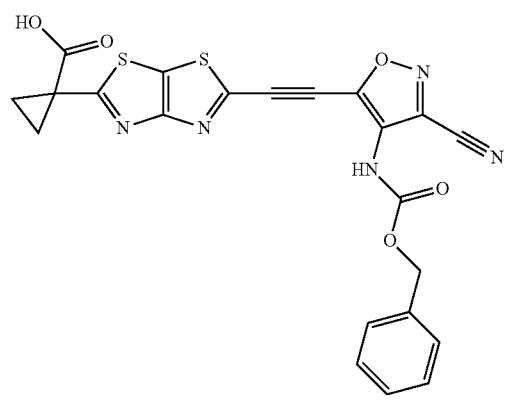
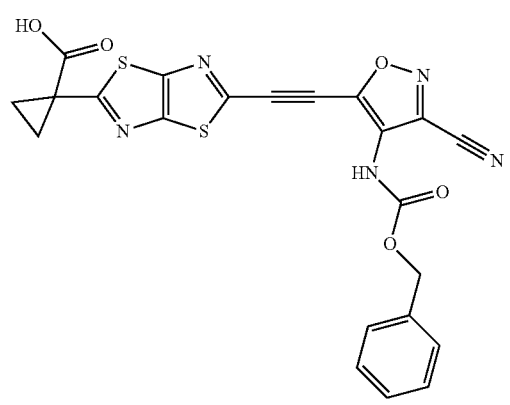 [SMILES: N#Cc1noc(C#Cc2nc3sc(C4(C(=O)O)CC4)nc3s2)c1NC(=O)OCc1ccccc1]
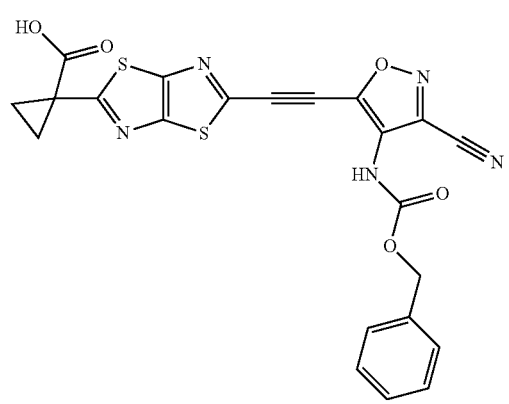
TABLE 16
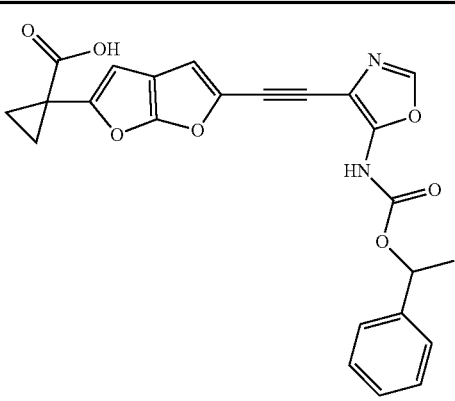
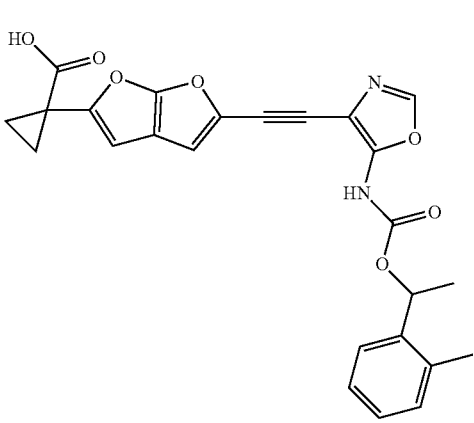
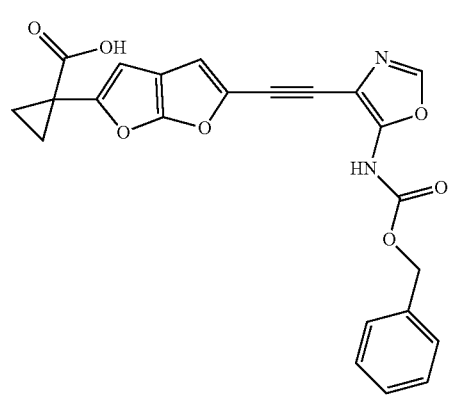 [SMILES: O=C(Nc1ocnc1C#Cc1cc2cc(C3(C(=O)O)CC3)oc2o1)OCc1ccccc1]
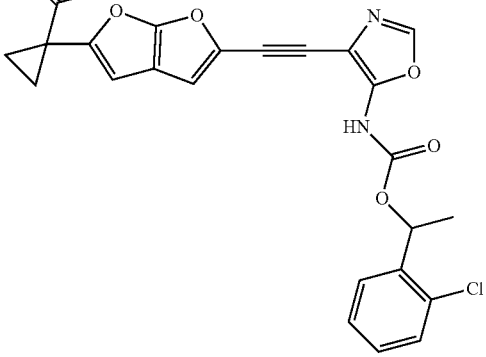
In some embodiments, compounds of Formula (I) are selected from the following compounds as listed in Table 16.

TABLE 16-continued
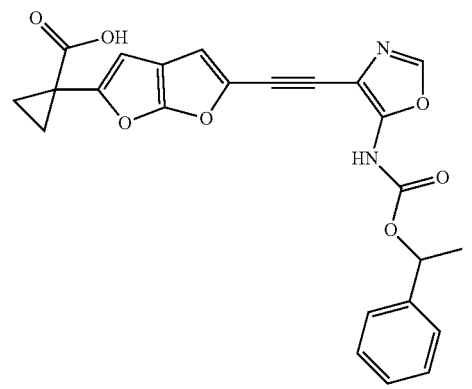 [SMILES: CC(OC(=O)Nc1ocnc1C#Cc1cc2cc(C3(C(=O)O)CC3)oc2o1)c1ccccc1]
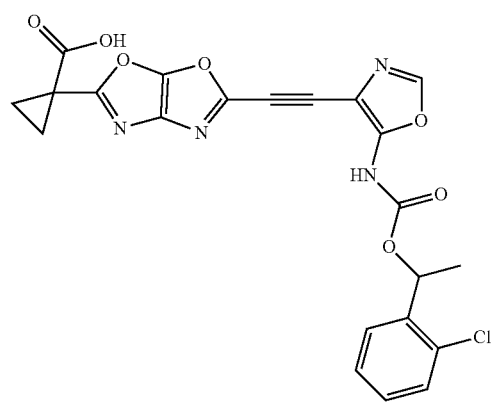 [SMILES: CC(OC(=O)Nc1ocnc1C#Cc1nc2nc(C3(C(=O)O)CC3)oc2o1)c1ccccc1Cl]
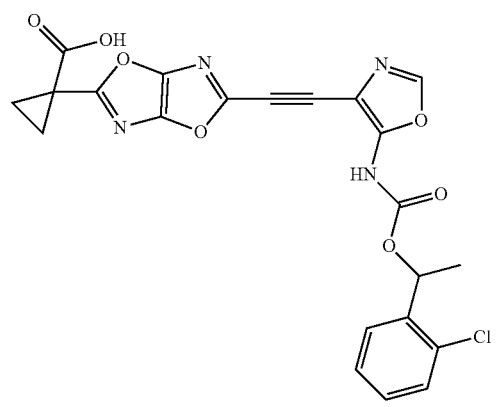 [SMILES: CC(OC(=O)Nc1ocnc1C#Cc1nc2oc(C3(C(=O)O)CC3)nc2o1)c1ccccc1Cl]
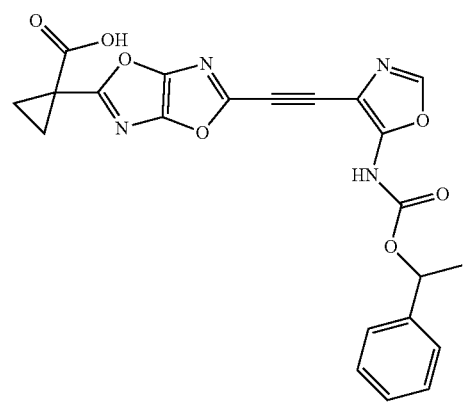 [SMILES: CC(OC(=O)Nc1ocnc1C#Cc1nc2oc(C3(C(=O)O)CC3)nc2o1)c1ccccc1]
TABLE 16-continued
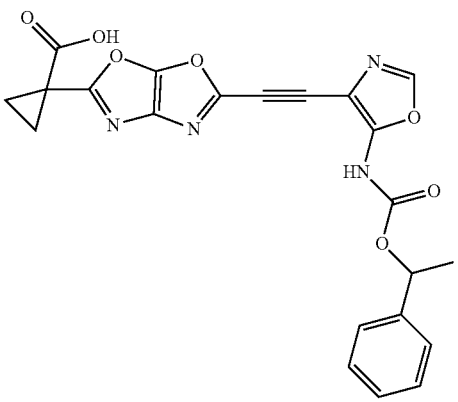 [SMILES: CC(OC(=O)Nc1ocnc1C#Cc1nc2nc(C3(C(=O)O)CC3)oc2o1)c1ccccc1]
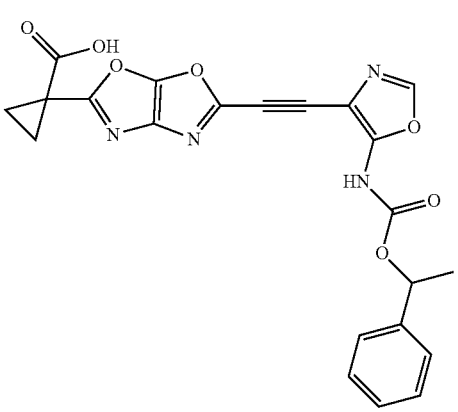 [SMILES: CC(OC(=O)Nc1ocnc1C#Cc1nc2nc(C3(C(=O)O)CC3)oc2o1)c1ccccc1]
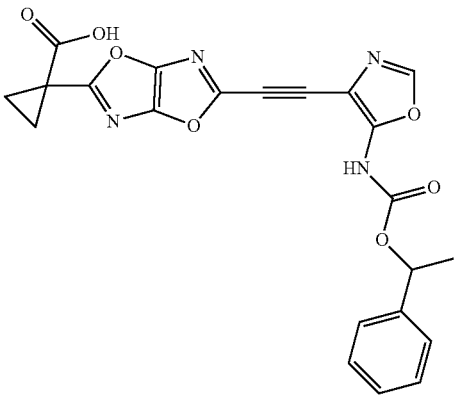 [SMILES: CC(OC(=O)Nc1ocnc1C#Cc1nc2oc(C3(C(=O)O)CC3)nc2o1)c1ccccc1]
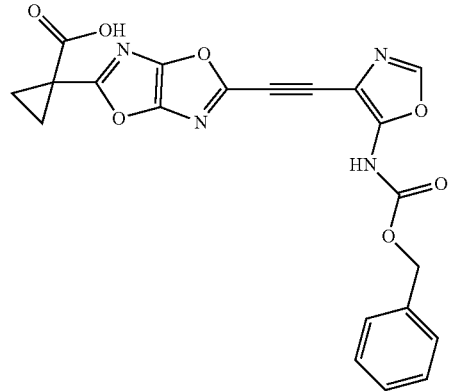 [SMILES: O=C(Nc1ocnc1C#Cc1nc2oc(C3(C(=O)O)CC3)nc2o1)OCc1ccccc1]

TABLE 16-continued
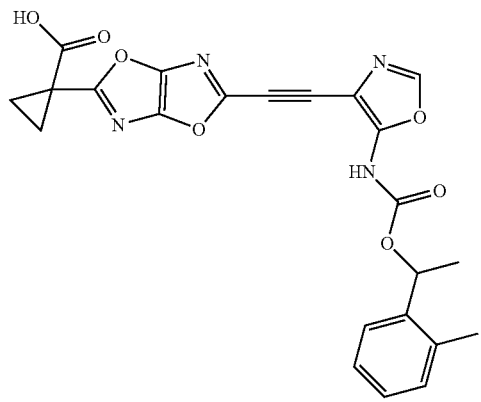 [SMILES: Cc1ccccc1C(C)OC(=O)Nc1ocnc1C#Cc1nc2oc(C3(C(=O)O)CC3)nc2o1]
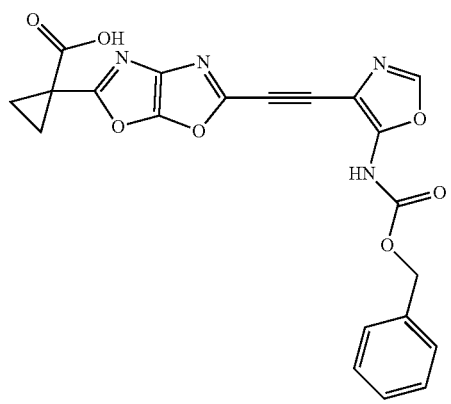 [SMILES: O=C(Nc1ocnc1C#Cc1nc2nc(C3(C(=O)O)CC3)oc2o1)OCc1ccccc1]
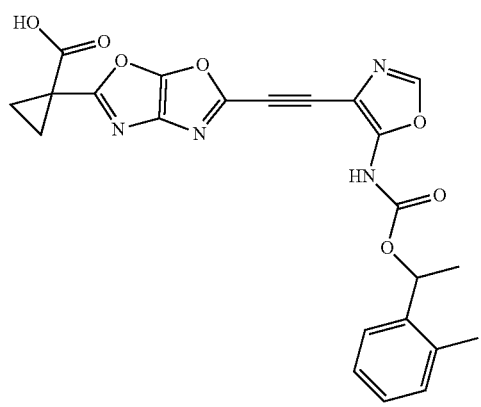 [SMILES: Cc1ccccc1C(C)OC(=O)Nc1ocnc1C#Cc1nc2nc(C3(C(=O)O)CC3)oc2o1]
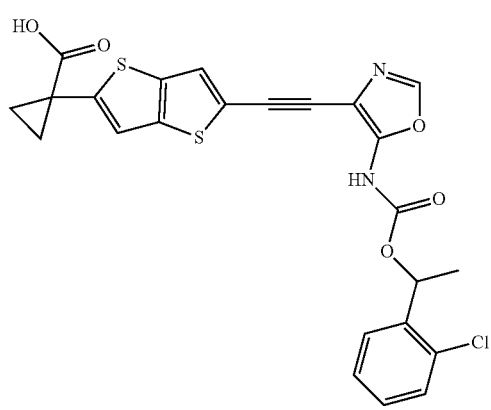 [SMILES: CC(OC(=O)Nc1ocnc1C#Cc1cc2sc(C3(C(=O)O)CC3)cc2s1)c1ccccc1Cl]
TABLE 16-continued
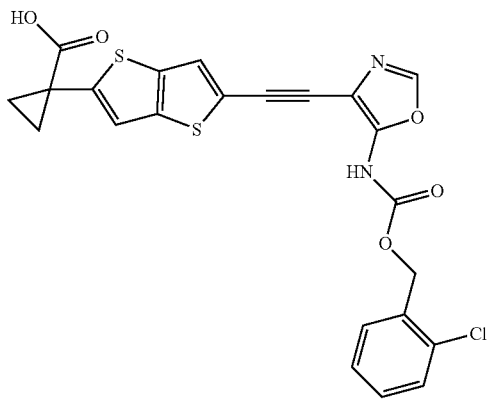 [SMILES: O=C(Nc1ocnc1C#Cc1cc2sc(C3(C(=O)O)CC3)cc2s1)OCc1ccccc1Cl]
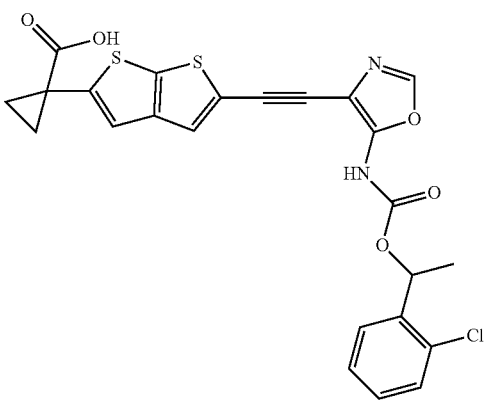
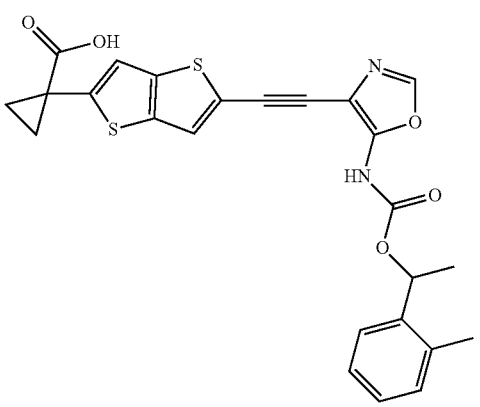 [SMILES: Cc1ccccc1C(C)OC(=O)Nc1ocnc1C#Cc1cc2sc(C3(C(=O)O)CC3)cc2s1]
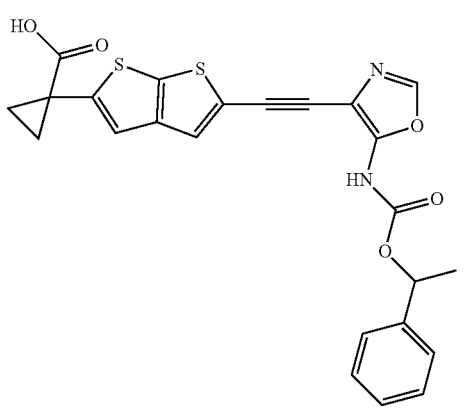 [SMILES: CC(OC(=O)Nc1ocnc1C#Cc1cc2cc(C3(C(=O)O)CC3)sc2s1)c1ccccc1]

TABLE 16-continued
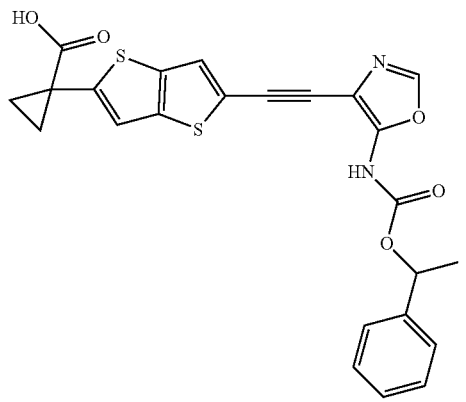 [SMILES: CC(OC(=O)Nc1ocnc1C#Cc1cc2sc(C3(C(=O)O)CC3)cc2s1)c1ccccc1]
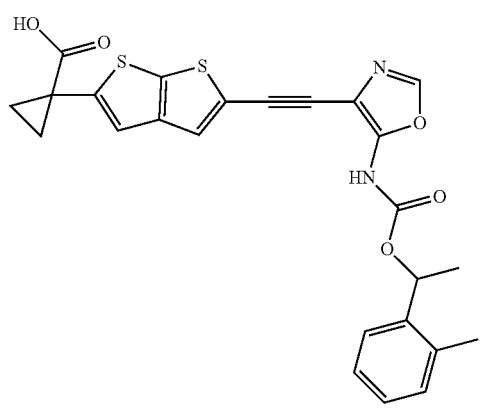 [SMILES: Cc1ccccc1C(C)OC(=O)Nc1ocnc1C#Cc1cc2cc(C3(C(=O)O)CC3)sc2s1]
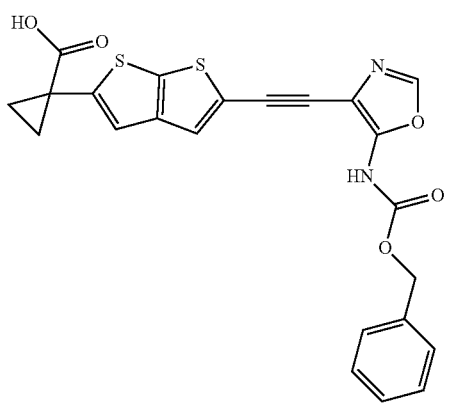 [SMILES: O=C(Nc1ocnc1C#Cc1cc2cc(C3(C(=O)O)CC3)sc2s1)OCc1ccccc1]
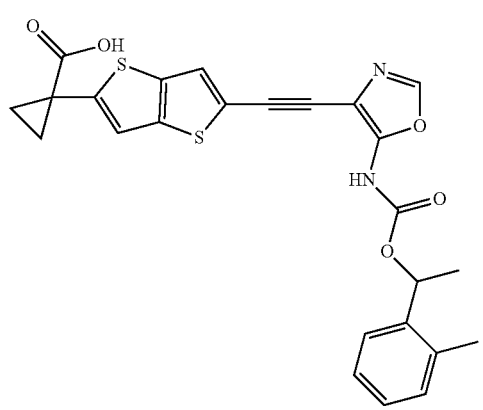 [SMILES: Cc1ccccc1C(C)OC(=O)Nc1ocnc1C#Cc1cc2sc(C3(C(=O)O)CC3)cc2s1]
TABLE 16-continued
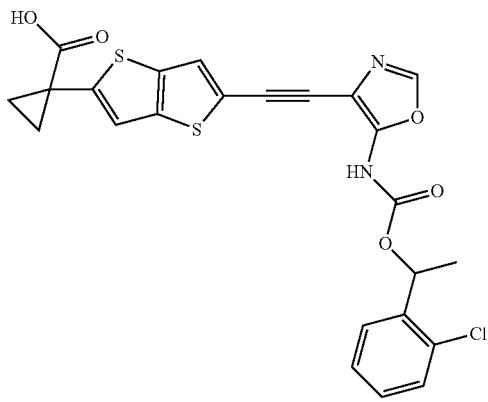 [SMILES: CC(OC(=O)Nc1ocnc1C#Cc1cc2sc(C3(C(=O)O)CC3)cc2s1)c1ccccc1Cl]
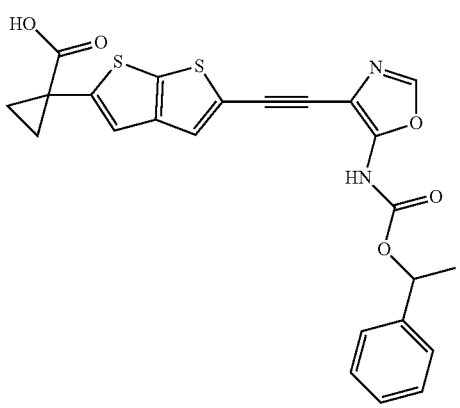 [SMILES: CC(OC(=O)Nc1ocnc1C#Cc1cc2cc(C3(C(=O)O)CC3)sc2s1)c1ccccc1]
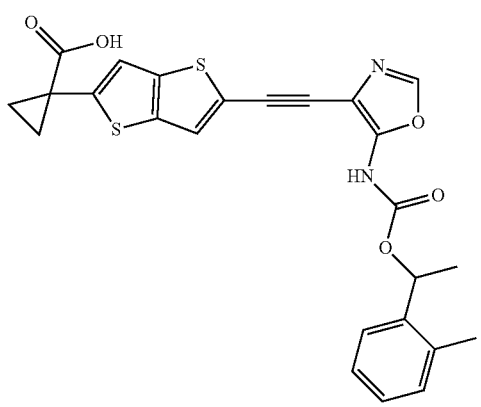 [SMILES: Cc1ccccc1C(C)OC(=O)Nc1ocnc1C#Cc1cc2sc(C3(C(=O)O)CC3)cc2s1]
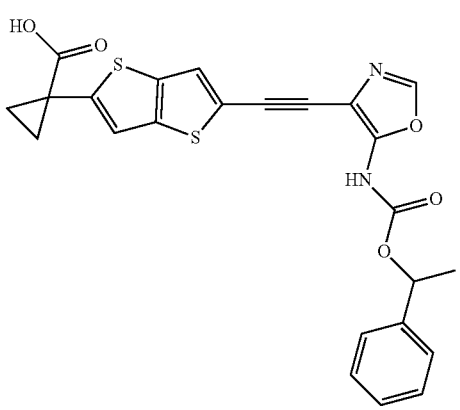 [SMILES: CC(OC(=O)Nc1ocnc1C#Cc1cc2sc(C3(C(=O)O)CC3)cc2s1)c1ccccc1]

TABLE 16-continued
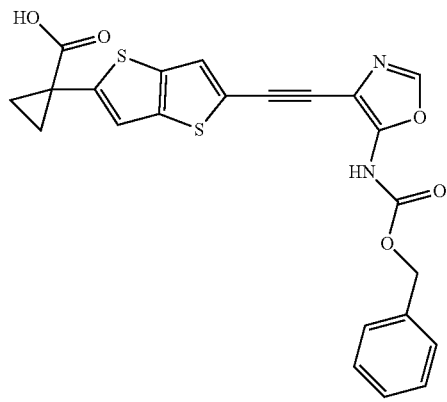 [SMILES: O=C(Nc1ocnc1C#Cc1cc2sc(C3(C(=O)O)CC3)cc2s1)OCc1ccccc1]
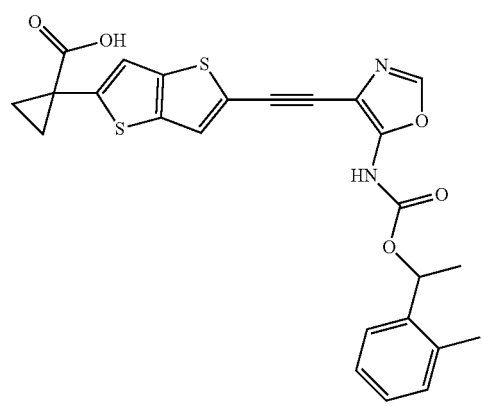 [SMILES: Cc1ccccc1C(C)OC(=O)Nc1ocnc1C#Cc1cc2sc(C3(C(=O)O)CC3)cc2s1]
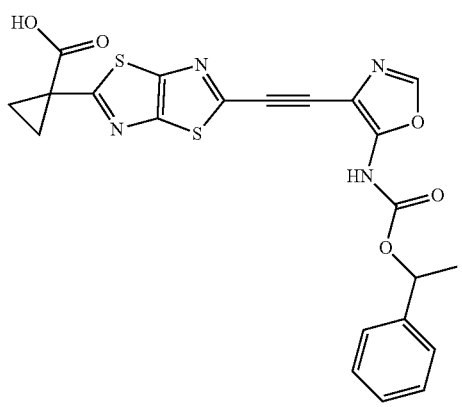 [SMILES: CC(OC(=O)Nc1ocnc1C#Cc1nc2sc(C3(C(=O)O)CC3)nc2s1)c1ccccc1]
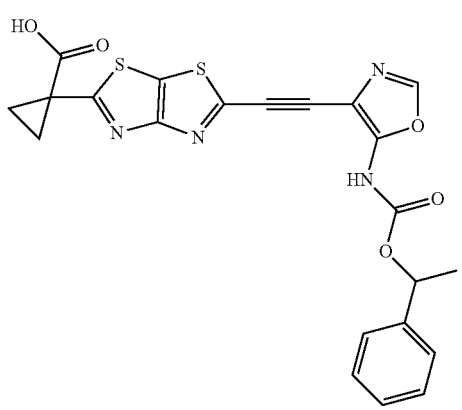 [SMILES: CC(OC(=O)Nc1ocnc1C#Cc1nc2nc(C3(C(=O)O)CC3)sc2s1)c1ccccc1]
TABLE 16-continued
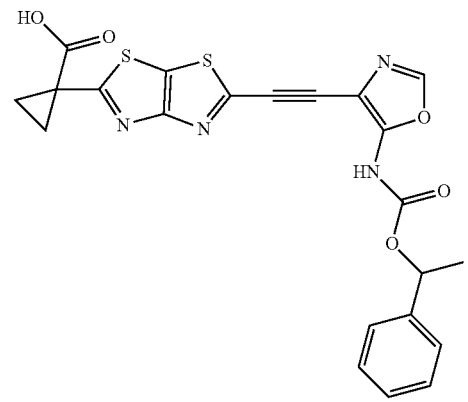 [SMILES: CC(OC(=O)Nc1ocnc1C#Cc1nc2nc(C3(C(=O)O)CC3)sc2s1)c1ccccc1]
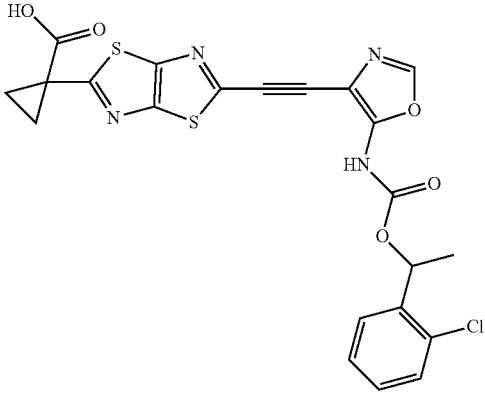 [SMILES: CC(OC(=O)Nc1ocnc1C#Cc1nc2sc(C3(C(=O)O)CC3)nc2s1)c1ccccc1Cl]
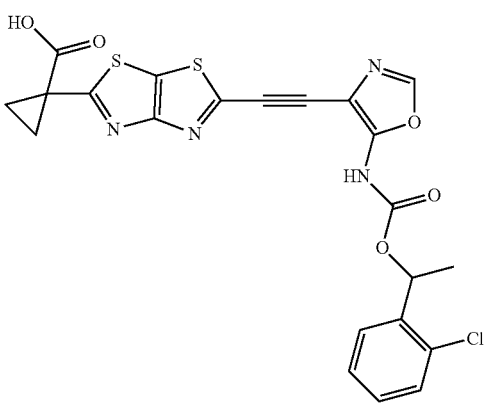 [SMILES: CC(OC(=O)Nc1ocnc1C#Cc1nc2nc(C3(C(=O)O)CC3)sc2s1)c1ccccc1Cl]
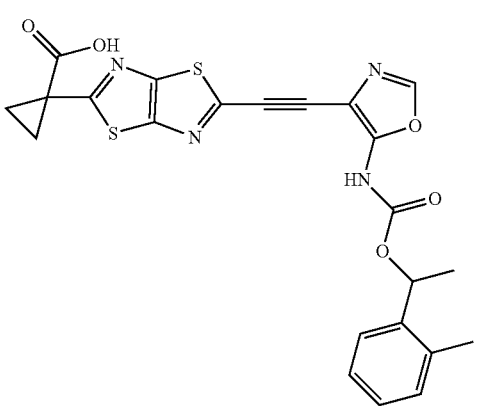 [SMILES: Cc1ccccc1C(C)OC(=O)Nc1ocnc1C#Cc1nc2sc(C3(C(=O)O)CC3)nc2s1]

TABLE 16-continued
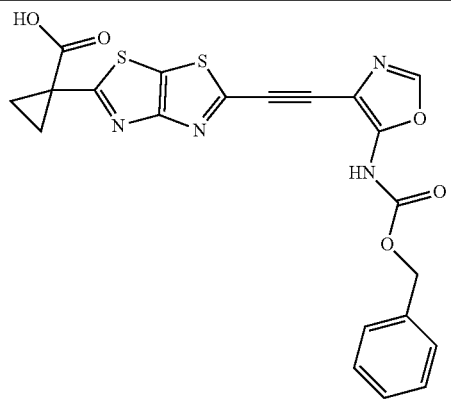
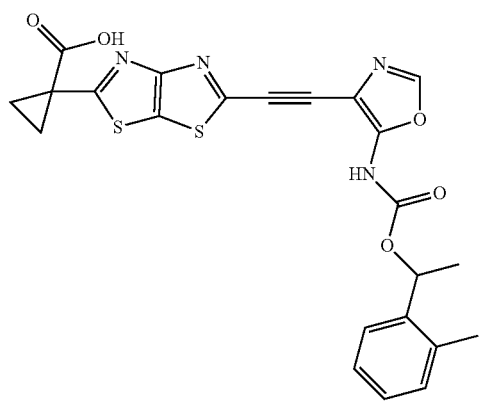 [SMILES: Cc1ccccc1C(C)OC(=O)Nc1ocnc1C#Cc1nc2nc(C3(C(=O)O)CC3)sc2s1]
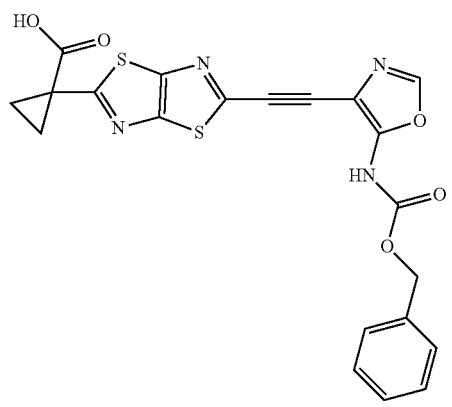 [SMILES: O=C(Nc1ocnc1C#Cc1nc2sc(C3(C(=O)O)CC3)nc2s1)OCc1ccccc1]
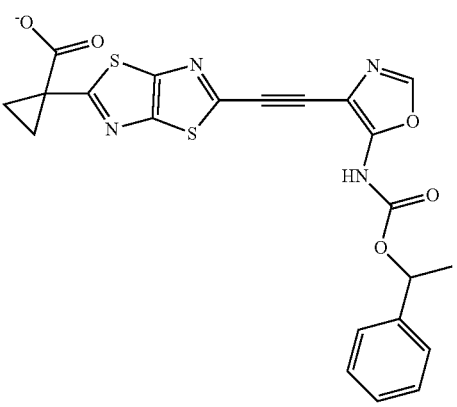
TABLE 17
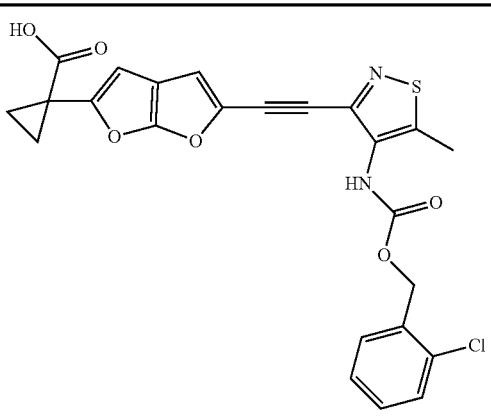
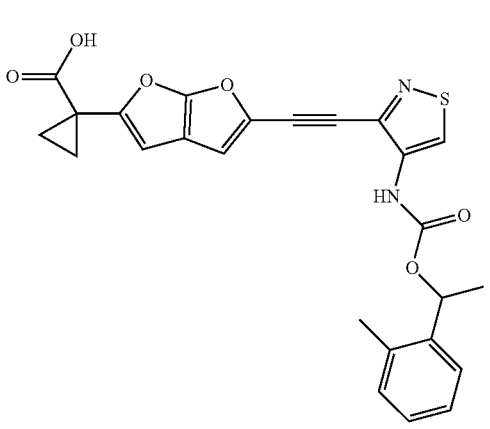 [SMILES: Cc1ccccc1C(C)OC(=O)Nc1csnc1C#Cc1cc2cc(C3(C(=O)O)CC3)oc2o1]
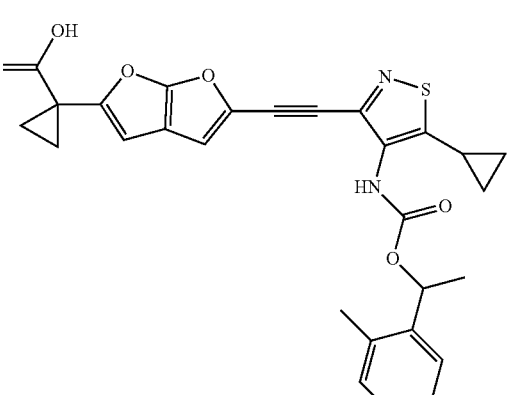
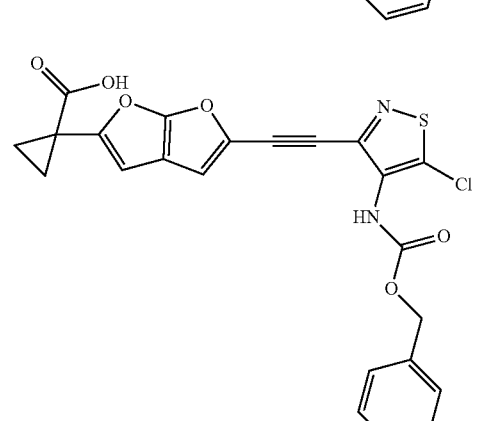
In some embodiments, compounds of Formula (I) are selected from the following compounds as listed in Table 17.

571
TABLE 17-continued
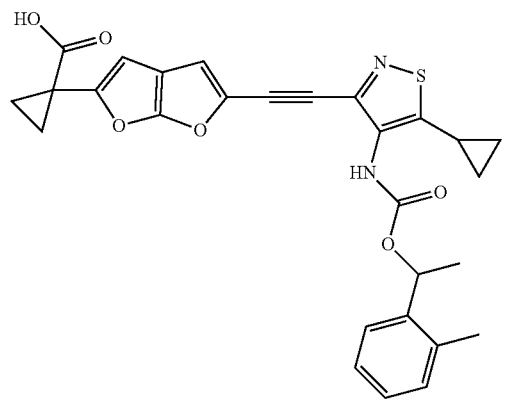
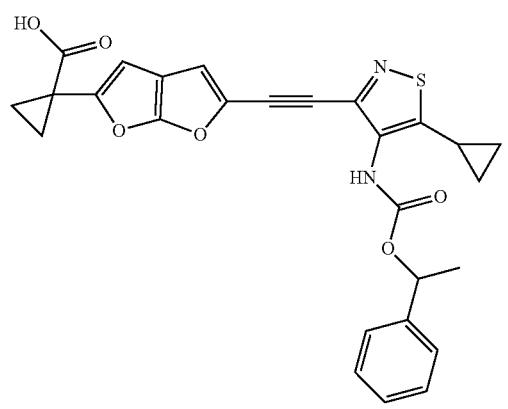 [SMILES: CC(OC(=O)Nc1c(C#Cc2cc3cc(C4(C(=O)O)CC4)oc3o2)nsc1C1CC1)c1ccccc1]
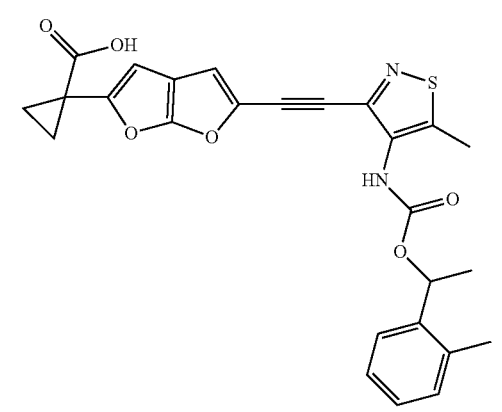 [SMILES: Cc1ccccc1C(C)OC(=O)Nc1c(C#Cc2cc3cc(C4(C(=O)O)CC4)oc3o2)nsc1C]
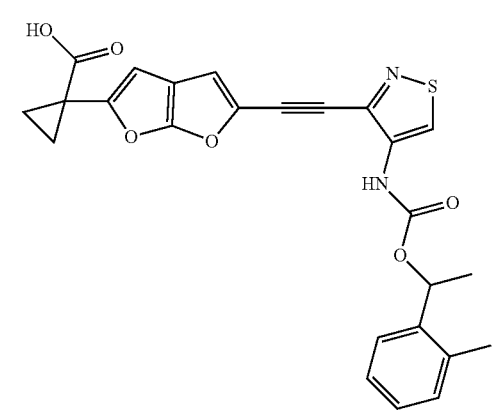 [SMILES: Cc1ccccc1C(C)OC(=O)Nc1csnc1C#Cc1cc2cc(C3(C(=O)O)CC3)oc2o1]
572
TABLE 17-continued
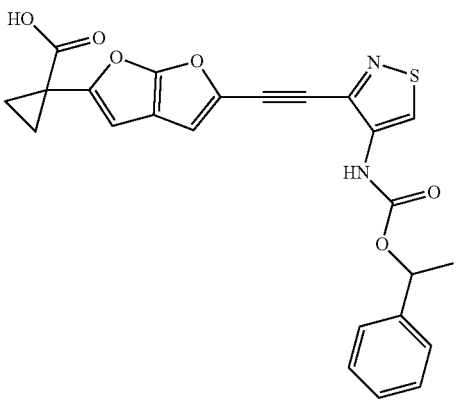 [SMILES: CC(OC(=O)Nc1csnc1C#Cc1cc2cc(C3(C(=O)O)CC3)oc2o1)c1ccccc1]
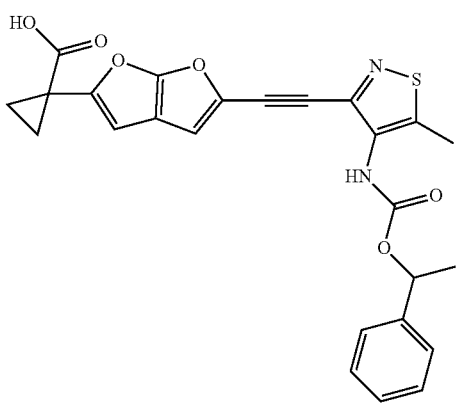 [SMILES: Cc1snc(C#Cc2cc3cc(C4(C(=O)O)CC4)oc3o2)c1NC(=O)OC(C)c1ccccc1]
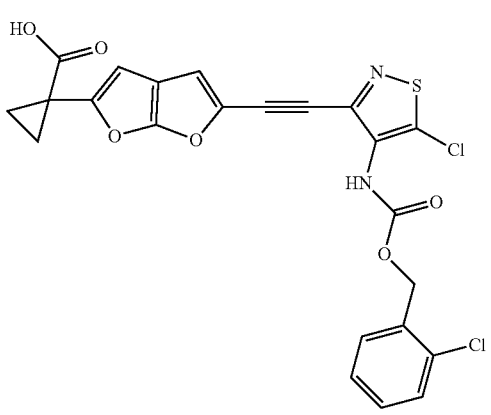

TABLE 17-continued
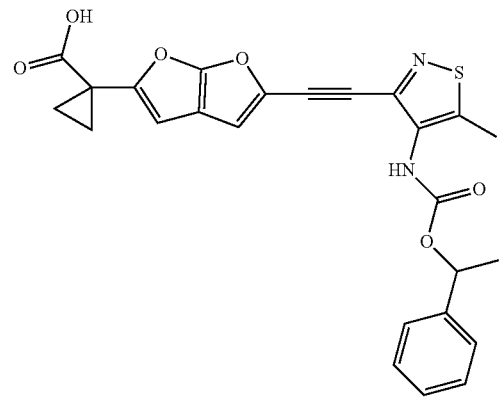 [SMILES: Cc1snc(C#Cc2cc3cc(C4(C(=O)O)CC4)oc3o2)c1NC(=O)OC(C)c1ccccc1]
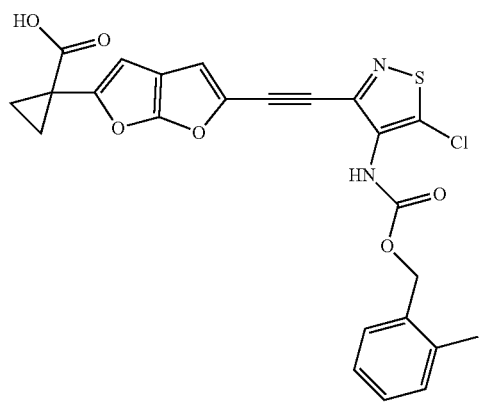
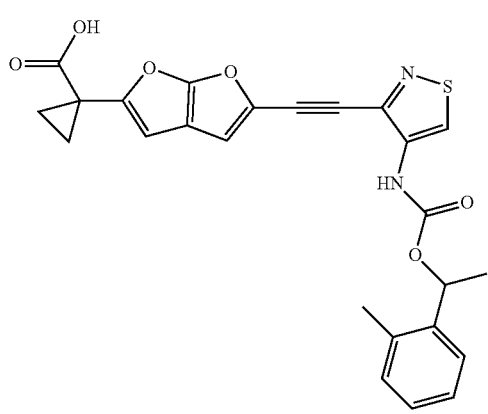 [SMILES: Cc1ccccc1C(C)OC(=O)Nc1csnc1C#Cc1cc2cc(C3(C(=O)O)CC3)oc2o1]
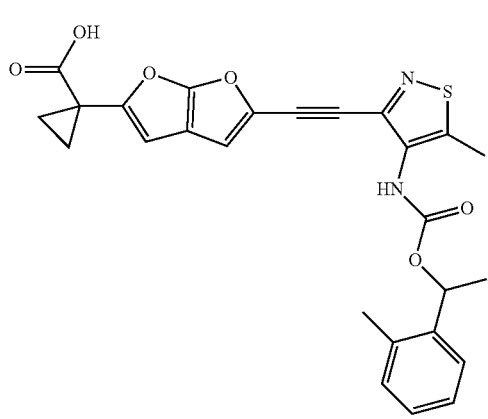 [SMILES: Cc1ccccc1C(C)OC(=O)Nc1c(C#Cc2cc3cc(C4(C(=O)O)CC4)oc3o2)nsc1C]
TABLE 17-continued
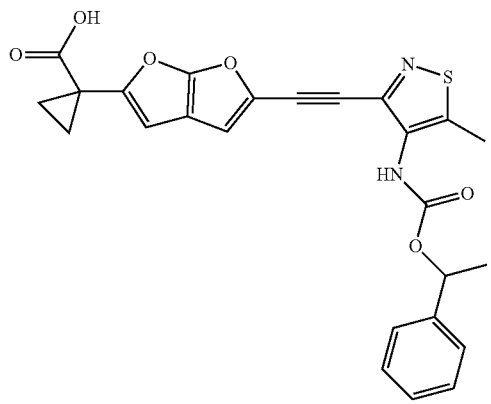 [SMILES: Cc1snc(C#Cc2cc3cc(C4(C(=O)O)CC4)oc3o2)c1NC(=O)OC(C)c1ccccc1]
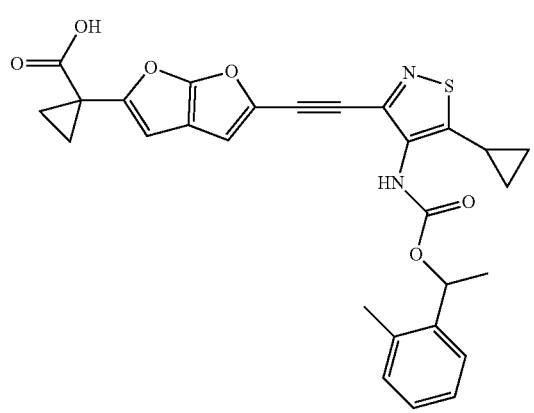 [SMILES: Cc1ccccc1C(C)OC(=O)Nc1c(C#Cc2cc3cc(C4(C(=O)O)CC4)oc3o2)nsc1C1CC1]
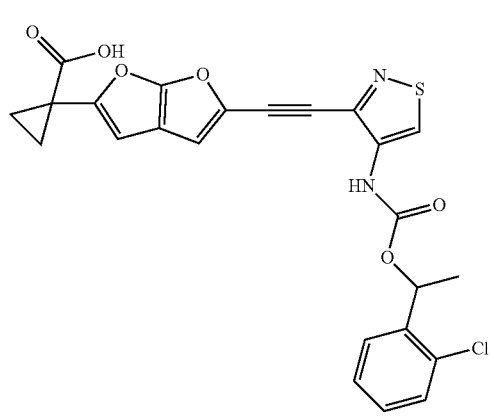 [SMILES: CC(OC(=O)Nc1csnc1C#Cc1cc2cc(C3(C(=O)O)CC3)oc2o1)c1ccccc1Cl]
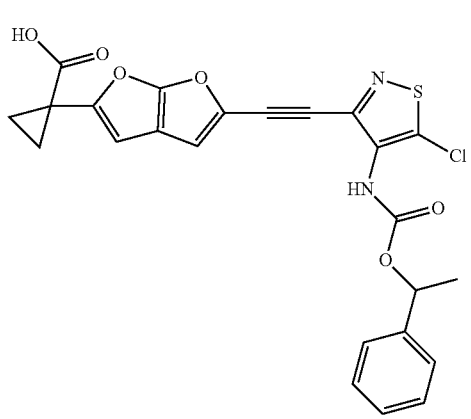

TABLE 17-continued
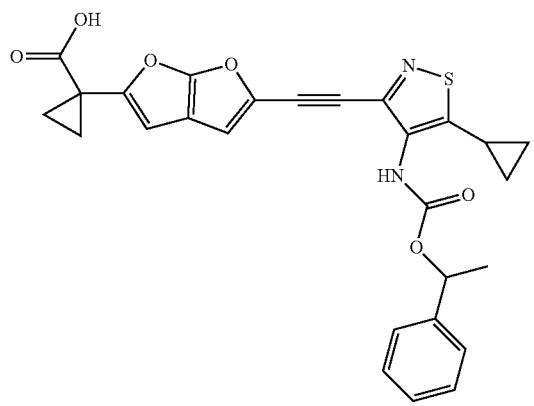
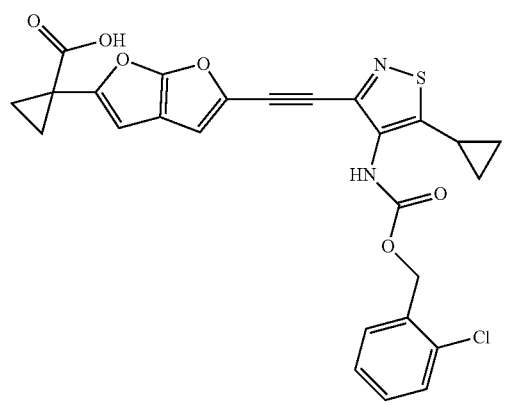 [SMILES: O=C(Nc1c(C#Cc2cc3cc(C4(C(=O)O)CC4)oc3o2)nsc1C1CC1)OCc1ccccc1Cl]
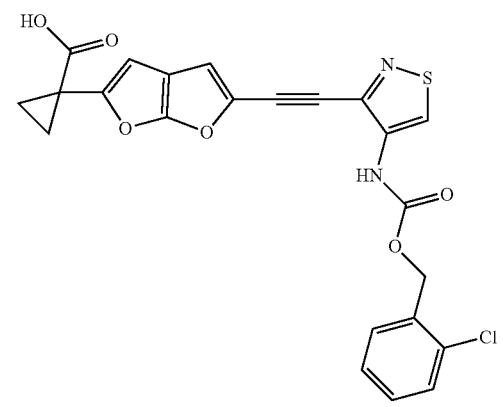 [SMILES: O=C(Nc1csnc1C#Cc1cc2cc(C3(C(=O)O)CC3)oc2o1)OCc1ccccc1Cl]
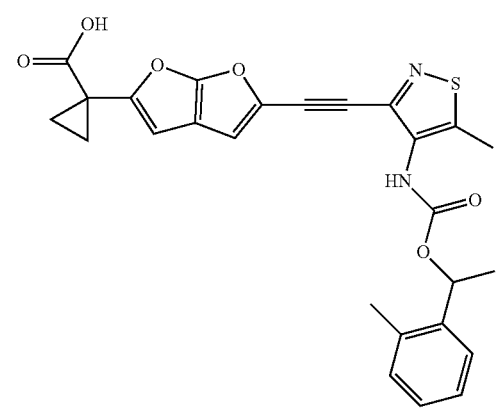 [SMILES: Cc1ccccc1C(C)OC(=O)Nc1c(C#Cc2cc3cc(C4(C(=O)O)CC4)oc3o2)nsc1C]
TABLE 17-continued
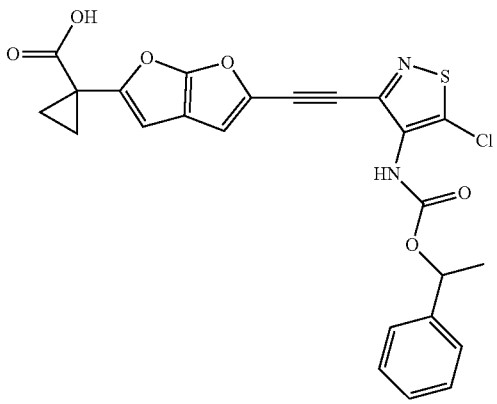 [SMILES: CC(OC(=O)Nc1c(C#Cc2cc3cc(C4(C(=O)O)CC4)oc3o2)nsc1Cl)c1ccccc1]
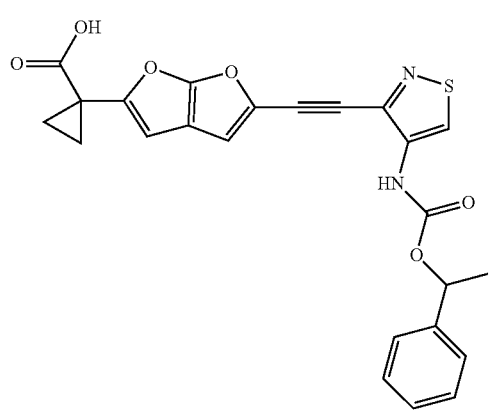 [SMILES: CC(OC(=O)Nc1csnc1C#Cc1cc2cc(C3(C(=O)O)CC3)oc2o1)c1ccccc1]
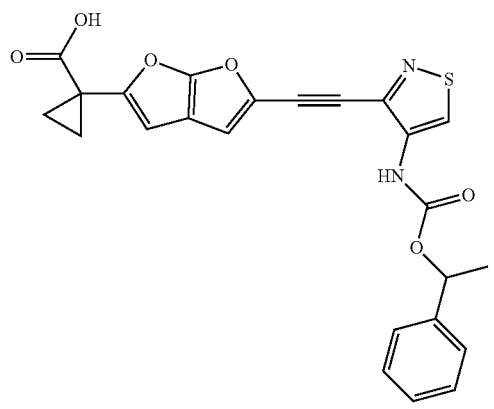 [SMILES: CC(OC(=O)Nc1csnc1C#Cc1cc2cc(C3(C(=O)O)CC3)oc2o1)c1ccccc1]
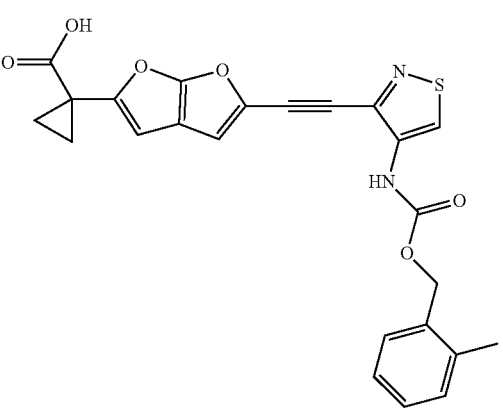 [SMILES: Cc1ccccc1COC(=O)Nc1csnc1C#Cc1cc2cc(C3(C(=O)O)CC3)oc2o1]

TABLE 17-continued
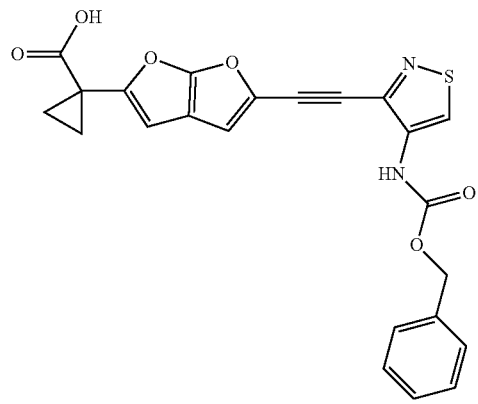 [SMILES: O=C(Nc1csnc1C#Cc1cc2cc(C3(C(=O)O)CC3)oc2o1)OCc1ccccc1]
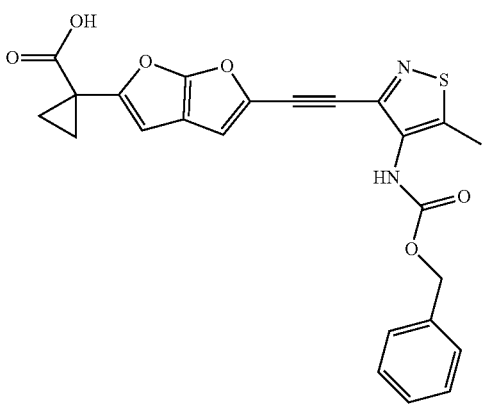 [SMILES: Cc1snc(C#Cc2cc3cc(C4(C(=O)O)CC4)oc3o2)c1NC(=O)OCc1ccccc1]

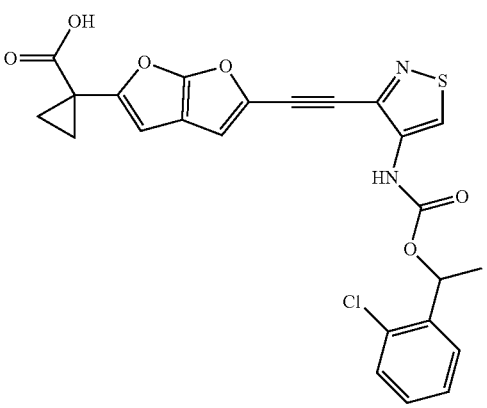
TABLE 17-continued
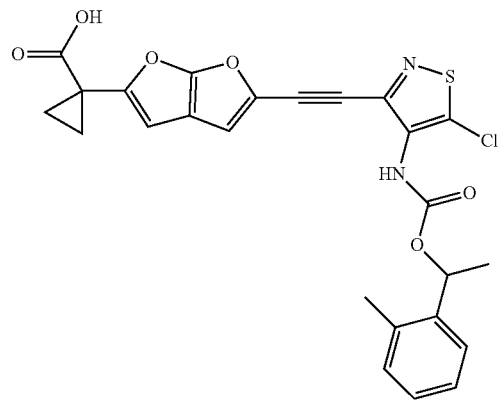 [SMILES: Cc1ccccc1C(C)OC(=O)Nc1c(C#Cc2cc3cc(C4(C(=O)O)CC4)oc3o2)nsc1Cl]
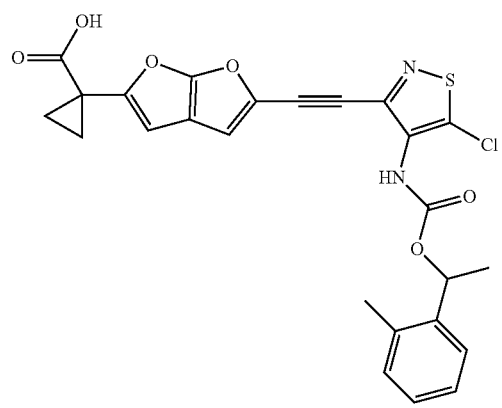 [SMILES: Cc1ccccc1C(C)OC(=O)Nc1c(C#Cc2cc3cc(C4(C(=O)O)CC4)oc3o2)nsc1Cl]
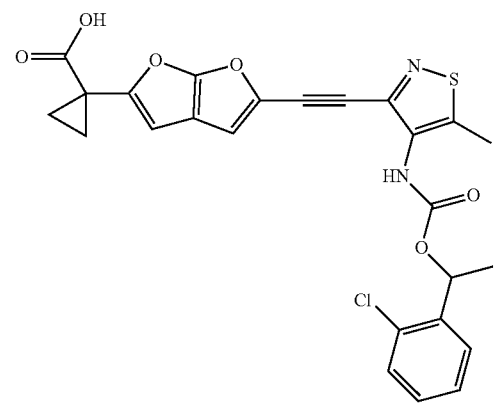 [SMILES: Cc1snc(C#Cc2cc3cc(C4(C(=O)O)CC4)oc3o2)c1NC(=O)OC(C)c1ccccc1Cl]
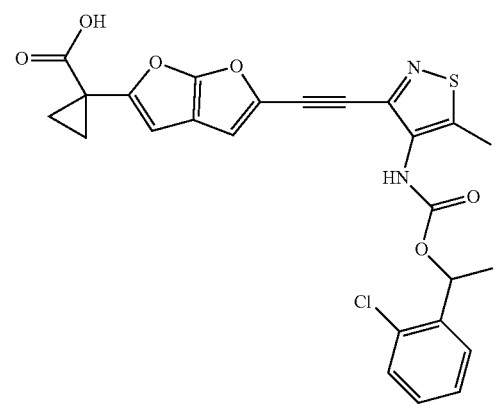 [SMILES: Cc1snc(C#Cc2cc3cc(C4(C(=O)O)CC4)oc3o2)c1NC(=O)OC(C)c1ccccc1Cl]

579
TABLE 17-continued
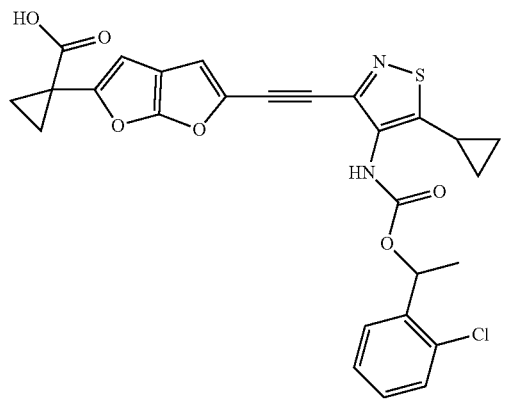 [SMILES: CC(OC(=O)Nc1c(C#Cc2cc3cc(C4(C(=O)O)CC4)oc3o2)nsc1C1CC1)c1ccccc1Cl]
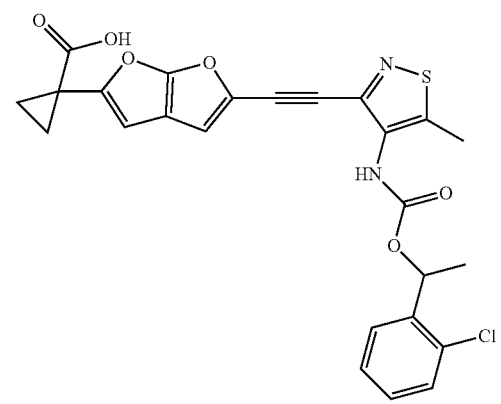 [SMILES: Cc1snc(C#Cc2cc3cc(C4(C(=O)O)CC4)oc3o2)c1NC(=O)OC(C)c1ccccc1Cl]
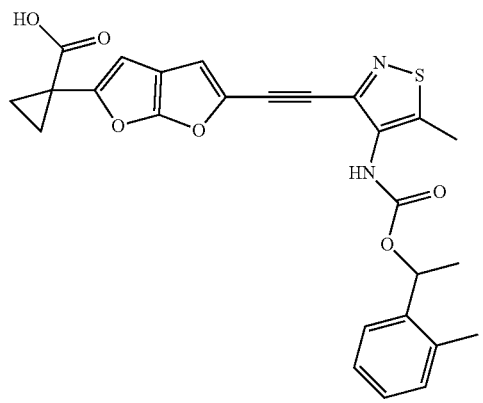 [SMILES: Cc1ccccc1C(C)OC(=O)Nc1c(C#Cc2cc3cc(C4(C(=O)O)CC4)oc3o2)nsc1C]
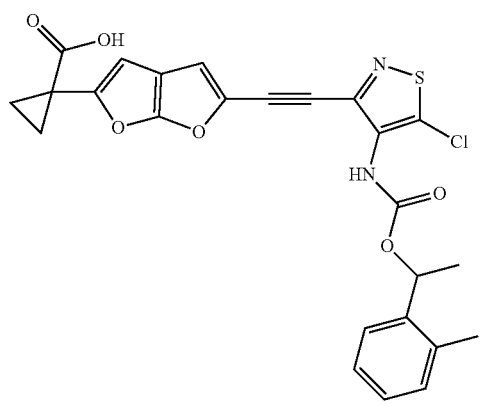 [SMILES: Cc1ccccc1C(C)OC(=O)Nc1c(C#Cc2cc3cc(C4(C(=O)O)CC4)oc3o2)nsc1Cl]
580
TABLE 17-continued
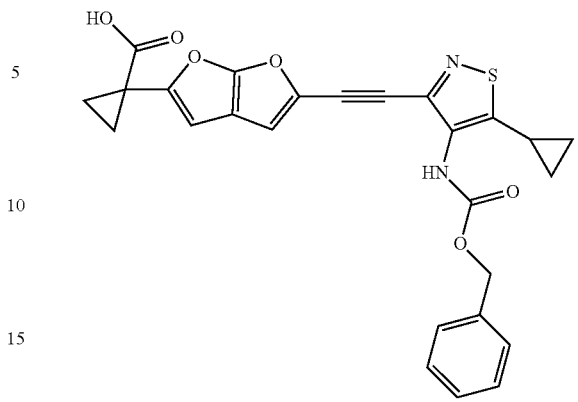
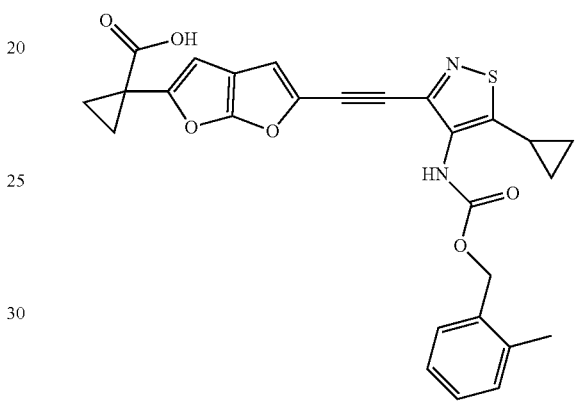

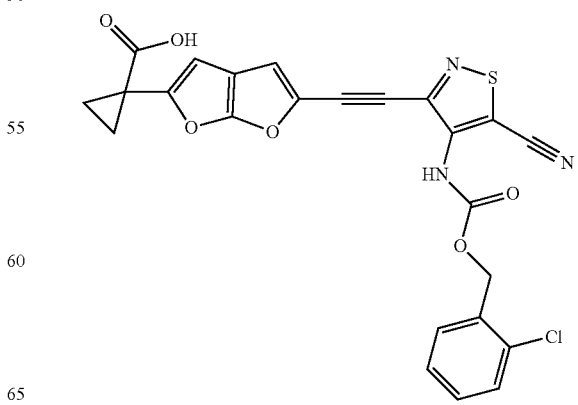

TABLE 17-continued
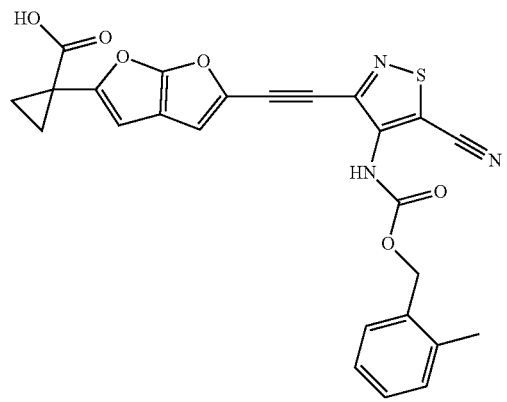 [SMILES: Cc1ccccc1COC(=O)Nc1c(C#Cc2cc3cc(C4(C(=O)O)CC4)oc3o2)nsc1C#N]
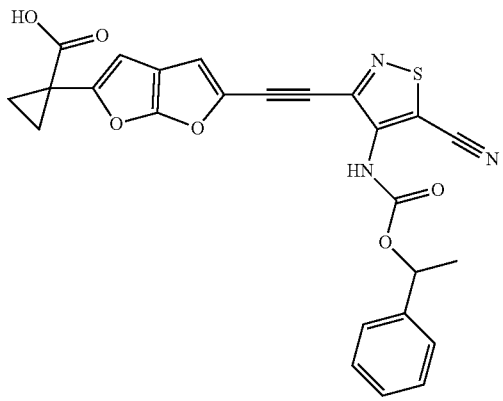
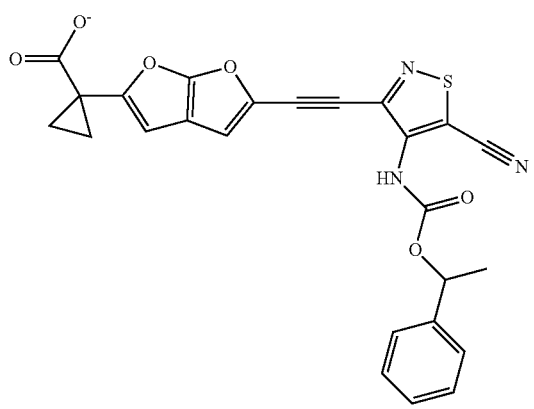 [SMILES: CC(OC(=O)Nc1c(C#Cc2cc3cc(C4(C(=O)[O-])CC4)oc3o2)nsc1C#N)c1ccccc1]
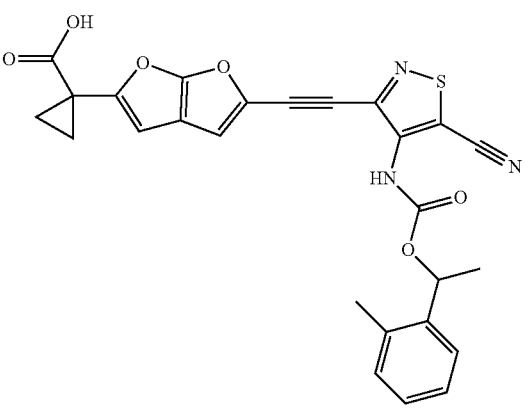
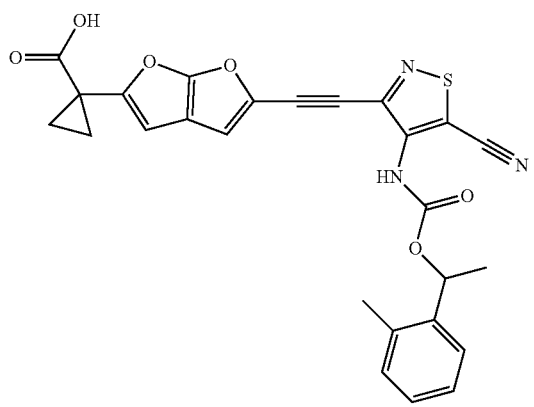
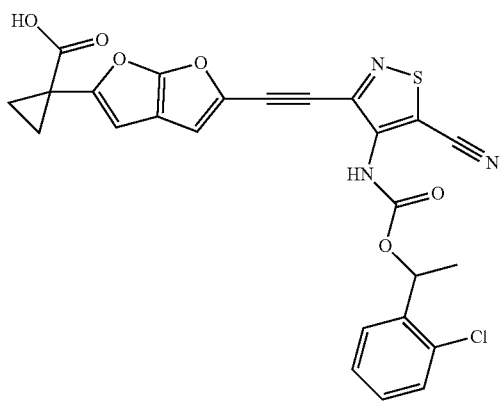 [SMILES: CC(OC(=O)Nc1c(C#Cc2cc3cc(C4(C(=O)O)CC4)oc3o2)nsc1C#N)c1ccccc1Cl]
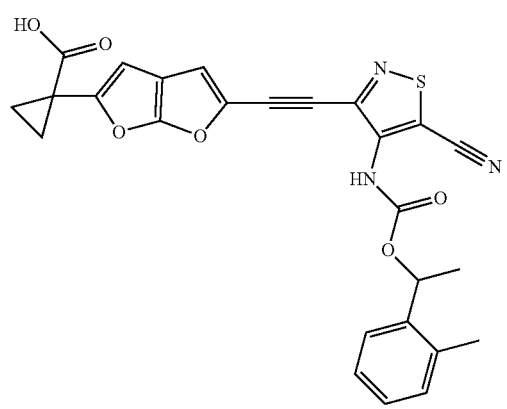
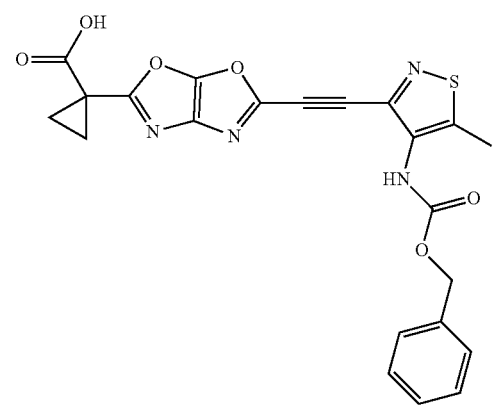 [SMILES: Cc1snc(C#Cc2nc3nc(C4(C(=O)O)CC4)oc3o2)c1NC(=O)OCc1ccccc1]

583
TABLE 17-continued
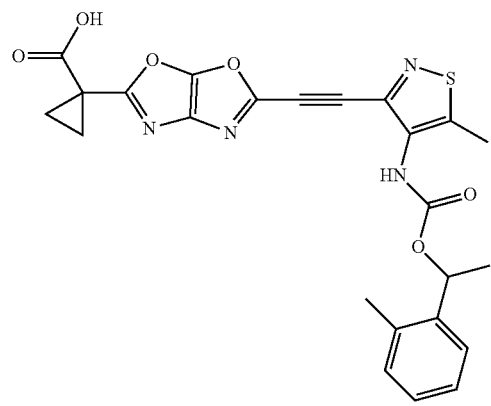 [SMILES: Cc1ccccc1C(C)OC(=O)Nc1c(C#Cc2nc3nc(C4(C(=O)O)CC4)oc3o2)nsc1C]
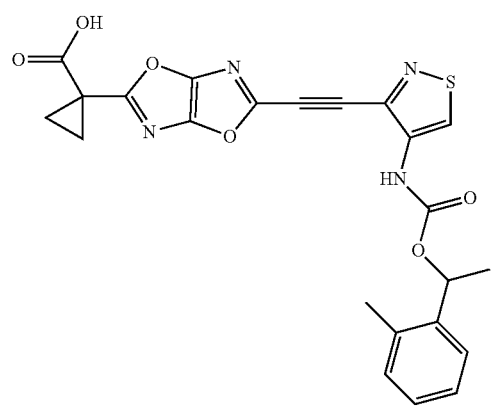 [SMILES: Cc1ccccc1C(C)OC(=O)Nc1csnc1C#Cc1nc2oc(C3(C(=O)O)CC3)nc2o1]
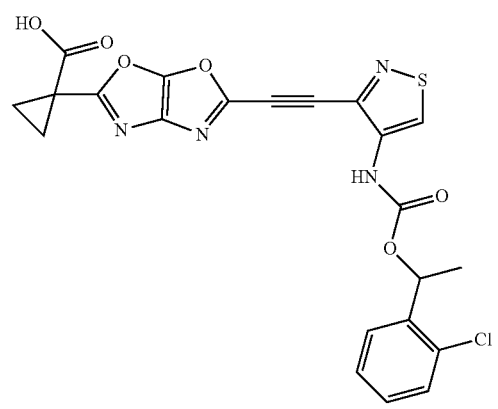
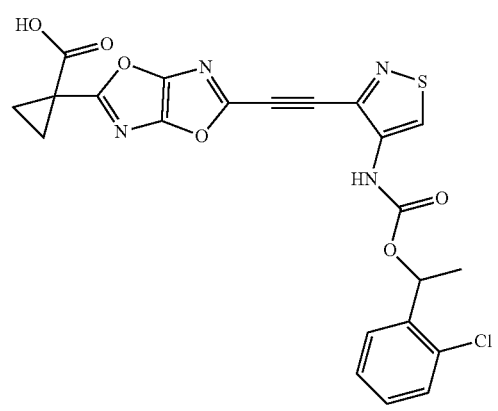
584
TABLE 17-continued
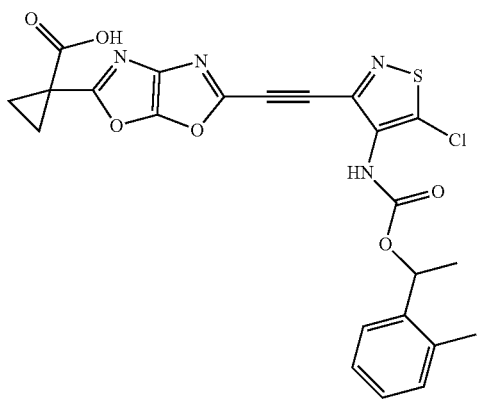 [SMILES: Cc1ccccc1C(C)OC(=O)Nc1c(C#Cc2nc3nc(C4(C(=O)O)CC4)oc3o2)nsc1Cl]
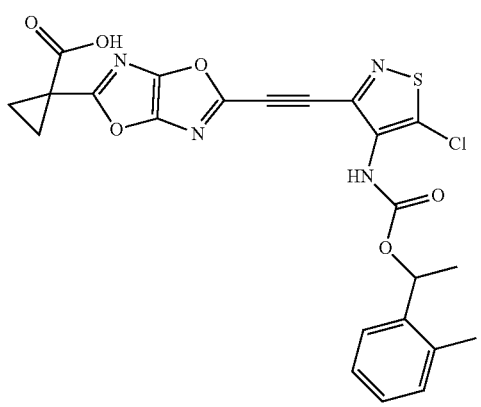 [SMILES: Cc1ccccc1C(C)OC(=O)Nc1c(C#Cc2nc3oc(C4(C(=O)O)CC4)nc3o2)nsc1Cl]
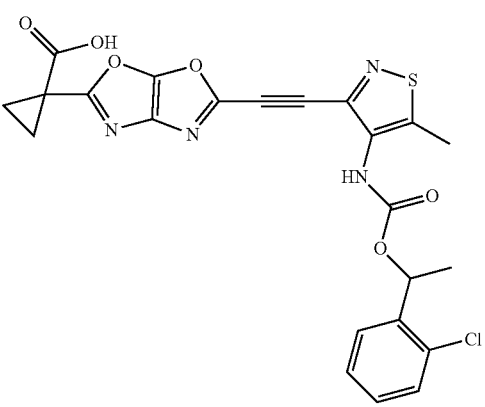
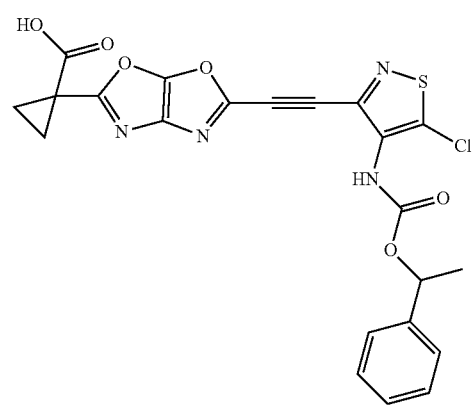

TABLE 17-continued
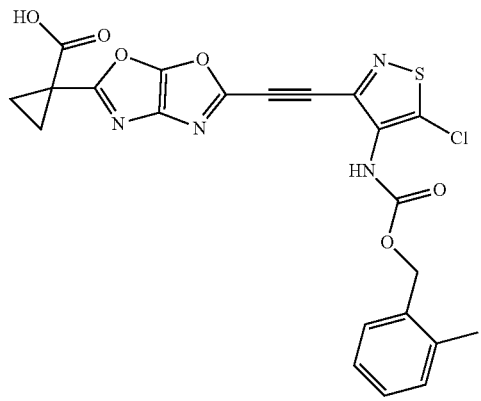 [SMILES: Cc1ccccc1COC(=O)Nc1c(C#Cc2nc3nc(C4(C(=O)O)CC4)oc3o2)nsc1Cl]
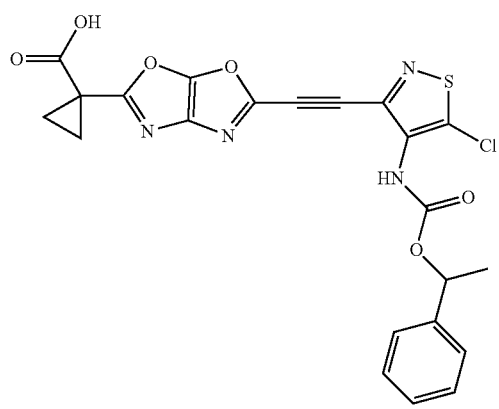 [SMILES: CC(OC(=O)Nc1c(C#Cc2nc3nc(C4(C(=O)O)CC4)oc3o2)nsc1Cl)c1ccccc1]
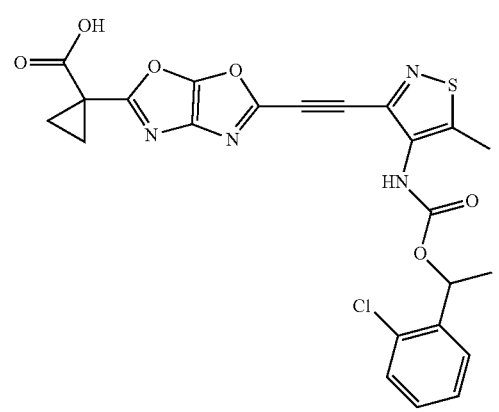 [SMILES: Cc1snc(C#Cc2nc3nc(C4(C(=O)O)CC4)oc3o2)c1NC(=O)OC(C)c1ccccc1Cl]
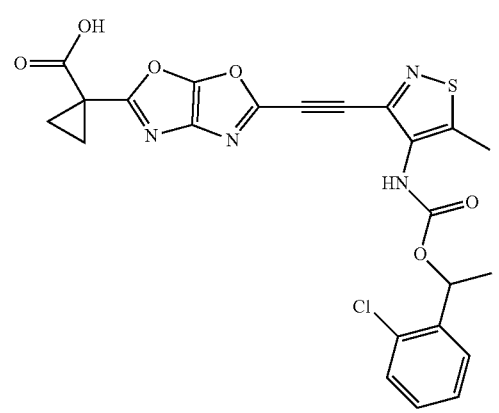 [SMILES: Cc1snc(C#Cc2nc3nc(C4(C(=O)O)CC4)oc3o2)c1NC(=O)OC(C)c1ccccc1Cl]
TABLE 17-continued
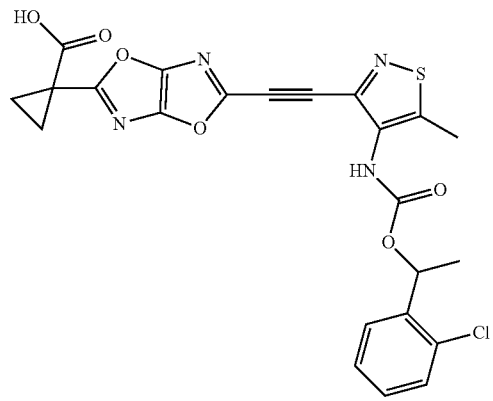 [SMILES: Cc1snc(C#Cc2nc3oc(C4(C(=O)O)CC4)nc3o2)c1NC(=O)OC(C)c1ccccc1Cl]
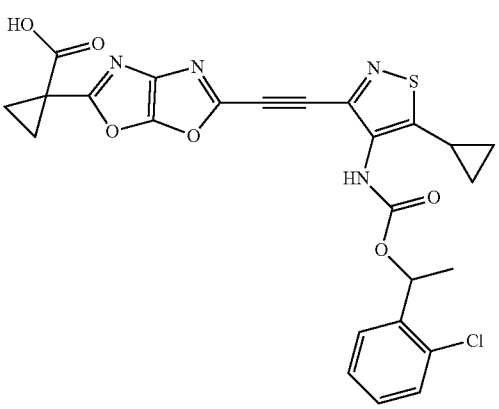 [SMILES: CC(OC(=O)Nc1c(C#Cc2nc3nc(C4(C(=O)O)CC4)oc3o2)nsc1C1CC1)c1ccccc1Cl]
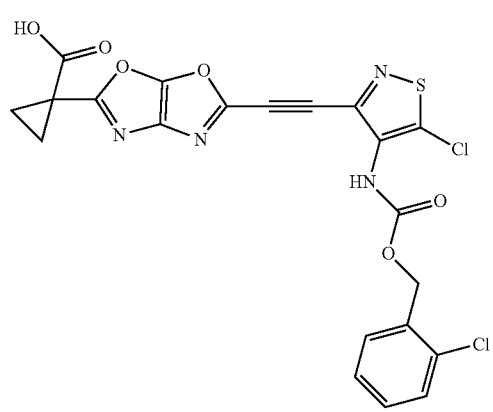
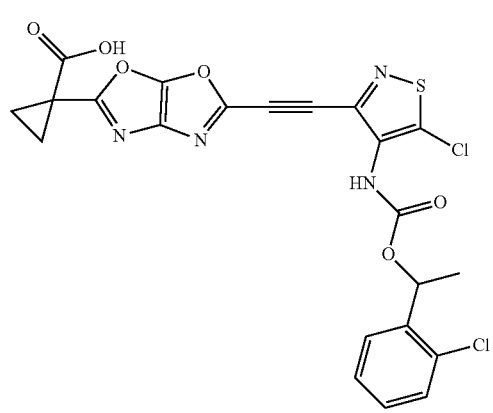

TABLE 17-continued
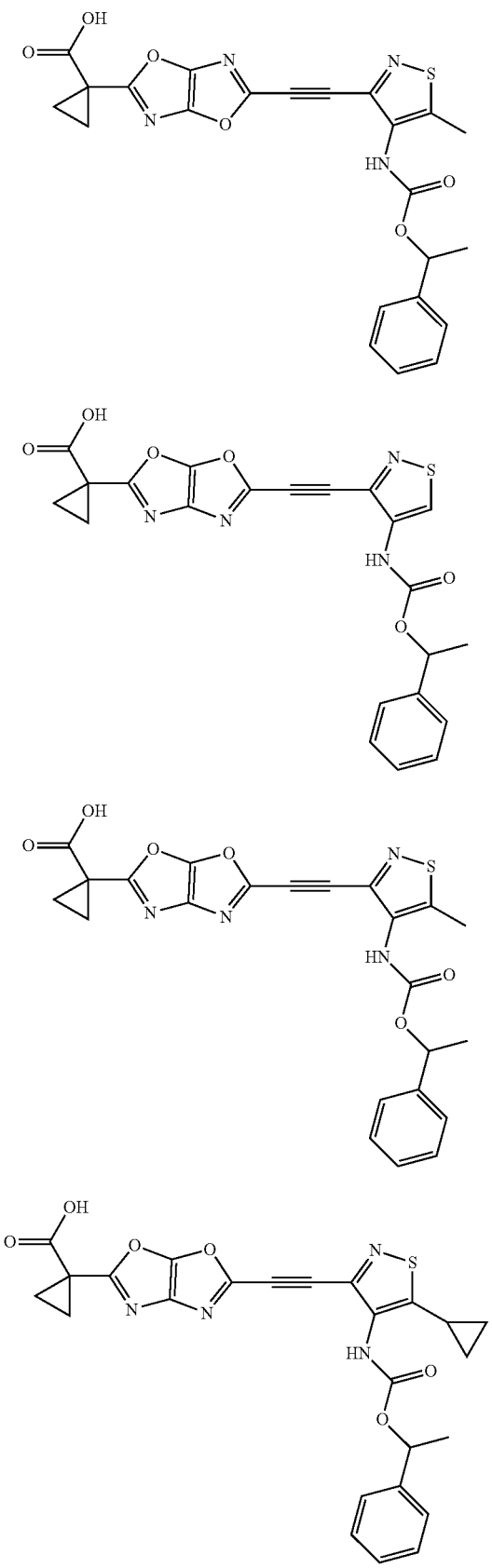
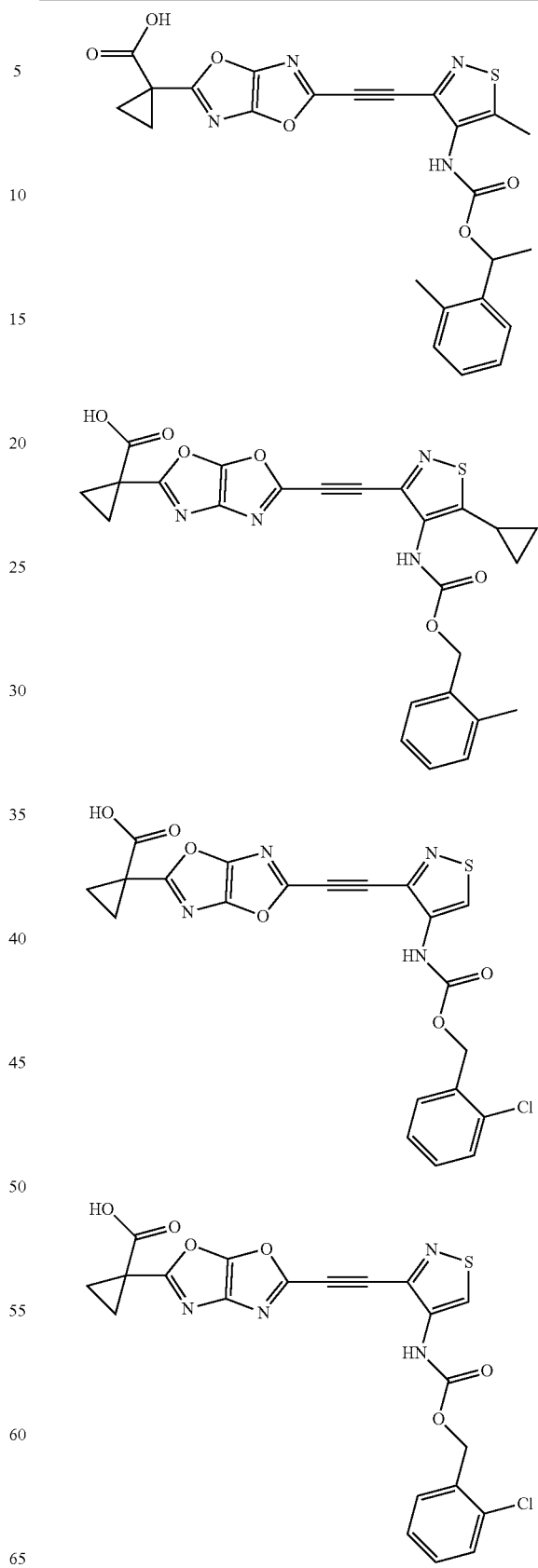

TABLE 17-continued
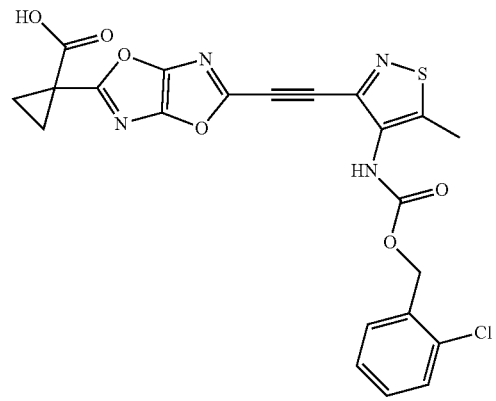 [SMILES: Cc1snc(C#Cc2nc3oc(C4(C(=O)O)CC4)nc3o2)c1NC(=O)OCc1ccccc1Cl]
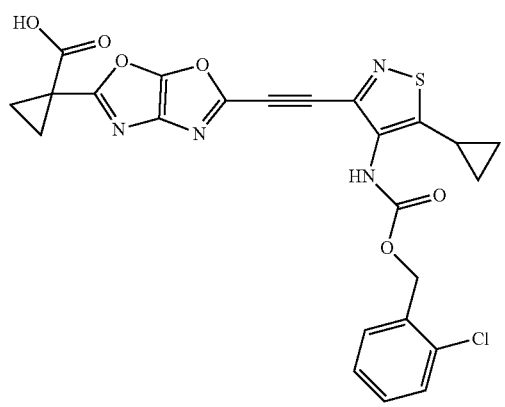 [SMILES: O=C(Nc1c(C#Cc2nc3nc(C4(C(=O)O)CC4)oc3o2)nsc1C1CC1)OCc1ccccc1Cl]
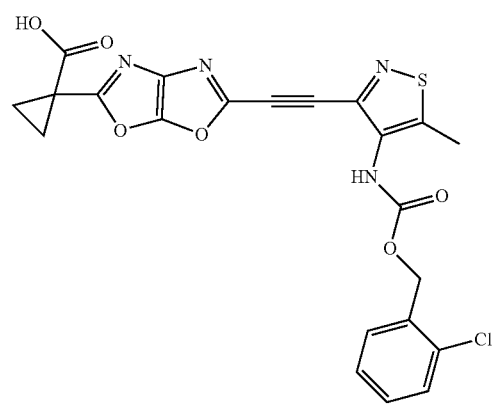
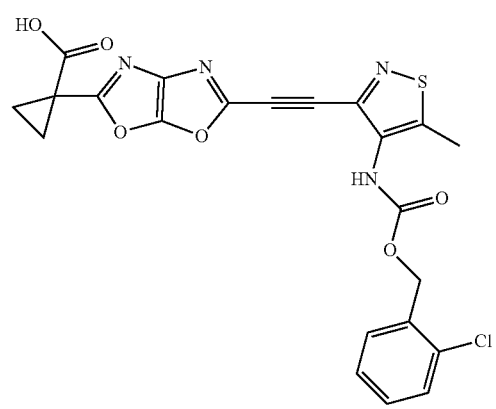
TABLE 17-continued
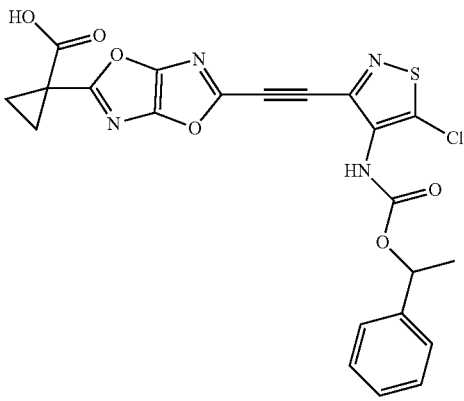 [SMILES: CC(OC(=O)Nc1c(C#Cc2nc3oc(C4(C(=O)O)CC4)nc3o2)nsc1Cl)c1ccccc1]
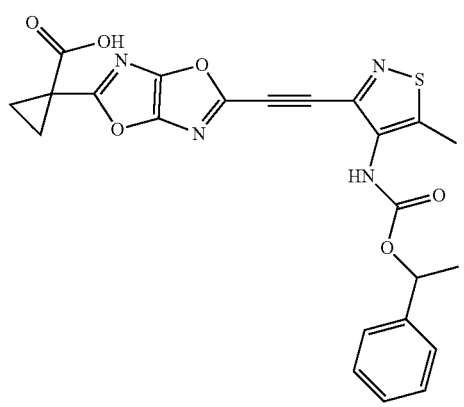 [SMILES: Cc1snc(C#Cc2nc3oc(C4(C(=O)O)CC4)nc3o2)c1NC(=O)OC(C)c1ccccc1]
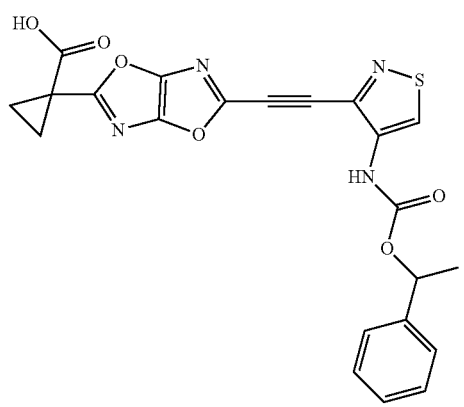 [SMILES: CC(OC(=O)Nc1csnc1C#Cc1nc2oc(C3(C(=O)O)CC3)nc2o1)c1ccccc1]
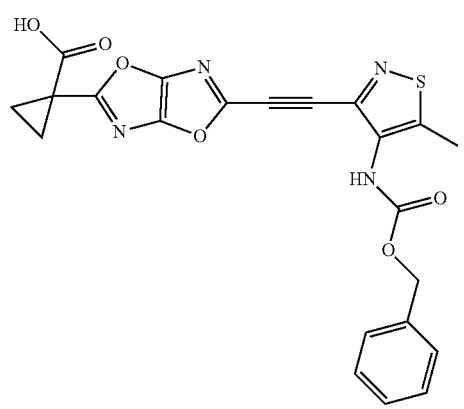 [SMILES: Cc1snc(C#Cc2nc3oc(C4(C(=O)O)CC4)nc3o2)c1NC(=O)OCc1ccccc1]

591
TABLE 17-continued
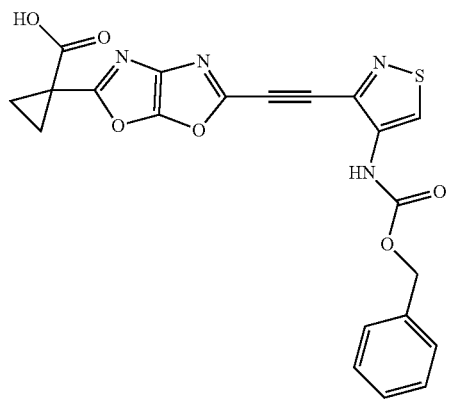 [SMILES: O=C(Nc1csnc1C#Cc1nc2nc(C3(C(=O)O)CC3)oc2o1)OCc1ccccc1]
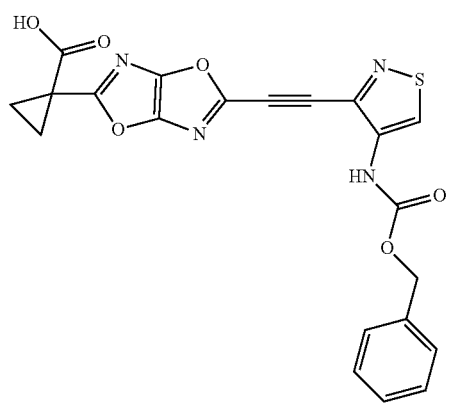 [SMILES: O=C(Nc1csnc1C#Cc1nc2oc(C3(C(=O)O)CC3)nc2o1)OCc1ccccc1]
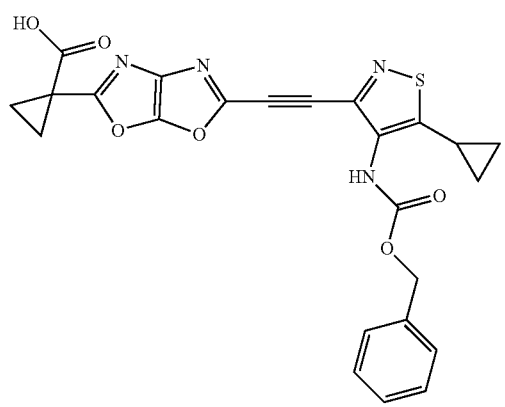 [SMILES: O=C(Nc1c(C#Cc2nc3nc(C4(C(=O)O)CC4)oc3o2)nsc1C1CC1)OCc1ccccc1]
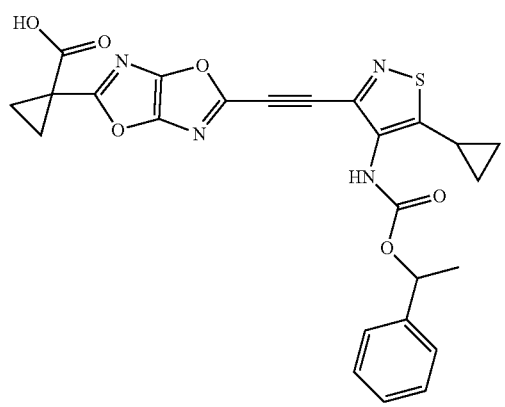 [SMILES: CC(OC(=O)Nc1c(C#Cc2nc3oc(C4(C(=O)O)CC4)nc3o2)nsc1C1CC1)c1ccccc1]
592
TABLE 17-continued
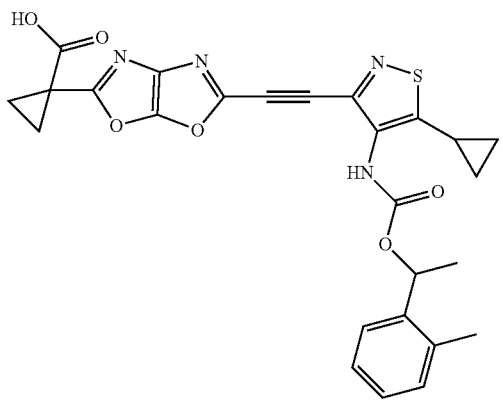 [SMILES: Cc1ccccc1C(C)OC(=O)Nc1c(C#Cc2nc3nc(C4(C(=O)O)CC4)oc3o2)nsc1C1CC1]
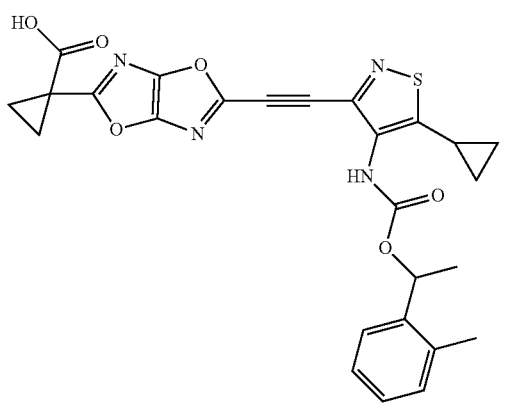 [SMILES: Cc1ccccc1C(C)OC(=O)Nc1c(C#Cc2nc3oc(C4(C(=O)O)CC4)nc3o2)nsc1C1CC1]
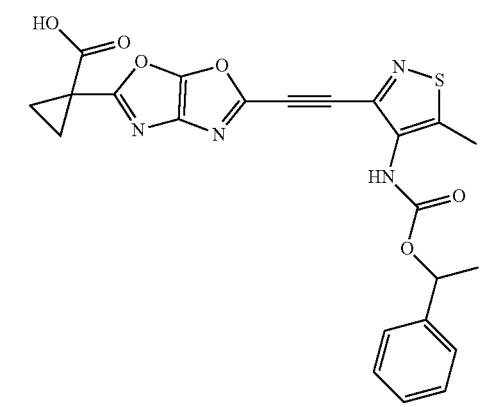 [SMILES: Cc1snc(C#Cc2nc3nc(C4(C(=O)O)CC4)oc3o2)c1NC(=O)OC(C)c1ccccc1]
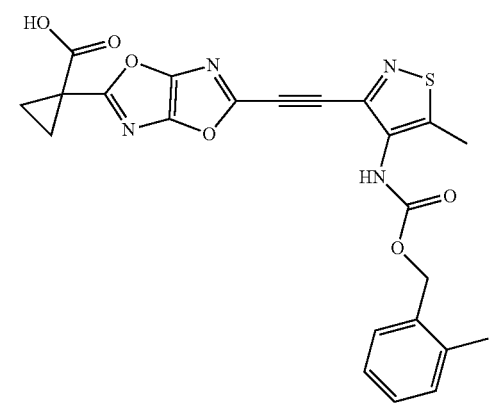

TABLE 17-continued
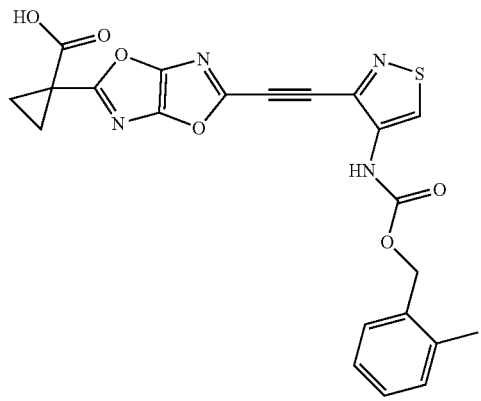 [SMILES: Cc1ccccc1COC(=O)Nc1csnc1C#Cc1nc2oc(C3(C(=O)O)CC3)nc2o1]
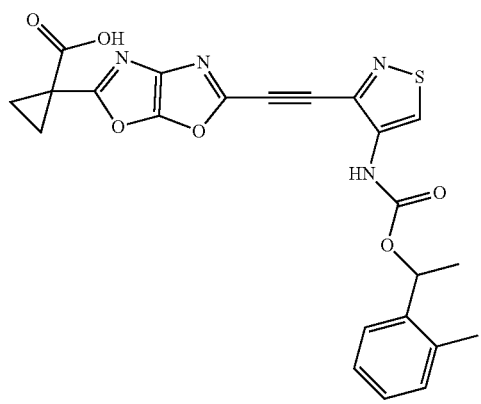 [SMILES: Cc1ccccc1C(C)OC(=O)Nc1csnc1C#Cc1nc2nc(C3(C(=O)O)CC3)oc2o1]
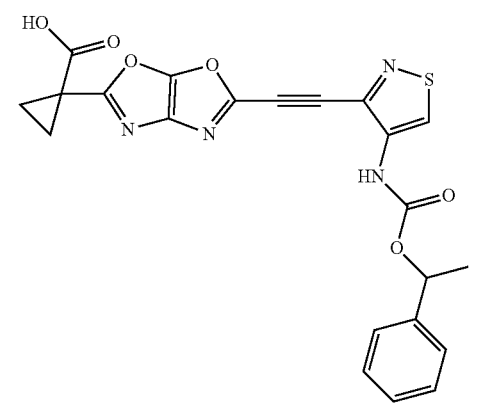 [SMILES: CC(OC(=O)Nc1csnc1C#Cc1nc2nc(C3(C(=O)O)CC3)oc2o1)c1ccccc1]
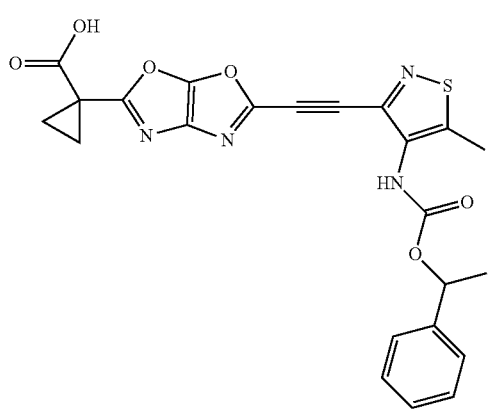 [SMILES: Cc1snc(C#Cc2nc3nc(C4(C(=O)O)CC4)oc3o2)c1NC(=O)OC(C)c1ccccc1]
TABLE 17-continued
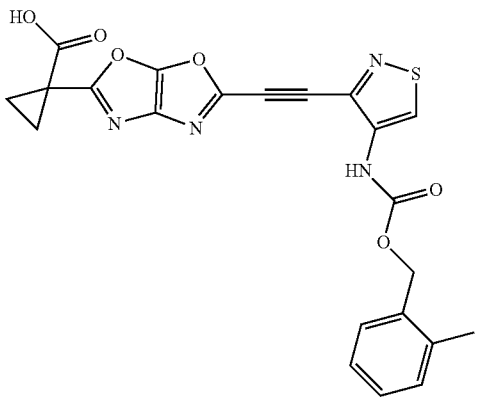 [SMILES: Cc1ccccc1COC(=O)Nc1csnc1C#Cc1nc2nc(C3(C(=O)O)CC3)oc2o1]
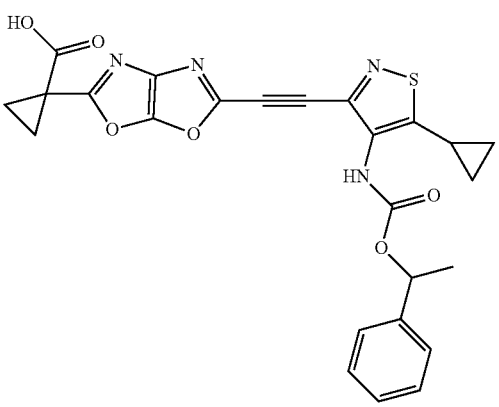 [SMILES: CC(OC(=O)Nc1c(C#Cc2nc3nc(C4(C(=O)O)CC4)oc3o2)nsc1C1CC1)c1ccccc1]
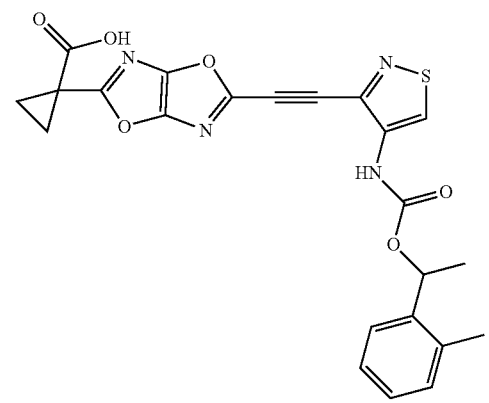 [SMILES: Cc1ccccc1C(C)OC(=O)Nc1csnc1C#Cc1nc2oc(C3(C(=O)O)CC3)nc2o1]
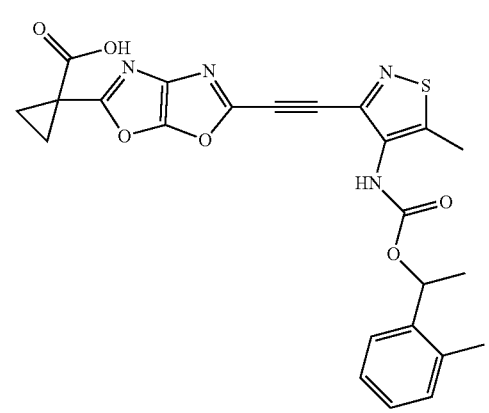

TABLE 17-continued
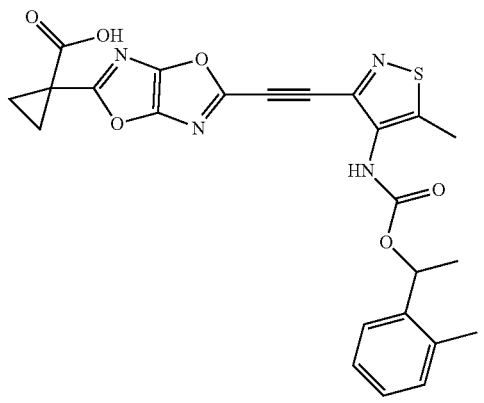 [SMILES: Cc1ccccc1C(C)OC(=O)Nc1c(C#Cc2nc3oc(C4(C(=O)O)CC4)nc3o2)nsc1C]
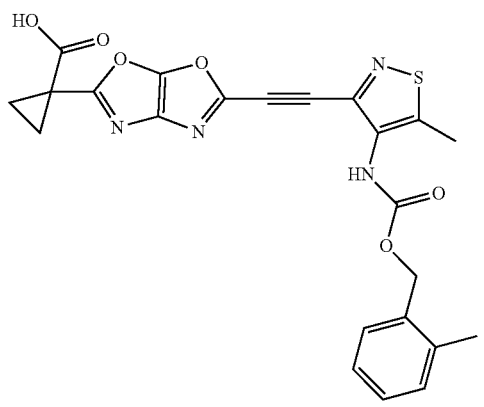 [SMILES: Cc1ccccc1COC(=O)Nc1c(C#Cc2nc3nc(C4(C(=O)O)CC4)oc3o2)nsc1C]
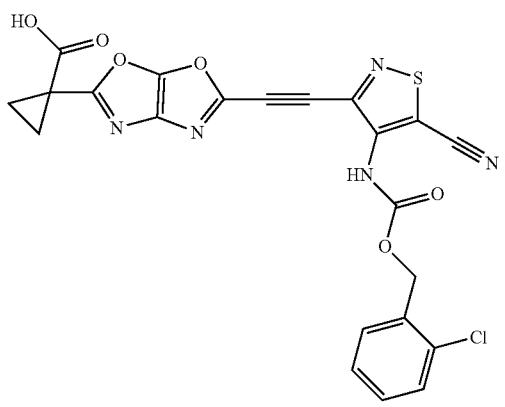 [SMILES: N#Cc1snc(C#Cc2nc3nc(C4(C(=O)O)CC4)oc3o2)c1NC(=O)OCc1ccccc1Cl]
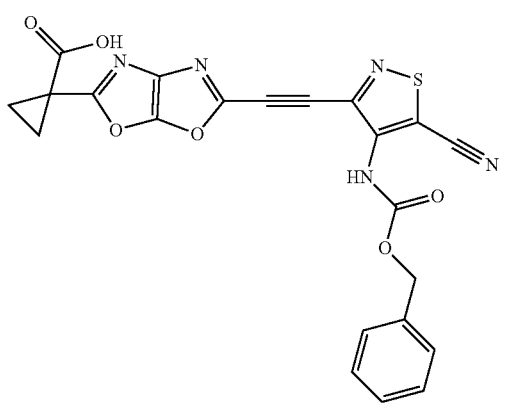 [SMILES: N#Cc1snc(C#Cc2nc3nc(C4(C(=O)O)CC4)oc3o2)c1NC(=O)OCc1ccccc1]
TABLE 17-continued
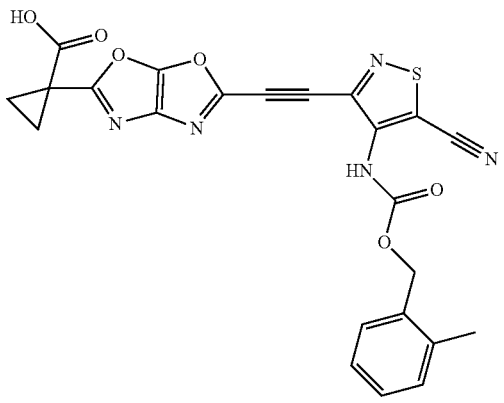 [SMILES: Cc1ccccc1COC(=O)Nc1c(C#Cc2nc3nc(C4(C(=O)O)CC4)oc3o2)nsc1C#N]
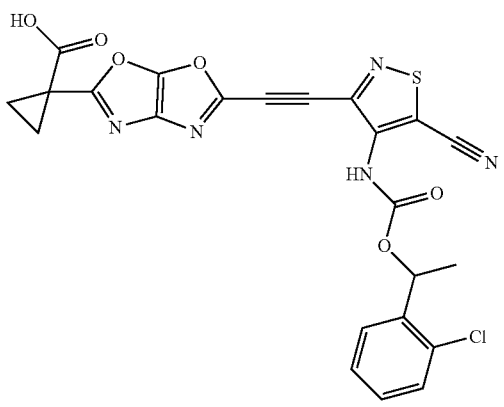 [SMILES: CC(OC(=O)Nc1c(C#Cc2nc3nc(C4(C(=O)O)CC4)oc3o2)nsc1C#N)c1ccccc1Cl]
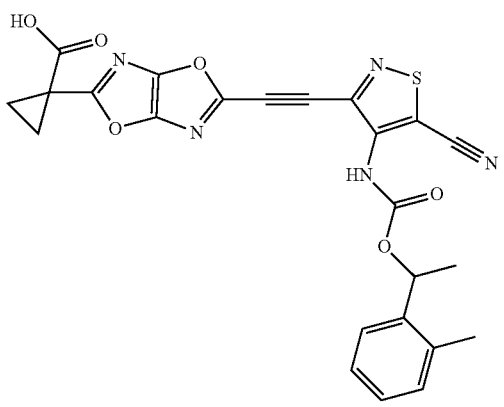
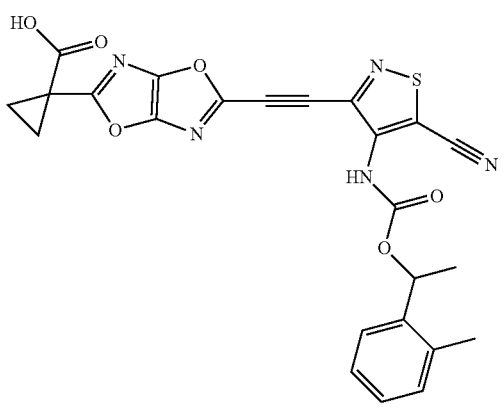

TABLE 17-continued
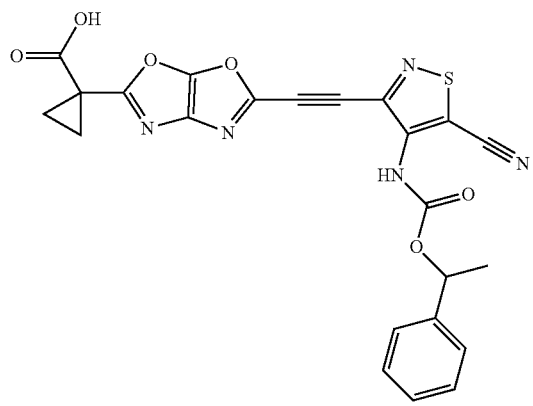 [SMILES: CC(OC(=O)Nc1c(C#Cc2nc3nc(C4(C(=O)O)CC4)oc3o2)nsc1C#N)c1ccccc1]
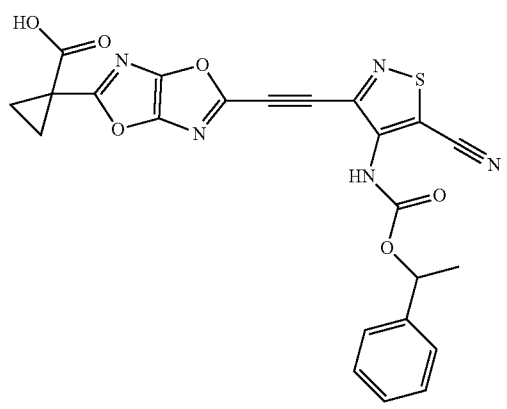 [SMILES: CC(OC(=O)Nc1c(C#Cc2nc3oc(C4(C(=O)O)CC4)nc3o2)nsc1C#N)c1ccccc1]
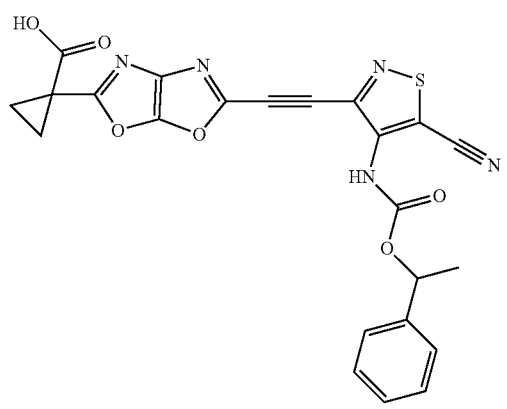 [SMILES: CC(OC(=O)Nc1c(C#Cc2nc3nc(C4(C(=O)O)CC4)oc3o2)nsc1C#N)c1ccccc1]
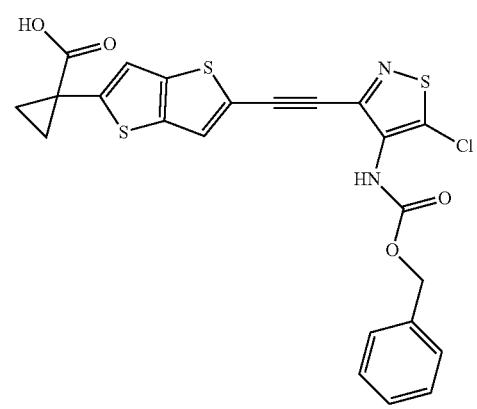 [SMILES: O=C(Nc1c(C#Cc2cc3sc(C4(C(=O)O)CC4)cc3s2)nsc1Cl)OCc1ccccc1]
TABLE 17-continued
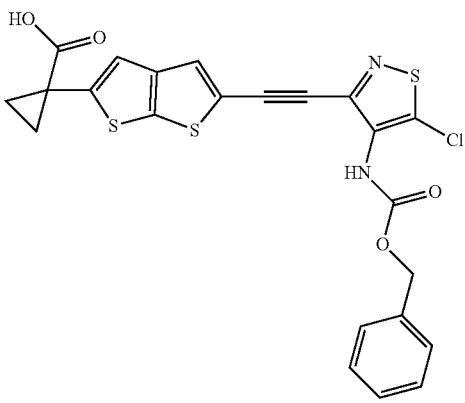 [SMILES: O=C(Nc1c(C#Cc2cc3cc(C4(C(=O)O)CC4)sc3s2)nsc1Cl)OCc1ccccc1]
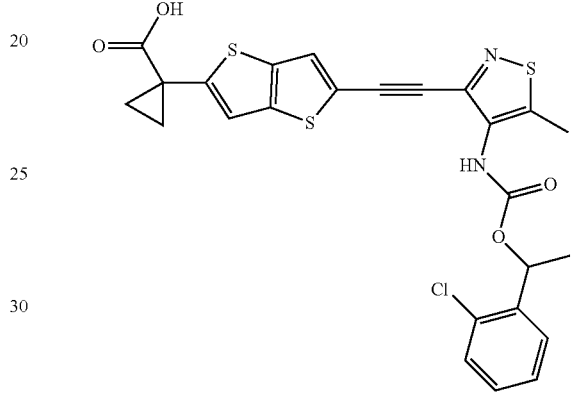
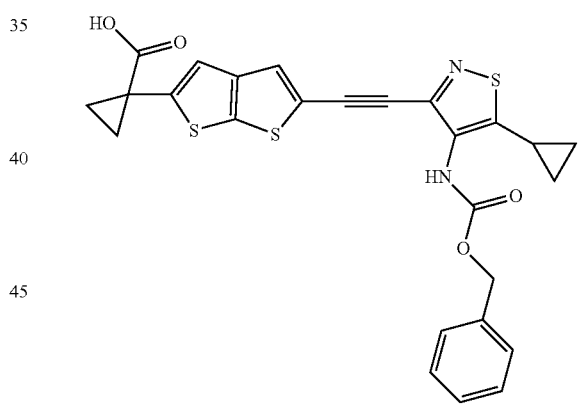
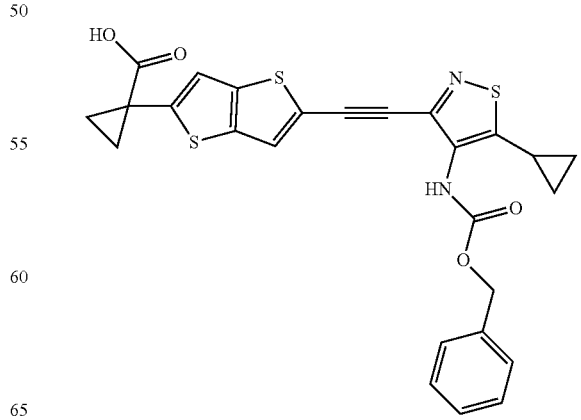

TABLE 17-continued
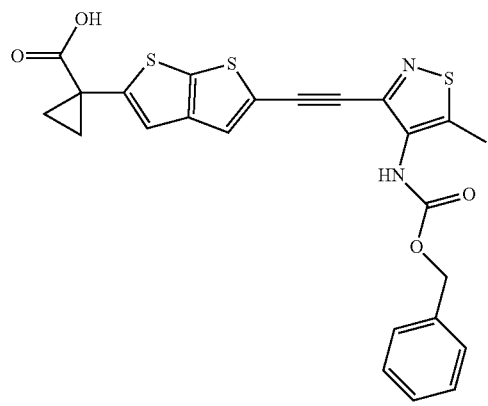
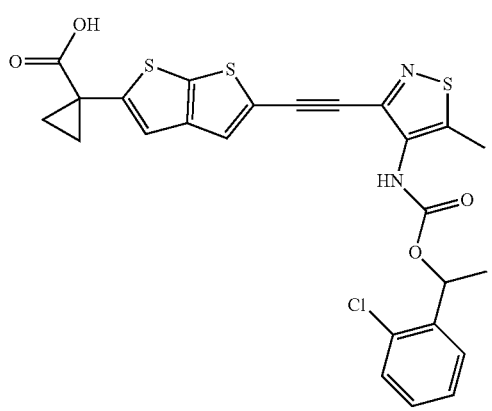
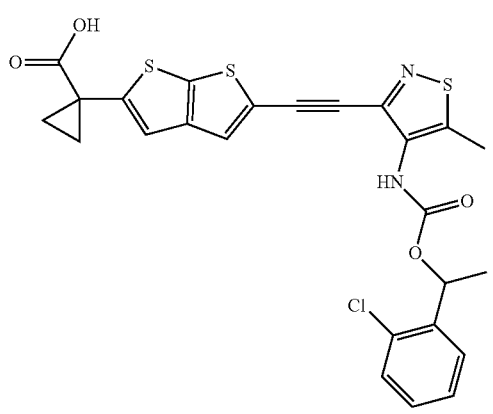
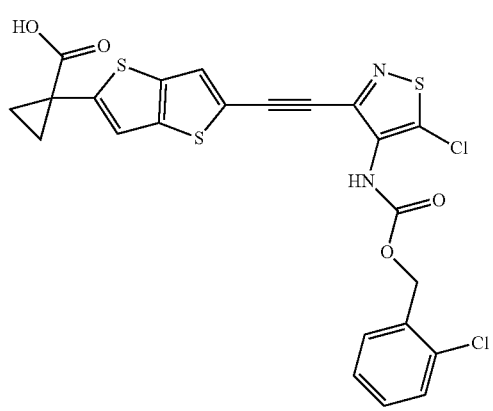 [SMILES: O=C(Nc1c(C#Cc2cc3sc(C4(C(=O)O)CC4)cc3s2)nsc1Cl)OCc1ccccc1Cl]
TABLE 17-continued
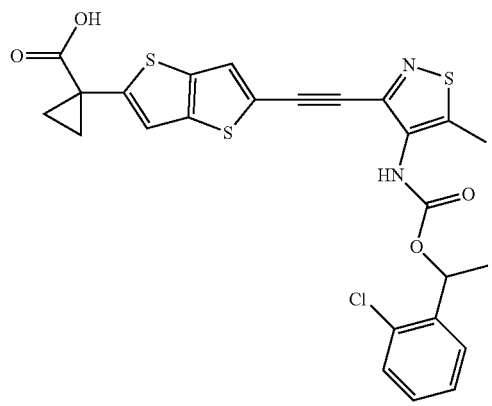 [SMILES: Cc1snc(C#Cc2cc3sc(C4(C(=O)O)CC4)cc3s2)c1NC(=O)OC(C)c1ccccc1Cl]
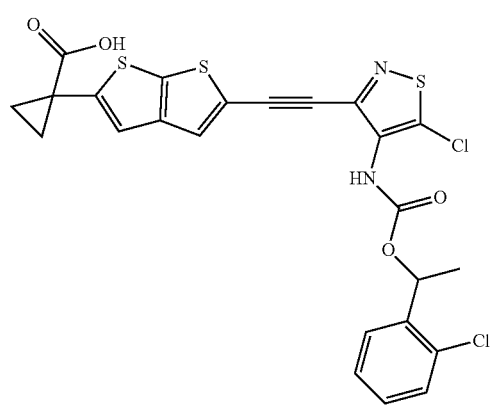
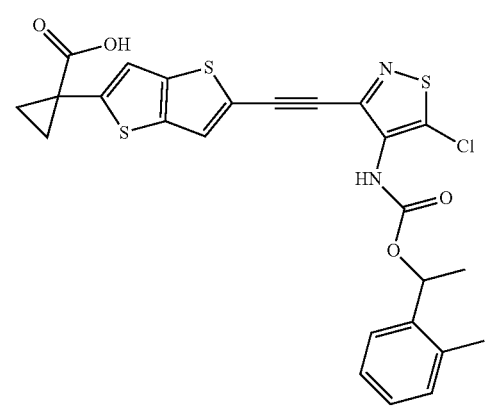
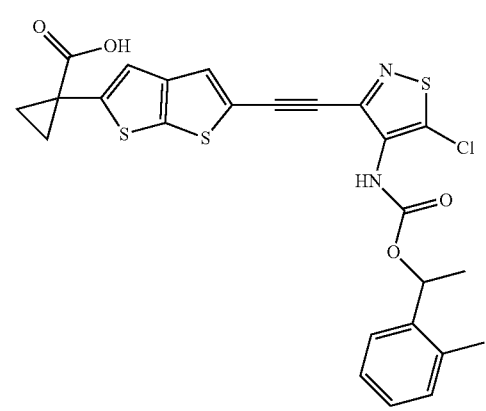

TABLE 17-continued
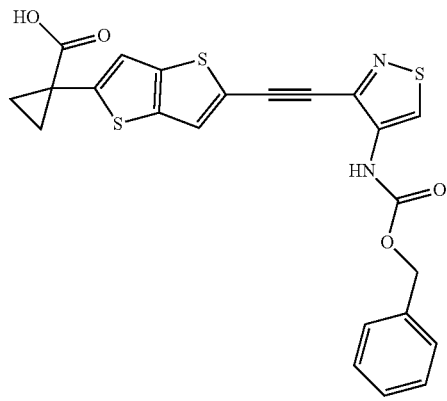 [SMILES: O=C(Nc1csnc1C#Cc1cc2sc(C3(C(=O)O)CC3)cc2s1)OCc1ccccc1]
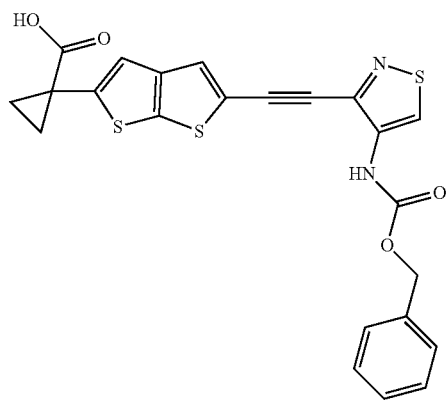 [SMILES: O=C(Nc1csnc1C#Cc1cc2cc(C3(C(=O)O)CC3)sc2s1)OCc1ccccc1]
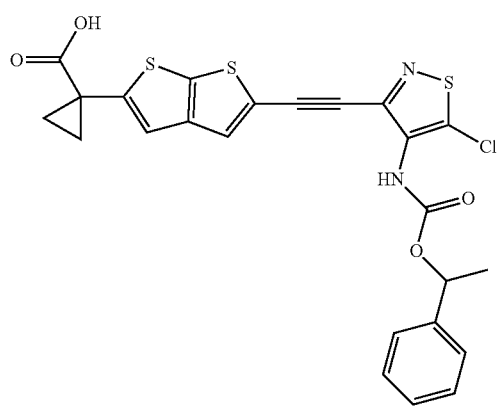
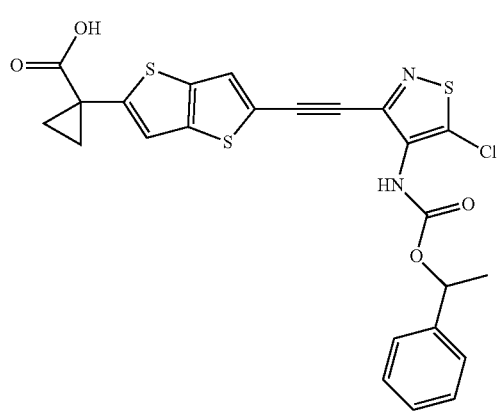 [SMILES: CC(OC(=O)Nc1c(C#Cc2cc3sc(C4(C(=O)O)CC4)cc3s2)nsc1Cl)c1ccccc1]
TABLE 17-continued
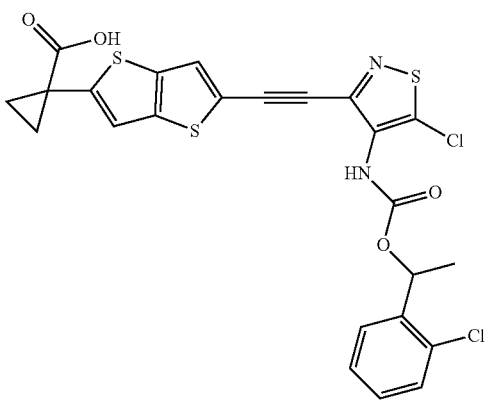 [SMILES: CC(OC(=O)Nc1c(C#Cc2cc3sc(C4(C(=O)O)CC4)cc3s2)nsc1Cl)c1ccccc1Cl]
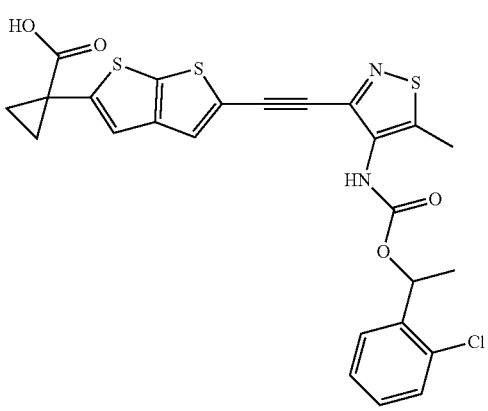 [SMILES: Cc1snc(C#Cc2cc3cc(C4(C(=O)O)CC4)sc3s2)c1NC(=O)OC(C)c1ccccc1Cl]
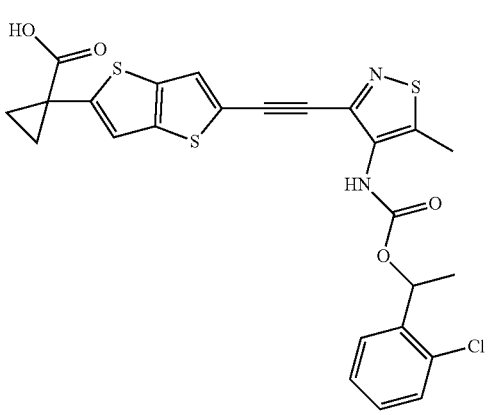 [SMILES: Cc1snc(C#Cc2cc3sc(C4(C(=O)O)CC4)cc3s2)c1NC(=O)OC(C)c1ccccc1Cl]
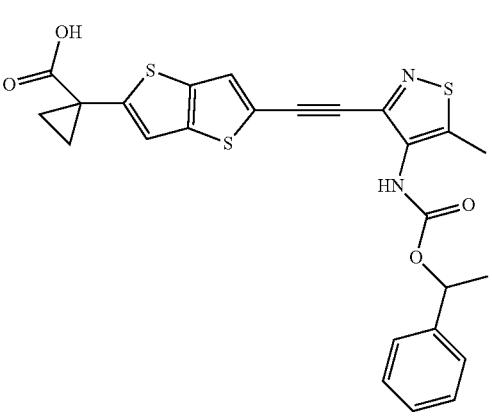 [SMILES: Cc1snc(C#Cc2cc3sc(C4(C(=O)O)CC4)cc3s2)c1NC(=O)OC(C)c1ccccc1]

TABLE 17-continued
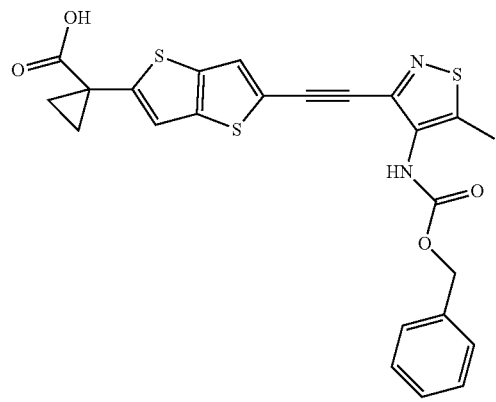 [SMILES: Cc1snc(C#Cc2cc3sc(C4(C(=O)O)CC4)cc3s2)c1NC(=O)OCc1ccccc1]
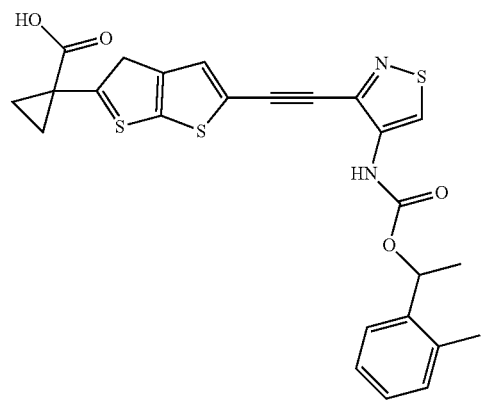
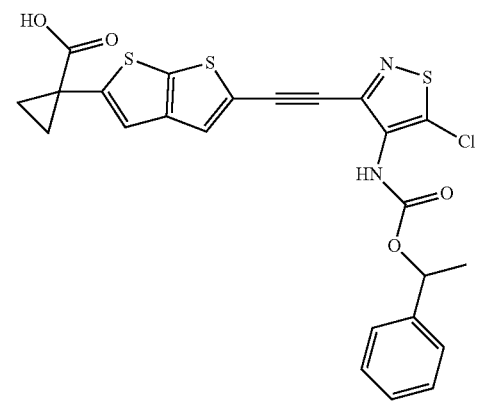 [SMILES: CC(OC(=O)Nc1c(C#Cc2cc3cc(C4(C(=O)O)CC4)sc3s2)nsc1Cl)c1ccccc1]
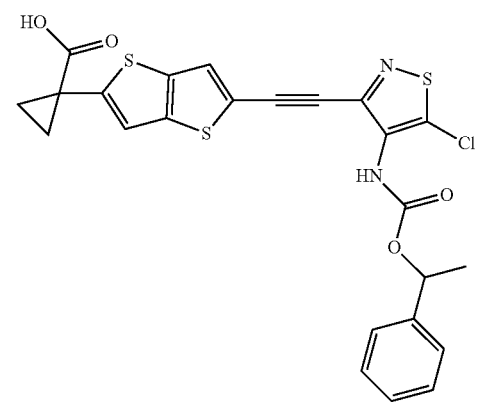 [SMILES: CC(OC(=O)Nc1c(C#Cc2cc3sc(C4(C(=O)O)CC4)cc3s2)nsc1Cl)c1ccccc1]
TABLE 17-continued
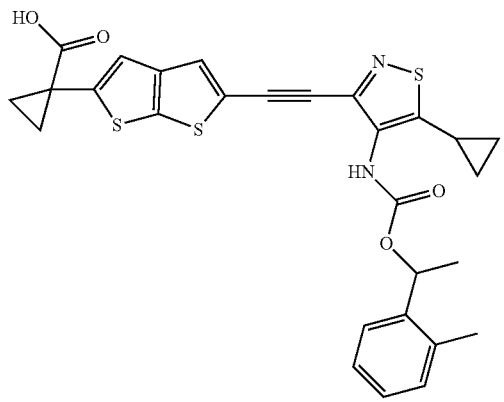 [SMILES: Cc1ccccc1C(C)OC(=O)Nc1c(C#Cc2cc3cc(C4(C(=O)O)CC4)sc3s2)nsc1C1CC1]
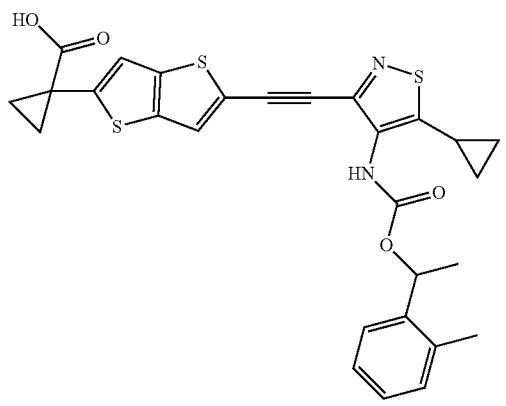 [SMILES: Cc1ccccc1C(C)OC(=O)Nc1c(C#Cc2cc3sc(C4(C(=O)O)CC4)cc3s2)nsc1C1CC1]
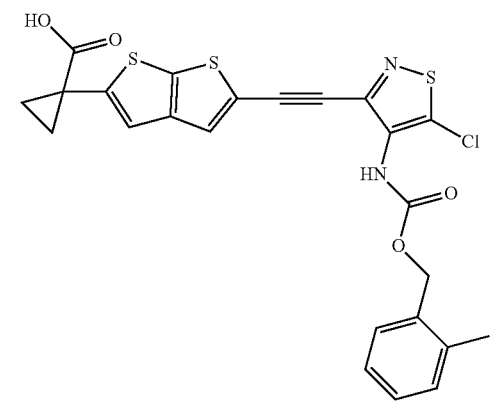 [SMILES: Cc1ccccc1COC(=O)Nc1c(C#Cc2cc3cc(C4(C(=O)O)CC4)sc3s2)nsc1Cl]
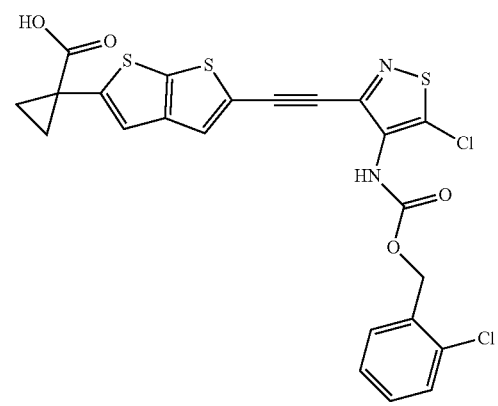 [SMILES: O=C(Nc1c(C#Cc2cc3cc(C4(C(=O)O)CC4)sc3s2)nsc1Cl)OCc1ccccc1Cl]

TABLE 17-continued
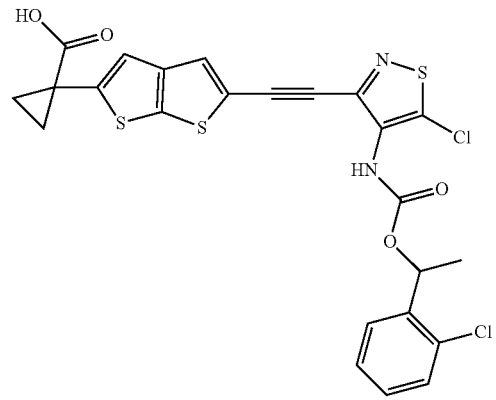 [SMILES: CC(OC(=O)Nc1c(C#Cc2cc3cc(C4(C(=O)O)CC4)sc3s2)nsc1Cl)c1ccccc1Cl]
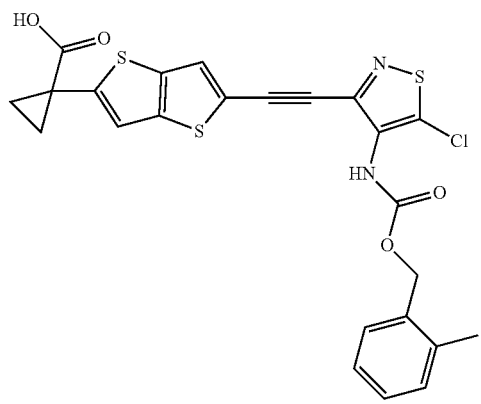 [SMILES: Cc1ccccc1COC(=O)Nc1c(C#Cc2cc3sc(C4(C(=O)O)CC4)cc3s2)nsc1Cl]
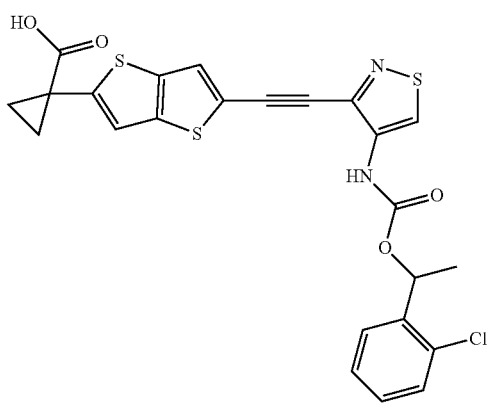 [SMILES: CC(OC(=O)Nc1csnc1C#Cc1cc2sc(C3(C(=O)O)CC3)cc2s1)c1ccccc1Cl]
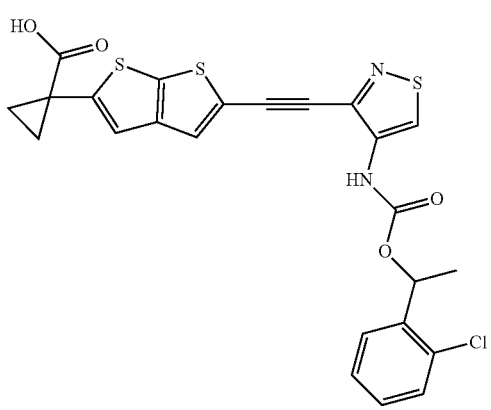 [SMILES: CC(OC(=O)Nc1csnc1C#Cc1cc2cc(C3(C(=O)O)CC3)sc2s1)c1ccccc1Cl]
TABLE 17-continued
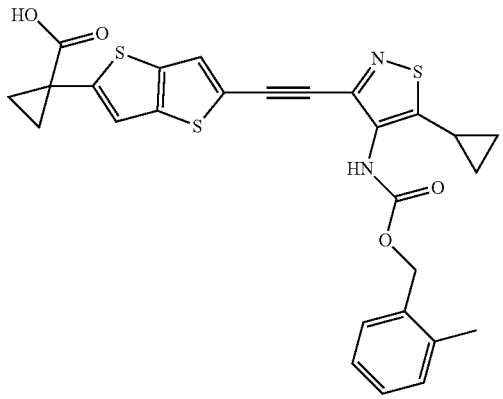 [SMILES: Cc1ccccc1COC(=O)Nc1c(C#Cc2cc3sc(C4(C(=O)O)CC4)cc3s2)nsc1C1CC1]
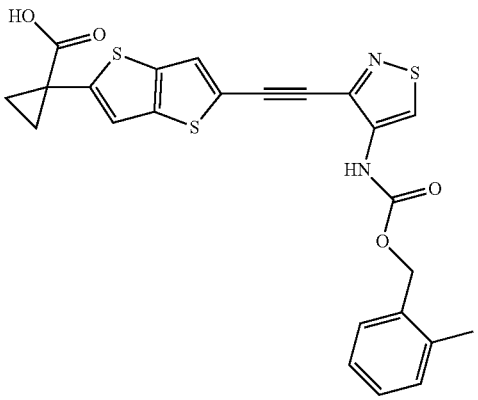 [SMILES: Cc1ccccc1COC(=O)Nc1csnc1C#Cc1cc2sc(C3(C(=O)O)CC3)cc2s1]
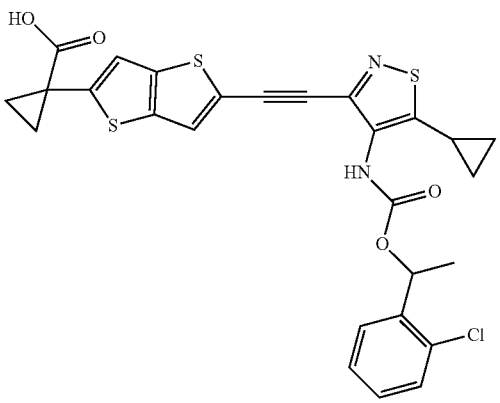 [SMILES: CC(OC(=O)Nc1c(C#Cc2cc3sc(C4(C(=O)O)CC4)cc3s2)nsc1C1CC1)c1ccccc1Cl]
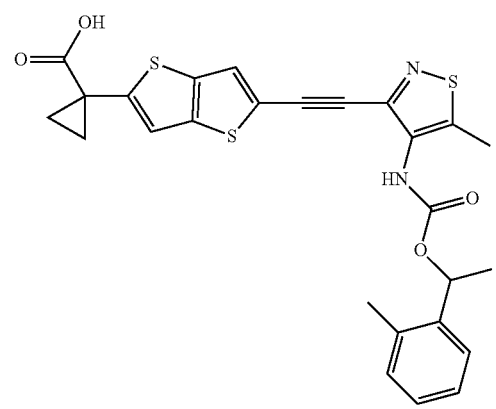 [SMILES: Cc1ccccc1C(C)OC(=O)Nc1c(C#Cc2cc3sc(C4(C(=O)O)CC4)cc3s2)nsc1C]

607
TABLE 17-continued
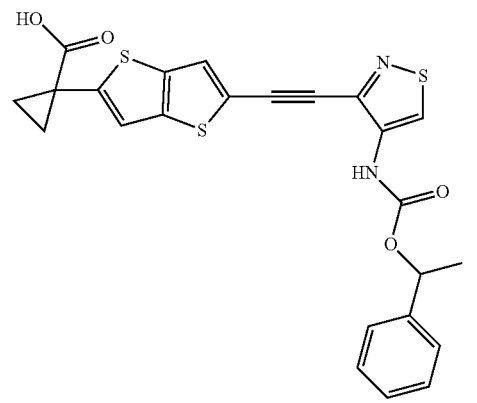 [SMILES: CC(OC(=O)Nc1csnc1C#Cc1cc2sc(C3(C(=O)O)CC3)cc2s1)c1ccccc1]
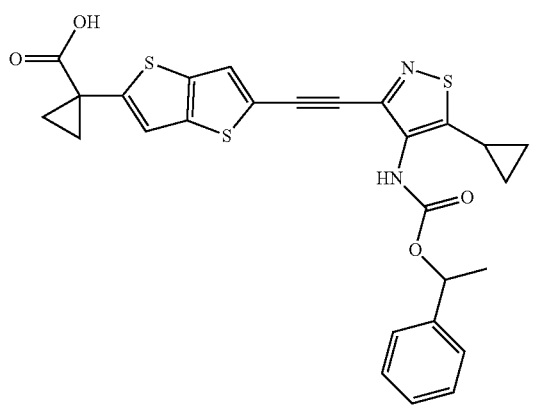 [SMILES: CC(OC(=O)Nc1c(C#Cc2cc3sc(C4(C(=O)O)CC4)cc3s2)nsc1C1CC1)c1ccccc1]
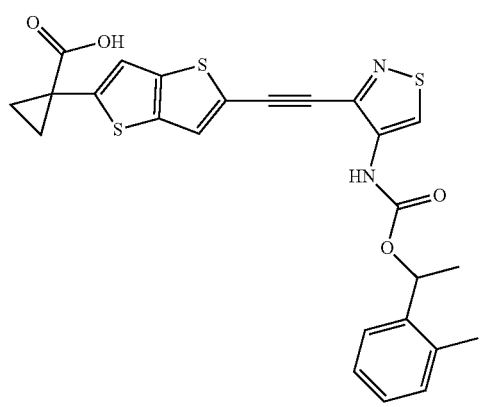 [SMILES: Cc1ccccc1C(C)OC(=O)Nc1csnc1C#Cc1cc2sc(C3(C(=O)O)CC3)cc2s1]
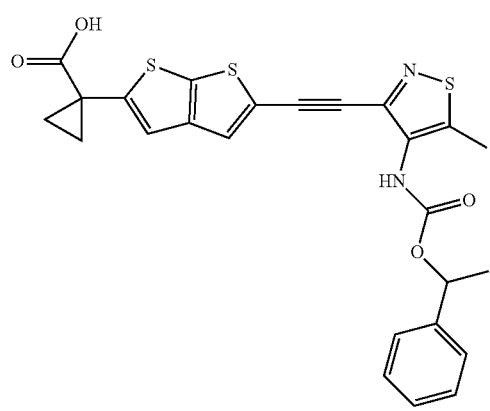 [SMILES: Cc1snc(C#Cc2cc3cc(C4(C(=O)O)CC4)sc3s2)c1NC(=O)OC(C)c1ccccc1]
608
TABLE 17-continued
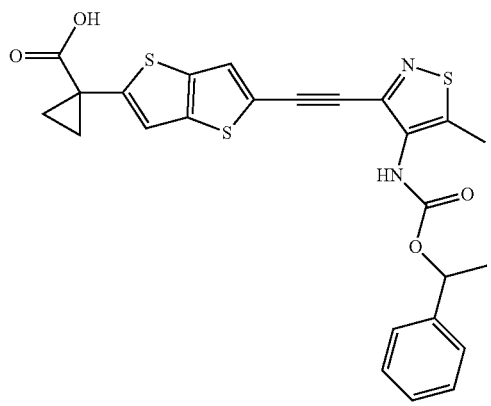 [SMILES: Cc1snc(C#Cc2cc3sc(C4(C(=O)O)CC4)cc3s2)c1NC(=O)OC(C)c1ccccc1]
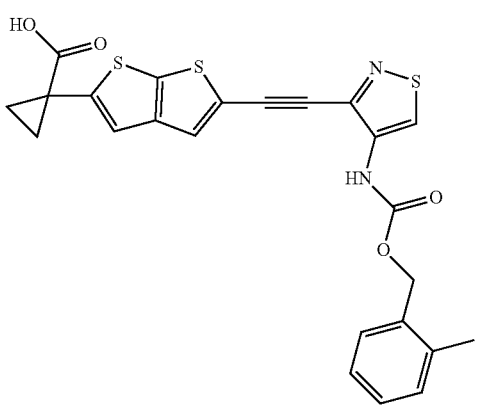 [SMILES: Cc1ccccc1COC(=O)Nc1csnc1C#Cc1cc2cc(C3(C(=O)O)CC3)sc2s1]
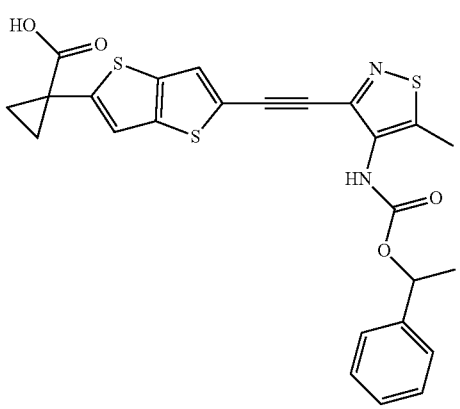 [SMILES: Cc1snc(C#Cc2cc3sc(C4(C(=O)O)CC4)cc3s2)c1NC(=O)OC(C)c1ccccc1]
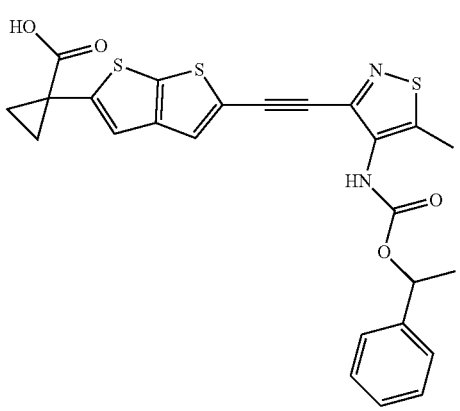 [SMILES: Cc1snc(C#Cc2cc3cc(C4(C(=O)O)CC4)sc3s2)c1NC(=O)OC(C)c1ccccc1]

TABLE 17-continued
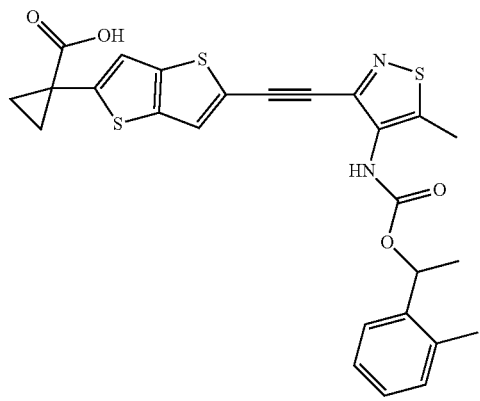 [SMILES: Cc1ccccc1C(C)OC(=O)Nc1c(C#Cc2cc3sc(C4(C(=O)O)CC4)cc3s2)nsc1C]
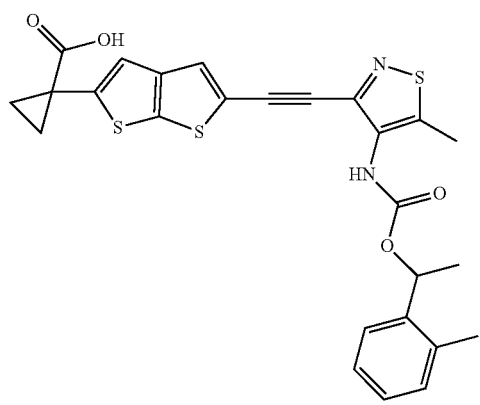
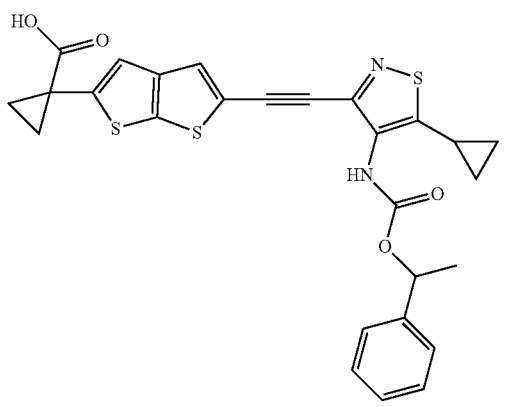
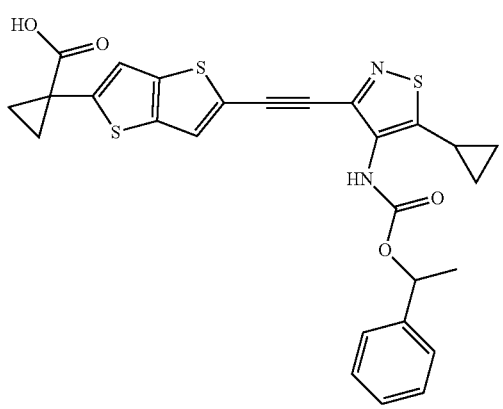 [SMILES: CC(OC(=O)Nc1c(C#Cc2cc3sc(C4(C(=O)O)CC4)cc3s2)nsc1C1CC1)c1ccccc1]
TABLE 17-continued
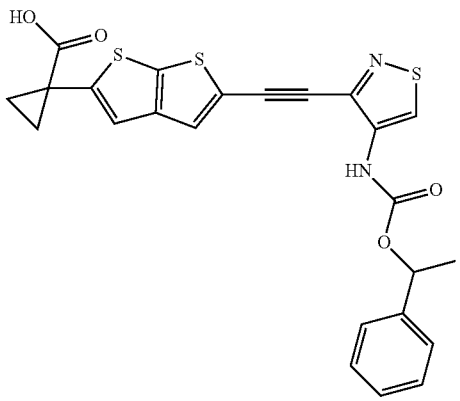 [SMILES: CC(OC(=O)Nc1csnc1C#Cc1cc2cc(C3(C(=O)O)CC3)sc2s1)c1ccccc1]
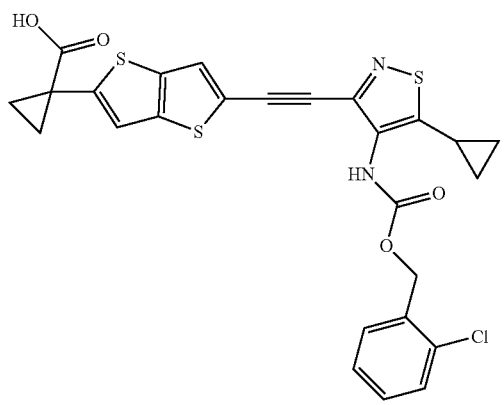 [SMILES: O=C(Nc1c(C#Cc2cc3sc(C4(C(=O)O)CC4)cc3s2)nsc1C1CC1)OCc1ccccc1Cl]
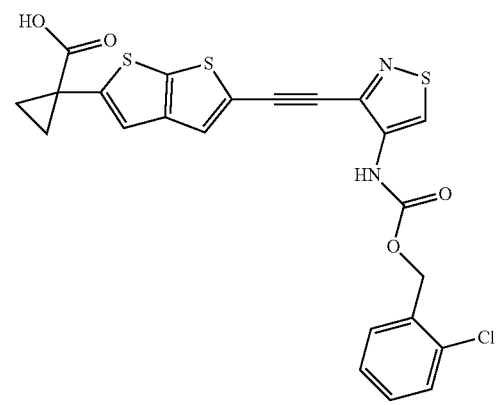
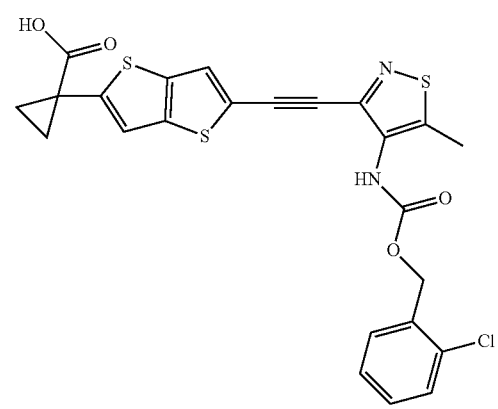 [SMILES: Cc1snc(C#Cc2cc3sc(C4(C(=O)O)CC4)cc3s2)c1NC(=O)OCc1ccccc1Cl]

TABLE 17-continued
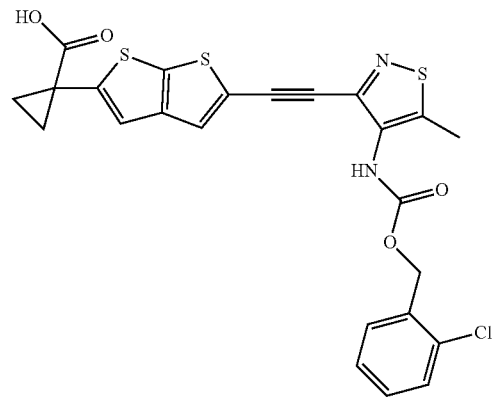 [SMILES: Cc1snc(C#Cc2cc3cc(C4(C(=O)O)CC4)sc3s2)c1NC(=O)OCc1ccccc1Cl]
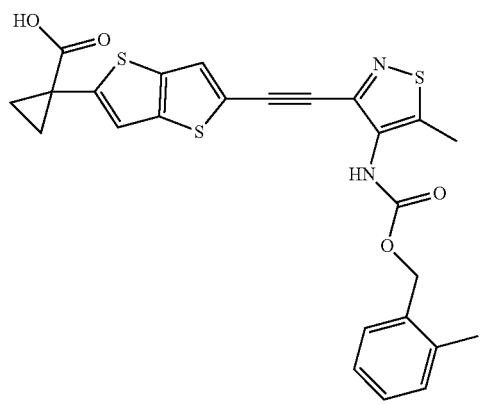
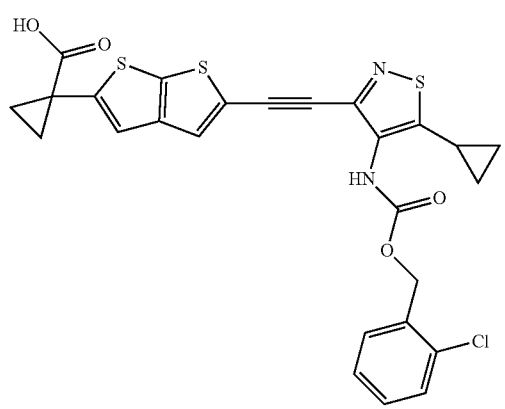 [SMILES: O=C(Nc1c(C#Cc2cc3cc(C4(C(=O)O)CC4)sc3s2)nsc1C1CC1)OCc1ccccc1Cl]
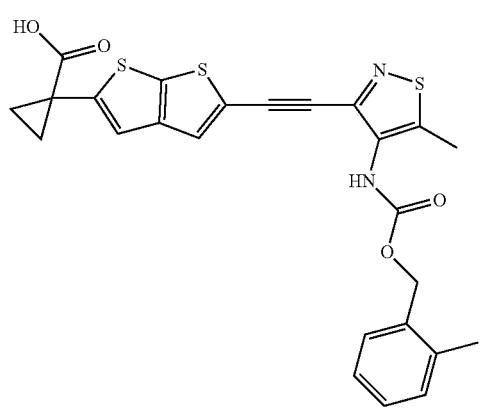
TABLE 17-continued
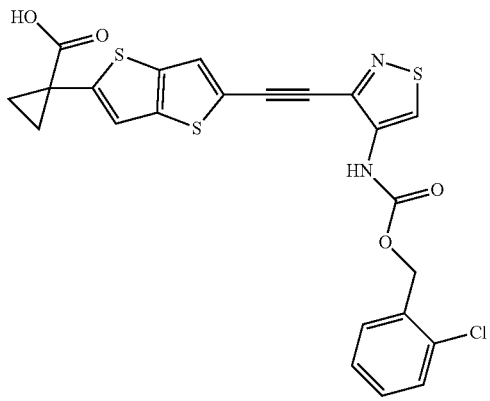 [SMILES: O=C(Nc1csnc1C#Cc1cc2sc(C3(C(=O)O)CC3)cc2s1)OCc1ccccc1Cl]
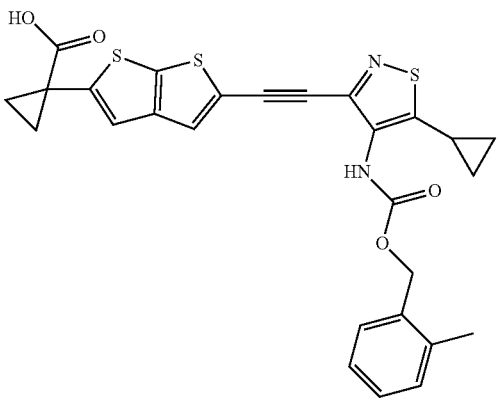 [SMILES: Cc1ccccc1COC(=O)Nc1c(C#Cc2cc3cc(C4(C(=O)O)CC4)sc3s2)nsc1C1CC1]
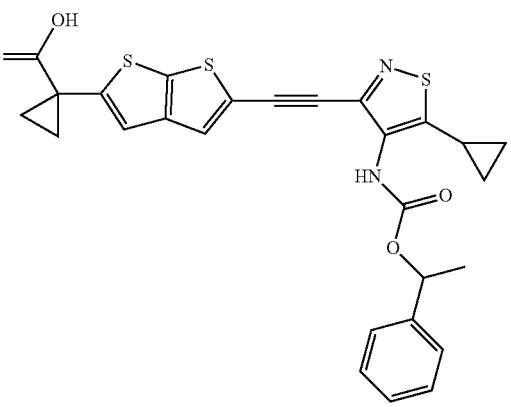
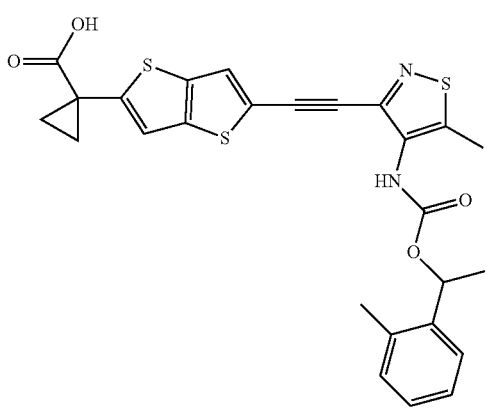 [SMILES: Cc1ccccc1C(C)OC(=O)Nc1c(C#Cc2cc3sc(C4(C(=O)O)CC4)cc3s2)nsc1C]

TABLE 17-continued
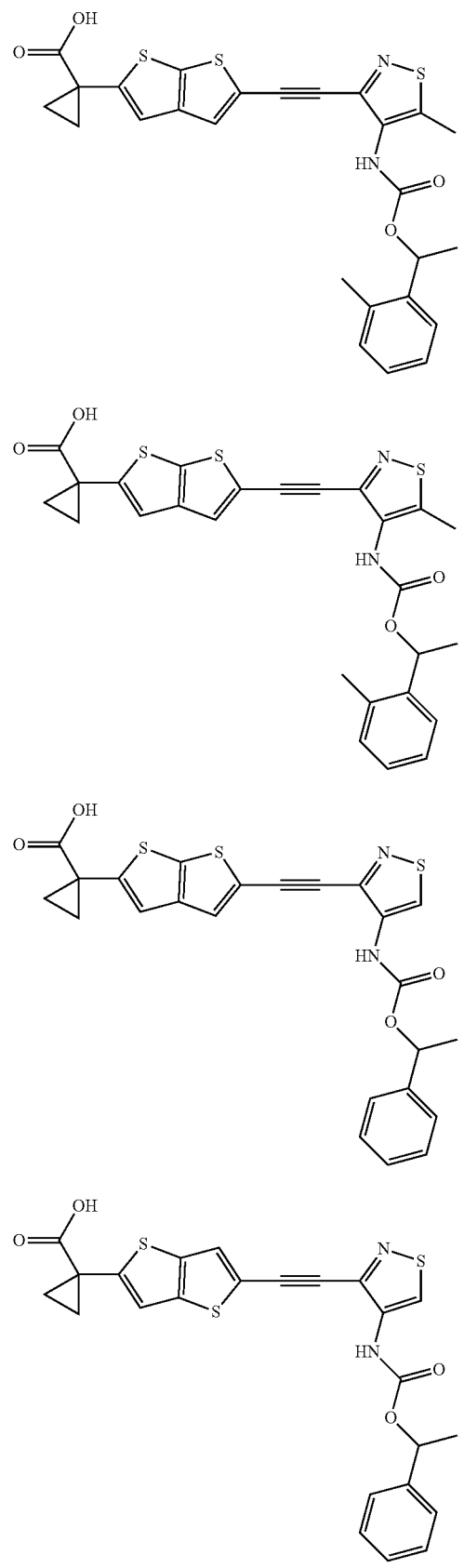
TABLE 17-continued
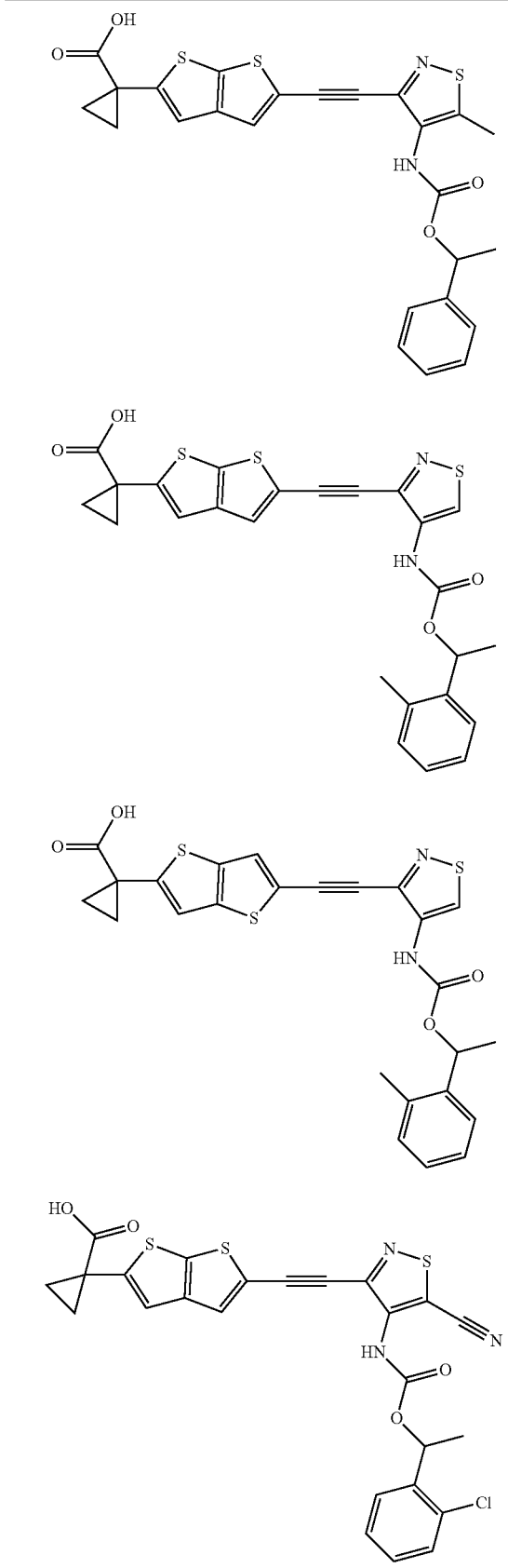

615
TABLE 17-continued
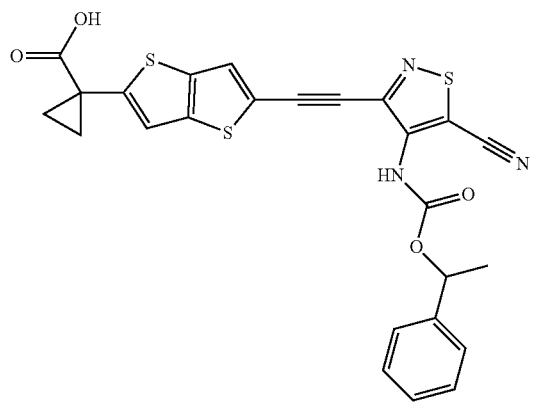 [SMILES: CC(OC(=O)Nc1c(C#Cc2cc3sc(C4(C(=O)O)CC4)cc3s2)nsc1C#N)c1ccccc1]
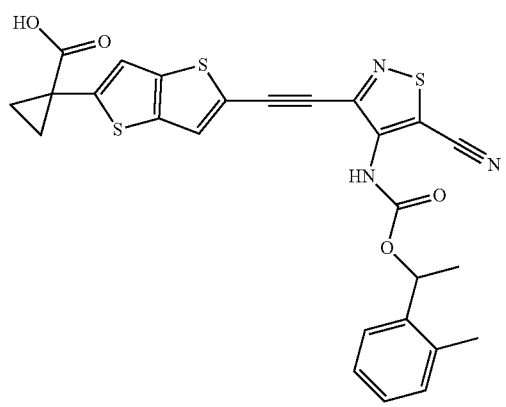 [SMILES: Cc1ccccc1C(C)OC(=O)Nc1c(C#Cc2cc3sc(C4(C(=O)O)CC4)cc3s2)nsc1C#N]
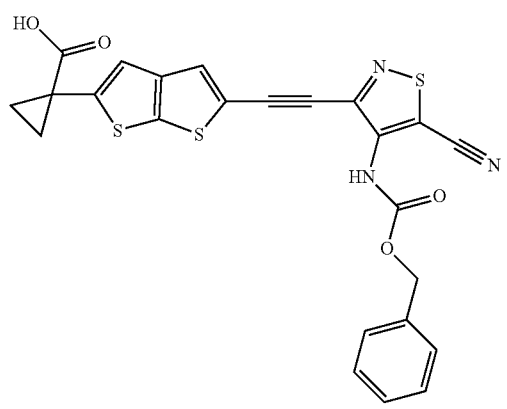 [SMILES: N#Cc1snc(C#Cc2cc3cc(C4(C(=O)O)CC4)sc3s2)c1NC(=O)OCc1ccccc1]
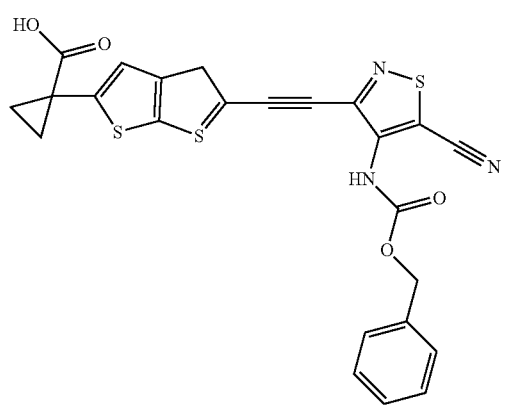
616
TABLE 17-continued
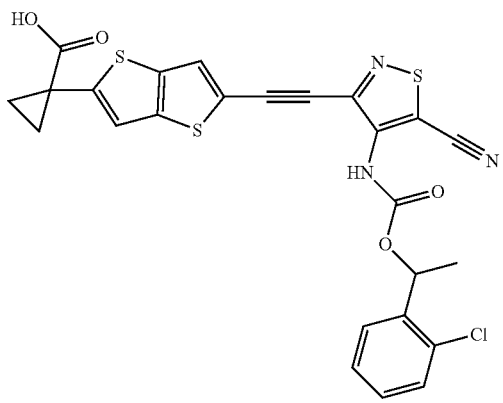 [SMILES: CC(OC(=O)Nc1c(C#Cc2cc3sc(C4(C(=O)O)CC4)cc3s2)nsc1C#N)c1ccccc1Cl]
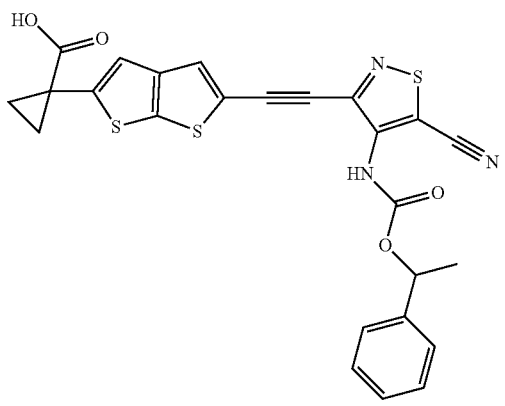 [SMILES: CC(OC(=O)Nc1c(C#Cc2cc3cc(C4(C(=O)O)CC4)sc3s2)nsc1C#N)c1ccccc1]
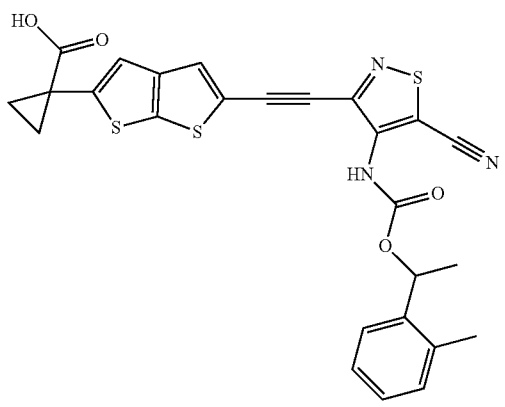 [SMILES: Cc1ccccc1C(C)OC(=O)Nc1c(C#Cc2cc3cc(C4(C(=O)O)CC4)sc3s2)nsc1C#N]
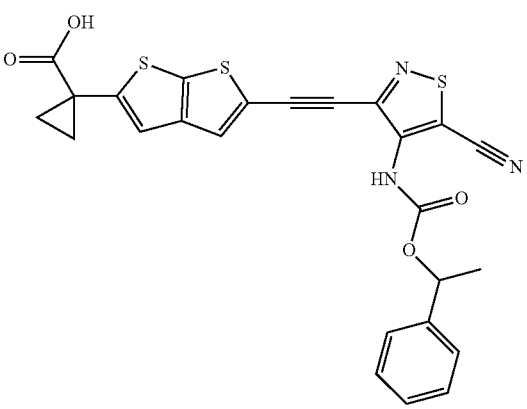 [SMILES: CC(OC(=O)Nc1c(C#Cc2cc3cc(C4(C(=O)O)CC4)sc3s2)nsc1C#N)c1ccccc1]

617
TABLE 17-continued
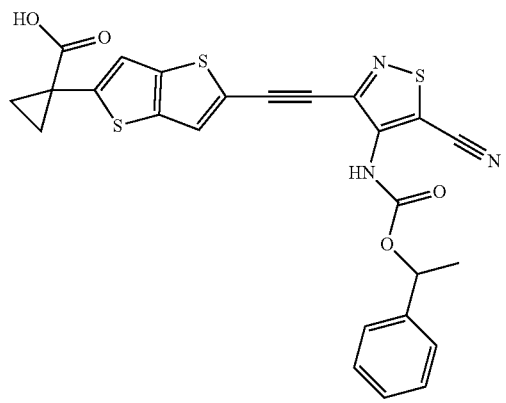 [SMILES: CC(OC(=O)Nc1c(C#Cc2cc3sc(C4(C(=O)O)CC4)cc3s2)nsc1C#N)c1ccccc1]
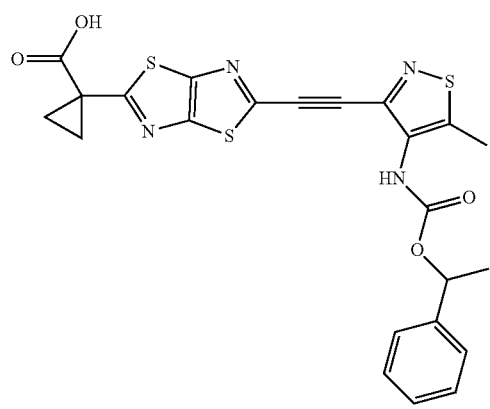 [SMILES: Cc1snc(C#Cc2nc3sc(C4(C(=O)O)CC4)nc3s2)c1NC(=O)OC(C)c1ccccc1]
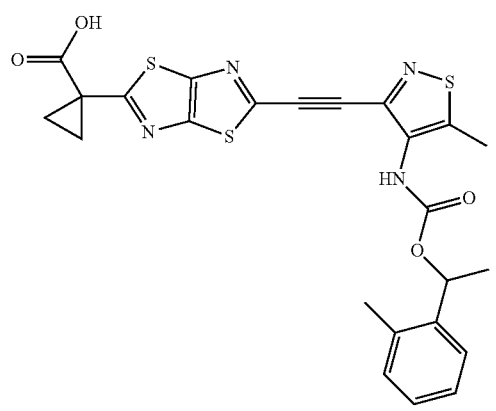 [SMILES: Cc1ccccc1C(C)OC(=O)Nc1c(C#Cc2nc3sc(C4(C(=O)O)CC4)nc3s2)nsc1C]
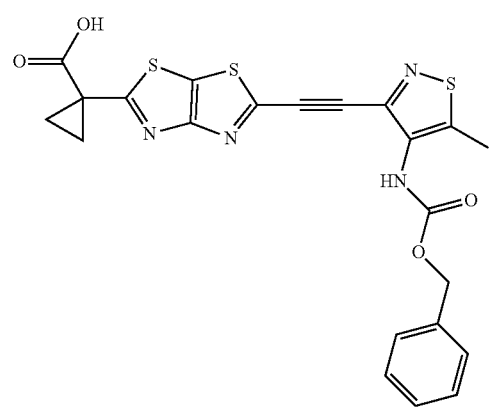
618
TABLE 17-continued
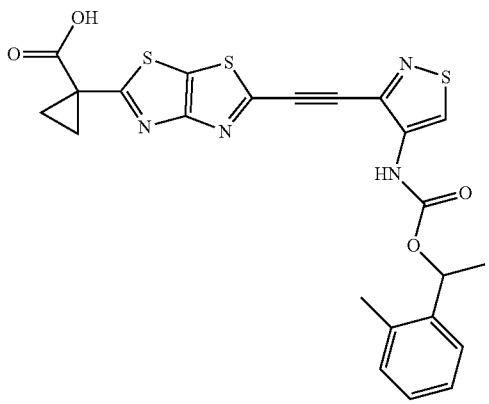
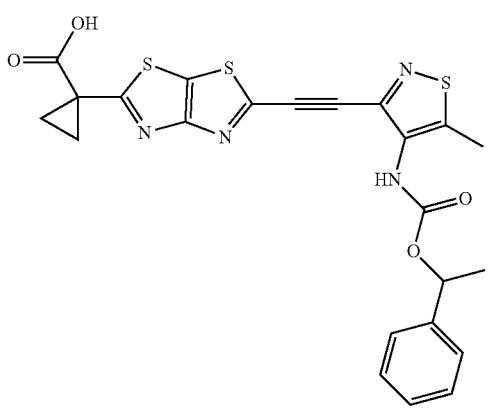 [SMILES: Cc1snc(C#Cc2nc3nc(C4(C(=O)O)CC4)sc3s2)c1NC(=O)OC(C)c1ccccc1]
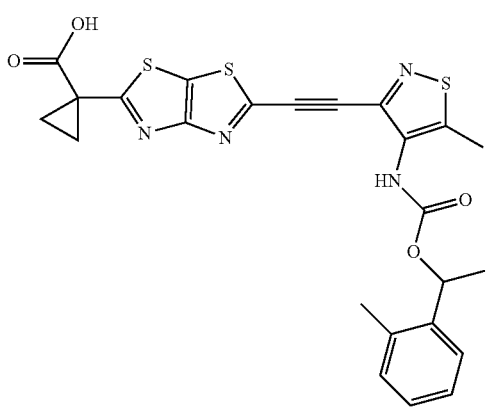
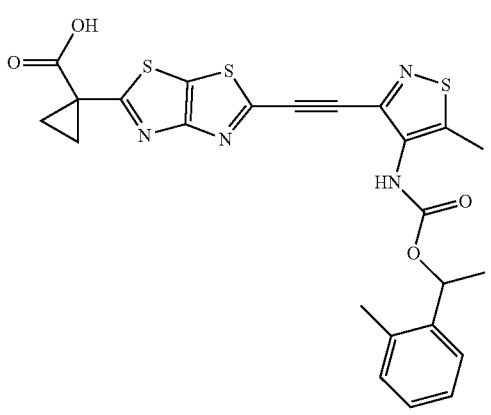 [SMILES: Cc1ccccc1C(C)OC(=O)Nc1c(C#Cc2nc3nc(C4(C(=O)O)CC4)sc3s2)nsc1C]

619
TABLE 17-continued
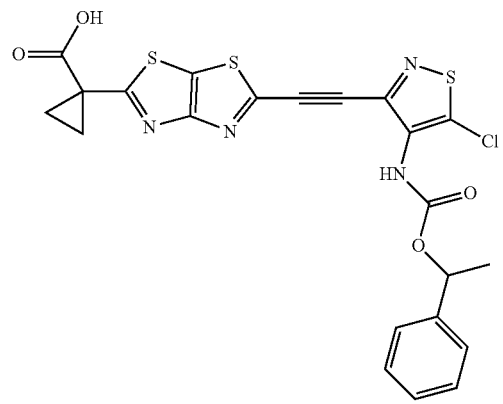 [SMILES: CC(OC(=O)Nc1c(C#Cc2nc3nc(C4(C(=O)O)CC4)sc3s2)nsc1Cl)c1ccccc1]
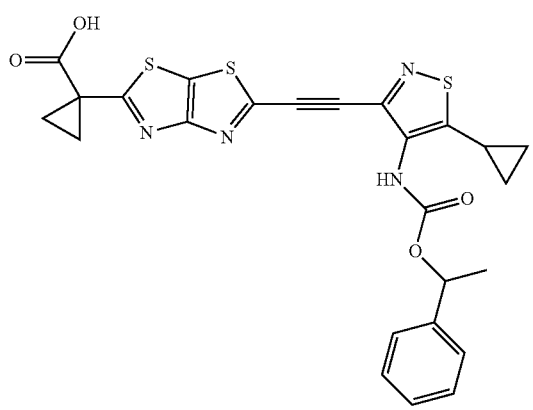 [SMILES: CC(OC(=O)Nc1c(C#Cc2nc3nc(C4(C(=O)O)CC4)sc3s2)nsc1C1CC1)c1ccccc1]
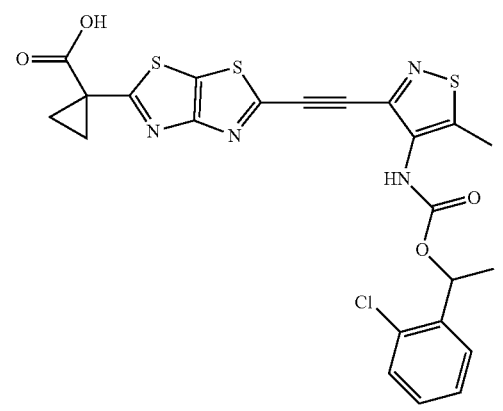
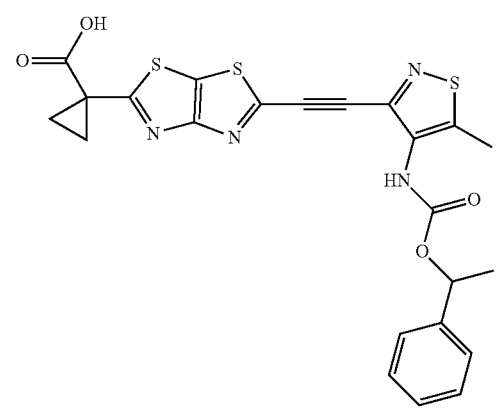 [SMILES: Cc1snc(C#Cc2nc3nc(C4(C(=O)O)CC4)sc3s2)c1NC(=O)OC(C)c1ccccc1]
620
TABLE 17-continued
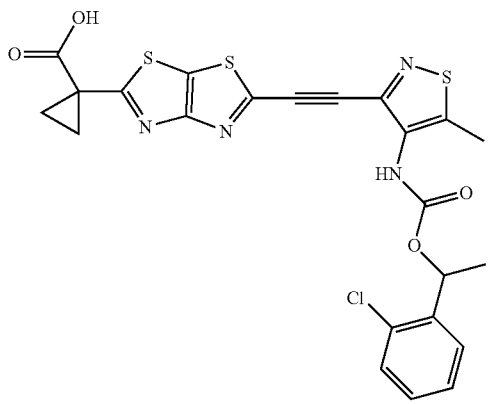 [SMILES: Cc1snc(C#Cc2nc3nc(C4(C(=O)O)CC4)sc3s2)c1NC(=O)OC(C)c1ccccc1Cl]
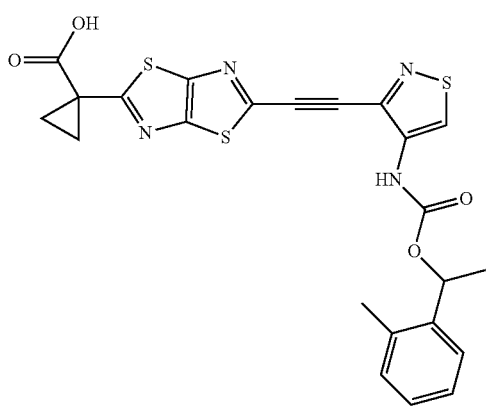 [SMILES: Cc1ccccc1C(C)OC(=O)Nc1csnc1C#Cc1nc2sc(C3(C(=O)O)CC3)nc2s1]
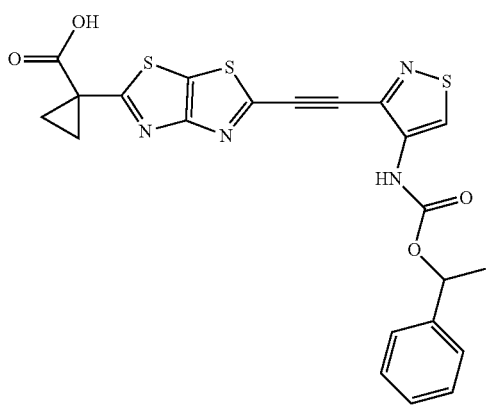
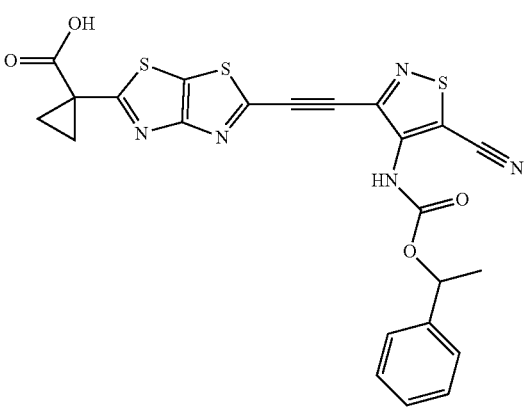 [SMILES: CC(OC(=O)Nc1c(C#Cc2nc3nc(C4(C(=O)O)CC4)sc3s2)nsc1C#N)c1ccccc1]

In some embodiments, compounds of Formula (I) are selected from the following compounds as listed in Table 18.
TABLE 18
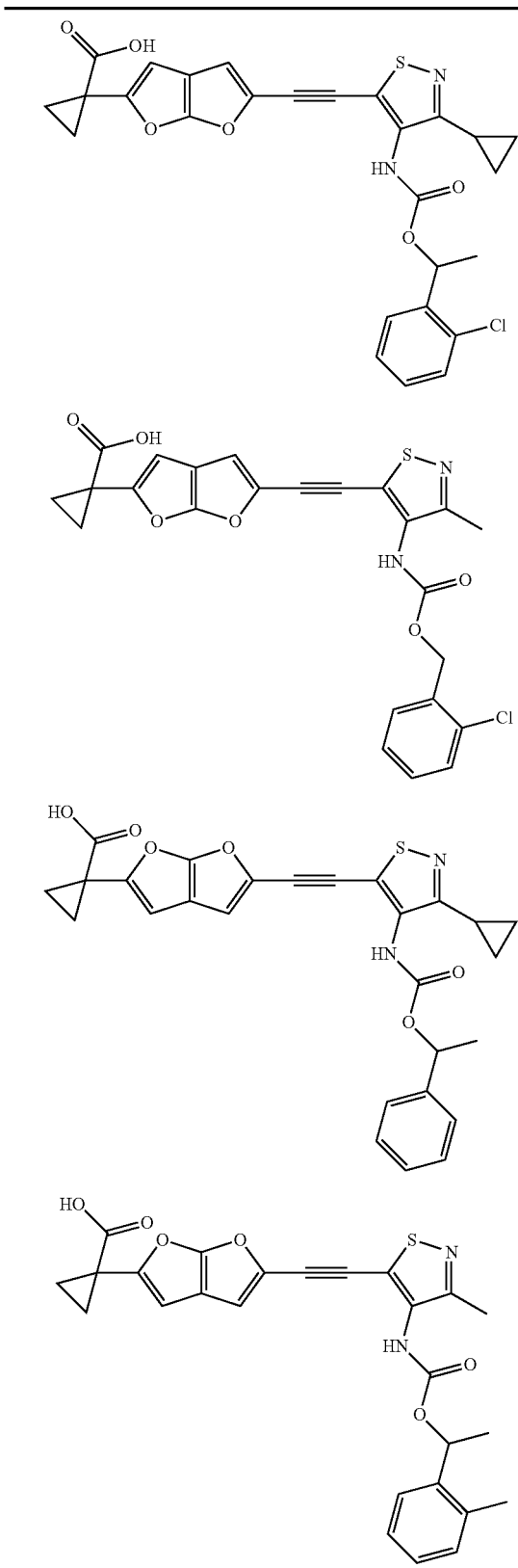
TABLE 18-continued
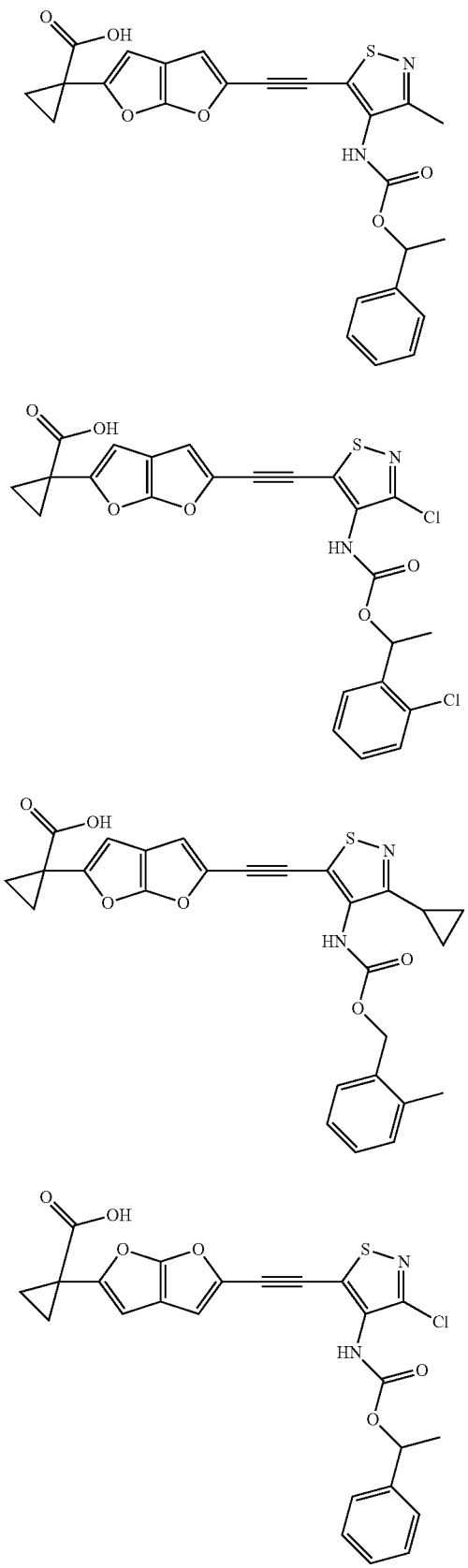

TABLE 18-continued
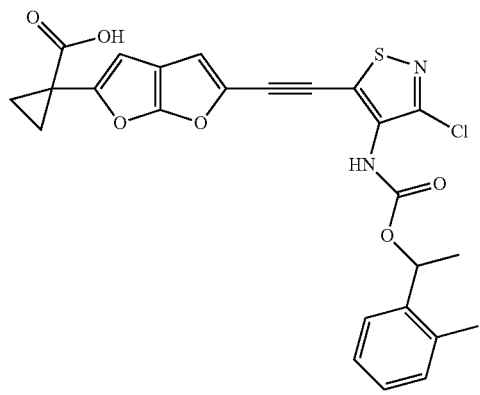 [SMILES: Cc1ccccc1C(C)OC(=O)Nc1c(Cl)nsc1C#Cc1cc2cc(C3(C(=O)O)CC3)oc2o1]
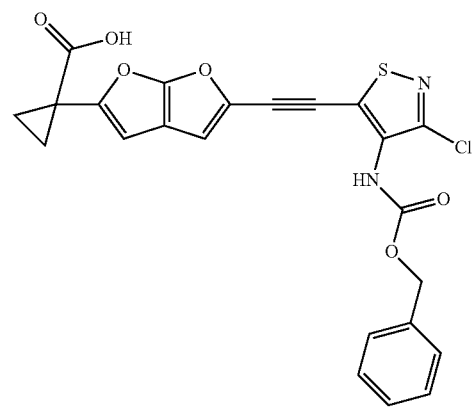 [SMILES: O=C(Nc1c(Cl)nsc1C#Cc1cc2cc(C3(C(=O)O)CC3)oc2o1)OCc1ccccc1]
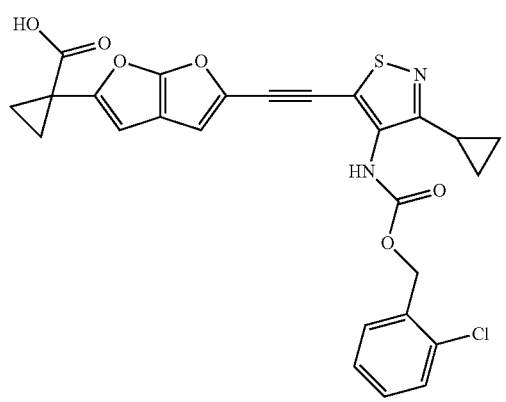 [SMILES: O=C(Nc1c(C2CC2)nsc1C#Cc1cc2cc(C3(C(=O)O)CC3)oc2o1)OCc1ccccc1Cl]
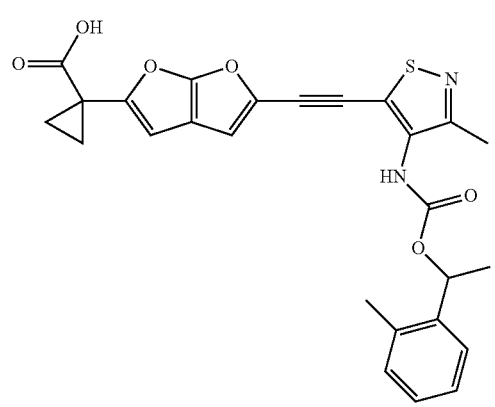
TABLE 18-continued
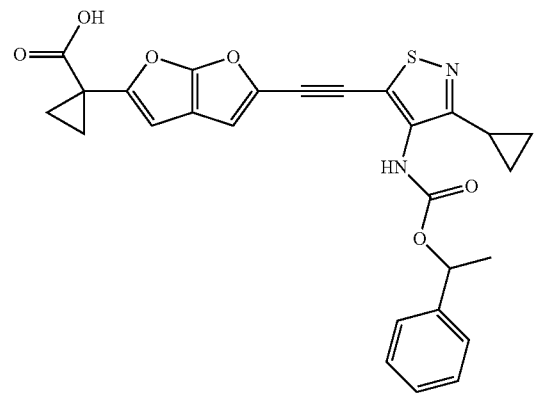
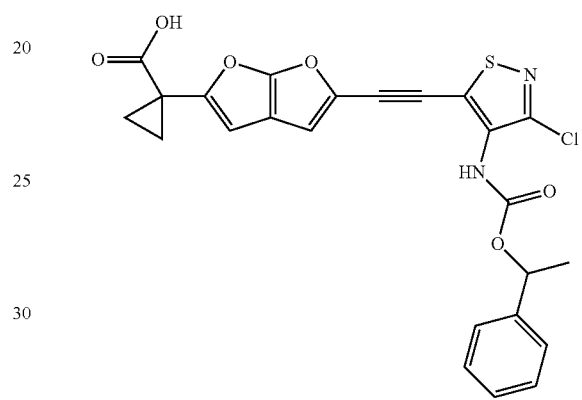
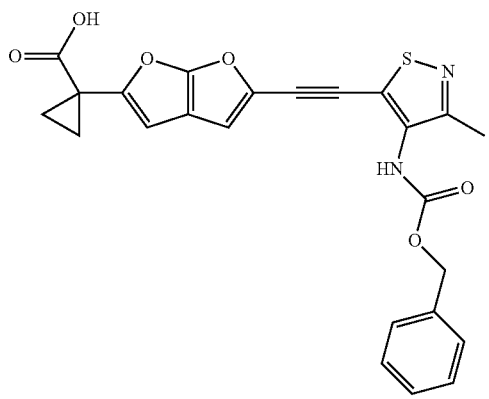 [SMILES: Cc1nsc(C#Cc2cc3cc(C4(C(=O)O)CC4)oc3o2)c1NC(=O)OCc1ccccc1]
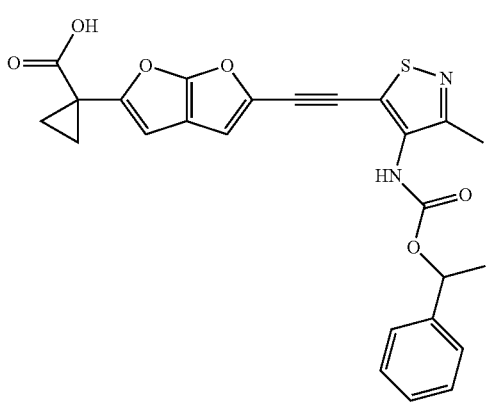 [SMILES: Cc1nsc(C#Cc2cc3cc(C4(C(=O)O)CC4)oc3o2)c1NC(=O)OC(C)c1ccccc1]

TABLE 18-continued
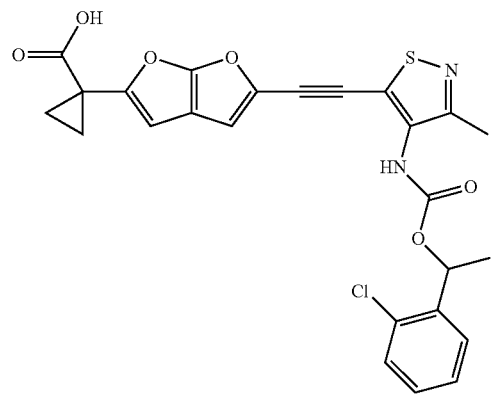 [SMILES: Cc1nsc(C#Cc2cc3cc(C4(C(=O)O)CC4)oc3o2)c1NC(=O)OC(C)c1ccccc1Cl]
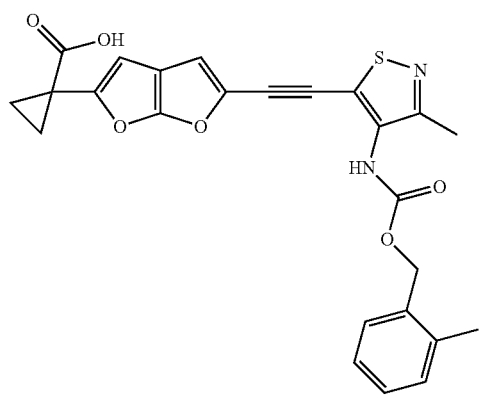 [SMILES: Cc1ccccc1COC(=O)Nc1c(C)nsc1C#Cc1cc2cc(C3(C(=O)O)CC3)oc2o1]
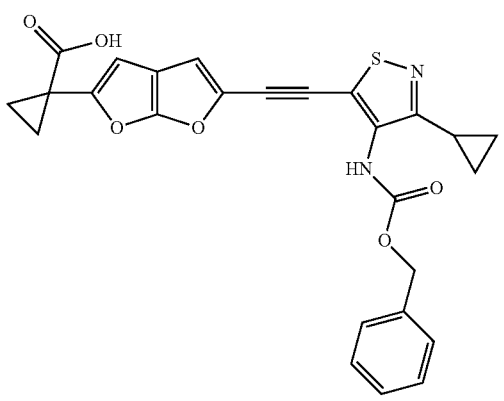 [SMILES: O=C(Nc1c(C2CC2)nsc1C#Cc1cc2cc(C3(C(=O)O)CC3)oc2o1)OCc1ccccc1]
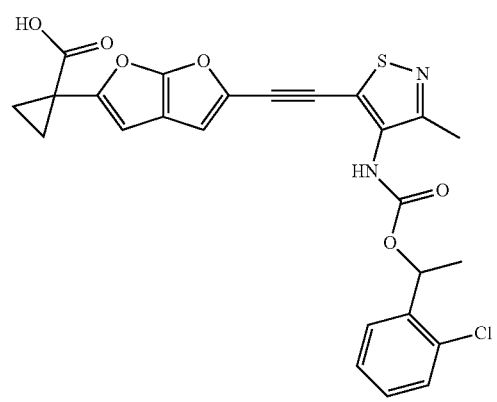 [SMILES: Cc1nsc(C#Cc2cc3cc(C4(C(=O)O)CC4)oc3o2)c1NC(=O)OC(C)c1ccccc1Cl]
TABLE 18-continued
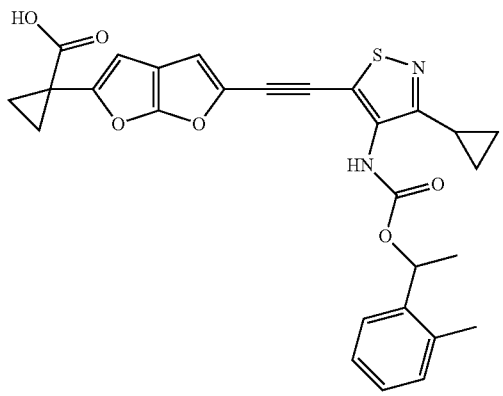 [SMILES: Cc1ccccc1C(C)OC(=O)Nc1c(C2CC2)nsc1C#Cc1cc2cc(C3(C(=O)O)CC3)oc2o1]
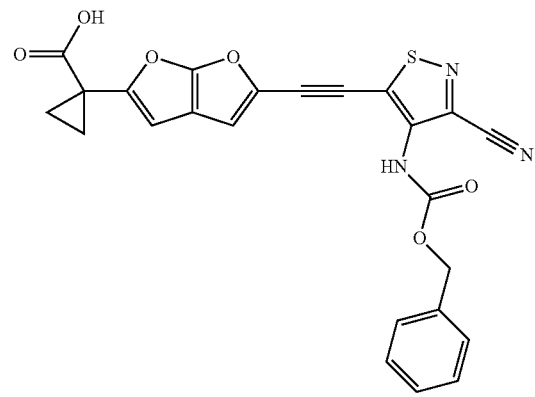
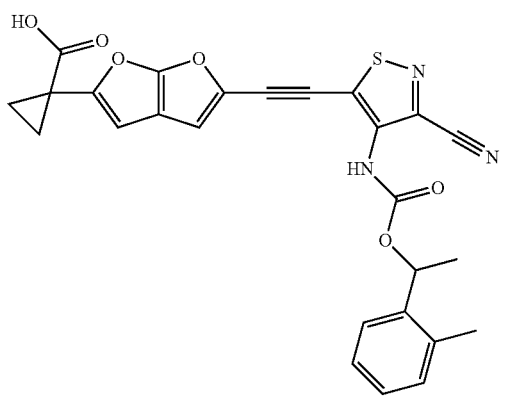 [SMILES: Cc1ccccc1C(C)OC(=O)Nc1c(C#N)nsc1C#Cc1cc2cc(C3(C(=O)O)CC3)oc2o1]
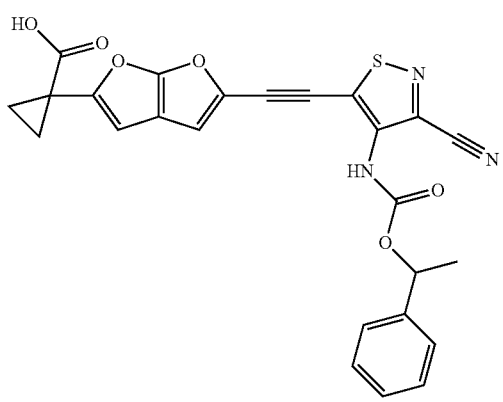 [SMILES: CC(OC(=O)Nc1c(C#N)nsc1C#Cc1cc2cc(C3(C(=O)O)CC3)oc2o1)c1ccccc1]

TABLE 18-continued
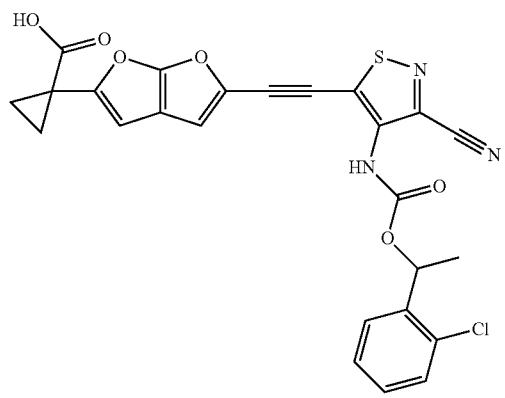 [SMILES: CC(OC(=O)Nc1c(C#N)nsc1C#Cc1cc2cc(C3(C(=O)O)CC3)oc2o1)c1ccccc1Cl]
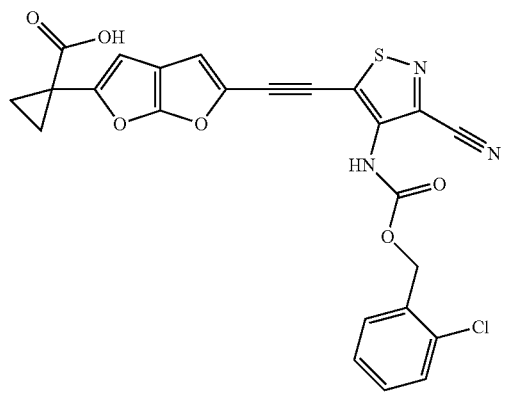 [SMILES: N#Cc1nsc(C#Cc2cc3cc(C4(C(=O)O)CC4)oc3o2)c1NC(=O)OCc1ccccc1Cl]
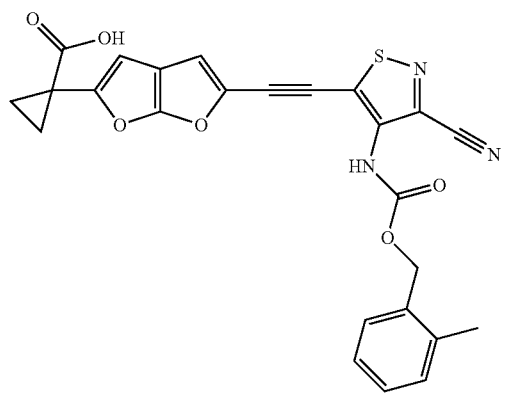 [SMILES: Cc1ccccc1COC(=O)Nc1c(C#N)nsc1C#Cc1cc2cc(C3(C(=O)O)CC3)oc2o1]
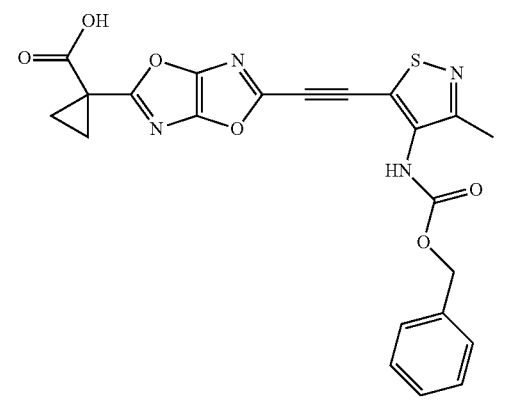
TABLE 18-continued
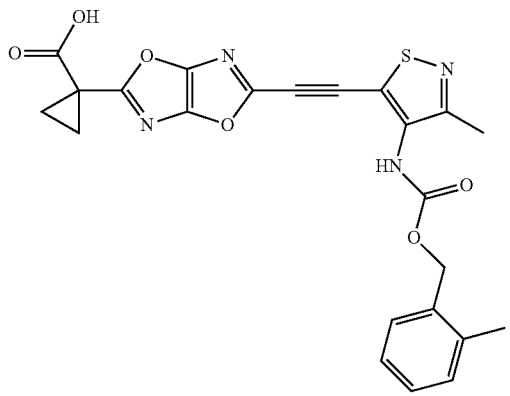
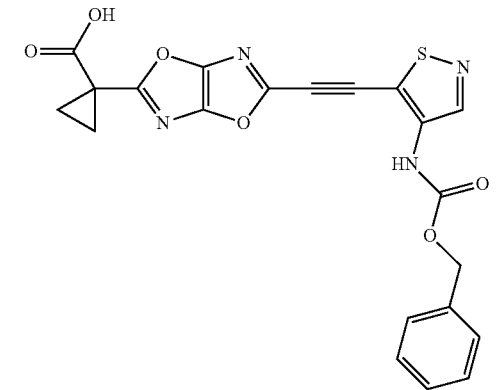 [SMILES: O=C(Nc1cnsc1C#Cc1nc2oc(C3(C(=O)O)CC3)nc2o1)OCc1ccccc1]
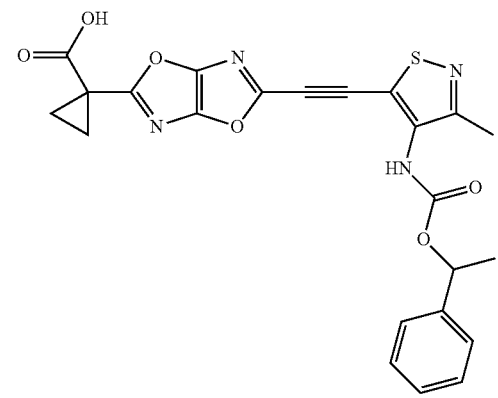 [SMILES: Cc1nsc(C#Cc2nc3oc(C4(C(=O)O)CC4)nc3o2)c1NC(=O)OC(C)c1ccccc1]
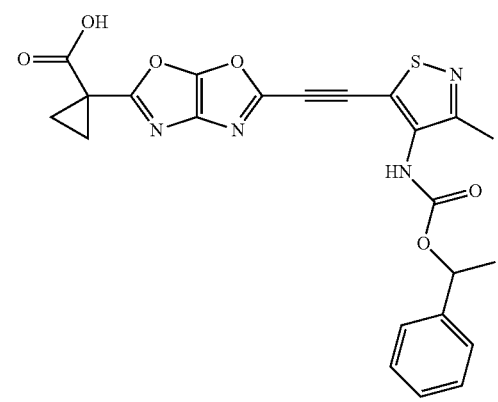 [SMILES: Cc1nsc(C#Cc2nc3nc(C4(C(=O)O)CC4)oc3o2)c1NC(=O)OC(C)c1ccccc1]

| 629 | 630 |
|---|---|
| TABLE 18-continued | TABLE 18-continued |
| 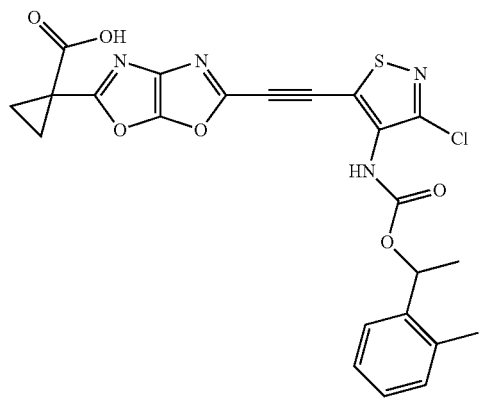 [SMILES: Cc1ccccc1C(C)OC(=O)Nc1c(Cl)nsc1C#Cc1nc2nc(C3(C(=O)O)CC3)oc2o1] | 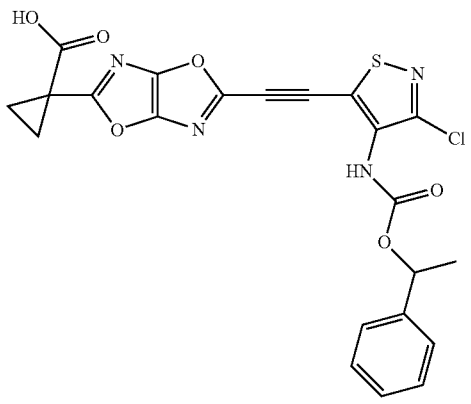 |
| 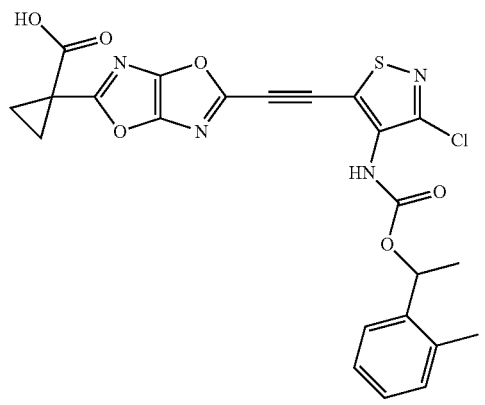 [SMILES: Cc1ccccc1C(C)OC(=O)Nc1c(Cl)nsc1C#Cc1nc2oc(C3(C(=O)O)CC3)nc2o1] | 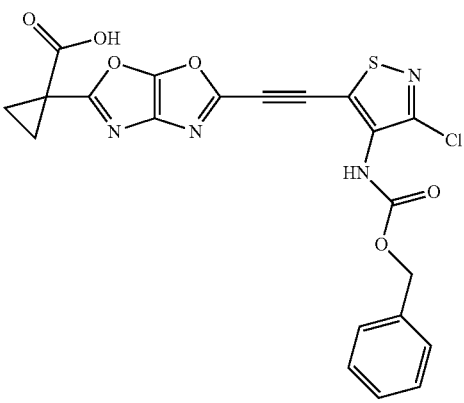 |
| 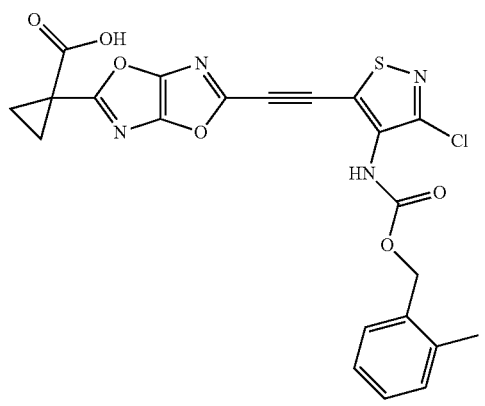 [SMILES: Cc1ccccc1COC(=O)Nc1c(Cl)nsc1C#Cc1nc2oc(C3(C(=O)O)CC3)nc2o1] | 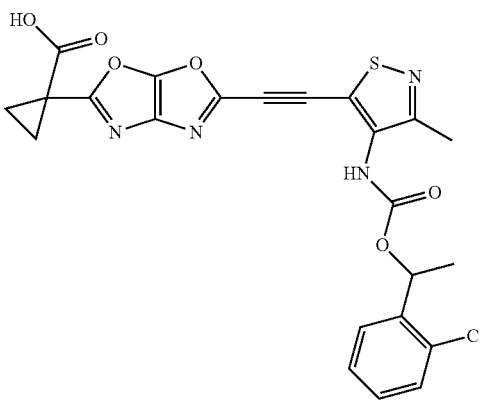 |
| 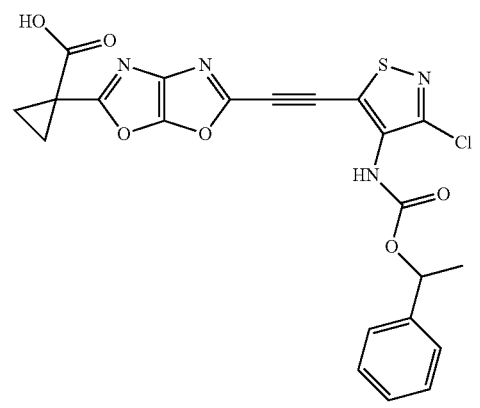 [SMILES: CC(OC(=O)Nc1c(Cl)nsc1C#Cc1nc2nc(C3(C(=O)O)CC3)oc2o1)c1ccccc1] | 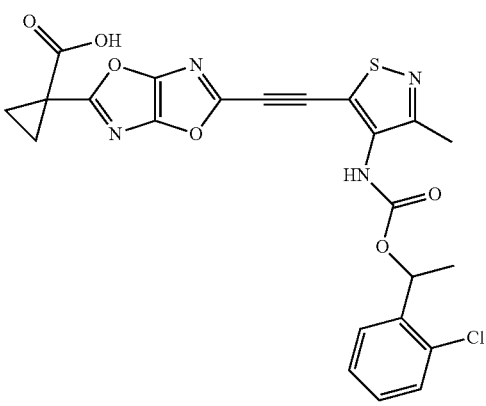 |

TABLE 18-continued
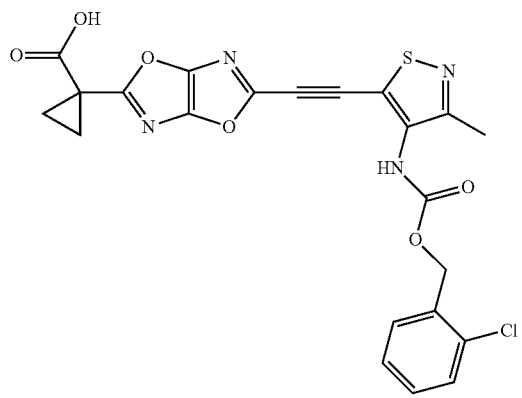
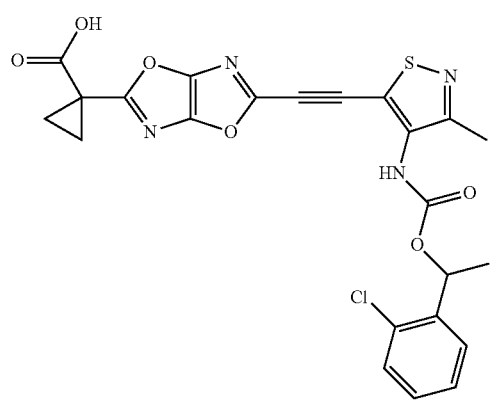
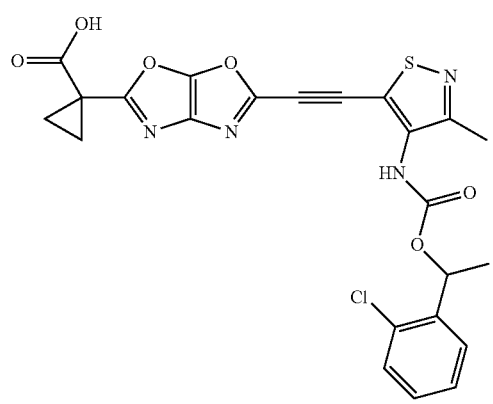
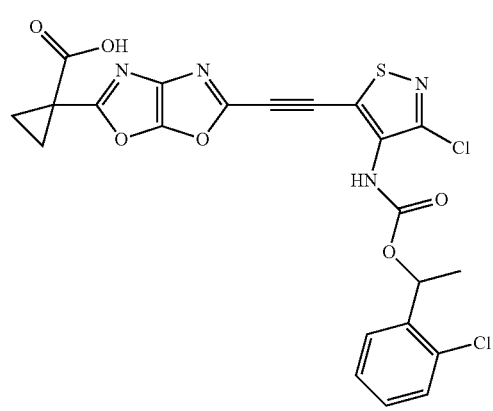 [SMILES: CC(OC(=O)Nc1c(Cl)nsc1C#Cc1nc2nc(C3(C(=O)O)CC3)oc2o1)c1ccccc1Cl]
TABLE 18-continued
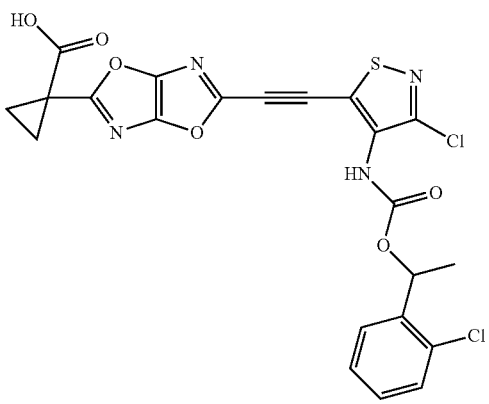 [SMILES: CC(OC(=O)Nc1c(Cl)nsc1C#Cc1nc2oc(C3(C(=O)O)CC3)nc2o1)c1ccccc1Cl]
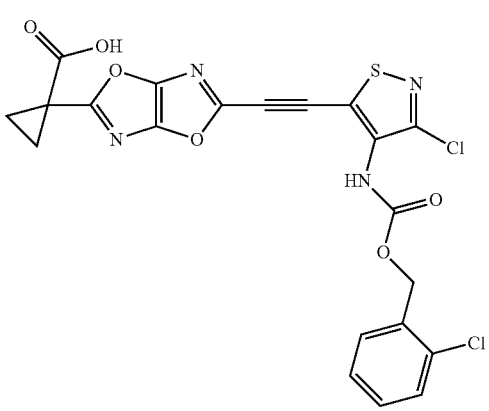 [SMILES: O=C(Nc1c(Cl)nsc1C#Cc1nc2oc(C3(C(=O)O)CC3)nc2o1)OCc1ccccc1Cl]
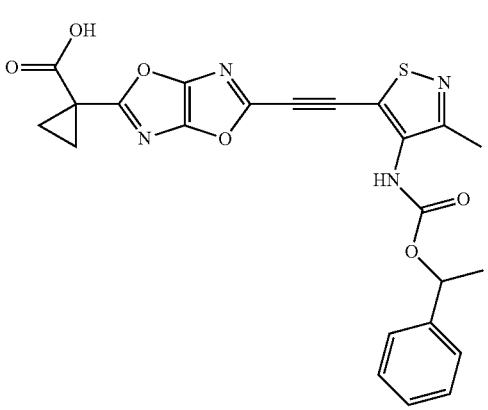 [SMILES: Cc1nsc(C#Cc2nc3oc(C4(C(=O)O)CC4)nc3o2)c1NC(=O)OC(C)c1ccccc1]
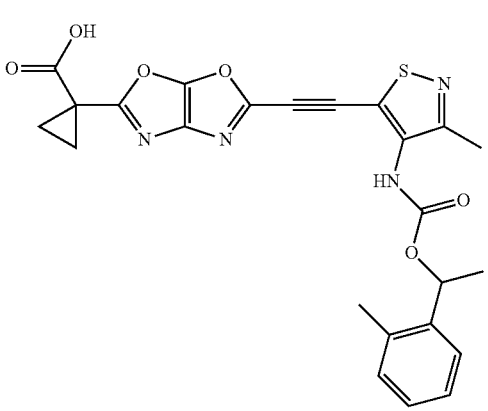 [SMILES: Cc1ccccc1C(C)OC(=O)Nc1c(C)nsc1C#Cc1nc2nc(C3(C(=O)O)CC3)oc2o1]

TABLE 18-continued
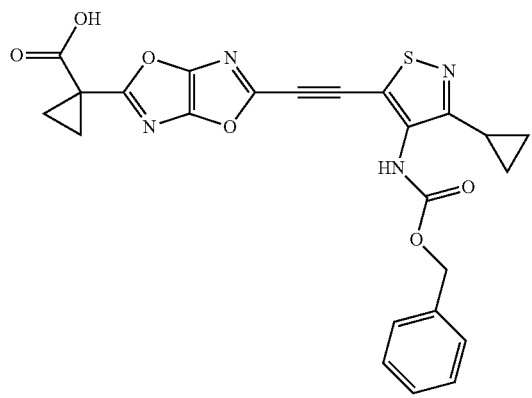
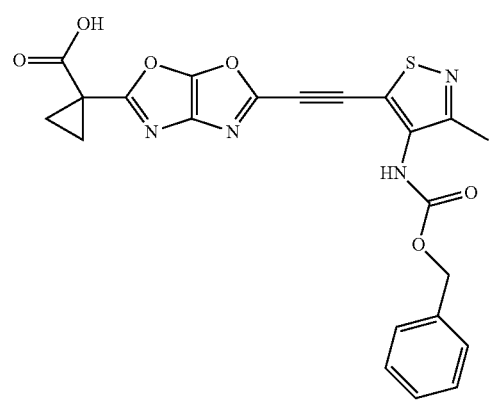
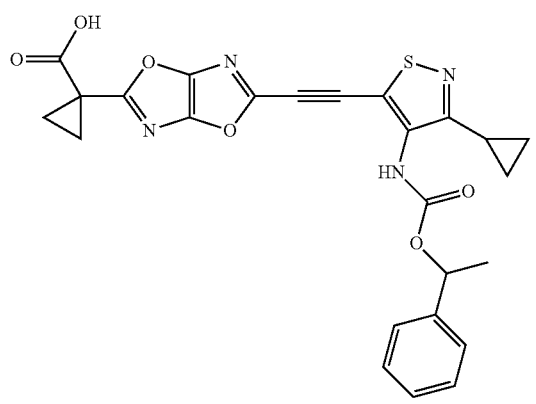
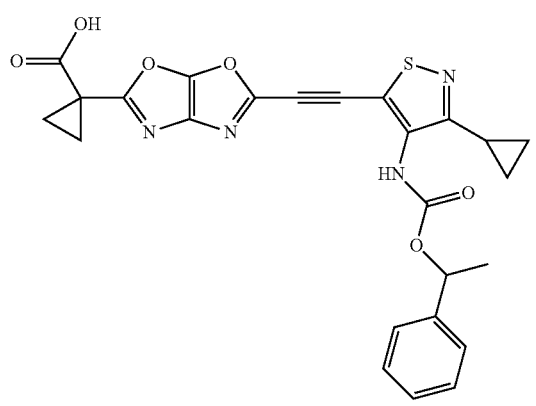
TABLE 18-continued
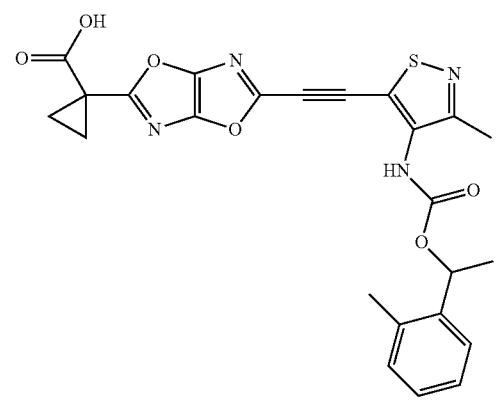
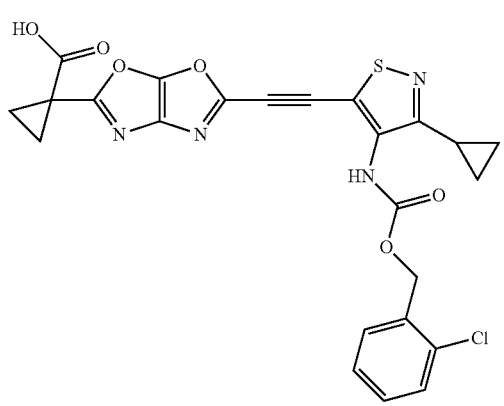 [SMILES: O=C(Nc1c(C2CC2)nsc1C#Cc1nc2nc(C3(C(=O)O)CC3)oc2o1)OCc1ccccc1Cl]
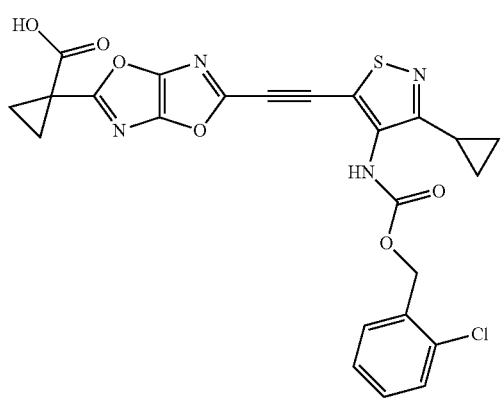 [SMILES: O=C(Nc1c(C2CC2)nsc1C#Cc1nc2oc(C3(C(=O)O)CC3)nc2o1)OCc1ccccc1Cl]
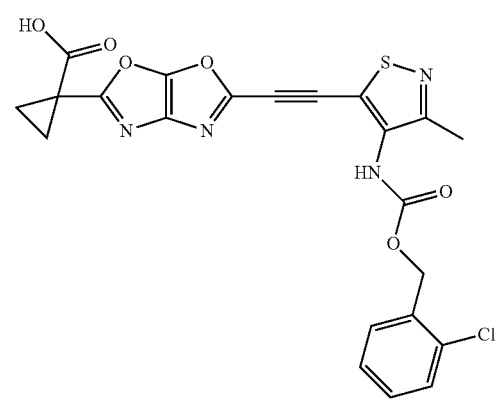 [SMILES: Cc1nsc(C#Cc2nc3nc(C4(C(=O)O)CC4)oc3o2)c1NC(=O)OCc1ccccc1Cl]

TABLE 18-continued
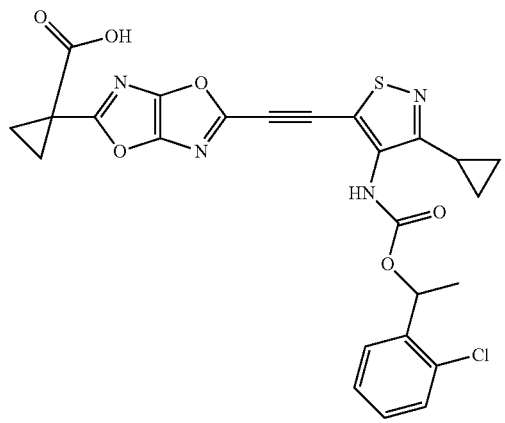 [SMILES: CC(OC(=O)Nc1c(C2CC2)nsc1C#Cc1nc2oc(C3(C(=O)O)CC3)nc2o1)c1ccccc1Cl]
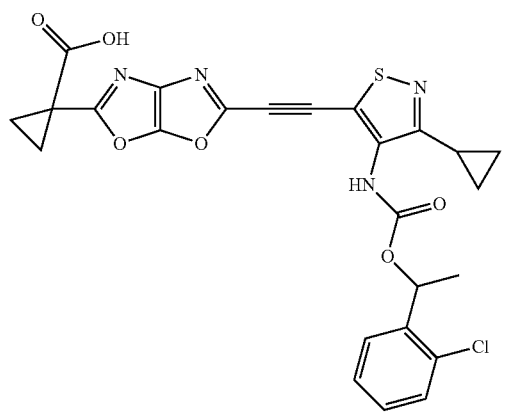 [SMILES: CC(OC(=O)Nc1c(C2CC2)nsc1C#Cc1nc2nc(C3(C(=O)O)CC3)oc2o1)c1ccccc1Cl]
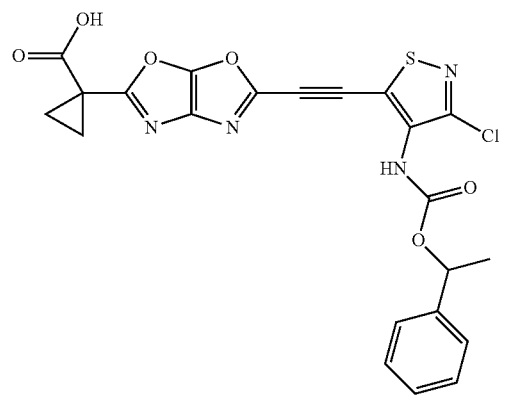
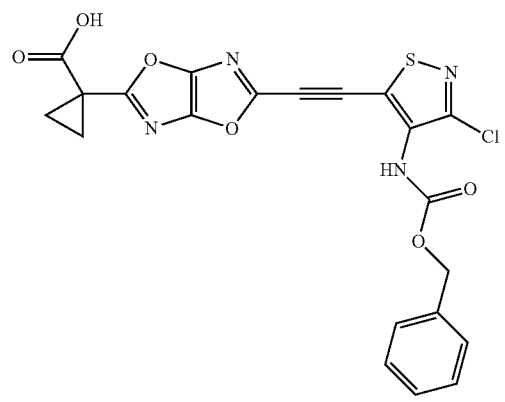 [SMILES: O=C(Nc1c(Cl)nsc1C#Cc1nc2oc(C3(C(=O)O)CC3)nc2o1)OCc1ccccc1]
TABLE 18-continued
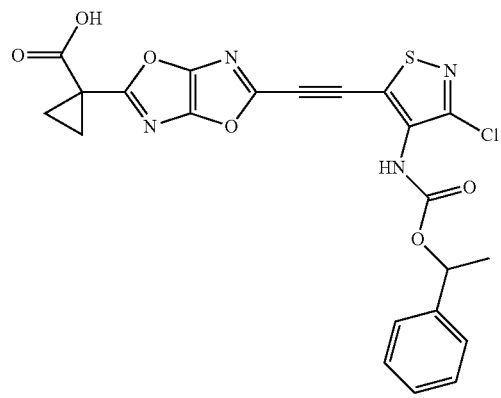
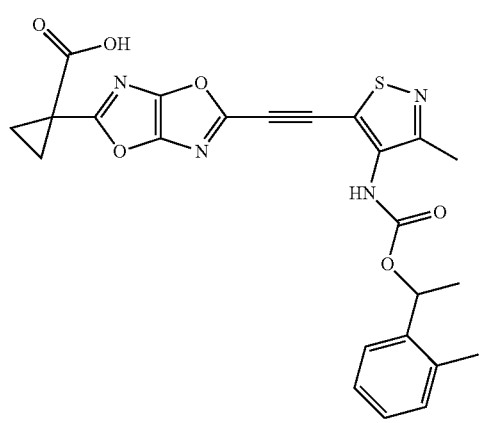 [SMILES: Cc1ccccc1C(C)OC(=O)Nc1c(C)nsc1C#Cc1nc2oc(C3(C(=O)O)CC3)nc2o1]
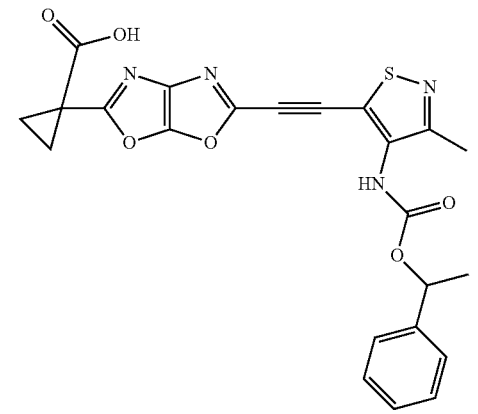 [SMILES: Cc1nsc(C#Cc2nc3nc(C4(C(=O)O)CC4)oc3o2)c1NC(=O)OC(C)c1ccccc1]
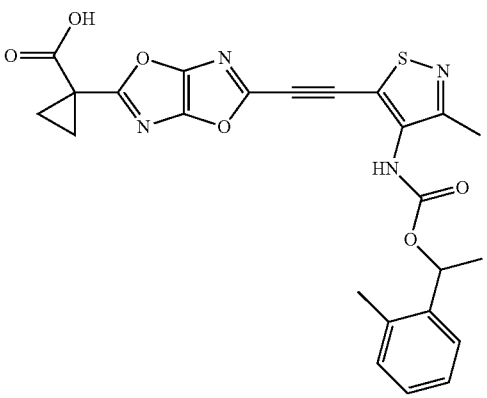

TABLE 18-continued
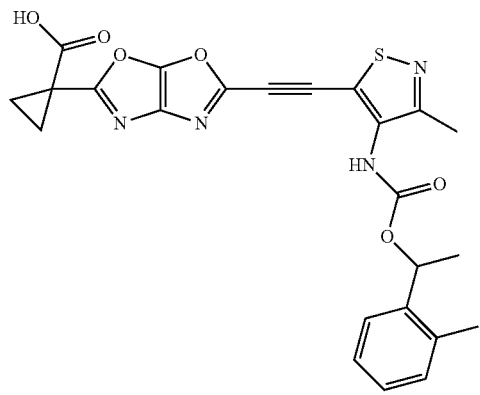 [SMILES: Cc1ccccc1C(C)OC(=O)Nc1c(C)nsc1C#Cc1nc2nc(C3(C(=O)O)CC3)oc2o1]
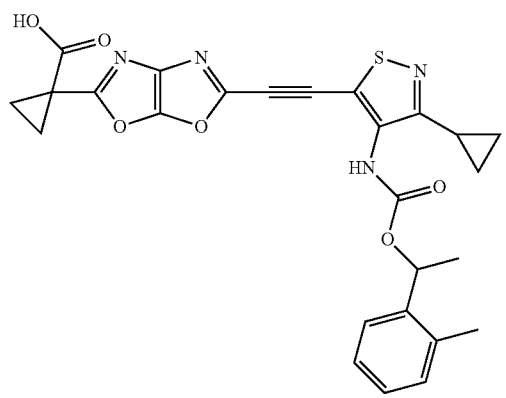 [SMILES: Cc1ccccc1C(C)OC(=O)Nc1c(C2CC2)nsc1C#Cc1nc2nc(C3(C(=O)O)CC3)oc2o1]
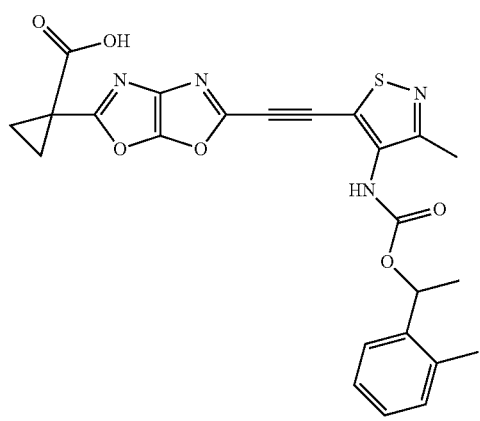 [SMILES: Cc1ccccc1C(C)OC(=O)Nc1c(C)nsc1C#Cc1nc2nc(C3(C(=O)O)CC3)oc2o1]
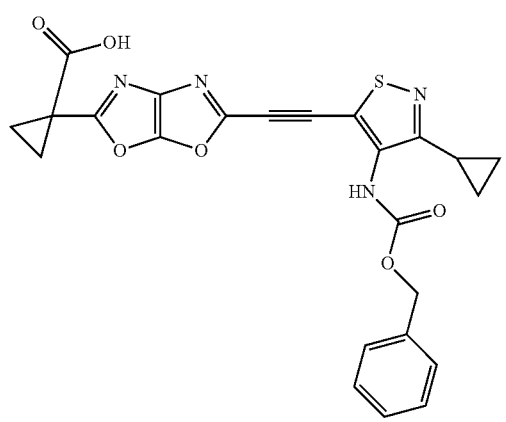 [SMILES: O=C(Nc1c(C2CC2)nsc1C#Cc1nc2nc(C3(C(=O)O)CC3)oc2o1)OCc1ccccc1]
TABLE 18-continued
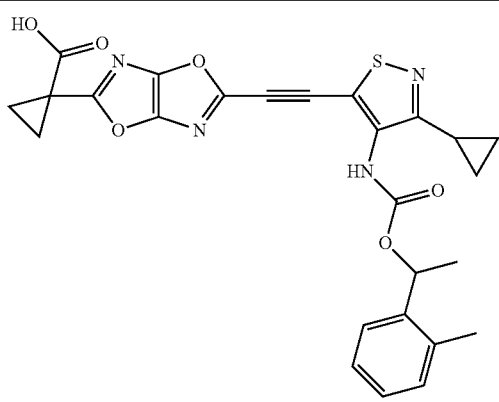
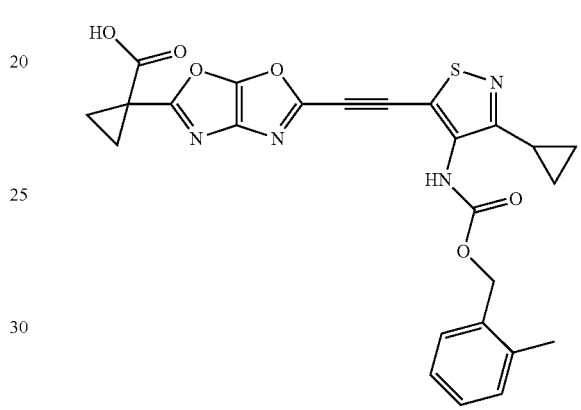
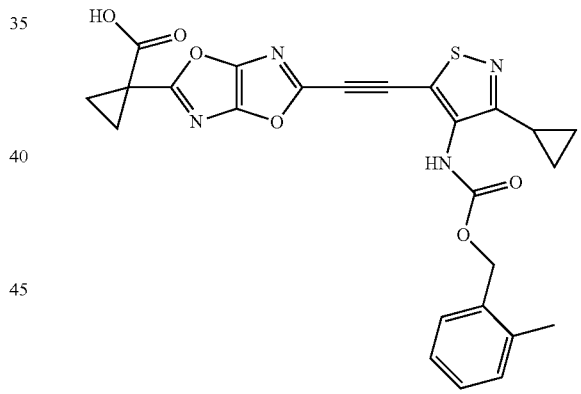
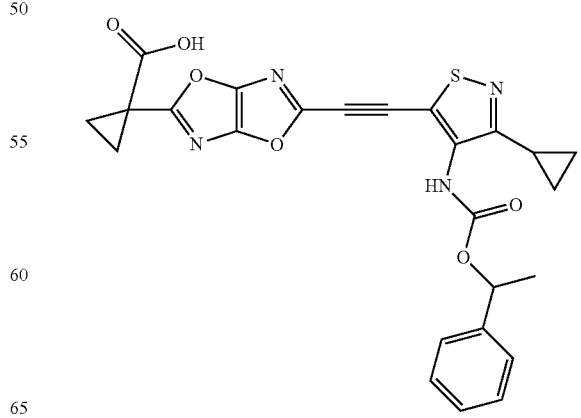

TABLE 18-continued
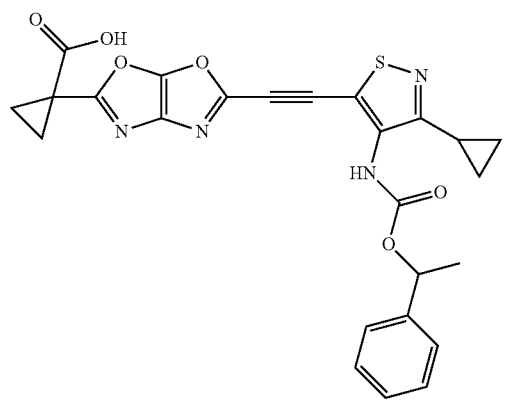 [SMILES: CC(OC(=O)Nc1c(C2CC2)nsc1C#Cc1nc2nc(C3(C(=O)O)CC3)oc2o1)c1ccccc1]
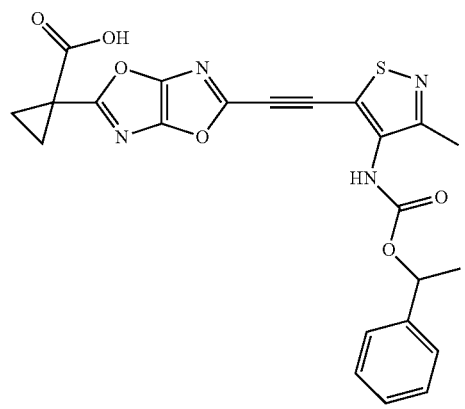 [SMILES: Cc1nsc(C#Cc2nc3oc(C4(C(=O)O)CC4)nc3o2)c1NC(=O)OC(C)c1ccccc1]
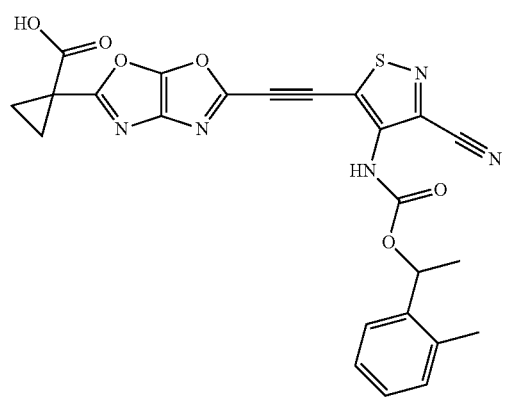 [SMILES: Cc1ccccc1C(C)OC(=O)Nc1c(C#N)nsc1C#Cc1nc2nc(C3(C(=O)O)CC3)oc2o1]
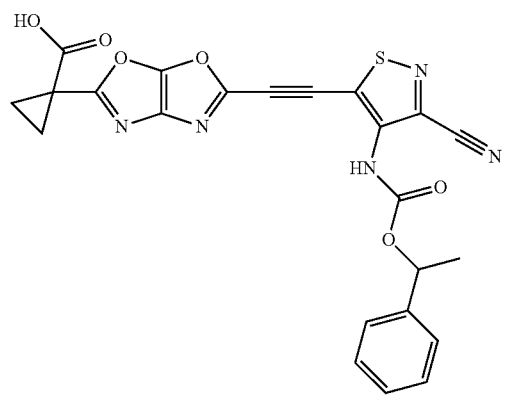 [SMILES: CC(OC(=O)Nc1c(C#N)nsc1C#Cc1nc2nc(C3(C(=O)O)CC3)oc2o1)c1ccccc1]
TABLE 18-continued
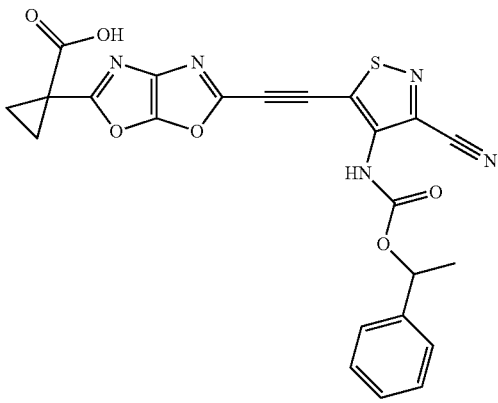 [SMILES: CC(OC(=O)Nc1c(C#N)nsc1C#Cc1nc2nc(C3(C(=O)O)CC3)oc2o1)c1ccccc1]
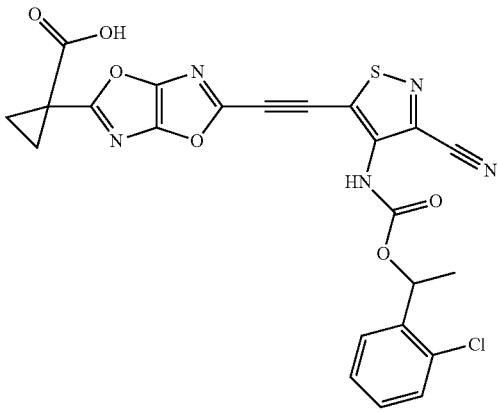 [SMILES: CC(OC(=O)Nc1c(C#N)nsc1C#Cc1nc2oc(C3(C(=O)O)CC3)nc2o1)c1ccccc1Cl]
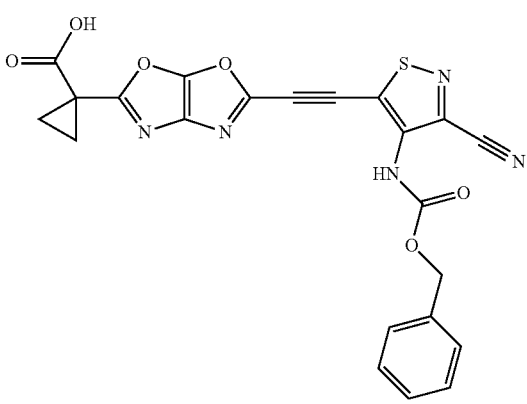 [SMILES: N#Cc1nsc(C#Cc2nc3nc(C4(C(=O)O)CC4)oc3o2)c1NC(=O)OCc1ccccc1]
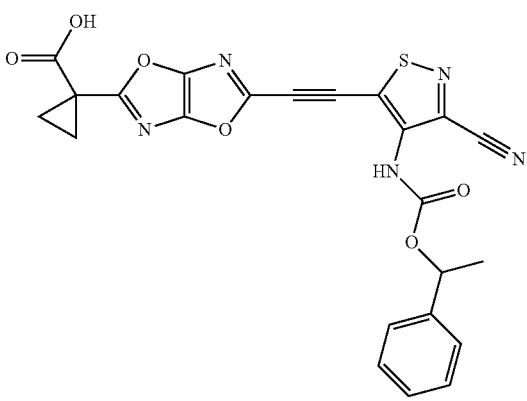 [SMILES: CC(OC(=O)Nc1c(C#N)nsc1C#Cc1nc2oc(C3(C(=O)O)CC3)nc2o1)c1ccccc1]

TABLE 18-continued
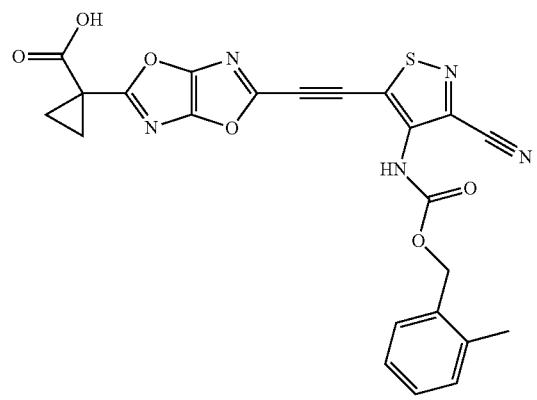 [SMILES: Cc1ccccc1COC(=O)Nc1c(C#N)nsc1C#Cc1nc2oc(C3(C(=O)O)CC3)nc2o1]
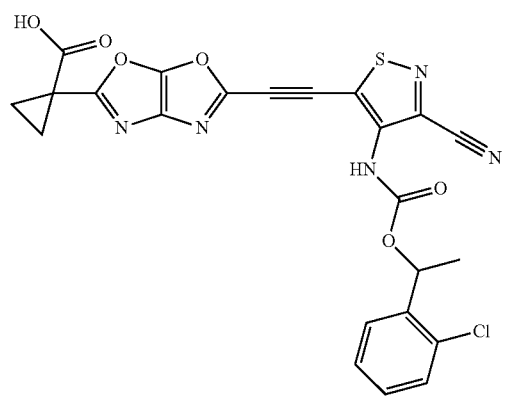 [SMILES: CC(OC(=O)Nc1c(C#N)nsc1C#Cc1nc2nc(C3(C(=O)O)CC3)oc2o1)c1ccccc1Cl]
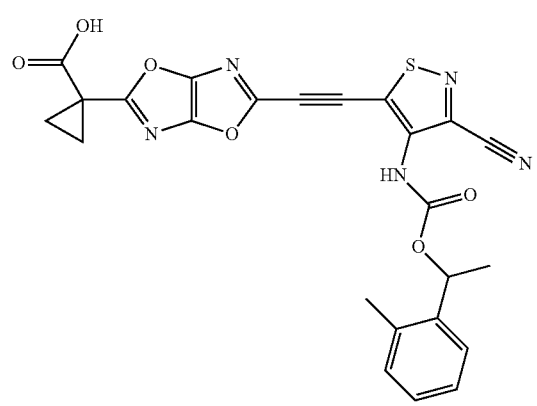 [SMILES: Cc1ccccc1C(C)OC(=O)Nc1c(C#N)nsc1C#Cc1nc2oc(C3(C(=O)O)CC3)nc2o1]
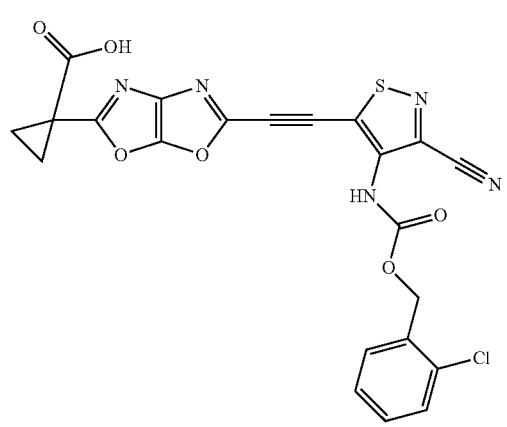 [SMILES: N#Cc1nsc(C#Cc2nc3nc(C4(C(=O)O)CC4)oc3o2)c1NC(=O)OCc1ccccc1Cl]
TABLE 18-continued
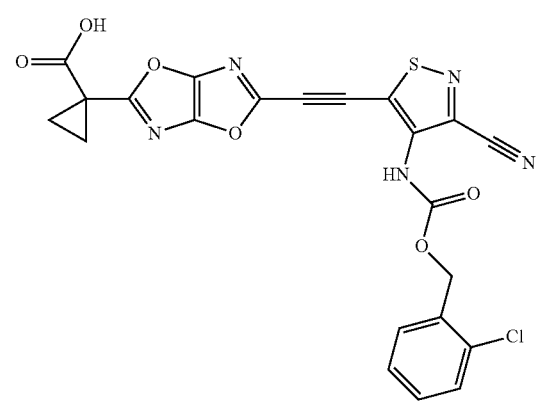 [SMILES: N#Cc1nsc(C#Cc2nc3oc(C4(C(=O)O)CC4)nc3o2)c1NC(=O)OCc1ccccc1Cl]
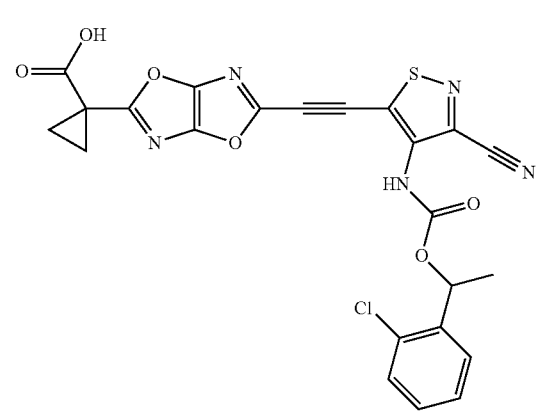 [SMILES: CC(OC(=O)Nc1c(C#N)nsc1C#Cc1nc2oc(C3(C(=O)O)CC3)nc2o1)c1ccccc1Cl]
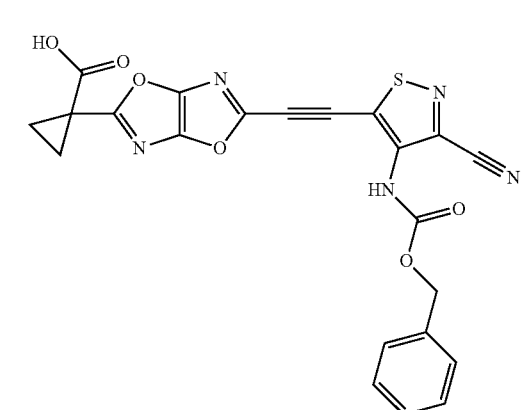
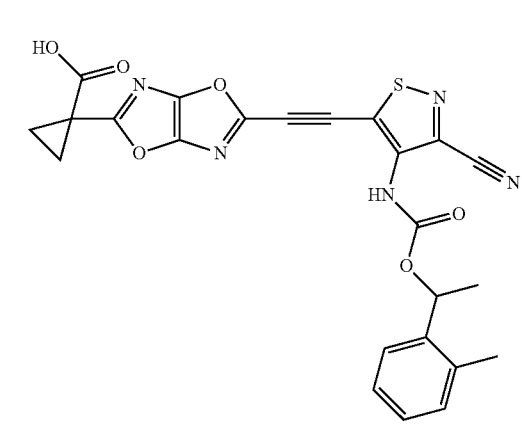 [SMILES: Cc1ccccc1C(C)OC(=O)Nc1c(C#N)nsc1C#Cc1nc2oc(C3(C(=O)O)CC3)nc2o1]

TABLE 18-continued
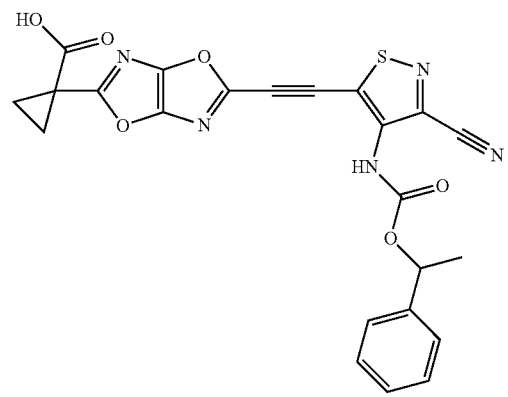 [SMILES: CC(OC(=O)Nc1c(C#N)nsc1C#Cc1nc2oc(C3(C(=O)O)CC3)nc2o1)c1ccccc1]
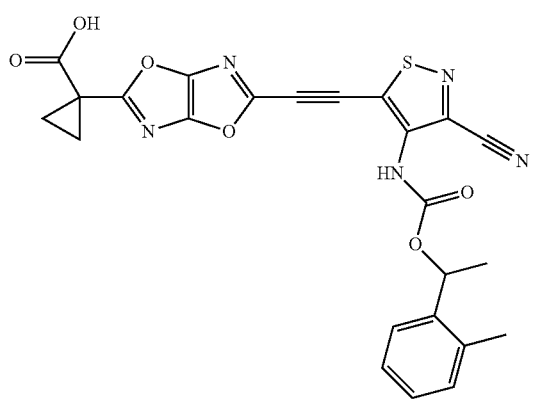 [SMILES: Cc1ccccc1C(C)OC(=O)Nc1c(C#N)nsc1C#Cc1nc2oc(C3(C(=O)O)CC3)nc2o1]
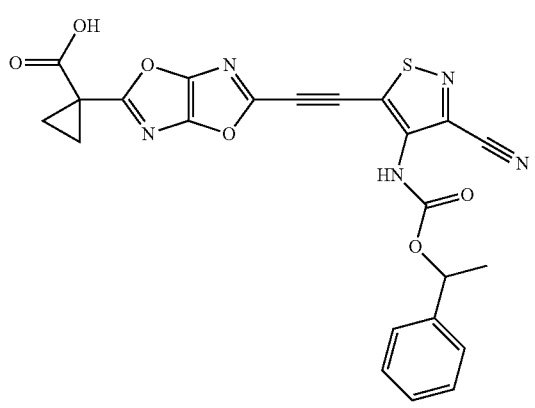 [SMILES: CC(OC(=O)Nc1c(C#N)nsc1C#Cc1nc2oc(C3(C(=O)O)CC3)nc2o1)c1ccccc1]
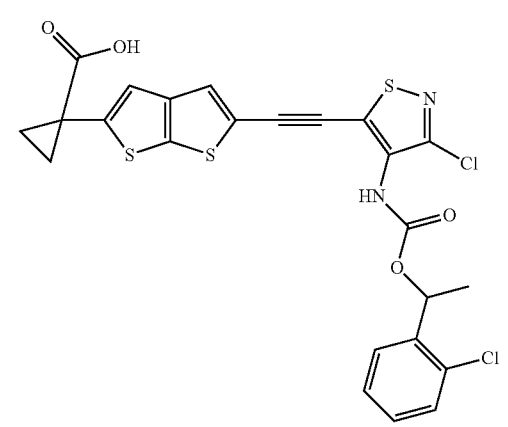 [SMILES: CC(OC(=O)Nc1c(Cl)nsc1C#Cc1cc2cc(C3(C(=O)O)CC3)sc2s1)c1ccccc1Cl]
TABLE 18-continued
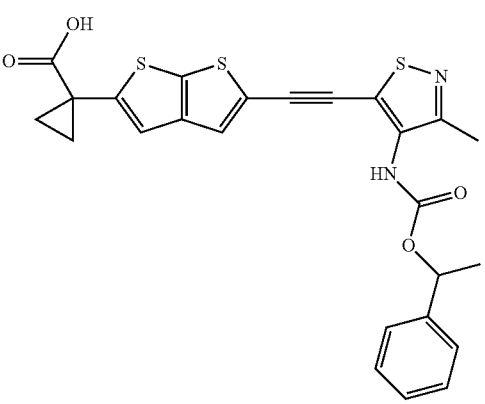
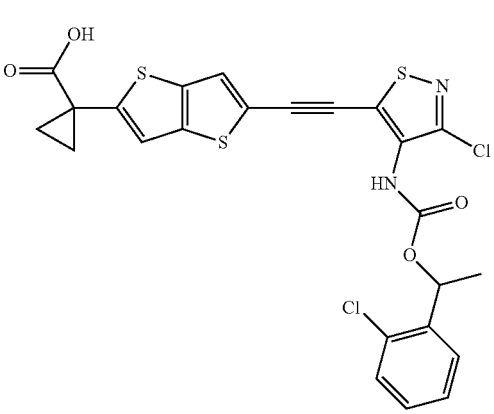 [SMILES: CC(OC(=O)Nc1c(Cl)nsc1C#Cc1cc2sc(C3(C(=O)O)CC3)cc2s1)c1ccccc1Cl]
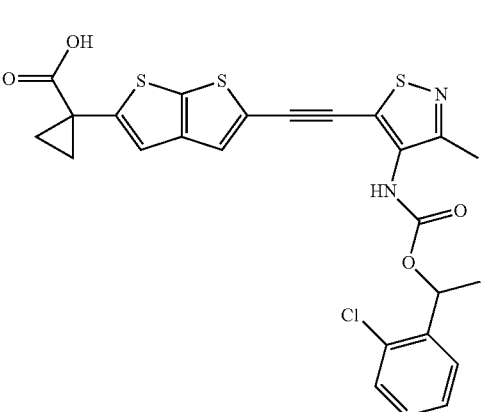
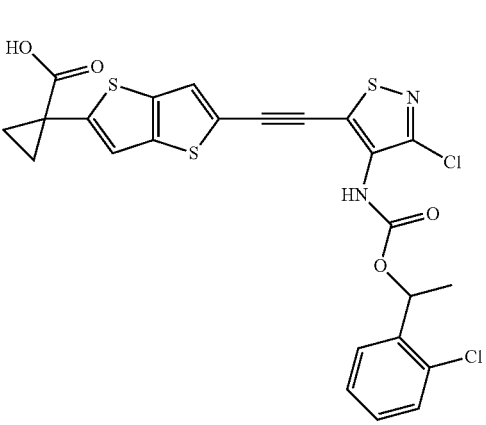 [SMILES: CC(OC(=O)Nc1c(Cl)nsc1C#Cc1cc2sc(C3(C(=O)O)CC3)cc2s1)c1ccccc1Cl]

TABLE 18-continued
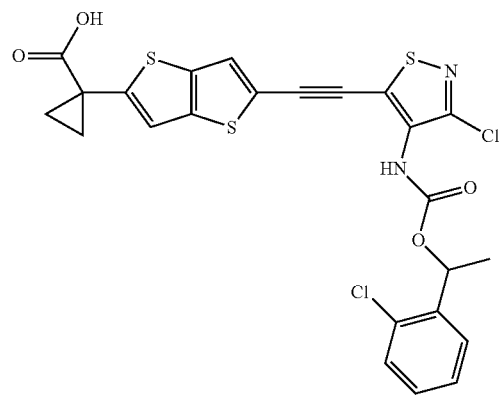 [SMILES: CC(OC(=O)Nc1c(Cl)nsc1C#Cc1cc2sc(C3(C(=O)O)CC3)cc2s1)c1ccccc1Cl]
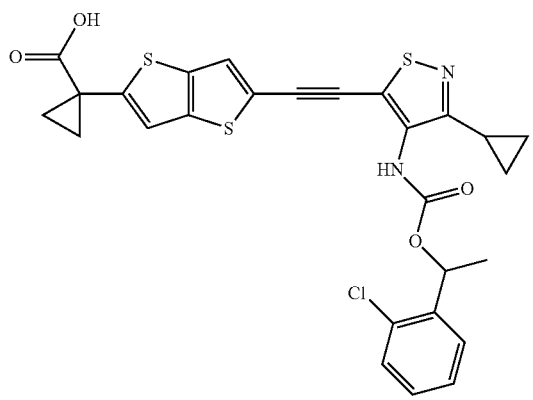 [SMILES: CC(OC(=O)Nc1c(C2CC2)nsc1C#Cc1cc2sc(C3(C(=O)O)CC3)cc2s1)c1ccccc1Cl]
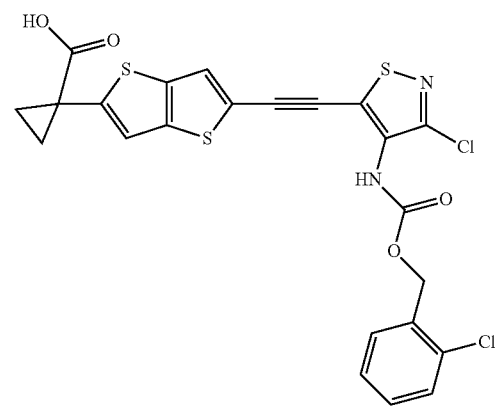 [SMILES: O=C(Nc1c(Cl)nsc1C#Cc1cc2sc(C3(C(=O)O)CC3)cc2s1)OCc1ccccc1Cl]
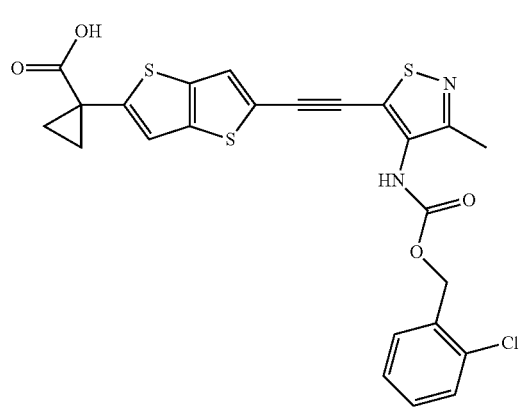 [SMILES: Cc1nsc(C#Cc2cc3sc(C4(C(=O)O)CC4)cc3s2)c1NC(=O)OCc1ccccc1Cl]
TABLE 18-continued
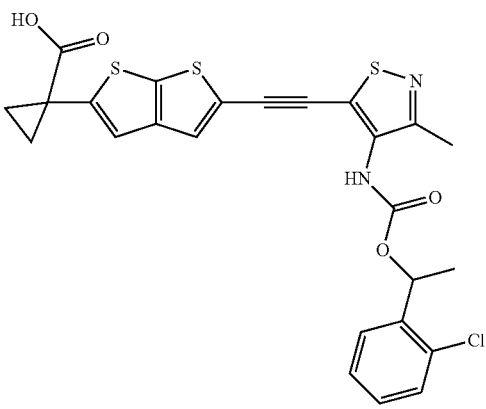 [SMILES: Cc1nsc(C#Cc2cc3cc(C4(C(=O)O)CC4)sc3s2)c1NC(=O)OC(C)c1ccccc1Cl]
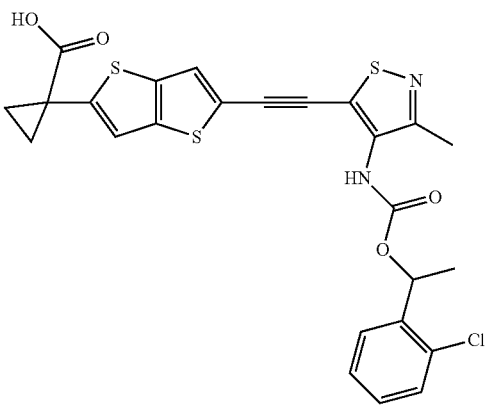 [SMILES: Cc1nsc(C#Cc2cc3sc(C4(C(=O)O)CC4)cc3s2)c1NC(=O)OC(C)c1ccccc1Cl]
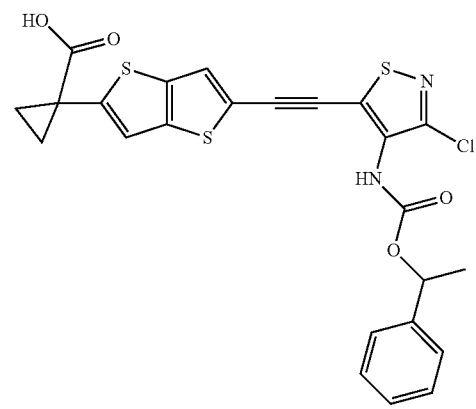 [SMILES: CC(OC(=O)Nc1c(Cl)nsc1C#Cc1cc2sc(C3(C(=O)O)CC3)cc2s1)c1ccccc1]
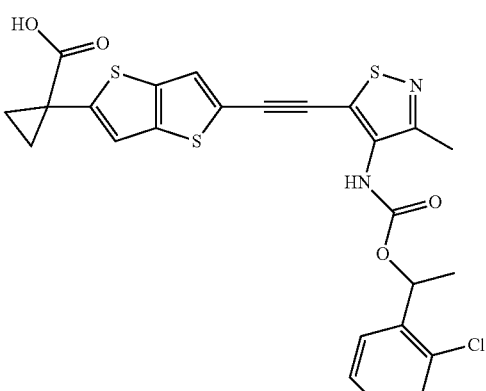

TABLE 18-continued
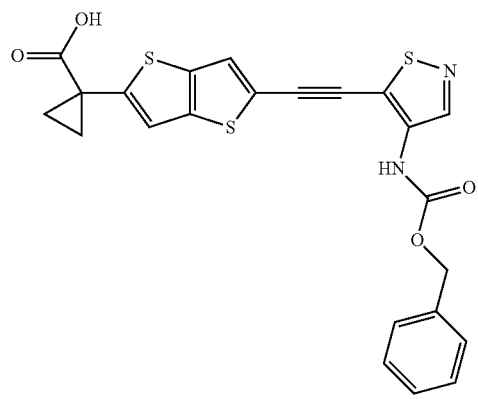 [SMILES: O=C(Nc1cnsc1C#Cc1cc2sc(C3(C(=O)O)CC3)cc2s1)OCc1ccccc1]
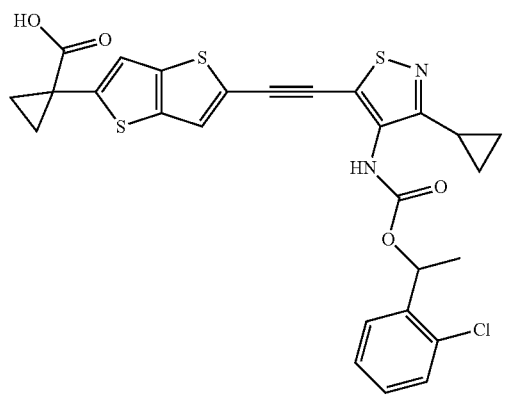
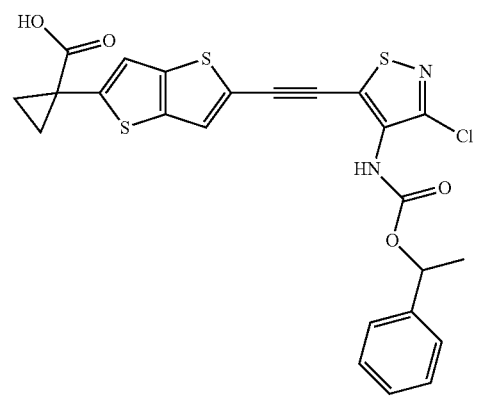 [SMILES: CC(OC(=O)Nc1c(Cl)nsc1C#Cc1cc2sc(C3(C(=O)O)CC3)cc2s1)c1ccccc1]
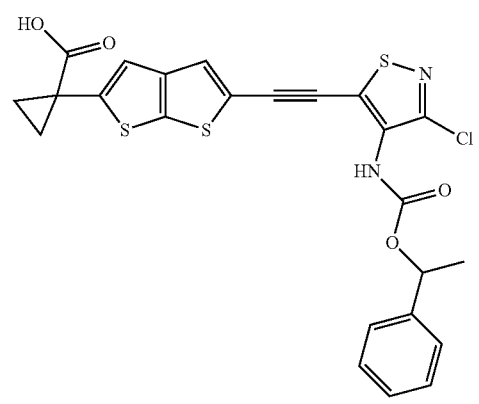 [SMILES: CC(OC(=O)Nc1c(Cl)nsc1C#Cc1cc2cc(C3(C(=O)O)CC3)sc2s1)c1ccccc1]
TABLE 18-continued
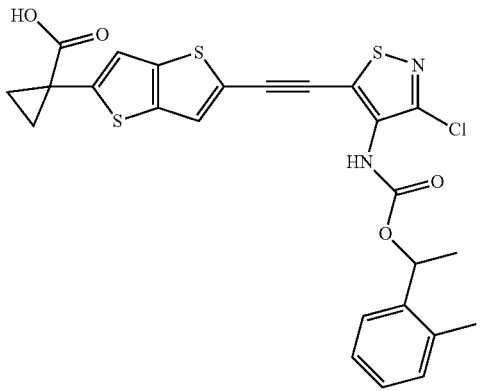 [SMILES: Cc1ccccc1C(C)OC(=O)Nc1c(Cl)nsc1C#Cc1cc2sc(C3(C(=O)O)CC3)cc2s1]
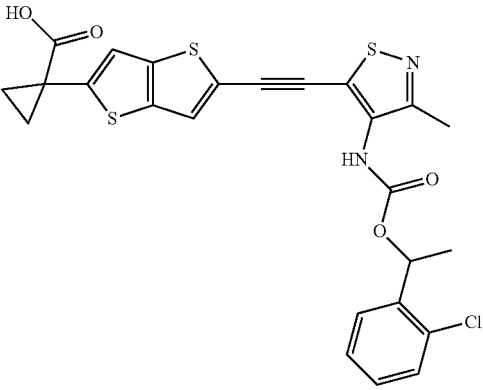
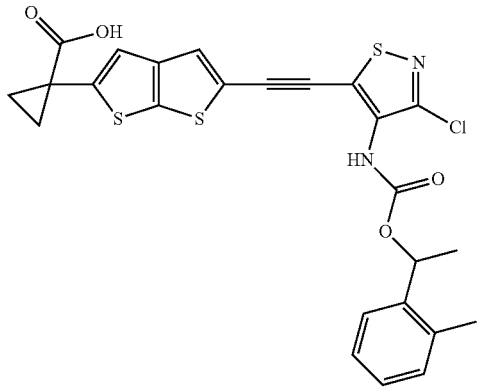 [SMILES: Cc1ccccc1C(C)OC(=O)Nc1c(Cl)nsc1C#Cc1cc2cc(C3(C(=O)O)CC3)sc2s1]
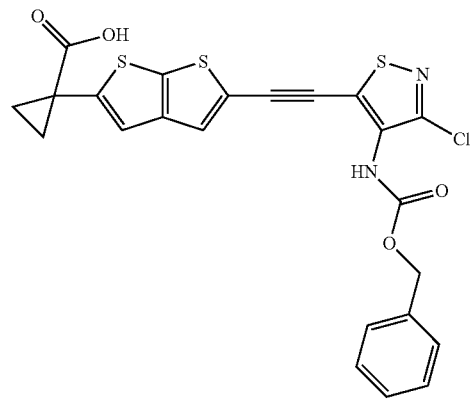 [SMILES: O=C(Nc1c(Cl)nsc1C#Cc1cc2cc(C3(C(=O)O)CC3)sc2s1)OCc1ccccc1]

TABLE 18-continued
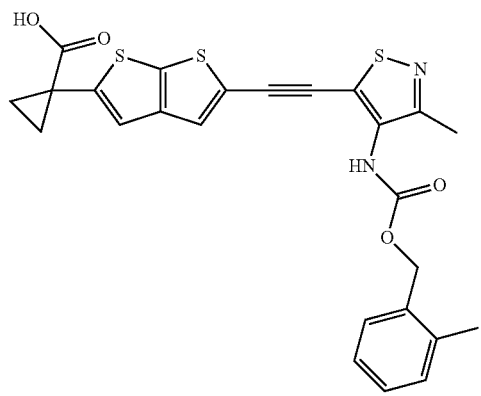 [SMILES: Cc1ccccc1COC(=O)Nc1c(C)nsc1C#Cc1cc2cc(C3(C(=O)O)CC3)sc2s1]
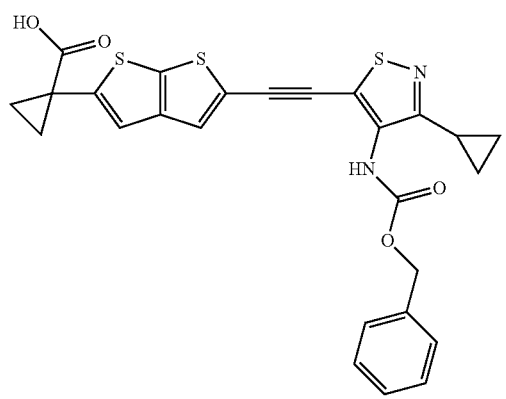 [SMILES: O=C(Nc1c(C2CC2)nsc1C#Cc1cc2cc(C3(C(=O)O)CC3)sc2s1)OCc1ccccc1]
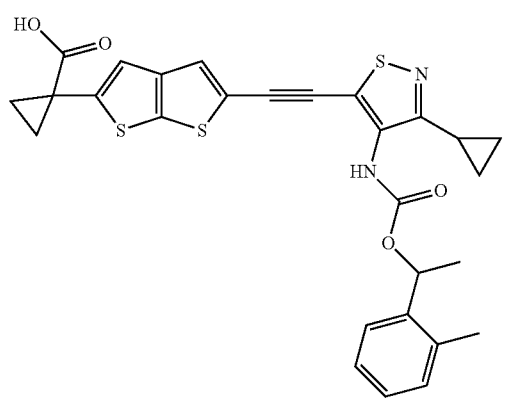 [SMILES: Cc1ccccc1C(C)OC(=O)Nc1c(C2CC2)nsc1C#Cc1cc2cc(C3(C(=O)O)CC3)sc2s1]
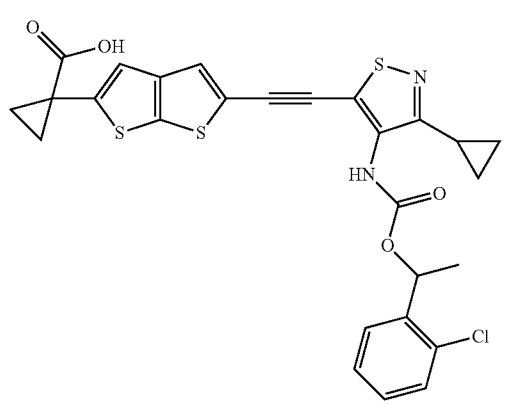 [SMILES: CC(OC(=O)Nc1c(C2CC2)nsc1C#Cc1cc2cc(C3(C(=O)O)CC3)sc2s1)c1ccccc1Cl]
TABLE 18-continued
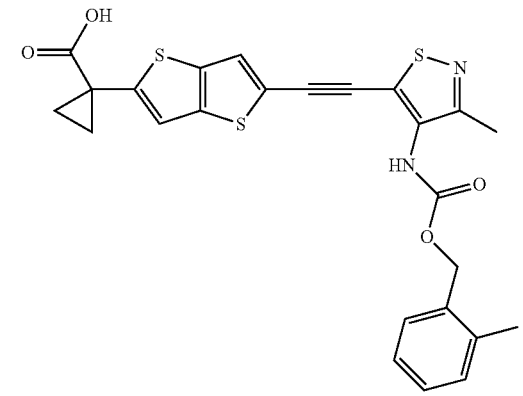 [SMILES: Cc1ccccc1COC(=O)Nc1c(C)nsc1C#Cc1cc2sc(C3(C(=O)O)CC3)cc2s1]
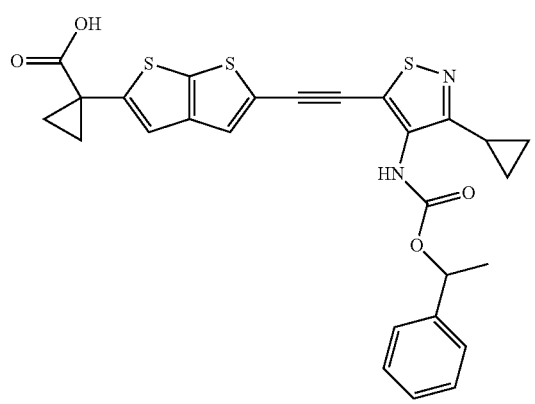 [SMILES: CC(OC(=O)Nc1c(C2CC2)nsc1C#Cc1cc2cc(C3(C(=O)O)CC3)sc2s1)c1ccccc1]
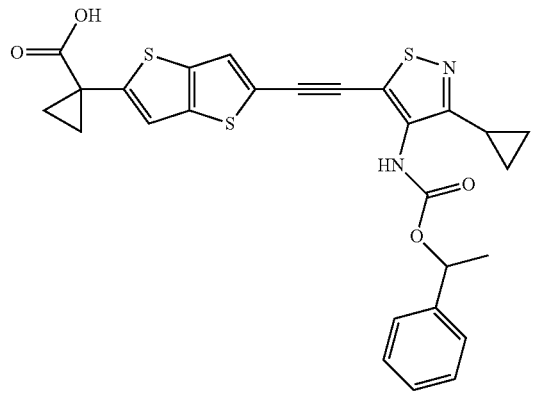 [SMILES: CC(OC(=O)Nc1c(C2CC2)nsc1C#Cc1cc2sc(C3(C(=O)O)CC3)cc2s1)c1ccccc1]
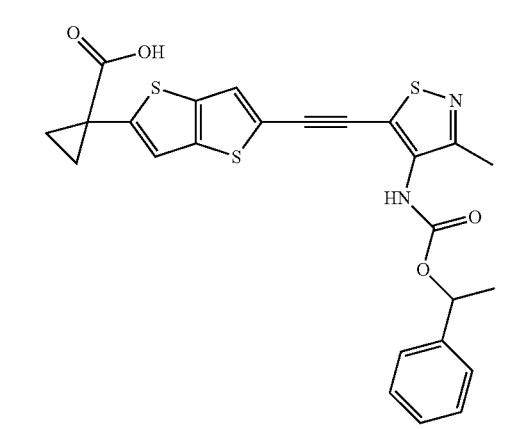 [SMILES: Cc1nsc(C#Cc2cc3sc(C4(C(=O)O)CC4)cc3s2)c1NC(=O)OC(C)c1ccccc1]

TABLE 18-continued
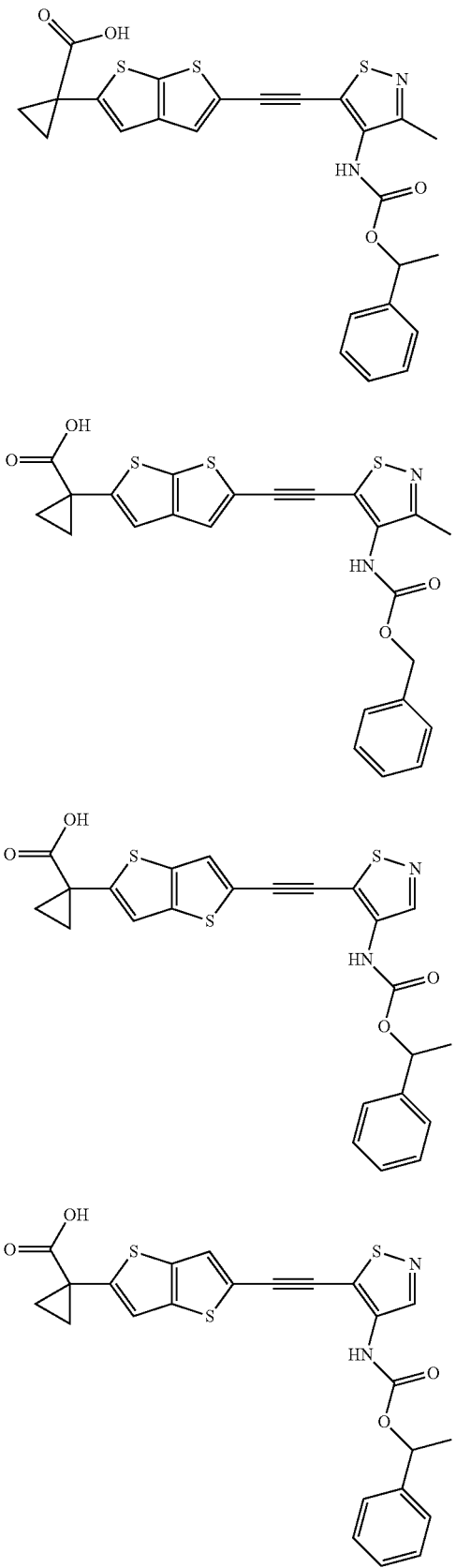
TABLE 18-continued
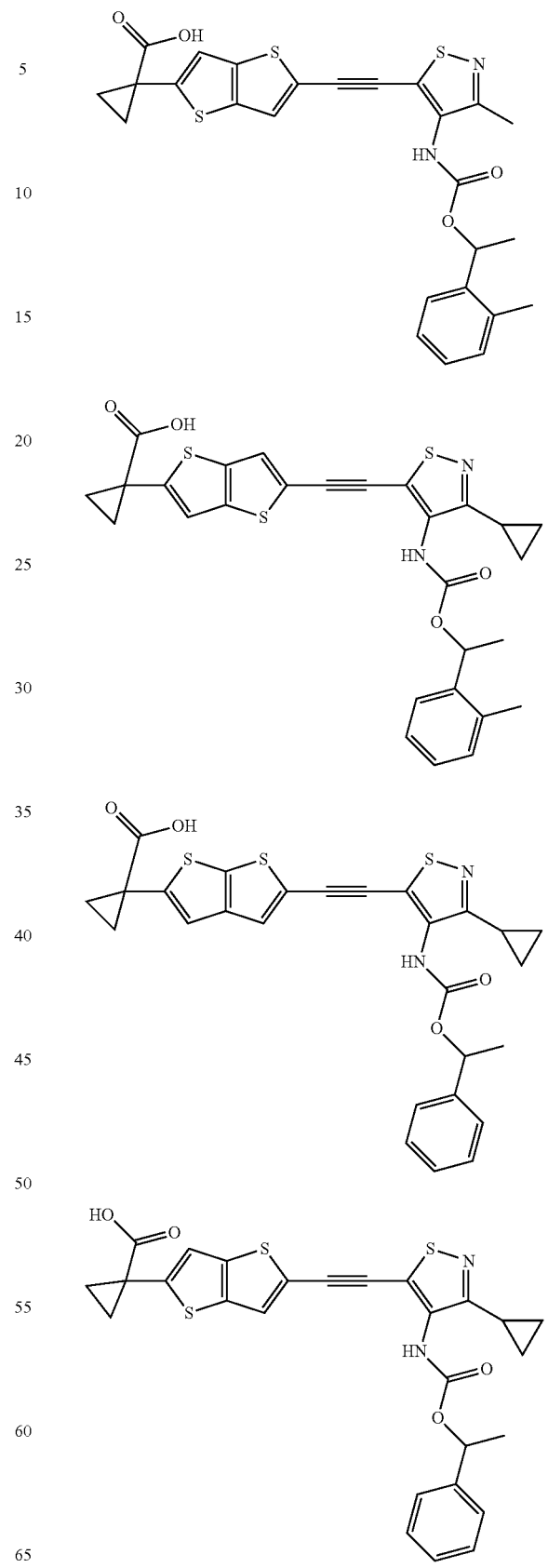

TABLE 18-continued
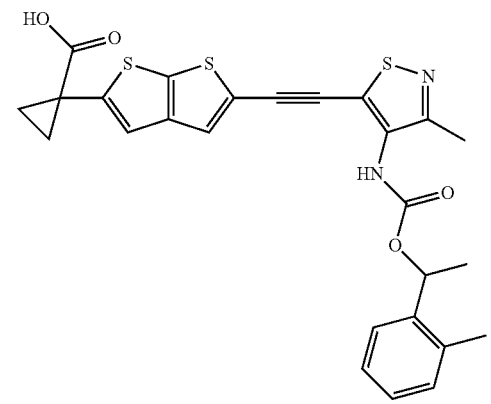 [SMILES: Cc1ccccc1C(C)OC(=O)Nc1c(C)nsc1C#Cc1cc2cc(C3(C(=O)O)CC3)sc2s1]
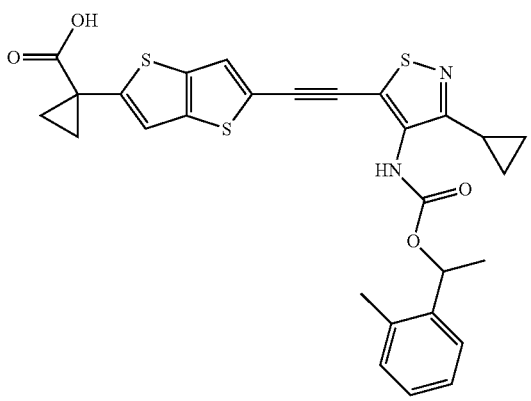 [SMILES: Cc1ccccc1C(C)OC(=O)Nc1c(C2CC2)nsc1C#Cc1cc2sc(C3(C(=O)O)CC3)cc2s1]
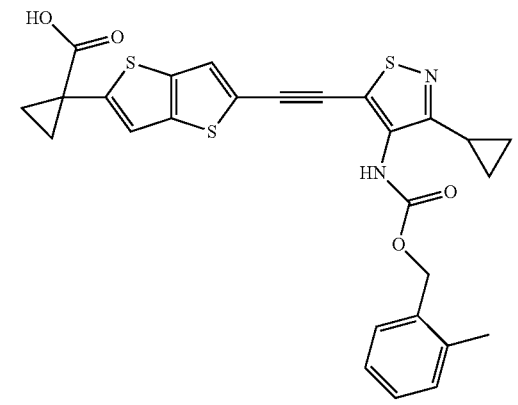 [SMILES: Cc1ccccc1COC(=O)Nc1c(C2CC2)nsc1C#Cc1cc2sc(C3(C(=O)O)CC3)cc2s1]
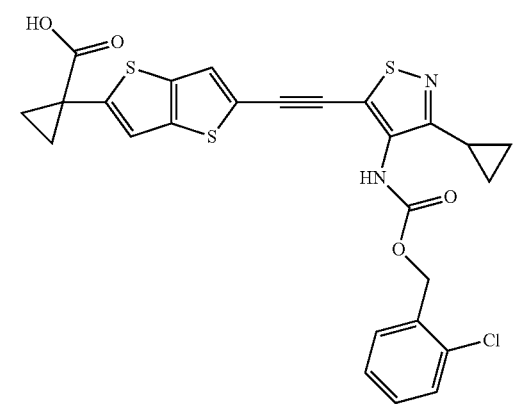
TABLE 18-continued
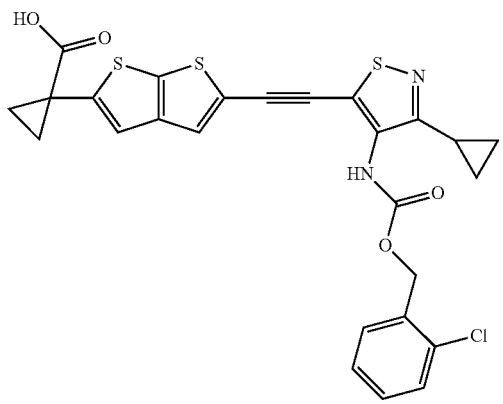 [SMILES: O=C(Nc1c(C2CC2)nsc1C#Cc1cc2cc(C3(C(=O)O)CC3)sc2s1)OCc1ccccc1Cl]
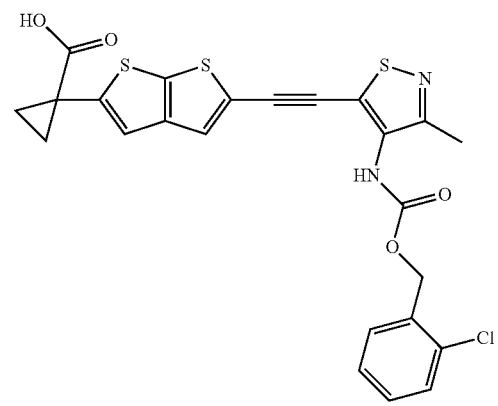 [SMILES: Cc1nsc(C#Cc2cc3cc(C4(C(=O)O)CC4)sc3s2)c1NC(=O)OCc1ccccc1Cl]
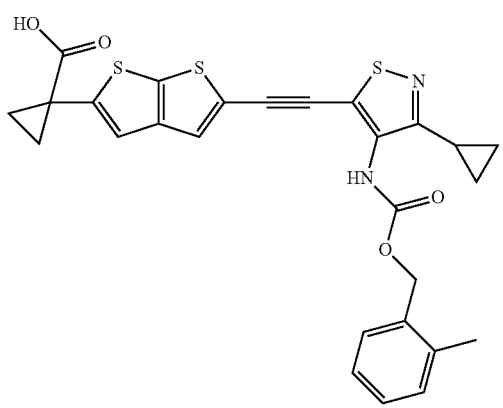 [SMILES: Cc1ccccc1COC(=O)Nc1c(C2CC2)nsc1C#Cc1cc2cc(C3(C(=O)O)CC3)sc2s1]
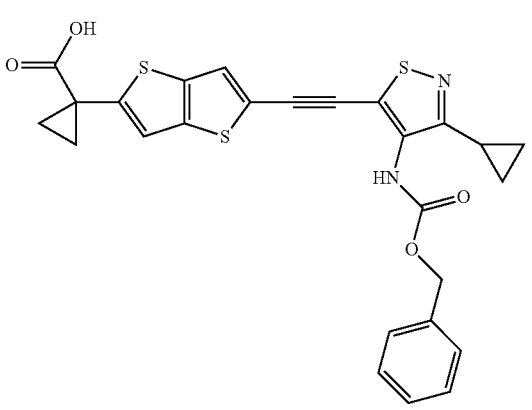 [SMILES: O=C(Nc1c(C2CC2)nsc1C#Cc1cc2sc(C3(C(=O)O)CC3)cc2s1)OCc1ccccc1]

655
TABLE 18-continued
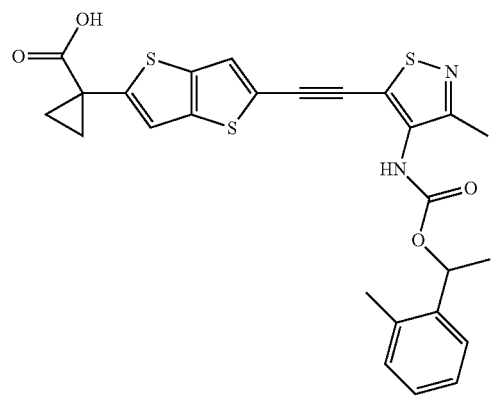 [SMILES: Cc1ccccc1C(C)OC(=O)Nc1c(C)nsc1C#Cc1cc2sc(C3(C(=O)O)CC3)cc2s1]
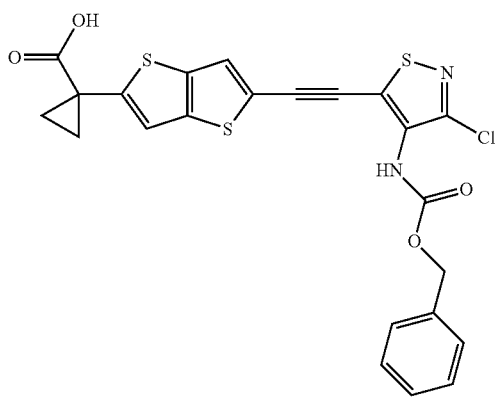 [SMILES: O=C(Nc1c(Cl)nsc1C#Cc1cc2sc(C3(C(=O)O)CC3)cc2s1)OCc1ccccc1]
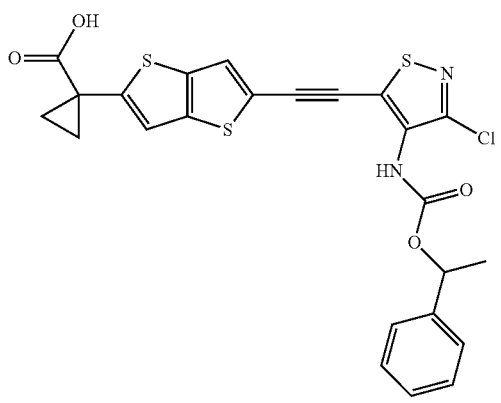 [SMILES: CC(OC(=O)Nc1c(Cl)nsc1C#Cc1cc2sc(C3(C(=O)O)CC3)cc2s1)c1ccccc1]
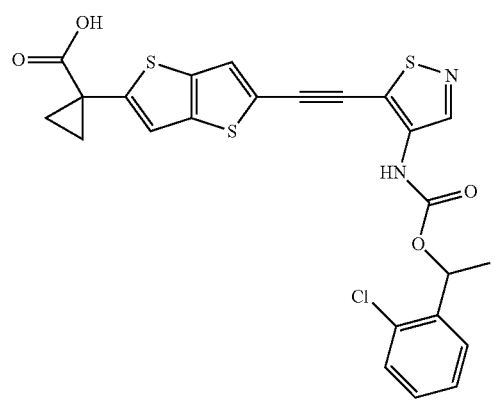 [SMILES: CC(OC(=O)Nc1cnsc1C#Cc1cc2sc(C3(C(=O)O)CC3)cc2s1)c1ccccc1Cl]
656
TABLE 18-continued
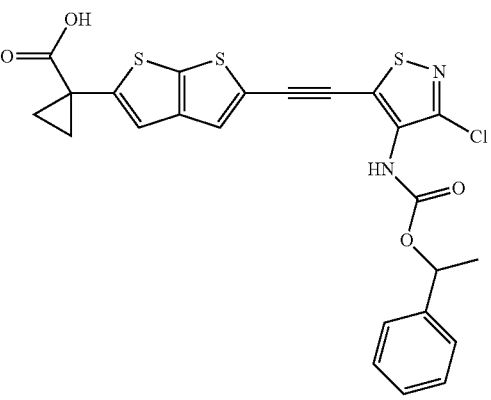 [SMILES: CC(OC(=O)Nc1c(Cl)nsc1C#Cc1cc2cc(C3(C(=O)O)CC3)sc2s1)c1ccccc1]

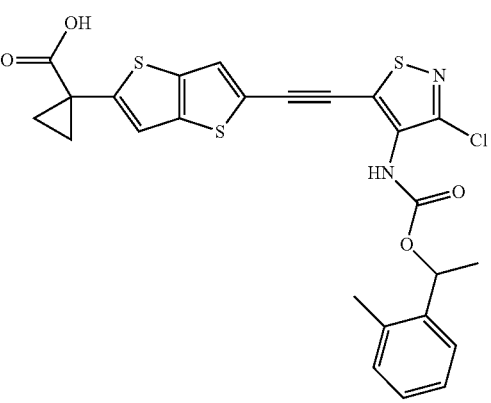 [SMILES: Cc1ccccc1C(C)OC(=O)Nc1c(Cl)nsc1C#Cc1cc2sc(C3(C(=O)O)CC3)cc2s1]
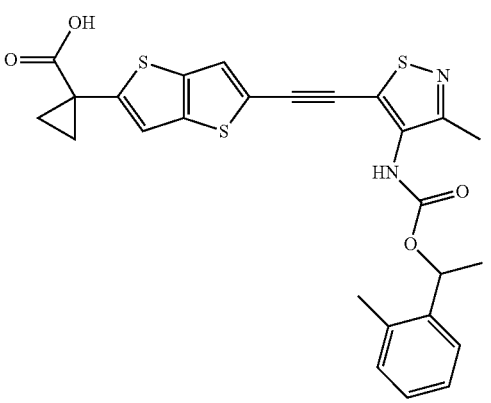 [SMILES: Cc1ccccc1C(C)OC(=O)Nc1c(C)nsc1C#Cc1cc2sc(C3(C(=O)O)CC3)cc2s1]

TABLE 18-continued
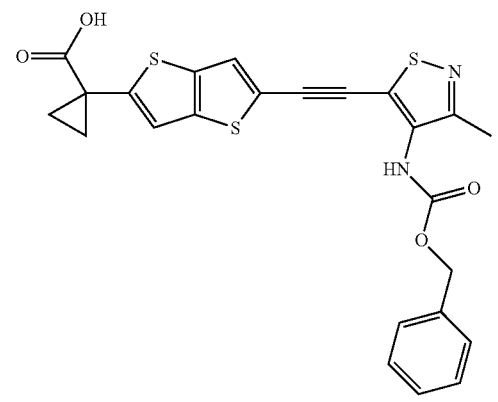 [SMILES: Cc1nsc(C#Cc2cc3sc(C4(C(=O)O)CC4)cc3s2)c1NC(=O)OCc1ccccc1]
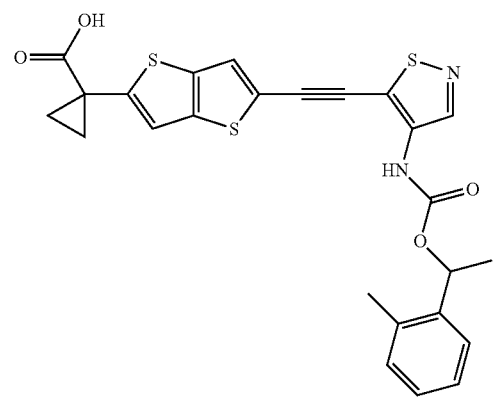 [SMILES: Cc1ccccc1C(C)OC(=O)Nc1cnsc1C#Cc1cc2sc(C3(C(=O)O)CC3)cc2s1]
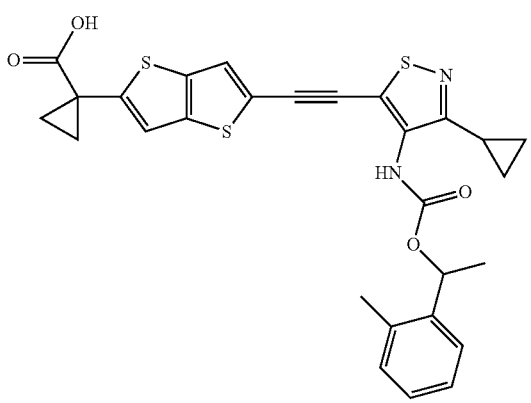 [SMILES: Cc1ccccc1C(C)OC(=O)Nc1c(C2CC2)nsc1C#Cc1cc2sc(C3(C(=O)O)CC3)cc2s1]
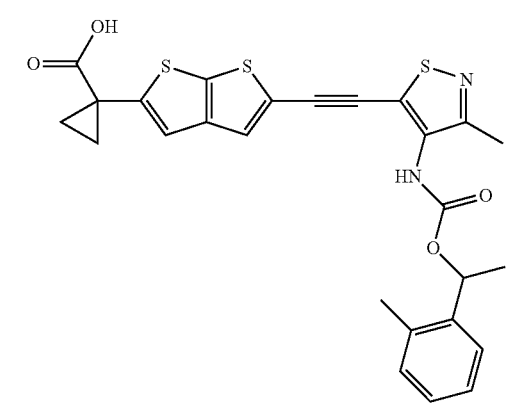 [SMILES: Cc1ccccc1C(C)OC(=O)Nc1c(C)nsc1C#Cc1cc2cc(C3(C(=O)O)CC3)sc2s1]
TABLE 18-continued
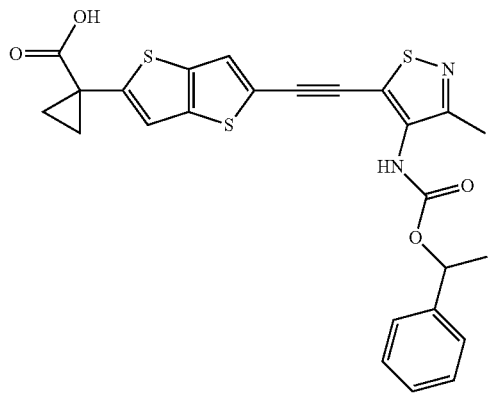 [SMILES: Cc1nsc(C#Cc2cc3sc(C4(C(=O)O)CC4)cc3s2)c1NC(=O)OC(C)c1ccccc1]
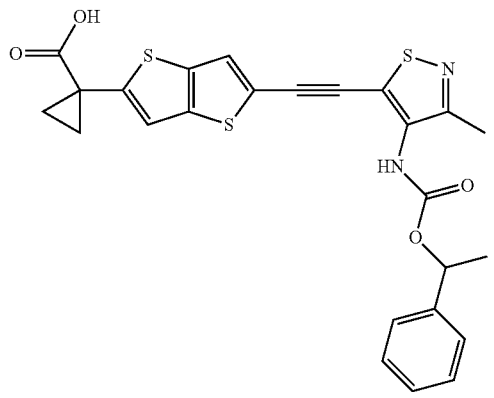 [SMILES: Cc1nsc(C#Cc2cc3sc(C4(C(=O)O)CC4)cc3s2)c1NC(=O)OC(C)c1ccccc1]
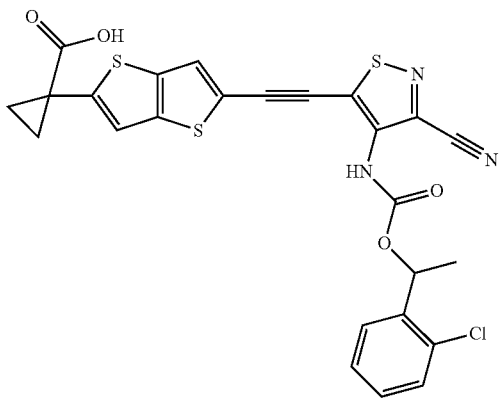 [SMILES: CC(OC(=O)Nc1c(C#N)nsc1C#Cc1cc2sc(C3(C(=O)O)CC3)cc2s1)c1ccccc1Cl]
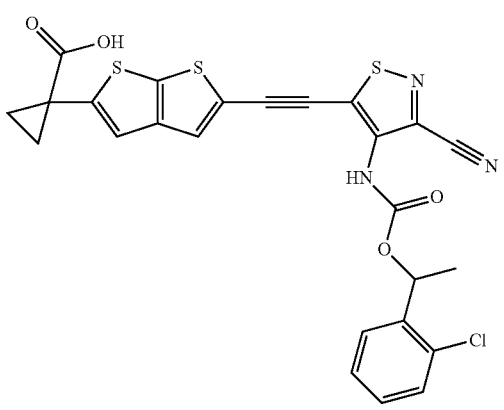 [SMILES: CC(OC(=O)Nc1c(C#N)nsc1C#Cc1cc2cc(C3(C(=O)O)CC3)sc2s1)c1ccccc1Cl]

TABLE 18-continued
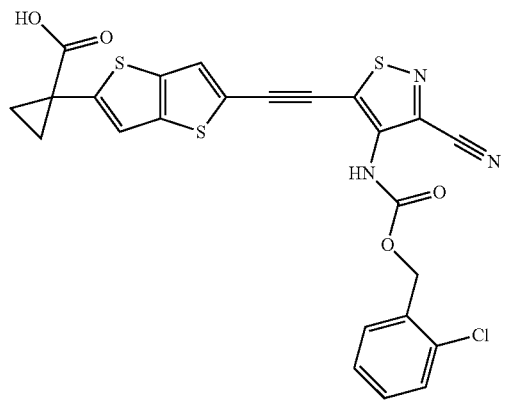 [SMILES: N#Cc1nsc(C#Cc2cc3sc(C4(C(=O)O)CC4)cc3s2)c1NC(=O)OCc1ccccc1Cl]
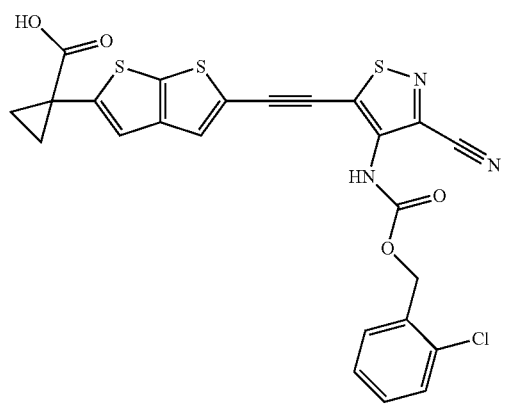 [SMILES: N#Cc1nsc(C#Cc2cc3cc(C4(C(=O)O)CC4)sc3s2)c1NC(=O)OCc1ccccc1Cl]
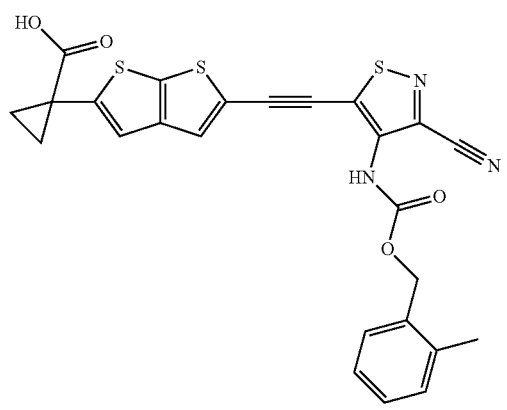 [SMILES: Cc1ccccc1COC(=O)Nc1c(C#N)nsc1C#Cc1cc2cc(C3(C(=O)O)CC3)sc2s1]
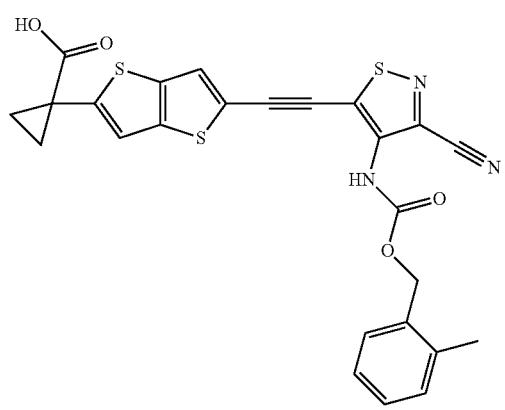 [SMILES: Cc1ccccc1COC(=O)Nc1c(C#N)nsc1C#Cc1cc2sc(C3(C(=O)O)CC3)cc2s1]
TABLE 18-continued
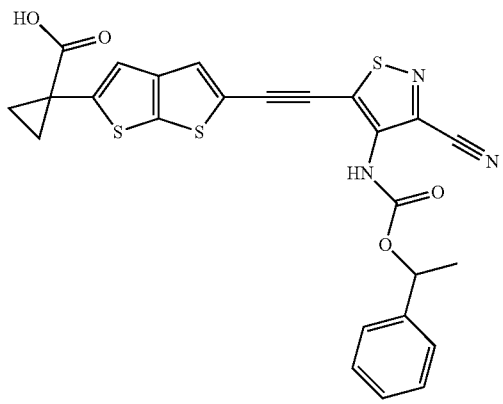 [SMILES: CC(OC(=O)Nc1c(C#N)nsc1C#Cc1cc2cc(C3(C(=O)O)CC3)sc2s1)c1ccccc1]
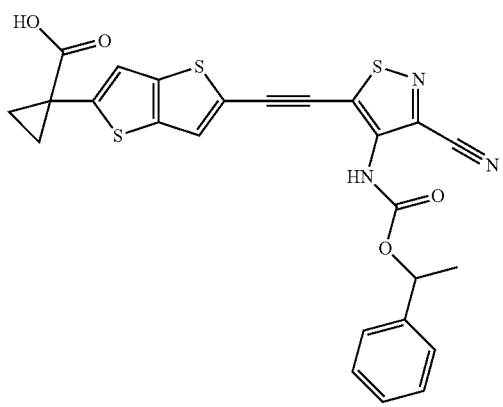 [SMILES: CC(OC(=O)Nc1c(C#N)nsc1C#Cc1cc2sc(C3(C(=O)O)CC3)cc2s1)c1ccccc1]
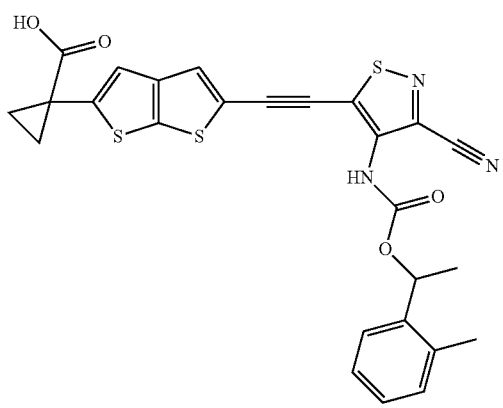 [SMILES: Cc1ccccc1C(C)OC(=O)Nc1c(C#N)nsc1C#Cc1cc2cc(C3(C(=O)O)CC3)sc2s1]
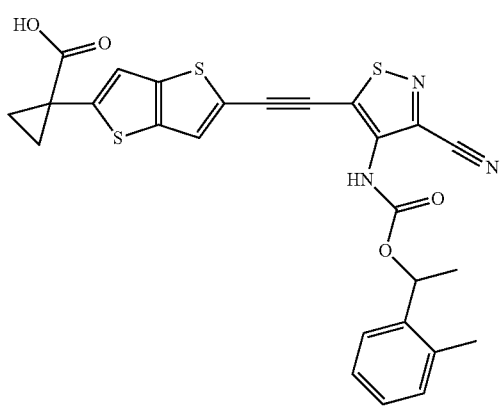 [SMILES: Cc1ccccc1C(C)OC(=O)Nc1c(C#N)nsc1C#Cc1cc2sc(C3(C(=O)O)CC3)cc2s1]

TABLE 18-continued
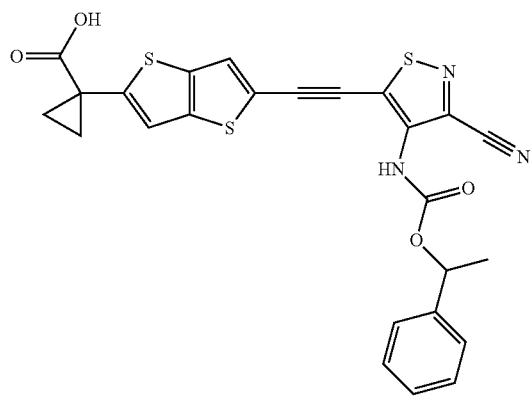 [SMILES: CC(OC(=O)Nc1c(C#N)nsc1C#Cc1cc2sc(C3(C(=O)O)CC3)cc2s1)c1ccccc1]
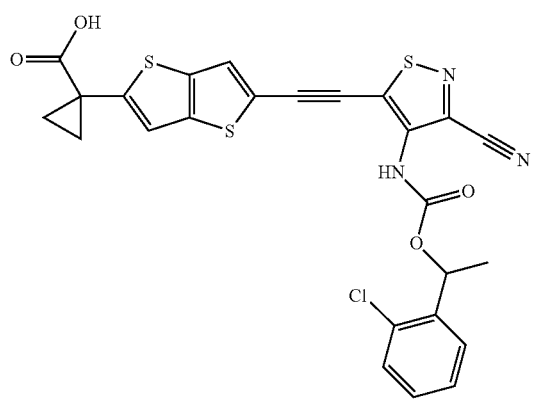 [SMILES: CC(OC(=O)Nc1c(C#N)nsc1C#Cc1cc2sc(C3(C(=O)O)CC3)cc2s1)c1ccccc1Cl]
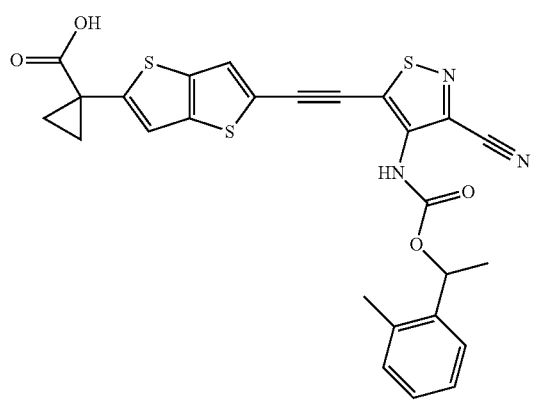
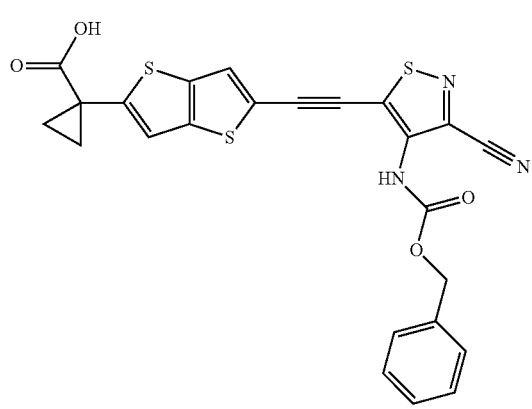 [SMILES: N#Cc1nsc(C#Cc2cc3sc(C4(C(=O)O)CC4)cc3s2)c1NC(=O)OCc1ccccc1]
TABLE 18-continued
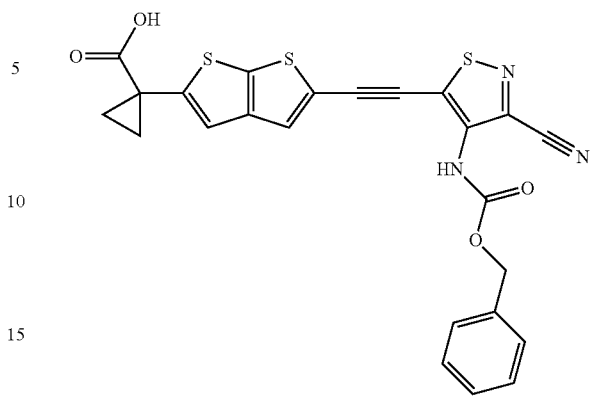
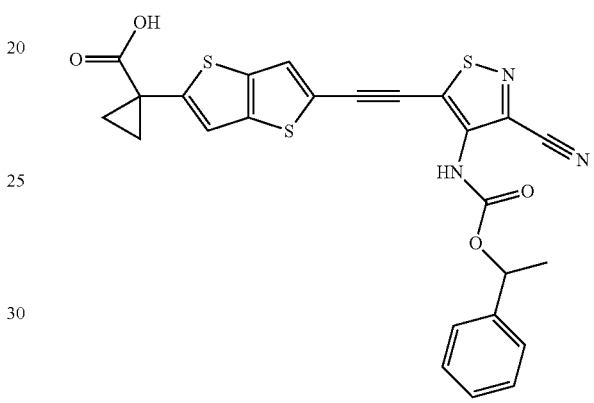
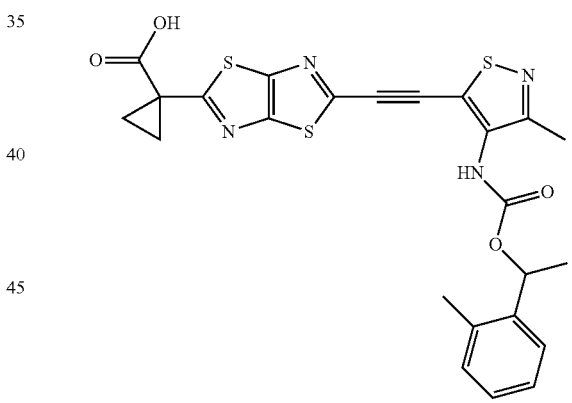
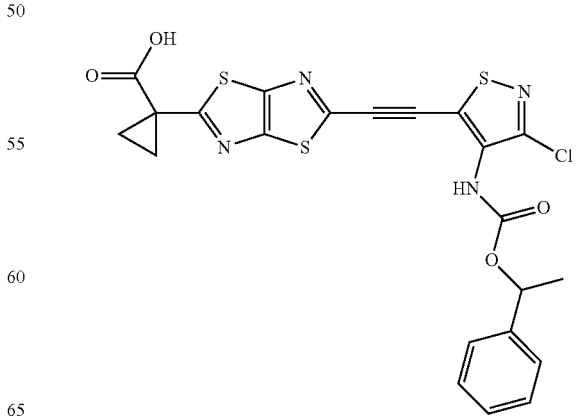

TABLE 18-continued
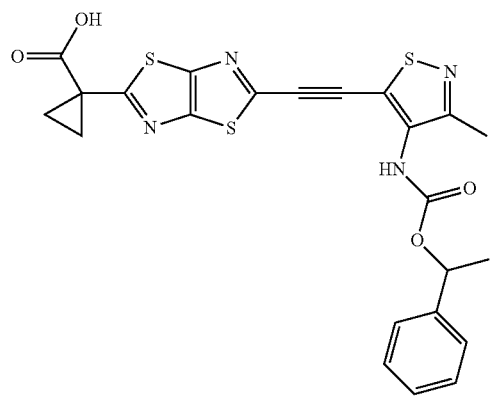 [SMILES: Cc1nsc(C#Cc2nc3sc(C4(C(=O)O)CC4)nc3s2)c1NC(=O)OC(C)c1ccccc1]
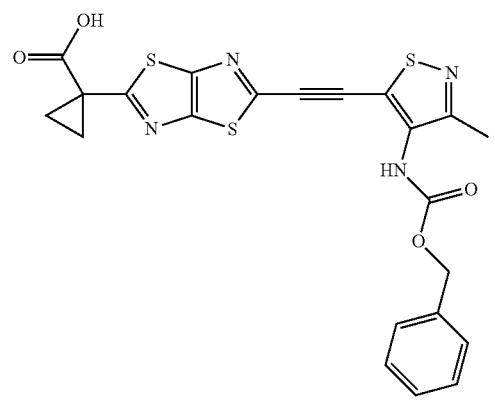 [SMILES: Cc1nsc(C#Cc2nc3sc(C4(C(=O)O)CC4)nc3s2)c1NC(=O)OCc1ccccc1]
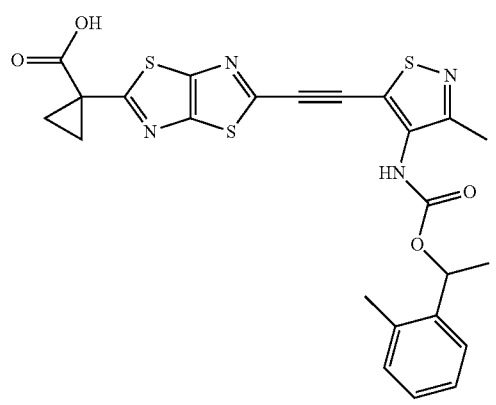 [SMILES: Cc1ccccc1C(C)OC(=O)Nc1c(C)nsc1C#Cc1nc2sc(C3(C(=O)O)CC3)nc2s1]
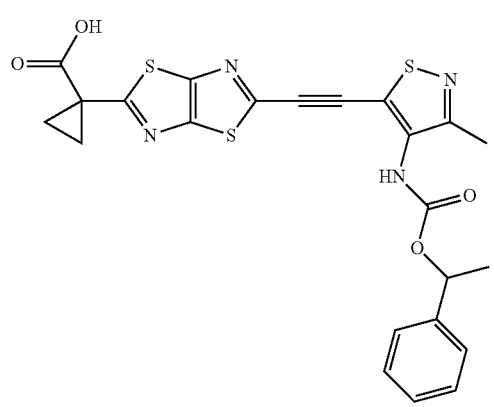 [SMILES: Cc1nsc(C#Cc2nc3sc(C4(C(=O)O)CC4)nc3s2)c1NC(=O)OC(C)c1ccccc1]
TABLE 18-continued
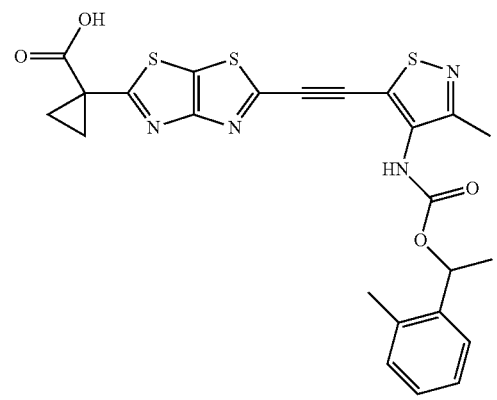 [SMILES: Cc1ccccc1C(C)OC(=O)Nc1c(C)nsc1C#Cc1nc2nc(C3(C(=O)O)CC3)sc2s1]
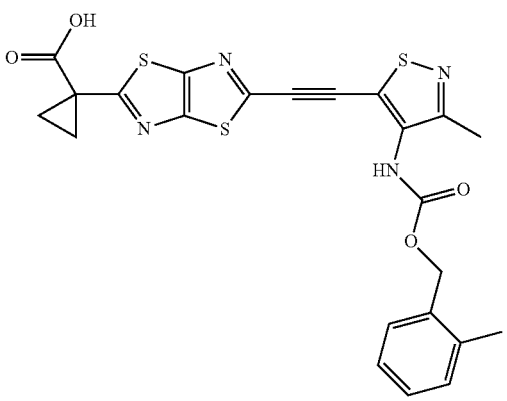 [SMILES: Cc1ccccc1COC(=O)Nc1c(C)nsc1C#Cc1nc2sc(C3(C(=O)O)CC3)nc2s1]
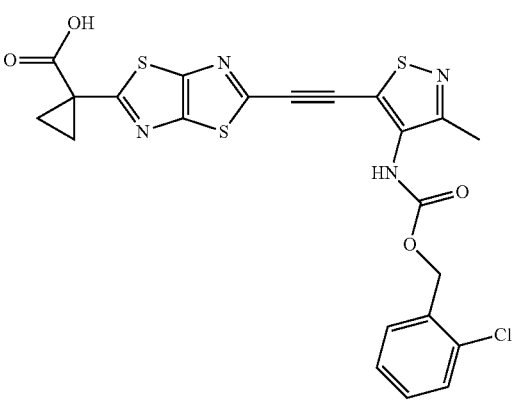 [SMILES: Cc1nsc(C#Cc2nc3sc(C4(C(=O)O)CC4)nc3s2)c1NC(=O)OCc1ccccc1Cl]
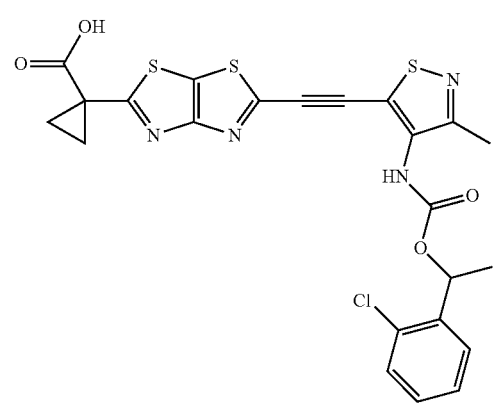 [SMILES: Cc1nsc(C#Cc2nc3nc(C4(C(=O)O)CC4)sc3s2)c1NC(=O)OC(C)c1ccccc1Cl]

TABLE 18-continued
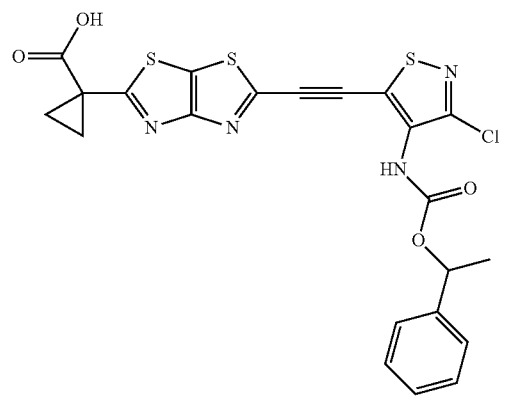 [SMILES: CC(OC(=O)Nc1c(Cl)nsc1C#Cc1nc2nc(C3(C(=O)O)CC3)sc2s1)c1ccccc1]
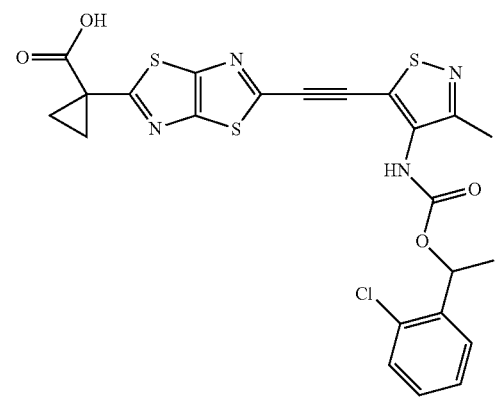 [SMILES: Cc1nsc(C#Cc2nc3sc(C4(C(=O)O)CC4)nc3s2)c1NC(=O)OC(C)c1ccccc1Cl]
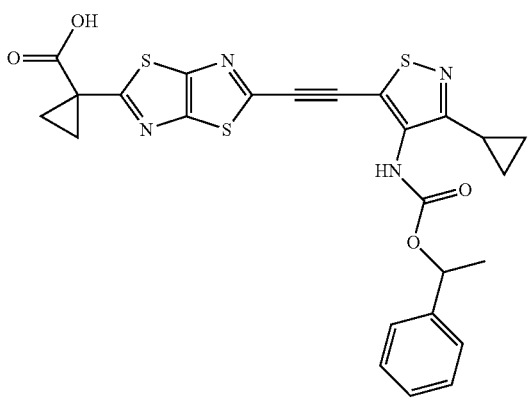 [SMILES: CC(OC(=O)Nc1c(C2CC2)nsc1C#Cc1nc2sc(C3(C(=O)O)CC3)nc2s1)c1ccccc1]
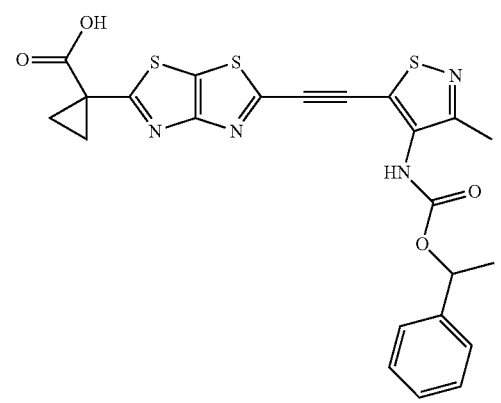 [SMILES: Cc1nsc(C#Cc2nc3nc(C4(C(=O)O)CC4)sc3s2)c1NC(=O)OC(C)c1ccccc1]
TABLE 18-continued
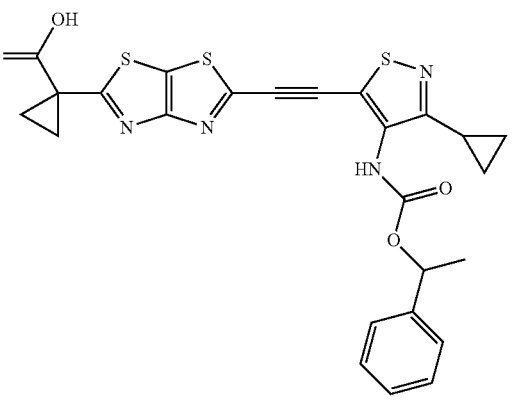
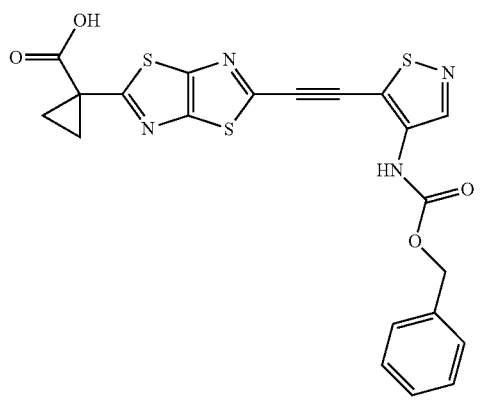
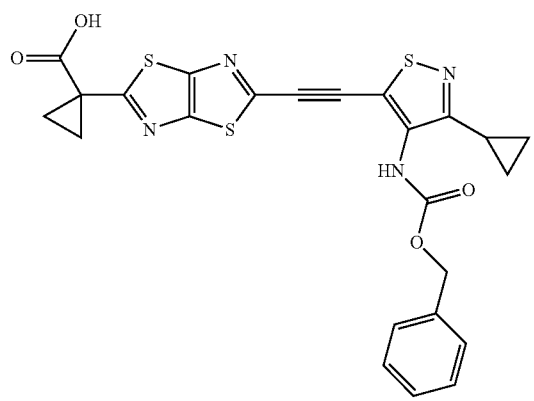
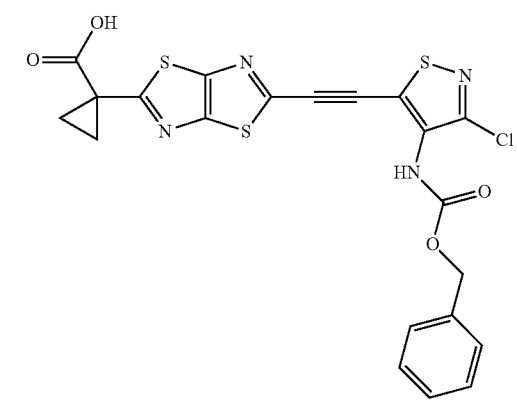 [SMILES: O=C(Nc1c(Cl)nsc1C#Cc1nc2sc(C3(C(=O)O)CC3)nc2s1)OCc1ccccc1]

TABLE 18-continued
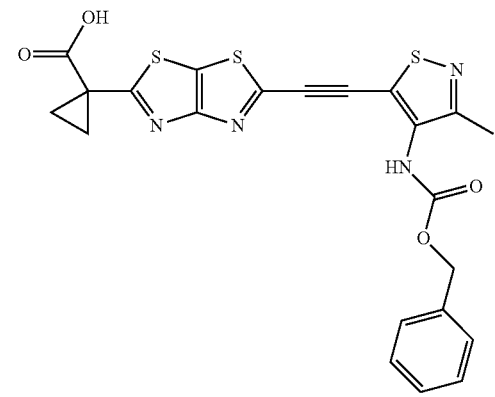 [SMILES: Cc1nsc(C#Cc2nc3nc(C4(C(=O)O)CC4)sc3s2)c1NC(=O)OCc1ccccc1]
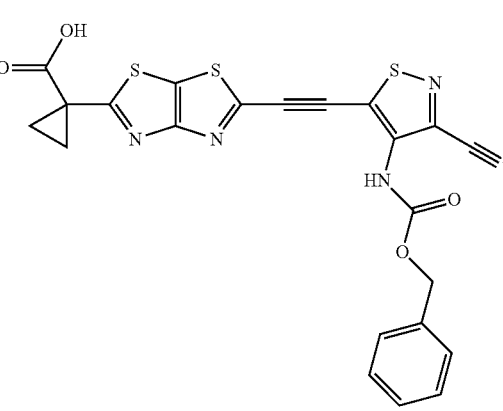
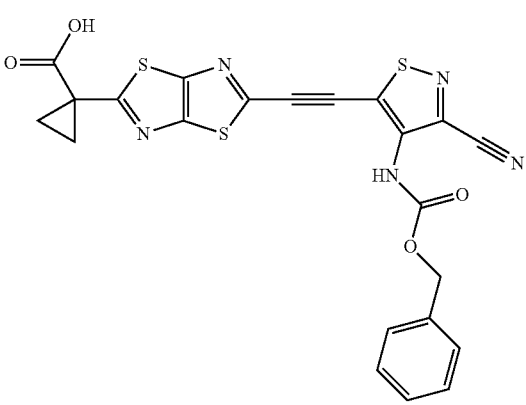 [SMILES: N#Cc1nsc(C#Cc2nc3sc(C4(C(=O)O)CC4)nc3s2)c1NC(=O)OCc1ccccc1]
TABLE 19
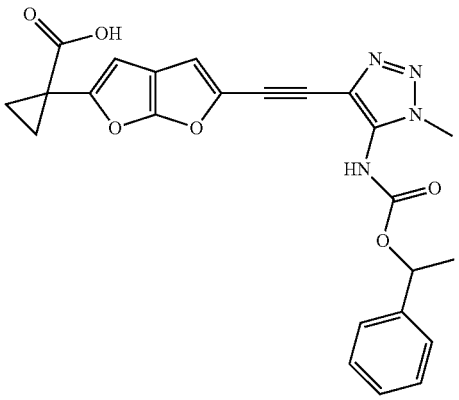 [SMILES: CC(OC(=O)Nc1c(C#Cc2cc3cc(C4(C(=O)O)CC4)oc3o2)nnn1C)c1ccccc1]
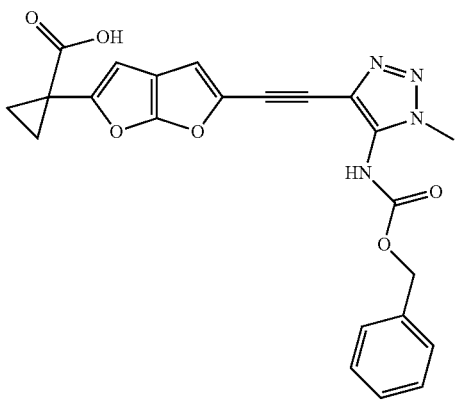 [SMILES: Cn1nnc(C#Cc2cc3cc(C4(C(=O)O)CC4)oc3o2)c1NC(=O)OCc1ccccc1]
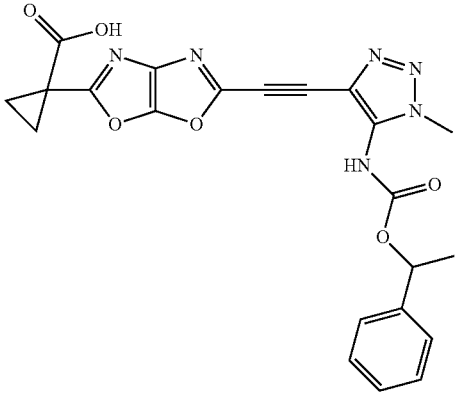 [SMILES: CC(OC(=O)Nc1c(C#Cc2nc3nc(C4(C(=O)O)CC4)oc3o2)nnn1C)c1ccccc1]
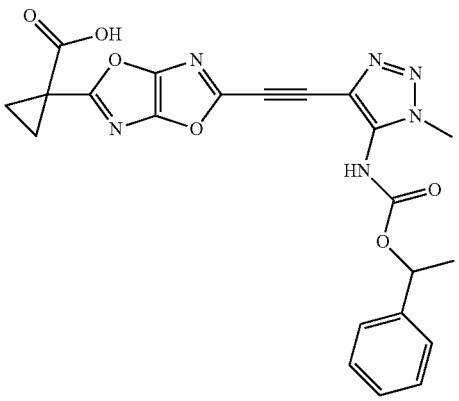 [SMILES: CC(OC(=O)Nc1c(C#Cc2nc3oc(C4(C(=O)O)CC4)nc3o2)nnn1C)c1ccccc1]
In some embodiments, compounds of Formula (I) are selected from the following compounds as listed in Table 19.

669
TABLE 19-continued
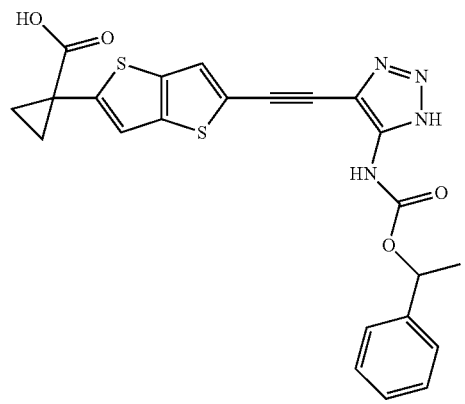 [SMILES: CC(OC(=O)Nc1[nH]nnc1C#Cc1cc2sc(C3(C(=O)O)CC3)cc2s1)c1ccccc1]
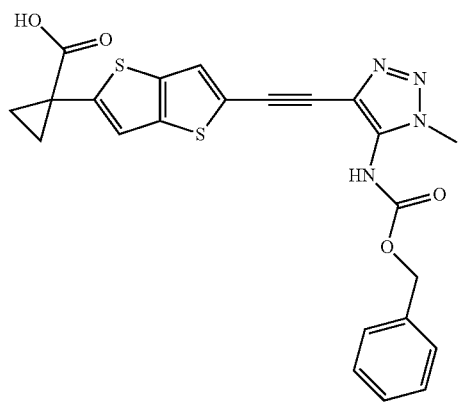 [SMILES: Cn1nnc(C#Cc2cc3sc(C4(C(=O)O)CC4)cc3s2)c1NC(=O)OCc1ccccc1]
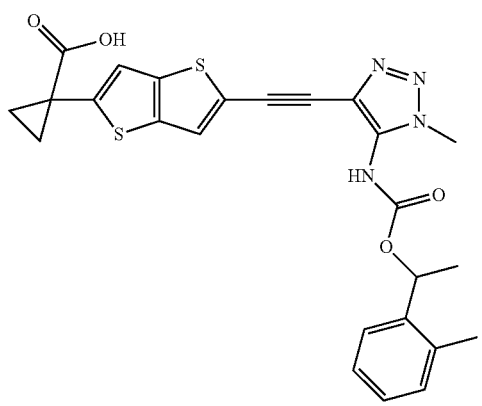 [SMILES: Cc1ccccc1C(C)OC(=O)Nc1c(C#Cc2cc3sc(C4(C(=O)O)CC4)cc3s2)nnn1C]
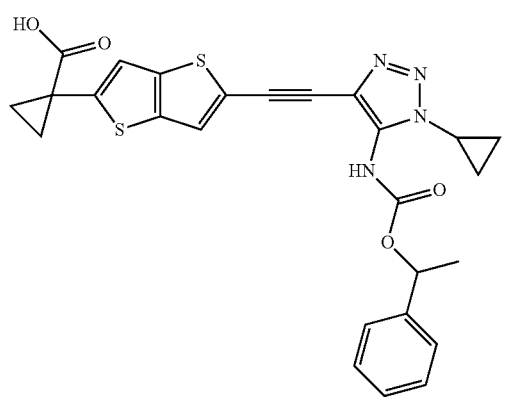 [SMILES: CC(OC(=O)Nc1c(C#Cc2cc3sc(C4(C(=O)O)CC4)cc3s2)nnn1C1CC1)c1ccccc1]
670
TABLE 19-continued
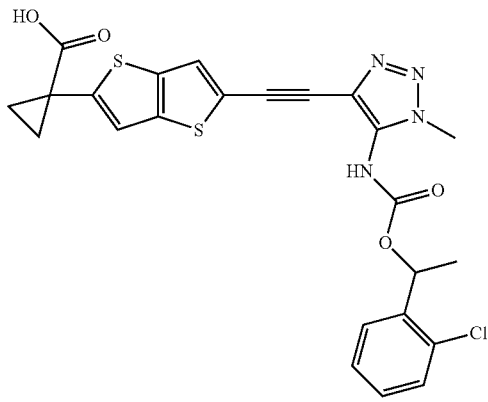 [SMILES: CC(OC(=O)Nc1c(C#Cc2cc3sc(C4(C(=O)O)CC4)cc3s2)nnn1C)c1ccccc1Cl]
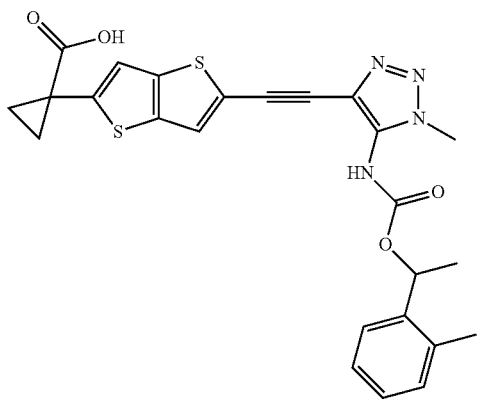 [SMILES: Cc1ccccc1C(C)OC(=O)Nc1c(C#Cc2cc3sc(C4(C(=O)O)CC4)cc3s2)nnn1C]
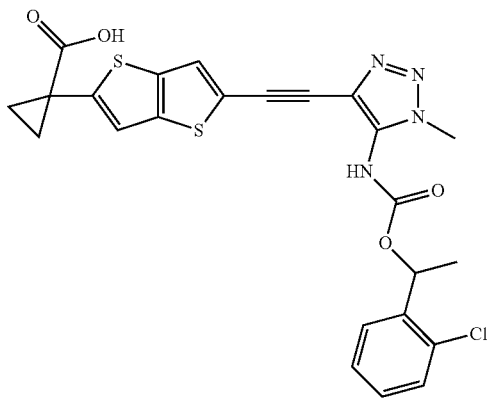 [SMILES: CC(OC(=O)Nc1c(C#Cc2cc3sc(C4(C(=O)O)CC4)cc3s2)nnn1C)c1ccccc1Cl]
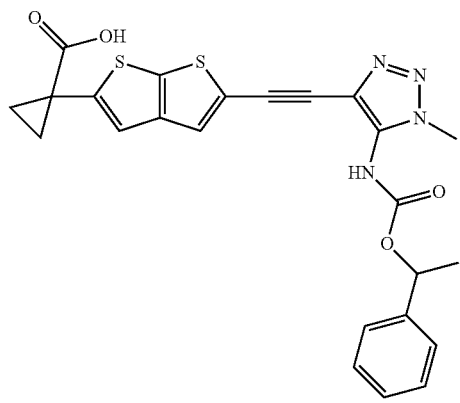 [SMILES: CC(OC(=O)Nc1c(C#Cc2cc3cc(C4(C(=O)O)CC4)sc3s2)nnn1C)c1ccccc1]

TABLE 19-continued

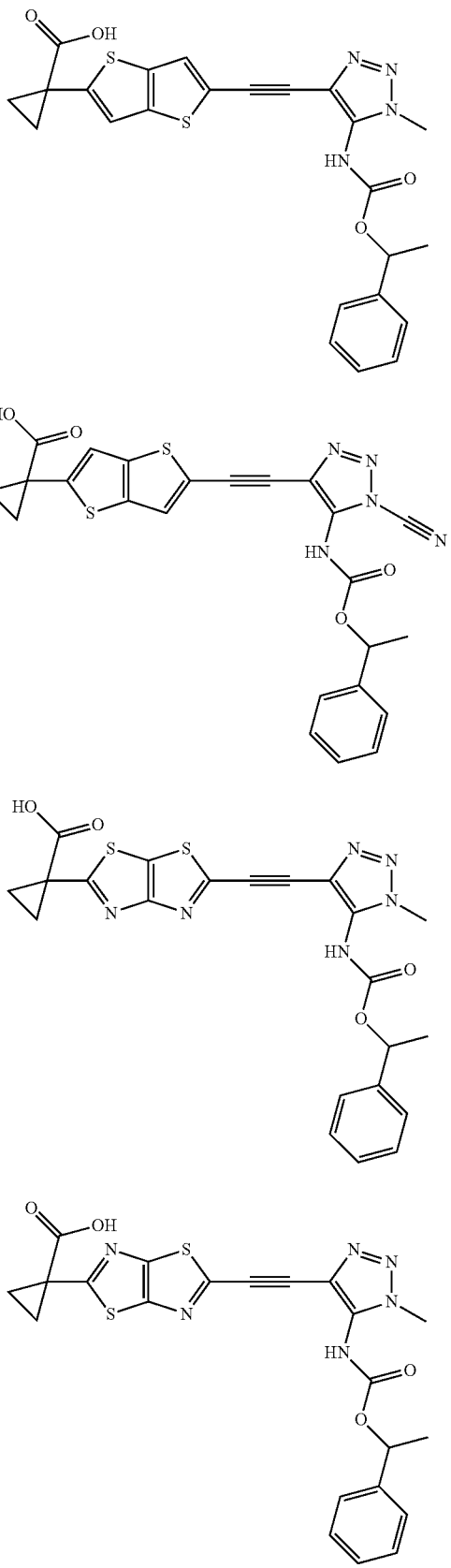

Synthesis of Compounds

Compounds of Formula (I) described herein are synthesized using standard synthetic techniques or using methods known in the art in combination with methods described herein. In additions, solvents, temperatures and other reaction conditions presented herein may vary.

The starting material used for the synthesis of the compounds of Formula (I) are either synthesized or obtained from commercial sources, such as, but not limited to, Sigma-Aldrich, Fluka, Acros Organics, Alfa Aesar, or the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

Pharmaceutical Compositions/Formulations, Routes of Administration, and Methods of Treatment In some embodiments, the compounds described herein are prepared into pharmaceutical compositions. Pharmaceutical compositions suitable for administration to a patient in need thereof can be prepared using techniques known in the art. Pharmaceutically acceptable inactive ingredients that facilitate processing of the active compounds into pharmaceutical compositions can also be employed. Once a route of administration chosen, a pharmaceutical composition can be developed. Suitable pharmaceutical compositions include those described, e.g., in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), the contents of which are hereby expressly incorporated by reference herein.

Pharmaceutical compositions suitable for use in the methods of preferred embodiments include a mixture of one or more compounds of a preferred embodiment with other chemical components (e.g., pharmaceutically acceptable inactive or active ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a patient in need thereof.

The pharmaceutical compositions of preferred embodiments can be systemically and/or locally administrable to a patent in need thereof in a variety of ways and by multiple administration routes, including, but not limited to, oral, parenteral (e.g., intravenous, subcutaneous, intramuscular, intramedullary injections, intrathecal, direct intraventricular, intraperitoneal, intralymphatic, intranasal injections), inhalation, injection (e.g., intramuscular, subcutaneous, or intravenous), rectal (e.g., enemas, rectal gels, rectal foams, rectal aerosols, suppositories, jelly suppositories, or retention enemas), intranasal, buccal, topical or transdermal administration routes. Such pharmaceutical compositions can be in a form of aqueous liquid dispersions, aqueous oral dispersions, emulsions, solutions, elixirs, gels, syrups, self-emulsifying dispersions, solid solutions, liposomal dispersions, aerosols, mists, solid dosage forms, powders, nasal sprays, nasal mists, eye drops immediate release formulations, controlled release formulations, fast melt formulations, tablets, lozenge, capsules, pills, delayed release formulations, extended release formulations, pulsatile release formulations, multiparticulate formulations, and mixed immediate and controlled release formulations. Topically administrable compositions include solutions, suspensions, lotions, gels, pastes, shampoos, scrubs, rubs, smears, medicated sticks, medicated bandages, balms, creams, or ointments.

The compounds of preferred embodiments and pharmaceutical compositions comprising the same can be used for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering the compound to a subject in need thereof, e.g., a subject that has a LPA-dependent or LPA-mediated disease or condition at the time of administration, or is at risk of developing a LPA-dependent or LPA-mediated disease or condition.

Also provided are methods that include the diagnosis or determination of whether or not a patient is suffering from a LPA-dependent or LPA-mediated disease or condition by administering to the subject a therapeutically effective amount of a compound of a preferred embodiment and determining whether or not the patient responds to the treatment.

The pharmaceutical compositions can be administered continuously or intermittently, e.g., in single administrations of an effective amount of the compound, or administrations twice, three times, or four times or more over the span of one day. The pharmaceutical compositions can be administered over a single day or multiple days, with a time between administrations of, e.g., 4, 5, 6, 7, 8, 9, 10, 11, 12 or 24 hours. For example, the compound of preferred embodiments can be administered continuously or intermittently as in a single dose; or in multiple doses with a dose administered every 6 hours, or 8 hours, or 12 hours, or 24 hours. Also contemplated are administration methods including a drug holiday, wherein the administration of the compound is temporarily suspended or the dose of the compound being administered is temporarily reduced; at the end of the drug holiday, dosing of the compound is resumed. The length of the drug holiday varies from 2 days, or 1 month, or two months, or 3 months, or 6 months, or 9 months, to 1 year or more. The pharmaceutical composition can be administered therapeutically or prophylactically for a fixed period of time indefinitely.

The compounds of preferred embodiments can be used in the preparation of medicaments for the treatment of LPA-dependent or LPA-mediated diseases or conditions. Treatment involves administration of pharmaceutical compositions that include at least one compound of preferred embodiments or a pharmaceutically acceptable salt, active metabolite, prodrug, or solvate thereof, in a therapeutically effective amount, to said patient. The compounds of preferred embodiments can be administered for prophylactic and/or therapeutic treatment. In certain therapeutic applications, the compositions are administered to a patient already suffering from a disease or condition, in an amount sufficient to cure or at least partially mitigate at least one of the symptoms of the disease or condition. Amounts effective for this use depend on the severity and course of the disease or condition, previous therapy, the patient's health status, weight, and response to the drugs, and the judgment of the treating physician. Therapeutically effective amounts can be determined by methods including, but not limited to, a dose escalation clinical trial. In prophylactic applications, the compounds of preferred embodiments are administered to a patient susceptible to or otherwise at risk of a particular disease, disorder, or condition. The dose of drug being administered may be temporarily reduced or temporarily suspended for a certain length of time (i.e., a "drug holiday").

Doses employed for adult human treatment are typically in the range of 0.01 mg to 5000 mg per day, or from about 1 mg to about 1000 mg per day. The desired dose can be provided in a single dose or in divided doses.

In certain embodiments, patients in need of treatment can be identified by screening for LPA receptor gene SNPs. Patients can be further selected based on increased LPA receptor expression in the tissue of interest. LPA receptor expression are determined by methods including, but not limited to, northern blotting, western blotting, quantitative PCR (qPCR), flow cytometry, autoradiography (using a small molecule radioligand or PET ligand). In some embodiments, patients are selected based on the concentration of serum or tissue LPA measured by mass spectrometry. In some embodiments, patients are selected based on a combination of the above markers (increased LPA concentrations and increased LPA receptor expression).

In certain embodiments, the compounds of preferred embodiments are administered with another therapeutic treatment or another therapeutic agent, e.g., a second therapeutic agent that modulates different aspects of the disease, disorder or condition being treated, thereby providing a greater overall benefit than administration of either therapeutic agent alone. For combination therapies, the dosages of the co-administered compounds vary depending on the type or specific drug employed, on the disease or condition being treated, and other factors. When co-administered with one or more other therapeutic agents, the compounds of preferred embodiments can be administered either simultaneously with the one or more other therapeutic agents, or sequentially, and can be present in the same unit dosage form or in different unit dosage forms. If administration is simultaneous, the multiple therapeutic agents are, by way of example only, provided in a single, unified form, or in multiple forms. In the treatment of cancer, it is advantageous to administer a compound of a preferred embodiment in combination with one or more anti-cancer agents and/or radiation therapy. In the treatment of fibrosis, it is advantageous to administer a compound of a preferred embodiment in combination with one or more immunosuppresants and/or with corticosteroids. In treating LPA-dependent or LPA-mediated conditions or diseases, such as the therapy of respiratory disorders (e.g., pulmonary fibrosis, asthma, COPD, rhinitis), it is advantageous to administer a compound of a preferred embodiment in combination with one or more agents used in the treatment of respiratory conditions, e.g., anti-inflammatory agents or inhaled corticosteroids.

EXAMPLES

These examples are provided for illustrative purposes only and not to limit the scope of the claims provided herein.

Synthesis of Compounds

Synthesis of Compound 6 R-isomer

Synthetic Route (Scheme I-A)

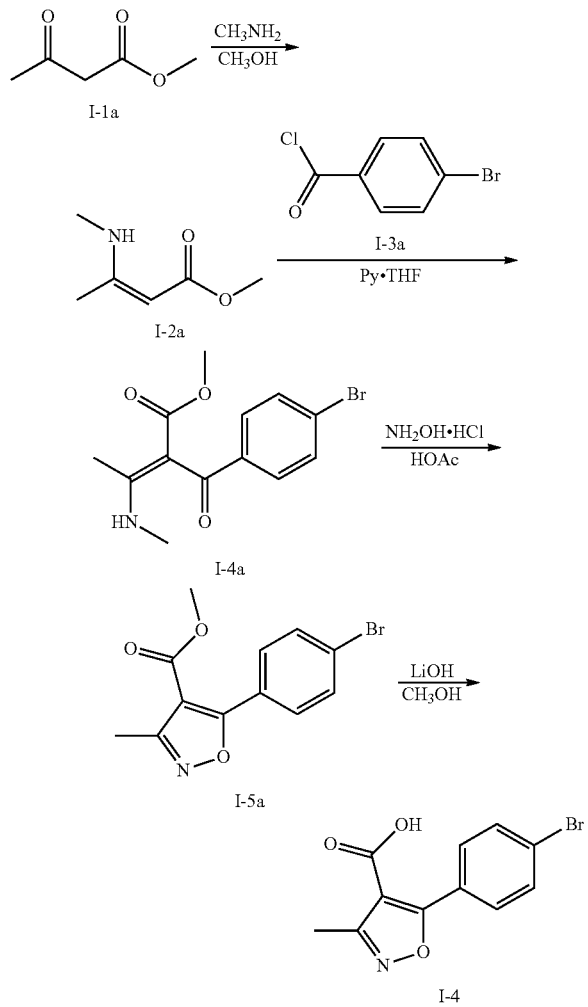

Methylamine solution in MeOH (45 g, 517 mmol, 37% w/w) was added into compound I-1a (30 g, 258.6 mmol) at rt, then the mixture was heated to 45° C. for 18 hrs. After being cooled to rt, the mixture was extracted with DCM (250 mL×3), the combined organic layer a washed with water, dried over $Na_2SO_4$, and concentrated in vacuo to give compound I-2a (29 g, yield 88%).

To a stirred solution of compound I-2a (1.00 g, 7.82 mmol) and pyridine (0.74 mL, 7.82 mmol) in THF was added dropwise compound I-3a (1.71 g, 7.82 mmol) at 0° C. under nitrogen. After the addition, the solution was stirred for 0.5 h, then warmed slowly to the rt, and stirred overnight. $H_2O$ (60 mL) was added, and the mixture was extracted with EtOAc (60 mL×3). The organic layer was combined and washed with brine, dried over $Na_2SO_4$, concentrated in vacuo. The residue was purified by column chromatography on silica gel (Petroleum ether:EtOAc=10:1) to afford compound I-4a (0.8 g, yield 33%).

To a stirred solution of I-4a (0.78 g, 2.5 mmol) in HOAc (10 mL) was added hydroxylamine hydrochloride (0.17 g, 2.5 mmol) under nitrogen. After the addition, the solution was heated to reflux under nitrogen for 2 hrs. The solution was concentrated in vacuo to afford compound I-5a (0.66 g, yield 89%), which was used for next step without further purification.

To a stirred solution of I-5a (0.66 g, 2.23 mmol) in 10 mL of $MeOH/H_2O$ (v/v=5:1) was added lithium hydroxide (0.12 g, 2.74 mmol). The solution was heated to reflux under nitrogen for 1 hr. MeOH was removed in vacuo and the residue was adjusted to pH=2. The aqueous phase was extracted with DCM (50 mL×3). The combined organic layer was washed with brine, dried over $Na_2SO_4$, concentrated to afford compound I-4 (0.36 g, yield 58%). MS (ESI) m/z $(M+H)^+$ 280.

Synthetic Route (Scheme I-B)

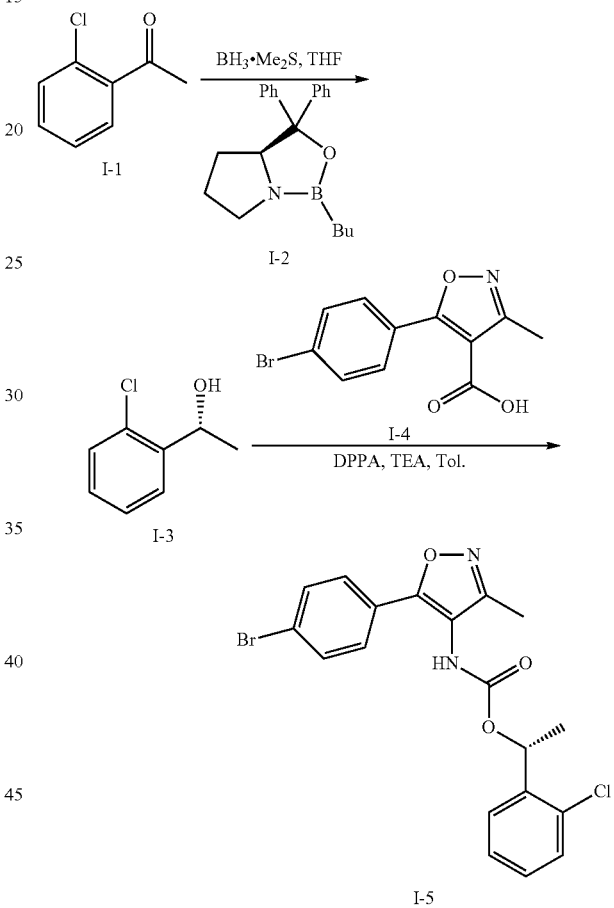

Borane dimethyl sulfide complex (10 mL, 100 mmol) was added to a solution of catalyst I-2 (7.8 mL, 7.8 mmol) in 100 mL of THF, then compound I-1 (20 g, 129 mmol) in THF (50 mL) was added dropwise at room temperature within 20 min. The reaction was stirred for further 10 min, and then quenched with $CH_3OH$. The mixture filtered and concentrated in vacuo. The residue was purified by column chromatography on silica gel (Petroleum ether: EtOAc=80:1) to provide compound I-3 (8 g, yield 79%, ee %~80%).

A mixture of compound I-3 (1.87 g, 12 mmol), compound I-4 (2.82 g, 10 mmol), DPPA (3.3 g, 12 mmol) and TEA (2.02 g, 20 mmol) in toluene was stirred at 90° C. for 3 hrs. The mixture was diluted with EtOAc (100 mL), washed with water and brine. The organic layer was dried over $Na_2SO_4$, filtered, and concentrated. The residue was purified by column chromatography on silica gel (Petroleum ether: EtOAc=30:1) to afford I-5 (3 g, yield 69%).

Synthetic Route (Scheme I-C)
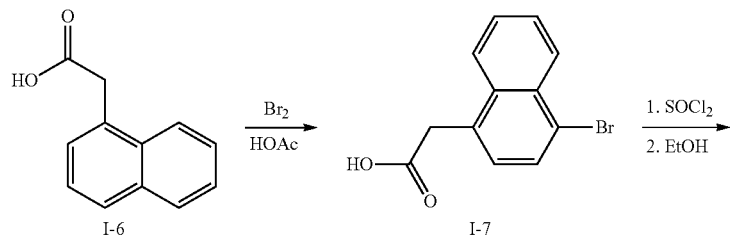
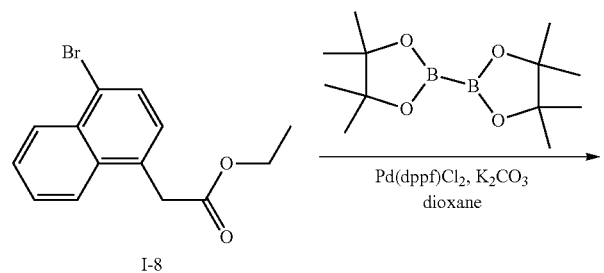
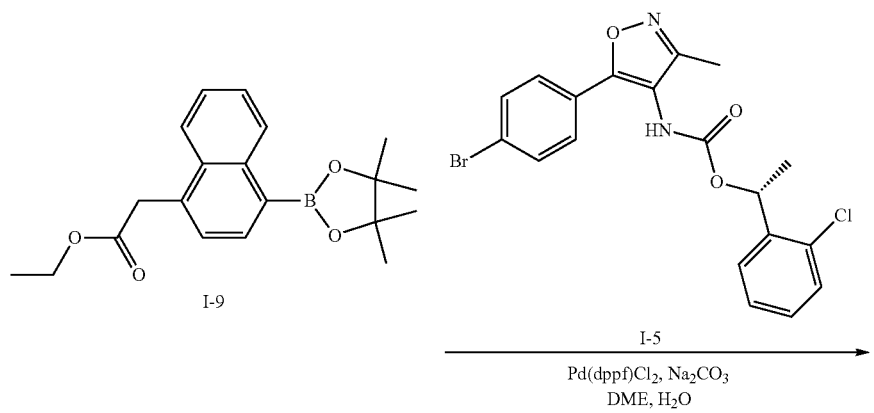
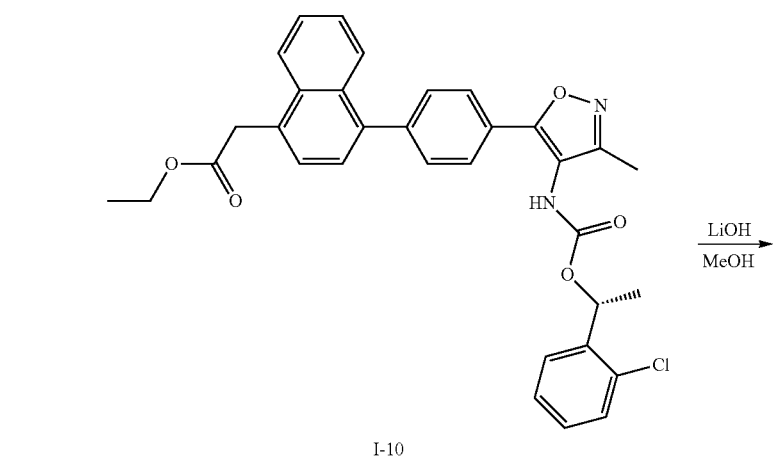

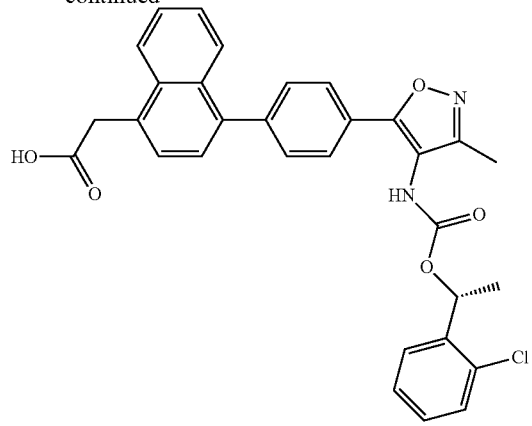

Compound 6

Bromine (1.46 mL, 28.3 mmol) was added to the mixture of compound I-6 (5.27 g, 28.3 mmol) in 25 mL of HOAc. The reaction mixture was heated to 80° C. for 3 hrs. After standing overnight, the crude product was precipitated. Recrystallized from chloroform to afford compound I-7 (2.8 g, yield 37%).

A mixture of compound I-7 (2.6 g, 10 mmol) and thionyl chloride (5 mL) in EtOH (10 mL) was stirred at rt for 12 hrs. The mixture was concentrated in vacuo, and re-dissolved with EtOAc (100 mL), and then the organic layer was washed with water and brine, dried over $Na_2SO_4$ and concentrated to give compound I-8 (2 g, yield 69%).

To a stirred mixture of compound I-8 (1.8 g, 6.14 mmol), bis(pinacolato)diboron (1.87 g, 7.37 mmol) and $K_2CO_3$ (1.68 g, 12.3 mmol) in 1,4-dioxane (20 mL) was added Pd(dppf)Cl$_2$ (200 mg) under $N_2$ protection, and the mixture was stirred at 90° C. for 3 hrs. After being cooled to rt, the mixture was diluted with EtOAc (100 mL), washed with water and brine, dried over $Na_2SO_4$, filtered, and concentrated. The residue was purified by column chromatography on silica gel (Petroleum ether:EtOAc=50:1) to give product I-9 (1.2 g, yield 58%).

Preparation of Intermediate I-10 (Compound 5)

To a stirred mixture of compound I-9 (586 mg, 1.72 mmol), I-5 (500 mg, 1.15 mmol), and $Na_2CO_3$ (244 mg, 2.3 mmol) in DME/$H_2O$ (8 mL/2 mL) was added Pd(dppf)Cl$_2$ (50 mg) under $N_2$ protection, and the mixture was stirred at 90° C. for 3 hrs. After being cooled to rt, the mixture was diluted with EtOAc (80 mL), washed with water and brine, dried over $Na_2SO_4$, filtered, and concentrated. The residue was purified by column chromatography on silica gel (Petroleum ether: EtOAc=10:1) to yield I-10 (400 mg, yield 61%). $^1$H NMR (CDCl$_3$, 400 MHz): δ 8.07 (d, J=7.6 Hz, 1 H), 7.86-7.88 (m, 3H), 7.44-7.59 (m, 6H), 7.22-37 (m, 4H), 6.23-6.28 (m, 1H), 4.23-4.18 (q, 2H), 4.12 (s, 2H), 2.29 (s, 3H), 1.44-1.68 (m, 3H), 1.28 (t, J=7.2 Hz, 3H). MS (ESI) m/z (M+H)$^+$569.0.

Preparation of Compound 6

A mixture of I-10 (285 mg, 0.5 mmol) and lithium hydroxide monohydrate (42 mg, 1 mmol) in MeOH/$H_2O$ (6 mL, v/v=5/1) was stirred at 60° C. for 1 h. The mixture was concentrated in vacuo to remove MeOH, and acidified with aq. HCl (2 N) to pH ~3, extracted with DCM (30 mL×3). The combined organic layers was dried over $Na_2SO_4$, filtered, and concentrated. The residue was purified by prep-HPLC and chiral HPLC to afford Compound 6 (R) isomer (85 mg, yield: 30%). $^1$H NMR (DMSO-d$_6$, 400 MHz): δ 9.49 (s, 1H), 8.07 (d, J=8.4 Hz, 1H), 7.88 (d, J=7.6 Hz, 2H), 7.79 (d, J=8.4 Hz, 1H), 7.39-7.60 (m, 9H), 7.31 (d, J=7.6 Hz, 1 H), 5.97-6.02 (q, 1H), 4.08 (s, 2H), 2.14 (s, 3H), 1.54 (d, J=6.0 Hz, 3H). MS (ESI) m/z (M+H)$^+$ 541.0.

Preparation of Compound 7 R-Isomer

Synthetic Route (Scheme II)

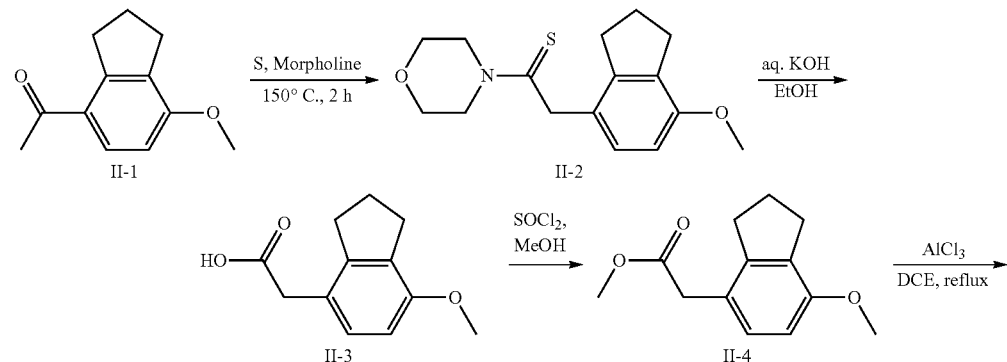

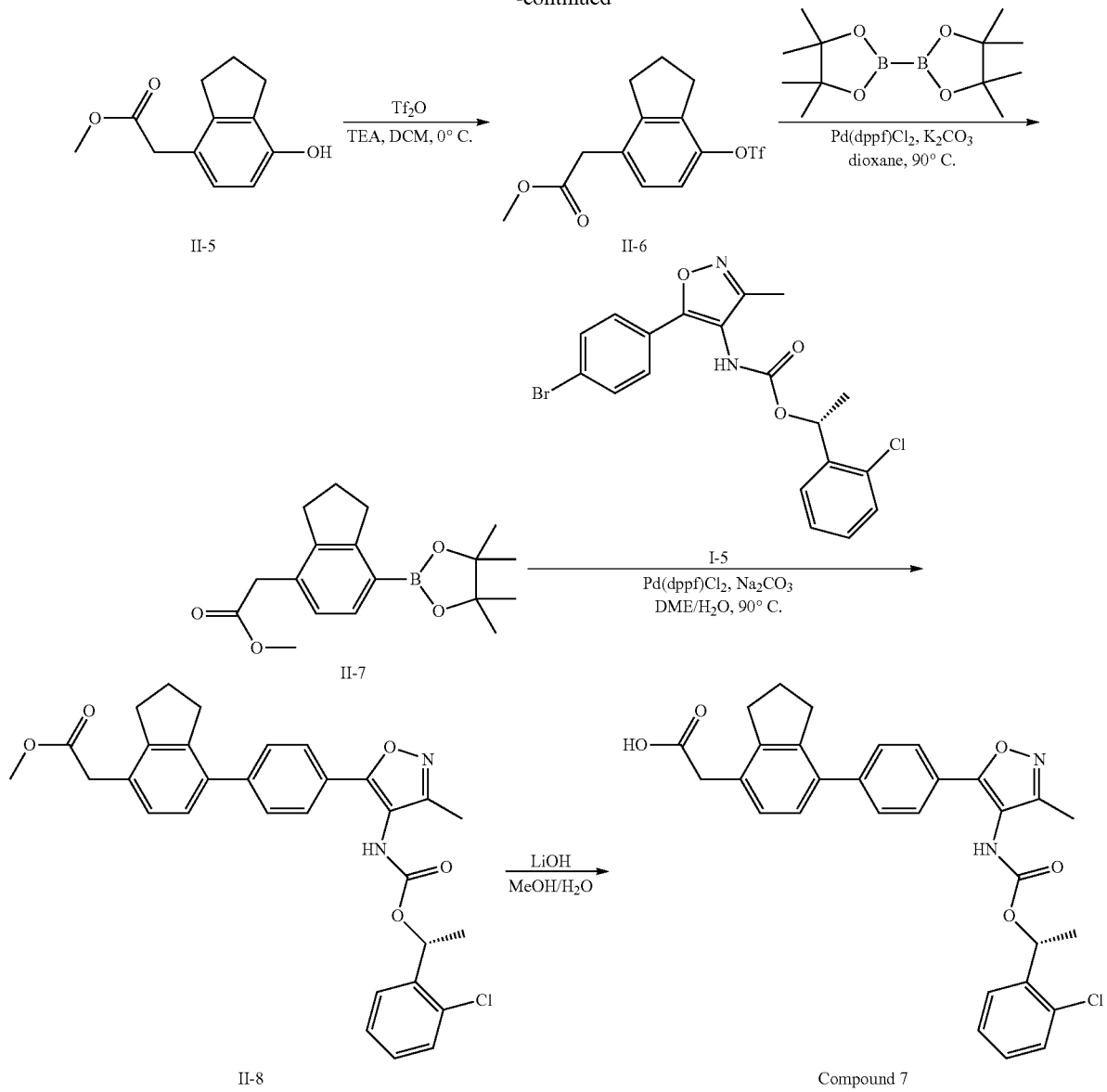

A mixture of compound II-1 (1.9 g, 10 mmol), sulfur (0.5 g, 25 mmol) and morpholine (1.74 g, 20 mmol) was heated to 150° C. for 2.5 hrs. After being cooled in an ice bath, the mixture was treated with ethanol for a period of 60 min. The precipitated solid was collected by suction filtration and re-crystallized from ethanol to give compound II-2 (2.1 g, yield 72%).

The mixture of compound II-2 (1.6 g, 5.5 mmol), 50% KOH aqueous solution (10 mL) and EtOH (10 mL) was stirred at reflux for 6 hrs. EtOH was removed in vacuo, the residue was diluted with water (20 mL), washed with toluene. The aqueous layer was adjusted to pH=1 with conc. HCl, then extracted with DCM (50 mL×3). The combined organic layer was washed with brine, dried over $Na_2SO_4$, and concentrated to give compound II-3 (1.0 g, yield 88%).

Preparation of Intermediate II-4

A mixture of compound II-3 (1.0 g, 4.8 mmol) and thionyl chloride (2 mL) in MeOH (10 mL) was stirred at rt for 12 hrs. The mixture was concentrated in vacuo, and re-dissolved with EtOAc (100 mL), then washed with water and brine. The organic layer was dried over $Na_2SO_4$ and concentrated. The residue was purified by column chromatography on silica gel (Petroleum ether:EtOAc=70:1) to afford compound II-4 (700 mg, yield 66%).

Preparation of Intermediate II-5

$AlCl_3$ (634 mg, 4.77 mmol) was added to a solution of compound II-4 (700 mg, 3.18 mmol) in 1,2-dichloroethane (10 mL), the reaction mixture was stirred at reflux overnight. After being cooled to room temperature, the mixture was poured into 20 mL of ice/water, then extracted with DCM (30 mL×3). The combined organic layer was washed with brine, dried over sodium sulfate, and concentrated to give the crude product, which was purified by column chromatography on silica gel (Petroleum ether:EtOAc=20:1) to afford compound II-5 (300 mg, yield 46%).

Preparation of Intermediate II-6

Tf$_2$O (820 mg, 3.6 mmol) was added to a solution of compound II-5 (0.5 g, 2.8 mmol) and TEA (0.57 g, 5.6 mmol) in dry DCM (10 mL) at 0° C. The resulting solution was stirred at 0° C. for 2 hours. TLC (Petroleum ether: EtOAc=5:1) showed the starting material was consumed completely. The reaction mixture was diluted with DCM (50 mL) and washed with water (5 mL). The organic layer was dried over Na$_2$SO$_4$, filtered, and concentrated under reduced pressure. The residue was purified by column chromatography on silica gel (Petroleum ether:EtOAc=70:1) to provide compound II-6 (300 mg, yield 64%).

Preparation of Intermediate II-7

To a mixture of compound II-6 (300 mg, 0.93 mmol), bis(pinacolato)diboron (353 mg, 1.39 mmol) and K$_2$CO$_3$ (190 mg, 1.86 mmol) in 1,4-dioxane (5 mL) was added Pd(dppf)Cl$_2$ (50 mg) under N$_2$ protection, and the mixture was stirred at 90° C. for 3 hrs. The mixture was diluted with EtOAc (60 mL), washed with water and brine, dried over Na$_2$SO$_4$, filtered, and concentrated. The residue was purified by prep-TLC (Petroleum ether:EtOAc=10:1) to yield product II-7 (150 mg, yield 51%).

Preparation of Intermediate II-8

To a mixture of compound II-7 (150 mg, 0.47 mmol), I-5 (227 mg, 0.52 mmol), and Na$_2$CO$_3$ (100 mg, 0.95 mmol) in DME (3 mL) and H$_2$O (0.8 mL) was added Pd(dppf)Cl$_2$ (20 mg) under N$_2$ protection. The mixture was stirred at 90° C. for 3 hrs. After diluted with EtOAc (60 mL), the mixture was washed with water and brine, dried over Na$_2$SO$_4$, filtered, and concentrated. The residue was purified by prep-TLC (Petroleum ether:EtOAc=2:1) to give product II-8 (150 mg, yield 58%). MS (ESI) m/z (M+H)$^+$ 545.1.

Preparation of Compound 7

A mixture of compound II-8 (130 mg, 0.24 mmol) and lithium hydroxide monohydrate (20 mg, 0.48 mmol) in MeOH/H$_2$O (3 mL, v/v=5/1) was stirred at 60° C. for 1 h. The mixture was concentrated in vacuo to remove MeOH, and then acidified with aq. HCl (2 N) to pH=3, and then extracted with DCM (30 mL×3). The combined organic layer was washed with brine, dried over Na$_2$SO$_4$, filtered, and concentrated. The residue was purified by prep-HPLC and chiral HPLC to give Compound 7 (R) isomer (85 mg, yield 30%). $^1$H NMR (CD$_3$OD, 400 MHz): δ 7.83 (d, J=8.0 Hz, 2H), 7.52-7.66 (m, 3H), 7.17-7.29 (m, 5H), 6.16-6.19 (q, 1 H), 3.65 (s, 2H), 2.98 (t, J=7.2 Hz, 4H), 2.22 (s, 3H), 2.00-2.09 (m, 2H), 1.62 (d, J=6.4 Hz, 3H). MS (ESI) m/z (M+H)$^+$ 531.1.

Synthesis of Compound 8 R-Isomer

Synthetic Route (Scheme III)

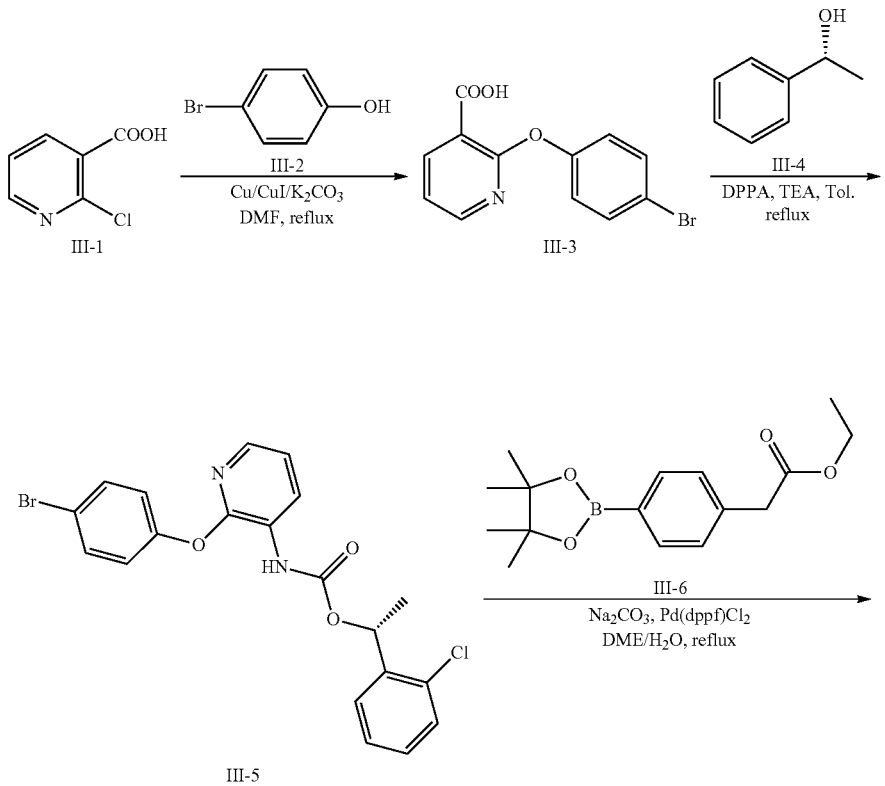

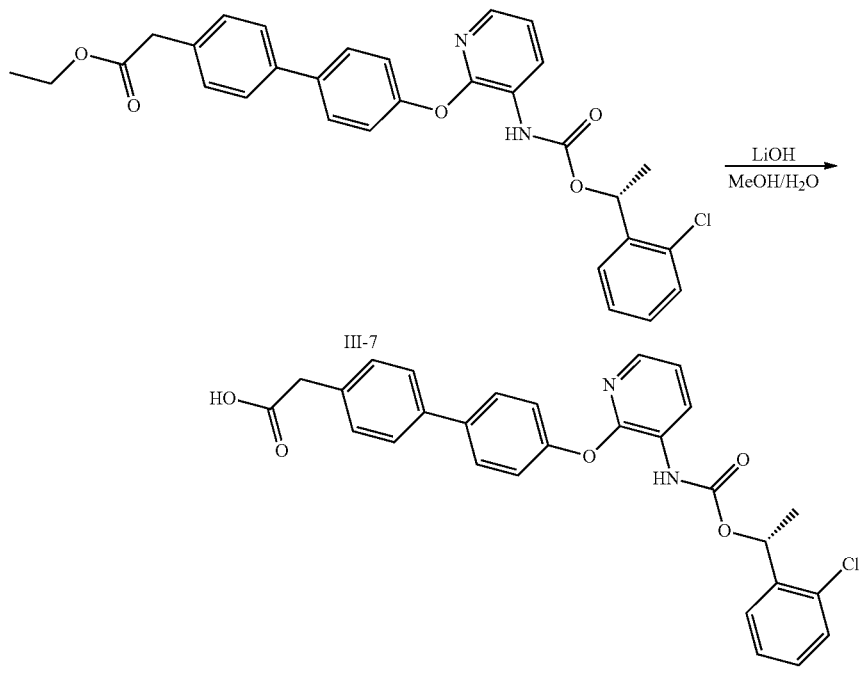

Compound 8

A mixture of compound III-1 (5 g, 31.73 mmol), compound III-2 (6.63 g, 38.32 mmol), $K_2CO_3$ (9.69 g, 70.21 mmol), Cu (449 mg, 7.01 mmol) and CuI (488 mg, 2.56 mmol) in DMF (100 mL) was heated to reflux under nitrogen for 6 hours. The mixture was filtered and concentrated, the residue was partitioned between $H_2O$ (30 mL) and DCM (100 mL), the organic layer was separated, washed with brine, dried over $Na_2SO_4$, and concentrated under reduced pressure. The residue was purified by Prep-HPLC to afford compound III-3 (3 g, yield 32%).

The mixture of compound III-3 (3 g, 10.2 mmol), compound III-4 (1.91 g, 12.2 mmol), DPPA (3.35 g, 12.3 mmol) and TEA (2.06 g, 20.4 mmol) in toluene (80 mL) was heated to reflux under nitrogen for 1 hour. The mixture was concentrated, and the residue was partitioned between $H_2O$ (30 mL) and DCM (100 mL). The organic layer was separated, washed with brine, dried over $Na_2SO_4$, concentrated. The residue was purified by column chromatography on silica gel (Petroleum ether:EtOAc=10:1) to afford compound III-5 (3.0 g, yield 66%). MS (ESI) m/z (M+H)+ 447.

The mixture of compound III-5 (2.5 g, 5.59 mmol), compound III-6 (1.79 g, 6.17 mmol), $Na_2CO_3$ (1.79 g, 16.88 mmol) and Pd(dppf)$Cl_2$ (204 mg, 0.28 mmol) in 40 mL of DME:$H_2O$ (v/v=3/1) was heated to reflux under nitrogen for 2 hours. The mixture was concentrated, and the residue was diluted with water (50 mL), the aqueous phase was extracted with DCM (50 mL×3). The combined organic layer was washed with brine, dried over $Na_2SO_4$, concentrated. The residue was purified by column chromatography on silica gel (Petroleum ether:EtOAc=5:1) to afford compound III-7 (0.7 g, yield 24%). MS (ESI) m/z (M+H)+ 531.0.

Preparation of Compound 8

To a stirred solution of III-7 (0.71 g, 1.34 mmol) in 10 mL of MeOH/$H_2O$ (v/v=5/1) was added lithium hydroxide monohydrate (0.07 g, 1.67 mmol) under argon. After the addition, the solution was heated to reflux under argon for 1 hour. The solution was concentrated in vacuo and the residue was adjusted to pH=2 with conc. HCl. The aqueous phase was extracted with DCM (30 mL×3). The combined organic layer was washed with brine, dried over $Na_2SO_4$, concentrated. The residue was purified by prep-HPLC to afford Compound 8 (R) isomer (0.6 g, yield 89%). $^1$H NMR (DMSO-$d_6$, 400 MHz): δ 12.37 (s, 1H), 9.49 (s, 1H), 8.13 (d, J=7.6 Hz, 1H), 7.81 (d, J=3.2 Hz, 1H), 7.59-7.68 (m, 5H), 7.40-7.46 (m, 5H), 7.08-7.20 (m, 3H), 6.08 (q, J=6.4 Hz, 1H), 3.60 (s, 2H), 1.51 (d, J=6.8 Hz, 3H). MS (ESI) m/z (M+H)+ 503.0.

Synthesis of Compounds 14 and 16

Synthetic Route (Scheme IV)

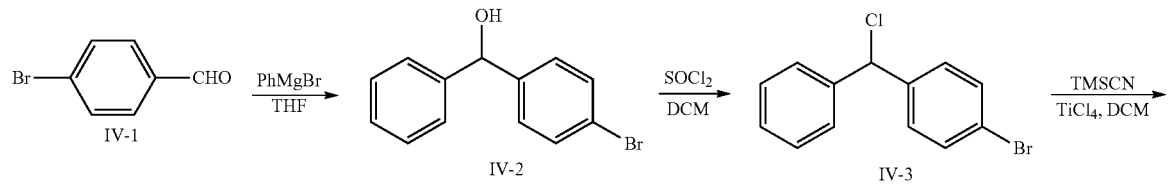

-continued
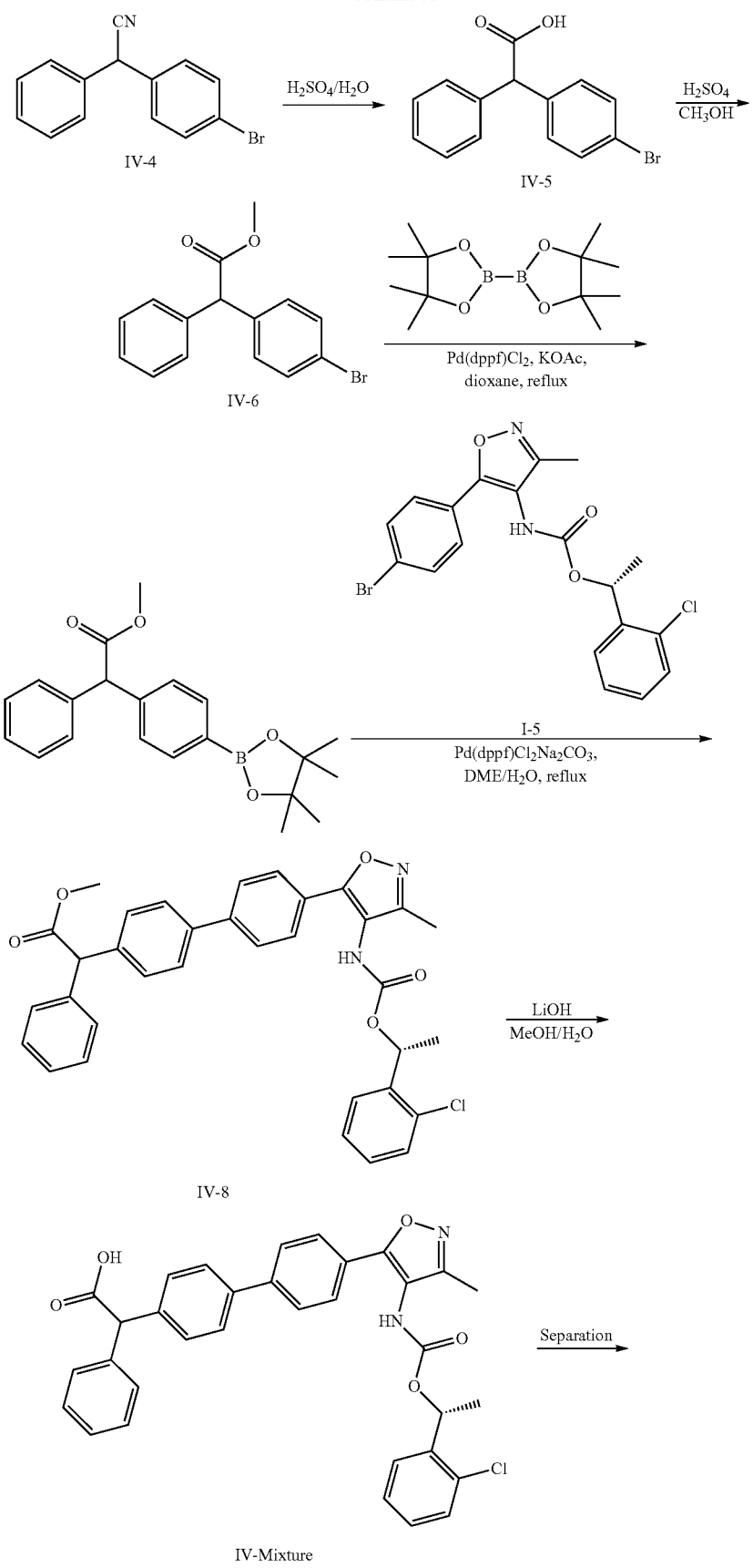

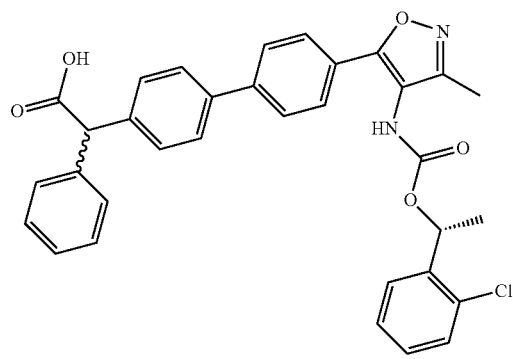

Compound 14

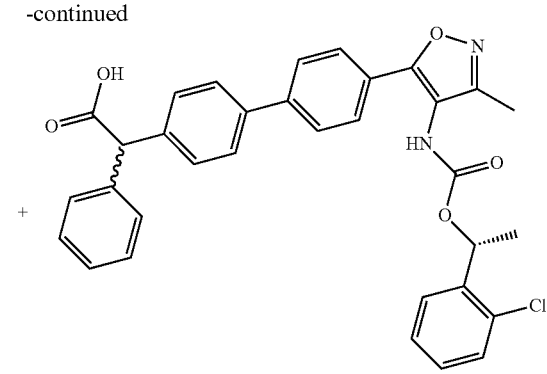

Compound 16

To a stirred solution of IV-1 (20 g, 108.1 mmol) in THF (100 mL) was added dropwise a solution of phenylmagnesium bromide (3 M in THF, 37.8 mL, 113.4 mmol) at 0° C. under nitrogen. After the addition, the solution was warmed slowly to the room temperature and stirred for 0.5 hour. The solution was quenched with 100 mL $H_2O$. The aqueous layer was separated and extracted with EtOAc (100 mL×3). The organic layer was combined and washed with brine, dried over $Na_2SO_4$, concentrated in vacuo. The residue was purified by column chromatography on silica gel (Petroleum ether:EtOAc=10:1) to afford compound IV-2 (19 g, yield 67%).

To a stirred solution of IV-2 (7.0 g, 26.7 mmol) in DCM (70 mL) was added dropwise $SOCl_2$ (3.82 g, 32.06 mmol) at 0° C. under nitrogen. After addition, the solution was stirred for 1 hour at 0° C., and then warmed slowly to room temperature, continued stiffing for 1 hour. Water (50 mL) was added, and the mixture was extracted with DCM (50 mL×2). The organic layer was combined and washed with brine, dried over $Na_2SO_4$, concentrated in vacuo. The residue was purified by column chromatography on silica gel (Petroleum ether:EtOAc=100:1) to provide compound IV-3 (5.6 g, yield 75%).

Titanium tetrachloride (2 mL) was added dropwise to a stirred solution of IV-3 (5.60 g, 19.89 mmol) and trimethylsilyl cyanide (1.97 g, 19.85 mmol) in DCM (60 mL) at 0° C. under nitrogen. The reaction mixture was stirred at 0° C. for 2 hours. The solution was quenched with 40 mL of $H_2O$, and extracted with EtOAc (50 mL×2). The organic layer was combined and washed with brine, dried over $Na_2SO_4$, and concentrated under reduced pressure. The residue was purified by column chromatography on silica gel (Petroleum ether:EtOAc=50:1) to afford compound IV-4 (4.46 g, yield 82%).

To a stirred solution of IV-4 (4.46 g, 16.39 mmol) in water (37 mL) was added dropwise conc. $H_2SO_4$ (37 mL) at 0° C. under nitrogen. After the addition, the solution was refluxed overnight. After cooled to rt, the mixture was diluted with water (30 mL), and extracted with $CHCl_3$ (50 mL×3). The combined organic layer was washed with brine, dried over $Na_2SO_4$, and concentrated under reduced pressure to afford compound IV-5 (4.7 g, yield 98%).

To a solution of compound IV-5 (4.7 g, 16.15 mmol) in methanol (50 mL) was added conc. $H_2SO_4$ (2 mL) dropwise at 0° C. After addition, the resulting mixture was refluxed for 4 hours. After being cooled to rt, the mixture was diluted with water (30 mL) and extracted with EtOAc (50 mL×3). The combined organic layer was washed with brine, dried over $Na_2SO_4$ and concentrated under reduced pressure to provide compound IV-6 (4.7 g, yield 95%).

A flask was charged with compound IV-6 (4.70 g, 15.41 mmol), bis(pinacolato)diboron (7.8 g, 30.71 mmol), KOAc (3.00 g, 30.71 mmol) and 100 mL of dioxane. The flask was purged with nitrogen three times, and then $Pd(dppf)Cl_2$ (563 mg, 0.77 mmol) was added thereto. The reaction mixture was stirred at reflux for 4 hours under nitrogen atmosphere. After cooled to rt, the solvent was removed under reduced pressure, the residue was diluted with water (50 mL), and the aqueous phase was extracted with DCM (50 mL×3). The combined organic layer was washed with brine, dried over $Na_2SO_4$, and concentrated. The residue was purified by column chromatography on silica gel (Petroleum ether:EtOAc=50:1) to yield compound IV-7 (5.0 g, yield 75%).

A flask was charged with compound IV-7 (2 g, 4.59 mmol), 1-5 (1.78 g, 5.06 mmol), $Na_2CO_3$ (1.46 g, 13.77 mmol) and 40 mL of $DME:H_2O$ (v/v=3:1). The flask was purged with nitrogen three times, and then $Pd(dppf)Cl_2$ (168 mg, 0.23 mmol) was added thereto. The reaction mixture was stirred at reflux for 2 hours under nitrogen atmosphere. After cooled to rt, the solvent was removed under reduced pressure, the residue was diluted with water (50 mL), the aqueous phase was extracted with DCM (50 mL×3). The combined organic layer was washed with brine, dried over $Na_2SO_4$, and concentrated in vacuo. The residue was purified by column chromatography on silica gel (Petroleum ether:EtOAc=4:1) to afford compound IV-8 (0.95 g, yield 36%). MS (ESI) m/z (M+H)$^+$ 581.2.

Preparation of Compound 14

To a stirred solution of compound IV-8 (0.95 g, 1.64 mmol) in 10 mL of $MeOH/H_2O$ (v/v=5:1) was added lithium hydroxide monohydrate (0.08 g, 1.9 mmol) under nitrogen. After the addition, the solution was heated to reflux for 1 hour. MeOH was removed under reduced pressure, and the residue was adjusted to pH=2 with aq. HCl (1 N). The aqueous phase was extracted with DCM (20 mL×3). The combined organic layer was washed with brine, dried over $Na_2SO_4$, and concentrated. The residue was purified by Prep-HPLC to give IV-Mixture (0.2 g, yield 16%). MS (ESI) m/z (M+H)$^+$ 567.1.

Separation of the Stereoisomers of IV-Mixture 0.2 g of IV-Mixture was separated by SFC to afford the two diastereomers Compound 14 (50 mg) and Compound 16 (132 mg). Compound 14: $^1$H NMR (DMSO-$d_6$, 300 MHz): δ 9.40 (s, 1H), 7.64-7.77 (m, 7H), 7.23-7.45 (m, 10H), 5.96 (q, 1H), 5.11 (s, 1H), 2.09 (s, 3H), 1.52 (d, J=5.7 Hz, 3H). MS (ESI) m/z (M+H)$^+$ 567.1. Compound 16: $^1$H NMR (DMSO-$d_6$, 300 MHz): δ 12.80 (s, 1H), 9.42 (s, 1H), 7.67-7.81 (m, 7H), 7.25-7.47 (m, 10H), 5.98 (q, 1H), 5.14 (s, 1H), 2.11 (s, 3H), 1.53 (d, J=4.5 Hz, 3H). MS (ESI) m/z (M+H)$^+$ 567.1.

Synthesis of Compound 20 R-Isomer

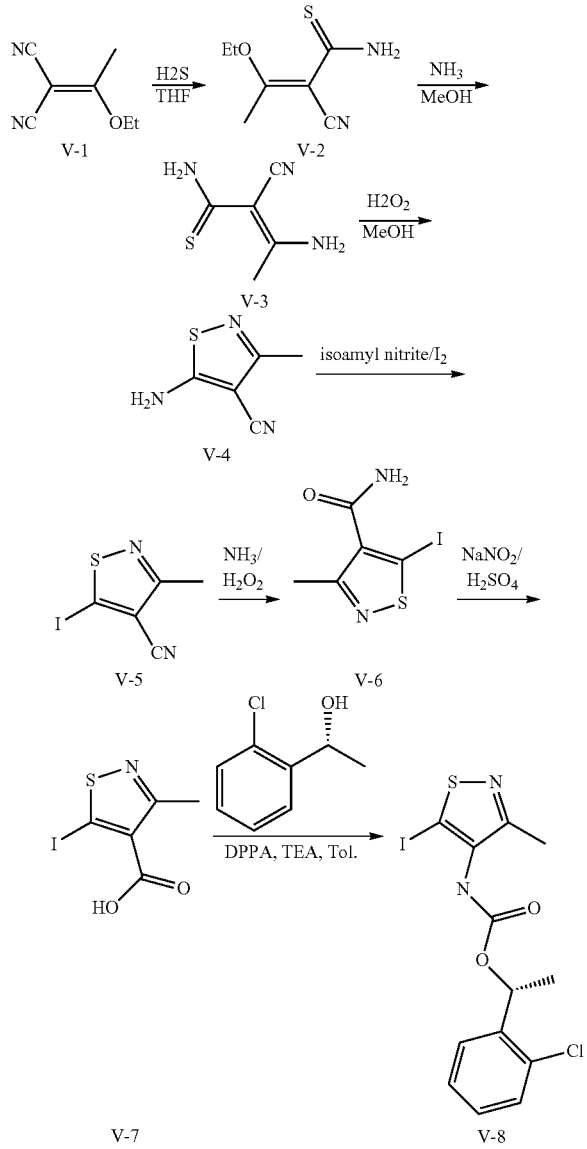

Synthetic Route (Scheme V-A)

H2S gas was bubbled to a stirred solution of compound V-1 (50.0 g, 360 mmol) and TEA (0.85 mL) in THF (1000 mL) at 0° C. The mixture was stirred for 0.5 hour, and the precipitated solid was collected by filtration to afford compound V-2 (30 g, yield 59%).

A stirred solution of V-2 (30 g, 210 mmol) in a saturated solution of ammonia in methanol (500 mL) was stirred at rt overnight. MeOH was removed under reduced pressure, the aqueous layer was stood overnight, and the precipitate was collected to provide compound V-3 (24 g, yield 80%).

To a stirred solution of V-3 (2.05 g, 14.53 mmol) in methanol (90 mL) was added dropwise hydrogen peroxide (30%, 4.08 mL) at 0° C. After addition, the solution was refluxed for 4 hours. The mixture was concentrated, and about 30 mL of solvent was remained. The residue was cooled in an ice-bath. The crystallized product was filtered off and dried in vacuo to give compound V-4 (1 g, yield 51%). MS (ESI) m/z (M+H)+ 140.

To a stirred solution of iodine (5.48 g, 21.57 mmol) and isoamyl nitrite (3.36 g, 28.71 mmol) in nitromethane (10 mL) was added compound V-4 (1.0 g, 7.19 mmol), and then the mixture was stirred at 110° C. for 4 hours. The solution was quenched with 10 mL $H_2O$ and extracted with EtOAc (30 mL×3). The organic layer was combined and washed with brine, dried over $Na_2SO_4$, and concentrated in vacuo. The residue was purified by column chromatography on silica gel (Petroleum ether:EtOAc=10:1) to give compound V-5 (0.84 g, yield 47%).

To a stirred solution of compound V-5 (0.84 g, 3.36 mmol) in 30% aqueous $NH_4OH$ (10 mL) was added dropwise hydrogen peroxide (30%, 16.8 mL) at 0° C., and then the mixture was stirred at reflux for 4 hours. Then the mixture was concentrated, till about 10 mL of solvent remained. The residue was cooled in an ice-bath, and the crystallized product was filtered off and dried in vacuo to afford compound V-6 (0.5 g, yield 56%).

$NaNO_2$ (1.28 g, 18.55 mmol) was added to a solution of compound V-6 (0.5 g, 1.86 mmol) in conc. $H_2SO_4$ (10 mL). And the mixture was stirred at rt for 4 hours. The solution was diluted with 50 mL of chloroform. The aqueous layer was separated and extracted with chloroform (20 mL×3). The organic layer was combined and washed with brine, dried over $Na_2SO_4$, and concentrated in vacuo to give compound V-7 (0.45 g, yield 89%).

A mixture of compound V-7 (0.45 g, 1.67 mmol), (R)-1-(2-chloro-phenyl)-ethanol (0.31 g, 2.00 mmol), DPPA (0.55 g, 2.00 mmol) and TEA (338 mg, 3.34 mmol) in toluene (10 mL) was heated to reflux under nitrogen for 1 hour. After concentration, the residue was diluted with water (50 mL), the aqueous phase was extracted with DCM (50 mL×3). The combined organic layer was washed with brine, dried over $Na_2SO_4$, and concentrated. The residue was purified by column chromatography on silica gel (Petroleum ether: EtOAc=10:1) to give compound V-8 (0.54 g, yield 88%). MS (ESI) m/z (M+H)+ 422.3.

Synthetic Route (Scheme V-B)

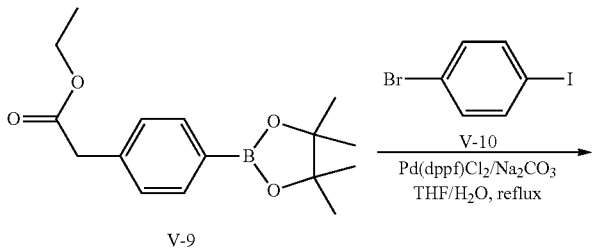

-continued

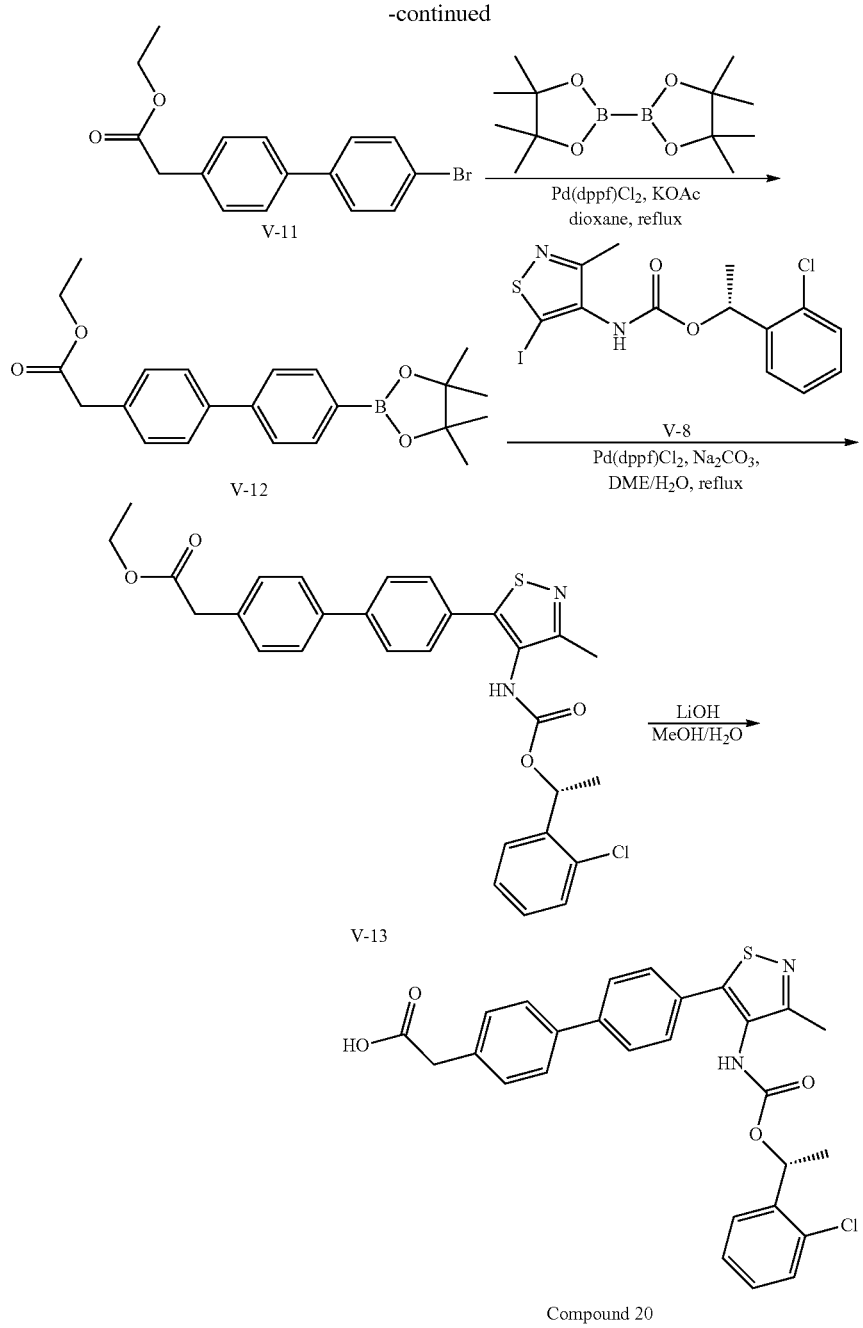

Compound 20

A flask was charged with compound V-9 (4 g, 13.80 mmol), compound V-10 (3.90 g, 13.80 mmol), Na₂CO₃ (2.92 g, 27.54 mmol) and 80 mL of THF/H₂O (v/v=5:1). The flask was purged with nitrogen three times, and then Pd(dppf)Cl₂ (504 mg, 0.68 mmol) was added thereto. The reaction mixture was stirred at reflux overnight under nitrogen atmosphere. After being cooled to rt, the mixture was concentrated to give a residue, and it was diluted with water (50 mL), the aqueous phase was extracted with DCM (50 mL×3). The combined organic layer was washed with brine, dried over Na₂SO₄, and concentrated. The residue was purified by column chromatography on silica gel (Petroleum ether:EtOAc=100:1) to afford compound V-11 (1.80 g, yield 42%).

A flask was charged with compound V-11 (1.80 g, 5.64 mmol), bis(pinacolato)diboron (2.87 g, 11.30 mmol), KOAc (1.11 g, 11.33 mmol) and 50 mL of dioxane. The flask was purged with nitrogen three times, and then Pd(dppf)Cl₂ (206 mg, 0.28 mmol) was added thereto. The reaction mixture was heated to reflux for 4 hours under nitrogen atmosphere. After being cooled to rt, the mixture was concentrated to give a residue, and it was diluted with water (50 mL), the aqueous phase was extracted with DCM (50 mL×3). The combined organic layer was washed with brine, dried over Na₂SO₄, and concentrated. The residue was purified by column chromatography on silica gel (Petroleum ether:EtOAc=100:1) to give compound V-12 (1.70 g, yield 82%).

The mixture of compound V-8 (0.55 g, 1.30 mmol), compound V-12 (0.48 g, 1.30 mmol), Na₂CO₃ (0.28 g, 2.60 mmol) and Pd(dppf)Cl₂ (50 mg, 0.07 mmol) in 15 mL of DME:H₂O (v/v=3:1) was heated to reflux for 2 hours under nitrogen atmosphere. After being cooled to rt, the mixture was concentrated to give a residue, and it was diluted with water (50 mL), the aqueous phase was extracted with DCM (50 mL×3). The combined organic layer was washed with brine, dried over $Na_2SO_4$, and concentrated. The residue was purified by column chromatography on silica gel (Petroleum ether:EtOAc=3:1) to provide compound V-13 (0.42 g, yield 36%). MS (ESI) m/z $(M+H)^+$ 534.

Preparation of Compound 20

To a solution of compound V-13 (0.42 g, 0.78 mmol) in 10 mL of $MeOH:H_2O$ (v/v=5:1) was added lithium hydroxide monohydrate (42 mg, 1 mmol). The mixture was stirred at reflux for 1 hour. MeOH was removed under reduced pressure, and the residue was adjusted with aq. HCl (2 N) to pH=2. The aqueous phase was extracted with DCM (20 mL×3). The combined organic layer was washed with brine, dried over $Na_2SO_4$, and concentrated. The residue was purified by Prep-HPLC to afford Compound 20 (R) Isomer (0.04 g, yield 10%). $^1$H NMR ($CD_3OD$, 400 MHz): δ 7.55-7.68 (m, 8H), 7.25-7.41 (m, 5H), 6.10-6.12 (m, 1H), 3.67 (s, 2H), 2.33 (s, 3H), 1.55 (d, J=6.4 Hz, 3H). MS (ESI) m/z $(M+H)^+$ 507.0.

Synthesis of Compound 21

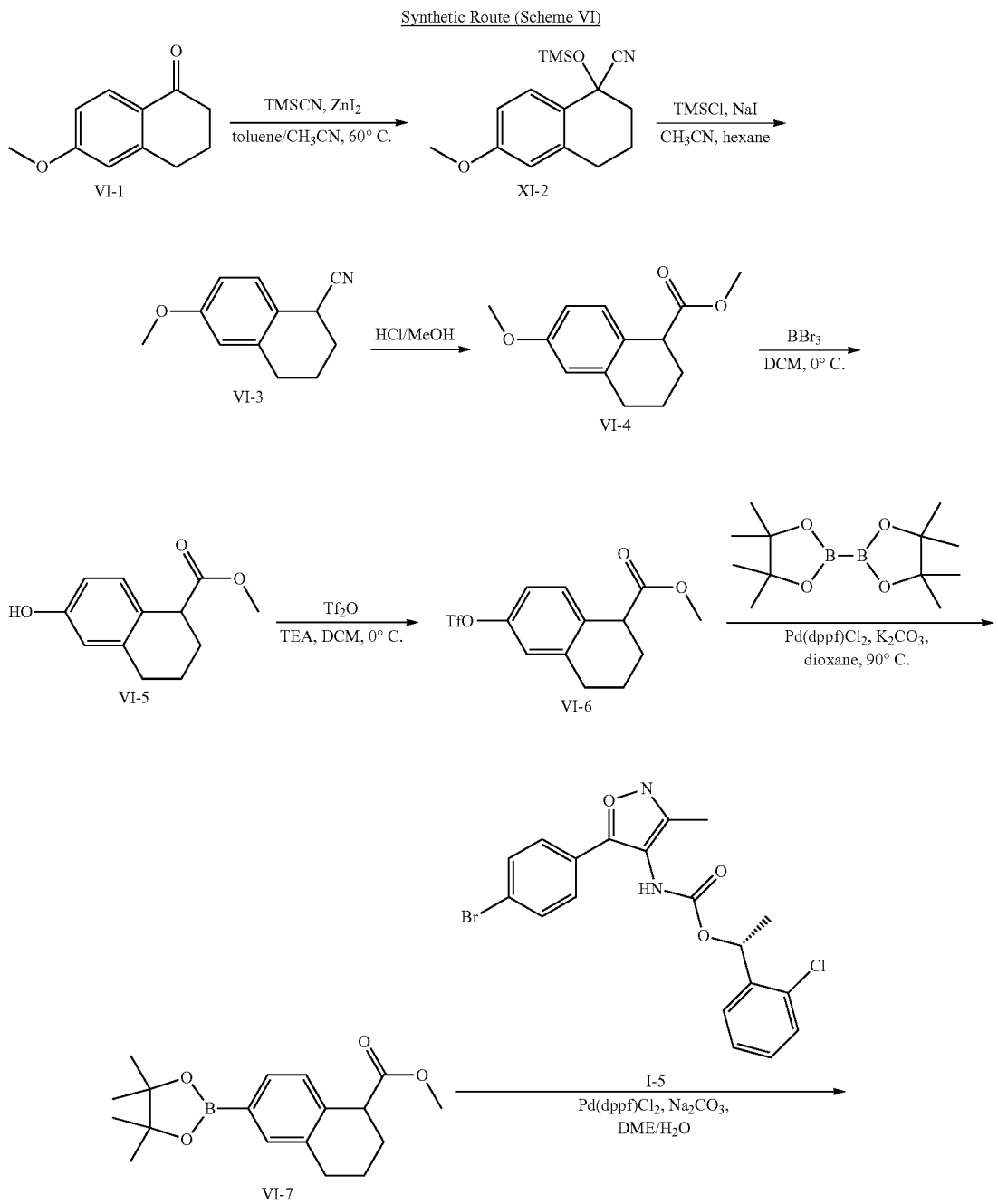

-continued

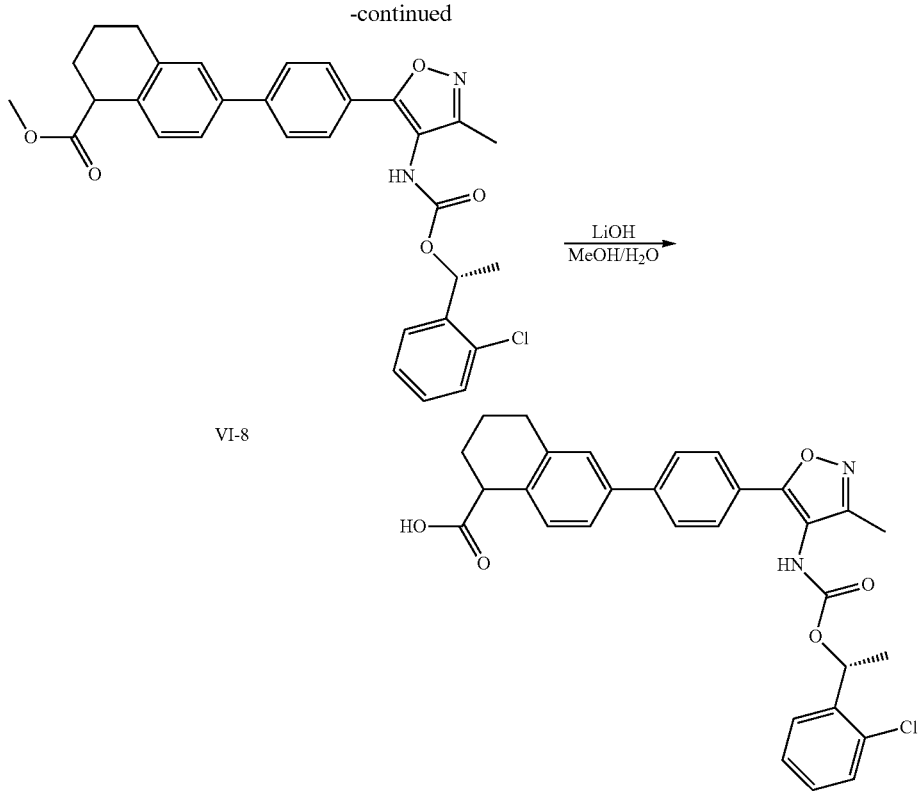

VI-8

Compound 21

To a stirred mixture of compound VI-1 (10 g, 57 mmol) and $ZnI_2$ (0.2 g) in toluene/$CH_3CN$ (v/v=3:1, 100 mL) was added TMSCN (7.3 g, 73.8 mmol). The mixture was stirred at 60° C. for 5 hrs. Then the mixture was diluted with EtOAc (100 mL), the organic layer was separated, washed with water and brine, dried over $Na_2SO_4$ and concentrated. The residue was purified by column chromatography on silica gel to give product VI-2 (8.8 g, yield 56%). MS (ESI) m/z (M+H)$^+$ 276.1.

A mixture of TMSCl (19.5 g, 180 mmol) and NaI (27 g, 180 mmol) in $CH_3CN$ (7.4 g, 180 mmol) was stirred at rt for 20 min., then a solution of compound VI-2 (8.25 g, 30 mmol) in hexane (150 mL) was added, the reaction mixture was stirred at rt for 1 h. Then the mixture was diluted with EtOAc (150 mL), the organic layer was separated, washed with water and brine, dried over $Na_2SO_4$, filtered and concentrated. The residue was purified by column chromatography on silica gel (Petroleum ether:EtOAc=40:1) to give compound VI-3 (3.5 g, yield 62%). $^1$H NMR (DMSO-$d_6$, 300 MHz): δ 7.19 (d, J=8.4 Hz, 1H), 6.76-6.80 (m, 1H), 6.69 (d, J=2.7 Hz, 1H), 4.22 (t, J=6.0 Hz, 1H), 3.70 (s, 3H), 2.64-2.78 (m, 2H), 1.94-2.02 (m, 2H), 1.72-1.82 (m, 2H).

A solution of compound VI-3 (3.5 g, 18.7 mmol) in HCl/MeOH (4N, 50 mL) was refluxed for 48 hrs. The mixture was concentrated in vacuo to remove MeOH, and the resulting residue was re-dissolved with EtOAc (100 mL), the organic layer was washed with saturated aq. $Na_2CO_3$, dried over $Na_2SO_4$, and concentrated. The residue was purified by column chromatography on silica gel (Petroleum ether:EtOAc=50:1) to give product VI-4 (1.2 g, yield 29%). $^1$H NMR (CDCl$_3$, 300 MHz): δ 7.07 (d, J=8.4 Hz, 1H), 6.61-6.70 (m, 2H), 3.76-3.78 (m, 4H), 3.69 (s, 3H), 2.66-2.86 (m, 2H), 1.67-2.17 (m, 4H).

$BBr_3$ (27.5 g, 11 mmol) was added to a stirred solution of compound VI-4 (1.2 g, 5.5 mmol) in DCM (10 mL) at 0° C., the reaction mixture was stirred at 0° C. for 30 min. The mixture was poured onto ice, and extracted with DCM (50 mL×3). The combined organic layer was washed with brine, dried over $Na_2SO_4$ and concentrated to afford compound VI-5 (0.4 g, yield 36%).

To a solution of compound VI-5 (400 mg, 1.96 mmol) and TEA (594 mg, 5.88 mmol) in DCM (10 mL) was added trifluoromethanesulfonic anhydride (1.1 g, 3.92 mmol) at 0° C. The reaction mixture was stirred at 0° C. for 30 min. The mixture was poured onto ice, and extracted with DCM (50 mL×3), combined the organic layer, washed with brine, dried over $Na_2SO_4$ and concentrated to get product VI-6 (0.35 g, yield 53%).

A flask was charged with compound VI-6 (900 mg, 2.66 mmol), bis(pinacolato)diboron (1.01 g, 3.99 mmol), $K_2CO_3$ (730 mg, 5.32 mmol) and 1,4-dioxane (10 ml). The flask was purged with nitrogen three times, and then Pd(dppf)Cl$_2$ (100 mg) was added thereto. The reaction mixture was stirred at 90° C. for 12 hrs under nitrogen atmosphere. After being cooled to rt, the mixture was diluted with EtOAc (100 mL), washed with water and brine, dried over $Na_2SO_4$, filtered, and concentrated. The residue was purified by prep-TLC (Petroleum ether:EtOAc=10:1) to give product VI-7 (500 mg, yield 59%).

A flask was charged with compound VI-7 (500 mg, 1.58 mmol), 1-5 (690 mg, 1.58 mmol), $Na_2CO_3$ (335 mg, 3.16 mmol) and 1,4-dioxane/$H_2O$ (10 mL/2 mL). The flask was purged with nitrogen three times, and then Pd(dppf)Cl$_2$ (50 mg) was added thereto. The reaction mixture was stirred at 80° C. for 3 hrs. After being cooled to rt, the mixture was diluted with EtOAc (100 mL), washed with water and brine, dried over $Na_2SO_4$, filtered, and concentrated. The residue was purified by column chromatography on silica gel (Petroleum ether:EtOAc=20:1-10:1) to give product VI-8 (300 mg, yield 35%). MS (ESI) m/z (M+H)$^+$ 545.1.

Preparation of Compound 21

To a solution of compound VI-8 (300 mg, 0.55 mmol) in MeOH/H$_2$O (v/v=5:1, 6 mL) was added lithium hydroxide monohydrate (46 mg, 1.1 mmol). The mixture was stirred at 60° C. for 1 hr, and then it was concentrated in vacuo to remove MeOH, aq. HCl (2 N) was added to adjust pH~3. The mixture was extracted with DCM (30 mL×3). The combined organic layer was washed with brine, dried over Na$_2$SO$_4$, filtered, and concentrated. The residue was purified by prep-HPLC to give Compound 21 as a mixture of diastereomers (160 mg, yield 55%). $^1$H NMR (CD$_3$OD, 400 MHz): δ 7.65-7.86 (m, 5H), 7.30-7.46 (m, 6H), 6.15-6.21 (m, 1H), 3.85-3.88 (m, 1H), 2.84-2.98 (m, 2H), 2.15-2.30 (m, 4H), 1.98-2.13 (m, 2H), 1.79-1.89 (m, 1H), 1.63 (d, J=6.4 Hz, 3H). MS (ESI) m/z (M+H)$^+$531.1.

Synthesis of Compound 17 sodium sulfate, concentrated in vacuo. The residue was purified by prep-TLC (Petroleum ether:EtOAc=3:1) to afford compound VII-2 (250 mg, yield 66%).

A flask was charged with compound VII-2 (50 mg, 0.14 mmol), compound VII-3 (82.4 mg, 0.28 mmol), Na$_2$CO$_3$ (30 mg, 0.28 mmol), dioxane/H$_2$O (12 mL, v/v=5/1) and Pd(dppf)Cl$_2$ (20 mg, 0.03 mmol). The flask was purged with nitrogen and the mixture was refluxed overnight. After being cooled to rt, the mixture was diluted with water (10 mL), extracted with EtOAc (20 mL×3). The combined organic layer was washed with brine, dried over anhydrous Na$_2$SO$_4$, and concentrated in vacuo. The residue was purified by prep-TLC (Petroleum ether:EtOAc=3:1) to give compound VII-4 (30 mg, yield 48%). $^1$H NMR (CDCl$_3$, 400 MHz): δ 7.88 (d, J=7.2 Hz, 2H), 7.69 (d, J=6.4 Hz, 2H), 7.59 (d, J=6.4 Hz, 2H), 7.39 (d, J=8.4 Hz, 2 H), 5.8 (brs, 1H), 4.18 (q, 2H), 3.67 (s, 2H), 2.30 (s, 3H), 1.51 (brs, 9H), 1.28 (t, J=7.2 Hz, 3H). MS (ESI) m/z (M+H)$^+$ 437.

Synthetic Route (Scheme VII)

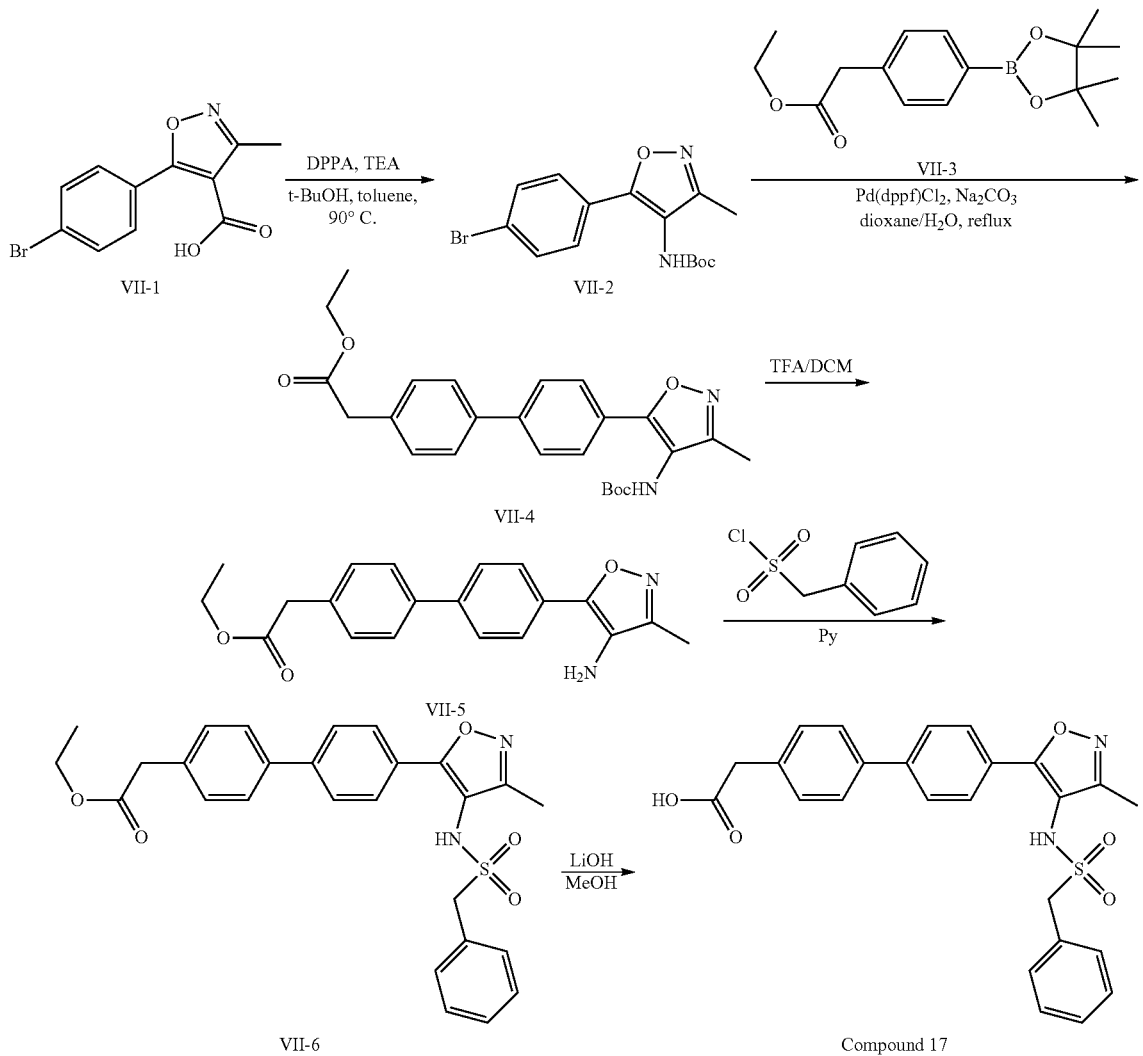

Compound VII-1 (300 mg, 1.02 mmol) was dissolved in 15 mL of toluene. To the resulting solution was added DPPA (353 mg, 1.28 mmol), t-BuOH (95 mg, 1.28 mmol) and Et$_3$N (216 mg, 2.14 mmol), and then the solution was stirred at 90° C. for 3 hrs. After cooling to rt, the mixture was poured into water and extracted with EtOAc (30 mL×3). The combined organic layer was washed with brine, dried over anhydrous To a solution of compound VII-4 (30 mg, 0.068 mmol) in DCM (4 mL) was added TFA (1.0 mL). The mixture was stirred at rt for 4 hrs, and then the solution was concentrated. The resulting residue was diluted with EtOAc (30 mL) and washed with brine, dried over anhydrous Na$_2$SO$_4$ and concentrated in vacuo to give intermediate VII-5 (20 mg, yield 86%) as pale-yellow solid.

Preparation of Intermediate VII-6 (Compound 15)

To a solution of compound VII-5 (35 mg, 0.104 mmol) in pyridine (5 mL) was added phenylmethanesulfonyl chloride (39 mg, 0.208 mmol). The solution was stirred at 50° C. overnight. After cooled to rt, the mixture was diluted with EtOAc (30 mL) and washed with brine, dried over anhydrous $Na_2SO_4$ and concentrated. The residue was purified by prep-TLC (Petroleum ether:EtOAc=2:1) to give VII-6 (12 mg, yield 23%) as pale-yellow solid. $^1H$ NMR (CDCl$_3$, 400 MHz): δ 7.96 (d, J=8.4 Hz, 2H), 7.72 (d, J=8.4 Hz, 2H), 7.59 (d, J=8.0 Hz, 2H), 7.39 (d, J=8.0 Hz, 2H), 7.32 (m, 5H), 5.93 (s, 1H), 4.18 (m, 4H), 3.67 (s, 2H), 2.39 (s, 3H), 1.28 (t, J=7.2 Hz, 3H). MS (ESI) m/z (M+H)$^+$ 491.0.

Preparation of Compound 17

To a solution of VII-6 (6 mg, 0.01 mmol) in MeOH (3 mL) was added lithium hydroxide monohydrate (2.5 mg, 0.06 mmol). The mixture was stirred at rt overnight. The mixture was acidified with aq. HCl (1 N) to pH=3~4, and extracted with EtOAc (10 mL×3). The combined organic layer was washed with brine, dried over anhydrous $Na_2SO_4$, and concentrated in vacuo to give Compound 17 (3.5 mg, yield 62%). $^1H$ NMR (DMSO-d$_6$, 400 MHz): δ 9.65 (brs, 1H), 8.02 (d, J=8.4 Hz, 2H), 7.80 (d, J=8.4 Hz, 2 H), 7.68 (d, J=8.4 Hz, 2 H), 7.35 (m, 7H), 4.38 (s, 2H), 3.62 (s, 2H), 2.24 (s, 3H). MS (ESI) m/z (M+H)$^+$ 462.9.

Synthesis of Compound 19

Synthetic Route (Scheme VIII)

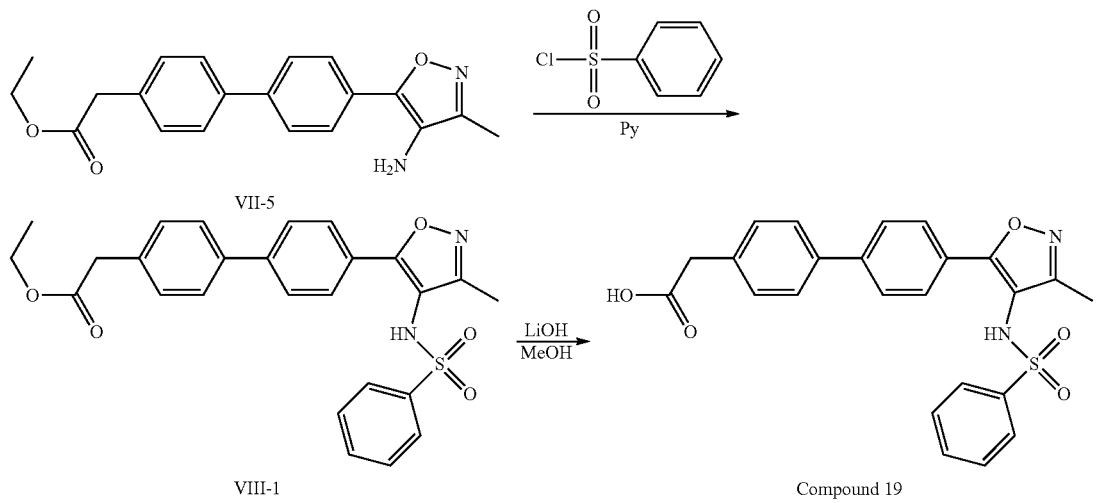

Preparation of Intermediate VIII-1 (Compound 18)

To a solution of compound VII-5 (30 mg, 0.09 mmol) in pyridine (5 mL) was added benzenesulfonyl chloride (31 mg, 0.18 mmol). The solution was stirred at rt for 1 h, and then diluted with EtOAc (30 mL) and washed with brine, dried over anhydrous $Na_2SO_4$ and concentrated. The residue was purified by prep-HPLC to give VIII-1 (14 mg, yield 33%) as white solid. $^1H$ NMR (CDCl$_3$, 400 MHz): δ 7.71 (d, J=7.2 Hz, 2H), 7.64 (d, J=8.4 Hz, 2H), 7.52 (d, J=8.0 Hz, 2H), 7.49-7.39 (m, 5 H), 7.35-7.30 (m, 2H), 6.18 (brs, 1H), 4.20 (q, 2H), 3.68 (s, 2H), 2.09 (s, 3H), 1.29 (t, J=7.2 Hz, 3H). MS (ESI) m/z (M+H)$^+$ 477.1.

Preparation of Compound 19

The preparation of Compound 19 is similar to that of Compound 17. Compound 19 was obtained (6.4 mg, yield 76%) as white solid. $^1H$ NMR (CD$_3$OD, 400 MHz): δ7.69 (m, 4H), 7.61 (d, J=8.0 Hz, 2H), 7.56 (d, J=8.4 Hz, 2H), 7.44 (m, 3 H), 7.38 (m, 2H), 3.69 (s, 2H), 2.08 (s, 3H). MS (ESI) m/z (M+H)$^+$ 449.0.

Synthesis of Compound 22

Synthetic Route (Scheme VIII)

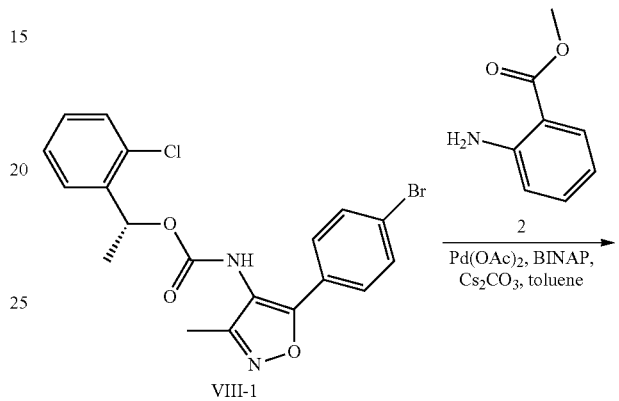

-continued

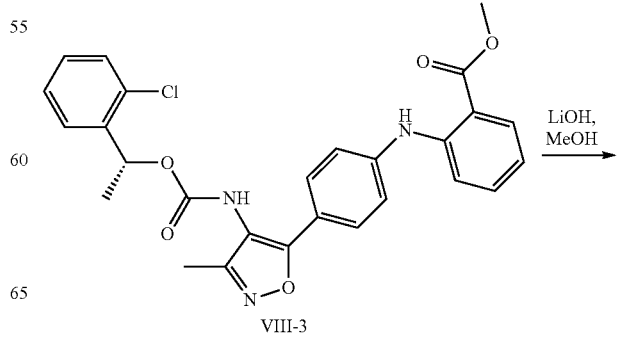

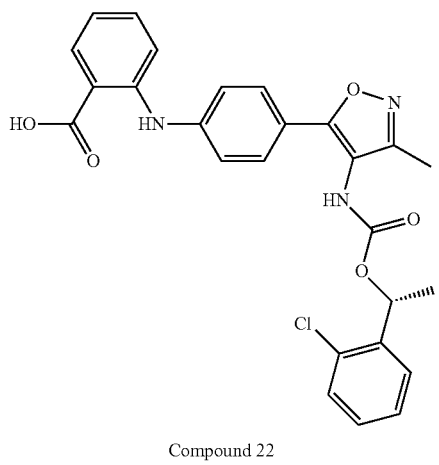

Compound 22

A mixture of compound VIII-1 (2 g, 4.6 mmol), compound VIII-2 (1.4 g, 9.2 mmol), Pd(OAc)$_2$ (20 mg), BINAP (40 mg) and Cs$_2$CO$_3$ (3.2 g, 9.6 mmol) in toluene was stirred at reflux for 12 h under nitrogen protection. The mixture was filtered, and the filtrate was diluted with EA. The organic layer was washed with water and brine, dried over Na$_2$SO$_4$, and concentrated under reduced pressure. The residue was purified by column chromatography on silica gel (PE:EA=10:1) to give product VIII-3 (1.1 g, yield 47.4%). MS (ESI) m/z (M+H)$^+$ 506.

Preparation of Compound 22

A mixture of compound VIII-3 (1 g, 2 mmol) and LiOH.H$_2$O (160 mg, 4 mmol) in MeOH/H$_2$O (v/v=5:1, 12 ml) was stirred at 60° C. for 1 h. The mixture was concentrated in vacuo to remove MeOH, aq. HCl (2 N) was added to adjust pH to 3, and extracted with DCM (40 mL×3). The combined organic layers was washed with brine, dried over Na$_2$SO$_4$, filtered, and concentrated. The residue was purified by prep-HPLC to give Compound 22 (400 mg, yield 42%). $^1$H NMR (DMSO-d$_6$, 400 MHz) δ 9.76 (s, 1H), 9.31 (s, 1H), 7.94 (d, J=8.0 Hz, 1H), 7.58-7.68 (m, 3H), 7.29-7.51 (m, 7H), 6.91 (t, J=8.0 Hz, 1H), 5.95-6.01 (m, 1H), 2.08 (s, 3H), 1.53 (d, J=6.0 Hz, 3H). MS (ESI) m/z (M+H)$^+$ 492.0.

Synthesis of Compound 23 and Compound 24

Synthetic Route (Scheme IX)

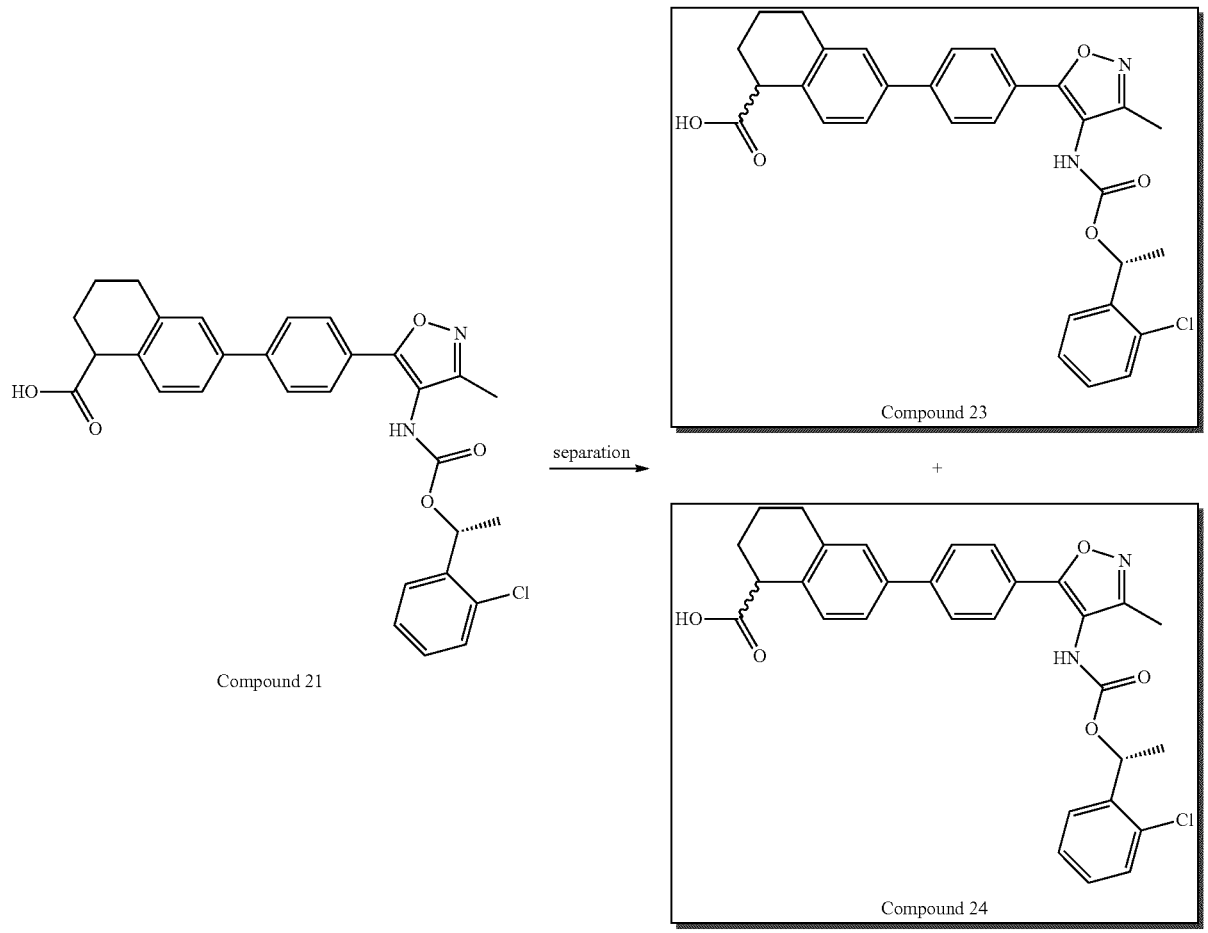

Compound 21 was separated by SFC to afford Compound 23 and Compound 24. Compound 23: ¹H NMR (CD₃OD, 300 MHz): δ 7.82 (d, J=8.4 Hz, 2H), 7.61-7.70 (m, 3H), 7.27-7.42 (m, 6H), 6.10-6.20 (m, 1H), 3.79-3.81 (m, 1H), 2.86-2.90 (m, 2H), 2.08-2.21 (m, 4H), 2.00-2.05 (m, 2H), 1.79-1.84 (m, 1H), 1.63 (d, J=6.3 Hz, 3H) MS (ESI) m/z (M+H)⁺ 531.1.
Compound 24: ¹H NMR (CD₃OD, 300 MHz): δ 7.82 (d, J=8.4 Hz, 2H), 7.61-7.70 (m, 3H), 7.27-7.42 (m, 6H), 6.10-6.20 (m, 1H), 3.79-3.81 (m, 1H), 2.84-2.88 (m, 2H), 2.10-2.18 (m, 4H), 2.02-2.05 (m, 2H), 1.76-1.82 (m, 1H), 1.63 (d, J=6.3 Hz, 3H) MS (ESI) m/z (M+H)⁺ 531.1.
Synthesis of Compounds 26 and 27
Synthetic Route (Scheme X)
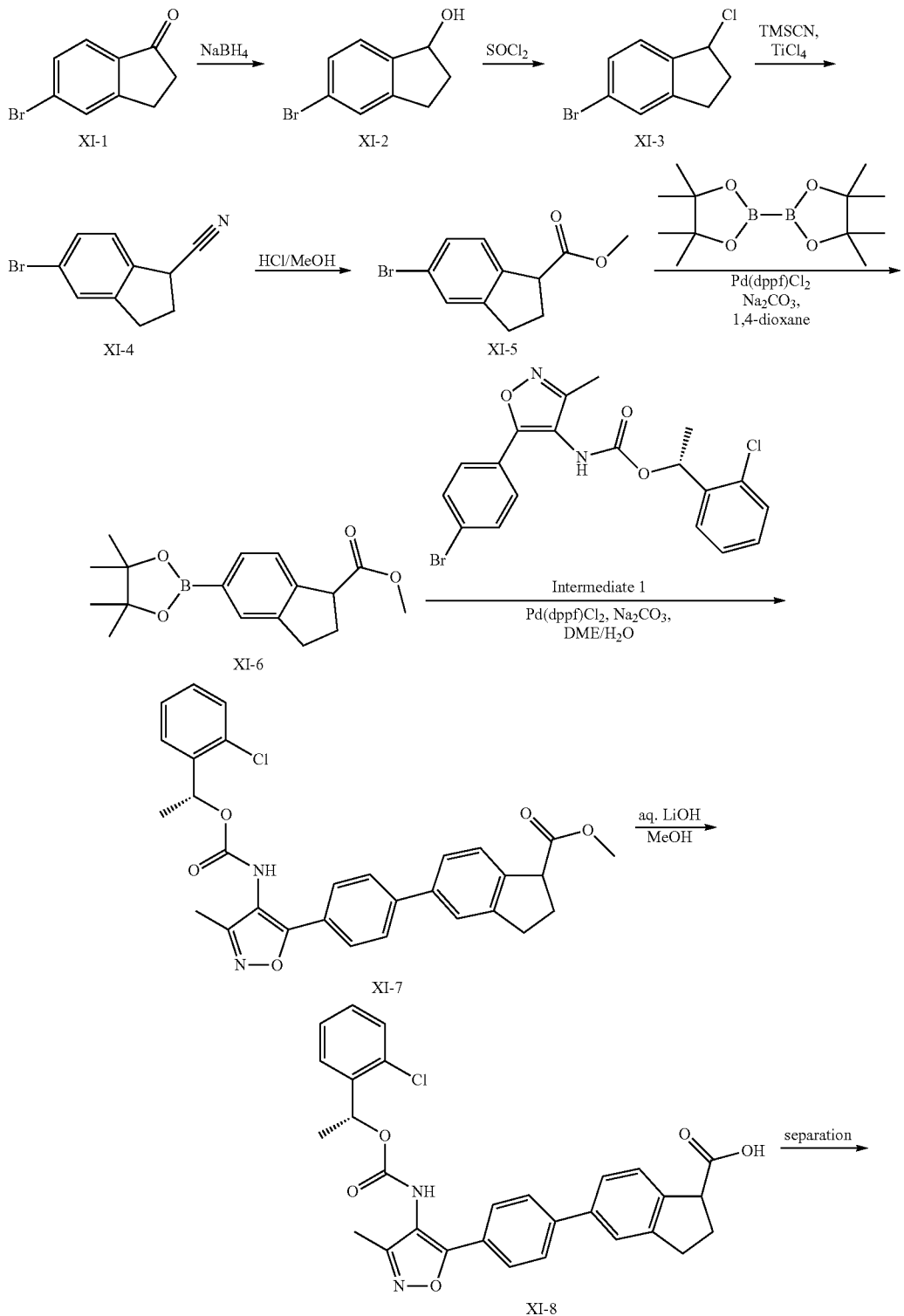

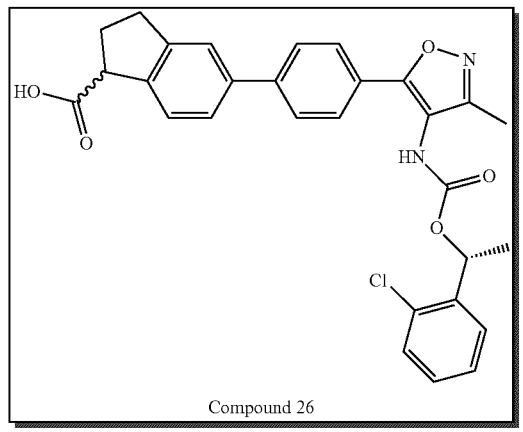

Compound 26

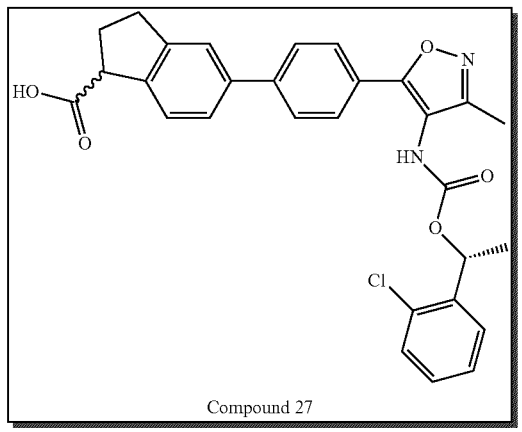

Compound 27

To a stirred solution of compound XI-1 (2.5 g, 11.8 mmol) in THF (30 mL) was added NaBH$_4$ (900 mg, 23.6 mmol), the mixture was stirred at rt. for 30 min. The reaction was quenched with water, and extracted with EtOAc (50 mL×3). The organic layer was separated, dried over Na$_2$SO$_4$, filtered and concentrated to give desired product XI-2 (2.0 g, yield 79%), which was used for next step without further purification.

SOCl$_2$ (5 mL) was added to a stirred solution of compound XI-2 (2.0 g, 9.4 mmol) in dry DCM (20 mL), the mixture was stirred at rt. for 30 min. The mixture was concentrated in vacuo to get crude product XI-3 (2.0 g, yield: 92%), which was used for next step directly.

To a stirred mixture of compound XI-3 (2.0 g, 8.6 mmol) and TMSCN (1.28 g, 12.9 mmol) in dry DCM (20 mL) was added TiCl$_4$ (1 mL), and the reaction mixture was stirred at rt. for 5 h. The reaction was quenched with MeOH, diluted with DCM. The organic layer was separated, washed with water and brine, dried over Na$_2$SO$_4$, filtered, and concentrated. The residue was purified by column chromatography (PE:EA=50:1) to give desired product XI-4 (1.2 g, yield 61%).

A solution of compound XI-4 (1.2 g, 5.4 mmol) in HCl/MeOH (4M, 20 mL) was stirred at reflux for 12 h. The mixture was concentrated under reduced pressure, and the residue was re-dissolved in EA, washed with saturated Na$_2$CO$_3$ solution and brine, then dried over Na$_2$SO$_4$ and concentrated under reduced pressure. The residue was purified by column chromatography on silica gel (PE:EA=50:1) to give product XI-5 (850 mg, yield: 62%).

To a stirred mixture of compound XI-5 (700 mg, 2.77 mmol), bis(pinacolato)diboron (1.05 g, 4.15 mmol) and Na$_2$CO$_3$ (587 mg, 5.54 mmol) in 1,4-dioxane (10 mL) was added Pd(dppf)Cl$_2$ (70 mg) under N$_2$ protection, and the mixture was stirred at 90° C. for 12 hrs. The mixture was diluted with EA (100 mL). The organic layer was separated, washed with water and brine, dried over Na$_2$SO$_4$ and concentrated. The residue was purified by column chromatography on silica gel (PE:EA=70:1) to give product XI-6 (500 mg, yield 60%).

$^1$H NMR (CDCl$_3$, 400 MHz) δ 7.71 (s, 1H), 7.64 (d, J=7.6 Hz, 1H), 7.38 (d, J=7.6 Hz, 1H), 4.07 (t, J=7.2 Hz, 1H), 2.87-3.13 (m, 2H), 2.28-2.48 (m, 2H), 1.34 (s, 12H).

To a stirred mixture of compound XI-6 (500 mg, 1.65 mmol), intermediate XI-1 (720 mg, 1.65 mmol), and Na$_2$CO$_3$ (350 mg, 3.3 mmol) in DME (10 mL) and H$_2$O (2 mL) was added Pd(dppf)Cl$_2$ (70 mg) under N$_2$ protection, and the mixture was stirred at 80° C. for 3 hrs. The mixture was diluted with EA (100 mL), washed with water and brine, dried over Na$_2$SO$_4$, and concentrated. The residue was purified by column chromatography on silica gel (PE:EA=70:1) to give product XI-7 (300 mg, yield 34%). MS (ESI) m/z (M+H)$^+$ 531.

Preparation of Compound 26 and Compound 27

A mixture of compound XI-7 (300 mg, 0.57 mmol) and LiOH (45 mg, 1.1 mmol) in MeOH/H$_2$O (v/v=5:1, 6 mL) was stirred at 60° C. for 1 h. The mixture was concentrated in vacuo to remove MeOH, then aq. HCl (2 N) was added to adjust pH~3. The mixture extracted with DCM (30 mL×3), dried over Na$_2$SO$_4$, filtered and concentrated. The residue was purified by prep-HPLC to give desired product XI-8 (180 mg, yield 62%), which was separated by SFC to afford Compound 26 and Compound 27. Compound 26: $^1$H NMR (CD$_3$OD, 400 MHz): δ 7.83 (d, J=8.0 Hz, 2H), 7.63-7.71 (m, 3H), 7.54 (s, 1H), 7.29-7.50 (m, 5H), 6.13-6.17 (m, 1H), 4.02-4.06 (m, 1H), 2.94-3.19 (m, 2H), 2.36-2.45 (m, 2H), 2.19 (s, 3H), 1.61 (d, J=6.4 Hz, 3H); MS (ESI) m/z (M+H)$^+$ 517.1. Compound 27: $^1$H NMR (CD$_3$OD, 400 MHz): δ 7.86 (d, J=8.0 Hz, 2H), 7.65-7.73 (m, 3H), 7.56 (s, 1H), 7.31-7.50 (m, 5H), 6.16-6.21 (m, 1H), 4.05-4.10 (m, 1H), 2.97-3.21 (m, 2H), 2.39-2.47 (m, 2H), 2.21 (s, 3H), 1.63 (d, J=6.4 Hz, 3H); MS (ESI) m/z (M+H)$^+$ 517.1.

Synthesis of Compound 29
Synthetic Route (Scheme XII)
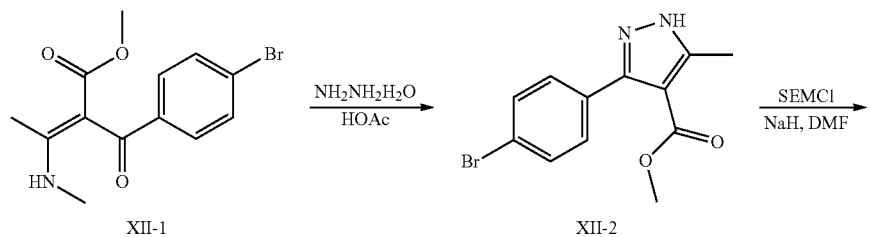
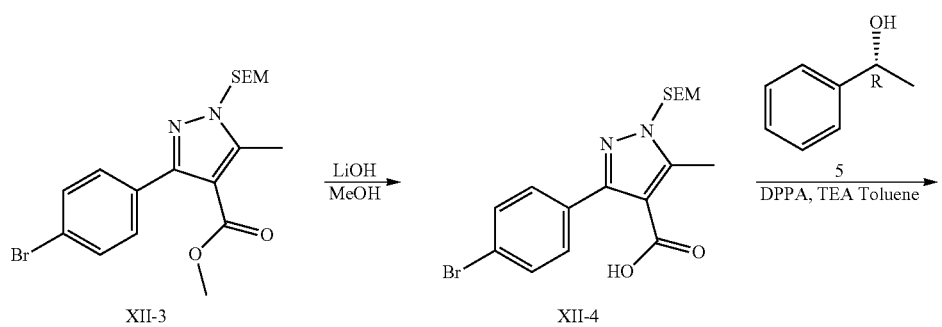
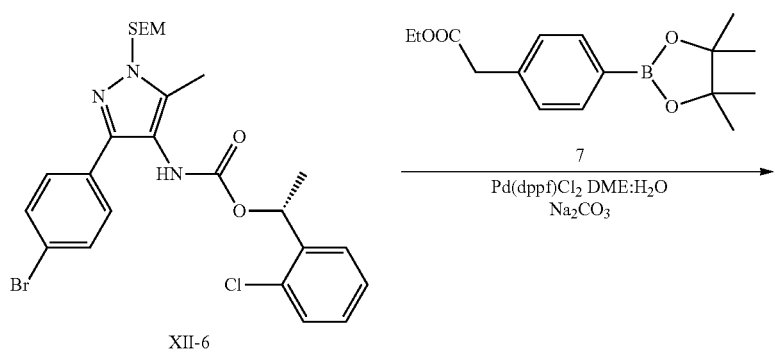
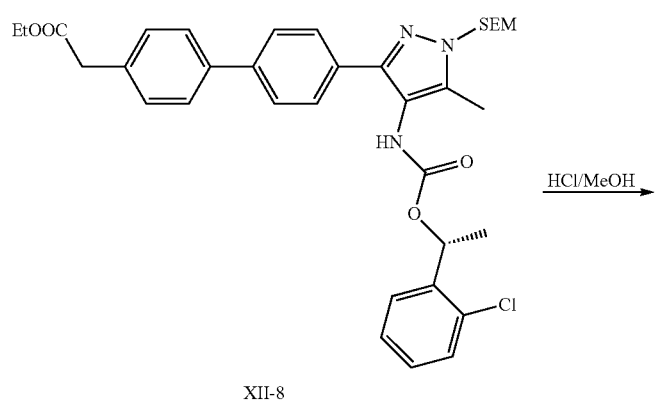

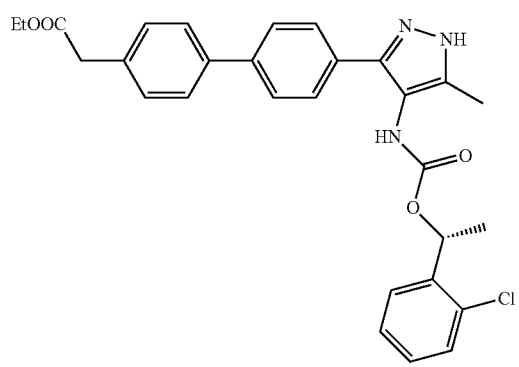

XII-9

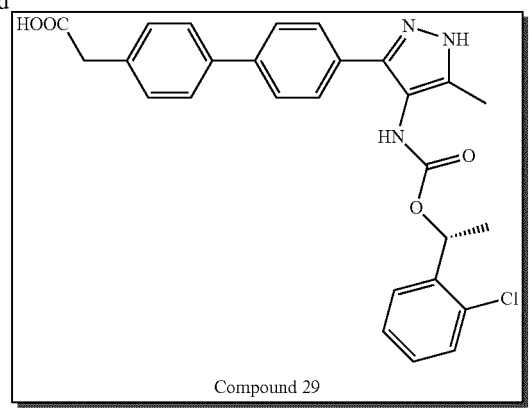

Compound 29

To a stirred solution of XII-1 (5 g, 16 mmol) in HOAc (50 mL) was added hydroxylamine hydrochloride (1.6 g, 32 mmol) under nitrogen protection. After the addition, the solution was heated to reflux under nitrogen for 2 hours. The solution was concentrated under reduced pressure to afford compound XII-2 (3.9 g, yield 82.9%), which was used for next step without further purification.

SEM-Cl (2.92 g, 17.6 mmol) was added dropwise to a stirred solution of XII-2 (4.4 g, 14.96 mmol) and NaH (0.431 g, 17.6 mmol) in DMF (50 mL) at 0° C. After stirred at 0° C. for 30 min., the mixture was quenched with water (20 mL) and extracted with EA (60 mL×3). The combined organic layer were washed with the brine, dried over $Na_2SO_4$, and concentrated in vacuo. The residue was purified by chromatography on silica gel (PE/EA=20/1) to afford compound XII-3 (3.3 g, yield 52%). MS (ESI) m/z $(M+H)^+$ 425.

To a stirred solution of XII-3 (3.3 g, 7.76 mmol) in 55 mL of $MeOH/H_2O$ (v/v=5:1) was added $LiOH.H_2O$ (0.62 g, 14.8 mmol). The solution was heated to reflux for 1 hour.

MeOH was removed in vacuo and the residue was adjusted pH to 3. The aqueous phase was extracted with DCM (50 mL×3). The combined organic layer was washed with brine, dried over $Na_2SO_4$, and concentrated to afford compound XII-4 (2 g, yield 63%). MS (ESI) m/z $(M+H)^+$ 412.

The mixture of compound XII-4 (0.5 g, 1.216 mmol), compound XII-5 (0.178 g, 1.46 mmol), DPPA (0.4 g, 1.46 mmol) and $Et_3N$ (250 mg, 2.4 mmol) in toluene (10 mL) was stirred at reflux under nitrogen for 1 hour. The mixture was concentrated, and the residue was partitioned between $H_2O$ and DCM, the aqueous phase was extracted with DCM (50 mL×3). The combined organic layer was washed with brine, dried over $Na_2SO_4$, and concentrated. The residue was purified by chromatography on silica gel (PE:EA=5:1) to afford compound XII-6 (0.2 g, yield 25%). MS (ESI) m/z $(M+H)^+$ 565.9.

The mixture of compound XII-6 (0.2 g, 0.35 mmol), compound XII-7 (0.12 g, 0.412 mmol), $Na_2CO_3$ (0.38 g, 1.06 mmol) and $Pd(dppf)Cl_2$ (12 mg, 0.0175 mmol) in $DME/H_2O$ (10 mL, v/v=3:1) was heated to reflux under nitrogen for overnight. After concentrated, the residue was partitioned between $H_2O$ and DCM, the aqueous phase was extracted with DCM. The combined organic layer was washed with brine, dried over $Na_2SO_4$, and concentrated. The residue was purified by chromatography on silica gel (PE:EA=5:1) to afford compound XII-8 (90 mg, yield 39%). MS (ESI) m/z $(M+H)^+$ 648.2.

A solution of compound XII-8 (300 mg, 0.436) in methanol (5 mL) was added a solution of HCl in methanol (4 M, 2.5 mL) and the mixture was stirred at rt. overnight. LCMS detected the reaction was completed. The reaction solution was concentrated under reduced pressure to afford compound XII-9 (200 mg, 84%) as a white solid, which was used for next step directly.

Preparation of Compound 29

To a stirred solution of XII-9 (0.2 g, 0.39 mmol) in 10 mL of $MeOH/H_2O$ (v/v=5:1) was added $LiOH.H_2O$ (20 mg, 0.5 mmol). After the addition, the solution was heated to reflux for 1 hour. The solution was concentrated in vacuo and the residue was adjusted to pH=2 with conc. HCl. The aqueous phase was extracted with DCM. The organic layer was washed with brine, dried over $Na_2SO_4$, and concentrated. The residue was purified by prep-HPLC to afford Compound 29 (35 mg, yield 18.5%). $^1H$ NMR ($CD_3OD$, 400 MHz) δ 7.61-7.79 (m, 7H), 7.28-7.42 (m, 5H), 6.12-6.17 (q, 1H), 3.66 (s, 1H), 2.20 (s, 2H), 1.26 (d, J=6.0 Hz, 3H). MS (ESI) m/z $(M+H)^+$ 490.2.

Synthesis of Compound 31

Synthetic Route (Scheme XIII)

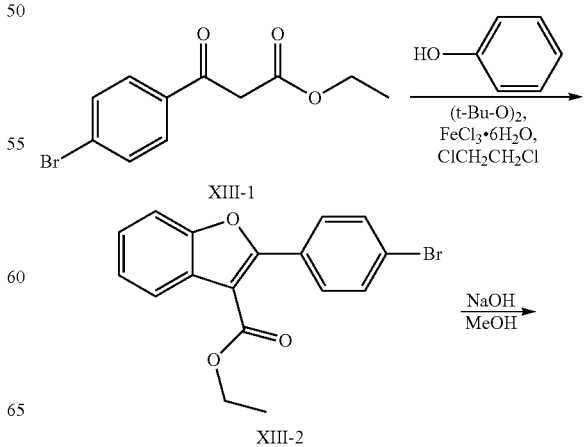

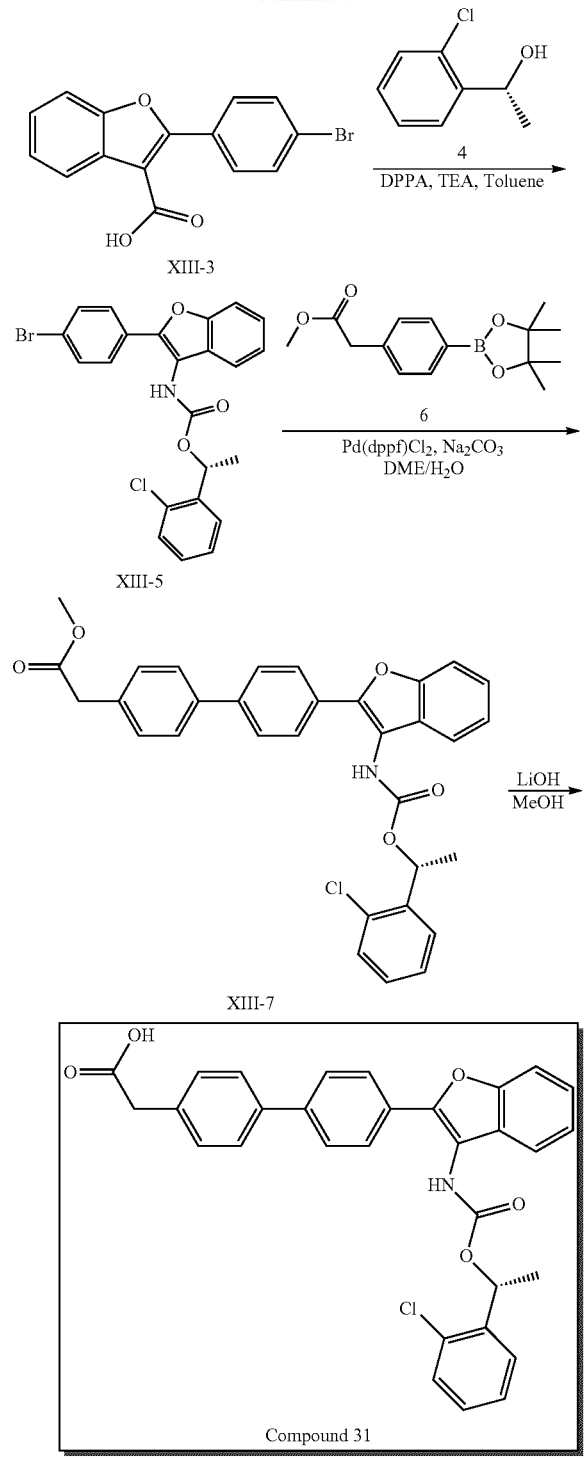

To a stirred solution of compound XIII-2 (2.60 g, 7.54 mmol) in MeOH/H₂O (v/v=5/1, 50 mL) was added NaOH (437 mg, 10.93 mmol) and the resulting mixture was stirred at 60° C. overnight. After concentrated in vacuo, the aqueous layer was adjust pH to 3 with conc. HCl, and extracted with EA. The organic layers were separated, dried, and concentrated to afford compound XIII-3 (1.7 g, yield 71%). MS (ESI) m/z (M+H)⁺ 317.

To a stirred solution of compound XIII-3 (700 mg, 2.21 mmol), compound XIII-4 (413 mg, 2.64 mmol) and DPPA (726 mg, 2.64 mmol) in toluene (15 mL) was added TEA (446 mg, 4.41 mmol) at room temperature under nitrogen. After the addition, the solution was stirred at 100° C. for 1 hour. Then the mixture was quenched with water, and the organic layer was separated, dried, and concentrated. The residue was purified by Prep-HPLC to afford compound XIII-5 (776 mg, yield 75%). MS (ESI) m/z (M+1)⁺470.

The mixture of compound XIII-5 (776 mg, 1.65 mmol), compound XIII-6 (479 g, 1.65 mmol), Na₂CO₃ (350 mg, 3.30 mmol) and Pd (dppf)Cl₂ (60 mg, 0.08 mmol) in DME/H₂O (v/v=4/1, 20 mL) was stirred at 80° C. overnight under nitrogen protection. TLC monitored the reaction. After the reaction was completed, the mixture was poured into water (30 mL), extract with EtOAc (30 mL×3). The combined organic layers were dried over Na₂SO₄, and concentrated in vacuo. The residue was purified by column chromatography on silica gel (PE:EA=4:1) to afford compound XIII-7 (336 mg, yield 37%). MS (ESI) m/z (M+1)⁺ 540.

Preparation of Compound 31

To a stirred solution of compound XIII-7 (336 g, 0.61 mmol) in 20 mL of MeOH/H₂O (v/v=5:1) was added LiOH.H₂O (31 mg, 0.74 mmol). After the addition, the solution was heated to reflux for 1 hour. The solution was concentrated in vacuo and the residue was adjusted to pH=2 with conc. HCl. The aqueous phase was extracted with EA. The organic layer was washed with brine, dried over Na₂SO₄, and concentrated. The residue was purified by prep-HPLC to afford Compound 31 (168 mg, yield 53%). ¹H NMR (DMSO-d₆, 400 MHz): δ 12.41 (s, 1 H), 9.70 (s, 1 H), 7.81-7.95 (m, 2H), 7.53-7.78 (m, 6H), 7.28-7.51 (m, 8H), 6.06 (q, 4 H), 3.65 (s, 2 H), 1.61 (d, J=5.2 Hz, 3 H). MS (ESI) m/z (M+H)⁺ 526.1.

Synthesis of Compound 25

To a stirred solution of compound XIII-1 (7.00 g, 25.83 mmol), phenol (7.28 g, 77.49 mmol) and FeCl₃.6H₂O (698 mg, 0.25 mmol) in DCE (30 mL) was added di-tert-butyl peroxide (7.55 g, 51.66 mmol) at room temperature under nitrogen. After the addition, the solution was stirred for 1 hour at 100° C. Then the mixture was quenched with water, and the organic layer was separated, dried, and concentrated. The residue was purified by Pre-HPLC to afford compound XIII-2 (2.6 g, yield 29%). MS (ESI) m/z (M+1)⁺ 345.

Synthetic Route (Scheme XIV)

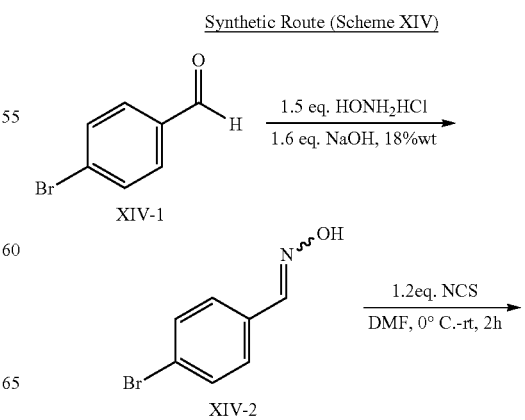

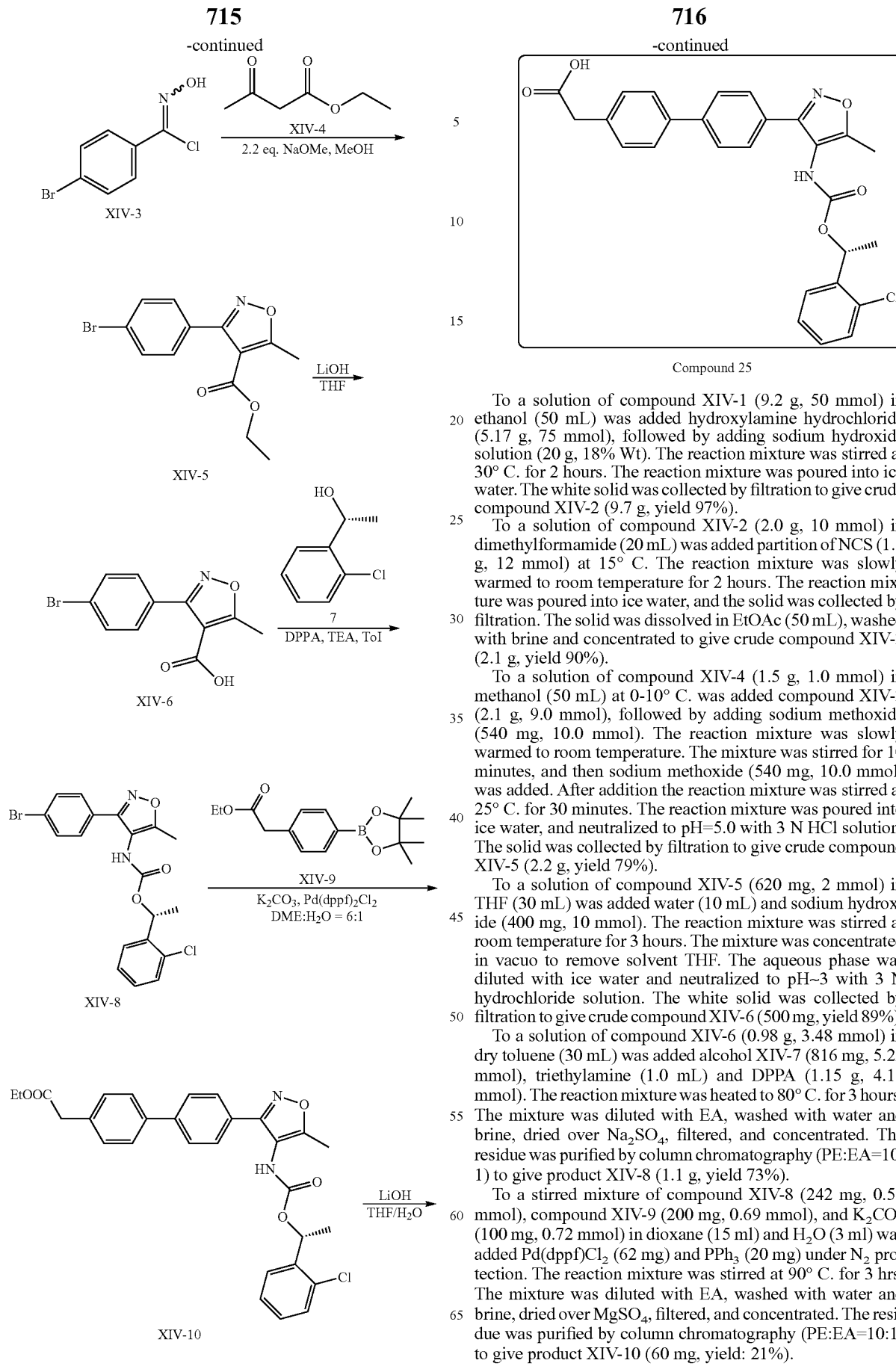

Compound 25

To a solution of compound XIV-1 (9.2 g, 50 mmol) in ethanol (50 mL) was added hydroxylamine hydrochloride (5.17 g, 75 mmol), followed by adding sodium hydroxide solution (20 g, 18% Wt). The reaction mixture was stirred at 30° C. for 2 hours. The reaction mixture was poured into ice water. The white solid was collected by filtration to give crude compound XIV-2 (9.7 g, yield 97%).

To a solution of compound XIV-2 (2.0 g, 10 mmol) in dimethylformamide (20 mL) was added partition of NCS (1.6 g, 12 mmol) at 15° C. The reaction mixture was slowly warmed to room temperature for 2 hours. The reaction mixture was poured into ice water, and the solid was collected by filtration. The solid was dissolved in EtOAc (50 mL), washed with brine and concentrated to give crude compound XIV-3 (2.1 g, yield 90%).

To a solution of compound XIV-4 (1.5 g, 1.0 mmol) in methanol (50 mL) at 0-10° C. was added compound XIV-3 (2.1 g, 9.0 mmol), followed by adding sodium methoxide (540 mg, 10.0 mmol). The reaction mixture was slowly warmed to room temperature. The mixture was stirred for 10 minutes, and then sodium methoxide (540 mg, 10.0 mmol) was added. After addition the reaction mixture was stirred at 25° C. for 30 minutes. The reaction mixture was poured into ice water, and neutralized to pH=5.0 with 3 N HCl solution. The solid was collected by filtration to give crude compound XIV-5 (2.2 g, yield 79%).

To a solution of compound XIV-5 (620 mg, 2 mmol) in THF (30 mL) was added water (10 mL) and sodium hydroxide (400 mg, 10 mmol). The reaction mixture was stirred at room temperature for 3 hours. The mixture was concentrated in vacuo to remove solvent THF. The aqueous phase was diluted with ice water and neutralized to pH~3 with 3 N hydrochloride solution. The white solid was collected by filtration to give crude compound XIV-6 (500 mg, yield 89%).

To a solution of compound XIV-6 (0.98 g, 3.48 mmol) in dry toluene (30 mL) was added alcohol XIV-7 (816 mg, 5.22 mmol), triethylamine (1.0 mL) and DPPA (1.15 g, 4.18 mmol). The reaction mixture was heated to 80° C. for 3 hours. The mixture was diluted with EA, washed with water and brine, dried over $Na_2SO_4$, filtered, and concentrated. The residue was purified by column chromatography (PE:EA=10:1) to give product XIV-8 (1.1 g, yield 73%).

To a stirred mixture of compound XIV-8 (242 mg, 0.55 mmol), compound XIV-9 (200 mg, 0.69 mmol), and $K_2CO_3$ (100 mg, 0.72 mmol) in dioxane (15 ml) and $H_2O$ (3 ml) was added $Pd(dppf)Cl_2$ (62 mg) and $PPh_3$ (20 mg) under $N_2$ protection. The reaction mixture was stirred at 90° C. for 3 hrs. The mixture was diluted with EA, washed with water and brine, dried over $MgSO_4$, filtered, and concentrated. The residue was purified by column chromatography (PE:EA=10:1) to give product XIV-10 (60 mg, yield: 21%).

Preparation of Compound 25

To a solution of compound XIV-10 (90 mg, 0.17 mmol) in THF (30 mL) was added water (10 mL) and LiOH.H$_2$O (150 mg, 3.57 mmol). The reaction mixture was stirred at room temperature overnight. The mixture was cooled down to 0° C. and neutralized to pH~6 with aq. HCl (3 N). The mixture was concentrated in vacuo to remove solvent THF, the residue was freeze-dried and purified by prep-HPLC to give Compound 25 (40 mg, yield 47%). $^1$HNMR (DMSO-d$_6$, 400 MHz) δ 9.20 (s, 1H), 7.73-7.36 (m, 12H), 5.95 (s, 1H), 3.62 (s, 2H), 2.30 (s, 3H), 1.51 (s, 3H). MS (ESI) m/z (M+H)$^+$ 491.2.

Synthesis of Compound 28 toluene (280 mL) at room temperature. TBAB (4.03 g, 10.3 mmol) and 1,2-dibromoethane (23.14 g, 123.08 mmol) were added and the solution was heated to 65° C. overnight. Reaction was monitored by TLC. The organic layer was washed 2 times with dilute hydrochloric acid, dried and evaporated to yield compound XV-2 (8 g, yield 35%).

A mixture of compound XV-2 (7.5 g, 33.78 mmol), KOH (7.6 g, 135 mmol) and ethylene glycol (50 mL) were heated to 160° C. for 6 hrs. The mixture was cooled to room temperature, water (200 mL) was added and the mixture was acidified to pH=3~4 with aq. HCl (2 N) to precipitate the product. The product was collected by filtration to yield compound XV-3 (5.6 g, yield 69%). MS (ESI) m/z (M+H)$^+$ 240.

To a solution of compound XV-3 (7 g, 29 mmol) in methanol (80 mL) was added dropwise sulfuric acid (30 mL). After

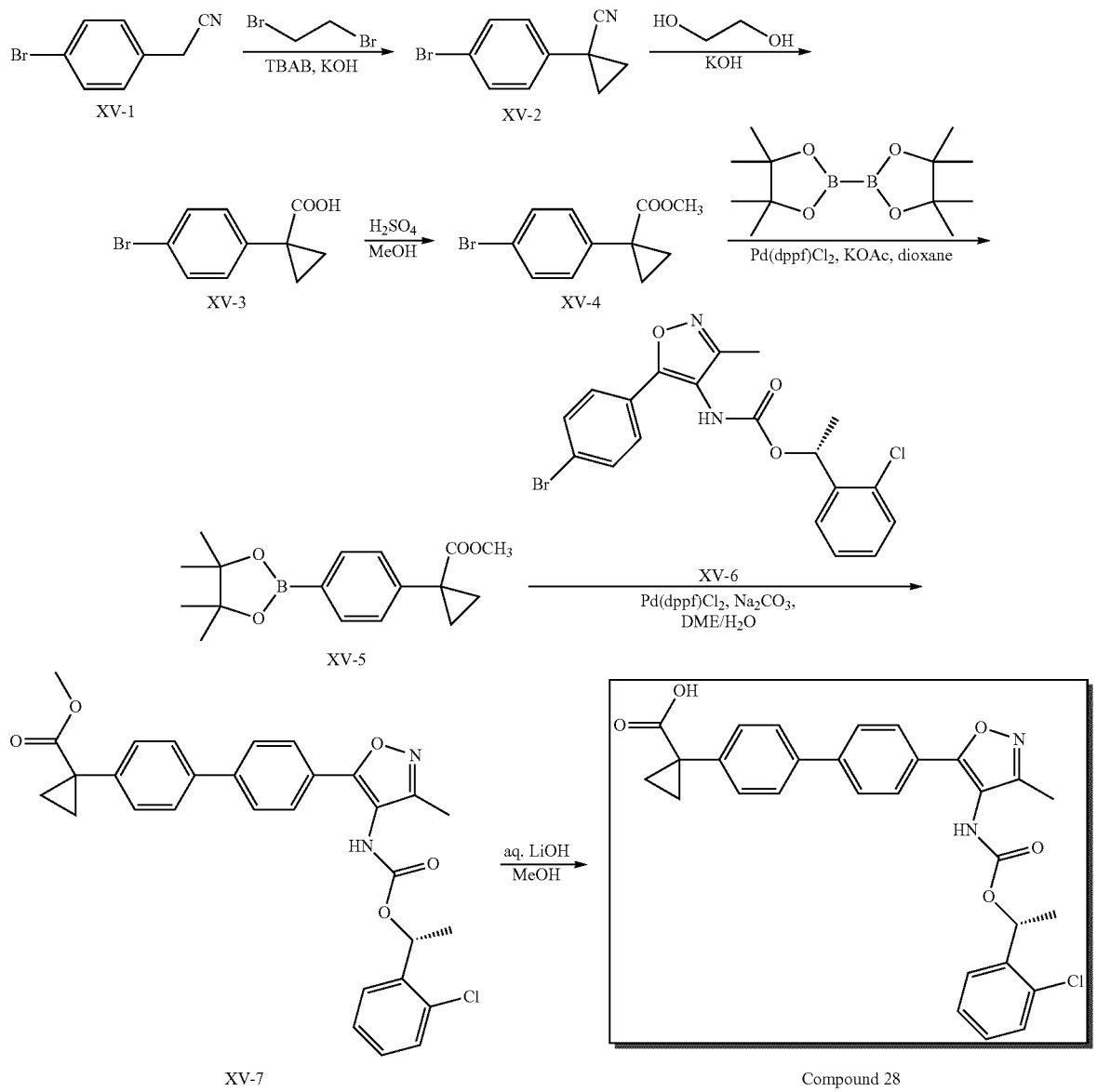

Synthetic Route (Scheme XV)

Compound XV-1 (20 g, 102.56 mmol) was added to a solution of KOH (57.43 g, 1.02 mol) in water (85 mL) and addition, the mixture was heated to 65° C. for 4 hrs. The mixture was cooled to room temperature and diluted with $CH_2Cl_2$ (200 mL), washed with water, dried over $Na_2SO_4$, filtered and concentrated to yield compound XV-4 (6.5 g, yield 88%).

To a solution of compound XV-4 (5.5 g, 21.65 mmol) in dioxane (100 mL) was added bis(pinacolato)diboron (11 g, 43.3 mmol) and $Pd(dppf)Cl_2$ (0.5 g, catalyzed amount). The mixture was purged with nitrogen for 5 minutes and heated to 90° C. overnight. After being cooled to room temperature, the mixture was diluted with water (200 mL) and extracted with EtOAc (150 mL×3). The combined organic layers were washed with brine, dried over $Na_2SO_4$, and concentrated under reduced pressure. The residue was purified by chromatography on silica gel to afford compound XV-5 (5.5 g, yield 84%).

A flask was charged with compound XV-5 (1 g, 3.3 mmol), compound XV-6 (1.44 g, 3.3 mmol), and $Na_2CO_3$ (0.7 g, 6.6 mmol). DME (100 mL) and water (20 mL) were added thereto. The mixture was purged with nitrogen, and then $Pd(dppf)Cl_2$ (120 mg) was added. The resulting mixture was stirred at 90° C. under nitrogen overnight. The reaction was cooled down to room temperature and poured into ice water. The aqueous phase was neutralized with aq. HCl (2 N) at 0° C. The mixture was extracted with EtOAc (50 mL×3). The combined organic phase was dried over $Na_2SO_4$ and concentrated. The residue was purified by chromatography on silica gel (PE:EA=2:1) to give compound XV-7 (0.5 g, yield 57%). MS (ESI) m/z (M+H)$^+$ 531.

Preparation of Compound 28

To a solution of compound XV-7 (1 g, 1.88 mmol) in methanol (100 mL) was added $LiOH.H_2O$ (250 mg, 5.95 mmol) and water (100 mL). The reaction mixture was stirred at room temperature overnight. The mixture was evaporated to remove methanol, the aqueous layer was acidified to pH=4~5 with 1 N HCl and extracted with EtOAc (100 mL×3). The combined organic layers was washed with brine, dried over $Na_2SO_4$, and concentrated, and the residue was purified by preparative HPLC to give Compound 28 (256 mg, yield 26%). $^1$H NMR: (DMSO-$d_6$, 300 MHz) δ 9.46 (s, 1H), 7.81~7.77 (m, 4H), 7.63~7.61 (m, 3H), 7.53~7.50 (m, 2H), 7.43~7.39 (m, 3H), 6.02~5.99 (m, 1H), 2.13 (s, 3H), 1.57 (d, J=3.2 Hz, 3 H), 1.38~1.37 (m, 2H), 1.01~0.98 (m, 2H). MS (ESI) m/z (M+H)$^+$ 517.2.

Synthesis of Compound 30

Synthetic Route (Scheme XVI)

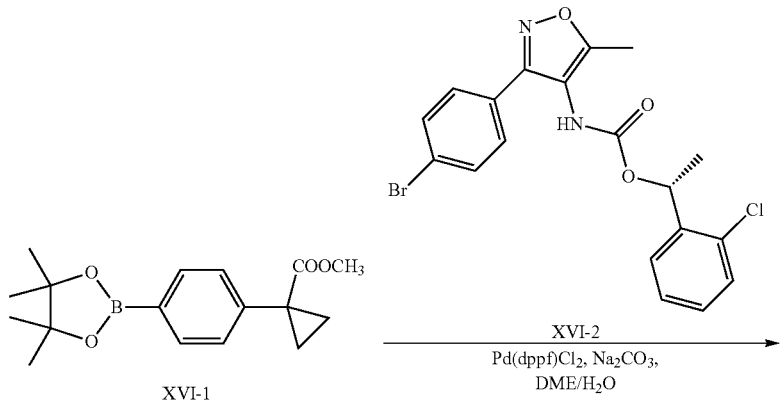

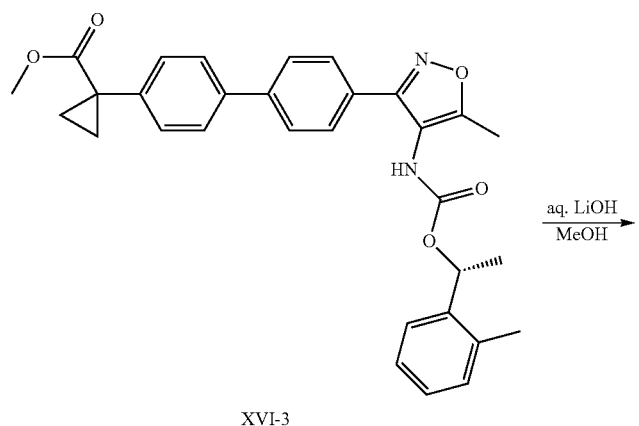

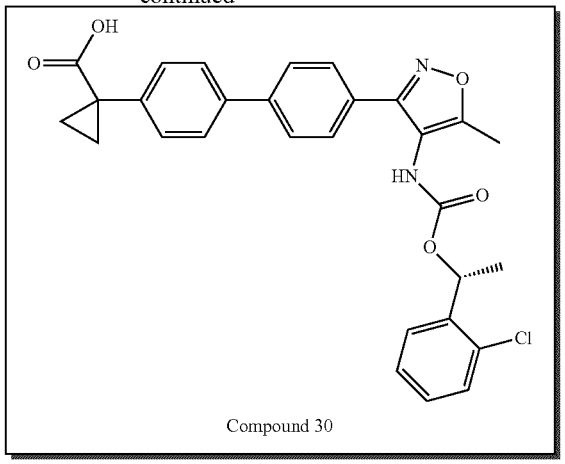

Compound 30

Intermediate XVI-2 was prepared as described in Compound 28.

A flask was charged with compound XVI-1 (0.4 g, 1.33 mmol), compound XVI-2 (0.58 g, 1.33 mmol), $Na_2CO_3$ (0.28 g, 2.66 mmol), DME (60 mL) and water (12 mL). The mixture was purged with nitrogen, and then $Pd(dppf)Cl_2$ (50 mg) was added. The resulting mixture was stirred at 90° C. under nitrogen overnight. The reaction was cooled down to room temperature and poured into ice water. The aqueous phase was neutralized with aq. HCl (2 N) at 0° C. The mixture was extracted with EtOAc (50 mL×3). The combined organic phase was dried over $Na_2SO_4$ and concentrated. The residue was purified by chromatography on silica gel to give compound XVI-3 (0.228 g, yield 53%). MS (ESI) m/z (M+H)⁺ 531.1.

Preparation of Compound 30

To a solution of compound XVI-3 (0.4 g, 0.75 mmol) in methanol (80 mL) was added $LiOH.H_2O$ (90 mg, 2.14 mmol) and water (80 mL). The reaction was stirred at room temperature overnight. The mixture was evaporated to remove methanol, the aqueous layer was acidified to pH=4~5 with 1 N HCl and extracted with EtOAc (80 mL×3). The combined organic layers was washed with brine, dried over $Na_2SO_4$, and concentrated. The residue was purified by preparative HPLC to give Compound 30 (178 mg, yield 46%). $^1$H NMR: (DMSO-$d_6$, 300 MHz) δ 9.18 (s, 1H), 7.79~7.77 (m, 4H), 7.62~7.61 (m, 3H), 7.34~7.32 (m, 5H), 5.93~5.92 (m, 1H), 2.28 (s, 3H), 1.49~1.44 (m, 5H), 1.16~1.15 (m, 2H). MS (ESI) m/z (M+H)⁺ 517.1.

Synthesis of Compound 32

Synthetic Route (Scheme XVII)

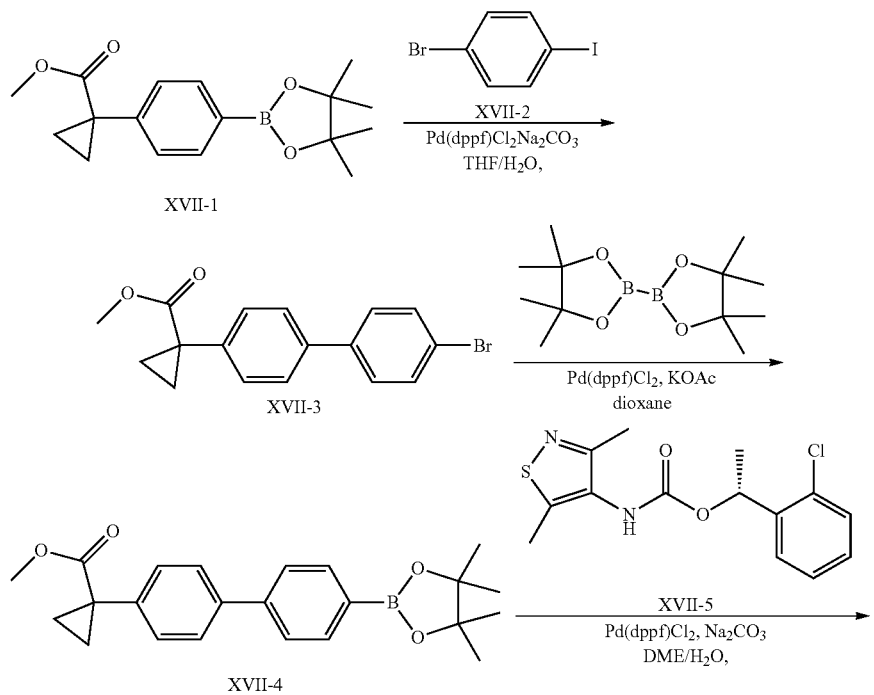

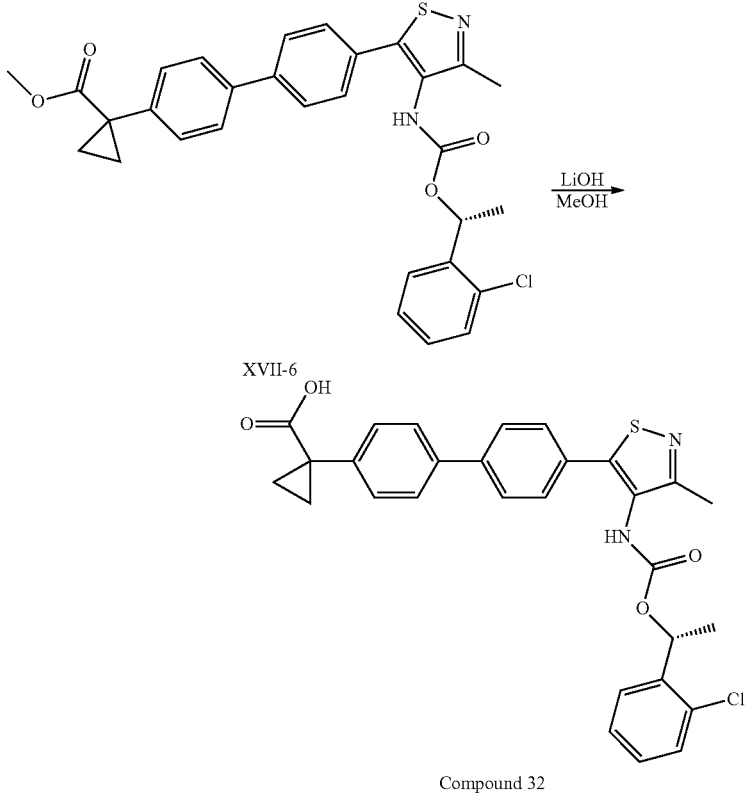

Compound 32

To a solution of compound XVII-1 (2.0 g, 6.62 mmol) in THF/H$_2$O (60 mL, 5:1) was added Na$_2$CO$_3$ (1.403 g, 13.24 mmol), compound XVII-2 (2.05 g, 7.28 mmol), Pd(dppf)Cl$_2$ (484 mg, 0.66 mmol). The mixture was purged with nitrogen and then heated at reflux overnight. The mixture was cooled to rt, diluted with water, extracted with EtOAc (100 mL×3). The combined organic layer was washed with brine, dried over anhydrous Na$_2$SO$_4$, and concentrated in vacuo. The residue was purified by silica gel column (PE/EA 100:1→40:1) to give compound XVII-3 (1.0 g, yield 46%).

To a solution of compound XVII-3 (440 mg, 1.33 mmol) in dioxane (20 mL) was added KOAc (260 mg, 2.66 mmol), compound XVII-13 (676 mg, 2.66 mmol), Pd(dppf)Cl$_2$ (97 mg, 0.13 mmol). The mixture was purged with nitrogen and the mixture was heated at reflux overnight. After being cooled to rt, the mixture was concentrated, diluted with water (40 mL), and extracted with EtOAc (100 mL×3). The combined organic layer was washed with brine, dried over anhydrous Na$_2$SO$_4$, and concentrated in vacuo. The residue was purified by prep-TLC (PE:EA=3:1) to give compound XVII-4 (380 mg, yield 76%) as pale-yellow solid. MS (ESI) m/z (M+H)$^+$ 378.9.

To a solution of compound XVII-4 (300 mg, 0.79 mmol) in DME/H$_2$O (20 mL, v/v=3/1) was added Na$_2$CO$_3$ (167 mg, 1.58 mmol), compound XVII-5 (334 mg, 0.79 mmol), Pd(dppf)Cl$_2$ (58 mg, 0.08 mmol). The mixture was purged with nitrogen and the mixture was heated at reflux overnight. After being cooled to rt, the mixture was concentrated, diluted with water (30 mL), and extracted with EtOAc (30 mL×3). The combined organic layer was washed with brine, dried over anhydrous Na$_2$SO$_4$, and concentrated in vacuo. The residue was purified by prep-TLC (PE:EA=3:1) to give compound XVII-6 (120 mg, yield 28%) as white solid.

Preparation of Compound 32

Compound XVII-6 (240 mg, 0.438 mmol) and LiOH.H$_2$O (147 mg, 3.5 mmol) was added into 20 mL of MeOH/H$_2$O (v:v=4:1). The mixture was stirred at 40° C. overnight. The mixture was concentrated, diluted with water, acidified to pH=3~4 with aq. HCl (1 N), and extracted with EtOAc (20 mL×3). The combined organic layer was washed with water and brine, dried over anhydrous Na$_2$SO$_4$, and concentrated in vacuo. The residue was purified by prep-TLC (PE/EA=1:4) to give Compound 32 (122 mg, yield 52%). $^1$H NMR (DMSO-d$_6$, 400 MHz) δ 12.39 (s, 1H), 9.42 (s, 1H), 7.76-7.74 (m, 2H), 7.65-7.58 (m, 5 H), 7.53-76.82 (m, 5H), 5.60-5.95 (q, 1H), 32.26 (s, 3H), 1.53-1.47 (m, 4H), 1.20-1.18 (m, 3H). MS (ESI) m/z (M+H)$^+$ 533.1.

Synthesis of Compound 41

Synthetic Route (Scheme XVIII)

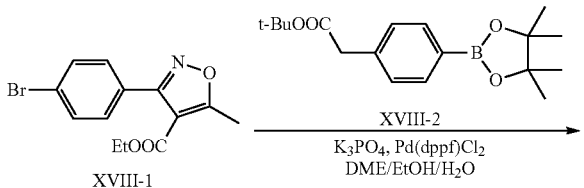

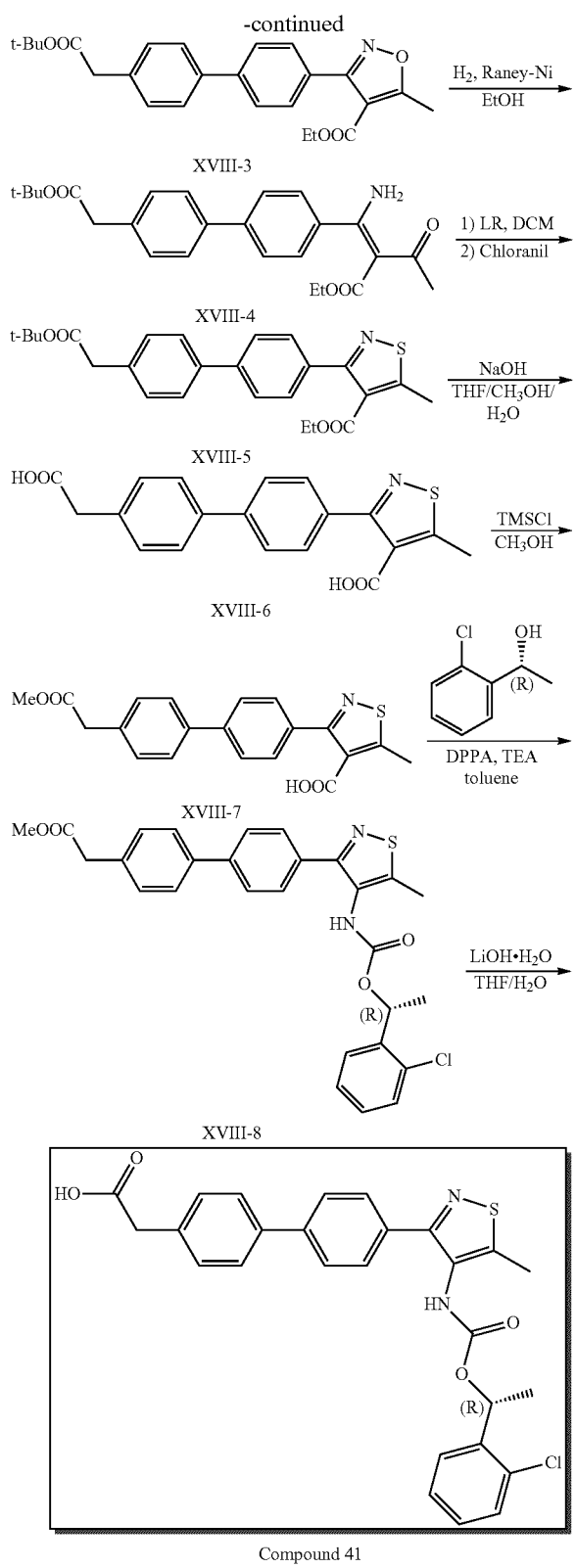

Compound 41

To a stirred mixture of compound VXIII-1 (2.0 g, 6.47 mmol), compound VXIII-2 (4.32 g, 13.6 mmol), and K₃PO₄ (1.65 g, 7.76 mmol) in dimethoxyethane (30 mL), ethanol (10 mL) and H₂O (4 ml) was added Pd(dppf)Cl₂ (530 mg). The reaction mixture was flushed with nitrogen and heated to 80° C. for 5 hrs. The mixture was diluted with EtOAc (50 mL), washed with water and brine, dried over Na₂SO₄, filtered and concentrated. The residue was purified by column chromatography (PE:EA=10:1) to give compound VXIII-3 (1.9 g, yield: 70%).

To a solution of compound XVIII 3 (1.9 g, 4.5 mmol) in ethanol (35 mL) was added Raney nickel (0.5 g). The reaction mixture was flushed with hydrogen and stirred at room temperature for 3 hours. The reaction mixture was filtrated and concentrated to give crude compound XVIII 4 (1.9 g, yield 99%), which was used to next step directly.

To a solution of compound XVIII-4 (1.72 g, 4.1 mmol) in dry DCM (30 mL) was added lawesson's reagent (1.64 g, 4.1 mmol). The reaction mixture was stirred at room temperature overnight, then added chloranil (1.0 g, 4.1 mmol). The reaction mixture was stirred for another day. The mixture was diluted with ice water, extracted with DCM (50 mL×3). The combined organic phase was dried over Na₂SO₄ and concentrated. The residue was purified by column chromatography (PE:EA=10:1) to give compound XVIII-5 (700 mg, yield 39%). MS (ESI) m/z (M+H)⁺ 437.5.

To a solution of compound XVIII-5 (530 mg, 1.2 mmol) in THF/CH₃OH (18 mL/18 mL) was added sodium hydroxide solution (18 mL, 1N). The reaction mixture was stirred at room temperature overnight. The mixture was cooled down to 0° C. and neutralized to pH=4.0 with 3 N hydrochloride solution. The mixture was concentrated to remove solvent THF and methanol, and then extracted with EtOAc (50 mL×3). The combined organic phase was dried over Na₂SO₄ and concentrated to give crude compound XVIII-6 (376 mg, yield: 76%), which was used to next step directly.

To a solution of compound XVIII-6 (376 mg, 1.06 mmol) in dry methanol (20 mL) was added trimethyl chlorosilane (92 uL, 1.06 mmol) at 0° C. The reaction mixture was stirred at room temperature for 3 hours. The reaction mixture was quenched by adding ice water and neutralized to pH=8.0 with 10% sodium hydroxide solution. The mixture was concentrated to remove solvent methanol then extracted with EtOAc (50 mL×3). The combined organic phase was dried over Na₂SO₄ and concentrated to give crude compound XVIII-7 (321 mg, yield: 82.5%).

To a solution of compound XVIII-7 (321 mg, 0.87 mmol) in dry toluene (20 mL) was added (R)-1-(2-chlorophenyl) ethanol (407 mg, 2.61 mmol), triethylamine (0.6 mL) and DPPA (288 mg, 1.05 mmol). The reaction mixture was stirred at 80° C. for 3 hours. The mixture was diluted with EtOAc (50 mL), washed with brine, dried over Na₂SO₄, filtered and concentrated. The residue was purified by column chromatography (PE:EA=20:1) to give compound XVIII-8 (110 g, yield: 72.8%). MS (ESI) m/z (M+H)⁺ 521.0.

Preparation of Compound 41

To a solution of compound XVIII-8 (110 mg, 0.21 mmol) in THF (15 mL) was added water (5 mL) and lithium hydroxide monohydrate (45 mg, 1.06 mmol). The reaction mixture was stirred at room temperature overnight. The mixture was cooled down to 0° C. and neutralized to pH=5.0 with 3 N hydrochloride solution. The mixture was extracted with EtOAc (50 mL). The combined organic phase was dried over Na₂SO₄ and concentrated. The residue was purified by Prep. HPLC to give Compound 41 (50 mg, yield: 46.7%). ¹HNMR (CD₃CN 400 MHz) δ 7.58-7.80 (m, 7H), 7.43-7.30 (m, 6H), 6.03-6.05 (m, 1H), 3.71 (s, 2H), 2.44 (s, 3H), 1.54 (d, J=4.6 Hz, 3H). MS (ESI) m/z (M+H)+ 507.0.
Synthesis of Compound 56
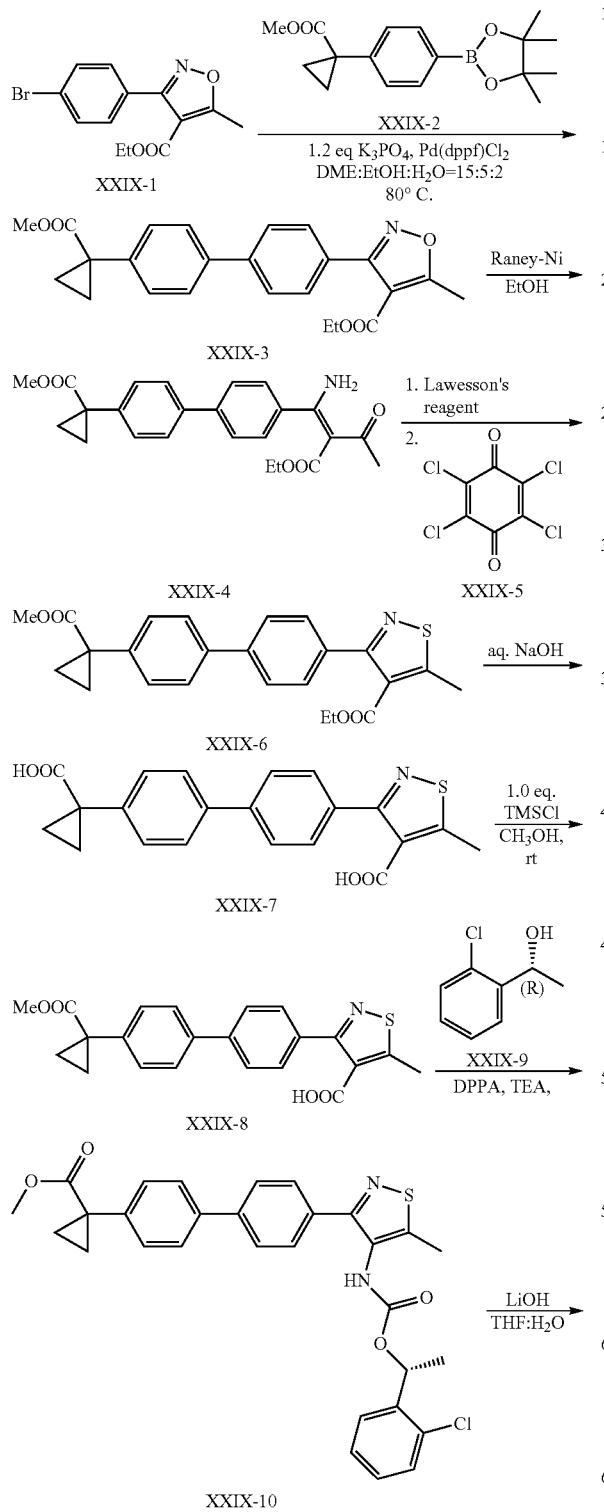
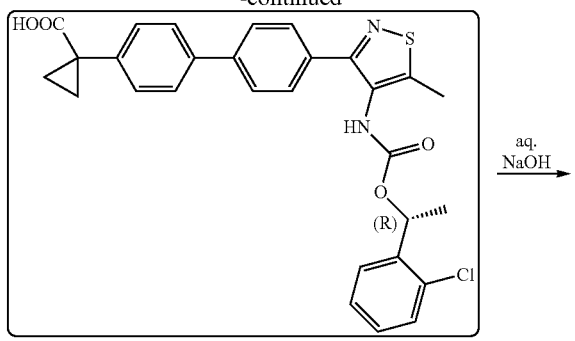
Compound 56 was prepared analogously to the procedure described in the synthesis of Compound 41. Compound 56: ¹HNMR (Methanol-$d_4$ 400 MHz) δ 7.56-7.84 (m, 6H), 7.10-7.47 (m, 6H), 6.11 (q, 1H), 2.49 (s, 3H), 1.63 (m, 2H), 1.55 (d, J=6.4 Hz, 3H). 1.23 (m, 2H). MS (ESI) m/z (M+H)+ 533.1.
Compound 56a was prepared analogously to Compound 41a. Compound 46a: ¹HNMR (DMSO-$d_6$ 400 MHz) δ 7.79-7.81 (m, 2H), 7.65-7.66 (m, 2H), 7.31-7.52 (m, 8H), 5.98 (q, 1H), 2.39 (s, 3H), 1.45 (br, 3H), 1.29 (br, 2H), 0.75 (br, 2H). MS (ESI) m/z (M+H)+ 533.1.
Synthesis of Compound 51

729
-continued
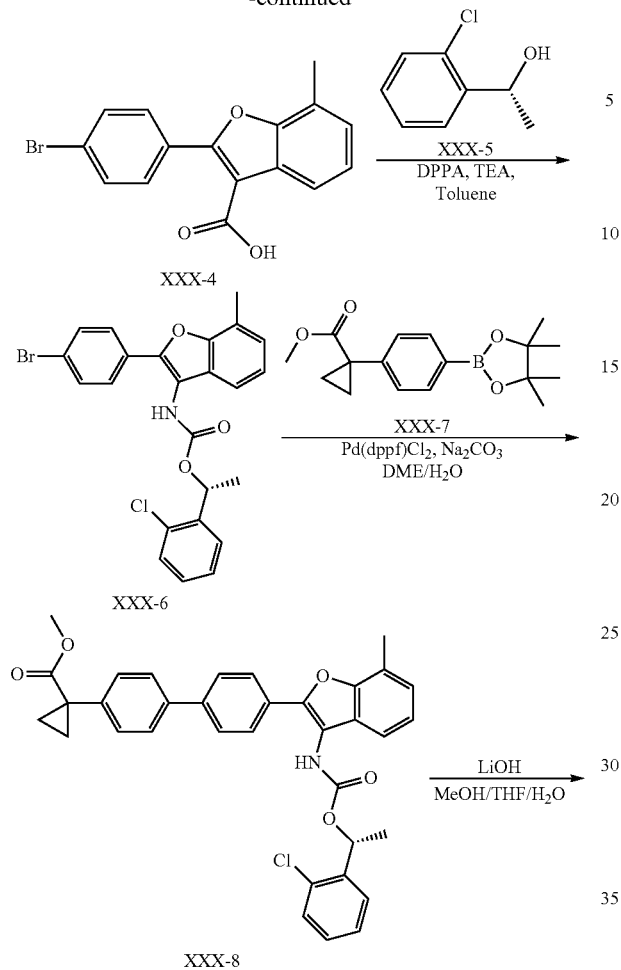
730
-continued
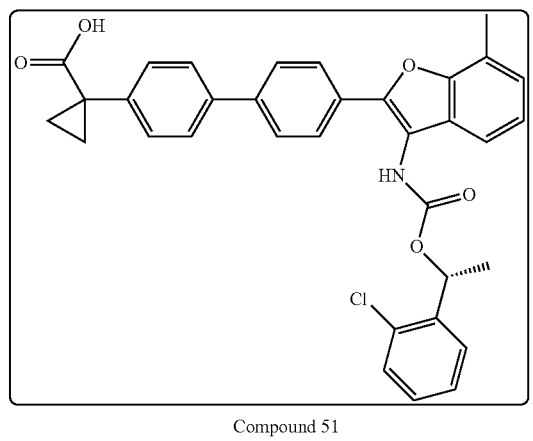 [SMILES: Cc1cccc2c(NC(=O)O[C@H](C)c3ccccc3Cl)c(-c3ccc(-c4ccc(C5(C(=O)O)CC5)cc4)cc3)oc12 ; "Compound 51"]
Compound 51
Compound 51 was prepared analogously to the procedure described in the synthesis of Compound 31. Compound 51: $^1$H NMR (Methanol-$d_4$, 400 MHz): δ 8.01 (m, 2H), 7.61-7.71 (m, 5H), 7.15-7.49 (m, 8H), 7.22 (s, 1H), 6.15 (t, 1H), 2.53 (s, 3H), 1.57-1.60 (m, 5H) 1.20-1.25 (m, 2H). MS (ESI) m/z (M+H)$^+$ 566.1.
Synthesis of Compound 52
Synthetic Route (Scheme XXXI)
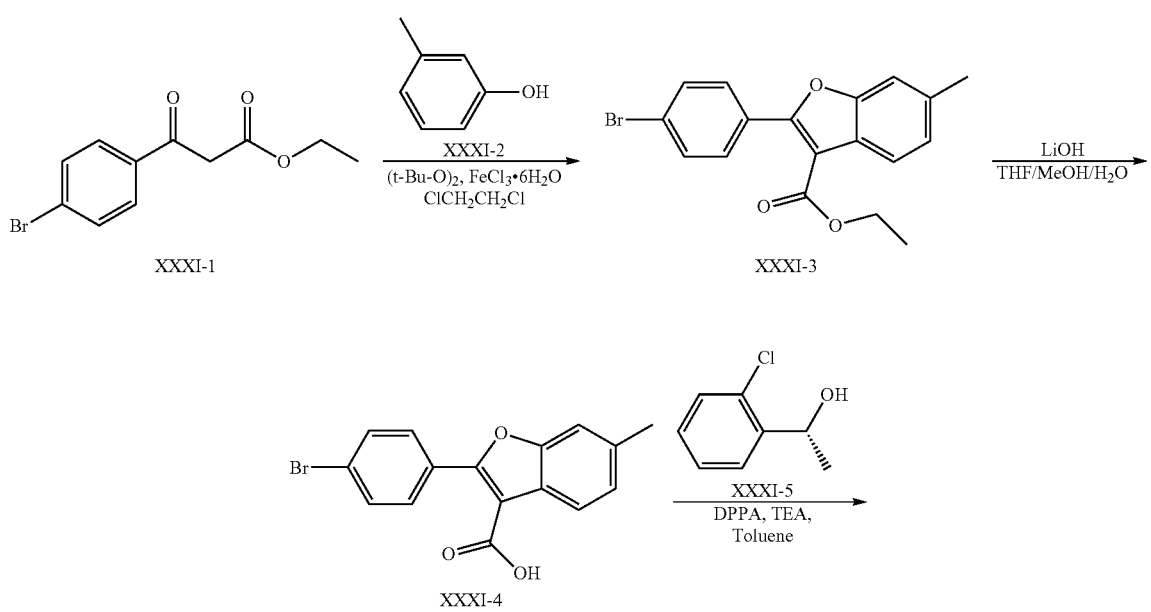

-continued
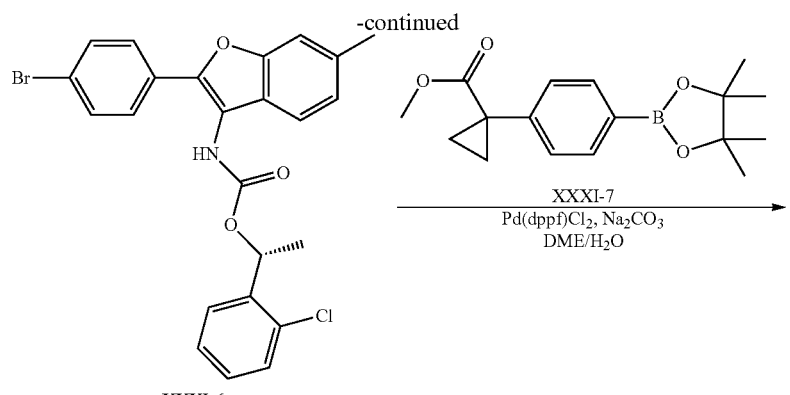
XXXI-6
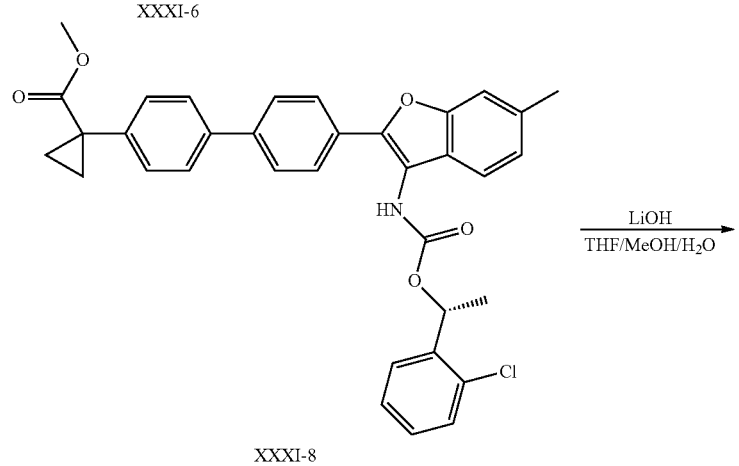
XXXI-8
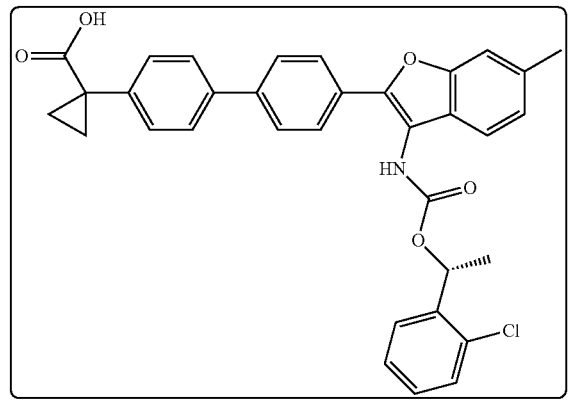
Compound 52
Compound 52 was prepared analogously to the procedure described in the synthesis of Compound 31. Compound 52: $^1$H NMR (CD$_3$OD, 400 MHz): δ 7.95 (d, J=8.4 Hz, 2H), 7.69-7.74 (m, 3H), 7.63 (d, J=8.4 Hz, 2H), 7.43-7.49 (m, 4H), 7.35-7.40 (m, 3H), 7.12 (m, 1H), 6.21 (q, J=7.6 Hz, 1H), 1.60-1.67 (m, 5H), 1.23-1.24 (m, 2H). MS (ESI) m/z (M+H)$^+$ 566.2.
Synthesis of Compound 53
Synthetic Route (Scheme XXXII)
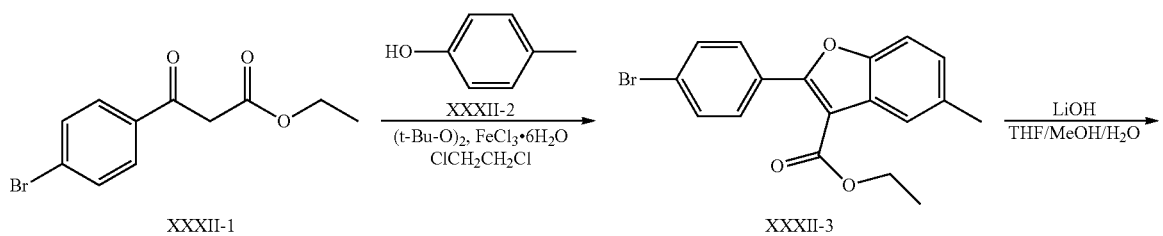

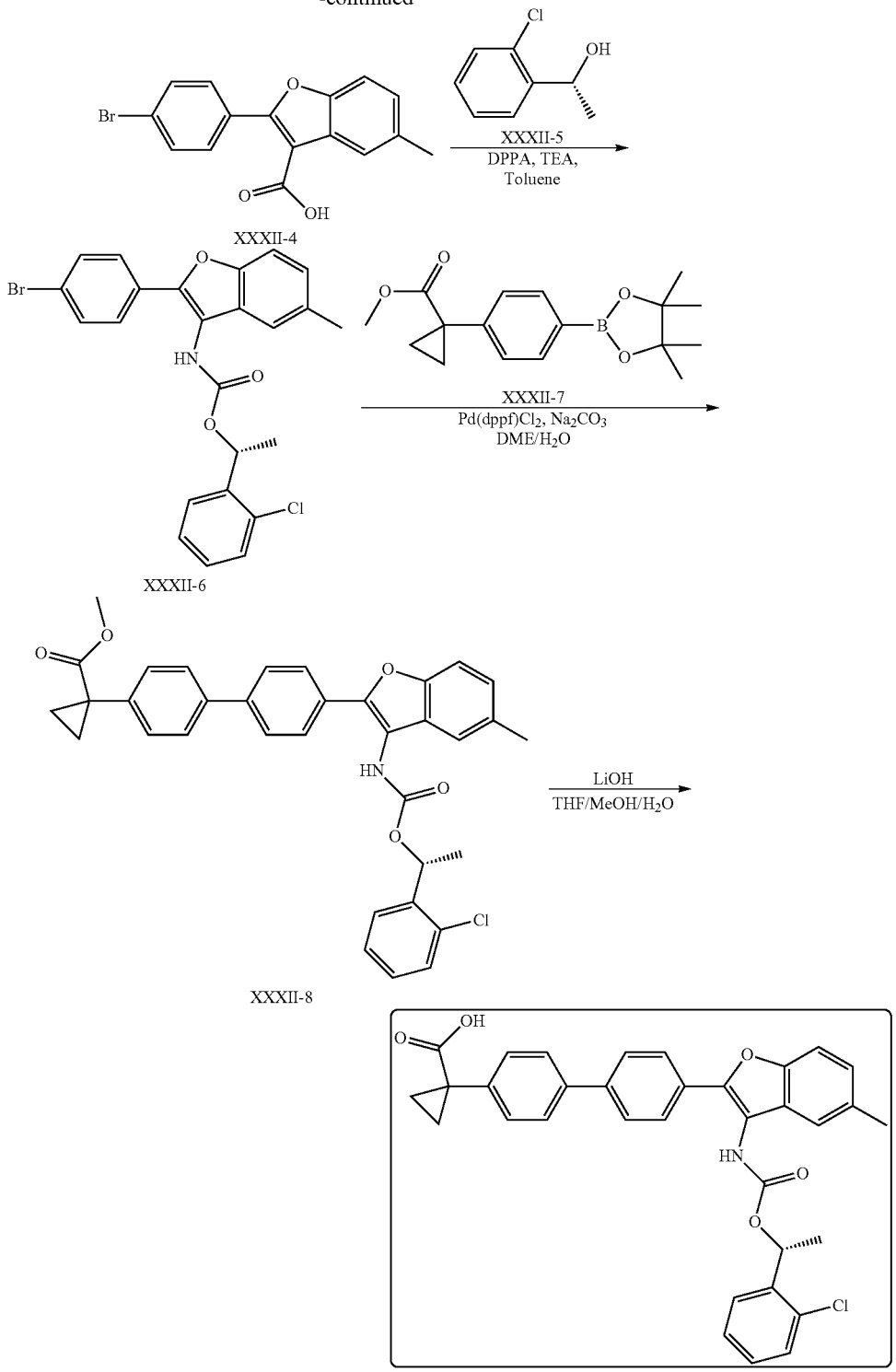
Compound 53
Compound 53 was prepared analogously to the procedure described in the synthesis of Compound 31. Compound 53: $^1$H NMR (CD$_3$OD, 400 MHz): δ 7.96-7.98 (m, 2H), 7.69-7.75 (m, 3H), 7.63 (d, J=8.0 Hz, 2H), 7.36-7.49 (m, 6H), 7.12-7.21 (m, 2H), 6.21 (m, 1H), 2.43 (s, 3H), 1.60-1.67 (m, 5H), 1.23-1.24 (m, 2H). MS (ESI) m/z (M+H)$^+$ 566.3 Compound 53a was prepared analogously to Compound 31a. $^1$H NMR (CD$_3$OD, 400 MHz): δ 9.62 (s, 1H), 7.89 (d, J=7.6 Hz, 2H), 7.72 (d, J=7.6 Hz, 2H), 7.47-7.54 (m, 5H), 7.33-7.35 (m, 3H), 7.14 (d, J=6.0 Hz, 2H), 6.25 (q, J=9.8 Hz, 1H), 2.37 (s, 3H), 1.58 (d, J=6.0 Hz, 3H), 1.20-1.21 (m, 2H), 0.70-0.71 (m, 2H). MS (ESI) m/z (M+H)$^+$ 566.1.

Synthesis of Compound 60
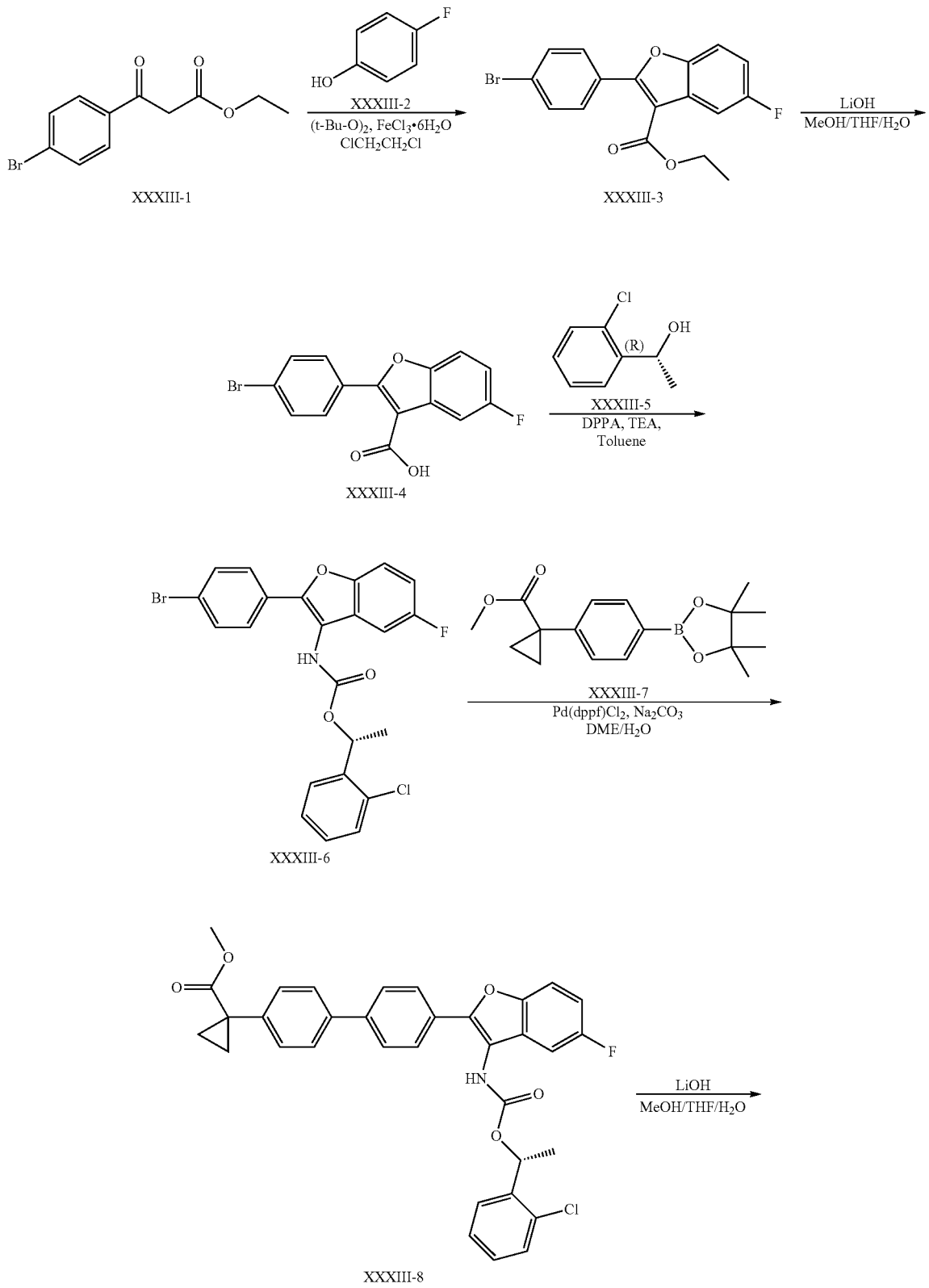

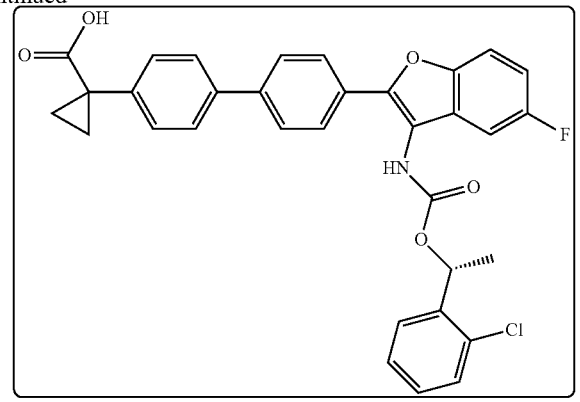
Compound 60
Compound 60 was prepared analogously to the procedure described in the synthesis of Compound 31. Compound 60: $^1$H NMR (DMSO-d6, 400 MHz): δ 9.68 (s, 1 H), 7.90 (d, J=8.0 Hz, 2H), 7.76 (d, J=8.0 Hz, 2H), 7.47-7.50 (m, 4H), 7.36-7.47 (m, 5H), 7.11-7.20 (m, 2H), 6.00-6.02 (q, 1H), 1.56 (d, J=4.2 Hz, 3H), 1.44-1.47 (q, 2H), 1.15-1.20 (q, 2H). MS (ESI) m/z (M+H)$^+$ 570.1.
Synthesis of Compound 61
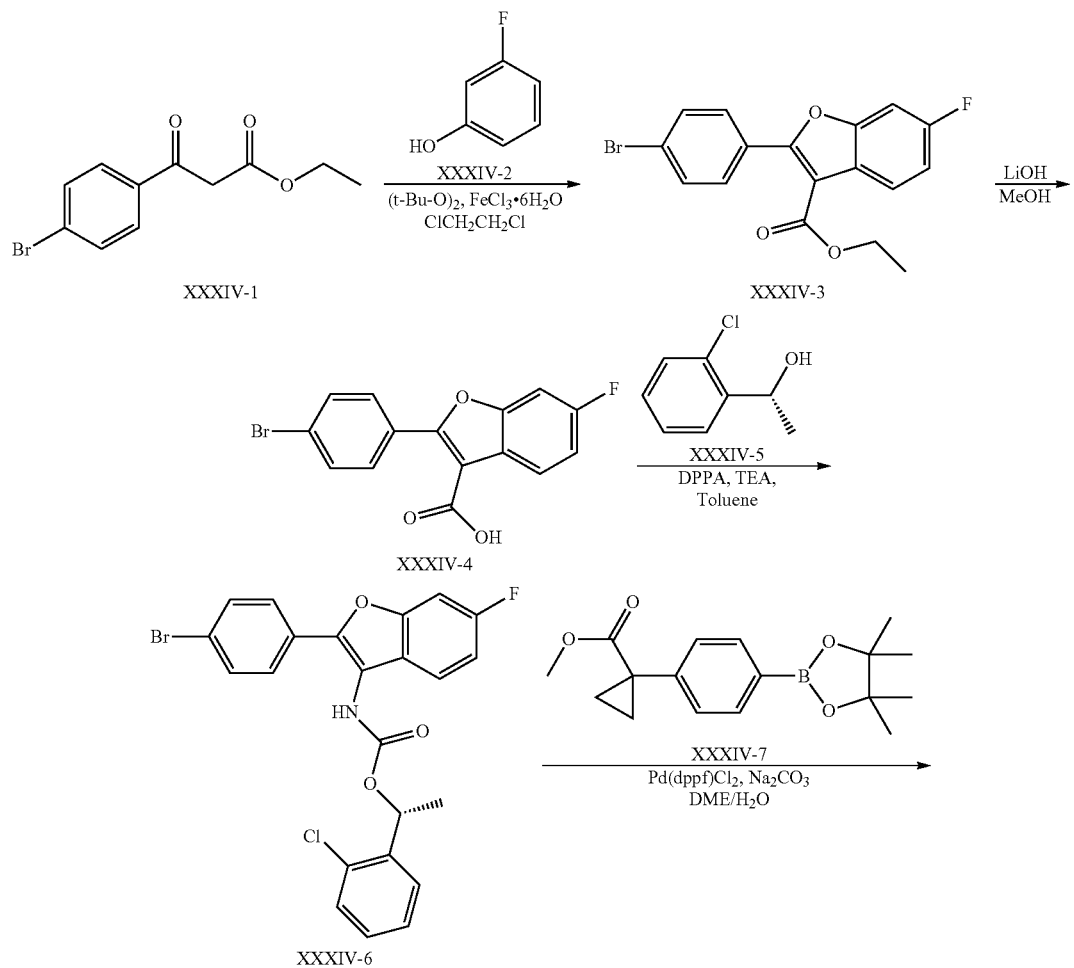

-continued
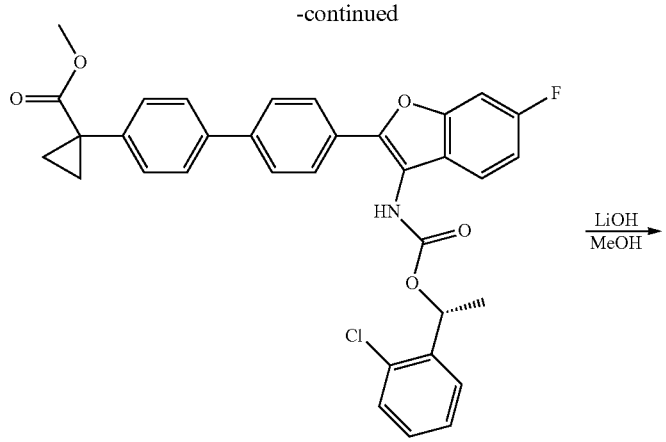
XXXIV-8
Compound 61
Compound 61 was prepared analogously to the procedure described in the synthesis of Compound 31. Compound 61: $^1$H NMR (DMSO-d6, 400 MHz): δ 9.71 (s, 1 H), 7.86-7.88 (m, 2H), 7.60-7.76 (m, 6H), 7.41-7.48 (m, 6H), 7.16-7.39 (m, 1H), 6.01-6.02 (q, 1H), 1.56-1.57 (d, J=5.6 Hz, 3H) 1.45-1.48 (m, 2H), 1.15-1.18 (m, 2H). MS (ESI) m/z (M+H)$^+$ 570.2.
Synthesis of Compound 62
Synthetic Route (Scheme XXXV)
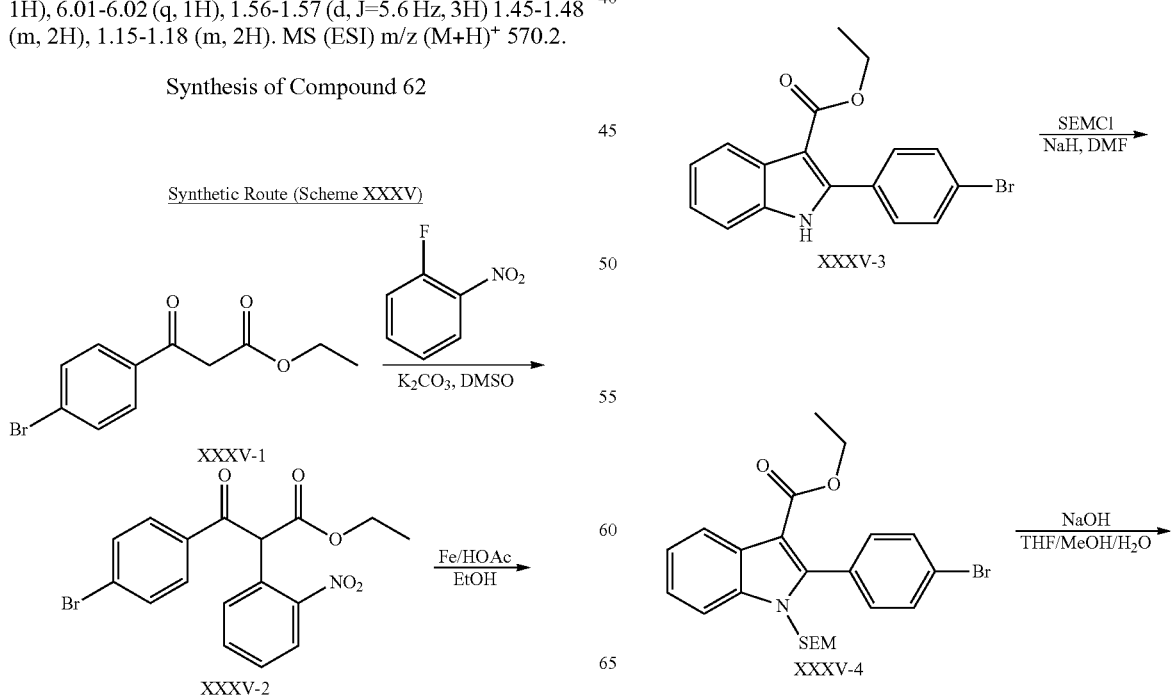

741
-continued

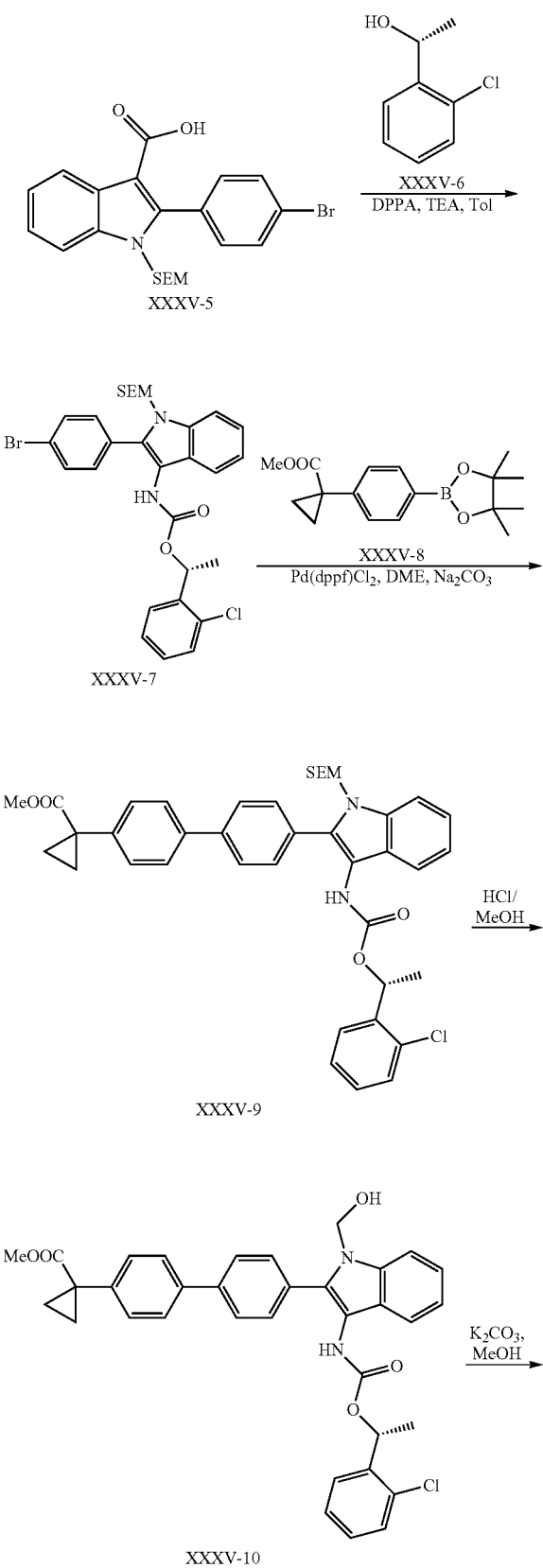

XXXV-5

XXXV-7

XXXV-9

XXXV-10

742
-continued

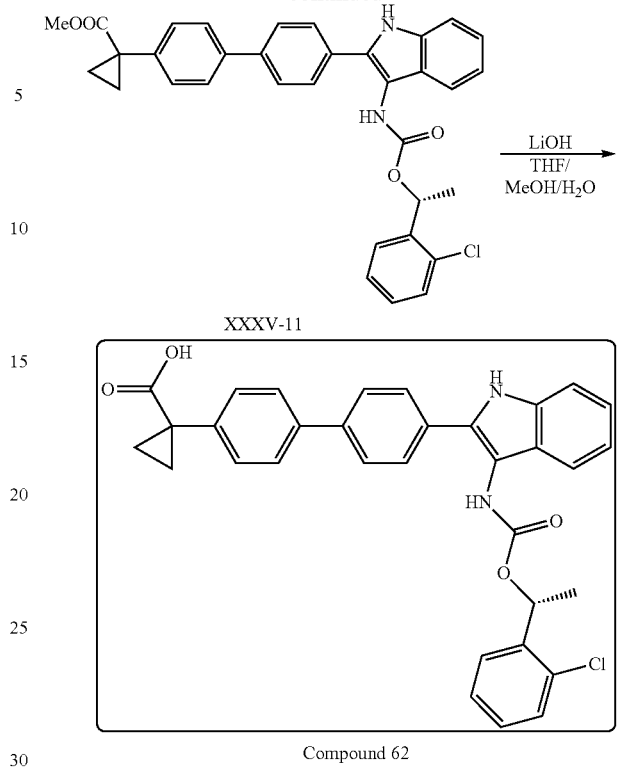

XXXV-11

Compound 62

To a stirring solution of 1-Fluoro-2-nitro-benzene (3.1 g, 22.13 mmol) in DMSO (25 mL) was added compound XXXV-1 (4.0 g, 14.75 mmol) and $K_2CO_3$ (4.1 g, 29.5 mmol). Then the mixture was stirred overnight at room temperature. The mixture was poured into water and extracted with ethyl acetate (3×100 mL), the combined organic layer was washed with brine, dried over $MgSO_4$, and concentrated in vacuo to give compound XXXV-2 (6.1 g, crude yield 105%), which was used directly.

Fe powder (4.5 g, 81.1 mmol) was added to a solution of compound XXXV-2 (6.10 g, 14.7 mmol) in a mixture of acetic acid (96 mL) and ethanol (120 mL). The mixture was placed in a preheated (100° C.) oil bath and stirred overnight at this temperature. The mixture was filtered through celite and the filtrate was concentrated. The residue was partitioned between ethyl acetate and water. The organic layer washed with saturated $NaHCO_3$ solution, brine, dried and concentrated. The resulting solids were washed with t-butylmethyl-ether and dried to afford compound XXXV-3 (2.4 g, yield 47%). MS (ESI) m/z $(M+H)^+$ 343.7.

To a stirred solution of compound XXXV-3 (2.4 g, 6.97 mmol) in DMF (20 mL) was added NaH (0.34 g, 8.37 mmol) followed by SEMCl (1.3 g, 7.66 mmol) at 0° C. under nitrogen. After the addition, the mixture was stirred for 2 hours at room temperature under nitrogen. The mixture was poured into ice water and extracted with ethyl acetate (3×30 mL). The combined organic layer was washed with brine, dried and concentrated. The residue was purified by column chromatography over silica gel (eluent: PE/EA=30/1) to afford compound XXXV-4 (3.3 g, yield 100%).

To a stirred solution of XXXV-4 (3.3 g, 7.38 mmol) in 15 mL of MeOH/THF/$H_2O$ (v/v=1:1:1) was added sodium hydroxide (1.2 g, 30.00 mmol). The solution was heated to 80° C. for 20 hours. The solvent was removed in vacuo and the resulting solid was washed with PE, then treated with 1 N HCl aqueous solution and extracted with ethyl acetate (3×50 mL). The combined organic layer was washed with brine, dried over MgSO$_4$, concentrated to afford compound XXXV-5 (3.0 g, yield 97%). MS (ESI) m/z (M+H)$^+$ 448.1.

The mixture of compound XXXV-5 (1.60 g, 3.36 mmol), compound XXXV-6 (0.63 g, 4.03 mmol), DPPA (1.11 g, 4.03 mmol) and Et$_3$N (0.94 mL, 6.72 mmol) in toluene (20 mL) was heated to reflux under nitrogen for 2 hours. The mixture was concentrated, and the residue was partitioned between H$_2$O and DCM. The organic layer was washed with brine, dried over Na$_2$SO$_4$, and concentrated. The residue was purified by column chromatography on silica gel (Petroleum ether/EtOAc=10/1) to afford compound XXXV-7 (1.1 g, yield 55%).

The mixture of compound XXXV-7 (0.7 g, 1.17 mmol), compound XXXV-8 (0.42 g, 1.40 mmol), Na$_2$CO$_3$ (0.25 g, 2.34 mmol) and Pd(dppf)Cl$_2$ (42 mg, 0.06 mmol) in DME/H$_2$O (8 mL, v/v=3:1) was heated to reflux under nitrogen for 2 hours. After cooled, the mixture was filtered through celite and the filtrate was partitioned between ethyl acetate and water. The organic layer was separated and the aqueous layer was extracted with ethyl acetate (3×15 mL). The combined organic layer was washed with brine, dried over MgSO$_4$ and concentrated. The residue was purified by column chromatography over silica gel (eluent: petroleum ether/ethyl acetate=5/1) to afford compound XXXV-9 (0.27 g, yield 33%). MS (ESI) m/z (M+Na)$^+$ 717.3.

To a stirred solution of XXXV-9 (0.25 g, 0.36 mmol) in 2 mL of MeOH was added a solution of HCl in MeOH (4 N, 2 mL). The mixture was heated to 40° C. and stirred for 4 hours. Water and ethyl acetate was added to the mixture. The organic layer was separated and the aqueous layer was extracted with ethyl acetate (3×10 mL). The combined organic layer was washed with water, saturated NaHCO$_3$ aqueous solution, brine and dried over MgSO$_4$. After filtered, the filtrate was concentrated in vacuo to afford compound XXXV-10 (0.25 g, crude yield 117%) as crude product which was used for next step without further purification.

To a stirred solution of XXXV-10 (0.2 g, 0.34 mmol) in 5 mL of MeOH was added K$_2$CO$_3$ (0.3 g, 2.2 mmol) at 0° C. The mixture was stirred for 10 minutes at room temperature. The mixture was treated with H$_2$O and extracted with ethyl acetate (3×15 mL). The combined organic layer was washed with brine, dried and concentrated. The residue was purified by prep-HPLC to afford compound XXXV-11 (0.11 g, yield 47%).

Preparation of Compound 62

A mixture of compound XXXV-11 (100 mg, 0.18 mmol) and Lithium hydroxide monohydrate (30 mg, 0.71 mmol) in MeOH/THF/H$_2$O (5 mL, v/v/v=1/1/1) was stirred overnight at room temperature. The mixture was concentrated in vacuo to remove MeOH and THF, and then acidified with aq. HCl (2 N) to pH=3, and then extracted with ethyl acetate (30 mL×3). The combined organic layer was washed with brine, dried over Na$_2$SO$_4$, filtered and concentrated. The residue was purified by prep-HPLC to afford Compound 62 (20 mg, yield 21%). $^1$H NMR (CD$_3$OD, 400 MHz): δ 11.21 (s, 1H), 8.77 (br, 1H), 7.88 (d, J=8.4 Hz, 2H), 7.72 (d, J=8 Hz, 2H), 7.65 (d, J=8 Hz, 2H), 7.34-7.49 (m, 8H), 7.14 (t, J=7.6 Hz, 1H), 7.02 (t, J=7.2 Hz, 1H), 6.04 (q, J=6 Hz, 1H), 1.50-1.53 (m, 5H), 1.19-1.21 (m, 2H). MS (ESI) m/z (M+H)$^+$ 551.1.

Synthesis of Compound 63

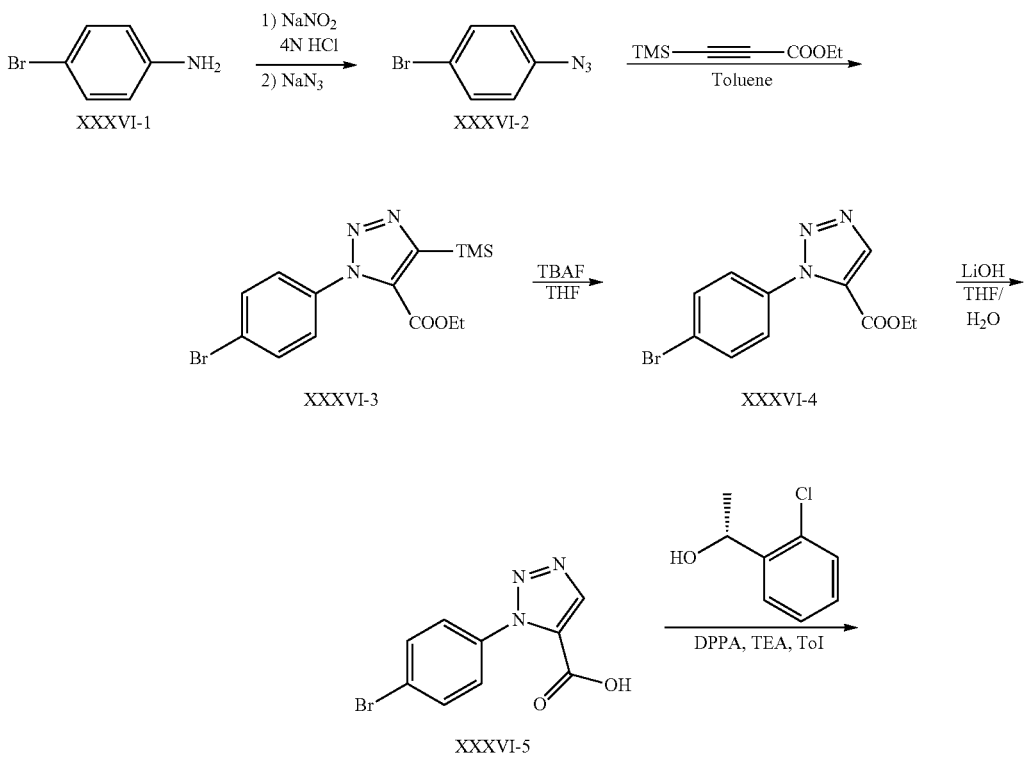

Synthetic Route (Scheme XXXVI)

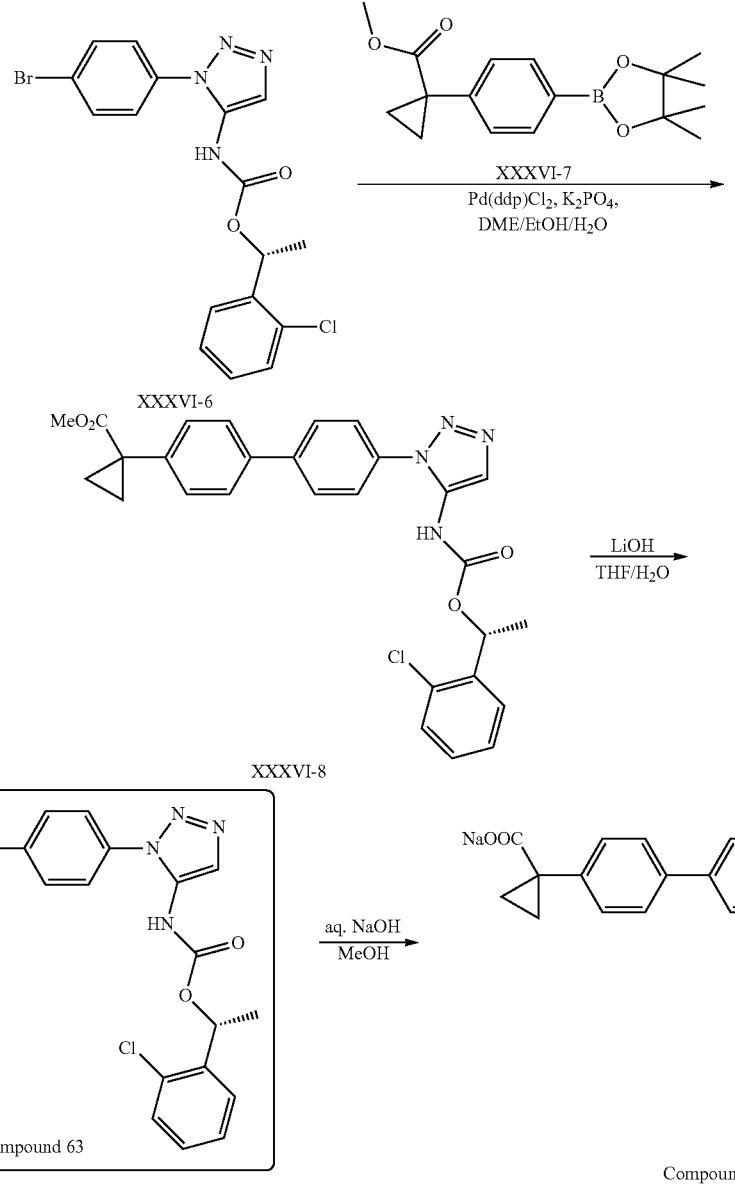

To a solution of compound XXXVI-1 (8.55 g, 50 mmol) in 4 N hydrochloride solution (60 mL) was added dropwise of NaNO$_2$ (3.8 g, 55 mmol) in water (10 mL) at 0° C. After addition the mixture was stirred for 30 minutes, then NaN$_3$ (3.9 g, 60 mmol) was added portionwise. The reaction mixture was slowly warmed to room temperature and stirred for 1 hour. The reaction mixture was extracted with MTBE (50 mL×3). The combined organic phase was dried over Na$_2$SO$_4$, filtered and concentrated to give crude compound XXXVI-2 (10 g, yield: 100%), which was used to next step directly.

To a solution of compound XXXVI-2 (1.97 g, 10 mmol) in toluene (20 mL) was added ethyl 3-(trimethylsilyl)propiolate (1.7 g, 10 mmol). The reaction mixture was flushed with nitrogen and stirred at reflux overnight. Then reaction mixture was concentrated to give crude compound XXXVI-3 (3.67 g, crude), which was used to next step directly.

To a solution of compound XXXVI-3 (3.67 g, 10 mmol) in THF (30 mL) was added TABF (3.9 g, 15 mmol). The reaction mixture was stirred at room temperature for 4 hours. TLC analysis showed the reaction to be complete. The reaction mixture was concentrated, the residue was purified by column chromatography (PE:EA=15:1) to give compound XXXVI-4 (1.98 g, yield 67%).

To a solution of compound XXXVI-4 (2.0 g, 6.7 mmol) in THF/H$_2$O (30 mL/10 mL) was added lithium hydroxide (1.43 g, 33.9 mmol). The reaction mixture was stirred at room temperature overnight. The mixture was cooled down to 0° C. and neutralized to pH=4.0 with 3 N hydrochloride solution. The mixture was extracted with EtOAc (50 mL×3). The combined organic phase was dried over Na$_2$SO$_4$ and concentrated to give crude compound XXXVI-5 (1.8 g, crude), which was used to next step directly.

To a solution of compound XXXVI-5 (1.8 g, 6.7 mmol) in dry toluene (50 mL) was added (R)-1-(2-chlorophenyl)ethanol (1.58 g, 10.1 mmol), triethylamine (2.0 mL) and DPPA (2.2 g, 8.1 mmol). The reaction mixture was heated to 80° C. for 3 hours. The mixture was diluted with EtOAc, washed with brine, dried over Na$_2$SO$_4$, filtered and concentrated. The residue was purified by column chromatography (PE:EA=15:1) to give compound XXXVI-6 (1.9 g, yield: 67.6%). $^1$HNMR (CD$_3$CN, 400 MHz) δ 7.95 (s, 1 H), 7.75 (m, 3 H), 7.46-7.32 (m, 5 H), 6.08 (m, 1 H), 1.49 (d, J=6.4 Hz, 3 H).

To a stirred mixture of compound XXXVI-6 (630 mg, 1.5 mmol), compound XXXVI-7 (5.21 g, 1.65 mmol), and K$_3$PO$_4$ (382 mg, 1.8 mmol) in dimethoxyethane (30 ml) ethanol (10 mL) and H$_2$O (4 ml) was added Pd(dppf)$_2$Cl$_2$ (200 mg). The reaction mixture was flushed with nitrogen and heated to 80° C. for 5 hrs. The mixture was diluted with EtOAc (50 mL), washed with water and brine, dried over Na$_2$SO$_4$, filtered and concentrated. The residue was purified by column chromatography (PE:EA=15:1) to give compound XXXVI-8 (0.5 g, yield: 62.9%). MS (ESI) m/z (M+H)$^+$ 517.0.

Preparation of Compound 63

To a solution of compound XXXVI-8 (454 mg, 0.88 mmol) in THF (30 mL) was added water (10 mL) and lithium hydroxide monohydrate (180 mg, 4.5 mmol). The reaction mixture was stirred at room temperature overnight. The mixture was cooled down to 0° C. and neutralized to pH=4.0 with 3 N hydrochloride solution. The mixture was extracted with EtOAc (50 mL×3). The combined organic phase was dried over Na$_2$SO$_4$ and concentrated. The residue was purified by TLC (PE:EA=1:1) to give Compound 63 (200 mg, yield: 45.2%). MS (ESI) m/z (M+H)$^+$ 503.1.

Preparation of Compound 63a

To a solution of Compound 63 (75 mg, 0.15 mmol) in MeOH (2 mL) was added 0.1 N sodium hydroxide solution (1.5 mL) at 0° C. The reaction mixture was stirred for 30 minutes, then lyophilized to give Compound 63a (78 mg, yield: 100%). $^1$HNMR (DMSO-d$_6$ 400 MHz) δ7.75-7.83 (m, 4 H), 7.58-7.64 (m, 3 H), 7.39-7.48 (m, 4 H), 7.25-7.35 (m, 2 H), 5.95 (m, 1 H), 1.41 (d, J=6.4 Hz, 3H), 1.33 (br, 2 H), 0.94 (br, 2 H). MS (ESI) m/z (M+H)$^+$ 503.1.

Synthesis of Compound 64

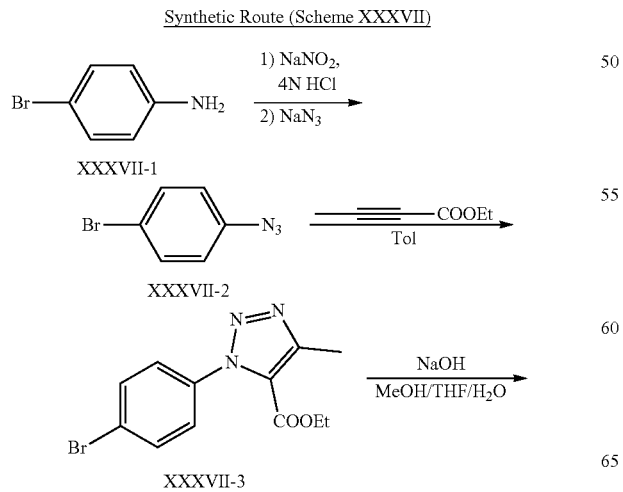

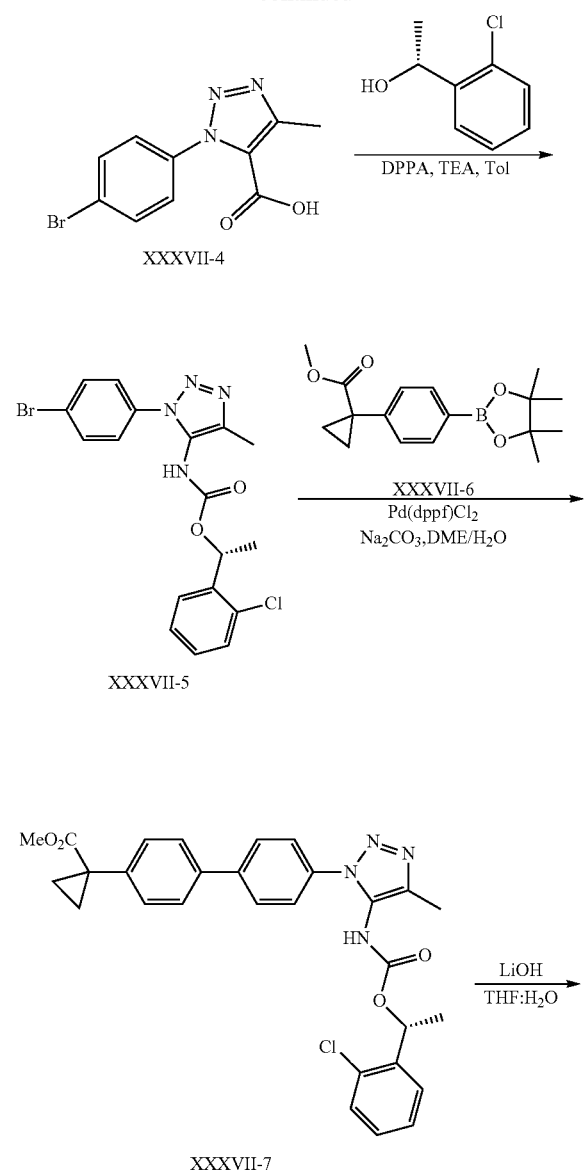

Compound 64

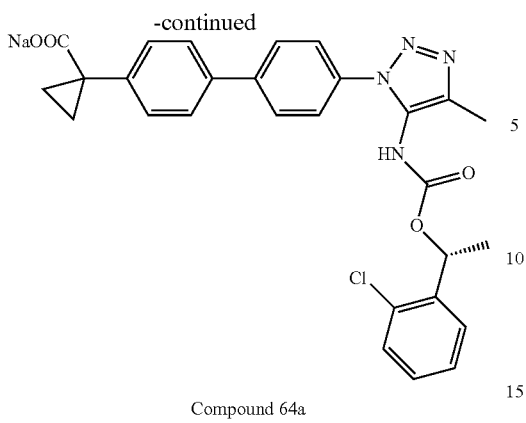

Compound 64a

To a solution of compound XXXVII-1 (8.55 g, 50 mmol) in 4 N hydrochloride solution (60 mL) was added dropwise of NaNO$_2$ (3.8 g, 55 mmol) in water (10 mL) at 0° C. After addition, the mixture was stirred for 30 minutes, then NaN$_3$ (3.9 g, 60 mmol) was added portionwise. The reaction mixture was slowly warmed to room temperature and stirred for 1 hour. The reaction mixture was extracted with MTBE (50 mL×3). The combined organic phase was dried over Na$_2$SO$_4$, filtered and concentrated to give crude product XXXVII-2 (10 g, yield: 100%), which was used to next step directly.

To a solution of compound XXXVII-2 (1.0 g, 5.05 mmol) in toluene (20 mL) was added But-2-ynoic acid ethyl ester (0.7 mL, 6.06 mmol). The reaction mixture was flushed with nitrogen and heated to reflux overnight. The reaction mixture was concentrated, and the residue was purified by column chromatography (PE:EA=5:1) to give compound XXXVII-3 (400 mg, yield: 32%). MS (ESI) m/z (M+H)$^+$ 309.9.

To a solution of compound XXXVII-3 (1.33 g, 4.29 mmol) in MeOH/THF/H$_2$O (10 mL/10 mL/10 mL) was added NaOH (0.86 g, 21.45 mmol). The reaction mixture was stirred at room temperature overnight. The mixture was cooled down to 0° C. and neutralized to pH=4.0 with 3 N hydrochloride solution. The mixture was extracted with EtOAc (40 mL×3). The combined organic phase was dried over Na$_2$SO$_4$ and concentrated to give crude compound XXXVII-4 (1.15 g, yield: 96%), which was used to next step directly. MS (ESI) m/z (M+H)$^+$ 281.9.

To a solution of compound XXXVII-4 (0.4 g, 1.42 mmol) in dry toluene (10 mL) was added (R)-1-(2-chlorophenyl)ethanol (287 mg, 1.84 mmol), triethylamine (287 mg) and DPPA (0.51 g, 1.84 mmol). The reaction mixture was heated to 80° C. for 3 hours. The mixture was diluted with EtOAc, washed with brine, dried over Na$_2$SO$_4$, filtered and concentrated. The residue was purified by column chromatography (PE:EA=10:1) to give compound XXXVII-5 (370 mg, yield: 60%). MS (ESI) m/z (M+H)$^+$ 435.0.

To a stirred mixture of compound XXXVII-5 (370 mg, 0.85 mmol), compound XXXVII-6 (308 mg, 1.02 mmol), and Na$_2$CO$_3$ (190 mg, 1.79 mmol) in DME (9 mL) and H$_2$O (3 mL) was added Pd(dppf)Cl$_2$ (62 mg, 0.085 mmol). The reaction mixture was flushed with nitrogen and heated to 80° C. overnight. The mixture was diluted with EtOAc (40 mL), washed with water and brine, dried over Na$_2$SO$_4$, filtered and concentrated. The residue was purified by column chromatography (PE:EA=10:1) to give compound XXXVII-7 (200 mg, yield: 44%). MS (ESI) m/z (M+H)$^+$ 531.2.

Compound 64 was prepared analogously to the procedure described in the synthesis of Compound 63. Compound 64: MS (ESI) m/z (M+H)$^+$ 517.2. Compound 64a was prepared analogously to the procedure described in the synthesis of Compound 63a. $^1$HNMR (DMSO-d$_6$ 400 MHz) δ 9.99 (s, 1H), 7.78 (d, J=8.4 Hz, 2H), 7.59 (d, J=8.4 Hz, 2H), 7.54 (d, J=8.0 Hz, 2H), 7.31-7.43 (m, 6 H), 5.91 (q, J=6.4 Hz, 1 H), 2.15 (s, 3H), 1.41 (br, 3H), 1.23 (br, 2 H), 0.75 (br, 2 H). MS (ESI) m/z (M+H)$^+$ 517.1.

Synthesis of Compound 65

Synthetic Route (Scheme XXXVIII)

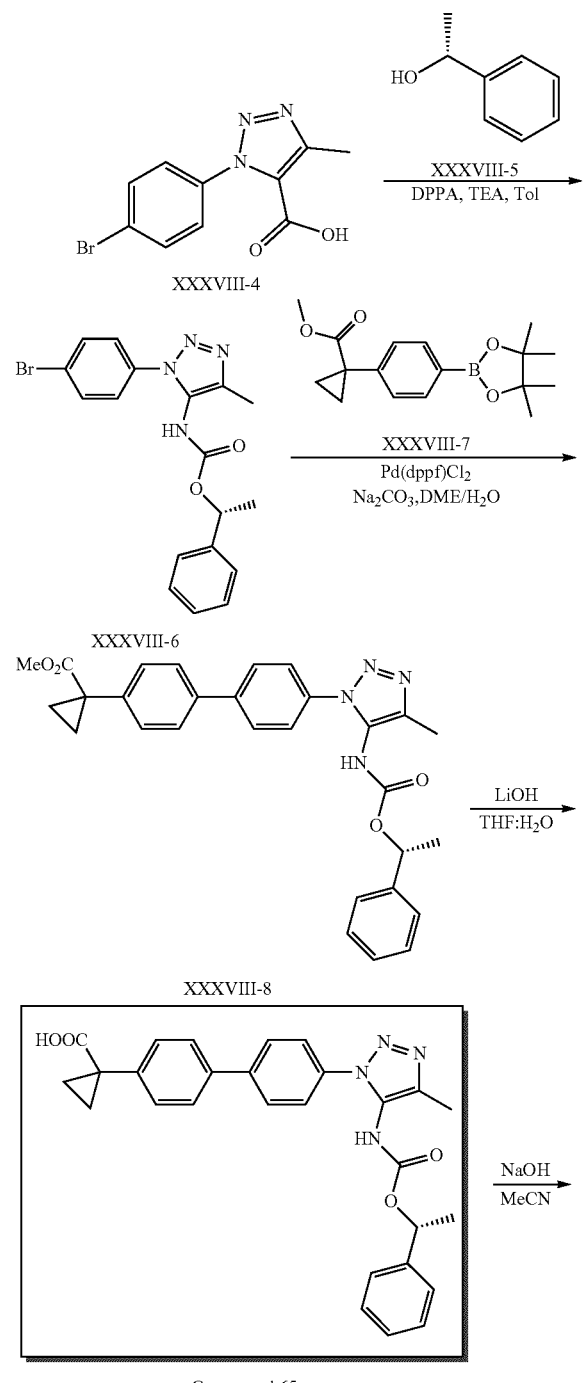

Compound 65

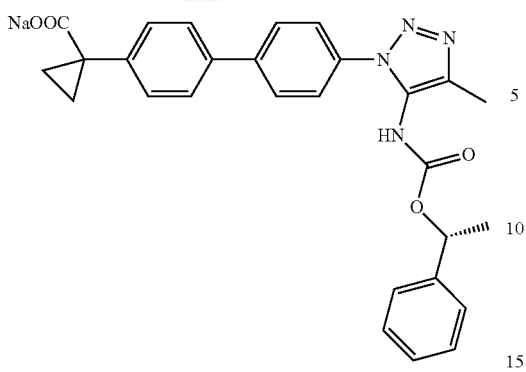

Compound 65a

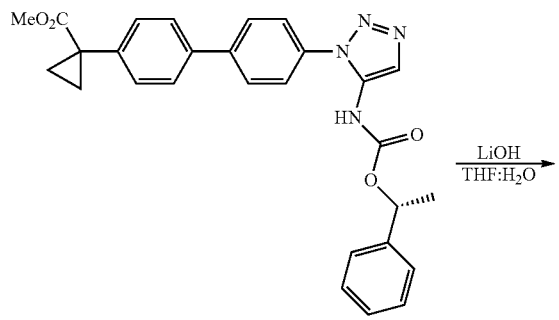

XXXIX-4

Intermediate XXXVIII-4 was prepared by the same synthetic method as described in the synthesis of intermediate XXXVII-4 (Scheme XXXVII).

Compound 65 was prepared analogously to the procedure described in the synthesis of Compound 64. Compound 65: MS (ESI) m/z (M+H)$^+$ 483.2.

Compound 65a was prepared analogously to the procedure described in the synthesis of Compound 64a. Compound 65a: $^1$HNMR (DMSO-d$_6$ 400 MHz) δ 7.73 (d, J=8.4 Hz, 2H), 7.55 (d, J=8.4 Hz, 2H), 7.50 (d, J=8.0 Hz, 2H), 7.24-7.35 m, 7 H), 5.65 (q, J=6.4 Hz, 1 H), 2.11 (s, 3H), 1.37 (br, 3H), 1.19 (br, 2 H), 0.69 (br, 2 H). MS (ESI) m/z (M+H)$^+$ 483.2.

Synthesis of Compound 66

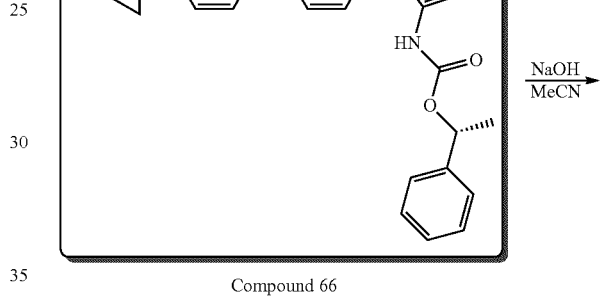

Compound 66

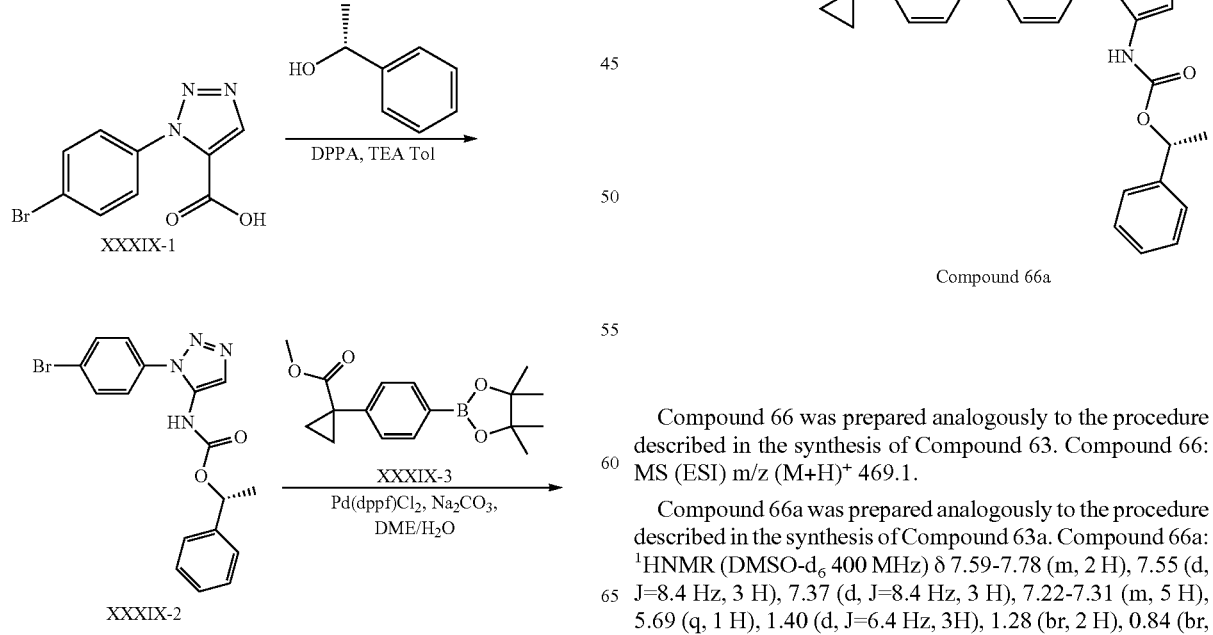

Compound 66a

Compound 66 was prepared analogously to the procedure described in the synthesis of Compound 63. Compound 66: MS (ESI) m/z (M+H)$^+$ 469.1.

Compound 66a was prepared analogously to the procedure described in the synthesis of Compound 63a. Compound 66a: $^1$HNMR (DMSO-d$_6$ 400 MHz) δ 7.59-7.78 (m, 2 H), 7.55 (d, J=8.4 Hz, 3 H), 7.37 (d, J=8.4 Hz, 3 H), 7.22-7.31 (m, 5 H), 5.69 (q, 1 H), 1.40 (d, J=6.4 Hz, 3H), 1.28 (br, 2 H), 0.84 (br, 2 H). MS (ESI) m/z (M+H)$^+$ 469.1.

Synthesis of Compound 67

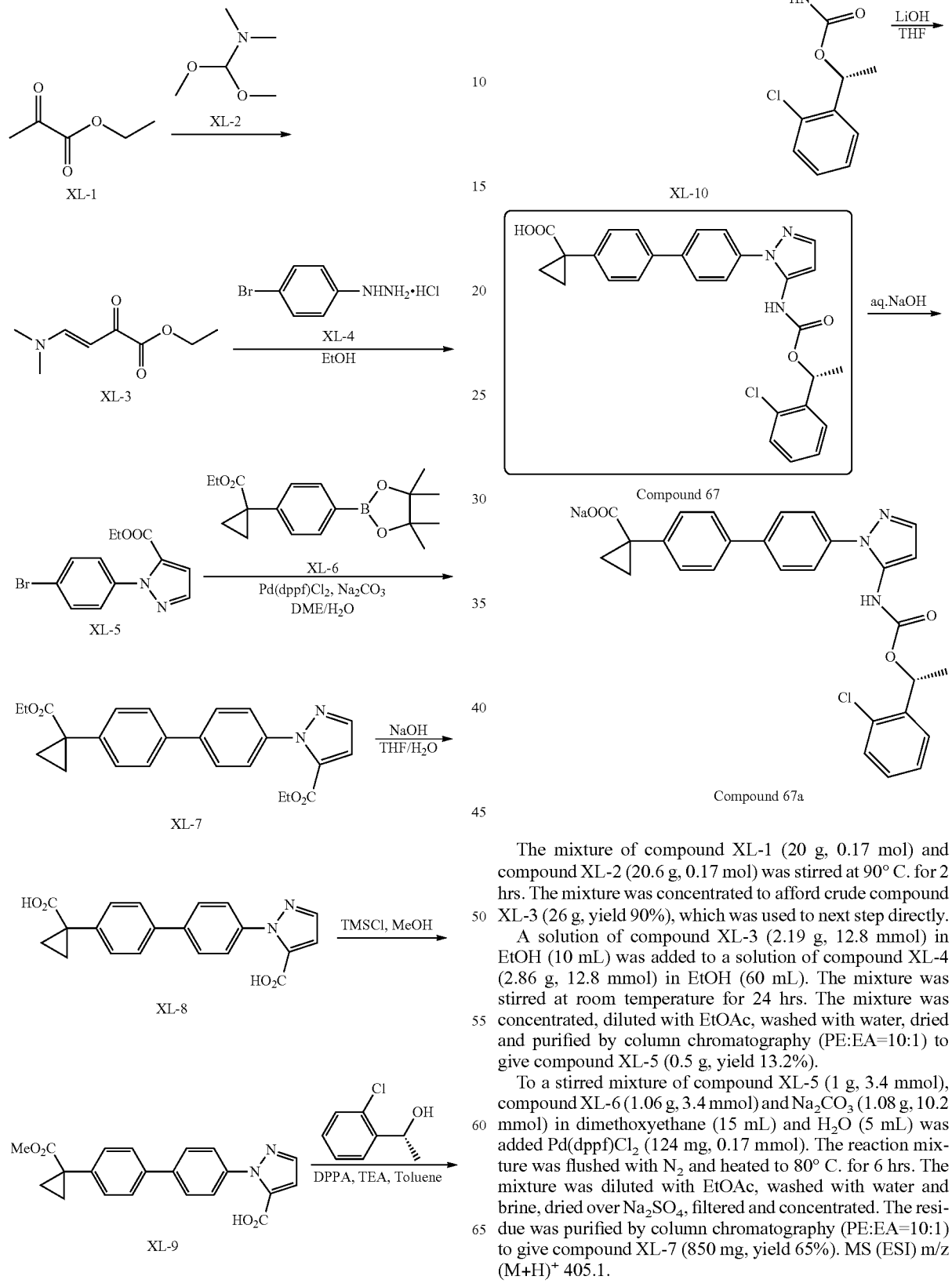

The mixture of compound XL-1 (20 g, 0.17 mol) and compound XL-2 (20.6 g, 0.17 mol) was stirred at 90° C. for 2 hrs. The mixture was concentrated to afford crude compound XL-3 (26 g, yield 90%), which was used to next step directly.

A solution of compound XL-3 (2.19 g, 12.8 mmol) in EtOH (10 mL) was added to a solution of compound XL-4 (2.86 g, 12.8 mmol) in EtOH (60 mL). The mixture was stirred at room temperature for 24 hrs. The mixture was concentrated, diluted with EtOAc, washed with water, dried and purified by column chromatography (PE:EA=10:1) to give compound XL-5 (0.5 g, yield 13.2%).

To a stirred mixture of compound XL-5 (1 g, 3.4 mmol), compound XL-6 (1.06 g, 3.4 mmol) and $Na_2CO_3$ (1.08 g, 10.2 mmol) in dimethoxyethane (15 mL) and $H_2O$ (5 mL) was added Pd(dppf)Cl$_2$ (124 mg, 0.17 mmol). The reaction mixture was flushed with $N_2$ and heated to 80° C. for 6 hrs. The mixture was diluted with EtOAc, washed with water and brine, dried over $Na_2SO_4$, filtered and concentrated. The residue was purified by column chromatography (PE:EA=10:1) to give compound XL-7 (850 mg, yield 65%). MS (ESI) m/z $(M+H)^+$ 405.1.

To a solution of compound XL-7 (100 mg, 0.256 mmol) in THF (6 mL) was added water (2 mL) and sodium hydroxide (51 mg, 1.27 mol). The reaction was stirred at room temperature overnight. The mixture was diluted with water, neutralized to pH=4.0 with 1N hydrochloride solution, extracted with EtOAc (50 mL). The combined organic phase was dried over MgSO$_4$ and concentrated to afford crude compound XL-8 (85 mg, yield 95%), which was used to next step directly.

To a solution of compound XL-8 (90 mg, 0.259 mmol) in MeOH (5 mL) was added TMSCl (28 mg, 0.26 mmol) at 80° C. The reaction mixture was stirred at room temperature for 2 days. The mixture was diluted with water, and extracted with EtOAc (50 mL). The combined organic phase was dried over MgSO$_4$ and concentrated. The residue was purified by Prep. TLC (DCM:MeOH=10:1) to give compound XL-9 (10 mg, yield 10.7%).

To a solution of compound XL-9 (100 mg, 0.276 mmol) in dry toluene (5 mL) was added (R)-1-(2-chlorophenyl)ethanol (50 mg, 0.331 mmol), triethylamine (55 mg, 0.552 mmol) and DPPA (90 mg, 0.331 mmol). The reaction mixture was heated to 80° C. overnight. The mixture was diluted with EtOAc (50 mL), washed with brine, dried over MgSO$_4$, filtered and concentrated. The residue was purified by Prep. TLC (PE:EA=5:1) to give compound XL-10 (40 mg, yield 28%). MS (ESI) m/z (M+H)$^+$ 516.1.

Preparation of Compound 67

To a solution of compound XL-10 (100 mg, 0.19 mmol) in THF (6 mL) was added water (2 mL) and lithium monohydrate (40 mg, 0.95 mmol). The reaction mixture was stirred at room temperature overnight. The mixture was neutralized to pH=4.0 with 1N hydrochloride solution, extracted with EtOAc (20 mL). The combined organic phase was dried over MgSO$_4$ and concentrated. The residue was purified by prep. HPLC to give Compound 67 (91 mg, yield 90.9%).

Preparation of Compound 67a

To a solution of Compound 67 (91 mg, 0.182 mmol) in MeOH (2 mL) was added 0.1N sodium hydroxide solution (1.8 mL). The reaction mixture was stirred at r.t. for 30 minutes. The mixture was lyophilized to give Compound 67a (91 mg, yield 100%). $^1$HNMR: (DMSO-d6 400 MHz) δ 7.65-7.74 (m, 4H), 7.28-7.52 (m, 9H), 6.32 (s, 1H), 5.93 (q, 1H), 1.41 (d, J=6.0 Hz, 3H), 1.23 (br, 2H), 0.74 (br, 2H). MS (ESI) m/z (M+H)$^+$ 502.1

Synthesis of Compound 68

Synthetic Route (Scheme XLI)

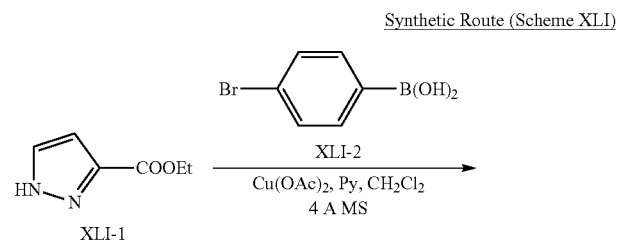

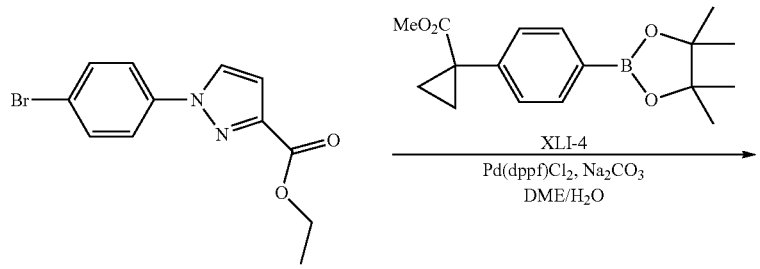

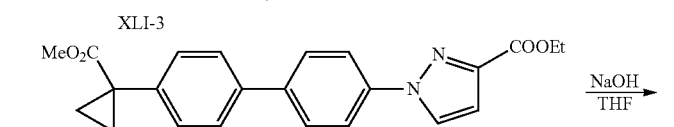

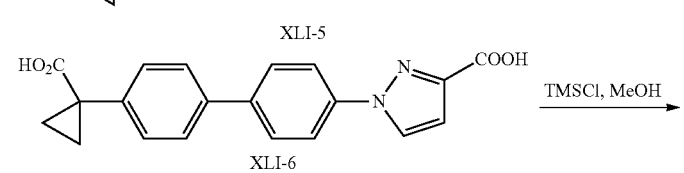

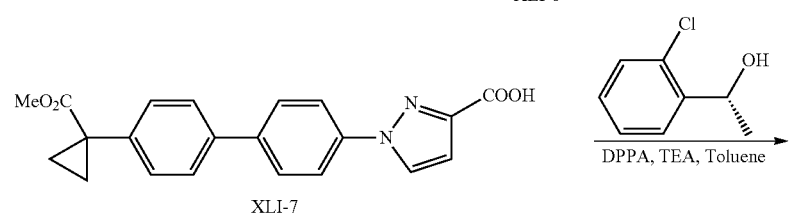

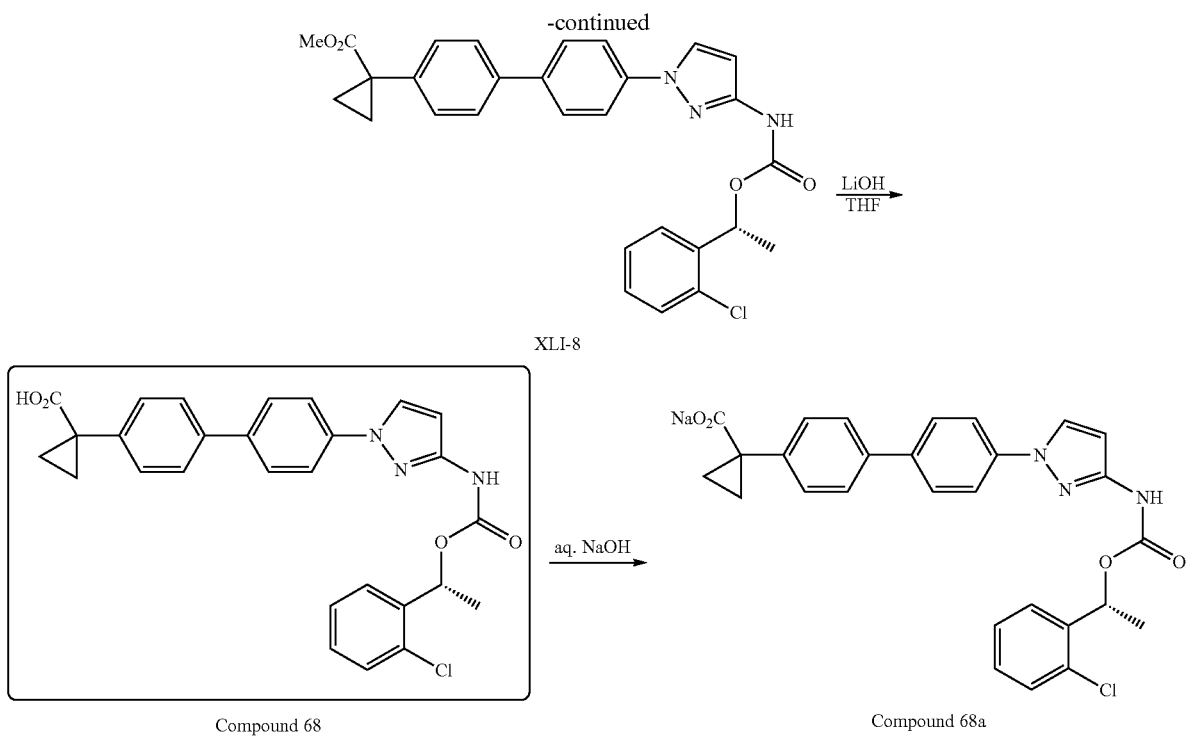

Compound 68 → Compound 68a (aq. NaOH)

To a mixture of compound XLI-1 (3.7 g, 26.6 mmol), compound XLI-2 (10.6 g, 53.4 mmol), Cu(OAc)$_2$ and Py. in dichloromethane (400 mL) was added to powdered 4 A molecular sieves. The reaction mixture was flushed with O$_2$ and stirred at room temperature for 16 hours. The mixture was filtered through celite, the filtrated was concentrated, and the residue was purified by column chromatography (PE:EA=10:1) to give compound XLI-3 (4.5 g, yield 57.5%).

Compound 68 was prepared analogously to the procedure described in the synthesis of Compound 67 (30 mg, yield 68%). MS (ESI) m/z (M+H)$^+$ 502.2. Compound 68a was prepared analogously to the procedure described in the synthesis of Compound 67a. $^1$HNMR (DMSO-d$_6$ 400 MHz) δ 8.52 (s, 1H), 7.93-7.95 (m, 3H), 7.78 (d, J=7.2 Hz, 2H), 7.61 (s, 2H), 7.28-7.41 (m, 5H), 6.94 (s, 1H), 5.96 (q, 1H), 1.45 (d, J=5.2 Hz, 3H), 1.20-1.26 (m, 4H). MS (ESI) m/z (M+H)$^+$ 502.2.

Synthesis of Compound 69

Synthetic Route (Scheme XLII)

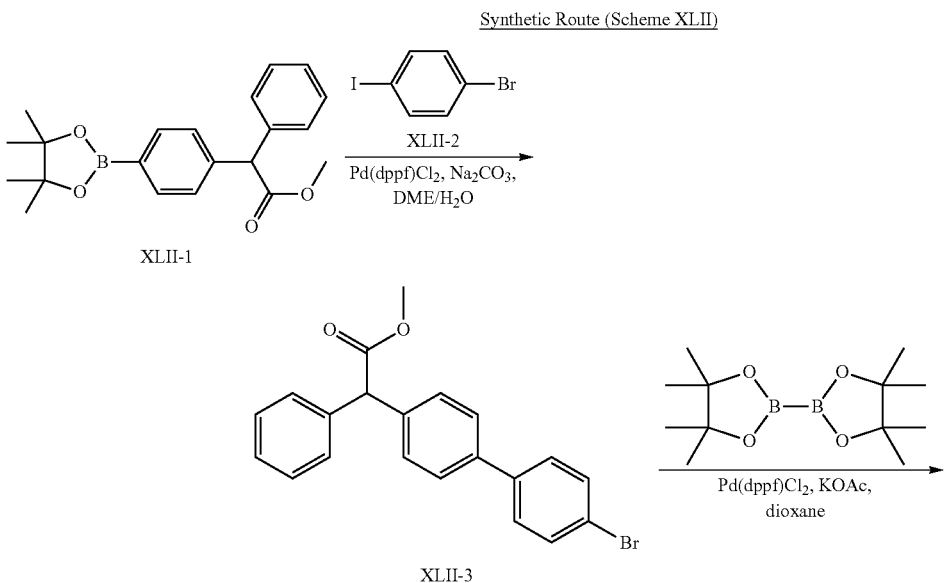

-continued

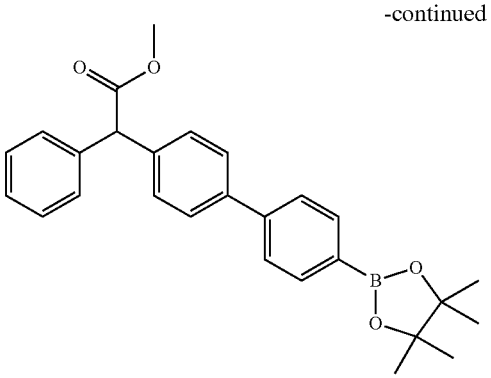

XLII-4

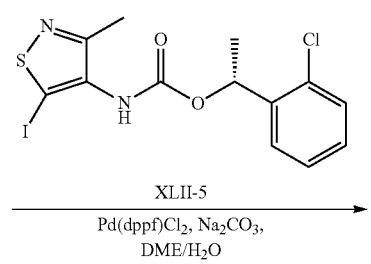

XLII-5
—————————→
Pd(dppf)Cl$_2$, Na$_2$CO$_3$,
DME/H$_2$O

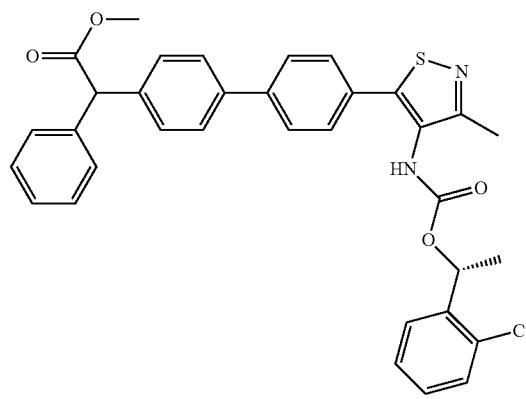

XLII-6 aq. LiOH
————→
MeOH

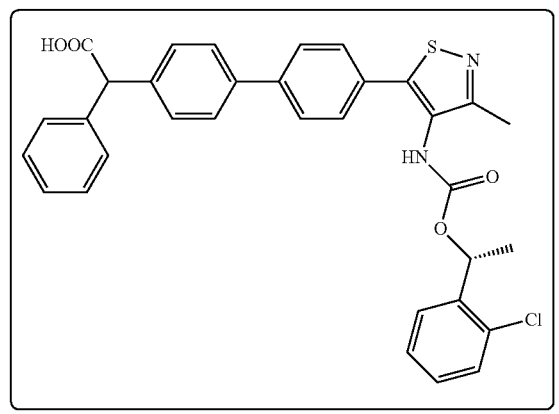

Compound 69

The mixture of compound XLII-1 (4 g, 11.36 mmol), compound XLII-2 (3.52 g, 12.5 mmol), Na$_2$CO$_3$ (2.4 g, 22.72 mmol) and Pd(dppf)Cl$_2$ (930 mg, 1.14 mmol) in 160 mL of DME:H$_2$O (v/v=3/1) was heated to reflux under nitrogen for 2 hours. The mixture was concentrated, and the residue was partitioned between H$_2$O (100 mL) and DCM (100 mL), the aqueous phase was extracted with DCM (100 mL). The combined organic layer was washed with brine, dried over Na$_2$SO$_4$, concentrated. The residue was purified by chromatography on silica gel (PE:EA=10:1) to afford compound XLII-3 (2.5 g, yield 58.1%). MS (ESI) m/z (M+H)$^+$ 381.0.

Compound 69 was prepared analogously to the procedure described in the synthesis of Compound 32. Compound 69: $^1$H NMR (DMSO 400 MHz): δ 9.45 (s, 1H), 7.68-7.70 (m, 2H), 7.53-7.55 (m, 5H), 7.44-7.46 (m, 6H), 7.21-7.22 (m, 1H), 7.19-7.23 (m, 2H), 7.08-7.10 (m, 1H), 5.94-5.96 (m, 1H), 4.67 (s, 1H), 2.24 (s, 3H), 1.51 (d, J=6.4 Hz, 3H). MS (ESI) m/z (M+H)$^+$ 583.1.

Preparation of Compound 70 and Compound 71

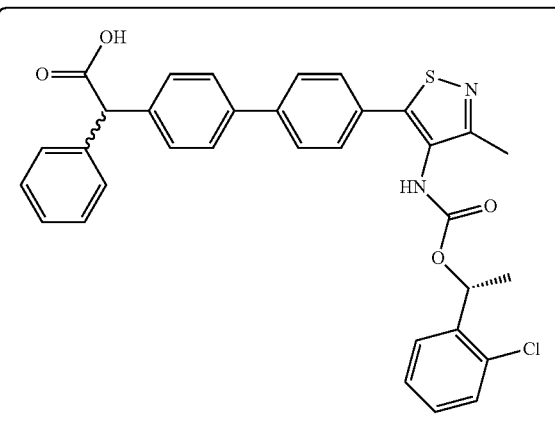

Compound 70

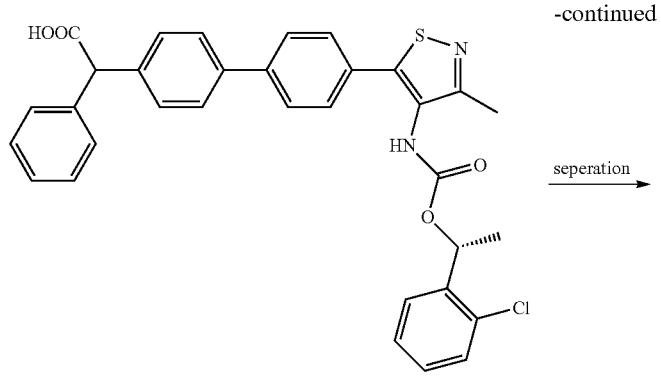
Compound 69
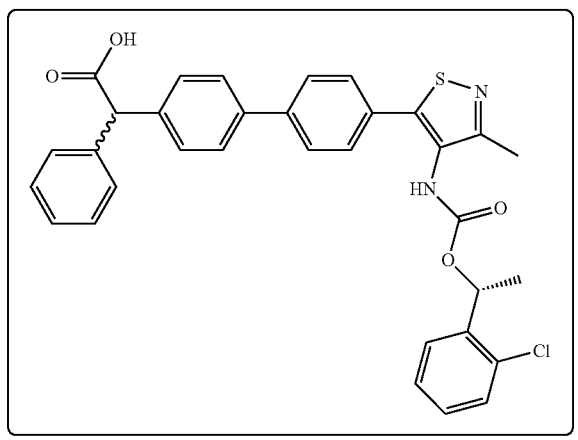
Compound 71
0.2 g of Compound 69 was separated by SFC to afford Compound 70 (77 mg) and Compound 71 (100 mg). Compound 70: ¹H NMR (DMSO 400 MHz) δ9.47 (s, 1H), 7.70-7.72 (m, 2H), 7.55-7.57 (m, 5H), 7.46-7.48 (m, 6H), 7.21-7.20 (m, 1H), 7.19-7.18 (m, 2H), 7.10-7.07 (m, 1H), 5.98-5.94 (m, 1H), 4.68 (s, 1H), 2.22 (s, 3H), 1.51 (d, J=5.6 Hz, 3H). MS (ESI) m/z (M+H)⁺ 583.1. Compound 71: ¹H NMR (DMSO 400 MHz) δ 9.39 (s, 1H), 7.70-7.71 (m, 2H), 7.57-7.59 (m, 5H), 7.46-7.48 (m, 6H), 7.19-7.21 (m, 3H), 7.17-7.19 (m, 1H), 5.97-5.96 (m, 1H), 4.95 (s, 1H), 2.33 (s, 3H), 1.51 (d, J=6.4 Hz, 3H). MS (ESI) m/z (M+H)⁺ 583.1.
Synthesis of Compound 72
Synthetic Route (Scheme XLIII)
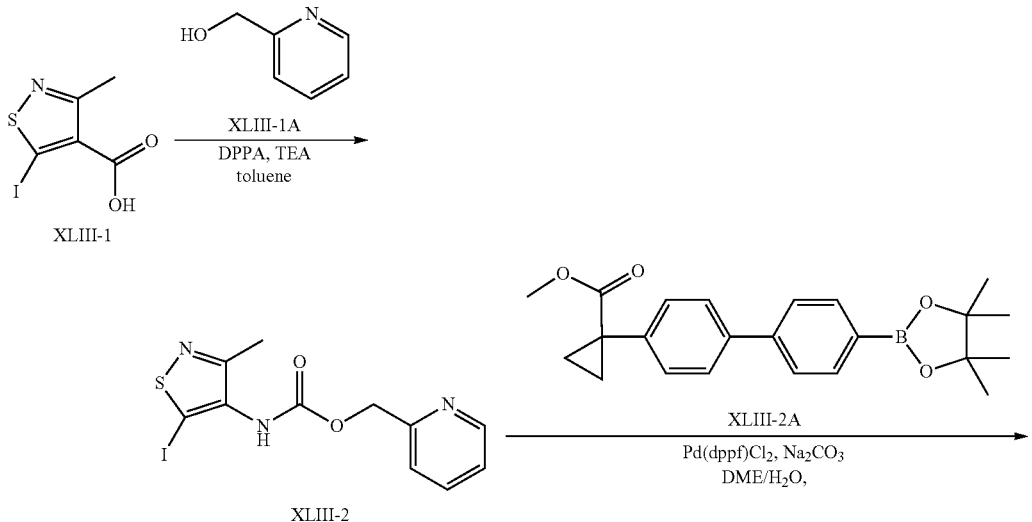

-continued

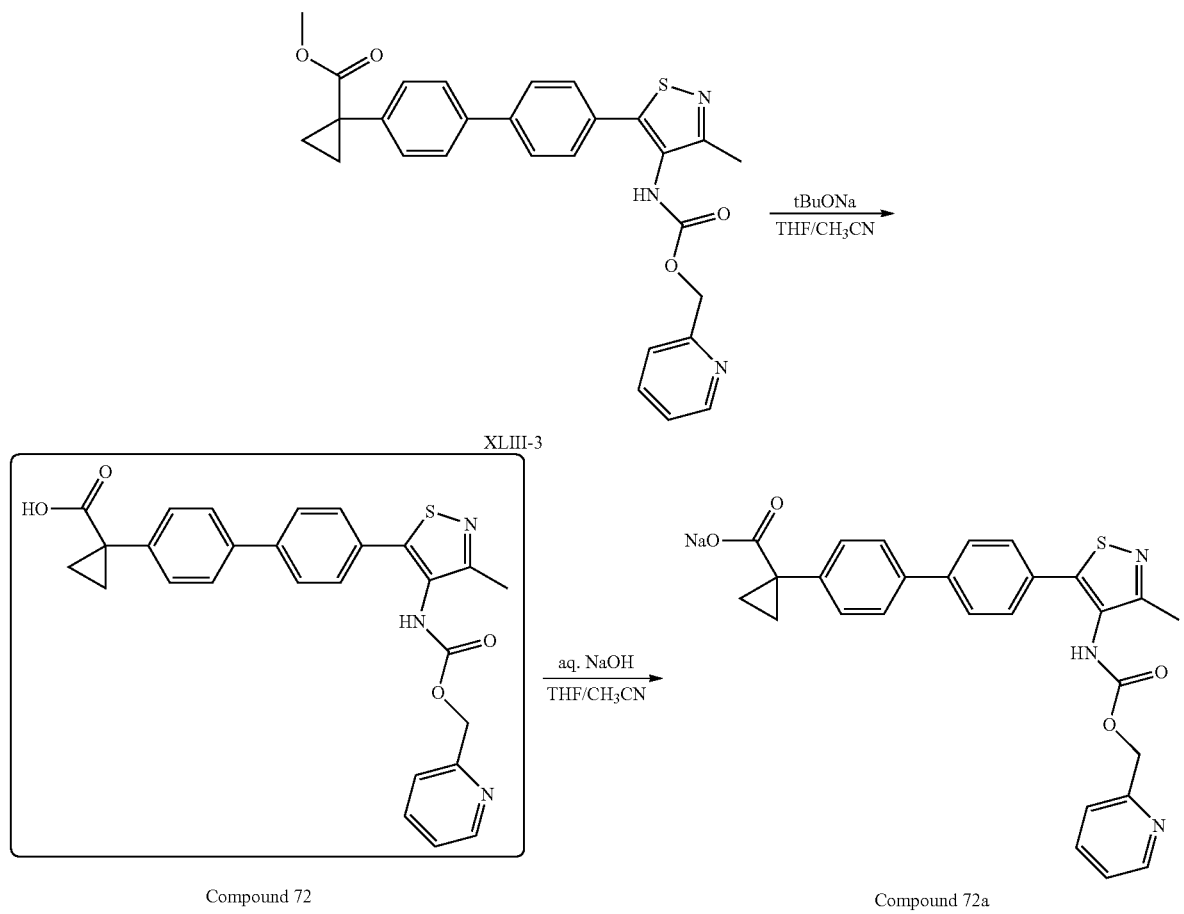

Compound 72

Compound 72a

To a stirred solution of compound XLIII-1 (1 g, 3.72 mmol), compound XLIII-1A (0.49 g 4.46 mmol), TEA (0.75 g 7.44 mmol) in toluene (30 mL) was added DPPA (1.23 g, 4.46 mmol) under nitrogen. After the addition, the solution was heated to reflux under nitrogen for 2 hours. The solution was concentrated, then $H_2O$ (20 mL) was added, and the mixture was extracted with EtOAc (50 mL×3). The organic layer was combined and washed with brine, dried over $Na_2SO_4$, concentrated in vacuo. The residue was purified by column chromatography on silica gel (Petroleum ether: EtOAc=10:1) to afford compound XLIII-2 (0.45 g, yield 32%). MS (ESI) m/z $(M+H)^+$ 375.1.

Compound 72 was prepared analogously to the procedure described in the synthesis of Compound 44. Compound 72: MS (ESI) m/z $(M+H)^+$ 486.0.

Compound 72a was prepared analogously to Compound 44a. Compound 72a: $^1H$ NMR (DMSO-$d_6$, 400 MHz): δ 8.55 (d, J=4.4 Hz, 1H), 7.77-7.78 (m, 3H), 7.64 (d, J=8.4 Hz, 2H), 7.51 (d, J=8.4 Hz, 2H), 7.40 (d, J=8.4 Hz, 2H), 7.28-7.39 (m, 2H), 5.18 (s, 2H), 2.34 (s, 3H), 1.27-1.24 (br, 2H), 0.73-0.7 (br, 2H). MS (ESI) m/z $(M+H)^+$ 486.1.

Synthesis of Compound 73

Synthetic Route (Scheme XLIV)

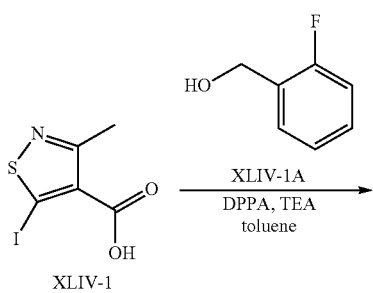

-continued

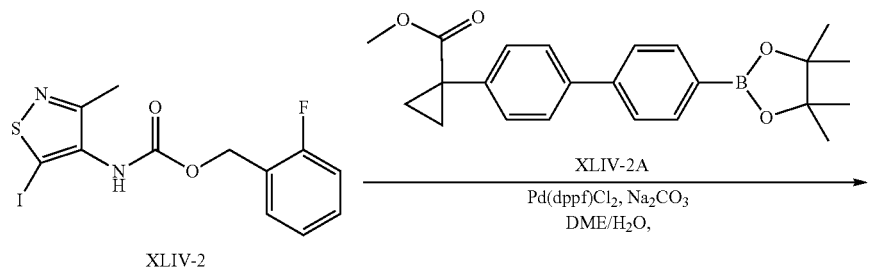

XLIV-2

XLIV-2A
Pd(dppf)Cl$_2$, Na$_2$CO$_3$
DME/H$_2$O,

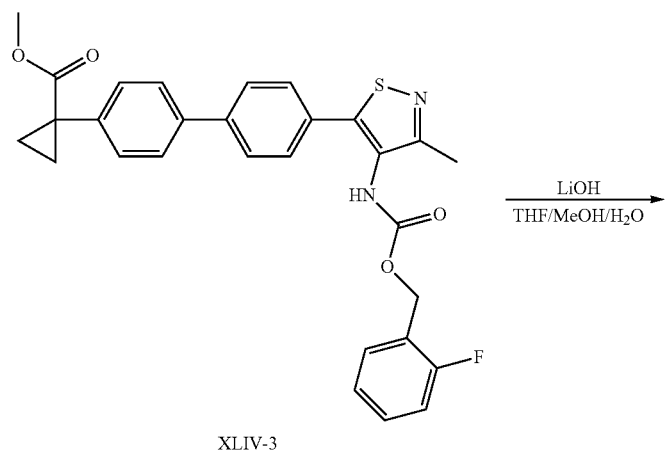

XLIV-3

LiOH
THF/MeOH/H$_2$O

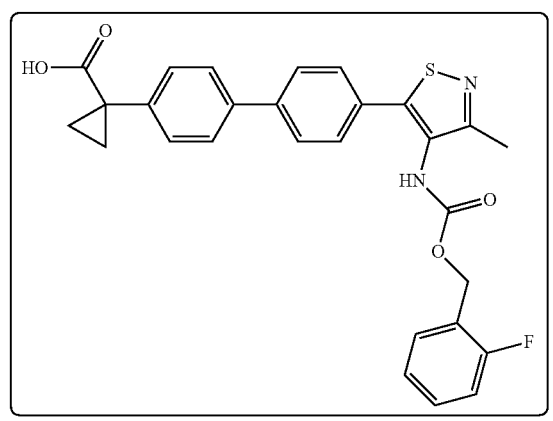

Compound 73 aq. NaOH

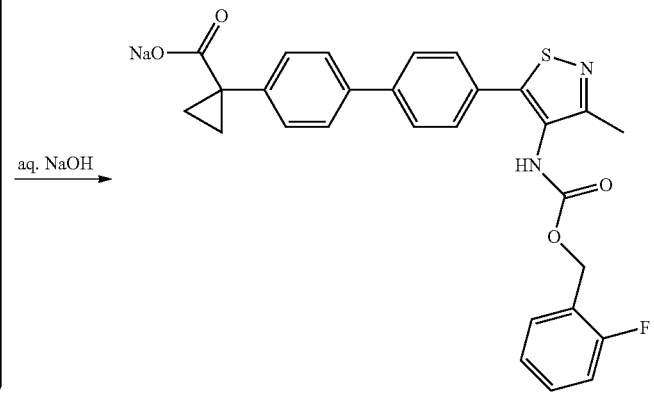

Compound 73a

Compound 73 was prepared analogously to the procedure described in the synthesis of Compound 44. Compound 73: MS (ESI) m/z (M+H)$^+$ 503.1.

Compound 73a was prepared analogously to the procedure described in the synthesis of Compound 44a. Compound 73a: $^1$H NMR (DMSO-d$_6$, 400 MHz): δ 9.017 (s, 1H), 7.72 (d, J=8.4 Hz, 2H), 7.57-7.61 (m, 4H), 7.37-7.44 (m, 4H), 7.17-7.23 (m, 2H), 5.18 (s, 2H), 2.31 (s, 3H), 1.40 (br, 2H), 0.99 (br, 2H) MS (ESI) m/z (M+H)$^+$ 503.1.

Synthesis of Compound 74
Synthetic Route (Scheme XLV)
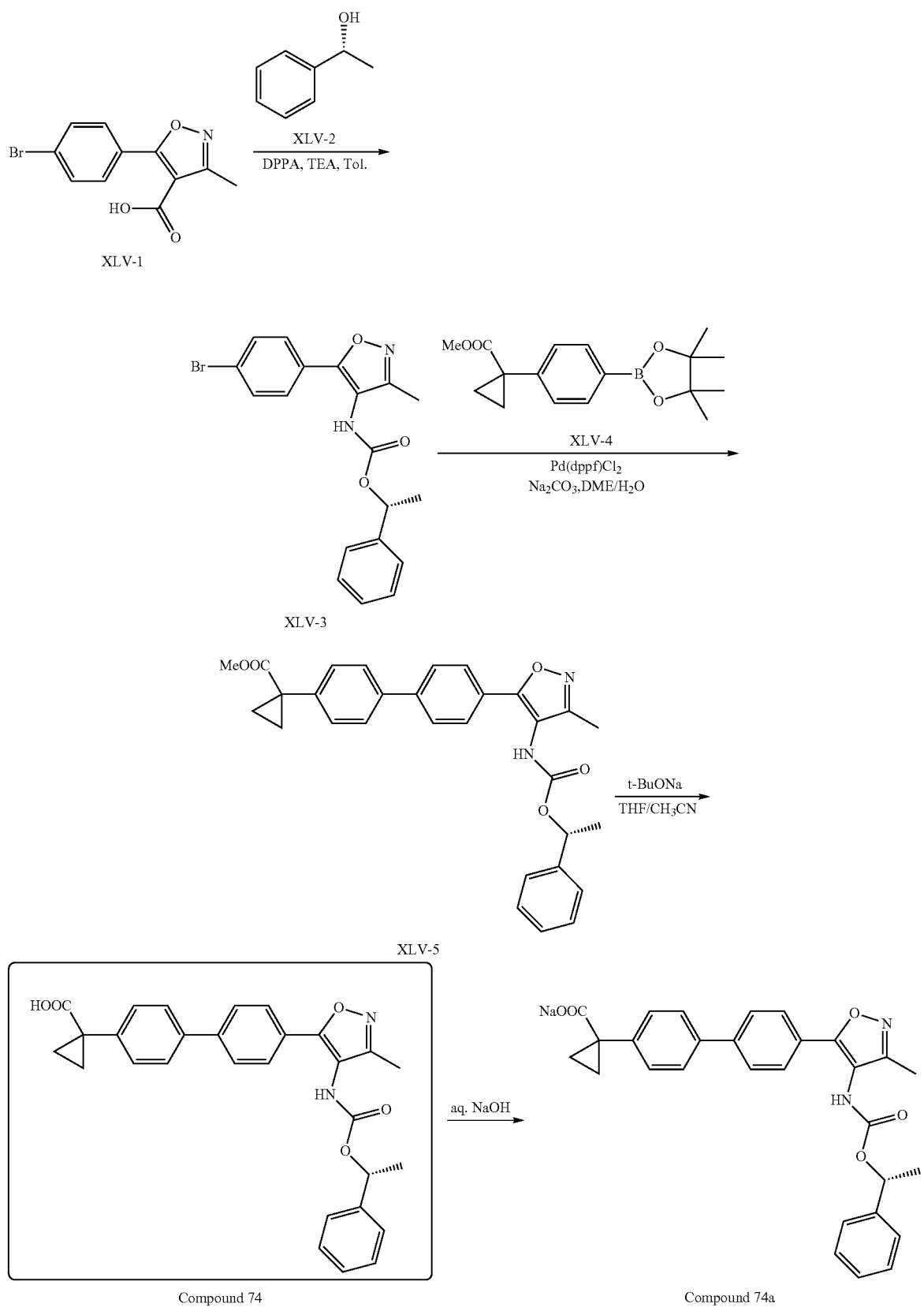
Compound 74
Compound 74a Compound XLV-1 was prepared by the same method as described in the synthesis of compound 1-4 (Scheme 1-A).

To a solution of compound XLV-1 (8 g, 28.08 mmol) in dry toluene (150 mL) was added compound XLV-2 (1.58 g, 10.1 mmol), triethylamine (8.0 mL) and DPPA (9.2 g, 33.6 mmol). The reaction mixture was heated to 80° C. for 3 hours. The mixture was diluted with EtOAc (50 mL), washed with brine, dried over $Na_2SO_4$, filtered and concentrated. The residue was purified by column chromatography (PE/EA=10/1) to give compound XLV-3 (9.4 g, yield: 83%). MS (ESI) m/z $(M+H)^+$ 402.0.

Compound 74 was prepared analogously to the procedure described in the synthesis of Compound 28 and was carried through without further characterization.

Compound 74a was prepared analogously to the procedure described in the synthesis of Compound 44a. Compound 74a: $^1$HNMR (DMSO-$d_6$ 400 MHz) δ 7.81 (d, J=8.4 Hz, 2H), 7.41 (d, J=8.4 Hz, 2H), 7.52 (d, J=8.4 Hz, 2H), 7.29-7.32 (m, 7 H), 5.78 (q, 1 H), 2.15 (s, 3 H), 1.52 (d, J=6.0 Hz, 3H), 1.28 (br, 2 H), 0.74 (br, 2 H). MS (ESI) m/z $(M+H)^+$ 483.1.

Synthesis of Compound 75

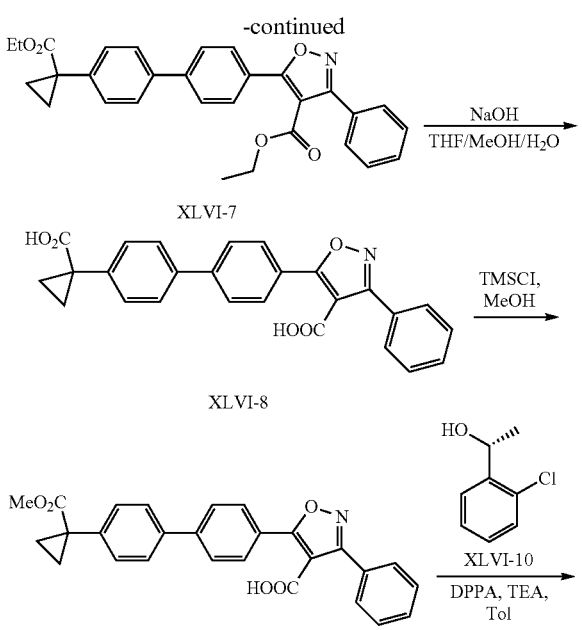

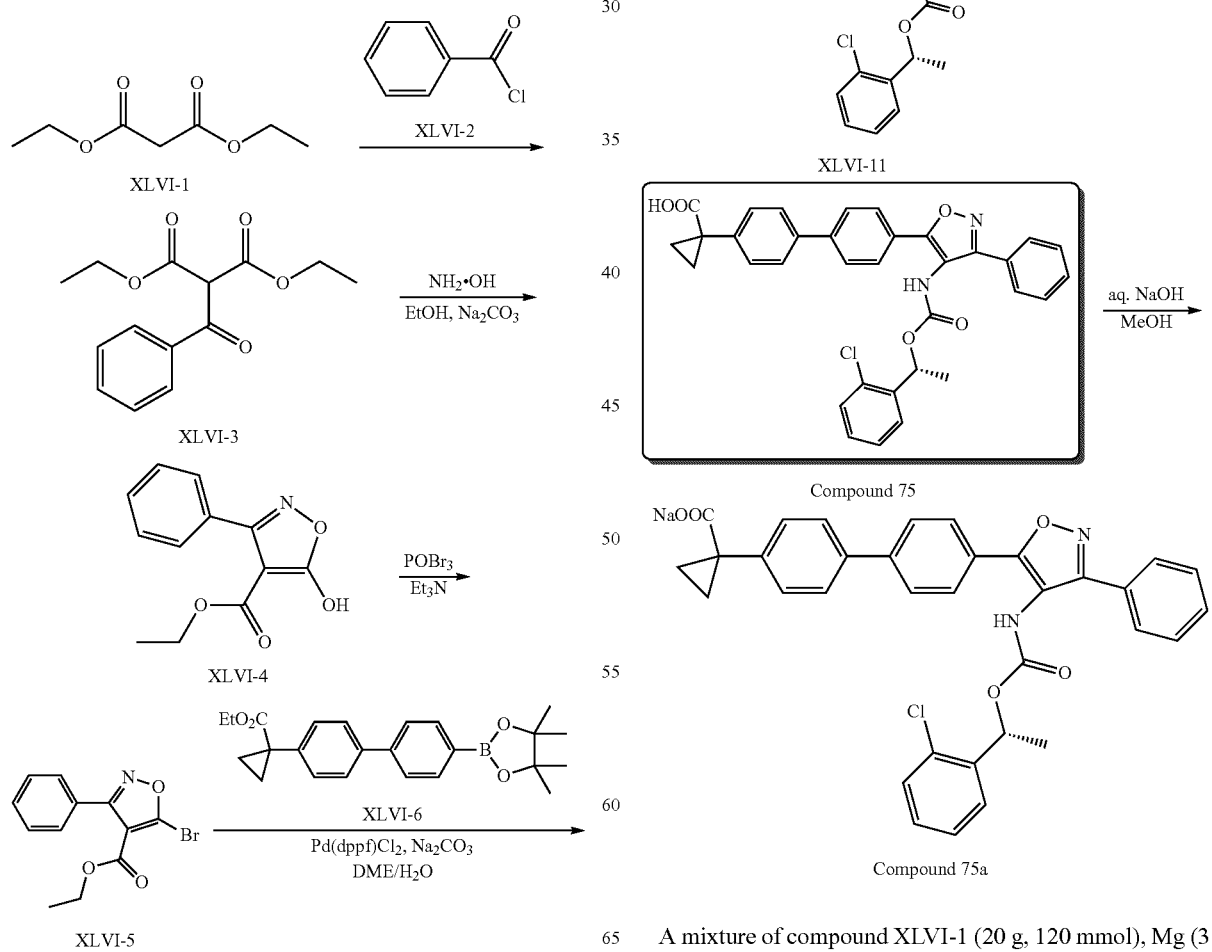

Compound 75

Compound 75a

A mixture of compound XLVI-1 (20 g, 120 mmol), Mg (3 g, 121 mmol), ethanol/$CCl_4$ (30 mL/3 mL) and anhydrous toluene (300 mL) was stirred under argon at r.t for 0.5 hours, then at refluxed for 1 h. After being cooled to 0-5° C., compound XLVI-2 (16.4 g, 121 mmol) was added dropwise over 30 min. and the reaction mixture was stirred at r.t for 1 h. The reaction mixture was washed with aq. HCl (1N), aq.NaHCO$_3$ and brine, dried over MgSO$_4$, filtered and concentrated to afford crude compound XLVI-3 (25.0 g, yield: 76%), which was used directly for next step.

To a solution of compound XLVI-3 (34 g, 128.8 mmol) in ethanol (200 mL) was added HONH$_2$.HCl (9.8 g, 141.6 mmol), Na$_2$CO$_3$ (3.4 g, 64.4 mmol). The reaction mixture was heated to 90° C. overnight. The mixture was concentrated, and the solid was collect by filtrated, wash with EtOAc to give compound XLVI-4 (14 g, yield: 47%). MS (ESI) m/z (M+H)$^+$ 234.1.

A mixture of compound XLVI-4 (2 g, 8.5 mmol), POBr$_3$ (19.6 g, 68.6 mmol) and TEA (1.14 mL, 8.5 mmol) was stirred at 50° C. overnight. The reaction mixture was quenched by ice water, extracted with EtOAc (50 mL×3). The combined organic phase was dried over Na$_2$SO$_4$, filtered and concentrated. The residue was purified by column to give compound XLVI-5 (400 mg, yield: 16%). MS (ESI) m/z (M+H)$^+$ 297.1.

To a stirred mixture of compound XLVI-5 (1.2 g, 4.05 mmol), compound XLVI-6 (1.53 g, 4.05 mmol), and Na$_2$CO$_3$ (945 mg, 8.91 mmol) in DME (40 mL) and H$_2$O (10 mL) was added Pd(dppf)Cl$_2$ (296 mg, 0.405 mmol). The reaction mixture was flushed with nitrogen and heated to 90° C. overnight. The mixture was diluted with EtOAc (150 mL), washed with water and brine, dried over Na$_2$SO$_4$, filtered and concentrated. The residue was purified by column (PE:EA=10:1) to give compound XLVI-7 (1.36 g, yield: 92%). MS (ESI) m/z (M+H)$^+$ 482.1.

To a solution of compound XLVI-7 (820 mg, 1.76 mmol) in THF/MeOH/water (10 mL/10 mL/10 mL) was added sodium hydroxide (840 mg, 21 mmol). The reaction was stirred at room temperature overnight. The mixture was diluted with water, acidified to pH=4.0 with 1N hydrochloride solution, and extracted with EtOAc (50 mL×2). The combined organic phase was dried over MgSO$_4$ and concentrated to afford compound XLVI-8 (740 mg, yield: 75%), which was used directly for next step.

Compound 75 was prepared analogously to the procedure described in the synthesis of Compound 28 (80 mg, yield: 59%) and was carried through without characterization.

Compound 75a was prepared analogously to the procedure described in the synthesis of Compound 44a (82 mg, yield: 92%). $^1$H NMR: (400 MHz, DMSO-d$_6$) δ 7.89-7.91 (m, 2 H), 7.75-7.80 (m, 4 H), 7.32-7.56 (m, 11 H), 5.96 (br, 1 H), 1.47 (br, 3 H), 1.28 (brs, 2 H), 1.28 (brs, 2 H). MS (ESI) m/z (M+H)$^+$ 479.1.

Synthesis of Compound 76

Synthetic Route (Scheme XLVII)

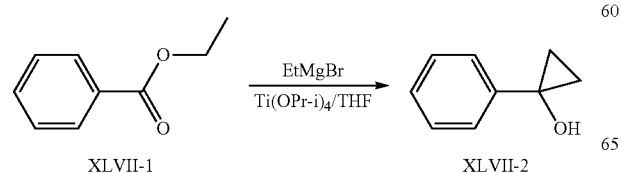

XLVII-1    XLVII-2

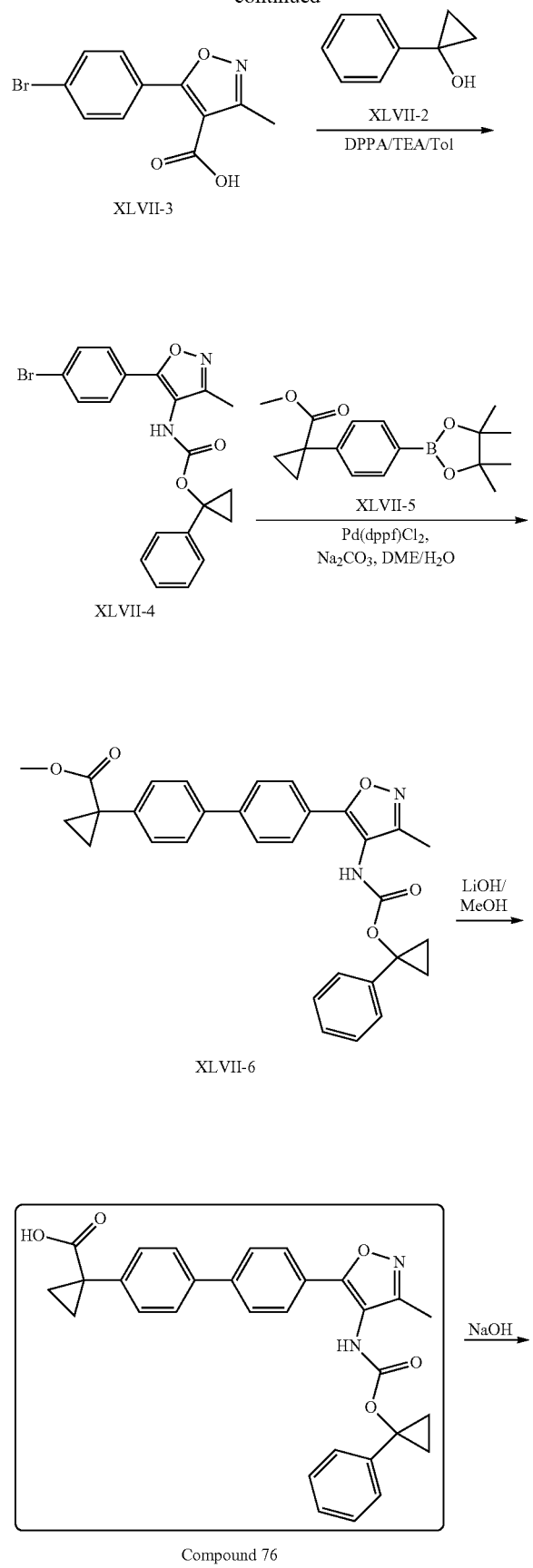

Compound 76

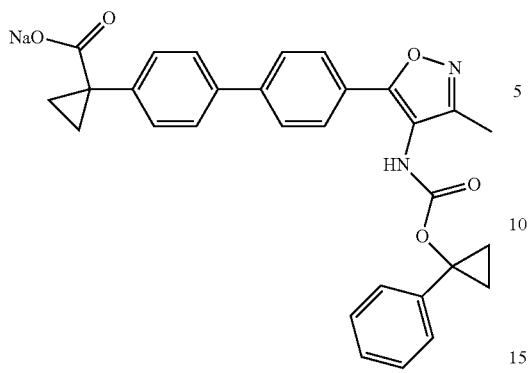
Compound 76a
Compound 76 was prepared analogously to Compound 28. Compound 76: MS (ESI) m/z (M+H)$^+$ 495.2. Compound 76a was prepared analogously to Compound 28a. Compound 76a: $^1$H NMR: (400 MHz, DMSO-d$_6$) δ 9.48 (s, 1 H), 7.77-7.83 (m, 4 H), 7.54-7.56 (m, 2 H), 7.35-7.38 (m, 4 H), 7.26-7.28 (m, 2 H), 2.14 (s, 3 H), 1.40 (br, 2H), 1.28 (br, 2H), 1.21 (br, 2H), 0.71 (br, 2H). MS (ESI) m/z (M+H)$^+$ 495.2.
Synthesis of Compound 77
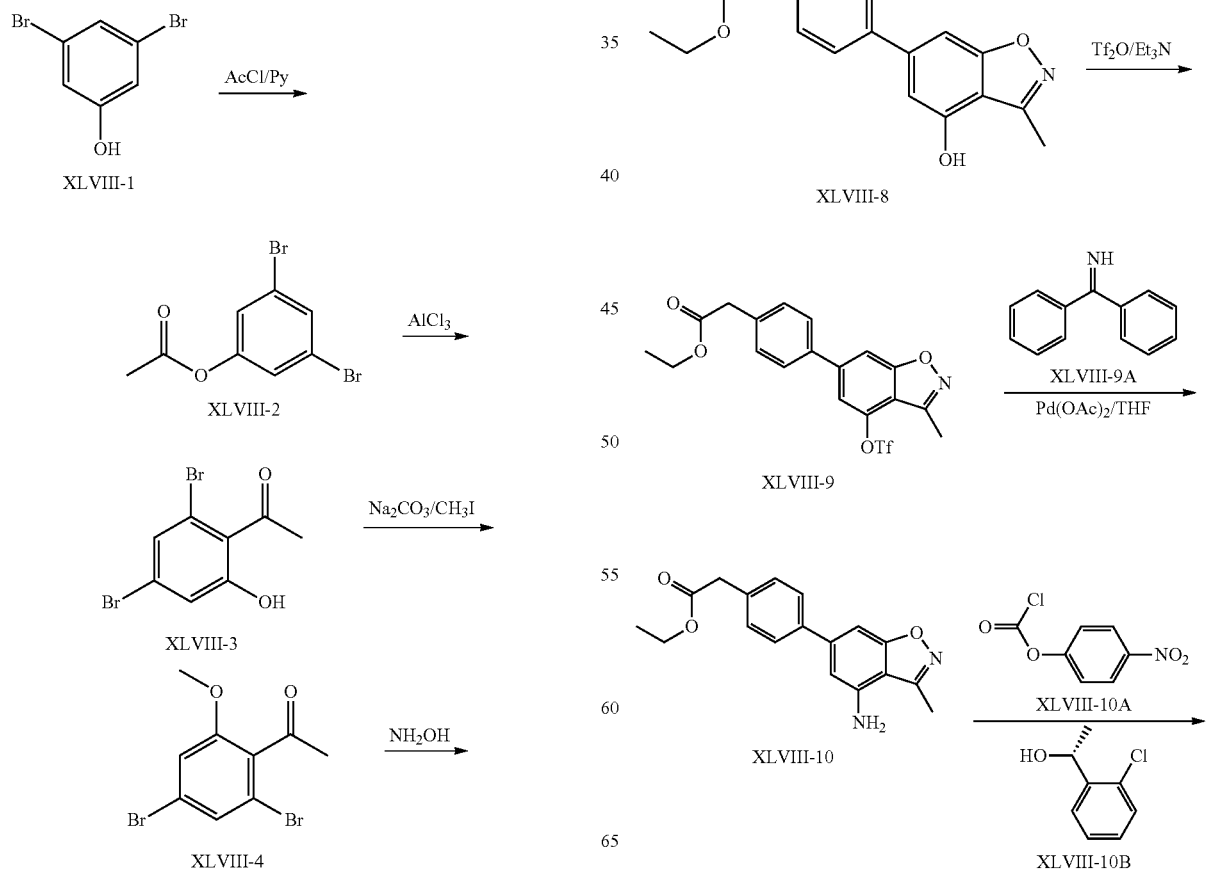

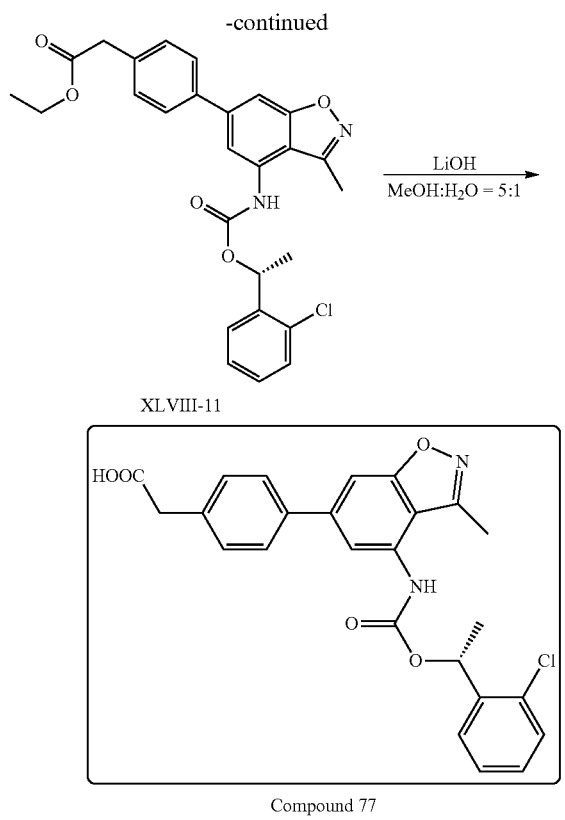

Compound 77

To a stirred solution of compound XLVIII-1 (10.00 g, 39.69 mmol) in DCM (20 mL) and Py (50 mL) was added dropwise acetyl chloride (3.73 g, 47.51 mmol) at 0° C. under argon. After the addition, the solution was stirred overnight at room temperature. TLC monitored the reaction. After completion of the reaction, the mixture was poured into ice/water (100 mL), extract with DCM (50 mL×3), the combined organic layers were dried over Na$_2$SO$_4$, concentrated in vacuo. The residue was purified by column chromatography (PE:EA=100:1) to afford compound XLVIII-2 (11.67 g, yield: 92%).

A stirred solution of compound XLVIII-2 (8.00 g, 54.43 mmol) and AlCl$_3$ (7.26 g, 54.43 mmol) was heated to 160° C. for 3 hours under argon. The solution was quenched with water, extract with EtOAc (60 mL×3), the combined organic layers were dried over Na$_2$SO$_4$, concentrated in vacuo, and purified by chromatography (PE:EA=50:1) to afford compound XLVIII-3 (6.5 g, yield 81.25%). $^1$H NMR (400 MHz, DMSO-d$_6$) δ10.94 (s, 1 H), 7.32 (s, 1H), 7.07 (s, 1 H), 2.43 (s, 3 H).

To a stirred solution of compound XLVIII-3 (5.00 g, 17.10 mmol) and Na$_2$CO$_3$ (3.52 g, 25.5 mmol) in DMF (50 mL) was added dropwise CH$_3$I (5.8 g, 40.8 mmol) at 0° C. under argon. After the addition, the solution was stirred overnight at room temperature. After completion of the reaction, the mixture was poured into water, and extract with DCM (50 mL×3), the combined organic layers were dried over Na$_2$SO$_4$, concentrated in vacuo. The residue was purified by chromatography (PE:EA=80:1) to afford compound XLVIII-4 (5.1 g, yield: 98.1%).

A stirred solution of compound XLVIII-4 (5.1 g, 16.61 mmol) and hydroxylamine hydrochloride (5.77 g, 83.03 mmol) in Py (50 mL) was heated to 130° C. for 6 hours under argon. The solution was concentrated in vacuo. The crude material was taken up with water, extract with EtOAc (60 mL×3). The combined organic layers were dried over Na$_2$SO$_4$, concentrated in vacuo to afford compound XLVIII-5 (5.2 g, yield: 97%), which was used to next step directly.

To a stirred solution of compound XLVIII-5 (4.9 g, 15.2 mmol), CuI (289 mg, 1.52 mmol) and DMEDA (401 mg, 4.65 mmol) in THF (30 mL) was added t-BuONa (2.92 g, 30.4 mmol) at room temperature under argon. After the addition, the solution was stirred for 1 hour at room temperature. Then the solution was quenched with water and extract with EtOAc (60 mL×3). The combined organic layers were dried over Na$_2$SO$_4$, concentrated in vacuo. The residue was purified by column chromatography (PE:EA=100:1) to afford compound XLVIII-6 (1.13 g, yield: 30.7%).

To a stirred solution of XLVIII-6 (626 mg, 2.59 mmol) in DCM (10 mL) was added dropwise BBr$_3$ (1 mL, 10.4 mmol) at 0° C. under argon. The reaction mixture was stirred at reflux overnight. After being cooled to r.t., the mixture was poured into water, and extract with DCM (50 mL×3). The combined organic layers were dried over Na$_2$SO$_4$, concentrated in vacuo. The residue was purified by column chromatography (PE:EA=50:1) to afford compound XLVIII-7 (11.67 g, yield 92%).

To a solution of compound XLVIII-7 (694 mg, 3.04 mmol), Na$_2$CO$_3$ (645 mg, 6.08 mmol) and compound 7A (883 g, 3.04 mmol) in DME:H$_2$O=3:1 (20 mL) were added Pd(dppf)Cl$_2$ (111 mg, 0.15 mmol), the resulting mixture was purged with nitrogen. The reaction mixture was stirred at 80° C. overnight under nitrogen protection. After completion of the reaction, the mixture was poured into water, extract with EtOAc (30 mL×3). The combined organic layers were dried over Na$_2$SO$_4$, concentrated in vacuo. The residue was purified by column chromatography (PE:EA=2:1) to afford compound XLVIII-8 (650 mg, yield: 68.6%). MS (ESI) m/z (M+1)$^+$ 312.

To a stirred solution of compound XLVIII-8 (650 mg, 2.1 mmol) and Et$_3$N (1.11 g, 5.25 mmol) in DCM (10 mL) was added dropwise Tf$_2$O (648 mg, 2.4 mmol) at 0° C. under argon. After the addition, the solution was stirred overnight at room temperature. After completion of the reaction, the mixture was poured into water, extract with DCM (10 mL×3). The combined organic layers were dried over Na$_2$SO$_4$, concentrated in vacuo. The residue was purified by chromatography (PE:EA=20:1) to afford compound XLVIII-9 (700 mg, yield: 75.6%). MS (ESI) m/z (M+1)$^+$444.

Pd (OAc)$_2$ (58 mg, 0.26 mmol) and Xantphos (103 mg, 0.17 mmol) were added to a solution of compound XLVIII-9 (715 mg, 1.61 mmol), Cs$_2$CO$_3$ (582 mg, 1.11 mmol) and compound XLVIII-9A (315 mg, 1.74 mmol) in THF (15 mL), the resulting mixture was purged with nitrogen. The reaction mixture was stirred at 80° C. overnight under nitrogen protection. After completion of the reaction, the mixture was poured into 3N aq HCl, extract with EtOAc (30 mL×3). The combined organic layers were dried over Na$_2$SO$_4$, concentrated in vacuo. The residue was purified by column chromatography (PE:EA=2:1) to afford compound XLVIII-10 (200 mg, yield: 45.4%). MS (ESI) m/z (M+1)$^+$311.3.

To a stirred solution of compound XLVIII-10 (176 mg, 0.56 mmol) in DCE (10 mL) and Py (110 mg, 1.39 mmol) was added dropwise compound XLVIII-10A (302 mg, 1.43 mmol) at 0° C. under argon. After the addition, the solution was stirred for 1 hour at room temperature and compound XLVIII-10B (581 mg, 3.71 mmol) was added. The reaction mixture was stirred at 80° C. overnight under nitrogen protection. After completion of the reaction, the mixture was poured into water, extract with EtOAc (30 mL×3). The combined organic layers were dried over Na$_2$SO$_4$, concentrated in vacuo. The residue was purified by chromatography (PE:

EA=2:1) to afford compound XLVIII-11 (152 mg, yield: 50.2%). MS (ESI) m/z (M+1)⁺493.

Preparation of Compound 77

To a stirred solution of compound XLVIII-11 (152 mg, 0.31 mmol) in MeOH:H$_2$O=5:1 (20 mL) was added LiOH (16 mg, 0.38 mmol) under argon. After the addition, the solution was stirred overnight at 60° C. The solution was concentrated in vacuo and was extracted by ether (30 mL×3). The aqueous layer was acidified, and extracted by EtOAc (30 mL). The organic layer was separated, dried and concentrated to afford Compound 77 (20 mg, yield: 14.2%). $^1$H NMR (400 MHz, DMSO-d$_6$) δ 12.40 (s, 1 H), 9.80 (s, 1 H), 7.79 (s, 1 H), 7.69 (d, J=8.4 Hz, 2H), 7.36-7.66 (m, 7 H), 6.12-6.10 (q, 1 H), 3.64 (s, 2 H), 2.52 (s, 3 H), 1.58 (d, J=6.8 Hz, 2 H). MS (ESI) m/z (M+H)⁺ 465.1.

Synthesis of Compound 78

Synthetic Route (Scheme XLIX)

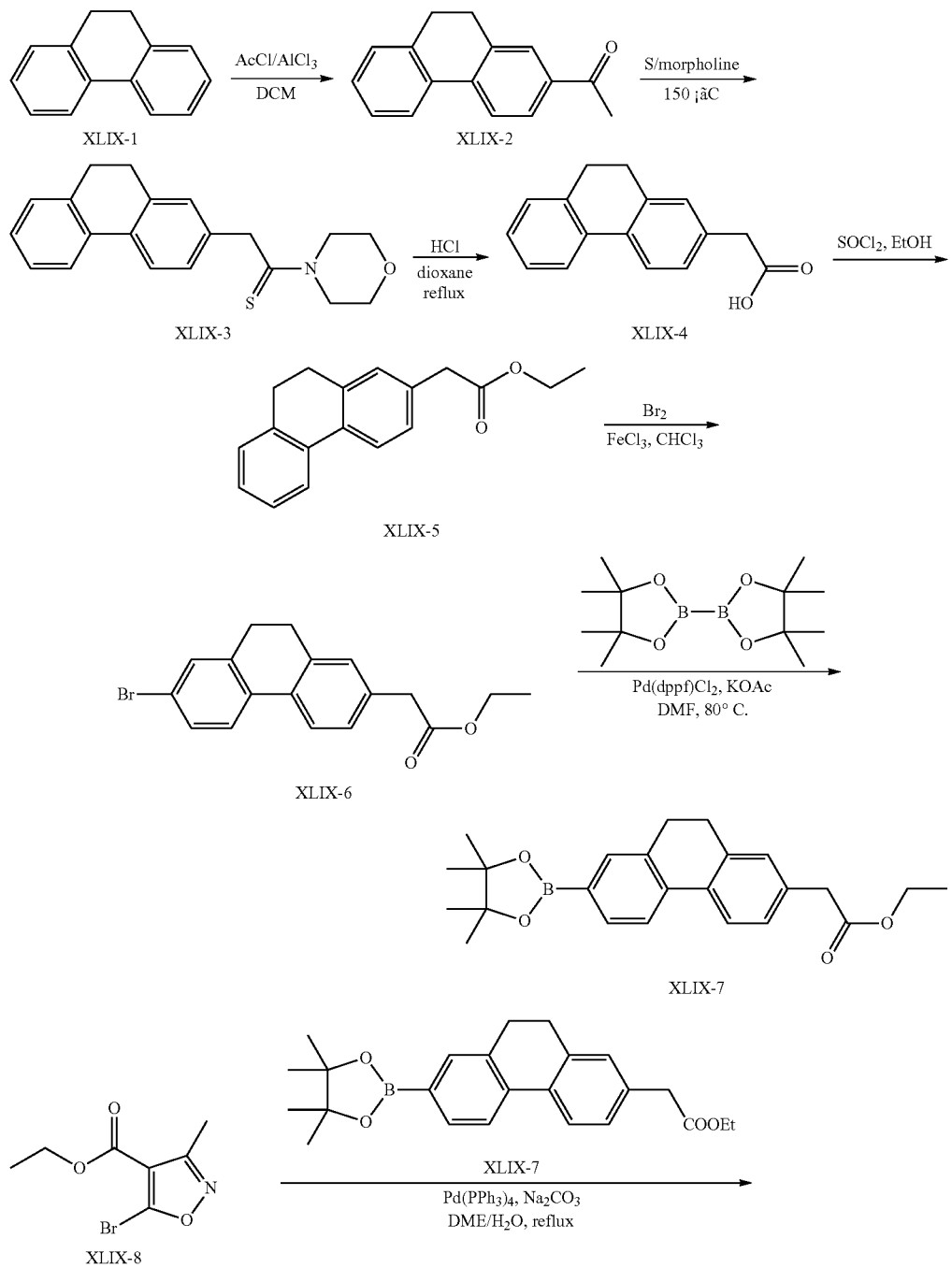

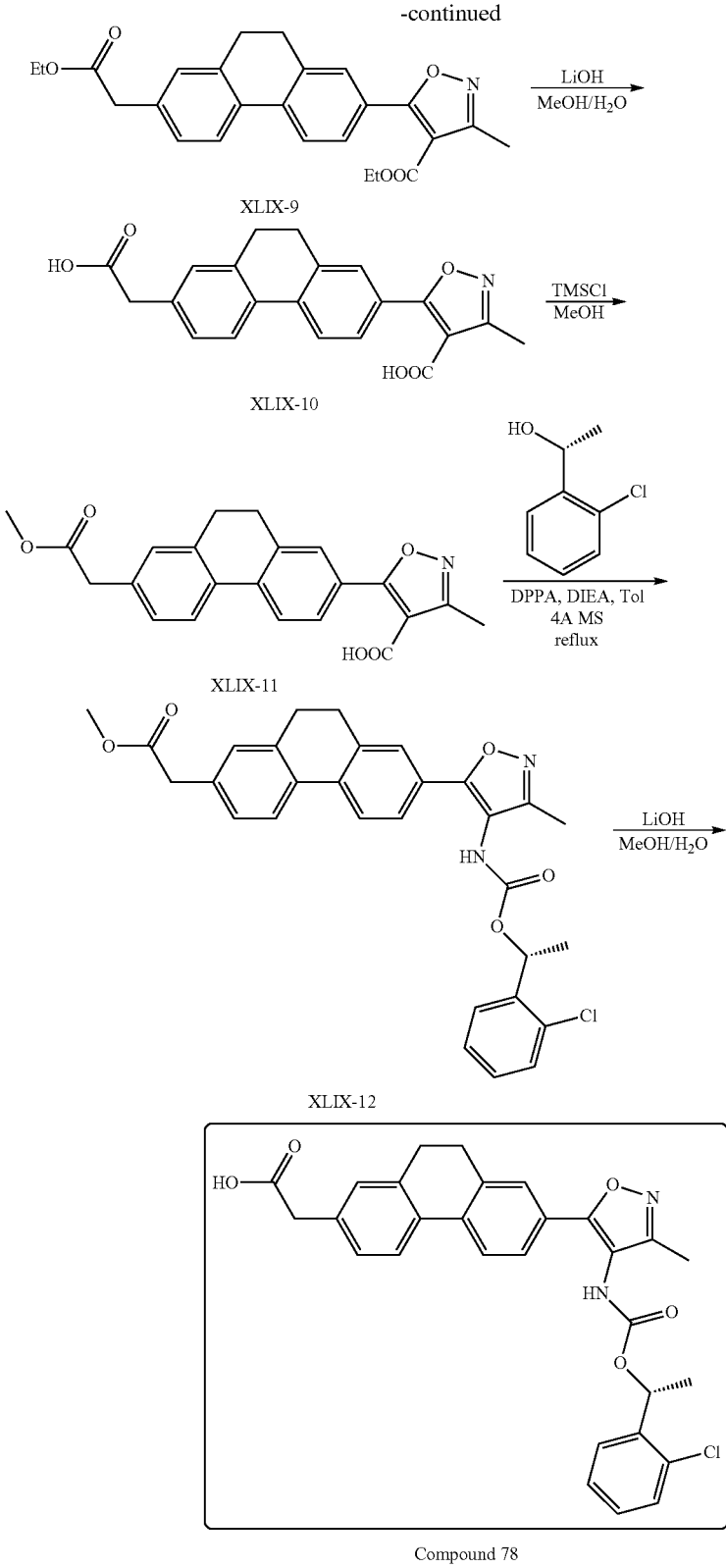

Compound 78

To the solution of compound XLIX-1 (10 g, 0.056 mol) in dry DCM (300 mL) was added acetyl chloride (4.8 g, 0.06 mol), then $AlCl_3$ (15.6 g, 0.118 mol) was added for several batches, the reaction mixture was stirred at r.t overnight. Then the reaction mixture was poured into ice water, then HCl solution was added to the mixture, extracted with EtOAc, the combined organic layers was washed with brine, dried over $Na_2SO_4$, and concentrated. The residue was purified by column chromatography to give compound XLIX-2 (5.1 g, yield: 41.4%).

A mixture of compound XLIX-2 (5.1 g, 23 mmol), sulfur (1.8 g, 57.5 mmol) and morpholine (14.0 g, 87 mmol) was heated to 150° C. for 2.5 hrs. After being cooled in an ice bath, the mixture was treated with ethanol for a period of 60 mins. The precipitated solid was collected by suction filtration and re-crystallized from ethanol to give compound XLIX-3 (7.3 g, yield: 98.2%).

To the solution of compound XLIX-3 (7.3 g, 22.6 mol) in dioxane (300 mL) was added HCl solution (40 mL). The mixture was heated to reflux overnight, and then concentrated; the residue was diluted with water, extracted with EtOAc (300 mL×3). The combined organic layers were washed with brine, concentrated under reduce pressure to give compound XLIX-4 (5 g, yield: 93.0%).

A mixture of compound XLIX-4 (5.0 g, 4.8 mmol) and thionyl chloride (10 mL) in EtOH (10 mL) was stirred at r.t. for 12 hrs. The mixture was concentrated in vacuo, and redissolved with EtOAc (300 mL), then washed with water and brine. The organic layer was dried over $Na_2SO_4$ and concentrated to give compound XLIX-5 (5.5 g, yield: 98.5%).

To the solution of compound XLIX-5 (1 g, 3.76 mmol) in $CHCl_3$ was added $Br_2$ (0.6 g, 3.76 mmol) and $FeCl_3$ (100 mg, 0.61 mmol). The mixture was stirred overnight at room temperature, then the mixture was concentrated and purified by column chromatography to provide a crude compound XLIX-6 (85% purity, 1 g, yield: 77%), which was used directly without further purification.

To the solution of compound XLIX-6 (1 g, 2.9 mmol) in DMF was added potassium acetate (0.57 g, 5.8 mmol), bis(pinacolato)diboron (0.81 g, 3.19 mmol), $Pd(dppf)Cl_2$ (200 mg). The mixture was degassed over 10 min, then heated to 80° C. overnight. The reaction mixture was concentrated under reduce pressure, the residue was purified by column chromatography to give a crude compound XLIX-7 (500 mg, yield 43.8%, 80% purity, impurity come from last step) which was used directly without further purification.

To the solution of compound XLIX-8 (500 mg, 2.14 mmol) and compound XLIX-7 (0.84 g, 2.14 mmol) in $DME/H_2O$ (30 mL, 3:1) was added $Na_2CO_3$ (500 mg, 4.7 mmol) and $Pd(PPh_3)_4$ (300 mg). The mixture was degassed over 10 min, then heated to reflux overnight. The reaction mixture was concentrated under reduce pressure; the residue was purified by column chromatography to give compound XLIX-9 (450 mg, yield: 50.2%).

To the solution of compound XLIX-9 (450 mg, 1.07 mmol) in $MeOH/H_2O$ (2:1, 20 mL) was added LiOH solution (1N, 2.5 mL). The reaction was stirred at room temperature overnight. The mixture was concentrated, and the solution was adjusted to pH=1, and extracted with EtOAc. The organic layer was washed with brine, dried over $Na_2SO_4$, concentrated under reduce pressure to give compound XLIX-10 (300 mg, yield: 77.0%).

To the solution of compound XLIX-10 (500 mg, 1.37 mmol) in absolute MeOH was added TMSCl at 0° C., the mixture was stirred over 1 h, and then TLC checked. The reaction mixture was quenched by water, and then concentrated under reduce pressure. The aqueous layer was extracted with EtOAc (100 mL×3). The combined organic layers were washed with brine, dried over $Na_2SO_4$, concentrated under reduce pressure to afford compound XLIX-11 (400 mg, yield: 77.0%).

To the solution of compound XLIX-11 (400 mg, 1.06 mmol) in toluene was added DIEA (273 mg, 2.11 mmol) and 4 A MS (500 mg). The mixture was heated to reflux for 1 hour, then (R)-1-(2-chlorophenyl)ethanol (183 mg, 1.17 mol) and DPPA (321 mg, 1.17 mmol) were added. After that, the mixture was reflux overnight. The reaction mixture was filtered, the cake was washed with EtOAc, and then the filtrate was concentrated under reduce pressure, the residue was purified by column chromatography to give compound XLIX-12 (380 mg, yield: 69.3%).

Preparation of Compound 78

To the solution of compound XLIX-12 (380 mg, 0.69 mmol) in MeOH (10 mL) and water (5 mL) was added LiOH solution (1N, 1.3 mL). The mixture was stirred overnight at room temperature, the reaction mixture was concentrated under reduced pressure. The remained aqueous layer was washed with EtOAc (40 mL×3), and then the aqueous was adjusted to pH=1 by aq. HCl, then extracted with DCM/isopropanol (3:1). The combined organic layers were washed brine, dried over $Na_2SO_4$, concentrated under reduce pressure to give Compound 78 as a white solid (270 mg, yield: 74.9%). $^1$HNMR ($CDCl_3$, 400 MHz): δ 9.48 (brs, 1 H), 7.87 (d, J=8.4 Hz, 1 H), 7.64-7.71 (m, 4 H), 7.47-7.49 (m, 2 H), 7.38 (m, 1 H), 7.16 (d, J=8.0 Hz, 1 H), 7.14 (s, 1 H), 6.01 (q, J=7.8 Hz, 1 H), 3.20 (s, 2 H), 2.83 (s, 4 H), 2.13 (s, 3 H), 1.30 (d, J=6.4 Hz, 3 H).

Synthesis of Compound 79

Synthetic Route (Scheme L)

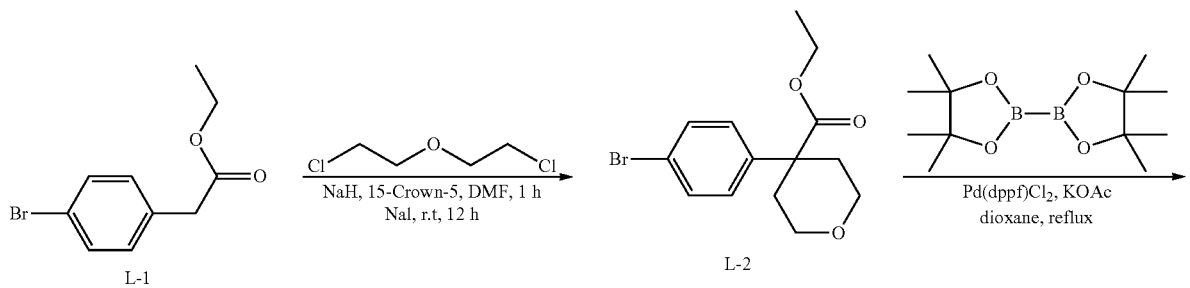

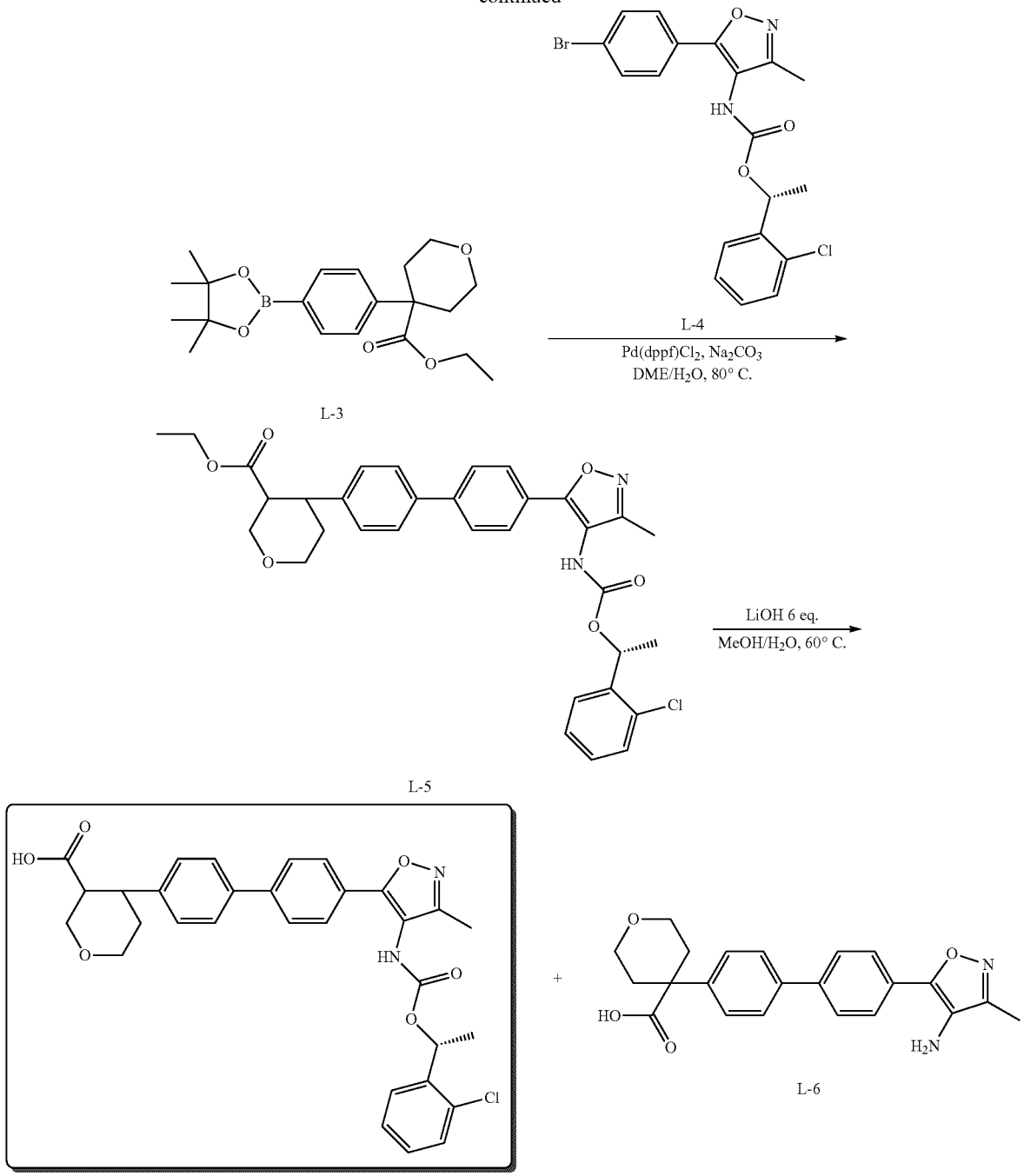

Compound 79

To a solution of compound L-1 (12 g, 50 mmol) in DMF (50 mL) was added NaH (60% dispersion in mineral oil, 4.4 g, 110 mmol) in portions. After stirring for 10 min, 15-crown-5 was added. The reaction mixture was stirred at r.t. for 30 min. And then NaI and 1-chloro-2-(2-chloroethoxy) ethane were added. The mixture was stirred at r.t. for 12 hrs. Then the reaction was quenched with water carefully and adjusted pH to 6-7 with aq. HCl (2N), extracted with EtOAc (50 mL×3). The combined organic layer was washed with brine, dried over $Na_2SO_4$, and concentrated in vacuo. The residue was purified by flash chromatography (PE/EA=10/1 to 5/1) to afford compound L-2 as colorless oil (2.7 g, yield: 17%).

A flask was charged with compound L-2 (2 g, 6.4 mmol), bis(pinacolato)diboron (1.6 g, 6.4 mmol) and KOAc (1.26 g, 12.8 mmol) in 1,4-dioxane (20 mL). The flask was purged with nitrogen for three times. Pd(dppf)Cl$_2$ (234 mg, 0.32 mmol) was added thereto and then the mixture was purged with nitrogen again. The mixture was stirred at 110° C. for 12 hrs. TLC (PE:EA=5:1) monitored the reaction. After the starting material was consumed, the mixture was cooled to r.t, the solvent was evaporated in vacuo. The residue was diluted with water (20 mL), extracted with EA (50 mL×3). The combined organic layer was washed with brine, dried over Na$_2$SO$_4$ and concentrated. The residue was purified by column chromatography on silica gel (PE:EA=10:1 to 5:1) to provide compound L-3 as pale yellow solid (1 g, yield: 44%).

A flask was charged with compound L-3 (172 mg, 0.477 mmol), compound L-4 (160 mg, 0.367 mmol), Na$_2$CO$_3$ (58 mg, 0.5505 mmol), DME (3 mL) and H$_2$O (0.8 mL). The flask was purged with nitrogen for three times. Pd(dppf)Cl$_2$ (13.5 mg, 0.01835 mmol) was added thereto and then the mixture was purged with nitrogen again. The mixture was stirred at 80° C. for 12 hrs. TLC (PE:EA=2:1) monitored the reaction. After the starting material was consumed, the mixture was cooled to r.t, the mixture was diluted with EA (100 mL), washed with brine, dried over Na$_2$SO$_4$ and concentrated. The residue was purified by Prep-TLC (PE:EA=2:1) to afford compound L-5 (190 mg, yield: 88%). MS (ESI) m/z (M+H)$^+$ 589.3.

Preparation of Compound 79

To a solution of compound L-5 (130 mg, 0.22 mmol) in MeOH/H$_2$O (v/v=5:1, 12 mL) was added LiOH.H$_2$O (57 mg, 1.32 mmol). The mixture was stirred at 60° C. for 5 hrs. LCMS monitored the reaction and the desired product and by-product L-6 were detected. The mixture was concentrated in vacuo to remove MeOH, then aq. HCl (2N) was added to adjust pH=4-5, and extracted with EtOAc (30 mL×3), dried over Na$_2$SO$_4$, filtered and concentrated. The residue was purified by prep-HPLC to give Compound 79 (14 mg, yield: 11.4%). $^1$HNMR (CDCl$_3$, 400 MHz) δ 8.07-7.75 (m, 3H), 7.65-7.48 (m, 6H), 7.40-7.27 (m, 2H), 7.15-6.95 (m, 2H), 6.28-6.18 (m, 1H), 4.01-3.92 (m, 2H), 3.67 (t, J=11.2 Hz, 2H), 2.57 (d, J=13.2 Hz, 2H), 2.30 (m, 3H), 2.10-1.95 (m, 3H), 1.41 (m, 2H). MS (ESI) m/z (M+H)$^+$ 561.1.

Synthesis of Compound 80

Synthetic Route (Scheme LI)

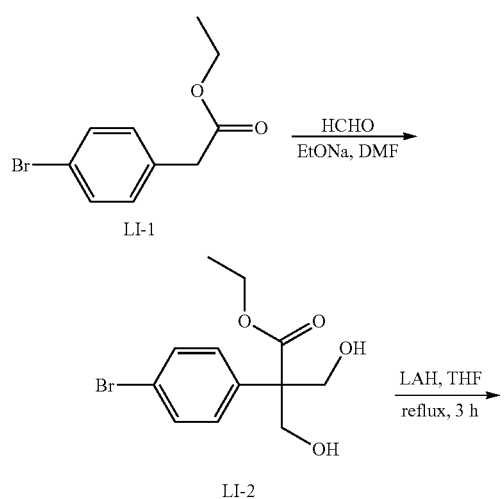

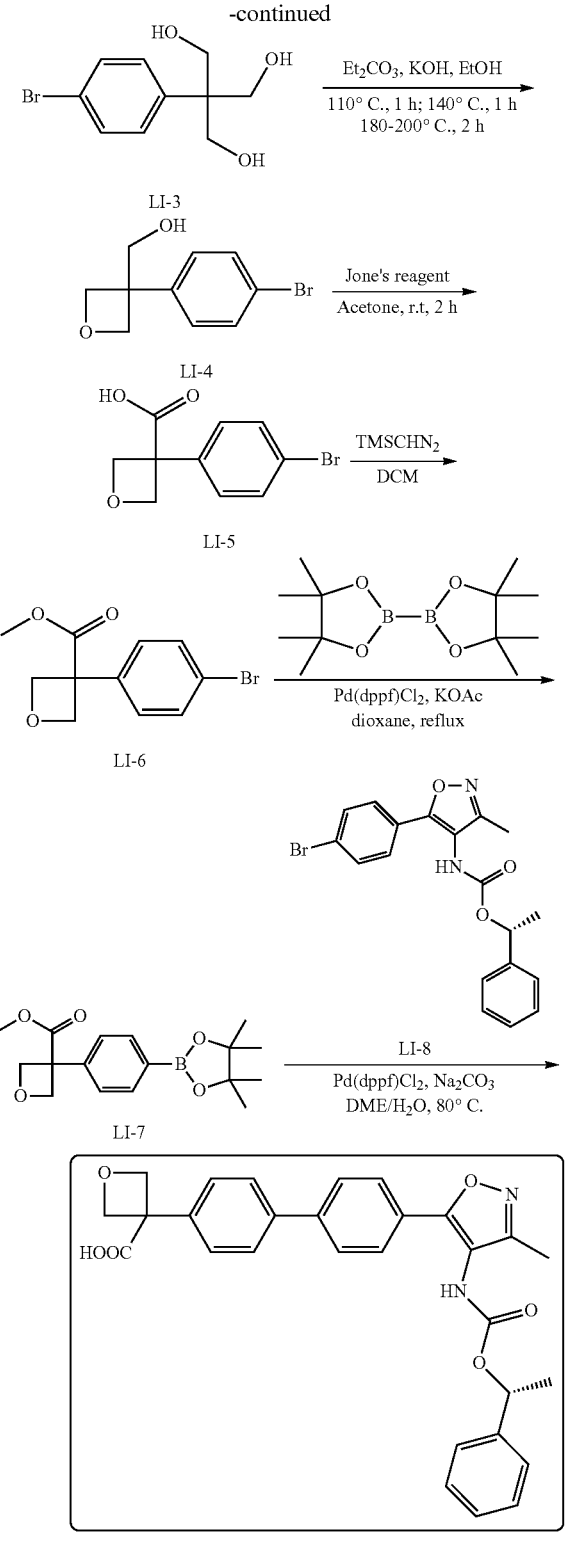

Compound 80

Metal Sodium (0.92 g 0.04 mol) was dissolved in EtOH (30 mL). After stirring for 30 min, the solvent was removed under vacuo. The freshly prepared EtONa was added to the mixture of compound LI-1 (48.6 g, 0.2 mol) and HCHO (18 g, 0.6 mol) in DMF (500 mL). Then the mixture was stirred at r.t overnight. The reaction was quenched with water, extracted with EA (150 Ml×3). The combined organic layer was washed with brine, dried over $Na_2SO_4$ and concentrated. The residue was purified by column chromatography on silica gel (PE:EA=10:1~2:1) to give compound LI-2 (22.3 g, yield: 37%).

To a suspension of LAH (17.06 g, 0.45 mol) in THF (500 mL) was added dropwise a solution of compound LI-2 (45.5 g, 0.15 mol) in THF (200 mL) at r.t. The mixture was stirred at r.t for 20 min. Then it was refluxed under 60° C. for 2 hours. After cooling to r.t, the reaction mixture was quenched with ice water (100 mL) carefully, and then it was acidified with aq. HCl (2 N) to pH=2~3. It was extracted with EtOAc (200 mL×3). The combined organic layer was washed with brine, dried over $Na_2SO_4$ and concentrated. The residue was purified by column chromatography on silica gel (DCM: MeOH=25:1) to yield compound LI-3 (23.4 g, yield: 60%).

To a mixture of compound LI-3 (17 g, 65.1 mmol) and ethyl carbonate (7.7 g, 65.1 mmol) was added absolute EtOH (2 mL) and KOH (0.5 mg, 0.009 mmol). The mixture was heated at 110° C. for 1 h. And then the mixture was distilled for 1 h to remove EtOH. After that, the mixture was heated at 140° C. for 1 h, and 180-200° C. for 1 h. After being cooled to r.t, the mixture was purified by flash chromatography (PE/EA=1/1) to give compound LI-4 (2.2 g, yield: 14%) and 12 g of compound LI-3 was recovered.

To a solution of compound LI-4 (972.4 mg, 4 mmol) in acetone (10 mL) was added Jone's reagent (3 mL) at r.t. The mixture was stirred at r.t for 5 hrs. TLC (PE/EA=1/1) monitored the reaction. The solvent was removed under reduced pressure, the remaining mixture was diluted with EtOAc (100 mL), washed with water and brine, dried over $Na_2SO_4$, filtered and concentrated to provide crude compound LI-5 (1 g, crude yield: 97%), which was used directly in next step without further purification.

To a solution of compound LI-5 (520 mg, 2 mmol) in DCM (10 mL) was added a solution of $TMSCHN_2$ in hexanes (2M, 1.2 mL, 2.4 mmol) at 0° C. And then the mixture was stirred at r.t for 1 h. The mixture was diluted with EtOAc (60 mL), washed with brine, dried over $Na_2SO_4$, filtered and concentrated to provide crude compound LI-6 (600 mg, crude yield 110%), which was used directly in next step without further purification.

A flask was charged with compound LI-6 (50 mg, 0.18 mmol), bis(pinacolato)diboron (46 mg, 0.18 mmol), KOAc (35 mg, 0.36 mmol) and 10 mL of dioxane. It was flushed with nitrogen for three minutes, and then $Pd(dppf)Cl_2$ (6.6 mg, 0.009 mmol, 0.05 eq) was added thereto. After flushing with nitrogen for additional three minutes, the mixture was heated to reflux for 16 hrs. TLC analysis (PE:EA=10:1) showed the reaction completed. The reaction mixture was cooled down to room temperature. The solvent was removed under reduced pressure. The residual was diluted with water (20 mL), extract with EtOAc (20 mL×3). The combined organic layers was washed with brine, dried over anhydrous sodium sulfate, filtered and concentrated. The residue was purified by prep-TLC (PE:EA=10:1) to afford compound LI-7 as light yellow solid (25 mg, yield: 43%).

Preparation of Compound 80

A flask was charged with compound LI-7 (25 mg, 0.0786 mmol), compound LI-8 (31.5 mg, 0.0786 mmol), $Na_2CO_3$ (13 mg, 0.12 mmol), DME (1 mL) and water (0.2 mL). It was degassed with nitrogen for three times, and then $Pd(dppf)Cl_2$ (3 mg, 0.004 mmol, 0.05 eq) was added thereto. After degassed with nitrogen for additional three minutes, the mixture was heated to reflux for 3 hrs under nitrogen atmosphere. LCMS showed the reaction was completed and the acid product was detected. The reaction mixture was cooled down to room temperature, diluted with water (10 mL), acidified with aq. HCl (1N) to pH=4-5, extracted with EtOAc (20 mL×3). The combined organic layer was washed with brine, dried over anhydrous sodium sulfate, filtered and concentrated. The residue was purified by prep-HPLC to afford Compound 80 (10.5 mg, yield: 43%). $^1$H NMR (CDCl$_3$, 300 MHz) δ 7.95-7.70 (m, 3H), 7.64-7.52 (m, 4H), 7.45-7.30 (m, 4H), 7.22-7.09 (m, 2H), 5.86 (brs, 2H), 5.34-5.27 (m, 2H), 5.09-5.02 (m, 2H), 2.22 (s, 3H), 1.62 & 1.42 (double s, 3H). MS (ESI) m/z (M+H)$^+$ 499.4.

Synthesis of Compound 81

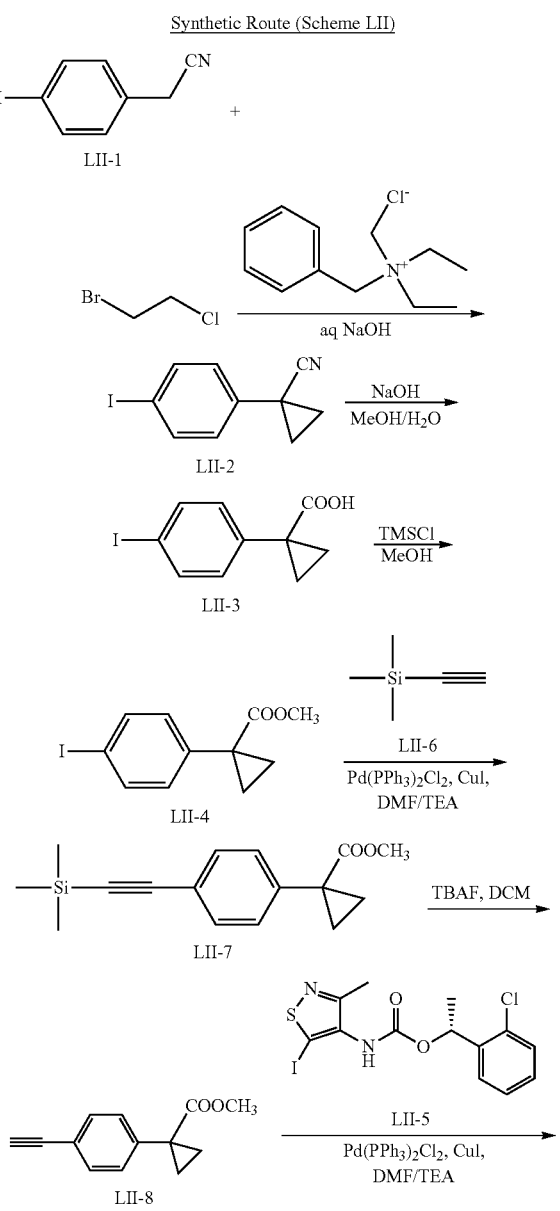

Synthetic Route (Scheme LII)

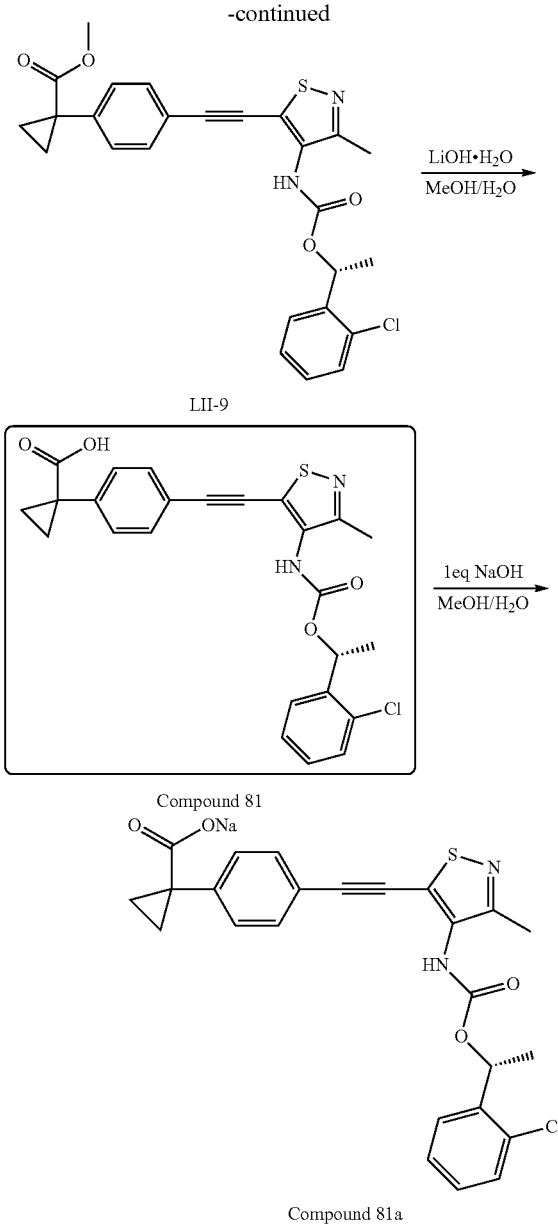

To a solution of compound LII-3 (0.86 g, 3 mmol) in methanol (15 mL) was added dropwise chloro-trimethyl-silane (0.33 g, 3 mmol) at 0° C. After addition, the mixture was stirred overnight at room temperature and then the solvent was evaporated under vacuum to yield compound LII-4 (0.9 g, yield 100%).

To a mixture of compound LII-4 (0.604 g, 2 mmol) and compound LII-6 (0.4 g, 4 mmol) in DMF (10 mL) and TEA (2 mL) was added CuI (0.04 g, 0.2 mmol) and Pd(PPh$_3$)$_2$Cl$_2$ (0.14 g, 0.2 mmol). The mixture was purged with nitrogen for 5 minutes and stirred under N$_2$ at room temperature overnight. The mixture was diluted with water (20 mL) and extracted with EtOAc (30 mL×3). The combined organic layers were washed with brine, dried over Na$_2$SO$_4$, and concentrated under reduced pressure. The residue was purified by column chromatography on silica gel (PE:EA=20:1) to afford compound LII-7 (0.48 g, yield: 88%).

A mixture of compound LII-7 (0.48 g, 1.76 mmol) and TBAF (0.524 g, 2 mmol) in DCM (30 mL) was stirred at room temperature for 3 hours. The reaction was poured into water. The aqueous phase was extracted with DCM (25 mL×3). The combined organic phase was dried over Na$_2$SO$_4$ and concentrated to afford compound LII-8 (0.35 g, yield: 99%).

To a mixture of compound LII-8 (0.14 g, 0.7 mmol) and compound LII-5 (0.268 g, 0.64 mmol) in DMF (10 mL) and TEA (0.3 mL) was added CuI (0.012 g, 0.06 mmol) and Pd(PPh$_3$)$_2$Cl$_2$ (0.044 g, 0.06 mmol). The mixture was stirred under N$_2$ at room temperature overnight. The mixture was diluted with water (40 mL) and extracted with EtOAc (50 mL×3). The combined organic layers were washed with brine, dried over Na$_2$SO$_4$, and concentrated under reduced pressure. The residue was purified by column chromatography on silica gel (PE:EA=10:1~4:1) to afford compound LII-9 (0.22 g, yield: 69%).

Preparation of Compound 81

To a solution of LII-9 (0.22 g, 0.44 mmol) in methanol (5 mL) was added LiOH.H$_2$O (0.094 g, 2.22 mmol) and water (1 mL). The reaction mixture was stirred at room temperature overnight. The mixture was diluted with water (20 mL) and acidified with 2N aq HCl to pH=4~5 and then extracted with EtOAc (30 mL×3). The combined organic layers were washed with brine, dried over Na$_2$SO$_4$, and concentrated under reduced pressure to give Compound 81 (0.18 g, yield: 85.3%). $^1$H NMR: (CDCl$_3$, 400 MHz) δ 7.41~7.33 (m, 6H), 7.22-7.16 (m, 2 H), 6.22 (q, J=6.4 Hz, 1 H), 2.39 (s, 3H), 1.73~1.70 (m, 2H), 1.57 (d, J=6.4 Hz, 3 H), 1.29~1.25 (m, 2H). MS (ESI) m/z (M+H)$^+$ 481.1.

Preparation of Compound 81a

To a solution of Compound 81 (0.13 g, 0.27 mmol) in MeOH (10 mL) was added aq. NaOH (0.1 M, 2.7 mL, 0.27 mmol). The mixture was stirred at room temperature for 20 minutes. The solvent was evaporated under vacuum and freeze dried to afford Compound 81a (0.135 g, yield: 100%). $^1$H NMR: (DMSO-d6, 400 MHz) δ 9.57 (brs, 1H), 7.62~7.42 (m, 2H), 7.35~7.22 (m, 6H), 6.02 (q, J=6.4 Hz, 1H), 2.31 (s, 3H), 1.51 (d, J=6.4 Hz, 3H), 1.22~1.18 (m, 2H), 0.71~0.66 (m, 2H). MS (ESI) m/z (M+H)$^+$ 481.1.

A solution of NaOH (50%, 8 ml) was added dropwise to a mixture of compound LII-1 (2 g, 8.23 mmol), 1-bromo-2-chloroethane (2.37 g, 16.5 mmol) and benzyl-triethylammonium chloride (0.094 g, 0.41 mmol) at room temperature. The reaction mixture was stirred and heated to 60° C. overnight. Reaction was monitored by TLC. The reaction mixture was quenched with water and extracted with CH$_2$Cl$_2$. The organic layer was washed two times with dilute hydrochloric acid, dried over Na$_2$SO$_4$ and concentrated. The residue was purified by column chromatography (PE:EA=50:1~20:1) to give compound LII-2 (1.35 g, yield: 61%).

A mixture of compound LII-2 (0.8 g, 3 mmol), NaOH (2.4 g, 60 mmol) in MeOH (15 mL) and H$_2$O (10 mL) was heated to 100° C. overnight. The mixture was cooled to room temperature, water (200 mL) was added and the mixture was acidified to pH=3~4 with aq. HCl (2N), the mixture was extracted with EtOAc. The organic layer was dried over Na$_2$SO$_4$, concentrated to yield compound LII-3 (0.86 g, yield: 100%).

Synthesis of Compound 82

Synthetic Route (Scheme LIII)

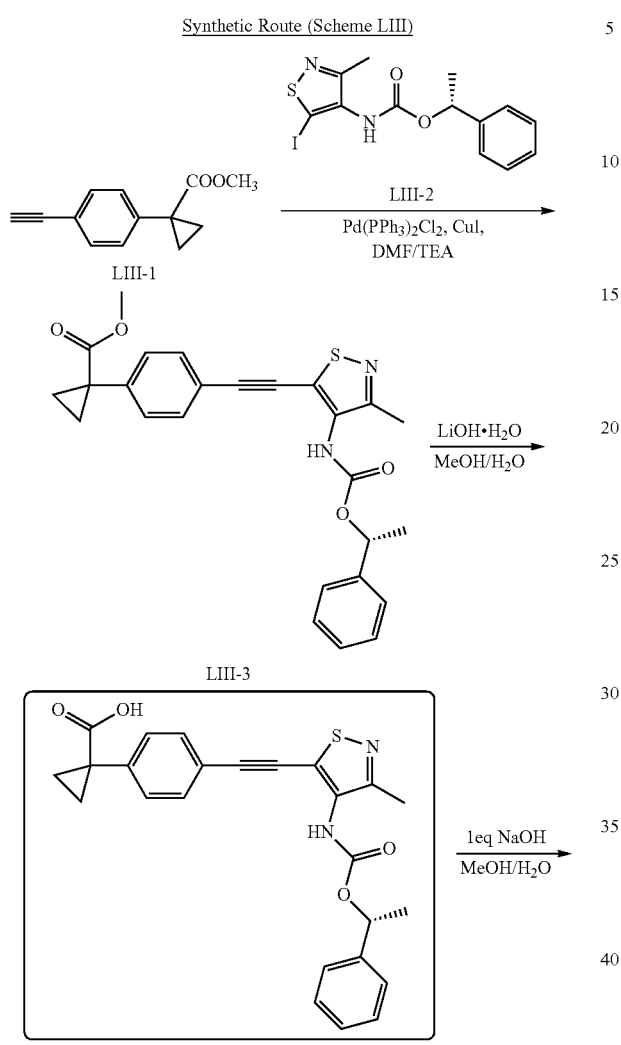

Compound 82

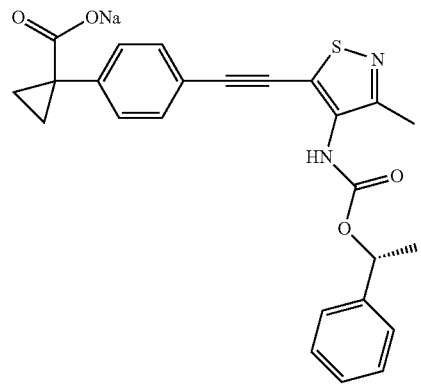

Compound 82a

Compound LIII-1 was prepared by the same method as described in the synthesis of compound LII-8 (Scheme LII).

Compound 82 was prepared analogously to the procedure described in the synthesis of Compound 81. Compound 82: $^1$H NMR: (CDCl$_3$, 400 MHz) δ 7.41~7.28 (m, 9H), 6.45 (s, 1H), 5.89 (q, J=6.4 Hz, 1H), 2.37 (s, 3H), 1.73~1.70 (m, 2H), 1.50 (d, J=6.4 Hz, 3H), 1.29~1.24 (m, 2H). MS (ESI) m/z (M+H)$^+$ 447.1, (M+Na)$^+$ 469.1. Compound 82a was prepared analogously to the procedure described in the synthesis of Compound 81a.

Compound 82a: $^1$H NMR: (DMSO-d6, 400 MHz) δ 9.49 (brs, 1H), 7.45~7.24 (m, 9H), 5.79 (q, J=6.4 Hz, 1H), 2.27 (s, 3H), 1.52 (d, J=6.4 Hz, 3H), 1.22~1.18 (m, 2H), 0.70~0.65 (m, 2H). MS (ESI) m/z (M+H)$^+$ 447.1, (M+Na)$^+$ 469.1

Synthesis of Compound 83

Synthetic Route (Scheme LIV)

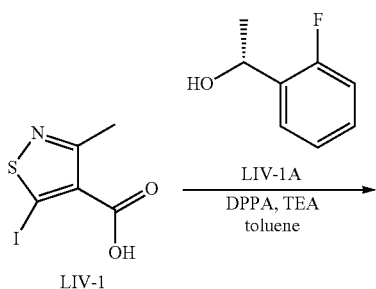

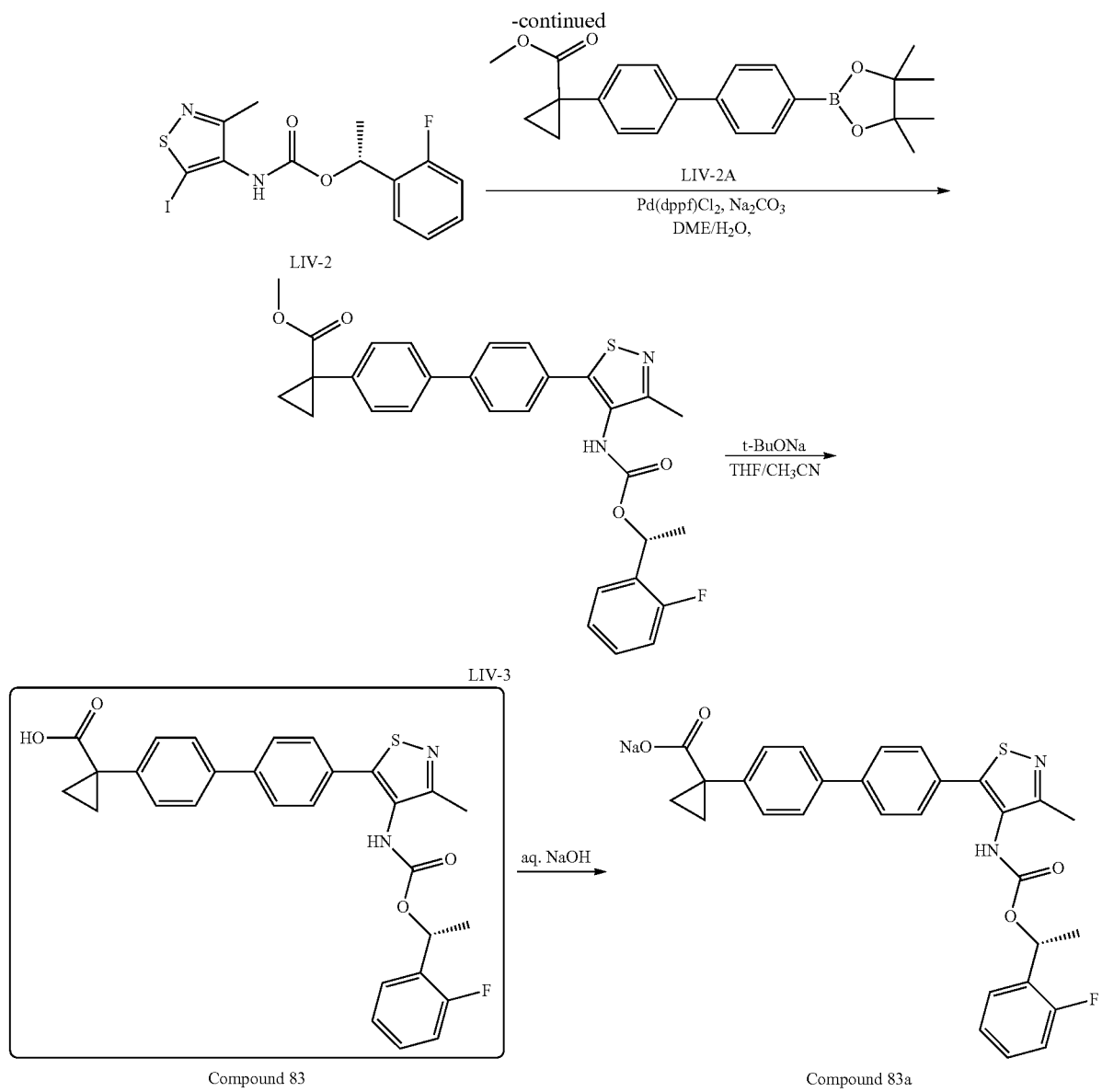
Compound 83 was prepared analogously to the procedure described in the synthesis of Compound 44.
Compound 83a was prepared analogously to the procedure described in the synthesis of Compound 44a. $^1$H NMR (DMSO-d6, 400 MHz): δ 9.01 (s, 1H), 7.69 (d, J=8.4 Hz, 2H), 7.57 (d, J=8.4 Hz, 2H), 7.51 (d, J=8.0 Hz, 2H), 7.32-7.42 (m, 4H), 7.13-7.210 (m, 2H), 5.95 (q, 1H), 2.28 (s, 3H), 1.50 (br, 3H), 1.28 (br, 2H), 0.75 (br, 2H). MS (ESI) m/z (M+H)$^+$ 517.1.
Synthesis of Compound 84
Synthetic Route (Scheme LV)
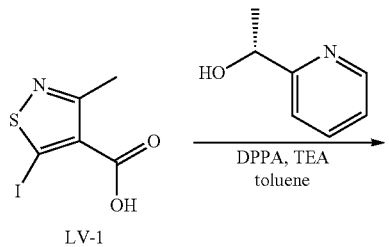

-continued
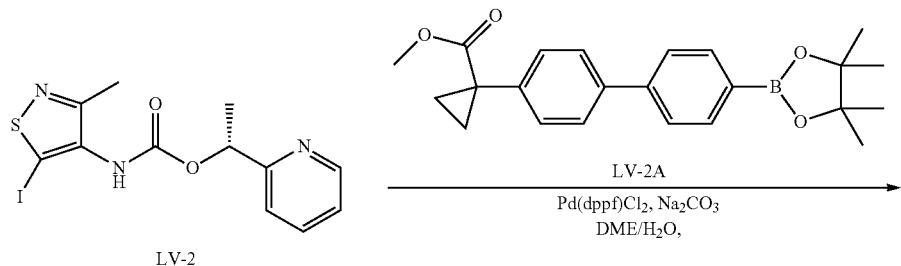
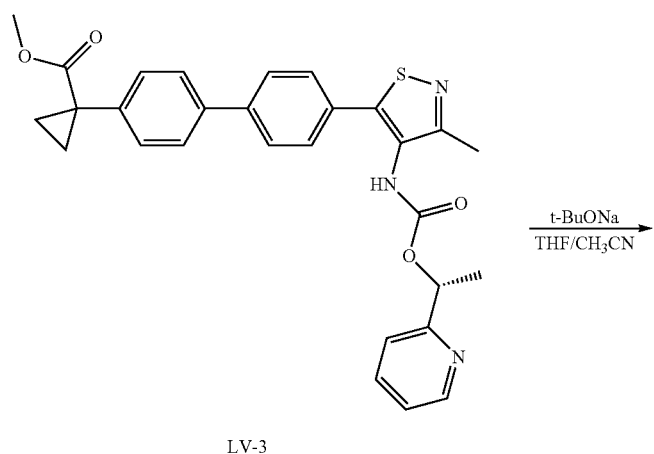
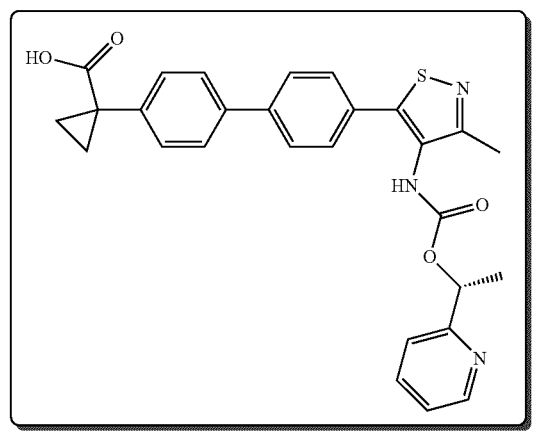
Compound 84
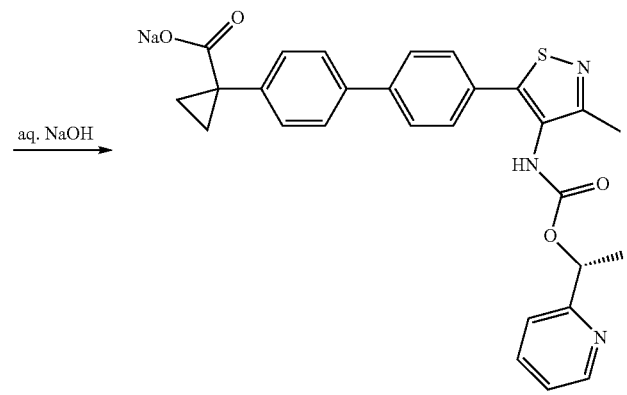
Compound 84a
Compound 84 was prepared analogously to the procedure described in the synthesis of Compound 44. Compound 84a was prepared analogously to the procedure described in the synthesis of Compound 44a.
Compound 84a: $^1$H NMR (DMSO-$d_6$, 400 MHz): δ 8.53-8.54 (m, 1H), 7.71-7.77 (m, 3H), 7.61 (d, J=8.4 Hz, 2H), 7.52 (d, J=8.4 Hz, 2H), 7.41 (d, J=8.4 Hz, 2H), 7.27-7.33 (m, 2H), 5.74 (q, 1H), 2.31 (s, 3H), 1.52 (d, J=6.0 Hz, 3H), 1.22-1.29 (m, 2H), 0.73-0.75 (m, 2H). MS (ESI) m/z (M+H)$^+$ 500.1.

Synthesis of Compound 85
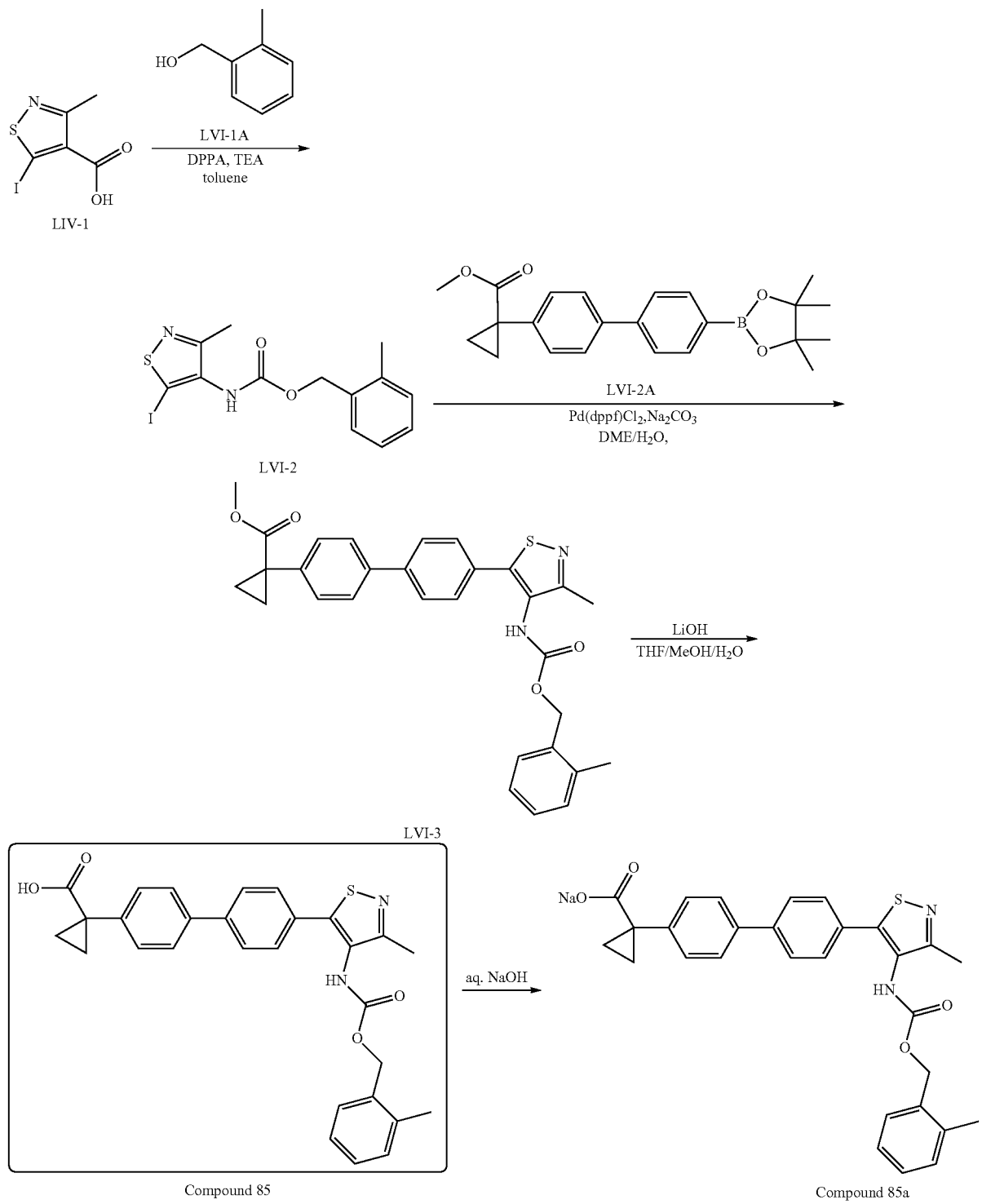
Compound 85 was prepared analogously to the procedure described in the synthesis of Compound 44. Compound 85: MS (ESI) m/z (M+H)+ 499.2.
Compound 85a was prepared analogously to the procedure described in the synthesis of Compound 44a. $^1$H NMR (DMSO-$d_6$, 400 MHz): δ 7.69 (d, J=8.0 Hz, 2H), 7.60 (d, J=8.0 Hz, 2H), 7.50 (d, J=8.0 Hz, 2H), 7.40 (d, J=8.0 Hz, 2H), 7.15-7.24 (m, 4H), 5.13 (s, 2H), 2.30 (s, 3H), 2.29 (s, 3H), 1.25-1.26 (m, 2H), 0.71-0.72 (m, 2H). MS (ESI) m/z (M+H)+ 499.2.

Synthesis of Compound 86
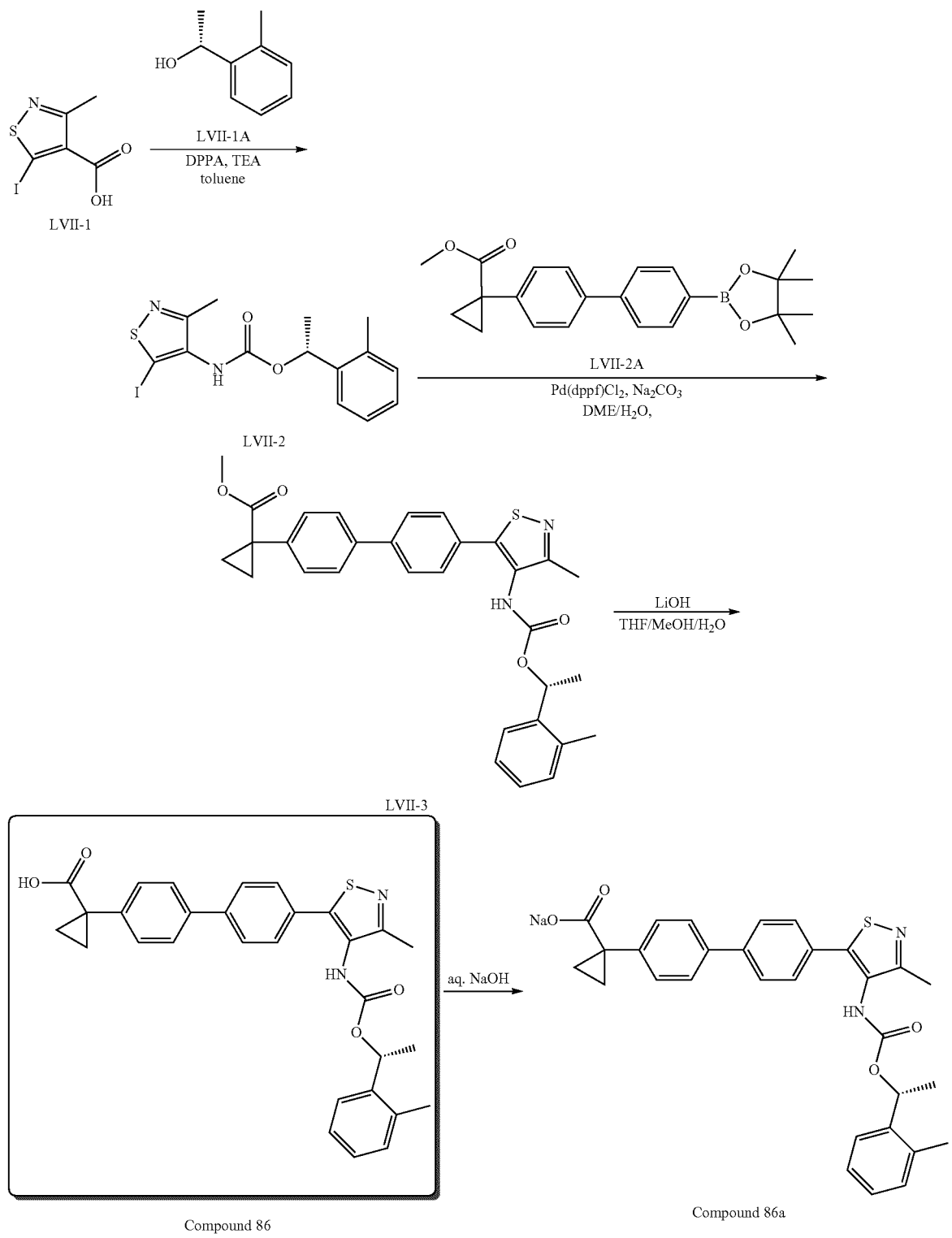
Compound 86 was prepared analogously to Compound 44. Compound 86: MS (ESI) m/z (M+H)+ 513.2.
Compound 86a was prepared analogously to Compound 44a. Compound 86a: 1H NMR (DMSO-d6, 400 MHz): δ 8.93 (br, 1H), 7.68 (d, J=8.4 Hz, 2H), 7.56 (d, J=8.4 Hz, 2H), 7.50 (d, J=8.4 Hz, 2H), 7.34-7.41 (m, 3H), 7.16-7.18 (m, 3H), 5.90 (s, 2H), 2.03 (s, 3H), 2.27 (s, 3H), 1.45 (br, 3H), 1.25-1.26 (m, 2H), 0.72-0.73 (m, 2H). MS (ESI) m/z (M+H)+ 513.2.

Synthesis of Compound 87
Synthetic Route (Scheme LVIII)
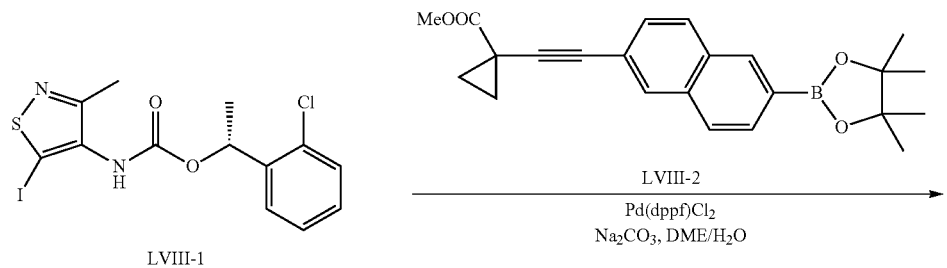
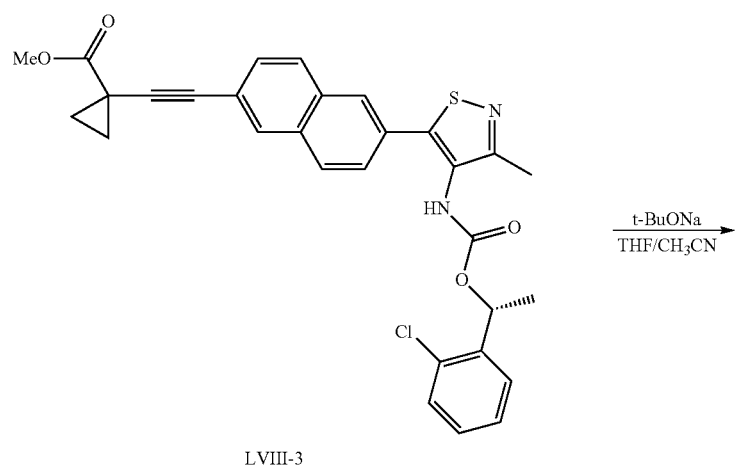
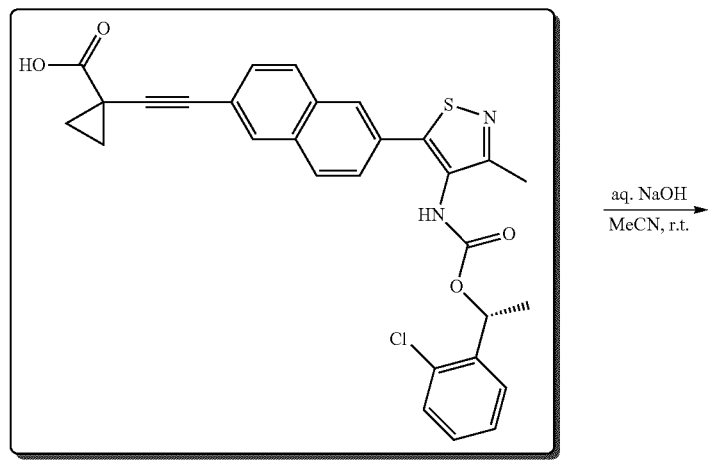
Compound 87

-continued

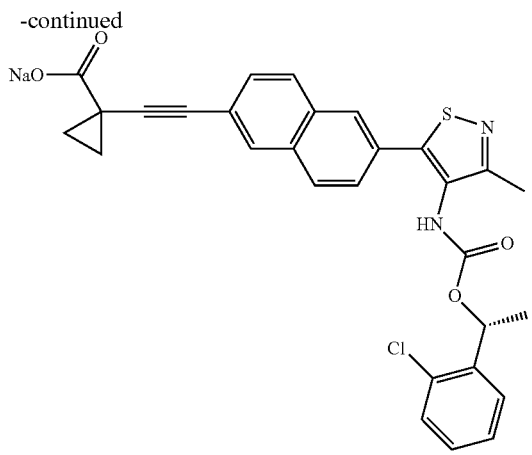

Compound 87a

To a stirred mixture of compound LVIII-1 (100 mg, 0.266 mmol), compound LVIII-2 (112 mg, 0.266 mmol), and $Na_2CO_3$ (56 mg, 0.532 mmol) in DME (4.5 mL) and $H_2O$ (1.5 mL) was added $Pd(dppf)Cl_2$ (20 mg, 0.03 mmol). The reaction mixture was flushed with nitrogen and heated to 80° C. overnight. The mixture was diluted with EtOAc (40 mL), washed with water and brine, dried over $Na_2SO_4$, filtered and concentrated. The residue was purified by column (PE:EA=4:1) to give compound IVIII-3 (65 mg, yield: 45%). MS (ESI) m/z (M+H)⁺ 545.1.

Prepare of Compound 87

To a solution of compound LVIII-3 (65 mg, 0.119 mmol) in THF (1 mL) was added $CH_3CN$ (3 mL) and t-BuONa (14 mg, 0.143 mmol). The reaction mixture was stirred at room temperature overnight. The mixture was cooled down to 0° C. and neutralized to pH=4.0 with 3N hydrochloride solution. The mixture was extracted with EtOAc (30 mL×3). The combined organic phase was dried over $Na_2SO_4$, concentrated, and then lyophilized to give Compound 87 (60 mg, yield: 95%). MS (ESI) m/z (M+H)⁺ 531.2.

Prepare of Compound 87a

To a solution of Compound 87 (60 mg, 0.113 mmol) in MeCN (3 mL) was added 0.05N sodium hydroxide solution (2.2 mL) at 0° C. The reaction mixture was stirred for 30 minutes, then lyophilized to give Compound 87a. ¹HNMR (DMSO-d₆ 400 MHz) δ9.15 (s, 1 H), 8.27 (s, 1 H), 7.94-7.97 (m, 2H), 7.82-7.86 (m, 2H), 7.33-7.49 (m, 5 H), 6.05 (q, 1 H), 2.18 (s, 3H), 1.53 (br, 3H), 1.27-1.29 (m, 2 H), 0.93-0.96 (m, 2 H). MS (ESI) m/z (M+H)⁺ 531.2.

Synthesis of Compound 88

Synthetic Route (Scheme LIX)

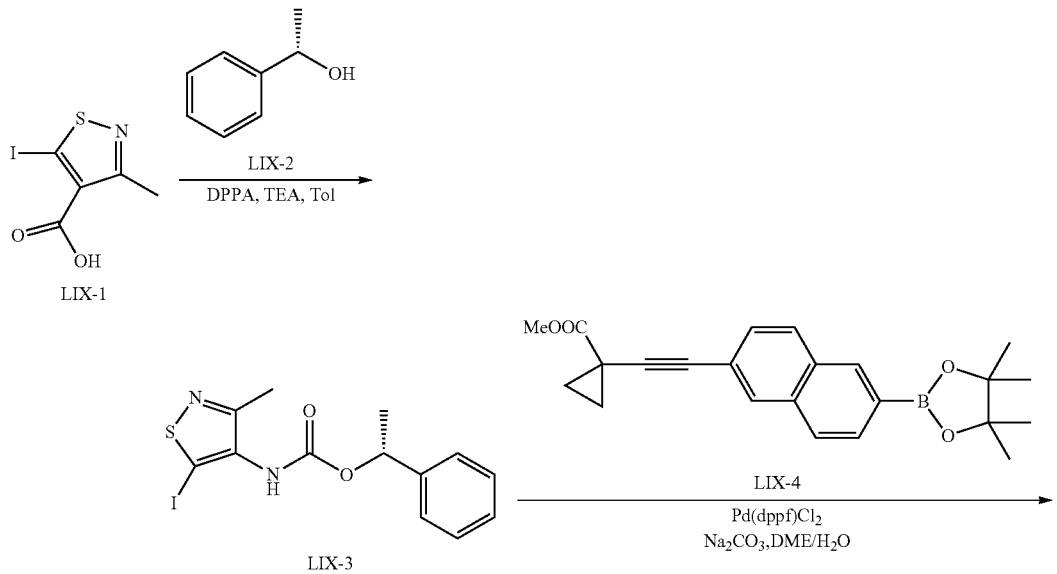

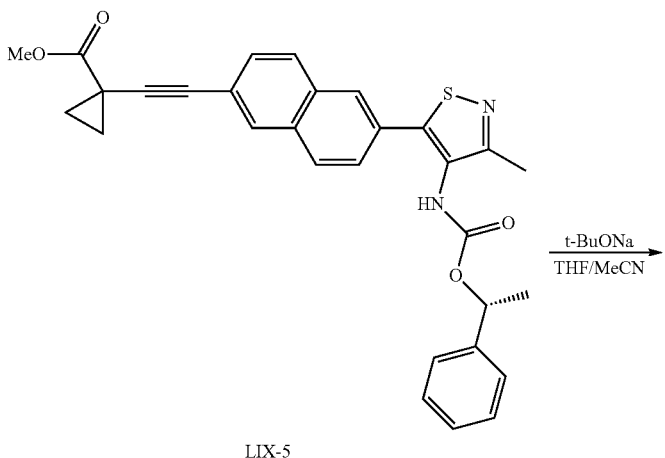
LIX-5
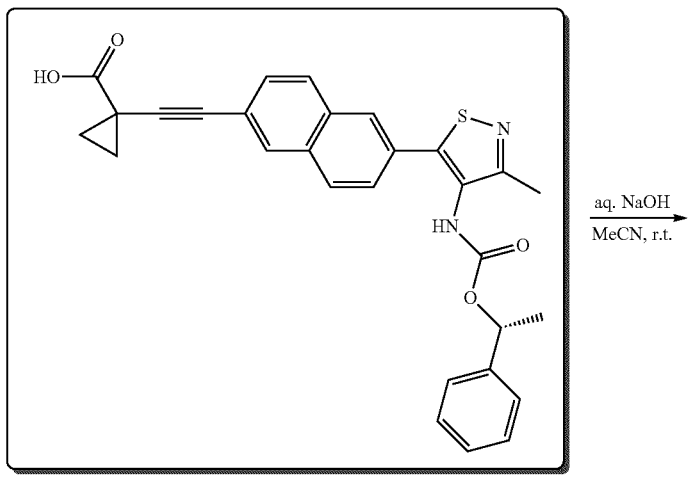
Compound 88
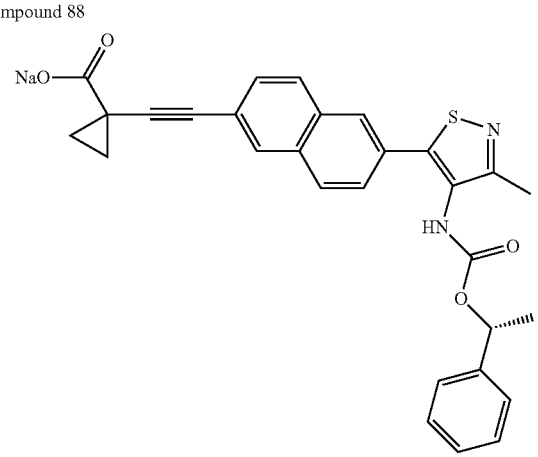
Compound 88a
Compound 88 was prepared analogously to the procedure described in the synthesis of Compound 87. Compound 88: MS (ESI) m/z (M+H)⁺ 497.0.
Compound 88a was prepared analogously to the procedure described in the synthesis of Compound 87a. Compound 88a: ¹HNMR (DMSO-$d_6$ 400 MHz) δ 8.02 (s, 1 H), 7.89-7.93 (m, 2 H), 7.78 (d, J=8.4 Hz, 1H), 7.60 (d, J=8.4 Hz, 1H), 7.46 (d, J=8.4 Hz, 1H), 7.29 (br, 5H), 5.73 (q, 1 H), 2.31 (s, 3H), 1.46 (br, 3H), 1.27-1.29 (m, 2 H), 0.92-0.95 (m, 2 H). MS (ESI) m/z (M+H)⁺ 497.0.

Synthesis of Compound 89
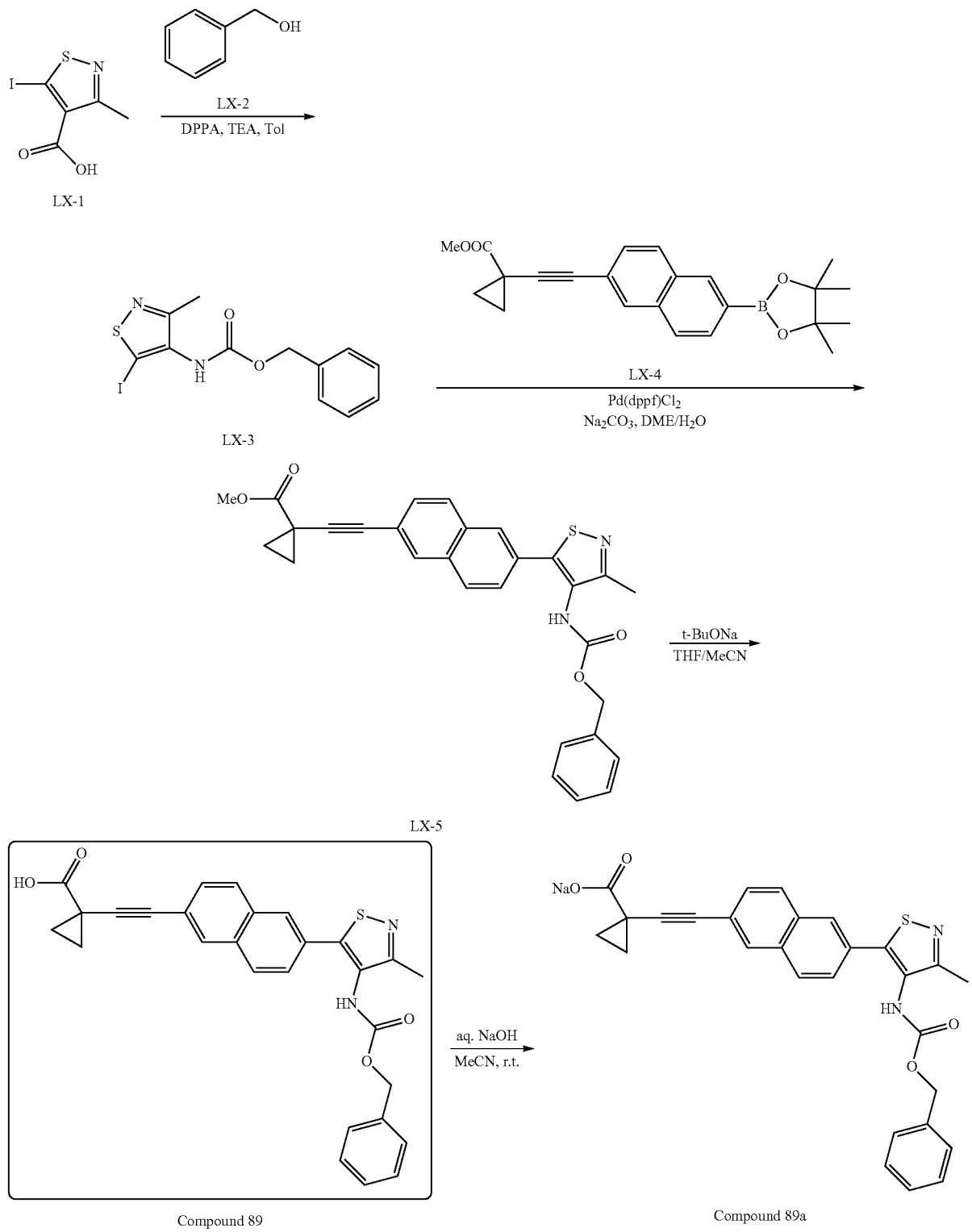
Compound 89 was prepared analogously to the procedure described in the synthesis of Compound 87. Compound 89: MS (ESI) m/z (M+H)$^+$ 483.2.
Compound 89a was prepared analogously to the procedure described in the synthesis of Compound 87a. Compound 89a: $^1$H NMR (DMSO-d$_6$ 400 MHz) δ 9.41 (br, 1 H), 8.06 (s, 1 H), 7.96-7.97 (m, 2 H), 7.82 (d, J=8.4 Hz, 1H), 7.62 (d, J=8.4 Hz, 1H), 7.47 (d, J=8.4 Hz, 1H), 7.36 (br, 5H), 5.14 (s, 2 H), 2.32 (s, 3H), 1.21-1.23 (m, 2 H), 0.91-0.93 (m, 2 H). MS (ESI) m/z (M+H)$^+$ 483.2.

Synthesis of Compound 90

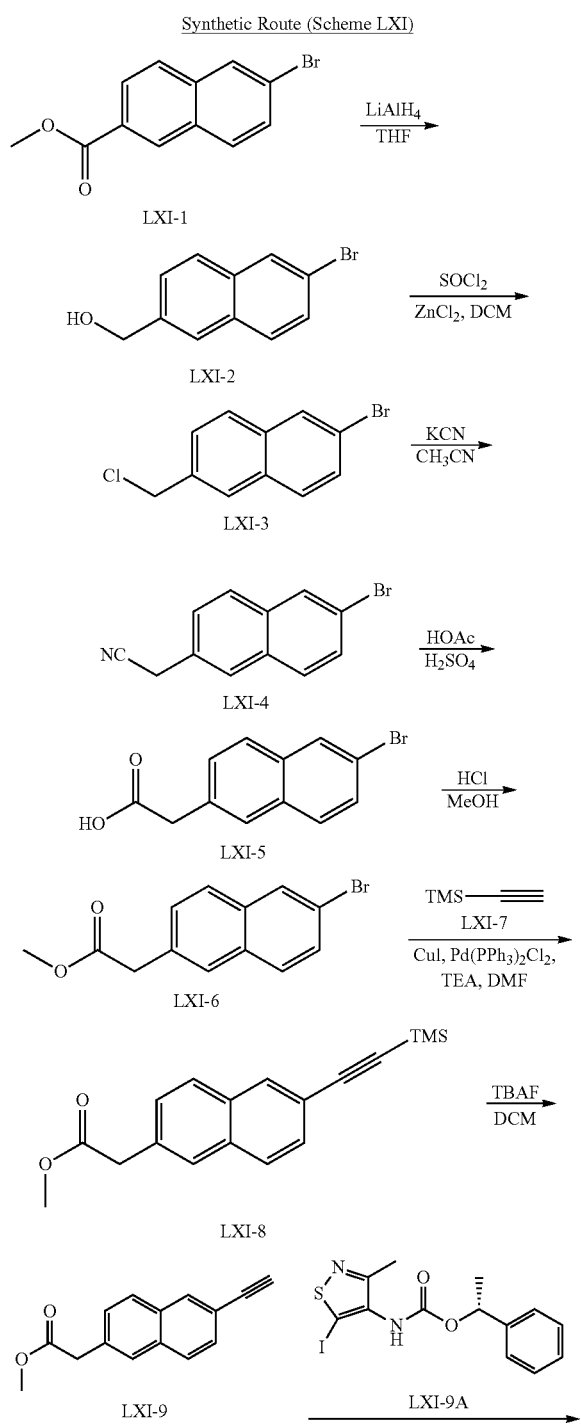

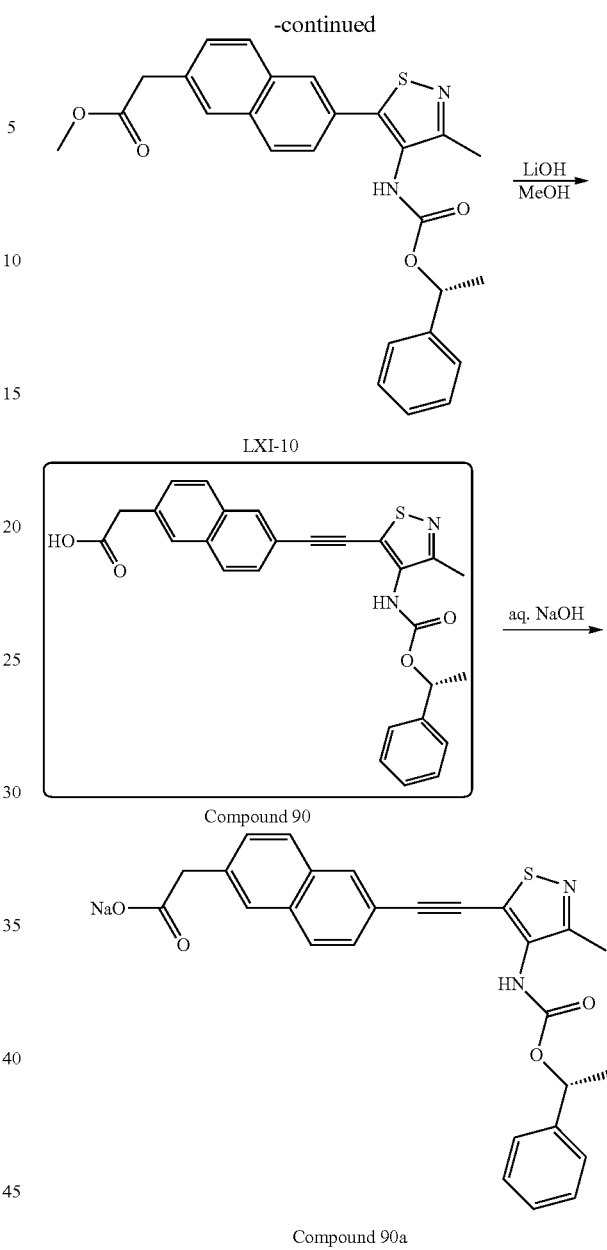

To a solution of LAH (22.8 g, 0.6 mol) in THF (1000 mL) was added compound LXI-1 (53.2 g, 0.2 mol in THF 1000 mL) dropwise at 0° C. The mixture was stirred for 1.5 h at room temperature, the mixture was quenched with water (22.8 mL) and aq. NaOH (10% in water, 22.8 mL), then MgSO$_4$ (40 g) was added. The resulting mixture was stirred for 1 h, filtered and concentrated to get compound LXI-2 (41.5 g, yield: 88.3%).

To a solution of compound LXI-2 (39.0 g, 164.6 mmoml) and ZnCl$_2$ (0.41 g, 3.1 mmoml) in DCM (600 mL) was added SOCl$_2$ (39.0 g, 329.2 mmol) at −5° C. The mixture was stirred for overnight at room temperature and then concentrated to get residue and washed with heptane at −10° C. to get compound LXI-3 (38.5 g, yield: 92.0%).

To a solution of compound LXI-3 (10.2 g, 40 mmoml) in MeCN (100 mL) was added NaCN (2.0 g, 40 mmol). The mixture was heated to reflux for overnight. After being cooled to room temperature, Water (300 mL) was added, the resulting slurry was cooled to 0° C., compound LXI-4 (9.4 g, yield: 93.0%) was collected by filtration, which was used directly in the next step.

The mixture of compound LXI-4 (4.0 g, 16.3 mmol) in $H_2SO_4$ (60 g), HOAc (77 g) and water (250 mL) was stirred at reflux for 2 hrs. After being cooled to room temperature, water (300 mL) was added and stirred for 1 h. The precipitated solid was collected by filtration to afford compound LXI-5 (3.6 g, yield: 83.9%).

The mixture of compound LXI-5 (3.0 g, 11.4 mmol) in HCl/MeOH (50 mL) was stirred at reflux for 2 h. After concentrated, water (50 mL) was added, and extracted with EtOAc (40 mL×3). The combined organic layers were washed with brine (10 mL×2), and concentrated under reduced pressure to give compound LXI-6 (2.45 g, yield: 77.3%).

To a stirred solution of compound LXI-6 (277 mg, 1.0 mmol), compound LXI-7 (294 mg, 3.0 mmol), CuI (20 mg, 0.1 mmol) in TEA (5 mL) was added $Pd(PPh_3)_2Cl_2$ (70 mg, 0.01 mmol) under Ar. After the addition, the solution was heated to reflux under Ar overnight. The solution was concentrated, then $H_2O$ (20 mL) was added, and the mixture was extracted with EtOAc (20 mL×3). The organic layer was combined and washed with brine, dried over $Na_2SO_4$, concentrated in vacuo to get compound LXI-8 (0.25 g, crude yield: 77.6%), which was used directly without further purification.

The mixture of compound LXI-8 (710 mg, 2.2 mmol), TBAF (690 mg, 2.65 mmol) in DCM (20 mL) was stirred at room temperature for 2 hours. Then $H_2O$ was added, the residue was partitioned between $H_2O$ and DCM, the aqueous phase was extracted with DCM, the combined organic layer was washed with brine, dried over $Na_2SO_4$, concentrated. The residue was purified by chromatography on silica gel (PE/EA=50/1) to afford compound LXI-9 (400 mg, yield 81.4%).

To a stirred solution of compound LXI-9 (100 mg, 0.45 mmol), compound LXI-9A (207.3 mg, 0.54 mmol), CuI (10 mg, 0.05 mmol) in TEA (5 mL) was added $Pd(PPh_3)_2Cl_2$ (35 mg, 0.05 mmol) under Ar. After the addition, the solution was heated to reflux under Ar for 2 hours. The solution was concentrated, then $H_2O$ (20 mL) was added, and the mixture was extracted with EtOAc (20 mL×3). The organic layer was combined and washed with brine, dried over $MgSO_4$, concentrated in vacuo. The residue was purified by column chromatography on silica gel (Petroleum ether: EtOAc=10:1) to afford compound LXI-10 (125 mg, yield 47.7%). MS (ESI) m/z $(M+H)^+$ 485.1.

Preparation of Compound 90

To a solution of compound LXI-10 (120 mg, 0.248 mmol) in MeOH (10 mL), THF (10 mL, $H_2O$ (10 ml) was added lithium hydroxide monohydrate (41 mg, 1.0 mmol). The mixture was stirred for overnight at room temperature, then concentrated, water (20 mL) and HCl (2N) was added to adjust pH=2, extracted with EtOAc (25 mL×3). The combined organic layers were washed with brine (10 mL×2), and concentrated under reduced pressure to get residue which was purified by prep-HPLC to give Compound 90 (110 mg, yield: 83.5%). MS (ESI) m/z $(M+H)^+$ 471.0.

Preparation of Compound 90a

To a solution of Compound 90 (104 mg, 0.221 mmol) in MeOH (1 mL) and water (10 mL) was added NaOH (0.05N, 4.25 mL) stirred for one hour, then the reaction mixture was lyophilized to give Compound 90a. $^1H$ NMR (DMSO-$d_6$, 400 MHz): δ9.57 (br, 1 H), 8.00 (s, 1 H), 7.80 (d, J=8.8 Hz, 1H), 7.73 (d, J=8.4 Hz, 1H), 7.66 (s, H), 7.36 (d, J=8.4 Hz, 1H), 7.24-7.33 (m, 6H), 5.79 (q, 1H), 3.34 (s, 2H), 2.26 (s, 3H), 1.50 (d, J=6.4 Hz, 3H). MS (ESI) m/z $(M+H)^+$ 471.0.

Synthesis of Compound 91

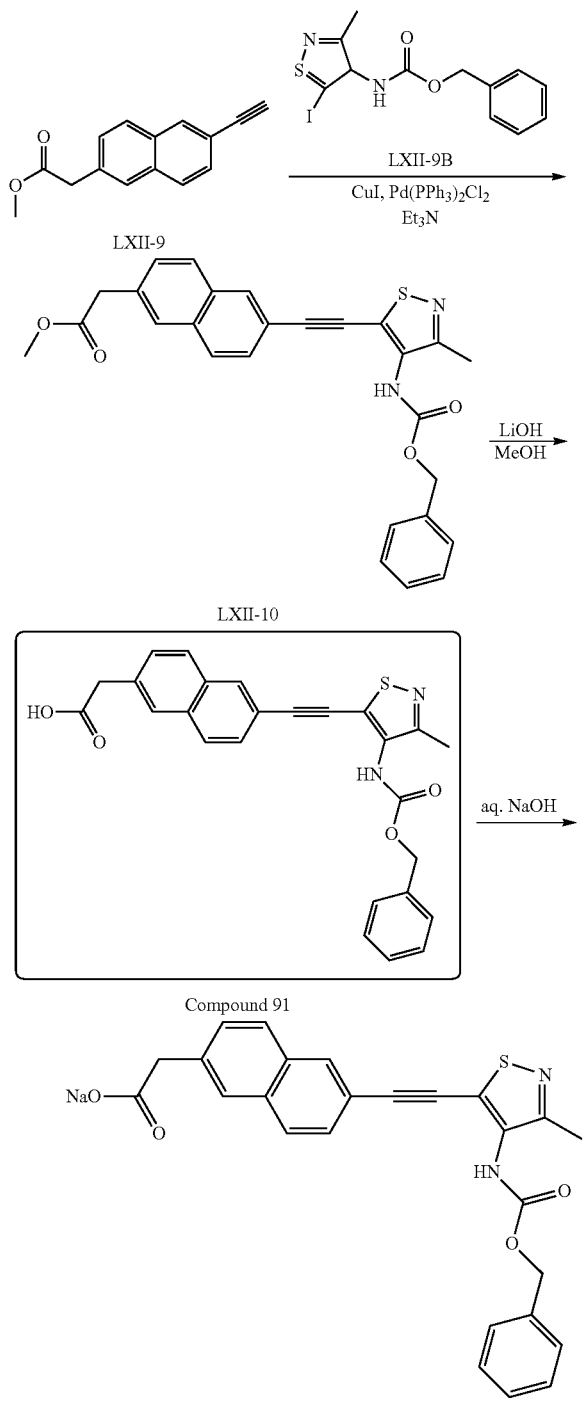

Compound 91 was prepared analogously to the procedure described in the synthesis of Compound 90. Compound 91: MS (ESI) m/z (M+H)+ 457.0.
Compound 91a was prepared analogously to the procedure described in the synthesis of Compound 90a. Compound 91a: $^1$H NMR (DMSO-d$_6$, 400 MHz): δ 9.53 (s, 1H), 8.03 (s, 1H), 7.81 (d, J=8.4 Hz, 1H), 7.75 (d, J=8.4 Hz, 1H), 7.67 (s, 1H), 7.48 (d, J=8.8 Hz, 1H), 7.29-7.36 (m, 3H), 7.25-7.27 (m, 3H), 5.16 (s, 2H), 3.39 (s, 2H), 2.28 (s, 3H). MS (ESI) m/z (M+H)+ 457.1.
Synthesis of Compound 92
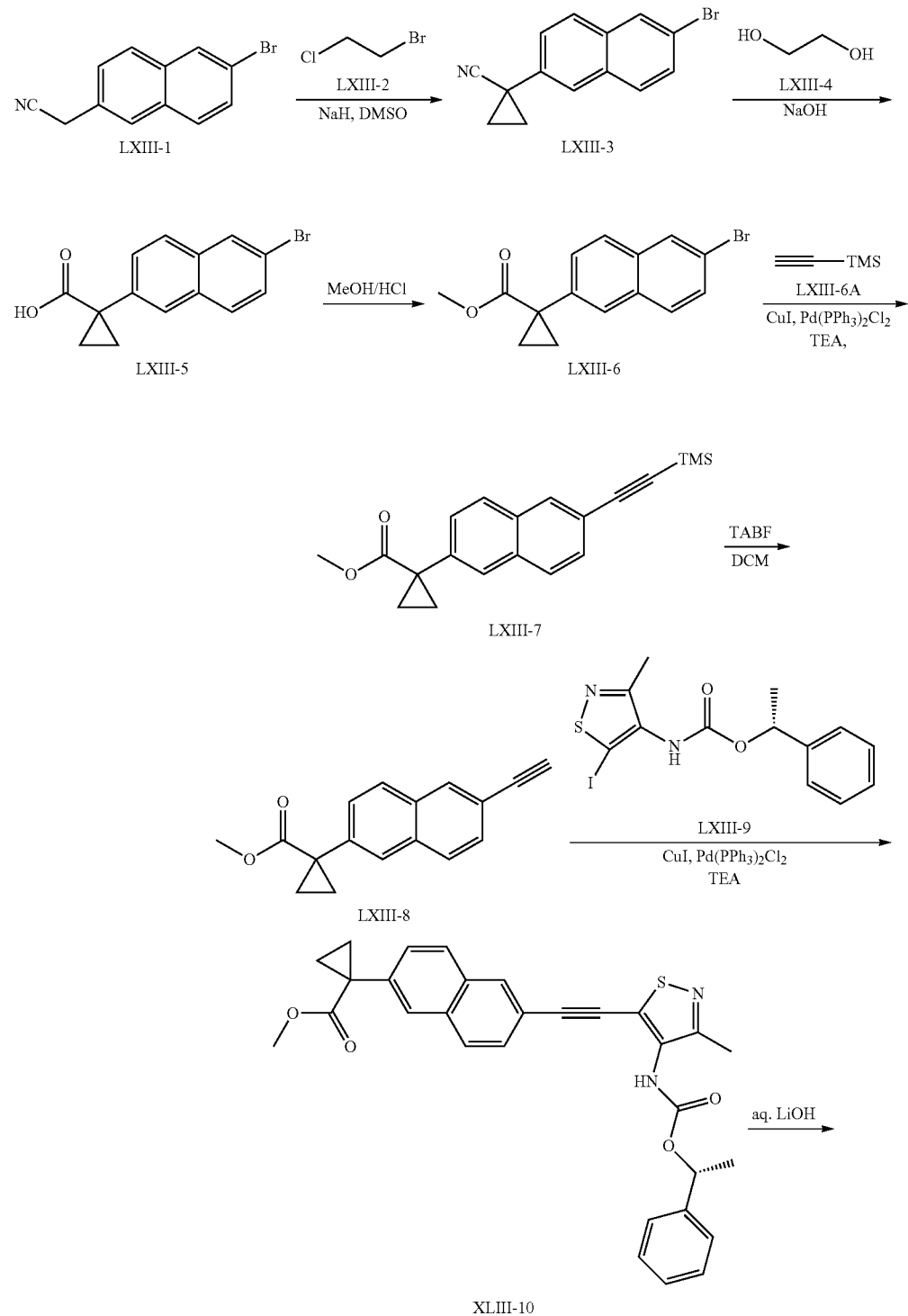

-continued

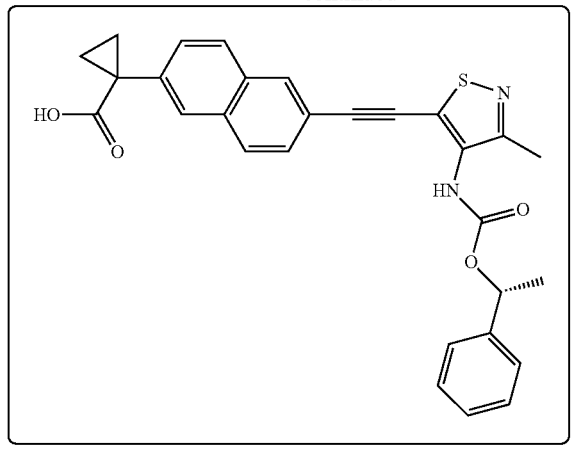

Compound 92

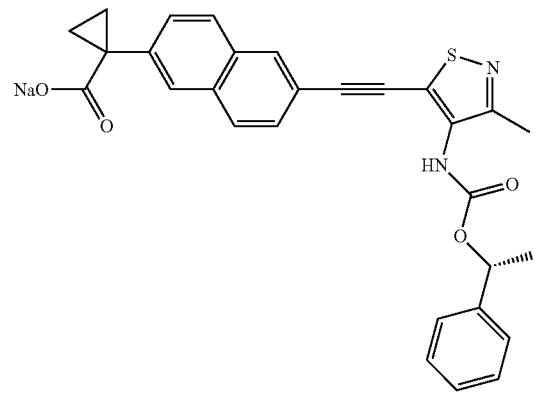

Compound 92a

To a stirred solution of compound LXIII-1 (2.46 g, 10 mmol) and compound LXIII-2 (1.86 g, 13 mmol) in DMSO (25 mL) was added NaH (1.0 g, 25 mmol) at 0° C. The reaction mixture was stirred at r.t. for 2 h. Water (50 mL) was added, and extracted with EtOAc (50 mL×3). The combined organic layers were washed with brine (20 mL×2), dried and concentrated under reduced pressure to give compound LXIII-3 (2.45 g, crude yield: 77.3%), which was used directly without further purification.

The mixture of compound LXIII-3 (2.2 g, 8.1 mmol), NaOH (3.24 g, 81 mmol) in ethane-1,2-diol (20 mL) was stirred at 150° C. for 3 days in a sealed tube. After being cooled to r.t., $H_2O$ (100 mL) was added, and the mixture was washed with t-BuOMe, the aqueous was adjust pH=2 with HCl (2N) and extracted with EtOAc (50 mL×3). The organic layer was combined and washed with brine, dried over $Na_2SO_4$, concentrated in vacuo to get compound LXIII-5 (2.0 g, yield: 94.3%). The residue was used directly without further purification.

The mixture of compound LXIII-5 (2.0 g, 6.9 mmol) in HCl/MeOH (4N, 40 mL) was stirred at reflux for 3 h. After concentrated, the mixture was diluted with water (40 mL), and extracted with EtOAc (40 mL×3). The combined organic layers were washed with brine (10 mL), and concentrated under reduced pressure to give compound LXIII-6 (1.60 g, yield: 76%).

To a stirred solution of compound LXIII-6 (1.60 g, 5.26 mmol), compound LXIII-6A (1.29 g, 13.16 mmol), CuI (105 mg, 0.526 mmol) in TEA (20 mL) was added $Pd(PPh_3)_2Cl_2$ (368 mg, 0.526 mmol) under Ar. After the addition, the solution was heated at reflux under Ar for 5 hours. The solution was concentrated, then $H_2O$ (100 mL) was added, and the mixture was extracted with EtOAc (100 mL×3). The organic layer was combined and washed with brine, dried over $Na_2SO_4$, and concentrated in vacuo to get compound LXIII-7 (1.50 g, yield 91.7%), which was used directly without further purification.

The mixture of compound LXIII-7 (1.50 g, 4.65 mmol), TBAF (2.0 g, 7.60 mmol) in DCM (30 mL) was stirred at room temperature for 2 hours. Then $H_2O$ was added, the residue was partitioned between $H_2O$ (30 mL) and DCM (60 mL), the aqueous phase was extracted with DCM, the combined organic layer was washed with brine, dried over $MgSO_4$, concentrated. The residue was purified by chromatography on silica gel (PE/EA=20/1) to afford compound LXIII-8 (0.95 g, yield: 81.8%).

Compound 92 was prepared analogously to the procedure described in the synthesis of Compound 90 and was used without further characterization.

Compound 92a was prepared analogously to the procedure described in the synthesis of Compound 90a. Compound 92a: $^1H$ NMR (DMSO-$d_6$, 400 MHz): δ 7.96 (s, 1 H), 7.79 (d, J=8.4 Hz, 1H), 7.64-7.69 (m, 2H), 7.52 (d, J=8.4 Hz, 2H), 7.21-7.33 (m, 6H), 5.71 (q, 1H), 2.24 (s, 3H), 1.48 (d, J=6.8 Hz, 3H), 1.20-1.21 (m, 2H), 0.74-0.75 (m, 2H). MS (ESI) m/z $(M+H)^+$ 497.1.

Synthesis of Compound 93
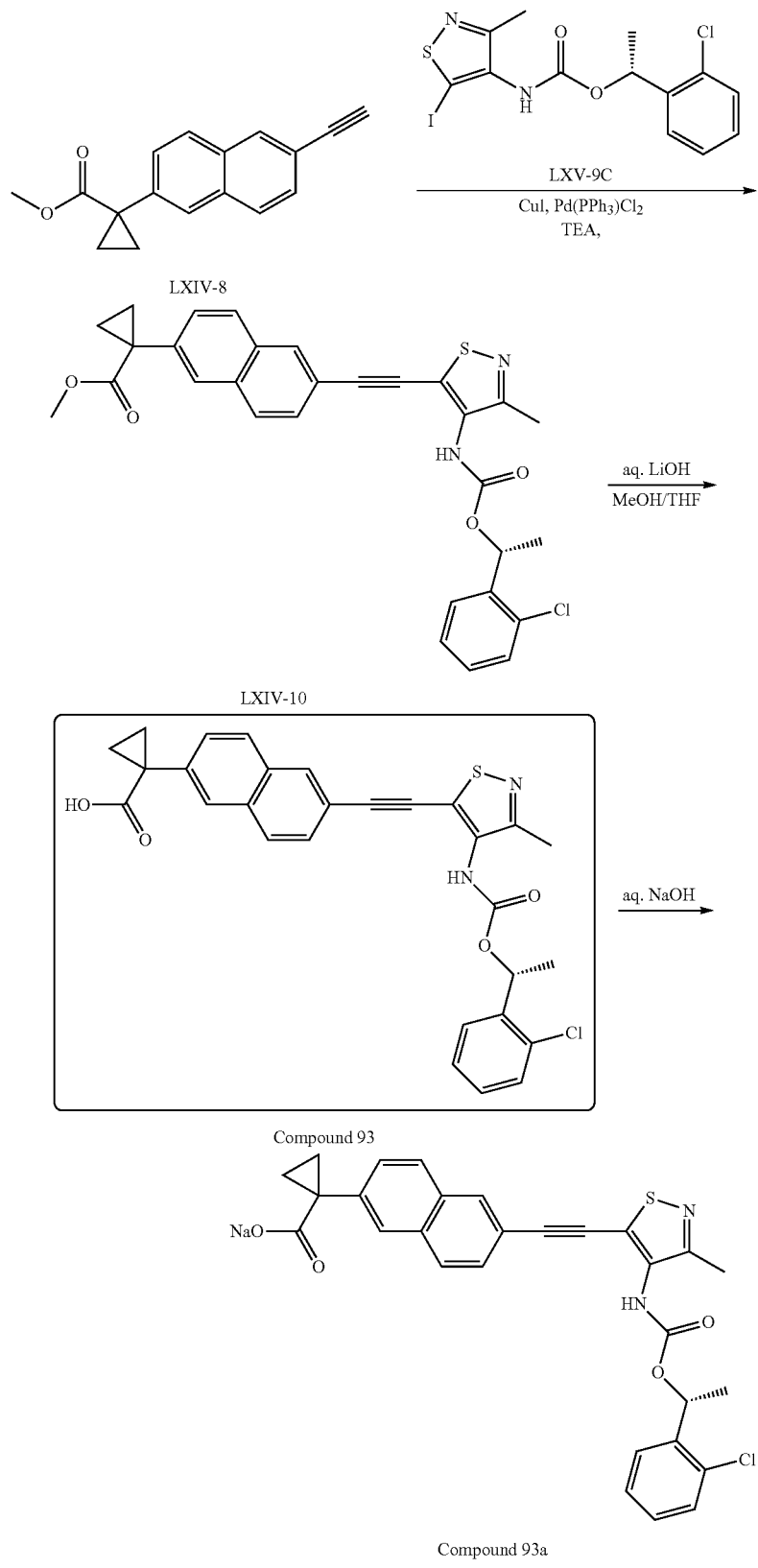

Compound 93 was prepared analogously to the procedure described in the synthesis of Compound 90. Compound 93: MS (ESI) m/z (M+H)⁺ 531.1.

Compound 93a was prepared analogously to the procedure described in the synthesis of Compound 90a. Compound 93a: $^1$H NMR (DMSO-d$_6$, 400 MHz): δ9.67 (s, 1H), 8.02 (s, 1H), 7.84 (d, J=8.4 Hz, 1H), 7.70-7.75 (m, 2H), 7.57 (d, J=8.4 Hz, 2H), 7.45-7.47 (m, 1H), 7.32-7.38 (m, 3H), 6.05 (q, 1H), 2.30 (s, 3H), 1.53 (d, J=5.2 Hz, 3H), 1.25 (br, 2H), 0.81 (br, 2H). MS (ESI) m/z (M+H)⁺ 531.1.

Synthesis of Compound 94

Synthetic Route (Scheme LXV)

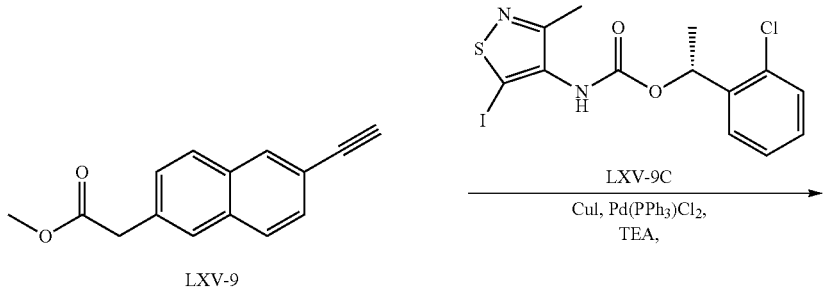

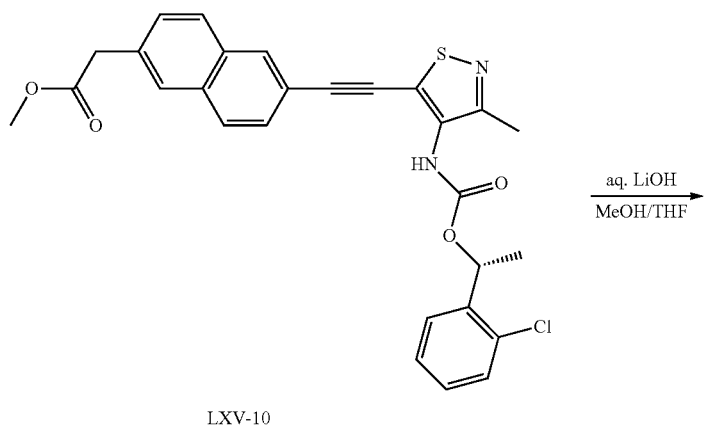

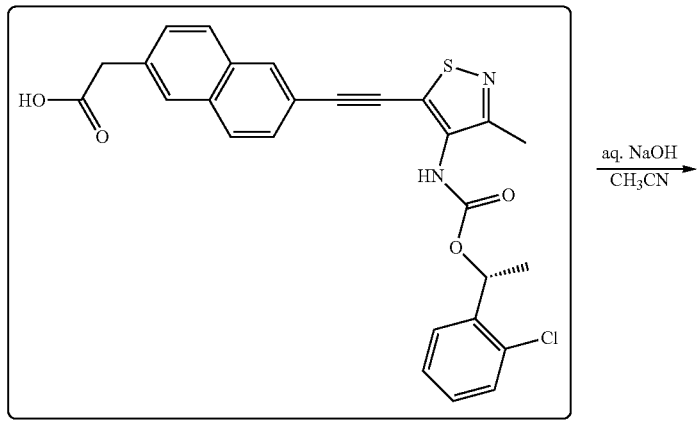

Compound 94

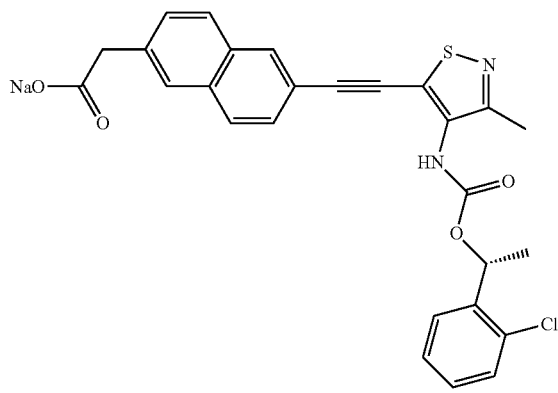
Compound 94a
Compound 94 was prepared analogously to the procedure described in the synthesis of Compound 90 and was used without further characterization.
Compound 94a was prepared analogously to Compound 90a. Compound 94a: $^1$H NMR (DMSO-d$_6$, 400 MHz): δ 9.73 (s, 1H), 8.03 (s, 1H), 7.83 (d, J=8.4 Hz, 1H), 7.77 (d, J=8.4 Hz, 1H), 7.70 (s, 1H), 7.51-7.54 (m, 2H), 7.30-7.44 (m, 4H), 6.05 (q, 1H), 3.40 (s, 2H), 2.3 (s, 3H), 1.22 (br, 3H). MS (ESI) m/z (M+H)$^+$ 505.1.
Synthesis of Compound 95
Synthetic Route (Scheme LXVI)
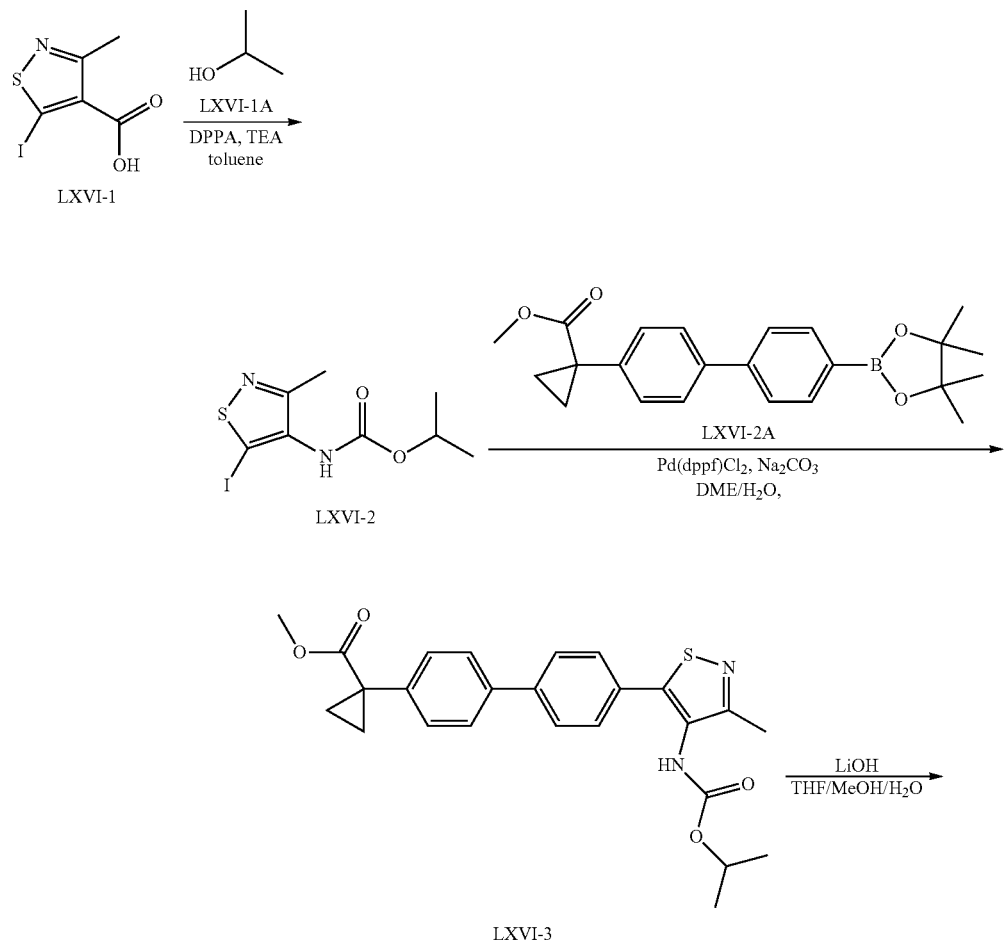

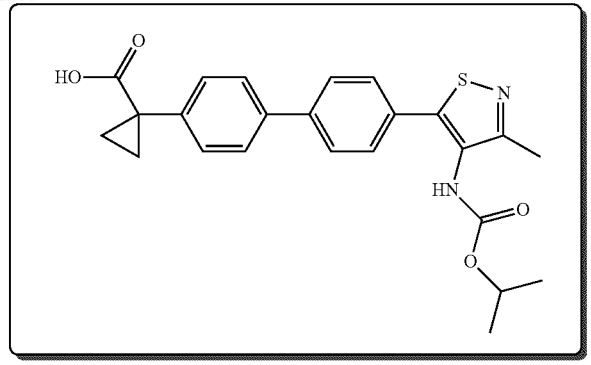
Compound 95
Compound 95 was prepared analogously to the procedure described in the synthesis of Compound 44. Compound 95: $^1$H NMR (DMSO-$d_6$, 400 MHz): δ 8.69 (s, 1H), 7.78 (d, J=8.8 Hz, 2H), 7.63-7.65 (m, 4H), 7.44 (d, J=8.4 Hz, 2H), 4.78-4.85 (m, 1H), 2.33 (s, 3H), 1.49-1.52 (m, 2H), 1.18-1.20 (m, 8H). MS (ESI) m/z (M+H)$^+$ 437.2.
Synthesis of Compound 96
Synthetic Route (Scheme LXVII)
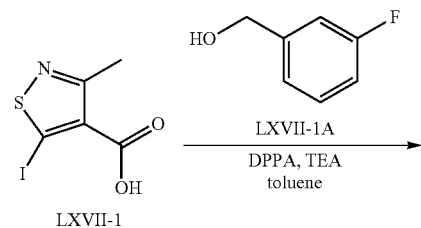
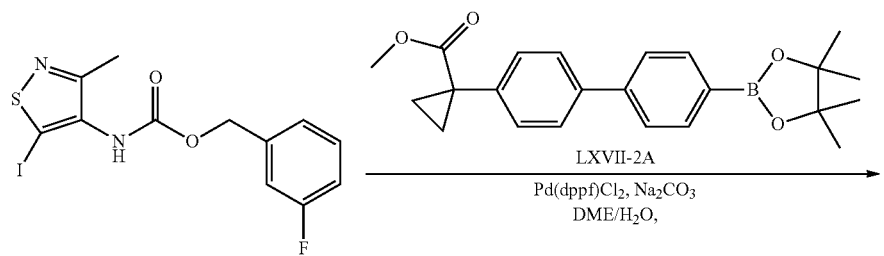
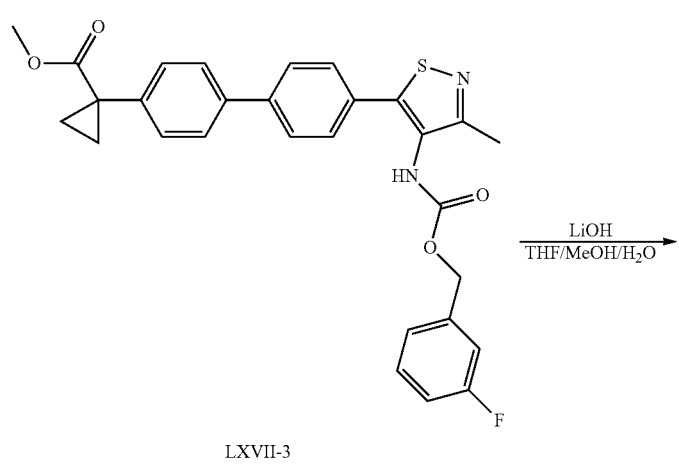

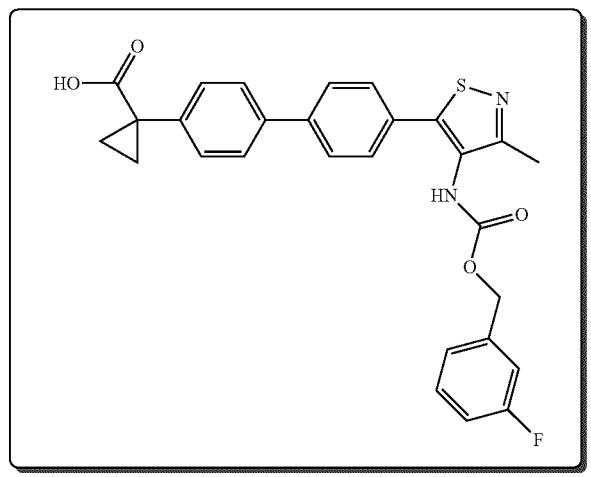
Compound 96
Compound 96 was prepared analogously to the procedure described in the synthesis of Compound 44. Compound 96: $^1$H NMR (DMSO-d$_6$, 400 MHz): δ 9.38 (s, 1H), 7.77 (d, J=8.4 Hz, 2H), 7.61-7.66 (m, 4 H), 7.41-7.46 (m, 3H), 7.16-7.25 (m, 3 H), 5.17 (s, 2H) 2.31 (s, 3H), 1.48-1.51 (m, 2H), 1.18-1.21 (m, 2H). MS (ESI) m/z (M+H)$^+$ 503.1.
Synthesis of Compound 97
Synthetic Route (Scheme LXVIII)
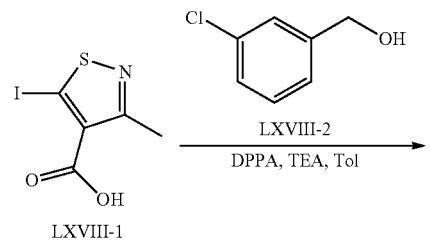
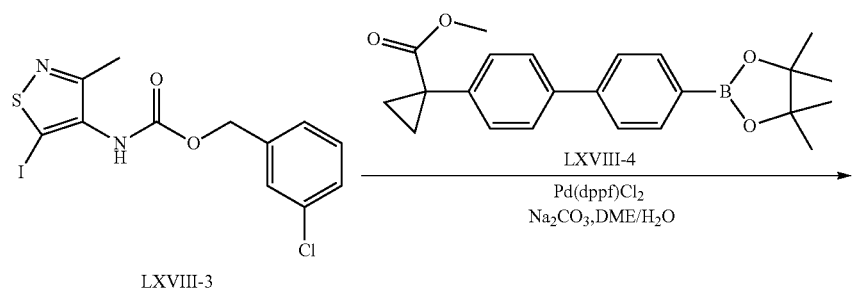

-continued
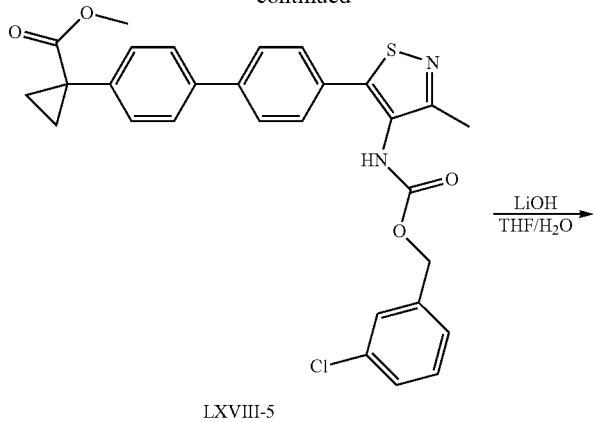
LXVIII-5
LiOH
THF/H₂O
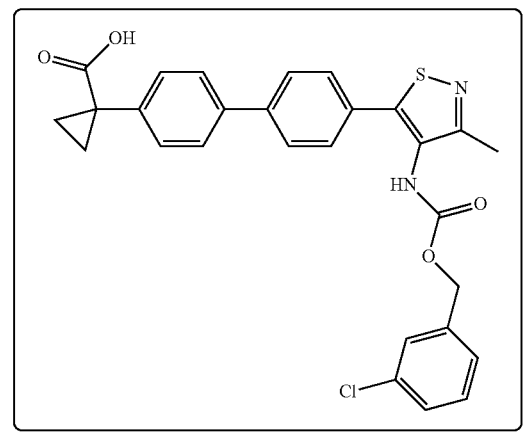
Compound 97
Compound 97 was prepared analogously to the procedure described in the synthesis of Compound 44. Compound 97: 4-1 NMR (DMSO-d₆, 400 MHz): δ 9.01 (s, 1H), 7.74 (d, J=8.4 Hz, 2H), 7.61-7.65 (m, 4 H), 7.45 (d, J=8.4 Hz, 2H), 7.27-7.38 (m, 4 H), 5.12 (s, 2H) 2.32 (s, 3H), 1.50-1.53 (m, 2H), 1.18-1.21 (m, 2H). MS (ESI) m/z (M+H)⁺ 519.1.
Synthesis of Compound 98
Synthetic Route (Scheme LXIX)
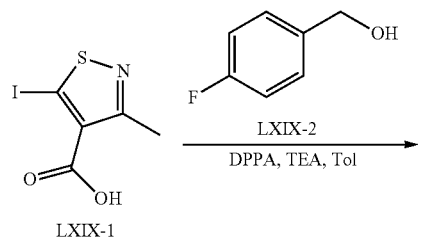
LXIX-1
LXIX-2
DPPA, TEA, Tol
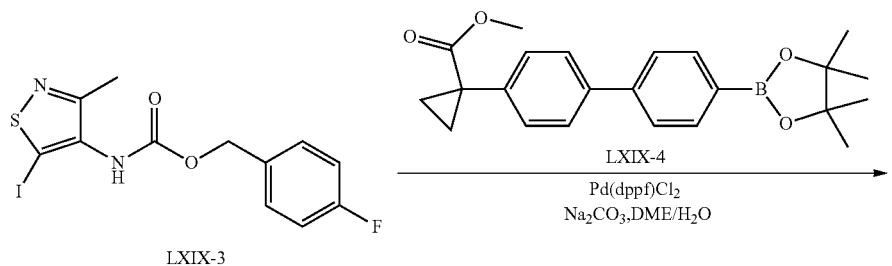
LXIX-3
LXIX-4
Pd(dppf)Cl₂
Na₂CO₃,DME/H₂O -continued
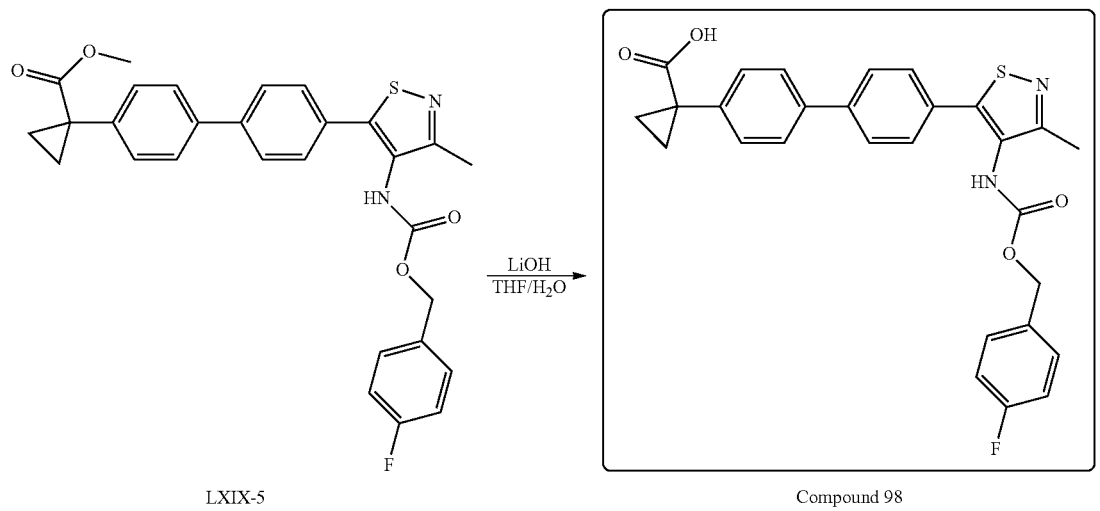
LXIX-5
Compound 98
Compound 98 was prepared analogously to the procedure described in the synthesis of Compound 44. Compound 98: $^1$H NMR (DMSO-$d_6$, 400 MHz): δ 8.95 (s, 1H), 7.74 (d, J=8.8 Hz, 2H), 7.60-7.72 (m, 4H), 7.44 (d, J=8.8 Hz, 2H), 7.37-7.38 (m, 2H), 7.12-7.17 (m, 2H), 5.10 (s, 2H) 2.31 (s, 3H), 1.50-1.52 (m, 2H), 1.17-1.18 (m, 2H). MS (ESI) m/z (M+H)$^+$ 503.2.
Synthesis of Compound 99
Synthetic Route (Scheme LXX)
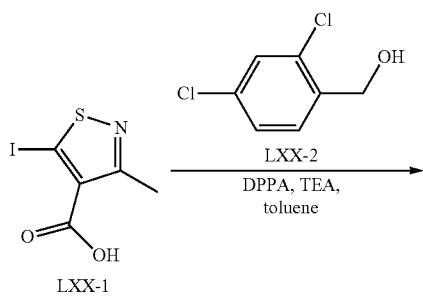
LXX-1
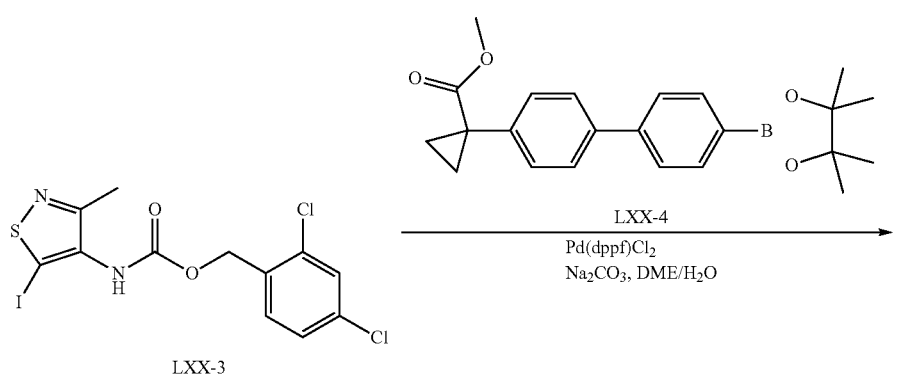

-continued
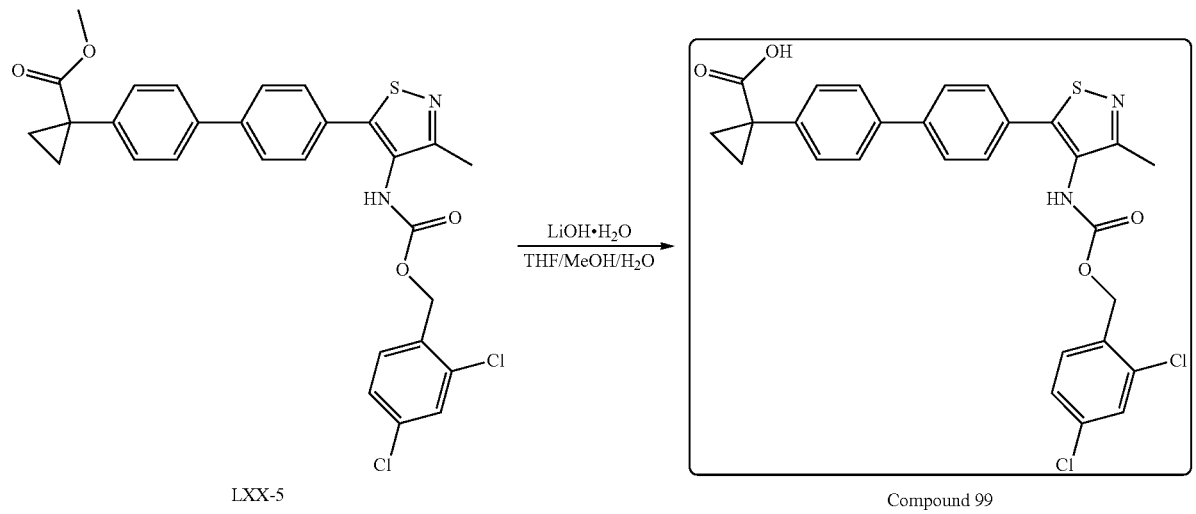
LXX-5 → Compound 99
Compound 99 was prepared analogously to the procedure described in the synthesis of Compound 44. Compound 99: ¹H NMR (Methanol-$d_4$ 400 MHz): δ 7.71 (d, J=8.0 Hz, 2H), 7.60-7.65 (m, 4H), 7.46-7.52 (m, 4H), 7.32-7.34 (m, 1H), 5.26 (s, 2H), 2.40 (s, 3H), 1.63-1.64 (m, 2H), 1.26-1.28 (m, 2H). MS (ESI) m/z (M+H)⁺ 553.1.
Synthesis of Compound 100
Synthetic Route (Scheme LXXI)
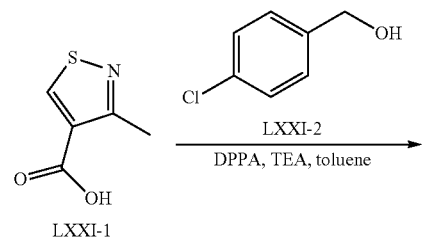
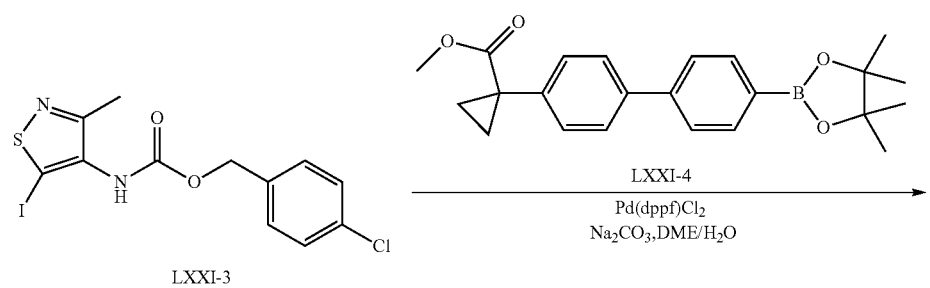

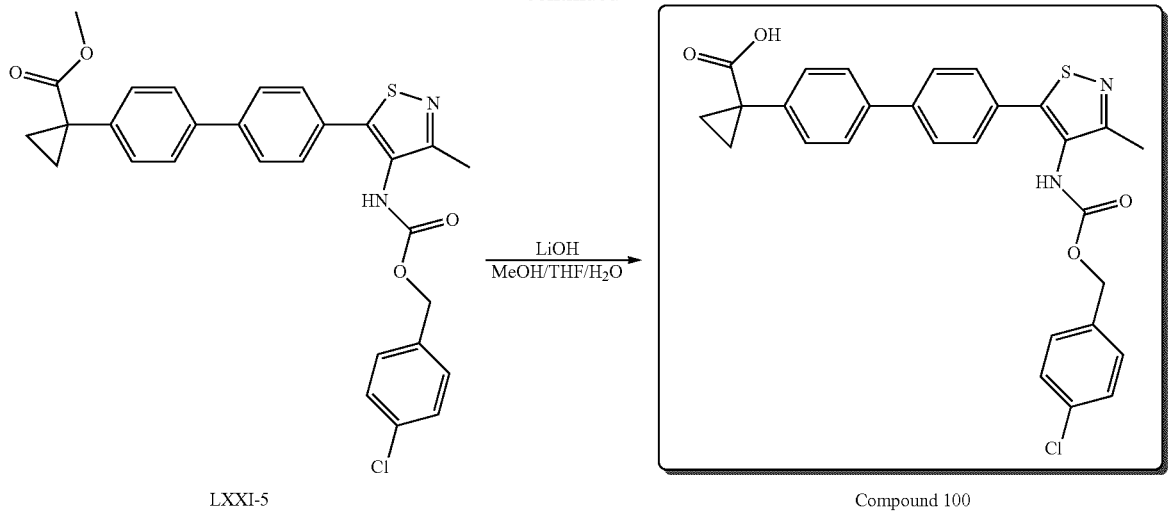
LXXI-5 → Compound 100
Compound 100 was prepared analogously to the procedure described in the synthesis of Compound 44. $^1$H NMR (DMSO-d$_6$ temp=80): δ: 8.97 (s, 1H), 7.72-7.75 (m, 2H), 7.60-7.64 (m, 4H), 7.40-7.46 (m, 2H), 7.33-7.40 (m, 4H), 5.10 (s, 2H), 2.31 (s, 3H), 1.50-1.51 (m, 2H), 1.17-1.18 (m, 2H). MS (ESI) m/z (M+H)$^+$ 519.2.
Synthesis of Compound 101
Synthetic Route (Scheme LXXII)
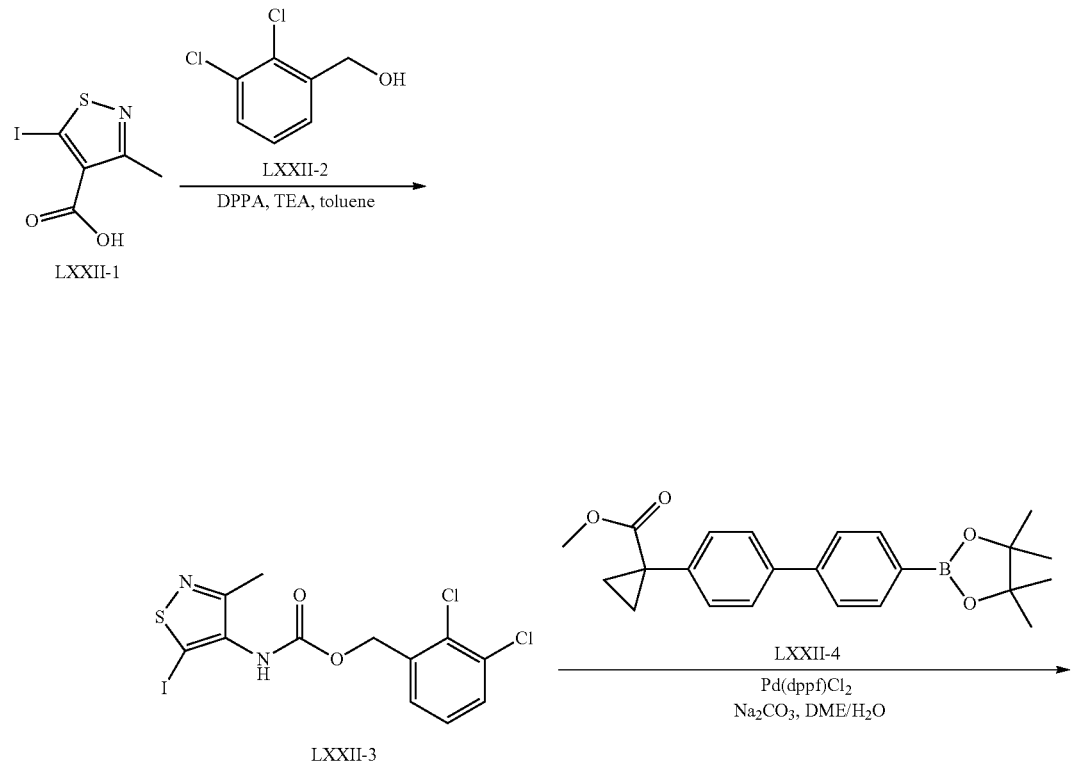

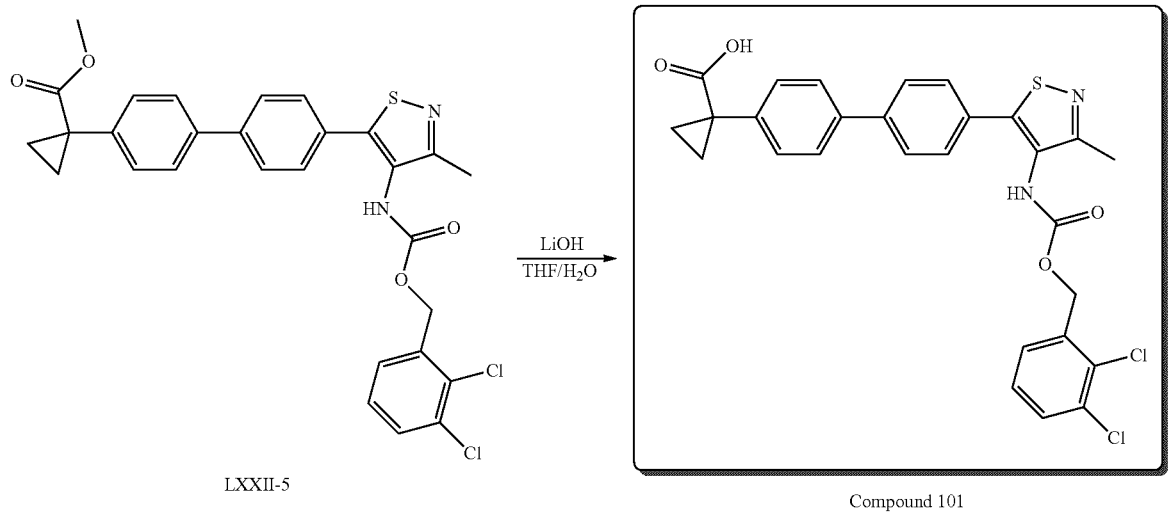
LXXII-5 →(LiOH, THF/H₂O)→ Compound 101
Compound 101 was prepared analogously to the procedure described in the synthesis of Compound 44. Compound 101: ¹H NMR (DMSO-d₆ temp=80): δ: 9.06 (s, 1H), 7.72-7.75 (m, 2H), 7.46-7.64 (m, 5H), 7.43-7.45 (m, 2H), 7.32-7.38 (m, 2H), 5.22 (s, 2H), 2.32 (s, 3H), 1.50-1.53 (m, 2H), 1.17-1.20 (m, 2H). MS (ESI) m/z (M+H)⁺ 553.0.
Synthesis of Compound 102
Synthetic Route (Scheme LXXIII)
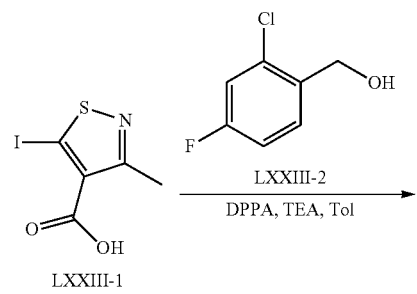
LXXIII-1 + LXXIII-2 →(DPPA, TEA, Tol)→
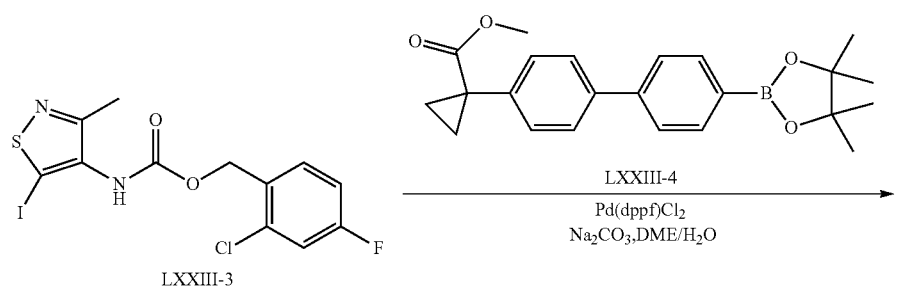
LXXIII-3 →(LXXIII-4, Pd(dppf)Cl₂, Na₂CO₃, DME/H₂O)→

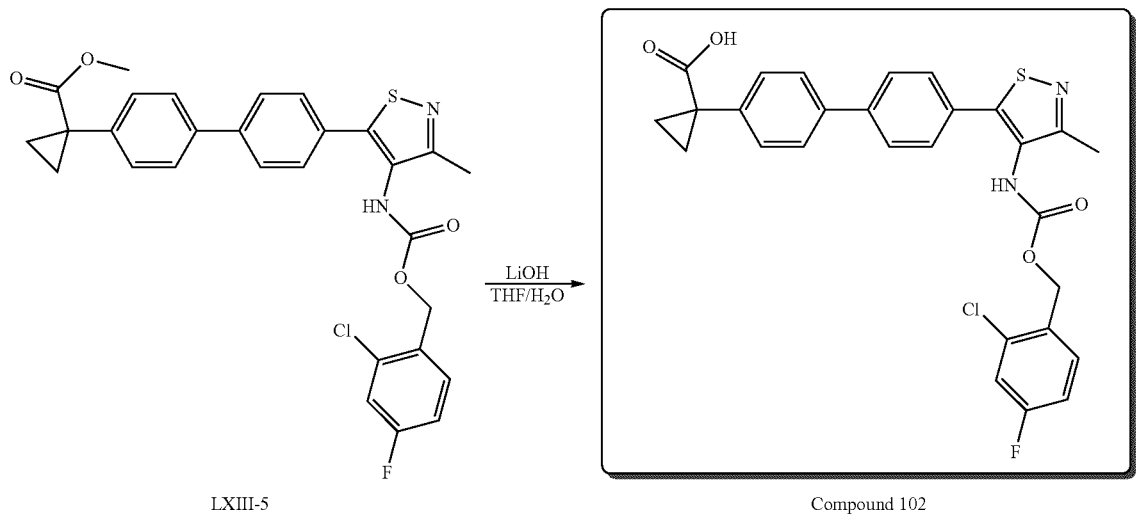
LXIII-5
Compound 102
Compound 102 was prepared analogously to the procedure described in the synthesis of Compound 44. Compound 102: $^1$H NMR (DMSO-d$_6$ temp=80): δ 9.07 (s, 1H), 7.75 (d, J=8.0 Hz, 2H), 7.61-7.65 (m, 5H), 7.41-7.46 (m, 4H), 7.20-7.22 (m, 1H), 5.18 (s, 2H), 2.32 (s, 3H), 1.51-1.52 (m, 2H), 1.19-1.21 (m, 2H). MS (ESI) m/z (M+H)$^+$ 537.1.
Synthesis of Compound 103
Synthetic Route (Scheme LXXIV)
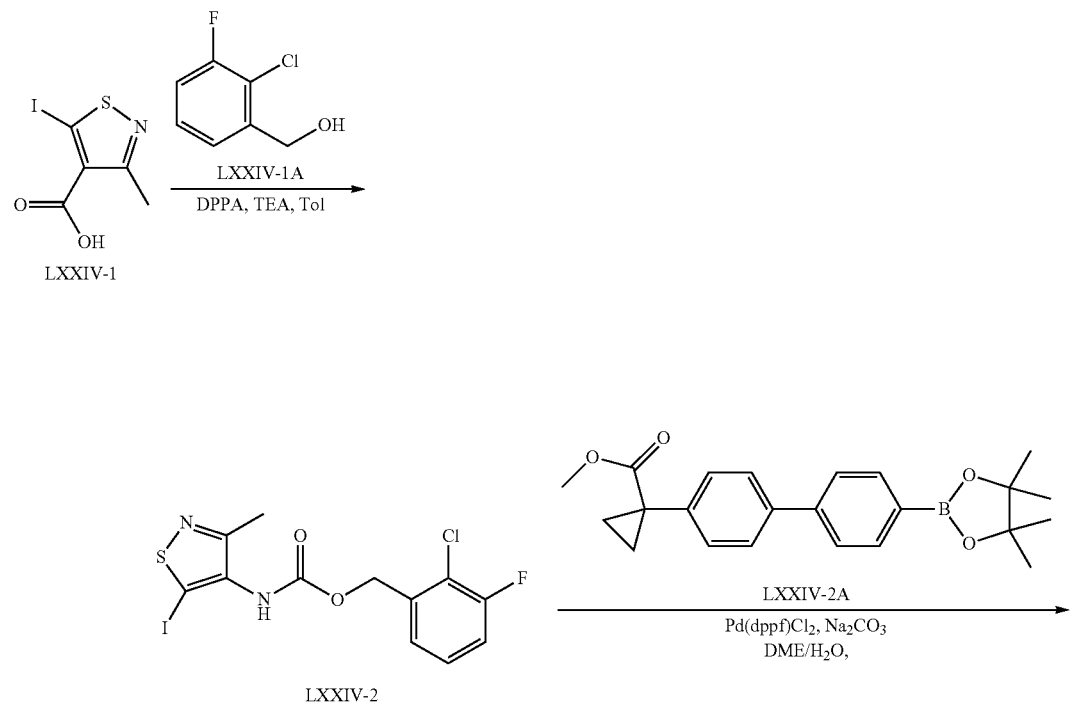

-continued
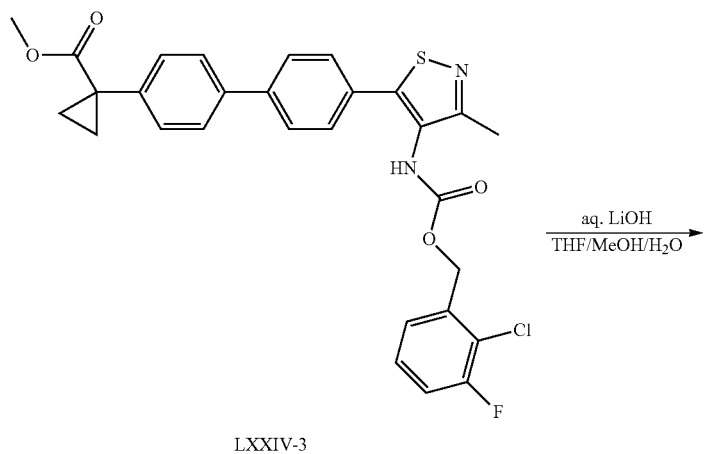
LXXIV-3
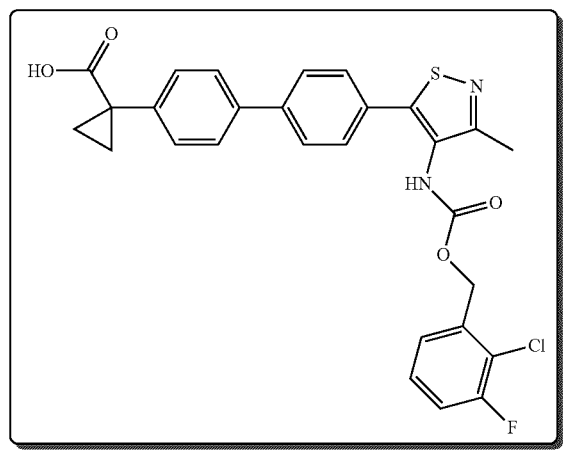
Compound 103
Compound 103 was prepared analogously to the procedure described in the synthesis of Compound 44. Compound 103: $^1$H NMR (DMSO-$d_6$, 400 MHz): δ 9.45 (s, 1H), 7.78 (d, J=8.4 Hz, 2H), 7.62-7.66 (m, 4H), 7.41-7.46 (m, 5H), 5.26 (s, 2H), 2.32 (s, 3H), 1.48-1.51 (m, 2H), 1.19-1.21 (m, 2H) MS (ESI) m/z (M+H)$^+$ 537.1
Synthesis of Compound 104
Synthetic Route (Scheme LXXV)
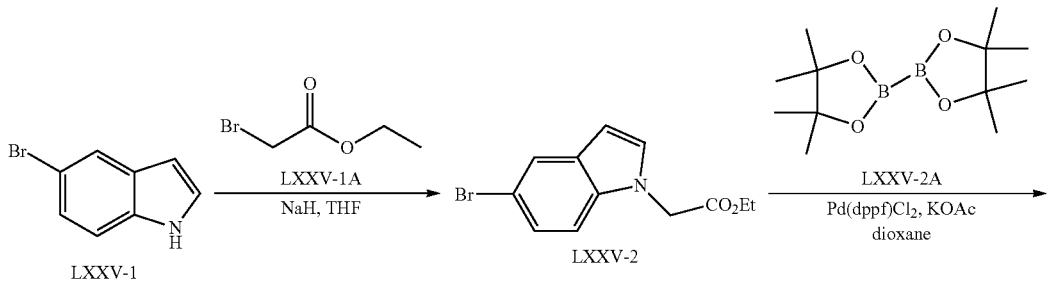

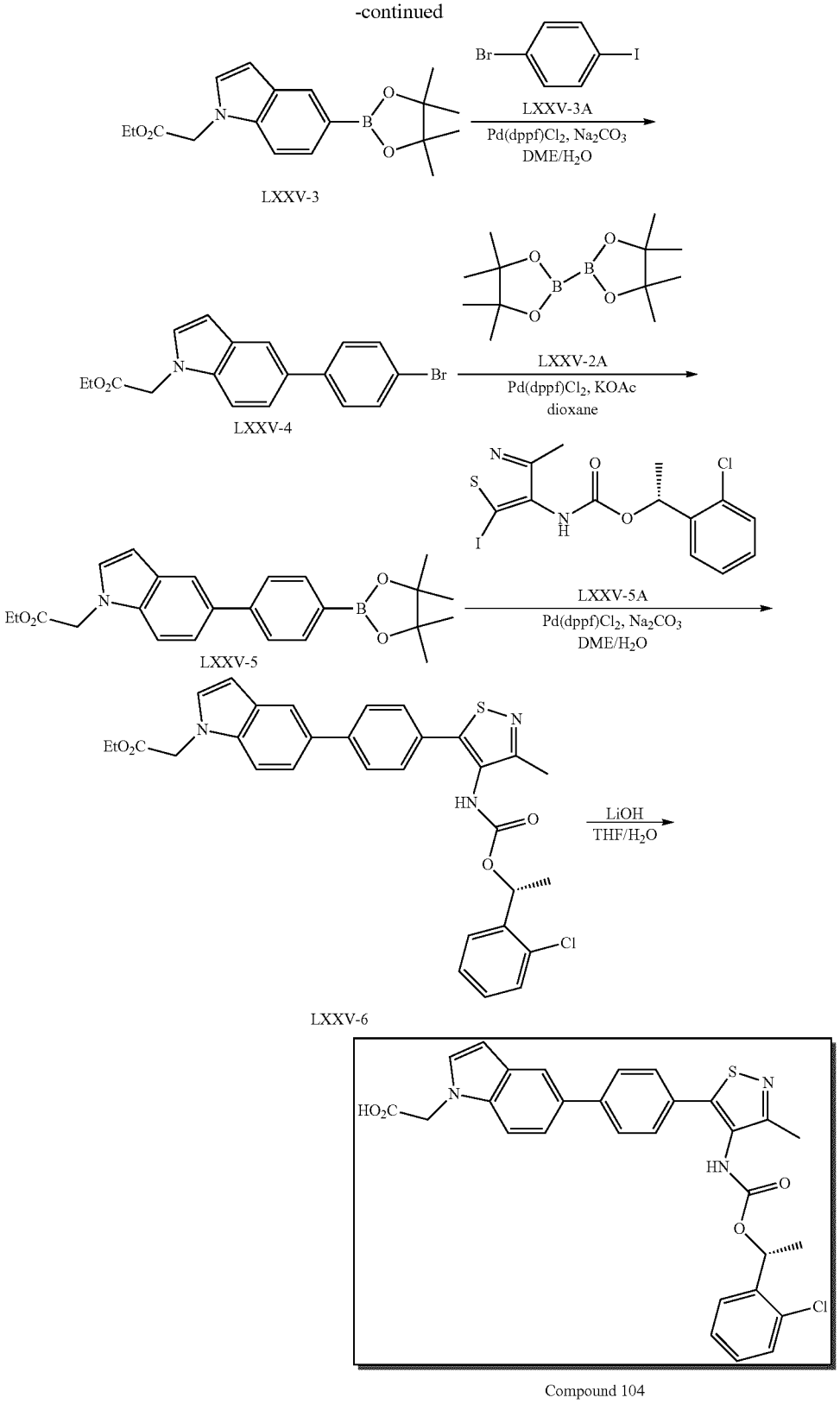
Compound 104
NaH (2.2 g, 55 mmol) was added to a solution of compound LXXV-1 (5.0 g, 25.6 mmol) in THF (80 mL) at 0° C. The mixture was stirred at 0° C. for 30 min, then compound LXXV-1A (5.1 g, 30.7 mmol) was added dropwise, the reaction mixture was stirred at r.t. overnight. Water (20 mL) was added, and extracted with EtOAc (50 mL×2), the combined organic layer was concentrated, and the residue was purified by column chromatography (PE/EA=10/1) to afford compound LXXV-2 (3.1 g, yield: 47.7%). MS (ESI) m/z (M+H)+ 282.2.

The mixture of compound LXXV-2 (3 g, 10.7 mmol), compound LXXV-2A (4.07 g, 16 mmol), KOAc (2.1 g, 21.4 mmol) and Pd(dppf)Cl$_2$ (780 mg, 1.07 mmol) in 50 mL dioxane was heated to reflux under argon for 4 hours. The mixture was concentrated, the residue was partitioned between H$_2$O and DCM, the aqueous phase was extracted with DCM, and the combined organic layer was washed with brine, dried over Na$_2$SO$_4$, concentrated. The residue was purified by chromatography on silica gel (PE/EA=10/1) to afford compound LXXV-3 (3.1 g, yield 85.7%).

To a solution of compound LXXV-3 (3.0 g, 9.12 mmol) in DME:H$_2$O=3:1 (20 mL), Na$_2$CO$_3$ (1.93 g, 18.24 mmol) and compound LXXV-3A (3.1 g, 11 mmol) were added, the resulting mixture was purged with nitrogen, then Pd (dppf)Cl$_2$ (664 mg, 0.91 mmol) was added. The reaction mixture was stirred at 80° C. overnight under nitrogen protection. Then the mixture was poured into water, extract with EtOAc (30 mL×3), the combined organic layers were dried over Na$_2$SO$_4$, concentrated in vacuo. The residue was purified by chromatography (PE:EA=50:1) to afford compound LXXV-4 (2.1 g, yield 64.6%). MS (ESI) m/z (M+H)+ 358.2.

The mixture of compound LXXV-4 (1 g, 2.8 mmol), compound LXXV-2A (1.07 g, 4.2 mmol), KOAc (0.55 g, 5.6 mmol) and Pd(dppf)Cl$_2$ (204 mg, 0.28 mmol) in 50 mL dioxane was heated to reflux under argon for 4 hours. The mixture was concentrated, the residue was partitioned between H$_2$O and DCM, the aqueous phase was extracted with DCM, and the combined organic layer was washed with brine, dried over Na$_2$SO$_4$, concentrated. The residue was purified by chromatography on silica gel (PE:EA=50:1) to afford compound LXXV-5 (0.8 g, yield 70.8%). MS (ESI) m/z (M+H)+ 406.1.

To a solution of compound LXXV-5 (330 mg, 0.81 mmol) in DME:H$_2$O=3:1 (20 mL), Na$_2$CO$_3$ (172 mg, 1.62 mmol) and compound LXXV-5A (409 mg, 0.97 mmol) were added, the resulting mixture was purged with nitrogen, then Pd (dppf)Cl$_2$ (59 mg, 0.081 mmol) was added. The reaction mixture was stirred at 80° C. overnight under nitrogen protection. Then the mixture was poured into water, and extract with EtOAc (10 mL×3), the combined organic layers were dried over Na$_2$SO$_4$, concentrated in vacuo. The residue was purified by chromatography (PE:EA=10:1) to afford compound LXXV-6 (0.12 g, yield 25.7%). MS (ESI) m/z (M+1)+ 574.1.

Preparation of Compound 104

To a solution of compound LXXV-6 (120 mg, 0.21 mmol) in THF (25 mL) was added water (25 mL) and lithium hydroxide monohydrate (101 mg, 4.2 mmol). The reaction mixture was stirred at room temperature overnight. The mixture was cooled down to 0° C. and neutralized to pH=5.0 with 3N hydrochloride solution. The mixture was extracted with EtOAc (50 mL×3). The combined organic phase was dried over Na$_2$SO$_4$ and concentrated. The residue was purified by prep. HPLC to give Compound 104 (20.2 mg, yield: 17.7%). $^1$HNMR (DMSO-d$_6$ 400 MHz): δ 8.38 (s, 1H), 7.34-7.89 (m, 12H), 6.56 (br, 1H), 6.02 (br, 1H), 5.02 (s, 1H), 2.31 (s, 1H), 1.48 (d, J=5.2 Hz, 3 H). MS (ESI) m/z (M+H)+ 546.0.

Synthesis of Compound 105

Synthetic Route (Scheme LXXVI)

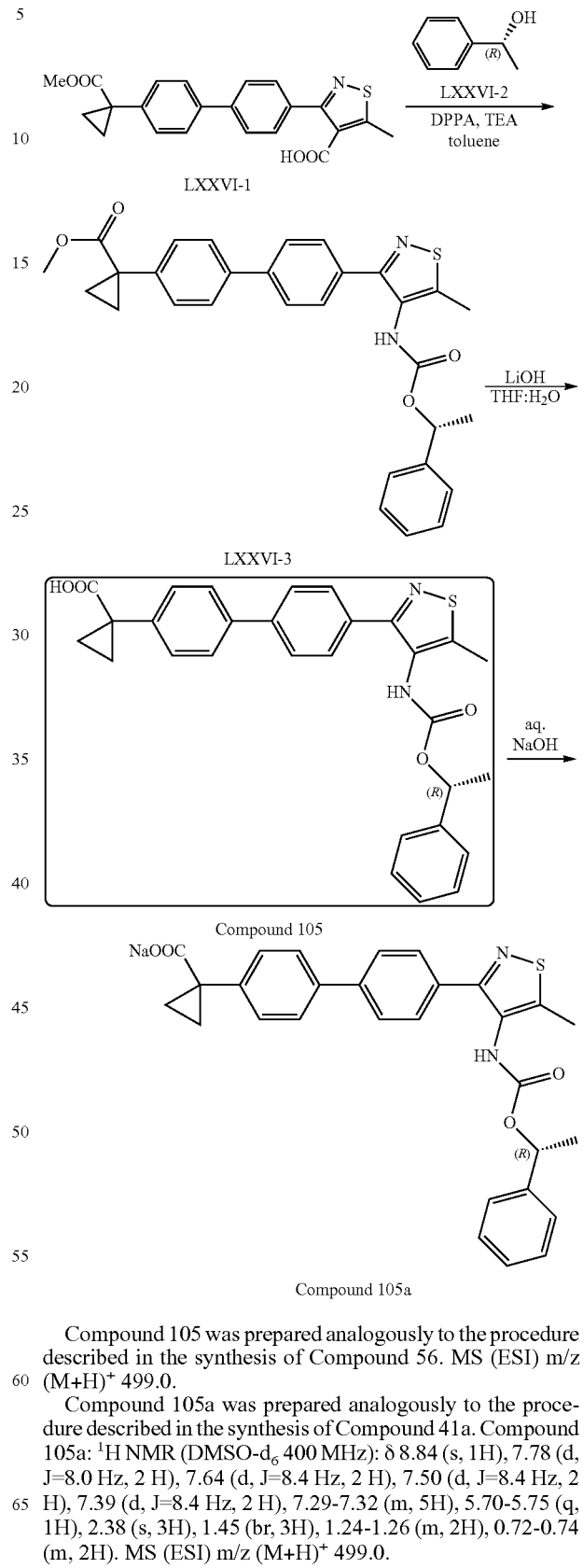

Compound 105 was prepared analogously to the procedure described in the synthesis of Compound 56. MS (ESI) m/z (M+H)+ 499.0.

Compound 105a was prepared analogously to the procedure described in the synthesis of Compound 41a. Compound 105a: $^1$H NMR (DMSO-d$_6$ 400 MHz): δ 8.84 (s, 1H), 7.78 (d, J=8.0 Hz, 2 H), 7.64 (d, J=8.4 Hz, 2 H), 7.50 (d, J=8.4 Hz, 2 H), 7.39 (d, J=8.4 Hz, 2 H), 7.29-7.32 (m, 5H), 5.70-5.75 (q, 1H), 2.38 (s, 3H), 1.45 (br, 3H), 1.24-1.26 (m, 2H), 0.72-0.74 (m, 2H). MS (ESI) m/z (M+H)+ 499.0.

Synthesis of Compound 106

Synthetic Route (Scheme LXXVII)

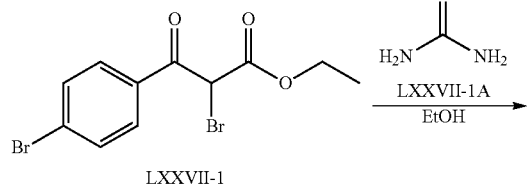
LXXVII-1

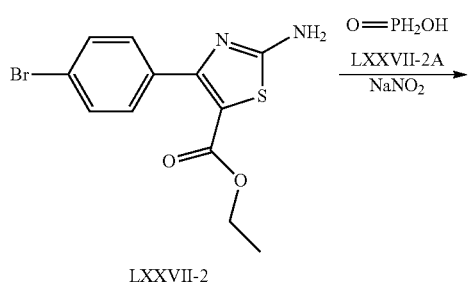
LXXVII-2

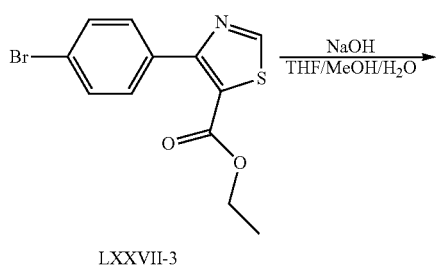
LXXVII-3

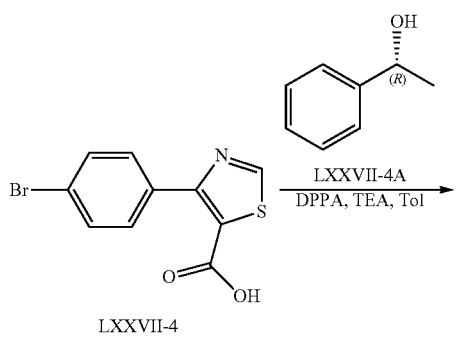
LXXVII-4

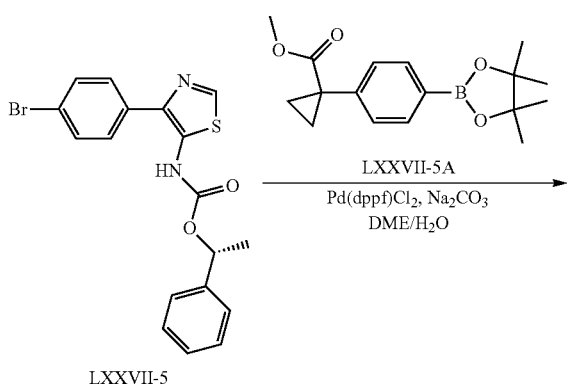
LXXVII-5

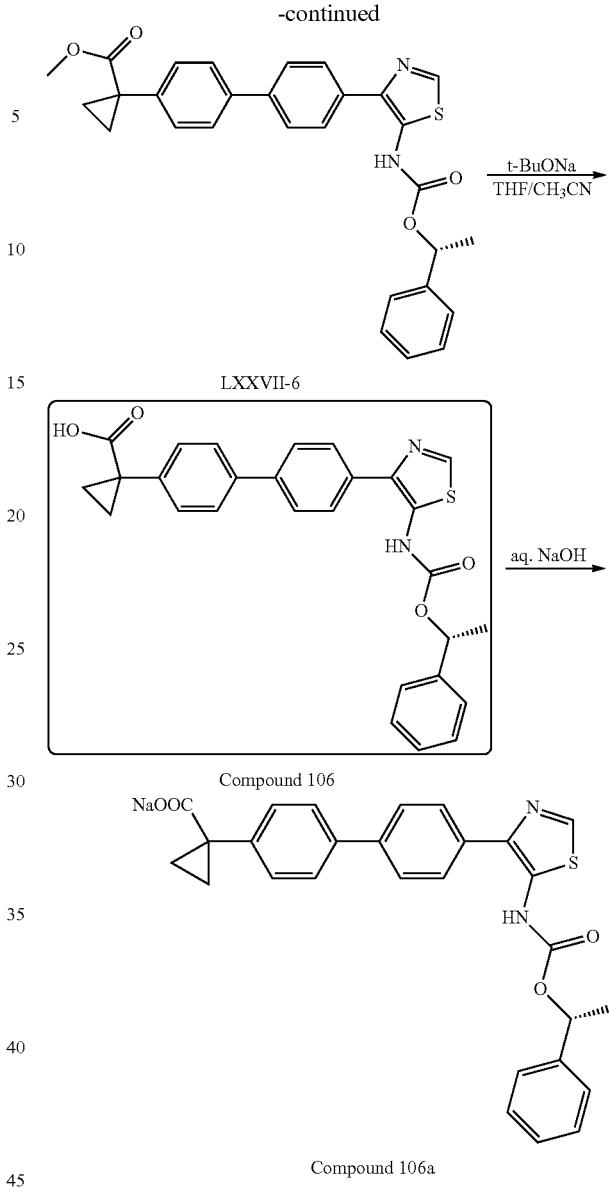

LXXVII-6

Compound 106

Compound 106a

A mixture of compound LXXVII-1 (1.48 g, 1.0 eq) and compound LXXVII-1A (0.328 g, 1.02 eq) in EtOH (32 ml) was heated to 75° C. for 2 h. The resulting mixture was concentrated under reduced pressure, then diluted with ice water, and the aqueous layer was extracted with dichloromethane (100 mL). The organic layer was combined and dried over $Na_2SO_4$ and concentrated under reduced pressure to afford crude compound LXXVII-2 (1.41 g, crude yield 100%). MS (ESI) m/z (M+H)$^+$ 328.9.

$NaNO_2$ (0.595 g, 2.0 eq) dissolved in $H_2O$ (8.7 mL) was added dropwise to a solution of compound LXXVII-2 (1.41 g, 1.0 eq) and compound LXXVII-2A (88.2 ml) at 0° C. The resulting mixture was stirred at 0° C. for 3 h and at 25° C. overnight. Then the mixture was adjusted to pH=8.0 with saturated $NaHCO_3$ solution and extracted with EtOAc (100 mL). The combined organic layer was washed with brine (50 mL), dried over $MgSO_4$, filtered and concentrated under reduced pressure. The residue was purified by column chromatography (PE/EA=10/1) to afford compound LXXVII-3 (360 mg, yield 26.77%). MS (ESI) m/z (M+H)$^+$ 313.8.

To a solution of compound LXXVII-3 (800 mg, 2.56 mmol) in THF (4 mL), MeOH (4 mL) and $H_2O$ (4 mL) was added sodium hydroxide (512 mg, 12.8 mmol). The reaction mixture was stirred at room temperature for 3 hours. The mixture was concentrated in vacuo to remove solvent. The aqueous phase was diluted with ice water and neutralized to pH~3 with 3N hydrochloride solution, and then extracted by EA, dried and concentrated to give crude compound LXXVII-4 (680 mg, yield: 94%), which was used to next step without further purification. MS (ESI) m/z (M+H)$^+$ 286.0.

To a solution of compound LXXVII-4 (283 mg, 1 mmol) in dry toluene (8 mL) was added (R)-1-(phenyl)ethanol (159 mg, 1.3 mmol), triethylamine (202 mg) and DPPA (357 mg, 1.3 mmol). The reaction mixture was heated to 80° C. for 3 hours. The mixture was diluted with EtOAc, washed with brine, dried over Na$_2$SO$_4$, filtered and concentrated. The residue was purified by column chromatography (PE/EA=6/1) to give compound LXXVII-5 (170 mg, yield: 42%). MS (ESI) m/z (M+H)$^+$ 405.0.

To a stirred mixture of compound LXXVII-5 (170 mg, 0.42 mmol), compound LXXVII-5A (140 mg, 0.46 mmol), and Na$_2$CO$_3$ (89 mg, 0.84 mmol) in DME (9 mL) and H$_2$O (3 mL) was added Pd(dppf)Cl$_2$ (31 mg, 0.042 mmol). The reaction mixture was flushed with nitrogen and heated to 80° C. overnight. The mixture was diluted with EtOAc (40 mL), washed with water and brine, dried over Na$_2$SO$_4$, filtered and concentrated. The residue was purified by column (PE:EA=4:1) to give compound LXXVII-6 (90 mg, yield: 43%). MS (ESI) m/z (M+H)$^+$ 499.2.

Preparation of Compound 106

To a solution of compound LXXVII-6 (90 mg, 0.181 mmol) in THF (4 mL) was added CH$_3$CN (1. mL) and t-BuONa (21 mg, 0.217 mmol). The reaction mixture was stirred at room temperature overnight. The mixture was cooled down to 0° C. and neutralized to pH=4 with 3N hydrochloride solution. The mixture was extracted with EtOAc (30 mL×3). The combined organic phase was dried over Na$_2$SO$_4$, concentrated, and then purified by Prep-HPLC to give Compound 106 (42 mg, yield: 48%). MS (ESI) m/z (M+H)$^+$ 485.3.

Preparation of Compound 106a

To a solution of Compound 106 (42 mg, 0.0.087 mmol) in MeCN (4 mL) was added 0.05N sodium hydroxide solution (1.7 mL) at 0° C. The reaction mixture was stirred for 30 minutes, and then lyophilized to give Compound 106a. $^1$H NMR (DMSO-d$_6$, 400 MHz): δ 8.48 (s, 1H), 8.15 (d, J=8.4 Hz, 2H), 7.62 (d, J=8.4 Hz, 2H), 7.54 (d, J=8.4 Hz, 2H), 7.24-7.41 (m, 7H), 5.85 (q, 1H), 1.51 (d, J=6.8 Hz, 3H), 1.35-1.37 (m, 2H), 0.89-0.91 (m, 2H). MS (ESI) m/z (M+H)$^+$ 485.3.

Synthesis of Compound 107

Synthetic Route (Scheme LXXVIII)

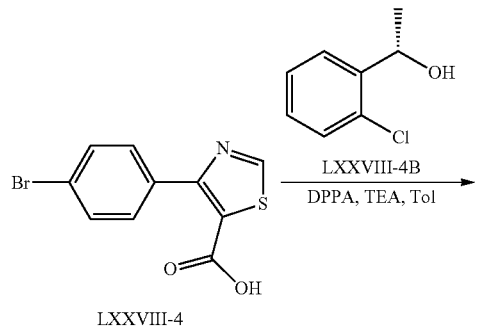

LXXVIII-4

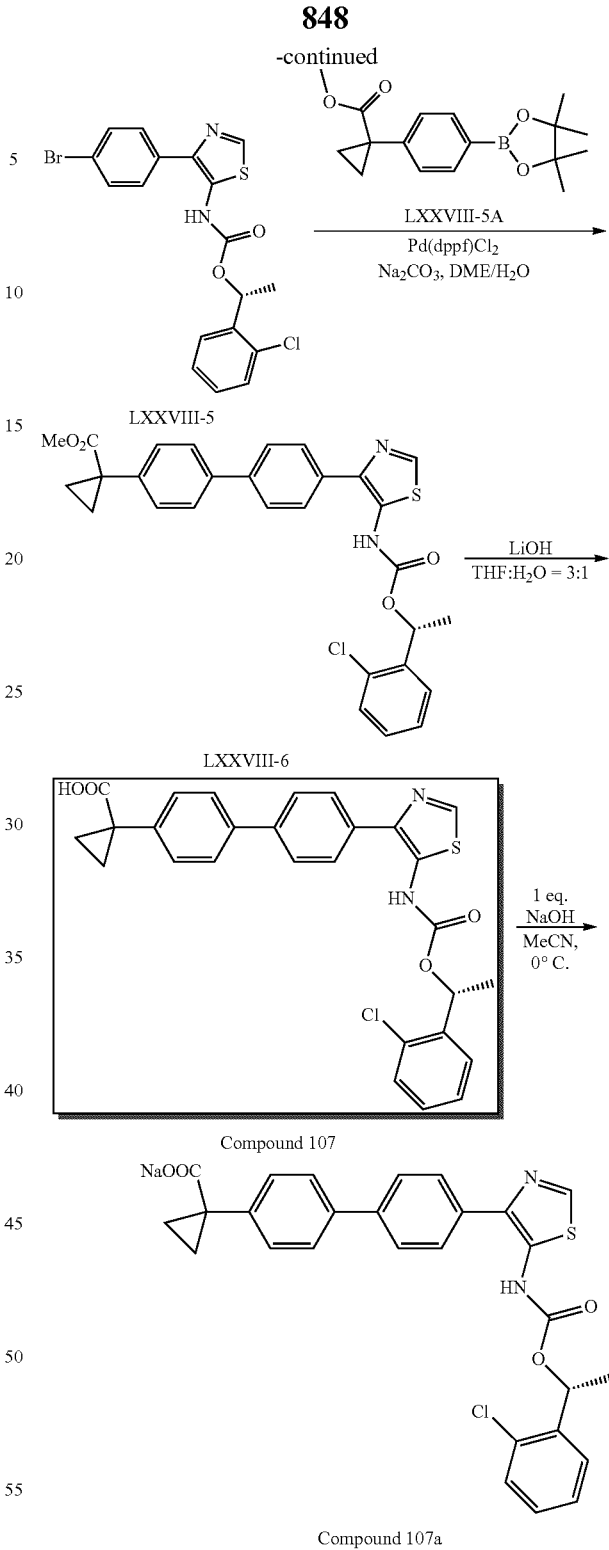

Compound 107 was prepared analogously to the procedure described in the synthesis of Compound 106. MS (ESI) m/z (M+H)$^+$ 519.2.

Compound 107a was prepared analogously to the procedure described in the synthesis of Compound 106a. Compound 107a: $^1$H NMR (, DMSO-d$_6$, 400 MHz): δ 8.33 (s, 1H), 8.26 (d, J=8.0 Hz, 2H), 7.54-7.61 (m, 5H), 7.23-7.43 (m, 5H), 6.12 (q, 1H), 1.49 (d, J=6.4 Hz, 3H), 1.37-1.39 (m, 2H), 0.96-0.98 (m, 2H). MS (ESI) m/z (M+H)+ 519.2.
Synthesis of Compound 108
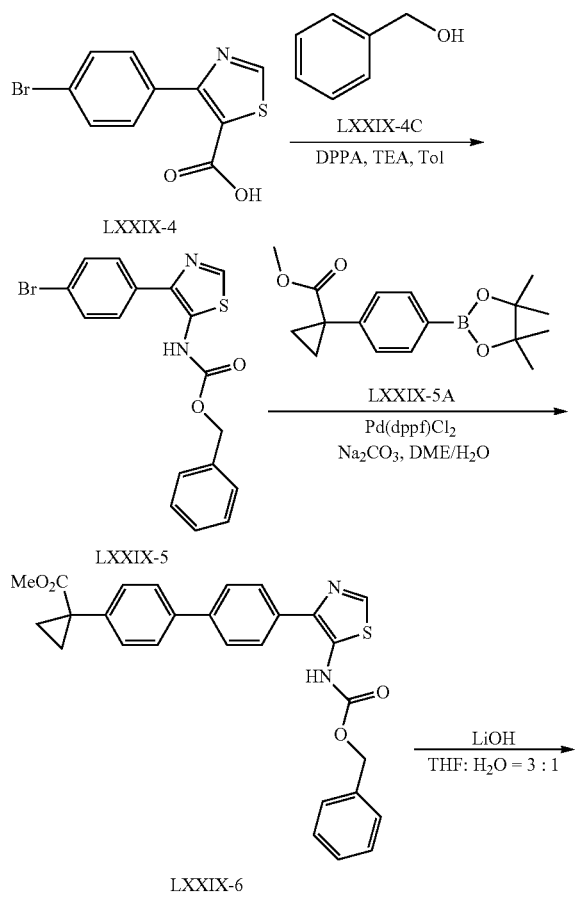
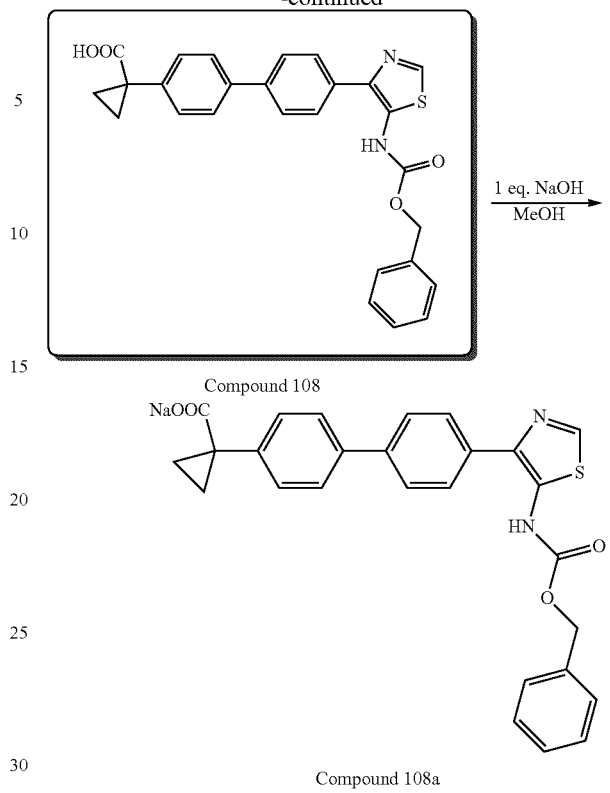
Compound 108 was prepared analogously to the procedure described in the synthesis of Compound 106. MS (ESI) m/z (M+H)+ 471.1.
Compound 108a was prepared analogously to the procedure described in the synthesis of Compound 106. ¹HNMR (DMSO-$d_6$ 400 MHz) δ 8.23-8.38 (br, 3H), 7.61 (d, J=8.4 Hz, 2H), 7.53 (d, J=8.0 Hz, 2H), 7.28-7.40 (m, 7H), 5.13 (s, 2H), 1.28-1.29 (m, 2 H), 0.84-0.85 (m, 2H). MS (ESI) m/z (M+H)+ 471.1.
Synthesis of Compound 109
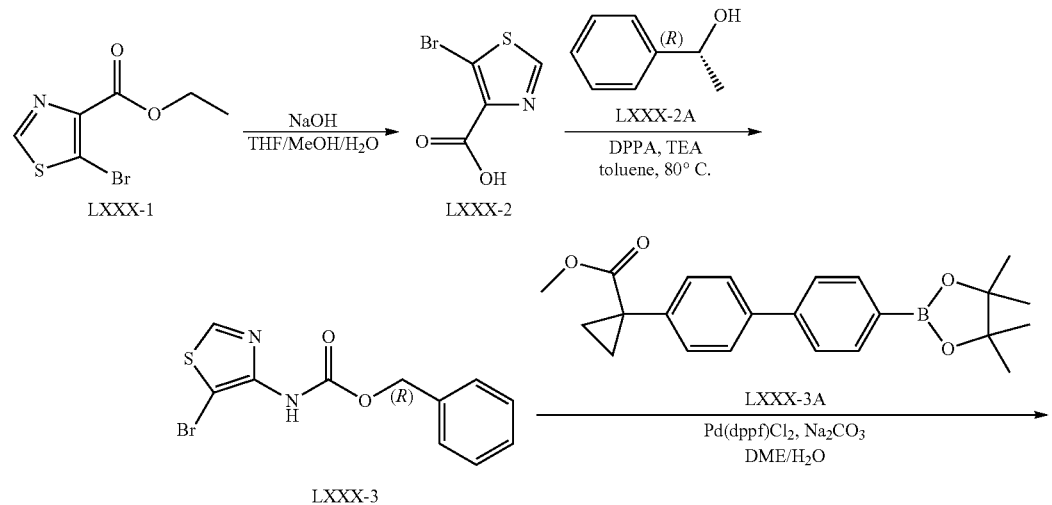

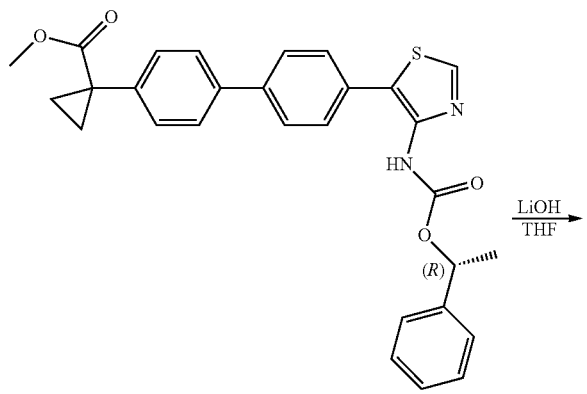

LXXX-4

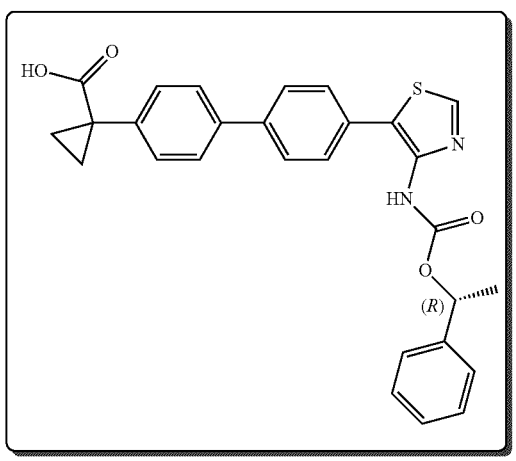

Compound 109

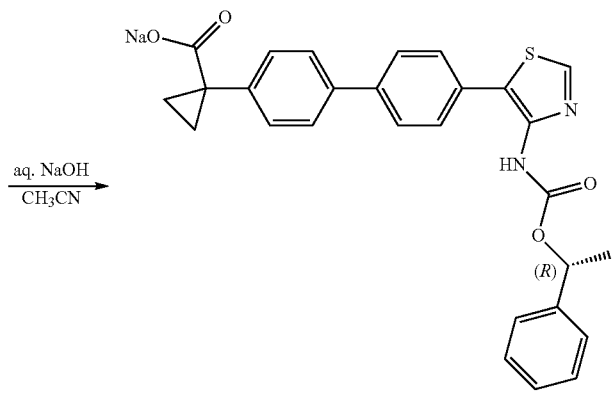

Compound 109a

To a stirred solution of compound LXXX-1 (3 g, 12.69 mmol) in methanol (30 mL), THF (30 mL) and water (30 mL), NaOH (1.52 g, 38.1 mmol) was added. The mixture was stirred at room temperature for 1 hour. The solution was concentrated, then $H_2O$ (20 mL) was added, and the mixture was extracted with EtOAc (50 mL×3). The organic layer was combined and washed with brine, dried over $Na_2SO_4$, concentrated in vacuo to afford compound LXXX-2 (2.2 g, yield 83%).

To a stirred solution of compound LXXX 2 (0.7 g, 3.37 mmol), compound LXXX-2A (0.53 g, 4.36 mmol), TEA (677 mg, 6.7 mmol) in toluene (10 mL) was added DPPA (1.2 g, 4.36 mmol) under nitrogen. After the addition, the solution was heated to reflux under nitrogen over night. The solution was concentrated. The residue was purified by column chromatography on silica gel (Petroleum ether:EtOAc=3:1) to afford compound LXXX-3 (0.76 g, yield 69%). MS (ESI) m/z (M+Na)+ 350.9.

The mixture of compound LXXX-3 (400 mg, 1.22 mmol), compound LXXX-3A (462 mg, 1.22 mmol), $Na_2CO_3$ (259 mg, 2.44 mmol) and Pd(dppf)$Cl_2$ (40 mg) in DME (12 mL) and water (4 mL) was stirred under microwave for 15 min at 120° C. Then water (20 mL) was added, and extracted with EtOAc (15 mL×3). The combined organic layers were washed with brine (20 mL), dried and concentrated under reduced pressure. The residue was purified by column chromatography on silica gel (EtOAc/HOAc=2:1) to afford compound LXXX-4 (520 mg, yield: 88%). MS (ESI) m/z (M+Na)+ 521.1.

Compound 109 was prepared analogously to the procedure described in the synthesis of Compound 106 (0.13 g, yield 45%). MS (ESI) m/z (M+Na)+ 507.0.

Compound 109a was prepared analogously to the procedure described in the synthesis of Compound 106a (108 mg, yield: 79%). $^1$H NMR (DMSO-$d_6$, 400 MHz): δ 9.51 (br, 1H), 9.02 (s, 1H), 7.66 (d, J=8.4 Hz, 2H), 7.58 (d, J=8 Hz, 2H), 7.51 (d, J=8.2 Hz, 2H), 7.29-7.35 (m, 7H), 5.69 (q, 1H), 1.43 (m, 3H), 1.19 (br, 2H), 0.69 (br, 2H). MS (ESI) m/z (M+H)+ 507.2.

Synthesis of Compound 110
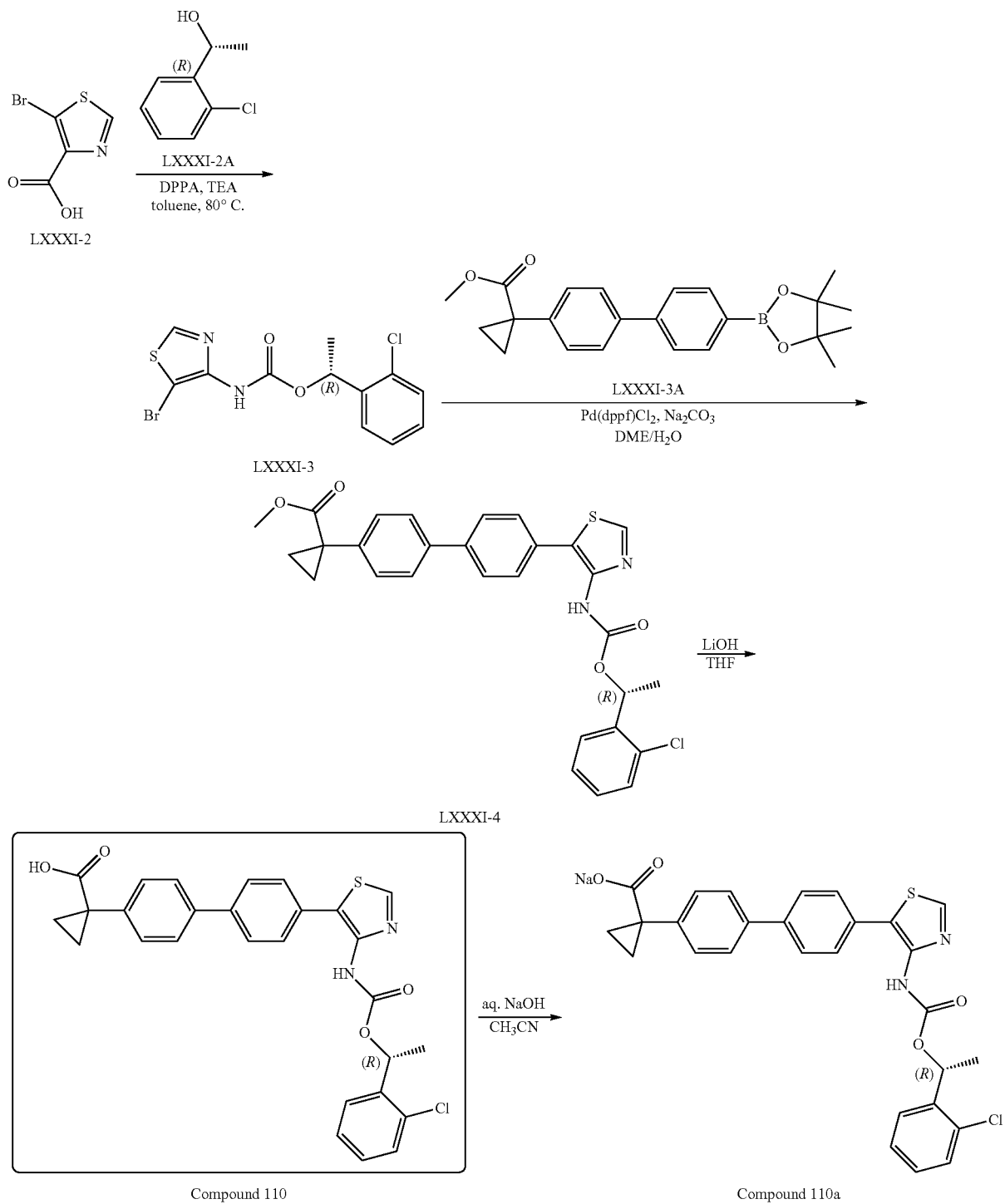
Compound 110 was prepared analogously to the procedure described in the synthesis of Compound 109. MS (ESI) m/z (M+H)+ 519.1.
Compound 110a was prepared analogously to the procedure described in the synthesis of Compound 109a. $^1$H NMR (DMSO-$d_6$, 400 MHz): δ 9.62 (br, 1H), 8.96 (s, 1H), 7.64 (d, J=8.4 Hz, 2H), 7.56 (d, J=8.4 Hz, 2H), 7.47 (d, J=8.4 Hz, 2H), 7.42 (d, J=8.4 Hz, 2H), 7.30-7.32 (m, 4H), 5.91 (q, 1H), 1.40 (m, 3H), 1.17 (br, 2H), 0.66 (br, 2H). MS (ESI) m/z (M+H)+ 541.2

Synthesis of Compound 111
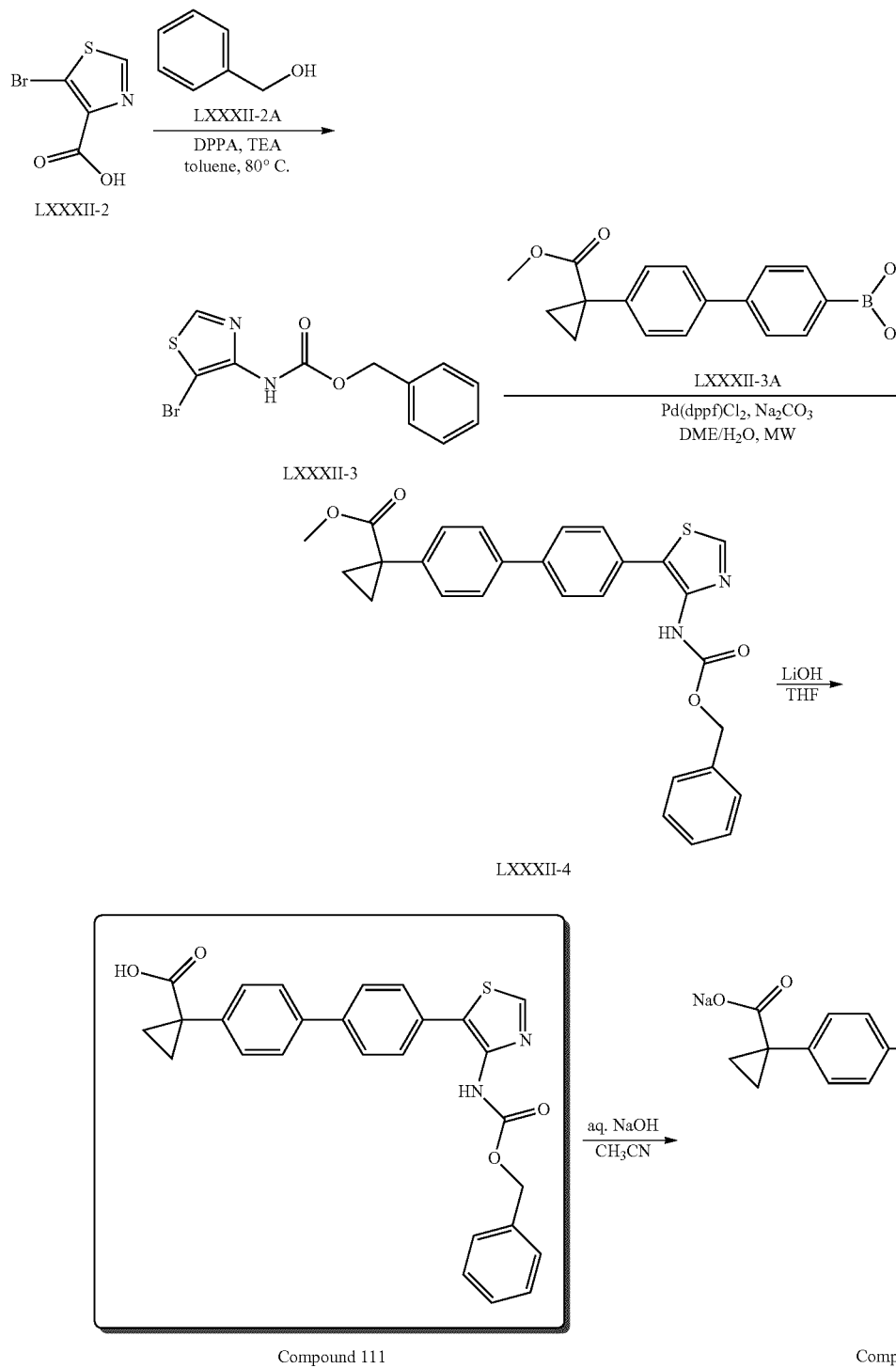
Compound 111 was prepared analogously to the procedure described in the synthesis of Compound 109. MS (ESI) m/z (M+H)+ 471.0.
Compound 111a was prepared analogously to the procedure described in the synthesis of Compound 109a. $^1$H NMR (DMSO-$d_6$, 400 MHz): δ 9.58 (br, 1H), 9.00 (s, 1H), 7.69 (d, J=8.4 Hz, 2H), 7.61 (d, J=8.4 Hz, 2H), 7.52 (d, J=8.4 Hz, 2H), 7.33-7.37 (m, 7H), 5.09 (q, 1H), 1.20 (br, 2H), 0.70 (br, 2H) MS (ESI) m/z (M+H)+ 493.0.

Synthesis of Compound 112

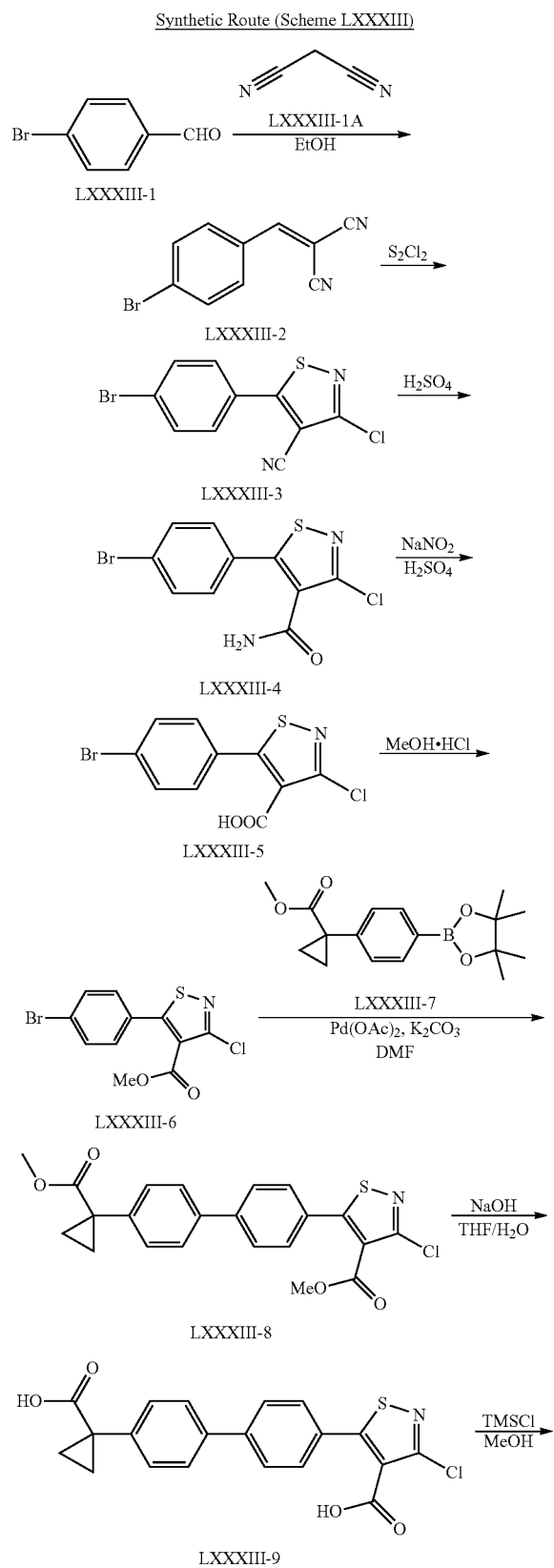

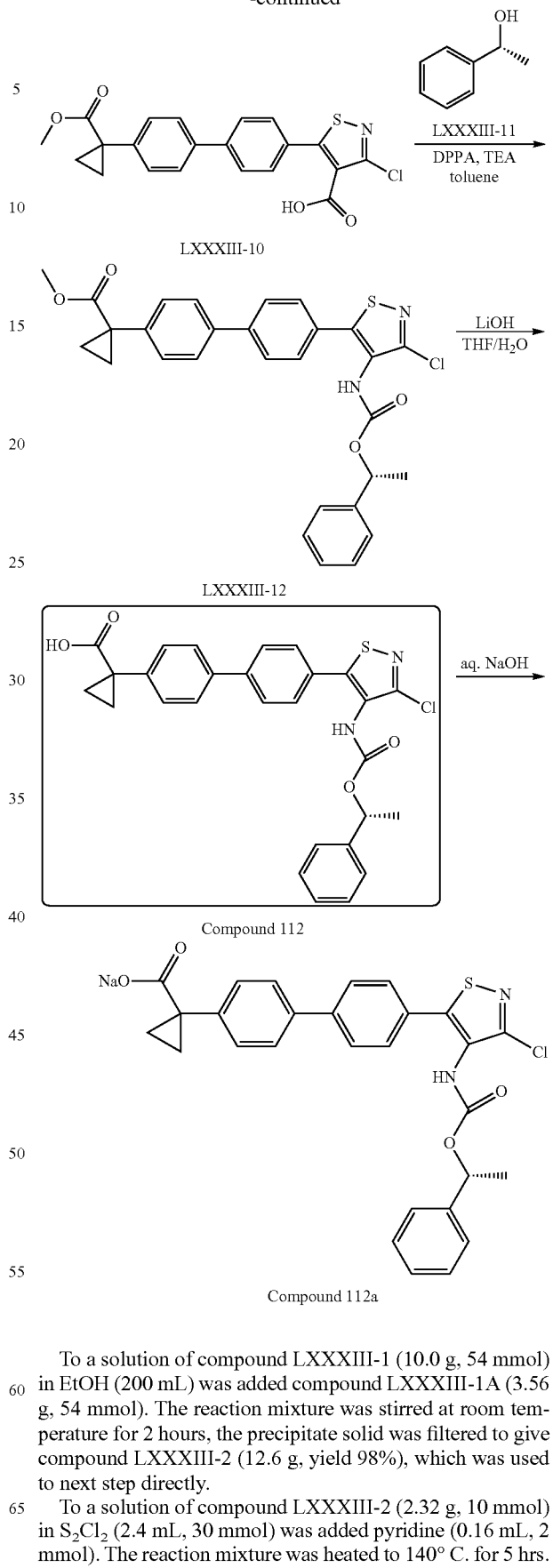

To a solution of compound LXXXIII-1 (10.0 g, 54 mmol) in EtOH (200 mL) was added compound LXXXIII-1A (3.56 g, 54 mmol). The reaction mixture was stirred at room temperature for 2 hours, the precipitate solid was filtered to give compound LXXXIII-2 (12.6 g, yield 98%), which was used to next step directly.

To a solution of compound LXXXIII-2 (2.32 g, 10 mmol) in $S_2Cl_2$ (2.4 mL, 30 mmol) was added pyridine (0.16 mL, 2 mmol). The reaction mixture was heated to 140° C. for 5 hrs.

After being cooled to r.t., the precipitate solid was filtered to give crude compound LXXXIII-3, which was washed with hot EtOH, and purified by column chromatography (PE: EA=10:1) to afford pure compound LXXXIII-3 (1.7 g, yield 58%). MS (ESI) m/z (M+H)$^+$ 298.9.

The mixture of compound LXXXIII-3 (1.0 g, 3.34 mmol) in conc. H$_2$SO$_4$ (12 mL) was stirred at 100° C. for 2 hrs. The mixture was poured into ice water to afford a white precipitate. The white precipitate was filtered, washed with H$_2$O, and dried to give compound LXXXIII-4 (0.9 g, yield 89%). MS (ESI) m/z (M+H)$^+$ 317.1.

To a stirred solution of compound LXXXIII-4 (500 mg, 1.57 mmol) in conc.H$_2$SO$_4$ (12 mL) protected with CaCl$_2$ drying tube, was added NaNO$_2$ (1.08 g, 15.7 mmol) in portions at 0° C. After addition, the mixture was heated to 100° C. for 2 hours. Then the mixture was poured into ice water to afford a white precipitate. The white precipitate was filtered, washed with H$_2$O, and dried to give compound LXXXIII-5 (450 mg, yield 90%). $^1$H NMR (DMSO-d$_6$, 400 MHz): δ 7.59 (d, J=8.4 Hz, 2H), 7.35 (d, J=8.4 Hz, 2H).

The solution of compound LXXXIII-5 (100 mg, 0.313 mmol) in MeOH/HCl (4N, 5 mL) was stirred at 60° C. for overnight. After concentrated under reduced pressure, the residue was extracted with EtOAc, washed with aqueous NaHCO$_3$, and brine, the organic layer was dried, concentrated, and purified by prep-TLC (PE:EA=10:1) to give compound LXXXIII-6 (88 mg, yield 85%). MS (ESI) m/z (M+H)$^+$ 331.9.

To a stirred mixture of compound LXXXIII-6 (1.24 g, 3.74 mmol), compound LXXXIII-7 (1.36 g, 4.49 mmol) and K$_2$CO$_3$ (0.77 g, 5.61 mmol) in DMF (10 mL) was added Pd(OAc)$_2$ (83 mg). The reaction mixture was flushed with N$_2$ and heated to 140° C. for 10 minutes in microwave. The mixture was diluted with EtOAc (40 mL), washed with water and brine, dried over Na$_2$SO$_4$, filtered and concentrated. The residue was purified by column chromatography (PE:EA=5:1) to give compound LXXXIII-8 (0.96 g, yield 30%). MS (ESI) m/z (M+H)$^+$ 428.1.

To a solution of compound LXXXIII-8 (168 mg, 0.393 mmol) in THF (3 mL) was added water (1 mL) and sodium hydroxide (79 mg, 1.97 mmol). The reaction was stirred at room temperature for overnight. The mixture was diluted with water, neutralized to pH=4.0 with 1N hydrochloride solution, extracted with EtOAc (20 mL). The organic phase was dried over MgSO$_4$ and concentrated to afford compound LXXXIII-9 (141 mg, yield 90%), which was used to next step directly. MS (ESI) m/z (M+H)$^+$ 400.0.

To a solution of compound LXXXIII-9 (157 mg, 0.393 mmol) in MeOH (5 mL) was added TMSCl (334 mg, 3.15 mmol) at 0° C. The reaction mixture was stirred at room temperature for 24 hrs. The mixture was diluted with water, and extracted with EtOAc (20 mL). The organic phase was dried over MgSO$_4$, concentrated to give compound LXXXIII-10 (130 mg, yield 80%), which was used to next step directly. MS (ESI) m/z (M+H)$^+$ 414.1.

To a solution of compound LXXXIII-10 (130 mg, 0.315 mmol) in dry toluene (2 mL) was added compound LXXXIII-11 (45.3 mg, 0.378 mmol), triethylamine (63.6 mg, 0.630 mmol) and DPPA (104 mg, 0.378 mmol). The reaction mixture was heated to 80° C. for overnight. The mixture was diluted with EtOAc (30 mL), washed with brine, dried over MgSO$_4$, filtered and concentrated. The residue was purified by prep-TLC (PE:EA=3:1) to give compound LXXXIII-12 (85 mg, yield 81%). MS (ESI) m/z (M+H)$^+$ 533.2.

Preparation of Compound 112

To a solution of compound LXXXIII-12 (85.3 mg, 0.16 mmol) in THF (6 mL) was added water (2 mL) and lithium monohydrate (33.7 mg, 0.80 mmol). The reaction mixture was stirred at room temperature overnight. The mixture was neutralized to pH=4.0 with 1N hydrochloride solution, extracted with EtOAc (20 mL). The organic phase was dried over MgSO$_4$ and concentrated. The residue was purified by HPLC to give Compound 112 (31 mg, yield 37.3%). MS (ESI) m/z (M+H)$^+$ 519.1.

Preparation of Compound 112a

To a solution of Compound 112 (31 mg, 0.06 mmol) in MeOH (2 mL) was added 0.05N sodium hydroxide solution (1.197 mL). The reaction mixture was stirred for 30 minutes and lyophilized to give Compound 112a. $^1$H NMR (DMSO-d$_6$ t=80 400 MHz): δ 7.74 (d, J=8.4 Hz, 2H), 7.63 (d, J=8.4 Hz, 2H), 7.52 (d, J=8.4 Hz, 2H), 7.41 (d, J=8.4 Hz, 2H), 7.28-7.35 (m, 5H), 5.75 (q, 1H), 1.49 (d, J=6.4 Hz, 3H), 1.28-1.29 (m, 2H), 0.74-0.76 (m, 2H). MS (ESI) m/z (M+H)$^+$ 519.3.

Synthesis of Compound 113

Synthetic Route (Scheme LXXXIV)

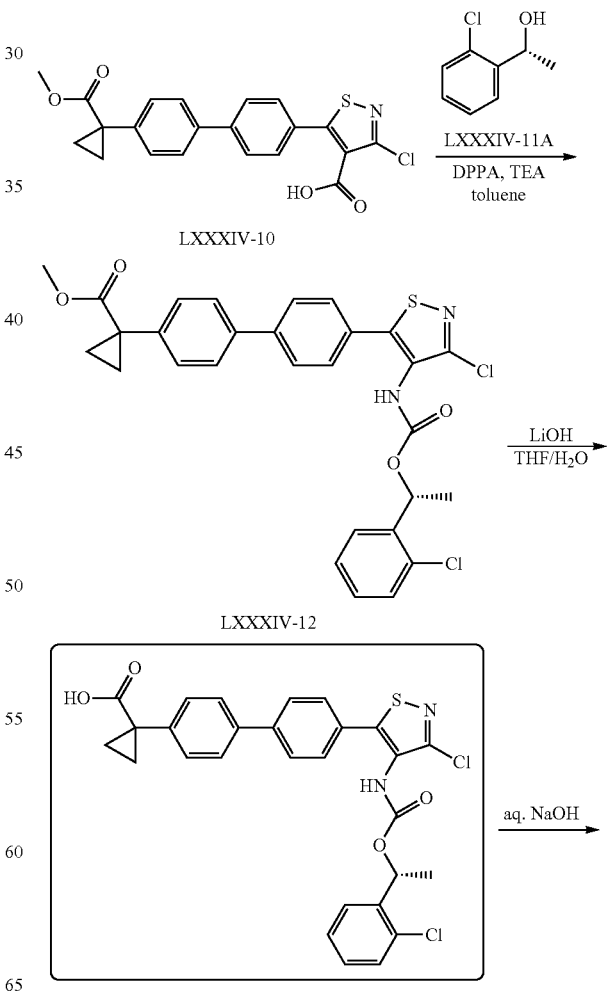

Compound 113

-continued

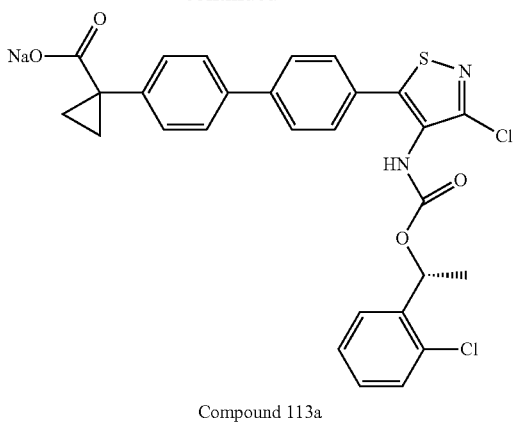

Compound 113a

Compound 113 was prepared analogously to the procedure described in the synthesis of Compound 112. MS (ESI) m/z (M+H)+ 533.2.

Compound 113a was prepared analogously to the procedure described in the synthesis of Compound 112a. $^1$HNMR (DMSO-d$_6$, t=80, 400 MHz): δ 9.60 (br, 1H), 7.76 (d, J=8.0 Hz, 2H), 7.65 (d, J=8.0 Hz, 2H), 7.34-7.55 (m, 8H), 5.98 (q, 1H), 1.50 (brs, 3H), 1.22-1.23 (m, 2H), 0.71-0.73 (m, 2H). MS (ESI) m/z (M+H)+ 575.1.

Synthesis of Compound 114

Synthetic Route (Scheme LXXXV)

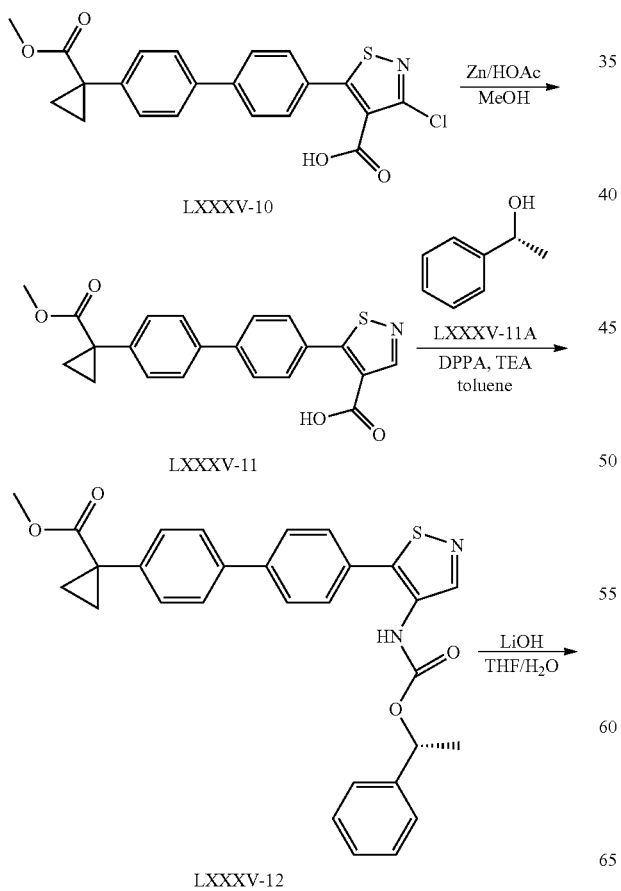

-continued

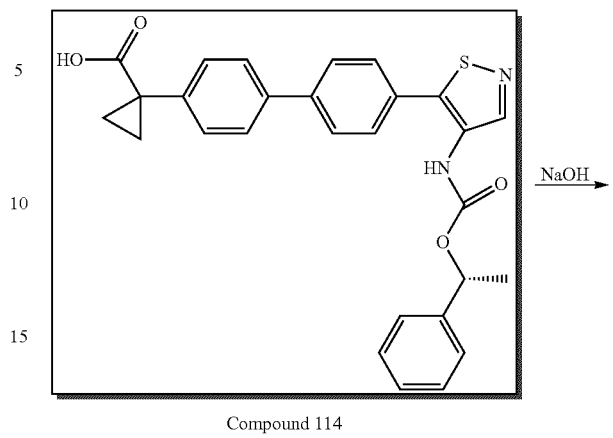

Compound 114

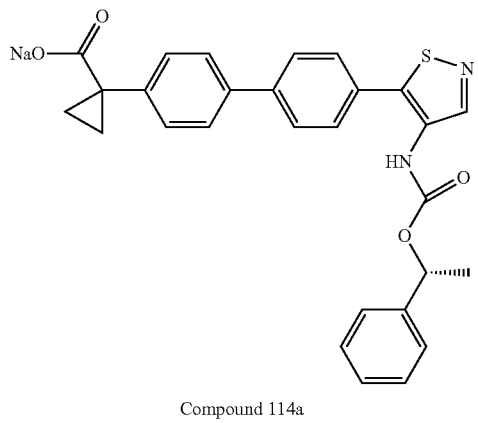

Compound 114a

To the solution of compound LXXXV-10 (1.3 g, 3.15 mmol) in MeOH (30 mL) and acetic acid (20 mL) was added Zn (0.15 mol). The mixture was stirred at 90° C. for overnight. The mixture was filtered, the filtrate was concentrated and purified by prep-HPLC to afford compound LXXXV-11 (56.5 mg, yield 4.7%). MS (ESI) m/z (M+H)+ 380.1.

To a solution of compound LXXXV-11 (46.5 mg, 0.12 mmol) in dry toluene (3 mL) was added (R)-1-(phenyl)ethanol (18 mg, 0.15 mmol), triethylamine (25 mg, 0.25 mmol) and DPPA (40 mg, 0.15 mmol). The reaction mixture was heated to 80° C. for 3 hours. The mixture was diluted with EtOAc, washed with brine, dried over Na$_2$SO$_4$, filtered and concentrated. The residue was purified by TLC (PE:EA=10:3) to give compound LXXXV-12 (40.5 mg, yield: 55%). MS (ESI) m/z (M+H)+ 499.3.

Compound 114 was prepared analogously to the procedure described in the synthesis of Compound 44 (11 mg, yield: 28%). MS (ESI) m/z (M+H)+ 485.0.

Compound 114a was prepared analogously to the procedure described in the synthesis of Compound 44a. $^1$HNMR (Methanol-d$_4$, 400 MHz) δ 8.59 (s, 1H), 7.73 (d, J=8.4 Hz, 2H), 7.59-7.63 (m, 4H), 7.30-7.49 (m, 7 H), 5.82 (br, 1 H), 1.56-1.59 (m, 5 H), 1.15-1.18 (q, 2 H). MS (ESI) m/z (M+H)+ 485.1.

Synthesis of Compound 115
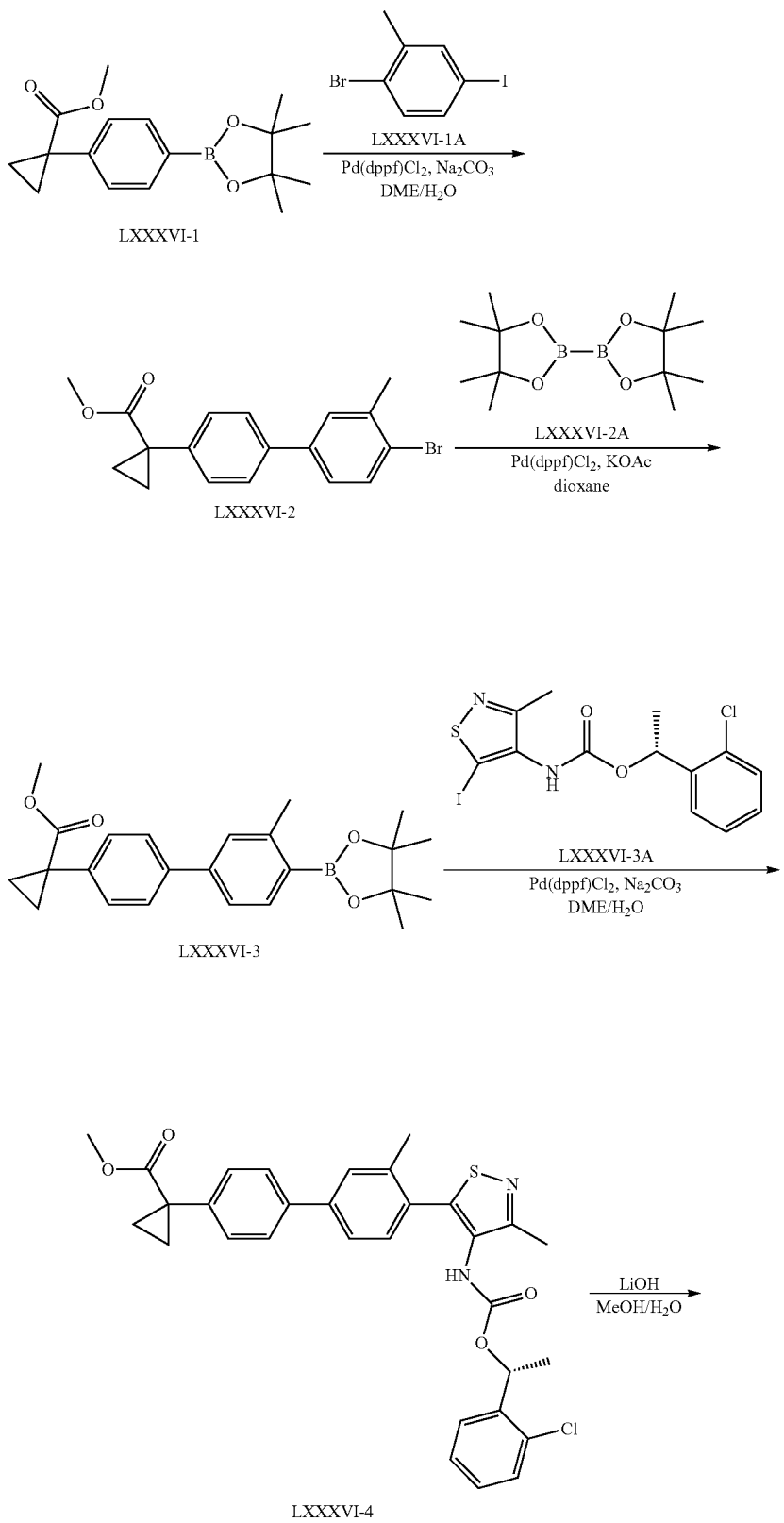

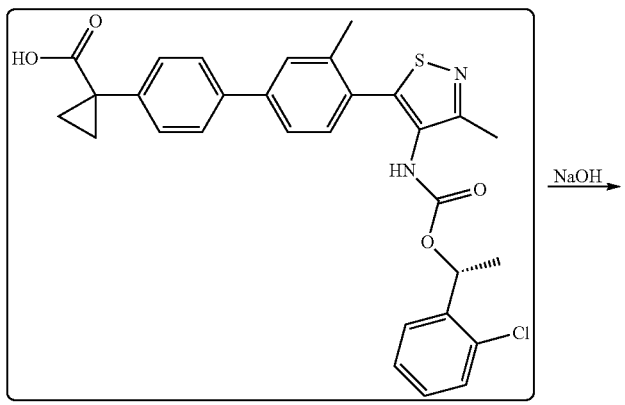

Compound 115

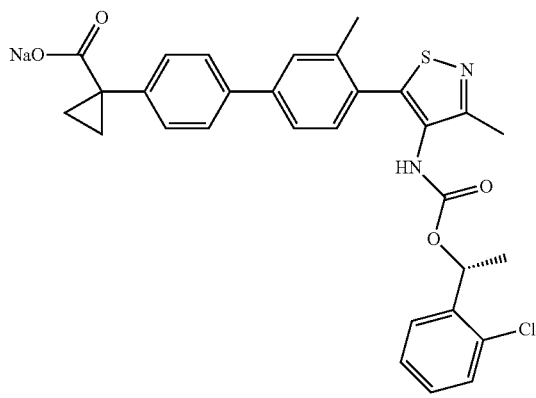

Compound 115a pTo a solution of compound LXXXVI-1 (1.5 g, 4.9 mmol) in DME:H$_2$O=3:1 (20 mL), Na$_2$CO$_3$ (1.05 g, 9.9 mmol) and compound LXXXVI-1A (1.47 mg, 4.9 mmol) were added, the resulting mixture was purged with nitrogen, then Pd(dppf)Cl$_2$ (182 mg, 0.2 mmol) was added. The reaction mixture was stirred at 80° C. overnight under nitrogen protection. After completion of the reaction, the mixture was poured into water, extract with EtOAc (30 mL×3), the combined organic layers were dried over Na$_2$SO$_4$, concentrated in vacuo. The residue was purified by chromatography (PE:EA=100:1) to afford compound LXXXVI-2 (1.06 g, yield 59.6%).

Compound 115 was prepared analogously to the procedure described in the synthesis of Compound 32 (153.6 mg, yield 42.7%). MS (ESI) m/z (M+H)$^+$ 547.2.

Compound 115a was prepared analogously to the procedure described in the synthesis of Compound 44a. $^1$H NMR (400 MHz, DMSO-d$_6$): δ9.20 (s, 1 H), 7.53-7.64 (m, 4 H), 7.23-7.45 (m, 7 H), 5.90 (q, 1 H), 2.28 (s, 3 H), 2.22 (s, 3 H), 1.50-1.44 (m, 5 H), 1.20-1.17 (m, 2 H). MS (ESI) m/z (M+H)$^+$ 547.2.

Synthesis of Compound 116

Synthetic Route (Scheme LXXXVII)

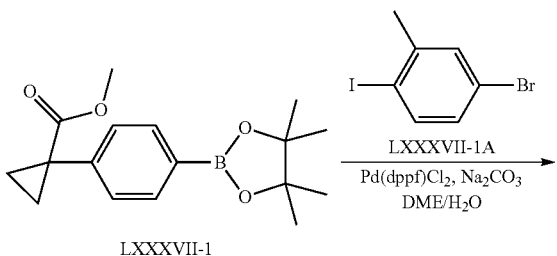

-continued
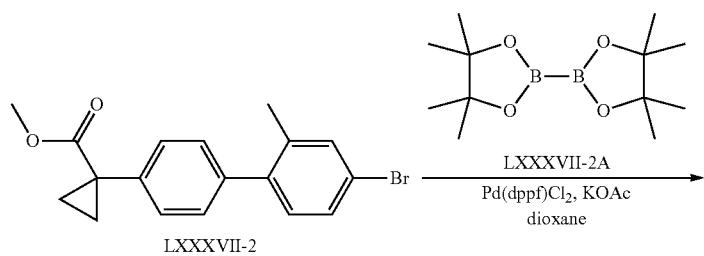
LXXXVII-2
LXXXVII-2A
Pd(dppf)Cl$_2$, KOAc
dioxane
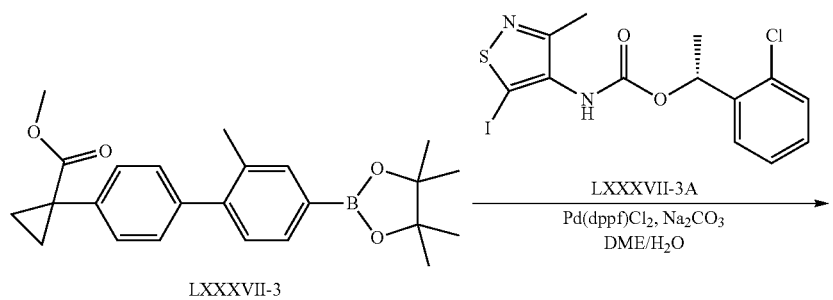
LXXXVII-3
LXXXVII-3A
Pd(dppf)Cl$_2$, Na$_2$CO$_3$
DME/H$_2$O
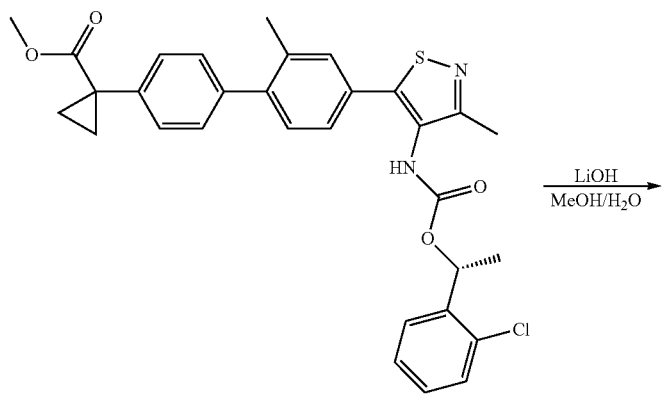
LXXXVII-4
LiOH
MeOH/H$_2$O
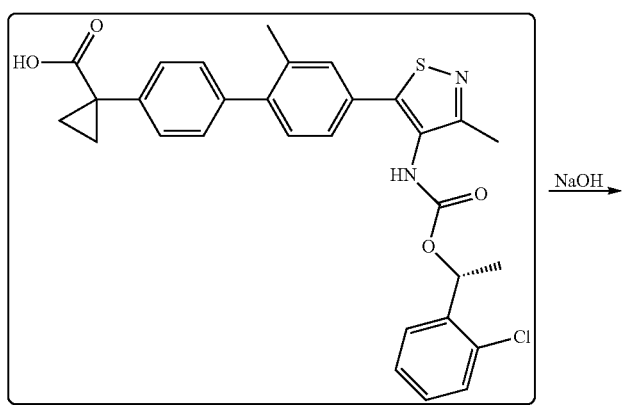
Compound 116
NaOH

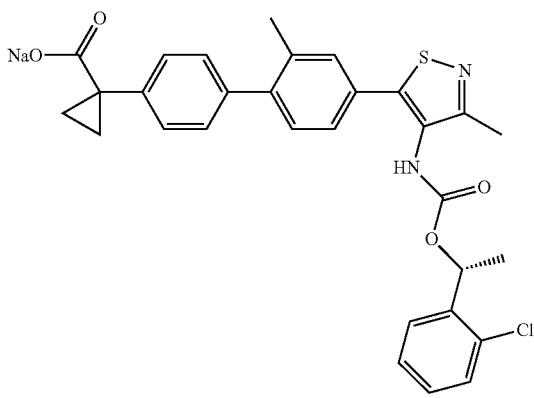
Compound 116a
Compound 116 was prepared analogously to the procedure described in the synthesis of Compound 115. MS (ESI) m/z (M+H)⁺ 547.2.
Compound 116a was prepared analogously to the procedure described in the synthesis of Compound 115a. $^1$H NMR (400 MHz, DMSO-d$_6$): δ 9.38 (s, 1 H), 7.56-7.58 (m, 1 H), 7.56-7.29 (m, 10 H), 5.98 (q, 1 H), 2.26 (s, 6 H), 1.48-1.53 (m, 5 H), 1.19-1.22 (m, 2 H). MS (ESI) m/z (M+H)⁺ 547.2.
Synthesis of Compound 117
Synthetic Route (Scheme LXXXVIII)
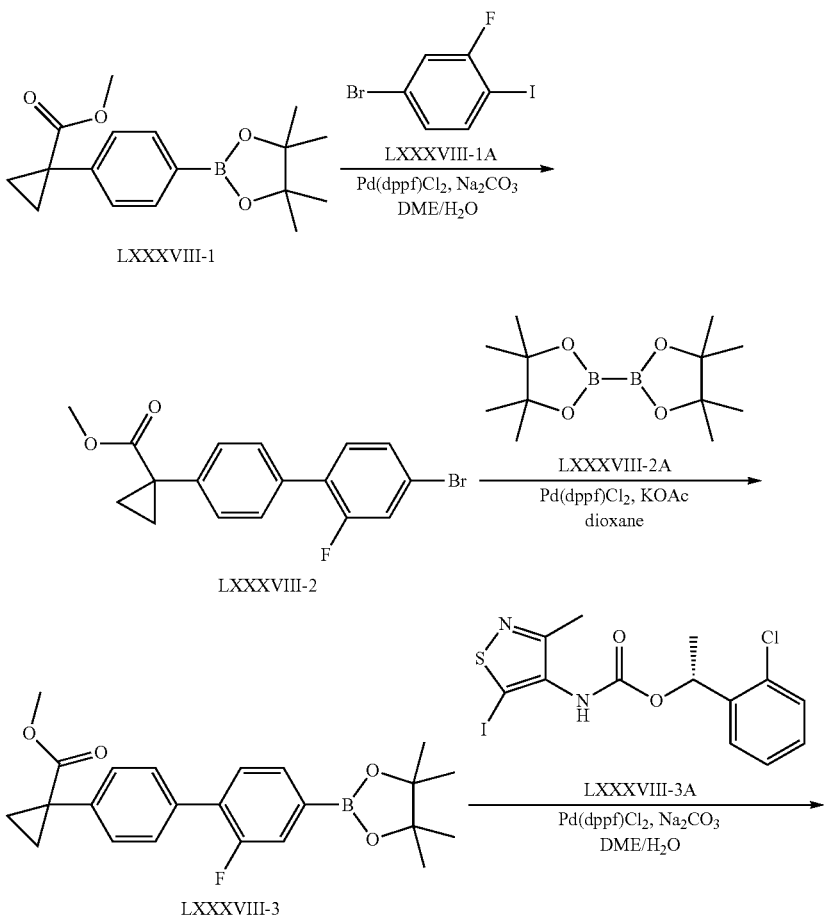

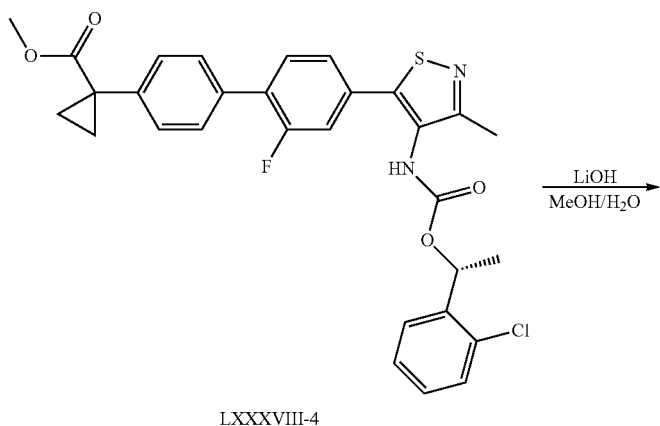
LXXXVIII-4
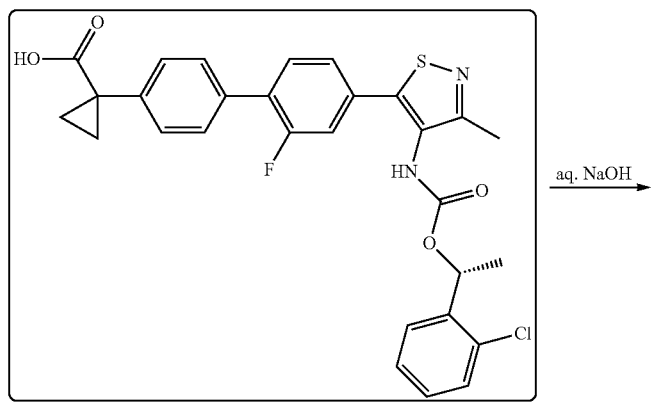
Compound 117
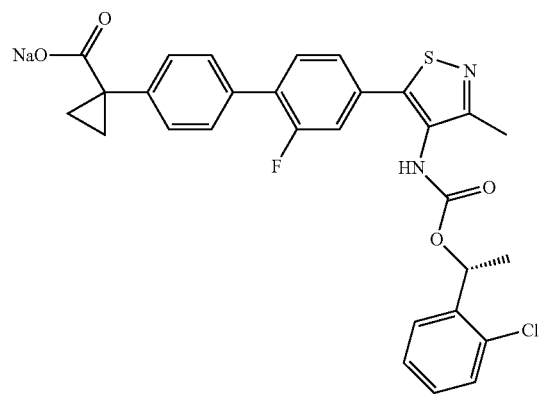
Compound 117a
Compound 117 was prepared analogously to the procedure described in the synthesis of Compound 115 (57 mg, yield: 58.7%). MS (ESI) m/z (M+H)$^+$ 551.2.
Compound 117a was prepared analogously to the procedure described in the synthesis of Compound 115a. $^1$H NMR (DMSO-d$_6$, 400 MHz): δ 9.09 (s, 1H), 7.28-7.61 (m, 11H), 5.99-6.04 (q, 1H), 2.31 (s, 3H), 1.50 (d, J=6.4 Hz, 3H), 1.28-1.31 (m, 2H), 0.66-0.69 (m, 2H). MS (ESI) m/z (M+H)$^+$ 551.2.

Synthesis of Compound 118
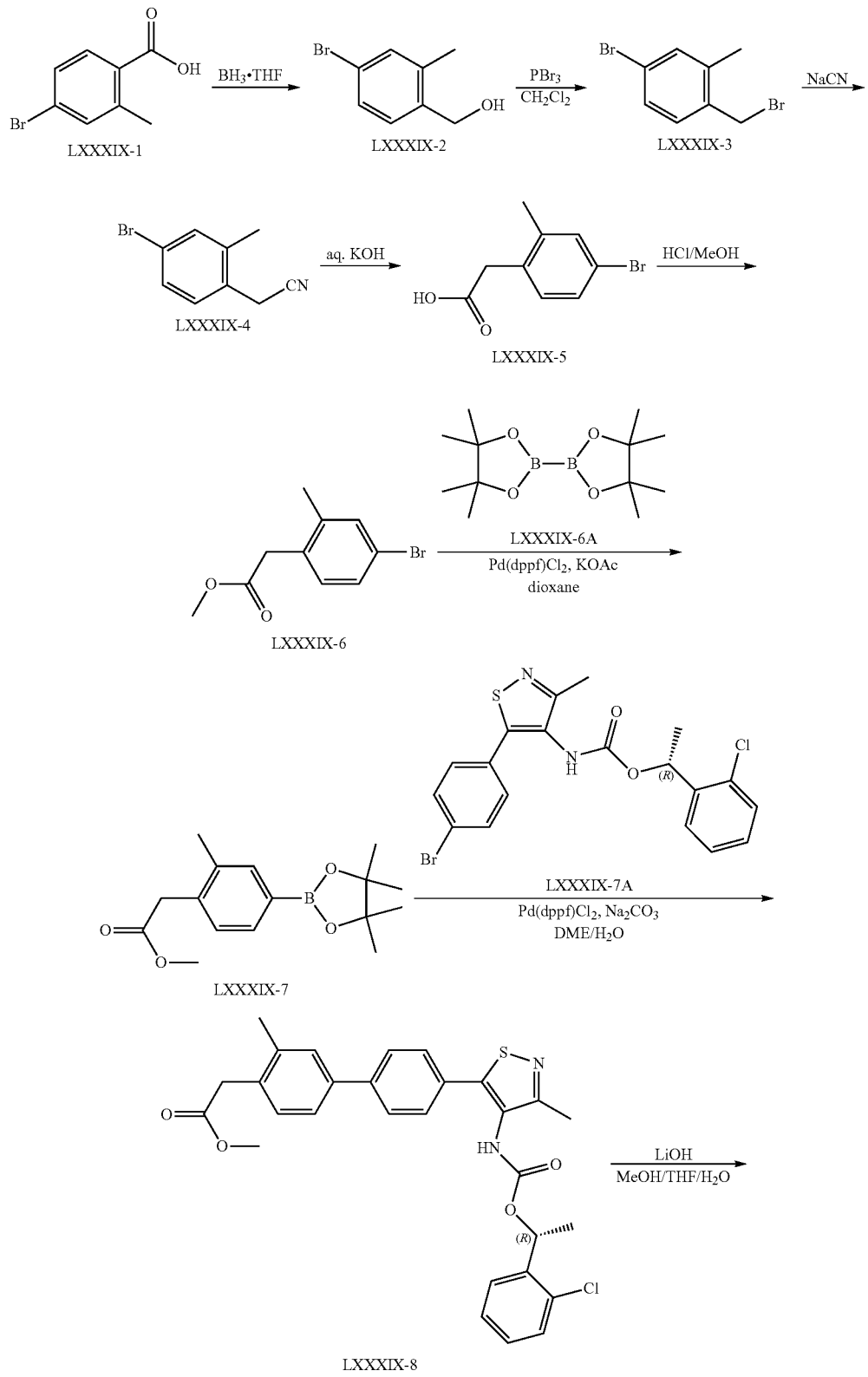

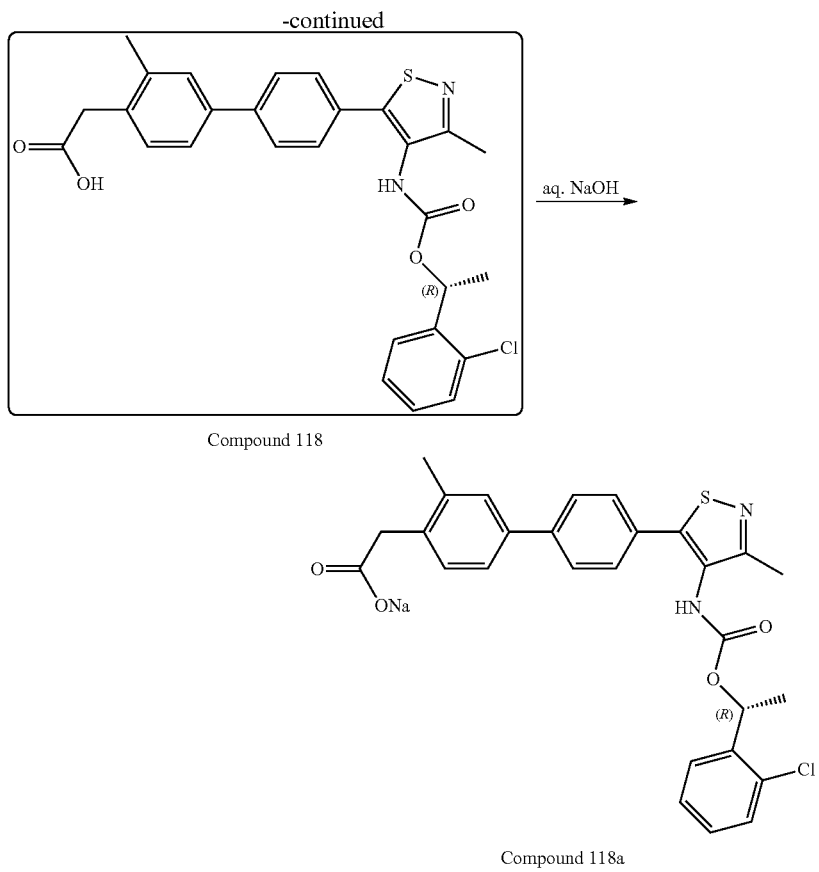

Compound 118

Compound 118a

To a solution of compound LXXXIX-1 (20 g, 93 mmol) in THF (30 mL) was added $BH_3$·THF (1 M, 223 ml) at 0° C. The mixture was stirred at r.t. for 12 hours. After being cooled to r.t., water (200 mL) was added to the mixture and then washed with saturated $NaHCO_3$. The aqueous was extracted with EtOAc (300 mL×3) and the organic layer was washed with brine, dried with over $Na_2SO_4$ and concentrated under vacuum to give the desired compound LXXXIX-2 (16 g, yield: 85.5%).

To a solution of compound LXXXIX-2 (10 g, 50 mmol) in DCM (120 mL) was added $PBr_3$ (6.77 g, 25 mmol at 0° C. The resulting mixture was stirred at r.t. overnight. After being cooled to r.t., water (120 mL) was added to the mixture. The organic layer was separated and washed with brine, dried with over $Na_2SO_4$ and concentrated under vacuum to give compound LXXXIX-3 (12 g, yield: 93.4%).

To a solution of compound LXXXIX-3 (6 g, 25 mmol) in DMF (70 mL) was added NaCN (1.7 g, 37 mmol) at 0° C. and then was added $H_2O$ (6 mL). This mixture was stirred at 25° C. for 15 h. After completing, water (100 mL) was added followed by satur. $NaHCO_3$ (90 mL). The mixture was extracted with ethyl acetate (100 mL×3). The organic layers was separated, dried over $Na_2SO_4$, filtered, and concentrated under vacuum to give compound LXXXIX-4 (5 g, yield: 92%).

To a solution of compound LXXXIX-4 (4 g, 19 mmol) in $H_2O$ (45 mL) was added KOH (4.27 g, 76 mmol). This mixture was heated under reflux for 15 hours. After cooled, the mixture was washed with ethyl acetate (40 mL), and then adjusted pH to 5-6 by 1N HCl. The mixture was extracted with ethyl acetate (60 mL×3). The organic layers was dried with $Na_2SO_4$, filtered and concentrated under vacuum to give compound LXXXIX-5 (3.5 g, yield: 80%).

The mixture of compound LXXXIX-5 (1 g, 4.39 mmol) in 50 mL of HCl/MeOH was heated to reflux for 4 hours. The mixture was concentrated under reduced pressure to afford compound LXXXIX-6 (800 mg, yield: 75.47%), which was used to next step directly.

To a stirred solution of compound LXXXIX-6 (1.1 g, 4.5 mmol), compound LXXXIX-6A (1.38 g, 5.45 mmol) KOAc (872 mg, 9.19 mmol) in 50 mL of dioxane was added Pd(dppf)$Cl_2$ at room temperature. The solution was heated to reflux under nitrogen for 4 hours. After being cooled to room temperature, water (50 mL) was added and extracted with EtOAc (50 mL×3). The extracts were washed with brine, dried over $Na_2SO_4$, concentrated to afford crude product, which was purification by column chromatography (PE:EA=20:1) to afford compound LXXXIX-7 (800 mg, yield: 60.61%).

To a stirred solution of compound LXXXIX-7 (300 mg, 0.667 mmol), compound LXXXIX-7A (212 mg, 0.733 mmol) and $Na_2CO_3$ (141 mg, 0.736 mmol) in 10 mL of DME/$H_2O$ (v/v=5:1) was added Pd(dppf)$Cl_2$ at room temperature. The solution was heated to reflux under nitrogen for 4 hours. After being cooled to room temperature, water (10 mL) was added and extracted with EtOAc (20 mL×3). The extracts were washed with brine, dried over $Na_2SO_4$, concentrated to afford crude product, which was purified by Prep. TLC (PE:EA=1:1) to afford compound LXXXIX-8 (72 mg, yield: 19.7%). MS (ESI) m/z (M+H)$^+$ 535.2.

Preparation of Compound 118

To a solution of compound LXXXIX-8 (60 mg, 0.1123 mmol) in MeOH (3 mL), THF (3 mL) and $H_2O$ (3 mL), was added LiOH (23 mg, 0.5618 mmol). The reaction mixture was stirred at room temperature overnight. After concentrated, the mixture was adjust to pH=2 with HCl (1N) and extracted with EtOAc (20 mL×3). The organic layers was washed with brine, dried over $Na_2SO_4$, and concentrated. The residue was purified by prep. HPLC to afford Compound 118 (28 mg, yield: 47.92%). MS (ESI) m/z $(M+H)^+$ 521.2.

Preparation of Compound 118a

To a solution of Compound 118 (28 mg, 0.054 mmol) in MeOH (1 mL) and MeCN (5 mL) was added 0.05 N sodium hydroxide solution (1.07 mL) at 0° C. The reaction mixture was stirred for 20 minutes. The mixture was freeze-dried to give Compound 118a. $^1$H NMR (DMSO-$d_6$, 400 MHz): δ 9.01 (s, 1H), 7.69 (d, J=8.4 Hz, 2H), 7.58 (d, J=8.4 Hz, 2H), 7.24-7.43 (m, 7H), 5.99-6.04 (q, 1H), 3.30 (s, 2H), 2.38 (s, 3H), 2.30 (s, 3H), 1.48 (d, J=5.2 Hz, 3H) MS (ESI) m/z $(M+H)^+$ 521.2.

Synthesis of Compound 119

Synthetic Route (Scheme XC)

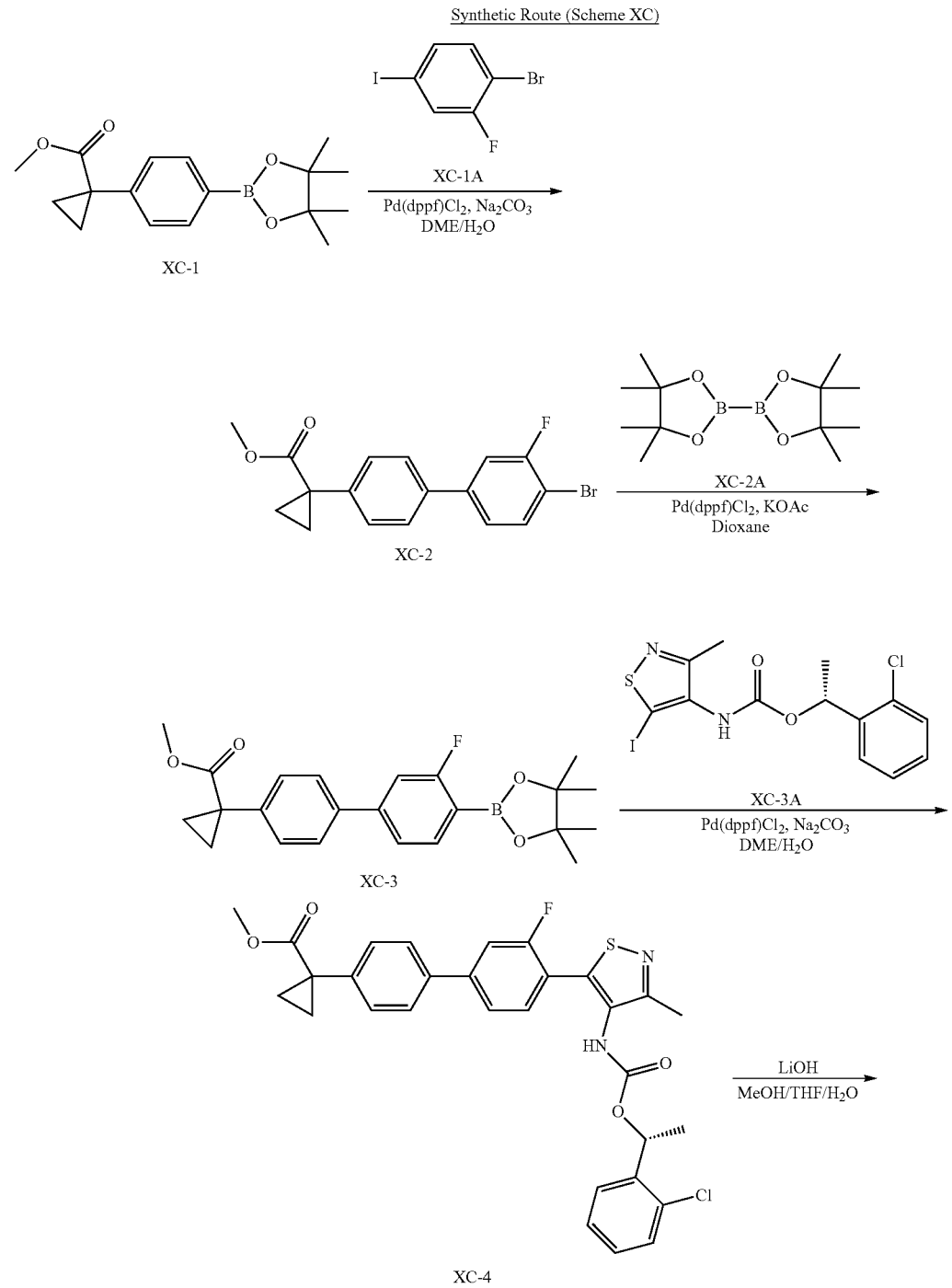

-continued
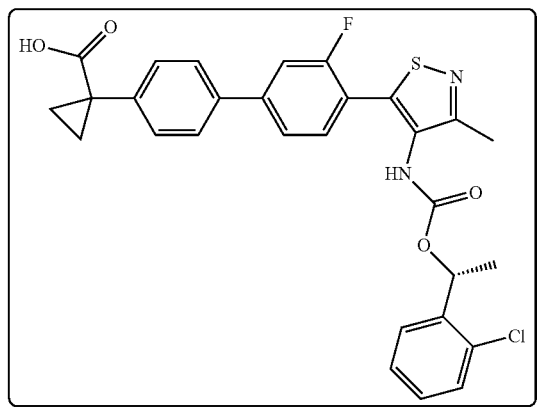
Compound 119
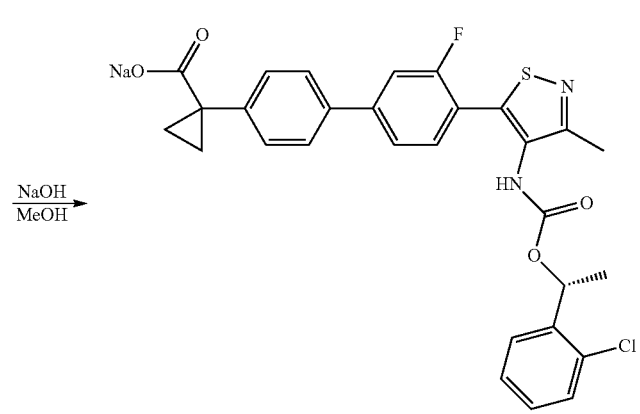
Compound 119a
Compound 119 was prepared analogously to the procedure described in the synthesis of Compound 117. Compound 119a. $^1$H NMR (Methanol-d$_4$, 400 MHz): δ 7.47-7.60 (m, 8H), 7.25-7.36 (m, 3H), 6.09-6.12 (q, 1H), 2.38 (s, 3H), 1.55 (d, J=6.0 Hz, 3H), 1.46-1.49 (m, 2H), 0.98-1.01 (m, 2H). MS (ESI) m/z (M+H)$^+$ 551.1.
Synthesis of Compound 120
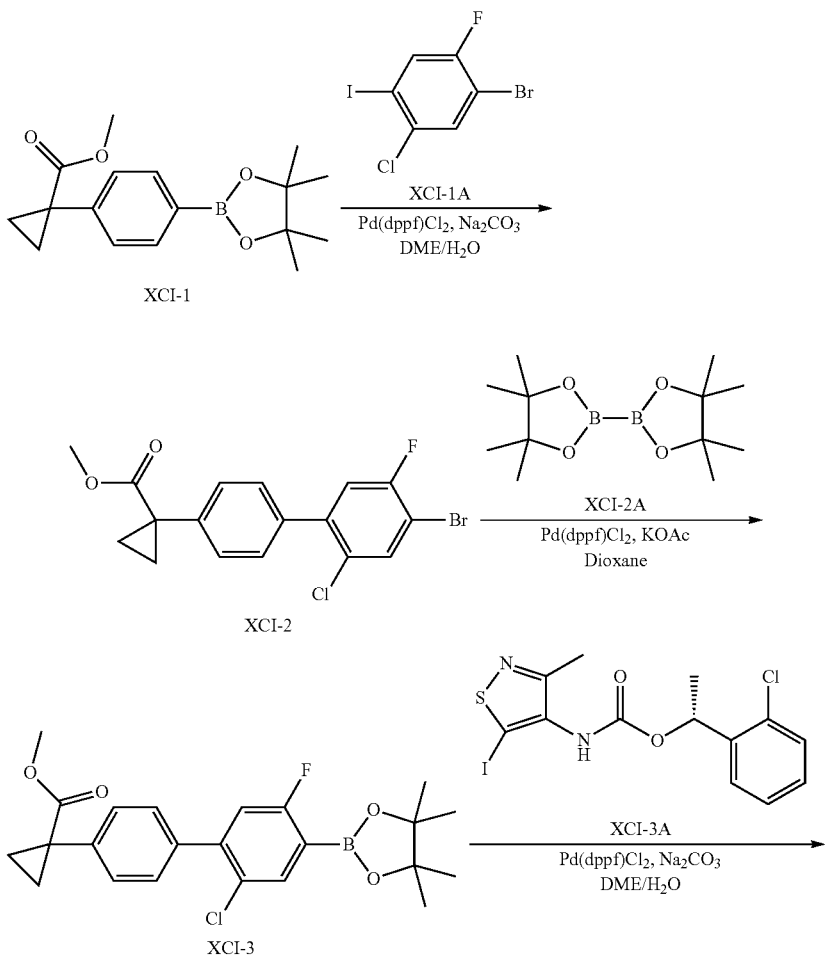

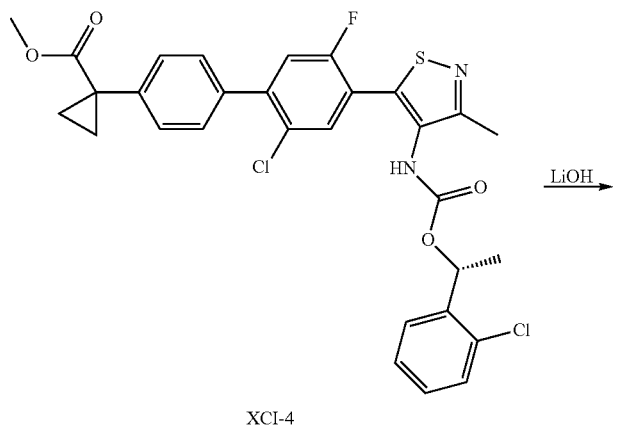
XCI-4
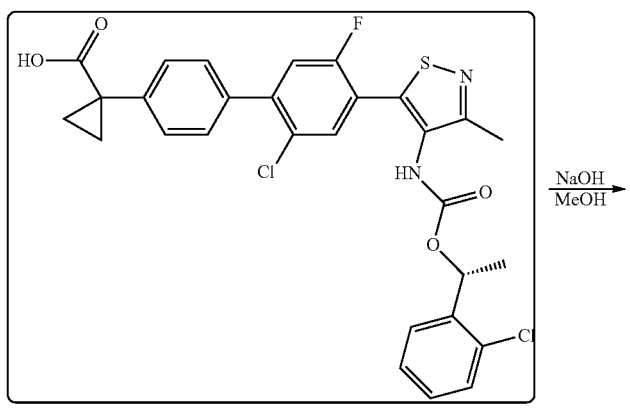
Compound 120
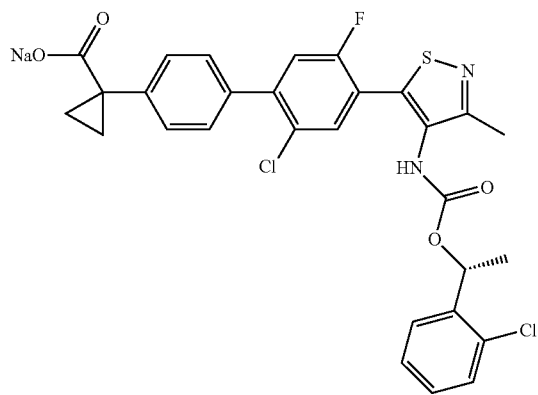
Compound 120a
Compound 120 was prepared analogously to the procedure described in the synthesis of Compound 117. MS (ESI) m/z (M+H)⁺ 585.
Compound 120a was prepared analogously to the procedure described in the synthesis of Compound 117a. ¹H NMR: (DMSO-$d_6$, 400 MHz) δ 9.56 (s, 1 H), 7.77 (d, J=6.8 Hz, 1H), 7.33-7.55 (m, 9 H), 5.95-5.96 (q, 1 H), 2.32 (s, 3 H), 1.49-1.52 (m, 5 H), 1.18-1.22 (m, 2 H). MS (ESI) m/z (M+H)⁺ 585.2.

Synthesis of Compound 121
Synthetic Route (Scheme XCII)
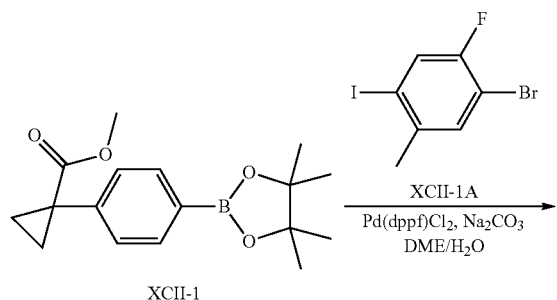
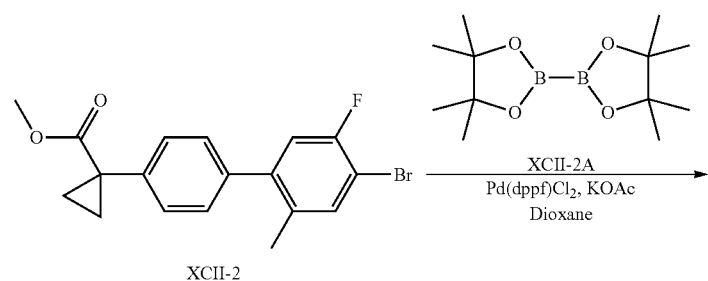
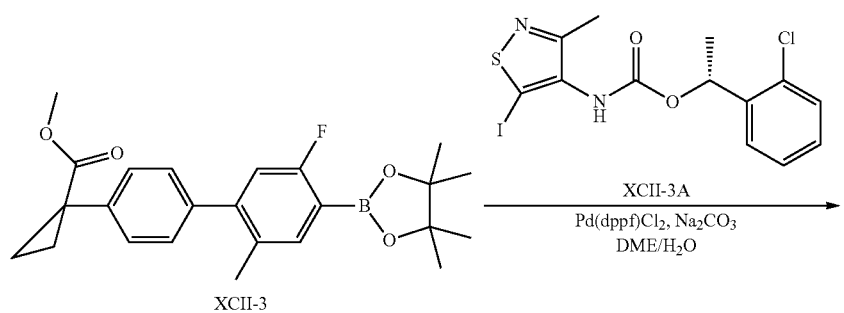
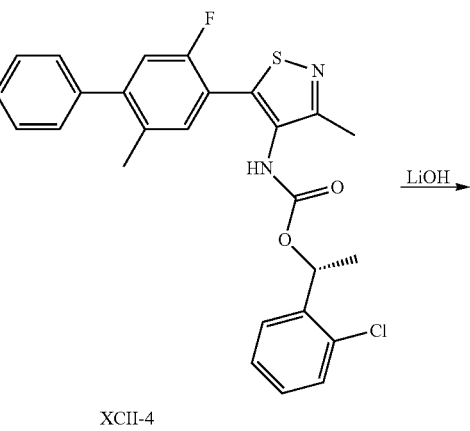

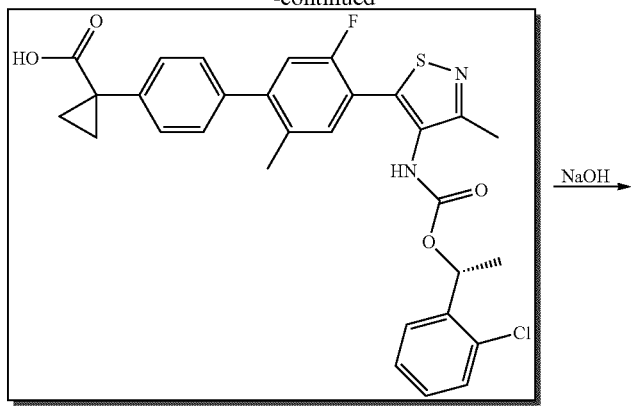
Compound 121
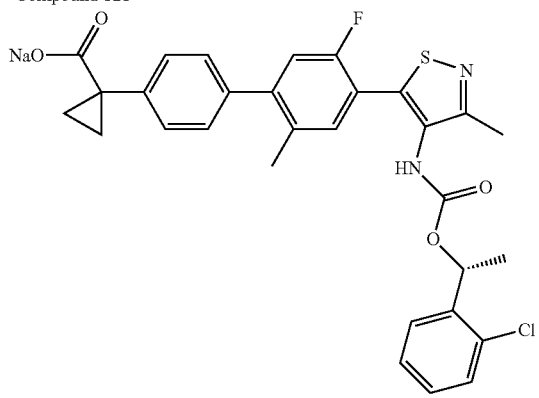
Compound 121a
Compound 121 was prepared analogously to the procedure described in the synthesis of Compound 115. MS (ESI) m/z (M+H)+ 565.1.
Compound 121a was prepared analogously to the procedure described in the synthesis of Compound 115a. $^1$H NMR (DMSO-d$_6$, 400 MHz) δ 9.42 (s, 1 H), 8.39 (s, 1 H), 7.54-7.56 (m, 6 H), 7.47-7.32 (m, 3 H), 7.24-7.21 (m, 1 H), 5.96-5.98 (q, 1H), 2.33 (s, 3H), 2.21 (s, 3H), 1.48-1.52 (m, 5 H), 1.20-1.22 (m, 2 H). MS (ESI) m/z (M+H)+ 565.1.
Synthesis of Compound 122
Synthetic Route (Scheme XCIII)
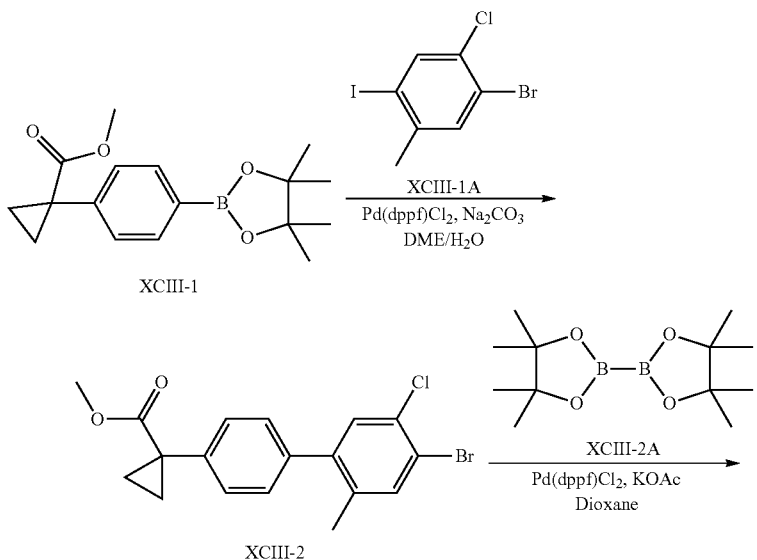

-continued
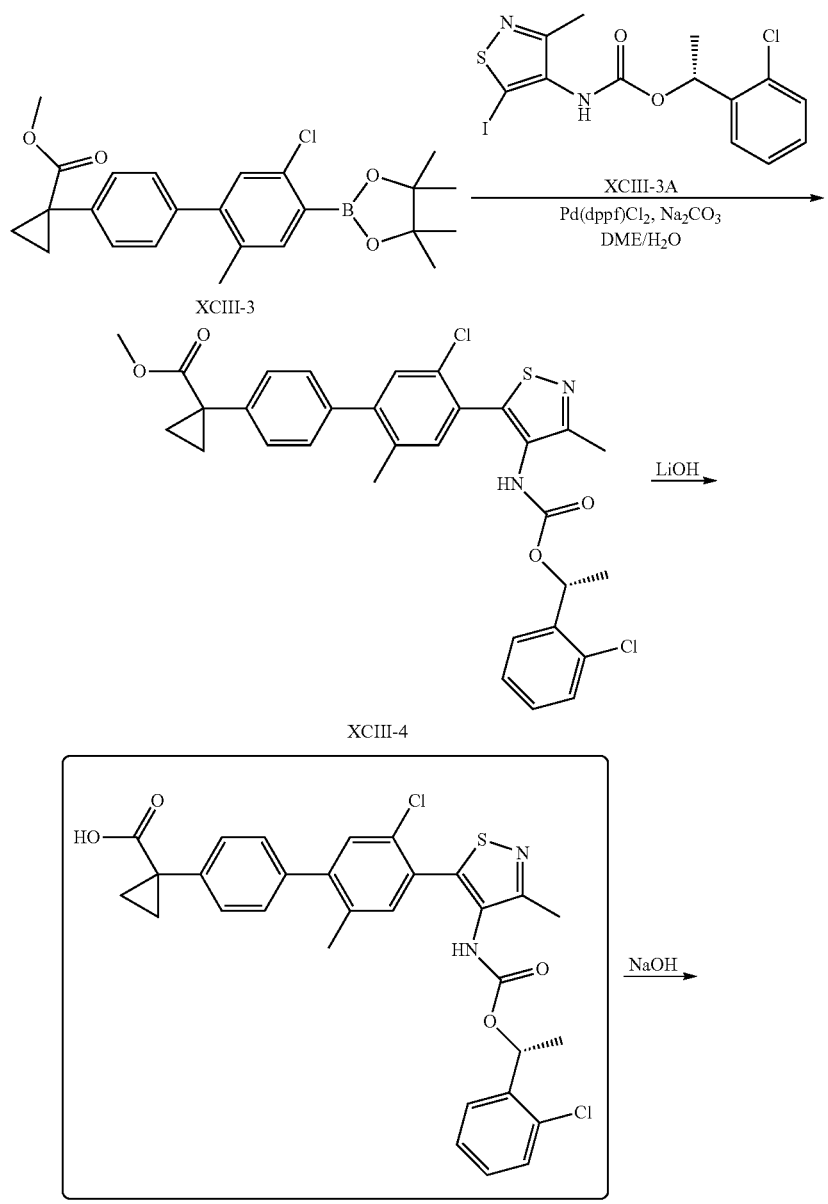
Compound 122
Compound 122a

Compound 122 was prepared analogously to the procedure described in the synthesis of Compound 115. MS (ESI) m/z (M+H)+ 581.0.
Compound 122a was prepared analogously to the procedure described in the synthesis of Compound 115a. $^1$HNMR (DMSO-d$_6$ t=80 400 MHz) δ 7.31-7.43 (m, 8H), 7.16 (d, J=8.0 Hz, 2H), 6.02 (q, 1 H), 2.33 (s, 3 H), 2.21 (s, 3 H), 1.47 (d, J=6.4 Hz, 2H), 1.23-1.25 (m, 2 H), 0.68-0.71 (m, 2 H). MS (ESI) m/z (M+H)+ 581.1.
Synthesis of Compound 123
Synthetic Route (Scheme XCIV)
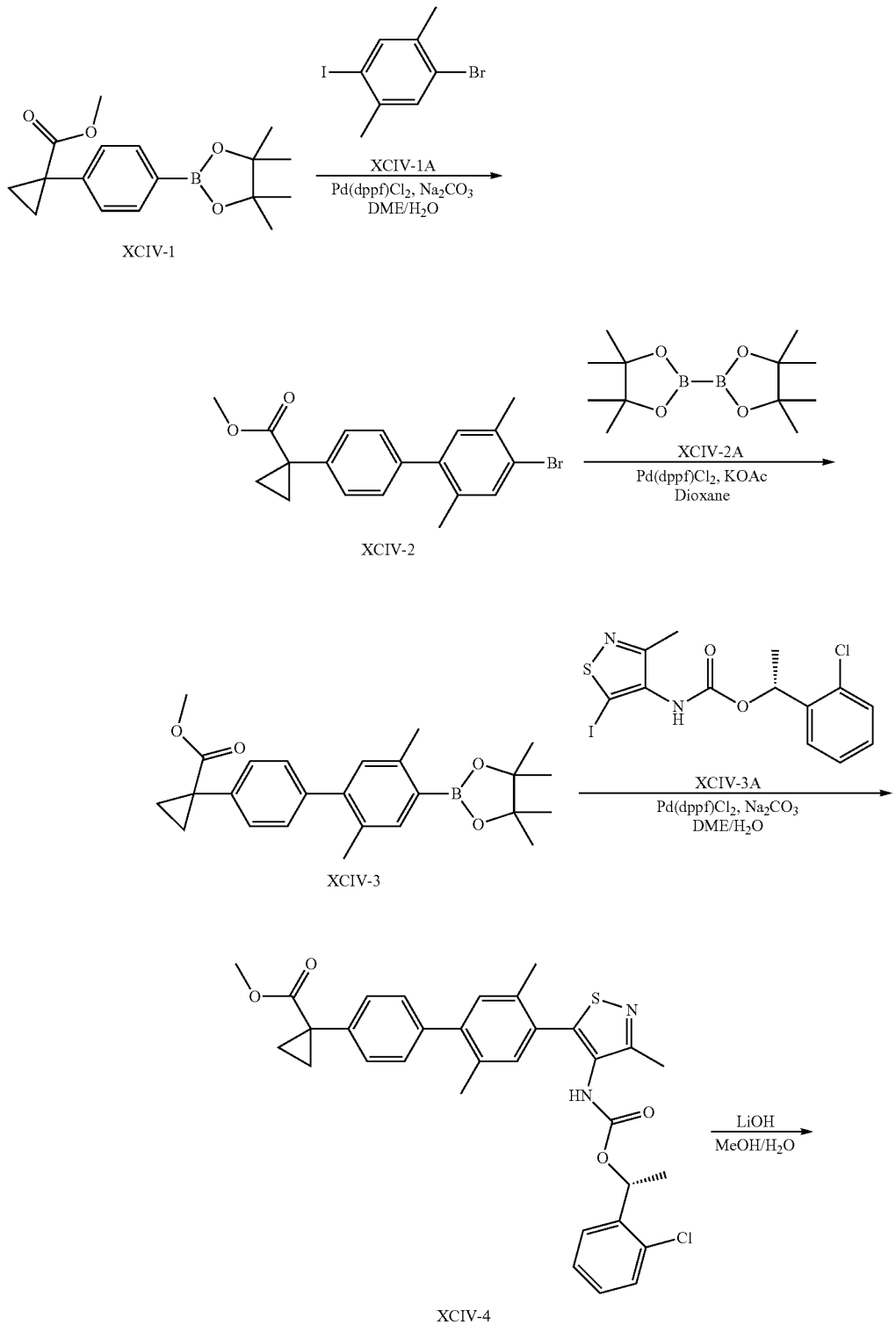

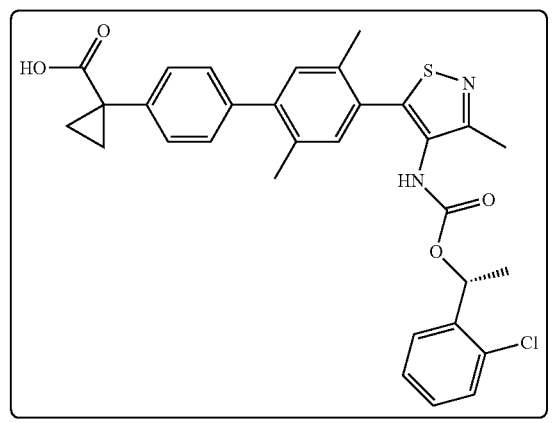
Compound 123
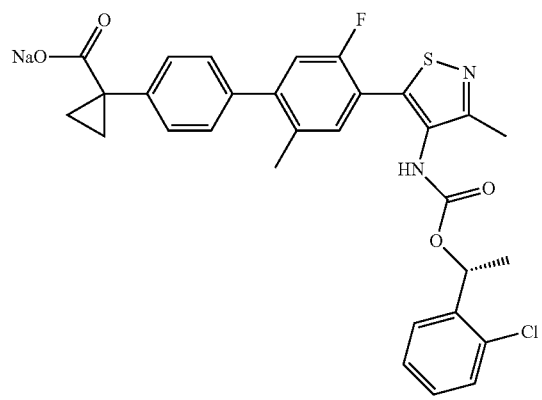
Compound 123a
Compound 123 was prepared analogously to the procedure described in the synthesis of Compound 115. MS (ESI) m/z (M+H)+ 561.0.
Compound 123a was prepared analogously to the procedure described in the synthesis of Compound 115a. $^1$H NMR (DMSO-d$_6$ 400 MHz): δ9.35 (s, 1 H), 7.35-7.46 (m, 2 H), 7.19-7.33 (m, 4 H), 7.09-7.17 (m, 3 H), 6.93-6.99 (m, 1 H), 5.98 (q, 1 H), 2.33 (s, 3 H), 2.21 (s, 3 H), 2.05 (s, 3 H), 1.46-1.60 (br, 2H), 1.26 (brs, 3 H), 0.76-0.73 (m, 2 H). MS (ESI) m/z (M+H)+ 561.0.
Synthesis of Compound 124
Synthetic Route (Scheme XCV)
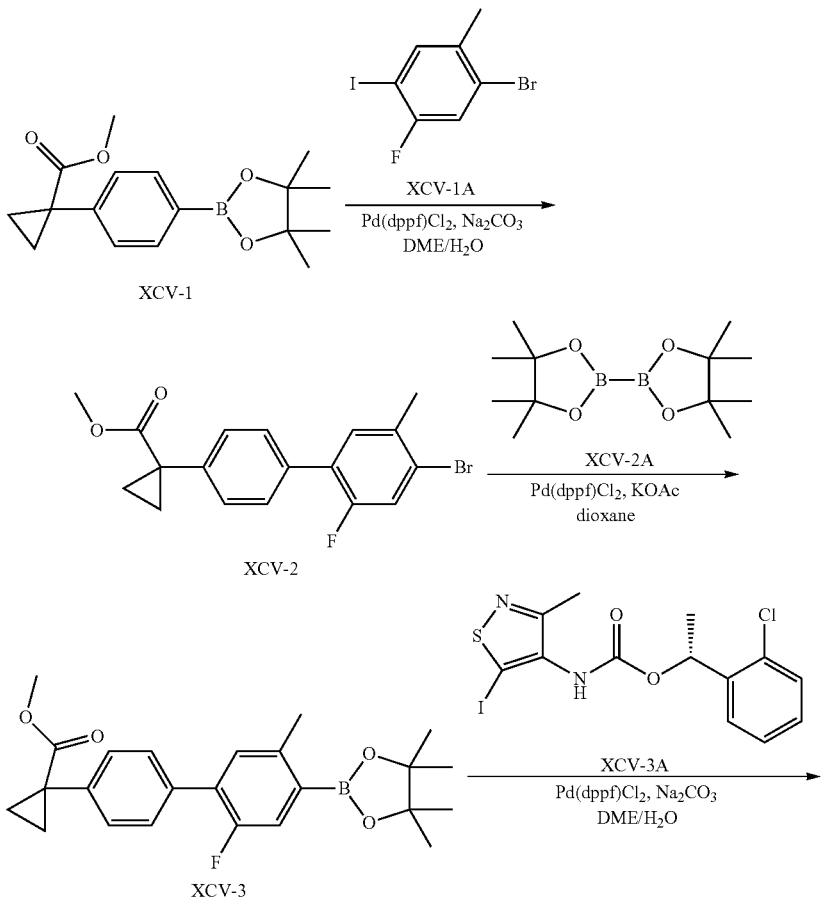

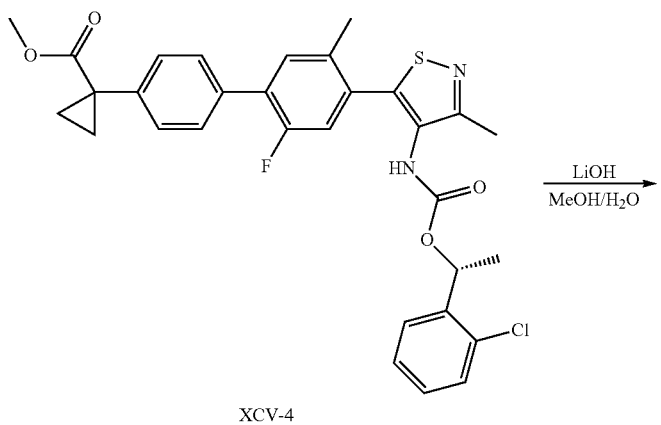
XCV-4
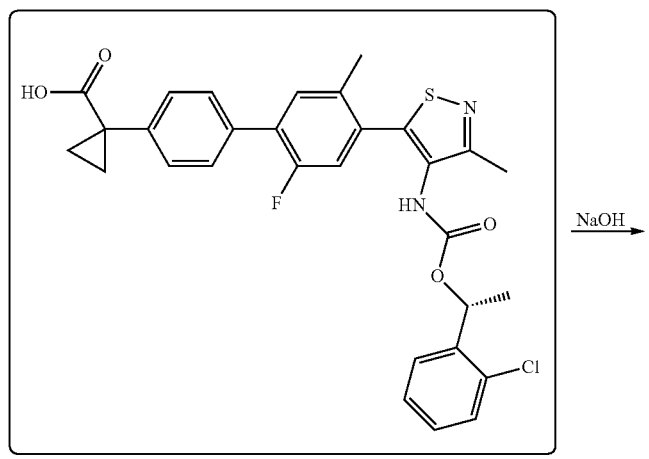
Compound 124
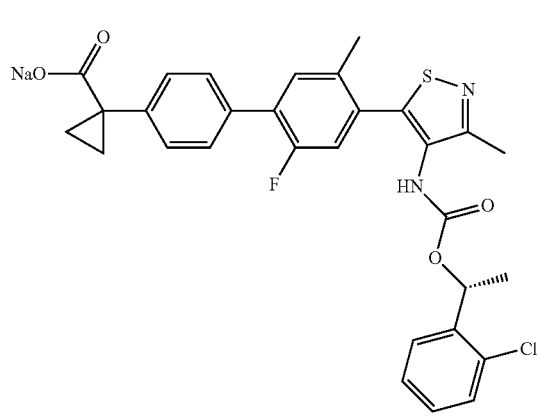
Compound 124a
Compound 124 was prepared analogously to the procedure described in the synthesis of Compound 115. MS (ESI) m/z (M+H)$^+$ 565.1.
Compound 124a was prepared analogously to the procedure described in the synthesis of Compound 115a. $^1$H NMR (DMSO-d$_6$ 400 MHz): δ 8.93 (s, 1 H), 7.22-7.53 (m, 9 H), 7.01-7.18 (m, 1 H), 6.02-5.96 (q, 1 H), 2.33 (s, 3 H), 2.21 (s, 3 H), 1.54 (br, 3 H), 1.31-1.45 (m, 2 H), 0.74-0.82 (m, 2 H). MS (ESI) m/z (M+H)$^+$ 565.1.
Synthesis of Compound 125
Synthetic Route (Scheme XCVI)
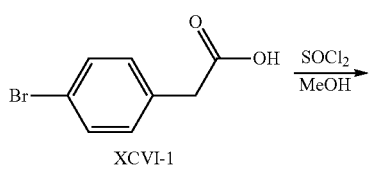
XCVI-1

-continued

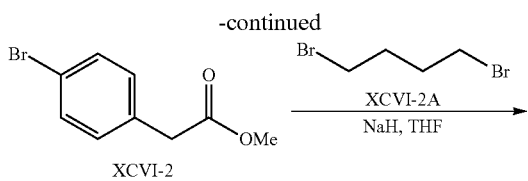

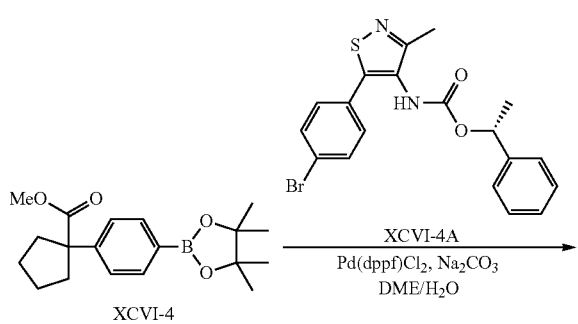

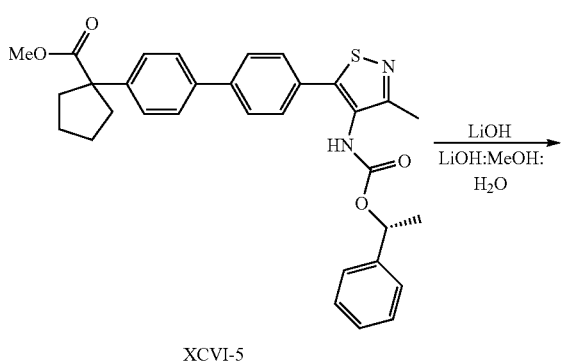

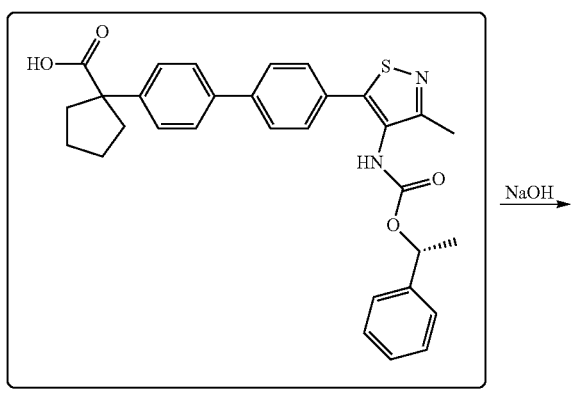

Compound 125

-continued

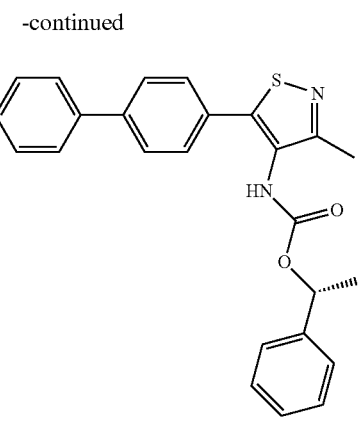

Compound 125a

To a stirred solution of compound XCVI-1 (20 g, 93.5 mmol) in MeOH (200 mL) was added $SOCl_2$ (33 g, 208.5 mmol) dropwise and the reaction mixture was stirred at r.t. for 16 h. The reaction was quenched with water and the mixture was adjusted to pH=9 with aqueous $NaHCO_3$, extracted with EtOAc, combined the organic layer, washed with water and brine, dried over $Na_2SO_4$, filtered and concentrated. The mixture was purified by column (PE:EA=100:1) to give compound XCVI-2 (17 g, yield: 79.8%).

NaH (2.2 g, 55 mmol) was added to a solution of compound XCVI-2 (5.0 g, 22 mmol) in THF (80 mL) at 0° C. The mixture was stirred at 0° C. for 30 min, then compound XCVI-2A (4.7 g, 22 mmol) was added dropwise, the reaction mixture was stirred at rt overnight. After being cooled to r.t., water (20 mL) was added, and extracted with EtOAc (50 mL×2), the combined organic layer was concentrated and re-crystallized to give compound XCVI-3 (1.7 g, yield: 27.4%).

The mixture of compound XCVI-3 (1 g, 3.546 mmol), compound XCVI-3A (1.08 g, 4.25 mmol), KOAc (0.68 g, 7.09 mmol) and $Pd(dppf)Cl_2$ (0.1 g) in dioxane was heated to reflux under nitrogen for overnight. After concentrated, the residue was partitioned between $H_2O$ and DCM, the aqueous phase was extracted with DCM, and the combined organic layer was washed with brine, dried over $Na_2SO_4$, concentrated. The residue was purified by chromatography on silica gel (PE/EA=50/1) to afford compound XCVI-4 (500 mg, yield: 42.7%). MS (ESI) m/z $(M+H)^+$ 331.2.

The mixture of compound XCVI-4A (500 mg, 1.2 mmol), compound XCVI-4 (475.9 mg, 1.44 mmol), $Na_2CO_3$ (254 mg, 2.4 mmol) and $Pd(dppf)Cl_2$ (50 mg) in DME/$H_2O$ (10 mL, v/v=3:1) was heated to reflux under nitrogen for overnight. After concentrated, the residue was partitioned between $H_2O$ and DCM, the aqueous phase was extracted with DCM, and the combined organic layer was washed with brine, dried over $Na_2SO_4$, and concentrated. The residue was purified by chromatography on silica gel (PE/EA=10/1) to afford compound XCVI-5 (500 mg, yield: 61.1%). MS (ESI) m/z $(M+H)^+$ 541.2.

Preparation of Compound 125

To a solution of compound XCVI-5 (500 mg, 0.9259 mmol) in MeOH (3 mL), THF (3 mL) and $H_2O$ (3 mL), was added LiOH (194 mg, 4.629 mmol). The reaction mixture was stirred at room temperature overnight. After concentrated, the mixture was adjust to pH=2 with HCl (1N) and extracted with EtOAc (20 mL×3). The organic layers was washed with brine, dried over Na$_2$SO$_4$, and concentrated. The residue was purified by prep. HPLC to afford Compound 125 (167 mg, yield: 34.3%). MS (ESI) m/z (M+H)$^+$ 527.2.

Preparation of Compound 125a

To a solution of Compound 125 (154 mg, 0.2927 mmol) in MeOH (1 mL) and MeCN (5 mL) was added 0.05 N sodium hydroxide solution (5.8 mL) at 0° C. The reaction mixture was stirred for 20 minutes. The mixture was freeze-dried to give Compound 125a. $^1$H NMR (DMSO-d$_6$, 400 MHz): δ 8.95 (brs, 1H), 7.68 (d, J=8.4 Hz, 2H), 7.57 (d, J=8.4 Hz, 2H), 7.47-7.53 (m, 4H), 7.28-7.34 (m, 5H), 5.75 (q, 1H), 2.67-2.71 (br, 2H), 2.28 (s, 3H), 1.48-1.66 (m, 6H), 1.47 (d, J=4.4 Hz, 3H). MS (ESI) m/z (M+H)$^+$ 527.2.

Synthesis of Compound 126

Synthetic Route (Scheme XCVII)

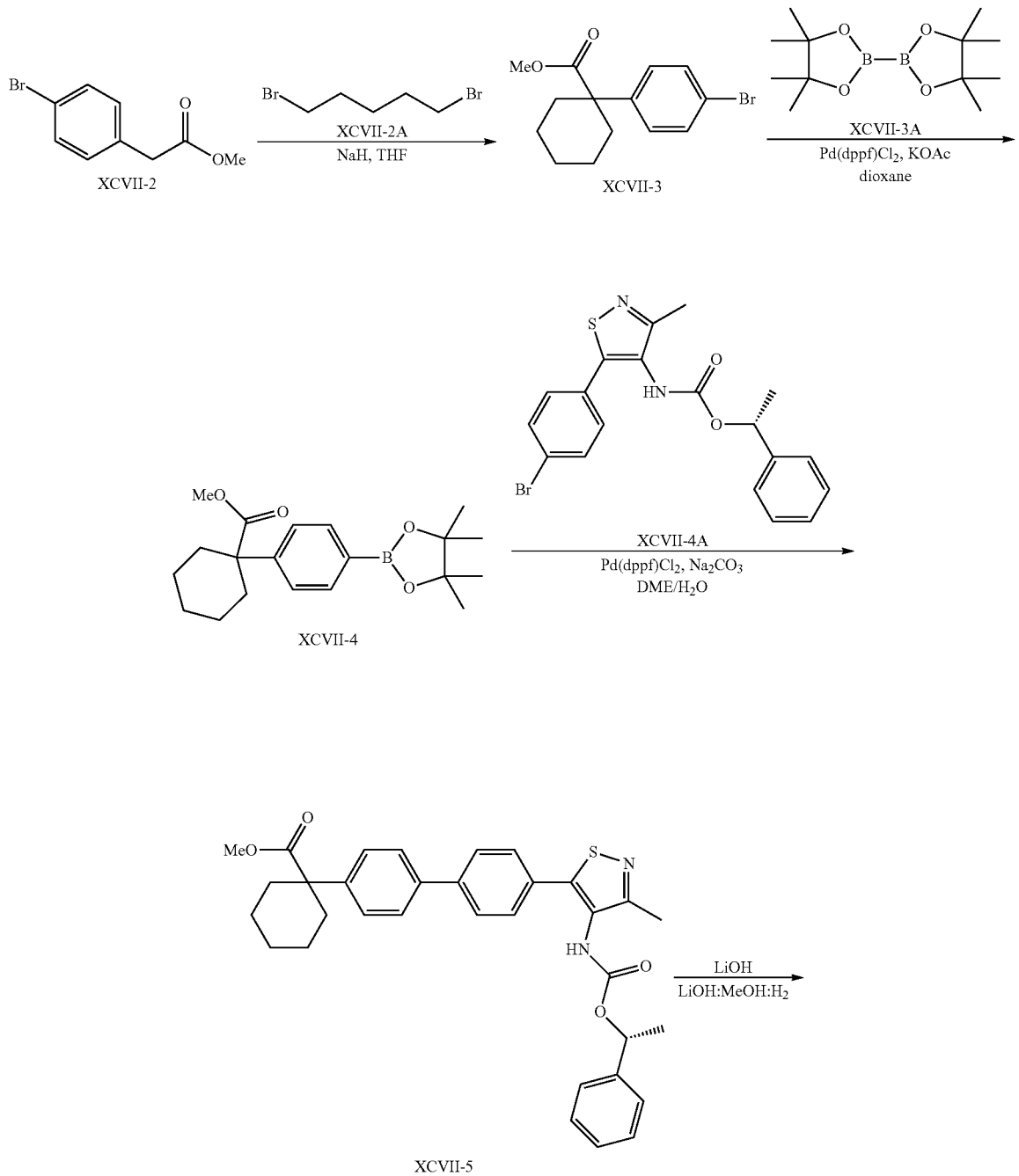

-continued

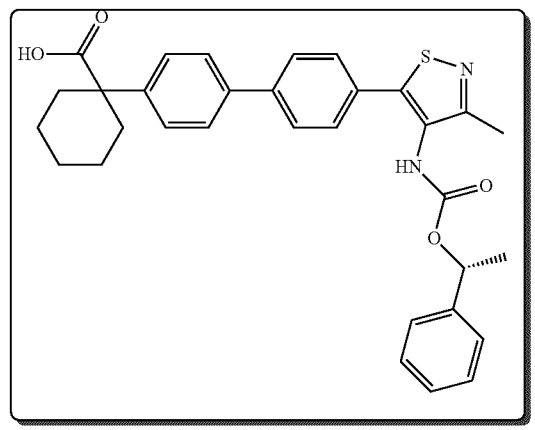

Compound 126

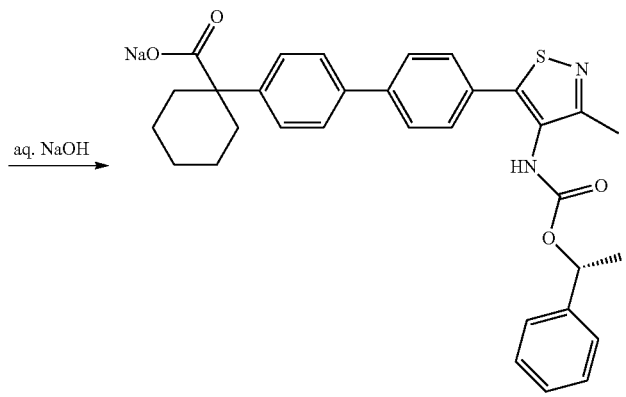

Compound 126a

NaH (2.2 g, 55 mmol) was added to a solution of compound XCVII-2 (5.0 g, 22 mmol) in THF (80 mL) at 0° C. The mixture was stirred at 0° C. for 30 min, then compound XCVII-2A (5.04 g, 22 mmol) was added portionwise, the reaction mixture was stirred at r.t. overnight. After being cooled to r.t., water (20 mL) was added, and extracted with EtOAc (50 mL×2), the combined organic layer was concentrated, and the residue was purified by column chromatography (PE/EA=100/1) to afford compound XCVII-3 (3.1 g, yield: 47.7%). MS (ESI) m/z (M+H)+ 297.1.

Compound 126 was prepared analogously to the procedure described in the synthesis of Compound 125 (31 mg, yield: 26.5%). MS (ESI) m/z (M+H)+ 541.2.

Compound 126a was prepared analogously to the procedure described in the synthesis of Compound 125a. $^1$H NMR (DMSO-$d_6$, 400 MHz): δ 9.44 (brs, 1H), 7.86-7.94 (m, 2H), 7.41-7.70 (m, 6H), 7.09-7.32 (m, 4H), 6.94-7.03 (m, 1H), 5.64-5.85 (m, 1H), 2.39-2.51 (m, 2H), 2.26 (s, 3H), 1.54-1.67 (m, 9H), 1.05-1.18 (m, 2H). MS (ESI) m/z (M+H)+ 541.1.

Synthesis of Compound 127

Synthetic Route (Scheme XCVIII)

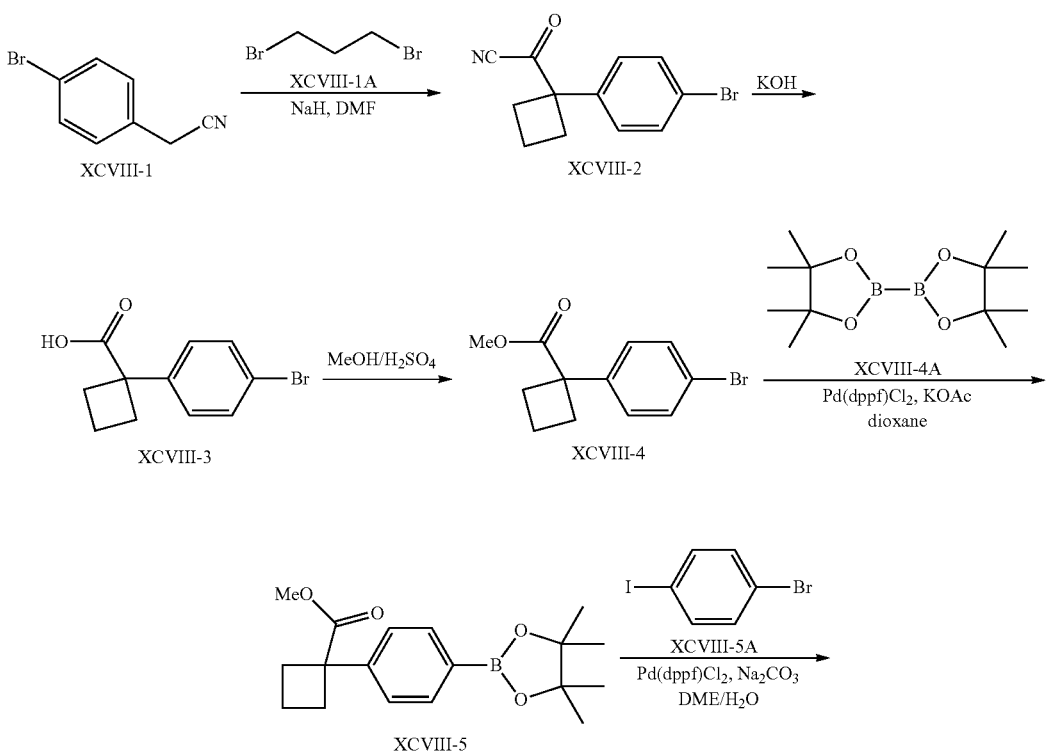

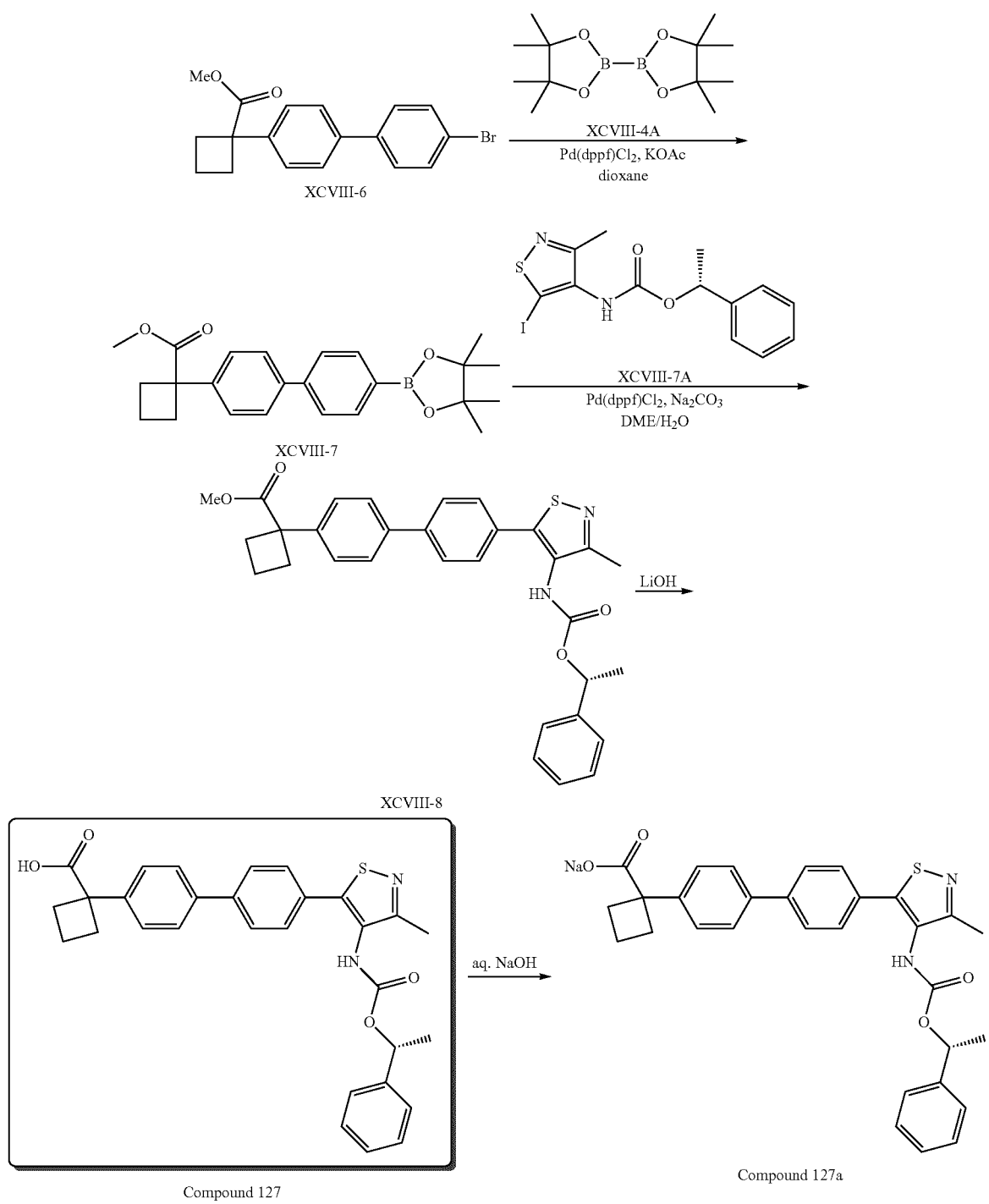

To a stirred solution of NaH (5.10 g, 127.5 mmol) in DMF (60 mL) was added compound XCVIII-1 (10 g, 51 mmol) and compound XCVIII-1A (10.3 g, 51 mmol) at 0° C. under argon. After the addition, the solution was stirred overnight at room temperature. Then the mixture was poured into water, extract with DCM (50 mL×3), the combined organic layers were dried over Na₂SO₄, concentrated in vacuo. The residue was purified by chromatography (PE:EA=100:1) to afford compound XCVIII-2 (4.6 g, yield 38%).

A stirred solution of compound XCVIII-2 (4.62 g, 19.6 mmol), KOH (4.39 g, 78.4 mmol) and ethylene glycol (20 mL) was heated to 160° C. for 2 hours under argon. The solution was quenched with water, extract with EtOAc (60 mL×3), the water layers was acidified to pH~3 and extracted with EtOAc (50 mL×3), dried over Na₂SO₄, concentrated in vacuo and purified by chromatography (PE:EA=50:1) to afford compound XCVIII-3 (4.32 g, yield 98%).

A stirred solution of compound XCVIII-3 (5 g, 19.6 mmol), H₂SO₄ (6.4 mL) and CH₃OH (60 mL) was heated to 70° C. for 4 hours under argon. The solution was quenched with water, and extract with EtOAc (60 mL×3), the combined organic layers was dried over Na₂SO₄, concentrated in vacuo. and purified by chromatography (PE:EA=100:1) to afford compound XCVIII-4 (4.3 g, yield 81.6%).

The mixture of compound XCVIII-4 (3.67 g, 13.7 mmol), compound XCVIII-4A (6.95 g, 27.4 mmol), KOAc (2.68 g, 27.4 mmol) and Pd (dppf)Cl₂ (500 mg, 0.70 mmol) in 60 mL of dioxane was heated to reflux under argon for 4 hours. The mixture was concentrated, the residue was partitioned between H₂O and DCM, the aqueous phase was extracted with DCM, and the combined organic layer was washed with brine, dried over Na₂SO₄, concentrated. The residue was purified by chromatography on silica gel (PE:EA=100:1) to afford compound XCVIII-5 (3 g, yield 69.4%).

To a solution of compound XCVIII-5 (3.00 g, 9.5 mmol) in DME:H₂O=3:1 (30 mL), Na₂CO₃ (2.01 g, 18.9 mmol) and compound XCVIII-5A (2.68 g, 9.5 mmol) were added, the resulting mixture was purged with nitrogen, then Pd (dppf)Cl₂ (347 mg, 0.50 mmol) was added. The reaction mixture was stirred at 80° C. overnight under nitrogen protection. TLC monitored the reaction. After completion of the reaction, the mixture was poured into water, extract with EtOAc (60 mL×3), the combined organic layers were dried over Na₂SO₄, concentrated in vacuo. The residue was purified by chromatography (PE:EA=50:1) to afford compound XCVIII-6 (2.05 g, yield 62.7%).

The mixture of compound XCVIII-6 (2.05 g, 5.94 mmol), compound XCVIII-4A (3.00 g, 11.81 mmol), KOAc (1.16 g, 11.81 mmol) and Pd(dppf)Cl₂ (217 mg, 0.29 mmol) in 50 mL of dioxane was heated to reflux under argon for 4 hours. The mixture was concentrated, the residue was partitioned between H₂O and DCM, the aqueous phase was extracted with DCM, and the combined organic layer was washed with brine, dried over Na₂SO₄, and concentrated. The residue was purified by chromatography on silica gel (PE:EA=40:1) to afford compound XCVIII-7 (1.98 g, yield 84.9%).

To a solution of compound XCVIII-7 (1.00 g, 2.55 mmol), Na₂CO₃ (540 mg, 5.09 mmol) and compound XCVIII-7A (0.99 g, 2.55 mmol) in DME:H₂O=3:1 (20 mL) were added Pd (dppf)Cl₂ (93 mg, 0.12 mmol). The resulting mixture was purged with nitrogen and stirred at 80° C. overnight under nitrogen protection. TLC monitored the reaction. After completion of the reaction, the mixture was poured into water, extract with EtOAc (30 mL×3), the combined organic layers were dried over Na₂SO₄, and concentrated in vacuo. The residue was purified by chromatography (PE:EA=5:1) to afford compound XCVIII-8 (890 mg, yield 65.9%). MS (ESI) m/z (M+1)⁺ 527.1.

Compound 127 was prepared analogously to the procedure described in the synthesis of Compound 44 (211 mg, yield 24.3%). MS (ESI) m/z (M+H)⁺ 513.3.

Compound 127a was prepared analogously to the procedure described in the synthesis of Compound 44a. ¹H NMR (400 MHz, DMSO-d₆): δ9.30 (s, 1 H), 7.57-7.74 (m, 6 H), 7.41-7.58 (m, 6 H), 7.41-7.58 (m, 1H), 5.76 (q, 1 H), 2.72-2.78 (m, 2 H), 2.44-2.47 (m, 2 H), 2.07 (s, 3 H), 1.80-1.97 (m, 2 H), 1.52 (d, J=6.0 Hz, 3 H). MS (ESI) m/z (M+H)⁺ 513.3.

Synthesis of Compound 128

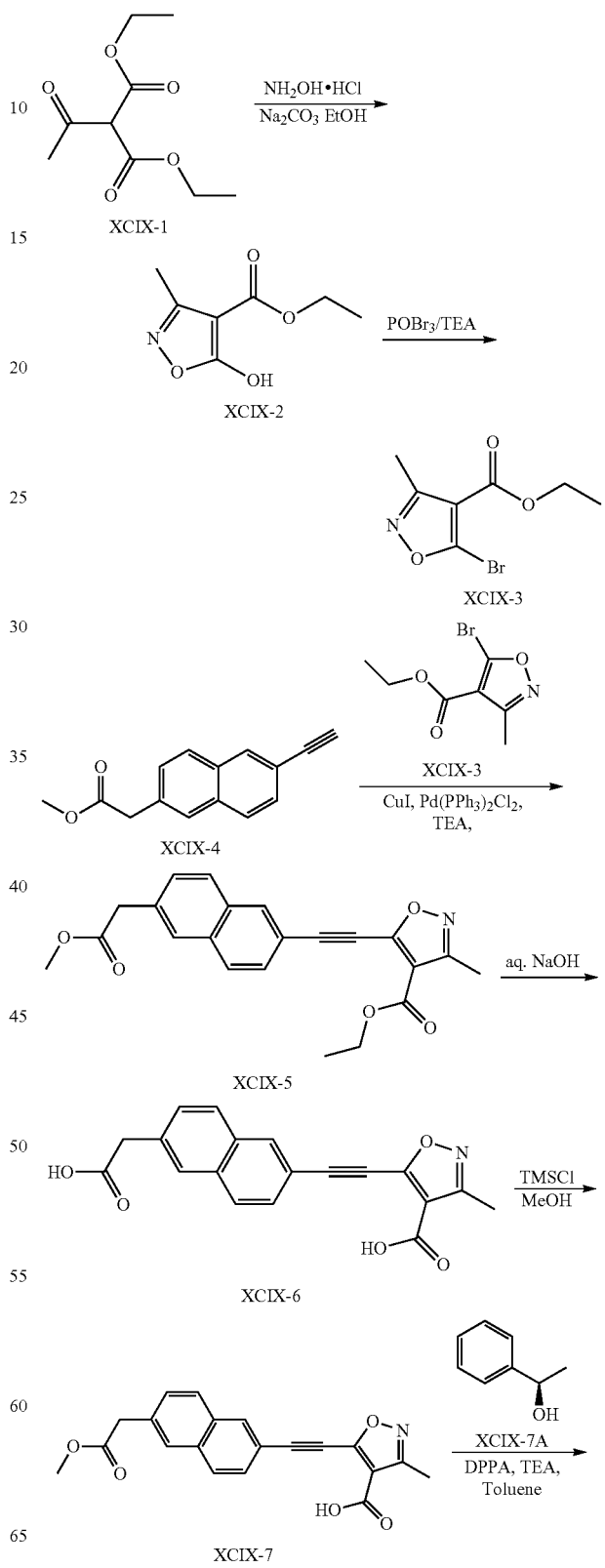

Synthetic Route (Scheme XCIX)

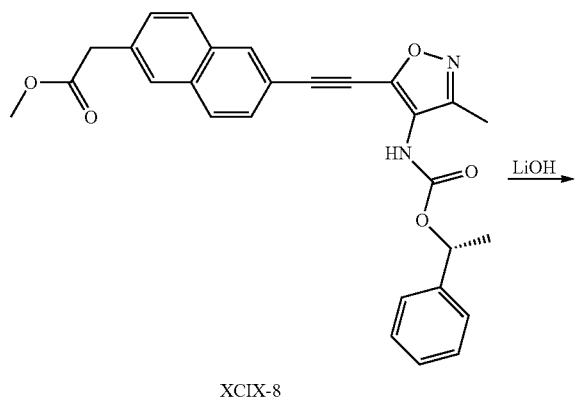

XCIX-8

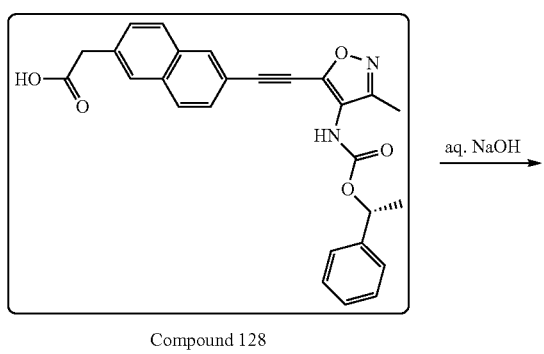

Compound 128

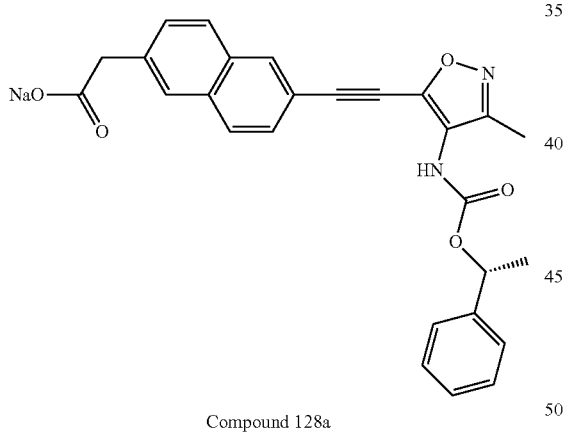

Compound 128a

A solution of compound XCIX-1 (20.2 g, 0.1 mol), NH₂OH.HCl (7.20 g, 0.11 mol) and Na₂CO₃ (5.3 g, 50 mmol) in EtOH (500 mL) was heated to reflux for 2 hours. After concentrated, the residue was poured into ice water (200 mL), the precipitated solid was collected to afford compound XCIX-2 (13.50 g, yield: 76%).

The mixture of compound XCIX-2 (13.5 g, 78.9 mmol) in POBr₃ (180 g, 631 mmol) and TEA (8.0 g, 78.9 was stirred at r.t. under nitrogen for 75 hours. Then ice water (60 mL) was added, the aqueous phase was extracted with EtOAc (100 mL×3), and the combined organic layer was washed with brine, dried over MgSO₄, concentrated. The residue was purified by column chromatography on silica gel (petroleum ether:EtOAc=5:1) to afford compound XCIX-3 (9.5 g, yield: 51.9%).

Pd(PPh₃)₂Cl₂ (30 mg) and CuI (30 mg) was added to a stirred solution of compound XCIX-4 (0.3 g, 1.34 mmol), compound XCIX-3 (0.3 g, 1.29 mmol) in TEA (5 mL) under argon. The reaction mixture was stirred at 80° C. for 1 hour. The solution was concentrated, then H₂O (10 mL) was added, and the mixture was extracted with EtOAc (20 mL×3). The organic layer was combined and washed with brine, dried over Na₂SO₄, and concentrated in vacuo. The residue was purified by Prep. TLC (PE:EA=5:1) to afford compound XCIX-5 (65 mg, yield 12.8%).

To a stirred solution of compound XCIX-5 (65 mg, 0.17 mmol) in THF (4 mL) and water (1 mL), NaOH (14 mg, 0.34 mmol) was added. The mixture was stirred at room temperature for 1 hour. Then concentrated, water (10 mL) was added, adjust pH to 4 with HCl (1 N), and extracted with EtOAc (15 mL×3). The combined organic layers were washed with brine (20 mL), dried and concentrated under reduced pressure to afford crude compound XCIX-6 (49 mg, yield 84.9%). MS (ESI) m/z (M+H)⁺ 336.0.

TMSCl (116 mg, 1.07 mmol) was added to a mixture of compound XCIX-6 (90 mg, 0.268 mmol) in 8 mL of MeOH. The reaction mixture was stirred at r.t. for 6 hrs. Then water (10 mL) was added, and extracted with EtOAc (20 mL). The organic layers were washed with brine (20 mL), dried and concentrated under reduced pressure to afford compound XCIX-7 (crude 88 mg), which was used to next step directly.

To a stirred solution of compound XCIX-7 (66 mg, 0.189 mmol), compound XCIX-7A (25.3 mg, 0.2 mmol), TEA (38 mg, 0.37 mmol) in toluene (10 mL) was added DPPA (62 mg, 0.22 mmol) under nitrogen. After the addition, the solution was heated to reflux under nitrogen for 2 hours. The solution was concentrated. The residue was purified by column chromatography on silica gel (petroleum ether: EtOAc=10:1) to afford compound XCIX-8 (46 mg, yield 52%). MS (ESI) m/z (M+H)⁺ 469.1.

Preparation of Compound 128

To a stirred solution of compound XCIX-8 (46 mg, 1.0 mmol) in THF/MeOH/H₂O (2 mL/2 mL/1 mL) was added LiOH (11.8 mg, 0.49 mmol). The mixture was stirred at room temperature overnight. Then concentrated, water (10 mL) was added, adjusts pH to 3 with 1N HCl, and extracted with EtOAc (15 mL×3). The combined organic layers were washed with brine (20 mL), dried and concentrated under reduced pressure. The residue was purified by Prep. HPLC to afford Compound 128 (18 mg, yield: 40.3%). MS (ESI) m/z (M+H)⁺ 455.0.

Preparation of Compound 128a

To a solution of Compound 128 (16 mg, 0.035 mmol) in CH₃CN (2 mL) was added aq. NaOH (0.05N, 0.7 mL), and the mixture was stirred for one hour at r.t., then the reaction mixture was lyophilized to give Compound 128a. ¹H NMR (Methanol-d₄, 400 MHz): δ8.05 (s, 1H), 7.81-7.86 (m, 3H), 7.59 (d, J=8.8 Hz, 1H), 7.27-7.47 (m, 6H), 5.85 (q, 1H), 3.68 (s, 2H), 2.22 (s, 3H), 1.60 (d, J=6.0 Hz, 3H). MS (ESI) m/z (M+H)⁺ 455.0.

Synthesis of Compound 129
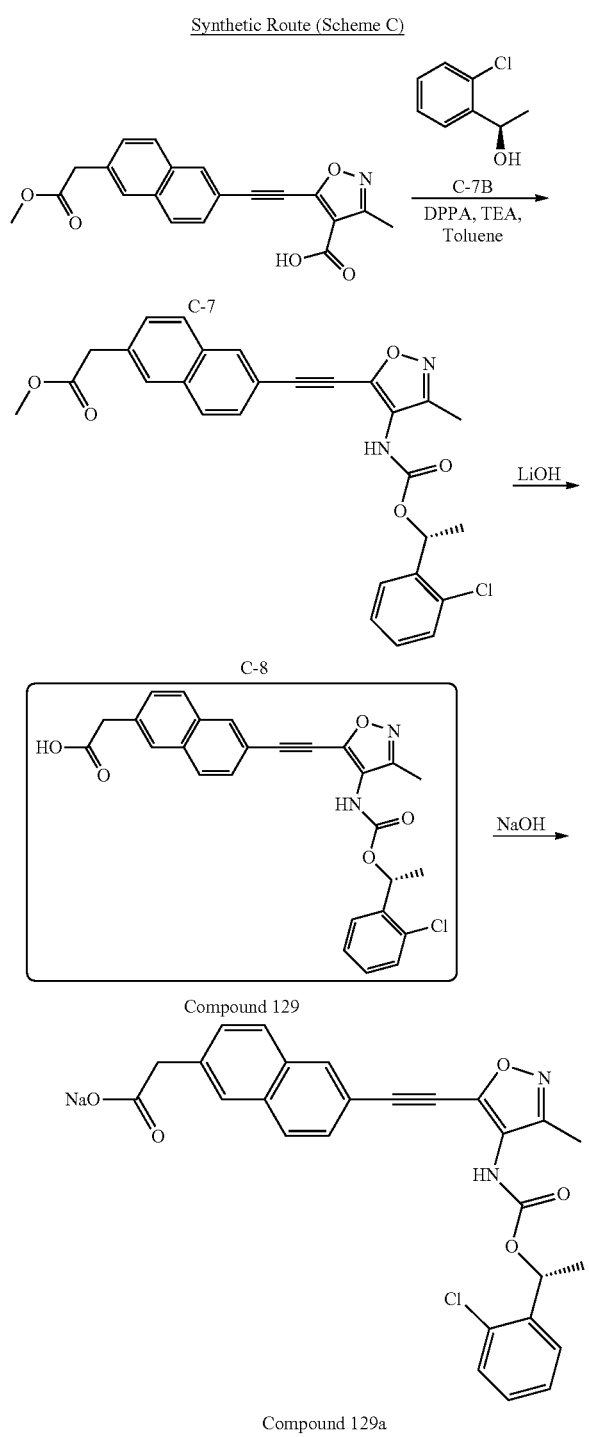
Compound 129 was prepared analogously to the procedure described in the synthesis of Compound 128 (30 mg, yield: 51%). MS (ESI) m/z (M+H)+ 489.2.
Compound 129a was prepared analogously to the procedure described in the synthesis of Compound 128a. $^1$H NMR (Methanol-$d_4$, 400 MHz): δ 8.05 (s, 1H), 7.80-7.86 (m, 3H), 7.60 (d, J=8.4 Hz, 2H), 7.46 (d, J=8.4 Hz, 1H), 7.38 (d, J=8.4 Hz, 1H), 7.22-7.29 (m, 2H) 6.22 (q, 1H), 3.68 (s, 2H), 2.24 (s, 3H), 1.60 (d, J=6.0 Hz, 3H). MS (ESI) m/z (M+H)+ 489.2.
Synthesis of Compound 130
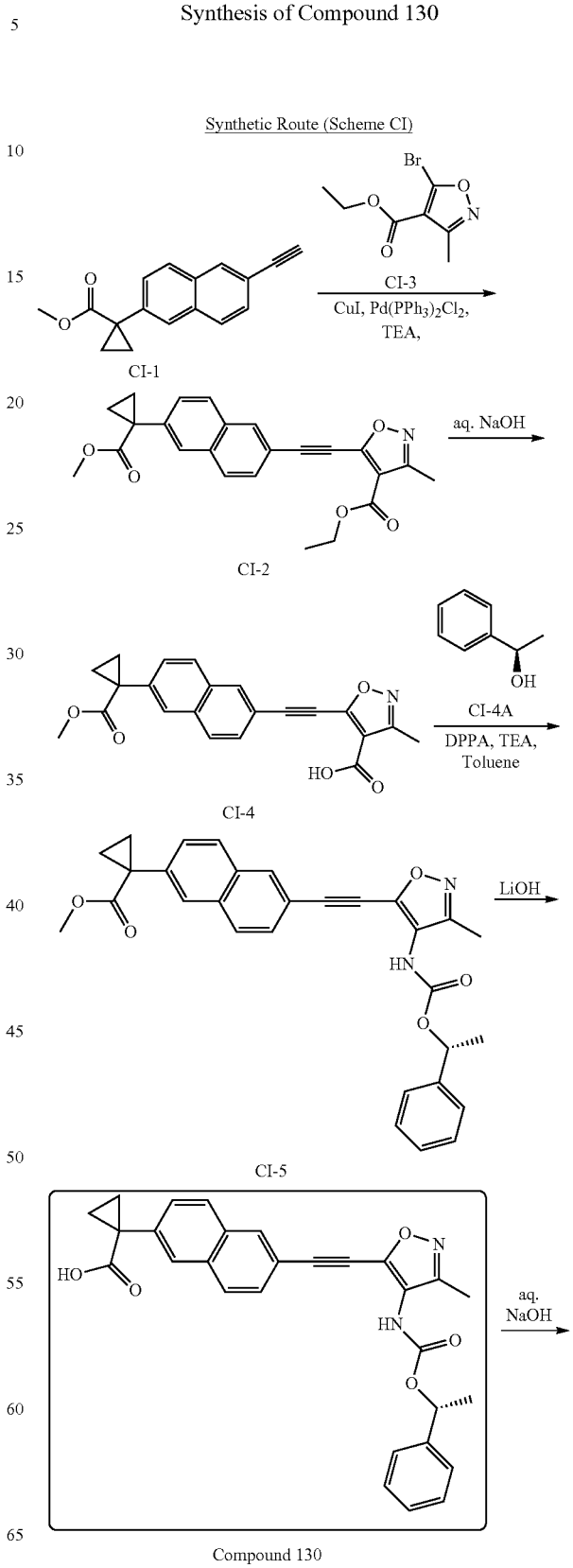

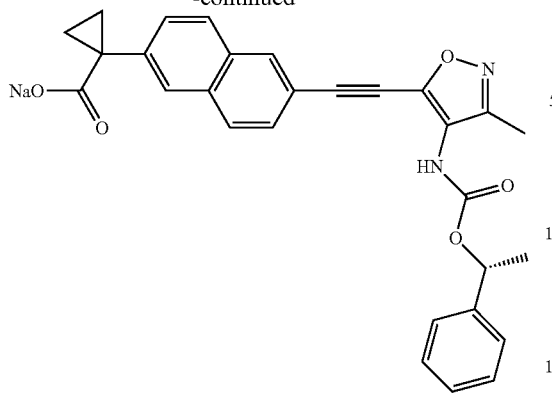

Compound 130a

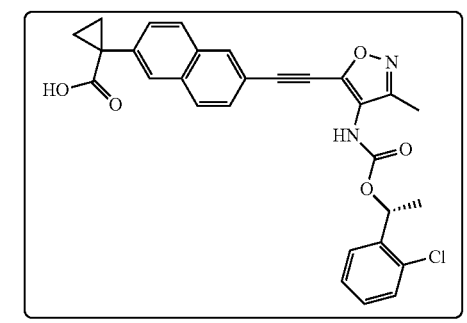

Compound 131

The detailed procedure for compound CI-1 has been described in synthesis of Compound 92. Compound 130 was prepared analogously to the procedure described in the synthesis of Compound 128. MS (ESI) m/z (M+H)+ 481.2.

Compound 130a was prepared analogously to the procedure described in the synthesis of Compound 128a. $^1$H NMR (Methanol-$d_4$, 400 MHz): δ 9.53 (br, 1H), 8.14 (s, 1H), 7.92 (d, J=8.4 Hz, 1H), 7.82-7.86 (m, 2H), 7.60 (d, J=8.4 Hz, 1H), 7.28-7.41 (m, 6H), 5.78-5.84 (q, 1H), 2.19 (s, 3H), 1.54 (d, J=6.4 Hz, 3H), 1.42 (br, 2H), 1.09 (br, 2H). MS (ESI) m/z (M+H)+ 481.2.

Synthesis of Compound 131

Synthetic Route (Scheme CII)

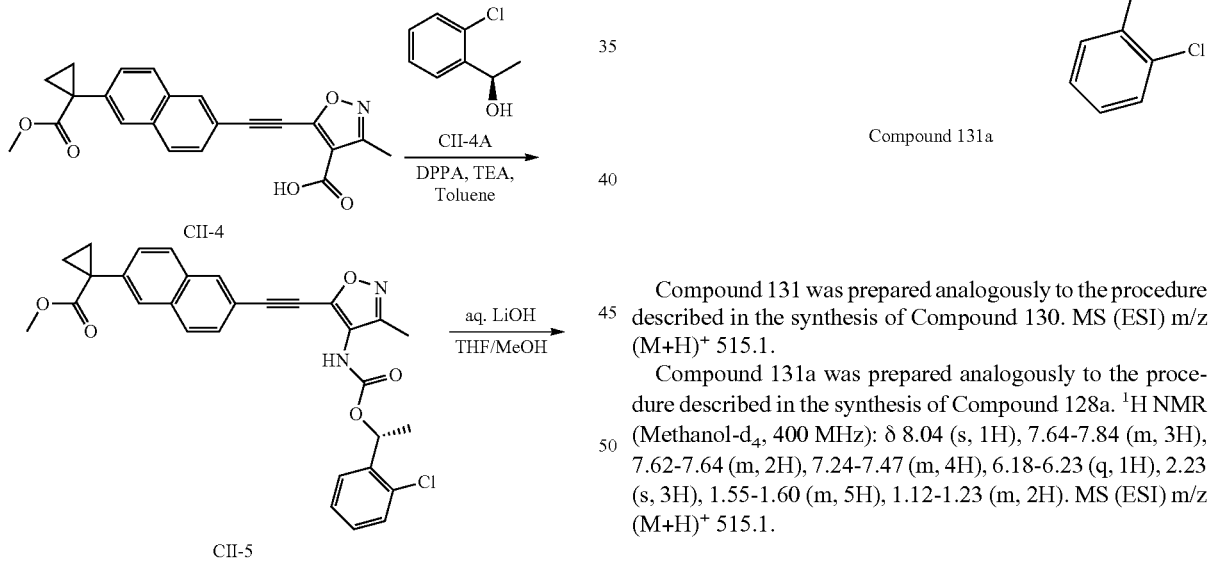

Compound 131 was prepared analogously to the procedure described in the synthesis of Compound 130. MS (ESI) m/z (M+H)+ 515.1.

Compound 131a was prepared analogously to the procedure described in the synthesis of Compound 128a. $^1$H NMR (Methanol-$d_4$, 400 MHz): δ 8.04 (s, 1H), 7.64-7.84 (m, 3H), 7.62-7.64 (m, 2H), 7.24-7.47 (m, 4H), 6.18-6.23 (q, 1H), 2.23 (s, 3H), 1.55-1.60 (m, 5H), 1.12-1.23 (m, 2H). MS (ESI) m/z (M+H)+ 515.1.

Synthesis of Compound 132

Synthetic Route (Scheme CIII)

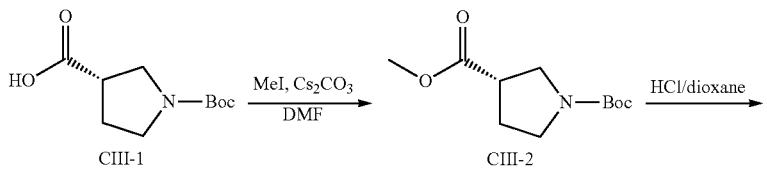

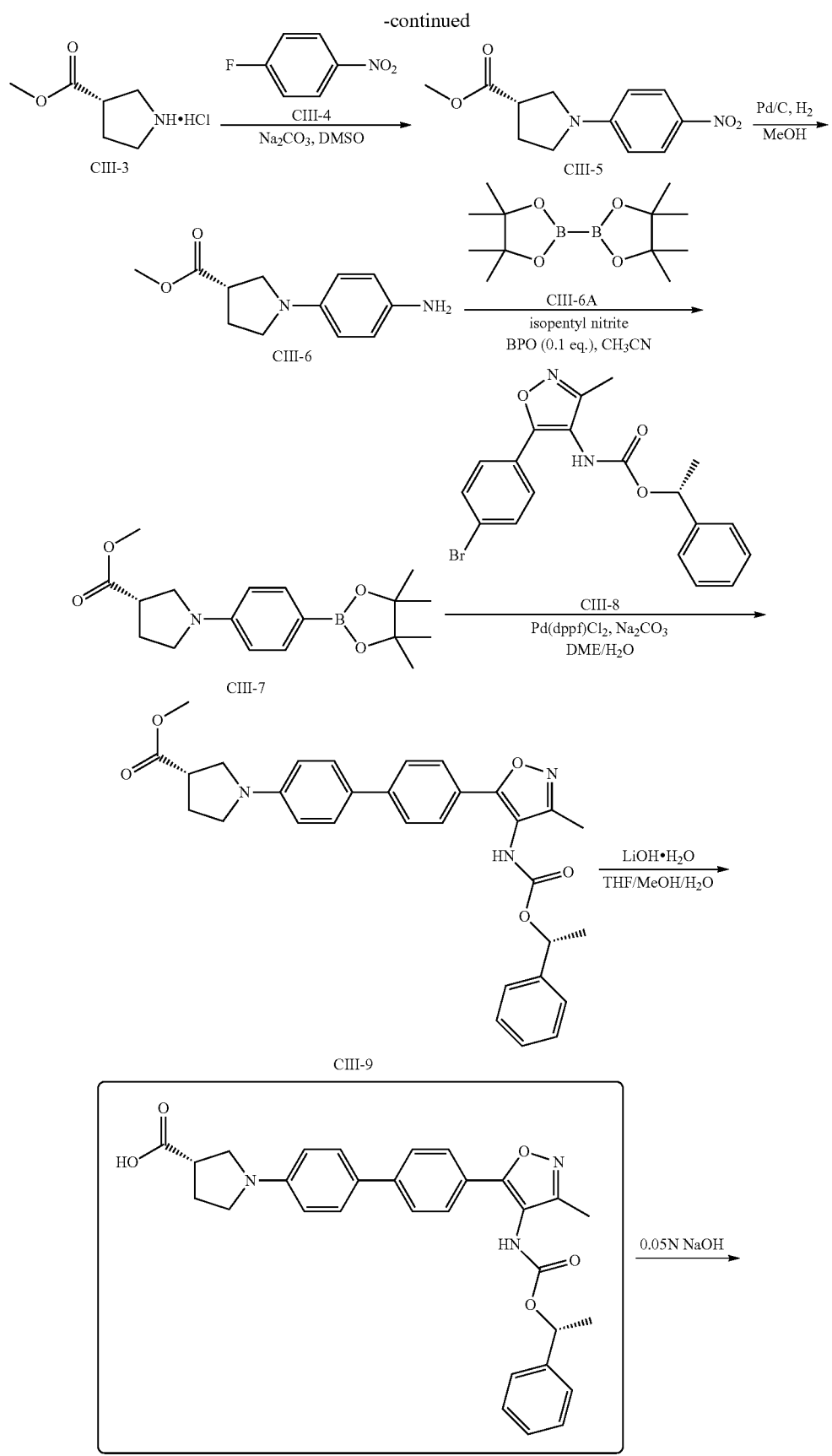
Compound 132

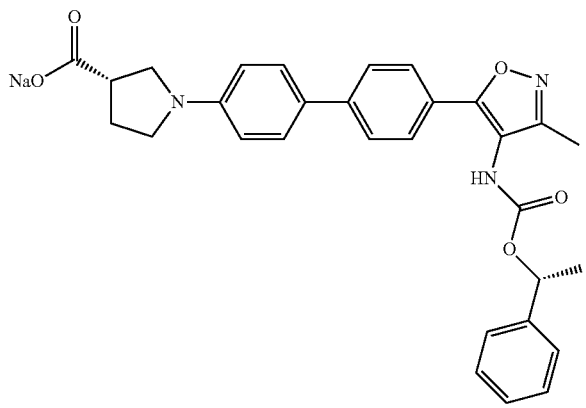

Compound 132a

A mixture of compound CIII-1 (8.0 g, 48.30 mmol), MeI (19.8 g, 139.46 mmol) and $Cs_2CO_3$ (45.4 g, 139.46 mmol) in 120 mL of DMF was stirred overnight at room temperature. The mixture was poured into water and extracted with ethyl acetate (200 mL×3). The combined organic layer was washed with brine, dried and concentrated to yield compound CIII-2 (10 g, yield 94%).

80 mL of HCl in dioxane (4 N, 320 mmol) was added to a solution of compound CIII-2 (10.0 g, 48.5 mmol) in 25 mL of THF. The mixture was stirred overnight at room temperature. The mixture was concentrated in vacuum to yield compound CIII-3 (7.8 g, crude yield 100%).

To a suspension of compound CIII-3 (7.8 g, 47.10 mmol) and $Na_2CO_3$ (20.0 g, 180.38 mmol) in DMSO (50 mL) was added compound CIII-4 (6.6 g, 47.10 mmol). The mixture was heated to 85° C. and stirred overnight. After cooled, the mixture was poured into water and extracted with ethyl acetate (100 mL×3). The combined organic layer was washed with saturated $NaHCO_3$, brine and dried over $MgSO_4$. After filtered, the filtrate was concentrated in vacuum. The residue was washed with TBME to yield compound CIII-5 (5.5 g, yield 47%).

A mixture of compound CIII-5 (5.5 g, 22.0 mmol) and catalyst Pd/C (1.1 g) in methanol (150 mL) was stirred for 1 day at 40° C. under hydrogen atmosphere. The mixture was filtered through Celite. The filtrate was concentrated in vacuum to yield compound CIII-6 (4.7 g, yield 97%).

To a mixture of compound CIII-6 (4.7 g, 21.35 mmol), bis(pinacolato)diboron CIII-6A (6.5 g, 25.62 mmol) and BPO (0.52 g, 2.14 mmol) in $CH_3CN$ (80 mL) was added tert-butyl nitrite (3.3 g, 32.03 mmol) slowly. The mixture was stirred for overnight at room temperature. The mixture was concentrated and the residue was partitioned between water and ethyl acetate. The aqueous layer was extracted with ethyl acetate (100 mL×2). The combined organic layer was washed with saturated $Na_2SO_3$, brine, dried and concentrated. The residue was purified by column chromatography over silica gel (PE/EA=15/1) to yield compound CIII-7 (2.7 g, yield 38%).

Argon was bubbled through the mixture of compound CIII-7 (200 mg, 0.6 mmol), compound CIII-8 (242 mg, 0.6 mmol) and $Na_2CO_3$ (127 mg, 1.20 mmol) in a mixed solvent of $DME/H_2O$ (6 mL, v/v=3/1). Then the catalyst $Pd(dppf)Cl_2$ (22 mg, 0.03 mmol) was added. The mixture was heated to 80° C. and stirred for 2 hours. The mixture was filtered through Celite and the filtrate was concentrated. The residue was purified by column chromatography over silica gel (PE/EA=5/1) to yield compound CIII-9 (290 mg, yield 91%). MS (ESI) m/z $(M+H)^+$ 526.3.

Preparation of Compound 132

To a stirred solution of CIII-9 (285 mg, 0.54 mmol) in 10 mL of $THF/MeOH/H_2O$ (v/v/v=1/1/1) was added lithium hydroxide monohydrate (91 mg, 2.17 mmol). The mixture was stirred overnight at room temperature. The volatile solvent was evaporated in vacuum. The resulting aqueous solution was acidified to pH=3 by citric acid aqueous solution, and extracted with ethyl acetate (15 mL×3). The combined organic layer was washed with brine, dried and concentrated. The residue was purified by prep-HPLC to yield Compound 132 (181 mg, yield 65%). MS (ESI) m/z $(M+H)^+$ 512.3.

Preparation of Compound 132a

To a stirred solution of Compound 132 (180 mg, 0.351 mmol) in 1 mL of THF was added 0.05 N NaOH aqueous solution (7.029 mL, 0.351 mmol). The mixture was stirred for 15 minutes at room temperature and the volatile solvent was evaporated. The residue was lyophilized to yield Compound 132a. $^1$H NMR (DMSO-$d_6$, 400 MHz): δ 9.43 (s, 1H), 7.68-7.78 (m, 4H), 7.58 (d, J=8.4 Hz, 2H), 7.09-7.44 (m, 5H), 6.58 (d, J=8.4 Hz, 2H), 5.74-5.77 (m, 1H), 3.48-3.50 (m, 1H), 3.19-3.27 (m, 3H), 2.76-2.80 (m, 1H), 2.16-2.20 (m, 4H), 2.00-2.06 (m, 1H), 1.56 (d, J=6.4 Hz, 3H). MS (ESI) m/z $(M+H)^+$ 512.3.

Synthesis of Compound 133
Synthetic Route (Scheme CIV)
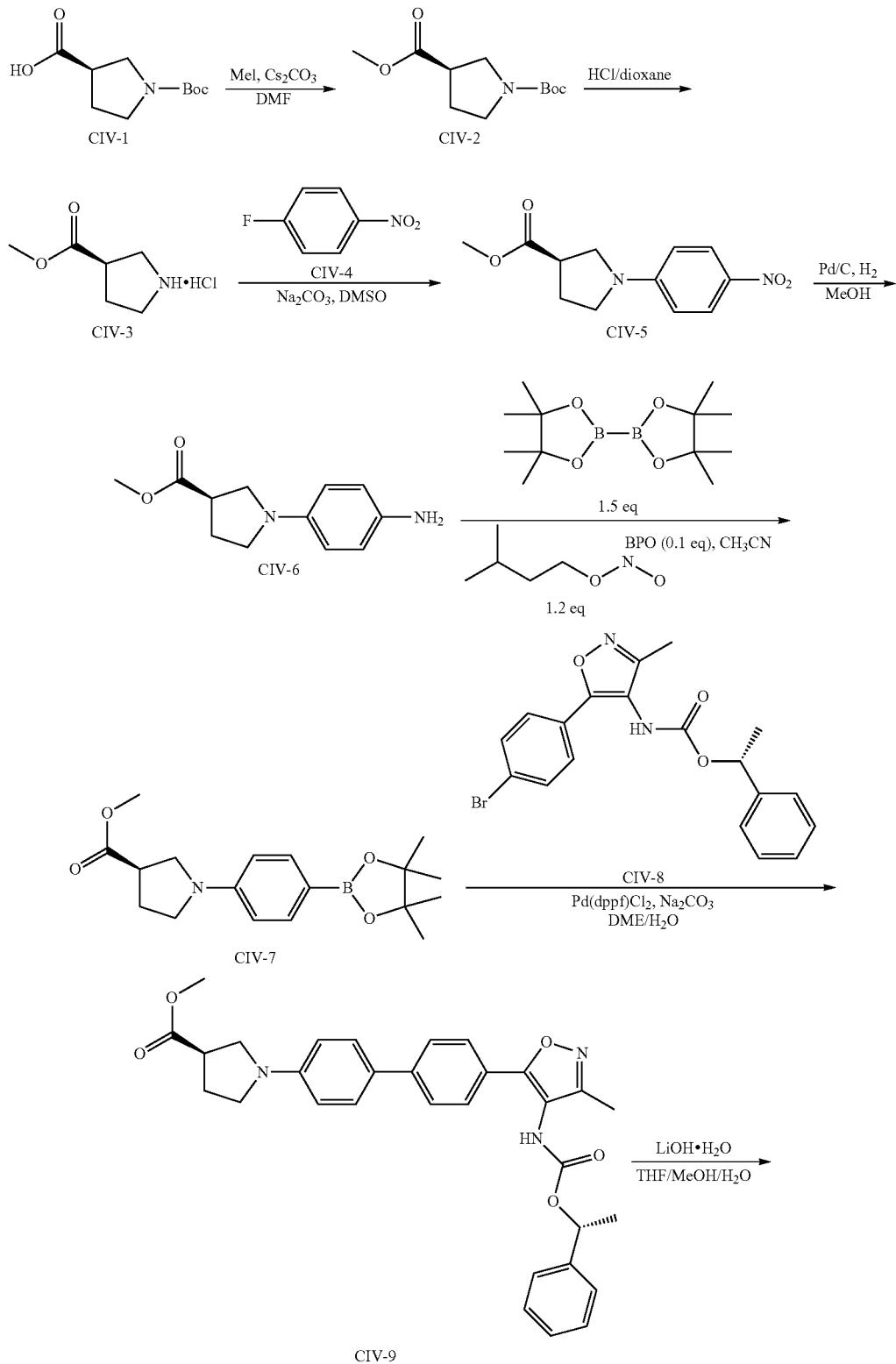

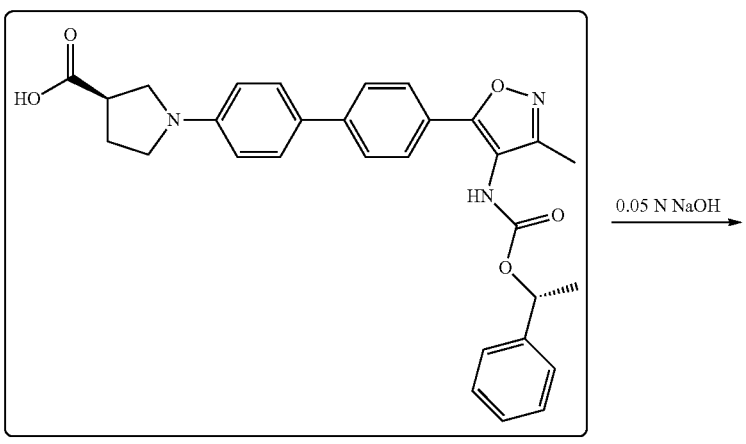

Compound 133

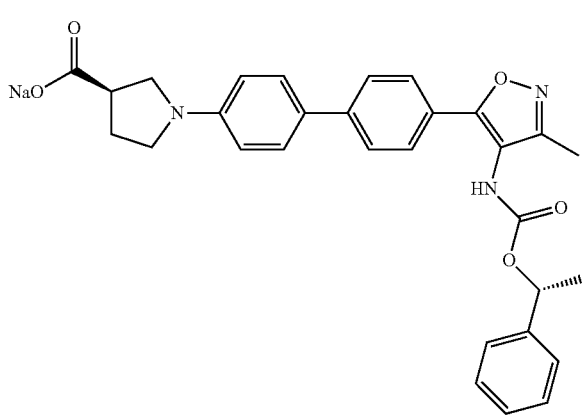

Compound 133a

Compound 133 was prepared analogously to the procedure described in the synthesis of Compound 132. MS (ESI) m/z (M+H)+ 511.1.

Compound 133a was prepared analogously to the procedure described in the synthesis of Compound 132a. $^1$H NMR (DMSO-d$_6$, 400 MHz): δ 8.92 (s, 1H), 7.73 (d, J=8.0 Hz, 2H), 7.66 (d, J=8.4 Hz, 2H), 7.54 (d, J=8.4 Hz, 2H), 7.28-7.35 (m, 5H), 6.60 (d, J=8.4 Hz, 2H), 5.75-5.80 (q, 1H), 3.41-3.53 (m, 1H), 3.33-3.39 (m, 1H), 3.29-3.33 (m, 1H), 3.21-3.27 (m, 1H), 2.83-2.84 (m, 1H), 2.18-2.20 (m, 1H), 1.99-2.08 (m, 5H), 1.50-1.52 (d, J=6.4 Hz, 3H). MS (ESI) m/z (M+H)+ 511.1.

Synthesis of Compound 134

Synthetic Route (Scheme CV)

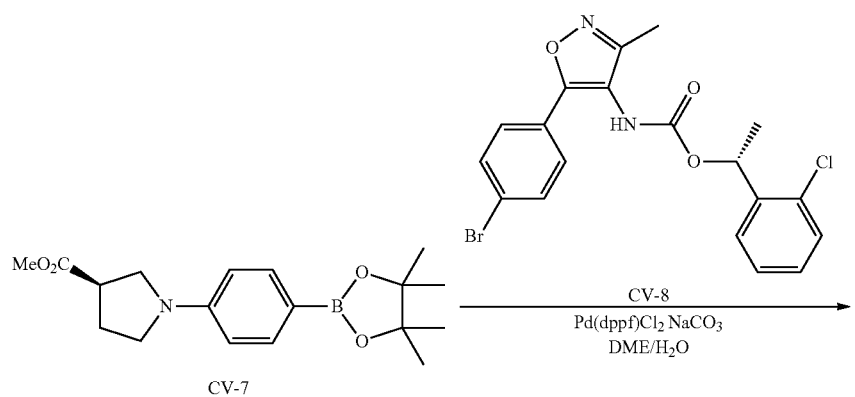

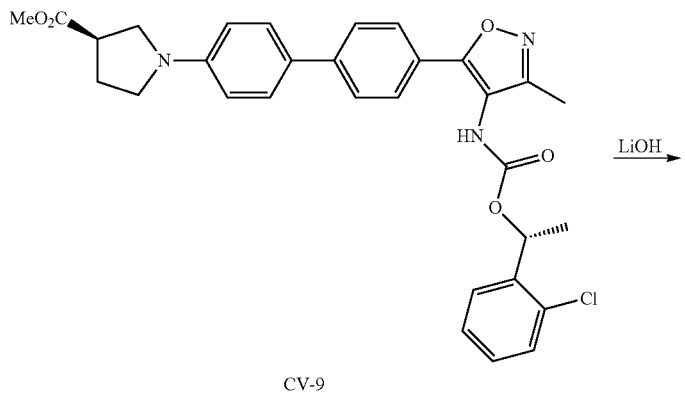
CV-9
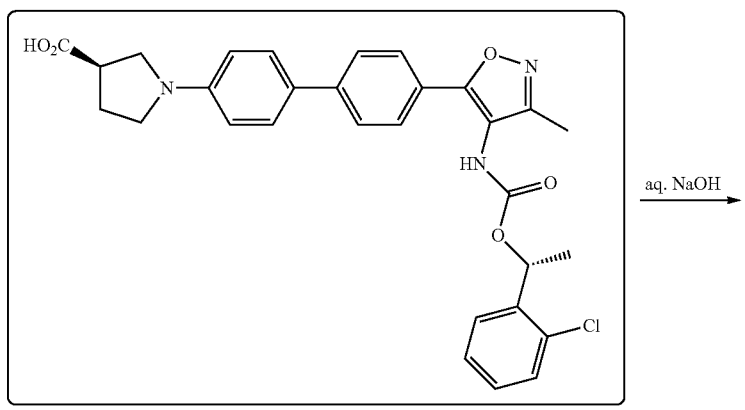
Compound 134
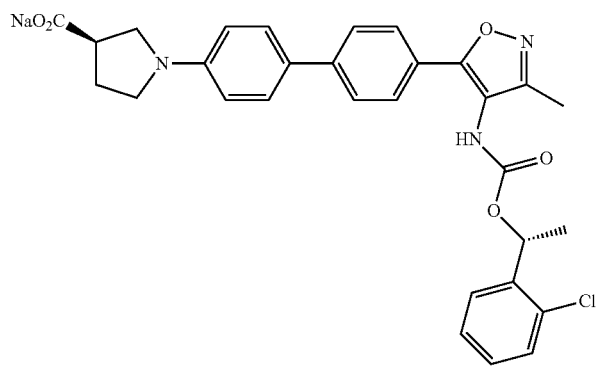
Compound 134a
Compound 134 was prepared analogously to the procedure described in the synthesis of Compound 132 (48.0 mg, yield: 49.2%). MS (ESI) m/z (M+H)+ 546.3.
Compound 134a was prepared analogously to the procedure described in the synthesis of Compound 132a. $^1$H NMR ((DMSO-$d_6$, 400 MHz): δ 7.79 (d, J=8.0 Hz, 2H), 7.75 (d, J=8.4 Hz, 2H), 7.70-7.75 (m, 4H), 7.46-7.55 (m, 2H), 6.60 (d, J=8.8 Hz, 2H), 6.02-6.07 (q, 1H), 3.39-3.53 (m, 1H), 3.21-3.37 (m, 3H), 2.78-2.85 (m, 1H), 2.14-2.25 (m, 1H), 2.11 (s, 3H), 2.00-2.08 (m, 1H), 1.52 (d, J=6.4 Hz, 3H). MS (ESI) m/z (M+H)+ 545.1.

Synthesis of Compound 135
Synthetic Route (Scheme CVI)
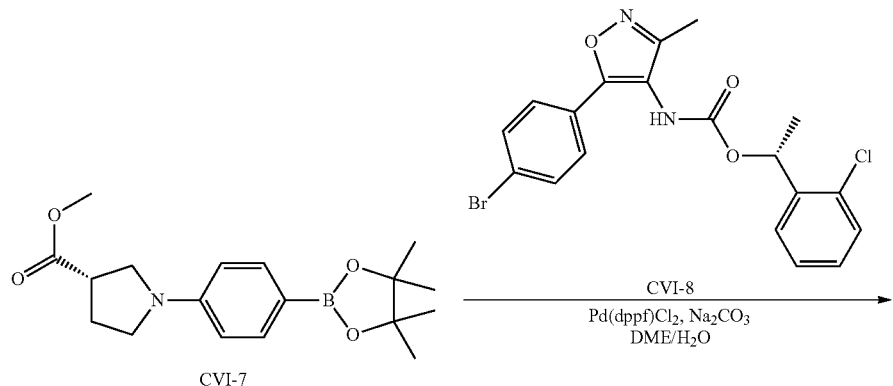
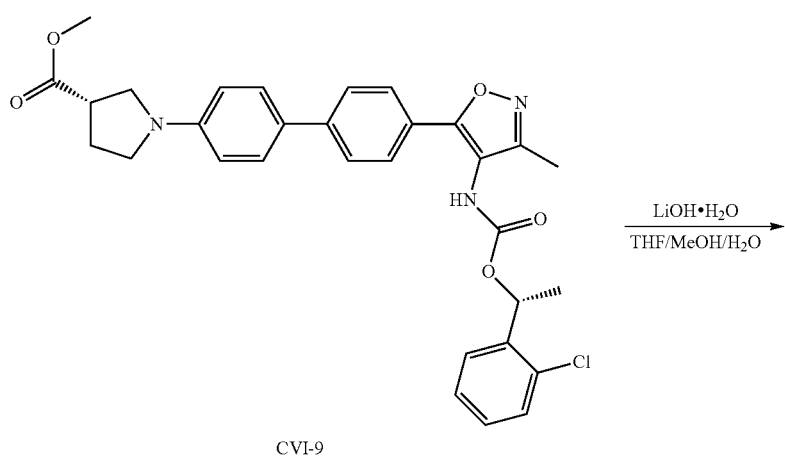
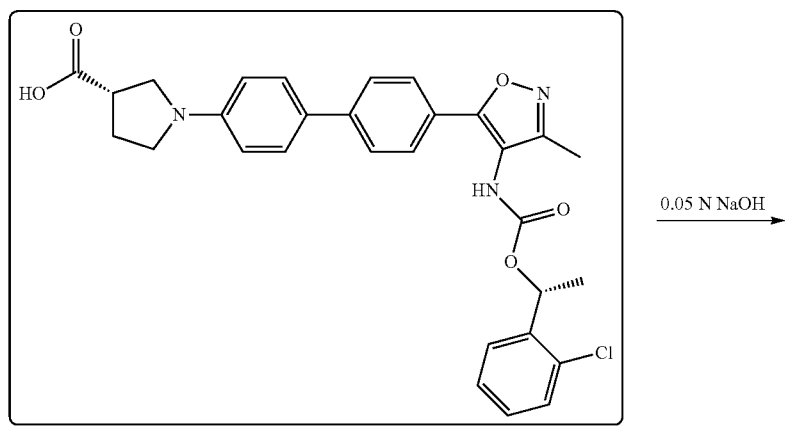
Compound 135

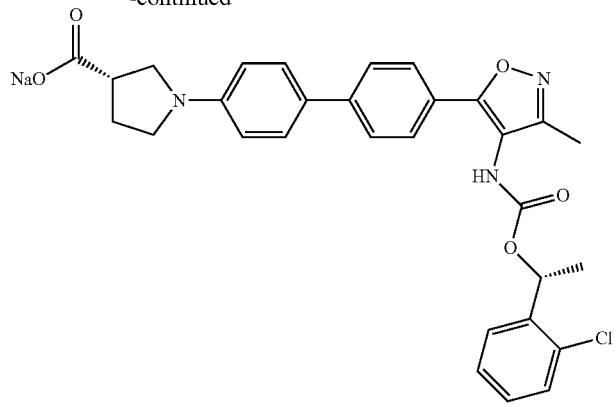
Compound 135a
Compound 135 was prepared analogously to the procedure described in the synthesis of Compound 132. Compound 135a was prepared analogously to the procedure described in the synthesis of Compound 132a. $^1$H NMR (DMSO-$d_6$, 400 MHz): δ 8.97 (br, 1H), 7.77 (d, J=8.4 Hz, 2H), 7.70 (d, J=8 Hz, 2H), 7.59 (d, J=8.4 Hz, 2H), 7.32-7.47 (m, 4H), 6.68 (d, J=8 Hz, 2H), 6.06 (q, J=6.4 Hz, 1H), 3.56-3.59 (m, 2H), 3.34-3.48 (m, 2H), 3.14-3.20 (m, 1H), 2.21-2.24 (m, 2H), 2.15 (s, 3H), 1.52 (d, J=6.4 Hz, 3H). MS (ESI) m/z (M+H)$^+$ 546.0.
Synthesis of Compound 136
Synthetic Route (Scheme CVII)
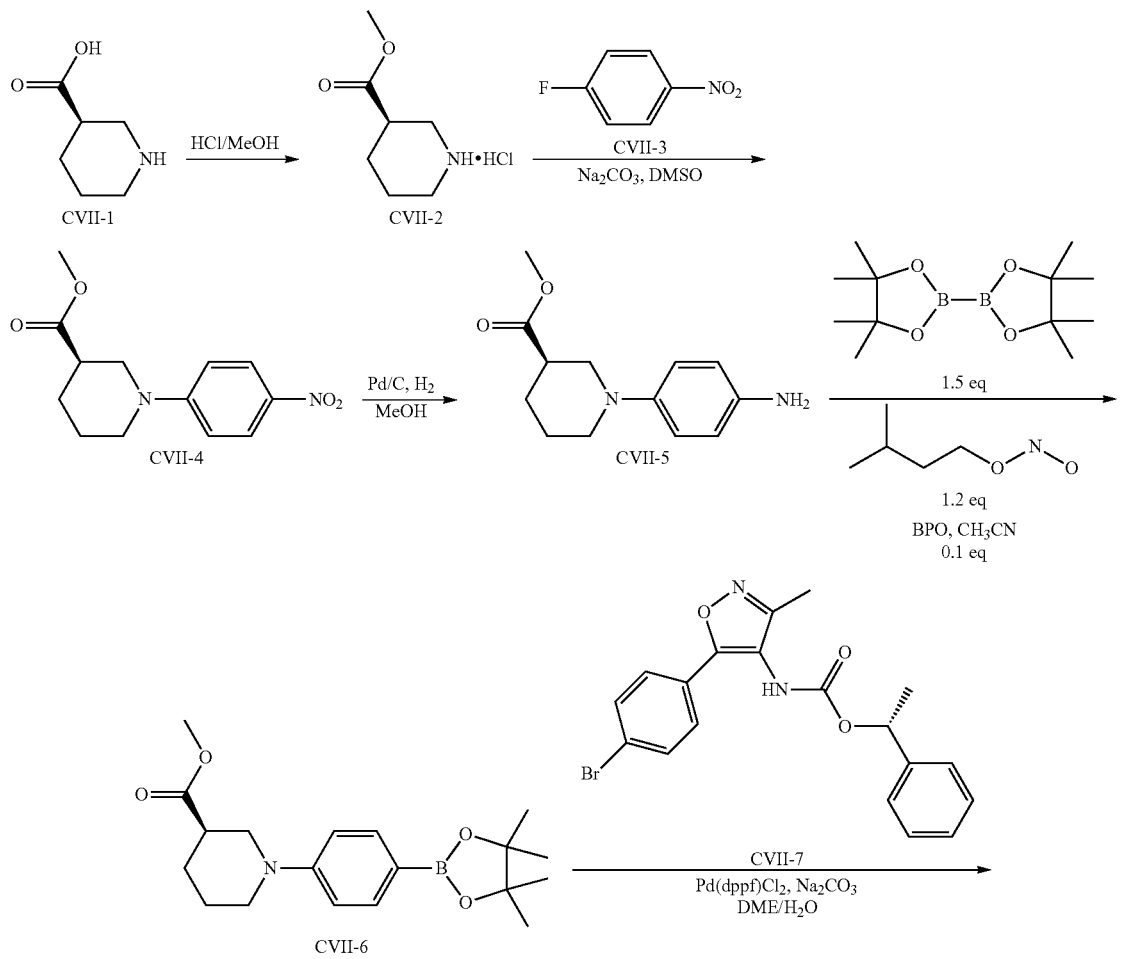

-continued

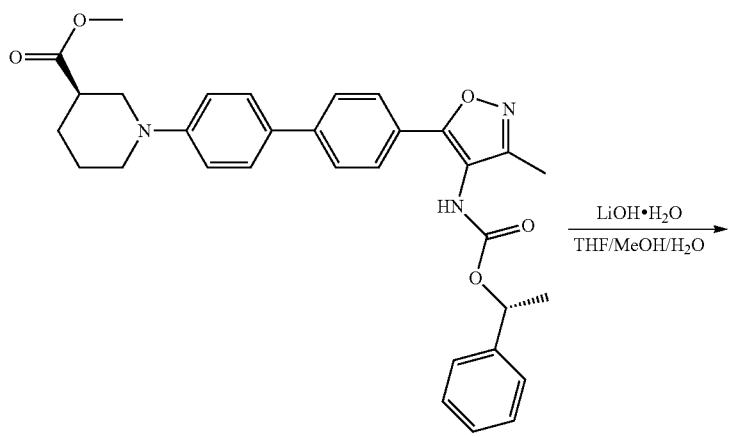

CVII-8

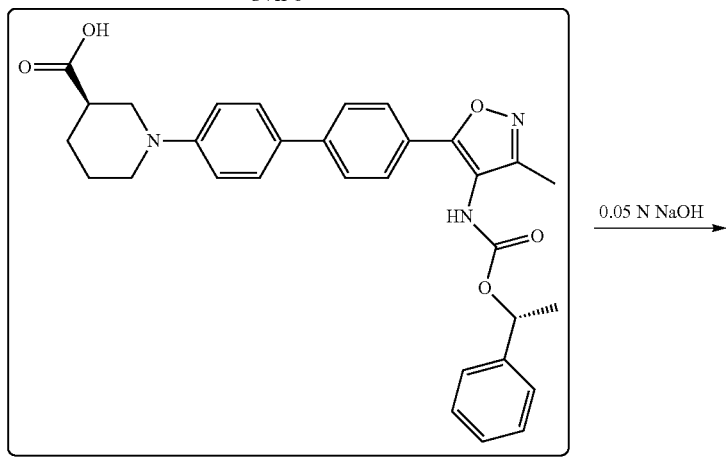

Compound 136

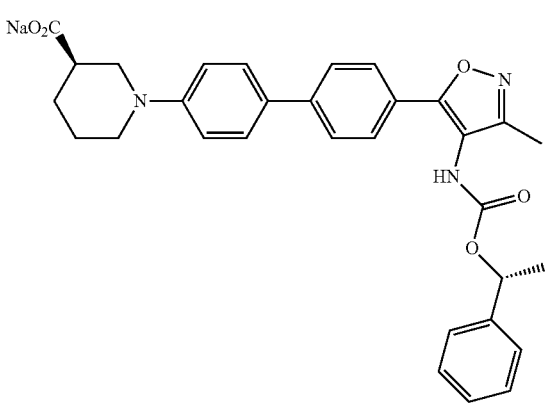

Compound 136a

A mixture of compound CVII-1 (8.0 g, 48.30 mmol) in 4 N HCl in MeOH (120 mL) was heated to reflux for 3 hours. The mixture was concentrated to yield compound CVII-2 (10.6 g, yield 95%), which was used in next step directly.

Compound 136 was prepared analogously to the procedure described in the synthesis of Compound 132 (95 mg, yield 49%). $^1$H NMR (DMSO-$d_6$, 400 MHz): δ 9.33 (s, 1H), 7.72-7.77 (m, 4H), 7.63 (d, J=8.4 Hz, 2H), 7.21-7.44 (m, 5H), 7.06 (d, J=8.4 Hz, 2H), 5.77 (q, J=6.4 Hz, 1H), 3.74-3.78 (m, 1H), 3.57-3.60 (m, 1H), 3.03-3.08 (m, 1H), 2.88-2.93 (m, 1H), 2.56-2.58 (m, 1H), 2.12 (s, 3H), 1.92-1.94 (m, 1H), 1.72-1.75 (m, 1H), 1.60-1.68 (m, 2H), 1.56 (d, J=6.4 Hz, 3H). MS (ESI) m/z (M+H)$^+$ 526.1.

Compound 136a was prepared analogously to the procedure described in the synthesis of Compound 132a (80 mg, yield 81%). $^1$H NMR (DMSO-$d_6$, 400 MHz): δ 9.32 (s, 1H), 7.72-7.74 (m, 4H), 7.60 (d, J=8.4 Hz, 2H), 7.21-7.43 (m, 5H), 7.02 (d, J=8.4 Hz, 2H), 5.77 (m, 1H), 3.79-3.82 (m, 1H), 3.62-3.65 (m, 1H), 2.87-2.92 (m, 1H), 2.76-2.81 (m, 1H), 2.33-2.36 (m, 1H), 2.12 (s, 3H), 1.92-1.94 (m, 1H), 1.69-1.71 (m, 1H), 1.53-1.55 (m, 5H). MS (ESI) m/z (M+H)$^+$ 526.3.

Synthesis of Compound 137
Synthetic Route (Scheme CVIII)
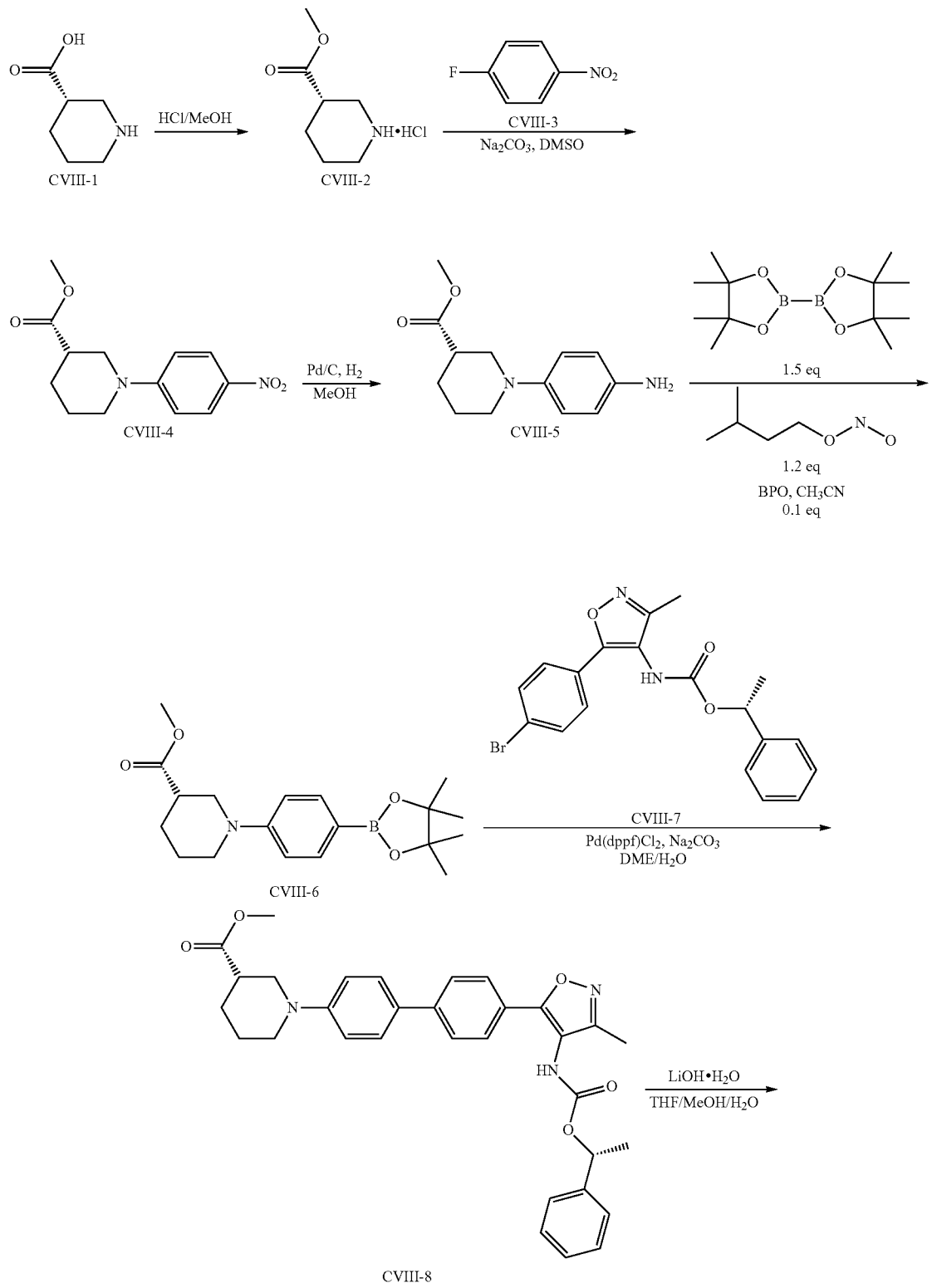

-continued

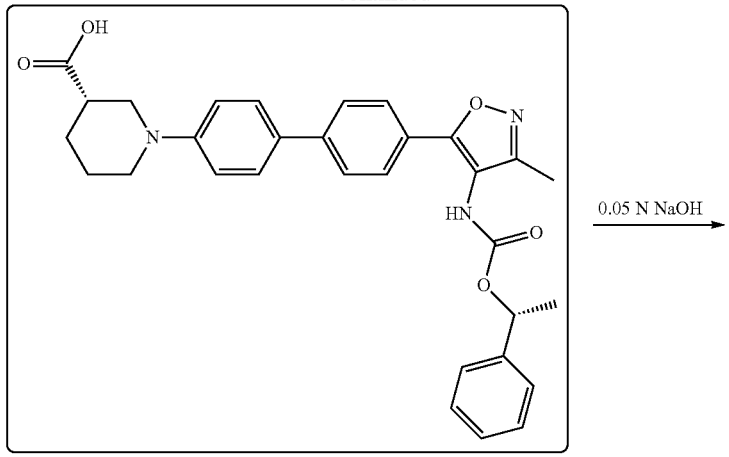

Compound 137

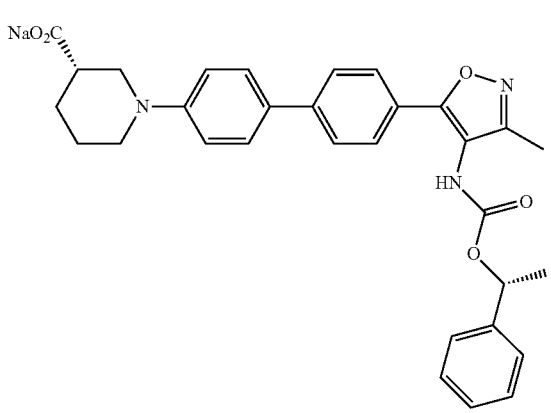

Compound 137a

Compound 137 was prepared analogously to the procedure described in the synthesis of Compound 136. $^1$H NMR (DMSO-d$_6$, 400 MHz): δ 12.37 (br, 1H), 9.29 (s, 1H), 7.73-7.75 (m, 4H), 7.62 (d, J=8.8 Hz, 2H), 7.21-7.43 (m, 5H), 7.05 (d, J=8.8 Hz, 2H), 5.76-5.78 (m, 1H), 3.74-3.76 (m, 1H), 3.56-3.62 (m, 1H), 3.03-3.08 (m, 1H), 2.87-2.93 (m, 1H), 2.55-2.57 (m, 1H), 2.12 (s, 3H), 1.92-1.94 (m, 1H), 1.71-1.76 (m, 1H), 1.56-1.65 (m, 5H). MS (ESI) m/z (M+H)$^+$ 526.1.

Compound 137a was prepared analogously to the procedure described in the synthesis of Compound 132a. $^1$H NMR (DMSO-d$_6$, 400 MHz): δ 9.40 (br, 1H), 7.72-7.75 (m, 4H), 7.59 (d, J=8.4 Hz, 2H), 7.21-7.43 (m, 5H), 6.99 (d, J=8.4 Hz, 2H), 5.76 (m, 1H), 3.82-3.85 (m, 1H), 3.67-3.70 (m, 1H), 2.66-2.79 (m, 2H), 2.13 (s, 3H), 2.05-2.09 (m, 1H), 1.93-1.95 (m, 1H), 1.67-1.70 (m, 1H), 1.40-1.55 (m, 5H). MS (ESI) m/z (M+H)$^+$ 526.1.

Synthesis of Compound 138

Synthetic Route (Scheme CIX)

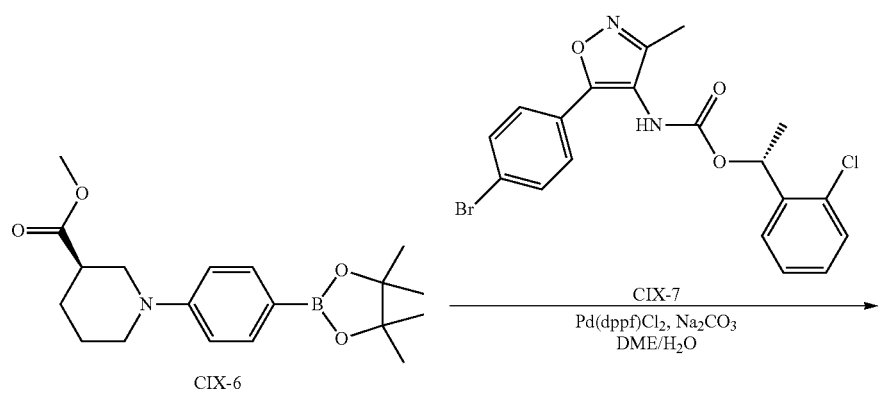

-continued

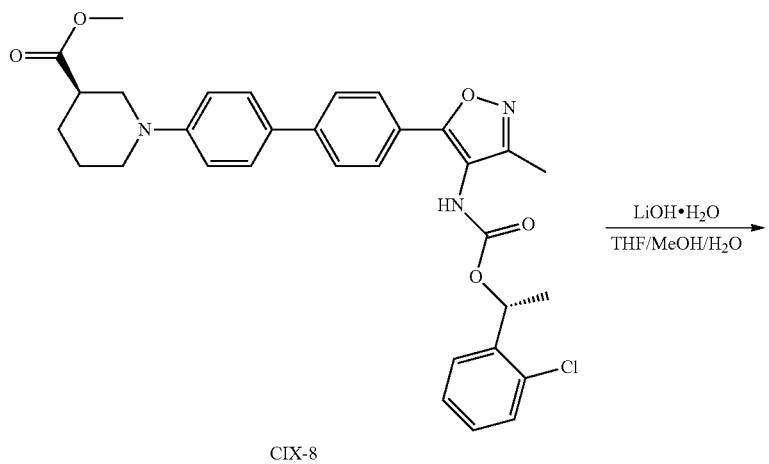

CIX-8

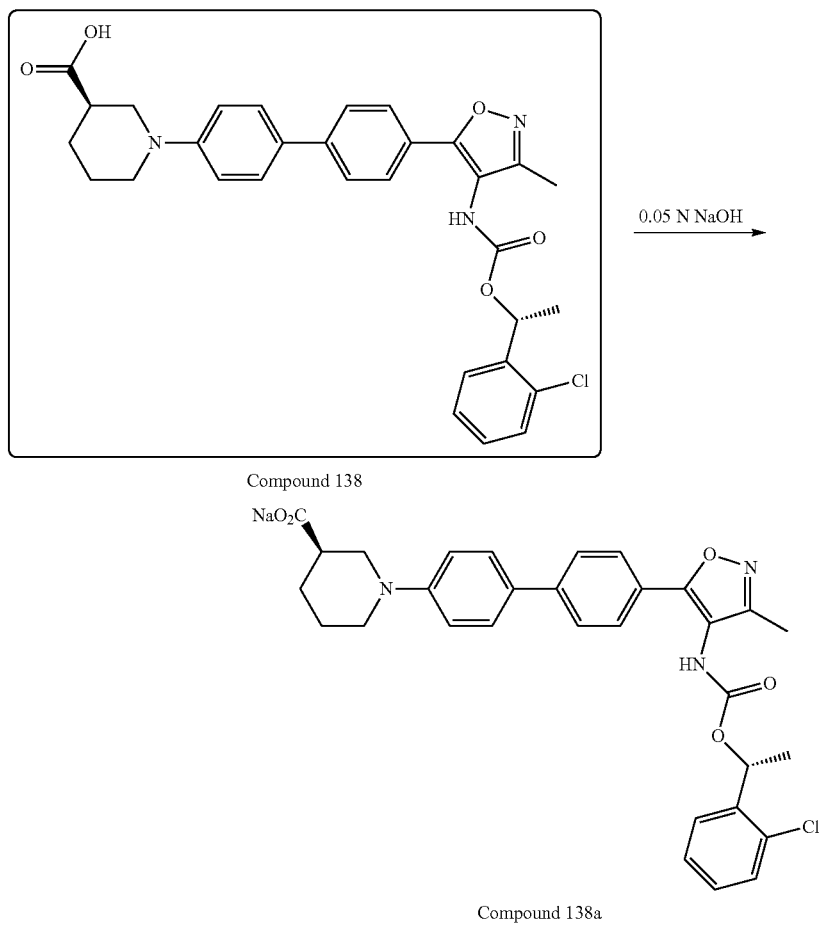

Compound 138

Compound 138a

Compound 138 was prepared analogously to the procedure described in the synthesis of Compound 136 (120 mg, yield 56%). $^1$H NMR (DMSO-d$_6$, 400 MHz): δ 7.81-7.88 (m, 2H), 7.59-7.74 (m, 5H), 7.31-7.44 (m, 5H), 6.19 (m, 1H), 3.80-3.83 (m, 1H), 3.59-3.62 (m, 1H), 3.08-3.14 (m, 1H), 2.90-2.96 (m, 1H), 2.67-2.72 (m, 1H), 2.26 (s, 3H), 2.04-2.09 (m, 1H), 1.84-1.89 (m, 1H), 1.71-1.78 (m, 2H), 1.63 (d, J=6.4 Hz, 3H). MS (ESI) m/z (M+H)$^+$ 560.2.

Compound 138a was prepared analogously to the procedure described in the synthesis of Compound 132a. $^1$H NMR (DMSO-d$_6$, 400 MHz): δ 9.60 (br, 1H), 7.71-7.78 (m, 4H), 7.59-7.65 (m, 3H), 6.99-7.52 (m, 5H), 6.01 (q, J=6.4 Hz, 1H), 3.84-3.87 (m, 1H), 3.69-3.72 (m, 1H), 2.69-2.79 (m, 2H), 2.07-2.20 (m, 4H), 1.92-1.95 (m, 1H), 1.67-1.70 (m, 1H), 1.57 (d, J=6.4 Hz, 3H), 1.38-1.58 (m, 2H). MS (ESI) m/z (M+H)$^+$ 560.0.

Synthesis of Compound 139
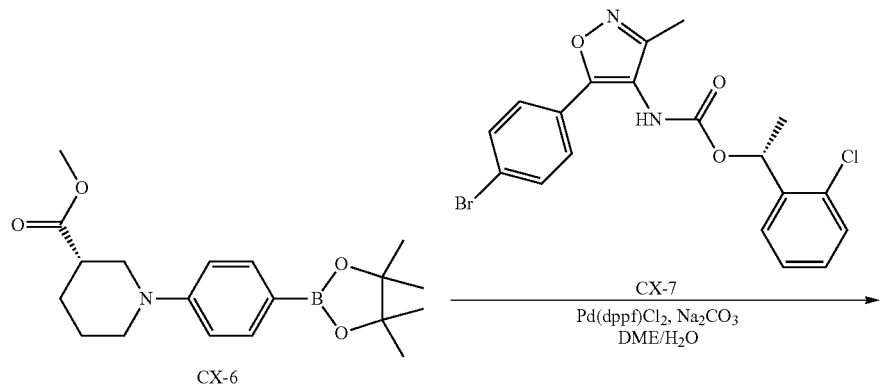
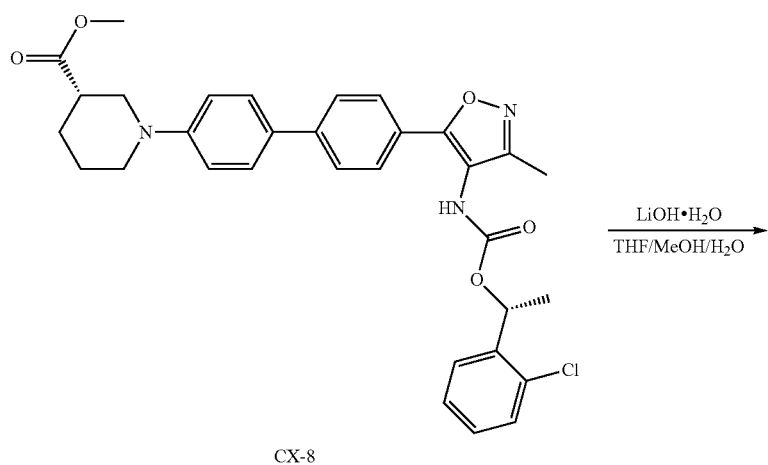
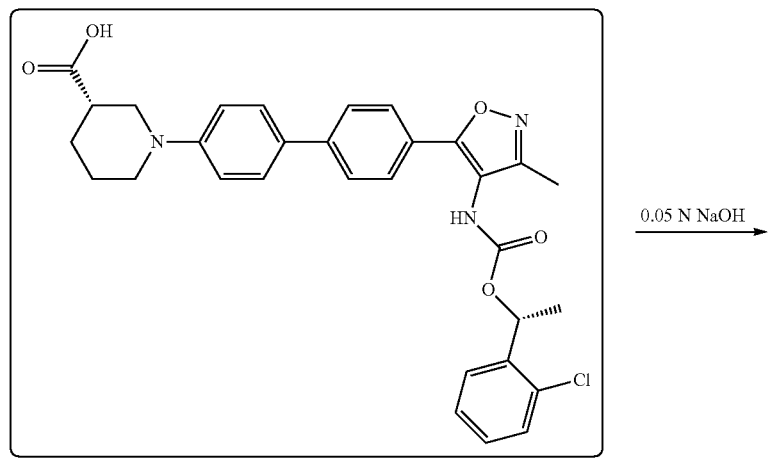
Compound 139

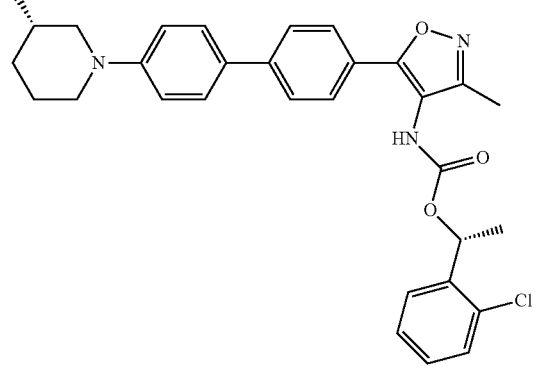
Compound 139a
Compound 139 was prepared analogously to the procedure described in the synthesis of Compound 137. MS (ESI) m/z (M+H)+ 560.1.
Compound 139a was prepared analogously to the procedure described in the synthesis of Compound 132a. $^1$H NMR (DMSO-$d_6$, 400 MHz): δ 7.80 (d, J=8.4 Hz, 2H), 7.55-7.63 (m, 5H), 7.31-7.37 (m, 3H), 6.99 (d, J=8.4 Hz, 2H), 5.97 (q, J=6.4 Hz, 1H), 3.84-3.86 (m, 1H), 3.67-3.70 (m, 1H), 2.65-2.79 (m, 2H), 2.09-2.10 (m, 4H), 1.93-1.96 (m, 1H), 1.67-1.71 (m, 1H), 1.36-1.49 (m, 5H). MS (ESI) m/z (M+H)+ 560.3.
Synthesis of Compound 140
Synthetic Route (Scheme CXI)
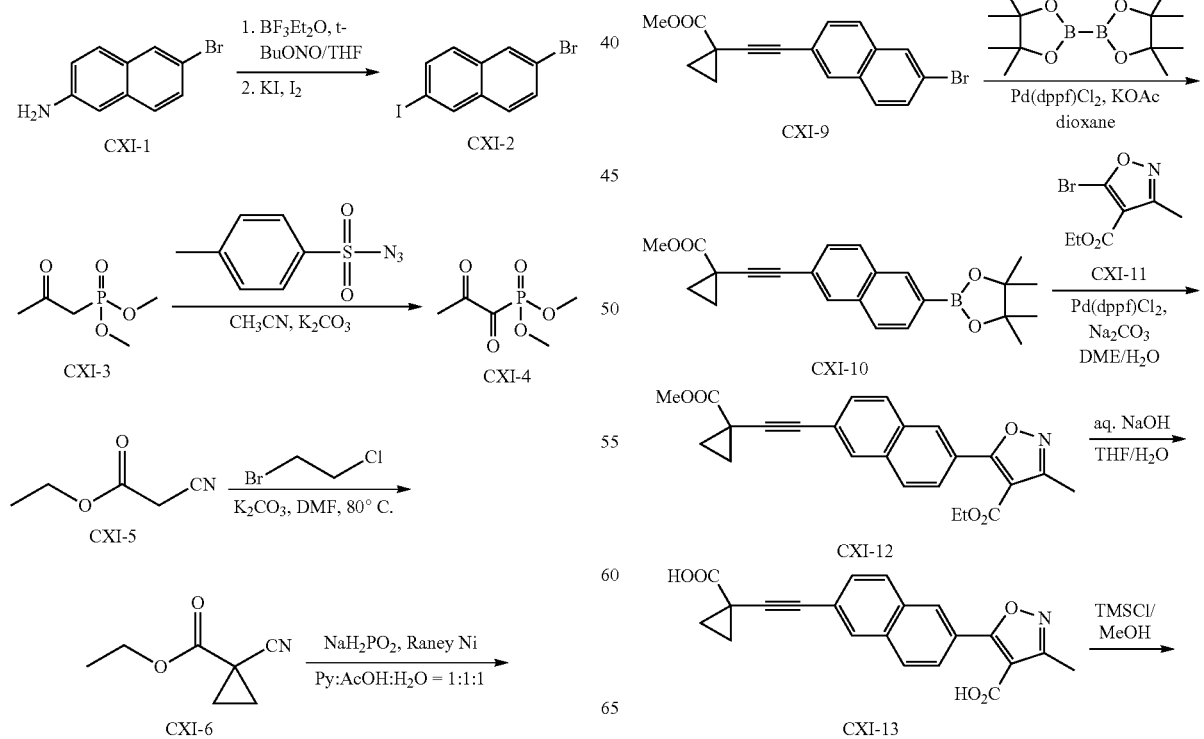

-continued

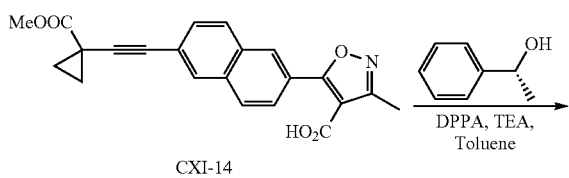

CXI-14

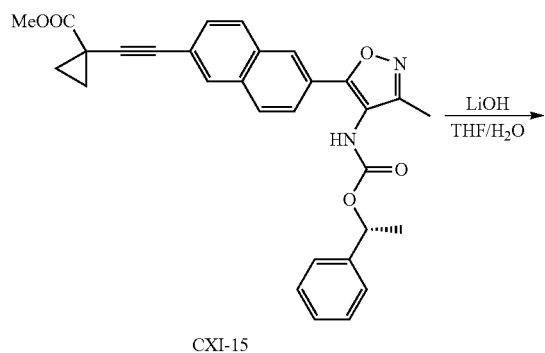

CXI-15

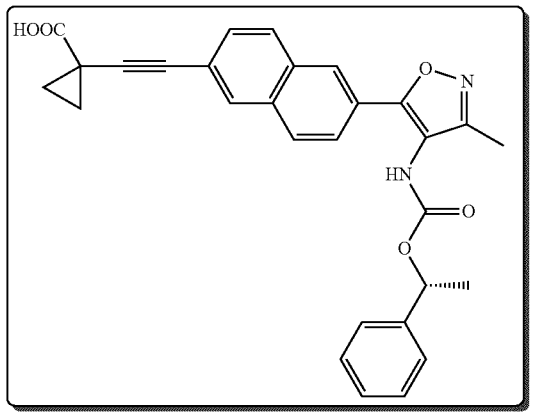

Compound 140

To a 500 mL round bottom containing a stir bar was added borontrifluoride diethyletherate (14.5 mL, 115 mmol) and the flask was cooled to −30° C. Compound CXI-1 (6.0 g, 27.3 mmol) dissolved in THF (75 mL) was added dropwise. 90% tert-butylnitrite (12 mL, 100 mmol) was dissolved in THF (75 mL) and added dropwise. The reaction was allowed to warm to −5° C. at which time 100 mL of diethyl ether was added and the mixture was allowed to stir at −5° C. for 10 min until a pale solid precipitated. The solid was filtered and washed with ether to afford a pale solid which was then added in one portion to a 500 mL round bottom containing a stir bar, potassium iodide (6.4 g, 38.7 mmol), iodine (4.92 g, 19.4 mmol), and acetonitrile (100 mL). The reaction was allowed to stir at room temperature for 15 mins. 150 mL of a saturated aqueous solution of sodium thiosulfate was added as well as 150 mL of DCM. The mixture was allowed to stir for 5 mins, the layers were separated, the organics were dried using anhydrous $MgSO_4$, and the solvent was removed in vacuo. The residue was purified by column (PE) to give compound CXI-2 (4.6 g, yield 51.1%).

To a solution of $TsN_3$ (10.4 g, 0.528 mmol) in dry $CH_3CN$ (100 mL) was added compound CXI-3 (8.77 g, 52.8 mmol) and $K_2CO_3$ (14.6 g, 106 mmol). The reaction was stirred at room temperature for 2 hours. Then filtered, the filtrated was used to next step directly.

To a stirred mixture of compound CXI-5 (30 g, 0.265 mol), 1-bromo-2-chloroethane (75 g, 0.528 mol) in DMF (200 mL) was added $K_2CO_3$ (110 g, 0.8 mol). The reaction mixture was heated to 80° C. overnight. The mixture was diluted with ice water, extracted with hexane, washed with water and brine, dried over $Na_2SO_4$, filtered and concentrated. The residue was main compound CXI-6 (22 g, yield 59.6%) and used directly.

To a stirred mixture of 70 mL of pyridine/acetic acid/water (1/1/1) was added compound CXI-6 (crude from above procedure) and $NaH_2PO_2$ (10 eq.) at 0° C. The reaction mixture was flushed with $N_2$ and to it was added Raney Ni (5 g). The reaction was stirred at room temperature for 1 h. The mixture was diluted with ice-water, extracted with hexane, washed with water and brine, dried over $Na_2SO_4$, filtered and concentrated. The residue was main compound CXI-7 and used directly.

To a solution of compound CXI-4 (crude, obtained from last step) was added compound CXI-7 (crude, obtained from above procedure) and 200 mL of methanol at 0° C. Then the reaction was stirred at room temperature for 2 hours. The mixture was diluted with ice-water, extracted with hexane, washed with water and brine, dried over $Na_2SO_4$, filtered and concentrated. The crude compound CXI-8 was used to next step directly.

To a stirred mixture of compound CXI-2 (100 mg, 0.301 mmol), crude compound CXI-8 (41.6 mg, 0.301 mmol) and CuI (19 mg, 0.100 mmol) in DMF (5 mL) and TEA (1 mL) was added $Pd(PPh_3)_2Cl_2$ (21 mg, 0.030 mmol). The reaction mixture was flushed with $N_2$ and stirred at room temperature overnight. The mixture was diluted with EtOAc (15 mL), washed with water (10 mL) and brine (10 mL), dried over $Na_2SO_4$, filtered and concentrated. The residue was purified by Prep-TLC (PE:EA=10:1) to give compound CXI-9 (50 mg, yield 50%).

To a stirred mixture of compound CXI-9 (107 mg, 0.31 mmol), compound CXI-9A (159 mg, 0.62 mmol) and KOAc (63 mg, 0.63 mmol) in 1,4-dioxane (5 mL) was added Pd(dppf)$Cl_2$ (11 mg, 0.015 mmol). The reaction mixture was flushed with $N_2$ and stirred at reflux overnight. The mixture was diluted with EtOAc (20 mL), washed with water (10 mL) and brine (10 mL), dried over $Na_2SO_4$, filtered and concentrated. The residue was purified by Prep-TLC (PE:EA=10:1) to give compound CXI-10 (97 mg, yield 82.2%).

To a stirred mixture of compound CXI-10 (122 mg, 0.324 mmol), compound CXI-11 (90 mg, 0.386 mmol) and $Na_2CO_3$ (103 mg, 0.972 mmol) in dimethoxyethane (3 mL) and $H_2O$ (1 mL) was added Pd(dppf)$Cl_2$ (12 mg, 0.016 mmol). The reaction mixture was flushed with $N_2$ and stirred at 80° C. overnight. The mixture was diluted with EtOAc (20 mL), washed with water (10 mL) and brine (10 mL), dried over $Na_2SO_4$, filtered and concentrated. The residue was purified by Prep-TLC (PE:EA=5:1) to give compound CXI-12 (97 mg, yield 82.2%). MS (ESI) m/z (M+H)$^+$ 404.2.

To a solution of compound CXI-12 (130 mg, 0.322 mmol) in THF (18 mL) was added water (6 mL) and sodium hydroxide (64.7 mg, 1.61 mmol). The reaction was stirred at room temperature overnight. The mixture was diluted with water, neutralized to pH=4.0 with 1N hydrochloride solution, extracted with EtOAc (20 mL). The combined organic phase was dried over $MgSO_4$ and concentrated to afford compound CXI-13 (50 mg, crude yield 43.1%), which was used to next step directly.

To a solution of compound CXI-13 (50 mg, 0.138 mmol) in MeOH (20 mL) was added TMSCl (15 mg, 0.138 mmol) at 0° C. The reaction mixture was stirred at room temperature for 2 days. The mixture was diluted with water, and extracted with EtOAc (20 mL). The combined organic phase was dried over MgSO₄ and concentrated. The residue was purified by TLC (PE:EA=1:1) to give compound CXI-14 (30 mg, yield 57.7%). MS (ESI) m/z (M+H)⁺ 376.0.

To a solution of compound CXI-14 (30 mg, 0.068 mmol) in dry toluene (3 mL) was added (R)-phenyl ethanol (1.15 mg, 0.096 mmol), triethylamine (15.9 mg, 0.158 mmol) and DPPA (26.1 mg, 0.095 mmol). The reaction mixture was stirred at 80° C. overnight. The mixture was diluted with EtOAc (20 mL), washed with brine, dried over MgSO₄ and concentrated. The residue was purified by Prep-TLC (PE:EA=3:1) to give compound CXI-15 (30 mg, yield 75.4%). MS (ESI) m/z (M+H)⁺ 495.2.

Preparation of Compound 140

To a solution of compound CXI-15 (20 mg, 0.04 mmol) in THF (4.5 mL) was added water (1.5 mL) and lithium monohydrate (6.4 mg, 0.20 mmol). The reaction mixture was stirred at room temperature for overnight. The mixture was neutralized to pH=4.0 with 1N hydrochloride solution, extracted with EtOAc (20 mL). The combined organic phase was dried over MgSO₄ and concentrated. The residue was purified by prep-HPLC to give Compound 140 (3.9 mg, yield 19.5%). ¹HNMR (Methanol-d₄ 400 MHz) δ 8.22 (s, 1H), 7.96 (s, 1H), 7.84-7.88 (m, 2H), 7.73 (d, J=8.0 Hz, 2H), 7.02-7.52 (m, 6H), 5.83-5.85 (m, 1H), 2.21 (s, 3H), 1.64-1.62 (m, 5H), 1.44-1.46 (m, 2H). MS (ESI) m/z (M+H)⁺481.1.

Synthesis of Compound 141

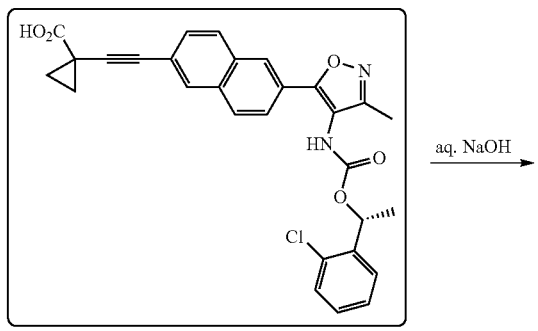

Compound 141

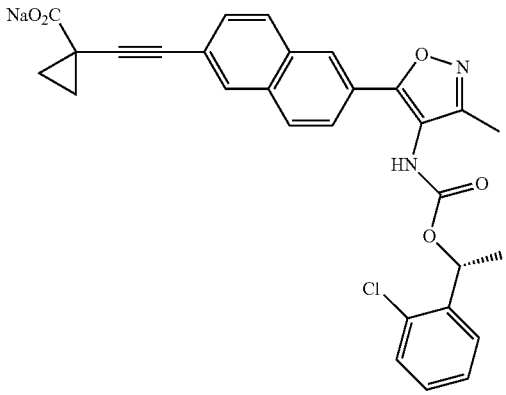

Compound 141a

Compound 141 was prepared analogously to the procedure described in the synthesis of Compound 140. MS (ESI) m/z (M+H)⁺ 515.2.

Compound 141a was prepared analogously to the procedure described in the synthesis of Compound 87a. ¹H NMR (DMSO-d₆ 400 MHz) δ 9.15 (s, 1H), 8.27 (s, 1H), 7.93-7.96 (m, 2H), 7.81-7.86 (m, 2H), 7.33-7.49 (m, 5H), 6.04 (q, 1 H), 2.18 (s, 3H), 1.52 (br, 3H), 1.26-1.29 (m, 2 H), 0.93-0.96 (m, 2 H). MS (ESI) m/z (M+H)⁺ 515.2.

Synthesis of Compound 142

Synthetic Route (Scheme CXII)

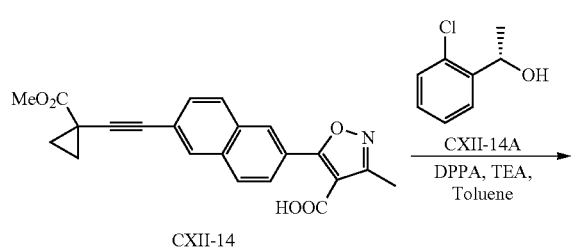

CXII-14

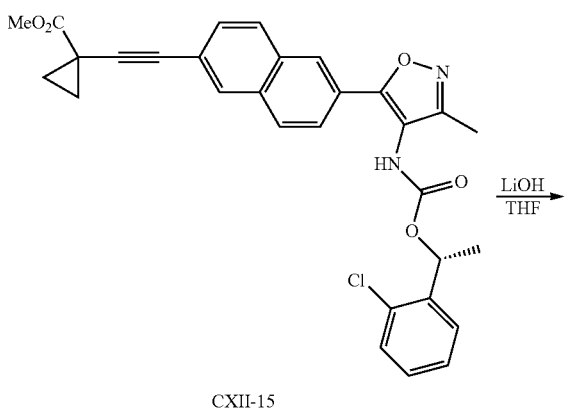

CXII-15

Synthetic Route (Scheme CXIII)

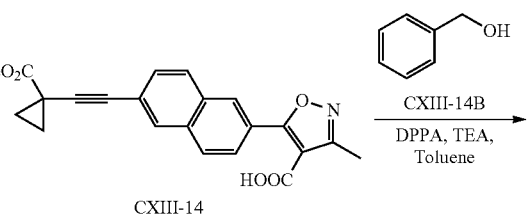

CXIII-14

941
-continued
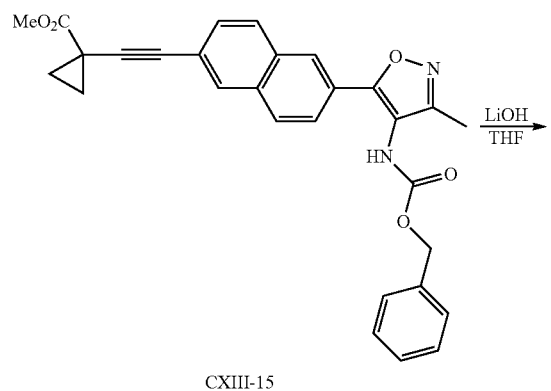
CXIII-15
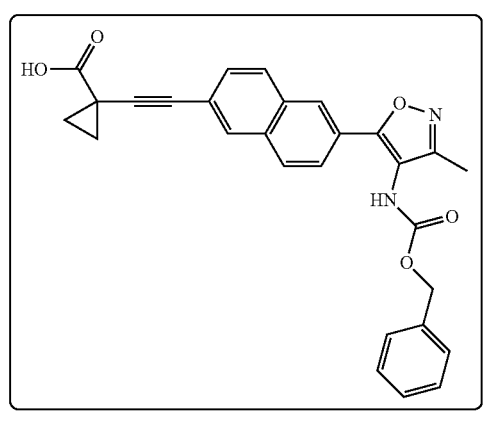
Compound 142
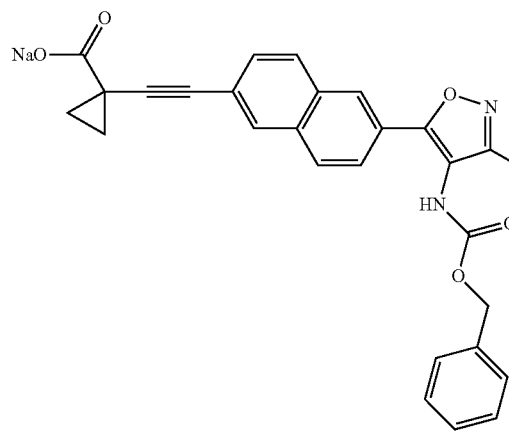
Compound 142a
Compound 142 was prepared analogously to the procedure described in the synthesis of Compound 140. MS (ESI) m/z (M+H)+ 467.1.
Compound 142a was prepared analogously to the procedure described in the synthesis of Compound 87a. $^1$H NMR (DMSO-d$_6$ 400 MHz) δ 8.28 (s, 1H), 7.93-7.97 (m, 2H), 7.80-7.88 (m, 2H), 7.47 (d, J=8.4 Hz, 1H), 7.33-7.45 (m, 5H), 5.17 (s, 2 H), 2.19 (s, 3H), 1.26-1.27 (m, 2 H), 0.91-0.92 (m, 2 H). MS (ESI) m/z (M+H)+ 467.1.
942
Synthesis of Compound 143
Synthetic Route (Scheme CXIV)
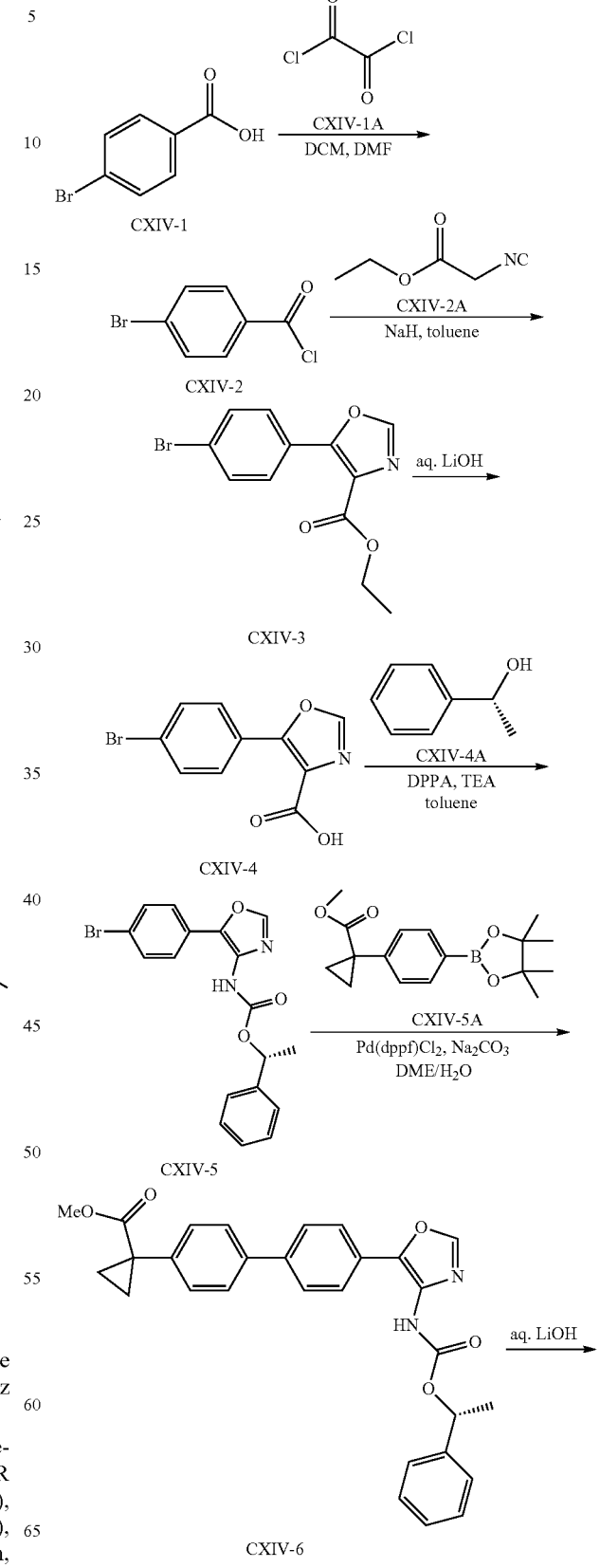

-continued

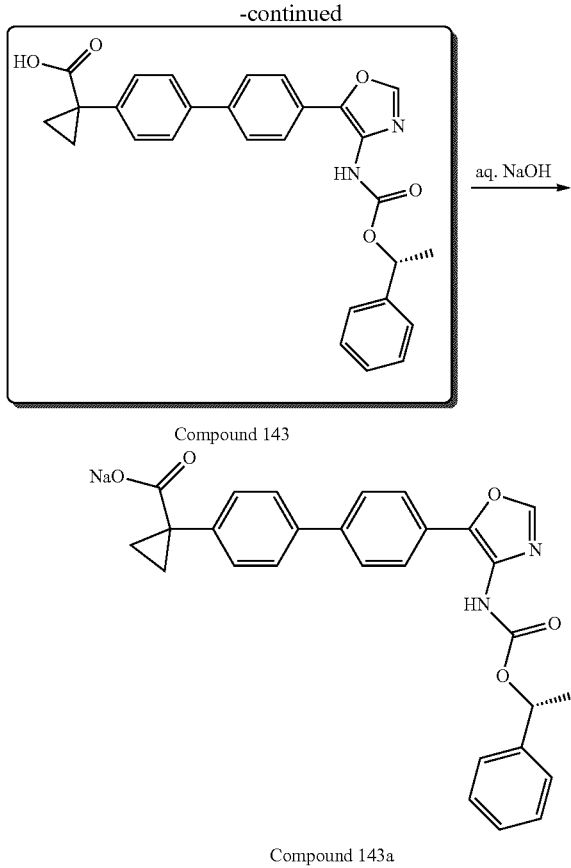

Compound 143

Compound 143a

To a solution of compound CXIV-1 (5 g, 24.8 mmol) in toluene (50 mL) was added compound CXIV-1A (16 g, 124 mmol) followed by addition of DMF (0.1 mL). The reaction was stirred at room temperature for 3 hours. After concentrated, the crude compound CXIV-2 (crude 5 g) was used for the next step without further purification.

NaH (0.55 g, 22.6 mmol) was added to a mixture of the compound CXIV-2A (2.3 g, 20.35 mmol) in 30 mL toluene. After stirred for 2 hours at r.t, a solution of compound CXIV-2 (5 g, 23 mmol) in 20 mL of toluene was added. The reaction mixture was stirred overnight at r.t. After quenched with $H_2O$, the mixture was filtered, the filtrate was concentrated. The residue was purified by column chromatography on silica gel (petroleum ether:EtOAc=5:1) to afford compound CXIV-3 (1.8 g, yield 30%). MS (ESI) m/z (M+H)$^+$ 296.1.

To a stirred solution of compound CXIV-3 (1.00 g, 3.38 mmol) in MeOH:$H_2O$=5:1 (20 mL) was added LiOH (276 mg, 6.57 mmol). After the addition, the solution was stirred overnight at 60° C. The solution was concentrated in vacuo and the aqueous layer was extracted by ether (30 mL×3) and acidified, the product was extracted by EA to afford compound CXIV-4 (0.98 g, yield 95%).

To a stirred solution of compound CXIV-4 (918 mg, 3.42 mmol), compound CXIV-4A (502 mg, 4.11 mmol) and DPPA (1.13 g, 4.11 mmol) in toluene (15 mL) was added TEA (692 mg, 6.85 mmol) at room temperature under argon. After the addition, the solution was stirred for 1 hour at 100° C., The solution was quenched with water, and extracted with EtOAc, the organic layer was separated, dried, and purified by Pre-HPLC to afford compound CXIV-5 (1 g, yield 69.4%). MS (ESI) m/z (M+1)$^+$ 388.2.

To a solution of compound CXIV-5 (1.0 g, 2.58 mmol) in DME:$H_2O$=3:1 (20 mL), $Na_2CO_3$ (548 mg, 5.16 mmol) and compound CXIV-5A (780 mg, 2.58 mmol) were added Pd(dppf)Cl$_2$ (94 mg, 0.13 mmol), the resulting mixture was purged with nitrogen. Then the reaction mixture was stirred at 80° C. overnight under nitrogen protection. TLC monitored the reaction, the mixture was poured into water, extract with EtOAc (30 mL×3), the combined organic layers were dried over $Na_2SO_4$, concentrated in vacuo. The residue was purified by chromatography (PE:EA=4:1) to afford compound CXIV-6 (0.35 g, yield 28%). MS (ESI) m/z (M+1)$^+$483.1.

Preparation of Compound 143

To a stirred solution of CXIV-6 (350 mg, 0.73 mmol) in MeOH:$H_2O$=5:1 (12 mL) was added LiOH (38 mg, 0.90 mmol). After the addition, the solution was stirred overnight at r.t. The solution was concentrated in vacuo and the aqueous layer was acidified with 1N HCl, and then extracted by EtOAc (50 mL), the organic layer was separated, dried and concentrated to afford Compound 143 (93.4 mg, yield 27.3%). MS (ESI) m/z (M+H)$^+$ 469.1.

Preparation of Compound 143a

To a stirred solution of Compound 143 (93.4 mg, 0.2 mmol) in MeOH (3 mL) was added 0.05N NaOH (7.9 mg, 0.2 mmol). After the addition, the solution was stirred for 30 min. at 0° C., and then lyophilized to afford Compound 143a. $^1$HNMR (400 MHz, DMSO-d$_6$) δ 9.56 (s, 1H), 8.39 (s, 1 H), 7.62-7.73 (m, 6 H), 7.38-7.44 (m, 7 H), 5.76 (q, 1 H), 1.48-1.48 (br, 5 H), 1.19-1.18 (br, 2 H). MS (ESI) m/z (M+H)$^+$ 469.2.

Synthesis of Compound 144

Synthetic Route (Scheme CXV)

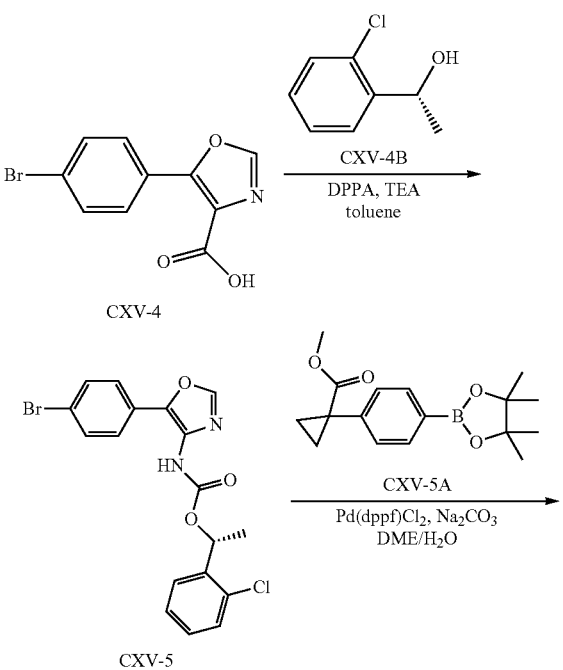

945
-continued

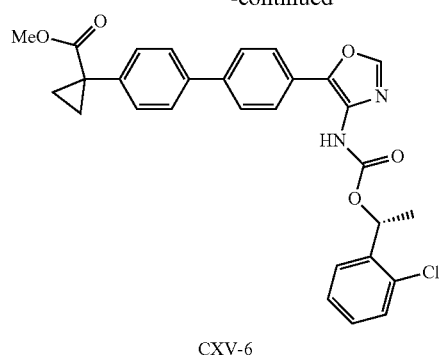

CXV-6

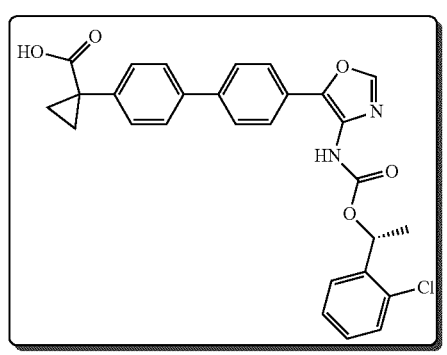

Compound 144

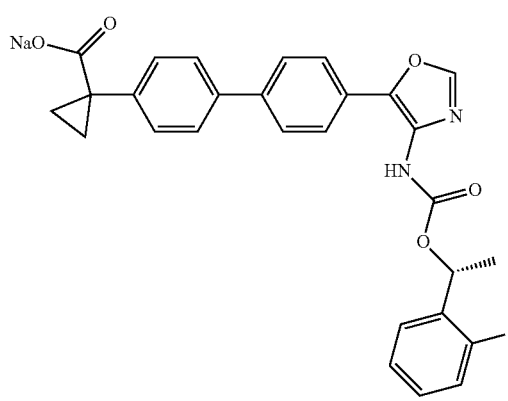

Compound 144a

Compound 144 was prepared analogously to the procedure described in the synthesis of Compound 143. $^1$H NMR (400 MHz, DMSO-$d_6$): δ 9.67 (s, 1 H), 8.41 (s, 1 H), 7.74-7.62 (m, 7 H), 7.45-7.42 (m, 5 H), 6.01 (q, 1 H), 1.50-1.47 (m, 5 H), 1.19-1.18 (m, 2 H). MS (ESI) m/z (M+H)$^+$ 503.3. Compound 144a was prepared analogously to the procedure described in the synthesis of Compound 143a. $^1$H NMR: (400 MHz, DMSO-$d_6$): δ 9.67 (s, 1 H), 8.38 (s, 1 H), 7.59-7.72 (m, 7 H), 7.34-7.45 (m, 5 H), 6.00 (q, 1 H), 1.47-1.46 (br, 5 H), 1.17-1.16 (br, 2 H). MS (ESI) m/z (M+H)$^+$ 503.3.

946
Synthesis of Compound 145

Synthetic Route (Scheme CXVI)

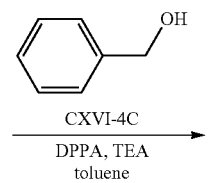

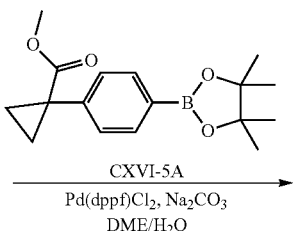

CXVI-4

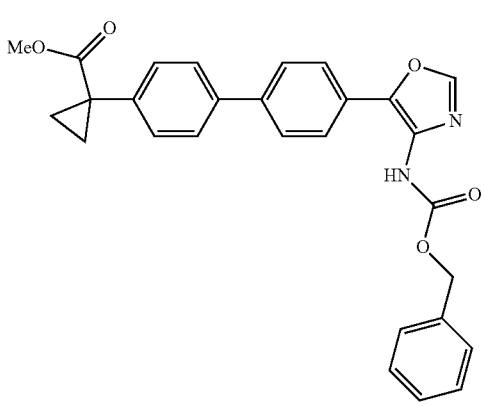

CXVI-5

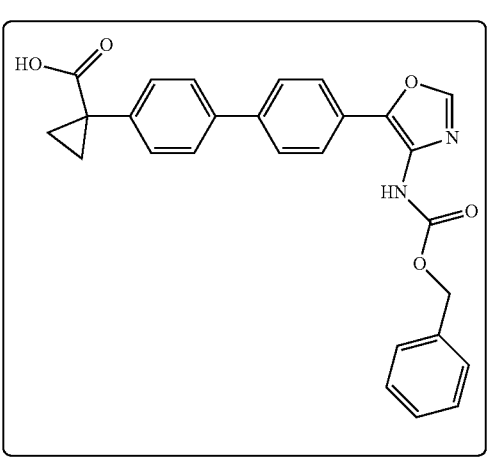

CXVI-6

Compound 145

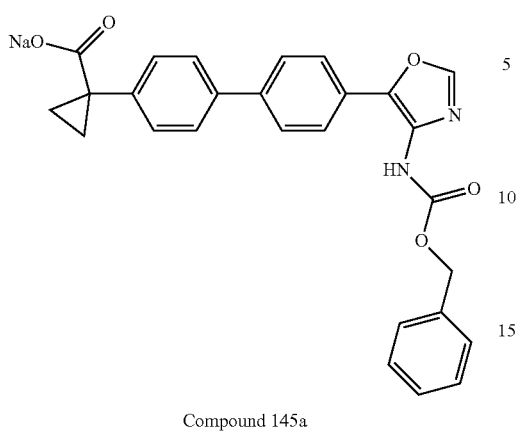

Compound 145a

Compound 145 was prepared analogously to the procedure described in the synthesis of Compound 143. MS (ESI) m/z (M+H)+ 455.2.

Compound 145 prepared analogously to the procedure described in the synthesis of Compound 143a. $^1$H NMR: (400 MHz, DMSO-d$_6$) δ 9.60 (s, 1 H), 8.42 (s, 1 H), 7.73-7.76 (m, 4 H), 7.64 (d, J=8.4 Hz, 4 H), 7.39-7.49 (m, 7 H), 5.14 (s, 2 H), 1.49-1.47 (brs, 2 H), 1.20-1.18 (brs, 2 H). MS (ESI) m/z (M+H)+ 456.2.

Synthesis of Compound 146

Synthetic Route (Scheme CXVII)

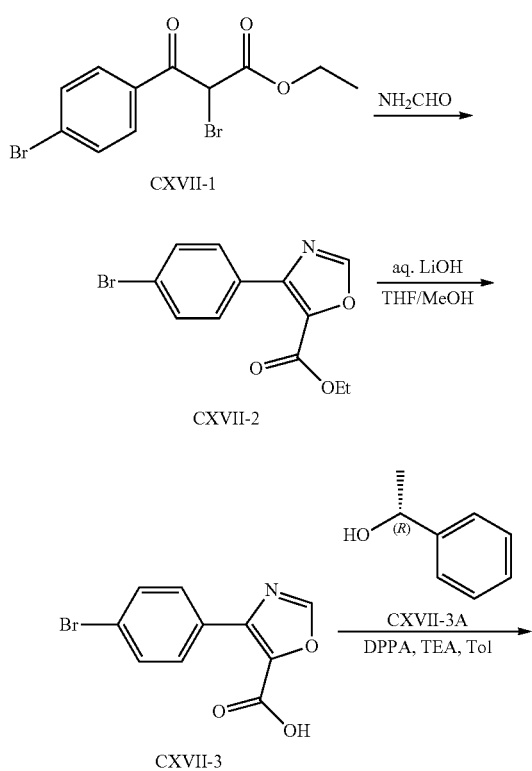

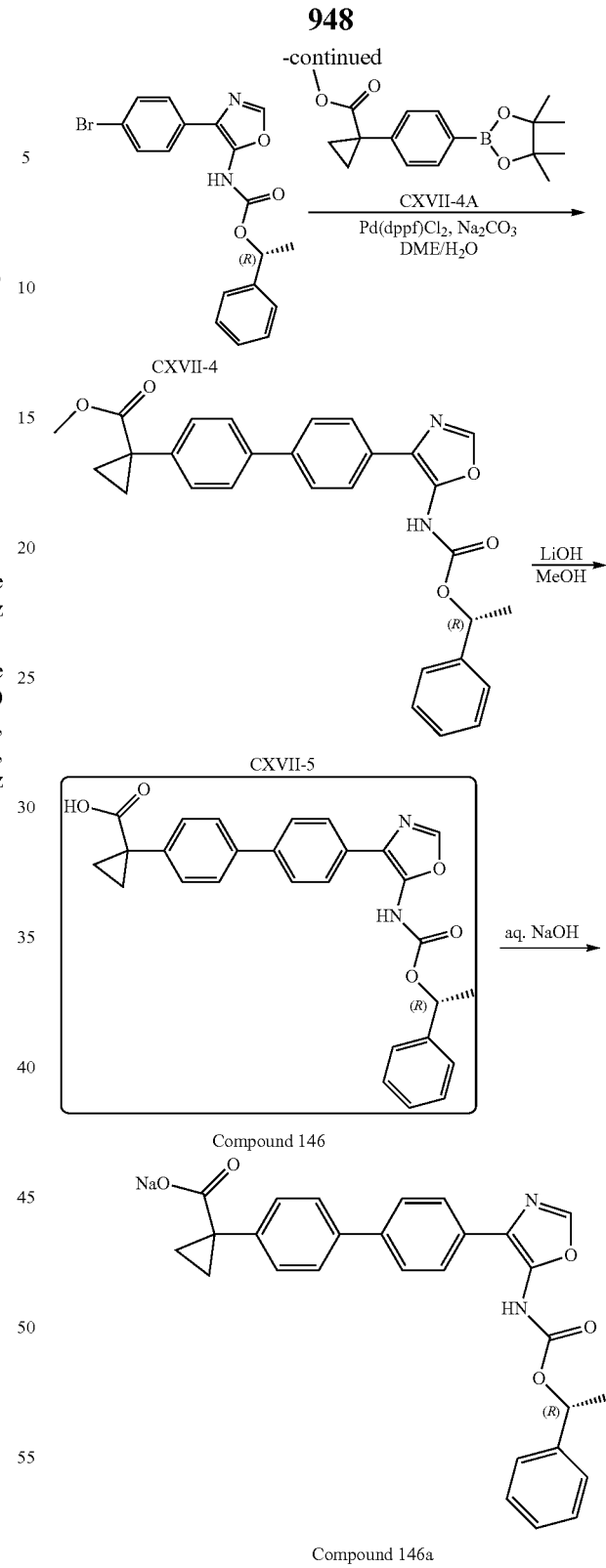

Compound CXVII-1 (1.50 g, 4.286 mmol) was dissolved in formamide (14.4 mL) and stirred for 30 min at 45° C., and then stirred for 1 h at 110° C. The reaction mixture was cooled to room temperature, diluted with water (40 mL), and extracted with ethyl acetate (50 mL×2). The combined organic layer was washed with brine (50 mL), dried over MgSO$_4$, filtered and concentrated under reduced pressure.

The residue was purified by flash silica gel column chromatography (PE/EA=10/1) to afford compound CXVII-2 (292 mg, yield 23.01%).

To a stirred solution of compound CXVII-2 (1.2 g, 4.06 mmol) in 30 mL of MeOH/H$_2$O/THF (v/v/v=1/1/1) was added lithium hydroxide monohydrate (649.6 mg, 16.24 mmol). After the addition, the solution was stirred for 12 hours. The mixture was concentrated in vacuo, and adjusted pH to 2 with HCl (2 N). The aqueous phase was extracted with EtOAc (40 mL×3). The combined organic layer was washed with brine, dried over Na$_2$SO$_4$, and concentrated to afford crude product, which was purified by Prep-HPLC to give compound CXVII-3 (820 mg, yield: 72.3%).

The mixture of compound CXVII-3 (350 mg, 1.32 mmol), compound CXVII-3A (197 mg, 1.57 mmol), DPPA (431 mg, 1.6 mmol) and Et$_3$N (266 mg, 2.64 mmol) in toluene (15 mL) was heated to reflux under nitrogen for 1 hour. The mixture was concentrated, and the residue was partitioned between H$_2$O and DCM, The organic layer was washed with brine, dried over Na$_2$SO$_4$, and concentrated. The residue was purified by column chromatography on silica gel (petroleum ether: EtOAc=1:1) to afford compound CXVII-4 (280 mg, yield 55%). MS (ESI) m/z (M+H)$^+$ 388.9.

Compound 146 was prepared analogously to the procedure described in the synthesis of Compound 143 (80 mg, yield: 85%). $^1$H NMR (DMSO-d$_6$, 400 MHz): δ 10.00 (s, 1H), 8.31 (s, 1H), 7.75 (d, J=8.0 Hz, 2H), 7.67 (d, J=8.4 Hz, 2H), 7.59 (d, J=8.4 Hz, 2H), 7.31-7.41 (m, 7H), 5.75 (q, 1H), 1.44-1.50 (m, 5H), 1.13-1.25 (m, 2H).

Compound 146a was prepared analogously to the procedure described in the synthesis of Compound 143a. $^1$H NMR (DMSO-d$_6$, 400 MHz): δ 8.24 (s, 1H), 7.78 (d, J=8.4 Hz, 2H), 7.63 (d, J=8.4 Hz, 2H), 7.50 (d, J=8.4 Hz, 2H), 7.29-7.36 (m, 7H), 5.77 (q, 1H), 1.49 (d, J=6.4 Hz, 3H), 1.23-1.24 (m, 2H), 0.73-0.75 (m, 2H). MS (ESI) m/z (M+H)$^+$ 469.1.

Synthesis of Compound 147

Synthetic Route (Scheme CXVIII)

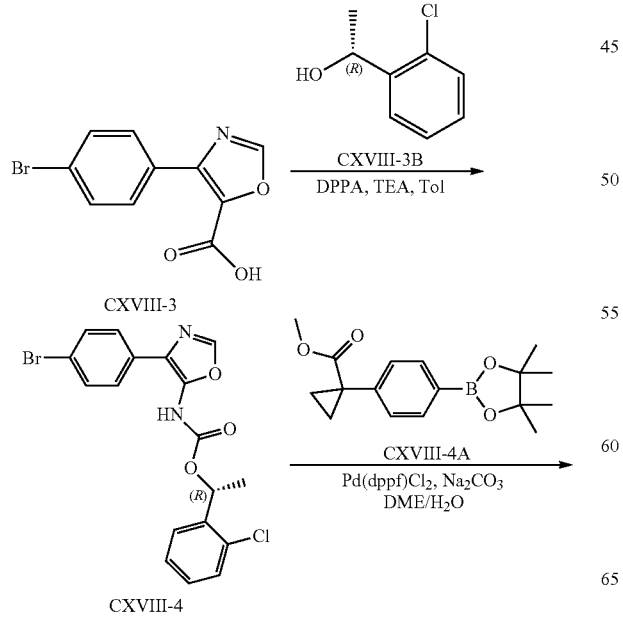

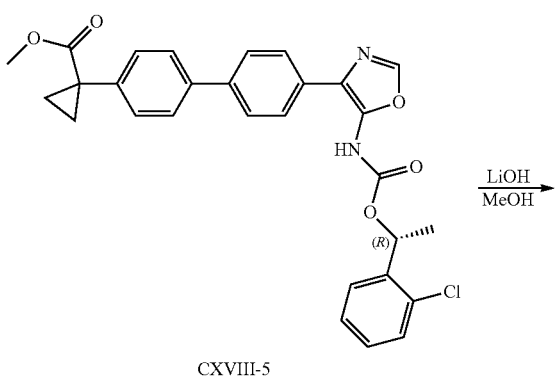

CXVIII-5

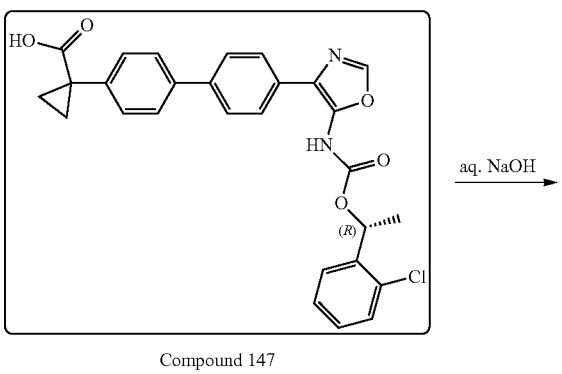

Compound 147

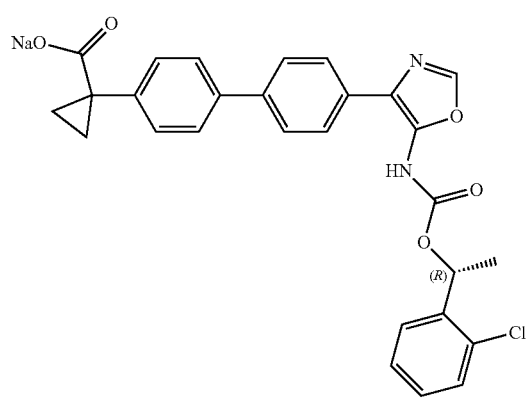

Compound 147a

Compound 147 was prepared analogously to the procedure described in the synthesis of Compound 146. MS (ESI) m/z (M+H)$^+$ 503.0.

Compound 147a was prepared analogously to the procedure described in the synthesis of Compound 143a. $^1$H NMR (DMSO-d$_6$, 400 MHz): δ 8.11 (s, 1 H), 7.79 (d, J=8.4 Hz, 2H), 7.63 (d, J=8.4 Hz, 2H), 7.32-7.51 (m, 8H), 6.01 (q, 1H), 1.48 (d, J=5.2 Hz, 3H), 1.22-1.24 (m, 2H), 0.75-0.76 (m, 2H). MS (ESI) m/z (M+H)+ 503.0.

Synthesis of Compound 148

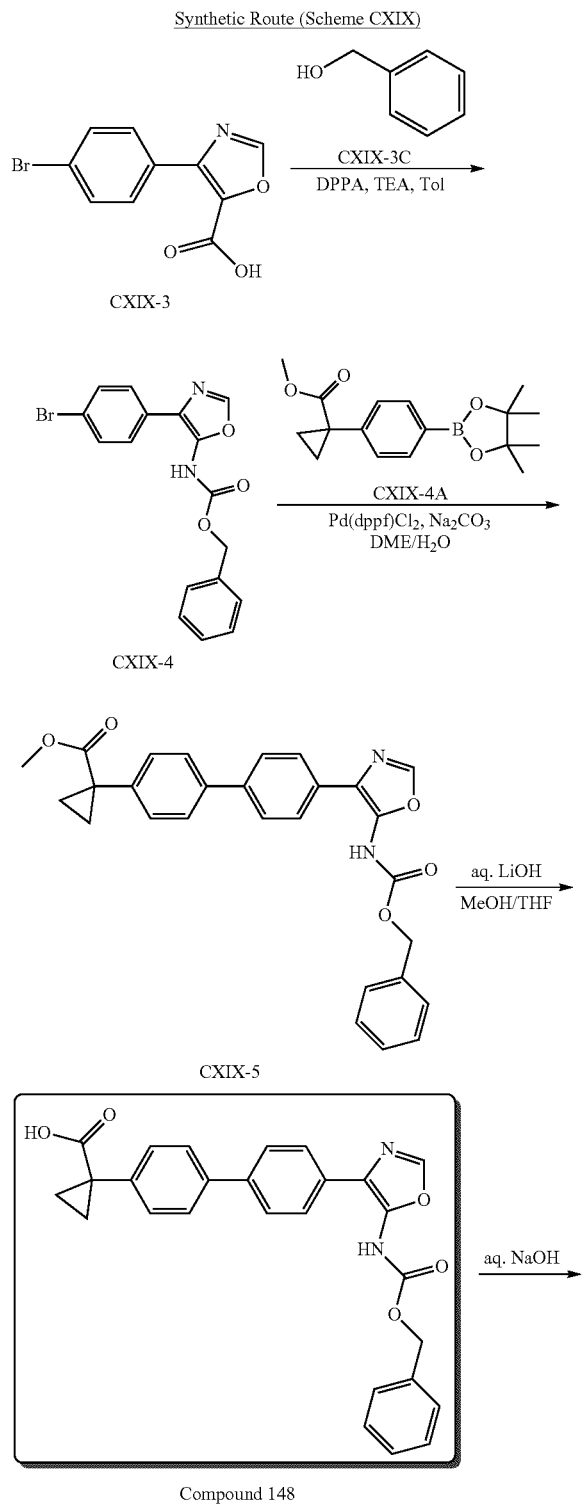

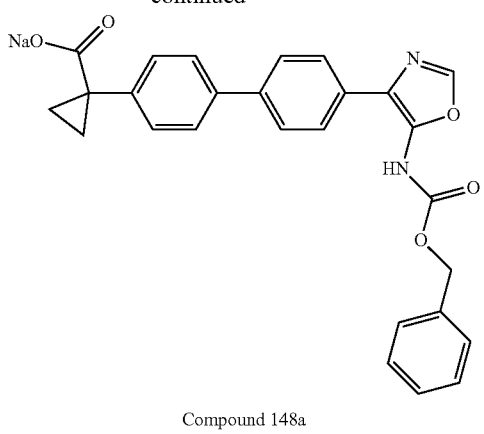

Compound 148a

Compound 148 was prepared analogously to the procedure described in the synthesis of Compound 146. MS (ESI) m/z (M+H)+ 455.2.

Compound 148a was prepared analogously to the procedure described in the synthesis of Compound 143a. $^1$H NMR (Methanol-$d_4$ 400 MHz): δ 8.15 (s, 1H), 7.81 (d, J=8.4 Hz, 2H), 7.66 (d, J=8.4 Hz, 2H), 7.61 (d, J=8.4 Hz, 2H), 7.46 (d, J=8.4 Hz, 2H), 7.38-7.40 (m, 5H), 5.24 (s, 2H), 1.60 (m, 2H), 1.22 (m, 2H). MS (ESI) m/z (M+H)+ 455.2.

Synthesis of Compound 149

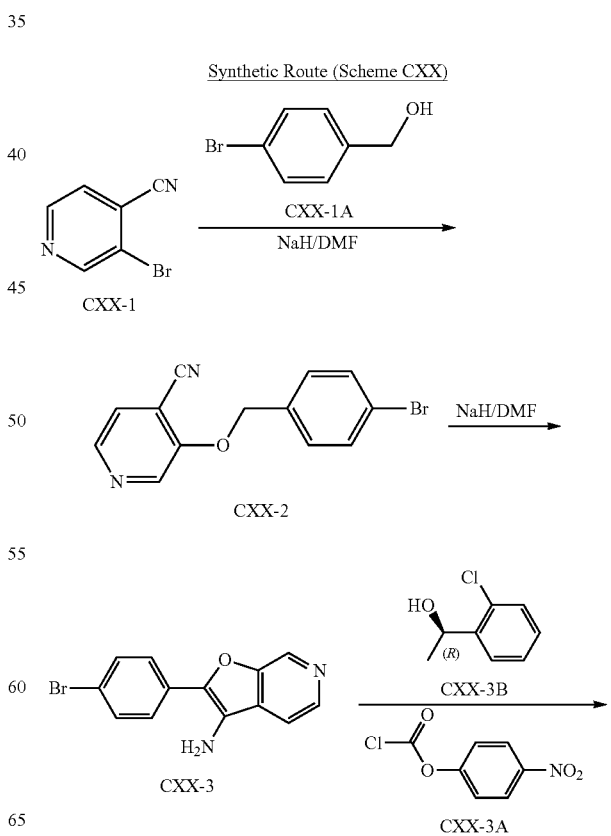

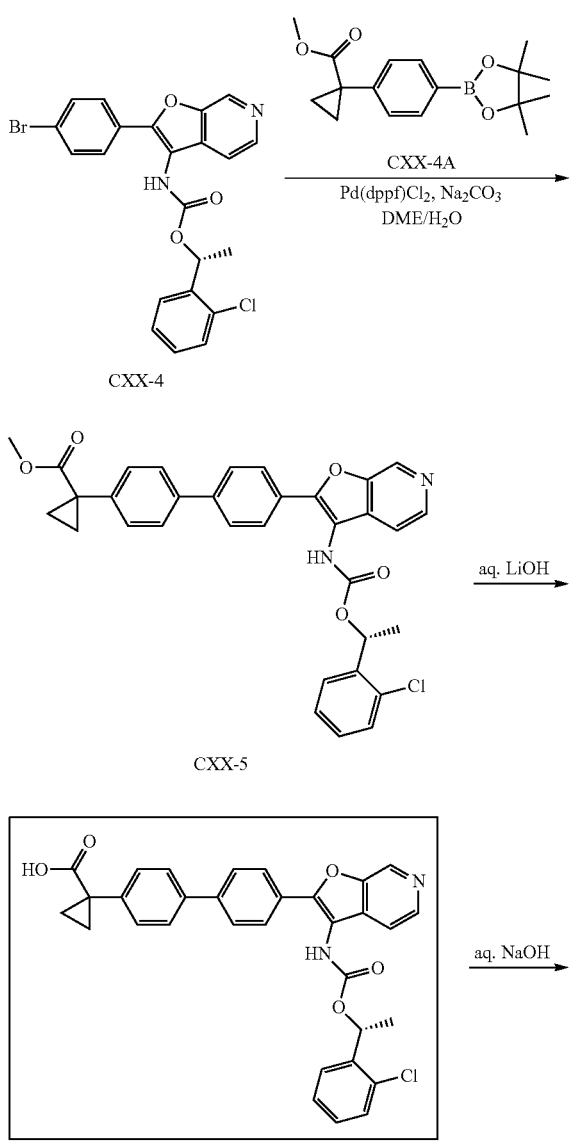

CXX-4

CXX-5

Compound 149

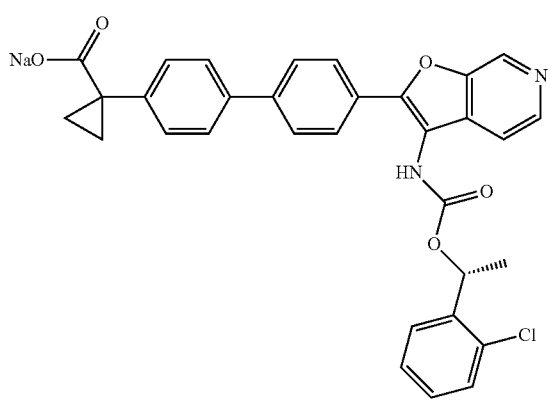

Compound 149a

NaH (768 mg, 19.7 mmol) in DMF (40 mL) was added to a stirred solution of compound CXX-1A (3.38 g, 18.1 mmol) at 0° C. under nitrogen, after stirred for 30 min., compound CXX-1 (3.00 g, 16.4 mmol) in DMF (20 mL) was added. After the addition, the solution was stirred overnight at 60° C. TLC monitored the reaction. Then the mixture was poured into water, extract with DCM (60 mL×3), the combined organic layers were dried over $Na_2SO_4$, concentrated in vacuo. The residue was purified by chromatography (PE:EA=5:1) to afford compound CXX-2 (3.0 g, yield 63.4%). MS (ESI) m/z (M+H)$^+$ 290.

NaH (0.3 g, 12.5 mmol) was added to a stirred solution of compound CXX-2 (1.69 g, 5.8 mmol) in DMF (50 mL) at 0° C. under nitrogen. After the addition, the solution was stirred overnight at 120° C. Then the mixture was poured into water, extract with DCM (60 mL×3), the combined organic layers were dried over $Na_2SO_4$, concentrated in vacuo. The residue was purified by chromatography (PE:EA=1:1) to afford compound CXX-3 (0.9 g, yield 53.2%). MS (ESI) m/z (M+H)$^+$ 290.

To a stirred solution of compound CXX-3 (450 mg, 1.56 mmol) in DCE (10 mL) and Py (303 mg, 3.83 mmol) was added dropwise compound CXX-3A (829 mg, 3.94 mmol) at 0° C. under argon. After the addition, the solution was stirred for 1 hour at room temperature and compound CXX-3B (1.59 g, 10.15 mmol) was added. The reaction mixture was stirred at 80° C. overnight under nitrogen protection. After being cooled to r.t., the mixture was poured into water, extract with EtOAc (30 mL×3), the combined organic layers were dried over $Na_2SO_4$, concentrated in vacuo. The residue was purified by chromatography (PE:EA=3:1) to afford compound CXX-4 (538 mg, yield 73.4%). MS (ESI) m/z (M+1)$^+$ 472.3.

To a solution of compound CXX-4 (538 mg, 1.14 mmol) in DME:$H_2O$=3:1 (20 mL), $Na_2CO_3$ (242 mg, 2.28 mmol) and compound CXX-4A (350 mg, 1.16 mmol) were added Pd(dppf)$Cl_2$ (42 mg, 0.05 mmol) The reaction mixture was stirred at 80° C. overnight under nitrogen protection. After completion of the reaction, the mixture was poured into water, extract with EtOAc (30 mL×3), the combined organic layers were dried over $Na_2SO_4$, concentrated in vacuo. The residue was purified by chromatography (PE:EA=2:1) to afford compound CXX-5 (436 mg, yield 67.6%). MS (ESI) m/z (M+1)$^+$ 568.2.

Preparation of Compound 149

To a stirred solution of CXX-5 (436 mg, 0.77 mmol) in MeOH/$H_2O$ (v/v=5:1, 12 mL) was added LiOH (133 mg, 3.17 mmol). After the addition, the solution was stirred overnight at r.t. The solution was concentrated in vacuo. The mixture was neutralized to pH=4.0 with 1N hydrochloride solution, extracted with EtOAc (20 mL). The combined organic phase was dried over $MgSO_4$ and concentrated. The residue was purified by prep. HPLC to give Compound 149 (105 mg, yield: 24.7%). MS (ESI) m/z (M+H)$^+$ 554.1.

Preparation of Compound 149a

To a stirred solution of Compound 149 (105 mg, 0.19 mmol) in MeOH (3 mL) was added 0.1N NaOH (7.59 mg, 0.11 mmol). After the addition, the solution was stirred for 0.5 h at 0° C. and freeze drying to afford Compound 149a. $^1$H NMR (400 MHz, DMSO-$d_6$) δ 9.95 (s, 1 H), 9.16 (s, 1 H), 8.48 (d, J=5.2 Hz, 1 H), 8.02 (d, J=8.0 Hz, 2H), 7.84 (d, J=8.8 Hz, 2H), 7.64-7.68 (m, 4H), 7.38-7.51 (m, 5H), 6.04 (q, 1H), 1.58 (br, 3 H), 1.47-1.49 (m, 2 H), 1.17-1.19 (m, 2 H). MS (ESI) m/z (M+H)+ 553.1.

Synthesis of Compound 150

Synthetic Route (Scheme CXXI)

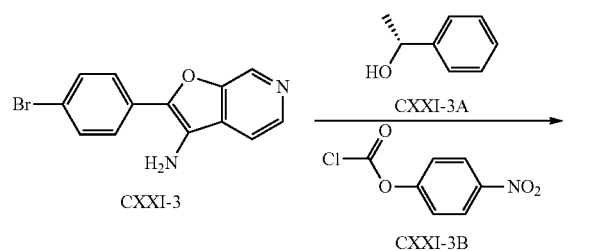

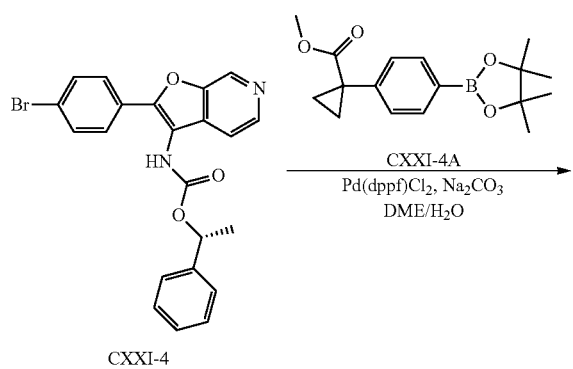

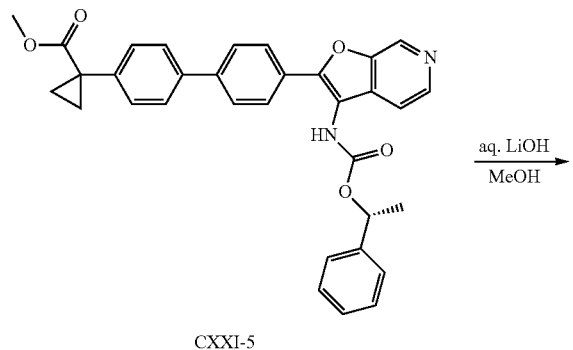

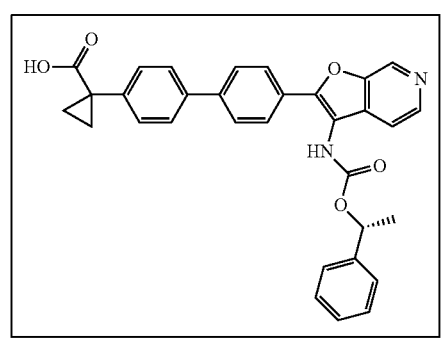

Compound 150

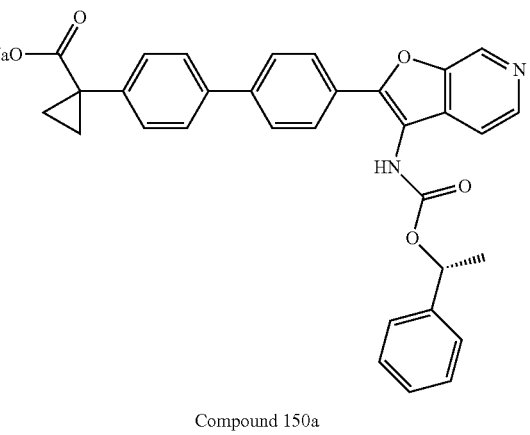

Compound 150a

Compound 150 was prepared analogously to the procedure described in the synthesis of Compound 149. MS (ESI) m/z (M+H)+ 519.3.

Compound 150a was prepared analogously to the procedure described in the synthesis of Compound 149a. $^1$H NMR (400 MHz, DMSO-d$_6$): δ 9.89 (s, 1 H), 9.26 (s, 1 H), 8.52 (s, 1 H), 8.02 (d, J=7.6 Hz, 2 H), 7.86 (d, J=7.6 Hz, 2 H), 7.67-7.69 (m, 3 H), 7.42-7.46 (m, 6 H), 5.81 (q, 1 H), 1.59 (br, 3 H), 1.47-1.49 (m, 2 H), 1.17-1.19 (m, 2 H). MS (ESI) m/z (M+H)+ 519.3.

Synthesis of Compound 151

Synthetic Route (Scheme CXXII)

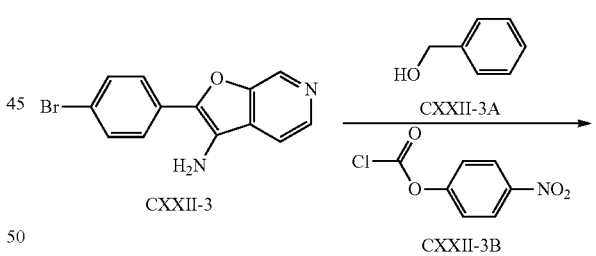

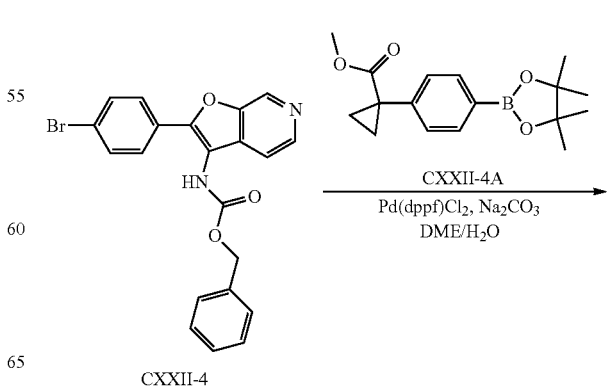

957

-continued

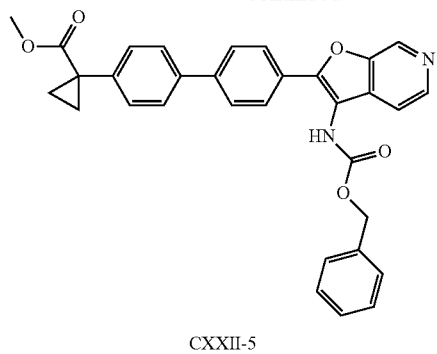

CXXII-5

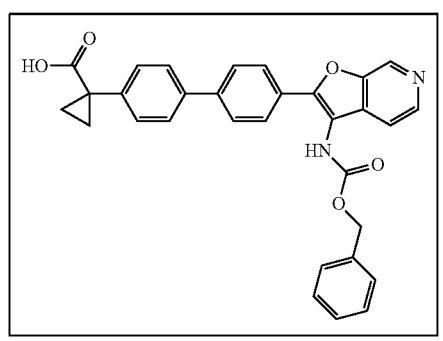

Compound 151

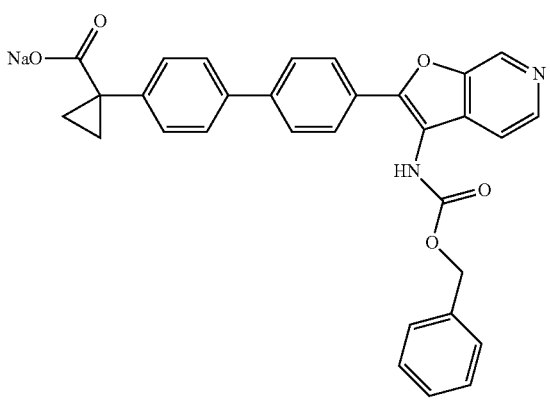

Compound 151a

Compound 151 was prepared analogously to the procedure described in the synthesis of Compound 149. MS (ESI) m/z (M+H)+ 505.2.

Compound 151a was prepared analogously to the procedure described in the synthesis of Compound 149a. $^1$H NMR (400 MHz, DMSO-$d_6$): δ 9.90 (s, 1 H), 9.26 (s, 1 H), 8.52 (d, J=5.2 Hz, 1 H), 8.06 (d, J=8.8 Hz, 2 H), 7.88 (d, J=8.8 Hz, 2 H), 7.81 (d, J=6.0 Hz, 1 H), 7.69 (d, J=8.4 Hz, 2 H), 7.43-7.45 (m, 6 H), 5.21 (s, 2 H), 1.46-1.48 (m, 2 H), 1.16-1.19 (m, 2 H). MS (ESI) m/z (M+H)+ 505.2.

958

Synthesis of Compound 152

Synthetic Route (Scheme CXXIII)

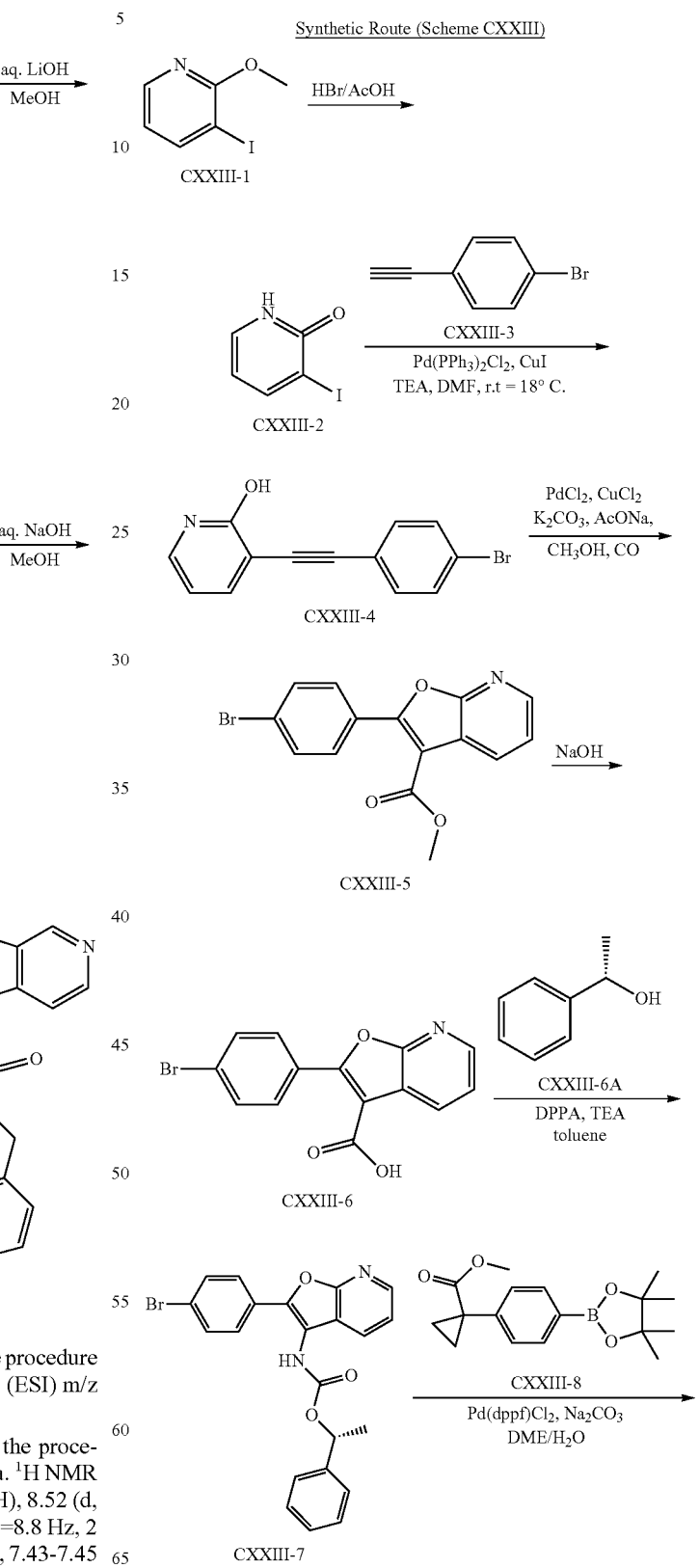

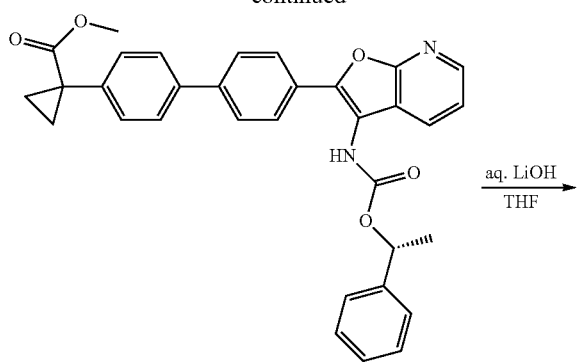

CXXIII-9

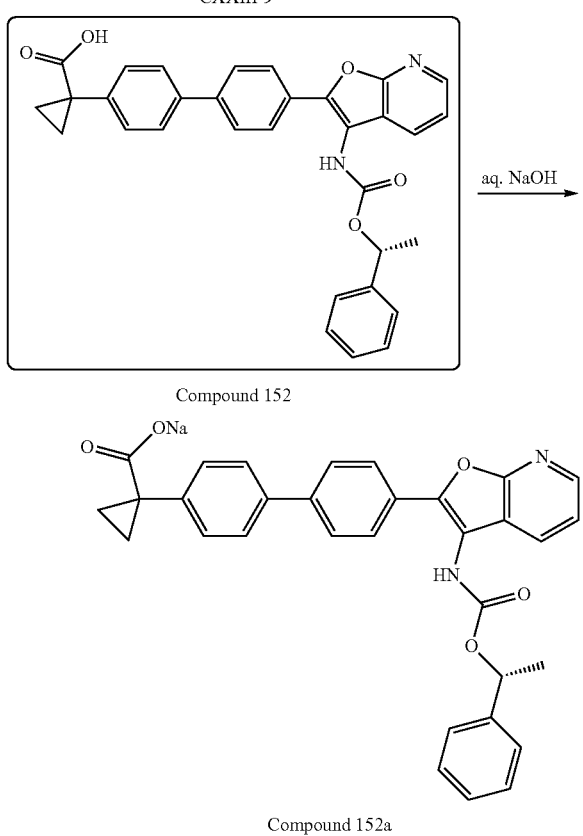

Compound 152

Compound 152a

A solution of compound CXXIII-1 (4.0 g, 16.3 mmol) in HBr/AcOH solution (4 mL) and was heated at 80° C. for 3 hours. After being cooled to r.t., the mixture was extracted with ethyl acetate. The combined organic extracts were dried over anhydrous $MgSO_4$, filtered and concentrated in vacuo. The residue compound CXXIII-2 (3.6 g, crude yield: 96%) was used directly for next step.

A mixture of compound CXXIII-2 (2.3 g, 10 mmol), compound CXXIII-3 (2.2 g, 10 mmol), $Pd(PPh_3)_2Cl_2$ (73.1 mg, 0.1 mmol) and CuI (20.2 mg, 0.1 mmol) in TEA (7 mL) and DMF (20 mL) was stirred at r.t. (18° C.) under argon overnight. After evaporating of the solvent, the residue was diluted with water (50 mL) and extracted with DCM (100 mL). The combined organic extracts were dried over anhydrous $MgSO_4$, filtered and concentrated in vacuo. The residue was purified by column chromatography to yield the desired compound CXXIII-4 (1.6 g, yield: 58%). MS (ESI) m/z $(M+H)^+$ 274.1.

A mixture of compound CXXIII-4 (1 g, 3.6 mmol), sodium acetate (620 mg, 7.2 mmol), potassium carbonate (0.994 g, 7.2 mmol), copper(II) dichloride (1.47 g, 10.8 mmol) and palladium chloride (87 mg, 0.36 mmol) in methanol (80 mL) was vigorously stirred under carbon monoxide atmosphere at 18° C. for 3 hours. After removal of the solvent, the residue was diluted with water and extracted with ethyl acetate. The combined organic layers were dried over $MgSO_4$ and evaporated. The residue was purified by chromatography on silica gel (petroleum ether/ethyl acetate=6/1) to afford compound CXXIII-5 (0.76 g, yield: 64%).

To a solution of compound CXXIII-5 (210 mg, 0.632 mmol) in THF (2 mL), MeOH (2 mL) and $H_2O$ (2 mL) was added sodium hydroxide (126 mg, 3.16 mmol). The reaction mixture was stirred at room temperature for 3 hours. The mixture was concentrated in vacuo to remove solvent. The aqueous phase was diluted with ice-water and neutralized to pH~3 with 3 N hydrochloride solution, and then extracted by EtOAc, dried and concentrated to give crude compound CXXIII-6 (200 mg, yield: 100%). MS (ESI) m/z $(M+H)^+$ 317.8.

Compound 152 was prepared analogously to the procedure described in the synthesis of Compound 149 (135 mg, yield: 58%). MS (ESI) m/z $(M+H)^+$ 519.2.

Compound 152a was prepared analogously to the procedure described in the synthesis of Compound 149a. $^1H$ NMR (DMSO-$d_6$, 400 MHz) δ 9.73 (s, 1H), 7.73 (d, J=6.4 Hz, 1H), 7.95 (d, J=8.4 Hz, 2H), 7.90 (d, J=7.6 Hz, 1H), 7.78 (d, J=8.0 Hz, 2H), 7.56 (d, J=8.4 Hz, 2H), 7.36-7.39 (m, 7H), 5.82 (q, 1 H), 1.60 (brs, 3H), 1.21-1.23 (m, 2 H), 0.71-0.73 (m, 2 H). MS (ESI) m/z $(M+H)^+$ 519.3.

Synthesis of Compound 153

Synthetic Route (Scheme CXXIV)

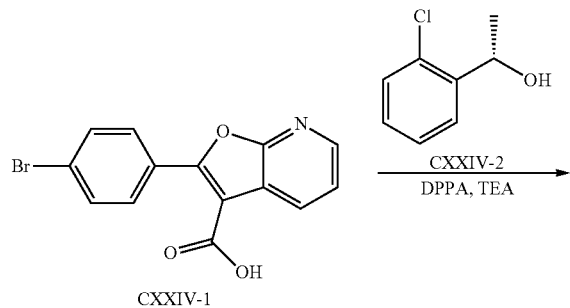

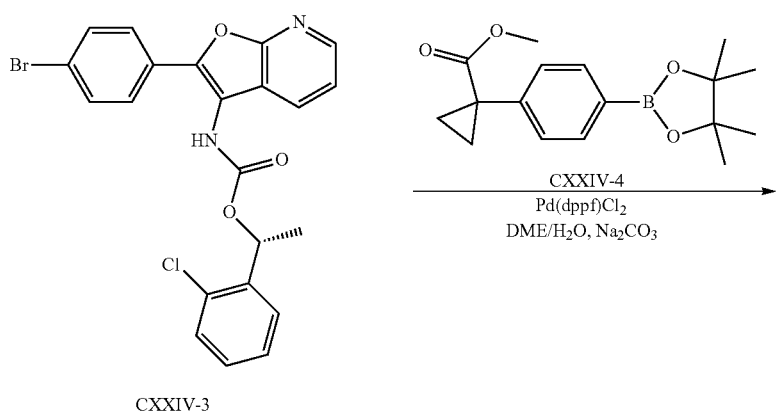
CXXIV-3
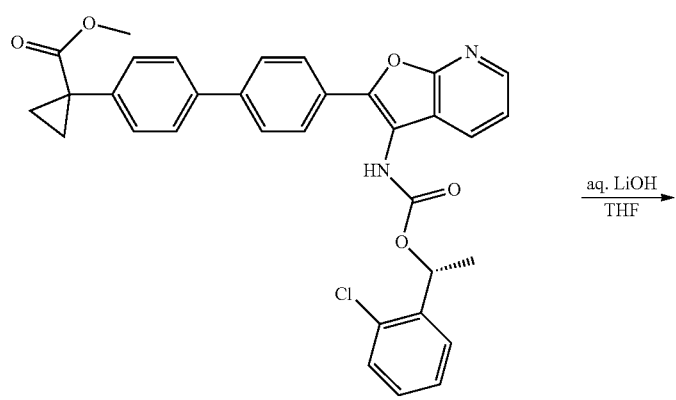
CXXIV-5
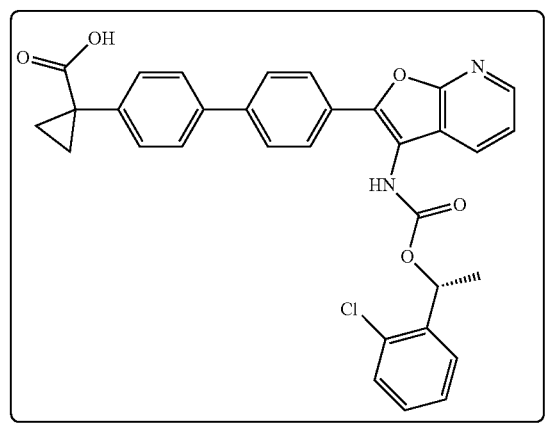
Compound 153
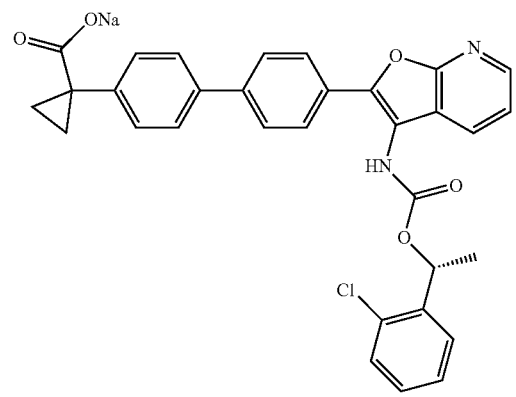
Compound 153a
Compound 153 was prepared analogously to the procedure described in the synthesis of Compound 152. MS (ESI) m/z (M+H)+ 553.1.
Compound 153a was prepared analogously to the procedure described in the synthesis of Compound 152a. $^1$H NMR (DMSO-$d_6$, 400 MHz) δ 9.92 (s, 1H), 8.33 (d, J=6.0 Hz, 1H), 7.91-7.98 (m, 3H), 7.71-7.79 (m, 3H), 7.47-7.58 (m, 4H), 7.36-7.39 (m, 4H), 6.06 (q, 1 H), 1.59 (brs, 3H), 1.25-1.27 (m, 2 H), 0.74-0.76 (m, 2 H). MS (ESI) m/z (M+H)+ 553.3.

Synthesis of Compound 154

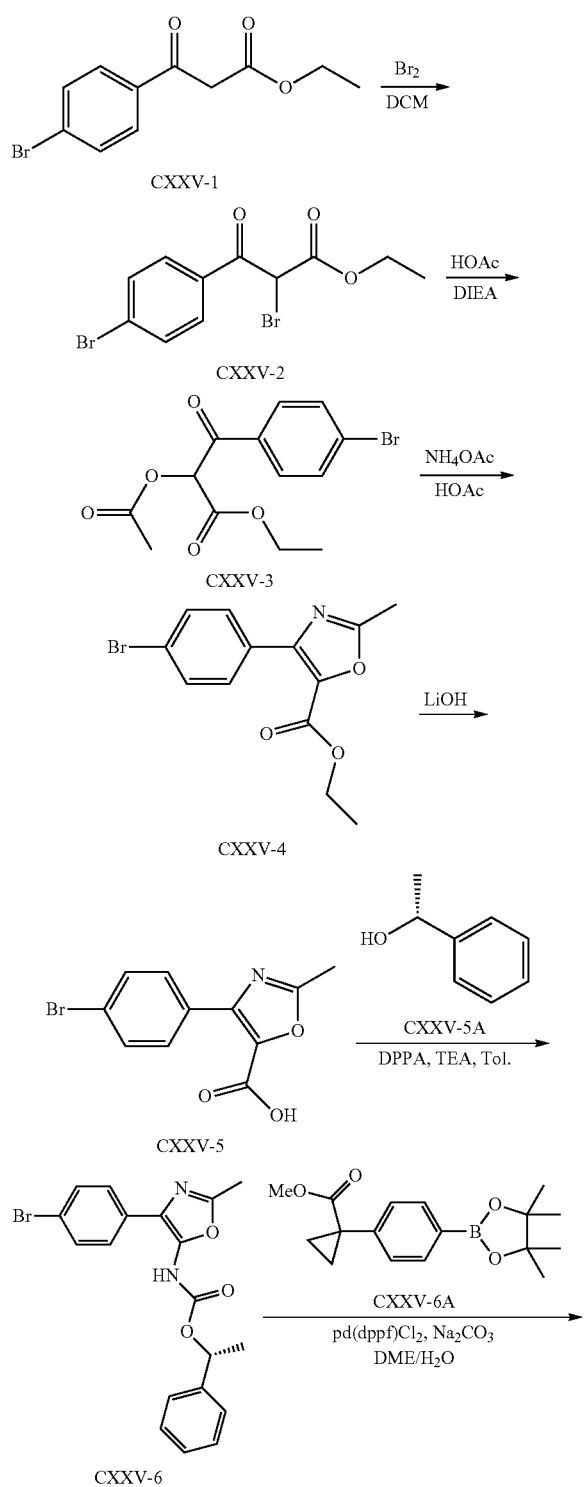

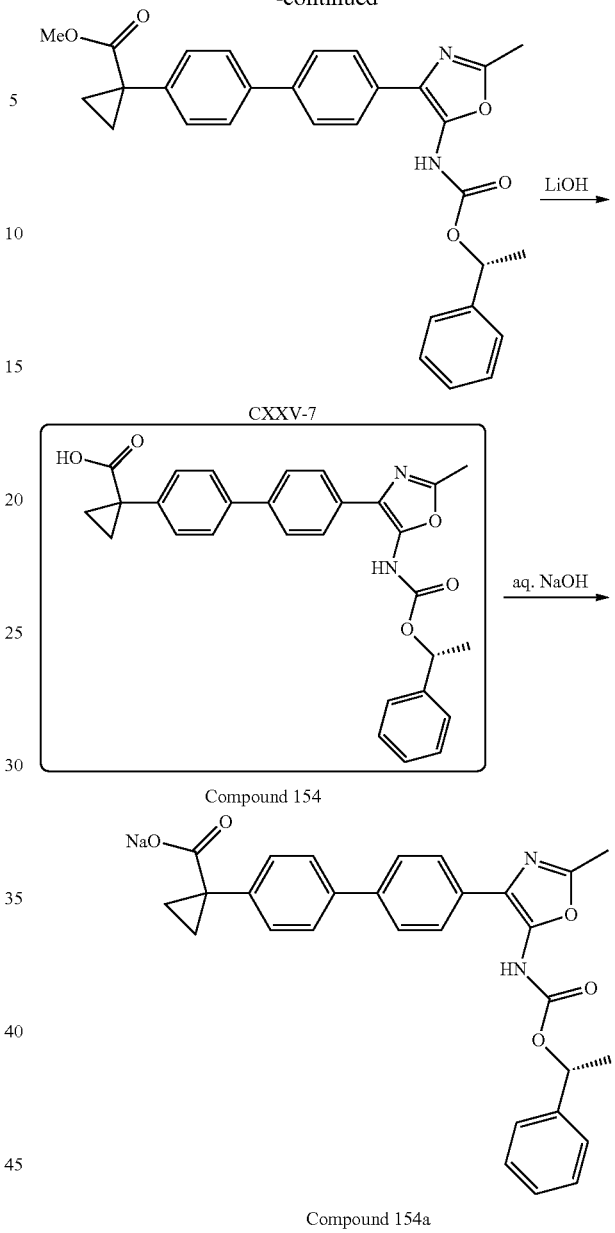

Br$_2$ (3.6 g, 1.0 eq) was added to the solution of compound CXXV-1 (10 g, 0.048 mol) in 50 mL of DCM at 0° C. The reaction mixture was stirred at r.t for 3 hours. Quenched with H$_2$O, and the organic layer was separated, dried, and concentrated in vacuo to afford crude compound CXXV-2 (12 g, yield: 87%).

A mixture of the compound CXXV-2 (10 g, 0.035 mol), HOAc (4.2 g, 0.07 mol), DIEA (9 g, 0.07 mol) was dissolved in 70 mL CH$_3$CN, and the mixture was stirred for overnight at r.t. After concentrated in vacuo, the residue was extracted with EA and washed with water, the organic layer was concentrated to afford crude compound CXXV-3 (9.2 g, crude yield: 99%).

A mixture of the compound CXXV-3 (9.2 g, 0.035 mol), NH$_4$OAc (5.36 g, 0.07 mol) was dissolved in 70 mL of HOAc. The mixture was stirred at reflux for overnight. After concentrated in vacuo, the residue was washed with water, and extracted EtOAc (250 mL). The organic layer was dried, concentrated, and purified by column chromatography on silica gel (PE:EA=50:1-25:1-10:1) to afford compound CXXV-4 (4.3 g, yield: 51%). MS (ESI) m/z (M+H)+ 246.3.

Compound 154 was prepared analogously to the procedure described in the synthesis of Compound 146 (362 mg, yield: 41.4%). MS (ESI) m/z (M+H)+ 483.

Compound 154a was prepared analogously to the procedure described in the synthesis of Compound 146a. ¹H NMR (400 MHz, DMSO-d6): δ 9.98 (s, 1 H), 7.61-7.74 (m, 6 H), 7.35-7.43 (m, 7 H), 5.78 (q, 1 H), 2.43 (s, 3 H), 1.47-1.55 (m, 5 H), 1.17-1.20 (m, 2 H). MS (ESI) m/z (M+H)+ 483.2.

Synthesis of Compound 155

Synthetic Route (Scheme CXXVI)

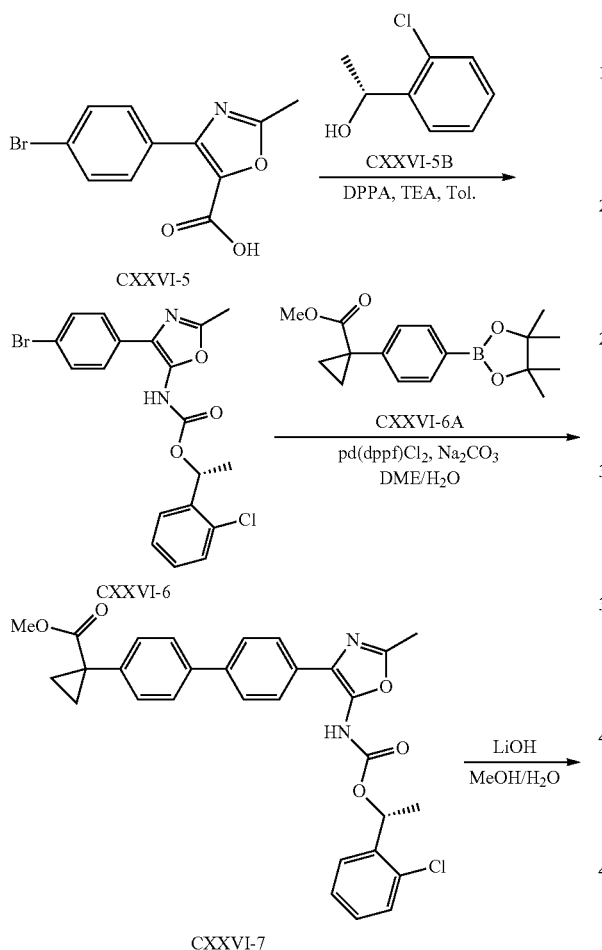

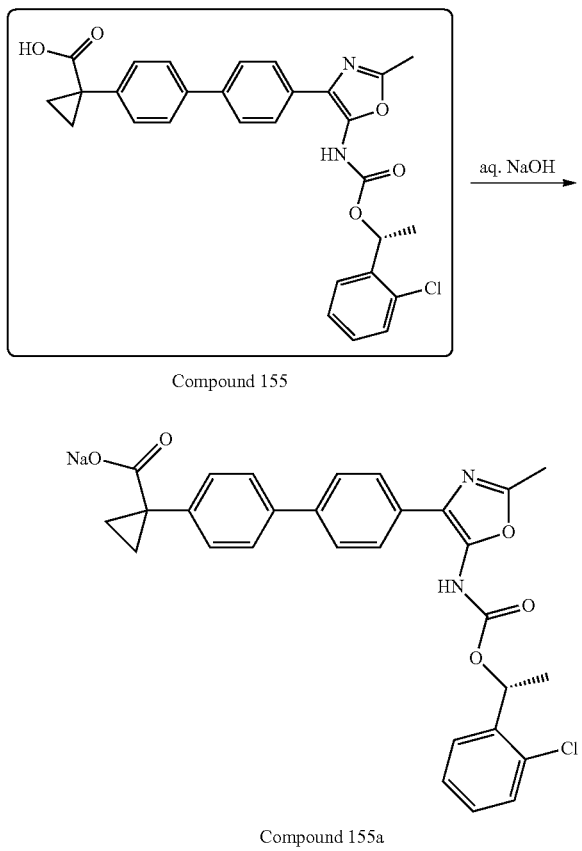

Compound 155 was prepared analogously to the procedure described in the synthesis of Compound 154 (100 mg, yield 12.8%). MS (ESI) m/z (M+H)+ 517.2.

Compound 155a was prepared analogously to the procedure described in the synthesis of Compound 146a. ¹H NMR (400 MHz, DMSO-d₆): δ 10.10 (s, 1 H), 7.61-7.74 (m, 7 H), 7.41-7.48 (m, 5 H), 6.03 (q, 1 H), 2.43 (s, 3 H), 1.47-1.56 (m, 5 H), 1.17-1.20 (m, 2 H). MS (ESI) m/z (M+H)+ 517.2.

Synthesis of Compound 156

Synthetic Route (Scheme CXXVII)

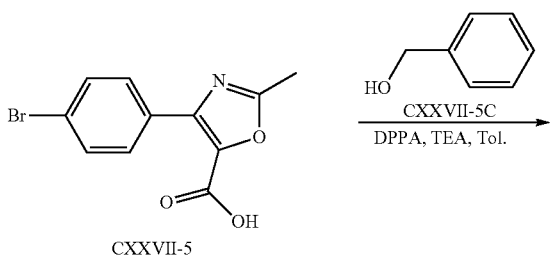

-continued
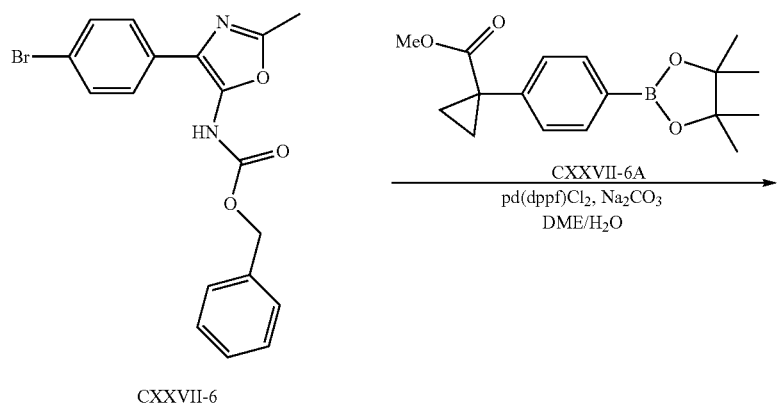
CXXVII-6
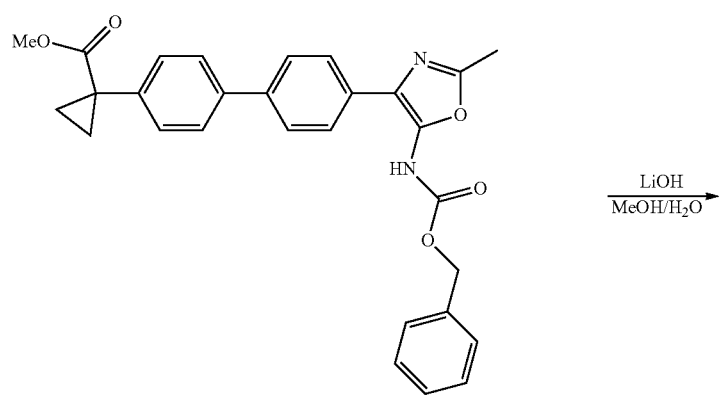
CXXVII-7
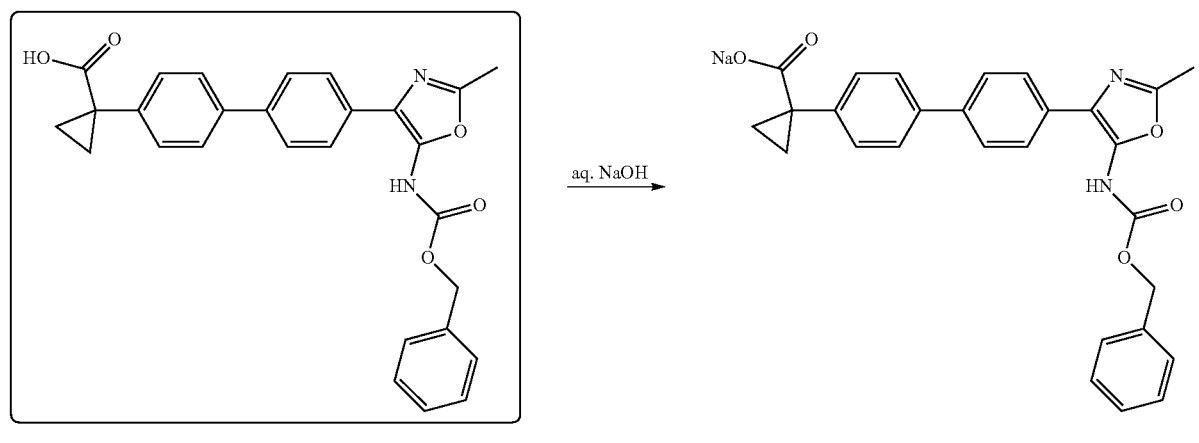
Compound 156
Compound 156a
Compound 156 was prepared analogously to the procedure described in the synthesis of Compound 154. MS (ESI) m/z (M+H)+ 469.1.
Compound 156a was prepared analogously to the procedure described in the synthesis of Compound 146a. $^1$H NMR (400 MHz, DMSO-d$_6$): δ 9.93 (s, 1 H), 7.62-7.78 (m, 6 H), 7.41-7.43 (m, 7 H), 5.18 (s, 2 H), 2.43 (s, 3 H), 1.47-1.50 (m, 2 H), 1.17-1.20 (m, 2 H). MS (ESI) m/z (M+H)⁺ 469.1.

Synthesis of Compound 157

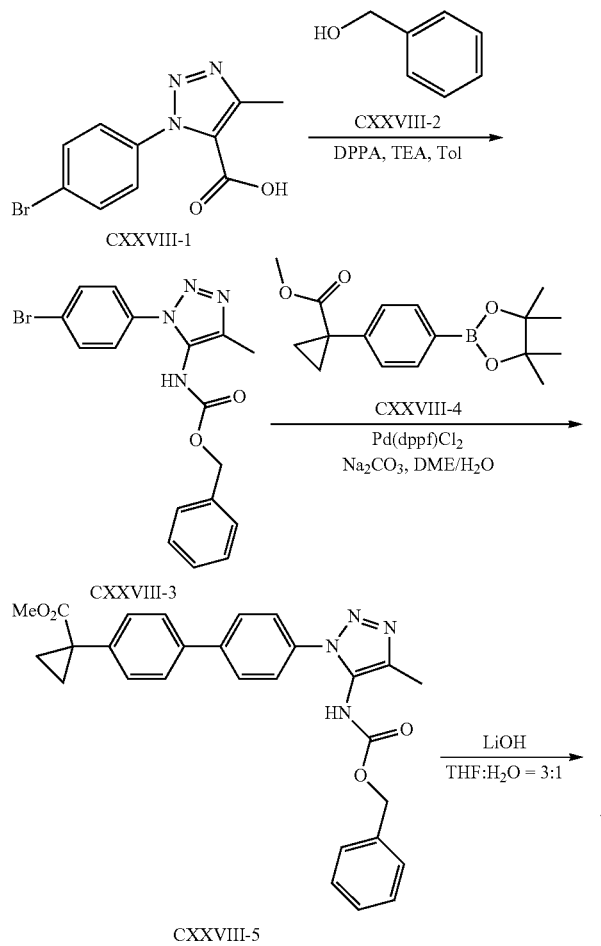

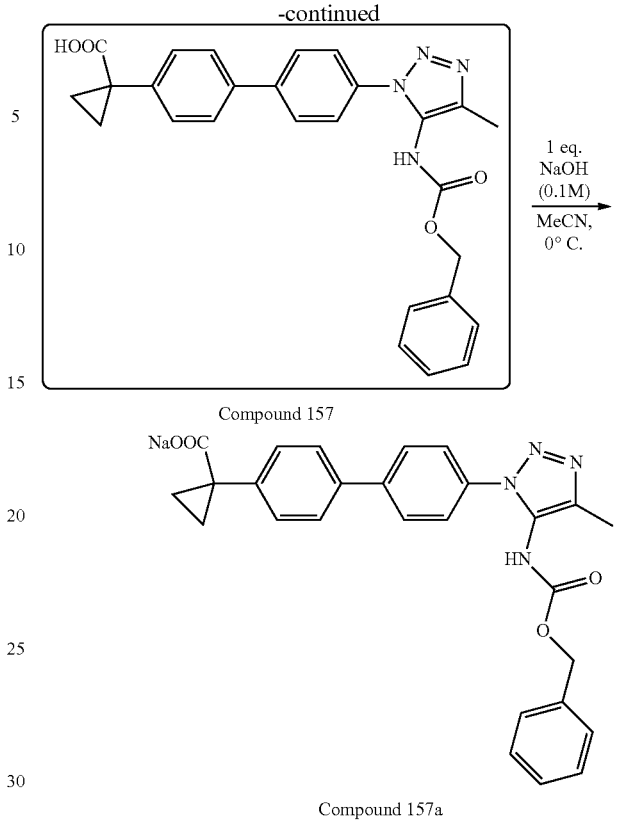

The detailed procedure for compound CXXVIII-1 has been described in synthesis of Compound 64.

Compound 157 was prepared analogously to the procedure described in the synthesis of Compound 64. MS (ESI) m/z (M+H)⁺ 469.2.

Compound 157a was prepared analogously to the procedure described in the synthesis of Compound 64a. ¹HNMR (DMSO-d₆ 400 MHz) δ 7.79 (d, J=8.4 Hz, 2H), 7.60 (d, J=8.4 Hz, 2H), 7.54 (d, J=8.0 Hz, 2H), 7.29-7.38 (m, 7H), 5.09 (s, 2H), 2.18 (s, 3H), 1.22 (brs, 2H), 0.73 (brs, 2H). MS (ESI) m/z (M+H)⁺ 469.2.

Synthesis of Compound 158

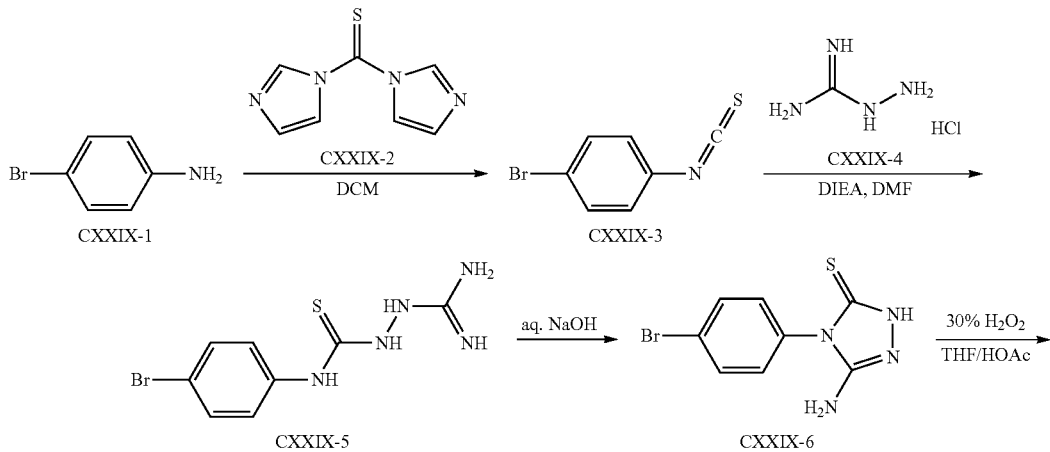

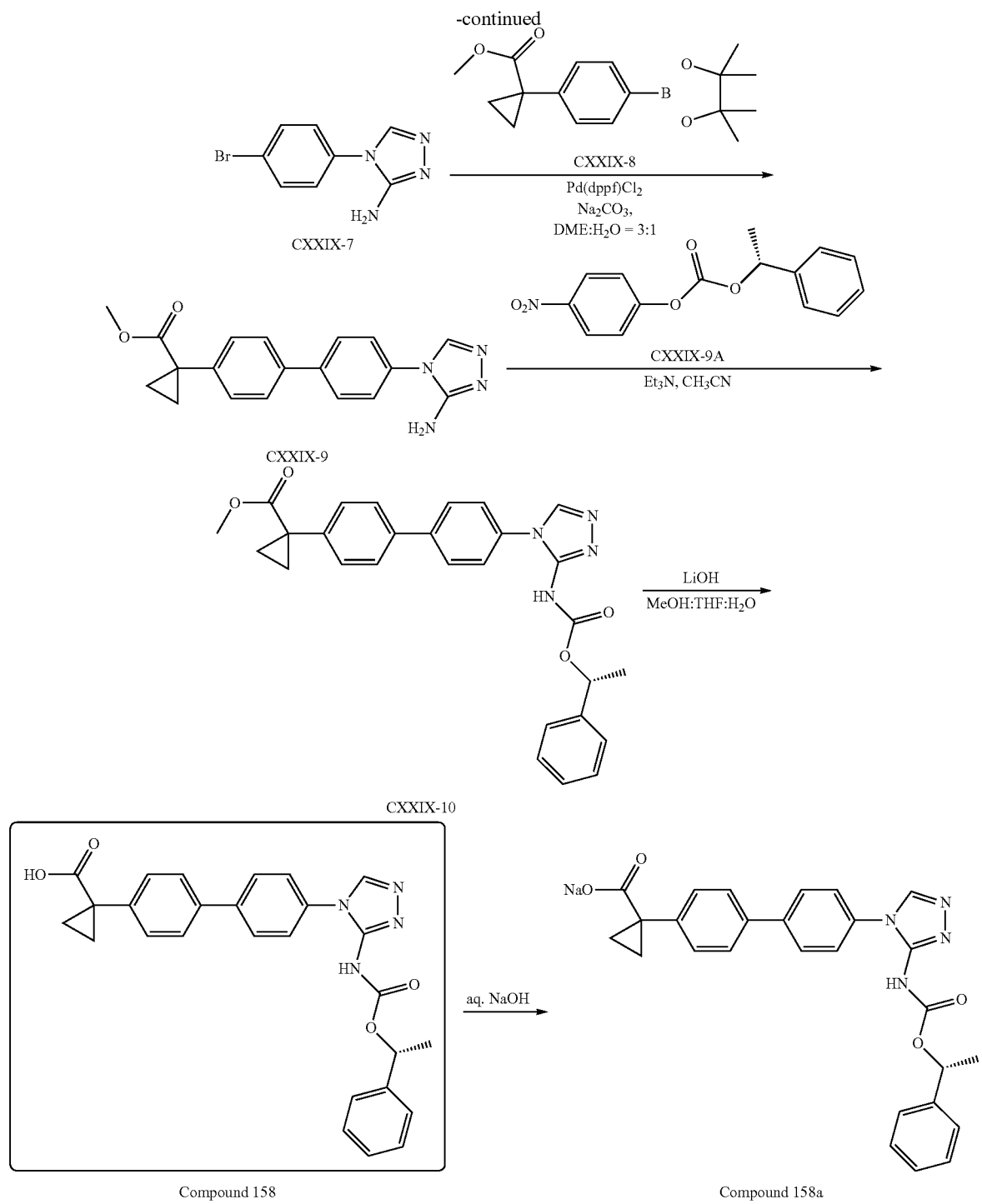

Compound 158

Compound 158a

To a solution of compound CXXIX-1 (30 g, 175 mmol) in dry DCM (250 mL) was added compound CXXIX-2 (37.5 g, 210.5 mmol) at 0° C. Then the reaction mixture was stirred at 0° C. for 2 hours. After concentrated, and the residue was purified by silica gel column chromatography (PE:EA=10:1) to afford compound CXXIX-3 (27 g, yield: 72.7%). MS (ESI) m/z (M+H)$^+$ 213.0.

Compound CXXIX-4 (15.5 g, 140.8 mmol) and DIPEA (14.2 g, 140.8 mmol) were added to a solution of compound 3 (20 g, 93.9 mmol) in DMF (80 mL) and the mixture stirred at 50° C. for 18 hours. The mixture was then concentrated under reduced pressure, and the residue was used to next step directly without purification.

Compound CXXIX-5 (26.95 g, 140.8 mmol) was added to a solution of sodium hydroxide (2M, 200 mL) and the mixture was stirred at 50° C. for 18 hours. After being cooled to room temperature, the mixture was neutralized with 1N HCl. The resulting precipitated was isolated to give compound CXXIX-6 (8.8 g, yield: 34.7%). MS (ESI) m/z (M+H)$^+$ 271.0.

A solution of 30% hydrogen peroxide (85 mL) in acetic acid (220 mL) was added dropwise to a suspension of compound CXXIX-6 (20 g, 74 mmol) in THF (350 mL) at 0° C.

After the addition, the mixture was stirred at room temperature overnight. Then the solvent was removed under reduced pressure. The residue was dissolved with water (100 mL), treated with aqueous sodium hydroxide to pH=12, extracted with DCM (100 mL×3). The combined organic phase was dried over $Na_2SO_4$ and concentrated. The residue was purified by column chromatography (DCM:MeOH=10:1) to afford compound CXXIX-7 (4 g, yield: 22.5%). MS (ESI) m/z (M+H)$^+$ 239.0.

The mixture of compound CXXIX-7 (1 g, 4.166 mmol), compound CXXIX-8 (1.38 g, 4.58 mmol), $Na_2CO_3$ (840 mg, 8.332 mmol) and Pd(dppf)Cl$_2$ in DME/H$_2$O (30 mL, v/v=3:1) was heated to reflux under nitrogen overnight. After concentrated, the residue was partitioned between H$_2$O and DCM. The aqueous phase was extracted with DCM, and the combined organic layer was washed with brine, dried over $Na_2SO_4$, and concentrated. The residue was washed with MeOH to afford compound CXXIX-9 (250 mg, yield: 17.9%).

The mixture of compound CXXIX-9 (200 mg, 0.0.598 mmol), compound CXXIX-9A (171.8 mg, 0.0.598 mmol), Et$_3$N (63.44 mg, 0.598 mmol) and DMAP (10 mg) in CH$_3$CN (10 mL) was heated to reflux under nitrogen for overnight. After concentrated, the residue was partitioned between H$_2$O and DCM, the aqueous phase was extracted with DCM, and the combined organic layer was washed with brine, dried over $Na_2SO_4$, and concentrated. The residue was purified by chromatography on silica gel (PE/EA=6/1) to afford compound CXXIX-10 (80 mg, yield: 27.7%).

Preparation of Compound 158

To a solution of compound CXXIX-10 (70 mg, 0.145 mmol) in MeOH (3 mL), THF (3 mL) and H$_2$O (3 mL), was added LiOH (30 mg, 0.725 mmol). The reaction mixture was stirred at room temperature overnight. After concentrated, the mixture was adjust to pH=2 with HCl (1N) and extracted with EtOAc (20 mL×3). The organic layers was washed with brine, dried over $Na_2SO_4$, and concentrated. The residue was purified by prep. HPLC to afford Compound 158 (40 mg, yield: 58.95%). MS (ESI) m/z (M+H)$^+$ 469.2.

Preparation of Compound 158a

To a solution of Compound 158 (40 mg, 0.085 mmol) in MeOH (1 mL) and MeCN (5 mL) was added 0.05 N sodium hydroxide solution (1.709 mL) at 0° C. The reaction mixture was stirred for 20 minutes. The mixture was freeze-dried to give Compound 158a. $^1$H NMR (DMSO-d$_6$, 400 MHz): δ 8.82 (s, 1H), 7.778 (d, J=8.0 Hz, 2H), 7.57 (d, J=8.0 Hz, 2H), 7.51 (d, J=8.0 Hz, 2H), 7.40 (d, J=8.0 Hz, 2H), 7.24-7.30 (m, 5H), 5.64 (q, 1H), 1.34 (brs, 5H), 0.92 (brs, 2H). MS (ESI) m/z (M+H)$^+$ 469.2.

Synthesis of Compound 159

Synthetic Route (Scheme CXXX)

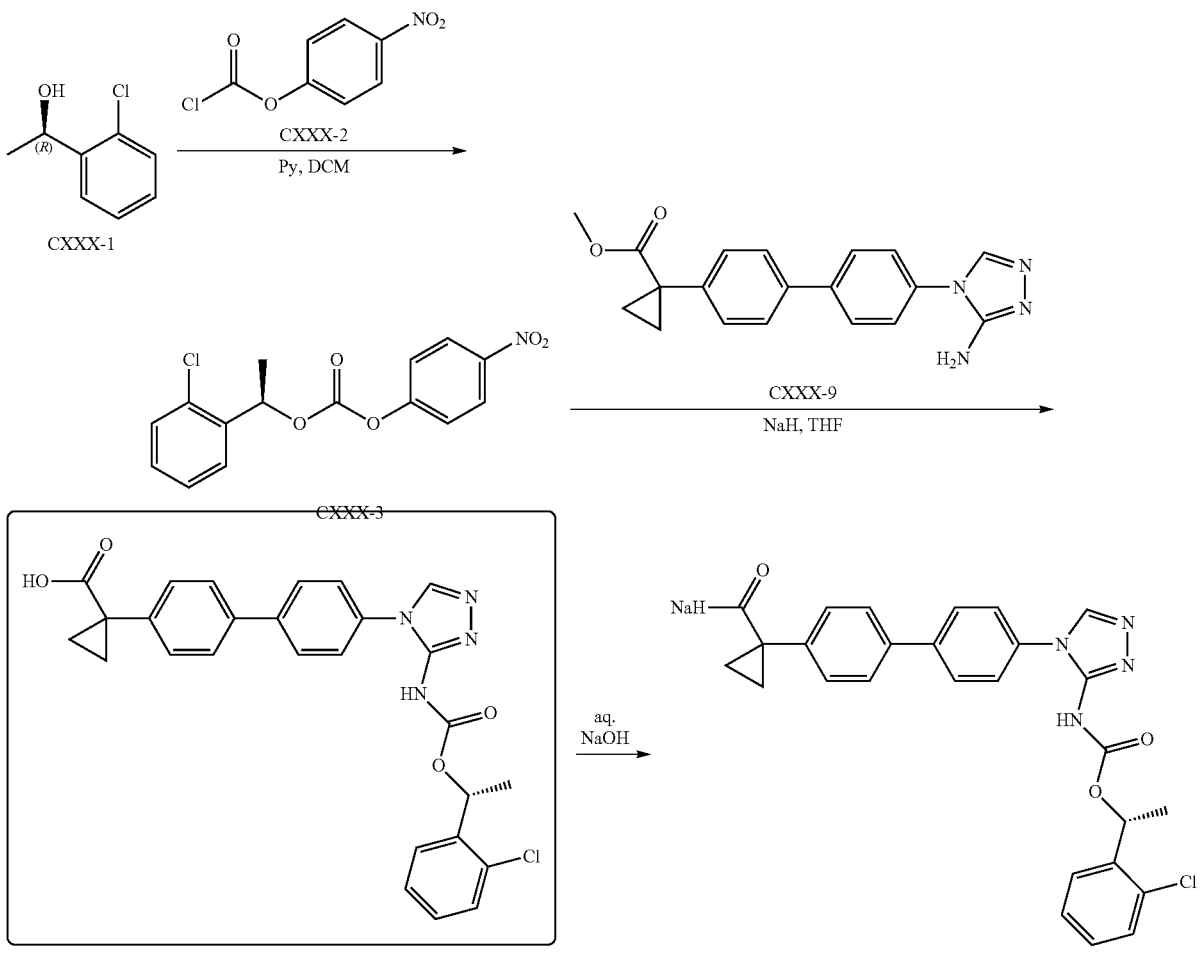

Compound 159

Compound 159a

Compound 159 was prepared analogously to the procedure described in the synthesis of Compound 158. MS (ESI) m/z (M+H)+503.1.

Compound 159a was prepared analogously to the procedure described in the synthesis of Compound 158a. ¹HNMR (DMSO-d$_6$, 400 MHz) δ 8.78 (s, 1H), 7.79 (d, J=8.8 Hz, 2H), 7.51-7.57 (m, 4H), 7.38-7.42 (m, 3H), 7.29-7.31 (m, 3H), 5.87 (q, 1H), 1.37 (d, J=6.4 Hz, 3H), 1.28 (br, 2H), 0.86 (br, 2H). MS (ESI) m/z (M+H)+ 503.1.

Synthesis of Compound 160

Synthetic Route (Scheme CXXXI)

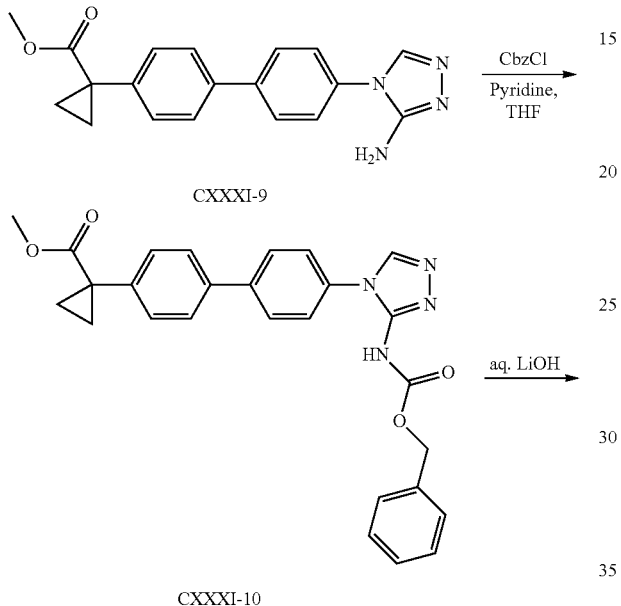

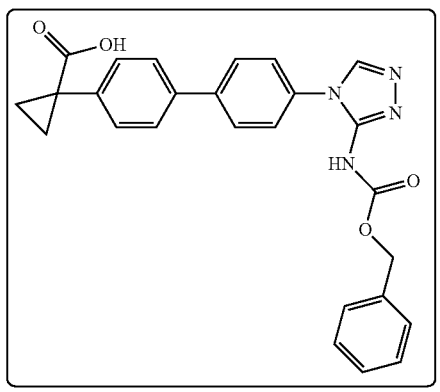

Compound 160

Compound 160 was prepared analogously to the procedure described in the synthesis of Compound 158. ¹HNMR (DMSO-d$_6$, 400 MHz): δ 10.5 (br, 1H), 8.84 (s, 1H), 7.81 (d, J=8.4 Hz, 2 H), 7.65 (d, J=8.4 Hz, 2 H), 7.45-7.54 (m, 4H), 7.25-7.31 (m, 5H), 5.04 (s, 2H), 1.49-1.52-(m, 2 H), 1.19-1.22 (m, 2H). MS (ESI) m/z (M+H)+ 455.2.

Synthesis of Compound 161

Synthetic Route (Scheme CXXXII)

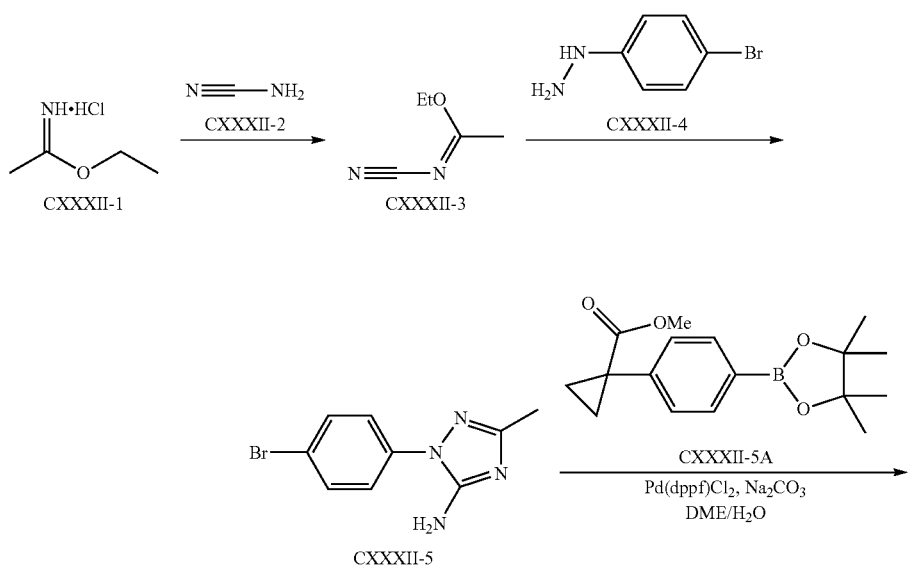

-continued

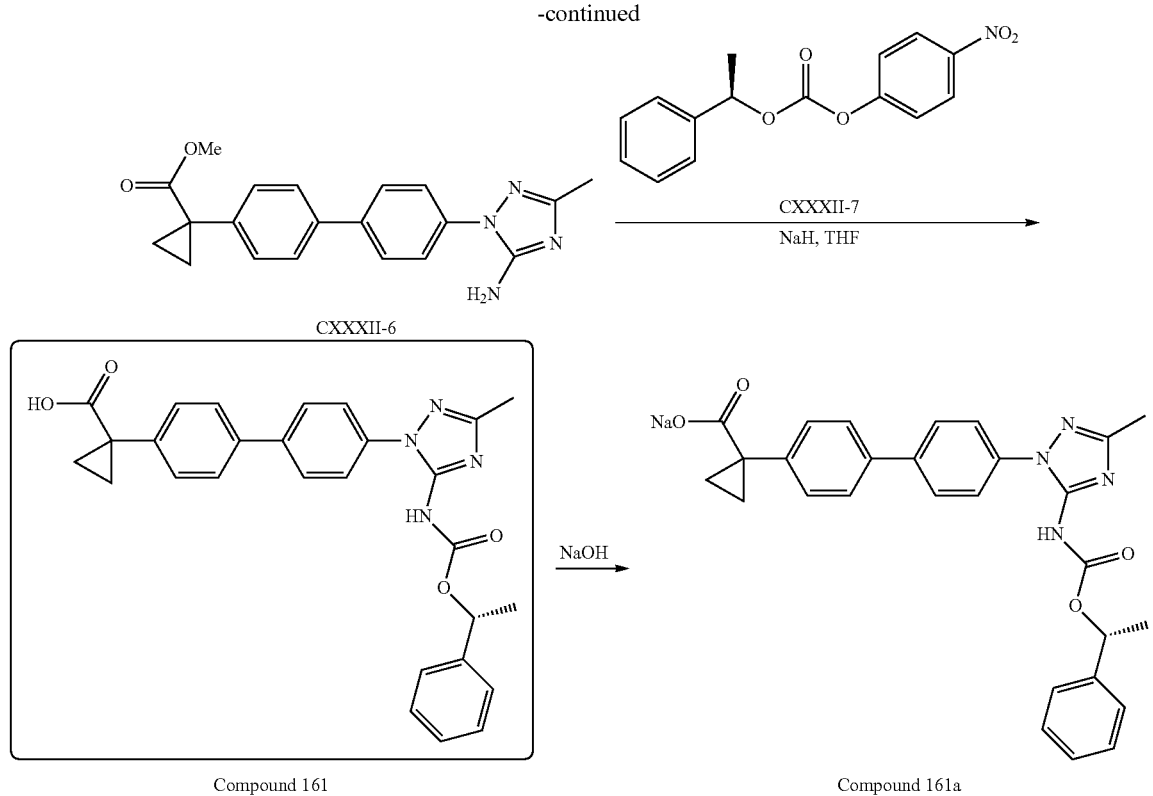

Compound 161

Compound 161a

A solution of compound CXXXII-1 (10.0 g, 1.0 eq) and compound CXXXII-2 (17.2 g, 5.0 eq) in ethanol (120 mL) was heated to 40° C. and stirred under nitrogen for 2 hours. Then the mixture was filtered, the filtrate was concentrated in vacuo, and the residue was dissolved in EtOAc (150 mL). The organic layer was washed with water and brine, dried over $MgSO_4$ and concentrated to afford compound CXXXII-3 (4.55 g, yield 50.17%), which was used to next step directly.

A solution of compound CXXXII-3 (4.55 g, 40.6 mmol) and compound CXXXII-4 (5.06 g, 27 mmol) in toluene (45 mL) was heated refluxed overnight. The solvent was removed by evaporation and the residue was purified by HPLC Separation to afford compound CXXXII-5 (2.66 g, yield 38.6%). MS (ESI) m/z (M+H)+ 252.9.

The mixture of compound CXXXII-5 (250 mg, 1.0 mmol), compound CXXXII-5A (360 mg, 1.2 mmol), $Na_2CO_3$ (2 00 mg, 2.0 mmol) and Pd(dppf)$Cl_2$ (25 mg) in DME/$H_2O$ (10 mL, v/v=3:1) was heated to reflux under nitrogen for overnight. After concentrated, the residue was partitioned between $H_2O$ and DCM, the aqueous phase was extracted with DCM, and the combined organic layer was washed with brine, dried over $Na_2SO_4$, and concentrated. The residue was purified by chromatography on silica gel (PE/EA=10/1) to afford compound CXXXII-6 (280 mg, yield: 80.4%). MS (ESI) m/z (M+H)+ 349.1.

Compound 161 was prepared analogously to the procedure described in the synthesis of Compound 158 (20 mg, yield: 14.5%). MS (ESI) m/z (M+H)+ 483.2.

Compound 161a was prepared analogously to the procedure described in the synthesis of Compound 158a. $^1$H NMR (DMSO-$d_6$, 400 MHz): δ 7.65 (br, 4H), 7.51 (d, J=8.0 Hz, 2H), 7.19-7.35 (m, 7H), 5.62 (q, 1H), 2.21 (s, 3H), 1.33 (d, J=6.8 Hz, 3H), 1.28 (brs, 2H), 0.88 (brs, 2H). MS (ESI) m/z (M+H)+ 483.2.

Synthesis of Compound 162

Synthetic Route (Scheme CXXXIV)

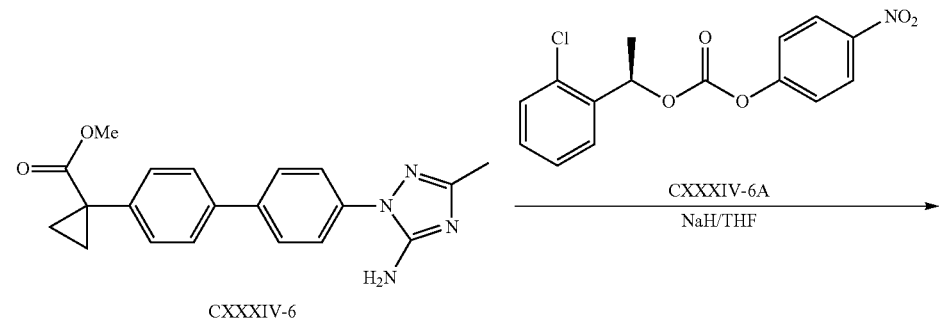

CXXXIV-6

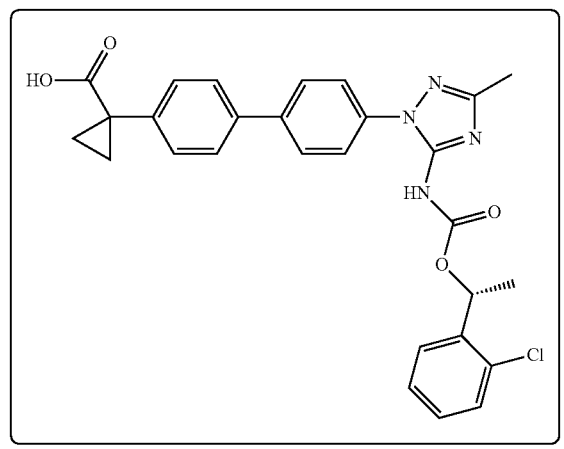

Compound 162

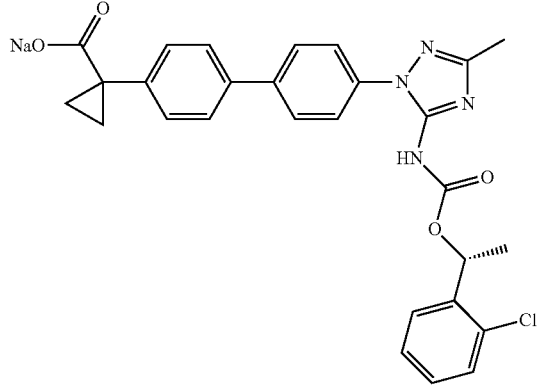

Compound 162a

Compound 162 was prepared analogously to the procedure described in the synthesis of Compound 161. MS (ESI) m/z (M+H)⁺ 517.2.

Compound 162a was prepared analogously to the procedure described in the synthesis of Compound 158a. $^1$H NMR (DMSO-$d_6$, 400 MHz): δ 10.35 (s, 1H), 7.76 (d, J=8.4 Hz, 2H), 7.63 (d, J=8.0 Hz, 2H), 7.57 (d, J=8.0 Hz, 2H), 7.41-7.46 (m, 3H), 7.30-7.36 (m, 3H), 5.87 (q, 1H), 2.31 (s, 3H), 1.59 (brs, 2H), 1.38 (d, J=6.4 Hz, 3H), 1.19 (brs, 2H). MS (ESI) m/z (M+H)⁺ 517.2.

Synthesis of Compound 163

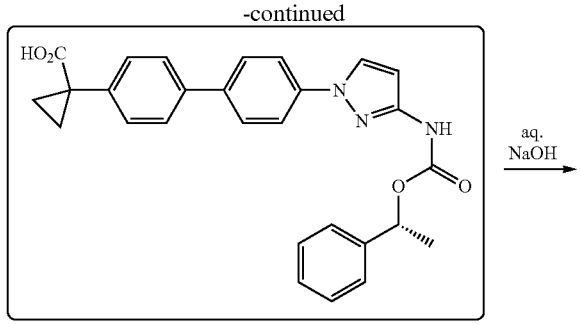

Compound 163

Synthetic Route (CXXXV)

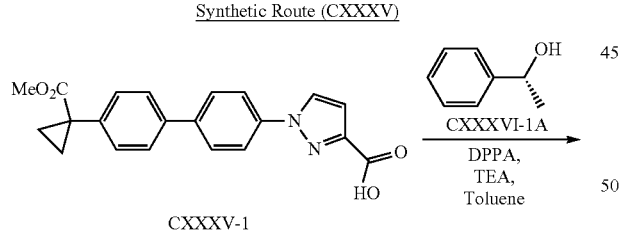

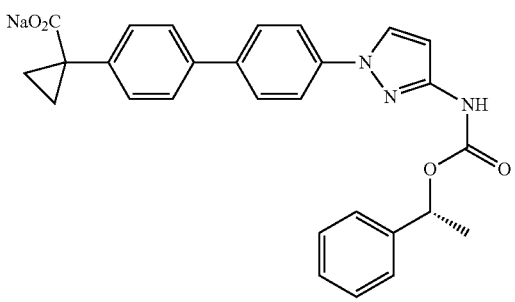

Compound 163a

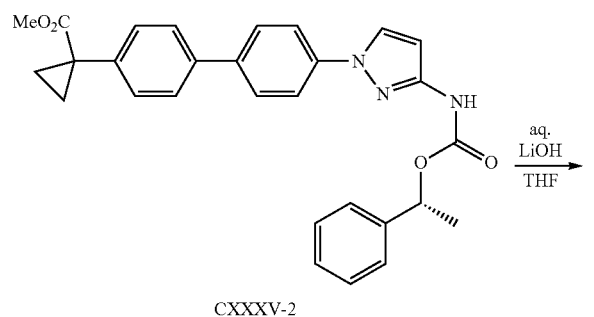

CXXXV-2

The detailed procedure for compound CXXXV-1 has been described in synthesis of Compound 68.

Compound 163 was prepared analogously to the procedure described in the synthesis of Compound 68. MS (ESI) m/z (M+H)⁺ 468.2.

Compound 163a was prepared analogously to the procedure described in the synthesis of Compound 68a. $^1$HNMR (DMSO-$d_6$, 400 MHz) δ 8.33 (s, 1H), 7.89 (d, J=8.4 Hz, 2H), 7.73 (d, J=8.4 Hz, 2H), 7.55 (d, J=8.4 Hz, 2H), 7.24-7.39 (m, 7H), 6.99 (s, 1H), 5.74 (q, 1H), 1.53 (d, J=6.4 Hz, 3H), 1.24-1.28 (m, 4H). MS (ESI) m/z (M+H)⁺ 468.1.

Synthesis of Compound 164

Synthetic Route (Scheme CXXXVI)

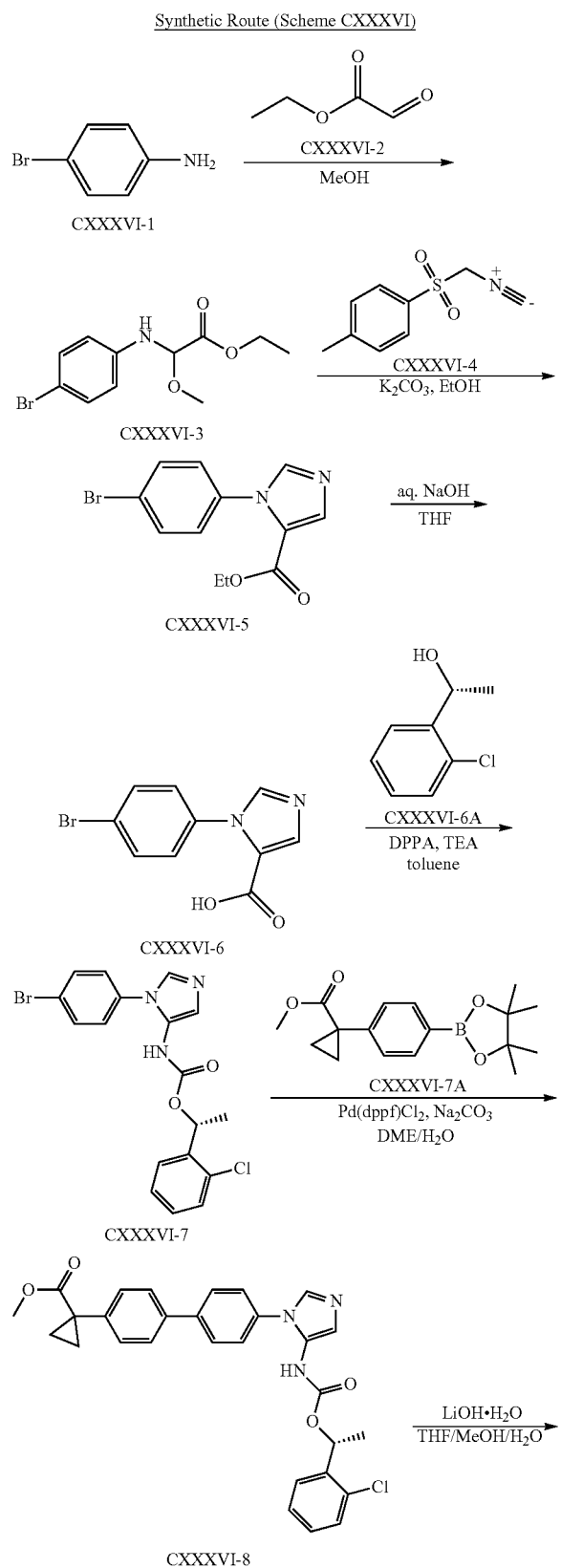

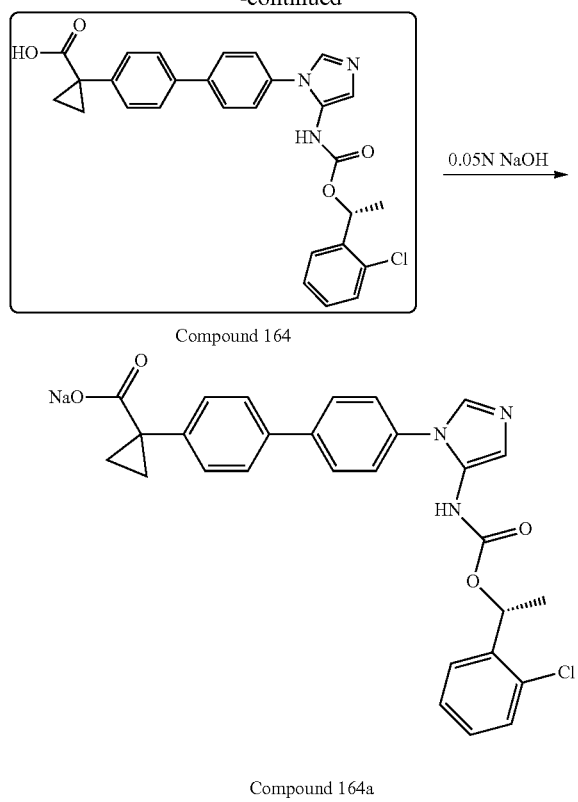

Compound 164

Compound 164a

To a solution of compound CXXXVI-1 (8.6 g, 50 mmol) in MeOH (100 mL) was added compound CXXXVI-2 (12 mL, 60 mmol, 50% in toluene) and the resulting mixture heated at reflux for 3.5 hours. The mixture was then concentrated under vacuum to afford crude compound CXXXVI-3, which was used to next step directly.

To a stirred solution of compound CXXXVI-3 in dry EtOH (100 mL) was added compound CXXXVI-4 (14.6 g, 75 mmol) and $K_2CO_3$ (13.8 g, 0.1 mol). The resulting mixture was heated at 65° C. for 4 hours, then cooled to 25° C. and poured to water (500 mL) and the resulting solid collected by filtration. The crude material thus isolated was crystallized from ethyl acetate/petroleum ether to give pure compound CXXXVI-5 (14 g, yield 94.8%).

NaOH (3.8 g, 95 mmol) was added to the mixture of compound CXXXVI-5 (14 g, 47.4 mmol) in THF/$H_2O$ (20 mL/20 mL) and the reaction mixture was stirred at r.t. for 2 h. Then concentrated to remove THF, and the aqueous layer was adjusted to pH=4-5 with HCl (1N) and the precipitated solid was collected by filtrated to afford compound CXXXVI-6 (8 g, yield 63.1%).

To a solution of compound CXXXVI-6 (0.42 g, 1.57 mmol) in dry toluene (10 mL) was added compound CXXXVI-6A (0.30 g, 1.89 mmol), TEA (0.32 g, 3.15 mmol) and DPPA (0.52 g, 1.89 mmol). The reaction mixture was heated to 80° C. for 3 hours. The mixture was diluted with EtOAc, washed with brine, dried over $Na_2SO_4$, filtered and concentrated to give crude compound CXXXVI-7 (crude 0.76 g), which was used to next step directly. MS (ESI) m/z $(M+H)^+$ 420.2.

To a stirred mixture of compound CXXXVI-7 (0.76 g, 1.81 mmol), compound CXXXVI-7A (0.66 g, 2.17 mmol), and $Na_2CO_3$ (0.38 g, 3.61 mmol) in DME (20 mL) and $H_2O$ (7 mL) was added Pd(dppf)$Cl_2$ (0.14 g, 0.09 mmol). The reaction mixture was flushed with nitrogen and heated to 80° C. overnight. The mixture was diluted with EtOAc (40 mL), washed with water and brine, dried over $Na_2SO_4$, filtered and concentrated. The residue was purified by prep-HPLC to give compound CXXXVI-8 (0.6 g, 64.3% yield). MS (ESI) m/z $(M+H)^+$ 516.0.

Preparation of Compound 164

A mixture of compound CXXXVI-8 (300 mg, 0.58 mmol) and lithium hydroxide monohydrate (97 mg, 2.32 mmol) in $MeOH/THF/H_2O$ (6 mL, v/v/v=1/1/1) was stirred at room temperature overnight. The mixture was concentrated in vacuo to remove MeOH and THF, acidified with aq. HCl (2 N) to pH=3, and then extracted with ethyl acetate (30 mL×3). The combined organic layer was washed with brine, dried over $MgSO_4$, filtered and concentrated. The residue was purified by prep-HPLC to afford Compound 164 (96 mg, yield 33%). $^1H$ NMR (DMSO-$d_6$, 400 MHz): δ 9.30 (s, 1H), 7.73-7.79 (m, 3H), 7.62 (d, J=8.4 Hz, 2H), 7.39-7.44 (m, 6H), 7.26-7.28 (m, 2H), 6.93-7.00 (m, 1H), 5.87-5.88 (m, 1H), 1.46-1.49 (m, 2H), 1.41-1.42 (m, 3H), 1.14-1.19 (m, 2H). MS (ESI) m/z $(M+H)^+$502.2.

Preparation of Compound 164a

To a solution of Compound 164 (96 mg, 0.19 mmol) in MeOH (1 mL) was added 0.05 N NaOH aqueous solution (3.82 mL, 0.19 mmol). The mixture was stirred for 15 minutes at room temperature. Then the volatile solvent was removed by evaporation and the resultant aqueous solution was lyophilized to yield Compound 164a. $^1H$ NMR (DMSO-$d_6$, 400 MHz): δ 9.32 (br, 1H), 7.85 (s, 1H), 7.70 (d, J=8.4 Hz, 2H), 7.50 (d, J=8.4 Hz, 2H), 7.34-7.51 (m, 6H), 7.26-7.29 (m, 3H), 6.91 (s, 1H), 5.87-5.90 (m, 1H), 1.34-1.46 (d, J=6.4 Hz, 3H), 1.27 (br, 2H), 0.74 (br, 2H). MS (ESI) m/z $(M+H)^+$ 502.0.

Synthesis of Compound 165

Synthetic Route (Scheme CXXXVII)

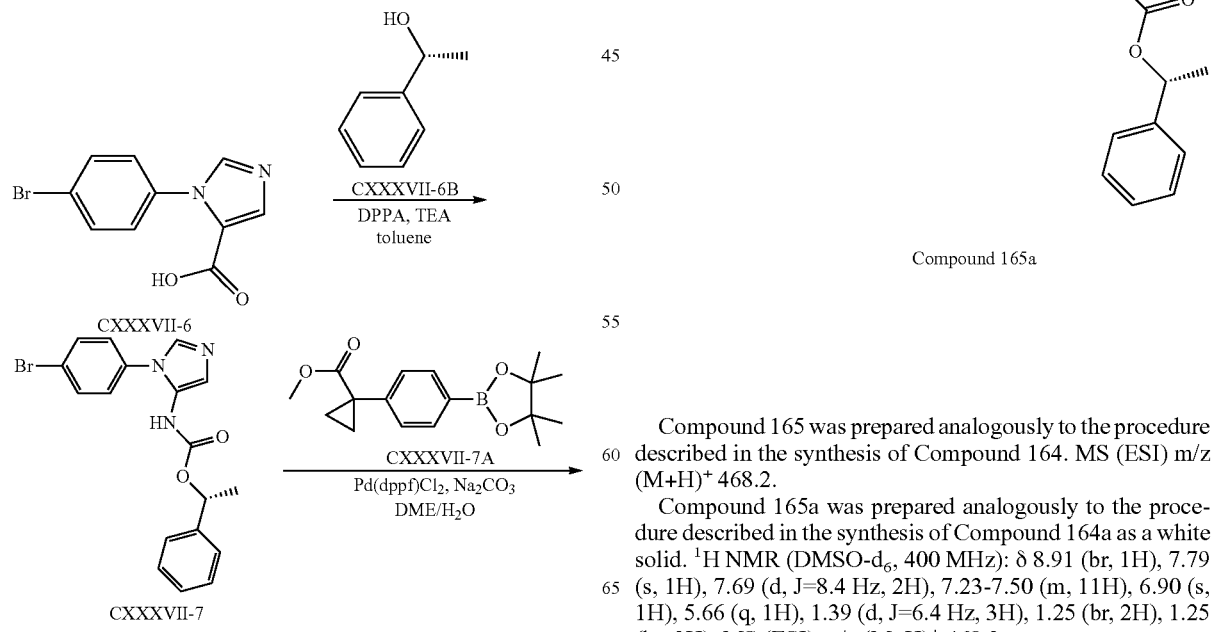

Compound 165 was prepared analogously to the procedure described in the synthesis of Compound 164. MS (ESI) m/z $(M+H)^+$ 468.2.

Compound 165a was prepared analogously to the procedure described in the synthesis of Compound 164a as a white solid. $^1H$ NMR (DMSO-$d_6$, 400 MHz): δ 8.91 (br, 1H), 7.79 (s, 1H), 7.69 (d, J=8.4 Hz, 2H), 7.23-7.50 (m, 11H), 6.90 (s, 1H), 5.66 (q, 1H), 1.39 (d, J=6.4 Hz, 3H), 1.25 (br, 2H), 1.25 (br, 2H). MS (ESI) m/z $(M+H)^+$ 468.2.

Synthesis of Compound 166

Synthetic Route (Scheme CXXXVIII)

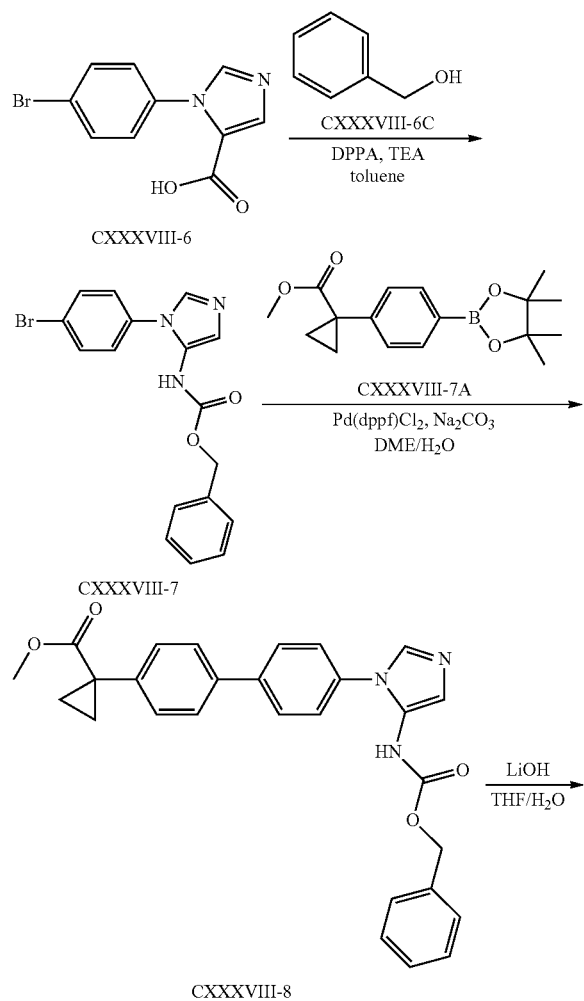

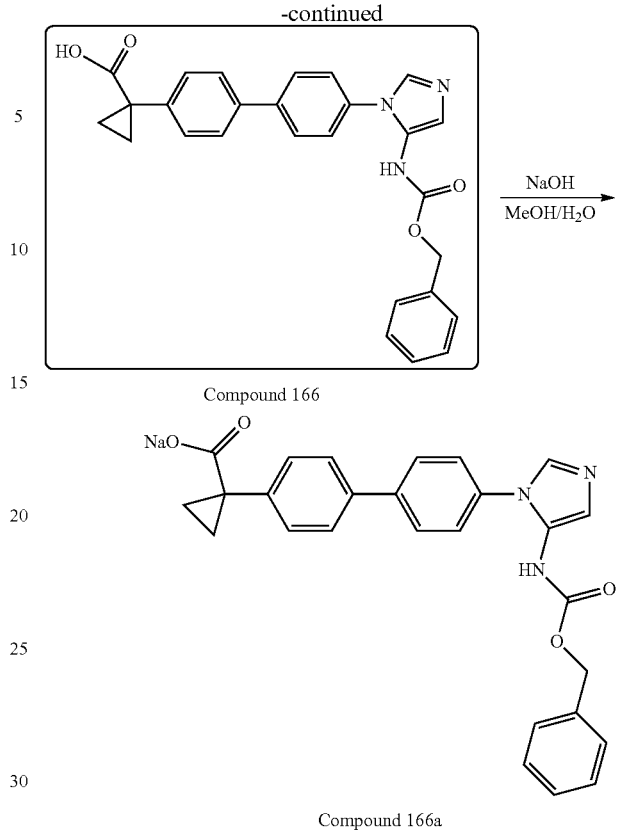

Compound 166 was prepared analogously to the procedure described in the synthesis of Compound 164. Compound 166a was prepared analogously to the procedure described in the synthesis of Compound 164a. $^1$HNMR (DMSO-$d_6$, 400 MHz) δ 7.77 (s, 1H), 7.72 (d, J=8.4 Hz, 2H), 7.51 (d, J=8.4 Hz, 2H), 7.40-7.46 (m, 4H), 7.24-7.32 (m, 5H), 6.92 (s, 1H), 5.04 (s, 2H), 1.27 (m, 2H), 0.74 (m, 2H). MS (ESI) m/z (M+H)$^+$ 476.1.

Synthesis of Compound 167

Synthetic Route (Scheme CXXXIX)

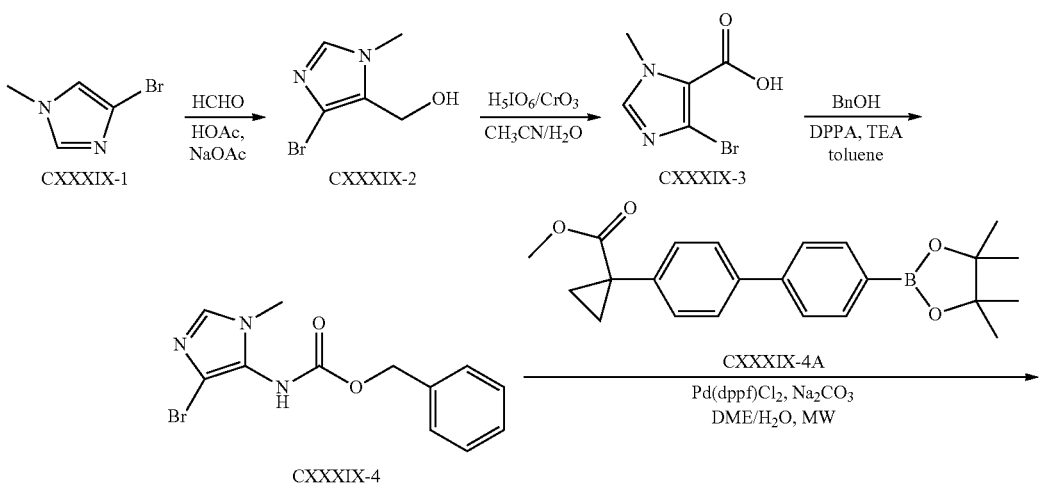

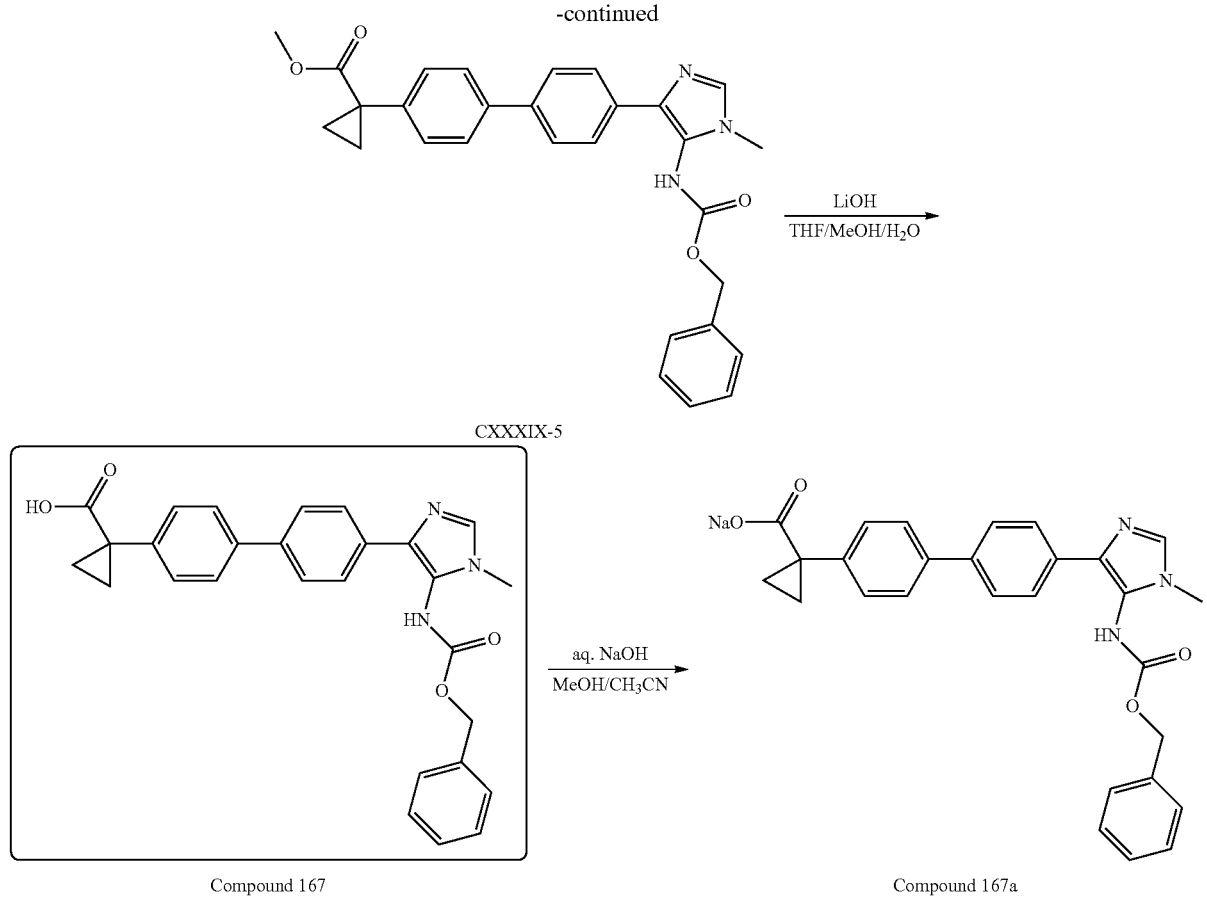

Compound 167

Compound 167a

The mixture of compound CXXXIX-1 (4 g, 25 mmol) in HCHO (40 mL, 35%), HOAc (3.4 mL), NaOAc.3H$_2$O (6.8 g, 50 mmol) was heated to reflux for 12 hours. After concentrated under vacuum, water (100 mL) was added and extracted with DCM. The organic layers was washed with brine, dried and concentrated under vacuum. The crude product was purified by column chromatography to give the desired compound CXXXIX-2 (4 g, yield: 85%).

To a solution of compound CXXXIX-2 (4 g, 21 mmol) in CH$_3$CN (20 mL) and H$_2$O (20 mL) was added H$_5$IO$_6$ (0.5 g, 2.1 mmol) and CrO$_3$ (0.42 g, 4.2 mmol). The mixture was heated to reflux for 12 hours. After filtered, the filtrated was concentrated under vacuum. The residue was purified by prep-HPLC to give compound CXXXIX-3 (1 g, yield 23%).

TEA (0.30 g, 2.93 mmol) and 4 A molecular sieve was added to a mixture of compound CXXXIX-3 (0.3 g, 1.46 mmol) in toluene (10 mL), followed by DPPA (0.48 g, 1.75 mmol). The mixture was stirred for 5 min. at room temperature. BnOH (0.19 g, 1.75 mmol) was added and the resulting mixture was heated at 80° C. for 2 hours under nitrogen. After cooled, ethyl acetate (20 mL) was added, the organic layer was washed with water, satur. NaHCO$_3$, brine, dried and concentrated under reduced pressure to afford crude compound CXXXIX-4 (0.40 g), which was used directly for next step.

Pd(dppf)Cl$_2$ (20 mg) was added to a stirred solution of compound CXXXIX-4 (200 mg, 0.6448 mmol), compound CXXXIX-4A (292 mg, 0.7738 mmol) and Na$_2$CO$_3$ (136.7 mg, 1.2896 mmol) in 10 mL of DME/H$_2$O (v/v=5:1). The mixture was stirred at 120° C. for 20 mins under MW condition. After being cooled to room temperature, water (10 mL) was added and extracted with DCM (20 mL×3). The extracts were washed with brine, dried over Na$_2$SO$_4$, concentrated to afford crude product, which was purification by Prep. TLC (PE:EA=1:1) to afford compound CXXXIX-5 (60 mg, yield: 19.35%). MS (ESI) m/z (M+H)$^+$ 482.2.

Preparation of Compound 167

To a solution of compound CXXXIX-5 (100 mg, 0.2074 mmol) in MeOH (3 mL), THF (6 mL) and H$_2$O (3 mL), was added LiOH (43.5 mg, 1.037 mmol). The reaction mixture was stirred at room temperature overnight. After concentrated, the mixture was adjust to pH=2 with HCl (1N) and extracted with EtOAc (20 mL×3). The organic layers was washed with brine, dried over Na$_2$SO$_4$, and concentrated. The residue was purified by Prep. HPLC to afford Compound 167 (50 mg, yield: 51.599%). MS (ESI) m/z (M+H)$^+$ 468.1.

Preparation of Compound 167a

To a solution of Compound 167 (50 mg, 0.107 mmol) in MeOH (1 mL) and MeCN (5 mL) was added 0.05 N sodium hydroxide solution (2.14 mL) at 0° C. The reaction mixture was stirred for 20 minutes. The mixture was lyophilized to give Compound 167a. $^1$H NMR (DMSO-d$_6$, 400 MHz): δ 7.67-7.75 (m, 3H), 7.51-7.59 (m, 4H), 7.41-7.46 (m, 6H), 7.12-7.20 (m, 1H), 5.26 (s, 2H), 3.59 (s, 3H), 1.56 (brs, 2H), 1.16 (brs, 2H). MS (ESI) m/z (M+H)$^+$ 468.1.

Synthesis of Compound 168

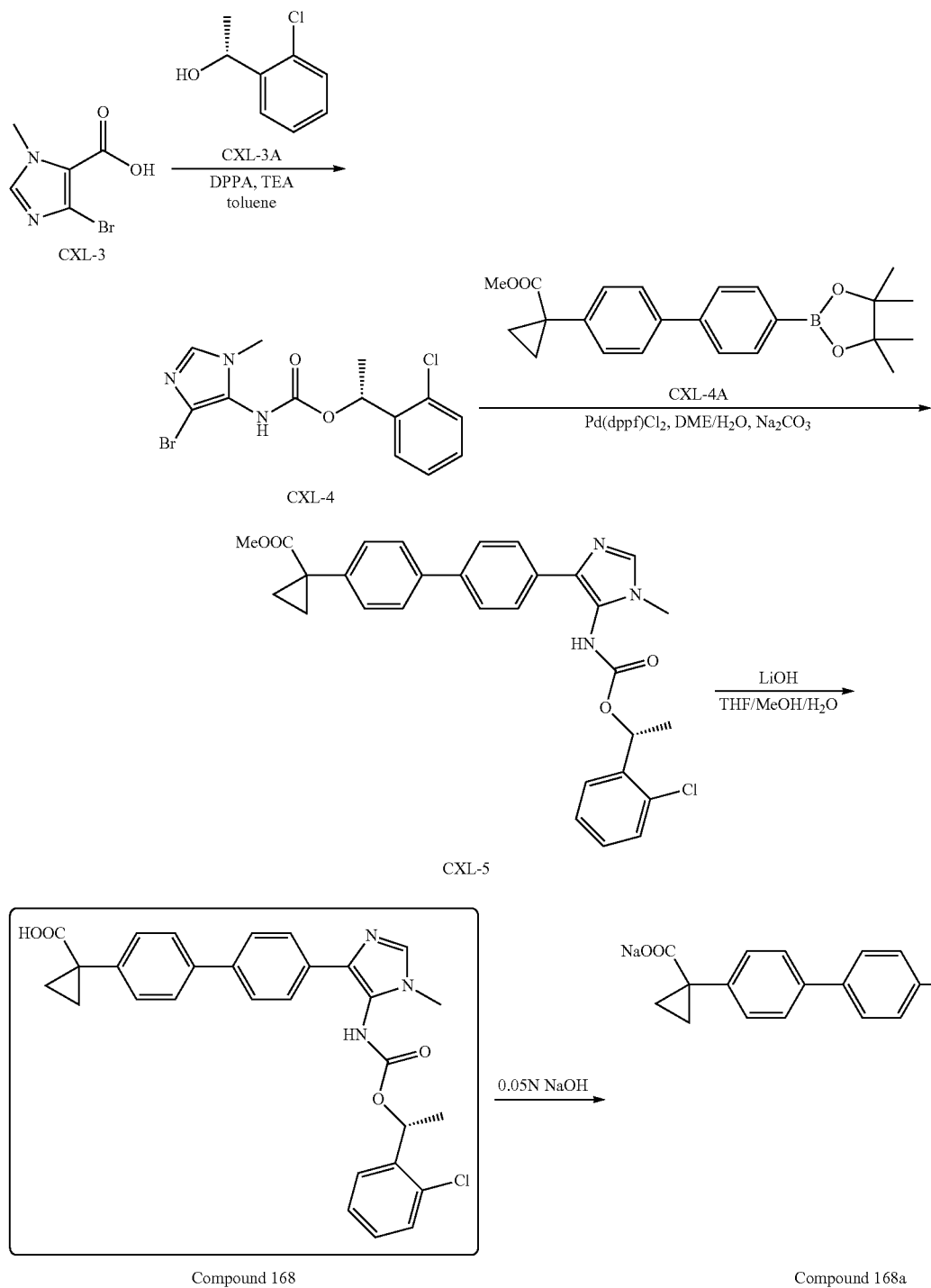

Synthetic Route (Scheme CXL)

Compound 168 was prepared analogously to the procedure described in the synthesis of Compound 167. $^1$H NMR (DMSO-$d_6$, 400 MHz): δ 10.10 (br, 1H), 8.93 (s, 1H), 7.71-7.77 (m, 4H), 7.62-7.64 (m, 3H), 7.36-7.42 (m, 5H), 6.00-6.02 (m, 1H), 3.62 (s, 3H), 1.46-1.56 (m, 5H), 1.14-1.18 (brs, 2H). MS (ESI) m/z (M+H)$^+$ 516.1.

Compound 168a was prepared analogously to the procedure described in the synthesis of Compound 167a. $^1$H NMR (DMSO-$d_6$, 400 MHz): δ 9.55 (s, 1H), 7.79-7.83 (m, 2H), 7.61-7.77 (m, 6H), 7.50-7.59 (m, 2H), 7.22-7.48 (m, 3H), 6.00-6.04 (m, 1H), 3.43 (s, 3H), 1.64 (d, J=6.4 Hz), 1.46 (brs, 2H), 1.15 (brs, 2H). MS (ESI) m/z (M+H)$^+$ 516.0.

Synthesis of Compound 169
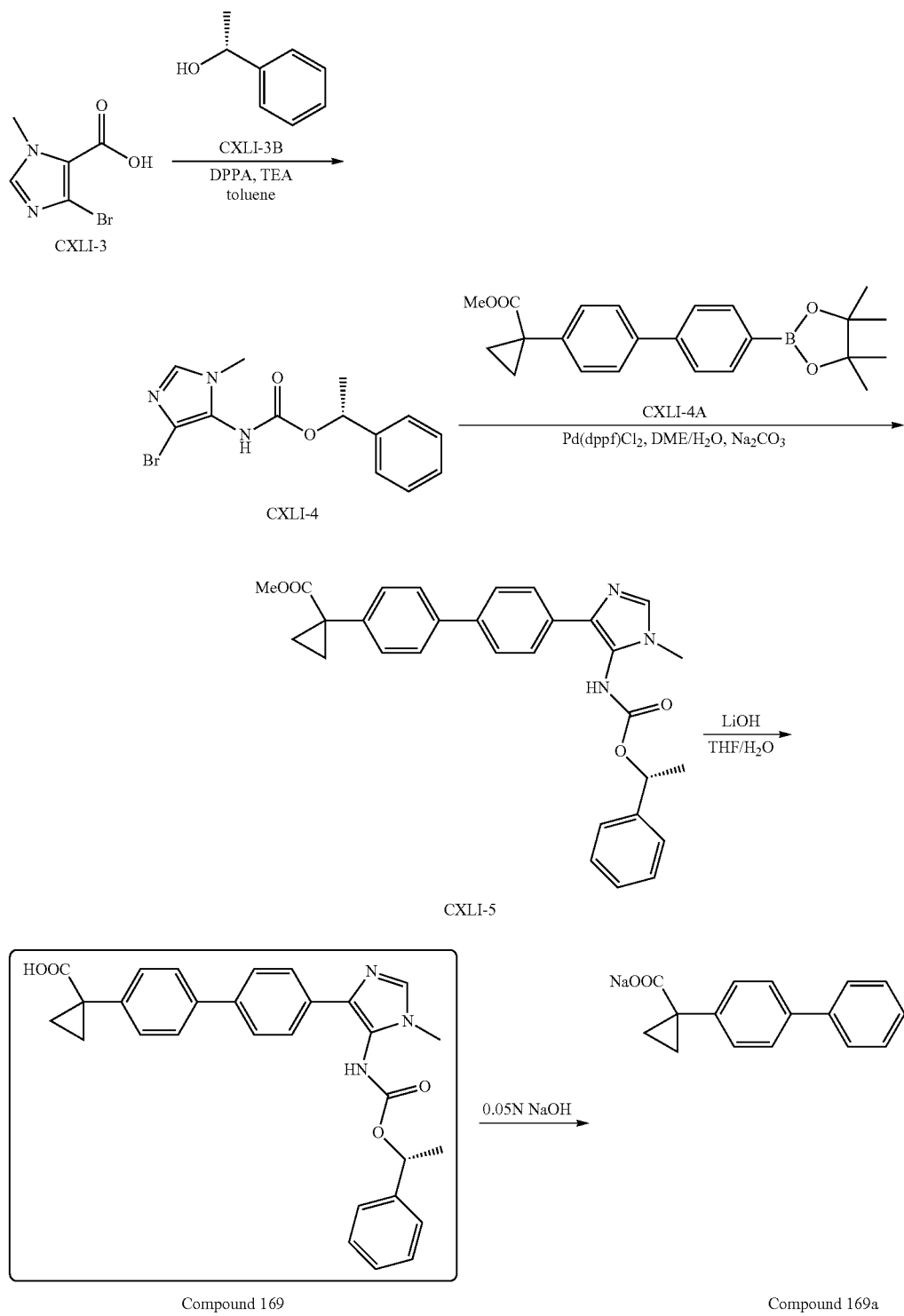
Compound 169 was prepared analogously to the procedure described in the synthesis of Compound 167. MS (ESI) m/z (M+H)+ 482.3.
Compound 169a was prepared analogously to the procedure described in the synthesis of Compound 167a. $^1$H NMR (DMSO-$d_6$, 400 MHz) δ 7.78 (d, J=8.4 Hz, 2H), 7.55-7.60 (m, 3H), 7.45-7.47 (m, 2H), 7.36-7.38 (m, 6H), 5.79-5.83 (q, 1H), 3.45 (s, 3H), 1.53 (brs, 3H), 1.26 (brs, 2H), 0.79 (brs, 2H). MS (ESI) m/z (M+H)+ 482.1.

Synthesis of Compound 170
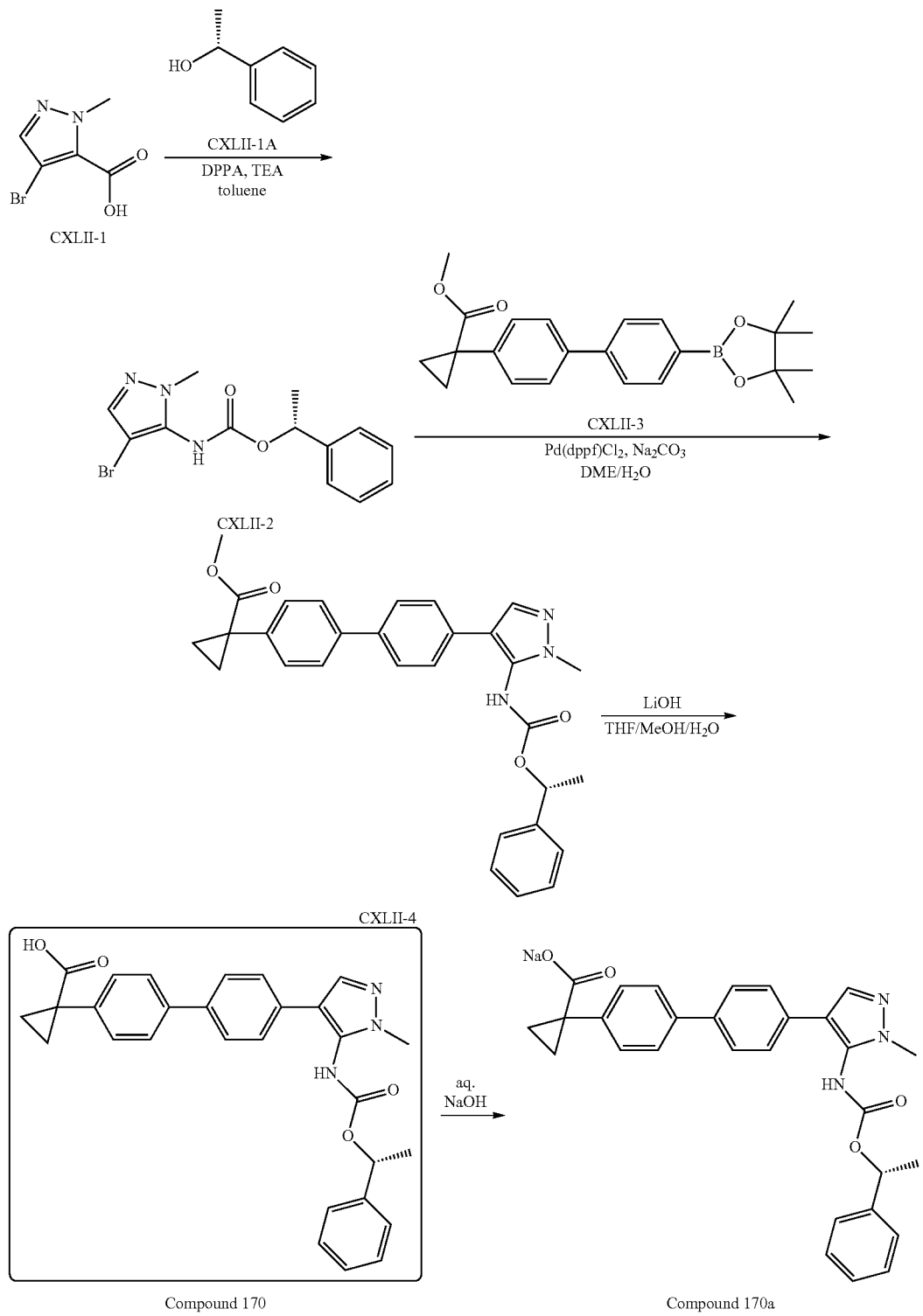
To a stirred solution of compound CXLII-1 (2 g, 9.8 mmol), compound CXLII-1A (1.43 g, 11.76 mmol) and TEA (1.98 g, 19.61 mmol) in toluene (50 mL) was added DPPA (3.23 g, 11.76 mmol) at room temperature. The reaction mixture was stirred at reflux for 2 hours and then cooled to room temperature. Water (50 mL) was added and extracted with EtOAc (60 mL×3), washed with brine, dried over Na$_2$SO$_4$ and concentrated. The residue was purified by Prep. TLC (PE: EA=5:1) to afford compound CXLII-2 (2 g, yield: 63.19%). MS (ESI) m/z (M+H)$^+$ 324.2.

To a stirred solution of compound CXLII-2 (1 g, 3.1 mmol), compound CXLII-3 (1.4 g, 3.72 mmol) and Na$_2$CO$_3$ (656 mg, 6.192 mmol) in 30 mL of DME/H$_2$O (v/v=3:1) was added Pd(dppf)Cl$_2$ (0.1 g) at room temperature. The solution was heated to reflux under nitrogen for 4 hours. After being cooled to room temperature, water (30 mL) was added and extracted with EtOAc (20 mL×3). The extracts were washed with brine, dried over Na$_2$SO$_4$, concentrated to afford crude product, which was purified by column chromatography (PE: EA=1:1) to afford compound CXLII-4 (600 mg, yield: 39.1%). MS (ESI) m/z (M+H)$^+$ 496.2.

Preparation of Compound 170

To a solution of compound CXLII-4 (80 mg, 0.1614 mmol) in MeOH (1 mL), THF (2 mL) and H$_2$O (1 mL) was added LiOH (40.64 mg, 0.9684 mmol). The reaction mixture was stirred at room temperature overnight. After concentrated, the mixture was adjust to pH=6 with HCl (1N) and extracted with EtOAc (20 mL×3). The organic layers was washed with brine, dried over Na$_2$SO$_4$, and concentrated. The residue was purified by prep. HPLC to afford Compound 170 (30 mg, yield: 38.7%). MS (ESI) m/z (M+H)$^+$ 482.3.

Preparation of Compound 170a

To a solution of Compound 170 (30 mg, 0.062 mmol) in MeOH (1 mL) and MeCN (5 mL) was added 0.05 N sodium hydroxide solution (1.246 mL) at 0° C. The reaction mixture was stirred for 30 minutes, and then freeze-dried to give Compound 170a. $^1$H NMR: (DMSO-d$_6$, 400 MHz): δ 7.78 (s, 1H), 7.52-7.55 (m, 5H), 7.34-7.47 (m, 5H), 7.30-7.34 (m, 4H), 5.78 (q, 1H), 3.63 (s, 3H), 1.54 (d, J=6.4 Hz, 3H), 1.17-1.18 (m, 2H), 0.66-0.67 (m, 2H). MS (ESI) m/z (M+H)$^+$ 482.3.

Synthesis of Compound 171

Synthetic Route (CXLIII)

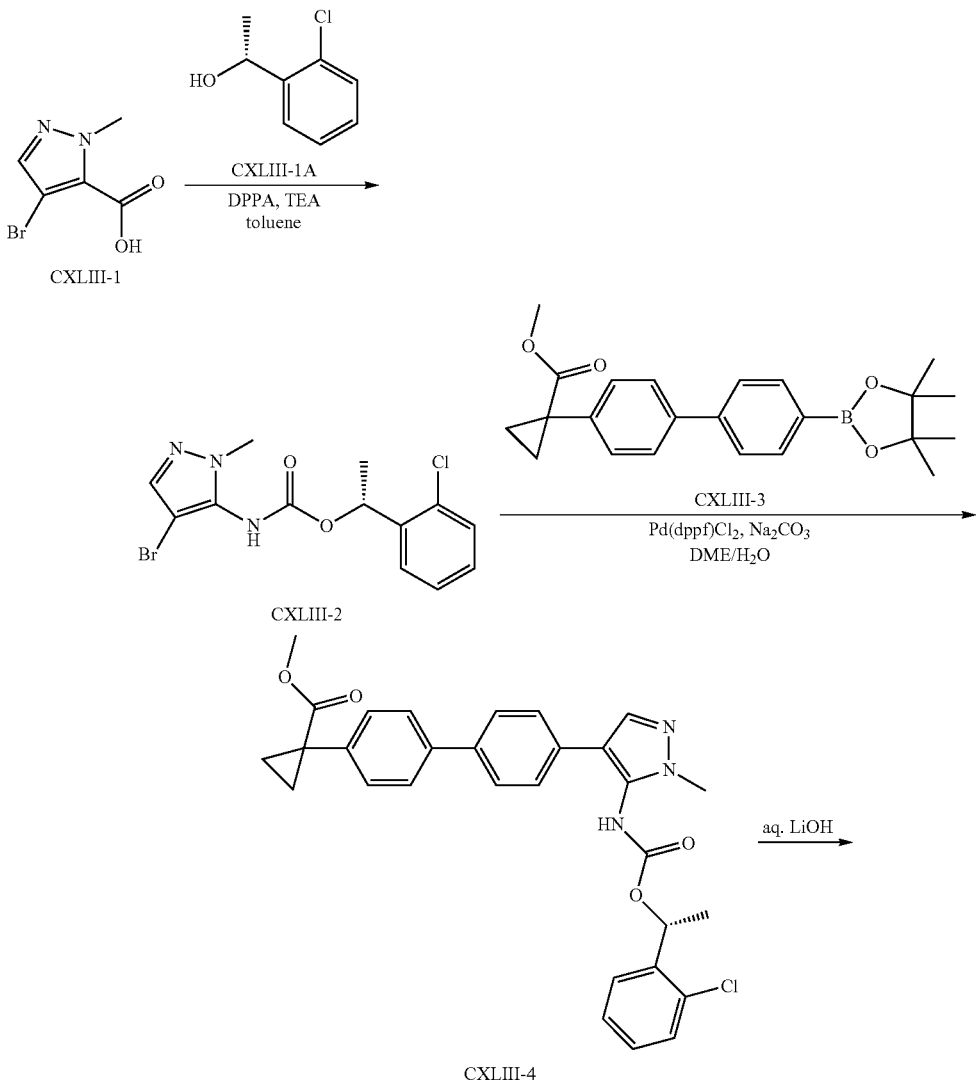

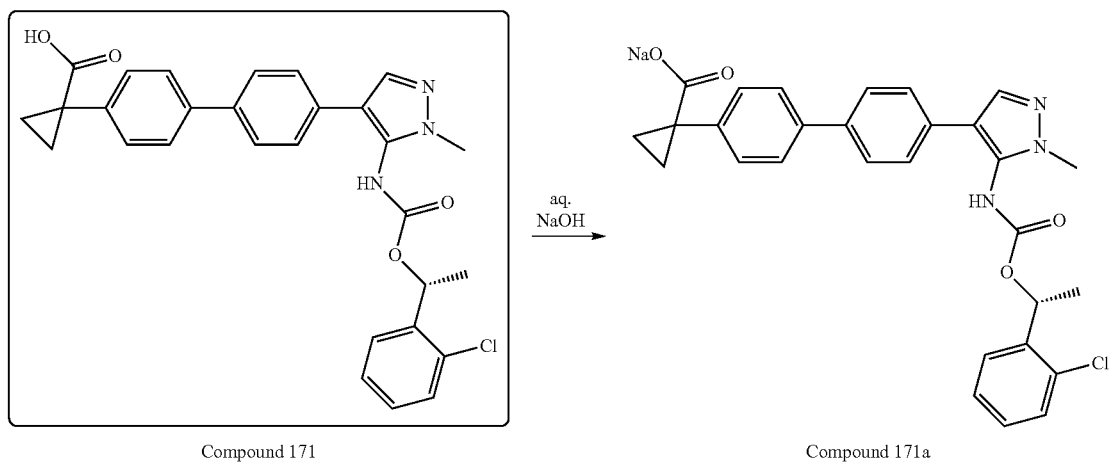
Compound 171                 Compound 171a
Compound 171 was prepared analogously to the procedure described in the synthesis of Compound 170. MS (ESI) m/z (M+H)$^+$516.2.
Compound 171a was prepared analogously to the procedure described in the synthesis of Compound 170a. $^1$H NMR (DMSO-d$_6$, 400 MHz): δ 7.73 (s, 1H), 7.49-7.59 (m, 8H), 7.28-7.42 (m, 4H), 6.15-6.16 (q, 1H), 3.71 (s, 3H), 1.59 (d, J=5.6 Hz, 3H), 1.42-1.44 (m, 2H), 0.93-0.96 (m, 2H). MS (ESI) m/z (M+H)$^+$ 516.2.
Synthesis of Compound 172
Synthetic Route (Scheme CXLIV)
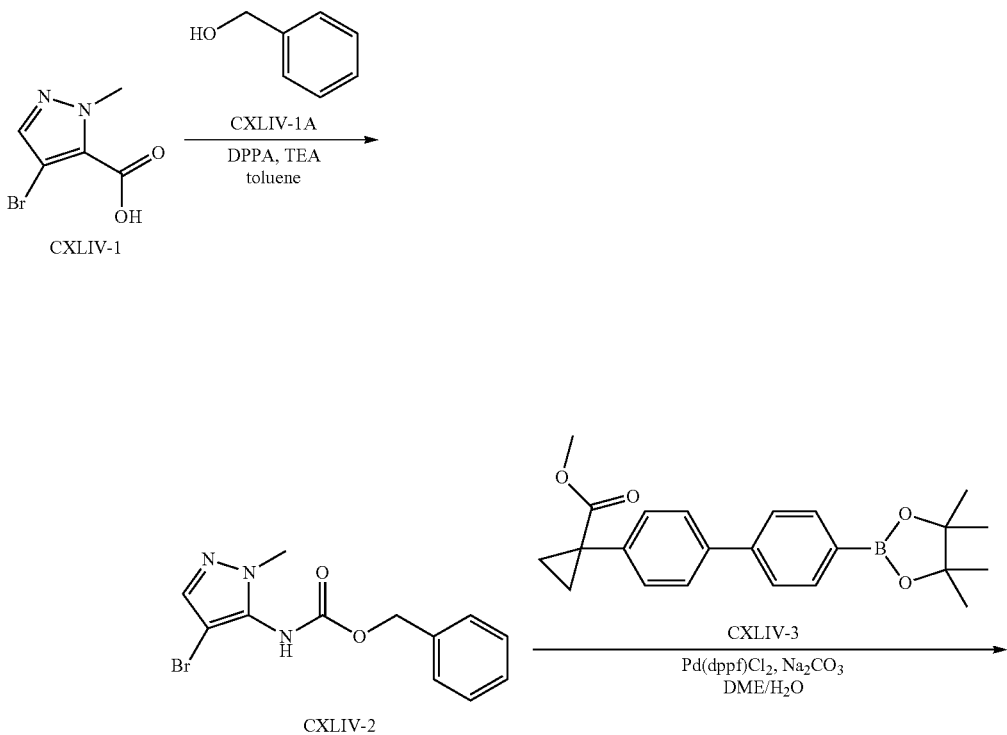

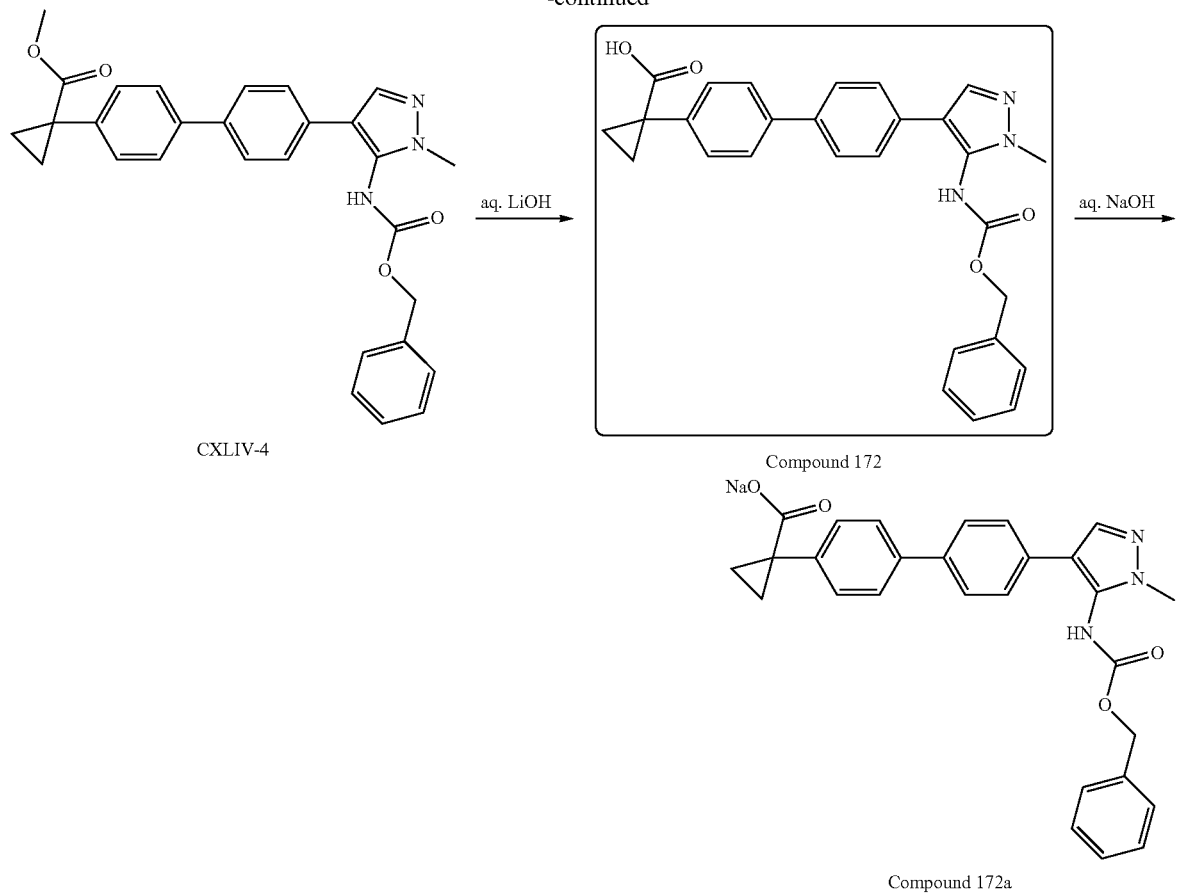
Compound 172 was prepared analogously to the procedure described in the synthesis of Compound 170. MS (ESI) m/z (M+H)+ 468.2.
Compound 172a was prepared analogously to the procedure described in the synthesis of Compound 170a. ¹H NMR (DMSO-$d_6$, 400 MHz): δ 7.74 (s, 1H), 7.47-7.56 (m, 7H), 7.34-7.42 (m, 6H), 5.21 (s, 2H), 3.73 (s, 3H), 1.42-1.44 (m, 2H), 0.94-0.97 (m, 2H) MS (ESI) m/z (M+H)+ 468.2.
Synthesis of Compound 173
Synthetic Route (Scheme CXLV)
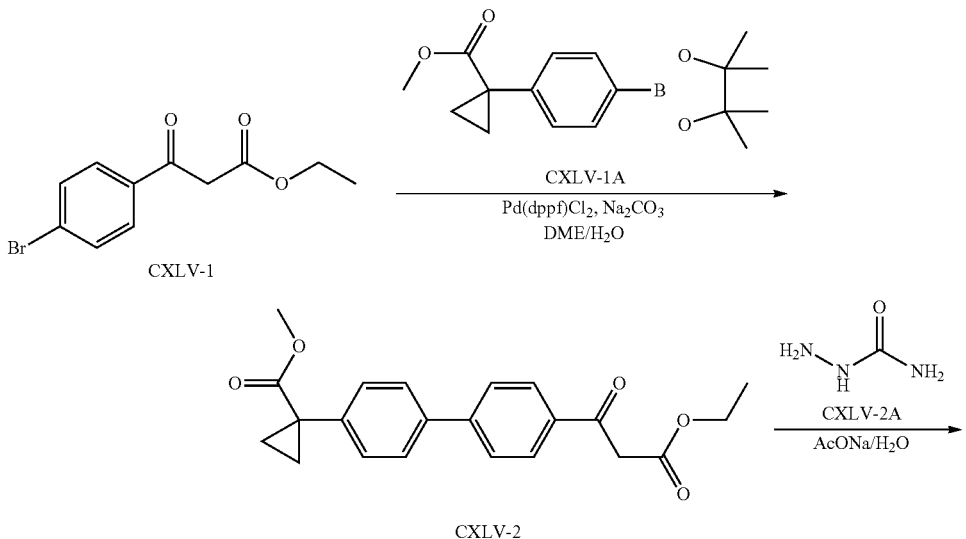

-continued

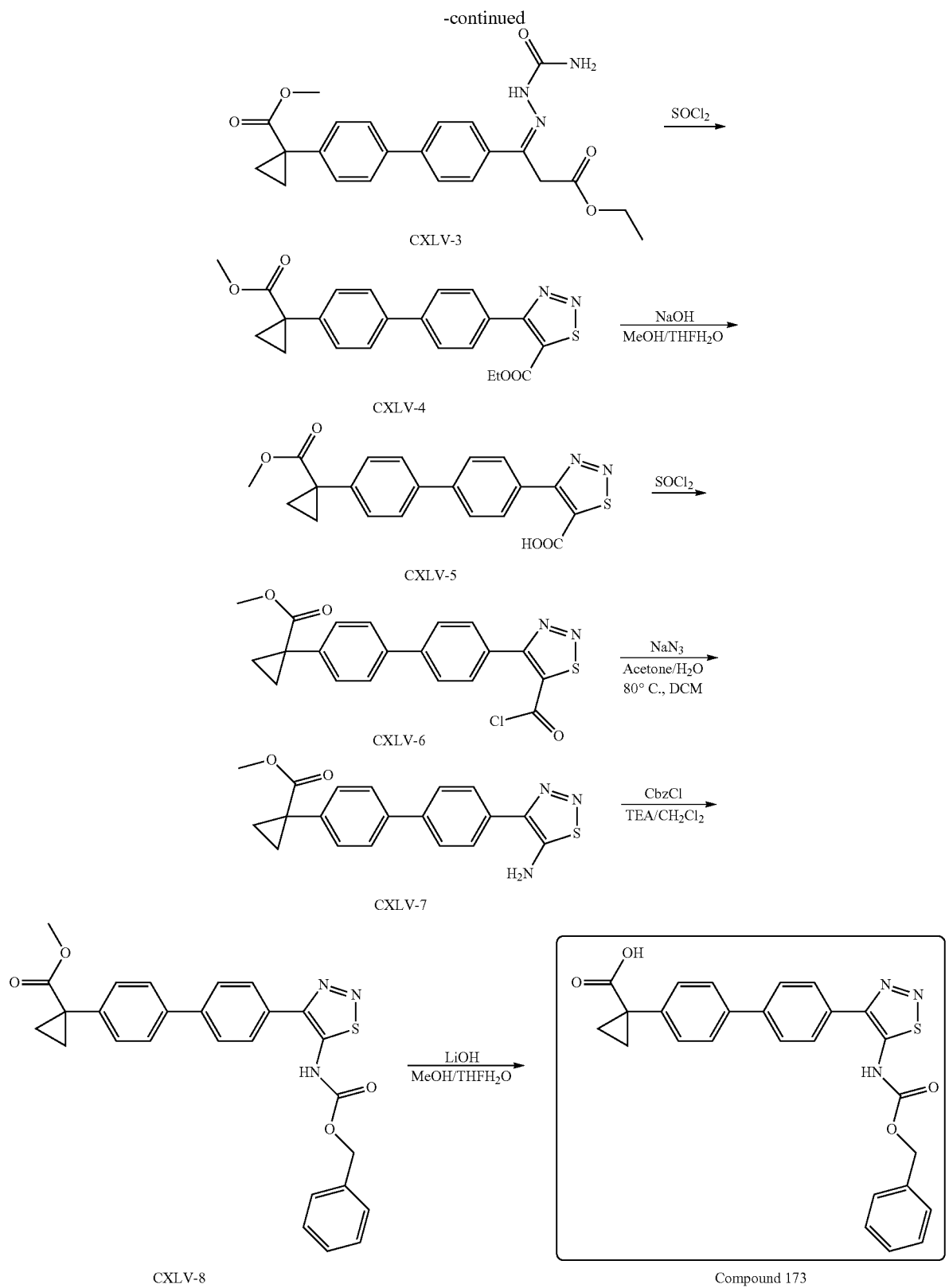

CXLV-3

CXLV-4

CXLV-5

CXLV-6

CXLV-7

CXLV-8

Compound 173

To a stirred solution of compound CXLV-1 (5.4 g, 20 mmol), compound CXLV-1A (7.3 g, 24 mmol), NaCO₃ (4.2 g, 40 mmol) in DME (90 mL) and H₂O (30 mL) was added Pd(dppf)Cl₂ (0.7 g, 0.1 mmol) under nitrogen. After the addition, the solution was heated to reflux under nitrogen overnight. The solution was concentrated, then H₂O (20 mL) was added, and the mixture was extracted with EtOAc (60 mL×3). The organic layer was combined and washed with brine, dried over Na$_2$SO$_4$, concentrated in vacuo. The residue was purified by prep HPLC to afford compound CXLV-2 (2.2 g, yield 31.4%).

To a solution of compound CXLV-2 (1.9 g, 5.2 mmol) in EtOH (50 mL), was added a mixture of NaOAc (82.03 mg, 5.24 mmol) and compound CXLV-2A (0.6 g, 5.2 mmol) in H$_2$O (5 mL). The mixture was stirred overnight at room temperature. Then concentrated, water (30 mL) was added, filtered, washed with water and t-BuOMe, the white crystals was dried by vacuo to afford compound CXLV-3 (2.2 g, yield: 54.6%). MS (ESI) m/z (M+H)$^+$ 424.1.

SOCl$_2$ (2 mL) was added dropwise to compound CXLV-3 (1 g, 2.35 mmol) and the resulting mixture was stirred for 2 hours at room temperature. The mixture was diluted with DCM (30 mL) and then satur. NaHCO$_3$ (50 mL) was added slowly. The organic layer was separated and the aqueous layer was extracted with DCM (30 mL×3). The combined organic layer was washed with brine, dried over Na$_2$SO$_4$, concentrated in vacuo. The residue was purified by column chromatography on silica gel (petroleum ether:EtOAc=10:1) to afford compound CXLV-4 (500 mg, yield: 52%). MS (ESI) m/z (M+H)$^+$ 409.1.

To a solution of compound CXLV-4 (0.5 g, 1.22 mmol) in MeOH (10 mL), THF (10 mL, H$_2$O (10 mL) was added NaOH (146.8 mg, 3.66 mmol). The mixture was stirred for 30 minutes at room temperature. The volatile solvent was removed by evaporation in vacuum and the resulting aqueous solution was acidified to pH=2 with 2N HCl, and extracted with EtOAc (25 mL×3). The combined organic layers were washed with brine (100 mL×2), dried and concentrated under reduced pressure to give compound CXLV-5 (450 mg, yield: 97%). MS (ESI) m/z (M+H)$^+$ 381.0.

The mixture of compound CXLV-5 (450 mg, 1.18 mmol) in 5 mL of SOCl$_2$ was heated to reflux for 3 hours, and then concentrated under reduced pressure to give the compound. CXLV-6 (460 mg, crude yield: 97%), which was used to next step directly.

To a solution of compound CXLV-6 (460 mg, 1.1 mmol) in acetone was added NaN$_3$ (100 mg, 1.4 mmol) and stirred overnight at room temperature. Then DCM (30 mL) and H$_2$O (1 mL) was added and heated to 80° C. for two hours. Then the mixture was cooled to room temperature, extracted with DCM (30 mL), washed with brine, dried and concentrated. The residue was purified by chromatography (PE/EA=4:1) to give compound CXLV-7 (120 mg yield: 97%). MS (ESI) m/z (M+H)$^+$ 351.9.

To a solution of compound CXLV-7 (30 mg, 0.085 mmol) in pyridine (3 mL) was added Cbz-Cl (22 mg, 0.128 mmol) and the resulting mixture was stirred overnight at room temperature. Then H$_2$O (10 mL) was added, and the mixture was extracted with EtOAc (10 mL×3). The organic layer was combined and washed with brine, dried over Na$_2$SO$_4$, concentrated in vacuo. The residue was purified by prep HPLC to afford compound CXLV-8 (11 mg, yield: 26%). MS (ESI) m/z (M+H)$^+$ 486.1.

Preparation of Compound 173

To a solution of compound CXLV-8 (10 mg, 0.02 mmol) in MeOH (1 mL), THF (1 mL), H$_2$O (1 mL) was added LiOH—H$_2$O (3.5 mg, 0.08 mmol). The mixture was stirred overnight at room temperature. The solvent was removed by evaporation, the resulting aqueous solution was acidified to pH=5 with 2 N HCl, and extracted with EtOAc (10 mL×3). The combined organic layers were washed with brine (5 mL×2), and concentrated under reduced pressure. The residue was purified by prep HPLC to afford Compound 173 (7 mg, yield: 74%). $^1$H NMR (DMSO-d$_6$, 400 MHz): δ 7.76-7.81 (m, 4H), 7.64 (d, J=8.4 Hz, 2H), 7.39-7.45 (m, 4H), 7.33-7.38 (m, 3H), 5.28 (s, 2H), 1.45-1.48 (m, 2H), 1.16-1.19 (m, 2H). MS (ESI) m/z (M+H)$^+$ 472.1.

Synthesis of Compound 174

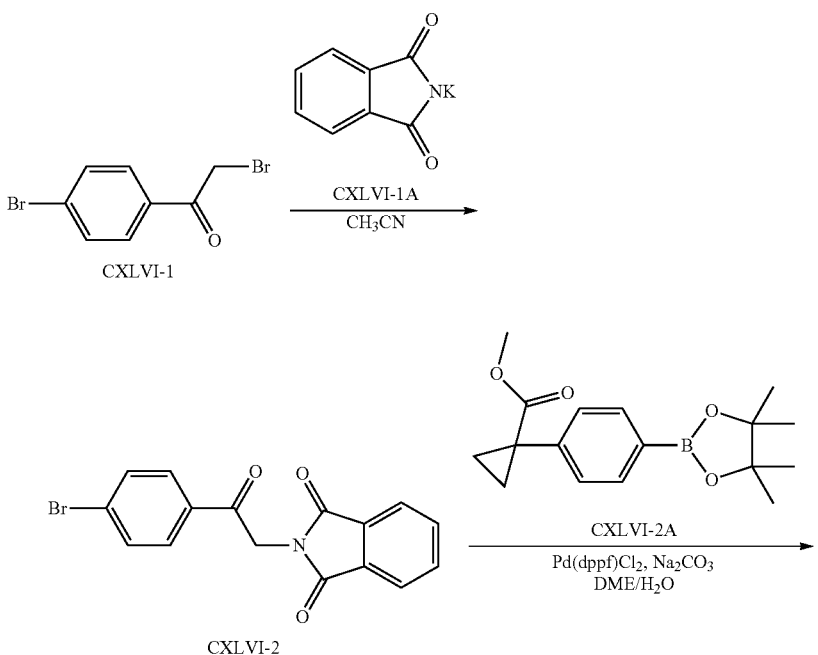

-continued
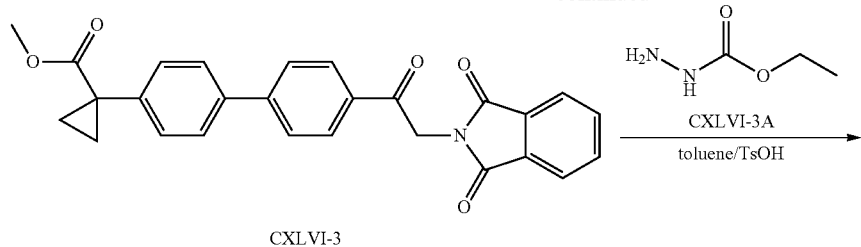
CXLVI-3
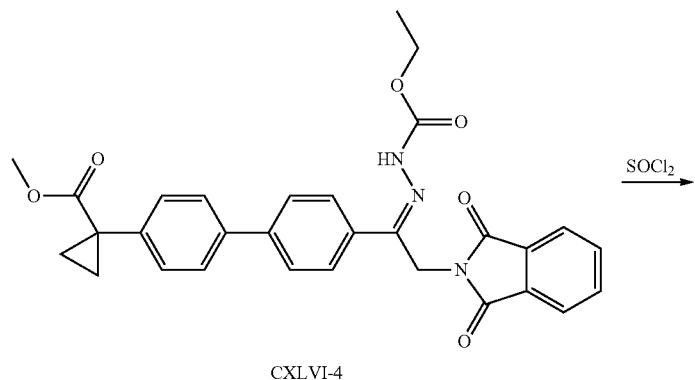
CXLVI-4
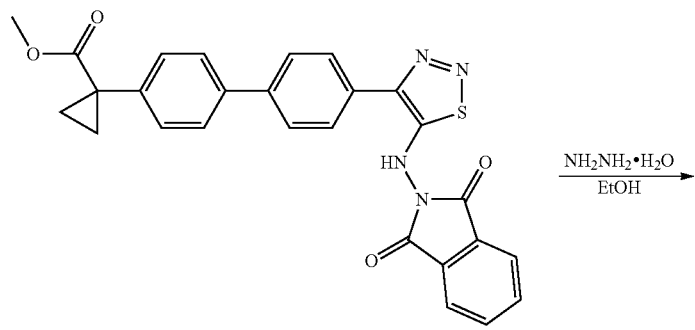
CXLVI-5
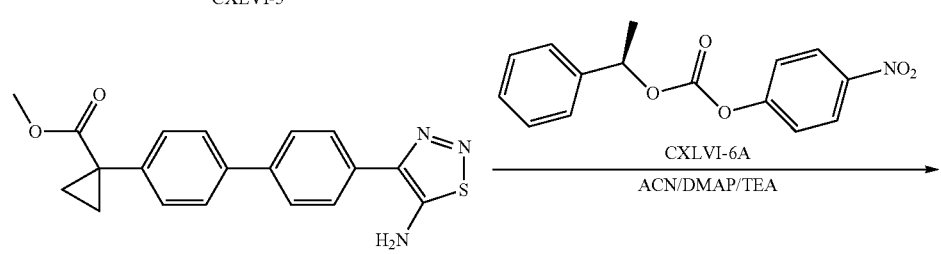
CXLVI-6
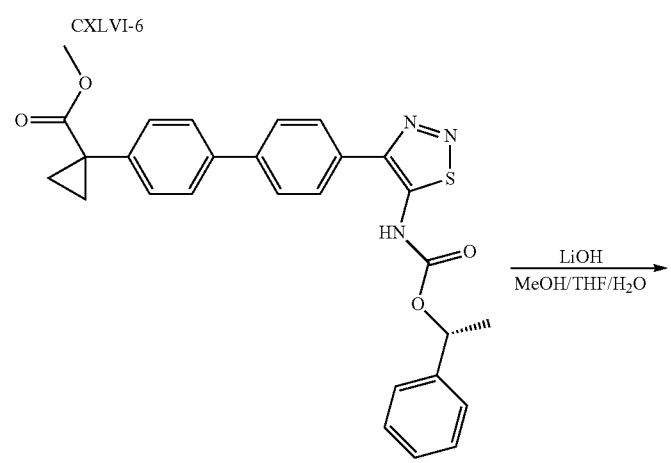
CXLVI-7

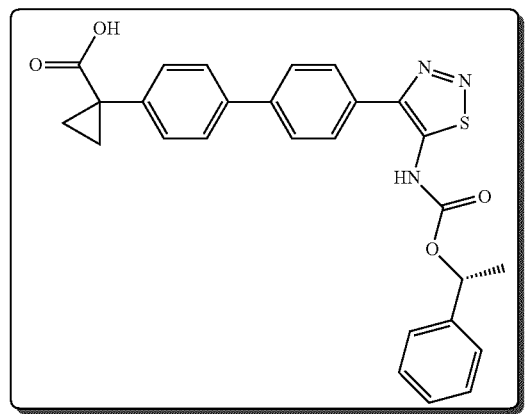

Compound 174 aq. NaOH →

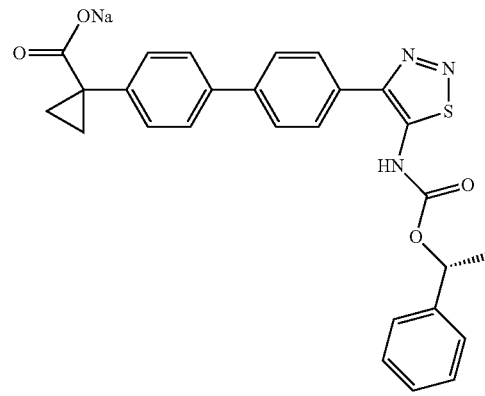

Compound 174a

The mixture of compound CXLVI-1 (20 g, 7.2 mmol) and compound CXLVI-1A (14 g, 7.6 mmol) in acetonitrile (350 mL) was heated to reflux overnight. After concentrated, $H_2O$ (200 mL) and DCM (500 mL) was added, the organic layer was separated, washed with 0.2N sodium hydroxide solution and brine, dried over $Na_2SO_4$ and concentrated. The residue was purified by column chromatography (PE/EA=5/1) to afford compound CXLVI-2 (8 g, yield 32.4%).

The mixture of compound CXLVI-2 (3.6 g, 10.48 mmol), compound CXLVI-2A (3.8 g, 12.56 mmol), $Na_2CO_3$ (2.2 g, 20.96 mmol) and Pd(dppf)$Cl_2$ (76.6 mg, 0.11 mmol) in 40 mL of DME:$H_2O$ (v/v=3:1) was heated to reflux for 2 hours under nitrogen atmosphere. After concentrated, the residue was partitioned between $H_2O$ (20 mL) and DCM (100 mL). The aqueous phase was extracted with DCM. The combined organic layer was washed with brine, dried over $Na_2SO_4$ and concentrated. The residue was purified by column chromatography on silica gel (PE/EA =1:1) to afford compound CXLVI-3 (3.8 g, yield 82.6%).

The mixture of compound CXLVI-3 (2.4 g, 5.45 mmol), compound CXLVI-3A (567 mg, 5.45 mmol), TsOH (102.6 mg, 0.054 mmol) in 40 mL of toluene was heated to reflux for 2 hours. After concentrated, the precipitate was filtered, washed with EtOH and $H_2O$, and dried to afford compound CXLVI-4 (2.6 g, yield 90.6%). MS (ESI) m/z (M+H)$^+$ 536.1.

SOCl$_2$ (15 mL) was added dropwise to compound CXLVI-4 (2.6 g, 4.9 mmol) and stirred for 2 hours at room temperature. Then DCM (30 mL) was added and status NaHCO$_3$ (50 mL) was added slowly. Extracted with DCM (30 mL×3), the organic layer was combined and washed with brine, dried over $Na_2SO_4$, concentrated in vacuo to afford compound CXLVI-5 (2.1 mg, yield 89%).

To a stirred solution of compound CXLVI-5 (2.1 g, 0.45 mmol) in EtOH (30 mL) was heated to refluxed, and then $N_2H_4 \cdot H_2O$ (90 mg, 1.8 mmol) was added dropwise. After the addition, the solution was stirred at reflux for 2 days. After concentrated, the residue was partitioned between $H_2O$ and DCM, the aqueous phase was extracted with DCM. The combined organic layer was washed with brine, dried over $Na_2SO_4$, and concentrated. The residue was purified by column chromatography on silica gel (PE/EA=5:1) to afford compound CXLVI-6 (1.2 g, yield 75%).

The mixture of compound CXLVI-6 (150 mg, 0.43 mmol), compound CXLVI-6A (146.2 mg, 0.51 mmol), TEA (51.75 mg, 0.51 mmol) and DMAP (5.2 mg, 0.043 mmol) in acetonitrile (5 mL) was heated to reflux under nitrogen overnight. After concentrated, the residue was partitioned between $H_2O$ (5 mL) and DCM (20 mL), the aqueous phase was extracted with DCM. The combined organic layer was washed with brine, dried over $Na_2SO_4$, and concentrated. The residue was purified by column chromatography on silica gel (PE:EA=8:1) to afford compound CXLVI-7 (200 mg, yield 93%). MS (ESI) m/z (M+H)$^+$ 500.1.

Preparation of Compound 174

To a solution of compound CXLVI-7 (200 mg, 0.4 mmol) in MeOH (10 mL), THF (10 mL, $H_2O$ (10 mL) was added LiOH—$H_2O$ (100.8 mg, 2.4 mmol). The mixture was stirred overnight at room temperature. Then the volatile solvent was removed by evaporation in vacuum and the resulting aqueous solution was acidified to pH=2 with 2 N HCl and extracted with EtOAc (25 mL×3). The combined organic layers were washed with brine (10 mL×2), and concentrated under reduced pressure. The residue was purified by prep HPLC to give Compound 174 (150 mg, yield: 70.2%). $^1$H NMR (DMSO-$d_6$, 400 MHz): δ 11.52 (s, 1H), 7.80 (d, J=8.4 Hz, 2H), 7.75 (d, J=8.4 Hz, 2H), 7.65 (d, J=8.4 Hz, 2H), 7.26-7.42 (m, 7H), 5.86-5.92 (q, 1H), 1.54 (d, J=6.8 Hz, 3H), 1.45-1.47 (m, 2H), 1.15-1.18 (m, 2H).

Preparation of Compound 174a

To a solution of Compound 174 (148.6 mg, 0.306 mmol) in MeOH (1 mL) was added 0.05 N NaOH aqueous solution (6.12 mL, 0.306 mmol), and the mixture was stirred for one hour at r.t. Then the volatile solvent was removed by evaporation and the resulting aqueous solution was lyophilized to give Compound 174a. $^1$H NMR (DMSO-$d_6$, 400 MHz): δ 8.59 (d, J=8.4 Hz, 2H), 7.68 (d, J=8.4 Hz, 2H), 7.64 (d, J=8.0 Hz, 2H), 7.41 (d, J=8.4 Hz, 2H), 7.20-7.32 (m, 5H), 5.80-5.84 (q, 1H), 1.47 (d, J=6.4 Hz, 3H), 1.45-1.46 (m, 2H), 1.15-1.16 (m, 2H). MS (ESI) m/z (M+H)$^+$ 486.1.

Synthesis of Compound 175

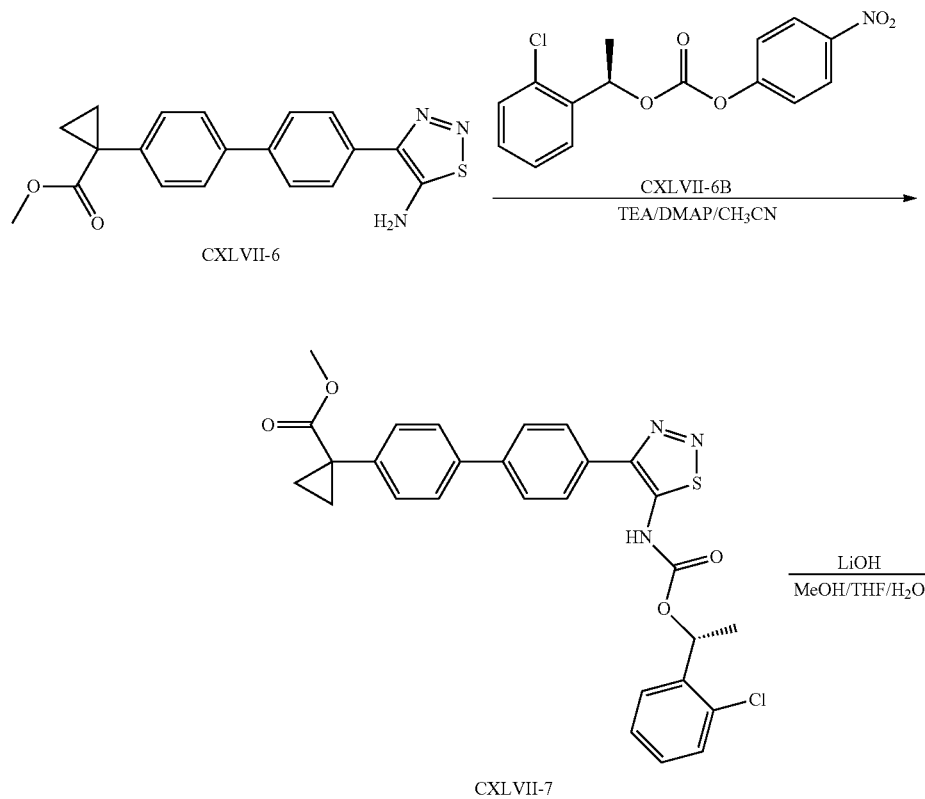

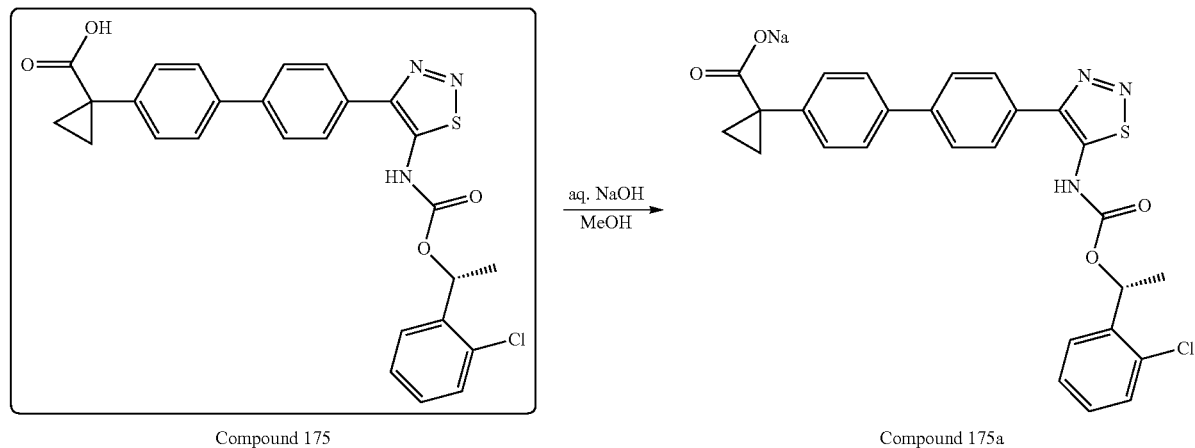

Compound 175 was prepared analogously to the procedure described in the synthesis of Compound 174. $^1$H NMR (DMSO-$d_6$, 400 MHz): δ 11.60 (br, 1H), 7.82 (d, J=8.4 Hz, 2H), 7.77 (d, J=8.4 Hz, 2H), 7.66 (d, J=8.4 Hz, 2H), 7.56 (dd, J=7.6 Hz, J=2.0 Hz, 1H), 7.46 (dd, J=7.6 Hz, J=2.0 Hz, 1H), 7.43 (d, J=8.4 Hz, 2H), 7.31-7.39 (m, 2H), 6.13 (q, J=6.4 Hz, 1H), 1.4 (d, J=6.4 Hz, 3H), 1.45-1.48 (m, 2H), 1.16-1.19 (m, 2H). MS (ESI) m/z (M+H)$^+$ 520.1.

Compound 175a was prepared analogously to the procedure described in the synthesis of Compound 174a. $^1$H NMR (DMSO-$d_6$, 400 MHz): δ 8.55 (d, J=8.4 Hz, 2H), 7.62-7.68 (m, 4H), 7.52-7.54 (m, 1H), 7.41-7.47 (m, 3H), 7.31-7.35 (m, 1H), 7.24-7.28 (m, 1H), 6.11 (q, J=6.4 Hz, 1H), 1.47-1.49 (m, 5H), 1.16-1.17 (m, 2H). MS (ESI) m/z (M+H)$^+$ 520.1.

Synthesis of Compound 176
Synthetic Route (Scheme CXLVIII)
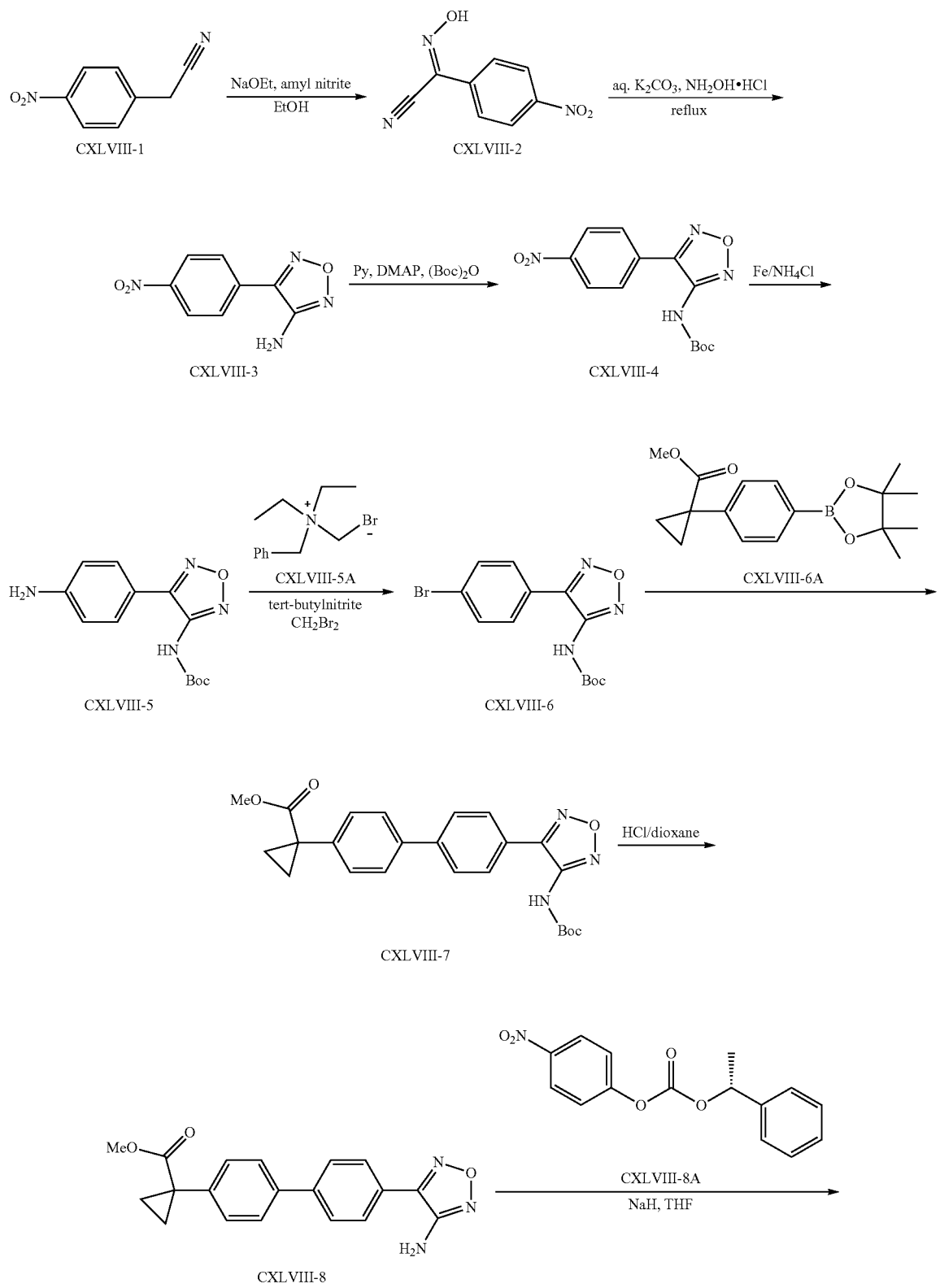

-continued

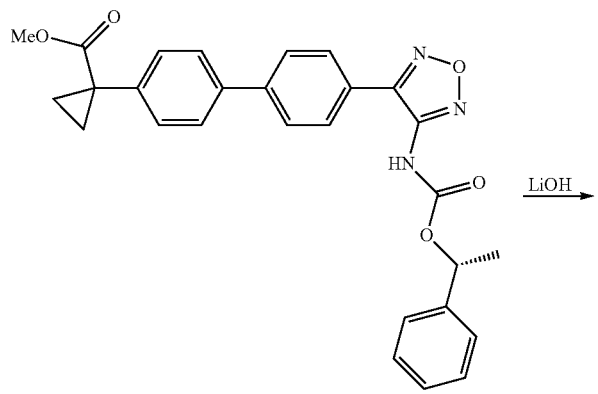

CXLVIII-9

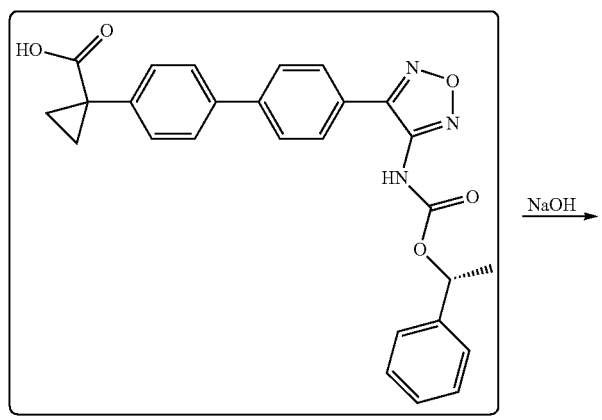

Compound 176          Compound 176a

To an ice-cold stirred suspension of compound CXLVIII-1 (5 g, 30.8 mmol) in anhydrous EtOH (25 mL) was added NaOEt (1.84 g, 27 mmol) in 20 mL anhydrous EtOH dropwise. The mixture was stirred for 20 mins at 0° C. and amyl nitrite (5.42 g, 46.2 mmol) was added dropwise. After 40 mins, 25 mL of EtOH was added. After stirred for 2 hours, NMR indicated that the reaction was complete. The reaction was diluted with EtOAc and washed with 1N HCl and saturated $NaHCO_3$, and concentrated. The residue was purified with flushed column (petroleum ether:EtOAc=100:1~4:1) to give the desired compound CXLVIII-2 (3 g, yield: 51%).

To a suspension of compound CXLVIII-2 (25 g, 130.8 mmol) and $K_2CO_3$ (108 g, 785 mmol) in $H_2O$ (130 mL) was added a suspension of $NH_2OH·HCl$ (90.9 g, 1.31 mol) and $K_2CO_3$ (90.9 g, 650 mmol) in 200 mL of water. The mixture was stirred at room temperature for 48 hours. Then the mixture was heated to 85° C. and stirred for 5 hours. After cooled, the mixture was extracted with EA (120 mL×3). The combined organic layers were washed with $H_2O$ (50 mL) and dried over $Na_2SO_4$, concentrated in vacuo. The residue was purified by column chromatography (petroleum ether/:EtOAc=5/1) to afford compound CXLVIII-3 (5.9 g, yield 22%).

To a solution of compound CXLVIII-3 (1 g, 4.85 mmol) in DCM (10 mL) and pyridine (20 mL) were added di-tertbutyl dicarbonate (2.72 g, 12.5 mmol) and DMAP (1.22 g, 9.7 mmol). The reaction mixture was stirred at 70° C. for 3 hours. The solvent was removed under reduced pressure. The residue was dissolved in $CH_2Cl_2$ (100 mL) and washed with $H_2O$ (50 mL×2). The aqueous layer was extracted with $CH_2Cl_2$ (30 mL×3). The combined organic layers were dried over $Na_2SO_4$, concentrated in vacuo. The residue was purified by flush column chromatography (petroleum ether:EtOAc=100:1~5:1) to afford compound CXLVIII-4 (1 g, yield: 67%).

A mixture of compound CXLVIII-4 (1 g, 3.2 mmol), iron powder (900 mg, 16 mmol) and $NH_4Cl$ (170 mg, 3.2 mmol) in EtOH (30 mL) and $H_2O$ (3 mL) was heated to reflux for 3 hours. After filtration, the filtrate was concentrated under reduced pressure. The residue was suspended in $CH_2Cl_2$ (200 mL), washed with brine, dried over $Na_2SO_4$, filtered and concentrated to give crude compound CXLVIII-5 (800 mg, yield: 90.6%), which was used directly without further purification.

To a solution of compound CXLVIII-5 (828 mg, 3 mmol) in 52 mL dried dibromomethane, was added benzyltriethyl ammonium bromide (3.11 g, 13.5 mmol) followed by dropwise addition of tert-butyl nitrite (3.1 g, 30 mmol). The solution was stirred at room temperature under nitrogen atmosphere for 3 hours and was monitored by TLC (petroleum ether: EtOAc=10:1). Upon completion, the reaction was quenched by addition of aq. $NaHCO_3$ solution and extracted with dichloromethane. The combined organic extracts were washed with brine, dried over $Na_2SO_4$ and concentrated in vacuo. The residue was purified by flash column chromatography (petroleum ether:EtOAc=100:1~7:1) to afford compound CXLVIII-6 (350 mg, yield 34%).

A mixture of compound CXLVIII-6 (350 mg, 0.8 mmol), compound CXLVIII-6A (364 mg, 1.2 mmol) Pd(dppf)Cl$_2$.CH$_2$Cl$_2$ (65 mg, 0.08 mmol), acetonitrile (6 mL) and saturated aqueous NaHCO$_3$ (6 mL) were stirred at 110° C. for 30 minutes under microwave. The mixture was cooled to room temperature and extracted with ethyl acetate (5 mL×2). The combined organic layers were washed with brine and concentrated under reduced pressure. The residue was purified by flush column chromatography (petroleum ether:EtOAc=100:1~2:1) to afford compound CXLVIII-7 (100 mg, yield 29%) and compound CXLVIII-8 (120 mg, yield 37.5%)

To an ice-cooled solution of compound CXLVIII-7 (100 mg, 0.23 mmol) in anhydrous DCM (3 mL) added HCl/EA (5 mL, 4N). The reaction mixture was stirred at room temperature overnight. After concentrated, the mixture was adjust to pH=7 with aq.Na$_2$CO$_3$ and extracted with EtOAc (20 mL×3). The organic layers was washed with brine, dried over Na$_2$SO$_4$, and concentrated. The residue was purified by flush column chromatography (petroleum ether:EtOAc=100:1~2:1) to afford compound CXLVIII-8 (50 mg, yield 65%).

NaH (15 mg, 0.375 mmol) was added to a solution of compound CXLVIII-8 (50 mg, 0.15 mmol) in THF (7 mL) at 0° C. The mixture was stirred at 0° C. for 30 min, then compound CXLVIII-8A (43 mg, 0.15 mmol) in 2 mL of THF was added dropwise, and the reaction mixture was stirred at reflux overnight. After being cooled to r.t., water (5 mL) was added, and extracted with EtOAc (20 mL×2), the combined organic layer was concentrated, the residue was used to next step directly without further purification.

Preparation of Compound 176

To a stirred solution of compound CXLVIII-9 (crude from above step) in MeOH/H$_2$O (5 mL/1 mL) was added LiOH (40 mg). The mixture was stirred at room temperature overnight. Then concentrated, water (10 mL) was added, adjusts pH to 3 with 1N HCl, and extracted with EtOAc (15 mL×2). The combined organic layers were washed with brine (20 mL), dried and concentrated under reduced pressure. The residue was purified by Prep. HPLC to afford Compound 176 (14 mg, over yield for two steps: 14.4%). MS (ESI) m/z (M+Na)$^+$ 492.1.

Preparation of Compound 176a

To a solution of Compound 176 (14 mg, 0.029 mmol) in CH$_3$CN (3 mL) was added aq. NaOH (0.05N, 0.58 mL), and the mixture was stirred for one hour at r.t., then the reaction mixture was lyophilized to give Compound 176a (10 mg, yield: 69.4%). $^1$H NMR (DMSO-d$_6$, 400 MHz): δ 7.79-7.81 (m, 4H), 7.64 (d, J=8.4 Hz, 2H), 7.45 (d, J=8.4 Hz, 2H), 7.29-7.38 (m, 5H), 5.70 (q, 1H), 1.45 (brs, 2H), 1.40 (d, J=6.8 Hz, 3H), 1.14 (brs, 2H). MS (ESI) m/z (M+Na)$^+$ 492.1.

Synthesis of Compound 177

Synthetic Route (Scheme CXLIX)

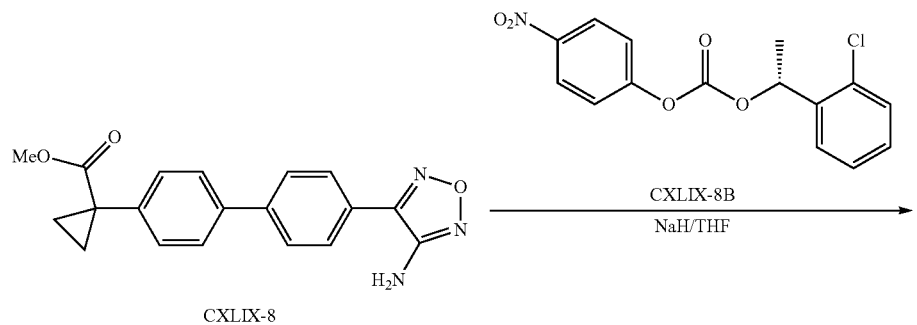

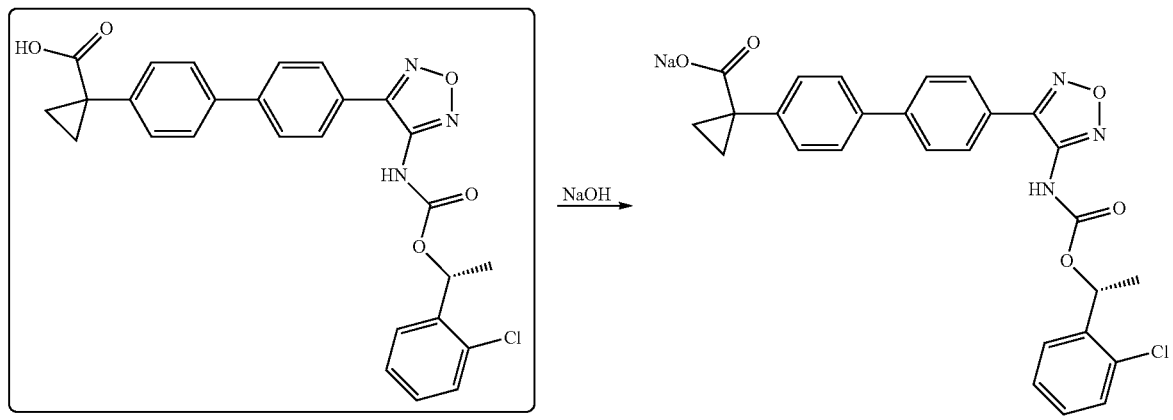

Compound 177

Compound 177a

Compound 177 was prepared analogously to the procedure described in the synthesis of Compound 176. MS (ESI) m/z (M+Na)+ 526.1.
Compound 177a was prepared analogously to the procedure described in the synthesis of Compound 176a. ¹H NMR (DMSO-d₆, 400 MHz): δ 7.77-7.84 (m, 4H), 7.64 (d, J=8.4 Hz, 2H), 7.32-7.46 (m, 6H), 5.94 (q, 1H), 1.46 (brs, 2H), 1.41 (d, J=6.4 Hz, 3H), 1.15 (brs, 2H). MS (ESI) m/z (M+Na)+ 526.1.
Synthesis of Compound 178
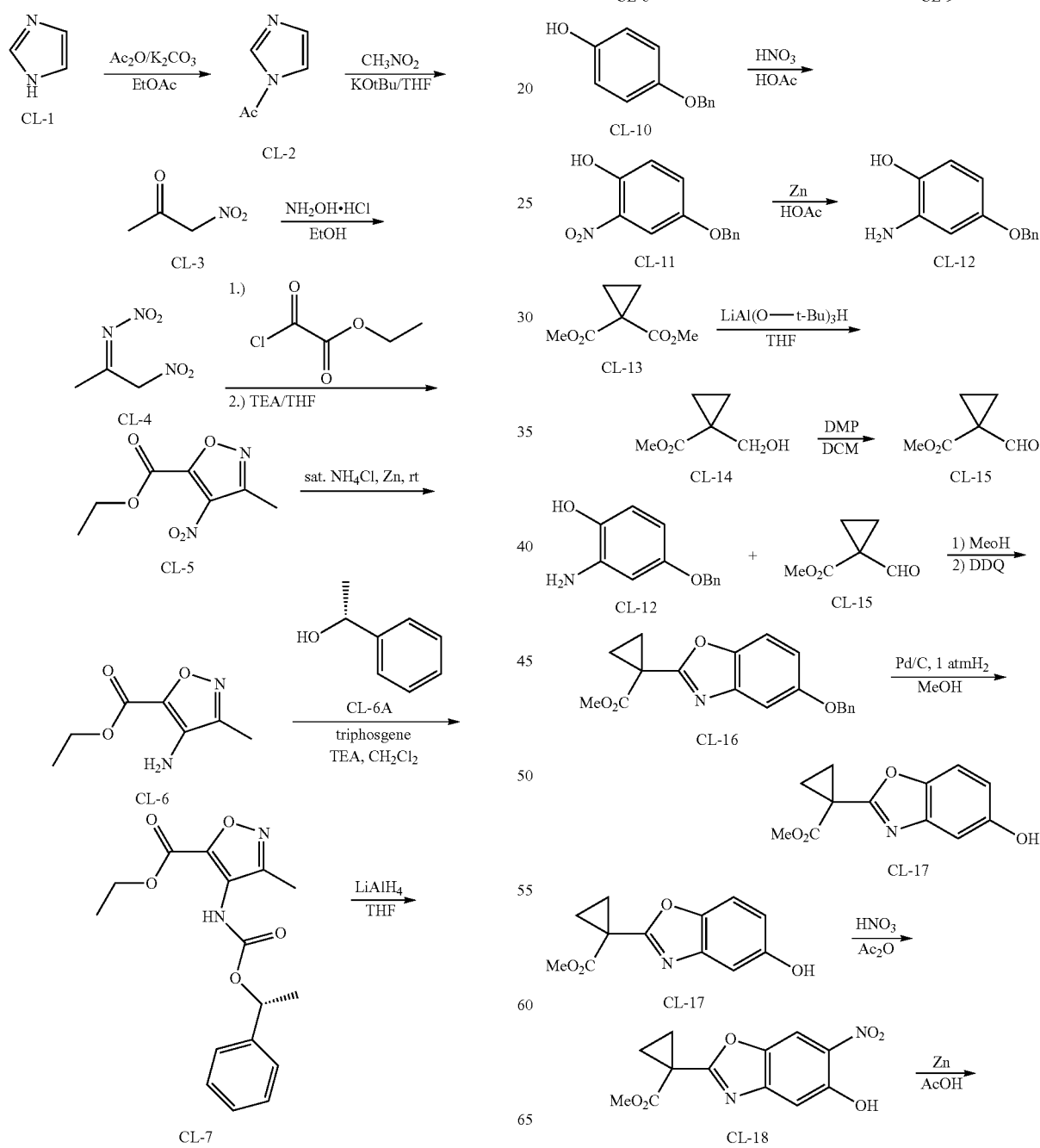

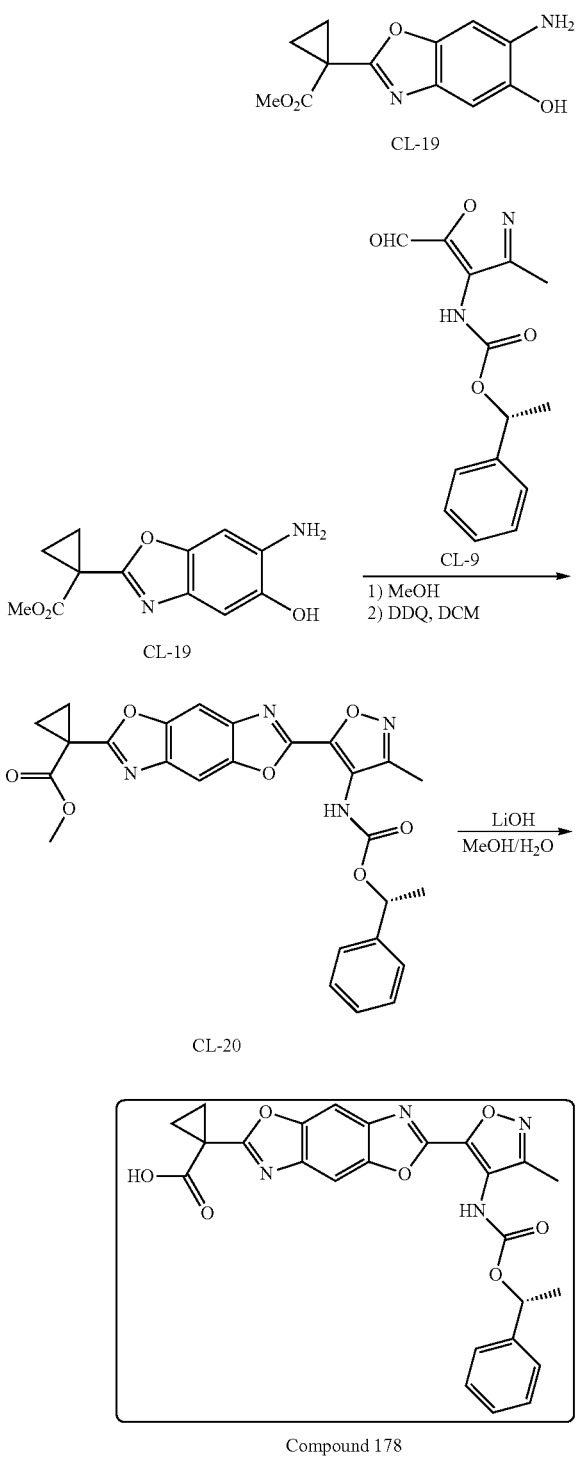

Compound 178

Acetic anhydride (50 mL, 0.55 mol) was added to a solution of compound CL-1 (34 g, 0.5 mol) in ethyl acetate (800 mL). The resulting mixture was stirred under nitrogen at room temperature for 12 h. Anhydrous potassium carbonate (137.5 g, 1 mol) was added, and stiffing was continued for 30 min. The reaction mixture was then filtered though a celite path and filtrate was concentrated to afford the desired compound CL-2 as a white solid (52 g, yield 95%).

Nitromethane (132 mL, 0.98 mol) was added dropwise to a solution of KOtBu (23 g, 0.21 mol) in anhydrous THF (400 mL) at room temperature. The mixture was cooled to 0° C. and a solution of compound CL-2 (23 g, 0.21 mol) in THF (400 mL) was added over a period of 30 min, after stirring for 12 hours at room temperature. The formed nitronate salt was filtered off, washed with THF and dissolved in water. The aqueous solution was acidified with conc. HCl to pH=3 and extracted with $CH_2Cl_2$. The combined organic phases were dried over anhydrous $Na_2SO_4$, and concentrated under reduced pressure; the crude product was obtained without further purification and used directly for next step (17.3 g, yield 80%).

To a solution of compound CL-3 (23 g, 0.22 mol) in EtOH (600 mL) was added hydroxylamine hydrochloride (15.6 g, 0.22 mol) and acetic acid (80 mL) at room temperature. The reaction was refluxed for 3 hours and cooled room temperature. The reaction mixture was concentrated under vacuum and extracted with ethyl acetate. The combined organic layer was dried with anhydrous $Na_2SO_4$. After the solvent was evaporated, the crude product was obtained without further purification and used directly for next step (20.6 g, yield 80%).

To a solution of compound CL-4 (19 g, 0.16 mol) in THF (200 mL) was added ethyl oxalyl chloride (19 mL, 0.16 mol) at room temperature. The reaction mixture was stirred for 12 hours and concentrated under vacuum. The residue was dissolved in THF and treated with a solution of $Et_3N$ (16 mL, 0.32 mol) in THF (20 mL) and stirred for 3 hours. Removed the solvent under vacuum and residue was purified by column chromatograph on silica gel (PE/EA=8/1) to give compound CL-5 as a yellow oil (5.4 g, yield 16.8%).

Compound CL-5 (5.4 g, 27 mmol) was suspended in sat. $NH_4Cl$ (200 mL) and treated Zn power (15 g, 230 mmol) at room temperature. The reaction mixture was stirred for 3 hours and ethyl acetate was added. After stirring for 20 min, Zn was filtered off. The organic phase was taken and washed with brine, dried over anhydrous $Na_2SO_4$ and concentrated under vacuum to afford the desired product as a pale yellow solid. (4 g, yield 87%).

To a stirred solution of compound CL-6 (2 g, 11.8 mmol) and $Et_3N$ (3.9 mL, 28.2 mmol) in dry $CH_2Cl_2$ (30 mL) was added a solution of triphosgene (1.17 g, 3.9 mmol) in $CH_2Cl_2$ (10 mL). The resulting mixture was stirred at 0° C. for 3 hours and then treated with compound CL-6A (1.43 g, 11.8 mmol). The reaction mixture was allowed to warm to room temperature for 10 hours. After removal of the solvent, the residue partitioned between ethyl acetate and saturated sodium hydrogen carbonate solution. The combined organic layer was dried over anhydrous $Na_2SO_4$ and filtered. The filtrated was concentrated to residue, which was purified by column chromatograph on silica gel (PE/EA=6/1) to give compound CL-7 as a pale yellow solid (1.8 g, yield 50%).

To a stirred solution of compound CL-7 (1.1 g, 3.5 mmol) in anhydrous THF (30 mL) was added lithium aluminum hydride (0.26 g, 6.9 mmol) at 0° C. The reaction mixture is stirred for another 2 hours at room temperature and quenched with dropwise addition of water. The mixture was washed 2N HCl and extracted with ethyl acetate. The combined organic layer was dried over anhydrous $Na_2SO_4$, filtered and concentrated. The residue was purified by column chromatograph on silica gel (PE/EA=4/1) to give compound CL-8 as pale yellow oil (0.76 g, yield 80%).

To a solution of compound CL-8 (0.82 g, 2.97 mmol) in CH$_2$Cl$_2$ (30 mL) was added Dess-Martin periodinane (2.5 g, 5.94 mmol). The suspension was stirred at under nitrogen at room temperature for 5 hours. A solution of saturated Na$_2$S$_2$O$_3$ and saturated NaHCO$_3$ (v/v=1:1, 50 mL) was added while keeping the temperature at 20° C. The mixture was stirred for 30 min followed by extraction with CH$_2$Cl$_2$. The combined organic phase was dried over anhydrous Na$_2$SO$_4$, filtered and evaporated to afford a crude product, and then it was purified by column chromatograph on silica gel (PE/EA=8/1) to give compound CL-9 as pale yellow oil (0.6 g, yield 73%).

To a solution of compound CL-11 (20 g, 0.1 mol) in HOAc (100 mL) was added dropwise nitric acid (7.26 mL, 0.1 mol) at room temperature. After completion of the addition, the reaction mixture was poured onto cold water and extracted with ethyl acetate. The organic phase was washed with brine and dried over anhydrous Na$_2$SO$_4$. Then the solvent was evaporated to give the crude product and purified by column chromatograph on silica gel (PE/EA=10/1) to give compound CL-11 as yellow solid (7.4 g, yield 30%).

To a solution of compound CL-11 (4.5 g, 18.4 mmol) in HOAc (50 mL) was added Zinc powder (24 g, 367.2 mmol) under cooling in ice bath, with stirring at room temperature for 2 hours. Zinc was filtered off using celite, the filtrate was adjusted to neutrality with sodium hydrogen carbonate, and extracted with ethyl acetate. The organic layer was washed with brine and dried over anhydrous Na$_2$SO$_4$, filtered and evaporated to give the crude product, which was purified by column chromatograph on silica gel (DCM/EA=7/1) to give compound CL-12 as brown solid (2.4 g, yield: 61.5%).

To a solution of compound CL-13 (10 g, 63.3 mmol) in THF (300 mL) was added lithium aluminum-tri-ter-butoxyhyride (48 g, 189.9 mmol). After stiffing for 12 hrs, the reaction mixture was diluted with CH$_2$Cl$_2$, and then washed with aq.HCl (1 M), the organic layer was dried over Na$_2$SO$_4$. Removal of the solvent under reduced pressure to obtain the title compound CL-14 that was used in the next step without further purification (7 g, yield: 87.5%).

To a solution of compound CL-14 (7 g, 53.8 mmol) in CH$_2$Cl$_2$ (300 mL) was added Dess-Martin periodinane (46 g, 107.7 mmol). The suspension was stirred at under nitrogen at room temperature for 5 hours. A solution of saturated Na$_2$S$_2$O$_3$ and saturated NaHCO$_3$ (v/v=1:1, 500 mL) was added while keeping the temperature at 20° C. The mixture was stirred for 30 min followed by extraction with CH$_2$Cl$_2$. The combined organic phase was washed with brine, dried over anhydrous Na$_2$SO$_4$, filtered and evaporated to afford a crude product, which was purified by column chromatograph on silica gel (PE/EA=10/1) to give compound CL-15 as pale yellow oil (1.6 g, yield: 24%).

Compound CL-15 (0.96 g, 7.42 mmol) and compound CL-12 (1.75 g, 8.16 mmol) were dissolved in anhydrous methanol (30 mL). To this solution was added 4 A molecular sieves. The reaction mixture was stirred at 45° C. The solvent was removed in vacuo and residue was dissolved in CH$_2$Cl$_2$. To this solution was added DDQ (1.85 g, 8.9 mmol) and the reaction mixture was stirred for 2 hours. The reaction mixture was diluted with saturated aqueous NH$_4$Cl, the aqueous phase was extracted with CH$_2$Cl$_2$. The organic phase was combined and dried over anhydrous Na$_2$SO$_4$, filtered and evaporated to afford a crude product, which was purified by column chromatograph on silica gel (PE/EA=10/1) to give compound CL-16 as yellow oil (1.9 g, yield: 80%).

To a solution of compound CL-16 (2 g, 618 mmol) in MeOH (20 mL) was added 10% Pd/C (200 mg), and the mixture was stirred under a hydrogen balloon for 1 h. After filtration though celite and washing with MeOH, the filtrate was concentrated in vacuo to afford the crude product, which was purified by prep-HPLC to give compound CL-17 as off-white solid (0.36 g, yield: 25.7%).

To a solution of compound CL-17 (300 mg, 1.29 mmol) in Ac$_2$O (6 mL) was added dropwise nitric acid (0.3 mL) at room temperature. After stirring for 10 min, the reaction mixture was poured onto cold water and extracted with ethyl acetate. The organic phase was washed with brine and dried over anhydrous Na$_2$SO$_4$. Then the solvent was evaporated to give the crude product, and then it was purified by column chromatograph on silica gel (PE/EA=5/1) to give compound CL-18 as yellow solid (100 mg, yield: 27.9%).

To a solution of compound CL-18 (100 mg, 0.26 mmol) in HOAc (5 mL) was added Zinc powder (468 mg, 7.19 mmol) under cooling in an ice-water bath, with stiffing at room temperature for 2 hours. Zinc was filtered off using celite, the filtrate was adjusted to neutrality with sodium hydrogen carbonate, and extracted with ethyl acetate. The organic layer was washed with brine and dried over anhydrous Na$_2$SO$_4$, filtered and evaporated to give the crude product, which was purified by column chromatograph on silica gel (PE/EA=1/1) to give compound CL-19 as brown solid (45 mg, yield: 50.5%).

Compound CL-9 (55 mg, 0.199 mmol) and compound CL-19 (45 mg, 0.18 mmol) were dissolved in anhydrous methanol (5 mL). To this solution was added 4 A molecular sieves. The reaction mixture was stirred at 45° C. The solvent was removed in vacuo and residue was dissolved in CH$_2$Cl$_2$. To this solution was added DDQ (49 mg, 0.216 mmol) and the reaction mixture was stirred for 2 hours. The reaction was diluted with saturated aqueous NH$_4$Cl, the aqueous phase was extracted with CH$_2$Cl$_2$. The combined organic phase was washed with brine and dried over anhydrous Na$_2$SO$_4$, filtered and evaporated to afford a crude product, which was purified by prep-TLC (PE/EA=2/1) to give compound CL-20 as pale yellow solid (40 mg, yield: 44.4%).

Preparation of Compound 178

To a solution of compound 20 (40 mg, 0.08 mmol) in MeOH/H$_2$O (v/v=4:1, 8 mL) was added LiOH.H$_2$O (17 mg, 0.4 mmol). The reaction mixture was stirred at 45° C. overnight. The solvent was removed in vacuo and the residue was partitioned with ethyl acetate, the organic phase was extracted with water. The combined aqueous extract was acidified to pH 5 with aq. HCl (1 M). The aqueous phase was extracted with ethyl acetate. The combined organic phase was dried over anhydrous Na$_2$SO$_4$, filtered and evaporated to afford a crude product, which was purified by prep-HPLC to afford Compound 178 as white solid (11 mg, yield: 28%). $^1$HNMR (CD$_3$OD, 400 MHz) δ 7.99 (s, 1H), 7.84 (s, 1H), 7.50-7.20 (m, 5H), 5.85 (q, J=6.4 Hz, 1H), 2.32 (s, 3H), 1.79-1.75 (m, 2H), 1.71-1.66 (m, 2H), 1.66 (d, J=6.4 Hz, 3H). MS (ESI) m/z (M+H)$^+$ 489.3.

Synthesis of Compound 179
Synthetic Route (Scheme CLI)
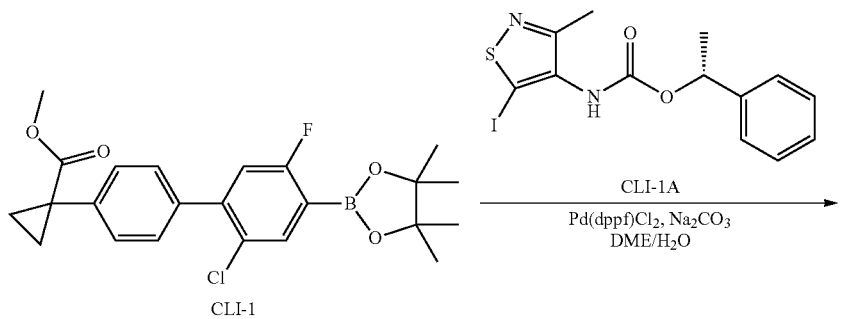
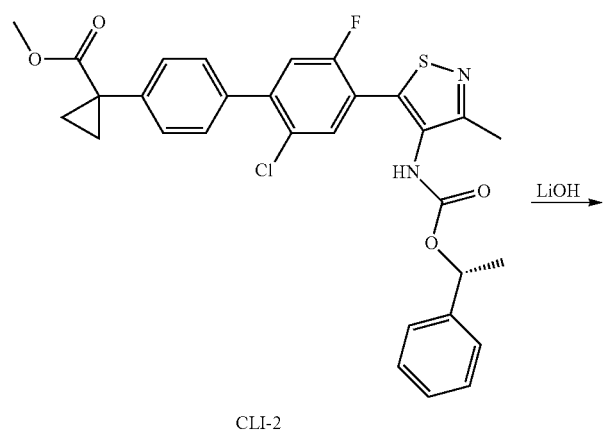
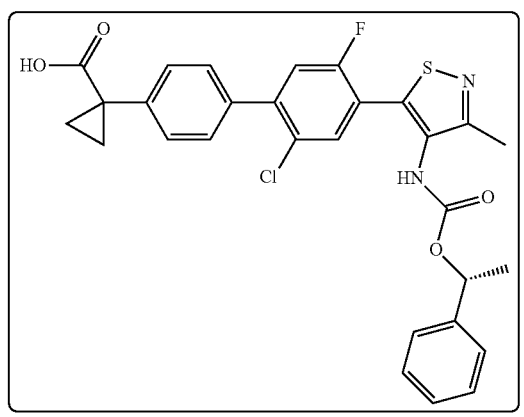
Compound 179                                      Compound 179a
Compound 179 was prepared analogously to the procedure described in the synthesis of Compound 117. MS (ESI) m/z (M+H)$^+$ 551.1.
Compound 179a was prepared analogously to the procedure described in the synthesis of Compound 117a. $^1$H NMR (400 MHz, DMSO-d$_6$): δ 9.56 (s, 1 H), 7.77 (d, J=6.8 Hz, 1H), 7.55-7.33 (m, 10 H), 5.72 (q, 1 H), 2.32 (s, 3 H), 1.49-1.51 (m, 5 H), 1.18-1.22 (m, 2 H). MS (ESI) m/z (M+H)$^+$ 551.1.

Synthesis of Compound 180
Synthetic Route (Scheme CLII)
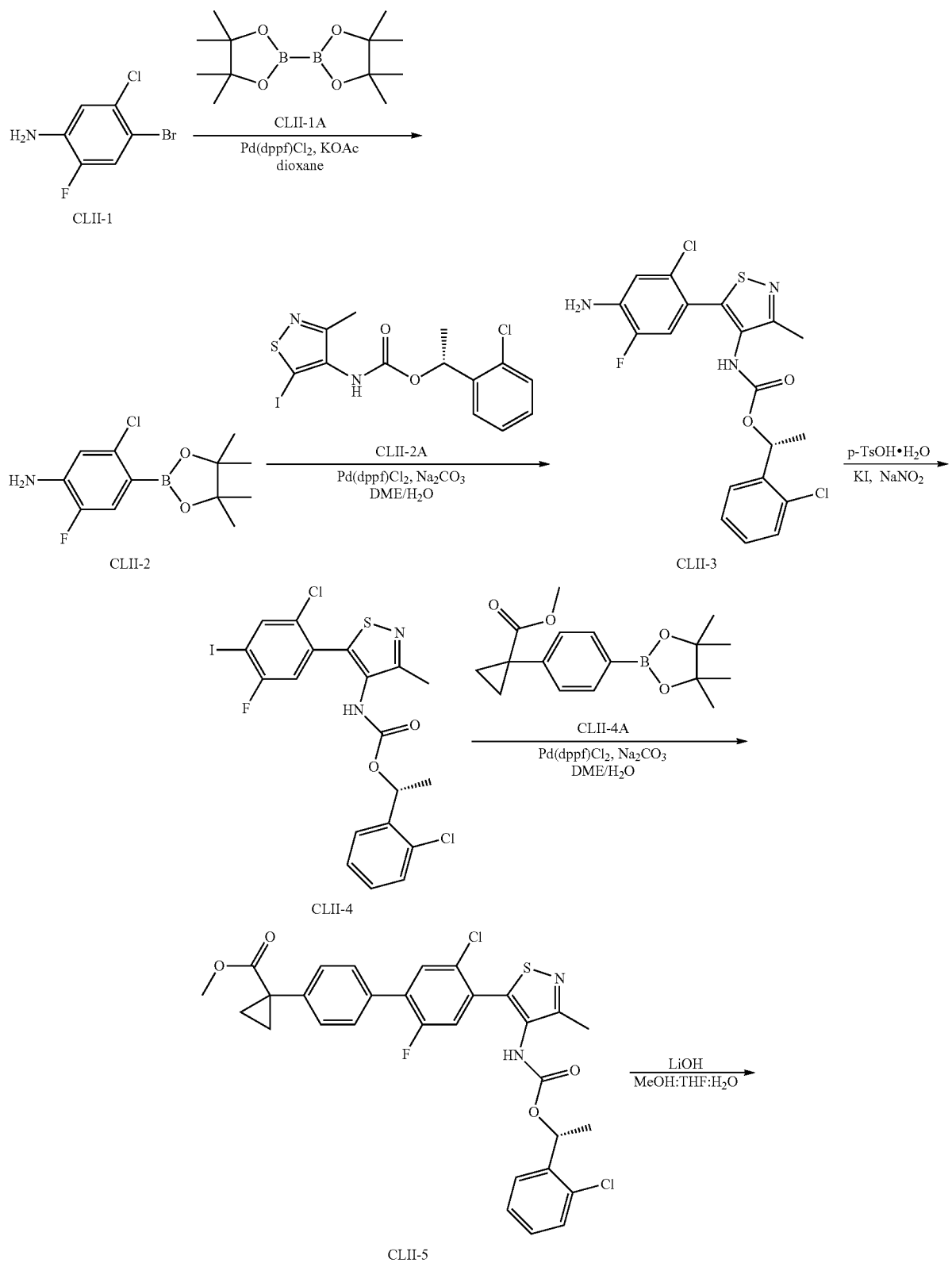

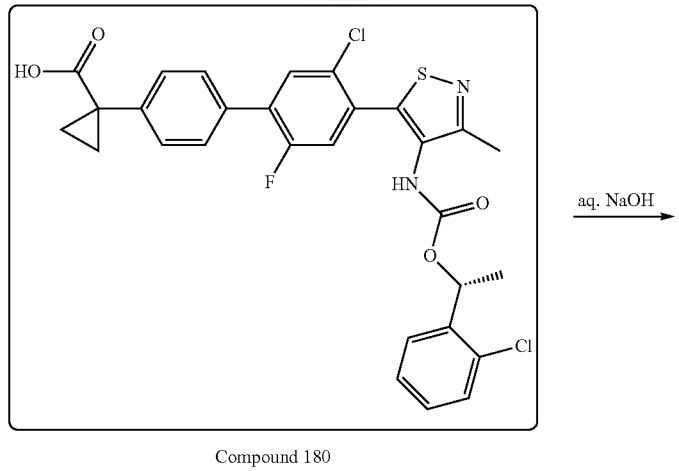

Compound 180 aq. NaOH →

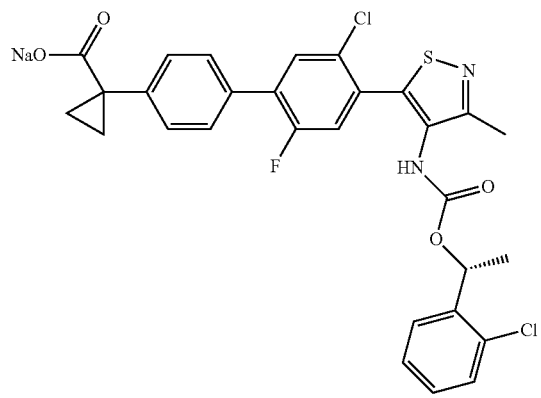

Compound 180a

The mixture of compound CLII-1 (3 g, 13.45 mmol), compound CLII-1A (3.65 g, 14.34 mmol), KOAc (2.64 g, 26.9 mmol) and Pd(dppf)Cl$_2$ (0.3 g) in dioxane (50 mL) was heated to reflux under nitrogen for overnight. After concentrated, the residue was partitioned between H$_2$O and DCM, the aqueous phase was extracted with DCM, and the combined organic layer was washed with brine, dried over Na$_2$SO$_4$, concentrated. The residue was purified by chromatography on silica gel (PE:EA=20:1) to afford compound CLII-2 (1.7 g, yield 46.45%) MS (ESI) m/z (M+H)$^+$ 271.0.

To a solution of compound CLII-2 (851 mg, 3.129 mmol) in DME/H$_2$O (20 mL, v/v=3:1), Na$_2$CO$_3$ (0.552 g, 2.61 mmol) and compound CLII-2A (1.1 g, 2.61 mmol) were added, the resulting mixture was purged with nitrogen, then Pd (dppf)Cl$_2$ (95 mg, 0.13 mmol) was added. The reaction mixture was stirred at 80° C. overnight under nitrogen protection. After being cooled to r.t., the mixture was poured into water, and extract with EtOAc (30 mL×3), the combined organic layers were dried over Na$_2$SO$_4$, concentrated in vacuo. The residue was purified by chromatography (PE:EA=5:1) to afford compound CLII-3 (500 mg, yield: 36.5%) MS (ESI) m/z (M+H)$^+$ 439.0.

To a solution of p-TsOH.H$_2$O (1.56 g, 8.2 mmol) in MeCN (30 mL) was added compound CLII-3 (1.2 g, 2.73 mmol) at 10-15° C. Then a solution of NaNO$_2$ (1.13 g, 6.8 mmol) and KI (0.377 g, 5.467 mmol) in H$_2$O (10 mL) was added dropwise. The reaction mixture was stirred for 10 min then allowed to stir at r.t. for 3 hours. TLC showed that reaction was completed, H$_2$O (10 mL), satur. NaHCO$_3$ (10 mL) and satur. Na$_2$S$_2$O$_3$ (20 mL) was added, and extracted with EtOAc (50 mL). The organic layer was separated, dried and concentrated, the residue was purified by chromatography (PE:EA=3:1) to afford compound CLII-4 (800 mg, yield 53.3%) MS (ESI) m/z (M+H)$^+$ 549.9.

To a solution of compound CLII-4 (800 mg, 1.45 mmol) in DME/H$_2$O (20 mL, v/v=3:1) was added Na$_2$CO$_3$ (307.4 mg, 2.9 mmol) and compound CLII-4A (527 mg, 1.745 mmol). The resulting mixture was purged with nitrogen, then Pd(dppf)Cl$_2$ (80 mg) was added. The reaction mixture was stirred at 80° C. overnight under nitrogen protection. After completion of the reaction, the mixture was poured into water, extract with EtOAc (30 mL×3), the combined organic layers were dried over Na$_2$SO$_4$, concentrated in vacuo. The residue was purified by chromatography (PE:EA=2:1) to afford compound CLII-5 (500 mg, yield 61.14%) MS (ESI) m/z (M+H)$^+$ 598.9.

Preparation of Compound 180

To a solution of compound CLII-5 (400 mg, 0.709 mmol) in MeOH (3 mL), THF (3 mL) and H$_2$O (3 mL), was added LiOH (148.9 mg, 3.5 mmol). The reaction mixture was stirred at room temperature overnight. After concentrated, the mixture was adjust to pH=2 with HCl (1N) and extracted with EtOAc (20 mL×3). The organic layers was washed with brine, dried over Na$_2$SO$_4$, and concentrated. The residue was purified by prep. HPLC to afford Compound 180 (90 mg, yield: 12.8%). MS (ESI) m/z (M+H)$^+$ 587.0.

Preparation of Compound 180a
To a solution of Compound 180 (30 mg, 0.0545 mmol) in MeOH (1 mL) and MeCN (5 mL) was added 0.05 N sodium hydroxide solution (1.091 mL) at 0° C. The reaction mixture was stirred for 20 minutes. The mixture was lyophilized to give Compound 180a. $^1$H NMR (400 MHz, DMSO-$d_6$): δ 7.68 (d, J=7.2 Hz, 1 H), 7.36-7.44 (m, 6 H), 7.28-7.33 (m, 3 H), 5.94-5.98 (q, 1 H), 2.33 (s, 3 H), 1.45 (d, J=6.8 Hz, 3 H), 1.23-1.26 (m, 2 H), 0.70-0.72 (m, 2 H). MS (ESI) m/z (M+H)$^+$ 587.0.
Synthesis of Compound 181
Synthetic Route (Scheme CLIII)
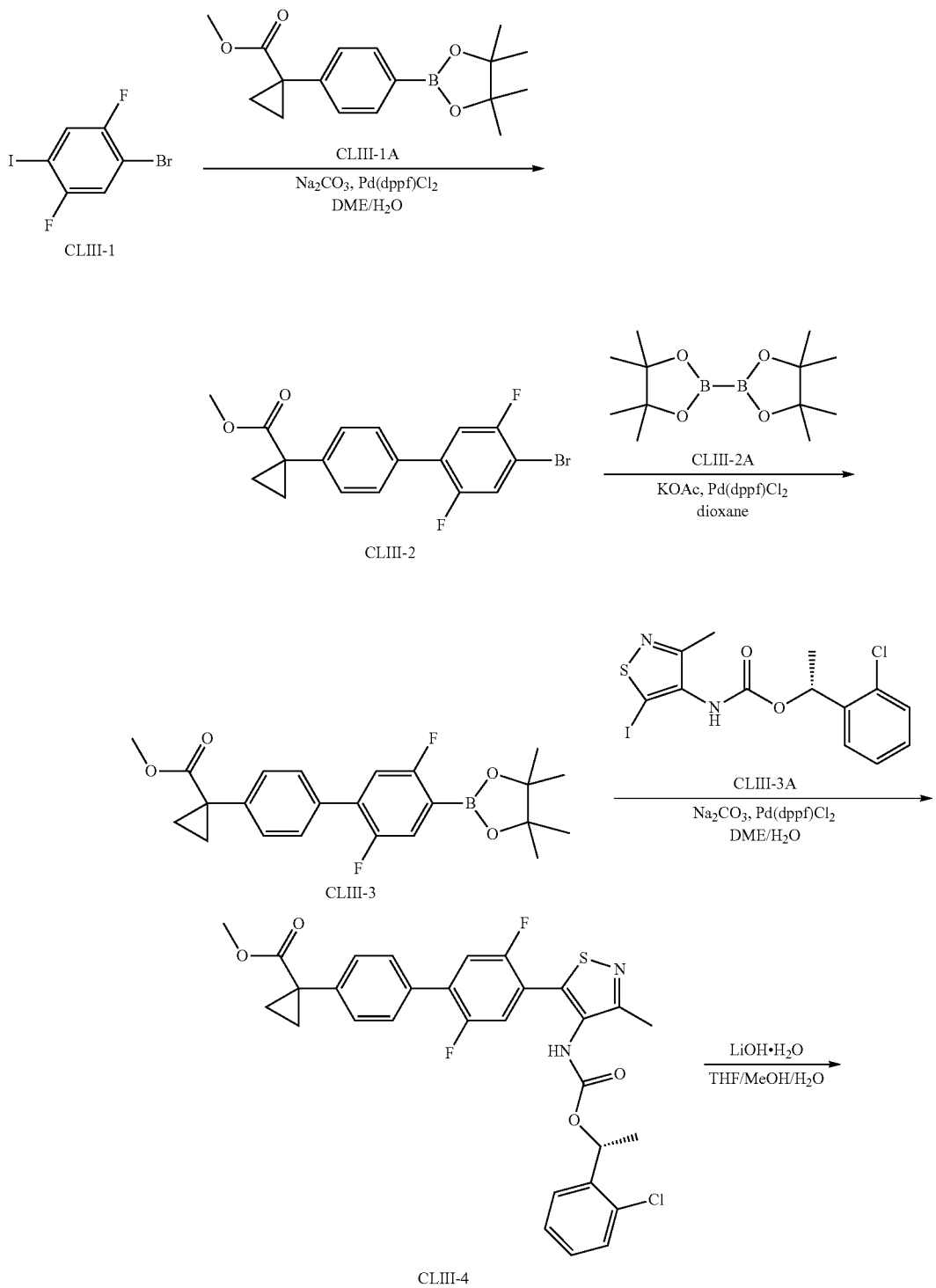

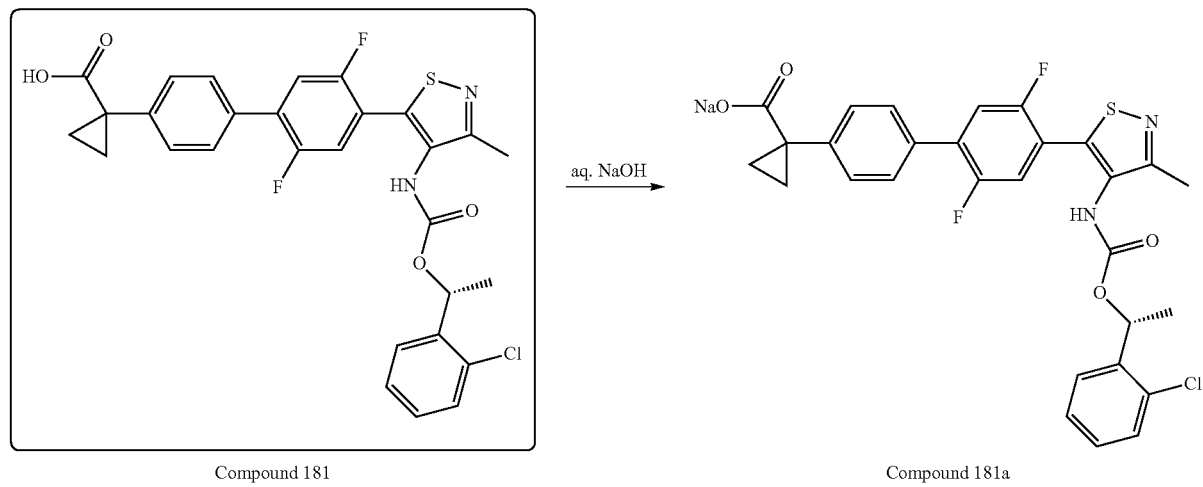
Compound 181
Compound 181a
Compound 181 was prepared analogously to the procedure described in the synthesis of Compound 117. MS (ESI) m/z (M+H)+ 516.1.
Compound 181a was prepared analogously to the procedure described in the synthesis of Compound 117a. $^1$H NMR (DMSO-d$_6$, 400 MHz): δ 9.55 (br, 1H), 7.60-7.65 (m, 1H), 7.51-7.56 (m, 4H), 7.40-7.46 (m, 3H), 7.34-7.38 (m, 2H), 5.94-5.96 (m, 1H), 2.31 (s, 3H), 1.51-1.53 (m, 3H), 1.41-1.43 (m, 2H), 1.06-1.08 (m, 2H). MS (ESI) m/z (M+H)+ 569.0.
Synthesis of Compound 182
Synthetic Route (Scheme CLIV)
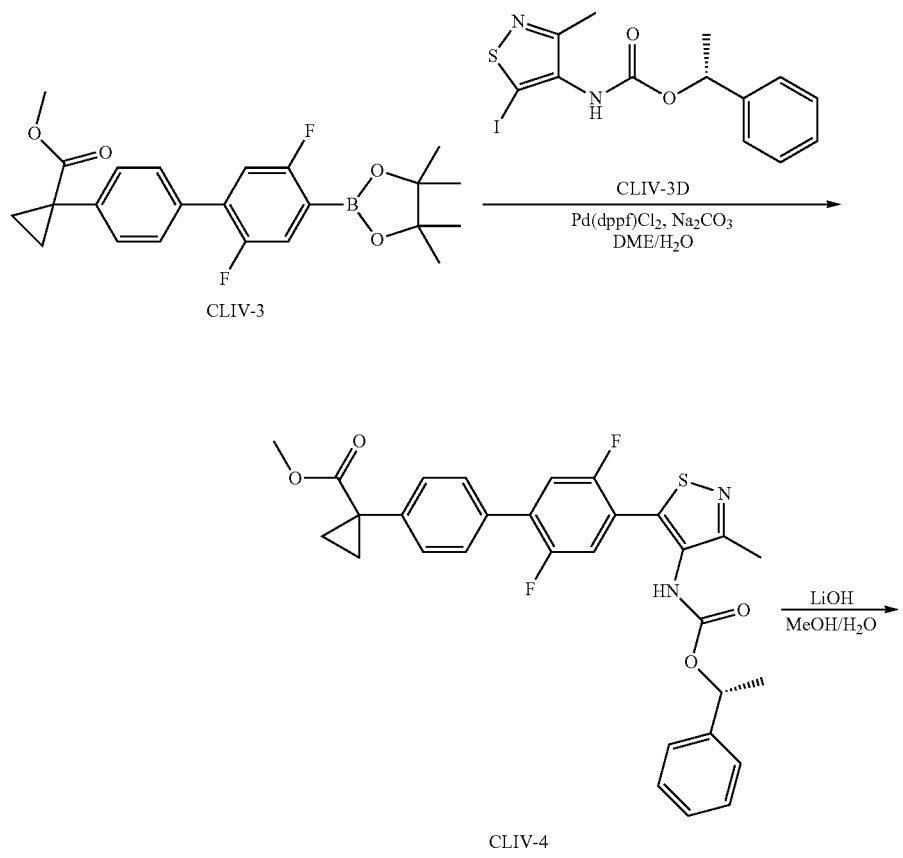

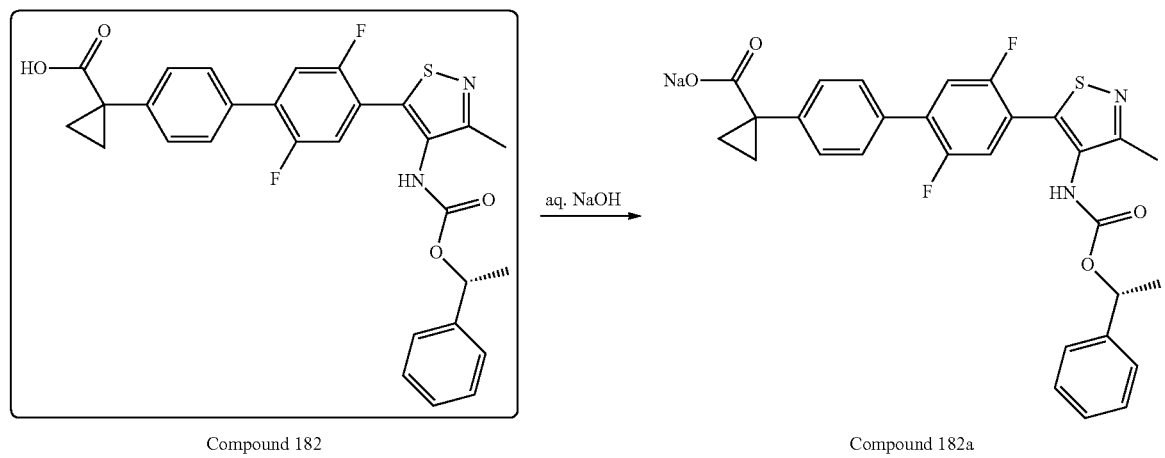
Compound 182
Compound 182a
Compound 182 was prepared analogously to the procedure described in the synthesis of Compound 117. MS (ESI) m/z (M+H)+ 535.1.
Compound 182a was prepared analogously to the procedure described in the synthesis of Compound 117a. ¹H NMR (DMSO-d₆, 400 MHz): δ 9.09 (s, 1H), 7.28-7.61 (m, 11H), 5.71-5.72 (q, 1H), 2.31 (s, 3H), 1.50 (d, J=6.4 Hz, 3H), 1.22-1.23 (m, 2H), 0.74-0.75 (m, 2H). MS (ESI) m/z (M+H)+ 535.1.
Synthesis of Compound 183
Synthetic Route (Scheme CLV)
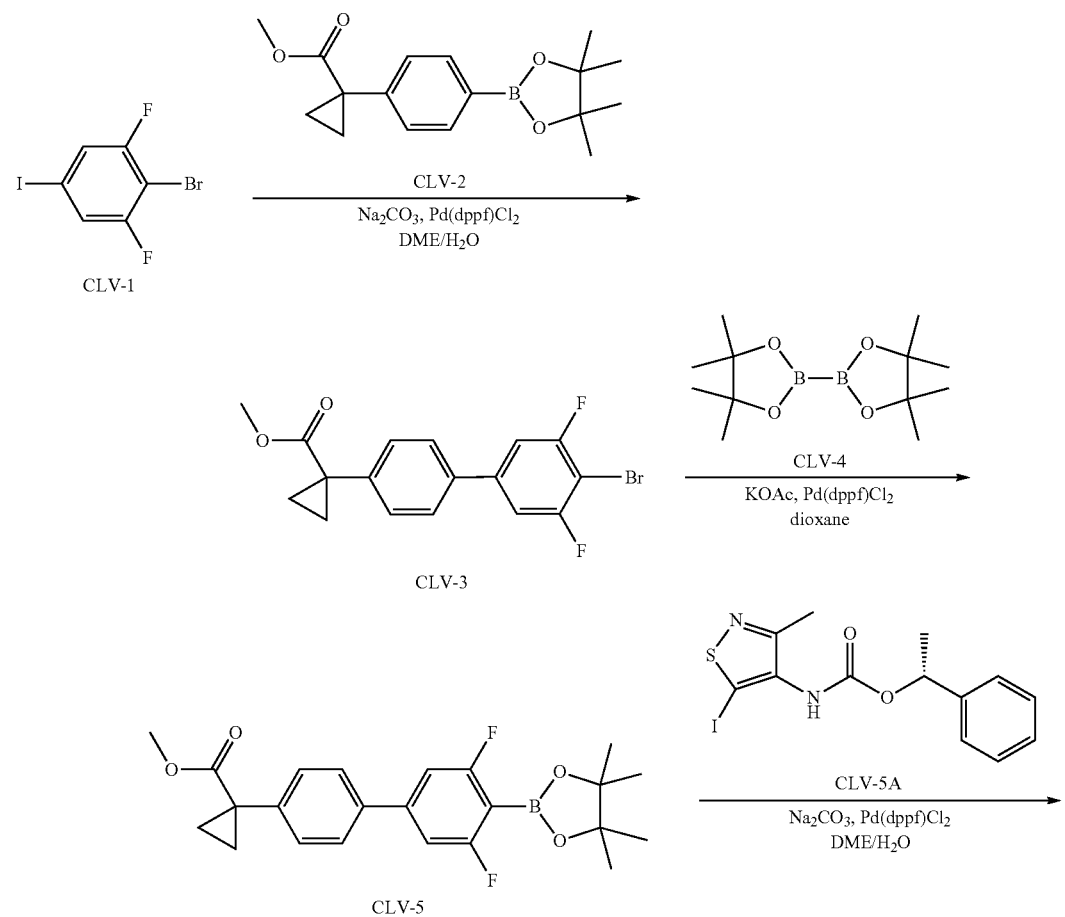

-continued
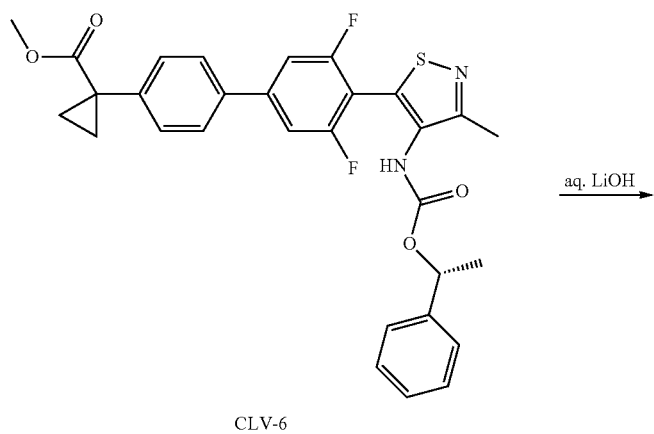
CLV-6
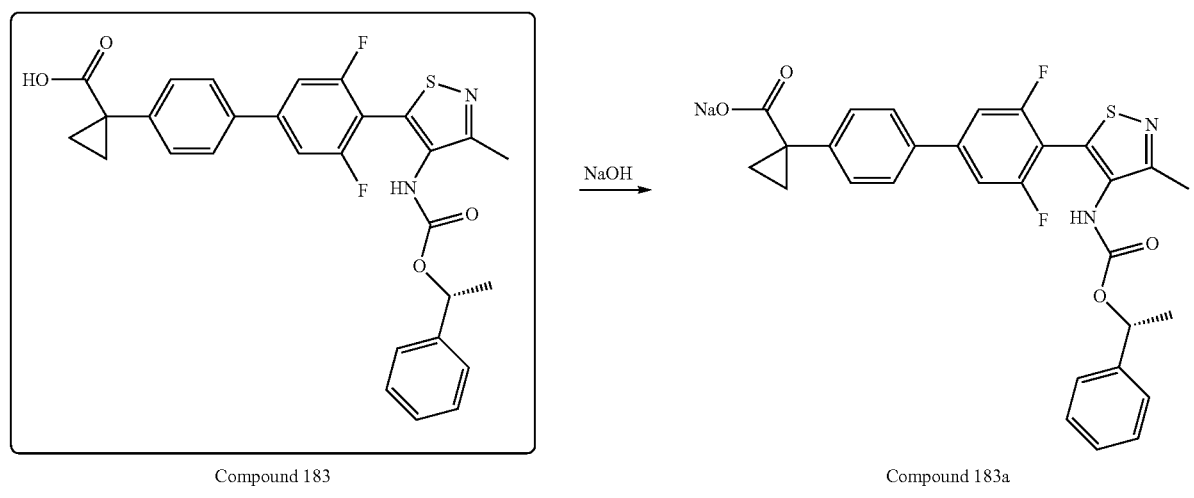
Compound 183
Compound 183a
Compound 183 was prepared analogously to the procedure described in the synthesis of Compound 117. MS (ESI) m/z (M+H)+ 535.1.
Compound 183a was prepared analogously to the procedure described in the synthesis of Compound 117a. $^1$H NMR (400 MHz, DMSO-d$_6$): δ 7.59-7.61 (m, 2H), 7.48-7.50 (m, 2H), 7.26-7.36 (m, 7H), 5.69-5.71 (m, 1H), 2.39 (s, 3H), 1.52 (br, 5H), 1.05 (m, 2H). MS (ESI) m/z (M+H)+ 535.0.
Synthesis of Compound 184
Synthetic Route (Scheme CLVI)
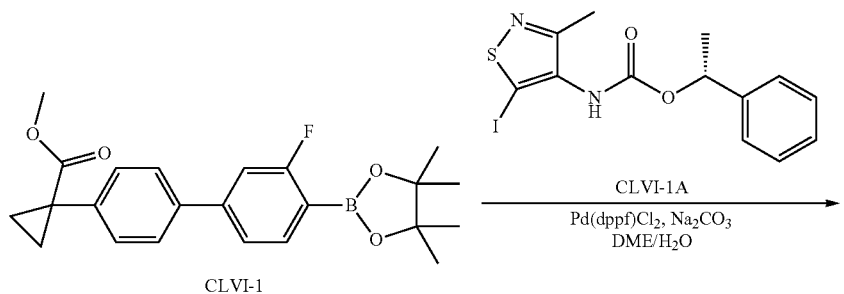

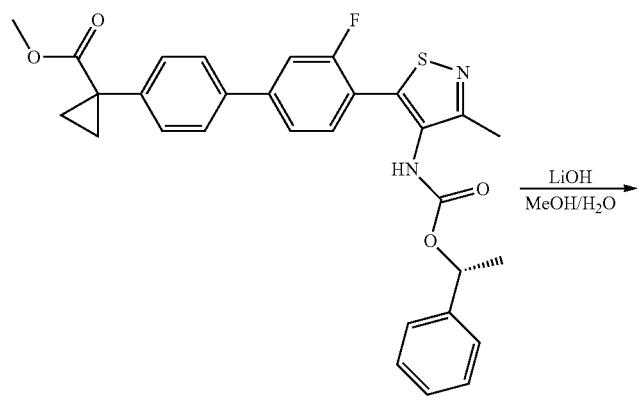

CLVI-2

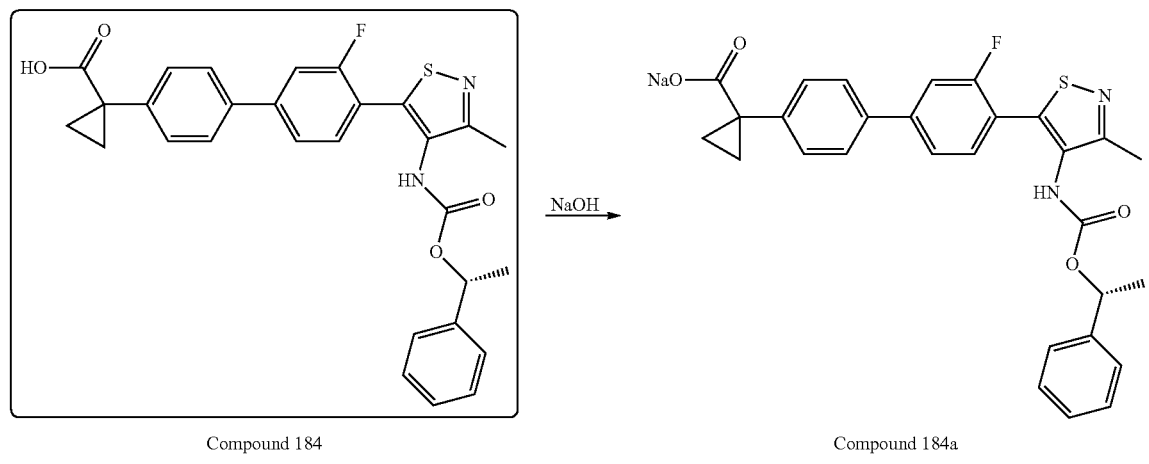

Compound 184

Compound 184a

The detailed synthetic procedure for compound CLVI-1 has been described in the synthesis of Compound 119.

Compound 184 was prepared analogously to the procedure described in the synthesis of Compound 119. MS (ESI) m/z (M+H)+ 517.1.

Compound 184a was prepared analogously to the procedure described in the synthesis of Compound 119a. $^1$H NMR (400 MHz, DMSO-d$_6$): δ 8.97 (s, 1 H), 7.56-7.62 (m, 5 H), 7.41 (d, J=8.4 Hz, 2H), 7.27-7.35 (m, 5 H), 5.69-5.70 (q, 1 H), 2.33 (s, 3 H), 1.45 (d, J=6.4 Hz, 3H), 1.29-1.31 (m, 2 H), 0.80-0.83 (m, 2 H). MS (ESI) m/z (M+H)+ 517.1.

Synthesis of Compound 185

Synthetic Route (Scheme CLVII)

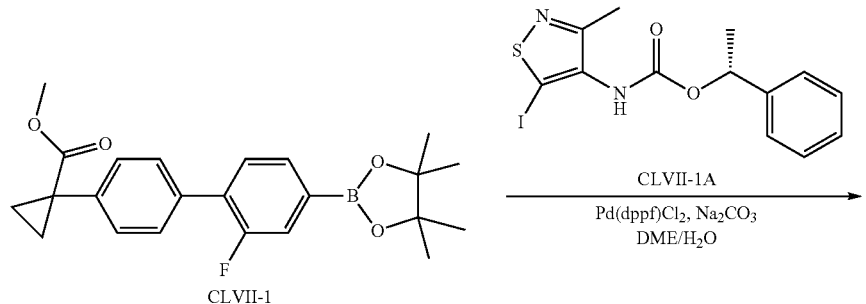

CLVII-1

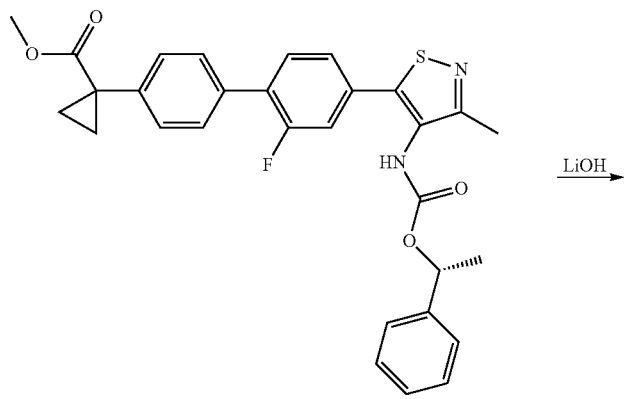

CLVII-2

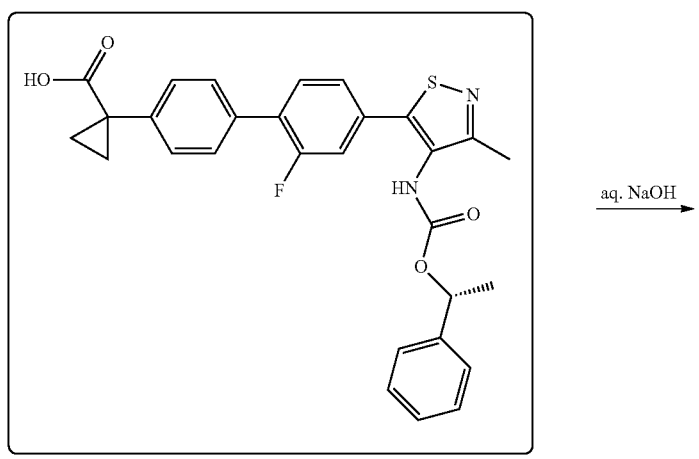

Compound 185

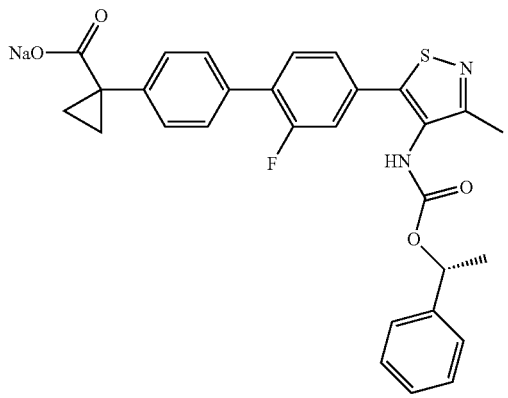

Compound 185a

The detailed synthetic procedure for compound CLVII-1 has been described in the synthesis of Compound 117.

Compound 185 was prepared analogously to the procedure described in the synthesis of Compound 117. MS (ESI) m/z (M+H)⁺ 517.2.

Compound 185a was prepared analogously to the procedure described in the synthesis of Compound 117a. $^1$H NMR (DMSO-$d_6$, 400 MHz): δ 9.01 (br, 1H), 7.57-7.61 (m, 1H), 7.40-7.47 (m, 6H), 7.27-7.34 (m, 5H), 5.73-5.78 (q, 1H), 2.30 (s, 3H), 1.48 (d, J=6.4 Hz, 3H), 1.34-1.36 (m, 2H), 0.85-0.88 (m, 2H). MS (ESI) m/z (M+H)⁺517.2.

Synthesis of Compound 186
Synthetic Route (Scheme CLVIII)
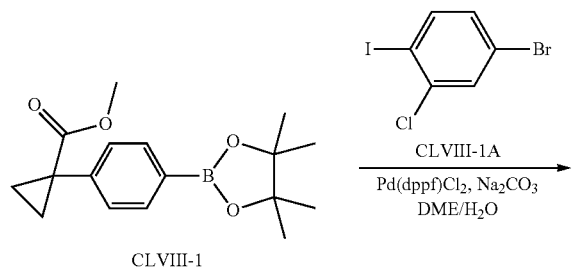
CLVIII-1
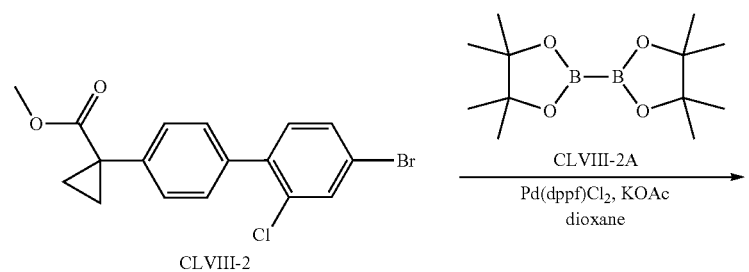
CLVIII-2
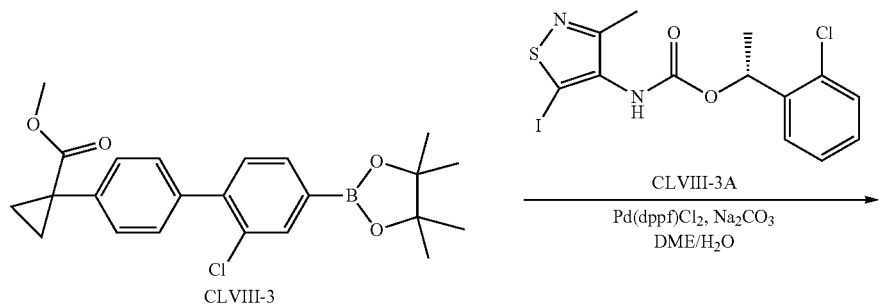
CLVIII-3
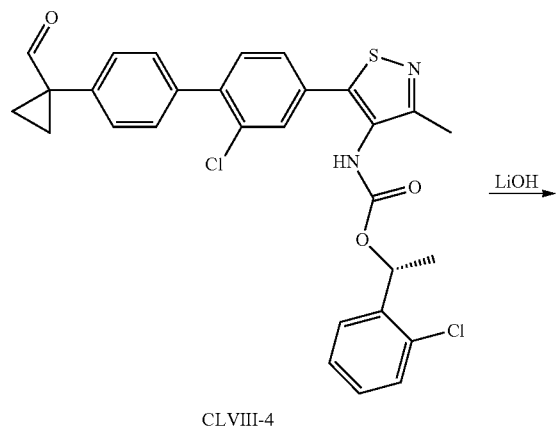
CLVIII-4

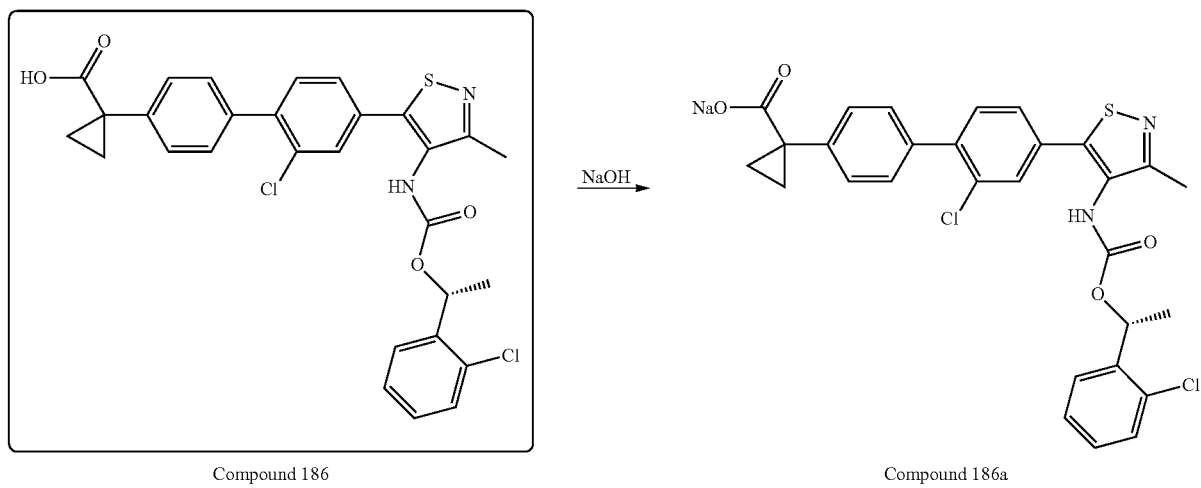
Compound 186
Compound 186a
Compound 186 was prepared analogously to the procedure described in the synthesis of Compound 117. MS (ESI) m/z (M+H)+ 567.1.
Compound 186a. $^1$H NMR (DMSO-d$_6$, 400 MHz): δ 7.81 (s, 1H), 7.52-7.61 (m, 2H), 7.42-7.45 (m, 2H), 7.28-7.38 (m, 6H), 5.95-6.01 (q, 1H), 2.25 (s, 3H), 1.45 (d, J=6.4 Hz, 3H), 1.21-1.22 (m, 2H), 0.72-0.74 (m, 2H). MS (ESI) m/z (M+H)+ 567.1.
Synthesis of Compound 187
Synthetic Route (Scheme CLIX)
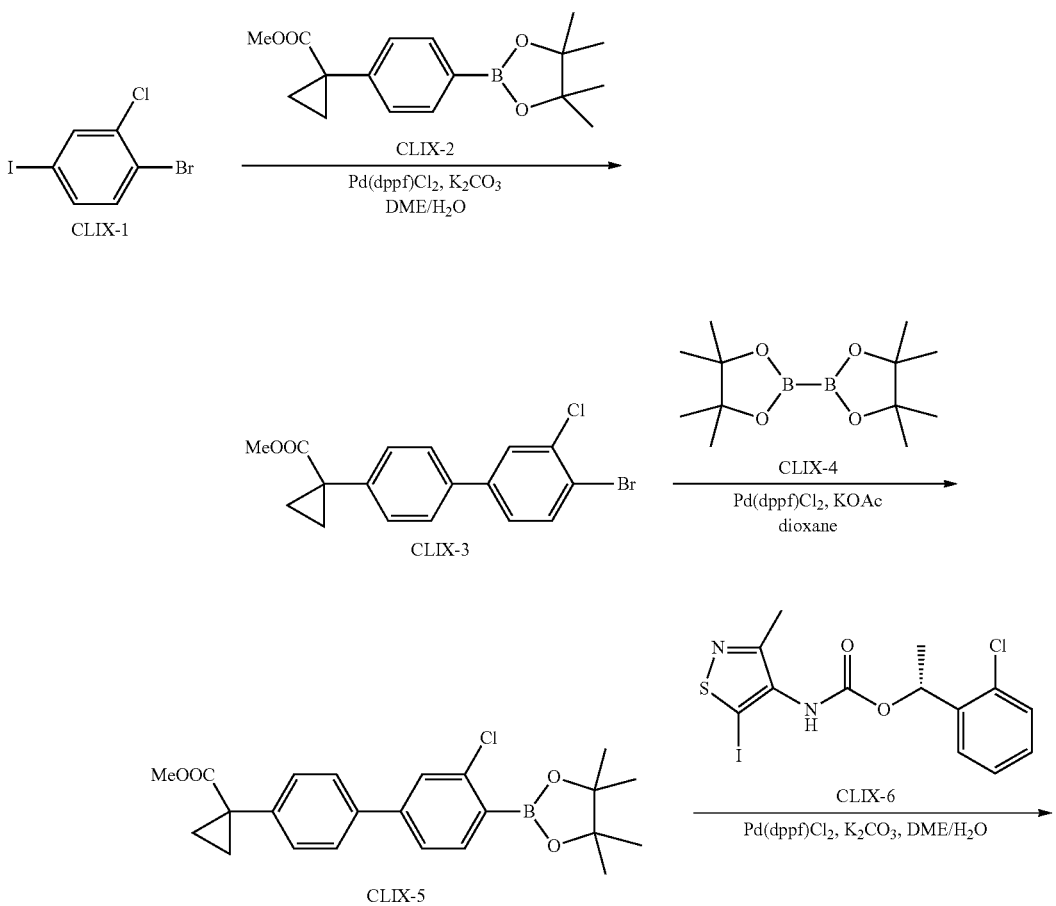

-continued

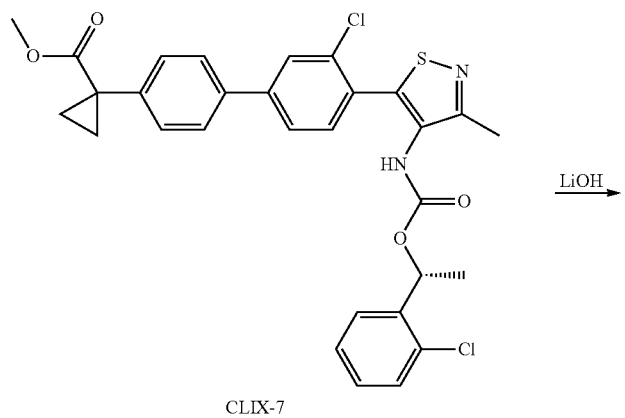

CLIX-7

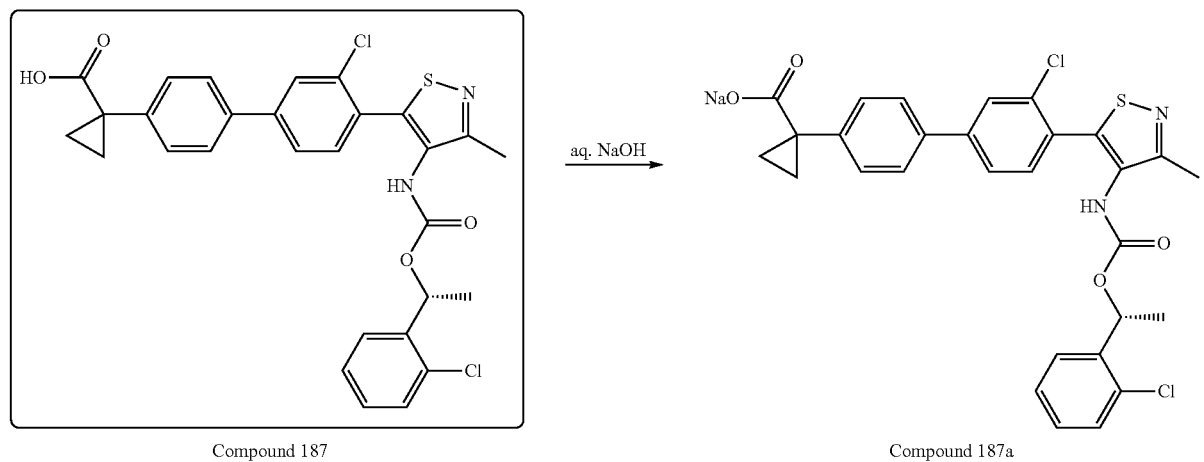

Compound 187

Compound 187a

Compound 187 was prepared analogously to the procedure described in the synthesis of Compound 117. MS (ESI) m/z (M+H)+ 567.1.

Compound 187a was prepared analogously to the procedure described in the synthesis of Compound 117a. $^1$HNMR (DMSO-d$_6$, t=80, 400 MHz): δ 8.92 (s, 1 H), 7.81 (s, 1 H), 7.66 (d, J=6.8 Hz, 1H), 7.60 (d, J=7.6 Hz, 2H), 7.46 (d, J=8.0 Hz, 3H), 7.40 (d, J=6.0 Hz, 2H), 7.26-7.33 (m, 2H), 5.97 (q, 1 H), 2.33 (s, 3 H), 1.44 (m, 5 H), 0.94 (br, 2 H). MS (ESI) m/z (M+H)+ 567.1.

Synthesis of Compound 188

Synthetic Route (Scheme CLX)

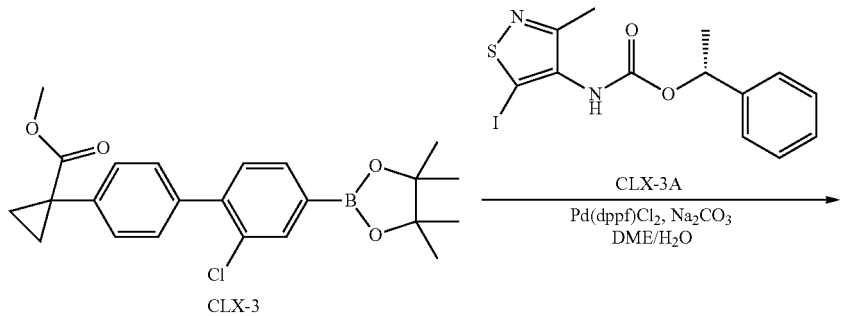

CLX-3

-continued
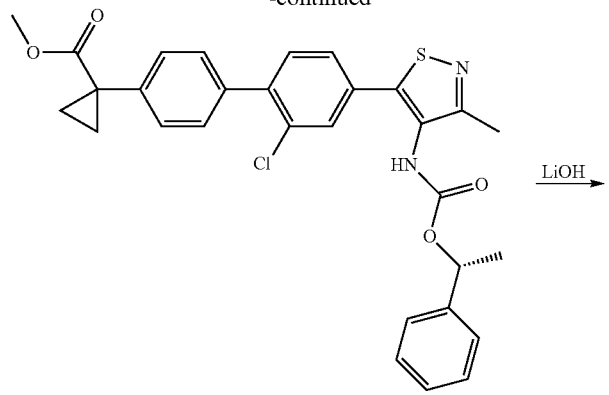
CLX-4
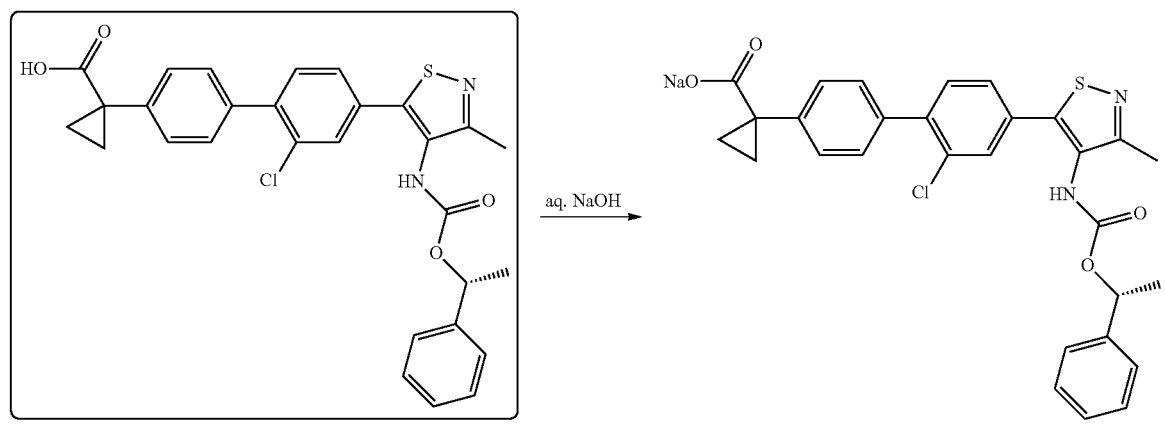
Compound 188            Compound 188a
Compound 188 was prepared analogously to the procedure described in the synthesis of Compound 117.
Compound 188a was prepared analogously to the procedure described in the synthesis of Compound 117a. $^1$H NMR (DMSO-$d_6$, 400 MHz): δ 9.40 (br, 1H), 7.72 (s, 1H), 7.27-7.72 (m, 11 H), 5.74-5.76 (q, 1H), 2.28 (s, 3H), 1.51-1.53 (m, 3H), 1.19-1.21 (m, 2H), 0.70-0.72 (m, 2H). MS (ESI) m/z (M+H)$^+$ 533.1.
Synthesis of Compound 189
Synthetic Route (Scheme CLXI)
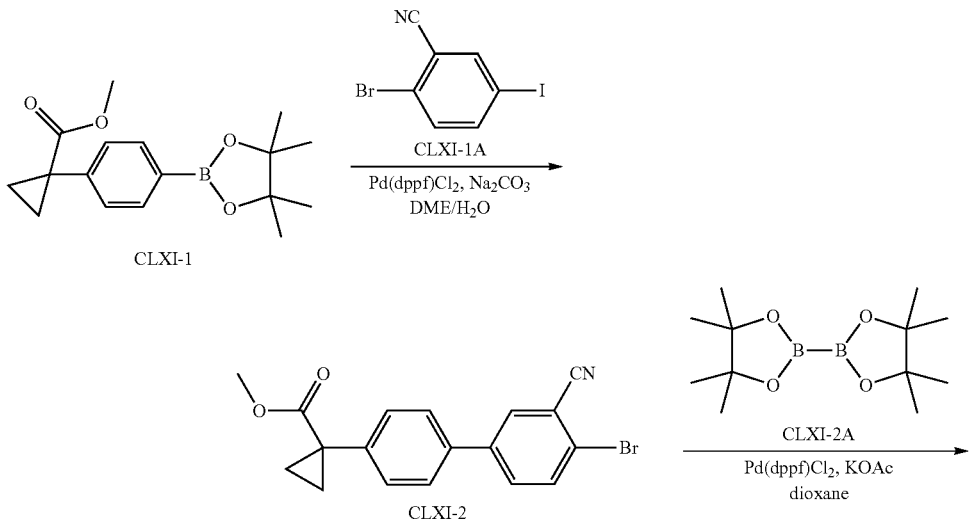

-continued
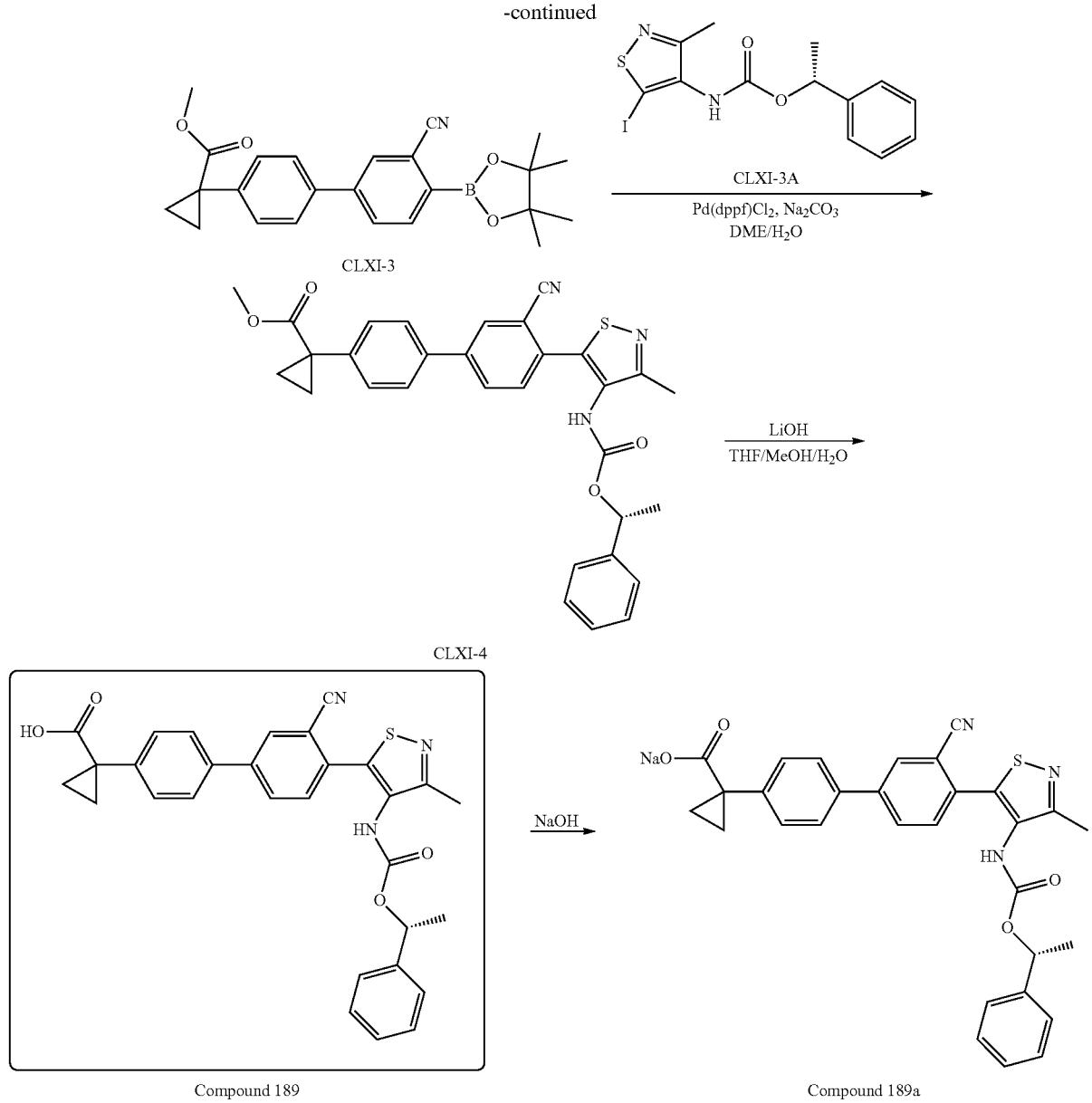
Compound 189
Compound 189a
Compound 189 was prepared analogously to the procedure described in the synthesis of Compound 117. MS (ESI) m/z (M+H)+ 524.1.
Compound 189a was prepared analogously to the procedure described in the synthesis of Compound 117a. $^1$H NMR (400 MHz, DMSO-$d_6$): δ 9.46 (s, 1H), 8.25 (s, 1H), 7.99-8.01 (m, 1H), 7.60-7.62 (d, J=8.0 Hz, 2H), 7.49-7.50 (m, 1H), 7.25-7.39 (m, 7H), 5.62-5.64 (q, 1H), 2.34 (s, 3H), 1.43 (br, 3H), 1.20-1.21 (br, 2H), 0.71-0.72 (br, 2H). MS (ESI) m/z (M+H)+ 524.0.
Synthesis of Compound 190
Synthetic Route (Scheme CLXII)
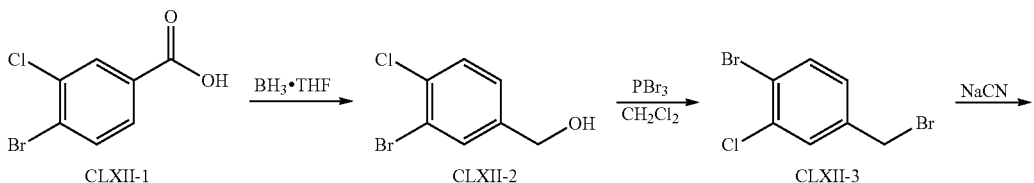

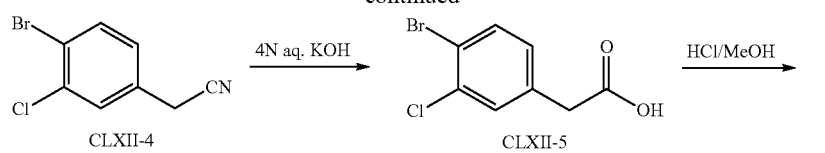
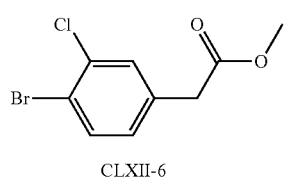
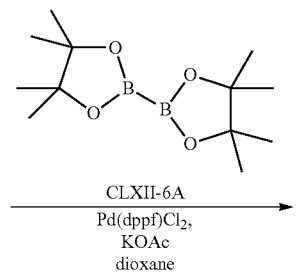
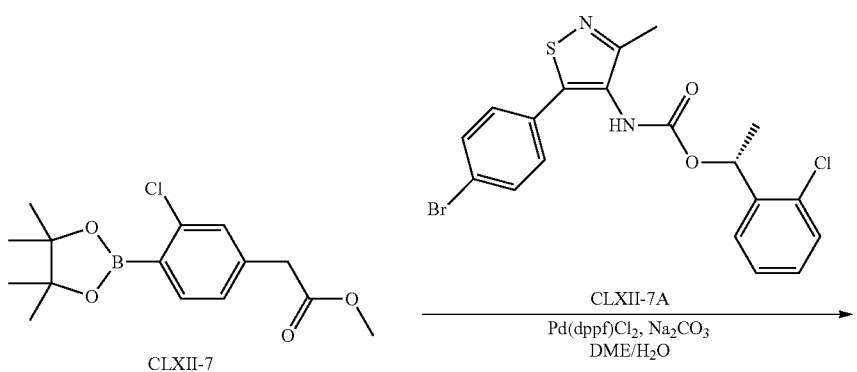
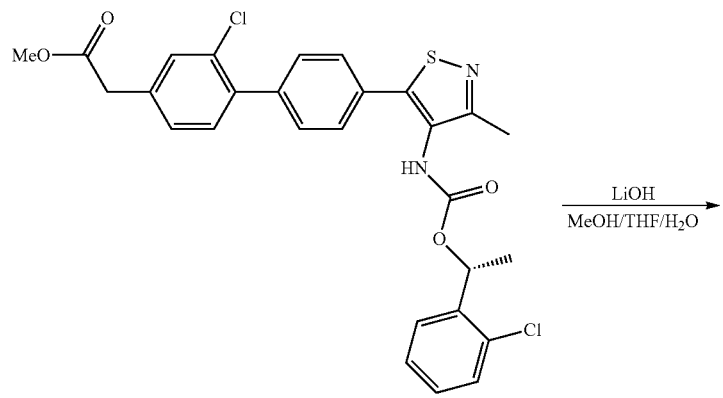
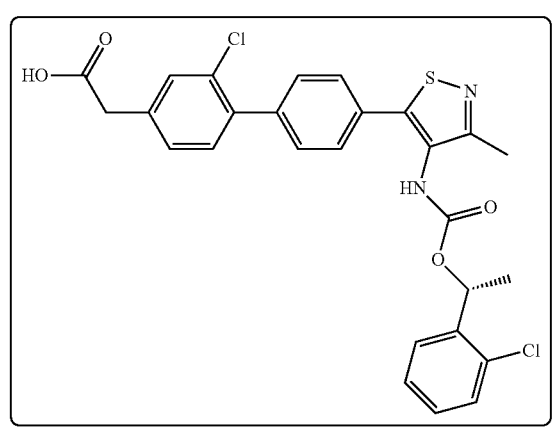
Compound 190
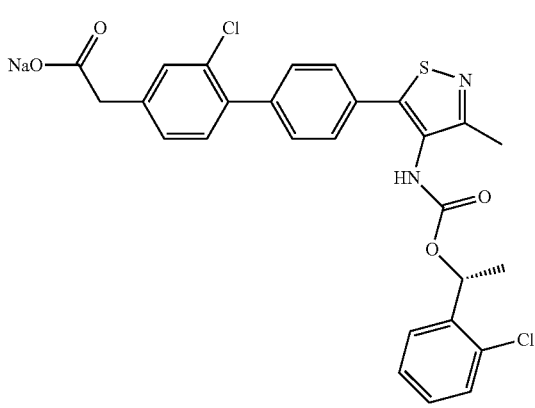
Compound 190a To a solution of compound CLXII-1 (6 g, 25 mmol) in THF (30 mL) was added $BH_3 \cdot THF$ (1 M, 60 mL) at 0° C. The mixture was stirred at r.t. for 12 h. After completing, water (50 mL) was added to the mixture and then washed with saturated $NaHCO_3$. The aqueous was extracted with EtOAc (50 mL×3) and the organic layer was washed with brine, dried over $Na_2SO_4$ and concentrated under vacuum to give compound CLXII-2 (4.5 g, yield: 79%).

To a solution of compound CLXII-2 (4 g, 18 mmol) in DCM (40 mL) was added $PBr_3$ (2.44 g, 9 mmol) at 0° C. The reaction mixture was stirred at r.t. overnight. After completed, water (50 mL) was added, the organic layer was separated and washed with brine, dried with over $Na_2SO_4$ and concentrated under vacuum to give compound CLXII-3 (4 g, yield: 78%).

To a solution of compound CLXII-3 (3 g, 10.5 mmol) in DMF (15 mL) was added NaCN (1 g, 21 mmol) at 0° C. and then $H_2O$ (2 mL) was added. The reaction mixture was stirred at 25° C. for 15 h. Then water (50 mL) was added followed by saturated $NaHCO_3$ (30 mL). This mixture was extracted with ethyl acetate (50 mL×3). The organic layers was dried over $Na_2SO_4$, filtered and concentrated under vacuum to give compound CLXII-4 (2.3 g, yield 93%).

To a solution of compound CLXII-4 (2 g, 8.6 mmol) in $H_2O$ (20 mL) was added KOH (1.9 g, 34.7 mmol). The reaction mixture was heated under reflux for 15 h. After completing, the mixture was washed with ethyl acetate (20 mL). Then adjusted pH to 5~6 by 1N HCl, the mixture was extracted with ethyl acetate (20 mL×3). The organic layers was dried with $Na_2SO_4$, filtered and concentrated under vacuum to give compound CLXII-5 (1.5 g, yield: 69%).

The mixture of compound CLXII-5 (1 g, 4 mmol) in HCl/MeOH (4M, 25 mL) was stirred at 80° C. for 3 hours. Then concentrated to afford compound CLXII-6 (0.8 g, yield 75.7%), which was used to next step directly without further purification.

To a stirred solution of compound CLXII-6 (0.8 g, 3 mmol), compound CLXII-6A (196 mg 3.6 mmol), KOAc (588 mg 6 mmol) in dioxane (30 mL) was added $Pd(dppf)Cl_2$ (100 mg, 0.15 mmol) under nitrogen. After the addition, the solution was heated to reflux under nitrogen for overnight. The solution was concentrated, then $H_2O$ (20 mL) was added, and the mixture was extracted with EtOAc (30 mL×3). The organic layer was combined and washed with brine, dried over $Na_2SO_4$, concentrated in vacuo. The residue was purified by column chromatography on silica gel (Petroleum ether: EtOAc=8:1) to afford compound CLXII-7 (600 mg, yield 64.3%). MS (ESI) m/z $(M+H)^+$ 311.2.

To a stirred solution of compound CLXII-7 (123.8 mg, 0.33 mmol), compound CLXII-7A (150 mg 0.33 mmol), $Na_2CO_3$ (127.4 mg, 0.399 mmol) in DME (30 mL) and $H_2O$ (10 mL) was added $Pd(dppf)Cl_2$ (70.6 mg, 0.66 mmol) under nitrogen. After the addition, the solution was heated to reflux under nitrogen for 2 hours. The solution was concentrated, then $H_2O$ (20 mL) was added, and the mixture was extracted with EtOAc (30 mL×3). The organic layer was combined and washed with brine, dried over $Na_2SO_4$, concentrated in vacuo. The residue was purified by column chromatography on silica gel (Petroleum ether: EtOAc=5:1) to afford compound CLXII-8 (150 mg, yield 82%). MS (ESI) m/z $(M+H)^+$ 555.1.

Preparation of Compound 190

To a solution of compound CLXII-8 (150 mg, 0.27 mmol) in MeOH (5 mL), THF (5 mL, $H_2O$ (5 mL) was added $LiOH \cdot H_2O$ (68 mg, 1.62 mmol). The mixture was stirred overnight at room temperature. Then concentrated, water (20 mL), HCl (2 N) was added to pH=3, extracted with EtOAc (25 mL×3). The combined organic layers were washed with brine (10 mL×2), and concentrated under reduced pressure. The residue was purified by prep-HPLC to give Compound 190 (90 mg, yield: 61.6%). MS (ESI) m/z $(M+H)^+$ 541.1.

Preparation of Compound 190a

To a solution of Compound 190 (91.8 mg 0.17 mmol) in MeOH (5 mL) was added NaOH (0.05N, 3.39 mL) at 0° C., the mixture was stirred for one hour, then the reaction mixture was lyophilized to give Compound 190a. $^1H$ NMR ($CD_3OD$-$d_4$, 400 MHz): δ 7.48-7.60 (m, 6H), 7.25-7.37 (m, 5H), 6.12-6.14 (q, 1H), 3.53 (s, 2H), 2.37 (s, 3H), 1.52-1.56 (br, 3H). MS (ESI) m/z $(M+H)^+$ 541.1.

Synthesis of Compound 191

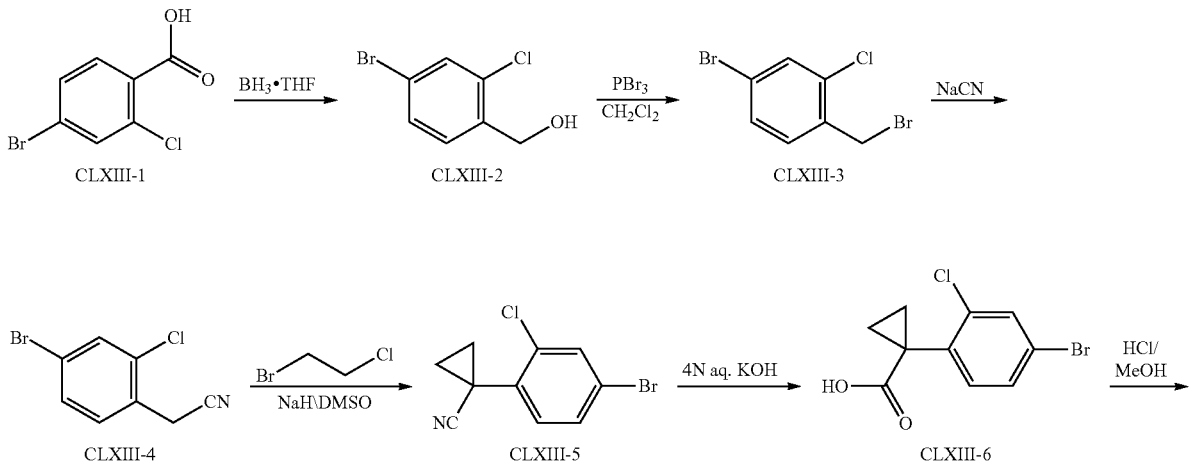

Synthetic Route (Scheme CLXIII)

-continued

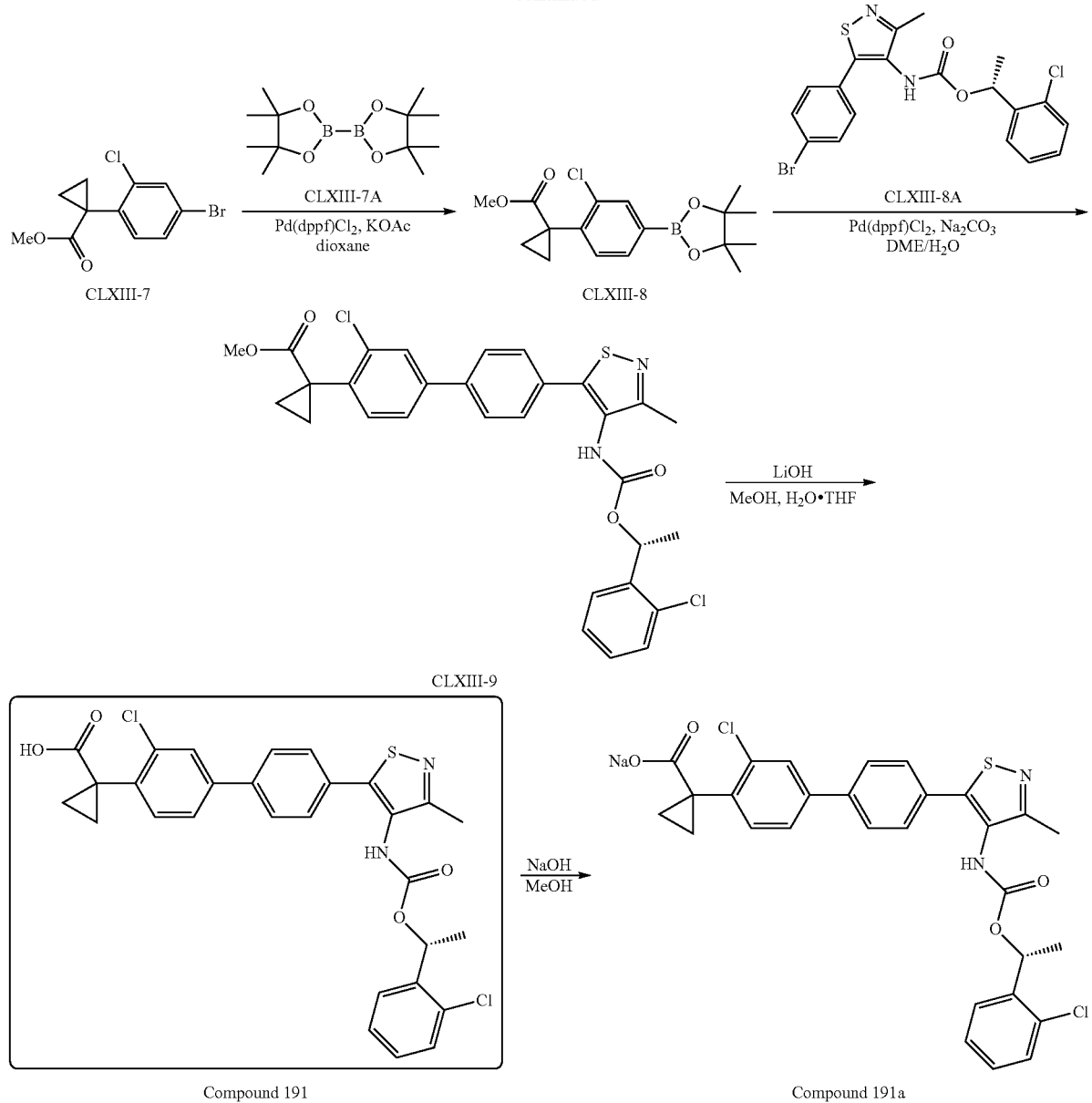

To a solution of compound CLXIII-1 (20 g, 85 mmol) in THF (300 mL) was added BH$_3$.THF (1 M, 204 mL) at 0° C. The mixture was stirred at r.t. for 12 h. After completing, water (100 mL) was added to the mixture and then washed with saturated NaHCO$_3$. The aqueous was extracted with EtOAc (200 mL×3) and the organic layer was washed with brine, dried with over Na$_2$SO$_4$ and concentrated under vacuum to give compound CLXIII-2 (11.1 g, yield: 59%).

To a solution of compound CLXIII-2 (11 g, 50 mmol) in DCM (120 mL) was added PBr$_3$ (6.8 g, 25 mmol) at 0° C. The reaction mixture was stirred at r.t. overnight. After completed, water (100 mL) was added to the mixture. The organic layer was separated and washed with brine, dried with over Na$_2$SO$_4$ and concentrated under vacuum to give compound CLXIII-3 (15 g, crude yield 100%).

To a solution of compound CLXIII-3 (15 g, 53 mmol) in DMF (150 mL) was added NaCN (3.9 g, 80 mmol) at 0° C. and then H$_2$O (20 mL) was added. This mixture was stirred at 25° C. for 15 h. After completed, water (120 mL) was added followed by sat. NaHCO$_3$ (300 mL). The mixture was extracted with ethyl acetate (150 mL×3). The organic layers was dried over Na$_2$SO$_4$, filtered, and concentrated under vacuum to give compound CLXIII-4 (10 g, yield: 90%).

To a stirred solution of compound CLXIII-4 (1.90 g, 8.3 mmol) and 1-bromo-2-chloroethane (1.43 g, 10 mmol) in DMSO (25 mL) was added NaH (0.65 g, 16.4 mmol) at 0° C. The reaction mixture was stirred for 2 h at r.t. Water (30 mL) was added, and extracted with EtOAc (30 mL×3), the combined organic layers were washed with brine (20 mL), and concentrated under reduced pressure to give compound CLXIII-5 (1.70 g, yield: 80.6%), which was used directly without further purification.

The mixture of compound CLXIII-5 (1.70 g, 6.7 mmol) in KOH (4N, 10 mL) was stirred at 100° C. for 12 hours. Then H$_2$O (30 mL) was added, and the mixture was washed with t-BuOMe, then HCl (2N) was added to pH=2, extracted with EtOAc (30 mL×3). The organic layer was combined and washed with brine, dried over $Na_2SO_4$, concentrated in vacuo to get compound CLXIII-6 (1.72 g, yield: 93.5%), which was used directly without further purification.

Compound 191 was prepared analogously to the procedure described in the synthesis of Compound 190 (70 mg, yield: 38.3%). MS (ESI) m/z (M+H)⁺ 567.1.

Compound 191a was prepared analogously to the procedure described in the synthesis of Compound 190a. ¹H NMR (400 MHz, DMSO-$d_6$): δ 7.21 (d, J=8.4 Hz, 2H), 7.57-7.62 (m, 3H), 7.41-7.49 (m, 3H), 7.31-7.37 (m, 3H), 5.98-6.18 (q, 1H), 2.29 (s, 3H), 1.48 (d, J=5.6 Hz, 3H), 1.34 (br, 2H), 0.71 (br, 2H). MS (ESI) m/z (M+H)⁺ 567.1.

Synthesis of Compound 192

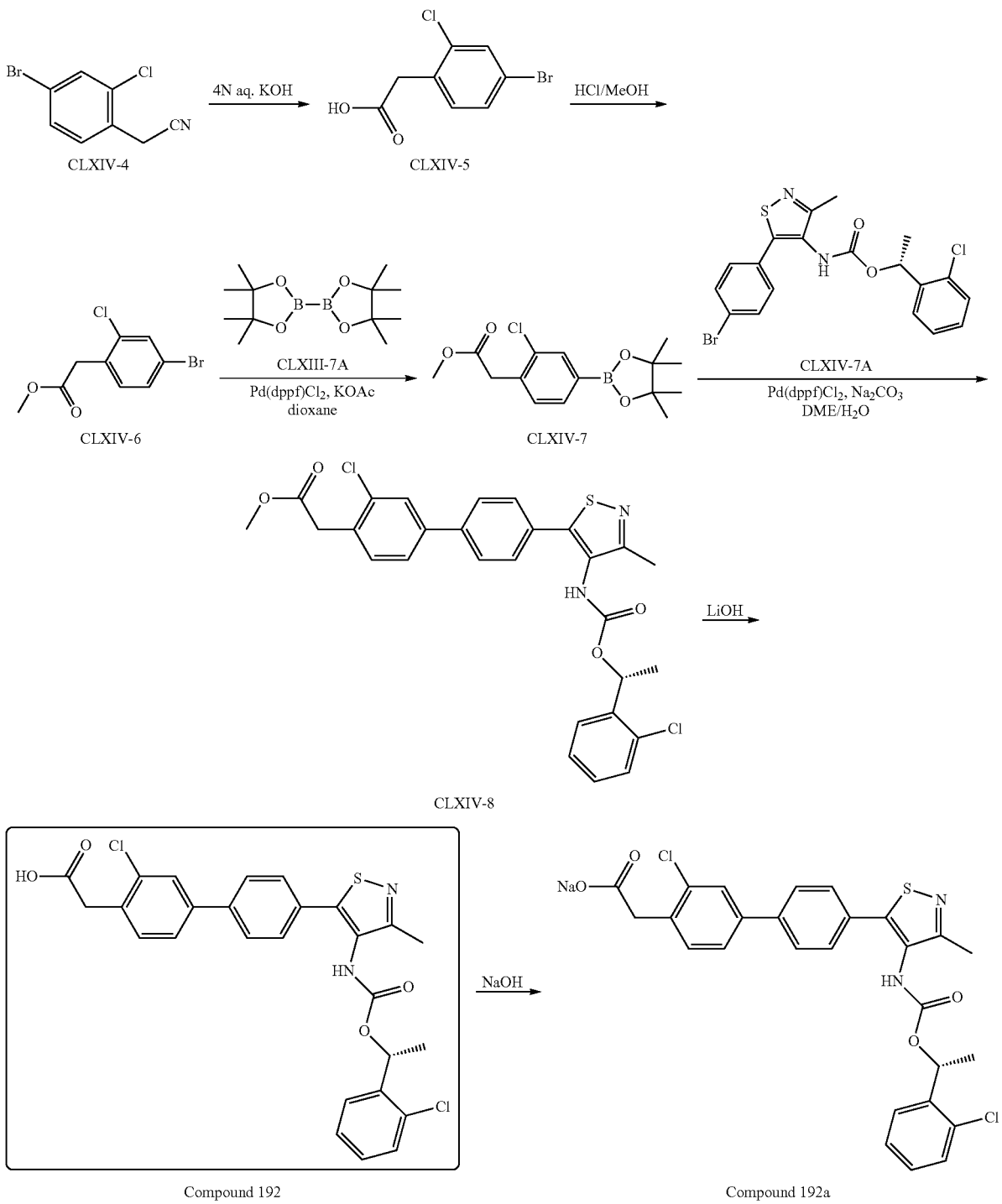

Synthetic Route (Scheme CLXIV)

Compound 192

Compound 192a

Compound 192 was prepared analogously to the procedure described in the synthesis of Compound 190. MS (ESI) m/z (M+H)+ 541.2.
Compound 192a was prepared analogously to the procedure described in the synthesis of Compound 190a. $^1$H NMR (400 MHz, DMSO-d$_6$, t=80): δ 9.04 (s, 1H), 7.72 (d, J=8.4 Hz, 2H), 7.58-7.62 (m, 3H), 7.39-7.49 (m, 4H), 7.28-7.39 (m, 2H), 5.97-6.02 (q, 1H), 3.45 (s, 2H), 2.49 (s, 3H), 1.47 (d, J=6.4 Hz, 3H). MS (ESI) m/z (M+H)+ 541.1.
Synthesis of Compound 193
Synthetic Route (Scheme CLXV)
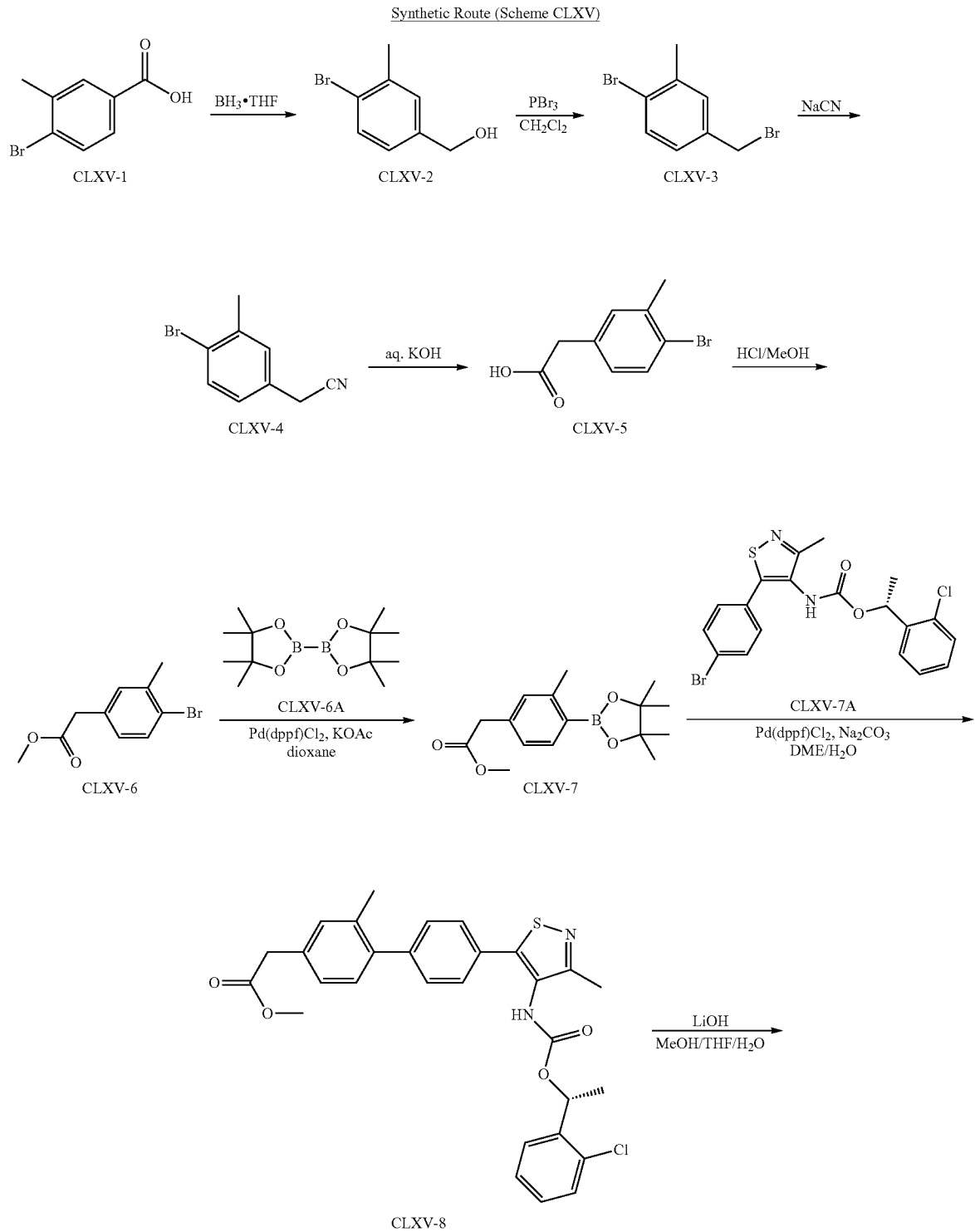

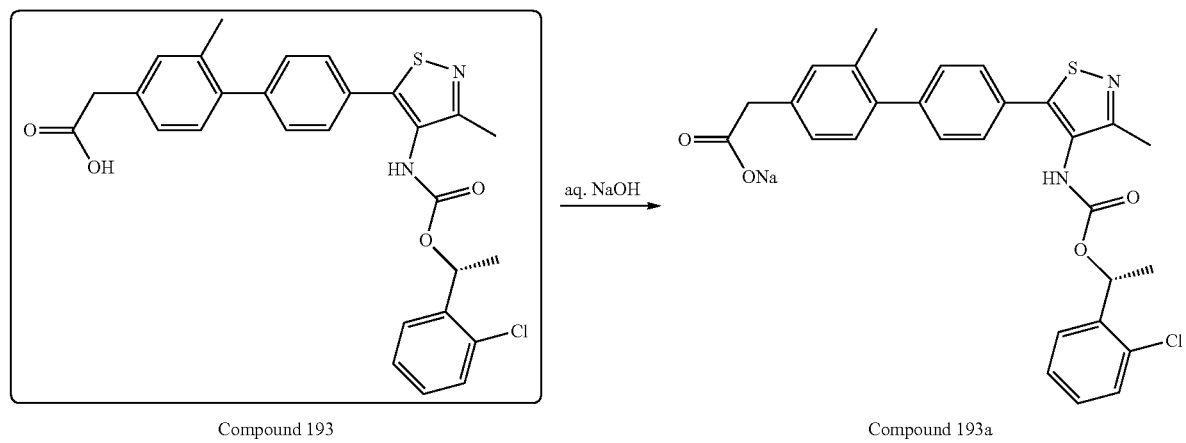
Compound 193
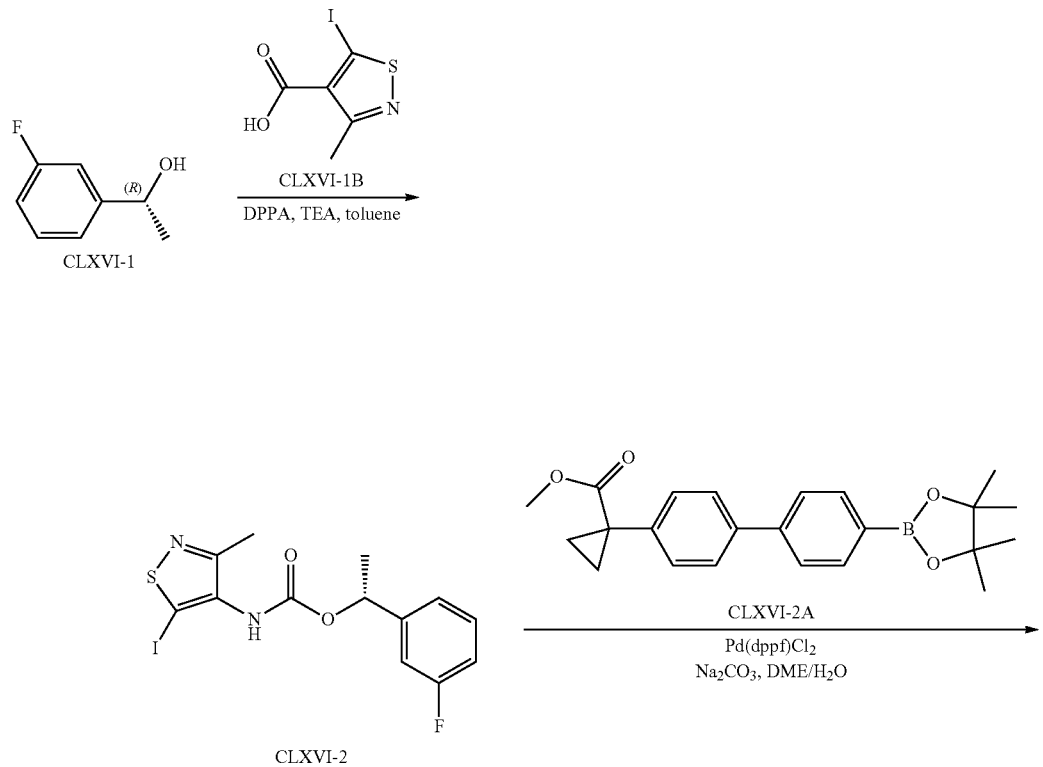
Compound 193a
Compound 193 was prepared analogously to the procedure described in the synthesis of Compound 190. MS (ESI) m/z (M+H)+ 521.2.
Compound 193a was prepared analogously to the procedure described in the synthesis of Compound 190a. $^1$H NMR (DMSO-d$_6$, 400 MHz): δ 9.01 (s, 1H), 7.59 (d, J=8.4 Hz, 2H), 7.30-7.43 (m, 6H), 7.07-7.28 (m, 4H), 5.99-6.04 (q, 1H), 3.35 (s, 2H), 2.30 (s, 3H), 2.23 (s, 3H), 1.47 (d, J=5.2 Hz, 3H) MS (ESI) m/z (M+H)+ 521.1.
Synthesis of Compound 194
Synthetic Route (Scheme CLXVI)

-continued

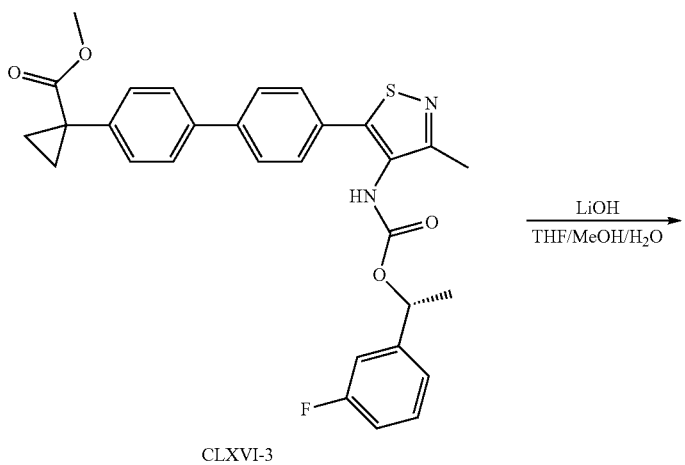

CLXVI-3

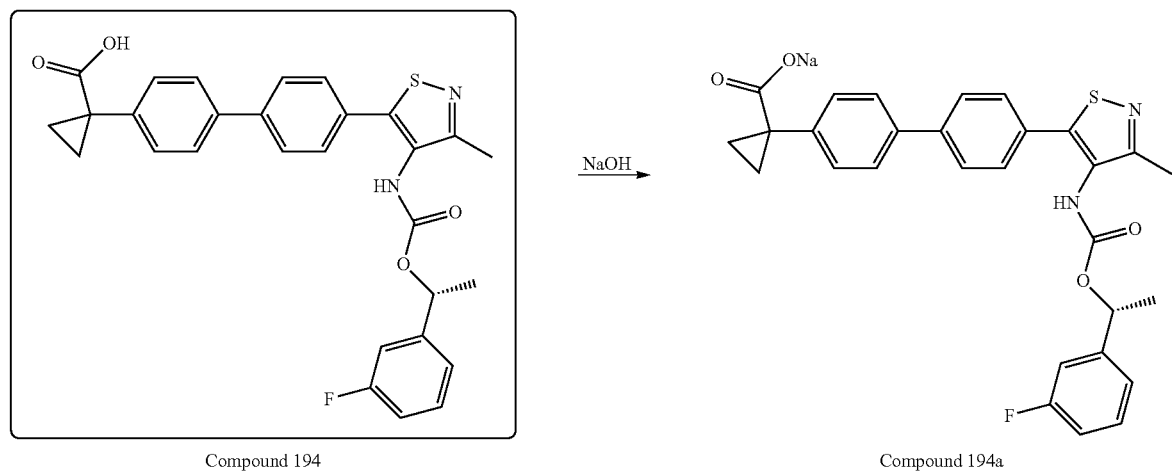

Compound 194

Compound 194a

The mixture of compound CLXVI-1 (652 mg, 2.42 mmol), compound CLXVI-1B (400 mg, 2.9 mmol), DPPA (800 mg, 2.9 mmol) and Et₃N (488 mg, 34.8 mmol) in toluene (100 mL) was stirred at reflux under nitrogen for 1 hour. The mixture was concentrated, and the residue was partitioned between H₂O and DCM, the aqueous phase was extracted with DCM. The combined organic layer was washed with brine, dried over Na₂SO₄, and concentrated. The residue was purified by chromatography on silica gel (PE:EA=5:1) to afford compound CLXVI-2 (450 mg, yield 45.7%).

Compound 194 was prepared analogously to the procedure described in the synthesis of Compound 44 (1 g, yield 68.9%). MS (ESI) m/z (M+H)⁺ 517.2.

Compound 194a was prepared analogously to the procedure described in the synthesis of Compound 44a. ¹H NMR (DMSO-d₆, 400 MHz): δ 8.99 (br, 1H), 7.70 (d, J=8.4 Hz, 2H), 7.58 (d, J=8.4 Hz, 2H), 7.51 (d, J=8.4 Hz, 2H), 7.36-7.42 (m, 3H), 7.01-7.17 (m, 3H), 5.73-5.78 (q, 1H), 2.30 (s, 3H), 1.48 (d, J=6.4 Hz, 3H), 1.27-1.30 (m, 2H), 0.74-0.76 (m, 2H). MS (ESI) m/z (M+H)⁺ 517.1.

Synthesis of Compound 195

Synthetic Route (Scheme CLXVII)

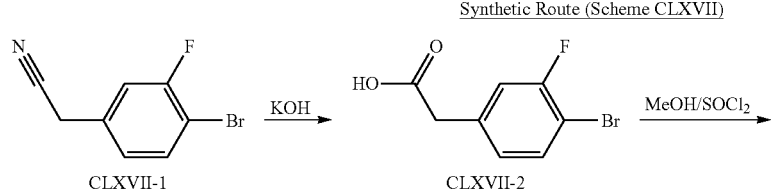

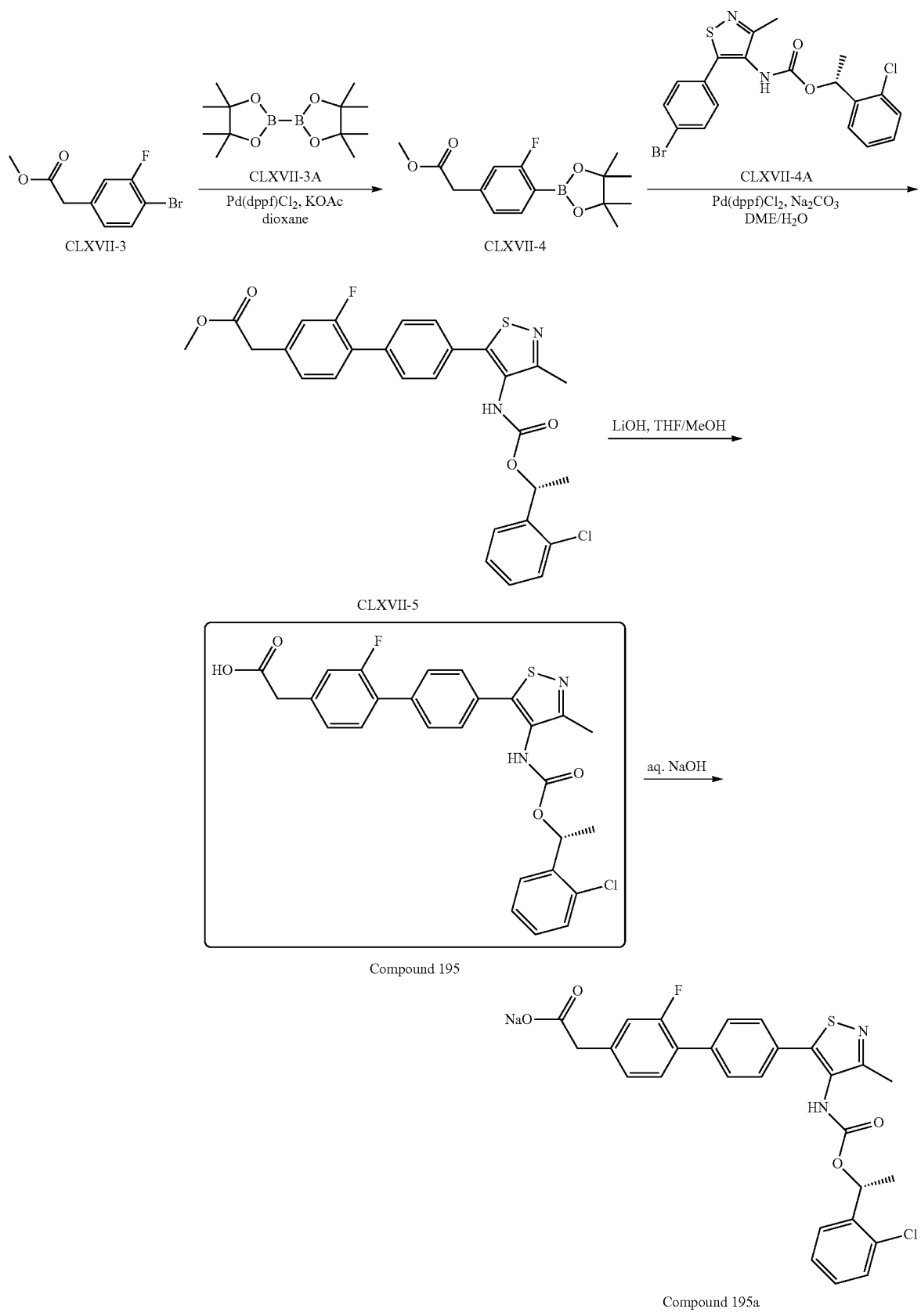

Compound 195 was prepared analogously to the procedure described in the synthesis of Compound 190. MS (ESI) m/z (M+H)+ 525.1.
Compound 195a was prepared analogously to the procedure described in the synthesis of Compound 190a. $^1$H NMR (400 MHz, DMSO-d$_6$): δ 9.20 (s, 1 H), 7.53-7.64 (m, 4 H), 7.23-7.45 (m, 7 H), 5.93-6.04 (q, 1 H), 3.29 (s, 2 H), 2.23 (s, 3 H), 1.49 (d, J=6.4 Hz, 3 H). MS (ESI) m/z (M+H)+ 525.1.
Synthesis of Compound 196
Synthetic Route (Scheme CLXVIII)
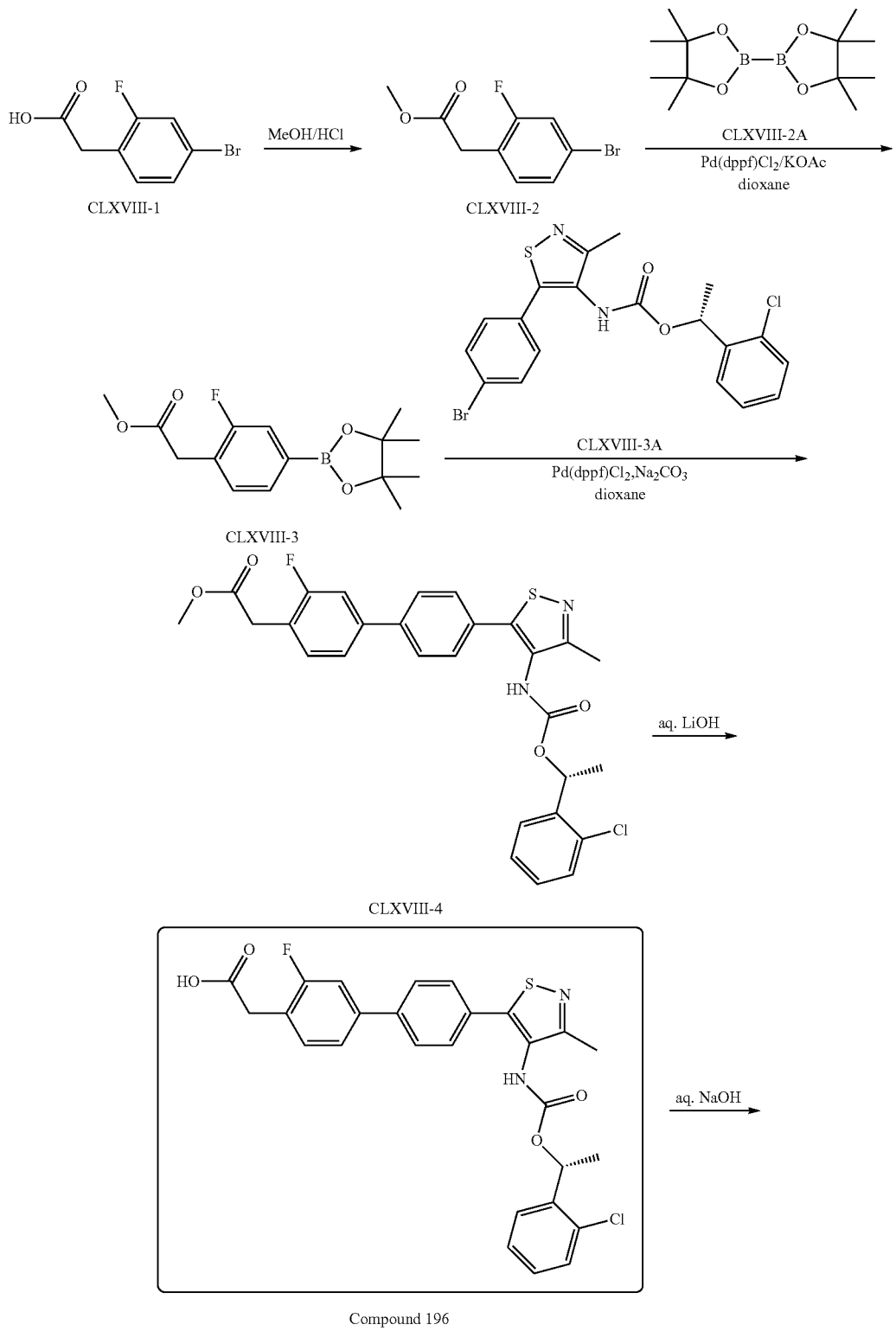
Compound 196

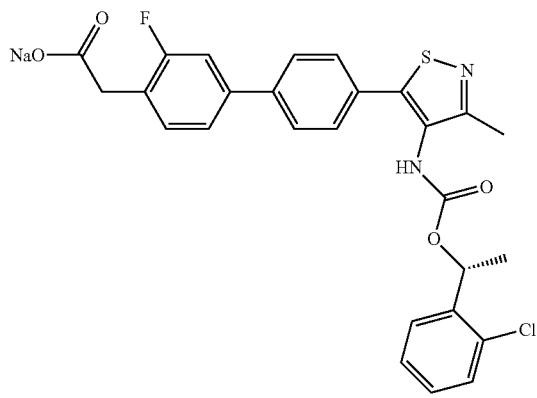
Compound 196a
Compound 196 and 196a were prepared analogously to the procedure described in the synthesis of Compound 190 and 190a. Compound 196a: $^1$H NMR (H13213-133-2A DMSO-$d_6$): δ 9.45 (s, 1H), 7.77-7.83 (m, 2H), 7.56-7.65 (m, 4H), 7.44-7.48 (m, 3H), 7.21-7.36 (m, 2H), 5.95-5.97 (q, 1H), 2.25 (s, 3H), 1.52 (d, J=6.4 Hz, 3H). MS (ESI) m/z (M+H)$^+$ 547.1.
Synthesis of Compound 197
Synthetic Route (Scheme CLXIX)
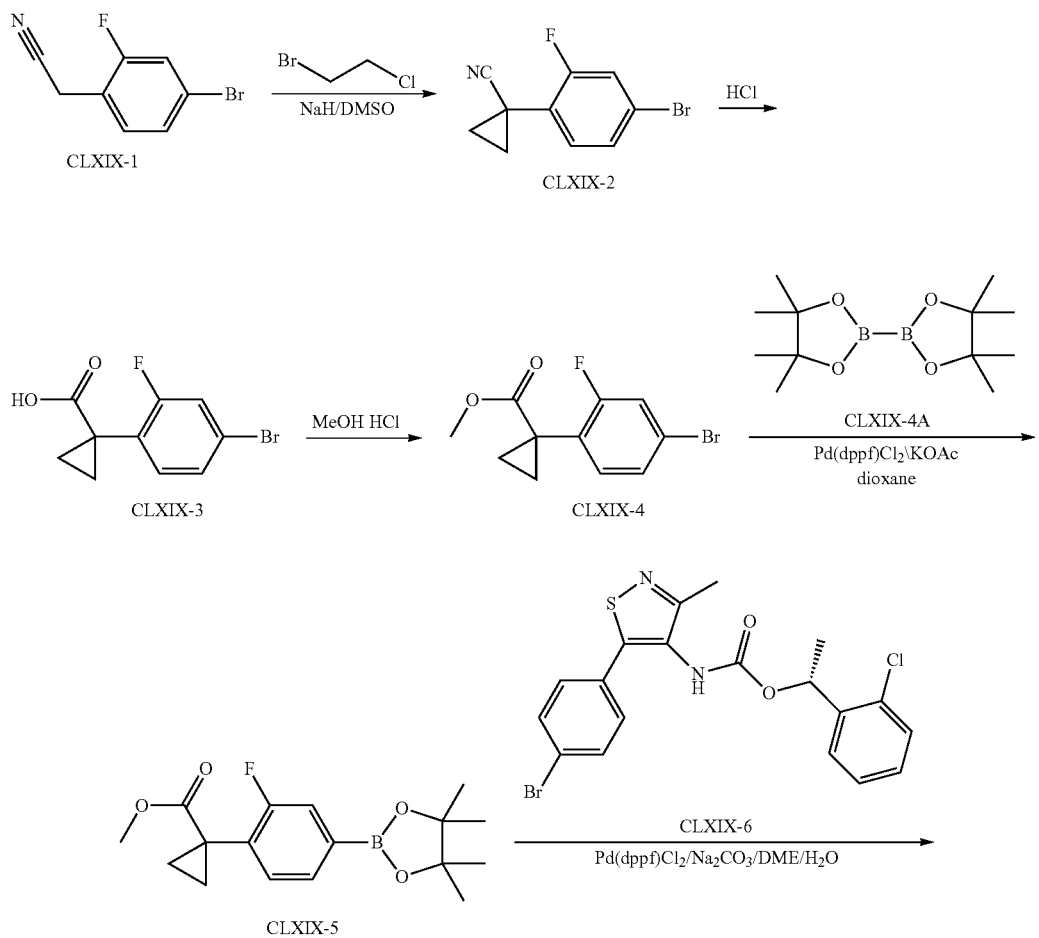

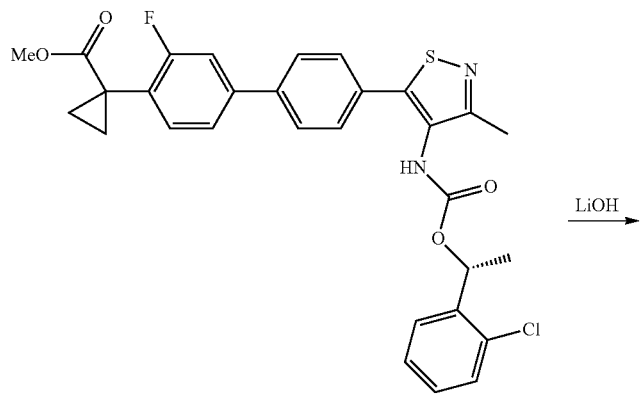
CLXIX-7
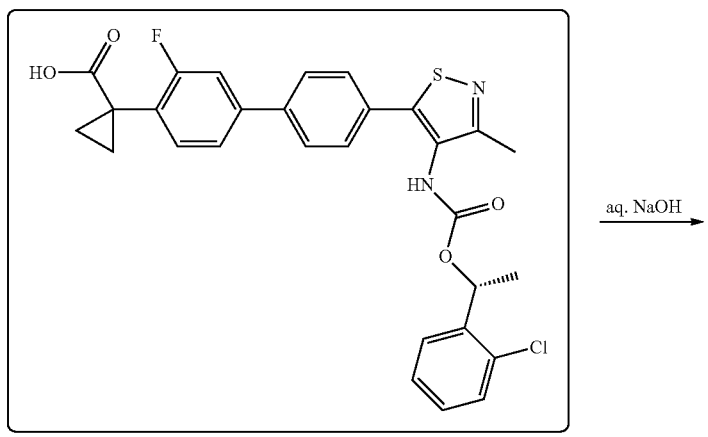
Compound 197
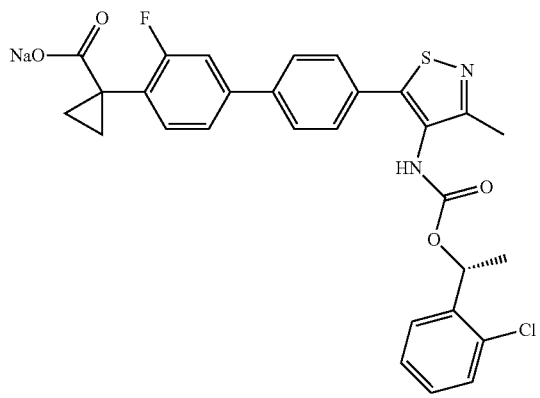
Compound 197a
Compound 197 was prepared analogously to the procedure described in the synthesis of Compound 191. MS (ESI) m/z (M+H)⁺ 551.1.
Compound 197a was prepared analogously to the procedure described in the synthesis of Compound 191a. $^1$H NMR (DMSO-d$_6$, 400 MHz): δ 9.00 (s, 1H), 7.72 (d, J=8.4 Hz, 2H), 7.59 (d, J=8.4 Hz, 2H), 7.40-7.48 (m, 2H), 7.30-7.36 (m, 5H), 5.97-6.00 (q, 1H), 2.29 (s, 3H), 1.47 (d, J=5.2 Hz, 3H), 1.28-1.29 (m, 2H), 0.73-0.74 (m, 2H). MS (ESI) m/z (M+H)⁺ 551.1.

Synthesis of Compound 198
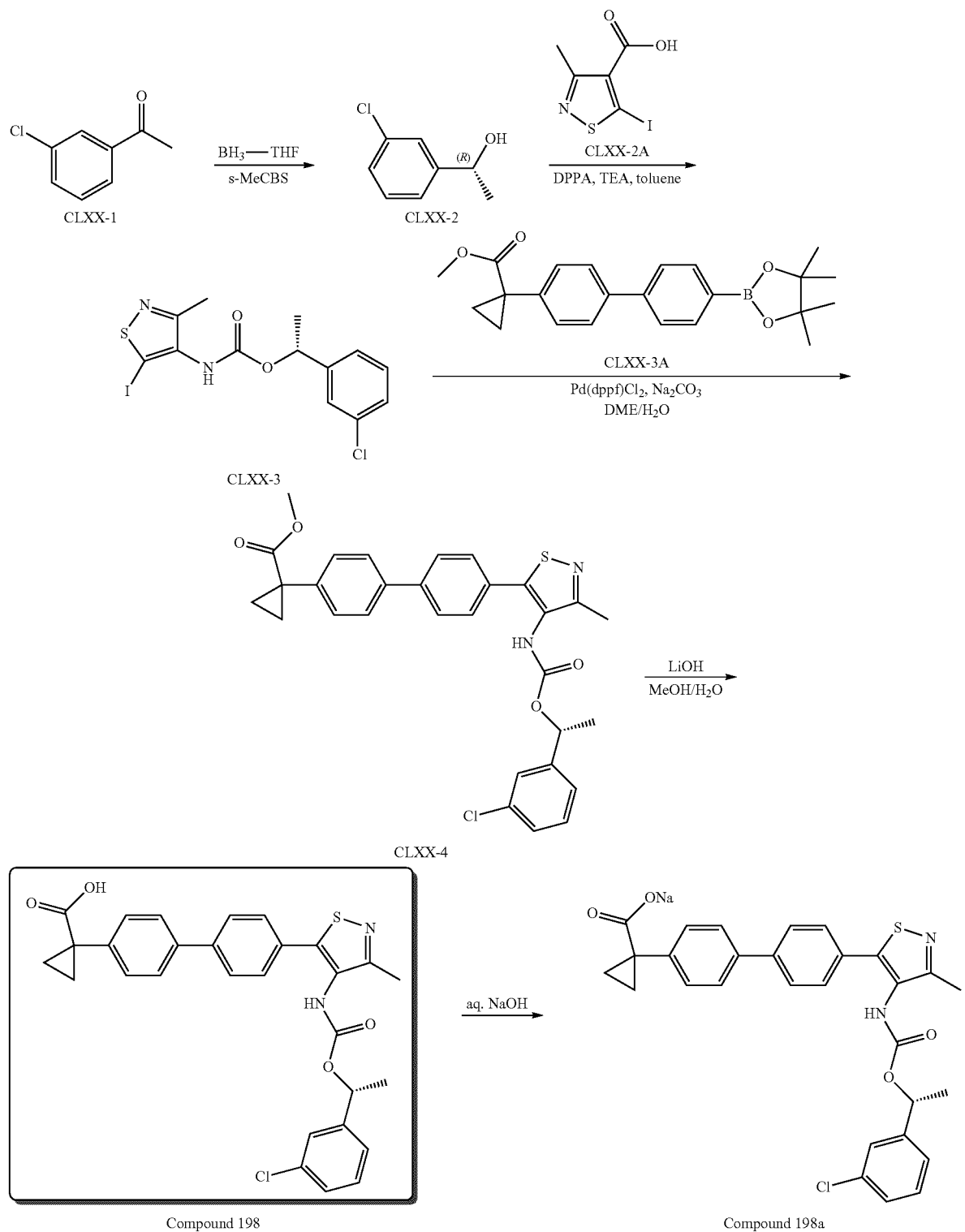
To a solution of (s)-MeCBS in toluene (3.3 mL of 1.0 M, 3.3 mmol) were added BH$_3$-THF solution in THF (42 mL of 0.94 M, 39.5 mmol) and compound CLXX-1 (10 g, 65.8 mmol) in THF (58 mL) simultaneously at room temperature over 30 min. After completing the addition of the BH$_3$-THF and compound CLXX-1 solutions, the reaction solution was allowed to stir for 10 min before quenching with a solution of HCl (132 mL of 2 M, 264 mmol). EtOAc (100 mL) was added, and the organic phase was washed with saturated aqueous solutions of KCl (30 mL×3), NaHCO$_3$ (30 mL×3), and KCl (30 mL×3). The organic phase was then dried over Na$_2$SO$_4$, filtered, concentrated in vacuo. The residue was purified by chromatography (PE:EA=3:1) to afford compound CLXX-2 (6.7 g, yield 67%).

Compound 198 was prepared analogously to the procedure described in the synthesis of Compound 44 (850 mg, yield 73.3%). MS (ESI) m/z (M+H)$^+$ 533.2.

Compound 198a was prepared analogously to the procedure described in the synthesis of Compound 44a. $^1$H NMR (400 MHz, DMSO-d$_6$): δ 7.71 (d, J=8.4 Hz, 2 H), 7.59 (d, J=8.4 Hz, 2 H), 7.51 (d, J=8.0 Hz, 2 H), 7.30-7.42 (m, 6 H), 5.77 (q, 1 H), 2.30 (s, 3 H), 1.49 (d, J=6.0 Hz, 3 H), 1.26-1.27 (m, 2 H), 0.72-0.73 (m, 2 H). MS (ESI) m/z (M+H)$^+$ 533.2.

Synthesis of Compound 199

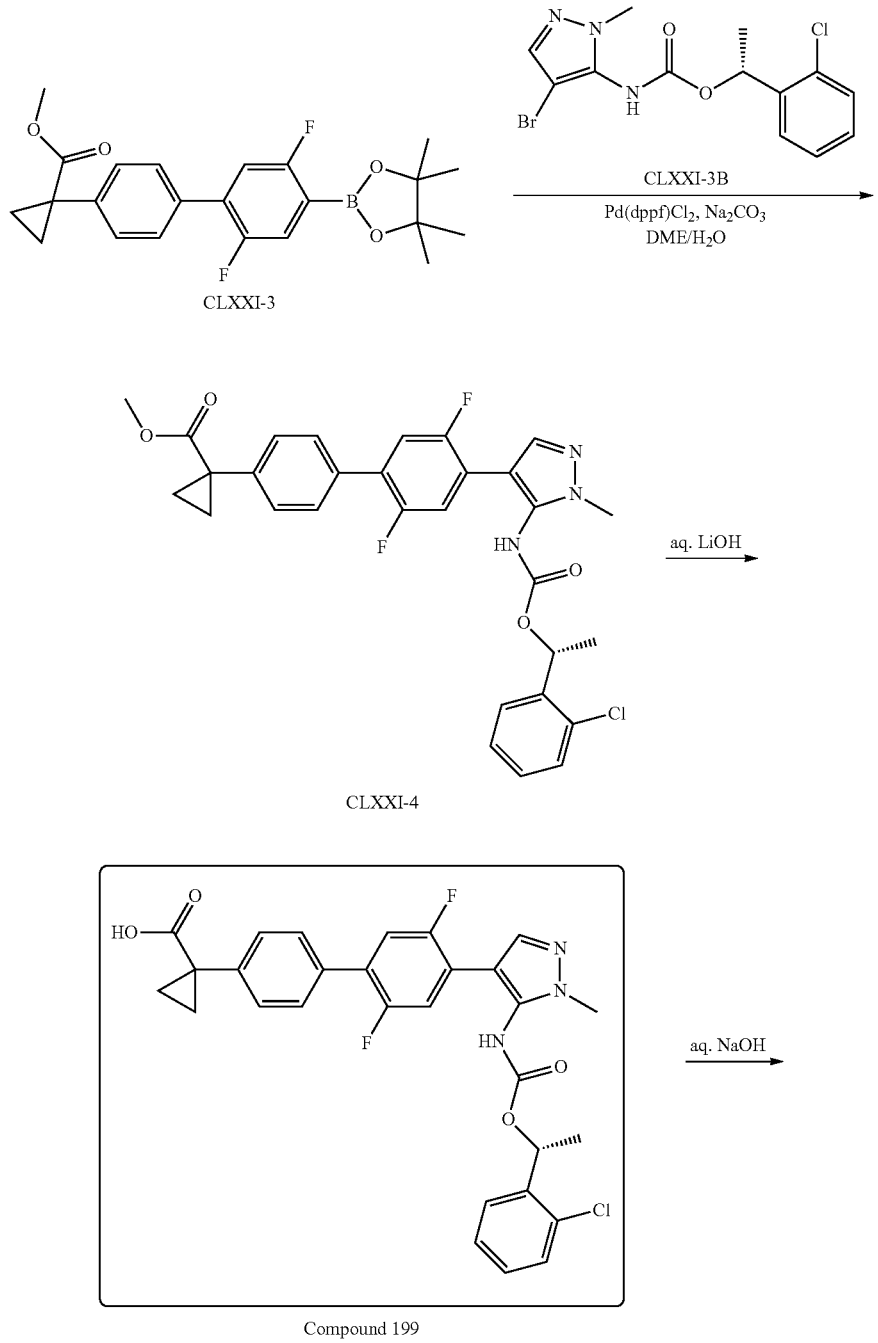

Compound 199

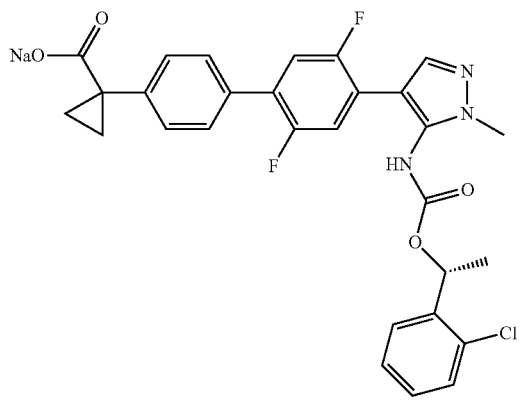

Compound 199a

The synthesis of compound CLXXI-3 was described in the synthesis of Compound 181. The synthesis of compound CLXXI-3B was described in the synthesis of Compound 171.

Compound 199 was prepared analogously to the procedure described in the synthesis of Compound 181. MS (ESI) m/z (M+H)+ 552.1.

Compound 199a was prepared analogously to the procedure described in the synthesis of Compound 181a. ¹H NMR (DMSO-$d_6$, 400 MHz): δ 9.48 (br, 1H), 7.72 (s, 1H), 7.30-7.48 (m, 10H), 6.00-6.04 (q, 1H), 3.69 (s, 3H), 1.48-1.49 (m, 3H), 1.41-1.42 (m, 2H), 1.02-1.03 (m, 2H). MS (ESI) m/z (M+H)+ 552.1.

Synthesis of Compound 200

Synthetic Route (Scheme CLXXII)

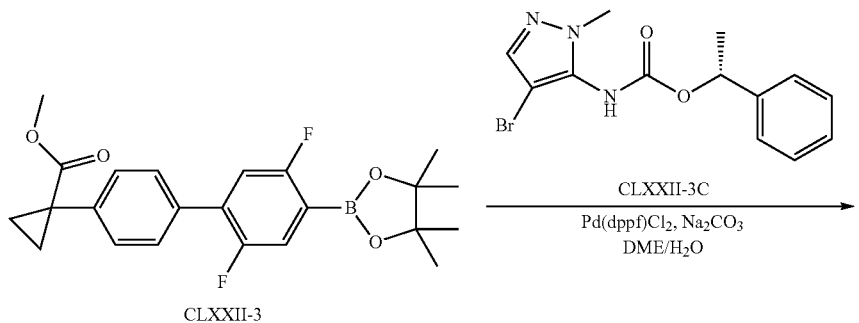

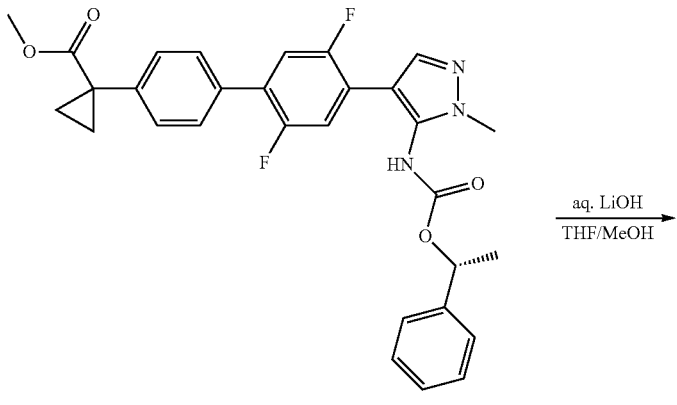

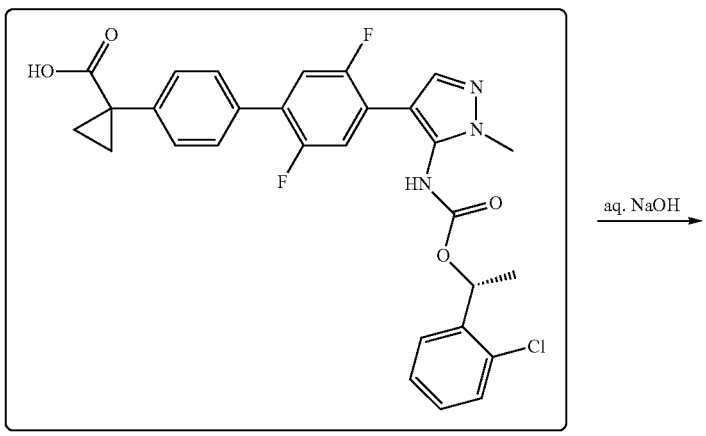

Compound 200

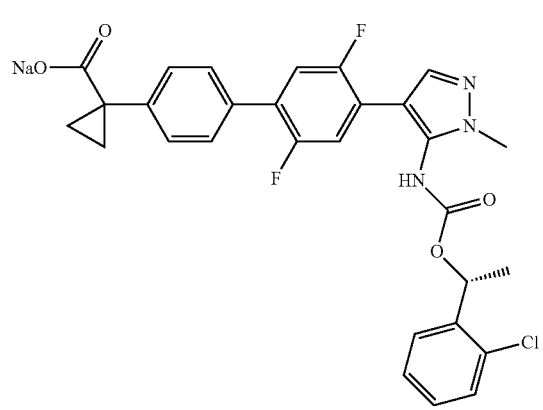

Compound 200a

The synthesis of compound CLXXII-3C was described in the synthesis of Compound 170.

Compound 200 was prepared analogously to the procedure described in the synthesis of Compound 199. MS (ESI) m/z (M+H)⁺ 518.2.

Compound 200a was prepared analogously to the procedure described in the synthesis of Compound 199a. $^1$H NMR (DMSO-$d_6$, 400 MHz): δ 7.68 (s, 1H), 7.32-7.41 (m, 11H), 5.77-5.79 (q, 1H), 3.68 (s, 3H), 1.49 (d, J=6.0 Hz, 3H), 1.31 (br, 2H), 0.79 (br, 2H). MS (ESI) m/z (M+H)⁺ 518.2.

Synthesis of Compound 201

Synthetic Route (Scheme CLXXIII)

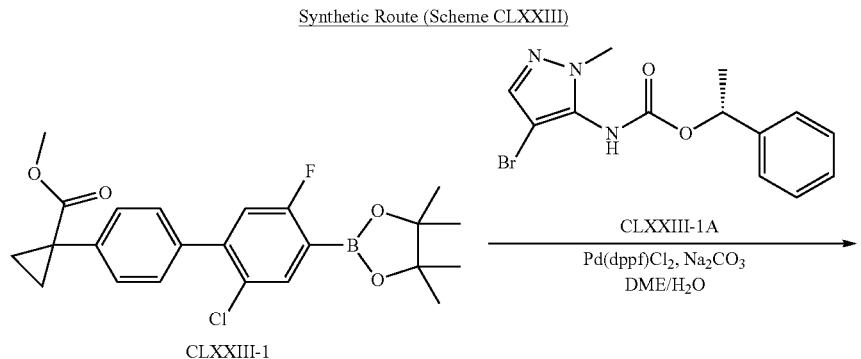

CLXXIII-1

CLXXIII-1A
Pd(dppf)Cl$_2$, Na$_2$CO$_3$
DME/H$_2$O

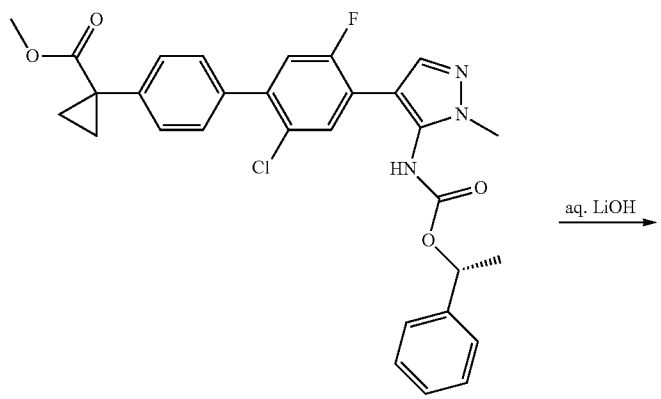
CLXXIII-2
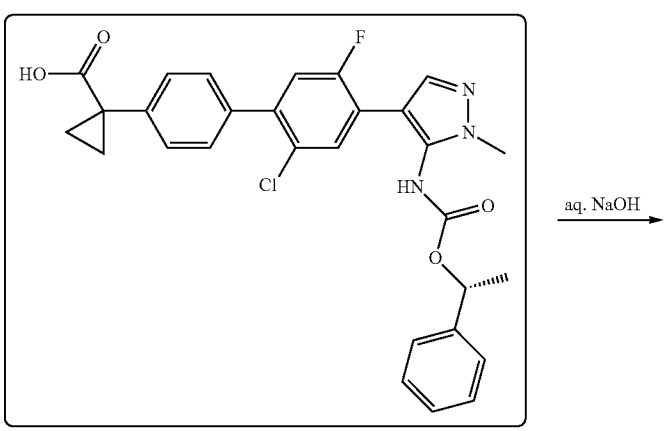
Compound 201
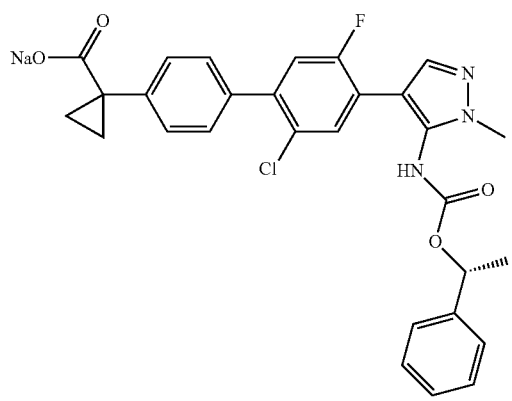
Compound 201a
Compound 201 was prepared analogously to the procedure described in the synthesis of Compound 199. MS (ESI) m/z (M+H)+ 531.1.
Compound 201a was prepared analogously to the procedure described in the synthesis of Compound 199a. $^1$H NMR (400 MHz, DMSO-d$_6$): δ 9.75 (s, 1 H), 7.74 (s, 1 H), 7.62 (d, J=6.8 Hz, 1 H), 7.33-7.45 (m, 10 H), 5.76 (q, 1 H), 3.67 (s, 3 H), 1.48-1.53 (m, 5 H), 1.19-1.21 (m, 2 H). MS (ESI) m/z (M+H)+ 534.2.

Synthesis of Compound 202
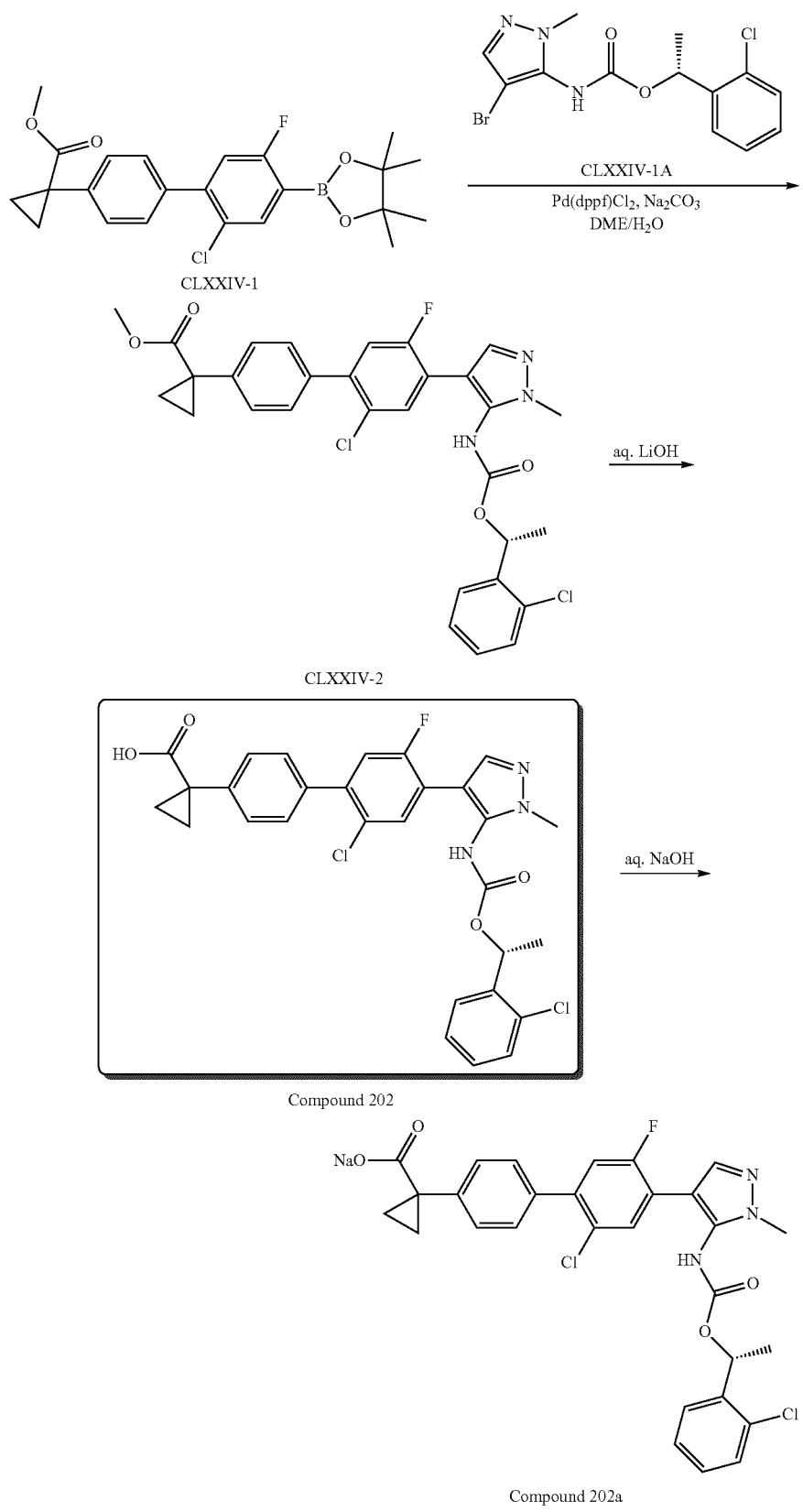

Compound 202 was prepared analogously to the procedure described in the synthesis of Compound 199. MS (ESI) m/z (M+H)+ 568.1.
Compound 202a was prepared analogously to the procedure described in the synthesis of Compound 199a. $^1$H NMR (400 MHz, DMSO-d$_6$): δ9.85 (s, 1 H), 7.74 (s, 1 H), 7.62 (m, 2 H), 7.33-7.45 (m, 8 H), 5.99-6.00 (q, 1 H), 3.68 (s, 3 H), 1.48-1.55 (m, 5 H), 1.19-1.21 (m, 2H). MS (ESI) m/z (M+H)+ 568.1.
Synthesis of Compound 203
Synthetic Route (Scheme CLXXV)
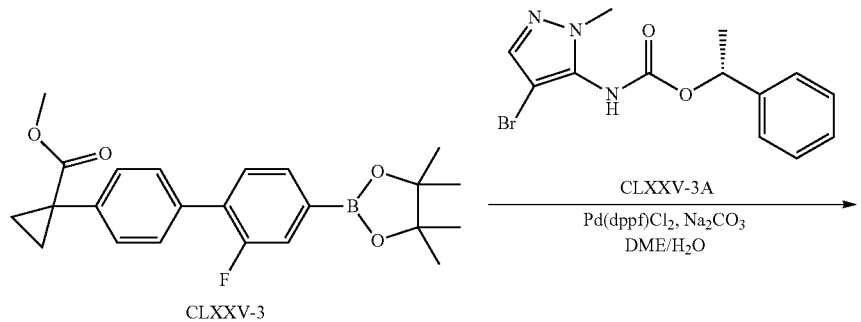
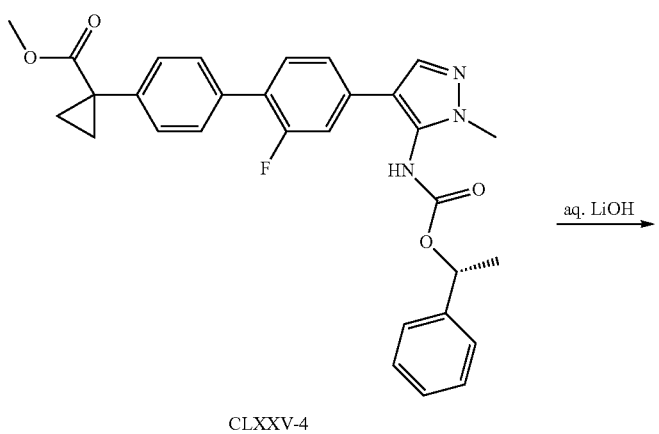
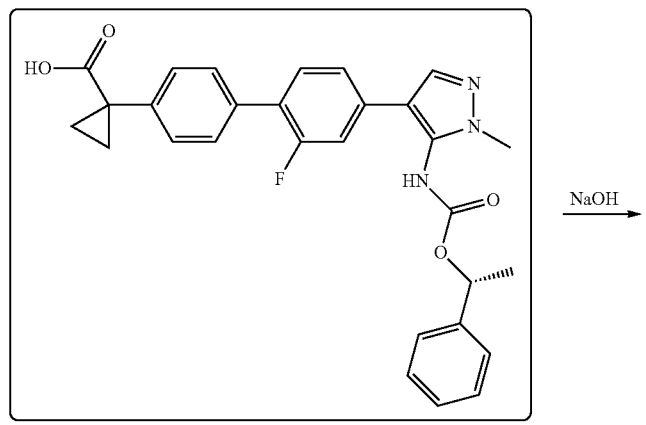
Compound 203

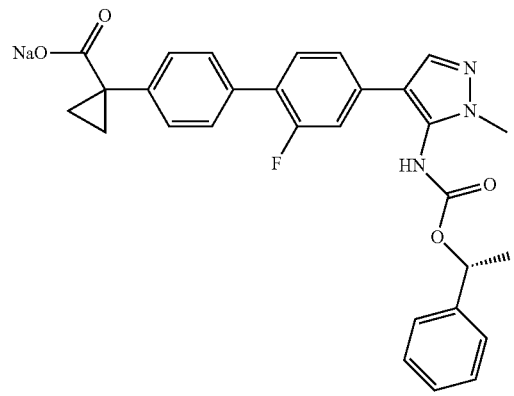
Compound 203a
Compound 203 was prepared analogously to the procedure described in the synthesis of Compound 199. MS (ESI) m/z (M+H)+ 500.2.
Compound 203a was prepared analogously to the procedure described in the synthesis of Compound 199a. $^1$H NMR (400 MHz, DMSO-d$_6$): δ 7.79 (s, 1H), 7.28-7.45 (m, 12H), 5.78-5.82 (m, 1H), 3.65 (s, 3H), 1.51 (d, J=6.8 Hz, 3H), 1.26-1.27 (m, 2H), 0.73-0.75 (m, 2H). MS (ESI) m/z (M+H)+ 500.2.
Synthesis of Compound 204
Synthetic Route (Scheme CLXXVI)
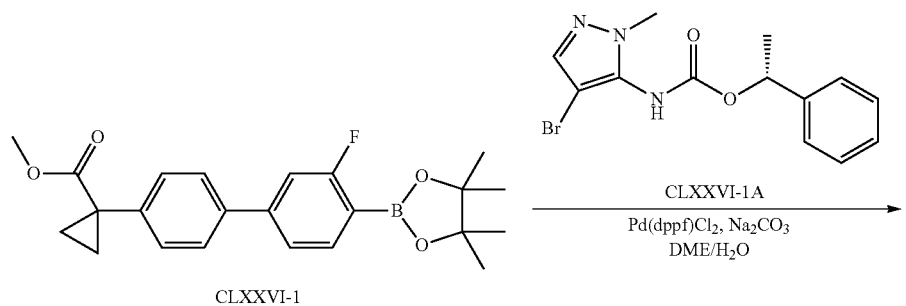
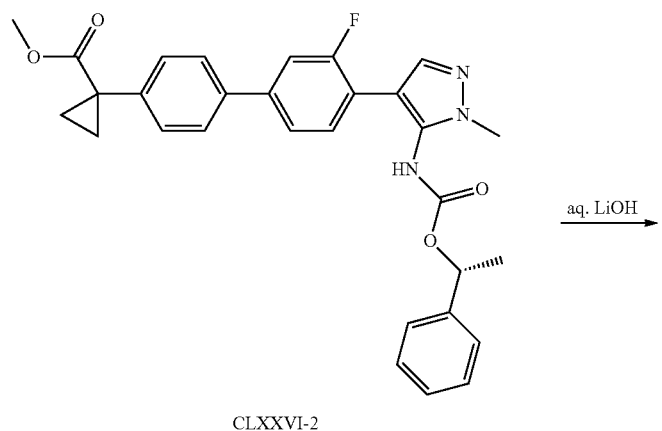

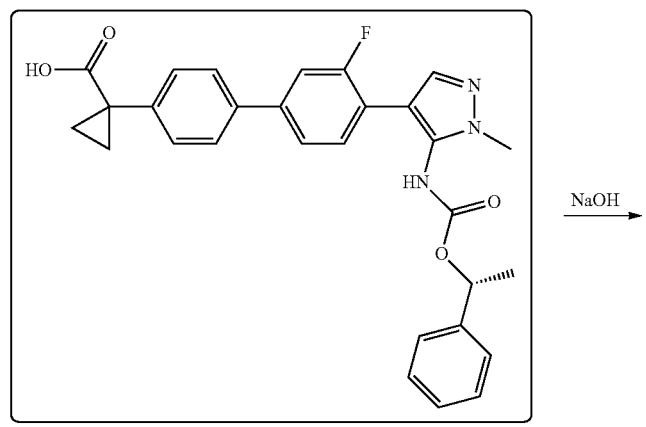
Compound 204
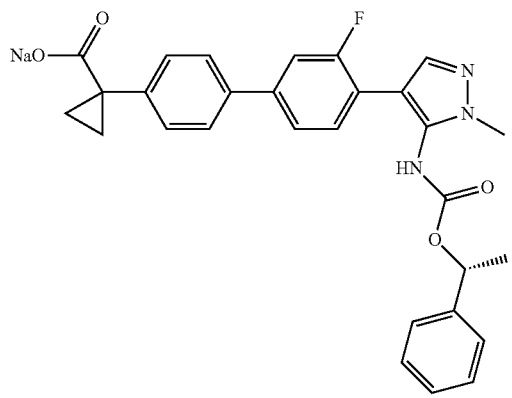
Compound 204a
Compound 204 was prepared analogously to the procedure described in the synthesis of Compound 199. MS (ESI) m/z (M+H)+ 500.1.
Compound 204a was prepared analogously to the procedure described in the synthesis of Compound 199a. $^1$H NMR (DMSO-$d_6$, 400 MHz): δ 7.65 (s, 1H), 7.28-7.52 (m, 12H), 3.68 (s, 3H), 1.48 (d, J=6.4 Hz, 2H), 1.31-1.32 (m, 2H), 0.79-0.80 (m, 2H). MS (ESI) m/z (M+H)+ 500.1.
Synthesis of Compound 205
Synthetic Route (Scheme CLXXVII)
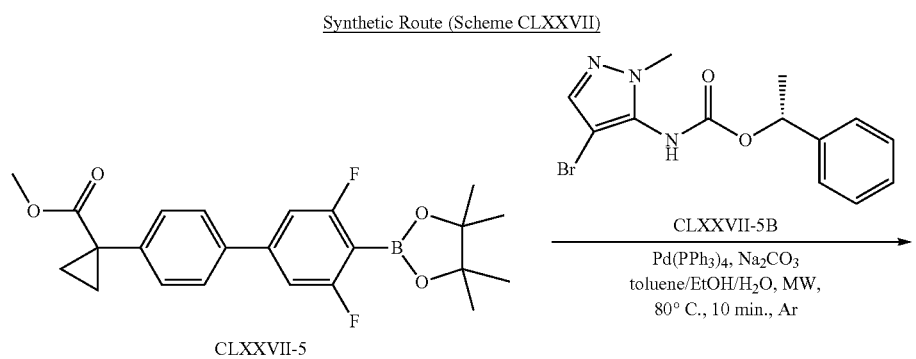

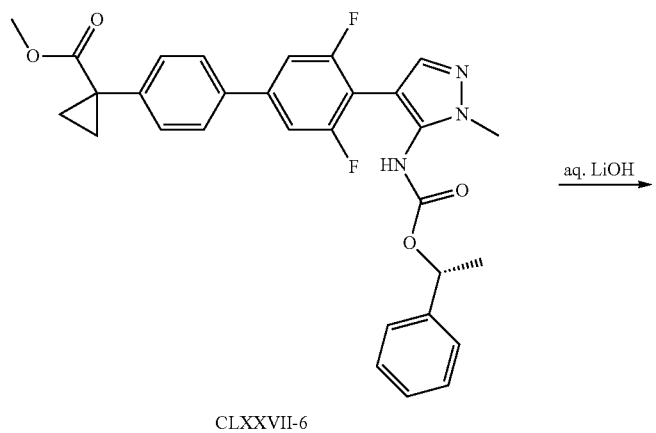
CLXXVII-6
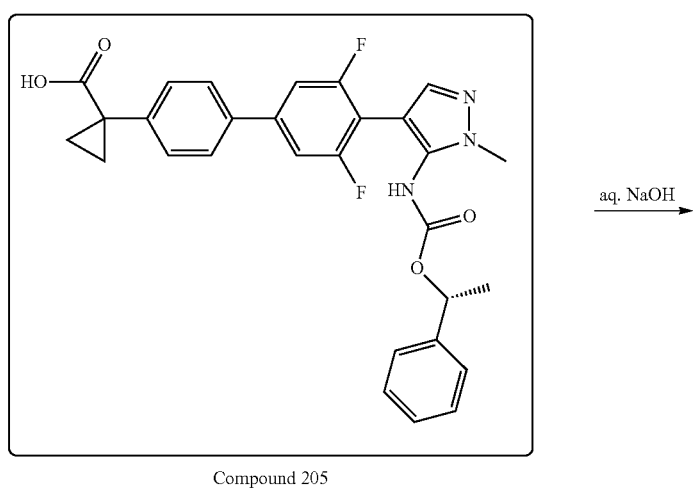
Compound 205
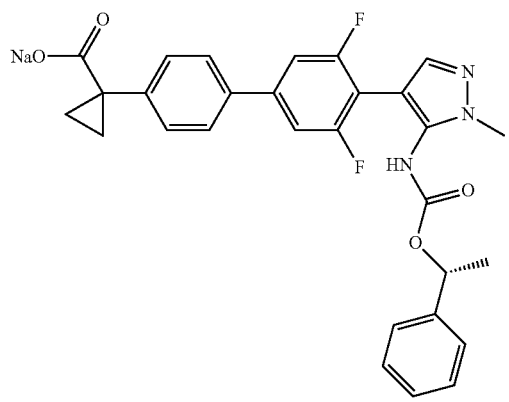
Compound 205a
Compound 205 was prepared analogously to the procedure described in the synthesis of Compound 199. MS (ESI) m/z (M+H)+ 518.1.
Compound 205a was prepared analogously to the procedure described in the synthesis of Compound 199a. $^1$H NMR (400 MHz, DMSO-d$_6$): δ 9.23 (br, 1H), 7.52-7.55 (m, 3H), 7.26-7.40 (m, 9H), 5.69-5.74 (q, 1H), 3.69 (s, 3H), 1.43-1.45 (d, J=6.4 Hz, 3H), 1.24-1.26 (br, 2H), 0.73-0.72 (br, 2H). MS (ESI) m/z (M+H)+ 518.0.

Synthesis of Compound 206

Synthetic Route (Scheme CLXXVIII)

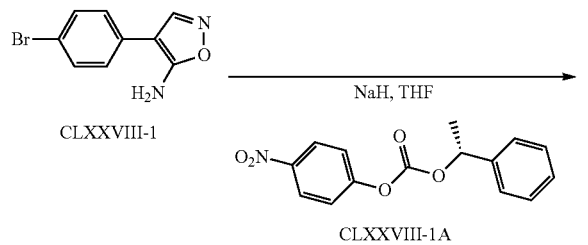

CLXXVIII-1

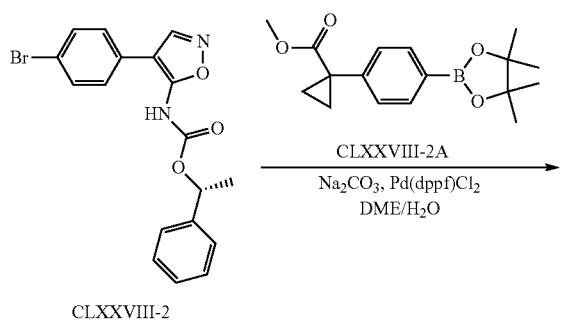

CLXXVIII-2

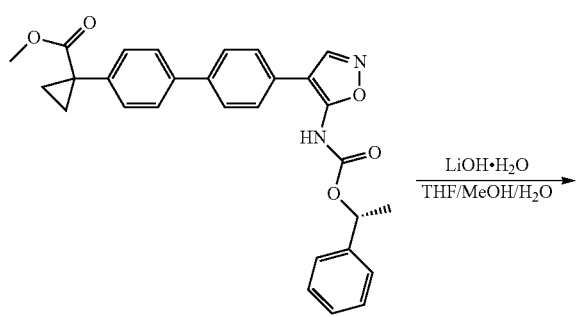

CLXXVIII-3

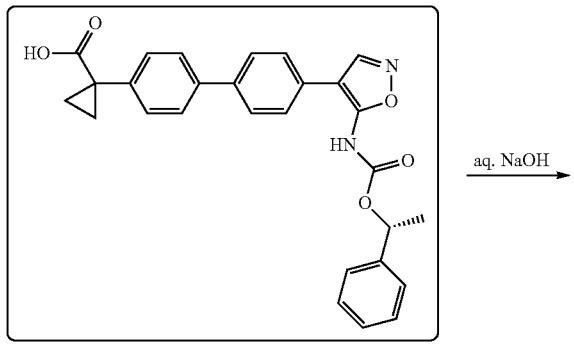

Compound 206

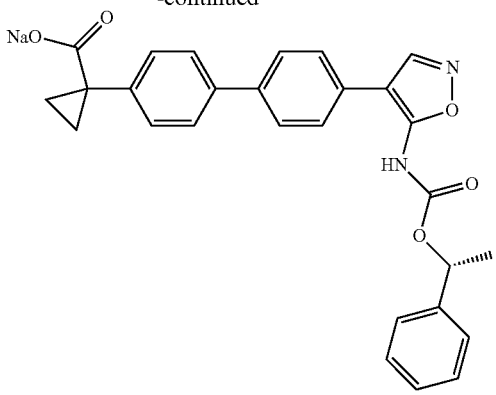

Compound 206a

To a stirred solution of compound CLXXVIII-1 (100 mg, 0.42 mmol), compound CLXXVIII-1A (144 mg 0.5 mmol) in THF (15 mL) was added NaH (28.8 mg 1.2 mmol) under nitrogen. After the addition, the solution was heated to reflux under nitrogen for overnight. The solution was concentrated, then $H_2O$ (20 mL) was added, and the mixture was extracted with EtOAc (30 mL×3). The organic layer was combined and washed with brine, dried over $Na_2SO_4$, concentrated in vacuo. The residue was purified by column chromatography on silica gel (PE:EA=4:1) to afford compound CLXXVIII-2 (80 mg, yield 50%).

To a stirred solution of compound CLXXVIII-2 (70 mg, 0.18 mmol), compound CLXXVIII-2A (65 mg 0.2 mmol), $Na_2CO_3$ (38 mg 0.36 mmol) in DME (10 mL) and $H_2O$ (2 mL) was added $Pd(dppf)Cl_2$ (7 mg, 0.01 mmol) under nitrogen. After the addition, the solution was heated to reflux under nitrogen for 2 hours. The solution was concentrated, then $H_2O$ (10 mL) was added, and the mixture was extracted with EtOAc (10 mL×3). The organic layer was combined and washed with brine, dried over $Na_2SO_4$, concentrated in vacuo. The residue was purified by HPLC to afford compound CLXXVIII-3 (30 mg, yield 34%).

Preparation of Compound 206

To a solution of compound CLXXVIII-3 (30 mg, 0.06 mmol) in MeOH (2 mL), THF (2 mL), $H_2O$ (2 mL) was added LiOH—$H_2O$ (13 mg, 0.3 mmol). The mixture was stirred overnight at room temperature. Then concentrated, water (10 mL), HCl (2 N) was added to pH=2, extracted with EtOAc (10 mL×3). The combined organic layers were washed with brine (10 mL×2), and concentrated under reduced pressure. The residue was purified by prep HPLC to give Compound 206 (17 mg, yield: 60.7%). MS (ESI) m/z $(M+H)^+$ 469.1.

Preparation of Compound 206a

To a solution of Compound 206 (17 mg) in MeOH (5 mL) was added NaOH (0.05N, 0.73 mL) stirred for one hour, then the reaction mixture was lyophilized to give Compound 206a. $^1$H NMR (400 MHz, DMSO-$d_6$): δ 8.99 (s, 1H), 7.64-7.65 (m, 4H), 7.58 (d, J=8.4 Hz, 2H), 7.30-7.41 (m, 7H), 5.51-5.61 (q, 1H), 1.46 (d, J=6.4 Hz, 3H), 1.42 (br, 2H), 1.07 (br, 2H). MS (ESI) m/z $(M+H)^+$ 469.1.

Synthesis of Compound 207

Synthetic Route (Scheme CLXXIX)

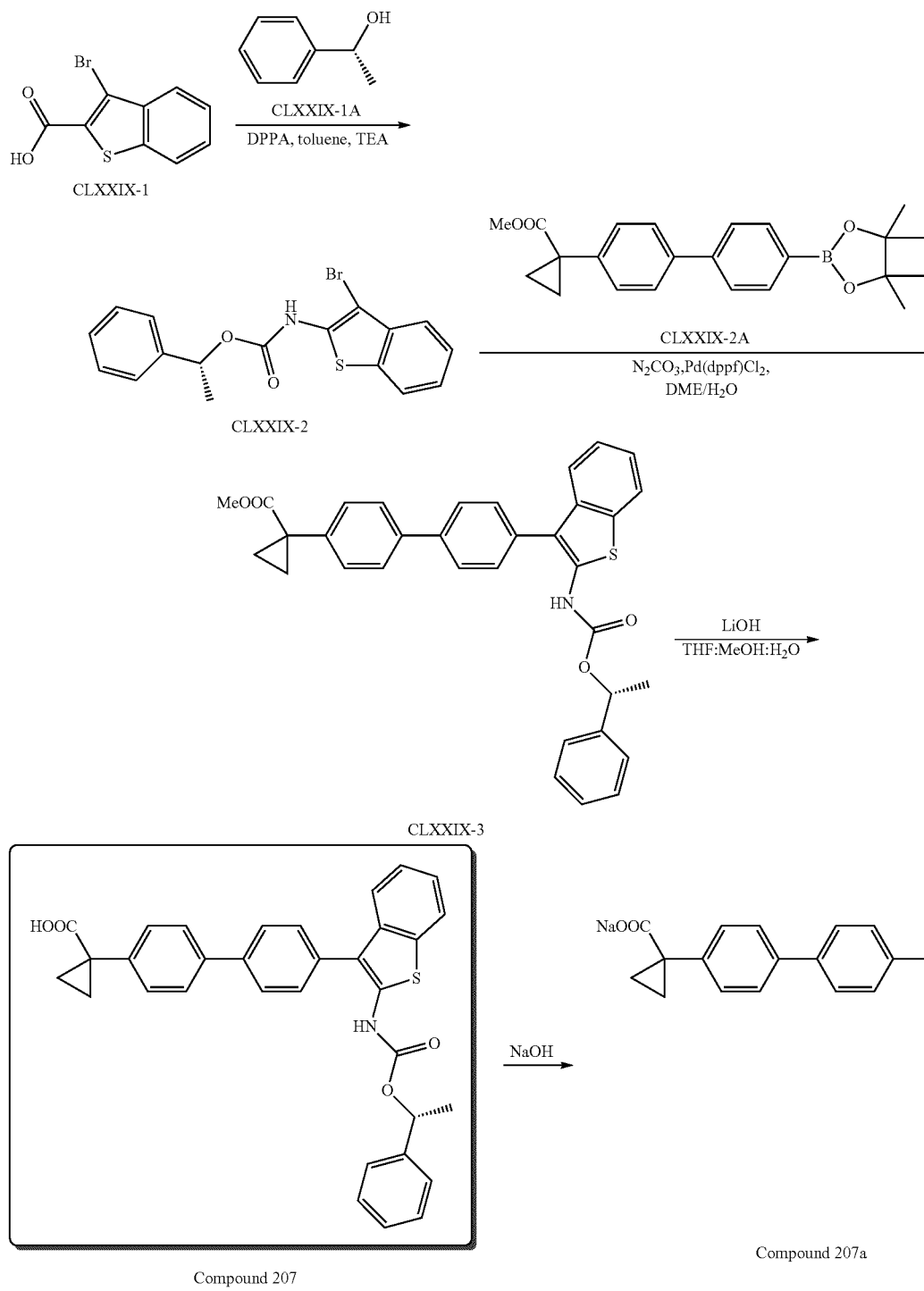

The mixture of compound CLXXIX-1 (2 g, 7.8 mmol), compound CLXXIX-1A (1.4 g, 9.4 mmol), DPPA (2.58 g, 9.4 mmol) and Et₃N (1.58 g, 15.6 mmol) in toluene (50 mL) was stirred at reflux under nitrogen for 1 hour. The mixture was concentrated, and the residue was partitioned between H₂O (20 mL) and DCM (50 mL), the aqueous phase was extracted with DCM (20 mL×2). The combined organic layer was washed with brine, dried over Na₂SO₄, and concentrated. The residue was purified by column chromatography on silica gel (PE:EA=5:1) to afford compound CLXXIX-2 (1.2 g, yield 40.96%).

Na₂CO₃ (294 mg, 2.77 mmol) and compound CLXXIX-2A (0.63 g, 1.66 mmol) were added to a solution of compound CLXXIX-2 (0.52 g, 1.38 mmol) in DME/H₂O (20 mL, v/v=3/

1), the resulting mixture was purged with nitrogen, then Pd(dppf)Cl$_2$ (60 mg) was added. The reaction mixture was stirred at 80° C. overnight under nitrogen protection. After completion of the reaction, the mixture was poured into water, extract with EtOAc (30 mL×3), the combined organic layers were dried over Na$_2$SO$_4$, concentrated in vacuo. The residue was purified by chromatography (PE:EA=5:1) to afford compound CLXXIX-3 (300 mg, yield: 39.5%).

Preparation of Compound 207

To a stirred solution of compound CLXXIX-3 (300 mg, 0.56 mmol) in MeOH/H$_2$O (15 mL, v/v=5/1) was added LiOH (118.8 mg, 2.83 mmol). After the addition, the solution was stirred overnight at r.t. The solution was concentrated in vacuo, the aqueous layer was adjust pH to 2 with 1N HCl, and extracted with EtOAc (10 mL×3). The organic layer was separated, dried and concentrated. The residue was purified by prep-HPLC to afford Compound 207 (90 mg, yield: 30.7%).

Preparation of Compound 207a

To a solution of Compound 207 (210 mg, 0.394 mmol) in MeOH (1 mL) and MeCN (5 mL) was added 0.05 N sodium hydroxide solution (7.88 mL) at 0° C. The reaction mixture was stirred for 20 minutes. The mixture was freeze-dried to give Compound 207a. $^1$H NMR (400 MHz, DMSO-d$_6$): δ 7.68-7.70 (m, 3H), 7.53-7.58 (m, 5H), 7.45 (d, J=8.0 Hz, 1H), 7.31-7.36 (m, 6H), 7.17-7.26 (m, 2H), 5.75-5.77 (q, 1H), 1.44 (d, J=6.4 Hz, 3H), 1.21 (br, 2H), 0.73 (br, 2H). MS (ESI) m/z (M−H)$^-$ 532.2.

Synthesis of Compound 208

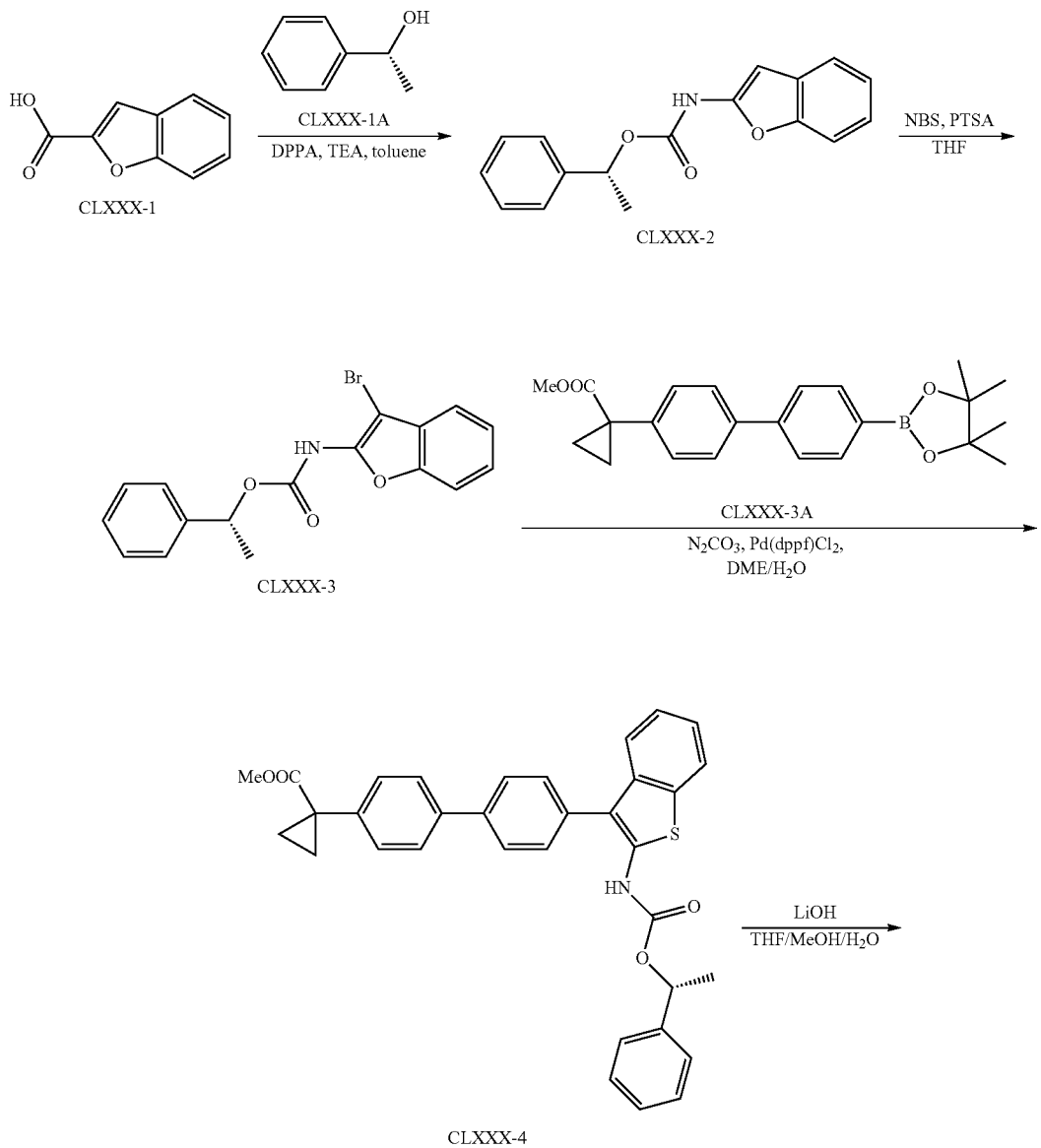

Synthetic Route (Scheme CLXXX)

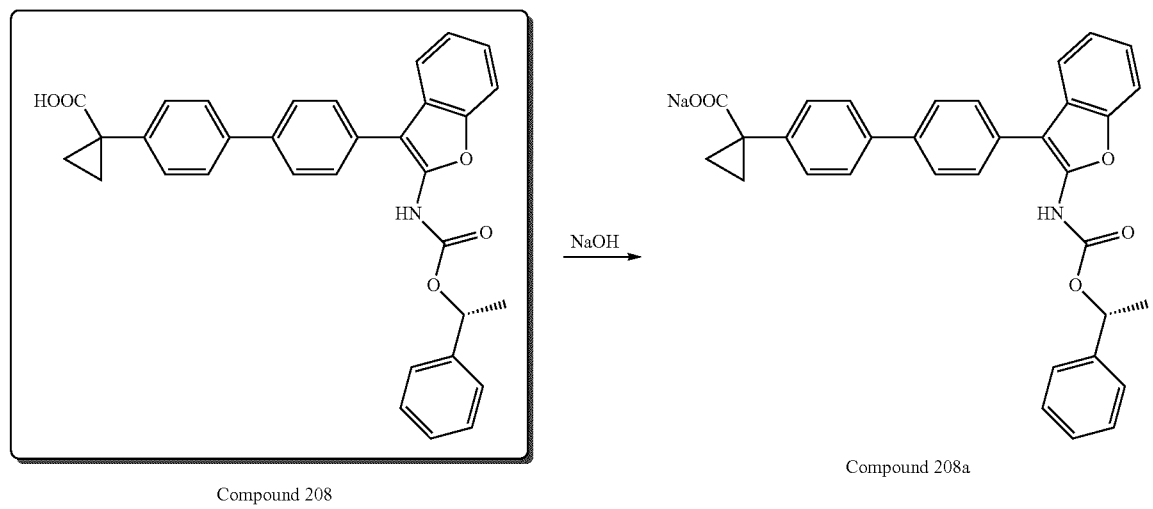

Compound 208                          Compound 208a

The mixture of compound CLXXX-1 (1 g, 6.17 mmol), compound CLXXX-1A (0.904 g, 7.41 mmol), DPPA (2.03 g, 7.41 mmol) and Et$_3$N (1.24 g, 7.41 mmol) in toluene (30 mL) was stirred at reflux under nitrogen for 1 hour. The mixture was concentrated, and the residue was partitioned between H$_2$O and DCM, the aqueous phase was extracted with DCM. The combined organic layer was washed with brine, dried over Na$_2$SO$_4$, and concentrated. The residue was purified by chromatography on silica gel (PE:EA=5:1) to afford compound CLXXX-2 (500 mg, yield: 28.9%).

NBS (380 mg, 2.13 mmol) was added to a solution of compound CLXXX-2 (500 mg, 1.779 mmol) and PTSA (32.9 mg, 0.177 mmol) in THF at 0° C. The mixture was stirred at 20° C. for 14 h, then diluted with CH$_2$Cl$_2$ (20 mL), and washed with water, brine. The organic phase was dried with anhydrous sodium sulfate, filtered, and concentrated, the residue was purified by chromatography on silica gel (PE:EA=5:1) to afford compound CLXXX-3 (330 mg, yield 51.7%).

Compound 208 was prepared analogously to the procedure described in the synthesis of Compound 207 (120 mg, yield 41.1%).

Compound 208a was prepared analogously to the procedure described in the synthesis of Compound 207a. $^1$H NMR (400 MHz, DMSO-d$_6$): δ 7.73-7.76 (m, 2H), 7.65-7.69 (m, 3H), 7.51 (d, J=8.4 Hz, 2H), 7.31-7.45 (m, 7H), 7.22-7.29 (m, 3H), 5.74-5.79 (q, 1H), 1.46 (d, J=6.4 Hz, 3H), 1.27 (br, 2H), 0.74 (br, 2H). MS (ESI) m/z (M–H)$^-$ 516.2.

Synthesis of Compound 209

Synthetic Route (Scheme CLXXXI)

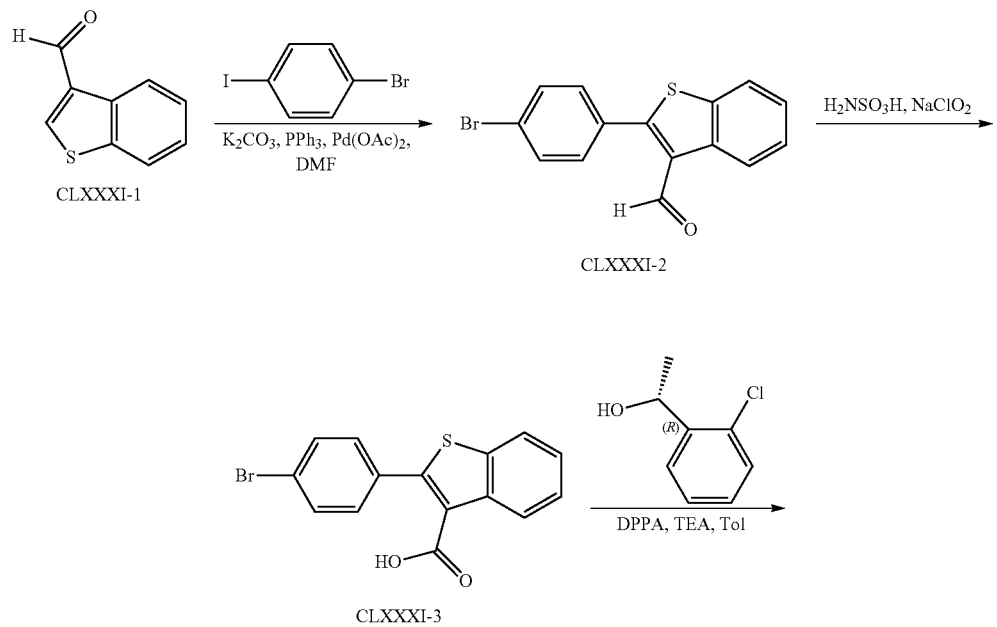

-continued
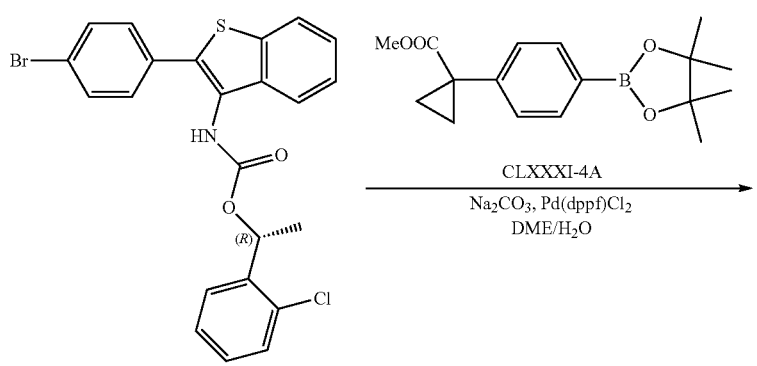
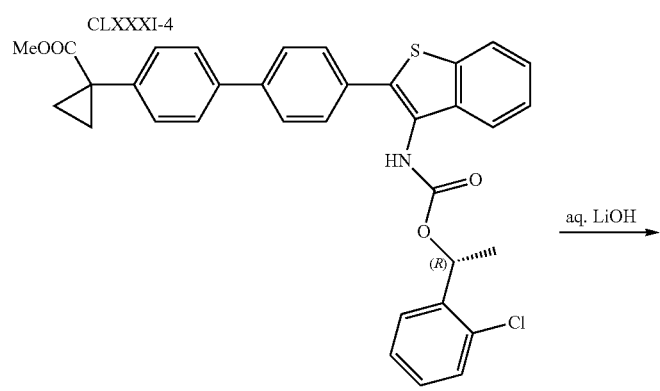
CLXXXI-4
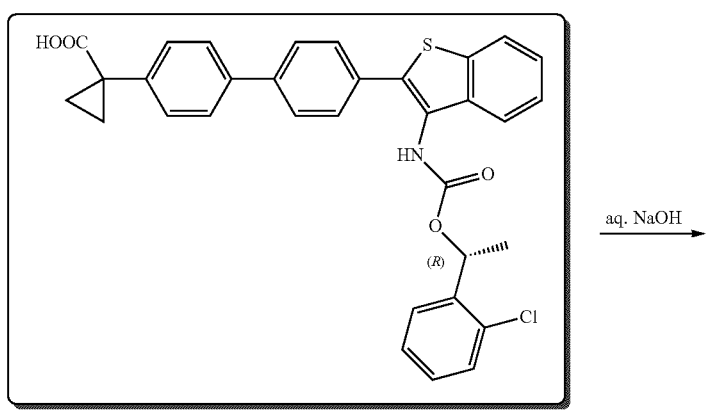
CLXXXI-5
Compound 209
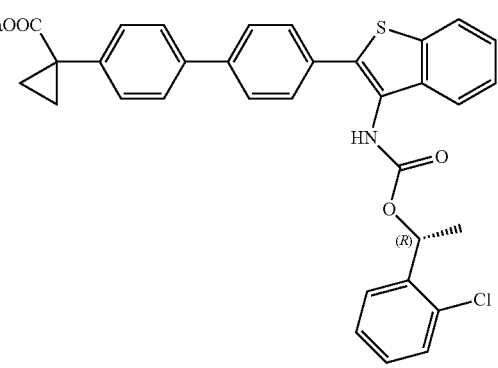
Compound 209a
Argon gas was bubbled through a mixture of compound CLXXXI-1 (8.1 g, 50.00 mmol), 1-bromo-4-iodobenzene (14.1 g, 50 mmol) and potassium carbonate (20.7 g, 150 mmol) in DMF (100 mL). Then PPh$_3$ (1.3 g, 5.0 mmol) and Pd(OAc)$_2$ (0.55 g, 2.5 mmol) was added. The mixture was heated to 120° C. and stirred overnight. After cooled, the reaction mixture was concentrated; the residue was treated with ethyl acetate, filtered through Celite. The filtrated was washed with water, brine, dried and concentrated. The residue was purified by flash column chromatography over silica gel (PE:EA=30/1) to afford compound CLXXXI-2 (8.9 g, 56% yield).

To a suspension of compound CLXXXI-2 (3.6 g, 11.35 mmol) in 150 mL of dioxane/H$_2$O (v/v=7/3) was added sulfamic acid (6.28 g, 64.70 mmol) and sodium chlorite (1.33 g, 14.75 mmol). The mixture was stirred for 2 hours at room temperature. The volatile solvent was evaporated. The residue was acidified to pH=3 with 2 N HCl, extracted with ethyl acetate (3×100 mL). The combined organic layer was washed with brine, dried and concentrated. The resulting solid was washed with t-butylmethylether to afford compound CLXXXI-3 (3.8 g, yield 100%).

Compound 209 was prepared analogously to the procedure described in the synthesis of Compound 31 (80 mg, yield 68%). MS (ESI) m/z (M+23)$^+$589.9.

Compound 209a. $^1$H NMR (DMSO-d$_6$, 400 MHz): δ 9.20 (br, 1H), 7.93-7.96 (m, 1H), 7.68-7.74 (m, 4H), 7.59-7.61 (m, 1H), 7.51-7.53 (m, 2H), 7.32-7.44 (m, 8H), 6.02 (q, J=6.4 Hz, 1H), 1.48 (d, J=6.4 Hz, 3H), 1.24-1.27 (m, 2H), 0.71-0.73 (m, 2H), 1.56 (d, J=6.4 Hz, 3H). MS (ESI) m/z (M+23)$^+$589.9.

Synthesis of Compound 210

Synthetic Route (Scheme CLXXXII)

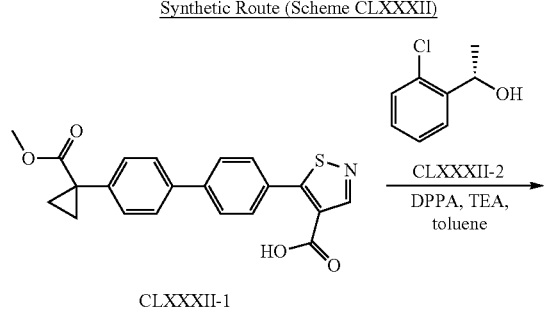

CLXXXII-1

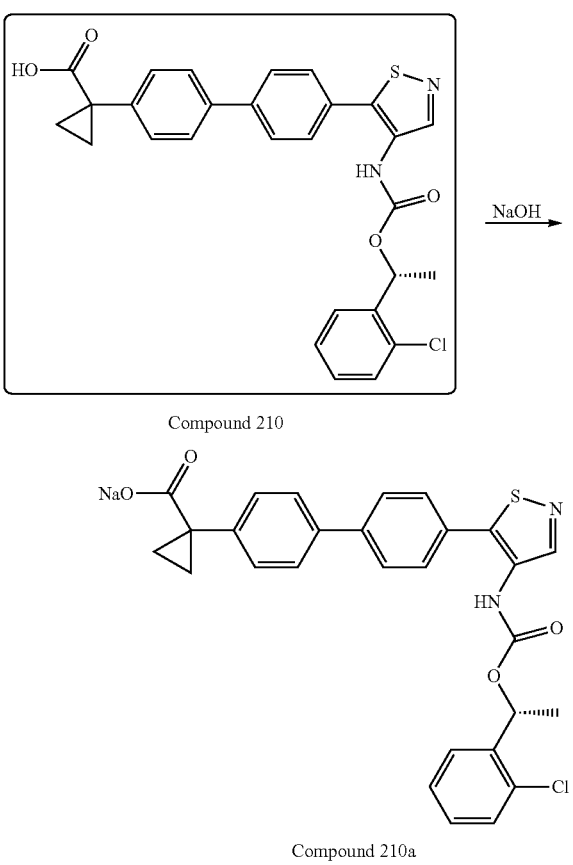

Compound 210

Compound 210a

Compound 210 was prepared analogously to the procedure described in the synthesis of Compound 114. MS (ESI) m/z (M+H)$^+$ 519.1.

Compound 210a was prepared analogously to the procedure described in the synthesis of Compound 114a. $^1$HNMR (Methanol-d$_4$ 400 MHz): δ 8.58 (s, 1H), 7.73 (d, J=8.0 Hz, 2H), 7.61-7.63 (m, 5H), 7.47 (d, J=8.0 Hz, 2H), 7.26-7.38 (m, 3 H), 6.16 (br, 1 H), 1.60-1.63 (q, 2 H), 1.55 (br, 3 H), 1.23-1.26 (q, 2 H). MS (ESI) z (M+H)$^+$ 518.9.

Synthesis of Compound 211

Synthetic Route (Scheme CLXXXIII)

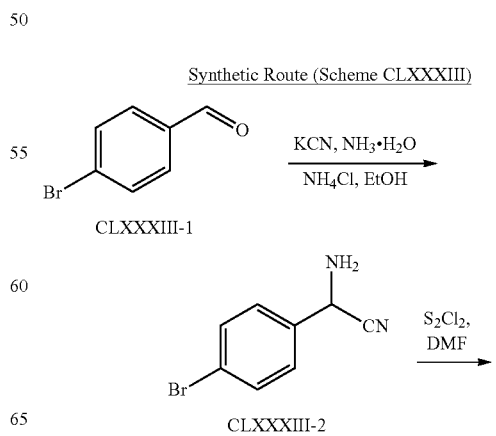

CLXXXIII-1

CLXXXIII-2

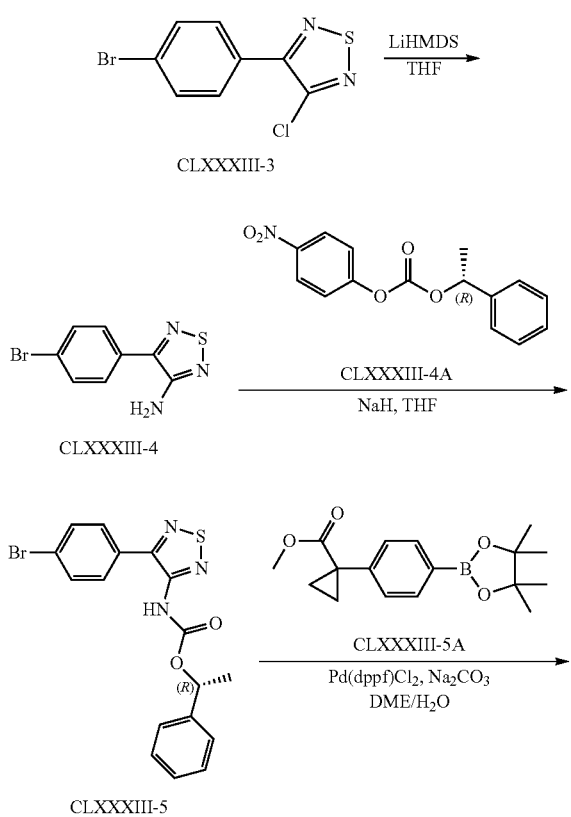

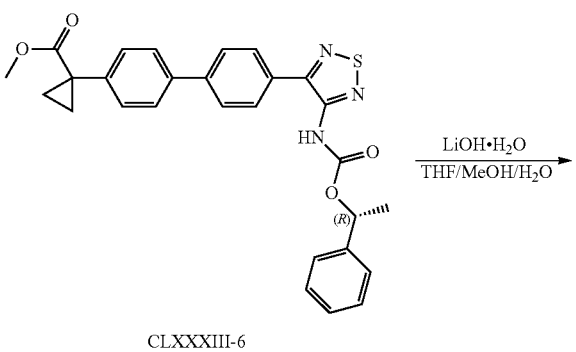

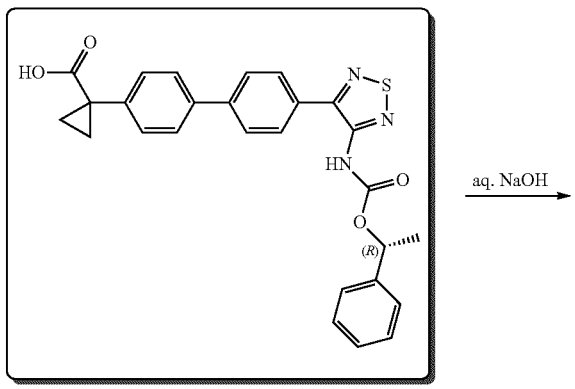

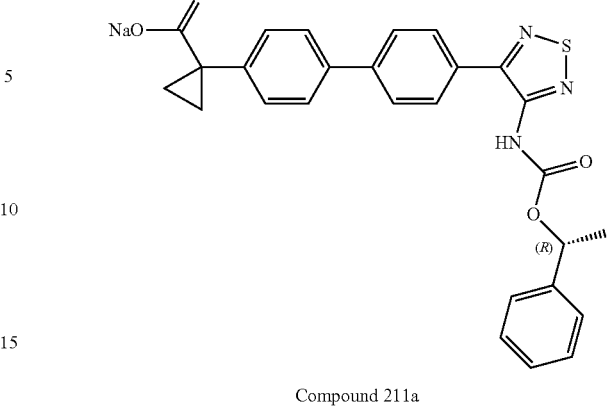

Compound 211a

To a solution of compound CLXXXIII-1 (10 g, 54.4 mmol) in EtOH (25 mL), KCN (4.25 g, 65.2 mmol), NH$_4$Cl (5.83 g, 108.8 mmol) in 25% NH$_3$ (aq.) was added over 10 min. The reaction mixture was stirred at room temperature for 2 hours under nitrogen protection. After completion of the reaction, the mixture was extracted with methyl-t-butyl ether washed with water. The organic layers were washed with brine, dried over Na$_2$SO$_4$ and concentrated to afford compound CLXXXIII-2 (crude 11 g), which was used to next directly.

To a solution of disulfur dichloride (3.18 mL, 39.75 mmol) in 15 mL of DMF was added compound CLXXXIII-2 (3.0 g, 14.21 mmol) in portions. The mixture was stirred overnight at room temperature. The mixture was poured into ice-water. The precipitate was filtered off and the filtrate was extracted with ethyl acetate (3×60 mL). The combined organic layer was washed brine, dried and concentrated. The residue was purified by flash column chromatography over silica gel (PE/EA=20/1) to afford compound CLXXXIII-3 (1.8 g, yield 46%).

A solution of 1 N lithium bis(trimethylsilyl)amide in THF (4.4 mL, 4.4 mmol) was added to a solution of compound CLXXXIII-3 (1.15 g, 4.17 mmol) in THF dropwise at 0° C. 15 minutes later the mixture temperature was allowed to rise to room temperature slowly and the mixture was stirred for 3 hours at room temperature. 2 N aq. HCl solution was added and the mixture was stirred for additional 30 minutes. Then the mixture was extracted with ethyl acetate, dried and concentrated. The residue was purified by flash column chromatography over silica gel (PE/EA=5/1) to afford compound CLXXXIII-4 (0.73 g, yield 68%).

To a solution of compound CLXXXIII-4 (715 mg, 2.79 mmol) in THF (20 mL) at 0° C. was added sodium hydride (279 mg, 6.98 mmol) in portions. 30 minutes later, a solution of compound CLXXXIII-4A (802 mg, 2.79 mmol) in 1 mL of THF was added. The mixture was heated to 60° C. and stirred for 2 hours. Then the mixture was diluted with ethyl acetate, washed with water, brine, dried and concentrated. The residue was purified by flash column chromatography over silica gel (PE/EA=5/1) to afford compound CLXXXIII-5 (900 mg, yield 80%).

Argon gas was bubbled through a solution of compound CLXXXIII-5 (900 mg, 2.23 mmol) and compound CLXXXIII-5A (674 mg, 2.23 mmol) in DME/H$_2$O (v/v=3/1, 10 mL). Then Na$_2$CO$_3$ (473 mg, 4.46 mmol) and Pd(dppf)Cl$_2$ (82 mg, 0.011 mmol) was added. The reaction mixture was stirred at 80° C. for 2 hours. The mixture was filtered through Celite and the filtrate was washed with brine, dried and concentrated. The residue was purified by flash column chromatography over silica gel (PE/EA=3/1) to afford compound CLXXXIII-6 (1.02 g, yield 92%).

Preparation of Compound 211

To a stirred solution of compound CLXXXIII-6 (1.01 g, 2.02 mmol) in 10 mL of THF/MeOH/H$_2$O (v/v/v=1/1/1) was added lithium hydroxide monohydrate (339 mg, 8.07 mmol). The mixture was stirred overnight at room temperature. The volatile solvent was evaporated in vacuum. The resulting aqueous solution was acidified to pH=3 with 2 N HCl, and extracted with ethyl acetate (3×45 mL). The combined organic layer was washed with brine, dried and concentrated. The residue was treated with 4 mL of methanol. The resulting precipitate was collected and dried to afford Compound 211 (720 mg, yield 73%). $^1$H NMR (DMSO-d$_6$, 400 MHz): δ 10.38 (s, 1H), 7.86 (d, J=8.0 Hz, 2H), 7.78 (d, J=8.0 Hz, 2H), 7.65 (d, J=8.0 Hz, 2H), 7.46 (d, J=8.0 Hz, 2H), 7.29-7.35 (m, 5H), 5.68 (q, J=6.8 Hz, 1H), 1.49-1.50 (m, 2H), 1.39 (d, J=6.8 Hz, 3H), 1.20-1.21 (m, 2H). MS (ESI) m/z (M+23)$^+$508.3.

Preparation of Compound 211a

To a stirred solution of Compound 211 (710.8 mg, 1.464 mmol) in 10 mL of MeOH was added 0.05 N NaOH aqueous solution (29.278 mL, 1.464 mmol). The mixture was stirred for 15 minutes at r.t. and the volatile solvent was evaporated. The residue was diluted with water and lyophilized to yield Compound 211a. $^1$H NMR (DMSO-d$_6$, 400 MHz): δ 7.93 (d, J=8.0 Hz, 2H), 7.72 (d, J=8.4 Hz, 2H), 7.55 (d, J=8.4 Hz, 2H), 7.29-7.39 (m, 7H), 5.69 (q, J=6.8 Hz, 1H), 1.40 (d, J=6.8 Hz, 3H), 1.265-1.27 (m, 2H), 0.78-0.79 (m, 2H). MS (ESI) m/z (M+23)$^+$ 507.9.

Synthesis of Compound 212

Synthetic Route (Scheme CLXXXIV)

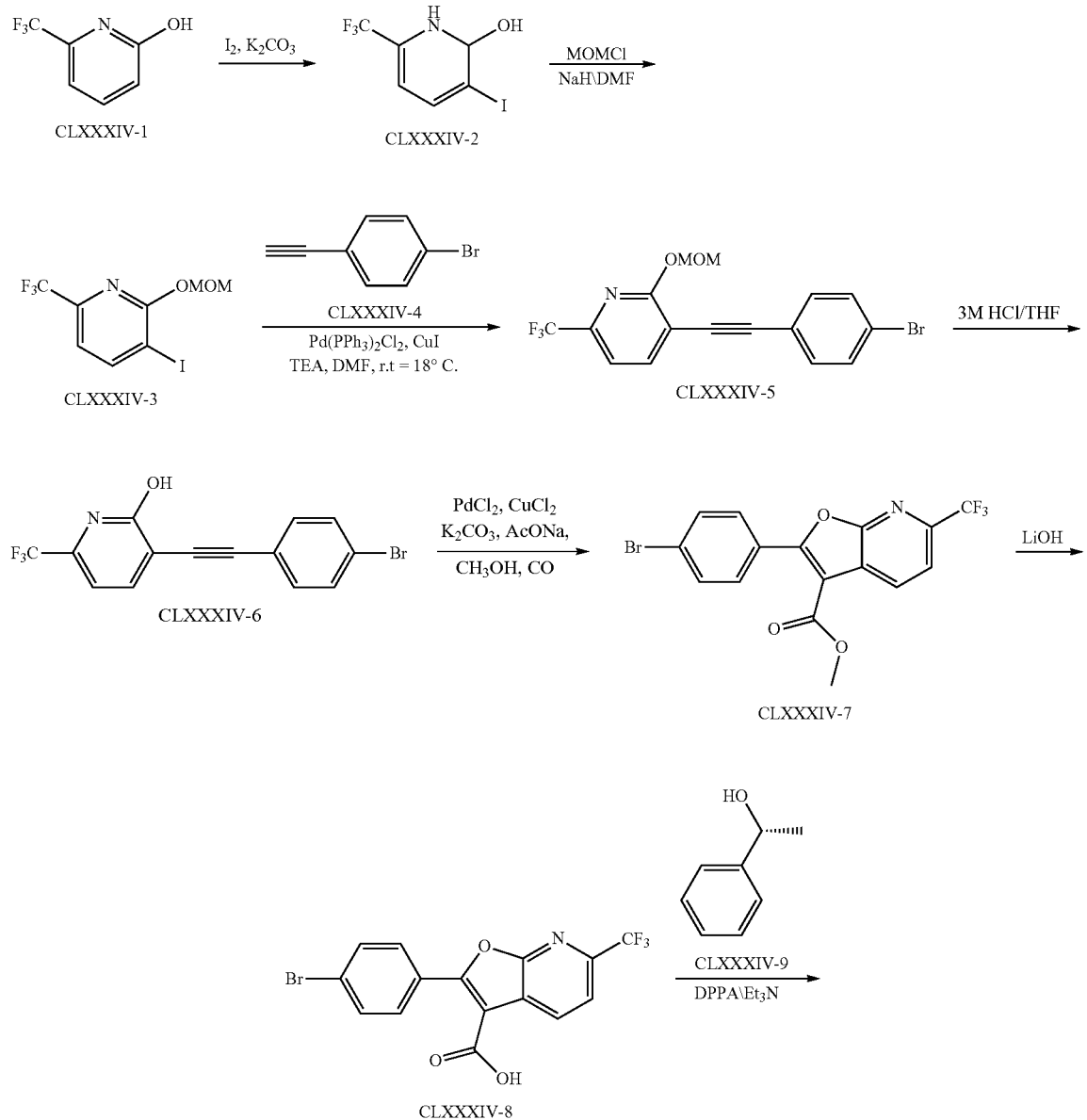

-continued
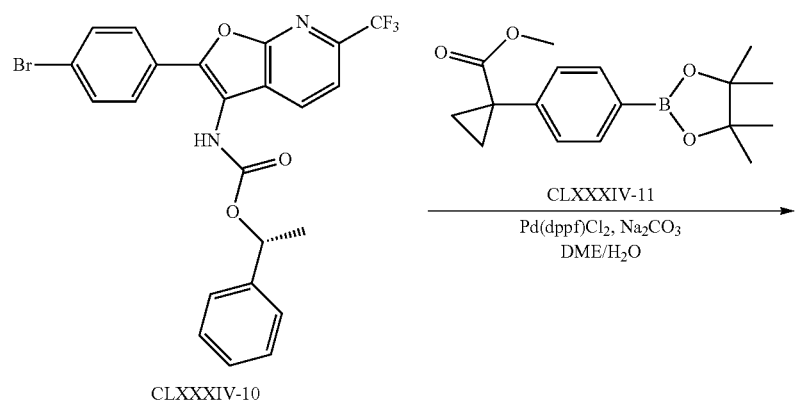
CLXXXIV-10
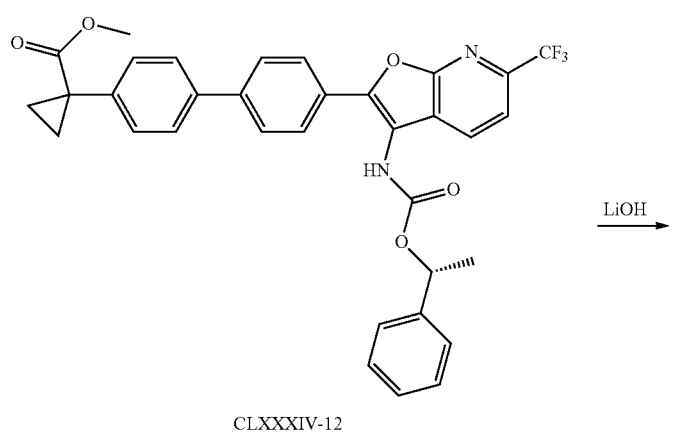
CLXXXIV-12
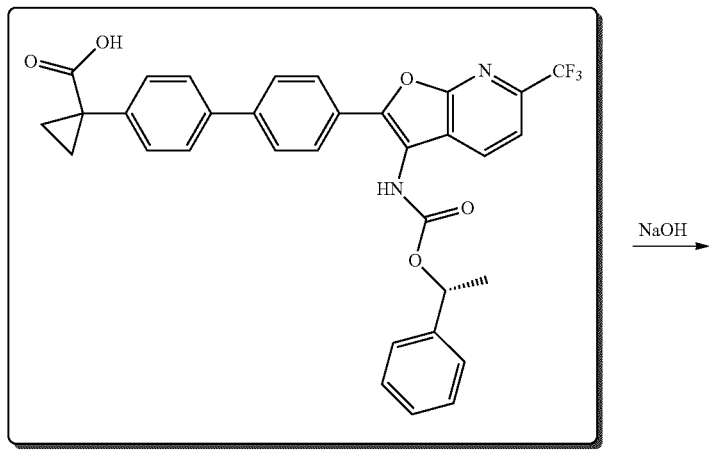
Compound 212

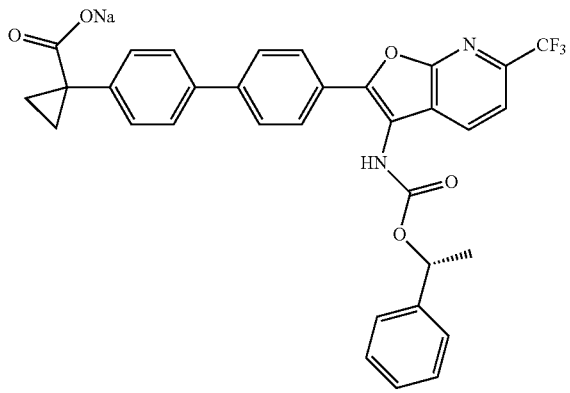

Compound 212a

The mixture of compound CLXXXIV-1 (3.0 g, 18.4 mmol), K₂CO₃ (5.1 g, 36.7 mmol) and I₂ (5.0 g, 18.4 mmol) in water (10 mL) was stirred for 24 h at room temperature. Then saturated Na₂S₂O₃ (20 mL) was added and followed by added HCl (1N) to adjust pH=2, and extracted with EtOAc (60 mL×3). The extracts were washed brine, dried over MgSO₄. The solvent was evaporated and the residue was purified by chromatography on silica (EA:PE=1:10) to afford compound CLXXXIV-2 (3.5 g, yield 62.7%).

NaH (83 mg, 2.08 mmol) was added to a stirred solution of compound CLXXXIV-2 (500 mg, 1.73 mmol) in DMF (3.5 mL), the mixture was stirred for 45 min, and MOMCl (160 mg, 1.98 mmol) was added dropwise. The reaction mixture was stirred for 2 h at room temperature. After diluted with water (10 mL), the mixture was extracted with EtOAc (20 mL×3), the organic layer was washed with brine, dried over MgSO₄ and concentrated, the residue was purified by chromatography on silica (EA:PE=1:15) to afford compound CLXXXIV-3 (260 mg, yield 45.1%).

To a stirred solution of compound CLXXXIV-3 (260 mg, 0.78 mmol), compound CLXXXIV-4 (170 mg, 0.94 mmol), CuI (7.5 mg, 0.039 mmol) in DMF (7.5 mL) and TEA (2.5 mL) was added Pd(PPh₃)₂Cl₂ (27.3 mg, 0.039 mmol) under Ar. After the addition, the solution was stirred at r.t. for 3 h under Ar. After diluted with water (15 mL), the mixture was extracted with EtOAc (20 mL×3), the organic layer was washed with brine, dried over MgSO₄ and concentrated, the residue was purified by chromatography on silica (EA:PE=1:20) to afford compound CLXXXIV-5 (200 mg, yield: 66.7%).

To a stirred solution of compound CLXXXIV-5 (200 mg, 0.518 mmol) HCl (3 N, 3 mL) was added at room temperature. The solution was heated to reflux for 3 hours. After being cooled to room temperature, water was added and extracted with EtOAc (20 ml×3). The extracts were washed with brine, dried over Na₂SO₄, and concentrated to afford crude product, which was purified by chromatography on silica (EA:PE=1:20) to afford compound CLXXXIV-6 (156 mg, yield 86.4%).

Compound 212 was prepared analogously to the procedure described in the synthesis of Compound 152 (45.0 mg, yield: 45.9%).

Compound 212a was prepared analogously to the procedure described in the synthesis of Compound 152a. ¹H NMR (DMSO-d₆, 400 MHz): δ 8.15 (d, J=8.0 Hz, 1H), 8.00 (d, J=8.0 Hz, 2H), 7.78-7.83 (m, 3H), 7.56 (d, J=8.0 Hz, 2H), 7.31-7.42 (m, 7H), 5.81-5.86 (q, 1H), 1.55 (d, J=6.4 Hz, 3H), 1.28 (br, 2H), 0.76 (br, 2H). MS (ESI) m/z (M+H)⁺ 587.1.

Synthesis of Compound 213

Syntheitc Route (Scheme CLXXXV)

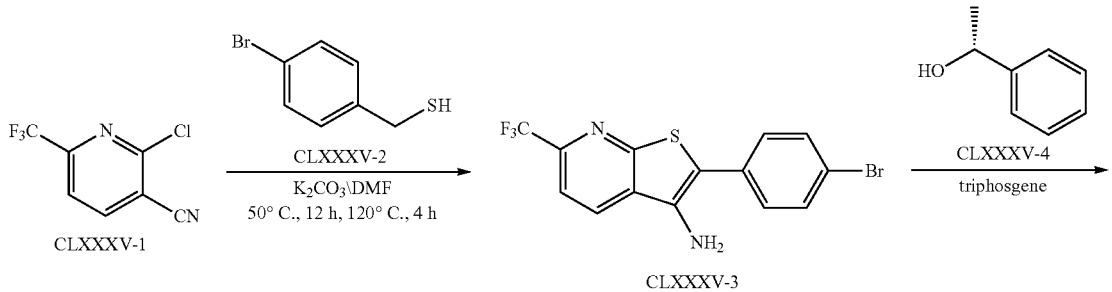

-continued
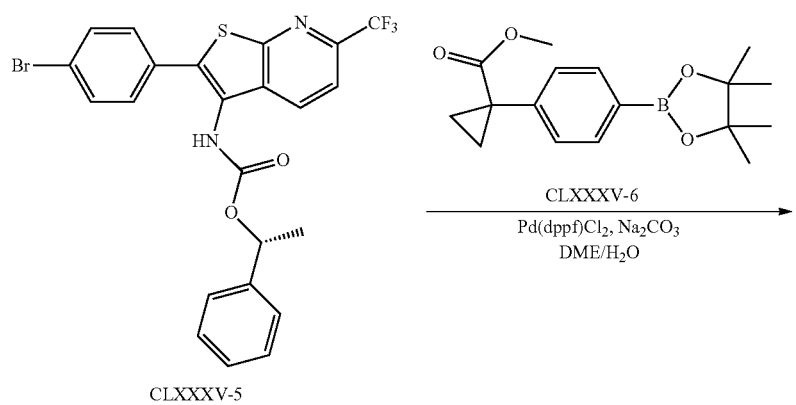
CLXXXV-5
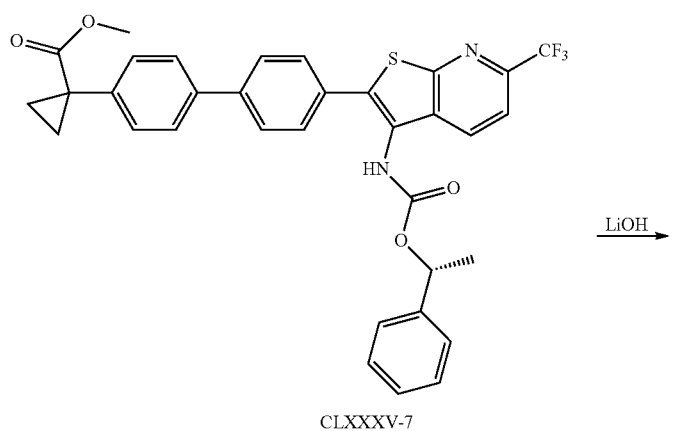
CLXXXV-7
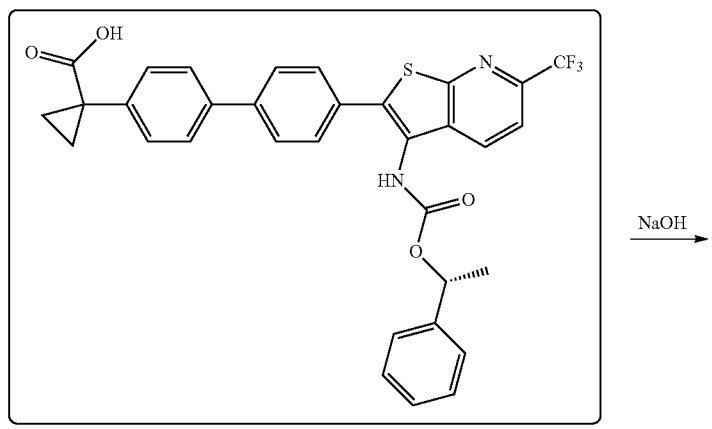
Compount 213

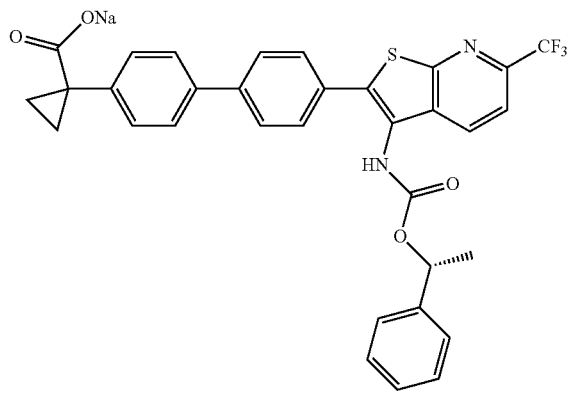

Compound 213a

To a solution of compound CLXXXV-1 (103 mg, 0.5 mmol) and compound CLXXXV-2 (131 mg, 0.5 mmol) in DMF (15 mL) was added $K_2CO_3$ (276 mg, 2.0 mmol) at room temperature. The reaction mixture was heated to 50° C. for 2 h and then 120° C. for 4 h. After being cooled to room temperature, water (10 mL) was added and extracted with EtOAc (20 mL×3). The extracts were washed brine, dried over $MgSO_4$. The solvent was evaporated and the residue was purified by prep. TLC (PE/EA=1/2) to afford compound CLXXXV-3 (110 mg, yield 59.1%).

Compound CLXXXV-4 (79.3 mg, 0.268 mmol) was added to a solution of compound CLXXXV-3 (110 mg, 0.268 mmol), DMAP (32.7 mg, 0.268 mmol), triphosgene (79.32 mg, 0.268 mmol) and TEA (135 mg, 1.34 mmol) in THF (5 mL). The reaction mixture was stirred for 0.5 h. After diluted with water, the reaction mixture was extracted with EtOAc (20 mL×3), washed with brine, dried over $MgSO_4$, and concentrated, the residue was purified by prep. TLC (PE/EA=5/1) to afford compound CLXXXV-5 (85 mg, yield 60.8%).

Compound 213 was prepared analogously to the procedure described in the synthesis of Compound 152 (42.0 mg, yield: 86.2%). MS (ESI) m/z (M+H)$^+$ 603.1.

Compound 213a was prepared analogously to the procedure described in the synthesis of Compound 152a. $^1$H NMR (DMSO-$d_6$, 400 MHz): δ 9.79 (br, 1H), 8.18 (d, J=7.6 Hz, 1H), 7.94 (d, J=8.4 Hz, 1H), 7.73-7.75 (m, 5H), 7.55 (d, J=8.4 Hz, 2H), 7.32-7.42 (m, 7H), 5.75 (br, 1H), 1.55 (br, 3H), 1.25 (br, 2H), 0.78 (br 2H). MS (ESI) m/z (M+H)$^+$ 603.1.

Synthesis of Compound 214

Synthetic Route (Scheme CLXXXVI)

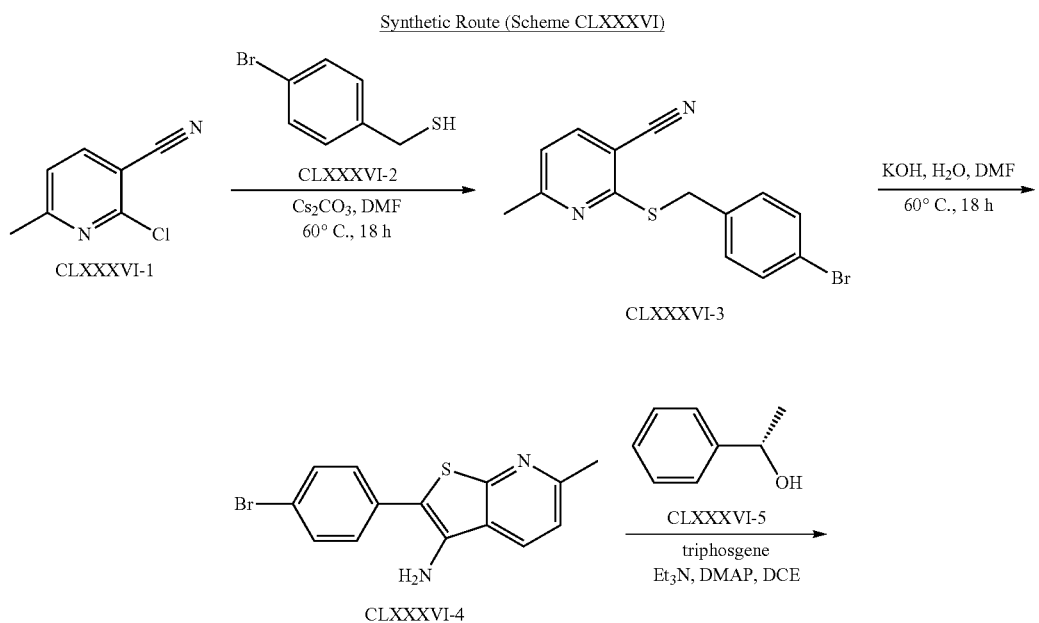

-continued
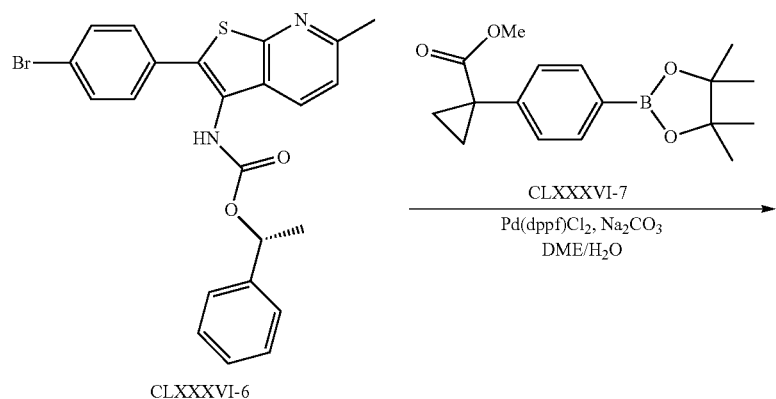
CLXXXVI-6
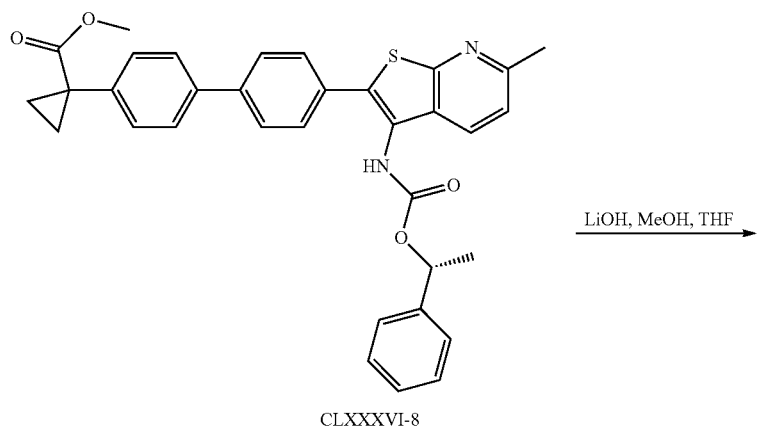
CLXXXVI-8
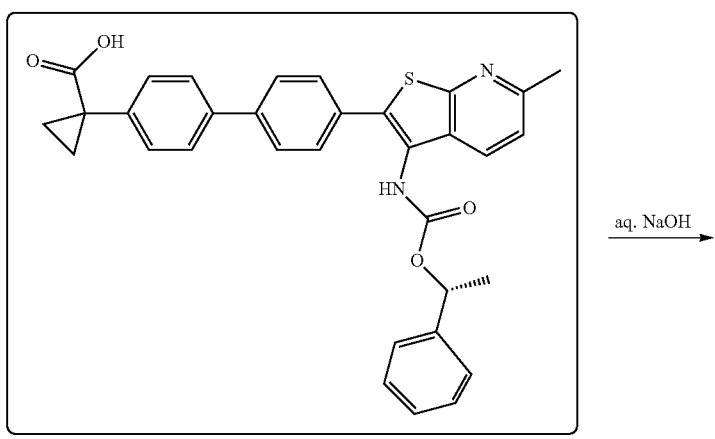
Compound 214

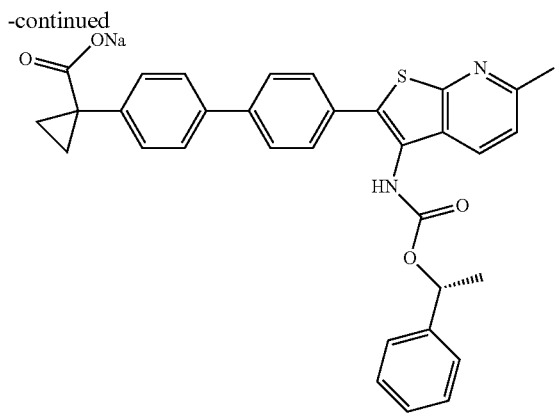

Compound 214a

To a solution of compound CLXXXVI-1 (1 g, 6.58 mmol) in DMF (30 mL) was added compound CLXXXVI-2 (1.6 g, 7.66 mmol) and $Cs_2CO_3$ (4.25 g, 13.16 mmol). The reaction mixture was stirred at 60° C. for 18 hours. After completion of the reaction, the mixture was poured into water, extract with EtOAc (30 mL×3), the combined organic layers were dried over $Na_2SO_4$, concentrated in vacuo. The residue was purified by column chromatography (PE:EA=10:1) to afford compound CLXXXVI-3 (1.5 g, yield 68.2%). MS (ESI) m/z $(M+H)^+$ 320.8.

To a solution of compound CLXXXVI-3 (1.5 g, 4.69 mmol) in DMF (30 mL) was added 5 N aqueous KOH (20 mL). The reaction mixture was stirred at 60° C. for 18 hours. After completion of the reaction, the mixture was poured into water, extract with EtOAc (30 mL×3), the combined organic layers were dried over $Na_2SO_4$, concentrated in vacuo. The residue was purified by column chromatography (PE:EA=5:1) to afford compound CLXXXVI-4 (0.8 g, yield 53.3%). MS (ESI) m/z $(M+H)^+$ 320.8.

Compound 214 was prepared analogously to the procedure described in the synthesis of Compound 213 (118 mg, yield 52.7%). MS (ESI) m/z $(M+H)^+$ 549.1.

Compound 214a was prepared analogously to the procedure described in the synthesis of Compound 213a. $^1$H NMR (DMSO-$d_6$ 400 MHz) δ 9.17 (b, 1H), 7.79 (d, J=8.4 Hz, 1H), 7.58-7.79 (m, 4H), 7.56 (d, J=8.4 Hz, 2H), 7.42 (d, J=8.4 Hz, 2H), 7.29-7.34 (m, 6H), 5.74-5.79 (q, 1H), 2.63 (s, 3H), 1.48 (br, 3H), 1.34-1.36 (m, 2 H), 0.89-0.92 (m, 2 H). MS (ESI) m/z $(M+H)^+$ 549.1.

Synthesis of Compound 215

Synthetic Route (Scheme CLXXXVII)

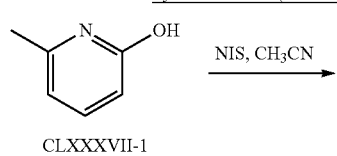

CLXXXVII-1

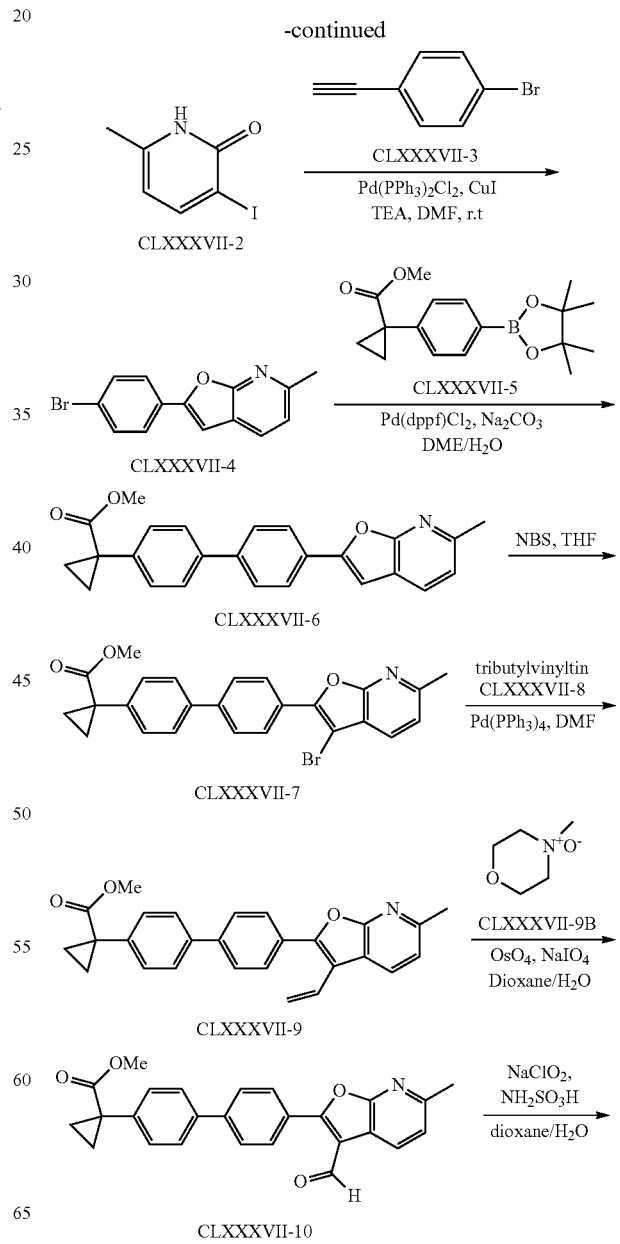

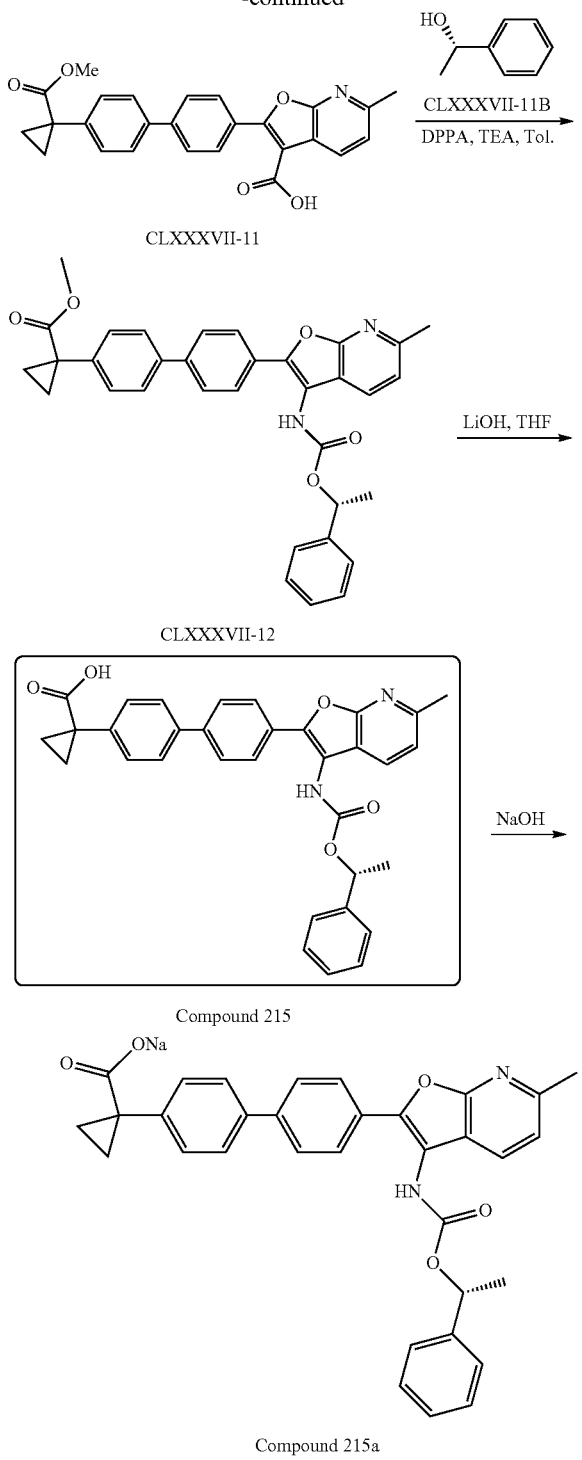

To a stirred solution of compound CLXXXVII-1 (10 g, 91.7 mmol) in CH$_3$CN (150 mL) was added NIS (20.6 g, 91.7 mmol). After the addition, the solution was stirred overnight at r.t. After concentrated, the residue was partitioned between H$_2$O and DCM, the aqueous phase was extracted with DCM, and the combined organic layer was washed with brine, dried over Na$_2$SO$_4$, concentrated. The residue was purified by rep. HPLC to give compound CLXXXVII-2 (2.5 g, yield 11.6%). MS (ESI) m/z (M+H)$^+$ 235.7.

A mixture of compound CLXXXVII-2 (2 g, 8.5 mmol), compound CLXXXVII-3 (1.84 g, 10.2 mmol), Pd(PPh$_3$)$_2$Cl$_2$ (700 mg, 10.2 mmol) and CuI (190 mg, 1 mmol) in triethylamine (10 mL) and DMF (30 mL) was stirred at r.t. (18° C.) under argon overnight. After evaporating of the solvent, the residue was diluted with water and extracted with dichloromethane. The combined organic extracts were dried over anhydrous MgSO$_4$, filtered and concentrated in vacuo. The residue was dissolved in DCM (60 mL) and stirred at room temperature for 5 hours. The solvent was removed under reduced pressure and the residue was purified by chromatography on silica gel to afford compound CLXXXVII-4 (1.3 g, yield 86.7%). MS (ESI) m/z (M+1)$^+$ 289.9.

To a solution of compound CLXXXVII-4 (130 mg, 0.45 mmol) in DME/H$_2$O (40 mL, v/v=3/1) were added Na$_2$CO$_3$ (95 mg, 0.9 mmol) and compound CLXXXVII-5 (163 mg, 0.54 mmol), the resulting mixture was purged with nitrogen, then Pd(dppf)Cl$_2$ (36 mg, 0.05 mmol) was added. The reaction mixture was stirred at 80° C. overnight under nitrogen protection. After completion of the reaction, the mixture was poured into water, extract with EtOAc (50 mL×3), the combined organic layers were dried over Na$_2$SO$_4$, concentrated in vacuo. The residue was purified by chromatography on silica gel (PE:EA=4:1) to afford compound CLXXXVII-6 (1 g, yield 57.8%). MS (ESI) m/z (M+1)$^+$ 384.2.

To a stirred solution of compound CLXXXVII-6 (1 g, 2.61 mmol) in THF (50 mL) was added NBS (924 mg, 5.22 mmol). After the addition, the solution was stirred overnight at r.t. After completion of the reaction, the mixture was poured into water, extract with EtOAc (100 mL×3), the combined organic layers were dried over Na$_2$SO$_4$, concentrated in vacuo. The residue was purified by chromatography on silica gel (PE:EA=4:1) to afford compound CLXXXVII-7 (0.4 g, yield 33.3%). MS (ESI) m/z (M+1)$^+$462.0.

To a solution of compound CLXXXVII-7 (0.4 g, 0.867 mmol) in DMF (20 mL) were added compound CLXXXVII-8 (0.73 g, 1.74 mmol) and Pd(PPh$_3$)$_4$ (1.01 g, 3.35 mmol). The reaction mixture was stirred at 120° C. overnight under nitrogen protection. After completion of the reaction, the mixture was poured into water, extract with EtOAc (100 mL×3), the combined organic layers were dried over Na$_2$SO$_4$, concentrated in vacuo. The residue was purified by chromatography on silica gel (PE:EA=5:1) to afford compound CLXXXVII-9 (50 mg, yield 14%). MS (ESI) m/z (M+H)$^+$ 410.2.

To a solution of compound CLXXXVII-9 (100 mg, 0.234 mmol) in dioxane/H$_2$O (30 mL, v/v=4/1) was added compound CLXXXVII-9B (54 mg, 0.468 mmol) and OsO$_4$ (5 mg, 0.02 mmol). The reaction mixture was stirred at room temperature overnight. Then NaIO$_4$ (498 mg, 2.34 mmol) was added and the mixture was stirred for addition 2.5 hours. After completion of the reaction, the mixture was poured into water, washed with aqueous NaHSO$_3$ and extract with EtOAc (50 mL×3), the combined organic layers were dried over Na$_2$SO$_4$, concentrated in vacuo. The residue was purified by chromatography on silica gel (PE:EA=4:1) to afford compound CLXXXVII-10 (50 mg, yield 14%). MS (ESI) m/z (M+H)$^+$ 412.1.

To a solution of compound CLXXXVII-10 (50 mg, 0.122 mmol) in dioxane:H$_2$O =7:3 (40 mL) was added NaClO$_2$ (15 mg, 0.158 mmol) and NH$_2$SO$_3$H (67 mg, 0.7 mmol). The reaction mixture was stirred at room temperature overnight. After completion of the reaction, the mixture was poured into water, extract with EtOAc (50 mL×3), the combined organic layers were dried over Na$_2$SO$_4$, concentrated in vacuo. The residue was purified by chromatography on silica gel (PE:

EA=3:1) to afford compound CLXXXVII-11 (42 mg, yield 80.7%). MS (ESI) m/z (M+H)+ 428.1.
Compound 215 was prepared analogously to the procedure described in the synthesis of Compound 212 (10 mg, yield 33%). MS (ESI) m/z (M+H)+ 533.1.
Compound 215a was prepared analogously to the procedure described in the synthesis of Compound 212a. $^1$H NMR (DMSO-$d_6$ 400 MHz): δ 7.95-7.97 (m, 2H), 7.77-7.79 (m, 3H), 7.71-7.73 (m, 2H), 7.48-7.61 (m, 6H), 7.22-7.24 (m, 2H), 5.81-5.92 (q, 1H), 2.63 (s, 3H), 1.66 (br, 3H), 1.49-1.52 (m, 2 H), 1.04-1.05 (m, 2 H). MS (ESI) m/z (M+H)+ 533.1.
Synthesis of Compounds 216 and 217
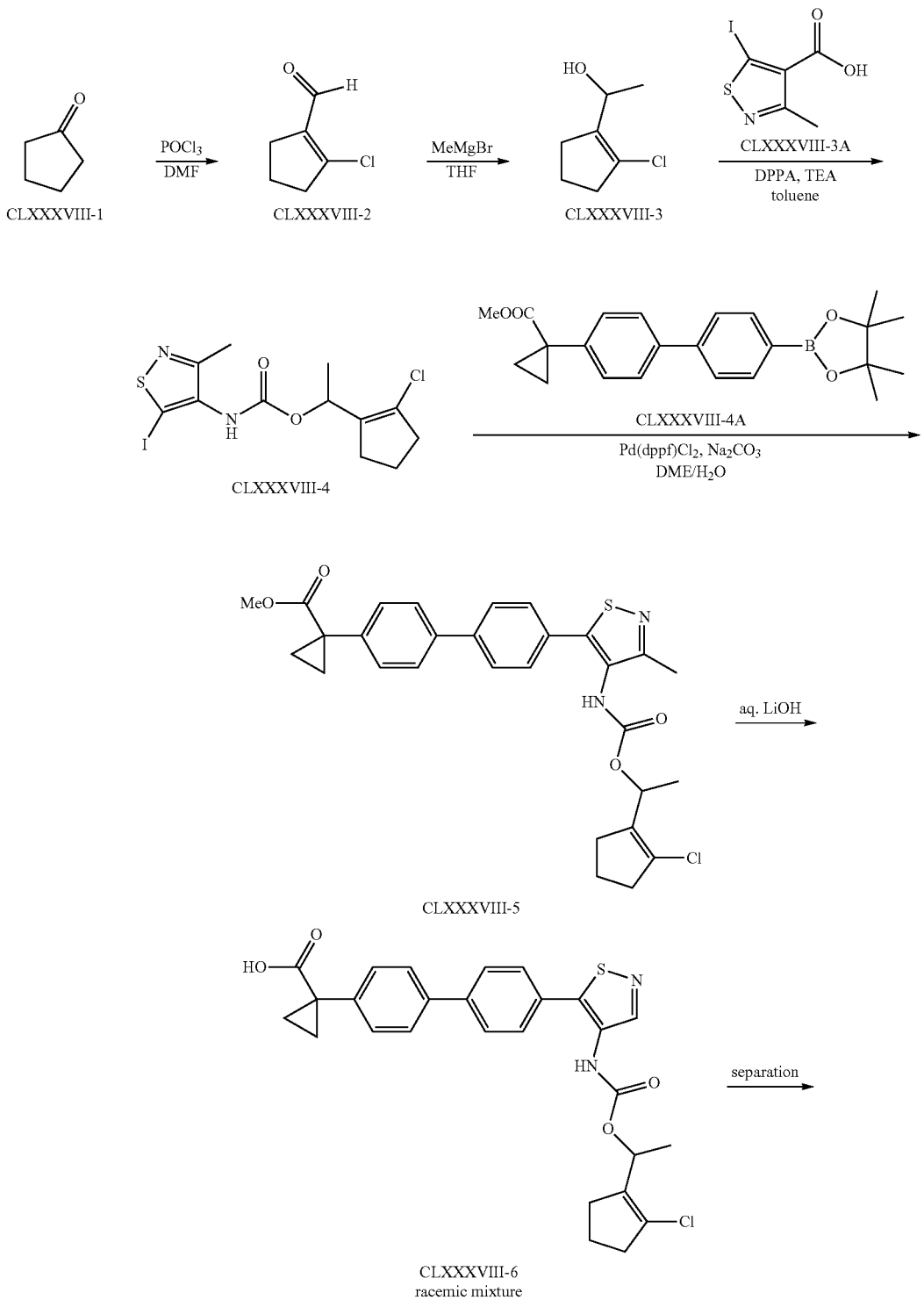

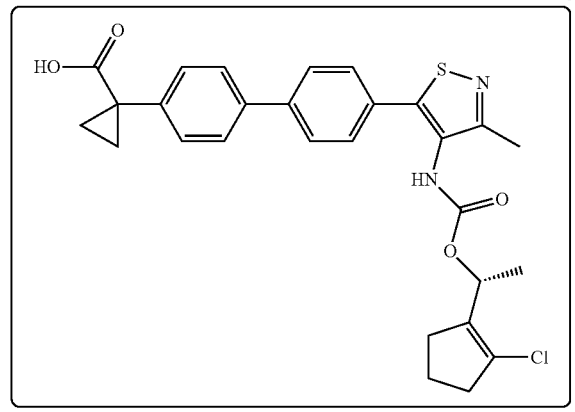

Compound 216

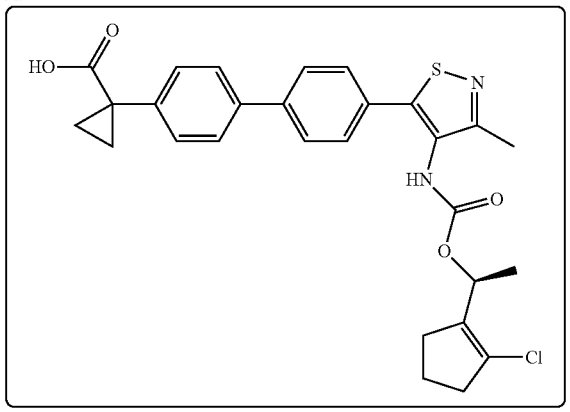

Compound 217

↓ aq. NaOH

↓ aq. NaOH

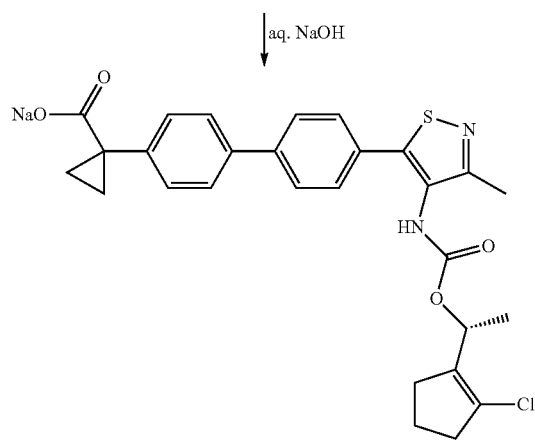

Compound 216a

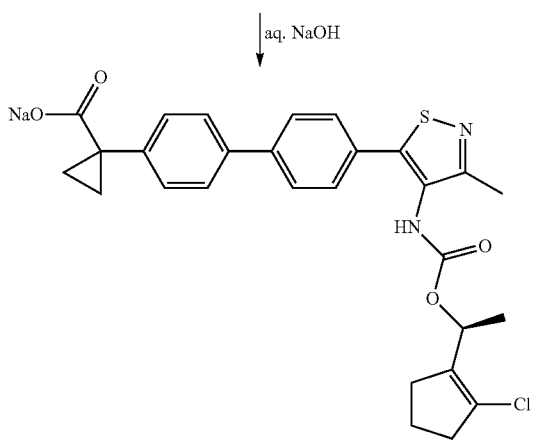

Compound 217a

POCl₃ (17.2 g, 112 mmol) was added to DMF (8.94 mL) at 0° C. After the addition, compound CLXXXVIII-1 (5 g, 60 mmol) was added dropwise to the reaction mixture at 0° C., then stirred at room temperature for one hour, and quenched with aq. NaHCO₃, the mixture was extracted with EtOAc (30 mL×3). The organic layer was combined and washed with brine, dried over Na₂SO₄, concentrated in vacuo to afford compound CLXXXVIII-2 (4 g, yield 51%), which was used to next step directly.

Methyl magnesium bromide (30 mL, 3.0 M in THF) was added dropwise to a solution of compound CLXXXVIII-2 (4 g, 0.03 mol) in THF (30 mL) at −50° C., and the mixture was stirred at room temperature for 1 hour. Then the reaction mixture was poured into ammonium chloride aqueous solution and extracted with ethyl acetate. The organic layers were combined, washed with brine and then dried with anhydrous magnesium sulfate, and concentrated in vacuo to afford compound CLXXXVIII-3 (4 g, yield 91%), which was used to next step directly.

To a stirred solution of compound CLXXXVIII-3 (720 mg, 4.8 mmol), compound CLXXXVIII-3A (1 g 3.7 mmol), TEA (720 mg 7.2 mmol) in toluene (30 mL) was added DPPA (1.3 g, 4.8 mmol) under nitrogen. After the addition, the solution was heated to reflux under nitrogen for 2 hours. The solution was concentrated, then H₂O (20 mL) was added, and the mixture was extracted with EtOAc (20 mL×3). The organic layer was combined and washed with brine, dried over Na₂SO₄, concentrated in vacuo. The residue was purified by column chromatography on silica gel (PE:EA=8:1) to afford compound CLXXXVIII-4 (1 g, yield 66%). MS (ESI) m/z (M+H)⁺ 412.6.

To a stirred solution of compound CLXXXVIII-4 (432.6 mg, 1.05 mmol), compound CLXXXVIII-4A (400 mg 1.05 mmol), Na₂CO₃ (222.6 mg, 2.1 mmol) in DME (25 mL) and H₂O (5 mL) was added Pd(dppf)Cl₂ (73.1 mg, 0.1 mmol) under nitrogen. After the addition, the solution was heated to reflux under nitrogen for 2 hours. The solution was concentrated, then H₂O (20 mL) was added, and the mixture was extracted with EtOAc (10 mL×3). The organic layer was combined and washed with brine, dried over Na₂SO₄, concentrated in vacuo. The residue was purified by column chromatography on silica gel (PE:EA=4:1) to afford compound CLXXXVIII-5 (300 mg, yield 65%). MS (ESI) m/z (M+H)⁺ 537.1.

Preparation of Compounds 216 and 217

To a solution of compound CLXXXVIII-5 (350 mg, 0.65 mmol) in MeOH (3 mL), THF (3 mL), H₂O (3 mL) was added LiOH—H₂O (136 mg, 3.25 mmol). The mixture was stirred overnight at room temperature. Then concentrated, water (10 mL), HCl (2 N) was added to pH=2, extracted with EtOAc (10 mL×3). The combined organic layers were washed with brine (10 mL×2), and concentrated under reduced pressure. The residue was purified by prep HPLC to give compound CLXXXVIII-6 as racemic mixture (230 mg, yield: 67.6%).

This compound was separate by SFC to give two stereoisomers Compound 216 (100 mg) and Compound 217 (110 mg).

Preparation of Compounds 216a and 271a

To a solution of Compound 216 (100 mg, 0.19 mmol) in MeOH (10 mL) was added NaOH (0.05 N, 3.83 mL) stirred for one hour, then the reaction mixture was lyophilized to give Compound 216a. $^1$H NMR (DMSO-$d_6$, 400 MHz): δ 7.73 (d, J=8.4 Hz, 2H), 7.61 (d, J=8.8 Hz, 2H), 7.51 (d, J=8.4 Hz, 2H), 7.39 (d, J=8.0 Hz, 2H), 5.49-5.54 (q, 1H), 2.25 (br, 2H), 2.31 (br, 5H), 1.81-1.87 (br, 2H), 1.26 (br, 2 H), 0.71 (br, 5 H). MS (ESI) m/z (M+H)$^+$ 523.0.

To a solution of Compound 217 (110 mg, 0.21 mmol) in MeOH (10 mL) was added NaOH (0.05N, 4.2 mL) stirred for one hour, then the reaction mixture was lyophilized to give Compound 217a. $^1$H NMR (DMSO-$d_6$, 400 MHz): δ 8.85 (s, 1H), 7.73 (d, J=8.0 Hz, 2H), 7.61 (d, J=8.0 Hz, 2H), 7.51 (d, J=8.4 Hz, 2H), 7.39 (d, J=8.4 Hz, 2H), 5.49-5.54 (q, 1H), 2.44 (br, 4H), 2.31 (s, 3H), 1.85 (br, 2 H), 1.25 (br, 5 H), 0.71 (br, 2H). MS (ESI) m/z (M+H)$^+$ 523.0.

Synthesis of Compounds 218 and 219

Synthetic Route (Scheme CLXXXIX)

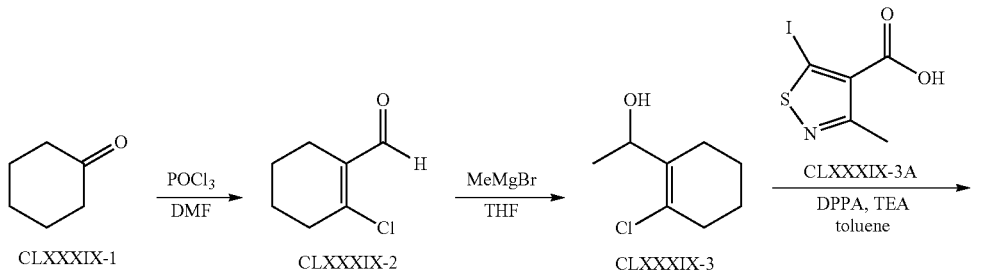

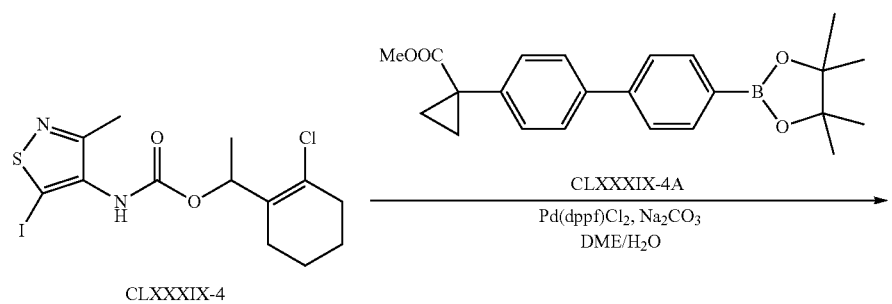

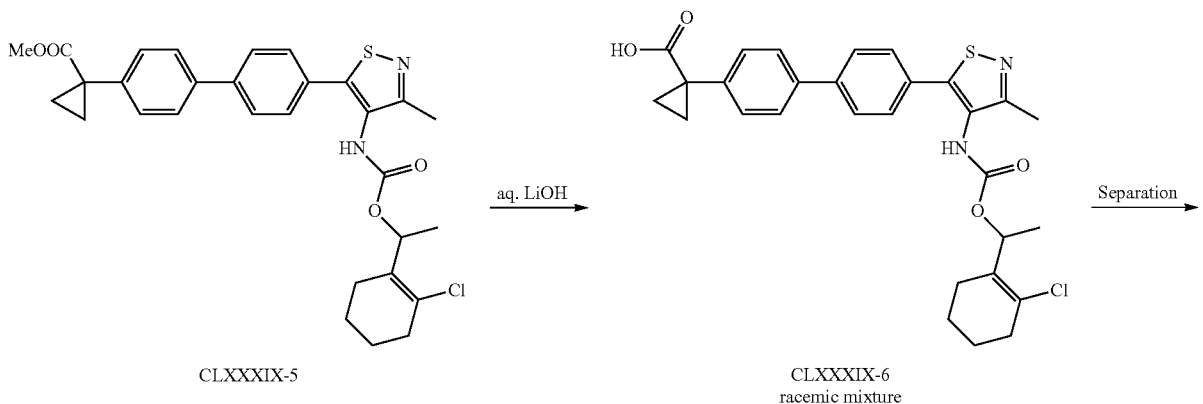

-continued

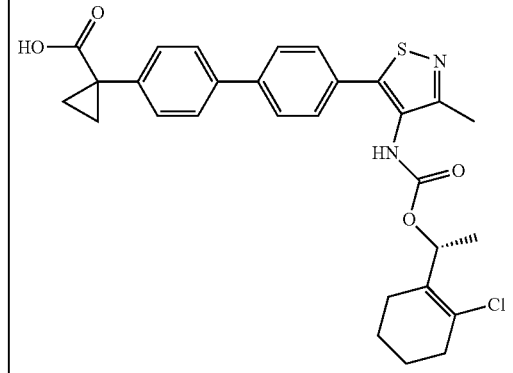

Compound 218

+

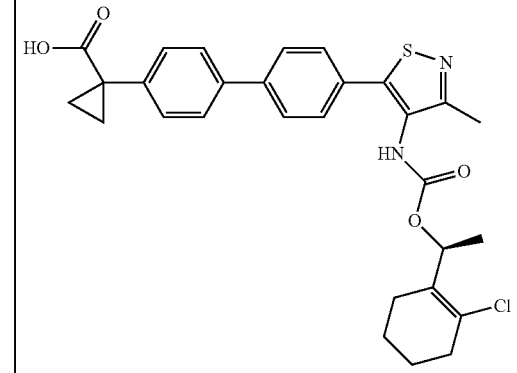

Compound 219

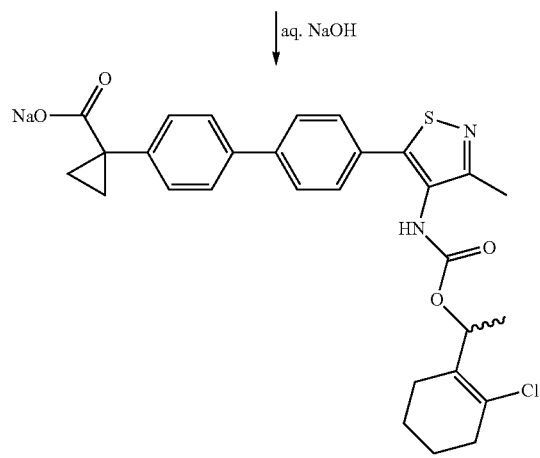

Compound 218a

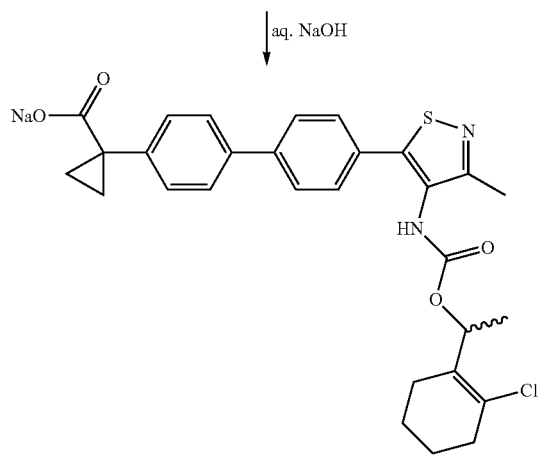

Compound 219a

Compounds 218, 218a, 219, and 219a were prepared analogously to the procedure described in the synthesis of Compounds 216, 216a, 217 and 217a.

Compound 218a: $^1$H NMR (DMSO-$d_6$, 400 MHz): δ 7.73 (d, J=8.4 Hz, 2H), 7.61 (d, J=8.0 Hz, 2H), 7.50 (d, J=8.4 Hz, 2H), 7.38 (d, J=8.0 Hz, 2H), 5.66-5.71 (q, 1H), 2.31 (br, 5H), 1.95-1.97 m, 2H), 1.54-1.64 (m, 4 H), 1.25 (br, 5 H), 0.71 (br, 2H). MS (ESI) m/z (M+H)$^+$ 537.0.

Compound 219a: $^1$H NMR (DMSO-$d_6$, 400 MHz): δ 7.73 (d, J=8.4 Hz, 2H), 7.61 (d, J=8.0 Hz, 2H), 7.54 (d, J=8.4 Hz, 2H), 7.39 (d, J=8.0 Hz, 2H), 5.66-5.71 (q, 1H), 2.31 (br, 5H), 1.92-1.97 (m, 2H), 1.54-1.63 (m, 4 H), 1.25 (br, 5 H), 0.71 (br, 2H). MS (ESI) m/z (M+H)$^+$ 537.0.

Synthesis of Compound 220

Synthetic Route (Scheme CXC)

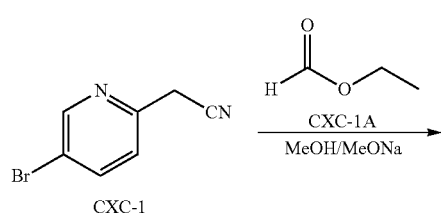

-continued

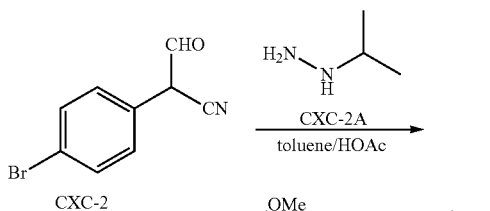

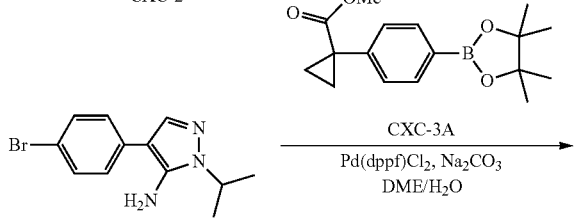

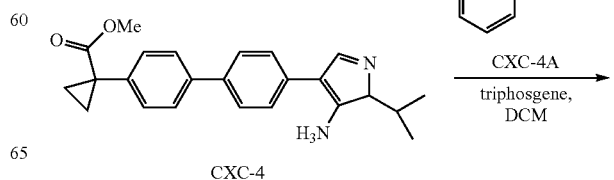

-continued

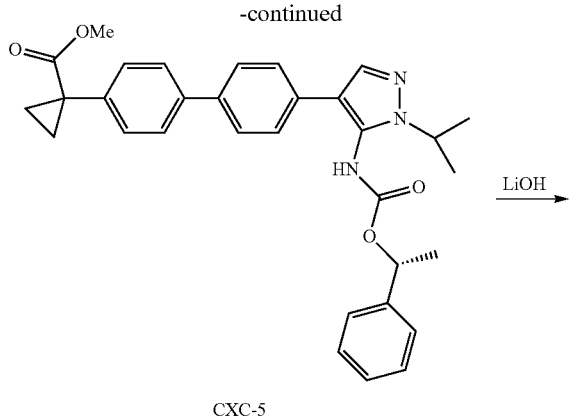

CXC-5

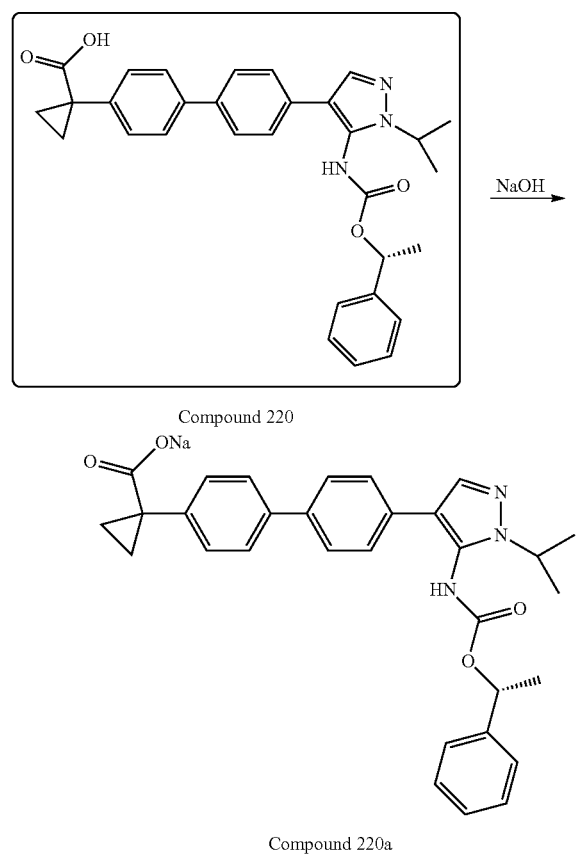

Compound 220

Compound 220a

To a mixture of compound CXC-1 (5.88 g, 30.0 mmol) and compound CXC-1A (2.59 g, 35.0 mmol) in 40 mL of EtOH (40 mL) was added EtONa (4.08 g, 60 mmol) at room temperature. The solution was heated to reflux under nitrogen for 2 hours. After being concentrated, AcOH and water was added to adjusted pH~2 and extracted with EtOAc (50 mL×3). The extracts were washed with brine, dried over Na$_2$SO$_4$, and concentrated to afford crude product, which was purified by chromatography on silica gel (PE:EA=5:1) to afford compound CXC-2 (6.89 g, yield 98%).

To a stirred solution of compound CXC-2 (2.01 g, 9 mmol) and compound CXC-2A (0.734 g, 9 mmol) in toluene (50 mL) was added HOAc (5 mL) at room temperature. The solution was heated to reflux under nitrogen overnight. The solution was concentrated then water (20 mL) was added and extracted with EtOAc (20 mL×3). The extracts were washed with brine, dried over Na$_2$SO$_4$, and concentrated to afford crude product, which was purification by prep. TLC (PE:EA=2:1) to afford compound CXC-3 (840 mg, yield 33.4%).

Compound 220 was prepared analogously to the procedure described in the synthesis of Compound 170 (15 mg, yield 12.8%). MS (ESI) m/z (M+H)$^+$ 510.2.

Compound 220a was prepared analogously to the procedure described in the synthesis of Compound 170a. $^1$H NMR (DMSO-d$_6$, 400 MHz): δ 9.19 (s, 1H), 7.79 (s, 1H), 7.47-7.57 (m, 6H), 7.39-7.37 (m, 7H), 5.76-5.81 (q, 1H), 4.42-4.49 (m, 1H), 1.49 (br, 3H), 1.29 (t, 3H), 1.28 (br, 2H), 0.77 (br, 2H). MS (ESI) m/z (M+H)$^+$ 510.2.

Synthesis of Compound 221

Synthetic Route (Scheme CXCI)

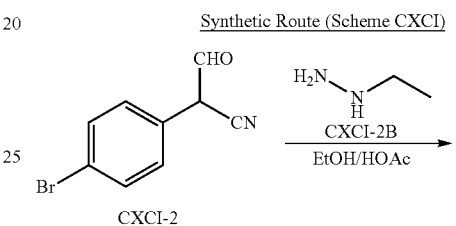

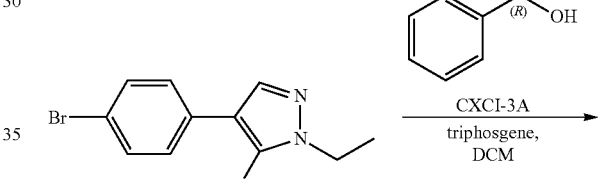

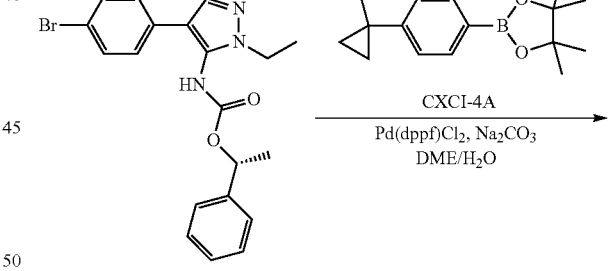

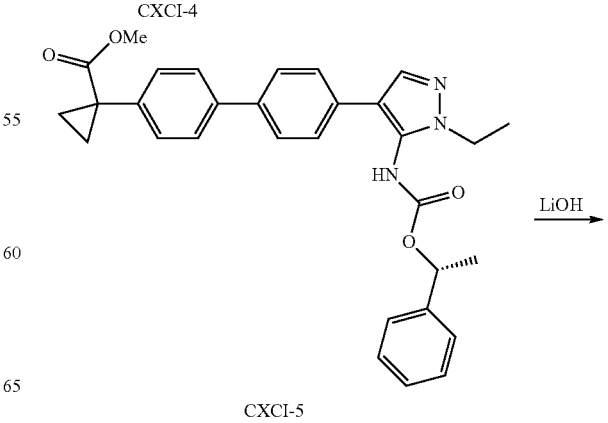

-continued

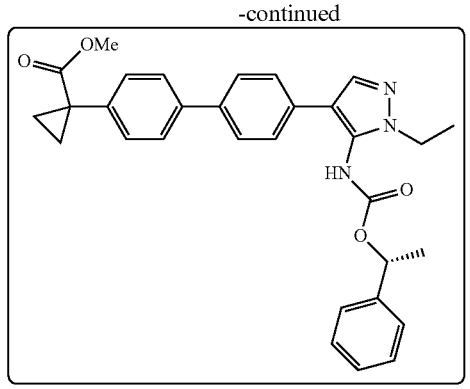

Compound 221

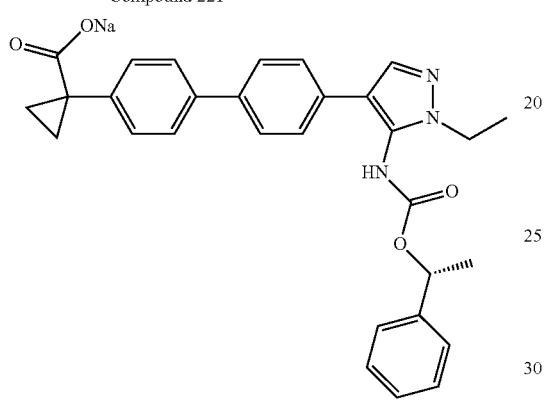

Compound 221a

To a stirred solution of compound CXCI-2 (2.69 g, 12 mmol) and compound CXCI-2B (1.8 g, 12 mmol) in EtOH (25 mL) was added HOAc (20 mL) at room temperature. The solution was heated to reflux under nitrogen for 4 hours. The solution was concentrated and adjusted pH to 9. Then water (20 mL) was added and extracted with EtOAc (20 mL×3). The extracts were washed with brine, dried over $Na_2SO_4$, and concentrated to afford crude product, which was purification by column chromatography (PE:EA=2:1) to afford compound CXCI-3 (651 mg, yield 21.2%).

Compound 221 was prepared analogously to the procedure described in the synthesis of Compound 220 (80 mg, yield 96.6%). MS (ESI) m/z (M+H)$^+$ 496.3.

Compound 221a was prepared analogously to the procedure described in the synthesis of Compound 220a. $^1$H NMR (DMSO-d$_6$, 400 MHz): δ 9.60 (s, 1H), 7.82 (s, 1H), 7.32-7.57 (m, 13H), 5.76 (q, 1H), 3.94-3.96 (m, 2H), 1.55 (br, 2H), 1.22-1.30 (m, 6H), 0.727 (br, 2H). MS (ESI) m/z (M+H)$^+$ 496.3.

Synthesis of Compound 222

Synthetic Route (Scheme CXCII)

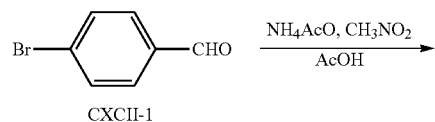

CXCII-1

-continued

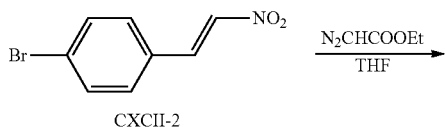

CXCII-2

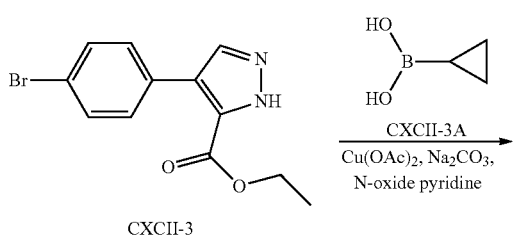

CXCII-3

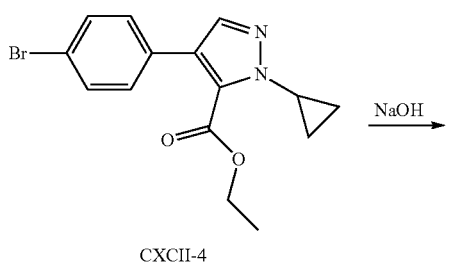

CXCII-4

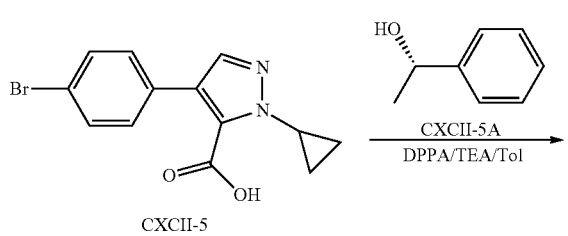

CXCII-5

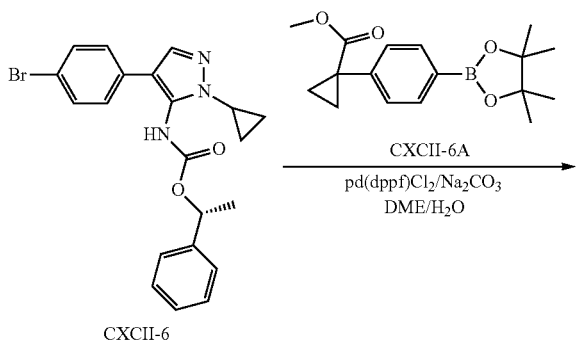

CXCII-6

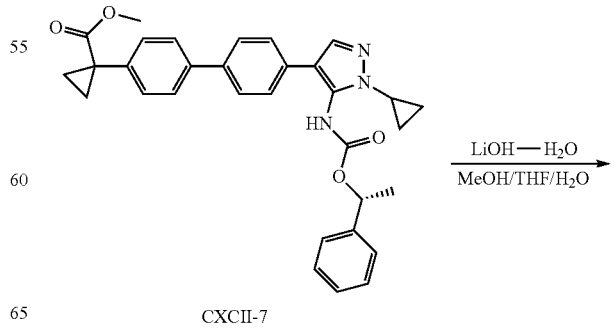

CXCII-7

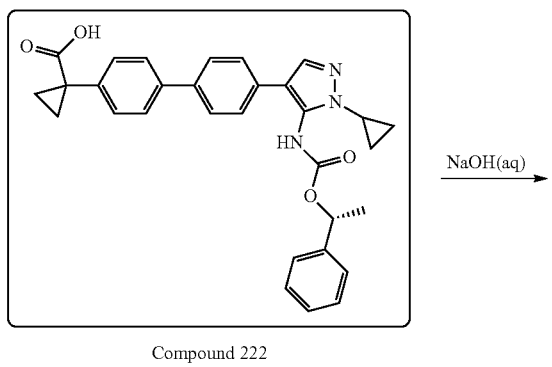

Compound 222

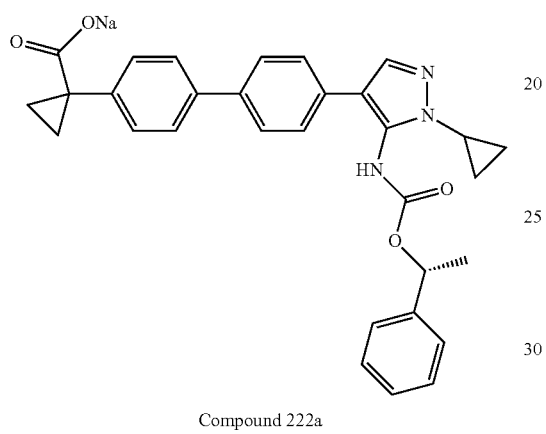

Compound 222a

Compound CXCII-1 (10 g, 54.34 mmol) were added to a solution of $CH_2NO_2$ (53.34 ml) in HOAc (53.34 mL), the resulting mixture was purged with nitrogen, then $NH_4OAc$ (418 mg, 5.434 mmol) was added. The reaction mixture was stirred at 80° C. overnight under nitrogen protection. After completion of the reaction, the mixture was poured into water, extract with EtOAc (30 mL×3), the combined organic layers were dried over $Na_2SO_4$, concentrated in vacuo. The residue was purified by chromatography (PE:EA=10:1) to afford compound CXCII-2 (7.5 g, yield 60.78%).

To a stirred solution of compound CXCII-2 (6.5 g, 28.63 mmol) in THF (50 mL) was added compound CXCII-2A (16.32 g, 614.3 mmol). After the addition, the solution was stirred overnight at r.t. overnight. After completion of the reaction, the mixture was poured into water, extract with EtOAc (30 mL×3), the combined organic layers were dried over $Na_2SO_4$, concentrated in vacuo. The residue was purified by chromatography (PE:EA=10:1) to afford compound CXCII-3 (3 g, yield 32.97%).

A mixture of compound CXCII-3 (600 mg, 2 mmol), compound CXCII-3A (342 mg, 4 mmol), $Cu(OAc)_2$ (304 mg, 2 mmol), $Na_2CO_3$ (414 mg, 4 mmol), N-oxide pyridine (190 mg, 2 mmol) in DCE (30 ml) was heated to reflux for 2 overnight. The solution was concentrated, then $H_2O$ (20 mL) was added, and the mixture was extracted with EtOAc (20 mL×3). The organic layer was combined and washed with brine, dried over $Na_2SO_4$, concentrated in vacuo. The residue was purified by column chromatography on silica gel (PE: EA=4:1) to afford compound CXCII-4 (0.2 g, yield 32%).

To a solution of compound CXCII-4 (180 mg, 0.53 mmol) in MeOH (3 mL), THF (3 mL), $H_2O$ (3 mL) was added NaOH (63.6 mg, 1.6 mmol). The mixture was stirred overnight at room temperature. Then concentrated, water (10 mL) and HCl (2 N) was added to pH=2, and extracted with EtOAc (10 mL×3). The combined organic layers were washed with brine (10 mL×2), and concentrated under reduced pressure to give compound CXCII-5 (130 mg, yield 79%).

Compound 222 was prepared analogously to the procedure described in the synthesis of Compound 220 (45.4 mg, yield 47.4%). MS (ESI) m/z (M+H)$^+$ 508.1.

Compound 222a was prepared analogously to the procedure described in the synthesis of Compound 220a. $^1$H NMR (DMSO-d$_6$, 400 MHz): δ 7.71 (s, 1H), 7.47-7.58 (m, 6H), 7.28-7.39 (m, 7H), 5.77-5.82 (q, 1H), 3.38-3.44 (m, 1H), 1.507 (br, 3H), 1.30 (br, 2 H), 1.02-1.05 (m, 2 H), 0.90-0.92 (m, 2H), 0.79-0.79 (m, 2H). MS (ESI) m/z (M+H)$^+$ 508.1.

Synthesis of Compound 223

Synthetic Route (Scheme CXCIII)

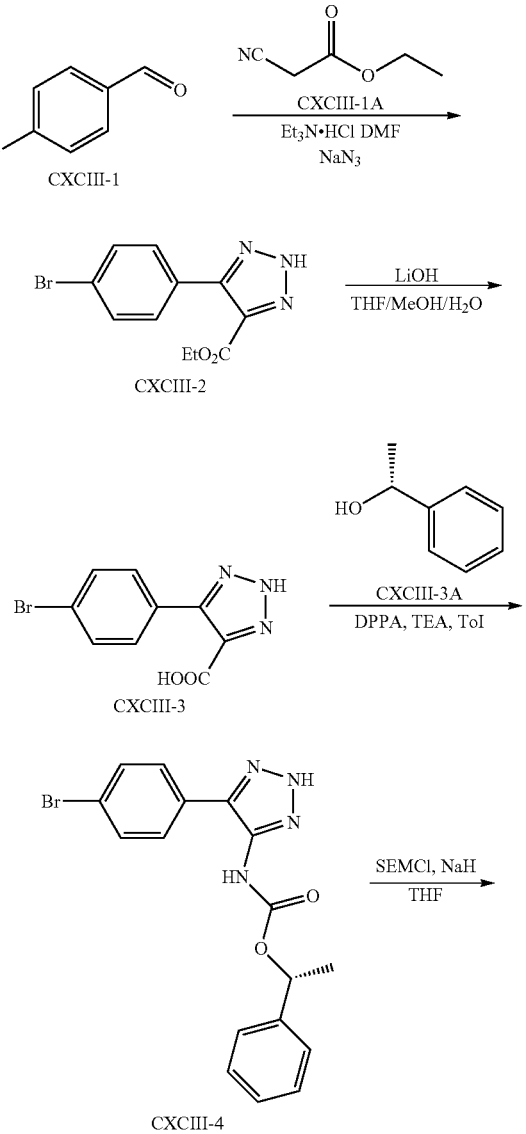

Et₃N·HCl (18.6 g, 136 mmol), NaN₃ (10.7 g, 163.2 mmol) and compound CXCIII-1A (5.28 g, 54.4 mmol) were added to a solution of compound CXCIII-1 (10 g, 54.4 mmol) in DMF (60 mL). The reaction mixture was stirred at 70° C. overnight under nitrogen protection. After completion of the reaction, the mixture was poured into water and extract with EtOAc (100 mL×3), the combined organic layers were dried over Na₂SO₄, concentrated in vacuo. The residue was washed with ether to afford compound CXCIII-2 (6 g, yield 37.5%).

To a stirred solution of compound CXCIII-2 (4.2 g, 14.2 mmol) in MeOH/THF/H₂O (v/v/v=1/2/1, 16 mL) was added LiOH (3 g, 71 mmol). After the addition, the solution was stirred overnight at r.t. The solution was concentrated in vacuo, the aqueous layer was adjusted pH to 2 with 1N HCl, and extracted with EtOAc (30 mL×3). The organic layer was separated, dried and concentrated to afford compound CXCIII-3 (3.5 mg, yield 92%).

To a solution of compound CXCIII-3 (1 g, 3.74 mmol) in toluene (30 mL) were added TEA (757 mg, 7.48 mmol), DPPA (1.3 g, 4.49 mmol) and compound CXCIII-3A (544 mg, 4.49 mmol). The reaction mixture was stirred at 80° C. overnight under nitrogen protection. After completion of the reaction, the mixture was extracted with EtOAc washed with water, and concentrated. The residue was purified by chromatography on silica gel (PE:EA=2:1) to afford compound CXCIII-4 (700 mg, yield 50%).

To a stirred solution of compound CXCIII-4 (865 mg, 2.24 mmol) in THF (12 mL) was added NaH (107.6 mg, 4.48 mmol) slowly at 0° C., then SEMCl (445.3 mg, 2.7 mmol) was added dropwise, the mixture was stirred at room temperature for 3 hours under nitrogen protection. After completion of the reaction, the mixture was poured into ice-water and extracted with EtOAC, the combined organic layer was washed with brine, dried over MgSO₄, then filtered and concentrated. The residue was purified by chromatography on silica gel (PE:EA=5:1) to afford compound CXCIII-5 (582 mg, yield 50.6%).

Na₂CO₃ (240 mg, 2.26 mmol) and compound CXCIII-5A (408 mg, 1.35 mmol) were added to a solution of compound CXCIII-5 (582 mg, 1.13 mmol) in DME/H₂O (12 ml, v/v=3/1), the resulting mixture was purged with nitrogen, then Pd(dppf)Cl₂ (41.2 mg, 0.06 mmol) was added. The reaction mixture was stirred at 80° C. overnight under nitrogen protection. After completion of the reaction, the mixture was poured into water, extract with EtOAc (30 ml×3), the combined organic layers were dried over MgSO₄, concentrated in vacuo. The residue was purified by column chromatography (PE:EA=2:1) to afford compound CXCIII-6 (570 mg, yield 82.2%). MS (ESI) m/z (M+H)+ 613.2.

Compound 223 was prepared analogously to the procedure described in the synthesis of Compound 170 (45 mg, yield 95.7%).

Compound 223a. $^1$H NMR (DMSO-$d_6$, 400 MHz): δ 7.79 (d, J=8.0 Hz, 2H), 7.61 (d, J=8.4 Hz, 2H), 7.56 (d, J=8.4 Hz, 2H), 7.42 (d, J=8.4 Hz, 2H), 5.73-5.78 (q, 1H), 1.40-1.48 (m, 5H), 0.99-1.05 (m, 2H). MS (ESI) m/z (M+H)+ 469.1.

Synthesis of Compound 224

Synthetic Route (Scheme CXCIV)

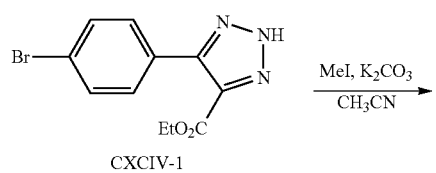
CXCIV-1

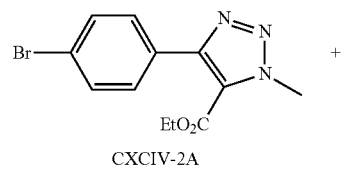
CXCIV-2A

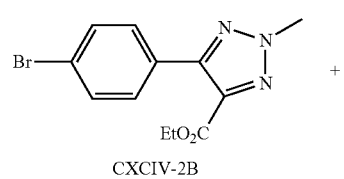
CXCIV-2B

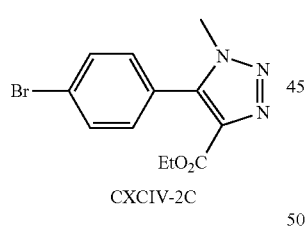
CXCIV-2C

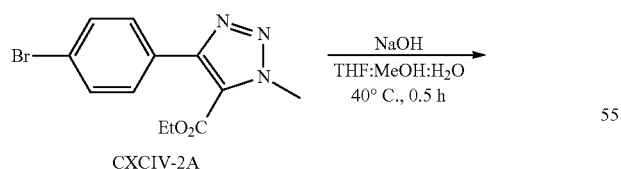
CXCIV-2A

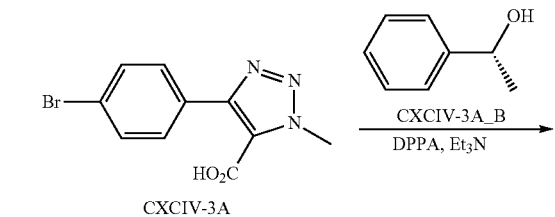
CXCIV-3A

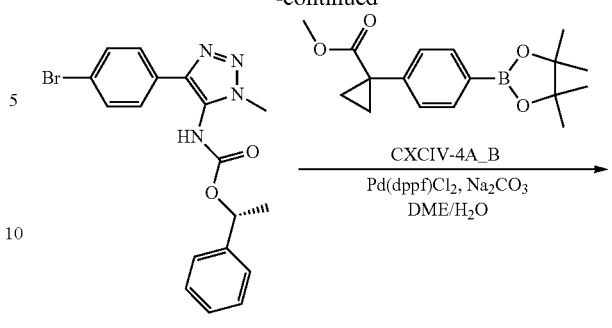
CXCIV-4A

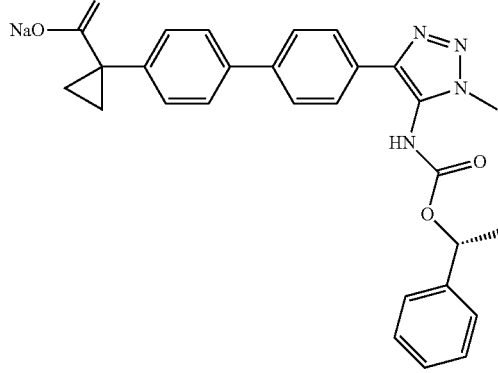

Compound 224

Compound 224a

MeI (2.8 g, 19.7 mmol) was added to a solution of compound CXCIV-1 (3 g, 10.2 mmol) and K$_2$CO$_3$ (2.8 g, 20.4 mmol) in CH$_3$CN (18 ml). The reaction mixture was stirred at room temperature overnight. Then water (20 mL) was added and extracted with CH$_2$Cl$_2$ (40 ml), the organic layers were dried over MgSO$_4$ and concentrated. The residue was purified by prep-HPLC to afford compound CXCIV-2A (960 mg, yield 30.9%), compound CXCIV-2B (240 mg, yield 7.7%), and compound CXCIV-2C (600 mg, yield 19.3%). NOE and HMBC confirmed.

To a solution of compound CXCIV-2A (653.2 mg, 2.115 mmol) in MeOH (3 mL), THF (3 mL) and H₂O (3 mL) was added NaOH (169 mg, 4.229 mmol) and the mixture was heated at 40° C. for 30 min. After cooled to r.t., the mixture was acidified with 1M aq. HCl, and the product was extracted with CH₂Cl₂. The organic phase was dried with anhydrous sodium sulfate, filtered, and concentrated on a rotary evaporator. The crude product CXCIV-3A (570 mg, yield: 54.54%) was used in the next step without further purification.

Compound 224 was prepared analogously to the procedure described in the synthesis of Compound 170 (272.8 mg, yield: 36.42%). MS (ESI) m/z (M+H)⁺ 483.2.

Compound 224a was prepared analogously to the procedure described in the synthesis of Compound 170a. ¹H NMR (DMSO-d₆, 400 MHz): δ 7.83 (d, J=8.4 Hz, 2H), 7.64 (d, J=8.4 Hz, 2H), 7.53 (d, J=8.4 Hz, 2H), 7.29-7.41 (m, 7H), 5.78-5.83 (q, 1H), 3.85 (s, 3H), 1.52 (d, J=6.4 Hz, 3H), 1.34 (br, 2H), 0.86 (br, 2H). MS (ESI) m/z (M+H)⁺ 483.2.

Synthesis of Compound 225

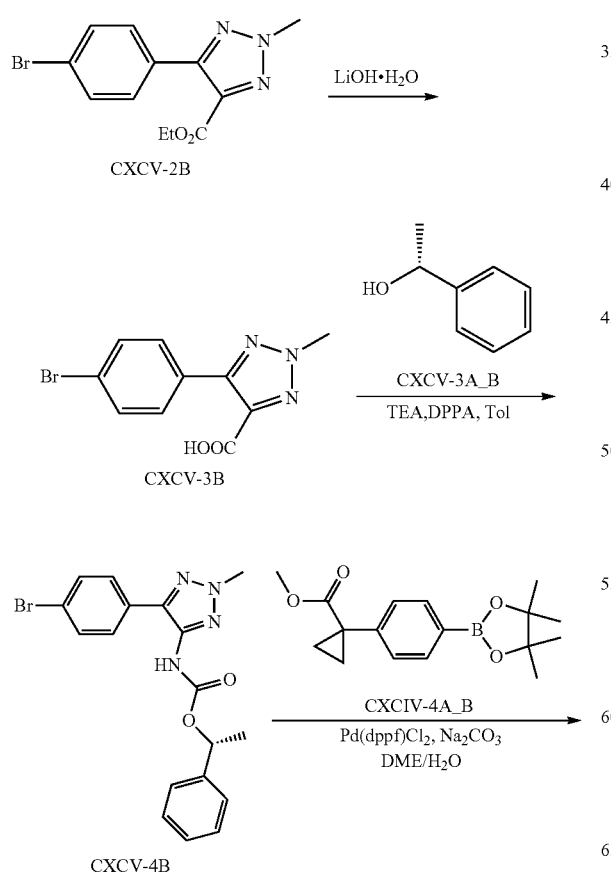

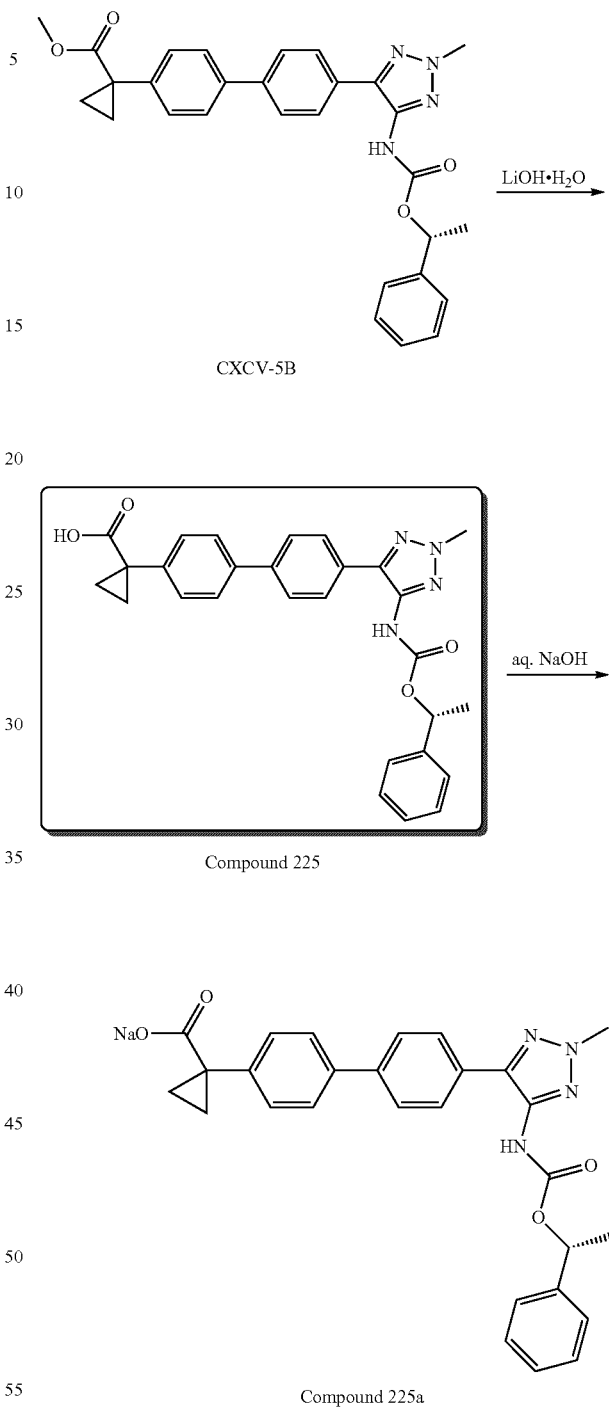

Compound 225 was prepared analogously to the procedure described in the synthesis of Compound 224 (210 mg, yield 63%).

Compound 225a. ¹H NMR (DMSO-d₆, 400 MHz): δ 9.28 (br, 1H), 7.74 (d, J=8.4 Hz, 2H), 7.63 (d, J=8.4 Hz, 2H), 7.49 (d, J=8.4 Hz, 2H), 7.28-7.40 (m, 5H), 5.72-5.79 (q, 1H), 4.14 (s, 3H), 1.47 (d, J=6.4 Hz, 2H), 1.28-1.31 (m, 2H), 0.78-0.81 (m, 2H). MS (ESI) m/z (M+H)⁺ 483.1.

Synthesis of Compound 226
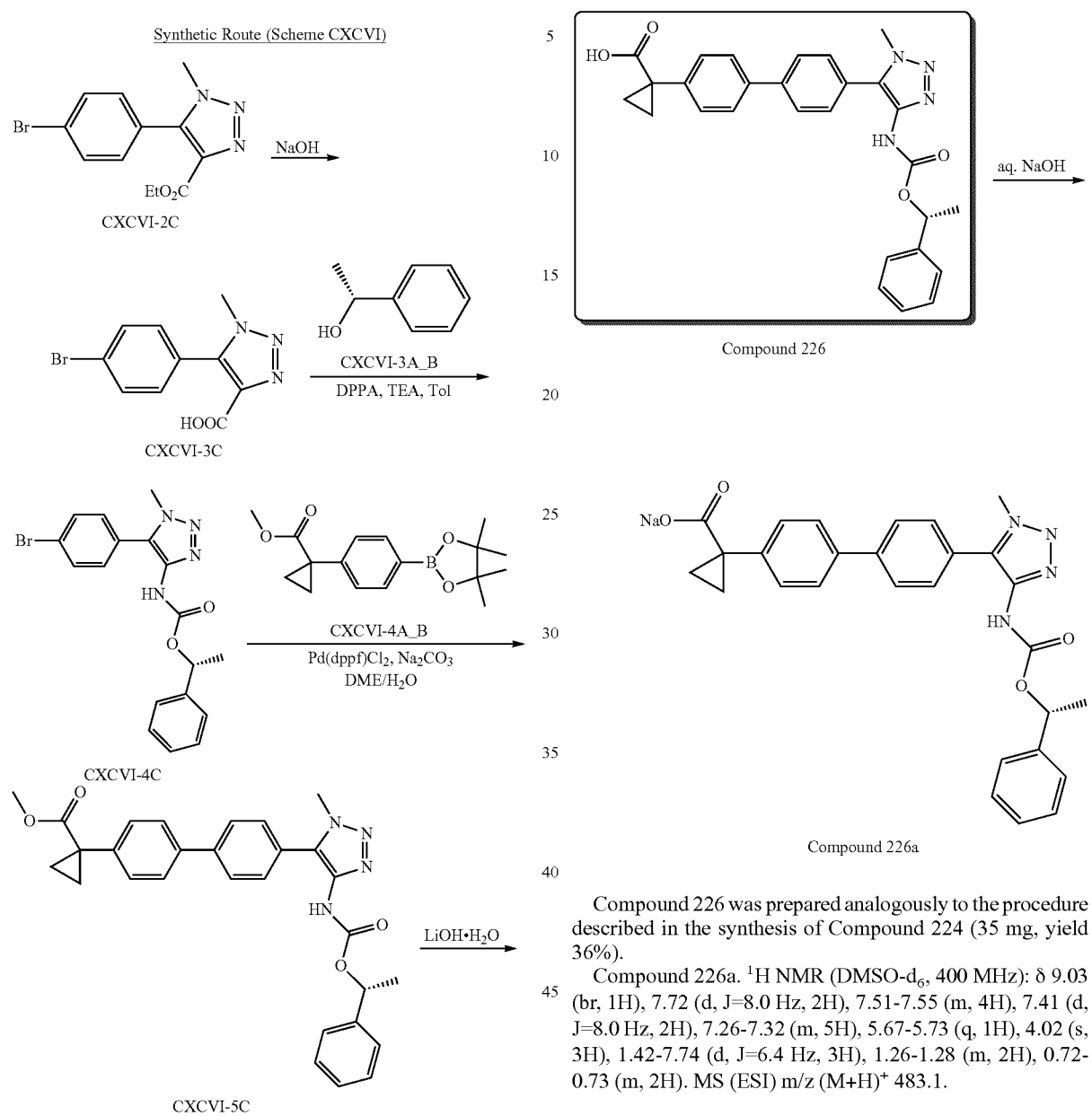
Compound 226
Compound 226 was prepared analogously to the procedure described in the synthesis of Compound 224 (35 mg, yield 36%).
Compound 226a. $^1$H NMR (DMSO-$d_6$, 400 MHz): δ 9.03 (br, 1H), 7.72 (d, J=8.0 Hz, 2H), 7.51-7.55 (m, 4H), 7.41 (d, J=8.0 Hz, 2H), 7.26-7.32 (m, 5H), 5.67-5.73 (q, 1H), 4.02 (s, 3H), 1.42-7.74 (d, J=6.4 Hz, 3H), 1.26-1.28 (m, 2H), 0.72-0.73 (m, 2H). MS (ESI) m/z (M+H)$^+$ 483.1.
Synthesis of Compound 227
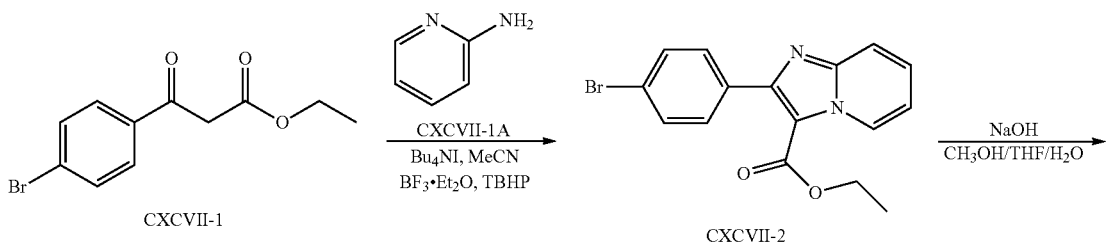

-continued
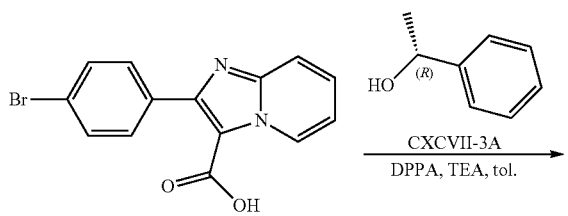
CXCVII-3
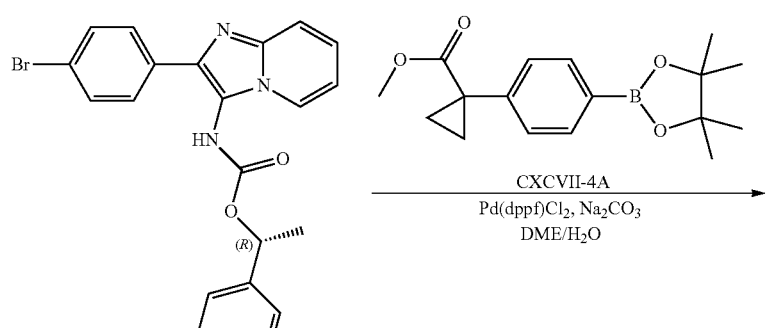
CXCVII-4
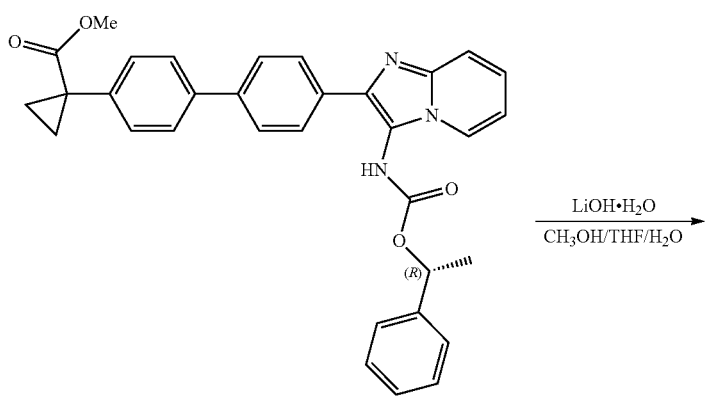
CXCVII-5
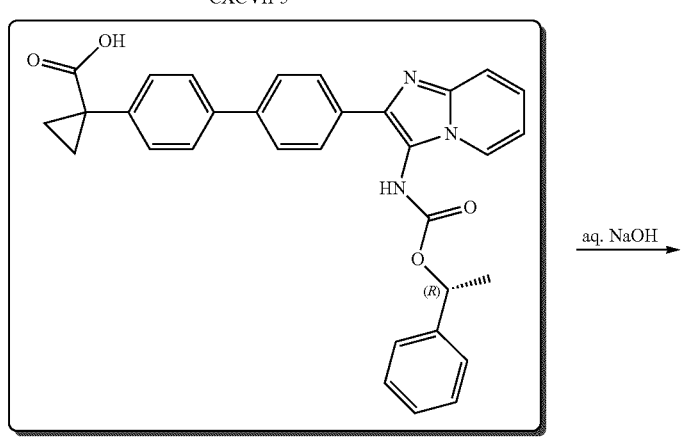
Compound 227

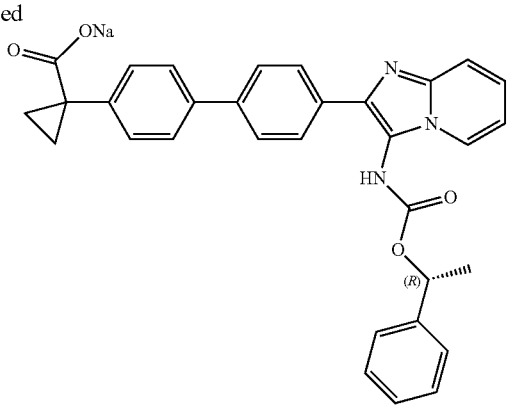

Compound 227a

The mixture of compound CXCVII-1 (5 g, 18.4 mmol), compound CXCVII-1A (1.15 g, 12.2 mmol), Bu₄NI (0.45 g, 1.22 mmol), BF₃·Et₂O (378 uL) and TBHP (2.20 g, 24.4 mmol) in MeCN (50 mL) was stirred at 80° C. under nitrogen overnight. The mixture was poured into saturated Na₂SO₃ solution, extracted with EtOAc. The combined organic layer was washed with brine and dried with anhydrous Na₂SO₄ and concentrated. The residue was purified by chromatography on silica gel (PE:EA=5:1) to afford compound CXCVII-2 (1.41 g, yield 33.6%).

To the solution of compound CXCVII-2 (860 mg, 2.5 mmol) in CH₃OH (3 mL), THF (3 mL) and H₂O (3 mL) was added NaOH (200 mg, 5 mmol). The mixture was stirred at room temperature overnight. The solvent was removed under reduced pressure. Then 1 N HCl was added until pH=4. The precipitate solid was collect to afford compound CXCVII-3 (700 mg, yield 88.6%).

Compound 227 was prepared analogously to the procedure described in the synthesis of Compound 31 (380 mg, yield 73.3%).

Compound 227a. ¹H NMR (400 MHz, DMSO-d₆): δ 7.97-8.03 (m, 3 H), 7.64 (d, J=8.4 Hz, 2 H), 7.49-7.66 (m, 3 H), 7.24-7.39 (m, 8 H), 7.89-7.92 (t, 1 H), 5.81-5.86 (q, 1 H), 1.53 (d, J=6.4 Hz 3 H), 1.24-1.26 (m, 2 H), 0.70-0.72 (m, 2H). MS (ESI) m/z (M+H)⁺518.1.

Synthesis of Compound 228

Synthetic Route (Scheme CXCVIII)

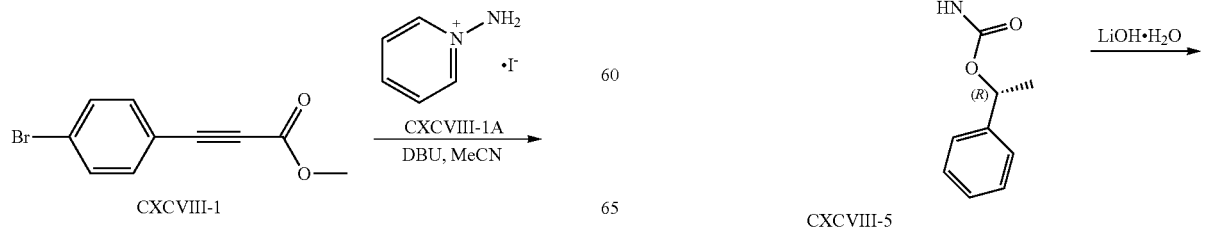

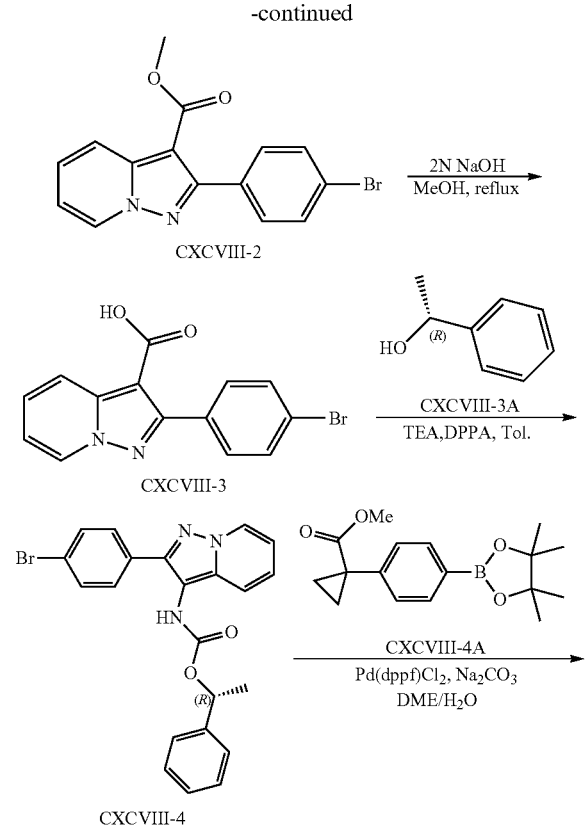

1149

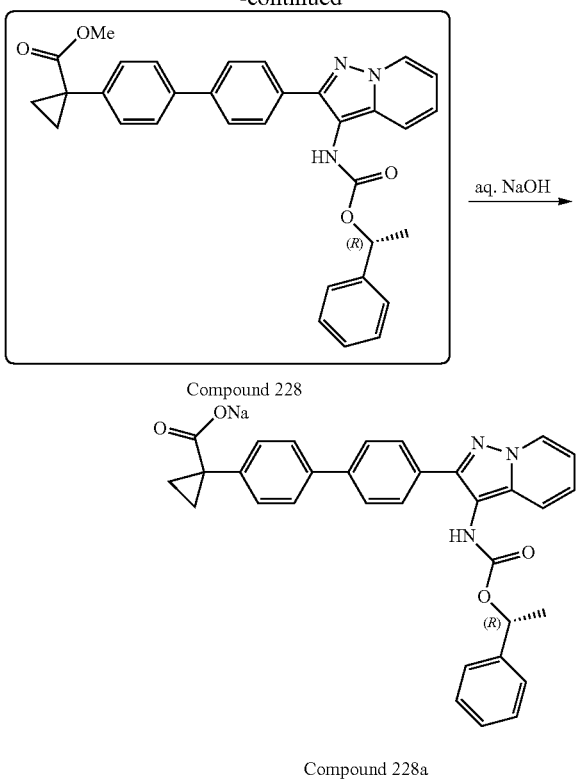

Compound 228

Compound 228a

1150

To a solution of compound CXCVIII-1 (500 mg, 2.09 mmol) and 1-aminopyridinium iodide (464 mg, 2.09 mmol) in acetonitrile (6 mL) was added a solution of 1,8-diazabicyclo[5.4.0]undec-7-ene in acetonitrile (2 mL) dropwise at 0° C. The mixture was stirred at room temperature overnight. The mixture was diluted with water, extracted with ethyl acetate (3×30 mL). The combined organic layer was washed with brine, dried over MgSO$_4$ and concentrated. The residue was washed with tert-butyl methyl ether to afford compound CXCVIII-2 (690 mg, 100% yield).

To a solution of compound CXCVIII-2 (690 mg, 2.08 mmol) in methanol (3 mL) was added 2 N NaOH aqueous solution (5 mL). The mixture was heated to reflux for 3 hours. After cooled, the mixture was diluted with water (10 mL), acidified to pH=3 with 2 N HCl, then extracted with ethyl acetate/THF (3×35 mL). The combined organic layer was washed with brine, dried over MgSO$_4$ and concentrated to afford compound CXCVIII-3 (630 mg, 95% yield).

Compound 228 was prepared analogously to the procedure described in the synthesis of Compound 31 (400 mg, yield 94.3%). MS (ESI) m/z (M+H)$^+$ 518.1.

Compound 228a. $^1$H NMR (DMSO-d$_6$, 400 MHz): δ 8.62 (d, J=6.8 Hz, 1 H), 7.64 (d, J=8.4 Hz, 2 H), 7.66 (d, J=7.2 Hz, 2 H), 7.43-7.52 (m, 3H), 7.31-7.38 (m, 6H), 7.14-7.18 (m, 1H), 6.85-6.88 (m, 1H), 5.77 (br, 1H), 1.52 (br, 3H), 1.25 (br, 2H), 0.75 (br, 2H). MS (ESI) m/z (M+H)$^+$ 518.1.

Synthesis of Compound 229

Synthetic Route (Scheme CXCIX)

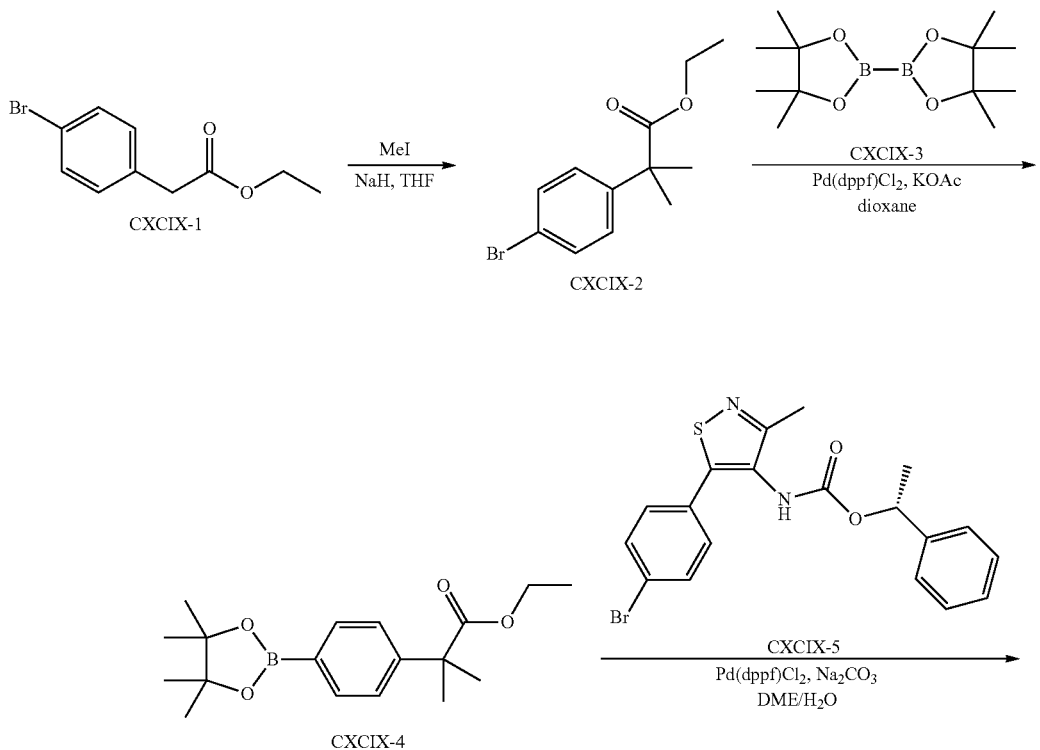

-continued

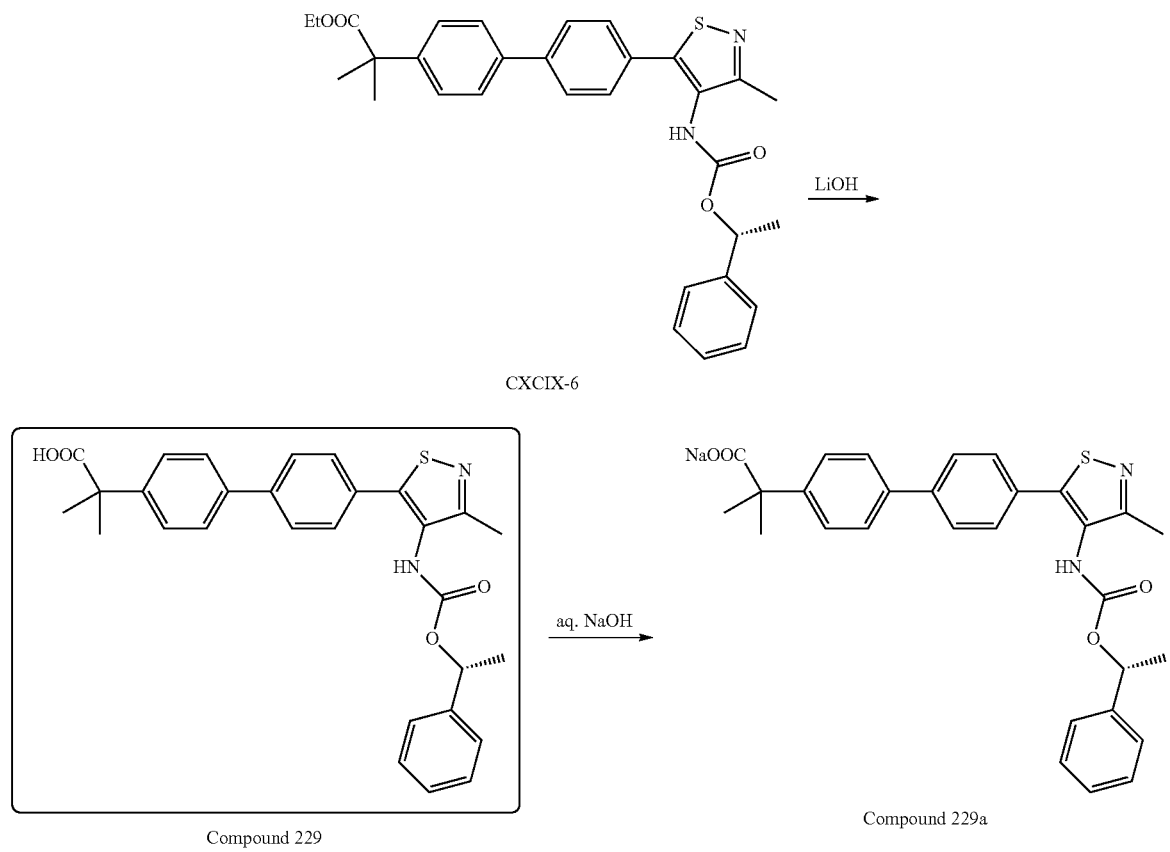

To a solution of compound CXCIX-1 (5 g, 20.7 mmol) in THF (100 mL) was added NaH (2.48 g, 62.1 mmol) portionwise. The reaction mixture was stirred at room temperature for 1 hour and MeI (8.82 g, 62.1 mmol) was added. The reaction mixture was heated to reflux for 18 hours. The reaction mixture was quenched with water (150 mL), neutralized to pH=5.0 with 3 N hydrochloride solution. The mixture was extracted with EtOAc (50 mL×3). The combined organic phase was dried over $Na_2SO_4$ and concentrated. The residue was purified by column chromatography (PE) to afford compound CXCIX-2 (2.0 g, yield 35.8%). MS (ESI) m/z (M+H)$^+$ 272.0.

The mixture of compound CXCIX-2 (2 g, 7.41 mmol), compound CXCIX-3 (2.82 g, 11.1 mmol), KOAc (1.45 g, 14.8 mmol) and Pd(dppf)Cl$_2$ (270 mg, 0.37 mmol) in 120 mL of dioxane was heated to reflux under argon for 4 hours. The mixture was concentrated, the residue was partitioned between $H_2O$ and DCM, the aqueous phase was extracted with DCM, and the combined organic layer was washed with brine, dried over $Na_2SO_4$, concentrated. The residue was purified by chromatography on silica gel (PE:EA=100:1) to afford compound CXCIX-4 (1.2 g, yield 50.9%). MS (ESI) m/z (M+H)$^+$ 319.2.

Compound 229 was prepared analogously to the procedure described in the synthesis of Compound 20 (55 mg, yield 43.5%). MS (ESI) m/z (M+H)$^+$ 501.0.

Compound 229a. $^1$H NMR (DMSO-d$_6$, 400 MHz): δ 8.89 (br, 1H), 7.68 (d, J=8.4 Hz, 2H), 7.58 (d, J=8.4 Hz, 2H), 7.53 (br, 4H), 7.28-7.34 (m, 5H), 5.74-5.76 (q, 1H), 2.29 (s, 3H), 1.48 (br, 3 H), 1.44 (s, 6 H). MS (ESI) m/z (M+H)$^+$ 501.0.

Synthesis of Compounds 230 and 231

Synthetic Route (Scheme CC)

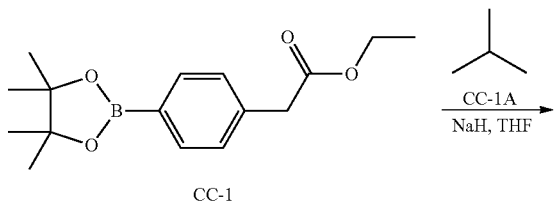

-continued
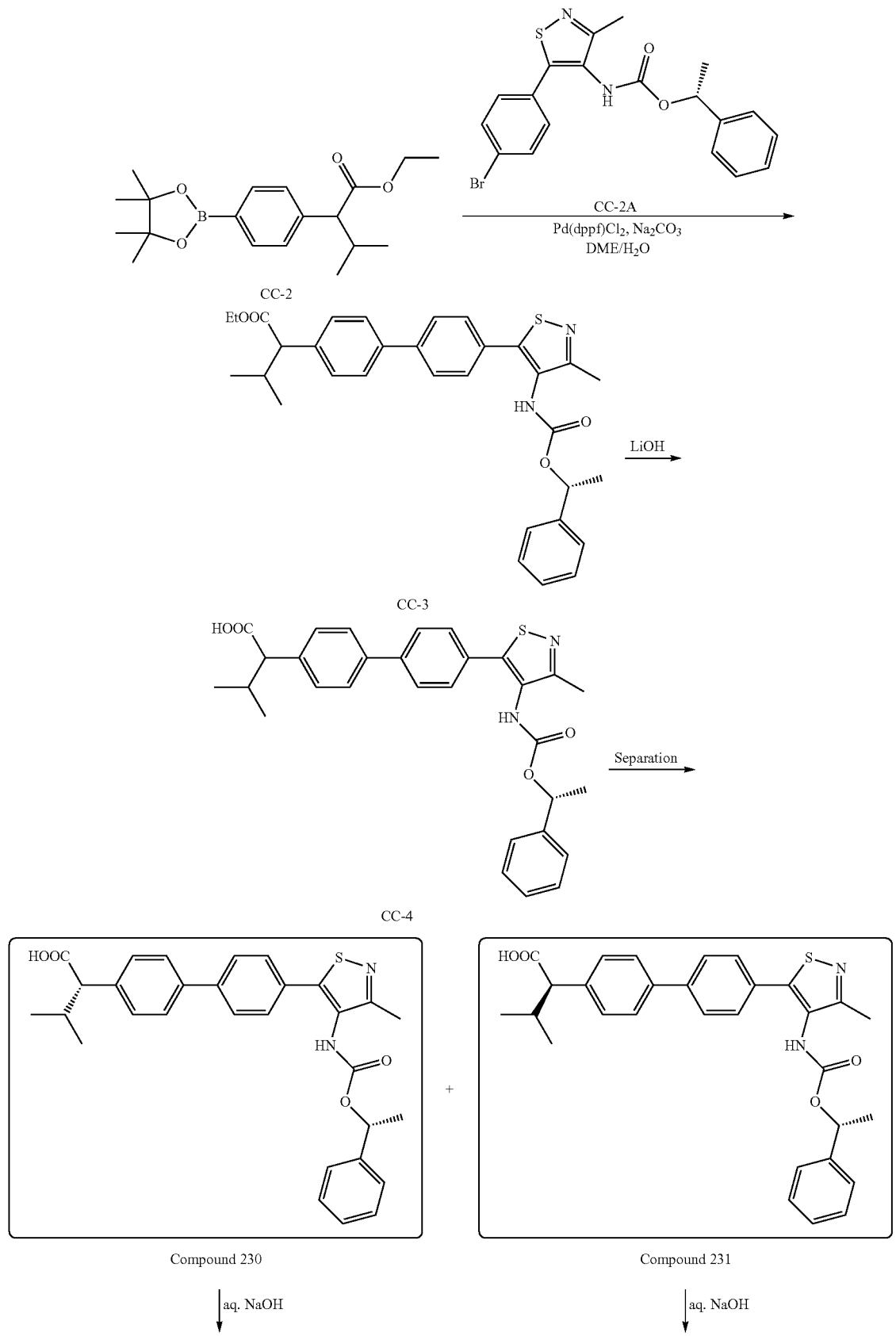

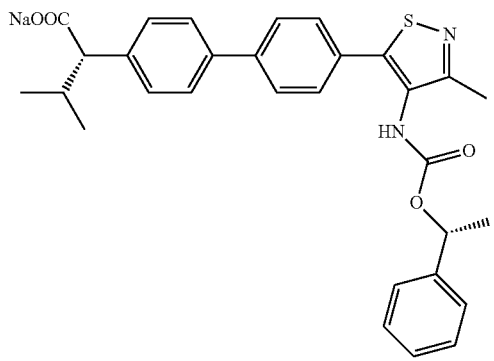

Compound 230a

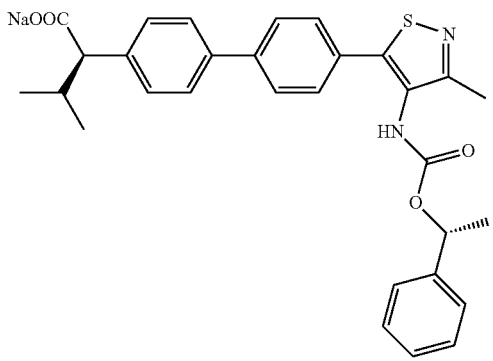

Compound 231a

To a stirred solution of compound CC-1 (3 g, 10.3 mmol) in THF (30 mL) was added NaH (0.45 g, 11 mmol), then compound CC-1A (2.1 g, 12.4 mmol) in THF (10 mL) was added dropwise at r.t. The reaction mixture and stirred at room temperature for overnight, then poured to water, and the mixture was extracted with EtOAc (30 mL×3). The organic layer was combined and washed with brine, dried over $Na_2SO_4$, concentrated in vacuo. The residue was purified by column chromatography on silica gel (PE:EA=50:1) to afford compound CC-2 (350 mg, yield 10%).

Compound CC-4 was prepared analogously to the procedure described in the synthesis of Compound 229 as racemic mixture (100 mg, yield 42%). This compound was separate by SFC to give two stereoisomers Compounds 230 and 231.

Compound 230a. $^1$H NMR (400 MHz, DMSO-$d_6$): δ 8.97 (br, 1 H), 7.68 (d, J=8.4 Hz, 2H), 7.57 (d, J=8.4 Hz, 2H), 7.52 (d, J=8.4 Hz, 2H), 7.45 (d, J=8.4 Hz, 2H), 7.27-7.33 (m, 5H), 5.72-5.77 (q, 1 H), 2.85 (d, J=10 Hz, 1H), 2.28 (s, 3H), 2.17-2.22 (m, 1 H), 1.47 (br, 3 H), 1.02 (d, J=6.4 Hz, 2 H), 0.65 (d, J=6.4 Hz, 2H). MS (ESI) m/z (M+H)$^+$ 515.1.

Compound 231a. $^1$H NMR (400 MHz, DMSO-$d_6$): δ 8.99 (br, 1 H), 7.69 (d, J=8.4 Hz, 2H), 7.57 (d, J=8.4 Hz, 2H), 7.53 (d, J=8.4 Hz, 2H), 7.45 (d, J=8.4 Hz, 2H), 7.27-7.33 (m, 5H), 5.72-5.77 (q, 1 H), 2.85 (d, J=10 Hz, 1H), 2.28 (s, 3H), 2.17-2.22 (m, 1 H), 1.47 (br, 3 H), 1.02 (d, J=6.4 Hz, 2 H), 0.65 (d, J=6.4 Hz, 2H). MS (ESI) m/z (M+H)$^+$ 515.1.

Synthesis of Compounds 232 and 233

Synthetic Route (Scheme CCI)

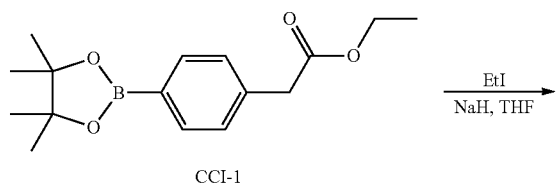

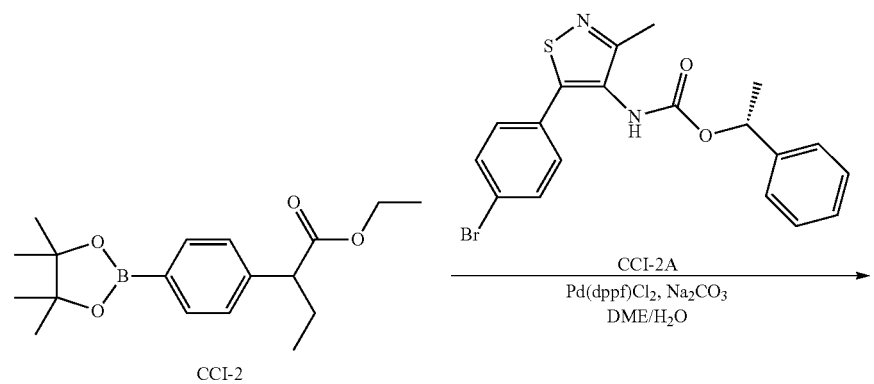

-continued
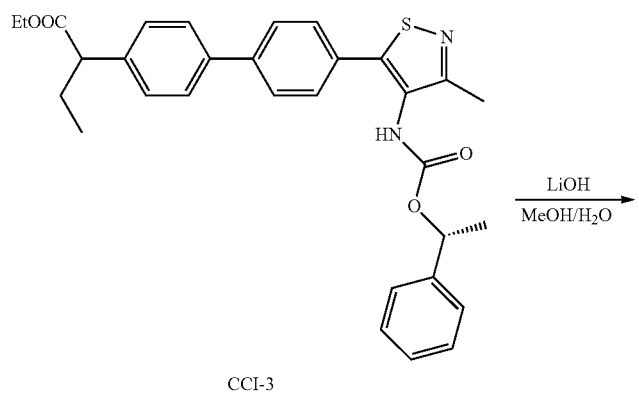
CCI-3
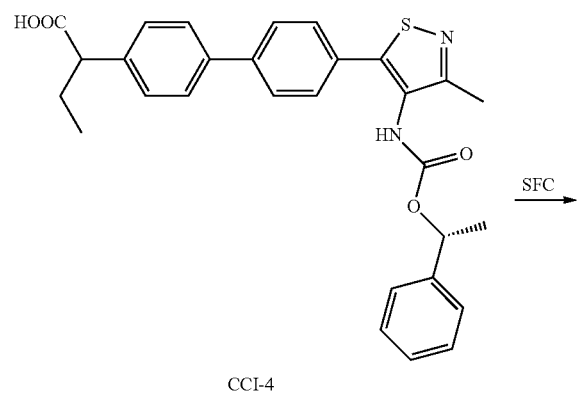
CCI-4
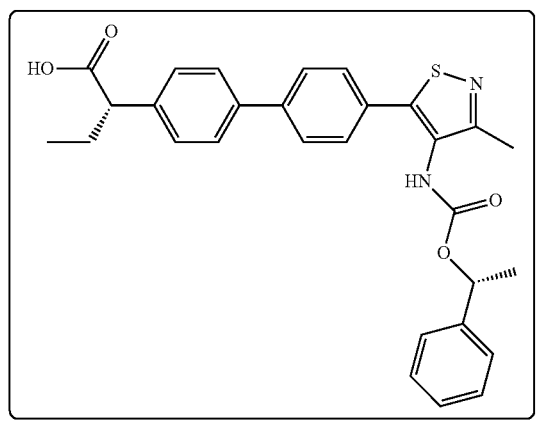
Compound 232
↓ NaOH
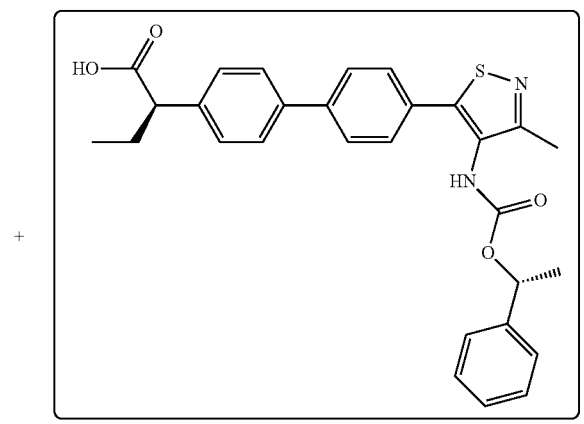
Compound 233
↓ NaOH

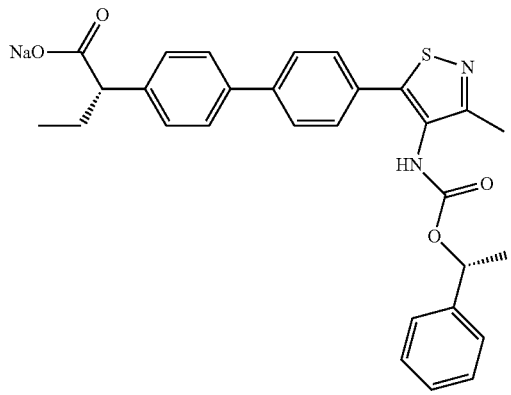

Compound 232a

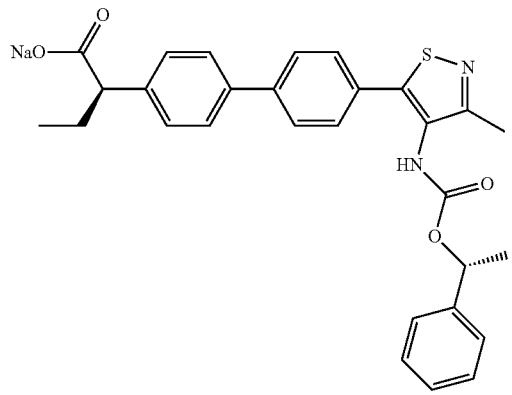

Compound 233a

To a stirred solution of compound CCI-1 (3 g, 10.3 mmol) in THF (30 mL) was added NaH (0.45 g, 11 mmol), then EtI (1.9 g, 12.4 mmol) in THF (10 mL) was added dropwise. The reaction mixture and stirred at room temperature for overnight. Then poured to water, and the mixture was extracted with EtOAc (30 mL×3). The organic layer was combined and washed with brine, dried over $Na_2SO_4$, concentrated in vacuo. The residue was purified by column chromatography on silica gel (PE:EA=50:1) to afford compound CCI-2 (410 mg, yield 12.5%).

Compound CCI-4 was prepared analogously to the procedure described in the synthesis of Compound 229 as racemic mixture (130 mg, yield 91.5%). This compound was separate by SFC to give two stereoisomers Compounds 232 and 233.

Compound 232a. $^1$H NMR (400 MHz, DMSO-$d_6$): δ 8.95 (s, 1 H), 7.69 (d, J=8.4 Hz, 2H), 7.57 (d, J=8.4 Hz, 2H), 7.54 (d, J=8.4 Hz, 2H), 7.42 (d, J=8.0 Hz, 2 H), 7.28-7.33 (m, 5 H), 5.77 (q, 1 H), 2.29 (s, 3 H), 1.99-2.04 (m, 1 H), 1.60-1.66 (m, 1 H), 1.48 (br, 3 H), 0.86 (t, J=7.2 Hz, 3 H). MS (ESI) m/z $(M+H)^+$ 501.0.

Compound 233a. $^1$H NMR (400 MHz, DMSO-$d_6$): δ 8.95 (s, 1 H), 7.71 (d, J=8.4 Hz, 2 H), 7.57 (d, J=8.4 Hz, 2H), 7.54 (d, J=8.4 Hz, 2H), 7.43 (d, J=8.0 Hz, 2 H), 7.28-7.33 (m, 5 H), 5.78 (q, 1 H), 2.29 (s, 3 H), 1.97-2.04 (m, 1 H), 1.59-1.66 (m, 1 H), 1.48 (s, 3 H), 0.86 (t, J=7.2 Hz, 3 H). MS (ESI) m/z $(M+H)^+$ 501.0.

Synthesis of Compounds 234 and 235

Synthetic Route (Scheme CCII)

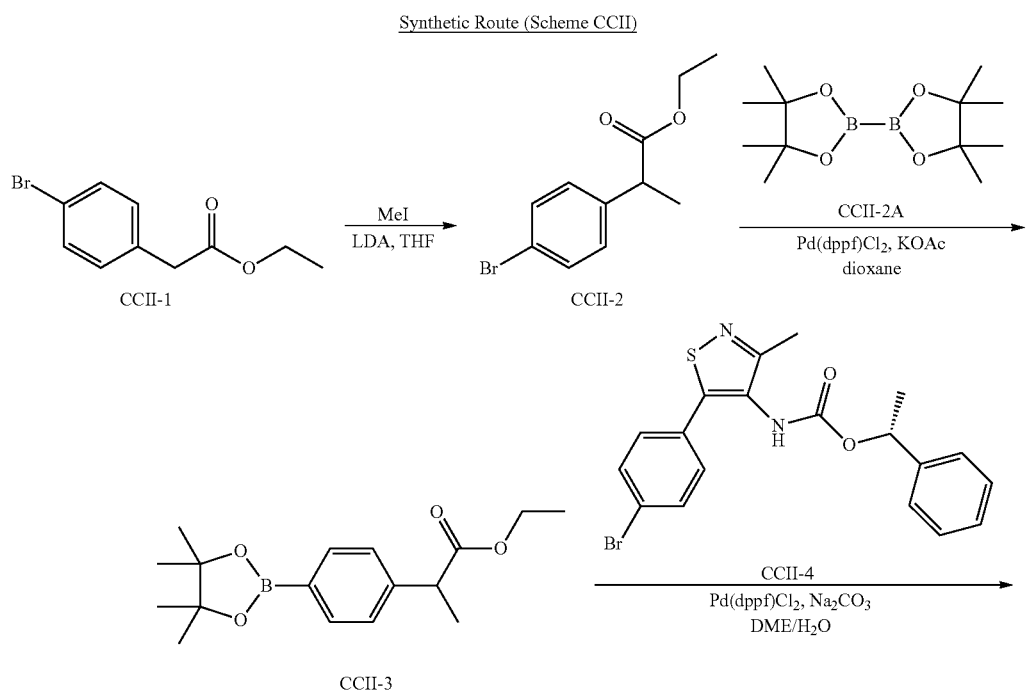

1161
-continued
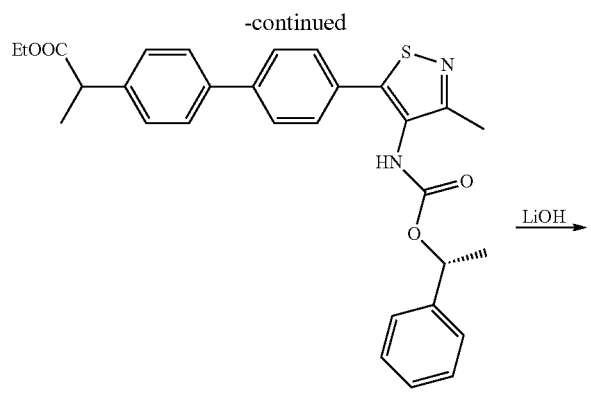
CCII-5
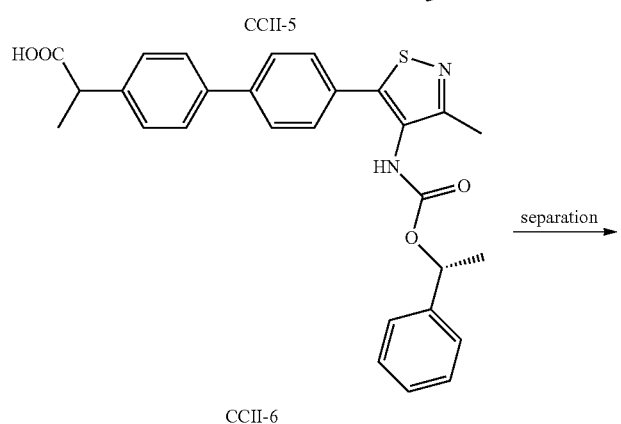
CCII-6
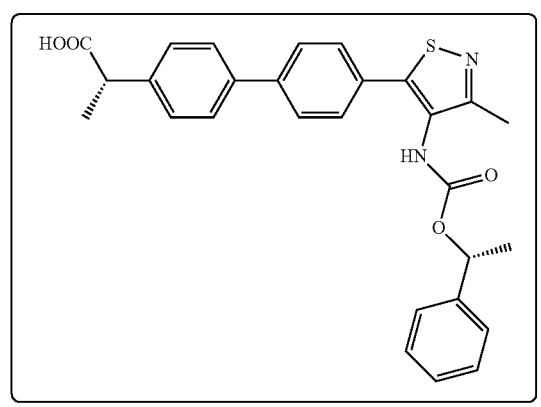
Compound 234
+
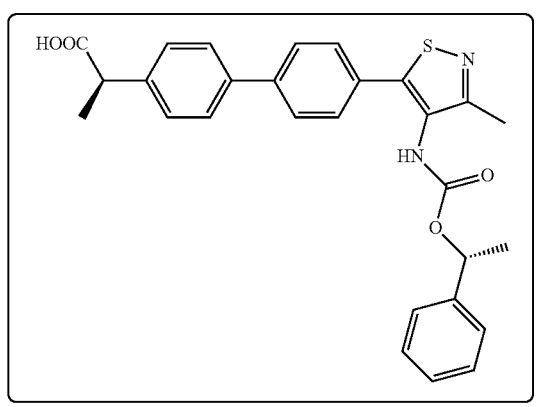
Compound 235
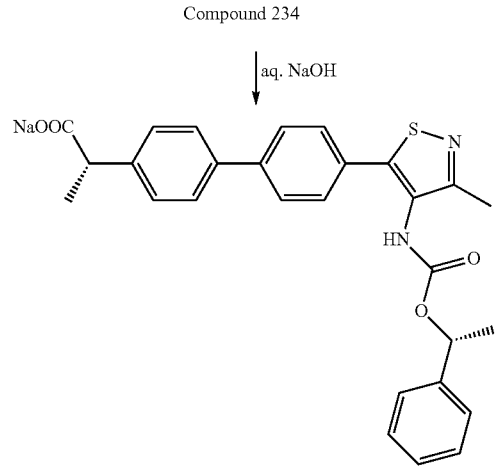
Compound 234a
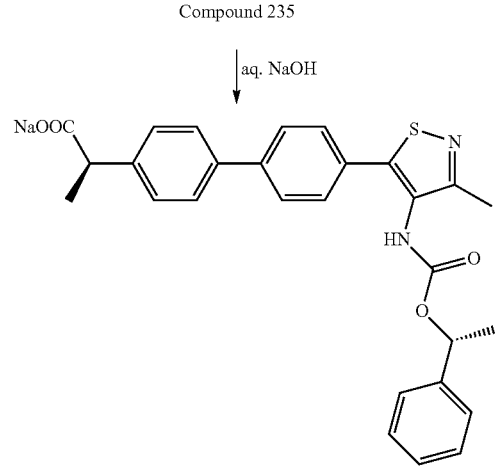
Compound 235a To a solution of diisopropylamine (2.3 g, 22.7 mmol) in anhydrous THF (30 mL) was added n-BuLi (9.1 mL, 2.5 N) dropwise at −78° C. After the addition was completed, the reaction mixture was stirred at −78° C. for 1 h, and then compound CCII-1 (5 g, 20.7 mmol) in THF (20 mL) was added. The reaction mixture was stirred at −78° C. for 1 hour and MeI (11.7 g, 82.8 mmol) was added dropwise. LC-MS monitored the reaction. After completion of the reaction, the mixture was poured into water, extract with EtOAc (60 mL×3), the combined organic layers were dried over $Na_2SO_4$, concentrated in vacuo. The residue was purified by chromatography (PE:EA=80:1) to afford compound CCII-2 (2 g, yield 37.8%). MS (ESI) m/z (M+H)$^+$ 258.0.

Compound CCII-6 was prepared analogously to the procedure described in the synthesis of Compound 20 as racemic mixture (300 mg, yield 91%). This compound was separate by SFC to give two stereoisomers Compounds 234 and 235.

Compounds 234a. $^1$H NMR (400 MHz, DMSO-d$_6$): δ 8.95 (s, 1 H), 7.69 (d, J=8.4 Hz, 2 H), 7.57 (d, J=8.4 Hz, 2H), 7.54 (d, J=8.0 Hz, 2H), 7.42 (d, J=8.0 Hz, 2 H), 7.28-7.33 (m, 5 H), 5.72-5.77 (q, 1 H), 3.37-3.42 (q, 1 H), 2.28 (s, 3H), 1.48 (br, 3 H), 1.34 (d, J=6.4 Hz, 3 H). MS (ESI) m/z (M+H)$^+$ 487.1.

Compounds 235a. $^1$H NMR (400 MHz, DMSO-d$_6$): δ 8.96 (s, 1 H), 7.69 (d, J=8.4 Hz, 2 H), 7.57 (d, J=8.4 Hz, 2H), 7.54 (d, J=8.0 Hz, 2H), 7.42 (d, J=8.0 Hz, 2 H), 7.28-7.33 (m, 5 H), 5.72-5.77 (q, 1 H), 3.37-3.41 (q, 1 H), 2.28 (s, 3H), 1.48 (br, 3 H), 1.34 (d, J=6.4 Hz, 3 H). MS (ESI) m/z (M+H)$^+$ 487.1.

Synthesis of Compound 236

Synthetic Route (Scheme CCIII)

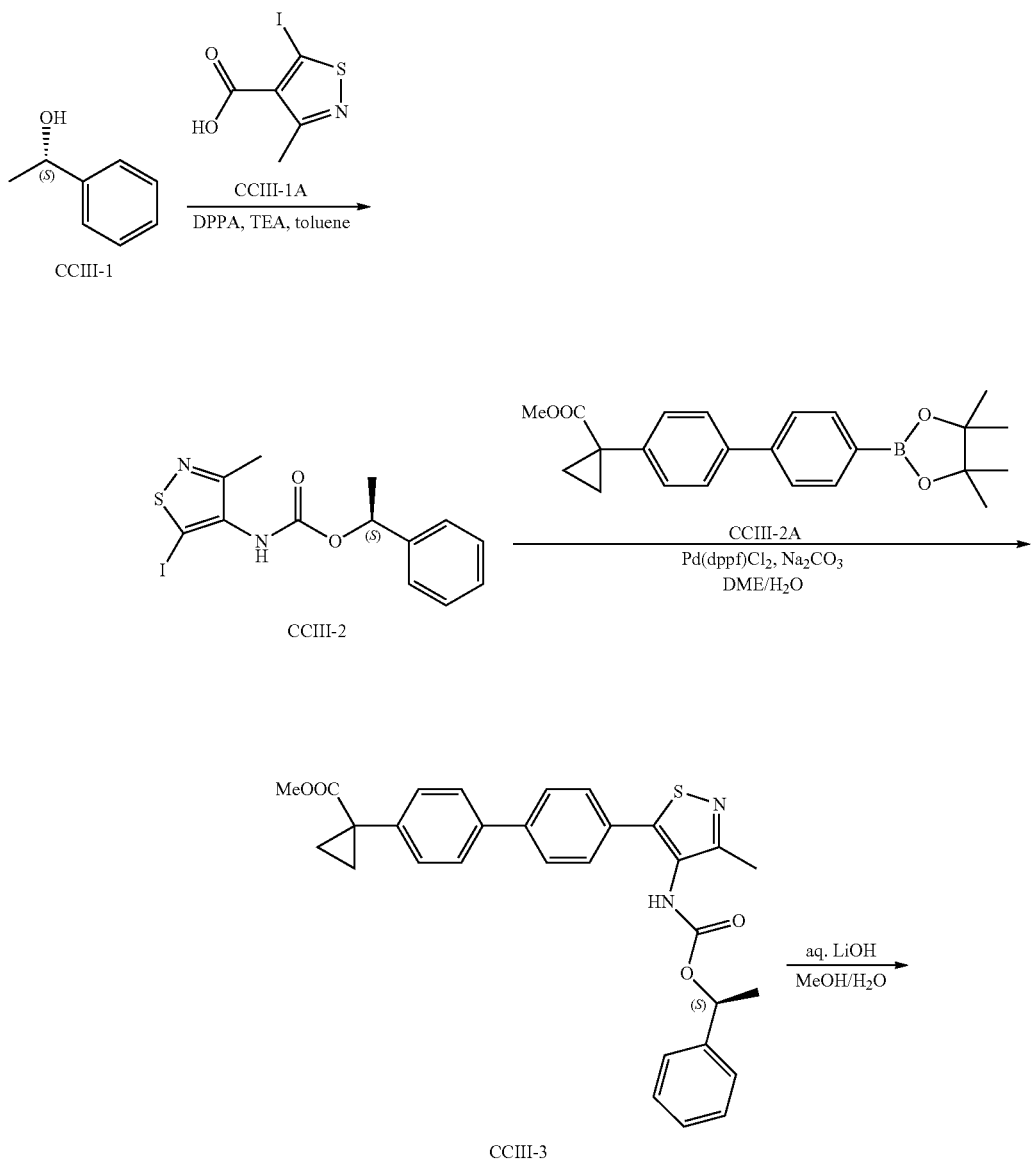

1165
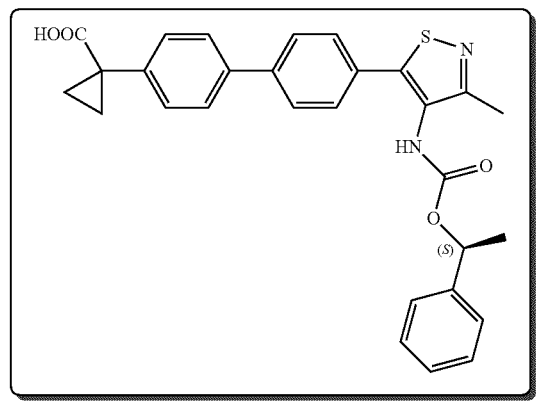
Compound 236
→ aq. NaOH →
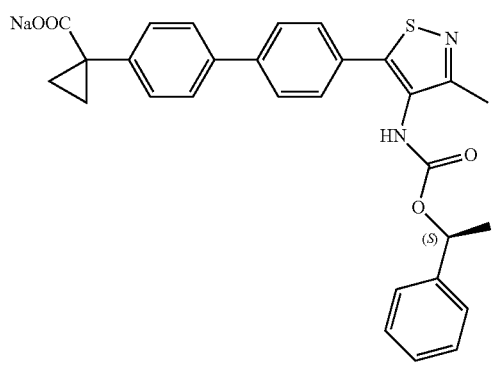
Compound 236a
Compound 236 was prepared analogously to the procedure described in the synthesis of Compound 44. Compound 236a: $^1$H NMR (400 MHz, DMSO-$d_6$): δ 7.69 (d, J=8.4 Hz, 2 H), 7.57 (d, J=8.4 Hz, 2 H), 7.50 (d, J=8.4 Hz, 2 H), 7.40 (d, J=8.4 Hz, 2 H), 7.28-7.39 (m, 5 H), 5.72-5.77 (q, 1 H), 2.29 (s, 3 H), 1.49 (d, J=6.4 Hz 3 H), 1.24-1.26 (m, 2 H), 0.70-0.72 (m, 2H). MS (ESI) m/z (M+H)$^+$ 499.1.
Synthesis of Compound 237
Synthetic Route (Scheme CCIV)
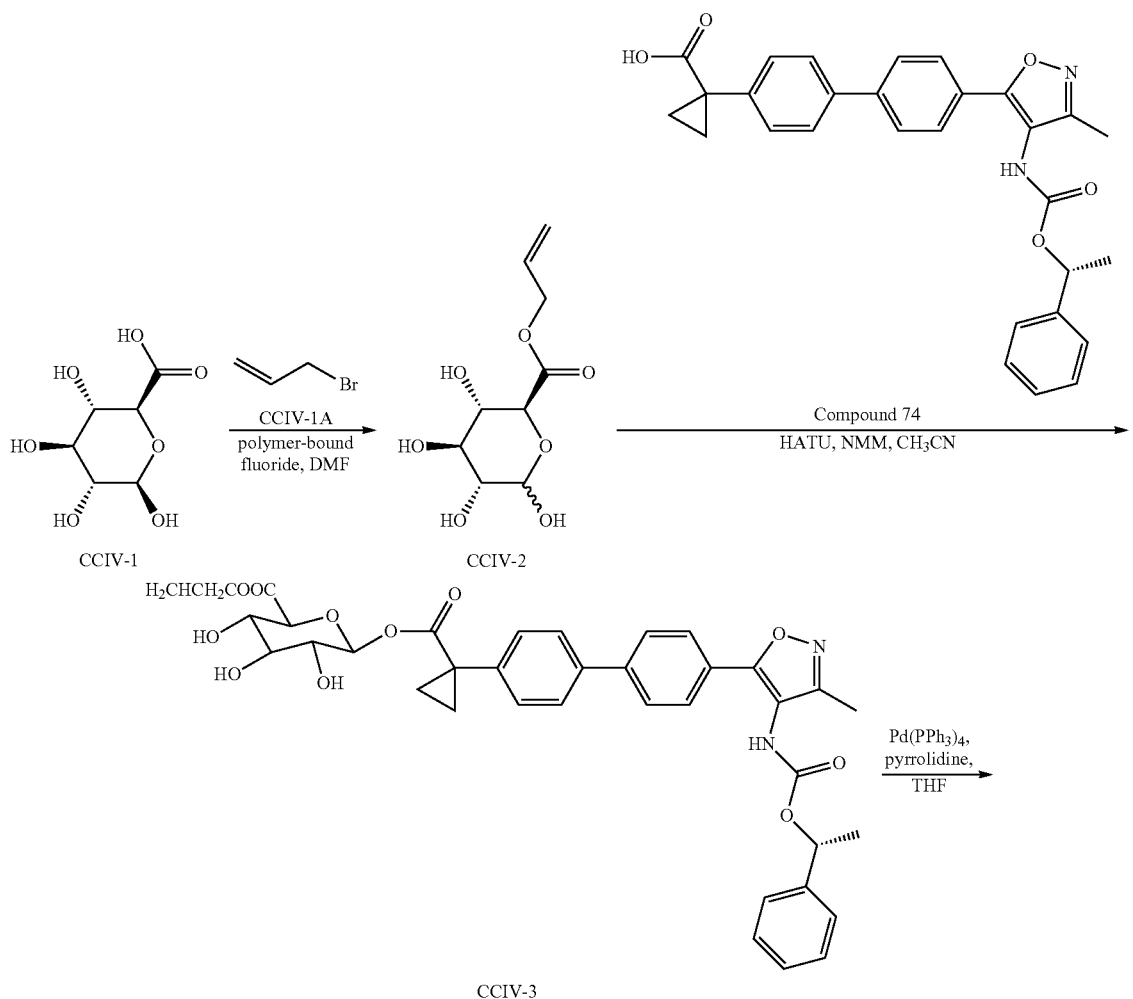

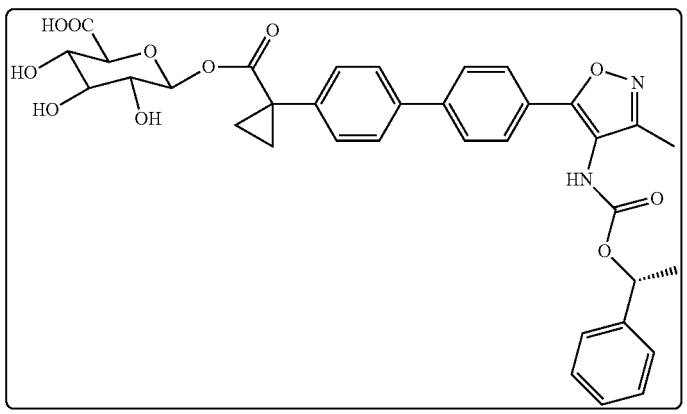

Compound 237

A commercial batch of polymer-bound fluoride (Sigma-Aldrich) was stirred in anhydrous DMF at 20° C. for 2 h, filtered, washed with ether and air-dried. This product (3 g, 9.0 mmol) was stirred in anhydrous DMF (15 mL) under $N_2$ with compound CCIV-1 (1.16 g, 6.0 mmol) for 3 h, then compound CCIV-1A (0.57 mL, 6.6 mmol) was added and the mixture was stirred at 40° C. for 20 h. The reaction mixture was filtered and the resin was washed with DMF (10 mL×3), then the combined filtrates were evaporated to dryness to give crude product, which was purified by chromatography ($CH_2Cl_2$:MeOH=100:6) to afford compound CCIV-2 (0.77 g, yield 55%).

Compound CCIV-2 (500 mg, 1.04 mmol), Compound 74 (243 mg, 1.04 mmol) and HATU (395 mg, 1.04 mmol) were stirred in dry acetonitrile with N-methyl morpholine (229 uL, 2.08 mmol) under nitrogen at 20° C. Then the reaction was heated to 70° C. for 24 hrs. This mixture was concentrated and purified by chromatography ($CH_2Cl_2$:MeOH=100:6) to afford compound CCIV-3 (200 mg, yield 27.5%).

Preparation of Compound 237

$Pd(PPh_3)_4$ (16.5 mg, 0.014 mmol) and pyrrolidine (10.2 mg, 0.14 mmol) were added to compound CCIV-3 (100 mg, 0.14 mmol) with stirring in THF (0.5 mL) at 0° C. for 0.75 h. Evaporation of solvent left a yellow gum, which was purified by HPLC to afford Compound 237 (30 mg, yield 31.9%). $^1$H NMR (400 MHz, Methanol-$d_4$): δ 7.84 (d, J=8.0 Hz, 2 H), 7.72 (d, J=8.4 Hz, 2 H), 7.65 (d, J=8.4 Hz, 2 H), 7.53 (d, J=8.0 Hz, 2 H), 7.34-7.48 (m, 5 H), 5.90 (q, 1 H), 5.54 (d, J=8.0 Hz, 1 H), 3.91 (d, J=9.6 Hz, 1 H), 3.54 (d, J=9.2 Hz, 1 H), 3.50 (d, J=11.6 Hz, 1 H), 3.30 (d, J=8.8 Hz, 1 H), 2.20 (s, 3 H), 1.75-1.85 (m, 2 H), 1.64 (d, J=6.4 Hz, 3 H), 1.35 (s, 2 H). MS (ESI) m/z (M+H)$^+$ 659.1.

Synthesis of Compound 238

Synthetic Route (Scheme CCV)

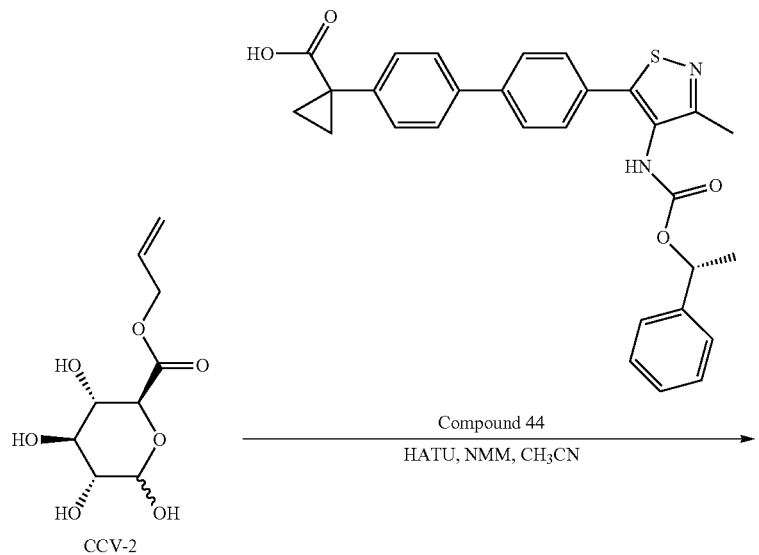

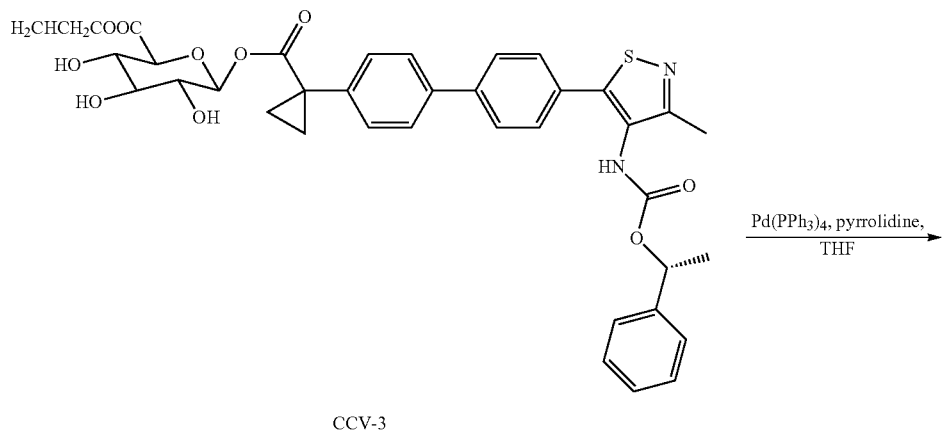
CCV-3
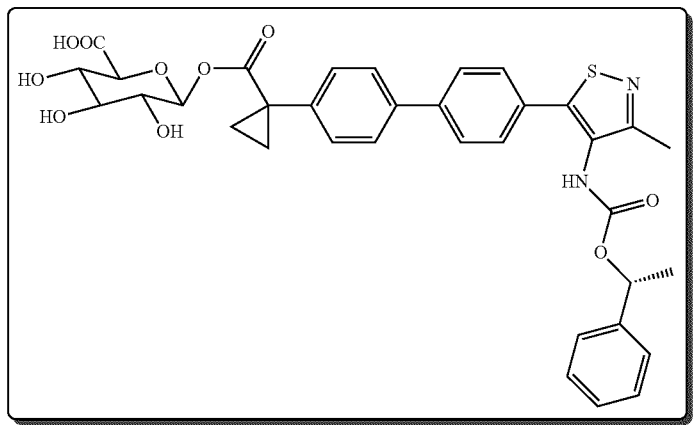
Compound 238
Compound 238 was prepared analogously to the procedure described in the synthesis of Compound 237. $^1$H NMR (400 MHz, Methanol-$d_4$): δ 7.51-7.68 (m, 8 H), 7.31-7.42 (m, 5 H), 5.80 (q, 1 H), 5.54 (d, J=8.0 Hz, 1 H), 3.92 (d, J=9.6 Hz, 1 H), 3.55 (d, J=9.2 Hz, 1 H), 3.50 (d, J=12.8 Hz, 1 H), 3.30 (d, J=8.4 Hz, 1 H), 2.34 (s, 3 H), 1.75-1.85 (m, 2 H), 1.59 (d, J=6.4 Hz, 3 H), 1.36 (s, 2 H). MS (ESI) m/z (M+H)$^+$ 675.0.
Synthesis of Compound 239
Synthetic Route (Scheme CCVI)
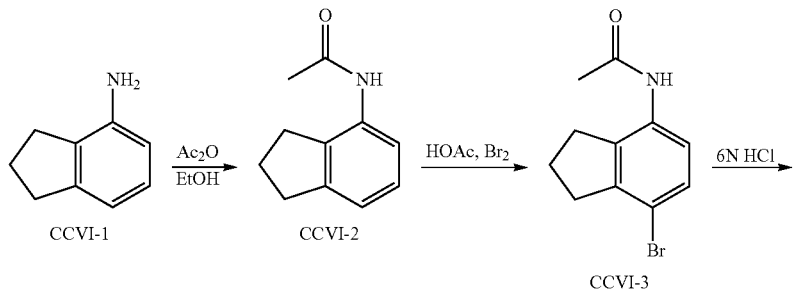

-continued
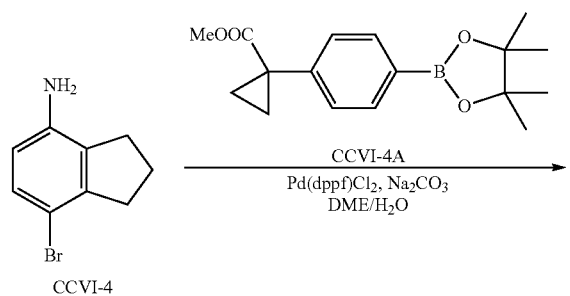
CCVI-4
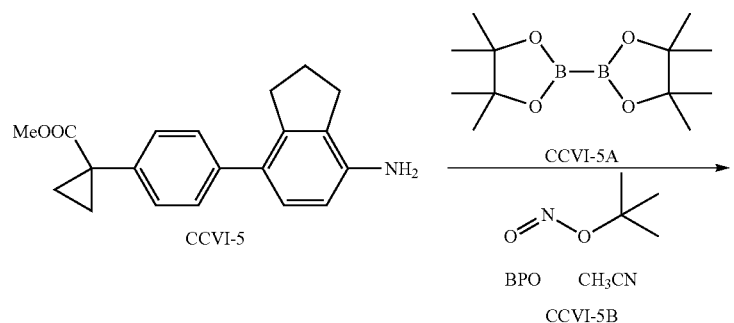
CCVI-5
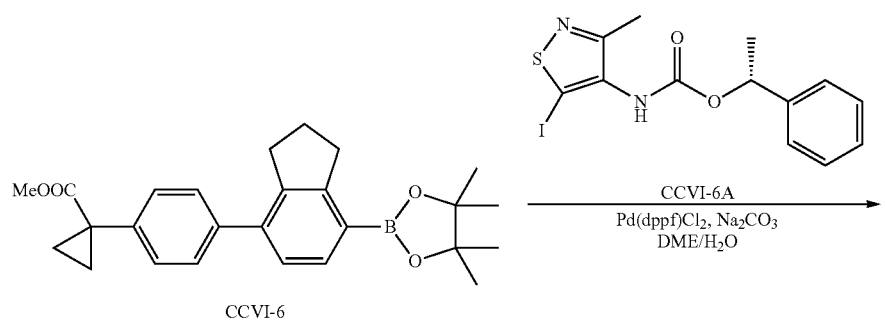
CCVI-6
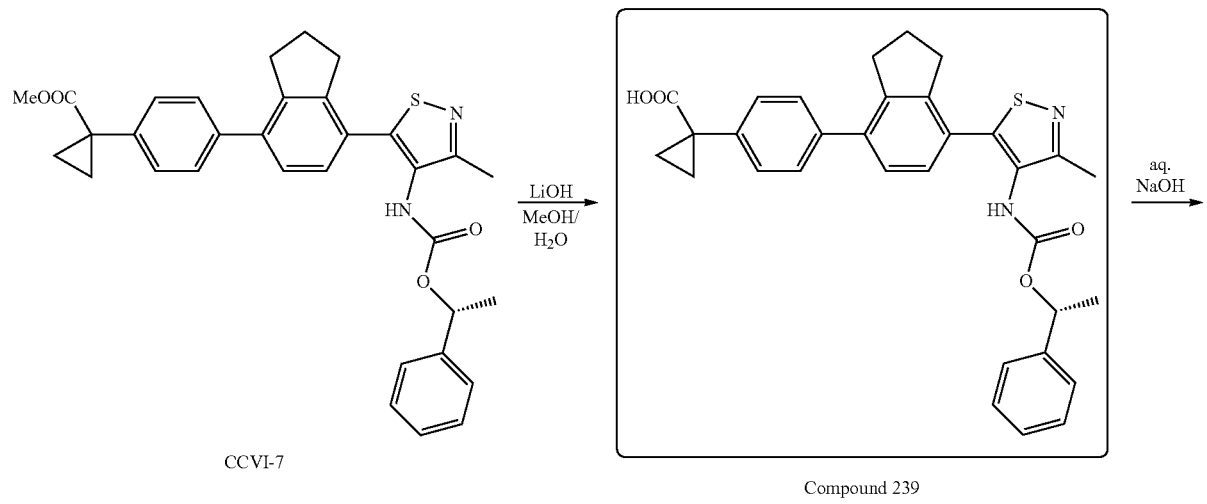
CCVI-7
Compound 239

-continued

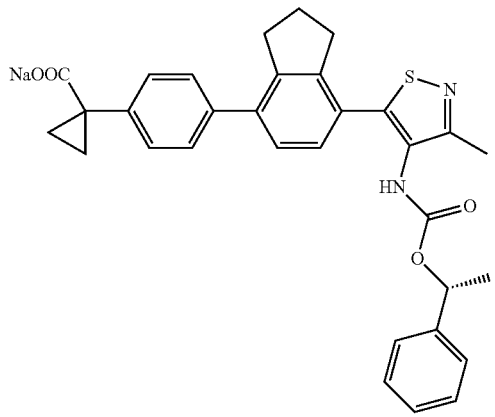

Compound 239a

Ac$_2$O (2 mL) was added dropwise to the mixture of compound CCVI-1 (5 g, 37 mmol) in 60 mL of EtOH at r.t., the reaction mixture was stirred at r.t. for 10 h. TLC (PE:EA=5:1) shows the starting material consumed completely. The mixture was concentrated under reduced pressure, washed with EtOAc to afford compound CCVI-2 (5.3 g, yield 80%) as white solid.

Br$_2$ (1.8 g, 11.4 mmol) in 10 mL of HOAc was added to the mixture of compound 2 (2.0 g, 11.4 mmol) in HOAc/DCM (10 mL/5 mL) at r.t., the reaction mixture was stirred at r.t. overnight. TLC (PE:EA=2:1) show the starting material consumed completely. The mixture was concentrated under reduced pressure, extracted with EtOAc (50 mL) and washed with aq. NaHCO$_3$ and brine, dried and concentrated to afford compound CCVI-3 (2.5 g, yield 86.5%) as white solid.

The mixture of compound CCVI-3 (1.0 g, 3.95 mmol) in 6 N HCl (50 mL) was stirred at reflux for 14 hours. After being cooled to r.t., Na$_2$CO$_3$ was added to adjusted to pH=7-8, and extracted with EtOAc (50 mL). The organic layer was separated, dried and concentrated to afford compound CCVI-4 (0.68 g, yield 82%).

Na$_2$CO$_3$ (1.05 g, 9.9 mmol) and compound CCVI-4A (1.096 g, 3.63 mmol) were added to a solution of compound CCVI-4 (700 mg, 3.3 mmol) in DME:H$_2$O=3:1 (15 mL), the resulting mixture was purged with nitrogen, then Pd(dppf)Cl$_2$ (241 mg, 0.33 mmol) was added. The reaction mixture was stirred at 80° C. overnight under nitrogen protection. After completion of the reaction, the mixture was poured into water, extract with EtOAc (30 mL×3), the combined organic layers were dried over Na$_2$SO$_4$, concentrated in vacuo. The residue was purified by chromatography (PE:EA=10:1) to afford compound CCVI-5 (800 mg, yield 79%).

To a stirred solution of compound CCVI-5 (850.0 mg, 2.6 mmol), compound CCVI-5A (792 mg, 3.12 mmol), compound CCVI-5B (409 mg, 3.9 mmol) in CH$_3$CN (10 mL) was added BPO (85 mg). Then the reaction mixture was stirred overnight at room temperature. After completion of the reaction, the mixture was poured into water, extract with EtOAc (30 mL×3), washed with sat. Na$_2$S$_2$SO$_3$, the combined organic layers were dried over Na$_2$SO$_4$, concentrated in vacuo. The residue was purified by chromatography (PE:EA=10:1) to afford compound CCVI-6 (380 mg, yield 35%).

Na$_2$CO$_3$ (608 mg, 5.7 mmol) and compound CCVI-6A (816 mg, 2.1 mmol) were added to a solution of compound CCVI-6 (800 mg, 1.9 mmol) in DME/H$_2$O (10 mL, v/v=3/1), the resulting mixture was purged with nitrogen, then Pd(dppf)Cl$_2$ (140 mg, 0.19 mmol) was added. The reaction mixture was stirred at 80° C. overnight under nitrogen protection. After completion of the reaction, the mixture was poured into water, extract with EtOAc (30 mL×3), the combined organic layers were dried over Na$_2$SO$_4$, concentrated in vacuo. The residue was purified by chromatography (PE:EA=15:1) to afford compound CCVI-7 (800 mg, yield 75%). MS (ESI) m/z (M+H)$^+$553.6.

Preparation of Compound 239

To a stirred solution of compound CCVI-7 (300 mg, 0.543 mmol) in MeOH/H$_2$O (12 mL, v/v=5/1) was added LiOH (114 mg, 1.63 mmol). After the addition, the solution was stirred overnight at r.t. The solution was concentrated in vacuo, the aqueous layer was adjusted pH to 2 with 1 N HCl, and extracted with EtOAc (10 mL×3). The organic layer was separated, dried and concentrated. The residue was purified by prep-HPLC to afford Compound 239 (138 mg, yield 47%).

Preparation of Compound 239a

To a stirred solution of Compound 239 (138 mg, 0.257 mmol) in MeOH (3 mL) was added 0.05 N NaOH (5.1 mL). After the addition, the solution was stirred for half an hour at 0° C. The solution was freeze drying to afford Compound 239a. $^1$H NMR (400 MHz, DMSO-d$_6$): δ 8.80 (br, 1H), 7.28-7.39 (m, 9H), 7.20-7.21 (m, 2H), 5.70-5.75 (q, 1H), 2.98 (t, J=6.4 Hz 2H), 2.85 (t, J=6.4 Hz 2H), 2.30 (s, 3H), 1.90-1.97 (m, 2H), 1.45 (d, J=6.0 Hz, 3H), 1.24-1.25 (m, 2H), 0.71-0.72 (m, 2H). MS (ESI) m/z (M+H)$^+$ 539.0.

Synthesis of Compound 240
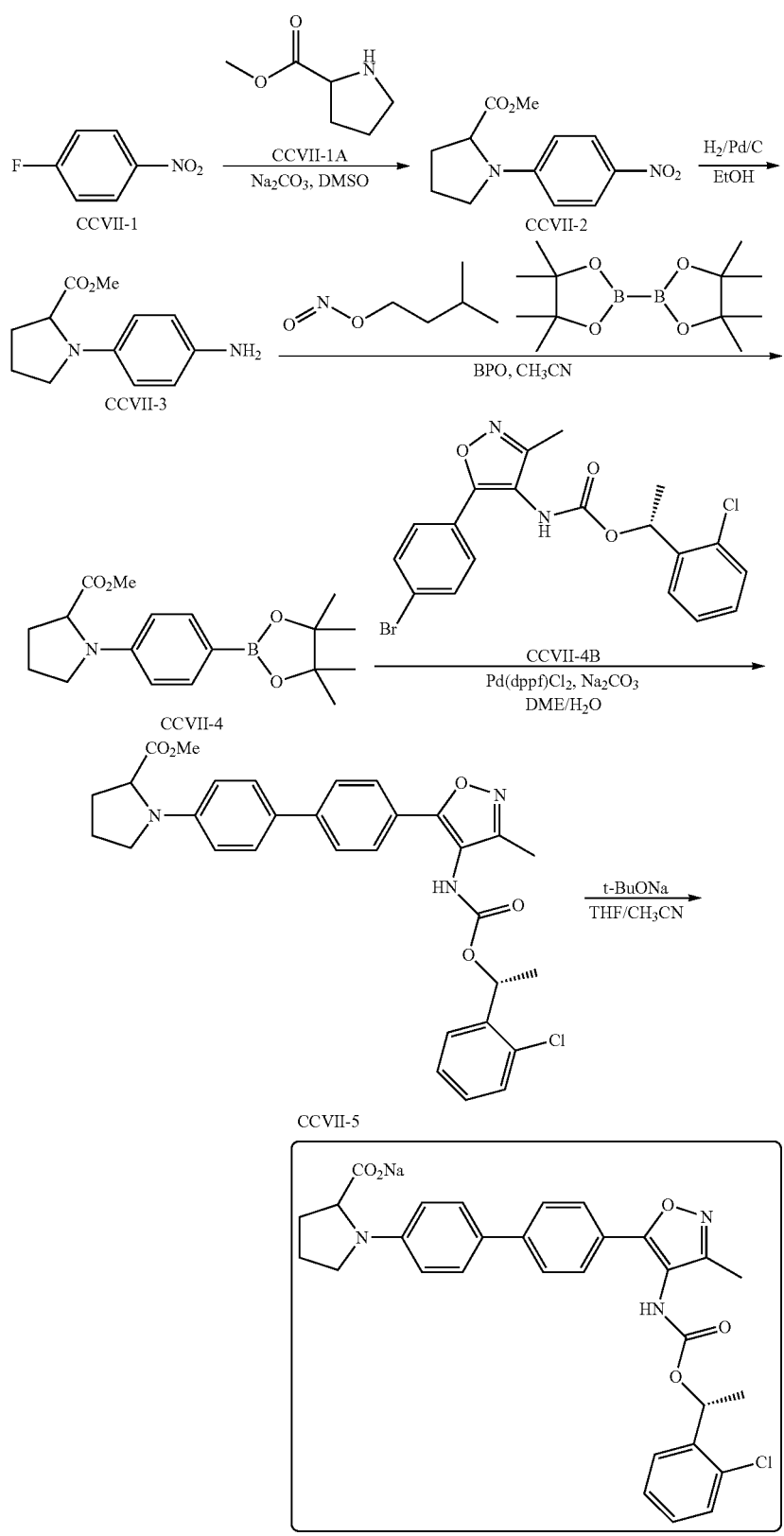

To a solution of compound CCVII-1 (14.1 g, 100 mmol) and compound CCVII-1A (15.5 g, 120 mmol) in 100 mL of DMSO was added $Na_2CO_3$ (31.8 g, 300 mmol). The mixture was heated to 80° C. and stirred overnight. After cooled, the mixture was poured into ice-water. The precipitate was collected and dried in vacuum to afford compound CCVII-2 (15 g, yield 60%).

To a solution of compound CCVII-2 (10 g, 0.04 mol) in EtOH (500 mL) was added Pd/C (10%, 1.0 g) under $N_2$. The suspension was degassed under vacuum and purged with $H_2$ several times. Then the reaction mixture was stirred under $H_2$ (45 psi) at room temperature overnight. After filtered, the filtrated was concentrated to afford compound CCVII-3 (8.7 g, yield 98.8%), which was used to next step directly.

Compound 240a was prepared analogously to the procedure described in the synthesis of Compound 132 (49 mg, 74% yield). $^1$H NMR (400 MHz, Methanol-$d_4$): δ 7.75 (d, J=7.6 Hz, 2H), 7.62-7.65 (m, 3H), 7.50 (d, J=8.4 Hz, 2H), 7.29-7.39 (m, 3H), 6.64 (d, J=8.8 Hz, 2H), 6.16 (q, J=6.4 Hz, 1H), 4.01-4.03 (m, 1H), 3.65-3.72 (m, 1H), 3.30-3.37 (m, 1H), 2.22-2.32 (m, 6H), 2.00-2.01 (m, 1H), 1.62 (d, J=6.4 Hz, 3H). MS (ESI) m/z (M+H)$^+$ 546.2.

Synthesis of Compound 241

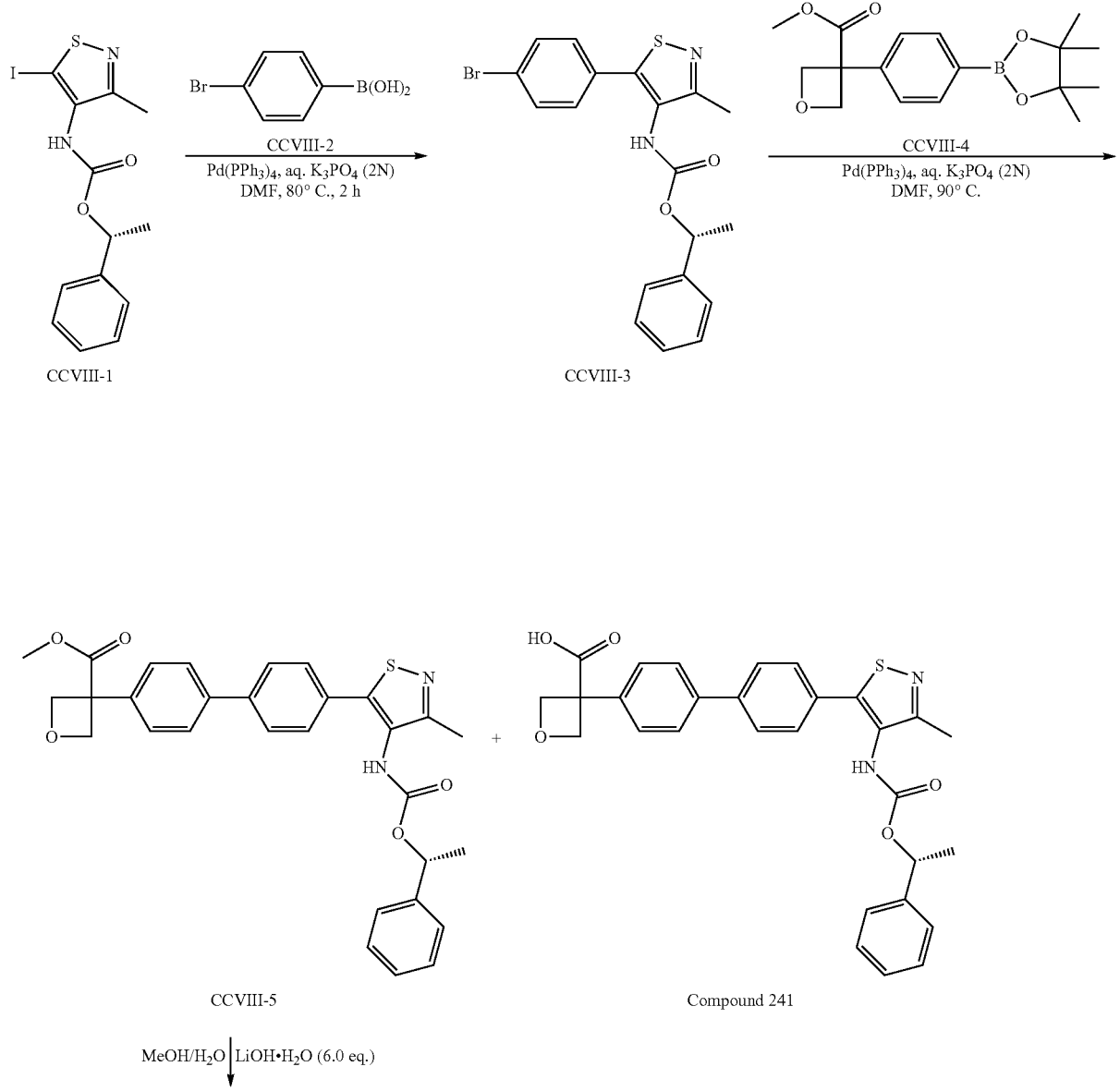

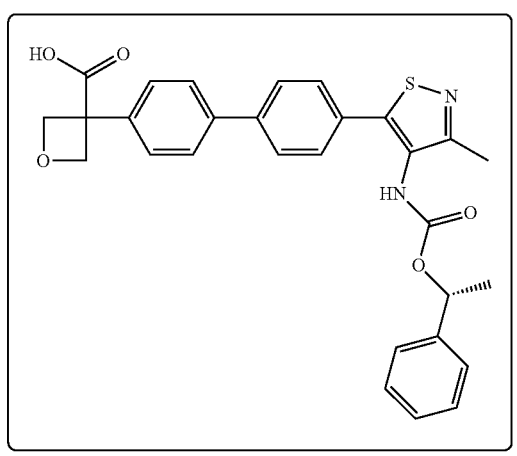

Compound 241

-continued

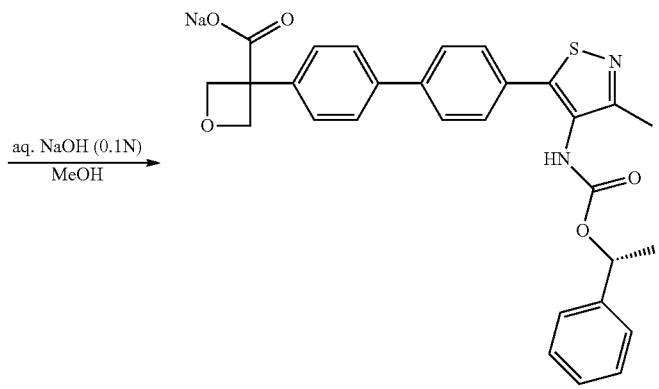

Compound 241a

A flask (10 mL) was charged with compound CCVIII-1 (194 mg, 0.5 mmol), compound CCVIII-2 (100 mg, 0.5 mmol), DMF (1 mL), followed by addition of aq. $K_3PO_4$ (2 M, 0.25 mL, 0.5 mmol). The flask was purged with nitrogen for three times. And then $Pd(PPh_3)_4$ (29 mg, 0.025 mmol) was added thereto and then the mixture was purged with nitrogen again. The mixture was stirred at 80° C. for 2 hrs. TLC (PE:EA=3:1) monitored the reaction. After the starting material was consumed, the mixture was cooled to r.t, diluted with EtOAc (60 mL), washed with brine, dried over $Na_2SO_4$ and concentrated. The residue was purified by prep-TLC (PE: EA=2:1) to afford compound CCVIII-3 (170 mg, 81% yield). MS (ESI) m/z (M+H)$^+$ 419.1.

Compound 241 was prepared analogously to the procedure described in the synthesis of Compound 80. $^1$HNMR (CD$_3$OD, 300 MHz) δ 7.70-7.60 (m, 4H), 7.58-7.50 (m, 2H), 7.45-7.22 (m, 6H), 7.20-6.96 (m, 1H), 5.80-5.69 (m, 1H), 5.25 (d, J=6.3 Hz, 2H), 5.02 (d, J=6.3 Hz, 2H), 2.31 (s, 3H), 1.54 (d, J=6.3 Hz, 3H). MS (ESI) m/z (M+H)$^+$ 515.1.

Compound 241a: $^1$HNMR (CD$_3$OD, 400 MHz) δ 7.64 (d, J=8.0 Hz, 4H), 7.54 (d, J=8.0 Hz, 4H), 7.40-7.24 (m, 4H), 7.20-6.96 (m, 1H), 5.80-5.70 (m, 1H), 5.29 (d, J=6.0 Hz, 2H), 4.93 (d, J=6.0 Hz, 2H), 2.32 (s, 3H), 1.56 (d, J=6.4 Hz, 3H). MS (ESI) m/z (M+H)$^+$ 515.1.

Synthesis of Compound 242

Synthetic Route (Scheme CCIX)

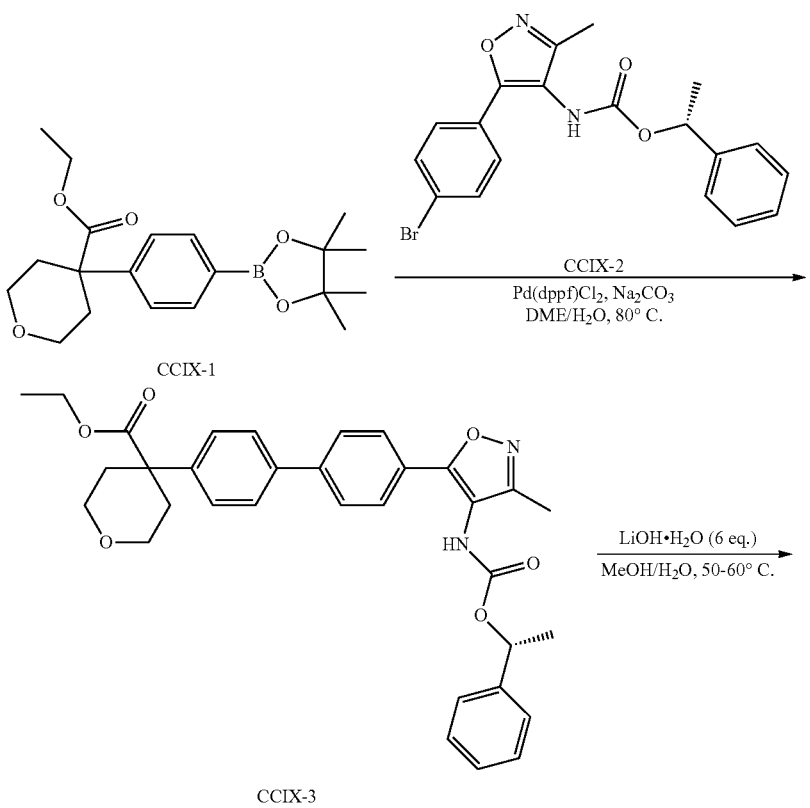

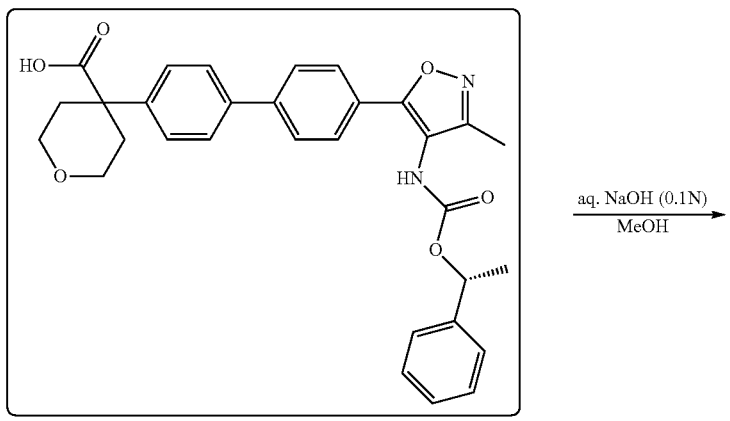

Compound 242

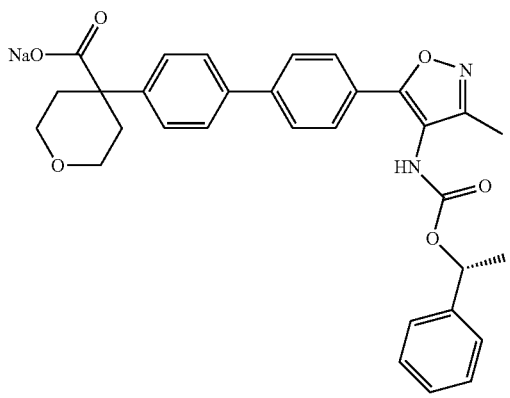

Compound 242a

The preparation of compound CCIX-1 was described in the synthesis of Compound 79 (intermediate L-3).

Compound 242 was prepared analogously to the procedure described in the synthesis of Compound 79. ¹HNMR (CD₃OD, 400 MHz) δ 7.84-7.81 (m, 2H), 7.74-7.75 (m, 4H), 7.59-7.56 (m, 2H), 7.47-7.30 (m, 4H), 7.18-7.06 (m, 1H), 5.84-5.78 (m, 1H), 3.97-3.92 (m, 2H), 3.65 (t, J=10.4 Hz, 2H), 2.55 (d, J=12.8 Hz, 2H), 2.18 (s, 3H), 2.05-1.96 (m, 2H), 1.60 (d, J=6.4 Hz, 3H). MS (ESI) m/z (M+H)⁺ 527.2.

Compound 242a: ¹HNMR (DMSO-d₆, 400 MHz) δ 9.37 (s, 1H), 7.82-7.71 (m, 4H), 7.57 (d, J=8.4 Hz, 2H), 7.48 (d, J=8.4 Hz, 2H), 7.45-7.38 (m, 3H), 7.36-7.03 (m, 2H), 5.78-5.71 (m, 1H), 3.75-3.68 (m, 2H), 3.57-3.50 (m, 2H), 2.47-2.41 (m, 2H), 2.11 (s, 3H), 1.61-1.52 (m, 5H). MS (ESI) m/z (M+H)⁺ 527.3.

Synthesis of Compound 243

Synthetic Route (Scheme CCX)

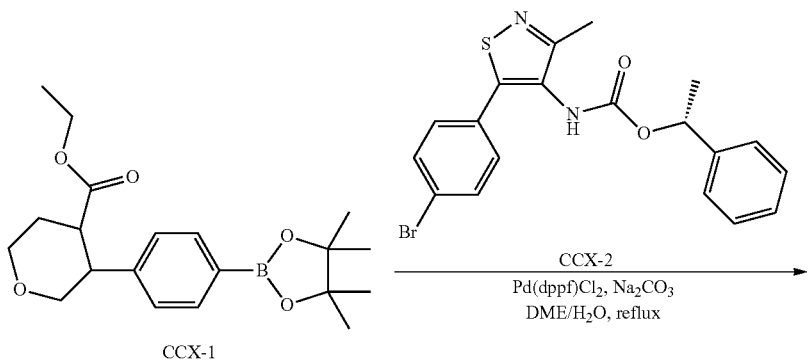

-continued
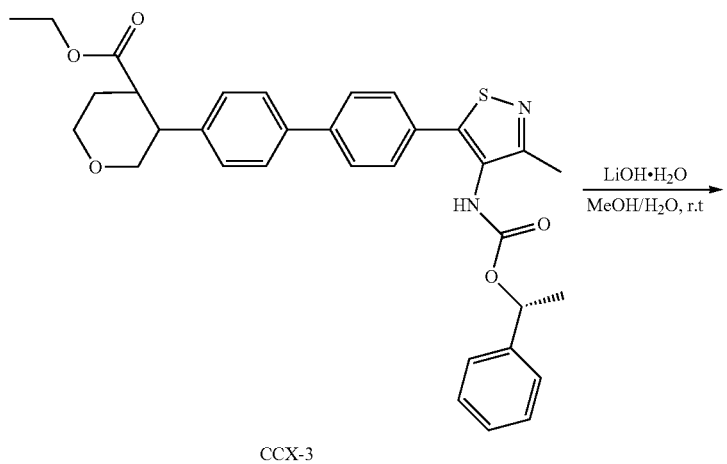
CCX-3
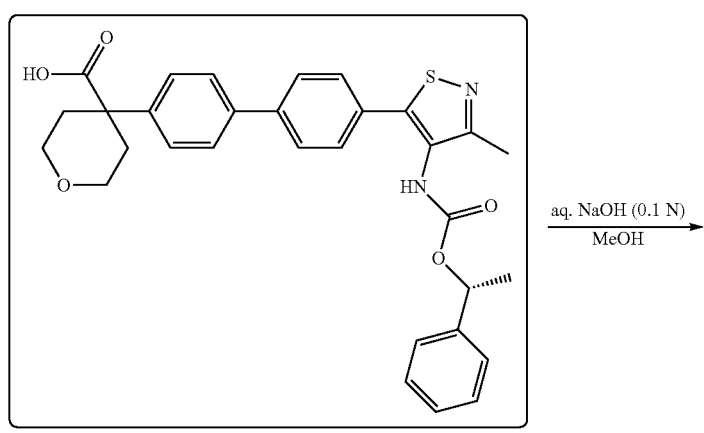
Compound 243
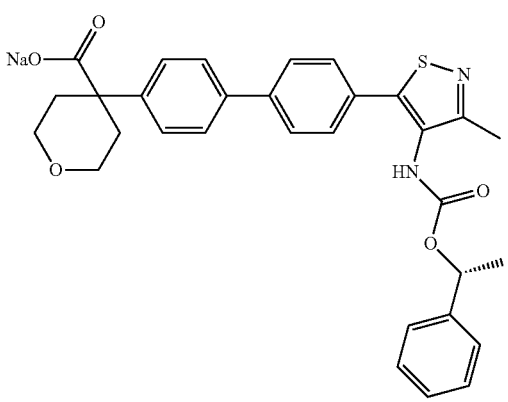
Compound 243a
Compound 243 was prepared analogously to the procedure described in the synthesis of Compound 79. $^1$HNMR (DMSO-d$_6$, 400 MHz) δ 9.28 (s, 1H), 7.75-7.71 (m, 4H), 7.56 (d, J=7.6 Hz, 2H), 7.50 (d, J=8.4 Hz, 2H), 7.41-7.35 (m, 3H), 7.30 (m, 1H), 7.22-6.99 (m, 1H), 5.74-5.69 (m, 1H), 3.87-3.81 (m, 2H), 3.47 (t, J=10.4 Hz, 2H), 2.44-2.39 (m, 2H), 2.24 (s, 3H), 1.90-1.83 (m, 2H), 1.51 (d, J=6.4 Hz, 3H).
Compound 243a: $^1$HNMR (DMSO-d$_6$, 400 MHz) δ 9.29 (s, 1H), 7.69 (d, J=7.6 Hz, 2H), 7.58-7.51 (m, 4H), 7.48 (d, J=8.4 Hz, 2H), 7.39-7.28 (m, 4H), 7.21-6.98 (m, 1H), 5.76-5.70 (m, 1H), 3.74-3.69 (m, 2H), 3.57-3.49 (m, 2H), 247-2.42 (m, 2H), 2.24 (s, 3H), 1.61-1.53 (m, 2H), 1.51 (d, J=6.0 Hz, 3H).

Synthesis of Compound 244

Synthetic Route (Scheme CCXI)

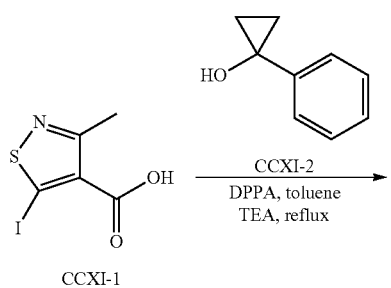

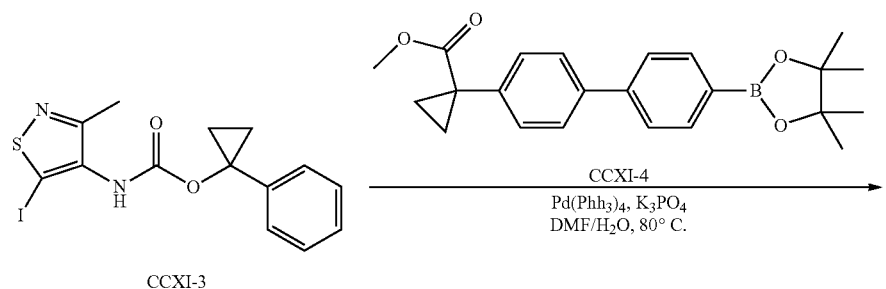

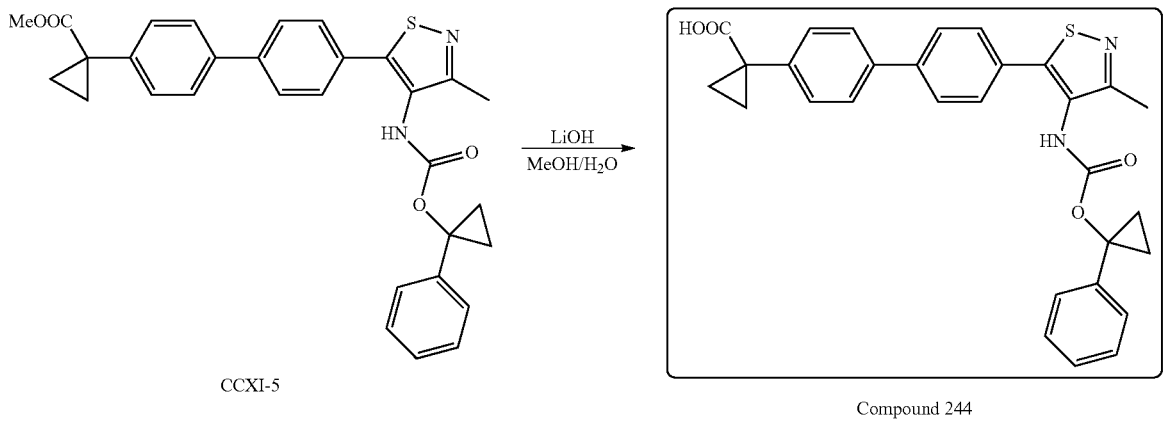

Compound 244

To a solution of compound CCXI-1 (0.54 g, 2 mmol) and compound CCXI-2 (0.323 g, 2.4 mmol) in toluene (40 mL) was added DPPA (0.58 g, 2.1 mmol) and TEA (0.51 g, 5 mmol). The reaction mixture was stirred at reflux overnight under $N_2$ protection. The mixture was evaporated and the residue was purified by column chromatography on silica gel (PE:EA=8:1-5:1) to yield compound CCXI-3 (0.42 g, yield 52%). MS (ESI) m/z (M+H)+ 401.0.

To a mixture of compound CCXI-3 (0.4 g, 1 mmol), $K_3PO_4$ (0.424 g, 2 mmol) and compound CCXI-4 (0.45 g, 1.2 mmol) in DMF (10 mL) and $H_2O$ (1 mL) was added $Pd(PPh_3)_4$ (0.24 g, 0.2 mmol). The mixture was purged with nitrogen for 5 minutes and heated to 80° C. for 2 hours under $N_2$ protection. After being cooled to room temperature, the mixture was diluted with water (20 mL) and extracted with EtOAc (30 mL×3). The combined organic layers were washed with brine, dried over $Na_2SO_4$, and concentrated under reduced pressure. The residue was purified by column chromatography on silica gel (PE:EA=8:1-5:1) to give compound CCXI-5 (0.3 g, 57% yield).

Preparation of Compound 244

To a solution of compound CCXI-5 (0.1 g, 0.19 mmol) in methanol (2 mL) was added $LiOH \cdot H_2O$ (0.14 g, 3.33 mmol) and water (0.5 mL). The reaction mixture was stirred at room temperature overnight. The mixture was evaporated to remove methanol, and the residue was purified by prep-HPLC to give Compound 244 (20 mg, yield 20%). $^1H$ NMR ($CD_3OD$, 400 MHz) δ 7.70 (d, J=8.0 Hz, 2H), 7.61 (d, J=8.0 Hz, 4H), 7.56 (d, J=8.0 Hz, 2H), 7.49 (d, J=8.0 Hz, 2H), 7.32-7.18 (m, 4H), 7.23-6.98 (m, 1H), 2.35 (s, 3H), 1.55 (m, 2H), 1.38 (m, 2H), 1.25 (m, 2H), 1.13 (m, 2H).

Synthesis of Compound 245
Synthetic Route (Scheme CCXII)
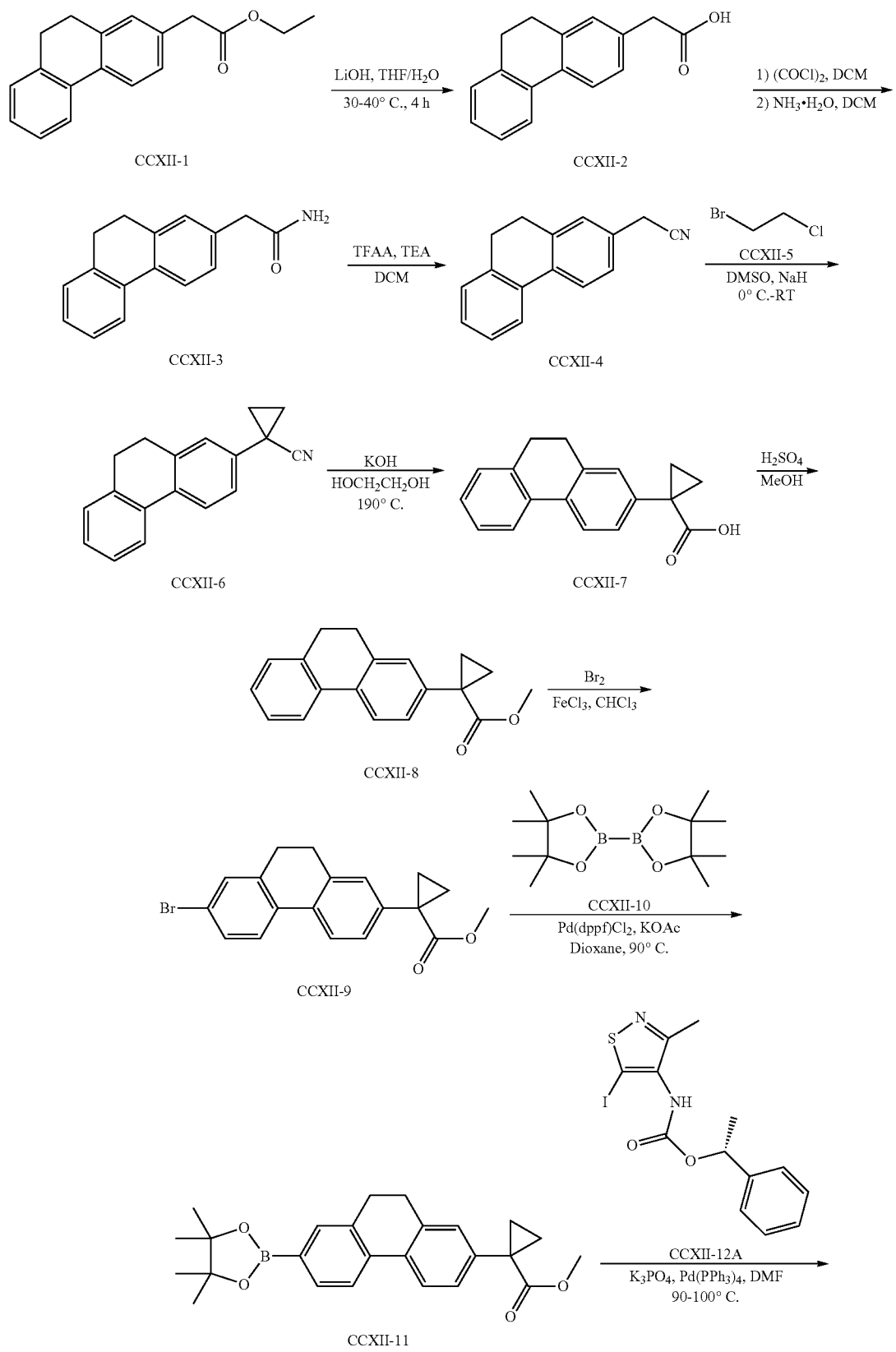

-continued

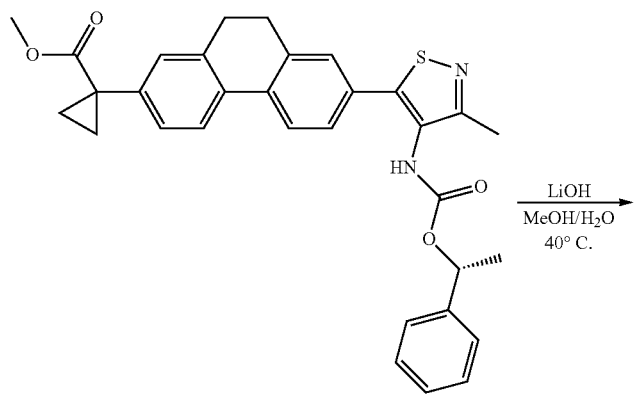

CCXII-13

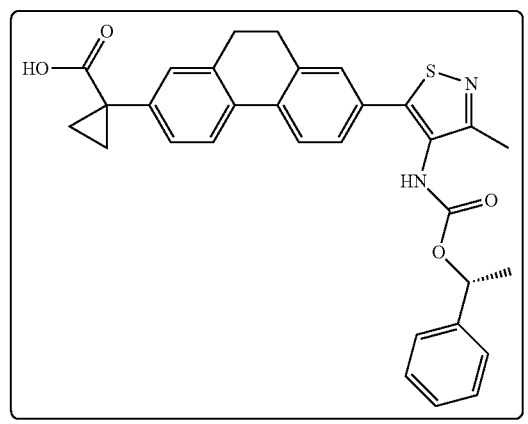

Compound 245

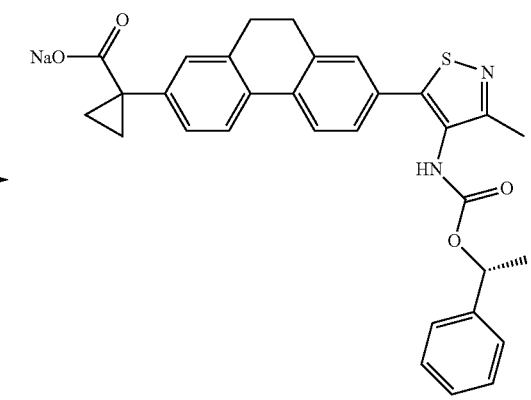

Compound 245a

The preparation of compound CCXII-1 was described in the synthesis of Compound 78 (XLIX-5).

To a solution of compound CCXII-1 (6 g, 22.6 mmol, 1 eq.) was added LiOH.H$_2$O (4.8 g, 112.8 mmol, 5 eq.) in 15 mL of water. The mixture was heated at 30-40° C. for 4 hrs. TLC (PE:EA=5:1) analysis showed the reaction completed. All the volatiles were removed under reduced pressure. The residual was diluted with water, adjusted pH=3-4 with aq. HCl (1 N), extracted with EtOAc (80 mL×3). The combined organic layer was washed with brine, dried over anhydrous sodium sulfate, filtered and concentrated to give light yellow solid (5.3 g, yield 99%).

To the solution of compound CCXII-2 (5.7 g, 23.9 mmol, 1 eq.) in 50 mL of DCM was added 3.4 mL of oxalyl chloride (adding a drop of DMF). The mixture was stirred for 18 h. All the volatiles were removed under reduced pressure. The residual was dried and used directly (6.1 g, 100%). The solid was dissolved in 30 mL of DCM and added into the solution of NH$_3$H$_2$O in DCM. The mixture was stirred for 18 h. LCMS analysis showed the reaction completed. All the volatiles were removed under reduced pressure. The residual were diluted with EtOAc (100 mL), washed with water and brine, dried over anhydrous sodium sulfate, filtered and concentrated to give white solid. (5 g, yield 87%).

To a solution of compound CCXII-3 (5 g, 21.1 mmol, 1 eq) in 80 mL of DCM was added TEA (9.6 g, 94.8 mmol, 4.5 eq.) and TFAA (12 g, 42.2 mmol, 2 eq). The mixture was stirred for 5 h at room temperature. TLC (PE:EA=5:1) analysis showed the reaction completed. All the volatiles were removed under reduced pressure. The residual were diluted with water, extracted with EtOAc (80 mL×3). The organic layer was washed with brine, dried over anhydrous sodium sulfate, filtered and concentrated to give crude compound CCXII-4 (4.6 g, yield 100%).

To a solution of compound CCXII-4 (6.6 g, 30.1 mmol, 1 eq) in 50 mL of DMSO was added NaH (60%, 3.0 g, 75.4 mmol, 2.5 eq) at 0° C. The suspension was stirred for 1 hour at room temperature. Compound CCXII-5 was added into the mixture at 0° C. The mixture was allowed to warm to room temperature, and stirred for another 18 h. TLC (PE:EA=10:1) analysis showed the reaction completed. The mixture was diluted with water, extracted with EtOAc (80 mL×3). The organic layer was washed with brine, dried over anhydrous sodium sulfate, filtered, concentrated and purified by column chromatography on silica gel (PE:EA=10:1) to give yellow solid CCXII-6 (3.8 g, yield 51%).

To a solution of compound CCXII-6 (1.5 g, 6.12 mmol, 1 eq) in 30 mL of ethylene glycol was added KOH (3.4 g, 61.2 mmol, 10 eq.). The mixture was sealed and heated at 190° C. for 72 h. TLC (PE:EA=3:1) analysis showed the reaction completed. The mixture was diluted with water, adjust pH=3-4 with HCl (1 N), extracted with EtOAc (30 mL×3). The combined organic layer was washed with brine, dried over anhydrous sodium sulfate, filtered and concentrated to give yellow solid CCXII-7 (1.3 g, yield 81%).

To a solution of compound CCXII-7 (0.76 g, 2.88 mmol, 1 eq.) in 12 mL of MeOH was added 2 mL of conc. $H_2SO_4$ at room temperature. The mixture was heated to reflux for 2 h. TLC (PE:EA=5:1) analysis showed the reaction completed. The mixture was cooled down to room temperature. The solvent was removed under reduced pressure; the residual was diluted with water, extracted with EtOAc (30 mL×3). The organic layer was washed with brine, dried over anhydrous sodium sulfate, filtered, concentrated to give compound CCXII-8 (0.77 g, yield 96%).

To a solution of compound CCXII-8 (870 mg, 3.12 mmol, 1 eq) in 15 mL of $CHCl_3$ was added $FeCl_3$ (76 mg, 0.47 mmol, 0.15 eq.) and $Br_2$ (500 mg, 3.12 mmol, 1 eq.) at 0° C. The mixture was stirred for 18 h. TLC (PE:EA=5:1) analysis showed the reaction completed. The mixture was diluted with EtOAc (100 mL), washed with water and brine. The organic layer was dried over anhydrous sodium sulfate, filtered, concentrated and purified by column chromatography on silica gel (PE:EA=5:1) to give compound CCXII-9 as yellow solid (0.93 g, yield 73%).

A flask was charged with compound CCXII-9 (1 g, 2.8 mmol, 1 eq.), compound CCXII-10 (0.78 g, 3.08 mmol, 1.1 eq.), KOAc (0.55 g, 5.6 mmol, 2 eq.), $Pd(dppf)Cl_2$ (0.21 g, 0.28 mmol, 0.1 eq.) and 25 mL of dioxane, and flushed with nitrogen for three times. The mixture was heated to reflux at 90° C. TLC analysis (PE:EA=5:1) showed the reaction completed. The reaction mixture was cooled down to room temperature. The solvent was removed under reduced pressure. The residue was diluted with water (15 mL), extract with EtOAc (30 mL×3). The combined organic layers was washed with brine, dried over anhydrous sodium sulfate, filtered and concentrated. Purification by column chromatography (PE:EA=5:1) affords compound CCXII-11 as light yellow solid (0.9 g, yield 82%).

A flask was charged with compound CCXII-11 (200 mg, 0.49 mmol, 1 eq.), compound CCXII-12A (200 mg, 0.51 mmol, 1.05 eq.), aq. $K_3PO_4$ (2 M, 0.5 mL, 1 mmol, 2 eq.), $Pd(PPh_3)_4$ (57 mg, 0.05 mmol, 0.1 eq.) and 7 mL of DMF and 2 mL of $H_2O$. The mixture was flushed with nitrogen for three minutes. The mixture was heated at 90-100° C. for 8 h. TLC analysis (PE:EA=3:1) showed the reaction completed. The reaction mixture was cooled down to room temperature. The solvent was removed under reduced pressure. The residue was diluted with water (10 mL), extracted with EtOAc (20 mL×3). The combined organic layers was washed with brine, dried over anhydrous sodium sulfate, filtered and concentrated. Purification by prep-TLC (PE:EA=3:1) gave compound CCXII-13 as light white solid (190 mg, yield 72%). MS (ESI) m/z $(M+H)^+$ 539.1.

Preparation of Compound 245

To a solution of compound CCXII-13 (150 mg, 0.28 mmol, 1 eq.) in 5 mL of MeOH was added $LiOH.H_2O$ (120 mg, 2.78 mmol, 10 eq.) in 1.5 mL of water. The solution was heated at 30-40° C. LCMS analysis showed the reaction completed. The mixture was cooled down to room temperature, adjusted pH=3-4 with aq. HCl (1 M), extracted with EtOAc (20 mL×3). The organic layer was washed with brine, dried over anhydrous sodium sulfate, filtered and concentrated. The crude compound was purified with prep-HPLC to yield Compound 245 (129.1 mg, yield 88%). $^1H$ NMR (DMSO-$d_6$, 400 MHz) δ 12.36 (s, 1H), 9.29 (s, 1H), 7.86 (d, J=8.0 Hz, 1H), 7.79 (d, J=8.0 Hz, 1H), 7.46-7.37 (m, 5H), 7.34-7.27 (m, 3H), 7.23-7.04 (m, 1H), 5.77 (q, J=6.4 Hz, 1H), 2.81 (m, 4H), 2.26 (s, 3H), 1.53 (d, J=6.4 Hz, 3H), 1.47 (m, 2H), 1.18 (m, 2H). (ESI) m/z $(M+H)^+$ 525.1.

Preparation of Compound 245a

To a solution of Compound 245a (115 mg, 0.22 mmol, 1 eq.) in 5 mL of MeOH was added aq. NaOH (0.1 M, 0.22 mL, 0.22 mmol). The mixture was stirred at r.t for 2 h. The solvent was removed under reduced pressure. The residue was dried to give the sodium salt Compound 245a as white solid. (119.7 mg, 100% yield). $^1H$ NMR (DMSO-$d_6$, 400 MHz) δ 9.28 (s, 1H), 7.81 (d, J=7.6 Hz, 1H), 7.66 (d, J=7.6 Hz, 1H), 7.41-7.33 (m, 6H), 7.20-7.16 (m, 3H), 5.77 (q, J=5.2 Hz, 1H), 2.77 (s, 4H), 2.26 (s, 3H), 1.54 (d, J=5.2 Hz, 3H), 1.17 (m, 2H), 0.68 (m, 2H). (ESI) m/z $(M+H)^+$ 525.1.

Synthesis of Compound 246

Synthetic Route (Scheme CCXIII)

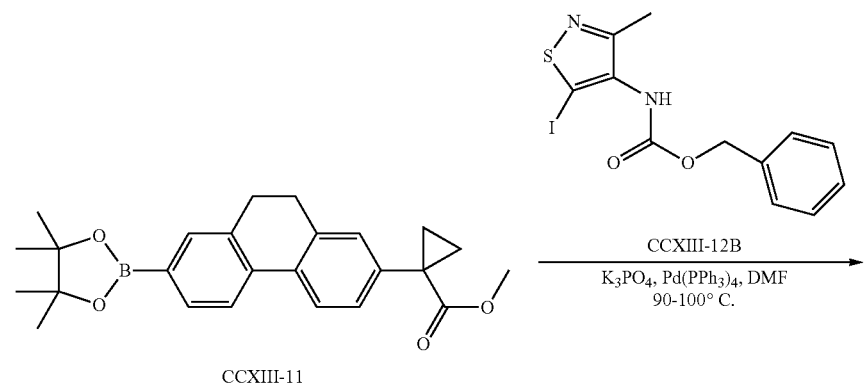

CCXIII-11

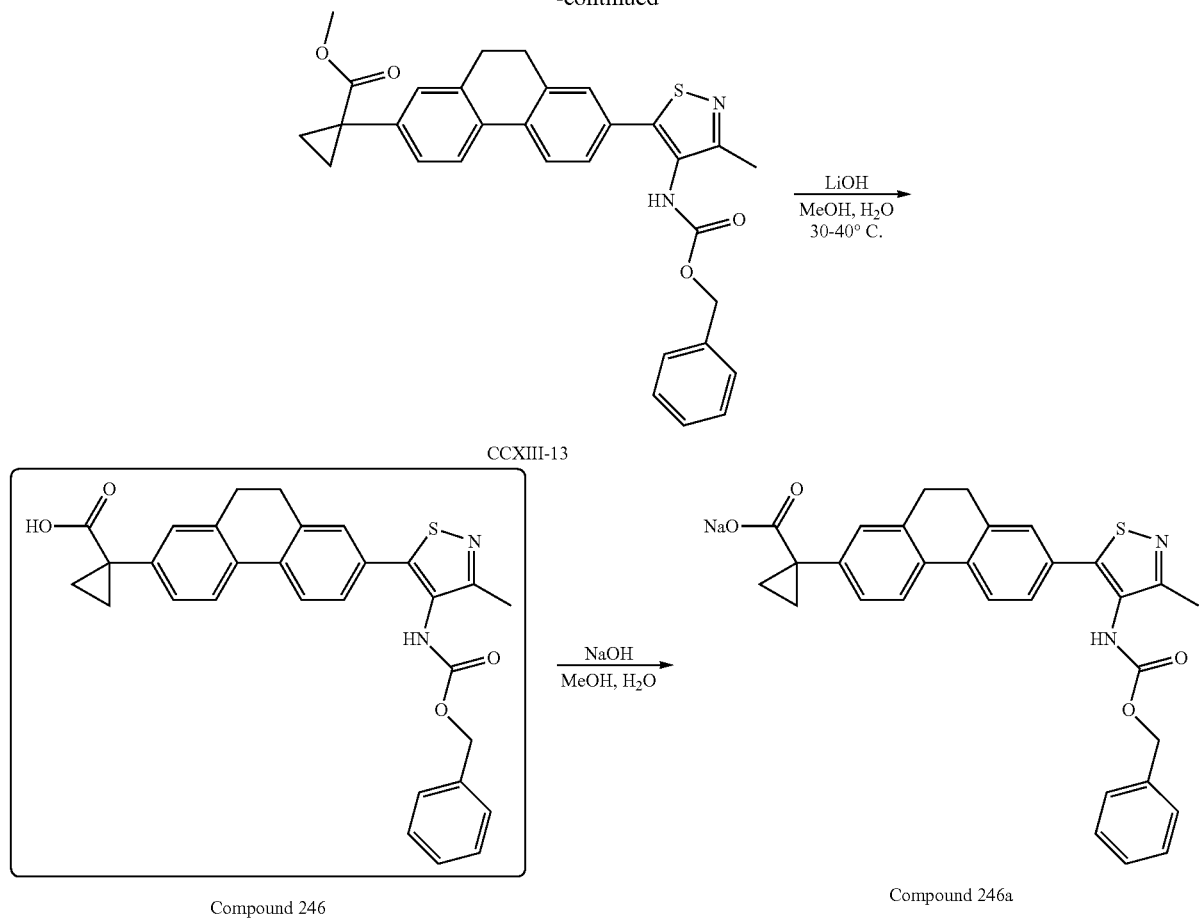

Compound 246   Compound 246a

The preparation of compound CCXIII-13 was followed the general procedure for preparation of compound CCXII-13 (70 mg, yield 53%). MS (ESI) m/z (M+H)$^+$ 525.1.

The preparation of Compound 246 was followed the general procedure for preparation of Compound 245. (52 mg, yield 76%). MS (ESI) m/z (M+H)$^+$ 511.0.

The preparation of Compound 246a was followed the general procedure for preparation of Compound 245a. (54 mg, yield 100%). $^1$H NMR (DMSO-d$_6$, 300 MHz) δ 9.27 (s, 1H), 7.80 (d, J=7.8 Hz, 1H), 7.64 (d, J=8.1 Hz, 1H), 7.43-7.37 (m, 6H), 7.17-7.14 (m, 3H), 5.12 (s, 2H), 2.75 (s, 4H), 2.25 (s, 3H), 1.16 (m, 2H), 0.67 (m, 2H). MS (ESI) m/z (M+H)$^+$ 511.0.

Synthesis of Compound 247

Synthetic Route (Scheme CCXIV)

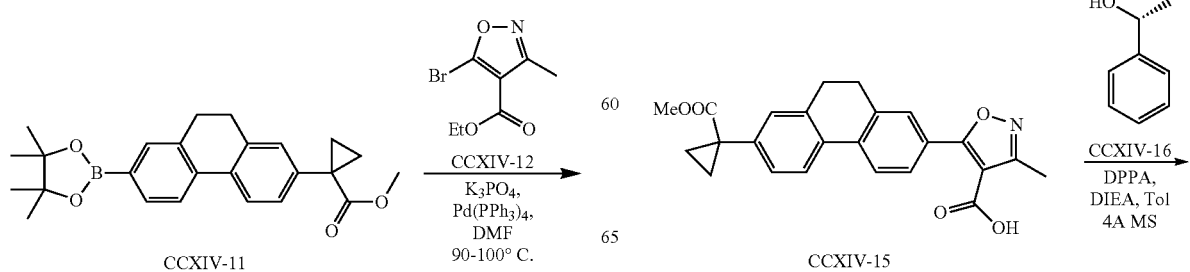

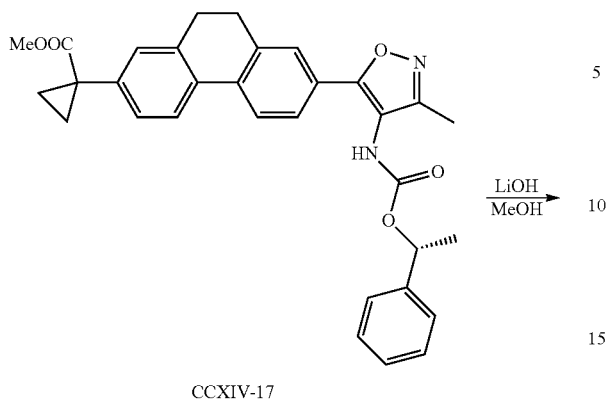

CCXIV-17

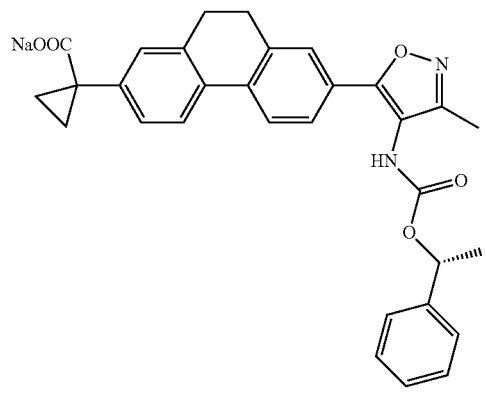

Compound 247a

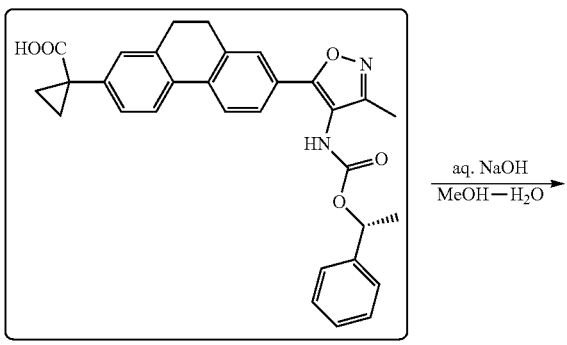

Compound 247

The preparation of compound CCXIV-13 was followed the general procedure for preparation of compound CCXIII-13 (180 mg, yield 42%). MS (ESI) m/z (M+H)+ 432.0.

The preparation of compound CCXIV-14 was followed the general procedure for preparation of Compound 245. (160 mg, yield 97%). $^1$H NMR (DMSO-d$_6$, 400 MHz) δ 7.95 (d, J=8.0 Hz, 1H), 7.87-7.79 (m, 3H), 7.29-7.25 (m, 2H), 2.92-2.84 (m, 4H), 2.41 (s, 3H), 1.45 (m, 2H), 1.18 (m, 2H). MS (ESI) m/z (M+H)+ 390.0.

Compound 247 was prepared analogously to the procedure described in the synthesis of Compound 78 (30 mg, yield 62%). MS (ESI) m/z (M+H)+ 509.1.

Compound 247a (30 mg, yield 62%). $^1$H NMR (DMSO-d$_6$, 300 MHz) δ 9.28 (s, 1H), 7.82 (d, J=7.2 Hz, 1H), 7.68-7.59 (m, 3H), 7.42-7.13 (m, 7H), 5.74 (q, J=7.2 Hz, 1H), 2.75 (s, 4H), 2.09 (s, 3H), 1.51 (d, J=7.2 Hz, 3H), 1.18 (m, 2H), 0.66 (m, 2H). MS (ESI) m/z (M+H)+ 509.2.

Synthesis of Compound 248

Synthetic Route (Scheme CCXV)

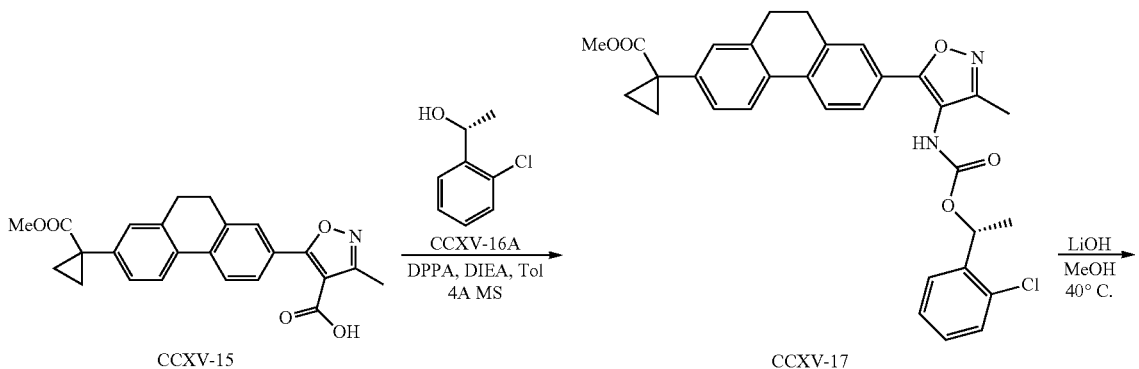

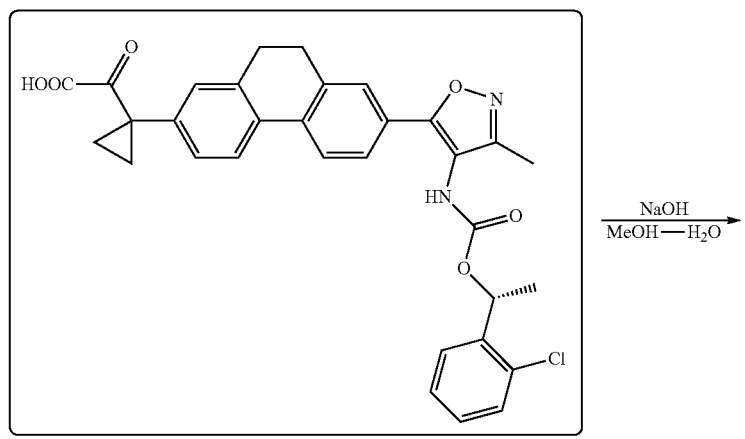

Compound 248

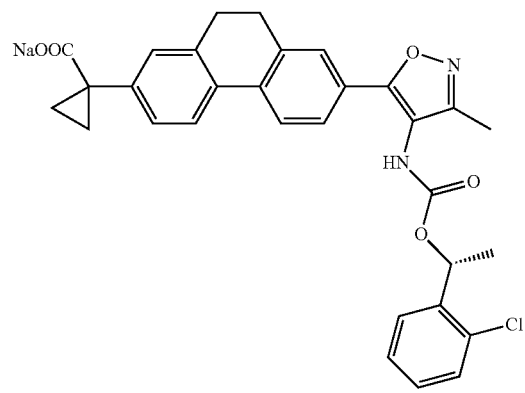

Compound 248a

The preparation of compound CCXV-17 was followed the general procedure for preparation of compound CCXIV-17. MS (ESI) m/z (M+H)+ 557.1.

Compound 248 was prepared analogously to the procedure described in the synthesis of Compound 78. MS (ESI) m/z (M+H)+ 543.0.

Compound 248a: $^1$H NMR (DMSO-$d_6$, 300 MHz): δ 9.40 (s, 1H), 7.79-7.63 (m, 5H), 7.45-7.28 (m, 3H), 7.20-7.12 (m, 2H), 5.98 (q, J=7.2 Hz, 1H), 2.76 (s, 4H), 2.08 (s, 3H), 1.47 (d, J=7.2 Hz, 3H), 1.17 (m, 2H), 0.68 (m, 2H). MS (ESI) m/z (M+H)+ 543.0.

Synthesis of Compound 249

Synthetic Route (Scheme CCXVI)

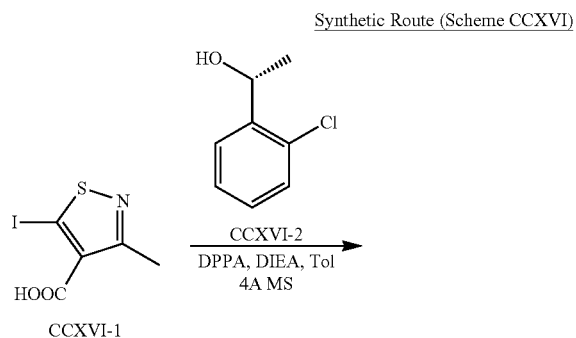

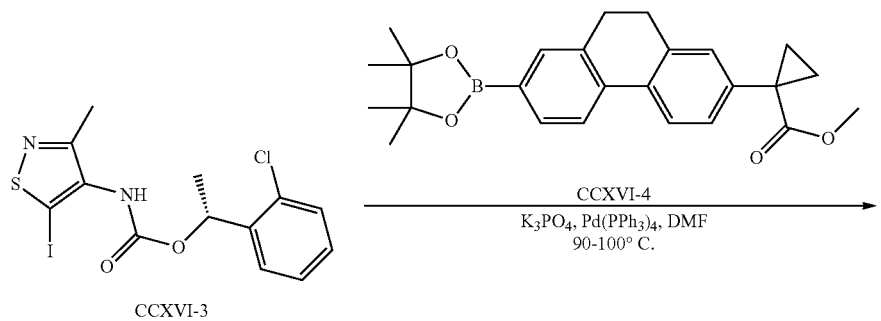

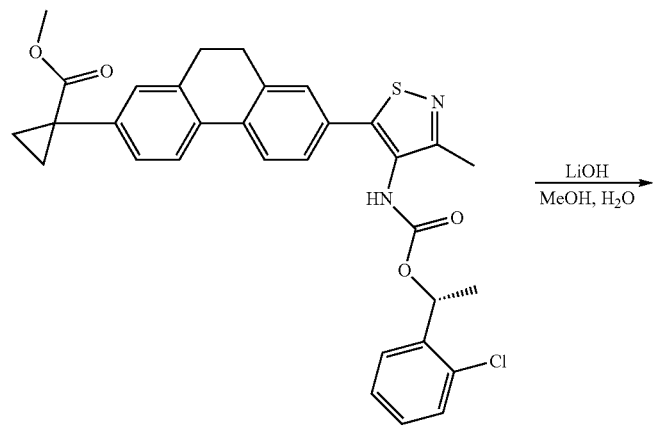

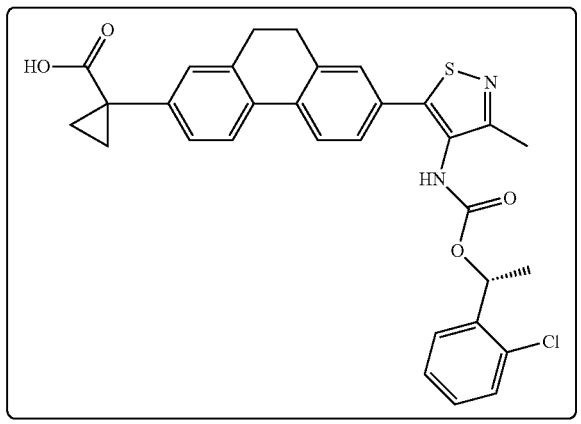

Compound 249

The preparation of compound CCXVI-3 was followed the general procedure for preparation of compound CCXIV-17 (840 mg, yield 76%). MS (ESI) m/z (M+H)⁺ 422.7.

The preparation of compound CCXVI-5 was followed the general procedure for preparation of compound CCXII-13. 80 mg, yield 56%. MS (ESI) m/z (M+H)⁺ 573.0.

The preparation of Compound 249 was followed the general procedure for preparation of Compound 245 (70 mg, yield 90%). $^1$H NMR (DMSO-d$_6$, 300 MHz) δ 12.34 (s, 1H), 9.38 (s, 1H), 7.85 (d, J=8.1 Hz, 1H), 7.77 (d, J=7.8 Hz, 1H), 7.56 (d, J=7.8 Hz, 1H), 7.47-7.23 (m, 7H), 5.96 (q, J=6.0 Hz, 1H), 2.79 (s, 4H), 2.22 (s, 3H), 1.50 (d, J=6.0 Hz, 3H), 1.44 (m, 2H), 1.15 (m, 2H). MS (ESI) m/z (M+Na)⁺ 581.0.

The preparation of sodium salt of Compound 249 (Compound 249a) was followed the general procedure for preparation of Compound 245a (60 mg, yield 43%). $^1$H NMR (DMSO-d$_6$, 400 MHz): δ 7.73 (d, J=7.2 Hz, 1H), 7.64 (d, J=8.0 Hz, 1H), 7.58-7.51 (m, 3H), 7.43-7.40 (m, 1H), 7.39-7.28 (m, 2H), 7.21-7.15 (m, 2H), 5.98 (q, J=6.4 Hz, 1H), 2.77 (s, 4H), 2.19 (s, 3H), 1.42 (d, J=6.4 Hz, 3H), 1.22 (m, 2H), 0.73 (m, 2H). MS (ESI) m/z (M+Na)⁺ 581.0.

Synthesis of Compound 250

Synthetic Route (Scheme CCXVII)

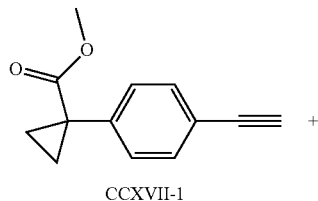

CCXVII-1

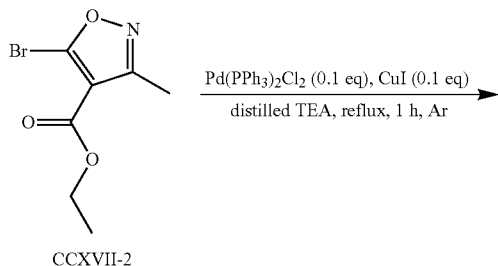

CCXVII-2

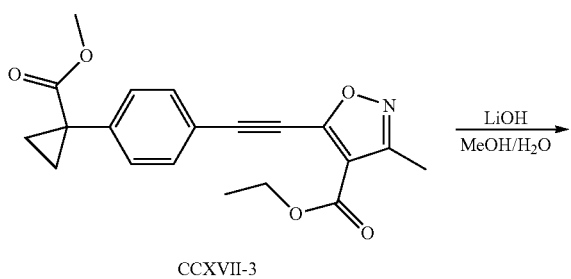

CCXVII-3

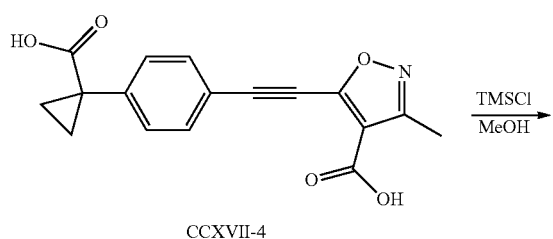

CCXVII-4

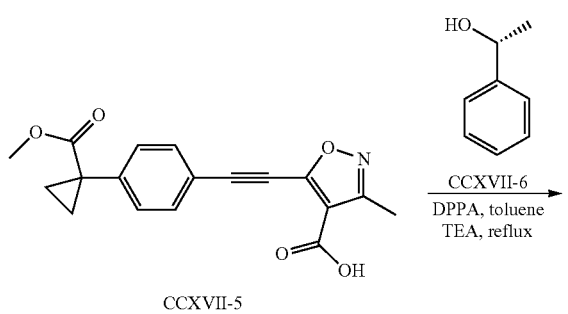

CCXVII-5

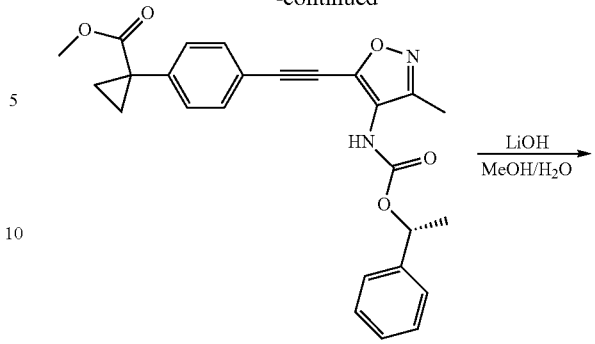

CCXVII-7

Compound 250

The preparation of CCXVII-1 was described in the synthesis of Compound 81 (intermediate LII-8).

To a mixture of compound CCXVII-1 (400 mg, 2 mmol) and compound CCXVII-2 (468 mg 2 mmol) in distilled TEA (15 mL) was added CuI (38 mg, 0.2 mmol) and Pd(PPh$_3$)$_2$Cl$_2$ (140 mg, 0.2 mmol). The mixture was purged with argon for three times, and then it was heated to reflux under argon for 1 hour. After being cooled to room temperature, the mixture was diluted with water (20 mL) and extracted with EtOAc (30 mL×3). The combined organic layers were washed with brine, dried over Na$_2$SO$_4$, and concentrated under reduced pressure. The residue was purified by column chromatography on silica gel (PE/EA=5/1) to afford compound CCXVII-3 (250 mg, 35% yield). MS (ESI) m/z (M+H)$^+$ 353.9.

To a solution of compound CCXVII-3 (0.26 g, 0.74 mmol) in methanol (20 mL) and water (5 mL) was added LiOH.H$_2$O (0.15 g, 3.68 mmol). The reaction mixture was stirred at room temperature overnight. The mixture was concentrated, and then the residue was acidified with aq. HCl (2 M) to pH=5~6 and extracted with EA (30 mL×3). The combined organic layer was washed with brine, dried over anhydrous Na$_2$SO$_4$ and concentrated to afford the crude compound CCXVII-4, which was used directly for next step.

To a solution of compound CCXVII-4 (0.13 g, 0.42 mmol) in methanol (20 mL) was added TMSCl (0.09 g, 0.84 mmol) at room temperature. The reaction mixture was stirred at room temperature overnight. The mixture was evaporated to dryness, and the residue CCXVII-5 was used directly for next step.

To a solution of compound CCXVII-5 (60 mg, 0.18 mmol) and compound CCXVII-6 (34 mg, 0.27 mmol) in toluene (3 mL) was added DPPA (0.075 g, 0.27 mmol) and TEA (0.036 g, 0.36 mmol). The reaction mixture was stirred at reflux under N$_2$ overnight. The mixture was evaporated and the residue was purified by preparative-HPLC to give the desired compound CCXVII-7 (6 mg, 7% yield).

Preparation of Compound 250

To a solution of compound CCXVII-7 (6 mg, 0.013 mmol) in methanol (1 mL) was added LiOH.H$_2$O (21 mg, 0.5 mmol) and water (0.2 mL). The reaction mixture was stirred at room temperature overnight. The mixture was evaporated to remove methanol, and the residue was purified by preparative-HPLC to give Compound 250 (4 mg, 69% yield). $^1$H NMR (CDCl$_3$, 400 MHz) δ 7.46-7.42 (m, 2H), 7.39-7.26 (m, 7H), 5.87 (q, J=6.8 Hz, 1H), 2.24 (s, 3H), 1.60 (m, 2H), 1.59 (d, J=6.4 Hz, 3H), 1.28 (m, 2H). MS (ESI) m/z (M+H)$^+$ 431.0.

Synthesis of Compound 251

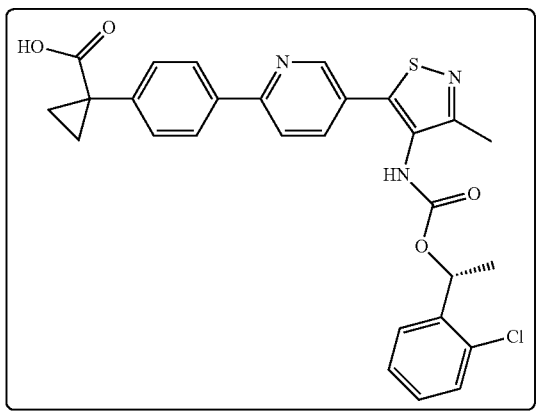

Compound 251

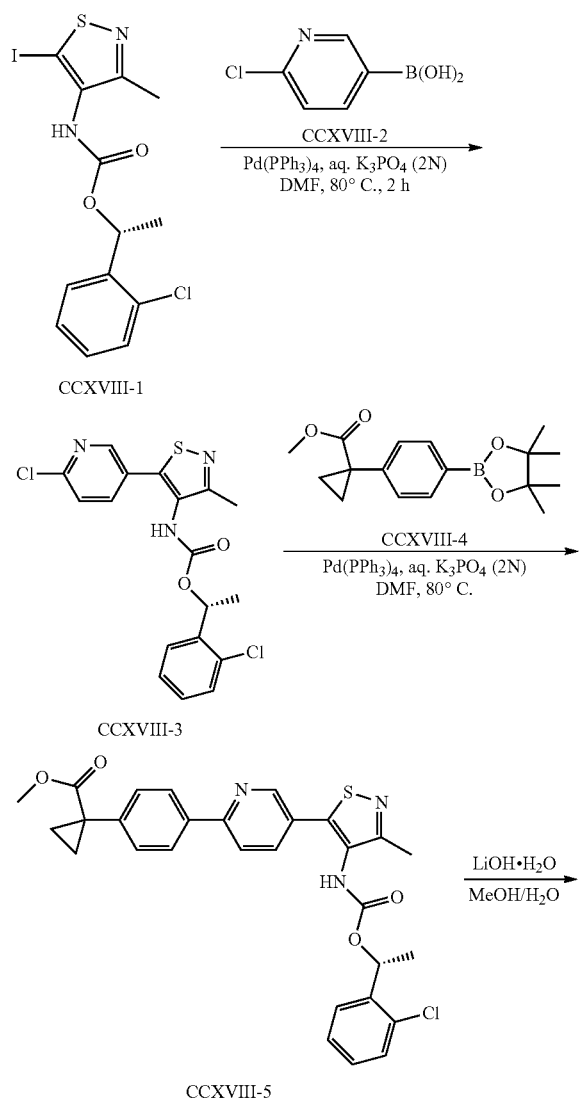

A flask was charged with compound CCXVIII-1 (100 mg, 0.23 mmol), compound CCXVIII-2 (52.3 mg 0.25 mmol) and DMF (2 mL), followed by addition of aq. K$_3$PO$_4$ (2 M, 0.12 mL, 0.24 mmol) and Pd(PPh$_3$)$_4$ (55 mg, 0.046 mmol). The mixture was heated at 80° C. overnight. After being cooled to r.t, the reaction mixture was diluted with EtOAc (90 mL), washed with brine, dried over Na$_2$SO$_4$ and concentrated. The residue was purified by prep-TLC (PE/EA=1/1) to afford compound CCXVIII-3 (68 mg, 73% yield). MS (ESI) m/z (M+H)$^+$ 408.1.

A flask was charged with compound CCXVIII-3 (68 mg, 0.167 mmol), compound CCXVIII-4 (25 mg 0.083 mmol) and DMF (2 mL), followed by addition of aq. K$_3$PO$_4$ (2 M, 0.09 mL, 0.18 mmol) and Pd(PPh$_3$)$_4$ (17 mg, 0.033 mmol). The mixture was heated at 80° C. overnight. After being cooled to r.t, the reaction mixture was diluted with EtOAc (50 mL), washed with brine, dried over Na$_2$SO$_4$ and concentrated. The residue was purified by prep-TLC (PE/EA=1/1) to afford compound CCXVIII-5 (36 mg, 39% yield). MS (ESI) m/z (M+H)$^+$ 548.1.

Preparation of Compound 251

Compound CCXVIII-5 (36 mg, 0.066 mmol) and LiOH.H$_2$O (13.8 mg, 0.330 mmol) was added into 10 mL of MeOH/H$_2$O (v:v=4:1). The mixture was stirred at 40° C. overnight. The mixture was concentrated, diluted with water, acidified with aq. HCl (1 M) to pH ~6, and extracted with EtOAc (20 mL×3). The combined organic layer was washed with brine, dried over anhydrous Na$_2$SO$_4$, and concentrated in vacuo. The residue was purified by prep-HPLC to yield Compound 251 (15.2 mg, 43% yield). $^1$H NMR (DMSO-d$_6$, 400 MHz) δ 9.45 (s, 1H), 8.55 (s, 1H), 8.13 (d, J=7.6 Hz, 2H), 7.84 (d, J=8.0 Hz, 1H), 7.72-7.69 (m, 1H), 7.63-7.55 (m, 3H), 7.46-7.39 (m, 2H), 7.35-7.30 (m, 1H), 5.96 (d, J=6.8 Hz, 2H), 2.24 (s, 3H), 1.52 (d, J=6.0 Hz, 3H), 1.25-1.21 (m, 2H), 0.79-0.76 (m, 2H). MS (ESI) m/z (M+H)+ 534.1.

Synthesis of Compound 252

Synthetic Route (Scheme CCXIX)

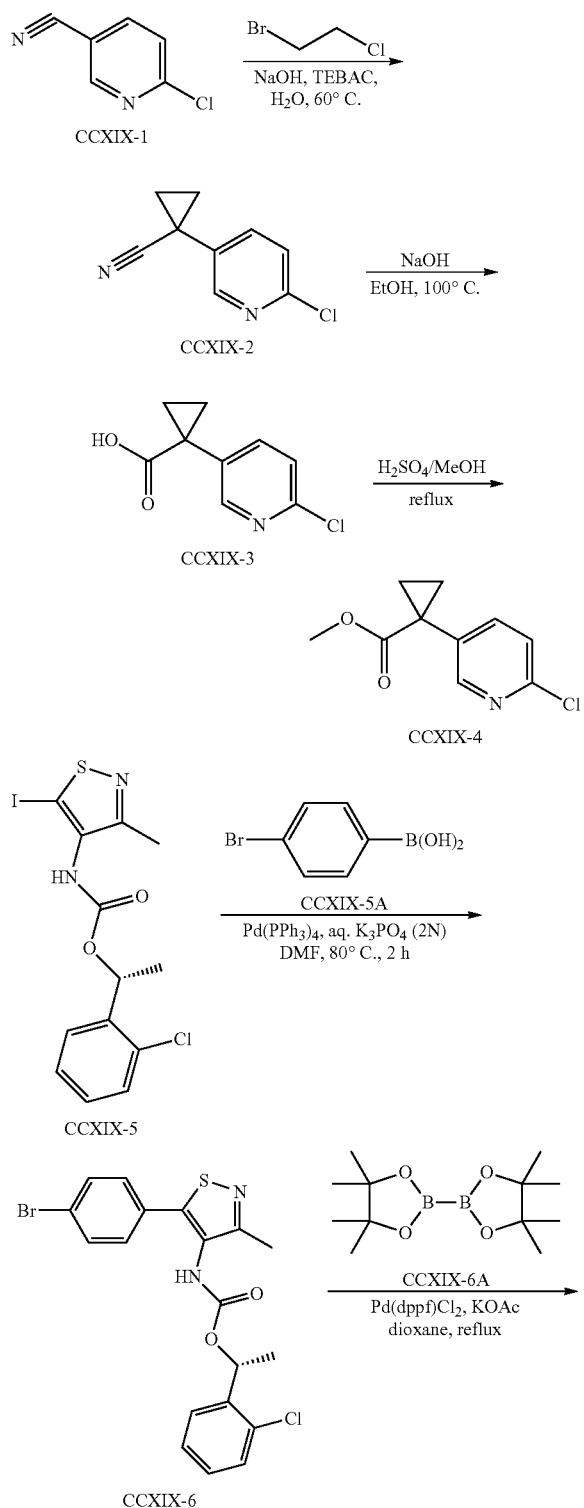

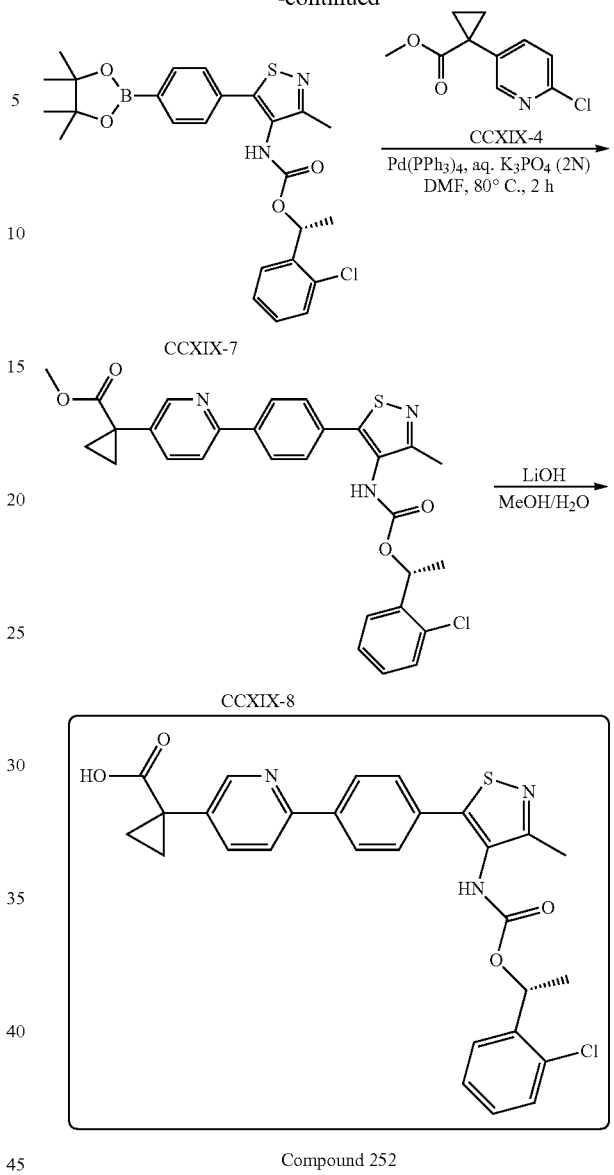

Compound CCXIX-1 (6.1 g, 0.04 mol) was added into a mixture of aq. NaOH (50%, 9.9 mL) and TEBAC (273 mg). Then 1-bromo-2-chloroethane (5.3 mL, 44 mmol) was added. The mixture was heated at 50° C. overnight. After cooled to r.t, the reaction mixture was extracted with EtOAc (30 mL×3). The combined organic phase was washed with brine, dried over $Na_2SO_4$ and concentrated. The residue was purified by column chromatograph (PE/EA=3/1) to give compound CCXIX-2 (6.4 g, 89% yield).

The mixture of compound CCXIX-2 (1.06 g, 0.006 mol), EtOH (12 mL) and aq. NaOH (25%, 6 mL) was heated at 100° C. overnight. After cooled to r.t, the reaction mixture was extracted with EtOAc (30 mL×3). The combined organic phase was washed with brine, dried over $Na_2SO_4$ and concentrated to afford crude compound CCXIX-3 (1.01 g, 86% yield), which was used directly for next step.

To a solution of compound CCXIX-3 (1.3 g, 6.9 mmol) in MeOH (20 mL) was added $H_2SO_4$ (5 mL) dropwise. The reaction mixture was refluxed overnight. The reaction mixture was concentrated, diluted with EtOAc (100 mL), washed with saturated aq. NaHCO$_3$ and brine, dried over Na$_2$SO$_4$ and concentrated. The residue was purified by column chromatograph (PE/EA=3/1) to give compound CCXIX-4 (1.21 g, 83% yield).

The mixture of compound CCXIX-5 (100 mg, 0.23 mmol), compound CCXIX-5A (52.3 mg, 0.30 mmol), K$_3$PO$_4$ (55 mg, 0.47 mmol) and Pd(PPh$_3$)$_4$ (55 mg, 0.046 mmol) in DMF (3 mL) was heated at 80° C. overnight under N$_2$ protection. After cooled to r.t, the reaction mixture was diluted with water (10 mL), extracted with EtOAc (30 mL×3). The combined organic phase was washed with brine, dried over Na$_2$SO$_4$ and concentrated. The residue was purified by prep-TLC (PE/EA=2/1) to give compound CCXIX-6 (35 mg, 33% yield). MS (ESI) m/z (M+H)$^+$ 452.7.

The mixture of compound CCXIX-6 (70 mg, 0.15 mmol), compound CCXIX-6A (40 mg 0.15 mmol), KOAc (30.4 mg, 0.30 mmol) and Pd(dppf)Cl$_2$ (17 mg, 0.023 mmol) in DMF (3 mL) was heated to 80° C. overnight under N$_2$ protection. After cooled to r.t, the reaction mixture was diluted with water (10 mL), extracted with EtOAc (20 mL×3). The combined organic phase was washed with brine, dried over Na$_2$SO$_4$ and concentrated. The residue was purified by prep-TLC (PE/EA=2/1) to give compound CCXIX-7 (35 mg, 45% yield). MS (ESI) m/z (M+H)$^+$ 498.9.

The mixture of compound CCXIX-7 (20 mg, 0.04 mmol), compound CCXIX-4 (10.15 mg, 0.048 mmol), aq. K$_3$PO$_4$ (2 M, 0.04 mL, 0.08 mmol) and Pd(PPh$_3$)$_4$ (5 mg, 0.008 mmol) in DMF (2 mL) was heated to 80° C. overnight under N$_2$ protection. After cooled to r.t, the reaction mixture was diluted with water (10 mL), extracted with EtOAc (20 mL×3). The combined reaction mixture was washed with brine, dried over Na$_2$SO$_4$ and concentrated. The residue was purified by prep-TLC (PE/EA=2/1) to give compound CCXIX-8 (15 mg, 68% yield). MS (ESI) m/z (M+H)$^+$ 547.9.

Preparation of Compound 252

Compound CCXIX-8 (15 mg, 0.027 mmol) and LiOH.H$_2$O (10.0 mg, 0.27 mmol) was added into 10 mL of MeOH/H$_2$O (v/v=4/1). The mixture was stirred at 40° C. overnight. Then the mixture was concentrated, diluted with water (2 mL), acidified with aq. HCl (1 M) to pH~5-6, and extracted with EtOAc (20 mL×3). The combined organic layer was washed with brine, dried over anhydrous Na$_2$SO$_4$, and concentrated in vacuo. The residue was purified by prep-HPLC to give Compound 252 (10.3 mg, 70.5% yield). $^1$H NMR (CD$_3$OD, 400 MHz) δ 8.64 (s, 1H), 8.04 (d, J=8.0 Hz, 2H), 7.92-7.85 (m, 2H), 7.70-7.55 (m, 3 H), 7.38-7.32 (m, 2H), 7.29-7.23 (m, 1H), 6.11 (q, J=6.4 Hz, 1H), 2.34 (s, 3H), 1.69 (m, 2H), 1.55 (d, J=6.4 Hz, 3H), 1.28 (m, 2H). MS (ESI) m/z (M+H)$^+$ 534.1.

Synthesis of Compound 253

Synthetic Route (Scheme CCXX)

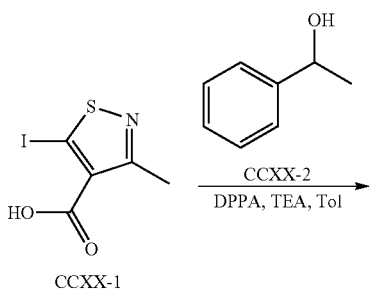

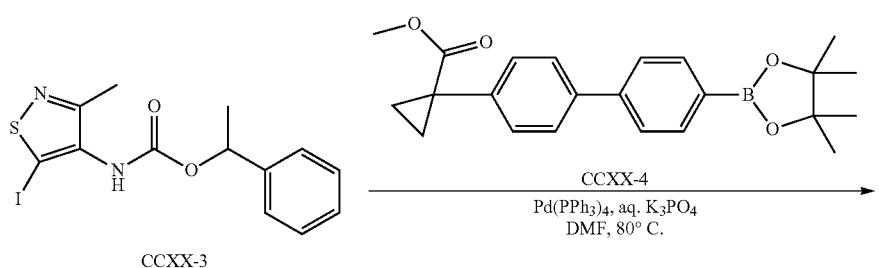

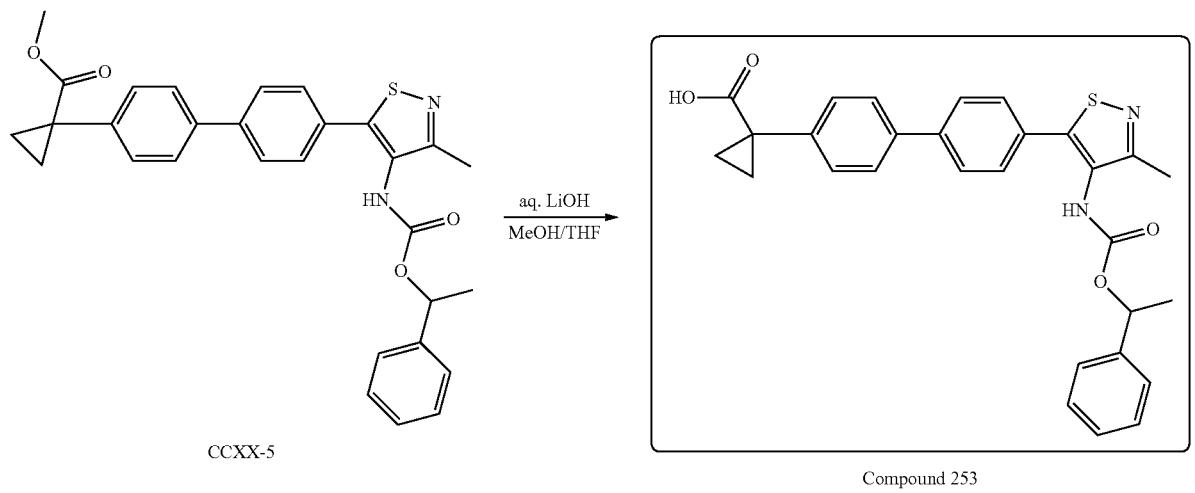
CCXX-5
Compound 253
Compound 253 was prepared analogously to the procedure described in the synthesis of Compound 44. $^1$H NMR (DMSO-d$_6$, 400 MHz) δ 9.32 (s, 1H), 7.71 (d, J=4.4 Hz, 2H), 7.61-7.53 (m, 4H), 7.42-7.30 (m, 6H), 7.23-6.99 (m, 1H), 5.75 (d, J=6.4 Hz, 1H), 2.26 (s, 3 H), 1.57-1.51 (m, 2H), 1.30 (s, 3 H), 0.88-0.84 (m, 2H). MS (ESI) m/z [M+H]$^+$ 498.9.
Synthesis of Compound 254
Synthetic Route (Scheme CCXXI)
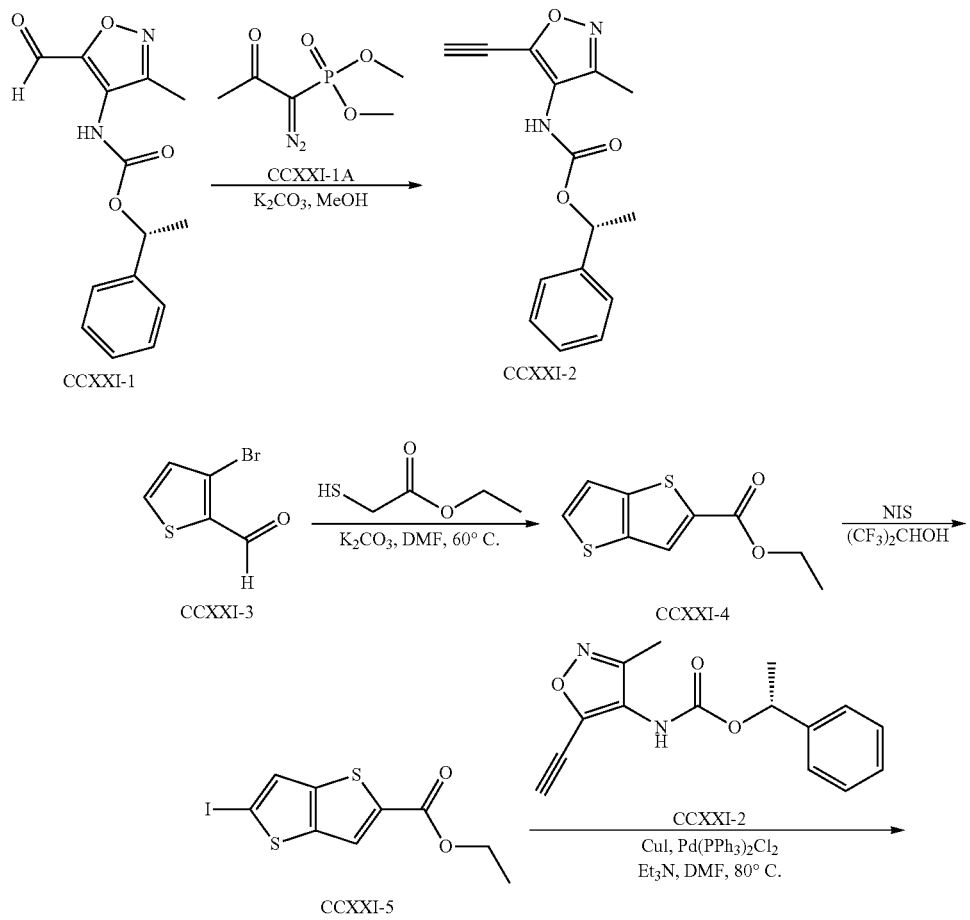

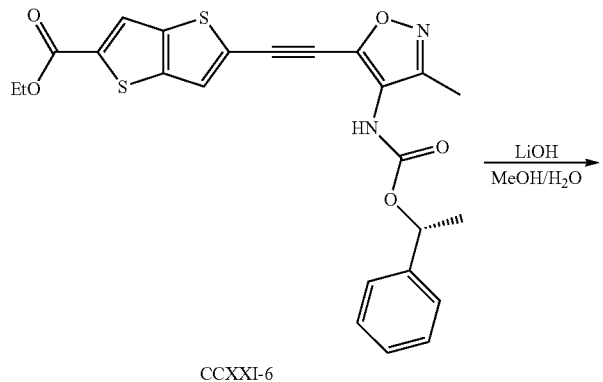

CCXXI-6

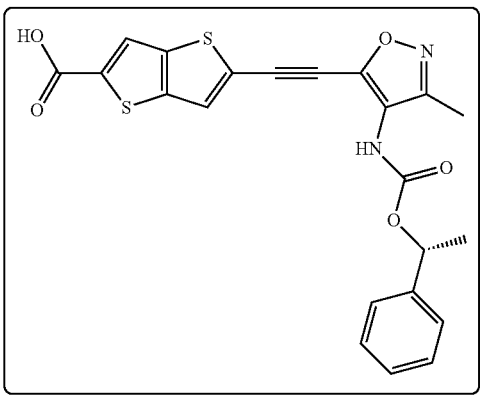

Compound 254

To a solution of compound CCXXI-1 (200 mg, 0.73 mmol) in methanol (10 mL) was added compound CCXXI-1A (168 mg, 0.87 mmol) and $K_2CO_3$ (201 mg, 1.46 mmol) at 0° C. The mixture was stirred at r.t for 12 hrs and then concentrated under reduced pressure. The mixture was acidified with sat. aq. citric acid to pH=5-6, extracted with EtOAc (30 mL×3). The combined organic layer was washed with brine, dried over anhydrous $Na_2SO_4$ and concentrated. The crude product was purified by prep-TLC (PE/EA=2/1) to yield compound CCXXI-2 (120 mg, 60% yield) as a pale yellow solid.

Compound CCXXI-3 (3.5 g, 18 mmol), ethyl thioglycolate (2.1 mL, 18 mmol) and $K_2CO_3$ (10.5 g, 73 mmol) was added into 15 mL of anhydrous DMF. The mixture was stirred at 60° C. overnight under $N_2$ protection. Then the mixture was diluted with $H_2O$ (10 mL), extracted with EA (30 mL×3). The combined organic layer was washed with brine, dried over anhydrous $Na_2SO_4$ and concentrated. The residue was purified by column chromatography on silica gel (PE/EA=20/1) to give compound CCXXI-4 (3.2 g, 82% yield). MS (ESI) m/z $(M+H)^+$ 213.0.

Compound CCXXI-4 (570 mg, 2.69 mmol), NIS (640 mg, 3.23 mmol) was added into 10 mL of $(CF_3)_2CHOH$. The mixture was stirred under $N_2$ at r.t. in the dark overnight. The solution was diluted with $H_2O$, extracted with EA (10 mL×3), the organic layer was washed with water, brine, dried over anhydrous $Na_2SO_4$ and concentrated, the residue was purified by column chromatograph (PE:EA=20:1) to give compound CCXXI-5 (506 mg, 78% yield). MS (ESI) m/z $(M+H)^+$ 338.9.

Compound CCXXI-5 (93.8 mg, 0.28 mmol), $Pd(PPh_3)_2Cl_2$ (13 g, 0.019 mmol) and CuI (4 mg, 0.021 mmol) were added into DMF (0.6 mL) and $Et_3N$ (1.8 mL). Phenylacetylene (1.9 mg, 0.019 mmol) was added to this mixture under $N_2$ atmosphere at r.t. for 5 min. Then a solution of compound CCXXI-2 (50 mg, 0.19 mmol) in DMF (0.3 ml) and $Et_3N$ (0.9 ml) was added slowly at r.t. Then the mixture was stirred at 80° C. for 2 h, TLC showed complete reaction. The mixture was concentrated, the residue was purified by prep-HPLC to give compound CCXXI-6 (55 mg, yield 62%). MS (ESI) m/z $(M+H)^+$ 481.1.

Preparation of Compound 254

To a solution of compound CCXXI-6 (50 mg, 0.10 mmol) in $MeOH/H_2O$ (v/v=4:1, 8 mL) was added $LiOH·H_2O$ (43.7 mg, 1.06 mmol). The reaction mixture was stirred at r.t. overnight. The solvent was removed in vacuo and the residue was acidified to pH~5 with aq. HCl (1 M), extracted with ethyl acetate (20 mL×3). The combined organic phase was washed with brine, dried over anhydrous $Na_2SO_4$, filtered and evaporated to afford a crude product, which was purified by prep-HPLC to give Compound 254 (45 mg, 95% yield). $^1H$ NMR (DMSO-$d_6$, 400 MHz) δ 9.51 (brs, 1H), 7.70 (s, 1H), 7.56 (s, 1H), 7.42-7.33 (m, 5H), 7.31-7.26 (m, 1H), 5.77 (q, J=6.4 Hz, 2H), 2.16 (s, 3H), 1.52 (d, J=6.4 Hz, 3H). MS (ESI) m/z $(M+H)^+$ 452.9.

Synthesis of Compound 255

Synthetic Route (Scheme CCXXII)

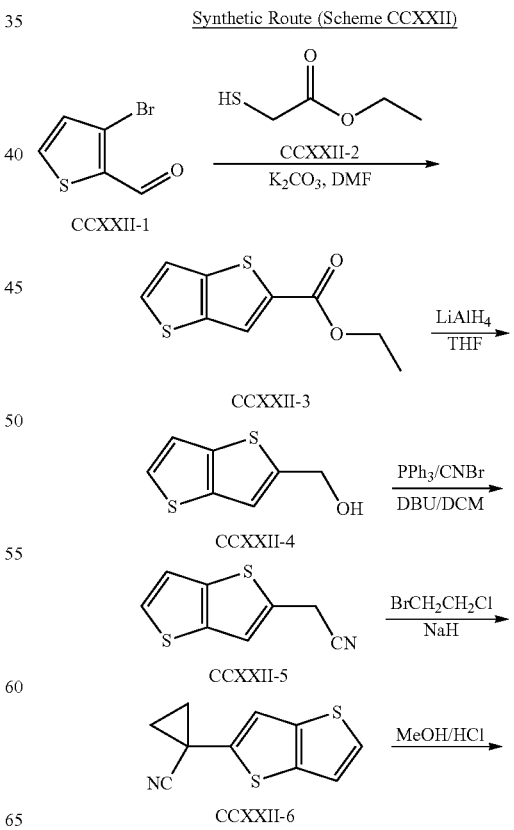

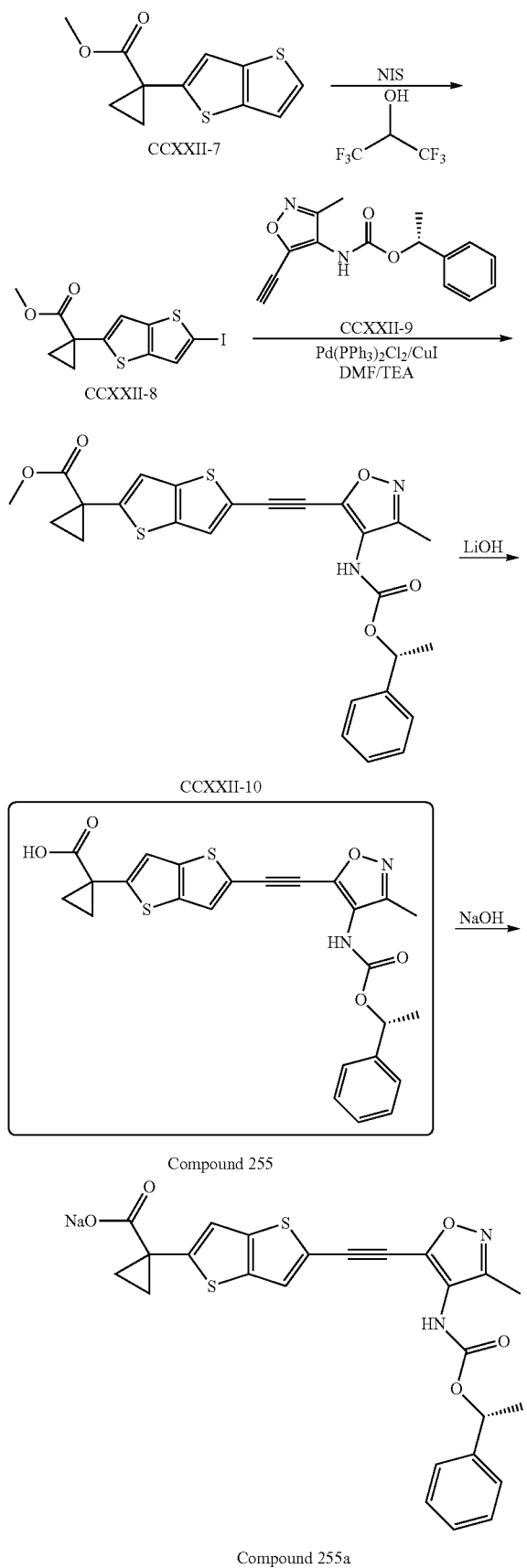

Compound CCXXII-3 was prepared according to the procedure described in the synthesis of compound CCXXI-4.

To a stirred solution of LAH (4.0 g, 100 mmol) in THF (70 mL) was added compound CCXXII-3 (7.7 g, 40.3 mmol, in 80 mL THF) dropwise at 0° C. under nitrogen. After the addition, the solution was stirred for 2 hours, then H$_2$O (4 mL) and NaOH (aq, 15% in water) was added. The mixture was warmed slowly to the room temperature, and stirred for 1.5 h. After filtered, the filtrate concentrated in vacuo to give compound CCXXII-4 (5.40 g, yield 79.8%).

To a stirred solution of compound CCXXII-4 (1.0 g, 6.05 mmol) and CNBr (0.73 g, 9.3 mmol) in DCM (20 mL) was added PPh$_3$ (1.50 g, 13.6 mmol). The solution was stirred for 2 hours and then DBU (1.03 g, 0.63 mmol) was added. The solution was stirred for 2 hours at room temperature. After being diluted with water (25 mL), the mixture was extracted with EtOAc (30 mL×3), the combined organic layer was washed with water, dried over Na$_2$SO$_4$, and concentrated in vacuo to give crude product, which was purified by column chromatography on silica gel (PE:EA=10:1) to afford compound CCXXII-5 (210 mg, yield 19.5%).

To a stirred solution of compound CCXXII-5 (210 mg, 1.17 mmol) in 10 mL of DMSO was added NaH (117 mg, 2.92 mmol) at ° C. The solution was stirred for 1 hour and BrCH$_2$CH$_2$Cl (185 mg, 1.29 mmol) was added. The reaction mixture was stirred for 1.5 h. After quenched with water. The mixture was extracted with DCM (30 mL×3). The combined organic layer was washed with brine, dried over Na$_2$SO$_4$, concentrated to get residue which purified by prep. TLC (PE:EA=10:1) to afford compound CCXXII-6 (150 mg, yield: 62.7%).

The mixture of compound CCXXII-6 (150 mg, 0.73 mmol) in HCl/MeOH (30 mL) was heated to reflux for 2 h. After concentrated, water (50 mL) was added, and extracted with EtOAc (40 mL×3). The combined organic layers were washed with brine (10 mL×2), and concentrated under reduced pressure to give residue which was purified by prep. TLC (PE:EA=5:1) to afford compound CCXXII-7 (75 mg, yield: 43.1%).

To a solution of compound CCXXII-7 (70 mg, 0.29 mmol) in 1,1,1,3,3,3-hexafluoropropan-2-ol (10 mL) was added NIS (72.5 mg, 0.32 mmol) at r.t. The reaction mixture was stirred at r.t. overnight. Then the mixture was diluted with water (20 mL) and extracted with EtOAc (30 mL×3). The combined organic layers were washed with brine (20 mL), and concentrated under reduced pressure. The residue was purified by prep. TLC (PE:EA=10:1) to give compound CCXXII-8 (36.4 mg, yield: 34.5%).

Compound 255 was prepared analogously to the procedure described in the synthesis of Compound 254 (35.0 mg, yield 79%). MS (ESI) m/z (M+H)$^+$ 493.0.

Compound 255a. $^1$H NMR (Methanol-d$_4$, 400 MHz): δ 7.44 (s, 1H), 7.26-7.38 (m, 5H), 7.21 (s, 1H), 5.81-5.83 (q, 1H), 2.19 (s, 3H), 1.74-1.77 (m, 2H), 1.57 (d, J=6.4 Hz, 3H), 1.43-1.46 (m, 2H). MS (ESI) m/z (M+H)$^+$ 493.0.

Syntheses of Compounds 256-264

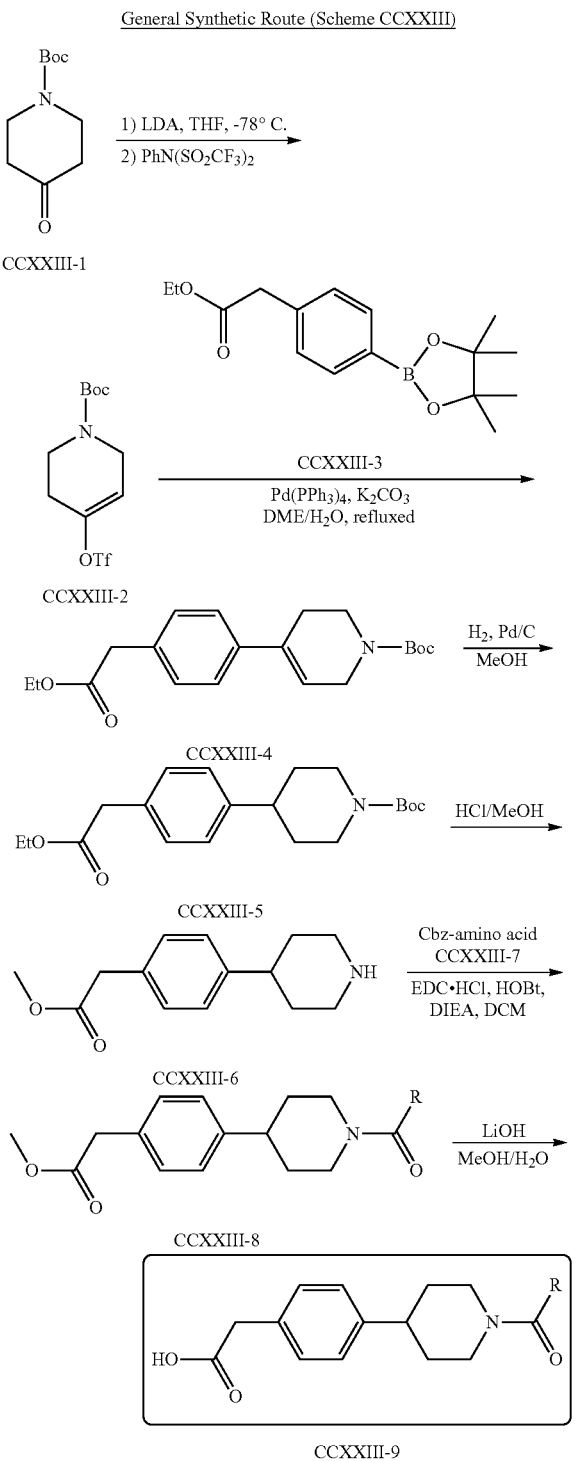

To a solution of compound CCXXIII-1 (10 g, 50 mmol) in dry THF (100 ml) was added LDA solution (1 M, 60 mL, 60 mmol) dropwise at −78° C. under nitrogen over a period of 50 min. The resulting solution was stirred at −78° C. for 30 min, and then a solution of PhN(SO₂CF₃)₂ (19.7 g, 55 mmol) in dry THF (70 mL) was added at −78° C. over another 50 min. Finally reaction mixture was allowed to warm to room temperature overnight. The solution was quenched with sat.aq. K₂CO₃ solution, extracted with EtOAc (100 mL×3), the combined organic layer was washed with brine, dried over sodium sulfate and concentrated to afford crude compound CCXXIII-2 (15.26 g, 92% yield) as a yellow liquid.

To a stirred mixture of compound CCXXIII-2 (12 g, 36 mmol), boronic ester CCXXIII-3 (11.5 g, 39.6 mmol) and K₂CO₃ (5.5 g, 39.6 mmol) in DME/H₂O (50 mL, v/v=9/1) was added Pd(PPh₃)₄ (2 g, 1.8 mmol). The mixture was purged with nitrogen for three times and then heated to reflux overnight. The mixture was concentrated, diluted with H₂O, extracted with EtOAc (100 mL×3), the organic layer was washed with water and brine, dried over anhydrous Na₂SO₄, and concentrated in vacuo, the residue was purified by flash column chromatography (PE) to give compound CCXXIII-4 (4.5 g, yield 36%).

A round-bottom flask containing compound CCXXIII-4 (6 g, 17.4 mmol) and Pd/C (5%, 0.60 g) in methanol (100 mL) was flushed with hydrogen gas three times. The mixture was stirred under hydrogen at atmospheric pressure for 3 h. The solution was filtered and concentrated in vacuo to obtain a viscous liquid compound CCXXIII-5 (4.94 g, 82%).

The solution of compound CCXXIII-5 (4.74 g, 13.7 mmol) in CH₃OH/HCl (80 ml) was stirred at room temperature overnight. The solution was concentrated to afford compound CCXXIII-6 as a yellow solid (3.0 g, yield 89.0%)

A flask was charged with Cbz-amino acid CCXXIII-7 (1 eq.), EDC.HCl (1.2 eq), HOBt (1.2 eq.) and DIEA (4 eq.) in dry DCM was added the solution of compound CCXXIII-6 (1 eq.) in dry DCM dropwise. The reaction mixture was stirred at room temperature overnight. The solution was diluted with water, extracted with EtOAc, the organic layer was washed with brine, dried over sodium sulfate and concentrated. The residue was purified by prep-TLC to afford compound CCXXIII-8.

The following compounds were prepared by the same procedure:

CCXXIII-8a (100 mg, yield 46%); CCXXIII-8b (100 mg, yield 57%); CCXXIII-8c (51 mg, yield 34%); CCXXIII-8d (70 mg, yield 33%); CCXXIII-8e (80 mg, yield 52%); CCXXIII-8f (87 mg, yield 58%); CCXXIII-8g (86 mg, yield 50%); CCXXIII-8h (64 mg, yield 43%); CCXXIII-8I (40 mg, yield 23%).

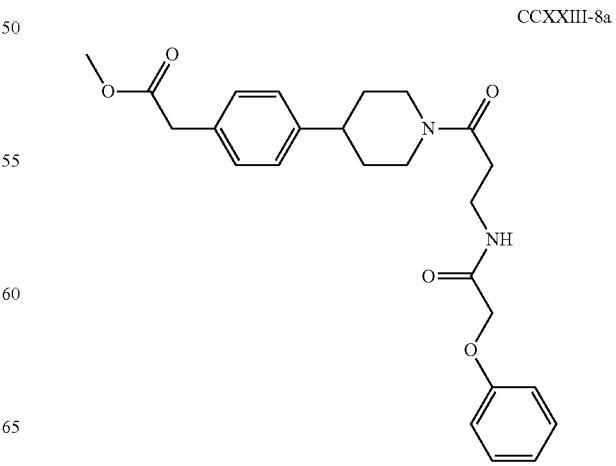

CCXXIII-8a

-continued

CCXXIII-8b
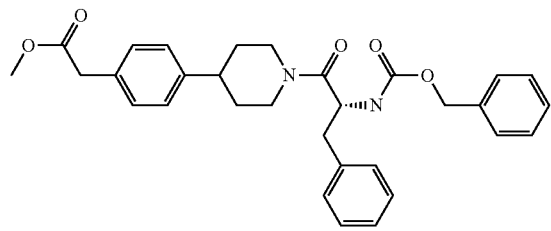

CCXXIII-8c
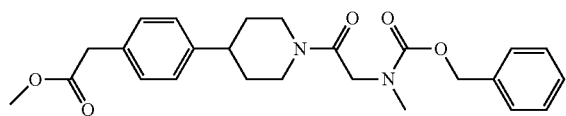

CCXXIII-8d
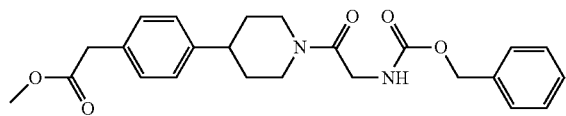

CCXXIII-8e
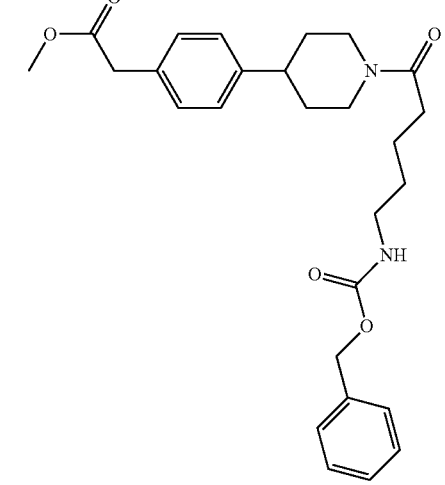

CCXXIII-8f
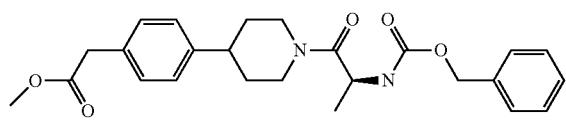

CCXXIII-8g

CCXXIII-8h
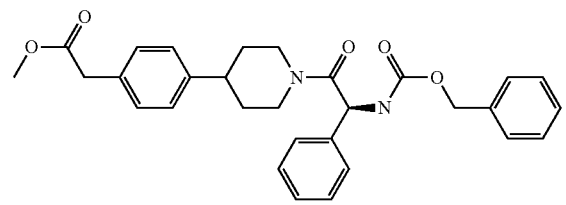

-continued

CCXXIII-8i
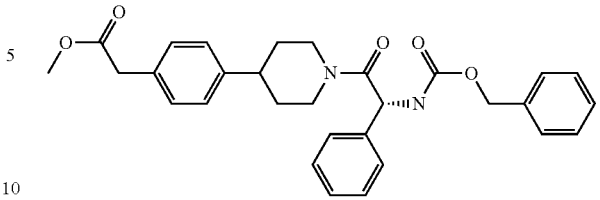

To a solution of compound CCXXIII-8 (1 eq.) in CH$_3$OH/H$_2$O (0.1 mmol/mL, v/v=5/1) was added LiOH.H$_2$O (5 eq.). The reaction mixture was stirred at room temperature overnight, diluted with water, acidified to pH~5 with aq. HCl (1 M), extracted with EtOAc, the organic layer was washed with water and brine, dried over anhydrous Na$_2$SO$_4$, and concentrated in vacuo. The residue was purified by prep-TLC to give final compounds CCXXIII-9.

The following compounds were prepared by the same procedure:

Compound 256: 12 mg, yield 11%. $^1$HNMR (CD$_3$OD, 400 MHz) δ 7.35-7.29 (m, 5H), 7.21-7.18 (m, 4H), 5.08 (s, 2H), 4.69 (d, J=13.2 Hz, 1H), 4.09 (d, J=13.2 Hz, 1H), 3.58 (s, 2H), 3.45-3.41 (m, 2H), 3.17-3.16 (m, 1H), 2.79-2.60 (m, 4H), 1.87 (m, 2H), 1.70-1.50 (m, 2H). MS (ESI) m/z M$^+$425.3.

Compound 257: 40 mg, yield 41%. $^1$HNMR (CDCl$_3$, 400 MHz) δ 7.38~7.16 (m, 12H), 7.09 (d, J=8.4 Hz, 1H), 6.98 (d, J=8.0 Hz, 1H), 5.94~5.87 (m, 1H), 5.14~5.06 (m, 2H), 5.00~4.94 (m, 1H), 4.71~4.66 (m, 1H), 3.86~3.63 (m, 1H), 3.63 (d, J=5.2 Hz, 2H), 3.04~2.93 (m, 3H), 2.58~2.32 (m, 3H), 1.82~1.68 (m, 2H), 1.56~1.45 (m, 2H), 1.27-1.21 (m, 1H).

Compound 258: 31 mg, yield 63%. $^1$HNMR (CDCl$_3$, 400 MHz) δ 7.39~7.28 (m, 5H), 7.24 (d, J=8.0 Hz, 2H), 7.15~7.07 (m, 2H), 5.16 (s, 2H), 4.74 (d, J=12.8 Hz, 1H), 4.23~4.08 (m, 2H), 3.90~3.70 (m, 1H), 3.63 (s, 2H), 3.13~3.09 (m, 1H), 3.04 (s, 3H), 2.74~2.63 (m, 2H), 1.90~1.80 (m, 2H), 1.66~1.50 (m, 2H).

Compound 259: 10 mg, yield 15.4%. $^1$HNMR (DMSO-d$_6$, 400 MHz) δ 7.39-7.29 (m, 5H), 7.23-7.18 (m, 4H), 5.11 (s, 2H), 4.64 (d, J=11.6 Hz, 1H), 4.11-3.97 (m, 3H), 3.56 (s, 2H), 3.19-3.12 (m, 1H), 2.80-2.73 (m, 2H), 1.89-1.81 (m, 2H), 1.72-1.51 (m, 2H). MS (ESI) m/z (M+23)$^+$433.2

Compound 260: 25.5 mg, yield 35%. $^1$HNMR (CDCl$_3$, 400 MHz) δ 7.35-7.34 (m, 5H), 7.24-7.22 (m, 2H), 7.15 (d, J=8.0 Hz, 2H), 5.15-5.08 (m, 3H), 4.76 (d, J=12 Hz, 1H), 3.94-3.91 (m, 1H), 3.62 (s, 2H), 3.28 (d, J=8.0 Hz, 2H), 3.11-3.05 (m, 1H), 2.72-2.33 (m, 4H), 1.87-1.81 (m, 4H), 1.58-1.55 (m, 3H). MS (ESI) m/z (M+Na)$^+$ 461.2.

Compound 261: 29 mg, yield 35%. $^1$HNMR (CDCl$_3$, 400 MHz) δ 7.42~7.03 (m, 5H), 7.26~7.22 (m, 4H), 7.16 (m, 2H), 5.99 (t, J=7.2 Hz, 1H), 5.11 (d, J=2.8 Hz, 2H), 4.72 (m, 2H), 3.98 (t, J=10.6 Hz, 1H), 3.63 (s, 2H), 3.20~3.11 (m, 1H), 2.74~2.64 (m, 2H), 1.93-1.86 (m, 2H), 1.70~1.50 (m, 3H), 1.40-1.30 (m, 3H).

Compound 262: 54 mg, yield 64%. $^1$HNMR (CDCl$_3$, 400 MHz) δ 7.44~7.31 (m, 10H), 7.23 (d, J=8.0 Hz, 1H), 7.13 (t, J=8.6 Hz, 2H), 6.91 (d, J=8.0 Hz, 1H), 6.51~6.46 (m, 1H), 5.69~5.62 (m, 1H), 5.15~5.11 (m, 1H), 5.04~4.99 (m, 1H), 4.79 (d, J=12.8 Hz, 1H), 3.91 (m, 1H), 3.61 (d, 2H), 3.06 (m, 1H), 2.71~2.57 (m, 2H), 1.85~1.60 (m, 2H), 1.43~1.35 (m, 1H).

Compound 263: 32 mg, yield 48%. $^1$HNMR (CDCl$_3$, 400 MHz) δ 7.52~7.24 (m, 5H), 7.22~7.16 (m, 2H), 7.14~7.12 (m, 2H), 5.99 (t, J=7.4 Hz, 1H), 5.14~5.08 (m, 2H), 4.75~4.71

(m, 2H), 3.98 (t, J=12.6 Hz, 1H), 3.62 (s, 2H), 3.14~3.07 (m, 1H), 2.77~2.61 (m, 2H), 2.01~1.80 (m, 2H), 1.72~1.53 (m, 2H), 1.46~1.33 (m, 3H).
Compound 264: 12 mg, yield 35%. ¹HNMR (CDCl₃, 400 MHz) δ 7.44-7.29 (m, 8H), 7.23-7.11 (m, 3H), 6.91 (d, J=8.0 Hz, 1H), 6.49-6.44 (m, 1H), 5.68-5.60 (m, 1H), 5.13-5.10 (m, 1H), 5.03-4.98 (m, 1H), 4.78 (m, 1H), 3.94-3.81 (m, 1H), 3.62-3.57 (m, 2H), 3.09-3.02 (m, 1H), 2.74-2.56 (m, 2H), 1.89-1.55 (m, 4H), 1.58-1.30 (m, 3H). MS (ESI) m/z (M+Na)⁺ 509.2.
-continued
Compound 256
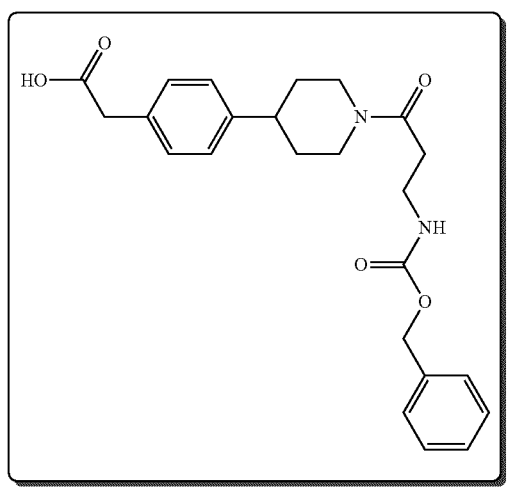
Compound 257
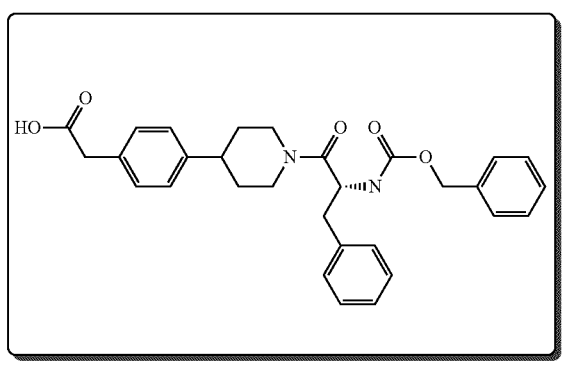
Compound 258
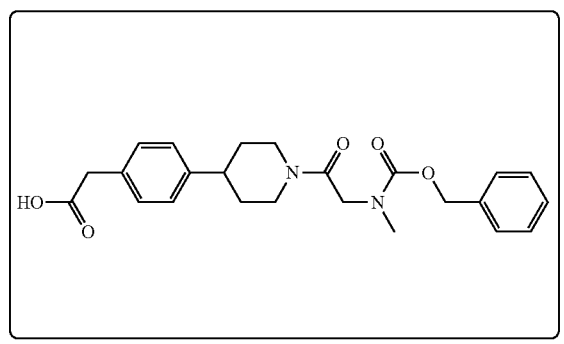
Compound 259
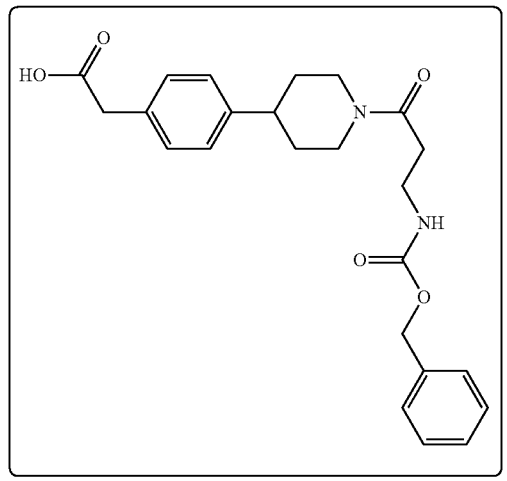
Compound 260
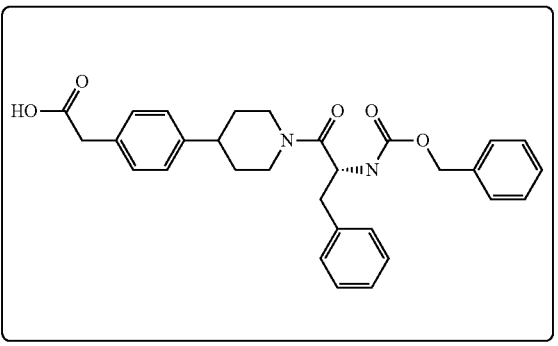
Compound 261
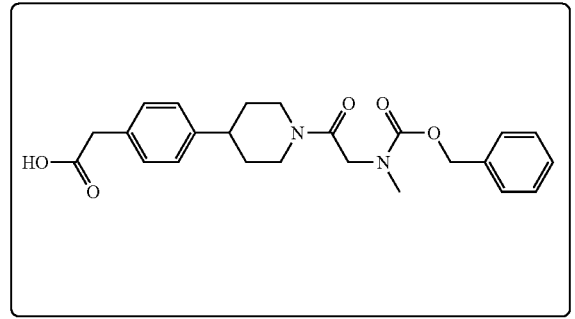

-continued

Compound 262

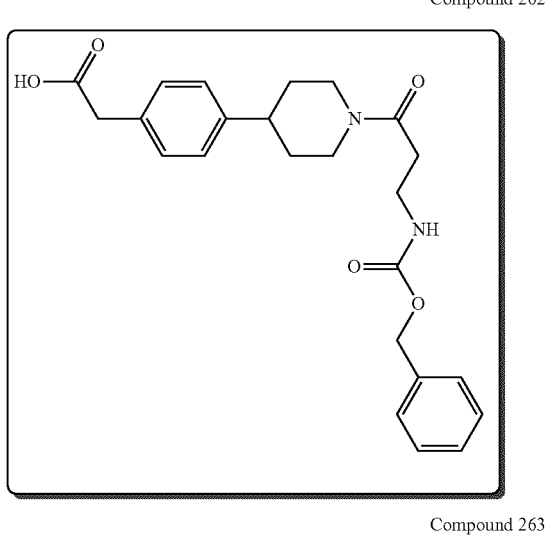

Compound 263

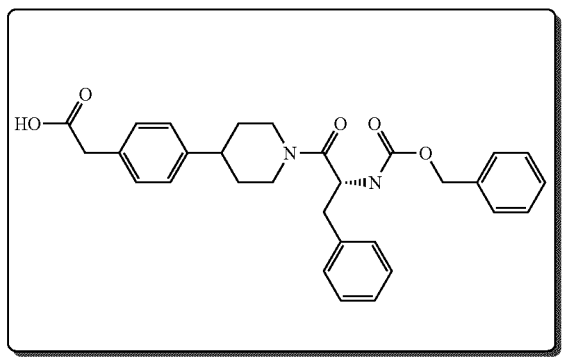

Compound 264

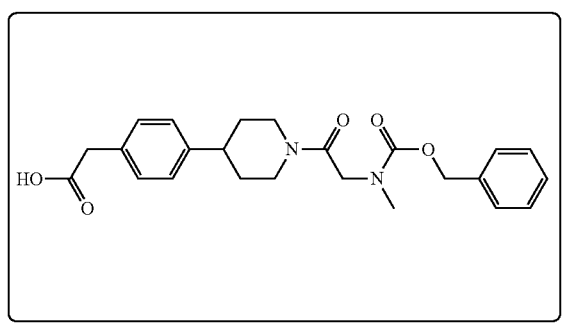

Syntheses of Compounds 265-273

General Synthetic Route (Scheme CCXXIV)

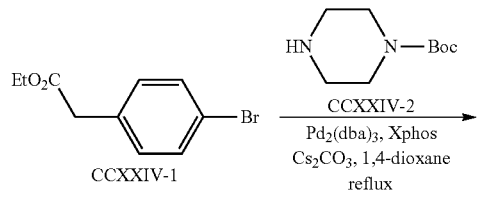

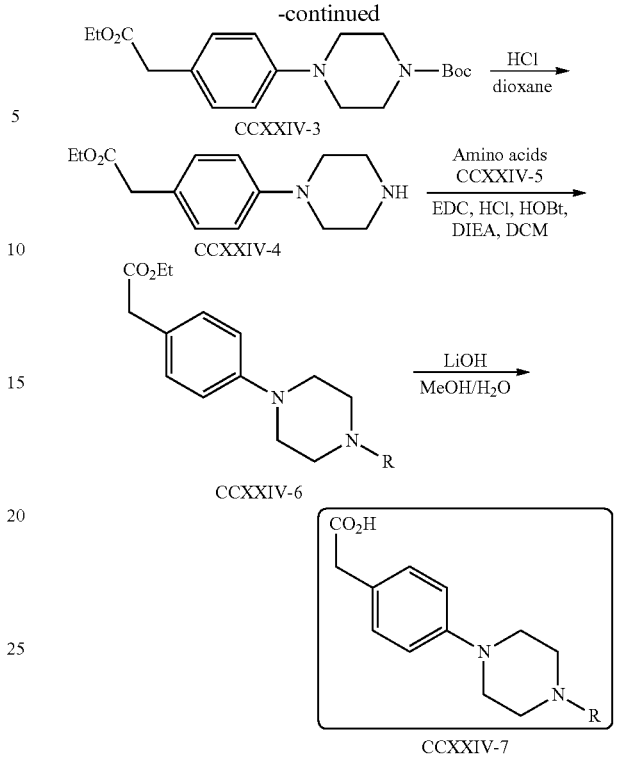

The compound CCXXIV-1 (2.5 g, 10 mmol), compound CCXXIV-2 (2.3 g, 12 mmol), Xphos (578 mg, 1 mmol) and $Cs_2CO_3$ (7.5 g, 20 mmol) were dissolved in 1,4-dioxane (50 mL). The solution was degassed by $N_2$ for three times and then $Pd_2(dba)_3$ (460 mg, 0.5 mmol) was added. The reaction mixture was stirred at 90-100° C. for 4 h under $N_2$ and then cooled to room temperature, diluted with EA (100 mL) and filtered, the filtrate was washed with water and brine. The separated organic phase was dried over $Na_2SO_4$, concentrated. The residue was purified by flash column chromatography (PE/EA=10/1) to gave compound CCXXIV-3 (577.5 mg, yield 17%) as a colorless oil. MS (ESI) m/z (M+H)$^+$ 348.9.

Compound CCXXIV-3 (577.5 mg (purity 60%, 0.98 mmol) was dissolved in 8 mL of a solution of hydrogen chloride (gas) in 1,4-dioxane (4 M). The solution was stirred at r.t for 16 h. The resulting suspension is filtered and the filter cake is immediately washed with little DCM. After drying under reduced pressure, compound CCXXIV-4 (249.7 g, yield 90%) hydrochloride was obtained. Compound CCXXIV-4 (as hydrochloride salt) would be utilized in next step without any further purification. M with Cbz-amino acid CCXXIV-5 (1 eq.), EDC.HCl (1.2 eq), HOBt (1.2 S (ESI) m/z (M+H)$^+$ 248.9.

A flask was charged 1 eq.) and DIEA (4 eq.) in dry DCM was added the solution of compound CCXXIV-4 (1 eq.) in dry DCM dropwise. The reaction mixture was stirred at room temperature overnight. The solution was diluted with water, extracted with EtOAc, the organic layer was washed with brine, dried over sodium sulfate and concentrated. The residue was purified by prep-TLC to afford compound CCXXIV-6.

The following compounds were prepared by the same procedure:
CCXXIV-6a (102.6 mg, yield 70%); CCXXIV-6b (40.5 mg, yield 42%); CCXXIV-6c (71.8 mg, yield 40%);

CCXXIV-6d (50 mg, yield 24%); CCXXIV-6e (70.5 mg, yield 40%); CCXXIV-6f (30 mg, yield 18%); CCXXIV-6g (102.6 mg, yield 15%); CCXXIV-6h (20 mg, yield 11%); CCXXIV-6I (30 mg, yield 15%.).
-continued
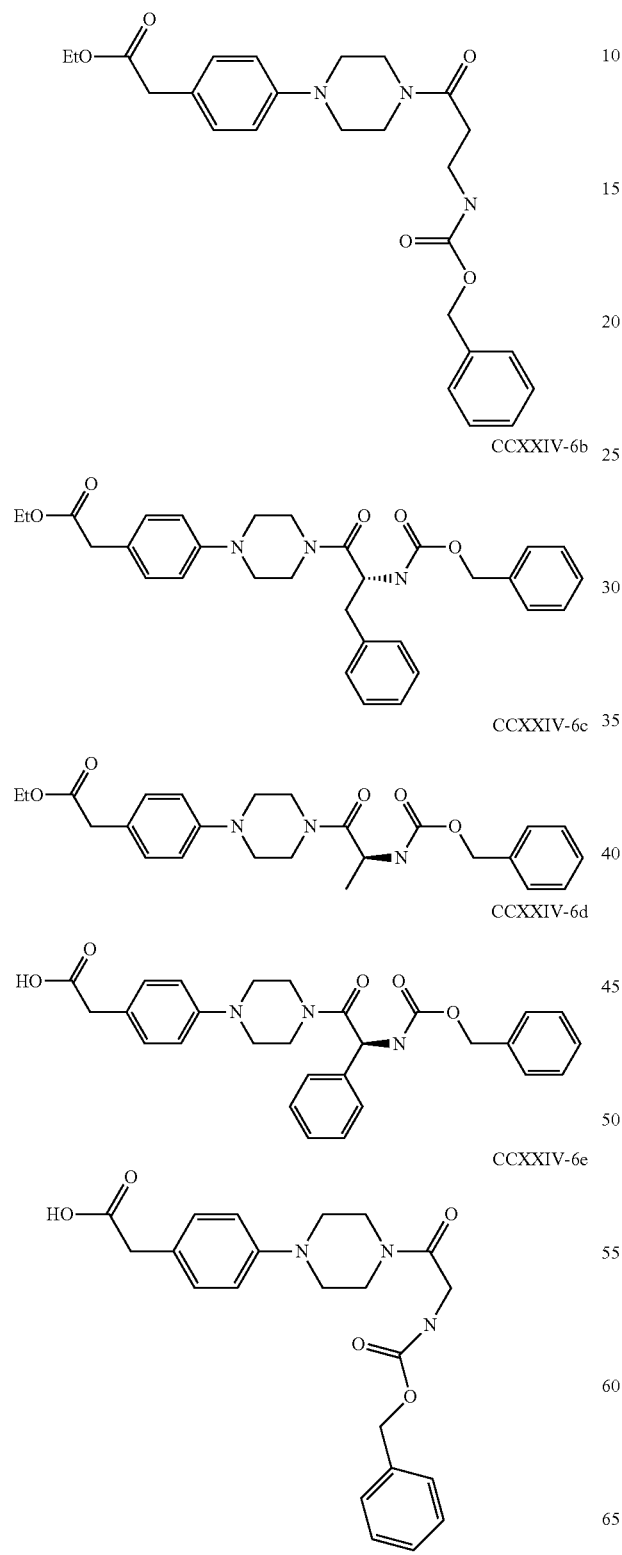
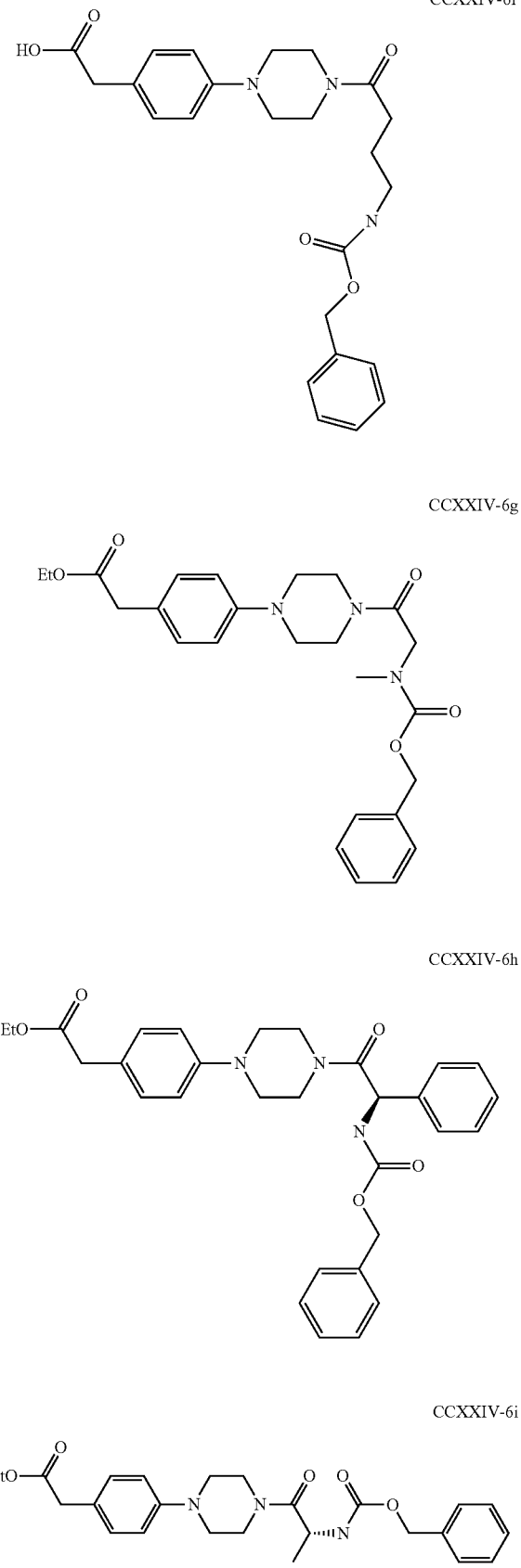

To a solution of compound CCXXIV-6 (1 eq.) in CH₃OH/H₂O (0.1 mmol/mL, v/v=5/1) was added LiOH.H₂O (5 eq.). The reaction mixture was stirred at room temperature overnight, diluted with water, acidified to pH~5 with aq. HCl (1 M), extracted with EtOAc, the organic layer was washed with water and brine, dried over anhydrous Na₂SO₄, and concentrated in vacuo. The residue was purified by prep-TLC to give final compounds CCXXIV-7.

The following compounds were prepared by the same procedure:

Compound 265: 25 mg, yield 32%. ¹H NMR (CDCl₃, 400 MHz) δ 7.40~7.28 (m, 5H), 7.20 (d, J=8.8 Hz, 2H), 6.89 (d, J=8.8 Hz, 2H), 5.57 (m, 1H), 5.15 (s, 2H), 3.69 (m, 2H), 3.65~3.45 (m, 7H), 3.27 (m, 4H), 2.60 (m, 2H). MS (ESI) m/z (M+H)⁺ 426.2.

Compound 266: 15 mg, yield 39%. ¹H NMR (CDCl₃, 400 MHz) δ 7.38~7.29 (m, 6H), 7.23~7.16 (m, 6H), 6.77 (d, J=8.8 Hz, 2H), 5.74 (d, J=8.8 Hz, 1H), 5.14~5.10 (m, 2H), 4.96~4.90 (m, 1H), 3.67 (m, 2H), 3.58 (s, 2H), 3.47~3.40 (m, 1H), 3.09~3.01 (m, 4H), 2.99~2.90 (m, 2H), 2.41~2.39 (m, 1H). MS (ESI) m/z (M+H)⁺ 502.3.

Compound 267: 25 mg, yield 32%. ¹H NMR (CDCl₃, 400 MHz) δ 7.36~7.31 (m, 5H), 7.20 (d, J=8.4 Hz, 2H), 6.88 (d, J=8.4 Hz, 2H), 5.88 (d, J=7.2 Hz, 1H), 5.11 (s, 2H), 4.77~4.70 (m, 1H), 3.85~3.82 (m, 1H), 3.71~3.67 (m, 2H), 3.59 (s, 3H), 3.16 (m, 4H), 1.36~1.34 (m, 3H), 1.26 (s, 1H). MS (ESI) m/z (M+H)⁺ 426.3.

Compound 268: 17 mg, yield 36%. ¹H NMR (CDCl₃, 400 MHz) δ 7.41~7.29 (m, 10H), 7.14 (d, J=8.0 Hz, 2H), 6.77 (d, J=8.0 Hz, 2H), 6.40 (d, J=7.2 Hz, 1H), 5.65 (d, J=7.2 Hz, 1H), 5.13 (d, J=12.4 Hz, 1H), 5.02 (d, J=12.4 Hz, 1H), 3.92~3.89 (m, 1H), 3.69~3.65 (m, 1H), 3.60~3.51 (m, 3H), 3.42~3.39 (m, 1H), 3.16 (m, 1H), 2.99~2.94 (m, 2H), 2.51~2.46 (m, 1H). MS (ESI) m/z (M+H)⁺ 488.1.

Compound 269: 28 mg, yield 42%. ¹H NMR (CDCl₃, 400 MHz) δ 7.37~7.33 (m, 5H), 7.21 (d, J=8.4 Hz, 2H), 6.88 (d, J=8.4 Hz, 2H), 5.83 (m, 1H), 5.13 (s, 2H), 4.07 (d, J=4.4 Hz, 2H), 3.79~3.76 (m, 2H), 3.59 (s, 2H), 3.53~3.52 (m, 2H), 3.16~3.15 (m, 4H). MS (ESI) m/z (M+Na⁺) 434.0.

Compound 270: 20 mg, yield 42%. ¹H NMR (CDCl₃, 400 MHz) δ 7.40~7.30 (m, 5H), 7.19 (d, J=8.4 Hz, 2H), 6.86 (d, J=8.4 Hz, 2H), 5.08 (m, 2H), 3.73 (m, 2H), 3.58 (m, 4H), 3.28 (m, 2H), 3.11 (m, 4H), 2.41 (m, 2H), 1.88 (m, 2H).

Compound 271: 30 mg, yield 22%. ¹H NMR (DMSO-d₆, 400 MHz) δ 12.21 (brs, 1H), 7.40~7.22 (m, 5H), 7.10 (d, J=8.0 Hz, 2H), 6.88 (t, J=8.0 Hz, 2H), 5.07 (s, 1H), 5.00 (s, 1H), 4.17 (d, J=11.2 Hz, 2H), 3.60~3.50 (m, 4H), 3.43 (s, 2H), 3.11-3.02 (m, 4H), 2.90-2.84 (m, 3H).

Compound 272: 32 mg, yield 34%. ¹H NMR (CDCl₃, 400 MHz) δ 7.40~7.26 (m, 5H), 7.19 (d, J=8.4 Hz, 2H), 6.90-6.82 (m, 2H), 5.18-5.11 (m, 2H), 4.16 (s, 1H), 4.08 (s, 1H), 3.75 (m, 2H), 3.60-3.45 (m, 4H), 3.11 (m, 3H), 3.05-3.00 (m, 4H).

Compound 273: 200 mg, yield 70%. ¹H NMR (CDCl₃, 400 MHz) δ 7.40~7.30 (m, 5H), 7.19 (d, J=8.4 Hz, 2H), 6.87 (d, J=8.4 Hz, 2H), 5.96 (d, J=8.0 Hz, 1H), 5.10 (s, 2H), 4.74 (m, 1H), 3.86-3.80 (m, 1H), 3.72-3.65 (m, 2H), 3.62-3.57 (m, 3H), 3.17-3.10 (m, 4H), 1.36 (d, J=6.8 Hz, 3H).

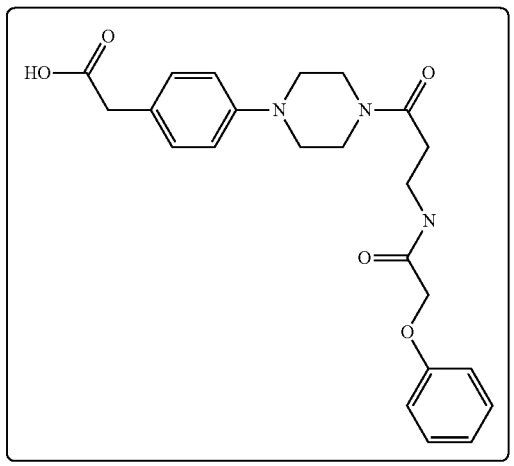

Compound 265

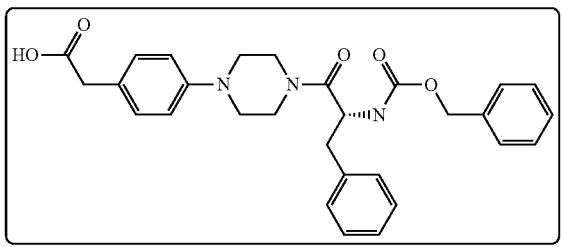

Compound 266

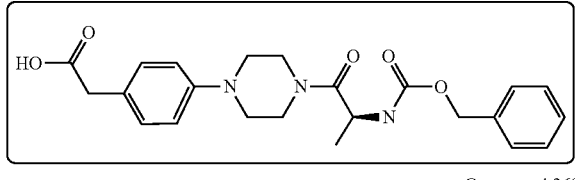

Compound 267

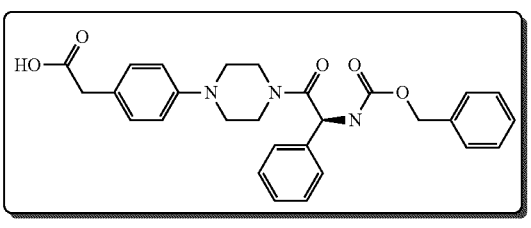

Compound 268

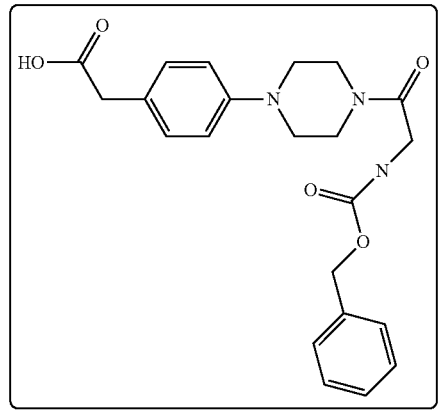

Compound 269

Compound 270
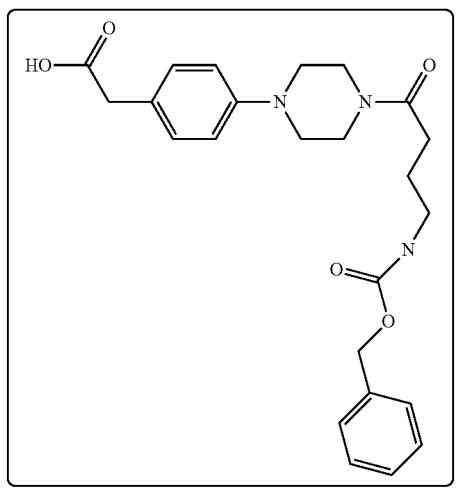
Compound 272
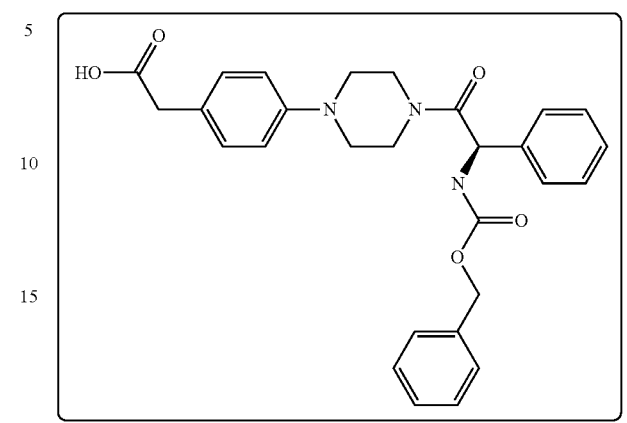
Compound 271
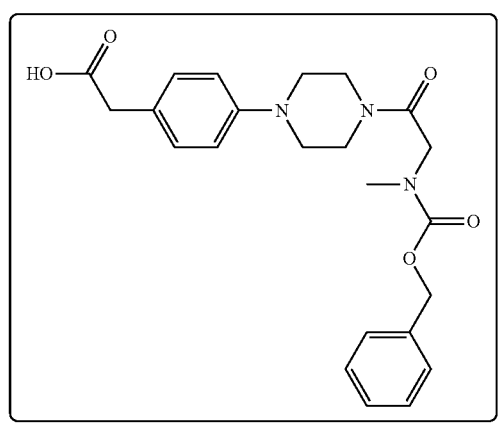
Compound 273
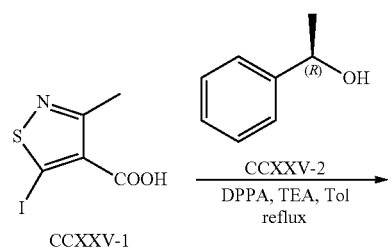
Synthesis of Compound 44
Synthetic Route CCXXV
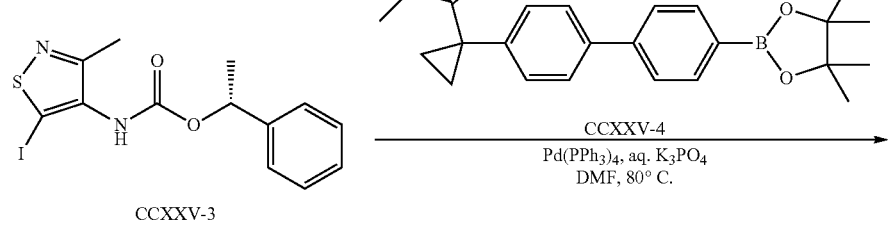

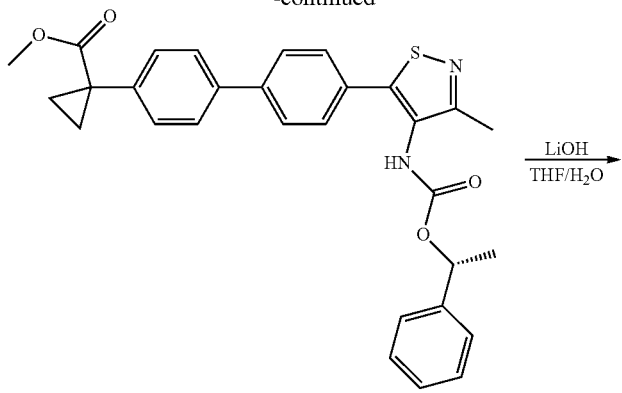

CCXXV-5

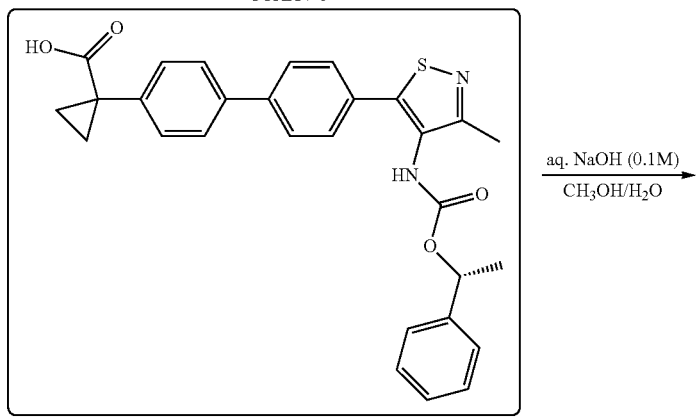

Compound 44

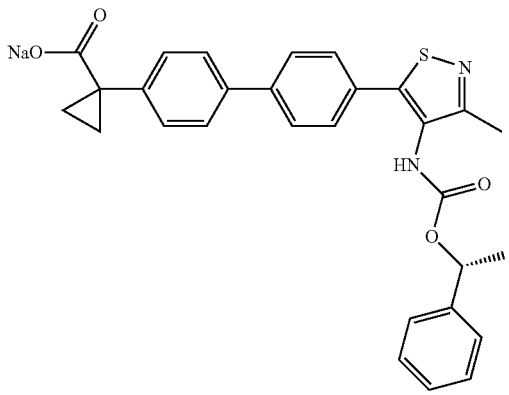

Compound 44a

To a solution of compound CCXXV-1 (3.5 g, 13.2 mmol) in Tol (35 mL) was added compound CCXXV-2 (1.9 g, 15.6 mmol), followed by adding molecular sieve (3 g), DPPA (3.8 g, 13.1 mmol) and TEA (3.34 g 33 mmol). The reaction mixture was reflux at 100° C. for 18 hours. The solvent was removed in vacuo and the residue was diluted with $H_2O$, and extracted with EtOAc. The combined organic extracts was washed with brine, dried over $Na_2SO_4$, and concentrated in vacuo to give crude compound CCXXV-3 (5.1 g, crude yield 99%). The crude product was used for next step directly without purification.

To a solution of compound CCXXV-3 (4.9 g, 12.6 mmol) in $DME/H_2O$ (v/v=4:1 mL) was added compound 4 (5.2 g, 13.8 mmol), Pd(dppf)$Cl_2$ (460 mg, 0.63 mmol), $Na_2CO_3$ (4 g, 37.8 mmol). The mixture was purged with nitrogen for three times and then heated at reflux under nitrogen for 48 hrs. After concentration, the residue was partitioned between $H_2O$ and EtOAc. The combined organic was washed with brine, dried over $Na_2SO_4$, concentrated in vacuo. The crude residue was purified by flash chromatography (PE/EA=2/1) to give compound CCXXV-5 (4.6 g, yield 71%).

Preparation of Compound 44

To a solution of compound CCXXV-5 (4.6 g, 9.0 mmol) in THF (30 mL) was added water (10 mL) and LiOH.$H_2O$ (755 mg, 18.0 mmol). The reaction mixture was stirred at room temperature overnight. The mixture was acidified to pH~6 with aq. HCl (2 N), and extracted with EtOAc (50 mL×3). The combined organic extracts was washed with brine, dried over Na₂SO₄, and concentrated in vacuo. The residue was purified by prep-HPLC to give Compound 44 (3 g, yield 70%). ¹HNMR (DMSO-d₆, 400 MHz) δ 12.3 (s, 1H), 9.27 (s, 1H), 7.72 (d, J=8.0 Hz, 2H), 7.66-7.55 (m, 4H), 7.48-7.40 (m, 5H), 7.38-7.02 (m, 2H), 5.73 (d, J=7.2 Hz, 1H), 2.24 (s, 3H), 1.51 (d, J=7.2 Hz, 3H), 1.48 (m, 2H), 1.18 (m, 2H).

Preparation of Compound 44a (Sodium Salt)

To a solution of Compound 44 (1.1 g, 2.2 mmol) in CH₃OH (4 mL) was added NaOH (0.1 M, 2.2 mL, 2.2 mmol). The reaction mixture was stirred at room temperature for 2 hours. The mixture was concentrated in vacuo to remove CH₃OH. The mixture was freeze-dried to give Compound 44a (1.14 g, yield 100%). ¹HNMR (DMSO-d₆, 400 MHz) δ 9.27 (s, 1H), 7.68 (d, J=8.0 Hz, 2H), 7.59-7.49 (m, 4H), 7.51-7.00 (m, 7H), 5.73 (d, J=6.0 Hz, 1H), 2.24 (s, 3H), 1.51 (d, J=6.0 Hz, 3H), 1.15 (m, 2H), 0.65 (m, 2H).

Preparation of Compound 44b (Potassium Salt)

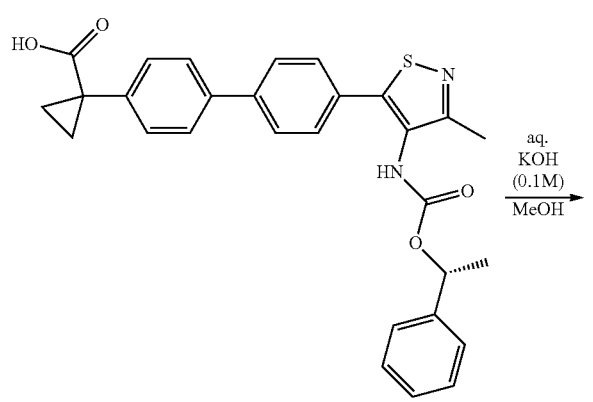

Compound 44

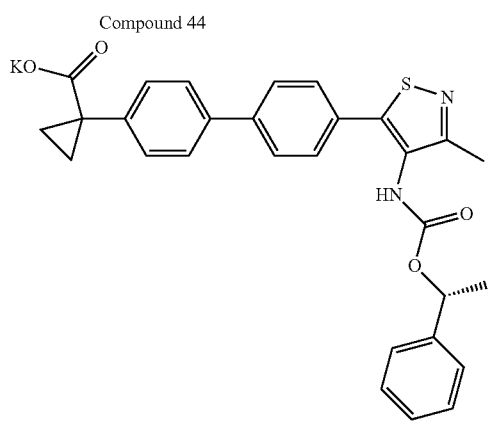

Compound 44b

To a solution of Compound 44 (1.05 g, 2.106 mmol) in MeOH (20 mL) was added drop wise a solution of aq. KOH (0.1 N, 21.06 mL, 2.106 mmol). The mixture was stirred at r.t for 30 min. Then the mixture was concentrated and freeze-dried under vacuum. The product Compound 44b was obtained as potassium salt and pure enough without further purification (1.13 g, ~100% yield). ¹HNMR (DMSO-d₆, 400 MHz) δ 9.34 (s, 1H), 7.68 (d, J=8.4 Hz, 2H), 7.60-7.48 (m, 4H), 7.42-7.25 (m, 6H), 7.22-6.98 (m, 1H), 5.77-5.69 (m, 1H), 2.24 (s, 3H), 1.51 (d, J=6.4 Hz, 2H), 1.18 (s, 2H), 0.69 (s, 2H). MS (ESI) m/z (M+H)⁺ 499.2.

Preparation of Compound 44c (Trisamine Salt)

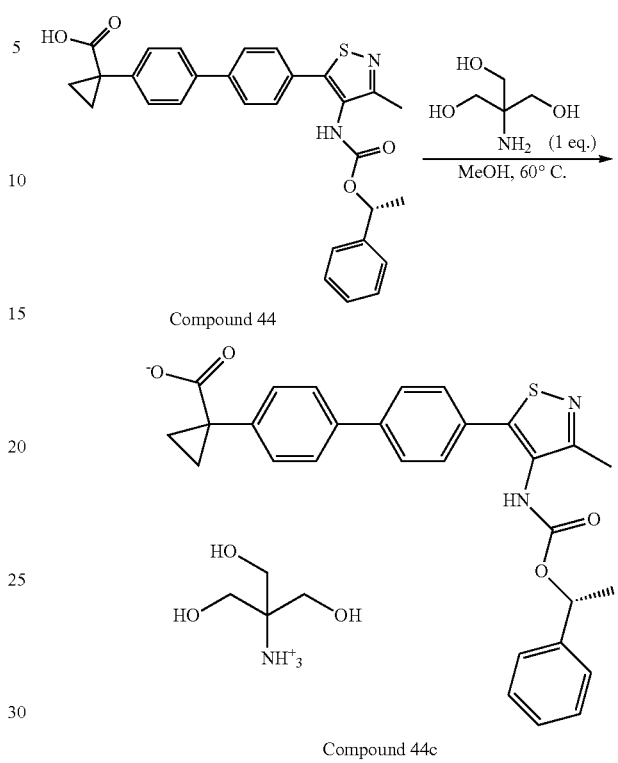

Compound 44c

To a solution of Compound 44 (1.01 g, 2.0 mmol) in MeOH (20 mL) was added trisamine (242 mg, 2.0 mmol). The mixture was refluxed at 60° C. for 2 hrs. Then the mixture was concentrated and dried under vacuum. The product Compound 44c was obtained as trisamine salt and pure enough without further purification (1.24 g, ~100% yield). ¹HNMR (CD₃OD, 400 MHz) δ 7.65 (d, J=8.0 Hz, 2H), 7.60-7.50 (m, 4H), 7.47 (d, J=8.0 Hz, 2H), 7.44-7.30 (m, 4H), 7.22-7.02 (m, 1H), 5.83-5.78 (m, 1H), 3.65 (s, 6H), 2.34 (s, 3H), 1.58 (d, J=6.4 Hz, 3H), 1.50 (q, J=3.6 Hz, 2H), 1.05 (q, J=3.6 Hz, 2H). MS (ESI) m/z (M+H)⁺ 499.2.

Preparation of Compound 44d (Calcium Salt)

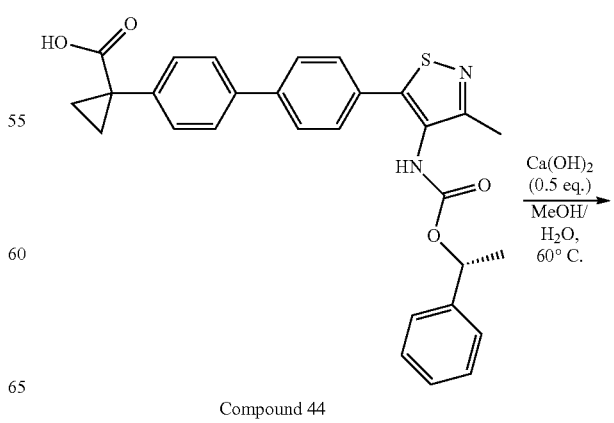

Compound 44

1233

-continued

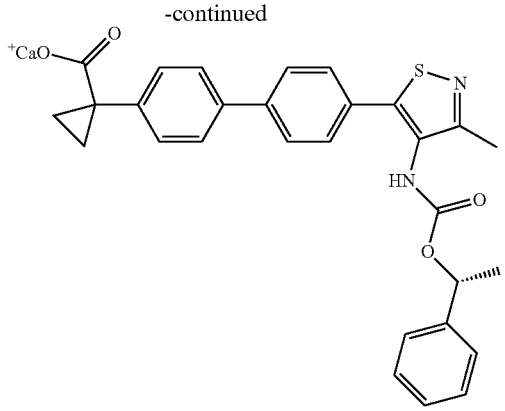

Compound 44d

To a solution of Compound 44 (1 g, 2.0 mmol) in MeOH (20 mL) and water (2 mL) was added Ca(OH)$_2$ (74 mg, 1.0 mmol) portion wise. The mixture was heated at 60° C. for 1 h. Then the mixture was concentrated and freeze-dried under vacuum. The product Compound 44d was obtained as calcium salt and pure enough without further purification (1.07 g, ~100% yield). $^1$HNMR (DMSO-d$_6$, 400 MHz) δ 9.30 (s, 1H), 7.72 (d, J=7.6 Hz, 2H), 7.65-7.54 (m, 4H), 7.45-7.35 (m, 5H), 7.32 (brs, 1H), 7.23-7.00 (m, 1H), 5.78-5.70 (m, 1H), 2.26 (s, 3H), 1.53 (d, J=6.4 Hz, 3H), 1.39 (s, 2H), 0.99 (s, 2H). MS (ESI) m/z (M+H)$^+$ 499.2.

Synthesis of Compound 45

Synthetic Route (Scheme CCXXVI)

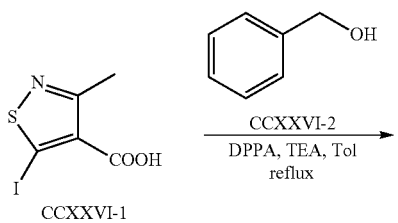

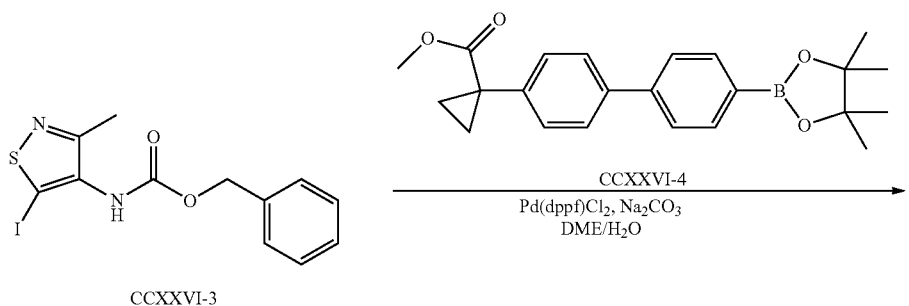

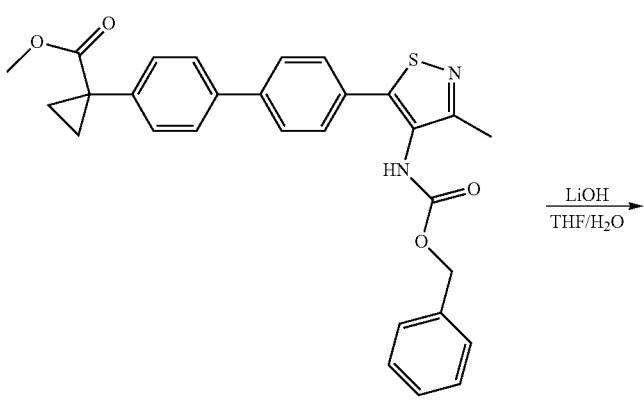

CCXXVI-5

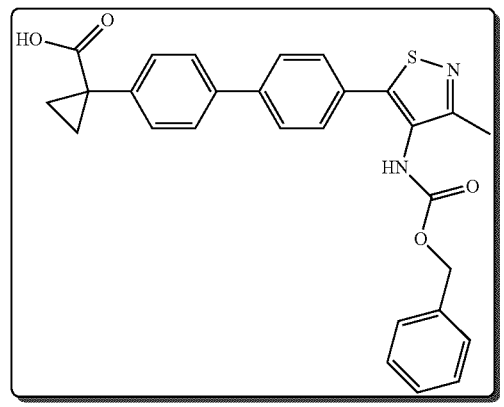

Compound 45

Compound 45 was purified by prep HPLC and carried through without further characterization. The sodium salt of Compound 45 (Compound 45a) was prepared analogously to the procedure described in the synthesis of Compound 44a. Compound 45a: $^1$HNMR (DMSO-$d_6$, 400 MHz) δ 9.36 (s, 1H), 7.73 (d, J=8.0 Hz, 2H), 7.59 (d, J=8.0 Hz, 2H), 7.53 (d, J=8.0 Hz, 2H), 7.43-7.35 (m, 6H), 7.27-7.05 (m, 1H), 5.15 (s, 2H), 2.30 (s, 3H), 1.21 (m, 2H), 0.72 (m, 2H). MS (ESI) m/z (M+H)$^+$ 485.1.

Compound 45b was prepared analogously to the procedure described in the synthesis of Compound 44b and pure enough without further purification (2.1 g, ~100% yield). $^1$HNMR (DMSO-$d_6$, 400 MHz) δ 9.40 (s, 1H), 7.73 (d, J=8.0 Hz, 2H), 7.60 (d, J=8.0 Hz, 2H), 7.53 (d, J=8.0 Hz, 2H), 7.42-7.32 (m, 6H), 7.26-7.05 (m, 1H), 5.15 (s, 2H), 2.30 (s, 3H), 1.21 (m, 2H), 0.71 (m, 2H). MS (ESI) m/z (M+H)$^+$ 485.2.

Compound 45c was prepared analogously to the procedure described in the synthesis of Compound 44c and pure enough without further purification (2 g, ~100% yield). $^1$HNMR (DMSO-$d_6$, 400 MHz) δ 9.30 (s, 1H), 7.73 (d, J=8.0 Hz, 2H), 7.61-7.55 (m, 4H), 7.40-7.32 (m, 6H), 7.26-7.05 (m, 1H), 5.13 (s, 2H), 3.32 (m, 6H), 2.28 (s, 3H), 1.32 (m, 2H), 0.91 (m, 2H). MS (ESI) m/z (M+H)$^+$ 485.2.

Compound 45d was prepared analogously to the procedure described in the synthesis of Compound 44d and pure enough without further purification (1.95 g, ~100% yield). $^1$HNMR (CD$_3$OD, 400 MHz) δ 7.70-7.30 (m, 13H), 5.18 (s, 2H), 2.36 (s, 3H), 1.61 (m, 2H), 1.23 (m, 2H). MS (ESI) m/z (M+H)$^+$ 485.2.

Synthesis of Compound 46

Synthetic Route (Scheme CCXXVII)

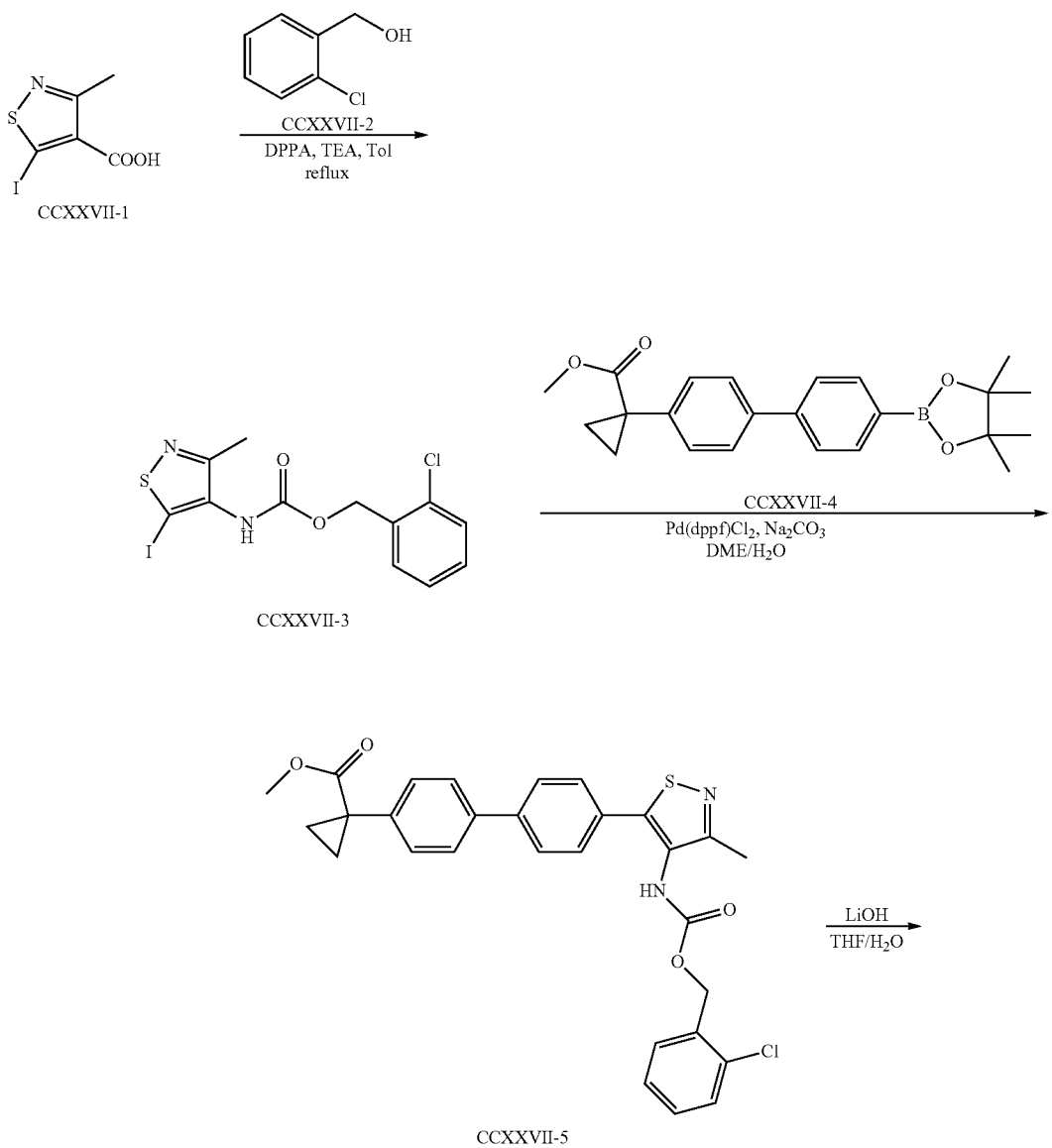

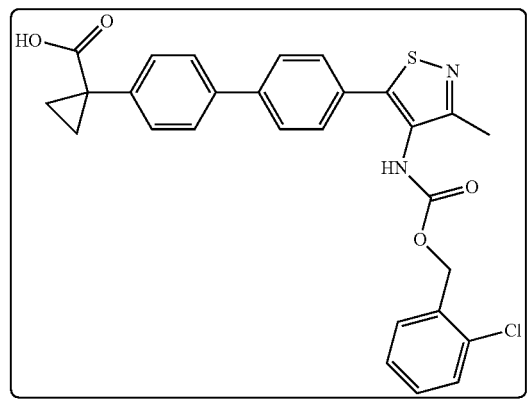
Compound 46
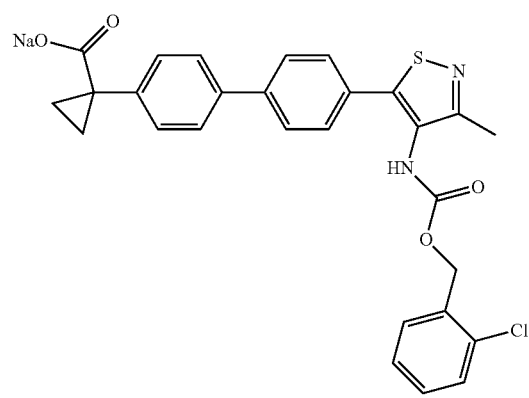
Compound 46a
Compound 46 was prepared analogously to the procedure described in the synthesis of Compound 44 and was purified by prep HPLC and carried on without further characterization. Compound 46a: $^1$HNMR (DMSO, 400 MHz) δ 7.71 (d, J=8.8 Hz, 2H), 7.65-7.56 (m, 4H), 7.54-7.43 (m, 4H), 7.38-7.32 (m, 2H), 5.30 (s, 2H), 2.40 (s, 3H), 1.49 (m, 2H), 0.99 (m, 2H).
Synthesis of Compound 33
Synthetic Route (Scheme CCXXVIII)
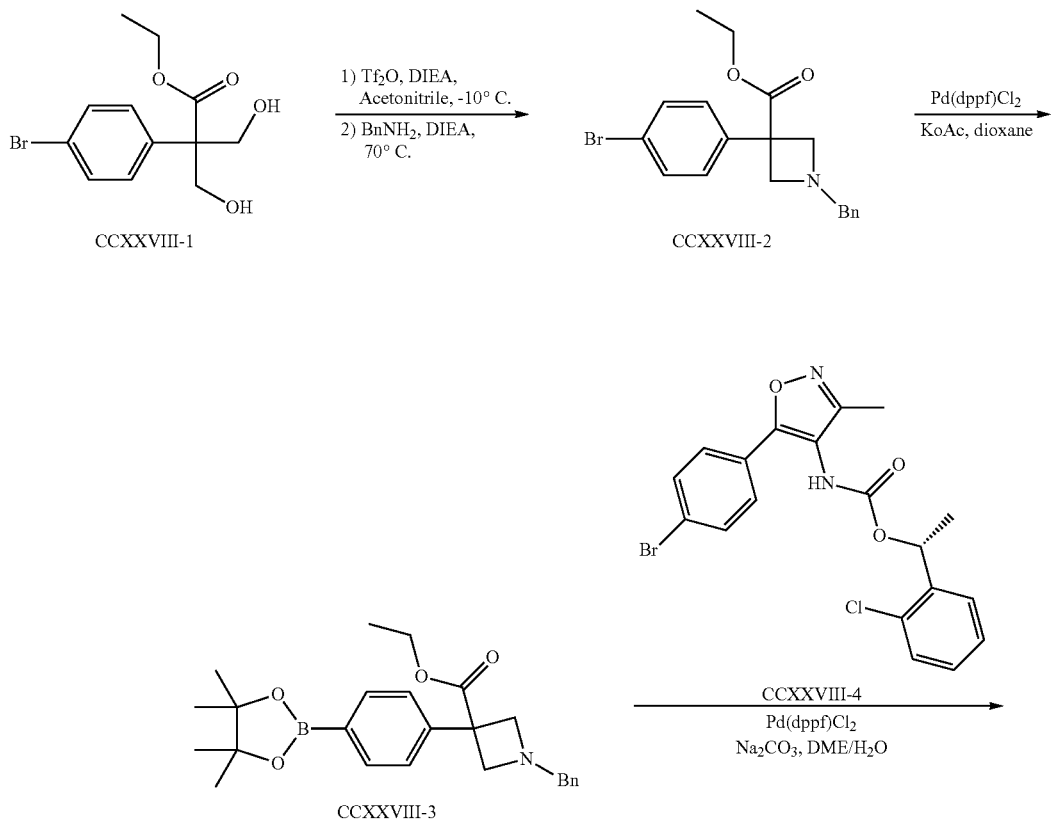

-continued

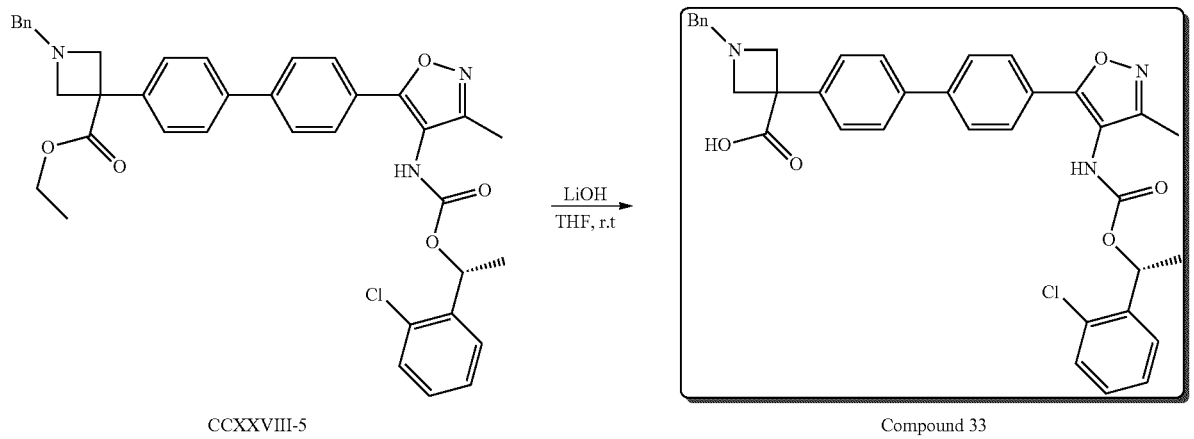

CCXXVIII-5

Compound 33

To a solution of compound CCXXVIII-1 (7.5 g, 24.7 mmol) in $CH_3CN$ (150 mL) was added $Tf_2O$ (8.7 mL, 51.98 mmol), followed by adding DIEA (10.1 mL, 61.75 mmol) while maintaining the temperature about −10° C. The reaction mixture was stirred at −10° C. for 1 hour. To the above reaction mixture was added $BnNH_2$ (3.95 mL, 37 mmol) and DIEA (10.1 mL, 61.75 mmol), and the mixture was stirred at 75° C. overnight. After being cooled to r.t., the mixture was diluted with EtOAc (100 mL), washed with water and brine, dried over $Na_2SO_4$, filtered and concentrated. The residue was purified by column (PE:EA=10:1) to give compound CCXXVIII-2 (4.0 g, yield: 43%) as a solid. MS (ESI) m/z $(M+H)^+$ 374.2.

To a solution of compound CCXXVIII-2 (4 g, 10.7 mmol) in dioxane (100 mL) was added Bis(pinacolato)diboron (4.07 g, 16 mmol), KOAc (3.14 g, 32.1 mmol) and $Pd(dppf)Cl_2$ (234 mg, 0.32 mmol). The reaction mixture was flushed with nitrogen and heated to 90° C. overnight. The mixture was diluted with EtOAc, washed with water and brine, dried over $Na_2SO_4$, filtered and concentrated. The residue was purified by column chromatography (PE:EA=10:1) to give product CCXXVIII-3 (4 g, yield 89%). MS (ESI) m/z $(M+H)^+$ 421.

To a solution of compound CCXXVIII-3 (100 mg, 0.237 mmol) in $DME/H_2O$ (4 mL/1 mL) was added CCXXVIII-4 (103 mg, 0.237 mmol), $Na_2CO_3$ (56 mg, 0.48 mmol) and $Pd(dppf)Cl_2$ (17 mg, 0.024 mmol). The reaction mixture was flushed with nitrogen and heated to 90° C. overnight. The mixture was diluted with EtOAc, washed with water and brine, dried over $Na_2SO_4$, filtered and concentrated. The residue was purified by column chromatography (PE:EA=15:1) to give product CCXXVIII-5 (60 mg, yield 39%). MS (ESI) m/z $(M+H)^+$ 650.1.

Preparation of Compound 33

To a solution of compound CCXXVIII-5 (40 mg, 0.06 mmol) in THF (3 mL) was added water (1 mL) and $LiOH.H_2O$ (28 mg, 0.6 mmol). The reaction mixture was stirred at room temperature overnight. The mixture was cooled down to 0° C. and neutralized to pH~6 with 1 N hydrochloride solution. The mixture was concentrated in vacuo to remove solvent THF, the residue was lyophilized and purified by pre-HPLC to give desired Compound 33 (15 mg, yield: 39%). $^1H$ NMR (400 MHz, DMSO-$d_6$): δ 9.42 (s, 1 H), 9.80 (s, 1 H), 7.77-7.81 (m, 4 H), 7.61-7.70 (m, 3 H), 7.21-7.49 (m, 10 H), 5.96-5.98 (q, 1 H), 3.85 (d, J=6.4 Hz, 2 H), 3.59 (s, 2 H), 3.46 (d, J=6.4 Hz, 2 H), 2.10 (s, 3 H), 1.53 (d, J=6.0 Hz, 3 H). MS (ESI) m/z $(M+H)^+$ 622.1

Synthesis of Compound 34

Synthetic Route (Scheme CCXXIX)

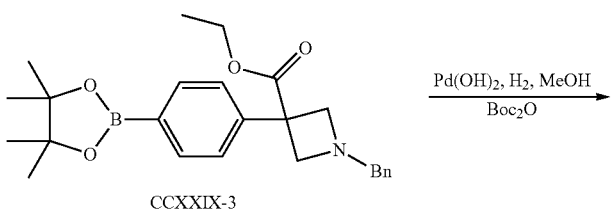

CCXXIX-3

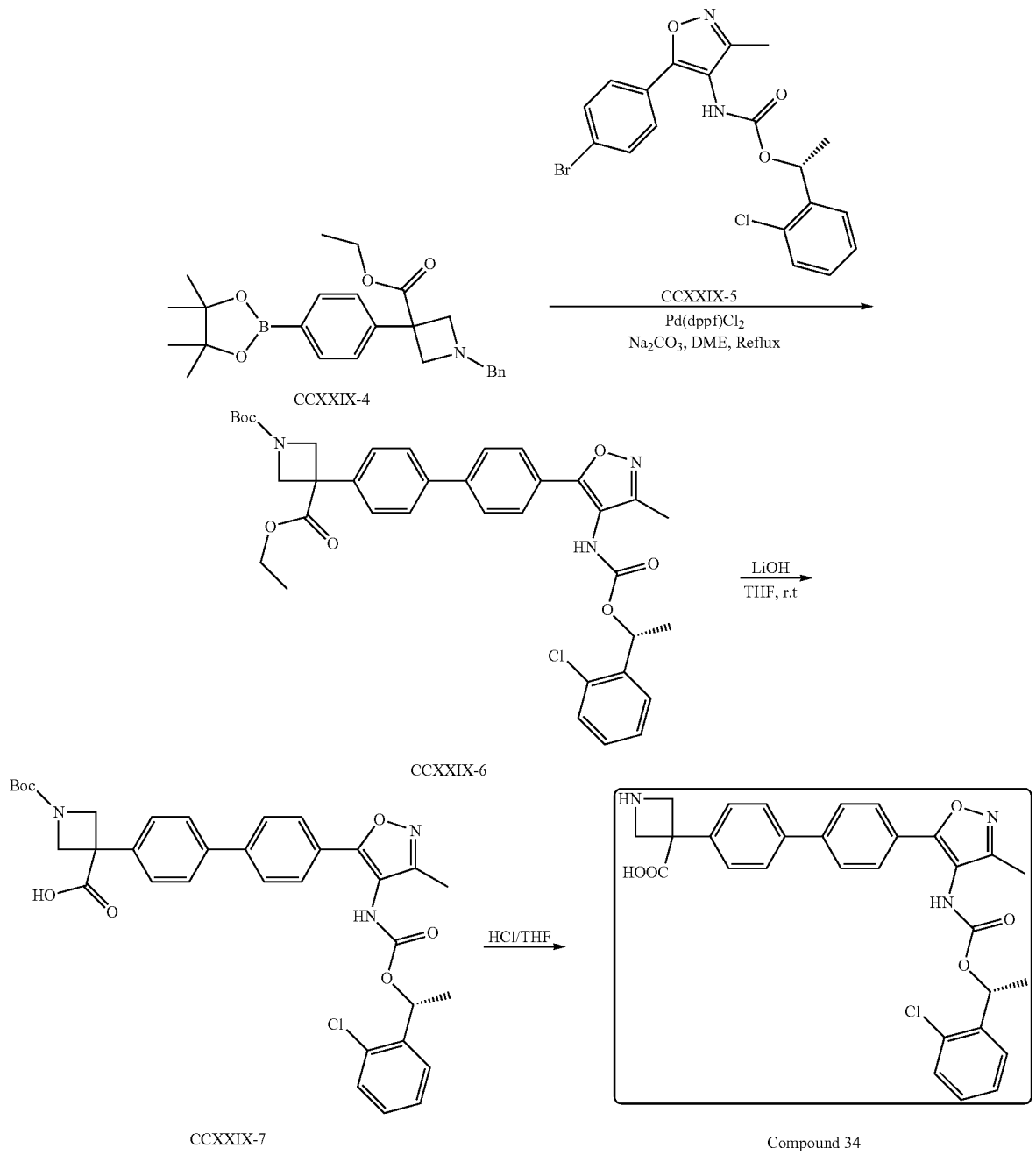

To a solution of compound CCXXIX-3 (4.22 g, 10 mmol) in methanol (150 mL) was added Pd(OH)$_2$ (1.0 g,), followed by adding Boc$_2$O (3.27 g, 15 mmol). The reaction mixture was stirred under H$_2$ (50 psi) at r.t overnight. The reaction mixture was filtered and the filtrated was concentrated to give crude compound CCXXIX-4 (3.4 g, yield 79%), which was used to next step without further purification.

To a stirred mixture of compound CCXXIX-4 (600 mg, 1.389 mmol), CCXXIX-5 (604 mg, 1.389 mmol), and Na$_2$CO$_3$ (295 mg, 2.778 mmol) in DME (12 mL) and H$_2$O (4 mL) was added Pd(dppf)Cl$_2$ (101 mg) under N$_2$ protection. The reaction mixture was stirred at 100° C. overnight. After being cooled to r.t., the mixture was diluted with EtOAc, washed with water and brine, dried over Na$_2$SO$_4$, filtered and concentrated. The residue was purified by column chromatography (PE:EA=3:1) to give product CCXXIX-6 (650 mg, yield: 72%). MS (ESI) m/z (M+H)$^+$ 660.1

To a solution of compound CCXXIX-6 (60 mg, 0.09 mmol) in THF (3 mL) was added water (1 mL) and LiOH (38 mg, 0.9 mmol). The reaction mixture was stirred at room temperature overnight. The mixture was cooled down to 0° C. and neutralized to pH~6 with 1 N hydrochloride solution. The mixture was concentrated in vacuo to remove solvent THF, the residue was freeze-dried to give compound CCXXIX-7 (45 mg, yield: 79%). MS (ESI) m/z (M+H)$^+$ 632.

Preparation of Compound 34

A solution of compound CCXXIX-7 (45 mg, 0.071 mmol) in HCl/THF solution (4 N, 3 mL) was stirred at 0° C. for 2 hrs. The reaction mixture was concentrated in vacuo to remove THF, the residue was lyophilized to give Compound 34 (32 mg, yield: 84%). $^1$H NMR (400 MHz, Methanol-$d_4$): δ 7.88-7.89 (m, 2 H), 7.65-7.84 (m, 5 H), 7.19-7.52 (m, 5 H), 6.17-6.19 (q, 1 H), 4.78 (d, J=11.6 Hz, 2H), 4.57 (d, J=11.6 Hz, 2H), 2.21 (s, 3 H), 1.62 (d, J=6.0 Hz, 3 H). MS (ESI) m/z (M+H)$^+$ 532.1.

Synthesis of Compounds 37-40

Synthetic Route (Scheme CCXXX)

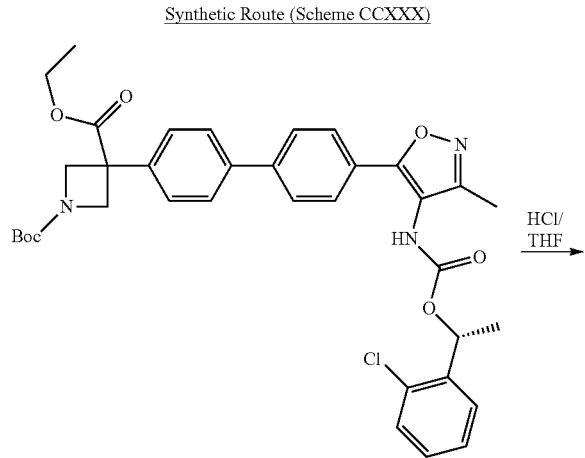

CCXXX-6

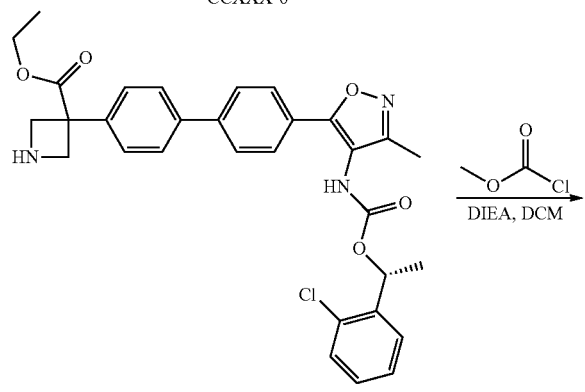

CCXXX-7

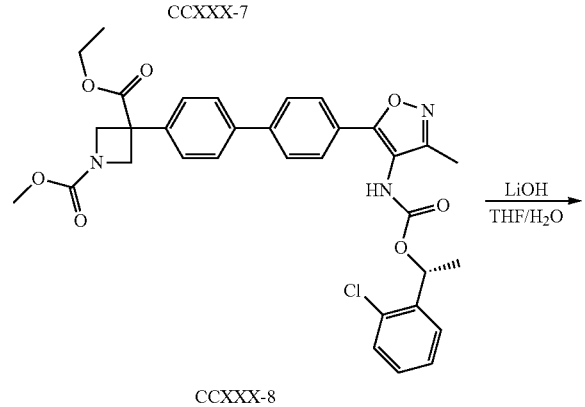

CCXXX-8

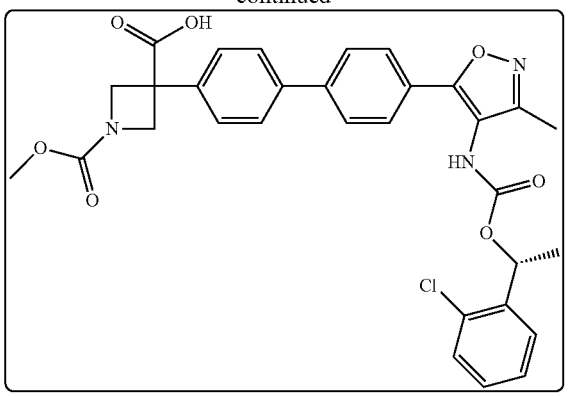

Compound 37

A solution of compound CCXXX-6 (660 mg, 1 mmol) in HCl/THF solution (10 mL) was stirred at 0° C. for 2 hrs. The reaction mixture was concentrated in vacuo to remove solvent THF, the residue was freeze-dried to give crude compound CCXXX-7 (560 mg, yield: 100%), which was used for next step directly.

To a solution of compound CCXXX-7 (100 mg, 0.178 mmol) in DCM (5 mL) was added methyl chloroformate (0.041 mL) and DIEA (0.3 mL) at 0-5° C. The reaction mixture was slowly warm to room temperature and stirred at r.t for 3 hours. Then the reaction mixture was poured into ice-water, and extracted with DCM (20 mL), washed with brine, dried and concentrated. The residue was purified by TLC (PE:EA=7:1) to give compound CCXXX-8 (60 mg, yield 54%). MS (ESI) m/z (M+H)$^+$ 618.

Preparation of Compound 37

To a solution of compound CCXXX-8 (55 mg, 0.089 mmol) in THF (3 mL) was added water (1 mL) and LiOH (37 mg, 0.89 mmol). The reaction mixture was stirred at room temperature overnight. The mixture was cooled down to 0° C. and neutralized to pH~6 with 1 N hydrochloride solution. The mixture was concentrated in vacuo to remove solvent THF, the residue was purified by Prep. HPLC and lyophilized to give Compound 37 (18 mg, yield: 27%). $^1$H NMR (400 MHz, DMSO-$d_6$): δ 9.47 (s, 1 H), 7.62-8.04 (m, 6 H), 7.38-7.49 (m, 6 H), 6.00-6.02 (q, 1 H), 4.51 (d, J=8.8 Hz, 2H), 4.24 (d, J=7.6 Hz, 2H), 3.65 (s, 3 H), 2.01 (s, 3 H), 1.56 (d, J=6.0 Hz, 3 H). MS (ESI) m/z (M+H)$^+$ 590.1.

Synthesis of Compound 38

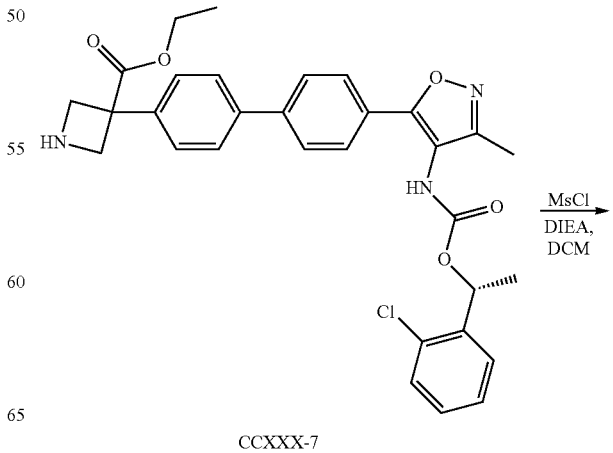

CCXXX-7

Synthesis of Compound 39

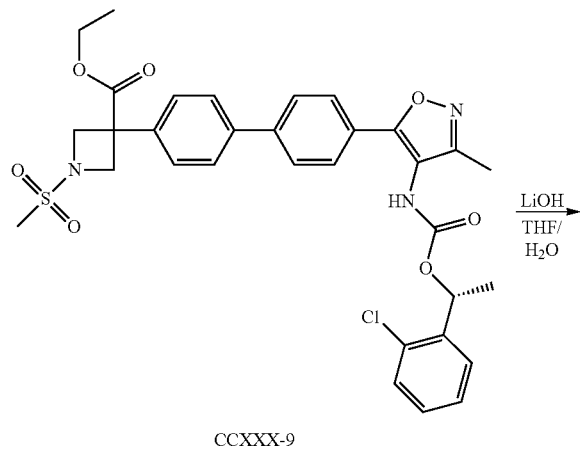

CCXXX-9

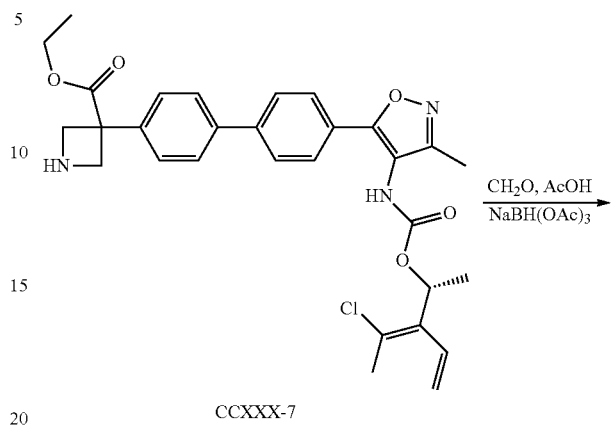

CCXXX-7

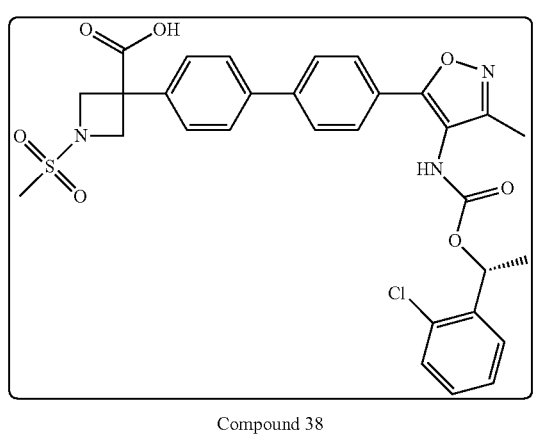

Compound 38

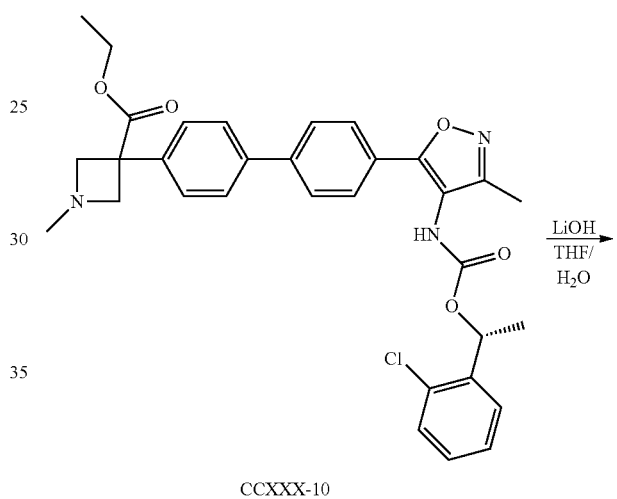

CCXXX-10

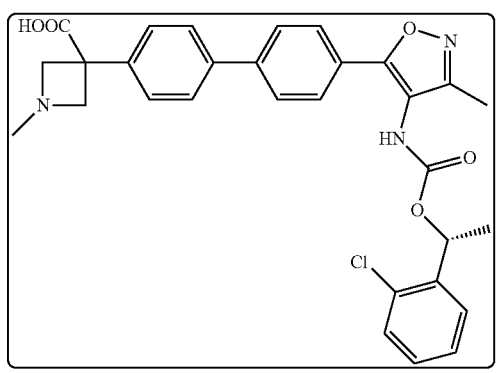

Compound 39

To a solution of compound CCXXX-7 (100 mg, 0.178 mmol) in DCM (5 mL) was added methanesulfonyl chloride (0.043 mL) and DIEA (0.3 mL) at 0-5° C. The reaction mixture was slowly warm to room temperature and stirred at r.t for 3 hours. The reaction mixture was poured into ice-water, and extracted with DCM, washed with brine and concentrated, purified by Prep. TLC (PE:EA=5:1) to give compound CCXXX-9 (65 mg, yield 57%). MS (ESI) m/z (M+H)+ 638.1.

To a solution of compound CCXXX-9 (60 mg, 0.094 mmol) in THF (3 mL) was added water (1 mL) and LiOH (39 mg, 0.94 mmol). The reaction mixture was stirred at room temperature overnight. The mixture was cooled down to 0° C. and neutralized to pH~6 with 1 N hydrochloride solution. The mixture was concentrated in vacuo to remove solvent THF, the residue was purified by Prep. HPLC and lyophilized to give Compound 38 (24 mg, yield: 42%). $^1$H NMR (400 MHz, DMSO): δ 13.33 (s, 1 H), 9.45 (s, 1 H), 7.77-7.98 (m, 6 H), 7.38-7.64 (m, 6H), 5.98-6.03 (q, 1 H), 4.45 (d, J=8.0 Hz, 2H), 4.28 (d, J=8.4 Hz, 2H), 3.04 (s, 3 H), 2.22 (s, 3 H), 1.41 (d, J=6.0 Hz, 3 H). MS (ESI) m/z (M+H)+ 610.0

To a stirred mixture of compound CCXXX-7 (100 mg, 0.178 mmol), NaBH(OAc)$_3$ (75 mg, 0.356 mmol), and AcOH (0.15 mL) in DCM (5 mL) was added HCHO solution (0.15 mL). The reaction mixture was stirred at r.t overnight. Then methanol (5 mL) was added, and the mixture was diluted with DCM (50 mL), washed with water and brine, dried over Na$_2$SO$_4$, filtered and concentrated. The residue was purified by prep. TLC (PE:EA=5:1) to afford give product CCXXX-10 (60 mg, yield: 59%).

To a solution of compound CCXXX-10 (50 mg, 0.087 mmol) in THF (3 mL) was added water (1 mL) and LiOH (36 mg, 0.87 mmol). The reaction mixture was stirred at room temperature overnight. The mixture was cooled down to 0° C. and neutralized to pH~6 with 1 N hydrochloride solution. The mixture was concentrated in vacuo to remove solvent THF, the residue was purified by Prep. HPLC and lyophilized to give Compound 39 (25 mg, yield: 35%). $^1$H NMR (400 MHz, DMSO-$d_6$): δ 9.45 (s, 1 H), 7.79-7.91 (m, 6 H), 7.38-7.64 (m, 6 H), 5.98-6.03 (q, 1 H), 4.63 (d, J=10 Hz, 2H), 4.42 (br, 2H), 2.81 (s, 3 H), 2.08 (s, 3 H), 1.56 (d, J=6.4 Hz, 3 H). MS (ESI) m/z (M+H)$^+$ 546.1.

Synthesis of Compound 40

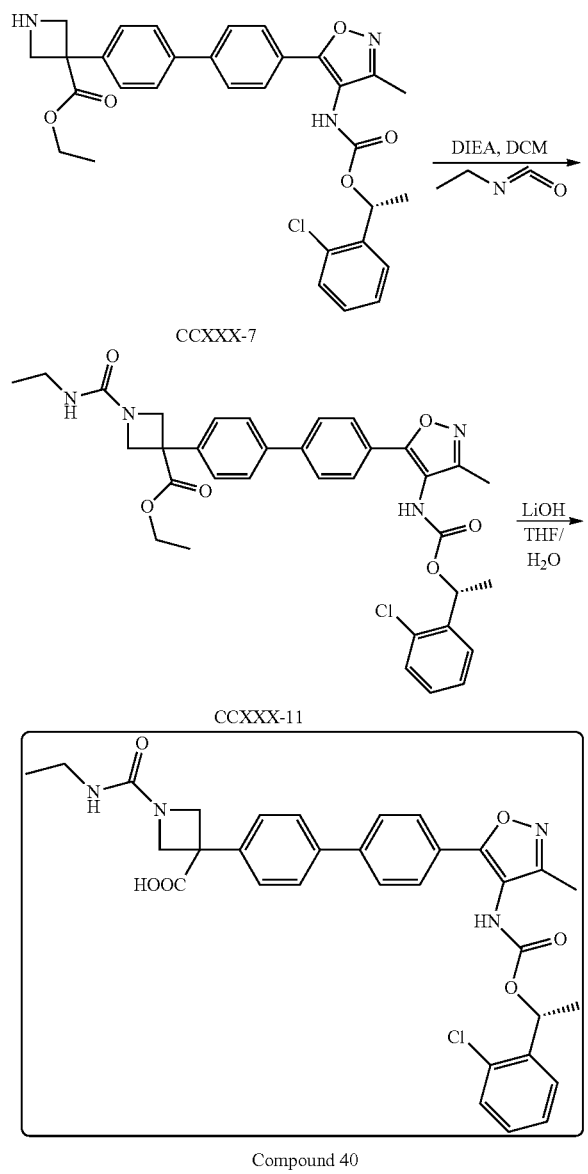

To a solution of compound CCXXX-7 (120 mg, 0.214 mmol) in DCM (5 mL) was added ethyl isocyanate (22.8 mg, 0.321 mmol) and DIEA (0.1 mL) at 0-5° C. The reaction mixture was slowly warm to room temperature and stirred at r.t for 2 hours. The reaction mixture was poured into ice-water, and extracted with DCM, washed with brine and concentrated. The residue was purified by Prep. TLC (PE:EA=5:1) to give compound CCXXX-11 (80 mg, yield 59%). MS (ESI) m/z (M+H)$^+$ 631.1.

To a solution of compound CCXXX-11 (70 mg, 0.113 mmol) in THF (3 mL) was added water (1 mL) and LiOH (45 mg, 1.13 mmol). The reaction mixture was stirred at room temperature overnight. The mixture was cooled down to 0° C. and neutralized to pH~6 with 1 N hydrochloride solution. The mixture was concentrated in vacuo to remove solvent THF, the residue was purified by Prep. HPLC and lyophilized to give Compound 40 (55 mg, yield: 72%). $^1$H NMR (400 MHz, DMSO-$d_6$): δ 9.42 (s, 1 H), 7.73-7.81 (m, 6 H), 7.36-7.47 (m, 6 H), 6.46-6.49 (q, 1 H), 5.97-5.99 (m, 1 H), 4.39 (d, J=8.4 Hz, 2H), 4.11 (d, J=8.4 Hz, 2H), 2.98-3.03 (m, 2H), 2.11 (s, 3 H), 1.54 (d, J=7.2 Hz, 3 H), 0.97 (t, J=7.2 Hz, 3 H). MS (ESI) m/z (M+H)$^+$ 603.1.

Synthesis of Compound 42

Synthetic Route (Scheme CCXXXI)

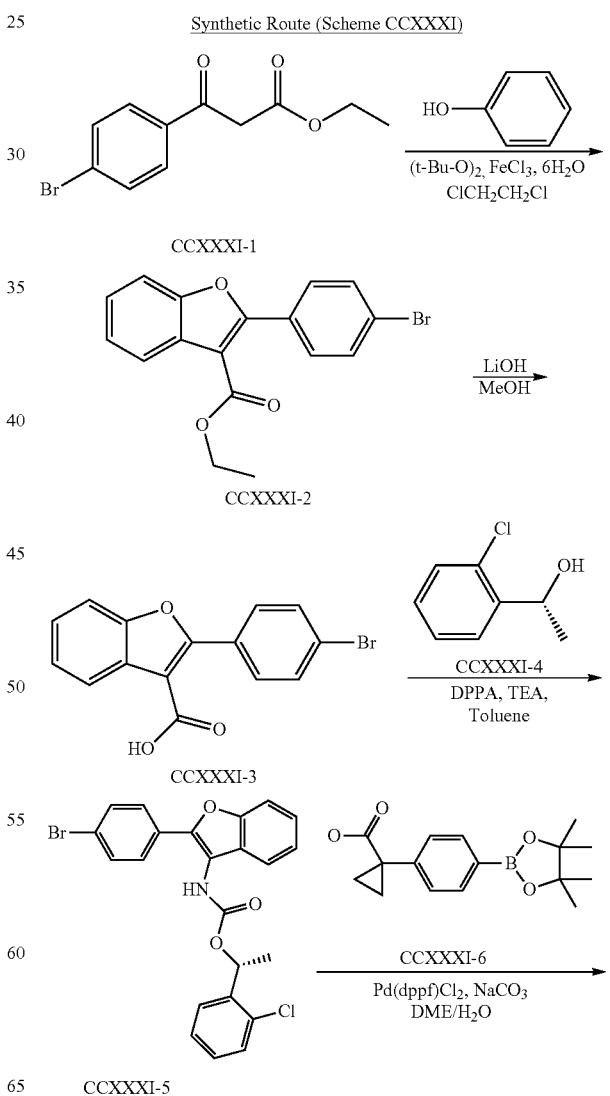

Synthesis of Compound 274
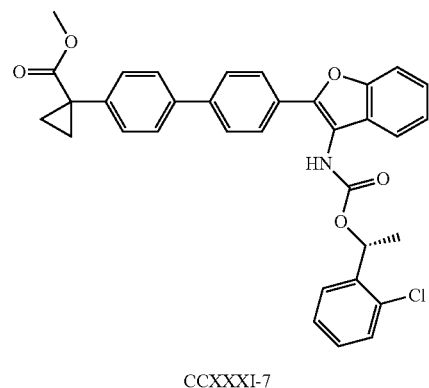
CCXXXI-7
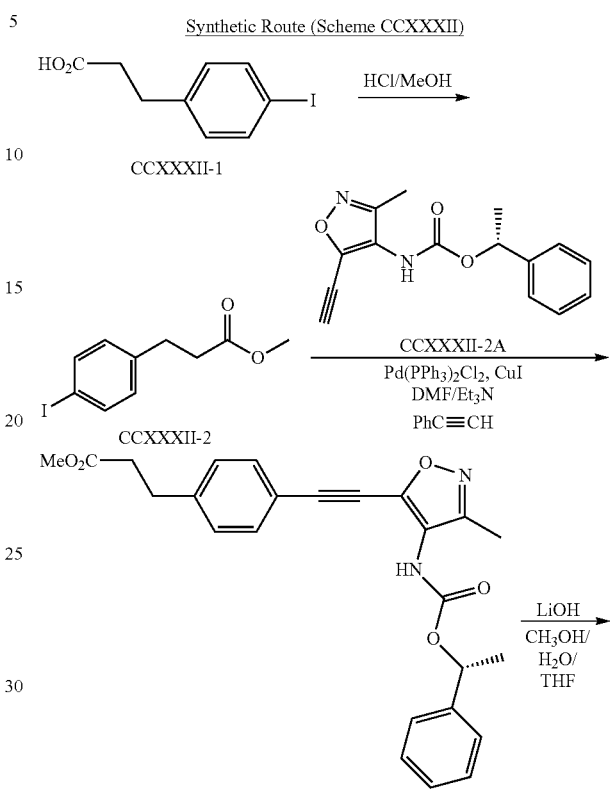
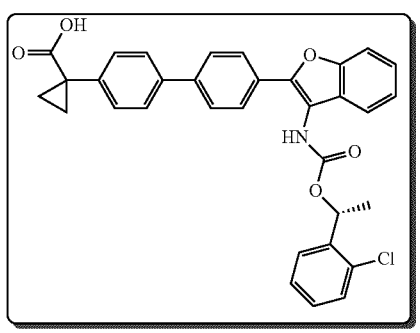
Compound 42
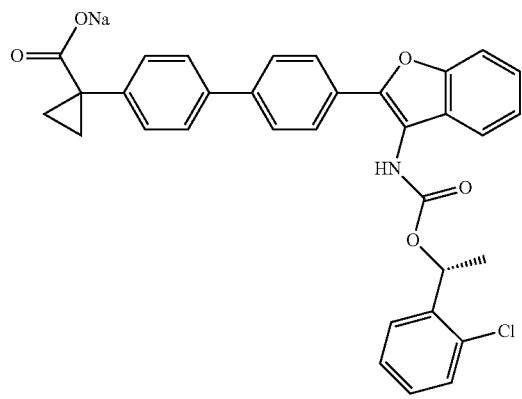
Compound 42a
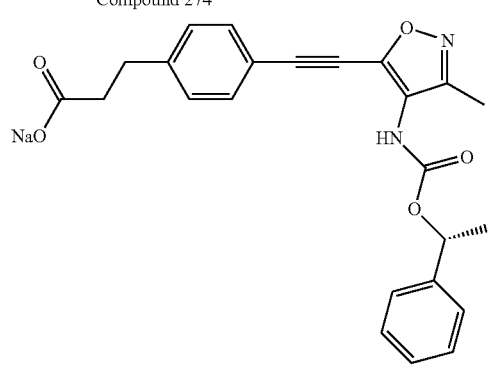
Compound 274a
Compound 42 was prepared analogously to the procedure described in the synthesis of Compound 31. Compound 42: $^1$HNMR (DMSO-$d_6$, 400 MHz) δ 12.37 (s, 1H), 9.68 (s, 1H), 7.94 (d, J=8.0 Hz, 2H), 7.78 (d, J=8.0 Hz, 2H), 7.71-7.60 (m, 4H), 7.59-7.25 (m, 8H), 6.04 (d, J=6.0 Hz, 1H), 1.60 (m, J=6.0 Hz, 3H), 1.50 (m, 2H), 1.20 (m, 2H). MS (ESI) m/z [M+Na]$^+$ 574.1.
Compound 42a $^1$HNMR (DMSO-$d_6$, 400 MHz) δ 9.71 (s, 1H), 7.93 (d, J=7.6 Hz, 2H), 7.80-7.62 (m, 4H), 7.59-7.26 (m, 10H), 6.05 (d, J=6.0 Hz, 1H), 1.60 (d, J=6.0 Hz, 3H), 1.23 (m, 2H), 0.73 (m, 2H). MS (ESI) m/z (M+Na)$^+$ 574.2.

The solution of compound CCXXXII-1 (1 g, 3.6 mmol) in HCl/MeOH (4N, 20 mL) was stirred at 80° C. overnight. The solvent was removed under reduced pressure to afford compound CCXXXII-2 (1 g, crude yield 95.2%), which was used to next step without further purification.

Compound CCXXXII-2 (110 mg, 0.38 mmol), Pd(PPh$_3$)$_2$Cl$_2$ (13 mg), and CuI (13 mg, 0.06 mmol) were mixed with DMF (1 mL) and Et$_3$N (3 mL) under Ar$_2$ protection. Ethynylbenzene (3 uL, 0.027 mmol) was added to this mixture at room temperature. Then a solution of compound 2A (80 mg, 0.3 mmol) in DMF (0.2 mL) and Et$_3$N (0.6 mL) was added slowly at room temperature. The mixture was stirred at room temperature for 1 h. TLC showed complete reaction. Then H$_2$O was added, and extracted with EtOAc. The organics were collected, dried with Na$_2$SO$_4$, filtered and concentrated. The residue was purified by column (PE:EA=3:1) to give pure compound CCXXXII-3 (66 mg, 51.4%). MS (ESI) m/z (M+H)$^+$ 433.1.

Compound 274 was prepared analogously to the procedure described in the synthesis of Compound 81. MS (ESI) m/z (M+H)$^+$419.1. Compound 274a: $^1$H NMR (DMSO-d$_6$, 400 MHz): δ7.28-7.37 (m, 9H), 5.75-5.80 (q, 1H), 2.79 (t, J=8.0 Hz, 2H) 2.15-2.18 (m, 5H), 1.52 (d, J=6.4 Hz, 3H). MS (ESI) m/z (M+H)$^+$ 419.1.

In Vitro Assays

Establishment of a CHO Cell Line Stably Expressing Human LPA$_1$

A 1.1 kb cDNA encoding the human LPA$_1$ receptor is cloned from human lung. Human lung RNA (Clontech Laboratories, Inc. USA) is reverse transcribed using the RETROscript kit (Ambion, Inc.) and the full-length cDNA for human LPA$_1$ is obtained by PCR of the reverse transcription reaction. The nucleotide sequence of the cloned human LPA$_1$ is determined by sequencing and is confirmed to be identical to the published human LPA$_1$ sequence (An et al. Biochem. Biophys. Res. Commun. 231:619 (1997). The cDNA is cloned into the pcDNA5 pcDNA5/FRT expression plasmid and is transfected in CHO cells using lipofectamine 2000 (Invitrogen Corp., USA). Clones stably expressing human LPA$_1$ are selected using hygromycin and identified as cells that show Ca-influx in response to LPA.

Generation of Cells Transiently Expressing Human LPA$_2$

A vector containing the human LPA$_2$ receptor cDNA is obtained from the Missouri S&T cDNA Resource Center (www.cdna.org). The full-length cDNA fragment for human LPA$_2$ is obtained by PCR from the vector. The nucleotide sequence of the cloned human LPA$_2$ is determined by sequencing and is confirmed to be identical to the published human LPA$_2$ sequence (NCBI accession number NM_004720). The cDNA is cloned into the pcDNA3 pcDNA3.1 expression plasmid and is transfected into B103 cells (Invitrogen Corp., USA) by seeding cells in a 96-well poly-D-lysine coated plate at 30,000-35,000 cells per well together with 0.2 μl lipofectamine 2000 and 0.2 μg of the LPA$_2$ expression vector. Cells are cultured overnight in complete media before being assayed for LPA-induced Ca-influx.

Establishment of a CHO Cell Line Stably Expressing Human LPA$_3$

A vector containing the human LPA$_3$ receptor cDNA is obtained from the Missouri S&T cDNA Resource Center (www.cdna.org). The full-length cDNA fragment for human LPA$_3$ is obtained by PCR from the vector. The nucleotide sequence of the cloned human LPA$_3$ is determined by sequencing and is confirmed to be identical to the published human LPA$_3$ sequence (NCBI accession number NM_012152). The cDNA is cloned into the pcDNA5 pcDNA5/FRT expression plasmid and is transfected in CHO cells using lipofectamine 2000 (Invitrogen Corp., USA). Clones stably expressing human LPA$_3$ are selected using hygromycin and identified as cells that show Ca-influx in response to LPA.

LPA1 and LPA3 Calcium Flux Assays

Human LPA$_1$ or LPA$_3$ expressing CHO cells were seeded at 20,000-45,000 cells per well in a 96-well poly-D-lysine coated plate one or two days before the assay. Prior to the assay, the cells were washed once with PBS and then cultured in serum-free media overnight. On the day of the assay, a calcium indicator dye (Calcium 4, Molecular Devices) in assay buffer (HBSS with Ca$^{2+}$ and Mg$^{2+}$ and containing 20 mM Hepes and 0.3% fatty-acid free human serum albumin) was added to each well and incubation continued for 1 hour at 37° C. 10 μl of test compounds in 2.5% DMSO were added to the cells and incubation continued at room temperature for 30 minutes. Cells were then stimulated by the addition of 10 nM LPA and intracellular Ca$^{2+}$ measured using the Flexstation 3 (Molecular Devices). IC$_{50s}$ were determined using Graphpad prism analysis of drug titration curves.

LPA2 Calcium Flux Assay

Following an overnight culture with lipofectamine 2000 and the LPA$_2$ expression vector, the B103 cells are washed once with PBS then serum starved for 4 hours. A calcium indicator dye (Calcium 4, Molecular Devices) in assay buffer (HBSS with Ca$^{2+}$ and Mg$^{2+}$ and containing 20 mM Hepes and 0.3% fatty-acid free human serum albumin) is added to each well and incubation continued for 1 hour at 37° C. 10 μl of test compounds in 2.5% DMSO are added to the cells and incubation continued at room temperature for 30 minutes. Cells are the stimulated by the addition of 10 nM LPA and intracellular Ca$^{2+}$ measured using the Flexstation 3 (Molecular Devices). IC$_{50}$, are determined using Graphpad prism analysis of drug titration curves.

GTPγS Binding Assay

The ability of a compound to inhibit binding of GTP to LPA$_1$ is assessed via a membrane GTPγS assay. CHO cells stably expressing the recombinant human LPA$_1$ receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~(−25 μg per well) are incubated in 96-well plates with 0.1 nM [$^{35}$S]-GTPγS, 900 nM LPA, 5 μM GDP, and test compound in Assay Buffer (50 mM Hepes, pH 7.4, 100 mM NaCl, 10 mM MgCl$_2$, 50 μg/ml saponin and 0.2% fatty-acid free human serum albumin) for 30 minutes at 30° C. The reactions are terminated by rapid filtration through Whatman GF/B glass fiber filter plates. The filter plates are washed 3 times with 1 ml cold Wash Buffer (50 mM Hepes, 7.5, 100 mM NaCl and 10 mM MgCl$_2$) and dried. Scintillant is then added to the plates and the radioactivity retained on the filters is determined on a Packard TopCount (Perkin Elmer). Specific binding is determined as total radioactive binding minus non-specific binding in the absence of the ligand (900 nM LPA). IC$_{50}$, are determined using Graphpad prism analysis of drug titration curves.

Beta-Arrestin Based Assays for Human LPA1R Antagonists and Agonists

A CHO cell line stably expressing the ProLink™ tagged human LPA1R was obtained from DiscoverX Inc, Fremont, Calif. In this system, β-Arrestin was fused to an N-terminal deletion mutant of β-galactosidase (termed the enzyme acceptor or EA), the human LPA1R was fused to a smaller (42 amino acids) weakly complementing fragment termed ProLink™. In cells that stably express these fusion proteins, agonist/ligand stimulation resulted in the interaction of β-Arrestin and the ProLink-tagged GPCR, forcing the complementation of the two β-galactosidase fragments and resulting in the formation of a functional enzyme that converted substrate to detectable signal. Cell handling and assays were performed according to protocols specified in the PathHunter® assays kits (DiscoverX, Fremont, Calif.). Assays were performed in quadruplicate in white 384 well plates. End point luminescence data were plotted and fit to a 4 parameter logistic function to obtain $IC_{50}$ values. For antagonist assays, an $IC_{80}$ concentration of agonist (LPA) equal to 0.5 micromolar was used.

Beta-Arrestin Based Assays for LPA and S1P Receptor Antagonists and Agonists (Human and Species Orthologs) Using Transiently Transfected Cells CMV promoter based DNA constructs expressing a fusion of the LPA/S1P GPCR of interest and ProLink™ tag were used to transfect EA Parental™ CHO cells (DiscoverX, Fremont, Calif.) using a FuGENE® transfection kit (Roche). Beta-Arrestin based assays were conducted 24-48 hrs post transfection using PathHunter® assay kits (DiscoverX, Fremont, Calif.). Agonist and antagonist assays were performed in quadruplicate in white 384 well plates. End point luminescence data were plotted and fit to a 4 parameter logistic function to obtain $IC_{50}$ values. For antagonist assays, an $IC_{80}$ concentration of agonist (LPA) equal to 0.5 micromolar was used.

cAMP Based Assays for Human LPA1R Antagonists and Agonists

A CHO cell line stably expressing the human LPA1R (DiscoverX Inc, Fremont, Calif.) was used according to manufacturer's protocol. HitHunter® assay kits (DiscoverX, Fremont, Calif.) were used to measure cAMP levels. HitHunter® cAMP assays are competitive immunoassays. Free cAMP from cell lysates competed for antibody binding against labeled cAMP (ED-cAMP conjugate). Unbound ED-cAMP was free to complement EA to form active enzyme, which subsequently hydrolyzed substrate to produce signal. A positive signal generated was directly proportional to the amount of free cAMP bound by the binding protein. Forskolin (15 micromolar) was used to elevate cAMP levels. Increased LPA (agonist) activity was measured as a decrease in cAMP levels. For antagonist assays, an $IC_{80}$ of LPA (agonist) equal to 50 micromolar was used, and increased antagonist activity of the test compound was recorded as an increase in cAMP levels. All assays were performed in quadruplicate in white 384 well plates. End point luminescence data were plotted and fit to a 4 parameter logistic function to obtain $IC_{50}$ values.

LPA1 Chemotaxis Assay

Chemotaxis of the A2058 human melanoma cells is measured using the Neuroprobe ChemoTx® System plates (8 μm pore size, 5.7 mm diameter sites). The filter sites are coated with 0.001% fibronectin (Sigma) in 20 mM Hepes, pH 7.4 and allowed to dry. A2058 cells are serum-starved for 24 hours, then are harvested with Cell Stripper and are resuspended in DMEM containing 0.1% fatty-acid-free bovine serum albumin (BSA) to a concentration of 1.times.10.sup.6/ ml. Cells are mixed with an equal volume of test compound (2×) in DMEM containing 0.1% fatty-acid-free BSA and incubated at 37° C. for 15 minutes. LPA (100 nM in DMEM containing 0.1% fatty-acid-free BSA) or vehicle is added to each well of the lower chamber and 50 μl of the cell suspension/test compound mix is applied to the upper portion of the ChemoTx® plate. Plates are incubated at 37° C. for three hours and then the cells are removed from the upper portion by rinsing with PBS and scraping. The filter is dried then stained with HEMA 3 Staining System (Fisher Scientific). The absorbance of the filter is read at 590 nM and $IC_{50}$, are determined using Symyx Assay Explorer.

LPA1 Migration Assay

Migration of primary fibroblasts (including lung, dermal), HFL-1, 3T3 and CHO cells expressing LPA1R were monitored using the Oris™ assay (Platypus Technologies, Madison, Wis.). These cells were dye (Cell Tracker Green™) loaded and serum starved for 12-24 hrs. In response to chemoattractants such as LPA and serum, the cells migrated inward in to the exclusion (detection) zone. After fixing, fluorescent cells in the detection zone were counted using a high content reader. The ability of LPA1 antagonists to inhibit cell migration is quantified by plotting cell number vs. compound concentration and curve fitting the resulting dose-response curve to a 4 parameter logistic function.

Assay of Inhibitory Effect on Cell Proliferation ([$^3$H] Thymidine Incorporation)

Fibroblasts (primary human lung and dermal, HFL-1, 3T3 etc) are plated on a 96-well plate and serum starved for 24-48 hours. The media are then exchanged for media containing stimulants (LPA, TGFb, serum etc) and cultured further for 16-24 hours before [$^3$H] thymidine addition. After culturing for another 8 hours, cells are washed with PBS and the amount of [$^3$H] thymidine incorporated into the cells are assayed by Betaplate filter counter system (Amersham Pharmacia Biotech). The difference between the amount of [$^3$H] thymidine incorporated in the stimulant-added well and the amount of [$^3$H] thymidine incorporated in the well containing no stimulant represents the amount of [$^3$H] thymidine incorporation accelerated by stimulant. The increase of [$^3$H] thymidine incorporation without the addition of test compounds is set as 100% and the concentration of compound with 50% inhibition in the increase of [$^3$H] thymidine incorporation ($IC_{50}$ value) is determined. The test compounds are added 0-30 min before stimulant addition.

Assay of Inhibitory Effect on Cell Proliferation (BrdU Incorporation)

Fibroblasts (primary human lung and dermal, HFL-1, 3T3 etc) were plated on a 96-well plate and serum starved for 24-48 hours. The media were then exchanged for media containing stimulants (LPA, TGFb, serum etc) and cultured further for 16-24 hours before BrdU addition. After culturing for another 8 hours, cells were washed with PBS and the amount of BrdU incorporated into the cells was assayed by absorbance at 450 nm using the Cell proliferation ELISA system (RPN250, Amersham LIFE SCIENCE). The difference between the amount of BrdU incorporated in the stimulant-added well and the amount of BrdU incorporated in the well containing no stimulant represented the amount of BrdU incorporation accelerated by stimulant. The increase of BrdU incorporation without the addition of test compounds was set as 100% and the concentration of compound with 50% inhibition in the increase of BrdU incorporation ($IC_{50}$ value) was determined. The test compounds were added 0-30 min before stimulant addition.

Myofibroblast Differentiation

Fibroblasts (primary human lung and dermal, HFL-1, 3T3 etc) are plated on a 96-well plate and serum starved for 24-48 hours. The media are then exchanged for media containing stimulants (LPA, TGFb, etc) and cultured further for 24-48 hours. The amount of alpha smooth muscle actin (aSMA) is quantitated using an ELISA kit (Thermo Scientific, USA). Alternatively after fixing and permeabilization, aSMA is also quantitated using immunohistochemical methods (FITC conjugated anti-aSMA, Sigma).

Assay for Effect of Compounds on Collagen Production

HFL-1 Cells (ATCC, Rockville, Md.) are grown under regular tissue culture conditions in complete media containing 10% fetal bovine serum (FBS; Mediatech, Inc. Herndon, Va.). Cells in early passage are plated in 6 well plates. When the cells reach confluence, the media is removed, cells are washed with PBS, and the cells are kept overnight in complete media containing 0.1% FBS. The media is then replaced with fresh media plus 0.1% FCS, 10 flM L-Proline (EMD Chemicals, Gibbstown, N.J.), 20 fig/mL ascorbic acid (EMD Chemicals, Gibbstown, N.J.). Compounds are added to triplicate wells to a final concentration of 1 mM from 100× stock solutions in DMSO. One hour after the addition of compound, the cells are treated with TGFb (Sigma-Aldrich, St. Louis, Mo.) to a final concentration of 10 ng/mL (25 ng total). Three days after addition of TGFb the media is removed, cells are washed with PBS and then lysed. The total collagen content of lysed cells is assessed with a dye-based collagen assay (Sircol Collagen Assay, Newtownabbey, Northern Ireland) and an flQuant plate-based spectrophotometer (BioTek Instruments, Inc., Winooski, Vt.) with appropriate standard curves. The dynamic range of the assay is defined by cells that were mock treated (1% DMSO without compound) in the presence and absence of TGFb.

Bleomycin-Induced Lung Fibrosis Model in Mice or Rats

Female C57B1/6CD-1 mice (Harlan, 25-30 g) or Wistar rats (Harlan, 200-250 g) are housed 4 per cage, given free access to food and water and allowed to acclimate for at least 7 days prior to test initiation. After the habituation phase, animals are lightly anesthetized with isoflurane (5% in 100% $O_2$) and administered with bleomycin sulfate (Henry Schein) via intratracheal instillation (Cuzzocrea S et al. Am J Physiol Lung Cell Mol. Physiol. 2007 May; 292(5):L1095-104. Epub 2007 Jan. 12.). Animals are returned to their cages and monitored daily for the duration of the experiment. Test compound or vehicle is delivered po, ip, or sc daily. The route and frequency of dosing is based on previously determined pharmacokinetic properties. All animals are sacrificed using inhaled isoflurane 3, 7, 14, 21 or 28 days after bleomycin instillation. Following sacrifice, animals are intubated with a 20 gauge angiocatheter attached to a 1 ml syringe. Lungs are lavaged with saline to obtain bronchoalveolar lavage fluid (BALF) and then removed and fixed in 10% neutral buffered formalin for subsequent histopathological analysis. BALF is centrifuged for 10 min at 800×g to pellet the cells and the cell supernatant removed and frozen at −80° C. for subsequent protein analysis using the DC protein assay kit (Biorad, Hercules, Calif.) and soluble collagen analysis using Sircol (Biocolor Ltd, UK). BALF is analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The cell pellet is re-suspended in PBS. Total cell counts are then obtained using a Hemavet hematology system (Drew Scientific, Wayne, Pa.) and differential cells counts are determined using Shandon cytospin (Thermo Scientific, Waltham, Mass.). Lung tissue is stained using hematoxylin and eosin (H&E) and trichrome and lung fibrosis is determined by semiquantitative histopathological scoring (Ashcroft T. et al. J. Clin. Path. 1988; 41; 4, 467-470) using light microscopy (10× magnification) and quantitative, computer-assisted densitometry of collagen in lung tissue sections using light microscopy. The data are plotted using Graphpad prism and statistical differences between groups determined.

Mouse Carbon Tetrachloride (CCl4)-Induced Liver Fibrosis Model

Female C57BL/6 mice (Harlan, 20-25 g) housed 4/cage are given free access to food and water and allowed to acclimate for at least 7 days prior to test initiation. After the habituation phase, mice receive CCl.sub.4 (0.5-1.0 ml/kg body weight) diluted in corn oil vehicle (100 µL volume) via i.p. injection twice a week for 84-6 weeks. (Higazi, A. A. et al., Clin Exp Immunol. 2008 April; 152(1):163-73. Epub 2008 Feb. 14.). Control mice receive an equivalent volume of corn oil vehicle only. Test compound or vehicle is delivered po, ip, or sc daily. At the end of the study (8 weeks after first i.p. injection of $CCl_4$), mice are sacrificed using inhaled isoflurane and blood is drawn via cardiac puncture for subsequent analysis of ALT/AST levels. The liver is harvested, and one half of the liver is frozen at −80° C. and the other half is fixed in 10% neutral buffered formalin for histological assessment of liver fibrosis using light microscopy (10× magnification). Liver tissue homogenates are analyzed for collagen levels using Sircol (Biocolor Ltd, UK). Fixed Liver tissue is stained using hematoxylin and eosin (H&E) and trichrome and liver fibrosis is determined by quantitative, computer-assisted densitometry of collagen in liver tissue sections using light microscopy. Plasma and liver tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor, and lactate dehydrogenase activity, using commercially available ELISA. The resulting data are plotted using Graphpad prism and statistical differences between groups determined.

Mouse Intravenous LPA-Induced Histamine Release

A mouse intravenous LPA-induced histamine release model is utilized to determine the in vivo potency of $LPA_1$ and $LPA_3$ receptor antagonists. Female CD-1 mice (weighing 25-35 grams) are administered compound (i.p., s.c. or p.o.) in a volume of 10 ml/kg 30 minutes to 24 hours prior to intravenous LPA challenge (300 µg/mouse in 0.1% FAF BSA). Immediately following LPA challenge mice are placed into an enclosed Plexiglas chamber and exposed to an isoflurane for a period of 2-10 minutes. They are removed, and blood collected into tubes containing EDTA. Blood is then centrifuged at 10,000×g for 10 minutes at 4° C. Histamine concentrations in the plasma are determined by EIA. Drug concentrations in plasma are determined by mass spectrometry. The dose to achieve 50% inhibition of blood histamine release is calculated by nonlinear regression (Graphpad Prism) and plotted as the $ED_{50}$. The plasma concentration associated with this dose is plotted as the $EC_{50}$.

Mouse Unilateral Ureteral Obstruction Kidney Fibrosis Model

Female C57BL/6 mice (Harlan, 20-25 g) housed 4/cage will be given free access to food and water and allowed to acclimate for at least 7 days prior to test initiation. After the habituation phase, mice undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. Mice are returned to their cages and monitored daily for the duration of the experiment. Test compound or vehicle is delivered po, ip, or sc daily. The route and frequency of dosing is based on previously determined pharmacokinetic properties. All animals are sacrificed using inhaled isoflurane 4, 8, 14, 21, or 28 days after UUO surgery. Following sacrifice blood is drawn via cardiac puncture, the kidneys are harvested and one half of the kidney is frozen at −80° C. and the other half is fixed in 10% neutral buffered formalin for histological assessment of kidney fibrosis using light microscopy (10× magnification). Kidney tissue homogenates are analyzed for collagen levels using Sircol (Biocolor Ltd, UK). Fixed kidney tissue is also stained using hematoxylin and eosin (H&E) and trichrome and kidney fibrosis is determined by quantitative, computer-assisted densitometry of collagen in liver tissue sections using light microscopy and collagen content in kidney lysate. Plasma and kidney tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and plasminogen activator inhibitor-1 lactate dehydrogenase activity, using commercially available ELISA. The resulting data are plotted using Graphpad prism and statistical differences between groups determined.

Mouse Dermal Vascular Leak Assay

Female BALB/c mice (Harlan) weighing 20-25 grams are given free access to standard mouse chow and water and are allowed to acclimate for two weeks prior to study initiation. Compounds are prepared in at a range of concentrations and delivered by oral gavage. Three hours following dose, mice are placed into a restraining device and given Evan's blue dye intravenously by tail vein injection (0.2 ml of a 0.5% solution). Mice are then anesthetized using 3% isoflurane anesthesia to allow for intradermal injection of LPA (30 μg in 20 μll 0.1% fatty acid free BSA). Thirty minutes after LPA injection mice are sacrificed by CO2 inhalation and the skin is removed from the challenge site and placed into 2 ml formamide for overnight extraction of Evan's blue dye. Following extraction, a 150 μl aliquot of formamide for each tissue sample is placed into a 96 well plate and read at 610 nm using a photospectrometer. The resulting data (OD units) are plotted using GraphPad Prizm.

Bleomycin Dermal Fibrosis Model

Bleomycin is dissolved in phosphate buffered saline (PBS) at 10 ug/ml, and sterilized by filtration. Bleomycin or PBS control (100 ul) is injected subcutaneously into two locations on the shaved back of C57/BL6 or 5129 mice (Charles River/Harlan Labs, 20-25 g) once daily for 28 days while under isoflourane anesthesia (5% in 100% O2). Test compounds or controls are administered throughout the study via subcutaneous or intraperitoneal injection, or via oral gavage. After 28 days, mice are euthanized and 6 mm-full thickness punch biopsies are obtained from each injection site. Dermal fibrosis is assessed by histopathology and hydroxyproline biochemical assays.

Rat Dermal Wound Healing

Female rats (Harlan Labs, 200-250 g) are given a single 1 cm-full thickness incisional wound on the back while under isoflourane anesthesia. The incision is placed parallel to the midline along the dorsal skin, using a surgical scalpel. For excisional wounds, an 8 mm-full thickness skin biopsy punch is made on the back of each animal opposite to the site of the incision. Test compounds are administered prior to wounding, and dosed for 14 days. Wounds are allowed to heal, and photographs are taken and analyzed digitally to measure wound healing throughout the study. At the end of the study animals are euthanized and wound closure determined.

Assay Data for Compounds

Compounds of the preferred embodiments were prepared according to the methods described herein and assay data obtained for one or more of the Beta Arrestin $EC_{50}$, Ca Flux LPA1 $IC_{50}$, and/or Ca Flux LPA3 $IC_{50}$ assays. Control compounds were also prepared and assay data obtained. The assay data obtained is presented in Tables 20 and 21, in which A=greater than 500 nM, B=greater than or equal to 50 nM and less than or equal to 500 nM; and C=less than 50 nM.

TABLE 20

| Compound | Beta Arrestin $EC_{50}$ | Ca Flux LPA1 $IC_{50}$ | Ca Flux LPA3 $IC_{50}$ |
|---|---|---|---|
| Compound 5 | B | NA | NA |
| Compound 6 | C | B | B |
| Compound 7 | C | C | B |
| Compound 8 | A | A | NA |
| Compound 14 (Isomer 1) | C | C | B |
| Compound 15 | A | NA | NA |
| Compound 16 (Isomer 2) | C | NA | NA |
| Compound 17 | A | NA | NA |
| Compound 18 | A | NA | NA |
| Compound 19 | A | A | NA |
| Compound 20 | B | C | A |
| Compound 21 (Mixture of Isomers) | B | NA | NA |
| Compound 22 | A | NA | NA |
| Compound 23 (Isomer 1) | B | NA | NA |
| Compound 24 (Isomer 2) | B | NA | NA |
| Compound 25 | C | NA | NA |
| Compound 26 (Isomer 1) | C | NA | NA |
| Compound 27 (Isomer 2) | C | NA | NA |
| Compound 28 | C | B | NA |
| Compound 29 | A | NA | NA |
| Compound 30 | C | C | NA |
| Compound 31 | B | NA | NA |
| Compound 32 | C | B | A |
| Compound 33 | C | NA | NA |

TABLE 20-continued

| Compound | Beta Arrestin EC$_{50}$ | Ca Flux LPA1 IC$_{50}$ | Ca Flux LPA3 IC$_{50}$ |
|---|---|---|---|
| Compound 34 | A | NA | NA |
| Compound 35 | A | NA | NA |
| Compound 36 | A | NA | NA |
| Compound 37 | C | NA | NA |
| Compound 38 | C | NA | NA |
| Compound 39 | B | NA | NA |
| Compound 40 | B | NA | NA |
| Compound 41 | C | NA | NA |
| Compound 42 | C | NA | NA |
| Compound 43 | A | NA | NA |
| Compound 44 | C | C | NA |
| Compound 45 | C | C | NA |
| Compound 46 | B | B | NA |
| Compound 47 | A | NA | NA |

TABLE 20-continued
| Compound | Beta Arrestin EC$_{50}$ | Ca Flux LPA1 IC$_{50}$ | Ca Flux LPA3 IC$_{50}$ |
| --- | --- | --- | --- |
| 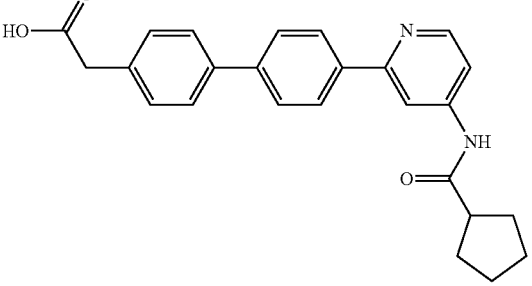  Compound 48 | A | NA | NA |
| 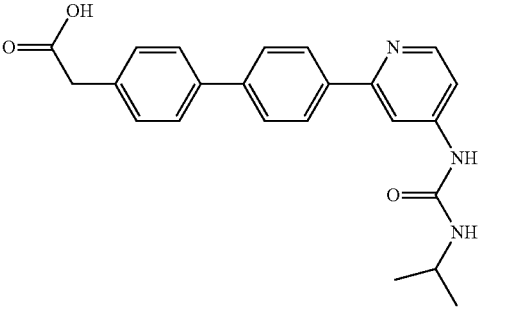  Compound 49 | A | NA | NA |
| 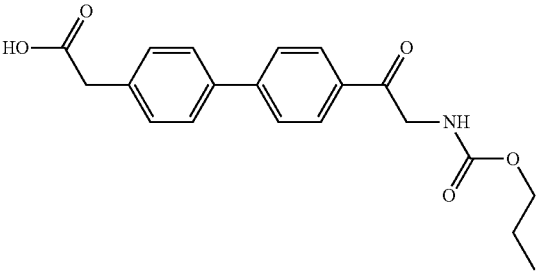  Compound 50 | A | NA | NA |
| Compound 51 | A | NA | NA |
| Compound 52 | A | NA | NA |
| Compound 53 | A | NA | NA |
| 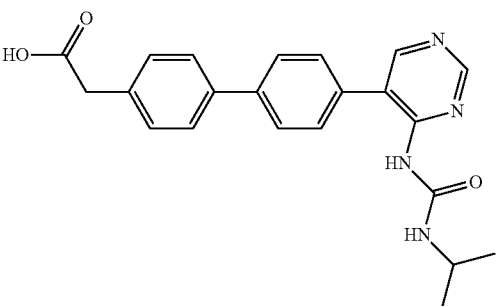  Compound 54 | A | NA | NA |
| Compound 56 | C | B | NA |
| Compound 60 | B | A | NA |

TABLE 20-continued

| Compound | Beta Arrestin EC$_{50}$ | Ca Flux LPA1 IC$_{50}$ | Ca Flux LPA3 IC$_{50}$ |
|---|---|---|---|
| Compound 61 | C | A | NA |
| Compound 62 | A | A | NA |
| Compound 63 | C | C | NA |
| Compound 64 | C | B | NA |
| Compound 65 | C | C | A |
| Compound 66 | B | NA | NA |
| Compound 67 | C | C | NA |
| Compound 68 | A | A | NA |
| Compound 69 | C | NA | NA |
| Compound 70 (isomer 1 of Compound 69) | C | A | NA |
| Compound 71 (isomer 2 of Compound 69) | B | A | NA |
| Compound 72 | A | NA | NA |
| Compound 73 | B | NA | NA |
| Compound 74 | C | C | A |
| Compound 75 | B | A | NA |
| Compound 76 | B | NA | NA |
| Compound 77 | A | NA | NA |
| Compound 78 | B | B | NA |
| Compound 79 | C | B | NA |
| Compound 80 | C | B | NA |
| Compound 81 | C | C | NA |
| Compound 82 | B | A | NA |
| Compound 83 | C | B | NA |
| Compound 84 | B | NA | NA |
| Compound 85 | B | NA | NA |
| Compound 86 | C | B | NA |
| Compound 87 | C | NA | NA |
| Compound 88 | B | NA | NA |
| Compound 89 | B | NA | NA |
| Compound 90 Sodium salt | B | NA | NA |
| Compound 91 | A | NA | NA |
| Compound 92 | C | NA | NA |
| Compound 93 | C | NA | NA |
| Compound 94 | B | NA | NA |
| Compound 95 | A | NA | NA |
| Compound 96 | C | NA | NA |
| Compound 97 | C | NA | NA |
| Compound 98 | B | NA | NA |
| Compound 99 | A | NA | NA |
| Compound 100 | B | NA | NA |
| Compound 101 | A | NA | NA |
| Compound 102 | B | NA | NA |
| Compound 103 | B | NA | NA |
| Compound 104 | A | NA | NA |
| Compound 105 | C | C | NA |
| Compound 106 | B | NA | NA |
| Compound 107 | C | C | NA |
| Compound 108 | B | NA | NA |
| Compound 109 | B | NA | NA |
| Compound 110 | B | NA | NA |
| Compound 111 | A | NA | NA |
| Compound 112 | C | NA | NA |
| Compound 113 | C | NA | NA |
| Compound 114 | C | NA | NA |
| Compound 115 | C | NA | NA |
| Compound 116 | C | NA | NA |
| Compound 117 | C | NA | NA |
| Compound 118 | B | NA | NA |
| Compound 119 | C | NA | NA |
| Compound 120 | C | NA | NA |
| Compound 121 | C | NA | NA |
| Compound 122 | C | NA | NA |
| Compound 123 | B | NA | NA |
| Compound 124 | C | NA | NA |
| Compound 125 | B | NA | NA |
| Compound 126 | B | NA | NA |
| Compound 127 | B | NA | NA |
| Compound 128 | B | NA | NA |
| Compound 129 | B | NA | NA |
| Compound 130 | C | NA | NA |
| Compound 131 | C | NA | NA |
| Compound 132 | B | NA | NA |
| Compound 133 | A | NA | NA |
| Compound 134 | B | NA | NA |

TABLE 20-continued

| Compound | Beta Arrestin EC$_{50}$ | Ca Flux LPA1 IC$_{50}$ | Ca Flux LPA3 IC$_{50}$ |
|---|---|---|---|
| Compound 135 | B | NA | NA |
| Compound 136 | B | NA | NA |
| Compound 137 | B | NA | NA |
| Compound 138 | B | NA | NA |
| Compound 139 | B | NA | NA |
| Compound 140 | C | C | NA |
| Compound 141 | C | NA | NA |
| Compound 142 | C | NA | NA |
| Compound 143 | B | NA | NA |
| Compound 144 | C | NA | NA |
| Compound 145 | B | NA | NA |
| Compound 146 | C | C | NA |
| Compound 147 | C | B | NA |
| Compound 148 | A | NA | NA |
| Compound 149 | C | B | A |
| Compound 150 | C | NA | NA |
| Compound 151 | B | NA | NA |
| Compound 152 | C | B | B |
| Compound 153 | C | A | A |
| Compound 154 | B | NA | NA |
| Compound 155 | B | NA | NA |
| Compound 156 | A | NA | NA |
| Compound 157 | B | NA | NA |
| Compound 158 | A | NA | NA |
| Compound 159 | A | NA | NA |
| Compound 160 | A | NA | NA |
| Compound 161 | A | NA | NA |
| Compound 162 | A | NA | NA |
| Compound 163 | A | NA | NA |
| Compound 164 | B | NA | NA |
| Compound 165 | B | NA | NA |
| Compound 166 | A | NA | NA |
| Compound 167 | A | NA | NA |
| Compound 168 | C | NA | NA |
| Compound 169 Sodium salt | B | NA | NA |
| Compound 170 | C | C | A |
| Compound 171 | C | C | A |
| Compound 172 | C | NA | NA |
| Compound 173 | A | NA | NA |
| Compound 174 | B | NA | NA |
| Compound 175 | B | NA | NA |
| Compound 176 | C | NA | NA |
| Compound 177 | C | NA | NA |
| Compound 178 | B | NA | NA |
| Compound 179 | C | B | NA |
| Compound 180 | C | NA | NA |
| Compound 181 | C | NA | NA |
| Compound 182 | C | C | NA |
| Compound 183 | B | NA | NA |
| Compound 184 | C | NA | NA |
| Compound 185 | C | C | NA |
| Compound 186 | C | NA | NA |
| Compound 187 | C | NA | NA |
| Compound 188 | C | NA | NA |
| Compound 189 | A | NA | NA |
| Compound 190 | B | NA | NA |
| Compound 191 | C | NA | NA |
| Compound 192 | B | NA | NA |
| Compound 193 | B | NA | NA |
| Compound 194 | C | NA | NA |
| Compound 195 | B | NA | NA |
| Compound 196 | B | NA | NA |
| Compound 197 | C | NA | NA |
| Compound 198 | C | NA | NA |
| Compound 199 | C | NA | NA |
| Compound 200 | C | B | NA |
| Compound 201 | C | C | NA |
| Compound 202 | C | NA | NA |
| Compound 203 | C | NA | NA |
| Compound 204 | C | NA | NA |
| Compound 205 | C | NA | NA |
| Compound 206 | C | NA | NA |
| Compound 207 | A | NA | NA |
| Compound 208 | A | NA | NA |
| Compound 209 | B | NA | NA |
| Compound 210 | B | NA | NA |

TABLE 20-continued

| Compound | Beta Arrestin $EC_{50}$ | Ca Flux LPA1 $IC_{50}$ | Ca Flux LPA3 $IC_{50}$ |
|---|---|---|---|
| Compound 211 | B | NA | NA |
| Compound 212 | A | NA | NA |
| Compound 213 | A | NA | NA |
| Compound 214 | A | NA | NA |
| Compound 215 | A | NA | NA |
| Compound 216 (isomer 1) | C | NA | NA |
| Compound 217 (isomer 2) | A | NA | NA |
| Compound 218 (isomer 1) | C | NA | NA |
| Compound 219 (isomer 2) | B | NA | NA |
| Compound 220 | C | NA | NA |
| Compound 221 | C | NA | NA |
| Compound 222 | C | NA | NA |
| Compound 223 | A | NA | NA |
| Compound 224 | C | NA | NA |
| Compound 225 | A | NA | NA |
| Compound 226 | A | NA | NA |
| Compound 227 | C | NA | NA |
| Compound 228 | C | NA | NA |
| Compound 229 | B | NA | NA |
| Compound 230 (isomer 1) | B | NA | NA |
| Compound 231 (isomer 2) | B | NA | NA |
| Compound 232 (isomer 1) | B | NA | NA |
| Compound 233 (isomer 2) | B | NA | NA |
| Compound 234 (isomer 1) | B | NA | NA |
| Compound 235 (isomer 2) | B | NA | NA |
| Compound 236 | A | NA | NA |
| Compound 237 | B | NA | NA |
| Compound 238 | A | NA | NA |
| Compound 239 | A | NA | NA |
| Compound 240 | B | NA | NA |
| Compound 241 | B | B | NA |
| Compound 242 | C | B | NA |
| Compound 243 | B | NA | NA |
| Compound 244 | A | NA | NA |
| Compound 245 | C | NA | NA |
| Compound 246 | B | NA | NA |
| Compound 247 | C | NA | NA |
| Compound 248 | C | NA | NA |
| Compound 249 | C | NA | NA |
| Compound 250 | B | NA | NA |
| Compound 251 | B | NA | NA |
| Compound 252 | B | NA | NA |
| Compound 253 | C | NA | NA |
| Compound 254 | B | NA | NA |
| Compound 255 | C | NA | NA |
| Compound 274 | NA | NA | NA |

TABLE 21

| Compound | Beta Arrestin $EC_{50}$ | Ca Flux LPA1 $IC_{50}$ | Ca Flux LPA3 $IC_{50}$ |
|---|---|---|---|
| Compound 256 | A | NA | NA |
| Compound 257 | A | NA | NA |
| Compound 258 | A | NA | NA |
| Compound 259 | A | NA | NA |
| Compound 260 | A | NA | NA |
| Compound 261 | A | NA | NA |
| Compound 262 | A | NA | NA |
| Compound 263 | A | NA | NA |
| Compound 264 | A | NA | NA |
| Compound 265 | A | NA | NA |
| Compound 266 | A | NA | NA |
| Compound 267 | A | NA | NA |
| Compound 268 | A | NA | NA |
| Compound 269 | A | NA | NA |
| Compound 270 | A | NA | NA |
| Compound 271 | A | NA | NA |
| Compound 272 | A | NA | NA |
| Compound 273 | A | NA | NA |

Clinical Trials in Humans

Clinical trials can be run in multiple conditions. The details of these trials differ based on the indication. Examples of clinical trials for assessment of clinical effect in idiopathic pulmonary fibrosis are provided below.

Although a duration of 72 weeks is specified in the examples below, other durations can also be employed, e.g., 52 weeks.

Clinical Trial in Humans with Idiopathic Pulmonary Fibrosis (IPF) Purpose—Example #1

The efficacy of treatment with a compound of a preferred embodiment compared with placebo in patients with idiopathic pulmonary fibrosis (IPF) and the safety of treatment with a compound of a preferred embodiments compared with placebo in patients with IPF is assessed.

The primary outcome variable is the absolute change in percent predicted forced vital capacity (FVC) from baseline to Week 72. Other possible end-points would include, but are not limited to: mortality, progression free survival, change in rate of FVC decline, change in SpO2, and change in biomarkers (HRCT image analysis; molecular and cellular markers of disease activity). Secondary outcome measures include: composite outcomes of important IPF-related events; progression-free survival; categorical assessment of absolute change in percent predicted FVC from baseline to Week 72; change in Shortness-of-Breath from baseline to Week 72; change in percent predicted hemoglobin (Hb)-corrected carbon monoxide diffusing capacity (DLco) of the lungs from baseline to Week 72; change in oxygen saturation during the 6 minute walk test (6MWT) from baseline to Week 72; change in high-resolution computed tomography (HRCT) assessment from baseline to Week 72; change in distance walked in the 6MWT from baseline to Week 72.

Patients eligible for this study include, but are not limited to: those patients that satisfy the following inclusion criteria: diagnosis of IPF; 40 to 80 years of age; FVC≥50% predicted value; DLco≥35% predicted value; either FVC or DLco≥90% predicted value; no improvement in past year; able to walk 150 meters in 6 minutes and maintain saturation≥83% while on no more than 6 L/min supplemental oxygen.

Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 72 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials.

Patients are orally dosed with either placebo or an amount of a compound of a preferred embodiment (1 mg/day-1000 mg/day). The primary outcome variable will be the absolute change in percent predicted FVC from Baseline to Week 72. Patients will receive blinded study treatment from the time of randomization until the last patient randomized has been treated for 72 weeks. A Data Monitoring Committee (DMC) will periodically review safety and efficacy data to ensure patient safety.

After week 72, patients who meet the Progression of Disease (POD) definition, which is a ≥10% absolute decrease in percent predicted FVC or a ≥15% absolute decrease in percent predicted DLco, will be eligible to receive permitted IPF therapies in addition to their blinded study drug. Permitted IPF therapies include, but are not limited to: corticosteroids, azathioprine, cyclophosphamide, and N-acetyl-cysteine.

In a preferred aspect, a method is provided of administering an LPA1 antagonist of a preferred embodiment to a patient with pulmonary fibrosis (e.g., a patient with IPF), wherein said patient is selected, or diagnosed, or identified to have one or more of the following criteria: (1) ratio of forced expiratory volume in one second (FEV1) to forced vital capacity volume (FVC), or FEV1/FVC, is greater than 0.80, (2) percent of predicted FVC (% FVC) is 90% or less, for example ranging from 50% to 90%, inclusive of both endpoints, and (3) time since diagnosis of IPF is at least six months and up to 48 months. The terms "selecting," "diagnosing" and "identifying" are used synonymously with respect to a patient.

Clinical Trial in Humans with Idiopathic Pulmonary Fibrosis (IPF) Purpose—Example #2

The efficacy of treatment with a compound of a preferred embodiment compared with placebo in patients with idiopathic pulmonary fibrosis (IPF) and the safety of treatment with a compound of a preferred embodiments compared with placebo in patients with IPF is assessed.

The primary outcome variable includes, but is not limited to, the absolute change in percent predicted forced vital capacity (FVC) from baseline to Week 72. Secondary outcome measures include, but are not limited to: composite outcomes of important IPF-related events; progression-free survival; categorical assessment of absolute change in percent predicted FVC from baseline to Week 72; change in Shortness-of-Breath from baseline to Week 72; change in percent predicted hemoglobin (Hb)-corrected carbon monoxide diffusing capacity (DLco) of the lungs from baseline to Week 72; change in oxygen saturation during the 6 minute walk test (6MWT) from baseline to Week 72; change in high-resolution computed tomography (HRCT) assessment from baseline to Week 72; change in distance walked in the 6MWT from baseline to Week 72.

Patients eligible for this study include, but are not limited to, those patients that satisfy the following inclusion criteria: diagnosis of IPF; 40 to 80 years of age; FVC≥50% predicted value; DLco≥35% predicted value; either FVC or DLco≥90% predicted value; no improvement in past year; able to walk 150 meters in 6 minutes and maintain saturation≥83% while on no more than 6 L/min supplemental oxygen.

Patients are excluded from this study if they satisfy any of the following criteria, including but not limited to: unable to undergo pulmonary function testing; evidence of significant obstructive lung disease or airway hyper-responsiveness; in the clinical opinion of the investigator, the patient is expected to need and be eligible for a lung transplant within 72 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials.

Patients are orally dosed with either placebo or an amount of a compound of a preferred embodiment (1 mg/day-1000 mg/day or more). The primary outcome variable includes, but is not limited to, the absolute change in percent predicted FVC from Baseline to Week 72. Patients receive blinded study treatment from the time of randomization until the last patient randomized has been treated for 72 weeks. A Data Monitoring Committee (DMC) periodically reviews safety and efficacy data to ensure patient safety.

After week 72, patients who meet the Progression of Disease (POD) definition, which is a ≥10% absolute decrease in percent predicted FVC or a ≥15% absolute decrease in percent predicted DLco, are eligible to receive permitted IPF therapies in addition to their blinded study drug. Permitted IPF therapies include, but are not limited to, corticosteroids, azathioprine, cyclophosphamide, and N-acetyl-cysteine.

Treatment of Ideopathic Pulmonary Fibrosis

A compound of a preferred embodiment can be administered to a patient in need of therapy, and can be used in methods of preparing or packaging medicaments, containers, packages, and kits comprising the compound of a preferred embodiment. The patient may have pulmonary fibrosis, such as IPF, and the medicament can be used for treatment of pulmonary fibrosis, or IPF. A selected group of IPF patients that are more likely to experience FVC decline and disease progression over a period of a year can be identified and treated. Their greater rate of progression, as reflected by a greater rate of decrease in respiratory parameters such as FVC, correlates with a greater relative magnitude of treatment effect. In certain embodiments, IPF patients with the following criteria experience a greater FVC decline, as measured by % FVC change from baseline or proportion of patients with 10% or greater % FVC decline at a specified timepoint, compared to patients that do not meet the criteria. Patients with the following criteria also exhibit a greater observed treatment effect on alleviating the extent of FVC decline compared to patients that do not meet the criteria: (a) % FVC 50%-90%; (b) FEV1/FVC ratio>0.80; (c) Time since IPF diagnosis>0.5 years and <48 months;

A method of treating pulmonary fibrosis, optionally IPF, is provided comprising (a) selecting a patient that exhibits (i) percent of predicted forced vital capacity volume (% FVC) of about 90% or less, or (ii) ratio of forced expiratory volume in one second (FEV1) to forced vital capacity volume (FVC) of about 0.80 or greater, or both, and (b) administering a therapeutically effective amount of the compound of a preferred embodiment.

In a related aspect, use is provided of the compound of a preferred embodiment in treating pulmonary fibrosis in a patient that exhibits (i) percent of predicted forced vital capacity volume (% FVC) of about 90% or less or (ii) ratio of forced expiratory volume in one second (FEV1) to forced vital capacity volume (FVC) of about 0.80 or greater, or both.

In a further related aspect, the compound of a preferred embodiment is used in preparation of a medicament for treating pulmonary fibrosis in a patient that exhibits (i) percent of predicted forced vital capacity volume (% FVC) of about 90% or less or (ii) ratio of forced expiratory volume in one second (FEY1) to forced vital capacity volume (FVC) of about 0.80 or greater, or both.

Optionally, in some or any of these embodiments, % FVC ranges from about 50% to about 90%. In some or any embodiments, the patient has been diagnosed with pulmonary fibrosis, optionally IPF, for at least six months, and optionally less than 48 months. In some or any embodiments, optionally the patient is also selected to exhibit a percent of diffusing capacity (% $DL_{co}$) of about 90% or less, for example, ranging from 30% to 90%, or 30% to 60%, inclusive of both endpoints. In some or any embodiments, the FEV1/FVC ratio is greater than 0.9. In some or any embodiments, the % FVC is less than 80%, 70%, or 60%. In some or any embodiments, the % $DL_{co}$ is less than 90%, 80%, 70%, 60%, or 50%, or less than 40%. In most cases the patient is diagnosed with IPF through a High Resolution Computed Tomography (HRCT) scan, optionally with confirmation through surgical lung biopsy.

In any of the aspects or embodiments, the therapeutically effective amount of the compound of a preferred embodiment being administered may be a total daily dosage of from 1-4000 mg per day or more, e.g., at least about 1800 mg per day, or about 2400 mg or about 2403 mg per day, optionally administered in divided doses three times per day, with food. In any of the aspects of embodiments, the total daily dosage may be about 1200 to about 4000 mg per day, or about 1600 to about 3600 mg per day. In any of the aspects of the invention, the daily dosage may be administered in divided doses three times a day, or two times a day, or alternatively is administered in a single dose once a day. In any of the aspects of the invention, the compound of a preferred embodiment may be administered with food. For example, the daily dosage of 2400 mg or 2403 mg the compound of a preferred embodiment per day may be administered as follows: 801 mg taken three times a day, with food.

The compound of a preferred embodiment can be dosed at a total amount of from 1-4000 mg per day or more, or from about 50 to about 2400 mg per day. The dosage can be divided into two or three doses over the day. Specific amounts of the total daily amount of the therapeutic contemplated for the disclosed methods include about 50 mg, about 100 mg, about 150 mg, about 200 mg, about 250 mg, about 267 mg, about 300 mg, about 350 mg, about 400 mg, about 450 mg, about 500 mg, about 534 mg, about 550 mg, about 600 mg, about 650 mg, about 700 mg, about 750 mg, about 800 mg, about 850 mg, about 900 mg, about 950 mg, about 1000 mg, about 1050 mg, about 1068 mg, about 1100 mg, about 1150 mg, about 1200 mg, about 1250 mg, about 1300 mg, about 1335 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1869 mg, about 1900 mg, about 1950 mg, about 2000 mg, about 2050 mg, about 2100 mg, about 2136 mg, about 2150 mg, about 2200 mg, about 2250 mg, about 2300 mg, about 2350 mg, and about 2400 mg.

Dosages of the compound of preferred embodiments can alternately be administered as a dose measured in mg/kg. Contemplated mg/kg doses of the disclosed therapeutics include, e.g., about 1 mg/kg to about 40 mg/kg. Specific ranges of doses in mg/kg include about 20 mg/kg to about 40 mg/kg, or about 30 mg/kg to about 40 mg/kg.

In another aspect, a package or kit is provided comprising the compound of a preferred embodiment, optionally in a container, and a package insert, package label, instructions, or other labeling including any of the criteria for patient selection described herein. The package insert, package label, instructions or other labeling may further comprise directions for treating IPF by administering the compound of a preferred embodiment, e.g., at a dosage of at least about 1800 mg per day, or a dosage of about 2400 mg or about 2403 mg per day.

In related aspect, a method of preparing or packaging a medicament comprising the compound of a preferred embodiment, optionally in a container, together with a package insert or package label or instructions including any of the foregoing information or recommendations.

In some embodiments, a method of treating IPF is disclosed comprising providing, selling, or delivering any of the kits of disclosed herein to a hospital, physician, or patient.

The following patent publications include disclosures relating to diseases, disorders, or conditions that may be associated with one or more of the lysophosphatidic acid receptors, the contents of which relating to said diseases, disorders, or conditions are hereby incorporated by reference herein: PCT Intl. Publ. No. WO/2011017350-A1; PCT Intl. Publ. No. WO/2010141768-A1; PCT Intl. Publ. No. WO/2010077883-A1; PCT Intl. Publ. No. WO/2010077882-A1; PCT Intl. Publ. No. WO/2010068775-A1; U.S. Pat. Publ. No. US-20110098352-A1; U.S. Pat. Publ. No. US-20110098302-A1; U.S. Pat. Publ. No. US-20110082181-A1; U.S. Pat. Publ. No. US-20110082164-A1; U.S. Pat. Publ. No. US-20100311799-A1; U.S. Pat. Publ. No. US-20100152257-A1; PCT Intl. Publ. No. WO/2010141761-A1; PCT Intl. Publ. No. WO/2011041729-A1; PCT Intl. Publ. No. WO/2011041694-A1; PCT Intl. Publ. No. WO/2011041462-A1; and PCT Intl. Publ. No. WO/2011041461-A1.

Pharmaceutical Compositions

Parenteral Pharmaceutical Composition

To prepare a parenteral pharmaceutical composition suitable for administration by injection (subcutaneous, intravenous, or the like), 100 mg of a water-soluble salt/soluble material itself/solubilized complex of a compound of a preferred embodiment is dissolved in sterile water and then mixed with 10 mL of 0.9% sterile saline. The mixture is incorporated into a dosage unit form suitable for administration by injection.

Injectable Pharmaceutical Composition

To prepare an injectable formulation, 1.2 g of a compound of Formulas (I), 2.0 mL of sodium acetate buffer solution (0.4 M), HCl (1 N) or NaOH (1 M) (q.s. to suitable pH), water (distilled, sterile) (q.s. to 20 mL) are mixed. All of the above ingredients, except water, are combined and stirred and if necessary, with slight heating if necessary. A sufficient quantity of water is then added.

Oral Pharmaceutical Composition

To prepare a pharmaceutical composition for oral delivery, 100 mg of a compound of a preferred embodiment is mixed with 750 mg of starch. The mixture is incorporated into an oral dosage unit, such as a hard gelatin capsule, or 100 mg of compound is granulated with binder solution such as starch solution along with suitable diluents such as microcrystalline cellulose or like, disintegrants such as cross caramellose sodium, dry the resultant mixture and add lubricant and compress into tablet which is suitable for oral administration.

Sublingual (Hard Lozenge) Pharmaceutical Composition

To prepare a pharmaceutical composition for buccal delivery, such as a hard lozenge, 100 mg of a compound of a preferred embodiment is mixed with 420 mg of powdered sugar/mannitol/xylitol or such sugars that provide negative heat of solution to the system, 1.6 mL of light corn syrup, 2.4 mL distilled water, and 0.42 mL mint extract or other flavorants. The mixture is blended and poured into a mold to form a lozenge suitable for buccal administration.

Fast-Disintegrating Sublingual Tablet

A fast-disintegrating sublingual tablet is prepared by mixing 48.5% by weigh of a compound of a preferred embodiment, 20% by weight of microcrystalline cellulose (KG-802), 24.5% by weight of either mannitol or modified dextrose or combination that help dissolve the compressed tablet faster in the mouth, 5% by weight of low-substituted hydroxypropyl cellulose (50 µm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of the compound of a preferred embodiment with the total quantity of microcrystalline cellulose (MCC) and mannitol/modified dextrose or combination, and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Pharmaceutical Composition

To prepare a pharmaceutical composition for inhalation delivery, 20 mg of a compound of a preferred embodiment is mixed with 50 mg of anhydrous citric acid and 100 mL of 0.9% sodium chloride solution. The mixture is incorporated into an inhalation delivery unit, such as a nebulizer, which is suitable for inhalation administration.

Nebulizer Suspension Pharmaceutical Composition

In another embodiment, a compound of a preferred embodiment (500 mg) is suspended in sterile water (100 mL); Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Rectal Gel Pharmaceutical Composition

To prepare a pharmaceutical composition for rectal delivery, 100 mg of a compound of a preferred embodiment is mixed with 2.5 g of methylcellulose (1500 mPa), 100 mg of methylparaben, 5 g of glycerin and 100 mL, of purified water. The resulting gel mixture is then incorporated into rectal delivery units, such as syringes, which are suitable for rectal administration.

Topical Gel Pharmaceutical Composition

To prepare a pharmaceutical topical gel composition, 100 mg of a compound of a preferred embodiment is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution

To prepare a pharmaceutical ophthalmic solution composition, 100 mg of a compound of a preferred embodiment is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound of a preferred embodiment is mixed with 30 mL of a 0.05M phosphate buffer solution (pH 4.4). The solution is placed in a nasal administrator designed to deliver 100 µl of spray for each application.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A compound of Formula (Ie):

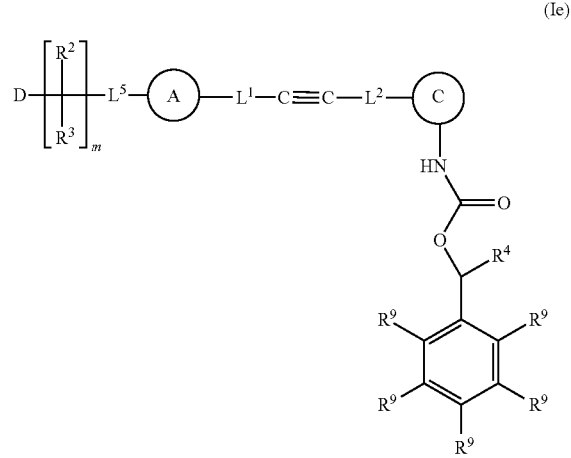

or a pharmaceutically acceptable salt thereof, wherein:

A is selected from

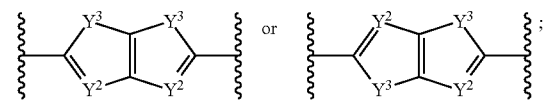

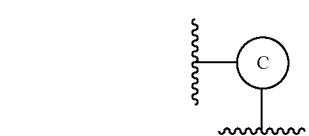
is selected from
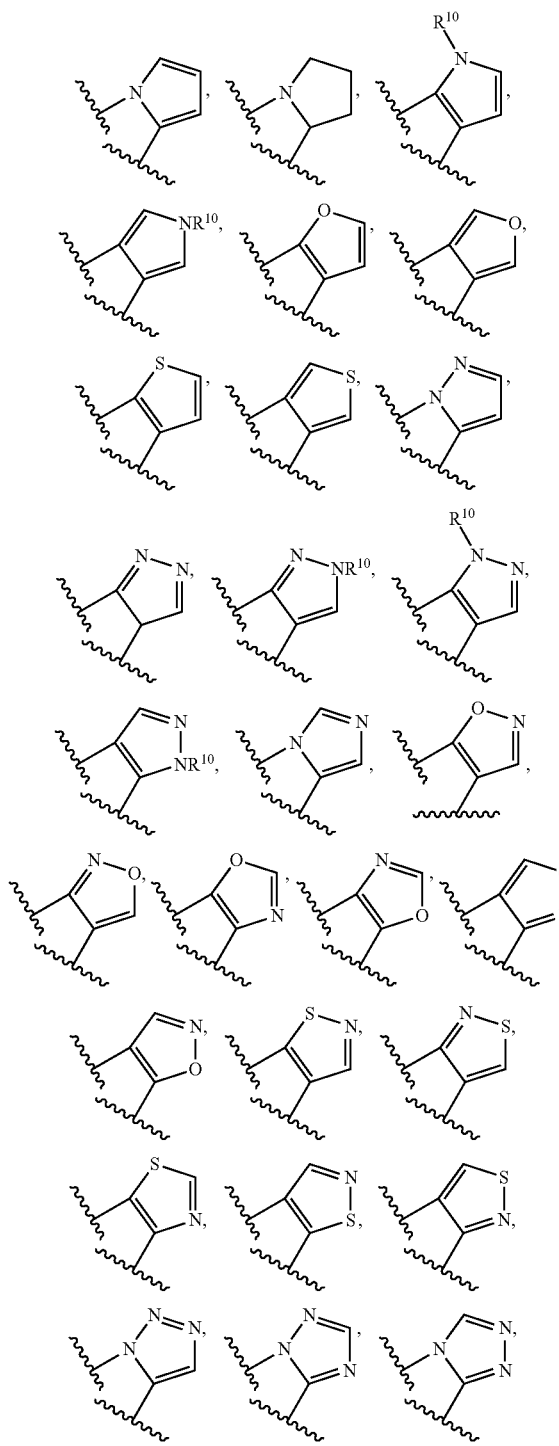
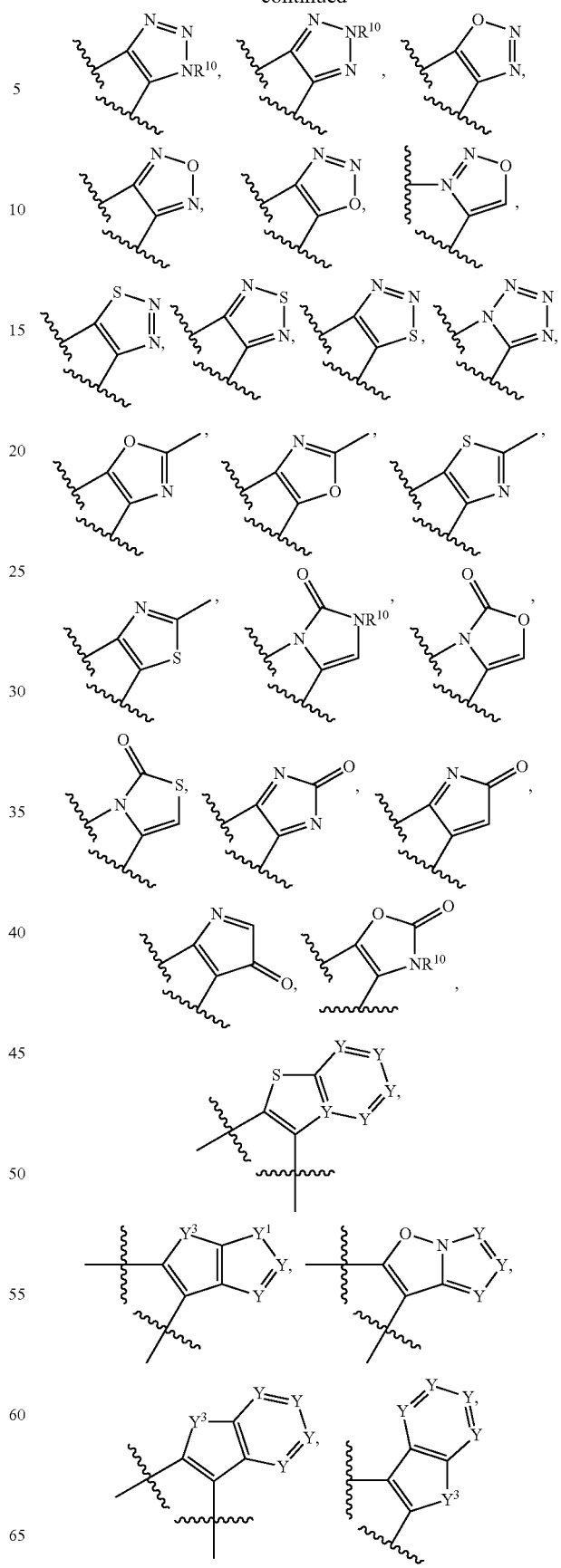

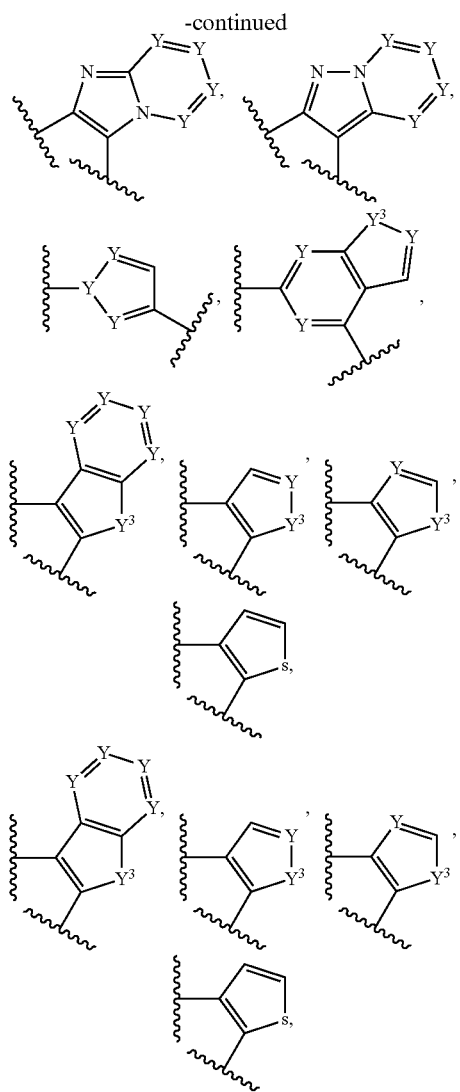

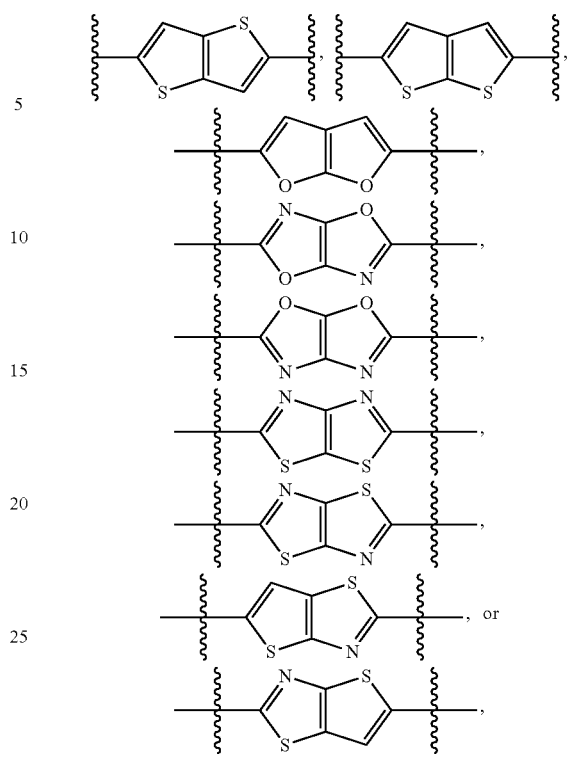

or optionally substituted variants thereof;

each of $L^1$, $L^2$ and $L^5$ is a single bond;

D is —C(O)OH;

$R^2$ and $R^3$ are each independently selected from H, alkyl, aryl, or heteroaryl; or $R^2$ and $R^3$ are joined together with the atom to which they are attached to form an optionally substituted cycloalkyl or an optionally substituted heterocycle;

$R^4$ is selected from H and alkyl;

each $R^6$ is independently selected from H, alkyl, halo, aryl, or $C_{3-6}$ cycloalkyl;

each $R^9$ is independently selected from H, alkyl or halogen;

each $R^{10}$ is independently selected from H, alkyl, halo, aryl, $C_{3-6}$ cycloalkyl, or cyano;

each Y is independently selected from $CR^6$ or N;

$Y^2$ is selected from —CH=, =CH—, or N;

$Y^3$ is selected from $C(R^6)_2$, $NR^6$, O, or S; and m is an integer from 0-3.

2. The compound or pharmaceutically acceptable salt thereof of claim 1, wherein A is selected from each unsubstituted or substituted with one or more substituents selected from alkyl, halo or oxo.

3. The compound or pharmaceutically acceptable salt thereof of claim 2, wherein A is selected from

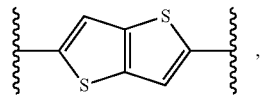 [SMILES: *c1cc2sc(*)cc2s1]

unsubstituted or substituted with one or more substituents selected from alkyl, halo or oxo.

4. The compound or pharmaceutically acceptable salt thereof of claim 2, wherein A is selected from

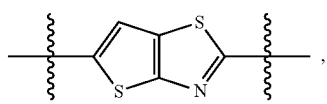 [SMILES: *c1cc2sc(*)nc2s1]

unsubstituted or substituted with one or more substituents selected from alkyl, halo or oxo.

5. The compound or pharmaceutically acceptable salt thereof of claim 1, wherein m is 1.

6. The compound or pharmaceutically acceptable salt thereof of claim 1, wherein m is 0.

7. The compound or pharmaceutically acceptable salt thereof of claim 1, wherein both $R^2$ and $R^3$ are hydrogen.

8. The compound or pharmaceutically acceptable salt thereof of claim 1, wherein $R^2$ and $R^3$ are joined together with the atom to which they are attached to form a cyclopropyl.

9. The compound or pharmaceutically acceptable salt thereof of claim 1, wherein $R^2$ and $R^3$ are joined together with the atom to which they are attached to form an optionally substituted azetidine, an optionally substituted oxetane, an optionally substituted beta-lactam, an optionally substituted tetrahydropyran, an optionally substituted cyclobutyl, an optionally substituted cyclopentyl, or an optionally substituted cyclohexyl.

10. The compound or pharmaceutically acceptable salt thereof of claim 1, wherein

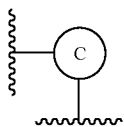

is selected from an optionally substituted oxazole, an optionally substituted isoxazole, an optionally substituted thiazole, or an optionally substituted isothiazole.

11. The compound or pharmaceutically acceptable salt thereof of claim 10, wherein

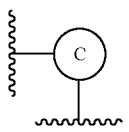

is selected from

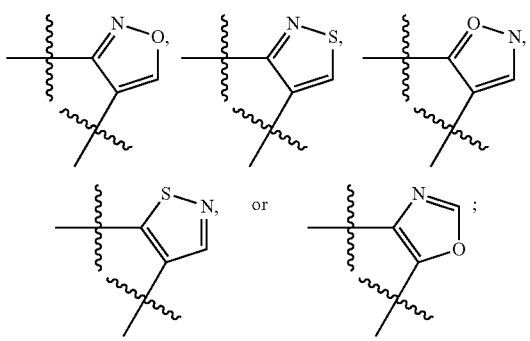

and wherein each ring C is unsubstituted or substituted with one or more substituents selected from $C_{1-3}$ alkyl, $C_{3-6}$ cycloalkyl, halogen or cyano.

12. The compound or pharmaceutically acceptable salt thereof of claim 11, wherein

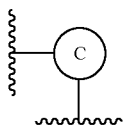

is selected from

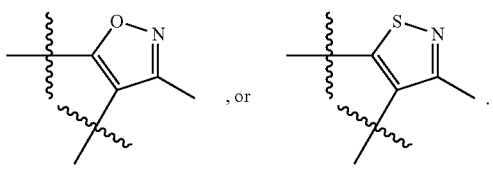

13. The compound or pharmaceutically acceptable salt thereof of claim 1, wherein

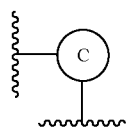

is optionally substituted

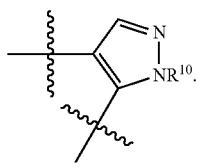

14. The compound or pharmaceutically acceptable salt thereof claim 13, wherein $R^{10}$ is selected from hydrogen, $C_{1-3}$ alkyl, $C_{3-6}$ cycloalkyl, or cyano.

15. The compound or pharmaceutically acceptable salt thereof claim 13, wherein $R^{10}$ is selected from $C_{1-3}$ alkyl.

16. The compound or pharmaceutically acceptable salt thereof claim 13, wherein $R^{10}$ is methyl.

17. The compound or pharmaceutically acceptable salt thereof of claim 1, wherein

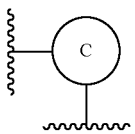

is optionally substituted

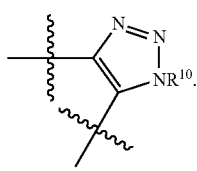

18. The compound or pharmaceutically acceptable salt thereof claim 17, wherein $R^{10}$ is selected from hydrogen, $C_{1-3}$ alkyl, $C_{3-6}$ cycloalkyl, or cyano.

19. The compound or pharmaceutically acceptable salt thereof of claim 17, wherein $R^{10}$ is $C_{1-3}$ alkyl.

20. The compound or pharmaceutically acceptable salt thereof claim 17, wherein $R^{10}$ is methyl.

21. The compound or pharmaceutically acceptable salt thereof of claim 1, wherein

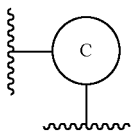

is selected from

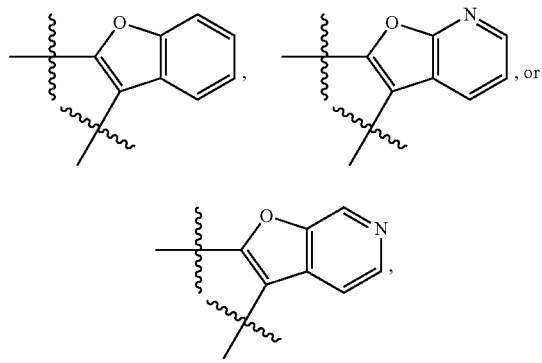 [SMILES: *c1oc2ccccc2c1* ; *c1oc2ncccc2c1* ; *c1oc2cnccc2c1*]

wherein each ring C is unsubstituted or substituted with one or more substituents selected from $C_{1-3}$ alkyl, $C_{3-6}$ cycloalkyl, halogen or cyano.

22. The compound or pharmaceutically acceptable salt thereof of claim 1, wherein $R^9$ is halo.

23. The compound or pharmaceutically acceptable salt thereof of claim 1, wherein both $R^4$ and $R^5$ are hydrogen.

24. The compound or pharmaceutically acceptable salt thereof of claim 1, wherein $R^4$ is alkyl and $R^5$ is hydrogen.

25. The compound or pharmaceutically acceptable salt thereof of claim 1, selected from the group consisting of:

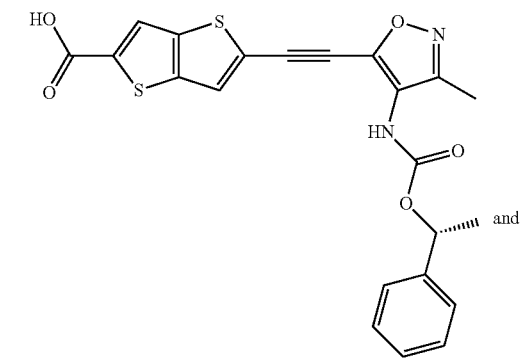

and

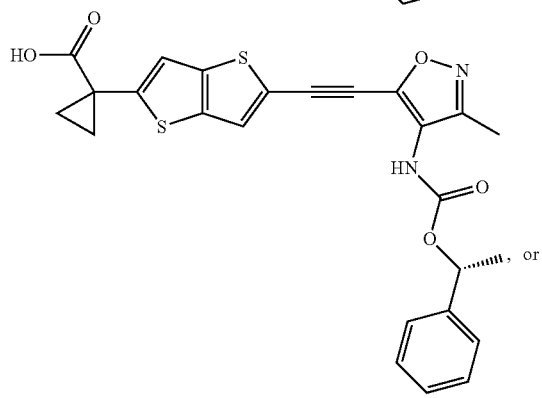

or pharmaceutically acceptable salts thereof.

26. The compound or pharmaceutically acceptable salt thereof of of claim 1, selected from the group consisting of:

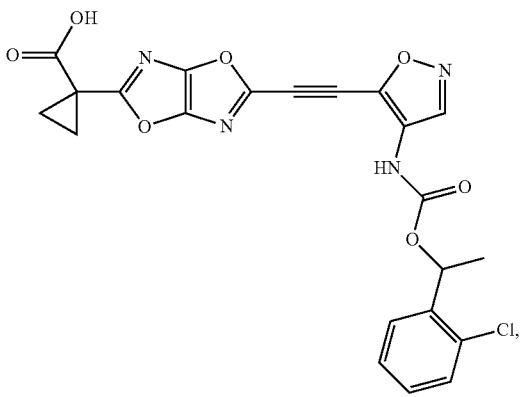

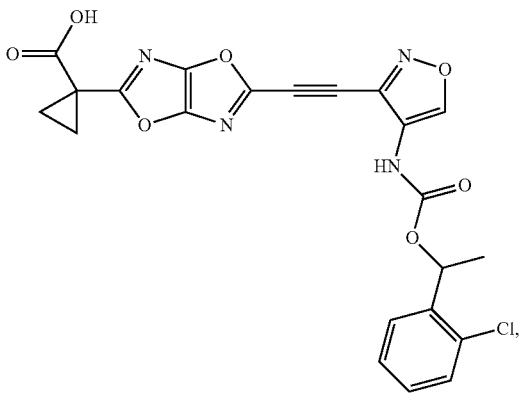

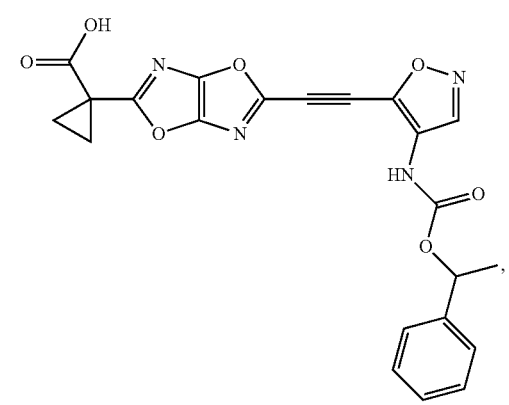

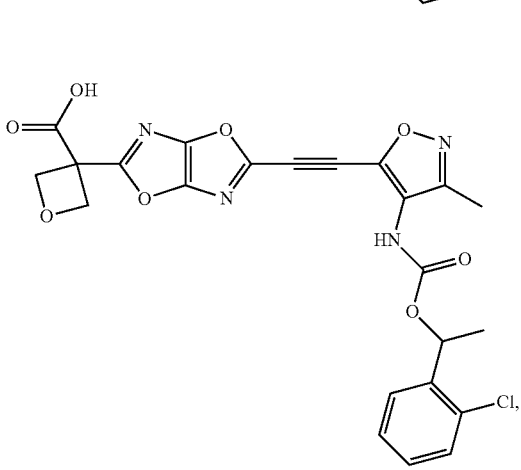

1285
-continued
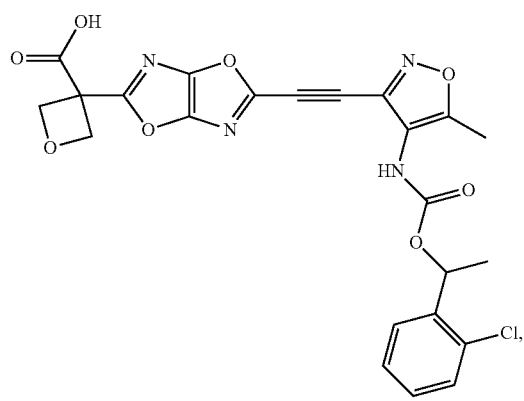
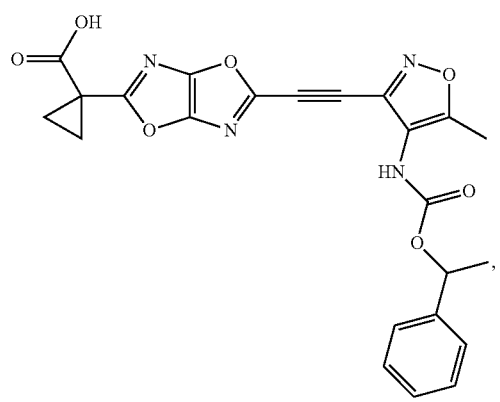
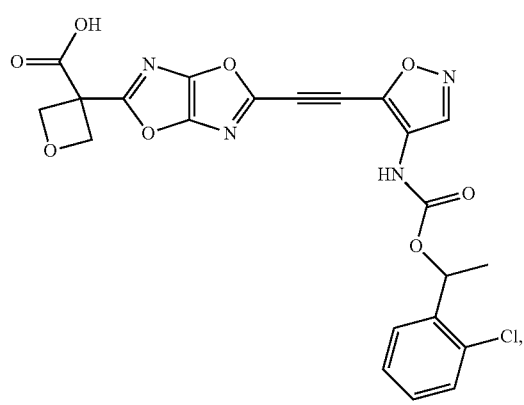
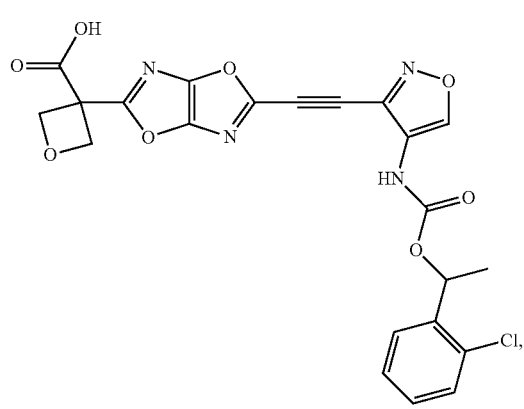
1286
-continued
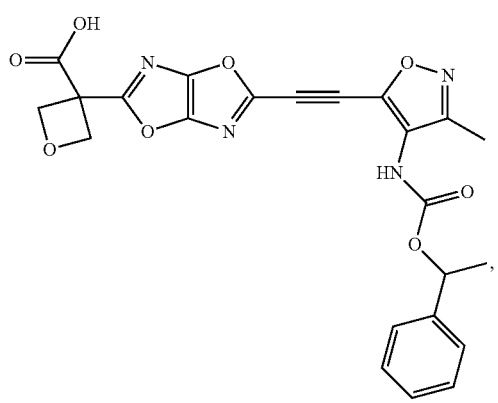
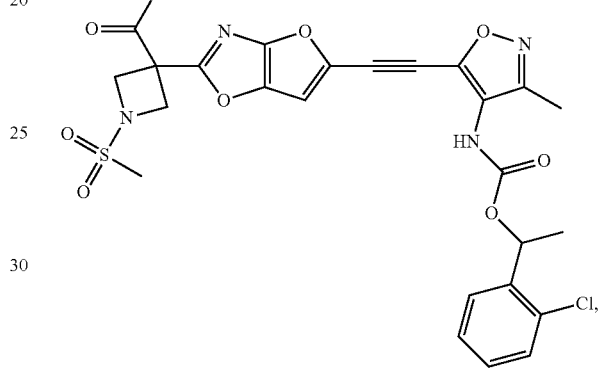
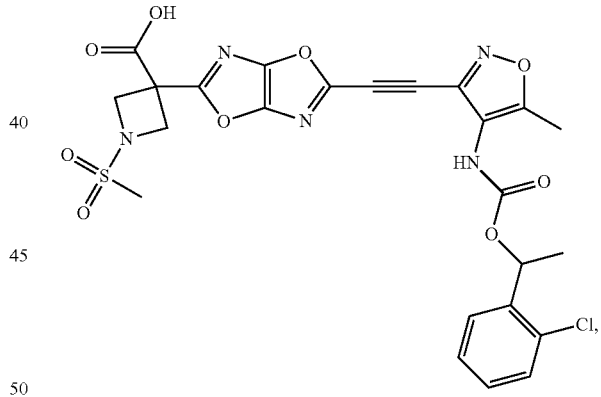

1287
-continued
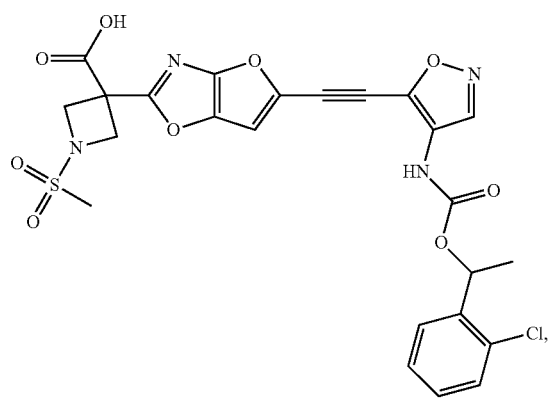
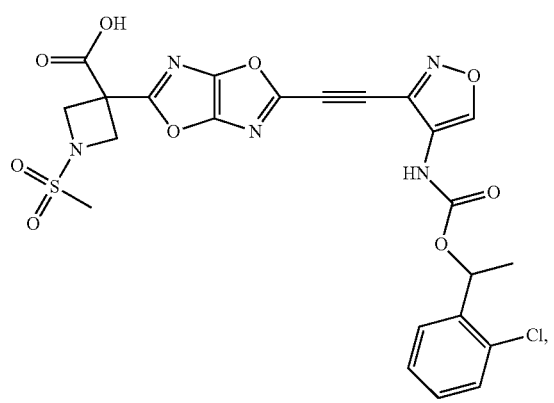
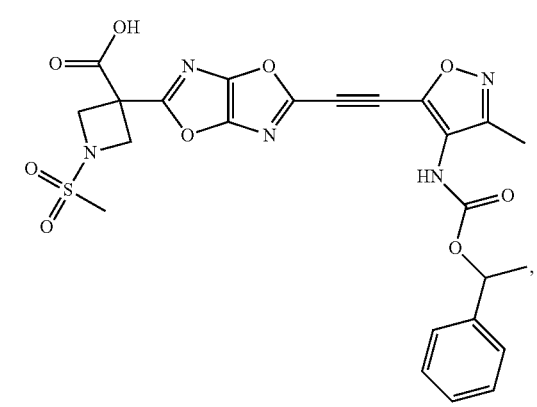
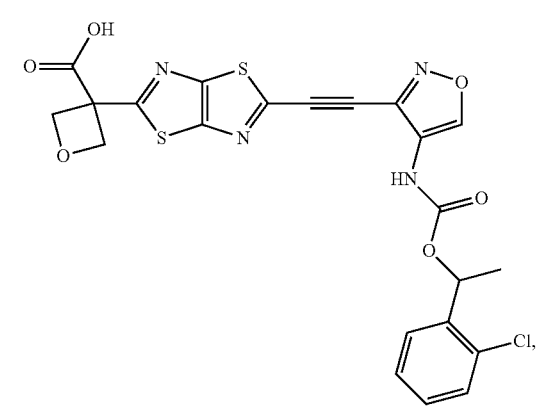
1288
-continued

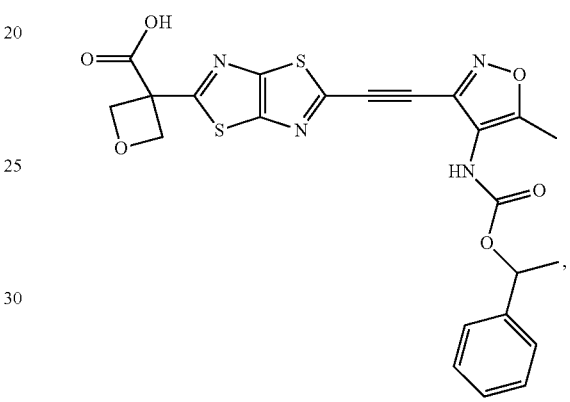
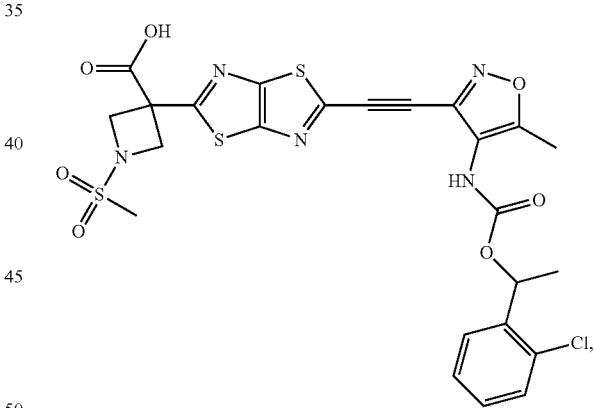
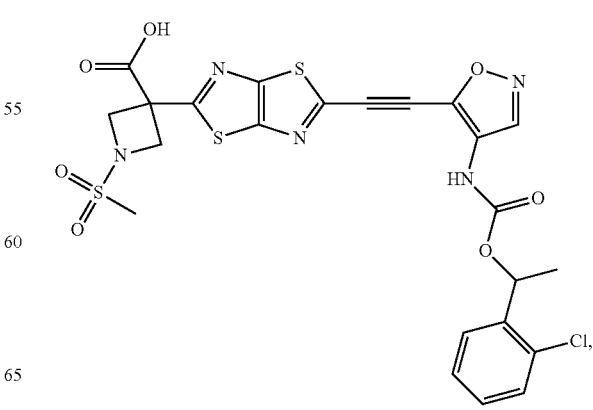

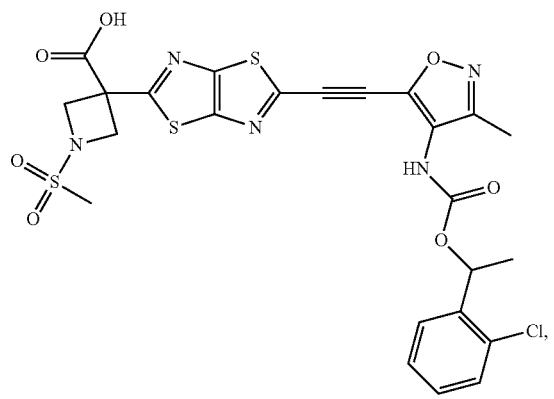
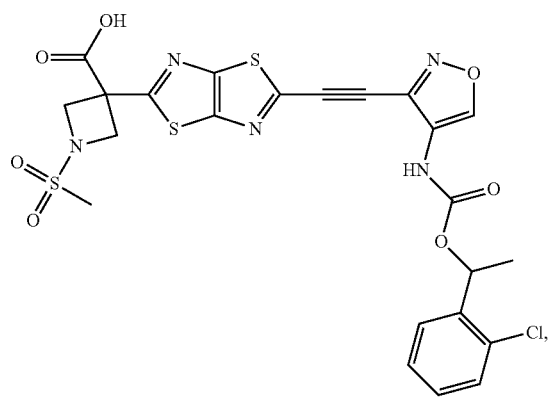
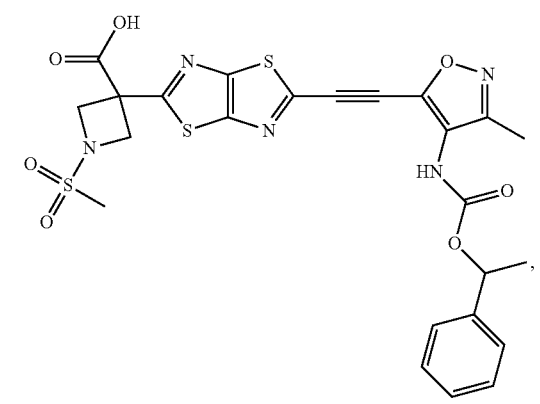
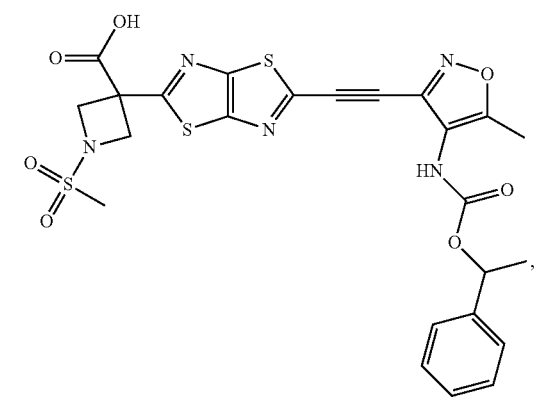
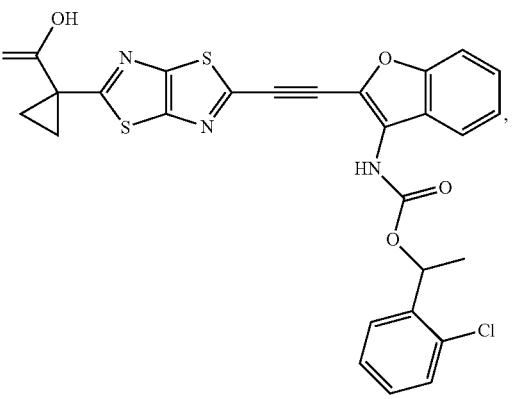
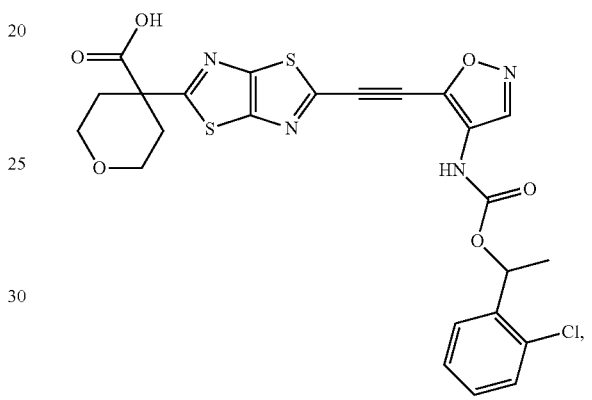
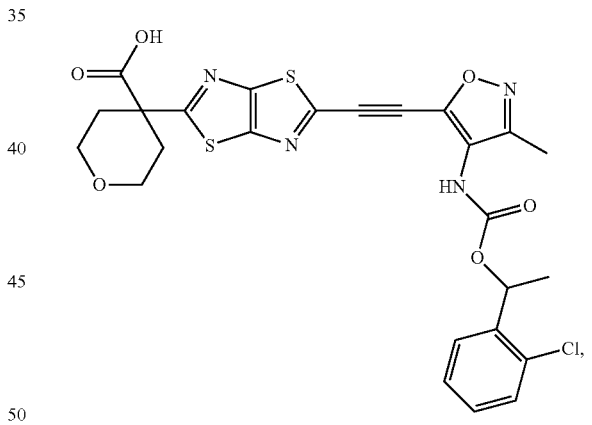
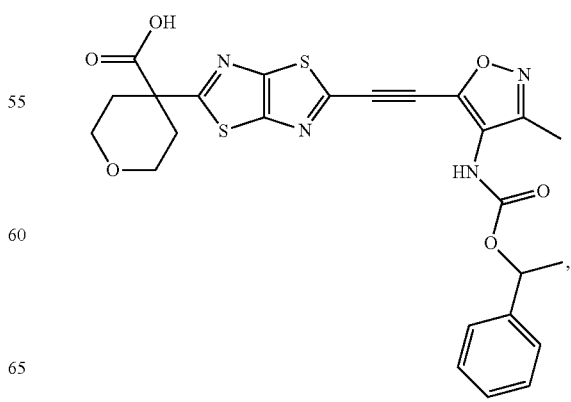

1291
-continued
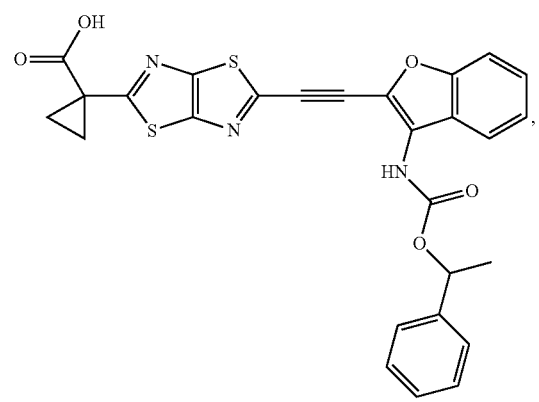
or pharmaceutically acceptable salts thereof.
27. The compound or pharmaceutically acceptable salt thereof of claim 1, selected from compounds of Table 11 having the following structures:
1292
TABLE 11
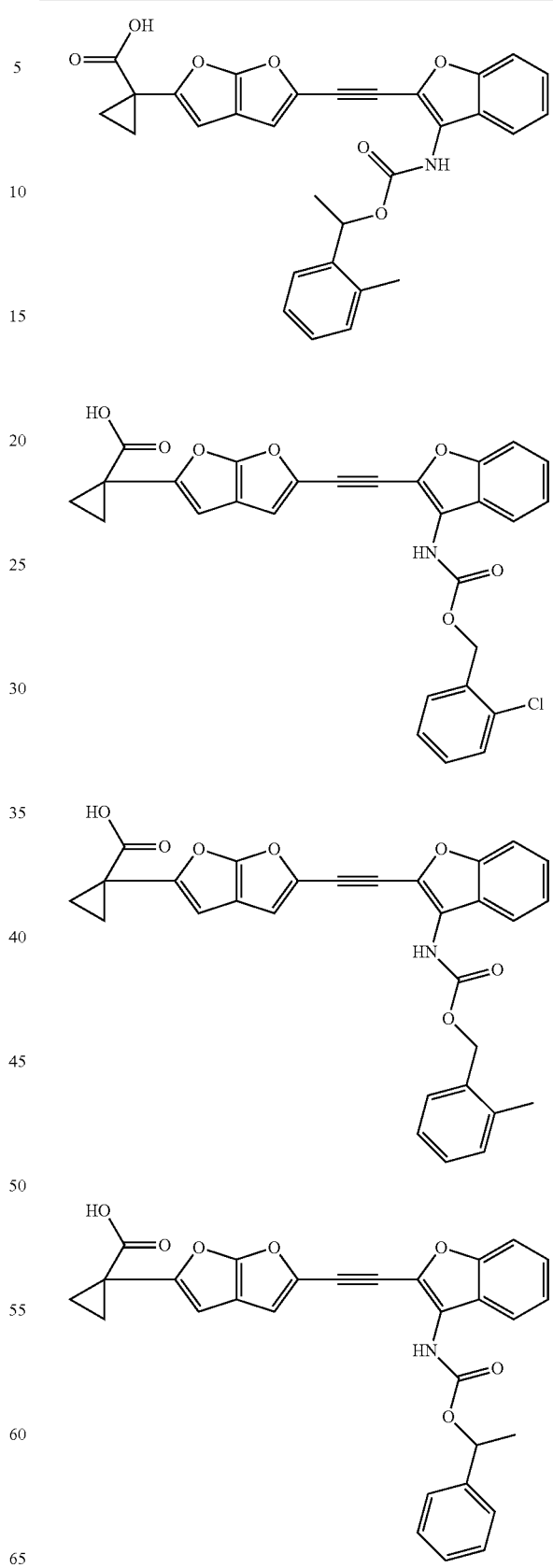

1293
TABLE 11-continued
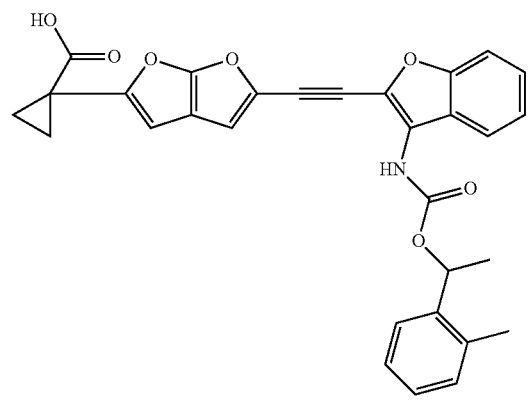 [SMILES: Cc1ccccc1C(C)OC(=O)Nc1c(C#Cc2cc3cc(C4(C(=O)O)CC4)oc3o2)oc2ccccc12]
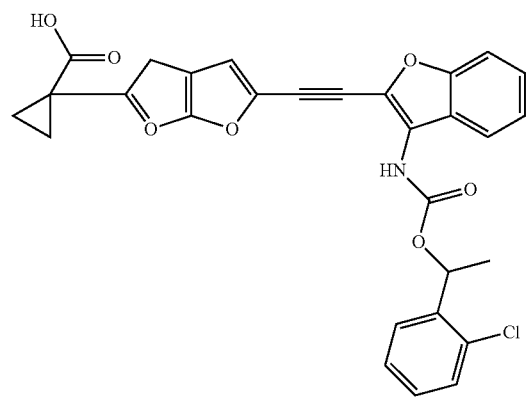
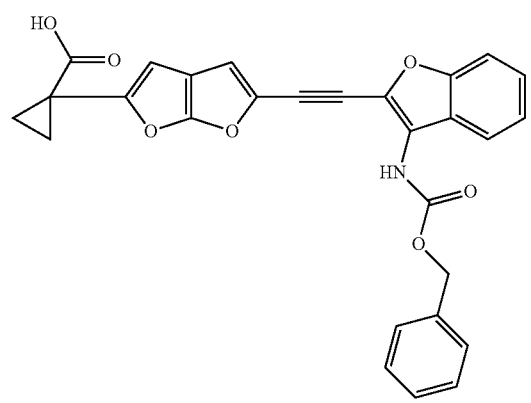 [SMILES: O=C(Nc1c(C#Cc2cc3cc(C4(C(=O)O)CC4)oc3o2)oc2ccccc12)OCc1ccccc1]
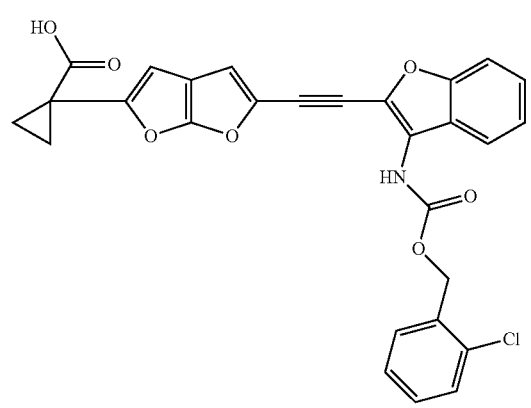 [SMILES: O=C(Nc1c(C#Cc2cc3cc(C4(C(=O)O)CC4)oc3o2)oc2ccccc12)OCc1ccccc1Cl]
1294
TABLE 11-continued
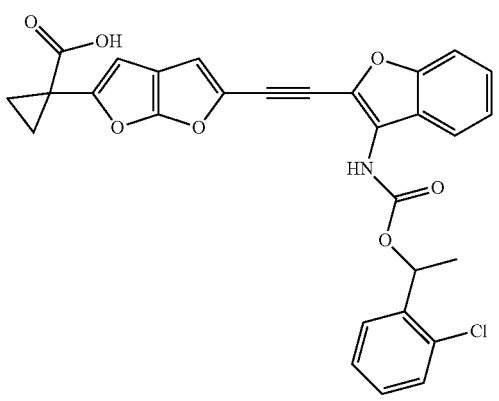 [SMILES: CC(OC(=O)Nc1c(C#Cc2cc3cc(C4(C(=O)O)CC4)oc3o2)oc2ccccc12)c1ccccc1Cl]
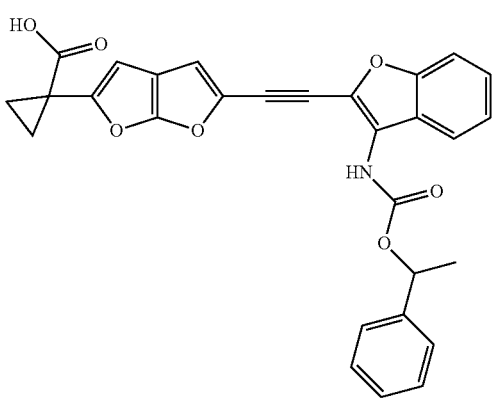 [SMILES: CC(OC(=O)Nc1c(C#Cc2cc3cc(C4(C(=O)O)CC4)oc3o2)oc2ccccc12)c1ccccc1]
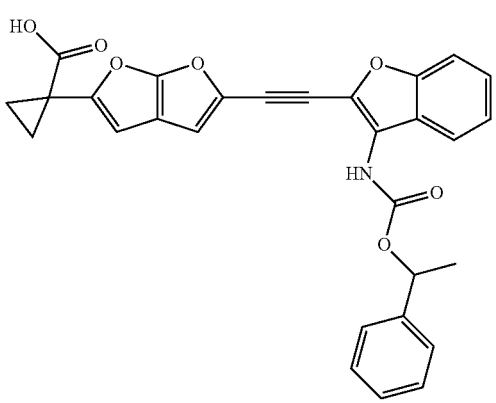
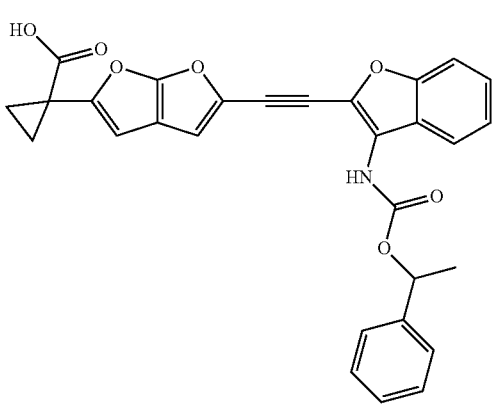 [SMILES: CC(OC(=O)Nc1c(C#Cc2cc3cc(C4(C(=O)O)CC4)oc3o2)oc2ccccc12)c1ccccc1]

TABLE 11-continued
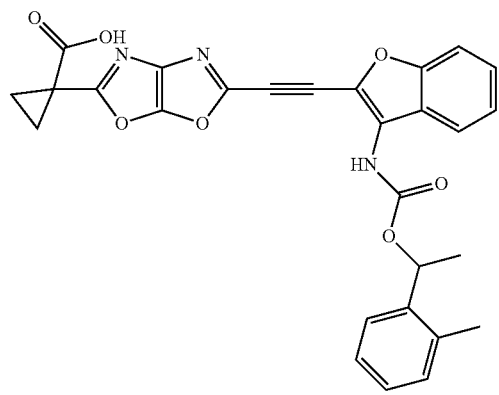 [SMILES: Cc1ccccc1C(C)OC(=O)Nc1c(C#Cc2nc3nc(C4(C(=O)O)CC4)oc3o2)oc2ccccc12]
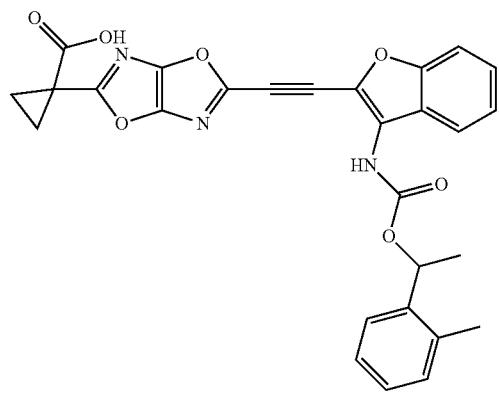 [SMILES: Cc1ccccc1C(C)OC(=O)Nc1c(C#Cc2nc3oc(C4(C(=O)O)CC4)nc3o2)oc2ccccc12]
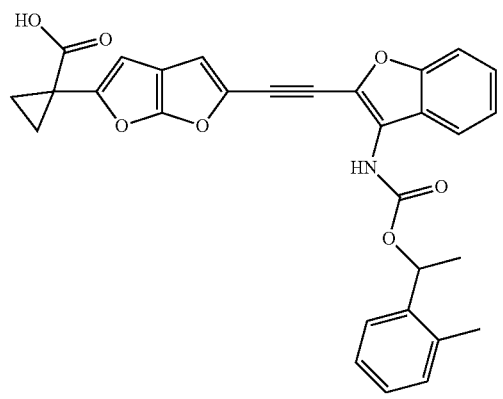
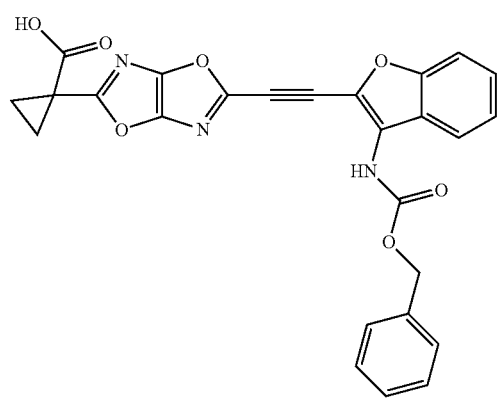 [SMILES: O=C(Nc1c(C#Cc2nc3oc(C4(C(=O)O)CC4)nc3o2)oc2ccccc12)OCc1ccccc1]
TABLE 11-continued
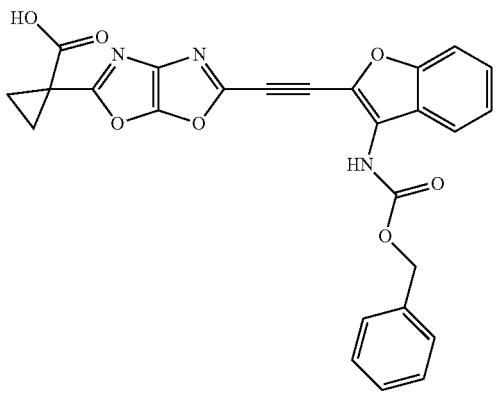
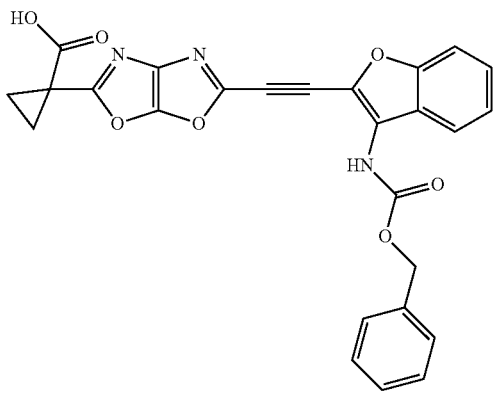
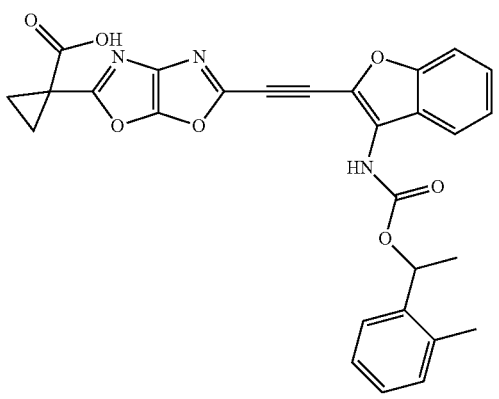 [SMILES: Cc1ccccc1C(C)OC(=O)Nc1c(C#Cc2nc3nc(C4(C(=O)O)CC4)oc3o2)oc2ccccc12]
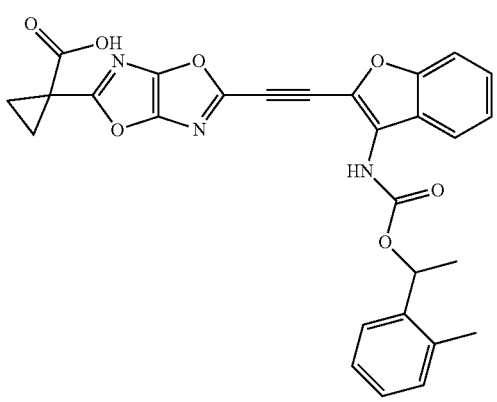 [SMILES: Cc1ccccc1C(C)OC(=O)Nc1c(C#Cc2nc3oc(C4(C(=O)O)CC4)nc3o2)oc2ccccc12]

TABLE 11-continued
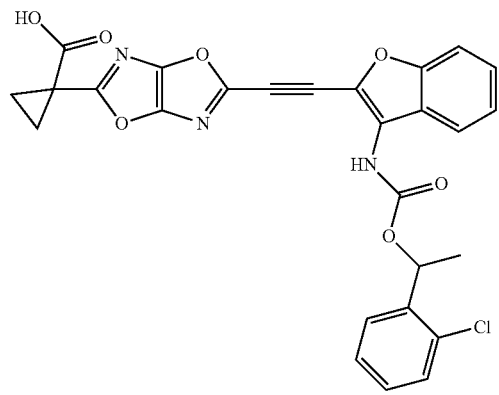 [SMILES: CC(OC(=O)Nc1c(C#Cc2nc3oc(C4(C(=O)O)CC4)nc3o2)oc2ccccc12)c1ccccc1Cl]
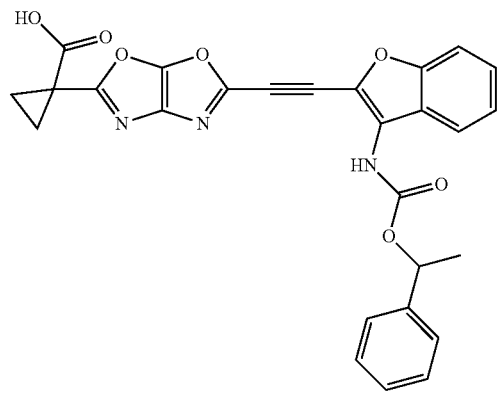 [SMILES: CC(OC(=O)Nc1c(C#Cc2nc3nc(C4(C(=O)O)CC4)oc3o2)oc2ccccc12)c1ccccc1]
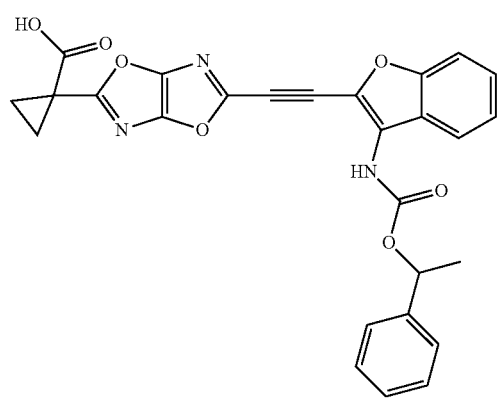 [SMILES: CC(OC(=O)Nc1c(C#Cc2nc3oc(C4(C(=O)O)CC4)nc3o2)oc2ccccc12)c1ccccc1]
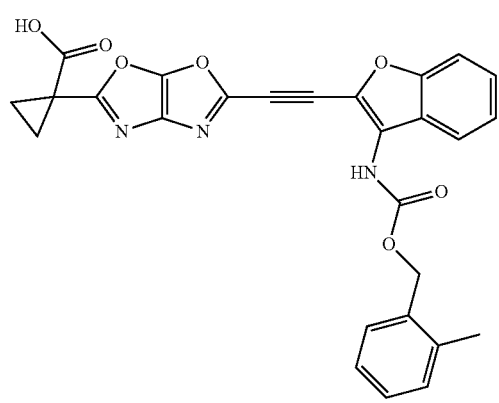 [SMILES: Cc1ccccc1COC(=O)Nc1c(C#Cc2nc3nc(C4(C(=O)O)CC4)oc3o2)oc2ccccc12]
TABLE 11-continued
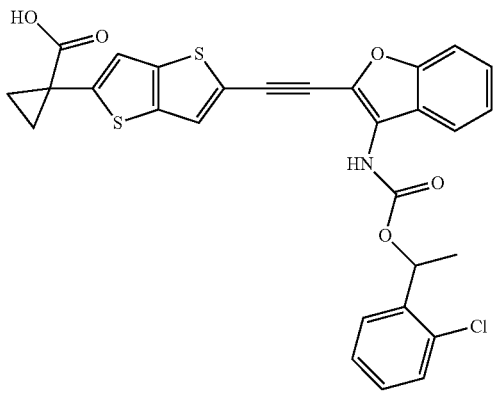 [SMILES: CC(OC(=O)Nc1c(C#Cc2cc3sc(C4(C(=O)O)CC4)cc3s2)oc2ccccc12)c1ccccc1Cl]
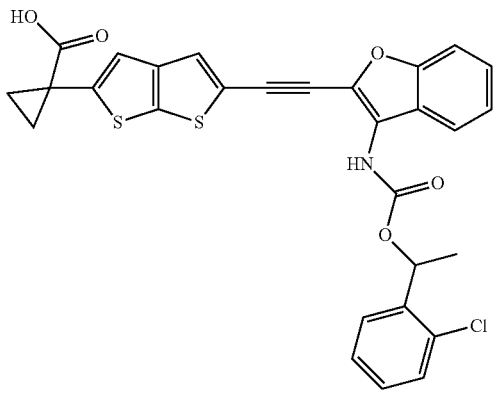
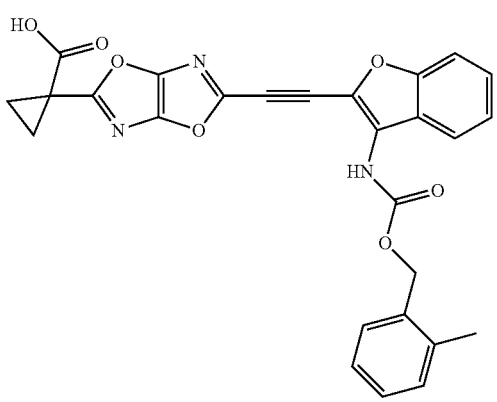
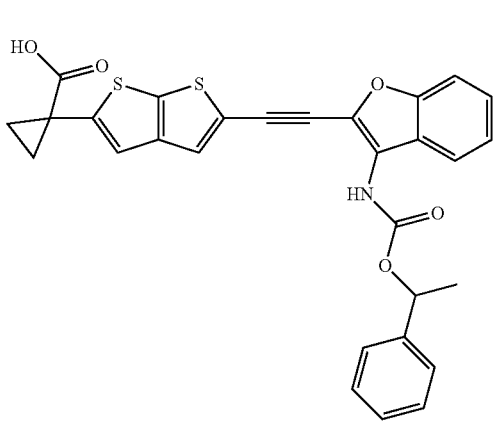 [SMILES: CC(OC(=O)Nc1c(C#Cc2cc3cc(C4(C(=O)O)CC4)sc3s2)oc2ccccc12)c1ccccc1]

TABLE 11-continued
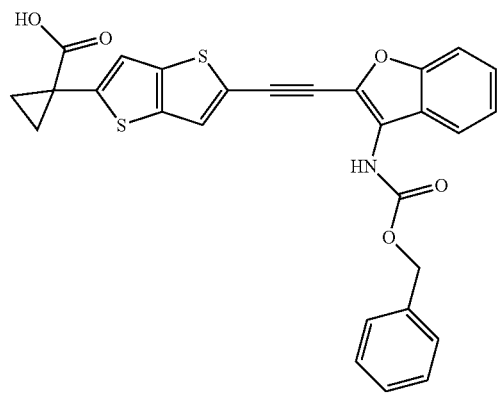 [SMILES: O=C(Nc1c(C#Cc2cc3sc(C4(C(=O)O)CC4)cc3s2)oc2ccccc12)OCc1ccccc1]
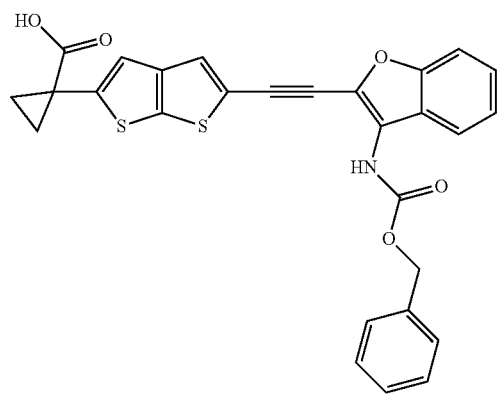 [SMILES: O=C(Nc1c(C#Cc2cc3cc(C4(C(=O)O)CC4)sc3s2)oc2ccccc12)OCc1ccccc1]
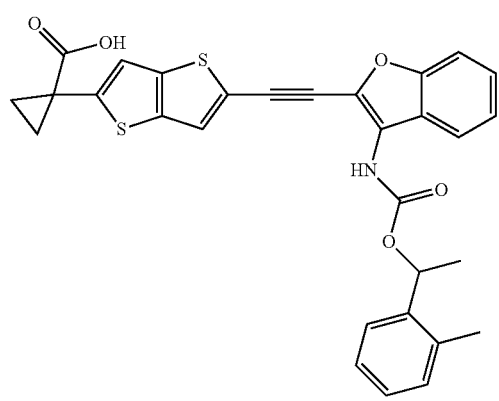 [SMILES: Cc1ccccc1C(C)OC(=O)Nc1c(C#Cc2cc3sc(C4(C(=O)O)CC4)cc3s2)oc2ccccc12]
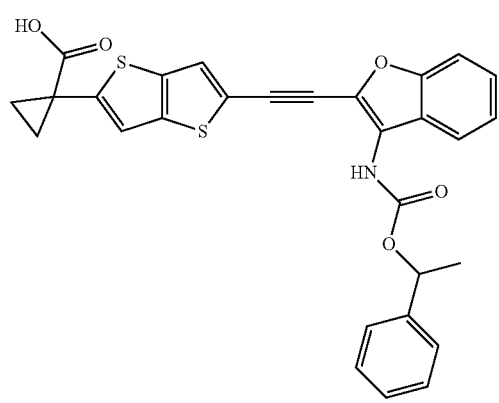 [SMILES: CC(OC(=O)Nc1c(C#Cc2cc3sc(C4(C(=O)O)CC4)cc3s2)oc2ccccc12)c1ccccc1]
TABLE 11-continued
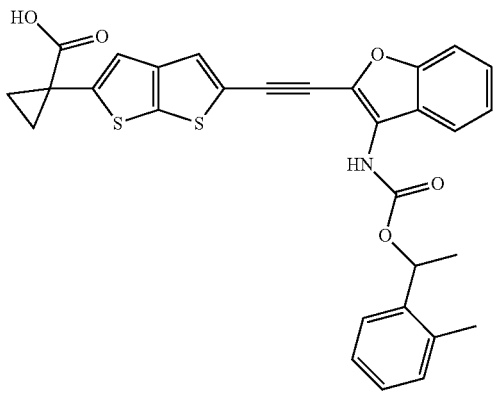 [SMILES: Cc1ccccc1C(C)OC(=O)Nc1c(C#Cc2cc3cc(C4(C(=O)O)CC4)sc3s2)oc2ccccc12]
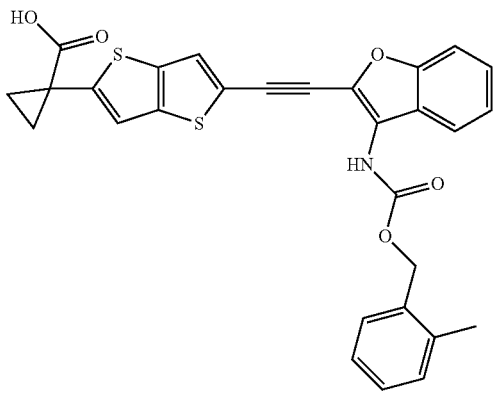 [SMILES: Cc1ccccc1COC(=O)Nc1c(C#Cc2cc3sc(C4(C(=O)O)CC4)cc3s2)oc2ccccc12]
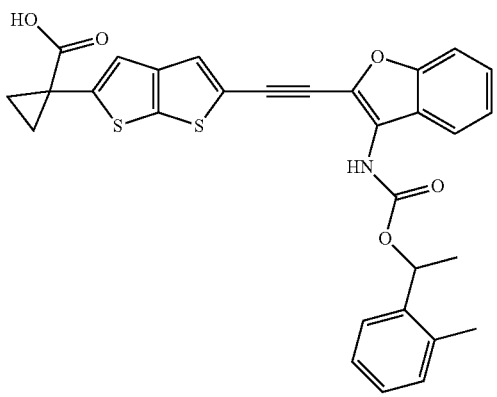
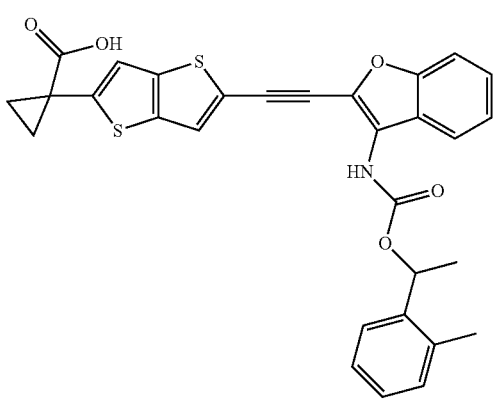 [SMILES: Cc1ccccc1C(C)OC(=O)Nc1c(C#Cc2cc3sc(C4(C(=O)O)CC4)cc3s2)oc2ccccc12]

TABLE 11-continued
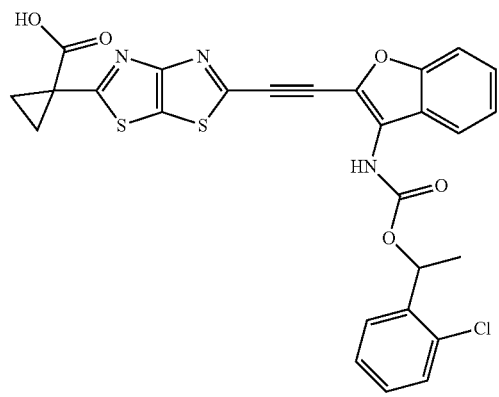 [SMILES: CC(OC(=O)Nc1c(C#Cc2nc3nc(C4(C(=O)O)CC4)sc3s2)oc2ccccc12)c1ccccc1Cl]
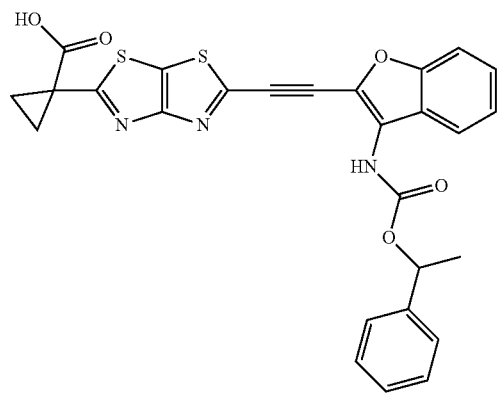 [SMILES: CC(OC(=O)Nc1c(C#Cc2nc3nc(C4(C(=O)O)CC4)sc3s2)oc2ccccc12)c1ccccc1]
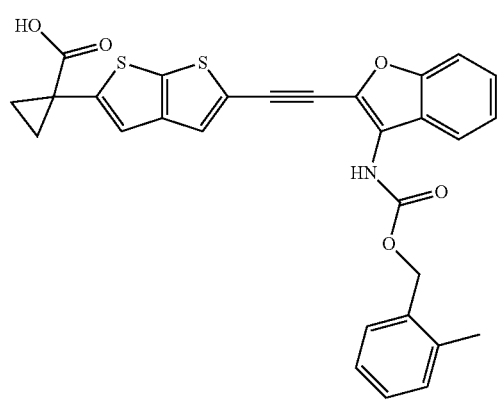 [SMILES: Cc1ccccc1COC(=O)Nc1c(C#Cc2cc3cc(C4(C(=O)O)CC4)sc3s2)oc2ccccc12]
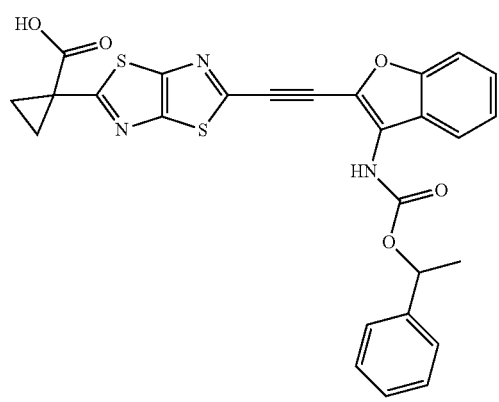 [SMILES: CC(OC(=O)Nc1c(C#Cc2nc3sc(C4(C(=O)O)CC4)nc3s2)oc2ccccc12)c1ccccc1]
TABLE 11-continued
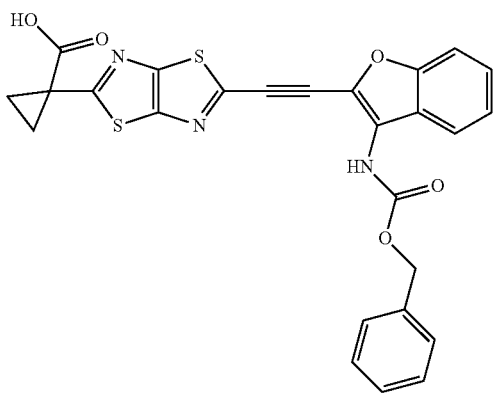 [SMILES: O=C(Nc1c(C#Cc2nc3sc(C4(C(=O)O)CC4)nc3s2)oc2ccccc12)OCc1ccccc1]
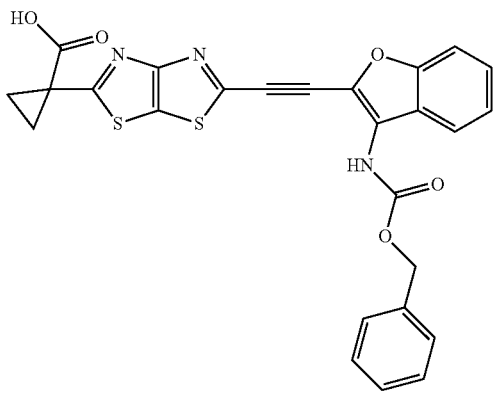 [SMILES: O=C(Nc1c(C#Cc2nc3nc(C4(C(=O)O)CC4)sc3s2)oc2ccccc12)OCc1ccccc1]
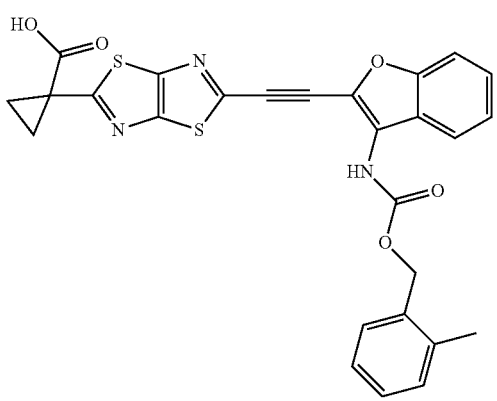 [SMILES: Cc1ccccc1COC(=O)Nc1c(C#Cc2nc3sc(C4(C(=O)O)CC4)nc3s2)oc2ccccc12]
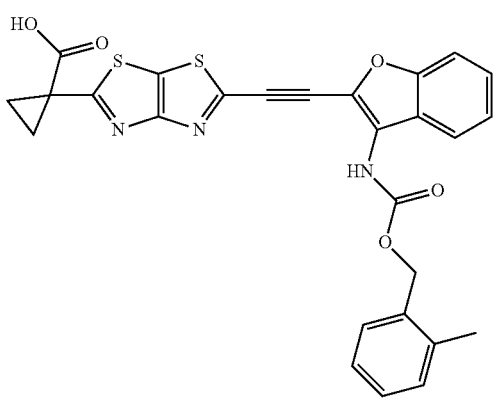 [SMILES: Cc1ccccc1COC(=O)Nc1c(C#Cc2nc3nc(C4(C(=O)O)CC4)sc3s2)oc2ccccc12]

TABLE 11-continued
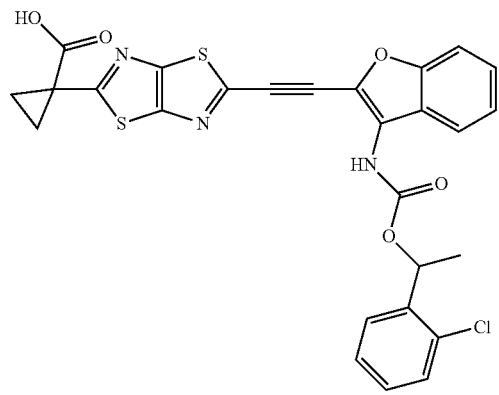 [SMILES: CC(OC(=O)Nc1c(C#Cc2nc3sc(C4(C(=O)O)CC4)nc3s2)oc2ccccc12)c1ccccc1Cl]
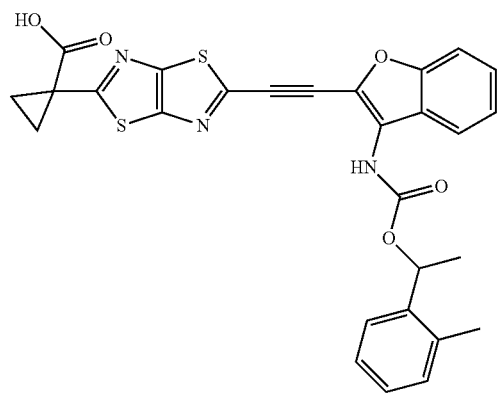 [SMILES: Cc1ccccc1C(C)OC(=O)Nc1c(C#Cc2nc3sc(C4(C(=O)O)CC4)nc3s2)oc2ccccc12]
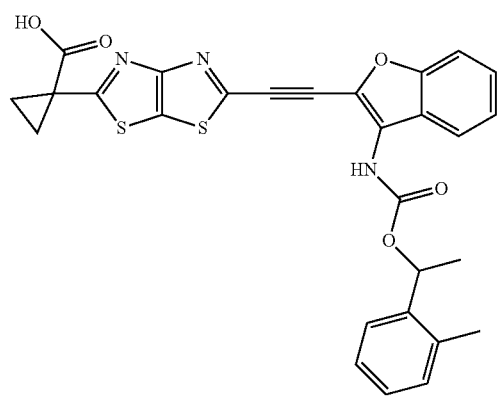 [SMILES: Cc1ccccc1C(C)OC(=O)Nc1c(C#Cc2nc3nc(C4(C(=O)O)CC4)sc3s2)oc2ccccc12]
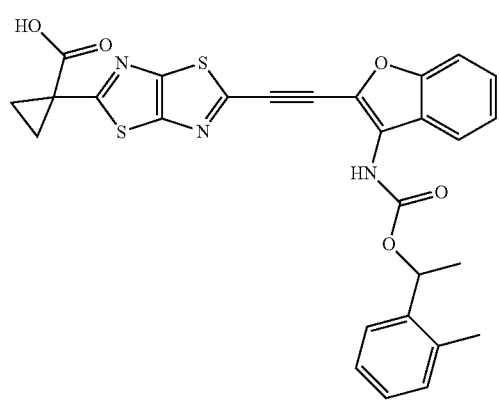 [SMILES: Cc1ccccc1C(C)OC(=O)Nc1c(C#Cc2nc3sc(C4(C(=O)O)CC4)nc3s2)oc2ccccc12]
TABLE 11-continued
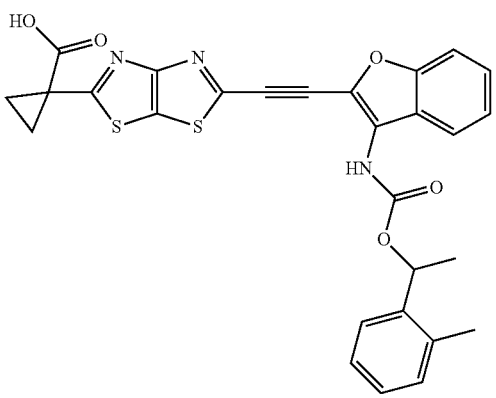
or pharmaceutically acceptable salts thereof.
28. The compound or pharmaceutically acceptable salt thereof of claim 1, selected from compounds of Table 12 having the following structures:
TABLE 12
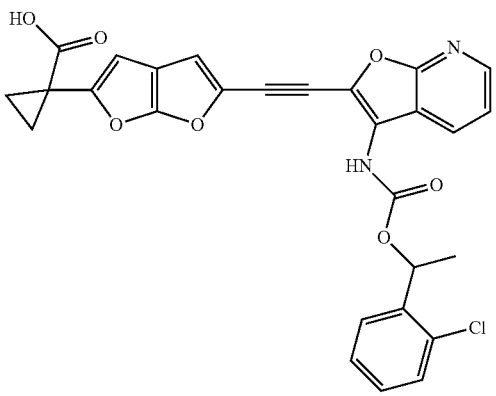
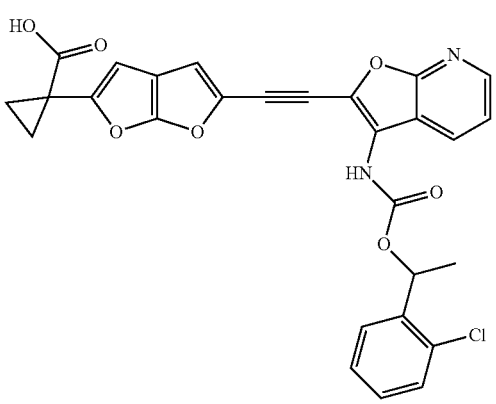

TABLE 12-continued
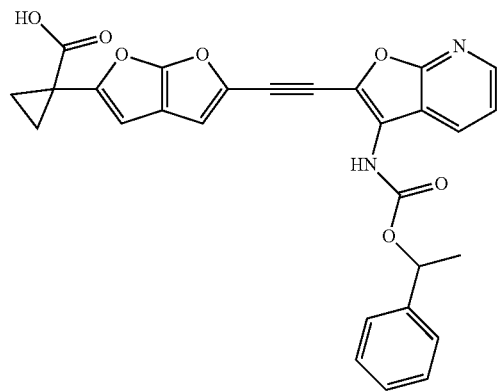 [SMILES: CC(OC(=O)Nc1c(C#Cc2cc3cc(C4(C(=O)O)CC4)oc3o2)oc2ncccc12)c1ccccc1]

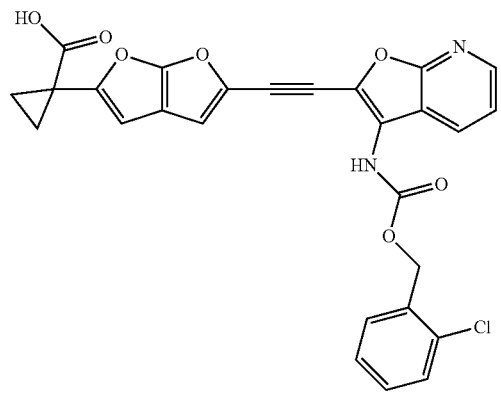 [SMILES: O=C(Nc1c(C#Cc2cc3cc(C4(C(=O)O)CC4)oc3o2)oc2ncccc12)OCc1ccccc1Cl]
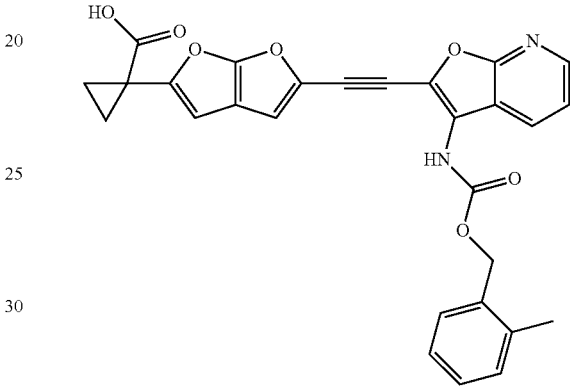
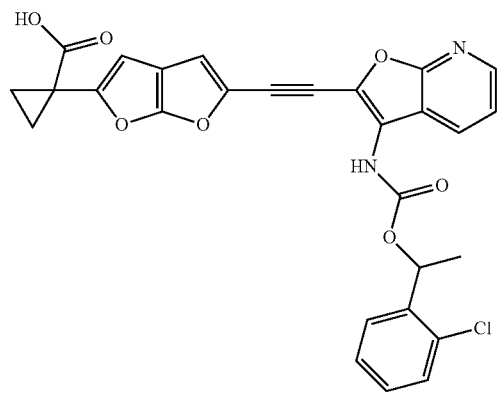 [SMILES: CC(OC(=O)Nc1c(C#Cc2cc3cc(C4(C(=O)O)CC4)oc3o2)oc2ncccc12)c1ccccc1Cl]
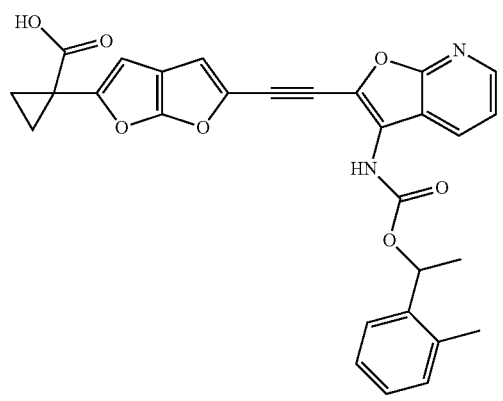 [SMILES: Cc1ccccc1C(C)OC(=O)Nc1c(C#Cc2cc3cc(C4(C(=O)O)CC4)oc3o2)oc2ncccc12]

TABLE 12-continued
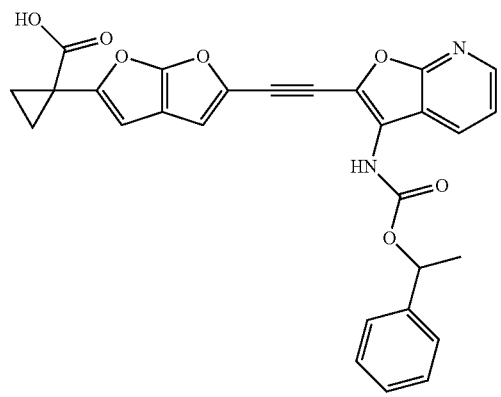 [SMILES: CC(OC(=O)Nc1c(C#Cc2cc3cc(C4(C(=O)O)CC4)oc3o2)oc2ncccc12)c1ccccc1]
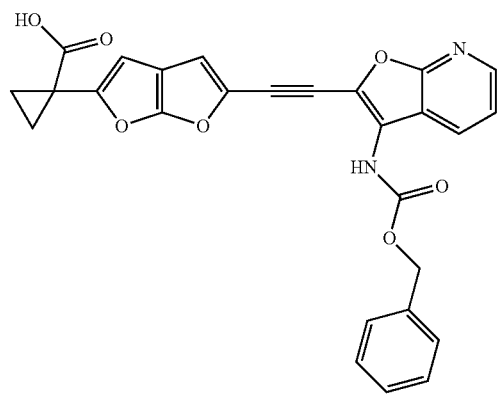 [SMILES: O=C(Nc1c(C#Cc2cc3cc(C4(C(=O)O)CC4)oc3o2)oc2ncccc12)OCc1ccccc1]
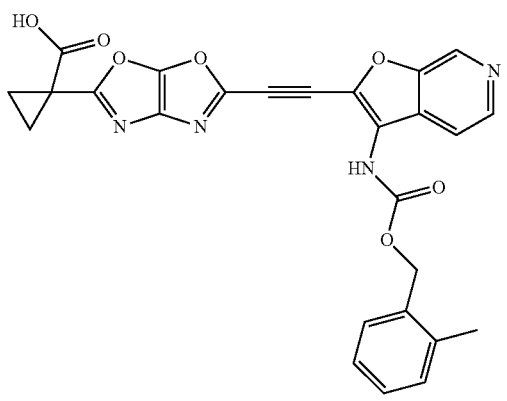
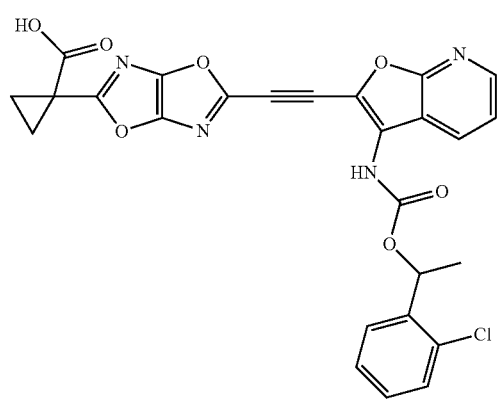 [SMILES: CC(OC(=O)Nc1c(C#Cc2nc3oc(C4(C(=O)O)CC4)nc3o2)oc2ncccc12)c1ccccc1Cl]
TABLE 12-continued
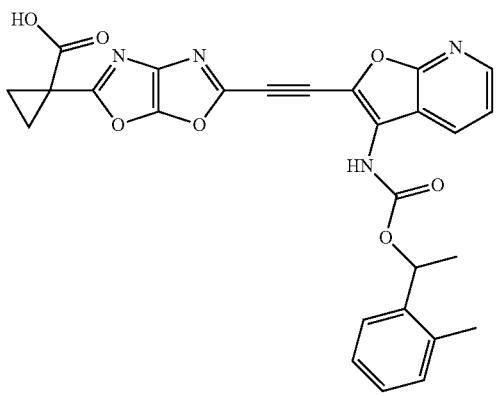 [SMILES: Cc1ccccc1C(C)OC(=O)Nc1c(C#Cc2nc3nc(C4(C(=O)O)CC4)oc3o2)oc2ncccc12]
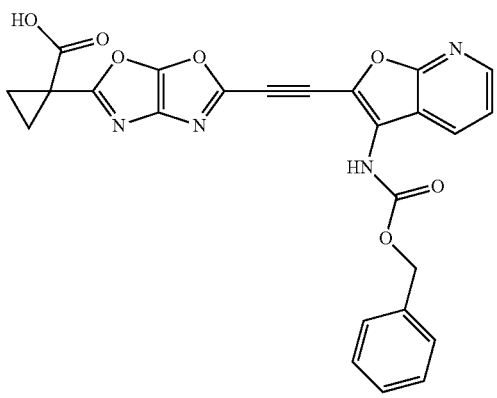 [SMILES: O=C(Nc1c(C#Cc2nc3nc(C4(C(=O)O)CC4)oc3o2)oc2ncccc12)OCc1ccccc1]
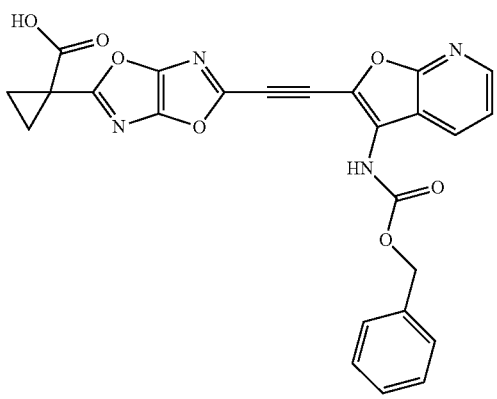
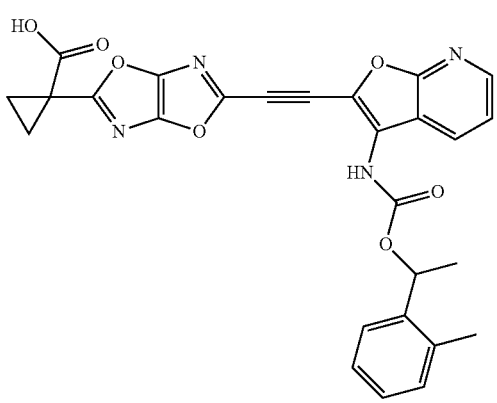 [SMILES: Cc1ccccc1C(C)OC(=O)Nc1c(C#Cc2nc3oc(C4(C(=O)O)CC4)nc3o2)oc2ncccc12]

TABLE 12-continued
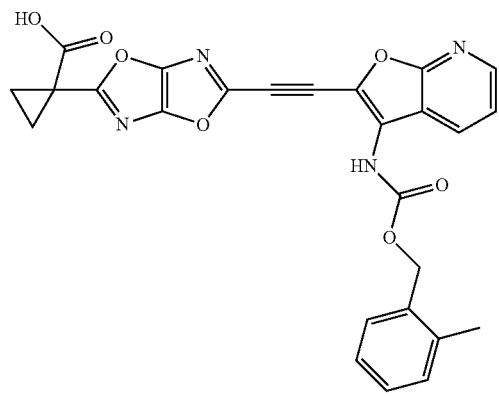 [SMILES: Cc1ccccc1COC(=O)Nc1c(C#Cc2nc3oc(C4(C(=O)O)CC4)nc3o2)oc2ncccc12]
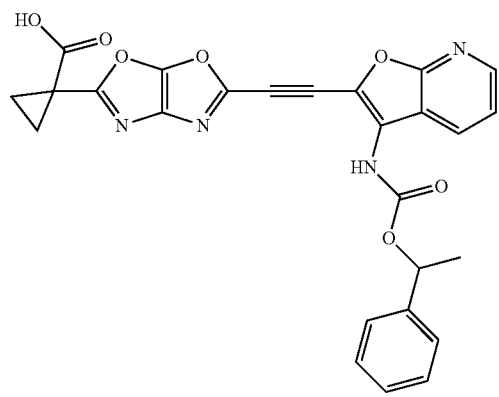 [SMILES: CC(OC(=O)Nc1c(C#Cc2nc3nc(C4(C(=O)O)CC4)oc3o2)oc2ncccc12)c1ccccc1]
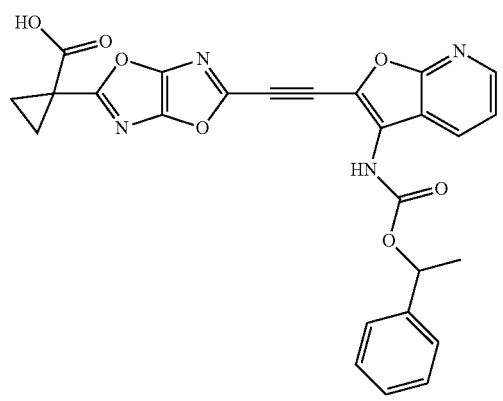 [SMILES: CC(OC(=O)Nc1c(C#Cc2nc3oc(C4(C(=O)O)CC4)nc3o2)oc2ncccc12)c1ccccc1]
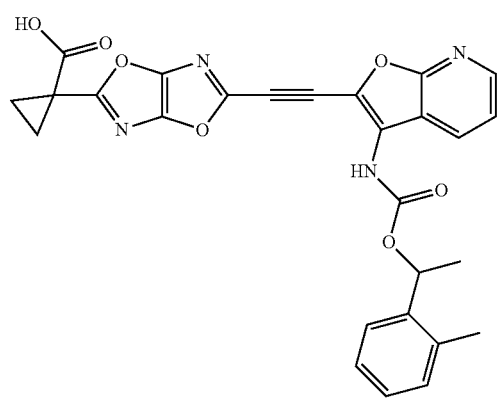 [SMILES: Cc1ccccc1C(C)OC(=O)Nc1c(C#Cc2nc3oc(C4(C(=O)O)CC4)nc3o2)oc2ncccc12]
TABLE 12-continued
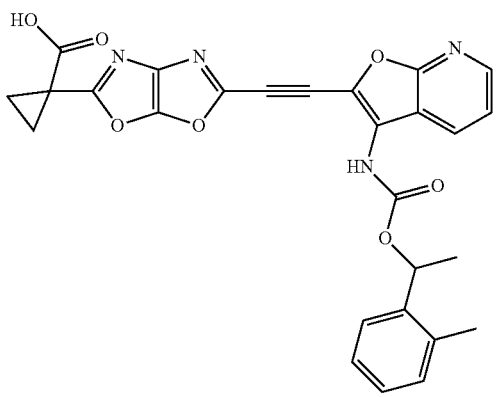 [SMILES: Cc1ccccc1C(C)OC(=O)Nc1c(C#Cc2nc3nc(C4(C(=O)O)CC4)oc3o2)oc2ncccc12]
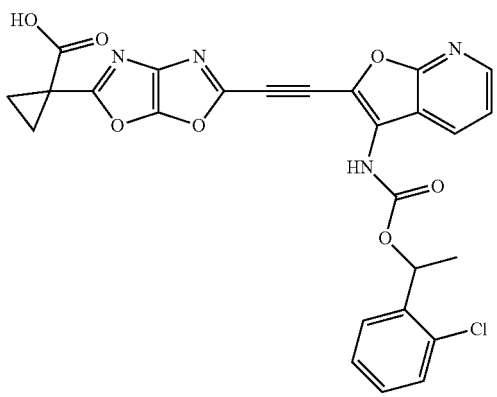
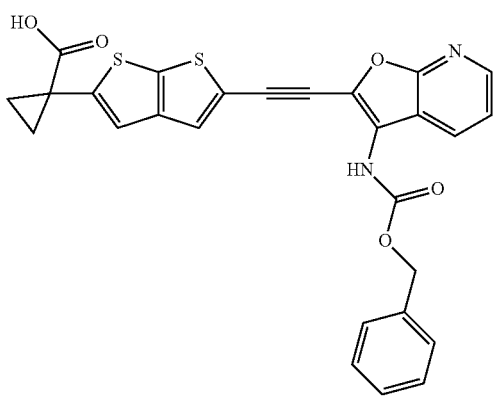 [SMILES: O=C(Nc1c(C#Cc2cc3cc(C4(C(=O)O)CC4)sc3s2)oc2ncccc12)OCc1ccccc1]
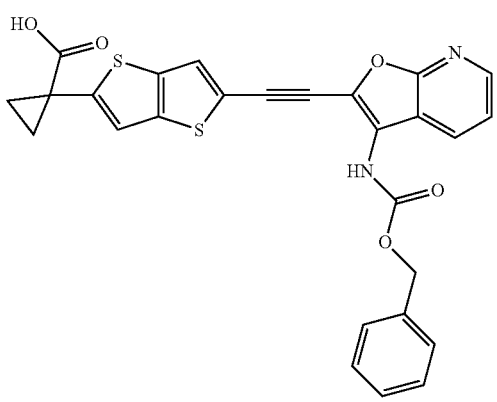 [SMILES: O=C(Nc1c(C#Cc2cc3sc(C4(C(=O)O)CC4)cc3s2)oc2ncccc12)OCc1ccccc1]

TABLE 12-continued
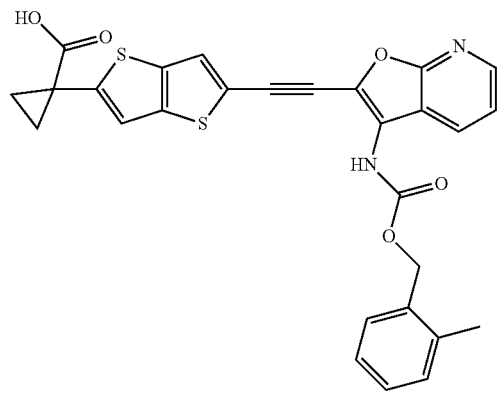 [SMILES: Cc1ccccc1COC(=O)Nc1c(C#Cc2cc3sc(C4(C(=O)O)CC4)cc3s2)oc2ncccc12]
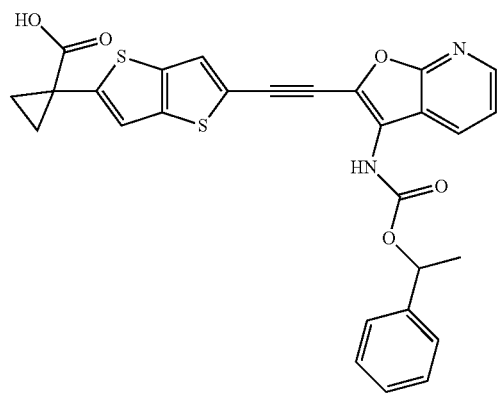 [SMILES: CC(OC(=O)Nc1c(C#Cc2cc3sc(C4(C(=O)O)CC4)cc3s2)oc2ncccc12)c1ccccc1]
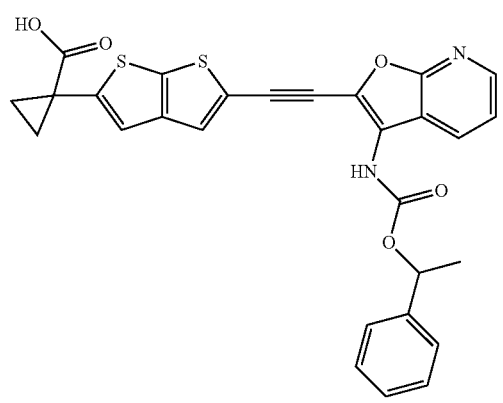
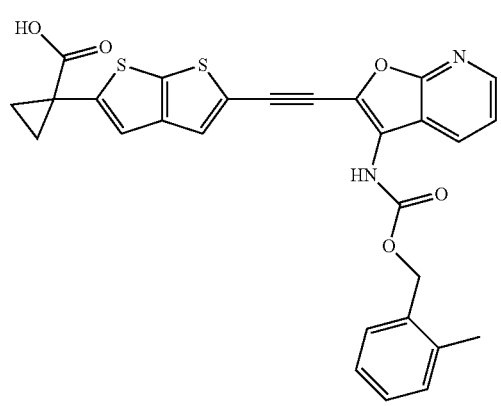 [SMILES: Cc1ccccc1COC(=O)Nc1c(C#Cc2cc3cc(C4(C(=O)O)CC4)sc3s2)oc2ncccc12]
TABLE 12-continued
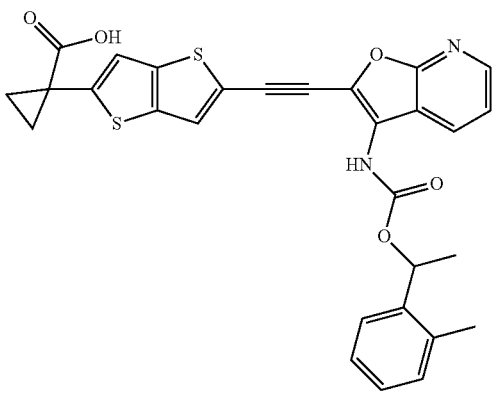 [SMILES: Cc1ccccc1C(C)OC(=O)Nc1c(C#Cc2cc3sc(C4(C(=O)O)CC4)cc3s2)oc2ncccc12]
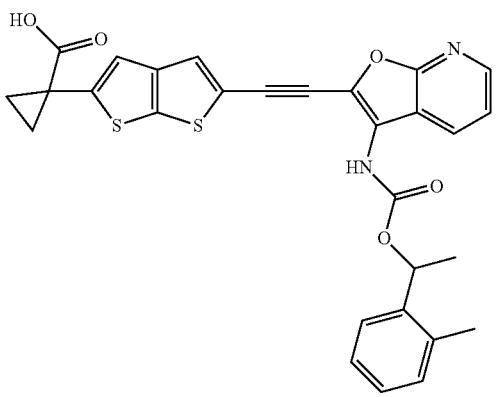 [SMILES: Cc1ccccc1C(C)OC(=O)Nc1c(C#Cc2cc3cc(C4(C(=O)O)CC4)sc3s2)oc2ncccc12]
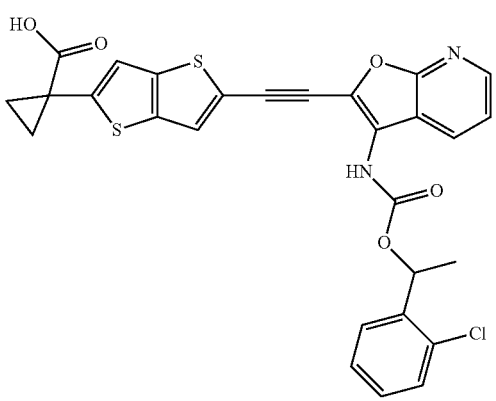 [SMILES: CC(OC(=O)Nc1c(C#Cc2cc3sc(C4(C(=O)O)CC4)cc3s2)oc2ncccc12)c1ccccc1Cl]
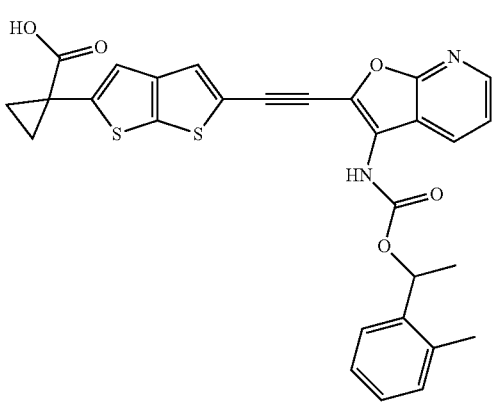 [SMILES: Cc1ccccc1C(C)OC(=O)Nc1c(C#Cc2cc3cc(C4(C(=O)O)CC4)sc3s2)oc2ncccc12]

TABLE 12-continued
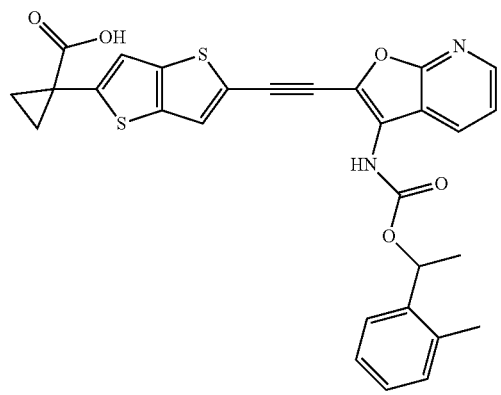 [SMILES: Cc1ccccc1C(C)OC(=O)Nc1c(C#Cc2cc3sc(C4(C(=O)O)CC4)cc3s2)oc2ncccc12]
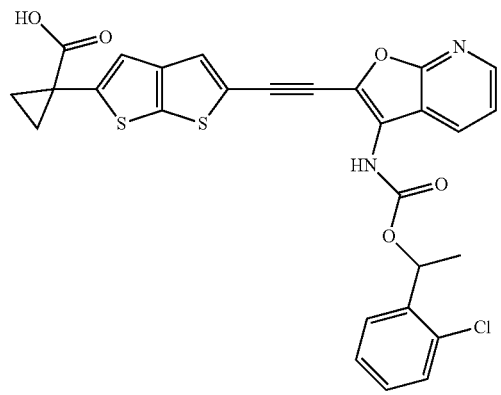 [SMILES: CC(OC(=O)Nc1c(C#Cc2cc3cc(C4(C(=O)O)CC4)sc3s2)oc2ncccc12)c1ccccc1Cl]
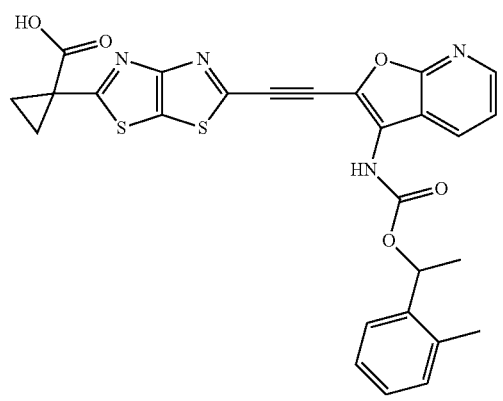
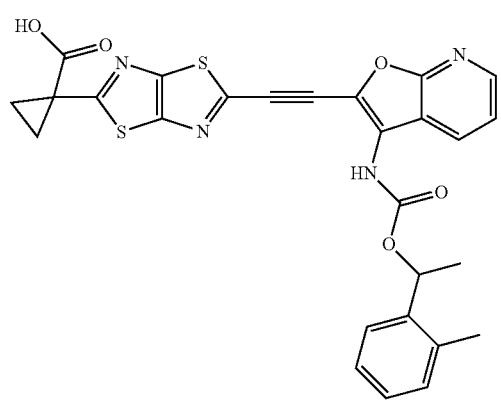 [SMILES: Cc1ccccc1C(C)OC(=O)Nc1c(C#Cc2nc3sc(C4(C(=O)O)CC4)nc3s2)oc2ncccc12]
TABLE 12-continued
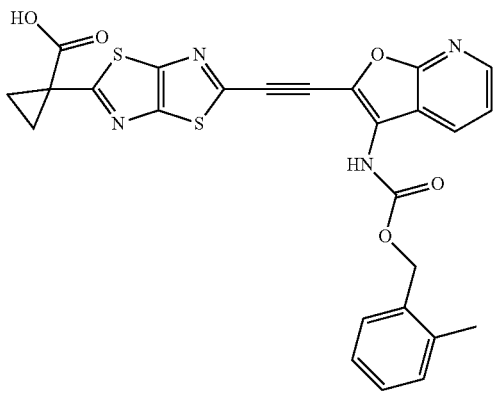 [SMILES: Cc1ccccc1COC(=O)Nc1c(C#Cc2nc3sc(C4(C(=O)O)CC4)nc3s2)oc2ncccc12]
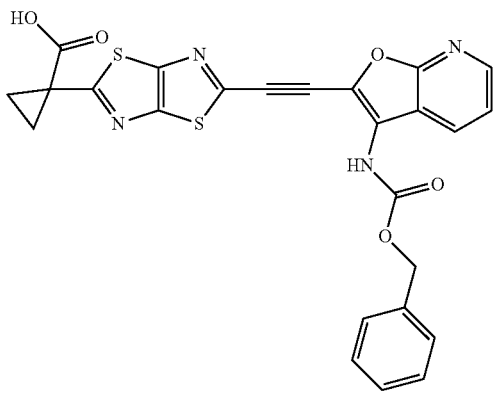 [SMILES: O=C(Nc1c(C#Cc2nc3sc(C4(C(=O)O)CC4)nc3s2)oc2ncccc12)OCc1ccccc1]
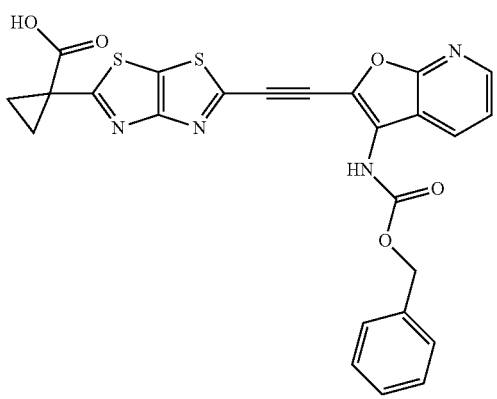
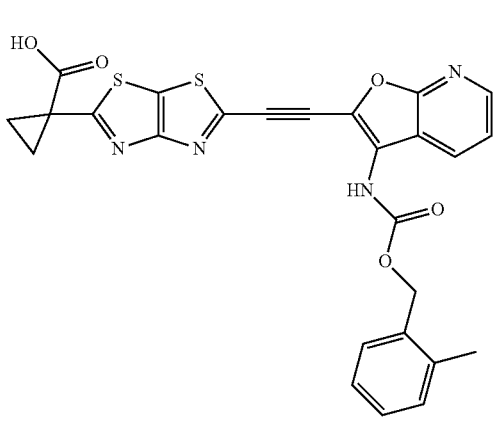 [SMILES: Cc1ccccc1COC(=O)Nc1c(C#Cc2nc3nc(C4(C(=O)O)CC4)sc3s2)oc2ncccc12]

1315
TABLE 12-continued
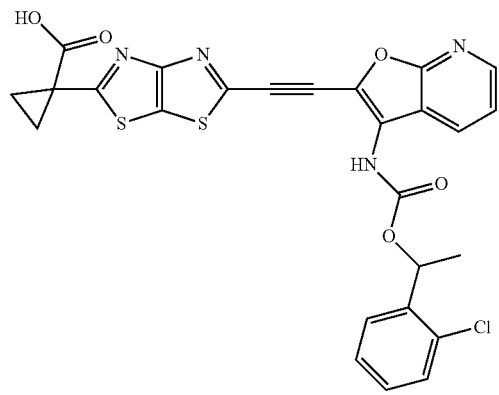 [SMILES: CC(OC(=O)Nc1c(C#Cc2nc3nc(C4(C(=O)O)CC4)sc3s2)oc2ncccc12)c1ccccc1Cl]
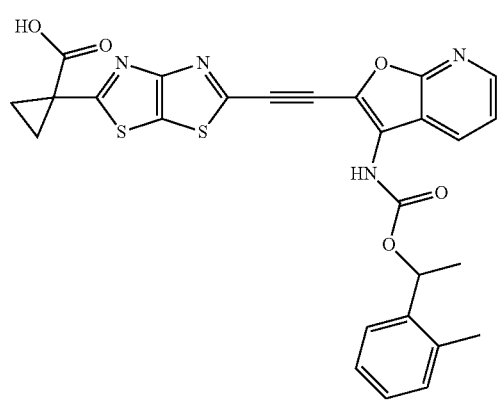
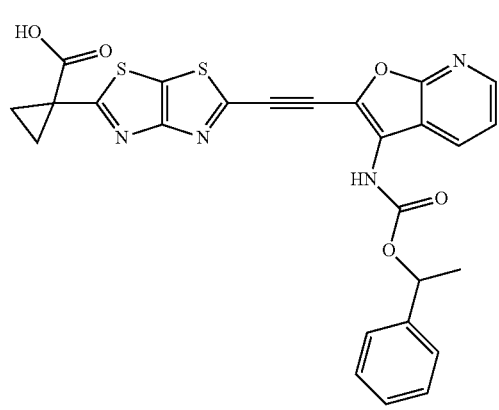 [SMILES: CC(OC(=O)Nc1c(C#Cc2nc3nc(C4(C(=O)O)CC4)sc3s2)oc2ncccc12)c1ccccc1]
1316
TABLE 12-continued
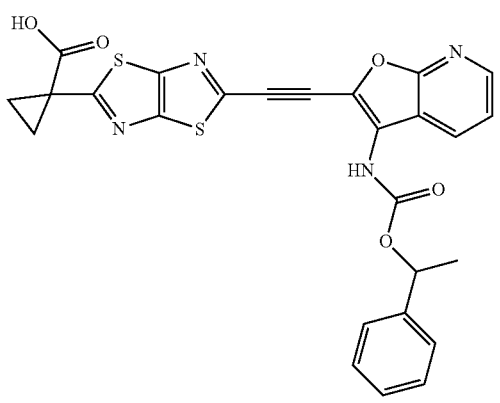 [SMILES: CC(OC(=O)Nc1c(C#Cc2nc3sc(C4(C(=O)O)CC4)nc3s2)oc2ncccc12)c1ccccc1]
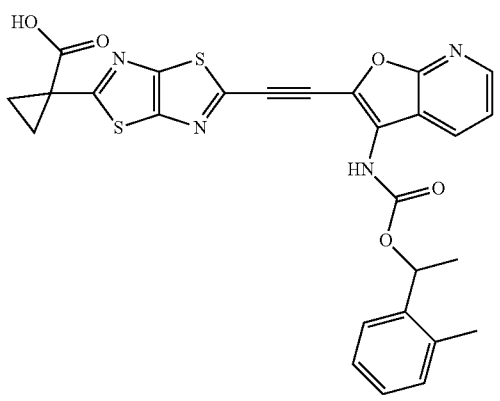 [SMILES: Cc1ccccc1C(C)OC(=O)Nc1c(C#Cc2nc3sc(C4(C(=O)O)CC4)nc3s2)oc2ncccc12]
or pharmaceutically acceptable salts thereof.
29. The compound or pharmaceutically acceptable salt thereof of claim 1, selected from compounds of Table 13 having the following structures:
TABLE 13
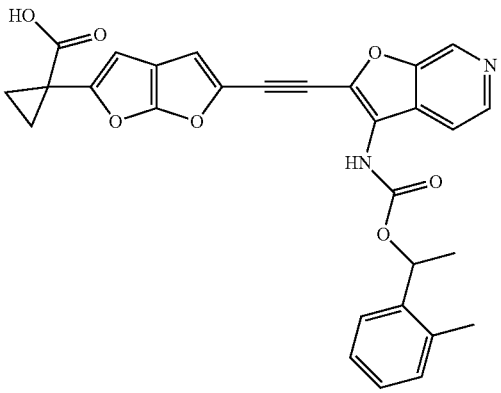

TABLE 13-continued
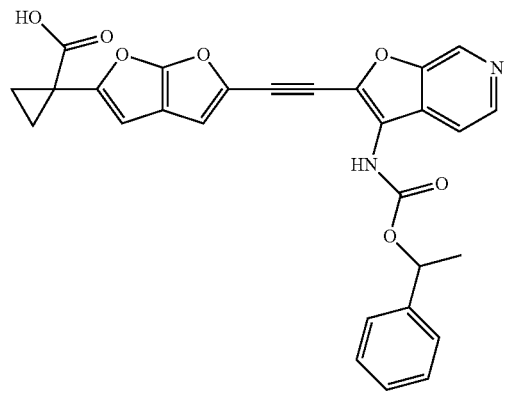 [SMILES: CC(OC(=O)Nc1c(C#Cc2cc3cc(C4(C(=O)O)CC4)oc3o2)oc2cnccc12)c1ccccc1]
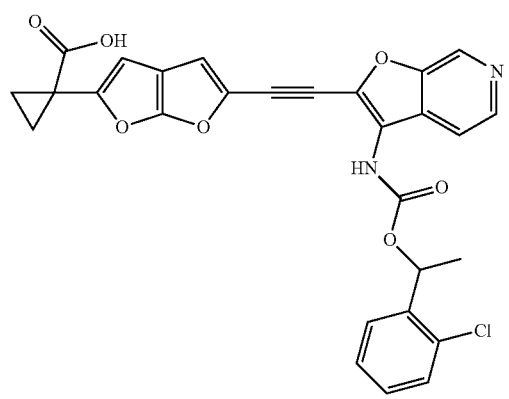 [SMILES: CC(OC(=O)Nc1c(C#Cc2cc3cc(C4(C(=O)O)CC4)oc3o2)oc2cnccc12)c1ccccc1Cl]
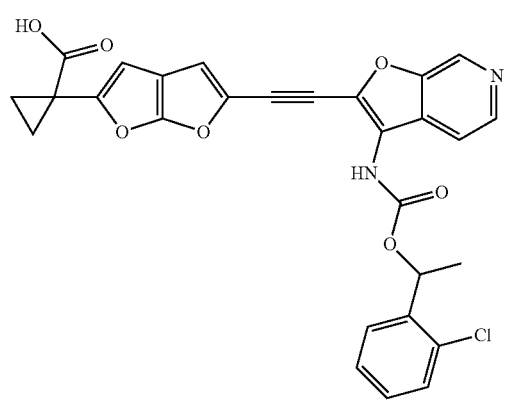
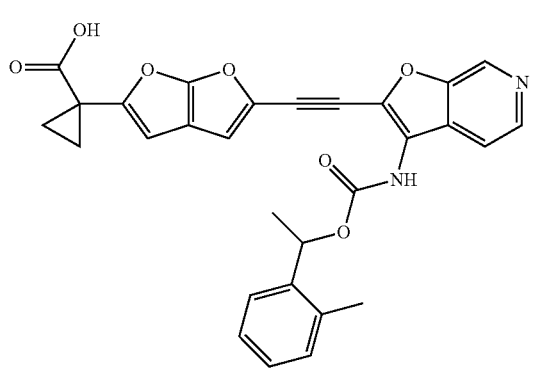 [SMILES: Cc1ccccc1C(C)OC(=O)Nc1c(C#Cc2cc3cc(C4(C(=O)O)CC4)oc3o2)oc2cnccc12]
TABLE 13-continued
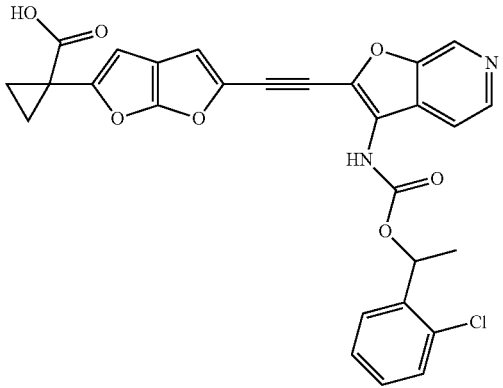
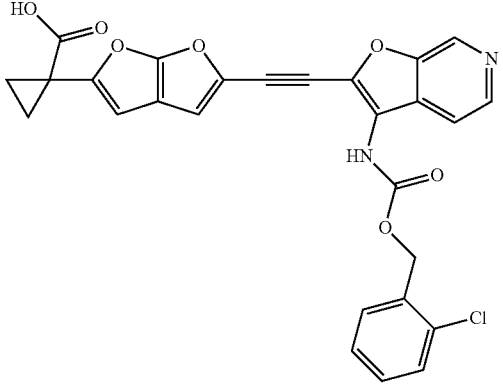
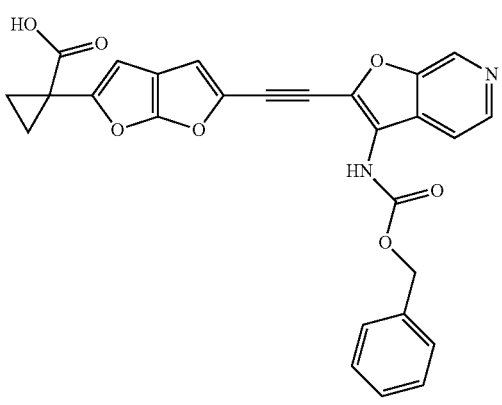 [SMILES: O=C(Nc1c(C#Cc2cc3cc(C4(C(=O)O)CC4)oc3o2)oc2cnccc12)OCc1ccccc1]
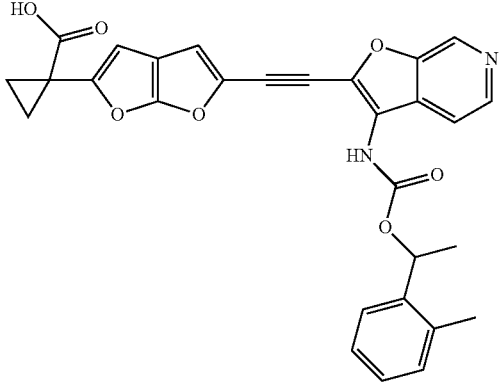 [SMILES: Cc1ccccc1C(C)OC(=O)Nc1c(C#Cc2cc3cc(C4(C(=O)O)CC4)oc3o2)oc2cnccc12]

TABLE 13-continued
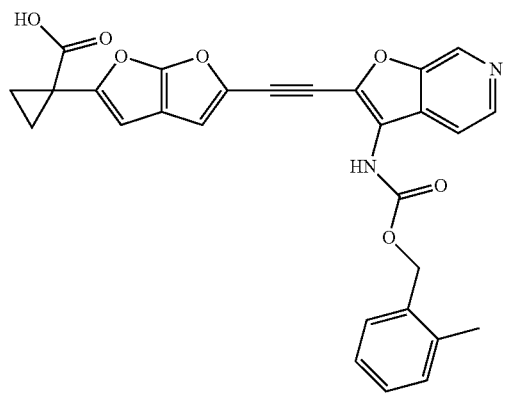 [SMILES: Cc1ccccc1COC(=O)Nc1c(C#Cc2cc3cc(C4(C(=O)O)CC4)oc3o2)oc2cnccc12]
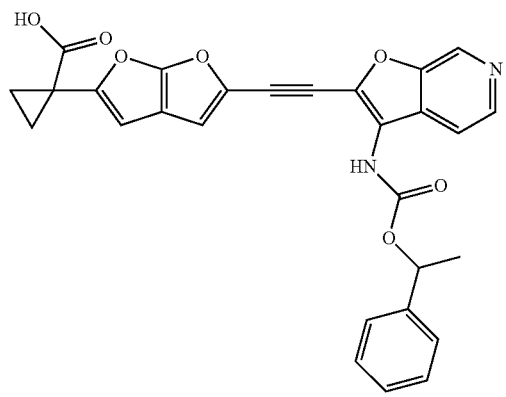 [SMILES: CC(OC(=O)Nc1c(C#Cc2cc3cc(C4(C(=O)O)CC4)oc3o2)oc2cnccc12)c1ccccc1]
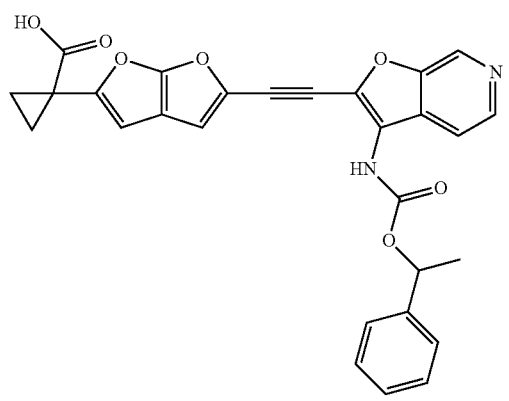 [SMILES: CC(OC(=O)Nc1c(C#Cc2cc3cc(C4(C(=O)O)CC4)oc3o2)oc2cnccc12)c1ccccc1]
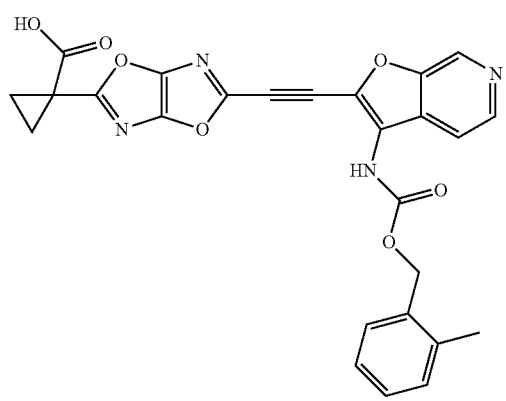 [SMILES: Cc1ccccc1COC(=O)Nc1c(C#Cc2nc3oc(C4(C(=O)O)CC4)nc3o2)oc2cnccc12]
TABLE 13-continued
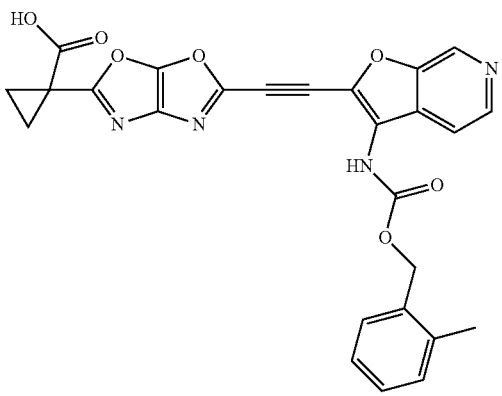 [SMILES: Cc1ccccc1COC(=O)Nc1c(C#Cc2nc3nc(C4(C(=O)O)CC4)oc3o2)oc2cnccc12]
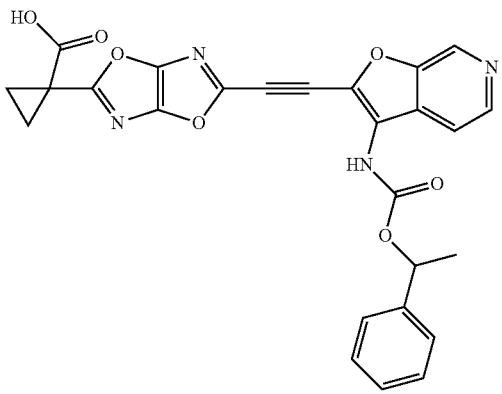 [SMILES: CC(OC(=O)Nc1c(C#Cc2nc3oc(C4(C(=O)O)CC4)nc3o2)oc2cnccc12)c1ccccc1]
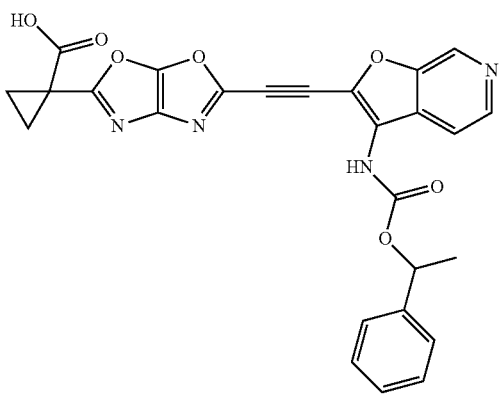 [SMILES: CC(OC(=O)Nc1c(C#Cc2nc3nc(C4(C(=O)O)CC4)oc3o2)oc2cnccc12)c1ccccc1]
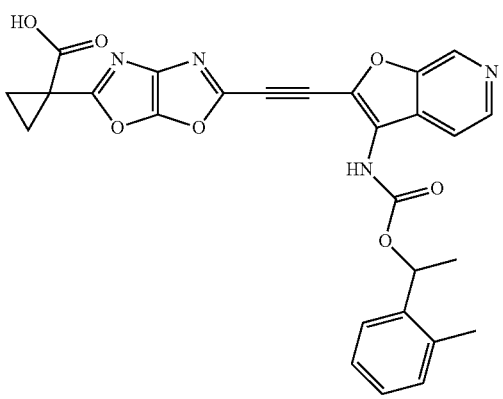 [SMILES: Cc1ccccc1C(C)OC(=O)Nc1c(C#Cc2nc3nc(C4(C(=O)O)CC4)oc3o2)oc2cnccc12]

TABLE 13-continued
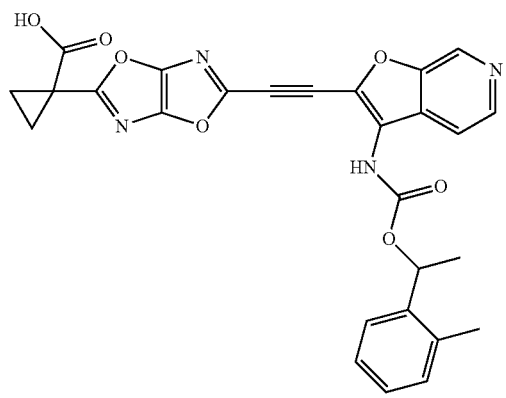 [SMILES: Cc1ccccc1C(C)OC(=O)Nc1c(C#Cc2nc3oc(C4(C(=O)O)CC4)nc3o2)oc2cnccc12]
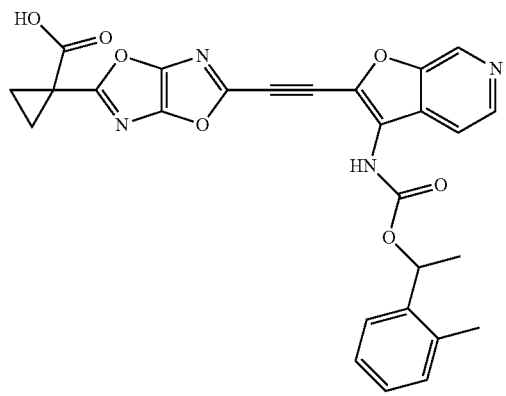
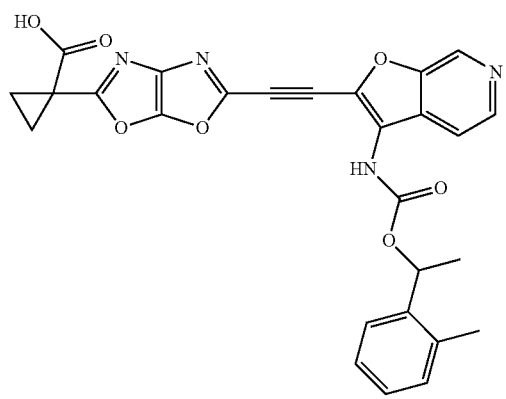 [SMILES: Cc1ccccc1C(C)OC(=O)Nc1c(C#Cc2nc3nc(C4(C(=O)O)CC4)oc3o2)oc2cnccc12]
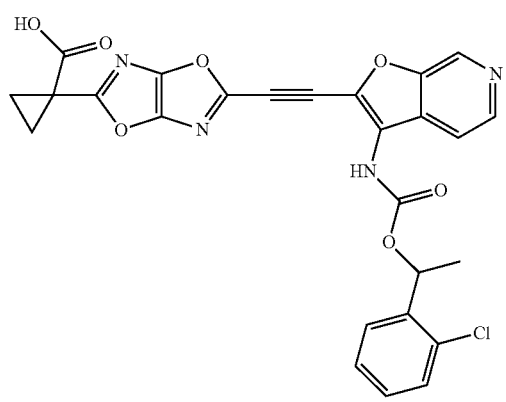 [SMILES: CC(OC(=O)Nc1c(C#Cc2nc3oc(C4(C(=O)O)CC4)nc3o2)oc2cnccc12)c1ccccc1Cl]
TABLE 13-continued
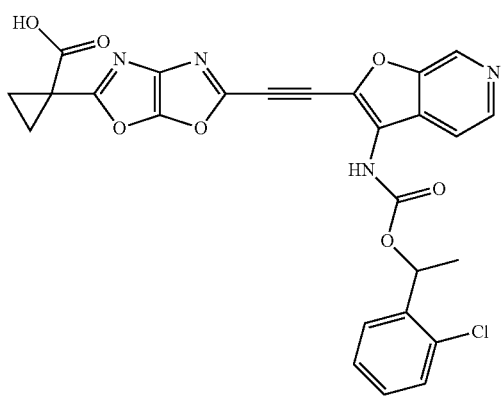 [SMILES: CC(OC(=O)Nc1c(C#Cc2nc3nc(C4(C(=O)O)CC4)oc3o2)oc2cnccc12)c1ccccc1Cl]
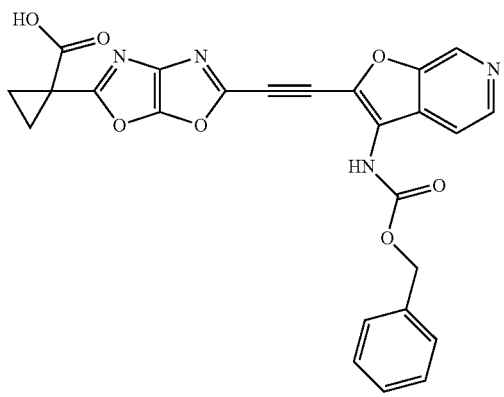 [SMILES: O=C(Nc1c(C#Cc2nc3nc(C4(C(=O)O)CC4)oc3o2)oc2cnccc12)OCc1ccccc1]
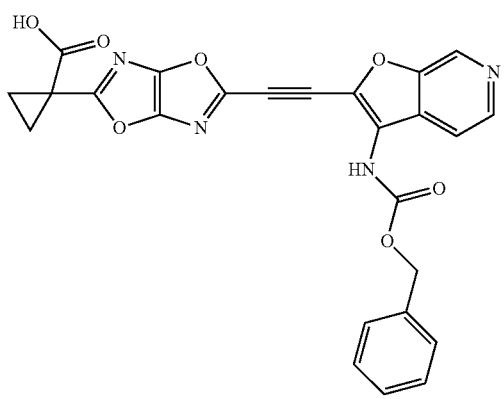 [SMILES: O=C(Nc1c(C#Cc2nc3oc(C4(C(=O)O)CC4)nc3o2)oc2cnccc12)OCc1ccccc1]
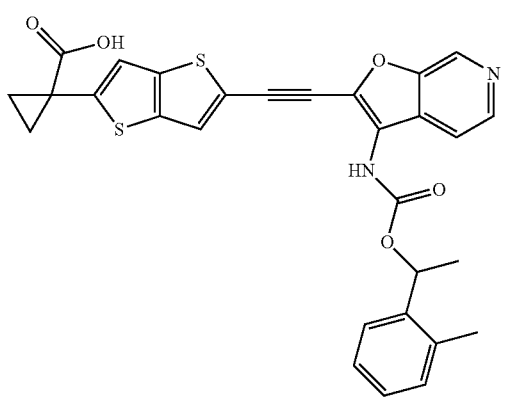 [SMILES: Cc1ccccc1C(C)OC(=O)Nc1c(C#Cc2cc3sc(C4(C(=O)O)CC4)cc3s2)oc2cnccc12]

TABLE 13-continued
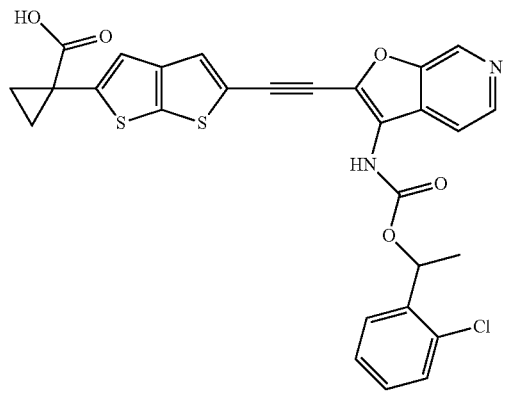 [SMILES: CC(OC(=O)Nc1c(C#Cc2cc3cc(C4(C(=O)O)CC4)sc3s2)oc2cnccc12)c1ccccc1Cl]
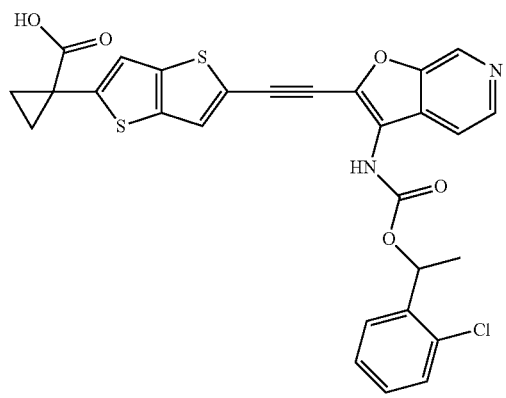 [SMILES: CC(OC(=O)Nc1c(C#Cc2cc3sc(C4(C(=O)O)CC4)cc3s2)oc2cnccc12)c1ccccc1Cl]
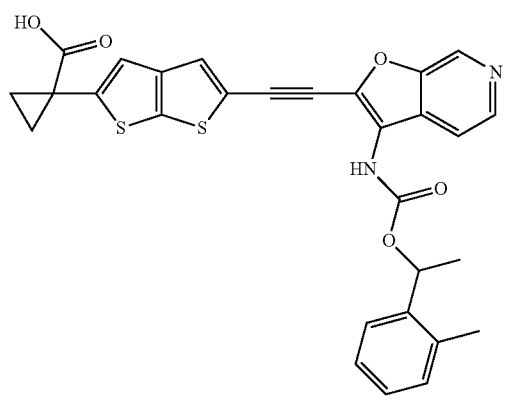
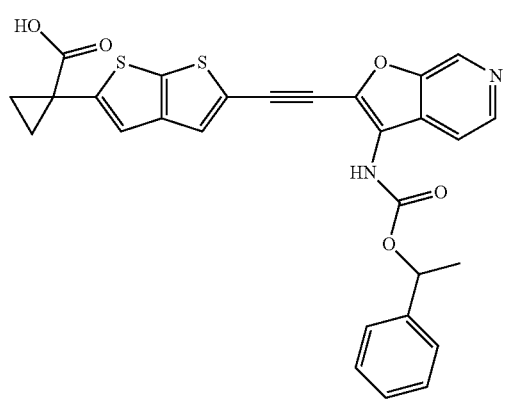
TABLE 13-continued
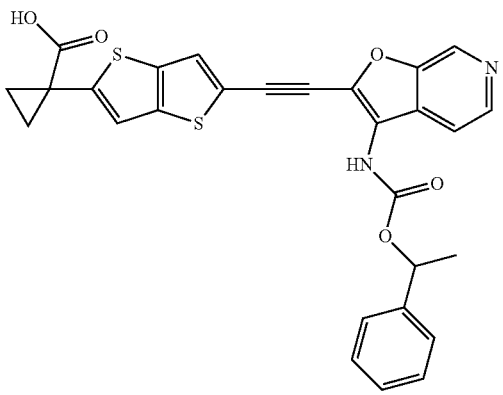 [SMILES: CC(OC(=O)Nc1c(C#Cc2cc3sc(C4(C(=O)O)CC4)cc3s2)oc2cnccc12)c1ccccc1]
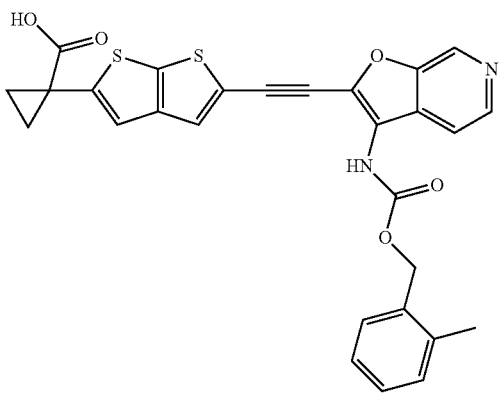 [SMILES: Cc1ccccc1COC(=O)Nc1c(C#Cc2cc3cc(C4(C(=O)O)CC4)sc3s2)oc2cnccc12]
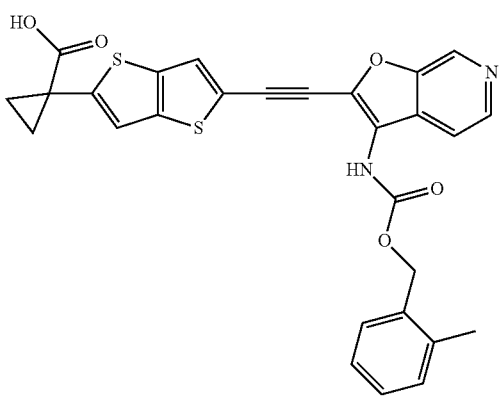 [SMILES: Cc1ccccc1COC(=O)Nc1c(C#Cc2cc3sc(C4(C(=O)O)CC4)cc3s2)oc2cnccc12]
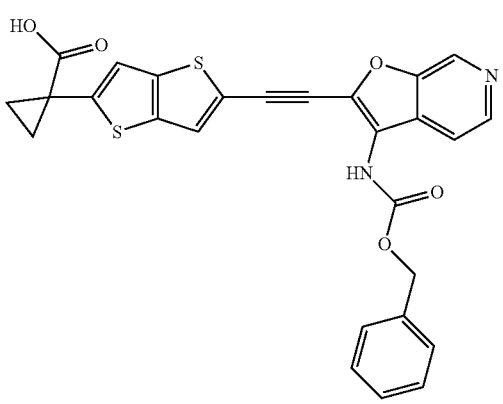 [SMILES: O=C(Nc1c(C#Cc2cc3sc(C4(C(=O)O)CC4)cc3s2)oc2cnccc12)OCc1ccccc1]

TABLE 13-continued
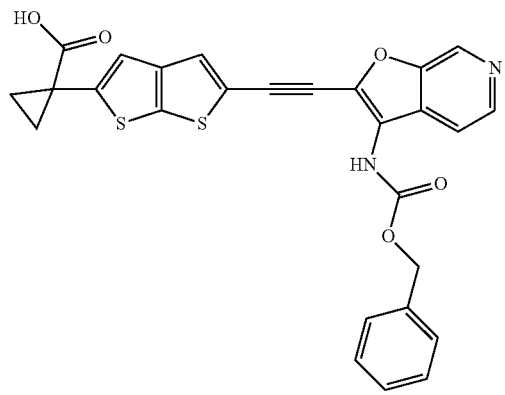
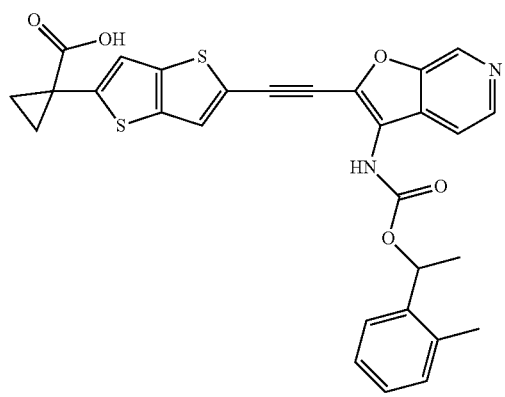 [SMILES: Cc1ccccc1C(C)OC(=O)Nc1c(C#Cc2cc3sc(C4(C(=O)O)CC4)cc3s2)oc2cnccc12]
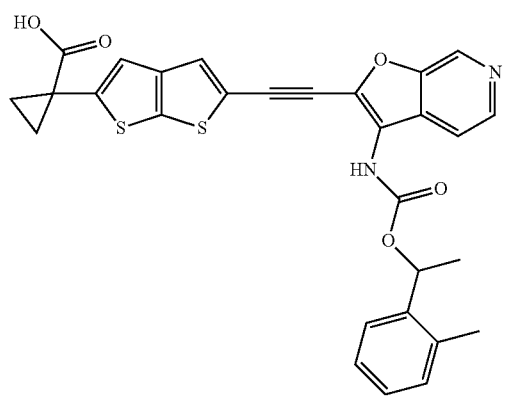
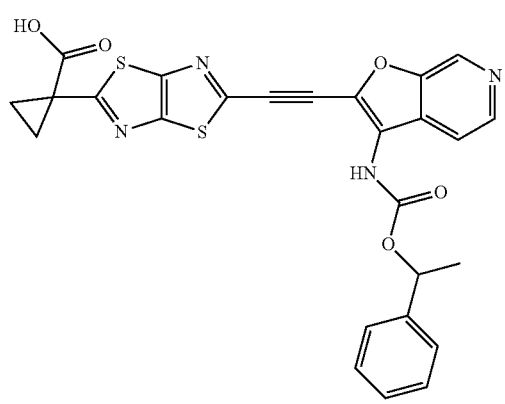 [SMILES: CC(OC(=O)Nc1c(C#Cc2nc3sc(C4(C(=O)O)CC4)nc3s2)oc2cnccc12)c1ccccc1]
TABLE 13-continued
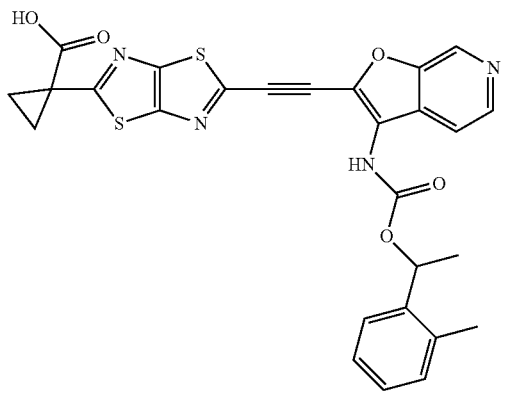 [SMILES: Cc1ccccc1C(C)OC(=O)Nc1c(C#Cc2nc3sc(C4(C(=O)O)CC4)nc3s2)oc2cnccc12]
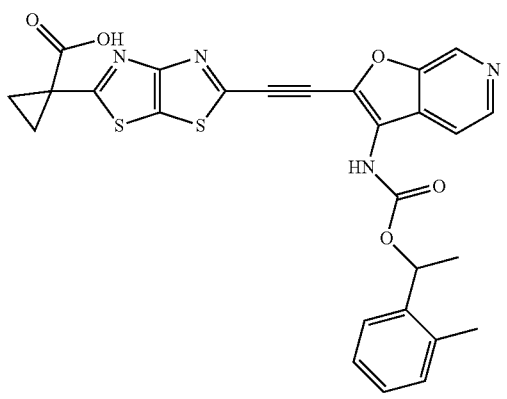 [SMILES: Cc1ccccc1C(C)OC(=O)Nc1c(C#Cc2nc3nc(C4(C(=O)O)CC4)sc3s2)oc2cnccc12]
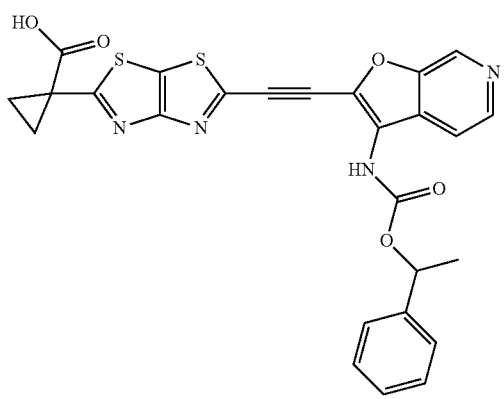
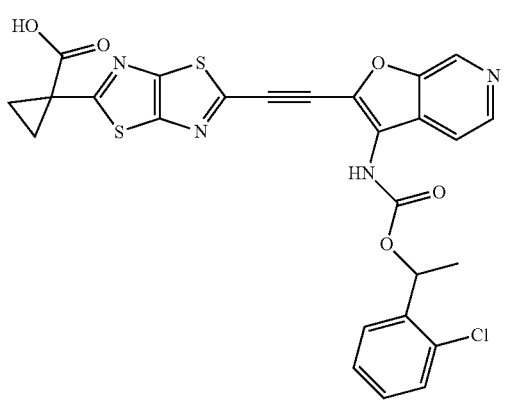 [SMILES: CC(OC(=O)Nc1c(C#Cc2nc3sc(C4(C(=O)O)CC4)nc3s2)oc2cnccc12)c1ccccc1Cl]

TABLE 13-continued
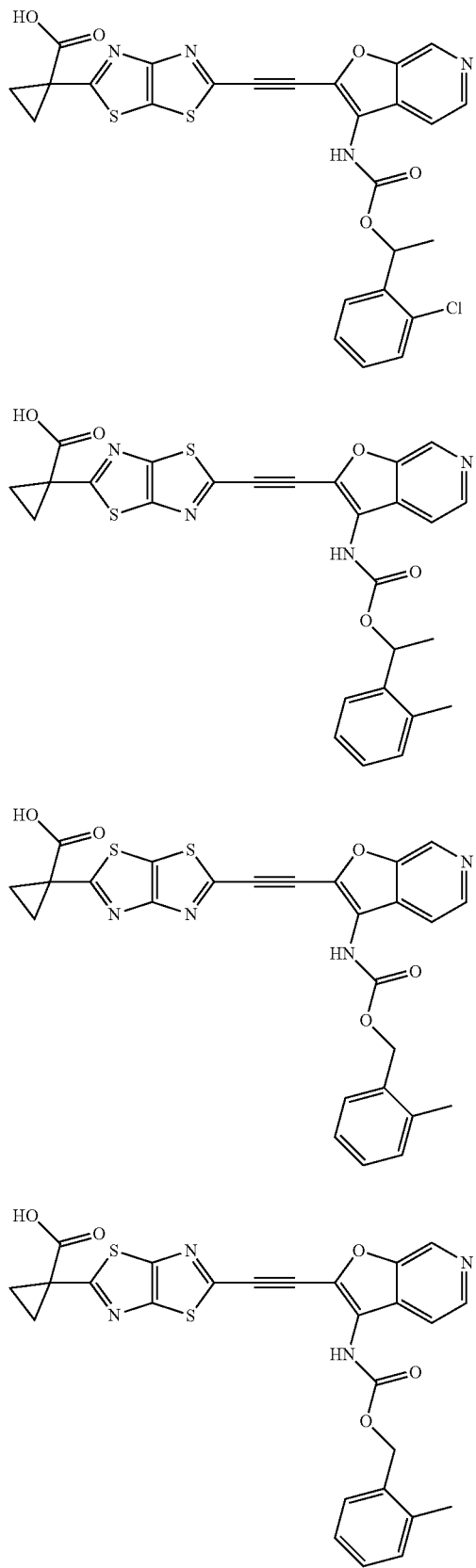
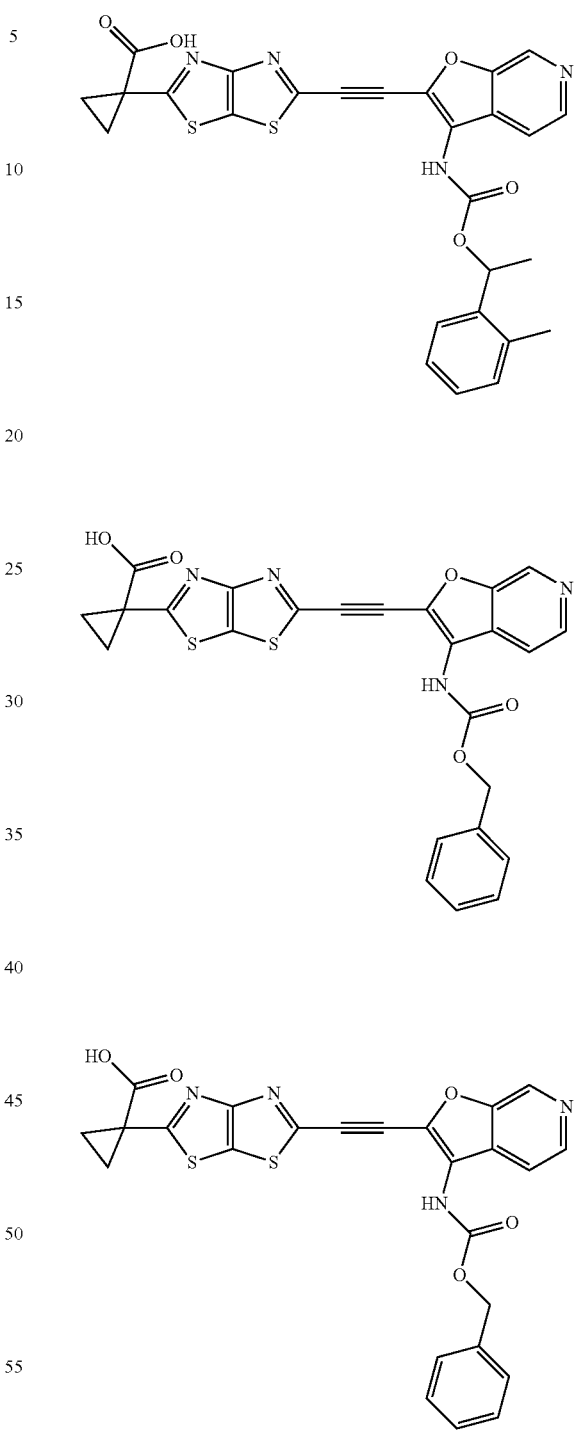
or pharmaceutically acceptable salts thereof.
30. The compound or pharmaceutically acceptable salt thereof of claim 1, selected from compounds of Table 14 having the following structures:

TABLE 14
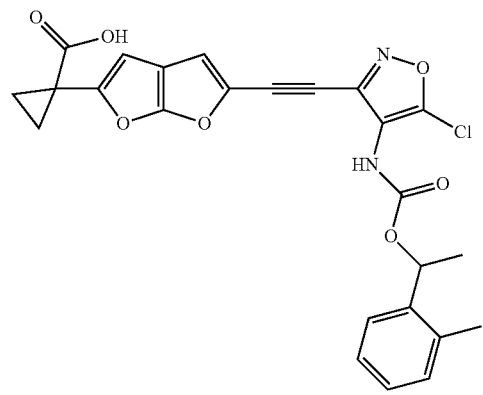
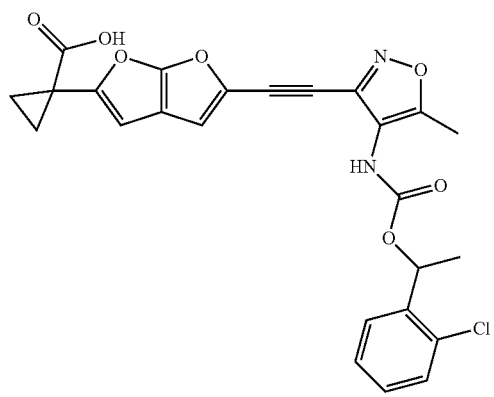 [SMILES: Cc1onc(C#Cc2cc3cc(C4(C(=O)O)CC4)oc3o2)c1NC(=O)OC(C)c1ccccc1Cl]
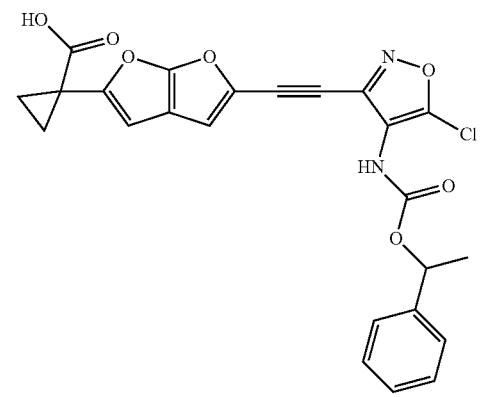 [SMILES: CC(OC(=O)Nc1c(C#Cc2cc3cc(C4(C(=O)O)CC4)oc3o2)noc1Cl)c1ccccc1]
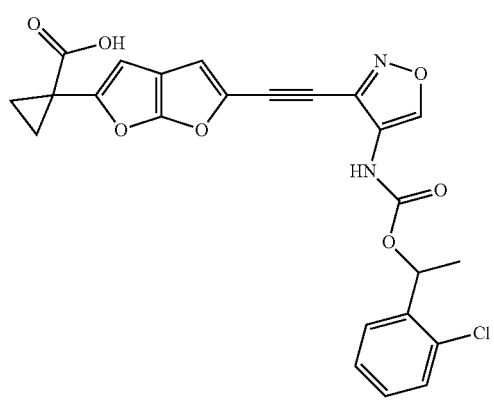 [SMILES: CC(OC(=O)Nc1conc1C#Cc1cc2cc(C3(C(=O)O)CC3)oc2o1)c1ccccc1Cl]
TABLE 14-continued
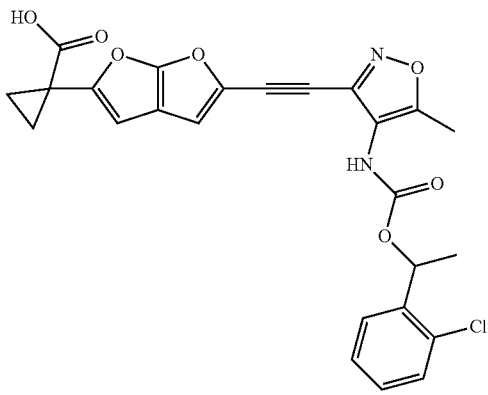
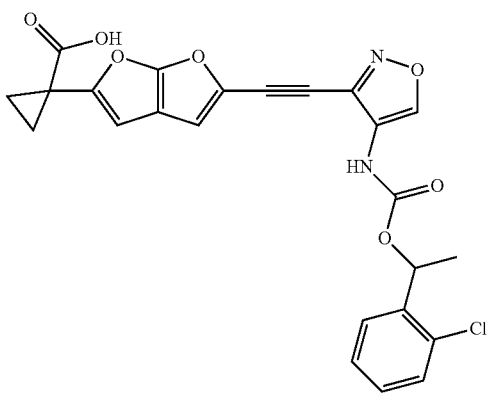
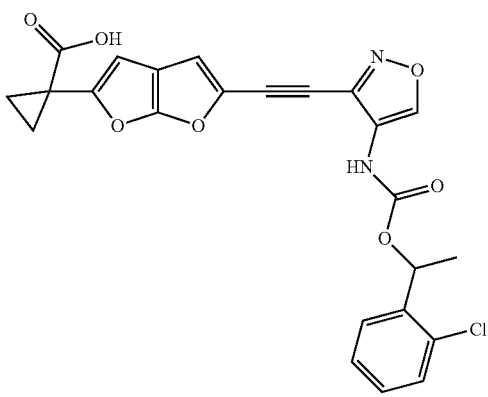
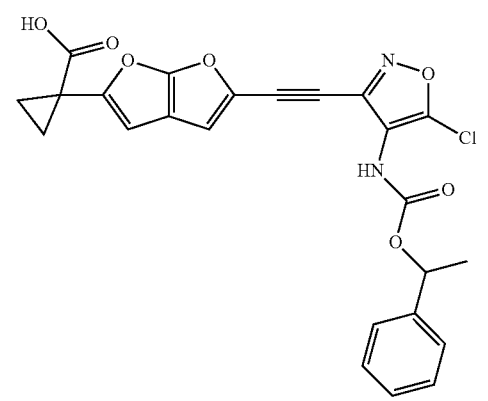

1331
TABLE 14-continued
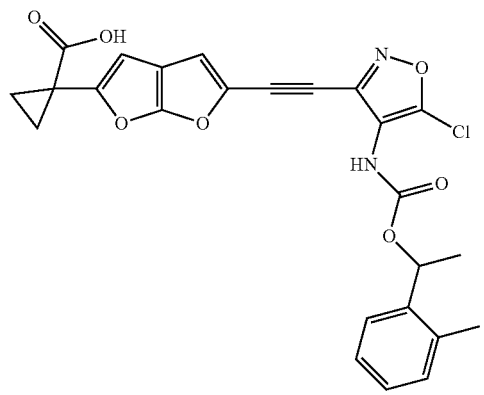
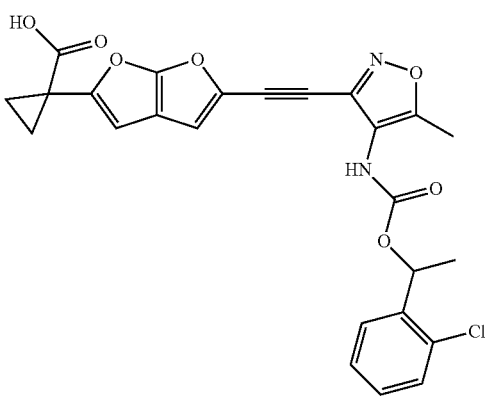
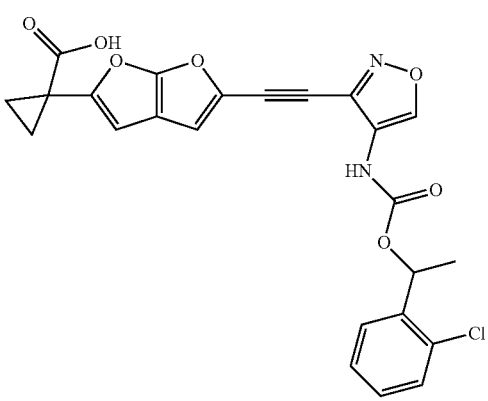
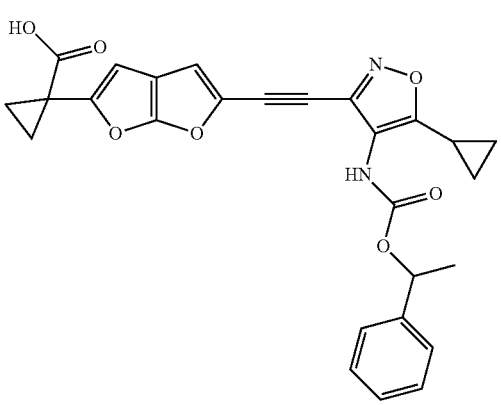
1332
TABLE 14-continued
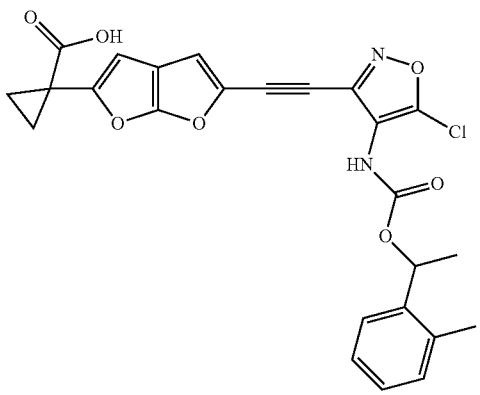
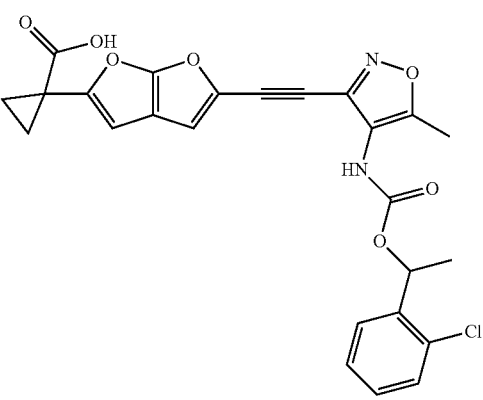
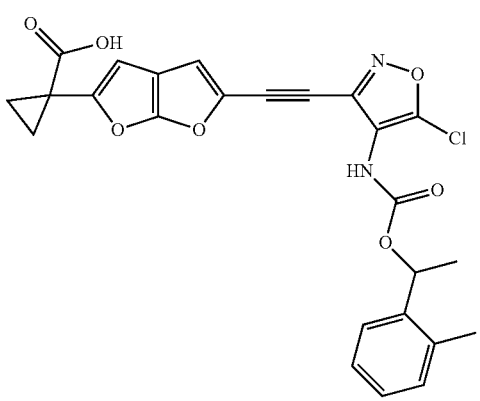 [SMILES: Cc1ccccc1C(C)OC(=O)Nc1c(C#Cc2cc3cc(C4(C(=O)O)CC4)oc3o2)noc1Cl]
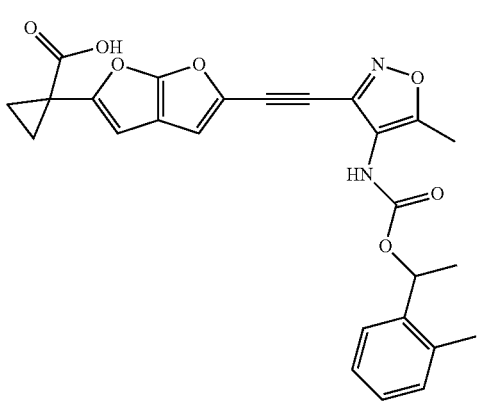 [SMILES: Cc1ccccc1C(C)OC(=O)Nc1c(C#Cc2cc3cc(C4(C(=O)O)CC4)oc3o2)noc1C]

1333
TABLE 14-continued
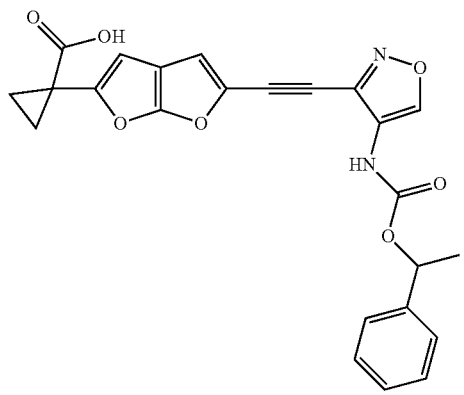 [SMILES: CC(OC(=O)Nc1conc1C#Cc1cc2cc(C3(C(=O)O)CC3)oc2o1)c1ccccc1]
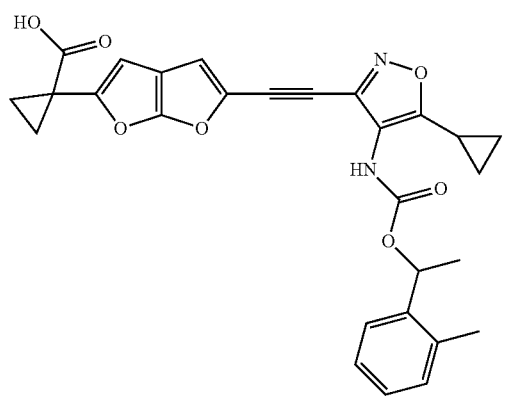 [SMILES: Cc1ccccc1C(C)OC(=O)Nc1c(C#Cc2cc3cc(C4(C(=O)O)CC4)oc3o2)noc1C1CC1]
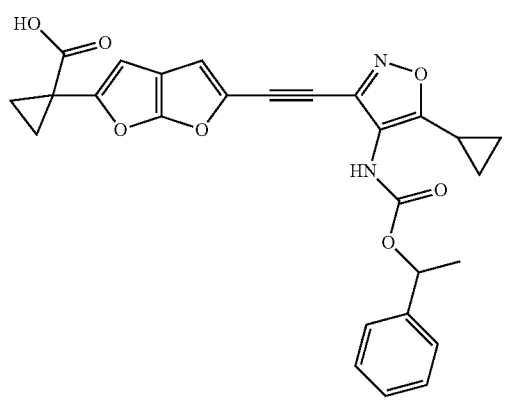
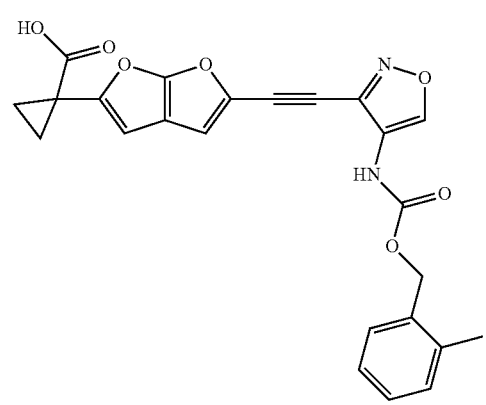 [SMILES: Cc1ccccc1COC(=O)Nc1conc1C#Cc1cc2cc(C3(C(=O)O)CC3)oc2o1]
1334
TABLE 14-continued
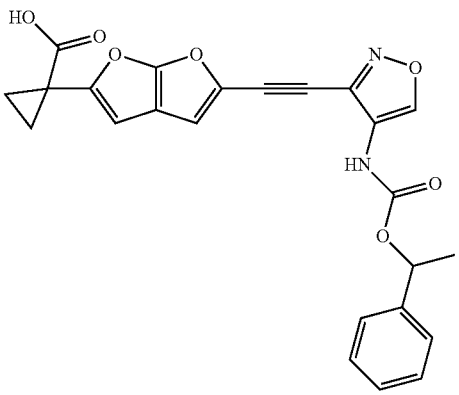
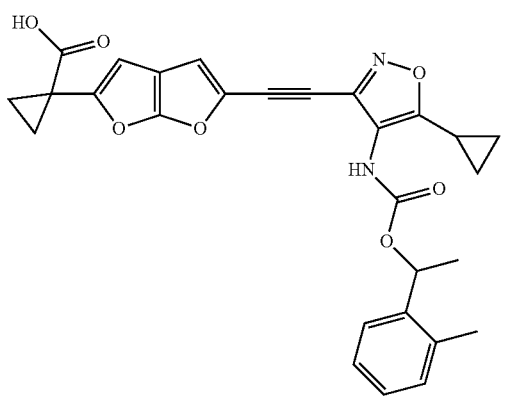
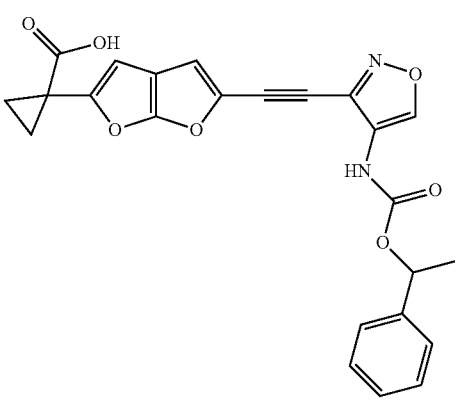 [SMILES: CC(OC(=O)Nc1conc1C#Cc1cc2cc(C3(C(=O)O)CC3)oc2o1)c1ccccc1]
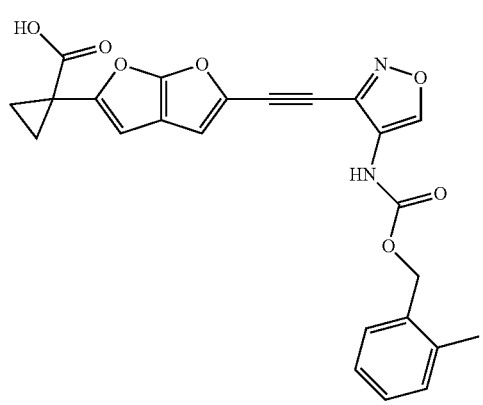

1335
TABLE 14-continued
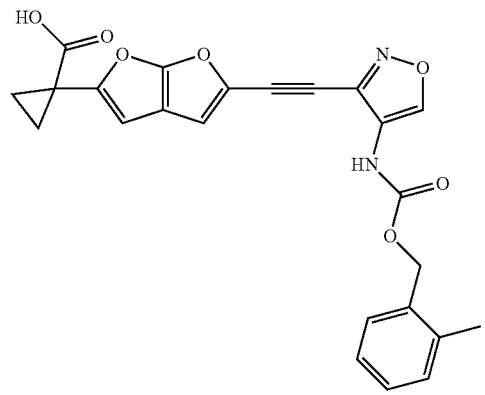
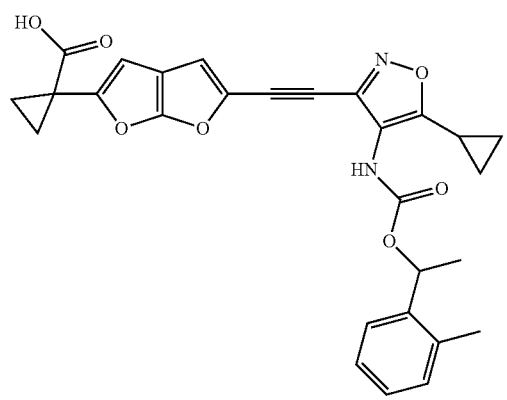 [SMILES: Cc1ccccc1C(C)OC(=O)Nc1c(C#Cc2cc3cc(C4(C(=O)O)CC4)oc3o2)noc1C1CC1]
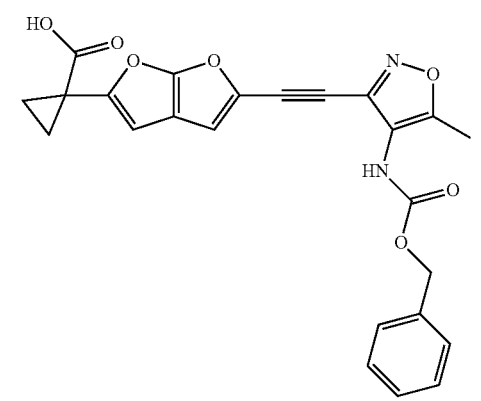
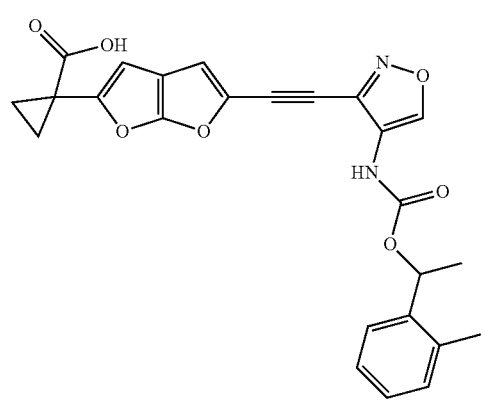 [SMILES: Cc1ccccc1C(C)OC(=O)Nc1conc1C#Cc1cc2cc(C3(C(=O)O)CC3)oc2o1]
1336
TABLE 14-continued
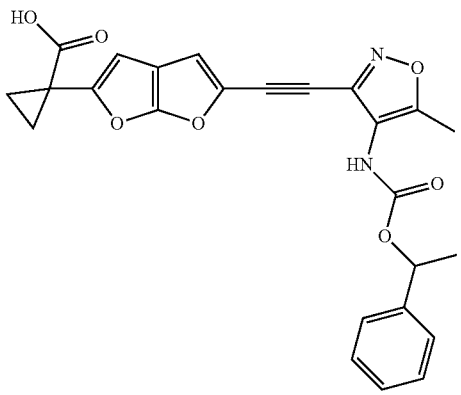 [SMILES: Cc1onc(C#Cc2cc3cc(C4(C(=O)O)CC4)oc3o2)c1NC(=O)OC(C)c1ccccc1]
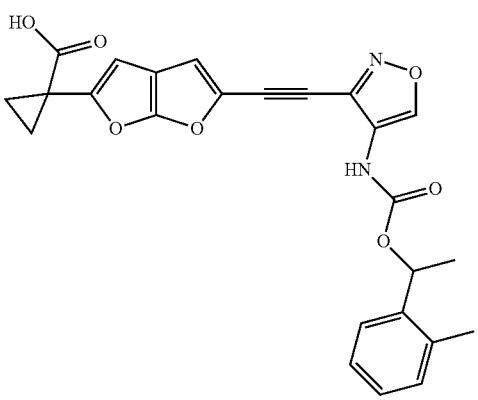 [SMILES: Cc1ccccc1C(C)OC(=O)Nc1conc1C#Cc1cc2cc(C3(C(=O)O)CC3)oc2o1]
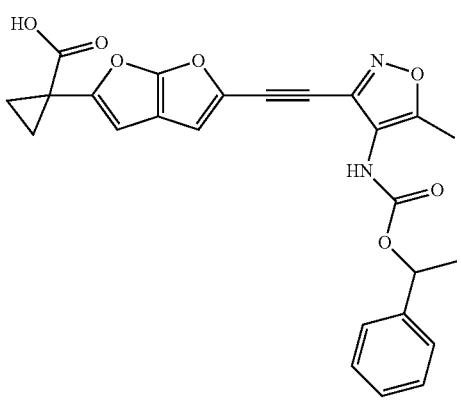 [SMILES: Cc1onc(C#Cc2cc3cc(C4(C(=O)O)CC4)oc3o2)c1NC(=O)OC(C)c1ccccc1]
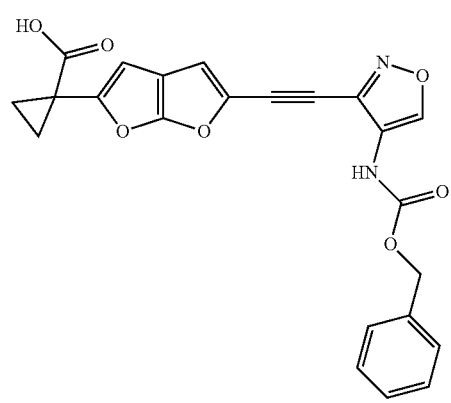 [SMILES: O=C(Nc1conc1C#Cc1cc2cc(C3(C(=O)O)CC3)oc2o1)OCc1ccccc1]

TABLE 14-continued
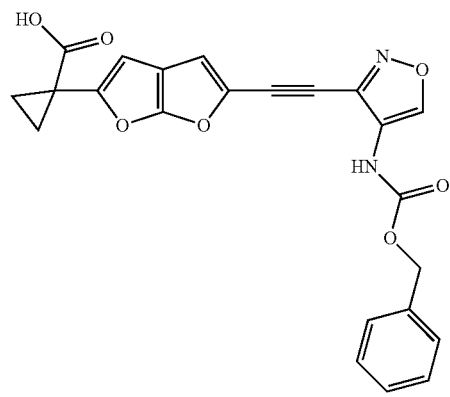 [SMILES: O=C(Nc1conc1C#Cc1cc2cc(C3(C(=O)O)CC3)oc2o1)OCc1ccccc1]
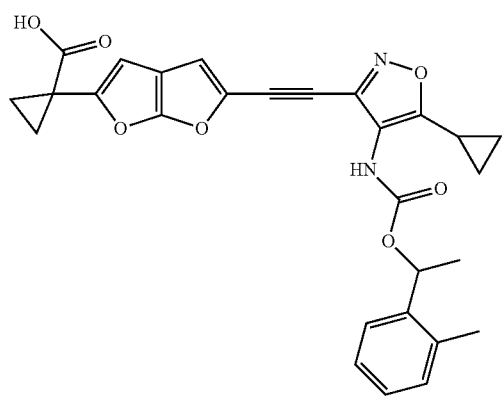 [SMILES: Cc1ccccc1C(C)OC(=O)Nc1c(C#Cc2cc3cc(C4(C(=O)O)CC4)oc3o2)noc1C1CC1]
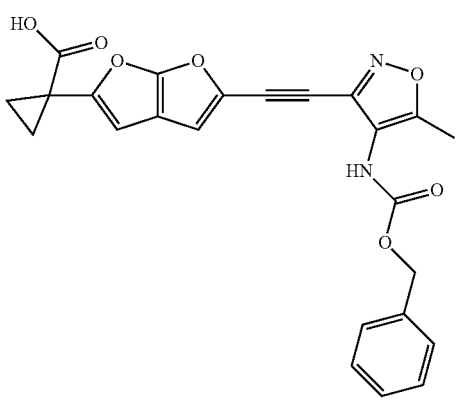
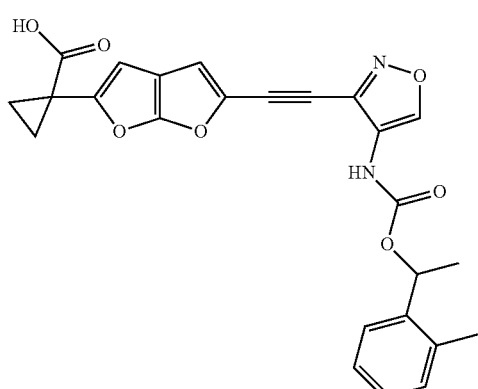
TABLE 14-continued
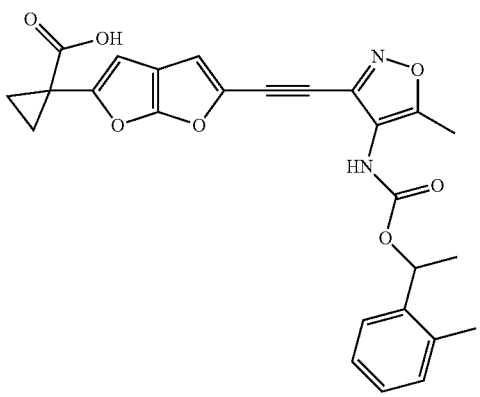
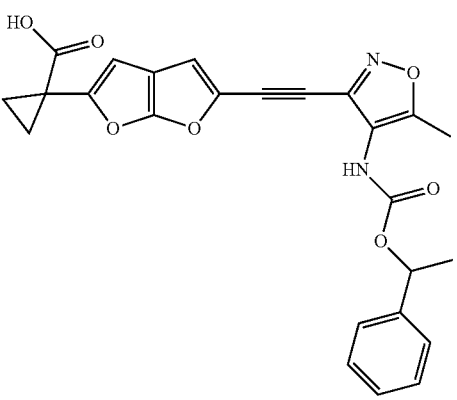 [SMILES: Cc1onc(C#Cc2cc3cc(C4(C(=O)O)CC4)oc3o2)c1NC(=O)OC(C)c1ccccc1]
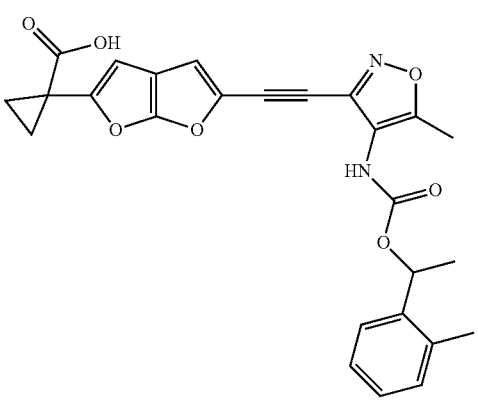 [SMILES: Cc1ccccc1C(C)OC(=O)Nc1c(C#Cc2cc3cc(C4(C(=O)O)CC4)oc3o2)noc1C]
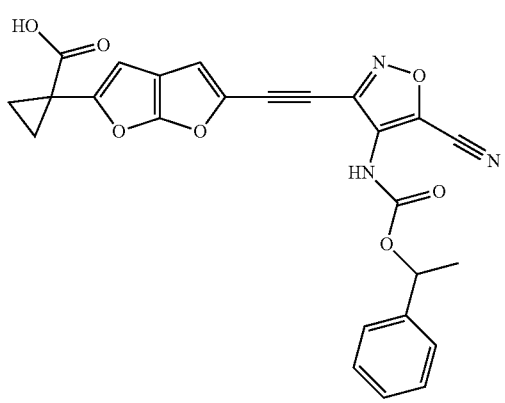

TABLE 14-continued
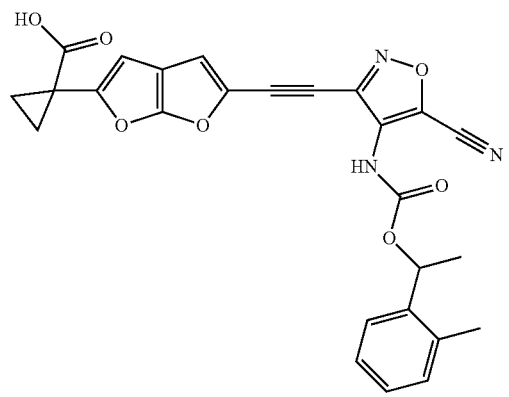
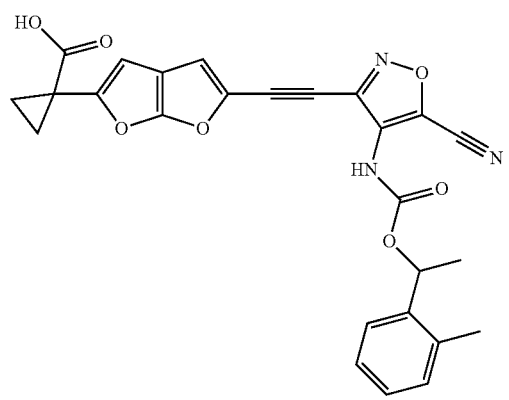
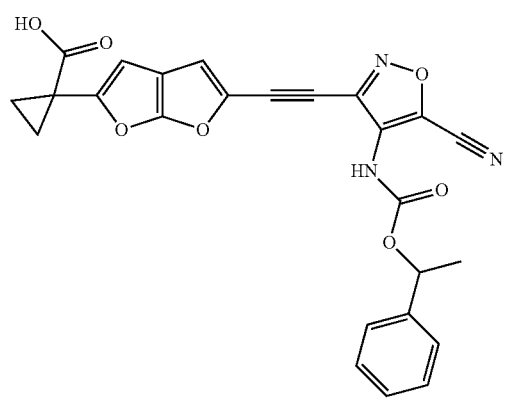 [SMILES: CC(OC(=O)Nc1c(C#Cc2cc3cc(C4(C(=O)O)CC4)oc3o2)noc1C#N)c1ccccc1]
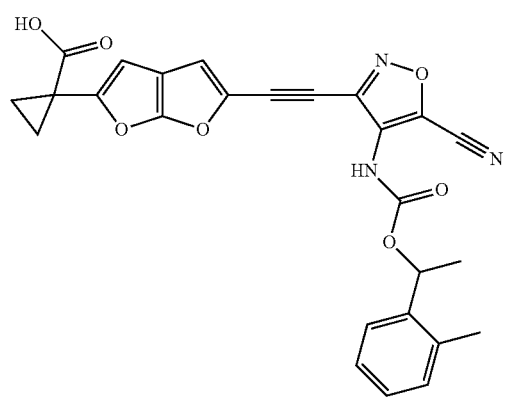 [SMILES: Cc1ccccc1C(C)OC(=O)Nc1c(C#Cc2cc3cc(C4(C(=O)O)CC4)oc3o2)noc1C#N]
TABLE 14-continued
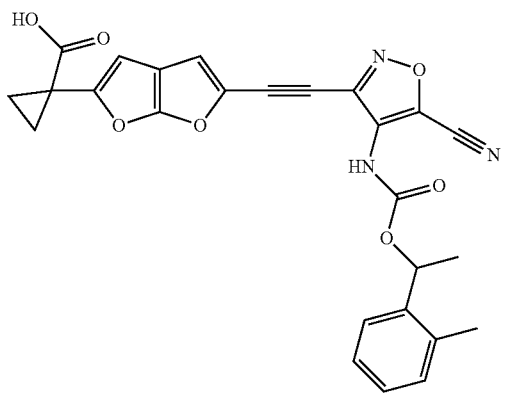 [SMILES: Cc1ccccc1C(C)OC(=O)Nc1c(C#Cc2cc3cc(C4(C(=O)O)CC4)oc3o2)noc1C#N]
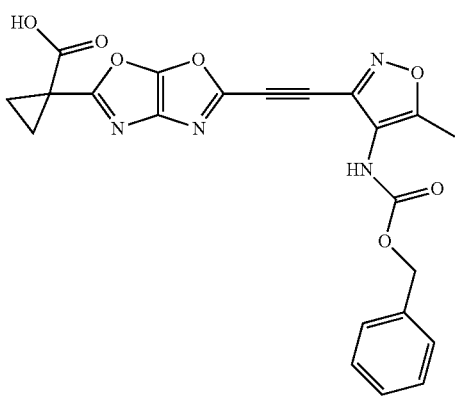
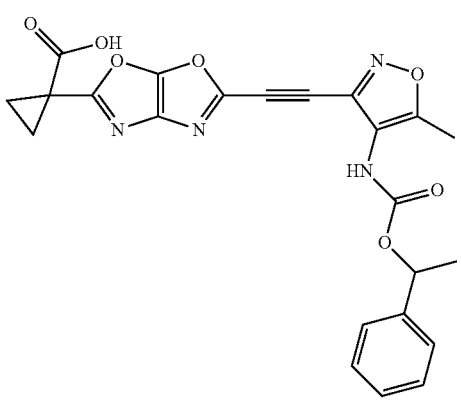 [SMILES: Cc1onc(C#Cc2nc3nc(C4(C(=O)O)CC4)oc3o2)c1NC(=O)OC(C)c1ccccc1]
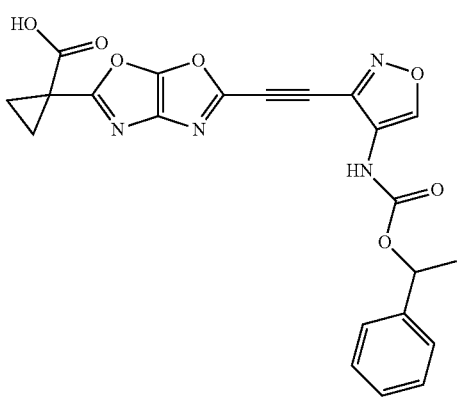

TABLE 14-continued
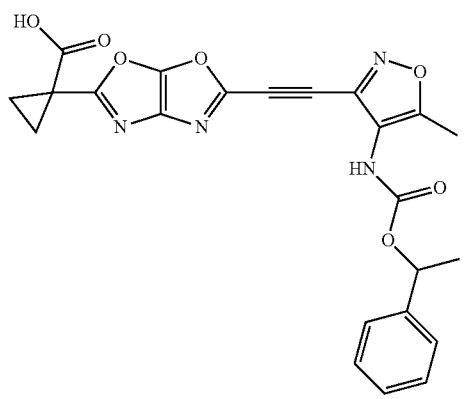
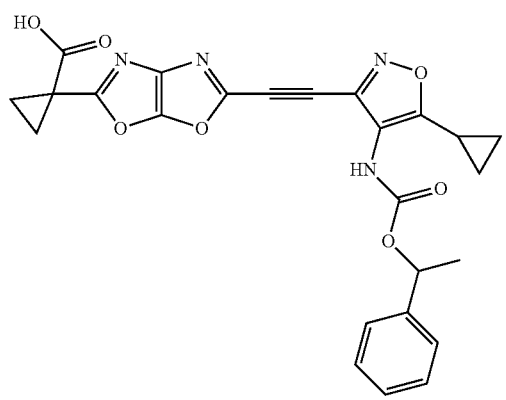
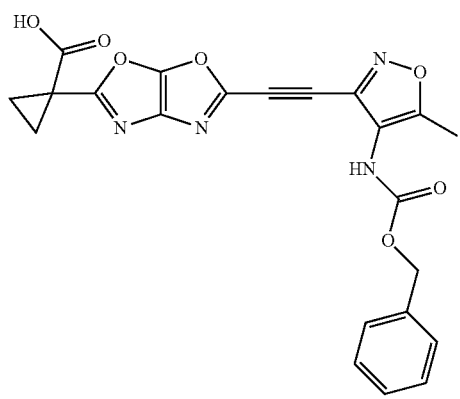
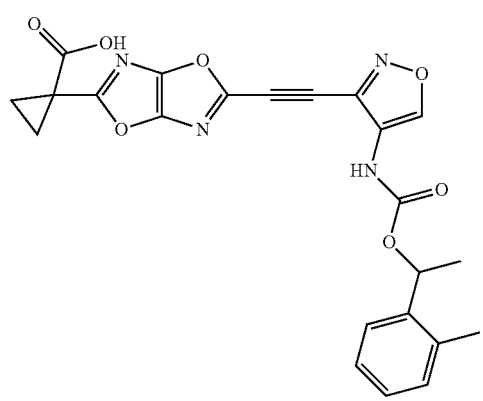
TABLE 14-continued
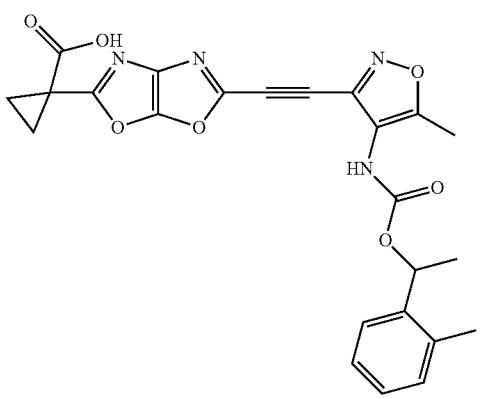
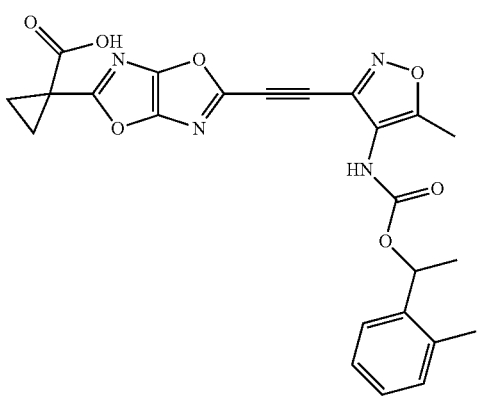
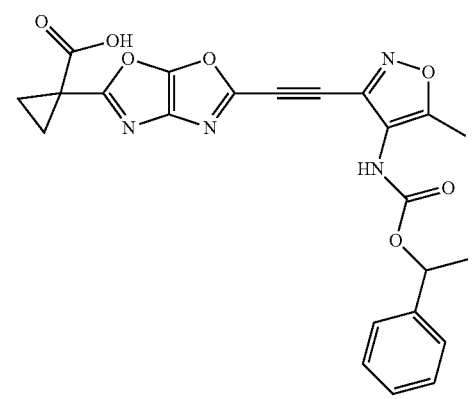 [SMILES: Cc1onc(C#Cc2nc3nc(C4(C(=O)O)CC4)oc3o2)c1NC(=O)OC(C)c1ccccc1]
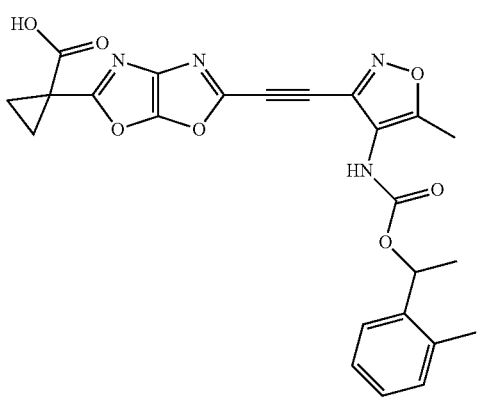

TABLE 14-continued
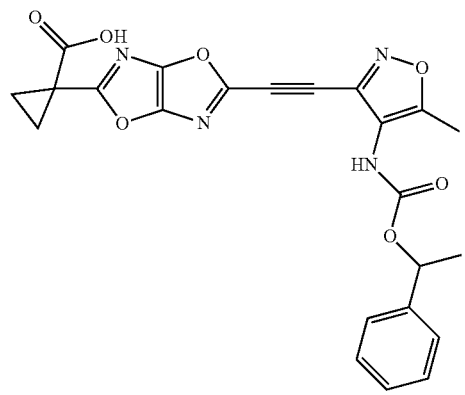
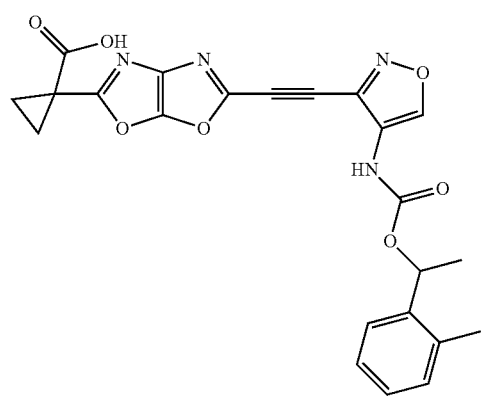
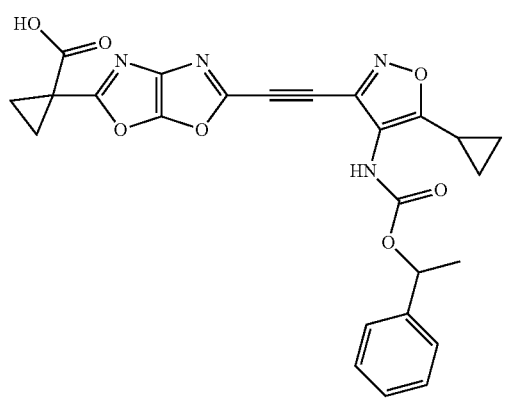
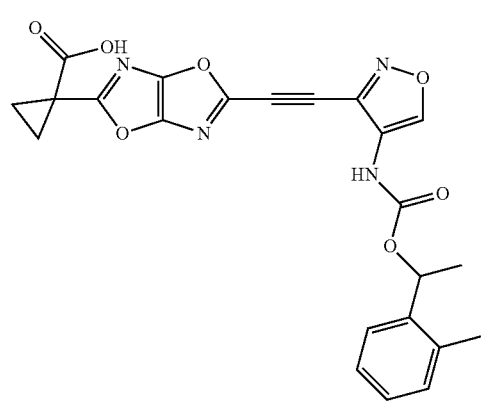
TABLE 14-continued
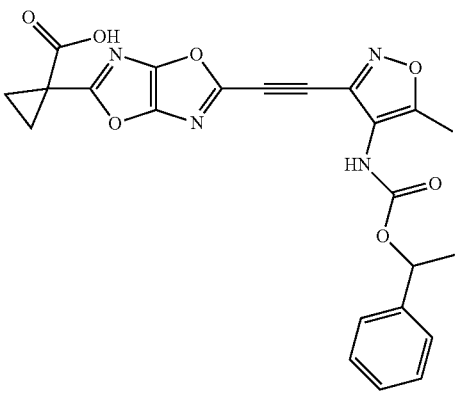
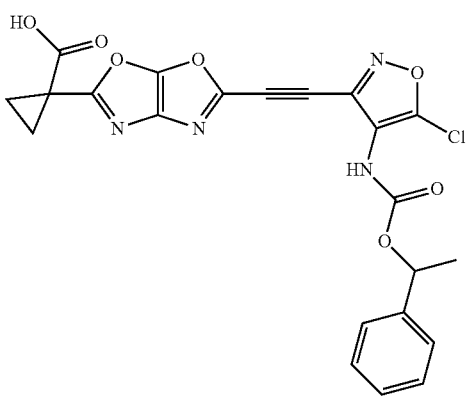
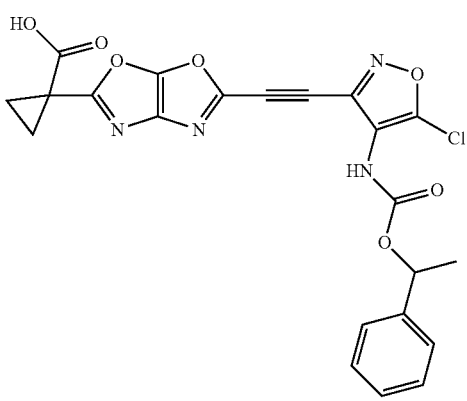
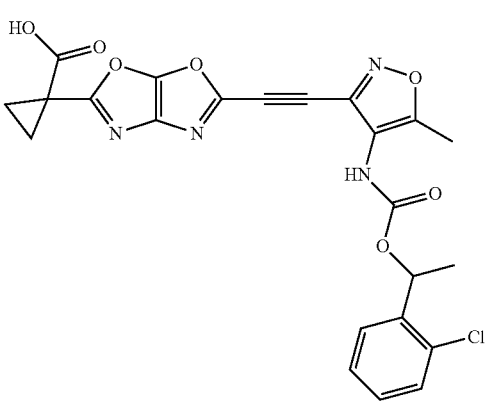

1345
TABLE 14-continued
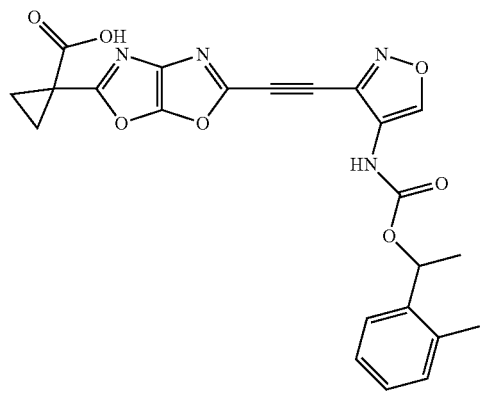
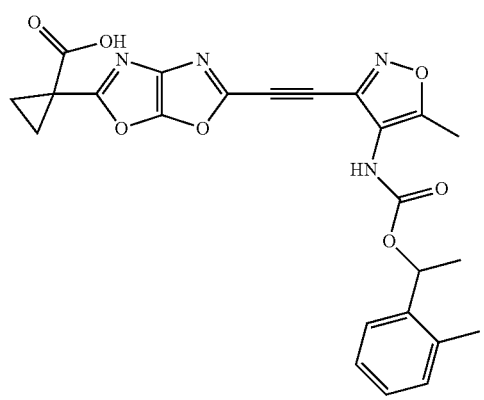
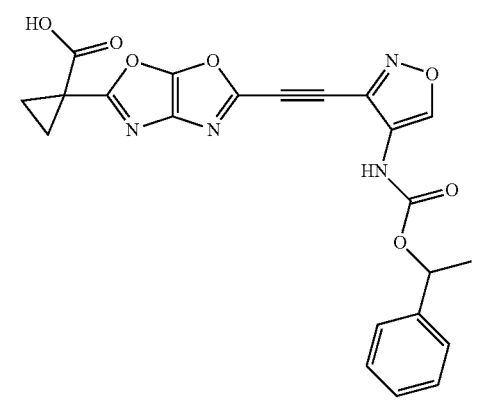
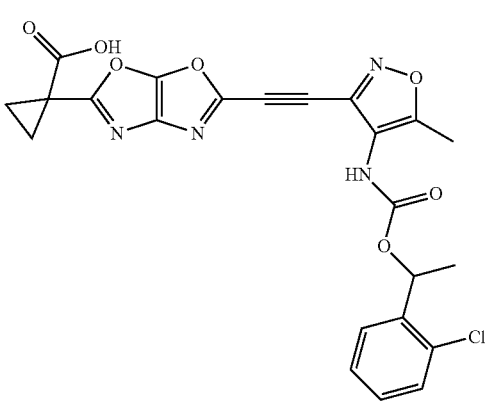
1346
TABLE 14-continued
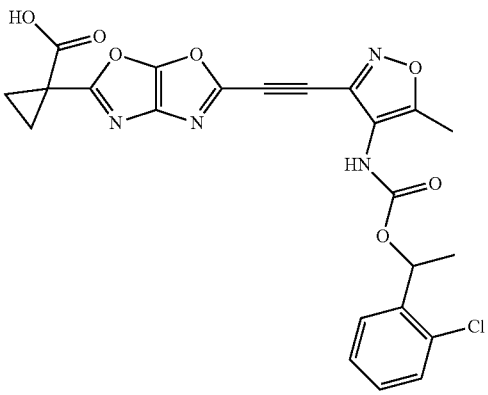
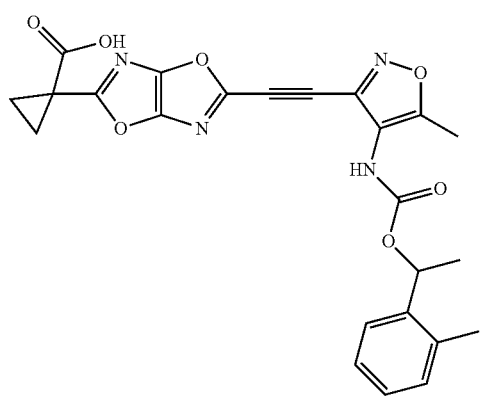
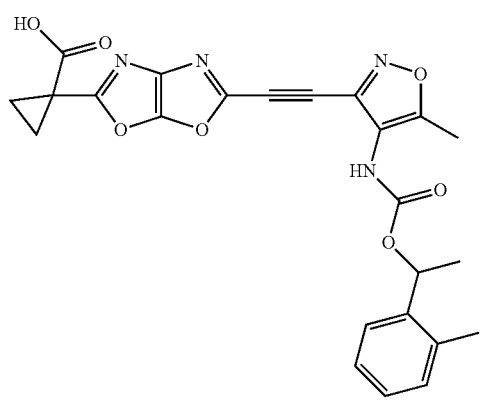 [SMILES: Cc1ccccc1C(C)OC(=O)Nc1c(C#Cc2nc3nc(C4(C(=O)O)CC4)oc3o2)noc1C]
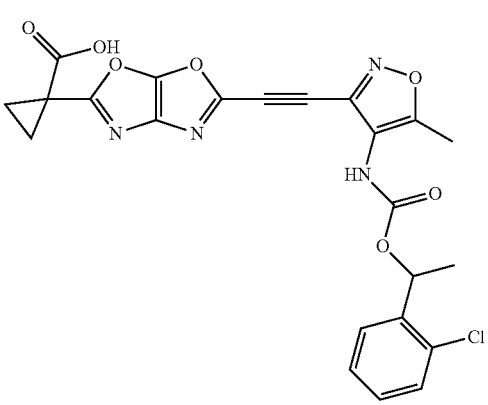

TABLE 14-continued
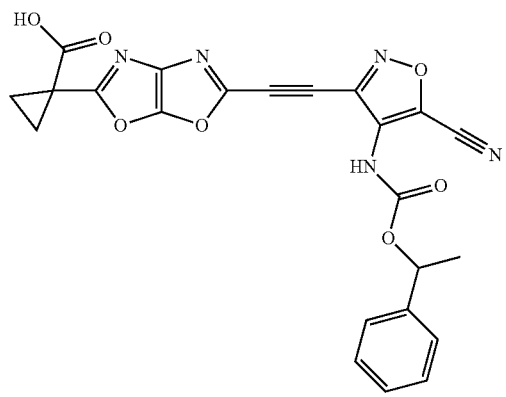
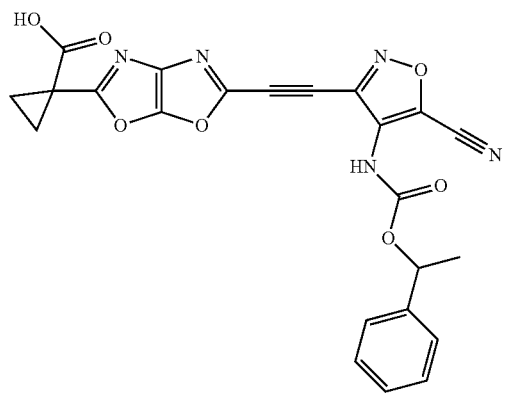
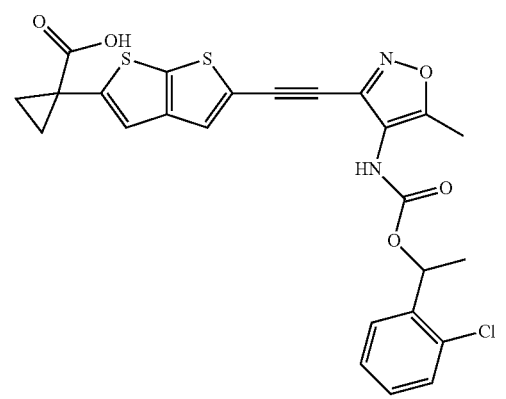 [SMILES: Cc1onc(C#Cc2cc3cc(C4(C(=O)O)CC4)sc3s2)c1NC(=O)OC(C)c1ccccc1Cl]
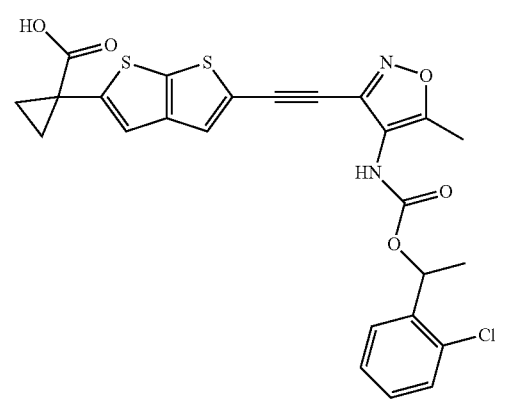
TABLE 14-continued
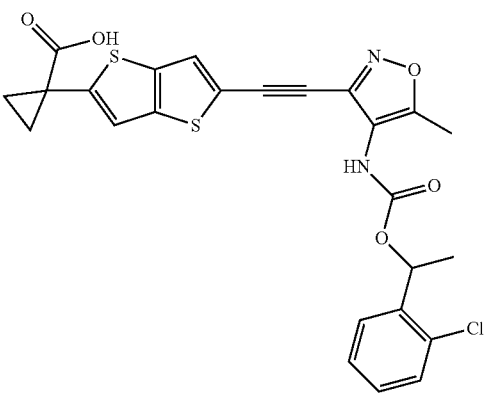 [SMILES: Cc1onc(C#Cc2cc3sc(C4(C(=O)O)CC4)cc3s2)c1NC(=O)OC(C)c1ccccc1Cl]
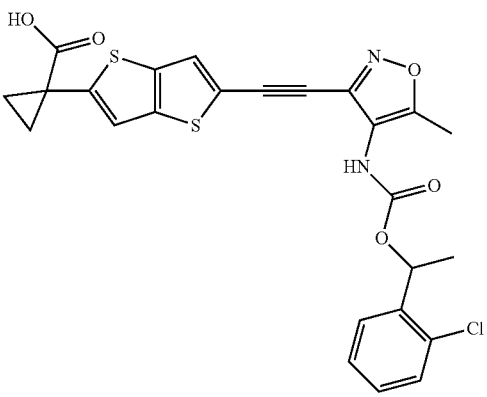
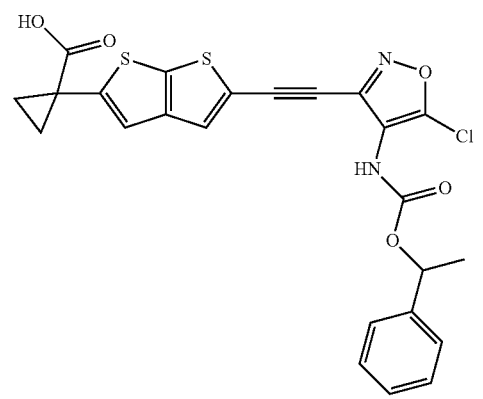 [SMILES: CC(OC(=O)Nc1c(C#Cc2cc3cc(C4(C(=O)O)CC4)sc3s2)noc1Cl)c1ccccc1]
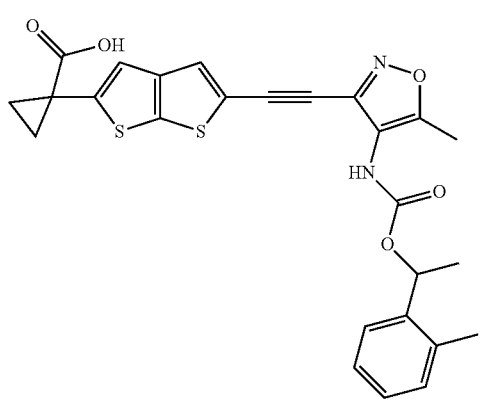

US 8,975,235 B2
TABLE 14-continued
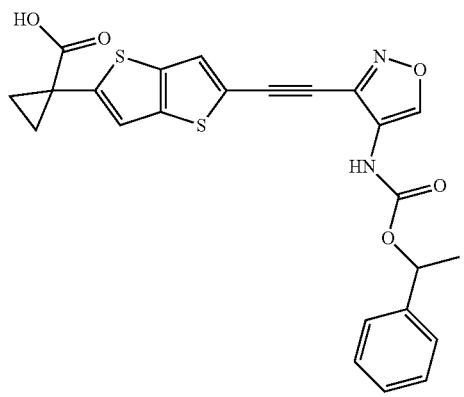
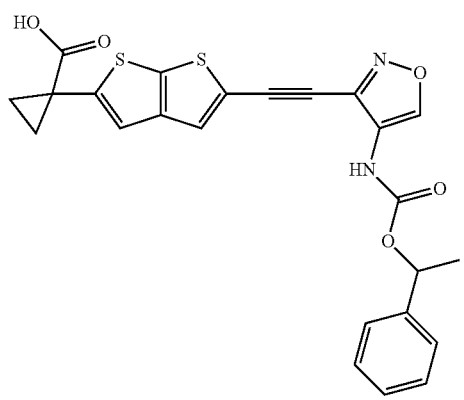
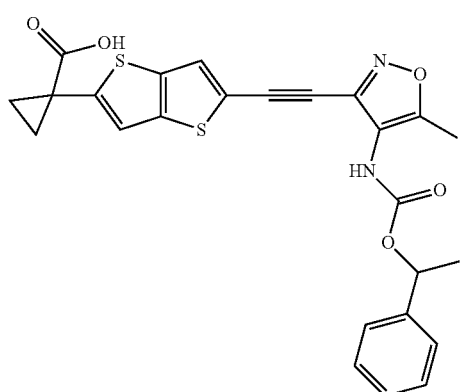
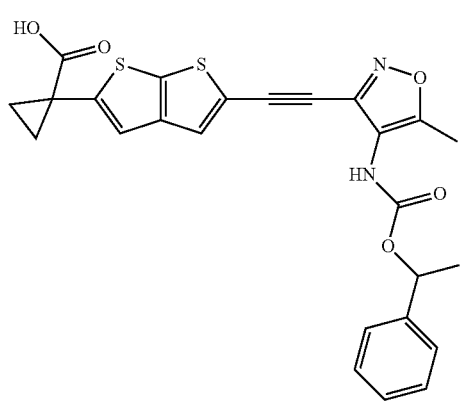
TABLE 14-continued
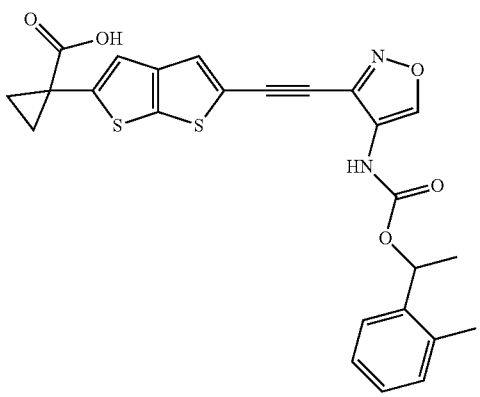 [SMILES: Cc1ccccc1C(C)OC(=O)Nc1conc1C#Cc1cc2cc(C3(C(=O)O)CC3)sc2s1]
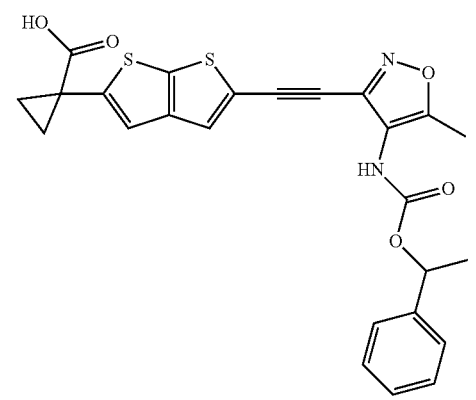
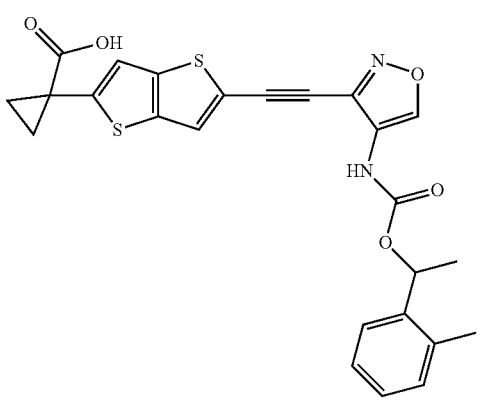 [SMILES: Cc1ccccc1C(C)OC(=O)Nc1conc1C#Cc1cc2sc(C3(C(=O)O)CC3)cc2s1]
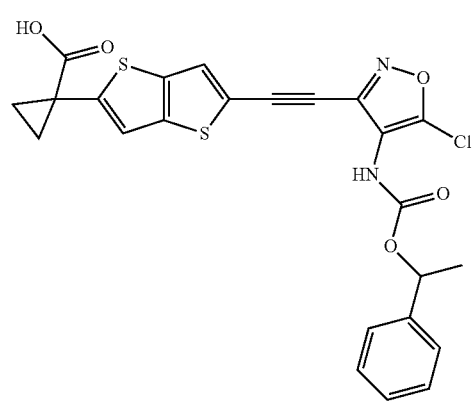

TABLE 14-continued
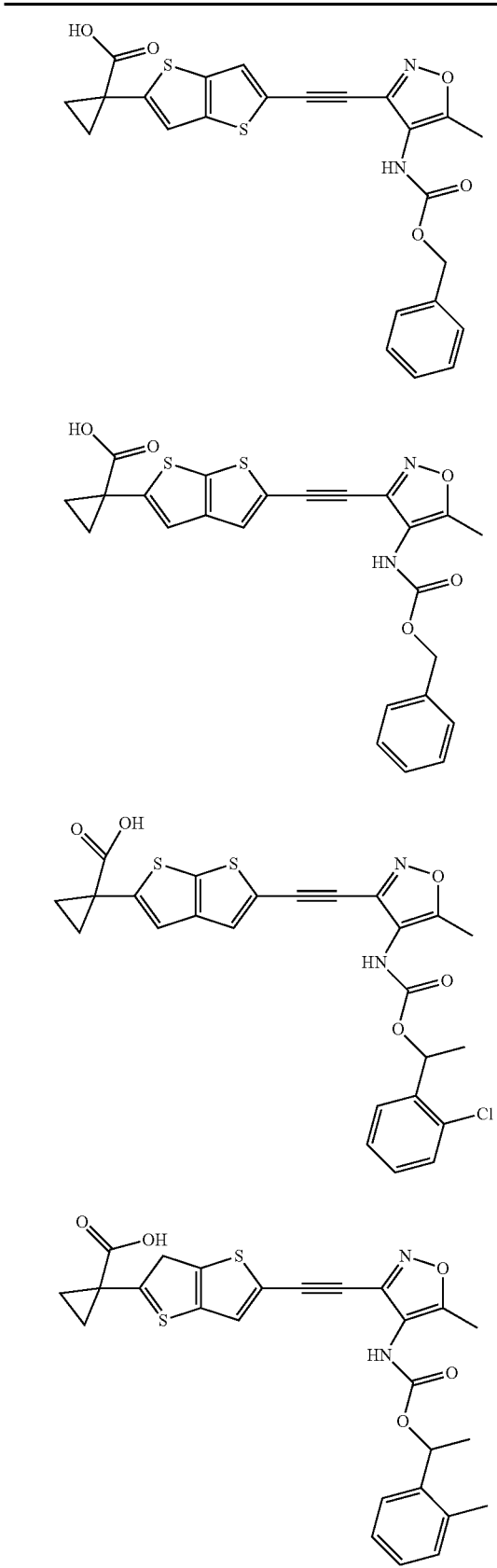
TABLE 14-continued
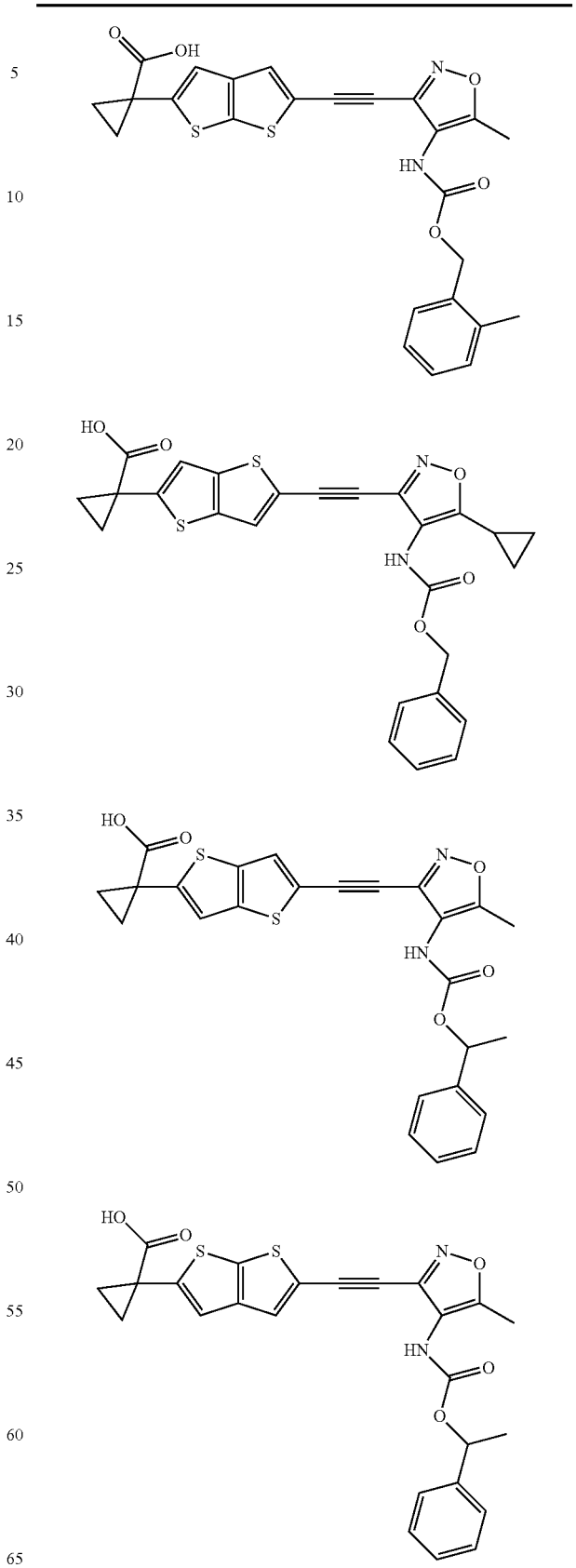

TABLE 14-continued
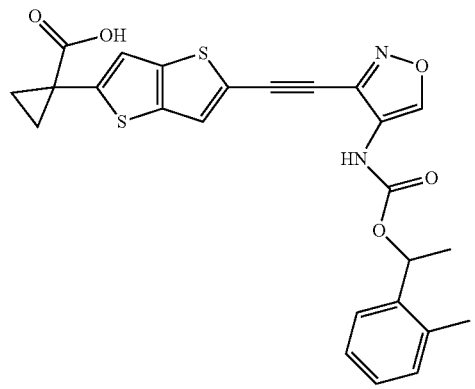 [SMILES: Cc1ccccc1C(C)OC(=O)Nc1conc1C#Cc1cc2sc(C3(C(=O)O)CC3)cc2s1]
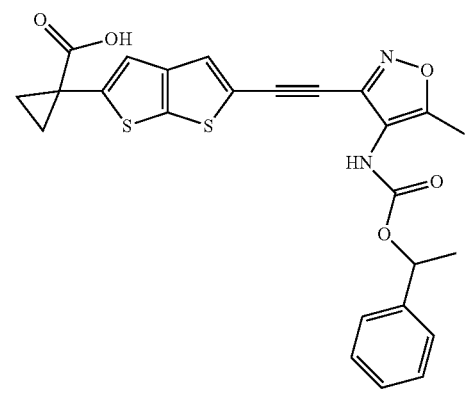 [SMILES: Cc1onc(C#Cc2cc3cc(C4(C(=O)O)CC4)sc3s2)c1NC(=O)OC(C)c1ccccc1]
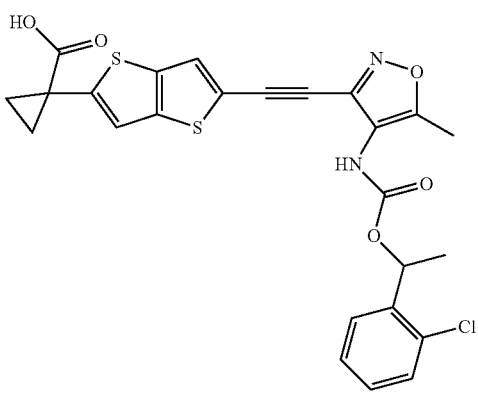 [SMILES: Cc1onc(C#Cc2cc3sc(C4(C(=O)O)CC4)cc3s2)c1NC(=O)OC(C)c1ccccc1Cl]
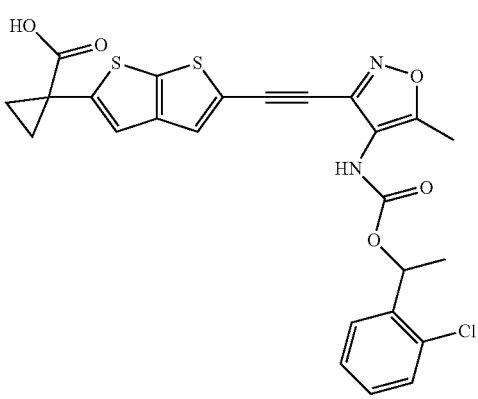 [SMILES: Cc1onc(C#Cc2cc3cc(C4(C(=O)O)CC4)sc3s2)c1NC(=O)OC(C)c1ccccc1Cl]
TABLE 14-continued
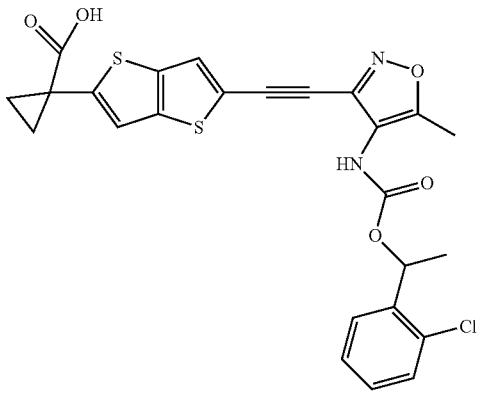 [SMILES: Cc1onc(C#Cc2cc3sc(C4(C(=O)O)CC4)cc3s2)c1NC(=O)OC(C)c1ccccc1Cl]
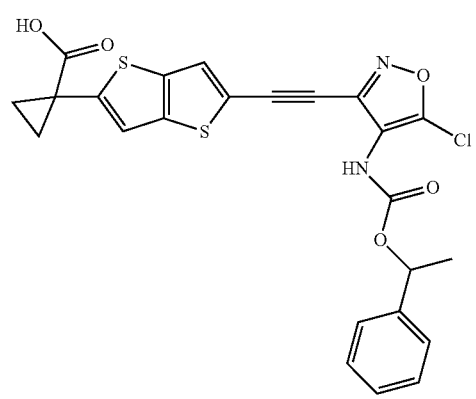 [SMILES: CC(OC(=O)Nc1c(C#Cc2cc3sc(C4(C(=O)O)CC4)cc3s2)noc1Cl)c1ccccc1]
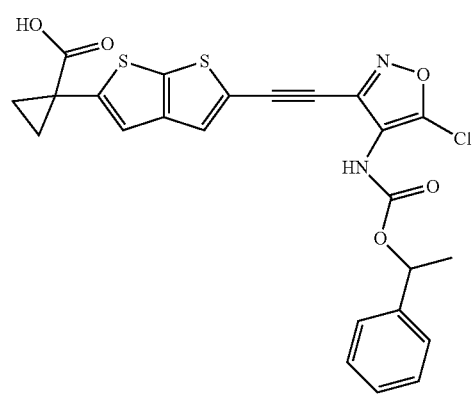 [SMILES: CC(OC(=O)Nc1c(C#Cc2cc3cc(C4(C(=O)O)CC4)sc3s2)noc1Cl)c1ccccc1]
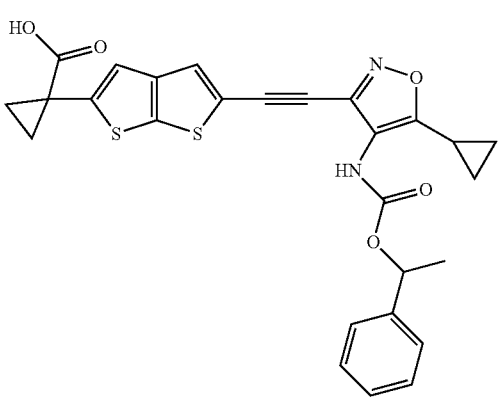 [SMILES: CC(OC(=O)Nc1c(C#Cc2cc3cc(C4(C(=O)O)CC4)sc3s2)noc1C1CC1)c1ccccc1]

TABLE 14-continued
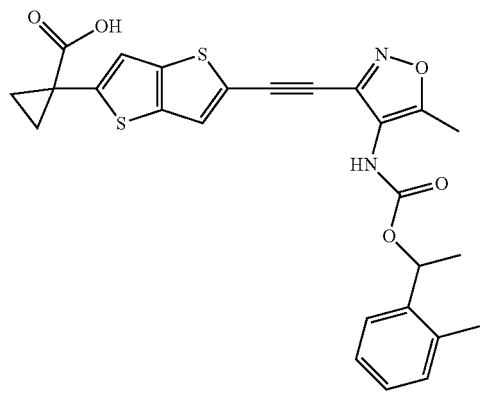 [SMILES: Cc1ccccc1C(C)OC(=O)Nc1c(C#Cc2cc3sc(C4(C(=O)O)CC4)cc3s2)noc1C]
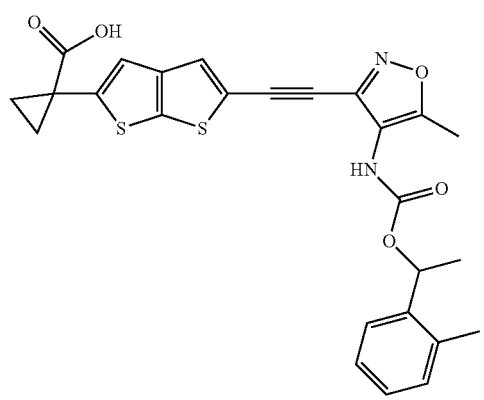 [SMILES: Cc1ccccc1C(C)OC(=O)Nc1c(C#Cc2cc3cc(C4(C(=O)O)CC4)sc3s2)noc1C]
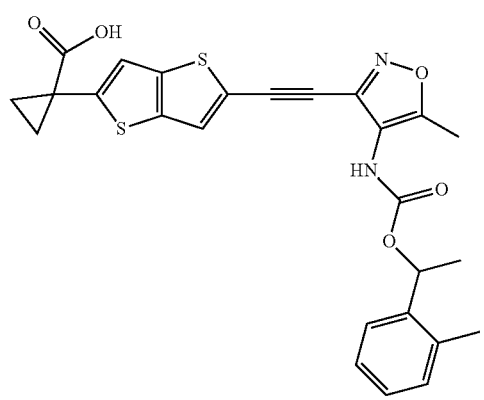 [SMILES: Cc1ccccc1C(C)OC(=O)Nc1c(C#Cc2cc3sc(C4(C(=O)O)CC4)cc3s2)noc1C]
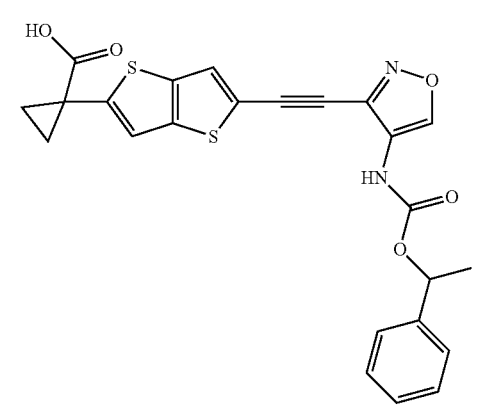 [SMILES: CC(OC(=O)Nc1conc1C#Cc1cc2sc(C3(C(=O)O)CC3)cc2s1)c1ccccc1]
TABLE 14-continued
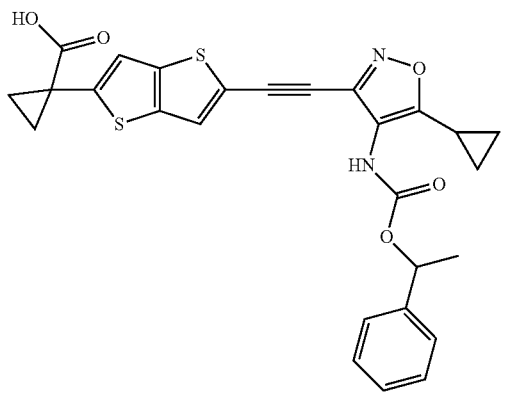 [SMILES: CC(OC(=O)Nc1c(C#Cc2cc3sc(C4(C(=O)O)CC4)cc3s2)noc1C1CC1)c1ccccc1]
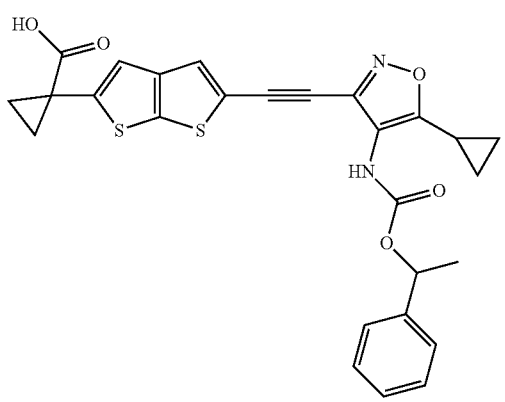 [SMILES: CC(OC(=O)Nc1c(C#Cc2cc3cc(C4(C(=O)O)CC4)sc3s2)noc1C1CC1)c1ccccc1]
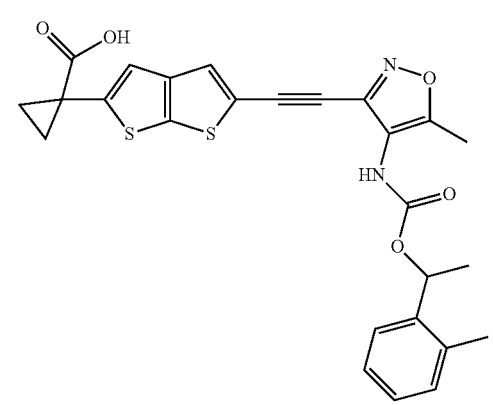 [SMILES: Cc1ccccc1C(C)OC(=O)Nc1c(C#Cc2cc3cc(C4(C(=O)O)CC4)sc3s2)noc1C]
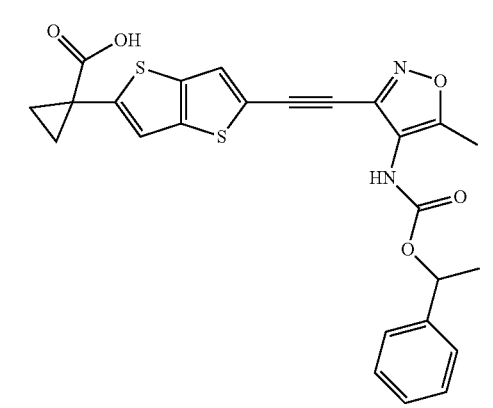 [SMILES: Cc1onc(C#Cc2cc3sc(C4(C(=O)O)CC4)cc3s2)c1NC(=O)OC(C)c1ccccc1]

TABLE 14-continued
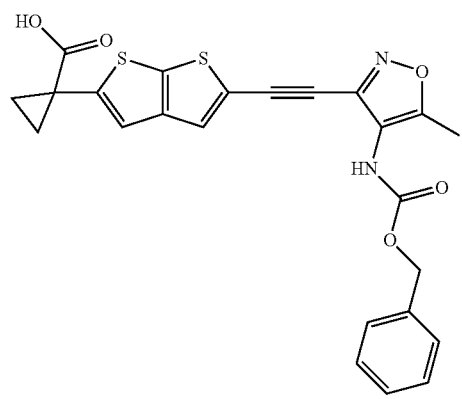 [SMILES: Cc1onc(C#Cc2cc3cc(C4(C(=O)O)CC4)sc3s2)c1NC(=O)OCc1ccccc1]
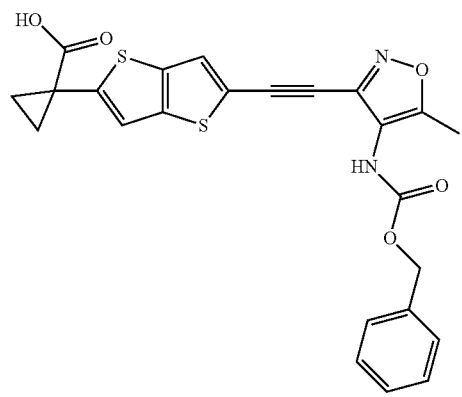 [SMILES: Cc1onc(C#Cc2cc3sc(C4(C(=O)O)CC4)cc3s2)c1NC(=O)OCc1ccccc1]
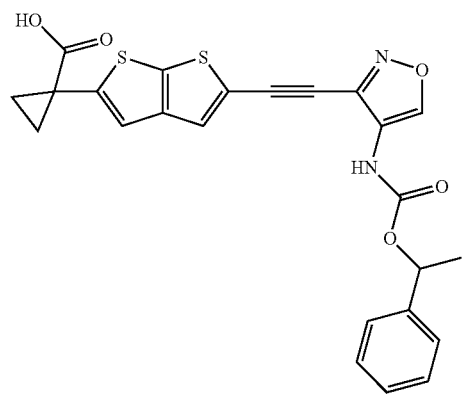 [SMILES: CC(OC(=O)Nc1conc1C#Cc1cc2cc(C3(C(=O)O)CC3)sc2s1)c1ccccc1]
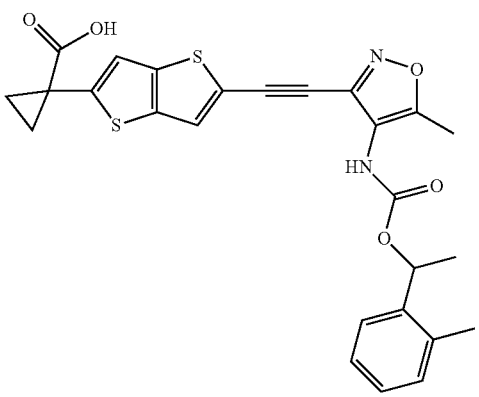 [SMILES: Cc1ccccc1C(C)OC(=O)Nc1c(C#Cc2cc3sc(C4(C(=O)O)CC4)cc3s2)noc1C]
TABLE 14-continued
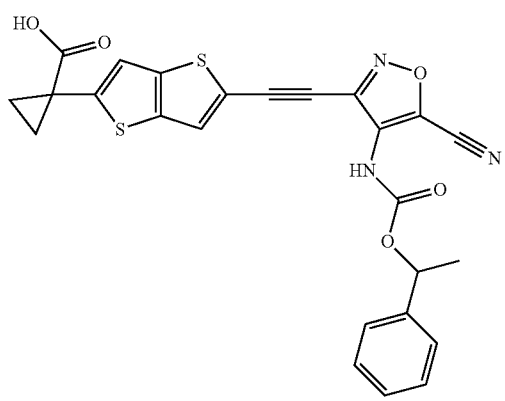 [SMILES: CC(OC(=O)Nc1c(C#Cc2cc3sc(C4(C(=O)O)CC4)cc3s2)noc1C#N)c1ccccc1]
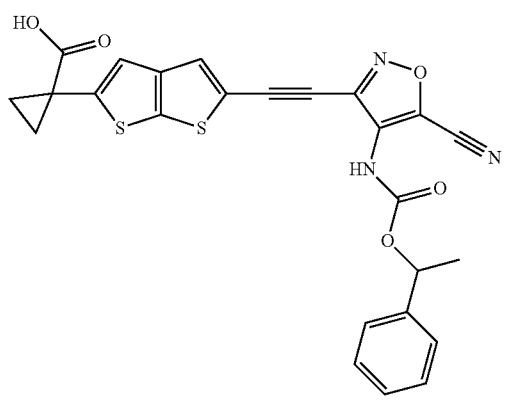 [SMILES: CC(OC(=O)Nc1c(C#Cc2cc3cc(C4(C(=O)O)CC4)sc3s2)noc1C#N)c1ccccc1]
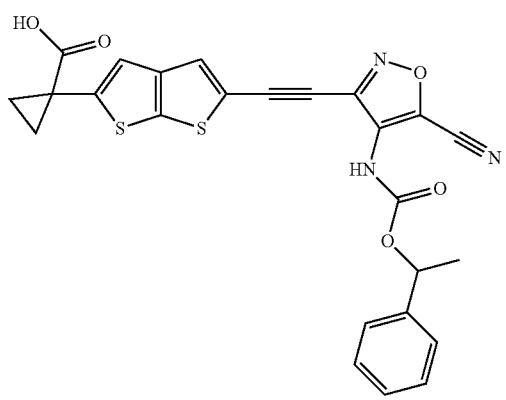 [SMILES: CC(OC(=O)Nc1c(C#Cc2cc3cc(C4(C(=O)O)CC4)sc3s2)noc1C#N)c1ccccc1]
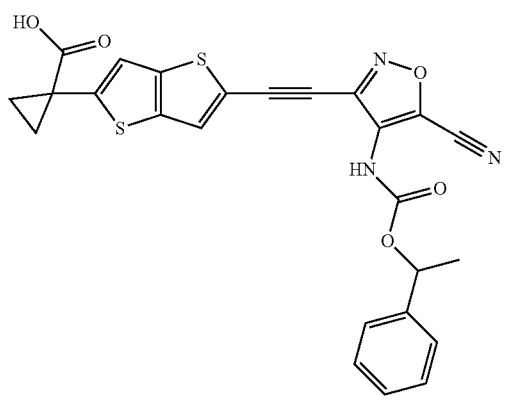 [SMILES: CC(OC(=O)Nc1c(C#Cc2cc3sc(C4(C(=O)O)CC4)cc3s2)noc1C#N)c1ccccc1]

TABLE 14-continued
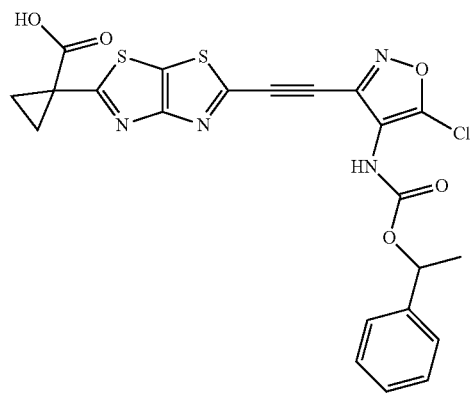 [SMILES: CC(OC(=O)Nc1c(C#Cc2nc3nc(C4(C(=O)O)CC4)sc3s2)noc1Cl)c1ccccc1]
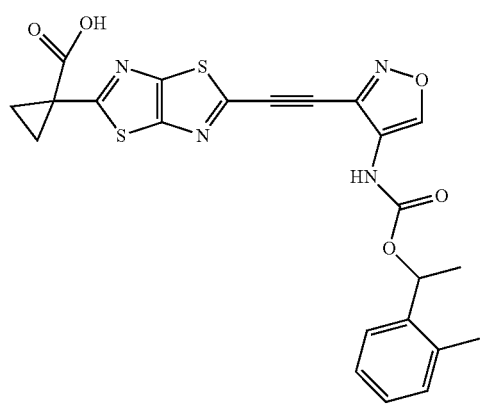 [SMILES: Cc1ccccc1C(C)OC(=O)Nc1conc1C#Cc1nc2sc(C3(C(=O)O)CC3)nc2s1]
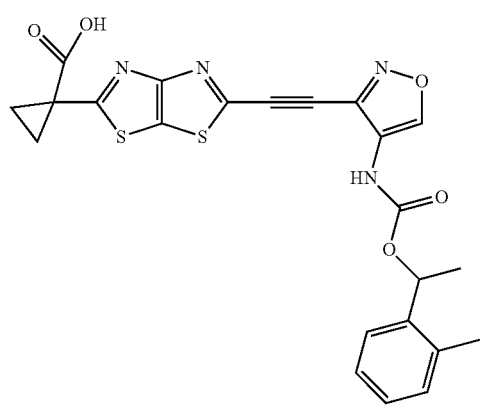 [SMILES: Cc1ccccc1C(C)OC(=O)Nc1conc1C#Cc1nc2nc(C3(C(=O)O)CC3)sc2s1]
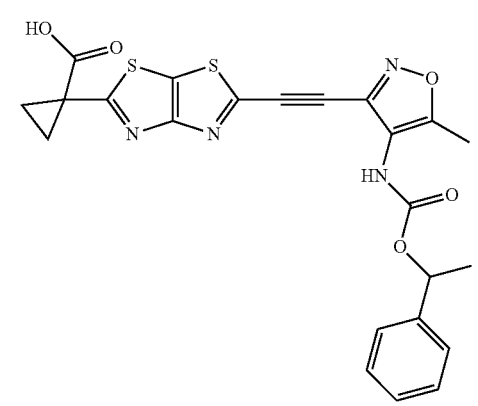 [SMILES: Cc1onc(C#Cc2nc3nc(C4(C(=O)O)CC4)sc3s2)c1NC(=O)OC(C)c1ccccc1]
TABLE 14-continued
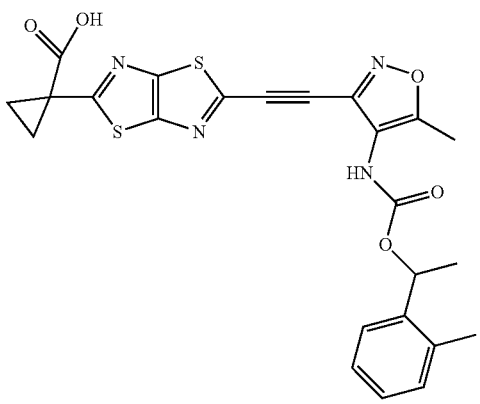 [SMILES: Cc1ccccc1C(C)OC(=O)Nc1c(C#Cc2nc3sc(C4(C(=O)O)CC4)nc3s2)noc1C]
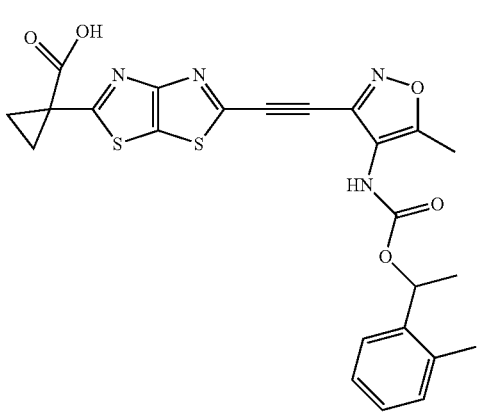 [SMILES: Cc1ccccc1C(C)OC(=O)Nc1c(C#Cc2nc3nc(C4(C(=O)O)CC4)sc3s2)noc1C]
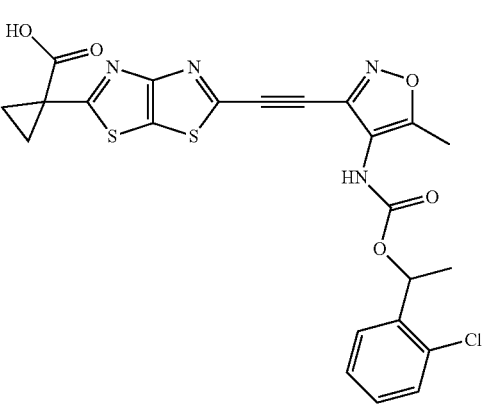 [SMILES: Cc1onc(C#Cc2nc3nc(C4(C(=O)O)CC4)sc3s2)c1NC(=O)OC(C)c1ccccc1Cl]
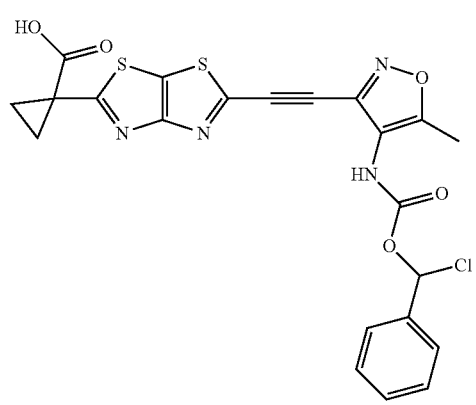 [SMILES: Cc1onc(C#Cc2nc3nc(C4(C(=O)O)CC4)sc3s2)c1NC(=O)OC(Cl)c1ccccc1]

TABLE 14-continued
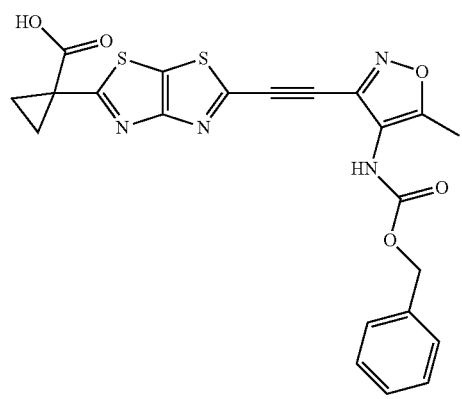 [SMILES: Cc1onc(C#Cc2nc3nc(C4(C(=O)O)CC4)sc3s2)c1NC(=O)OCc1ccccc1]
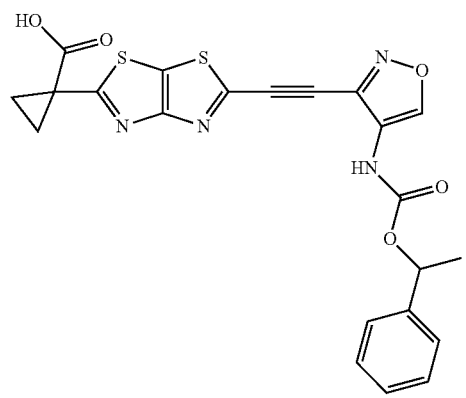
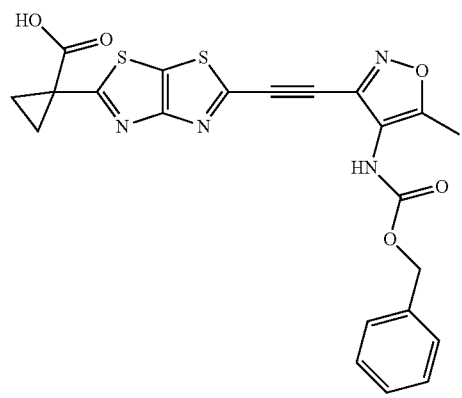 [SMILES: Cc1onc(C#Cc2nc3nc(C4(C(=O)O)CC4)sc3s2)c1NC(=O)OCc1ccccc1]
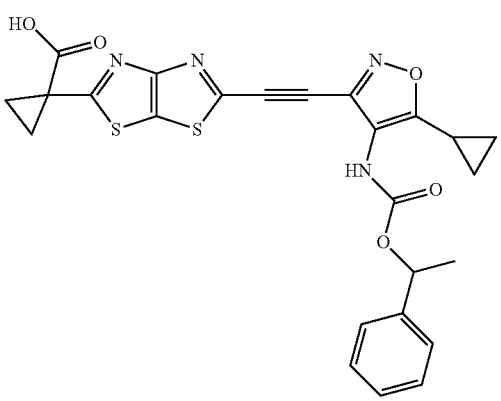 [SMILES: CC(OC(=O)Nc1c(C#Cc2nc3nc(C4(C(=O)O)CC4)sc3s2)noc1C1CC1)c1ccccc1]
TABLE 14-continued
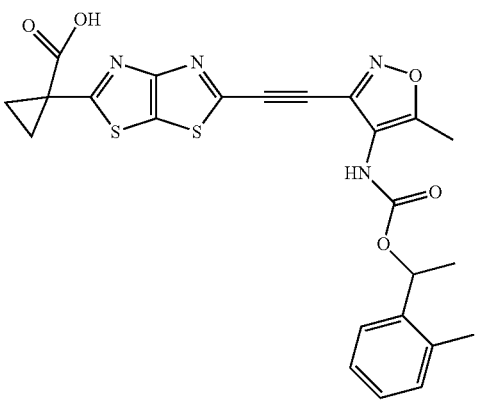 [SMILES: Cc1ccccc1C(C)OC(=O)Nc1c(C#Cc2nc3nc(C4(C(=O)O)CC4)sc3s2)noc1C]
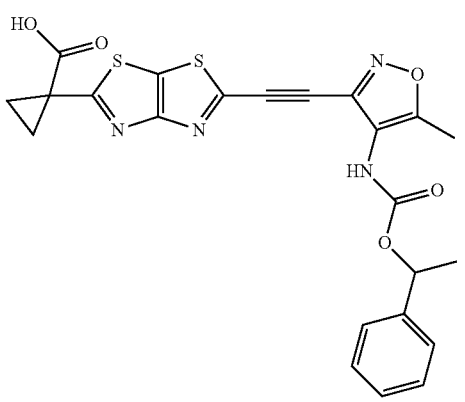
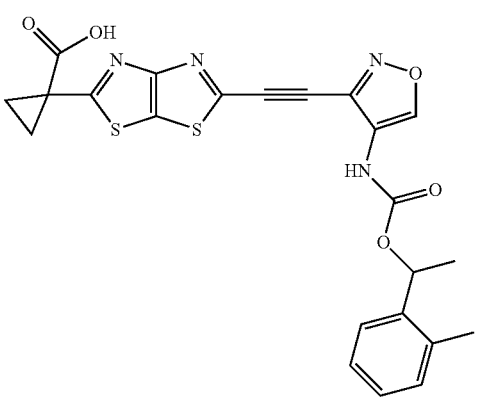 [SMILES: Cc1ccccc1C(C)OC(=O)Nc1conc1C#Cc1nc2nc(C3(C(=O)O)CC3)sc2s1]
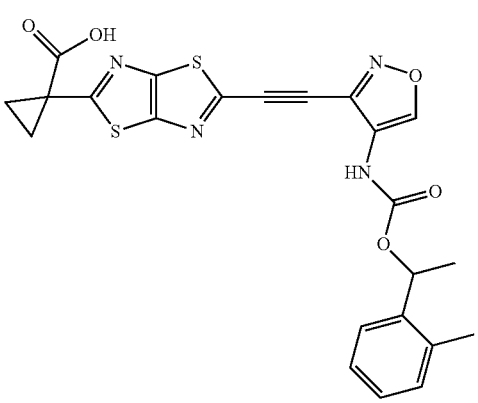 [SMILES: Cc1ccccc1C(C)OC(=O)Nc1conc1C#Cc1nc2sc(C3(C(=O)O)CC3)nc2s1]

TABLE 14-continued
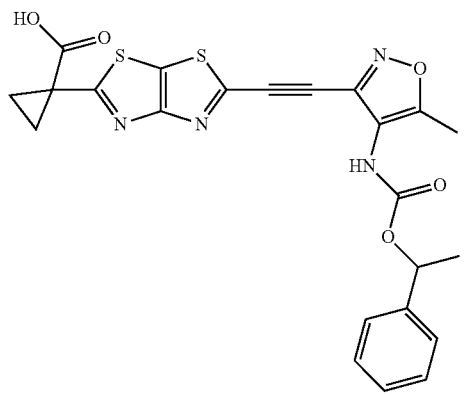 [SMILES: Cc1onc(C#Cc2nc3nc(C4(C(=O)O)CC4)sc3s2)c1NC(=O)OC(C)c1ccccc1]
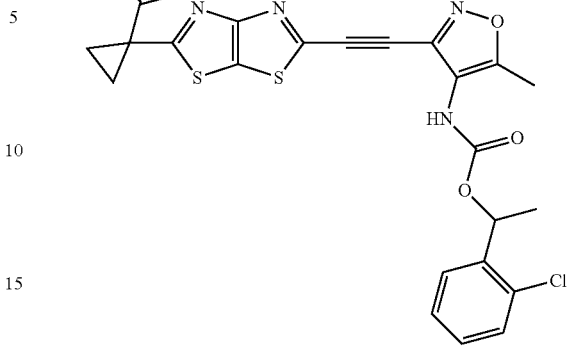
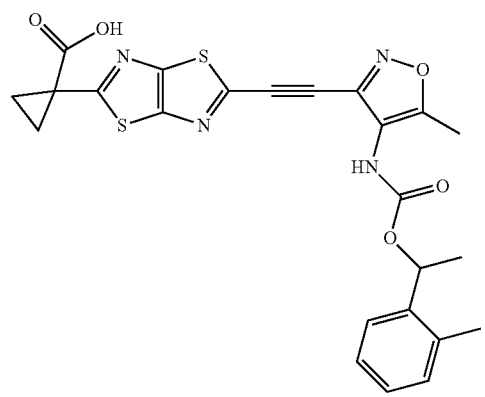
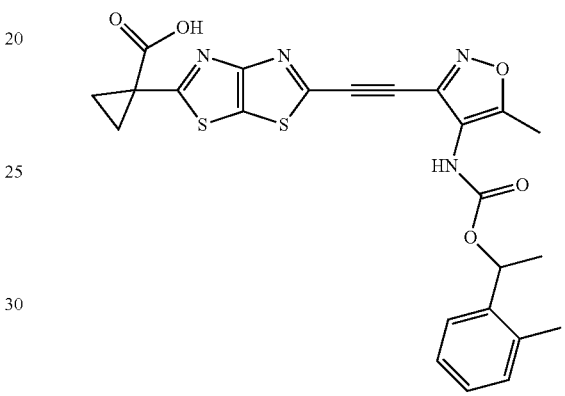
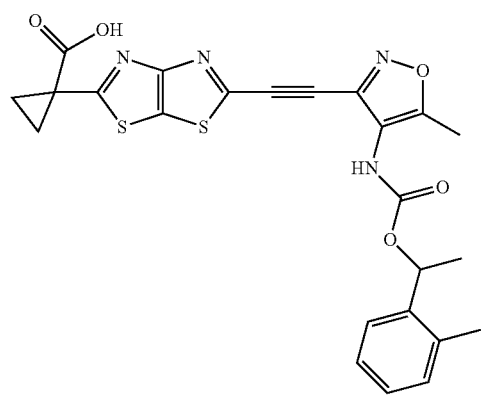
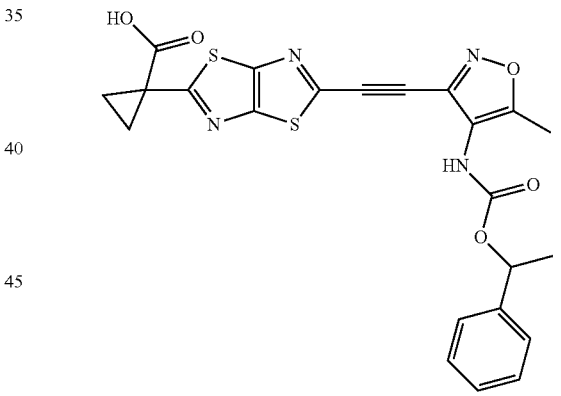
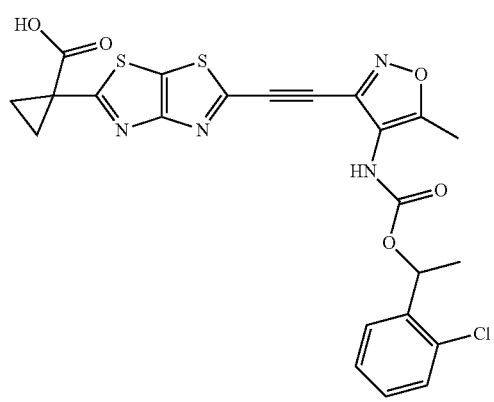 [SMILES: Cc1onc(C#Cc2nc3nc(C4(C(=O)O)CC4)sc3s2)c1NC(=O)OC(C)c1ccccc1Cl]
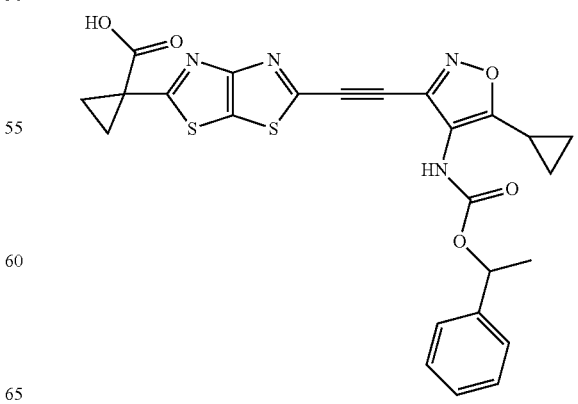

TABLE 14-continued
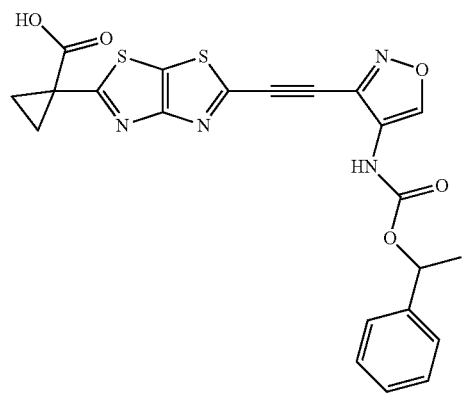 [SMILES: CC(OC(=O)Nc1conc1C#Cc1nc2nc(C3(C(=O)O)CC3)sc2s1)c1ccccc1]
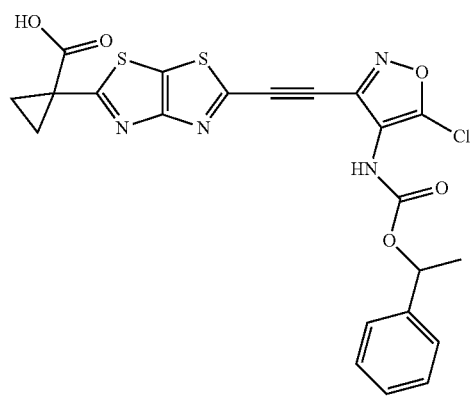 [SMILES: CC(OC(=O)Nc1c(C#Cc2nc3nc(C4(C(=O)O)CC4)sc3s2)noc1Cl)c1ccccc1]
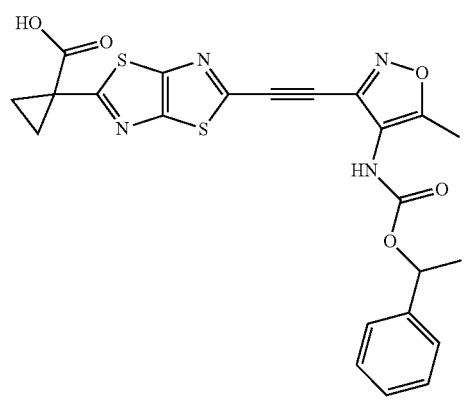 [SMILES: Cc1onc(C#Cc2nc3sc(C4(C(=O)O)CC4)nc3s2)c1NC(=O)OC(C)c1ccccc1]
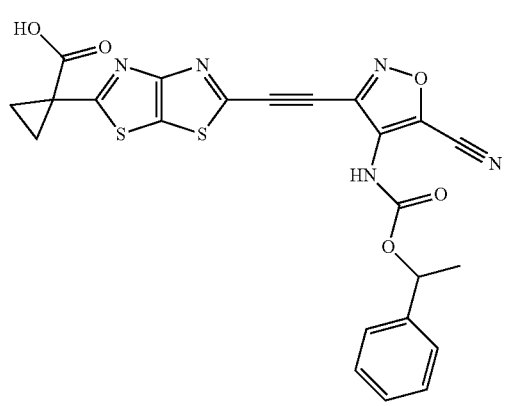 [SMILES: CC(OC(=O)Nc1c(C#Cc2nc3nc(C4(C(=O)O)CC4)sc3s2)noc1C#N)c1ccccc1]
TABLE 14-continued
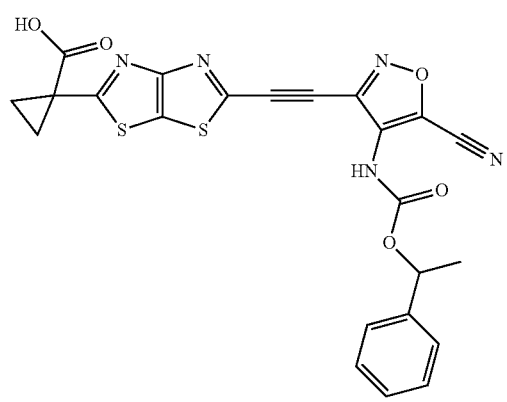 [SMILES: CC(OC(=O)Nc1c(C#Cc2nc3nc(C4(C(=O)O)CC4)sc3s2)noc1C#N)c1ccccc1]
or pharmaceutically acceptable salts thereof.
31. The compound or pharmaceutically acceptable salt thereof of claim 1, selected from compounds of Table 15 having the following structures:
TABLE 15
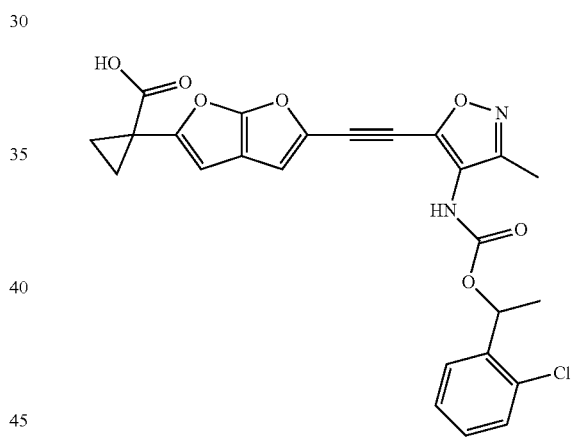
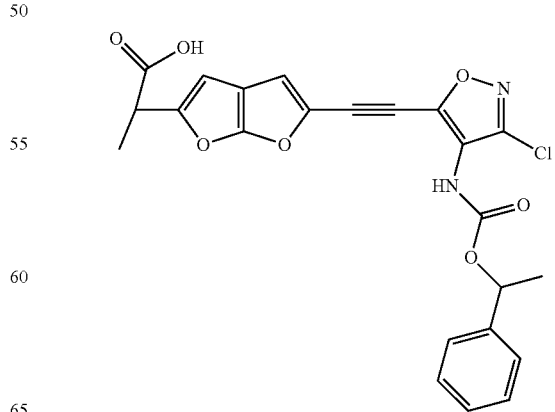

1367
TABLE 15-continued
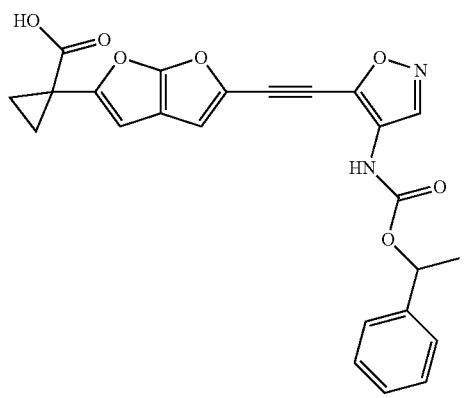
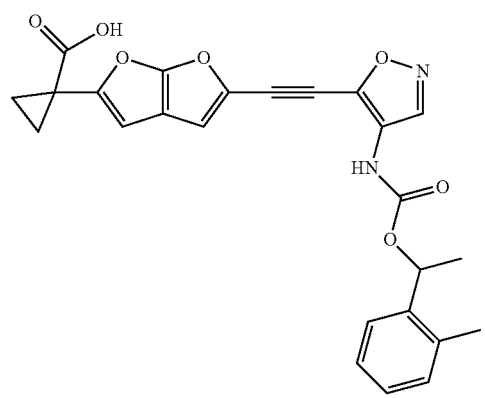 [SMILES: Cc1ccccc1C(C)OC(=O)Nc1cnoc1C#Cc1cc2cc(C3(C(=O)O)CC3)oc2o1]
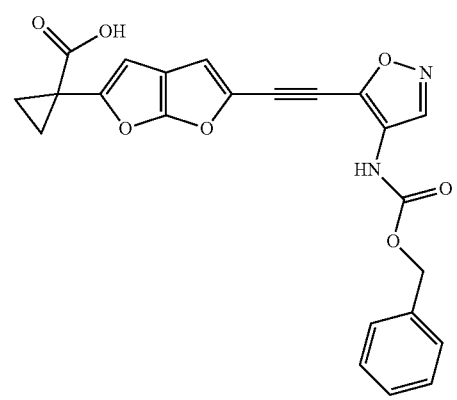 [SMILES: O=C(Nc1cnoc1C#Cc1cc2cc(C3(C(=O)O)CC3)oc2o1)OCc1ccccc1]
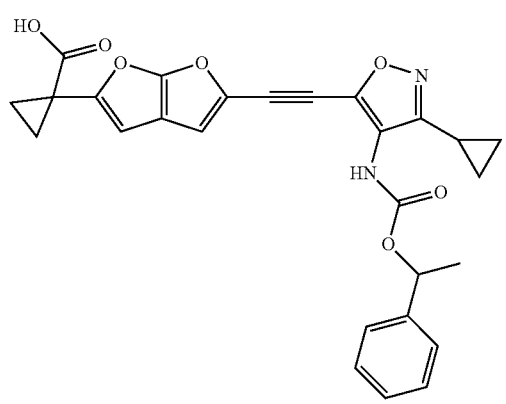 [SMILES: CC(OC(=O)Nc1c(C2CC2)noc1C#Cc1cc2cc(C3(C(=O)O)CC3)oc2o1)c1ccccc1]
1368
TABLE 15-continued
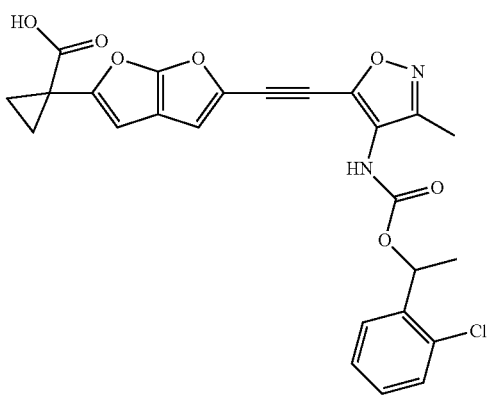
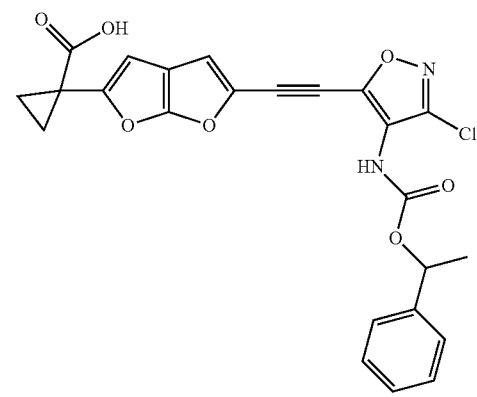 [SMILES: CC(OC(=O)Nc1c(Cl)noc1C#Cc1cc2cc(C3(C(=O)O)CC3)oc2o1)c1ccccc1]
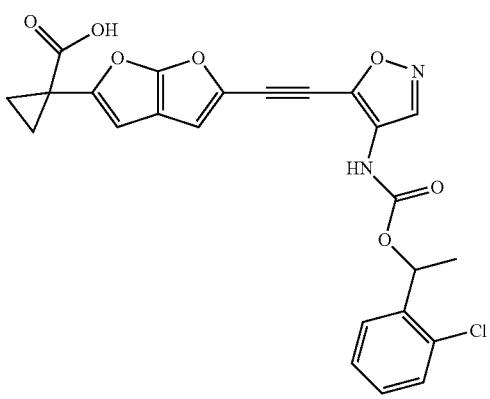 [SMILES: CC(OC(=O)Nc1cnoc1C#Cc1cc2cc(C3(C(=O)O)CC3)oc2o1)c1ccccc1Cl]
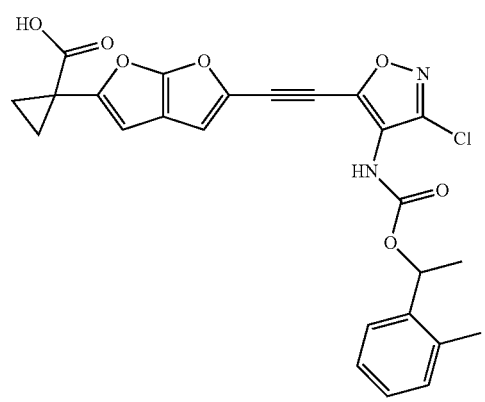 [SMILES: Cc1ccccc1C(C)OC(=O)Nc1c(Cl)noc1C#Cc1cc2cc(C3(C(=O)O)CC3)oc2o1]

TABLE 15-continued
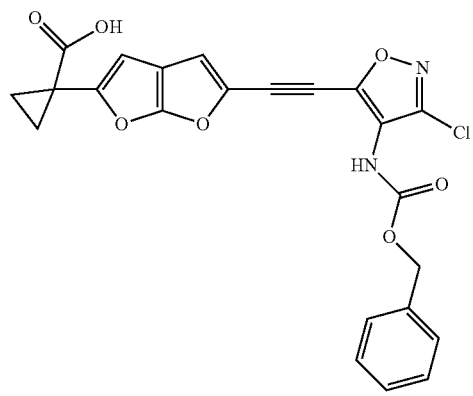 [SMILES: O=C(Nc1c(Cl)noc1C#Cc1cc2cc(C3(C(=O)O)CC3)oc2o1)OCc1ccccc1]
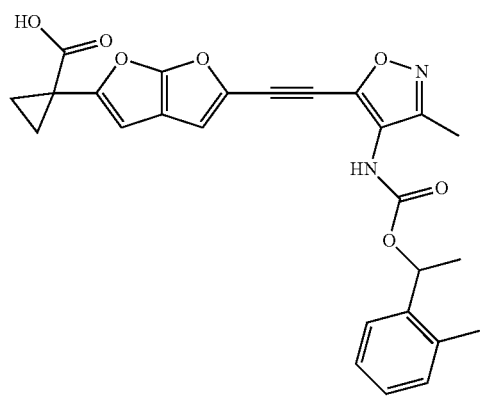 [SMILES: Cc1ccccc1C(C)OC(=O)Nc1c(C)noc1C#Cc1cc2cc(C3(C(=O)O)CC3)oc2o1]
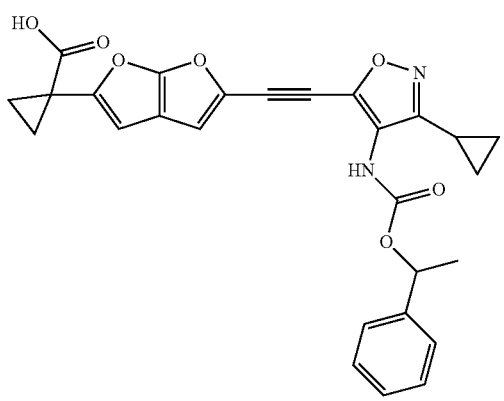
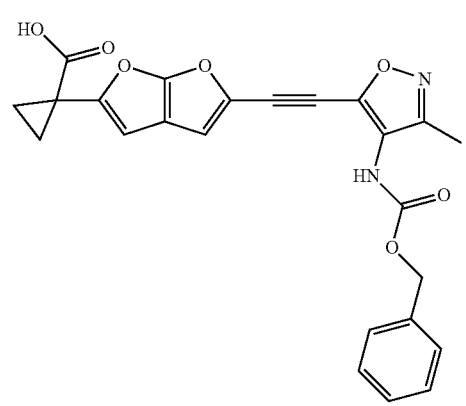 [SMILES: Cc1noc(C#Cc2cc3cc(C4(C(=O)O)CC4)oc3o2)c1NC(=O)OCc1ccccc1]
TABLE 15-continued
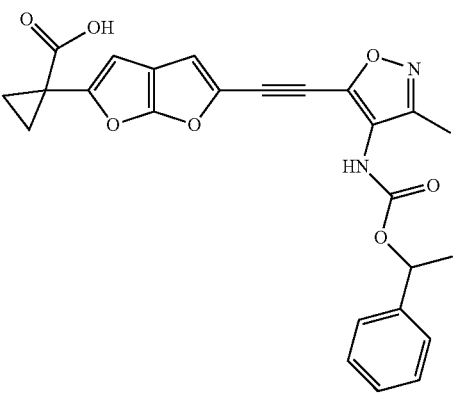 [SMILES: Cc1noc(C#Cc2cc3cc(C4(C(=O)O)CC4)oc3o2)c1NC(=O)OC(C)c1ccccc1]
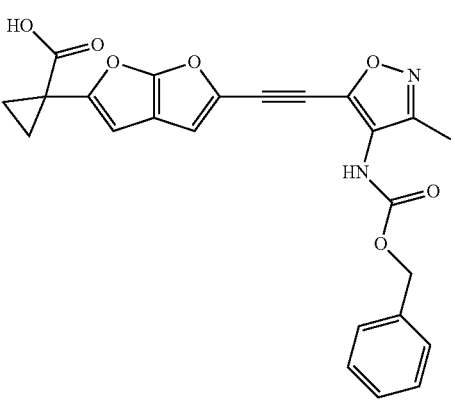 [SMILES: Cc1noc(C#Cc2cc3cc(C4(C(=O)O)CC4)oc3o2)c1NC(=O)OCc1ccccc1]
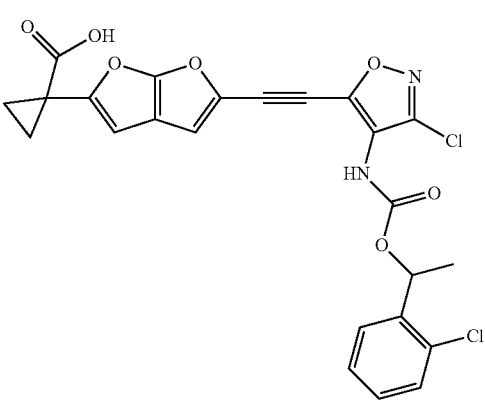 [SMILES: CC(OC(=O)Nc1c(Cl)noc1C#Cc1cc2cc(C3(C(=O)O)CC3)oc2o1)c1ccccc1Cl]
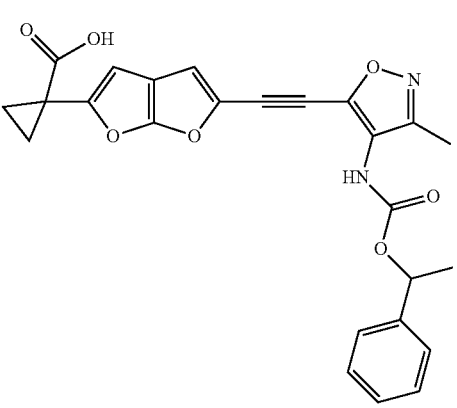 [SMILES: Cc1noc(C#Cc2cc3cc(C4(C(=O)O)CC4)oc3o2)c1NC(=O)OC(C)c1ccccc1]

TABLE 15-continued
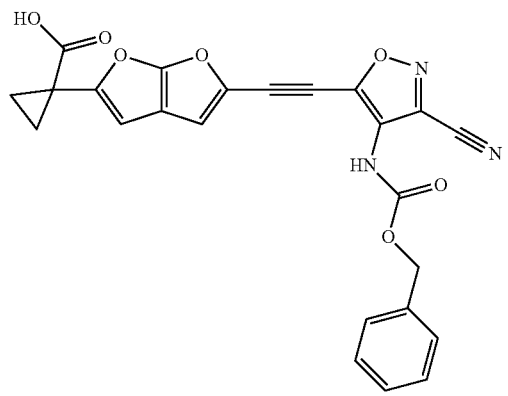 [SMILES: N#Cc1noc(C#Cc2cc3cc(C4(C(=O)O)CC4)oc3o2)c1NC(=O)OCc1ccccc1]
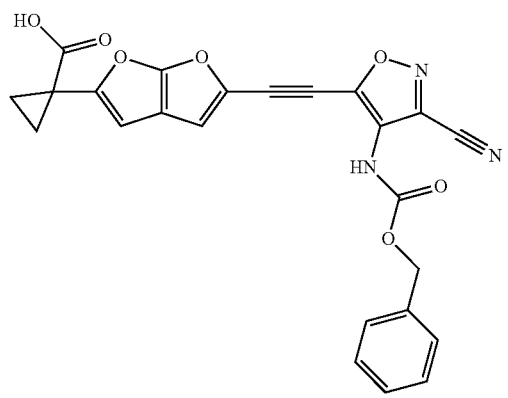 [SMILES: N#Cc1noc(C#Cc2cc3cc(C4(C(=O)O)CC4)oc3o2)c1NC(=O)OCc1ccccc1]
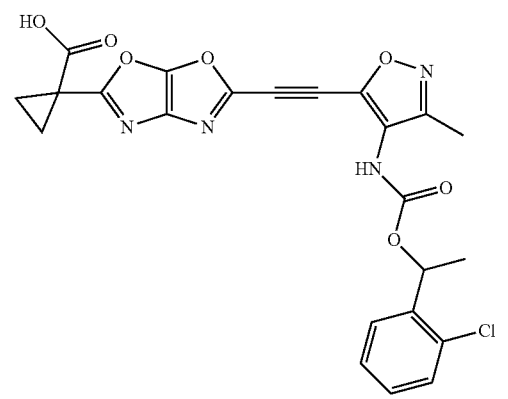 [SMILES: Cc1noc(C#Cc2nc3nc(C4(C(=O)O)CC4)oc3o2)c1NC(=O)OC(C)c1ccccc1Cl]
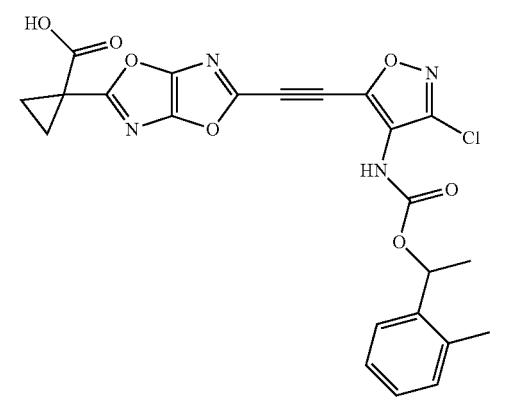 [SMILES: Cc1ccccc1C(C)OC(=O)Nc1c(Cl)noc1C#Cc1nc2oc(C3(C(=O)O)CC3)nc2o1]
TABLE 15-continued
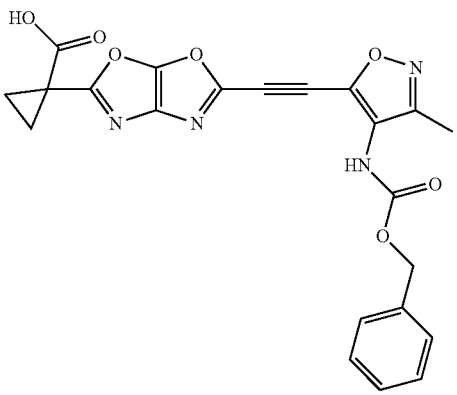 [SMILES: Cc1noc(C#Cc2nc3nc(C4(C(=O)O)CC4)oc3o2)c1NC(=O)OCc1ccccc1]
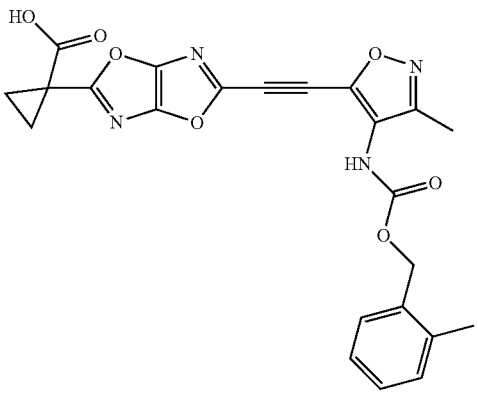
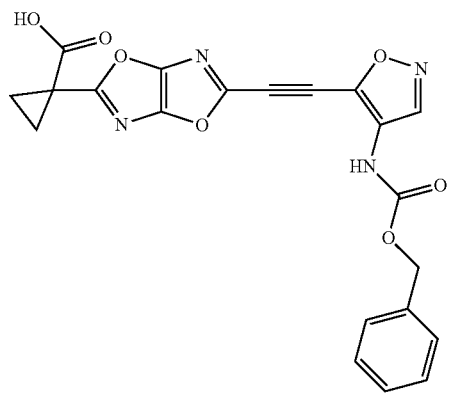
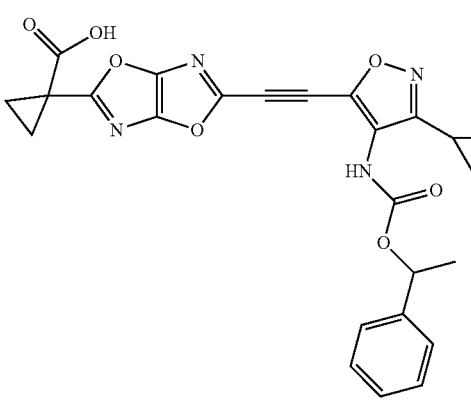

TABLE 15-continued
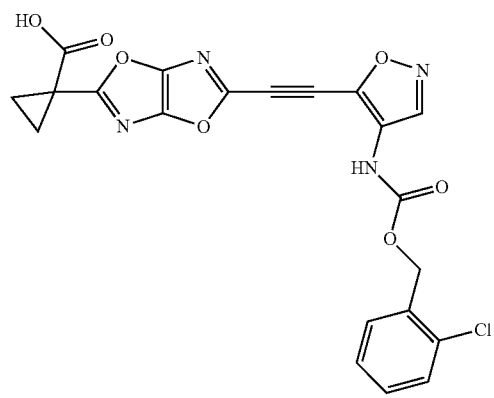
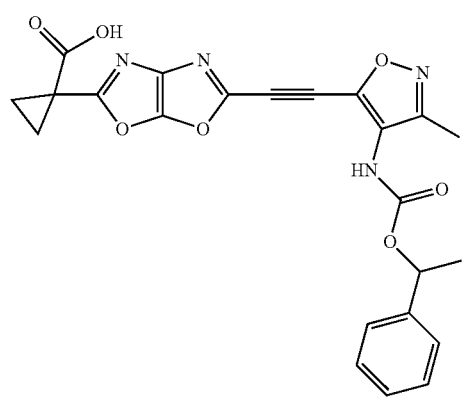 [SMILES: Cc1noc(C#Cc2nc3nc(C4(C(=O)O)CC4)oc3o2)c1NC(=O)OC(C)c1ccccc1]
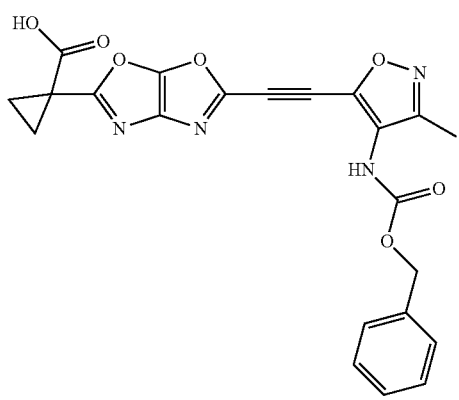 [SMILES: Cc1noc(C#Cc2nc3nc(C4(C(=O)O)CC4)oc3o2)c1NC(=O)OCc1ccccc1]
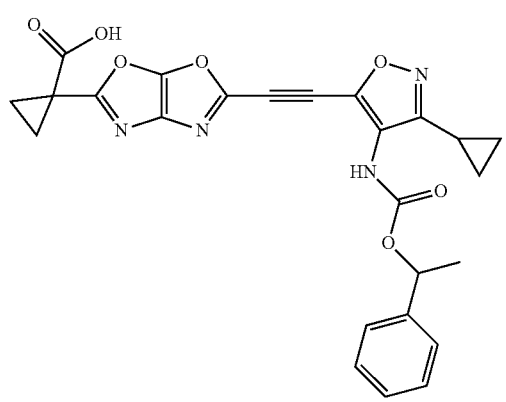 [SMILES: CC(OC(=O)Nc1c(C2CC2)noc1C#Cc1nc2nc(C3(C(=O)O)CC3)oc2o1)c1ccccc1]
TABLE 15-continued
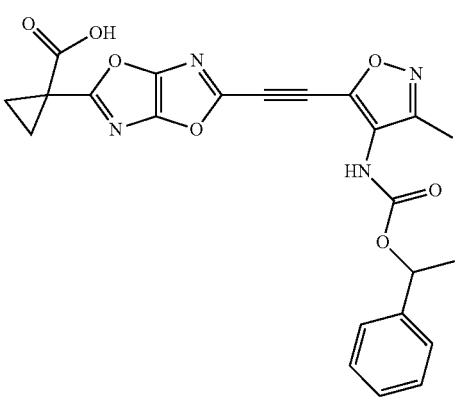 [SMILES: Cc1noc(C#Cc2nc3oc(C4(C(=O)O)CC4)nc3o2)c1NC(=O)OC(C)c1ccccc1]
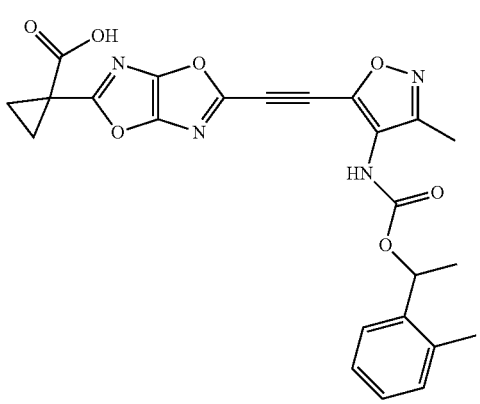 [SMILES: Cc1ccccc1C(C)OC(=O)Nc1c(C)noc1C#Cc1nc2oc(C3(C(=O)O)CC3)nc2o1]
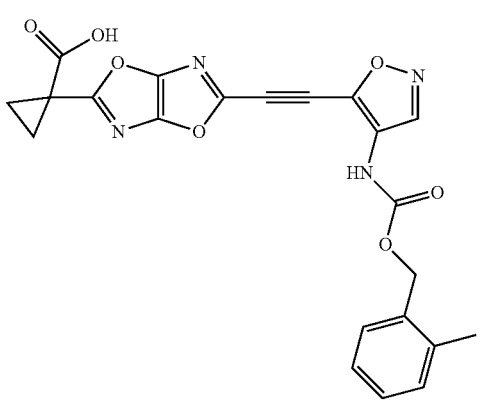 [SMILES: Cc1ccccc1COC(=O)Nc1cnoc1C#Cc1nc2oc(C3(C(=O)O)CC3)nc2o1]
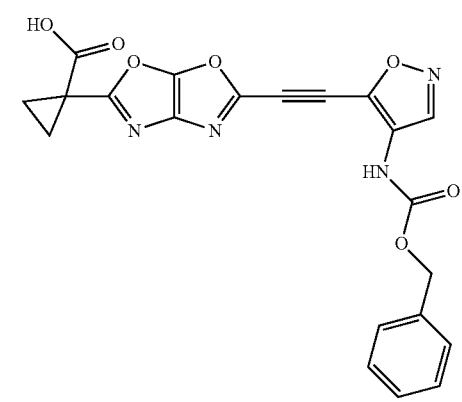

TABLE 15-continued
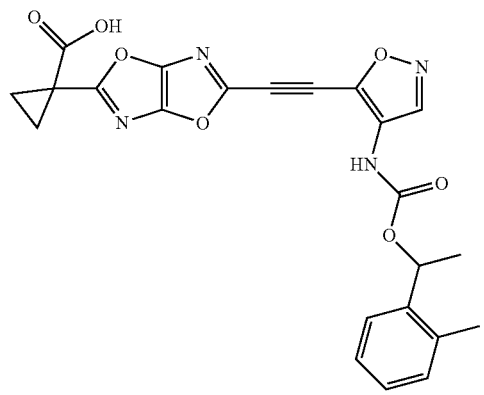 [SMILES: Cc1ccccc1C(C)OC(=O)Nc1cnoc1C#Cc1nc2oc(C3(C(=O)O)CC3)nc2o1]
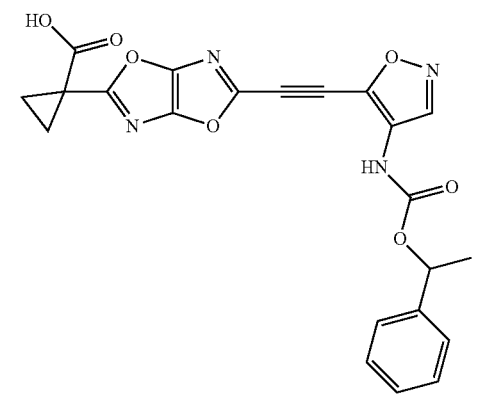 [SMILES: CC(OC(=O)Nc1cnoc1C#Cc1nc2oc(C3(C(=O)O)CC3)nc2o1)c1ccccc1]
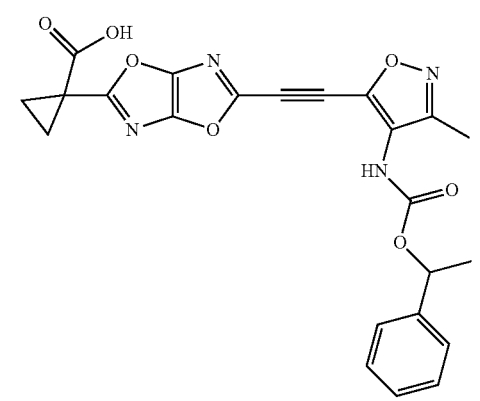 [SMILES: Cc1noc(C#Cc2nc3oc(C4(C(=O)O)CC4)nc3o2)c1NC(=O)OC(C)c1ccccc1]
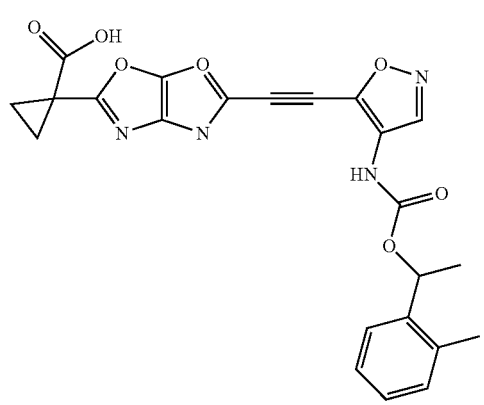
TABLE 15-continued
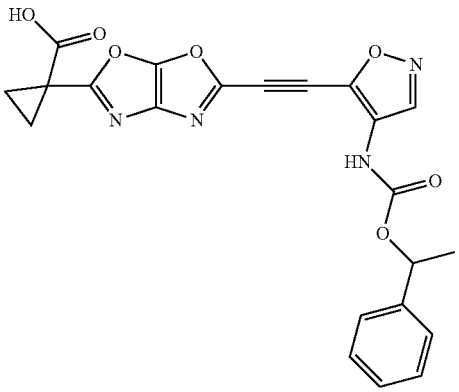 [SMILES: CC(OC(=O)Nc1cnoc1C#Cc1nc2nc(C3(C(=O)O)CC3)oc2o1)c1ccccc1]
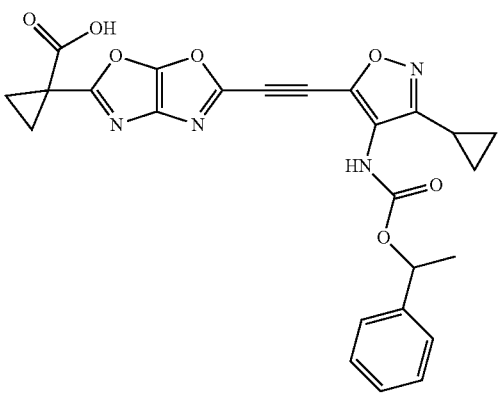 [SMILES: CC(OC(=O)Nc1c(C2CC2)noc1C#Cc1nc2nc(C3(C(=O)O)CC3)oc2o1)c1ccccc1]
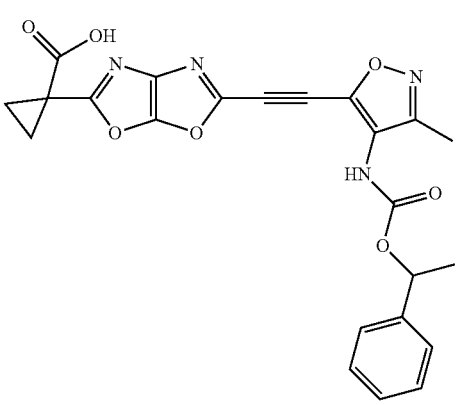 [SMILES: Cc1noc(C#Cc2nc3nc(C4(C(=O)O)CC4)oc3o2)c1NC(=O)OC(C)c1ccccc1]
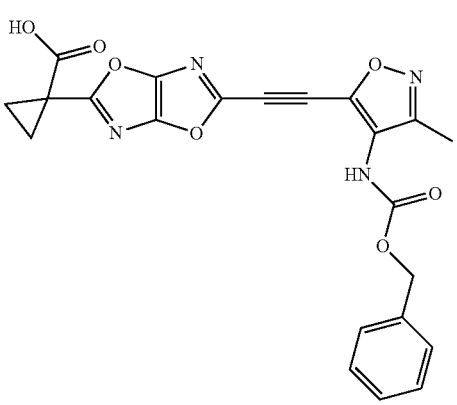 [SMILES: Cc1noc(C#Cc2nc3oc(C4(C(=O)O)CC4)nc3o2)c1NC(=O)OCc1ccccc1]

1377
TABLE 15-continued
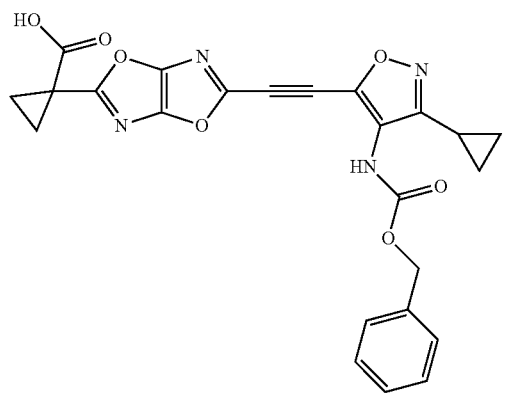 [SMILES: O=C(Nc1c(C2CC2)noc1C#Cc1nc2oc(C3(C(=O)O)CC3)nc2o1)OCc1ccccc1]
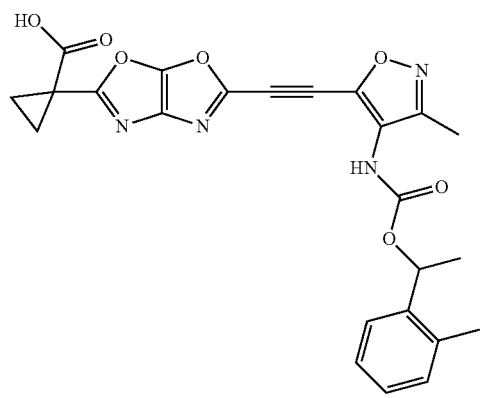 [SMILES: Cc1ccccc1C(C)OC(=O)Nc1c(C)noc1C#Cc1nc2nc(C3(C(=O)O)CC3)oc2o1]
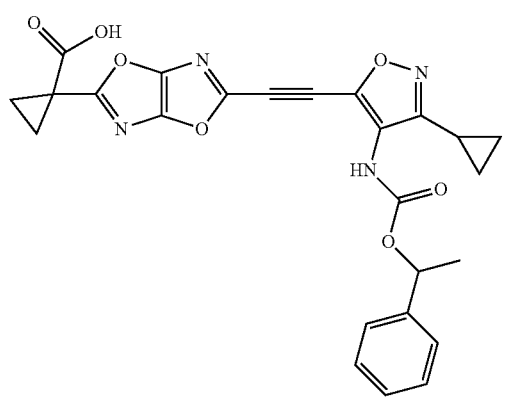 [SMILES: CC(OC(=O)Nc1c(C2CC2)noc1C#Cc1nc2oc(C3(C(=O)O)CC3)nc2o1)c1ccccc1]
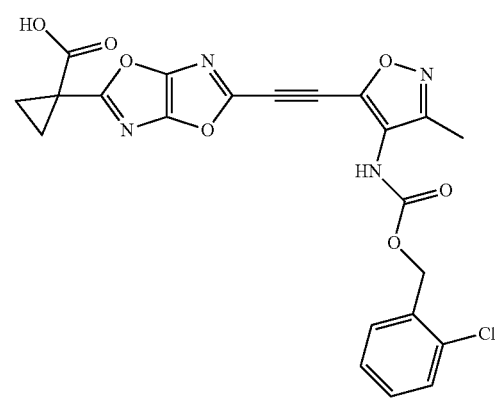 [SMILES: Cc1noc(C#Cc2nc3oc(C4(C(=O)O)CC4)nc3o2)c1NC(=O)OCc1ccccc1Cl]
1378
TABLE 15-continued
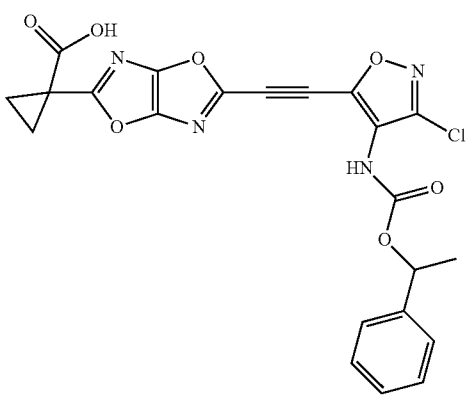 [SMILES: CC(OC(=O)Nc1c(Cl)noc1C#Cc1nc2oc(C3(C(=O)O)CC3)nc2o1)c1ccccc1]
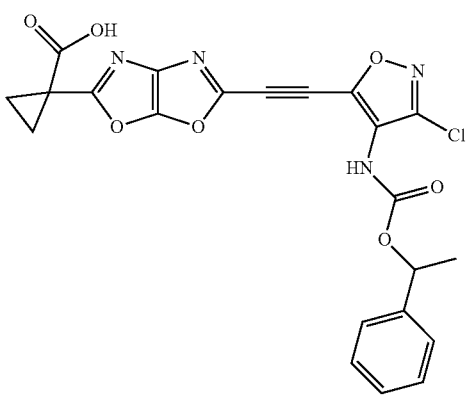 [SMILES: CC(OC(=O)Nc1c(Cl)noc1C#Cc1nc2nc(C3(C(=O)O)CC3)oc2o1)c1ccccc1]
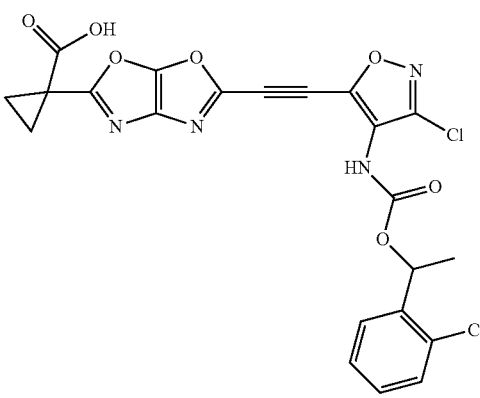
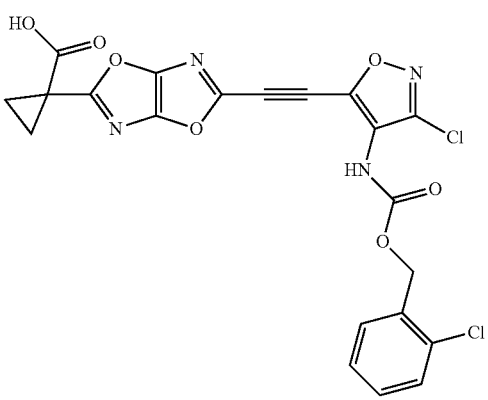 [SMILES: O=C(Nc1c(Cl)noc1C#Cc1nc2oc(C3(C(=O)O)CC3)nc2o1)OCc1ccccc1Cl]

TABLE 15-continued
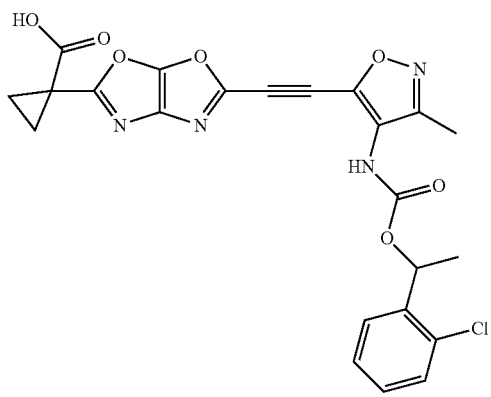 [SMILES: Cc1noc(C#Cc2nc3nc(C4(C(=O)O)CC4)oc3o2)c1NC(=O)OC(C)c1ccccc1Cl]
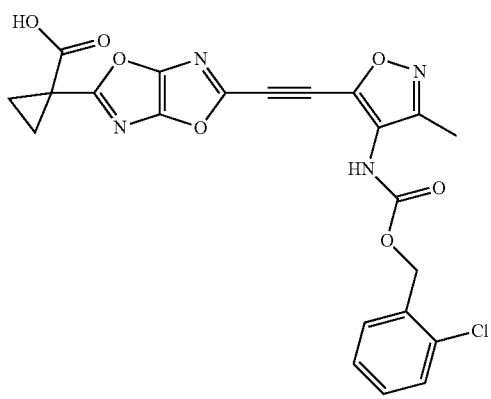 [SMILES: Cc1noc(C#Cc2nc3oc(C4(C(=O)O)CC4)nc3o2)c1NC(=O)OCc1ccccc1Cl]
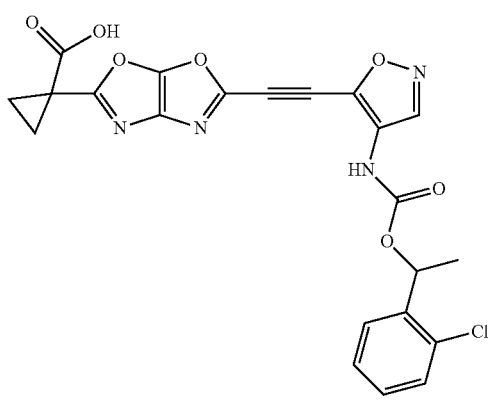 [SMILES: CC(OC(=O)Nc1cnoc1C#Cc1nc2nc(C3(C(=O)O)CC3)oc2o1)c1ccccc1Cl]
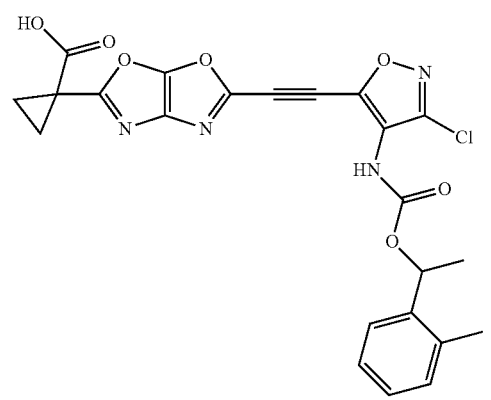 [SMILES: Cc1ccccc1C(C)OC(=O)Nc1c(Cl)noc1C#Cc1nc2nc(C3(C(=O)O)CC3)oc2o1]
TABLE 15-continued
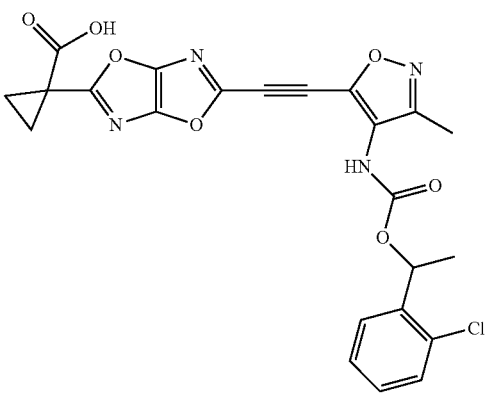 [SMILES: Cc1noc(C#Cc2nc3oc(C4(C(=O)O)CC4)nc3o2)c1NC(=O)OC(C)c1ccccc1Cl]
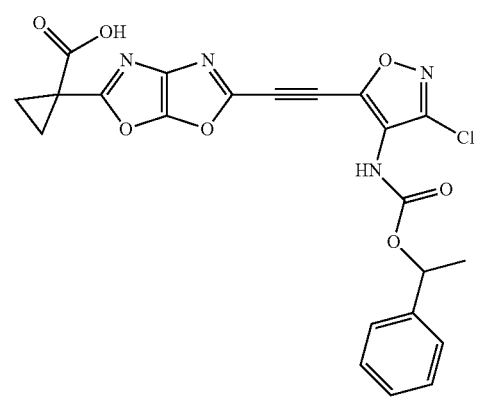 [SMILES: CC(OC(=O)Nc1c(Cl)noc1C#Cc1nc2nc(C3(C(=O)O)CC3)oc2o1)c1ccccc1]
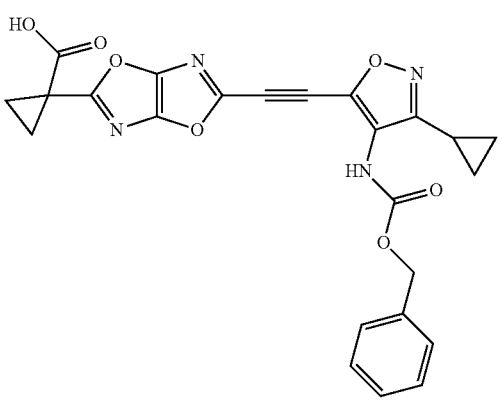
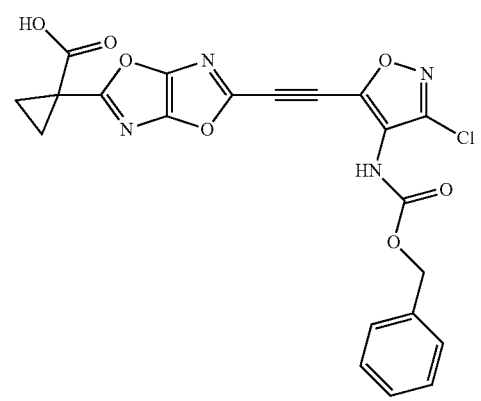

1381
TABLE 15-continued
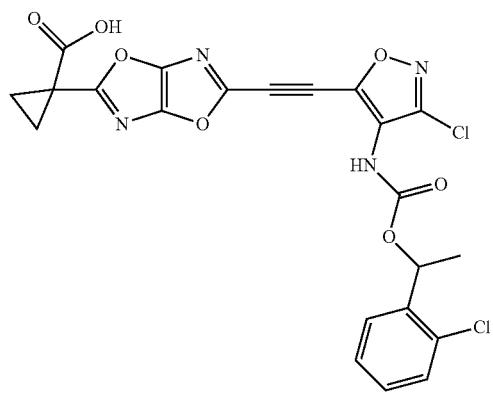 [SMILES: CC(OC(=O)Nc1c(Cl)noc1C#Cc1nc2oc(C3(C(=O)O)CC3)nc2o1)c1ccccc1Cl]
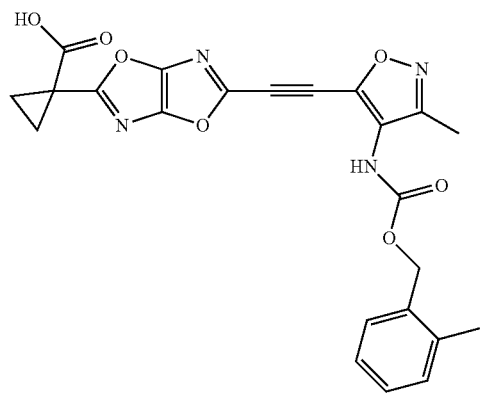
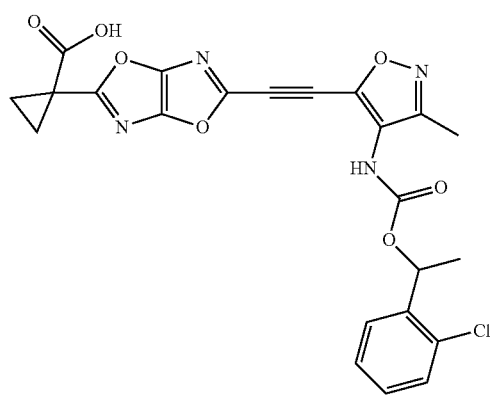 [SMILES: Cc1noc(C#Cc2nc3oc(C4(C(=O)O)CC4)nc3o2)c1NC(=O)OC(C)c1ccccc1Cl]
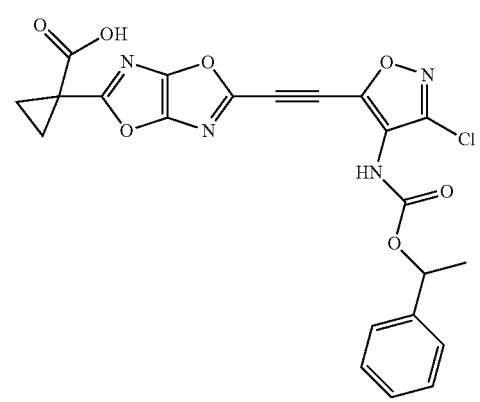
1382
TABLE 15-continued
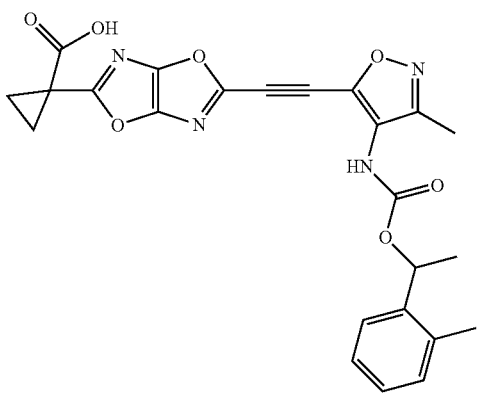 [SMILES: Cc1ccccc1C(C)OC(=O)Nc1c(C)noc1C#Cc1nc2oc(C3(C(=O)O)CC3)nc2o1]
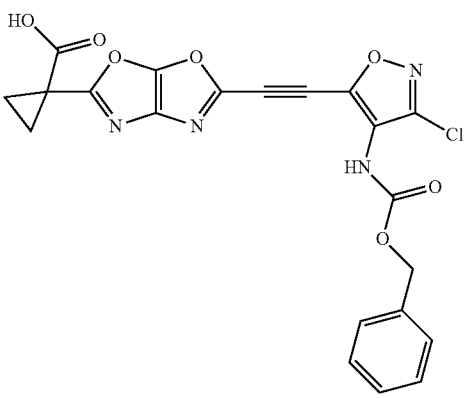 [SMILES: O=C(Nc1c(Cl)noc1C#Cc1nc2nc(C3(C(=O)O)CC3)oc2o1)OCc1ccccc1]
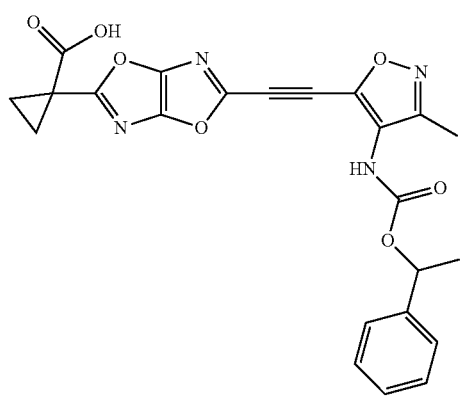 [SMILES: Cc1noc(C#Cc2nc3oc(C4(C(=O)O)CC4)nc3o2)c1NC(=O)OC(C)c1ccccc1]
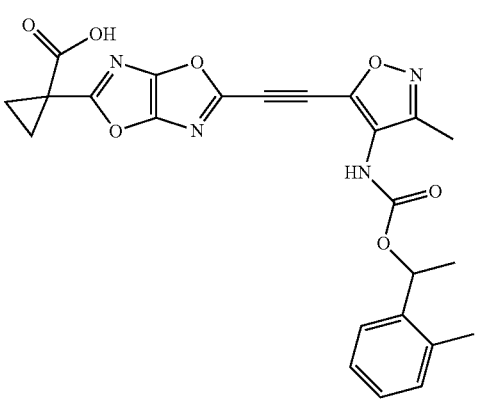 [SMILES: Cc1ccccc1C(C)OC(=O)Nc1c(C)noc1C#Cc1nc2oc(C3(C(=O)O)CC3)nc2o1]

1383
TABLE 15-continued
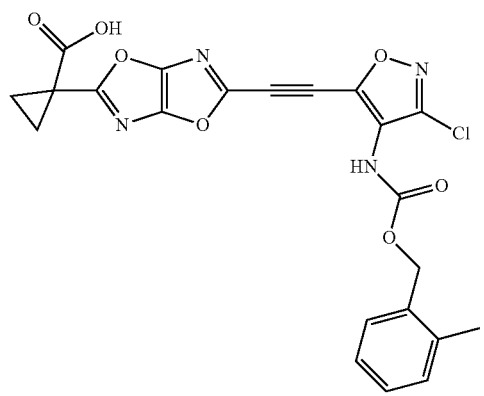 [SMILES: Cc1ccccc1COC(=O)Nc1c(Cl)noc1C#Cc1nc2oc(C3(C(=O)O)CC3)nc2o1]
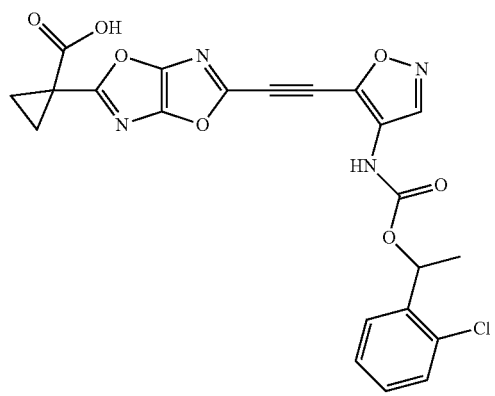 [SMILES: CC(OC(=O)Nc1cnoc1C#Cc1nc2oc(C3(C(=O)O)CC3)nc2o1)c1ccccc1Cl]
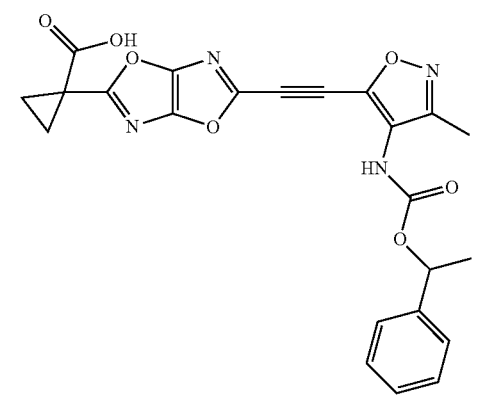 [SMILES: Cc1noc(C#Cc2nc3oc(C4(C(=O)O)CC4)nc3o2)c1NC(=O)OC(C)c1ccccc1]
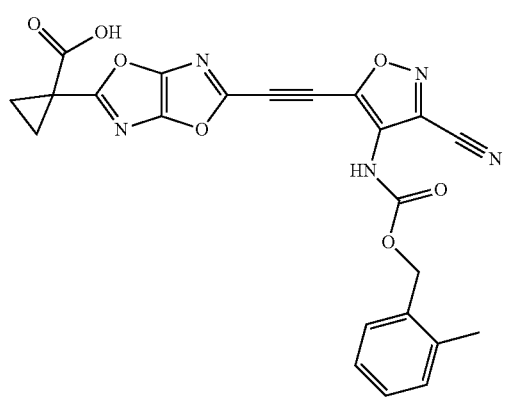 [SMILES: Cc1ccccc1COC(=O)Nc1c(C#N)noc1C#Cc1nc2oc(C3(C(=O)O)CC3)nc2o1]
1384
TABLE 15-continued
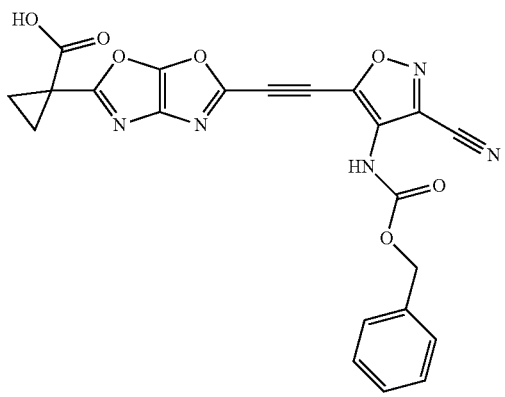 [SMILES: N#Cc1noc(C#Cc2nc3nc(C4(C(=O)O)CC4)oc3o2)c1NC(=O)OCc1ccccc1]
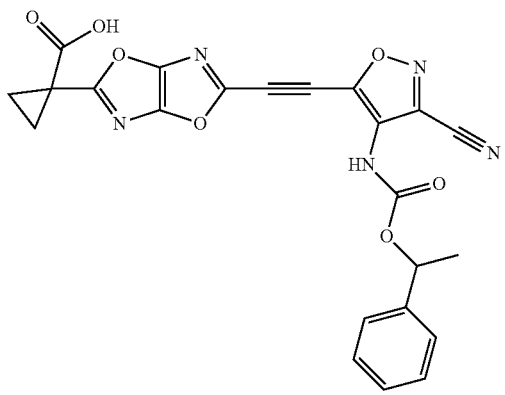 [SMILES: CC(OC(=O)Nc1c(C#N)noc1C#Cc1nc2oc(C3(C(=O)O)CC3)nc2o1)c1ccccc1]
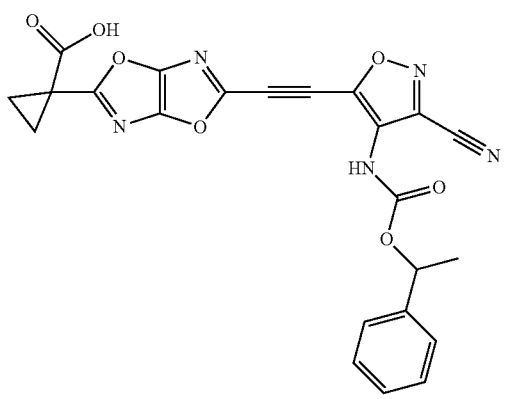 [SMILES: CC(OC(=O)Nc1c(C#N)noc1C#Cc1nc2oc(C3(C(=O)O)CC3)nc2o1)c1ccccc1]
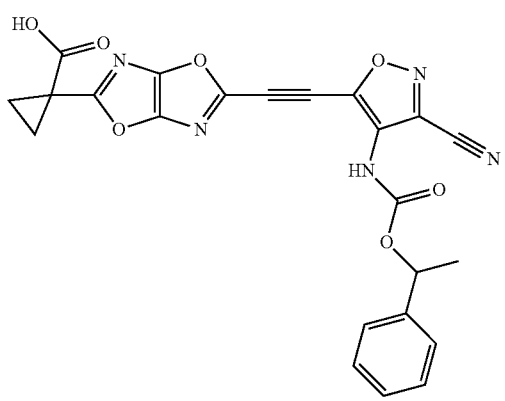 [SMILES: CC(OC(=O)Nc1c(C#N)noc1C#Cc1nc2oc(C3(C(=O)O)CC3)nc2o1)c1ccccc1]

TABLE 15-continued
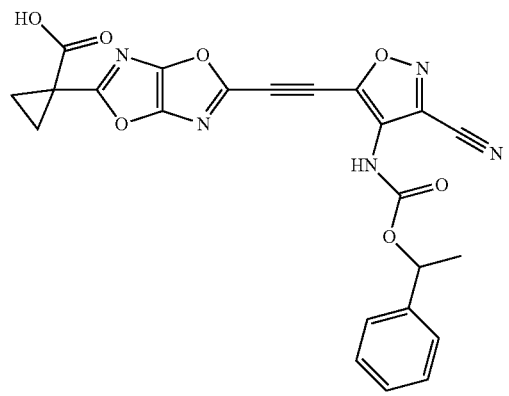 [SMILES: CC(OC(=O)Nc1c(C#N)noc1C#Cc1nc2oc(C3(C(=O)O)CC3)nc2o1)c1ccccc1]
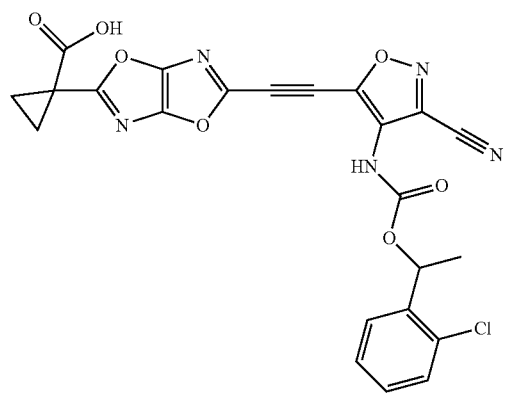 [SMILES: CC(OC(=O)Nc1c(C#N)noc1C#Cc1nc2oc(C3(C(=O)O)CC3)nc2o1)c1ccccc1Cl]
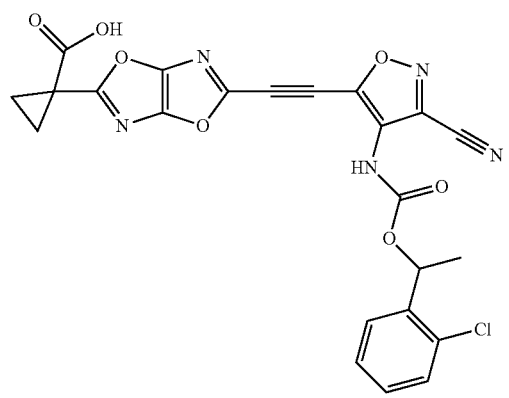 [SMILES: CC(OC(=O)Nc1c(C#N)noc1C#Cc1nc2oc(C3(C(=O)O)CC3)nc2o1)c1ccccc1Cl]
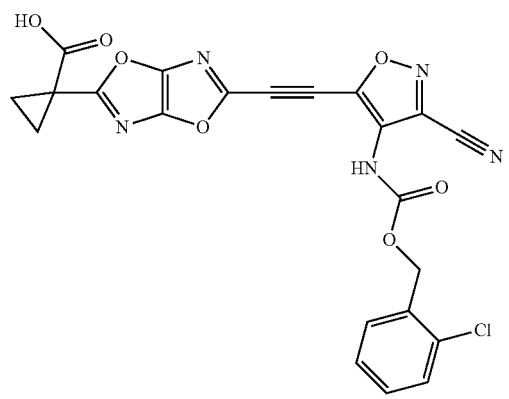 [SMILES: N#Cc1noc(C#Cc2nc3oc(C4(C(=O)O)CC4)nc3o2)c1NC(=O)OCc1ccccc1Cl]
TABLE 15-continued
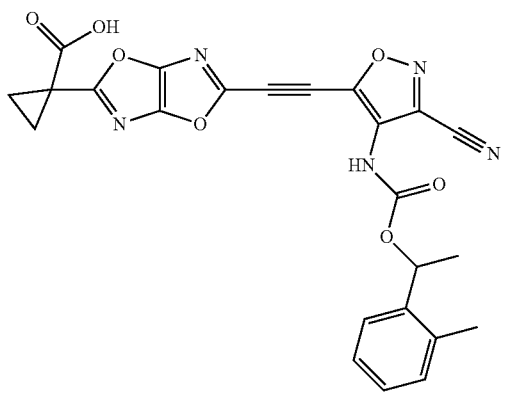 [SMILES: Cc1ccccc1C(C)OC(=O)Nc1c(C#N)noc1C#Cc1nc2oc(C3(C(=O)O)CC3)nc2o1]
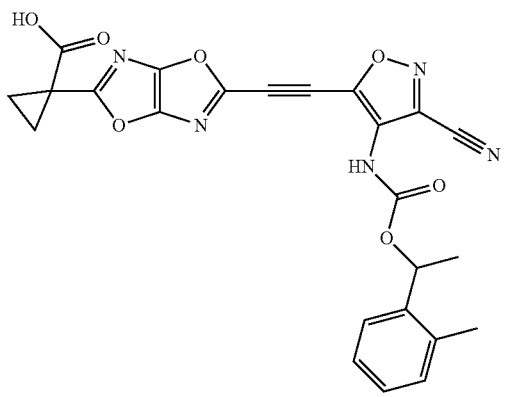 [SMILES: Cc1ccccc1C(C)OC(=O)Nc1c(C#N)noc1C#Cc1nc2oc(C3(C(=O)O)CC3)nc2o1]
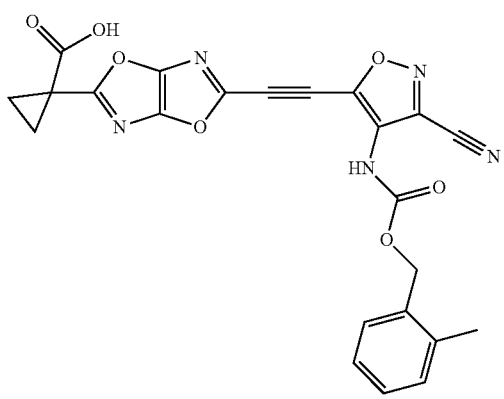
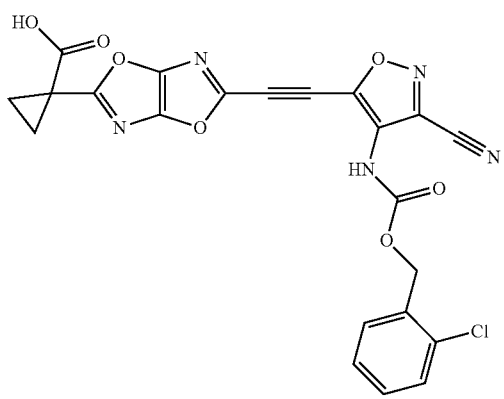 [SMILES: N#Cc1noc(C#Cc2nc3oc(C4(C(=O)O)CC4)nc3o2)c1NC(=O)OCc1ccccc1Cl]

TABLE 15-continued
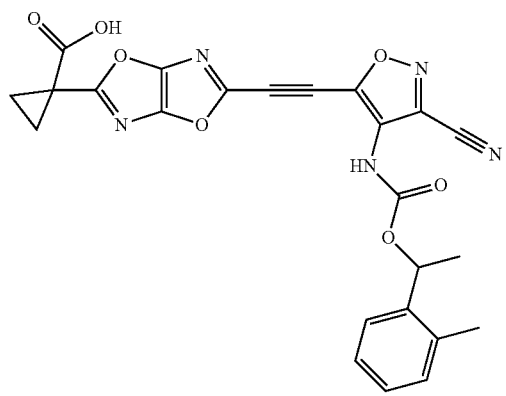 [SMILES: Cc1ccccc1C(C)OC(=O)Nc1c(C#N)noc1C#Cc1nc2oc(C3(C(=O)O)CC3)nc2o1]
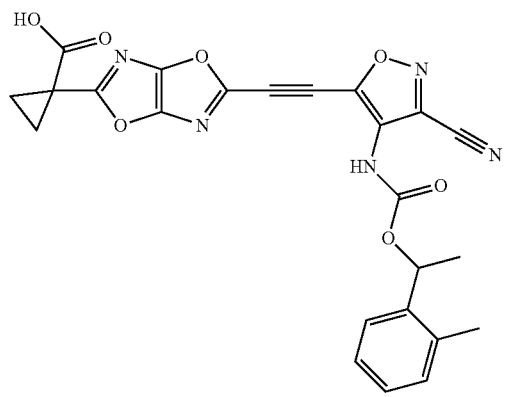 [SMILES: Cc1ccccc1C(C)OC(=O)Nc1c(C#N)noc1C#Cc1nc2oc(C3(C(=O)O)CC3)nc2o1]
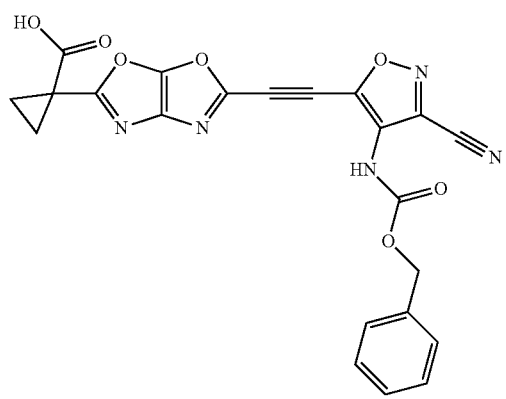
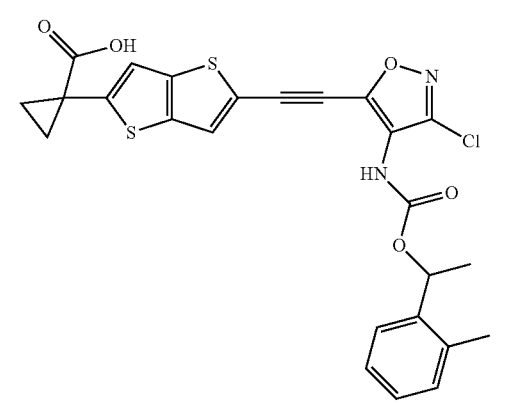
TABLE 15-continued
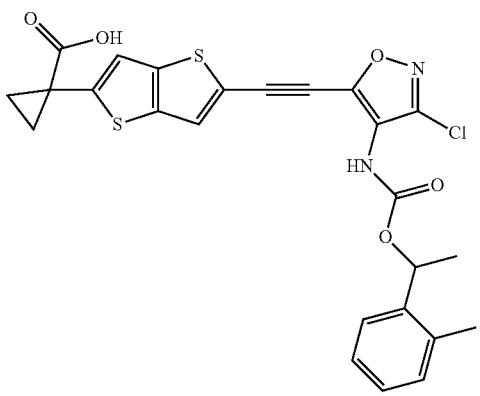 [SMILES: Cc1ccccc1C(C)OC(=O)Nc1c(Cl)noc1C#Cc1cc2sc(C3(C(=O)O)CC3)cc2s1]
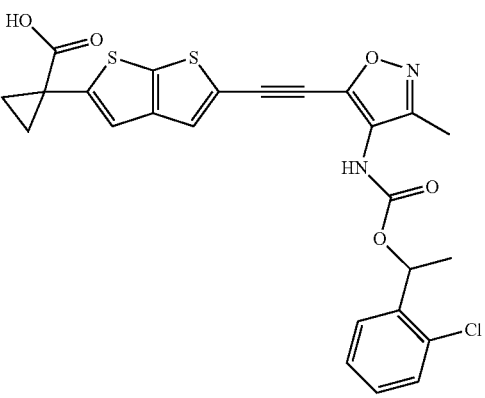 [SMILES: Cc1noc(C#Cc2cc3cc(C4(C(=O)O)CC4)sc3s2)c1NC(=O)OC(C)c1ccccc1Cl]
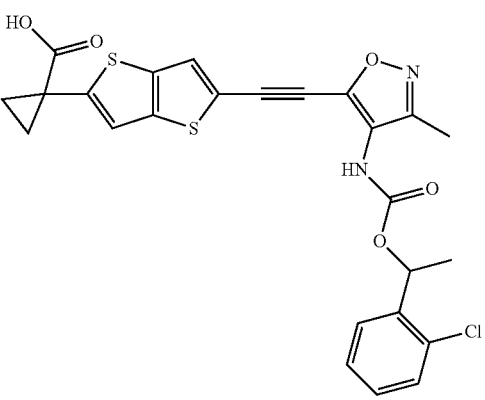 [SMILES: Cc1noc(C#Cc2cc3sc(C4(C(=O)O)CC4)cc3s2)c1NC(=O)OC(C)c1ccccc1Cl]
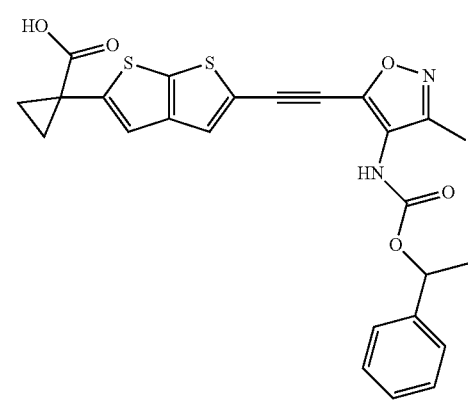 [SMILES: Cc1noc(C#Cc2cc3cc(C4(C(=O)O)CC4)sc3s2)c1NC(=O)OC(C)c1ccccc1]

TABLE 15-continued
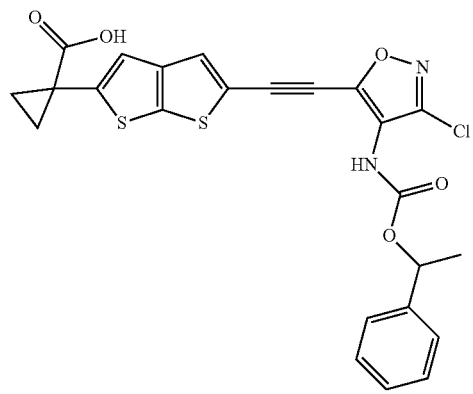 [SMILES: CC(OC(=O)Nc1c(Cl)noc1C#Cc1cc2cc(C3(C(=O)O)CC3)sc2s1)c1ccccc1]
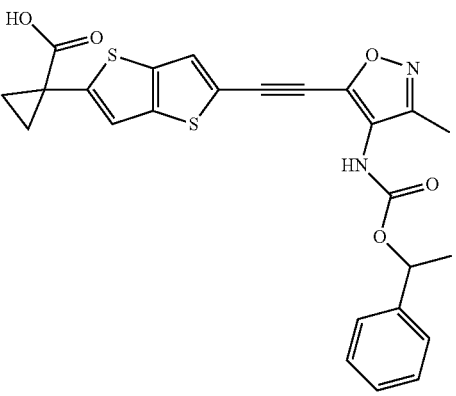
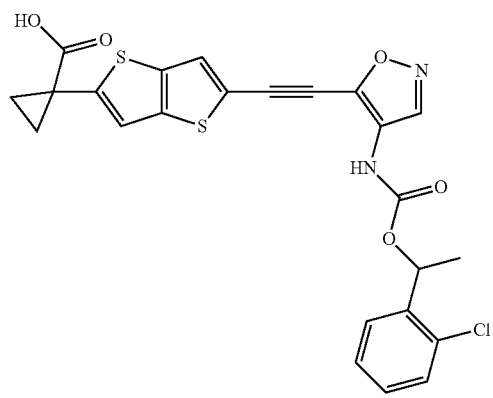 [SMILES: CC(OC(=O)Nc1cnoc1C#Cc1cc2sc(C3(C(=O)O)CC3)cc2s1)c1ccccc1Cl]
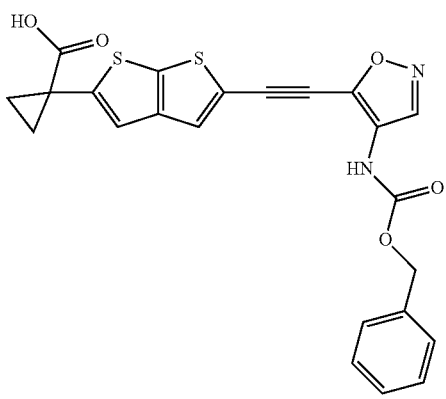
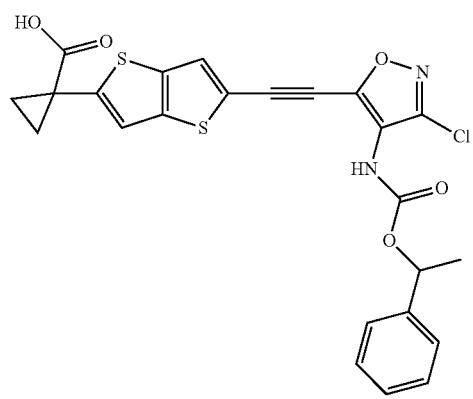 [SMILES: CC(OC(=O)Nc1c(Cl)noc1C#Cc1cc2sc(C3(C(=O)O)CC3)cc2s1)c1ccccc1]
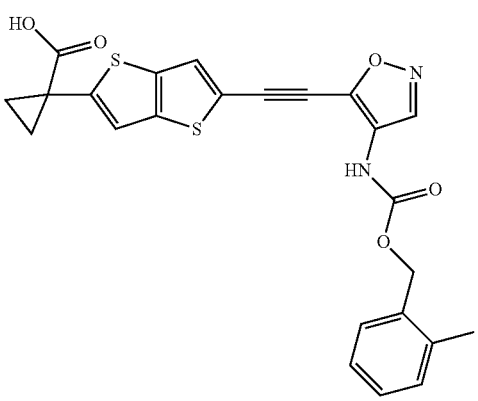
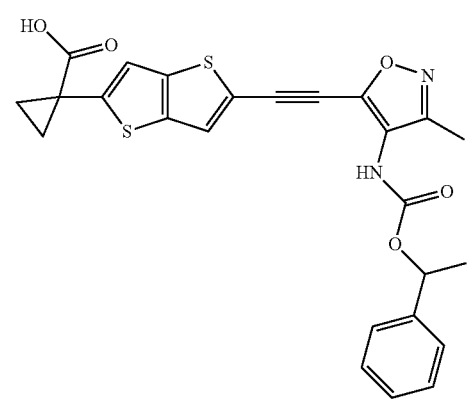 [SMILES: Cc1noc(C#Cc2cc3sc(C4(C(=O)O)CC4)cc3s2)c1NC(=O)OC(C)c1ccccc1]
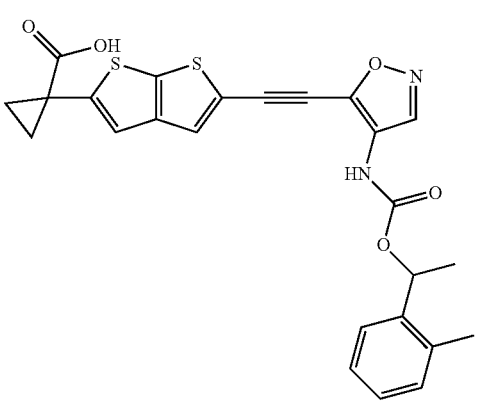 [SMILES: Cc1ccccc1C(C)OC(=O)Nc1cnoc1C#Cc1cc2cc(C3(C(=O)O)CC3)sc2s1]

1391
TABLE 15-continued
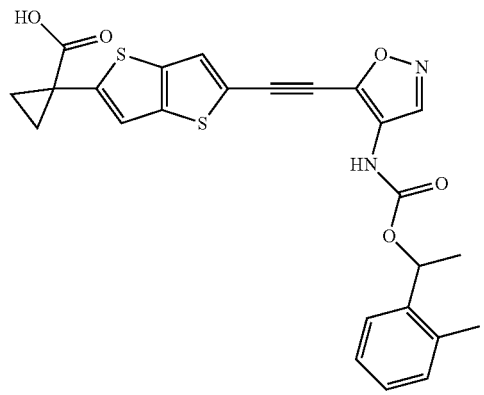 [SMILES: Cc1ccccc1C(C)OC(=O)Nc1cnoc1C#Cc1cc2sc(C3(C(=O)O)CC3)cc2s1]
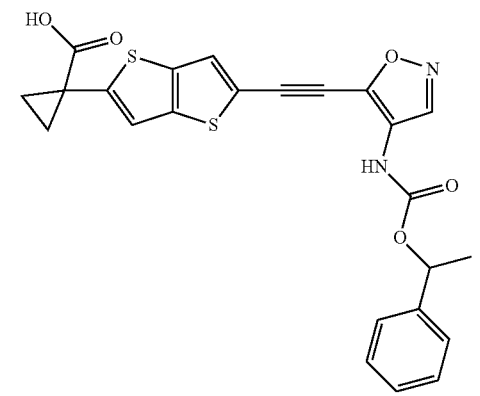 [SMILES: CC(OC(=O)Nc1cnoc1C#Cc1cc2sc(C3(C(=O)O)CC3)cc2s1)c1ccccc1]
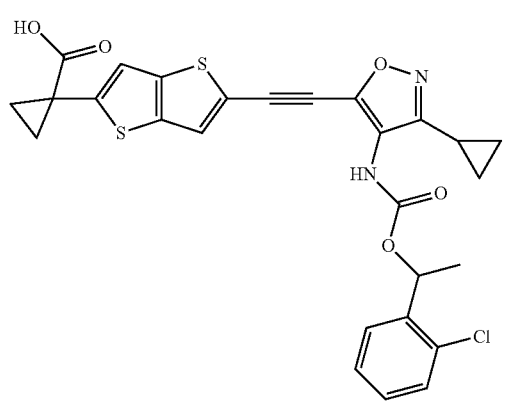
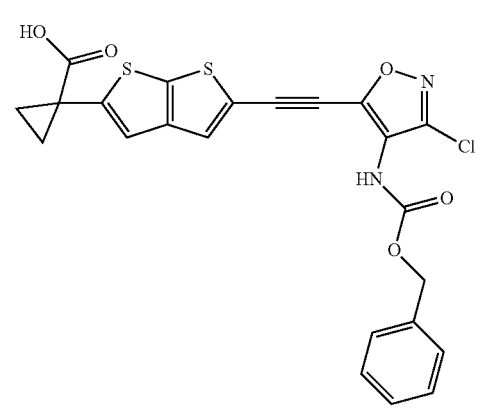 [SMILES: O=C(Nc1c(Cl)noc1C#Cc1cc2cc(C3(C(=O)O)CC3)sc2s1)OCc1ccccc1]
1392
TABLE 15-continued
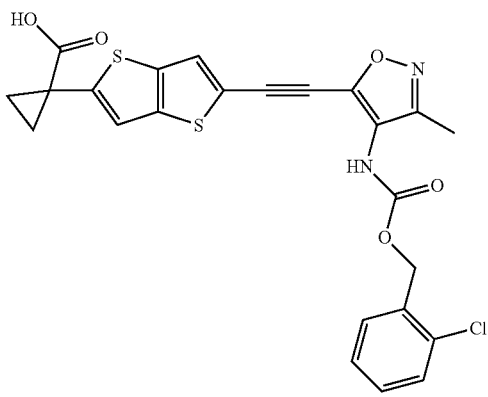 [SMILES: Cc1noc(C#Cc2cc3sc(C4(C(=O)O)CC4)cc3s2)c1NC(=O)OCc1ccccc1Cl]
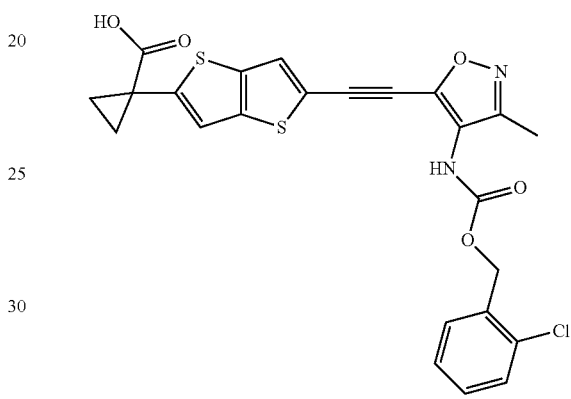
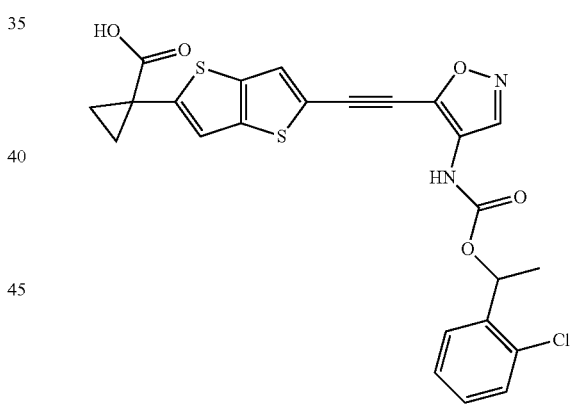
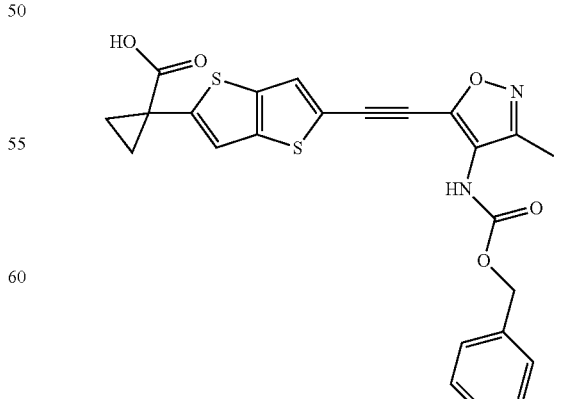

TABLE 15-continued
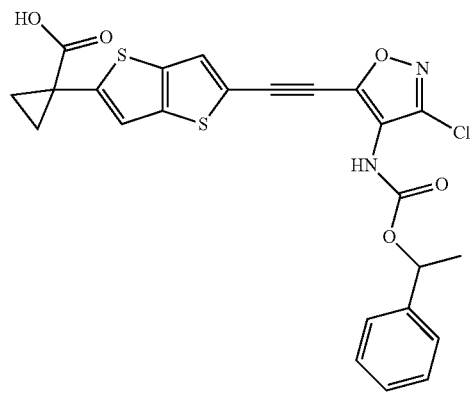 [SMILES: CC(OC(=O)Nc1c(Cl)noc1C#Cc1cc2sc(C3(C(=O)O)CC3)cc2s1)c1ccccc1]
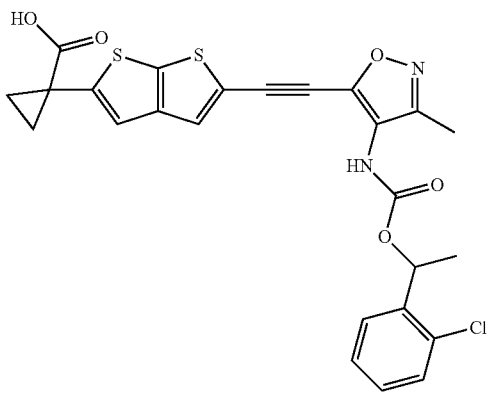
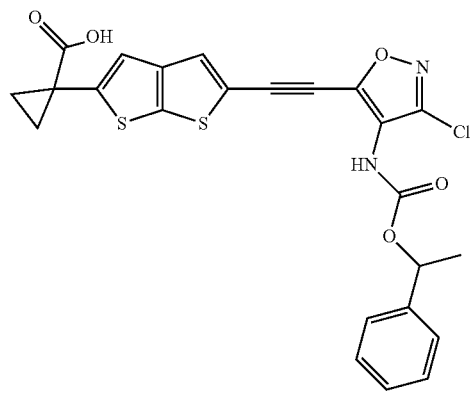 [SMILES: CC(OC(=O)Nc1c(Cl)noc1C#Cc1cc2cc(C3(C(=O)O)CC3)sc2s1)c1ccccc1]
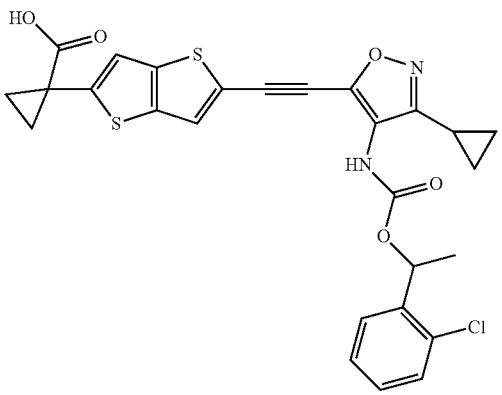
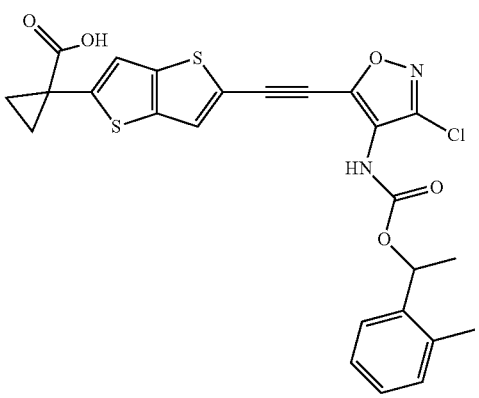 [SMILES: Cc1ccccc1C(C)OC(=O)Nc1c(Cl)noc1C#Cc1cc2sc(C3(C(=O)O)CC3)cc2s1]
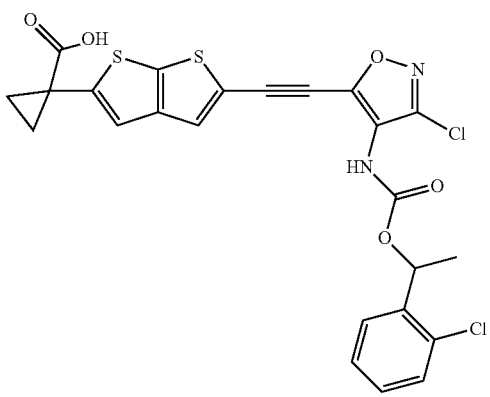
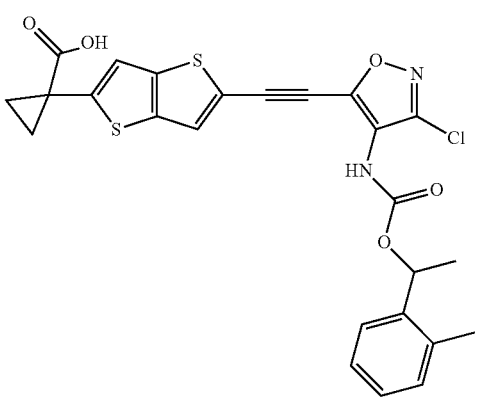 [SMILES: Cc1ccccc1C(C)OC(=O)Nc1c(Cl)noc1C#Cc1cc2sc(C3(C(=O)O)CC3)cc2s1]
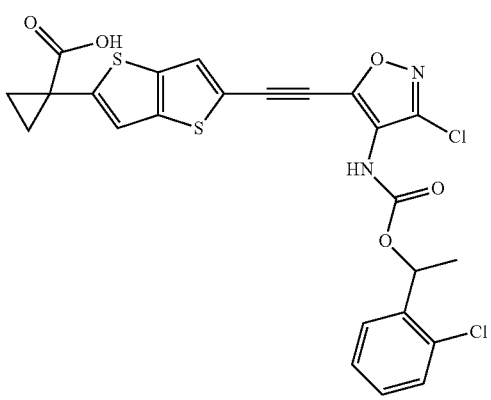 [SMILES: CC(OC(=O)Nc1c(Cl)noc1C#Cc1cc2sc(C3(C(=O)O)CC3)cc2s1)c1ccccc1Cl]

TABLE 15-continued
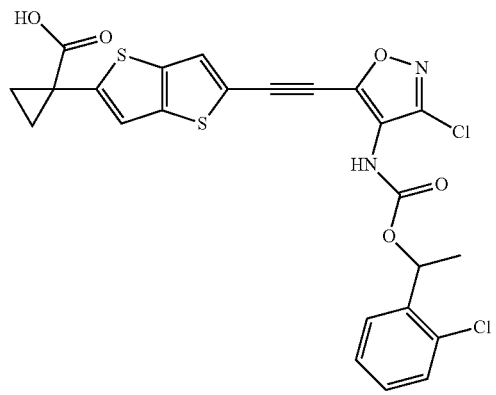 [SMILES: CC(OC(=O)Nc1c(Cl)noc1C#Cc1cc2sc(C3(C(=O)O)CC3)cc2s1)c1ccccc1Cl]
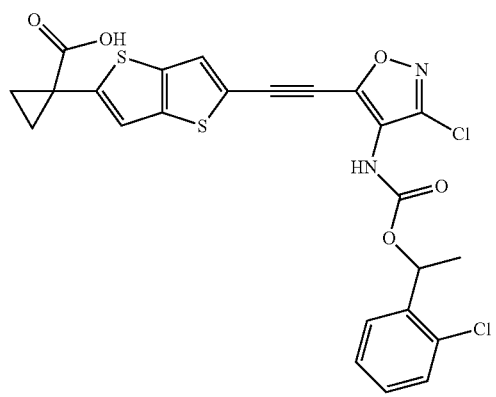 [SMILES: CC(OC(=O)Nc1c(Cl)noc1C#Cc1cc2sc(C3(C(=O)O)CC3)cc2s1)c1ccccc1Cl]
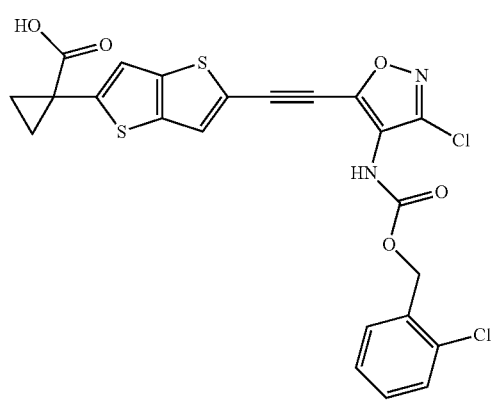 [SMILES: O=C(Nc1c(Cl)noc1C#Cc1cc2sc(C3(C(=O)O)CC3)cc2s1)OCc1ccccc1Cl]
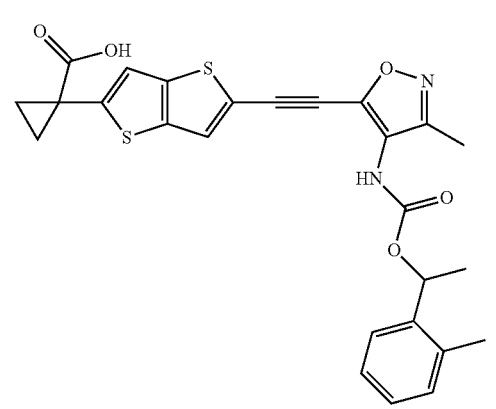 [SMILES: Cc1ccccc1C(C)OC(=O)Nc1c(C)noc1C#Cc1cc2sc(C3(C(=O)O)CC3)cc2s1]
TABLE 15-continued
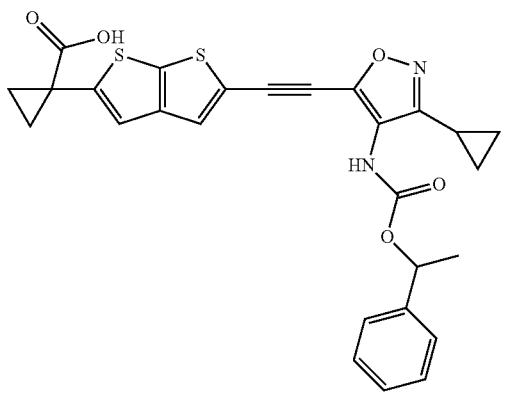 [SMILES: CC(OC(=O)Nc1c(C2CC2)noc1C#Cc1cc2cc(C3(C(=O)O)CC3)sc2s1)c1ccccc1]
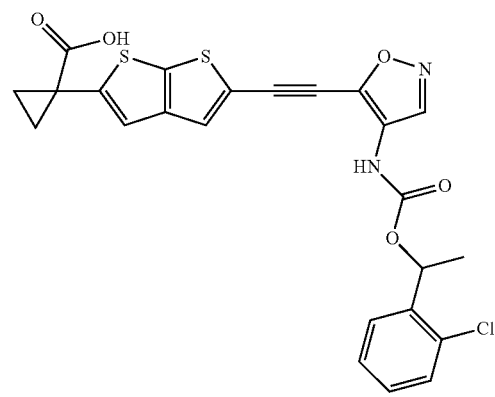 [SMILES: CC(OC(=O)Nc1cnoc1C#Cc1cc2cc(C3(C(=O)O)CC3)sc2s1)c1ccccc1Cl]
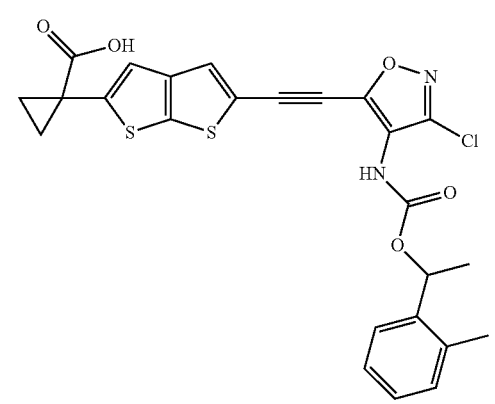 [SMILES: Cc1ccccc1C(C)OC(=O)Nc1c(Cl)noc1C#Cc1cc2cc(C3(C(=O)O)CC3)sc2s1]
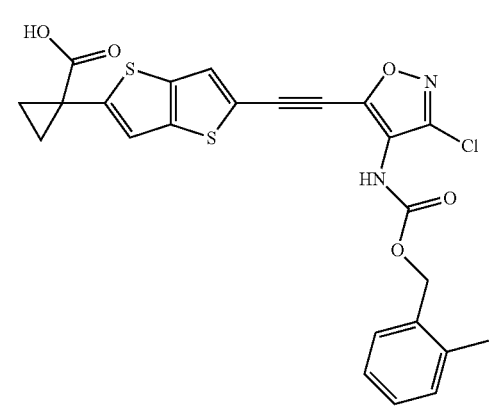

TABLE 15-continued
| 1397 | 1398 |
|---|---|
| 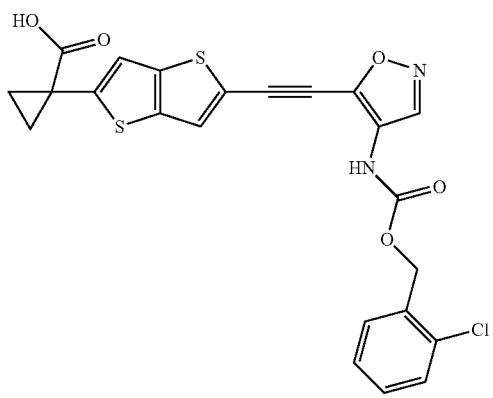 [SMILES: O=C(Nc1cnoc1C#Cc1cc2sc(C3(C(=O)O)CC3)cc2s1)OCc1ccccc1Cl] | 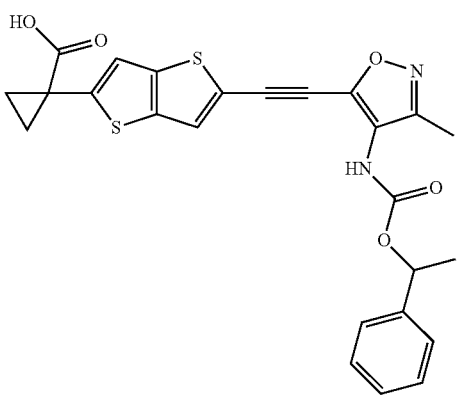 |
| 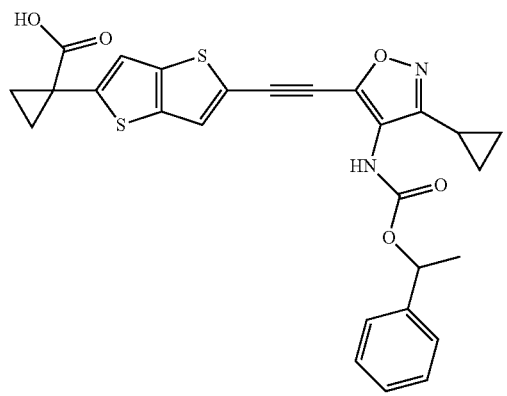 [SMILES: CC(OC(=O)Nc1c(C2CC2)noc1C#Cc1cc2sc(C3(C(=O)O)CC3)cc2s1)c1ccccc1] | 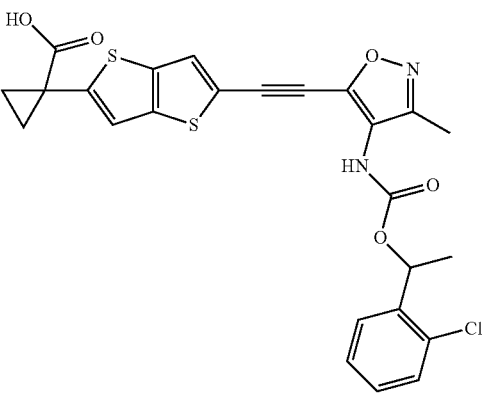 |
| 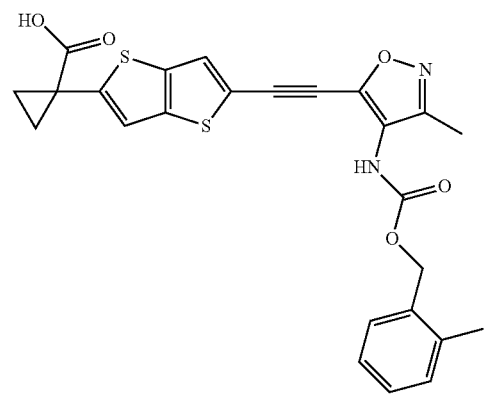 [SMILES: Cc1ccccc1COC(=O)Nc1c(C)noc1C#Cc1cc2sc(C3(C(=O)O)CC3)cc2s1] | 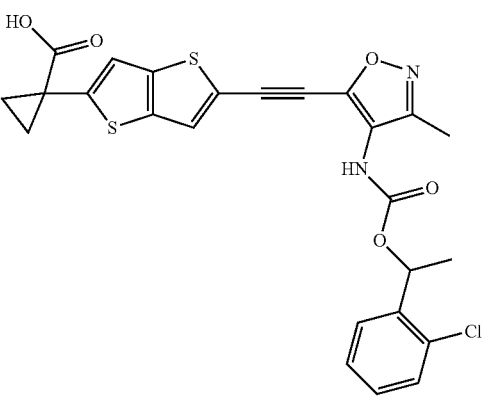 |
| 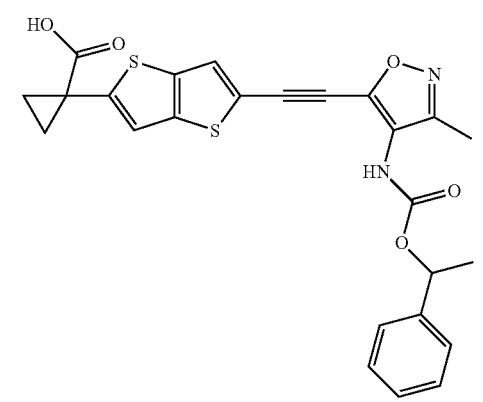 [SMILES: Cc1noc(C#Cc2cc3sc(C4(C(=O)O)CC4)cc3s2)c1NC(=O)OC(C)c1ccccc1] | 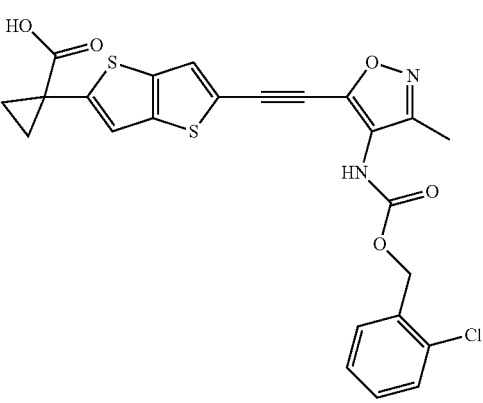 |

1399
TABLE 15-continued
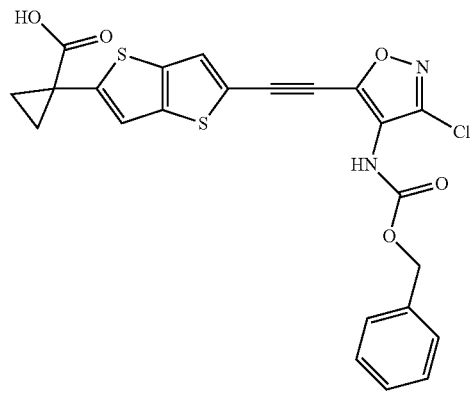
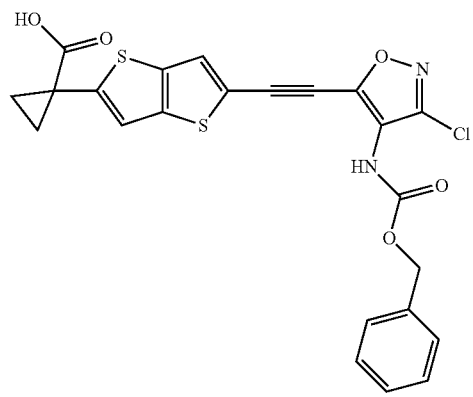
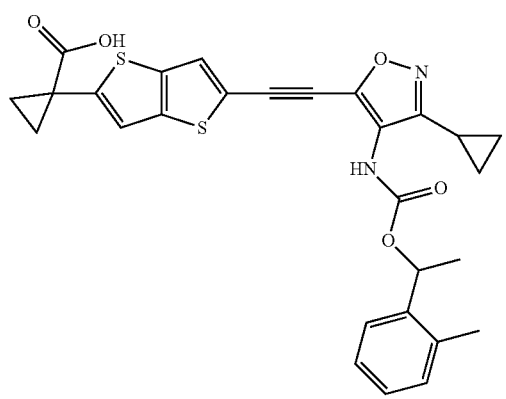 [SMILES: Cc1ccccc1C(C)OC(=O)Nc1c(C2CC2)noc1C#Cc1cc2sc(C3(C(=O)O)CC3)cc2s1]
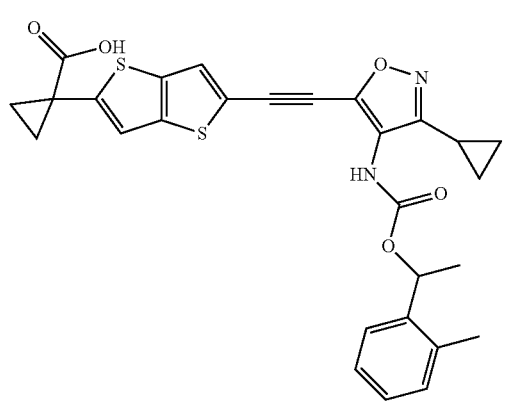
1400
TABLE 15-continued
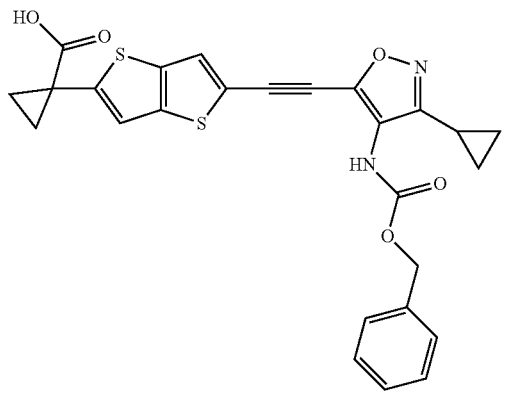
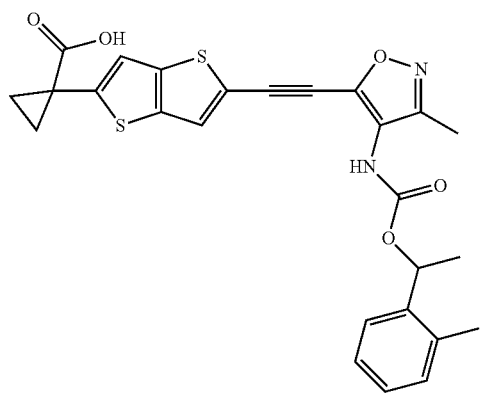
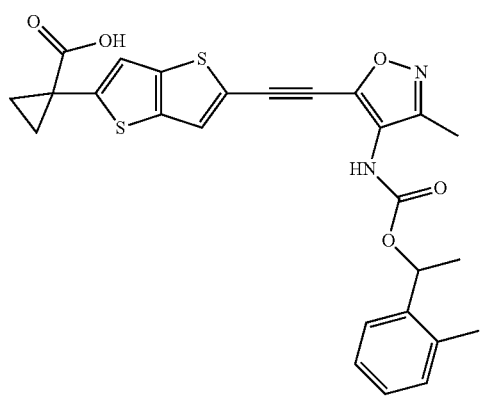
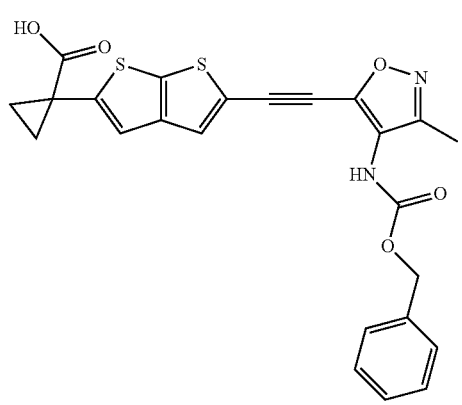

1401
TABLE 15-continued
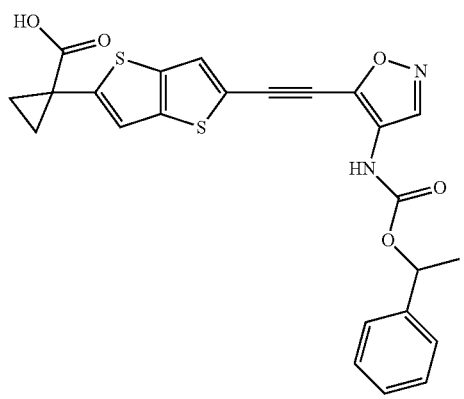 [SMILES: CC(OC(=O)Nc1cnoc1C#Cc1cc2sc(C3(C(=O)O)CC3)cc2s1)c1ccccc1]
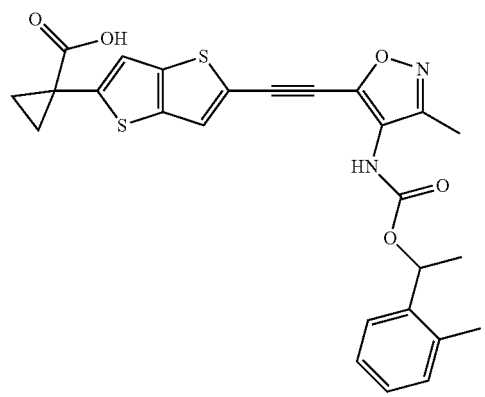
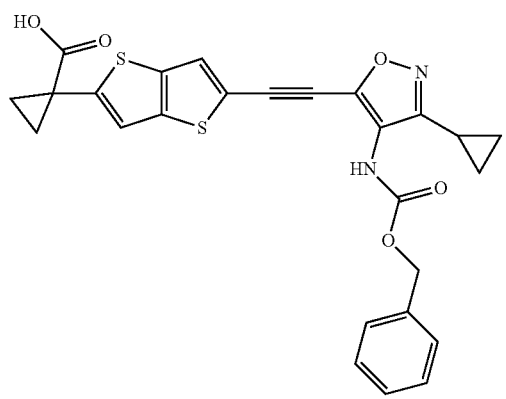 [SMILES: O=C(Nc1c(C2CC2)noc1C#Cc1cc2sc(C3(C(=O)O)CC3)cc2s1)OCc1ccccc1]
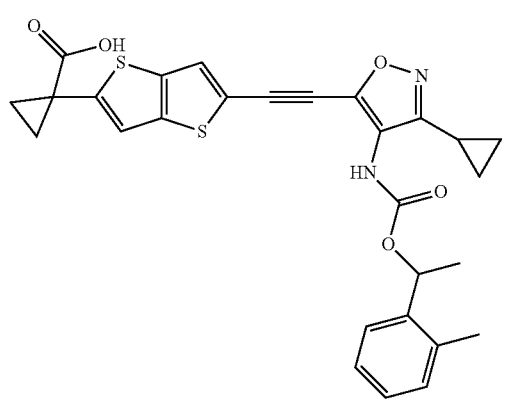
1402
TABLE 15-continued
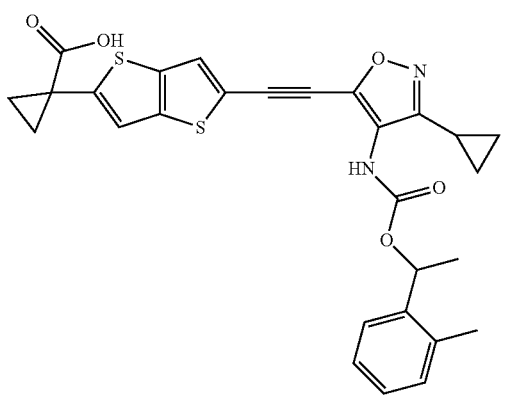
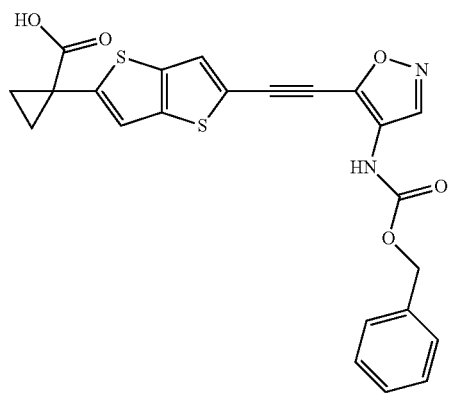 [SMILES: O=C(Nc1cnoc1C#Cc1cc2sc(C3(C(=O)O)CC3)cc2s1)OCc1ccccc1]
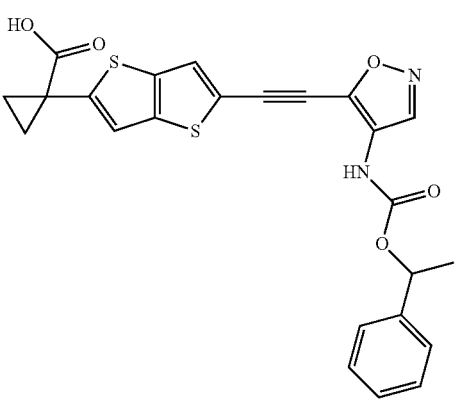
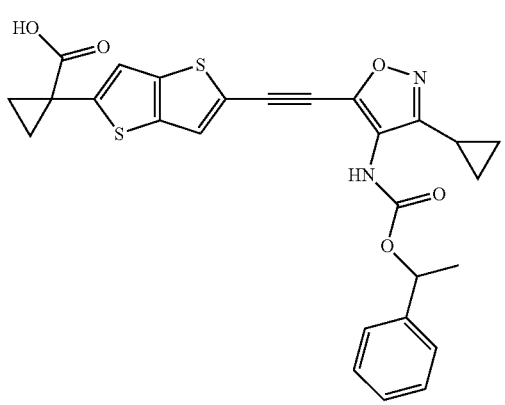 [SMILES: CC(OC(=O)Nc1c(C2CC2)noc1C#Cc1cc2sc(C3(C(=O)O)CC3)cc2s1)c1ccccc1]

1403
TABLE 15-continued
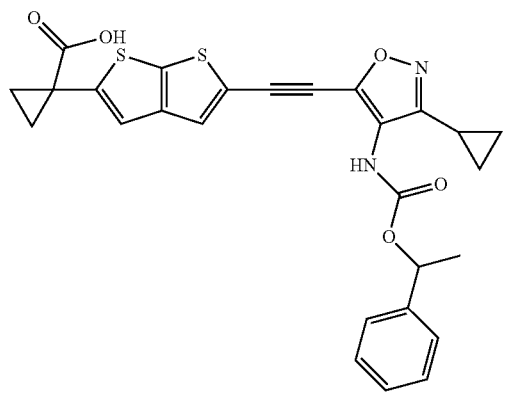 [SMILES: CC(OC(=O)Nc1c(C2CC2)noc1C#Cc1cc2cc(C3(C(=O)O)CC3)sc2s1)c1ccccc1]
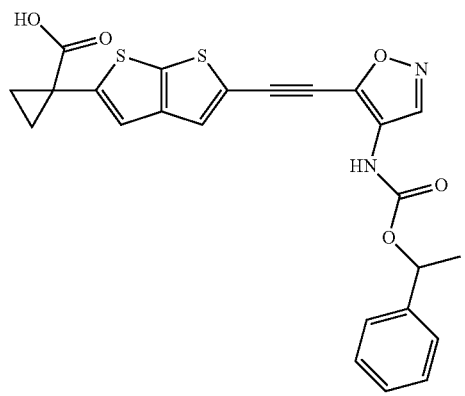 [SMILES: CC(OC(=O)Nc1cnoc1C#Cc1cc2cc(C3(C(=O)O)CC3)sc2s1)c1ccccc1]
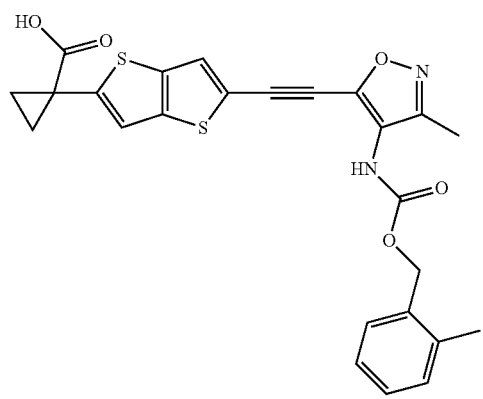 [SMILES: Cc1ccccc1COC(=O)Nc1c(C)noc1C#Cc1cc2sc(C3(C(=O)O)CC3)cc2s1]
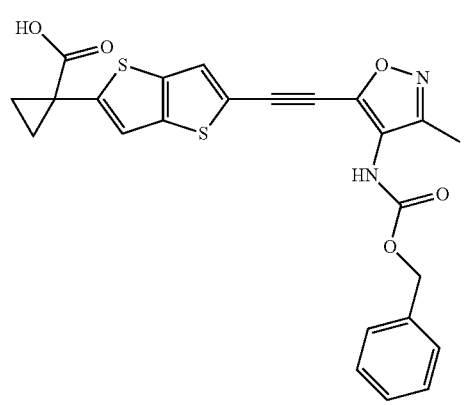
1404
TABLE 15-continued
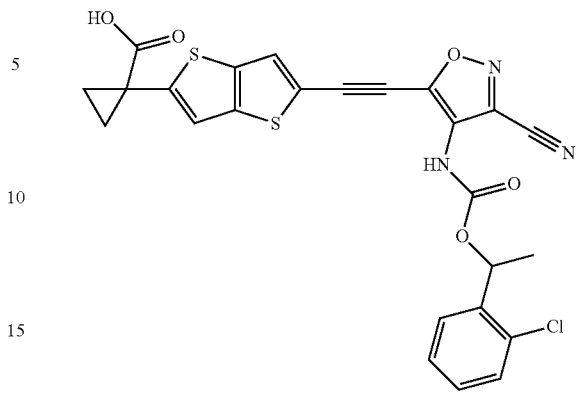
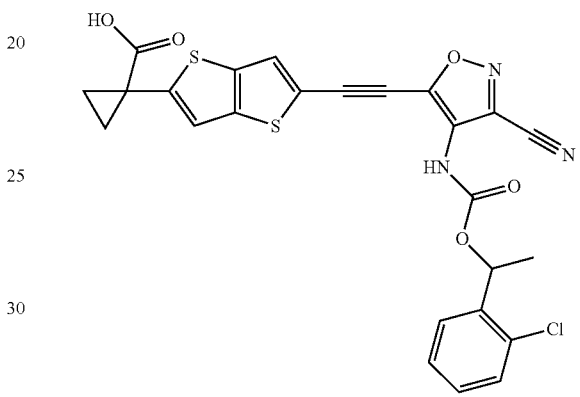
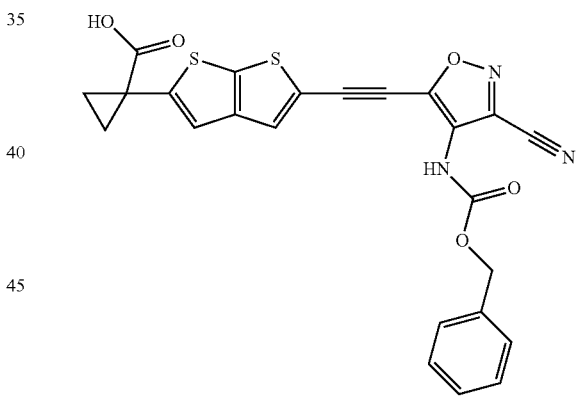
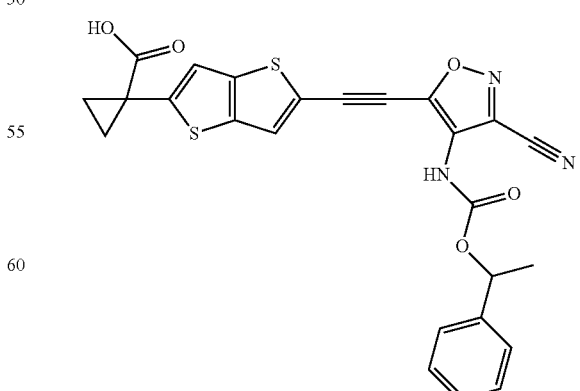

| 1405 | 1406 |
|---|---|
| 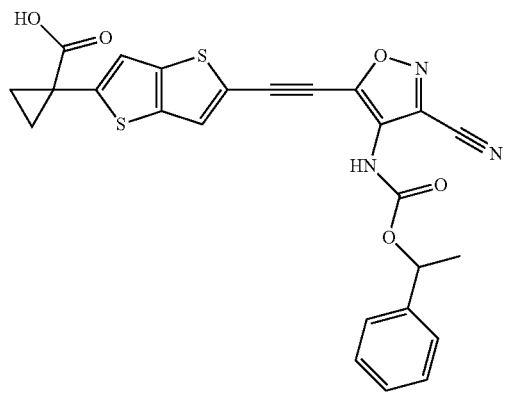 | 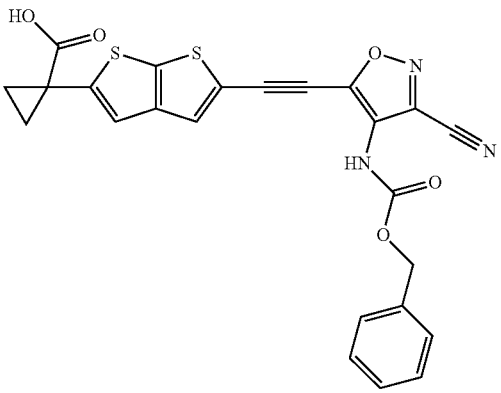 [SMILES: N#Cc1noc(C#Cc2cc3cc(C4(C(=O)O)CC4)sc3s2)c1NC(=O)OCc1ccccc1] |
| 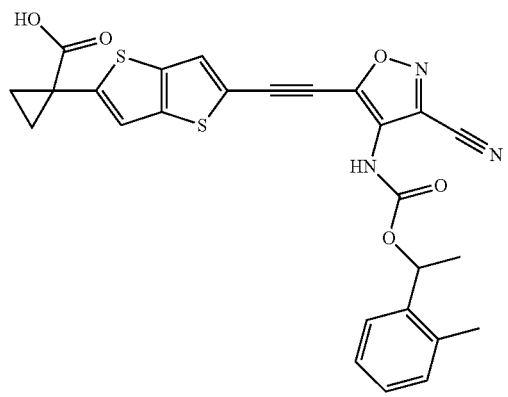 [SMILES: Cc1ccccc1C(C)OC(=O)Nc1c(C#N)noc1C#Cc1cc2sc(C3(C(=O)O)CC3)cc2s1] | 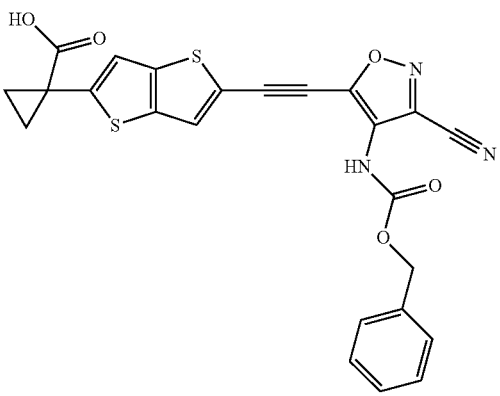 [SMILES: N#Cc1noc(C#Cc2cc3sc(C4(C(=O)O)CC4)cc3s2)c1NC(=O)OCc1ccccc1] |
| 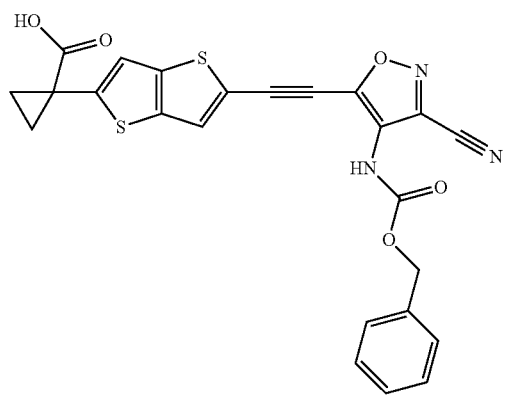 [SMILES: N#Cc1noc(C#Cc2cc3sc(C4(C(=O)O)CC4)cc3s2)c1NC(=O)OCc1ccccc1] | 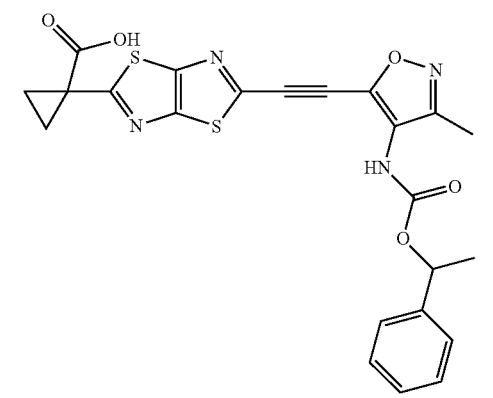 [SMILES: Cc1noc(C#Cc2nc3sc(C4(C(=O)O)CC4)nc3s2)c1NC(=O)OC(C)c1ccccc1] |
| 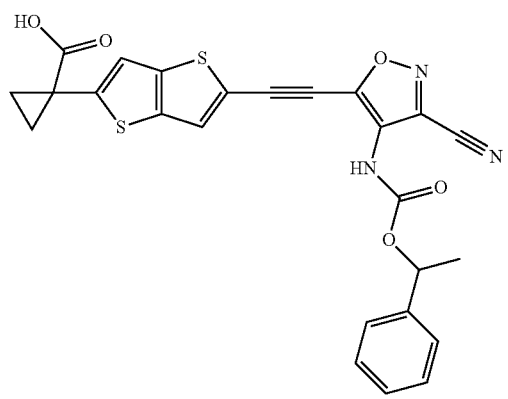 | 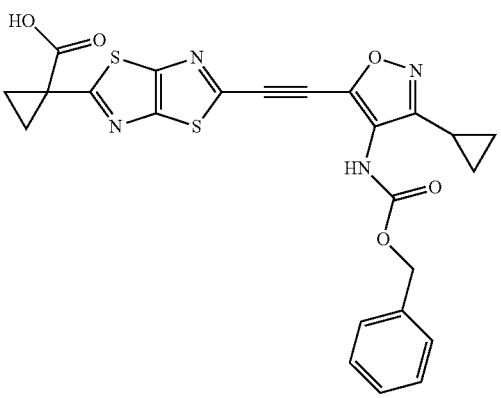 [SMILES: O=C(Nc1c(C2CC2)noc1C#Cc1nc2sc(C3(C(=O)O)CC3)nc2s1)OCc1ccccc1] |

TABLE 15-continued
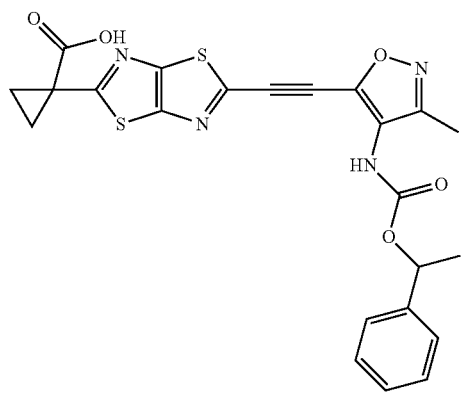 [SMILES: Cc1noc(C#Cc2nc3sc(C4(C(=O)O)CC4)nc3s2)c1NC(=O)OC(C)c1ccccc1]
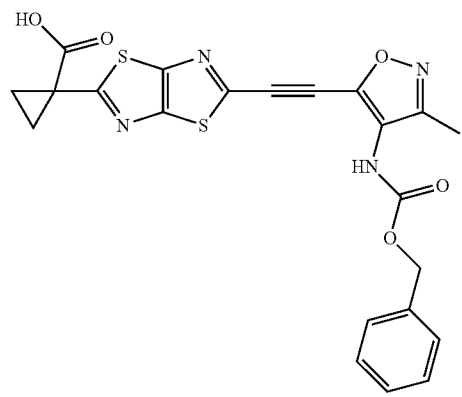 [SMILES: Cc1noc(C#Cc2nc3sc(C4(C(=O)O)CC4)nc3s2)c1NC(=O)OCc1ccccc1]
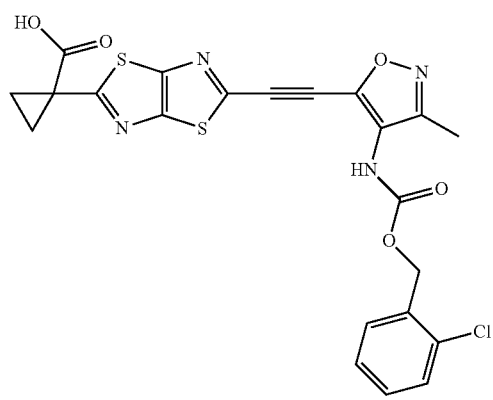 [SMILES: Cc1noc(C#Cc2nc3sc(C4(C(=O)O)CC4)nc3s2)c1NC(=O)OCc1ccccc1Cl]
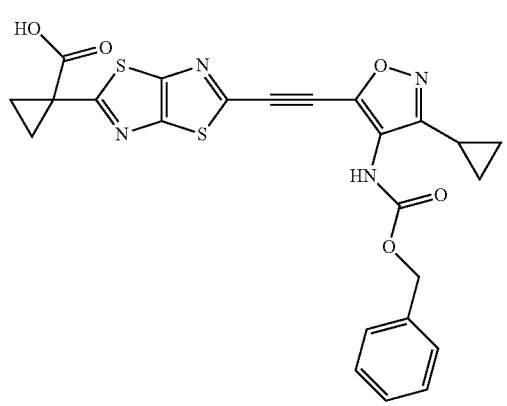 [SMILES: O=C(Nc1c(C2CC2)noc1C#Cc1nc2sc(C3(C(=O)O)CC3)nc2s1)OCc1ccccc1]
TABLE 15-continued
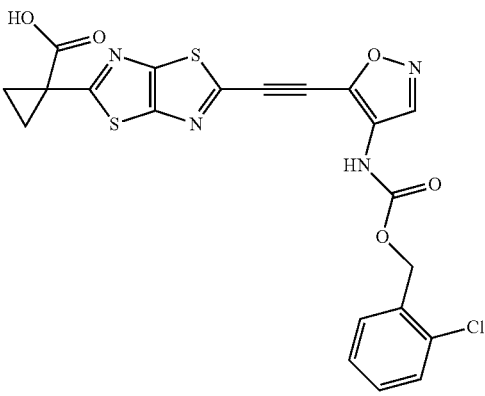 [SMILES: O=C(Nc1cnoc1C#Cc1nc2sc(C3(C(=O)O)CC3)nc2s1)OCc1ccccc1Cl]
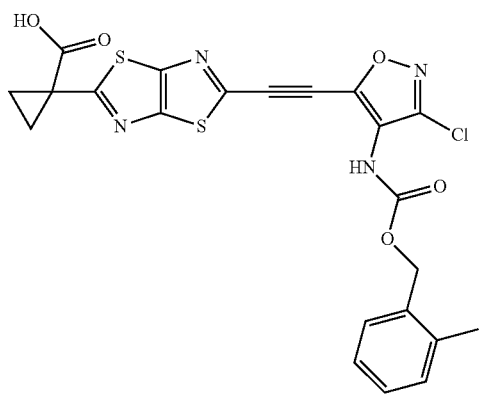
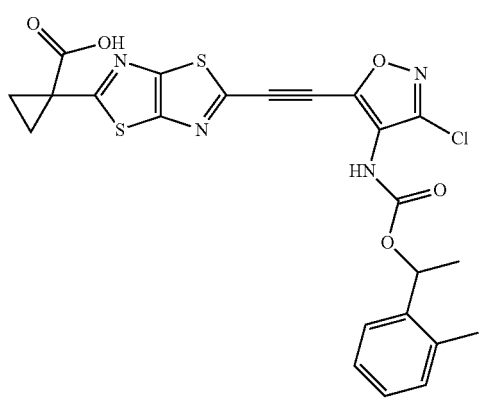
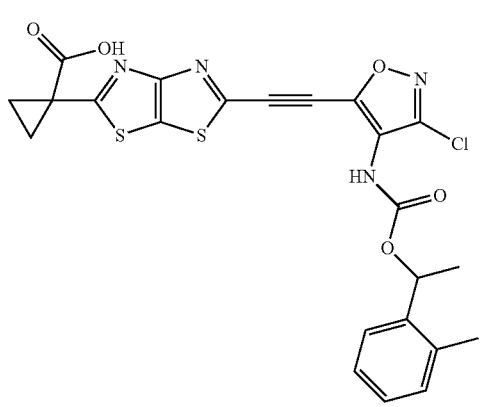 [SMILES: Cc1ccccc1C(C)OC(=O)Nc1c(Cl)noc1C#Cc1nc2nc(C3(C(=O)O)CC3)sc2s1]

TABLE 15-continued
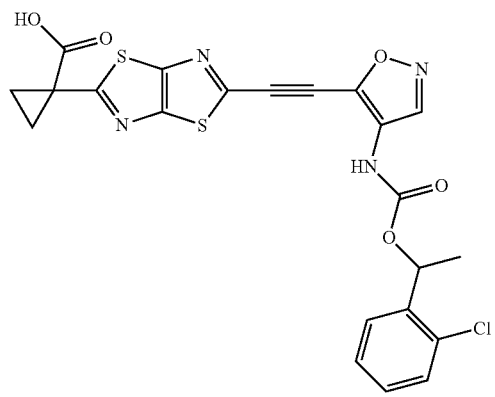 [SMILES: CC(OC(=O)Nc1cnoc1C#Cc1nc2sc(C3(C(=O)O)CC3)nc2s1)c1ccccc1Cl]
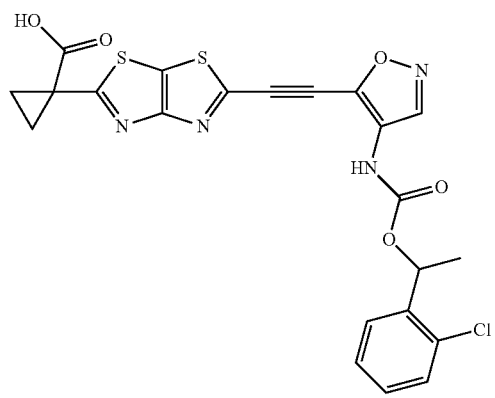 [SMILES: CC(OC(=O)Nc1cnoc1C#Cc1nc2nc(C3(C(=O)O)CC3)sc2s1)c1ccccc1Cl]
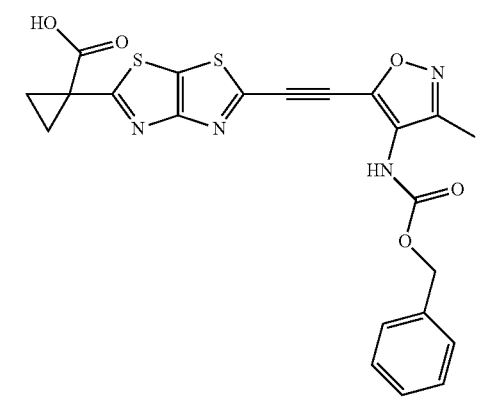
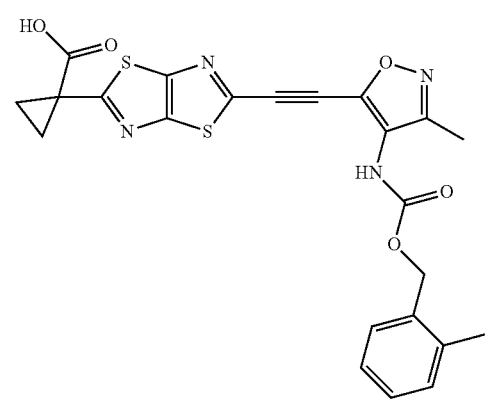
TABLE 15-continued
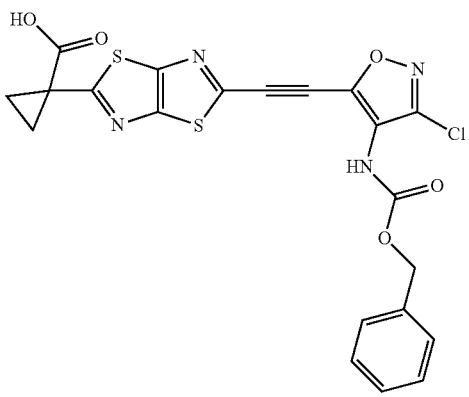
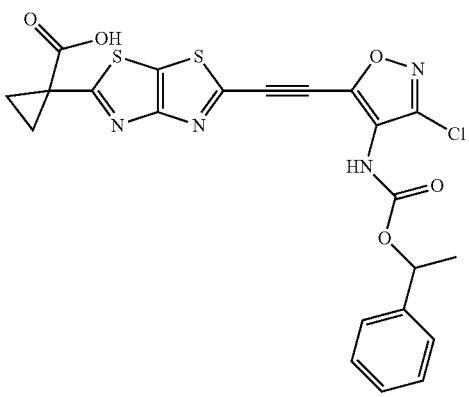
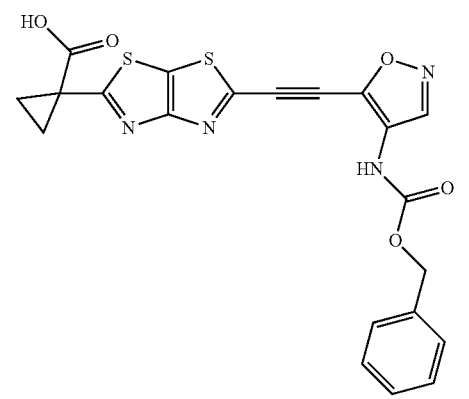 [SMILES: O=C(Nc1cnoc1C#Cc1nc2nc(C3(C(=O)O)CC3)sc2s1)OCc1ccccc1]
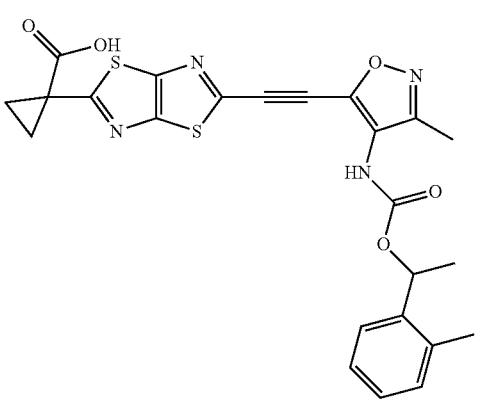 [SMILES: Cc1ccccc1C(C)OC(=O)Nc1c(C)noc1C#Cc1nc2sc(C3(C(=O)O)CC3)nc2s1]

TABLE 15-continued
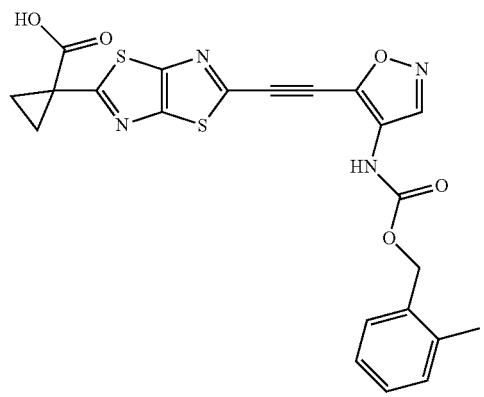
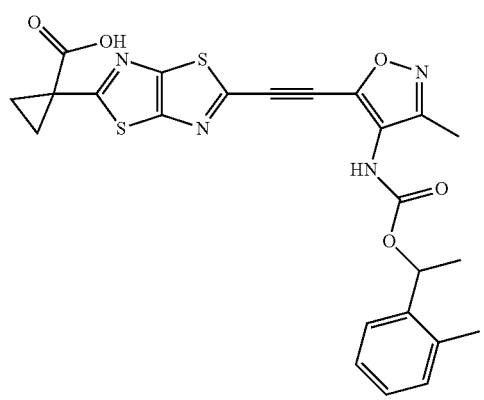
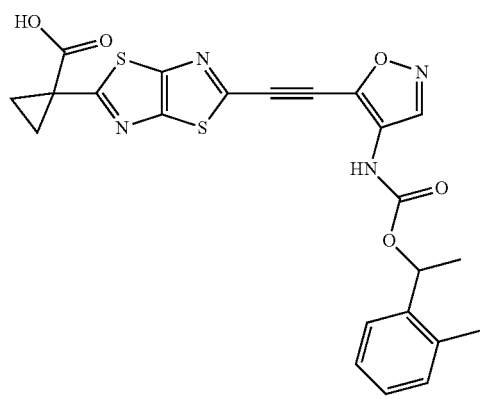 [SMILES: Cc1ccccc1C(C)OC(=O)Nc1cnoc1C#Cc1nc2sc(C3(C(=O)O)CC3)nc2s1]
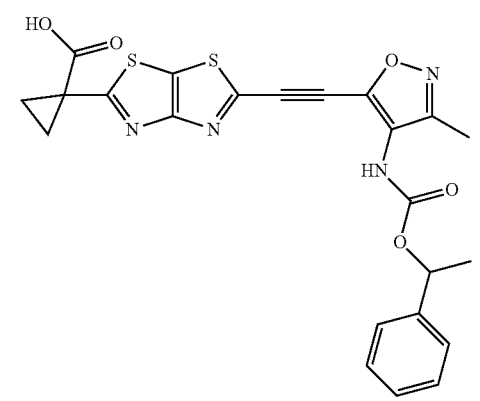
TABLE 15-continued
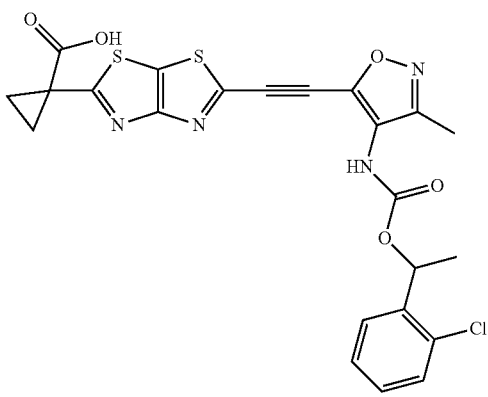
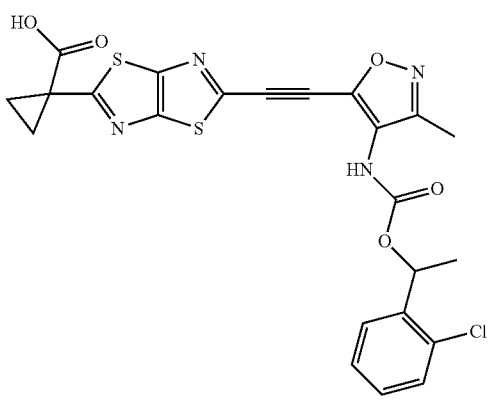
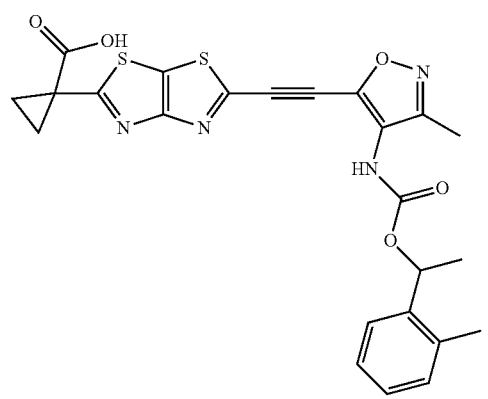 [SMILES: Cc1ccccc1C(C)OC(=O)Nc1c(C)noc1C#Cc1nc2nc(C3(C(=O)O)CC3)sc2s1]
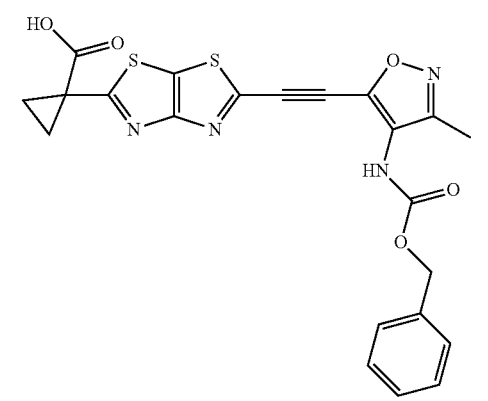

TABLE 15-continued

TABLE 15-continued
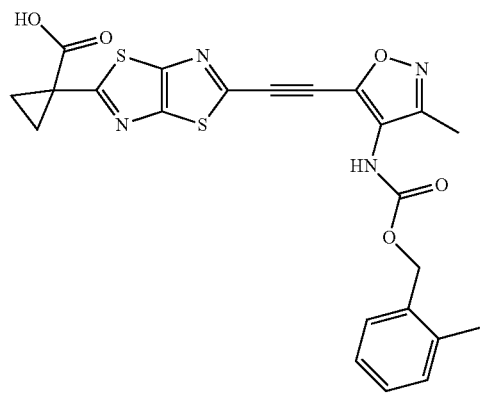
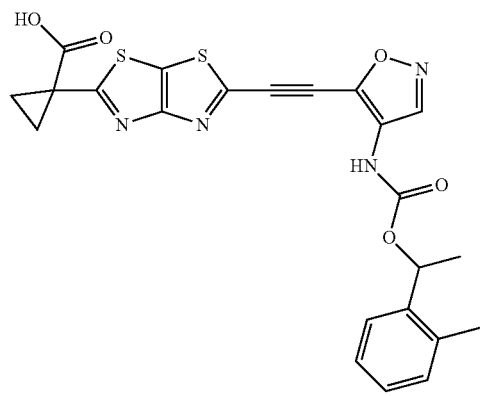
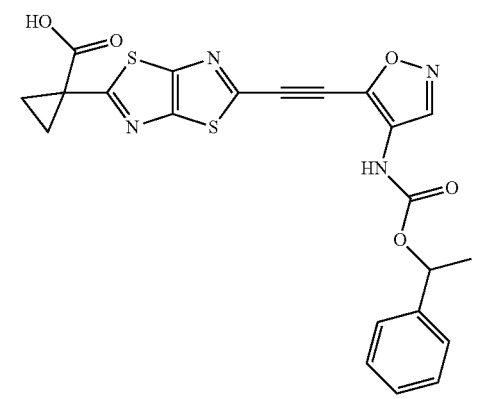
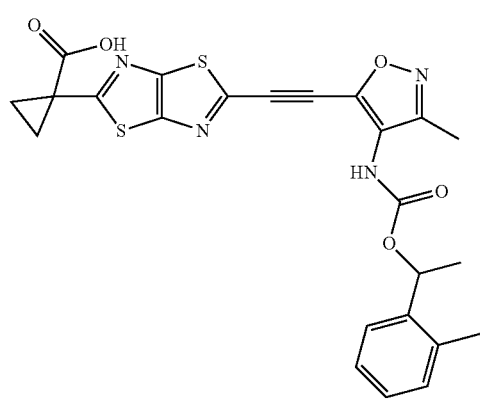
TABLE 15-continued
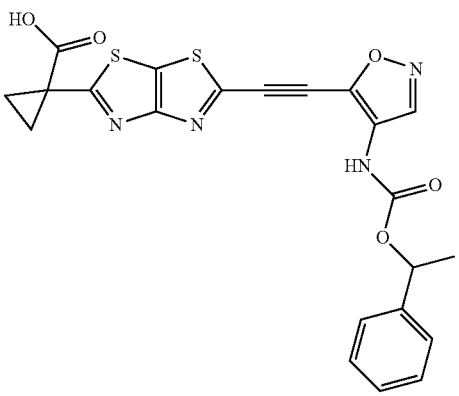 [SMILES: CC(OC(=O)Nc1cnoc1C#Cc1nc2nc(C3(C(=O)O)CC3)sc2s1)c1ccccc1]
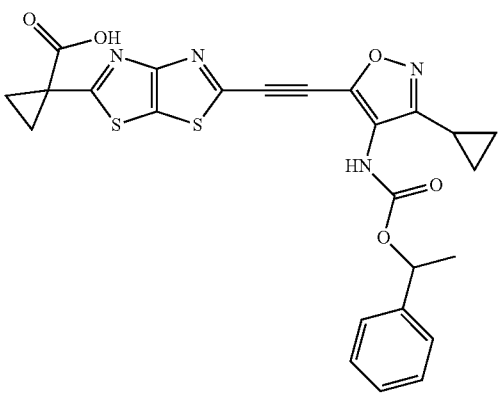 [SMILES: CC(OC(=O)Nc1c(C2CC2)noc1C#Cc1nc2nc(C3(C(=O)O)CC3)sc2s1)c1ccccc1]
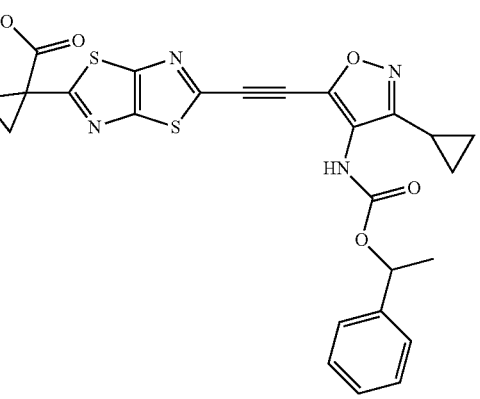
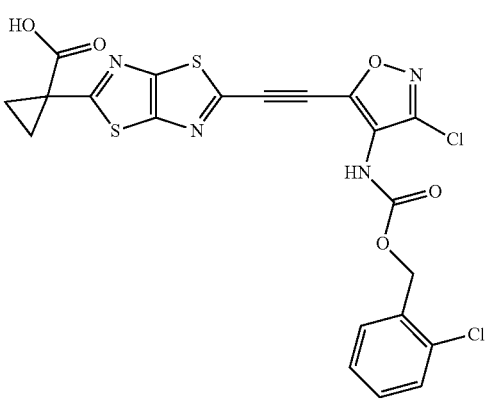

| 1417 | 1418 |
|---|---|
| TABLE 15-continued | TABLE 15-continued |
| 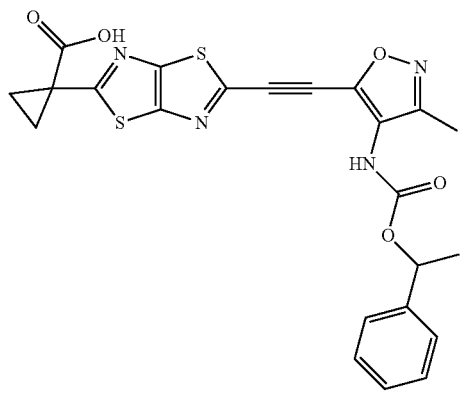 [SMILES: Cc1noc(C#Cc2nc3sc(C4(C(=O)O)CC4)nc3s2)c1NC(=O)OC(C)c1ccccc1] | 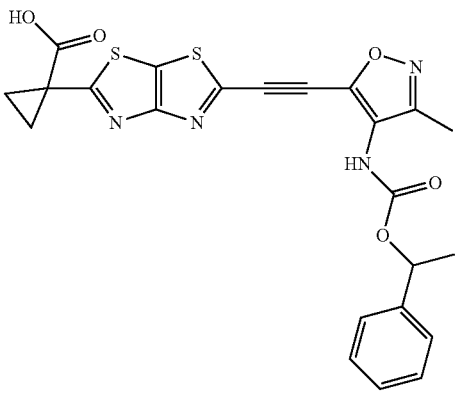 |
| 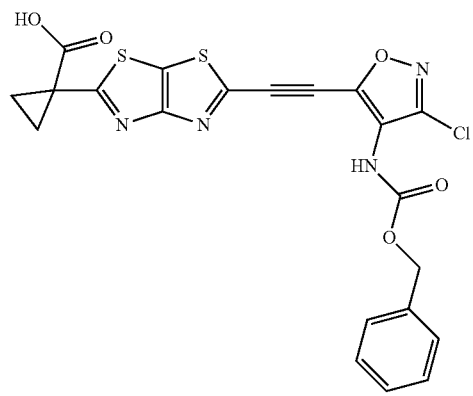 | 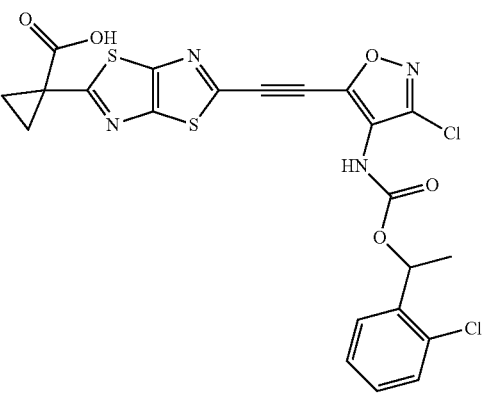 |
| 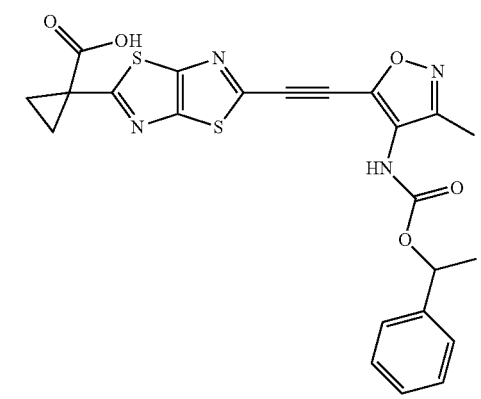 | 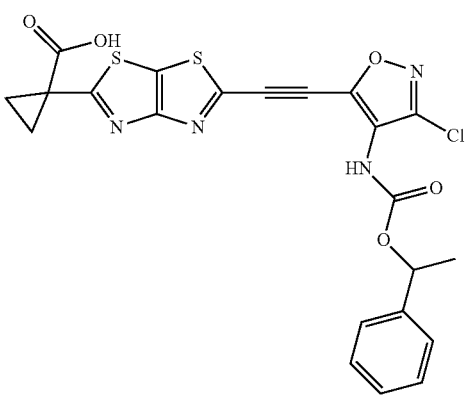 [SMILES: CC(OC(=O)Nc1c(Cl)noc1C#Cc1nc2nc(C3(C(=O)O)CC3)sc2s1)c1ccccc1] |
| 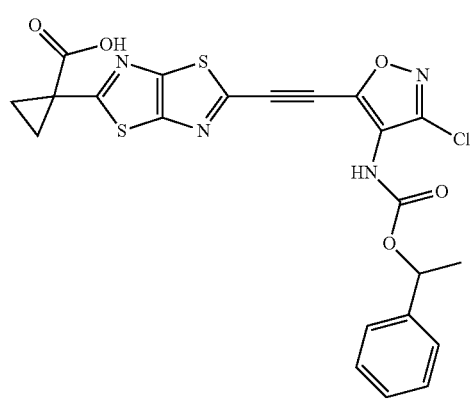 | 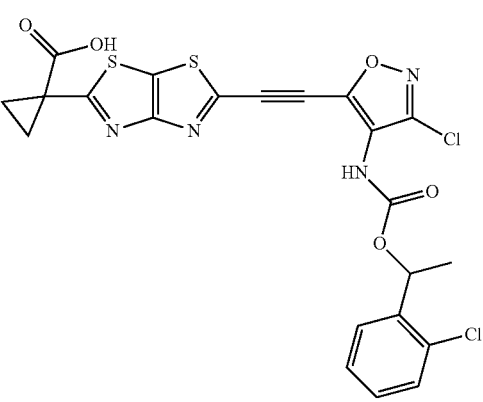 |

TABLE 15-continued
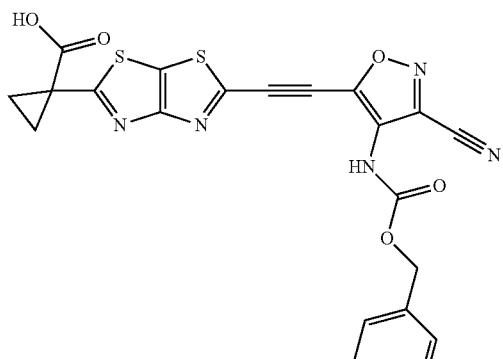
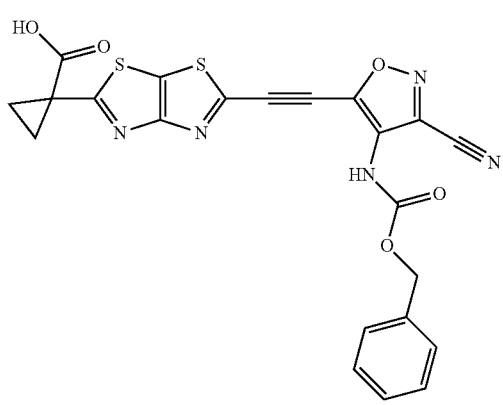
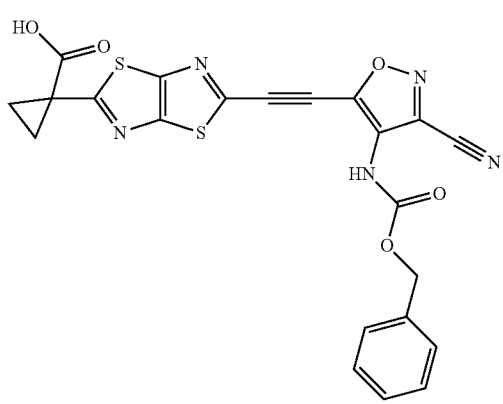 [SMILES: N#Cc1noc(C#Cc2nc3sc(C4(C(=O)O)CC4)nc3s2)c1NC(=O)OCc1ccccc1]
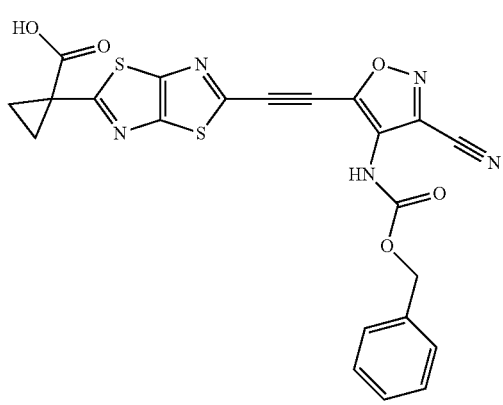
or pharmaceutically acceptable salts thereof.
32. The compound or pharmaceutically acceptable salt thereof of claim 1, selected from compounds of Table 16 having the following structures:
TABLE 16
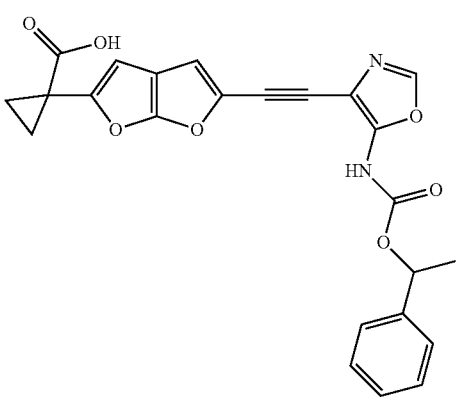 [SMILES: CC(OC(=O)Nc1ocnc1C#Cc1cc2cc(C3(C(=O)O)CC3)oc2o1)c1ccccc1]
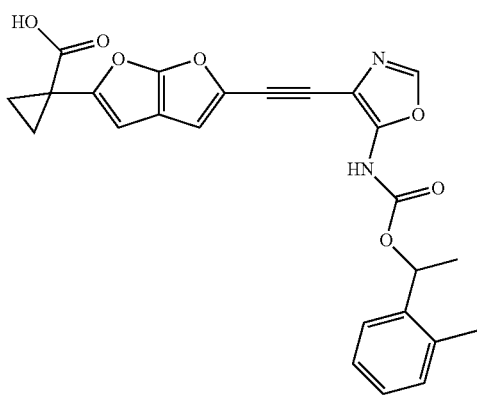 [SMILES: Cc1ccccc1C(C)OC(=O)Nc1ocnc1C#Cc1cc2cc(C3(C(=O)O)CC3)oc2o1]
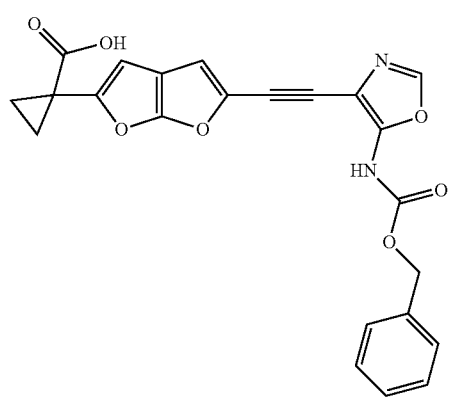 [SMILES: O=C(Nc1ocnc1C#Cc1cc2cc(C3(C(=O)O)CC3)oc2o1)OCc1ccccc1]

1421
TABLE 16-continued
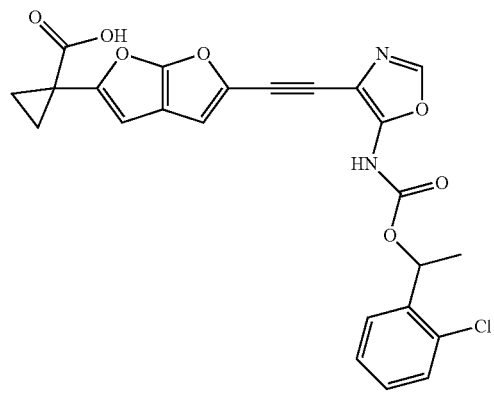 [SMILES: CC(OC(=O)Nc1ocnc1C#Cc1cc2cc(C3(C(=O)O)CC3)oc2o1)c1ccccc1Cl]
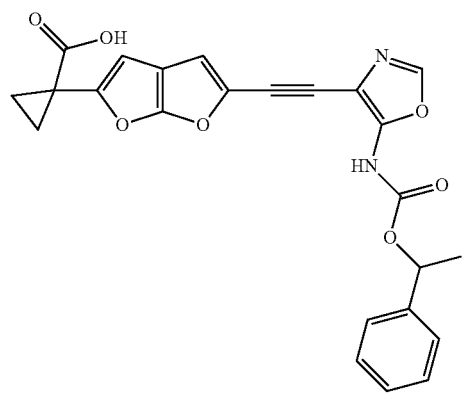 [SMILES: CC(OC(=O)Nc1ocnc1C#Cc1cc2cc(C3(C(=O)O)CC3)oc2o1)c1ccccc1]
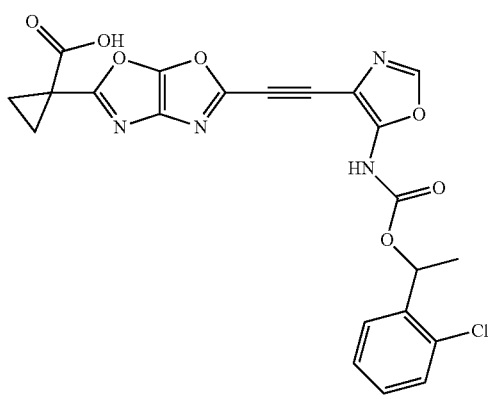 [SMILES: CC(OC(=O)Nc1ocnc1C#Cc1nc2nc(C3(C(=O)O)CC3)oc2o1)c1ccccc1Cl]
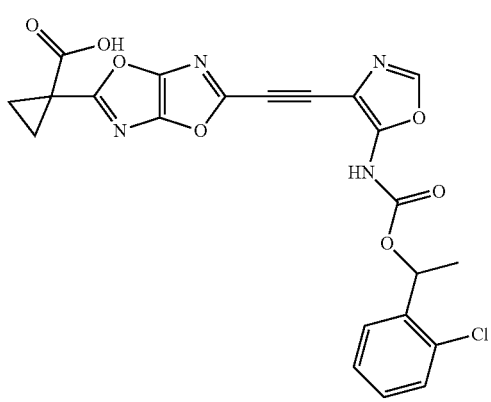 [SMILES: CC(OC(=O)Nc1ocnc1C#Cc1nc2oc(C3(C(=O)O)CC3)nc2o1)c1ccccc1Cl]
1422
TABLE 16-continued
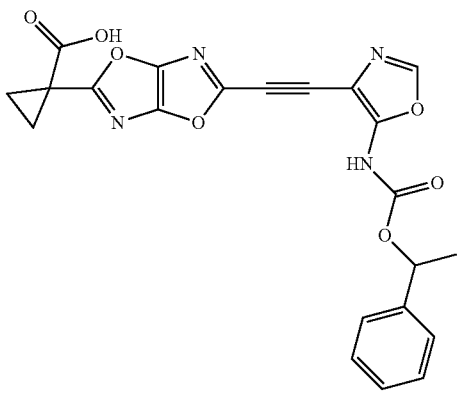 [SMILES: CC(OC(=O)Nc1ocnc1C#Cc1nc2oc(C3(C(=O)O)CC3)nc2o1)c1ccccc1]
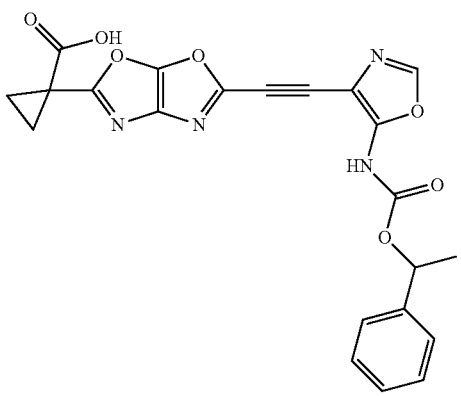 [SMILES: CC(OC(=O)Nc1ocnc1C#Cc1nc2nc(C3(C(=O)O)CC3)oc2o1)c1ccccc1]
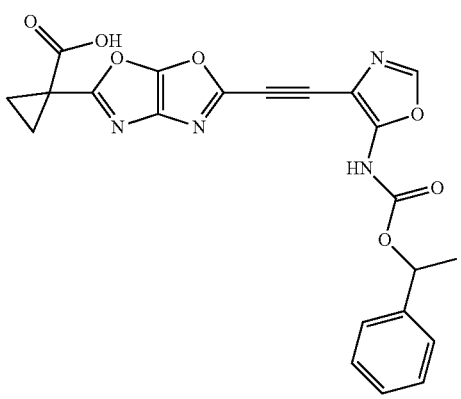 [SMILES: CC(OC(=O)Nc1ocnc1C#Cc1nc2nc(C3(C(=O)O)CC3)oc2o1)c1ccccc1]
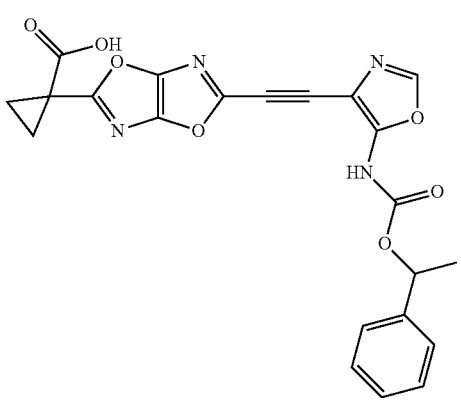 [SMILES: CC(OC(=O)Nc1ocnc1C#Cc1nc2oc(C3(C(=O)O)CC3)nc2o1)c1ccccc1]

US 8,975,235 B2
| 1423 | 1424 |
|---|---|
| TABLE 16-continued | TABLE 16-continued |
| 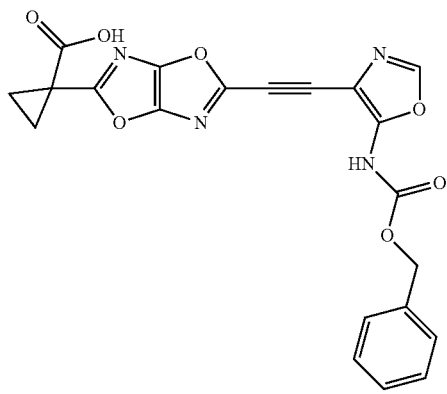 [SMILES: O=C(Nc1ocnc1C#Cc1nc2oc(C3(C(=O)O)CC3)nc2o1)OCc1ccccc1] | 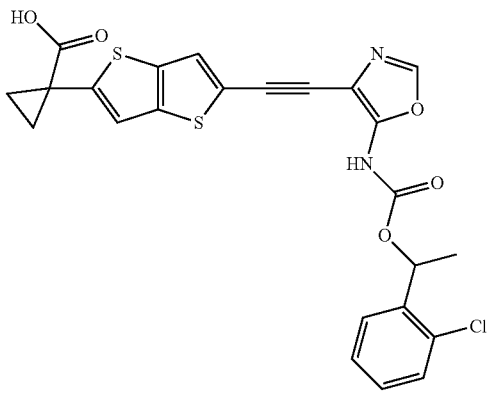 |
| 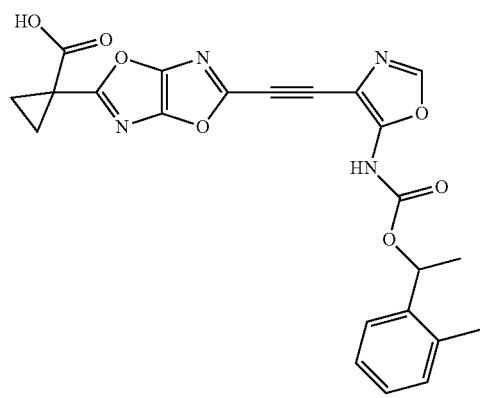 [SMILES: Cc1ccccc1C(C)OC(=O)Nc1ocnc1C#Cc1nc2oc(C3(C(=O)O)CC3)nc2o1] | 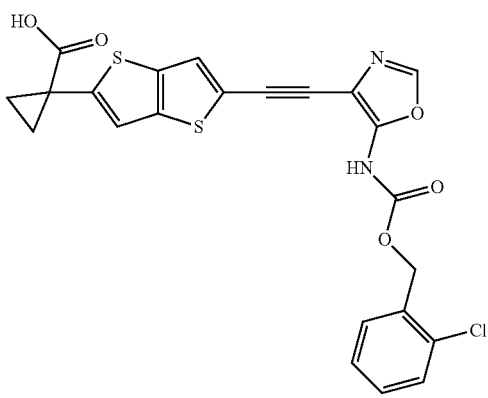 |
| 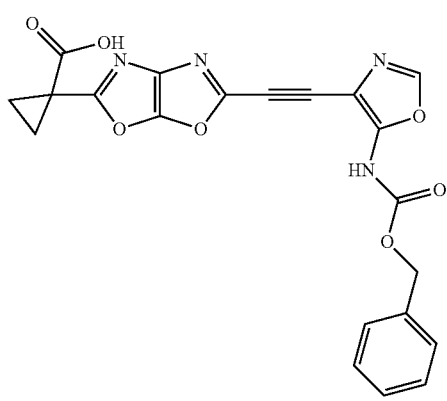 [SMILES: O=C(Nc1ocnc1C#Cc1nc2nc(C3(C(=O)O)CC3)oc2o1)OCc1ccccc1] | 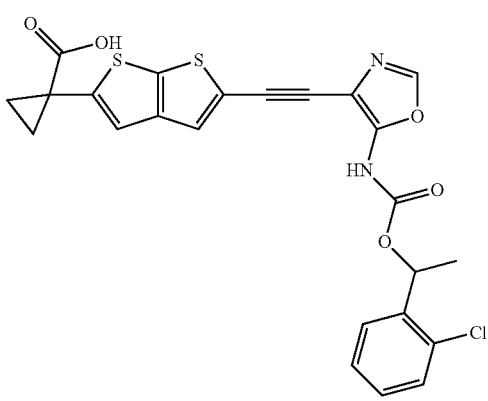 |
| 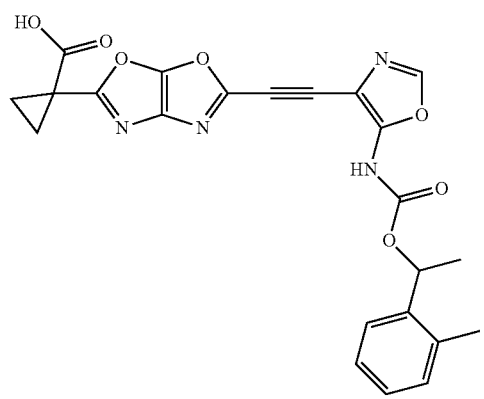 [SMILES: Cc1ccccc1C(C)OC(=O)Nc1ocnc1C#Cc1nc2nc(C3(C(=O)O)CC3)oc2o1] | 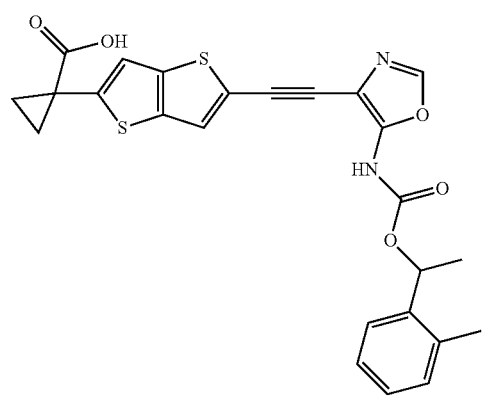 [SMILES: Cc1ccccc1C(C)OC(=O)Nc1ocnc1C#Cc1cc2sc(C3(C(=O)O)CC3)cc2s1] |

TABLE 16-continued
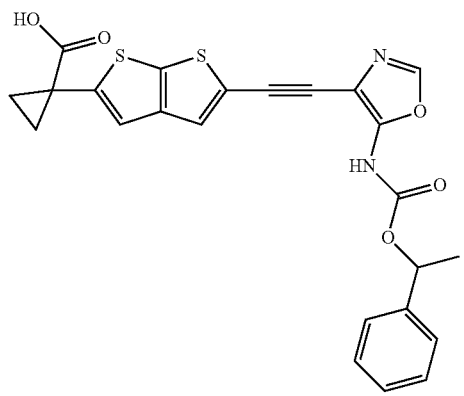 [SMILES: CC(OC(=O)Nc1ocnc1C#Cc1cc2cc(C3(C(=O)O)CC3)sc2s1)c1ccccc1]
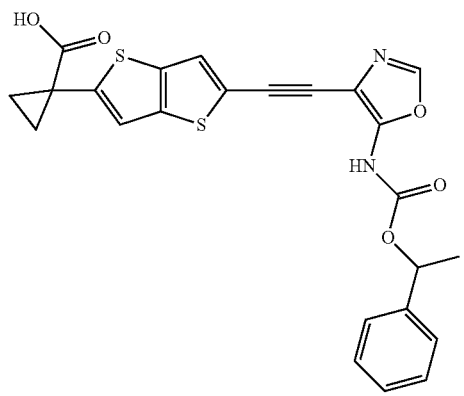 [SMILES: CC(OC(=O)Nc1ocnc1C#Cc1cc2sc(C3(C(=O)O)CC3)cc2s1)c1ccccc1]
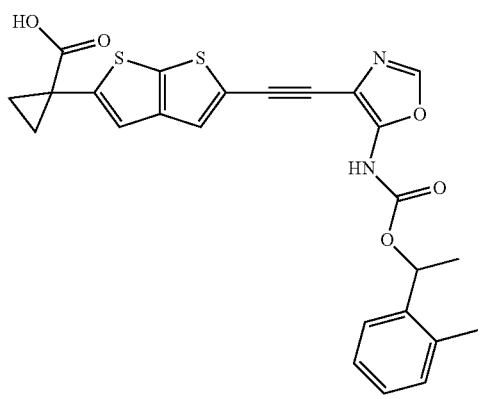 [SMILES: Cc1ccccc1C(C)OC(=O)Nc1ocnc1C#Cc1cc2cc(C3(C(=O)O)CC3)sc2s1]
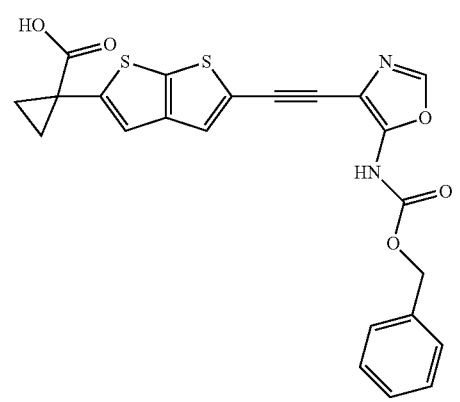 [SMILES: O=C(Nc1ocnc1C#Cc1cc2cc(C3(C(=O)O)CC3)sc2s1)OCc1ccccc1]
TABLE 16-continued
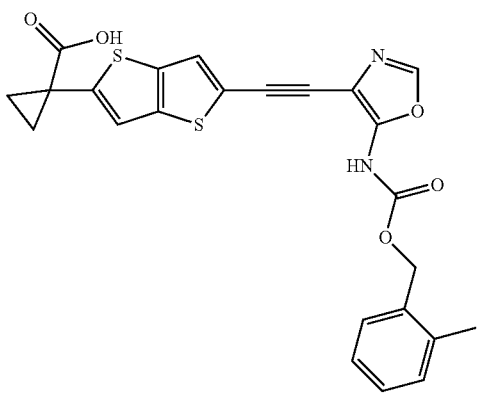 [SMILES: Cc1ccccc1COC(=O)Nc1ocnc1C#Cc1cc2sc(C3(C(=O)O)CC3)cc2s1]
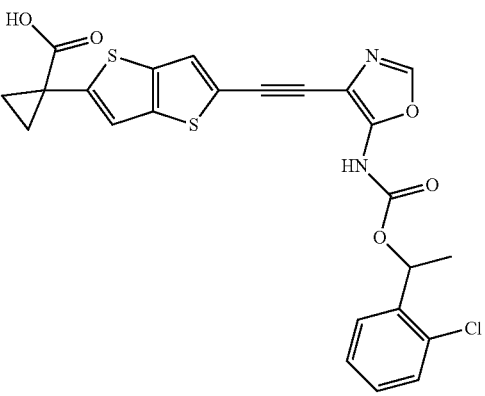
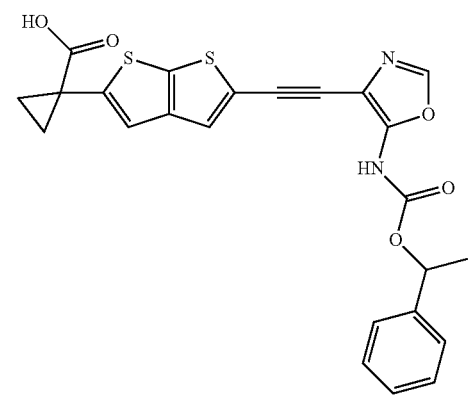 [SMILES: CC(OC(=O)Nc1ocnc1C#Cc1cc2cc(C3(C(=O)O)CC3)sc2s1)c1ccccc1]
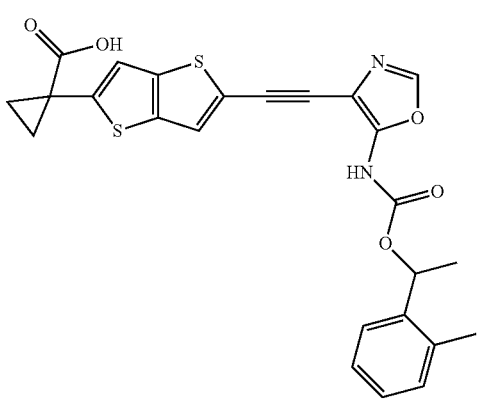 [SMILES: Cc1ccccc1C(C)OC(=O)Nc1ocnc1C#Cc1cc2sc(C3(C(=O)O)CC3)cc2s1]

TABLE 16-continued
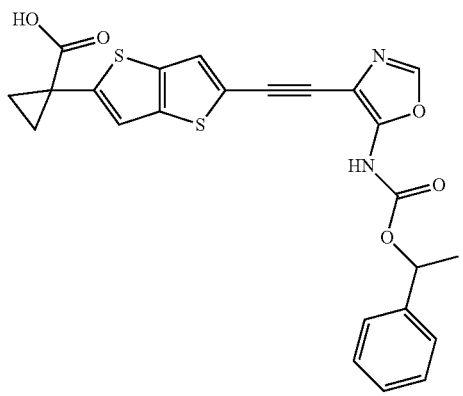 [SMILES: CC(OC(=O)Nc1ocnc1C#Cc1cc2sc(C3(C(=O)O)CC3)cc2s1)c1ccccc1]
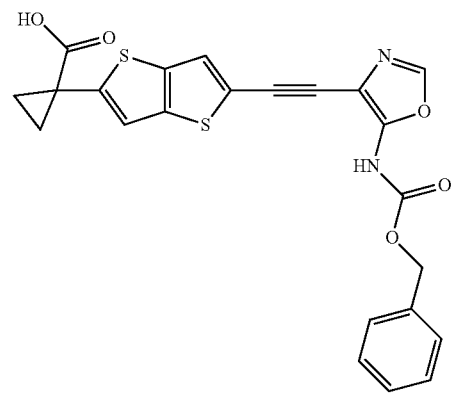 [SMILES: O=C(Nc1ocnc1C#Cc1cc2sc(C3(C(=O)O)CC3)cc2s1)OCc1ccccc1]
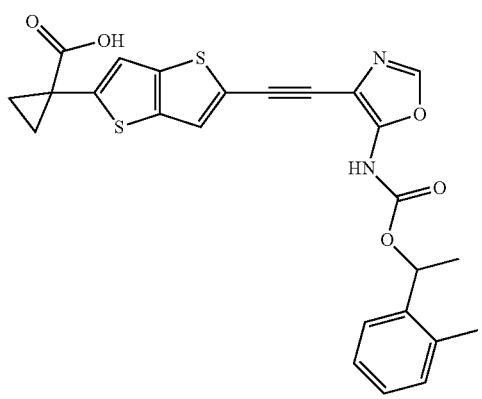 [SMILES: Cc1ccccc1C(C)OC(=O)Nc1ocnc1C#Cc1cc2sc(C3(C(=O)O)CC3)cc2s1]
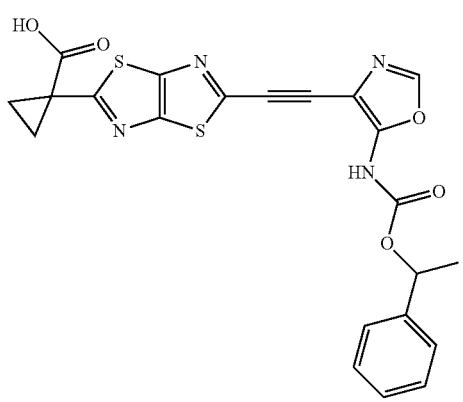 [SMILES: CC(OC(=O)Nc1ocnc1C#Cc1nc2sc(C3(C(=O)O)CC3)nc2s1)c1ccccc1]
TABLE 16-continued
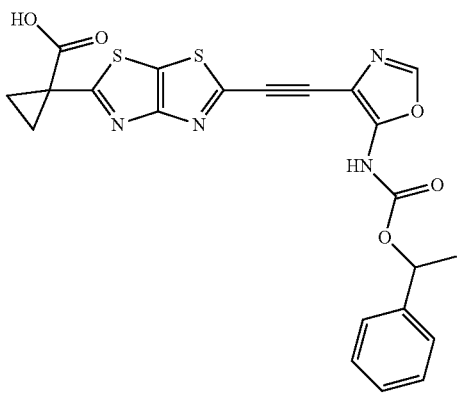 [SMILES: CC(OC(=O)Nc1ocnc1C#Cc1nc2nc(C3(C(=O)O)CC3)sc2s1)c1ccccc1]
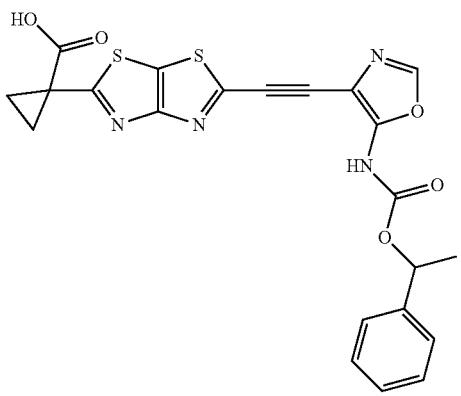 [SMILES: CC(OC(=O)Nc1ocnc1C#Cc1nc2nc(C3(C(=O)O)CC3)sc2s1)c1ccccc1]
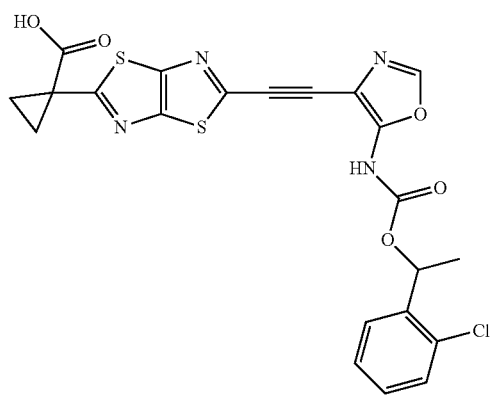 [SMILES: CC(OC(=O)Nc1ocnc1C#Cc1nc2sc(C3(C(=O)O)CC3)nc2s1)c1ccccc1Cl]
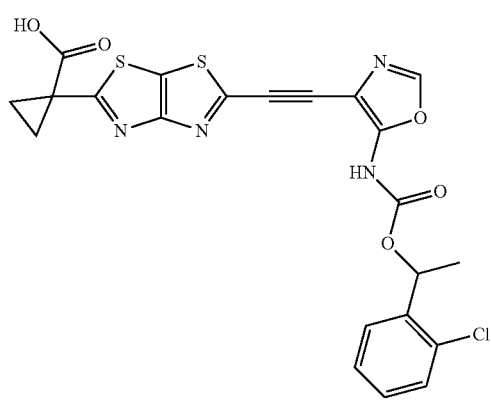 [SMILES: CC(OC(=O)Nc1ocnc1C#Cc1nc2nc(C3(C(=O)O)CC3)sc2s1)c1ccccc1Cl]

1429
TABLE 16-continued
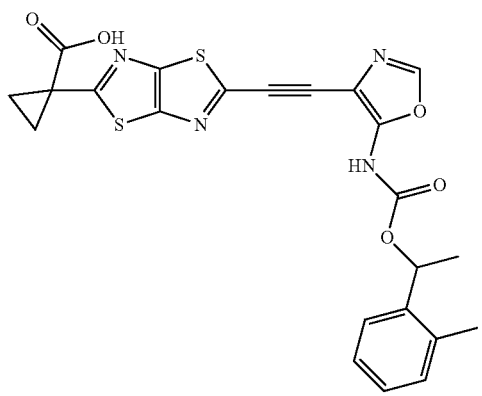 [SMILES: Cc1ccccc1C(C)OC(=O)Nc1ocnc1C#Cc1nc2sc(C3(C(=O)O)CC3)nc2s1]
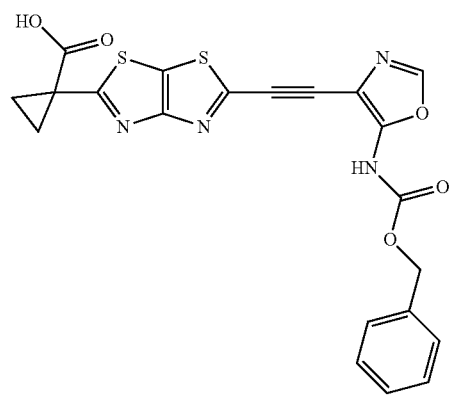 [SMILES: O=C(Nc1ocnc1C#Cc1nc2nc(C3(C(=O)O)CC3)sc2s1)OCc1ccccc1]
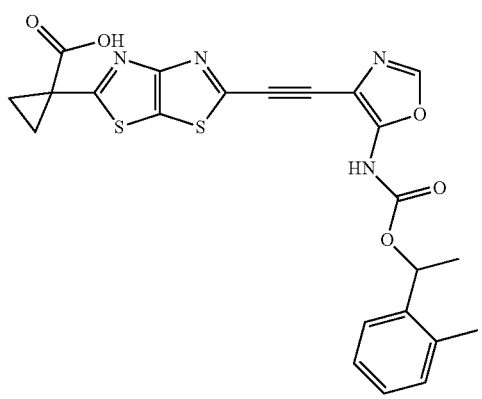 [SMILES: Cc1ccccc1C(C)OC(=O)Nc1ocnc1C#Cc1nc2nc(C3(C(=O)O)CC3)sc2s1]
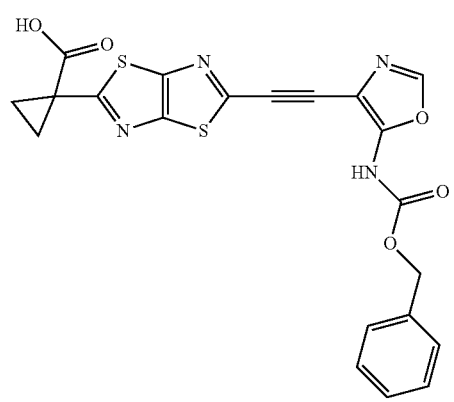 [SMILES: O=C(Nc1ocnc1C#Cc1nc2sc(C3(C(=O)O)CC3)nc2s1)OCc1ccccc1]
1430
TABLE 16-continued
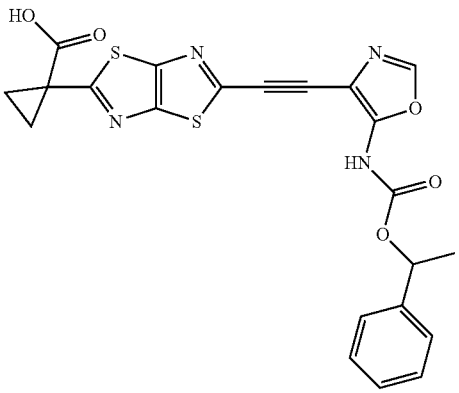 [SMILES: CC(OC(=O)Nc1ocnc1C#Cc1nc2sc(C3(C(=O)O)CC3)nc2s1)c1ccccc1]
or pharmaceutically acceptable salts thereof.
33. The compound or pharmaceutically acceptable salt thereof of claim 1, selected from compounds of Table 17 having the following structures:
TABLE 17
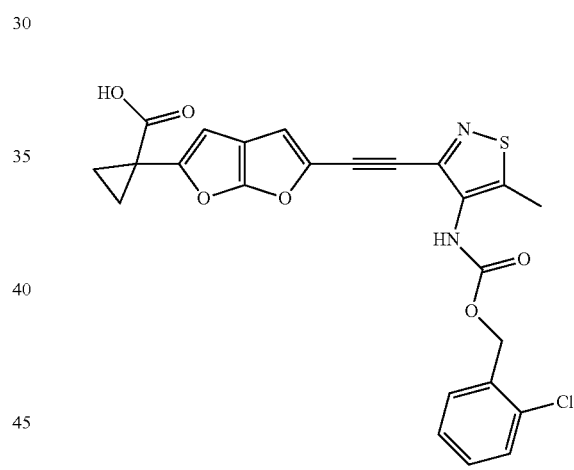

1431
TABLE 17-continued
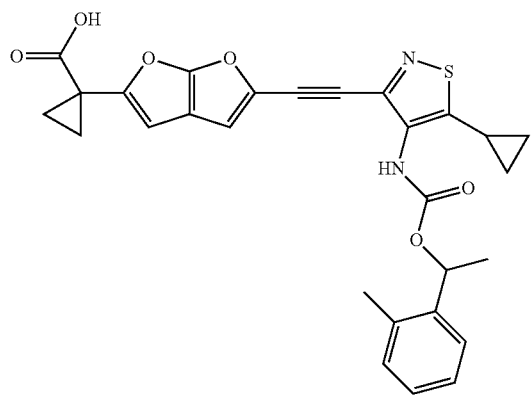
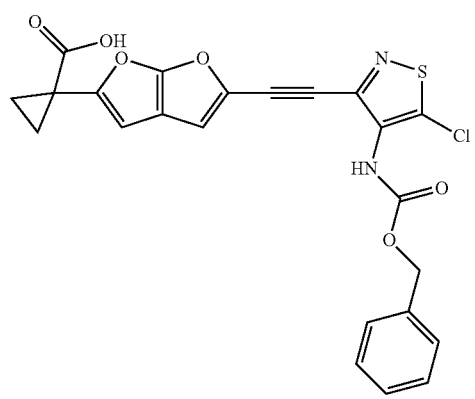 [SMILES: O=C(Nc1c(C#Cc2cc3cc(C4(C(=O)O)CC4)oc3o2)nsc1Cl)OCc1ccccc1]
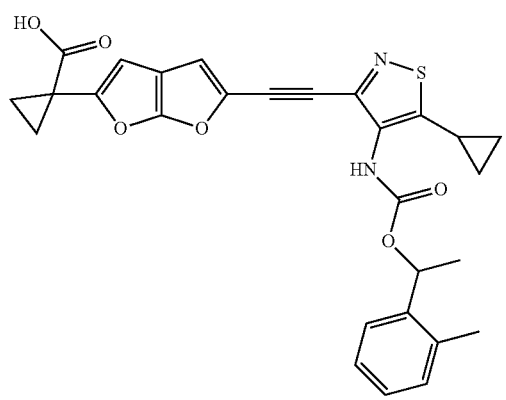 [SMILES: Cc1ccccc1C(C)OC(=O)Nc1c(C#Cc2cc3cc(C4(C(=O)O)CC4)oc3o2)nsc1C1CC1]
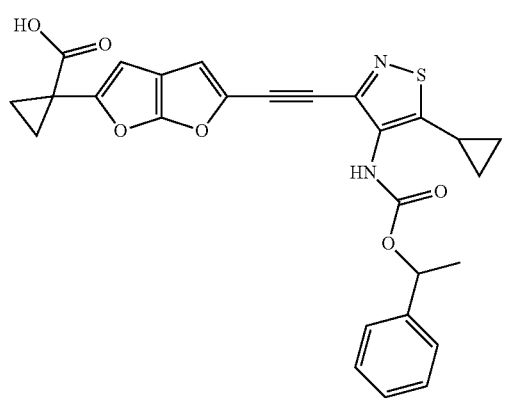
1432
TABLE 17-continued
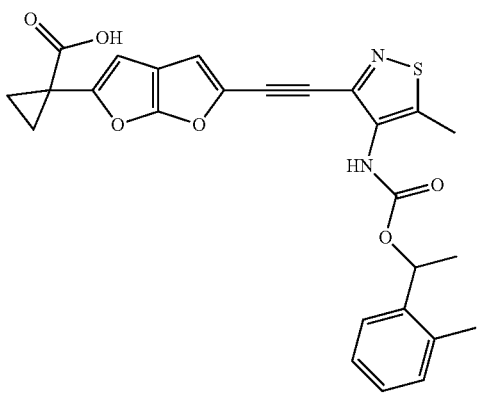 [SMILES: Cc1ccccc1C(C)OC(=O)Nc1c(C#Cc2cc3cc(C4(C(=O)O)CC4)oc3o2)nsc1C]
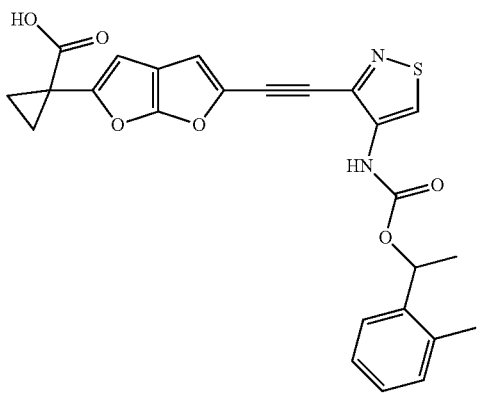 [SMILES: Cc1ccccc1C(C)OC(=O)Nc1csnc1C#Cc1cc2cc(C3(C(=O)O)CC3)oc2o1]
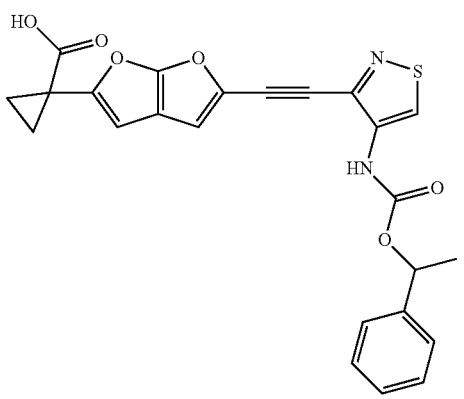
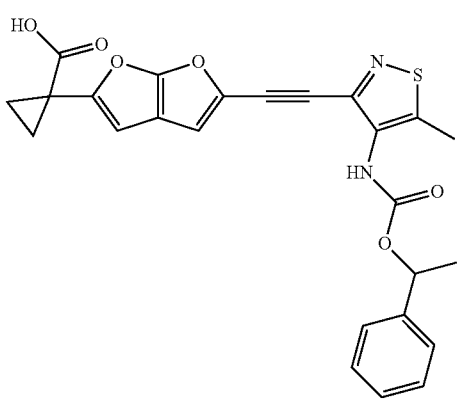 [SMILES: Cc1snc(C#Cc2cc3cc(C4(C(=O)O)CC4)oc3o2)c1NC(=O)OC(C)c1ccccc1]

1433
TABLE 17-continued
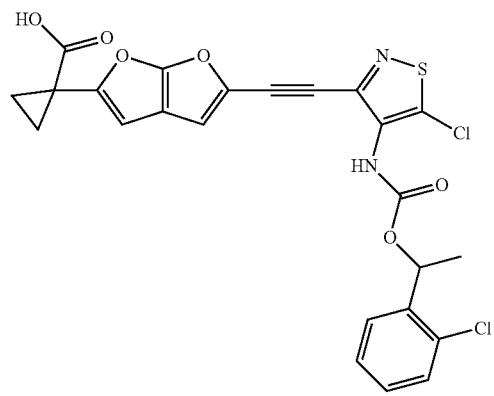 [SMILES: CC(OC(=O)Nc1c(C#Cc2cc3cc(C4(C(=O)O)CC4)oc3o2)nsc1Cl)c1ccccc1Cl]
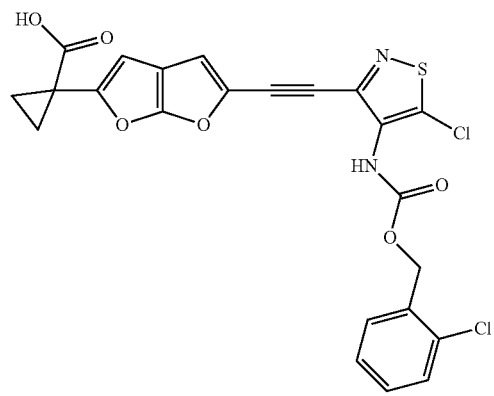 [SMILES: O=C(Nc1c(C#Cc2cc3cc(C4(C(=O)O)CC4)oc3o2)nsc1Cl)OCc1ccccc1Cl]
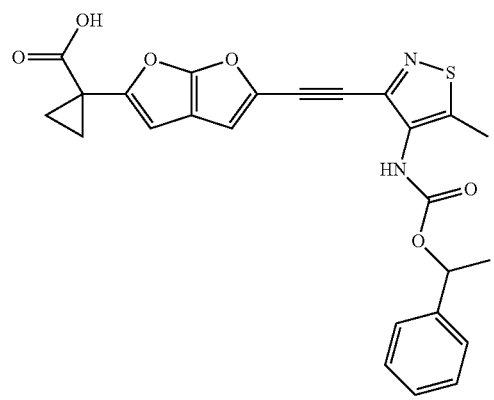
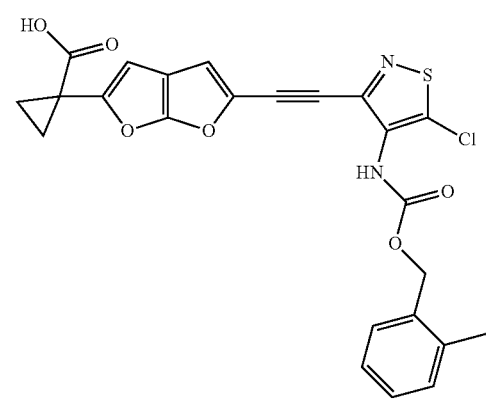
1434
TABLE 17-continued
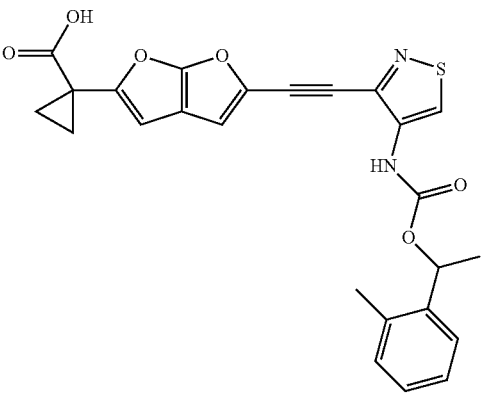
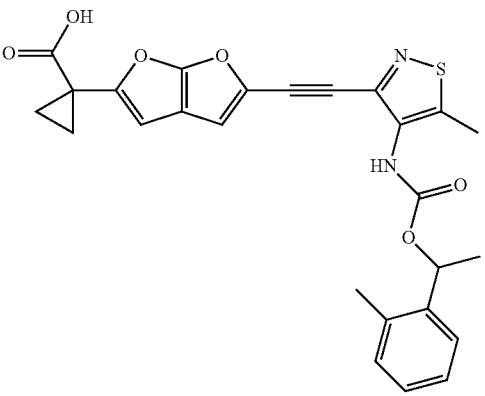
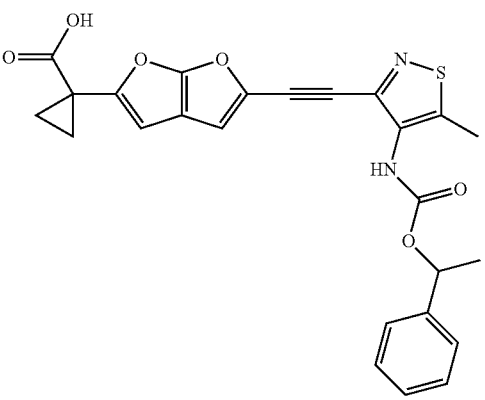
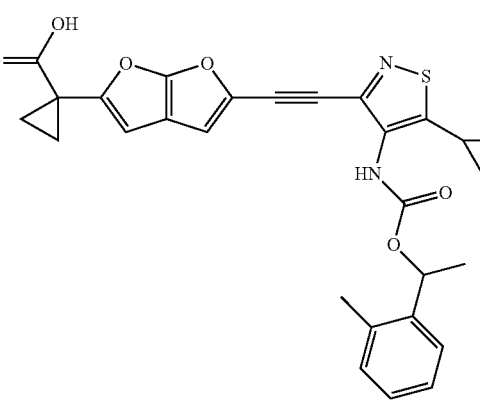

TABLE 17-continued
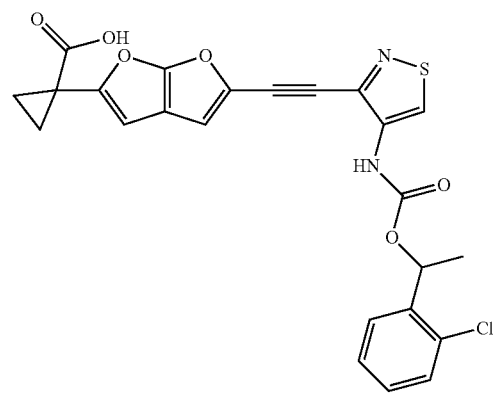 [SMILES: CC(OC(=O)Nc1csnc1C#Cc1cc2cc(C3(C(=O)O)CC3)oc2o1)c1ccccc1Cl]
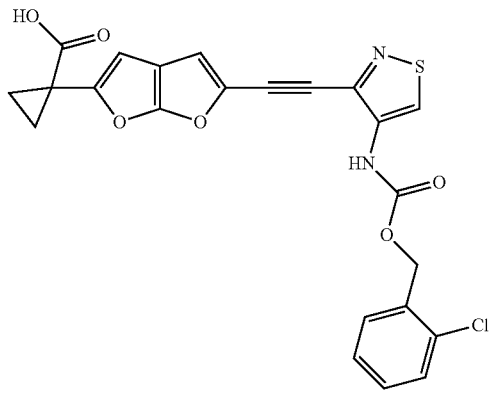
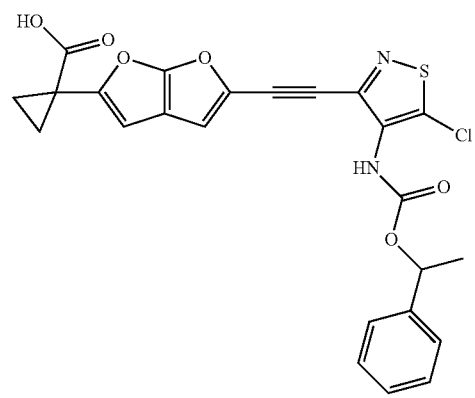
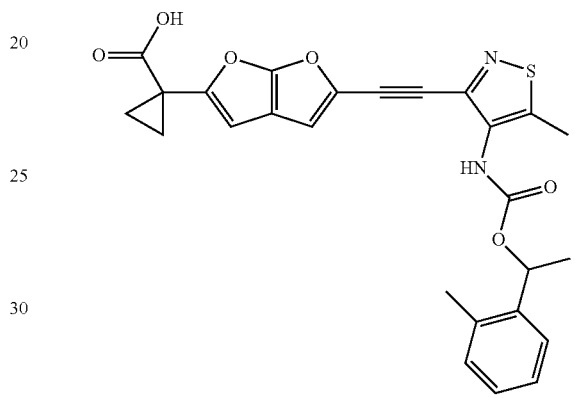
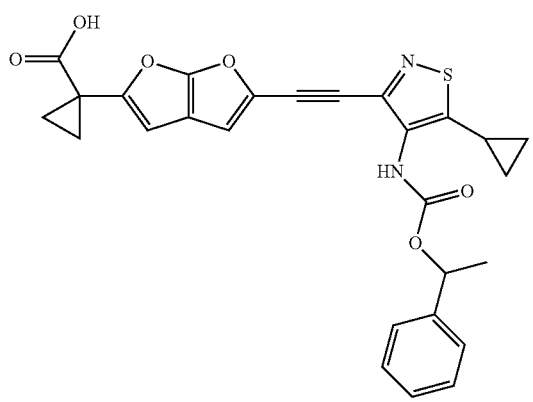
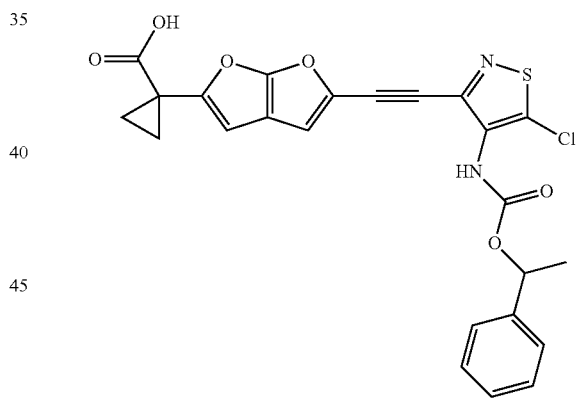
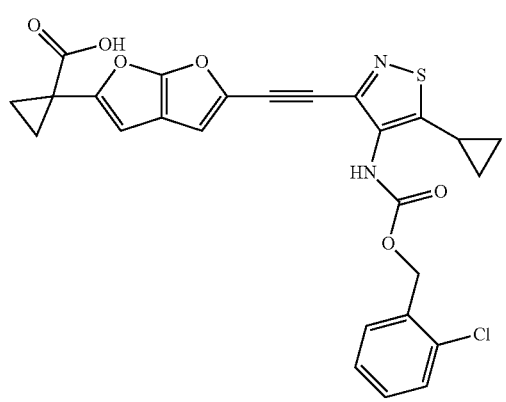 [SMILES: O=C(Nc1c(C#Cc2cc3cc(C4(C(=O)O)CC4)oc3o2)nsc1C1CC1)OCc1ccccc1Cl]
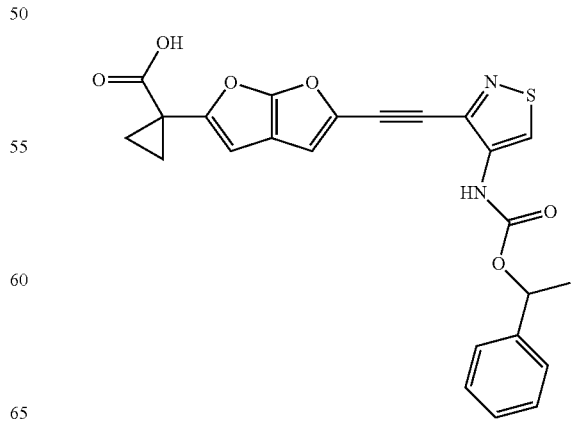

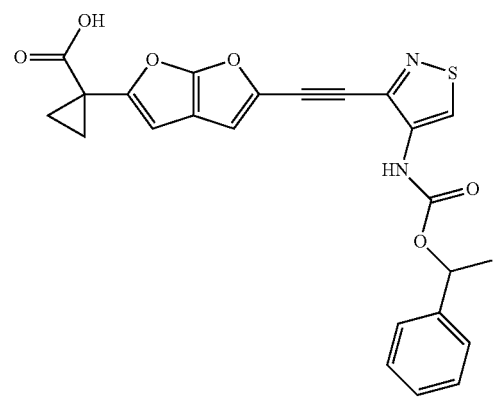
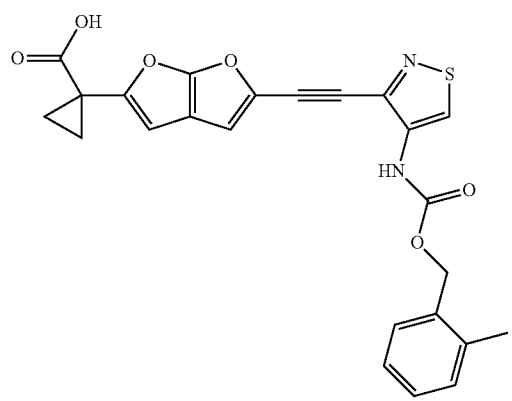 [SMILES: Cc1ccccc1COC(=O)Nc1csnc1C#Cc1cc2cc(C3(C(=O)O)CC3)oc2o1]
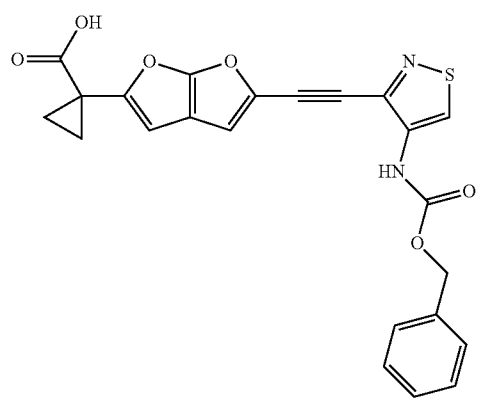 [SMILES: O=C(Nc1csnc1C#Cc1cc2cc(C3(C(=O)O)CC3)oc2o1)OCc1ccccc1]
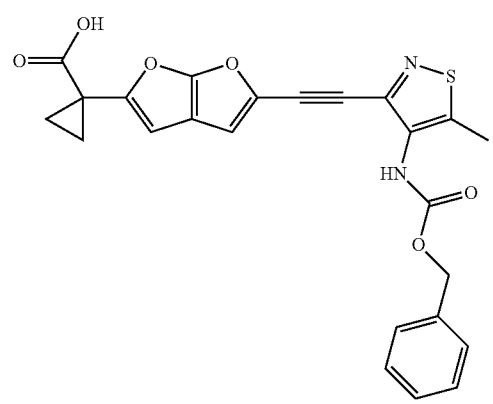
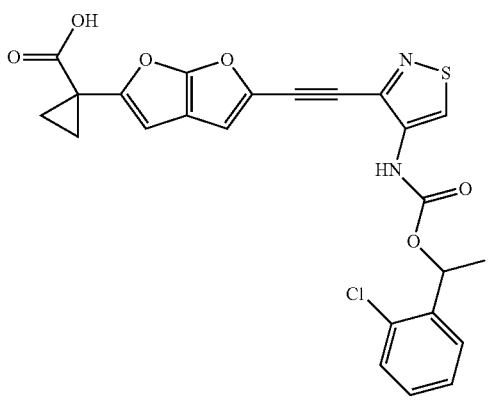
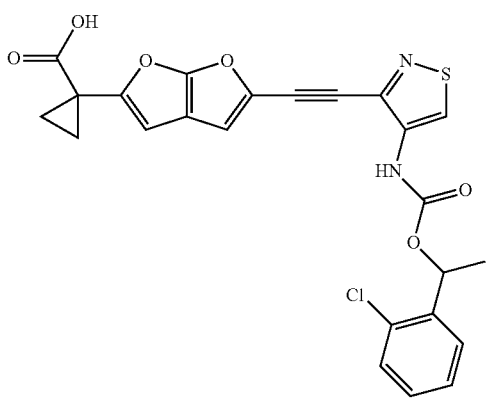
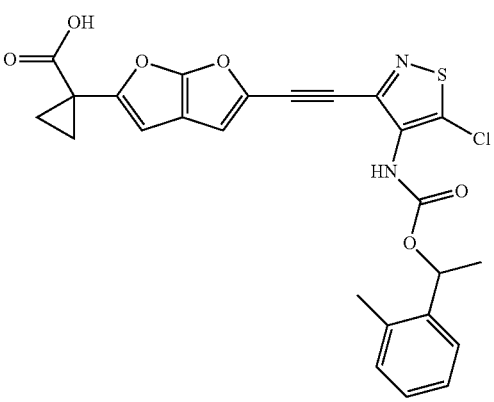 [SMILES: Cc1ccccc1C(C)OC(=O)Nc1c(C#Cc2cc3cc(C4(C(=O)O)CC4)oc3o2)nsc1Cl]
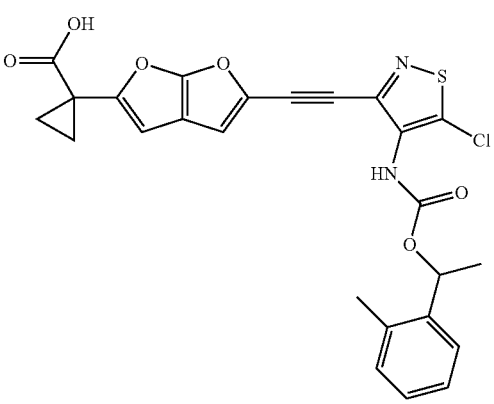 [SMILES: Cc1ccccc1C(C)OC(=O)Nc1c(C#Cc2cc3cc(C4(C(=O)O)CC4)oc3o2)nsc1Cl]

TABLE 17-continued
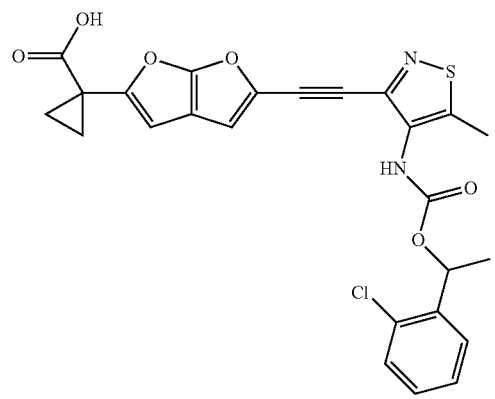 [SMILES: Cc1snc(C#Cc2cc3cc(C4(C(=O)O)CC4)oc3o2)c1NC(=O)OC(C)c1ccccc1Cl]
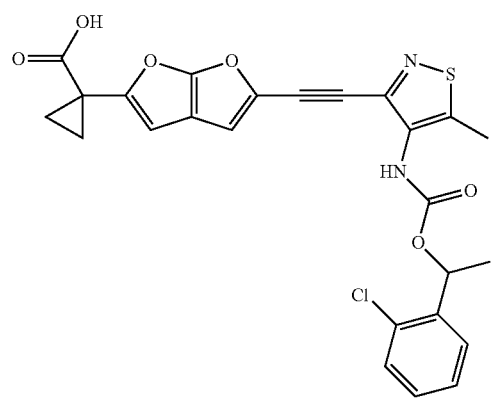 [SMILES: Cc1snc(C#Cc2cc3cc(C4(C(=O)O)CC4)oc3o2)c1NC(=O)OC(C)c1ccccc1Cl]
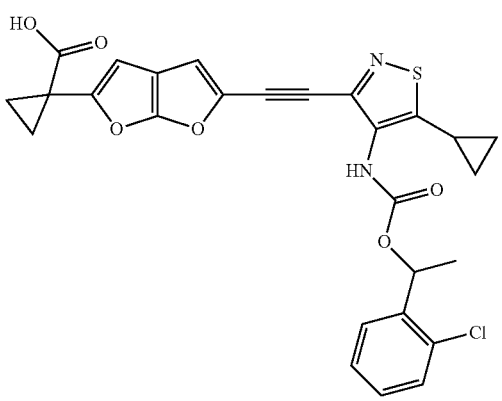
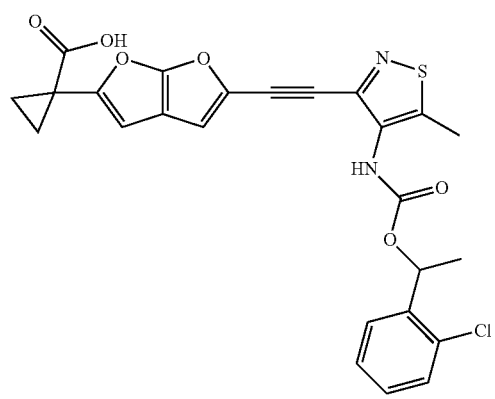 [SMILES: Cc1snc(C#Cc2cc3cc(C4(C(=O)O)CC4)oc3o2)c1NC(=O)OC(C)c1ccccc1Cl]
TABLE 17-continued
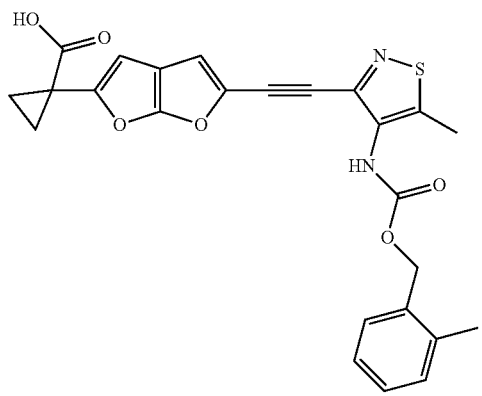 [SMILES: Cc1ccccc1COC(=O)Nc1c(C#Cc2cc3cc(C4(C(=O)O)CC4)oc3o2)nsc1C]
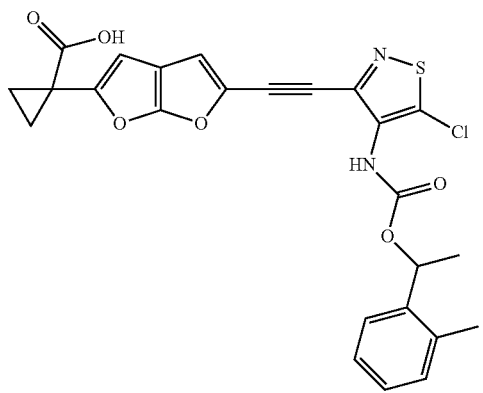 [SMILES: Cc1ccccc1C(C)OC(=O)Nc1c(C#Cc2cc3cc(C4(C(=O)O)CC4)oc3o2)nsc1Cl]
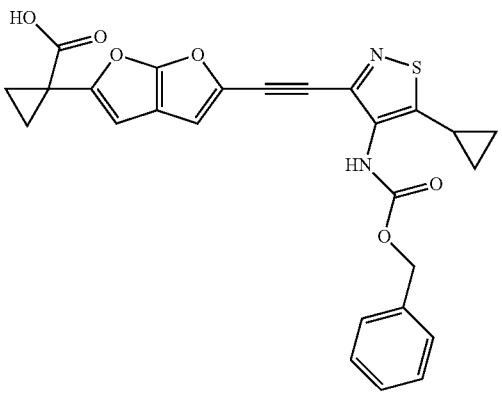 [SMILES: O=C(Nc1c(C#Cc2cc3cc(C4(C(=O)O)CC4)oc3o2)nsc1C1CC1)OCc1ccccc1]
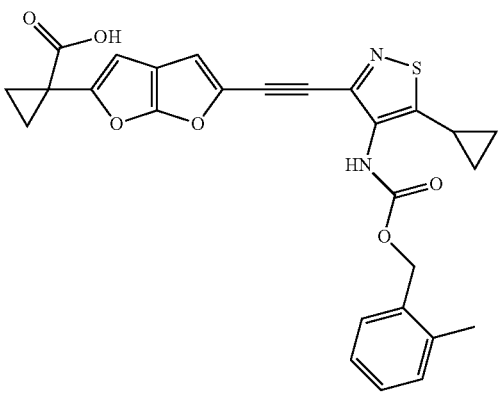 [SMILES: Cc1ccccc1COC(=O)Nc1c(C#Cc2cc3cc(C4(C(=O)O)CC4)oc3o2)nsc1C1CC1]

US 8,975,235 B2
| 1441 | 1442 |
|---|---|
| TABLE 17-continued | TABLE 17-continued |
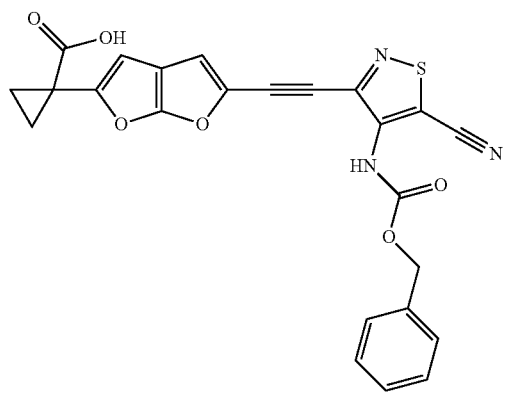 [SMILES: N#Cc1snc(C#Cc2cc3cc(C4(C(=O)O)CC4)oc3o2)c1NC(=O)OCc1ccccc1]
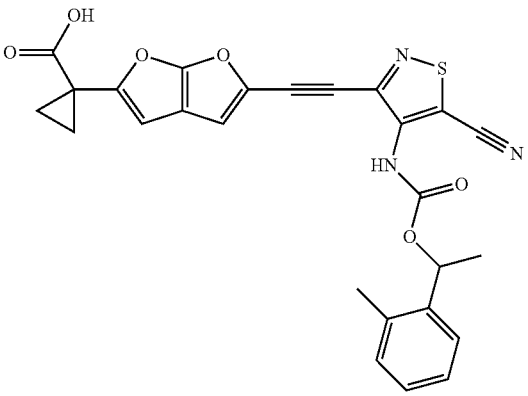
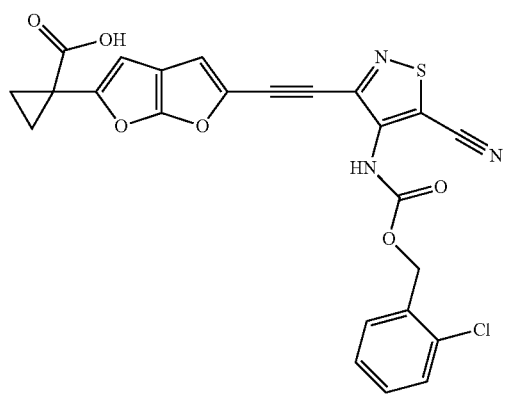 [SMILES: N#Cc1snc(C#Cc2cc3cc(C4(C(=O)O)CC4)oc3o2)c1NC(=O)OCc1ccccc1Cl]
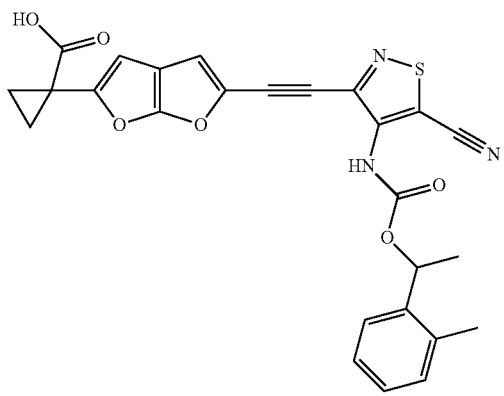
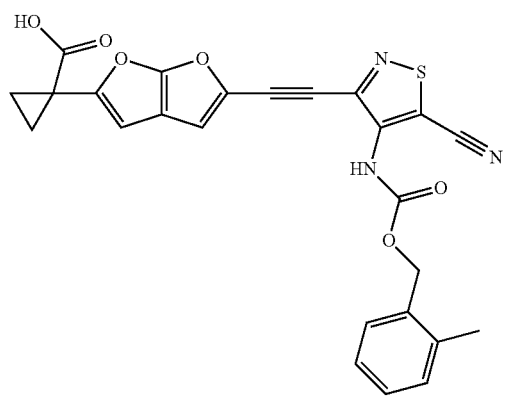 [SMILES: Cc1ccccc1COC(=O)Nc1c(C#Cc2cc3cc(C4(C(=O)O)CC4)oc3o2)nsc1C#N]
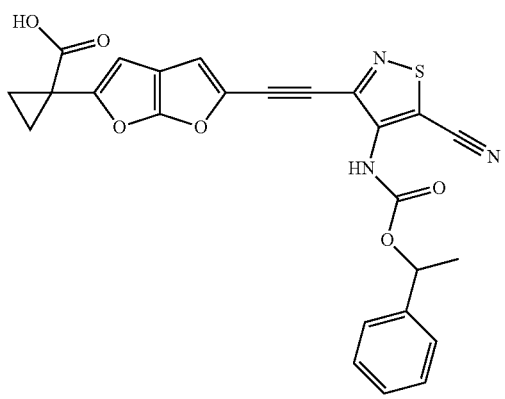 [SMILES: CC(OC(=O)Nc1c(C#Cc2cc3cc(C4(C(=O)O)CC4)oc3o2)nsc1C#N)c1ccccc1]
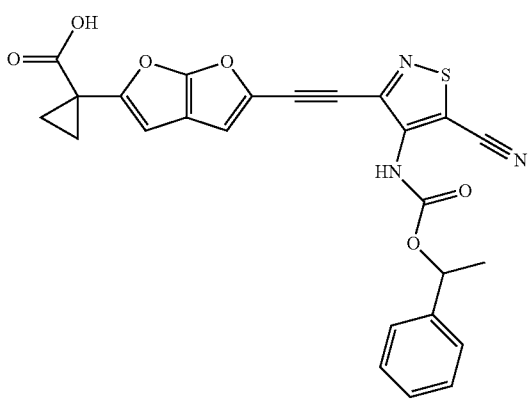
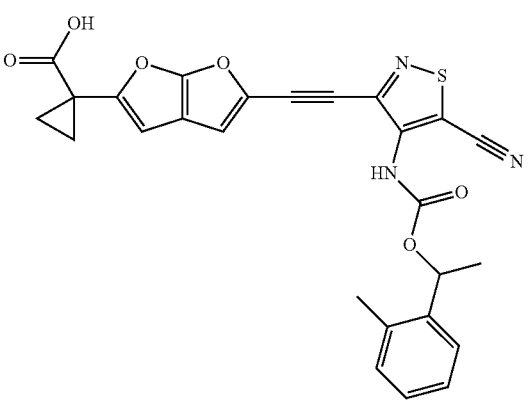 [SMILES: Cc1ccccc1C(C)OC(=O)Nc1c(C#Cc2cc3cc(C4(C(=O)O)CC4)oc3o2)nsc1C#N]

TABLE 17-continued
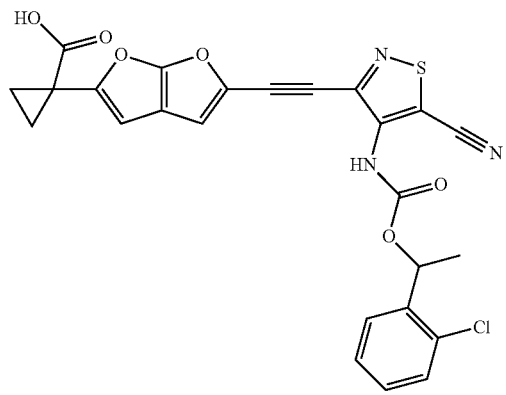
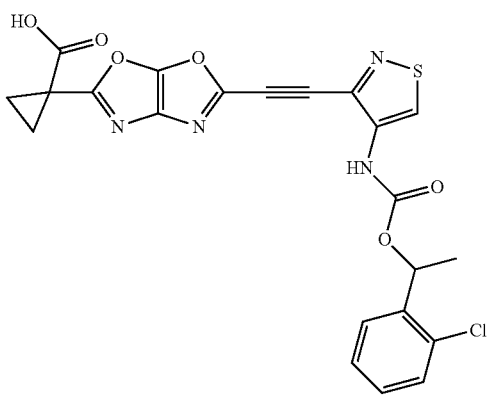
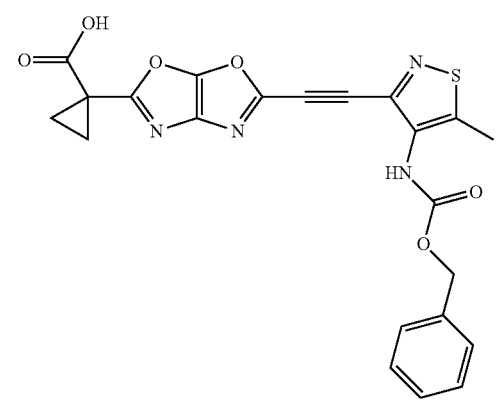 [SMILES: Cc1snc(C#Cc2nc3nc(C4(C(=O)O)CC4)oc3o2)c1NC(=O)OCc1ccccc1]
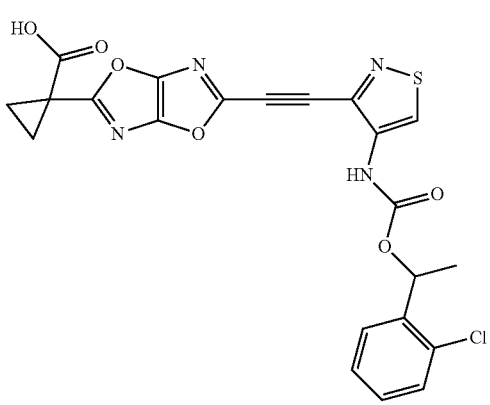 [SMILES: CC(OC(=O)Nc1csnc1C#Cc1nc2oc(C3(C(=O)O)CC3)nc2o1)c1ccccc1Cl]
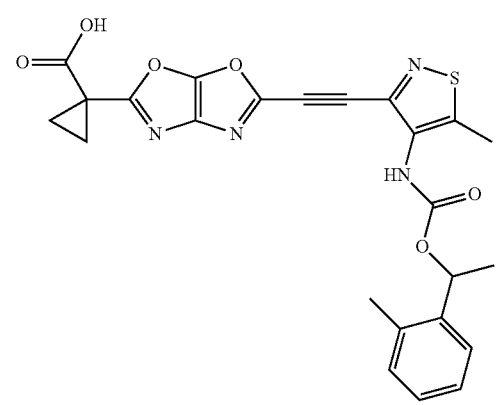
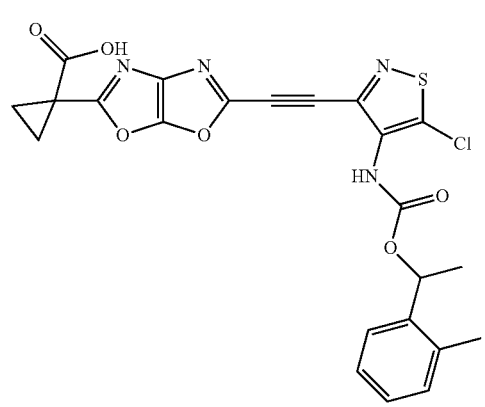 [SMILES: Cc1ccccc1C(C)OC(=O)Nc1c(C#Cc2nc3nc(C4(C(=O)O)CC4)oc3o2)nsc1Cl]
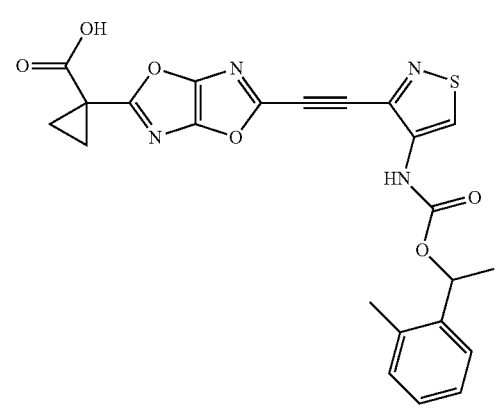
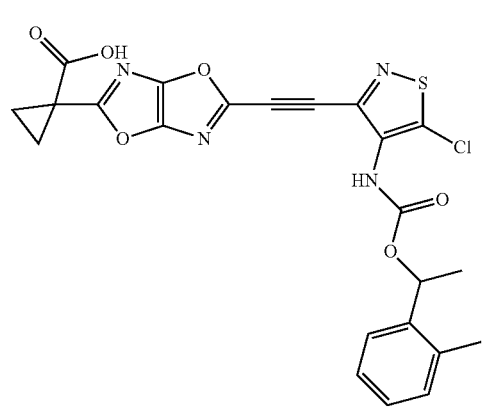 [SMILES: Cc1ccccc1C(C)OC(=O)Nc1c(C#Cc2nc3oc(C4(C(=O)O)CC4)nc3o2)nsc1Cl]

TABLE 17-continued
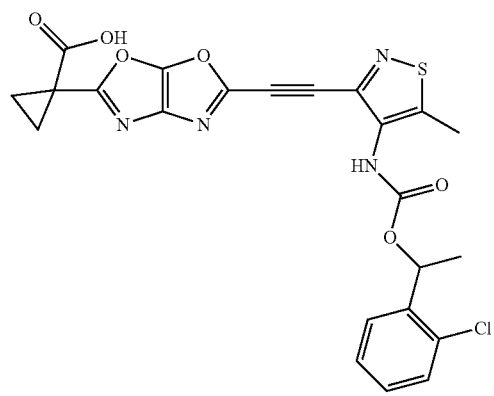 [SMILES: Cc1snc(C#Cc2nc3nc(C4(C(=O)O)CC4)oc3o2)c1NC(=O)OC(C)c1ccccc1Cl]
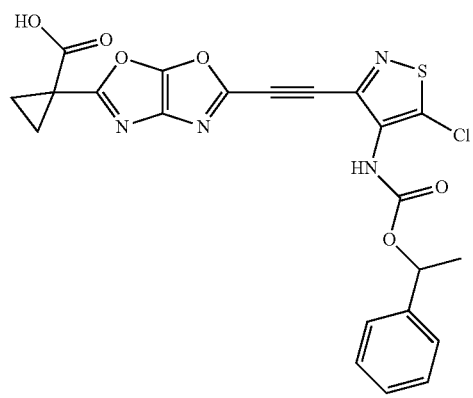
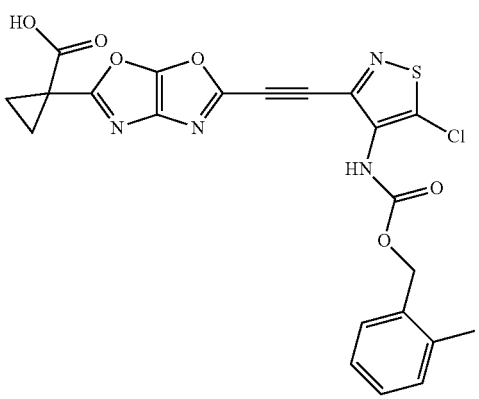
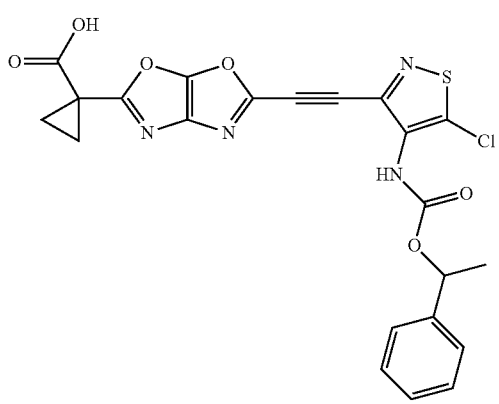 [SMILES: CC(OC(=O)Nc1c(C#Cc2nc3nc(C4(C(=O)O)CC4)oc3o2)nsc1Cl)c1ccccc1]
TABLE 17-continued
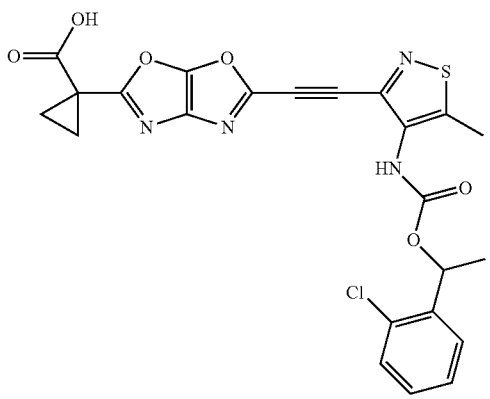
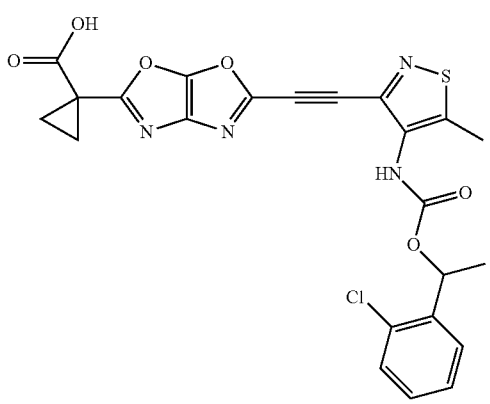
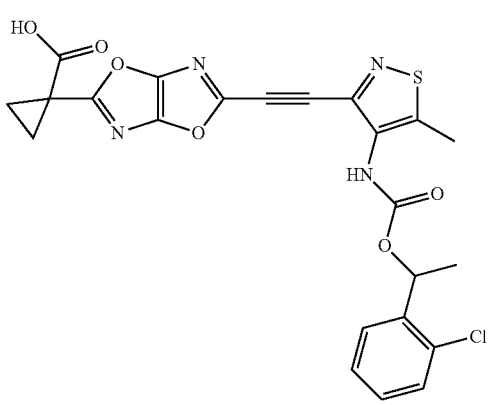
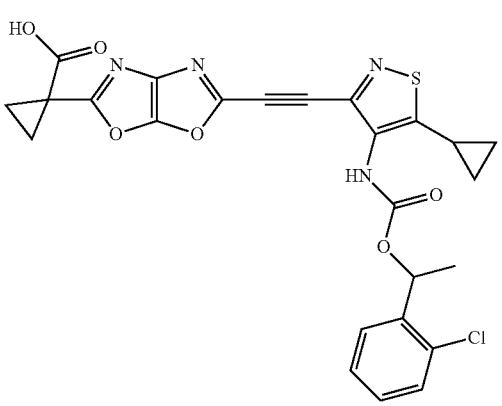 [SMILES: CC(OC(=O)Nc1c(C#Cc2nc3nc(C4(C(=O)O)CC4)oc3o2)nsc1C1CC1)c1ccccc1Cl]

1447
TABLE 17-continued
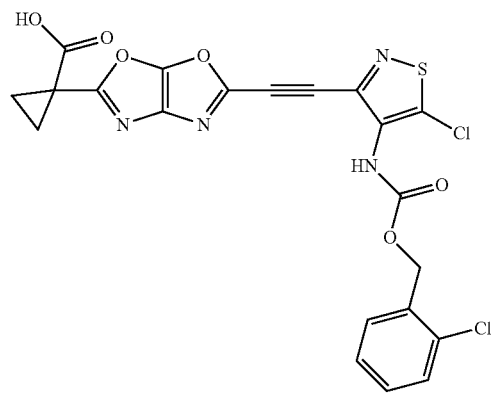 [SMILES: O=C(Nc1c(C#Cc2nc3nc(C4(C(=O)O)CC4)oc3o2)nsc1Cl)OCc1ccccc1Cl]
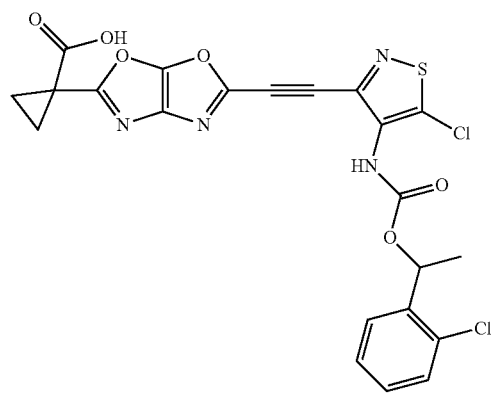 [SMILES: CC(OC(=O)Nc1c(C#Cc2nc3nc(C4(C(=O)O)CC4)oc3o2)nsc1Cl)c1ccccc1Cl]
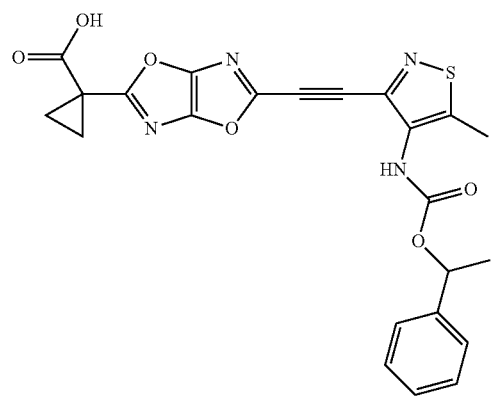 [SMILES: Cc1snc(C#Cc2nc3oc(C4(C(=O)O)CC4)nc3o2)c1NC(=O)OC(C)c1ccccc1]
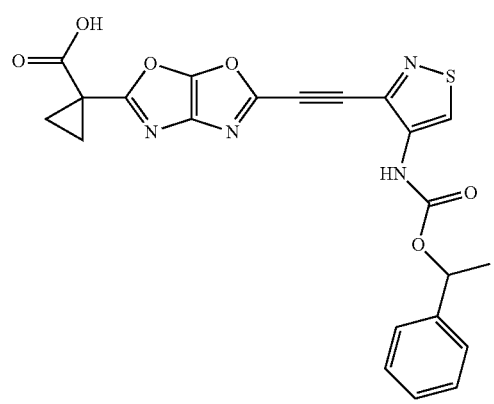
1448
TABLE 17-continued
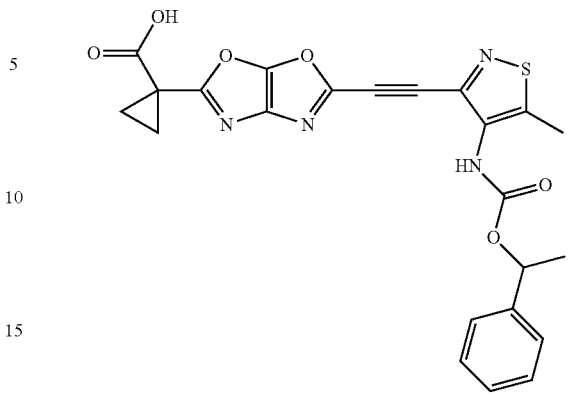
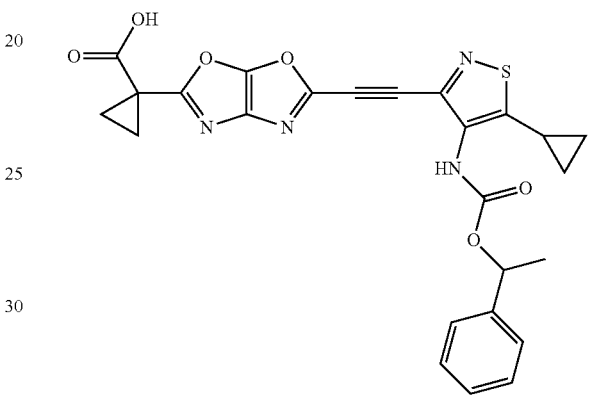
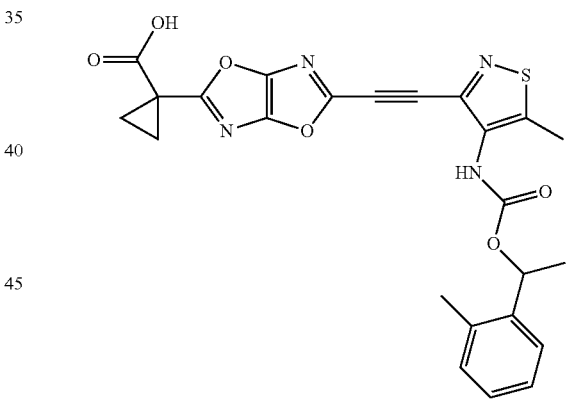
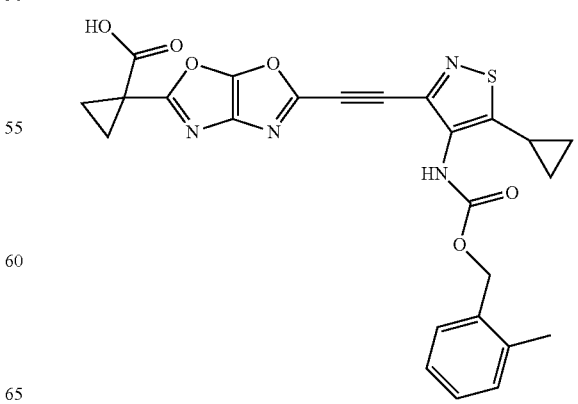

| 1449 | 1450 |
|---|---|
| TABLE 17-continued | TABLE 17-continued |
| 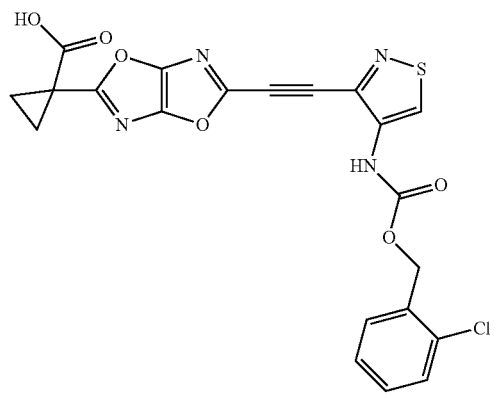 [SMILES: O=C(Nc1csnc1C#Cc1nc2oc(C3(C(=O)O)CC3)nc2o1)OCc1ccccc1Cl] | 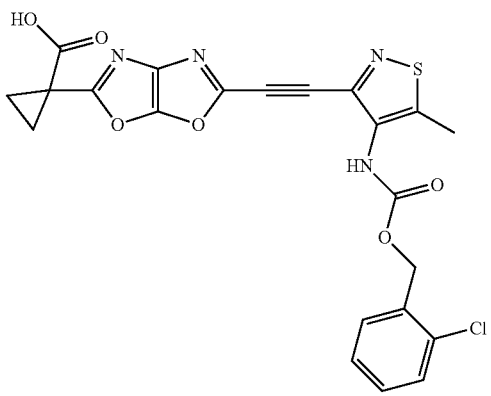 |
| 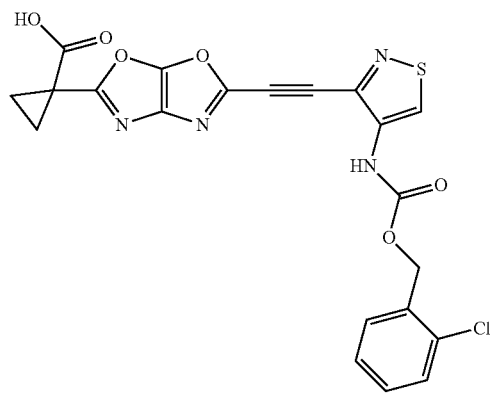 [SMILES: O=C(Nc1csnc1C#Cc1nc2nc(C3(C(=O)O)CC3)oc2o1)OCc1ccccc1Cl] | 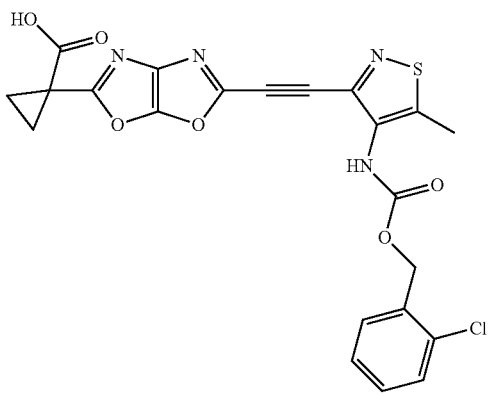 |
| 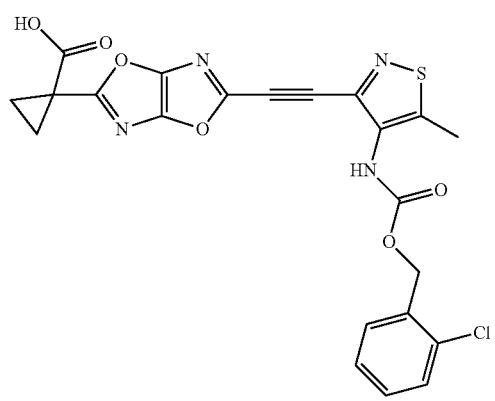 [SMILES: Cc1snc(C#Cc2nc3oc(C4(C(=O)O)CC4)nc3o2)c1NC(=O)OCc1ccccc1Cl] | 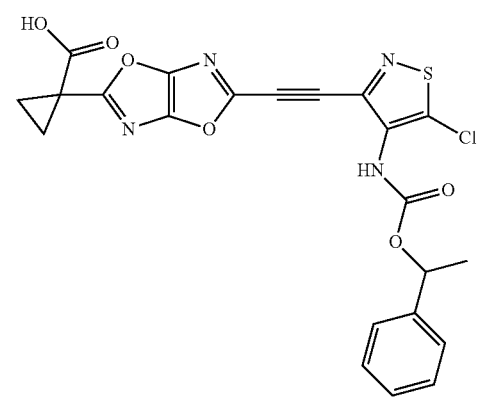 |
| 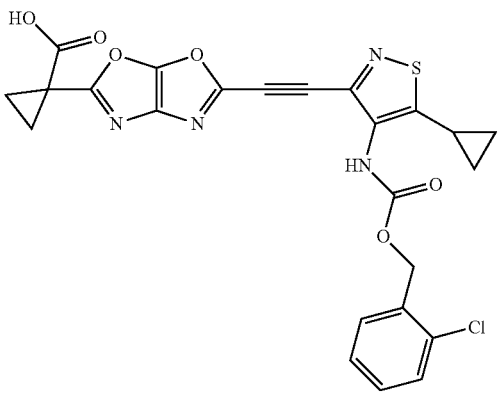 [SMILES: O=C(Nc1c(C#Cc2nc3nc(C4(C(=O)O)CC4)oc3o2)nsc1C1CC1)OCc1ccccc1Cl] | 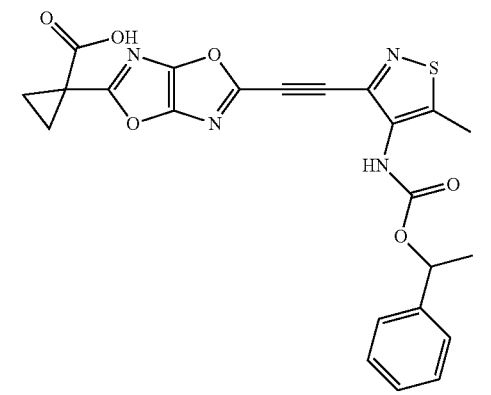 |

1451
TABLE 17-continued
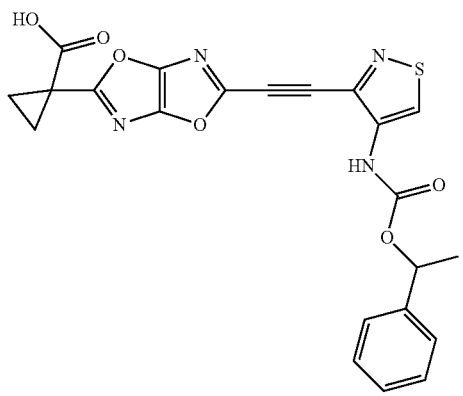 [SMILES: CC(OC(=O)Nc1csnc1C#Cc1nc2oc(C3(C(=O)O)CC3)nc2o1)c1ccccc1]
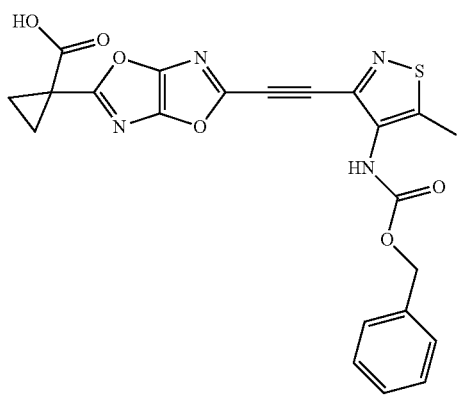
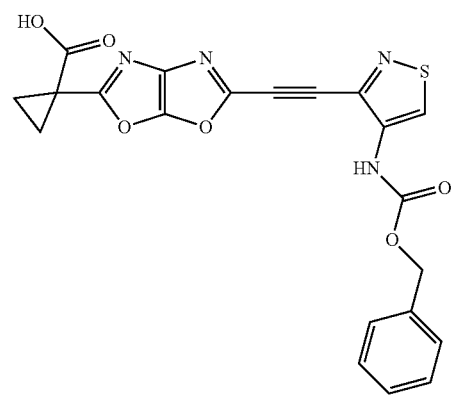 [SMILES: O=C(Nc1csnc1C#Cc1nc2nc(C3(C(=O)O)CC3)oc2o1)OCc1ccccc1]
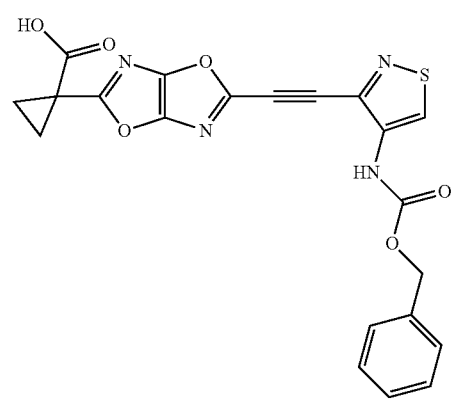 [SMILES: O=C(Nc1csnc1C#Cc1nc2oc(C3(C(=O)O)CC3)nc2o1)OCc1ccccc1]
1452
TABLE 17-continued
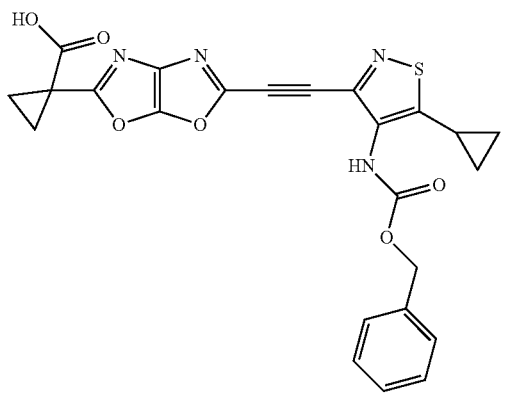 [SMILES: O=C(Nc1c(C#Cc2nc3nc(C4(C(=O)O)CC4)oc3o2)nsc1C1CC1)OCc1ccccc1]
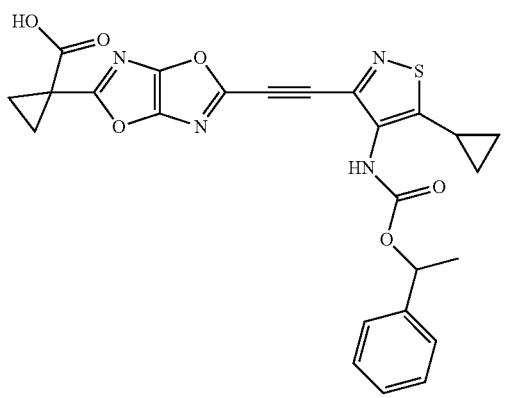
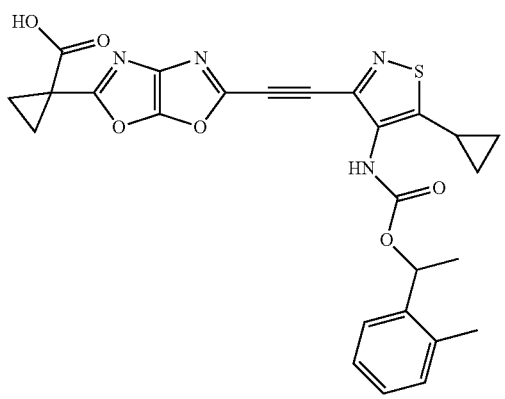 [SMILES: Cc1ccccc1C(C)OC(=O)Nc1c(C#Cc2nc3nc(C4(C(=O)O)CC4)oc3o2)nsc1C1CC1]
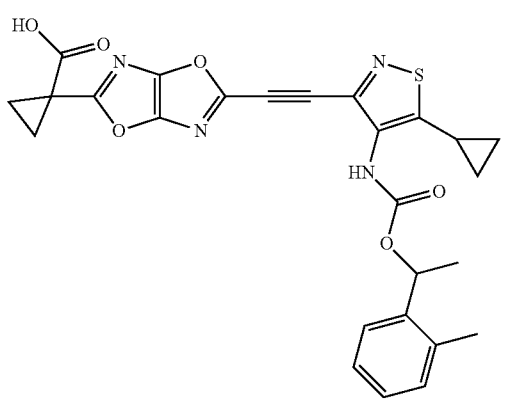 [SMILES: Cc1ccccc1C(C)OC(=O)Nc1c(C#Cc2nc3oc(C4(C(=O)O)CC4)nc3o2)nsc1C1CC1]

TABLE 17-continued
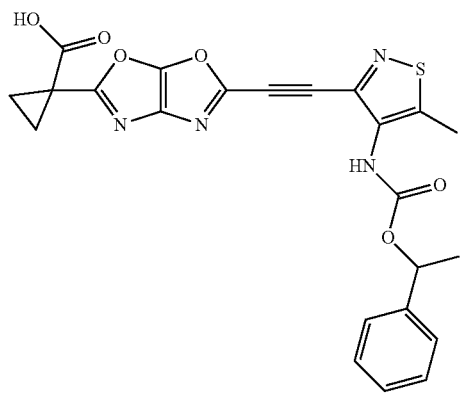
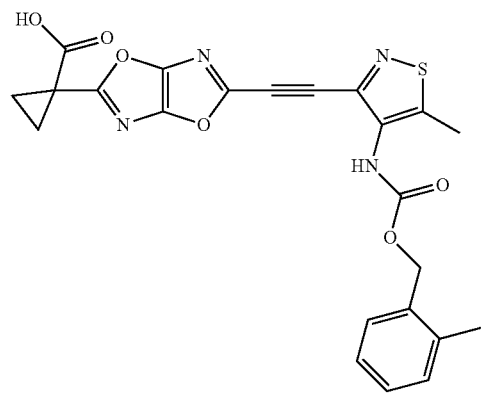 [SMILES: Cc1ccccc1COC(=O)Nc1c(C#Cc2nc3oc(C4(C(=O)O)CC4)nc3o2)nsc1C]
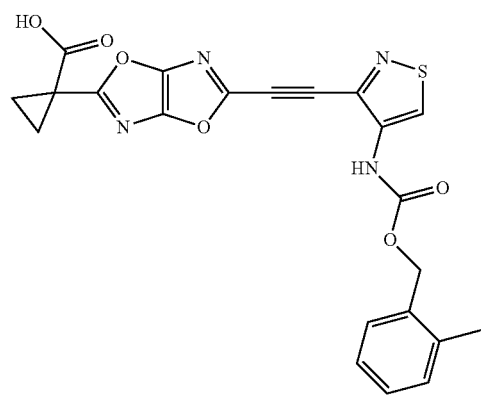 [SMILES: Cc1ccccc1COC(=O)Nc1csnc1C#Cc1nc2oc(C3(C(=O)O)CC3)nc2o1]
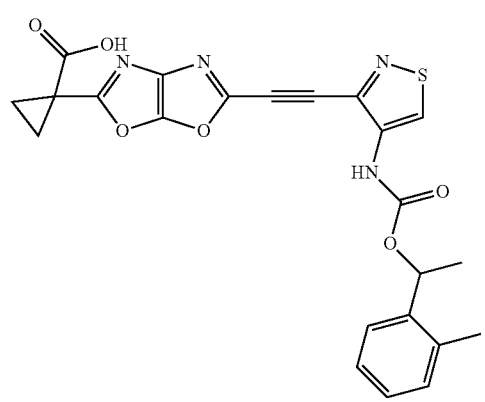 [SMILES: Cc1ccccc1C(C)OC(=O)Nc1csnc1C#Cc1nc2nc(C3(C(=O)O)CC3)oc2o1]
TABLE 17-continued
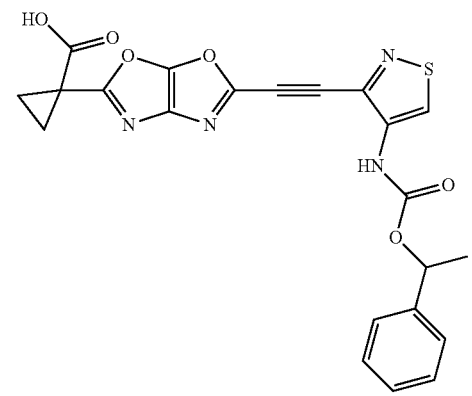
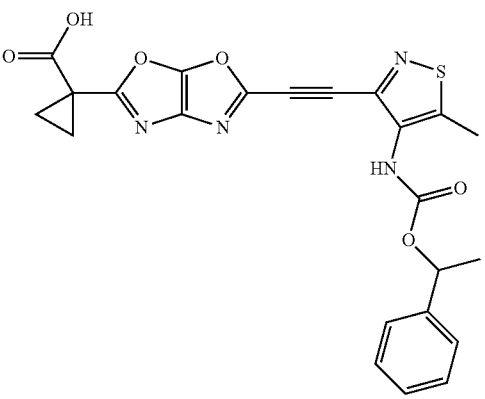 [SMILES: Cc1snc(C#Cc2nc3nc(C4(C(=O)O)CC4)oc3o2)c1NC(=O)OC(C)c1ccccc1]
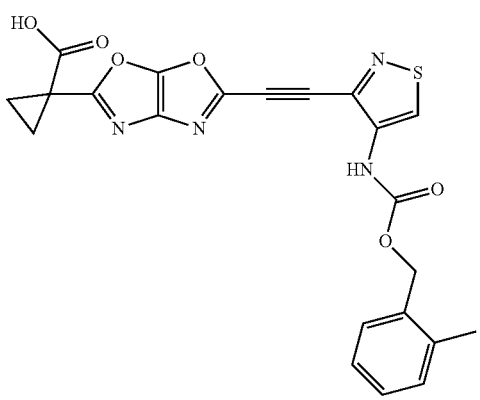 [SMILES: Cc1ccccc1COC(=O)Nc1csnc1C#Cc1nc2nc(C3(C(=O)O)CC3)oc2o1]
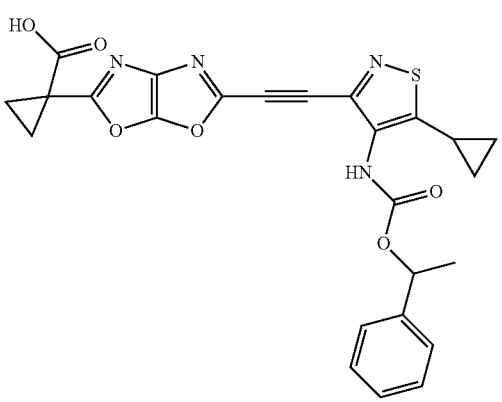

TABLE 17-continued
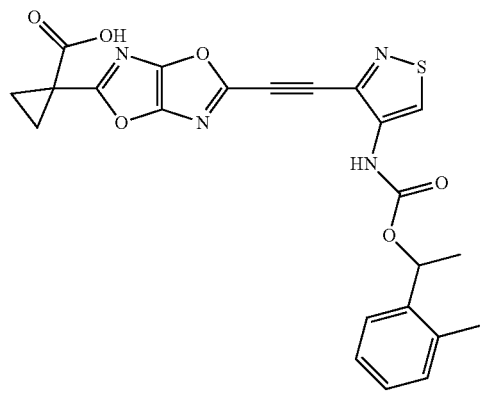 [SMILES: Cc1ccccc1C(C)OC(=O)Nc1csnc1C#Cc1nc2oc(C3(C(=O)O)CC3)nc2o1]
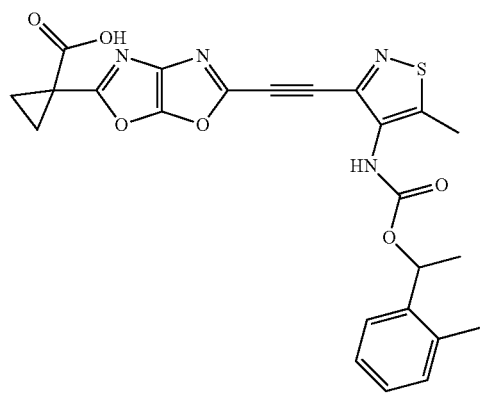 [SMILES: Cc1ccccc1C(C)OC(=O)Nc1c(C#Cc2nc3nc(C4(C(=O)O)CC4)oc3o2)nsc1C]
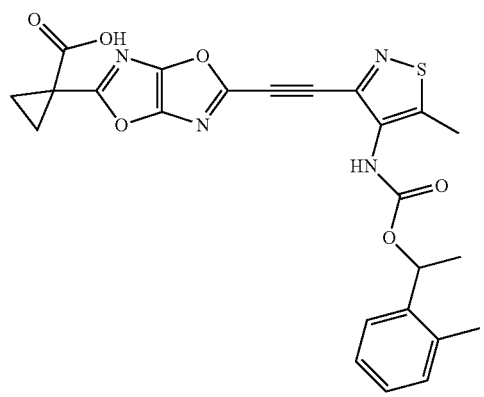 [SMILES: Cc1ccccc1C(C)OC(=O)Nc1c(C#Cc2nc3oc(C4(C(=O)O)CC4)nc3o2)nsc1C]
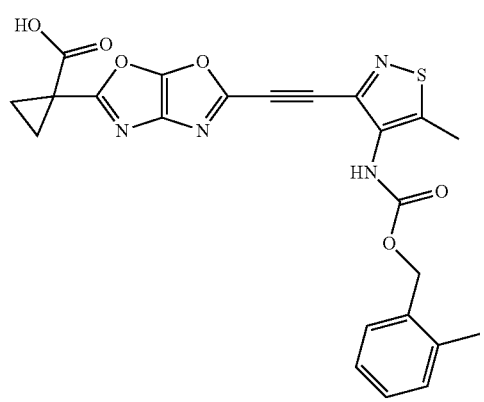 [SMILES: Cc1ccccc1COC(=O)Nc1c(C#Cc2nc3nc(C4(C(=O)O)CC4)oc3o2)nsc1C]
TABLE 17-continued
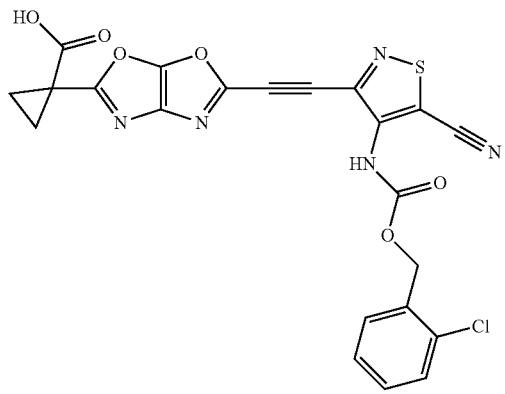 [SMILES: N#Cc1snc(C#Cc2nc3nc(C4(C(=O)O)CC4)oc3o2)c1NC(=O)OCc1ccccc1Cl]
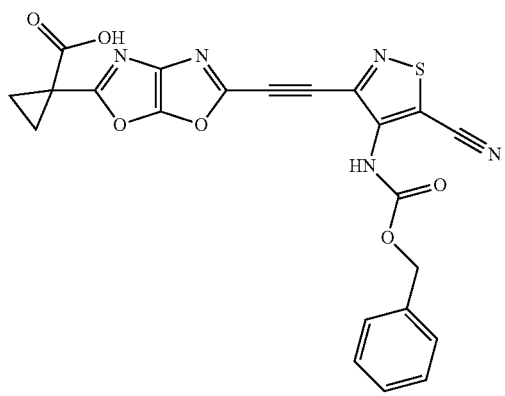 [SMILES: N#Cc1snc(C#Cc2nc3nc(C4(C(=O)O)CC4)oc3o2)c1NC(=O)OCc1ccccc1]
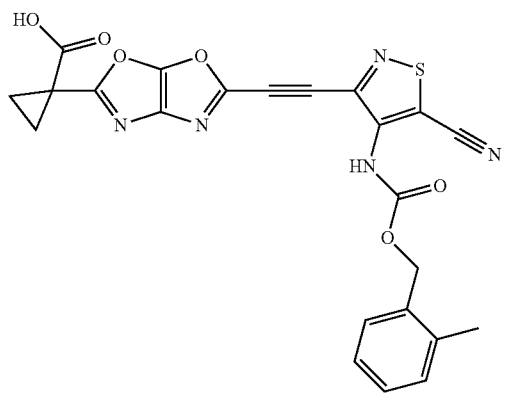 [SMILES: Cc1ccccc1COC(=O)Nc1c(C#Cc2nc3nc(C4(C(=O)O)CC4)oc3o2)nsc1C#N]
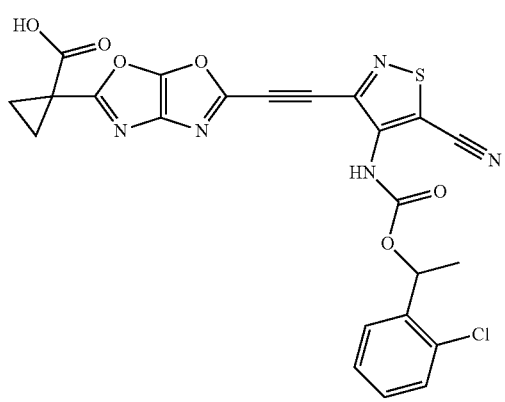 [SMILES: CC(OC(=O)Nc1c(C#Cc2nc3nc(C4(C(=O)O)CC4)oc3o2)nsc1C#N)c1ccccc1Cl]

US 8,975,235 B2
| 1457 | 1458 |
|---|---|
| TABLE 17-continued | TABLE 17-continued |
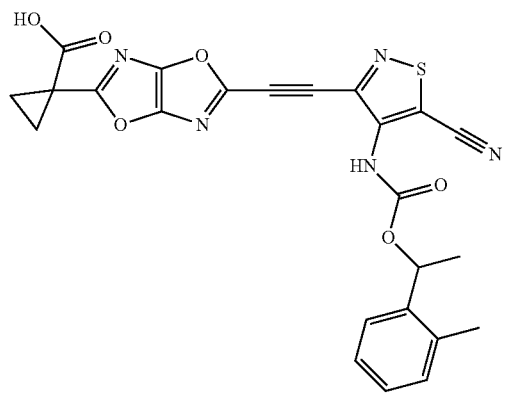 [SMILES: Cc1ccccc1C(C)OC(=O)Nc1c(C#Cc2nc3oc(C4(C(=O)O)CC4)nc3o2)nsc1C#N]
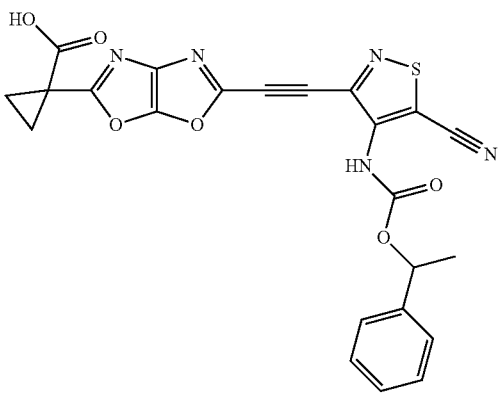
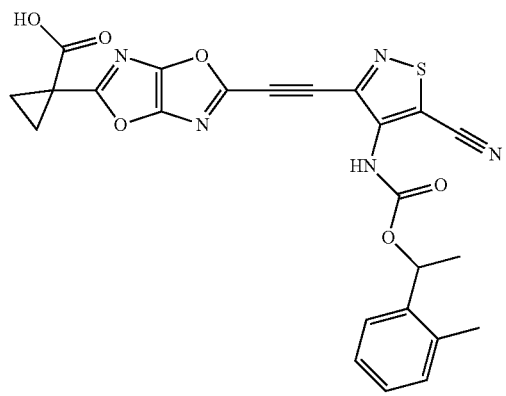 [SMILES: Cc1ccccc1C(C)OC(=O)Nc1c(C#Cc2nc3oc(C4(C(=O)O)CC4)nc3o2)nsc1C#N]
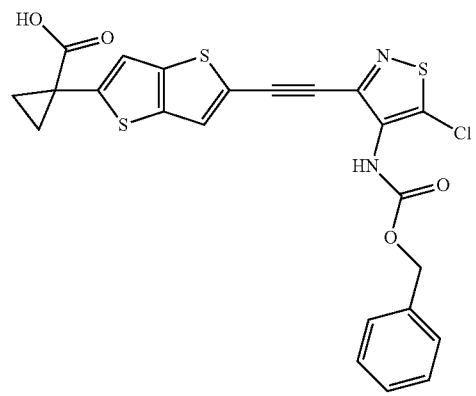 [SMILES: O=C(Nc1c(C#Cc2cc3sc(C4(C(=O)O)CC4)cc3s2)nsc1Cl)OCc1ccccc1]
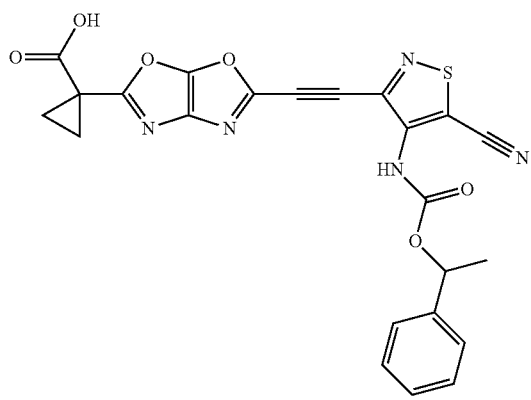
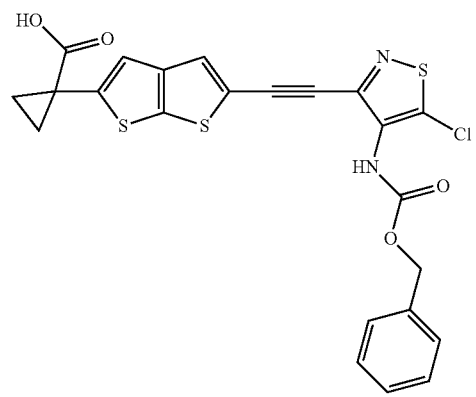 [SMILES: O=C(Nc1c(C#Cc2cc3cc(C4(C(=O)O)CC4)sc3s2)nsc1Cl)OCc1ccccc1]
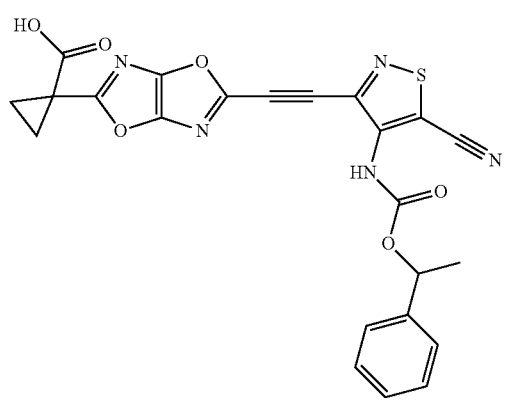
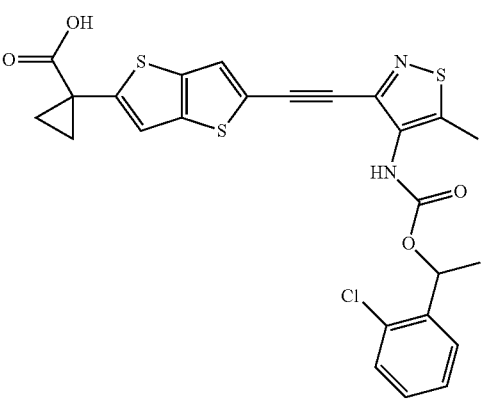 [SMILES: Cc1snc(C#Cc2cc3sc(C4(C(=O)O)CC4)cc3s2)c1NC(=O)OC(C)c1ccccc1Cl]

1459
TABLE 17-continued
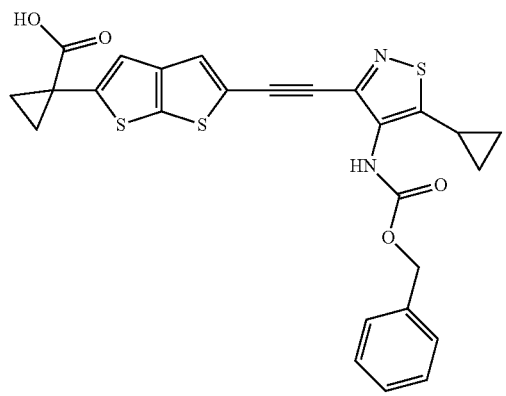 [SMILES: O=C(Nc1c(C#Cc2cc3cc(C4(C(=O)O)CC4)sc3s2)nsc1C1CC1)OCc1ccccc1]
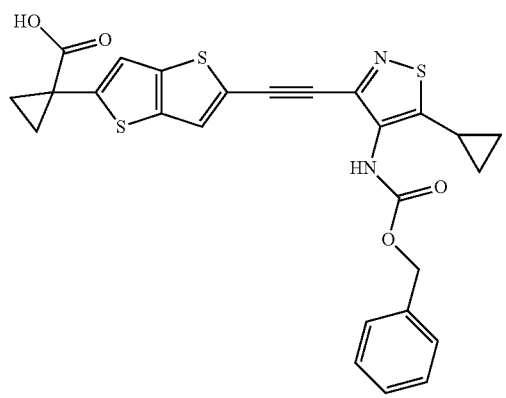
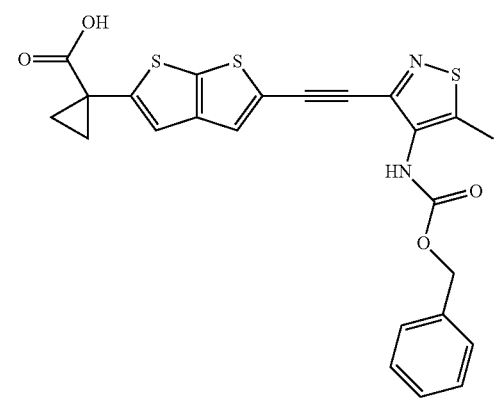
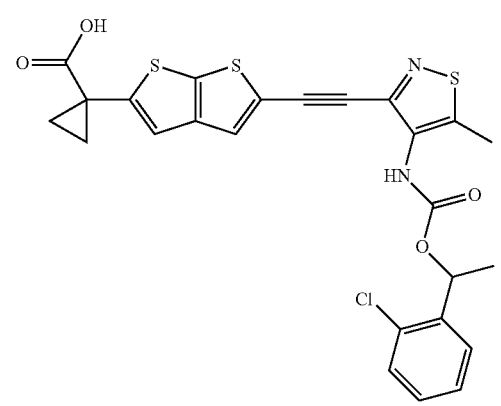 [SMILES: Cc1snc(C#Cc2cc3cc(C4(C(=O)O)CC4)sc3s2)c1NC(=O)OC(C)c1ccccc1Cl]
1460
TABLE 17-continued
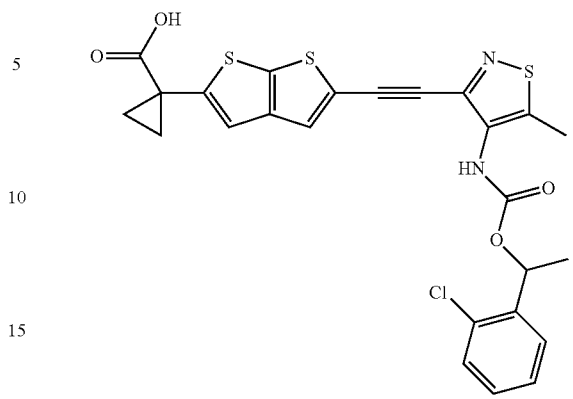
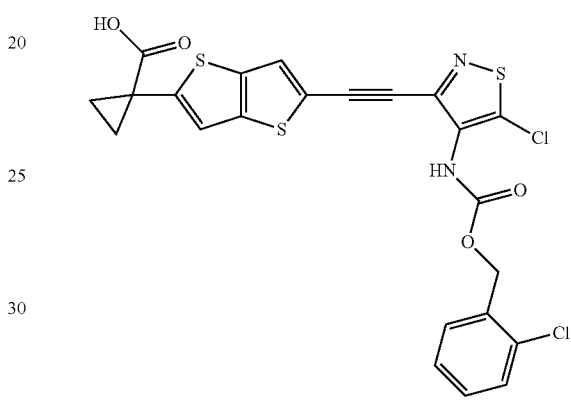
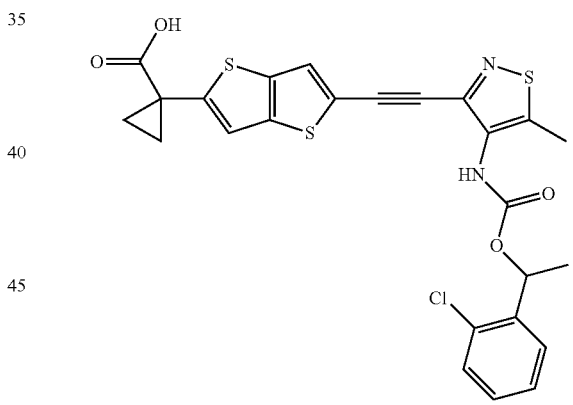
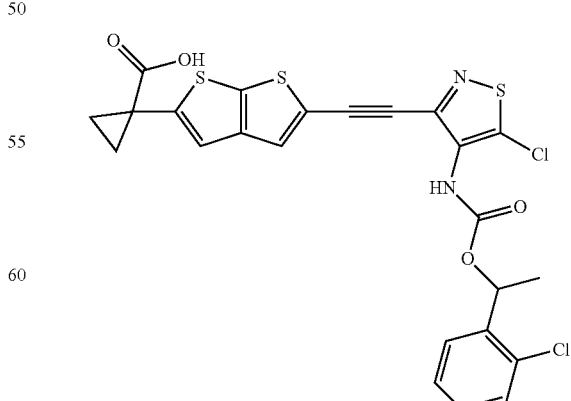

TABLE 17-continued
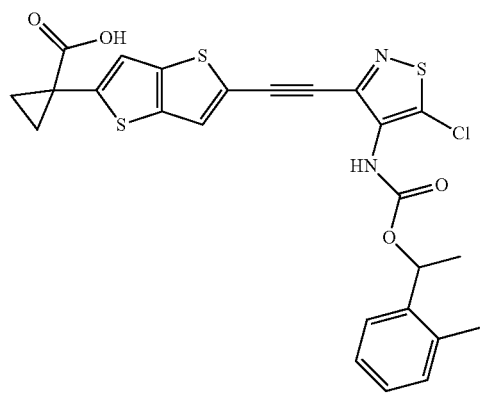 [SMILES: Cc1ccccc1C(C)OC(=O)Nc1c(C#Cc2cc3sc(C4(C(=O)O)CC4)cc3s2)nsc1Cl]
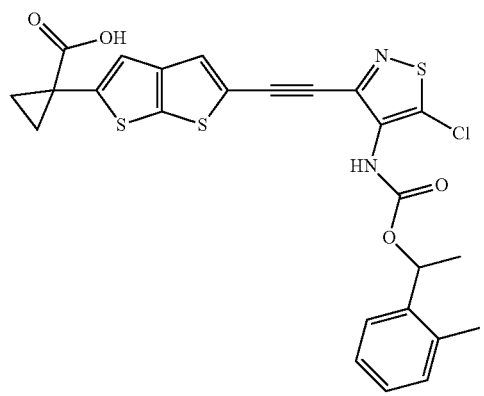
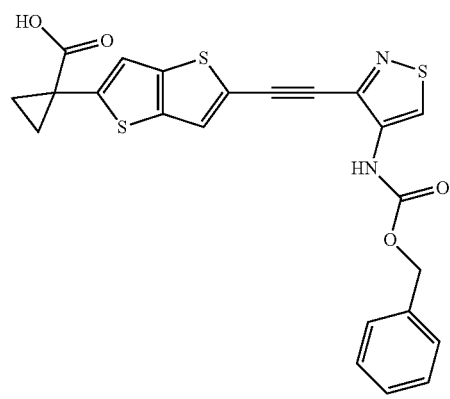 [SMILES: O=C(Nc1csnc1C#Cc1cc2sc(C3(C(=O)O)CC3)cc2s1)OCc1ccccc1]
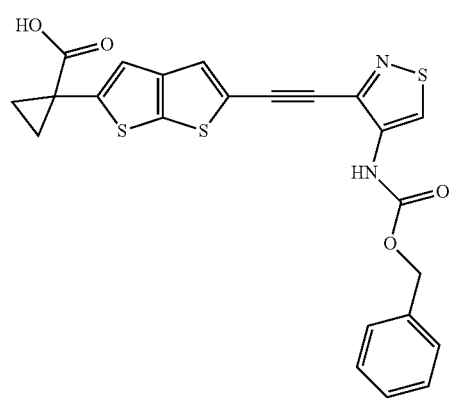 [SMILES: O=C(Nc1csnc1C#Cc1cc2cc(C3(C(=O)O)CC3)sc2s1)OCc1ccccc1]
TABLE 17-continued
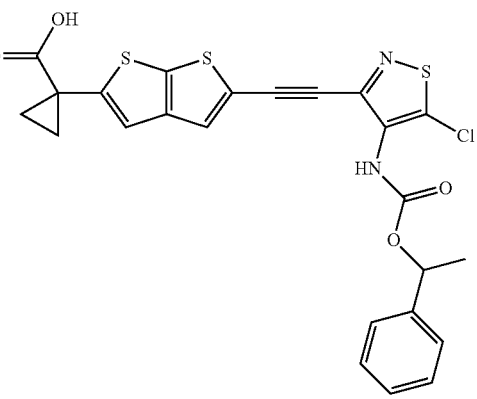
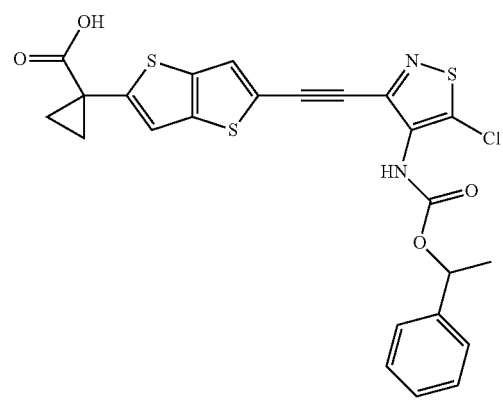 [SMILES: CC(OC(=O)Nc1c(C#Cc2cc3sc(C4(C(=O)O)CC4)cc3s2)nsc1Cl)c1ccccc1]
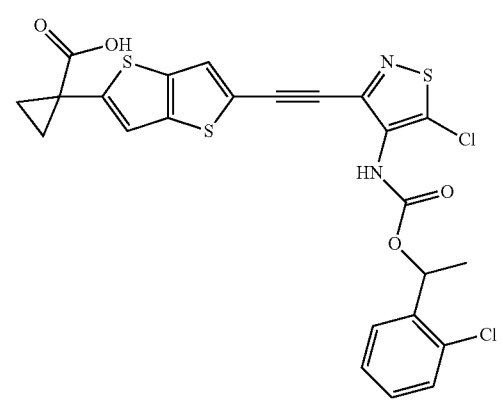 [SMILES: CC(OC(=O)Nc1c(C#Cc2cc3sc(C4(C(=O)O)CC4)cc3s2)nsc1Cl)c1ccccc1Cl]
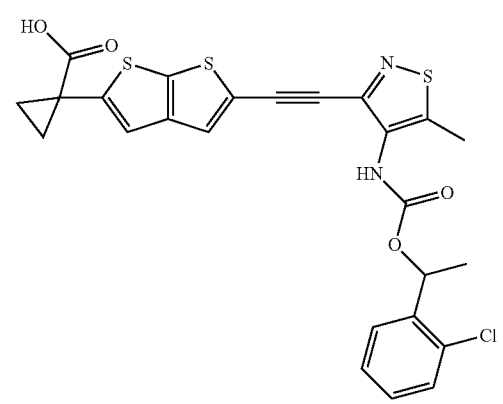 [SMILES: Cc1snc(C#Cc2cc3cc(C4(C(=O)O)CC4)sc3s2)c1NC(=O)OC(C)c1ccccc1Cl]

TABLE 17-continued
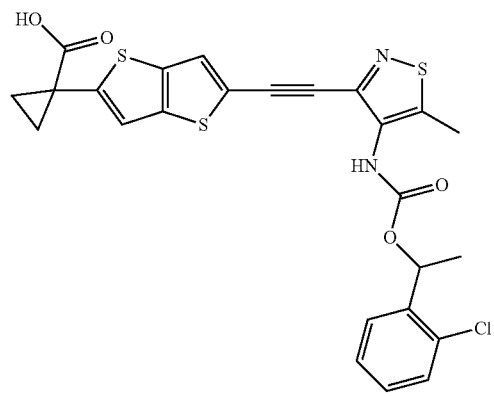 [SMILES: Cc1snc(C#Cc2cc3sc(C4(C(=O)O)CC4)cc3s2)c1NC(=O)OC(C)c1ccccc1Cl]
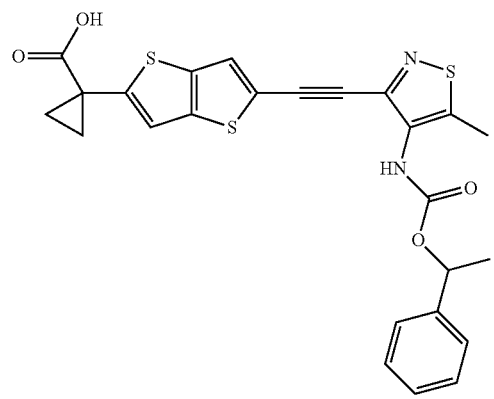
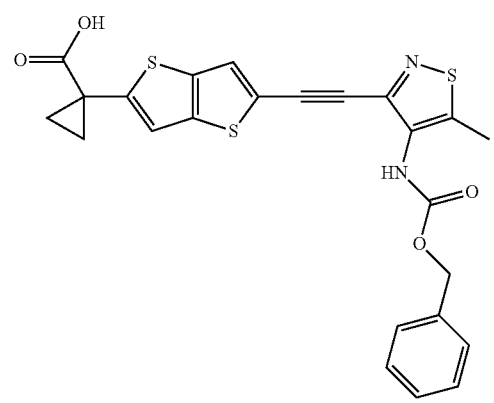 [SMILES: Cc1snc(C#Cc2cc3sc(C4(C(=O)O)CC4)cc3s2)c1NC(=O)OCc1ccccc1]
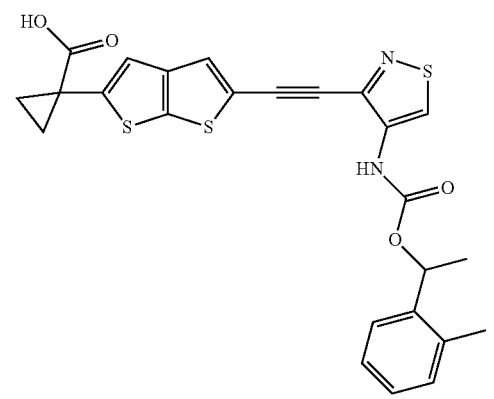 [SMILES: Cc1ccccc1C(C)OC(=O)Nc1csnc1C#Cc1cc2cc(C3(C(=O)O)CC3)sc2s1]
TABLE 17-continued
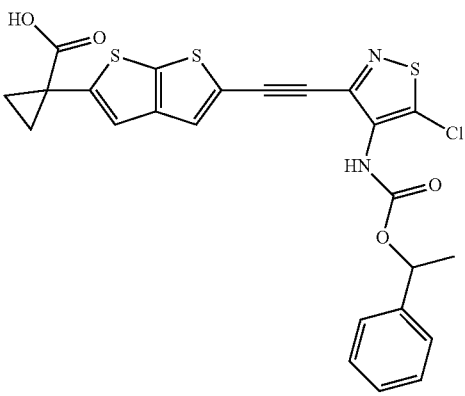
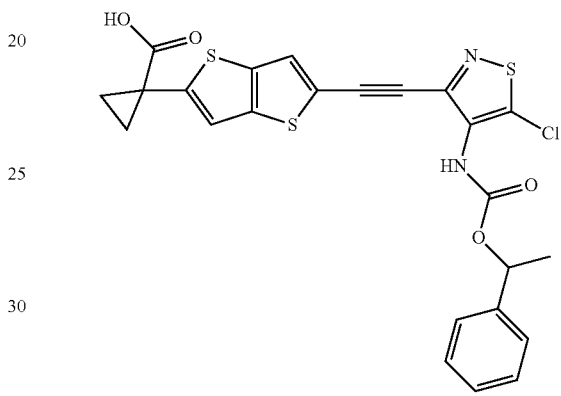
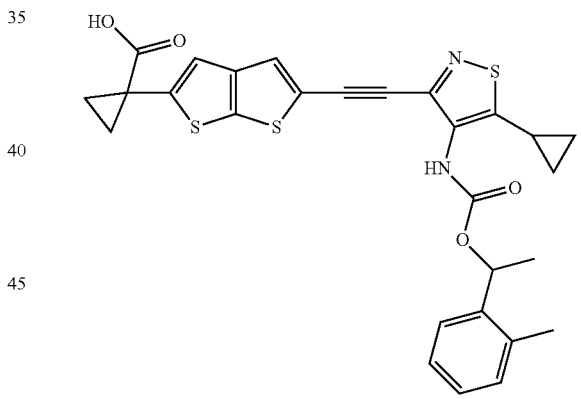
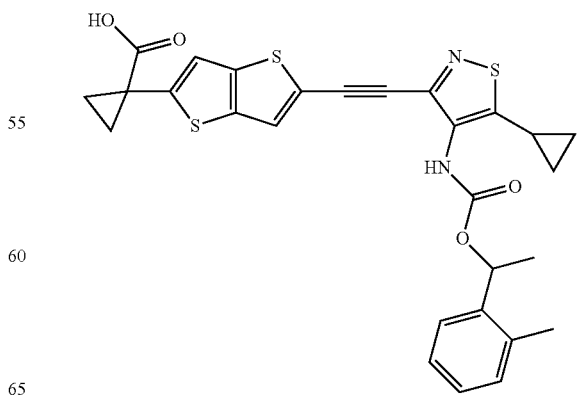

TABLE 17-continued
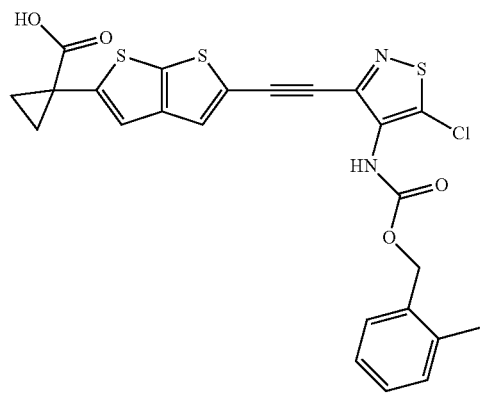 [SMILES: Cc1ccccc1COC(=O)Nc1c(C#Cc2cc3cc(C4(C(=O)O)CC4)sc3s2)nsc1Cl]
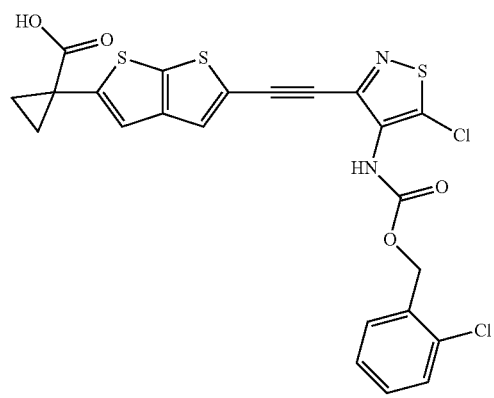
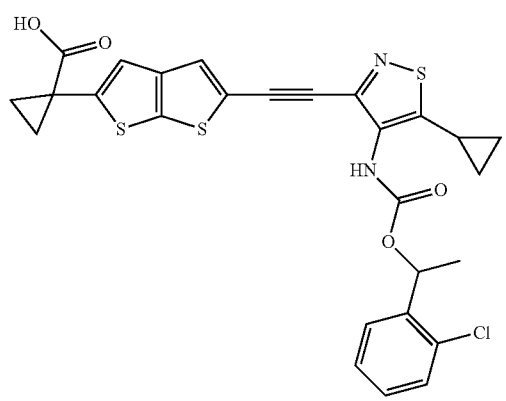 [SMILES: CC(OC(=O)Nc1c(C#Cc2cc3cc(C4(C(=O)O)CC4)sc3s2)nsc1C1CC1)c1ccccc1Cl]
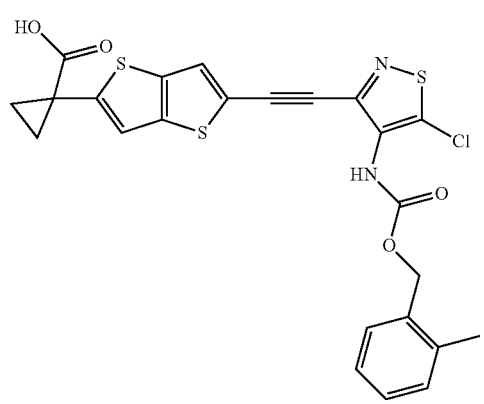 [SMILES: Cc1ccccc1COC(=O)Nc1c(C#Cc2cc3sc(C4(C(=O)O)CC4)cc3s2)nsc1Cl]
TABLE 17-continued
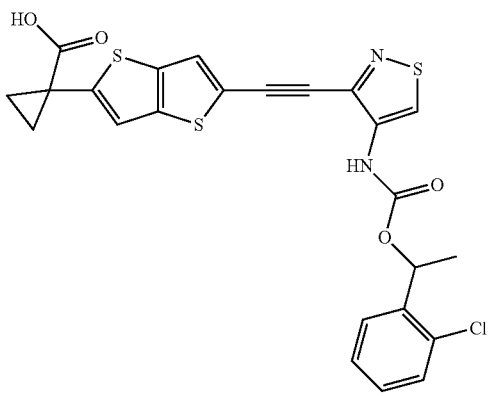 [SMILES: CC(OC(=O)Nc1csnc1C#Cc1cc2sc(C3(C(=O)O)CC3)cc2s1)c1ccccc1Cl]
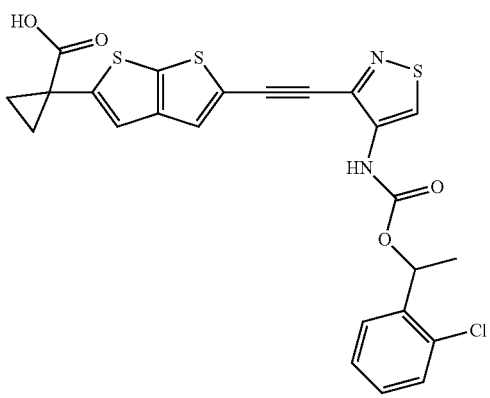 [SMILES: CC(OC(=O)Nc1csnc1C#Cc1cc2cc(C3(C(=O)O)CC3)sc2s1)c1ccccc1Cl]
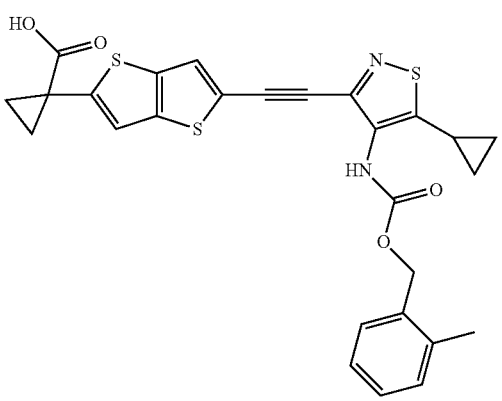 [SMILES: Cc1ccccc1COC(=O)Nc1c(C#Cc2cc3sc(C4(C(=O)O)CC4)cc3s2)nsc1C1CC1]
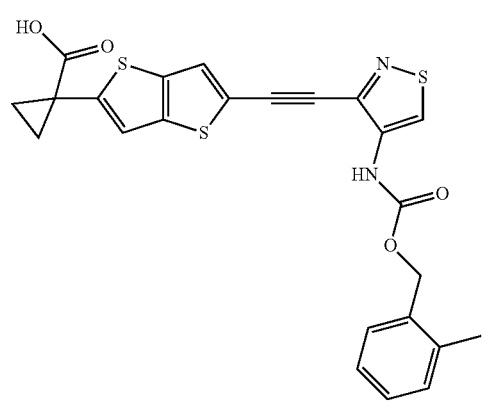 [SMILES: Cc1ccccc1COC(=O)Nc1csnc1C#Cc1cc2sc(C3(C(=O)O)CC3)cc2s1]

TABLE 17-continued
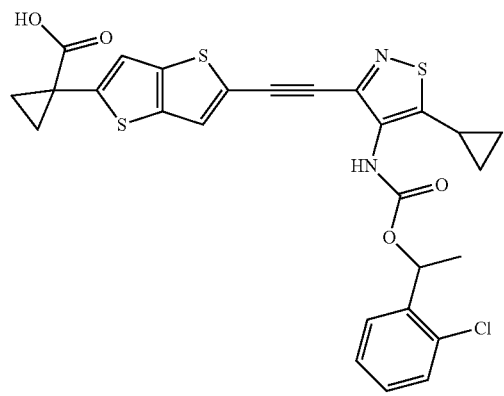 [SMILES: CC(OC(=O)Nc1c(C#Cc2cc3sc(C4(C(=O)O)CC4)cc3s2)nsc1C1CC1)c1ccccc1Cl]
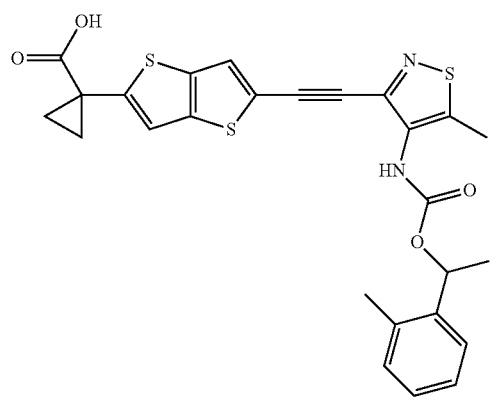
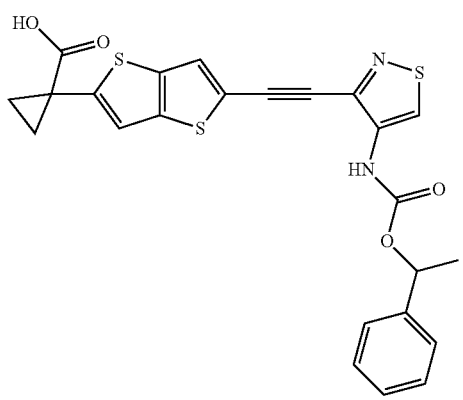
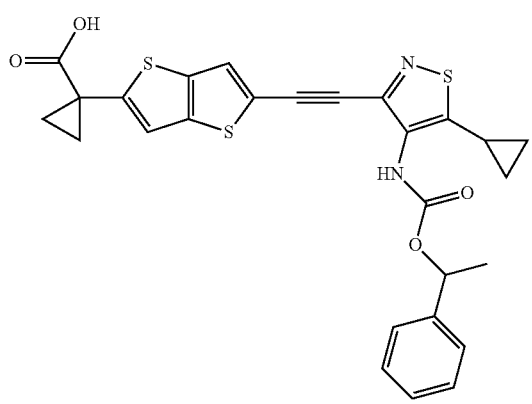 [SMILES: CC(OC(=O)Nc1c(C#Cc2cc3sc(C4(C(=O)O)CC4)cc3s2)nsc1C1CC1)c1ccccc1]
TABLE 17-continued
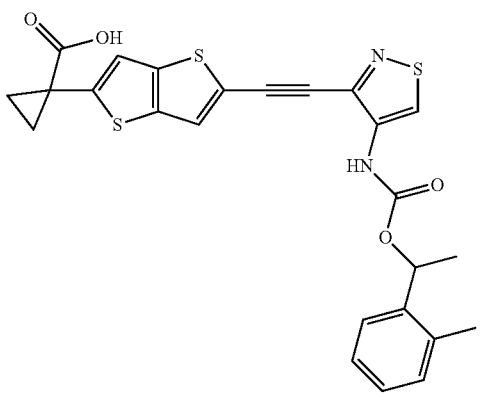 [SMILES: Cc1ccccc1C(C)OC(=O)Nc1csnc1C#Cc1cc2sc(C3(C(=O)O)CC3)cc2s1]
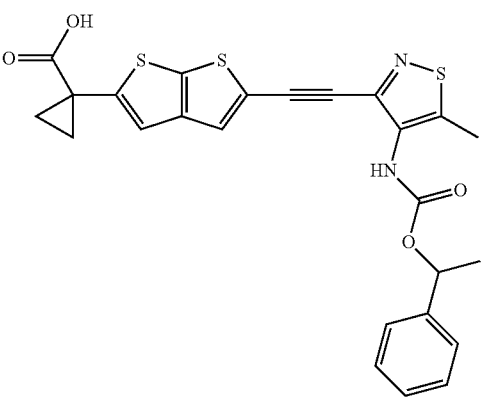 [SMILES: Cc1snc(C#Cc2cc3cc(C4(C(=O)O)CC4)sc3s2)c1NC(=O)OC(C)c1ccccc1]
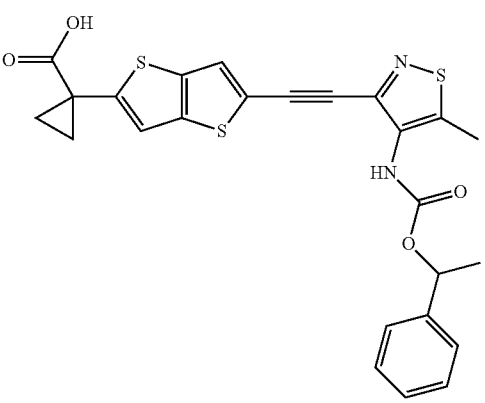 [SMILES: Cc1snc(C#Cc2cc3sc(C4(C(=O)O)CC4)cc3s2)c1NC(=O)OC(C)c1ccccc1]
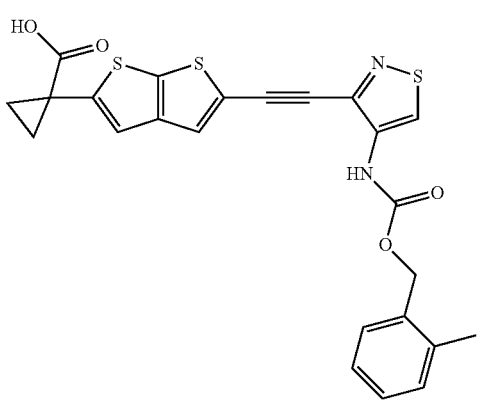 [SMILES: Cc1ccccc1COC(=O)Nc1csnc1C#Cc1cc2cc(C3(C(=O)O)CC3)sc2s1]

TABLE 17-continued
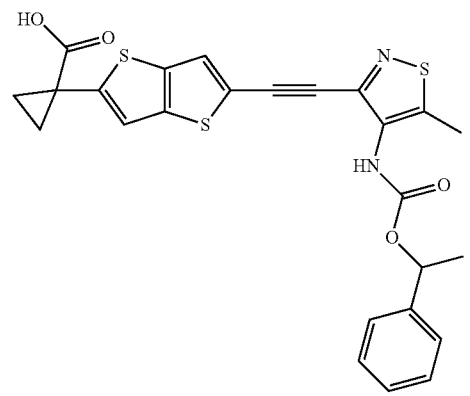
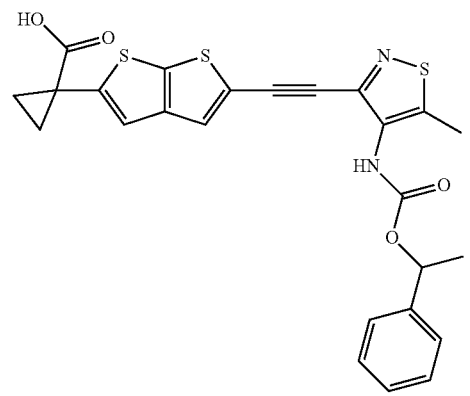
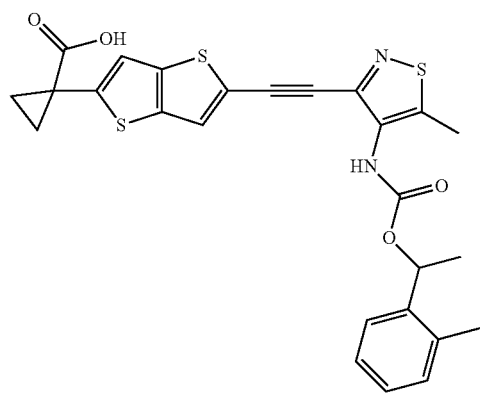 [SMILES: Cc1ccccc1C(C)OC(=O)Nc1c(C#Cc2cc3sc(C4(C(=O)O)CC4)cc3s2)nsc1C]
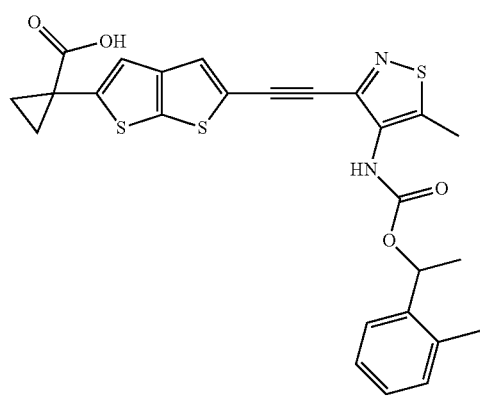
TABLE 17-continued
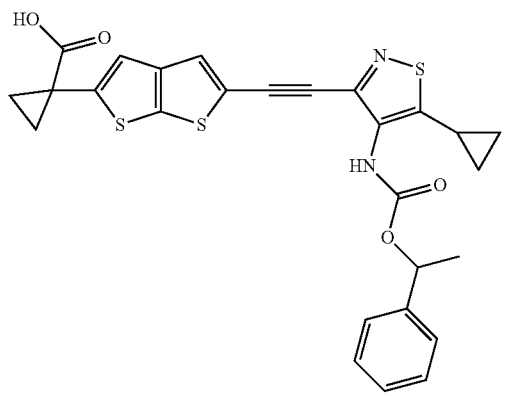
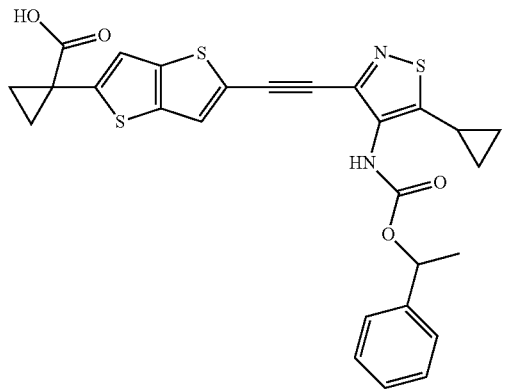 [SMILES: CC(OC(=O)Nc1c(C#Cc2cc3sc(C4(C(=O)O)CC4)cc3s2)nsc1C1CC1)c1ccccc1]
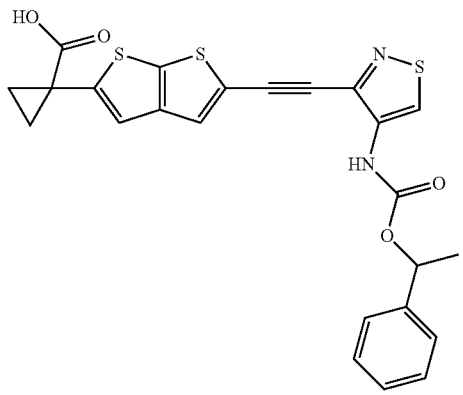 [SMILES: CC(OC(=O)Nc1csnc1C#Cc1cc2cc(C3(C(=O)O)CC3)sc2s1)c1ccccc1]
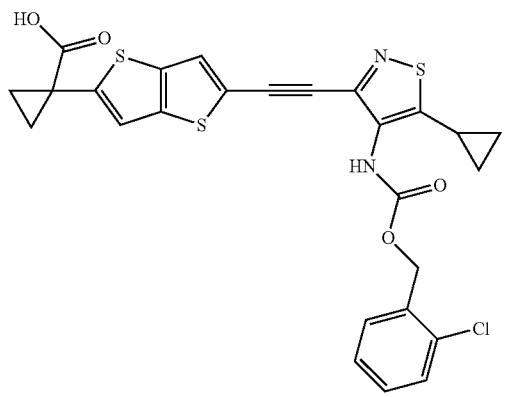 [SMILES: O=C(Nc1c(C#Cc2cc3sc(C4(C(=O)O)CC4)cc3s2)nsc1C1CC1)OCc1ccccc1Cl]

TABLE 17-continued
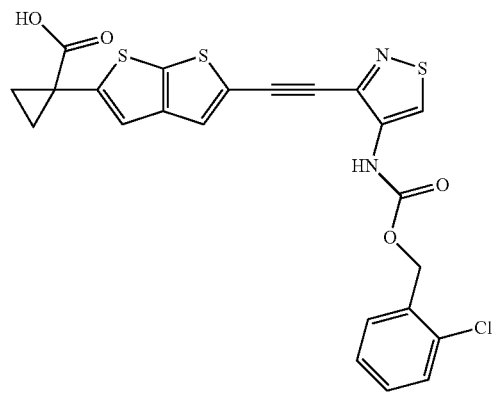 [SMILES: O=C(Nc1csnc1C#Cc1cc2cc(C3(C(=O)O)CC3)sc2s1)OCc1ccccc1Cl]
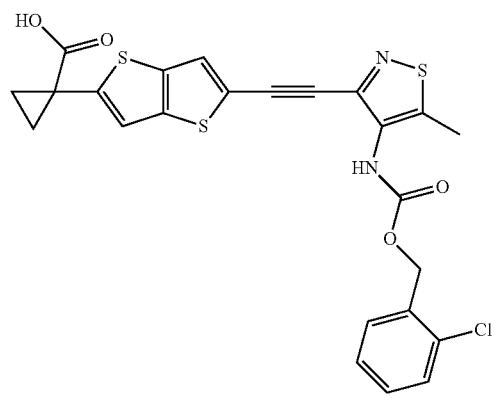 [SMILES: Cc1snc(C#Cc2cc3sc(C4(C(=O)O)CC4)cc3s2)c1NC(=O)OCc1ccccc1Cl]
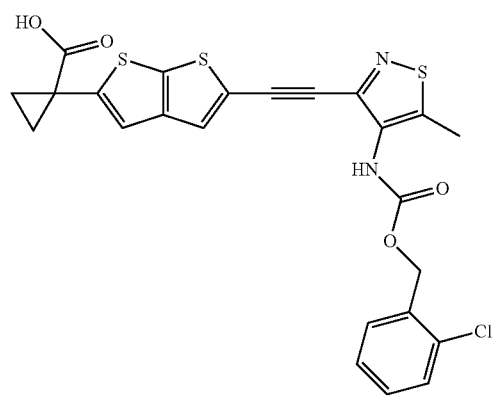 [SMILES: Cc1snc(C#Cc2cc3cc(C4(C(=O)O)CC4)sc3s2)c1NC(=O)OCc1ccccc1Cl]
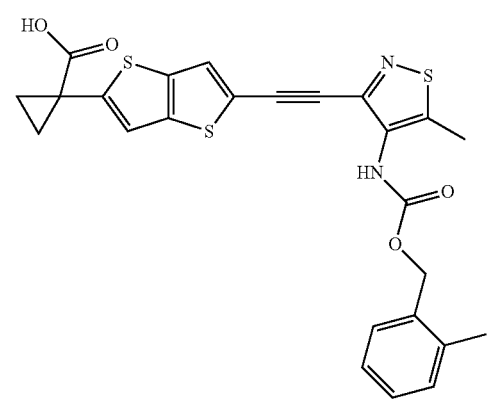 [SMILES: Cc1ccccc1COC(=O)Nc1c(C#Cc2cc3sc(C4(C(=O)O)CC4)cc3s2)nsc1C]
TABLE 17-continued
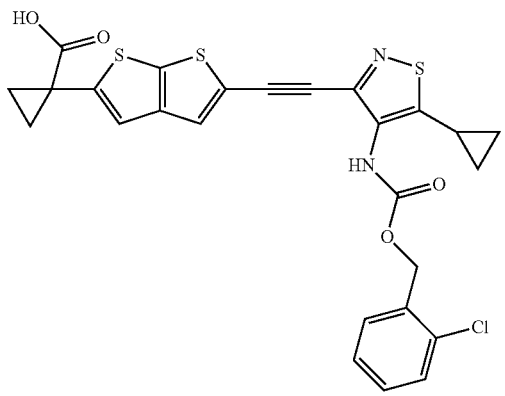
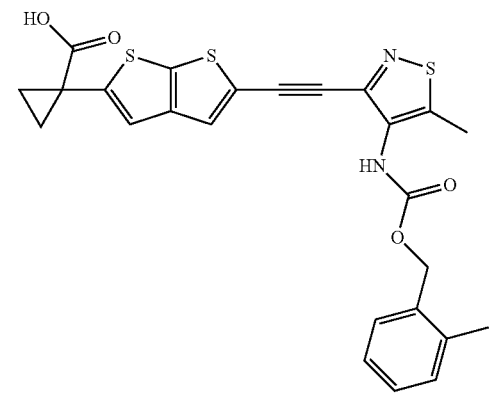 [SMILES: Cc1ccccc1COC(=O)Nc1c(C#Cc2cc3cc(C4(C(=O)O)CC4)sc3s2)nsc1C]
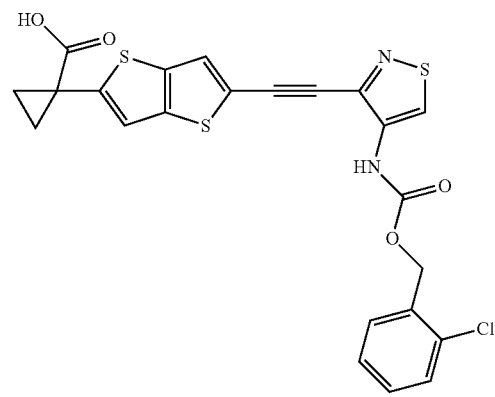 [SMILES: O=C(Nc1csnc1C#Cc1cc2sc(C3(C(=O)O)CC3)cc2s1)OCc1ccccc1Cl]
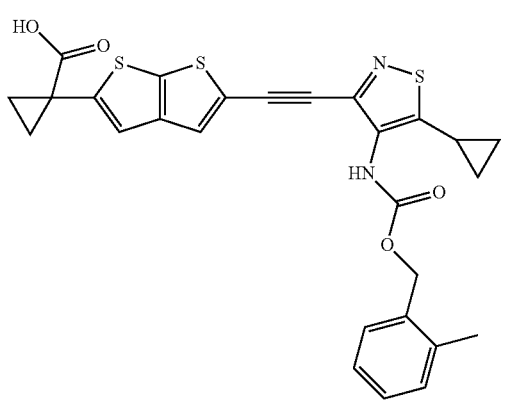 [SMILES: Cc1ccccc1COC(=O)Nc1c(C#Cc2cc3cc(C4(C(=O)O)CC4)sc3s2)nsc1C1CC1]

TABLE 17-continued
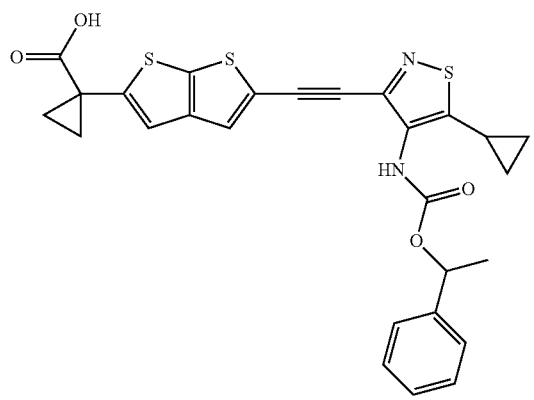 [SMILES: CC(OC(=O)Nc1c(C#Cc2cc3cc(C4(C(=O)O)CC4)sc3s2)nsc1C1CC1)c1ccccc1]
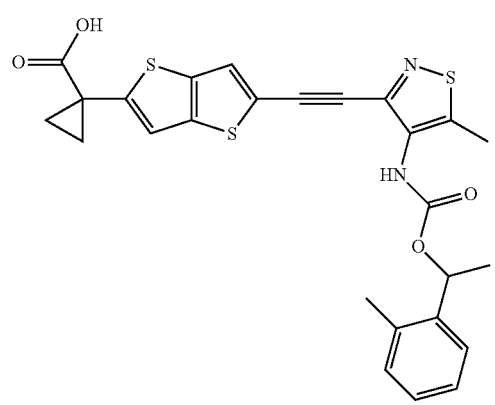 [SMILES: Cc1ccccc1C(C)OC(=O)Nc1c(C#Cc2cc3sc(C4(C(=O)O)CC4)cc3s2)nsc1C]
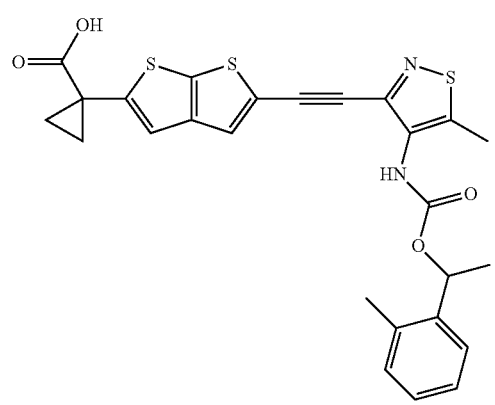 [SMILES: Cc1ccccc1C(C)OC(=O)Nc1c(C#Cc2cc3cc(C4(C(=O)O)CC4)sc3s2)nsc1C]
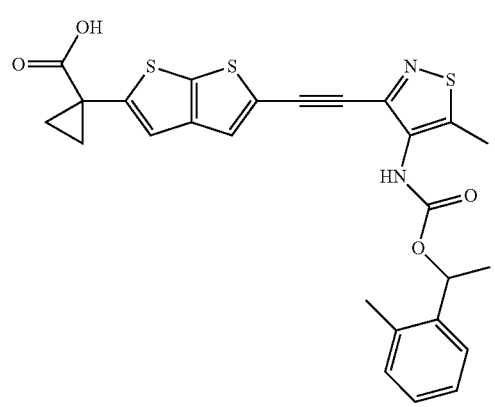 [SMILES: Cc1ccccc1C(C)OC(=O)Nc1c(C#Cc2cc3cc(C4(C(=O)O)CC4)sc3s2)nsc1C]
TABLE 17-continued
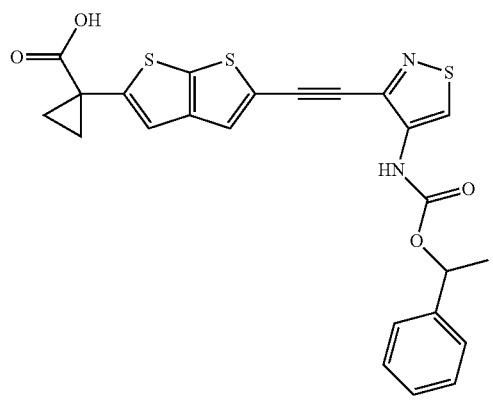 [SMILES: CC(OC(=O)Nc1csnc1C#Cc1cc2cc(C3(C(=O)O)CC3)sc2s1)c1ccccc1]
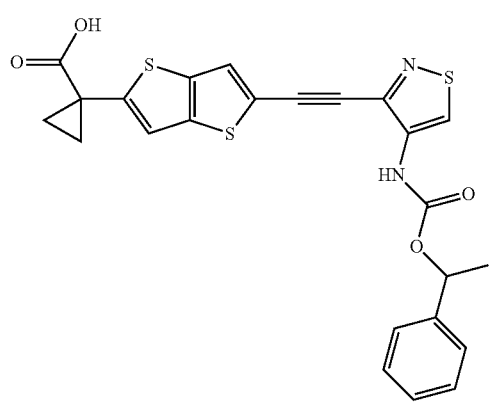 [SMILES: CC(OC(=O)Nc1csnc1C#Cc1cc2sc(C3(C(=O)O)CC3)cc2s1)c1ccccc1]
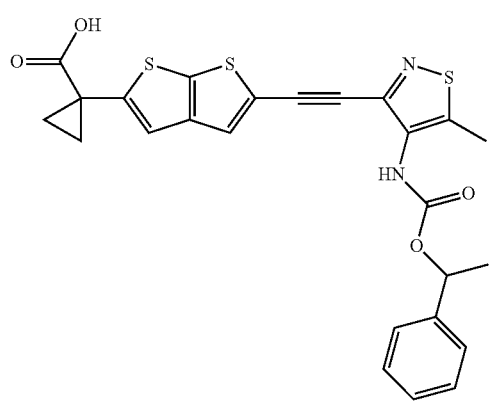 [SMILES: Cc1snc(C#Cc2cc3cc(C4(C(=O)O)CC4)sc3s2)c1NC(=O)OC(C)c1ccccc1]
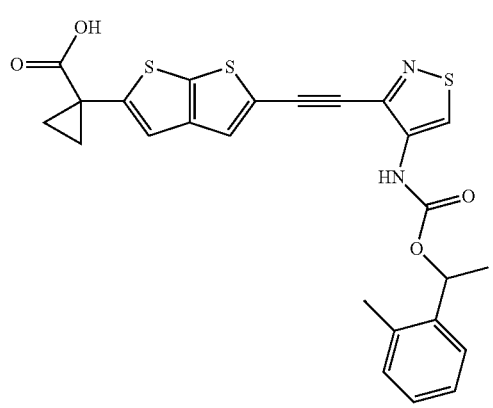 [SMILES: Cc1ccccc1C(C)OC(=O)Nc1csnc1C#Cc1cc2cc(C3(C(=O)O)CC3)sc2s1]

TABLE 17-continued
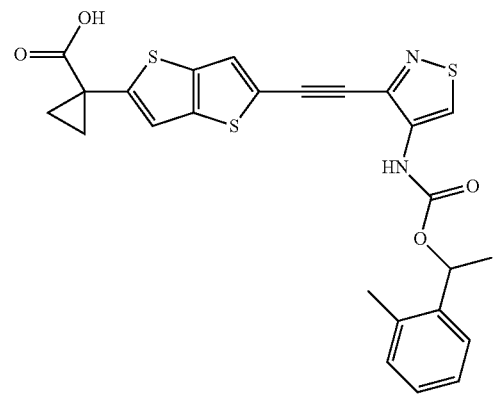 [SMILES: Cc1ccccc1C(C)OC(=O)Nc1csnc1C#Cc1cc2sc(C3(C(=O)O)CC3)cc2s1]
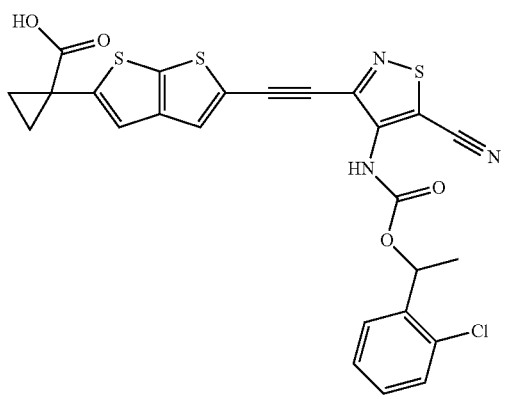 [SMILES: CC(OC(=O)Nc1c(C#Cc2cc3cc(C4(C(=O)O)CC4)sc3s2)nsc1C#N)c1ccccc1Cl]
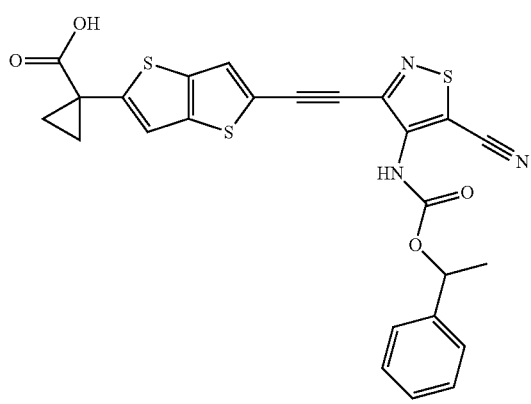 [SMILES: CC(OC(=O)Nc1c(C#Cc2cc3sc(C4(C(=O)O)CC4)cc3s2)nsc1C#N)c1ccccc1]
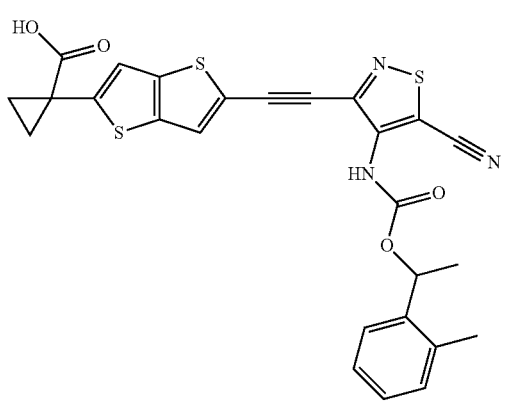 [SMILES: Cc1ccccc1C(C)OC(=O)Nc1c(C#Cc2cc3sc(C4(C(=O)O)CC4)cc3s2)nsc1C#N]
TABLE 17-continued
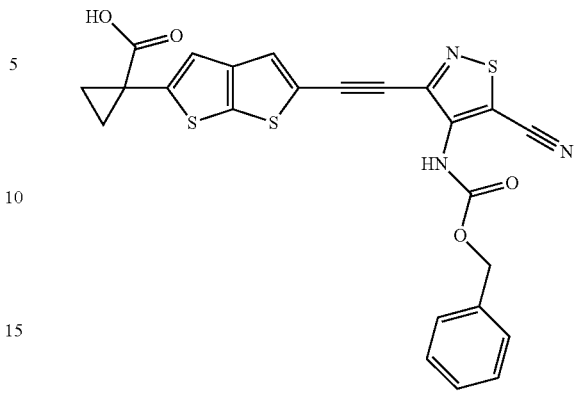
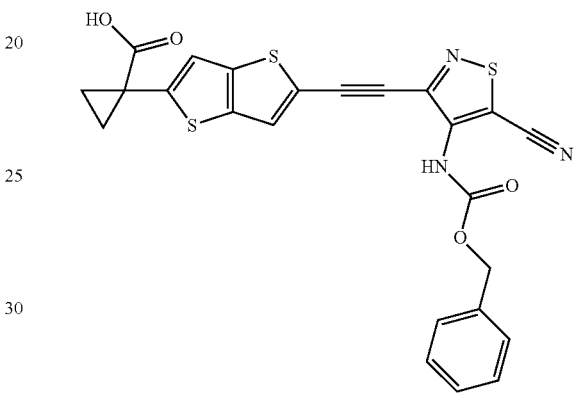
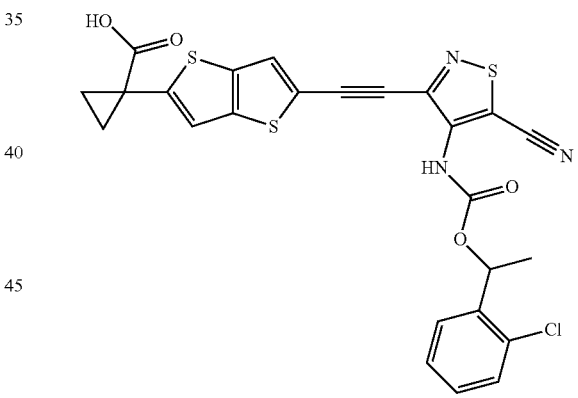
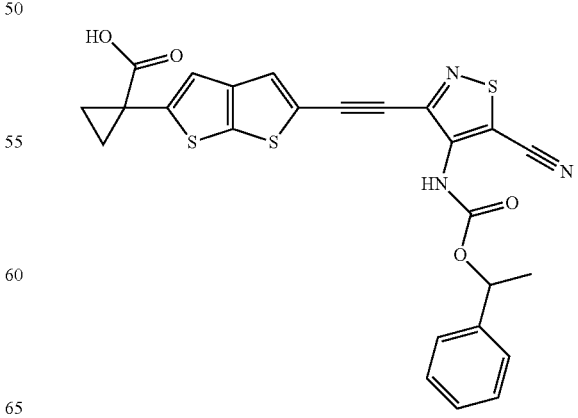

| 1477 | 1478 |
|---|---|
| 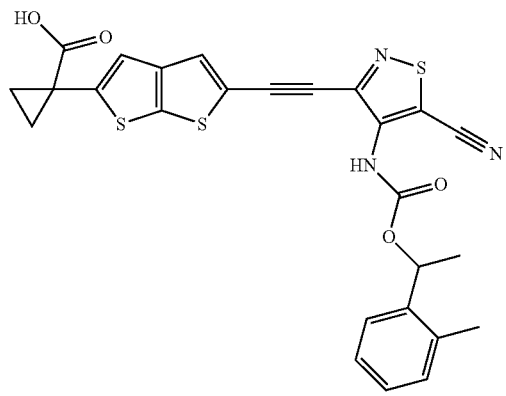 | 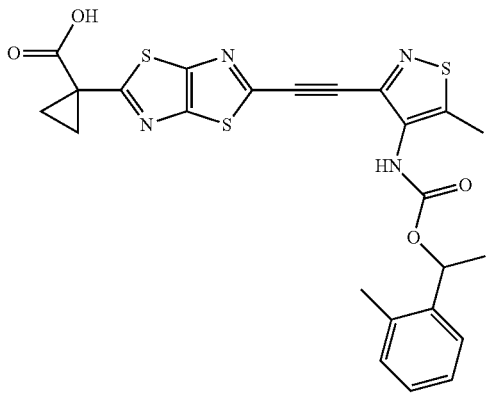 |
| 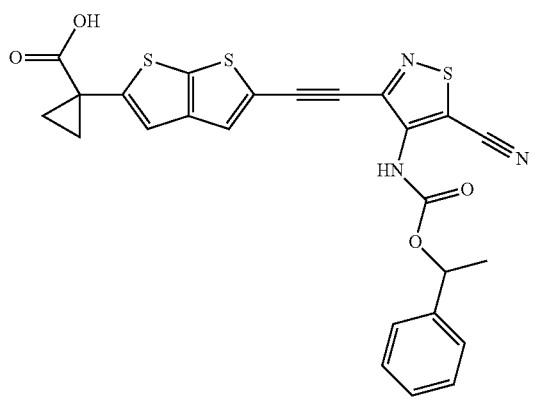 [SMILES: CC(OC(=O)Nc1c(C#Cc2cc3cc(C4(C(=O)O)CC4)sc3s2)nsc1C#N)c1ccccc1] | 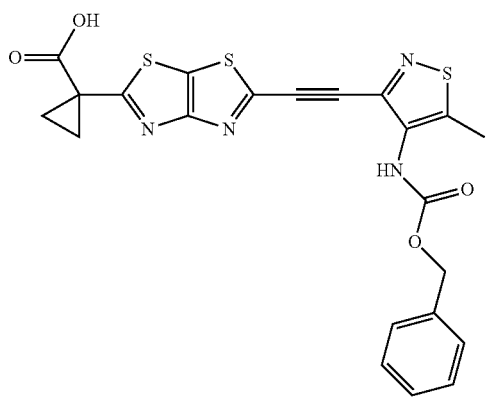 |
| 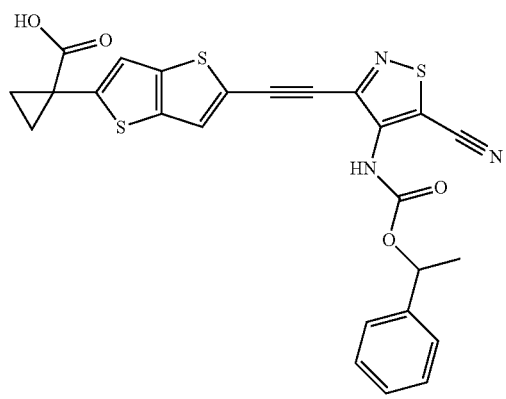 | 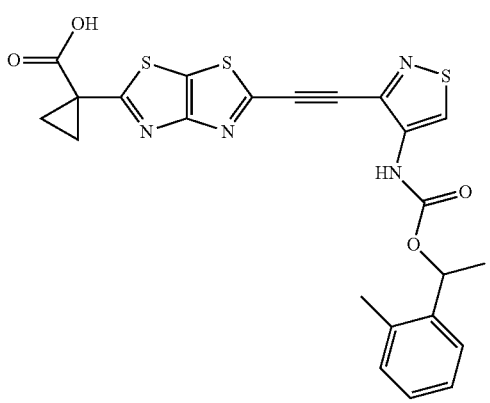 |
| 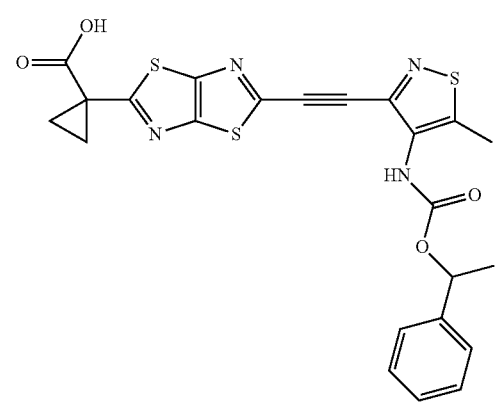 [SMILES: Cc1snc(C#Cc2nc3sc(C4(C(=O)O)CC4)nc3s2)c1NC(=O)OC(C)c1ccccc1] | 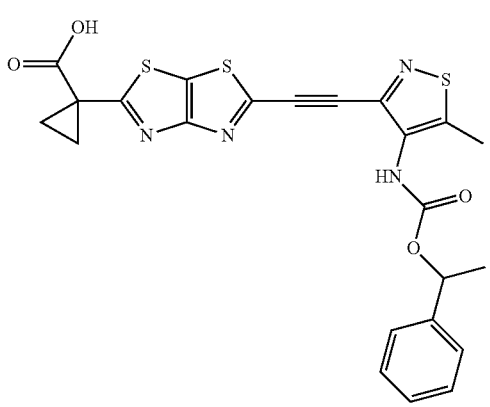 [SMILES: Cc1snc(C#Cc2nc3nc(C4(C(=O)O)CC4)sc3s2)c1NC(=O)OC(C)c1ccccc1] |

TABLE 17-continued
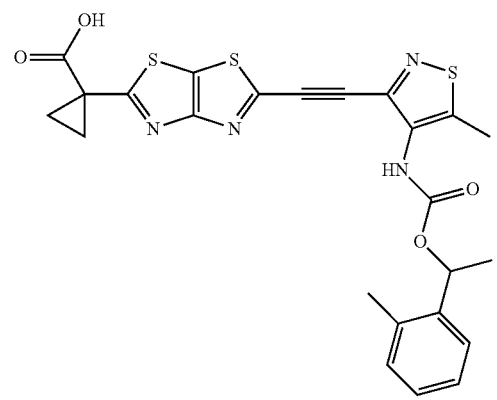
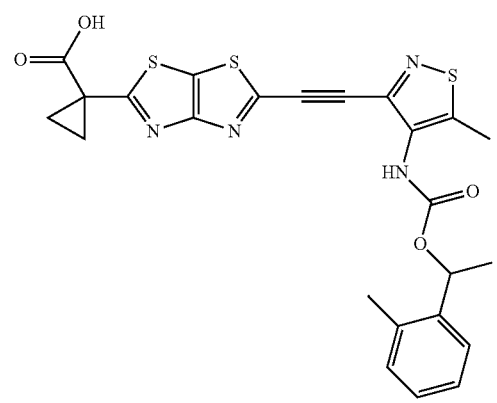
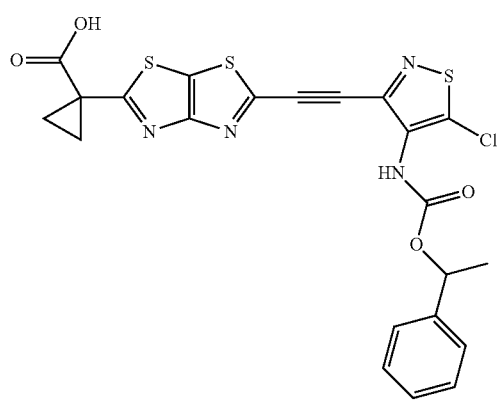
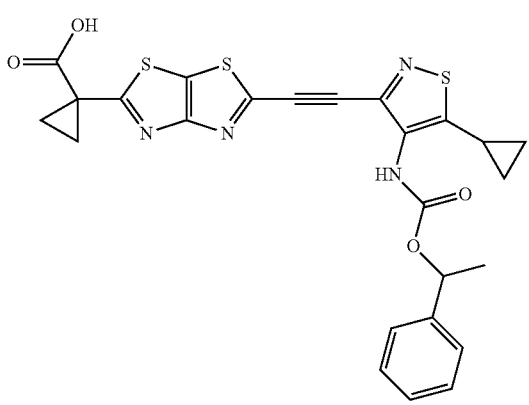
TABLE 17-continued
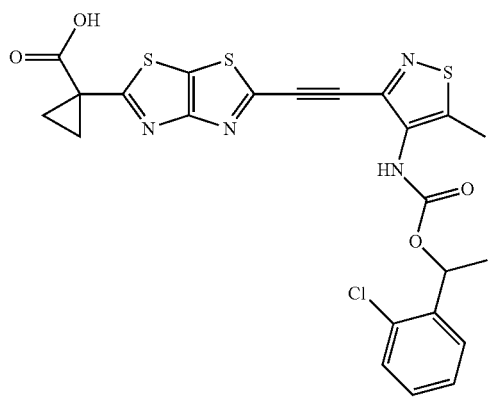 [SMILES: Cc1snc(C#Cc2nc3nc(C4(C(=O)O)CC4)sc3s2)c1NC(=O)OC(C)c1ccccc1Cl]
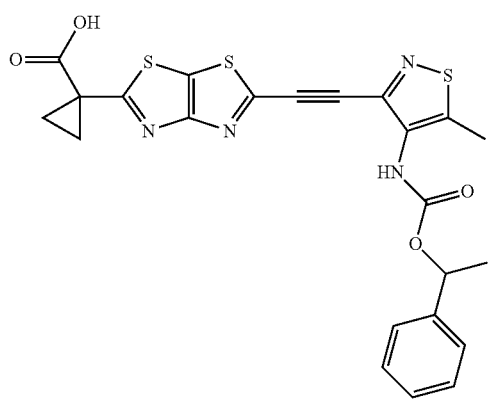
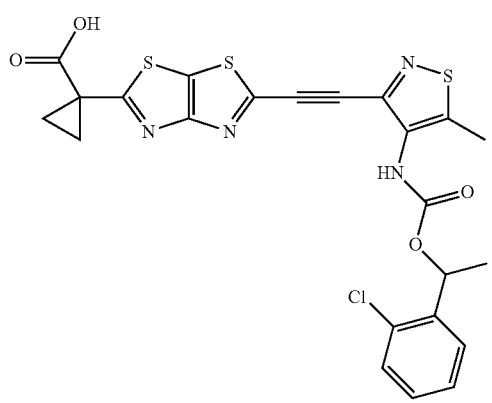 [SMILES: Cc1snc(C#Cc2nc3nc(C4(C(=O)O)CC4)sc3s2)c1NC(=O)OC(C)c1ccccc1Cl]
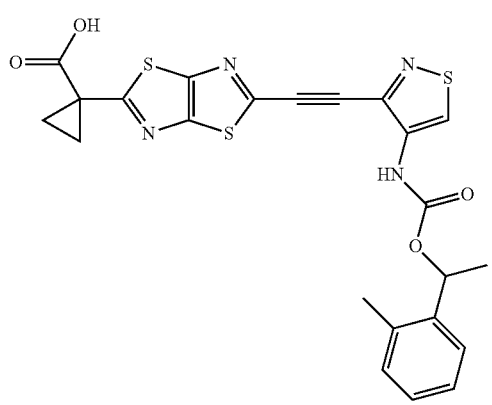

1481
TABLE 17-continued
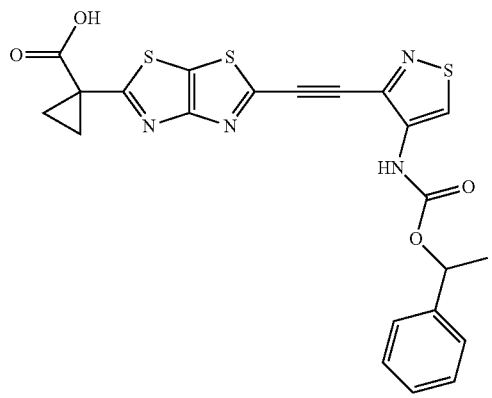 [SMILES: CC(OC(=O)Nc1csnc1C#Cc1nc2nc(C3(C(=O)O)CC3)sc2s1)c1ccccc1]
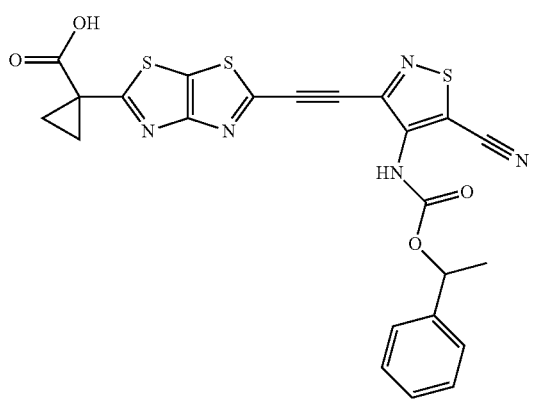
or pharmaceutically acceptable salts thereof.
34. The compound or pharmaceutically acceptable salt thereof claim 1, selected from compounds of Table 18 having the following structures:
TABLE 18
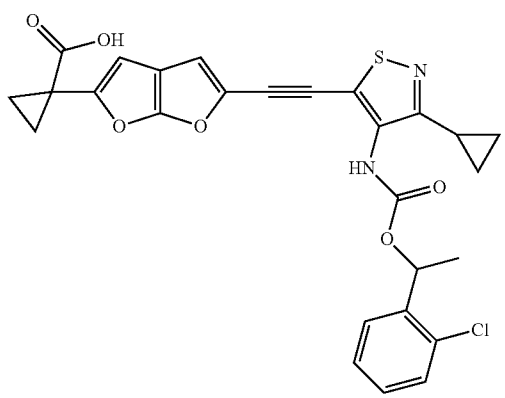 [SMILES: CC(OC(=O)Nc1c(C2CC2)nsc1C#Cc1cc2cc(C3(C(=O)O)CC3)oc2o1)c1ccccc1Cl]
1482
TABLE 18-continued
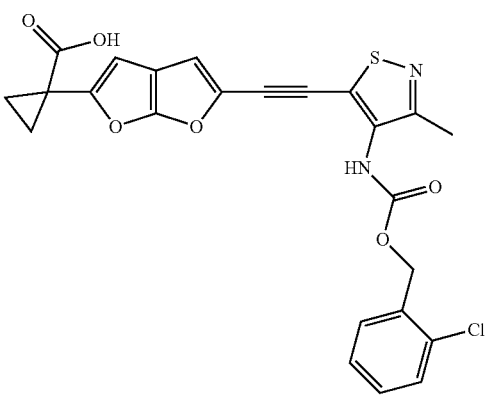 [SMILES: Cc1nsc(C#Cc2cc3cc(C4(C(=O)O)CC4)oc3o2)c1NC(=O)OCc1ccccc1Cl]
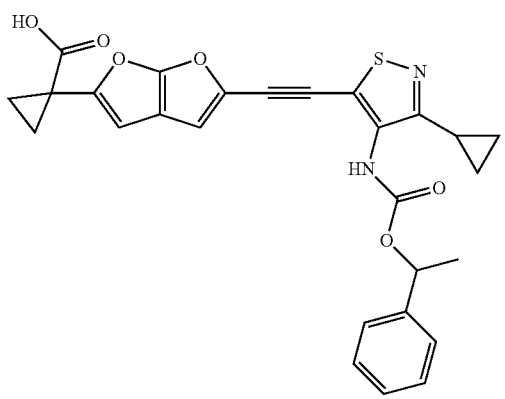
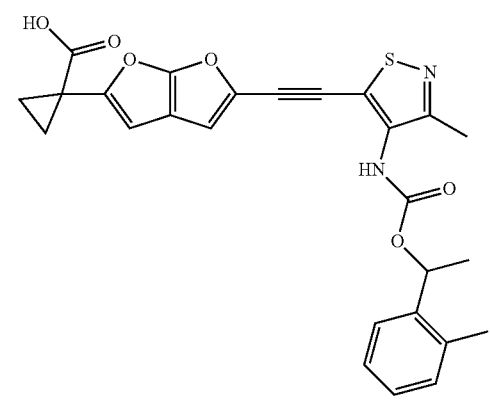
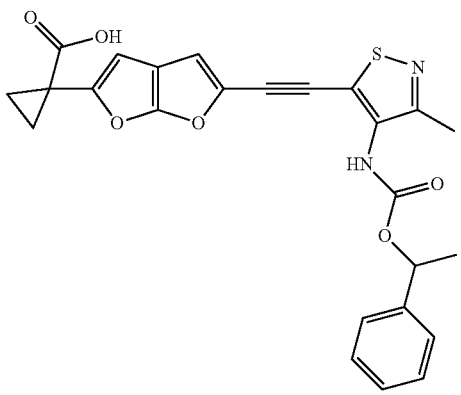 [SMILES: Cc1nsc(C#Cc2cc3cc(C4(C(=O)O)CC4)oc3o2)c1NC(=O)OC(C)c1ccccc1]

TABLE 18-continued
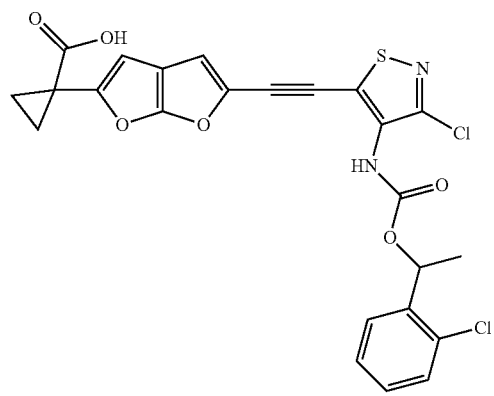 [SMILES: CC(OC(=O)Nc1c(Cl)nsc1C#Cc1cc2cc(C3(C(=O)O)CC3)oc2o1)c1ccccc1Cl]
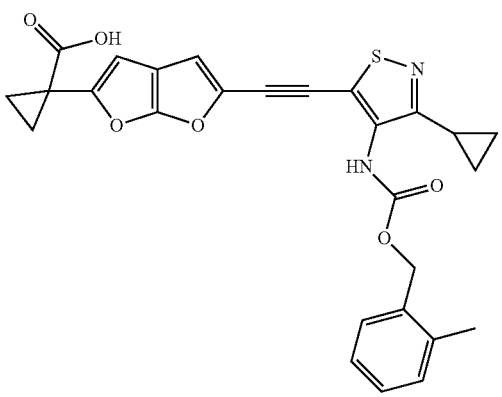 [SMILES: Cc1ccccc1COC(=O)Nc1c(C2CC2)nsc1C#Cc1cc2cc(C3(C(=O)O)CC3)oc2o1]
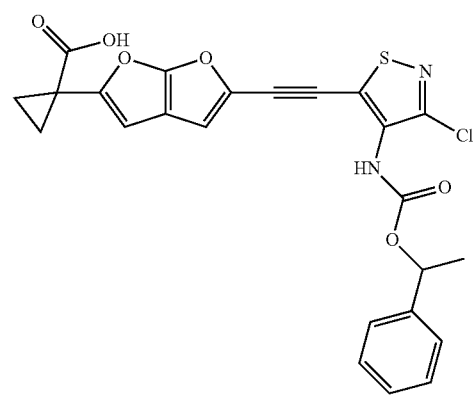
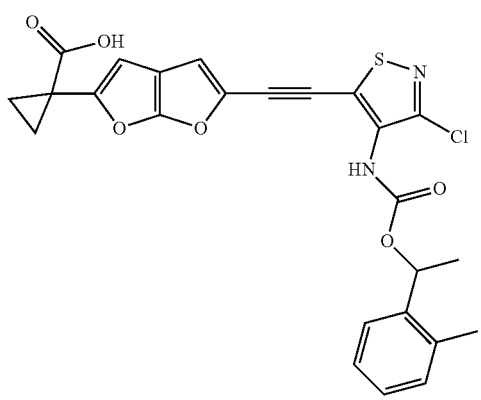 [SMILES: Cc1ccccc1C(C)OC(=O)Nc1c(Cl)nsc1C#Cc1cc2cc(C3(C(=O)O)CC3)oc2o1]
TABLE 18-continued
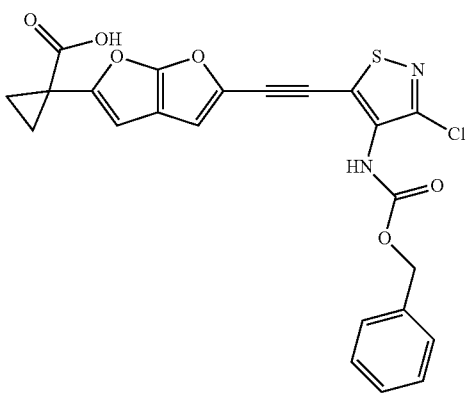 [SMILES: O=C(Nc1c(Cl)nsc1C#Cc1cc2cc(C3(C(=O)O)CC3)oc2o1)OCc1ccccc1]
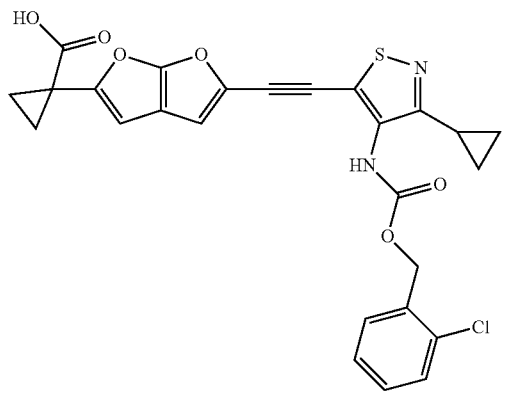 [SMILES: O=C(Nc1c(C2CC2)nsc1C#Cc1cc2cc(C3(C(=O)O)CC3)oc2o1)OCc1ccccc1Cl]
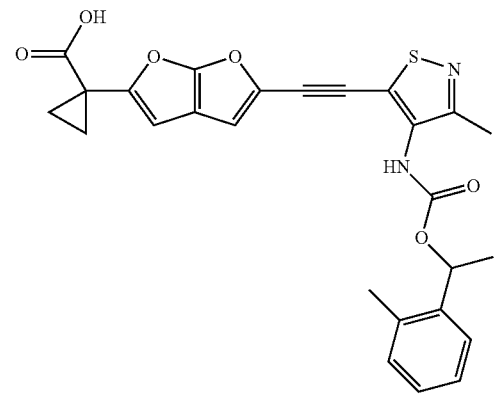
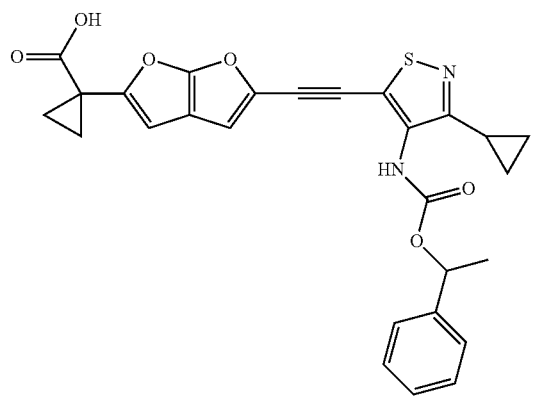

1485
TABLE 18-continued
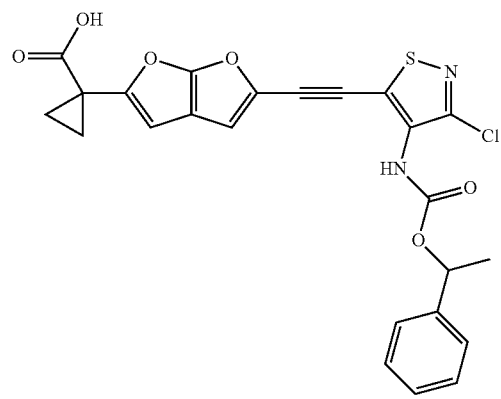
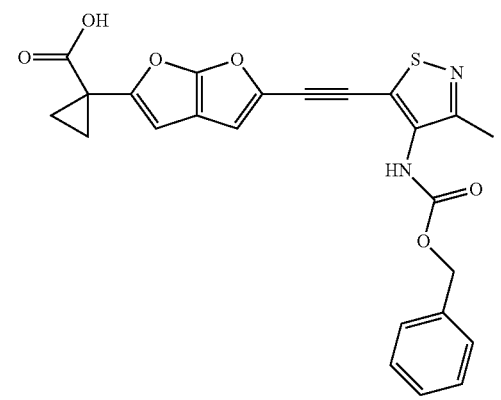
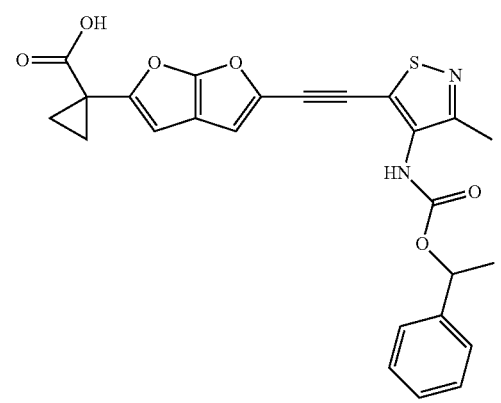
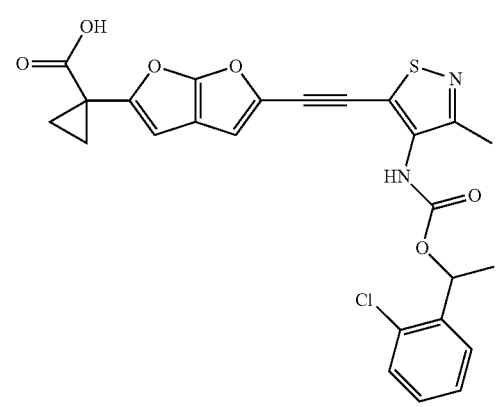
1486
TABLE 18-continued
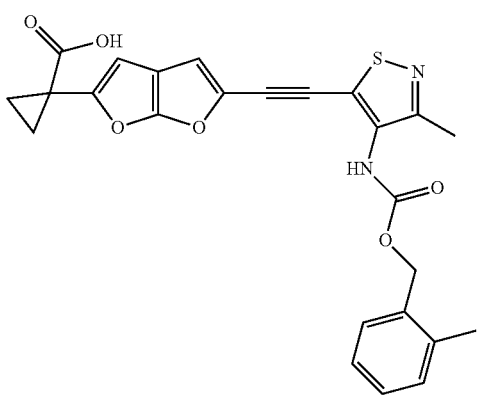 [SMILES: Cc1ccccc1COC(=O)Nc1c(C)nsc1C#Cc1cc2cc(C3(C(=O)O)CC3)oc2o1]
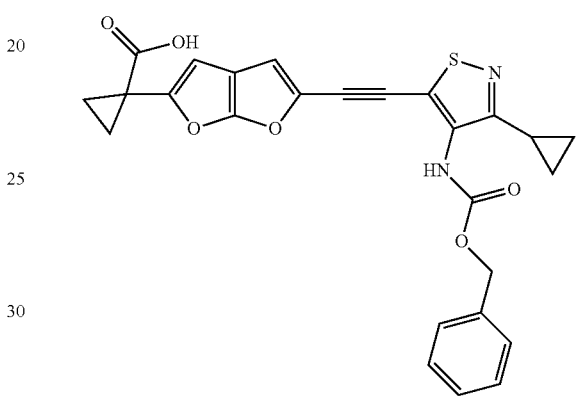
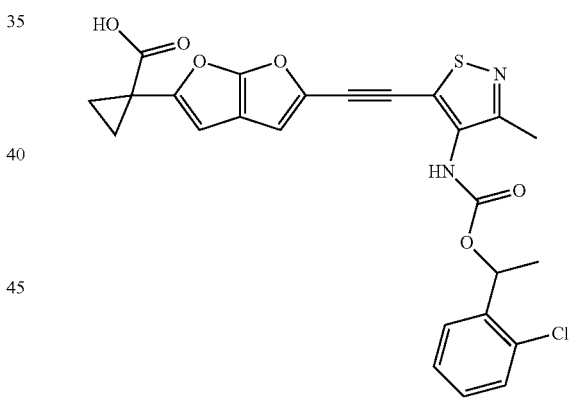
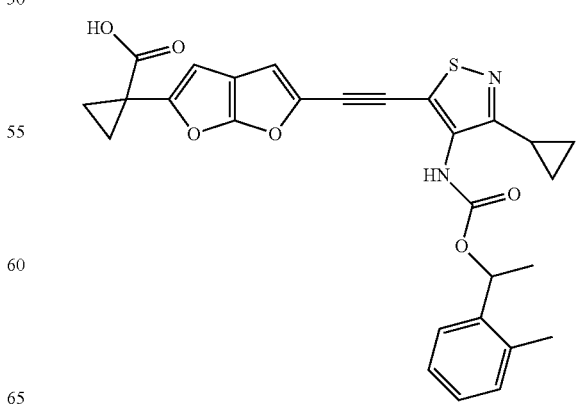

1487
TABLE 18-continued
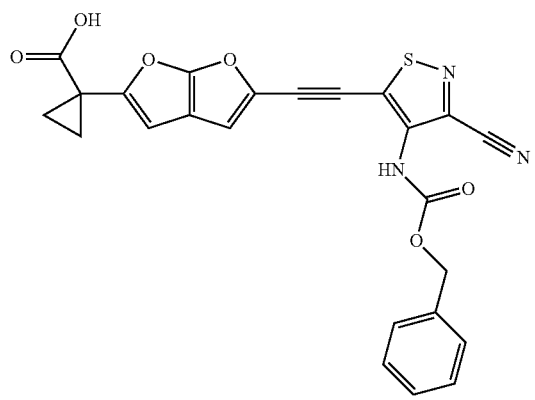
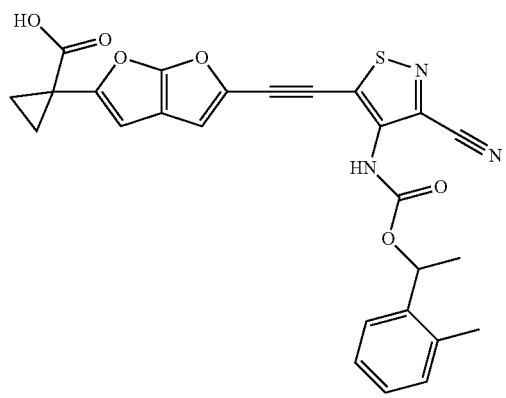 [SMILES: Cc1ccccc1C(C)OC(=O)Nc1c(C#N)nsc1C#Cc1cc2cc(C3(C(=O)O)CC3)oc2o1]
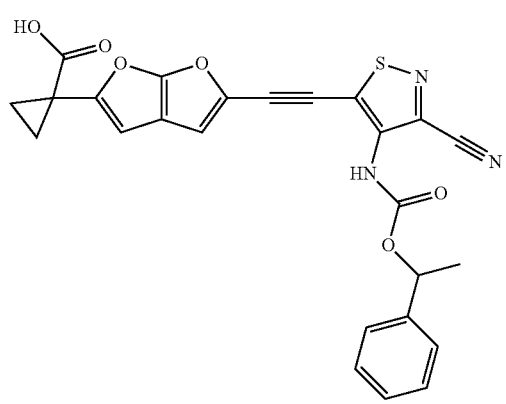
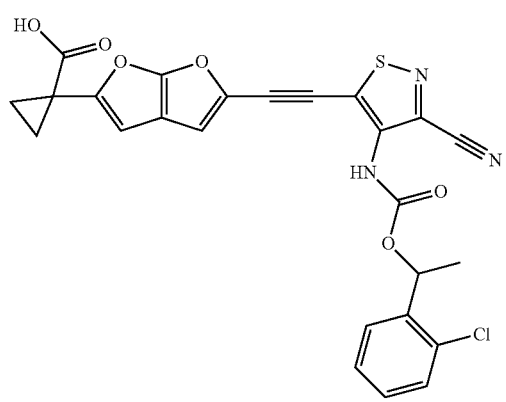 [SMILES: CC(OC(=O)Nc1c(C#N)nsc1C#Cc1cc2cc(C3(C(=O)O)CC3)oc2o1)c1ccccc1Cl]
1488
TABLE 18-continued
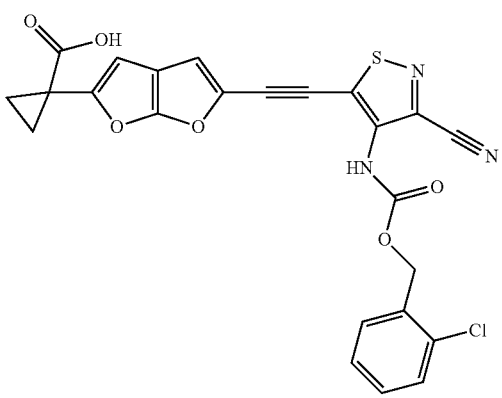 [SMILES: N#Cc1nsc(C#Cc2cc3cc(C4(C(=O)O)CC4)oc3o2)c1NC(=O)OCc1ccccc1Cl]
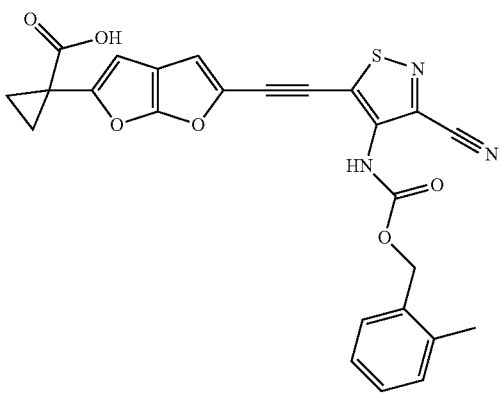 [SMILES: Cc1ccccc1COC(=O)Nc1c(C#N)nsc1C#Cc1cc2cc(C3(C(=O)O)CC3)oc2o1]
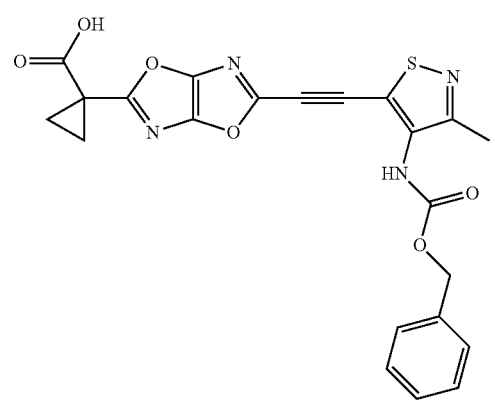
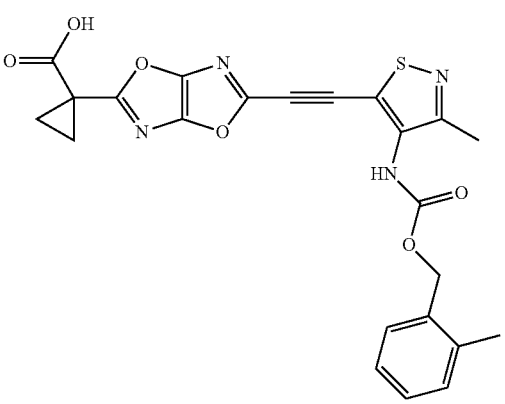

TABLE 18-continued
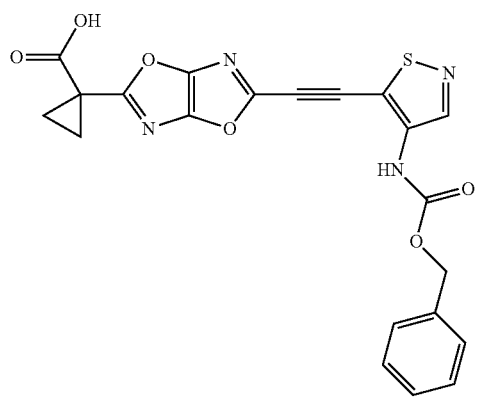
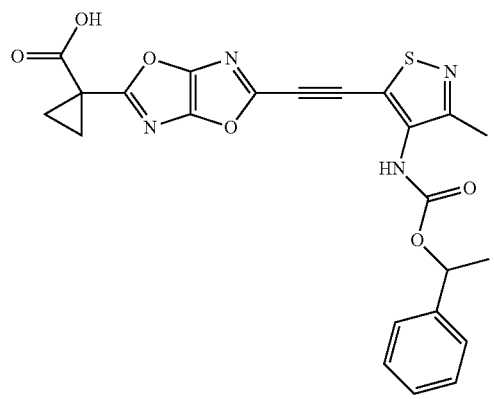
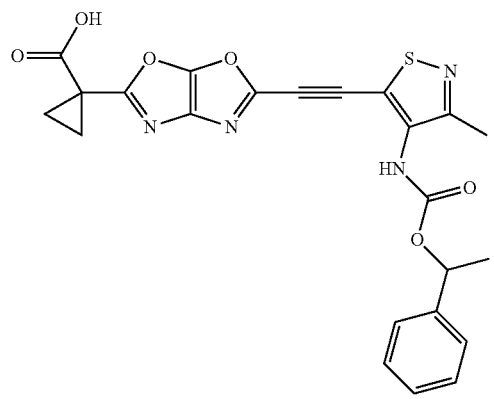
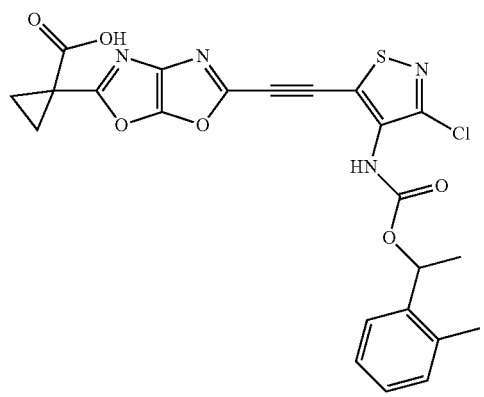 [SMILES: Cc1ccccc1C(C)OC(=O)Nc1c(Cl)nsc1C#Cc1nc2nc(C3(C(=O)O)CC3)oc2o1]
TABLE 18-continued
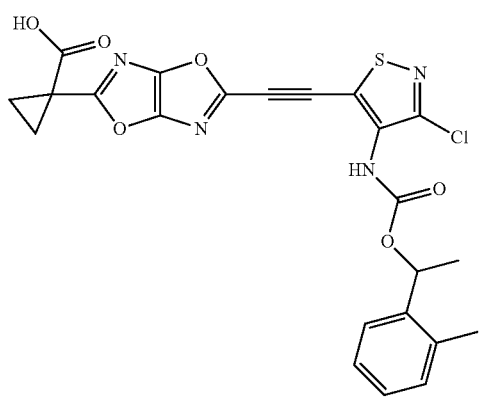 [SMILES: Cc1ccccc1C(C)OC(=O)Nc1c(Cl)nsc1C#Cc1nc2oc(C3(C(=O)O)CC3)nc2o1]
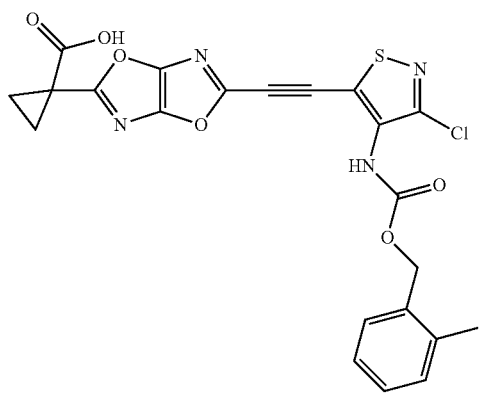
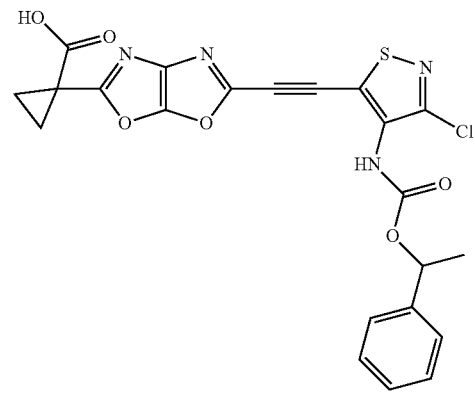 [SMILES: CC(OC(=O)Nc1c(Cl)nsc1C#Cc1nc2nc(C3(C(=O)O)CC3)oc2o1)c1ccccc1]
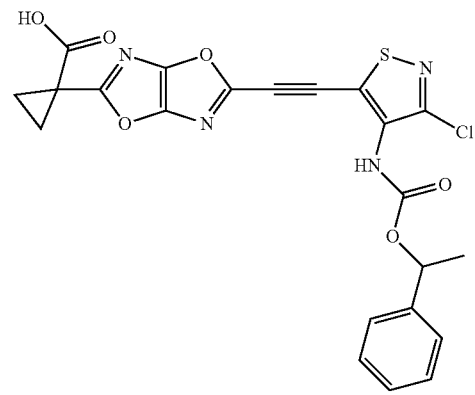 [SMILES: CC(OC(=O)Nc1c(Cl)nsc1C#Cc1nc2oc(C3(C(=O)O)CC3)nc2o1)c1ccccc1]

TABLE 18-continued
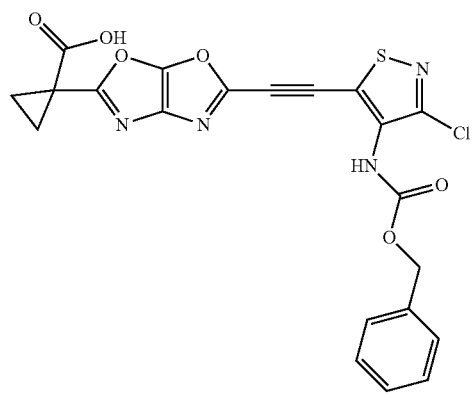
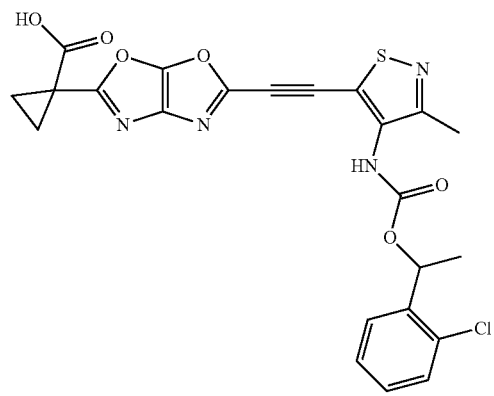
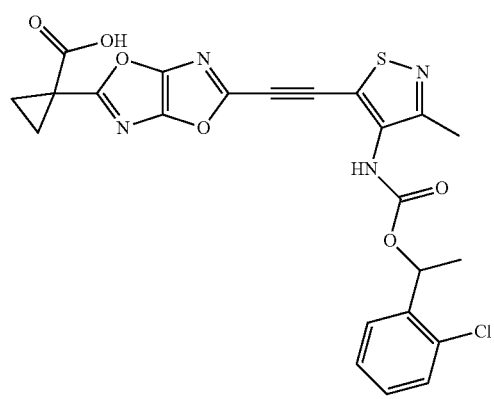
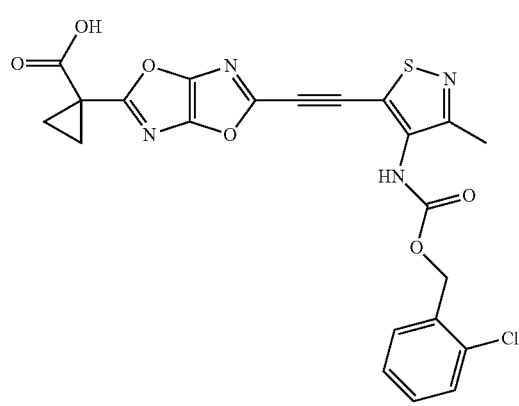
TABLE 18-continued
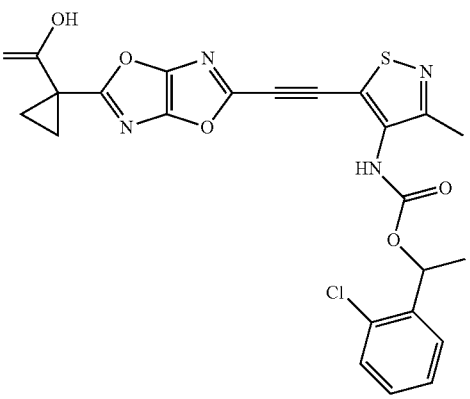
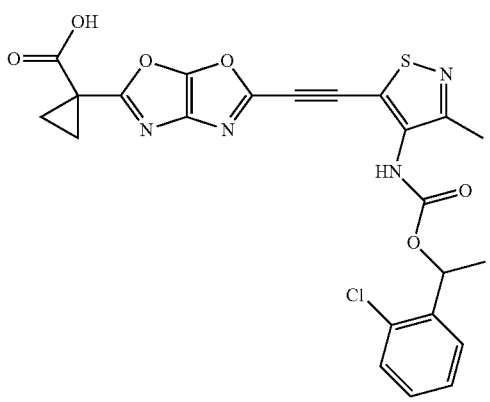
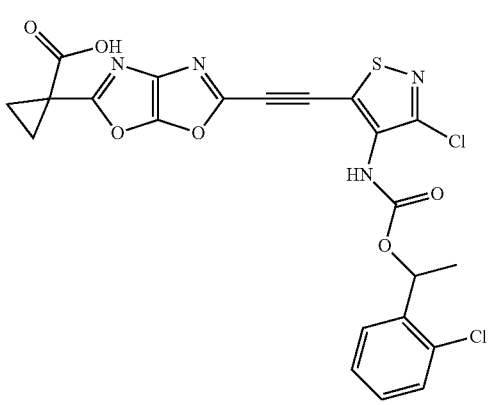 [SMILES: CC(OC(=O)Nc1c(Cl)nsc1C#Cc1nc2nc(C3(C(=O)O)CC3)oc2o1)c1ccccc1Cl]
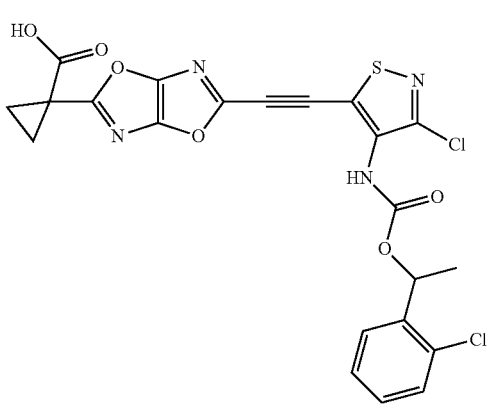

1493
TABLE 18-continued
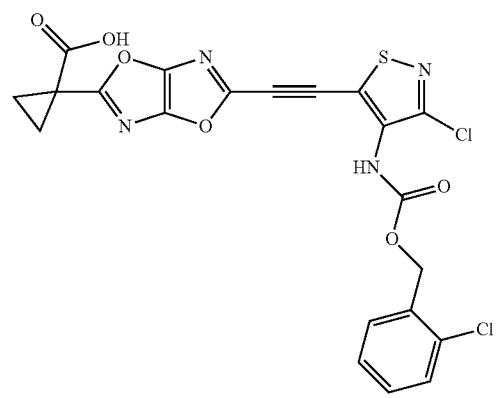 [SMILES: O=C(Nc1c(Cl)nsc1C#Cc1nc2oc(C3(C(=O)O)CC3)nc2o1)OCc1ccccc1Cl]
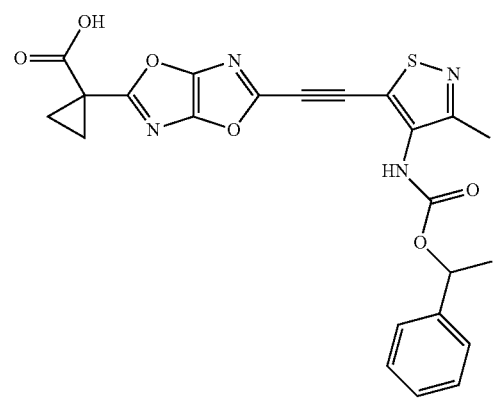
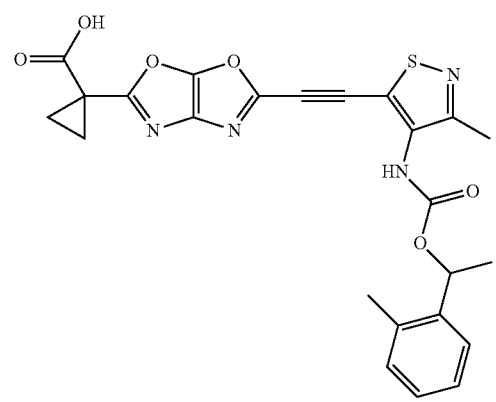
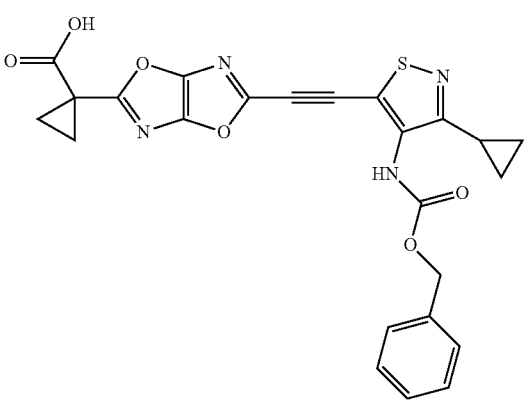
1494
TABLE 18-continued
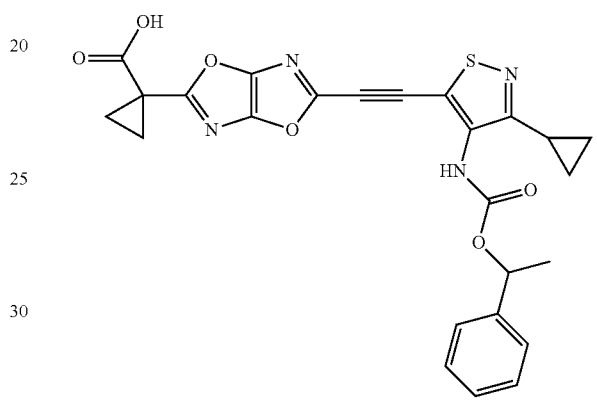
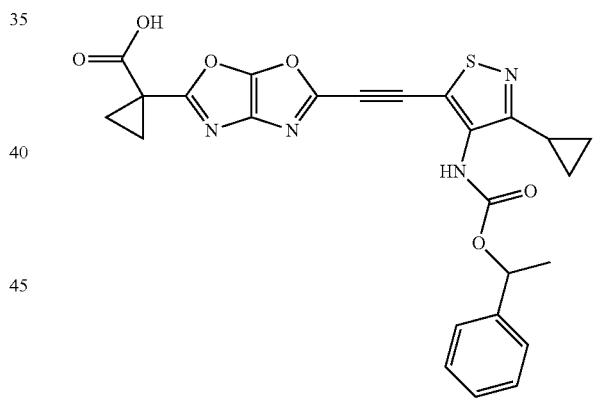
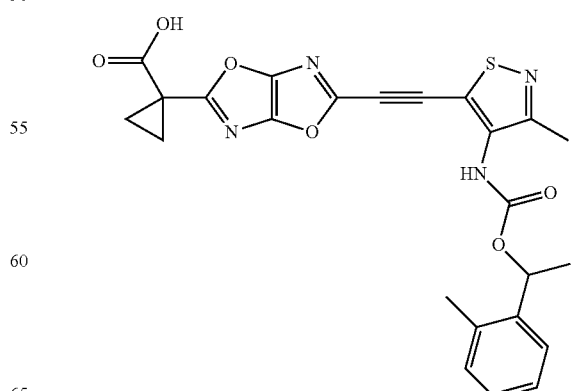
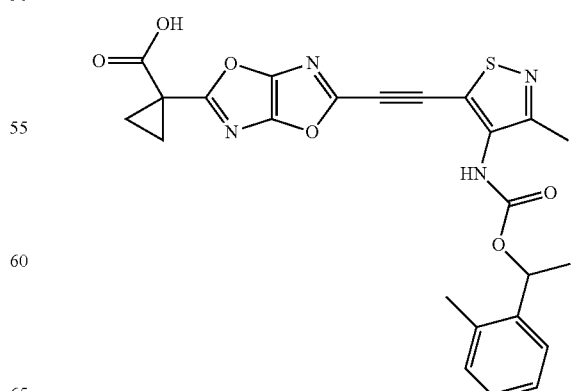

| 1495 | 1496 |
|---|---|
| 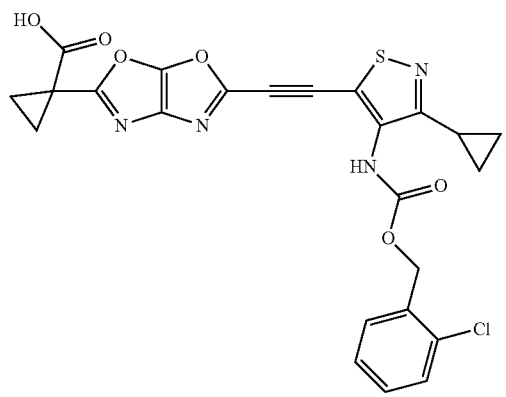 [SMILES: O=C(Nc1c(C2CC2)nsc1C#Cc1nc2nc(C3(C(=O)O)CC3)oc2o1)OCc1ccccc1Cl] | 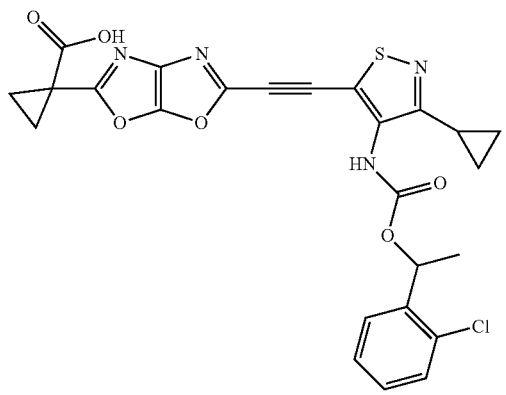 |
| 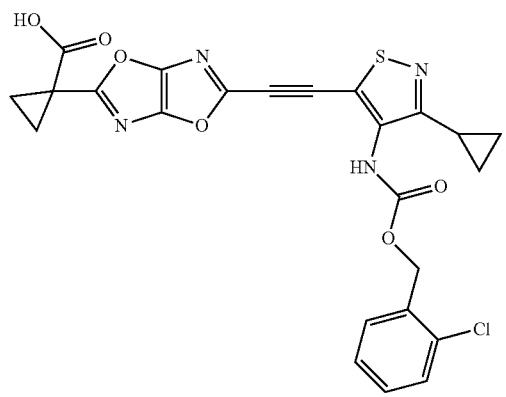 [SMILES: O=C(Nc1c(C2CC2)nsc1C#Cc1nc2oc(C3(C(=O)O)CC3)nc2o1)OCc1ccccc1Cl] | 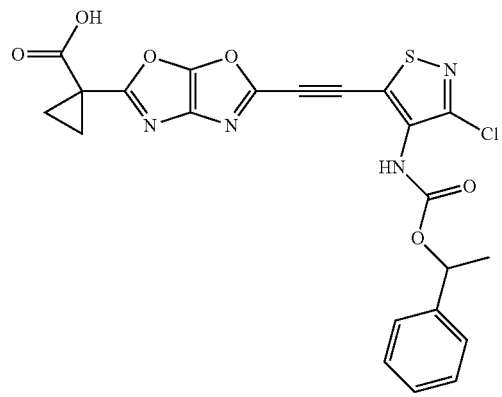 |
| 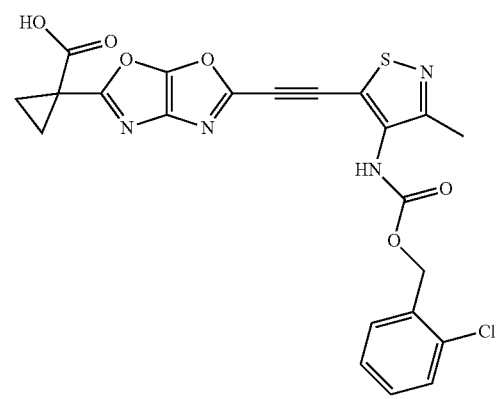 | 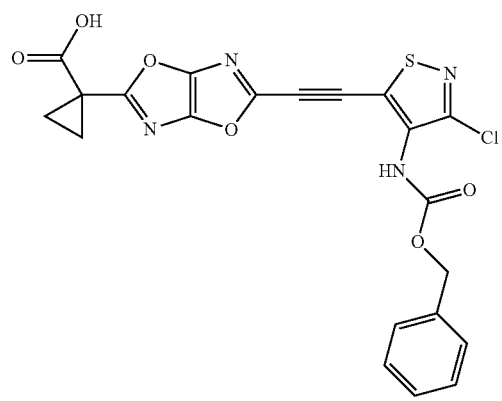 |
| 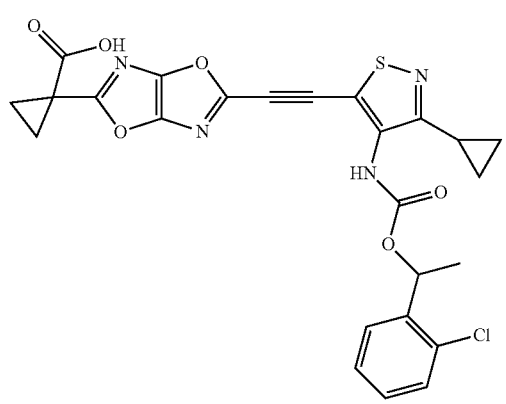 [SMILES: CC(OC(=O)Nc1c(C2CC2)nsc1C#Cc1nc2oc(C3(C(=O)O)CC3)nc2o1)c1ccccc1Cl] | 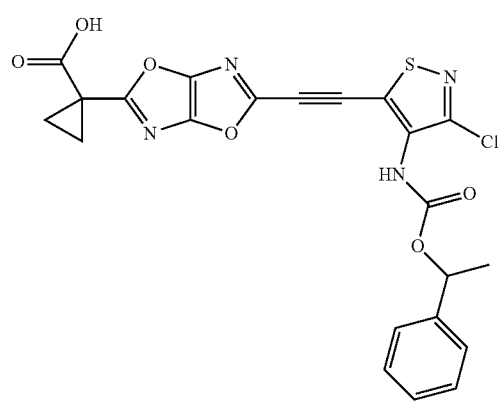 |

TABLE 18-continued
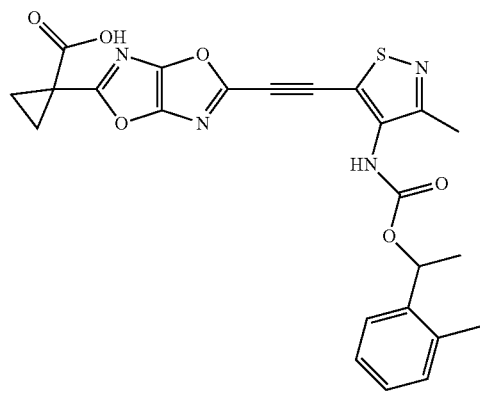
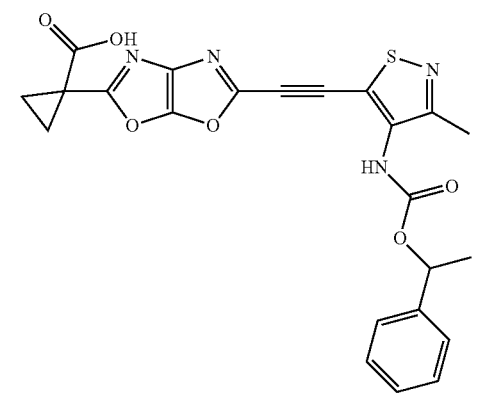
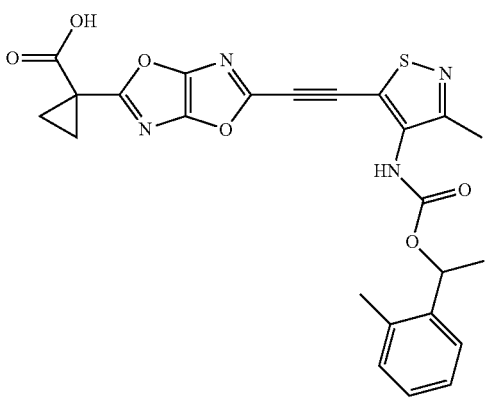
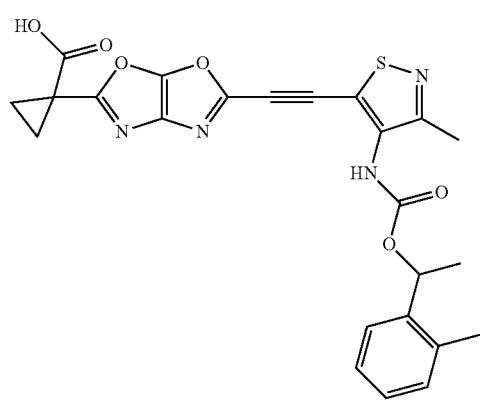
TABLE 18-continued
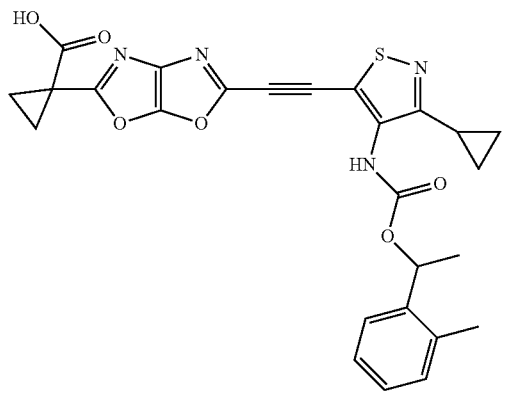 [SMILES: Cc1ccccc1C(C)OC(=O)Nc1c(C2CC2)nsc1C#Cc1nc2nc(C3(C(=O)O)CC3)oc2o1]
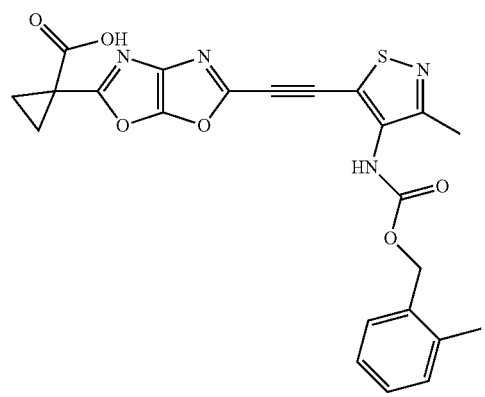 [SMILES: Cc1ccccc1COC(=O)Nc1c(C)nsc1C#Cc1nc2nc(C3(C(=O)O)CC3)oc2o1]
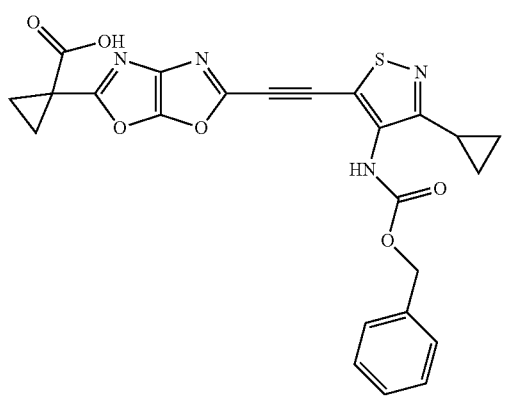 [SMILES: O=C(Nc1c(C2CC2)nsc1C#Cc1nc2nc(C3(C(=O)O)CC3)oc2o1)OCc1ccccc1]
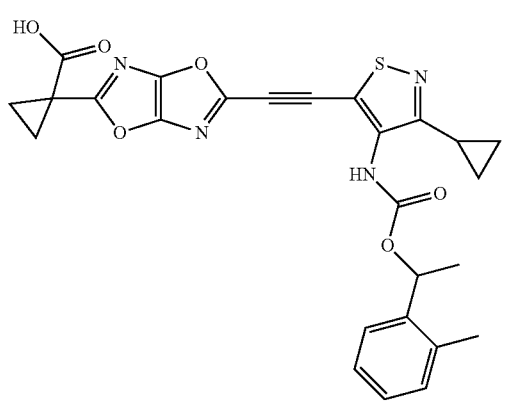 [SMILES: Cc1ccccc1C(C)OC(=O)Nc1c(C2CC2)nsc1C#Cc1nc2oc(C3(C(=O)O)CC3)nc2o1]

TABLE 18-continued
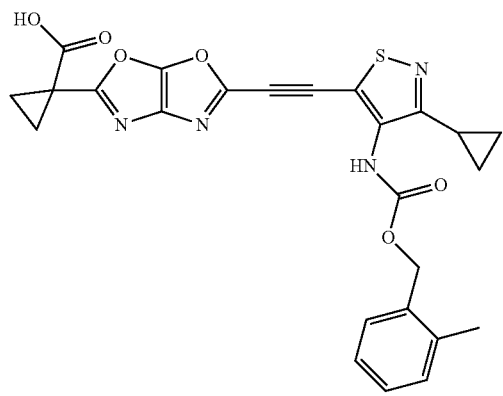 [SMILES: Cc1ccccc1COC(=O)Nc1c(C2CC2)nsc1C#Cc1nc2nc(C3(C(=O)O)CC3)oc2o1]
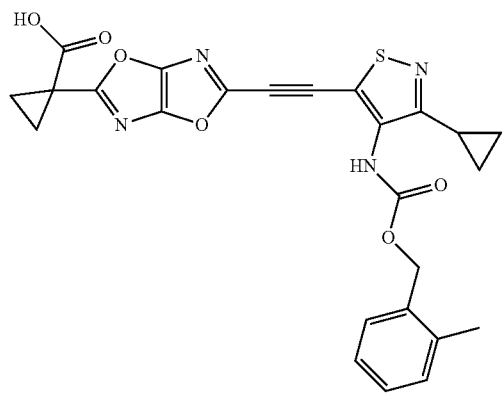
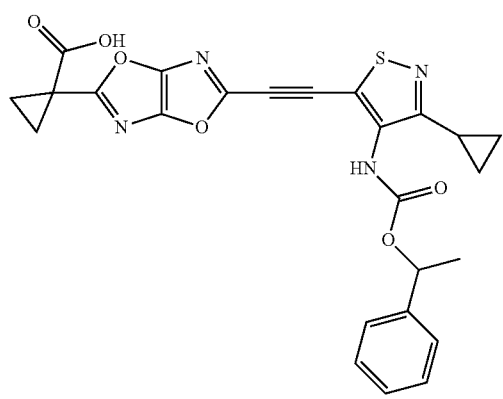
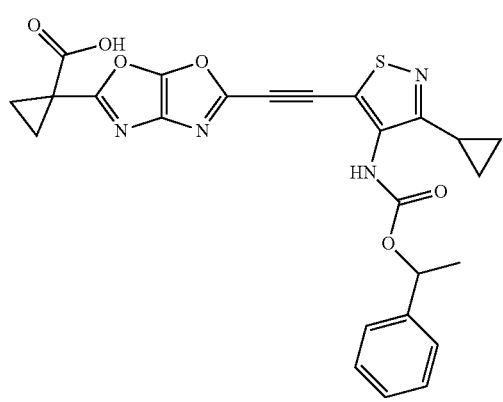
TABLE 18-continued
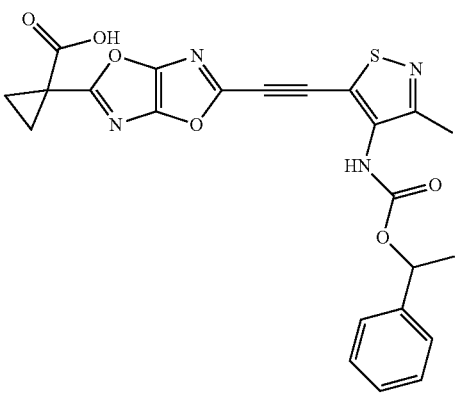
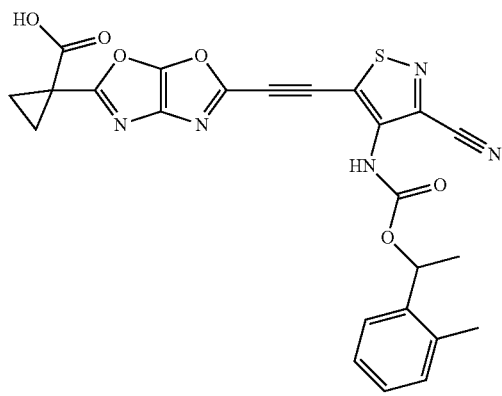 [SMILES: Cc1ccccc1C(C)OC(=O)Nc1c(C#N)nsc1C#Cc1nc2nc(C3(C(=O)O)CC3)oc2o1]
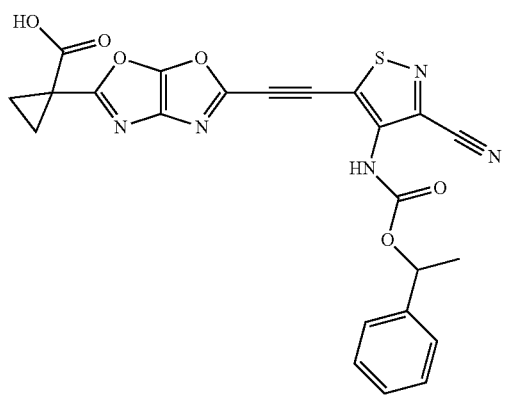 [SMILES: CC(OC(=O)Nc1c(C#N)nsc1C#Cc1nc2nc(C3(C(=O)O)CC3)oc2o1)c1ccccc1]
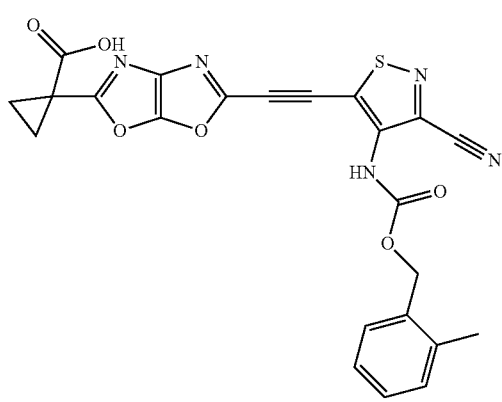 [SMILES: Cc1ccccc1COC(=O)Nc1c(C#N)nsc1C#Cc1nc2nc(C3(C(=O)O)CC3)oc2o1]

TABLE 18-continued
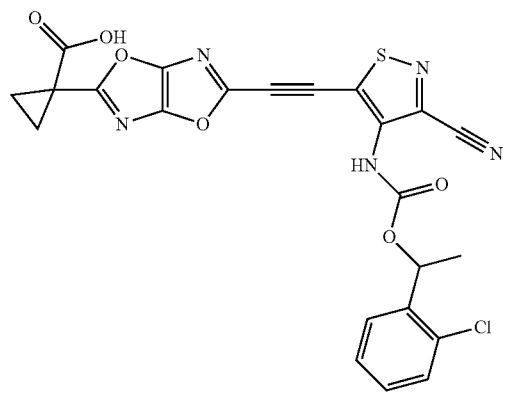
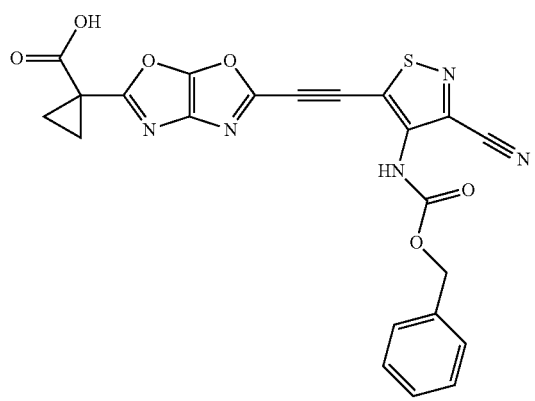
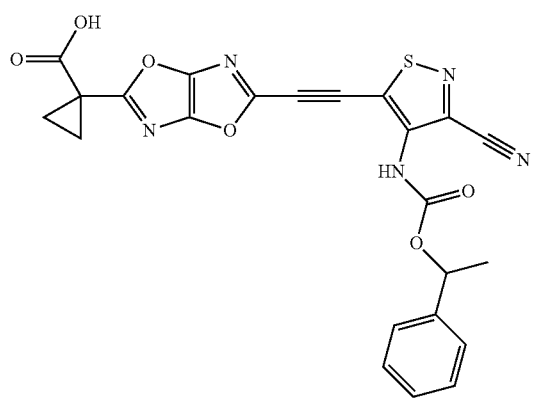
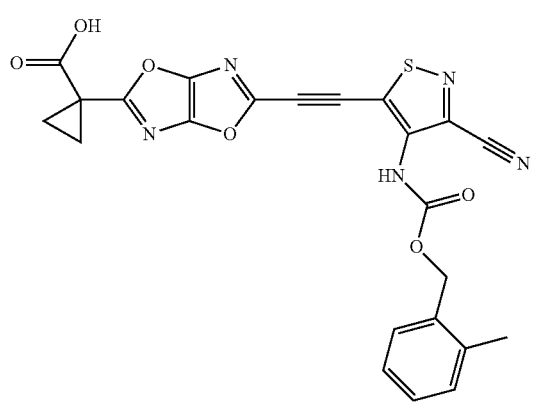
TABLE 18-continued
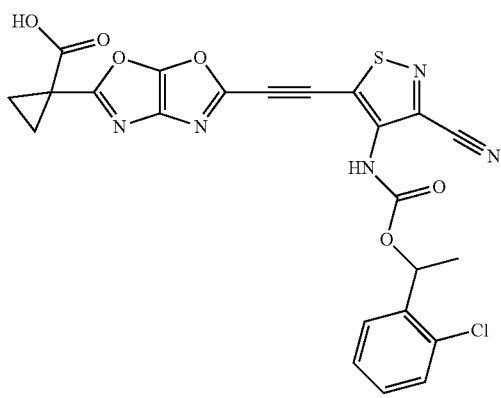 [SMILES: CC(OC(=O)Nc1c(C#N)nsc1C#Cc1nc2nc(C3(C(=O)O)CC3)oc2o1)c1ccccc1Cl]
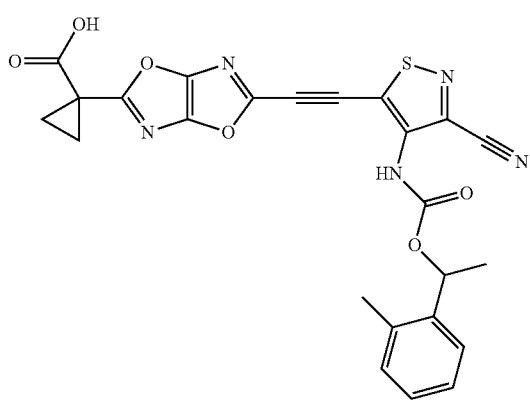
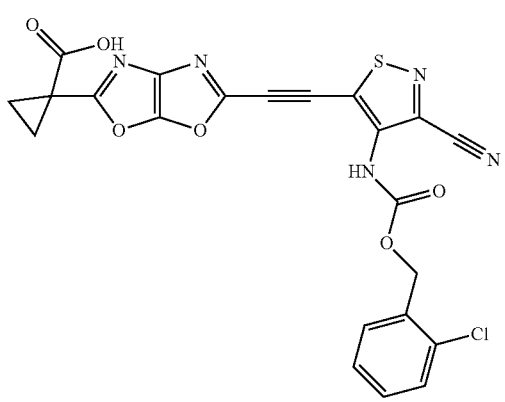 [SMILES: N#Cc1nsc(C#Cc2nc3nc(C4(C(=O)O)CC4)oc3o2)c1NC(=O)OCc1ccccc1Cl]
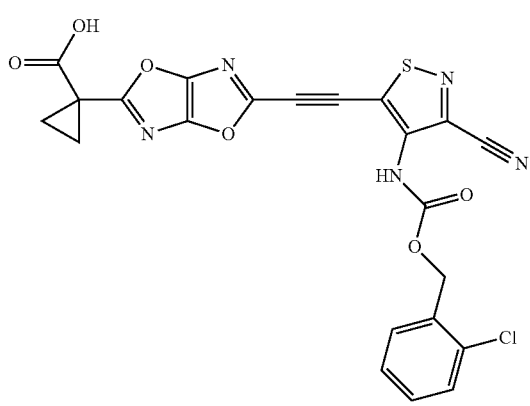

TABLE 18-continued
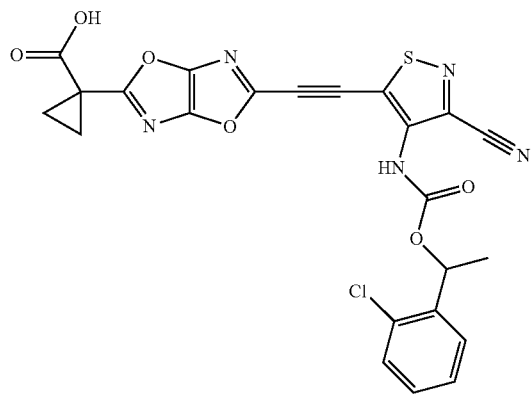
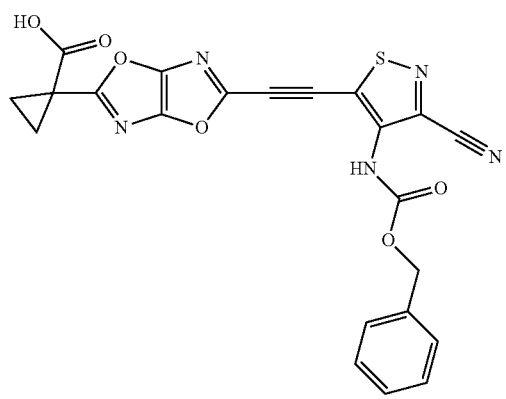
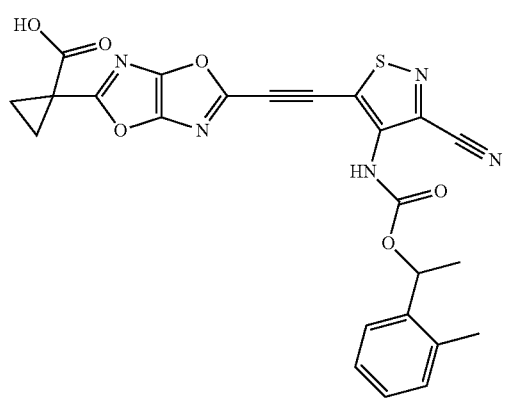
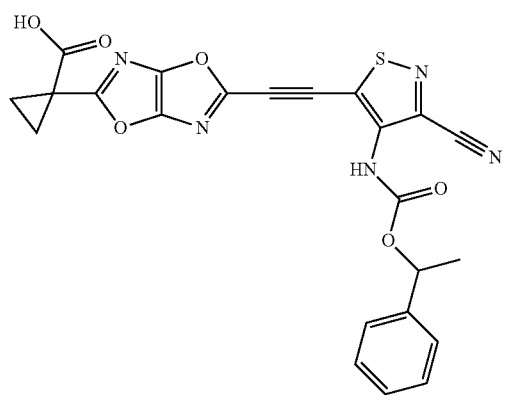
TABLE 18-continued
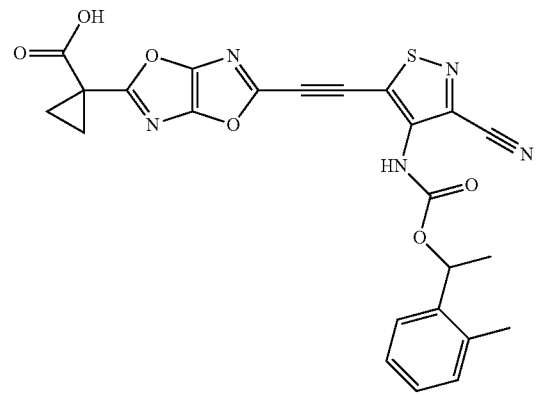 [SMILES: Cc1ccccc1C(C)OC(=O)Nc1c(C#N)nsc1C#Cc1nc2oc(C3(C(=O)O)CC3)nc2o1]
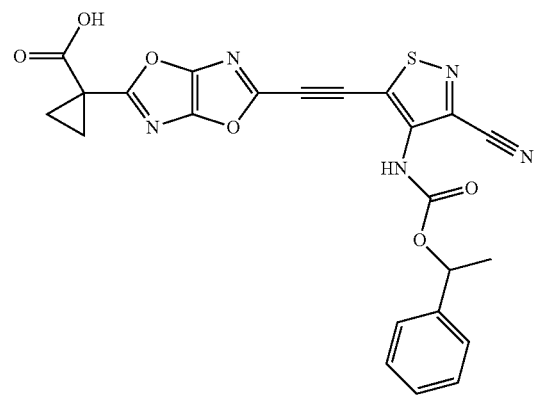
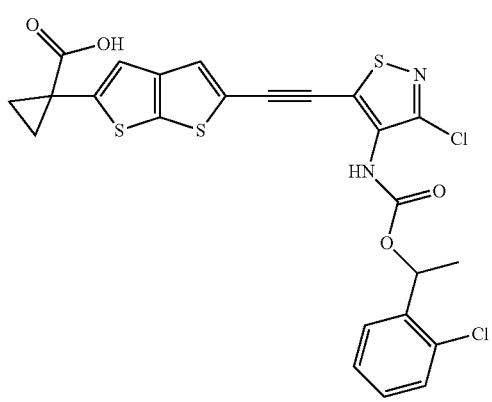 [SMILES: CC(OC(=O)Nc1c(Cl)nsc1C#Cc1cc2cc(C3(C(=O)O)CC3)sc2s1)c1ccccc1Cl]
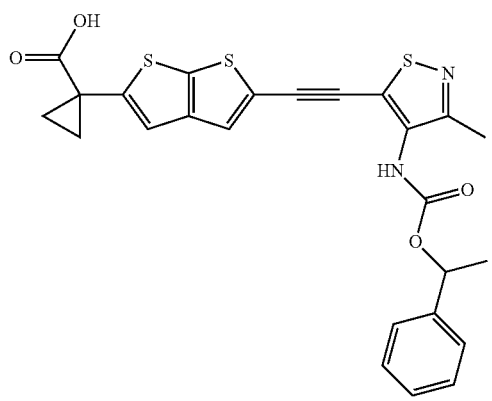

TABLE 18-continued
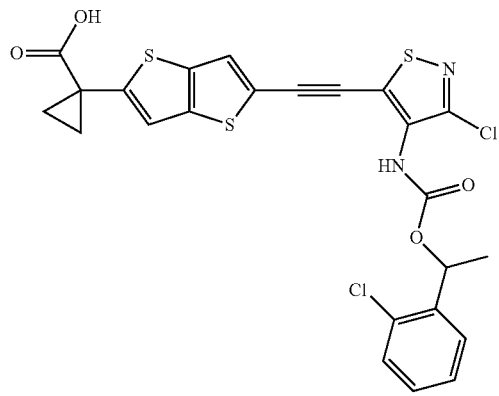 [SMILES: CC(OC(=O)Nc1c(Cl)nsc1C#Cc1cc2sc(C3(C(=O)O)CC3)cc2s1)c1ccccc1Cl]
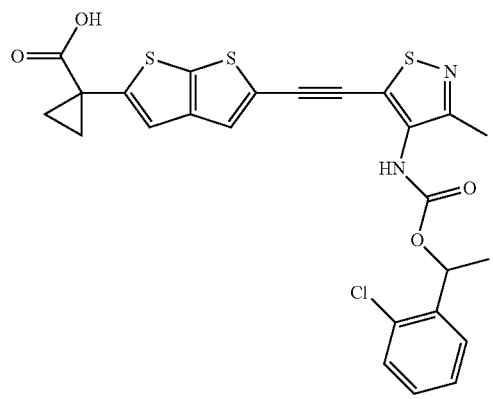
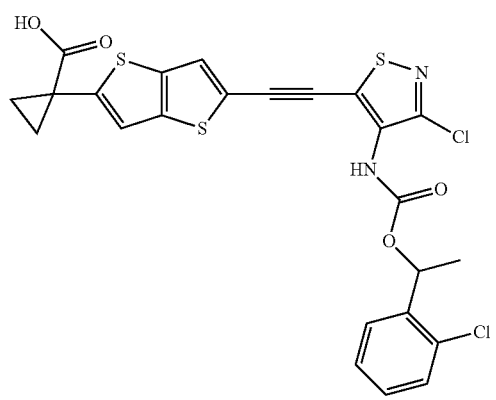
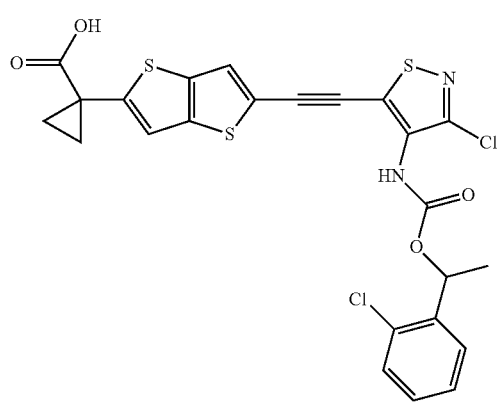 [SMILES: CC(OC(=O)Nc1c(Cl)nsc1C#Cc1cc2sc(C3(C(=O)O)CC3)cc2s1)c1ccccc1Cl]
TABLE 18-continued
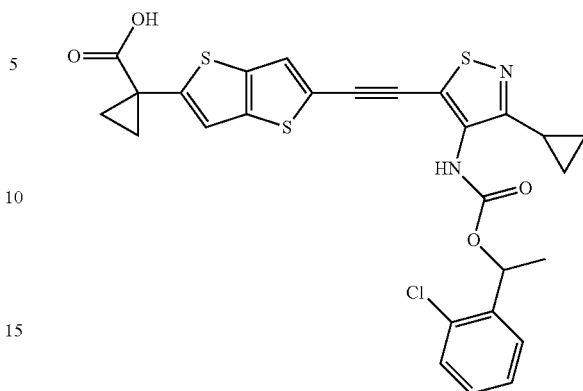
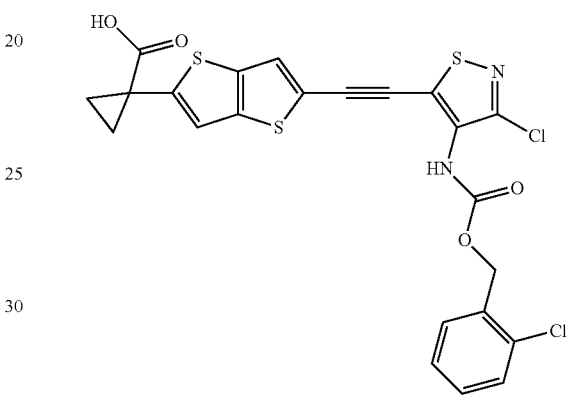
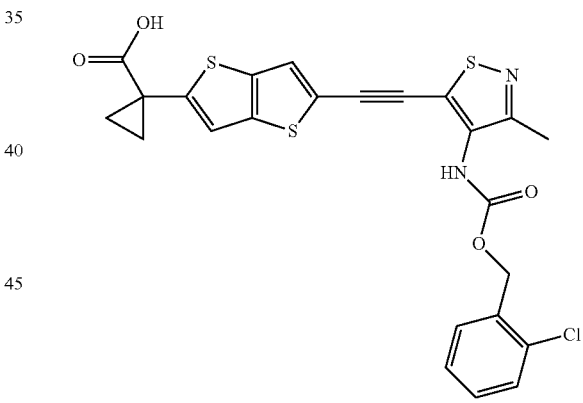
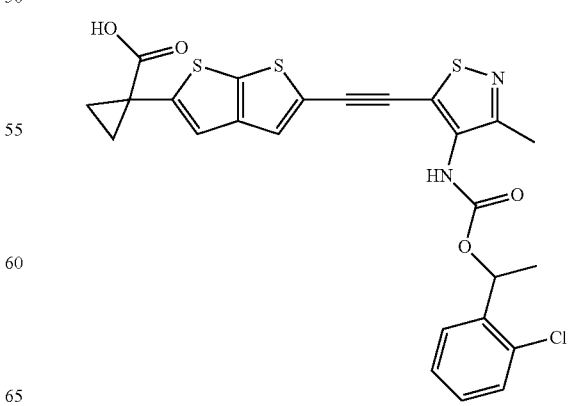

TABLE 18-continued
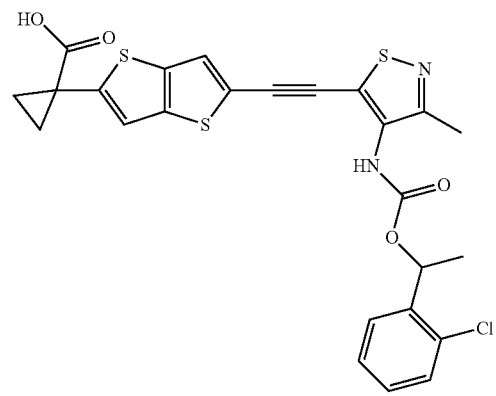
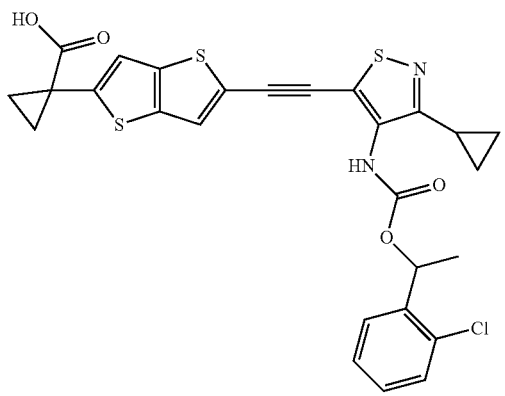
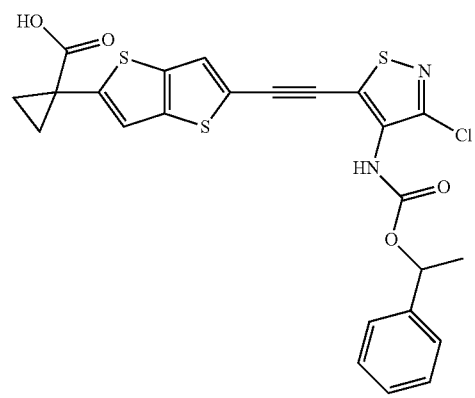
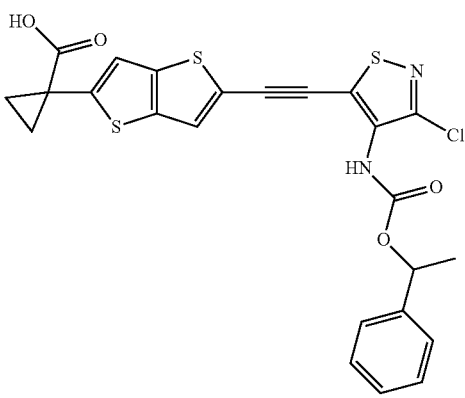
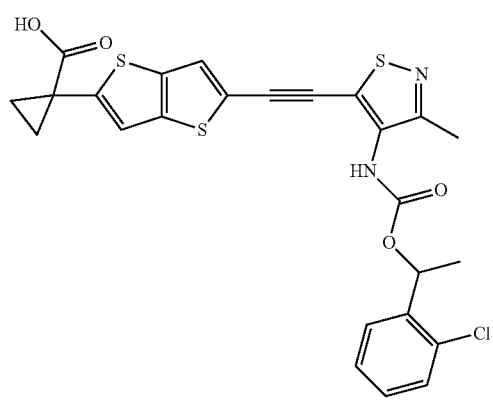
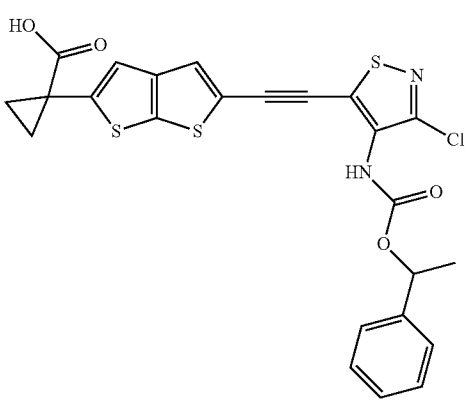
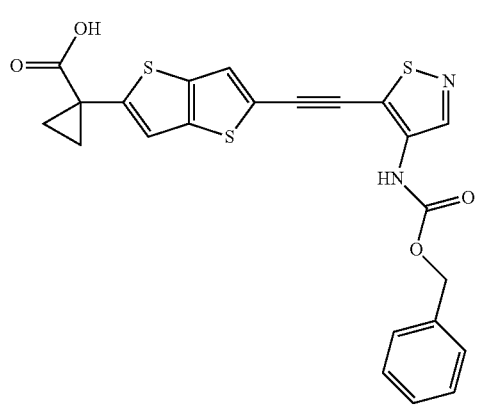 [SMILES: O=C(Nc1cnsc1C#Cc1cc2sc(C3(C(=O)O)CC3)cc2s1)OCc1ccccc1]
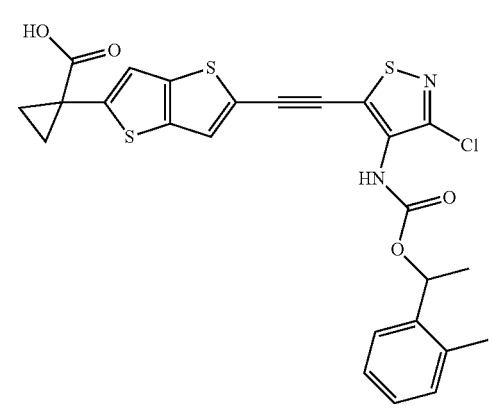 [SMILES: Cc1ccccc1C(C)OC(=O)Nc1c(Cl)nsc1C#Cc1cc2sc(C3(C(=O)O)CC3)cc2s1]

TABLE 18-continued
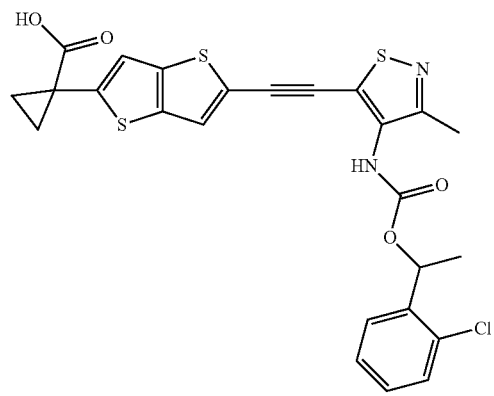 [SMILES: Cc1nsc(C#Cc2cc3sc(C4(C(=O)O)CC4)cc3s2)c1NC(=O)OC(C)c1ccccc1Cl]
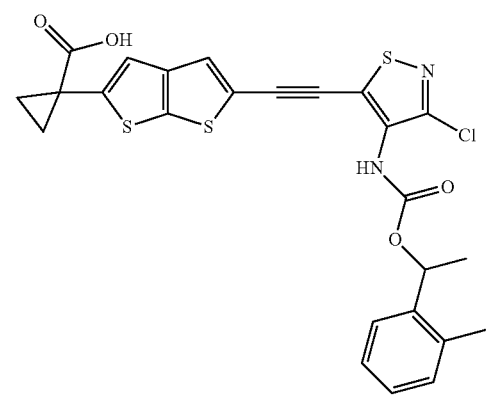 [SMILES: Cc1ccccc1C(C)OC(=O)Nc1c(Cl)nsc1C#Cc1cc2cc(C3(C(=O)O)CC3)sc2s1]
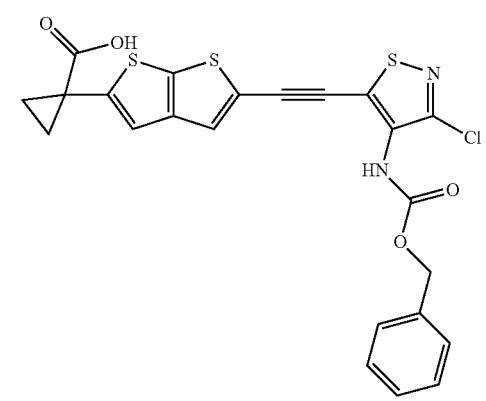 [SMILES: O=C(Nc1c(Cl)nsc1C#Cc1cc2cc(C3(C(=O)O)CC3)sc2s1)OCc1ccccc1]
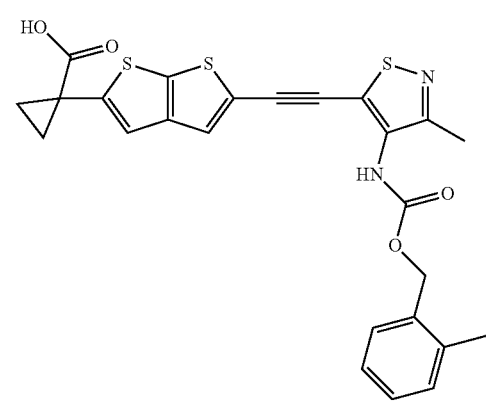 [SMILES: Cc1ccccc1COC(=O)Nc1c(C)nsc1C#Cc1cc2cc(C3(C(=O)O)CC3)sc2s1]
TABLE 18-continued
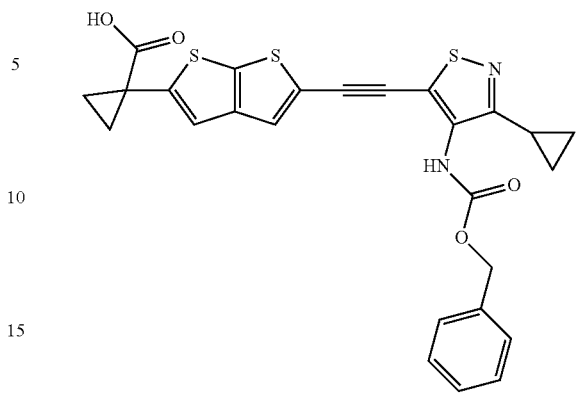
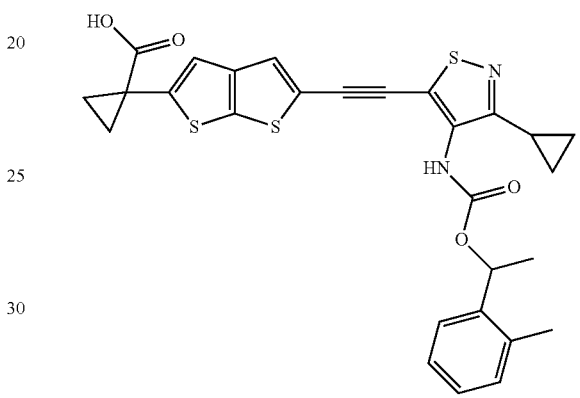
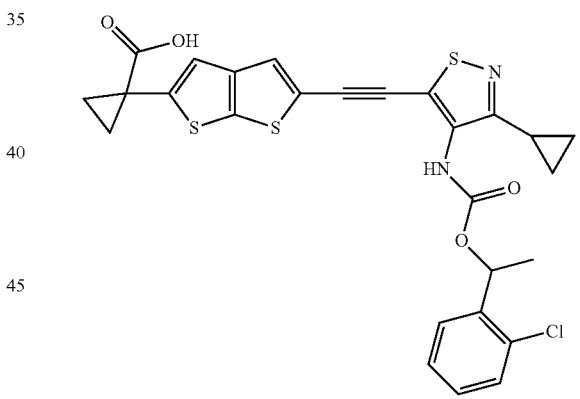
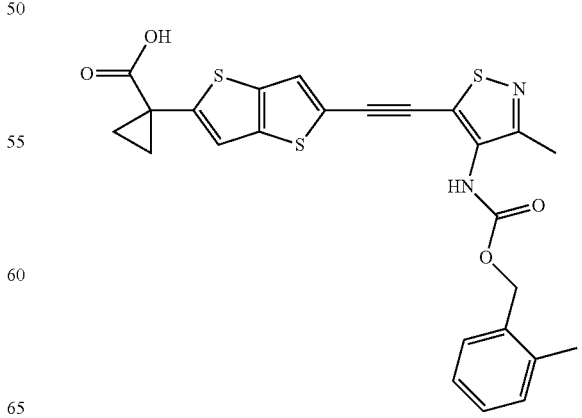

1511
TABLE 18-continued
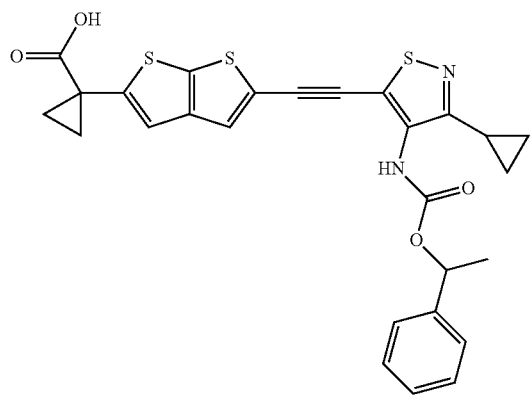
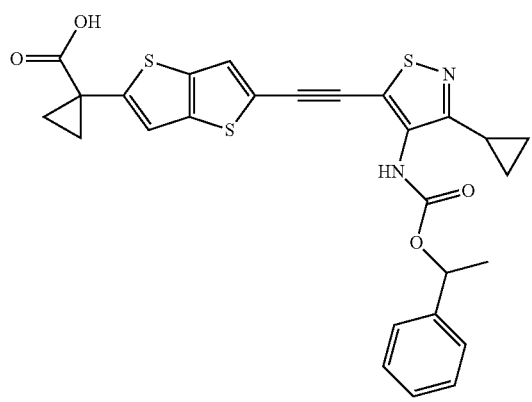
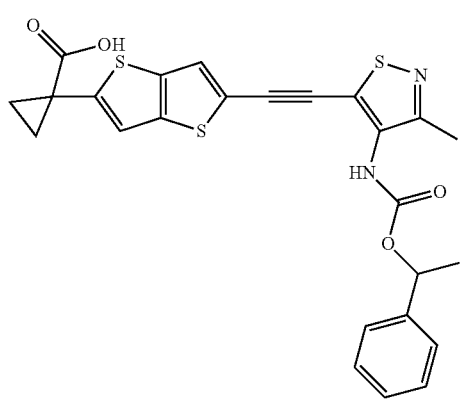
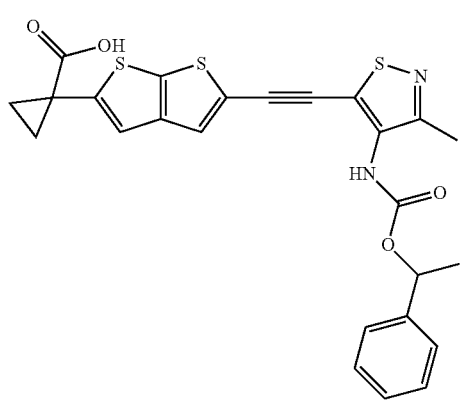 [SMILES: Cc1nsc(C#Cc2cc3cc(C4(C(=O)O)CC4)sc3s2)c1NC(=O)OC(C)c1ccccc1]
1512
TABLE 18-continued
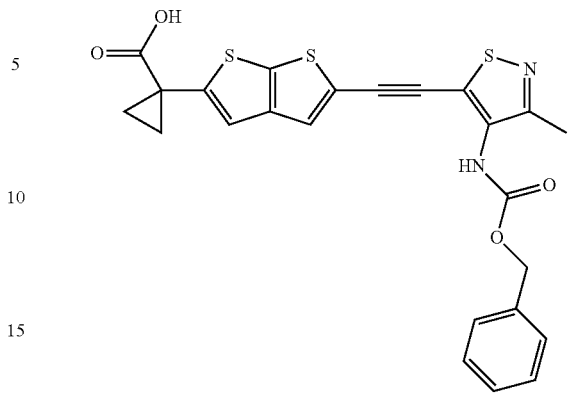
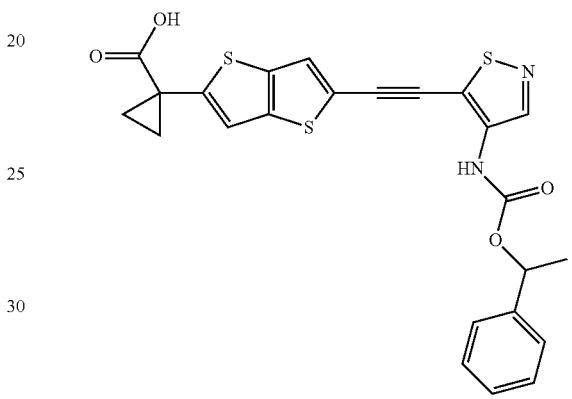
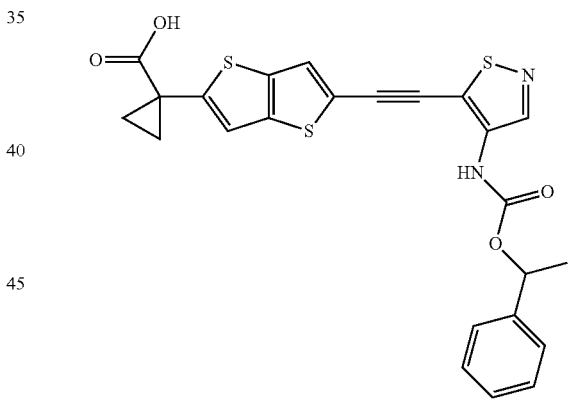
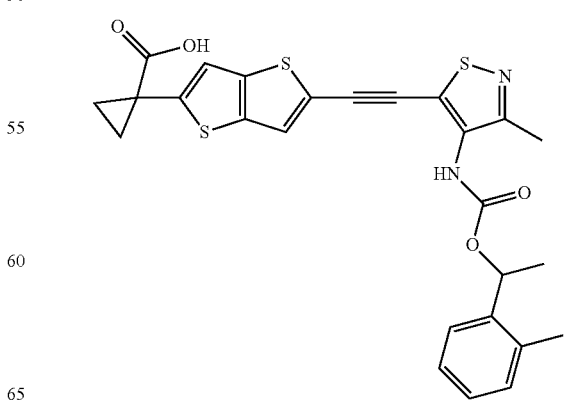

TABLE 18-continued
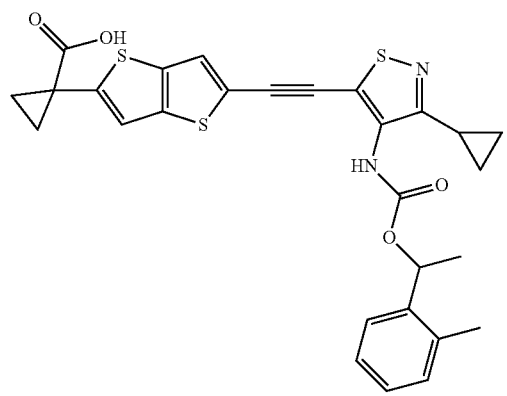
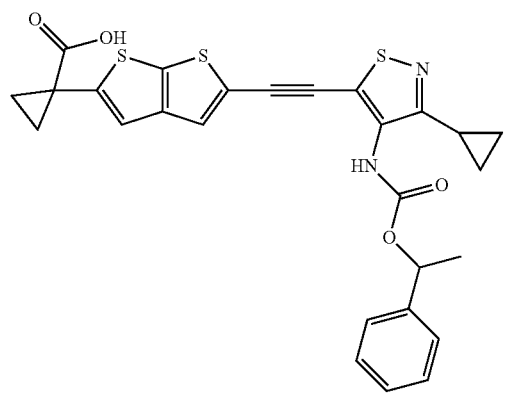
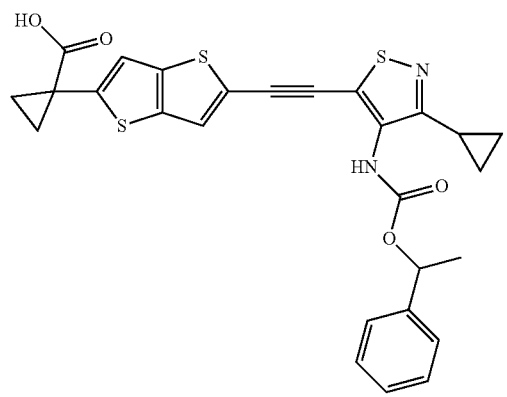
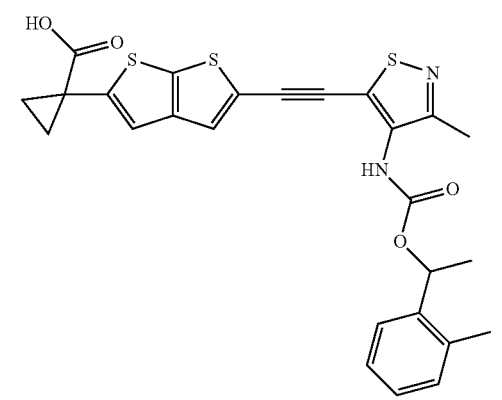
TABLE 18-continued
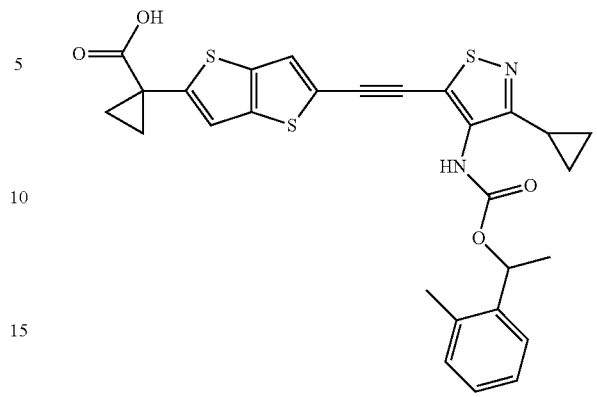
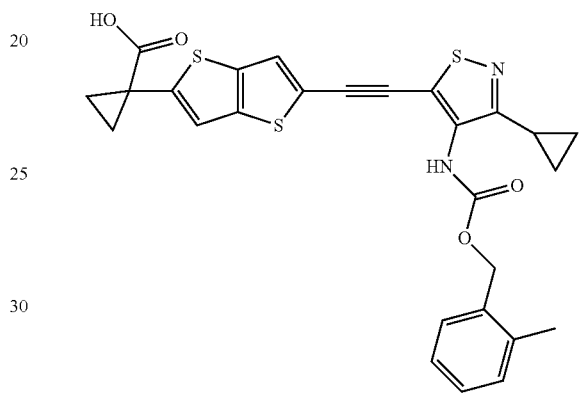
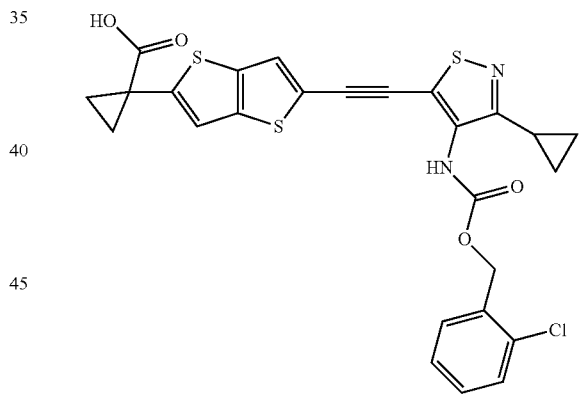
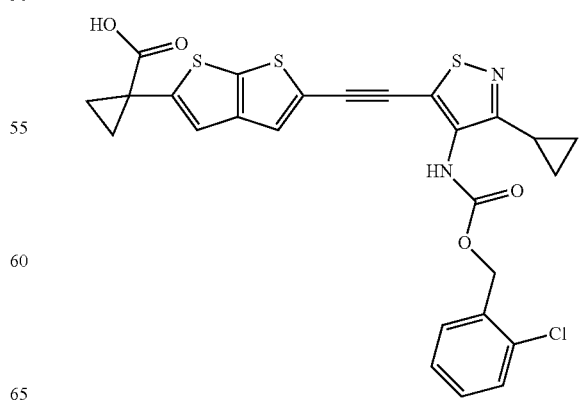

TABLE 18-continued
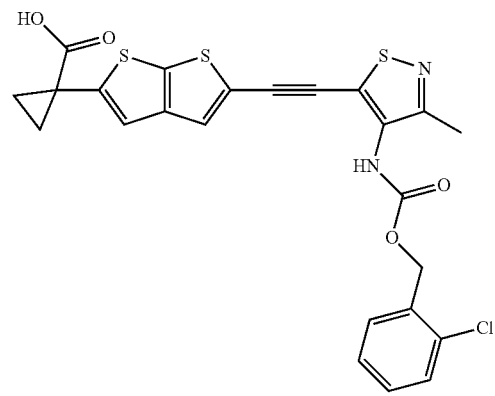 [SMILES: Cc1nsc(C#Cc2cc3cc(C4(C(=O)O)CC4)sc3s2)c1NC(=O)OCc1ccccc1Cl]
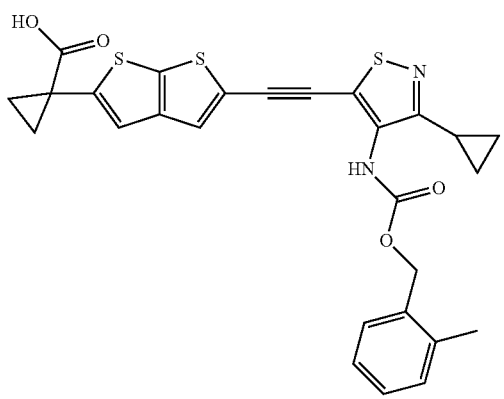 [SMILES: Cc1ccccc1COC(=O)Nc1c(C2CC2)nsc1C#Cc1cc2cc(C3(C(=O)O)CC3)sc2s1]
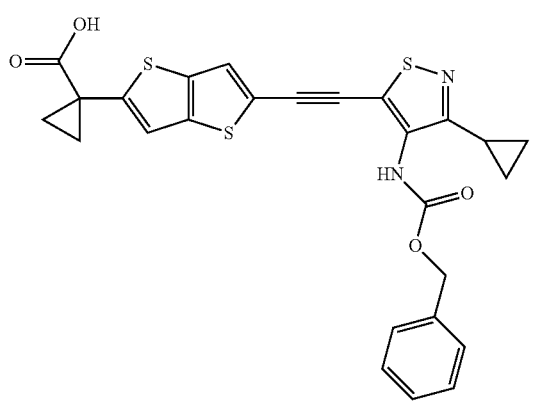
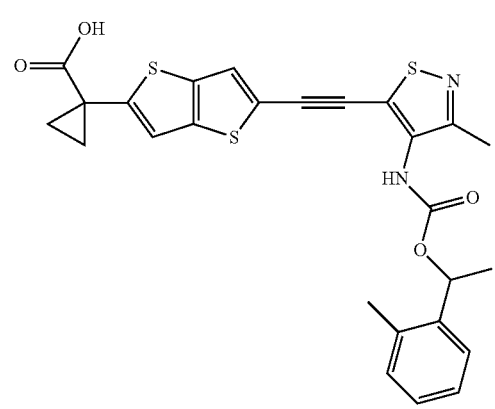
TABLE 18-continued
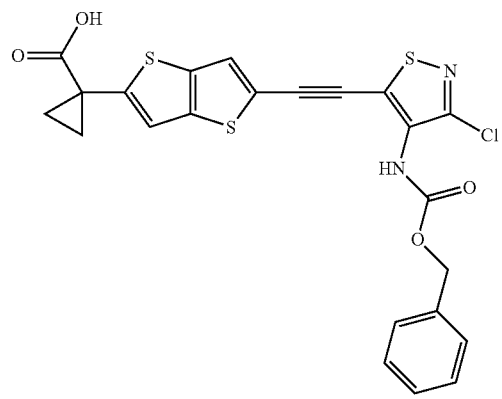
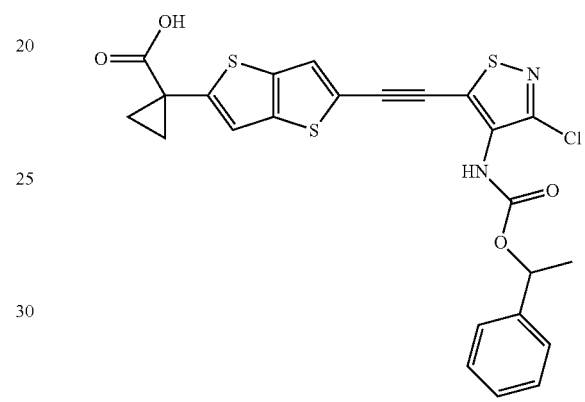
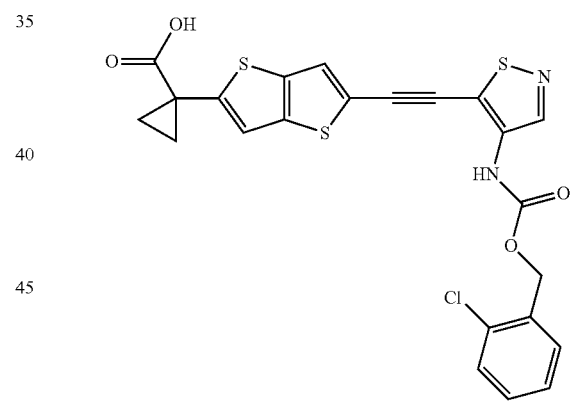
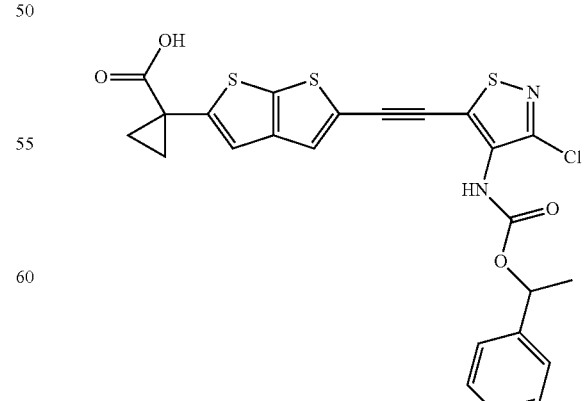

1517
TABLE 18-continued
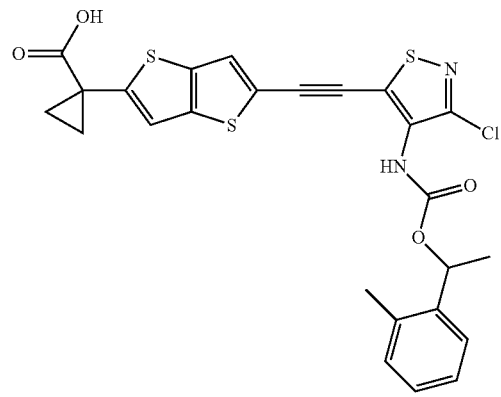
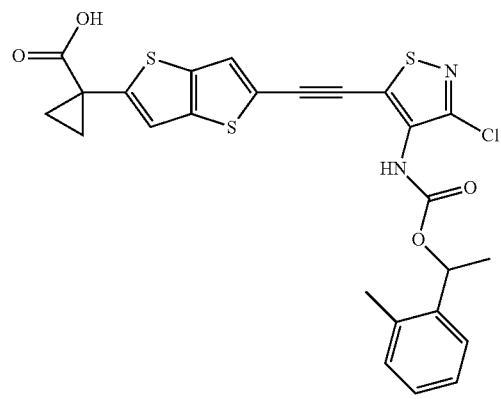
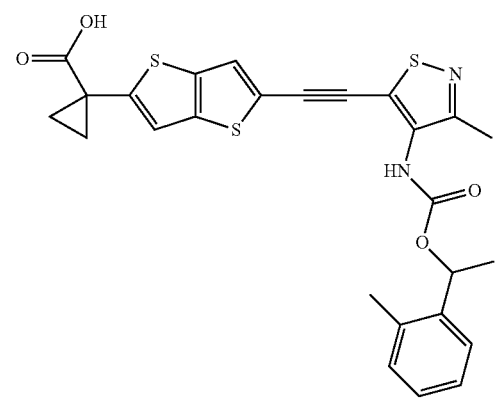
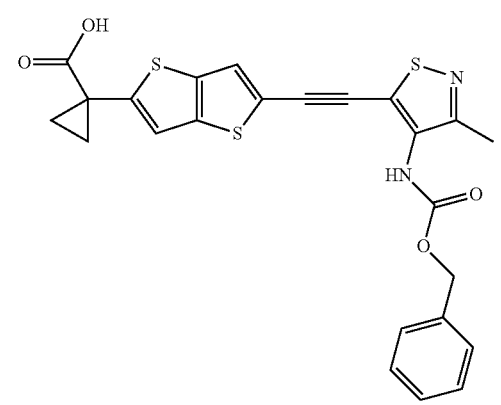
1518
TABLE 18-continued
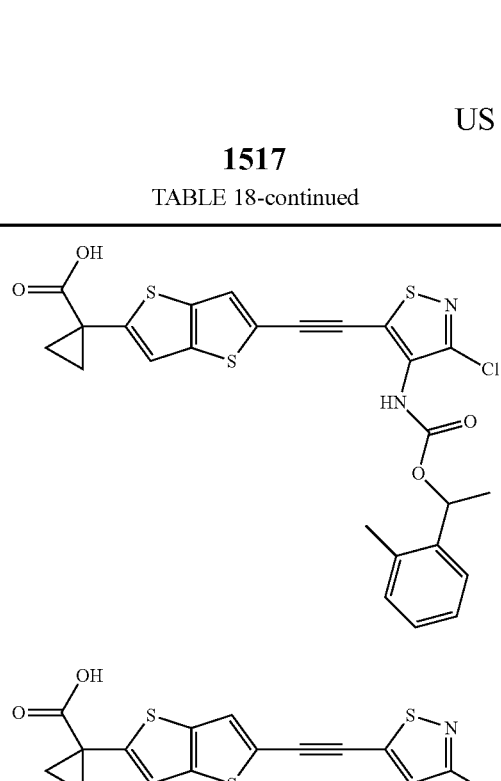
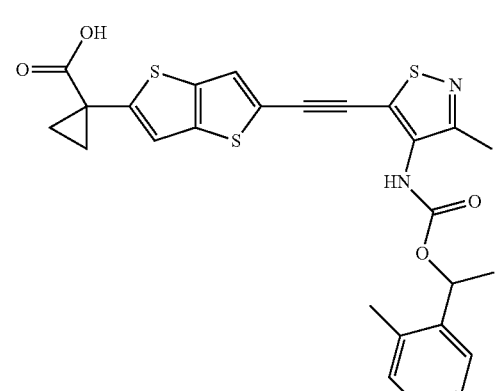
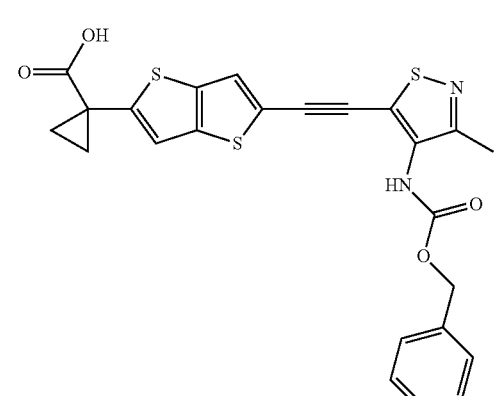

1519
TABLE 18-continued
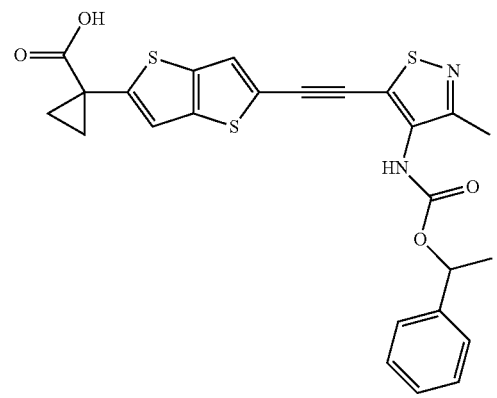
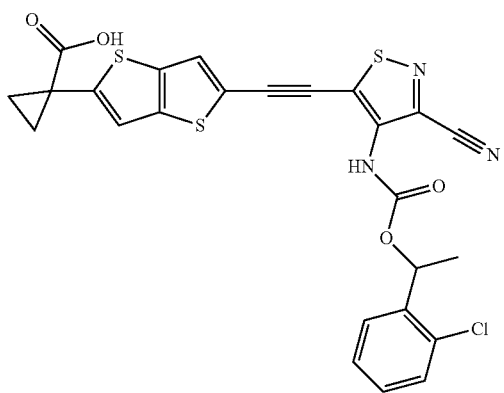
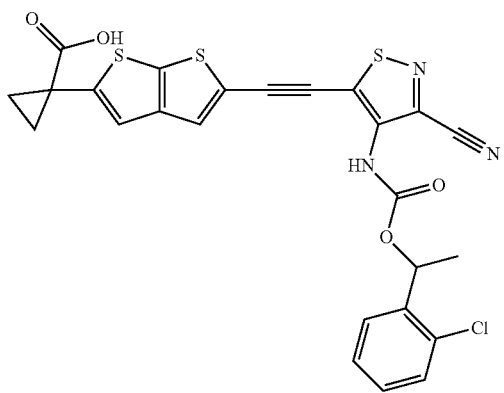 [SMILES: CC(OC(=O)Nc1c(C#N)nsc1C#Cc1cc2cc(C3(C(=O)O)CC3)sc2s1)c1ccccc1Cl]
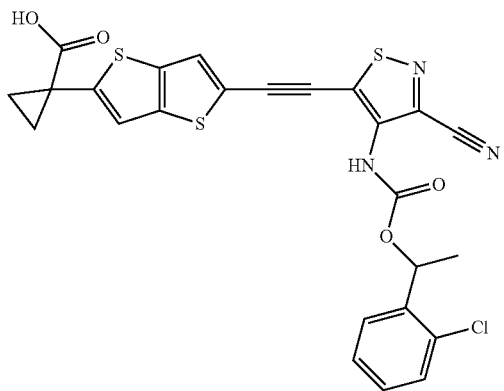 [SMILES: CC(OC(=O)Nc1c(C#N)nsc1C#Cc1cc2sc(C3(C(=O)O)CC3)cc2s1)c1ccccc1Cl]
1520
TABLE 18-continued
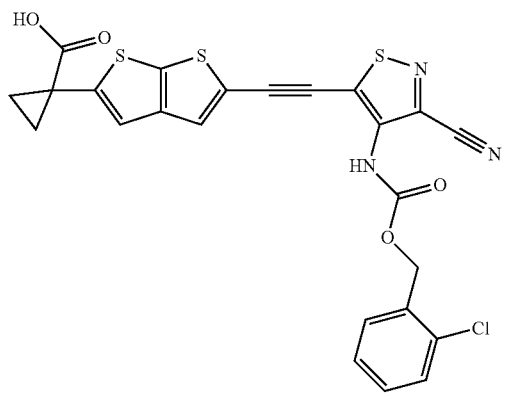 [SMILES: N#Cc1nsc(C#Cc2cc3cc(C4(C(=O)O)CC4)sc3s2)c1NC(=O)OCc1ccccc1Cl]
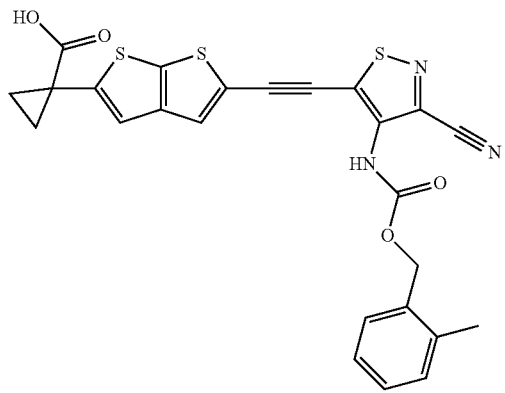 [SMILES: Cc1ccccc1COC(=O)Nc1c(C#N)nsc1C#Cc1cc2cc(C3(C(=O)O)CC3)sc2s1]
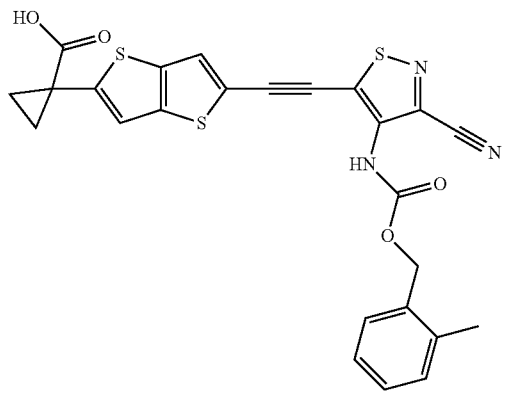 [SMILES: Cc1ccccc1COC(=O)Nc1c(C#N)nsc1C#Cc1cc2sc(C3(C(=O)O)CC3)cc2s1]
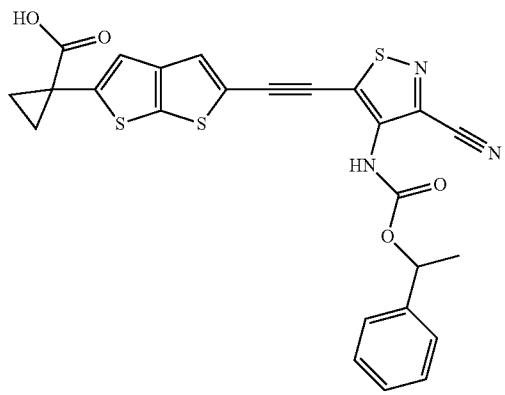 [SMILES: CC(OC(=O)Nc1c(C#N)nsc1C#Cc1cc2cc(C3(C(=O)O)CC3)sc2s1)c1ccccc1]

1521
TABLE 18-continued
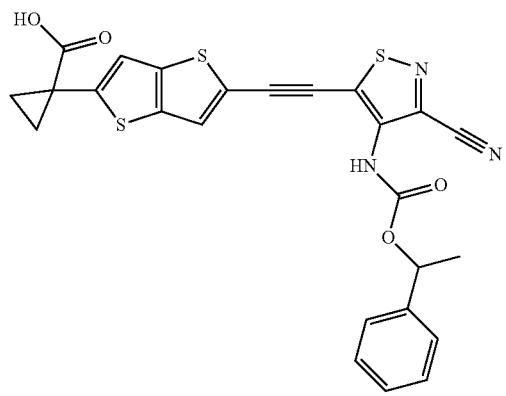 [SMILES: CC(OC(=O)Nc1c(C#N)nsc1C#Cc1cc2sc(C3(C(=O)O)CC3)cc2s1)c1ccccc1]
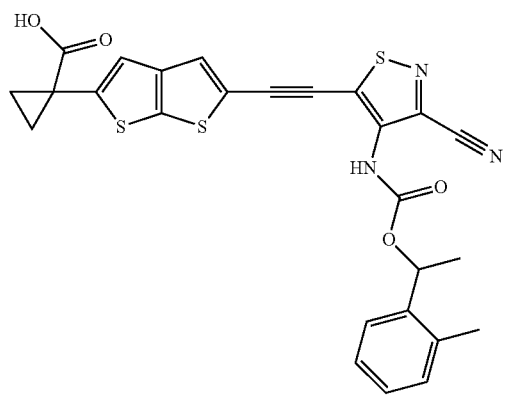 [SMILES: Cc1ccccc1C(C)OC(=O)Nc1c(C#N)nsc1C#Cc1cc2cc(C3(C(=O)O)CC3)sc2s1]
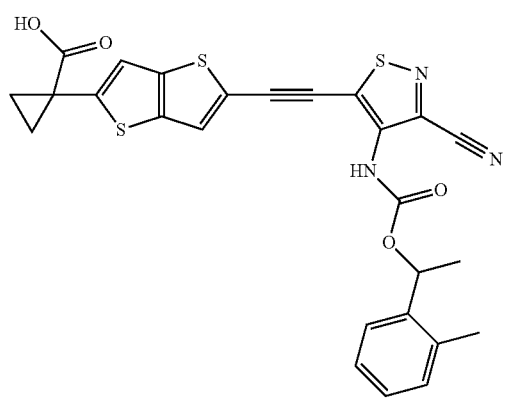 [SMILES: Cc1ccccc1C(C)OC(=O)Nc1c(C#N)nsc1C#Cc1cc2sc(C3(C(=O)O)CC3)cc2s1]
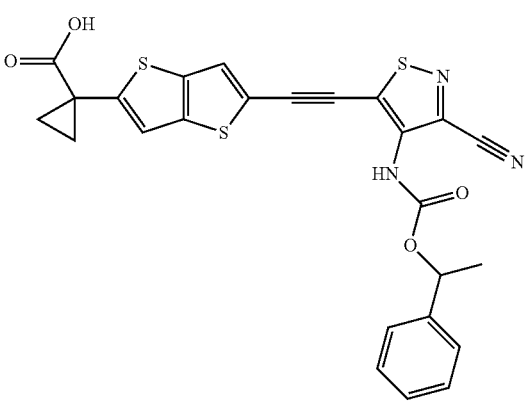 [SMILES: CC(OC(=O)Nc1c(C#N)nsc1C#Cc1cc2sc(C3(C(=O)O)CC3)cc2s1)c1ccccc1]
1522
TABLE 18-continued
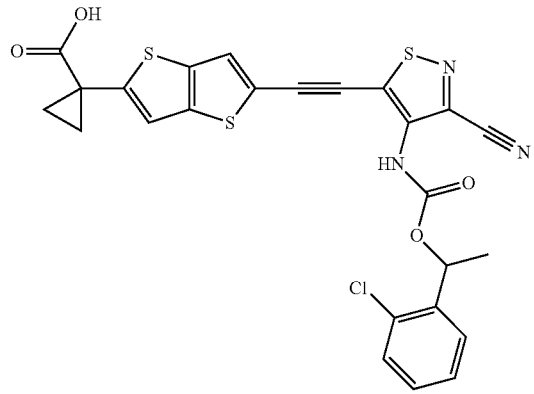
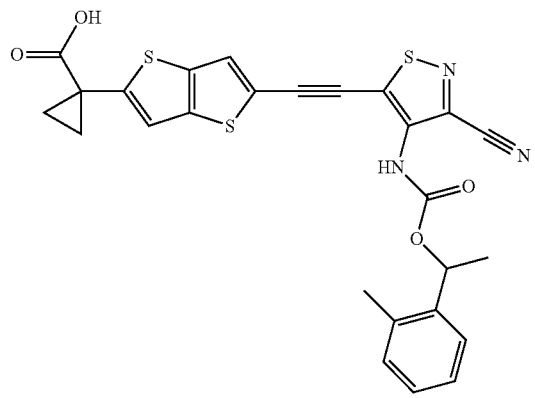 [SMILES: Cc1ccccc1C(C)OC(=O)Nc1c(C#N)nsc1C#Cc1cc2sc(C3(C(=O)O)CC3)cc2s1]
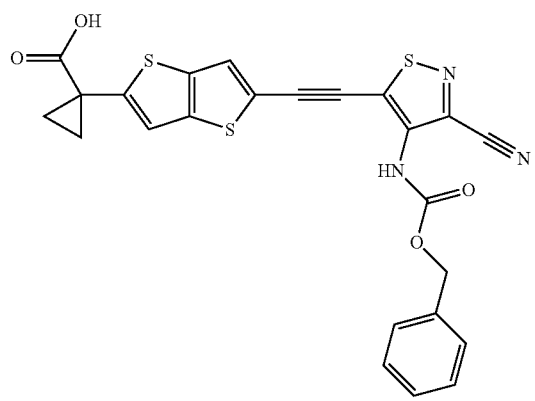 [SMILES: N#Cc1nsc(C#Cc2cc3sc(C4(C(=O)O)CC4)cc3s2)c1NC(=O)OCc1ccccc1]
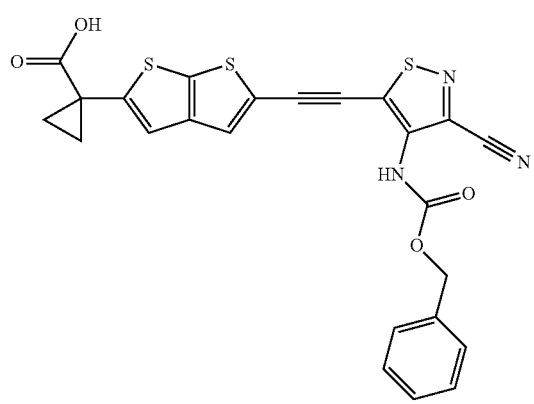

TABLE 18-continued
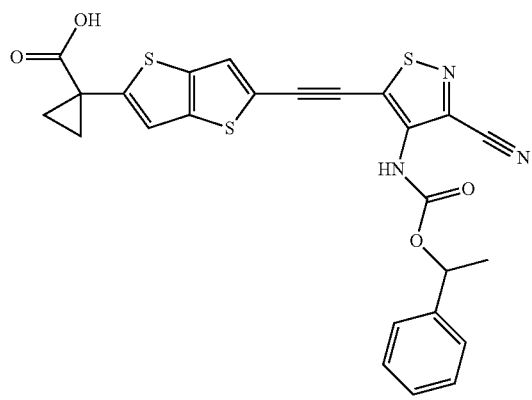 [SMILES: CC(OC(=O)Nc1c(C#N)nsc1C#Cc1cc2sc(C3(C(=O)O)CC3)cc2s1)c1ccccc1]
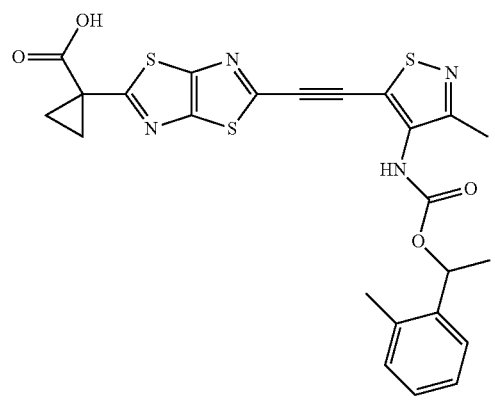
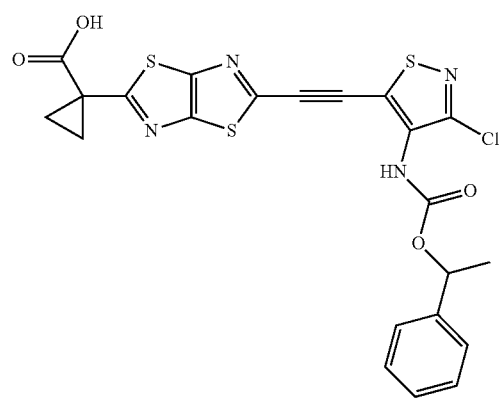 [SMILES: CC(OC(=O)Nc1c(Cl)nsc1C#Cc1nc2sc(C3(C(=O)O)CC3)nc2s1)c1ccccc1]
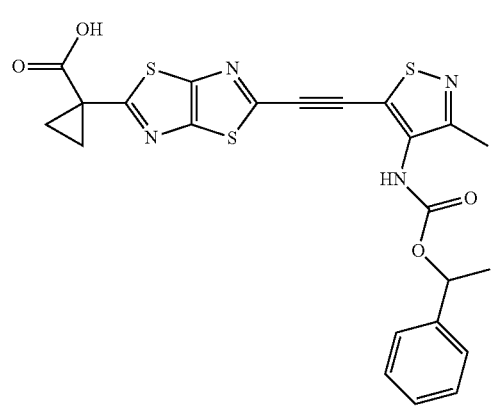
TABLE 18-continued
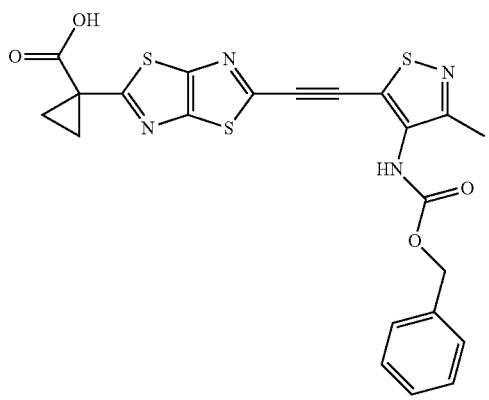 [SMILES: Cc1nsc(C#Cc2nc3sc(C4(C(=O)O)CC4)nc3s2)c1NC(=O)OCc1ccccc1]
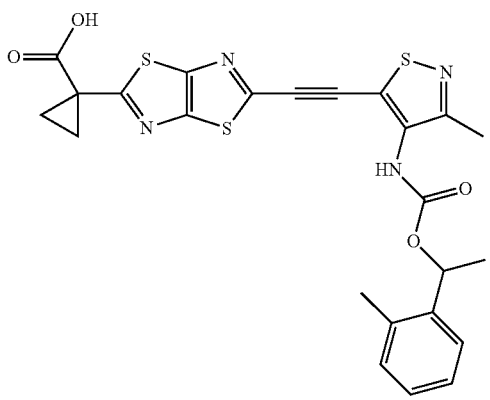
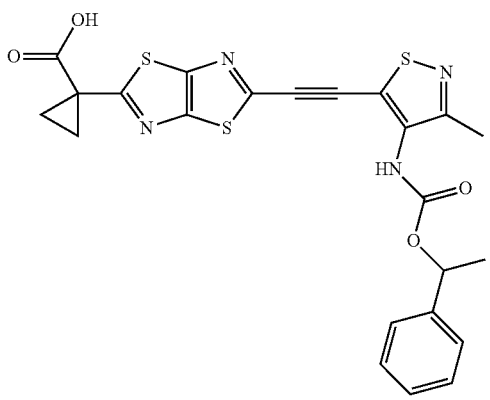
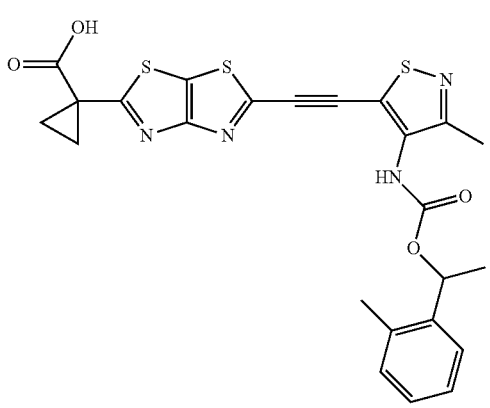

1525
TABLE 18-continued
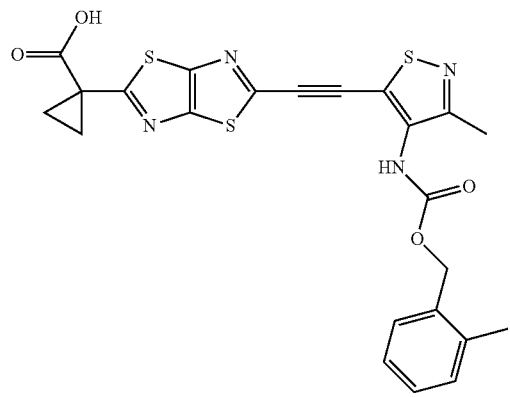 [SMILES: Cc1ccccc1COC(=O)Nc1c(C)nsc1C#Cc1nc2sc(C3(C(=O)O)CC3)nc2s1]
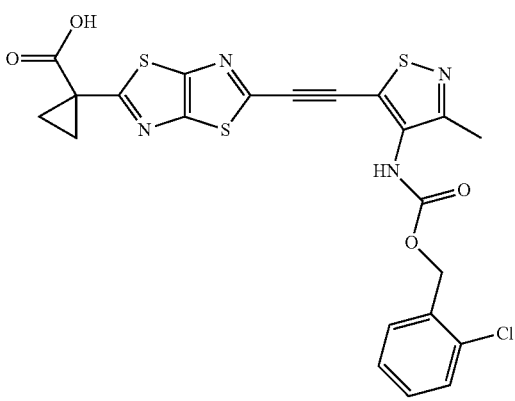
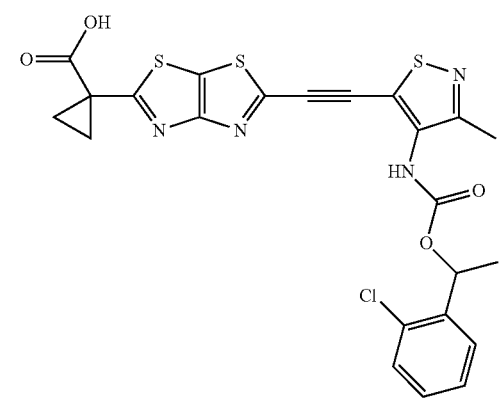
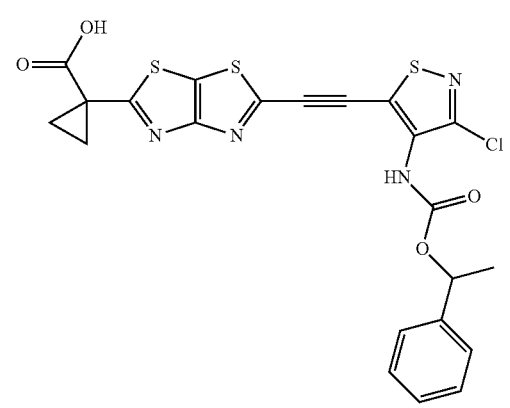 [SMILES: CC(OC(=O)Nc1c(Cl)nsc1C#Cc1nc2nc(C3(C(=O)O)CC3)sc2s1)c1ccccc1]
1526
TABLE 18-continued
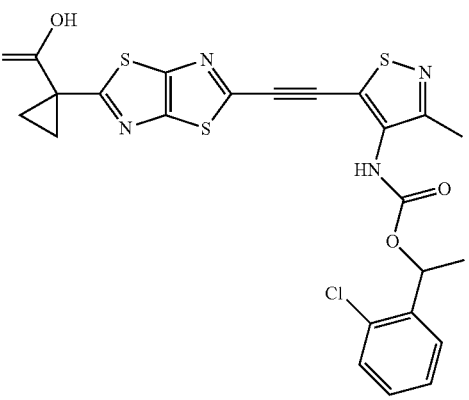
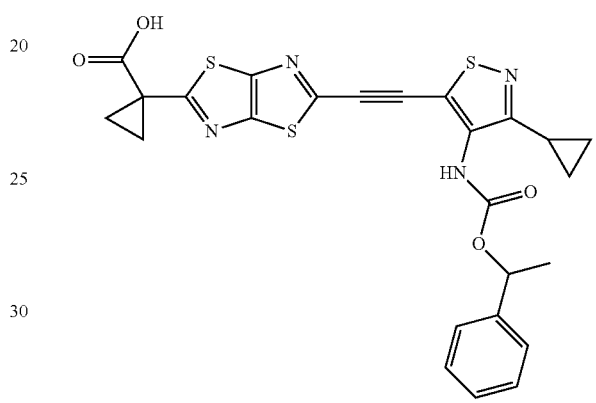
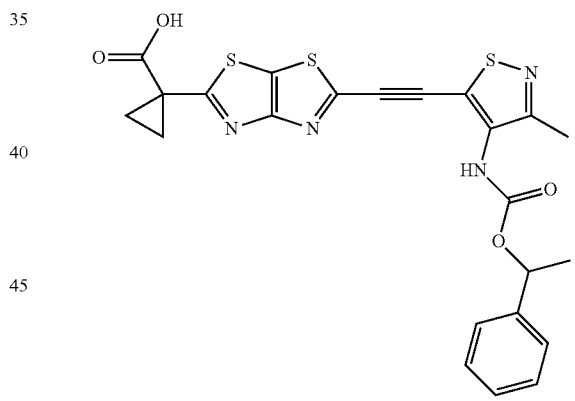
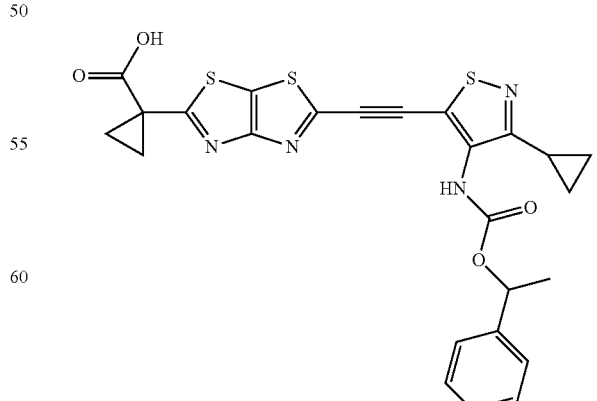

TABLE 18-continued
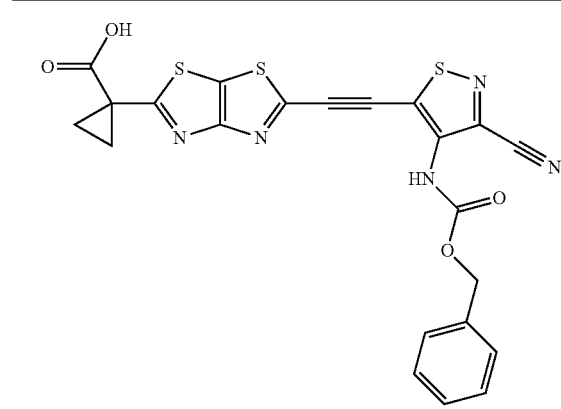
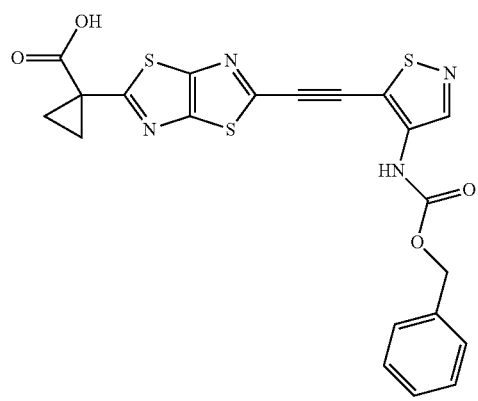 [SMILES: O=C(Nc1cnsc1C#Cc1nc2sc(C3(C(=O)O)CC3)nc2s1)OCc1ccccc1]
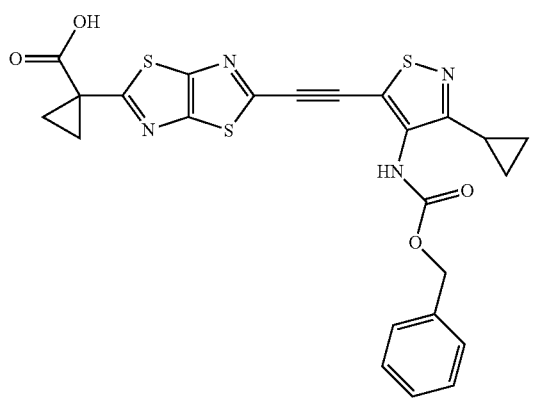 [SMILES: O=C(Nc1c(C2CC2)nsc1C#Cc1nc2sc(C3(C(=O)O)CC3)nc2s1)OCc1ccccc1]
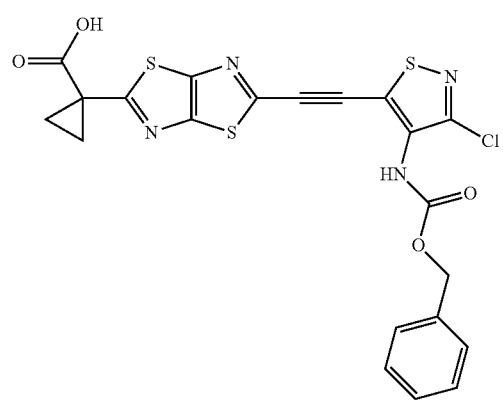 [SMILES: O=C(Nc1c(Cl)nsc1C#Cc1nc2sc(C3(C(=O)O)CC3)nc2s1)OCc1ccccc1]
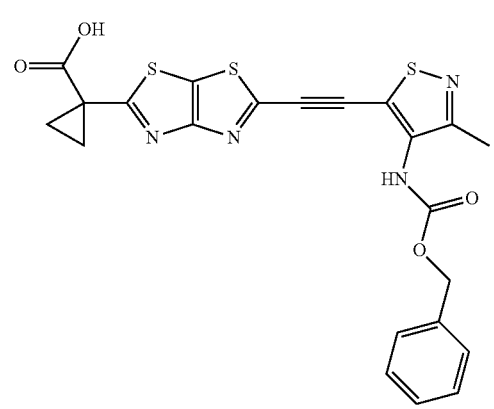 [SMILES: Cc1nsc(C#Cc2nc3nc(C4(C(=O)O)CC4)sc3s2)c1NC(=O)OCc1ccccc1]
TABLE 18-continued
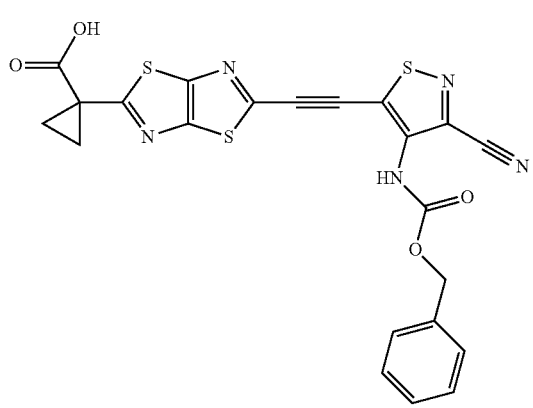 [SMILES: N#Cc1nsc(C#Cc2nc3sc(C4(C(=O)O)CC4)nc3s2)c1NC(=O)OCc1ccccc1]
or pharmaceutically acceptable salts thereof.
35. The compound or pharmaceutically acceptable salt thereof of claim 1, selected from compounds of Table 19 having the following structures:
TABLE 19
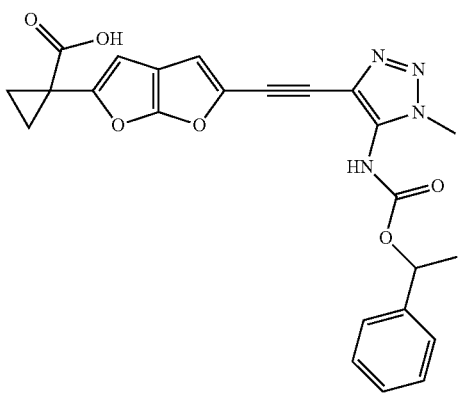 [SMILES: CC(OC(=O)Nc1c(C#Cc2cc3cc(C4(C(=O)O)CC4)oc3o2)nnn1C)c1ccccc1]

TABLE 19-continued
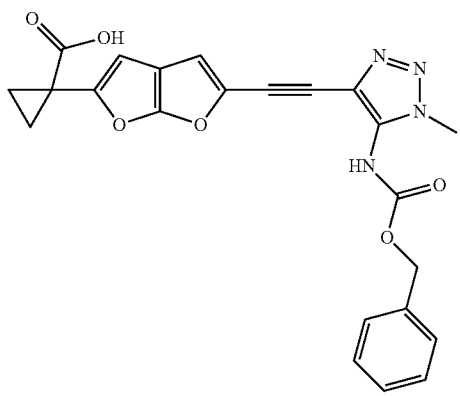 [SMILES: Cn1nnc(C#Cc2cc3cc(C4(C(=O)O)CC4)oc3o2)c1NC(=O)OCc1ccccc1]
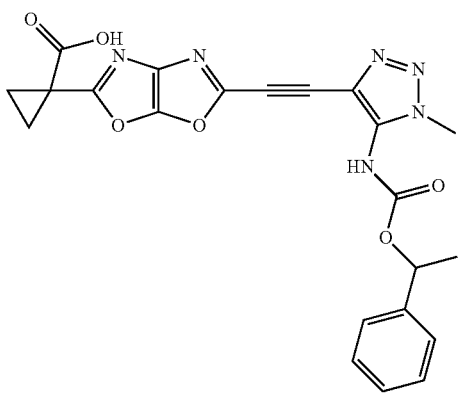 [SMILES: CC(OC(=O)Nc1c(C#Cc2nc3nc(C4(C(=O)O)CC4)oc3o2)nnn1C)c1ccccc1]
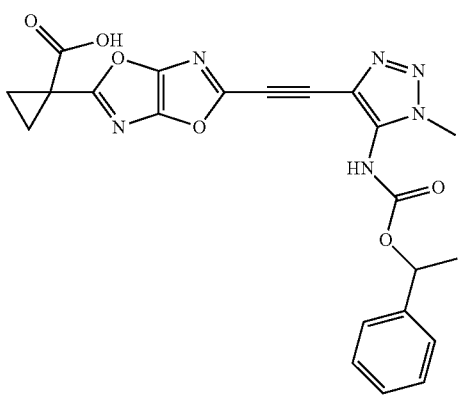 [SMILES: CC(OC(=O)Nc1c(C#Cc2nc3oc(C4(C(=O)O)CC4)nc3o2)nnn1C)c1ccccc1]
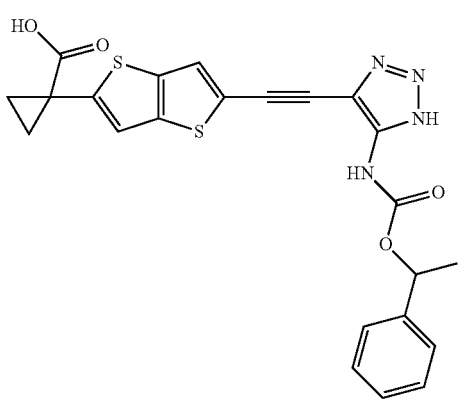 [SMILES: CC(OC(=O)Nc1[nH]nnc1C#Cc1cc2sc(C3(C(=O)O)CC3)cc2s1)c1ccccc1]
TABLE 19-continued
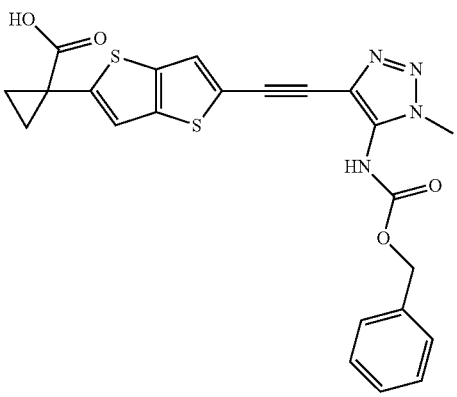 [SMILES: Cn1nnc(C#Cc2cc3sc(C4(C(=O)O)CC4)cc3s2)c1NC(=O)OCc1ccccc1]
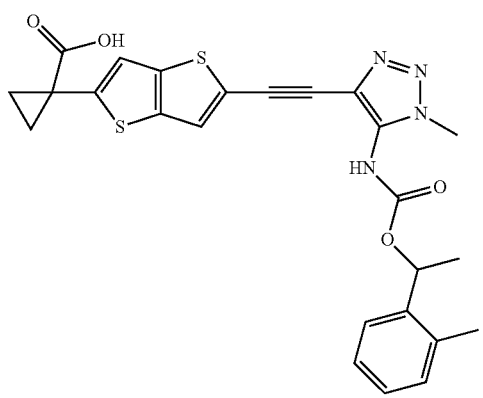 [SMILES: Cc1ccccc1C(C)OC(=O)Nc1c(C#Cc2cc3sc(C4(C(=O)O)CC4)cc3s2)nnn1C]
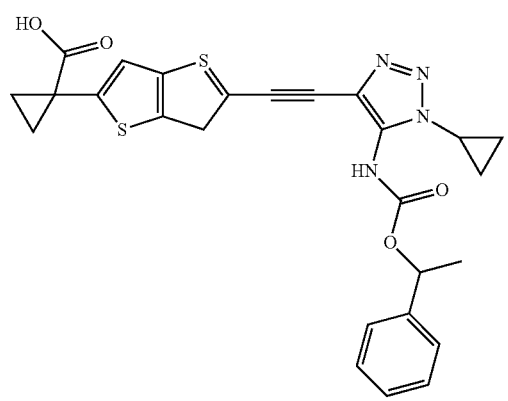
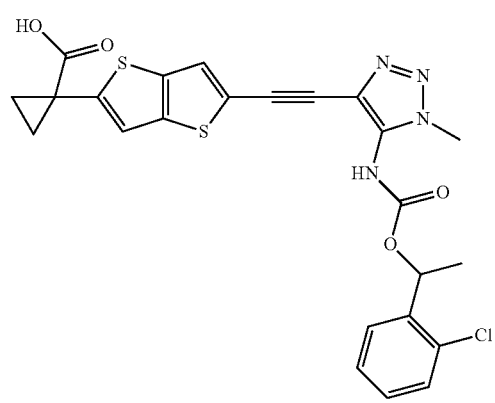 [SMILES: CC(OC(=O)Nc1c(C#Cc2cc3sc(C4(C(=O)O)CC4)cc3s2)nnn1C)c1ccccc1Cl]

TABLE 19-continued
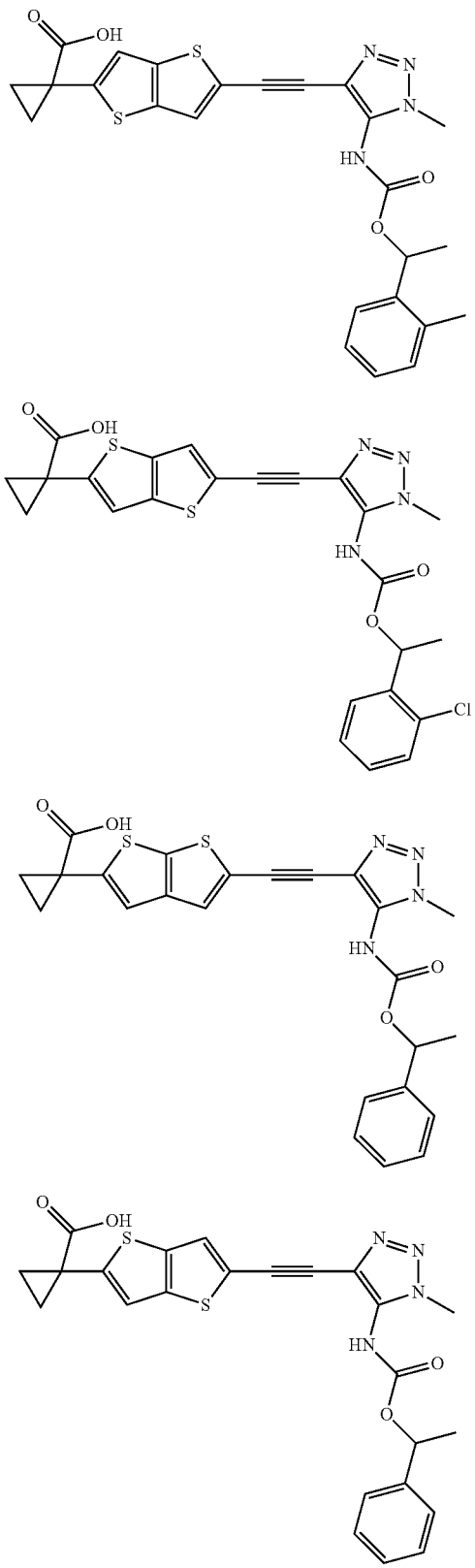
TABLE 19-continued
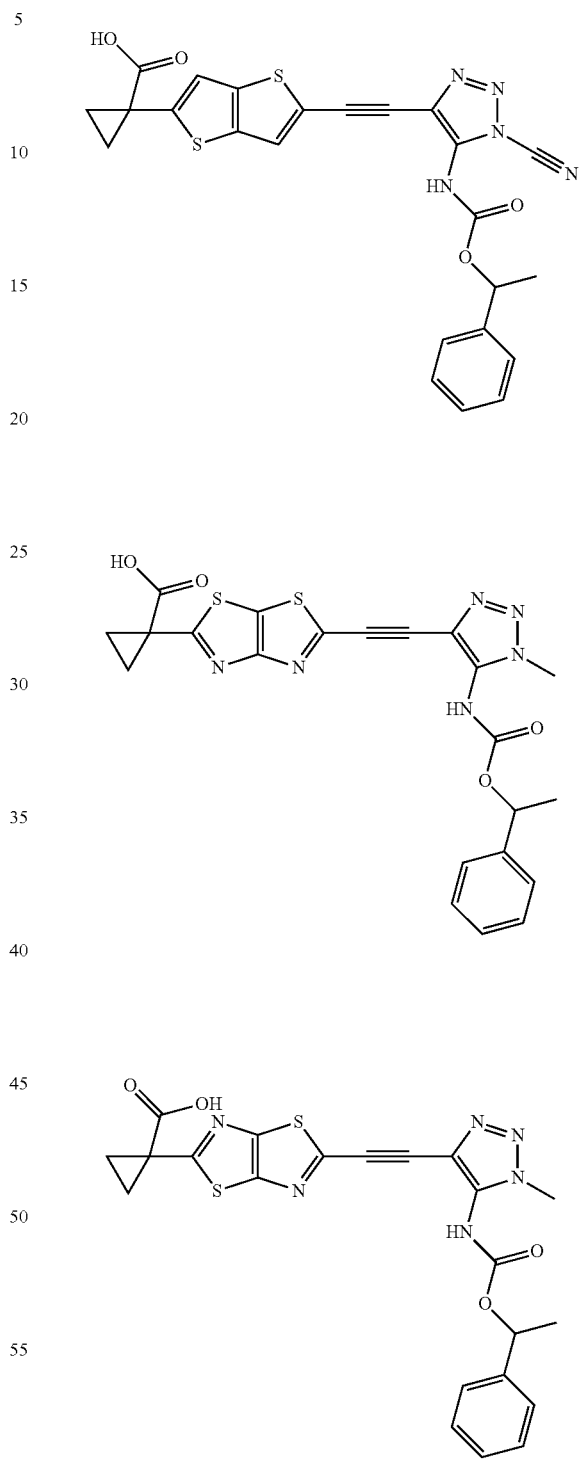
or pharmaceutically acceptable salts thereof.
* * * * *